US012291539B2

(12) United States Patent
Patel et al.

(10) Patent No.: US 12,291,539 B2
(45) Date of Patent: May 6, 2025

(54) KRAS G12C INHIBITORS

(71) Applicant: Frontier Medicines Corporation, South San Francisco, CA (US)

(72) Inventors: Snahel Patel, Foster City, CA (US); Philip A. Gerken, San Francisco, CA (US); Monika Jane Williams, Woodside, CA (US)

(73) Assignee: Frontier Medicines Corporation, South San Francisco, CA (US)

( * ) Notice: Subject to any disclaimer, the term of this patent is extended or adjusted under 35 U.S.C. 154(b) by 0 days.

(21) Appl. No.: 18/783,394

(22) Filed: Jul. 24, 2024

(65) Prior Publication Data
US 2025/0019387 A1    Jan. 16, 2025

Related U.S. Application Data

(63) Continuation of application No. 18/707,499, filed as application No. PCT/US2022/079324 on Nov. 4, 2022.

(60) Provisional application No. 63/403,565, filed on Sep. 2, 2022, provisional application No. 63/356,906, filed on Jun. 29, 2022, provisional application No. 63/276,478, filed on Nov. 5, 2021.

(51) Int. Cl.
*C07D 519/00* (2006.01)
*C07D 471/04* (2006.01)

(52) U.S. Cl.
CPC ......... *C07D 519/00* (2013.01); *C07D 471/04* (2013.01)

(58) Field of Classification Search
CPC .................................... C07D 519/00
USPC ........................................ 544/117
See application file for complete search history.

(56) References Cited

U.S. PATENT DOCUMENTS

| | | | |
|---|---|---|---|
| 2018/0072723 A1 | 3/2018 | Blake | |
| 2019/0144444 A1 | 5/2019 | Blake et al. | |
| 2020/0331911 A1 | 10/2020 | Marx | |
| 2024/0067662 A1 | 2/2024 | Condakes | |

FOREIGN PATENT DOCUMENTS

| | | |
|---|---|---|
| CN | 112694475 A | 4/2021 |
| WO | 2017201161 A1 | 11/2017 |
| WO | 2019099524 A1 | 5/2019 |
| WO | 2020055755 A1 | 3/2020 |
| WO | 2020055756 A1 | 3/2020 |
| WO | 2020055758 A1 | 3/2020 |
| WO | 2020055760 A1 | 3/2020 |
| WO | 2020055761 A1 | 3/2020 |
| WO | 2020118066 A1 | 6/2020 |
| WO | 2020146613 * | 7/2020 |
| WO | WO-2020146613 A1 * | 7/2020 ............. A61P 35/00 |
| WO | 2021129824 A1 | 7/2021 |
| WO | 2021141628 A1 | 7/2021 |
| WO | 2021168193 A1 | 8/2021 |
| WO | 2021244603 A1 | 12/2021 |
| WO | 2022042630 A1 | 3/2022 |
| WO | 2022132200 A1 | 6/2022 |
| WO | 2022187527 A1 | 9/2022 |
| WO | 2022248885 A2 | 12/2022 |
| WO | 2022256459 A1 | 12/2022 |
| WO | 2022262797 A1 | 12/2022 |
| WO | 2022271823 A1 | 12/2022 |
| WO | 2023004102 A2 | 1/2023 |
| WO | 2023081840 A1 | 5/2023 |
| WO | 2023133181 A1 | 7/2023 |
| WO | 2023137223 A1 | 7/2023 |
| WO | 2023225252 A1 | 11/2023 |
| WO | 2023240188 A1 | 12/2023 |
| WO | 2024006445 A1 | 1/2024 |
| WO | 2024036270 A1 | 2/2024 |
| WO | 2024138206 A1 | 6/2024 |
| WO | 2024158778 A1 | 8/2024 |

OTHER PUBLICATIONS

Chen, H. et al. (Nov. 23, 2020). "Small-Molecule Inhibitors Directly Targeting KRAS as Anticancer Therapeutics," Journal of Medicinal Chemistry 63:14404-14424.
Fell, J.B. et al. (Apr. 6, 2020). "Identification of the Clinical Development Candidate MRTX489, A Covalent KRASG12C Inhibitor for the Treatment of Cancer," J. Med. Chem. 63:6679-6693.
International Preliminary Report on Patentability date of completion Feb. 6, 2023, for PCT Application No. PCT/US2022/079324, filed on Nov. 4, 2022, 5 pages.
International Search Report and Written Opinion mailed on Feb. 6, 2023, for PCT Application No. PCT/US2022/079324, filed on Nov. 4, 2022, 8 pages.
U.S. Appl. No. 18/707,499, filed Nov. 4, 2022 for Snahel Patel et al. (submitted herewith pursuant to the waiver of 37 C.F.R. § 1.98(a)(2)(iii) issued by the Office on Sep. 21, 2004).

* cited by examiner

*Primary Examiner* — Niloofar Rahmani
(74) *Attorney, Agent, or Firm* — Morrison & Foerster LLP

(57) ABSTRACT

The present disclosure provides compounds and methods useful in the treatment and suppression of cancer, for example, useful for treating or suppressing cancers characterized by KRAS G12C. Also provided are pharmaceutical compositions containing such compounds and processes for preparing such compounds.

29 Claims, No Drawings

KRAS G12C INHIBITORS

CROSS REFERENCE TO RELATED APPLICATIONS

This application is a continuation application of U.S. patent application Ser. No. 18/707,499, which is a U.S. national stage application under 35 U.S.C. § 371 of International Application No. PCT/US2022/079324, filed internationally on Nov. 4, 2022, which claims priority to and the benefit of U.S. Provisional Patent Application Nos. 63/276,478 filed Nov. 5, 2021, 63/356,906 filed Jun. 29, 2022, and 63/403,565 filed Sep. 2, 2022, the contents of each of which are incorporated herein by reference in their entireties.

FIELD OF THE DISCLOSURE

The present disclosure provides compounds useful in treating or suppressing cancer, and in particular, useful in treating or suppressing cancers characterized by the KRAS G12C mutant.

Also provided are pharmaceutical formulations containing such compounds, processes for preparing such compounds, and methods of using such compounds in the treatment or suppression of cancers.

BACKGROUND

KRAS is a molecular switch. Under normal physiological conditions, the protein is bound to guanosine diphosphate (GDP) in the "off state." In response to signaling through receptor tyrosine kinases (RTKs) such as EGFR, the GDP is exchanged to guanosine triphosphate (GTP) in a process facilitated by guanine nucleotide exchange factors (GEFs) such as SOS. The GTP-bound form of KRAS is in the "on state," and interacts with proteins such as RAF and PI3K to promote downstream signaling that leads to cell proliferation and survival. KRAS can slowly hydrolyze GTP back to GDP, thus returning to the off-state, in a process facilitated by GAPs (GTPase-activating Proteins).

KRAS mutations are found in approximately 30% of all human cancers, and are highly prevalent among three of the deadliest forms of cancer: pancreatic (95%), colorectal (45%), and lung (35%). Together, these cancers occur in more than 200,000 patients annually in the US alone. One particular mutation, a glycine to cysteine substitution at position 12 (G12C), occurs in more than 40,000 patients per year. The KRAS G12C mutation impairs hydrolysis of GTP to GDP, thus trapping KRAS in the on-state and promoting cancer cell proliferation.

The cysteine residue of G12C provides an opportunity to develop targeted covalent drugs for this mutant KRAS. Early clinical trial results for KRAS G12C inhibitors AMG 510 and MRTX849 have shown encouraging results for non-small cell lung cancer (NSCLC), but the data are less compelling for colorectal cancer (CRC). Moreover, even in cases where patients respond to initial treatment, there are signs that the response may be limited in duration and that resistance could arise rapidly.

Most inhibitors of KRAS mutants bind preferentially to the GDP-bound form of the protein. For example, Amgen KRAS inhibitor AMG 510 and Mirati KRAS inhibitor MRTX849 react with the GDP-bound form of KRAS G12C at least 1000-fold more rapidly than with the GTP-bound form of the protein. One form of resistance that has been observed is for cancer cells to increase signaling through RTKs, thus increasing the amount of GTP-bound KRAS, which is less affected by current inhibitors. Thus, creating a molecule that could bind to and inhibit both the GDP- and GTP-bound forms of KRAS could have substantial utility.

What is needed are compounds useful in the treatment of cancer, such as cancers characterized by KRAS G12C. What is further needed are compounds useful in the treatment of cancers characterized by KRAS G12C, wherein the compounds bind to and inhibit both the inactive GDP- and activated GTP-bound forms of KRAS. What is further needed are compounds useful in the treatment of cancers characterized by KRAS G12C, wherein the compound has improved inhibition of the GTP-bound form of KRAS G12C.

The compounds of Formula (I) Formula (I-1) Formula (I-2), Formula (II), Formula (II-1) and Formula (II-2), and pharmaceutically acceptable salts and/or isotopologues thereof, including embodiments thereof disclosed herein, may be used for methods for inhibiting KRAS G12C in a cell, by contacting the cell in which inhibition of KRAS G12C activity is desired with an amount of the compound effective to inhibit KRAS G12C activity. Inhibition may be partial or total. In some embodiments, the contacting is in vitro. In some embodiments, the contacting is in vivo.

SUMMARY

In a first aspect, provided is a compound of Formula I or Formula II:

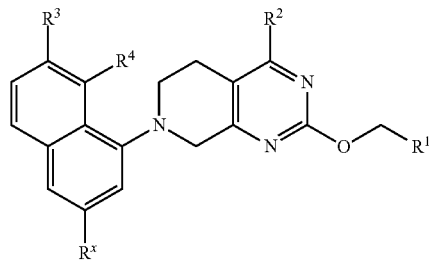

(Formula I)

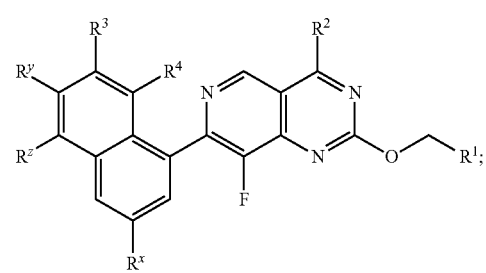

(Formula II)

or a salt thereof, and/or an isotopologue thereof,
wherein:
$R^x$ is selected from hydrogen, hydroxy, $C_1$-$C_4$ alkyl, $C_1$-$C_4$ haloalkyl, $C_1$-$C_4$ alkoxy and $C_1$-$C_4$ haloalkoxy;
$R^y$ is selected from hydrogen, $C_1$-$C_4$ alkyl, and halo;
$R^z$ is selected from hydrogen, $C_1$-$C_4$ alkyl, and halo;
$R^1$ is a 4-8 membered saturated carbocyclic or heterocyclic group comprising one nitrogen as the sole heteroatom within the ring atoms, wherein the carbocyclic or heterocyclic group is substituted with 0, 1, 2 or 3 substituents independently selected from halo, hydroxy, $C_1$-$C_4$ alkyl, spiro $C_3$-$C_4$ cycloalkyl, $C_1$-$C_4$ alkoxy, $C_1$-$C_4$ haloalkyl, and $C_1$-$C_4$ haloalkoxy;

$R^2$ is selected from the group consisting of $R^{2a}$, $R^{2b}$, $R^{2c}$, $R^{2d}$ and $R^{2e}$;

$R^3$ is selected from the group consisting of hydrogen, halo, $C_1$-$C_4$ alkyl, $C_1$-$C_4$ alkoxy, $C_1$-$C_4$ haloalkyl, $C_1$-$C_4$ haloalkoxy, and $C_2$-$C_3$ alkynyl;

$R^4$ is selected from the group consisting of hydrogen, halo, $C_1$-$C_4$ alkyl, $C_1$-$C_4$ alkoxy, $C_1$-$C_4$ haloalkyl, $C_1$-$C_4$ haloalkoxy, $C_3$-$C_7$ cycloalkyl, CN and $C_2$-$C_3$ alkynyl;

$R^{2a}$ is —$NR^5R^6$;

$R^5$ is selected from the group consisting of H, $C_1$-$C_4$ alkyl, $C_1$-$C_4$ alkoxy, $C_1$-$C_4$ haloalkyl, and $C_1$-$C_4$ haloalkoxy; and $R^6$ is —$C_1$-$C_6$ alkylene-$S(O)_2$—CH=$CHR^7$; or $R^5$ and $R^6$ together with the nitrogen to which they are attached form a 4-7 membered saturated heterocyclic group comprising one ring and comprising one nitrogen as the sole heteroatom within the ring atoms, wherein the 4-7 membered saturated heterocyclic group is substituted with —$(CH_2)_n$—$S(O)_2$—CH=$CHR^7$;

$R^7$ is selected from the group consisting of hydrogen, —$C_1$-$C_4$ alkyl, $C_1$-$C_4$ alkoxy, $C_1$-$C_4$ haloalkyl, $C_1$-$C_4$ haloalkoxy, and —$(CH_2)_m$—$NR^8R^9$;

$R^8$ and $R^9$ are independently selected from the group consisting of —H, $C_1$-$C_4$ alkyl, $C_1$-$C_4$ alkoxy, $C_1$-$C_4$ haloalkyl, and $C_1$-$C_4$ haloalkoxy; or $R^8$ and $R^9$ together with the nitrogen atom to which they are attached form a 4-7 membered saturated heterocyclic group comprising at least one nitrogen within the ring atoms, and which is optionally substituted by halo;

n is 0 or 1;

m is 1 or 2;

$R^{2b}$ is —$NR^{10}R^{11}$;

$R^{10}$ is selected from the group consisting of H, $C_1$-$C_4$ alkyl, $C_1$-$C_4$ alkoxy, $C_1$-$C_4$ haloalkyl, and $C_1$-$C_4$ haloalkoxy; and $R^{11}$ is selected from the group consisting of:
—($C_1$-$C_4$ alkylene)-$N(R^{12})$—CN, and
—$(CH_2)_w$—$R^{13}$; or $R^{10}$ and $R^{11}$ together with the nitrogen to which they are attached form a 4-8 membered saturated heterocyclic group optionally comprising a second nitrogen as the sole additional heteroatom within the ring atoms, wherein the 4-8 membered saturated heterocyclic group is substituted with one substituent selected from the group consisting of:
—$(CH_2)_x$—$N(R^{14})$—CN,
a 4-6 membered saturated heterocyclic group comprising one ring and comprising one nitrogen as the sole heteroatom within the ring atoms, wherein the nitrogen is substituted with cyano, and
cyano, with the proviso that when cyano is the substituent, then the 4-8 membered saturated heterocyclic group formed by $R^{10}$ and $R^{11}$ together with the nitrogen to which they are attached comprises the second nitrogen ring atom and the cyano is connected to the 4-8 membered saturated heterocyclic group at the second ring nitrogen;

$R^{12}$ is hydrogen, $C_1$-$C_4$ alkyl, $C_1$-$C_4$ alkoxy, $C_1$-$C_4$ haloalkyl, or $C_1$-$C_4$ haloalkoxy;

$R^{13}$ is a 4-5 membered saturated heterocyclic group comprising one nitrogen as the sole heteroatom within the ring atoms, wherein the nitrogen is substituted with cyano, and wherein the heterocyclic group is optionally further substituted with 1 substituent selected from the group consisting of hydroxy, CN, $C_1$-$C_4$ cyanoalkyl, $C_1$-$C_4$ alkyl, $C_1$-$C_4$ alkoxy, $C_1$-$C_4$ haloalkyl, $C_1$-$C_4$ haloalkoxy, or halo; or $R^{13}$ is a 6 membered saturated heterocyclic group comprising one or two nitrogens as the sole heteroatom(s) within the ring atoms, wherein one of the nitrogens is substituted with cyano, and wherein the heterocyclic group is optionally further substituted with 1 substituent selected from the group consisting of hydroxy, CN, $C_1$-$C_4$ cyanoalkyl, $C_1$-$C_4$ alkyl, $C_1$-$C_4$ alkoxy, $C_1$-$C_4$ haloalkyl, $C_1$-$C_4$ haloalkoxy, or halo, provided that the optional hydroxy, CN, cyanoalkyl and halo substituents are not attached to a heteroatom; or $R^{13}$ is a 7 membered saturated heterocyclic group comprising one nitrogen, and optionally one additional heteroatom selected from nitrogen, oxygen, and sulfur, as the sole heteroatom(s) within the ring atoms, wherein one of the nitrogen ring atom(s) is substituted with cyano, and wherein the heterocyclic group is optionally further substituted with 1 substituent selected from the group consisting of hydroxy, CN, $C_1$-$C_4$ cyanoalkyl, $C_1$-$C_4$ alkyl, $C_1$-$C_4$ alkoxy, $C_1$-$C_4$ haloalkyl, $C_1$-$C_4$ haloalkoxy, or halo provided that the optional hydroxy, CN, cyanoalkyl and halo substituents are not attached to a heteroatom;

$R^{14}$ is hydrogen, $C_1$-$C_4$ alkyl, $C_1$-$C_4$ alkoxy, $C_1$-$C_4$ haloalkyl, or $C_1$-$C_4$ haloalkoxy;

w is 0, 1, or 2;

x is 0 or 1;

$R^{2c}$ is —$NR^{15}R^{16}$;

$R^{15}$ is H, $C_1$-$C_4$ alkyl, optionally substituted with one instance of CN, $C_1$-$C_4$ alkoxy, $C_1$-$C_4$ haloalkyl, or $C_1$-$C_4$ haloalkoxy; and $R^{16}$ is selected from the group consisting of:
($C_1$-$C_4$ alkylene)-$N(R^{17})C(O)C(R^{19})$=$C(R^{20})R^{18}$, and
$(CH_2)_y$—$R^{21}$; or $R^{15}$ and $R^{16}$ together with the nitrogen to which they are attached form a 4-8 membered saturated heterocyclic group optionally comprising a second nitrogen as the sole additional heteroatom within the ring atoms, wherein the heterocyclic group is substituted with one substituent selected from the group consisting of:
$(CH_2)_q$—$N(R^{17})C(O)C(R^{19})$=$C(R^{20})R^{18}$, and
—$C(O)C(R^{19})$=$C(R^{20})R^{18}$, with the proviso that when —$C(O)C(R^{19})$=$C(R^{20})R^{18}$ is the substituent, then the 4-8 membered saturated heterocyclic group formed by $R^{15}$ and $R^{16}$ together with the nitrogen to which they are attached comprises the second nitrogen ring atom and the —$C(O)C(R^{19})$=$C(R^{20})R^{18}$ is connected to the heterocyclic group at the second ring nitrogen;

$R^{17}$ is selected from the group consisting of hydrogen, —$C_1$-$C_4$ alkyl, $C_1$-$C_4$ alkoxy, $C_1$-$C_4$ haloalkyl, and $C_1$-$C_4$ haloalkoxy;

$R^{18}$ is selected from the group consisting of hydrogen, —COOH, —C(O)O—$C_1$-$C_4$ alkyl, —C(O)O—$C_1$-$C_4$ haloalkyl, —C(O)—$C_1$-$C_4$ alkyl, —C(O)—$C_1$-$C_4$ haloalkyl, —$C(O)NR^{22}R^{23}$, —$(CH_2)_z$—$NR^{22}R^{23}$, —$(CH_2)_u$—$R^{34}$, —($C_1$-$C_2$ alkyl)-($C_1$-$C_2$ alkoxy), —$S(O)_2$—$C_1$-$C_4$ alkyl, —$S(O)_2$—$C_1$-$C_4$ haloalkyl, and $R^{35}$; and $R^{20}$ is selected from the group consisting of hydrogen, $C_1$-$C_4$ alkyl, $C_1$-$C_4$ alkoxy, $C_1$-$C_4$ haloalkyl, and $C_1$-$C_4$ haloalkoxy; or $R^{18}$ and $R^{20}$ together with the carbon to which they are attached can be taken together to form a 4-5 membered carbocyclic or heterocyclic ring containing one heteroatom selected from N, O and S, wherein the carbocyclic or heterocyclic ring can be optionally substituted with one instance of methyl, halo, hydroxy, methoxy or carbonyl;

$R^{19}$ is selected from the group consisting of hydrogen, $C_1$-$C_4$ alkyl, $C_1$-$C_4$ alkoxy, $C_1$-$C_4$ haloalkyl, and $C_1$-$C_4$ haloalkoxy;

$R^{21}$ is selected from:

a 4-5 membered saturated heterocyclic group comprising one nitrogen as the sole heteroatom within the ring atoms, wherein the nitrogen ring atom of the heterocyclic group is substituted with —C(O)C($R^{19}$)=C($R^{20}$)$R^{18}$ and wherein the heterocyclic group is not further substituted or is further substituted with 1 substituent selected from the group consisting of hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, and halo, or is further substituted with two halo substituents;

a 6 membered saturated heterocyclic group comprising one or two nitrogens as the sole heteroatom(s) within the ring atoms, wherein one of the nitrogens of the heterocyclic group is substituted with —C(O)C($R^{19}$)=C($R^{20}$)$R^{18}$, and wherein the heterocyclic group is not further substituted or is further substituted with 1 substituent selected from the group consisting of hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, or halo, or is further substituted with two halo substituents, provided that the optional hydroxy, CN, cyanoalkyl and halo substituents are not attached to a heteroatom; and a 7 membered saturated heterocyclic group comprising one nitrogen, and optionally one additional heteroatom selected from nitrogen, oxygen, and sulfur, as the sole heteroatom(s) within the ring atoms, wherein one of the nitrogen ring atom(s) of the heterocyclic group is substituted with —C(O)C($R^{19}$)=C($R^{20}$)$R^{18}$, and wherein the heterocyclic group is not further substituted or is further substituted with 1 substituent selected from the group consisting of hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, or halo, or is further substituted with two halo substituents, provided that the optional hydroxy, CN, cyanoalkyl and halo substituents are not attached to a heteroatom;

$R^{22}$ and $R^{23}$ are independently selected from the group consisting of hydrogen, $C_1$-$C_4$ alkyl, $C_1$-$C_4$ alkoxy, $C_1$-$C_4$ haloalkyl, and $C_1$-$C_4$ haloalkoxy;

$R^{34}$ is a 4-10 membered heterocycle which is substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy, $C_1$-$C_4$ hydroxyalkyl, $CH_2$—($C_3$-$C_6$ heterocyclyl) and $C_2$-$C_3$ alkynyl;

$R^{35}$ is a 5-6 membered heteroaryl group optionally substituted with 0, 1, 2 or 3 substituents independently selected from halo, hydroxy, $C_1$-$C_4$ alkyl, $C_1$-$C_4$ hydroxyalkyl, $C_1$-$C_4$ alkoxy, $C_1$-$C_4$ haloalkyl, $C_1$-$C_4$ haloalkoxy, $C_3$-$C_6$ heterocyclyl optionally substituted with one or two substituents independently selected from halo, hydroxy and methyl, and $C_3$-$C_6$ cycloalkyl optionally substituted with one or two substituents independently selected from halo, hydroxy and methyl;

y is 0, 1, or 2;
z is 1 or 2;
q is 0 or 1;
u is 0, 1 or 2;

$R^{2a}$ is selected from the group consisting of:
—NR$^{24}$R$^{25}$,
—C(O)N(R$^{27}$)—($C_1$-$C_4$ alkylene)-C(O)CH=CHR$^{26}$, and
—O—($C_1$-$C_2$ alkylene)-C(O)CH=CHR$^{26}$;

$R^{24}$ is H, $C_1$-$C_4$ alkyl, $C_1$-$C_4$ alkoxy, $C_1$-$C_4$ haloalkyl, or $C_1$-$C_4$ haloalkoxy; and $R^{25}$ is —($C_1$-$C_4$ alkylene)-C(O)CH=CHR$^{26}$; or $R^{24}$ and $R^{25}$ together with the nitrogen to which they are attached form a 4-8 membered saturated heterocyclic group comprising one nitrogen as the sole heteroatom within the ring atoms, wherein the heterocyclic group is substituted with —($C_0$-$C_2$ alkylene)-C(O)CH=CHR$^{26}$, and wherein the heterocyclic group is further optionally substituted with $C_1$-$C_4$ alkyl, $C_1$-$C_4$ alkoxy, $C_1$-$C_4$ haloalkyl, or $C_1$-$C_4$ haloalkoxy;

$R^{26}$ is hydrogen, $C_1$-$C_4$ alkyl, $C_1$-$C_4$ alkoxy, $C_1$-$C_4$ haloalkyl, or $C_1$-$C_4$ haloalkoxy; and $R^{27}$ is selected from hydrogen, $C_1$-$C_4$ alkyl, $C_1$-$C_4$ alkoxy, $C_1$-$C_4$ haloalkyl, and $C_1$-$C_4$ haloalkoxy;

$R^{2e}$ is —NR$^{28}$R$^{29}$;

$R^{28}$ is H, $C_1$-$C_4$ alkyl, $C_1$-$C_4$ alkoxy, $C_1$-$C_4$ haloalkyl, or $C_1$-$C_4$ haloalkoxy; and $R^{29}$ is —(CH$_2$)$_t$—R$^{30}$;

$R^{30}$ is selected from:

a 4-5 membered saturated heterocyclic group comprising one nitrogen as the sole heteroatom within the ring atoms, wherein the nitrogen ring atom of the heterocyclic group is substituted with —C(O)C≡CR$^{31}$ and wherein the heterocyclic group is not further substituted or is further substituted with 1 substituent selected from the group consisting of hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, and halo;

a 6 membered saturated heterocyclic group comprising one or two nitrogens as the sole heteroatom(s) within the ring atoms, wherein one of the nitrogens of the heterocyclic group is substituted with —C(O)C≡CR$^{31}$, and wherein the heterocyclic group is not further substituted or is further substituted with 1 substituent selected from the group consisting of hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, or halo provided that the optional hydroxy, CN, cyanoalkyl and halo substituents are not attached to a heteroatom; and a 7 membered saturated heterocyclic group comprising one nitrogen, and optionally one additional heteroatom selected from nitrogen, oxygen, and sulfur, as the sole heteroatom(s) within the ring atoms, wherein one of the nitrogen ring atom(s) of the heterocyclic group is substituted with —C(O)C≡CR$^{31}$, and wherein the heterocyclic group is not further substituted or is further substituted with 1 substituent selected from the group consisting of hydroxy, CN, $C_1$-$C_4$ alkyl, $C_1$-$C_4$ alkoxy, $C_1$-$C_4$ cyanoalkyl, $C_1$-$C_4$ haloalkyl, $C_1$-$C_4$ haloalkoxy, or halo, provided that the optional hydroxy, CN, cyanoalkyl and halo substituents are not attached to a heteroatom;

$R^{31}$ is selected from the group consisting of —(CH$_2$)$_v$—NR$^{32}$R$^{33}$ and —(CH$_2$)$_p$—R$^{36}$;

$R^{32}$ and $R^{33}$ are independently selected from the group consisting of hydrogen, $C_1$-$C_4$ alkyl, $C_1$-$C_4$ alkoxy, $C_1$-$C_4$ haloalkyl, and $C_1$-$C_4$ haloalkoxy;

t is 0, 1, or 2;
v is 1 or 2;
p is 0, 1 or 2;

$R^{36}$ is a 4-10 membered heterocycle which is substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl;

with the proviso that when the compound is of Formula I, then $R^{2e}$ is not

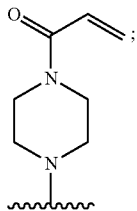 [SMILES: *N1CCN(C(=O)C=C)CC1]

and with the further proviso that when the compound is of Formula II, then $R^{2e}$ is not —$NR^{15}R^{16}$, wherein $R^{15}$ and $R^{16}$ together with the nitrogen to which they are attached form a 4-8 membered saturated heterocyclic group comprising a second nitrogen as the sole additional heteroatom within the ring atoms, wherein the second nitrogen is substituted with —C(O)—CH=$CH_2$.

In some embodiments, including any of the embodiments in the preceding paragraphs, the compound is selected from the group consisting of the compounds of Table 1; and all salts and isotopologues thereof.

In another aspect provided is a pharmaceutical formulation comprising a compound as described herein, including but not limited to a compound described in the preceding paragraphs, and a pharmaceutically acceptable carrier, wherein when the compound is a salt, the salt is a pharmaceutically acceptable salt.

In another aspect provided is a method of treating or suppressing cancer comprising: administering a therapeutically effective amount of a compound as described herein, including but not limited to a compound described in the preceding paragraphs, or a pharmaceutical formulation, including but not limited to the pharmaceutical formulation described in the preceding paragraphs, to a subject in need thereof, wherein when the compound is a salt, the salt is a pharmaceutically acceptable salt. In some embodiments, the cancer is selected from the group consisting of: lung, colorectal, pancreatic, bile duct, thyroid, gall bladder, uterine, mesothelioma, cervical, and bladder cancers. In some embodiments, the cancer is selected from the group consisting of: glioblastoma multiforme, lower grade glioma, head and neck squamous cell carcinoma, papillary thyroid carcinoma, anaplastic thyroid carcinoma, follicular thyroid carcinoma, lung adenocarcinoma, lung squamous cell carcinoma, breast invasive carcinoma, esophageal carcinoma, stomach adenocarcinoma, small intestine adenocarcinoma, colon adenocarcinoma, rectal adenocarcinoma, liver hepatocellular carcinoma, cholangiocarcinoma, gallbladder carcinoma, pancreatic adenocarcinoma, kidney renal clear cell carcinoma, bladder urothelial carcinoma, prostate adenocarcinoma, ovarian serous cystadenocarcinoma, uterine corpus endometrial carcinoma, cervical squamous carcinoma and endocervical adenocarcinoma, skin cutaneous melanoma, acute lymphoblastic leukemia, acute myeloid leukemia, chronic myeloid leukemia, plasma cell myeloma, uterine carcinosarcoma, mesothelioma, adrenocortical carcinoma, brain lower grade glioma, diffuse large B-cell lymphoma, esophageal adenocarcinoma, kidney chromophobe, kidney renal papillary cell carcinoma, pheochromocytoma and paraganglioma, sarcoma, testicular germ cell tumors, thymoma, uveal melanoma, metastatic colorectal cancer, bladder cancer, adenoid cystic carcinoma, myelodysplastic, breast cancer, thyroid carcinoma, glioma, esophageal/stomach cancer, pediatric Wilms' tumor, pediatric acute lymphoid leukemia, chronic lymphocytic leukemia, mature B-cell malignancies, pediatric neuroblastoma, and melanoma. In some embodiments, including any of the foregoing embodiments, the method is for treating the cancer. In some embodiments, including any of the foregoing embodiments, the method is for suppressing the cancer. In some embodiments, including any of the foregoing embodiments, the cancer is a KRAS G12C mediated cancer. In some embodiments, including any of the foregoing embodiments, the subject has been diagnosed as having a KRAS G12C mediated cancer. In some embodiments, the method further comprises administering to the subject a therapeutically effective amount of an additional chemotherapeutic agent.

In another aspect provided is the use of a compound as described herein, including but not limited to any of the foregoing embodiments, as a medicament. In another aspect is the use of a compound as described herein, including but not limited to any of the foregoing embodiments, for treating or suppressing cancer. In another aspect is the use of a compound as described herein, including but not limited to any of the foregoing embodiments, in the manufacture of a medicament for use in treating or suppressing cancer. In some embodiments, including any of the foregoing embodiments, the use is for treating the cancer. In some embodiments, including any of the foregoing embodiments, the use is for suppressing the cancer.

In another aspect provided is a compound as described herein, including but not limited to any of the foregoing embodiments for use in the manufacturing of a medicament for treating or suppressing cancer. In another aspect is a compound as described herein, including but not limited to any of the foregoing embodiments, for use in treating or suppressing cancer. In another aspect is the compound as described herein, including but not limited to any of the foregoing embodiments, for use in the manufacture of a medicament for treating or suppressing cancer. In some embodiments, including any of the foregoing embodiments, the use is for treating the cancer. In some embodiments, including any of the foregoing embodiments, the use is for suppressing the cancer.

It is to be understood that the description of compounds, compositions, formulations, and methods of treatment described herein include "comprising", "consisting of", and "consisting essentially of" embodiments. In some embodiments, for all compositions described herein, and all methods using a composition described herein, the compositions can either comprise the listed components or steps, or can "consist essentially of" the listed components or steps. When a composition is described as "consisting essentially of" the listed components, the composition contains the components listed, and may contain other components which do not substantially affect the condition being treated, but do not contain any other components which substantially affect the condition being treated other than those components expressly listed; or, if the composition does contain extra components other than those listed which substantially affect the condition being treated, the composition does not contain a sufficient concentration or amount of the extra components to substantially affect the condition being treated. When a method is described as "consisting essentially of" the listed steps, the method contains the steps listed, and may contain other steps that do not substantially affect the condition being treated, but the method does not contain any other steps which substantially affect the condition being treated other than those steps expressly listed. As a non-limiting specific example, when a composition is described as 'consisting essentially of' a component, the composition may additionally contain any amount of pharmaceutically acceptable carriers, vehicles, or diluents and other such components which do not substantially affect the condition being treated.

Additional embodiments, features, and advantages of the present disclosure will be apparent from the following detailed description and through practice of the present disclosure.

DETAILED DESCRIPTION

Provided herein are compounds useful in treating cancer, and methods of using such compounds for treating cancer. In some embodiments, the compounds are useful in treating cancers characterized by KRAS G12C. In some embodiments, the compounds advantageously inhibit both the inactive GDP- and activated GTP-bound forms of KRAS G12C. In some embodiments, the compounds advantageously have improved inhibition of the GTP-bound form of KRAS G12C.

The abbreviations used herein have their conventional meaning within the chemical and biological arts, unless otherwise specified.

It is to be understood that descriptions of compound structures, including possible substitutions, are limited to those which are chemically possible.

Unless otherwise indicated, the absolute stereochemistry of all chiral atoms is as depicted. Compounds with an (or) designation in the first column of Table 1 are single enantiomers wherein the absolute stereochemistry was arbitrarily assigned (e.g., based on chiral SFC elution as described in the Examples section). Compounds with an (and) designation in the first column of Table 1 are mixtures of enantiomers wherein the relative stereochemistry is as shown. Compounds that have a stereogenic center where the configuration is not indicated in the structure as depicted and that have no designation in the first column of Table 1 are mixtures of enantiomers at that center. Compounds that have no designation in the first column of Table 1 or that are marked with (abs) are single enantiomers wherein the absolute stereochemistry is as indicated. For example, compound 1 is a pure enantiomer with the stereochemistry as indicated.

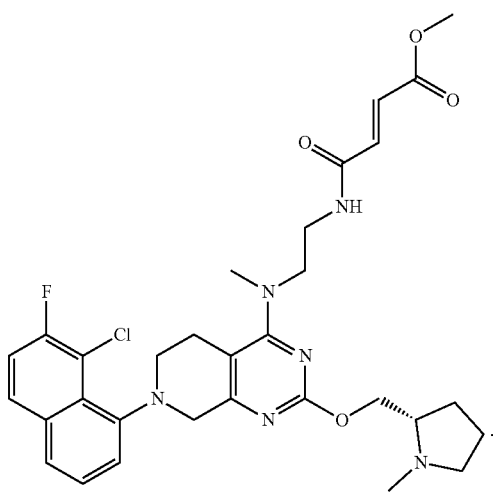 [SMILES: COC(=O)/C=C/C(=O)NCCN(C)c1nc(OC[C@@H]2CCCN2C)nc2c1CCN(c1cccc3ccc(F)c(Cl)c13)C2]

In some instances, the first column of Table 1 contains different indicators selected from (abs) (or) and (and) to refer to different stereocenters of the molecule.

For example, Compound 43 includes a notation of "(or) fused piperidine (abs) pyrrolidine" in column 1 of Table 1.

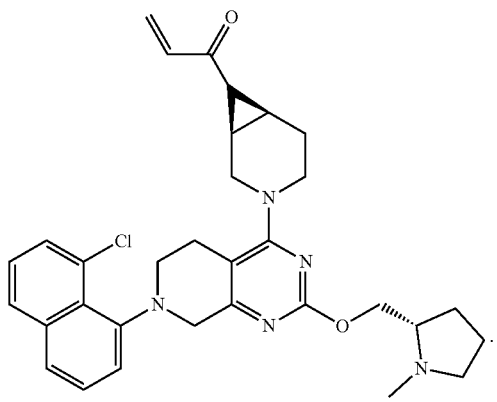

The compound is a single enantiomer wherein the stereochemistry at the pyrrolidine group is (S) as shown, because the pyrrolidine group was prepared from an enantiopure starting material, and the stereochemistry at the fused cyclopropyl group is either (R,S) or (S,R), but not a mixture of the two, and was arbitrarily assigned. Stereochemistry is often arbitrarily assigned when mixtures of enantiomers or diastereomers are separated into the corresponding single enantiomers or diastereomers by chromatography.

A person of skill in the art would be able to separate racemic compounds into the respective enantiomers using methods known in the art, such as chiral chromatography, chiral recrystallization and the like. References to compounds that are racemic mixtures are meant to also include the individual enantiomers contained in the mixture.

Reference to "about" a value or parameter herein includes (and describes) variations that are directed to that value or parameter per se. For example, description referring to "about X" includes description of "X". As used herein, and unless otherwise specified, the terms "about" and "approximately," when used in connection with temperatures, doses, amounts, or weight percent of ingredients of a composition or a dosage form, mean a dose, amount, or weight percent that is recognized by those of ordinary skill in the art to provide a pharmacological effect equivalent to that obtained from the specified dose, amount, or weight percent. Specifically, the terms "about" and "approximately," when used in this context, contemplate a dose, amount, or weight percent within 15%, within 10%, within 5%, within 4%, within 3%, within 2%, within 1%, or within 0.5% of the specified dose, amount, or weight percent.

The terms "a" and "an," as used in herein mean one or more, unless context clearly dictates otherwise.

The terms "subject," "individual," and "patient" mean an individual organism, preferably a vertebrate, more preferably a mammal, most preferably a human. Examples of patients include humans, livestock such as cows, goats, sheep, pigs, and rabbits, and companion animals such as dogs, cats, and horses. In some embodiments, the subject has been identified or diagnosed as having a cancer or tumor having a KRAS G12C mutation (e.g., as determined using a regulatory agency-approved, e.g., FDA-approved, assay or kit).

"Treating" a disorder with the compounds and methods discussed herein is defined as administering one or more of the compounds discussed herein, with or without additional therapeutic agents, in order to reduce or eliminate either the disorder or one or more symptoms of the disorder, or to retard the progression of the disorder or of one or more symptoms of the disorder, or to reduce the severity of the disorder or of one or more symptoms of the disorder.

"Suppression" of a disorder with the compounds and methods discussed herein is defined as administering one or more of the compounds discussed herein, with or without additional therapeutic agents, in order to suppress the clinical manifestation of the disorder, or to suppress the manifestation of adverse symptoms of the disorder. The distinction between treatment and suppression is that treatment occurs after adverse symptoms of the disorder are manifest in a subject, while suppression occurs before adverse symptoms of the disorder are manifest in a subject. Suppression may be partial, substantially total, or total. In some embodiments, genetic screening can be used to identify patients at risk of the disorder. The compounds and methods disclosed herein can then be administered to asymptomatic patients at risk of developing the clinical symptoms of the disorder, in order to suppress the appearance of any adverse symptoms.

"Therapeutic use" of the compounds discussed herein is defined as using one or more of the compounds discussed herein to treat or suppress a disorder, as defined herein. A "therapeutically effective amount" of a compound is an amount of the compound, which, when administered to a subject, is sufficient to reduce or eliminate either the disorder or one or more symptoms of the disorder, or to retard the progression of the disorder or of one or more symptoms of the disorder, or to reduce the severity of the disorder or of one or more symptoms of the disorder, or to suppress the clinical manifestation of a disorder, or to suppress the manifestation of adverse symptoms of a disorder. A therapeutically effective amount can be given in one or more administrations.

A "KRAS G12C mediated cancer" is used interchangeably herein with a "cancer characterized by KRAS G12C", and indicates that the cancer comprises cells which contain the KRAS G12C mutant.

While the compounds described herein can occur and can be used as the neutral (non-salt) compound, the description is intended to embrace all salts of the compounds described herein, as well as methods of using such salts of the compounds. In some embodiments, the salts of the compounds comprise pharmaceutically acceptable salts.

A "pharmaceutically acceptable salt" of a compound means a salt that is pharmaceutically acceptable to humans and/or animals, and which, upon administration, retains at least some of the desired pharmacological activity of the parent compound. Such salts include: (a) acid addition salts, formed with inorganic acids such as hydrochloric acid, hydrobromic acid, sulfuric acid, nitric acid, phosphoric acid, and the like; or formed with organic acids such as formic acid, acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (b) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. Additional information on suitable pharmaceutically acceptable salts can be found in Remington's Pharmaceutical Sciences, 17th ed., Mack Publishing Company, Easton, PA, 1985, which is incorporated herein by reference in its entirety.

Included herein, when chemically relevant, are all stereoisomers of the compounds, including diastereomers and enantiomers. Also included are mixtures of possible stereoisomers in any ratio, including, but not limited to, racemic mixtures. Unless stereochemistry is explicitly indicated in a structure, the structure is intended to embrace all possible stereoisomers of the compound depicted. If stereochemistry is explicitly indicated for one portion or portions of a molecule, but not for another portion or portions of a molecule, the structure is intended to embrace all possible stereoisomers for the portion or portions where stereochemistry is not explicitly indicated.

"Isotopologue" refers herein to a compound which differs in its isotopic composition from its "natural" isotopic composition. "Isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen," the position is understood to have hydrogen at its natural isotopic composition. The description of compounds herein also includes all isotopologues, in some embodiments, partially deuterated or perdeuterated analogs, of all compounds herein. "Isotopically enriched" may also refer to a compound containing at least one atom having an isotopic composition other than the natural isotopic composition of that atom. "Isotopic enrichment" refers to the percentage of incorporation of an amount of a specific isotope at a given atom in a molecule in the place of that atom's natural isotopic abundance. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

"Alkyl" means a linear, branched, cyclic, or a combination thereof, saturated monovalent hydrocarbon radical having the defined number of carbons. For example, $C_1$-$C_4$ alkyl includes e.g., methyl, ethyl, propyl, 2-propyl, butyl, cyclopropyl, cyclobutyl, and the like.

"Alkylene" means a linear, branched, cyclic, or a combination thereof, saturated divalent hydrocarbon radical having the defined number of carbons. For example, $C_1$-$C_4$ alkylene includes e.g., methylene, ethylene, propylene, 1-methylpropylene, 2-methylpropylene, butylene, and the like. "$C_0$ alkylene" means a bond. For example, $C_0$-$C_2$ alkylene includes a bond, methylene, ethylene, and the like.

"Alkynyl" means a linear or branched monovalent hydrocarbon radical having the defined number of carbons and at least one carbon-carbon triple bond. For example, $C_2$-$C_4$ alkyne includes e.g., ethynyl, propynyl, 2-propynyl, butynyl, and the like.

"Alkoxy" means an —$OR^o$ radical where $R^o$ is alkyl as defined above, or a —$R^{o\prime}OR^{o\prime\prime}$ radical where $R^{o\prime}$ is an alkylene and and $R^{o\prime\prime}$ is an alkyl group as defined above where the defined number of alkyl carbons in the alkoxy group are equal to the total number of carbons in $R^{o\prime}$ and $R^{o\prime\prime}$. For example, $C_1$-$C_4$ alkoxy indicates e.g., methoxy, ethoxy, propoxy, 2-propoxy, n-, iso-, tert-butoxy, cyclopropoxy, methoxymethyl, ethoxymethyl, propoxymethyl, isopropoxymethyl, and the like. In some embodiments, alkoxy is a —$OR^o$ radical. In some embodiments, alkoxy is a —$R^{o\prime}OR^{o\prime\prime}$ radical.

In some embodiments, when a nitrogen is substituted with an alkoxy group, the alkoxy group is not linked to the nitrogen via the oxygen or a carbon that is immediately adjacent to the oxygen in the alkoxy group. For example, the alkoxy-substituted nitrogen is not N—$OR^o$ or N—$CH_2$—O—$R^{o\prime\prime}$.

"Alkoxyalkoxy" means an —$OR^r$ radical where $R^r$ is alkoxy as defined above, provided that the attachment point of R is not an oxygen atom, or a —$R^{r\prime}OR^{r\prime\prime}$ radical where R is an alkylene and $R^{r\prime\prime}$ is an alkoxy group as defined above, provided that the attachment point of $R^{r\prime\prime}$ is not an oxygen atom, where the defined number of alkyl carbons in the alkoxyalkoxy group are equal to the total number of carbons in $R^{r\prime}$ and $R^{r\prime\prime}$. For example, $C_1$-$C_6$ alkoxyalkoxy indicates e.g., —$OCH_2OCH_3$, —$OCH_2CH_2OCH_3$, —$OCH_2CH_2OCH_3$, —$CH_2OCH_2OCH_3$, —$CH_2OCH_2CH_2OCH_3$, —$CH_2OCH_2CH_2OCH_2CH_3$, —$CH_2CH_2OCH_2CH_2OCH_2CH_3$ and the like. In some embodiments, alkoxyalkoxy is a —OW radical. In some embodiments, alkoxyalkoxy is a —$R^{r\prime}OR^{r\prime\prime}$ radical. In some embodiments, when a nitrogen is substituted with an alkoxyalkoxy group, the alkoxyalkoxy group is not linked to the nitrogen via the oxygen or a carbon that is immediately adjacent to the oxygen in the alkoxyalkoxy group. For example, the alkoxyalkoxy-substituted nitrogen is not N—$OR^r$ or N—$CH_2$—O—$R^{r\prime\prime}$.

"Aminoalkyl" means an —$NHR''$ radical where $R''$ is alkyl as defined above, or a —$NR''R'''$ radical where $R''$ and $R'''$ are alkyl groups as defined above, or an —$R''''NH_2$ radical where $R''''$ is an alkylene group as defined above, or an —$R''''NHR''$ radical where $R''''$ is an alkylene group as defined above and $R''$ is an alkyl group as defined above, or a —$R''''NR''R'''$ radical where $R''''$ is an alkylene group as defined above and $R''$ and $R'''$ are alkyl groups as defined above, where the defined number of alkyl carbons in the aminoalkyl group is equal to the total number of carbons in $R''$, $R'''$ and $R''''$ as applicable. For example, $C_1$-$C_6$ aminoalkyl indicates e.g., —$NHCH_3$, —$NHCH_2CH_3$, —$NHCH_2(CH_3)_2$, —$N(CH_3)_2$, —$N(CH_3)CH_2CH_3$, —$N(CH_2CH_3)_2$, —$CH_2NH_2$, —$CH_2CH_2NH_2$, —$CH_2NHCH_3$, —$CH_2N(CH_3)_2$, —$CH_2CH_2NHCH_3$, —$CH_2CH_2N(CH_3)_2$ and the like. In some embodiments, aminoalkyl is an —$NHR''$ radical. In some embodiments, aminoalkyl is an —$NR''R'''$ radical. In some embodiments, an aminoalkyl is an —$R''''NH_2$ radical. In some embodiments, aminoalkyl is a —$R''''NHR''$ radical. In some embodiments, aminoalkyl is a —$R''''NR''R'''$ radical. In some embodiments, when an oxygen is substituted with an aminoalkyl group, the aminoalkyl group is not linked to the oxygen via the nitrogen or a carbon that is immediately adjacent to the nitrogen in the aminoalkyl group. For example, the aminoalkyl-substituted oxygen is not O—$NR''$ or O—$CH_2$—$NHR''$.

"Cycloalkyl" means a monocyclic saturated monovalent hydrocarbon radical having the defined number of carbon atoms. For example, $C_3$-$C_6$ cycloalkyl includes cyclopropyl, cyclobutyl, cyclopentyl, and cyclohexyl.

"Cyanoalkyl" means an alkyl radical as defined above, which is substituted with a cyano group (—CN). A cyanoalkyl can also be referred to as an alkylnitrile.

"Halo" means fluoro, chloro, bromo, or iodo. In some embodiments, halo is fluoro or chloro.

"Haloalkyl" means an alkyl radical as defined above, which is substituted with one or more halogen atoms, e.g., one to five halogen atoms, such as fluorine or chlorine, including those substituted with different halogens, e.g., —$CH_2Cl$, —$CF_3$, —$CHF_2$, —$CH_2CF_3$, —$CF_2CF_3$, —$CF(CH_3)_2$, and the like. When the alkyl is substituted with only fluoro, it can be referred to in this application as fluoroalkyl.

"Haloalkoxy" means an —$OR^a$ radical where $R^a$ is haloalkyl as defined above, or a —$R^bOR^c$ radical where $R^b$ and $R^c$ are alkyl or haloalkyl groups as defined above where the defined number of alkyl carbons in the haloalkoxy group are equal to the total number of carbons in $R^b$ and $R^c$. Halo atom(s) may be present in $R^b$, or $R^c$, or both, provided that at least one of $R^b$ and $R^c$ comprises a halo atom. For example, $C_1$-$C_4$ haloalkoxy indicates e.g., —$OCF_3$, —$OCHF_2$, —$CH_2OCF_3$, —$CH_2CH(F)CH_2OCH_3$, —$CH_2CH(F)CH_2OCHF_2$, and the like. In some embodiments, haloalkoxy is a —$OR^a$ radical. In some embodiments, haloalkoxy is a —$R^bOR^c$ radical. When all of the halo atom(s) in the haloalkoxy group are fluoro, it can be referred to in this application as fluoroalkoxy. In some embodiments, when a nitrogen is substituted with a haloalkoxy group, the haloalkoxy group is not linked to the nitrogen via the oxygen or a carbon that is immediately adjacent to the oxygen in the haloalkoxy group. For example, the haloalkoxy-substituted nitrogen is not N—$OR^a$ or N—$C(H)_n(X)_{2-n}$—O—$R^c$.

"Hydroxyalkyl" means an alkyl radical as defined above, which is substituted with one or more hydroxyl (—OH) groups, e.g., one to three hydroxyl groups, e.g., —$CH_2OH$, —$CH_2CH_2OH$, —$C(OH)(CH_3)_2$, —$CH(OH)CH_3$ and the like.

A "heterocyclic group", unless otherwise specified, means a saturated or partially unsaturated cyclic group comprising 3-12 ring atoms, in which 1-4 ring atoms are heteroatoms independently selected from the group consisting of nitrogen, oxygen, and sulfur, the remaining rings being C. The sulfur group may be present either as —S— or as —$S(O)_2$—. Unless otherwise specified, the heterocyclic group includes single as well as multiple ring systems including fused, bridged, and spiro ring systems. In some embodiments, the heterocyclic group is a single ring. In some embodiments, the heterocyclic group comprises two fused rings. In some embodiments, the heterocyclic group comprises two spiro rings. In some embodiments, the heterocyclic group comprises a bridged ring system.

A "carbocyclic group", unless otherwise specified, means a saturated or partially unsaturated cyclic group comprising 3-12 ring atoms, in which the ring atoms are C. Unless otherwise specified, the carbocyclic group includes single as well as multiple ring systems including fused, bridged, and spiro ring systems. In some embodiments, the carbocyclic group is a single ring. In some embodiments, the carbocyclic group comprises two fused rings. In some embodiments, the carbocyclic group comprises two spiro rings. In some embodiments, the carbocyclic group comprises a bridged ring system.

"Heteroaryl" means a monovalent monocyclic or bicyclic aromatic radical of 5 to 10 ring atoms, unless otherwise stated, where one or more (in some embodiments, one, two, or three) ring atoms are heteroatom(s) independently selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like.

A "spiro" cycloalkyl group indicates that the cycloalkyl group is linked to the remaining portion of the compound through a spiro linkage. A "spiro" cycloalkyl substituent has two attachments that connect to the same carbon of the moiety that is substituted, forming a spiro connection. For example, a cyclohexyl group that is substituted with a "spiro $C_3$-$C_4$ cycloalkyl" group indicates:

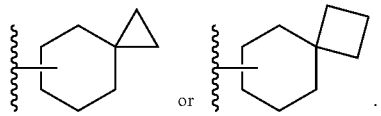

"In need of treatment" as used herein means the patient is being treated by a physician or other caregiver after diagnoses of the disease, or a determination that the patient is at risk for developing the disease. In some embodiments, the patient has been diagnosed as having a KRAS G12C mediated cancer. In some embodiments, the patient has been determined to be at risk of developing a KRAS G12C mediated cancer.

"Administration", "administer" and the like, as they apply to, for example, a patient, cell, tissue, organ, or biological fluid, refer to contact of, for example, a compound of Formula (I), Formula (I-1), Formula (I-2), Formula (II), Formula (II-1) or Formula (II-2), or a pharmaceutically acceptable salt and/or isotopologue thereof, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

"Optional" or "optionally" means that the subsequently described event or circumstance may but need not occur, and that the description includes instances where the event or circumstance occurs and instances in which it does not.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a disease or disorder described in the present disclosure. Such administration encompasses co-administration of these therapeutic agents in a substantially simultaneous manner, such as in a single capsule or a tablet having a fixed ratio of active ingredients or in multiple, separate capsules or tablets for each active ingredient. In addition, such administration also encompasses use of each type of therapeutic agent in a sequential manner. In either case, the treatment regimen will provide beneficial effects of the drug combination in treating the conditions or disorders described herein.

Methods for Treatment of Cancer

The compounds of Formula (I), Formula (I-1), Formula (I-2), Formula (II), Formula (II-1) and Formula (II-2), and pharmaceutically acceptable salts and/or isotopologues thereof, including embodiments thereof disclosed herein, are useful for the treatment of cancer, which include but are not limited to, various types of cancer including e.g. lung, colorectal, pancreatic, bile duct, thyroid, gall bladder, uterine, mesothelioma, cervical, and bladder cancers. More particularly, cancers that may be treated by the compounds of Formula (I), Formula (I-1), Formula (I-2), Formula (II), Formula (II-1) and Formula (II-2), and pharmaceutically acceptable salts and/or isotopologues thereof, including embodiments thereof disclosed herein, include, but are not limited to cancers such as glioblastoma multiforme, lower grade glioma, head and neck squamous cell carcinoma, papillary thyroid carcinoma, anaplastic thyroid carcinoma, follicular thyroid carcinoma, lung adenocarcinoma, lung squamous cell carcinoma, breast invasive carcinoma, esophageal carcinoma, stomach adenocarcinoma, small intestine adenocarcinoma, colon adenocarcinoma, rectal adenocarcinoma, liver hepatocellular carcinoma, cholangiocarcinoma, gallbladder carcinoma, pancreatic adenocarcinoma, kidney renal clear cell carcinoma, bladder urothelial carcinoma, prostate adenocarcinoma, ovarian serous cystadenocarcinoma, uterine corpus endometrial carcinoma, cervical squamous carcinoma and endocervical adenocarcinoma, skin cutaneous melanoma, acute lymphoblastic leukemia, acute myeloid leukemia, chronic myeloid leukemia, plasma cell myeloma, uterine carcinosarcoma, mesothelioma, adrenocortical carcinoma, brain lower grade glioma, diffuse large B-cell lymphoma, esophageal adenocarcinoma, kidney chromophobe, kidney renal papillary cell carcinoma, pheochromocytoma and paraganglioma, sarcoma, testicular germ cell tumors, thymoma, uveal melanoma, metastatic colorectal cancer, bladder cancer, adenoid cystic carcinoma, myelodysplastic, breast cancer, thyroid carcinoma, glioma, esophageal/stomach cancer, pediatric Wilms' tumor, pediatric acute lymphoid leukemia, chronic lymphocytic leukemia, mature B-cell malignancies, pediatric neuroblastoma, and melanoma. In some embodiments, including any of the foregoing embodiments, the cancer is a KRAS G12C mediated cancer. In some embodiments, including any of the foregoing embodiments, the subject has been diagnosed as having a KRAS G12C mediated cancer. In some embodiments, including any of the foregoing embodiments, the subject has been determined to be at risk of developing a KRAS G12C mediated cancer.

In some embodiments, including any of the foregoing embodiments, the subject and/or the cancer is resistant or refractory to treatment with KRAS inhibitors (e.g., G12C KRAS inhibitors).

Testing

The compounds of Formula (I), Formula (I-1), Formula (I-2), Formula (II), Formula (II-1) and Formula (II-2), and pharmaceutically acceptable salts and/or isotopologues thereof, including embodiments thereof disclosed herein, may be tested by, for example, methods described in the Examples below, or by known and generally accepted cell and/or animal models.

The ability of compounds of Formula (I), Formula (I-1), Formula (I-2), Formula (II), Formula (II-1) and Formula (II-2), and pharmaceutically acceptable salts and/or isotopologues thereof, to inhibit activity of the GTP-bound form of KRAS G12C can be tested using methods such as the in vitro assay described in Examples 308 and 309 below. Example 308 describes determining, for various compounds, the half-maximal inhibition ($IC_{50}$) of KRAS G12C loaded with GTP analogue GMPPNP from binding to cRaf, as the Ras-binding domain (RBD). Example 309 describes determining, for various compounds, the half-maximal inhibition ($IC_{50}$) of KRAS G12C loaded with GTP analogue GMPPNP from binding to PI3Kα, as the Ras-binding domain (RBD). Example 310 describes testing compounds for the ability to inhibit cell viability in MCF10A G12C/A59G mutant, which abrogates GTPase activity, thus preventing hydrolysis of GTP to GDP.

Pharmaceutical Compositions

In general, the compounds of Formula (I), Formula (I-1), Formula (I-2), Formula (II), Formula (II-1) and Formula (II-2), and pharmaceutically acceptable salts and/or isotopologues thereof, of this disclosure (also may be referred to herein as "compounds" or "compounds of this disclosure") will be administered in a therapeutically effective amount by any of the accepted modes of administration for agents that serve similar utilities. Therapeutically effective amounts of compounds of this disclosure may range from about 0.01 to about 500 mg per kg patient body weight per day, which can be administered in single or multiple doses. In some embodiments, a suitable dosage level may be from about 0.1 to about 250 mg/kg per day; or about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage can be about 0.05 to about 0.5, about 0.5 to about 5 or about 5 to about 50 mg/kg per day. For oral administration, the compositions can be provided in the form of tablets containing about 1.0 to about 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient.

The actual amount of a compound of this disclosure, i.e., the active ingredient, will depend upon numerous factors such as the severity of the disease to be treated, the age and relative health of the patient, the potency of the compound being utilized, the route and form of administration, and other factors.

In general, compounds of this disclosure will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules, including enteric coated or delayed release tablets, pills or capsules are preferred) and the bioavailability of the drug substance.

The compositions are comprised of in general, a compound of this disclosure in combination with at least one pharmaceutically acceptable excipient. Acceptable excipients are non-toxic, aid administration, and do not adversely affect the therapeutic benefit of the compound of this disclosure. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds of the disclosure may be administered topically, that is by non-systemic administration. This includes the application of the compounds externally to the epidermis or the buccal cavity and the instillation of such compounds into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose.

The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the disclosure may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator. Other suitable pharmaceutical excipients and their formulations are described in Remington's Pharmaceutical Sciences, edited by E. W. Martin (Mack Publishing Company, 20th ed., 2000).

The level of the compound in a formulation can vary within the full range employed by those skilled in the art. Typically, the formulation will contain, on a weight percent (wt. %) basis, from about 0.01-99.99 wt. % of a compound of this disclosure based on the total formulation, with the balance being one or more suitable pharmaceutical excipients. For example, the compound is present at a level of about 1-80 wt. %.

Combinations and Combination Therapies

The compounds of this disclosure may be used in combination with one or more other drugs in the treatment of diseases or conditions for which compounds of this disclosure or the other drugs may have utility. Such other drug(s) may be administered contemporaneously or sequentially with a compound of the present disclosure. When a compound of this disclosure is used contemporaneously with one or more other drugs, a pharmaceutical composition in unit dosage form containing such other drugs and the compound of the present disclosure is contemplated. However, the combination therapy may also include therapies in which the compound of this disclosure and one or more other drugs are administered on different overlapping schedules. It is also contemplated that when used in combination with one or more other active ingredients, the compounds of the present disclosure and the other active ingredients may be used in lower doses than when each is used singly.

Accordingly, the pharmaceutical compositions of the present disclosure also include those that contain one or more other drugs, in addition to a compound of the present disclosure.

The above combinations include combinations of a compound of this disclosure not only with one other drug, but also with two or more other active drugs. Likewise, a compound of this disclosure may be used in combination with other drugs that are used in the prevention, treatment, control, amelioration, or reduction of risk of the diseases or conditions for which a compound of this disclosure is useful. Such other drugs may be administered contemporaneously or sequentially with a compound of the present disclosure. When a compound of this disclosure is used contemporaneously with one or more other drugs, a pharmaceutical composition containing such other drugs in addition to the compound of this disclosure can be used. Accordingly, the pharmaceutical compositions of the present disclosure also include those that also contain one or more other active ingredients, in addition to a compound of this disclosure. The weight ratio of the compound of this disclosure to the second active ingredient may be varied and will depend upon the effective dose of each ingredient. Generally, a therapeutically effective dose of each will be used.

Where the subject in need is suffering from or at risk of suffering from cancer, the subject can be treated with a compound of this disclosure in any combination with one or more other anti-cancer agents.

In some embodiments, the compounds of the present disclosure are used in combination with a CDK 4/6 inhibitor. Examples of CDK 4/6 inhibitors suitable for the provided compositions and methods include, but are not limited to, abemaciclib (N-(5-((4-ethylpiperazin-1-yl)methyl)pyridin-2-yl)-5-fluoro-4-(4-fluoro-1-isopropyl-2-methyl-1H-benzo[d]imidazol-6-yl)pyrimidin-2-amine); palbociclib (6-acetyl-8-cyclopentyl-5-methyl-2-((5-(piperazin-1-yl)pyridin-2-yl)amino)-pyrido[2,3-d]pyrimidin-7(8H)-one) and ribociclib (7-cyclopentyl-N,N-dimethyl-2-((5-(piperazin-1-yl)pyridin-2-yl)amino)-7H-pyrrolo[2,3-d]pyrimidine-6-carboxamide) whereas the CDK 4/6 inhibitor trilaciclib (2'-((5-(piperazin-1-yl)pyridin-2-yl)amino)-7',8'-dihydro-6'H-spiro-[cyclohexane-1,9'-pyrazino[1',2':1,5]pyrrolo[2,3-d]pyrimidin]-6'-one) is in late stage clinical trials. Another CDK 4/6 inhibitor useful in the methods herein is the CDK 2/4/6 inhibitor PF-06873600 (pyrido[2,3-d]pyrimidin-7(8H)-one, 6-(difluoromethyl)-8-[(1R,2R)-2-hydroxy-2-methylcyclopentyl]-2-[[1-(methylsulfonyl)-4-piperidinyl]amino]).

In another embodiment the compounds of the present disclosure are used in combination with Raf family kinase inhibitors. Examples of Raf family kinase inhibitors suitable for the provided compositions and methods include, but are not limited to, encorafenib (LGX818): methyl (S)-(1-((4-(3-(5-chloro-2-fluoro-3-(methylsulfonamido)phenyl)-1-isopropyl-1H-pyrazol-4-yl)pyrimidin-2-yl)amino)propan-2-yl)carbamate; PLX-8394: N-(3-(5-(2-cyclopropylpyrimidin-5-yl)-3a, 7a-dihydro-1H-pyrrolo[2,3-b]pyridine-3-carbonyl)-2,4-difluorophenyl)-3-fluoropyrrolidine-1-sulfonamide; Raf-709: N-(2-methyl-5'-morpholino-6'-((tetrahydro-2H-pyran-4-yl)oxy)-[3,3'- bipyridin]-5-yl)-3-(trifluoromethyl)benzamide; LXH254: N-(3-(2-(2-hydroxyethoxy)-6-morpholinopyridin-4-yl)-4-methylphenyl)-2-(trifluoromethyl)

isonicotinamide; Sorafenib: 4-(4-(3-(4-chloro-3-(trifluoromethyl)pheny 1)ureido)phenoxy)-N-methylpicolinamide; L Y 3009120: 1-(3,3-dimethylbutyl)-3-(2-fluoro-4-methyl-5-(7-methyl-2-(methylamino)pyrido-[2,3-d]pyrimidin-6-yl)phenyl)urea; Lifirafenib (BGB-283); 5-((((1R,1aS,6bS)-1-(6-(trifhioro-methyl)-1H-benzo[d]imidazol-2-yl)-1a, 6b-dihydro-1H-cyclopropa[b]benzofuran-5-yl)methyl)-3,4-dihydro-1,8-naphthyridin-2(1H)-one; Tak-632: N-(7-cyano-6-(4-fluoro-3-(2-(3- (trifluoromethyl)phenyl)acetamido)phenoxy)benzo[d]thiazol-2-yl) cyclopropanecarboxamide; CEP-32496: 1-(3-((6,7-dimethoxyquinazolin-4-yl)oxy)phenyl)-3-(5-(1,1,1-trifluoro-2-methylpropan-2-yl)isoxazol-3-yl)urea; CCT196969: 1-(3-(tert-butyl)-1-phenyl-1H-pyrazol-5- yl)-3-(2-fluoro-4-((3-oxo-3,4-dihydropyrido[2,3-b]pyrazin-8-yl)oxy)phenyl)urea; and RO5126766: N-[3-fluoro-4-[[4-methyl-2-oxo-7-(2-pyrimidinyloxy)-2H-1-benzopyran-3-yl]methyl]-2-pyridinyl]-N'-methylsulfamide.

In another embodiment the compounds of the present disclosure are used in combination with Src family kinases. Examples of Src family kinase inhibitors suitable for the provided compositions and methods include, but are not limited to, Dasatinib (N-(2-chloro-6-methylphenyl)-2-((6-(4-(2- hydroxyethyl)piperazin-1-yl)-2-methylpyrimidin-4-yl)amino)thiazole-5-carboxamide; Ponatinib (3-(imidazo [1,2-b]pyridazin-3-ylethynyl)-4-methyl-N-(4-((4-methylpiperazin-1-yl)methyl)-3-(trifluoromethyl)phenyl) benzamide); Vandetanib (N-(4-bromo-2-fluorophenyl)-6-methoxy-7- ((1-methylpiperidin-4-yl)methoxy)quinazolin-4-amine); Bosutinib (4-((2,4-dichloro-5- methoxyphenyl) amino)-6-methoxy-7-(3-(4-methylpiperazin-1-yl)-propoxy) quinoline-3- carbonitrile); Saracatinib (N-(5-chlorobenzo[d][1,3]dioxol-4-yl)-7-(2-(4-methylpiperazin-1- yl)ethoxy)-5-((tetrahydro-2H-pyran-4-yl)oxy)quinazolin-4-amine); KX2-391 (N-benzyl-2-(5-(4-(2-morpholinoethoxy)phenyl) pyridin-2-yl)acetamide); SU6656 ((Z)—N,N-dimethyl-2-oxo-3- ((4,5,6,7-tetrahydro-1H-indol-2-yl)methylene) indoline-5-sulfonamide); PP1 (1-(tert-butyl)-3-(p- tolyl)-1H-pyrazolo[3,4-d]pyrimidin-4-amine); WH-4-023 (2,6-dimethylphenyl (2,4-dimethoxyphenyl)(2-((4-(4-methylpiperazin-1-yl)phenyl)amino)pyrimidin-4-yl) carbamate) and KX-01 (N-benzyl-2-(5-(4-(2-morpholinoethoxy)phenyl)pyridin-2-yl)acetamide). In one embodiment, the Src inhibitor is Dasatinib. In one embodiment, the Src inhibitor is Saracatinib. In one embodiment, the Src inhibitor is Ponatinib. In one embodiment, the Src inhibitor is Vandetanib. In one embodiment, the Src inhibitor is KX-01.

In another embodiment the compounds of the present disclosure are used in combination with a SHP-2 inhibitor which include, but are not limited to SHP-099 (6-(4-amino-4-methylpiperidin-1-yl)-3-(2,3-dichlorophenyl)pyrazine-2-amine dihydrochloride), RMC-4550 (3(3S,4S)-(4-amino-3-methyl-2-oxa-8-azaspiro[4.5]decan-8-yl)-6-(2,3-dichlorophenyl)pyrazin-2-yl)methanol), RMC-4360 (Revolution Medicines), TN0155 (Novartis), BBP-398 (BridgeBio), and ERAS-601 (Erasca).

In another embodiment the compounds of the present disclosure are used in combination with an mTOR inhibitor. Examples of mTOR inhibitors suitable for the provided compositions and methods include, but are not limited to, Everolimus, Rapamycin, Zotarolimus (ABT-578), ridaforolimus (Deforolimus; MK-8669), Sapanisertib (INK128; 5-(4-amino-1-isopropyl-1H-pyrazolo[3,4-d]pyrimidin-3-yl) benzo[d]oxazol-2-amine), Torin-1; 1-(4-(4-propionylpiperazin-1-yl)-3-(trifluoromethyl)cyclohexyl)-9-(quinolin-3-yl) benzo[h][1,6]naphthyridin-2(1H)-one, dactolisib (BEZ235); 2-methyl-2-(4-(3-methyl-2-oxo-8-(quinolin-3-yl)-2,3-dihydro-1H-imidazo[4,5-c]quinolin-1-yl)phenyl)propanenitrile, buparlisib (5-(2,6-dimorpholin-4-ylpyrimidin-4-yl)-4-(trifluoromethyl)pyridin-2-amine); GDC-0941 (pictilisib); 4-[2-(1H-indazol-4-yl)-6-[(4-methylsulfonylpiperazin-1-yl) methyl]thieno[3,2-d]pyrimidin-4-yl]morpholine); GDC-0349 ((S)-1-ethyl-3-(4-(4-(3-methylmorpholino)-7-(oxetan-3-yl)-5,6,7,8-tetrahydropyrido[3,4-d]pyrimidin-2-yl) phenyl)urea), VS-5584 (SB2343) (5-(8-methyl-2-morpholin-4-yl-9-propan-2- ylpurin-6-yl)pyrimidin-2-amine) and vistusertib (AZD-2014; 3-(2,4-bis((S)-3-methylmorpholino)pyrido-[2,3-d]pyrimidin-7-yl)-N-methylbenzamide).

In another embodiment the compounds of the present disclosure are used in combination with a pan ErbB family inhibitor. In one embodiment the KRAS and pan ErbB family inhibitors are the only active agents in the provided compositions and methods. In one embodiment, the pan ErbB family inhibitor is an irreversible inhibitor. Examples of irreversible pan ErbB family inhibitors suitable for the provided compositions and methods include, but are not limited to, Afatinib; Dacomitinib; Canertinib; Poziotinib, AV 412 (N-4-([3-(chloro-4-fluorophenyl)amino]-7-[3-methyl-3-(4-methyl-1-piperazin-1-butyn-1-yl]-6-quinazolinyl]-2-prepenamide); PF 6274484 N-4-([3-(chloro-4-fluorophenyl)amino]-7-methoxy-6-quinazolinyl]-2-propenamide) and HKI 357 N-(2(E)-N-[[4-[[3-chloro-4-[(fluorophenyl) methoxy]phenyl]amino]-3-cyano-7-ethoxy-6-quinolinyl]-4-(dimethylamino)-2-butenamide). In another embodiment, the pan ErbB family inhibitor is a reversible inhibitor. Examples of reversible pan ErbB family inhibitors suitable for the provided compositions and methods include, but are not limited to erlotinib, gefitinib, sapitinib; varlitinib; TAK-285 (N-[2-[4-[3- chloro-4-[3-(trifluoromethyl)phenoxy]phenylamino]-5H-pyrrolo[3,2-d]pyrimidin-5-yl]ethyl]-3-hydroxy-3-methylbutanamide); AEE788 (S)-(6-(4-((4-ethylpiperazin- 1-ylmethyl)phenyl]-N-(1-phenylethyl)-7H-pyrrolo[2,3-d]pyrimidin-4-amine); tarloxotinib 3-[N-[4-(3-bromo-4-chlorophenylamino)-pyrido[3,4-d]pyrimidin-6-yl] carbamoyl]-N,N-dimethyl-N-(1-methyl-4-nitro-1H-imidazol-5-ylmethyl)-2(E)-propen-1-aminium bromide); BMS 599626 ((3S)—3-morpholinylmethyl-[4-[[1-[(3-fluorophenyl)methyl]-1H-indazol-5-yl]amino]-5-methylpurrolo [2,1-f][1,2,4]triazine-6-yl]carbamate dihydrochloride); and GW 583340 (N-[3-chloro-4-(3- fluorobenzyloxy)phenyl]-6-[2-[2-(methylsulfonyl)ethylaminomethyl]thiazol-4-yl]quinazolin-4-amine dihydrochloride).

In one embodiment, the pan ErbB family inhibitor is a combination of an EGFR inhibitor and a HER2 inhibitor, wherein the EGFR inhibitor and the HER2 inhibitor are a combination of two of: AG 1478 (N-(3-chlorophenyl)-6,7-dimethoxyquinazolin-4-amine hydrochloride); AG 555 ((E)-2-cyano-3-(3,4-dihydoxyphenyl)-N-(3-phenylpropyl)-2-propenamide); AG 556 ((E)-2-cyano-3-(3,4-dihydroxyphenyl)-N-(4-phenylbutyl)-2-propenamide; AG 825 (E-3-[3-benzothiazol-2- ylsulfanylmethyl)-4-hydroxy-5-methoxyphenyl]-2-cyano-2-propenamide; CP 724714 (2-methoxy-N-[(2E)-3-[4-[3-methyl-4-(6-methylpyridin-3-yloxy)phenylamino]quinazolin-6-yl]-2-propen-1-yl]acetamide; BIBU 1361 (N-(3-chloro-4-fluorophenyl)-6-[4-(diethylaminomethyl)-piperidin-1-yl]pyrimido[5,4-d] pyrimidin-4-amine dihydrochloride); BIBU 1382; ($N^8$-(3-chloro-4-fluorophenyl)-$N^2$-(1-methyl-4-piperidinyl) pyrimidino[5,4-d]pyrimidin-4-amine dihydrochloride), JNJ 28871063 (5E-4-amino-6-[4-(benzyloxy)-3-chlorophenylamino] -pyrimidine-5-carbaldehyde N-[2-(4-morpholinyl)ethyl]oxime hydrochloride); PD 153035 (4-(3-bromophenylamino)-6,7-dimethoxyquinazoline hydrochloride); and PD 158780 ($N^4$-(3-bromophenyl)-$N^6$-methyl-pyrido[3,4-d]pyrimidine-4,6-diamine).

In one embodiment, the pan ErbB family inhibitor is an anti-EGFR antibody, an anti-HER2 antibody or combination of an anti-EGFR antibody and anti-HER2 antibody. Antibodies, including monoclonal antibodies, antibody conjugates and bispecific antibodies, targeting EGFR and/or HER2 are well known and several antibodies are commercially available for research and human clinical use. Examples of anti-EGFR antibodies suitable for the provided compositions and methods include necitumumab, panitumumab and cetuximab. Examples of anti-HER2 antibodies suitable for the provided compositions and methods include, pertuzumab, trastuzumab, and trastuzumab emtansine.

In some embodiments, the compounds of the present disclosure are used in combination with an immune checkpoint inhibitor. Examples of immune checkpoint inhibitors suitable for the provided compositions and methods include, but are not limited to, PD-1, PD-L1, CTLA-4, and LAG-3 inhibitors, such as Pembrolizumab (Keytruda®), Nivolumab (Opdivo®), Cemiplimab (Libtayo®), Atezolizumab (Tecentriq®), Avelumab (Bavencio®), Durvalumab (Imfinzi™), Ipilimumab (Yervoy®), Relatlimab, Opdualag, and Dostarlimab (Jemperli).

The compounds, pharmaceutically acceptable salts thereof and pharmaceutical compositions comprising such compounds and salts also may be co-administered with other anti-neoplastic compounds, e.g., chemotherapy, or used in combination with other treatments, such as radiation or surgical intervention, either as an adjuvant prior to surgery or post-operatively.

SELECTED EMBODIMENTS

Embodiment 1. A Compound of Formula I or Formula II

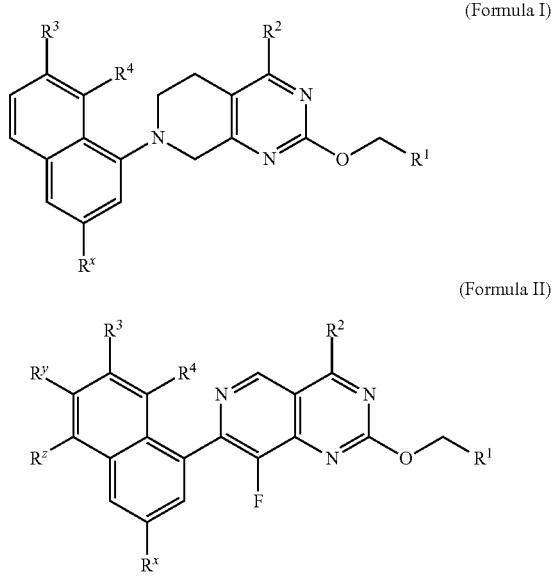

or a salt thereof; and/or an isotopologue thereof;

wherein:
$R^x$ is selected from hydrogen, hydroxy, $C_1$-$C_4$ alkyl, $C_1$-$C_4$ haloalkyl, $C_1$-$C_4$ alkoxy and $C_1$-$C_4$ haloalkoxy;
$R^y$ is selected from hydrogen, $C_1$-$C_4$ alkyl, and halo;
$R^z$ is selected from hydrogen, $C_1$-$C_4$ alkyl, and halo;
$R^1$ is a 4-8 membered saturated carbocyclic or heterocyclic group comprising one nitrogen as the sole heteroatom within the ring atoms, wherein the carbocyclic or heterocyclic group is substituted with 0, 1, 2 or 3 substituents independently selected from halo, hydroxy, $C_1$-$C_4$ alkyl, spiro $C_3$-$C_4$ cycloalkyl, $C_1$-$C_4$ alkoxy, $C_1$-$C_4$ haloalkyl, and $C_1$-$C_4$ haloalkoxy;
$R^2$ is selected from the group consisting of $R^{2a}$, $R^{2b}$, $R^{2c}$, $R^{2d}$ and $R^{2e}$;
$R^3$ is selected from the group consisting of hydrogen, halo, $C_1$-$C_4$ alkyl, $C_1$-$C_4$ alkoxy, $C_1$-$C_4$ haloalkyl, $C_1$-$C_4$ haloalkoxy, and $C_2$-$C_3$ alkynyl;
$R^4$ is selected from the group consisting of hydrogen, halo, $C_1$-$C_4$ alkyl, $C_1$-$C_4$ alkoxy, $C_1$-$C_4$ haloalkyl, $C_1$-$C_4$ haloalkoxy, $C_3$-$C_7$ cycloalkyl, CN and $C_2$-$C_3$ alkynyl;
$R^{2a}$ is —$NR^5R^6$;
$R^5$ is selected from the group consisting of H, $C_1$-$C_4$ alkyl, $C_1$-$C_4$ alkoxy, $C_1$-$C_4$ haloalkyl, and $C_1$-$C_4$ haloalkoxy; and
$R^6$ is —$C_1$-$C_6$ alkylene-S(O)$_2$—CH=CH$R^7$; or
$R^5$ and $R^6$ together with the nitrogen to which they are attached form a 4-7 membered saturated heterocyclic group comprising one ring and comprising one nitrogen as the sole heteroatom within the ring atoms, wherein the 4-7 membered saturated heterocyclic group is substituted with —(CH$_2$)$_n$—S(O)$_2$—CH=CH$R^7$;
$R^7$ is selected from the group consisting of: hydrogen, —$C_1$-$C_4$ alkyl, $C_1$-$C_4$ alkoxy, $C_1$-$C_4$ haloalkyl, $C_1$-$C_4$ haloalkoxy, and —(CH$_2$)$_m$—$NR^8R^9$;
$R^8$ and $R^9$ are independently selected from the group consisting of —H, $C_1$-$C_4$ alkyl, $C_1$-$C_4$ alkoxy, $C_1$-$C_4$ haloalkyl, and $C_1$-$C_4$ haloalkoxy; or
$R^8$ and $R^9$ together with the nitrogen atom to which they are attached form a 4-7 membered saturated heterocyclic group comprising at least one nitrogen within the ring atoms, and which is optionally substituted by halo;
n is 0 or 1;
m is 1 or 2;
$R^{2b}$ is —$NR^{10}R^{11}$;
$R^{10}$ is selected from the group consisting of H, $C_1$-$C_4$ alkyl, $C_1$-$C_4$ alkoxy, $C_1$-$C_4$ haloalkyl, and $C_1$-$C_4$ haloalkoxy; and
$R^{11}$ is selected from the group consisting of:
—($C_1$-$C_4$ alkylene)-N($R^{12}$)—CN, and
—(CH$_2$)$_w$—$R^{13}$; or
$R^{10}$ and $R^{11}$ together with the nitrogen to which they are attached form a 4-8 membered saturated heterocyclic group optionally comprising a second nitrogen as the sole additional heteroatom within the ring atoms, wherein the 4-8 membered saturated heterocyclic group is substituted with one substituent selected from the group consisting of:
—(CH$_2$)$_x$—N($R^{14}$)—CN,
a 4-6 membered saturated heterocyclic group comprising one ring and comprising one nitrogen as the sole heteroatom within the ring atoms, wherein the nitrogen is substituted with cyano, and
cyano, with the proviso that when cyano is the substituent, then the 4-8 membered saturated heterocyclic group formed by $R^{10}$ and $R^{11}$ together with the nitrogen to which they are attached comprises the second nitrogen ring atom and the cyano is connected to the 4-8 membered saturated heterocyclic group at the second ring nitrogen;

$R^{12}$ is hydrogen, $C_1$-$C_4$ alkyl, $C_1$-$C_4$ alkoxy, $C_1$-$C_4$ haloalkyl, or $C_1$-$C_4$ haloalkoxy;

$R^{13}$ is a 4-5 membered saturated heterocyclic group comprising one nitrogen as the sole heteroatom within the ring atoms, wherein the nitrogen is substituted with cyano, and wherein the heterocyclic group is optionally further substituted with 1 substituent selected from the group consisting of hydroxy, CN, $C_1$-$C_4$ cyanoalkyl, $C_1$-$C_4$ alkyl, $C_1$-$C_4$ alkoxy, $C_1$-$C_4$ haloalkyl, $C_1$-$C_4$ haloalkoxy, or halo; or $R^{13}$ is a 6 membered saturated heterocyclic group comprising one or two nitrogens as the sole heteroatom(s) within the ring atoms, wherein one of the nitrogens is substituted with cyano, and wherein the heterocyclic group is optionally further substituted with 1 substituent selected from the group consisting of hydroxy, CN, $C_1$-$C_4$ cyanoalkyl, $C_1$-$C_4$ alkyl, $C_1$-$C_4$ alkoxy, $C_1$-$C_4$ haloalkyl, $C_1$-$C_4$ haloalkoxy, or halo, provided that the optional hydroxy, CN, cyanoalkyl and halo substituents are not attached to a heteroatom; or $R^{13}$ is a 7 membered saturated heterocyclic group comprising one nitrogen, and optionally one additional heteroatom selected from nitrogen, oxygen, and sulfur, as the sole heteroatom(s) within the ring atoms, wherein one of the nitrogen ring atom(s) is substituted with cyano, and wherein the heterocyclic group is optionally further substituted with 1 substituent selected from the group consisting of hydroxy, CN, $C_1$-$C_4$ cyanoalkyl, $C_1$-$C_4$ alkyl, $C_1$-$C_4$ alkoxy, $C_1$-$C_4$ haloalkyl, $C_1$-$C_4$ haloalkoxy, or halo provided that the optional hydroxy, CN, cyanoalkyl and halo substituents are not attached to a heteroatom;

$R^{14}$ is hydrogen, $C_1$-$C_4$ alkyl, $C_1$-$C_4$ alkoxy, $C_1$-$C_4$ haloalkyl, or $C_1$-$C_4$ haloalkoxy;

w is 0, 1, or 2;

x is 0 or 1;

$R^{2c}$ is —$NR^{15}R^{16}$;

$R^{15}$ is H, $C_1$-$C_4$ alkyl, optionally substituted with one instance of CN, $C_1$-$C_4$ alkoxy, $C_1$-$C_4$ haloalkyl, or $C_1$-$C_4$ haloalkoxy; and $R^{16}$ is selected from the group consisting of:
—($C_1$-$C_4$ alkylene)-$N(R^{17})C(O)C(R^{19})$=$C(R^{20})R^{18}$, and
—$(CH_2)_y$—$R^{21}$; or $R^{15}$ and $R^{16}$ together with the nitrogen to which they are attached form a 4-8 membered saturated heterocyclic group optionally comprising a second nitrogen as the sole additional heteroatom within the ring atoms, wherein the heterocyclic group is substituted with one substituent selected from the group consisting of:
—$(CH_2)_q$—$N(R^{17})C(O)C(R^{19})$=$C(R^{20})R^{18}$, and
—$C(O)C(R^{19})$=$C(R^{20})R^{18}$, with the proviso that when —$C(O)C(R^{19})$=$C(R^{20})R^{11}$ is the substituent, then the 4-8 membered saturated heterocyclic group formed by $R^{15}$ and $R^{16}$ together with the nitrogen to which they are attached comprises the second nitrogen ring atom and the —$C(O)C(R^{19})$=$C(R^{20})R^{18}$ is connected to the heterocyclic group at the second ring nitrogen;

$R^{17}$ is selected from the group consisting of hydrogen, —$C_1$-$C_4$ alkyl, $C_1$-$C_4$ alkoxy, $C_1$-$C_4$ haloalkyl, and $C_1$-$C_4$ haloalkoxy;

$R^{18}$ is selected from the group consisting of hydrogen, —COOH, —C(O)O—$C_1$-$C_4$ alkyl, —C(O)O—$C_1$-$C_4$ haloalkyl, —C(O)—$C_1$-$C_4$ alkyl, —C(O)—$C_1$-$C_4$ haloalkyl, —C(O)$NR^{22}R^{23}$, —$(CH_2)_z$—$NR^{22}R^{23}$, —$(CH_2)_u$—$R^{34}$, —($C_1$-$C_2$ alkyl)-($C_1$-$C_2$ alkoxy), —$S(O)_2$—$C_1$-$C_4$ alkyl, —$S(O)_2$—$C_1$-$C_4$ haloalkyl, and $R^{35}$; and $R^{20}$ is selected from the group consisting of hydrogen, $C_1$-$C_4$ alkyl, $C_1$-$C_4$ alkoxy, $C_1$-$C_4$ haloalkyl, and $C_1$-$C_4$ haloalkoxy; or $R^{18}$ and $R^{20}$ together with the carbon to which they are attached can be taken together to form a 4-5 membered carbocyclic or heterocyclic ring containing one heteroatom selected from N, O and S, wherein the carbocyclic or heterocyclic ring can be optionally substituted with one instance of methyl, halo, hydroxy, methoxy or carbonyl;

$R^{19}$ is selected from the group consisting of hydrogen, $C_1$-$C_4$ alkyl, $C_1$-$C_4$ alkoxy, $C_1$-$C_4$ haloalkyl, and $C_1$-$C_4$ haloalkoxy;

$R^{21}$ is selected from:
a 4-5 membered saturated heterocyclic group comprising one nitrogen as the sole heteroatom within the ring atoms, wherein the nitrogen ring atom of the heterocyclic group is substituted with —$C(O)C(R^{19})$=$C(R^{20})R^{18}$ and wherein the heterocyclic group is not further substituted or is further substituted with 1 substituent selected from the group consisting of hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, and halo, or is further substituted with two halo substituents;

a 6 membered saturated heterocyclic group comprising one or two nitrogens as the sole heteroatom(s) within the ring atoms, wherein one of the nitrogens of the heterocyclic group is substituted with —$C(O)C(R^{19})$=$C(R^{20})R^{18}$, and wherein the heterocyclic group is not further substituted or is further substituted with 1 substituent selected from the group consisting of hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, or halo, or is further substituted with two halo substituents, provided that the optional hydroxy, CN, cyanoalkyl and halo substituents are not attached to a heteroatom; and a 7 membered saturated heterocyclic group comprising one nitrogen, and optionally one additional heteroatom selected from nitrogen, oxygen, and sulfur, as the sole heteroatom(s) within the ring atoms, wherein one of the nitrogen ring atom(s) of the heterocyclic group is substituted with —$C(O)C(R^{19})$=$C(R^{20})R^{18}$, and wherein the heterocyclic group is not further substituted or is further substituted with 1 substituent selected from the group consisting of hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, or halo, or is further substituted with two halo substituents, provided that the optional hydroxy, CN, cyanoalkyl and halo substituents are not attached to a heteroatom;

$R^{22}$ and $R^{23}$ are independently selected from the group consisting of hydrogen, $C_1$-$C_4$ alkyl, $C_1$-$C_4$ alkoxy, $C_1$-$C_4$ haloalkyl, and $C_1$-$C_4$ haloalkoxy;

$R^{34}$ is a 4-10 membered heterocycle which is substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy, $C_1$-$C_4$ hydroxyalkyl, $CH_2$—($C_3$-$C_6$ heterocyclyl) and $C_2$-$C_3$ alkynyl;

$R^{35}$ is a 5-6 membered heteroaryl group optionally substituted with 0, 1, 2 or 3 substituents independently selected from halo, hydroxy, $C_1$-$C_4$ alkyl, $C_1$-$C_4$ hydroxyalkyl, $C_1$-$C_4$ alkoxy, $C_1$-$C_4$ haloalkyl, $C_1$-$C_4$ haloalkoxy, $C_3$-$C_6$ heterocyclyl optionally substituted with one or two substituents independently selected from halo, hydroxy and methyl, and $C_3$-$C_6$ cycloalkyl optionally substituted with one or two substituents independently selected from halo, hydroxy and methyl;

y is 0, 1, or 2;

z is 1 or 2;

q is 0 or 1;

u is 0, 1 or 2;

$R^{2d}$ is selected from the group consisting of:
- —$NR^{24}R^{25}$,
- —C(O)N($R^{27}$)—($C_1$-$C_4$ alkylene)-C(O)CH=CHR$^{26}$, and
- O—($C_1$-$C_2$ alkylene)-C(O)CH=CHR$^{26}$;

$R^{24}$ is H, $C_1$-$C_4$ alkyl, $C_1$-$C_4$ alkoxy, $C_1$-$C_4$ haloalkyl, or $C_1$-$C_4$ haloalkoxy; and $R^{25}$ is —($C_1$-$C_4$ alkylene)-C(O)CH=CHR$^{26}$; or $R^{24}$ and $R^{25}$ together with the nitrogen to which they are attached form a 4-8 membered saturated heterocyclic group comprising one nitrogen as the sole heteroatom within the ring atoms, wherein the heterocyclic group is substituted with —($C_0$-$C_2$ alkylene)-C(O)CH=CHR$^{26}$, and wherein the heterocyclic group is further optionally substituted with $C_1$-$C_4$ alkyl, $C_1$-$C_4$ alkoxy, $C_1$-$C_4$ haloalkyl, or $C_1$-$C_4$ haloalkoxy;

$R^{26}$ is hydrogen, $C_1$-$C_4$ alkyl, $C_1$-$C_4$ alkoxy, $C_1$-$C_4$ haloalkyl, or $C_1$-$C_4$ haloalkoxy; and $R^{27}$ is selected from hydrogen, $C_1$-$C_4$ alkyl, $C_1$-$C_4$ alkoxy, $C_1$-$C_4$ haloalkyl, and $C_1$-$C_4$ haloalkoxy;

$R^{2e}$ is —$NR^{28}R^{29}$;

$R^{28}$ is H, $C_1$-$C_4$ alkyl, $C_1$-$C_4$ alkoxy, $C_1$-$C_4$ haloalkyl, or $C_1$-$C_4$ haloalkoxy; and $R^{29}$ is —$(CH_2)_t$—$R^{30}$;

$R^{30}$ is selected from:
- a 4-5 membered saturated heterocyclic group comprising one nitrogen as the sole heteroatom within the ring atoms, wherein the nitrogen ring atom of the heterocyclic group is substituted with —C(O)C≡CR$^{31}$ and wherein the heterocyclic group is not further substituted or is further substituted with 1 substituent selected from the group consisting of hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, and halo;
- a 6 membered saturated heterocyclic group comprising one or two nitrogens as the sole heteroatom(s) within the ring atoms, wherein one of the nitrogens of the heterocyclic group is substituted with —C(O)C≡CR$^{31}$, and wherein the heterocyclic group is not further substituted or is further substituted with 1 substituent selected from the group consisting of hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, or halo provided that the optional hydroxy, CN, cyanoalkyl and halo substituents are not attached to a heteroatom; and
- a 7 membered saturated heterocyclic group comprising one nitrogen, and optionally one additional heteroatom selected from nitrogen, oxygen, and sulfur, as the sole heteroatom(s) within the ring atoms, wherein one of the nitrogen ring atom(s) of the heterocyclic group is substituted with —C(O)C≡CR$^{31}$, and wherein the heterocyclic group is not further substituted or is further substituted with 1 substituent selected from the group consisting of hydroxy, CN, $C_1$-$C_4$ alkyl, $C_1$-$C_4$ alkoxy, $C_1$-$C_4$ cyanoalkyl, $C_1$-$C_4$ haloalkyl, $C_1$-$C_4$ haloalkoxy, or halo, provided that the optional hydroxy, CN, cyanoalkyl and halo substituents are not attached to a heteroatom;

$R^{31}$ is selected from the group consisting of —$(CH_2)_v$—$NR^{32}R^{33}$ and —$(CH_2)_p$—$R^{36}$;

$R^{32}$ and $R^{33}$ are independently selected from the group consisting of hydrogen, $C_1$-$C_4$ alkyl, $C_1$-$C_4$ alkoxy, $C_1$-$C_4$ haloalkyl, and $C_1$-$C_4$ haloalkoxy;

t is 0, 1, or 2;

v is 1 or 2;

p is 0, 1 or 2;

$R^{36}$ is a 4-10 membered heterocycle which is substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl;

with the proviso that when the compound is of Formula I, then $R^{2c}$ is not

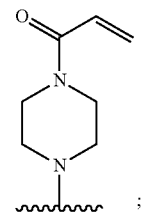

and with the further proviso that when the compound is of Formula II, then $R^{2c}$ is not —$NR^{15}R^{16}$, wherein $R^{15}$ and $R^{16}$ together with the nitrogen to which they are attached form a membered saturated heterocyclic group comprising a second nitrogen as the sole additional heteroatom within the ring atoms, wherein the second nitrogen is substituted with —C(O)—CH=CH$_2$.

Embodiment 2. The compound of embodiment 1, wherein the compound is a compound of Formula I, or a salt thereof.

Embodiment 3. The compound of embodiment 1, wherein the compound is a compound of Formula II, or a salt thereof.

Embodiment 4. The compound of any one of embodiments 1-3, wherein $R^y$ is selected from hydrogen and halo.

Embodiment 5. The compound of any one of embodiments 1-3, wherein $R^y$ is selected from hydrogen, Me, F and Cl.

Embodiment 6. The compound of any one of embodiments 1-3, wherein $R^y$ is selected from hydrogen, F and Cl.

Embodiment 7. The compound of any one of embodiments 1-3, wherein $R^y$ is H.

Embodiment 8. The compound of any one of embodiments 1-7, wherein $R^z$ is selected from hydrogen, Me, F and Cl.

Embodiment 9. The compound of any one of embodiments 1-7, wherein $R^z$ is selected from hydrogen, Me and F Embodiment 10. The compound of any one of embodiments 1-7, wherein $R^z$ is hydrogen.

Embodiment 11. A compound of Formula I-1 or Formula II-1:

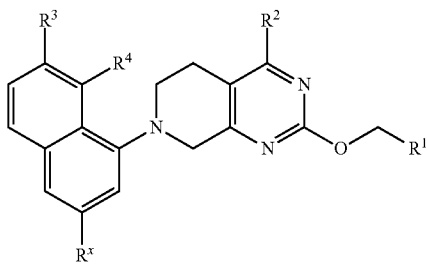
(Formula I-1)

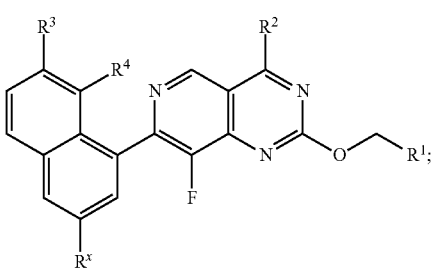
(Formula II-1)

or a salt thereof; and/or an isotopologue thereof; wherein:

$R^x$ is selected from hydrogen, hydroxy, $C_1$-$C_4$ alkyl, $C_1$-$C_4$ haloalkyl, $C_1$-$C_4$ alkoxy and $C_1$-$C_4$ haloalkoxy;

$R^1$ is a 4-8 membered saturated carbocyclic or heterocyclic group comprising one nitrogen as the sole heteroatom within the ring atoms, wherein the carbocyclic or heterocyclic group is substituted with 0, 1, 2 or 3 substituents independently selected from halo, hydroxy, $C_1$-$C_4$ alkyl, spiro $C_3$-$C_4$ cycloalkyl, $C_1$-$C_4$ alkoxy, $C_1$-$C_4$ haloalkyl, and $C_1$-$C_4$ haloalkoxy;

$R^2$ is selected from the group consisting of $R^{2a}$, $R^{2b}$, $R^{2c}$, $R^{2d}$ and $R^{2e}$;

$R^3$ is selected from the group consisting of hydrogen, halo, $C_1$-$C_4$ alkyl, $C_1$-$C_4$ alkoxy, $C_1$-$C_4$ haloalkyl, $C_1$-$C_4$ haloalkoxy, and $C_2$-$C_3$ alkynyl;

$R^4$ is selected from the group consisting of hydrogen, halo, $C_1$-$C_4$ alkyl, $C_1$-$C_4$ alkoxy, $C_1$-$C_4$ haloalkyl, $C_1$-$C_4$ haloalkoxy, and $C_2$-$C_3$ alkynyl;

$R^{2a}$ is —$NR^5R^6$;

$R^5$ is selected from the group consisting of H, $C_1$-$C_4$ alkyl, $C_1$-$C_4$ alkoxy, $C_1$-$C_4$ haloalkyl, and $C_1$-$C_4$ haloalkoxy; and $R^6$ is —$C_1$-$C_6$ alkylene-$S(O)_2$—CH=$CHR^7$; or $R^5$ and $R^6$ together with the nitrogen to which they are attached form a 4-7 membered saturated heterocyclic group comprising one ring and comprising one nitrogen as the sole heteroatom within the ring atoms, wherein the 4-7 membered saturated heterocyclic group is substituted with —$(CH_2)_n$—$S(O)_2$—CH=$CHR^7$;

$R^7$ is selected from the group consisting of: hydrogen, —$C_1$-$C_4$ alkyl, $C_1$-$C_4$ alkoxy, $C_1$-$C_4$ haloalkyl, $C_1$-$C_4$ haloalkoxy, and —$(CH_2)_m$—$NR^8R^9$;

$R^8$ and $R^9$ are independently selected from the group consisting of —H, $C_1$-$C_4$ alkyl, $C_1$-$C_4$ alkoxy, $C_1$-$C_4$ haloalkyl, and $C_1$-$C_4$ haloalkoxy; or $R^8$ and $R^9$ together with the nitrogen atom to which they are attached form a 4-7 membered saturated heterocyclic group comprising at least one nitrogen within the ring atoms, and which is optionally substituted by halo;

n is 0 or 1;
m is 1 or 2;

$R^{2b}$ is —$NR^{10}R^{11}$;

$R^{10}$ is selected from the group consisting of H, $C_1$-$C_4$ alkyl, $C_1$-$C_4$ alkoxy, $C_1$-$C_4$ haloalkyl, and $C_1$-$C_4$ haloalkoxy; and $R^{11}$ is selected from the group consisting of:
—($C_1$-$C_4$ alkylene)-$N(R^{12})$—CN, and
—$(CH_2)_w$—$R^{13}$; or $R^{10}$ and $R^{11}$ together with the nitrogen to which they are attached form a 4-8 membered saturated heterocyclic group optionally comprising a second nitrogen as the sole additional heteroatom within the ring atoms, wherein the 4-8 membered saturated heterocyclic group is substituted with one substituent selected from the group consisting of:
—$(CH_2)_x$—$N(R^{14})$—CN,
a 4-6 membered saturated heterocyclic group comprising one ring and comprising one nitrogen as the sole heteroatom within the ring atoms, wherein the nitrogen is substituted with cyano, and
cyano, with the proviso that when cyano is the substituent, then the 4-8 membered saturated heterocyclic group formed by $R^{10}$ and $R^{11}$ together with the nitrogen to which they are attached comprises the second nitrogen ring atom and the cyano is connected to the 4-8 membered saturated heterocyclic group at the second ring nitrogen;

$R^{12}$ is hydrogen, $C_1$-$C_4$ alkyl, $C_1$-$C_4$ alkoxy, $C_1$-$C_4$ haloalkyl, or $C_1$-$C_4$ haloalkoxy;

$R^{13}$ is a 4-5 membered saturated heterocyclic group comprising one nitrogen as the sole heteroatom within the ring atoms, wherein the nitrogen is substituted with cyano, and wherein the heterocyclic group is optionally further substituted with 1 substituent selected from the group consisting of hydroxy, CN, $C_1$-$C_4$ cyanoalkyl, $C_1$-$C_4$ alkyl, $C_1$-$C_4$ alkoxy, $C_1$-$C_4$ haloalkyl, $C_1$-$C_4$ haloalkoxy, or halo; or $R^{13}$ is a 6 membered saturated heterocyclic group comprising one or two nitrogens as the sole heteroatom(s) within the ring atoms, wherein one of the nitrogens is substituted with cyano, and wherein the heterocyclic group is optionally further substituted with 1 substituent selected from the group consisting of hydroxy, CN, $C_1$-$C_4$ cyanoalkyl, $C_1$-$C_4$ alkyl, $C_1$-$C_4$ alkoxy, $C_1$-$C_4$ haloalkyl, $C_1$-$C_4$ haloalkoxy, or halo, provided that the optional hydroxy, CN, cyanoalkyl and halo substituents are not attached to a heteroatom; or $R^{13}$ is a 7 membered saturated heterocyclic group comprising one nitrogen, and optionally one additional heteroatom selected from nitrogen, oxygen, and sulfur, as the sole heteroatom(s) within the ring atoms, wherein one of the nitrogen ring atom(s) is substituted with cyano, and wherein the heterocyclic group is optionally further substituted with 1 substituent selected from the group consisting of hydroxy, CN, $C_1$-$C_4$ cyanoalkyl, $C_1$-$C_4$ alkyl, $C_1$-$C_4$ alkoxy, $C_1$-$C_4$ haloalkyl, $C_1$-$C_4$ haloalkoxy, or halo provided that the optional hydroxy, CN, cyanoalkyl and halo substituents are not attached to a heteroatom;

$R^{14}$ is hydrogen, $C_1$-$C_4$ alkyl, $C_1$-$C_4$ alkoxy, $C_1$-$C_4$ haloalkyl, or $C_1$-$C_4$ haloalkoxy;

w is 0, 1, or 2;

x is 0 or 1;

$R^{2c}$ is —$NR^{15}R^{16}$;

$R^{15}$ is H, $C_1$-$C_4$ alkyl, $C_1$-$C_4$ alkoxy, $C_1$-$C_4$ haloalkyl, or $C_1$-$C_4$ haloalkoxy; and $R^{16}$ is selected from the group consisting of:
—($C_1$-$C_4$ alkylene)-N($R^{17}$)C(O)C($R^{19}$)=C($R^{20}$)$R^{18}$, and
—($CH_2$)$_y$—$R^{21}$; or
$R^{15}$ and $R^{16}$ together with the nitrogen to which they are attached form a 4-8 membered saturated heterocyclic group optionally comprising a second nitrogen as the sole additional heteroatom within the ring atoms, wherein the heterocyclic group is substituted with one substituent selected from the group consisting of:
—($CH_2$)$_q$—N($R^{17}$)C(O)C($R^{19}$)=C($R^{20}$)$R^{18}$, and
—C(O)C($R^{19}$)=C($R^{20}$)$R^{18}$, with the proviso that when —C(O)C($R^{19}$)=C($R^{20}$)$R^{18}$ is the substituent, then the 4-8 membered saturated heterocyclic group formed by $R^{15}$ and $R^{16}$ together with the nitrogen to which they are attached comprises the second nitrogen ring atom and the —C(O)C($R^{19}$)=C($R^{20}$)$R^{18}$ is connected to the heterocyclic group at the second ring nitrogen;
$R^{17}$ is selected from the group consisting of hydrogen, —$C_1$-$C_4$ alkyl, $C_1$-$C_4$ alkoxy, $C_1$-$C_4$ haloalkyl, and $C_1$-$C_4$ haloalkoxy;
$R^{18}$ is selected from the group consisting of hydrogen, —COOH, —C(O)O—$C_1$-$C_4$ alkyl, —C(O)O—$C_1$-$C_4$ haloalkyl, —C(O)—$C_1$-$C_4$ alkyl, —C(O)—$C_1$-$C_4$ haloalkyl, —C(O)N$R^{22}$$R^{23}$, —($CH_2$)$_z$—N$R^{22}$$R^{23}$, —($CH_2$)$_u$—$R^{34}$, —($C_1$-$C_2$ alkyl)-($C_1$-$C_2$ alkoxy), —S(O)$_2$—$C_1$-$C_4$ alkyl, —S(O)$_2$—$C_1$-$C_4$ haloalkyl, and $R^{35}$;
$R^{19}$ is selected from the group consisting of hydrogen, $C_1$-$C_4$ alkyl, $C_1$-$C_4$ alkoxy, $C_1$-$C_4$ haloalkyl, and $C_1$-$C_4$ haloalkoxy;
$R^{20}$ is selected from the group consisting of hydrogen, $C_1$-$C_4$ alkyl, $C_1$-$C_4$ alkoxy, $C_1$-$C_4$ haloalkyl, and $C_1$-$C_4$ haloalkoxy;
$R^{21}$ is selected from:
a 4-5 membered saturated heterocyclic group comprising one nitrogen as the sole heteroatom within the ring atoms, wherein the nitrogen ring atom of the heterocyclic group is substituted with —C(O)C($R^{19}$)=C($R^{20}$)$R^{18}$ and wherein the heterocyclic group is not further substituted or is further substituted with 1 substituent selected from the group consisting of hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, and halo;
a 6 membered saturated heterocyclic group comprising one or two nitrogens as the sole heteroatom(s) within the ring atoms, wherein one of the nitrogens of the heterocyclic group is substituted with —C(O)C($R^{19}$)=C($R^{20}$)$R^{18}$, and wherein the heterocyclic group is not further substituted or is further substituted with 1 substituent selected from the group consisting of hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, or halo provided that the optional hydroxy, CN, cyanoalkyl and halo substituents are not attached to a heteroatom; and
a 7 membered saturated heterocyclic group comprising one nitrogen, and optionally one additional heteroatom selected from nitrogen, oxygen, and sulfur, as the sole heteroatom(s) within the ring atoms, wherein one of the nitrogen ring atom(s) of the heterocyclic group is substituted with —C(O)C($R^{19}$)=C($R^{20}$)$R^{18}$, and wherein the heterocyclic group is not further substituted or is further substituted with 1 substituent selected from the group consisting of hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, or halo provided that the optional hydroxy, CN, cyanoalkyl and halo substituents are not attached to a heteroatom;
$R^{22}$ and $R^{23}$ are independently selected from the group consisting of hydrogen, $C_1$-$C_4$ alkyl, $C_1$-$C_4$ alkoxy, $C_1$-$C_4$ haloalkyl, and $C_1$-$C_4$ haloalkoxy;
$R^{34}$ is a 4-10 membered heterocycle which is substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl;
$R^{35}$ is a 5-6 membered heteroaryl group optionally substituted with 0, 1 or 2 substituents independently selected from halo, hydroxy, $C_1$-$C_4$ alkyl, $C_1$-$C_4$ hydroxyalkyl, $C_1$-$C_4$ alkoxy, $C_1$-$C_4$ haloalkyl, $C_1$-$C_4$ haloalkoxy, $C_3$-$C_6$ heterocyclyl optionally substituted with one or two substituents independently selected from halo and methyl, and $C_3$-$C_6$ cycloalkyl optionally substituted with one or two substituents independently selected from halo and methyl;
y is 0, 1, or 2;
z is 1 or 2;
q is 0 or 1;
u is 0, 1 or 2;
$R^{2d}$ is selected from the group consisting of:
—N$R^{24}$$R^2$,
—C(O)N($R^{27}$)—($C_1$-$C_4$ alkylene)-C(O)CH=CH$R^{26}$, and
—O—($C_1$-$C_2$ alkylene)-C(O)CH=CH$R^{26}$;
$R^{24}$ is H, $C_1$-$C_4$ alkyl, $C_1$-$C_4$ alkoxy, $C_1$-$C_4$ haloalkyl, or $C_1$-$C_4$ haloalkoxy; and
$R^{25}$ is —($C_1$-$C_4$ alkylene)-C(O)CH=CH$R^{26}$; or
$R^{24}$ and $R^{25}$ together with the nitrogen to which they are attached form a 4-8 membered saturated heterocyclic group comprising one nitrogen as the sole heteroatom within the ring atoms, wherein the heterocyclic group is substituted with —($C_0$-$C_2$ alkylene)-C(O)CH=CH$R^{26}$, and wherein the heterocyclic group is further optionally substituted with $C_1$-$C_4$ alkyl, $C_1$-$C_4$ alkoxy, $C_1$-$C_4$ haloalkyl, or $C_1$-$C_4$ haloalkoxy;
$R^{26}$ is hydrogen, $C_1$-$C_4$ alkyl, $C_1$-$C_4$ alkoxy, $C_1$-$C_4$ haloalkyl, or $C_1$-$C_4$ haloalkoxy; and
$R^{27}$ is selected from hydrogen, $C_1$-$C_4$ alkyl, $C_1$-$C_4$ alkoxy, $C_1$-$C_4$ haloalkyl, and $C_1$-$C_4$ haloalkoxy;
$R^{2e}$ is —N$R^{28}$$R^{29}$;
$R^{28}$ is H, $C_1$-$C_4$ alkyl, $C_1$-$C_4$ alkoxy, $C_1$-$C_4$ haloalkyl, or $C_1$-$C_4$ haloalkoxy; and
$R^{29}$ is —($CH_2$)$_t$—$R^{30}$;
$R^{30}$ is selected from:
a 4-5 membered saturated heterocyclic group comprising one nitrogen as the sole heteroatom within the ring atoms, wherein the nitrogen ring atom of the heterocyclic group is substituted with —C(O)C≡C$R^{31}$ and wherein the heterocyclic group is not further substituted or is further substituted with 1 substituent selected from the group consisting of hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, and halo;
a 6 membered saturated heterocyclic group comprising one or two nitrogens as the sole heteroatom(s) within the ring atoms, wherein one of the nitrogens of the heterocyclic group is substituted with —C(O)C≡C$R^{31}$, and wherein the heterocyclic group is not further substituted or is further substituted with 1 substituent selected from the group consisting of hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, or halo provided that the optional hydroxy, CN, cyanoalkyl and halo substituents are not attached to a heteroatom; and a 7 membered saturated heterocyclic group comprising one nitrogen, and optionally one additional heteroatom selected from nitrogen, oxygen, and sulfur, as the sole heteroatom(s) within the ring atoms, wherein one of the nitrogen ring atom(s) of the heterocyclic group is substituted with —C(O)C≡CR$^{31}$, and wherein the heterocyclic group is not further substituted or is further substituted with 1 substituent selected from the group consisting of hydroxy, CN, $C_1$-$C_4$ alkyl, $C_1$-$C_4$ alkoxy, $C_1$-$C_4$ cyanoalkyl, $C_1$-$C_4$ haloalkyl, $C_1$-$C_4$ haloalkoxy, or halo, provided that the optional hydroxy, CN, cyanoalkyl and halo substituents are not attached to a heteroatom;

$R^{31}$ is selected from the group consisting of —(CH$_2$)$_v$—NR$^{32}$R$^{33}$ and —(CH$_2$)$_p$—R$^{36}$;

$R^{32}$ and $R^{33}$ are independently selected from the group consisting of hydrogen, $C_1$-$C_4$ alkyl, $C_1$-$C_4$ alkoxy, $C_1$-$C_4$ haloalkyl, and $C_1$-$C_4$ haloalkoxy;

t is 0, 1, or 2;

v is 1 or 2;

p is 0, 1 or 2;

$R^{36}$ is a 4-10 membered heterocycle which is substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl;

with the proviso that when the compound is of Formula I-1, then $R^{2c}$ is not

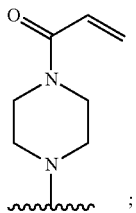 [SMILES: *N1CCN(C(=O)C=C)CC1]

and with the further proviso that when the compound is of Formula II-1, then $R^{2c}$ is not —NR$^{15}$R$^{16}$, wherein R$^{15}$ and R$^{16}$ together with the nitrogen to which they are attached form a 4-8 membered saturated heterocyclic group comprising a second nitrogen as the sole additional heteroatom within the ring atoms, wherein the second nitrogen is substituted with —C(O)—CH=CH$_2$.

Embodiment 12. The compound of embodiment 11, wherein the compound is a compound of Formula I-1, or a salt thereof.

Embodiment 13. The compound of embodiment 11, wherein the compound is a compound of Formula II-1, or a salt thereof.

Embodiment 14. The compound of any one of embodiments 11-13, wherein R$^x$ is selected from hydrogen, hydroxy, and $C_1$-$C_4$ haloalkoxy.

Embodiment 15. The compound of any one of embodiments 11-13, wherein R$^x$ is selected from hydrogen, hydroxy and —OCHF$_2$.

Embodiment 16. The compound of any one of embodiments 11-13, wherein R$^x$ is selected from hydrogen and hydroxy.

Embodiment 17. The compound of any one of embodiments 11-13, wherein R$^x$ is hydrogen.

Embodiment 18. A compound of Formula I-2 or Formula II-2:

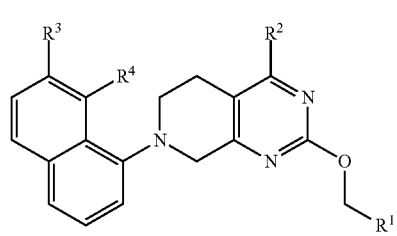
(Formula I-2)

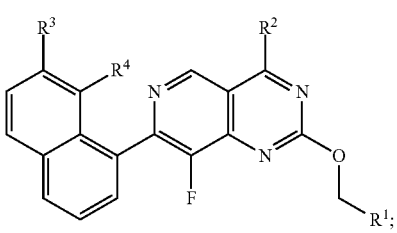
(Formula II-2)

or a salt thereof; and/or an isotopologue thereof; wherein:

$R^1$ is a 4-8 membered saturated carbocyclic or heterocyclic group comprising one nitrogen as the sole heteroatom within the ring atoms, optionally substituted with one or more substituents independently selected from $C_1$-$C_4$ alkyl, spiro $C_3$-$C_4$ cycloalkyl, $C_1$-$C_4$ alkoxy, $C_1$-$C_4$ haloalkyl, and $C_1$-$C_4$ haloalkoxy;

$R^2$ is selected from the group consisting of $R^{2a}$, $R^{2b}$, $R^{2c}$, and $R^{2d}$:

$R^3$ is selected from the group consisting of hydrogen, halo, $C_1$-$C_4$ alkyl, $C_1$-$C_4$ alkoxy, $C_1$-$C_4$ haloalkyl, $C_1$-$C_4$ haloalkoxy, and $C_1$-$C_3$ alkynyl;

$R^4$ is selected from the group consisting of hydrogen, halo, $C_1$-$C_4$ alkyl, $C_1$-$C_4$ alkoxy, $C_1$-$C_4$ haloalkyl, $C_1$-$C_4$ haloalkoxy, and $C_1$-$C_3$ alkynyl;

$R^{2a}$ is —NR$^5$R$^6$;

$R^5$ is selected from the group consisting of H, $C_1$-$C_4$ alkyl, $C_1$-$C_4$ alkoxy, $C_1$-$C_4$ haloalkyl, and $C_1$-$C_4$ haloalkoxy; and $R^6$ is —$C_1$-$C_6$ alkylene-S(O)$_2$—CH=CHR$^7$; or $R^5$ and $R^6$ together with the nitrogen to which they are attached form a 4-7 membered saturated heterocyclic group comprising one ring and comprising one nitrogen as the sole heteroatom within the ring atoms, wherein the 4-7 membered saturated heterocyclic group is substituted with —(CH$_2$)$_n$—S(O)$_2$—CH=CHR$^7$;

$R^7$ is selected from the group consisting of: hydrogen, —$C_1$-$C_4$ alkyl, $C_1$-$C_4$ alkoxy, $C_1$-$C_4$ haloalkyl, $C_1$-$C_4$ haloalkoxy, and —(CH$_2$)$_m$—NR$^8$R$^9$;

$R^8$ and $R^9$ are independently selected from the group consisting of —H, $C_1$-$C_4$ alkyl, $C_1$-$C_4$ alkoxy, $C_1$-$C_4$ haloalkyl, and $C_1$-$C_4$ haloalkoxy; or $R^8$ and $R^9$ together with the nitrogen atom to which they are attached form a 4-7 membered saturated heterocyclic group comprising at least one nitrogen within the ring atoms, and which is optionally substituted by halo;

n is 0 or 1;

m is 1 or 2;

$R^{2b}$ is —NR$^{10}$R$^{11}$;

$R^{10}$ is selected from the group consisting of H, $C_1$-$C_4$ alkyl, $C_1$-$C_4$ alkoxy, $C_1$-$C_4$ haloalkyl, and $C_1$-$C_4$ haloalkoxy; and

35

$R^{11}$ is selected from the group consisting of:
—($C_1$-$C_4$ alkylene)-N($R^{12}$)—CN, and
—($CH_2$)$_w$—$R^{13}$; or
$R^{10}$ and $R^{11}$ together with the nitrogen to which they are attached form a 4-8 membered saturated heterocyclic group optionally comprising a second nitrogen as the sole additional heteroatom within the ring atoms, wherein the 4-8 membered saturated heterocyclic group is substituted with one substituent selected from the group consisting of:
—($CH_2$)$_x$—N($R^{14}$)—CN,
a 4-6 membered saturated heterocyclic group comprising one ring and comprising one nitrogen as the sole heteroatom within the ring atoms, wherein the nitrogen is substituted with cyano, and
cyano, with the proviso that when cyano is the substituent, then the 4-8 membered saturated heterocyclic group formed by $R^{10}$ and $R^{11}$ together with the nitrogen to which they are attached comprises the second nitrogen ring atom and the cyano is connected to the 4-8 membered saturated heterocyclic group at the second ring nitrogen;
$R^{12}$ is hydrogen, $C_1$-$C_4$ alkyl, $C_1$-$C_4$ alkoxy, $C_1$-$C_4$ haloalkyl, or $C_1$-$C_4$ haloalkoxy; $R^{13}$ is a 4-5 membered saturated heterocyclic group comprising one nitrogen as the sole heteroatom within the ring atoms, wherein the nitrogen is substituted with cyano, and wherein the heterocyclic group is optionally further substituted with $C_1$-$C_4$ alkyl, $C_1$-$C_4$ alkoxy, $C_1$-$C_4$ haloalkyl, $C_1$-$C_4$ haloalkoxy, or halo; or
$R^{13}$ is a 6 membered saturated heterocyclic group comprising one or two nitrogens as the sole heteroatom(s) within the ring atoms, wherein one of the nitrogens is substituted with cyano, and wherein the heterocyclic group is optionally further substituted with $C_1$-$C_4$ alkyl, $C_1$-$C_4$ alkoxy, $C_1$-$C_4$ haloalkyl, $C_1$-$C_4$ haloalkoxy, or halo; or
$R^{13}$ is a 7 membered saturated heterocyclic group comprising one nitrogen, and optionally one additional heteroatom selected from nitrogen, oxygen, and sulfur, as the sole heteroatom(s) within the ring atoms, wherein one of the nitrogen ring atom(s) is substituted with cyano, and wherein the heterocyclic group is optionally further substituted with $C_1$-$C_4$ alkyl, $C_1$-$C_4$ alkoxy, $C_1$-$C_4$ haloalkyl, $C_1$-$C_4$ haloalkoxy, or halo;
$R^{14}$ is hydrogen, $C_1$-$C_4$ alkyl, $C_1$-$C_4$ alkoxy, $C_1$-$C_4$ haloalkyl, or $C_1$-$C_4$ haloalkoxy;
w is 0, 1, or 2;
x is 0 or 1;
$R^{2c}$ is —NR$^{15}$R$^{16}$;
$R^{15}$ is H, $C_1$-$C_4$ alkyl, $C_1$-$C_4$ alkoxy, $C_1$-$C_4$ haloalkyl, or $C_1$-$C_4$ haloalkoxy; and
$R^{16}$ is selected from the group consisting of:
—($C_1$-$C_4$ alkylene)-N($R^{17}$)C(O)C($R^{19}$)=C($R^{20}$)$R^{18}$, and
—($CH_2$)$_y$—$R^{21}$, wherein $R^{21}$ is a 4-7 membered saturated heterocyclic group comprising one nitrogen as the sole heteroatom within the ring atoms, wherein the nitrogen ring atom is substituted with —C(O)C($R^{19}$)=C($R^{20}$)$R^{18}$ and wherein the heterocyclic group is optionally further substituted with one substituent selected from the group consisting of $C_1$-$C_4$ alkyl, $C_1$-$C_4$ alkoxy, $C_1$-$C_4$ haloalkyl, $C_1$-$C_4$ haloalkoxy, and halo; or
$R^{15}$ and $R^{16}$ together with the nitrogen to which they are attached form a 4-8 membered saturated heterocyclic group optionally comprising a second nitrogen as the sole additional heteroatom within the ring atoms,

36 wherein the heterocyclic group is substituted with one substituent selected from the group consisting of:
—($CH_2$)$_q$—N($R^{17}$)C(O)C($R^{19}$)=C($R^{20}$)$R^{18}$, and
—C(O)C($R^{19}$)=C($R^{20}$)$R^{18}$, with the proviso that when —C(O)C($R^{19}$)=C($R^{20}$)$R^{11}$ is the substituent, then the 4-8 membered saturated heterocyclic group formed by $R^{15}$ and $R^{16}$ together with the nitrogen to which they are attached comprises the second nitrogen ring atom and the —C(O)C($R^{19}$)=C($R^{20}$)$R^{18}$ is connected to the heterocyclic group at the second ring nitrogen;
$R^{17}$ is selected from the group consisting of hydrogen, —$C_1$-$C_4$ alkyl, $C_1$-$C_4$ alkoxy, $C_1$-$C_4$ haloalkyl, and $C_1$-$C_4$ haloalkoxy;
$R^{18}$ is selected from the group consisting of hydrogen, —COOH, —C(O)O—$C_1$-$C_4$ alkyl, —C(O)O—$C_1$-$C_4$ haloalkyl, —C(O)—$C_1$-$C_4$ alkyl, —C(O)—$C_1$-$C_4$ haloalkyl, —C(O)NR$^{22}$R$^{23}$, —($CH_2$)$_z$—NR$^{22}$R$^{23}$, —($C_1$-$C_2$ alkyl)-($C_1$-$C_2$ alkoxy), —S(O)$_2$—$C_1$-$C_4$ alkyl, —S(O)$_2$—$C_1$-$C_4$ haloalkyl, and 5-6 membered heteroaryl group optionally substituted with $C_1$-$C_4$ alkyl, $C_1$-$C_4$ alkoxy, $C_1$-$C_4$ haloalkyl, or $C_1$-$C_4$ haloalkoxy;
$R^{19}$ is selected from the group consisting of hydrogen, $C_1$-$C_4$ alkyl, $C_1$-$C_4$ alkoxy, $C_1$-$C_4$ haloalkyl, and $C_1$-$C_4$ haloalkoxy;
$R^{20}$ is selected from the group consisting of hydrogen, $C_1$-$C_4$ alkyl, $C_1$-$C_4$ alkoxy, $C_1$-$C_4$ haloalkyl, and $C_1$-$C_4$ haloalkoxy;
$R^{22}$ and $R^{23}$ are independently selected from the group consisting of hydrogen, $C_1$-$C_4$ alkyl, $C_1$-$C_4$ alkoxy, $C_1$-$C_4$ haloalkyl, and $C_1$-$C_4$ haloalkoxy;
y is 0, 1, or 2;
z is 1 or 2;
q is 0 or 1;
$R^{2d}$ is selected from the group consisting of:
—NR$^{24}$R$^2$,
—C(O)N($R^{27}$)—($C_1$-$C_4$ alkylene)-C(O)CH=CHR$^{26}$, and
—O—($C_1$-$C_2$ alkylene)-C(O)CH=CHR$^{26}$;
$R^{24}$ is H, $C_1$-$C_4$ alkyl, $C_1$-$C_4$ alkoxy, $C_1$-$C_4$ haloalkyl, or $C_1$-$C_4$ haloalkoxy; and
$R^{25}$ is —($C_1$-$C_4$ alkylene)-C(O)CH=CHR$^{26}$; or
$R^{24}$ and $R^{25}$ together with the nitrogen to which they are attached form a 4-8 membered saturated heterocyclic group comprising one nitrogen as the sole heteroatom within the ring atoms, wherein the heterocyclic group is substituted with —($C_0$-$C_2$ alkylene)-C(O)CH=CHR$^{26}$, and wherein the heterocyclic group is further optionally substituted with $C_1$-$C_4$ alkyl, $C_1$-$C_4$ alkoxy, $C_1$-$C_4$ haloalkyl, or $C_1$-$C_4$ haloalkoxy;
$R^{26}$ is hydrogen, $C_1$-$C_4$ alkyl, $C_1$-$C_4$ alkoxy, $C_1$-$C_4$ haloalkyl, or $C_1$-$C_4$ haloalkoxy; and
$R^{27}$ is selected from hydrogen, $C_1$-$C_4$ alkyl, $C_1$-$C_4$ alkoxy, $C_1$-$C_4$ haloalkyl, and $C_1$-$C_4$ haloalkoxy;
with the proviso that when the compound is of Formula I-2, then $R^{2c}$ is not

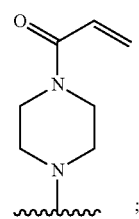

and with the further proviso that when the compound is of Formula II-2, then $R^{2c}$ is not —$NR^{15}R^{16}$, wherein $R^{15}$ and $R^{16}$ together with the nitrogen to which they are attached form a 4-8 membered saturated heterocyclic group comprising a second nitrogen as the sole additional heteroatom within the ring atoms, wherein the second nitrogen is substituted with —C(O)—CH=CH$_2$.

Embodiment 19. The compound of embodiment 18, wherein the compound is a compound of Formula I-2, or a salt thereof.

Embodiment 20. The compound of embodiment 18, wherein the compound is a compound of Formula II-2, or a salt thereof.

Embodiment 21. The compound of any one of embodiments 1-20, wherein the 4-8 membered saturated heterocyclic or carbocyclic group of $R^1$ comprises a heterocyclic group.

Embodiment 22. The compound of any one of embodiments 1-20, wherein the 4-8 membered saturated heterocyclic or carbocyclic group of $R^1$ comprises a carbocyclic group.

Embodiment 23. The compound of any one of embodiments 1-20, wherein the 4-8 membered saturated heterocyclic or carbocyclic group of $R^1$ comprises one ring.

Embodiment 24. The compound of any one of embodiments 1-20, wherein the 4-8 membered saturated heterocyclic or carbocyclic group of $R^1$ comprises two rings.

Embodiment 25. The compound of any one of embodiments 1-20, wherein the 4-8 membered saturated heterocyclic or carbocyclic group of $R^1$ is unsubstituted.

Embodiment 26. The compound of any one of embodiments 1-20, wherein the 4-8 membered saturated heterocyclic or carbocyclic group of $R^1$ is substituted with one $C_1$-$C_4$ alkyl.

Embodiment 27. The compound of any one of embodiments 1-20, wherein $R^1$ is a 4-8 membered saturated monocyclic carbocyclic or monocyclic heterocyclic group comprising one nitrogen as the sole heteroatom within the ring atoms, wherein the carbocyclic or heterocyclic group is substituted with 0, 1, 2 or 3 substituents independently selected from halo, hydroxy, $C_1$-$C_4$ alkyl, spiro $C_3$-$C_4$ cycloalkyl, $C_1$-$C_4$ alkoxy, $C_1$-$C_4$ haloalkyl, and $C_1$-$C_4$ haloalkoxy.

Embodiment 28. The compound of any one of embodiments 1-20, wherein $R^1$ is a 4-8 membered saturated bicyclic carbocyclic or bicyclic heterocyclic group comprising one nitrogen as the sole heteroatom within the ring atoms, wherein the carbocyclic or heterocyclic group is substituted with 0, 1, 2 or 3 substituents independently selected from halo, hydroxy, $C_1$-$C_4$ alkyl, spiro $C_3$-$C_4$ cycloalkyl, $C_1$-$C_4$ alkoxy, $C_1$-$C_4$ haloalkyl, and $C_1$-$C_4$ haloalkoxy.

Embodiment 29. The compound of any one of embodiments 1-28, wherein $R^1$ is a 4-8 membered saturated heterocyclic group comprising one nitrogen as the sole heteroatom within the ring atoms, wherein the heterocyclic group is substituted with 0, 1, 2 or 3 substituents independently selected from halo, hydroxy, $C_1$-$C_4$ alkyl, spiro $C_3$-$C_4$ cycloalkyl, $C_1$-$C_4$ alkoxy, $C_1$-$C_4$ haloalkyl, and $C_1$-$C_4$ haloalkoxy.

Embodiment 30. The compound of any one of embodiments 1-28, wherein $R^1$ is a 4-8 membered saturated carbocyclic group substituted with 0, 1, 2 or 3 substituents independently selected from halo, hydroxy, $C_1$-$C_4$ alkyl, spiro $C_3$-$C_4$ cycloalkyl, $C_1$-$C_4$ alkoxy, $C_1$-$C_4$ haloalkyl, and $C_1$-$C_4$ haloalkoxy.

Embodiment 31. The compound of any one of embodiments 1-30, wherein $R^1$ is an unsubstituted 4-8 membered saturated carbocyclic or heterocyclic group comprising one nitrogen as the sole heteroatom within the ring atoms.

Embodiment 32. The compound of any one of embodiments 1-30, wherein the carbocyclic or heterocyclic group of $R^1$ is unsubstituted, or substituted with one halo, hydroxy or $C_1$-$C_4$ alkyl.

Embodiment 33. The compound of any one of embodiments 1-30, wherein the carbocyclic or heterocyclic group of $R^1$ is unsubstituted, or substituted with one halo or hydroxy.

Embodiment 34. The compound of any one of embodiments 1-30, wherein the carbocyclic or heterocyclic group of $R^1$ is unsubstituted, or substituted with one fluoro.

Embodiment 35. The compound of any one of embodiments 1-30, wherein the carbocyclic or heterocyclic group of $R^1$ is unsubstituted, or substituted with one fluoro or hydroxy.

Embodiment 36. The compound of any one of embodiments 1-30, wherein the carbocyclic or heterocyclic group of $R^1$ is substituted with one fluoro.

Embodiment 37. The compound of any one of embodiments 1-30, wherein the carbocyclic or heterocyclic group of $R^1$ is substituted with one $C_1$-$C_4$ alkyl.

Embodiment 38. The compound of any one of embodiments 1-37, wherein $R^1$ is selected from the group consisting of:

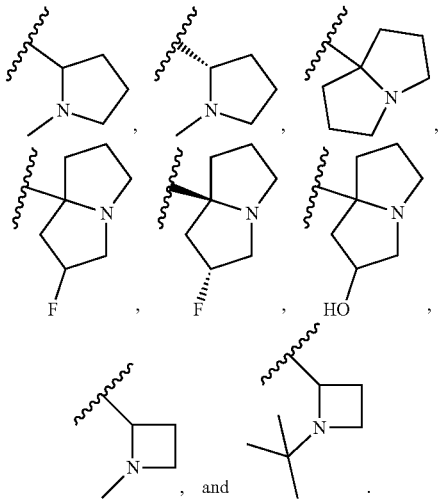

Embodiment 39. The compound of any one of embodiments 1-37, wherein $R^1$ is selected from the group consisting of:

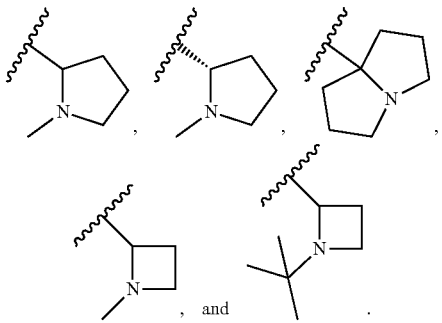

Embodiment 40. The compound of any one of embodiments 1-37, wherein $R^1$ is selected from the group consisting of:

[chemical structures]

Embodiment 41. The compound of any one of embodiments 1-37, wherein $R^1$ is selected from the group consisting of:

[chemical structures]

Embodiment 42. The compound of any one of embodiments 1-37, wherein $R^1$ is selected from the group consisting of:

[chemical structures]

Embodiment 43. The compound of any one of embodiments 1-41, wherein $R^3$ and $R^4$ are selected from the group consisting of: hydrogen, methyl, ethyl, ethynyl, fluoro, and chloro.

Embodiment 44. The compound of any one of embodiments 1-42, wherein $R^3$ and $R^4$ are selected from the group consisting of: hydrogen, fluoro, and chloro.

Embodiment 45. The compound of any one of embodiments 1-41, wherein $R^3$ is selected from the group consisting of: hydrogen and fluoro.

Embodiment 46. The compound of any one of embodiments 1-41, wherein $R^3$ is hydrogen.

Embodiment 47. The compound of any one of embodiments 1-41, wherein $R^3$ is fluoro.

Embodiment 48. The compound of any one of embodiments 1-47, wherein $R^4$ is selected from the group consisting of: hydrogen, methyl, ethyl, ethynyl, propynyl, difluoromethyl, CN, cyclopropyl, fluoro and chloro.

Embodiment 49. The compound of any one of embodiments 1-47, wherein $R^4$ is selected from the group consisting of: hydrogen, methyl, ethyl, ethynyl, fluoro and chloro.

Embodiment 50. The compound of any one of embodiments 1-47, wherein $R^4$ is selected from the group consisting of: hydrogen, fluoro and chloro.

Embodiment 51. The compound of any one of embodiments 1-47, wherein $R^4$ is propynyl.

Embodiment 52. The compound of any one of embodiments 1-47, wherein $R^4$ is CN.

Embodiment 53. The compound of any one of embodiments 1-47, wherein $R^4$ is cyclopropyl.

Embodiment 54. The compound of any one of embodiments 1-47, wherein $R^4$ is difluoromethyl.

Embodiment 55. The compound of any one of embodiments 1-47, wherein $R^4$ is chloro.

Embodiment 56. The compound of any one of embodiments 1-47, wherein $R^4$ is fluoro.

Embodiment 57. The compound of any one of embodiments 1-47, wherein $R^4$ is methyl.

Embodiment 58. The compound of any one of embodiments 1-47, wherein $R^4$ is ethyl.

Embodiment 59. The compound of any one of embodiments 1-47, wherein $R^4$ is ethynyl.

Embodiment 60. The compound of any one of embodiments 1-47, wherein $R^4$ is hydrogen.

Embodiment 61. The compound of any one of embodiments 1-60, wherein $R^2$ is selected from the group consisting of $R^{2a}$, $R^{2b}$, $R^{2c}$ and $R^{2e}$.

Embodiment 62. The compound of any one of embodiments 1-60, wherein $R^2$ is selected from the group consisting of $R^{2a}$, $R^{2b}$, and $R^{2c}$.

Embodiment 63. The compound of any one of embodiments 1-60, wherein $R^2$ is selected from the group consisting of $R^{2c}$ and $R^{2e}$.

Embodiment 64. The compound of any one of embodiments 1-60, wherein $R^2$ is selected from the group consisting of $R^{2a}$ and $R^{2b}$.

Embodiment 65. The compound of any one of embodiments 1-60, wherein $R^2$ is $R^{2a}$.

Embodiment 66. The compound of any one of embodiments 1-62, 64 and 65, wherein $R^5$ is methyl or ethyl.

Embodiment 67. The compound of any one of embodiments 1-62, 64 and 65, wherein $R^5$ is methyl.

Embodiment 68. The compound of any one of embodiments 1-62 and 64-67, wherein $R^6$ is —$C_1$-$C_6$ alkylene-S(O)$_2$—CH=CHR$^7$.

Embodiment 69. The compound of any one of embodiments 1-62 and 64-68, wherein the $C_1$-$C_6$ alkylene of $R^6$ is straight.

Embodiment 70. The compound of any one of embodiments 1-62 and 64-68, wherein the $C_1$-$C_6$ alkylene of $R^6$ is cyclic.

Embodiment 71. The compound of any one of embodiments 1-62 and 64-68, wherein the $C_1$-$C_6$ alkylene of $R^6$ is $C_1$-$C_4$ alkylene.

Embodiment 72. The compound of any one of embodiments 1-62 and 64-68, wherein the $C_1$-$C_6$ alkylene of $R^6$ is selected from the group consisting of: —(CH$_2$)$_2$—, —(CH$_2$)$_3$—, —(CH$_2$)$_4$—, and

[chemical structure]

Embodiment 73. The compound of any one of embodiments 1-62, 64 and 65, wherein $R^5$ and $R^6$ together with the nitrogen to which they are attached form a 4-7 membered saturated heterocyclic group comprising one ring and comprising one nitrogen as the sole heteroatom within the ring atoms, wherein the 4-7 membered saturated heterocyclic group is substituted with —(CH$_2$)$_n$—S(O)$_2$—CH=CHR$^7$.

Embodiment 74. The compound of embodiment 73, wherein R$^5$ and R$^6$ together with the nitrogen to which they are attached form a 4-7 membered saturated heterocyclic group selected from the group consisting of

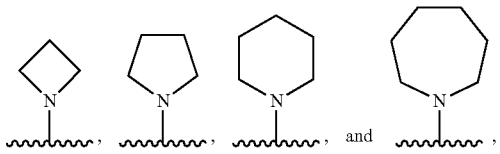

which is substituted with —(CH$_2$)$_n$—S(O)$_2$—CH=CHR$^7$.

Embodiment 75. The compound of any one of embodiments 1-62 and 64-74, wherein n is 0.

Embodiment 76. The compound of any one of embodiments 1-62 and 64-74, wherein n is 1.

Embodiment 77. The compound of any one of embodiments 1-62 and 64-76, wherein R$^7$ is hydrogen.

Embodiment 78. The compound of any one of embodiments 1-62 and 64-76, wherein R$^7$ is —C$_1$-C$_4$ alkyl.

Embodiment 79. The compound of any one of embodiments 1-62 and 64-76, wherein R$^7$ is —(CH$_2$)$_m$—NR$^8$R$^9$.

Embodiment 80. The compound of any one of embodiments 1-62 and 64-79, wherein R$^8$ and R$^9$ are independently —C$_1$-C$_2$ alkyl.

Embodiment 81. The compound of any one of embodiments 1-62 and 64-79, wherein R$^8$ and R$^9$ together with the nitrogen atom to which they are attached form a 4-7 membered saturated heterocyclic group comprising one nitrogen as the sole heteroatom within the ring atoms, and which is optionally substituted by halo.

Embodiment 82. The compound of any one of embodiments 1-62 and 64-79, wherein R$^8$ and R$^9$ together with the nitrogen atom to which they are attached form a 5-7 membered saturated heterocyclic group comprising two rings, wherein the ring atoms include one or two nitrogens as the sole heteroatoms within the ring atoms, and which is optionally substituted by halo.

Embodiment 83. The compound of embodiment 81 or 82, wherein the saturated heterocyclic group formed by R$^8$ and R$^9$ together with the nitrogen atom to which they are attached is substituted with —F.

Embodiment 84. The compound of any one of embodiments 1-62 and 64-76, wherein R$^7$ is selected from the group consisting of: hydrogen, methyl, ethyl, —CH$_2$N(CH$_3$)$_2$, —CH$_2$N(CH$_2$CH$_3$)$_2$, and

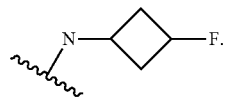 [SMILES: *NC1CC(F)C1]

Embodiment 85. The compound of any one of embodiments 1-60, wherein R$^2$ is R$^{2b}$.

Embodiment 86. The compound of any one of embodiments 1-62, 64 and 66-85, wherein R$^{10}$ is methyl or ethyl.

Embodiment 87. The compound of any one of embodiments 1-62 and 64-85, wherein R$^{10}$ is methyl.

Embodiment 88. The compound of any one of embodiments 1-62, 64 and 66-87, wherein R$^{11}$ is —(C$_1$-C$_4$ alkylene)-N(R$^{12}$)—CN.

Embodiment 89. The compound of any one of embodiments 1-62, 64 and 66-87, wherein R$^{11}$ is —(C$_1$-C$_2$ alkylene)-N(R$^{12}$)—CN.

Embodiment 90. The compound of any one of embodiments 1-62, 64 and 66-87, wherein R$^{11}$ is —(C$_3$-C$_4$ alkylene)-N(R$^{12}$)—CN wherein the C$_3$-C$_4$ alkylene is cyclic.

Embodiment 91. The compound of any one of embodiments 1-62, 64 and 66-90, wherein R$^{12}$ is hydrogen.

Embodiment 92. The compound of any one of embodiments 1-62, 64 and 66-90, wherein R$^{12}$ is methyl.

Embodiment 93. The compound of any one of embodiments 1-63 and 66-87, wherein R$^{11}$ is selected from the group consisting of:

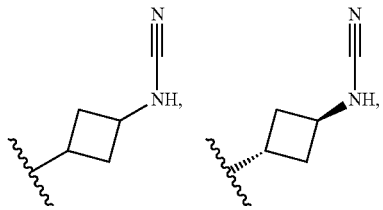 [SMILES: *C1CC(NC#N)C1 ; *[C@H]1C[C@H](NC#N)C1]

and —CH$_2$CH$_2$N(CH$_3$)CN.

Embodiment 94. The compound of any one of embodiments 1-62, 64 and 66-87, wherein R$^{11}$ is —(CH$_2$)$_w$—R$^{13}$.

Embodiment 95. The compound of embodiment 94, wherein w is 0 or 1.

Embodiment 96. The compound of any one of embodiments 1-62, 64, 66-87, 94 and 95, wherein R$^{13}$ is a 4-7 membered saturated heterocyclic group comprising one nitrogen as the sole heteroatom within the ring atoms, wherein the nitrogen is substituted with cyano, and wherein the heterocyclic group is optionally further substituted with 1 substituent selected from the group consisting of hydroxy, CN, C$_1$-C$_4$ cyanoalkyl, C$_1$-C$_4$ alkyl, C$_1$-C$_4$ alkoxy, or halo.

Embodiment 97. The compound of any one of embodiments 1-62, 64, 66-87, 94 and 95, wherein R$^{13}$ is a 4-7 membered saturated heterocyclic group comprising one nitrogen as the sole heteroatom within the ring atoms, wherein the nitrogen is substituted with cyano, and wherein the heterocyclic group is optionally further substituted with C$_1$-C$_4$ alkyl, C$_1$-C$_4$ alkoxy, or halo.

Embodiment 98. The compound of any one of embodiments 1-62, 64, 66-87 and 94-97, wherein the heterocyclic group of R$^{13}$ is not further substituted with hydroxy, CN, C$_1$-C$_4$ cyanoalkyl, C$_1$-C$_4$ alkyl, C$_1$-C$_4$ alkoxy, C$_1$-C$_4$ haloalkyl, C$_1$-C$_4$ haloalkoxy, or halo.

Embodiment 99. The compound of any one of embodiments 1-62, 64, 66-87 and 94-97, wherein the heterocyclic group of R$^{13}$ is not further substituted with C$_1$-C$_4$ alkyl, C$_1$-C$_4$ alkoxy, C$_1$-C$_4$ haloalkyl, C$_1$-C$_4$ haloalkoxy, or halo.

Embodiment 100. The compound of any one of embodiments 1-62, 64, 66-87 and 94-97, wherein the heterocyclic group of R$^{13}$ is further substituted with 1 substituent selected from the group consisting of hydroxy, CN, C$_1$-C$_4$ cyanoalkyl, C$_1$-C$_4$ alkyl, C$_1$-C$_4$ alkoxy, or halo.

Embodiment 101. The compound of any one of embodiments 1-62, 64, 66-87 and 94-97, wherein the heterocyclic group of R$^{13}$ is further substituted with 1 substituent selected from the group consisting of C$_1$-C$_4$ alkyl, C$_1$-C$_4$ alkoxy, or halo.

Embodiment 102. The compound of any one of embodiments 1-62, 64, 66-87 and 94-97, wherein the heterocyclic group of $R^{13}$ is further substituted with 1 substituent selected from the group consisting of methyl, methoxy, or fluoro.

Embodiment 103. The compound of any one of embodiments 1-62, 64 and 66-87, wherein $R^{11}$ is selected from the group consisting of:

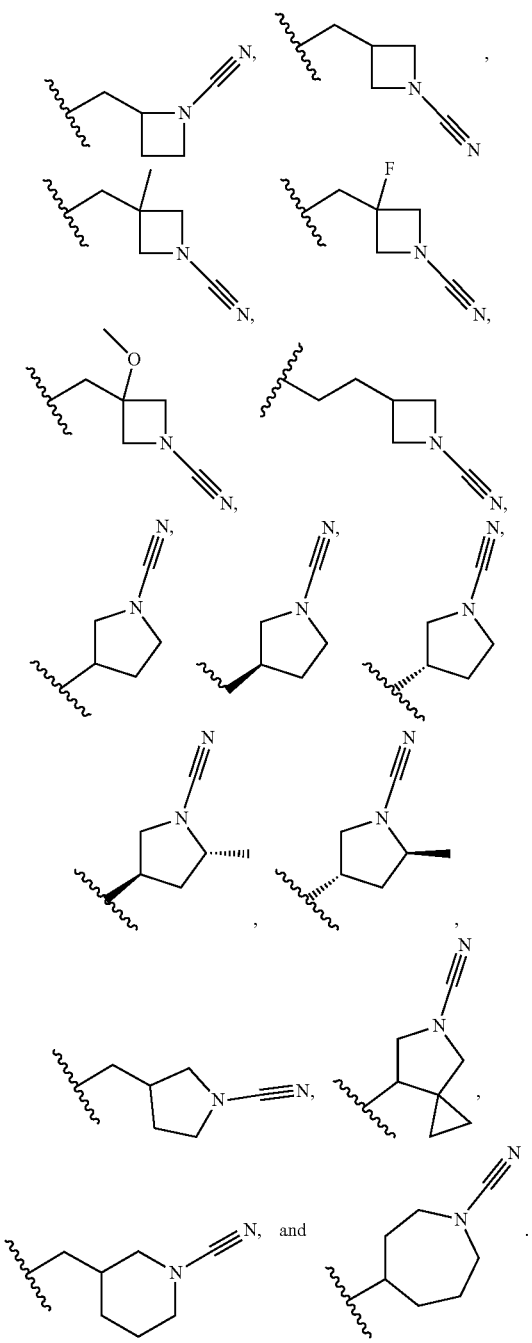

Embodiment 104. The compound of any one of embodiments 1-62, 64 and 66-85, wherein $R^{10}$ and $R^{11}$ together with the nitrogen to which they are attached form a 4-8 membered saturated heterocyclic group optionally comprising a second nitrogen as the sole additional heteroatom within the ring atoms, wherein the 4-8 membered saturated heterocyclic group is substituted with one substituent selected from the group consisting of:

—$(CH_2)_x$—$N(R^{14})$—CN;

a 4-6 membered saturated heterocyclic group comprising one ring and comprising one nitrogen as the sole heteroatom within the ring atoms, wherein the nitrogen is substituted with cyano; and cyano, with the proviso that when cyano is the substituent, then the 4-8 membered saturated heterocyclic group formed by $R^{10}$ and $R^{11}$ together with the nitrogen to which they are attached comprises the second nitrogen ring atom and the cyano is connected to the 4-8 membered saturated heterocyclic group at the second ring nitrogen.

Embodiment 105. The compound of any one of embodiments 1-62, 64, 66-85 and 104, wherein the 4-8 membered saturated heterocyclic group formed by $R^{10}$ and $R^{11}$ together with the nitrogen to which they are attached is a 4-7 membered saturated heterocyclic group.

Embodiment 106. The compound of any one of embodiments 1-62, 64, 66-85 and 104, wherein the 4-8 membered saturated heterocyclic group formed by $R^{10}$ and $R^{11}$ together with the nitrogen to which they are attached comprises a single nitrogen within the ring atoms.

Embodiment 107. The compound of any one of embodiments 1-62, 64, 66-85 and 104, wherein the 4-8 membered saturated heterocyclic group formed by $R^{10}$ and $R^{11}$ together with the nitrogen to which they are attached comprises two nitrogens within the ring atoms.

Embodiment 108. The compound of any one of embodiments 1-62, 64, 66-85 and 104, wherein the 4-8 membered saturated heterocyclic group formed by $R^{10}$ and $R^{11}$ together with the nitrogen to which they are attached is selected from the group consisting of:

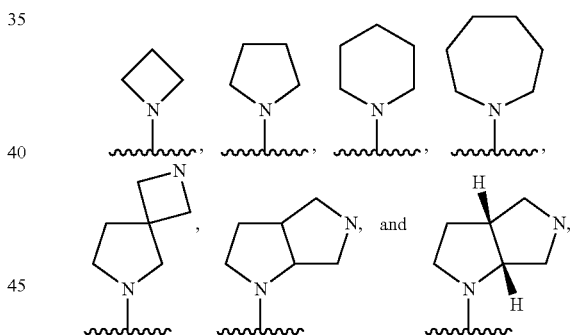

which is substituted with one substituent selected from the group consisting of:

—$(CH_2)_x$—$N(R^{14})$—CN;

a 4-6 membered saturated heterocyclic group comprising one ring and comprising one nitrogen as the sole heteroatom within the ring atoms, wherein the nitrogen is substituted with cyano; and cyano, with the proviso that when cyano is the substituent, then the 4-8 membered saturated heterocyclic group formed by $R^{10}$ and $R^{11}$ together with the nitrogen to which they are attached comprises the second nitrogen ring atom and the cyano is connected to the 4-8 membered saturated heterocyclic group at the second ring nitrogen.

Embodiment 109. The compound of any one of embodiments 1-62, 64, 66-85 and 104-108, wherein the 4-8 membered saturated heterocyclic group formed by $R^{10}$ and $R^{11}$ together with the nitrogen to which they are attached is substituted with —$(CH_2)_x$—$N(R^{14})$—CN.

Embodiment 110. The compound of embodiment 109, wherein $R^{14}$ is hydrogen or methyl.

Embodiment 111. The compound of embodiment 109, wherein the —$(CH_2)_x$—$N(R^{14})$—CN group is selected from the group consisting of: —$CH_2NHCN$, —$CH_2N(CH_3)CN$, —NHCN, and —$N(CH_3)CN$.

Embodiment 112. The compound of any one of embodiments 1-62, 64, 66-85 and 104-108, wherein the 4-8 membered saturated heterocyclic group formed by $R^{10}$ and $R^{11}$ together with the nitrogen to which they are attached is substituted with a 4-6 membered saturated heterocyclic group comprising one ring and comprising one nitrogen as the sole heteroatom within the ring atoms, wherein the nitrogen is substituted with cyano.

Embodiment 113. The compound of any one of embodiments 1-62, 64, 66-85 and 104-108, wherein the 4-8 membered saturated heterocyclic group formed by $R^{10}$ and $R^{11}$ together with the nitrogen to which they are attached is substituted with

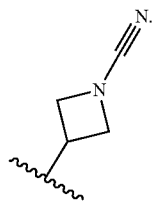 [SMILES: *C1CN(C#N)C1]

Embodiment 114. The compound of any one of embodiments 1-62, 64, 66-85, 104, 105, 107 and 108, wherein the 4-8 membered saturated heterocyclic group formed by $R^{10}$ and $R^{11}$ together with the nitrogen to which they are attached is substituted with cyano.

Embodiment 115. The compound of any one of embodiments 1-60, wherein $R^2$ is $R^{2c}$.

Embodiment 116. The compound of any one of embodiments 1-63, 66-84 and 86-115, wherein $R^{2c}$ is —$NR^{15}R^{16}$, wherein:
- $R^{15}$ is H, $C_1$-$C_4$ alkyl optionally substituted with one instance of CN, $C_1$-$C_4$ alkoxy, $C_1$-$C_4$ haloalkyl, or $C_1$-$C_4$ haloalkoxy; and
- $R^{16}$ is selected from the group consisting of: —$(C_1$-$C_4$ alkylene)-$N(R^{17})C(O)C(R^{19})$=$C(R^{20})R^{18}$, and —$(CH_2)_y$—$R^{21}$.

Embodiment 117. The compound of any one of embodiments 1-63, 66-84 and 86-115, wherein $R^{2c}$ is —$NR^{15}R^{16}$, wherein:
- $R^{15}$ is H, $C_1$-$C_4$ alkyl, $C_1$-$C_4$ alkoxy, $C_1$-$C_4$ haloalkyl, or $C_1$-$C_4$ haloalkoxy; and
- $R^{16}$ is selected from the group consisting of: —$(C_1$-$C_4$ alkylene)-$N(R^{17})C(O)C(R^{19})$=$C(R^{20})R^{18}$, and —$(CH_2)_y$—$R^{21}$.

Embodiment 118. The compound of any one of embodiments 1-63, 66-84 and 86-117, wherein $R^{15}$ is selected from the group consisting of $C_1$-$C_4$ alkyl, $C_1$-$C_4$ haloalkyl and $C_1$-$C_4$ alkoxy.

Embodiment 119. The compound of any one of embodiments 1-63, 66-84 and 86-117, wherein $R^{15}$ is selected from the group consisting of $C_1$-$C_4$ alkyl and $C_1$-$C_4$ alkoxy.

Embodiment 120. The compound of any one of embodiments 1-63, 66-84 and 86-117, wherein $R^{15}$ is selected from the group consisting of H, methyl, ethyl, —$CH_2$-cyclopropyl, —$CH_2CH_2CN$, —$CH_2CHF_2$ and —$CH_2CH_2OCH_3$.

Embodiment 121. The compound of any one of embodiments 1-63, 66-84 and 86-117, wherein $R^{15}$ is selected from the group consisting of methyl, ethyl, —$CH_2CHF_2$ and —$CH_2CH_2OCH_3$.

Embodiment 122. The compound of any one of embodiments 1-63, 66-84 and 86-117, wherein $R^{15}$ is selected from the group consisting of methyl, ethyl and —$CH_2CH_2OCH_3$.

Embodiment 123. The compound of any one of embodiments 1-63, 66-84 and 86-117, wherein $R^{15}$ is methyl or ethyl.

Embodiment 124. The compound of any one of embodiments 1-63, 66-84 and 86-117, wherein $R^{15}$ is methyl.

Embodiment 125. The compound of any one of embodiments 1-63, 66-84 and 86-124, wherein $R^{16}$ is —$(C_1$-$C_4$ alkylene)-$N(R^{17})C(O)C(R^{19})$=$C(R^{20})R^{18}$.

Embodiment 126. The compound of any one of embodiments 1-63, 66-84 and 86-125, wherein the $C_1$-$C_4$ alkylene of $R^{16}$ is straight.

Embodiment 127. The compound of any one of embodiments 1-63, 66-84 and 86-125, wherein the $C_1$-$C_4$ alkylene of $R^{16}$ is branched.

Embodiment 128. The compound of any one of embodiments 1-63, 66-84 and 86-125, wherein the $C_1$-$C_4$ alkylene of $R^{16}$ is cyclic.

Embodiment 129. The compound of any one of embodiments 1-63, 66-84 and 86-125, wherein the $C_1$-$C_4$ alkylene of $R^{16}$ is selected from the group consisting of —$CH_2CH_2$—, —$CH_2CH_2CH_2$—, —$CH_2CH(CH_3)$—, —$CH(CH_3)CH_2$—,

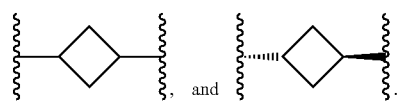

Embodiment 130. The compound of any one of embodiments 1-63, 66-84 and 86-125, wherein the $C_1$-$C_4$ alkylene of $R^{16}$ is —$CH_2CH_2$—.

Embodiment 131. The compound of any one of embodiments 1-63, 66-84 and 86-130, wherein $R^{17}$ is selected from the group consisting of hydrogen and methyl.

Embodiment 132. The compound of any one of embodiments 1-63, 66-84 and 86-131, wherein $R^{17}$ is hydrogen.

Embodiment 133. The compound of any one of embodiments 1-63, 66-84 and 86-124, wherein $R^{16}$ is —$(CH_2)_y$—$R^{21}$.

Embodiment 134. The compound of any one of embodiments 1-63, 66-84, 86-124 and 133, wherein y is 0 or 1.

Embodiment 135. The compound of any one of embodiments 1-63, 66-84, 86-124 and 133, wherein y is 0.

Embodiment 136. The compound of any one of embodiments 1-63, 66-84, 86-124 and 133, wherein y is 1.

Embodiment 137. The compound of any one of embodiments 1-63, 66-84, 86-124 and 133-136 wherein the 4-7 membered saturated heterocyclic group of $R^{21}$ comprises one ring.

Embodiment 138. The compound of any one of embodiments 1-63, 66-84, 86-124 and 133-136 wherein the 4-7 membered saturated heterocyclic group of $R^{21}$ comprises 4-6 ring atoms.

Embodiment 139. The compound of any one of embodiments 1-63, 66-84, 86-124 and 133-136 wherein $R^{21}$ is selected from:
a 4-5 membered saturated monocyclic heterocyclic group comprising one nitrogen as the sole heteroatom within the ring atoms, wherein the nitrogen ring atom is substituted with —C(O)C(R$^{19}$)=C(R$^{20}$)R$^{18}$ and wherein the heterocyclic group is not further substituted or is further substituted with 1 substituent selected from the group consisting of hydroxy, CN, C$_1$-C$_4$ alkyl, C$_1$—C$_4$ alkoxy, C$_1$-C$_4$ haloalkyl, C$_1$-C$_4$ cyanoalkyl, C$_1$-C$_4$ haloalkoxy, and halo, or is further substituted with two halo substituents;

a 6 membered saturated monocyclic heterocyclic group comprising one or two nitrogens as the sole heteroatom(s) within the ring atoms, wherein one of the nitrogens is substituted with —C(O)C(R$^{19}$)=C(R$^{20}$)R$^{18}$, and wherein the heterocyclic group is not further substituted or is further substituted with 1 substituent selected from the group consisting of hydroxy, CN, C$_1$-C$_4$ alkyl, C$_1$-C$_4$ alkoxy, C$_1$-C$_4$ haloalkyl, C$_1$-C$_4$ cyanoalkyl, C$_1$-C$_4$ haloalkoxy, or halo, or is further substituted with two halo substituents, provided that the optional hydroxy, CN, cyanoalkyl and halo substituents are not attached to a heteroatom; and a 7 membered saturated monocyclic heterocyclic group comprising one nitrogen, and optionally one additional heteroatom selected from nitrogen, oxygen, and sulfur, as the sole heteroatom(s) within the ring atoms, wherein one of the nitrogen ring atom(s) is substituted with —C(O)C(R$^{19}$)=C(R$^{20}$)R$^{18}$, and wherein the heterocyclic group is not further substituted or is further substituted with 1 substituent selected from the group consisting of hydroxy, CN, C$_1$-C$_4$ alkyl, C$_1$-C$_4$ alkoxy, C$_1$-C$_4$ haloalkyl, C$_1$-C$_4$ cyanoalkyl, C$_1$-C$_4$ haloalkoxy, or halo, or is further substituted with two halo substituents, provided that the optional hydroxy, CN, cyanoalkyl and halo substituents are not attached to a heteroatom.

Embodiment 140. The compound of any one of embodiments 1-63, 66-84, 86-124 and 133-136 wherein R$^{21}$ is selected from:

a 4-5 membered saturated monocyclic heterocyclic group comprising one nitrogen as the sole heteroatom within the ring atoms, wherein the nitrogen ring atom is substituted with —C(O)C(R$^{19}$)=C(R$^{20}$)R$^{18}$ and wherein the heterocyclic group is not further substituted or is further substituted with 1 substituent selected from the group consisting of hydroxy, CN, C$_1$-C$_4$ alkyl, C$_1$-C$_4$ alkoxy, C$_1$-C$_4$ haloalkyl, C$_1$-C$_4$ cyanoalkyl, C$_1$-C$_4$ haloalkoxy, and halo;

a 6 membered saturated monocyclic heterocyclic group comprising one or two nitrogens as the sole heteroatom(s) within the ring atoms, wherein one of the nitrogens is substituted with —C(O)C(R$^{19}$)=C(R$^{20}$)R$^{18}$, and wherein the heterocyclic group is not further substituted or is further substituted with 1 substituent selected from the group consisting of hydroxy, CN, C$_1$-C$_4$ alkyl, C$_1$-C$_4$ alkoxy, C$_1$-C$_4$ haloalkyl, C$_1$-C$_4$ cyanoalkyl, C$_1$-C$_4$ haloalkoxy, or halo provided that the optional hydroxy, CN, cyanoalkyl and halo substituents are not attached to a heteroatom; and a 7 membered saturated monocyclic heterocyclic group comprising one nitrogen, and optionally one additional heteroatom selected from nitrogen, oxygen, and sulfur, as the sole heteroatom(s) within the ring atoms, wherein one of the nitrogen ring atom(s) is substituted with —C(O)C(R$^{19}$)=C(R$^{20}$)R$^{18}$, and wherein the heterocyclic group is not further substituted or is further substituted with 1 substituent selected from the group consisting of hydroxy, CN, C$_1$-C$_4$ alkyl, C$_1$-C$_4$ alkoxy, C$_1$-C$_4$ haloalkyl, C$_1$-C$_4$ cyanoalkyl, C$_1$-C$_4$ haloalkoxy, or halo provided that the optional hydroxy, CN, cyanoalkyl and halo substituents are not attached to a heteroatom.

Embodiment 141. The compound of any one of embodiments 1-63, 66-84, 86-124 and 133-136, wherein R$^{21}$ is selected from:

a 4-5 membered monocyclic saturated heterocyclic group comprising one nitrogen as the sole heteroatom within the ring atoms, wherein the nitrogen ring atom of the heterocyclic group is substituted with —C(O)C(R$^{19}$)=C(R$^{20}$)R$^{18}$ and wherein the heterocyclic group is not further substituted or is further substituted with 1 substituent selected from the group consisting of hydroxy, CN, C$_1$-C$_4$ alkyl, C$_1$-C$_4$ alkoxy, C$_1$-C$_4$ haloalkyl, C$_1$-C$_4$ cyanoalkyl, C$_1$-C$_4$ haloalkoxy, and halo, or is further substituted with two halo substituents;

a 6 membered monocyclic saturated heterocyclic group comprising one or two nitrogens as the sole heteroatom(s) within the ring atoms, wherein one of the nitrogens of the heterocyclic group is substituted with —C(O)C(R$^{19}$)=C(R$^{20}$)R$^{18}$, and wherein the heterocyclic group is not further substituted or is further substituted with 1 substituent selected from the group consisting of hydroxy, CN, C$_1$-C$_4$ alkyl, C$_1$-C$_4$ alkoxy, C$_1$-C$_4$ haloalkyl, C$_1$-C$_4$ cyanoalkyl, C$_1$-C$_4$ haloalkoxy, or halo, or is further substituted with two halo substituents, provided that the optional hydroxy, CN, cyanoalkyl and halo substituents are not attached to a heteroatom;

a 7 membered saturated bicyclic spirocyclic heterocyclic group comprising one nitrogen as the sole heteroatom within the ring atoms, wherein the nitrogen ring atom is substituted with —C(O)C(R$^{19}$)=C(R$^{20}$)R$^{18}$, and wherein the heterocyclic group is not further substituted or is further substituted with 1 substituent selected from the group consisting of hydroxy, CN, C$_1$-C$_4$ alkyl, C$_1$-C$_4$ alkoxy, C$_1$-C$_4$ haloalkyl, C$_1$-C$_4$ cyanoalkyl, C$_1$-C$_4$ haloalkoxy, or halo, or is further substituted with two halo substituents, provided that the optional hydroxy, CN, cyanoalkyl and halo substituents are not attached to a heteroatom.

Embodiment 142. The compound of any one of embodiments 1-63, 66-84, 86-124 and 133-136, wherein R$^{21}$ is selected from:

a 4-5 membered monocyclic saturated heterocyclic group comprising one nitrogen as the sole heteroatom within the ring atoms, wherein the nitrogen ring atom of the heterocyclic group is substituted with —C(O)C(R$^{19}$)=C(R$^{20}$)R$^{18}$ and wherein the heterocyclic group is not further substituted or is further substituted with 1 substituent selected from the group consisting of hydroxy, CN, C$_1$-C$_4$ alkyl, C$_1$-C$_4$ alkoxy, C$_1$-C$_4$ haloalkyl, C$_1$-C$_4$ cyanoalkyl, C$_1$-C$_4$ haloalkoxy, and halo;

a 6 membered monocyclic saturated heterocyclic group comprising one or two nitrogens as the sole heteroatom(s) within the ring atoms, wherein one of the nitrogens of the heterocyclic group is substituted with —C(O)C(R$^{19}$)=C(R$^{20}$)R$^{18}$, and wherein the heterocyclic group is not further substituted or is further substituted with 1 substituent selected from the group consisting of hydroxy, CN, C$_1$-C$_4$ alkyl, C$_1$-C$_4$ alkoxy, C$_1$-C$_4$ haloalkyl, C$_1$-C$_4$ cyanoalkyl, C$_1$-C$_4$ haloalkoxy, or halo provided that the optional hydroxy, CN, cyanoalkyl and halo substituents are not attached to a heteroatom;

a 7 membered saturated bicyclic spirocyclic heterocyclic group comprising one nitrogen as the sole heteroatom within the ring atoms, wherein the nitrogen ring atom is substituted with —C(O)C(R$^{19}$)=C(R$^{20}$)R$^{18}$, and wherein the heterocyclic group is not further substituted or is further substituted with 1 substituent selected from the group consisting of hydroxy, CN, C$_1$-C$_4$ alkyl, C$_1$-C$_4$ alkoxy, C$_1$-C$_4$ haloalkyl, C$_1$-C$_4$ cyanoalkyl, C$_1$-C$_4$ haloalkoxy, or halo provided that the optional hydroxy, CN, cyanoalkyl and halo substituents are not attached to a heteroatom.

Embodiment 143. The compound of any one of embodiments 1-63, 66-84, 86-124 and 133-136, wherein R$^{21}$ is a 4-5 membered monocyclic saturated heterocyclic group comprising one nitrogen as the sole heteroatom within the ring atoms, wherein the nitrogen ring atom of the heterocyclic group is substituted with —C(O)C(R$^{19}$)=C(R$^{20}$)R$^{18}$ and wherein the heterocyclic group is not further substituted or is further substituted with 1 substituent selected from the group consisting of hydroxy, CN, C$_1$-C$_4$ alkyl, C$_1$-C$_4$ alkoxy, C$_1$-C$_4$ haloalkyl, C$_1$-C$_4$ cyanoalkyl, C$_1$-C$_4$ haloalkoxy, and halo, or is further substituted with two halo substituents.

Embodiment 144. The compound of any one of embodiments 1-63, 66-84, 86-124 and 133-136, wherein R$^{21}$ is a 4-5 membered monocyclic saturated heterocyclic group comprising one nitrogen as the sole heteroatom within the ring atoms, wherein the nitrogen ring atom of the heterocyclic group is substituted with —C(O)C(R$^{19}$)=C(R$^{20}$)R$^{18}$ and wherein the heterocyclic group is not further substituted or is further substituted with 1 substituent selected from the group consisting of hydroxy, CN, C$_1$-C$_4$ alkyl, C$_1$-C$_4$ alkoxy, C$_1$-C$_4$ haloalkyl, C$_1$-C$_4$ cyanoalkyl, C$_1$-C$_4$ haloalkoxy, and halo.

Embodiment 145. The compound of any one of embodiments 1-63, 66-84, 86-124 and 133-144 wherein the heterocyclic group of R$^{21}$ is not further substituted.

Embodiment 146. The compound of any one of embodiments 1-63, 66-84, 86-124 and 133-144 wherein the heterocyclic group of R$^{21}$ is further substituted with 1 substituent selected from the group consisting of hydroxy, CN, C$_1$-C$_4$ alkyl, C$_1$-C$_4$ alkoxy, C$_1$-C$_4$ haloalkyl, C$_1$-C$_4$ cyanoalkyl, C$_1$-C$_4$ haloalkoxy, and halo, or is further substituted with two halo substituents.

Embodiment 147. The compound of any one of embodiments 1-63, 66-84, 86-124 and 133-144 wherein the heterocyclic group of R$^{21}$ is further substituted with 1 substituent selected from the group consisting of hydroxy, CN, C$_1$-C$_4$ alkyl, C$_1$-C$_4$ alkoxy, C$_1$-C$_4$ haloalkyl, C$_1$-C$_4$ cyanoalkyl, C$_1$-C$_4$ haloalkoxy, and halo.

Embodiment 148. The compound of any one of embodiments 1-63, 66-84, 86-124 and 133-144 wherein the heterocyclic group of R$^{21}$ is further substituted with 1 substituent selected from the group consisting of C$_1$-C$_4$ alkyl, C$_1$-C$_4$ alkoxy, C$_1$-C$_4$ haloalkyl, C$_1$-C$_4$ haloalkoxy, and halo.

Embodiment 149. The compound of any one of embodiments 1-63, 66-84, 86-124 and 133-144 wherein the heterocyclic group of R$^{21}$ is further substituted with 1 substituent selected from the group consisting of hydroxy, CN, C$_1$-C$_4$ alkyl, C$_1$-C$_4$ cyanoalkyl, and halo.

Embodiment 150. The compound of any one of embodiments 1-63, 66-84, 86-124 and 133-144 wherein the heterocyclic group of R$^{21}$ is further substituted with 1 substituent selected from the group consisting of hydroxy, CN, Me, —CH$_2$CN and F.

Embodiment 151. The compound of any one of embodiments 1-63, 66-84, 86-124 and 133-144 wherein the heterocyclic group of R$^{21}$ is further substituted with two halo substituents.

Embodiment 152. The compound of any one of embodiments 1-63, 66-84, 86-124 and 133-144 wherein the heterocyclic group of R$^{21}$ is further substituted with 1 substituent selected from the group consisting of Me and F.

Embodiment 153. The compound of any one of embodiments 1-63, 66-84, 86-124 and 133-136, wherein the heterocyclic group of R$^{21}$ is selected from the group consisting of:

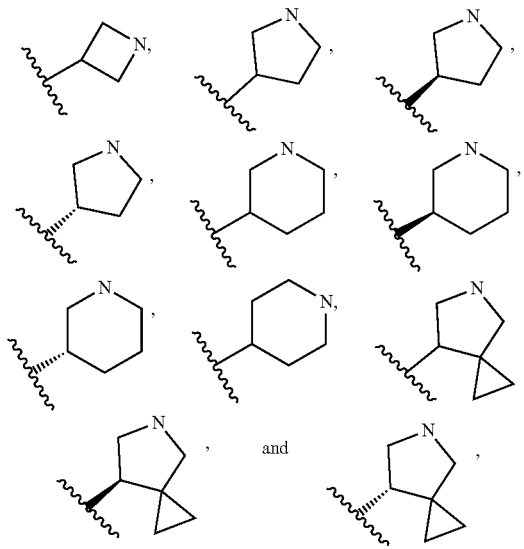

wherein the ring nitrogen of the heterocyclic group is substituted with —C(O)C(R$^{19}$)=C(R$^{20}$)R$^{18}$ and the heterocyclic group is not further substituted, or is substituted with one substituent selected from hydroxy, CN, C$_1$-C$_4$ alkyl, C$_1$-C$_4$ alkoxy, C$_1$-C$_4$ haloalkyl, C$_1$-C$_4$ cyanoalkyl, C$_1$-C$_4$ haloalkoxy, and halo, or is substituted with two halo.

Embodiment 154. The compound of any one of embodiments 1-63, 66-84, 86-124 and 133136, wherein the heterocyclic group of R$^{21}$ is selected from the group consisting of:

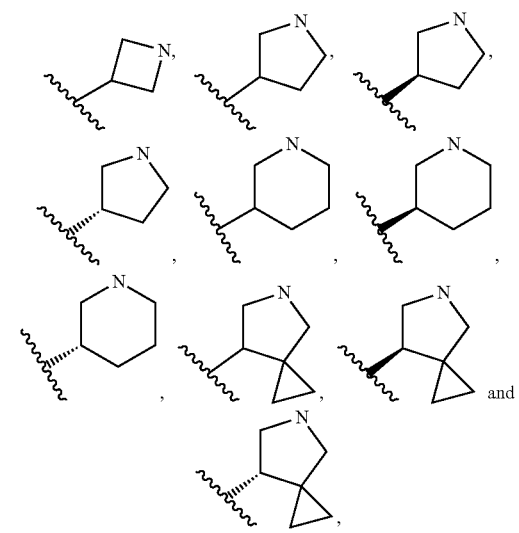

wherein the ring nitrogen of the heterocyclic group is substituted with —C(O)C(R$^{19}$)=C(R$^{20}$)R$^8$ and the heterocyclic group is not further substituted, or is substituted with one substituent selected from hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, and halo.

Embodiment 155. The compound of any one of embodiments 1-63, 66-84, 86-124 and 133-136, wherein the heterocyclic group of $R^{21}$ is selected from the group consisting of:

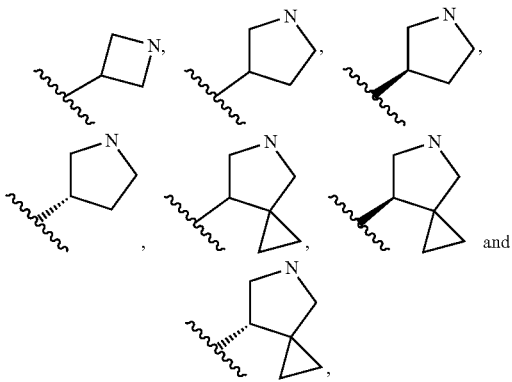

and wherein the ring nitrogen of the heterocyclic group is substituted with —C(O)C($R^{19}$)=C($R^{20}$)$R^{18}$ and the heterocyclic group is not further substituted, or is substituted with one substituent selected from hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, and halo.

Embodiment 156. The compound of any one of embodiments 1-63, 66-84, 86-124 and 133-136, wherein the heterocyclic group of $R^{21}$ is selected from the group consisting of:

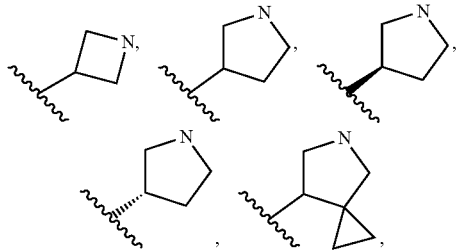

herein the ring nitrogen of the heterocyclic group is substituted with —C(O)C($R^{19}$)=C($R^{20}$)$R^{18}$ and the heterocyclic group is not further substituted, or is substituted with one substituent selected from hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, and halo.

Embodiment 157. The compound of any one of embodiments 153-156, wherein the heterocyclic group of $R^{21}$ is not further substituted.

Embodiment 158. The compound of any one of embodiments 153-156, wherein the heterocyclic group of $R^{21}$ is further substituted with 1 substituent selected from the group consisting of hydroxy, CN, $C_1$-$C_4$ alkyl, $C_1$-$C_4$ cyanoalkyl, and halo. or is further substituted with two halo.

Embodiment 159. The compound of any one of embodiments 153-156, wherein the heterocyclic group of $R^{21}$ is further substituted with 1 substituent selected from the group consisting of hydroxy, CN, $C_1$-$C_4$ alkyl, $C_1$-$C_4$ cyanoalkyl, and halo.

Embodiment 160. The compound of any one of embodiments 153-156, wherein the heterocyclic group of $R^{21}$ is further substituted with 1 substituent selected from the group consisting of $C_1$-$C_4$ alkyl or halo.

Embodiment 161. The compound of any one of embodiments 153-156, wherein the heterocyclic group of $R^{21}$ is further substituted with 1 substituent selected from the group consisting of hydroxy, CN, Me, —$CH_2CN$ and F.

Embodiment 162. The compound of any one of embodiments 153-156, wherein the heterocyclic group of $R^{21}$ is further substituted with 1 substituent selected from the group consisting of Me and F, or is further substituted with two fluoro.

Embodiment 163. The compound of any one of embodiments 153-156, wherein the heterocyclic group of $R^{21}$ is further substituted with 1 substituent selected from the group consisting of Me and F.

Embodiment 164. The compound of embodiment 153, wherein the heterocyclic group of $R^{21}$ is selected from the group consisting of:

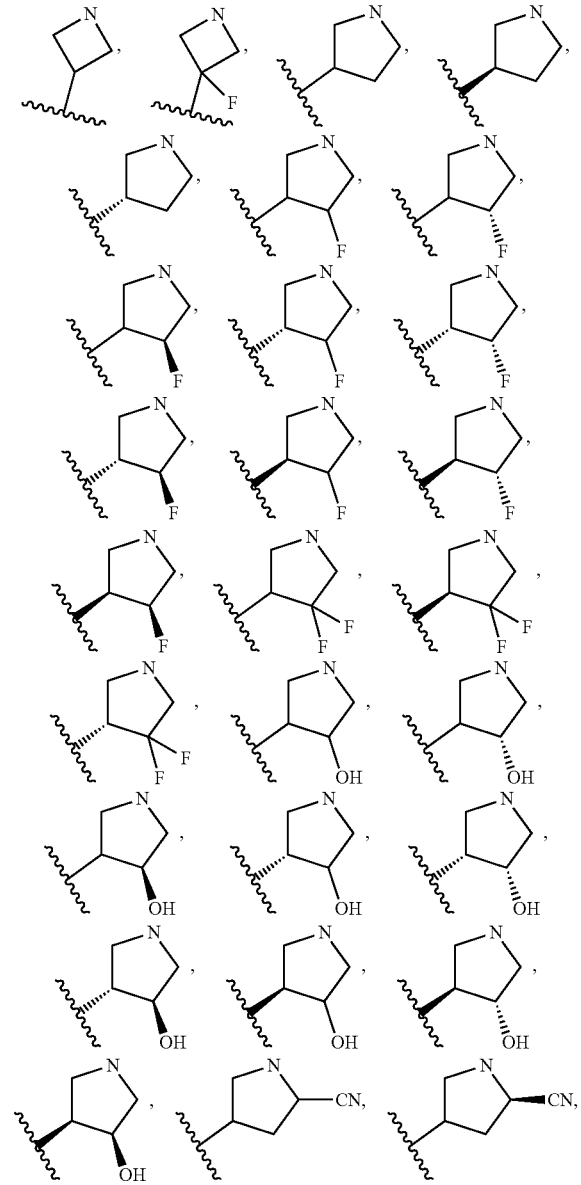

-continued
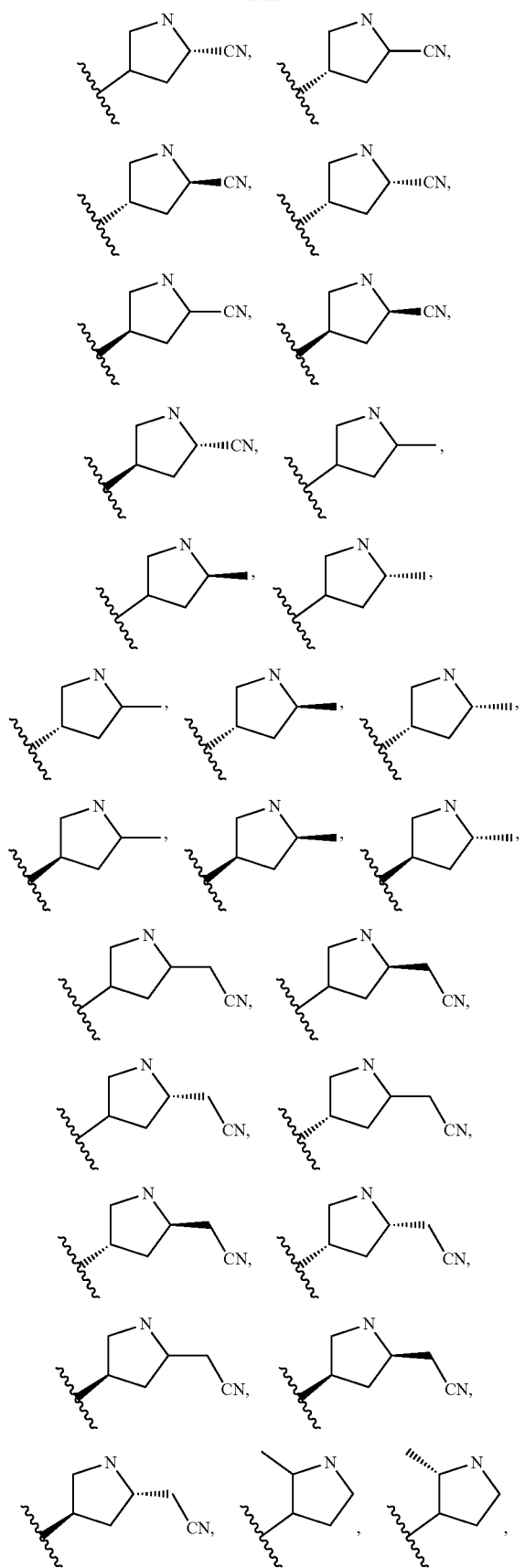
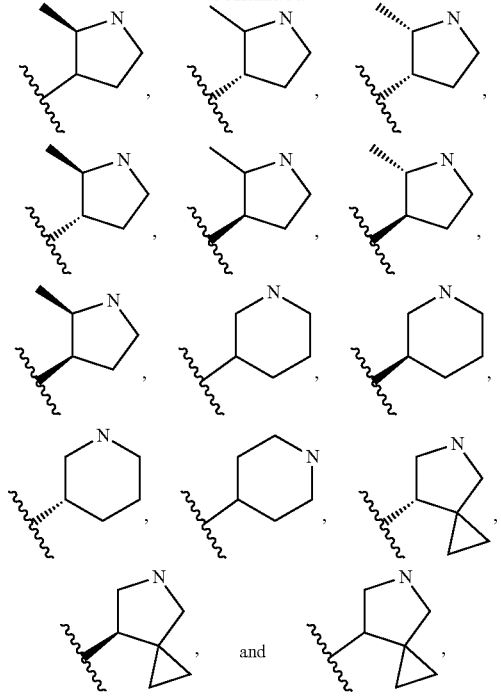
wherein the ring nitrogen of the heterocyclic group is substituted with —C(O)C(R$^{19}$)=C(R$^{20}$)R$^{18}$.
Embodiment 165. The compound of embodiment 153 or 154, wherein the heterocyclic group of R$^{21}$ is selected from the group consisting of:
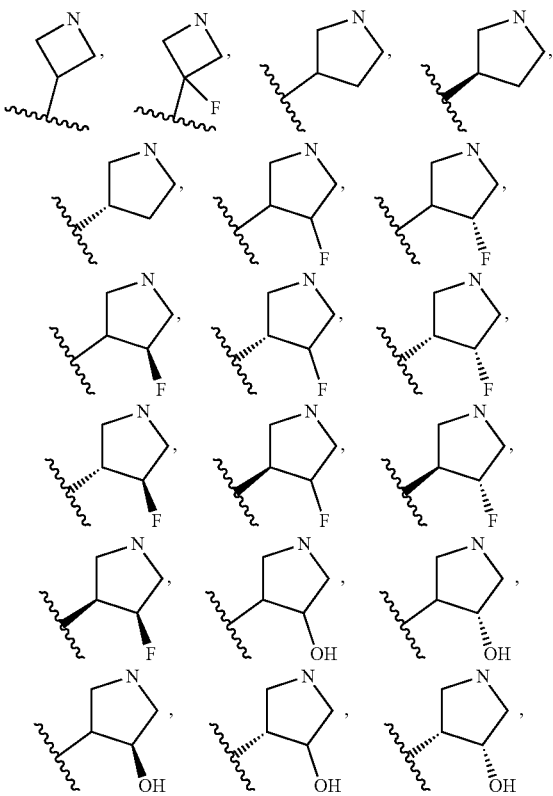

-continued
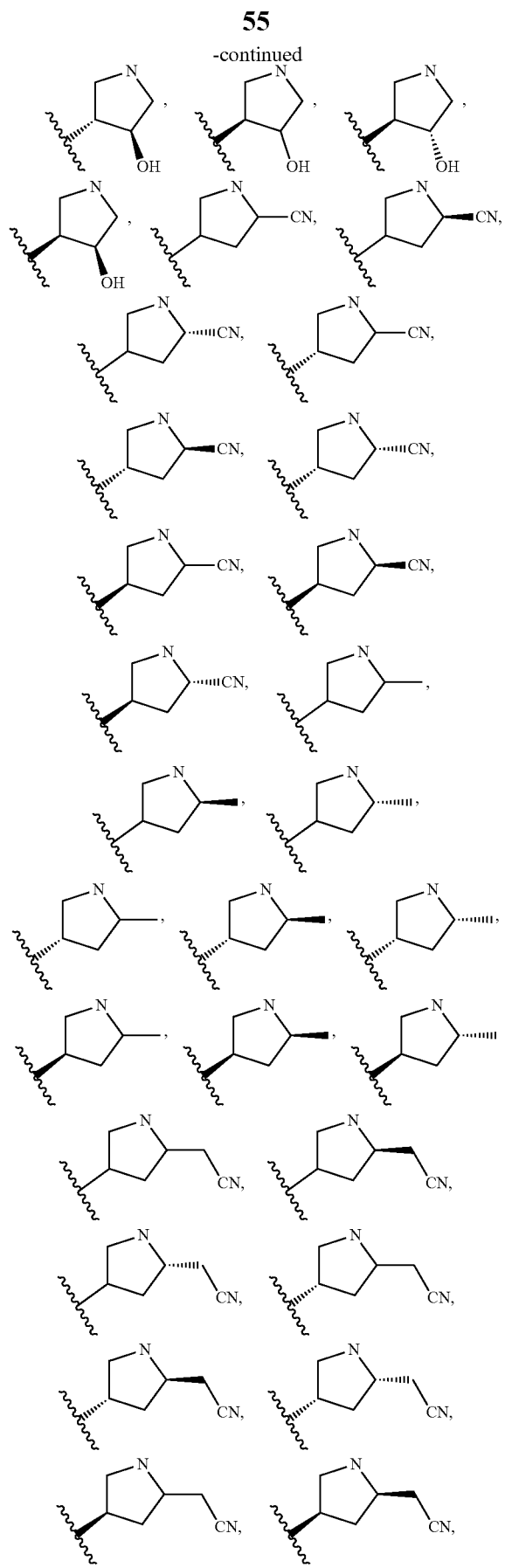
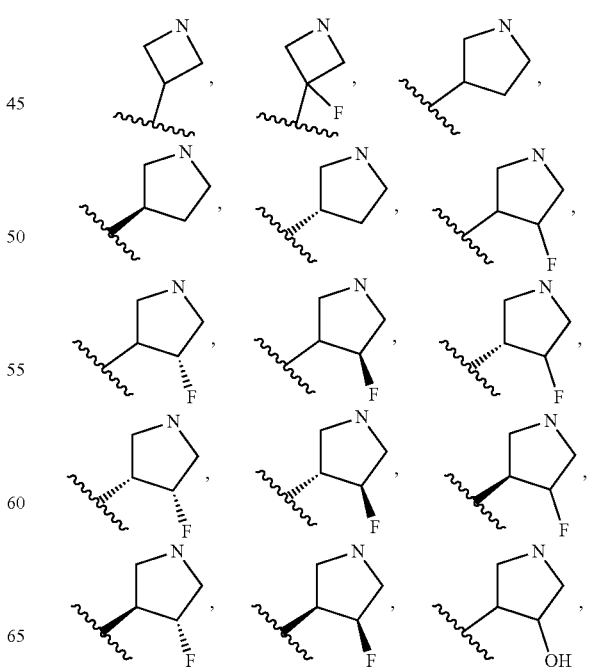
wherein the ring nitrogen of the heterocyclic group is substituted with —C(O)C(R$^{19}$)=C(R$^{20}$)R$^{18}$.
Embodiment 166. The compound of any one of embodiments 153-155, wherein the heterocyclic group of R$^{21}$ is selected from the group consisting of:

-continued

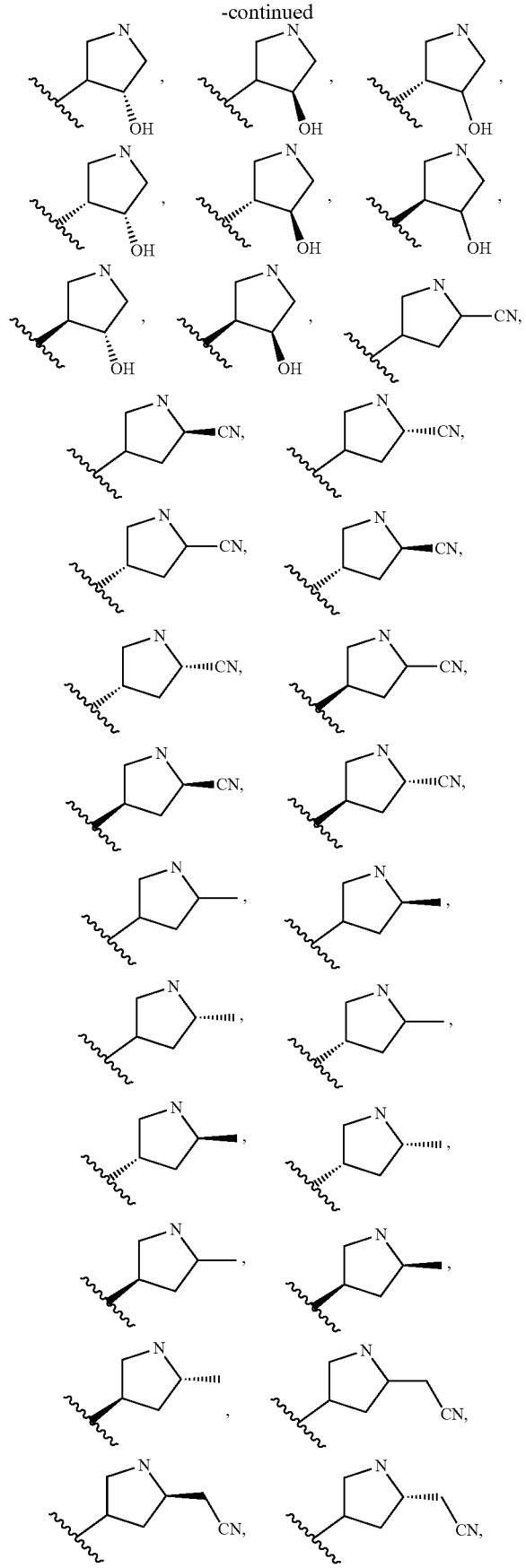

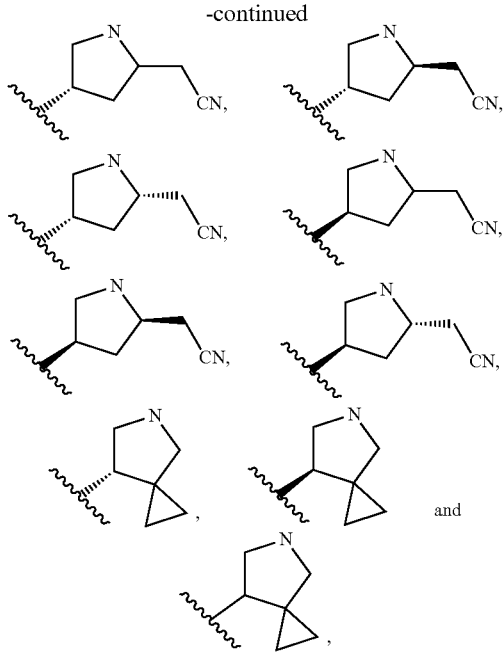

wherein the ring nitrogen of the heterocyclic group is substituted with —C(O)C(R$^{19}$)=C(R$^{20}$)R$^{18}$.

Embodiment 167. The compound of embodiment 153, wherein the heterocyclic group of R$^{21}$ is selected from the group consisting of:

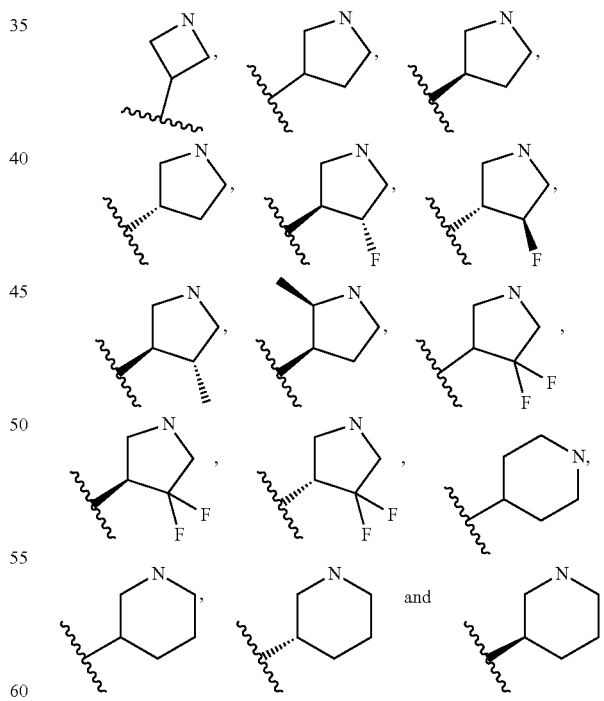

wherein the ring nitrogen of the heterocyclic group is substituted with —C(O)C(R$^{19}$)=C(R$^{20}$)R$^{18}$.

Embodiment 168. The compound of embodiment 153 or 154, wherein the heterocyclic group of R$^{21}$ is selected from the group consisting of:

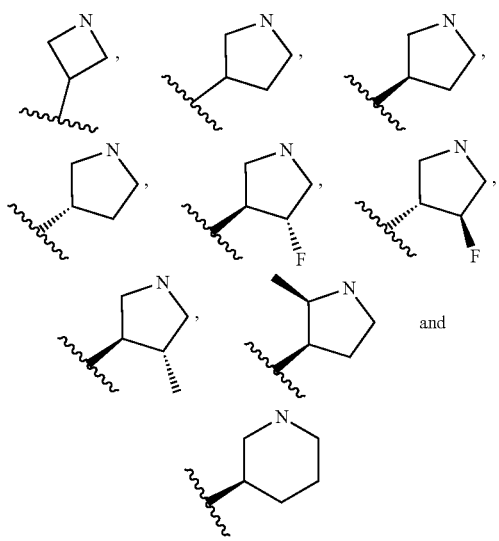

wherein the ring nitrogen of the heterocyclic group is substituted with —C(O)C($R^{19}$)=C($R^{20}$)$R^{18}$.

Embodiment 169. The compound of any one of embodiments 153-156, wherein the heterocyclic group of $R^{21}$ is selected from the group consisting of:

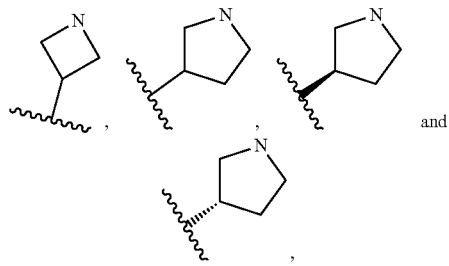

wherein the ring nitrogen of the heterocyclic group is substituted with —C(O)C($R^{19}$)=C($R^{20}$)$R^{18}$.

Embodiment 170. The compound of embodiment 153, wherein the heterocyclic group of $R^{21}$ is selected from the group consisting of:

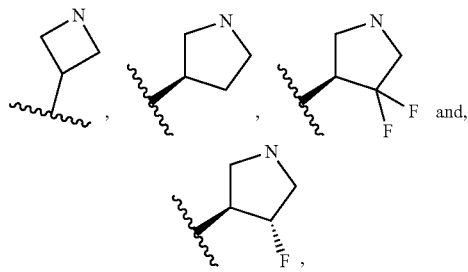

wherein the ring nitrogen of the heterocyclic group is substituted with —C(O)C($R^{19}$)=C($R^{20}$)$R^{18}$.

Embodiment 171. The compound of any one of embodiments 153-156, wherein the heterocyclic group of $R^{21}$ is selected from the group consisting of:

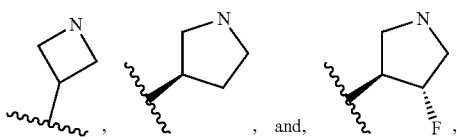 [SMILES: *C1CNC1 ; *[C@@H]1CCNC1 ; *[C@H]1CNC[C@@H]1F]

wherein the ring nitrogen of the heterocyclic group is substituted with —C(O)C($R^{19}$)=C($R^{20}$)$R^{18}$.

Embodiment 172. The compound of embodiment 153, wherein the heterocyclic group of $R^{21}$ is selected from the group consisting of:

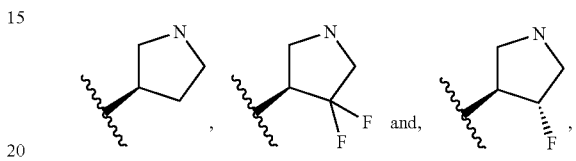

wherein the ring nitrogen of the heterocyclic group is substituted with —C(O)C($R^{19}$)=C($R^{20}$)$R^{18}$.

Embodiment 173. The compound of any one of embodiments 153-156t, wherein the heterocyclic group of $R^{21}$ is selected from the group consisting of:

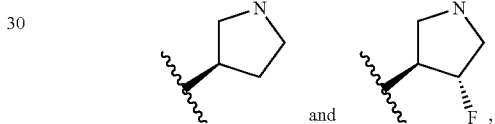

wherein the ring nitrogen of the heterocyclic group is substituted with —C(O)C($R^{19}$)=C($R^{20}$)$R^{18}$.

Embodiment 174. The compound of any one of embodiments 153-156, wherein the heterocyclic group of $R^{21}$ is

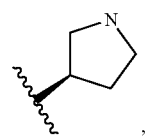 [SMILES: *[C@@H]1CCNC1]

wherein the ring nitrogen of the heterocyclic group is substituted with —C(O)C($R^{19}$)=C($R^{20}$)$R^{18}$.

Embodiment 175. The compound of any one of embodiments 1-63, 66-84, 86-124 and 133-136, wherein $R^{16}$ is selected from the group consisting of:

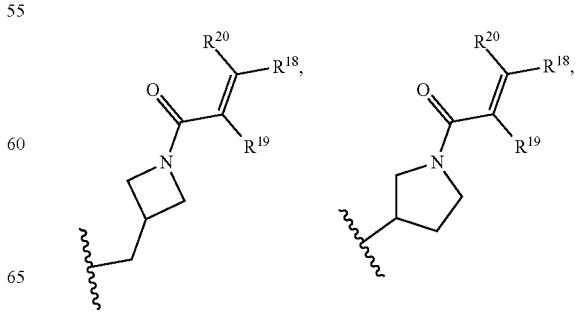

-continued

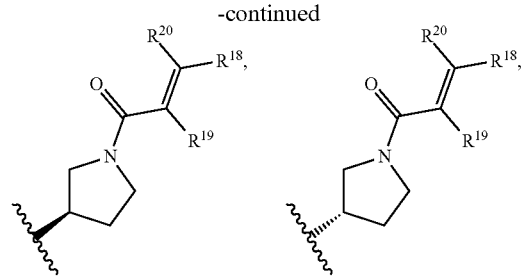

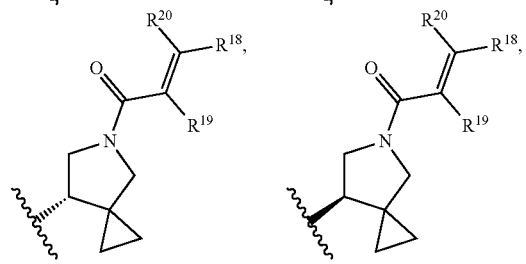

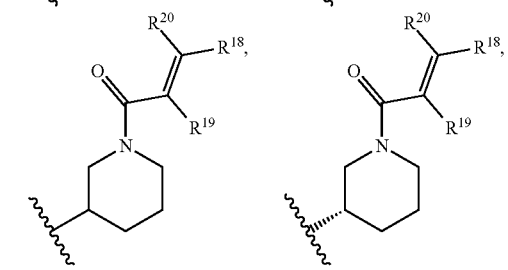

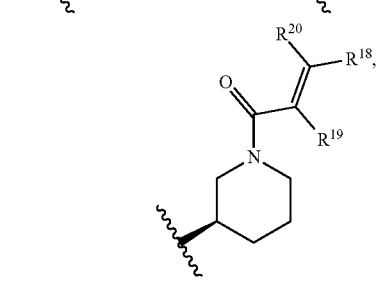

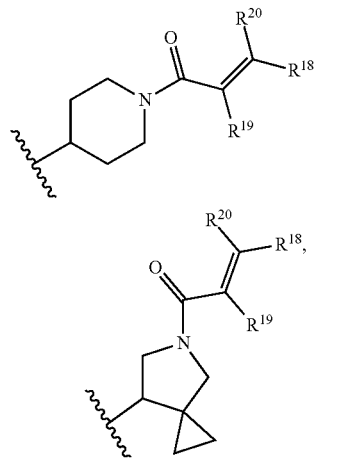

and wherein the azetidine, pyrrolidine, piperidine and 5-azaspiro [2.4]heptane groups are not further substituted, or are substituted with one substituent selected from hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy and halo, or with two halo.

Embodiment 176. The compound of any one of embodiments 1-63, 66-84, 86-124 and 133- 136, wherein $R^{16}$ is selected from the group consisting of:

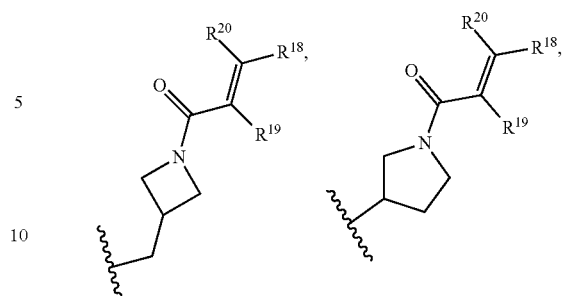

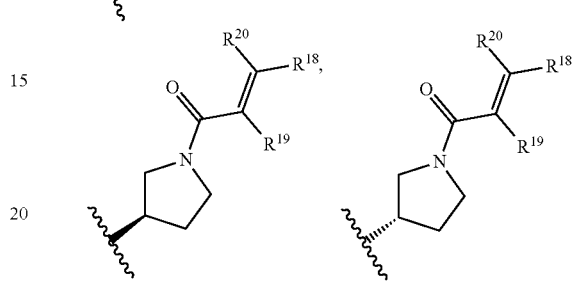

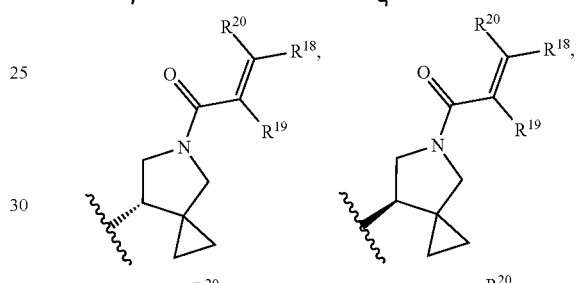

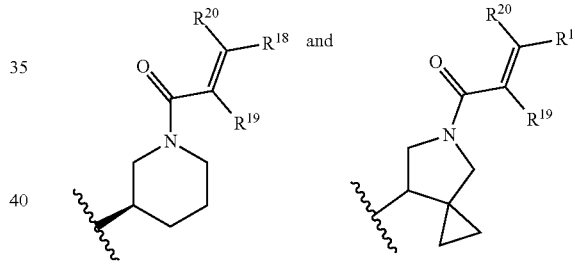

and wherein the azetidine, pyrrolidine, piperidine and 5-azaspiro [2.4]heptane groups are not further substituted, or are substituted with one substituent selected from hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, and halo.

Embodiment 177. The compound of any one of embodiments 1-63, 66-84, 86-124 and 133-136, wherein $R^{16}$ is selected from the group consisting of:

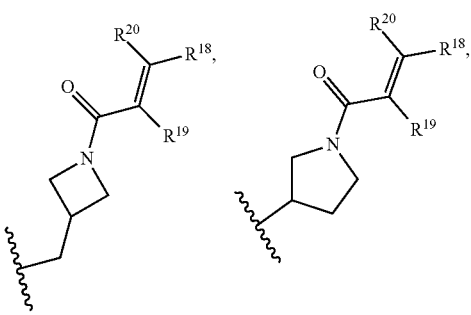

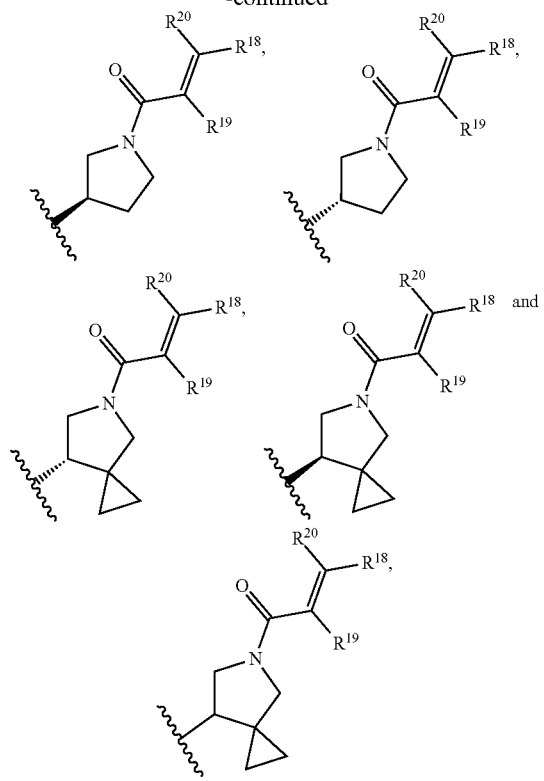

wherein the azetidine, pyrrolidine, and 5-azaspiro[2.4]heptane groups are not further substituted, or are substituted with one substituent selected from hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, and halo.

Embodiment 178. The compound of any one of embodiments 175-177, wherein the azetidine, pyrrolidine, piperidine and 5-azaspiro[2.4]heptane groups are not further substituted.

Embodiment 179. The compound of embodiment 177, wherein the azetidine, pyrrolidine, and 5-azaspiro[2.4]heptane groups are not further substituted.

Embodiment 180. The compound of embodiment 175, wherein the azetidine, pyrrolidine and 5-azaspiro[2.4]heptane groups are further substituted with 1 substituent selected from the group consisting of hydroxy, CN, $C_1$-$C_4$ alkyl, $C_1$-$C_4$ cyanoalkyl, and halo, or with two halo.

Embodiment 181. The compound of any one of embodiments 175-177, wherein the azetidine, pyrrolidine and 5-azaspiro[2.4]heptane groups are further substituted with 1 substituent selected from the group consisting of hydroxy, CN, $C_1$-$C_4$ alkyl, $C_1$-$C_4$ cyanoalkyl, and halo.

Embodiment 182. The compound of embodiment 175, wherein the azetidine, pyrrolidine and 5-azaspiro[2.4]heptane groups are further substituted with 1 substituent selected from the group consisting of hydroxy, CN, Me, —$CH_2CN$ and F, or with two fluoro.

Embodiment 183. The compound of any one of embodiments 175-177, wherein the azetidine, pyrrolidine and 5-azaspiro[2.4]heptane groups are further substituted with 1 substituent selected from the group consisting of hydroxy, CN, Me, —$CH_2CN$ and F.

Embodiment 184. The compound of embodiment 175, wherein $R^{16}$ is selected from the group

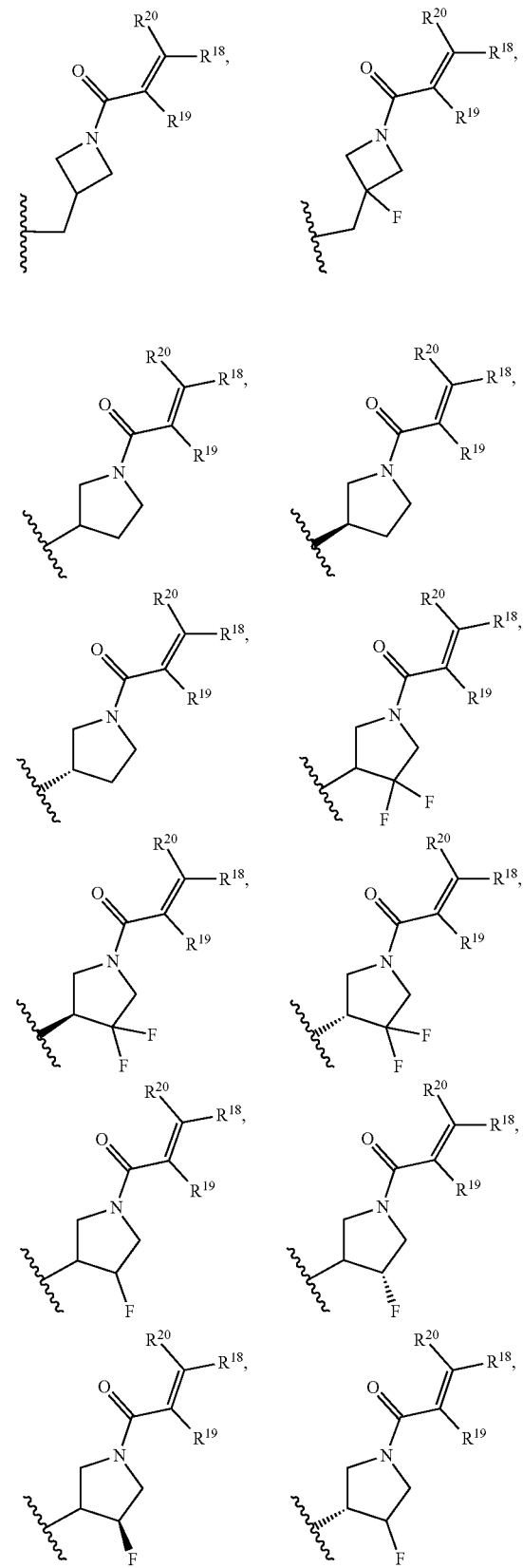

-continued
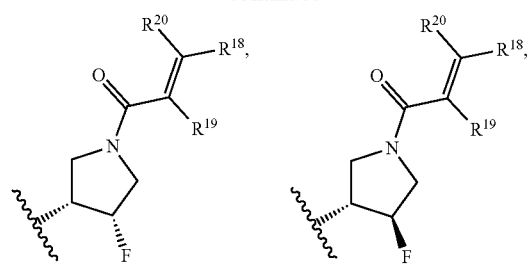
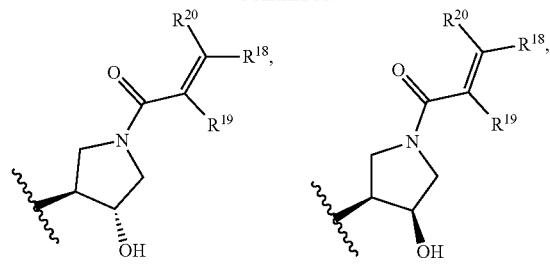
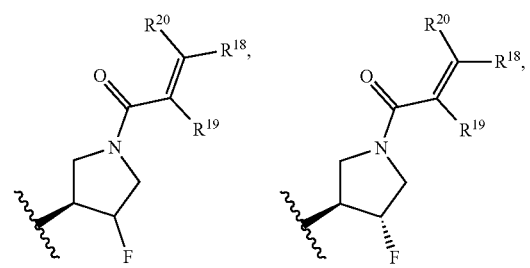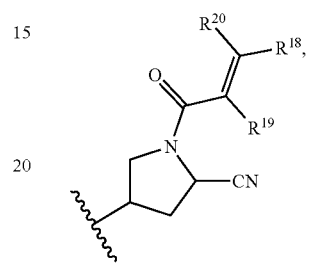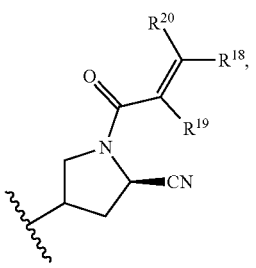
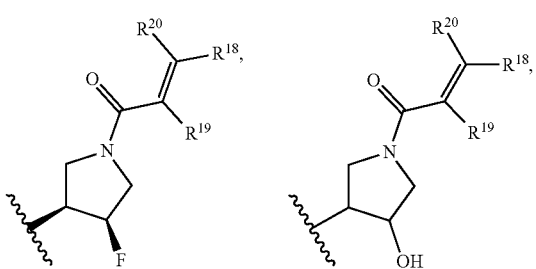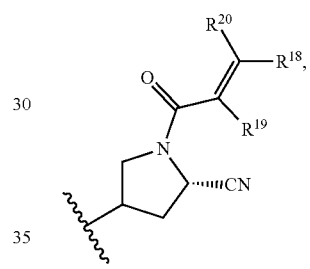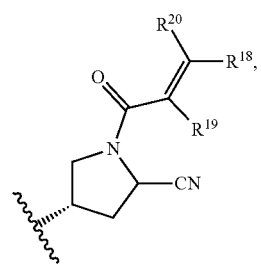
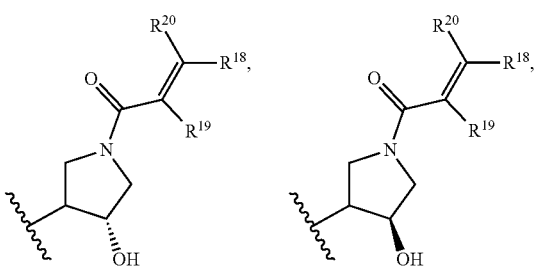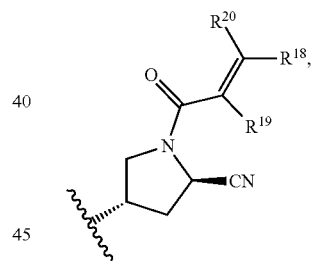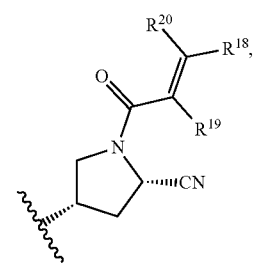
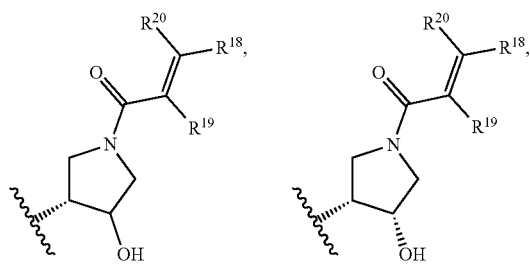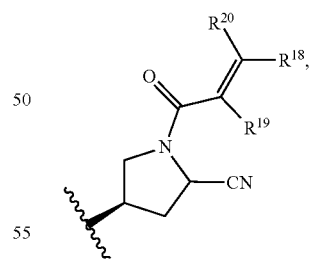
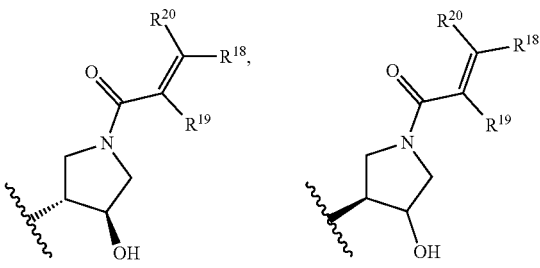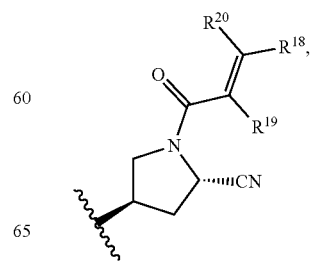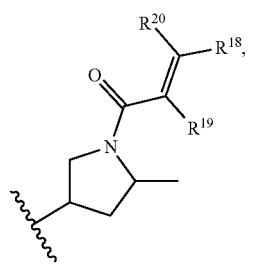

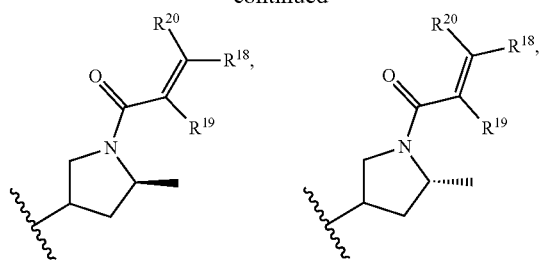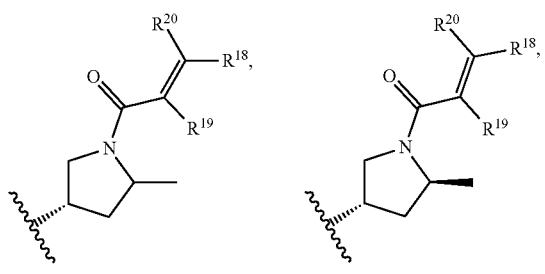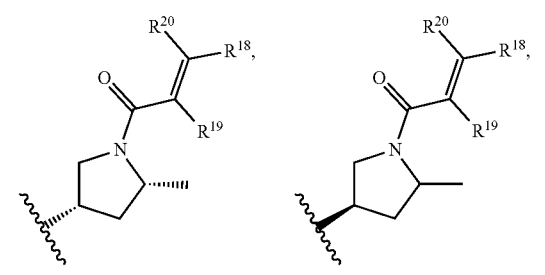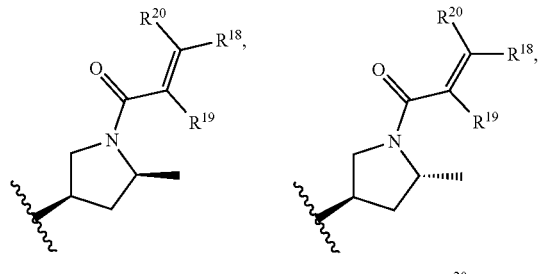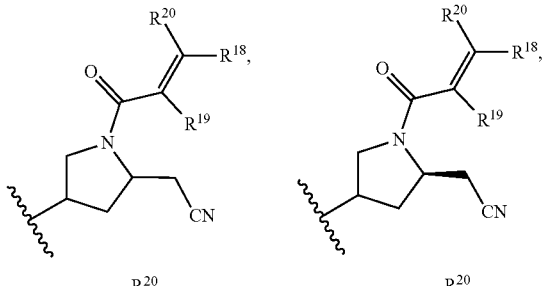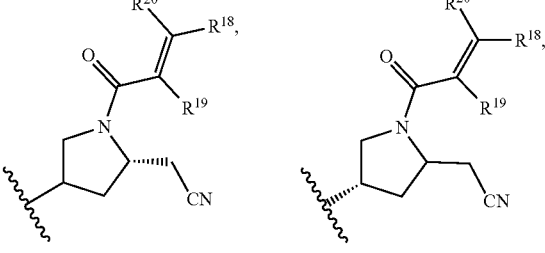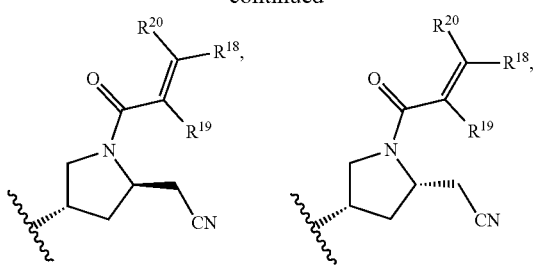

-continued
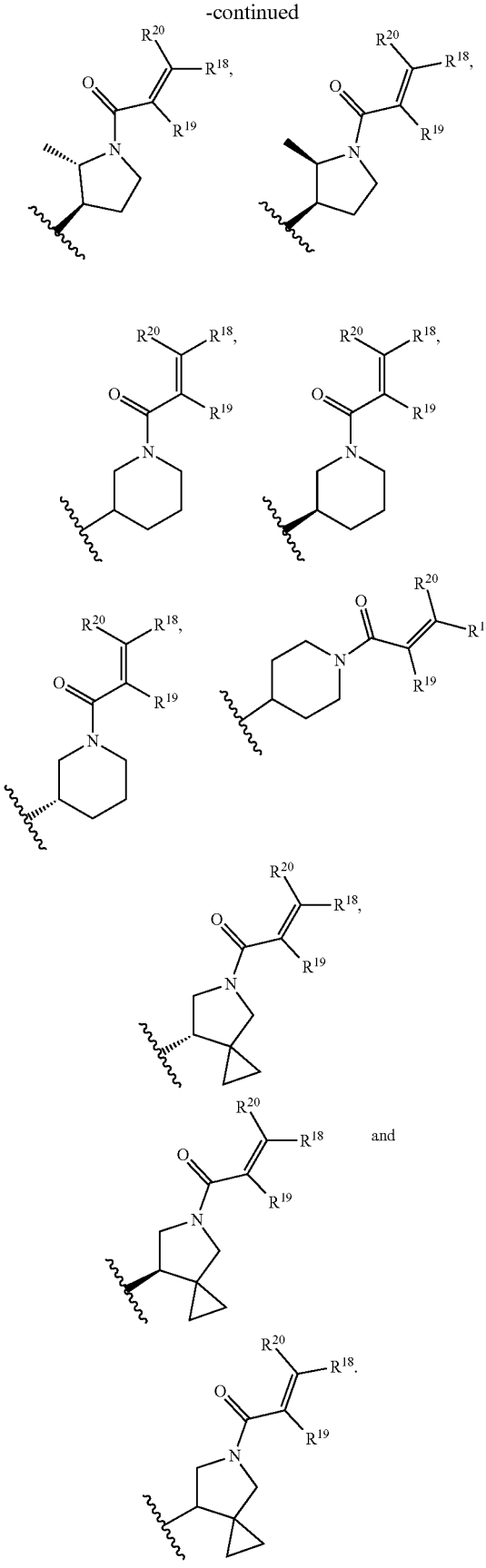
Embodiment 185. The compound of any one of embodiments 175-176e, wherein $R^{16}$ is selected from the group consisting of:
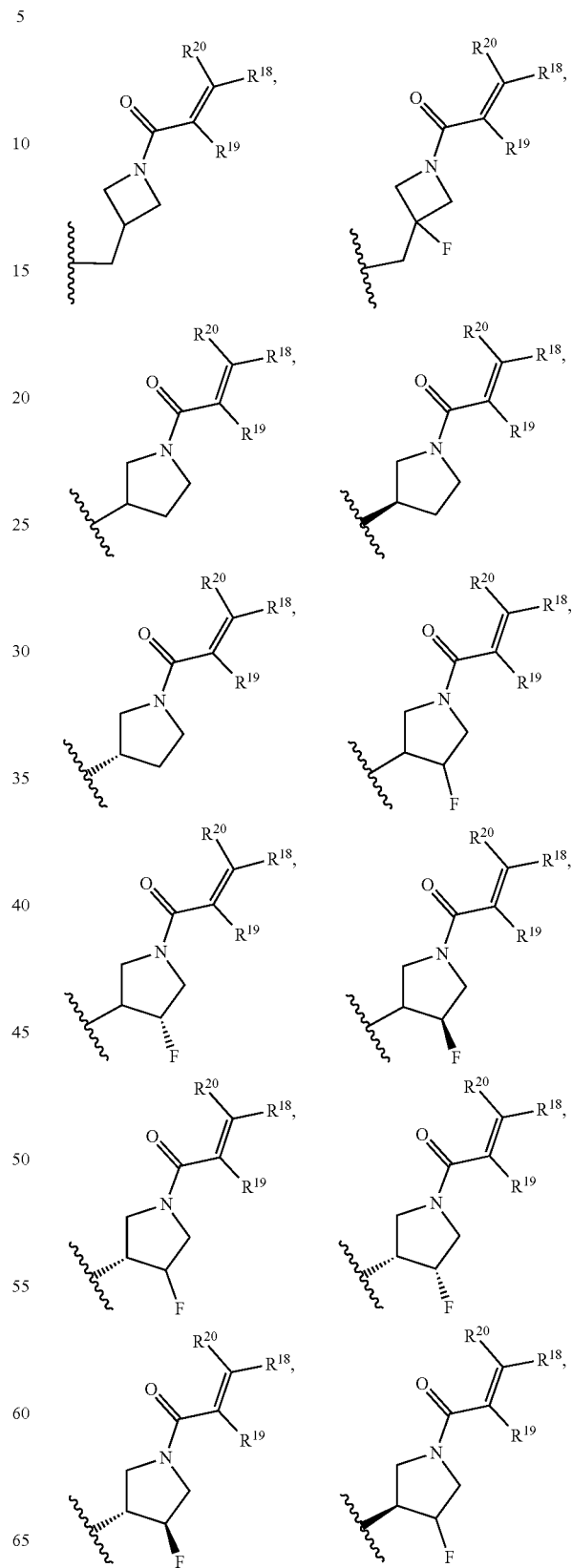

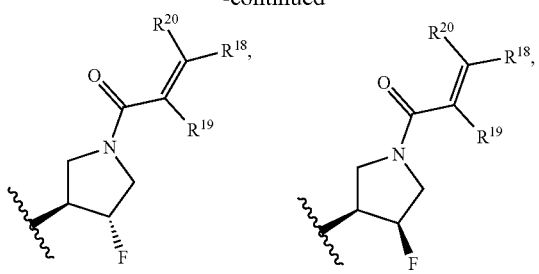
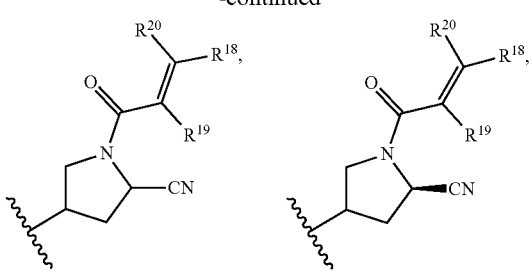
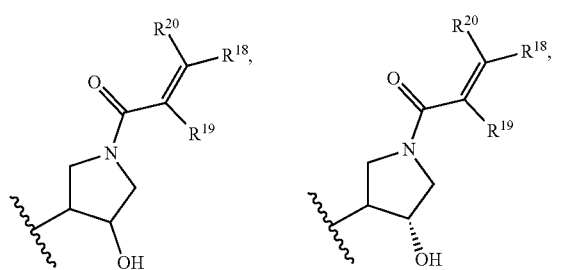
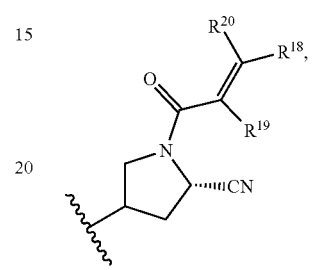
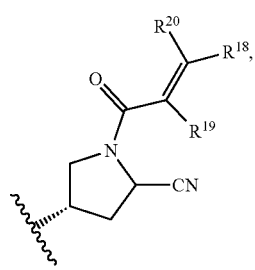
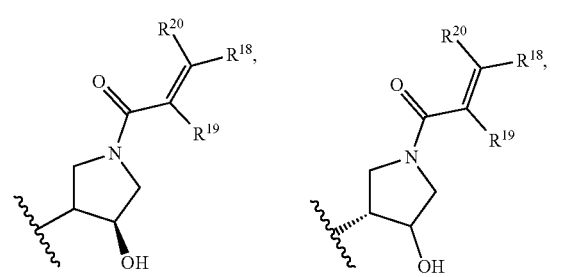
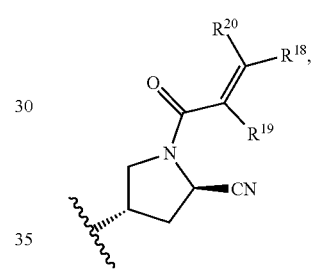
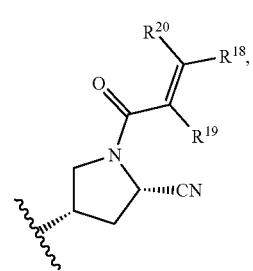
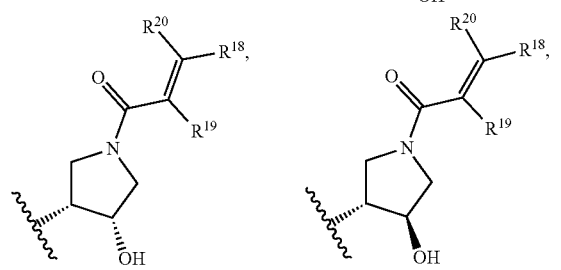
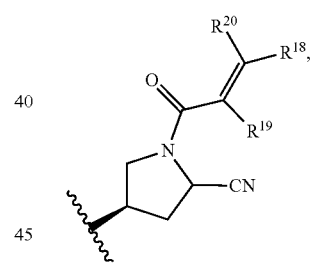
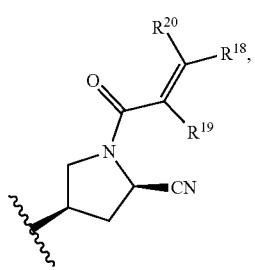
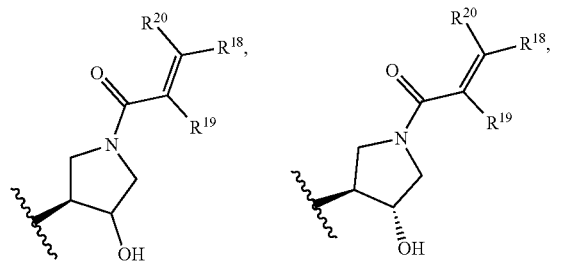
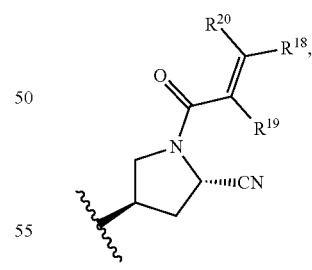
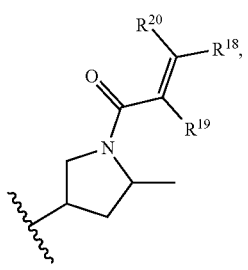
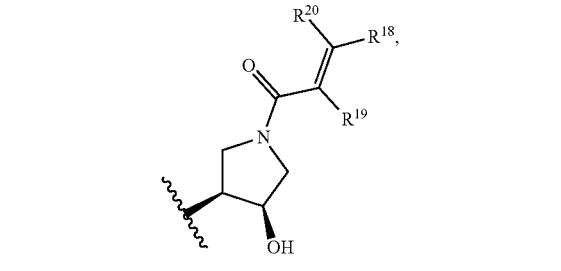
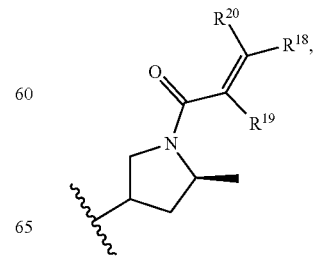
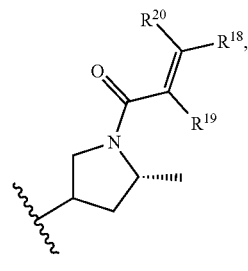

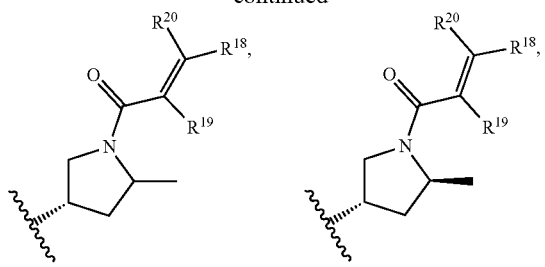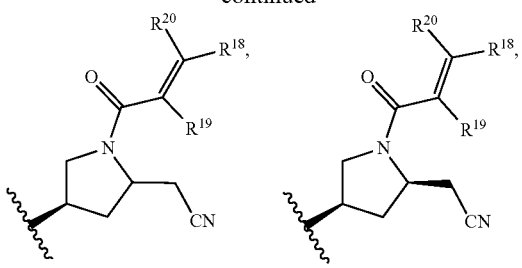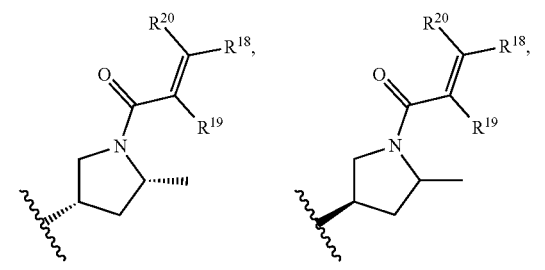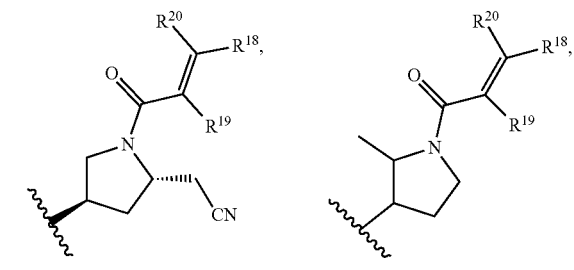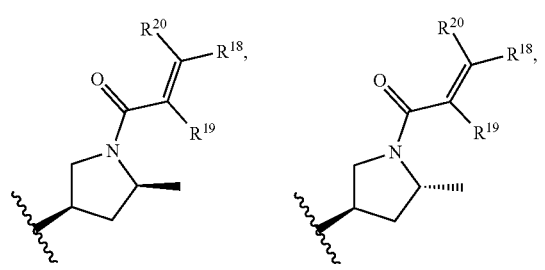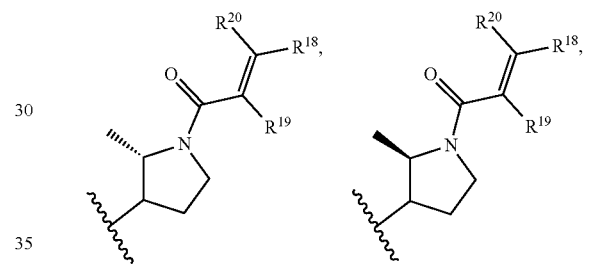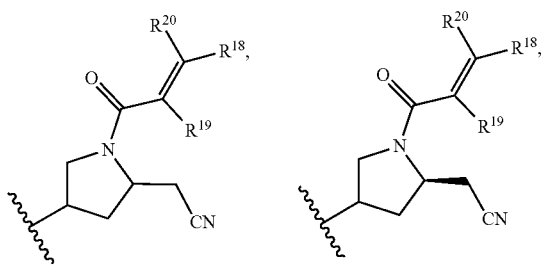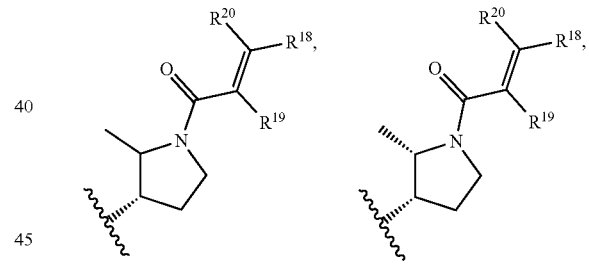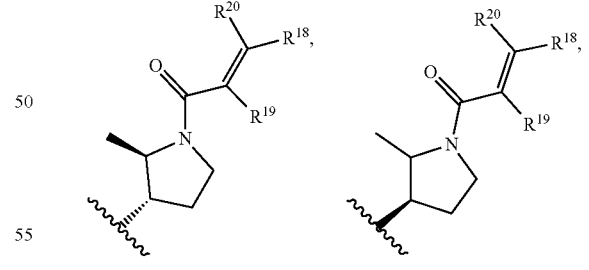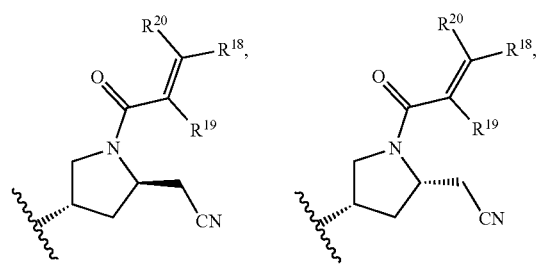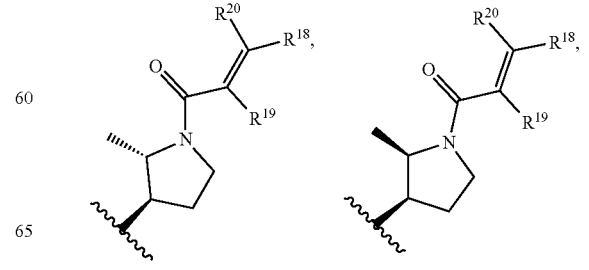

-continued
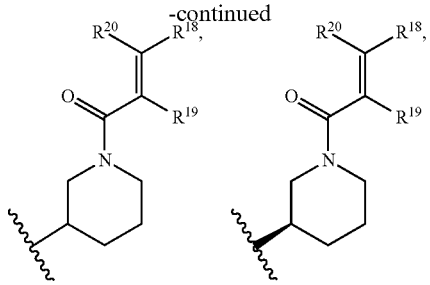
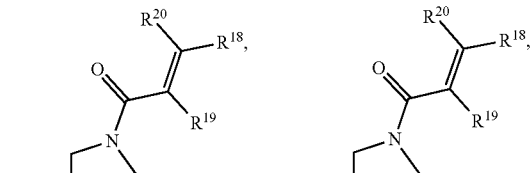
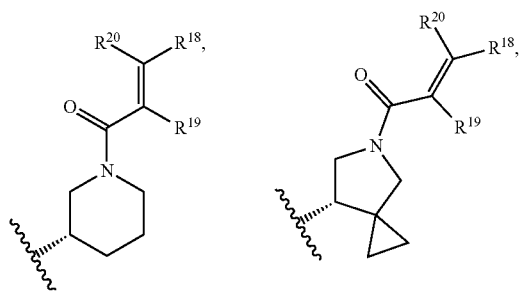
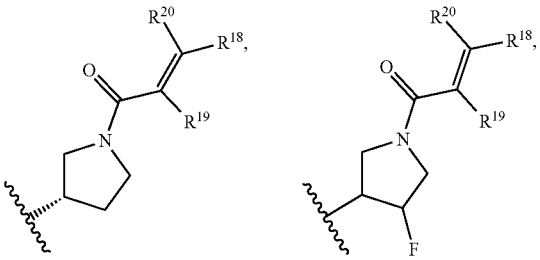
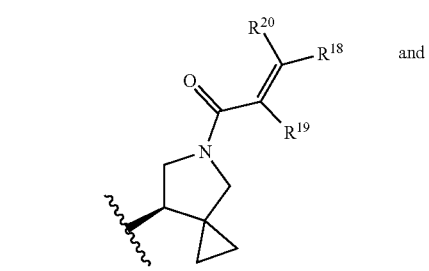
and
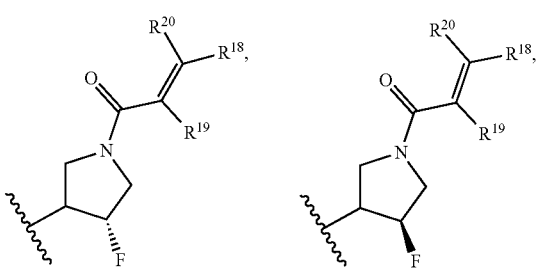
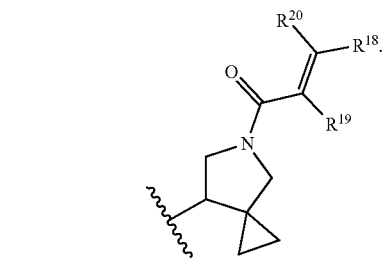
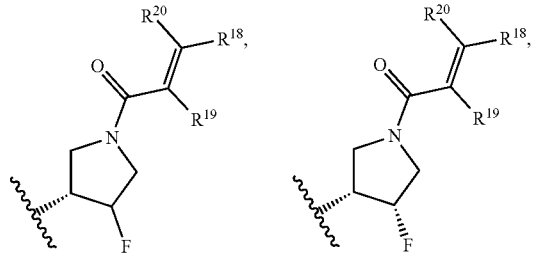
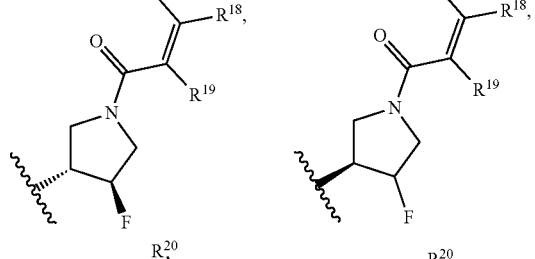
Embodiment 186. The compound of any one of embodiments 175-177, wherein $R^{16}$ is selected from the group consisting of:
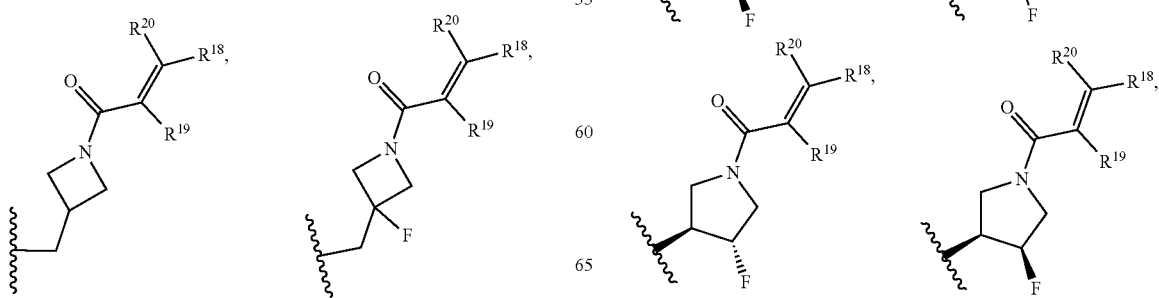
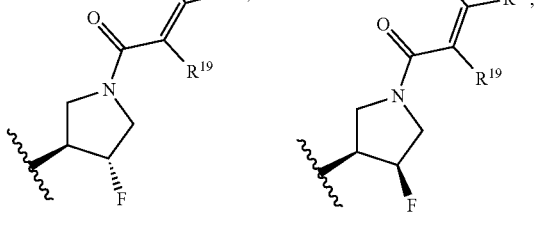

-continued
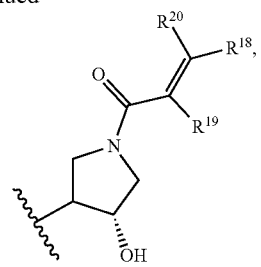 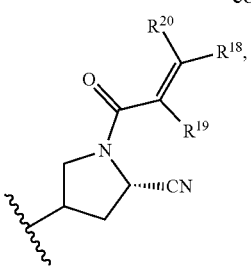 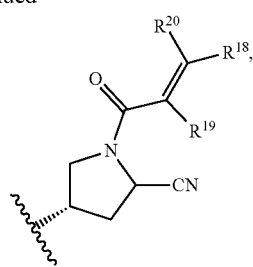
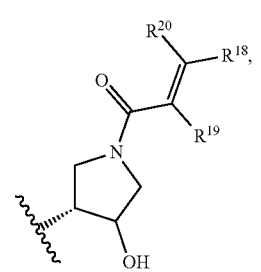 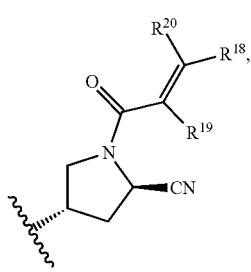 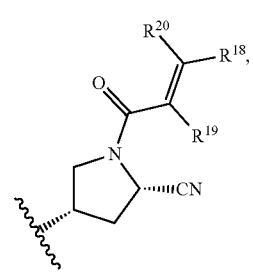
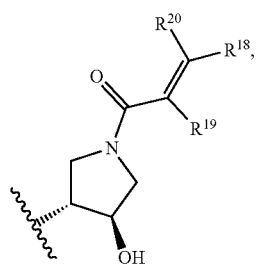 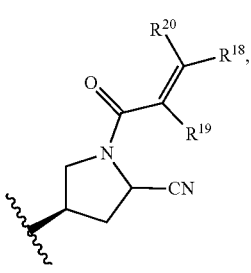 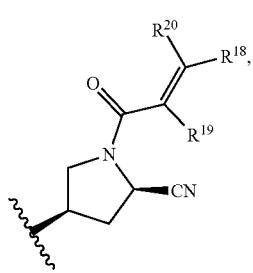
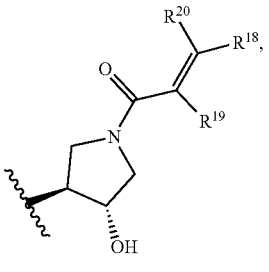 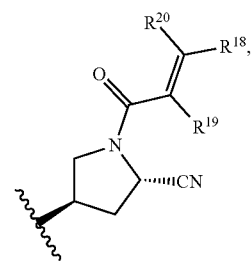 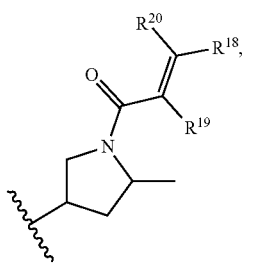
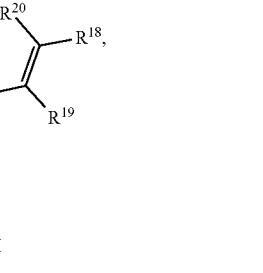 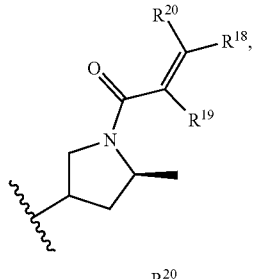 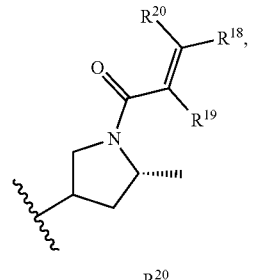
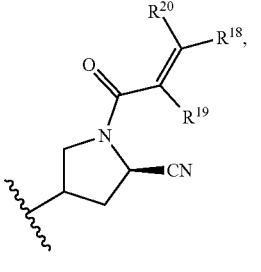 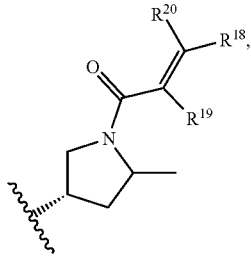 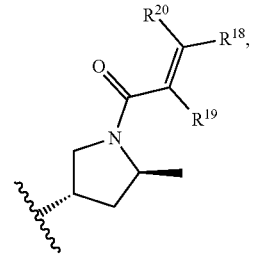

-continued
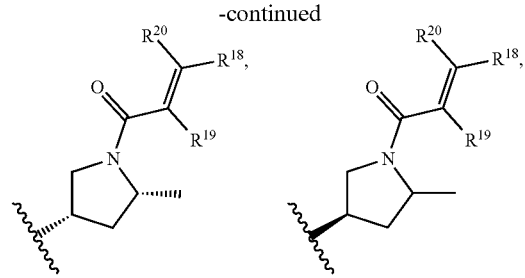
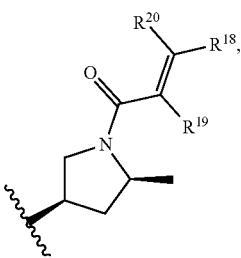
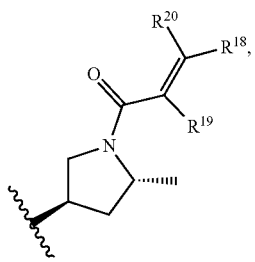
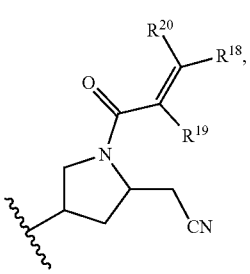
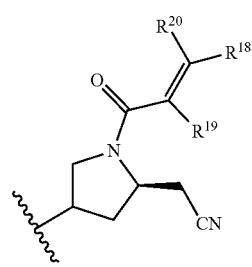
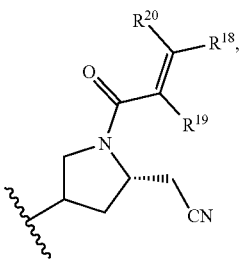
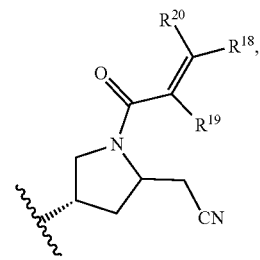
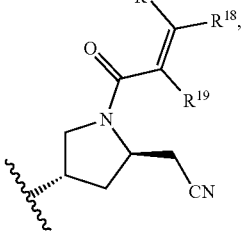
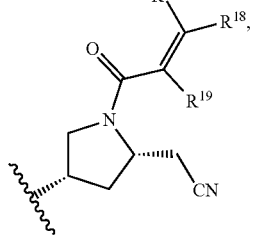
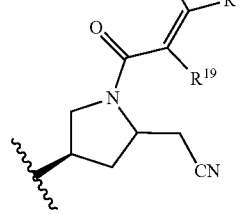
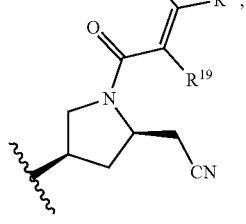
-continued
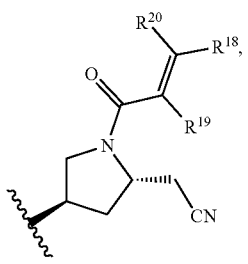
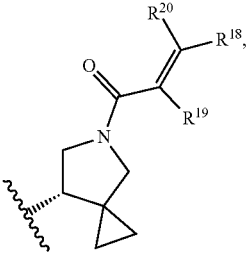
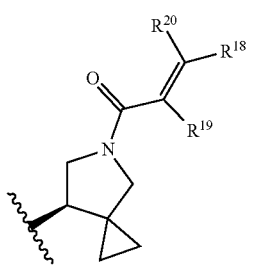
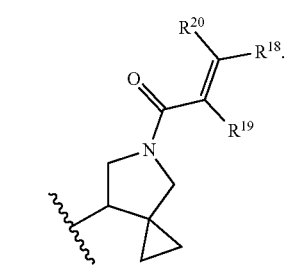
Embodiment 187. The compound of embodiment 175, wherein $R^{16}$ is selected from the group consisting of.
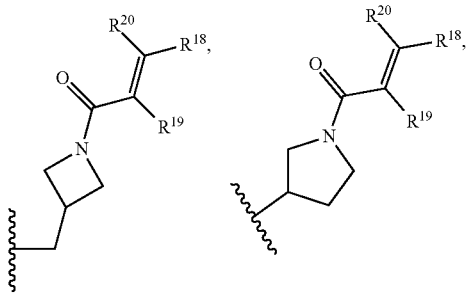
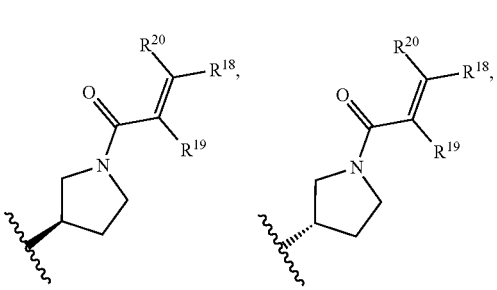

-continued
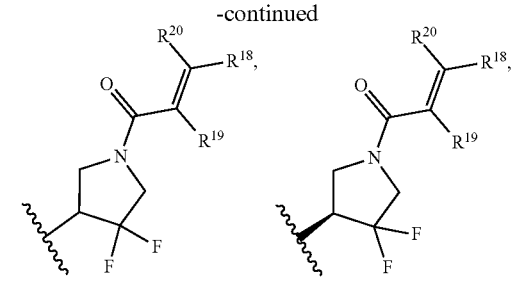
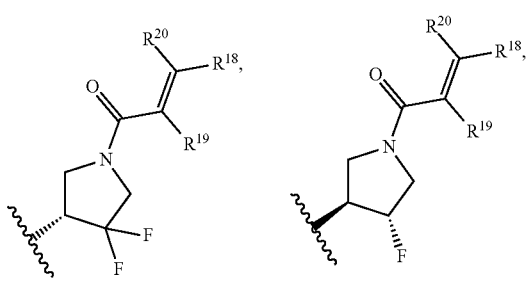
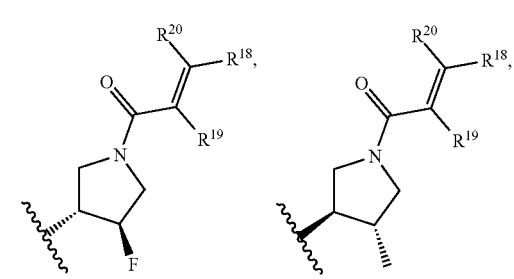
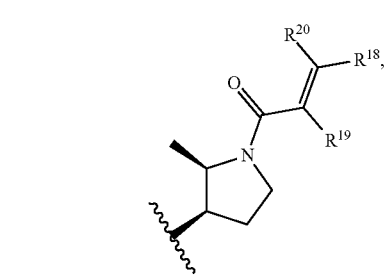
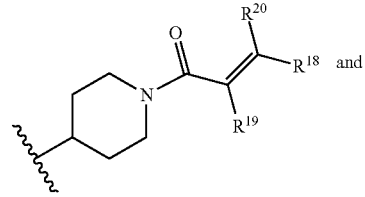
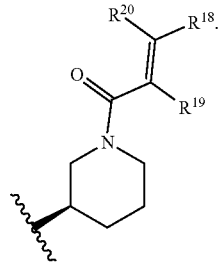
Embodiment 188. The compound of embodiment 175 or 176, wherein $R^{16}$ is selected from the group consisting of:
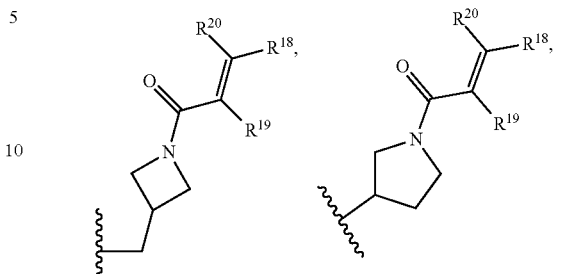

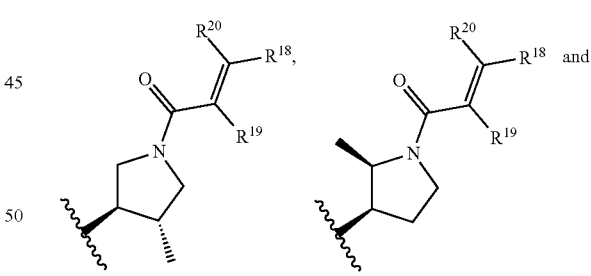
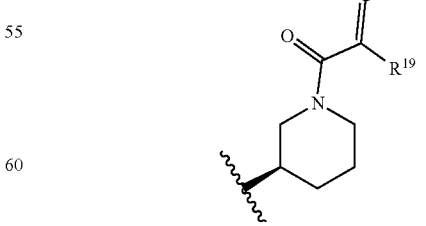
Embodiment 189. The compound of any one of embodiments 175-177, wherein $R^{16}$ is selected from the group consisting of:

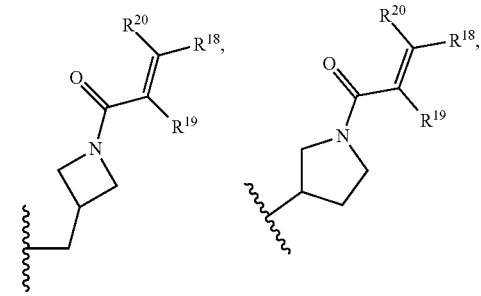

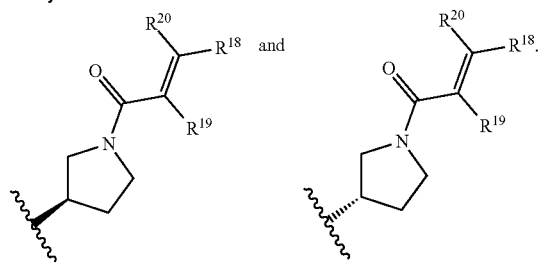

Embodiment 190. The compound of embodiment 175, wherein $R^{16}$ is selected from the group consisting of:

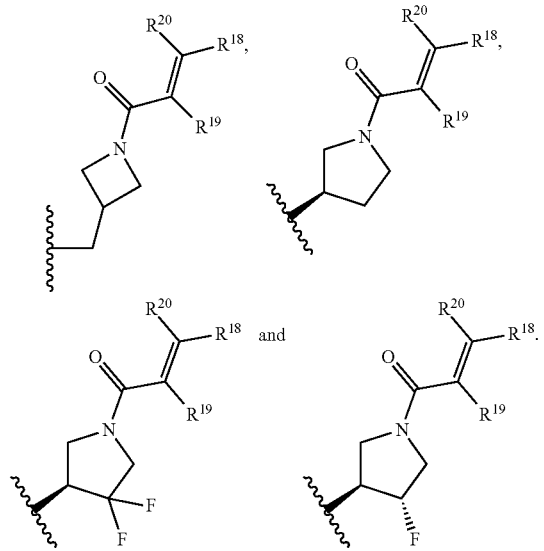

Embodiment 191. The compound of any one of embodiments 175-177, wherein $R^{16}$ is selected from the group consisting of:

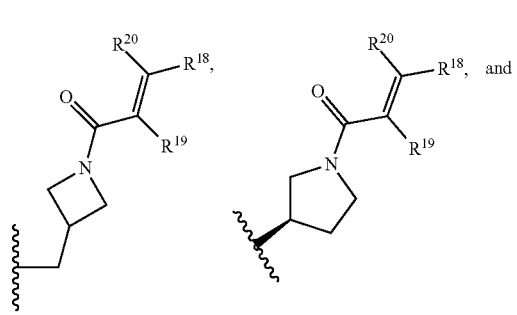

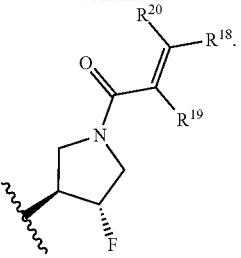

Embodiment 192. The compound of embodiment 175, wherein $R^{16}$ is selected from the group consisting of:

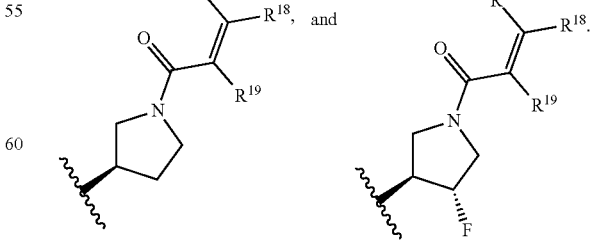

Embodiment 193. The compound of any one of embodiments 175-177, wherein $R^6$ is selected from the group consisting of:

Embodiment 194. The compound of any one of embodiments 175-177, wherein $R^{16}$ is.

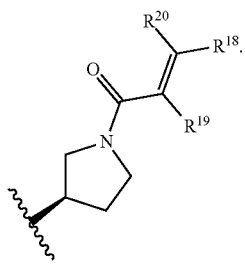

Embodiment 195. The compound of any one of embodiments 1-63, 66-84 and 86-115, wherein $R^{15}$ and $R^{16}$ together with the nitrogen to which they are attached form a 4-8 membered saturated heterocyclic group optionally comprising a second nitrogen as the sole additional heteroatom within the ring atoms, wherein the heterocyclic group is substituted with one substituent selected from the group consisting of:
—$(CH_2)_q$—$N(R^{17})C(O)C(R^{19})$=$C(R^{20})R^{18}$, and
—$C(O)C(R^{19})$=$C(R^{20})R^{18}$, with the proviso that when —$C(O)C(R^{19})$=$C(R^{20})R^{18}$ is the substituent, then the 4-8 membered saturated heterocyclic group formed by $R^{15}$ and $R^{16}$ together with the nitrogen to which they are attached comprises the second nitrogen ring atom and the —$C(O)C(R^{19})$=$C(R^{20})R^{18}$ is connected to the heterocyclic group at the second ring nitrogen.

Embodiment 196. The compound of embodiment 195, wherein the 4-8 membered saturated heterocyclic group of $R^{15}$ and $R^{16}$ together with the nitrogen to which they are attached comprises one ring.

Embodiment 197. The compound of embodiment 195, wherein the 4-8 membered saturated heterocyclic group of $R^{15}$ and $R^{16}$ together with the nitrogen to which they are attached comprises two rings.

Embodiment 198. The compound of embodiment 195, wherein the 4-8 membered saturated heterocyclic group of $R^{15}$ and $R^{16}$ together with the nitrogen to which they are attached is selected from the group consisting of:

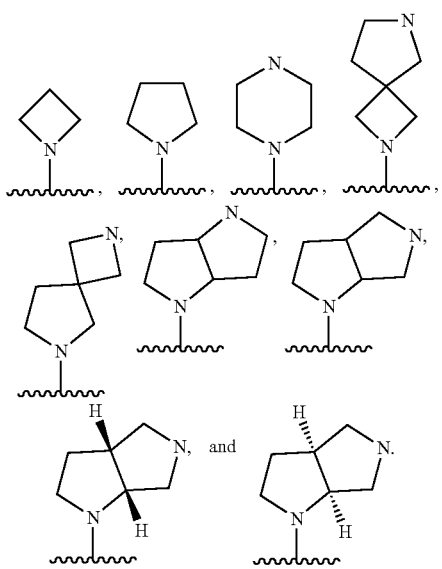

Embodiment 199. The compound of embodiment 195, wherein the 4-8 membered saturated heterocyclic group of $R^{15}$ and $R^{16}$ together with the nitrogen to which they are attached is selected from the group consisting of:

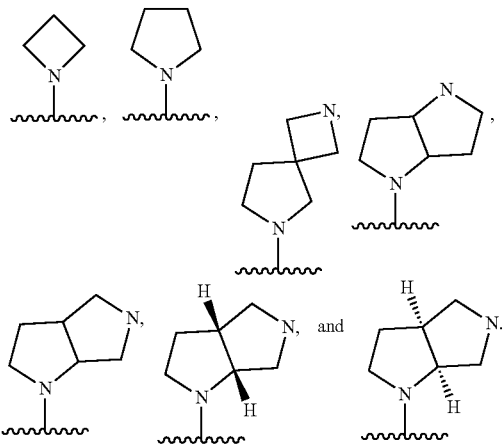

Embodiment 200. The compound of any one of embodiments 195-199, wherein the 4-8 membered saturated heterocyclic group of $R^{15}$ and $R^{16}$ together with the nitrogen to which they are attached is substituted with —$(CH_2)_q$—$N(R^{17})C(O)C(R^{19})$=$C(R^{20})R^{18}$.

Embodiment 201. The compound of any one of embodiments 1-63, 66-84, 86-115 and 118-200, wherein q is 0.

Embodiment 202. The compound of any one of embodiments 1-63, 66-84, 86-115 and 118-201, wherein $R^{17}$ is selected from the group consisting of hydrogen and $C_1$-$C_4$ alkyl.

Embodiment 203. The compound of any one of embodiments 1-63, 66-84, 86-115 and 118-201, wherein $R^{17}$ is selected from the group consisting of hydrogen and methyl.

Embodiment 204. The compound of any one of embodiments 1-63, 66-84, 86-115 and 118-201, wherein $R^{17}$ is hydrogen.

Embodiment 205. The compound of any one of embodiments 1-63, 66-84, 86-115 and 118-198, wherein the 4-8 membered saturated heterocyclic group of $R^{15}$ and $R^{16}$ together with the nitrogen to which they are attached is substituted with —$C(O)C(R^{19})$=$C(R^{20})R^{18}$.

Embodiment 206. The compound of any one of embodiments 1-63, 66-84 and 86-205, wherein $R^{19}$ is hydrogen.

Embodiment 207. The compound of any one of embodiments 1-63, 66-84 and 86-206, wherein $R^{20}$ is selected from the group consisting of hydrogen and methyl.

Embodiment 208. The compound of any one of embodiments 1-63, 66-84 and 86-206, wherein $R^{20}$ is hydrogen.

Embodiment 209. The compound of any one of embodiments 1-63, 66-84 and 86-206, wherein $R^{18}$ and $R^{20}$ together $R^{18}$ and $R^{20}$ together with the carbon to which they are attached can be taken together to form a 4-5 membered carbocyclic or heterocyclic ring containing one heteroatom selected from N, O and S, wherein the carbocyclic or heterocyclic ring can be optionally substituted with one instance of methyl, halo, hydroxy, methoxy or carbonyl.

Embodiment 210. The compound of any one of embodiments 1-63, 66-84 and 86-206, wherein $R^{18}$ and $R^{20}$ together with the carbon to which they are attached are taken together to form a cyclobutyl or an azetidine ring, wherein the cyclobutyl and azetidine can be optionally substituted with one instance of methyl.

Embodiment 211. The compound of any one of embodiments 1-63, 66-84 and 86-208, wherein $R^{18}$ is selected from the group consisting of hydrogen, —COOH, —C(O)O—C$_1$-C$_4$ alkyl, —C(O)—C$_1$-C$_4$ alkyl, —C(O)NR$^{22}$R$^{23}$, —(CH$_2$)$_z$—NR$^{22}$R$^{23}$, —(CH$_2$)$_u$—R$^{34}$, —(C$_1$-C$_2$ alkyl)-(C$_1$-C$_2$ alkoxy), —S(O)$_2$—C$_1$-C$_4$ alkyl, and R$^{35}$.

Embodiment 212. The compound of any one of embodiments 1-63, 66-84, 86-208 and 211, wherein R$^{22}$ and R$^{23}$ are independently selected from methyl, ethyl and methoxyethyl.

Embodiment 213. The compound of any one of embodiments 1-63, 66-84, 86-208 and 211, wherein R$^{22}$ and R$^{23}$ are independently selected from methyl and ethyl.

Embodiment 214. The compound of any one of embodiments 1-63, 66-84 and 86-208, wherein R$^{18}$ is selected from the group consisting of hydrogen, —COOH, —C(O)O—C$_1$-C$_4$ alkyl, —C(O)—C$_1$-C$_4$ alkyl, —C(O)NR$^{22}$R$^{23}$, —(CH$_2$)$_z$—NR$^{22}$R$^{23}$, —(C$_1$-C$_2$ alkyl)-(C$_1$-C$_2$ alkoxy), —S(O)$_2$—C$_1$-C$_4$ alkyl, and a 5-6 membered heteroaryl group optionally substituted with C$_1$-C$_4$ alkyl; and wherein N$^{22}$ and N$^{23}$ are independently selected from methyl and ethyl.

Embodiment 215. The compound of any one of embodiments 1-63, 66-84 and 86-208, wherein R$^{18}$ is selected from the group consisting of H, —(CH$_2$)$_u$—R$^{34}$ and R$^{35}$.

Embodiment 216. The compound of any one of embodiments 1-63, 66-84, 86-208 and 211-214, wherein u is 0 or 1.

Embodiment 217. The compound of any one of embodiments 1-63, 66-84, 86-208 and 211-214, wherein u is 0.

Embodiment 218. The compound of any one of embodiments 1-63, 66-84, 86-208 and 211-214, wherein u is 1.

Embodiment 219. The compound of any one of embodiments 1-63, 66-84, 86-208 and 211-214, wherein u is 2.

Embodiment 220. The compound of any one of embodiments 1-63, 66-84, 86-208 and 211-214, wherein R$^{18}$ is selected from H, —R$^{34}$, —CH$_2$—R$^{34}$ and —R$^{35}$.

Embodiment 221. The compound of any one of embodiments 1-63, 66-84, 86-208 and 211-214, wherein R$^{18}$ is selected from —R$^{34}$, —CH$_2$—R$^{34}$ and —R$^{35}$.

Embodiment 222. The compound of any one of embodiments 1-63, 66-84, 86-208 and 211-221, wherein R$^{34}$ is a 4-7 membered monocyclic heterocycle containing a nitrogen atom and zero, one or two additional heteroatoms independently selected from oxygen and sulfur, including sulfur dioxide, wherein the monocyclic heterocycle is substituted with 0, 1, 2, 3 or 4 substituents independently selected from halo, hydroxy, C$_1$-C$_4$ alkyl, C$_1$-C$_6$ aminoalkyl, C$_1$-C$_6$ alkoxy, C$_1$-C$_4$ haloalkyl, C$_1$-C$_4$ haloalkoxy, C$_1$-C$_4$ hydroxyalkyl, CH$_2$—(C$_3$-C$_6$ heterocyclyl) and C$_2$-C$_3$ alkynyl.

Embodiment 223. The compound of any one of embodiments 1-63, 66-84, 86-208 and 211-221, wherein R$^{34}$ is a 4-7 membered monocyclic heterocycle containing a nitrogen atom and zero, one or two additional heteroatoms independently selected from oxygen and sulfur, including sulfur dioxide, wherein the monocyclic heterocycle is substituted with 0, 1, 2, 3 or 4 substituents independently selected from halo, hydroxy, C$_1$-C$_4$ alkyl, C$_1$-C$_6$ aminoalkyl, C$_1$-C$_6$ alkoxy, C$_1$-C$_4$ haloalkyl, C$_1$-C$_4$ haloalkoxy, and C$_2$-C$_3$ alkynyl.

Embodiment 224. The compound of any one of embodiments 1-63, 66-84, 86-208 and 211-223, wherein the monocyclic heterocycle of R$^{34}$ is substituted with 0 or 1 instance of methyl, ethyl, isopropyl, methoxyethyl, hydroxyethyl, or CH$_2$-oxetanyl.

Embodiment 225. The compound of any one of embodiments 1-63, 66-84, 86-208 and 211-223, wherein the monocyclic heterocycle of R$^{34}$ is substituted with 0 or 1 instance of methyl.

Embodiment 226. The compound of any one of embodiments 1-63, 66-84, 86-208 and 211-223, wherein R$^{34}$ is selected from azetidinyl, pyrrolidinyl, tetrahydrofuranyl, and morpholinyl substituted with 0 or 1 instance of methyl, ethyl, isopropyl, methoxyethyl, hydroxyethyl or CH$_2$-oxetanyl.

Embodiment 227. The compound of any one of embodiments 1-63, 66-84, 86-208 and 211-223, wherein R$^{34}$ is selected from azetidinyl, pyrrolidinyl, and morpholinyl substituted with 0 or 1 instance of methyl, ethyl, isopropyl, methoxyethyl, hydroxyethyl or —CH$_2$-oxetanyl.

Embodiment 228. The compound of any one of embodiments 1-63, 66-84, 86-208 and 211-223, wherein R$^{34}$ is selected from azetidinyl, pyrrolidinyl and morpholinyl substituted with 0 or 1 instance of methyl.

Embodiment 229. The compound of one of embodiments 1-63, 66-84, 86-208 and 211-223, wherein R$^{34}$ is azetidinyl substituted with 0 or 1 instance of methyl, ethyl, isopropyl, methoxyethyl, hydroxyethyl or CH$_2$-oxetanyl.

Embodiment 230. The compound of one of embodiments 1-63, 66-84, 86-208 and 211-223, wherein R$^{34}$ is azetidinyl substituted with 0 or 1 instance of methyl.

Embodiment 231. The compound of any one of embodiments 1-63, 66-84, 86-208 and 211-223, wherein R$^{34}$ is pyrrolidinyl substituted with 0 or 1 instance of methyl.

Embodiment 232. The compound of any one of embodiments 1-63, 66-84, 86-208 and 211-223, wherein R$^{34}$ is unsubstituted morpholinyl.

Embodiment 233. The compound of any one of embodiments 1-63, 66-84, 86-208 and 211-223, wherein R$^{34}$ is morpholinyl substituted with 0 or 1 instance of methyl.

Embodiment 234. The compound of any one of embodiments 1-63, 66-84, 86-208 and 211-233, wherein the attachment point for R$^{34}$ is a carbon atom.

Embodiment 235. The compound of embodiment 234, wherein R$^{34}$ is selected from the group consisting of:

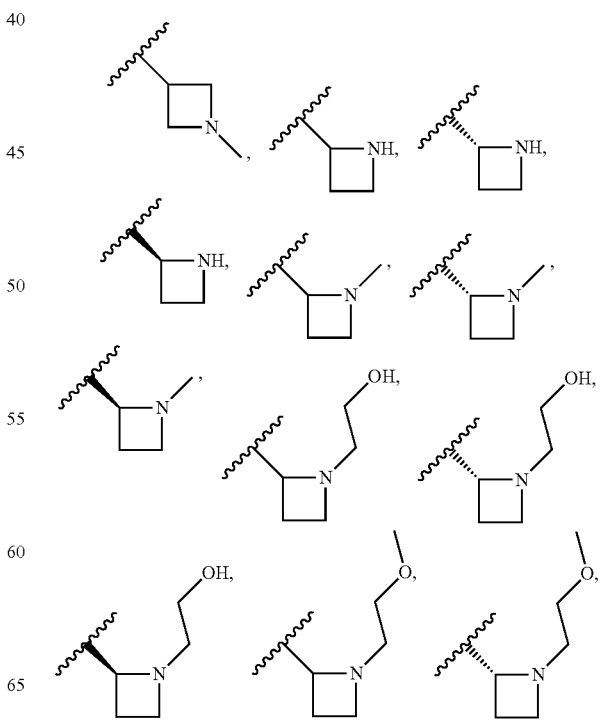

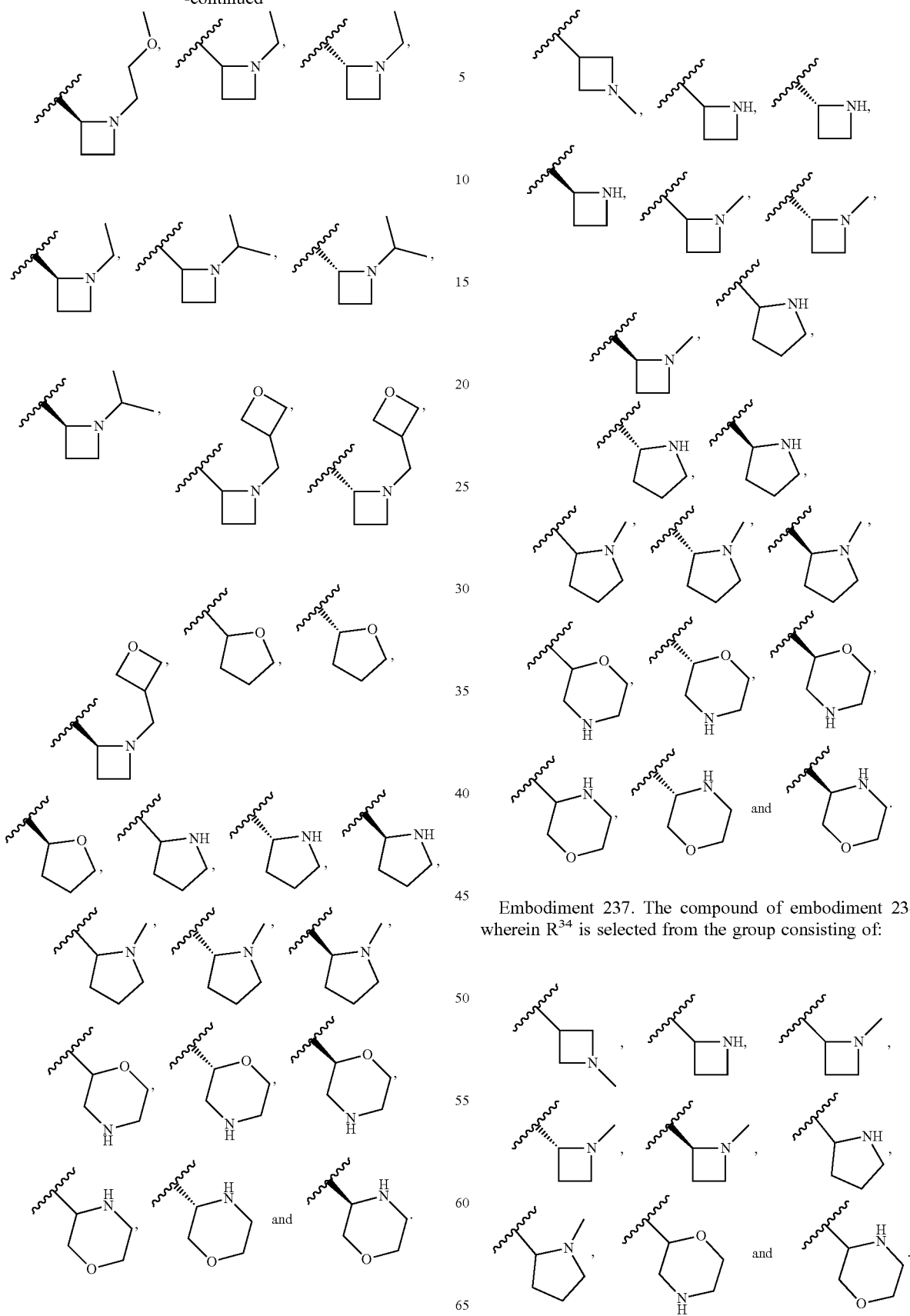
Embodiment 236. The compound of embodiment 234, wherein $R^{34}$ is selected from the group
Embodiment 237. The compound of embodiment 234, wherein $R^{34}$ is selected from the group consisting of:

Embodiment 238. The compound of embodiment 234, wherein $R^{34}$ is selected from the group consisting of:

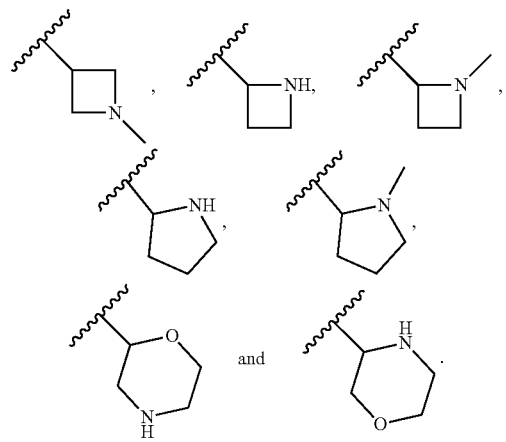

Embodiment 239. The compound of embodiment 234, wherein $R^{34}$ is

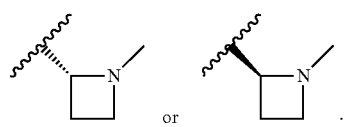

Embodiment 240. The compound of any one of embodiments 1-63, 66-84, 86-208 and 211-221 wherein $R^{34}$ is a 4-10 membered heterocycle containing a nitrogen atom and zero, one or two additional heteroatoms independently selected from oxygen and sulfur, including sulfur dioxide, wherein the 4-10 membered heterocycle is substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 241. The compound of embodiment 240, wherein $R^{34}$ is a 4-10 membered heterocycle containing a nitrogen atom and zero, one or two additional heteroatoms independently selected from oxygen and sulfur, including sulfur dioxide, selected from the group consisting of a 4-8 membered monocyclic heterocycle, a 6-10 membered fused bicyclic heterocycle, a 6-10 membered bridged heterocycle and a 6-10 membered spiro heterocycle, each substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 242. The compound of embodiment 240, wherein $R^{34}$ is a 4-8 membered monocyclic heterocycle substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 243. The compound of embodiment 240, wherein $R^{34}$ is a 6-10 membered fused bicyclic heterocycle substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 244. The compound of embodiment 240, wherein $R^{34}$ is a 6-10 membered bridged heterocycle substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 245. The compound of embodiment 240, wherein $R^{34}$ is a 6-10 membered spiro heterocycle substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 246. The compound of any one of embodiments 240 to 245, wherein $R^{34}$ is selected from azetidine, pyrrolidine, 2-azabicyclo[2.1.1]hexane, morpholine, 2-oxa-5-azabicyclo[4.1.0]heptane, 1, 4-oxazepane, 2-oxa-6-aza-adamantane, 5-oxa-8-azaspiro[2.6]nonane, 2-oxa-6-azabicyclo[3.2.1]octane, 6-oxa-3-azabicyclo[3.2.1]octane, 3-oxa-6-azabicyclo[3.2.1]octane, 6-oxa-2-azabicyclo[3.2.1]octane, 2-oxa-5-azabicyclo[2.2.1]heptane, 3-oxa-9-azabicyclo[3.3.1]nonane, 3,7-dioxa-9-azabicyclo[3.3.1]nonane, 3-oxa-7-azabicyclo[3.3.1]nonane, 3,9-dioxa-7-azabicyclo[3.3.1]nonane, 3-oxa-8-azabicyclo[3.2.1]octane, 2-oxa-5-azabicyclo[2.2.2]octane, 7-oxa-2-azabicyclo[3.3.1]nonane, 8-oxa-3-azabicyclo[3.2.1]octane, 9-oxa-3-azabicyclo[3.3.1]nonane, 6-oxa-8-azabicyclo[3.2.2]nonane, 2-oxa-6-azaspiro[3.3]heptane, 3-oxa-6-azabicyclo[3.1.1]heptane, 6-oxa-3-azabicyclo[3.1.1]heptane, thiomorpholine, thiomorpholine 1,1-dioxide, 1,4-thiazepane, 1,4-thiazepane 1,1-dioxide, 3-thia-6-azabicyclo[3.2.1]octane, 3-thia-8-azabicyclo[3.2.1]octane 3,3-dioxide, 3-thia-7-azabicyclo[3.3.1]nonane, 3-thia-6-azabicyclo[3.2.1]octane 3,3-dioxide, 3-thia-7-azabicyclo[3.3.1]nonane 3,3-dioxide, 2-thia-5-azabicyclo[2.2.1]heptane, 2-thia-5-azabicyclo[2.2.1]heptane 2,2-dioxide, 2-thia-6-azaspiro[3.4]octane 2,2-dioxide, 2-thia-6-azaspiro[3.3]heptane 2,2-dioxide, 2-thia-6-azaspiro[3.3]heptane and hexahydro-1H-thieno[3,4-c]pyrrole 2,2-dioxide, each substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 247. The compound of embodiment 246, wherein $R^{34}$ is pyrrolidine substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 248. The compound of embodiment 246, wherein $R^{34}$ is morpholine substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 249. The compound of any one of embodiments 240 to 248, wherein the attachment point for $R^{34}$ is the nitrogen atom of the heterocycle.

Embodiment 250. The compound of embodiment 249, wherein $R^{34}$ is selected from the group consisting of:

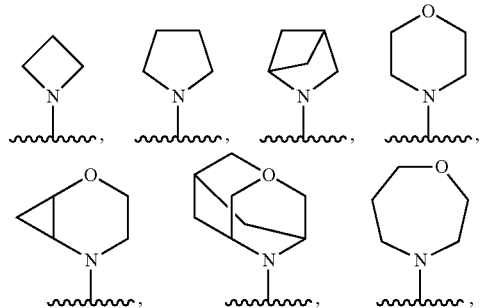

each substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 251. The compound of embodiment 249, wherein $R^{34}$ is selected from the group consisting of:

-continued

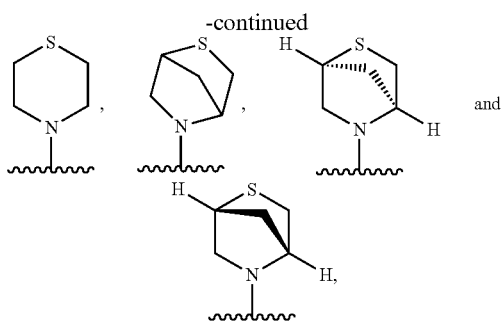

each substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 252. The compound of embodiment 249, wherein $R^{34}$ is selected from the group consisting of:

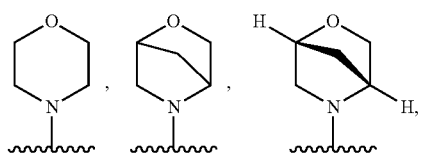

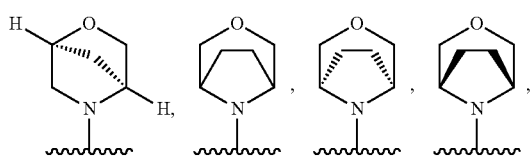

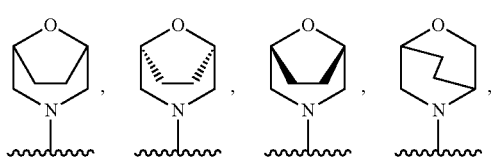

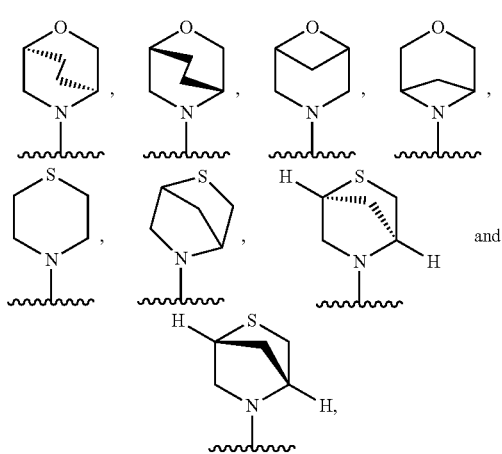

each substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 253. The compound of embodiment 249, wherein $R^{34}$ is selected from the group consisting of:

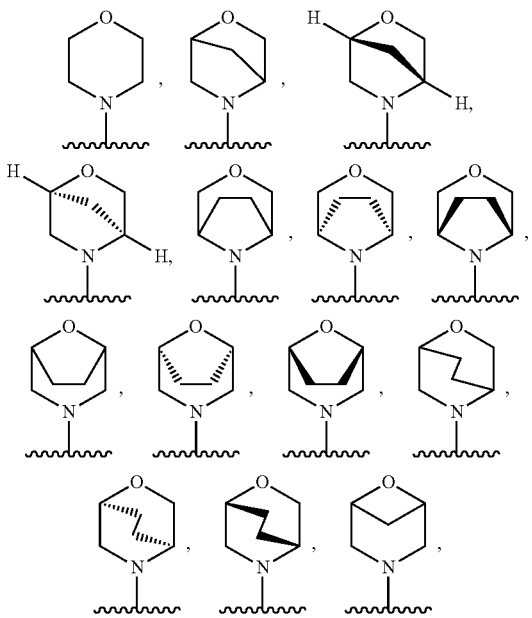

each substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 254. The compound of embodiment 250, wherein $R^{34}$ is

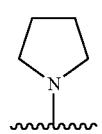 [SMILES: *N1CCCC1]

substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 255. The compound of embodiment 250, wherein $R^{34}$ is

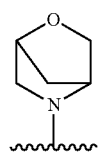 [SMILES: *N1CC2CC1CO2]

substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 256. The compound of embodiment 250, wherein $R^{34}$ is

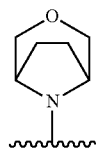

substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 257. The compound of embodiment 250, wherein $R^{34}$ is

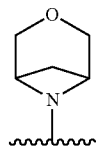

substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 258. The compound of embodiment 250, wherein $R^{34}$ is

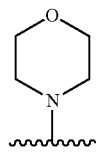

substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 259. The compound of any one of embodiments 240 to 258, wherein the 4-10 membered heterocycle of $R^{34}$ is substituted with 0, 1, 2, 3 or 4 substituents independently selected from fluoro, methyl, ethyl, hydroxy, methoxy, trifluoromethyl, trifluoromethoxy, —$CH_2OCH_3$, —$CH_2CH_2OCH_3$, —$CH_2CH_2OCH_2CH_2OCH_3$, —$CH_2N(CH_3)_2$, and —$CH_2CH_2N(CH_3)_2$.

Embodiment 260. The compound of any one of embodiments 240 to 258, wherein the 4-10 membered heterocycle of $R^{34}$ is substituted with 0, 1 or 2 substituents independently selected from fluoro, methyl, ethyl, hydroxy, methoxy, trifluoromethyl, trifluoromethoxy, $CH_2OCH_3$, $CH_2CH_2OCH_3$, $CH_2CH_2OCH_2CH_2OCH_3$, $CH_2N(CH_3)_2$, and $CH_2CH_2N(CH_3)_2$.

Embodiment 261. The compound of any one of embodiments 240 to 258, wherein the 4-10 membered heterocycle of $R^{34}$ is substituted with 0, 1 or 2 substituents independently selected from fluoro and methyl.

Embodiment 262. The compound of any one of embodiments 240 to 258, wherein the 4-10 membered heterocycle of $R^{34}$ is unsubstituted.

Embodiment 263. The compound of any one of embodiments 240 to 250, wherein $R^{34}$ is selected from the group consisting of.

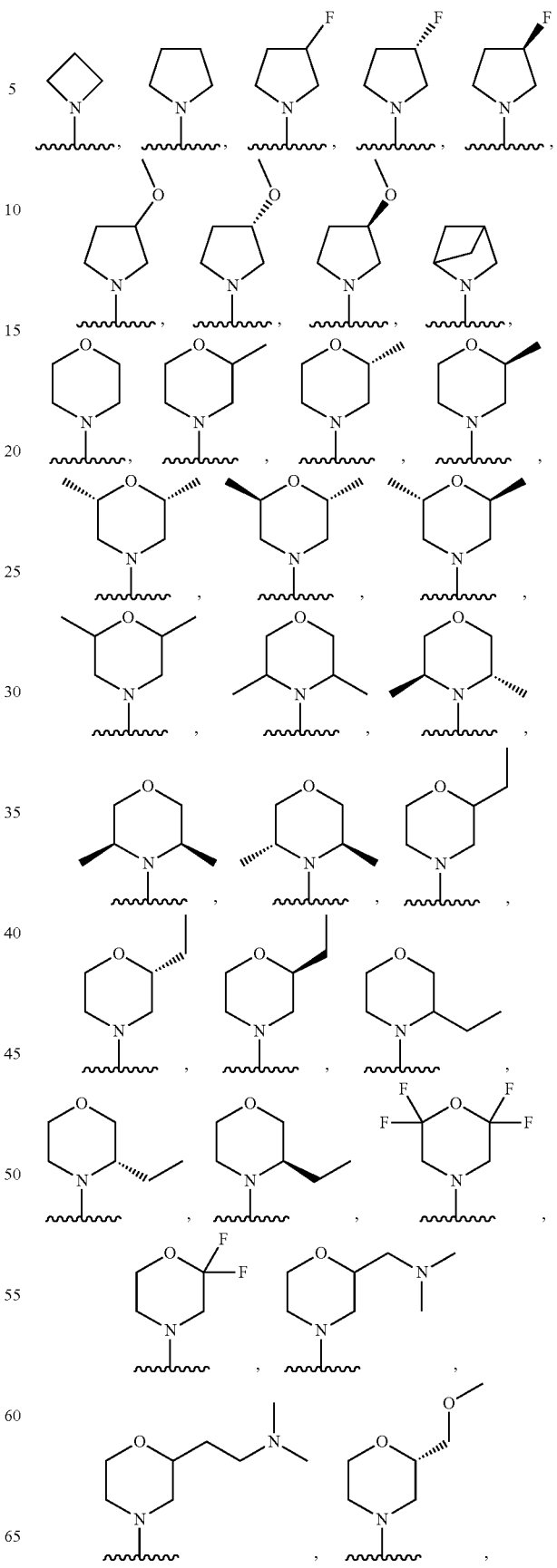

-continued
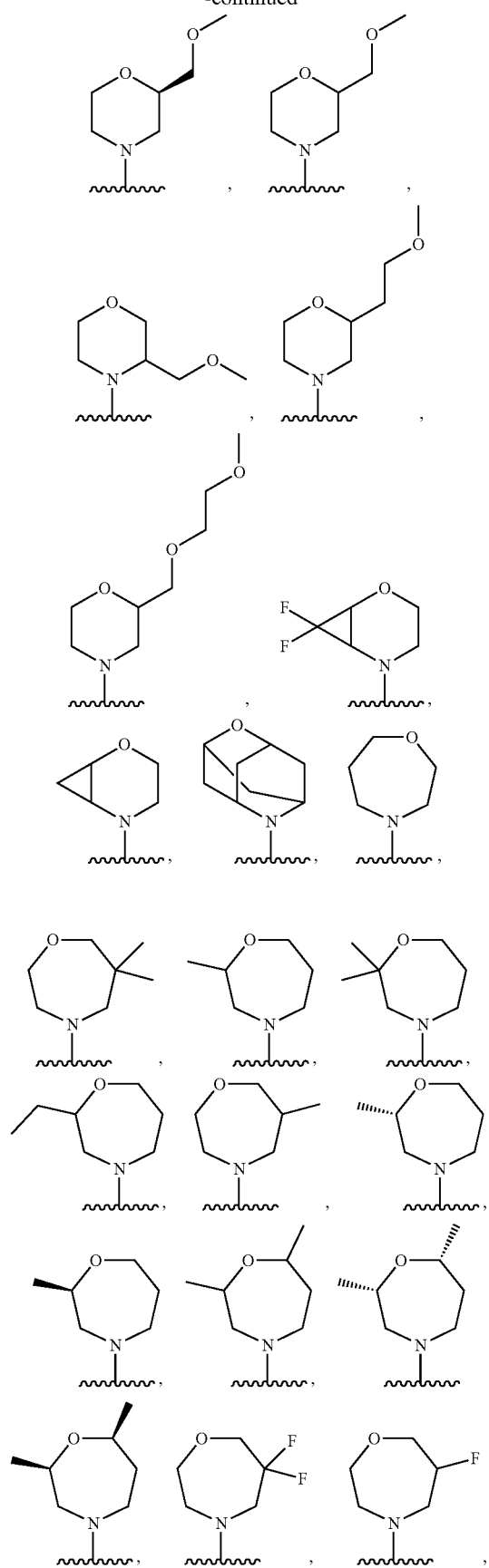
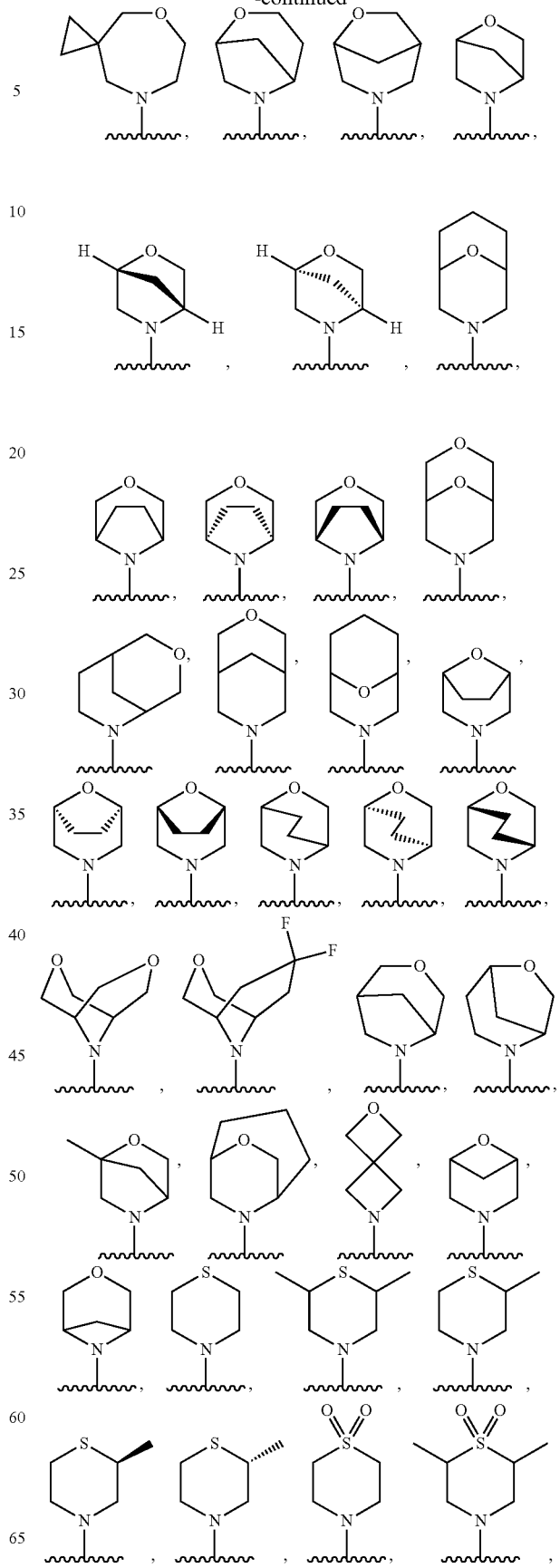

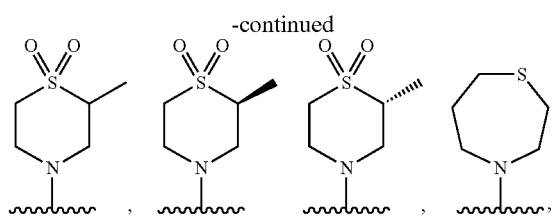
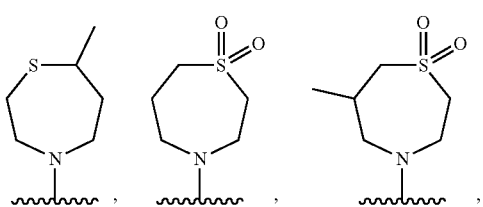
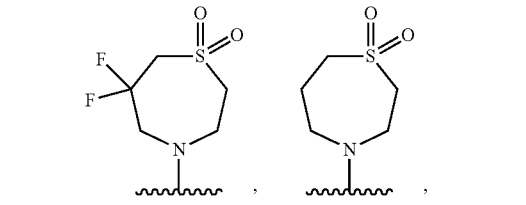
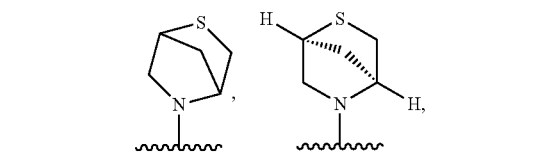
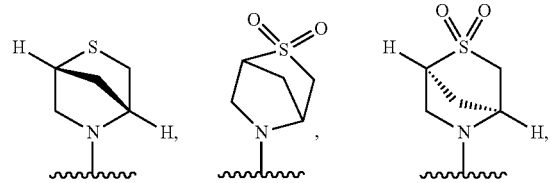
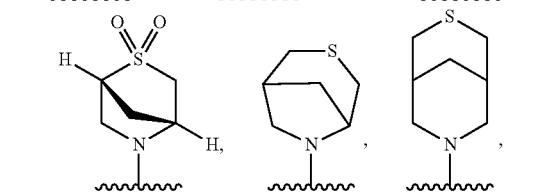
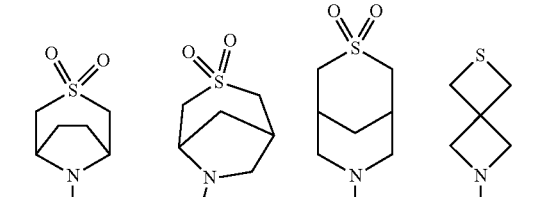
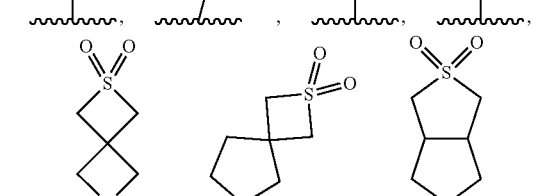
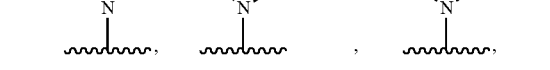
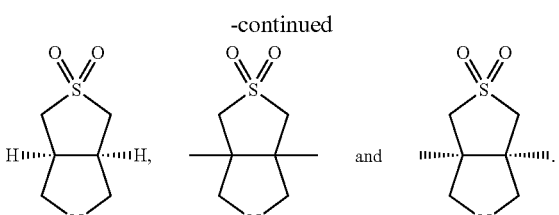 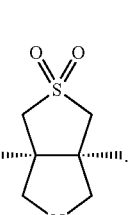
Embodiment 264. The compound of any one of embodiments 240 to 250, wherein $R^{34}$ is selected from the group consisting of.
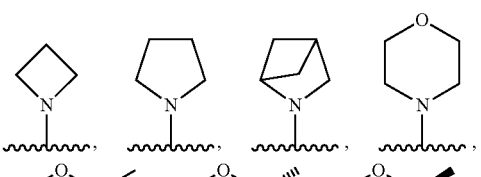
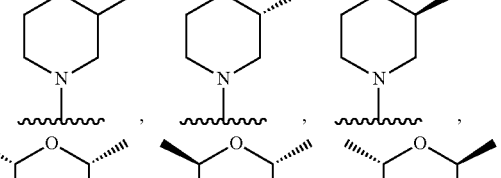
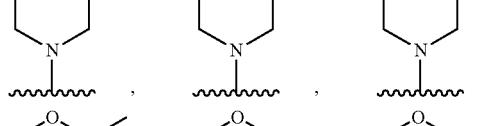
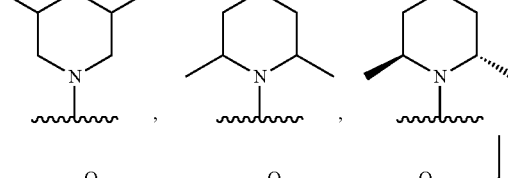
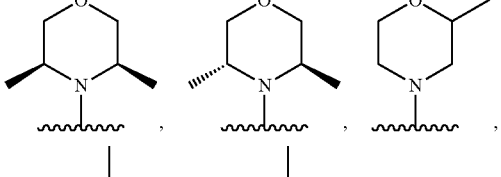
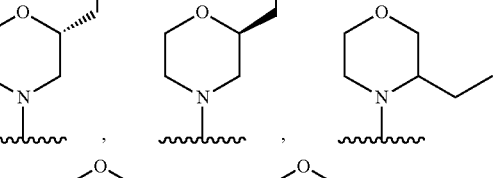
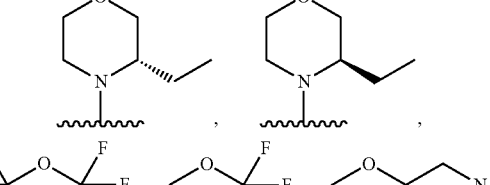
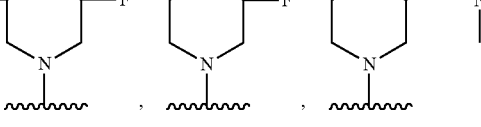

103
-continued
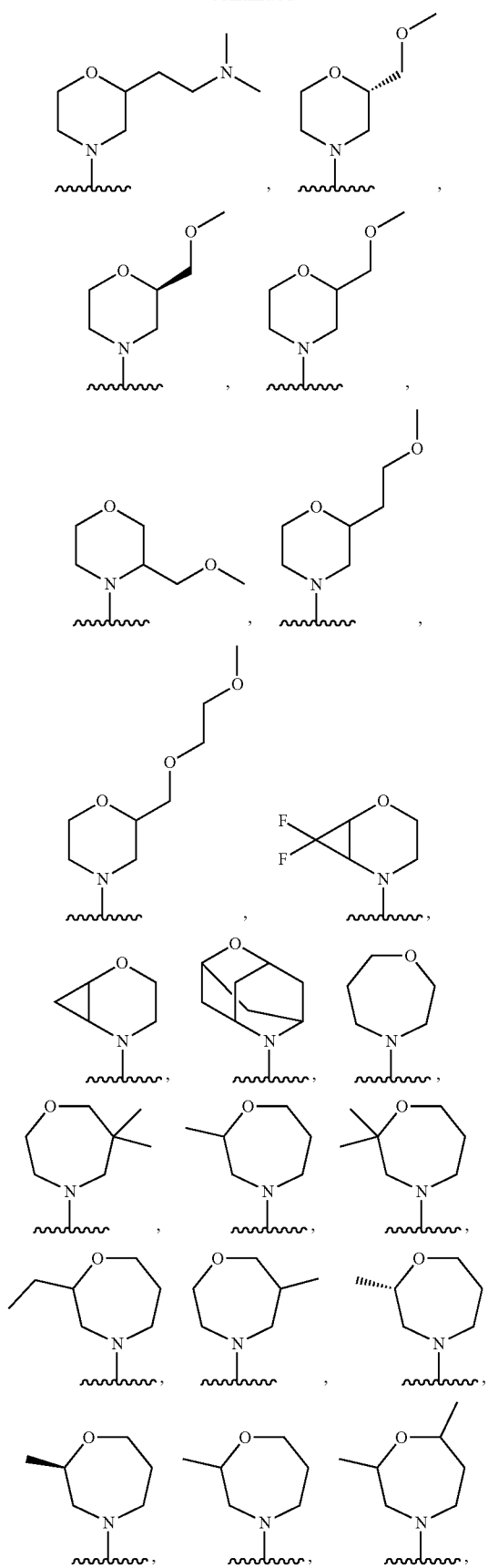
104
-continued
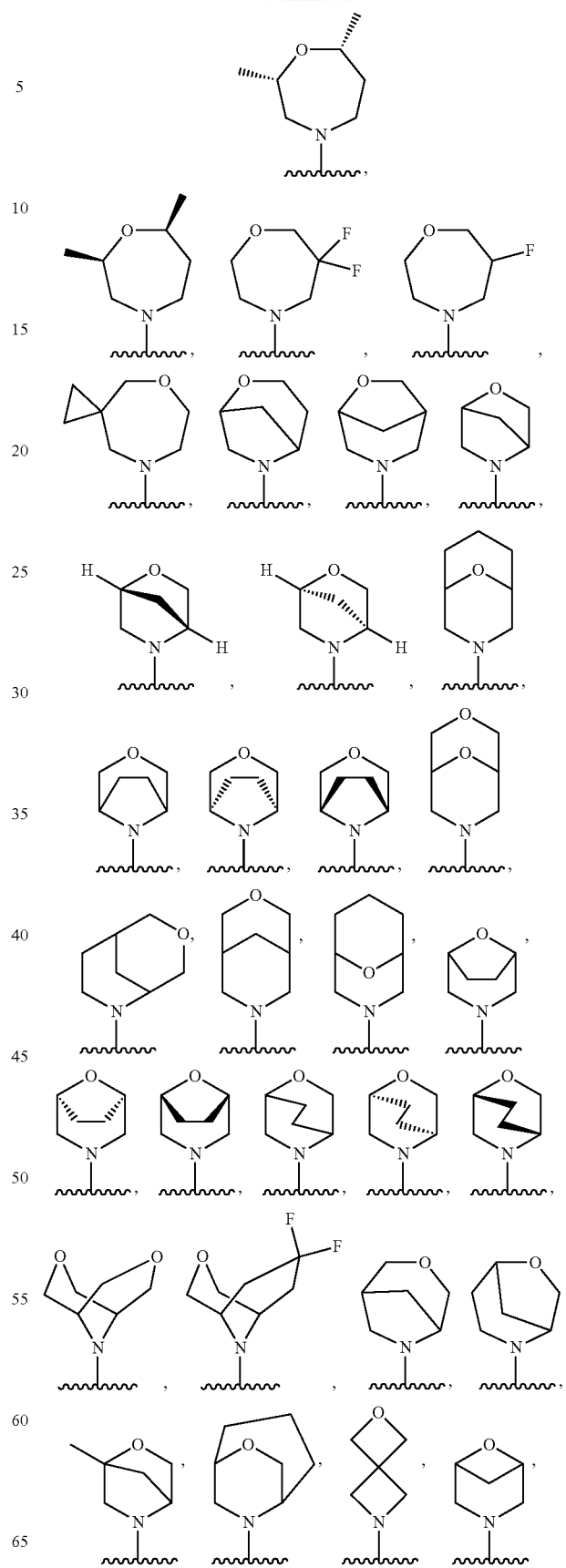

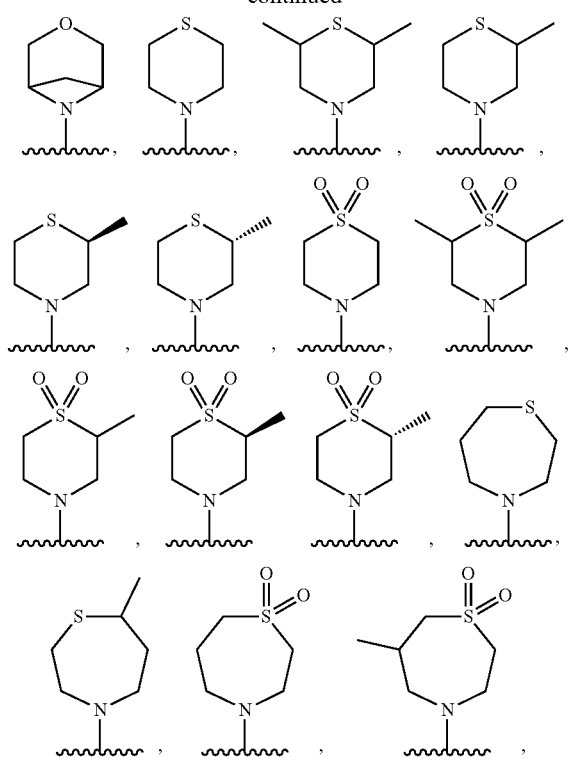
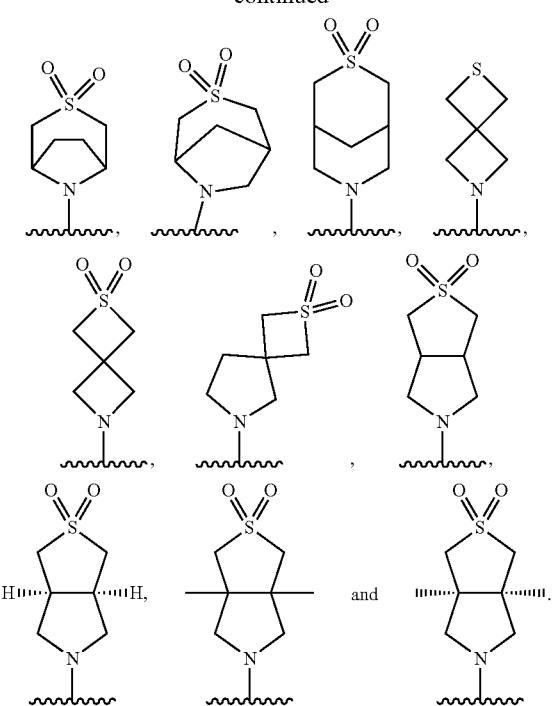
Embodiment 265. The compound of any one of embodiments 240 to 250, wherein $R^{34}$ is unsubstituted
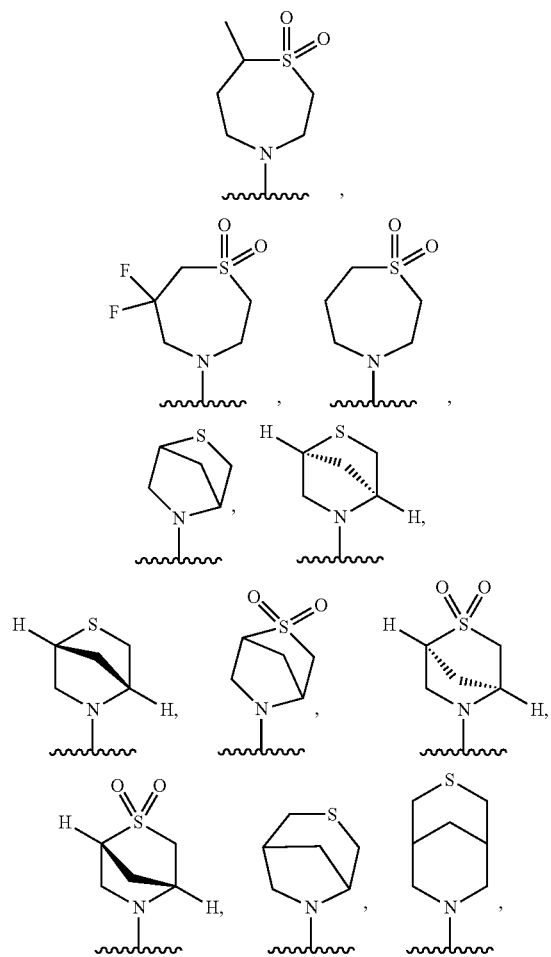
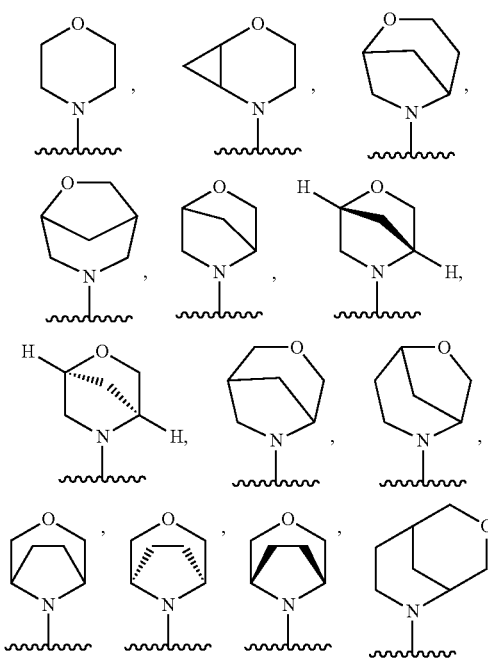

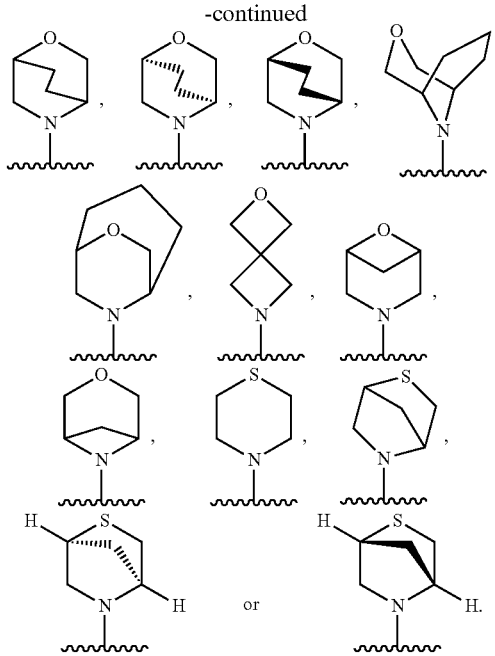

Embodiment 266. The compound of any one of embodiments 240 to 250, wherein $R^{34}$ is unsubstituted

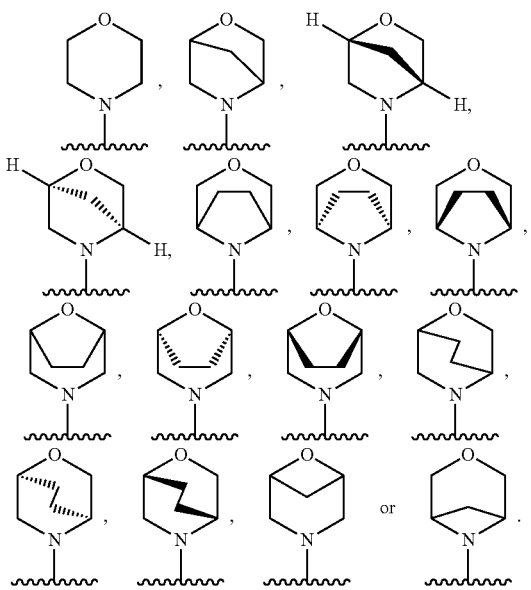

Embodiment 267. The compound of any one of embodiments 240 to 250, wherein $R^{34}$ is unsubstituted

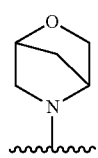

Embodiment 268. The compound of any one of embodiments 240 to 250, wherein $R^{34}$ is unsubstituted

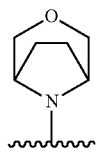 [SMILES: *N1C2CCC1COC2]

Embodiment 269. The compound of any one of embodiments 240 to 250, wherein $R^{34}$ is unsubstituted

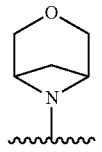 [SMILES: *N1C2COCC1C2]

Embodiment 270. The compound of any one of embodiments 240 to 250, wherein $R^{34}$ is unsubstituted

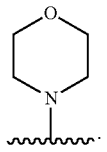

Embodiment 271. The compound of any one of embodiments 240 to 270, wherein u is 1.

Embodiment 272. The compound of any one of embodiments 1-63, 66-84, 86-208 and 211-271, wherein $R^{35}$ is a 5-6 membered heteroaryl group containing at least one nitrogen atom, wherein the heteroaryl is substituted with 0, 1, 2 or 3 substituents independently selected from halo, hydroxy, $C_1$-$C_4$ alkyl, $C_1$-$C_4$ hydroxyalkyl, $C_1$-$C_6$ alkoxy, $C_1$-$C_4$ haloalkyl, $C_1$-$C_4$ haloalkoxy, $C_3$-$C_6$ heterocyclyl optionally substituted with one or two substituents independently selected from halo, hydroxy and methyl, and $C_3$-$C_6$ cycloalkyl optionally substituted with one or two substituents independently selected from halo, hydroxy and methyl.

Embodiment 273. The compound of any one of embodiments 1-63, 66-84, 86-208 and 211-271, wherein $R^{35}$ is a 5-6 membered heteroaryl group containing at least one nitrogen atom, wherein the heteroaryl is substituted with 0, 1 or 2 substituents independently selected from halo, hydroxy, $C_1$-$C_4$ alkyl, $C_1$-$C_4$ hydroxyalkyl, $C_1$-$C_6$ alkoxy, $C_1$-$C_4$ haloalkyl, $C_1$-$C_4$ haloalkoxy, $C_3$-$C_6$ heterocyclyl optionally substituted with one or two substituents independently selected from halo and methyl, and $C_3$-$C_6$ cycloalkyl optionally substituted with one or two substituents independently selected from halo and methyl.

Embodiment 274. The compound of any one of embodiments 1-63, 66-84, 86-208 and 211-271, wherein $R^{35}$ is selected from the group consisting of pyrimidinyl, pyrazinyl, oxazolyl, 1,2,4-oxadiazolyl, 1,3,4-oxadiazolyl, 1H-1,2,4-triazolyl, imidazolyl, 4H-1,2,4-triazolyl, 1,2,4-thiadiazolyl and isoxazolyl, each substituted with 0, 1, 2 or 3 substituents independently selected from halo, hydroxy, $C_1$-$C_4$ alkyl, $C_1$-$C_4$ hydroxyalkyl, $C_1$-$C_6$ alkoxy, $C_1$-$C_4$ haloalkyl, $C_1$-$C_4$ haloalkoxy, $C_3$-$C_6$ heterocyclyl optionally substituted with one or two substituents independently selected from halo, hydroxy and methyl, and $C_3$-$C_6$ cycloalkyl optionally substituted with one or two substituents independently selected from halo, hydroxy and methyl.

Embodiment 275. The compound of any one of embodiments 1-63, 66-84, 86-208 and 211-271, wherein $R^{35}$ is selected from the group consisting of pyrimidinyl, pyrazinyl, oxazolyl, 1,2,4-oxadiazolyl, 1,3,4-oxadiazolyl, 1H-1,2,4-triazolyl, imidazolyl, 4H-1,2,4-triazolyl, 1,2,4-thiadiazolyl and isoxazolyl, each substituted with 0, 1 or 2 substituents independently selected from halo, hydroxy, $C_1$-$C_4$ alkyl, $C_1$-$C_4$ hydroxyalkyl, $C_1$-$C_6$ alkoxy, $C_1$-$C_4$ haloalkyl, $C_1$-$C_4$ haloalkoxy, $C_3$-$C_6$ heterocyclyl optionally substituted with one or two substituents independently selected from halo and methyl, and $C_3$-$C_6$ cycloalkyl optionally substituted with one or two substituents independently selected from halo and methyl.

Embodiment 276. The compound of any one of embodiments 1-63, 66-84, 86-208 and 211-271, wherein $R^{35}$ is selected from the group consisting of pyrimidinyl, oxazolyl, 1,2,4-oxadiazolyl, imidazolyl and 1,2,4-thiadiazolyl, each substituted with 0, 1, 2 or 3 substituents independently selected from halo, hydroxy, $C_1$-$C_4$ alkyl, $C_1$-$C_4$ hydroxyalkyl, $C_1$-$C_6$ alkoxy, $C_1$-$C_4$ haloalkyl, $C_1$-$C_4$ haloalkoxy, $C_3$-$C_6$ heterocyclyl optionally substituted with one or two substituents independently selected from halo, hydroxy and methyl, and $C_3$-$C_6$ cycloalkyl optionally substituted with one or two substituents independently selected from halo, hydroxy and methyl.

Embodiment 277. The compound of any one of embodiments 1-63, 66-84, 86-208 and 211-271, wherein $R^{35}$ is selected from the group consisting of pyrimidinyl, oxazolyl, 1,2,4-oxadiazolyl, imidazolyl and 1,2,4-thiadiazolyl, each substituted with 0, 1 or 2 substituents independently selected from halo, hydroxy, $C_1$-$C_4$ alkyl, $C_1$-$C_4$ hydroxyalkyl, $C_1$-$C_6$ alkoxy, $C_1$-$C_4$ haloalkyl, $C_1$-$C_4$ haloalkoxy, $C_3$-$C_6$ heterocyclyl optionally substituted with one or two substituents independently selected from halo and methyl, and $C_3$-$C_6$ cycloalkyl optionally substituted with one or two substituents independently selected from halo and methyl.

Embodiment 278. The compound of any one of embodiments 1-63, 66-84, 86-208 and 211-271, wherein $R^{35}$ is selected from the group consisting of

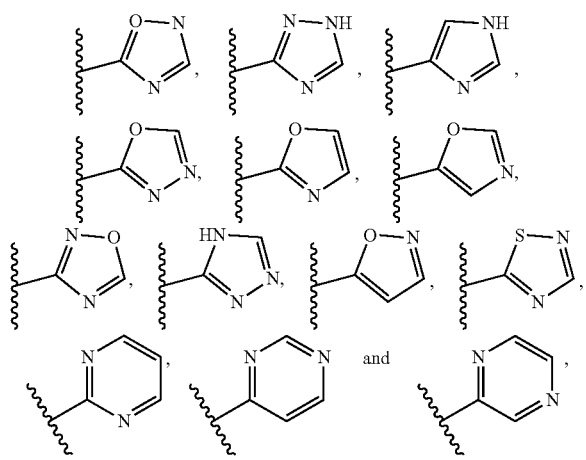

each substituted with 0, 1, 2 or 3 substituents independently selected from halo, hydroxy, $C_1$-$C_4$ alkyl, $C_1$-$C_4$ hydroxyalkyl, $C_1$-$C_6$ alkoxy, $C_1$-$C_4$ haloalkyl, $C_1$-$C_4$ haloalkoxy, $C_3$-$C_6$ heterocyclyl optionally substituted with one or two substituents independently selected from halo, hydroxy and methyl, and $C_3$-$C_6$ cycloalkyl optionally substituted with one or two substituents independently selected from halo, hydroxy and methyl.

Embodiment 279. The compound of any one of embodiments 1-63, 66-84, 86-208 and 211-271, wherein $R^{35}$ is selected from the group consisting of

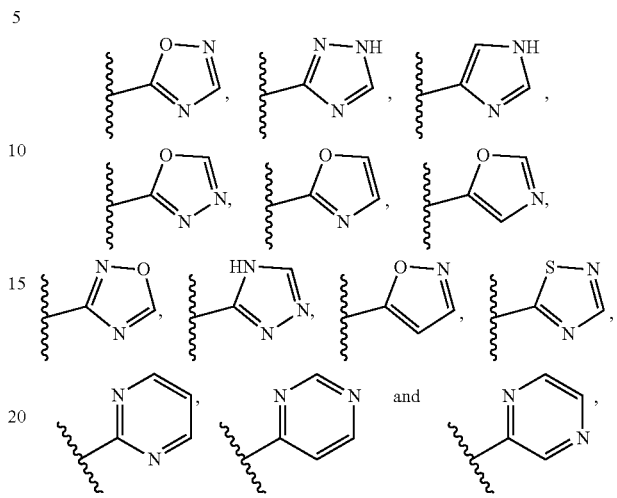

each substituted with 0, 1 or 2 substituents independently selected from halo, hydroxy, $C_1$-$C_4$ alkyl, $C_1$-$C_4$ hydroxyalkyl, $C_1$-$C_6$ alkoxy, $C_1$-$C_4$ haloalkyl, $C_1$-$C_4$ haloalkoxy, $C_3$-$C_6$ heterocyclyl optionally substituted with one or two substituents independently selected from halo and methyl, and $C_3$-$C_6$ cycloalkyl optionally substituted with one or two substituents independently selected from halo and methyl.

Embodiment 280. The compound of any one of embodiments 1-63, 66-84, 86-208 and 211-271, wherein $R^{35}$ is selected from the group consisting of

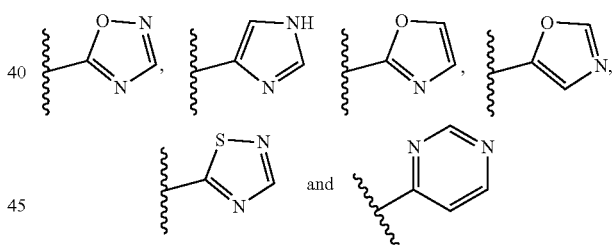

each substituted with 0, 1 or 2 substituents independently selected from halo, hydroxy, $C_1$-$C_4$ alkyl, $C_1$-$C_4$ hydroxyalkyl, $C_1$-$C_6$ alkoxy, $C_1$-$C_4$ haloalkyl, $C_1$-$C_4$ haloalkoxy, $C_3$-$C_6$ heterocyclyl optionally substituted with one or two substituents independently selected from halo, hydroxy and methyl, and $C_3$-$C_6$ cycloalkyl optionally substituted with one or two substituents independently selected from halo, hydroxy and methyl.

Embodiment 281. The compound of any one of embodiments 1-63, 66-84, 86-208 and 211-271, wherein $R^{35}$ is selected from the group consisting of

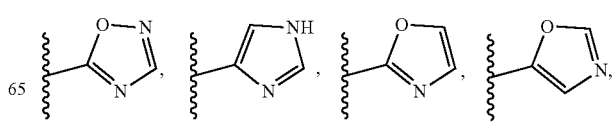

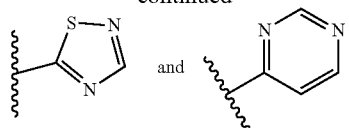
and each substituted with 0, 1 or 2 substituents independently selected from halo, hydroxy, $C_1$-$C_4$ alkyl, $C_1$-$C_4$ hydroxyalkyl, $C_1$-$C_6$ alkoxy, $C_1$-$C_4$ haloalkyl, $C_1$-$C_4$ haloalkoxy, $C_3$-$C_6$ heterocyclyl optionally substituted with one or two substituents independently selected from halo and methyl, and $C_3$-$C_6$ cycloalkyl optionally substituted with one or two substituents independently selected from halo and methyl.

Embodiment 282. The compound of any one of embodiments 1-63, 66-84, 86-208 and 211-271, wherein $R^{35}$ is a 6 membered heteroaryl group substituted with 0, 1, 2 or 3 substituents independently selected from halo, hydroxy, $C_1$-$C_4$ alkyl, $C_1$-$C_4$ hydroxyalkyl, $C_1$-$C_6$ alkoxy, $C_1$-$C_4$ haloalkyl, $C_1$-$C_4$ haloalkoxy, $C_3$-$C_6$ heterocyclyl optionally substituted with one or two substituents independently selected from halo and methyl, and $C_3$-$C_6$ cycloalkyl optionally substituted with one or two substituents independently selected from halo and methyl.

Embodiment 283. The compound of any one of embodiments 1-63, 66-84, 86-208 and 211-271, wherein $R^{35}$ is a 6 membered heteroaryl group substituted with 0, 1 or 2 substituents independently selected from halo, hydroxy, $C_1$-$C_4$ alkyl, $C_1$-$C_4$ hydroxyalkyl, $C_1$-$C_6$ alkoxy, $C_1$-$C_4$ haloalkyl, $C_1$-$C_4$ haloalkoxy, $C_3$-$C_6$ heterocyclyl optionally substituted with one or two substituents independently selected from halo and methyl, and $C_3$-$C_6$ cycloalkyl optionally substituted with one or two substituents independently selected from halo and methyl.

Embodiment 284. The compound of any one of embodiments 1-63, 66-84, 86-208 and 211-271, wherein $R^{35}$ is pyrimidinyl or pyridazinyl substituted with 0, 1, 2 or 3 substituents independently selected from halo, hydroxy, $C_1$-$C_4$ alkyl, $C_1$-$C_4$ hydroxyalkyl, $C_1$-$C_6$ alkoxy, $C_1$-$C_4$ haloalkyl, $C_1$-$C_4$ haloalkoxy, $C_3$-$C_6$ heterocyclyl optionally substituted with one or two substituents independently selected from halo and methyl, and $C_3$-$C_6$ cycloalkyl optionally substituted with one or two substituents independently selected from halo and methyl.

Embodiment 285. The compound of any one of embodiments 1-63, 66-84, 86-208 and 211-271, wherein $R^{35}$ is pyrimidinyl or pyridazinyl substituted with 0, 1 or 2 substituents independently selected from halo, hydroxy, $C_1$-$C_4$ alkyl, $C_1$-$C_4$ hydroxyalkyl, $C_1$-$C_6$ alkoxy, $C_1$-$C_4$ haloalkyl, $C_1$-$C_4$ haloalkoxy, $C_3$-$C_6$ heterocyclyl optionally substituted with one or two substituents independently selected from halo and methyl, and $C_3$-$C_6$ cycloalkyl optionally substituted with one or two substituents independently selected from halo and methyl.

Embodiment 286. The compound of any one of embodiments 1-63, 66-84, 86-208 and 211-271, wherein $R^{35}$ is selected from the group consisting of

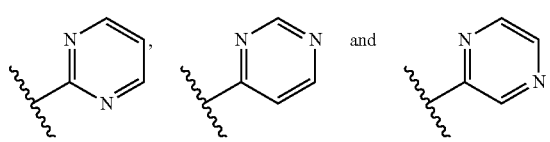 [SMILES: *c1ncccn1 ; *c1ccncn1 ; *c1cnccn1]

substituted with 0, 1, 2 or 3 substituents independently selected from halo, hydroxy, $C_1$-$C_4$ alkyl, $C_1$-$C_4$ hydroxyalkyl, $C_1$-$C_6$ alkoxy, $C_1$-$C_4$ haloalkyl, $C_1$-$C_4$ haloalkoxy, $C_3$-$C_6$ heterocyclyl optionally substituted with one or two substituents independently selected from halo and methyl, and $C_3$-$C_6$ cycloalkyl optionally substituted with one or two substituents independently selected from halo and methyl.

Embodiment 287. The compound of any one of embodiments 1-63, 66-84, 86-208 and 211-271, wherein $R^{35}$ is selected from the group consisting of

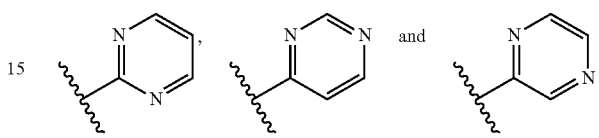

substituted with 0, 1 or 2 substituents independently selected from halo, hydroxy, $C_1$-$C_4$ alkyl, $C_1$-$C_4$ hydroxyalkyl, $C_1$-$C_6$ alkoxy, $C_1$-$C_4$ haloalkyl, $C_1$-$C_4$ haloalkoxy, $C_3$-$C_6$ heterocyclyl optionally substituted with one or two substituents independently selected from halo and methyl, and $C_3$-$C_6$ cycloalkyl optionally substituted with one or two substituents independently selected from halo and methyl.

Embodiment 288. The compound of any one of embodiments 1-63, 66-84, 86-208 and 211-271, wherein $R^{35}$ is a 5 membered heteroaryl group containing at least one nitrogen atom, wherein the heteroaryl is substituted with 0, 1 or 2 substituents independently selected from halo, hydroxy, $C_1$-$C_4$ alkyl, $C_1$-$C_4$ hydroxyalkyl, $C_1$-$C_6$ alkoxy, $C_1$-$C_4$ haloalkyl, $C_1$-$C_4$ haloalkoxy, $C_3$-$C_6$ heterocyclyl optionally substituted with one or two substituents independently selected from halo, hydroxy and methyl, and $C_3$-$C_6$ cycloalkyl optionally substituted with one or two substituents independently selected from halo, hydroxy and methyl.

Embodiment 289. The compound of any one of embodiments 1-63, 66-84, 86-208 and 211-271, wherein $R^{35}$ is a 5 membered heteroaryl group containing at least one nitrogen atom, wherein the heteroaryl is substituted with 0, 1 or 2 substituents independently selected from halo, hydroxy, $C_1$-$C_4$ alkyl, $C_1$-$C_4$ hydroxyalkyl, $C_1$-$C_6$ alkoxy, $C_1$-$C_4$ haloalkyl, $C_1$-$C_4$ haloalkoxy, $C_3$-$C_6$ heterocyclyl optionally substituted with one or two substituents independently selected from halo and methyl, and $C_3$-$C_6$ cycloalkyl optionally substituted with one or two substituents independently selected from halo and methyl.

Embodiment 290. The compound of any one of embodiments 1-63, 66-84, 86-208 and 211-271, wherein $R^{35}$ is selected from the group consisting of oxazolyl, 1,2,4-oxadiazolyl, 1,3,4-oxadiazolyl, 1H-1,2,4-triazolyl, imidazolyl, 4H-1,2,4-triazolyl, 1,2,4-thiadiazolyl and isoxazolyl, each substituted with 0, 1 or 2 substituents independently selected from halo, hydroxy, $C_1$-$C_4$ alkyl, $C_1$-$C_4$ hydroxyalkyl, $C_1$-$C_6$ alkoxy, $C_1$-$C_4$ haloalkyl, $C_1$-$C_4$ haloalkoxy, $C_3$-$C_6$ heterocyclyl optionally substituted with one or two substituents independently selected from halo, hydroxy and methyl, and $C_3$-$C_6$ cycloalkyl optionally substituted with one or two substituents independently selected from halo, hydroxy and methyl.

Embodiment 291. The compound of any one of embodiments 1-63, 66-84, 86-208 and 211-271, wherein $R^{35}$ is selected from the group consisting of oxazolyl, 1,2,4-oxadiazolyl, 1,3,4-oxadiazolyl, 1H-1,2,4-triazolyl, imidazolyl, 4H-1,2,4-triazolyl, 1,2,4-thiadiazolyl and isoxazolyl, each substituted with 0, 1 or 2 substituents independently selected from halo, hydroxy, C₁-C₄ alkyl, C₁-C₄ hydroxyalkyl, C₁-C₆ alkoxy, C₁-C₄ haloalkyl, C₁-C₄ haloalkoxy, C₃-C₆ heterocyclyl optionally substituted with one or two substituents independently selected from halo and methyl, and C₃-C₆ cycloalkyl optionally substituted with one or two substituents independently selected from halo and methyl.

Embodiment 292. The compound of any one of embodiments 1-63, 66-84, 86-208 and 211-271, wherein R³⁵ is selected from the group consisting of

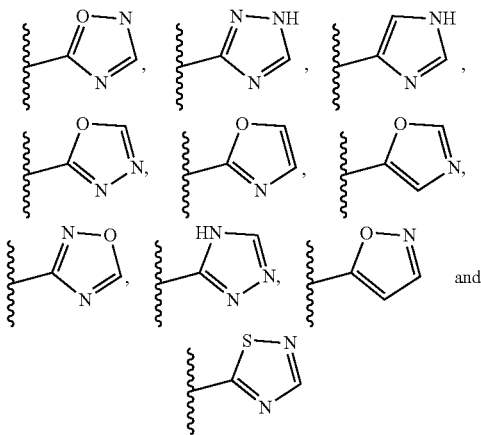

each substituted with 0, 1 or 2 substituents independently selected from halo, hydroxy, C₁-C₄ alkyl, C₁-C₄ hydroxyalkyl, C₁-C₆ alkoxy, C₁-C₄ haloalkyl, C₁-C₄ haloalkoxy, C₃-C₆ heterocyclyl optionally substituted with one or two substituents independently selected from halo, hydroxy and methyl, and C₃-C₆ cycloalkyl optionally substituted with one or two substituents independently selected from halo, hydroxy and methyl.

Embodiment 293. The compound of any one of embodiments 1-63, 66-84, 86-208 and 211-271, wherein R³⁵ is selected from the group consisting of

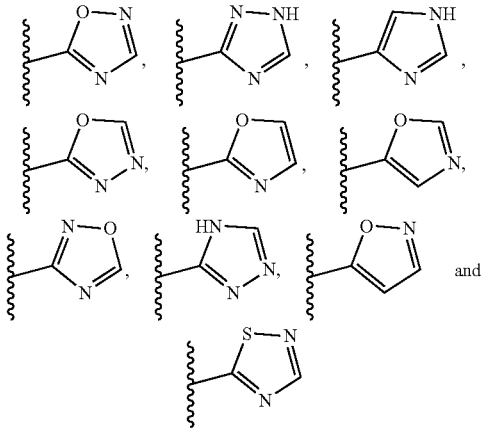

each substituted with 0, 1 or 2 substituents independently selected from halo, hydroxy, C₁-C₄ alkyl, C₁-C₄ hydroxyalkyl, C₁-C₆ alkoxy, C₁-C₄ haloalkyl, C₁-C₄ haloalkoxy, C₃-C₆ heterocyclyl optionally substituted with one or two substituents independently selected from halo and methyl, and C₃-C₆ cycloalkyl optionally substituted with one or two substituents independently selected from halo and methyl.

Embodiment 294. The compound of any one of embodiments 1-63, 66-84, 86-208 and 211-293, wherein the heteroaryl group of R³⁵ is substituted with 0 or 1 substituents selected from C₁-C₄ alkyl, C₁-C₄ hydroxyalkyl, C₁-C₄ haloalkyl, C₃-C₆ heterocyclyl optionally substituted with one or two substituents independently selected from halo, hydroxy and methyl, and C₃-C₆ cycloalkyl optionally substituted with one or two substituents independently selected from halo, hydroxy and methyl.

Embodiment 295. The compound of any one of embodiments 1-63, 66-84, 86-208 and 211-293, wherein the heteroaryl group of R³⁵ is substituted with 0 or 1 substituents selected from C₁-C₄ alkyl, C₁-C₄ hydroxyalkyl, C₁-C₄ haloalkyl, C₃-C₆ heterocyclyl optionally substituted with one or two substituents independently selected from halo and methyl, and C₃-C₆ cycloalkyl optionally substituted with one or two substituents independently selected from halo and methyl.

Embodiment 296. The compound of any one of embodiments 1-63, 66-84, 86-208 and 211-293, wherein the heteroaryl group of R³⁵ is substituted with 0 or 1 substituents selected from fluoro, methyl, ethyl, isopropyl, tert-butyl, difluoromethyl, 1-fluoroethyl, 1,1-difluoroethyl, —C(OH)(CH₃)₂, oxetan-3-yl, 3-methyloxetan-3-yl, cyclobutyl, 1-fluoroxycyclobutyl, 1-hydroxy cyclobutyl, cyclopropyl, 1-methylcyclopropyl and 2-fluorocyclopropyl.

Embodiment 297. The compound of any one of embodiments 1-63, 66-84, 86-208 and 211-293, wherein the heteroaryl group of R³⁵ is substituted with 0 or 1 substituents selected from methyl, ethyl, isopropyl, tert-butyl, difluoromethyl, 1-fluoroethyl, 1,1-difluoroethyl, —C(OH)(CH₃)₂, oxetan-3-yl, 3-methyloxetan-3-yl, cyclobutyl, cyclopropyl, 1-methylcyclopropyl and 2-fluorocyclopropyl.

Embodiment 298. The compound of any one of embodiments 1-63, 66-84, 86-208 and 211-271, wherein R³⁵ is selected from the group consisting of

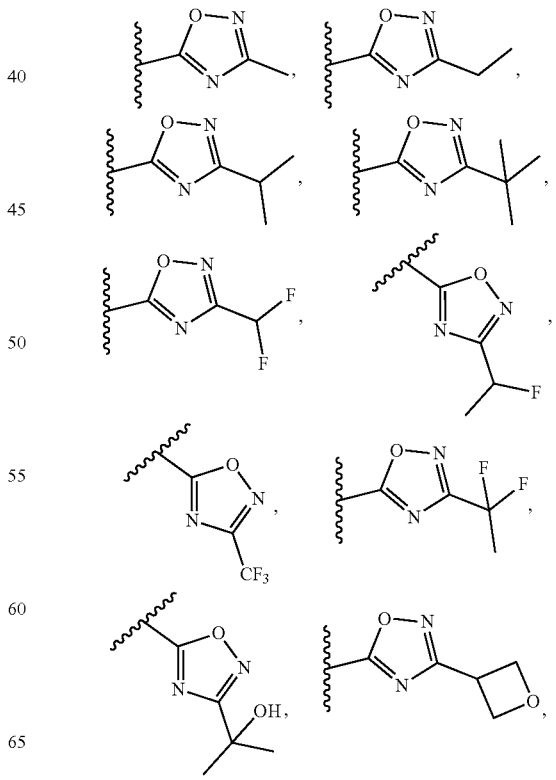

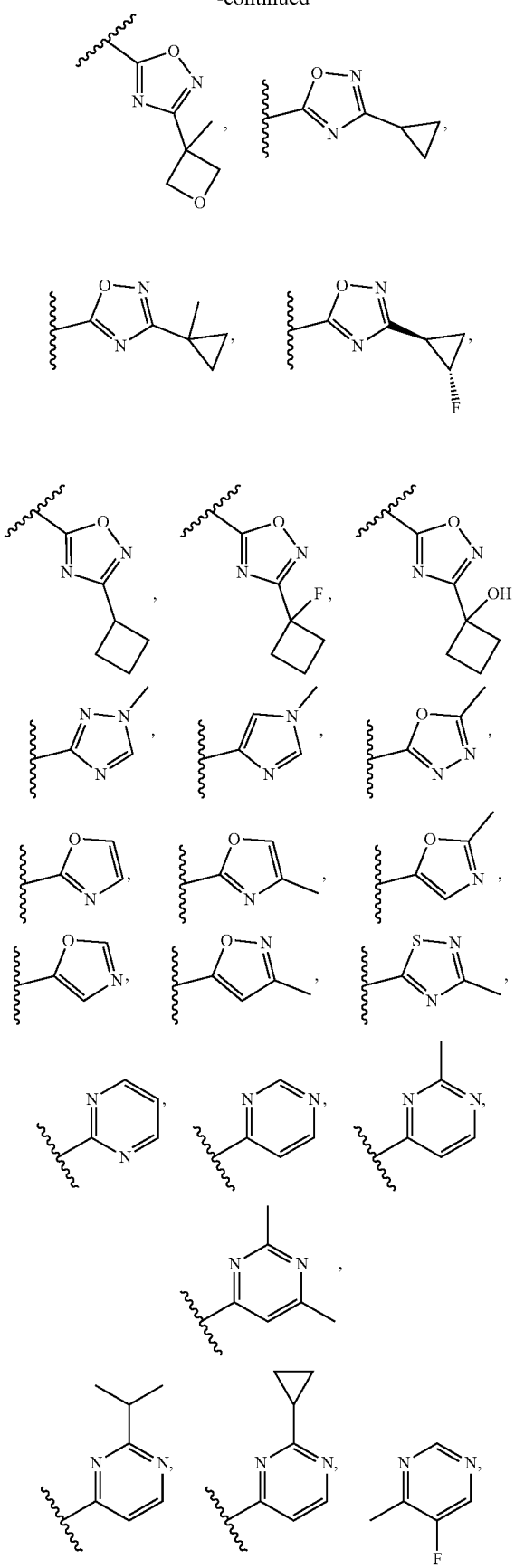
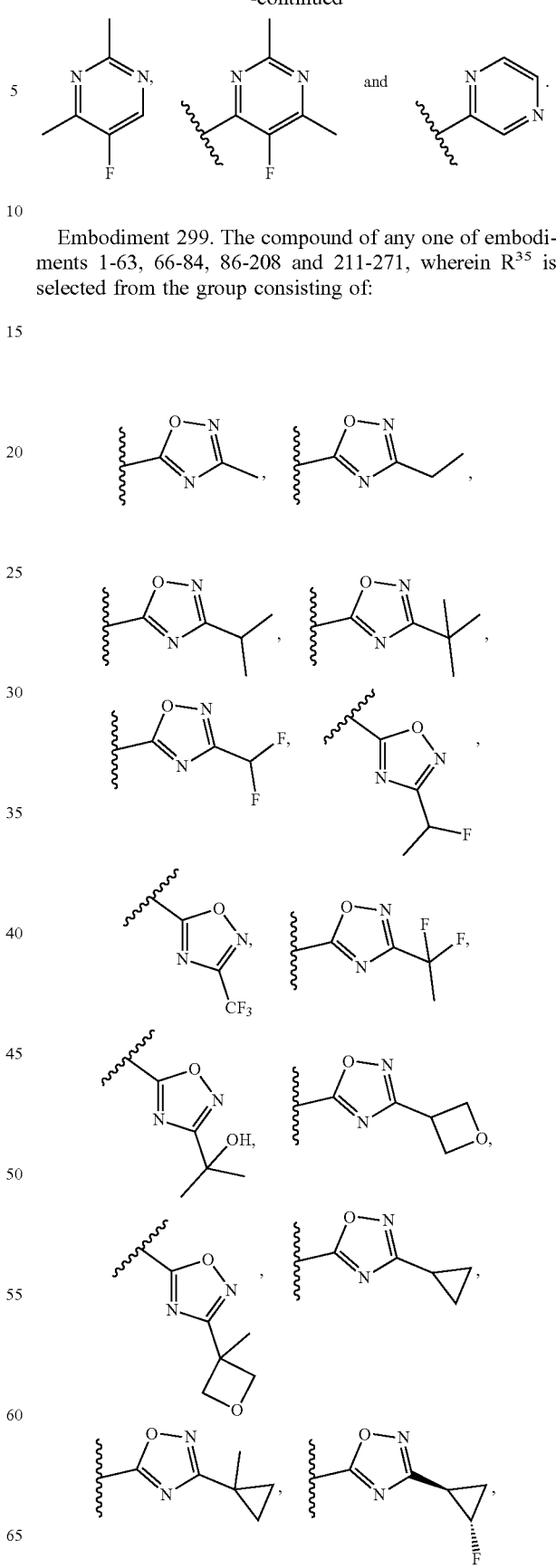
Embodiment 299. The compound of any one of embodiments 1-63, 66-84, 86-208 and 211-271, wherein $R^{35}$ is selected from the group consisting of:

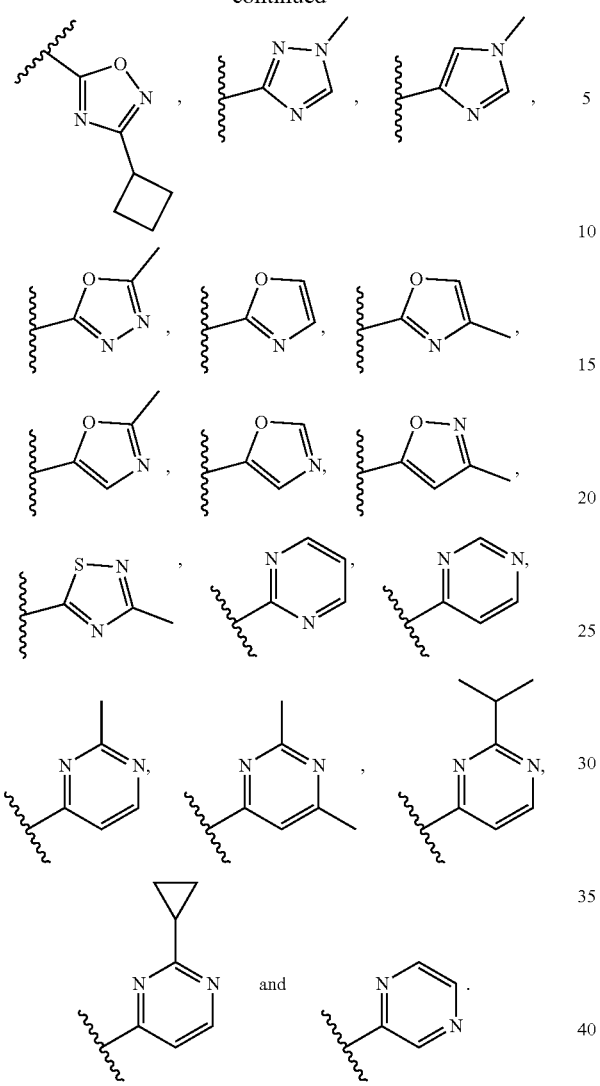
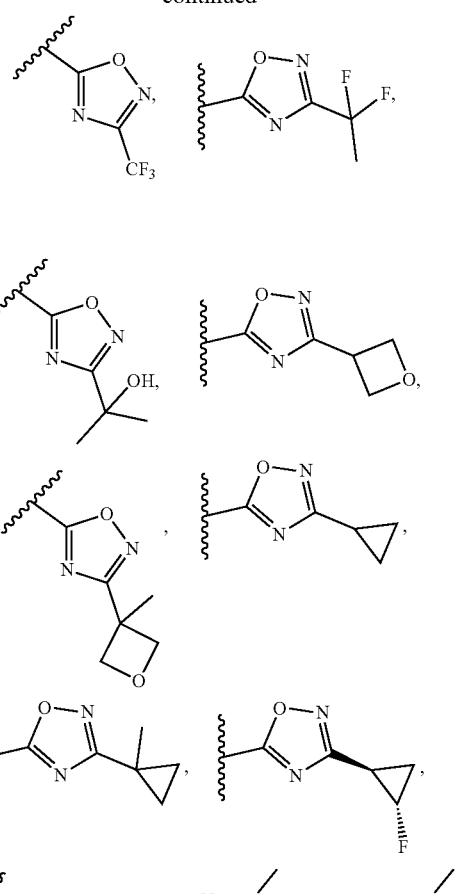
Embodiment 300. The compound of any one of embodiments 1-63, 66-84, 86-208 and 211-271, wherein $R^{35}$ is selected from the group consisting of:
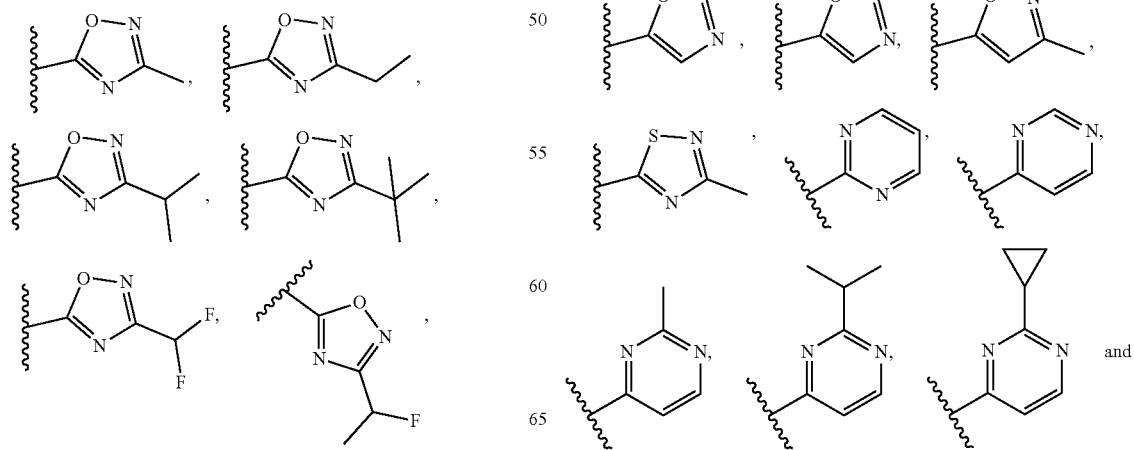

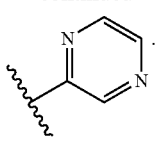
Embodiment 301. The compound of any one of embodiments 1-63, 66-84, 86-208 and 211-271, wherein $R^{35}$ is selected from the group consisting of
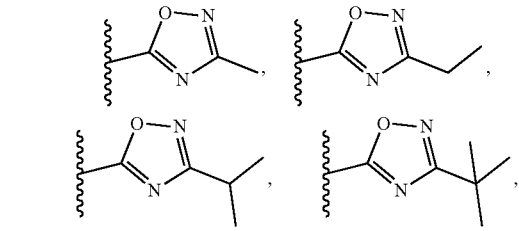
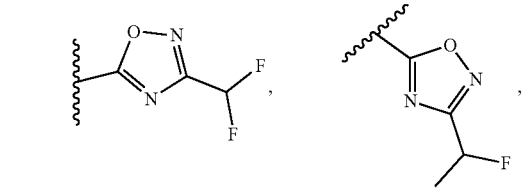
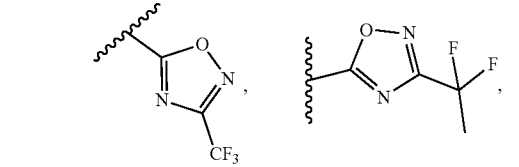
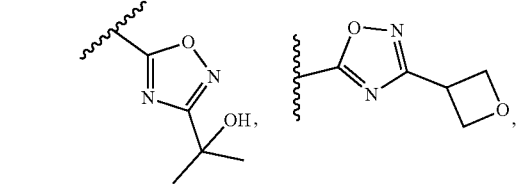
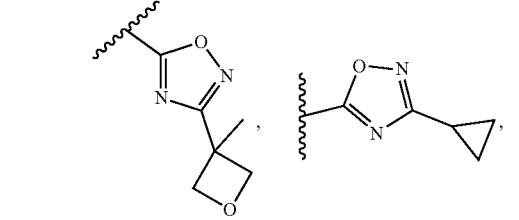
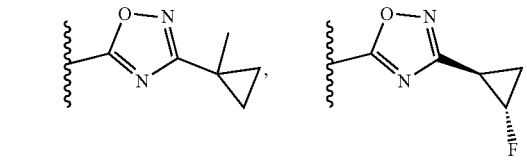
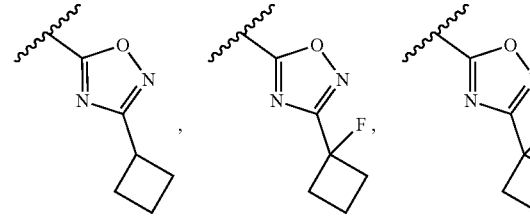
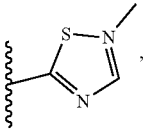, 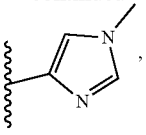, 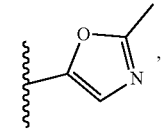
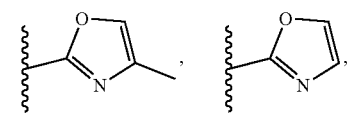
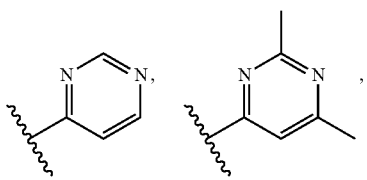
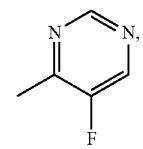
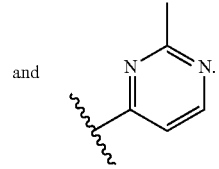 and
Embodiment 302. The compound of any one of embodiments 1-63, 66-84, 86-208 and 211-271, wherein $R^{35}$ is selected from the group consisting of:
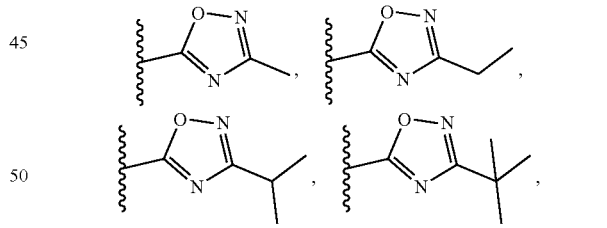
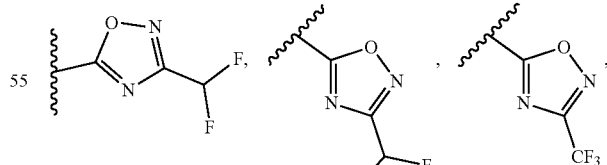
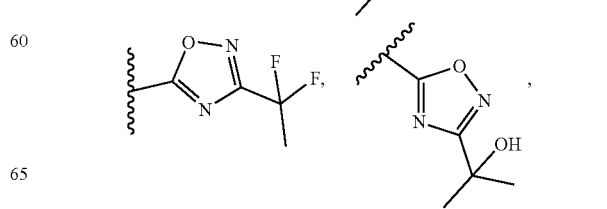

-continued

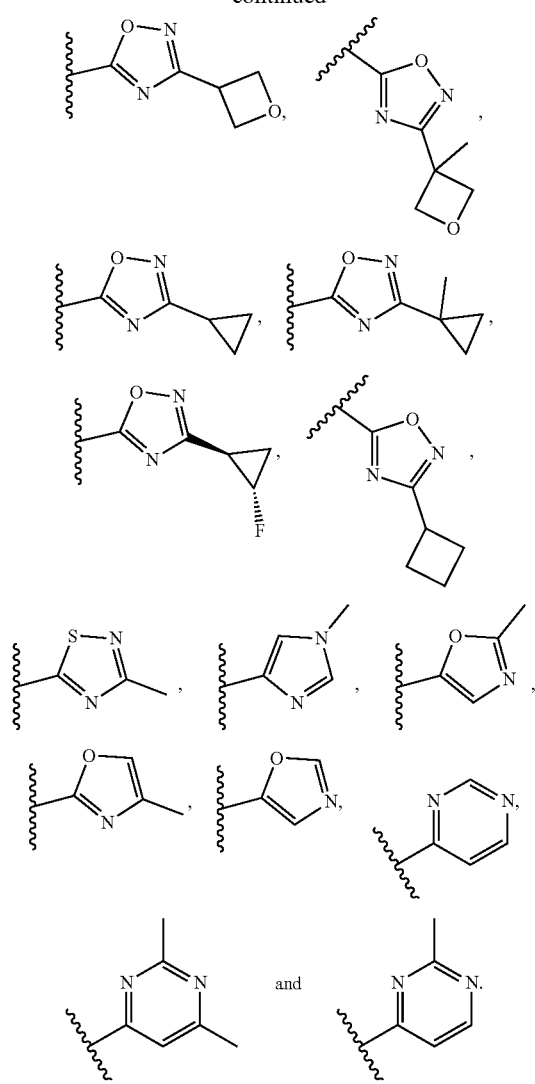

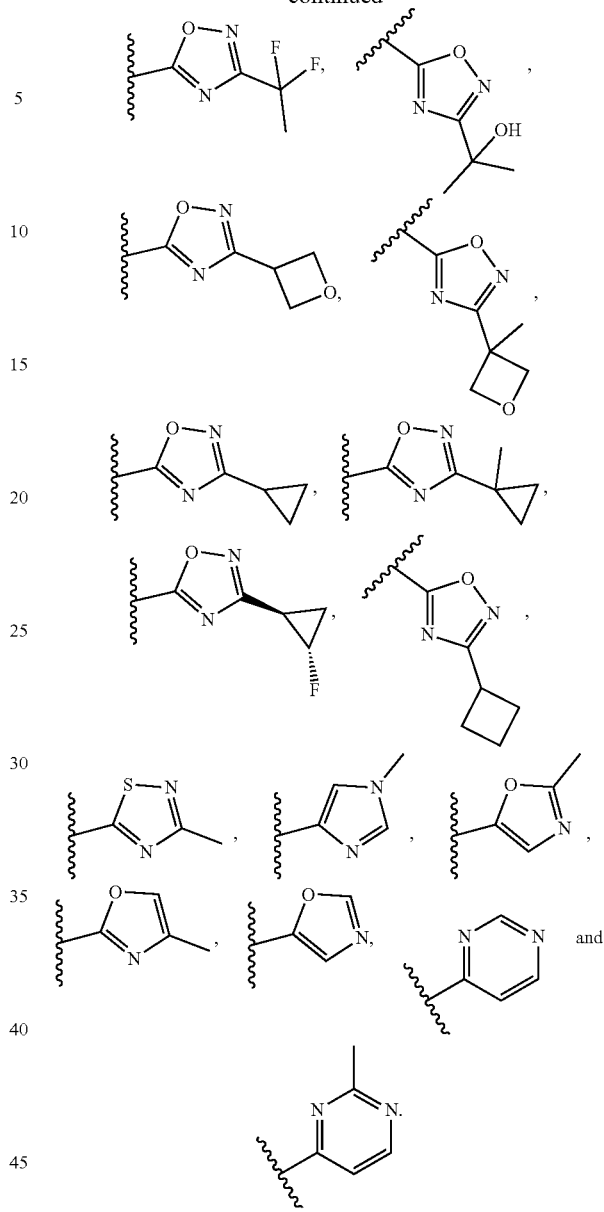

Embodiment 303. The compound of any one of embodiments 1-63, 66-84, 86-208 and 211-271, wherein $R^{35}$ is selected from the group consisting of:

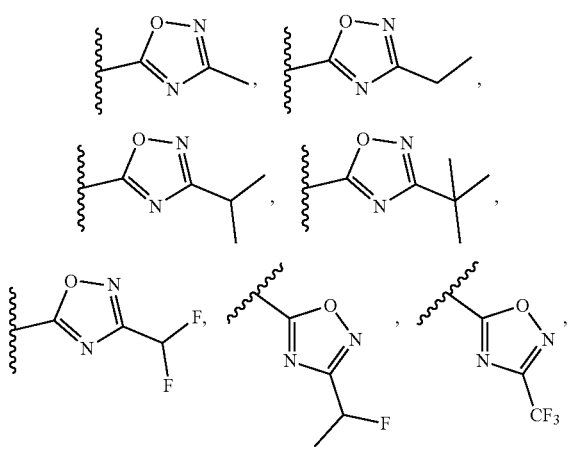

Embodiment 304. The compound of any one of embodiments 1-63, 66-84, 86-208 and 211-271, wherein $R^{35}$ is 1,2,4-oxadiazolyl substituted with 1 substituent selected from halo, hydroxy, $C_1$-$C_4$ alkyl, $C_1$-$C_4$ hydroxyalkyl, $C_1$-$C_6$ alkoxy, $C_1$-$C_4$ haloalkyl, $C_1$-$C_4$ haloalkoxy, $C_3$-$C_6$ heterocyclyl optionally substituted with one or two substituents independently selected from halo, hydroxy and methyl and $C_3$-$C_6$ cycloalkyl optionally substituted with one or two substituents independently selected from halo, hydroxy and methyl.

Embodiment 305. The compound of any one of embodiments 1-63, 66-84, 86-208 and 211-271, wherein $R^{35}$ is 1,2,4-oxadiazolyl substituted with 1 substituent selected from halo, hydroxy, $C_1$-$C_4$ alkyl, $C_1$-$C_4$ hydroxyalkyl, $C_1$-$C_6$ alkoxy, $C_1$-$C_4$ haloalkyl, $C_1$-$C_4$ haloalkoxy, $C_3$-$C_6$ heterocyclyl optionally substituted with one or two substituents independently selected from halo and methyl and $C_3$-$C_6$ cycloalkyl optionally substituted with one or two substituents independently selected from halo and methyl.

Embodiment 306. The compound of any one of embodiments 1-63, 66-84, 86-208 and 211-271, wherein $R^{35}$ is

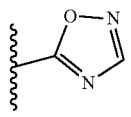

substituted with 1 substituent selected from halo, hydroxy, $C_1$-$C_4$ alkyl, $C_1$-$C_4$ hydroxyalkyl, $C_1$-$C_6$ alkoxy, $C_1$-$C_4$ haloalkyl, $C_1$-$C_4$ haloalkoxy, $C_3$-$C_6$ heterocyclyl optionally substituted with one or two substituents independently selected from halo, hydroxy and methyl, and $C_3$-$C_6$ cycloalkyl optionally substituted with one or two substituents independently selected from halo, hydroxy and methyl.

Embodiment 307. The compound of any one of embodiments 1-63, 66-84, 86-208 and 211-271, wherein $R^{35}$ is

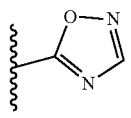 [SMILES: *c1ncno1]

substituted with 1 substituent selected from halo, hydroxy, $C_1$-$C_4$ alkyl, $C_1$-$C_4$ hydroxyalkyl, $C_1$-$C_6$ alkoxy, $C_1$-$C_4$ haloalkyl, $C_1$-$C_4$ haloalkoxy, $C_3$-$C_6$ heterocyclyl optionally substituted with one or two substituents independently selected from halo and methyl, and $C_3$-$C_6$ cycloalkyl optionally substituted with one or two substituents independently selected from halo and methyl.

Embodiment 308. The compound of embodiments 304 or 306, wherein the oxadiazolyl is substituted with one substituent selected from methyl, ethyl, isopropyl, tert-butyl, difluoromethyl, 1-fluoroethyl, 1,1-difluoroethyl, —C(OH)(CH$_3$)$_2$, oxetan-3-yl, 3-methyloxetan-3-yl, cyclobutyl, 1-fluorocyclobutyl, 1-hydroxy-cyclobutyl, cyclopropyl, 1-methylcyclopropyl and 2-fluorocyclopropyl.

Embodiment 309. The compound of any one of embodiments 304-307, wherein the oxadiazolyl is substituted with one substituent selected from methyl, ethyl, isopropyl, tert-butyl, difluoromethyl, 1-fluoroethyl, 1,1-difluoroethyl, —C(OH)(CH$_3$)$_2$, oxetan-3-yl, 3-methyloxetan-3-yl, cyclobutyl, cyclopropyl, 1-methylcyclopropyl and 2-fluorocyclopropyl.

Embodiment 310. The compound of any one of embodiments 1-63, 66-84, 86-208 and 211-271, wherein $R^{35}$ is selected from the group consisting of:

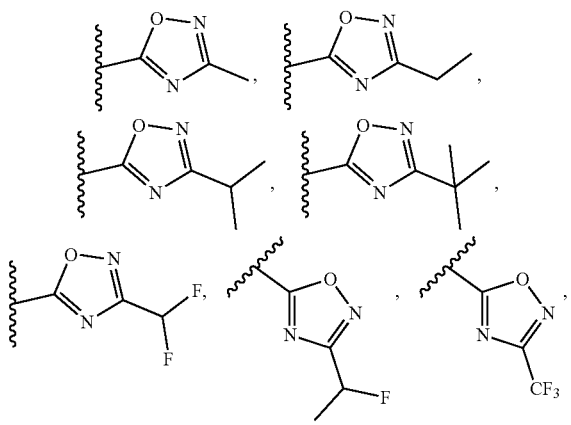

Embodiment 311. The compound of any one of embodiments 1-63, 66-84, 86-208 and 211-271, wherein $R^{35}$ is selected from the group consisting of:

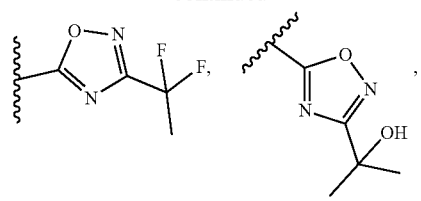

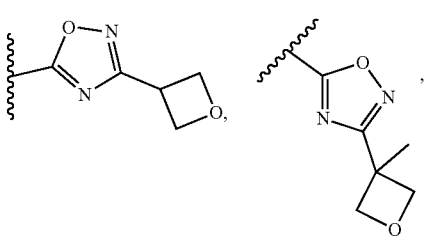

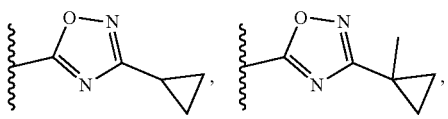

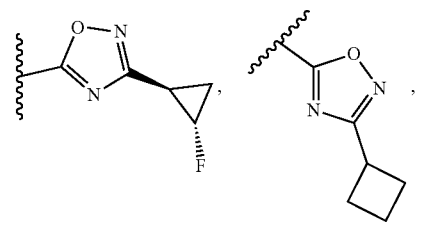

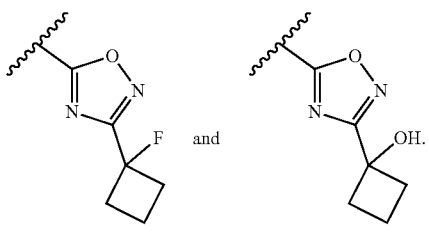

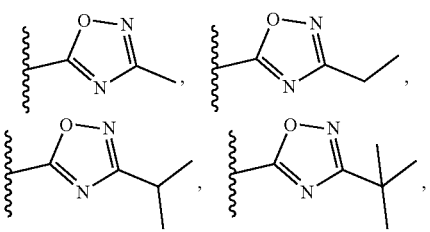

and

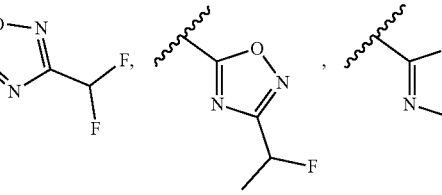

-continued

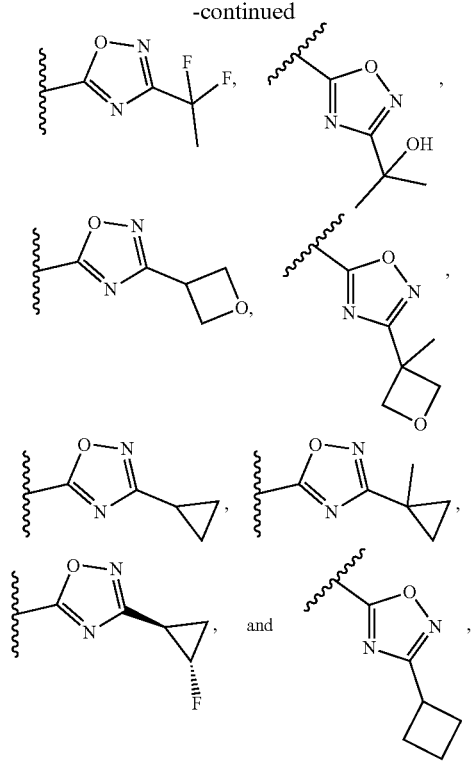

Embodiment 312. The compound of any one of embodiments 1-63, 66-84, 86-208 and 211-271, wherein $R^{35}$ is pyrimidinyl or pyridazinyl substituted with 1 or 2 substituents independently selected from methyl and fluoro.

Embodiment 313. The compound of any one of embodiments 1-63, 66-84, 86-208 and 211-271, wherein $R^{35}$ is pyrimidinyl or pyridazinyl substituted with 0 or 1 instance of methyl.

Embodiment 314. The compound of any one of embodiments 1-63, 66-84, 86-208 and 211-271, wherein $R^{35}$ is selected from:

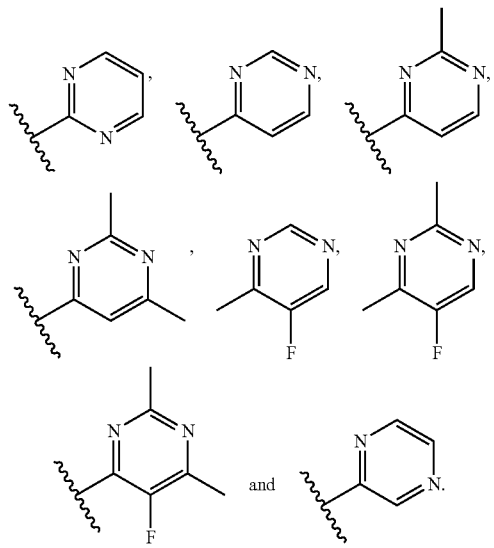

Embodiment 315. The compound of any one of embodiments 1-63, 66-84, 86-208 and 211-271, wherein $R^{35}$ is selected from:

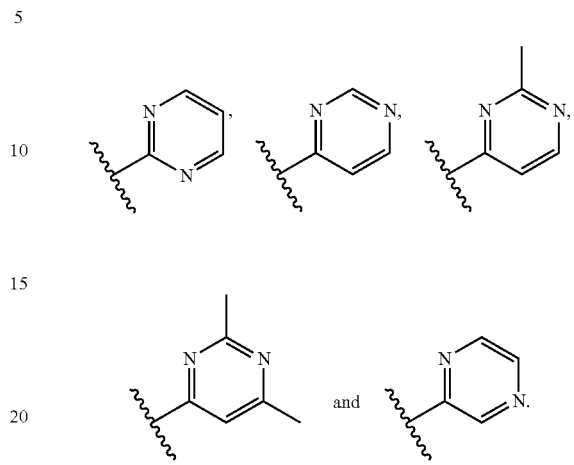

Embodiment 316. The compound of any one of embodiments 1-63, 66-84, 86-208 and 211-271, wherein $R^{35}$ is selected from:

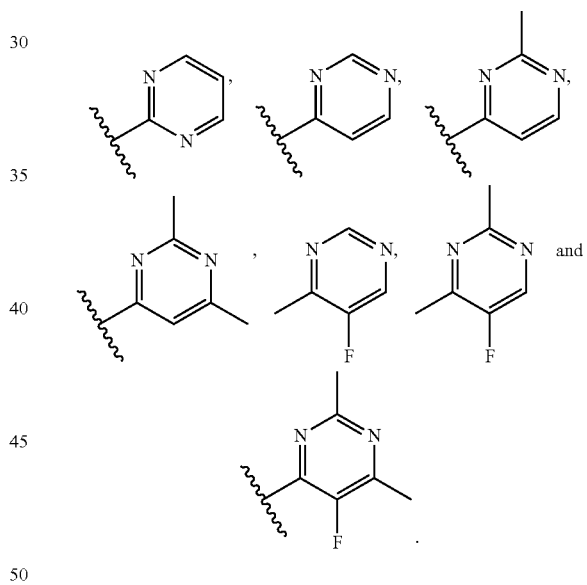

Embodiment 317. The compound of any one of embodiments 1-63, 66-84, 86-208 and 211-271, wherein $R^{35}$ is selected from:

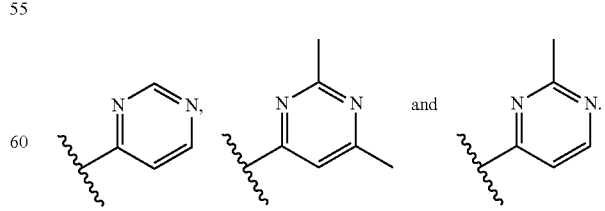

Embodiment 318. The compound of any one of embodiments 1-63, 66-84, 86-208 and 211-271, wherein $R^{35}$ is selected from:

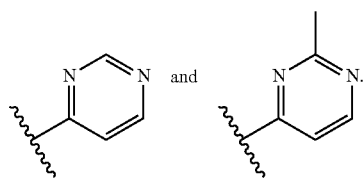

Embodiment 319. The compound of any one of embodiments 1-63, 66-84, 86-208 and 211-318 wherein the attachment point for $R^{35}$ is on a carbon atom.

Embodiment 320. The compound of any one of embodiments 1-63, 66-84, 86-208 and 211-271 wherein $R^{18}$ is —$(CH_2)_u R^{34}$.

Embodiment 321. The compound of any one of embodiments 1-63, 66-84, 86-208 and 211-271 wherein $R^{18}$ is —$CH_2$—$R^{34}$.

Embodiment 322. The compound of any one of embodiments 1-63, 66-84, 86-208 and 211-270 wherein $R^{18}$ is $R^{34}$.

Embodiment 323. The compound of any one of embodiments 1-63, 66-84, 86-208 and 272-318 wherein $R^{18}$ is $R^{35}$.

Embodiment 324. The compound of any one of embodiments 1-63, 66-84 and 86-208 wherein $R^{18}$ is H.

Embodiment 325. The compound of any one of embodiments 1-63, 66-84 and 86-208 wherein $R^{18}$ is not H.

Embodiment 326. The compound of any one of embodiments 1-63, 66-84 and 86-208, wherein $R^{18}$ is selected from the group consisting of hydrogen, —COOH, —C(O)OCH$_3$, —C(O)OCH$_2$CH$_3$, —C(O)OCH(CH$_3$)$_2$, —C(O)N(CH$_3$)$_2$, —C(O)-cyclopropyl, —CH$_2$OCH$_3$, —CH$_2$N(CH$_3$)$_2$, —S(O)$_2$CH$_3$, —S(O)$_2$CH$_2$CH$_3$, —S(O)$_2$-cyclopropyl, 1

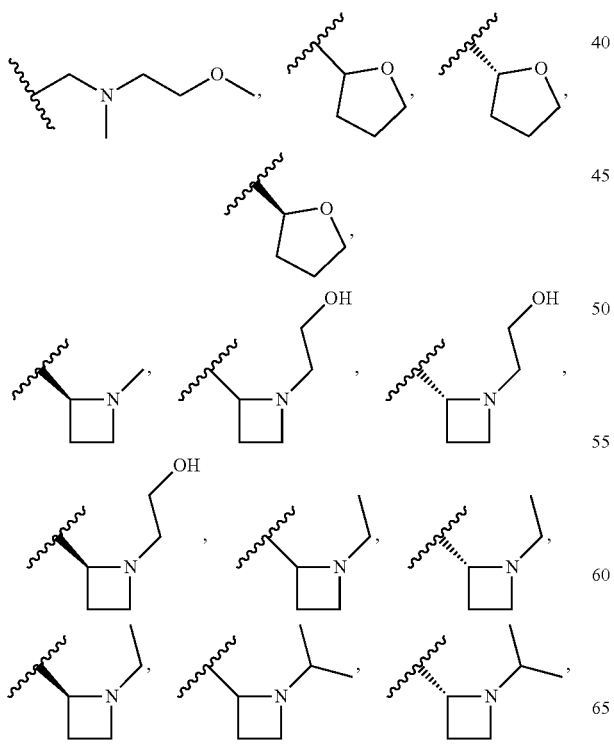

-continued

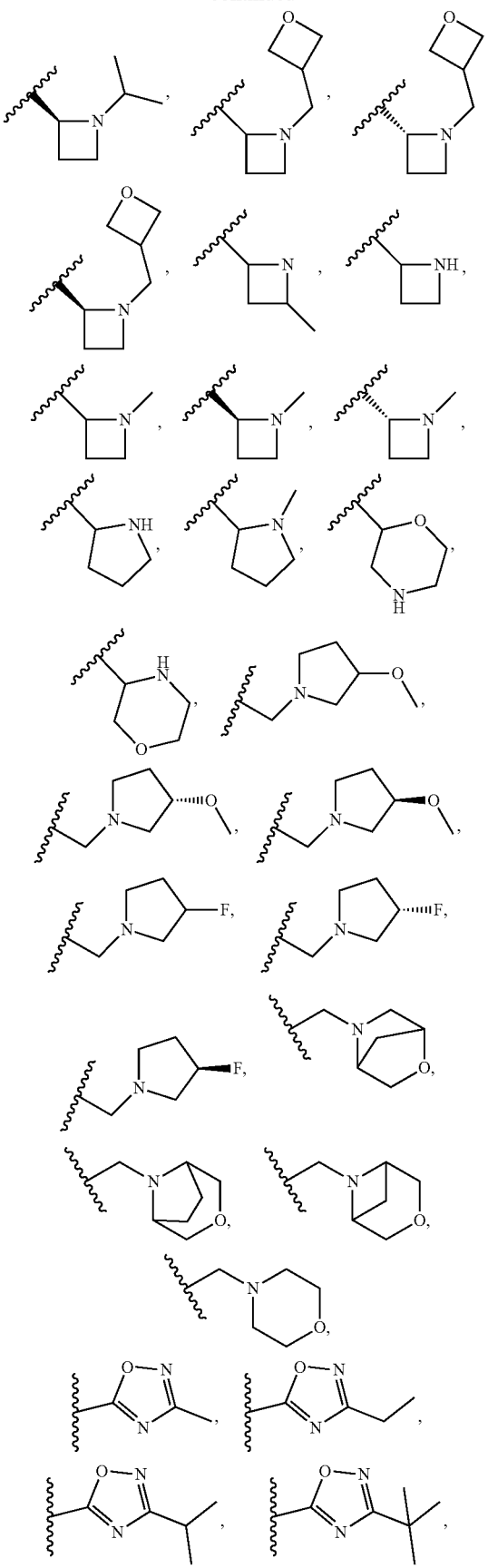

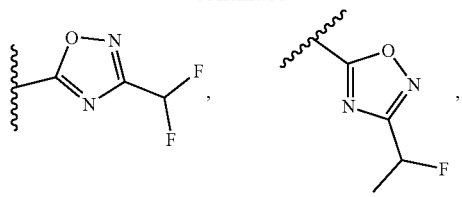
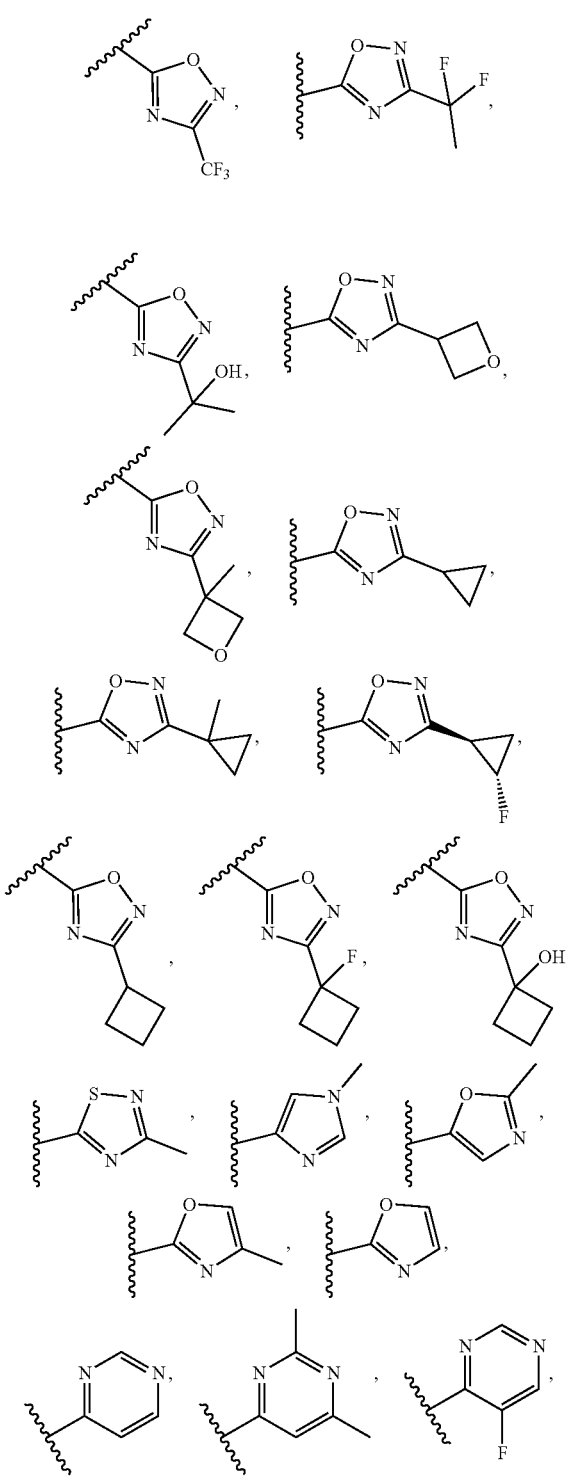
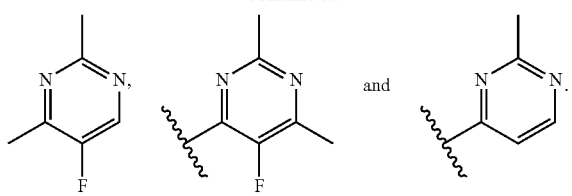
Embodiment 327. The compound of any one of embodiments 1-63, 66-84 and 86-208, wherein $R^{18}$ is selected from the group consisting of hydrogen, —COOH, —C(O)OCH$_3$, —C(O)OCH$_2$CH$_3$, —C(O)OCH(CH$_3$)$_2$, —C(O)N(CH$_3$)$_2$, —C(O)-cyclopropyl, —CH$_2$OCH$_3$, —CH$_2$N(CH$_3$)$_2$, —S(O)$_2$CH$_3$, —S(O)$_2$CH$_2$CH$_3$, —S(O)$_2$-cyclopropyl,
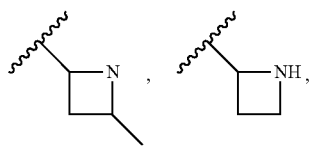
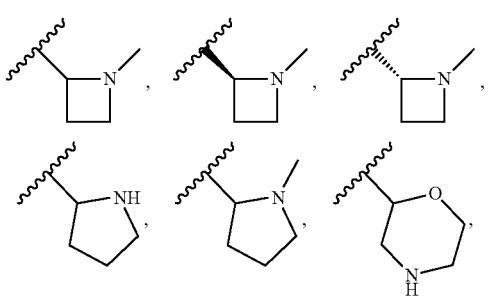
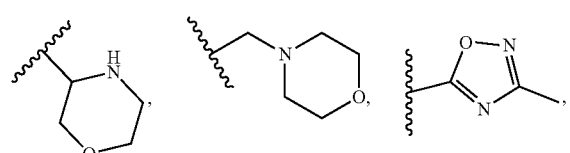
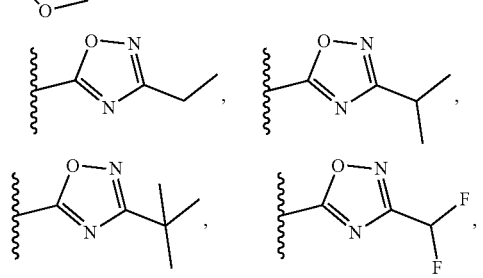
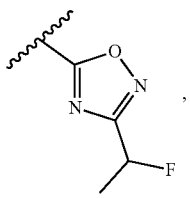
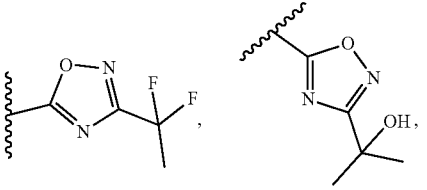

131
-continued
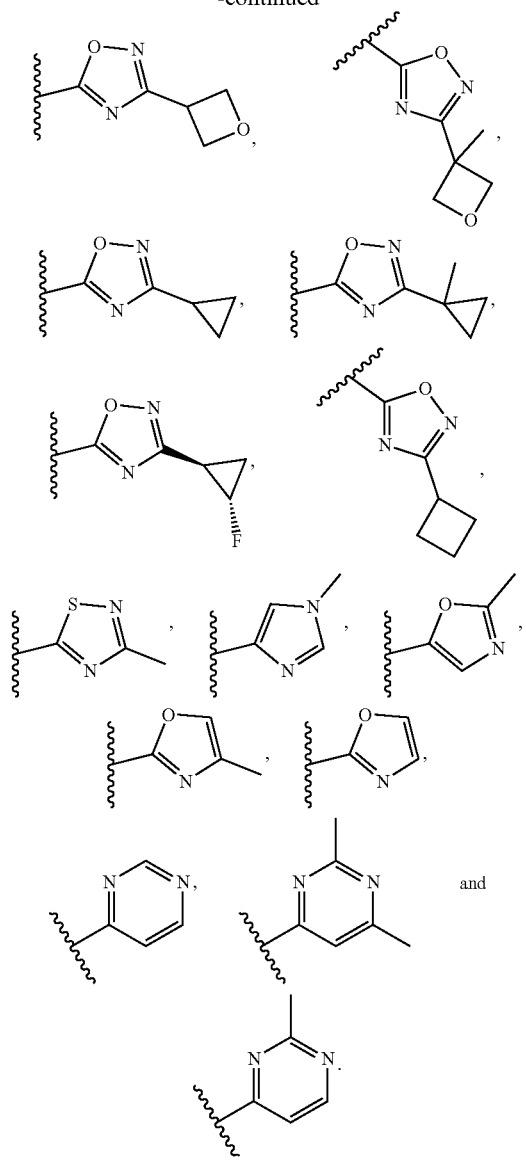
Embodiment 328. The compound of any one of embodiments 1-63, 66-84 and 86-208, wherein $R^{18}$ is selected from the group consisting of hydrogen, —COOH, —C(O)OCH$_3$, —C(O)OCH$_2$CH$_3$, —C(O)OCH(CH$_3$)$_2$, —C(O)N(CH$_3$)$_2$, —C(O)-cyclopropyl, —CH$_2$OCH$_3$, —CH$_2$N(CH$_3$)$_2$, —S(O)$_2$CH$_3$, —S(O)$_2$CH$_2$CH$_3$, —S(O)$_2$-cyclopropyl,
132
-continued
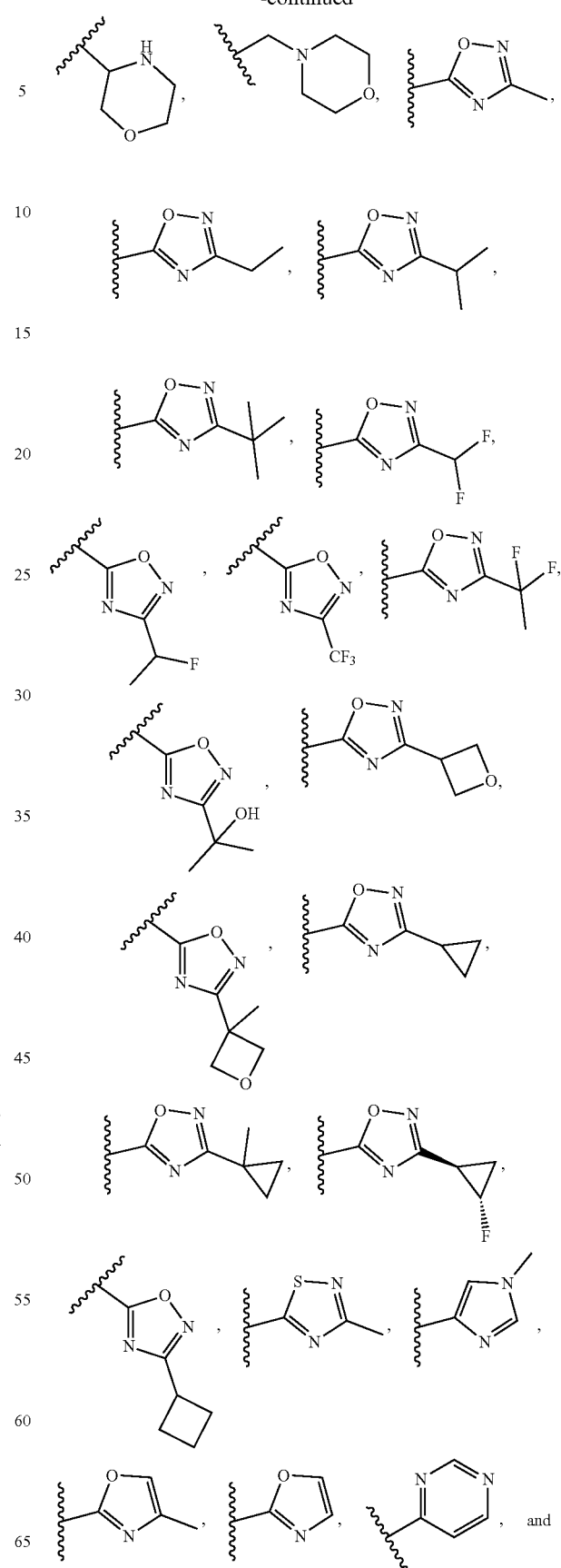
and

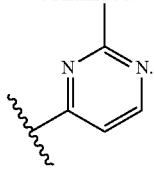

Embodiment 329. The compound of any one of embodiments 1-63, 66-84 and 86-208, wherein $R^{18}$ is selected from the group consisting of hydrogen, —COOH, —C(O)OCH$_3$, —C(O)OCH$_2$CH$_3$, —C(O)OCH(CH$_3$)$_2$, —C(O)N(CH$_3$)$_2$, —C(O)-cyclopropyl, —CH$_2$OCH$_3$, —CH$_2$N(CH$_3$)$_2$, —S(O)$_2$CH$_3$, —S(O)$_2$CH$_2$CH$_3$, —S(O)$_2$-cyclopropyl, oxazolyl, and 4-methyloxazolyl.

Embodiment 330. The compound of any one of embodiments 1-63, 66-84 and 86-208, wherein $R^{18}$ is not hydrogen.

Embodiment 331. The compound of any one of embodiments 1-63, 66-84 and 86-208, wherein $R^{18}$ is —C(O)OCH$_3$.

Embodiment 332. The compound of any one of embodiments 1-63, 66-84 and 86-331, wherein the double bond in the —C(O)C(R$^{19}$)═C(R$^{20}$)R$^{18}$ portion of the compound is in the E configuration.

Embodiment 333. The compound of any one of embodiments 1-60, wherein $R^2$ is $R^{2d}$.

Embodiment 334. The compound of any one of embodiments 1-60, 66-84, 86-114 and 116-333, wherein $R^2$ is —NR$^{24}$R$^{25}$.

Embodiment 335. The compound of any one of embodiments 1-60, 66-84, 86-114 and 116-334, wherein $R^{24}$ is methyl or ethyl.

Embodiment 336. The compound of any one of embodiments 1-60, 66-84, 86-114 and 116-334, wherein $R^{24}$ is methyl.

Embodiment 337. The compound of any one of embodiments 1-60, 66-84, 86-114 and 116-336, wherein $R^{25}$ is —(C$_1$-C$_4$ alkylene)-C(O)CH═CHR$^{26}$.

Embodiment 338. The compound of any one of embodiments 1-60, 66-84, 86-114 and 116-337, wherein the C$_1$-C$_4$ alkylene of $R^{25}$ is selected from the group consisting of —CH$_2$—, —CH$_2$CH$_2$—, —(CH$_2$)$_3$—, —(CH$_2$)$_4$—, —CH$_2$CH(CH$_3$)—, and

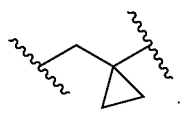 [SMILES: *CC1(*)CC1]

Embodiment 339. The compound any one of embodiments 1-60, 66-84, 86-114 and 116-334, wherein $R^{24}$ and $R^{25}$ together with the nitrogen to which they are attached form a 4-8 membered saturated heterocyclic group comprising one nitrogen as the sole heteroatom within the ring atoms, wherein the 4-8 membered saturated heterocyclic group is substituted with —(C$_0$-C$_2$ alkylene)-C(O)CH═CHR$^{26}$, and wherein the 4-8 membered saturated heterocyclic group is further optionally substituted with C$_1$-C$_4$ alkyl.

Embodiment 340. The compound of any one of embodiments 1-60, 66-84, 86-114, 116-334 and 339, wherein the 4-8 membered saturated heterocyclic group of $R^{24}$ and $R^{25}$ together with the nitrogen to which they are attached is selected from the group consisting of:

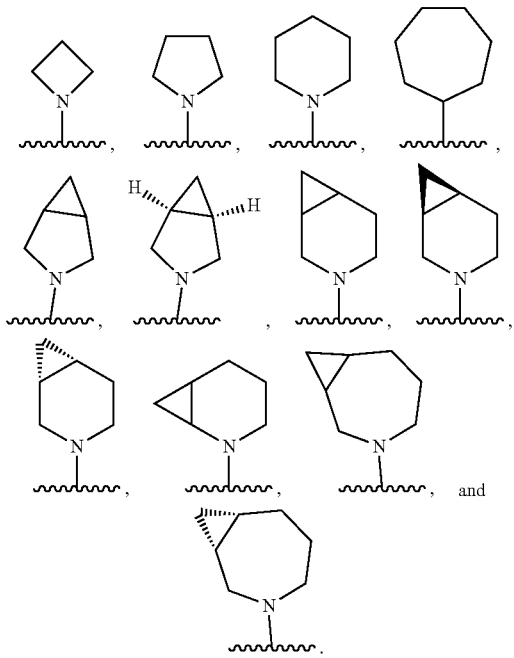

Embodiment 341. The compound of any one of embodiments 1-60, 66-84, 86-114, 116-334 and 339, wherein the 4-8 membered saturated heterocyclic group of $R^{24}$ and $R^{25}$ together with the nitrogen to which they are attached is selected from the group consisting of:

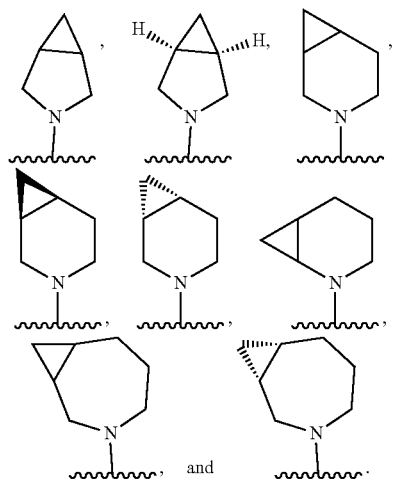

Embodiment 342. The compound of any one of embodiments 1-60, 66-84, 86-114, 116-334 and 339-341, wherein the 4-8 membered saturated heterocyclic group of $R^{24}$ and $R^{25}$ together with the nitrogen to which they are attached is not substituted with C$_1$-C$_4$ alkyl.

Embodiment 343. The compound of any one of embodiments 1-60, 66-84, 86-114, 116-334 and 339-341, wherein the 4-8 membered saturated heterocyclic group of $R^{24}$ and $R^{25}$ together with the nitrogen to which they are attached is substituted with methyl.

Embodiment 344. The compound of any one of embodiments 1-60, 66-84, 86-114, 116-334 and 339-343, wherein the C$_0$-C$_2$ alkylene group of the —(C$_0$-C$_2$ alkylene)-C(O)CH═CHR$^{26}$ group is selected from a bond and methylene.

Embodiment 345. The compound of any one of embodiments 1-60, 66-84, 86-114, 116-334 and 339-343, wherein the $C_0$-$C_2$ alkylene group of the —($C_0$-$C_2$ alkylene)-C(O)CH=CHR$^{26}$ group is a bond.

Embodiment 346. The compound of any one of embodiments 1-60, 66-84, 86-114 and 116-333, wherein R$^{2d}$ is —C(O)N(R$^{27}$)—($C_1$-$C_4$ alkylene)-C(O)CH=CHR$^{26}$.

Embodiment 347. The compound of any one of embodiments 1-60, 66-84, 86-114, 116-333 and 335-346, wherein R$^{27}$ is hydrogen.

Embodiment 348. The compound of any one of embodiments 1-60, 66-84, 86-114, 116-333 and 335-347, wherein the $C_1$-$C_4$ alkylene of the —C(O)N(R$^{27}$)—($C_1$-$C_4$ alkylene)-C(O)CH=CHR$^{26}$ group is methylene.

Embodiment 349. The compound of any one of embodiments 1-60, 66-84, 86-114 and 116-333, wherein R$^{2d}$ is —O—($C_1$-$C_4$ alkylene)-C(O)CH=CHR$^{26}$.

Embodiment 350. The compound of any one of embodiments 1-60, 66-84, 86-114, 116-333, 335-345 and 347-349, wherein the $C_1$-$C_4$ alkylene of the —O—($C_1$-$C_4$ alkylene)-C(O)CH=CHR$^{26}$ group is methylene.

Embodiment 351. The compound of any one of embodiments 1-60, 66-84, 86-114, 116-333, 335-345 and 347-350, wherein R$^{26}$ is hydrogen or methyl.

Embodiment 352. The compound of any one of embodiments 1-60, 66-84, 86-114, 116-333, 335-345 and 347-350, wherein R$^{26}$ is hydrogen.

Embodiment 353. The compound of any one of embodiments 1-60, 66-84, 86-114, 116-333, 335-345 and 347-350, wherein R$^{26}$ is methyl.

Embodiment 354. The compound of any one of embodiments 1-60, wherein R$^2$ is R$^{2e}$.

Embodiment 355. The compound of any one of embodiments 1-61, 63, 66-84, 86-114, 116-332 and 334-354, wherein R$^{28}$ is selected from the group consisting of $C_1$-$C_4$ alkyl and $C_1$-$C_4$ alkoxy.

Embodiment 356. The compound of any one of embodiments 1-61, 63, 66-84, 86-114, 116-332 and 334-354, wherein R$^{28}$ is selected from the group consisting of methyl, ethyl, and —CH$_2$CH$_2$OCH$_3$.

Embodiment 357. The compound of any one of embodiments 1-61, 63, 66-84, 86-114, 116-332 and 334-354, wherein R$^{28}$ is methyl or ethyl.

Embodiment 358. The compound of any one of embodiments 1-61, 63, 66-84, 86-114, 116-332 and 334-354, wherein R$^{28}$ is methyl.

Embodiment 359. The compound of any one of embodiments 1-61, 63, 66-84, 86-114, 116-332 and 334-358, wherein t is 0 or 1.

Embodiment 360. The compound of any one of embodiments 1-61, 63, 66-84, 86-114, 116-332 and 334-358, wherein t is 1.

Embodiment 361. The compound of any one of embodiments 1-61, 63, 66-84, 86-114, 116-332 and 334-358, wherein t is 0.

Embodiment 362. The compound of any one of embodiments 1-61, 63, 66-84, 86-114, 116-332 and 334-361, wherein R$^{30}$ is a 4-5 membered monocyclic saturated heterocyclic group comprising one nitrogen as the sole heteroatom within the ring atoms, wherein the nitrogen ring atom of the heterocyclic group is substituted with —C(O)C≡CR$^{31}$ and wherein the heterocyclic group is not further substituted or is further substituted with 1 substituent selected from the group consisting of hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, and halo.

Embodiment 363. The compound of any one of embodiments 1-61, 63, 66-84, 86-114, 116-332 and 334-362 wherein the heterocyclic group of R$^{30}$ is not further substituted.

Embodiment 364. The compound of any one of embodiments 1-61, 63, 66-84, 86-114, 116-332 and 334-362 wherein the heterocyclic group of R$^{30}$ is further substituted with 1 substituent selected from the group consisting of hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, and halo.

Embodiment 365. The compound of any one of embodiments 1-61, 63, 66-84, 86-114, 116-332 and 334-362, wherein the heterocyclic group of R$^{30}$ is selected from the group consisting of.

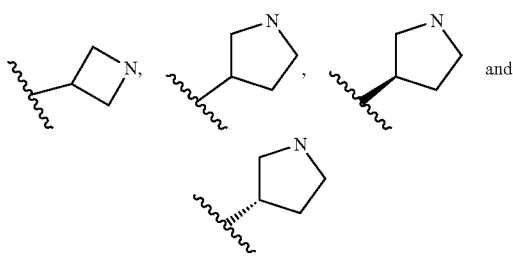

wherein the ring nitrogen of the heterocyclic group is substituted with —C(O)C≡CR$^{31}$ and the heterocyclic group is not further substituted, or is substituted with one substituent selected from hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, and halo.

Embodiment 366. The compound of embodiment 365, wherein the heterocyclic group of R$^{30}$ is not further substituted.

Embodiment 367. The compound of embodiment 365, wherein the heterocyclic group of R$^{30}$ is further substituted with 1 substituent selected from the group consisting of hydroxy, CN, $C_1$-$C_4$ alkyl, $C_1$-$C_4$ cyanoalkyl, and halo.

Embodiment 368. The compound of any one of embodiments 1-61, 63, 66-84, 86-114, 116-332 and 334-367, wherein R$^{29}$ is selected from the group consisting of:

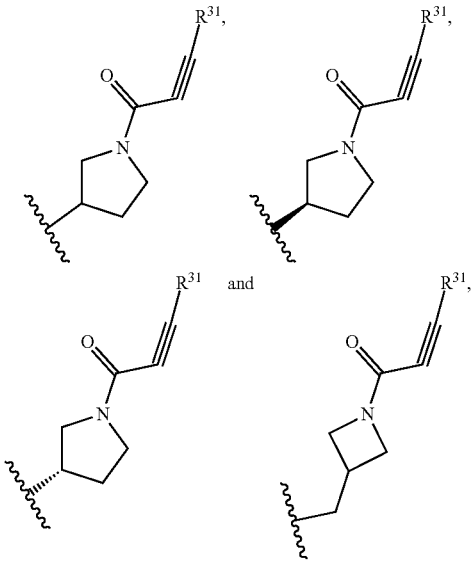

wherein the azetidine and pyrrolidine groups are not further substituted, or are substituted with one substituent selected from hydroxy, CN, $C_1$-$C_4$ alkyl, $C_1$-$C_4$ alkoxy, $C_1$-$C_4$ haloalkyl, $C_1$-$C_4$ cyanoalkyl, $C_1$-$C_4$ haloalkoxy, and halo.

Embodiment 369. The compound of embodiment 368, wherein the azetidine and pyrrolidine groups are not further substituted.

Embodiment 370. The compound of embodiment 368, wherein the azetidine and pyrrolidine groups are further substituted with 1 substituent selected from the group consisting of hydroxy, CN, $C_1$-$C_4$ alkyl, $C_1$-$C_4$ cyanoalkyl, and halo.

Embodiment 371. The compound of any one of embodiments 1-61, 63, 66-84, 86-114, 116-332 and 334-370 wherein v is 1.

Embodiment 372. The compound of any one of embodiments 1-61, 63, 66-84, 86-114, 116-332 and 334-370 wherein v is 2.

Embodiment 373. The compound of any one of embodiments 1-61, 63, 66-84, 86-114, 116-332 and 334-372 wherein p is 0 or 1.

Embodiment 374. The compound of any one of embodiments 1-61, 63, 66-84, 86-114, 116-332 and 334-372 wherein p is 0.

Embodiment 375. The compound of any one of embodiments 1-61, 63, 66-84, 86-114, 116-332 and 334-372 wherein p is 1.

Embodiment 376. The compound of any one of embodiments 1-61, 63, 66-84, 86-114, 116-332, 334-370 and 373-375, wherein $R^{31}$ is selected from the group consisting of —$CH_2$—$NR^{32}R^{33}$ and —$(CH_2)_p$—$R^{36}$.

Embodiment 377. The compound of any one of embodiments 1-61, 63, 66-84, 86-114, 116-332 and 334-376, wherein $R^{32}$ and $R^{33}$ are independently selected from methyl and ethyl.

Embodiment 378. The compound of any one of embodiments 1-61, 63, 66-84, 86-114, 116-332 and 334-370 and 373-375, wherein $R^{31}$ is —$(CH_2)_p$—$R^{36}$.

Embodiment 379. The compound of any one of embodiments 1-61, 63, 66-84, 86-114, 116-332 and 334-370 and 377, wherein $R^{31}$ is —$CH_2$—$NR^{32}R^{33}$.

Embodiment 380. The compound of any one of embodiments 1-61, 63, 66-84, 86-114, 116-332 and 334-378, wherein $R^{36}$ is a 4-7 membered monocyclic heterocycle containing a nitrogen atom and optionally an oxygen atom as the only heteroatoms, wherein the monocyclic heterocycle is substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 381. The compound of any one of embodiments 1-61, 63, 63, 66-84, 86-114, 116-332 and 334-378, wherein $R^{36}$ is a 4-7 membered monocyclic heterocycle containing a nitrogen atom as the only heteroatom, wherein the monocyclic heterocycle is substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 382. The compound of embodiment 380 or 381, wherein the monocyclic heterocycle of $R^{36}$ is substituted with 0, 1 or 2 substituents independently selected from methyl and hydroxy.

Embodiment 383. The compound of embodiment 380 or 381, wherein the monocyclic heterocycle of $R^{36}$ is substituted with 0, 1 or 2 instances of methyl.

Embodiment 384. The compound of embodiment 380 or 381, wherein the monocyclic heterocycle of $R^{36}$ is substituted with 0 or 1 substituents independently selected from methyl and hydroxy.

Embodiment 385. The compound of embodiment 380 or 381, wherein the monocyclic heterocycle of $R^{36}$ is substituted with 0 or 1 instance of methyl.

Embodiment 386. The compound of embodiment 384, wherein $R^{36}$ is selected from azetidinyl, pyrrolidinyl and morpholinyl substituted with 0, 1 or 2 substituents independently selected from methyl and hydroxy.

Embodiment 387. The compound of embodiment 385, wherein $R^{36}$ is selected from azetidinyl, pyrrolidinyl and morpholinyl substituted with 0 or 1 instance of methyl.

Embodiment 388. The compound of embodiment 384, wherein $R^{36}$ is azetidinyl substituted with 0, 1 or 2 substituents independently selected from methyl and hydroxy.

Embodiment 389. The compound of embodiment 385, wherein $R^{36}$ is azetidinyl substituted with 0 or 1 instance of methyl.

Embodiment 390. The compound of embodiment 384, wherein $R^{36}$ is pyrrolidinyl substituted with 0, 1 or 2 substituents independently selected from methyl and hydroxy Embodiment 391. The compound of embodiment 385, wherein $R^{36}$ is pyrrolidinyl substituted with 1 or 2 instances of methyl.

Embodiment 392. The compound of embodiment 385, wherein $R^{36}$ is pyrrolidinyl substituted with 0 or 1 instance of methyl.

Embodiment 393. The compound of any embodiment 385, wherein $R^{36}$ is morpholinyl substituted with 0 or 1 instance of methyl.

Embodiment 394. The compound of any one of embodiments 1-61, 63, 66-84, 86-114, 116-332, 334-378 and 380-393, wherein the attachment point for $R^{36}$ is a carbon atom.

Embodiment 395. The compound of embodiment 394, wherein $R^{36}$ is selected from the group consisting of:

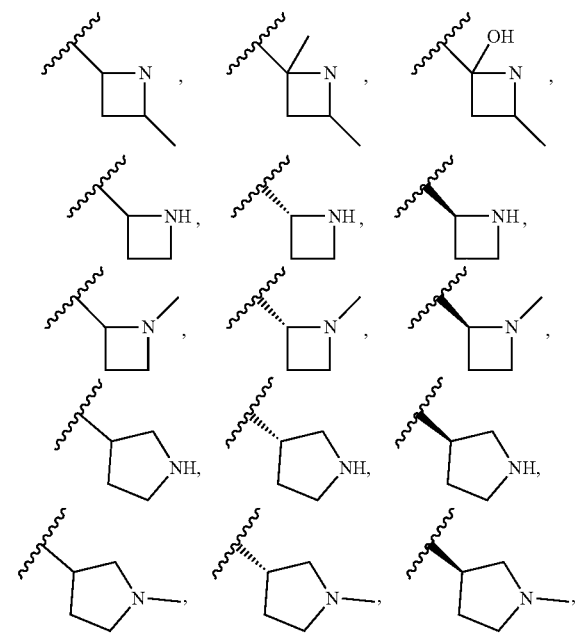

-continued
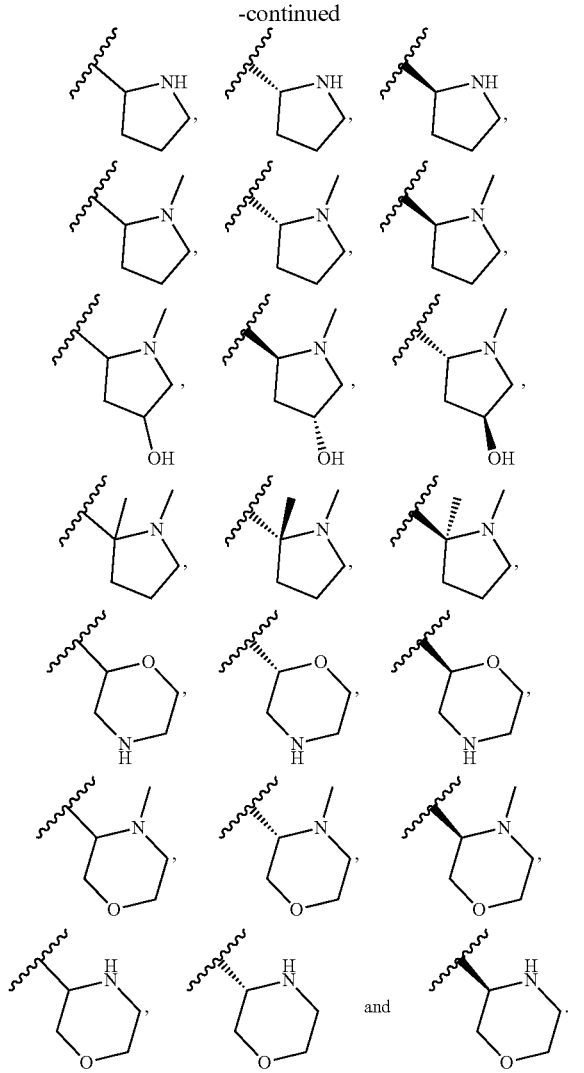
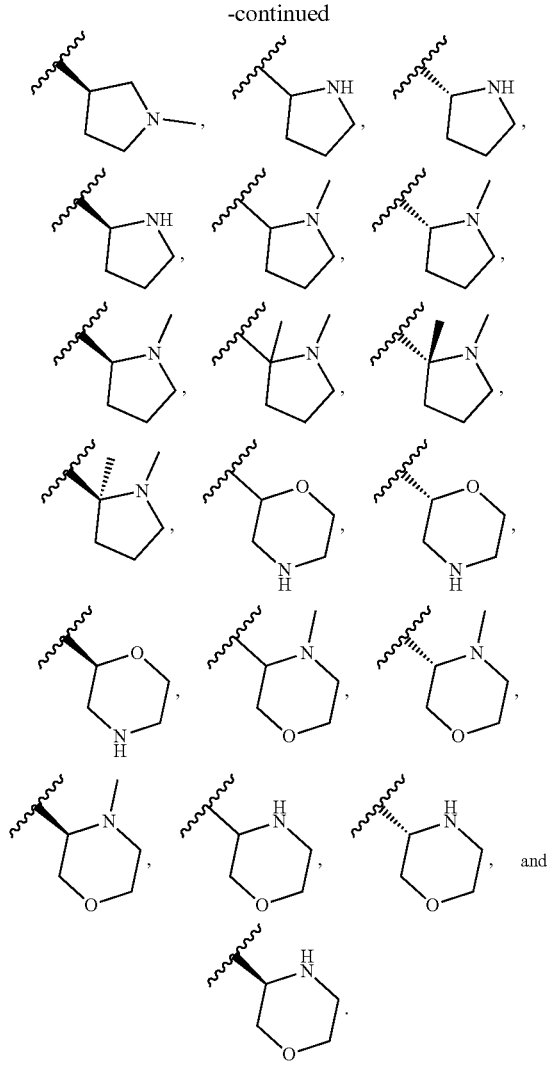
Embodiment 396. The compound of embodiment 394, wherein $R^{36}$ is selected from the group consisting of:
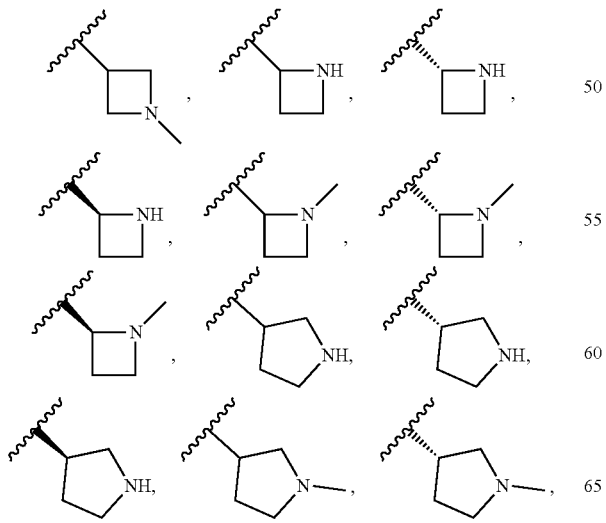
Embodiment 397. The compound of embodiment 394, wherein $R^{36}$ is selected from the group consisting of:
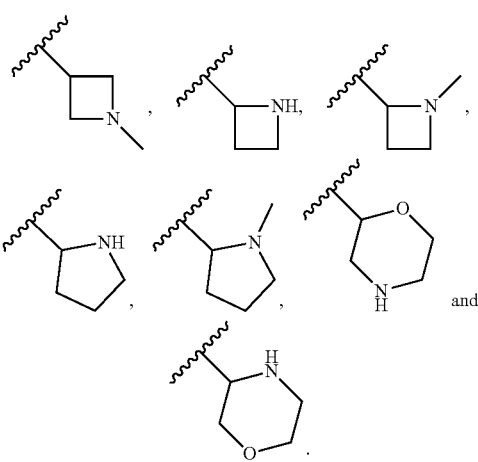
Embodiment 398. The compound of embodiment 394, wherein $R^{36}$ is selected from the group consisting of:

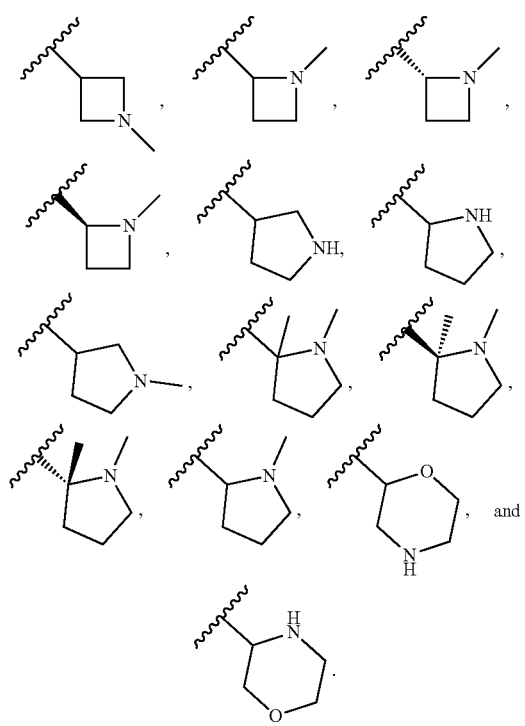

Embodiment 399. The compound of embodiment 394, wherein $R^{36}$ is selected from the group consisting of:

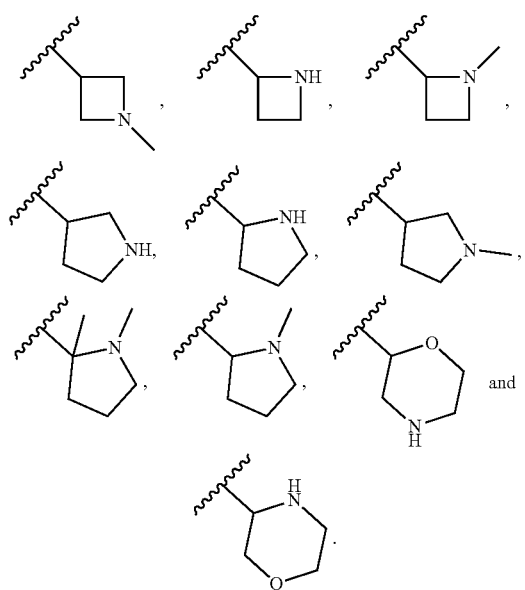

Embodiment 400. The compound of any one of embodiments 380-399 wherein p is 0.

Embodiment 401. The compound of any one of embodiments 1-61, 63, 66-84, 86-114, 116-332 and 334-378, wherein $R^{36}$ is a 4-10 membered heterocycle containing a nitrogen atom and zero, one or two additional heteroatoms selected from oxygen and sulfur, including sulfur dioxide, wherein the 4-10 membered heterocycle is substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 402. The compound of embodiment 401, wherein $R^{36}$ is a 4-10 membered heterocycle containing a nitrogen atom and zero, one or two additional heteroatoms selected from oxygen and sulfur, including sulfur dioxide, selected from the group consisting of a 4-8 membered monocyclic heterocycle, a 6-10 membered fused bicyclic heterocycle, a 6-10 membered bridged heterocycle and a 6-10 membered spiro heterocycle, each substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 403. The compound of embodiment 401, wherein $R^{36}$ is a 4-8 membered monocyclic heterocycle substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 404. The compound of embodiment 401, wherein $R^{36}$ is a 6-10 membered fused bicyclic heterocycle substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 405. The compound of embodiment 401, wherein $R^{36}$ is a 6-10 membered bridged heterocycle substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 406. The compound of embodiment 401, wherein $R^{36}$ is a 6-10 membered spiro heterocycle substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 407. The compound of any one of embodiments 401-406, wherein $R^{36}$ is selected from azetidine, pyrrolidine, 2-azabicyclo[2.1.1]hexane, morpholine, 2-oxa-5-azabicyclo[4.1.0]heptane, 1,4-oxazepane, 2-oxa-6-azaadamantane, 5-oxa-8-azaspiro[2.6]nonane, 2-oxa-6-azabicyclo[3.2.1]octane, 6-oxa-3-azabicyclo[3.2.1]octane, 3-oxa-6-azabicyclo[3.2.1]octane, 6-oxa-2-azabicyclo[3.2.1]octane, 2-oxa-5-azabicyclo[2.2.1]heptane, 3-oxa-9-azabicyclo[3.3.1]nonane, 3,7-dioxa-9-azabicyclo[3.3.1]nonane, 3-oxa-7-azabicyclo[3.3.1]nonane, 3,9-dioxa-7-azabicyclo[3.3.1]nonane, 3-oxa-8-azabicyclo[3.2.1]octane, 2-oxa-5-azabicyclo[2.2.2]octane, 7-oxa-2-azabicyclo[3.3.1]nonane, 8-oxa-3-azabicyclo[3.2.1]octane, 9-oxa-3-azabicyclo[3.3.1]nonane, 6-oxa-8-azabicyclo[3.2.2]nonane, 2-oxa-6-azaspiro[3.3]heptane, 3-oxa-6-azabicyclo[3.1.1]heptane, 6-oxa-3-azabicyclo[3.1.1]heptane, thiomorpholine, thiomorpholine 1,1-dioxide, 1,4-thiazepane, 1,4-thiazepane 1,1-dioxide, 3-thia-6-azabicyclo[3.2.1]octane, 3-thia-8-azabicyclo[3.2.1]octane 3,3-dioxide, 3-thia-7-azabicyclo[3.3.1]nonane, 3-thia-6-azabicyclo[3.2.1]octane 3,3-dioxide, 3-thia-7-azabicyclo[3.3.1]nonane 3,3-dioxide, 2-thia-5-azabicyclo[2.2.1]heptane, 2-thia-5-azabicyclo[2.2.1]heptane 2,2-dioxide, 2-thia-6-azaspiro[3.4]octane 2,2-dioxide, 2-thia-6-azaspiro[3.3]heptane 2,2-dioxide, 2-thia-6-azaspiro[3.3]heptane and hexahydro-1H-thieno[3,4-c]pyrrole 2,2-dioxide, each substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 408. The compound of embodiment 407, wherein $R^{36}$ is morpholine substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 409. The compound of any one of embodiments 401-408, wherein the attachment point for $R^{36}$ is the nitrogen atom of the heterocycle.

Embodiment 410. The compound of embodiment 409, wherein the $R^{36}$ is selected from the group consisting of.

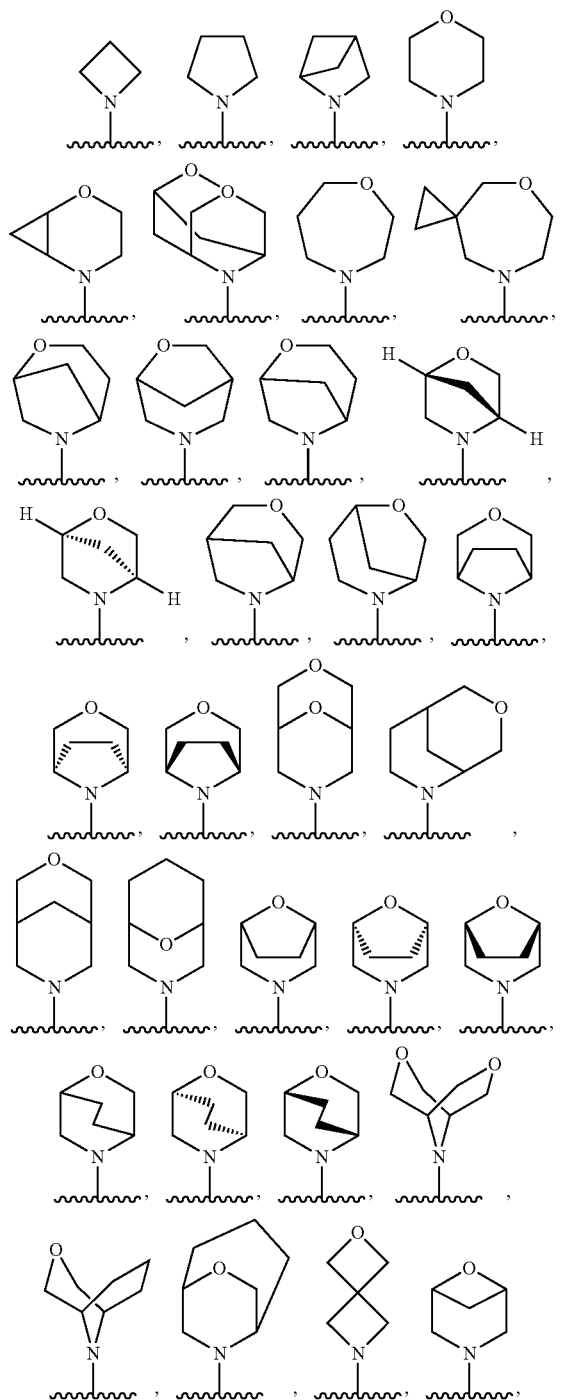

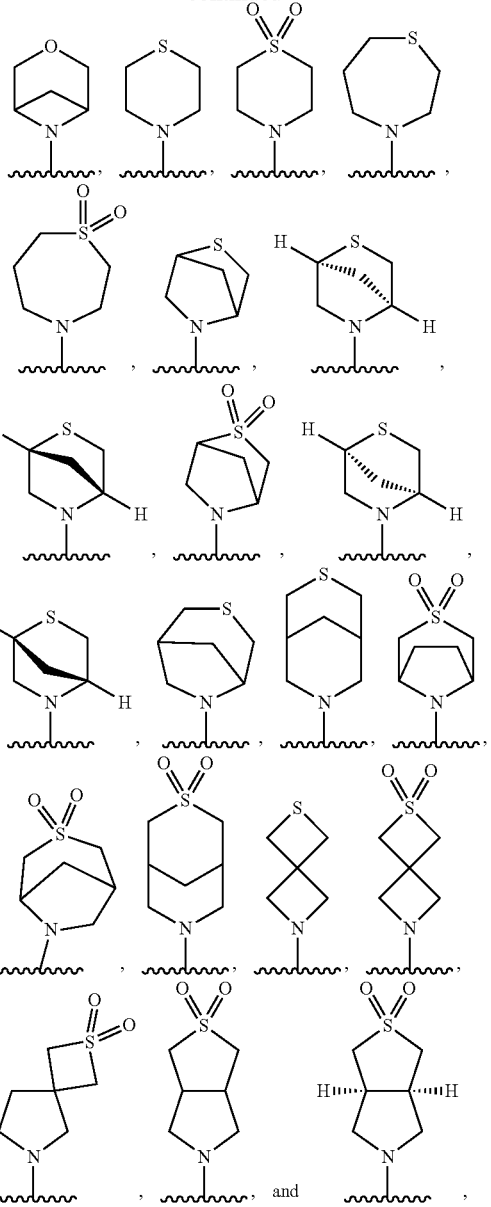

each substituted with 0, 1, 2, 3 or 4 substituents independently selected from halo, hydroxy, $C_1$-$C_4$ alkyl, $C_1$-$C_6$ ammnoalkyl, $C_1$-$C_6$ alkoxy, $C_1$-$C_4$ haloalkyl, $C_1$-$C_4$ haloalkoxy and $C_2$-$C_3$ alkynyl.

Embodiment 411. The compound of embodiment 410, wherein $R^{36}$ is

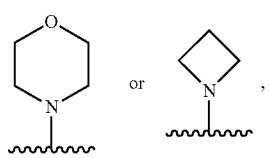 [SMILES: *N1CCOCC1 ; *N1CCC1]

each substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

145

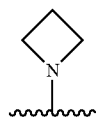

Embodiment 412. The compound of embodiment 410, wherein $R^{36}$ is substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 413. The compound of embodiment 410, wherein $R^{36}$ is

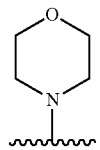

substituted with 0, 1, 2, 3 or 4 substituents independently selected from halo, hydroxy, $C_1$-$C_4$ alkyl, $C_1$-$C_6$ aminoalkyl, $C_1$-$C_6$ alkoxy, $C_1$-$C_4$ haloalkyl, $C_1$-$C_4$ haloalkoxy and $C_2$-$C_3$ alkynyl.

Embodiment 414. The compound of any one of embodiments 401-413, wherein the 4-10 membered heterocycle of $R^{36}$ is substituted with 0, 1, 2, 3 or 4 substituents independently selected from fluoro, methyl, ethyl, hydroxy, methoxy, trifluoromethyl, trifluoromethoxy, —$CH_2OCH_3$, —$CH_2CH_2OCH_3$, —$CH_2CH_2OCH_2CH_2OCH_3$, —$CH_2N(CH_3)_2$, —$CH_2CH_2N(CH_3)_2$.

Embodiment 415. The compound of any one of embodiments 401-413, wherein the 4-10 membered heterocycle of $R^{36}$ is substituted with 0, 1 or 2 substituents independently selected from fluoro, methyl, ethyl, hydroxy, methoxy, trifluoromethyl, trifluoromethoxy, —$CH_2OCH_3$, —$CH_2CH_2OCH_3$, —$CH_2CH_2OCH_2CH_2OCH_3$, —$CH_2N(CH_3)_2$, —$CH_2CH_2N(CH_3)_2$.

Embodiment 416. The compound of any one of embodiments 401-413, wherein the 4-10 membered heterocycle of $R^{36}$ is substituted with 0, 1 or 2 substituents independently selected from fluoro and methyl.

Embodiment 417. The compound of any one of embodiments 401-413, wherein the 4-10 membered heterocycle of $R^{36}$ is substituted with 0, 1 or 2 instances of fluoro.

Embodiment 418. The compound of any one of embodiments 401-413, wherein the 4-10 membered heterocycle of $R^{36}$ is unsubstituted.

Embodiment 419. The compound of any one of embodiments 401-410, wherein $R^{36}$ is selected from the group consisting of:

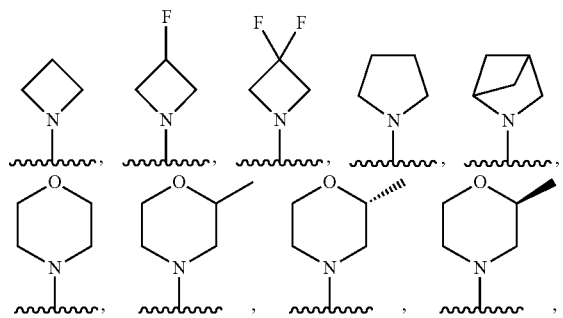

146

-continued

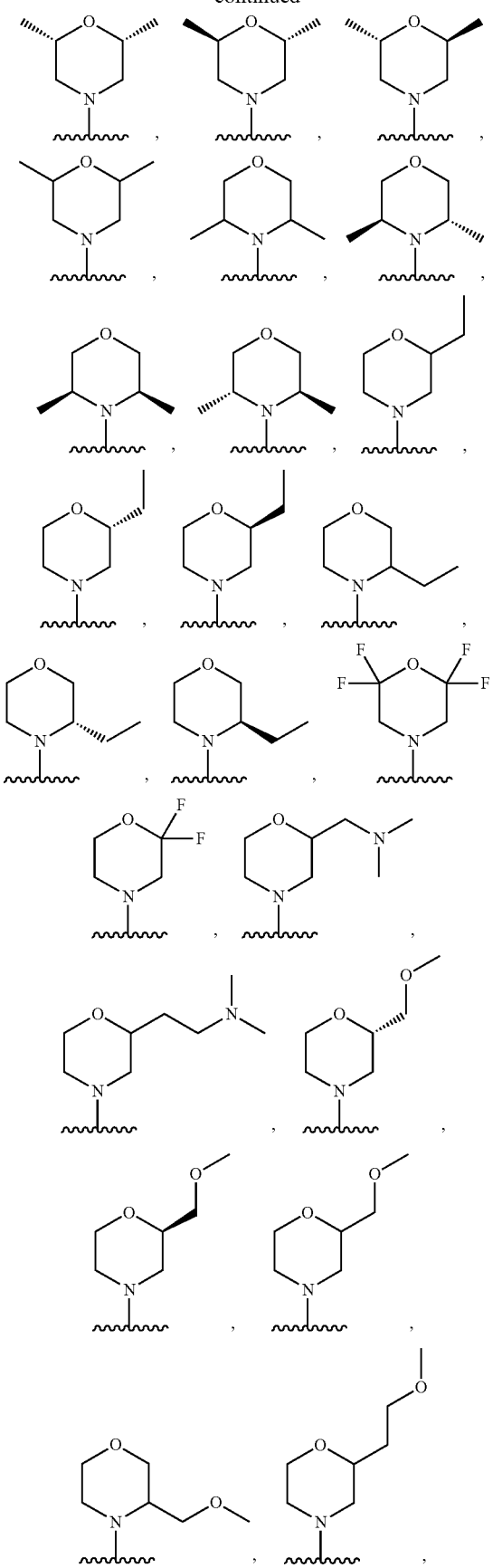

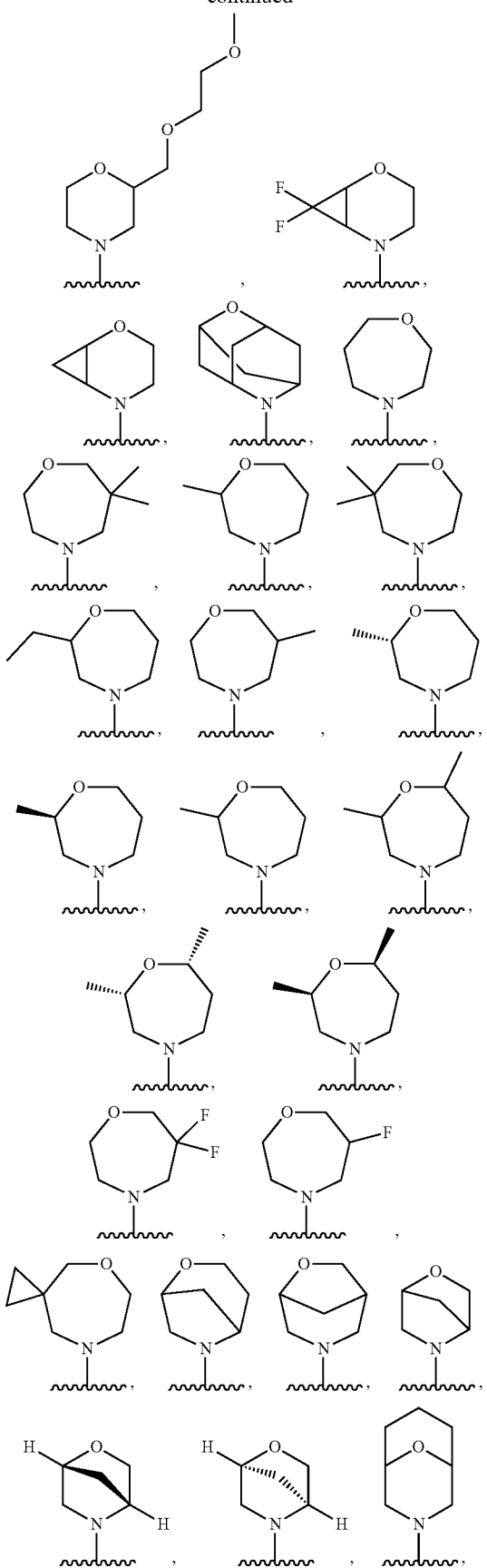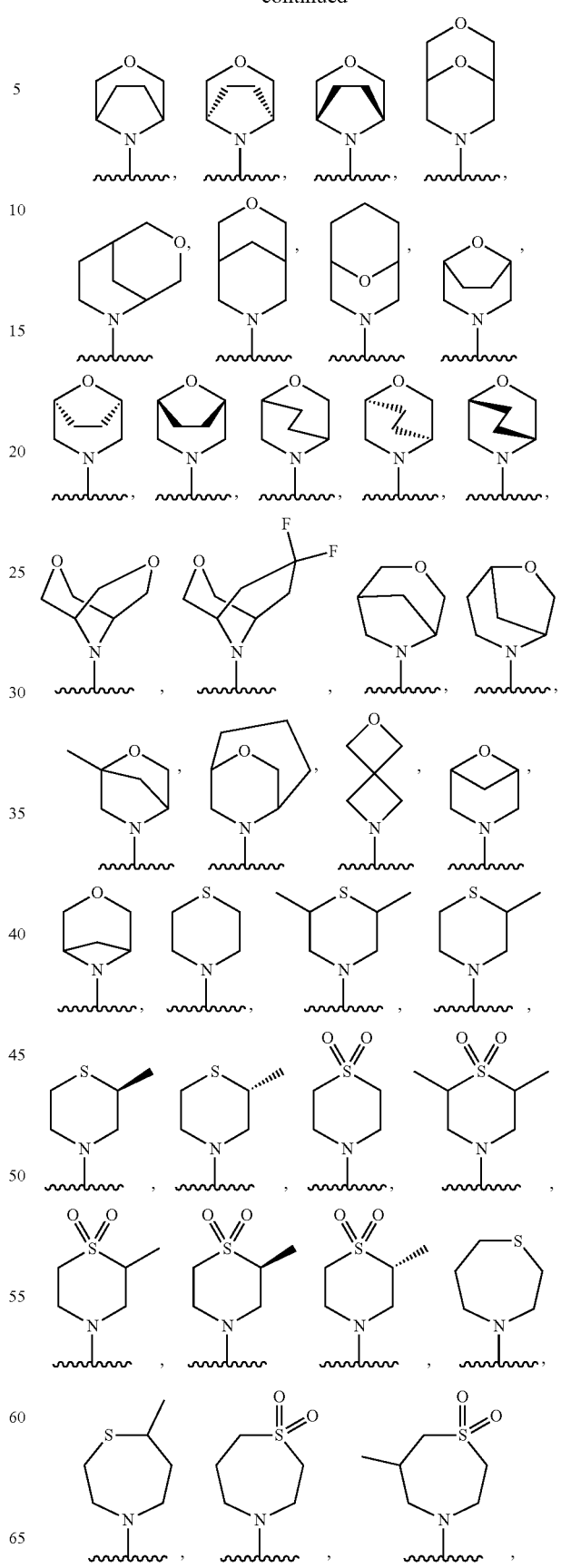

-continued
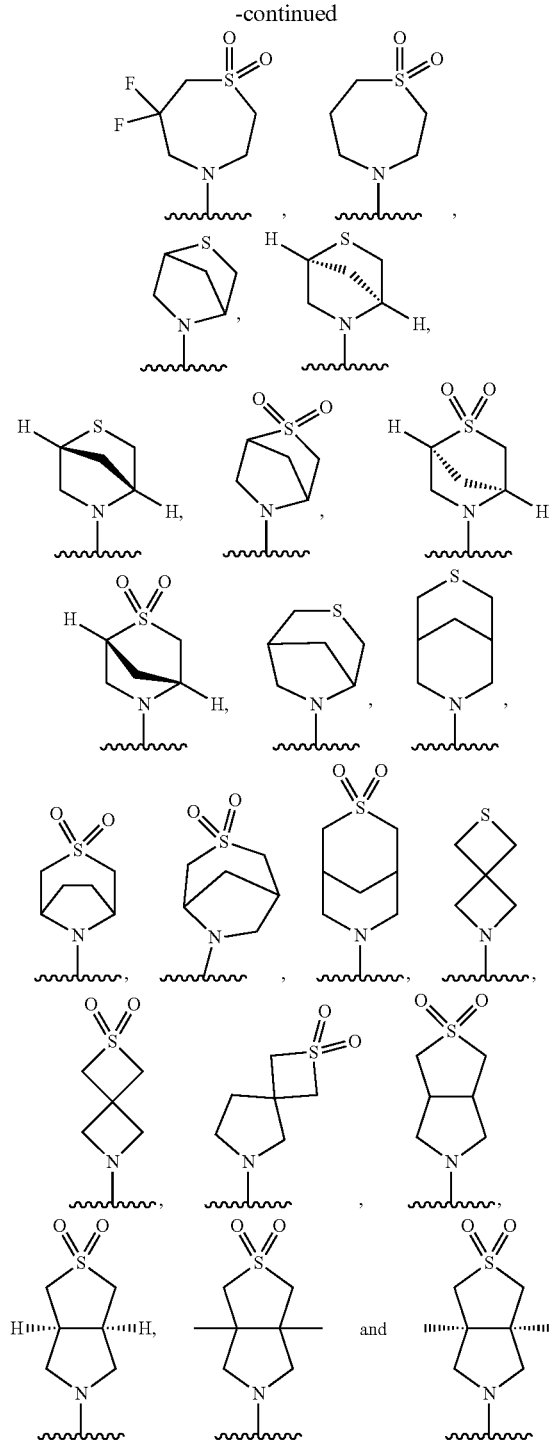
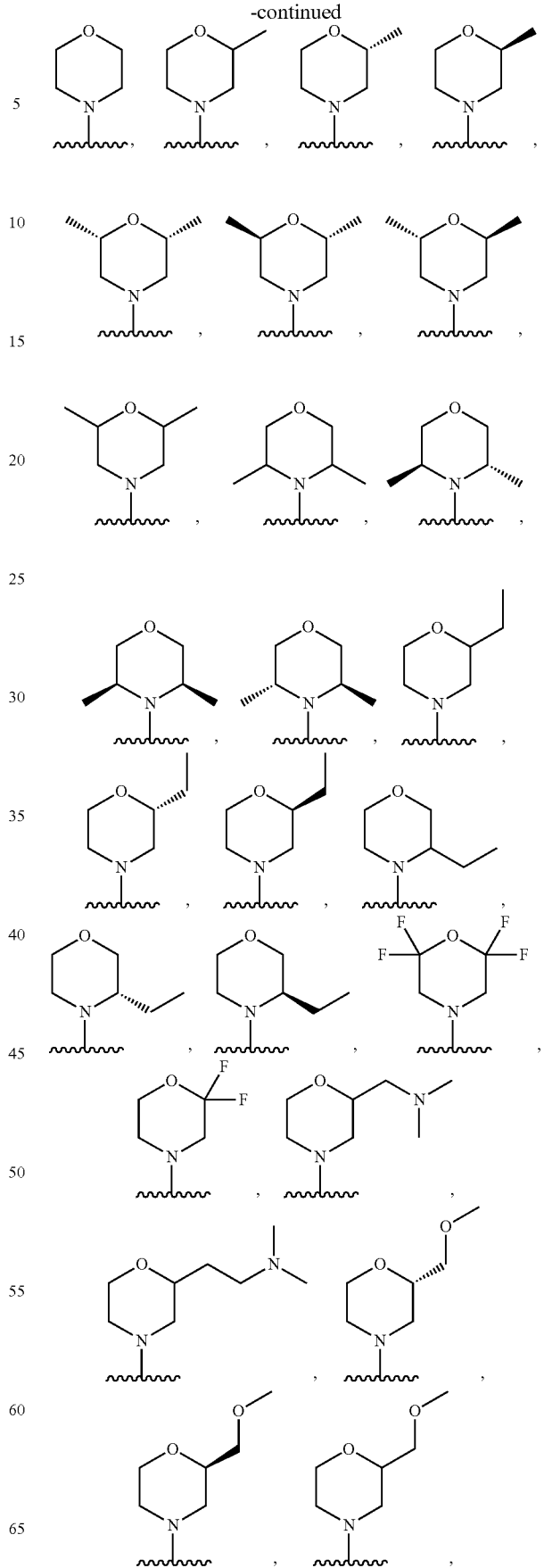
Embodiment 420. The compound of any one of embodiments 401-410, wherein $R^{36}$ is selected from the group consisting of:
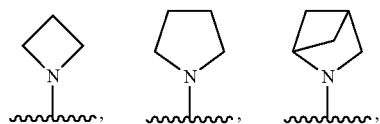

151
-continued
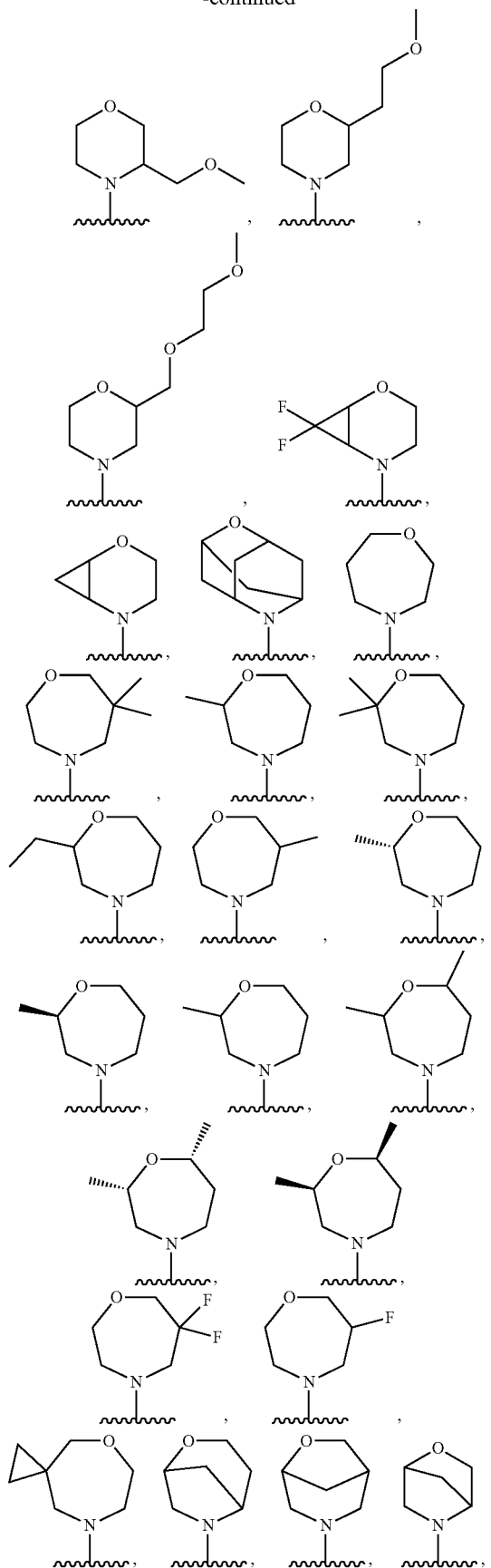
152
-continued
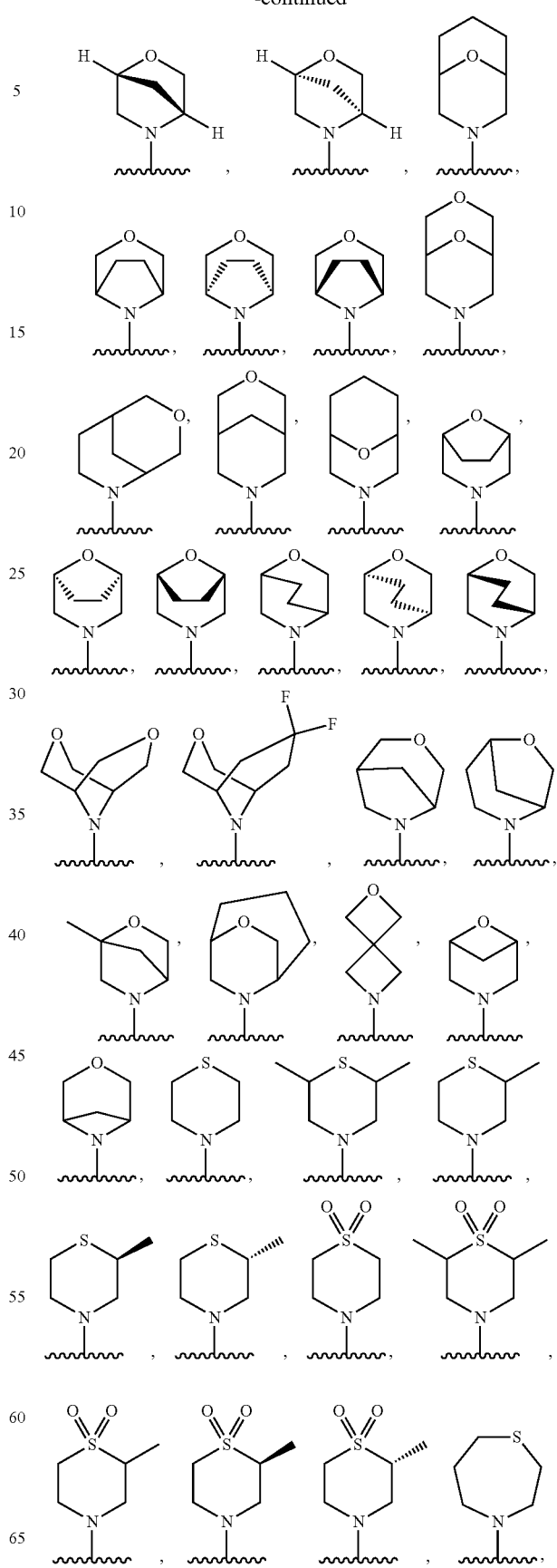

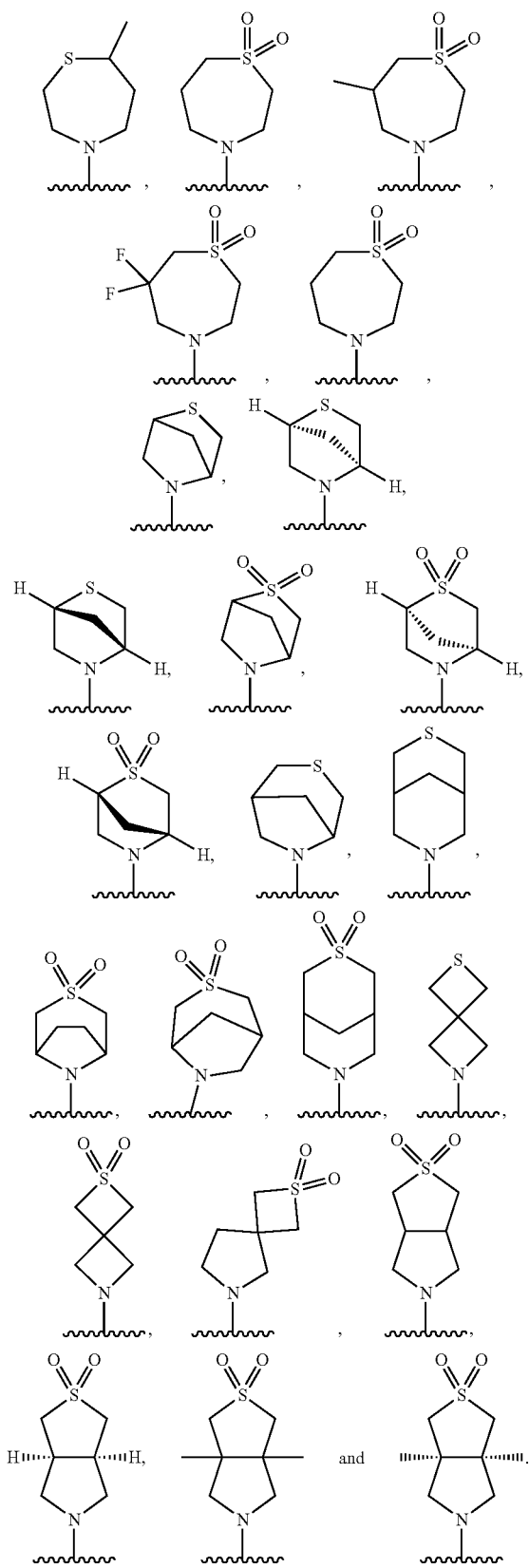
Embodiment 421. The compound of any one of embodiments 401-410, wherein R$^{36}$ is unsubstituted
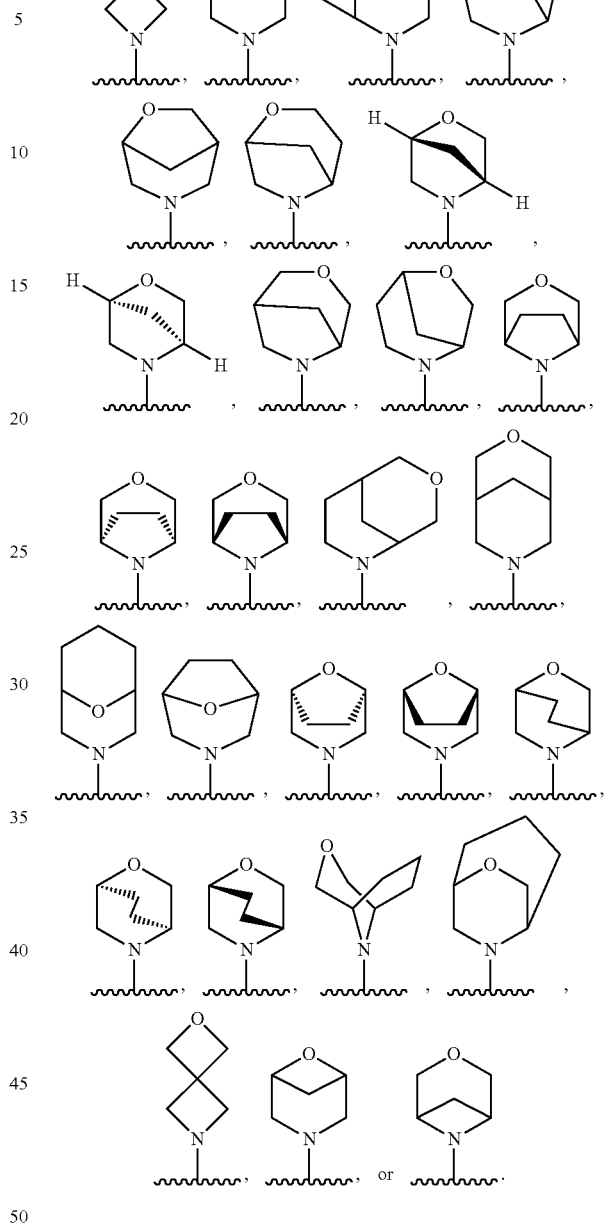
Embodiment 422. The compound of any one of embodiments 401-410, wherein R$^{36}$ is unsubstituted
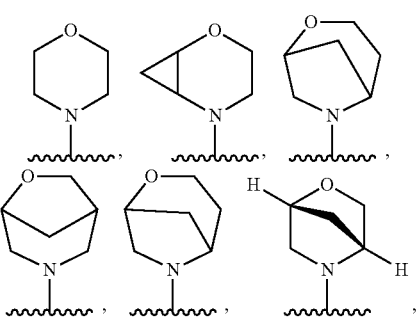

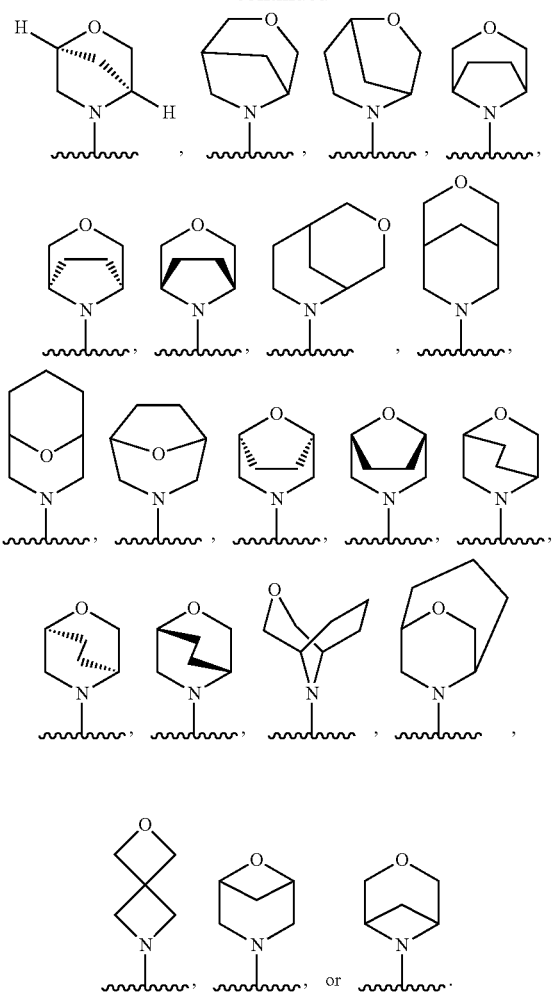

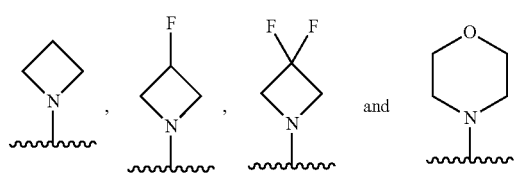

Embodiment 423. The compound of any one of embodiments 401-410, wherein $R^{36}$ is selected from the group consisting of:

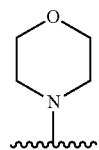

Embodiment 424. The compound of any one of embodiments 401-410, wherein $R^{36}$ is unsubstituted or unsubstituted

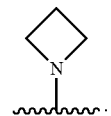

Embodiment 425. The compound of any one of embodiments 401-410, wherein $R^{36}$ is unsubstituted

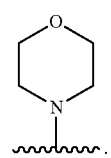

Embodiment 426. The compound of any one of embodiments 401-425, wherein p is 1.

Embodiment 427. The compound of any one of embodiments 1-61, 63, 66-84, 86-114, 116-332 and 334-370, wherein $R^{31}$ is selected from the group consisting of:

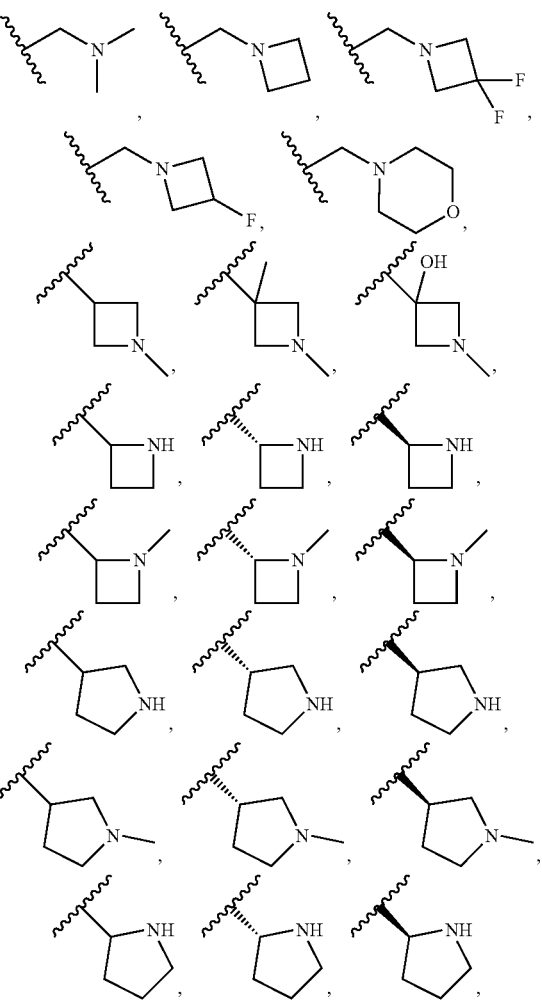

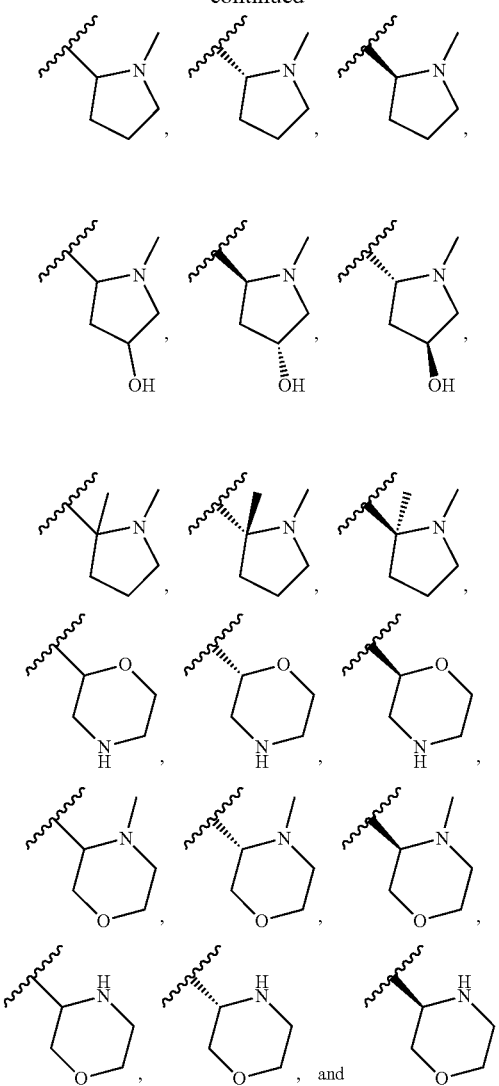
Embodiment 428. The compound of any one of embodiments 1-61, 63, 66-84, 86-114, 116-332 and 334-370, wherein $R^{31}$ is selected from the group consisting of:
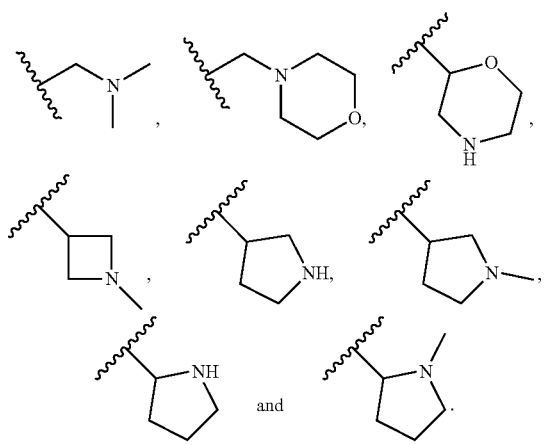
Embodiment 429. The compound of any one of embodiments 1, 11 and 18, selected from the group consisting of:
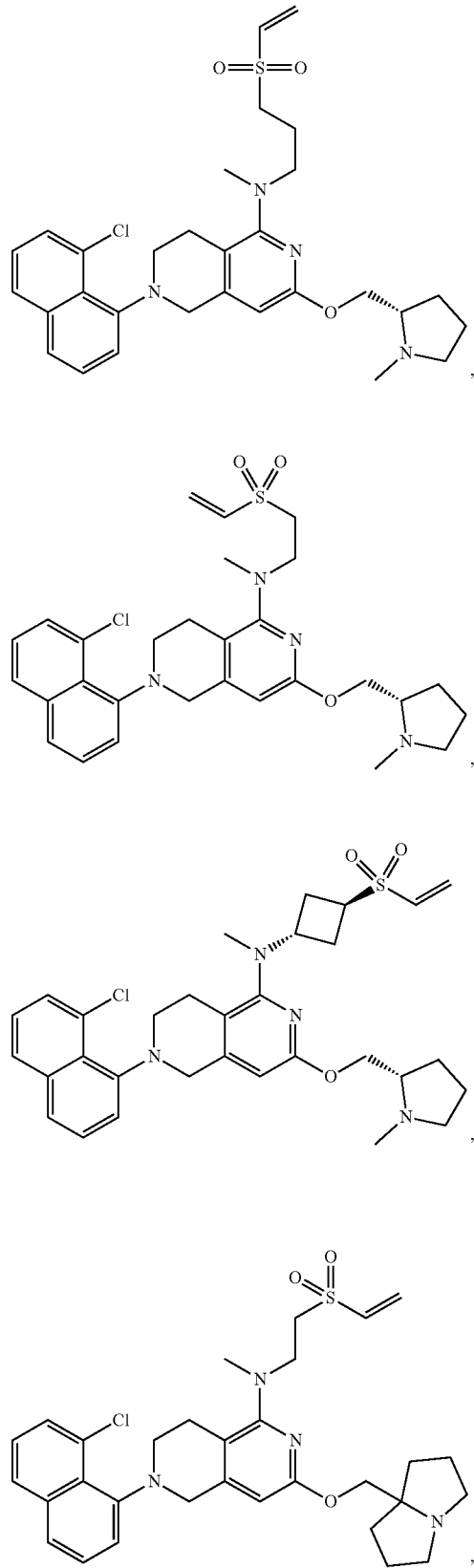

159
-continued
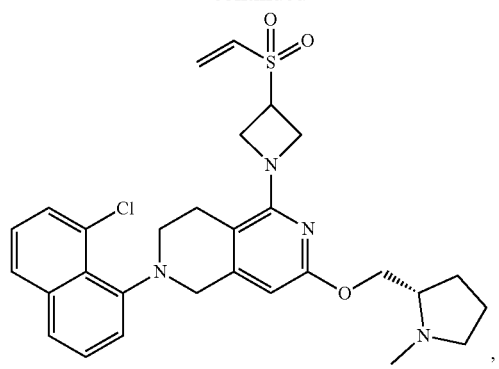
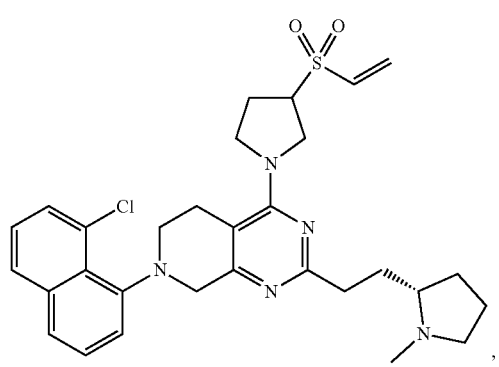
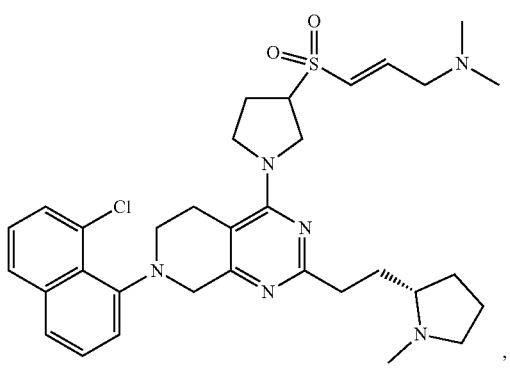
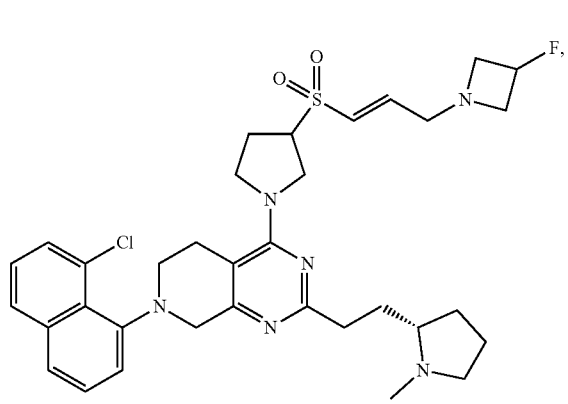
160
-continued
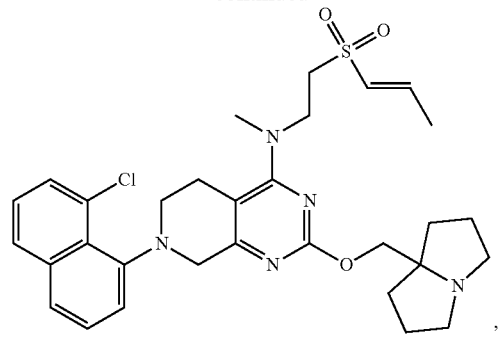
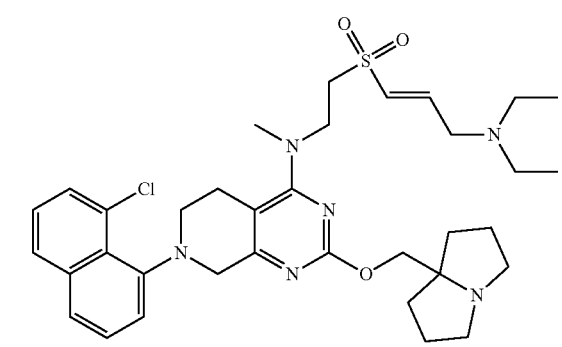
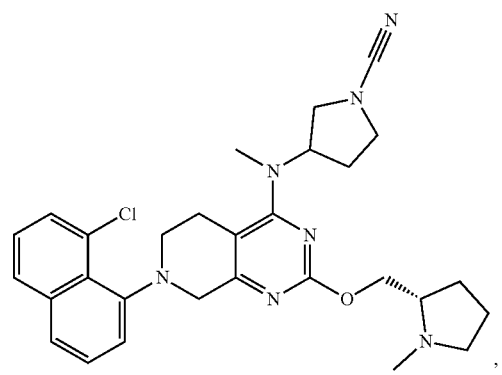
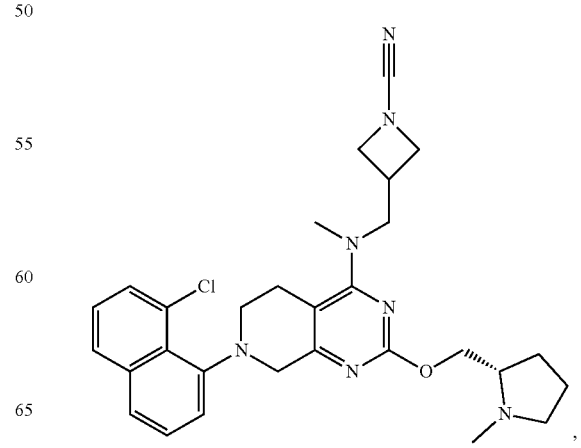

-continued
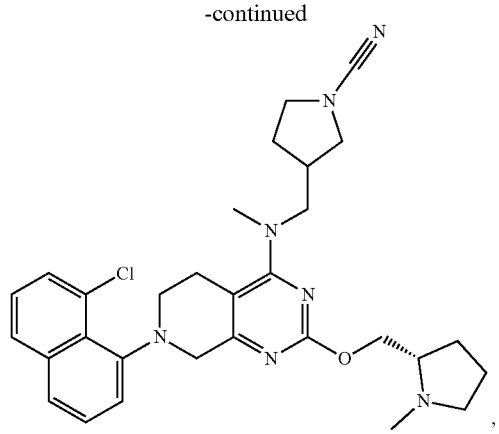
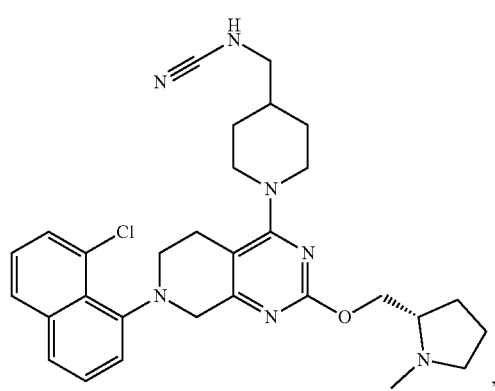
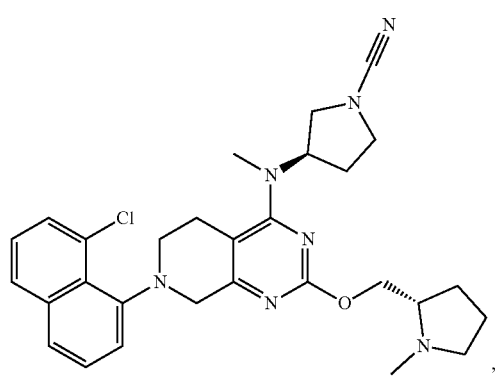
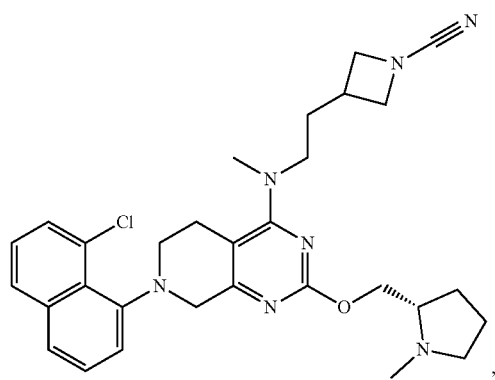
-continued
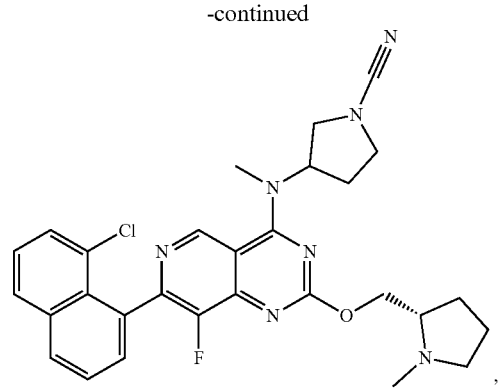
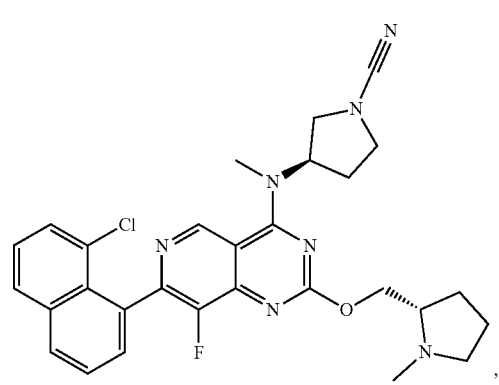
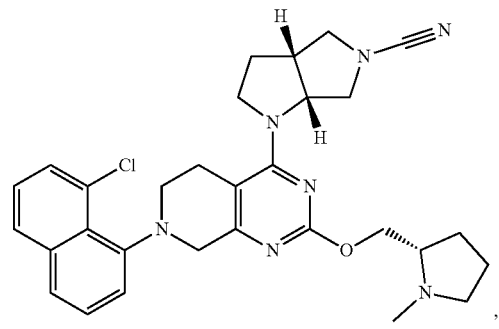
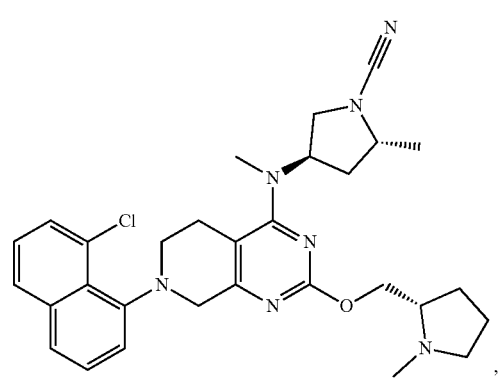

163
-continued
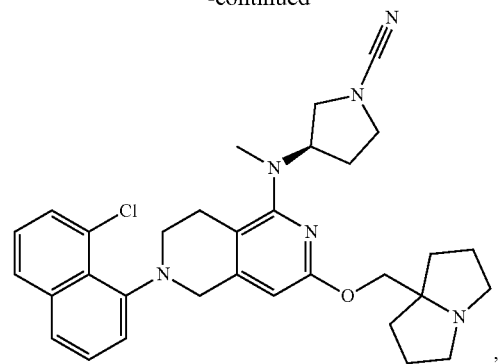
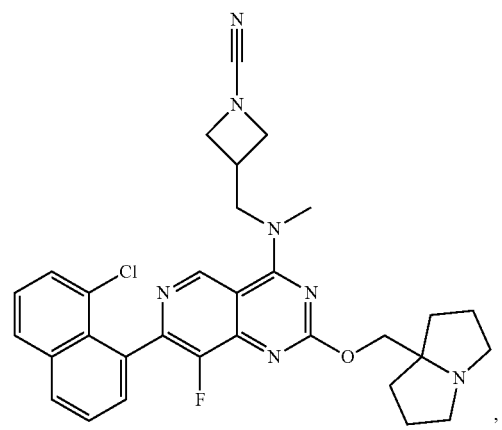
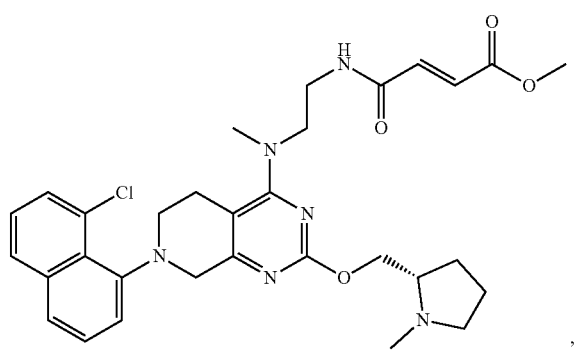
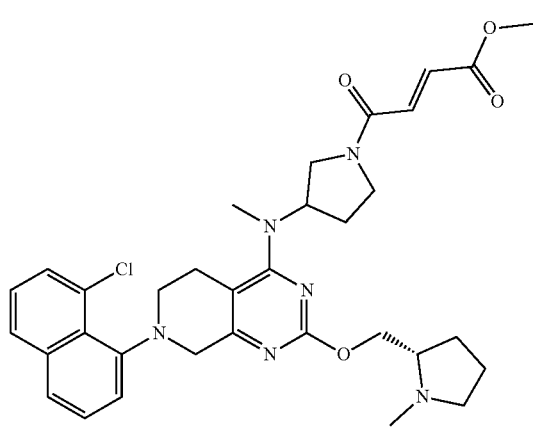
164
-continued
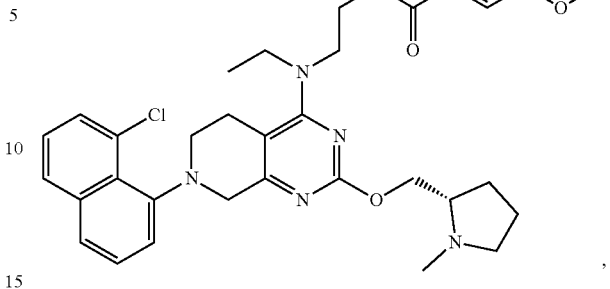
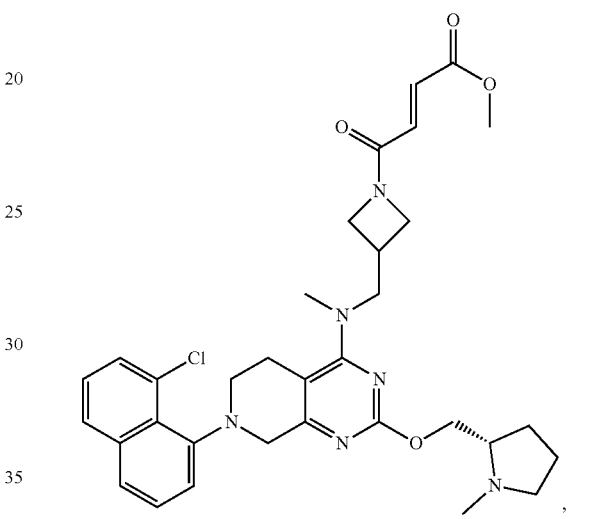
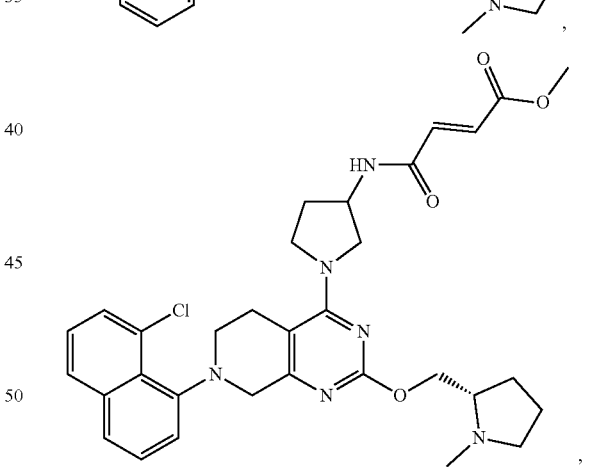
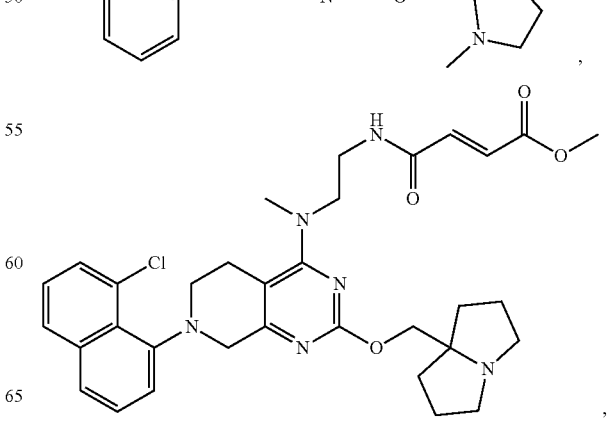

165
-continued
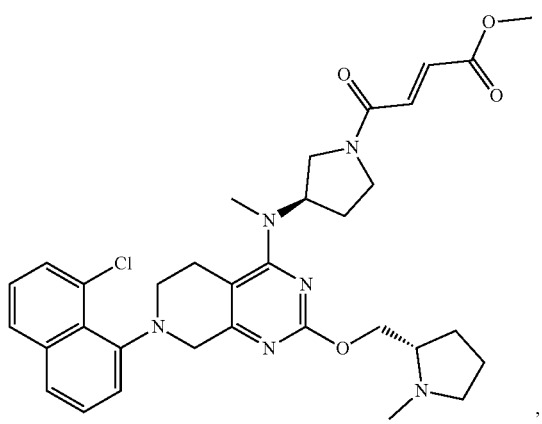
,
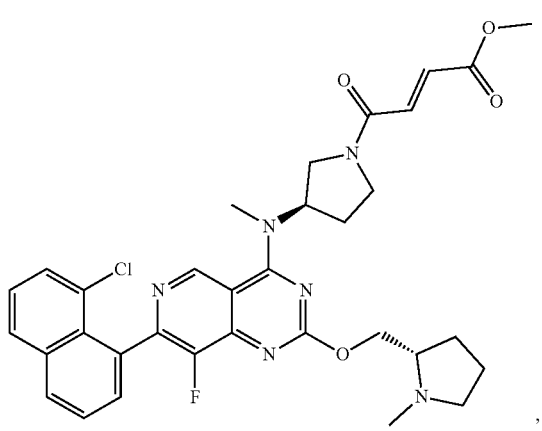
,
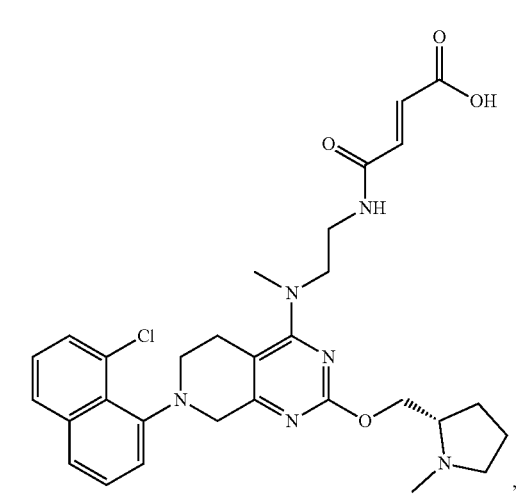
,
166
-continued
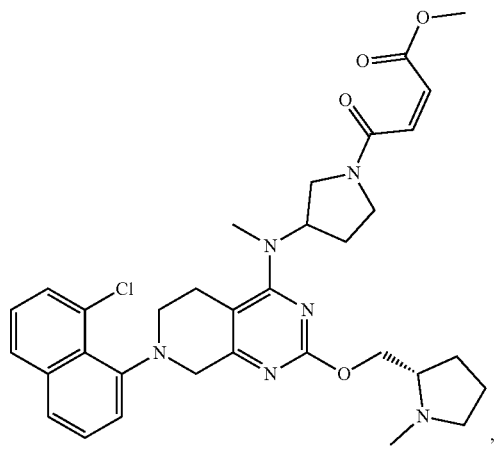
,
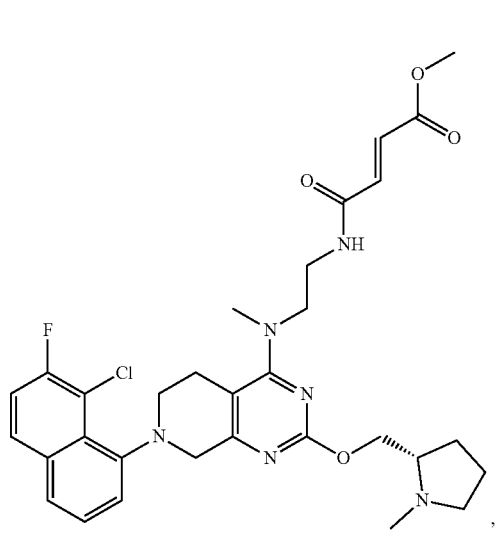
,
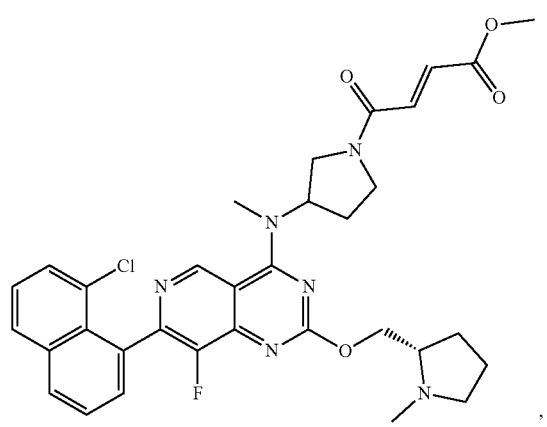
, 167
-continued
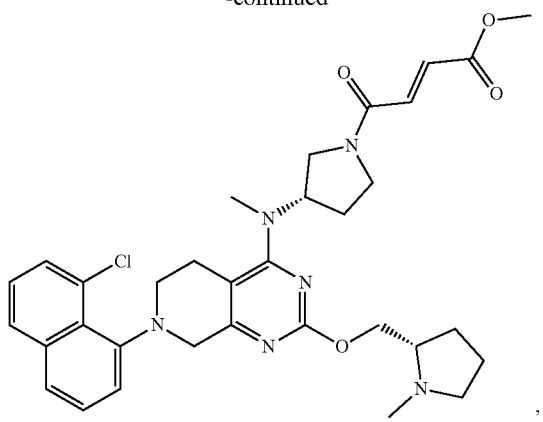
,
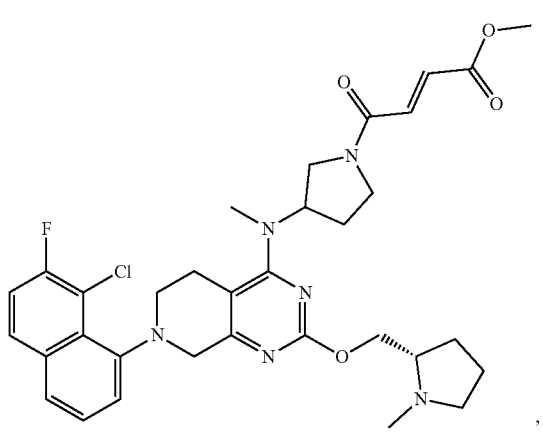
,
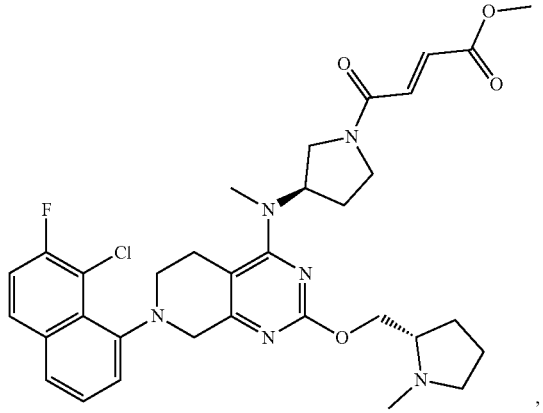
,
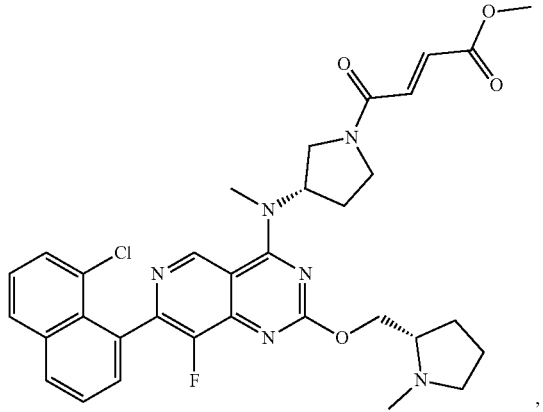
,
168
-continued
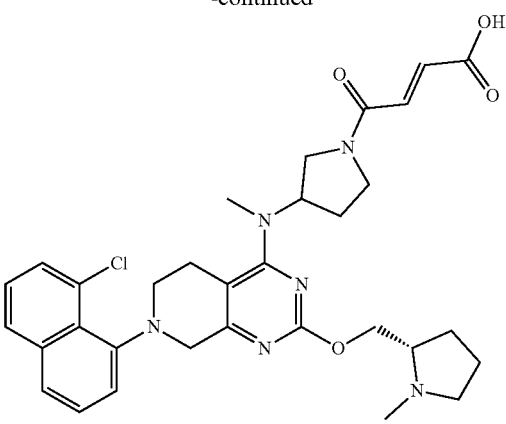
,
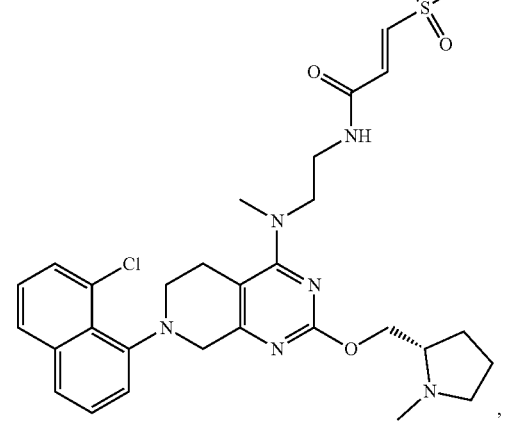
,
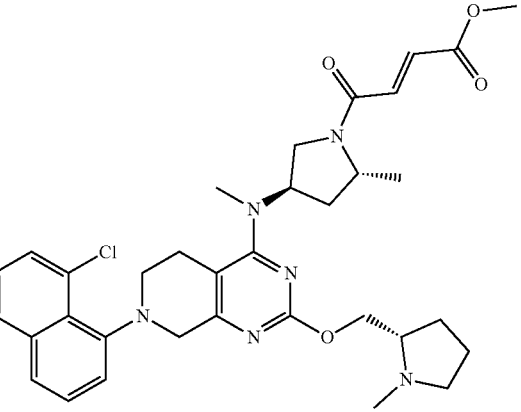
,
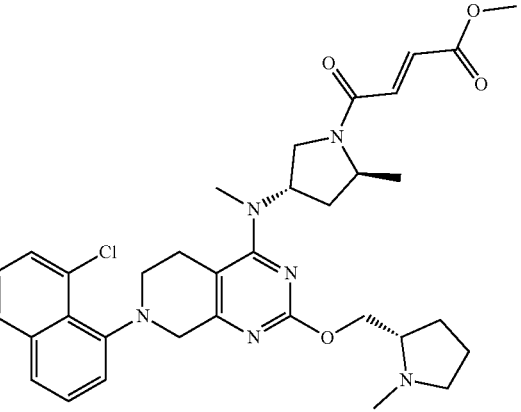
,

169
-continued
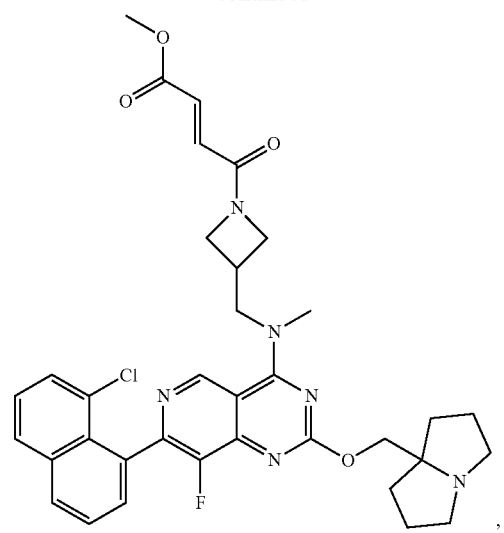
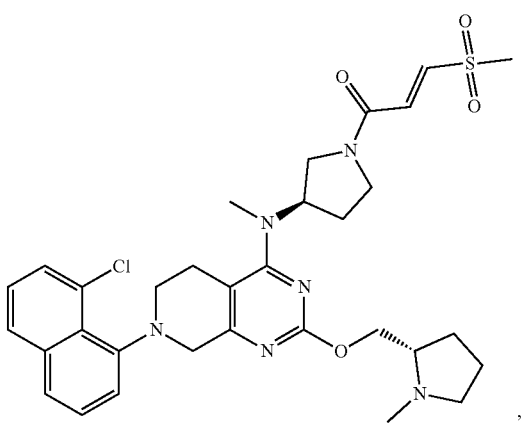
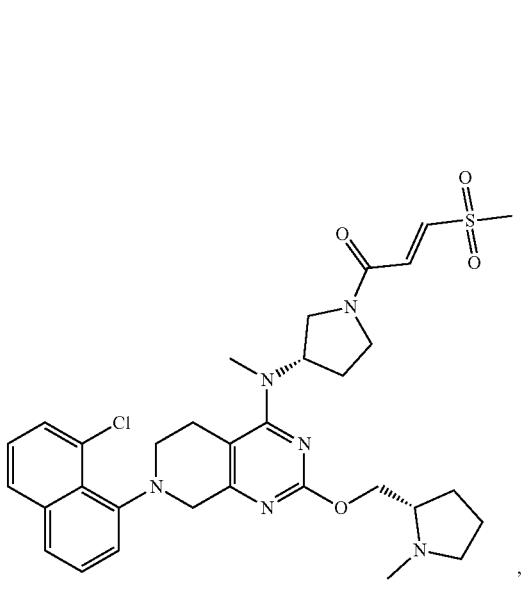
170
-continued
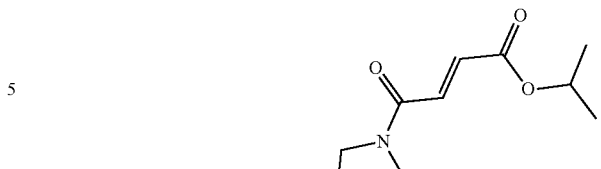

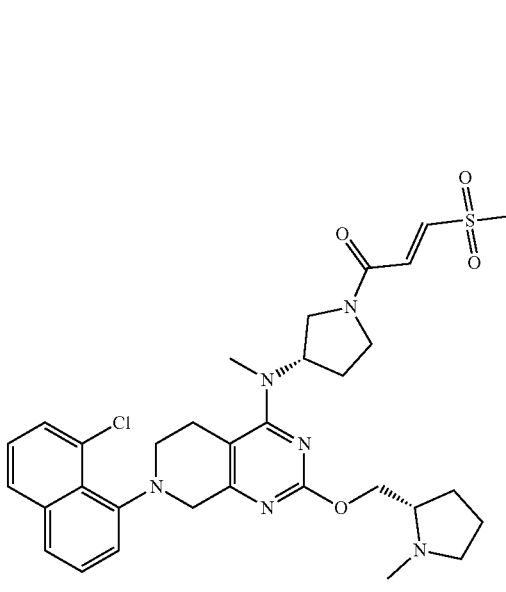
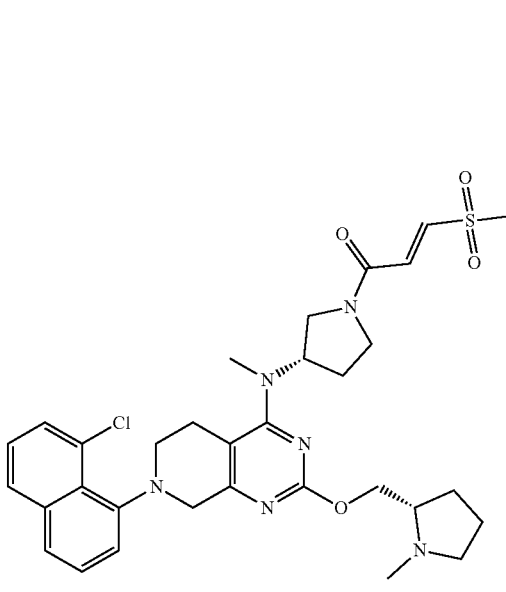

-continued
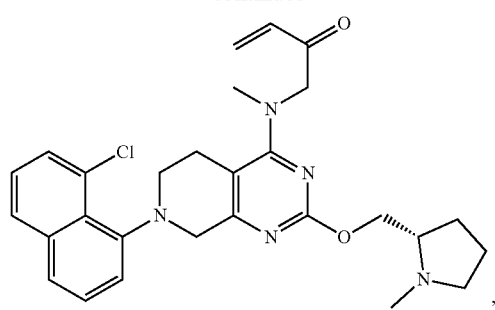
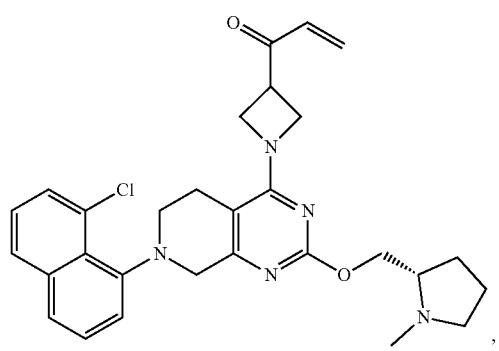
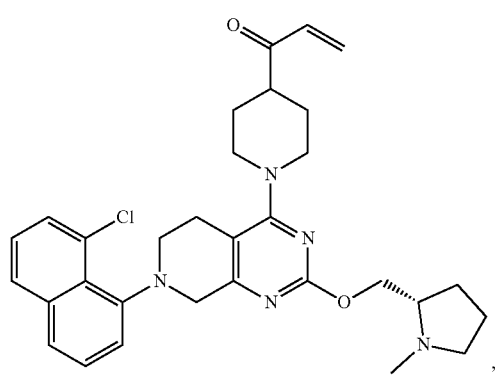
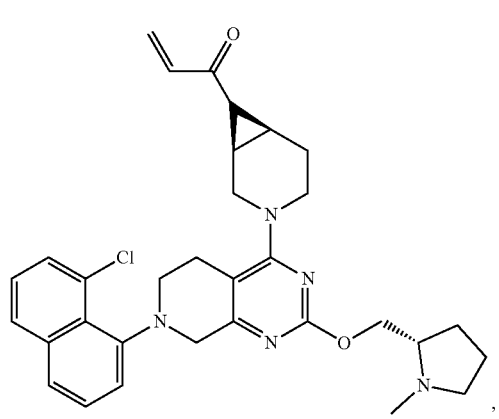
-continued
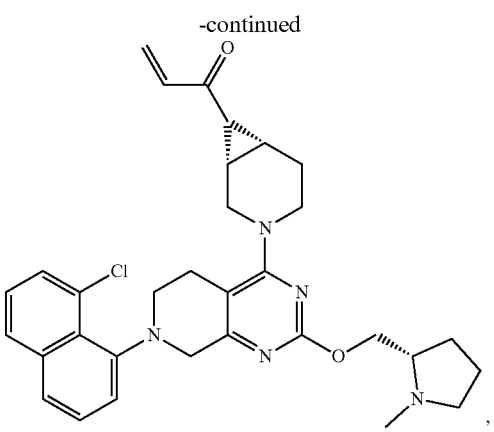
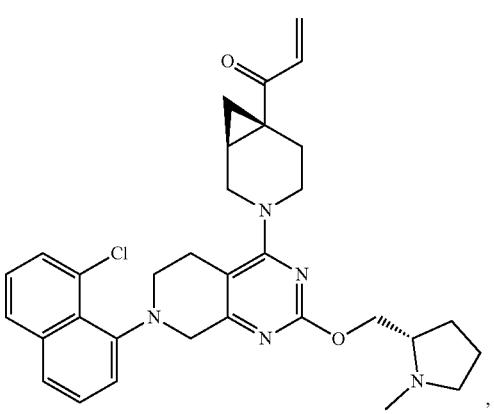
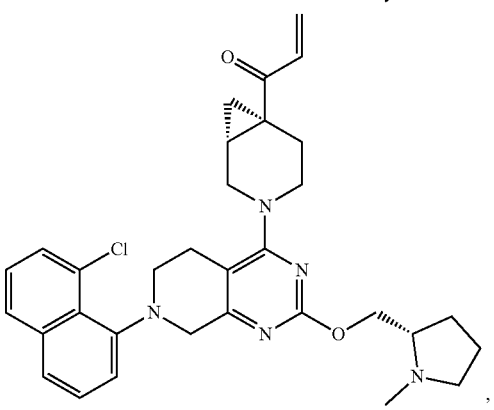
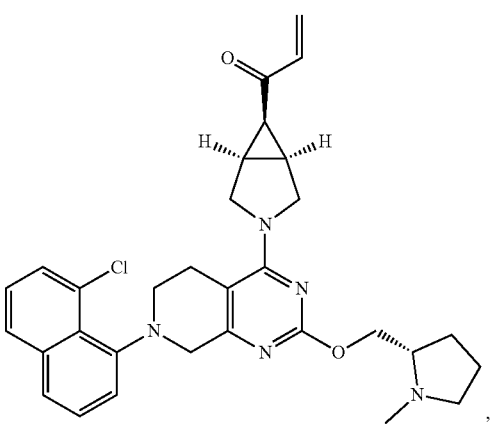

173
-continued
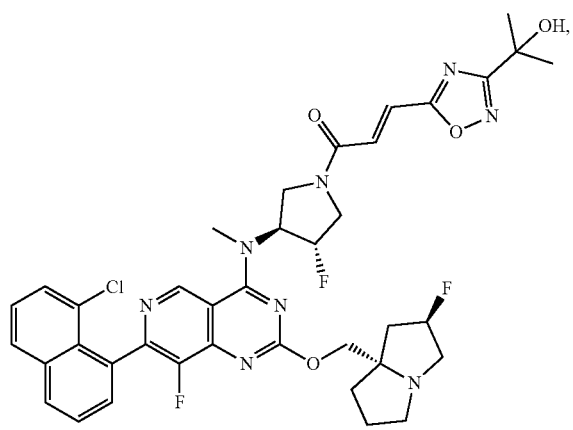
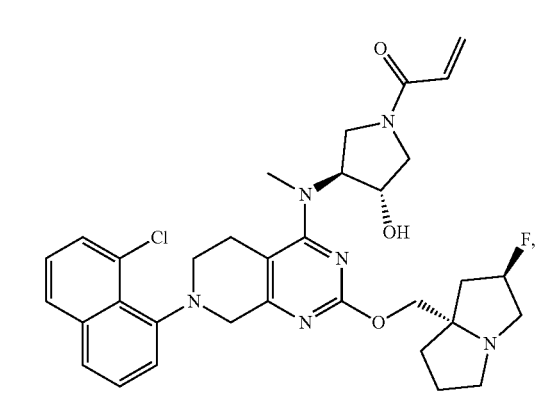
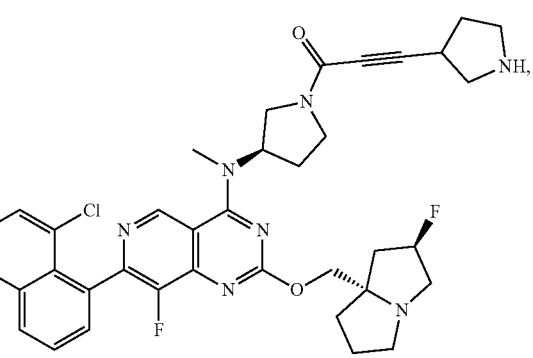
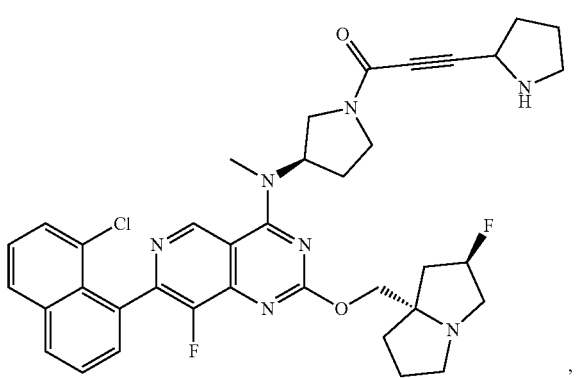
174
-continued
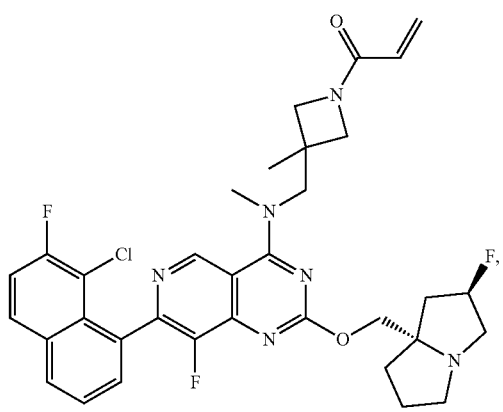
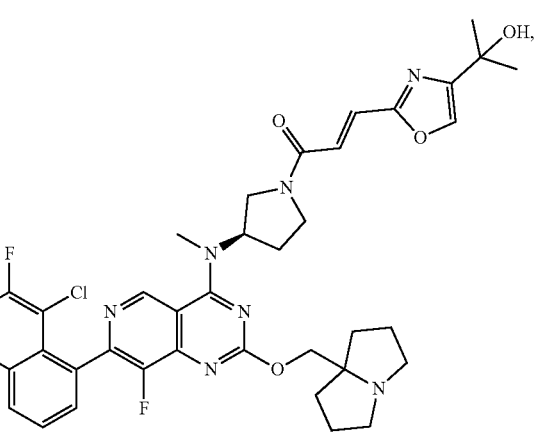
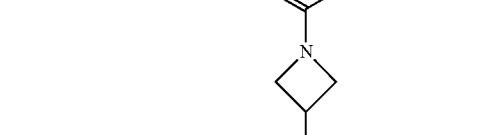
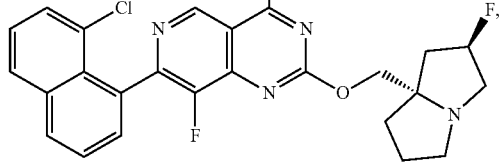

175
-continued
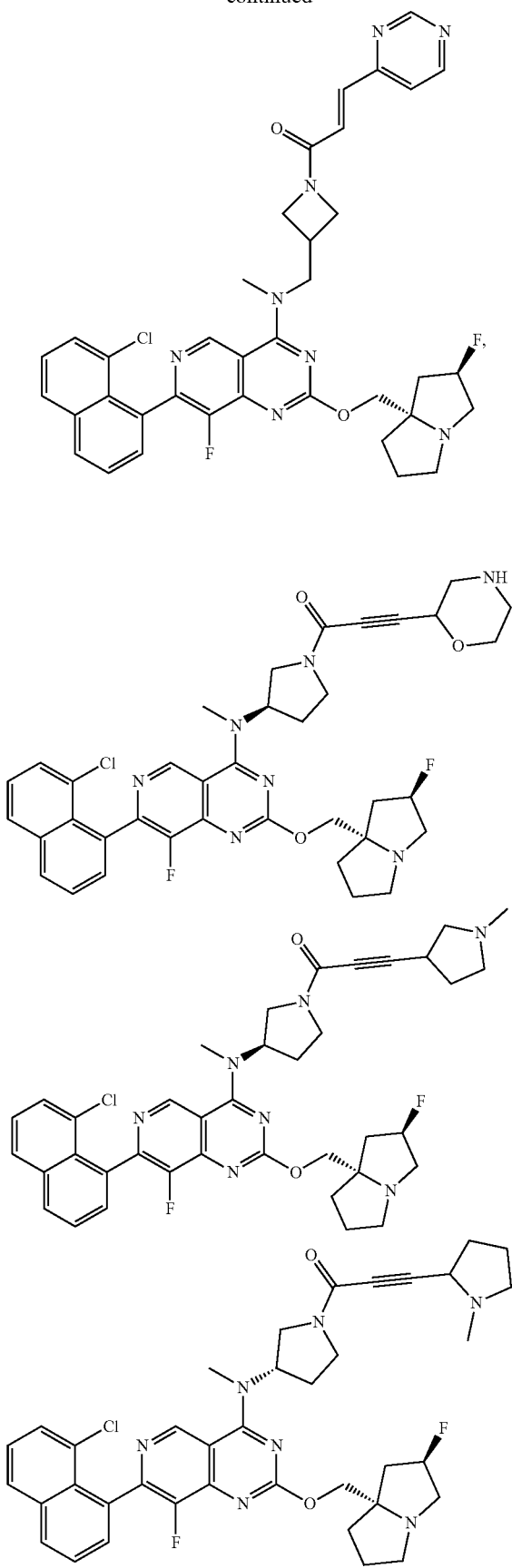
176
-continued
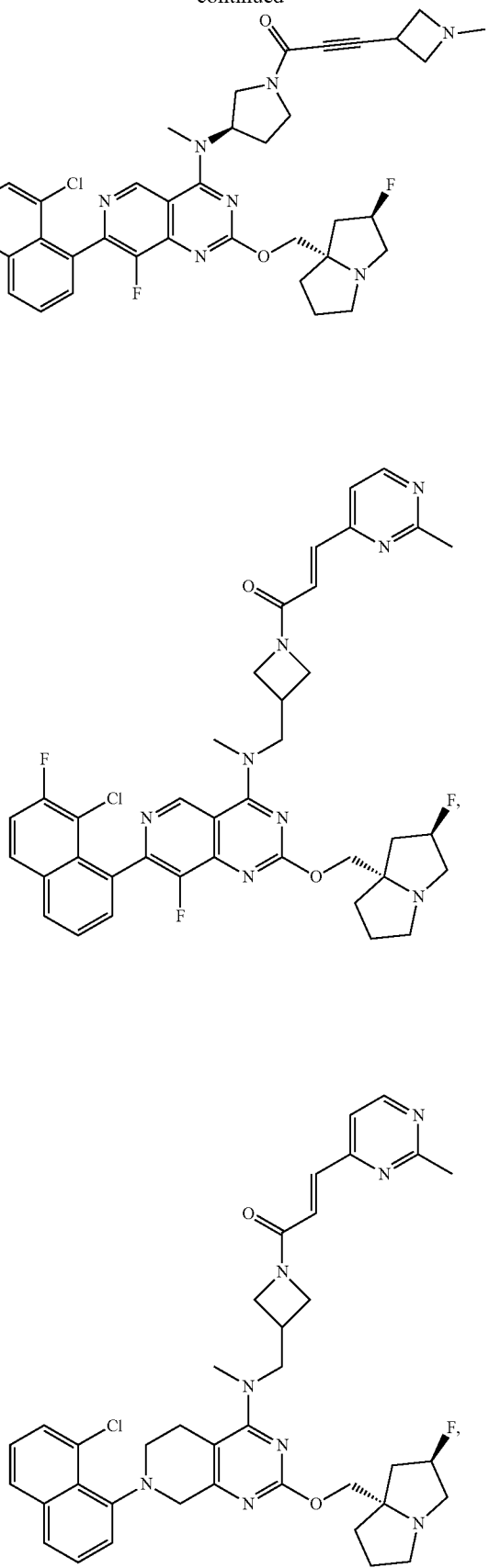

177
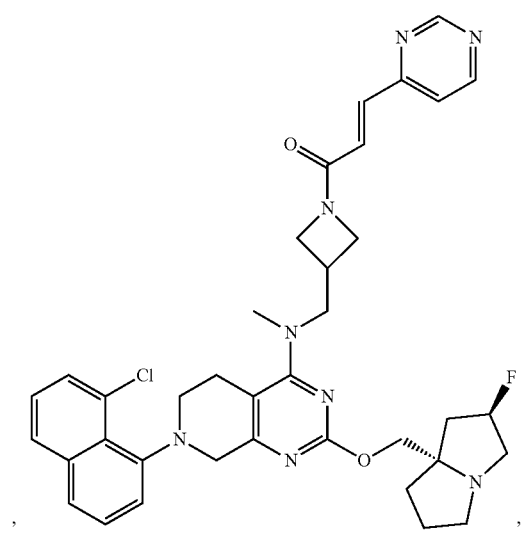
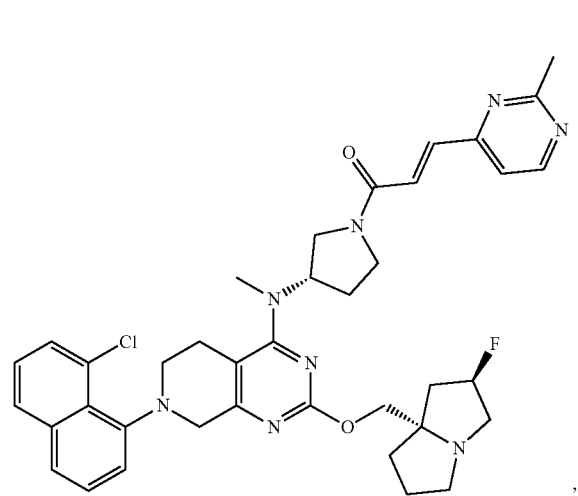
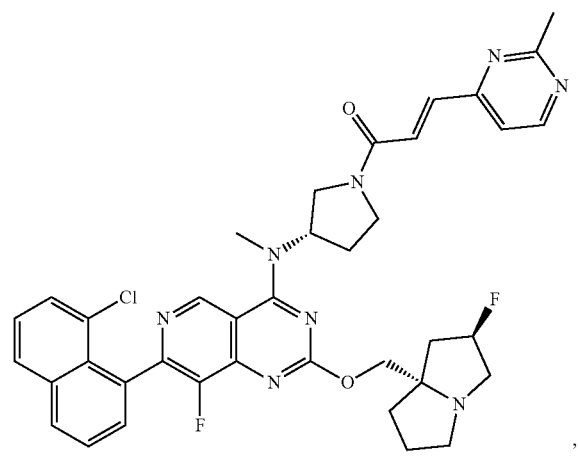
178
-continued
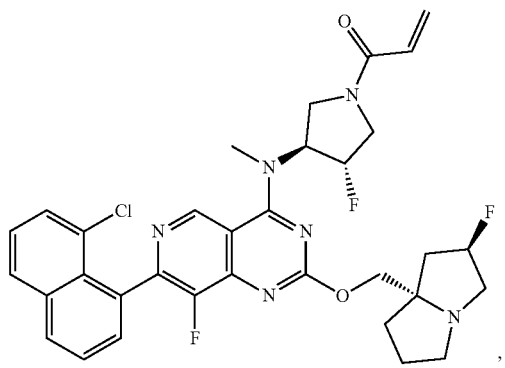
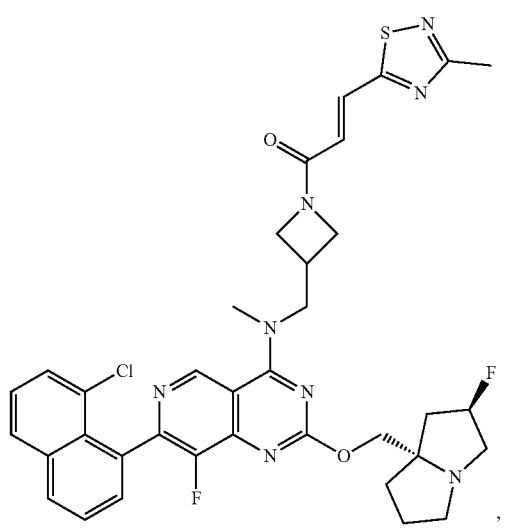
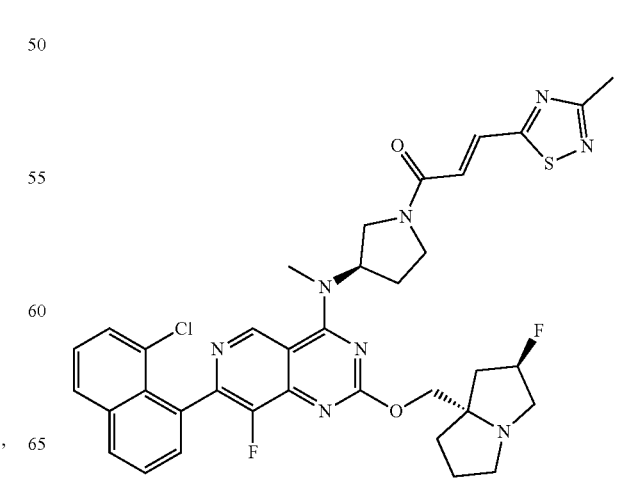

179
-continued
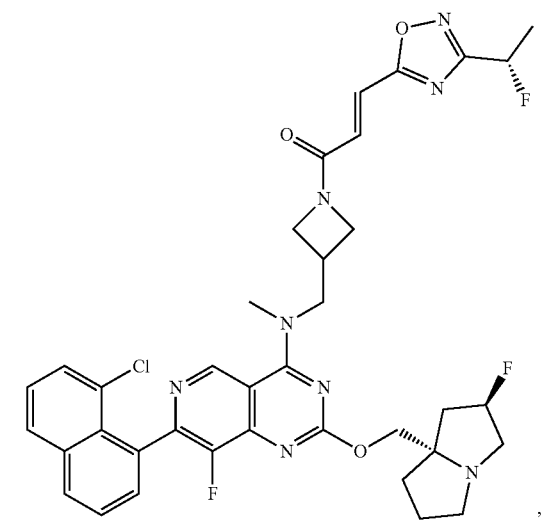
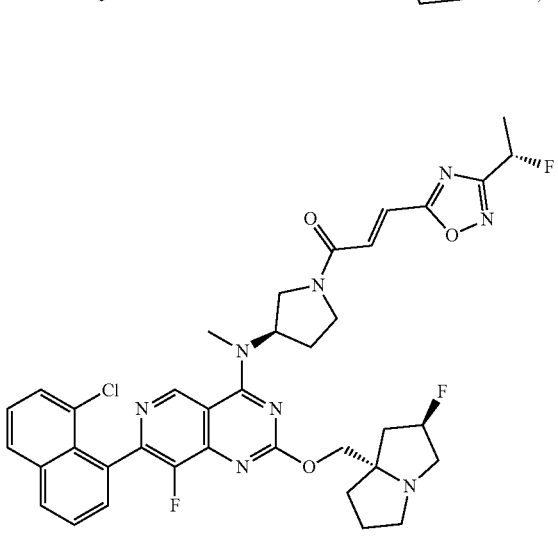
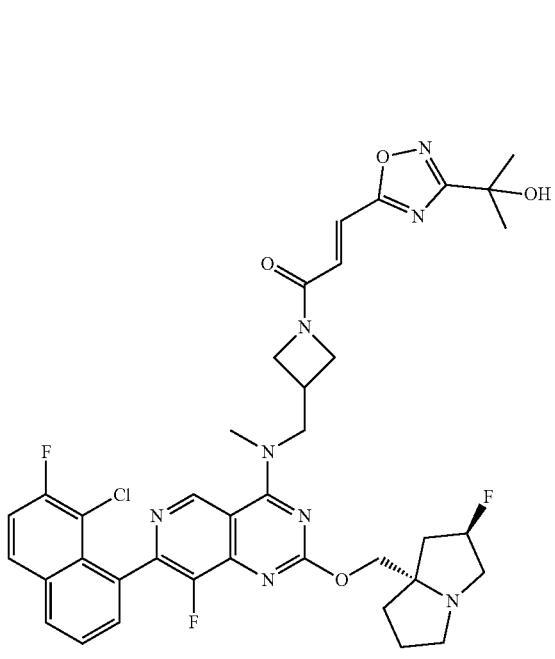
180
-continued
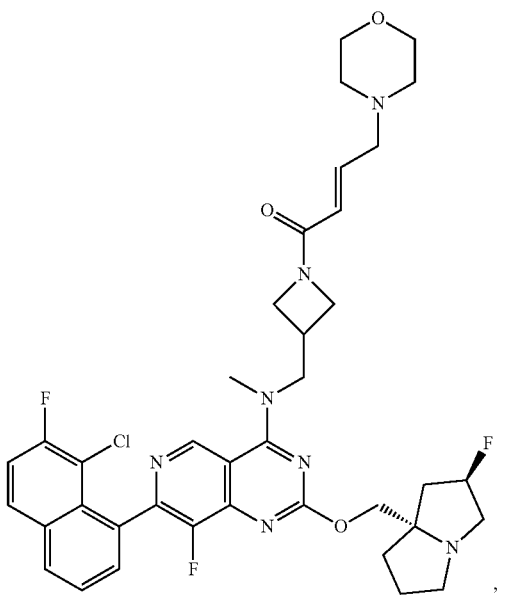

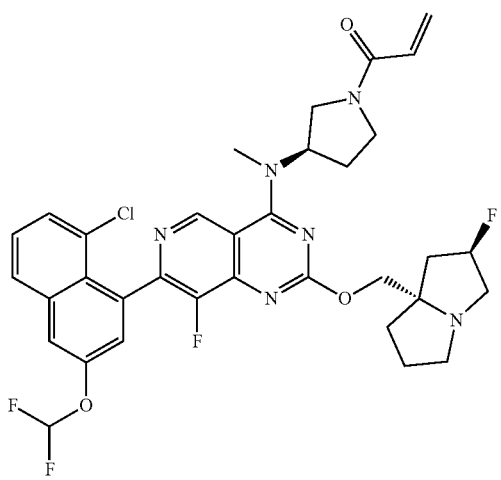
,
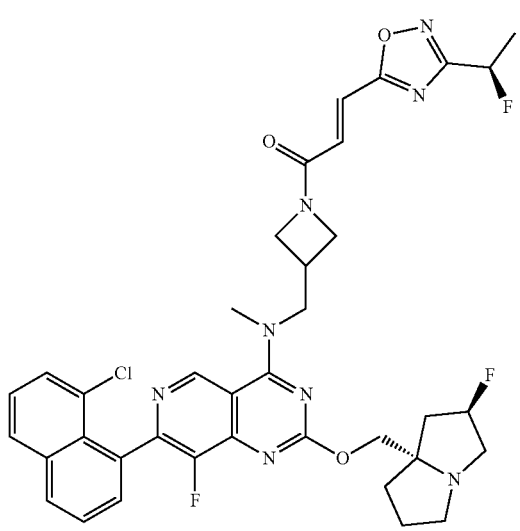
,
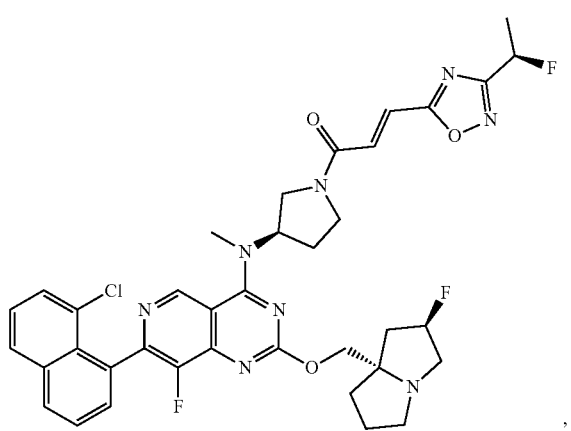
,
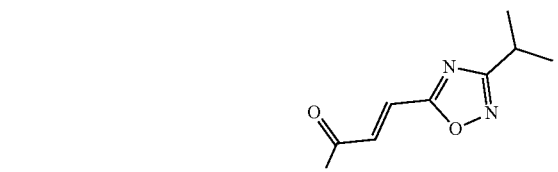
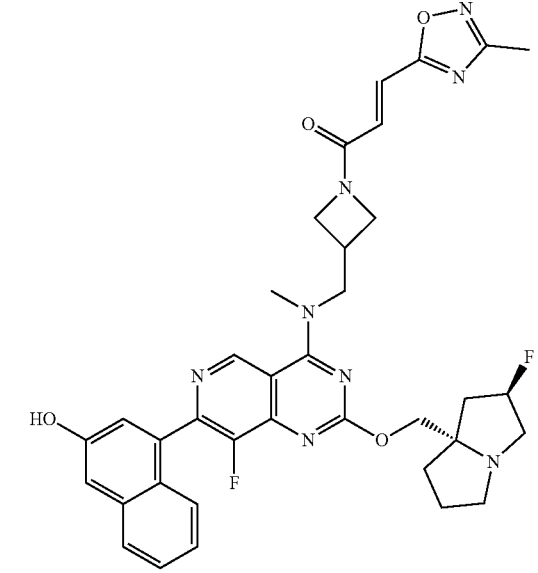
,
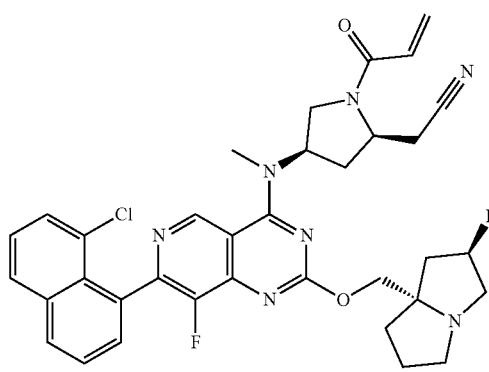
, 183
-continued
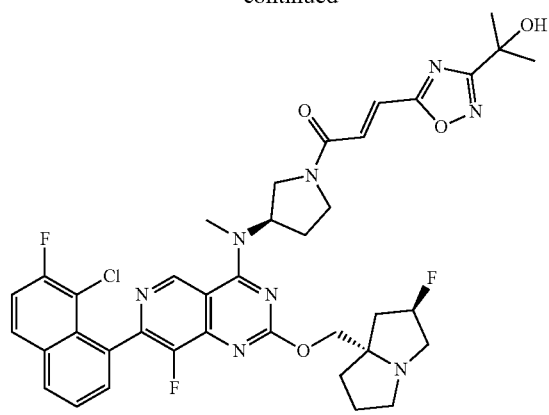
,
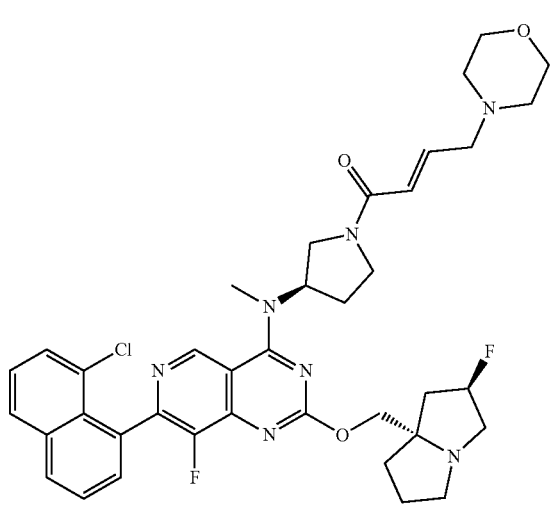
,
184
-continued
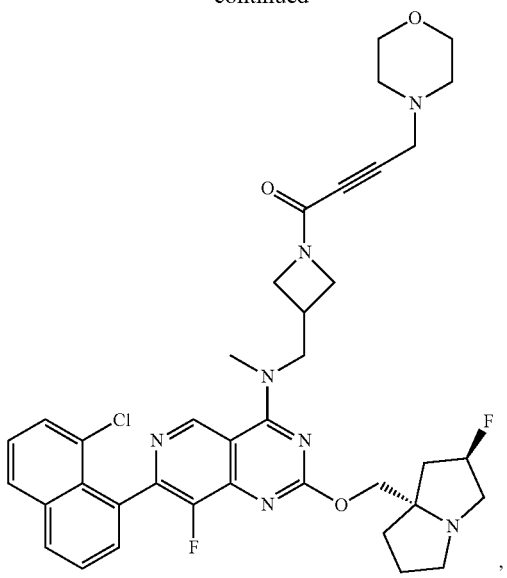
,
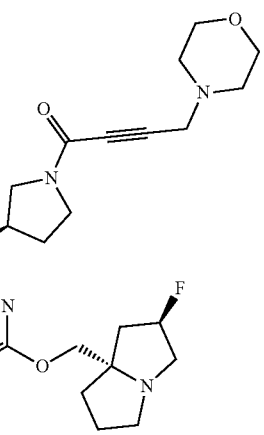
,
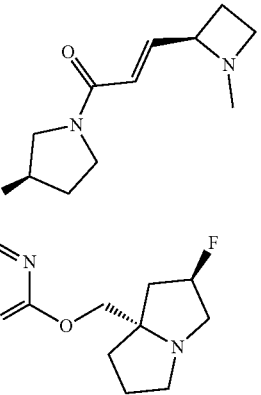
, 185
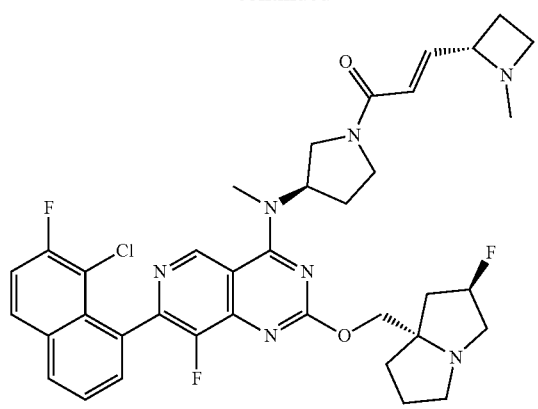
186
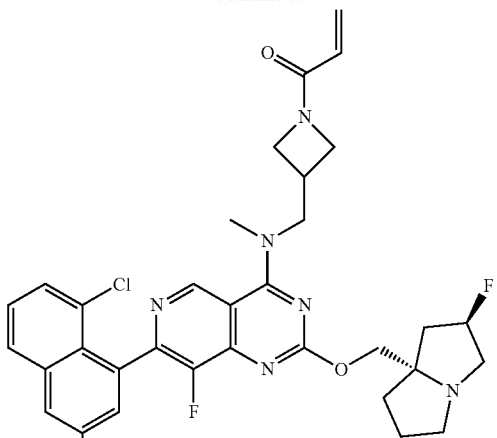
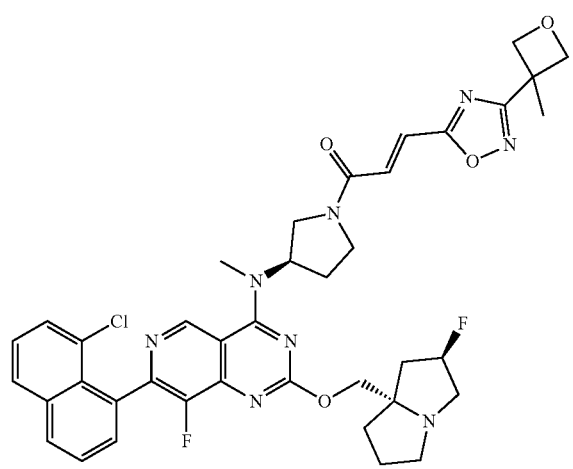
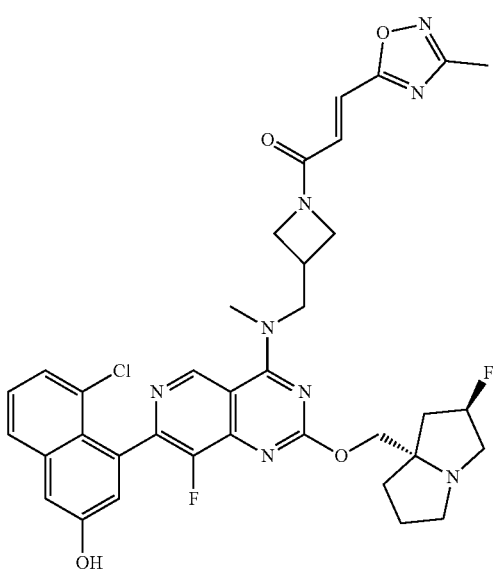
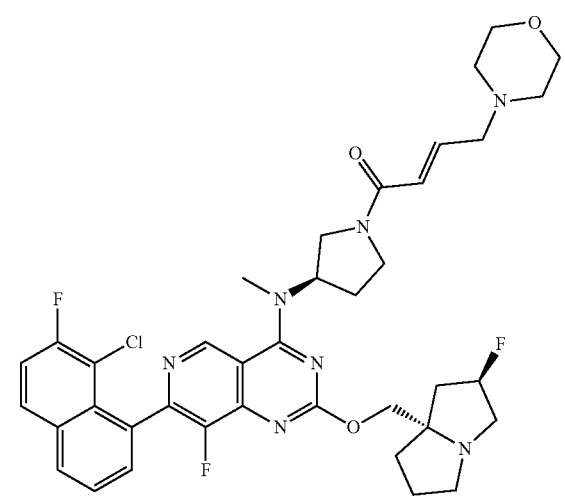
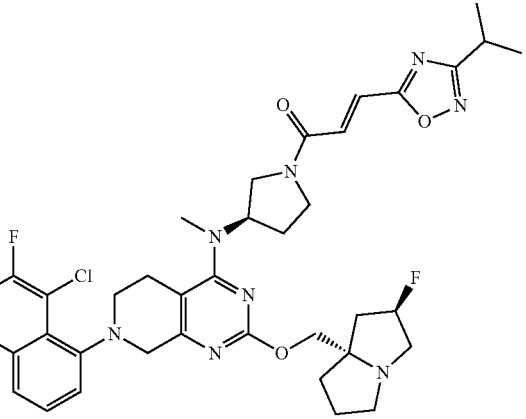

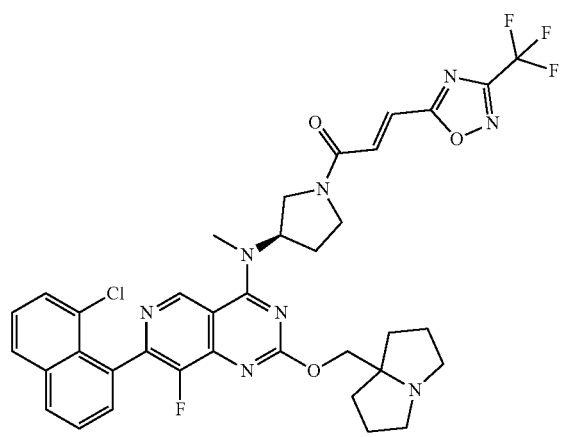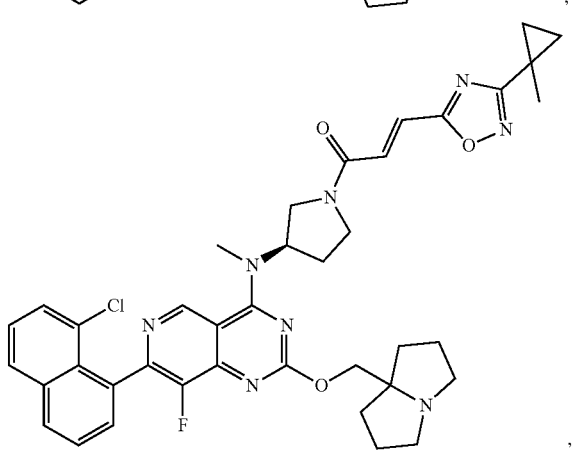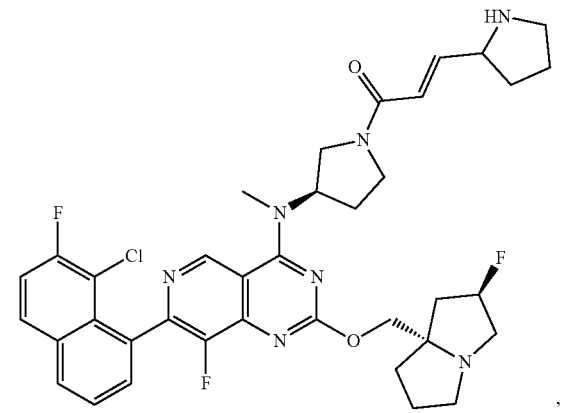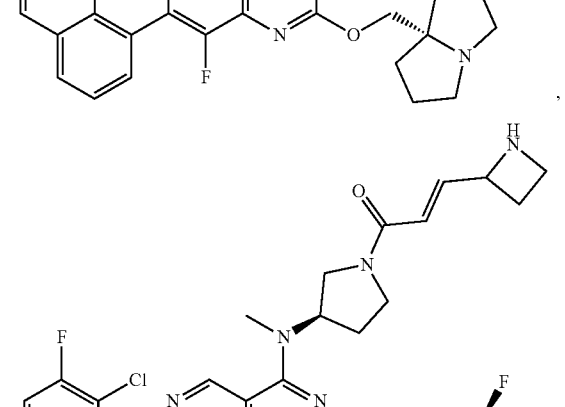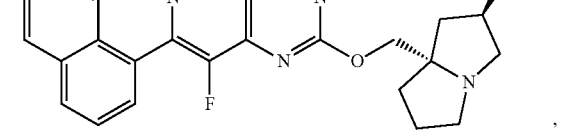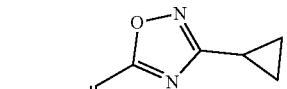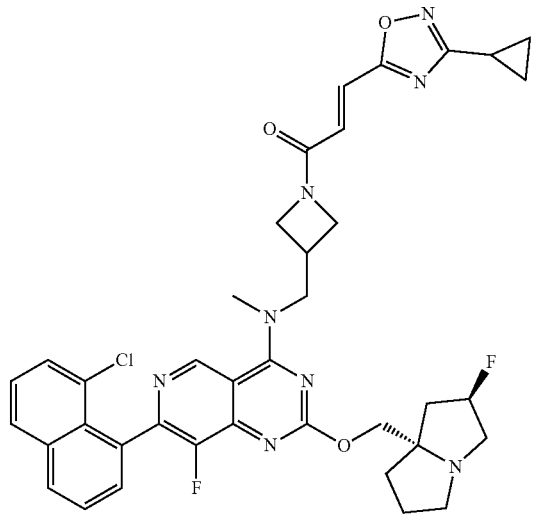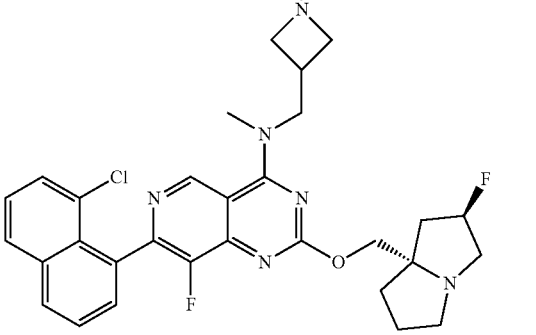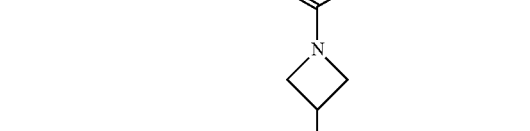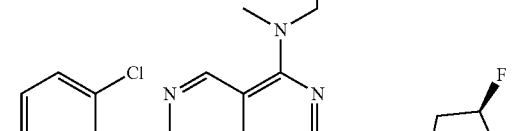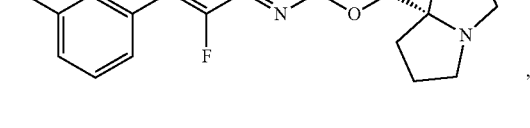

-continued
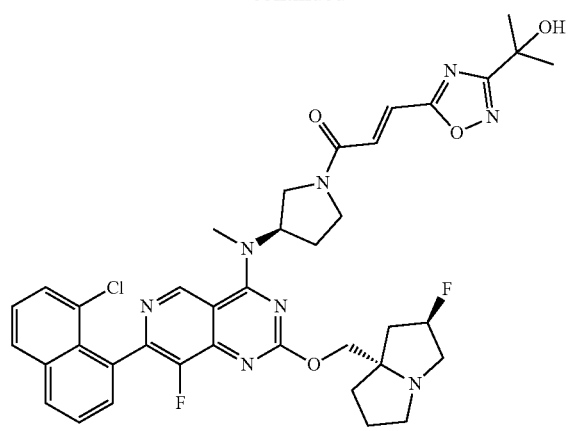
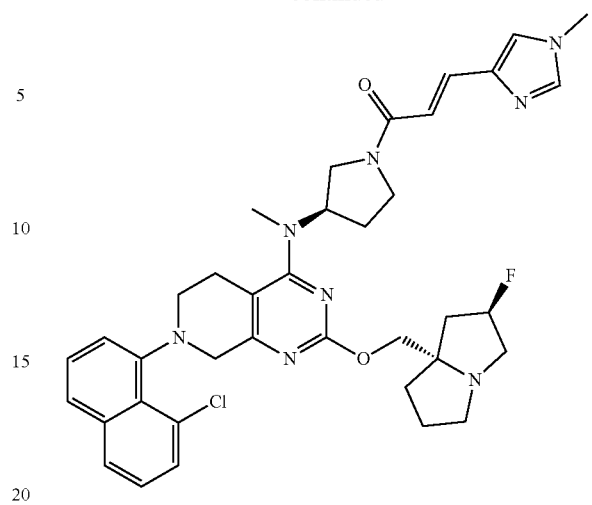
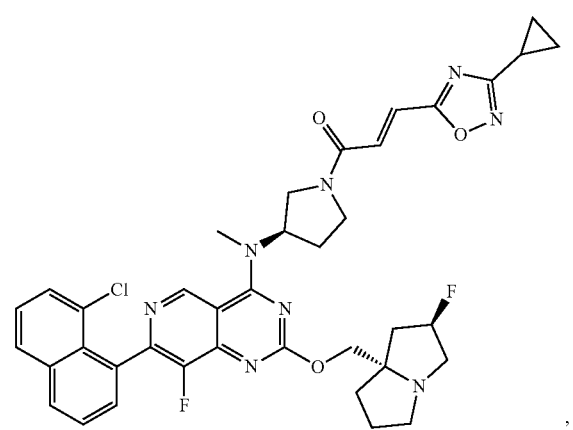
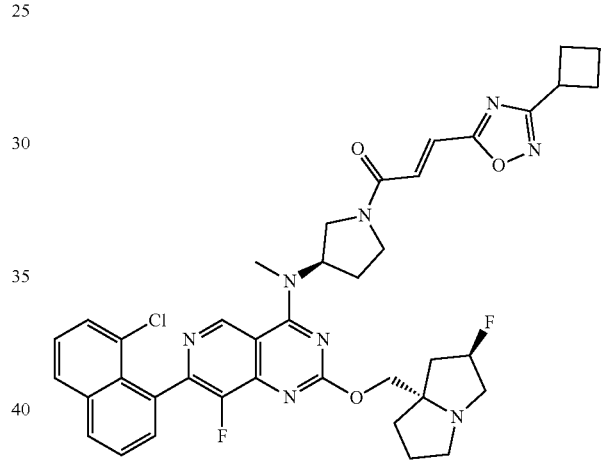
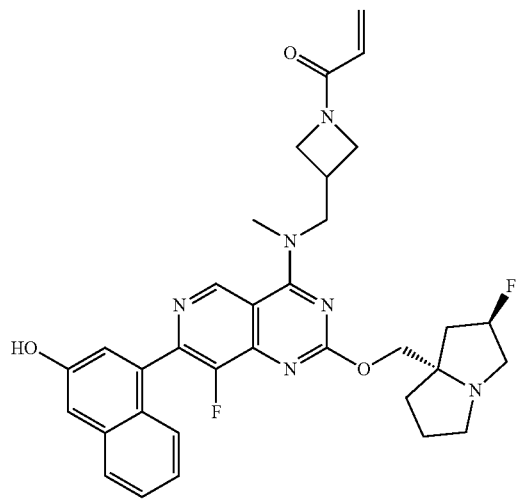
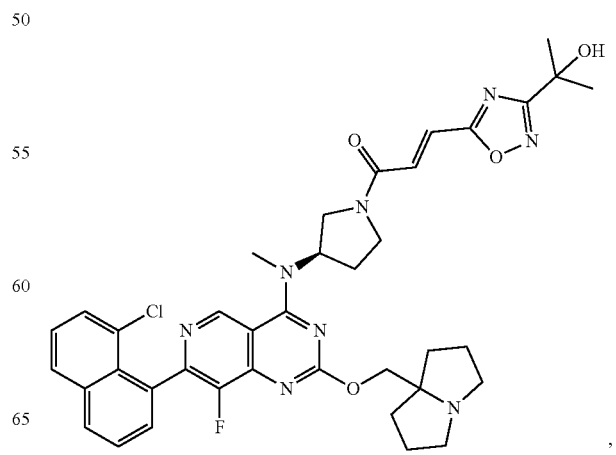

191
-continued
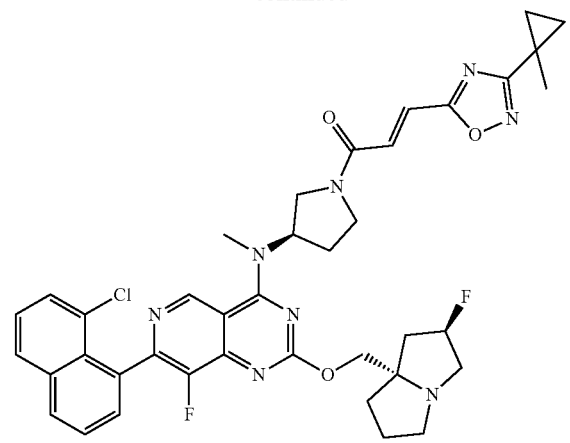
192
-continued
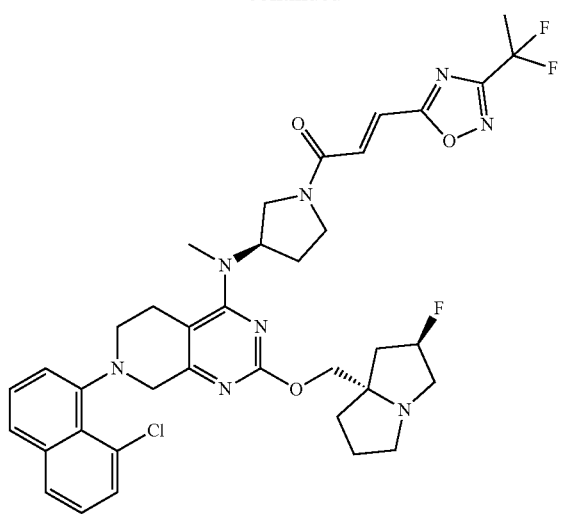
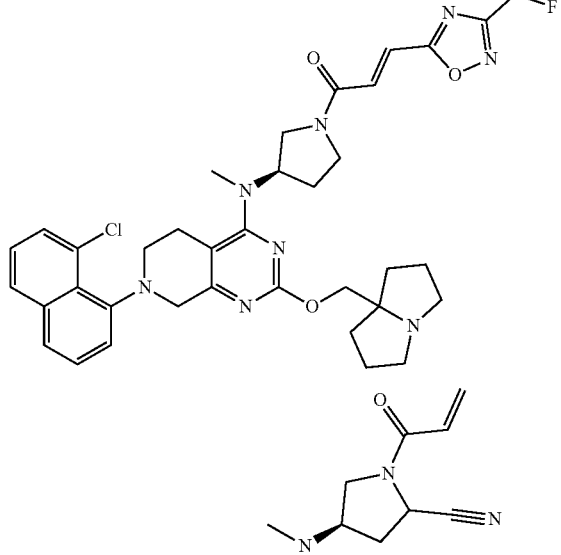
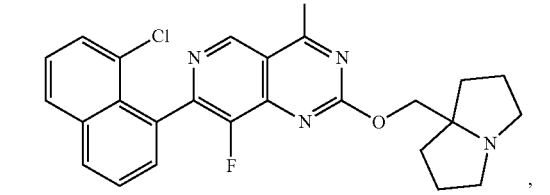
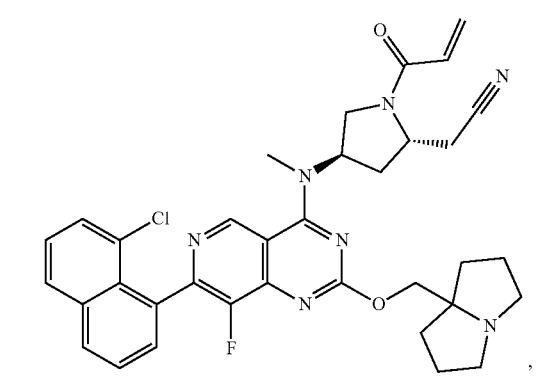

193
-continued
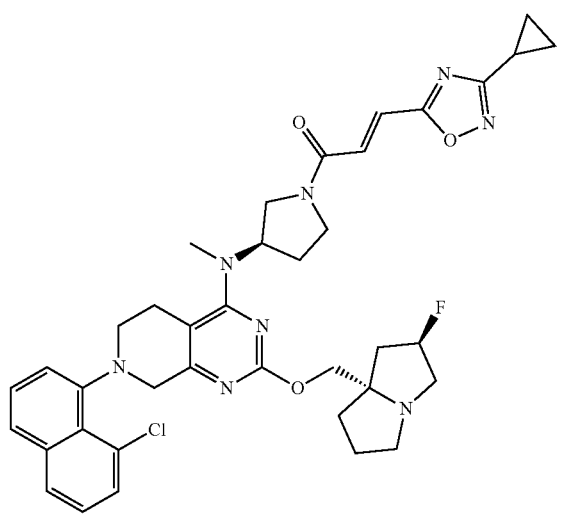
,
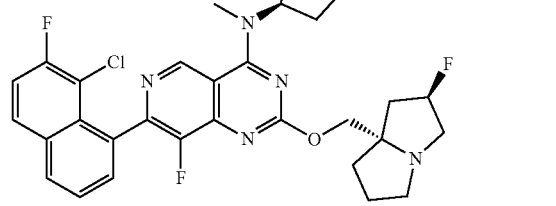
,
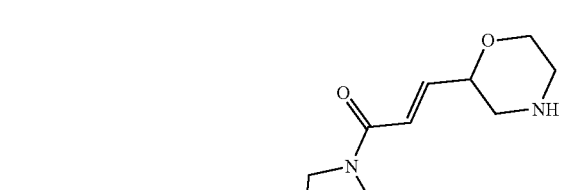
,
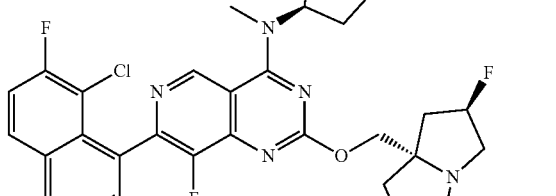
,
194
-continued
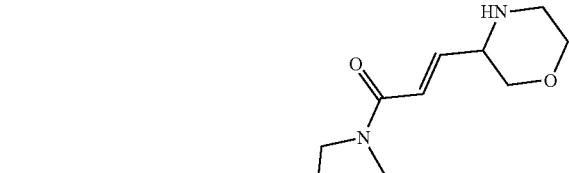
,
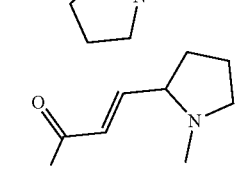
,
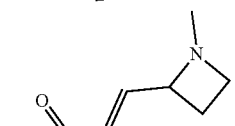
,
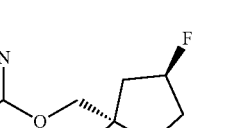
,
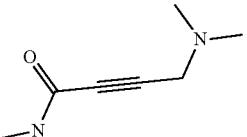
,
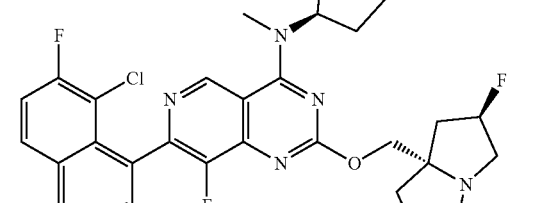
, 195
-continued
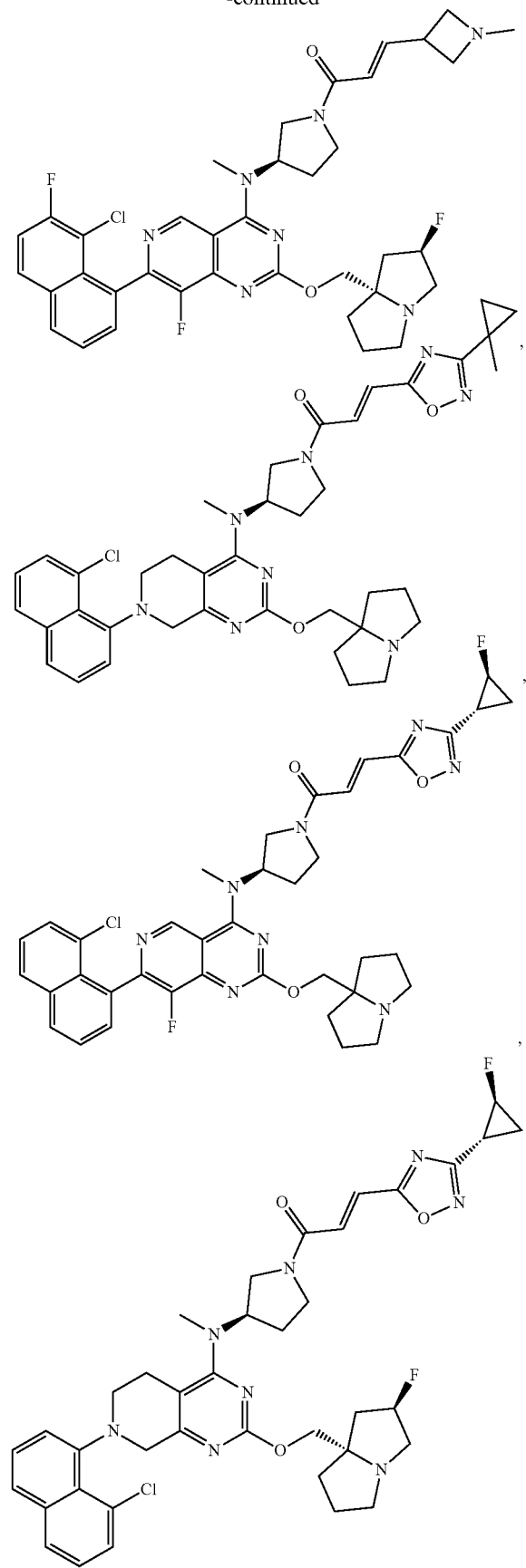
196
-continued
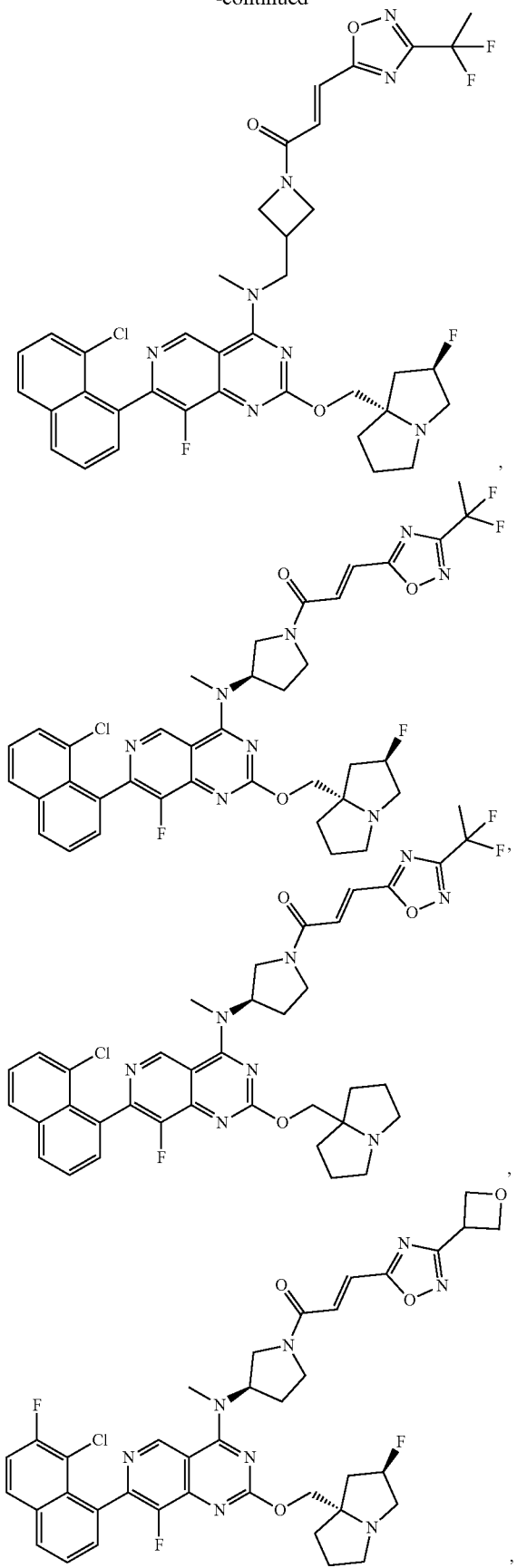

197
-continued
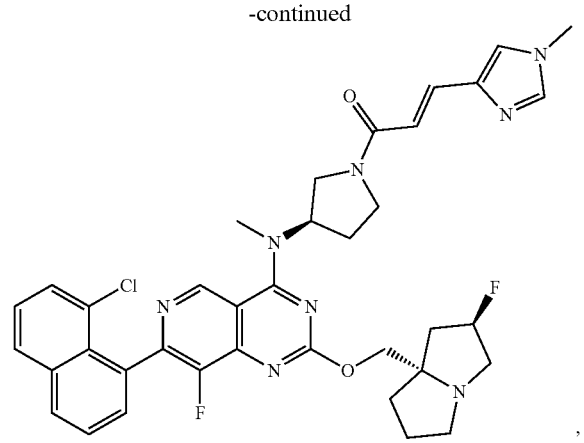
,
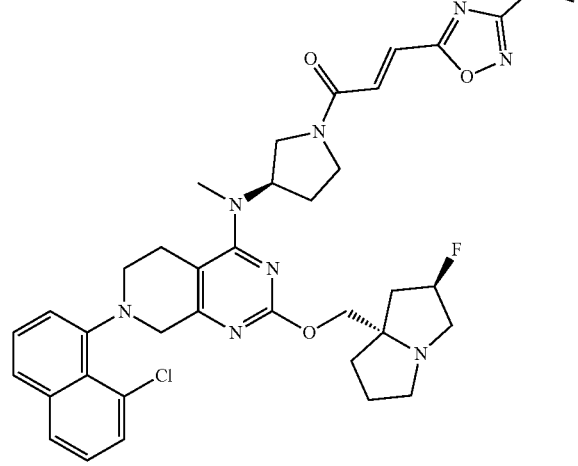
,

,

,
198
-continued
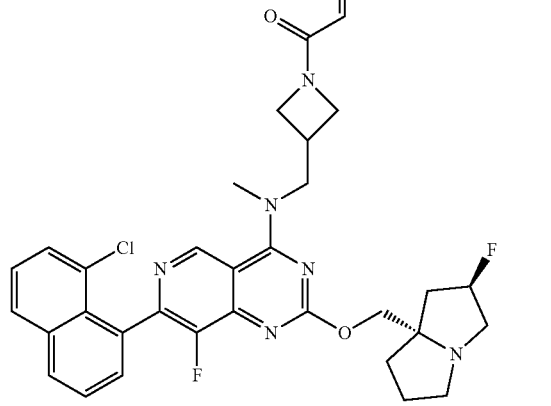
,
,
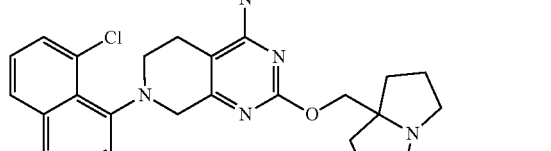
, 199
-continued
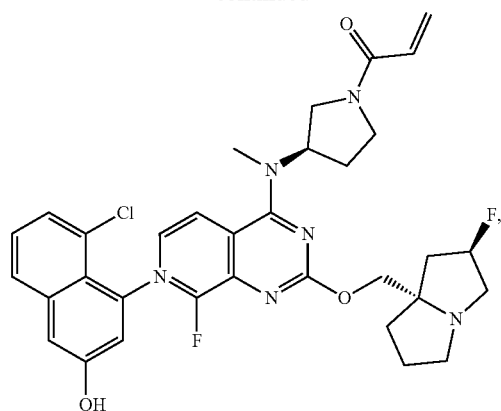
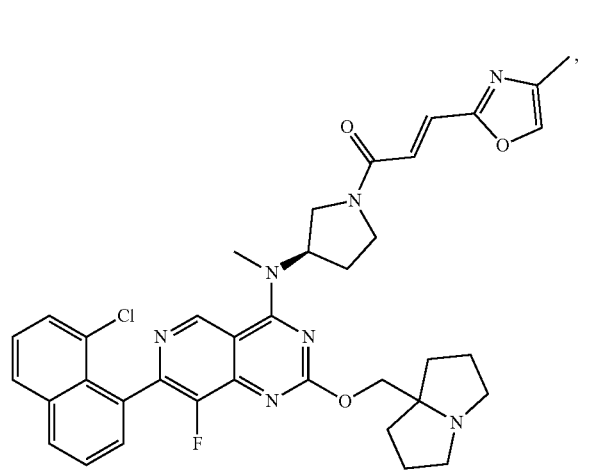
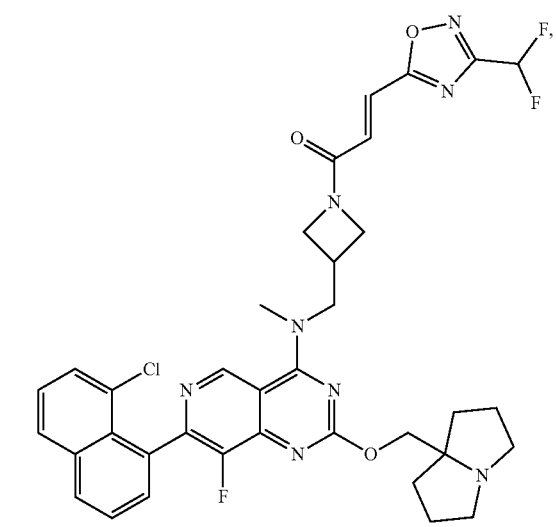
200
-continued
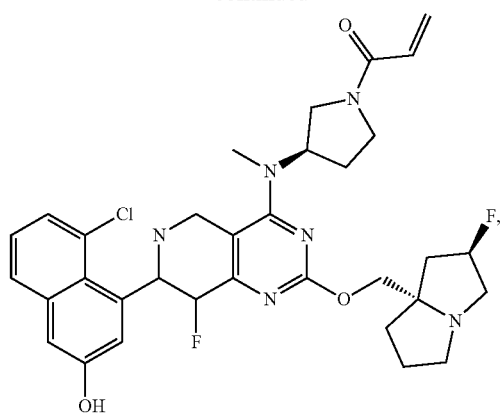
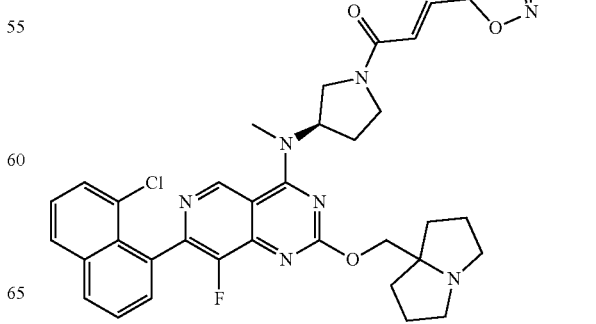

201
-continued
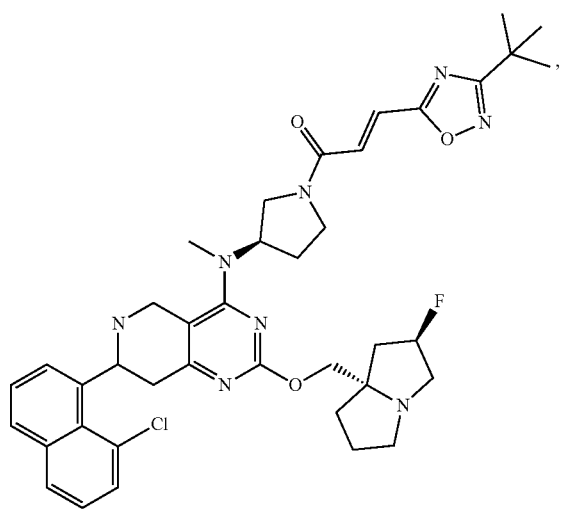
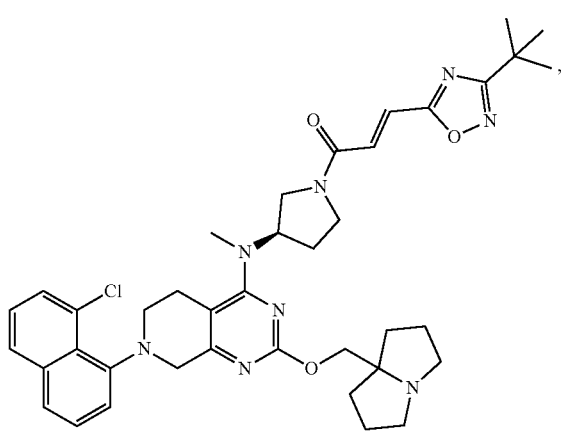
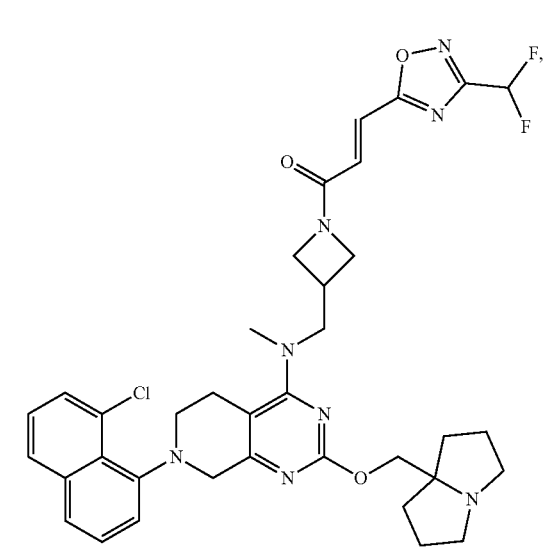
202
-continued
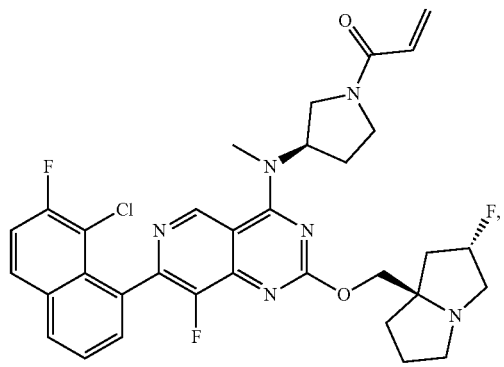
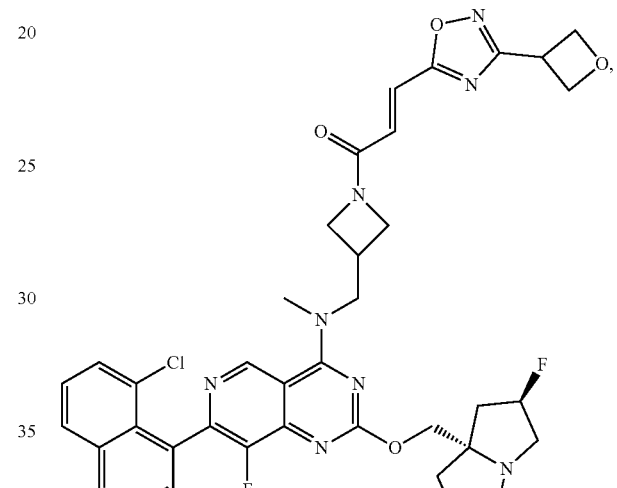
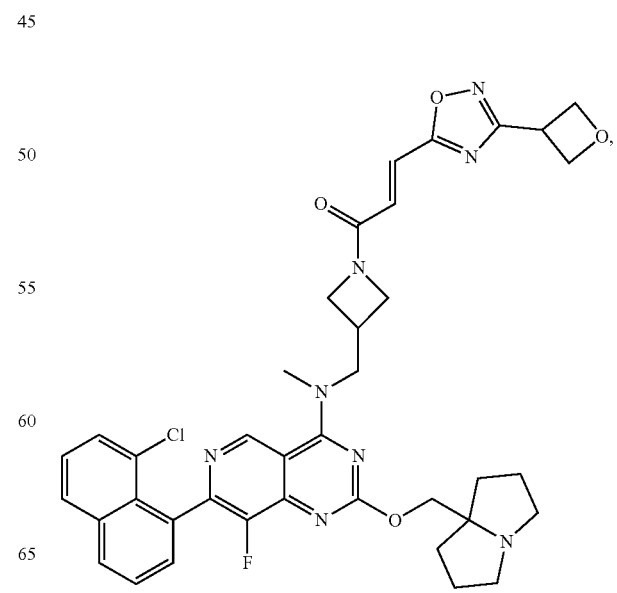

203
-continued
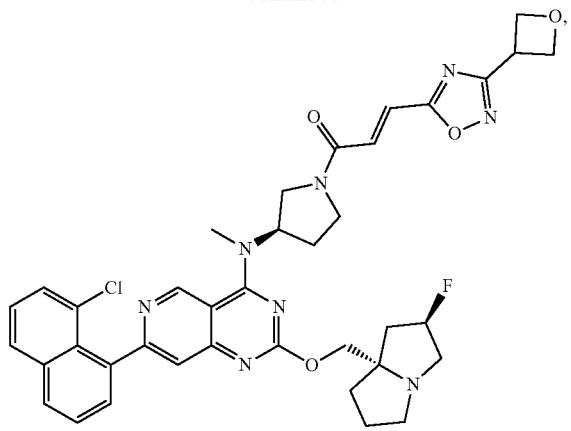
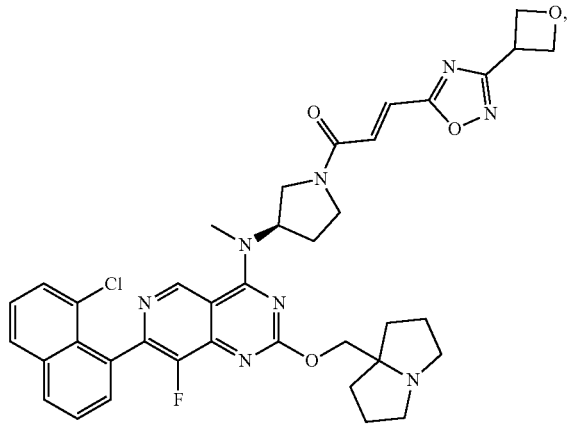
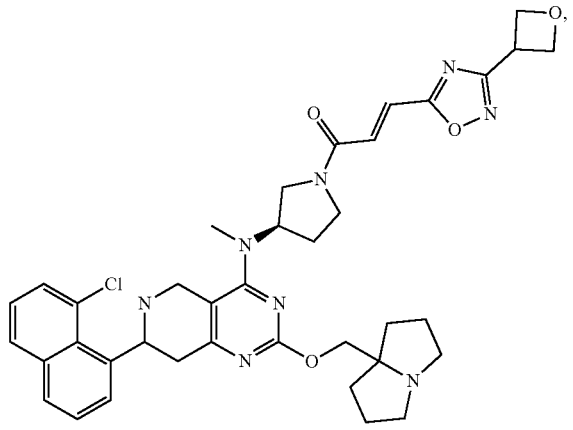
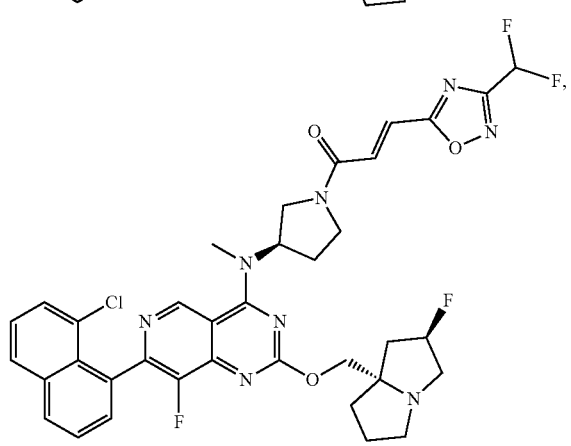
204
-continued
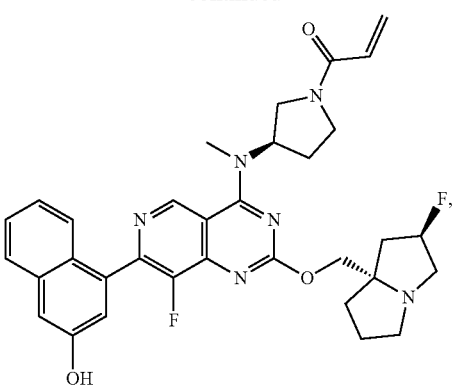
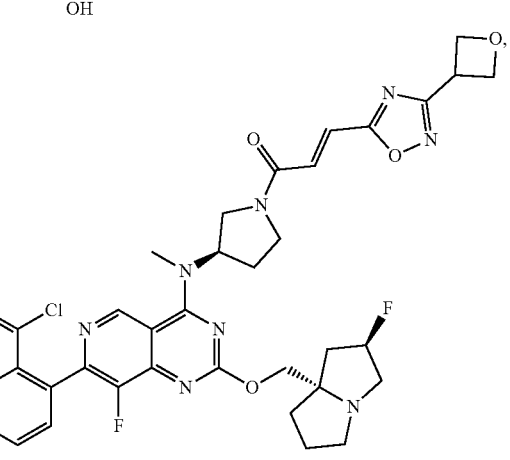
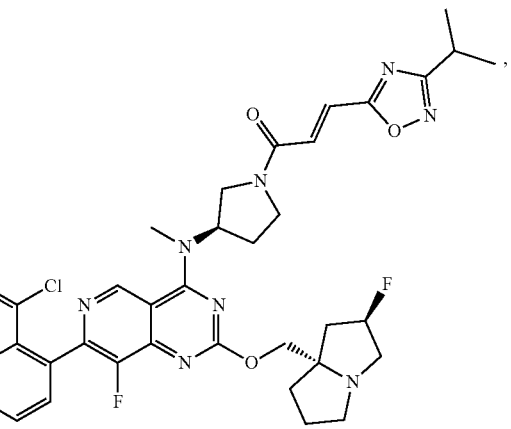
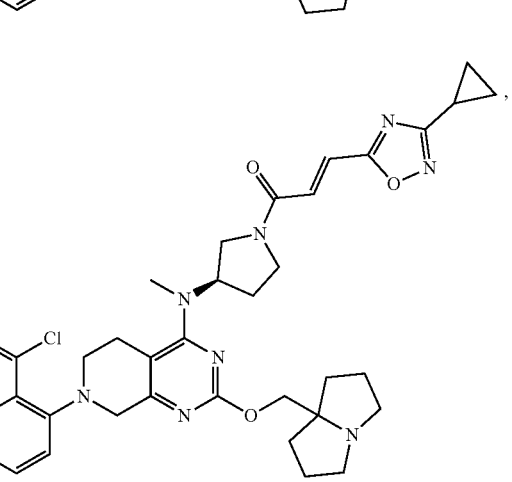

205
-continued
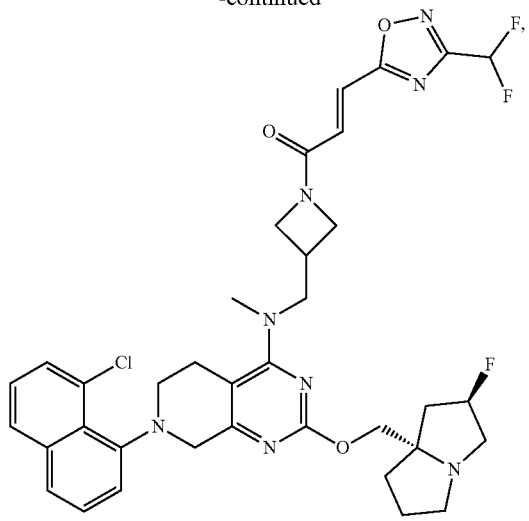
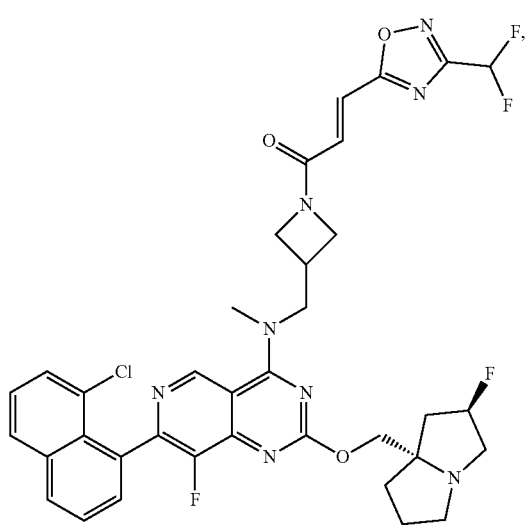
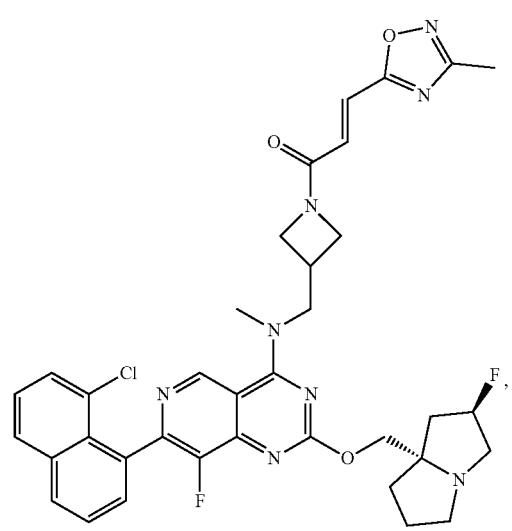
206
-continued
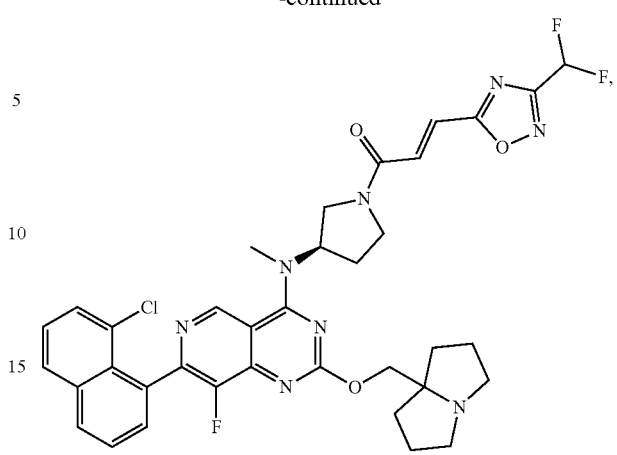

207
-continued
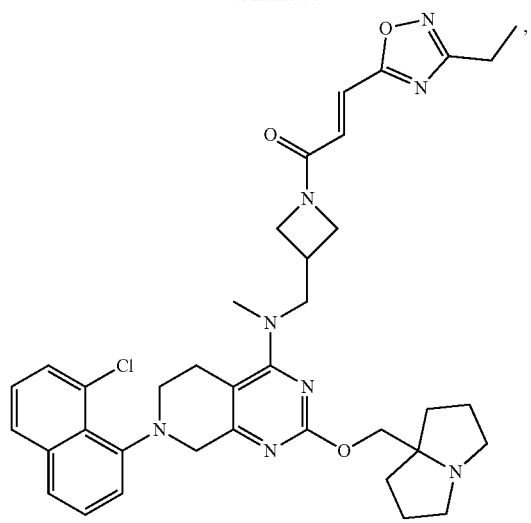
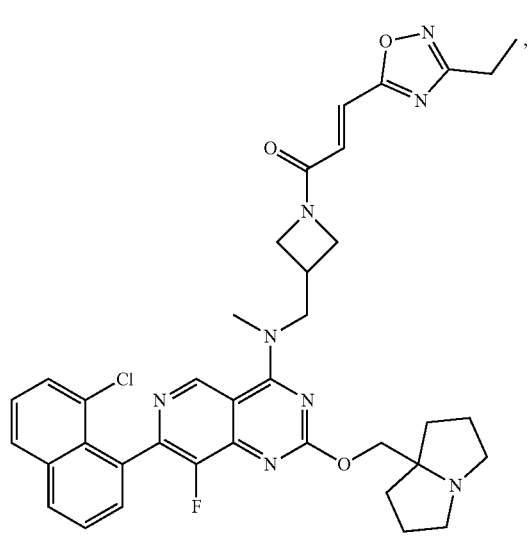
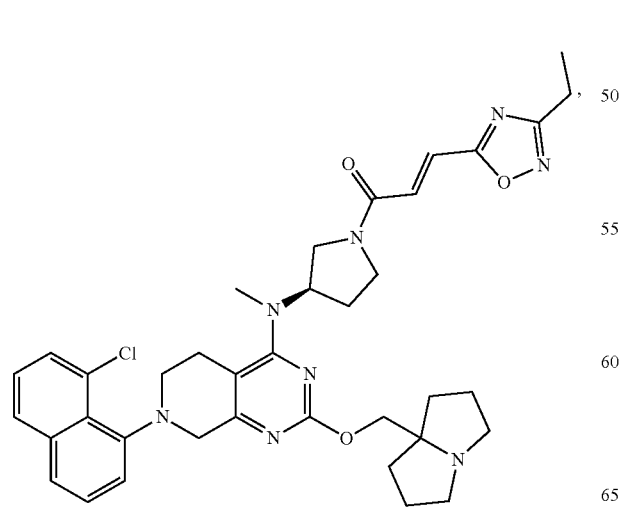
208
-continued
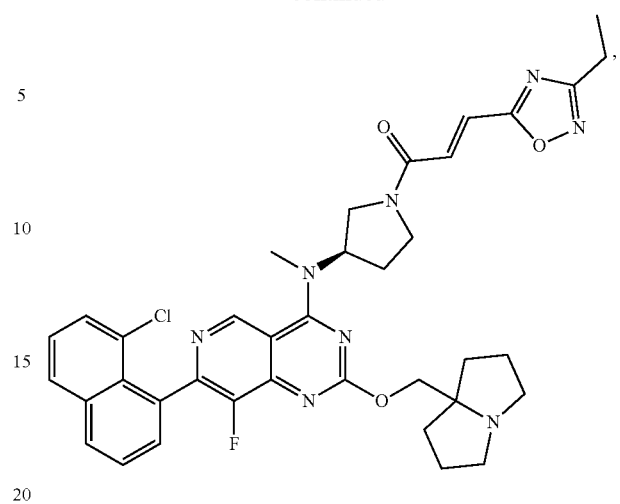
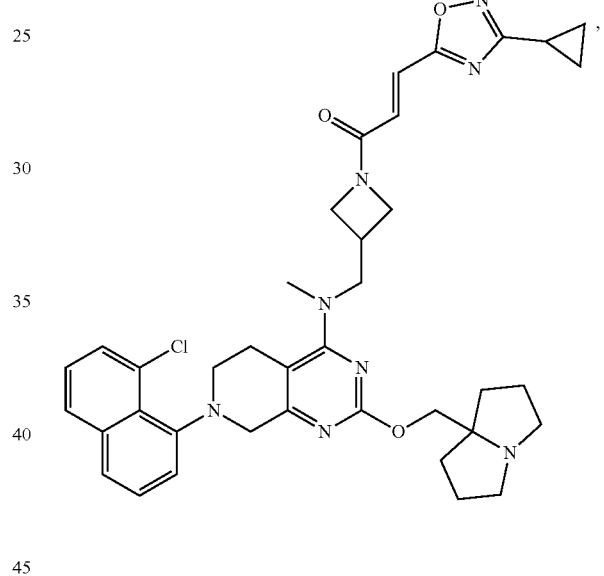
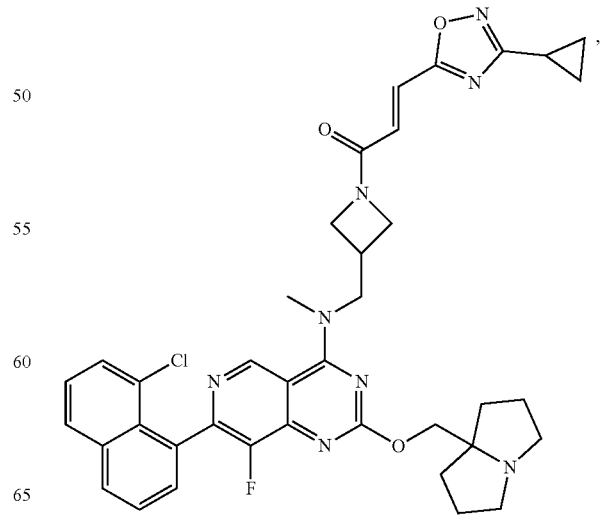

209
-continued
210
-continued
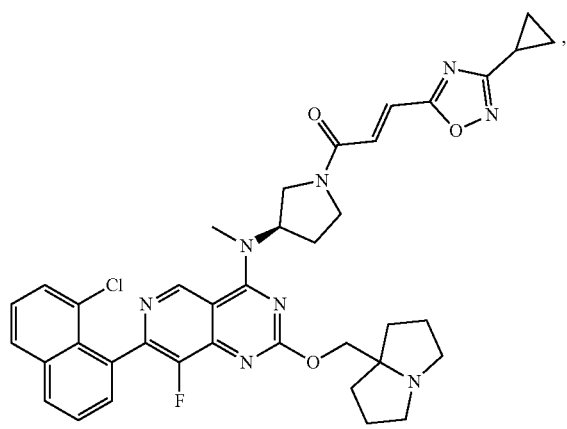
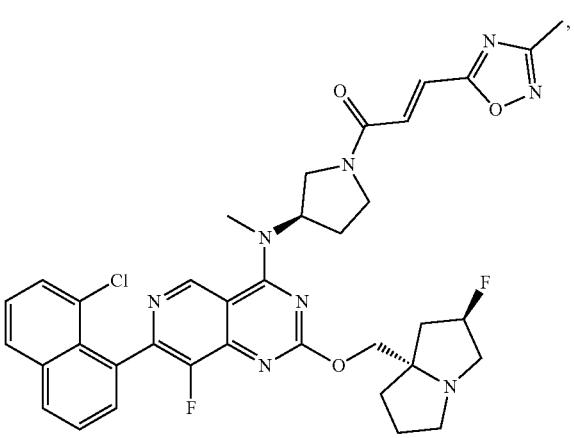
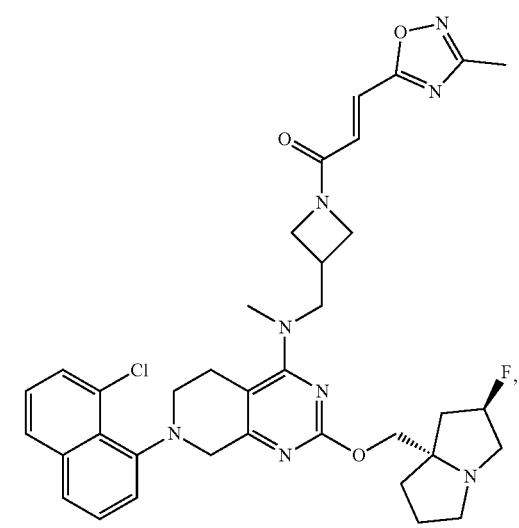

211
-continued
212
-continued
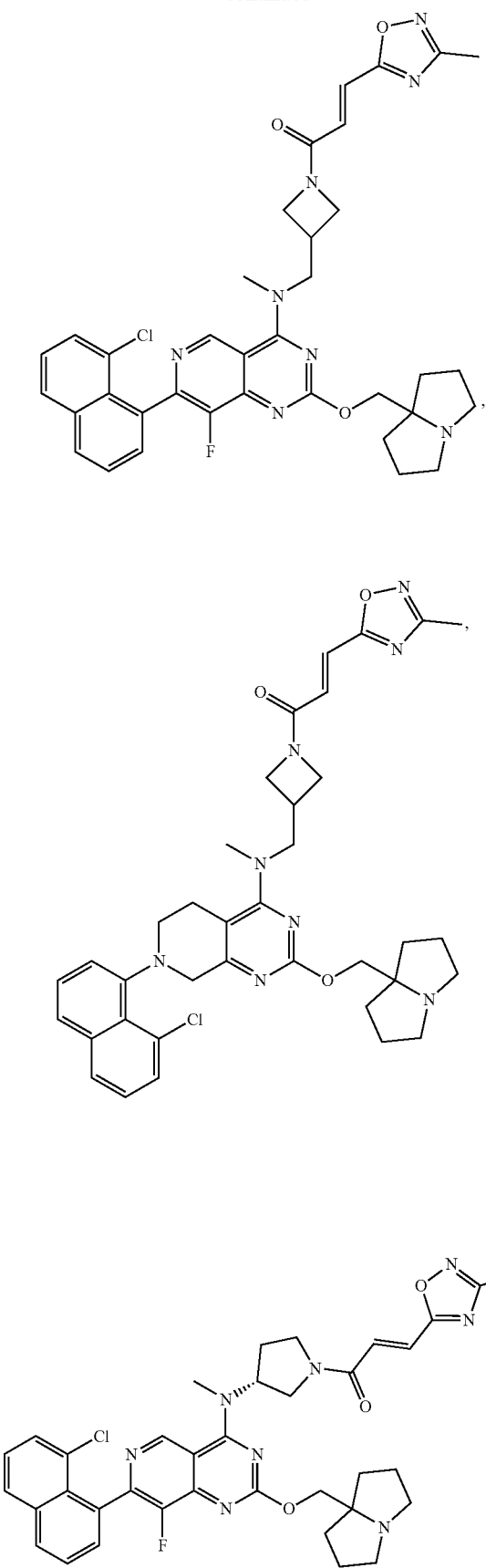
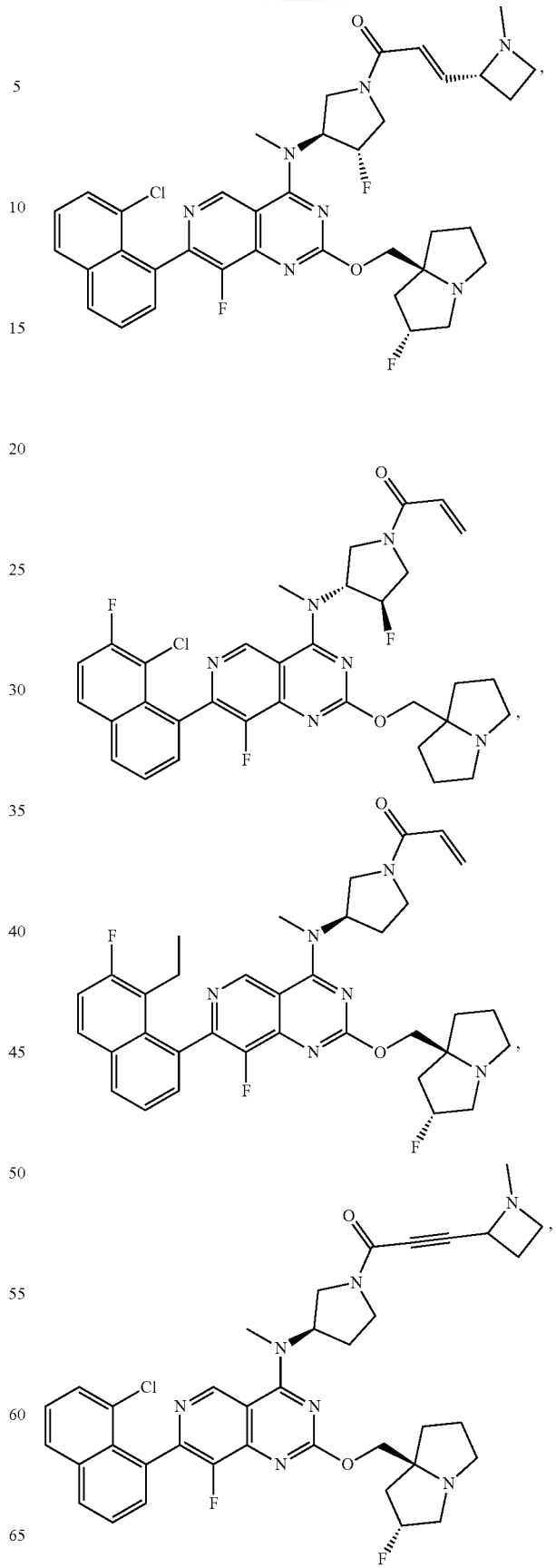

213
-continued
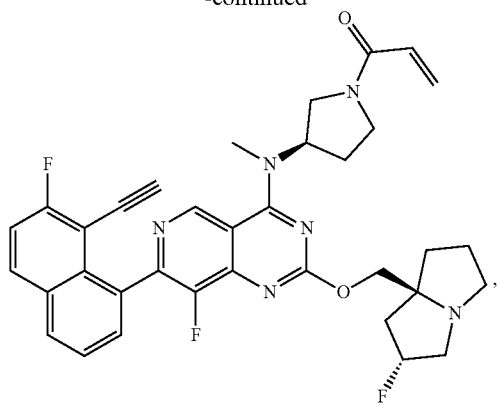
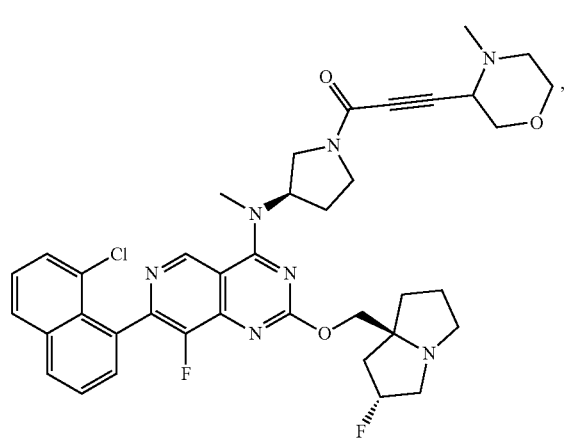
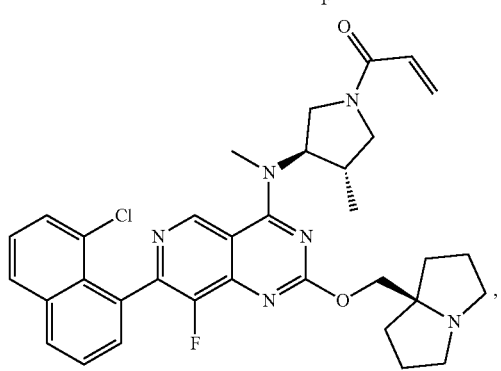
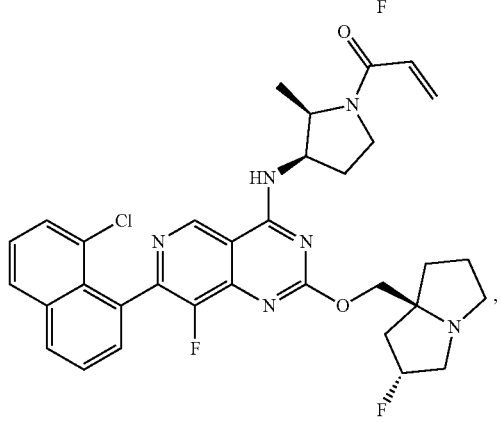
214
-continued
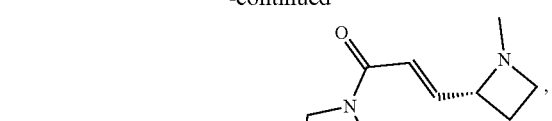
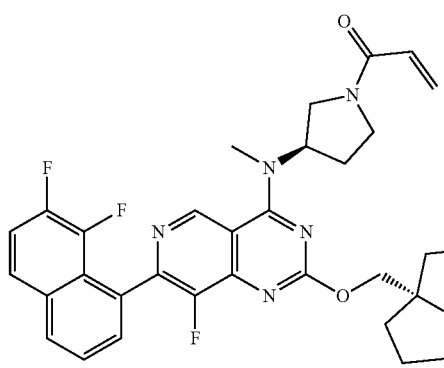
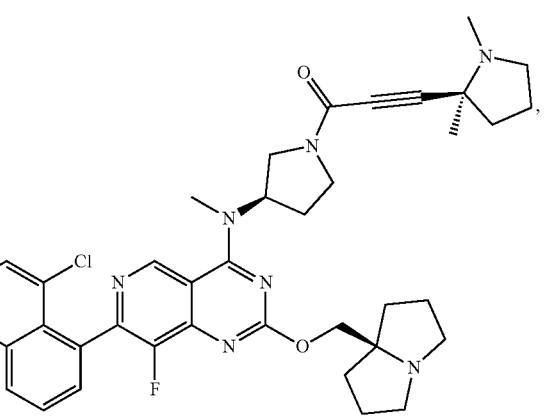
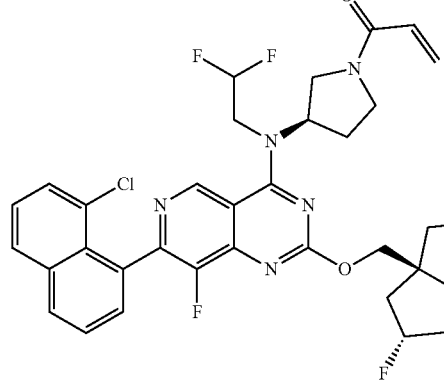

215
-continued
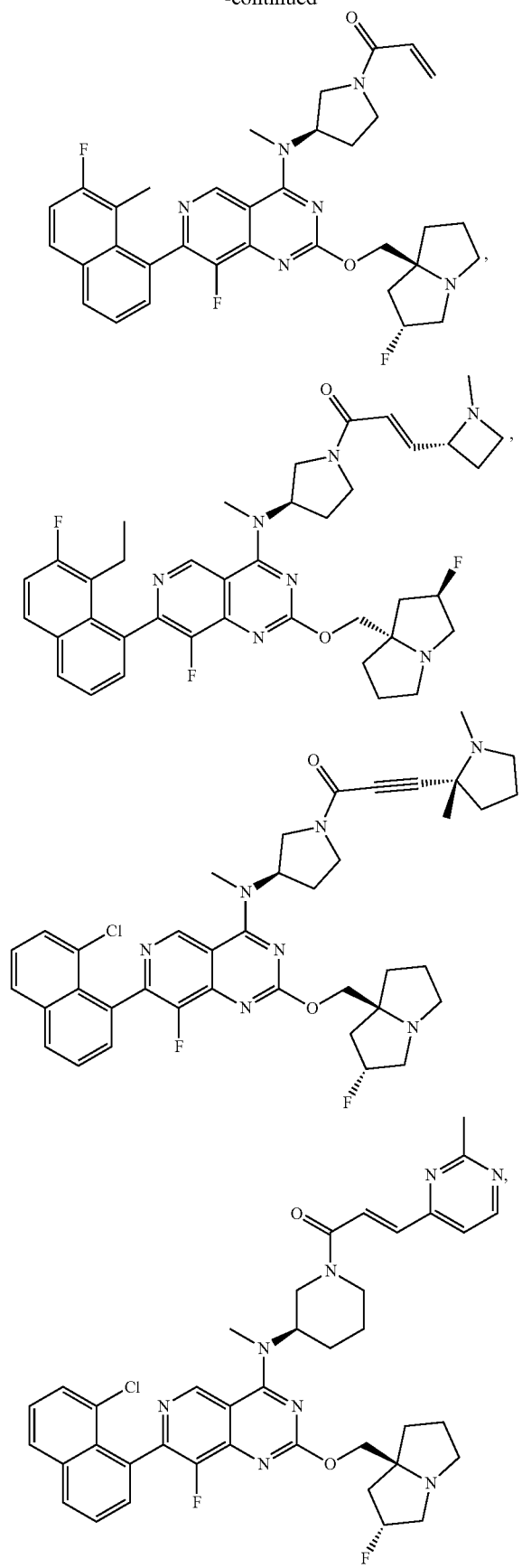
216
-continued
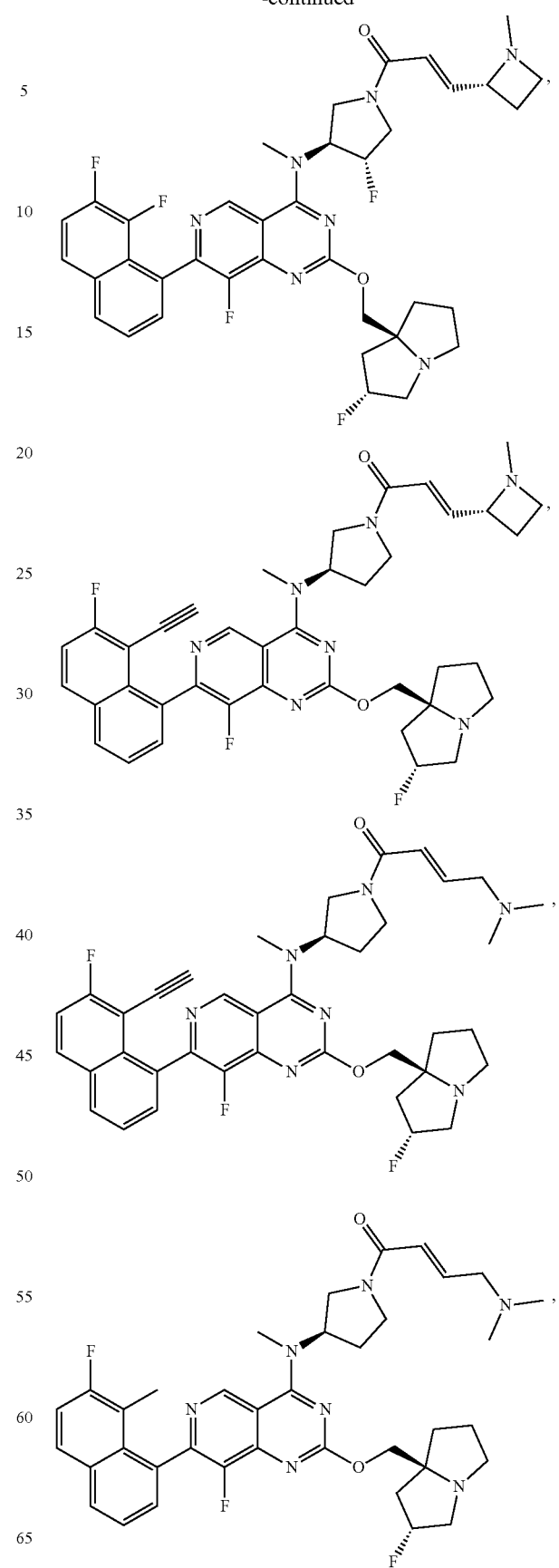

217
-continued
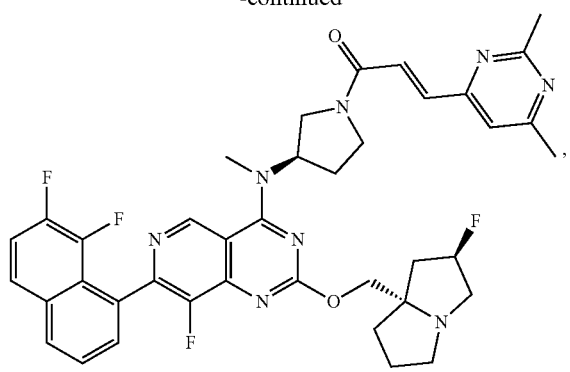
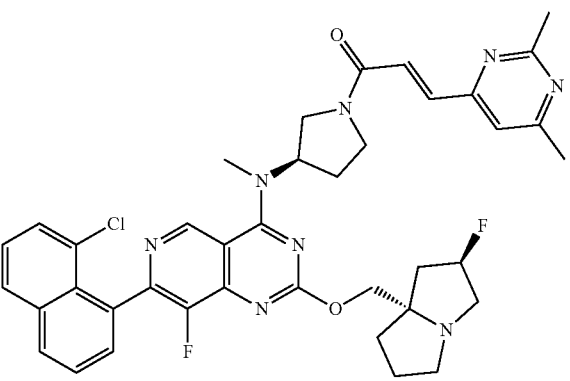
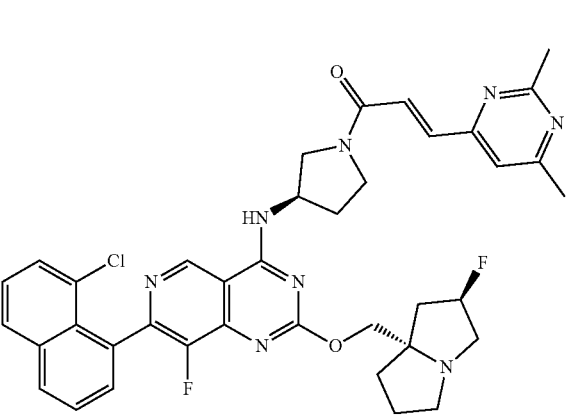
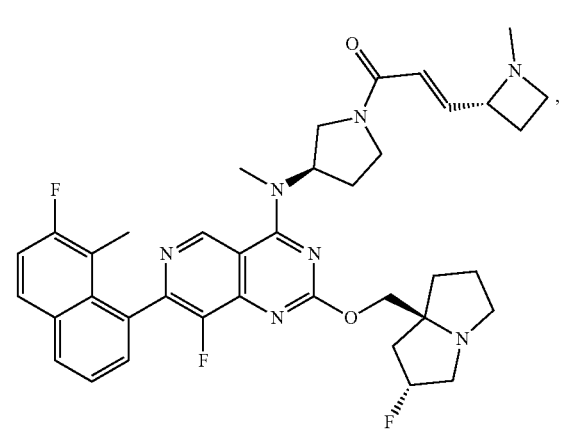
218
-continued
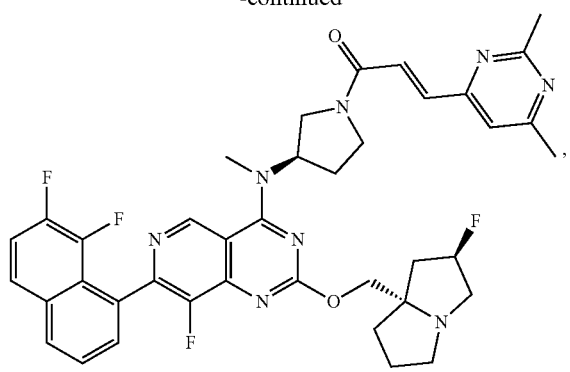
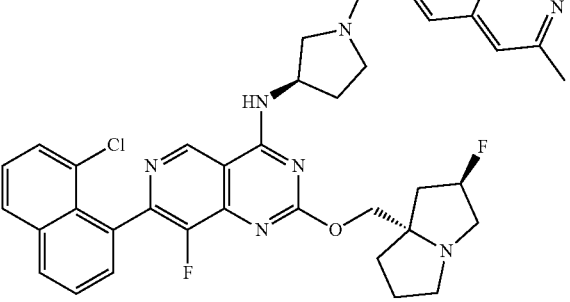
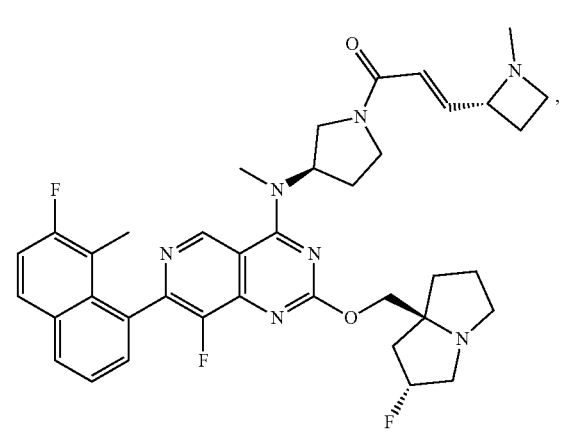
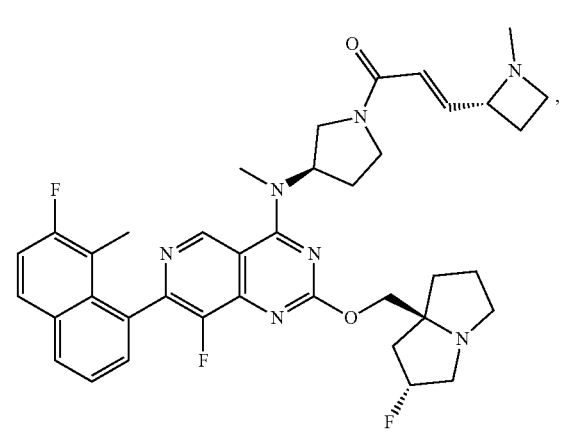

219
-continued
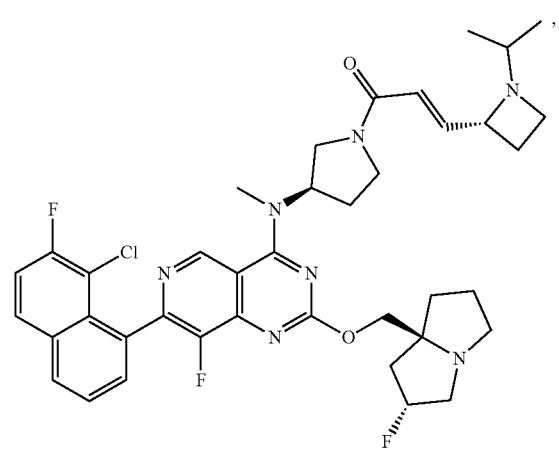
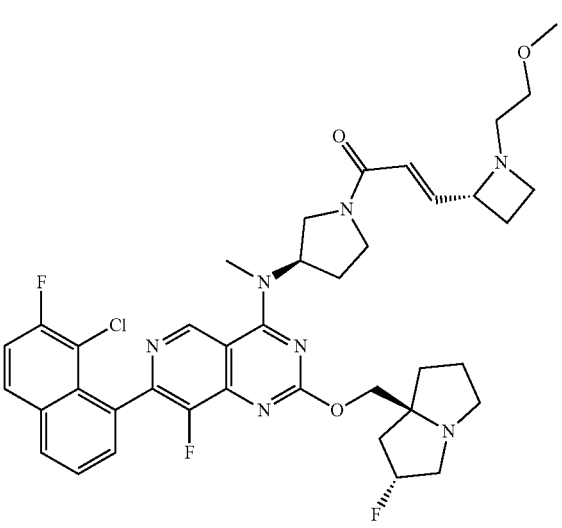
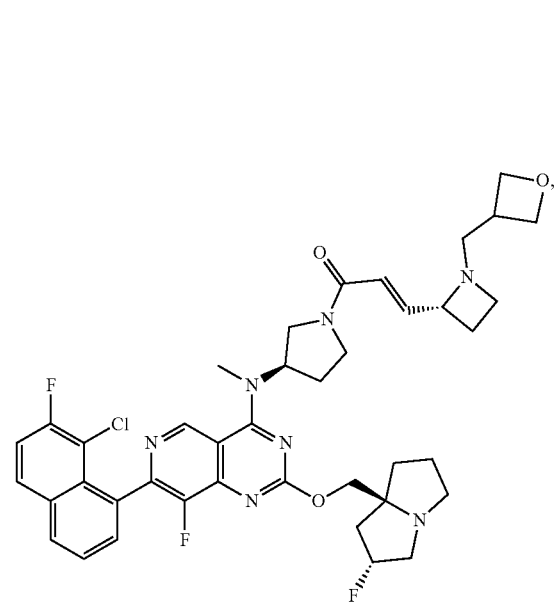
220
-continued
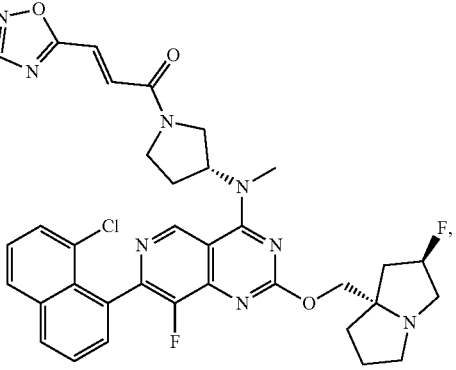
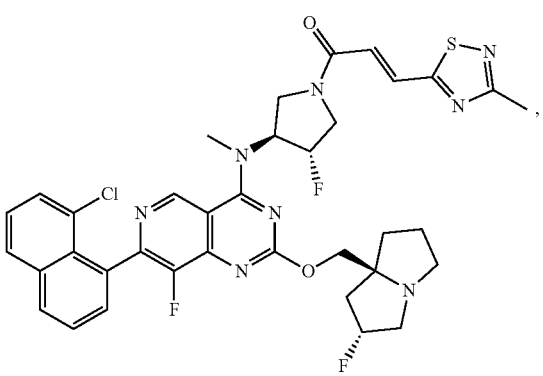
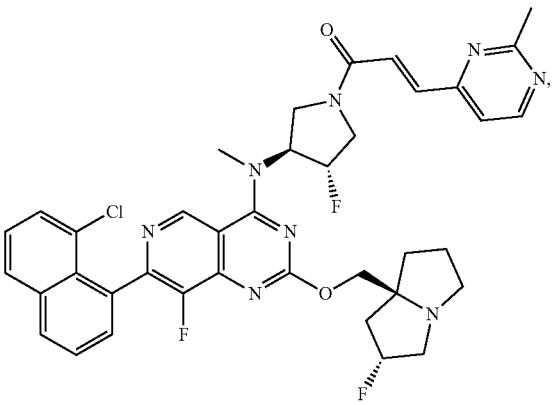
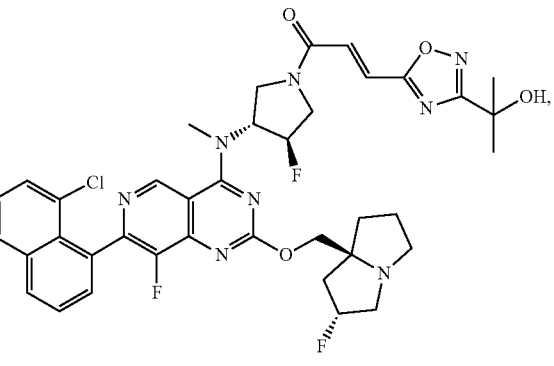

221
-continued
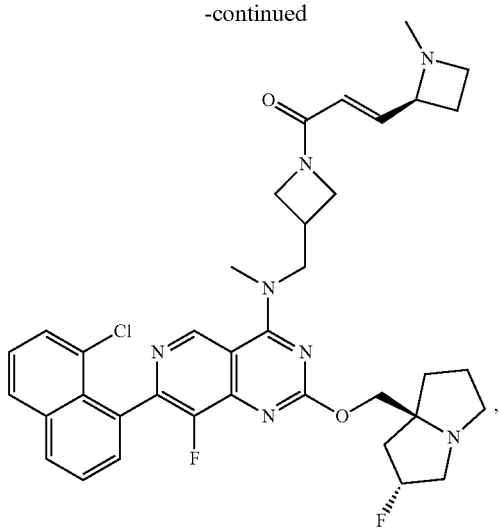
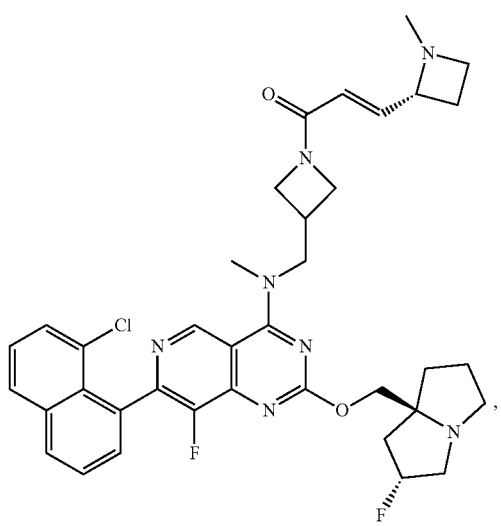
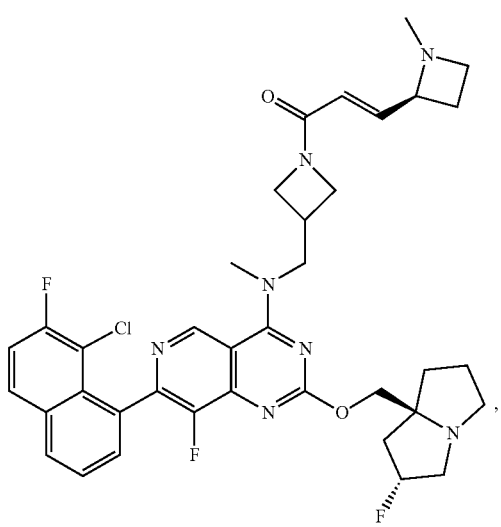
222
-continued
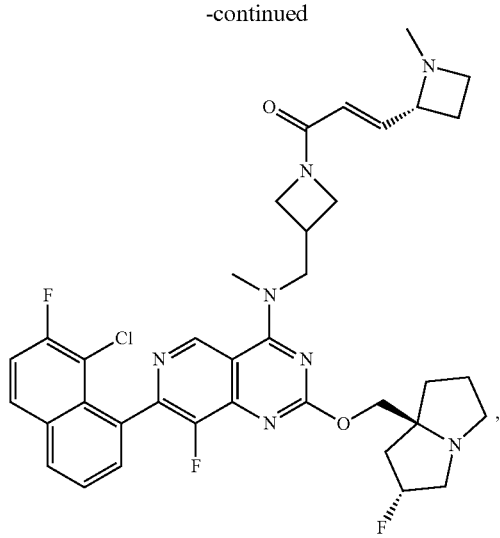
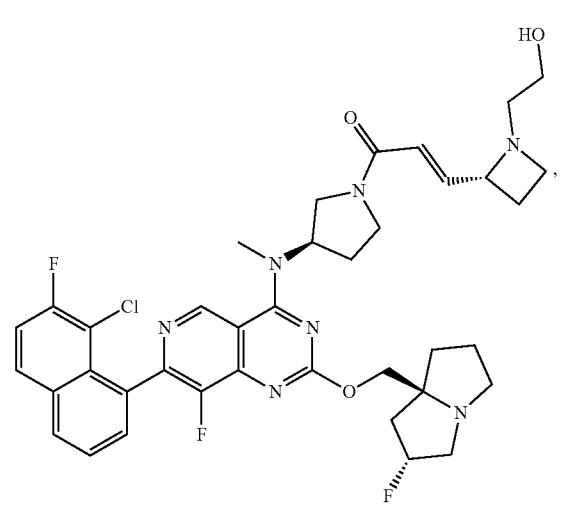
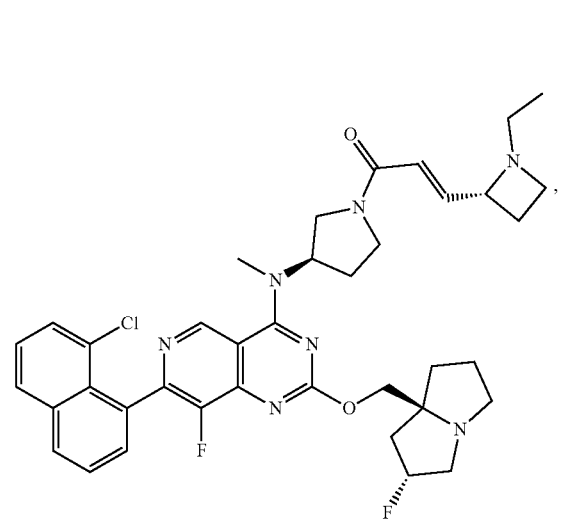

-continued
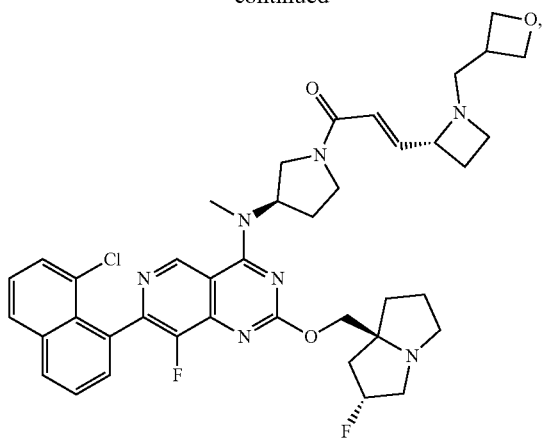
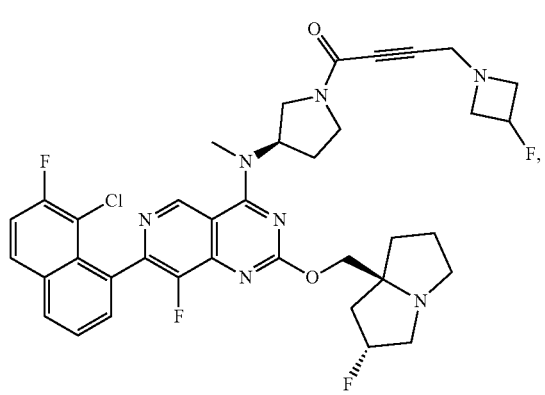
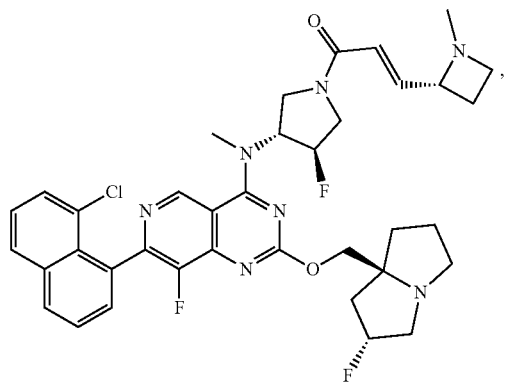
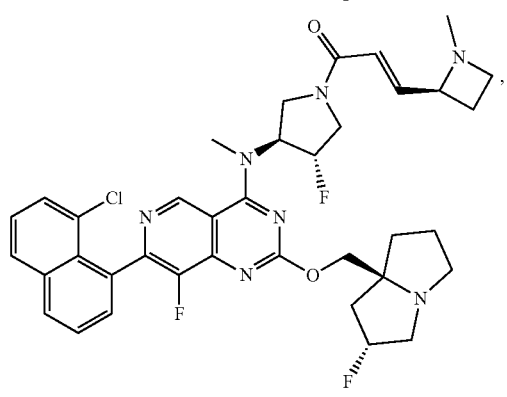
-continued
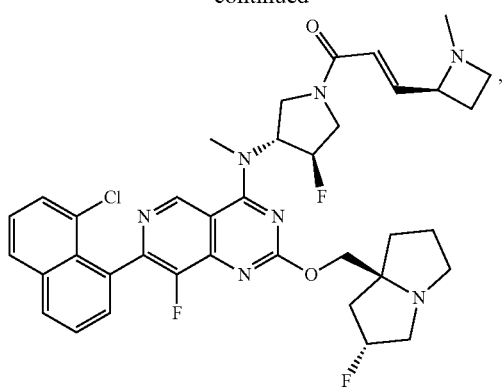
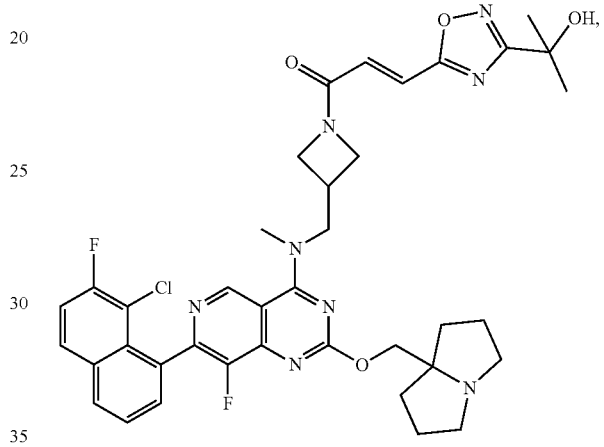
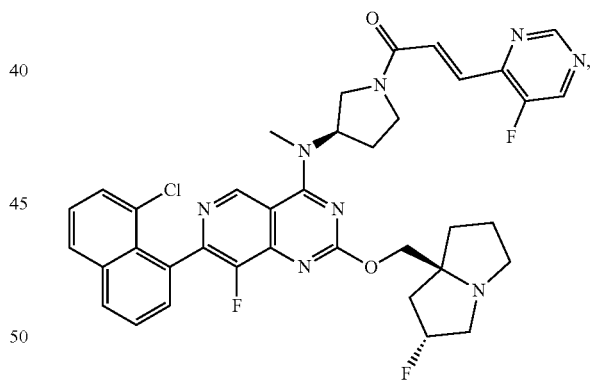
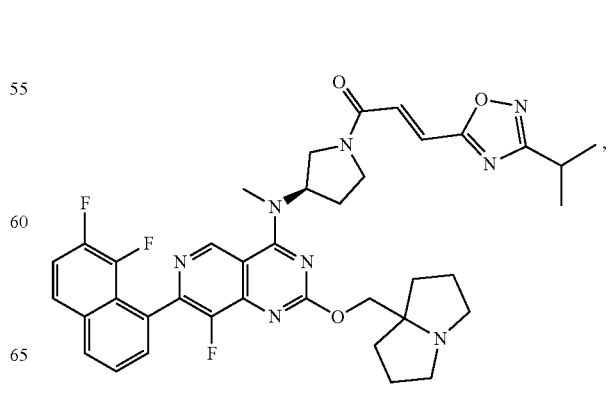

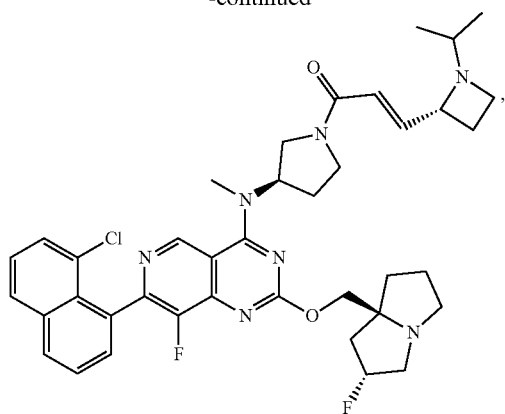
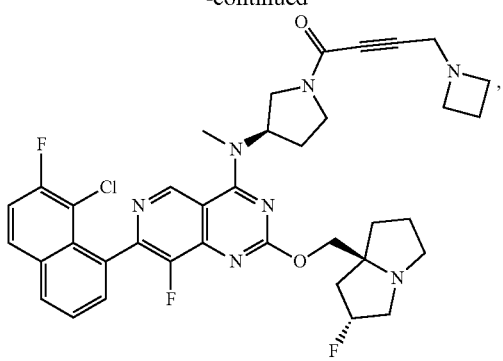
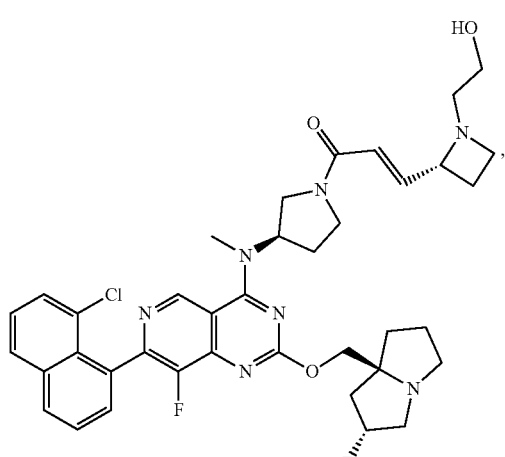
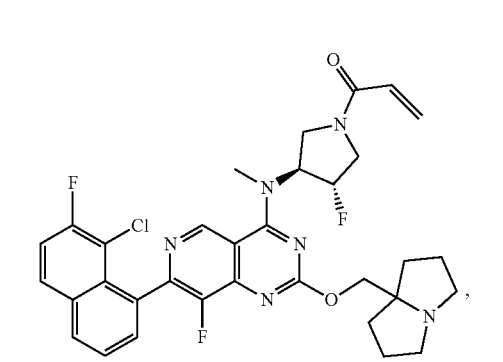
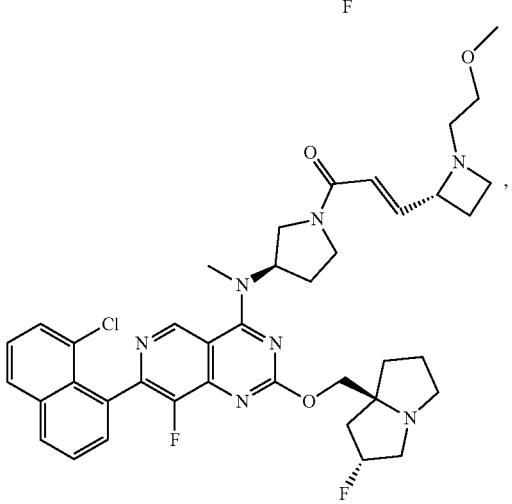
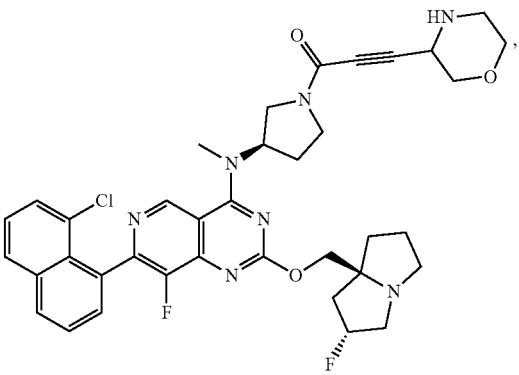
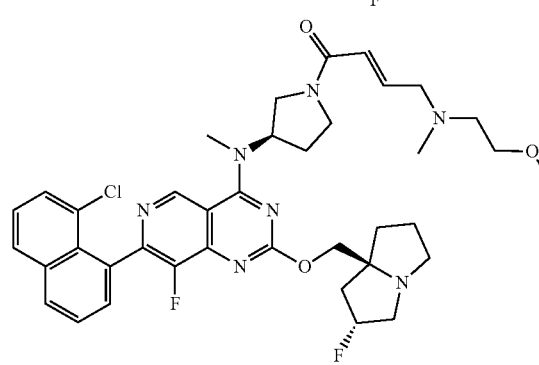
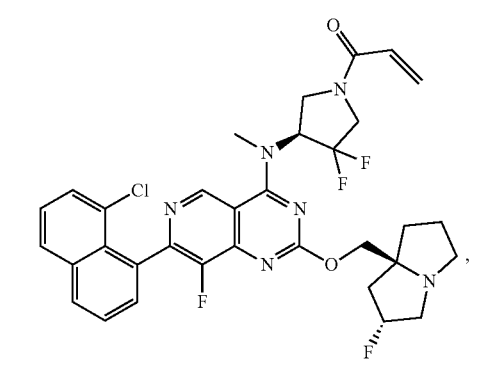

227
-continued
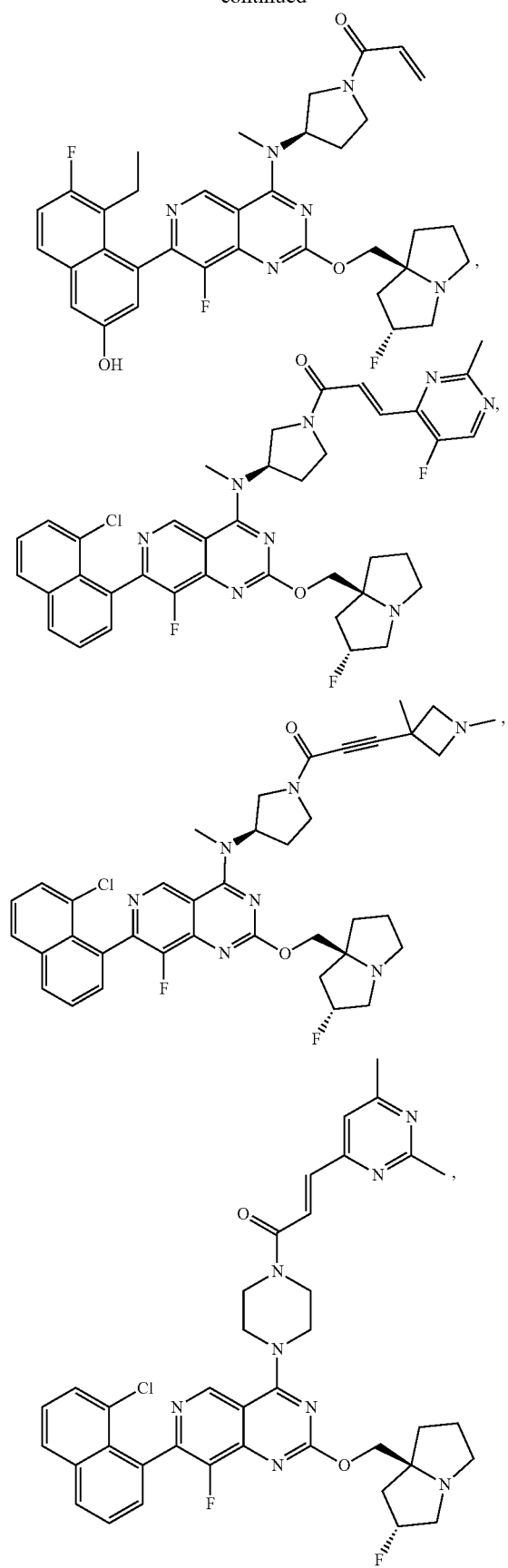
228
-continued
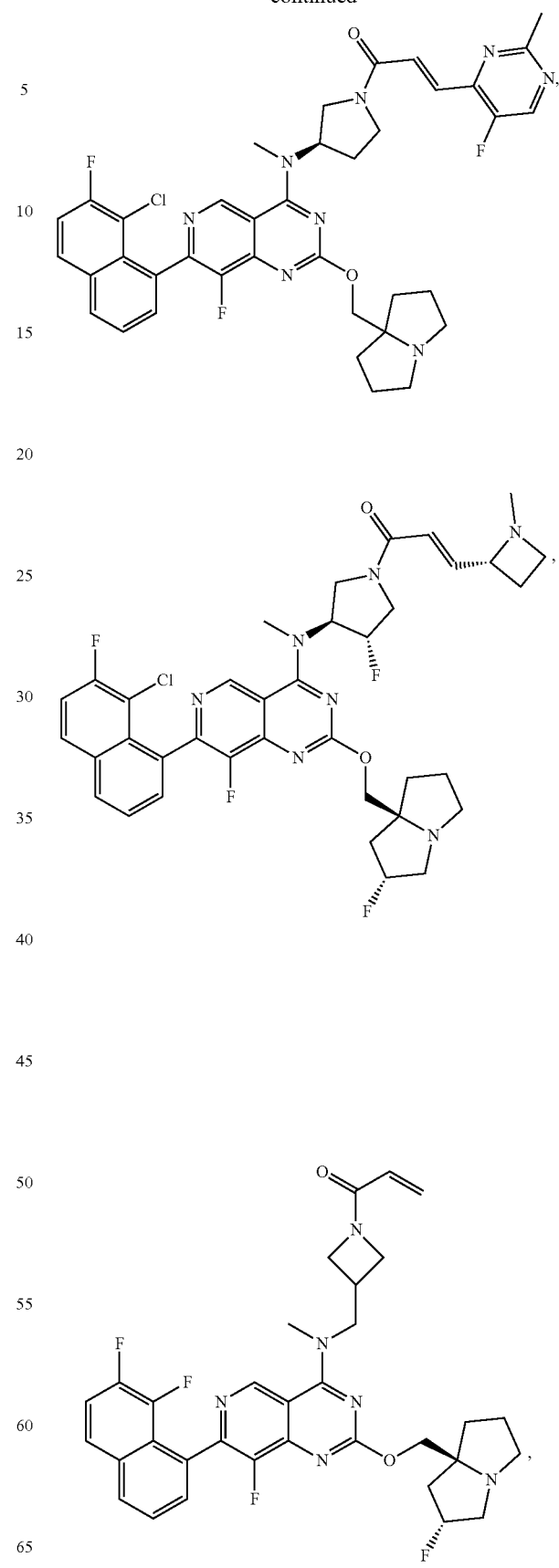

-continued
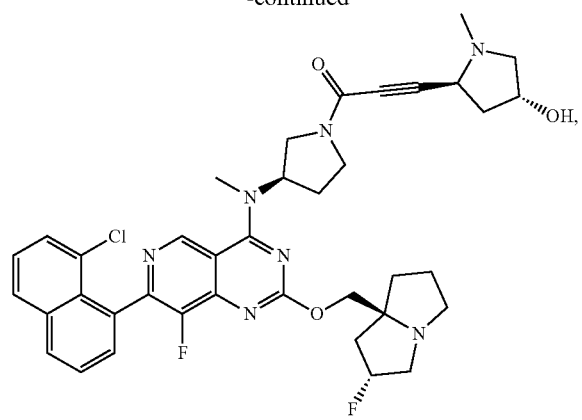
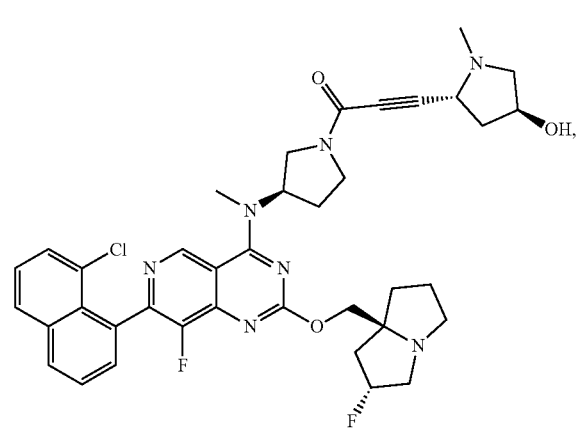
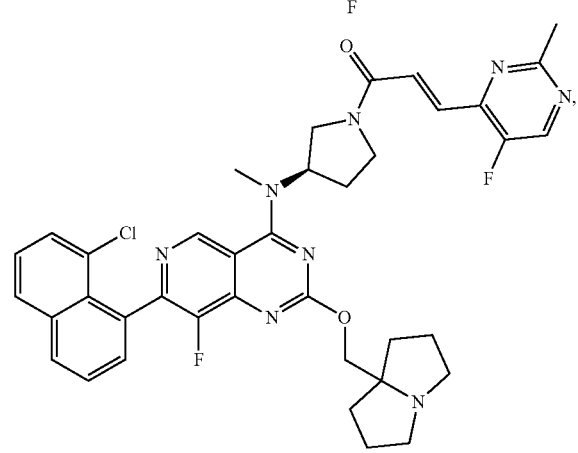
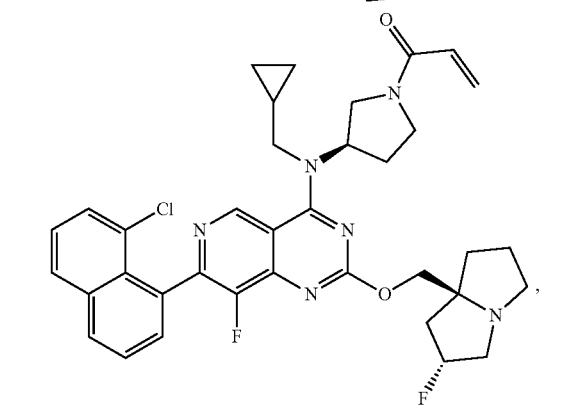
-continued
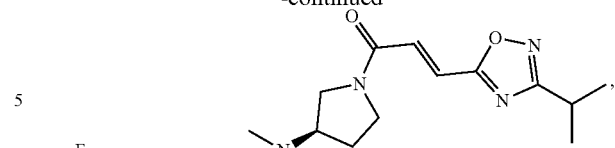
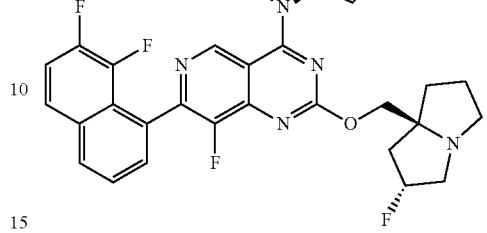
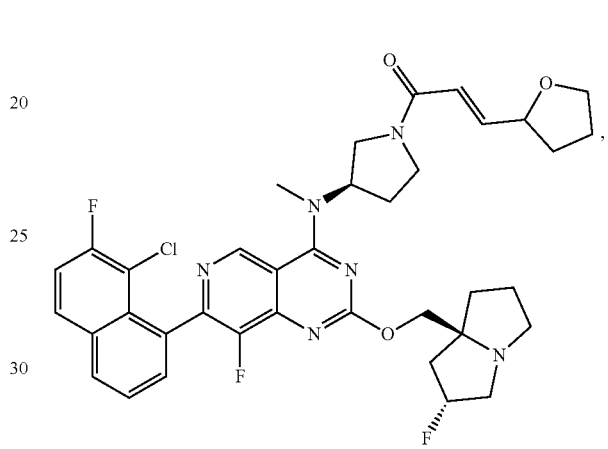
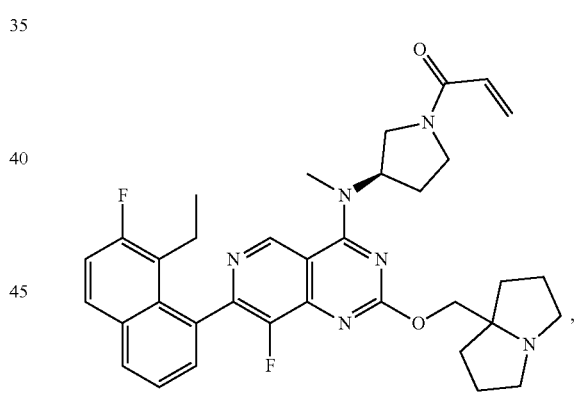

231
-continued
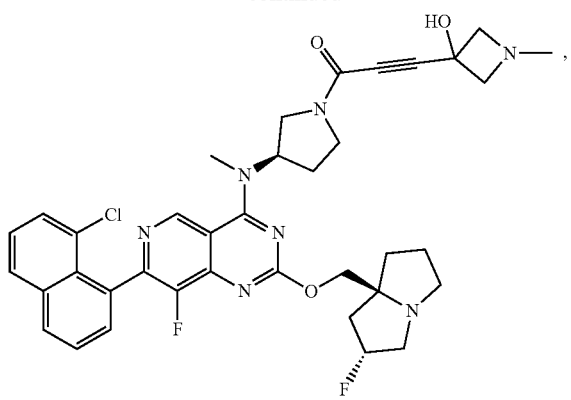
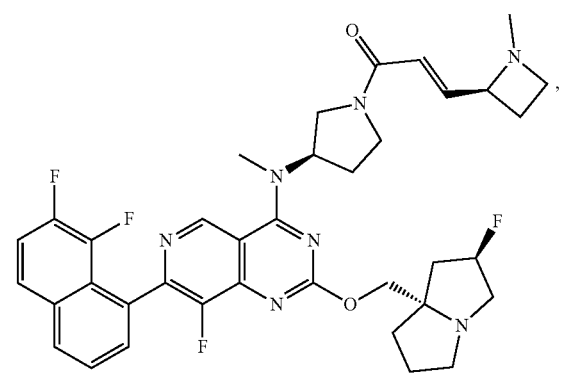
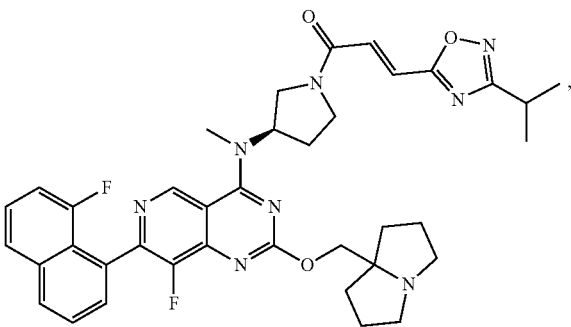
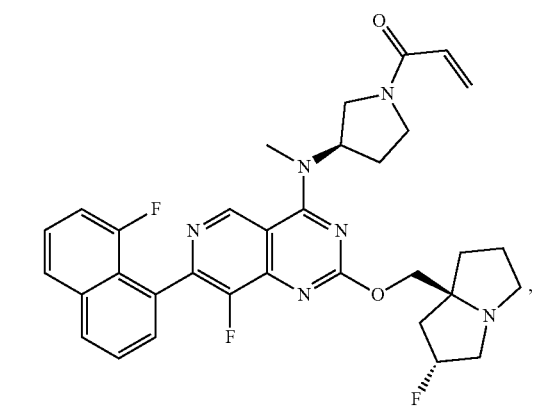
232
-continued
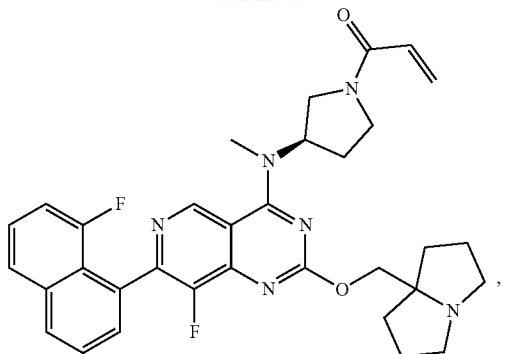
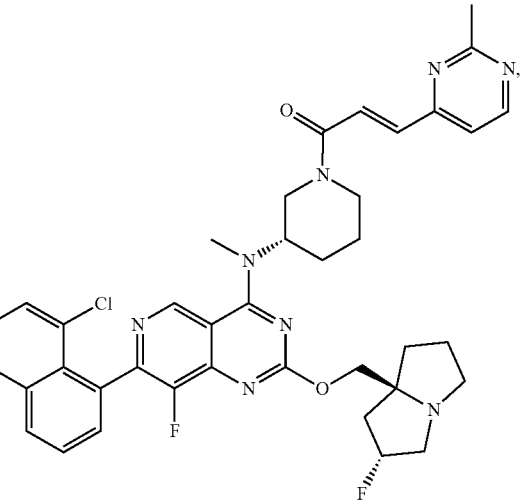
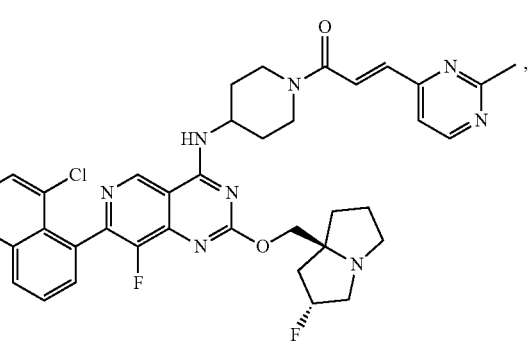
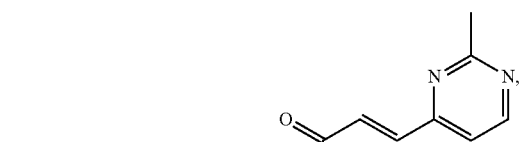
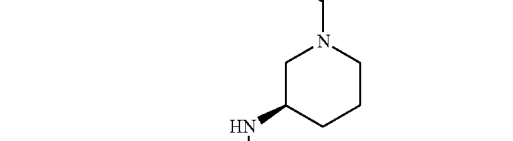

233
-continued
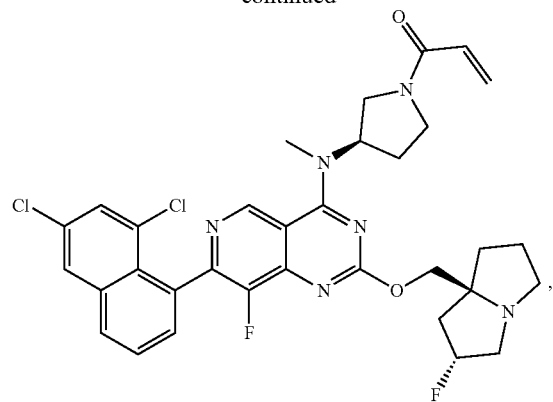
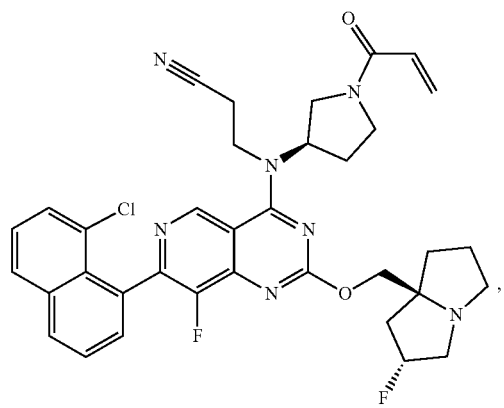
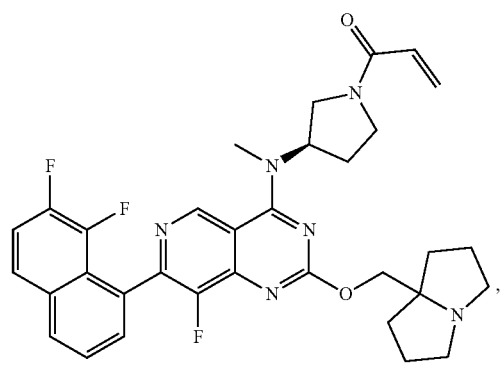
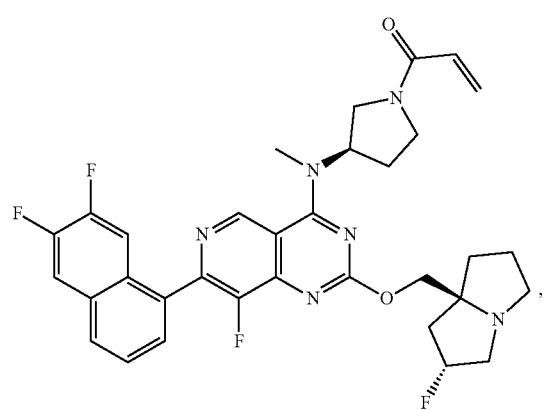
234
-continued
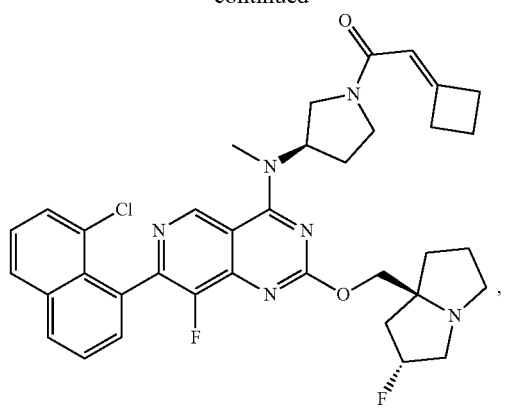
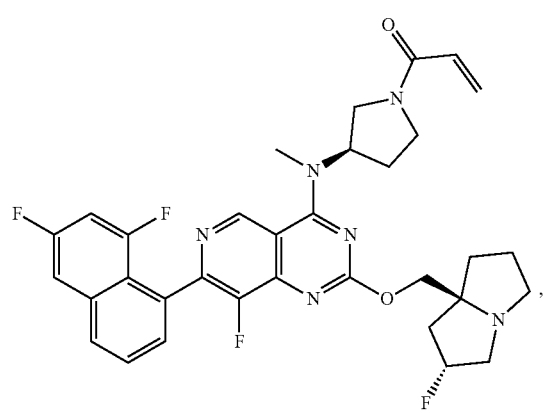
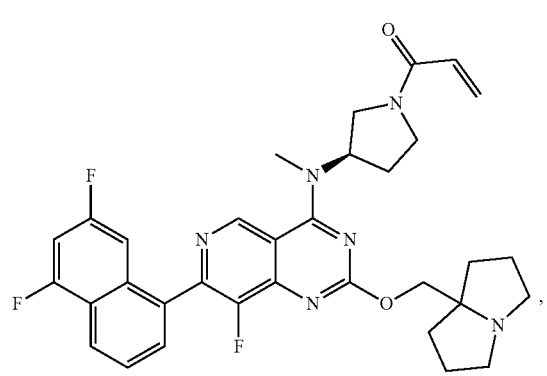
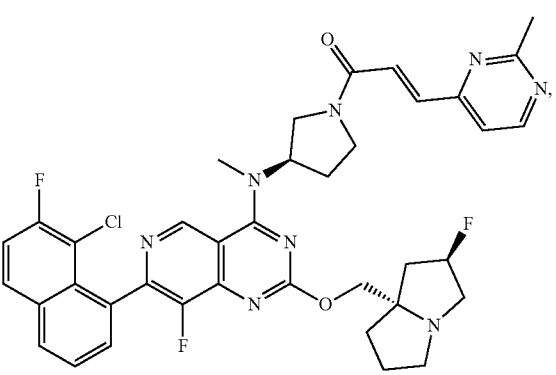

235
-continued
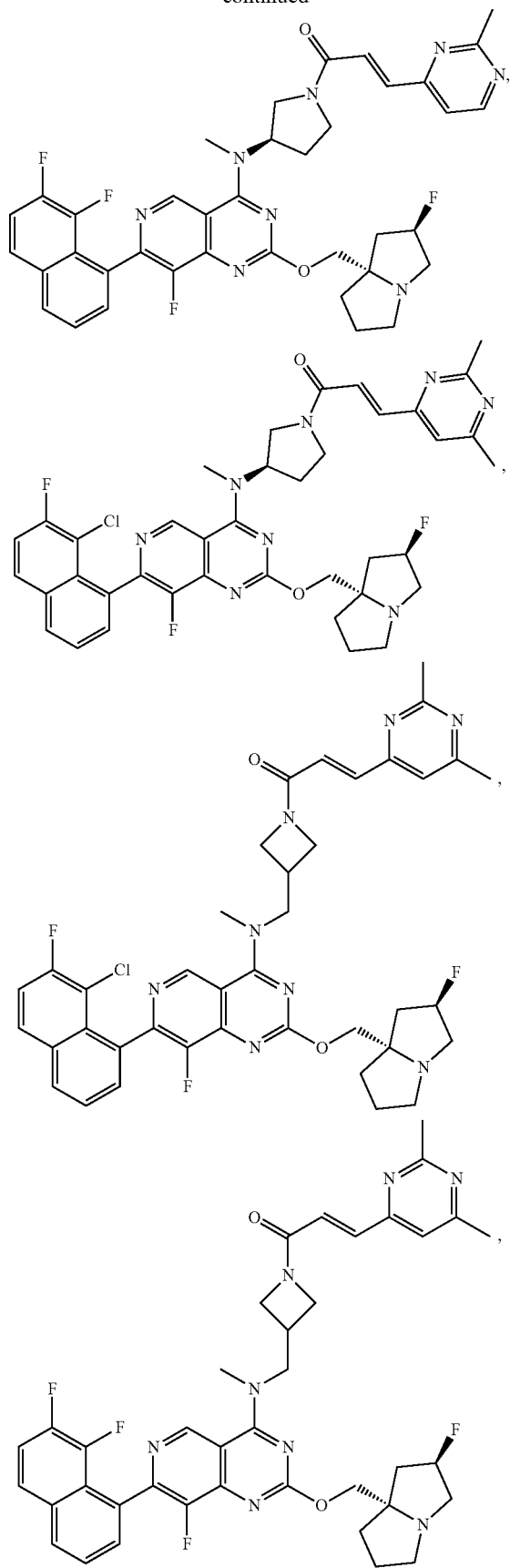
236
-continued
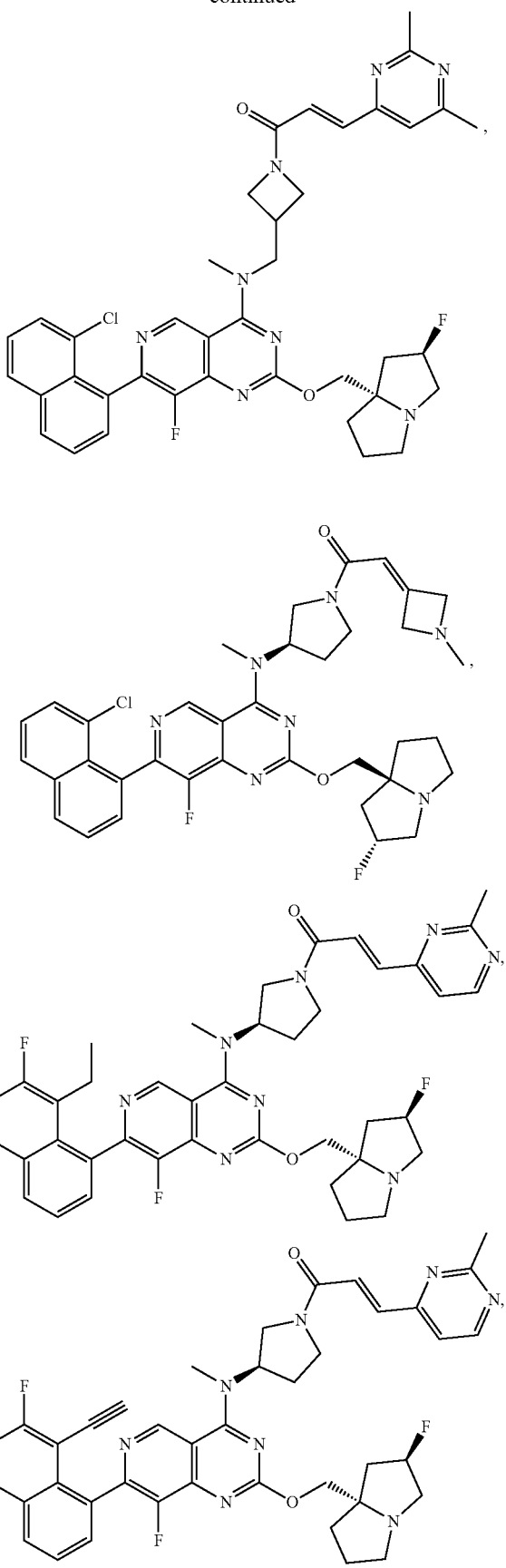

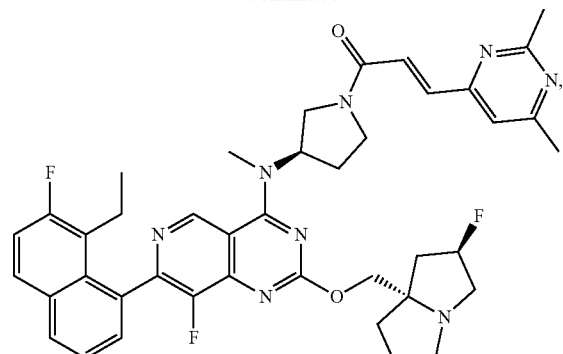
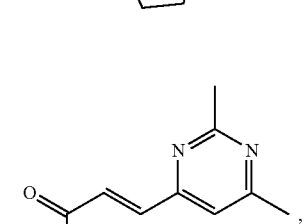
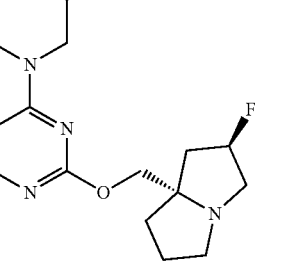
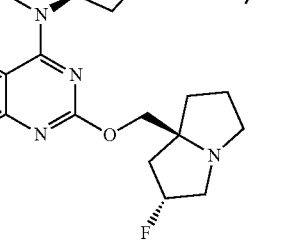
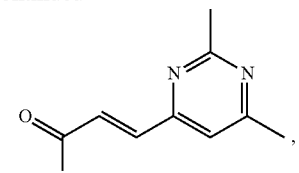
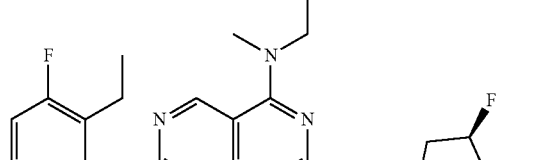
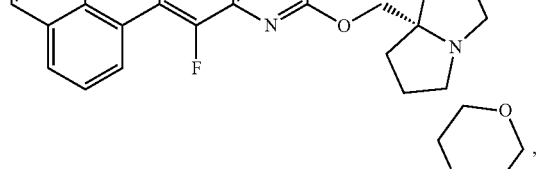
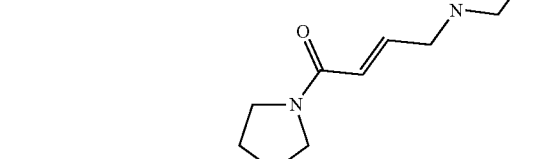
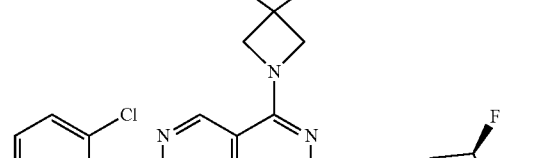
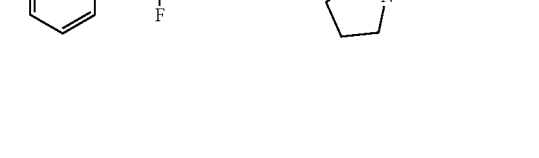

239
-continued
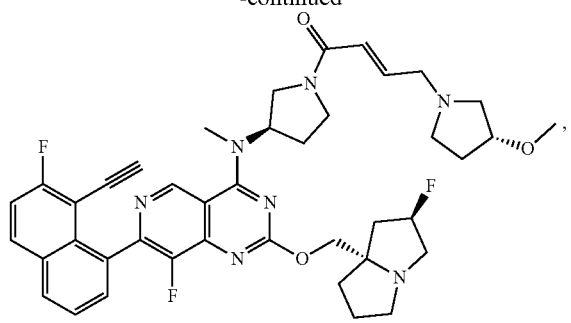
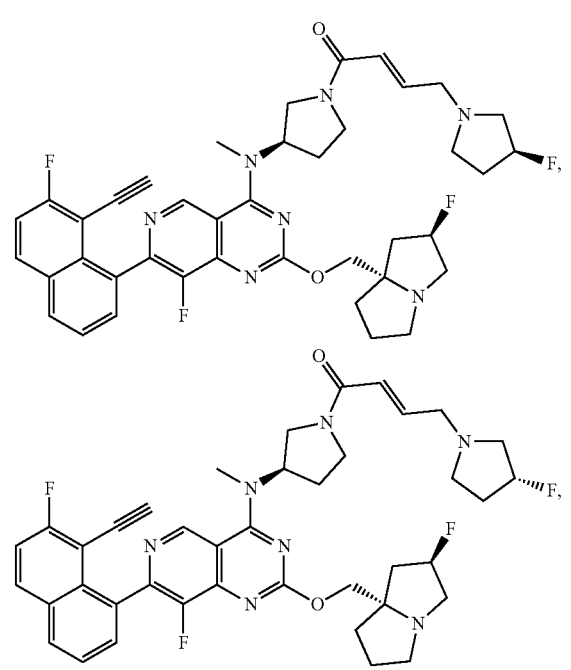
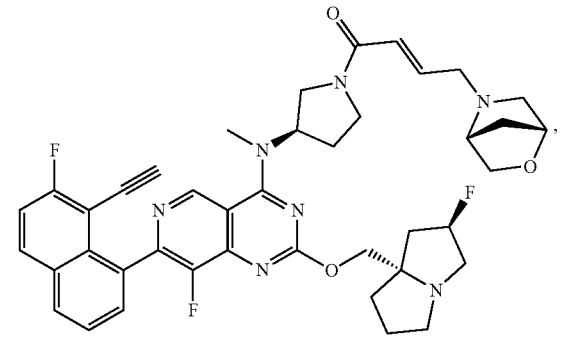
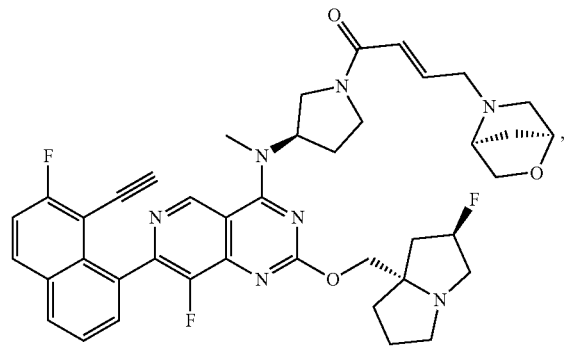
240
-continued
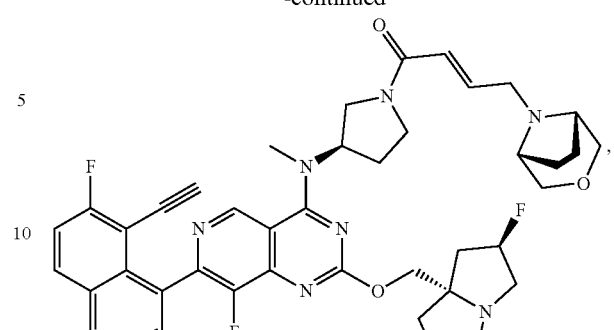

241
-continued
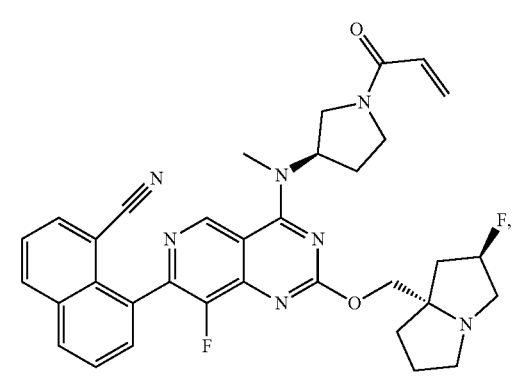
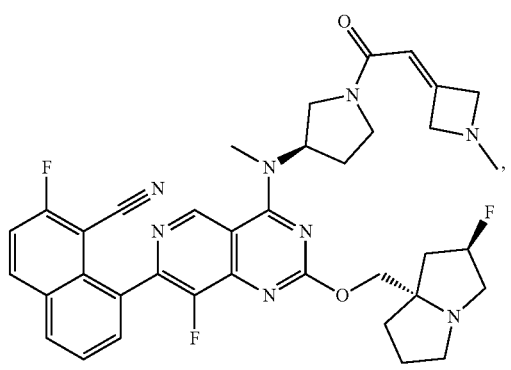
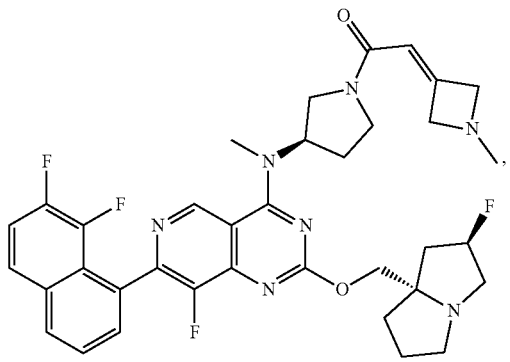
242
-continued
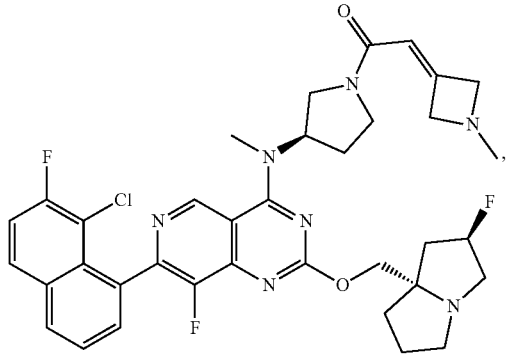
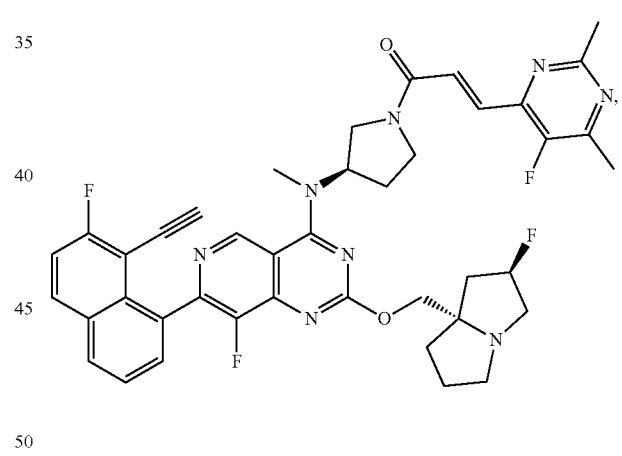
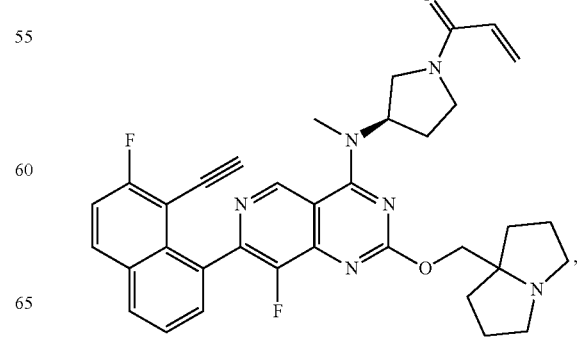

243
-continued
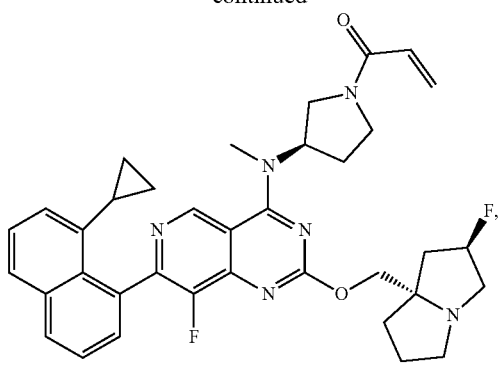
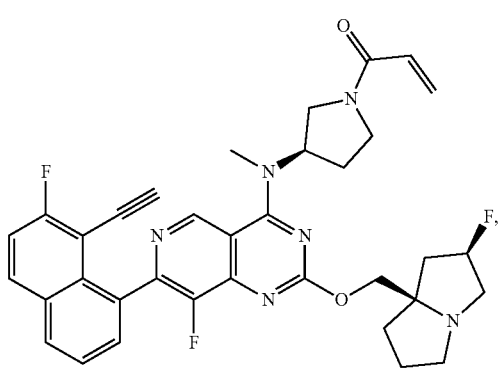
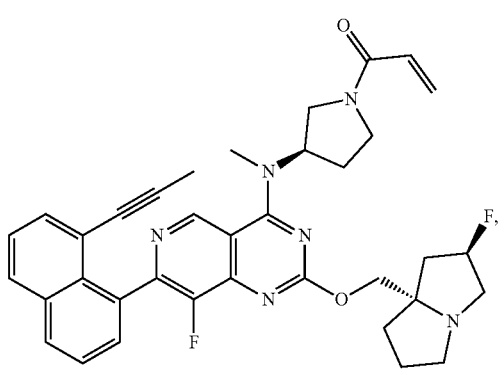
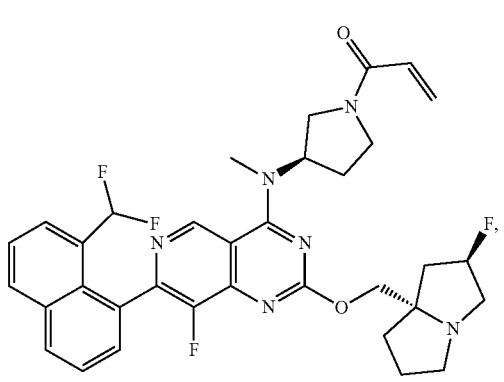
and all salts and isotopologues thereof.
244
Embodiment 430. The compound of any one of embodiments 1, 11 and 18, selected from the group consisting of:
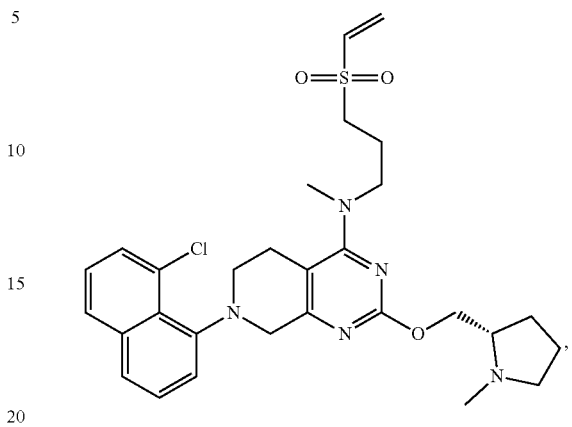
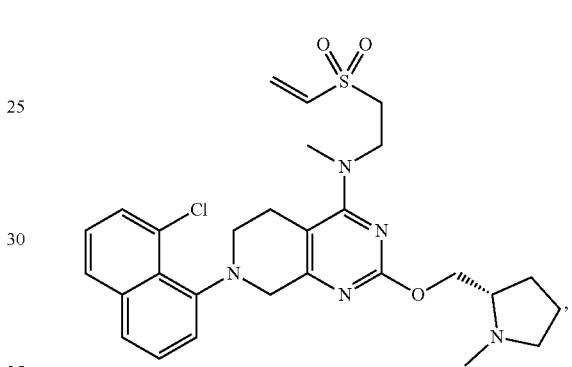
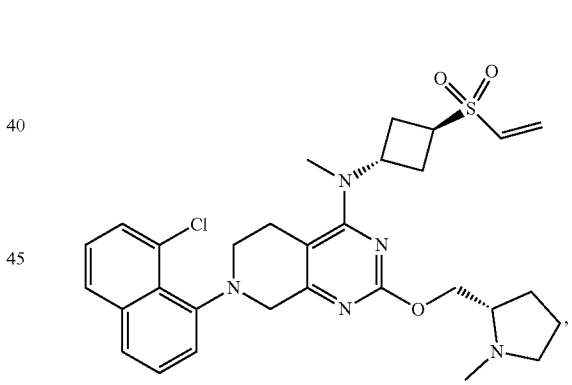

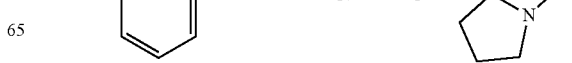

245
-continued
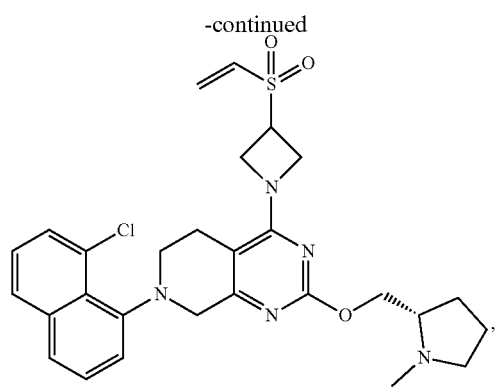
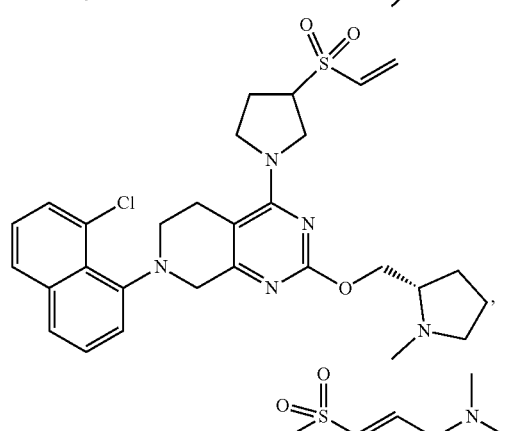
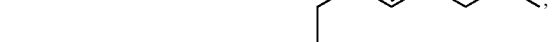
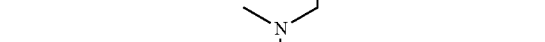
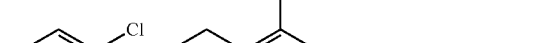

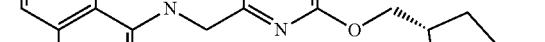
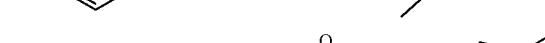
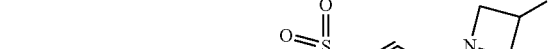

246
-continued
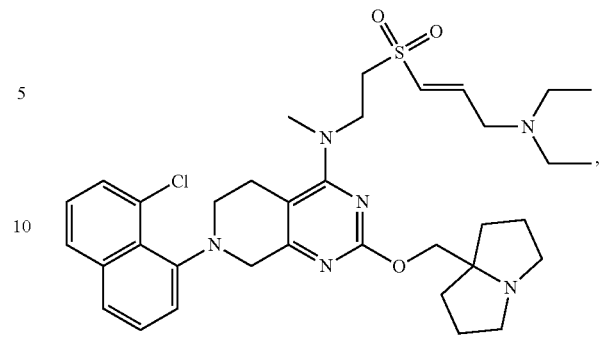
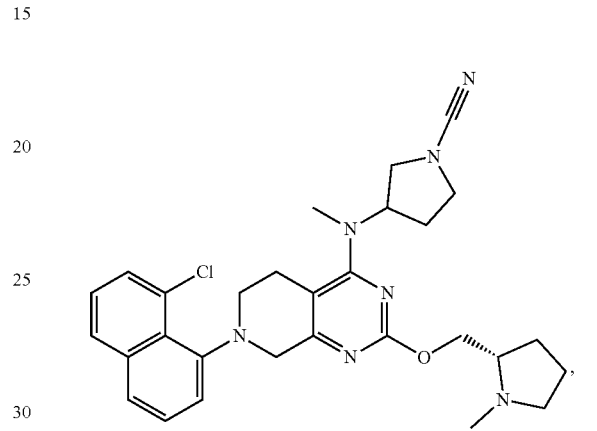
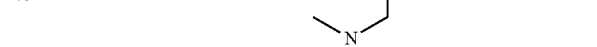
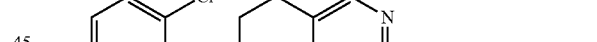
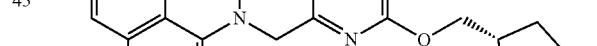

247
-continued
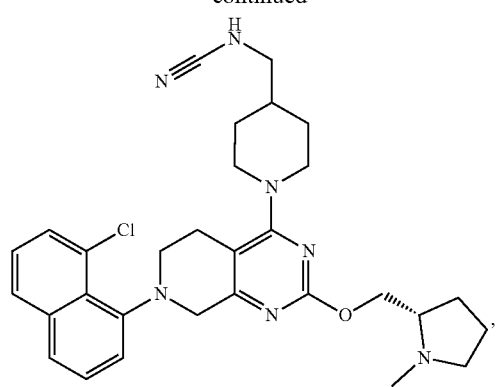
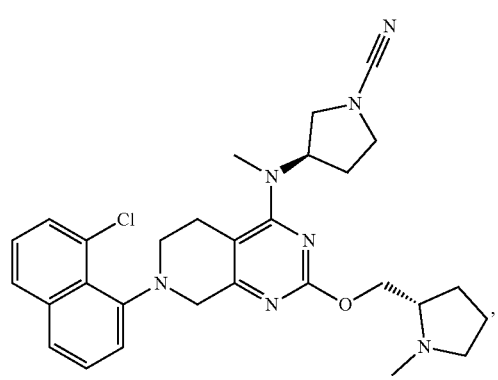

248
-continued
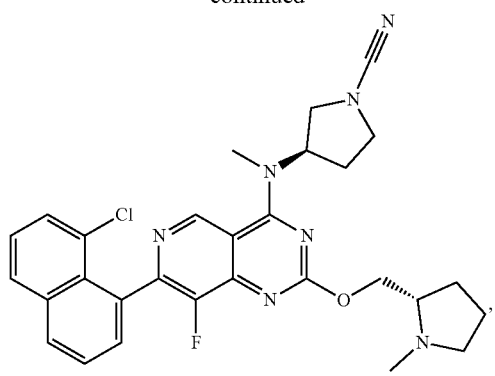
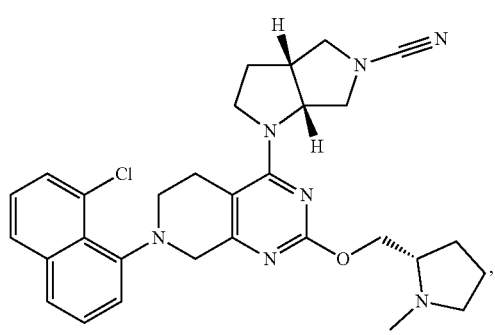
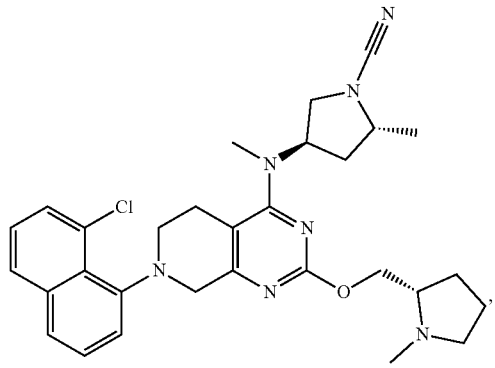
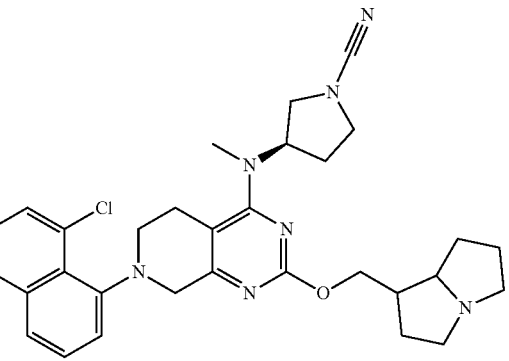

249
-continued
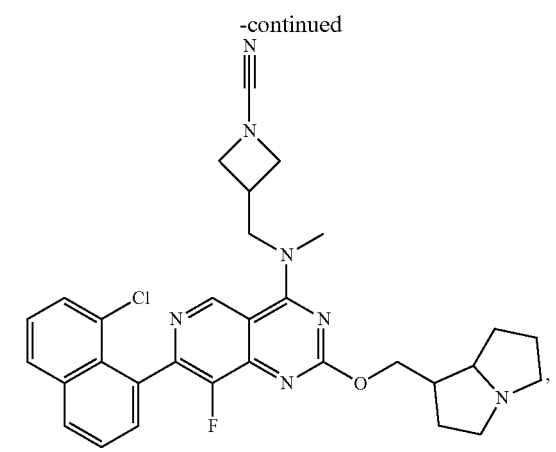
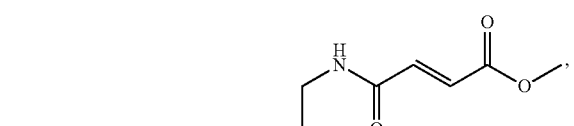
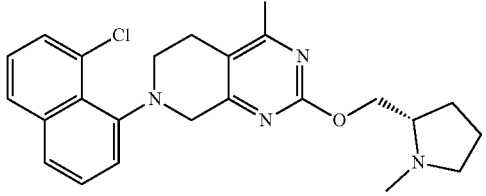
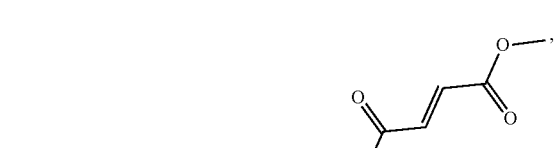
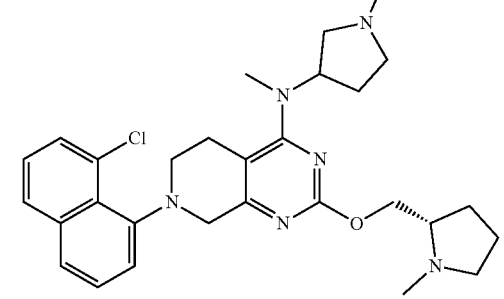
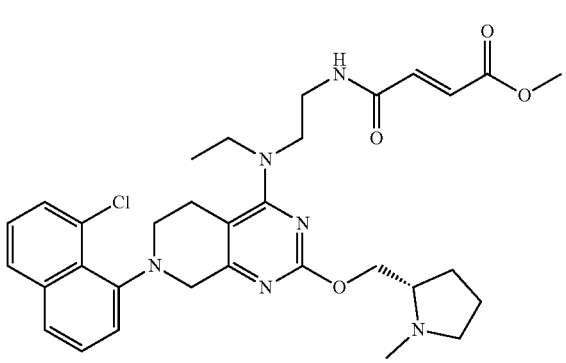
250
-continued
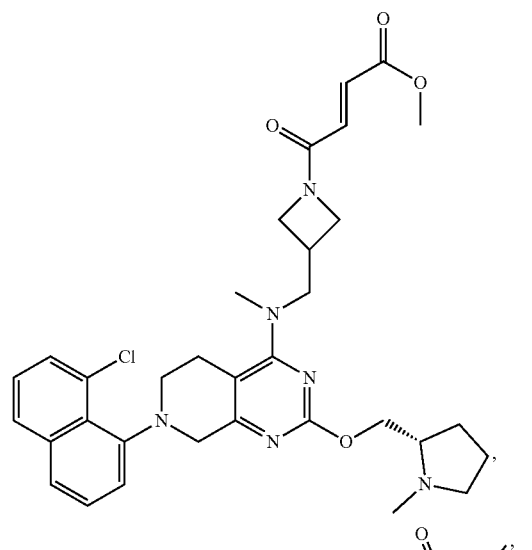
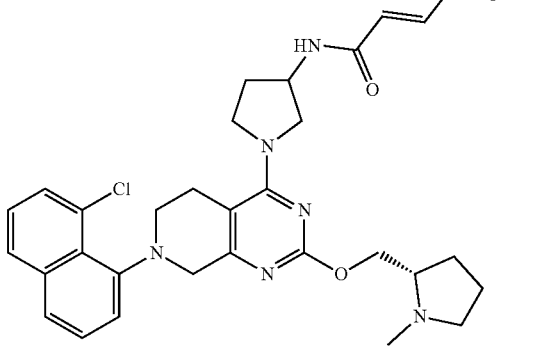
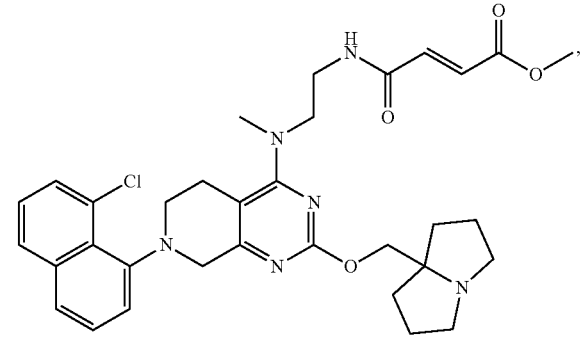
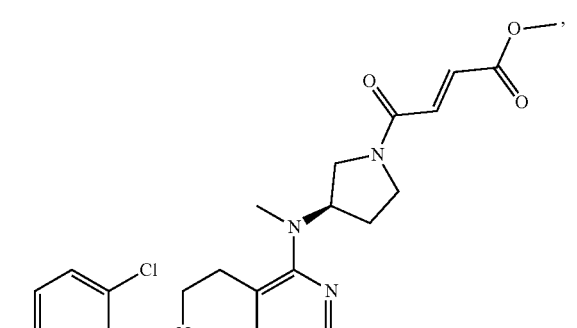
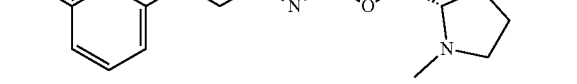

251
-continued
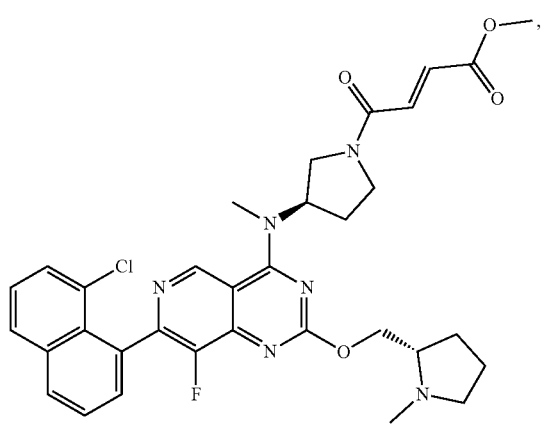
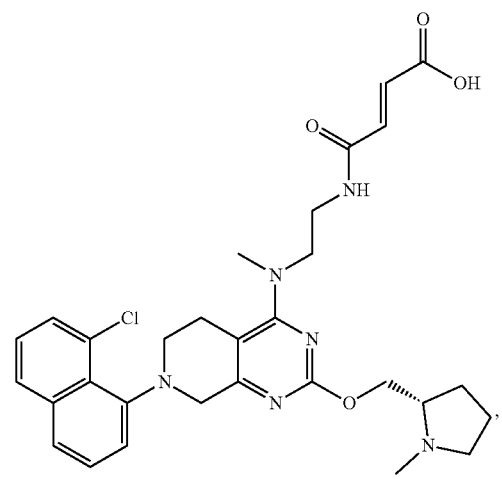
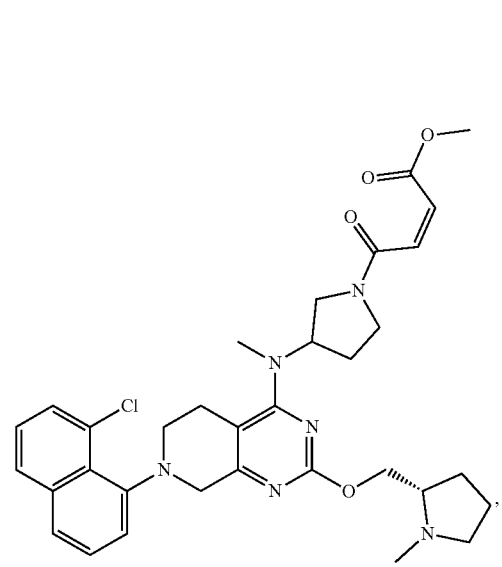
252
-continued
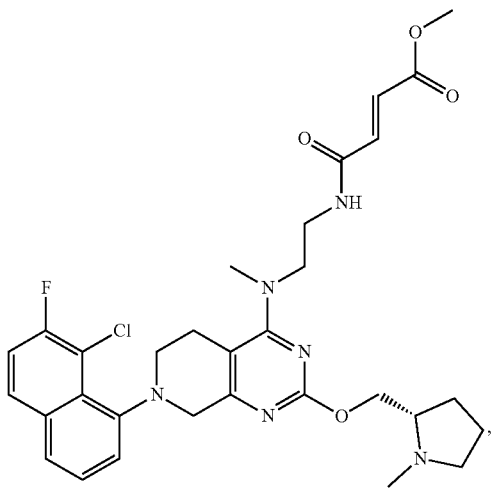
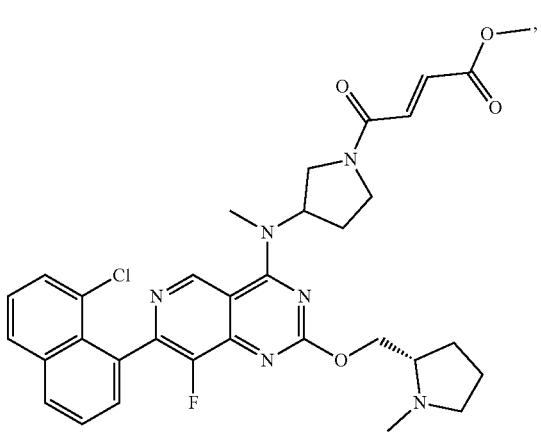
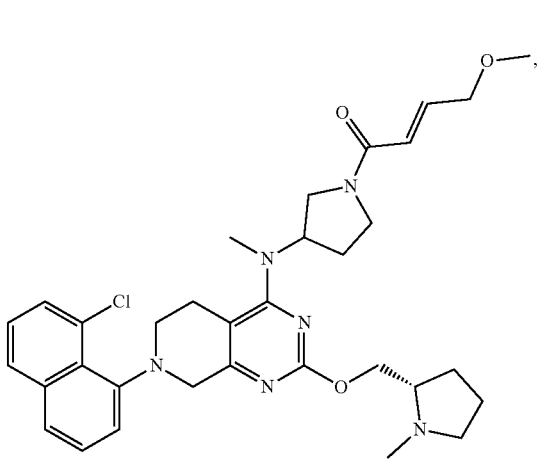

253
-continued
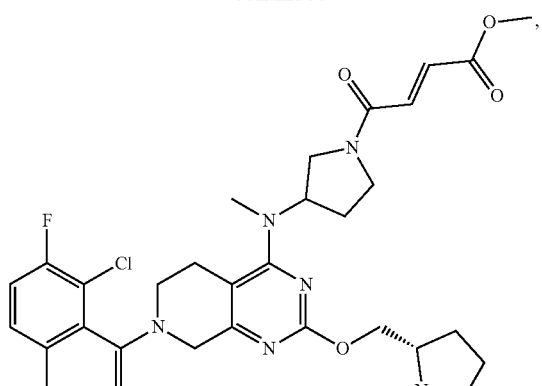
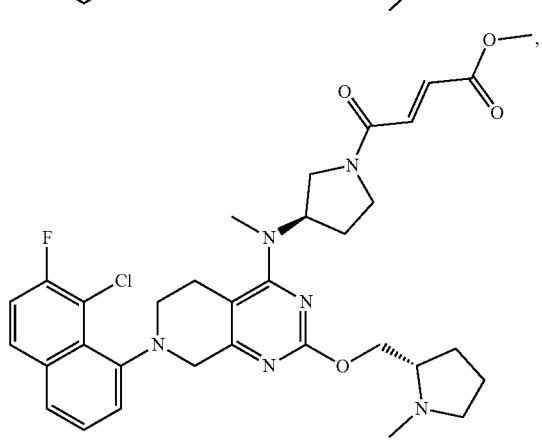
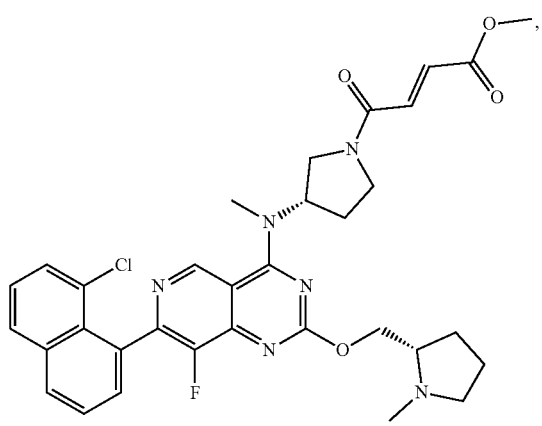
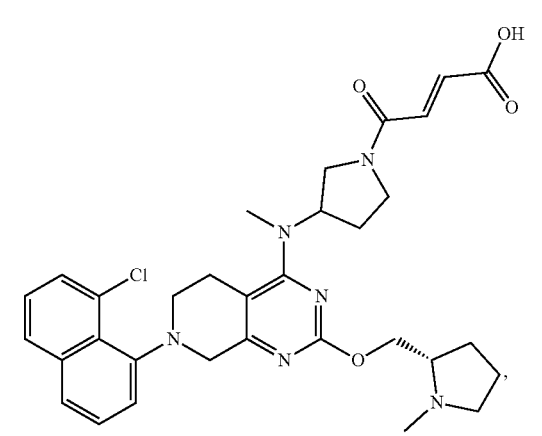
254
-continued
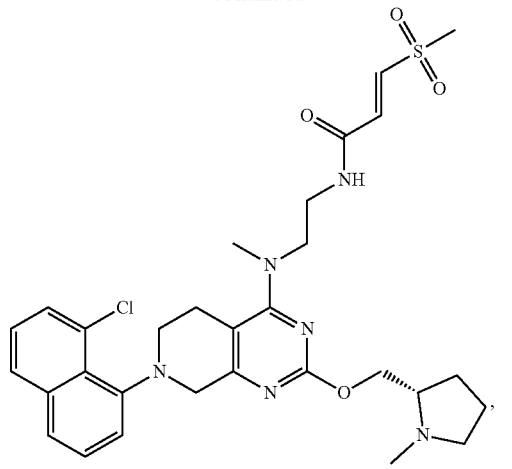

255
-continued
256
-continued
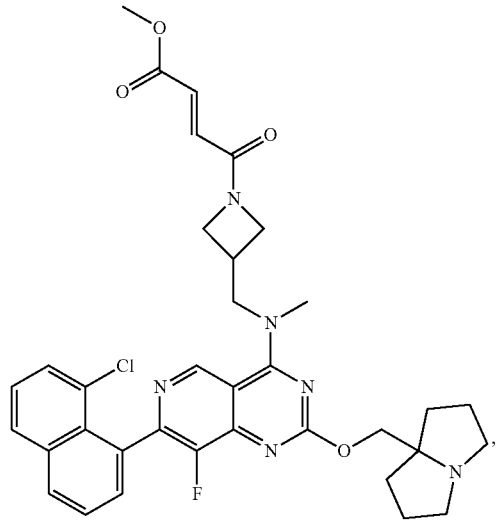

257
-continued

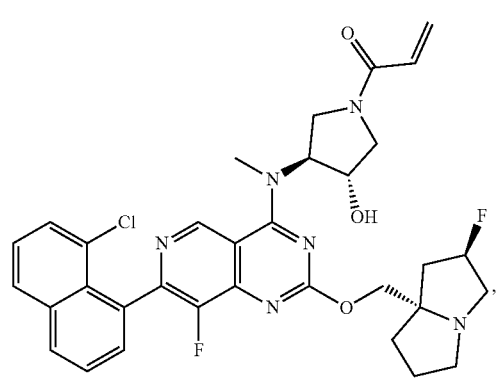
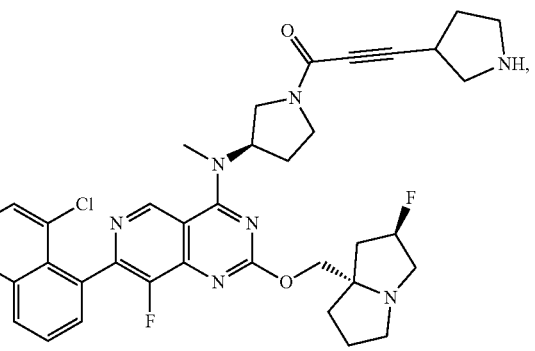
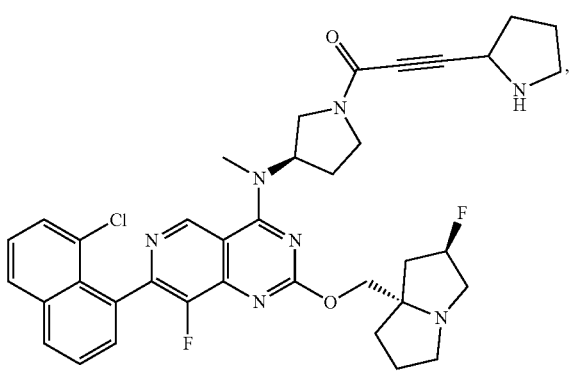
258
-continued
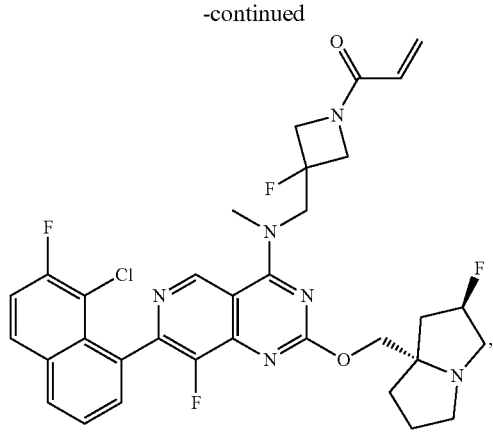
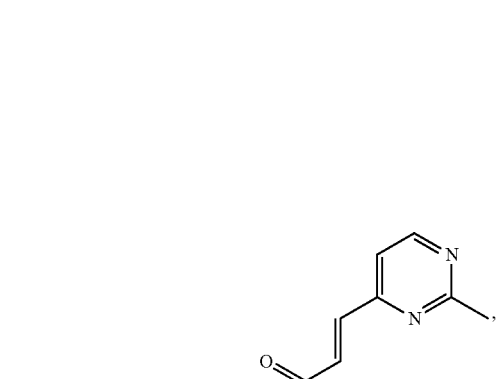
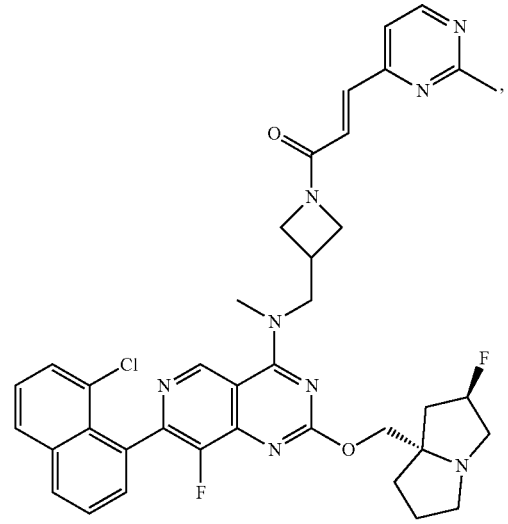

259
-continued
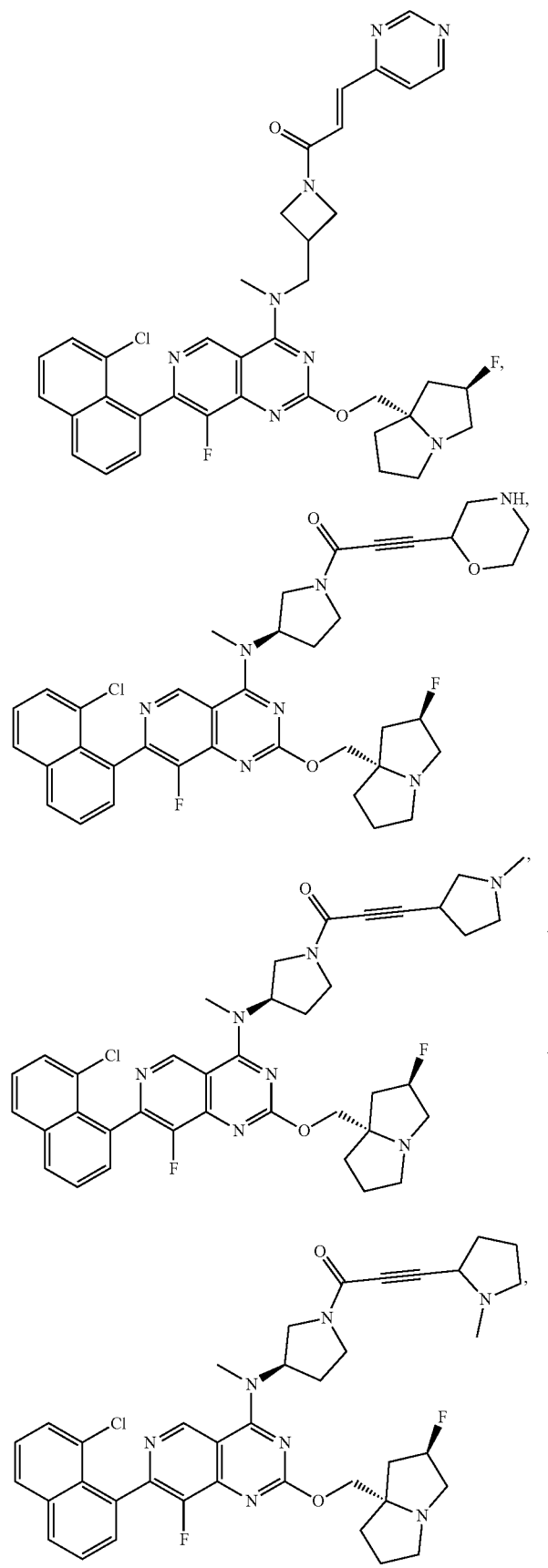
260
-continued
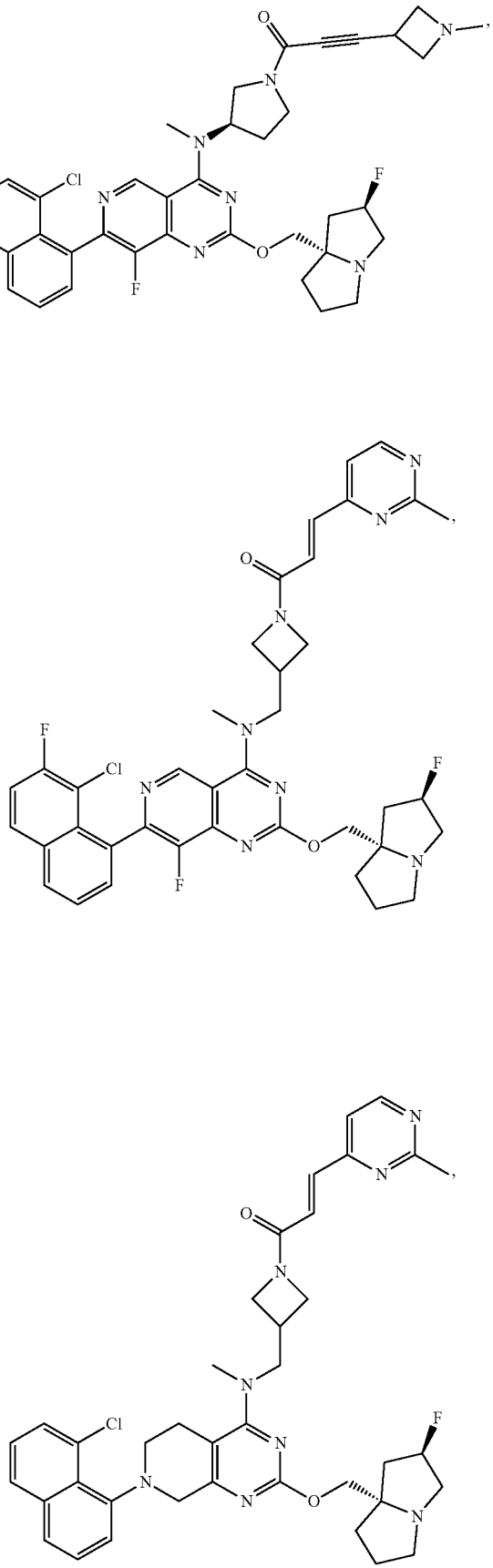

261
-continued
262
-continued
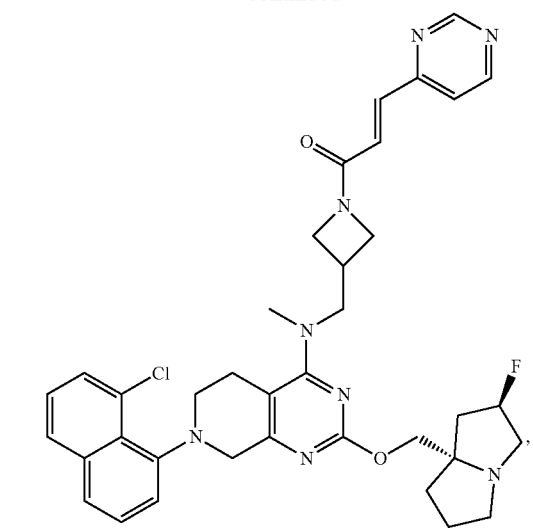
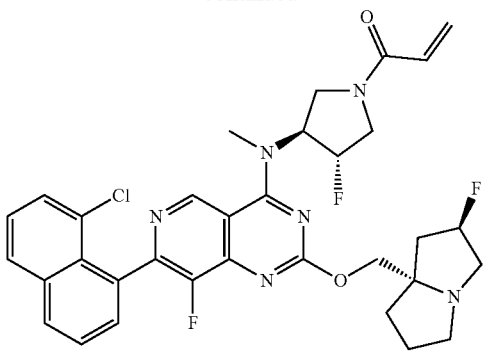
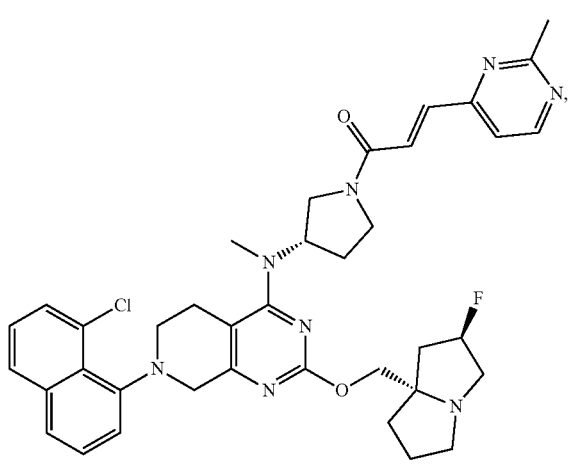
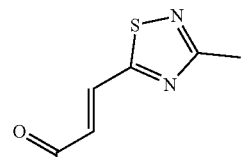
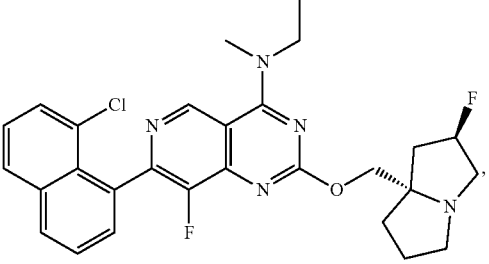
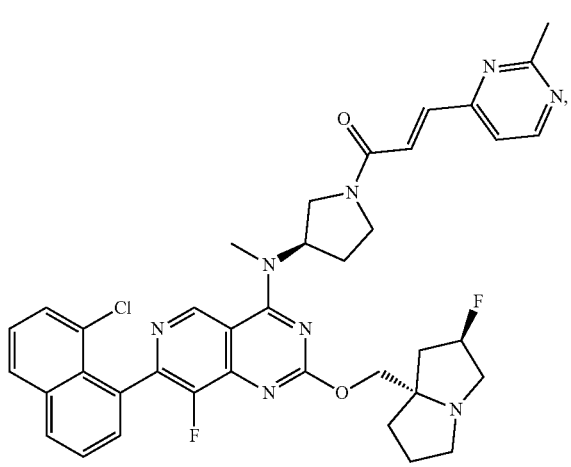

263
-continued
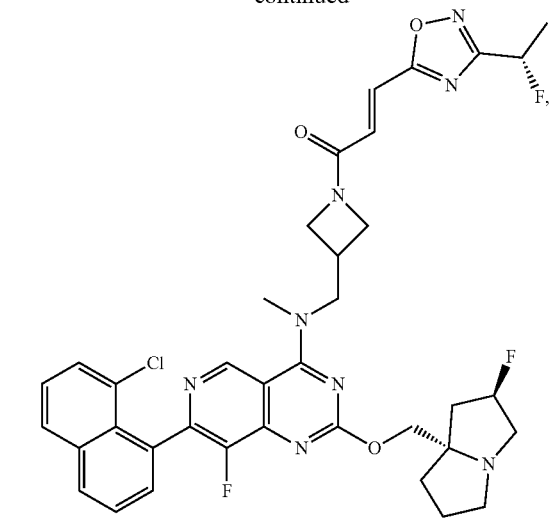
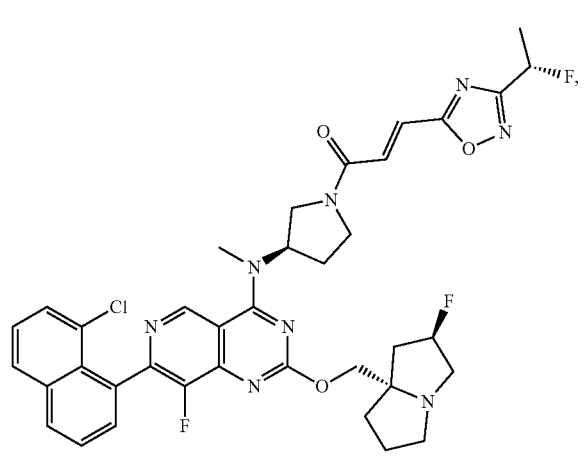
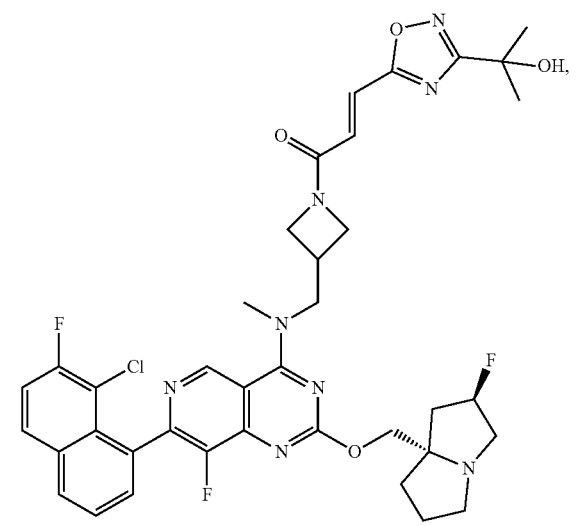
264
-continued
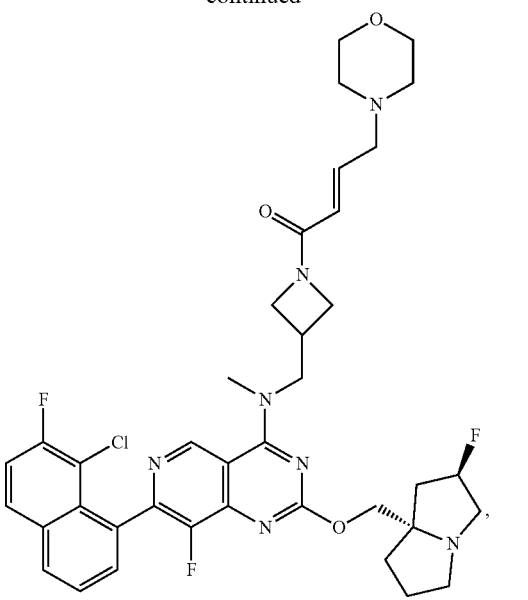
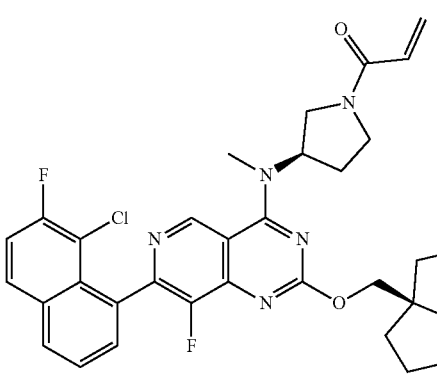

265
-continued
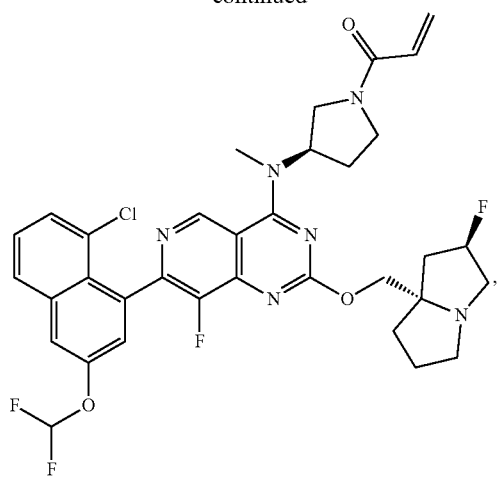
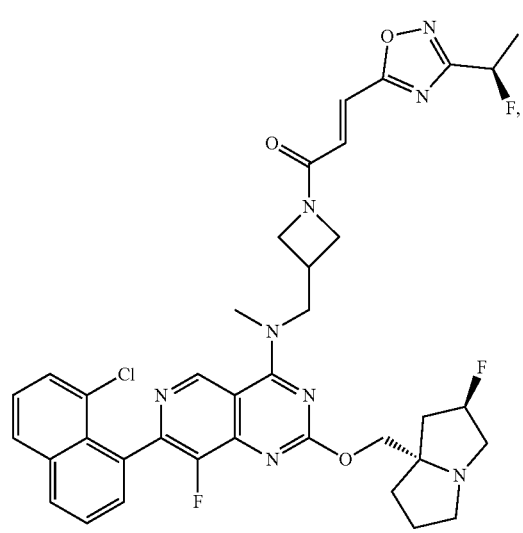
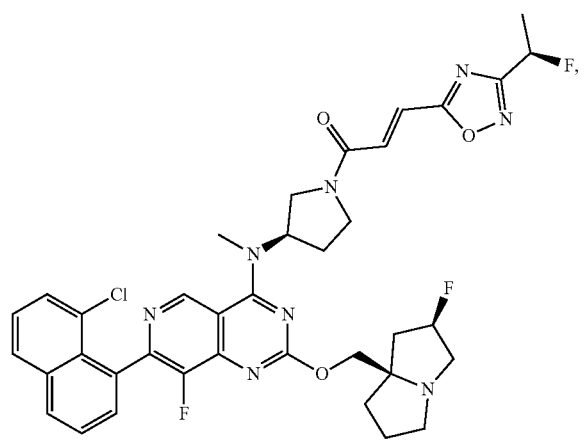
266
-continued
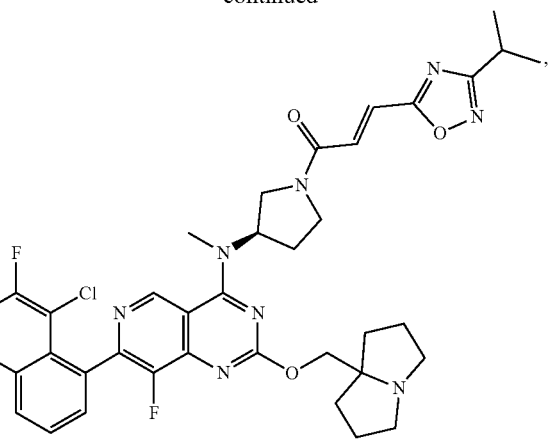
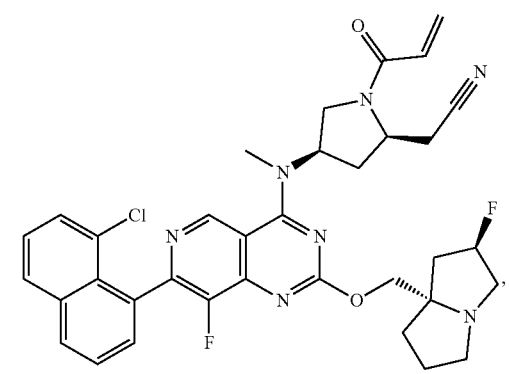

267
-continued
268
-continued
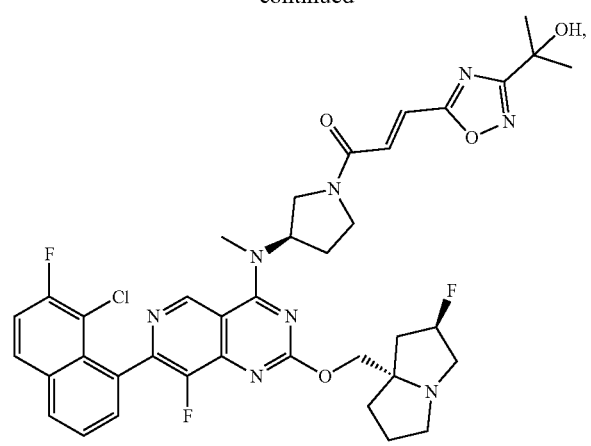
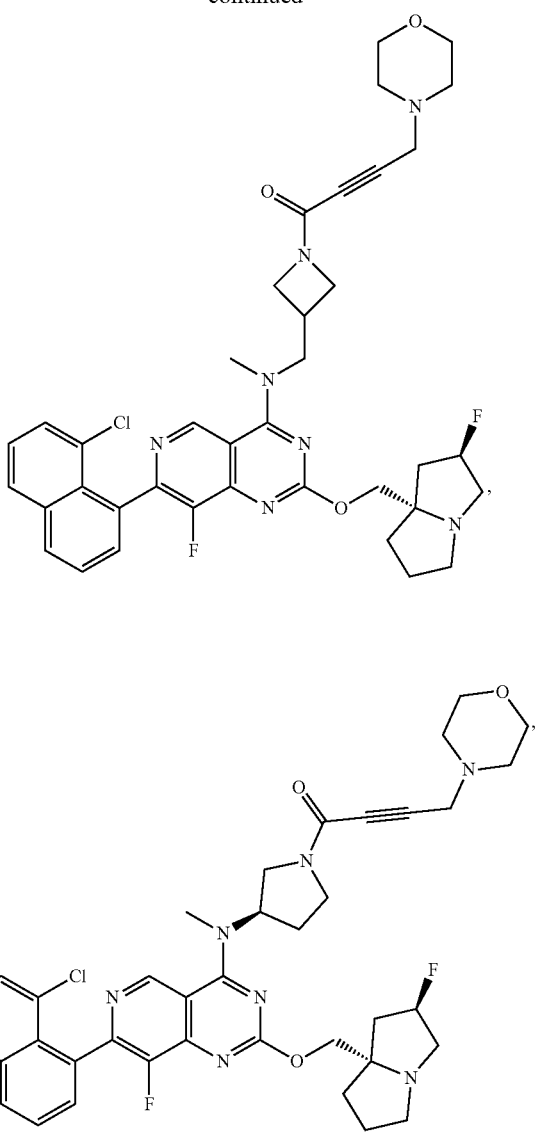
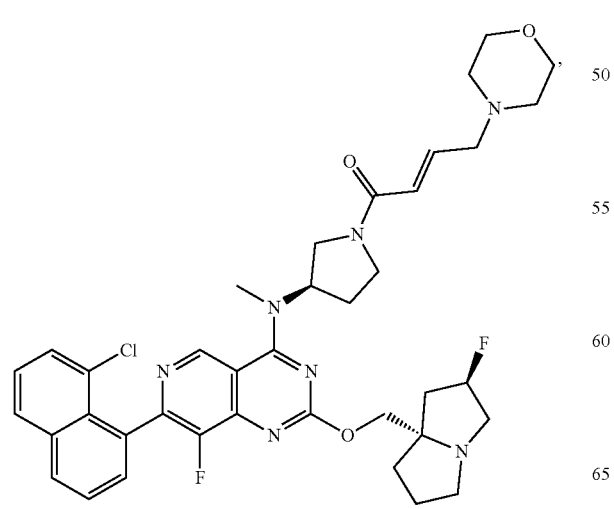

269
-continued
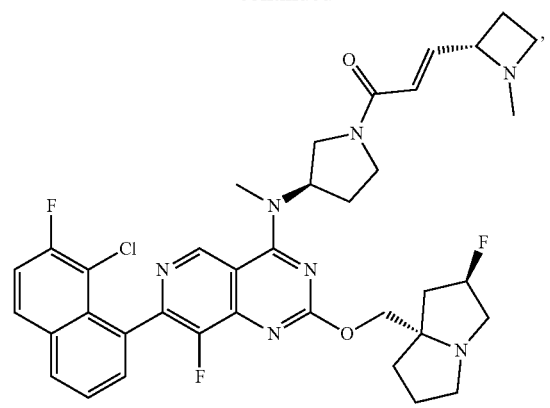
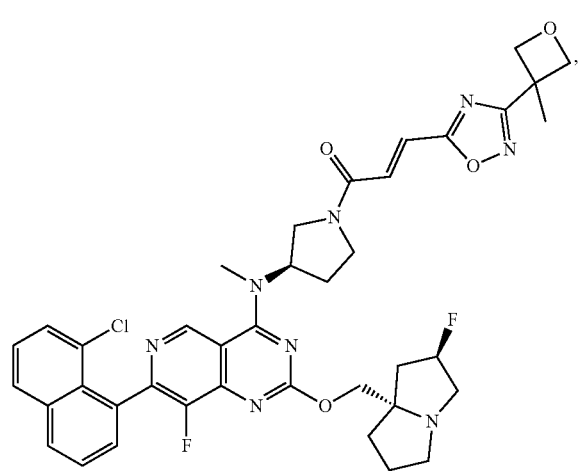
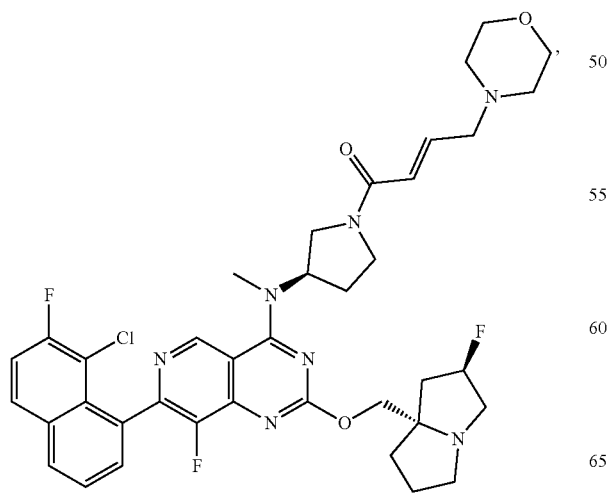
270
-continued
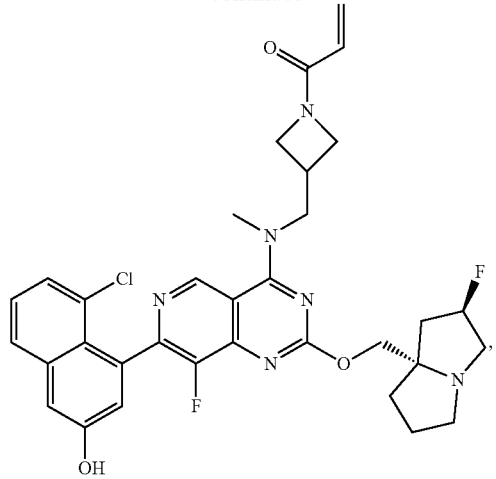
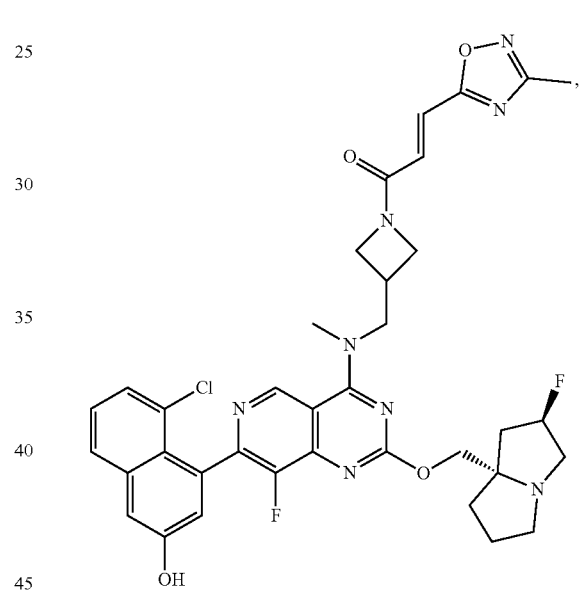
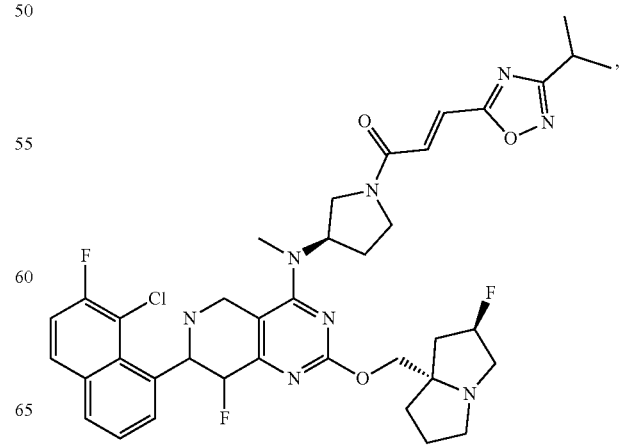

-continued
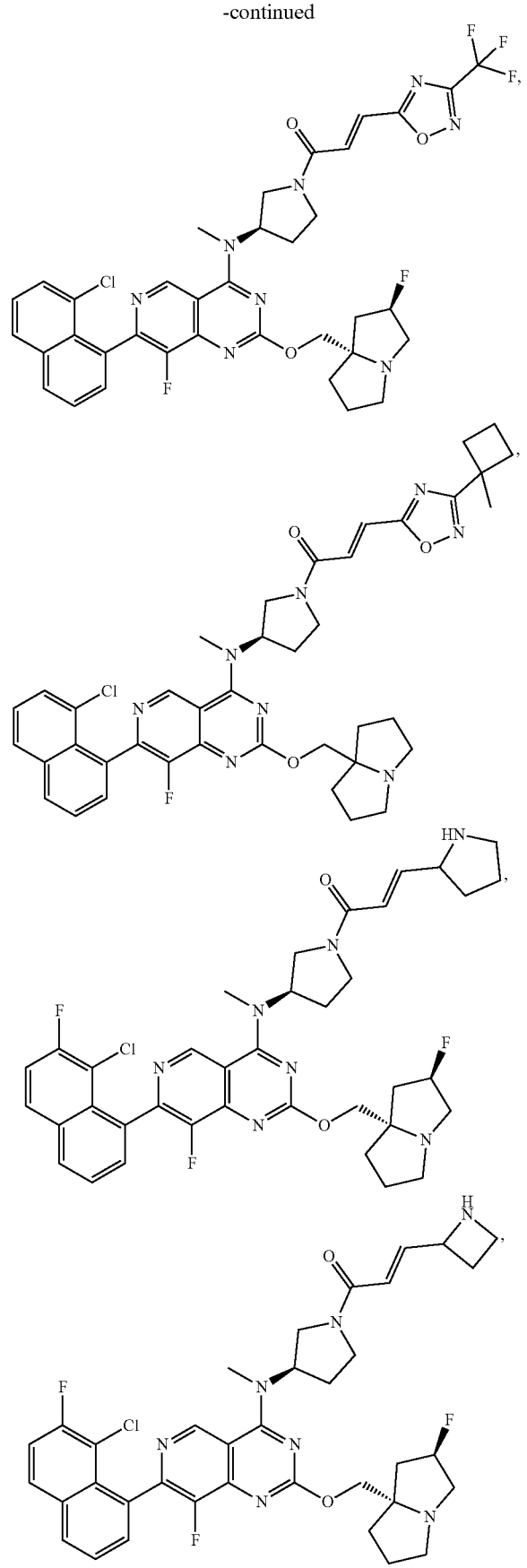
-continued
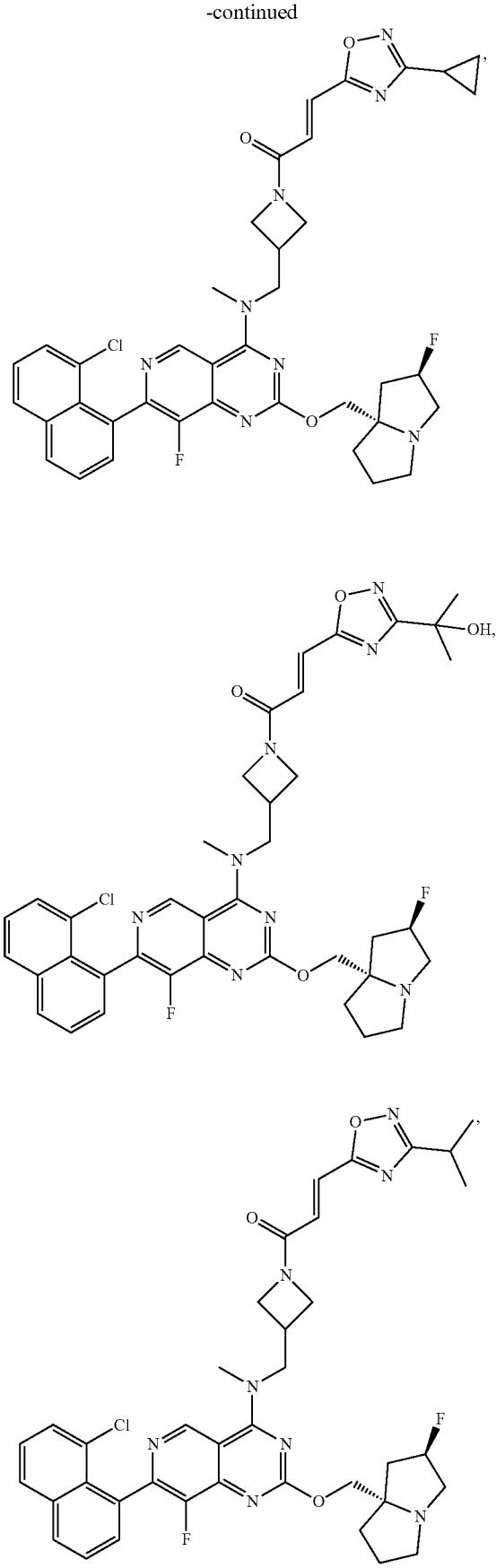

273
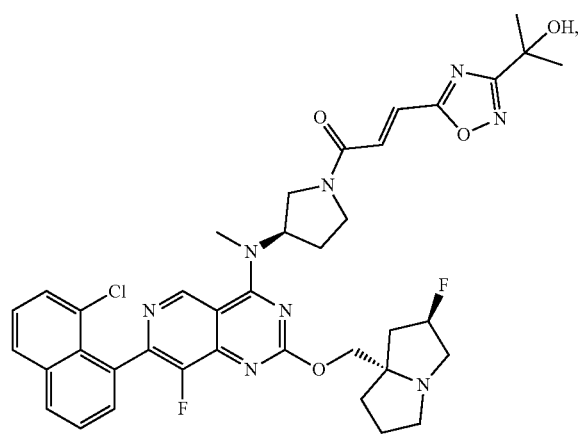

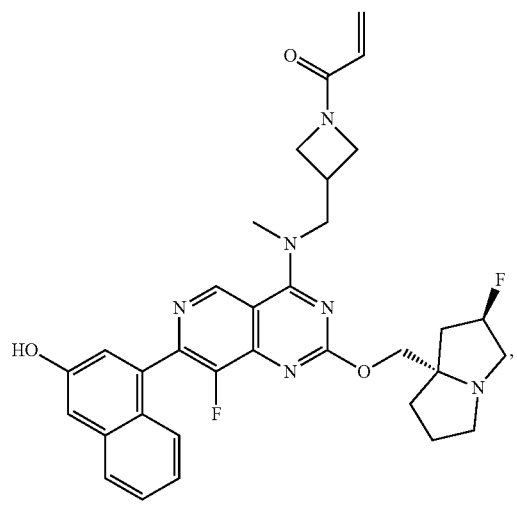
274
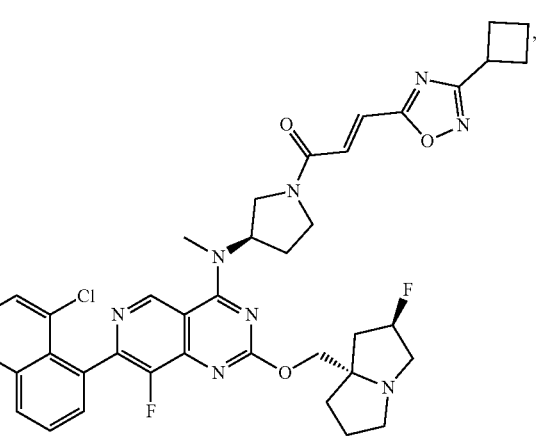
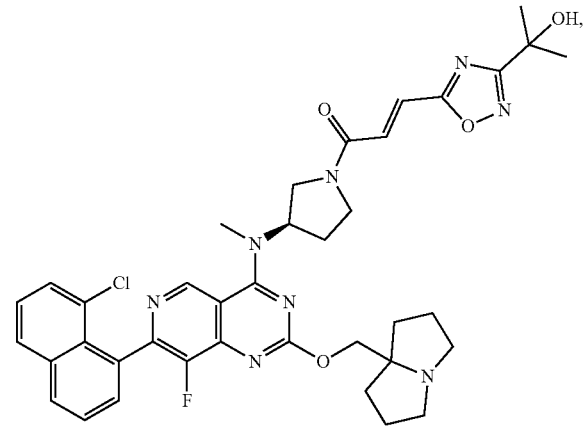

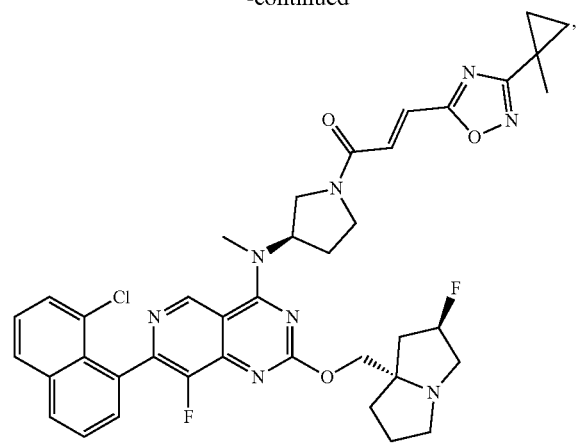
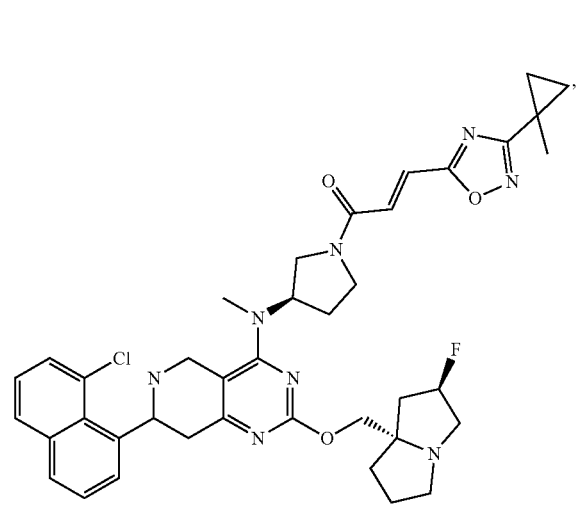
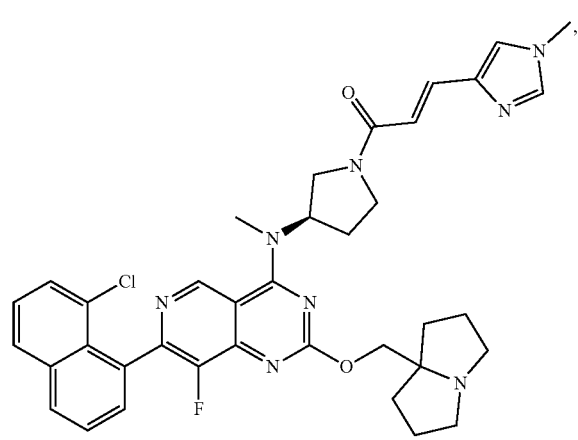
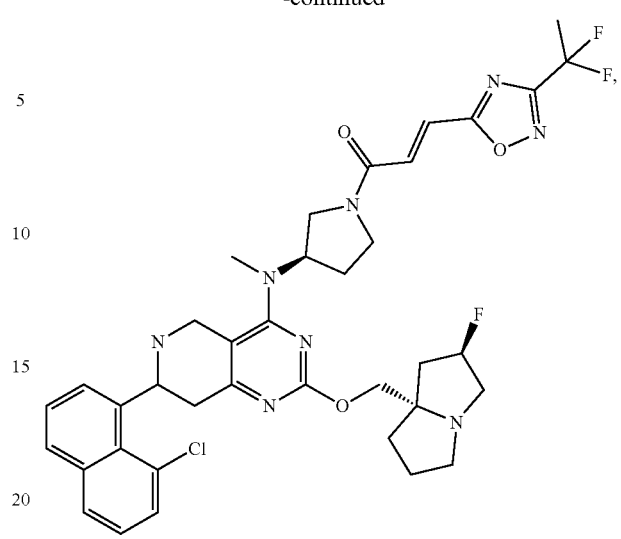
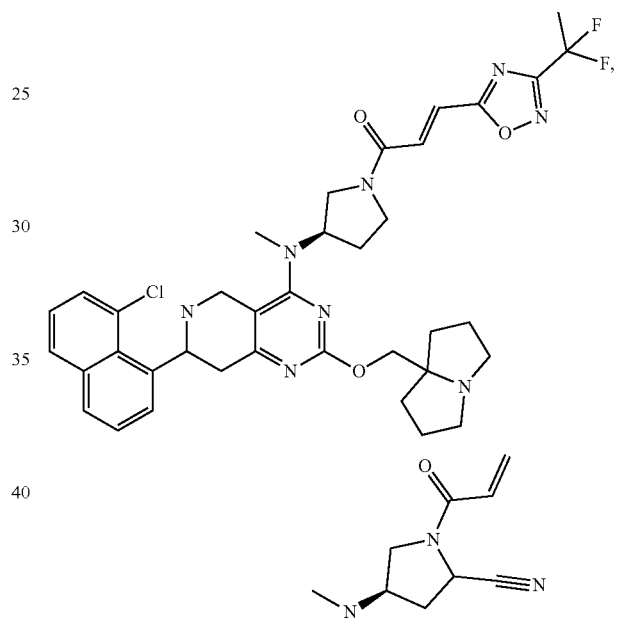
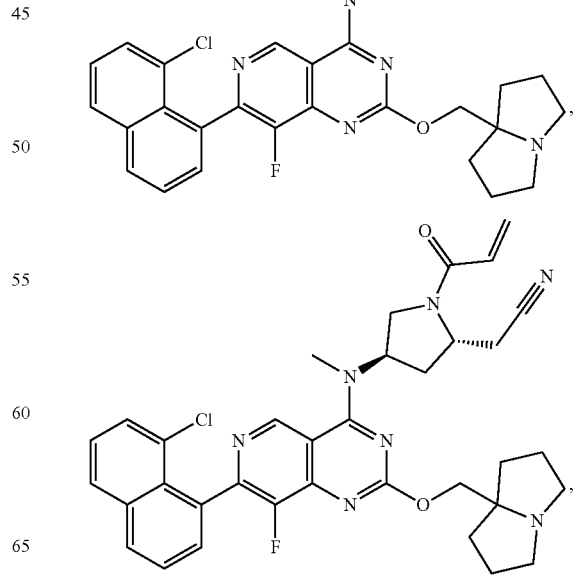

277
-continued
278
-continued
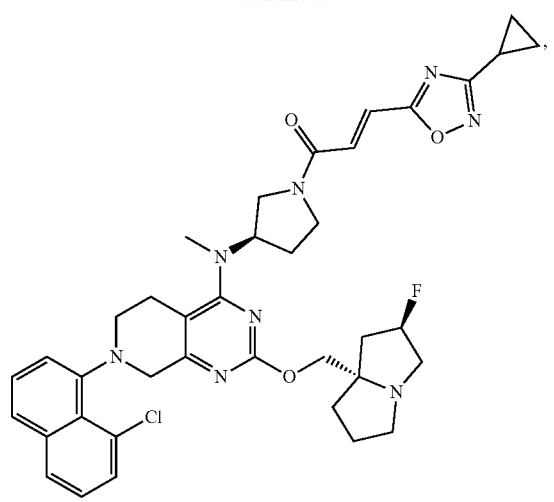
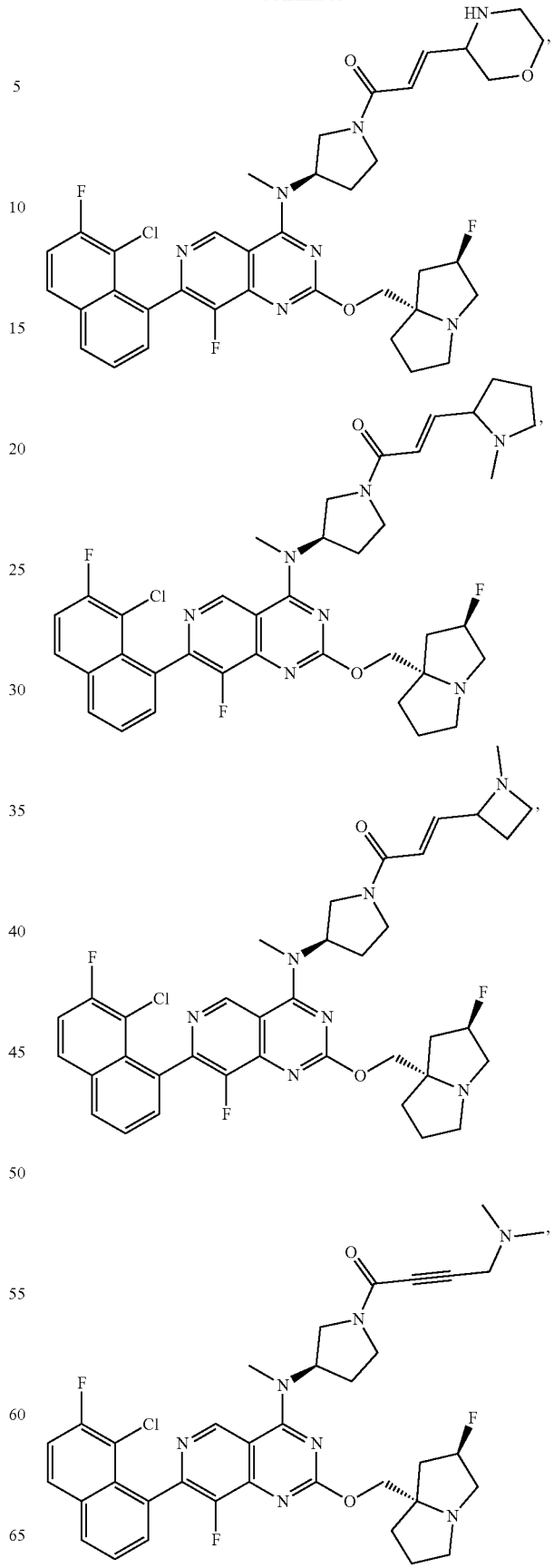

279
-continued
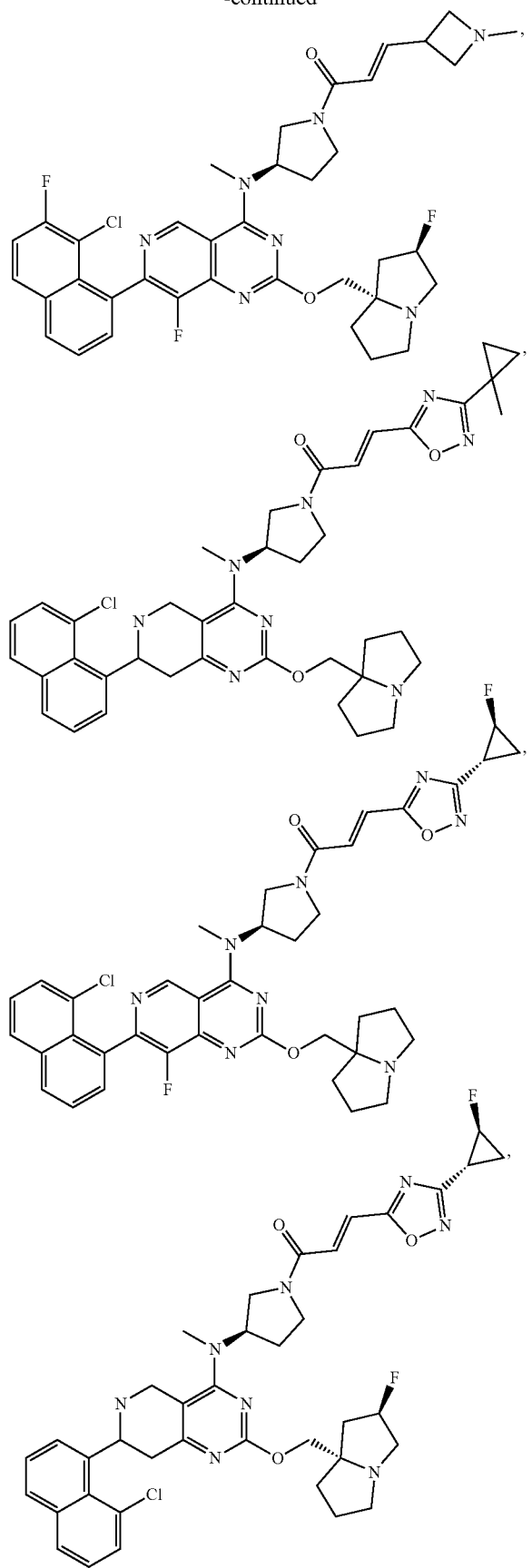
280
-continued
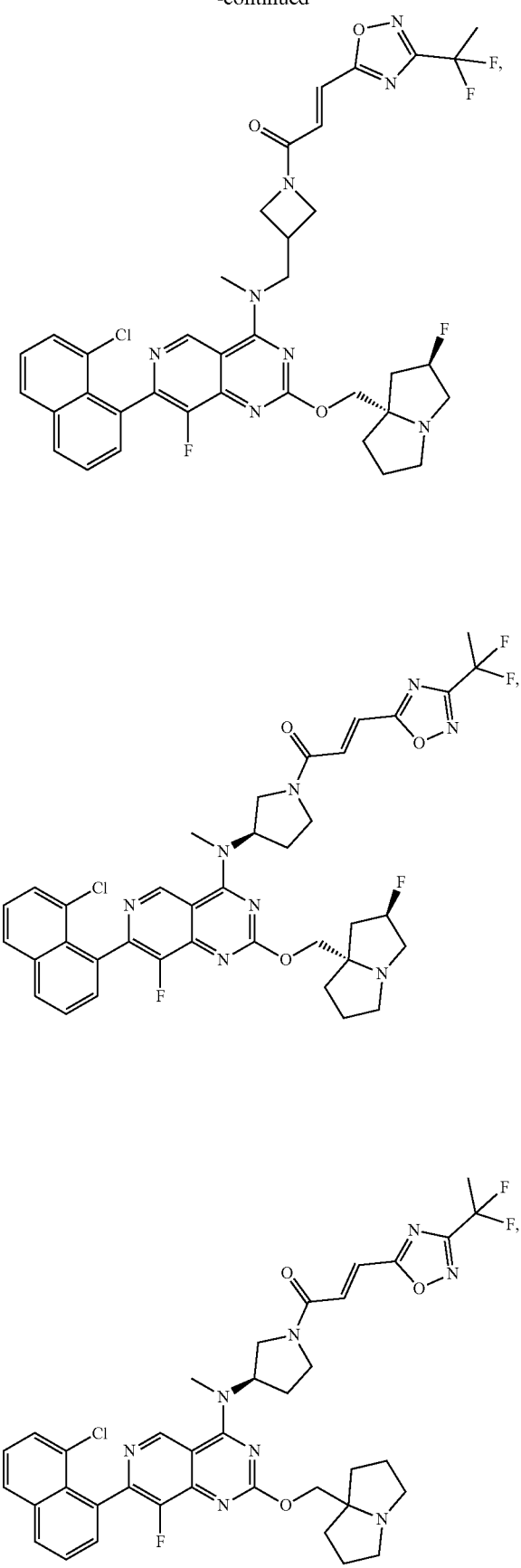

281
-continued
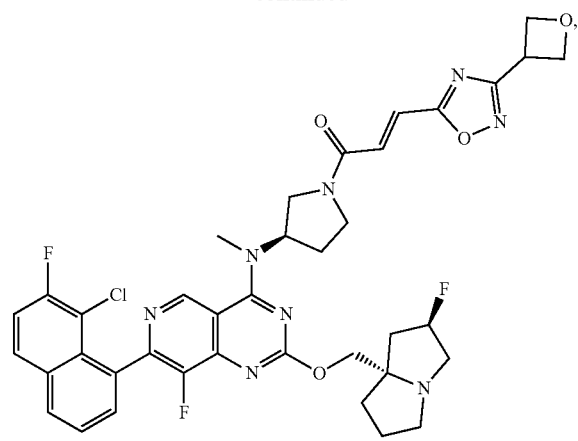
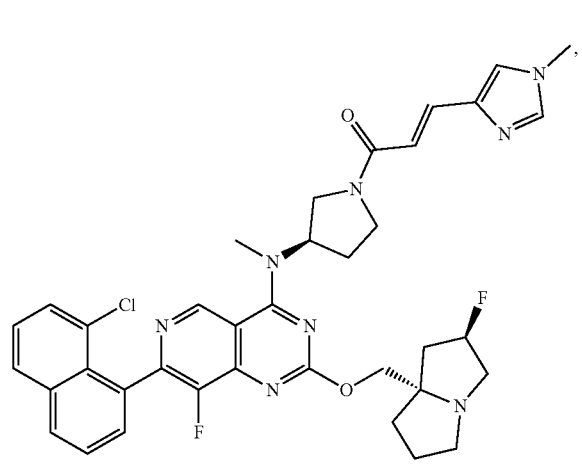
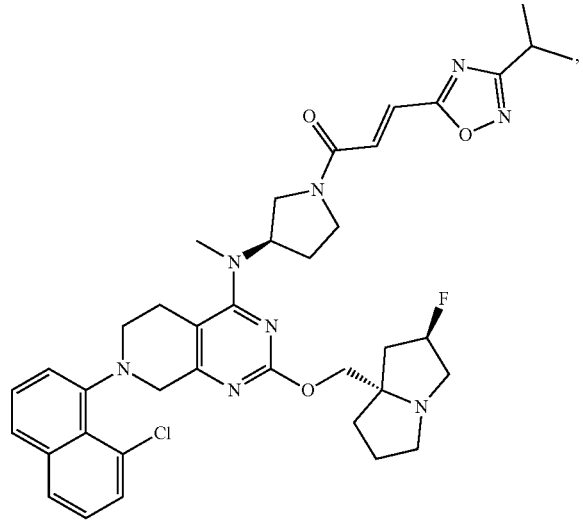
282
-continued
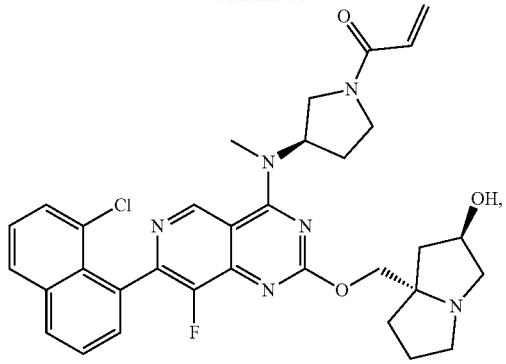
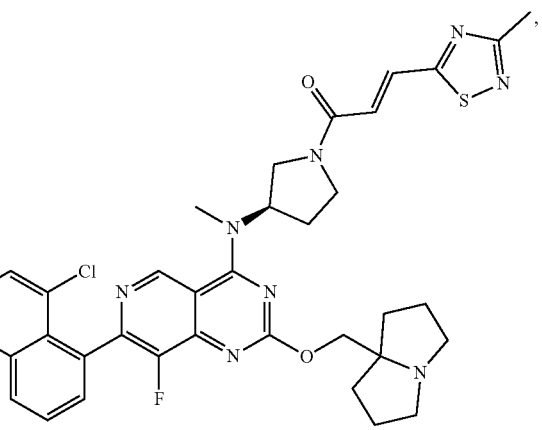
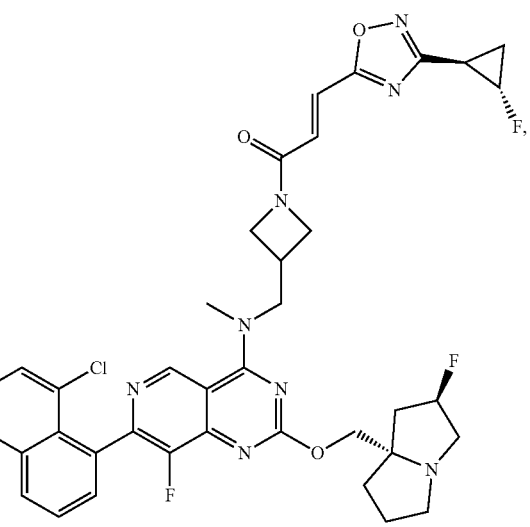

283
-continued
284
-continued
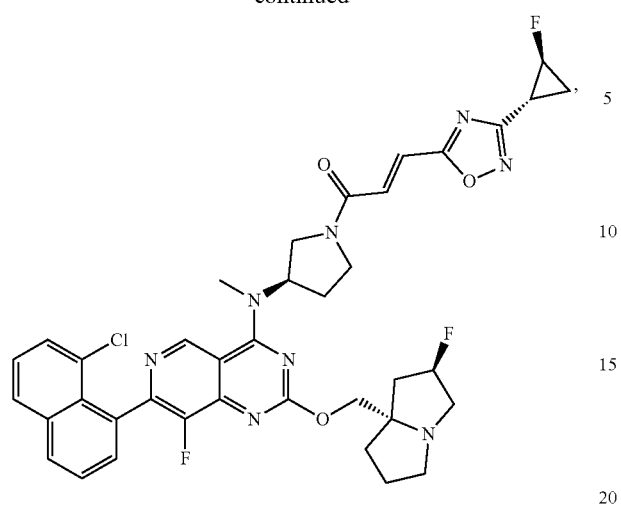
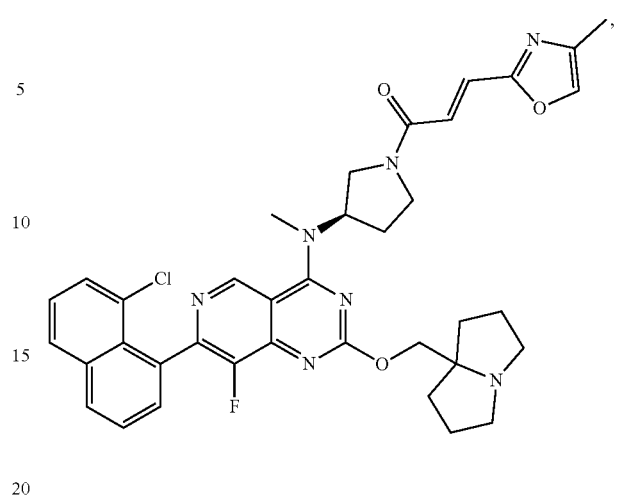
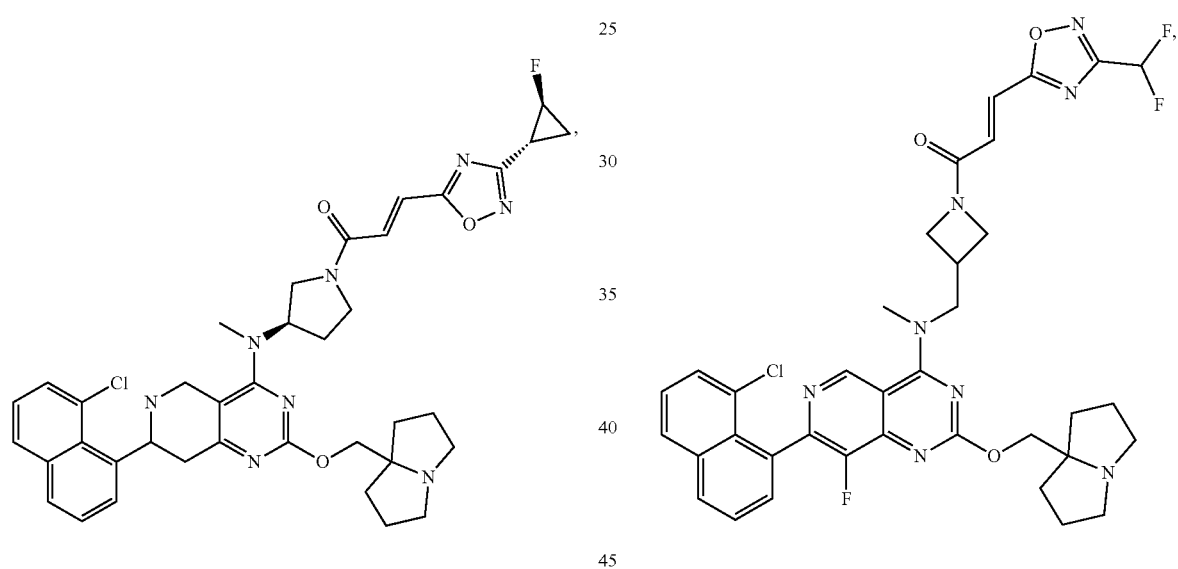
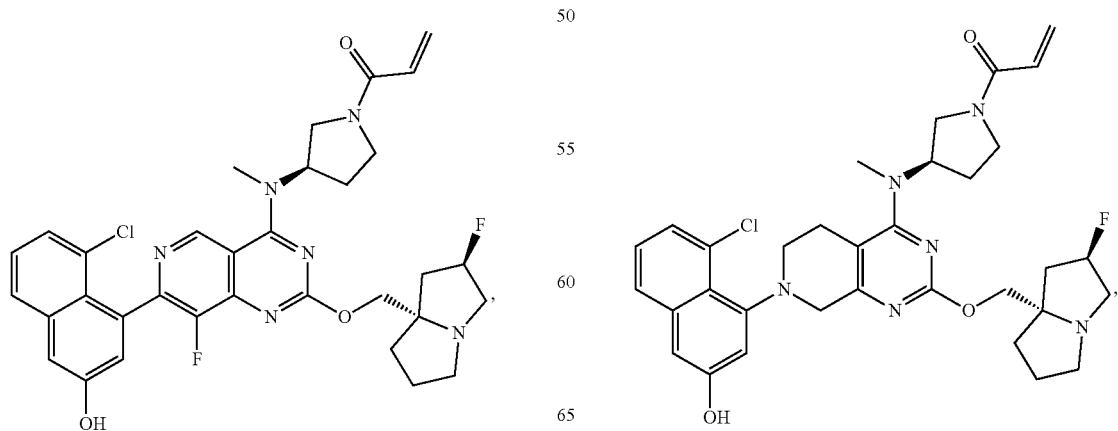

285
-continued
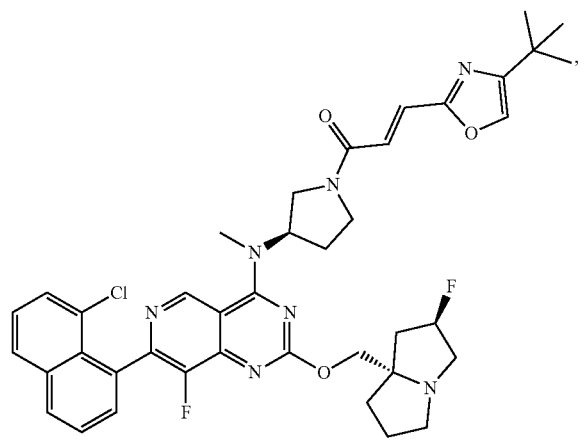
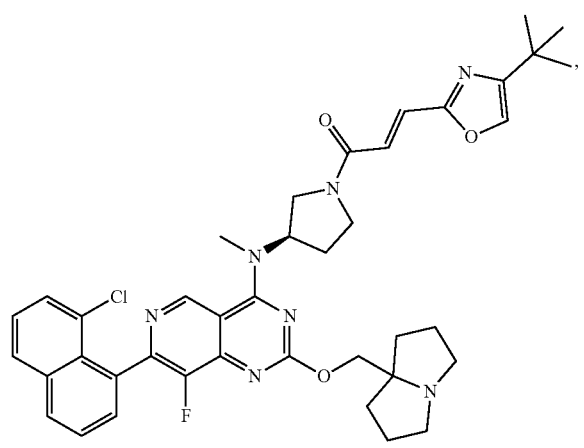
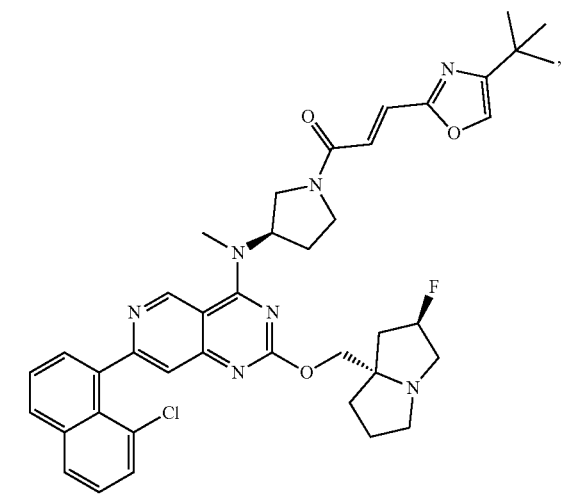
286
-continued
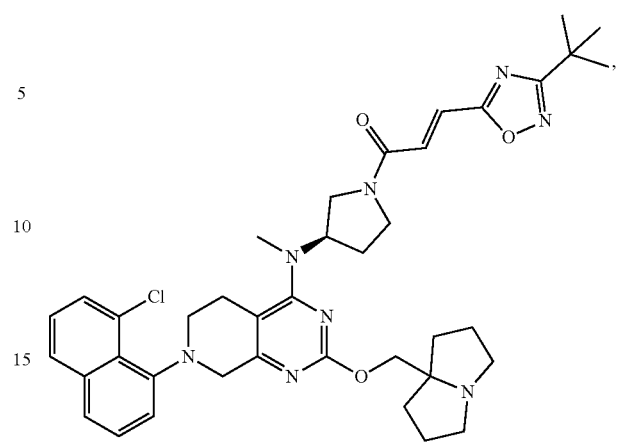
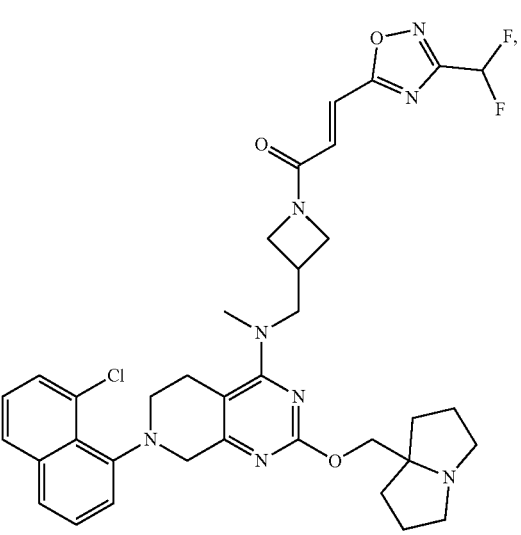
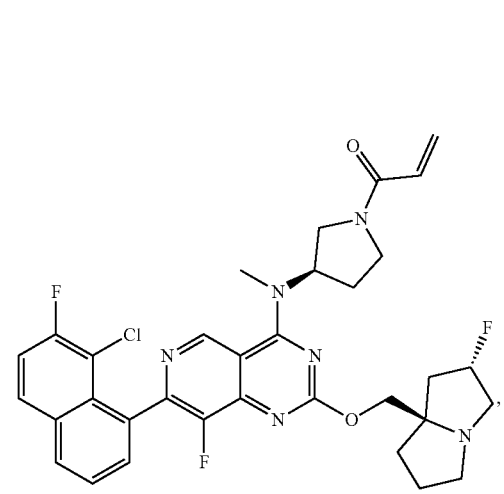

287
-continued
288
-continued
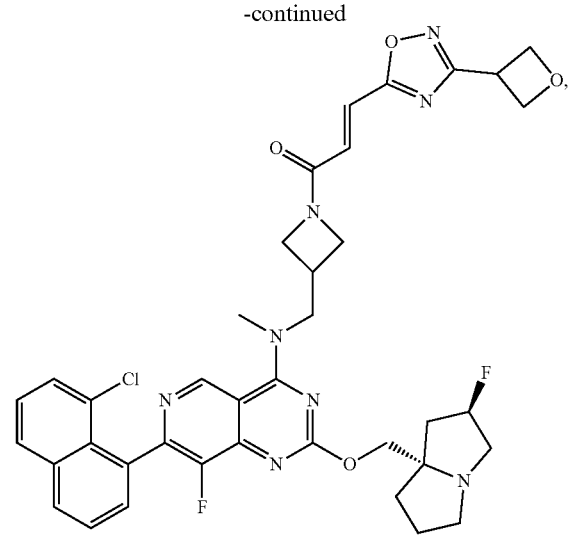
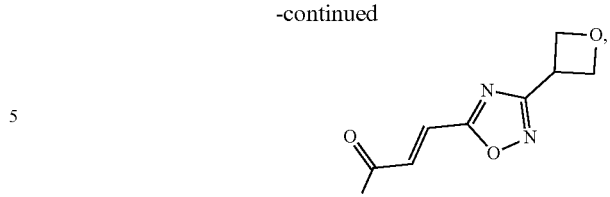
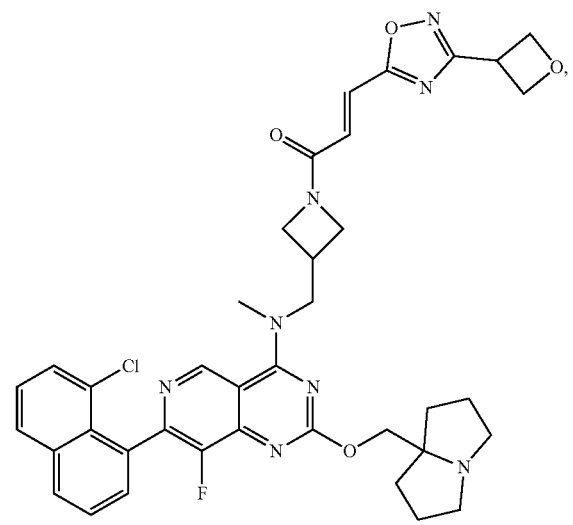
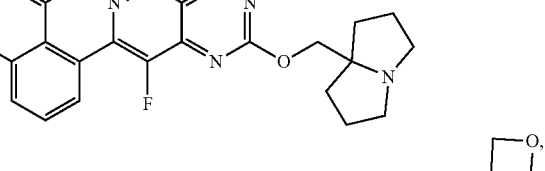
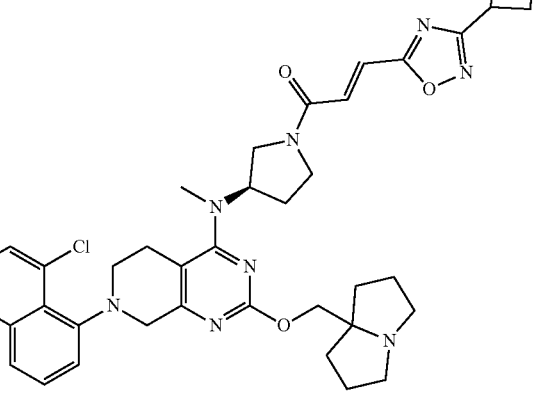
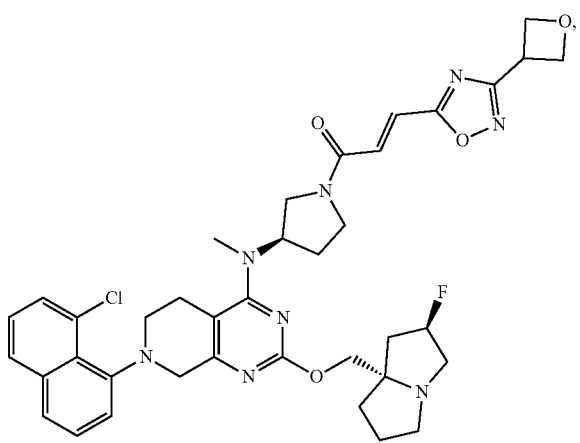
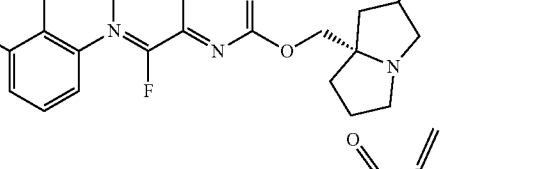
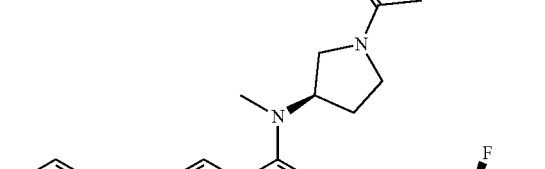
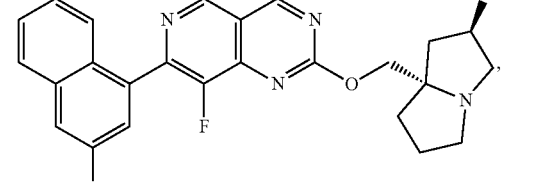

289
-continued
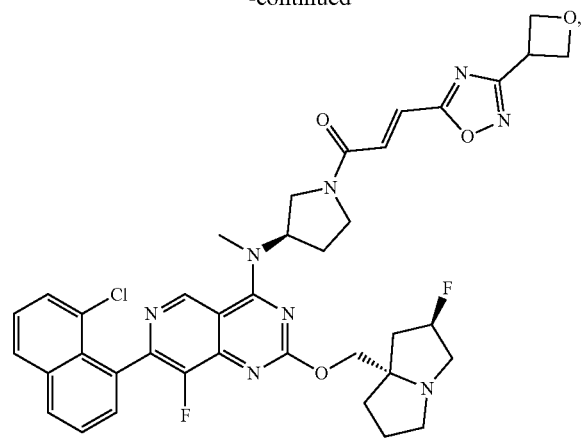
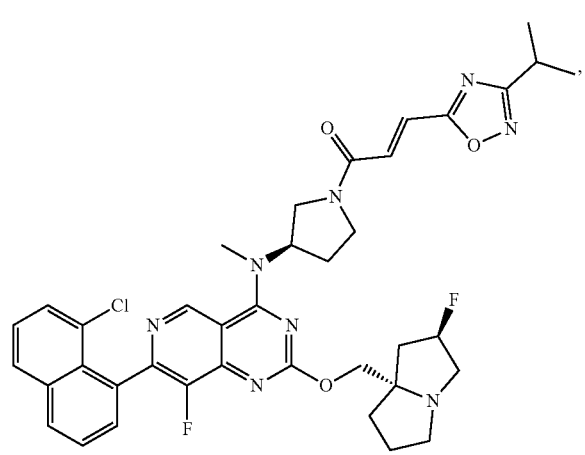
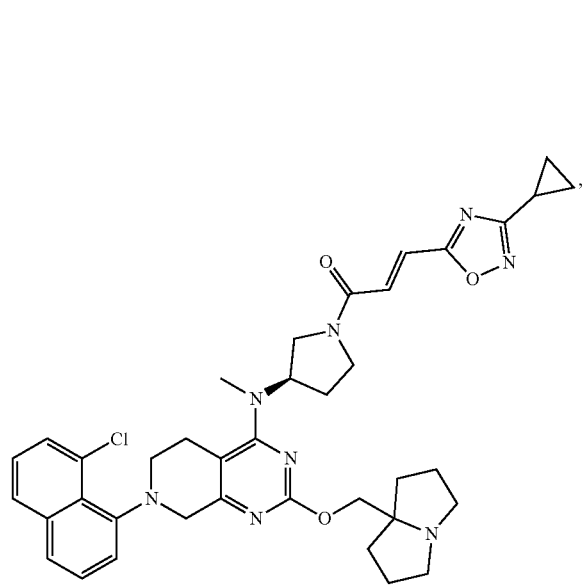
290
-continued
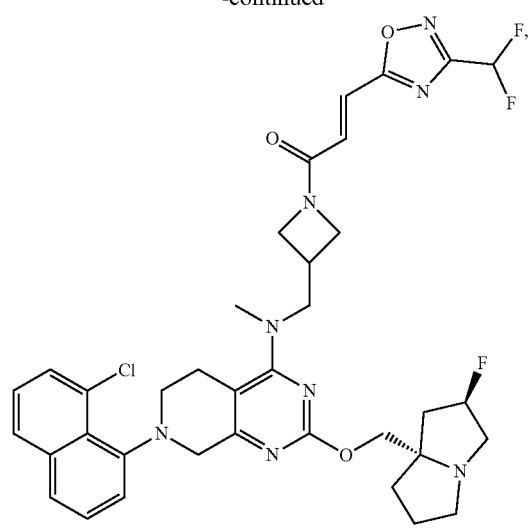
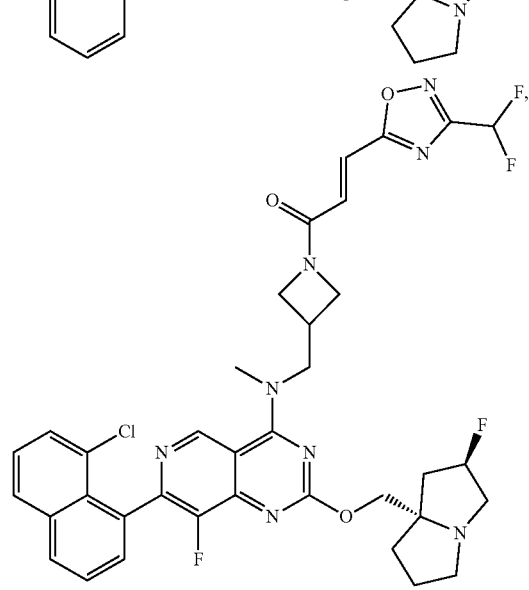
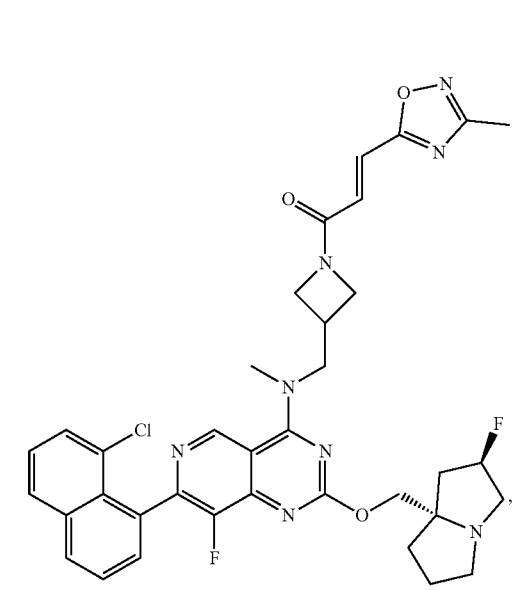

291
-continued
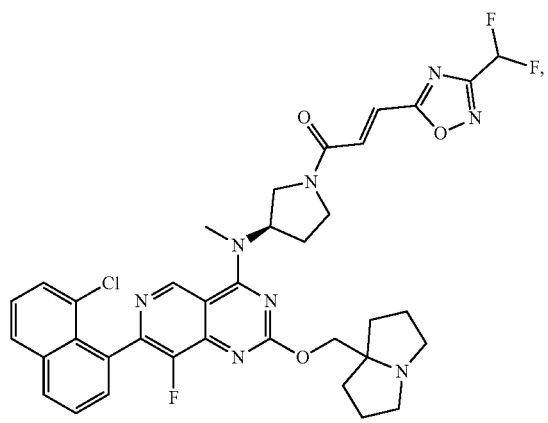
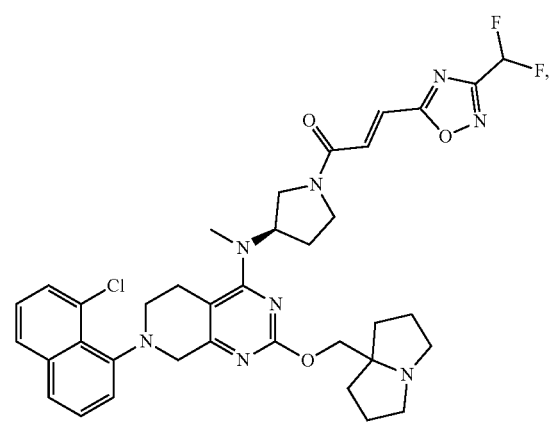
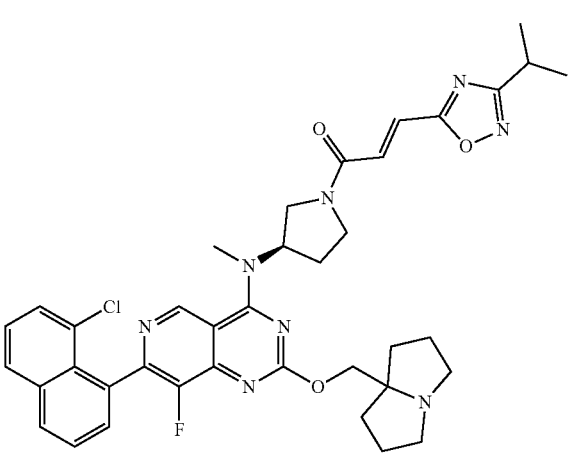
292
-continued
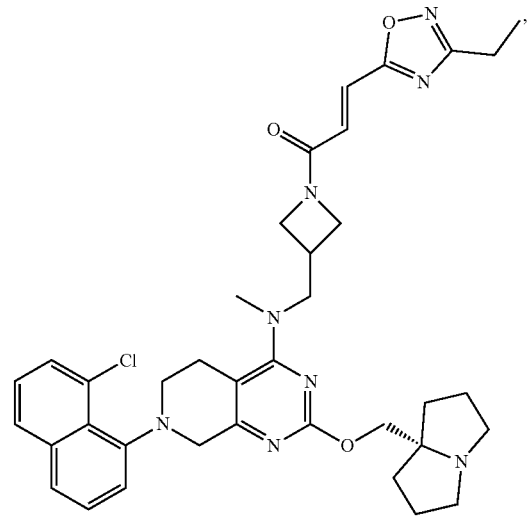
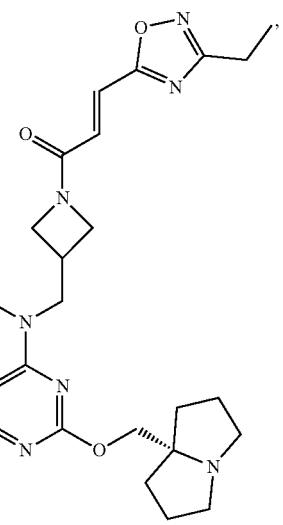
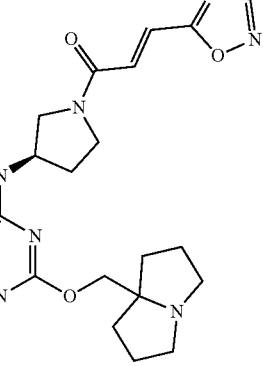

293
-continued
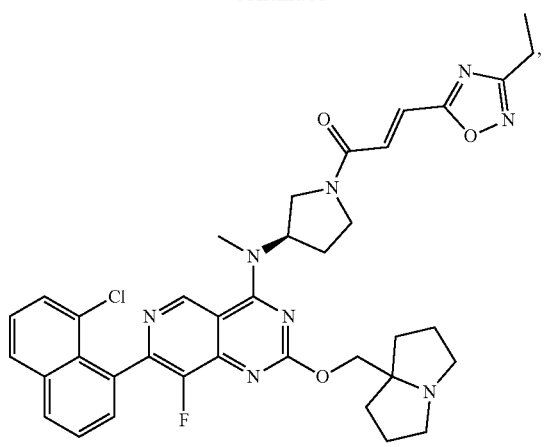
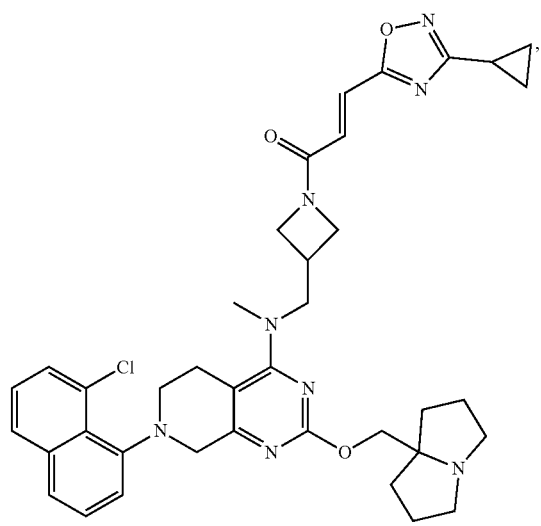
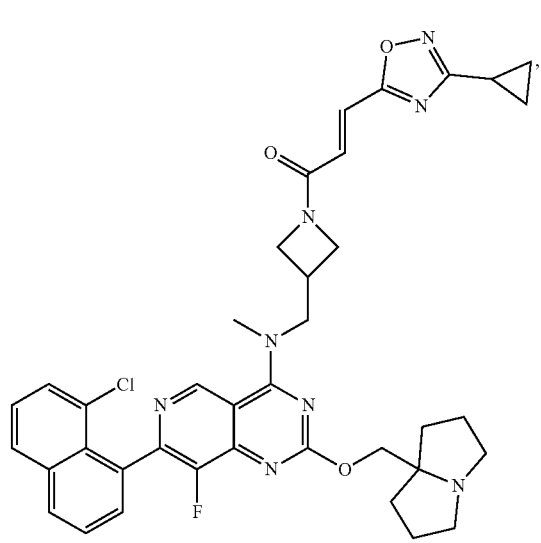
294
-continued
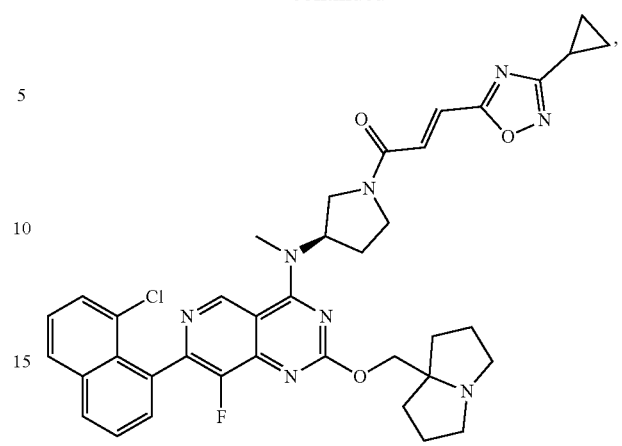
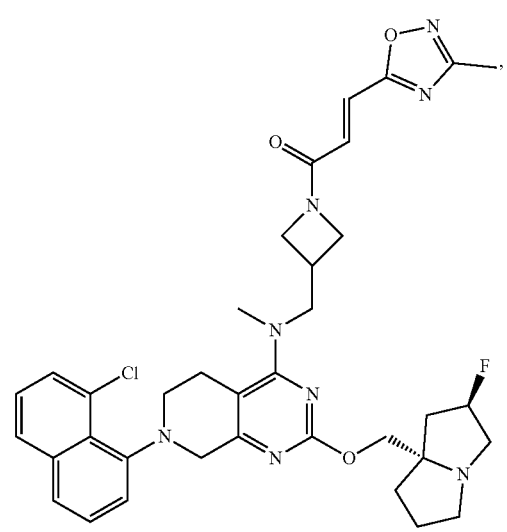

295
-continued
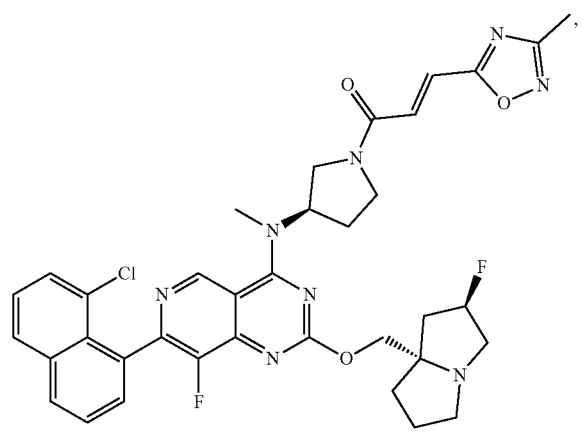
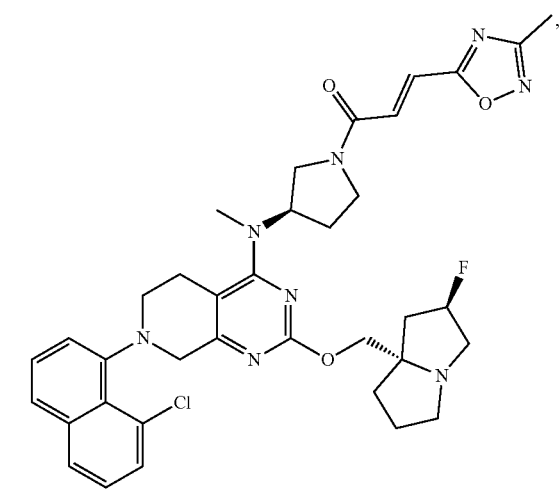
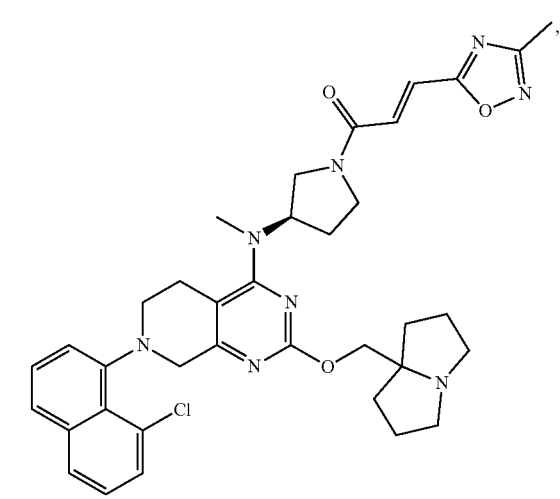 [SMILES: Cc1noc(/C=C/C(=O)N2CC[C@@H](N(C)c3nc(OCC45CCCN4CCC5)nc4c3CCN(c3cccc5cccc(Cl)c35)C4)C2)n1]
296
-continued
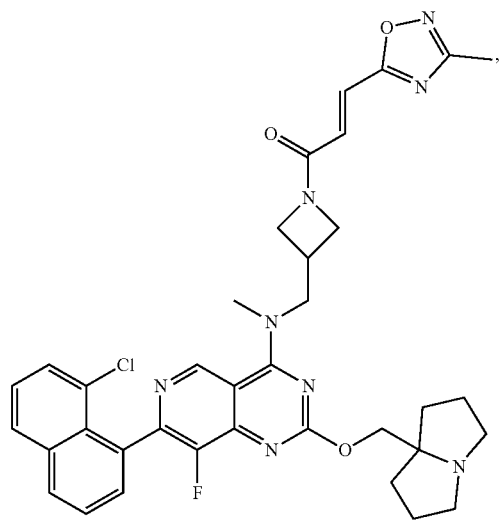
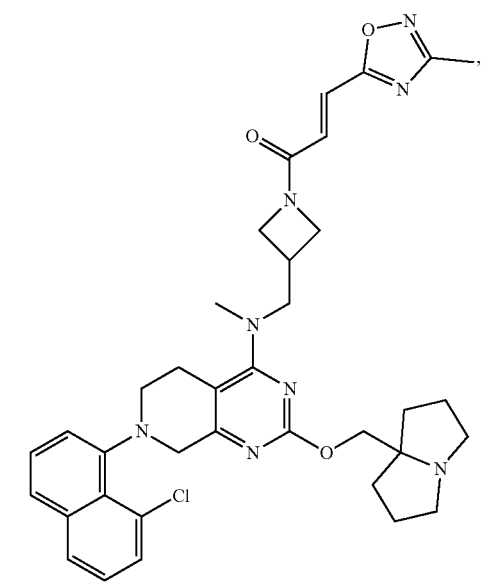
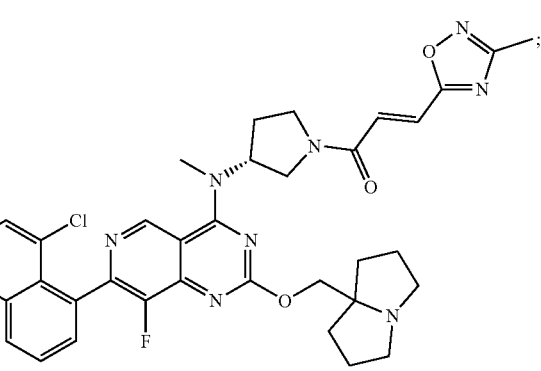

297
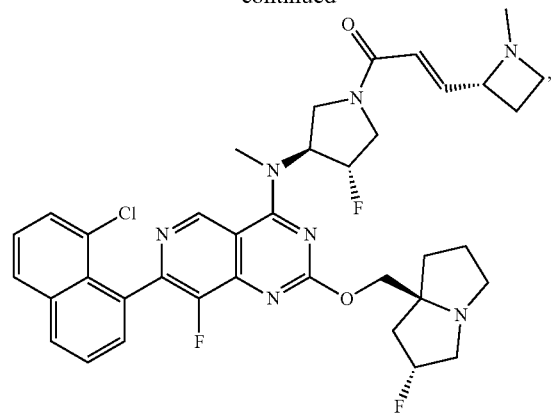
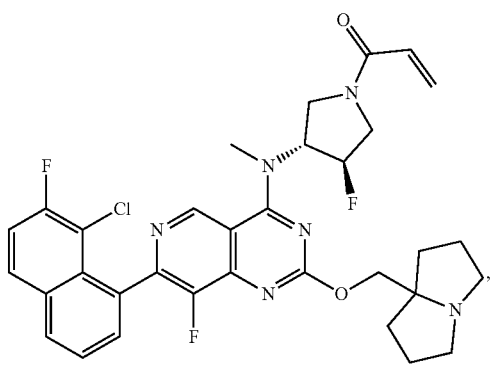
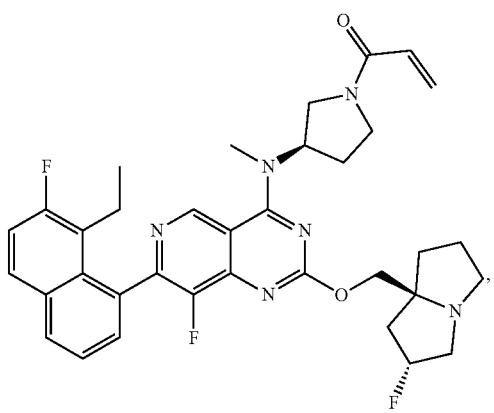
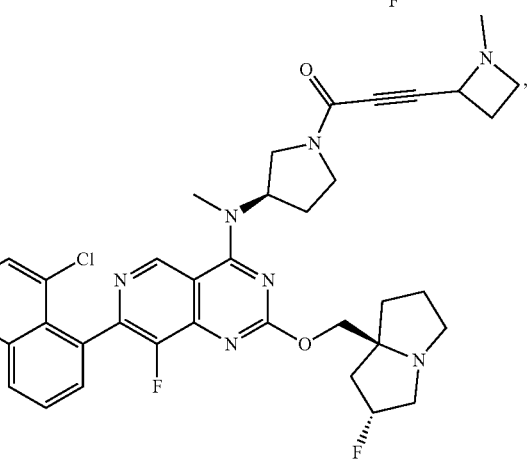
298
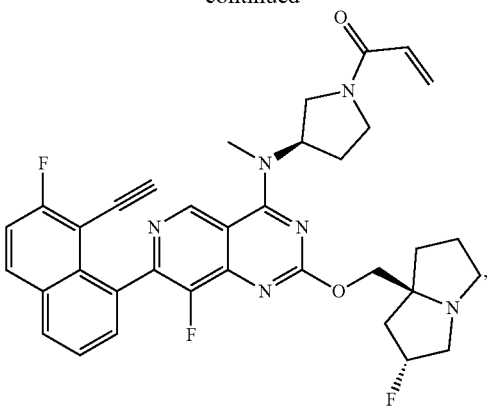
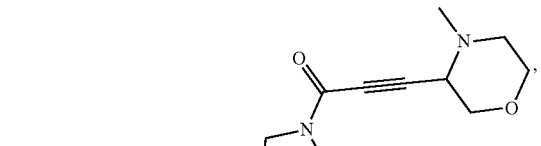
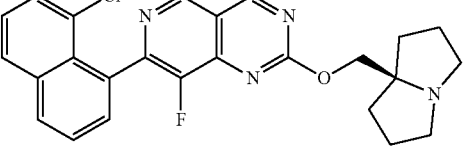
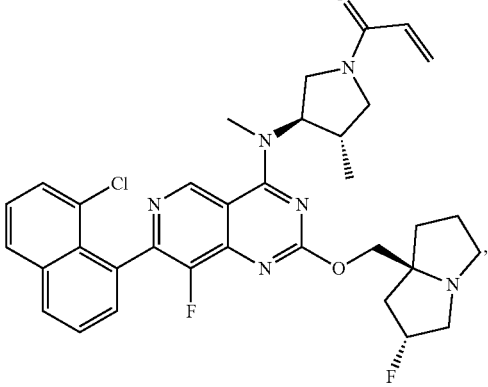
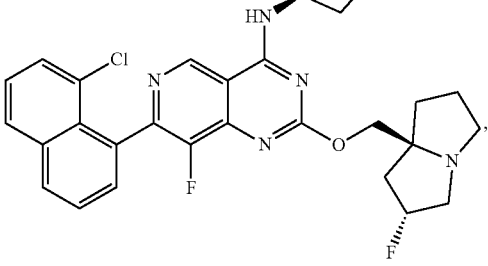

299
-continued
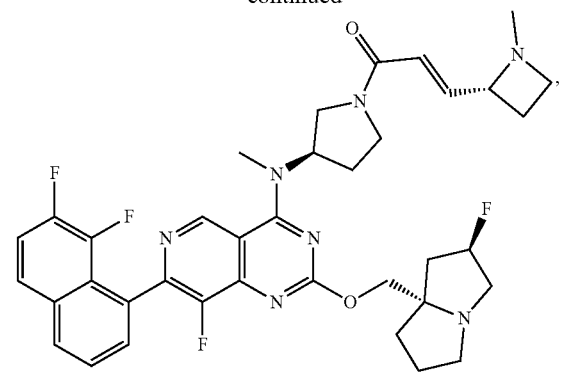
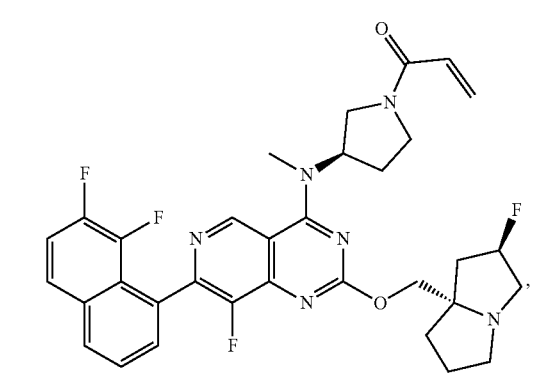
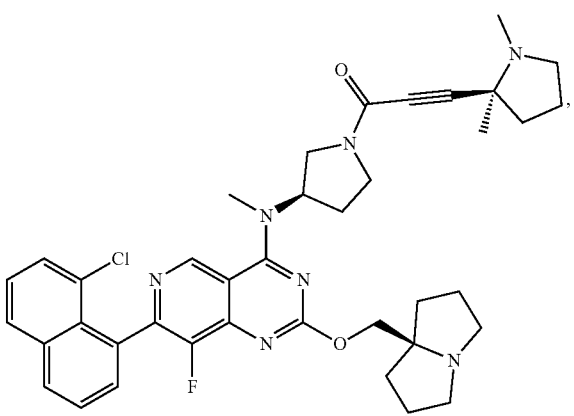
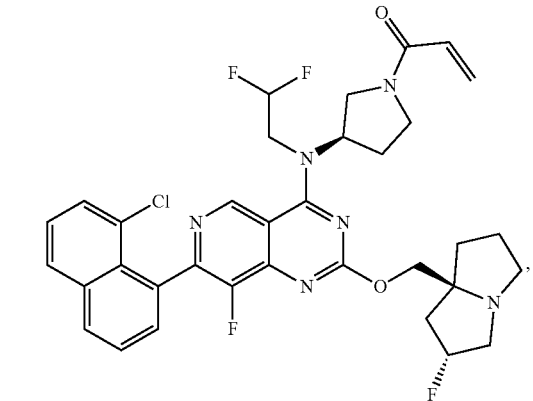
300
-continued
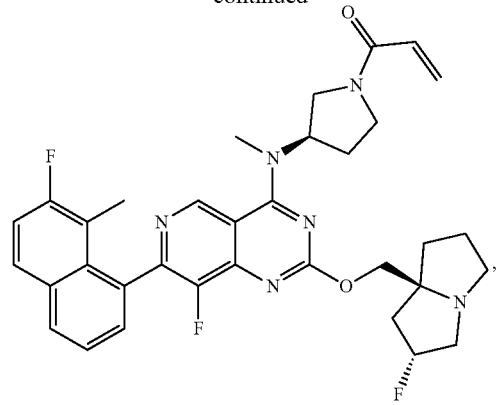
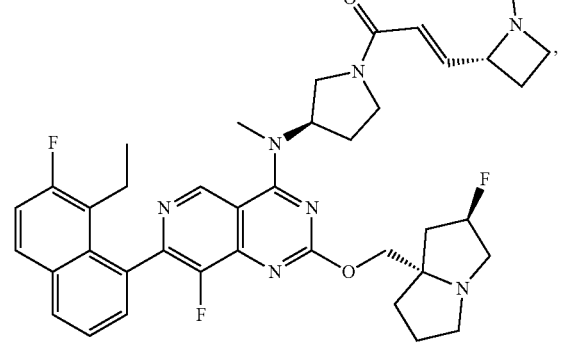
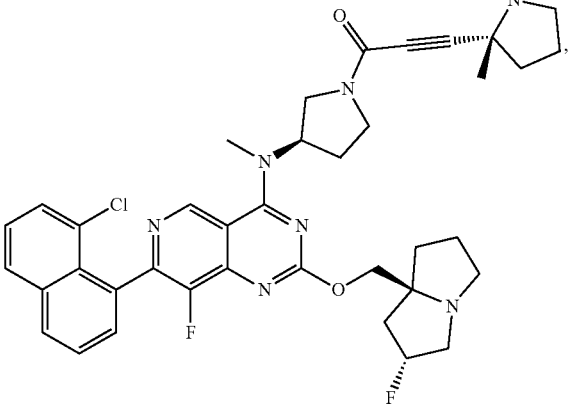
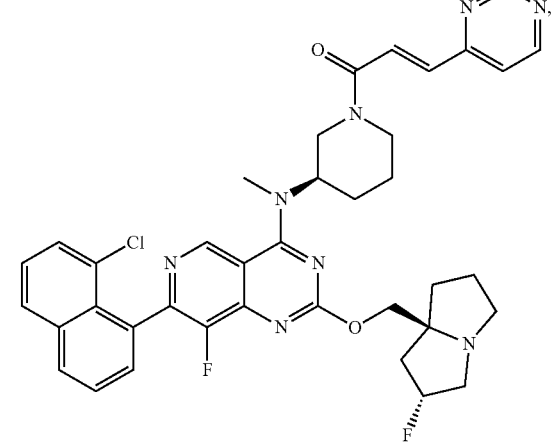

301
-continued
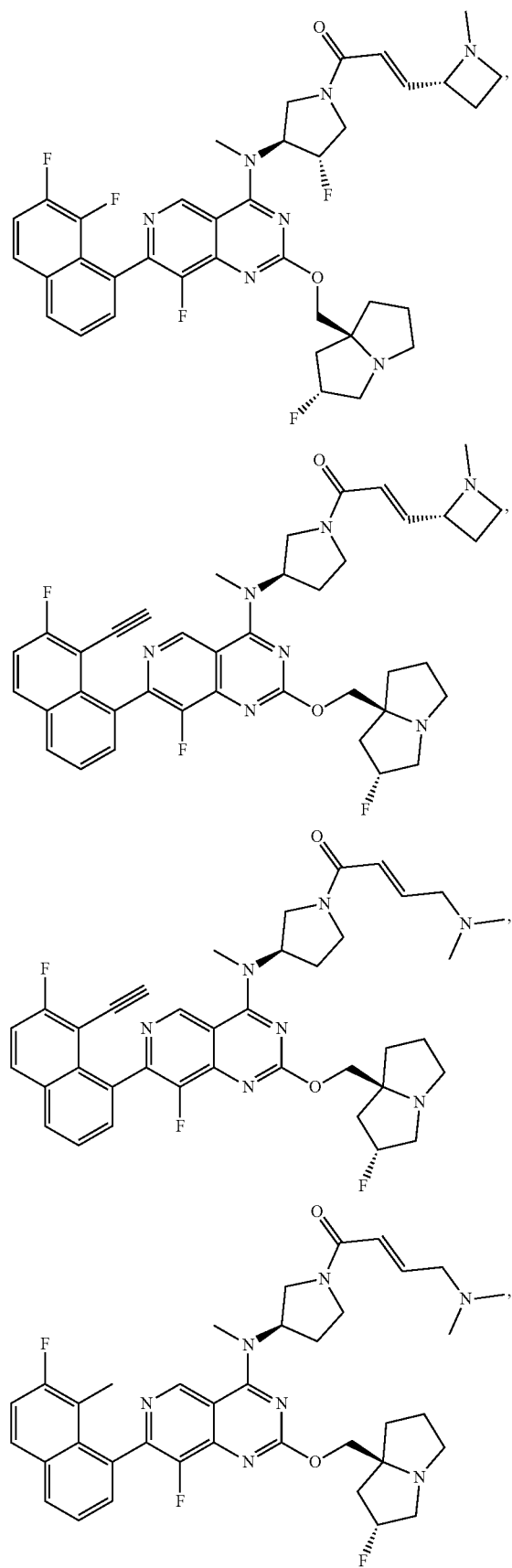
302
-continued
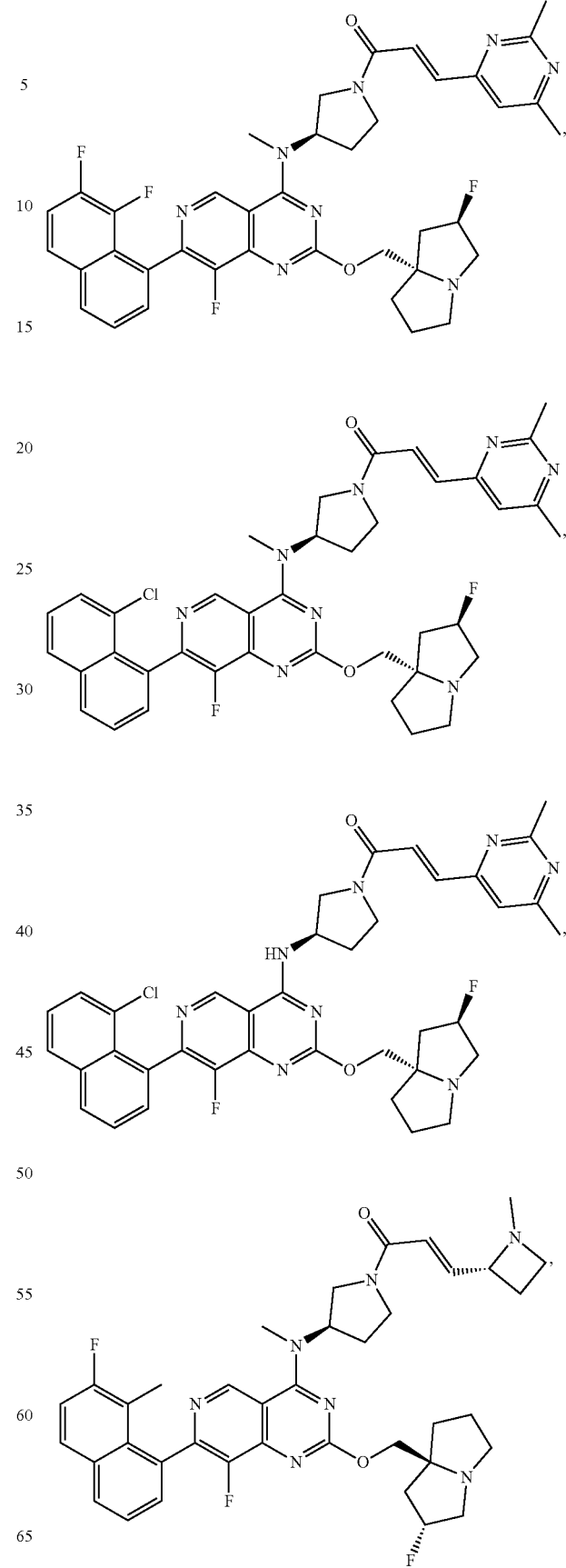

303
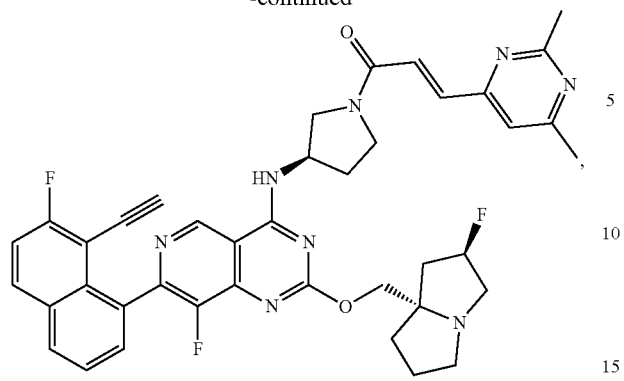
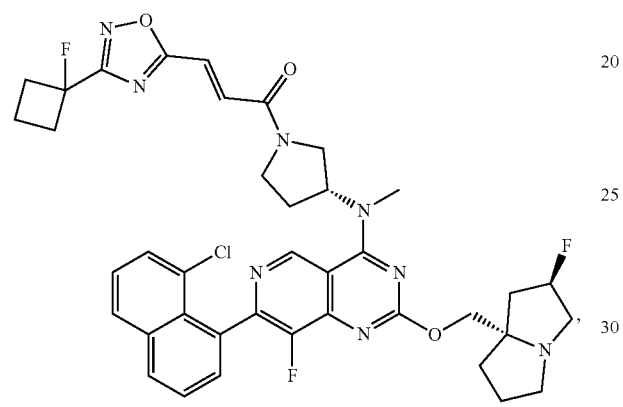
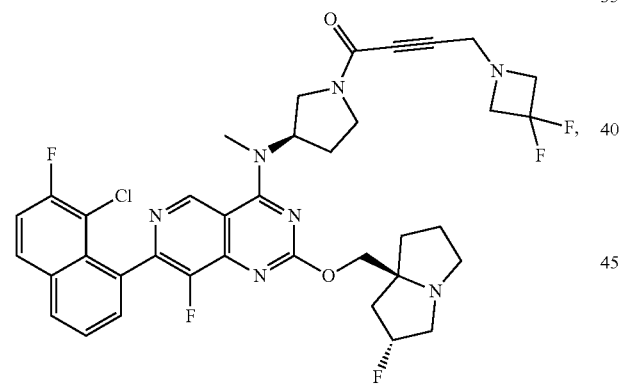
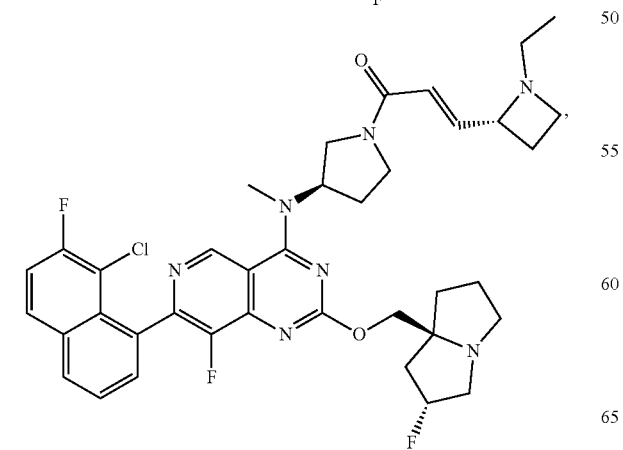
304
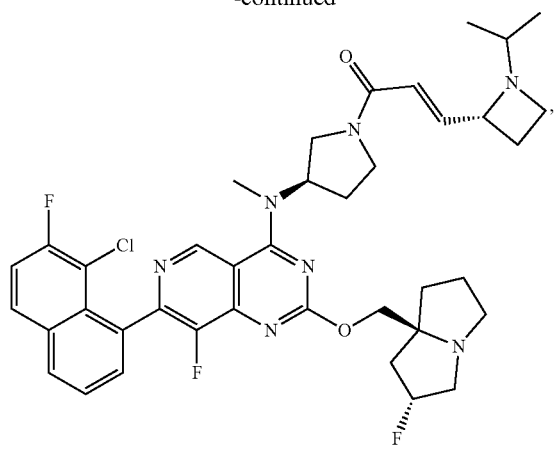
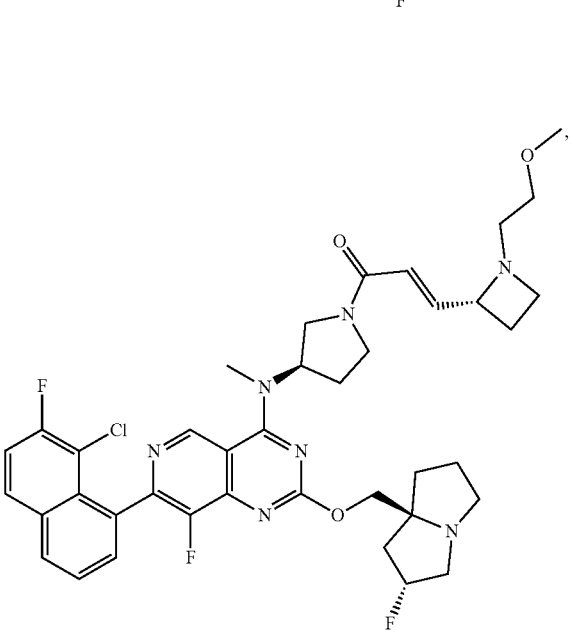
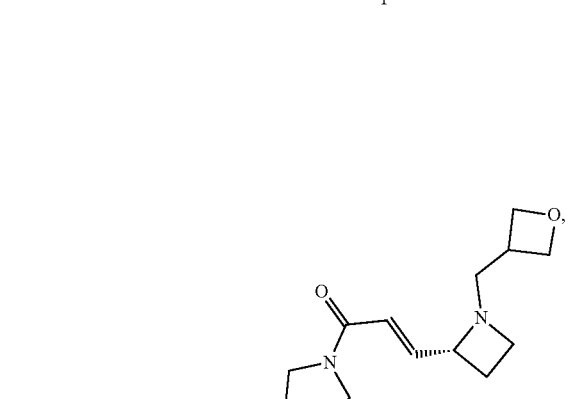
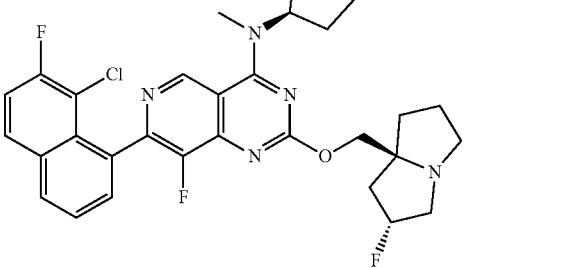

305
-continued
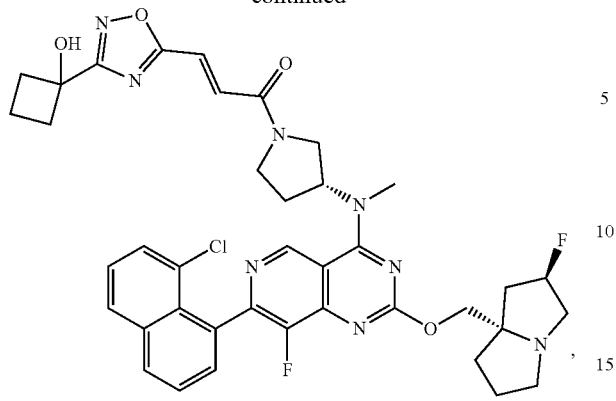
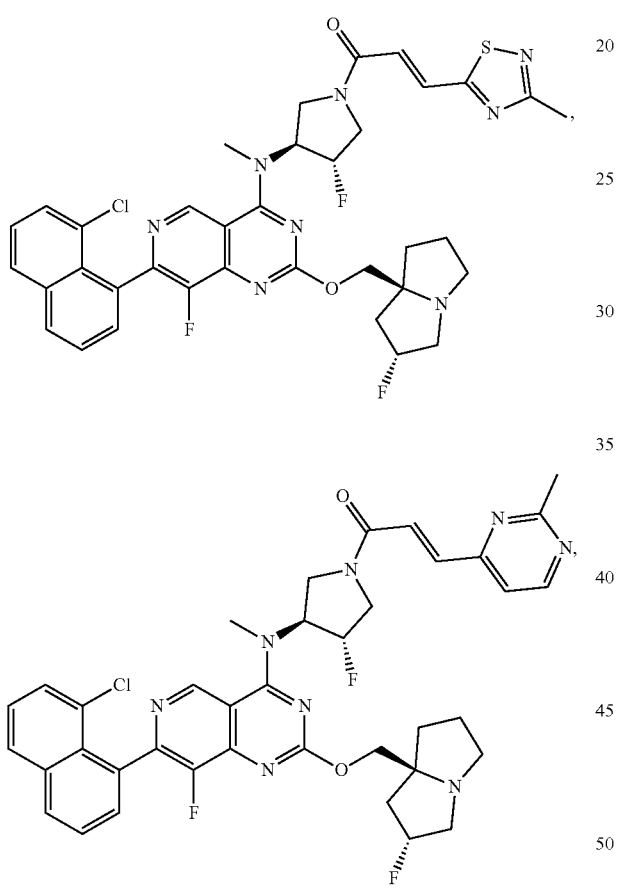
306
-continued
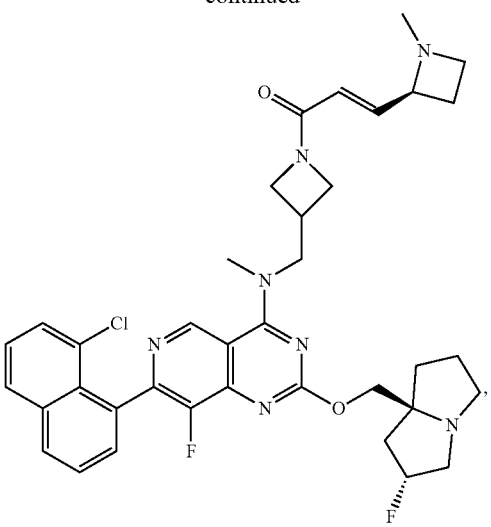
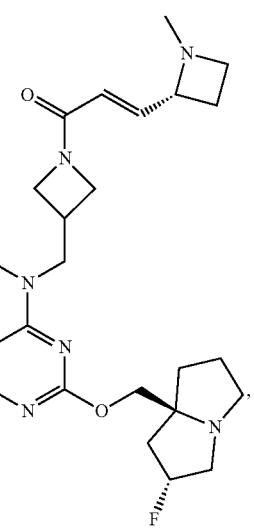
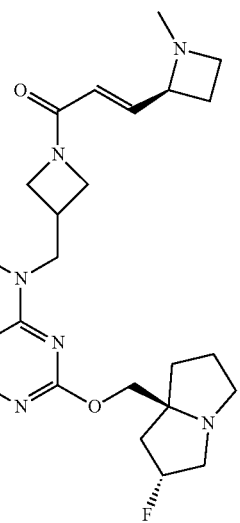

307
-continued
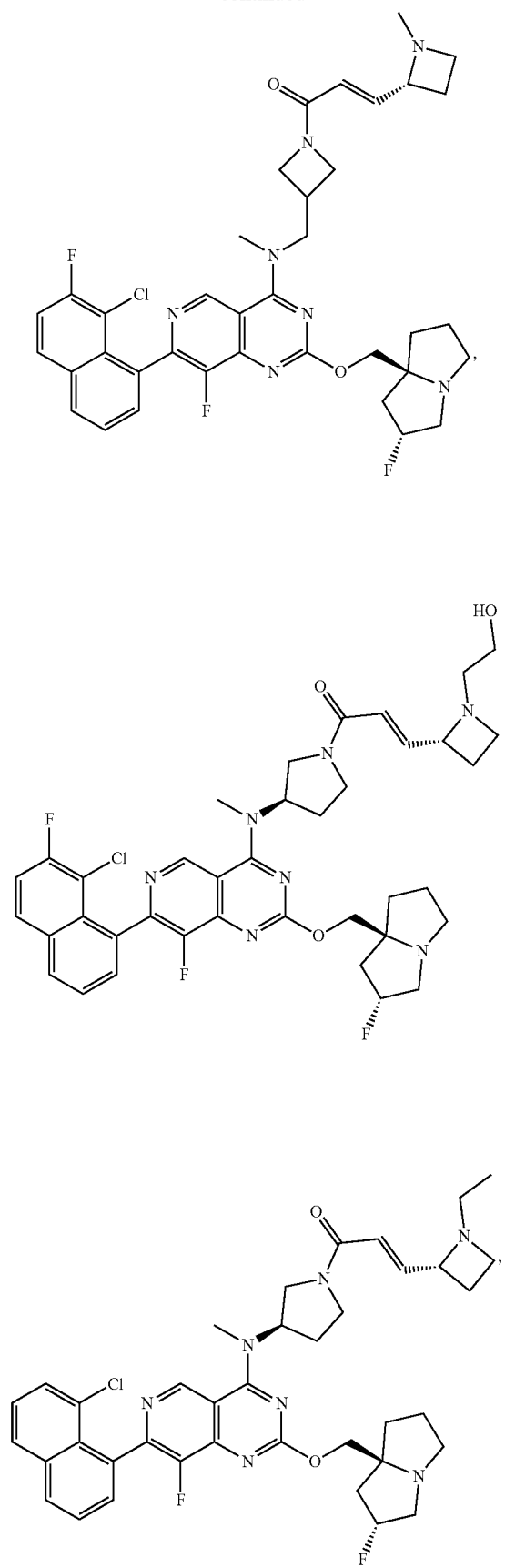
308
-continued
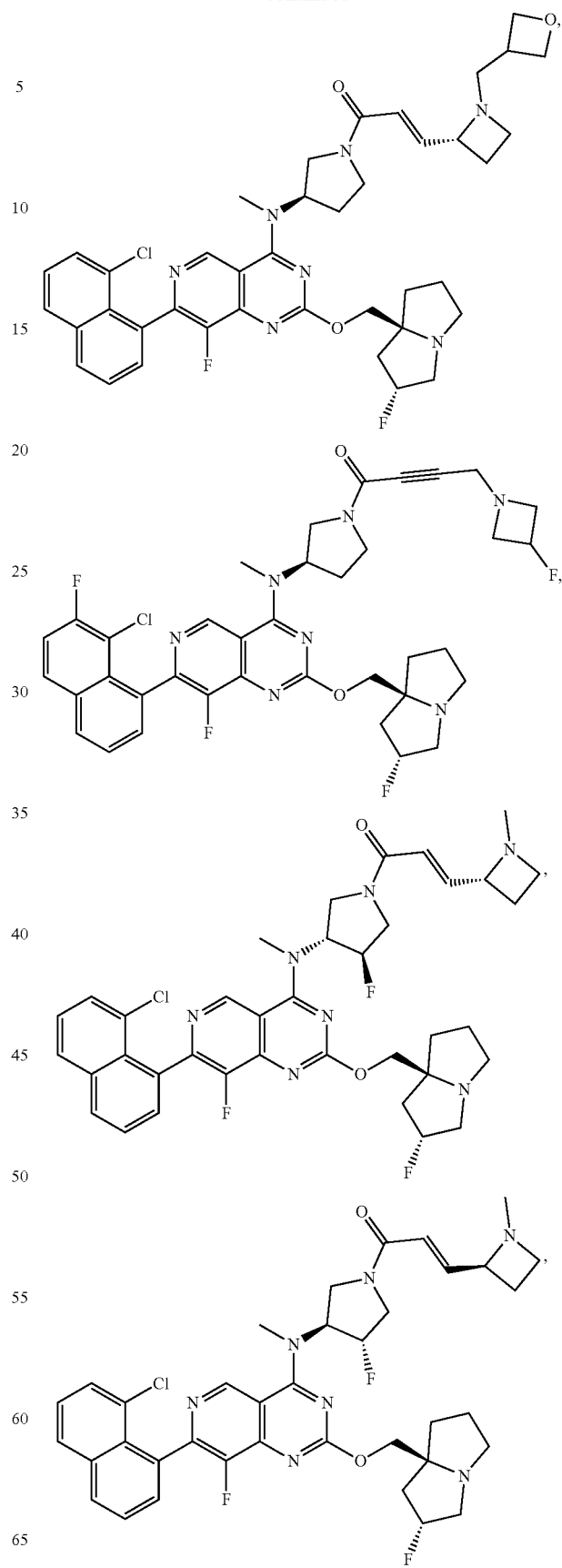

309
-continued
310
-continued
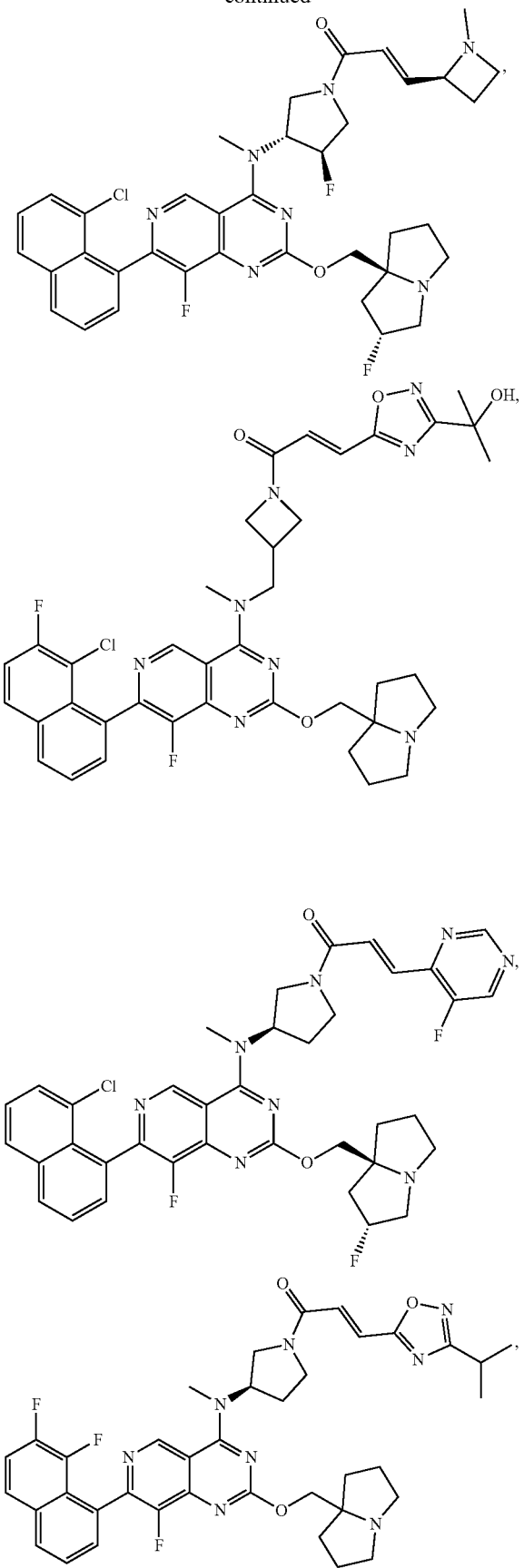
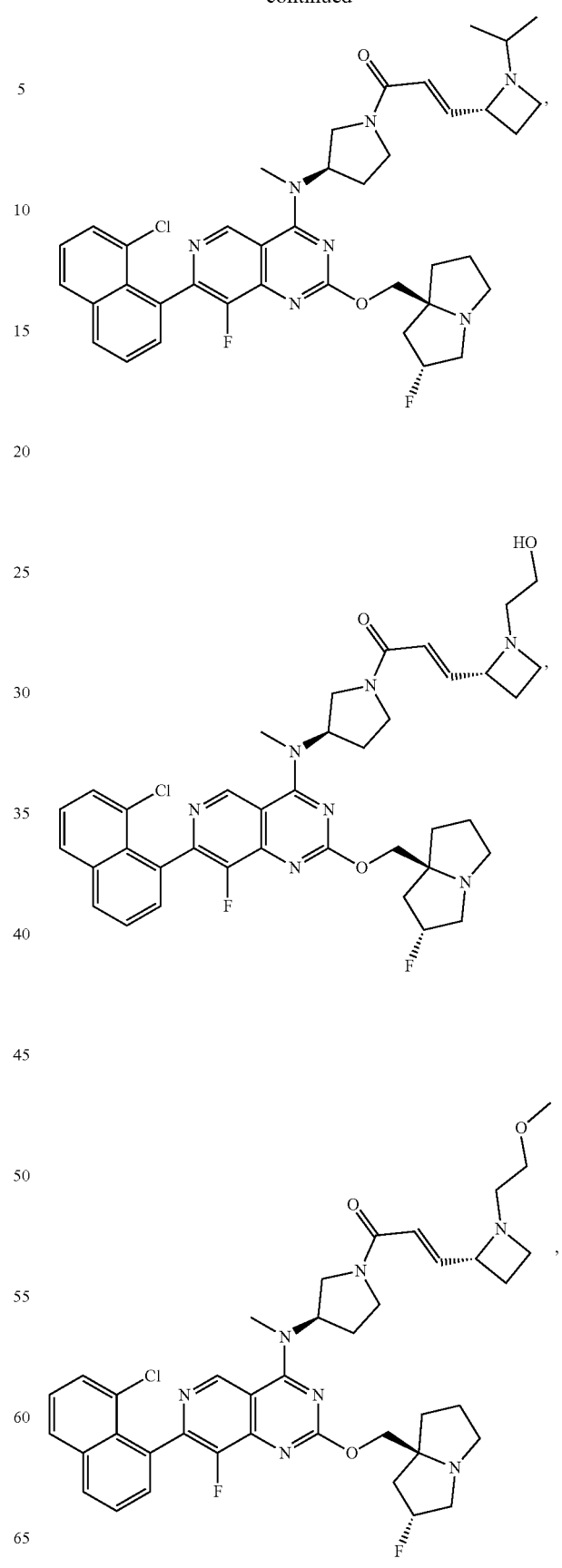

311
-continued
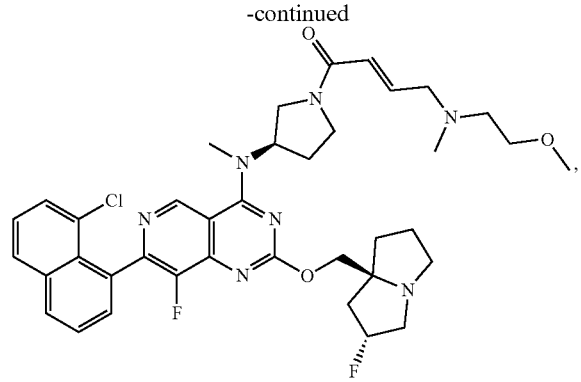
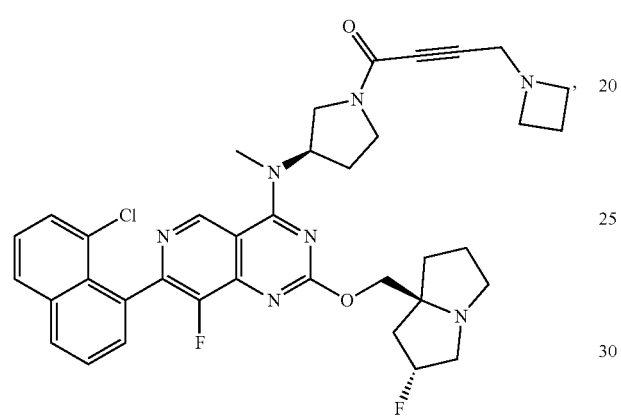
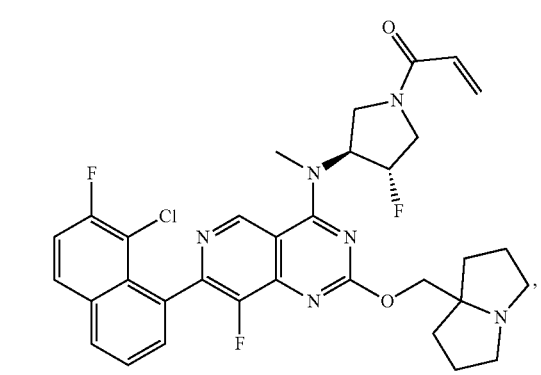
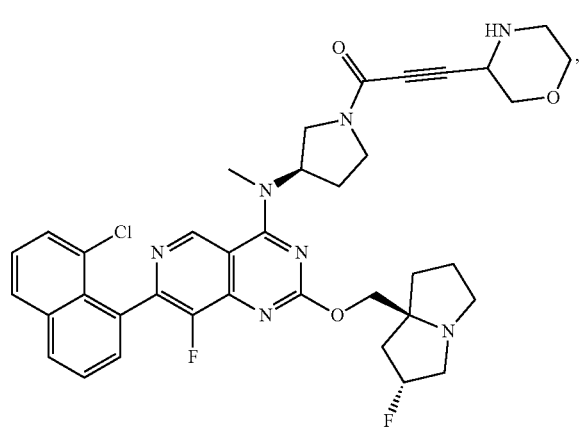
312
-continued
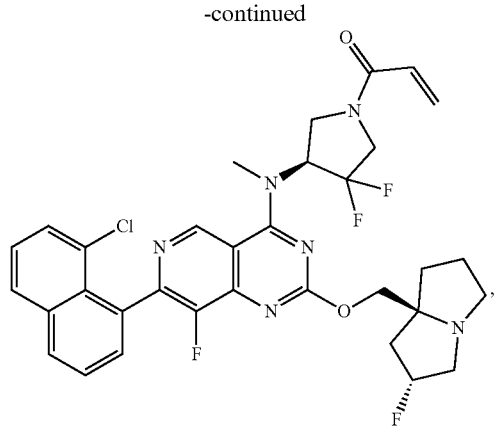
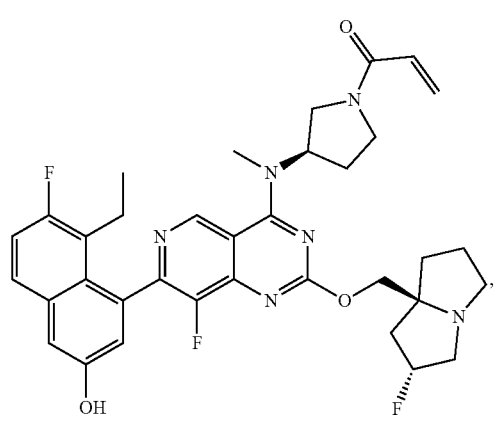
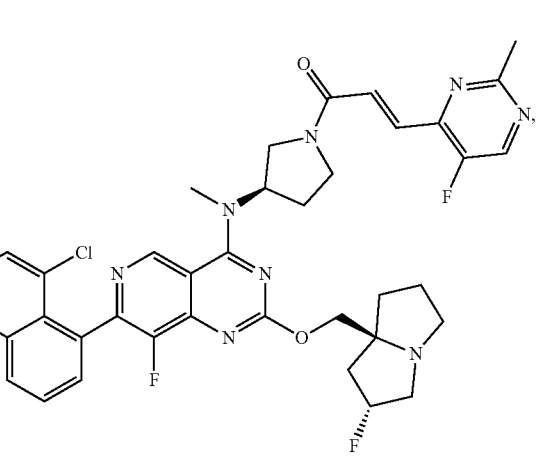
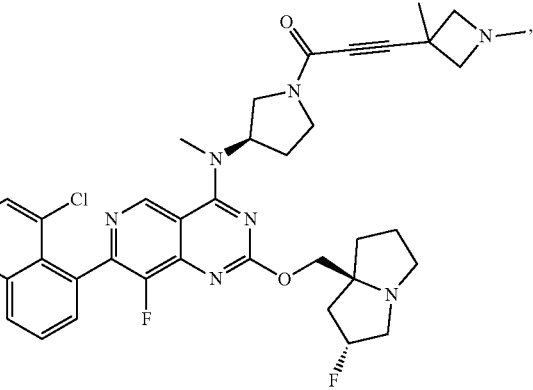

313
-continued
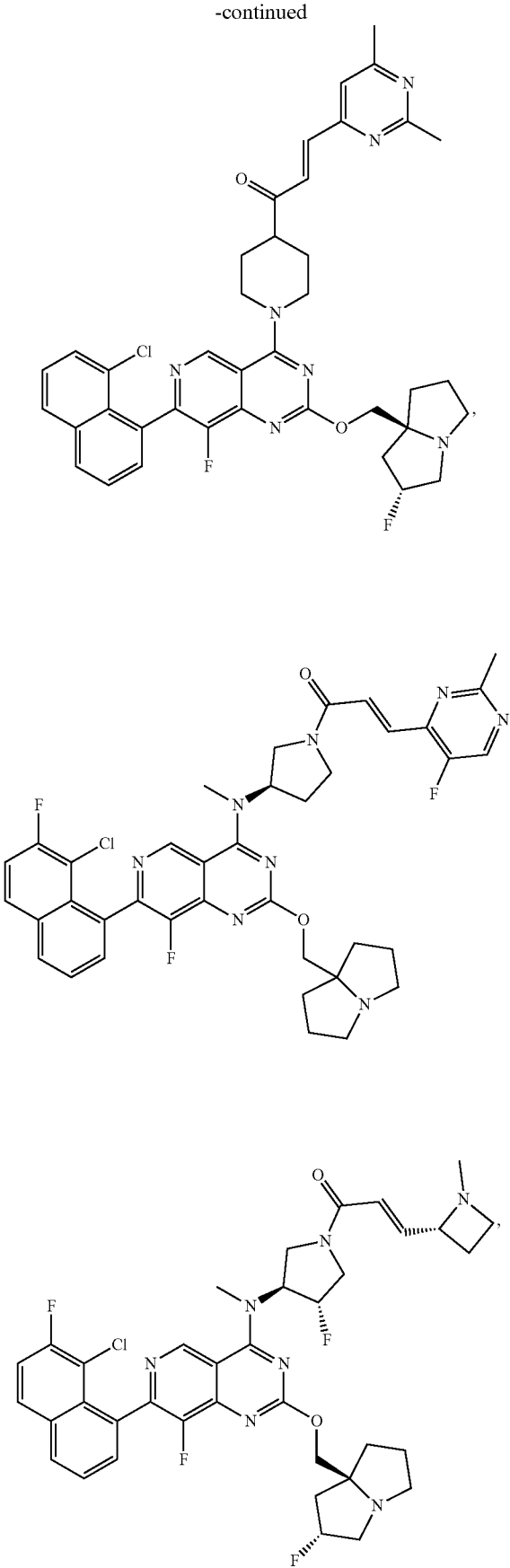
314
-continued
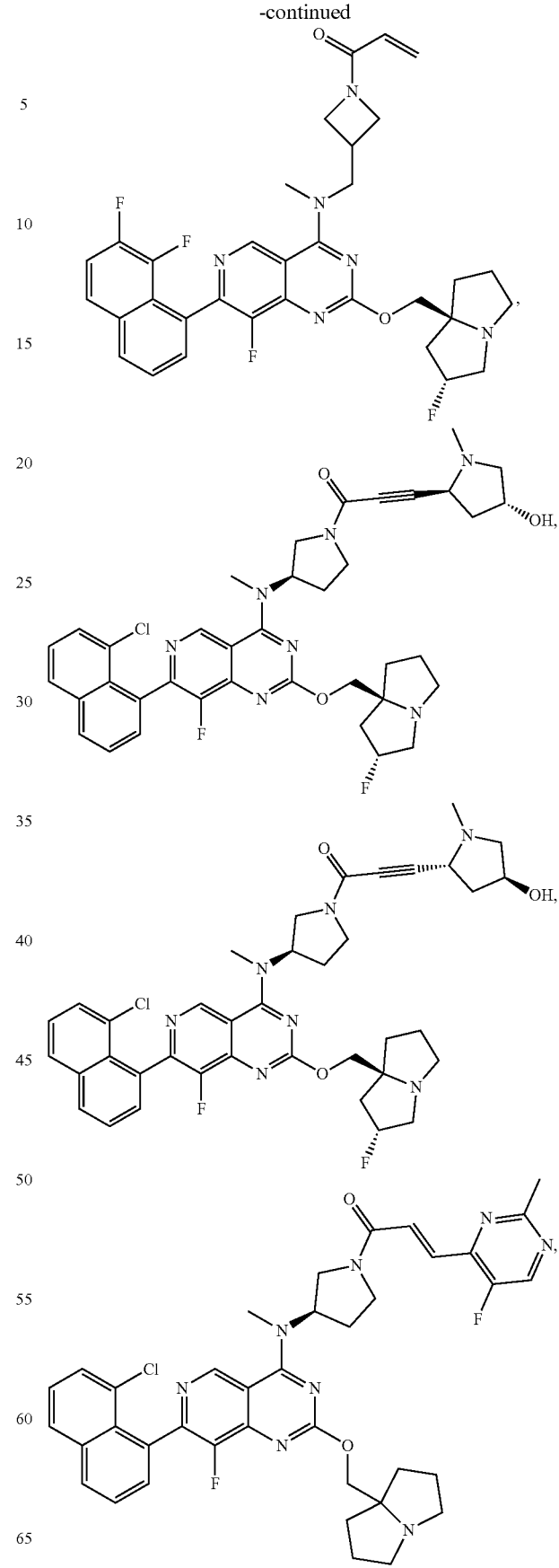

315
-continued
316
-continued
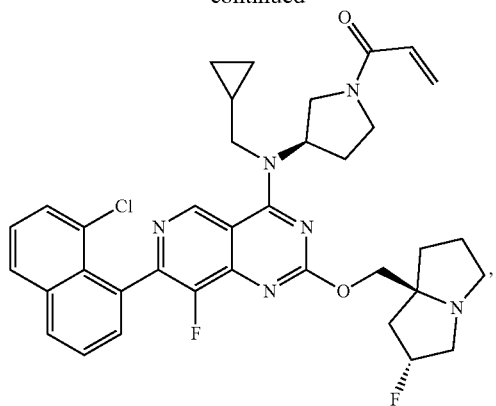
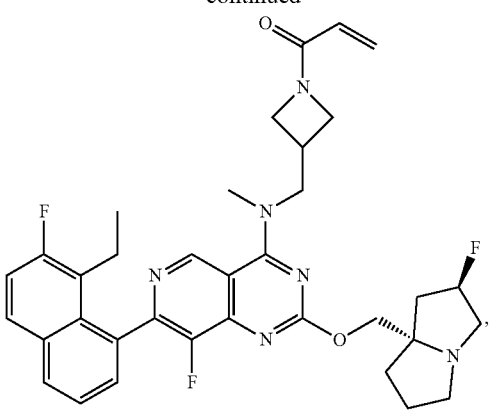

317
-continued
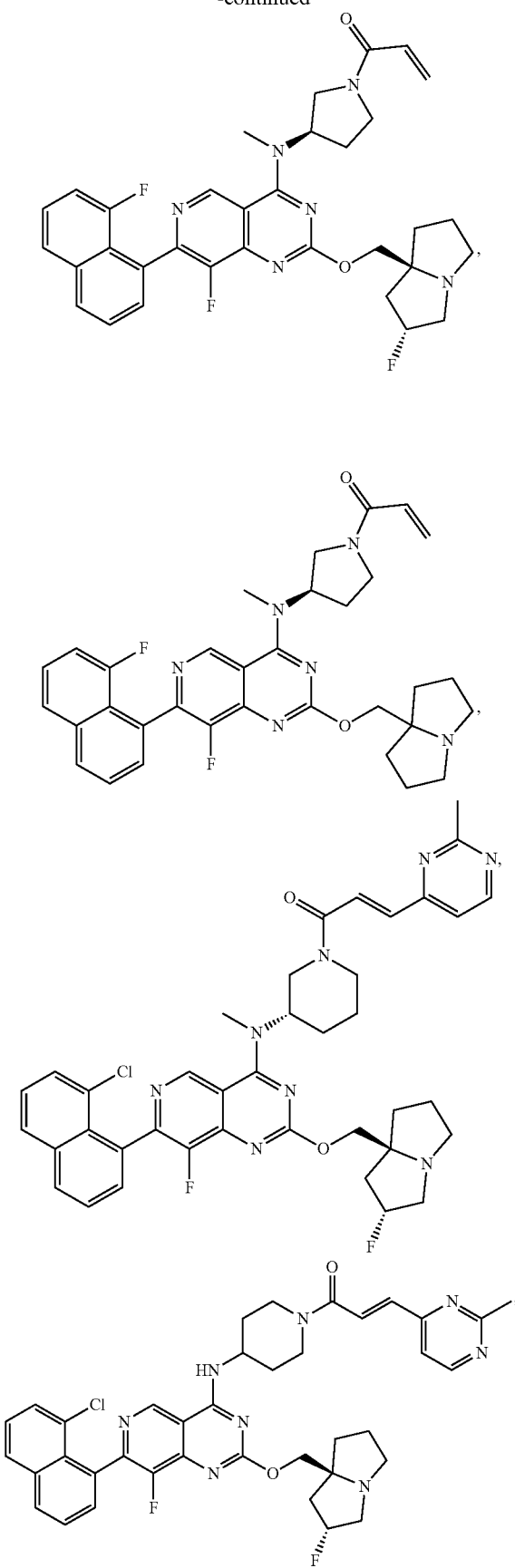
318
-continued
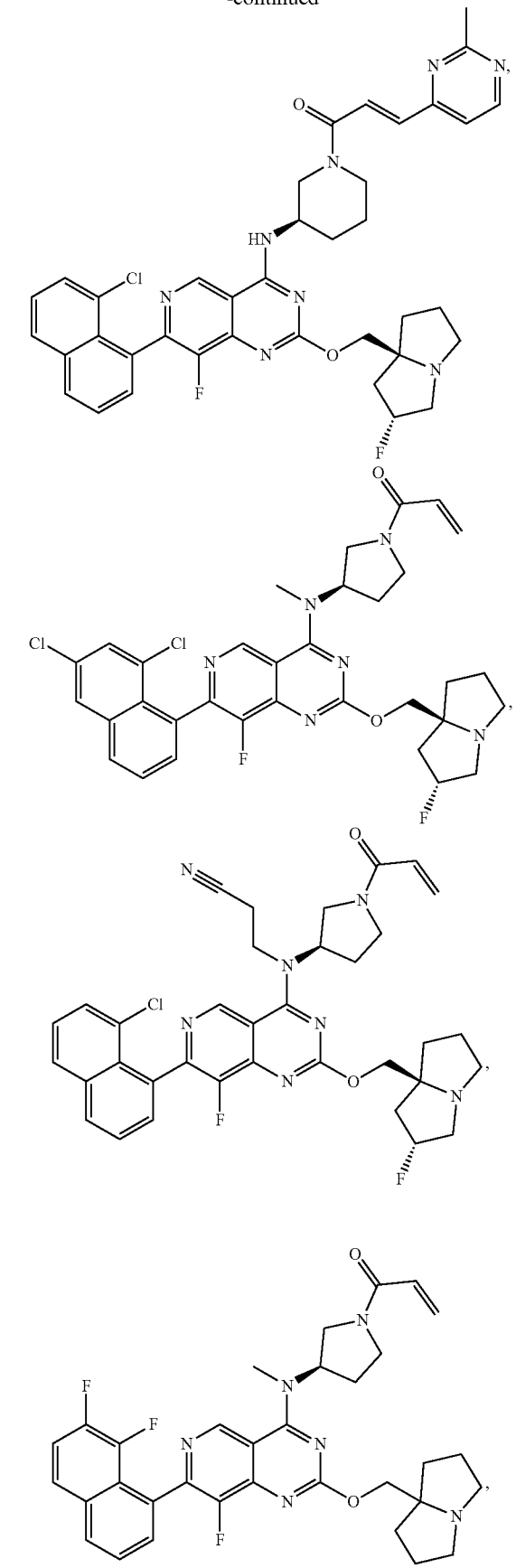

319
-continued
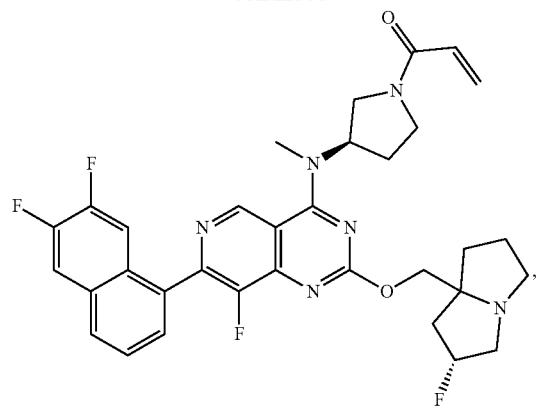
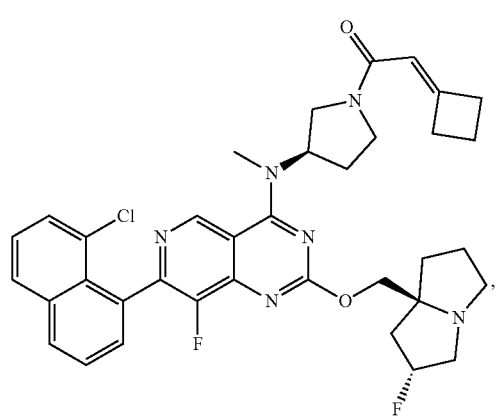
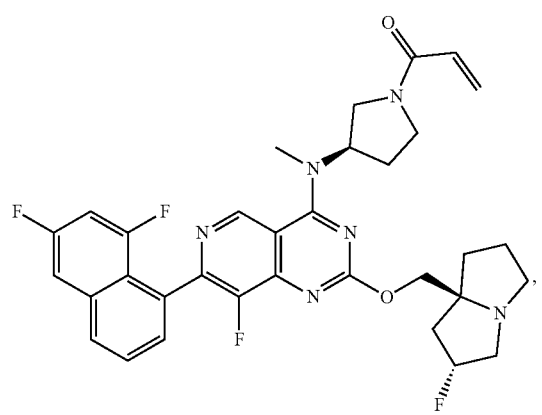
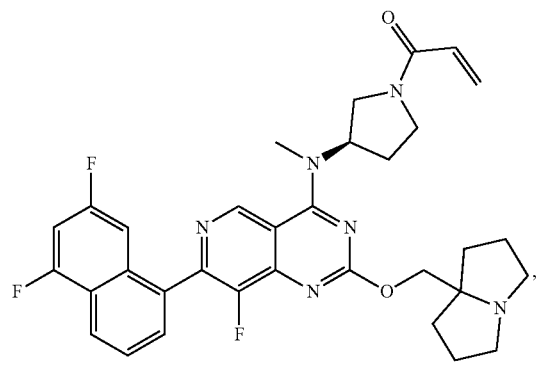
320
-continued
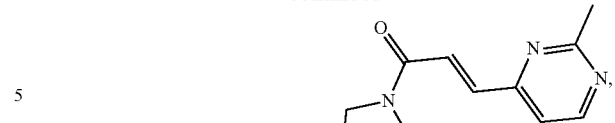
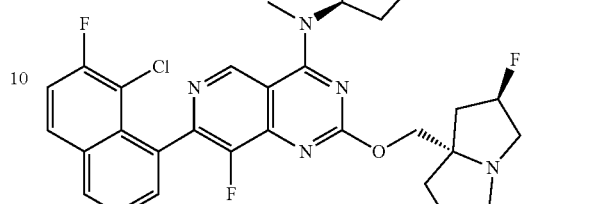
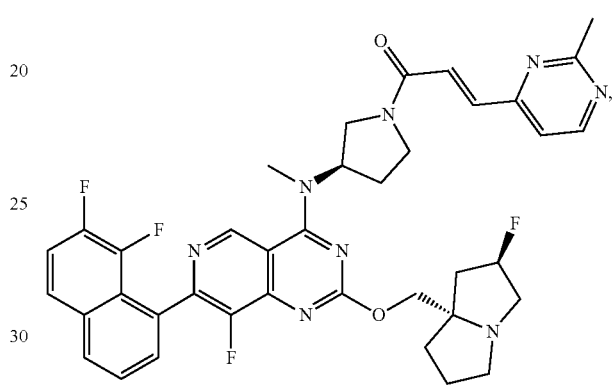
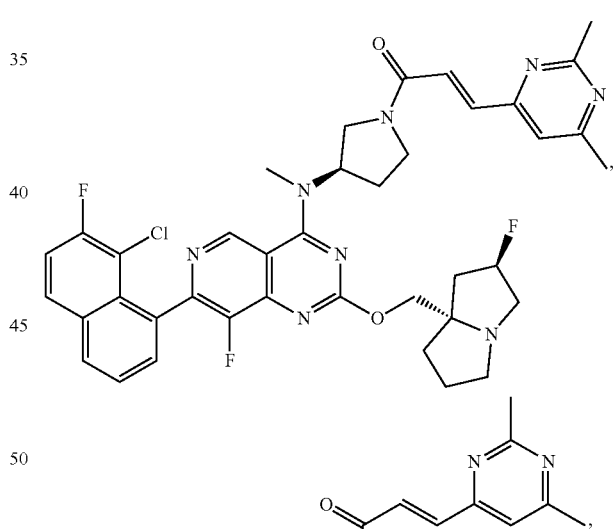
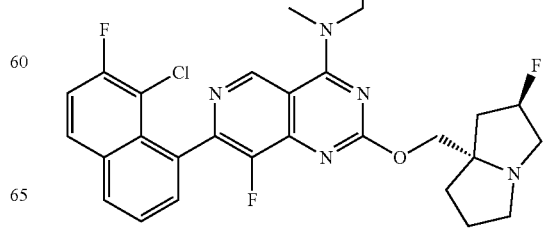

321
-continued
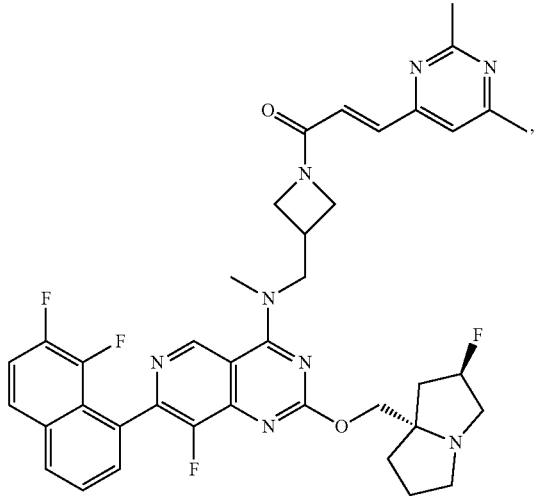
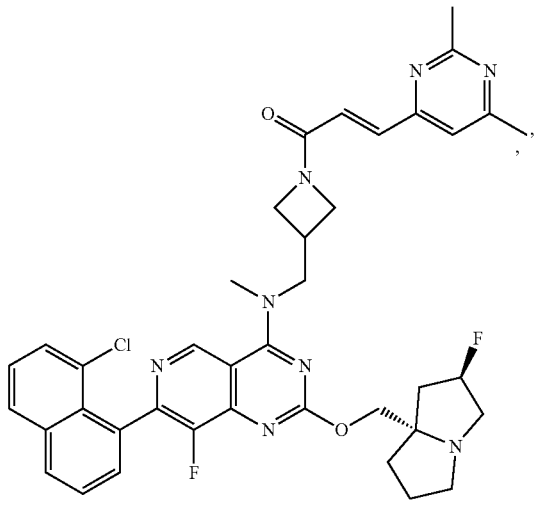
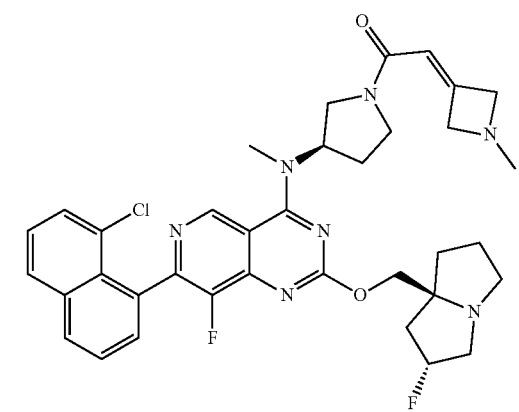 [SMILES: CN1CC(=CC(=O)N2CC[C@@H](N(C)c3nc(OC[C@@]45CCCN4C[C@H](F)C5)nc4c(F)c(-c5cccc6cccc(Cl)c56)ncc34)C2)C1]
322
-continued
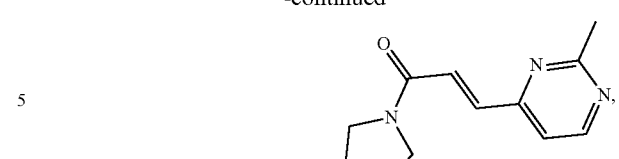
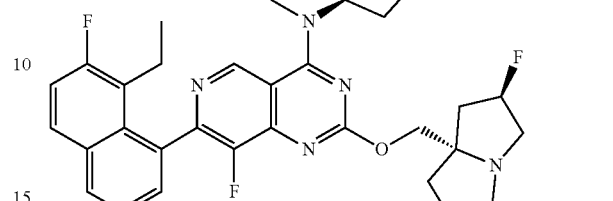

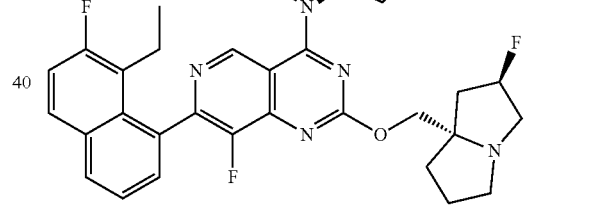
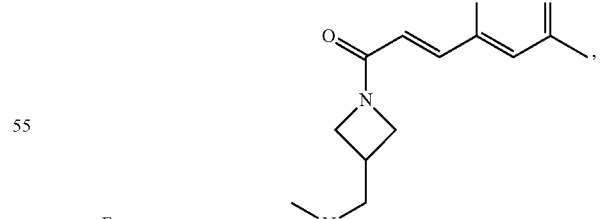
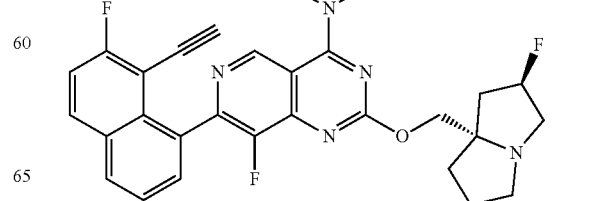

323
-continued
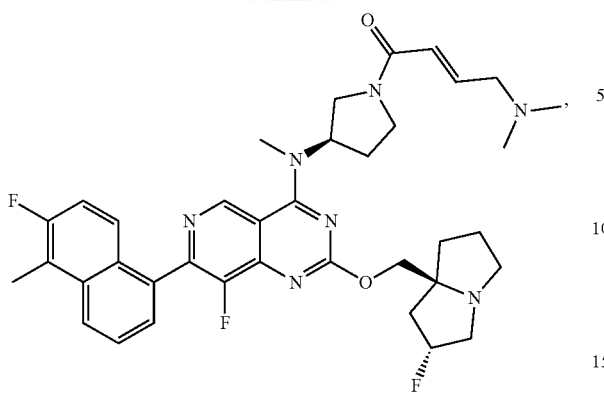
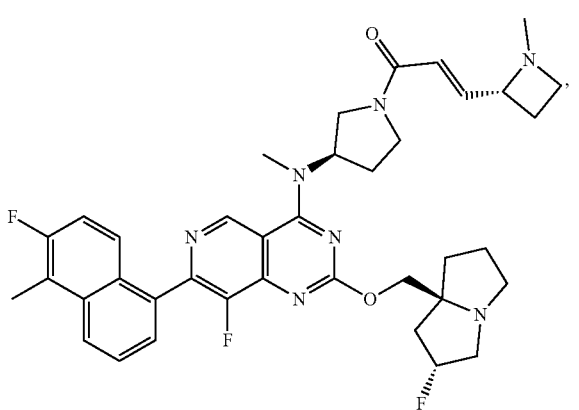
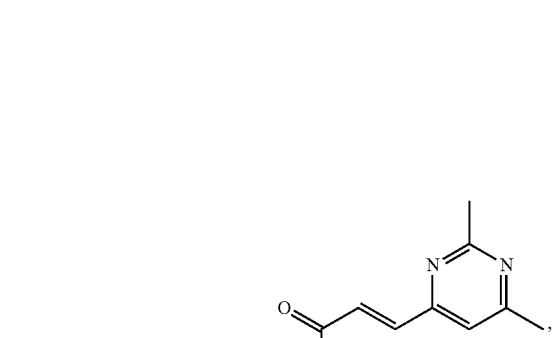
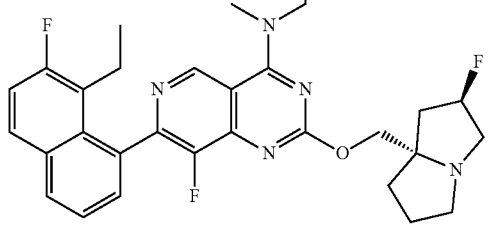
324
-continued
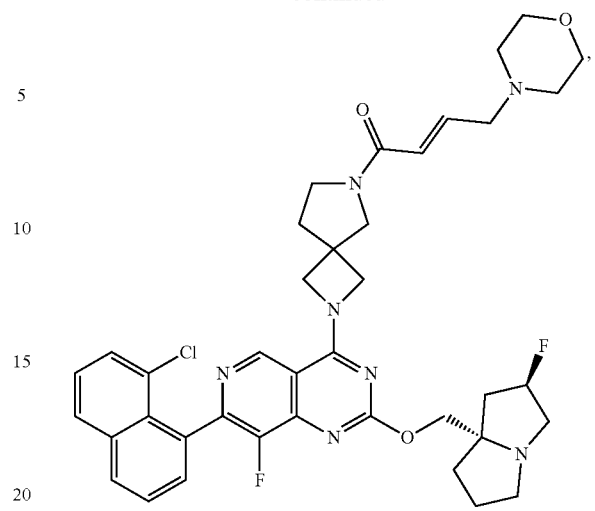
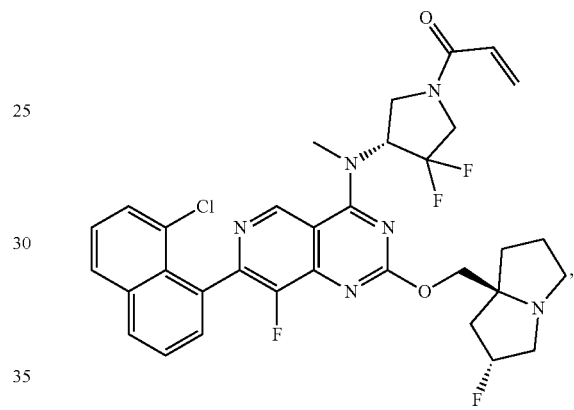
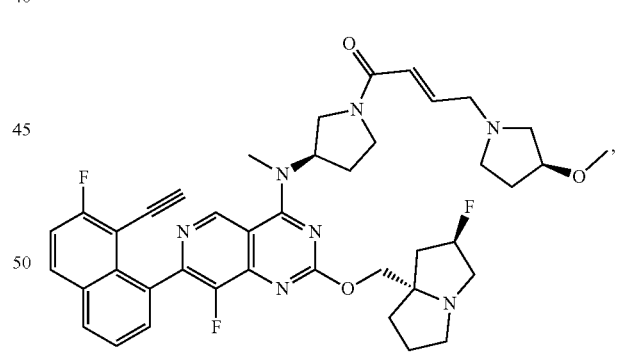
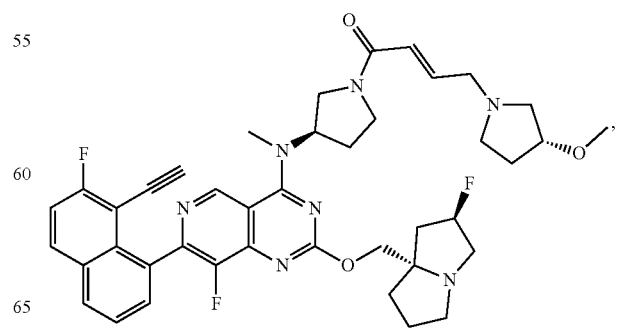

325
-continued
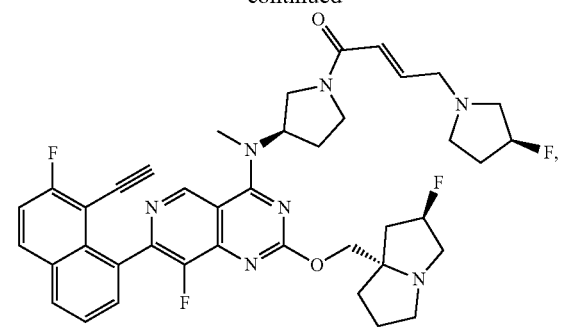

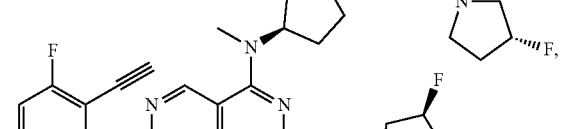

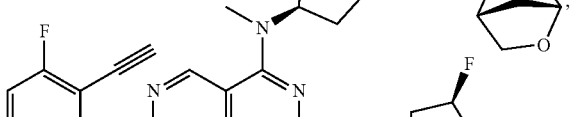
326
-continued
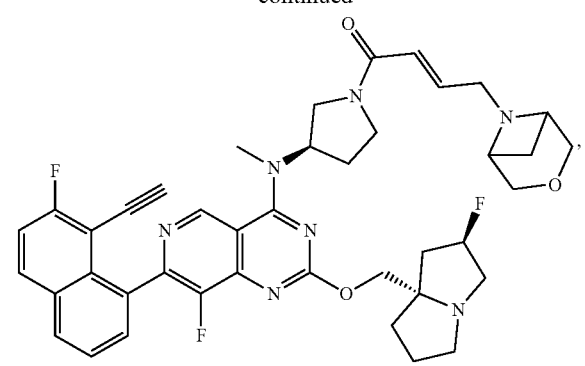
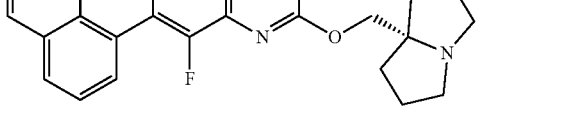
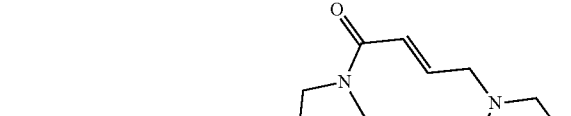
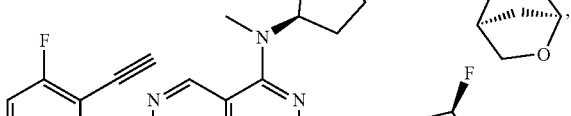
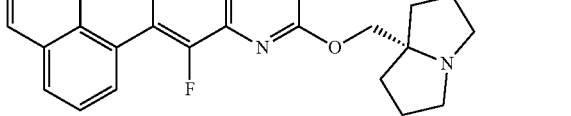
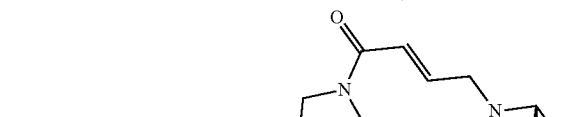
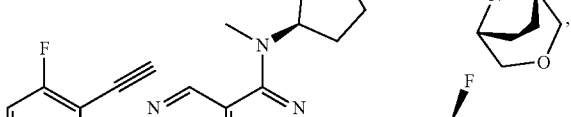

327
-continued
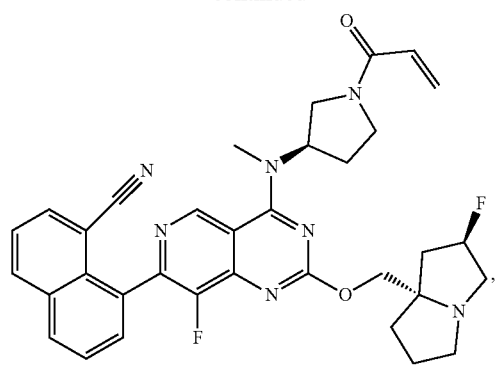
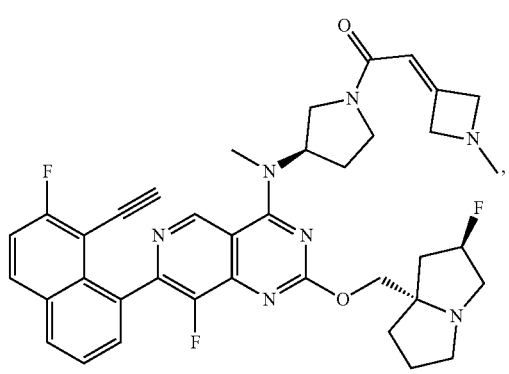
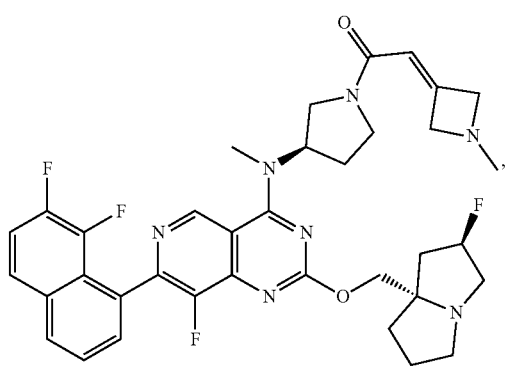
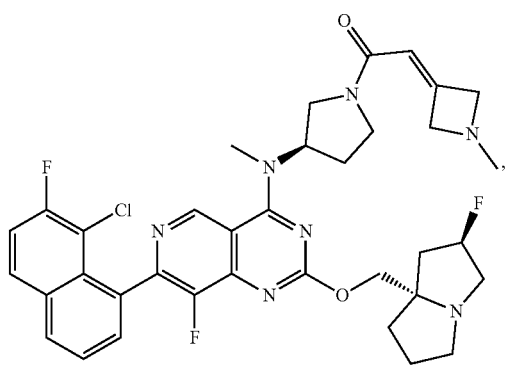
328
-continued
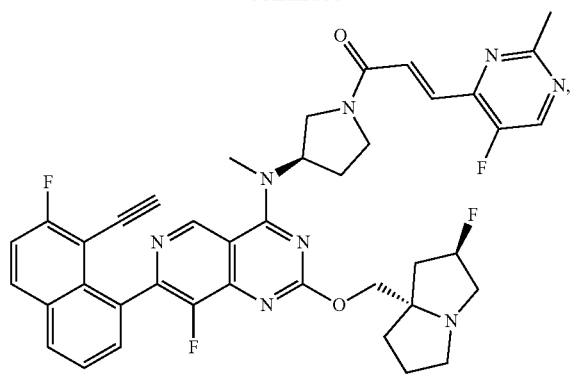
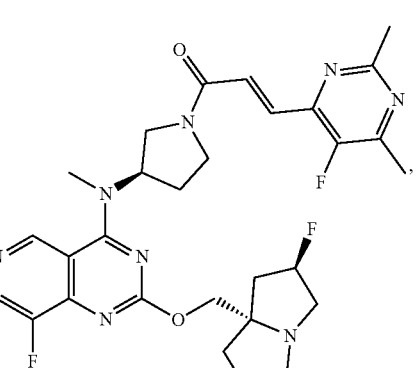
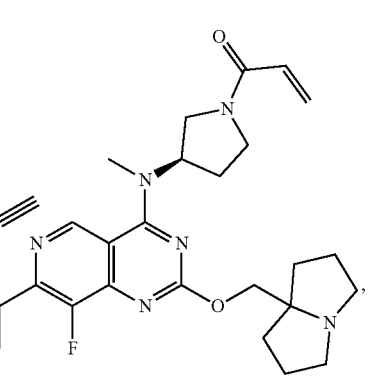
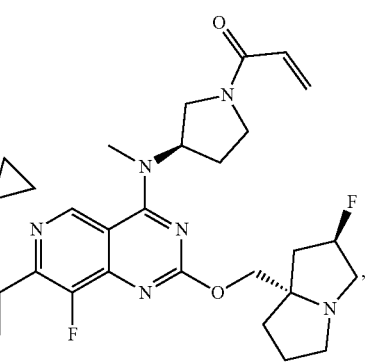

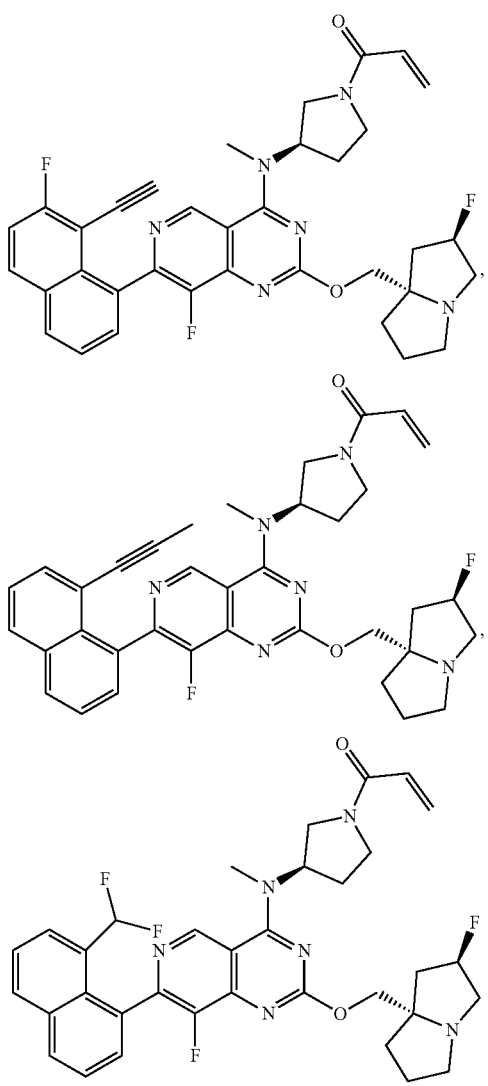
and all salts and isotopologues thereof.
Embodiment 431. The compound of any one of embodiments 1, 11 and 18, selected from the group consisting of:
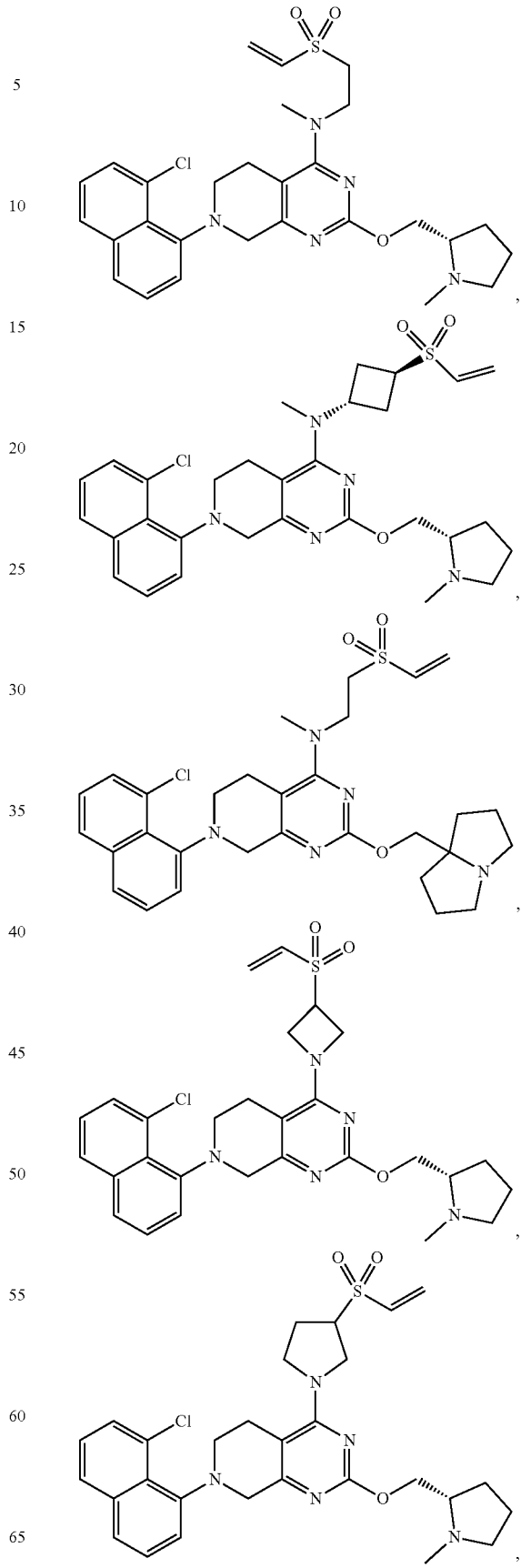

331
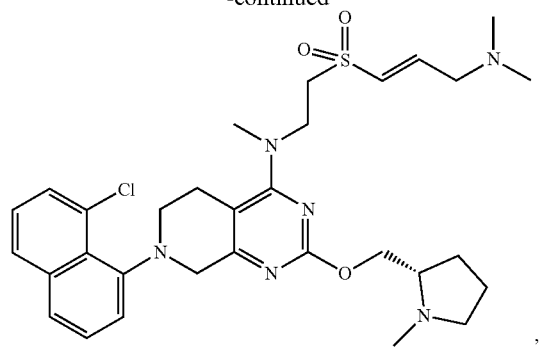
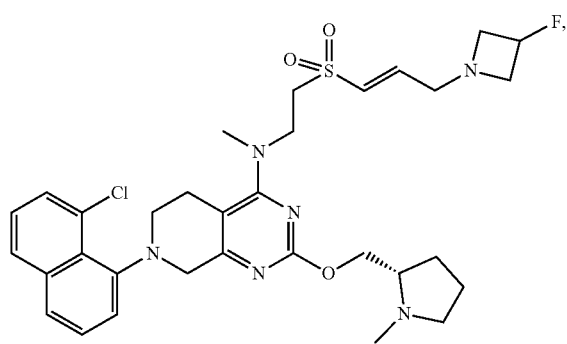
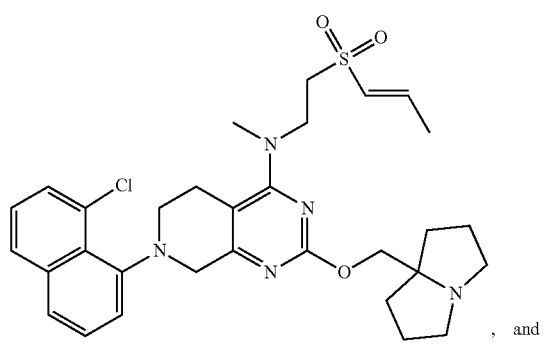, and
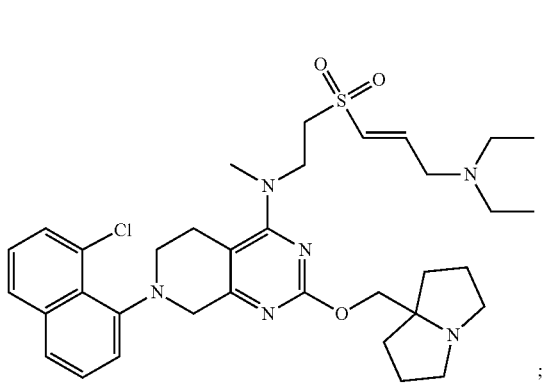;
and all salts and isotopologues thereof.
Embodiment 432. The compound of any one of embodiments 1, 11 and 18, selected from the group consisting of:
332
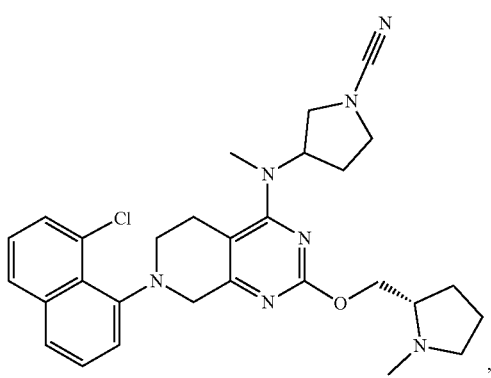,
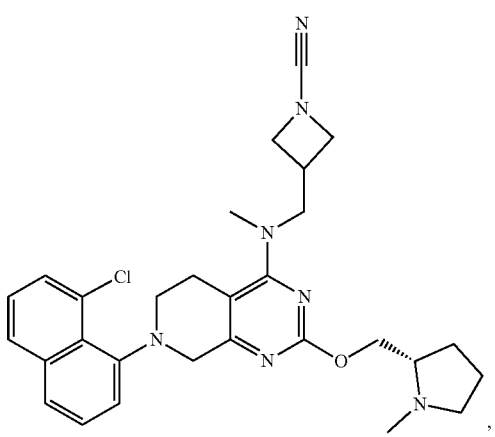,
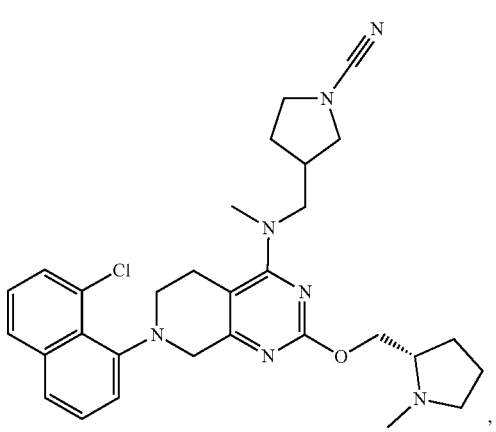,
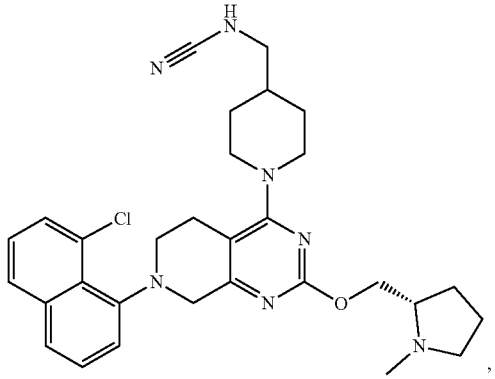,

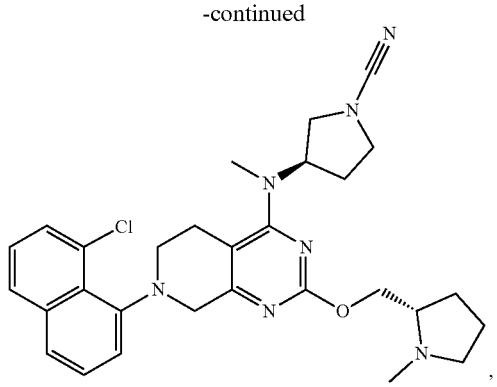
,
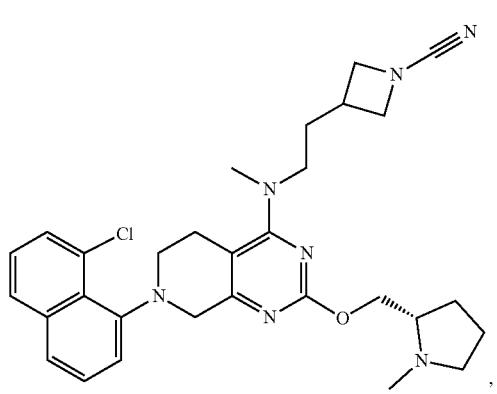
,
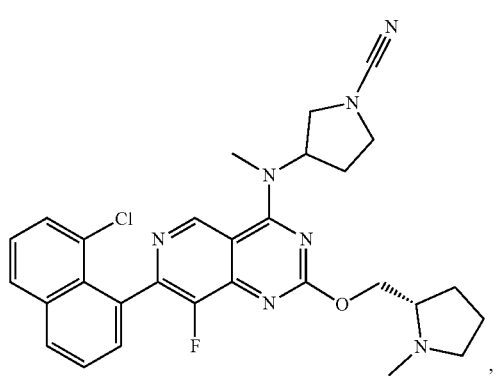
,
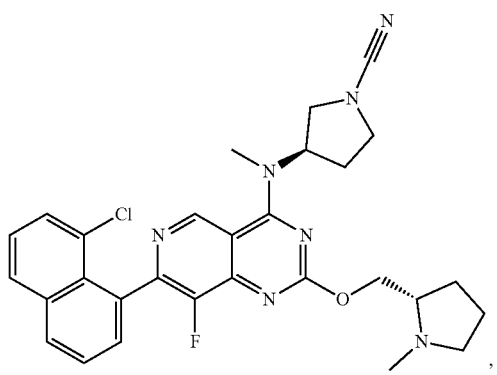
,
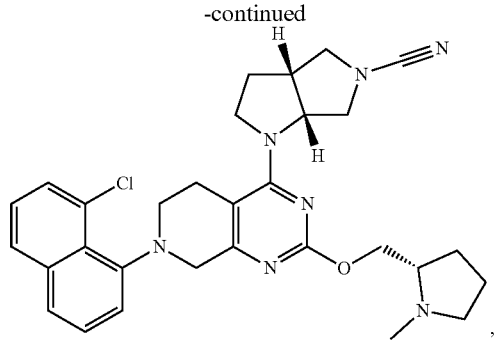
,
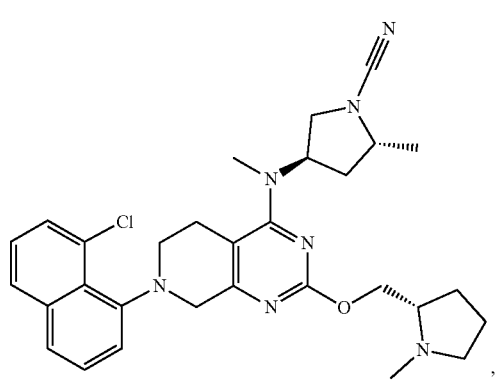
,
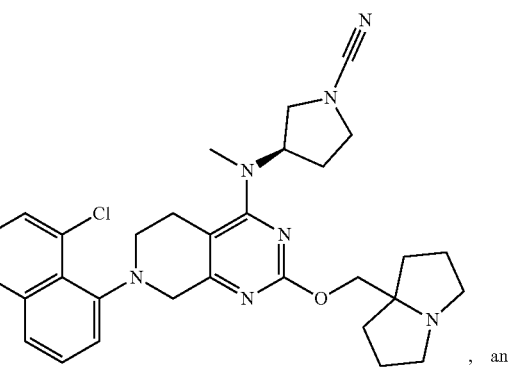
, and
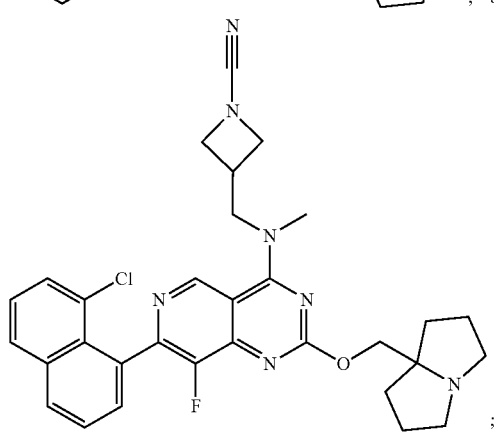
;
and all salts and isotopologues thereof.
Embodiment 433. The compound of any one of embodiments 1, 11 and 18e, selected from the group consisting of:

335
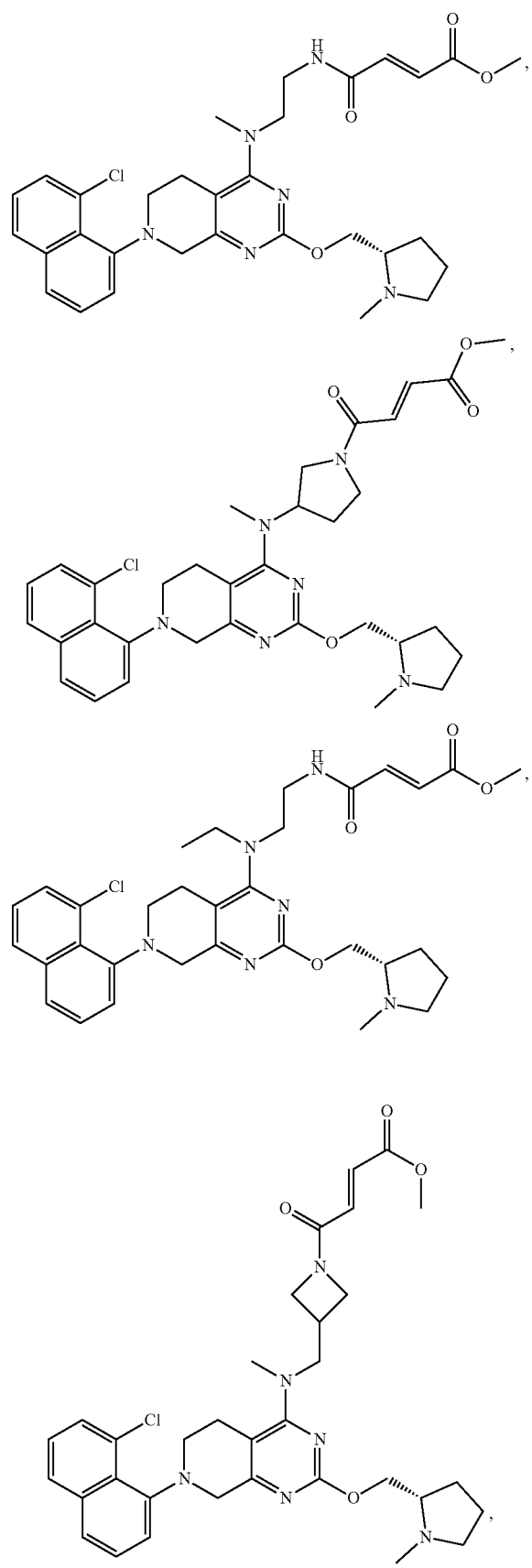
336
-continued
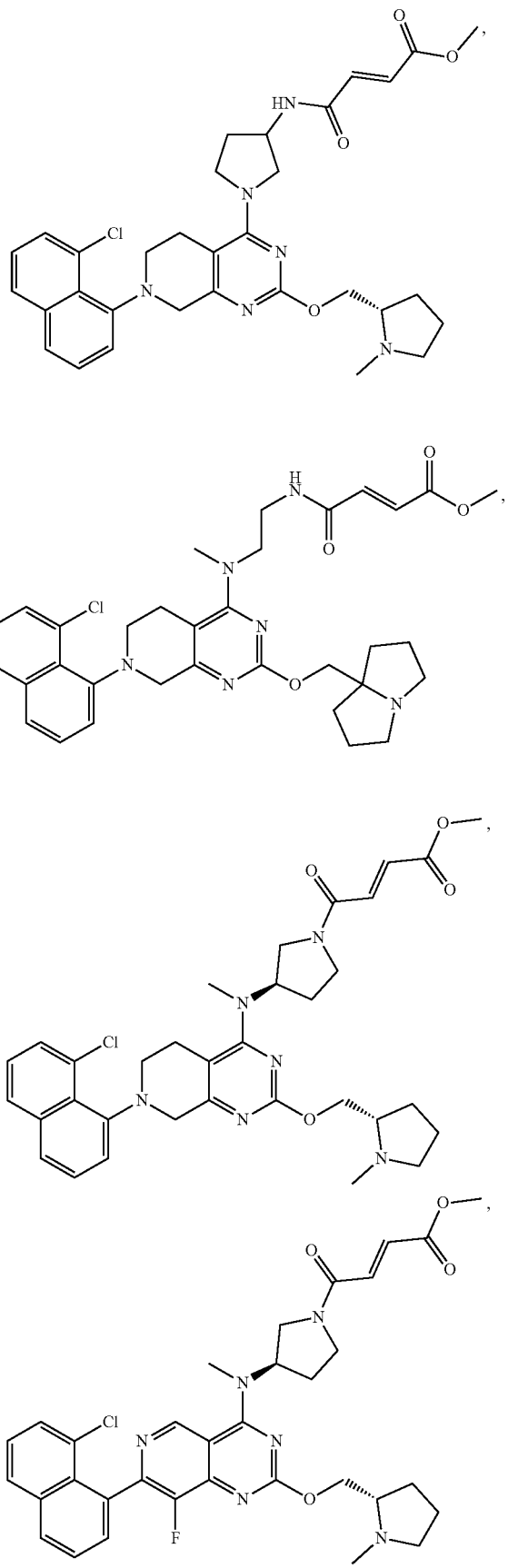

337
-continued
338
-continued
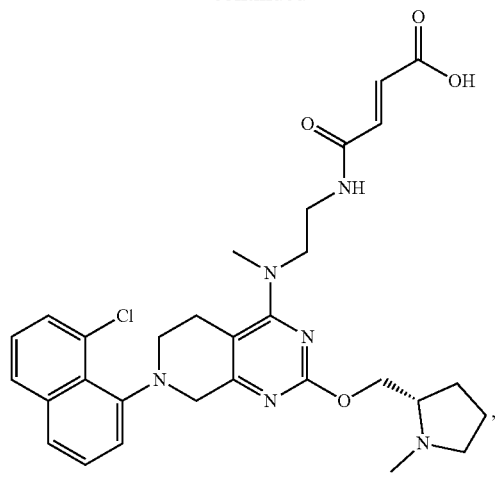
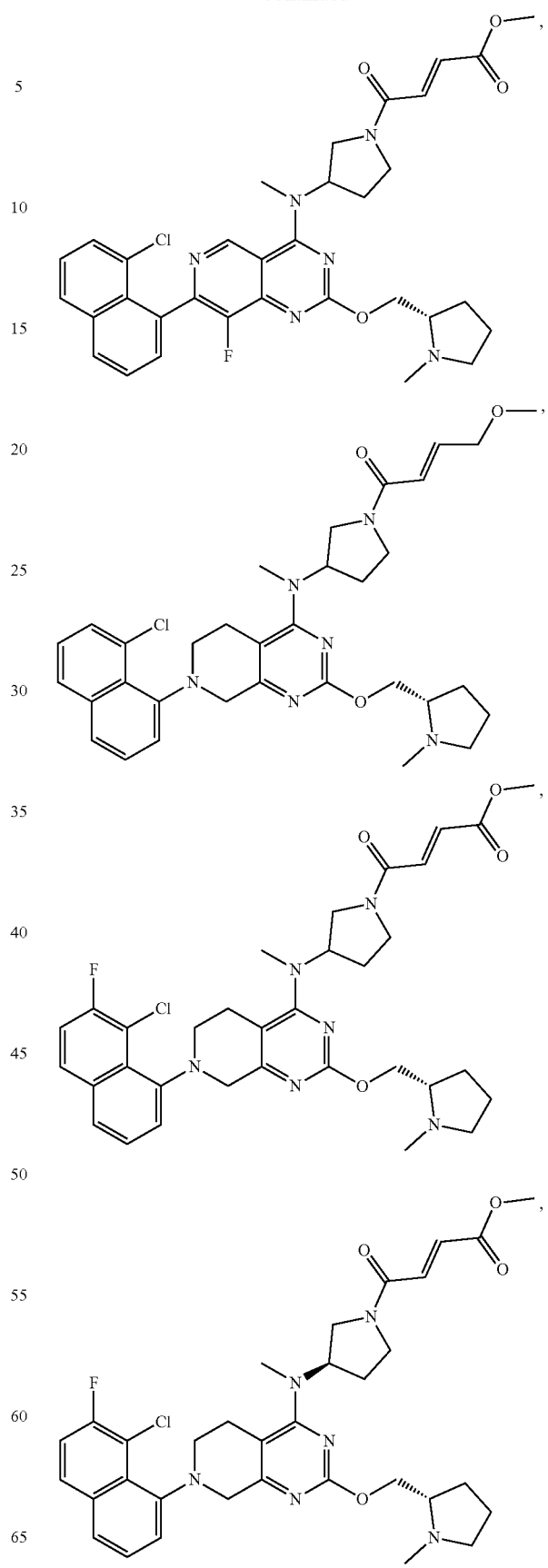

339
-continued
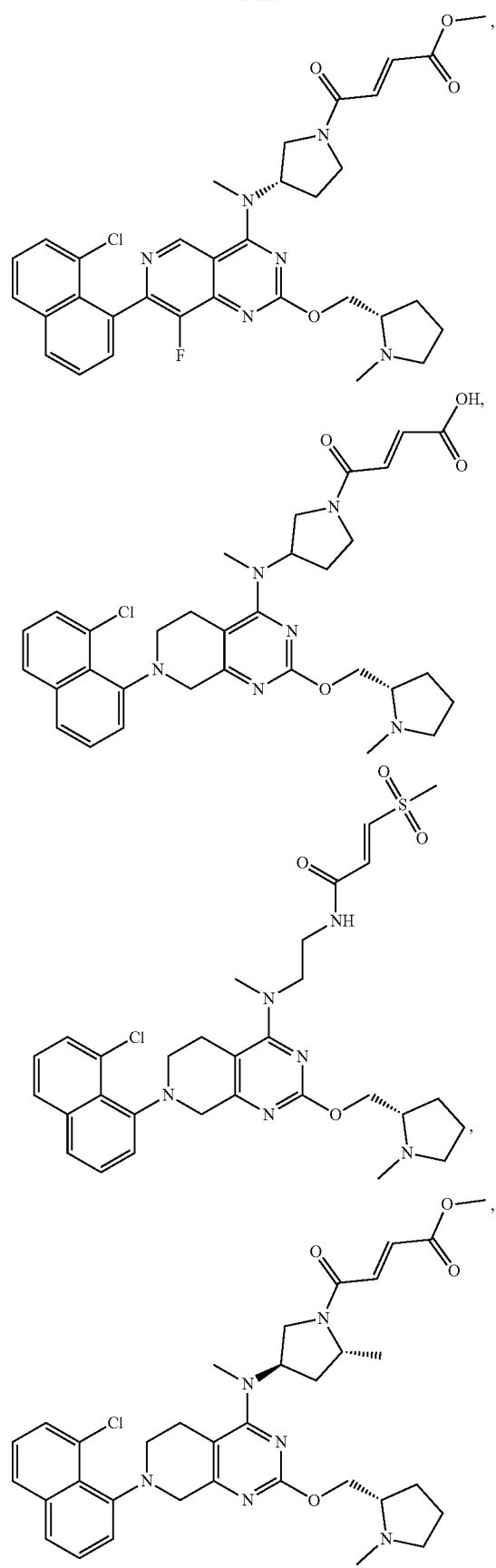
340
-continued
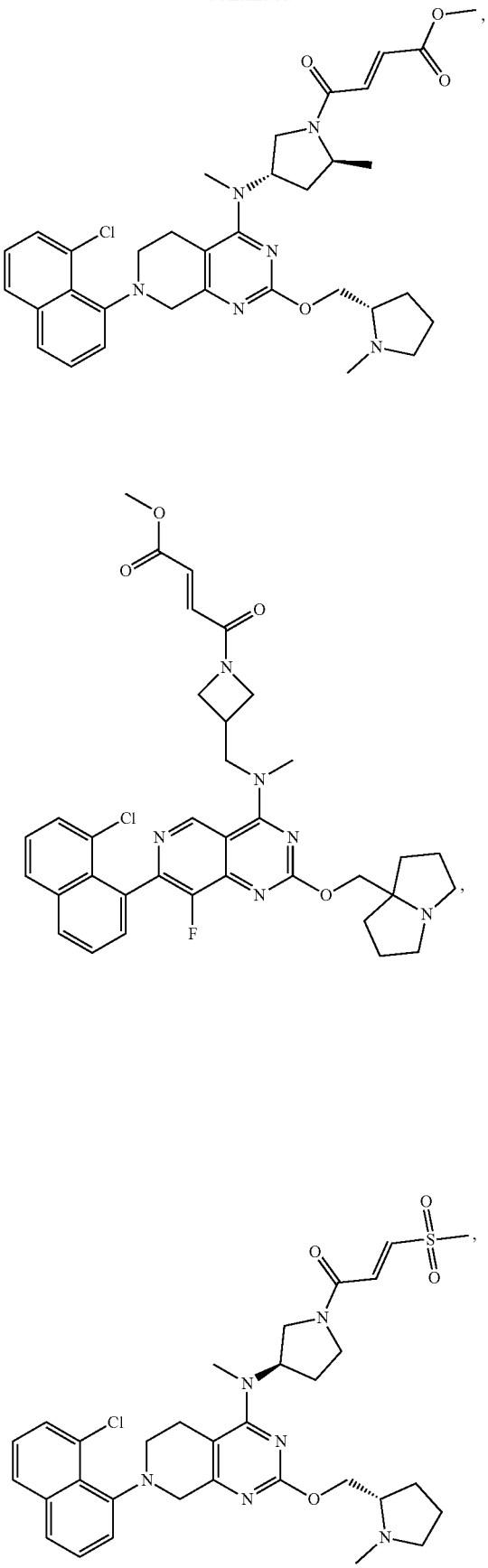

341
-continued
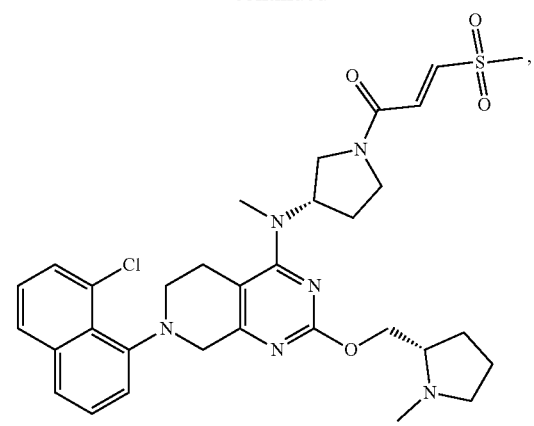
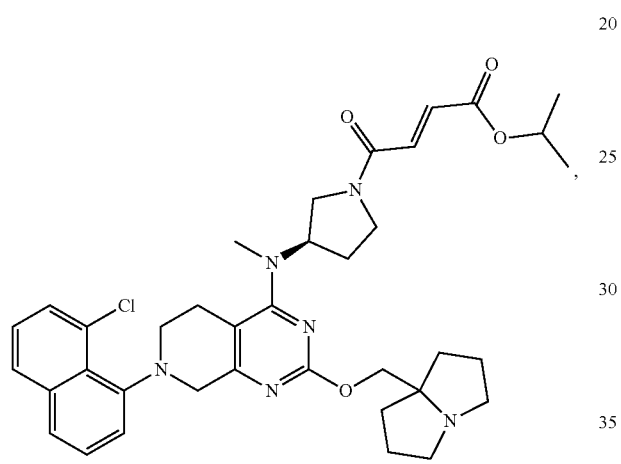
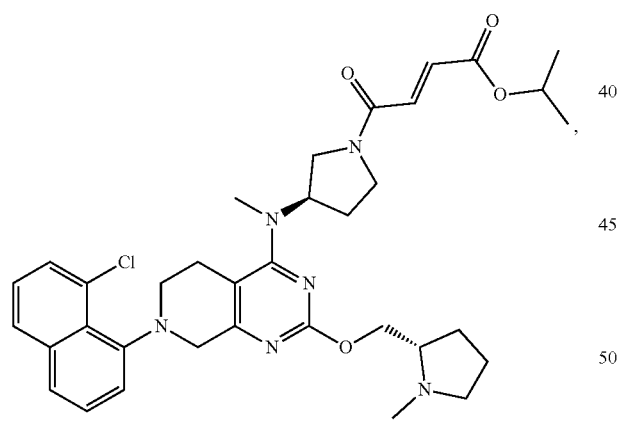
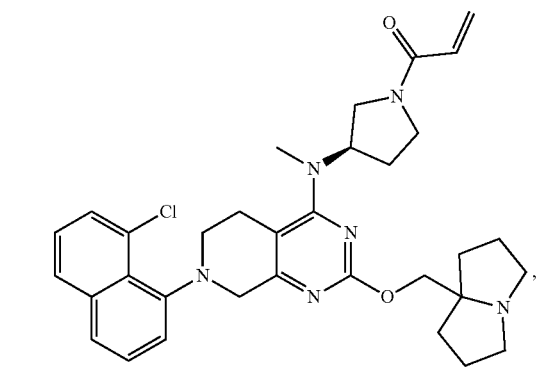
342
-continued
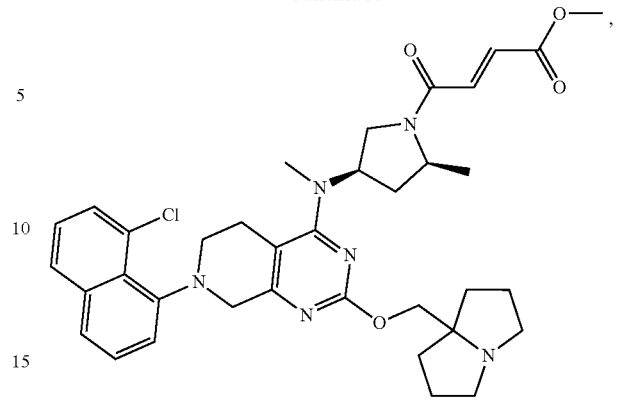
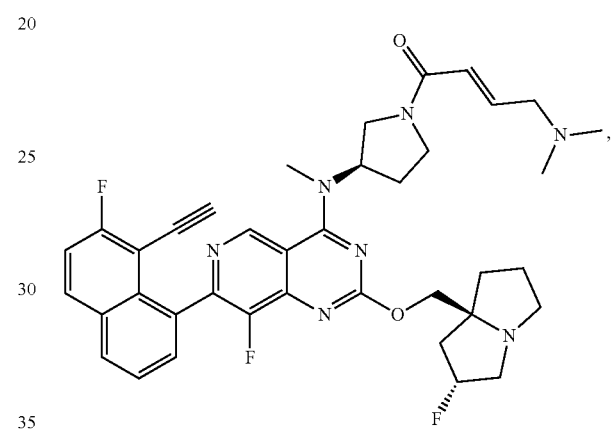
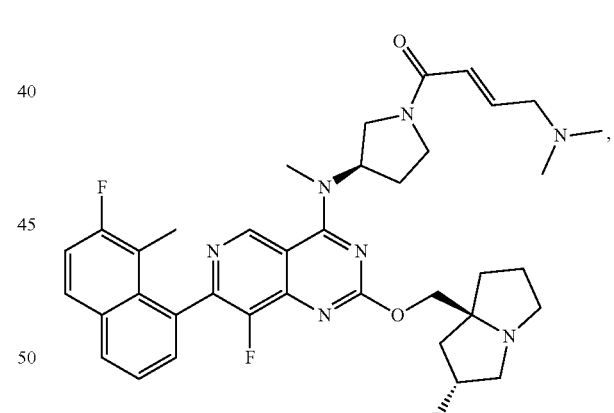
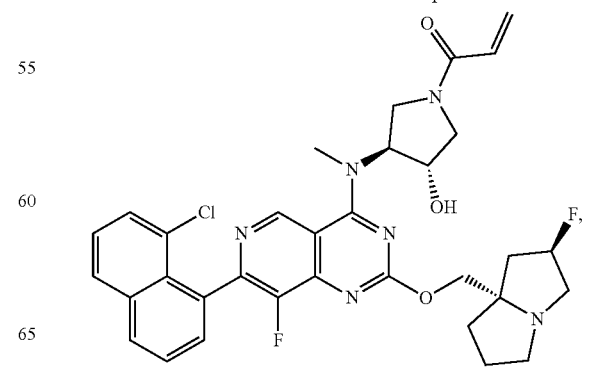

343
-continued
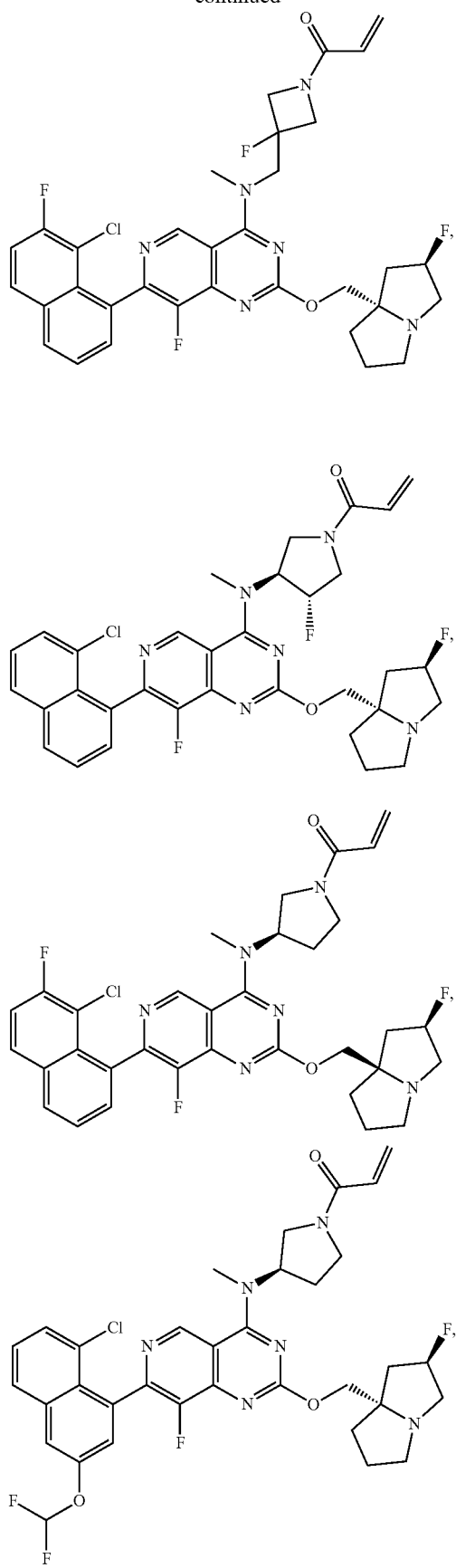
344
-continued
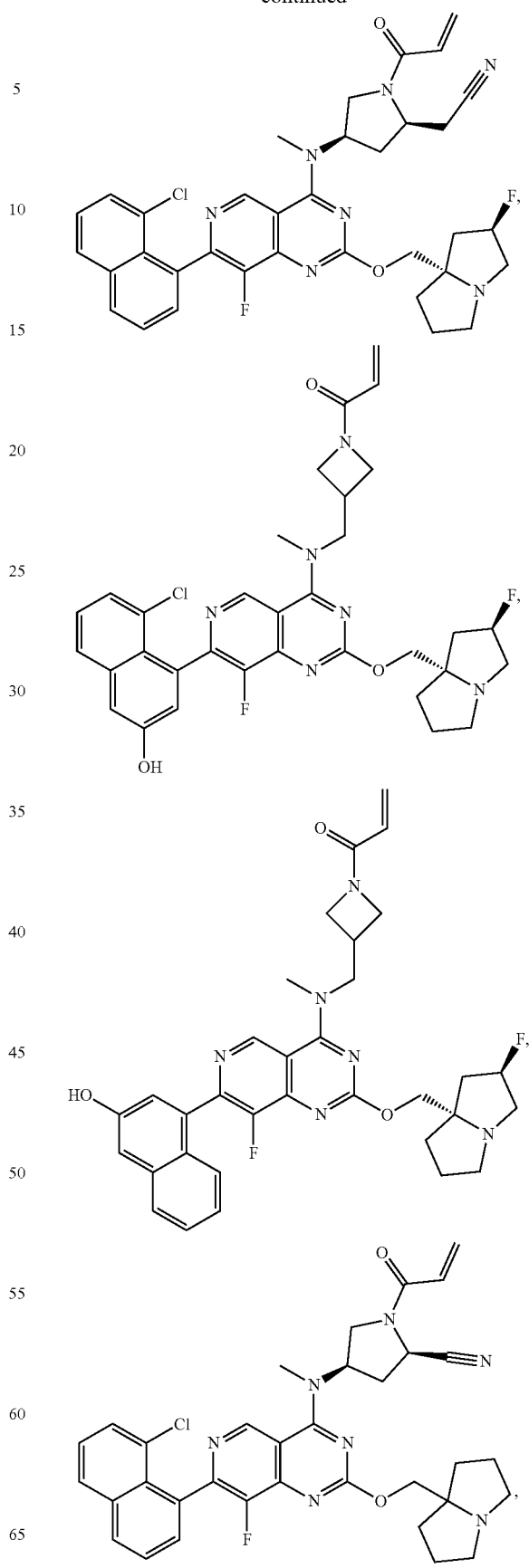

345
-continued
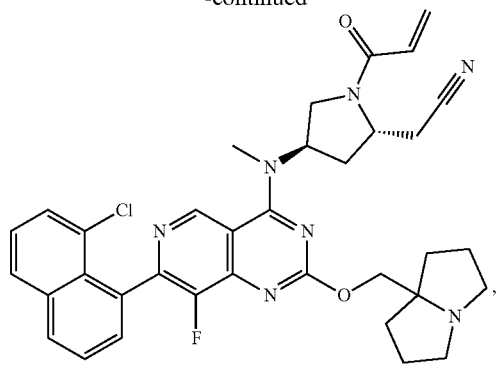
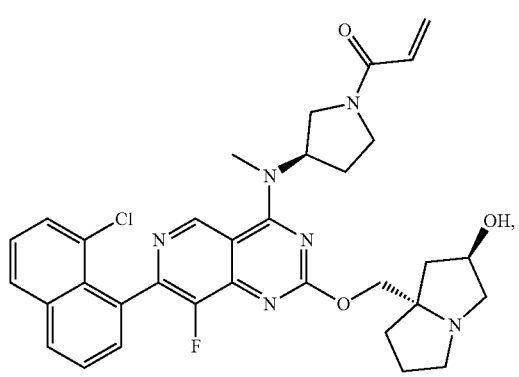
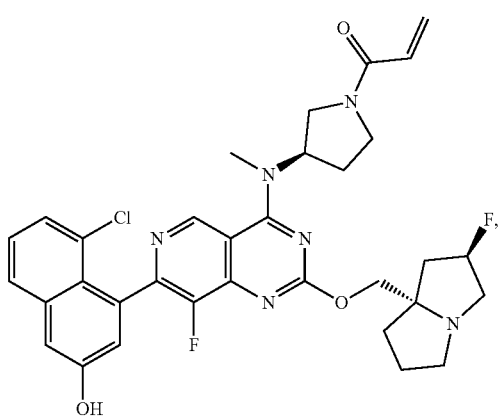
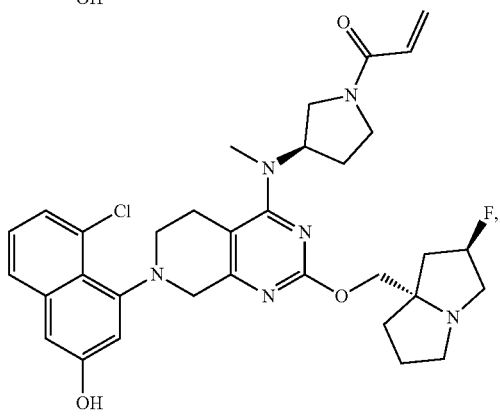
346
-continued
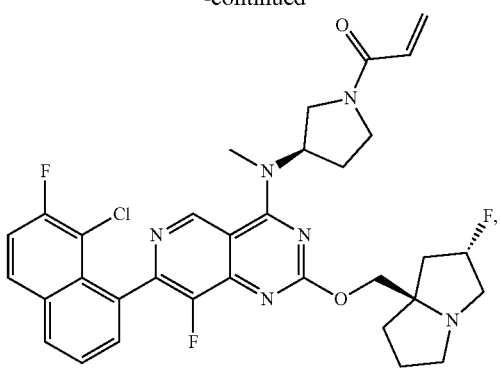
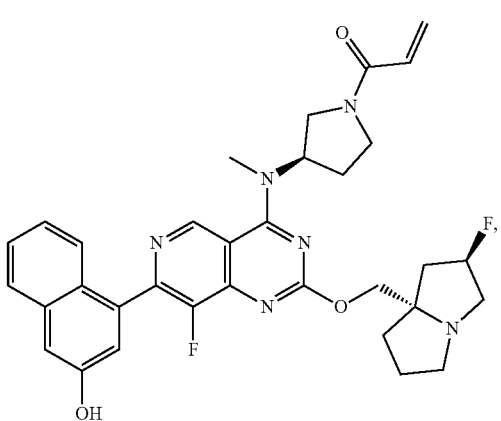
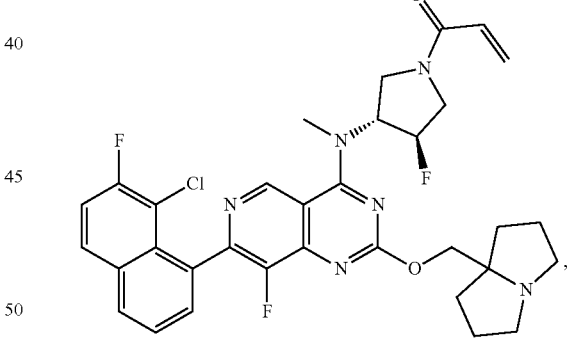
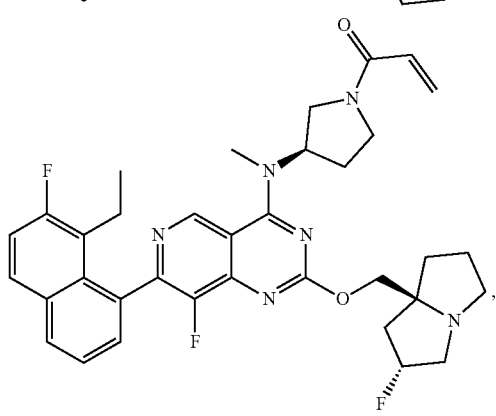

347
-continued
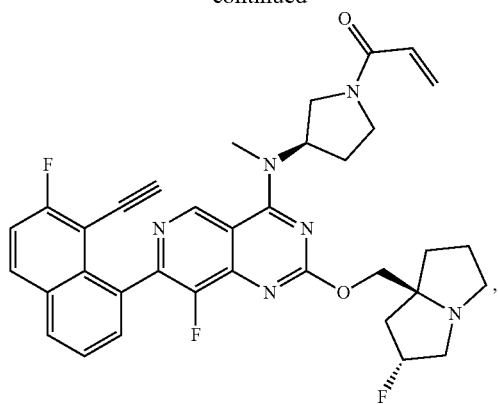
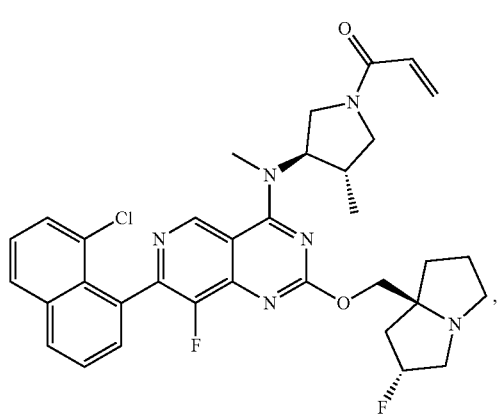
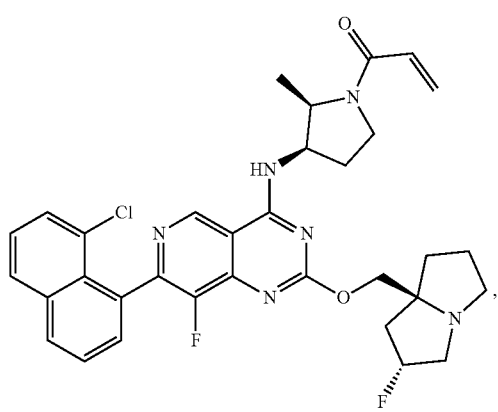
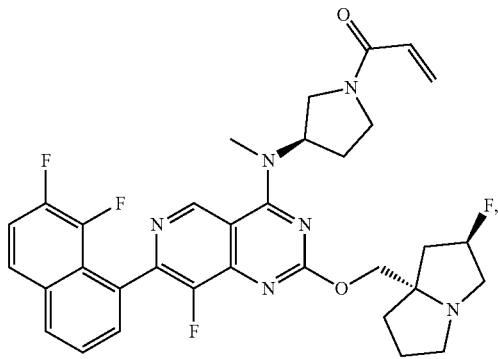
348
-continued
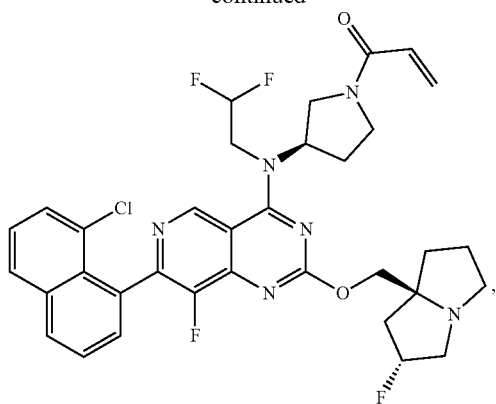
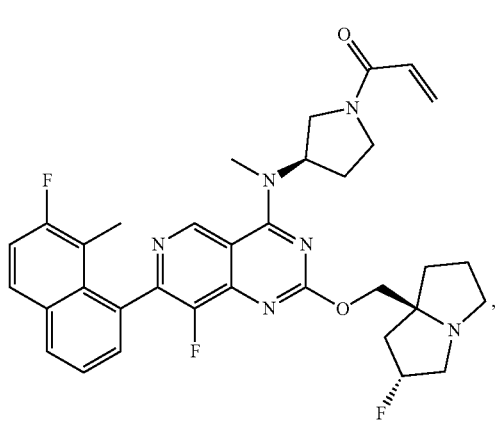
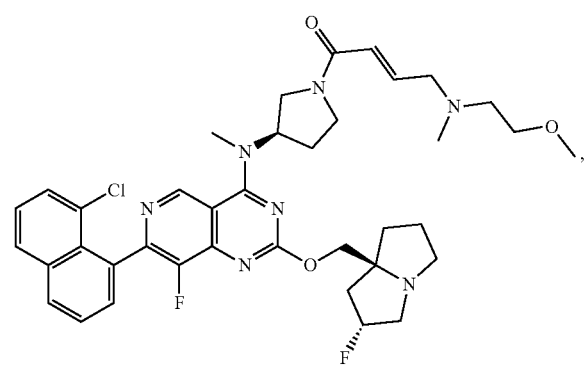
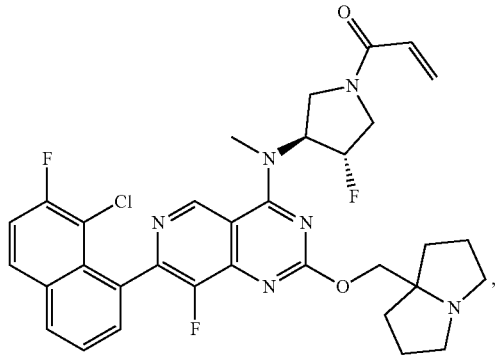

349
-continued
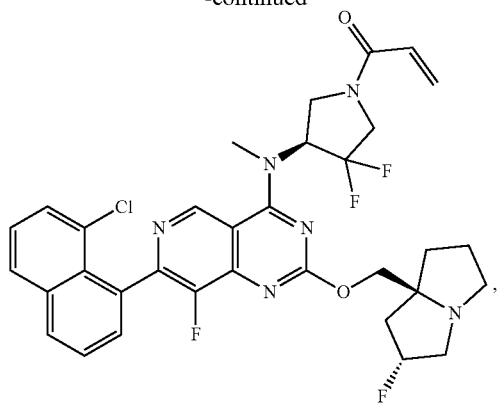
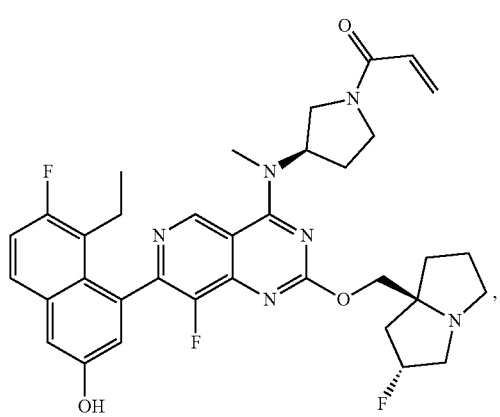
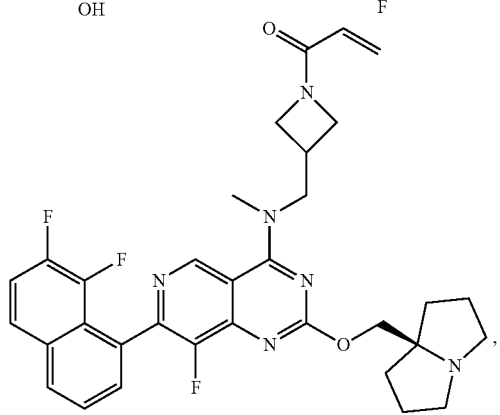
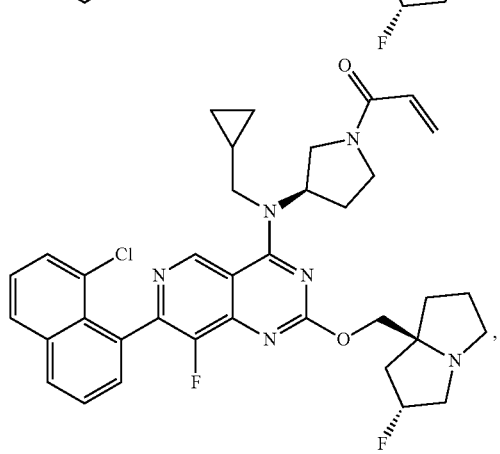
350
-continued
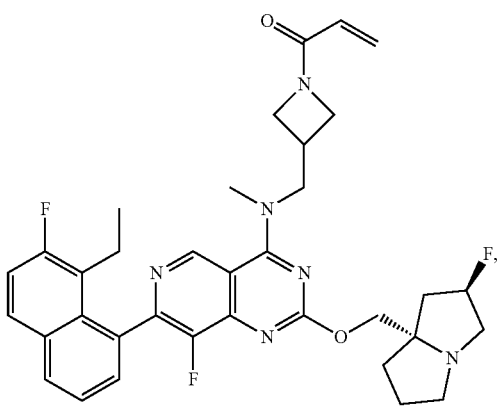
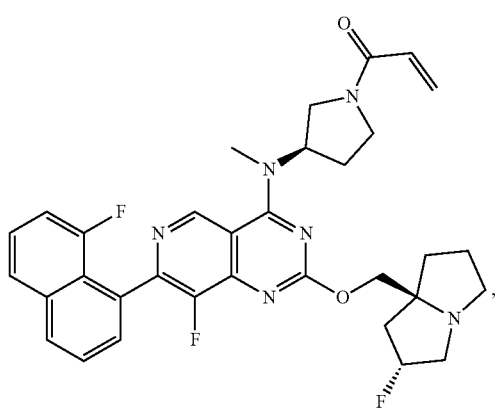
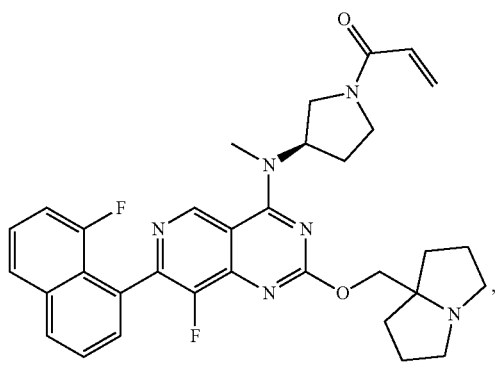

351
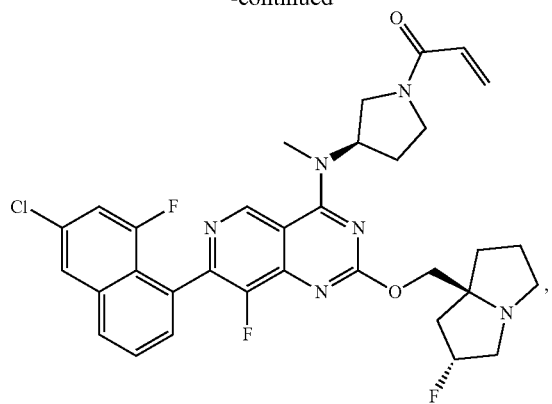
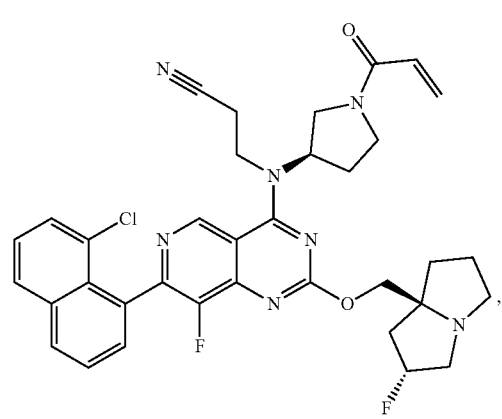
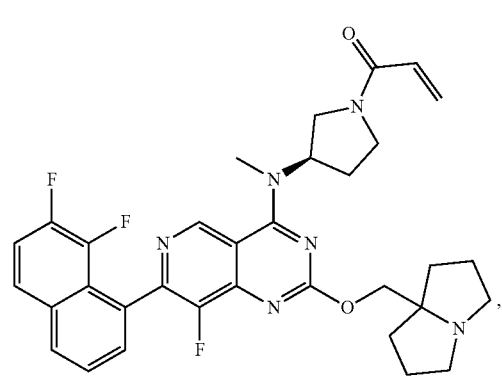
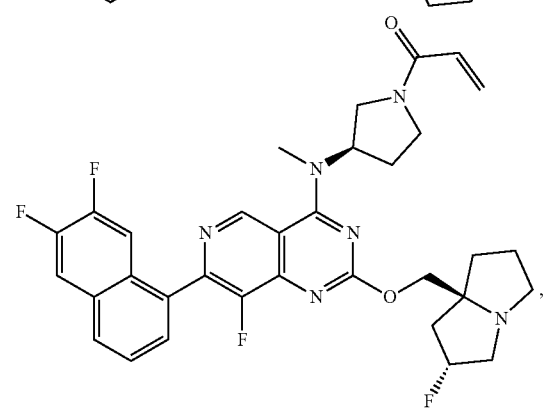
352
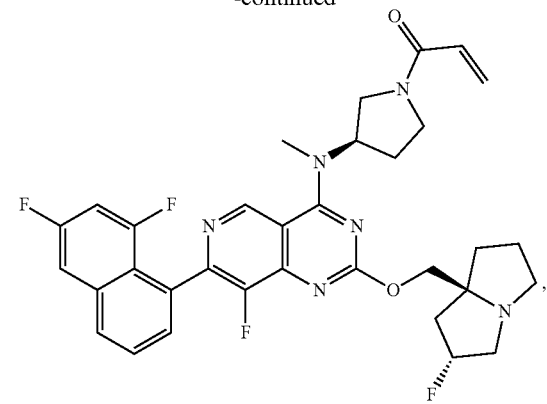
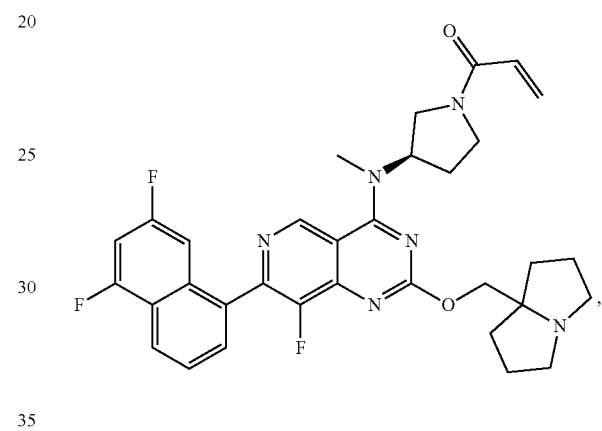
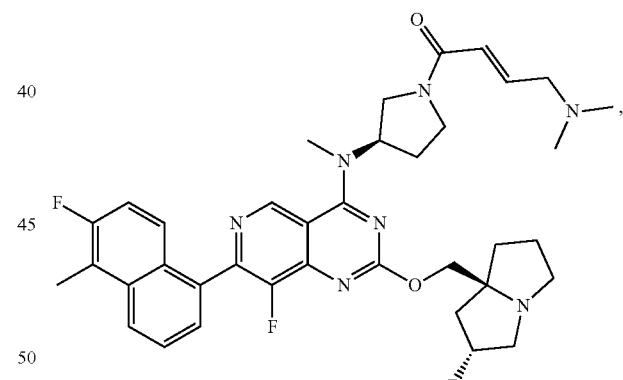
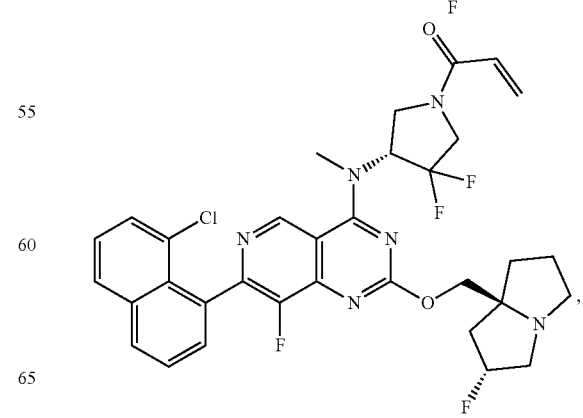

-continued
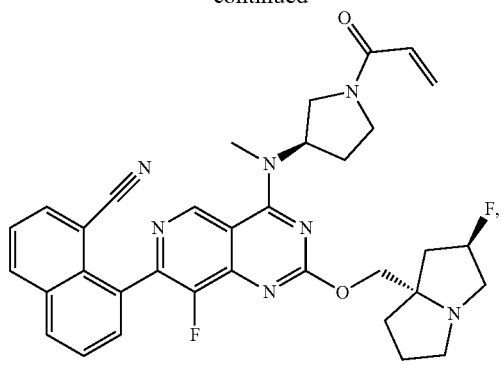
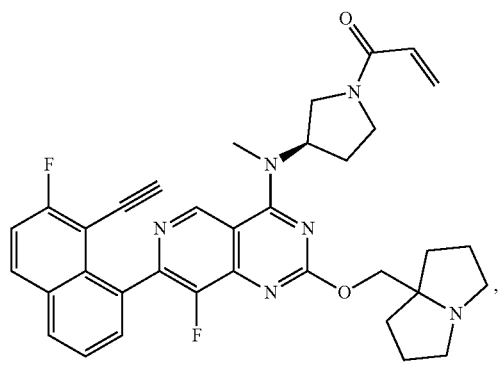
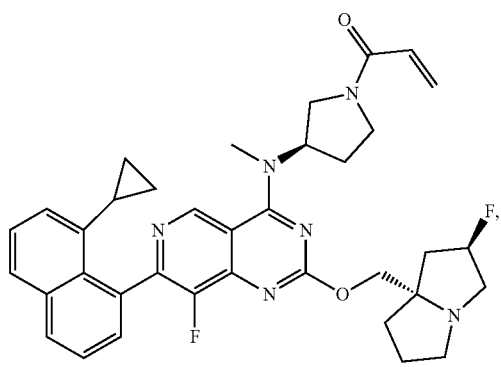
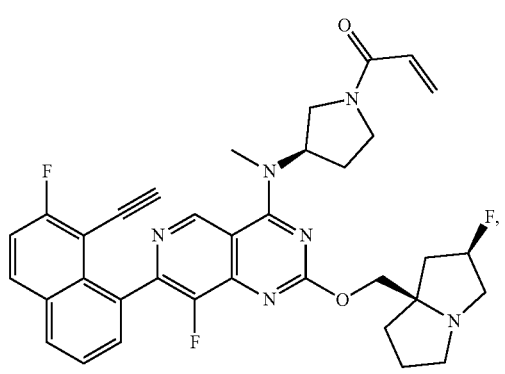
-continued
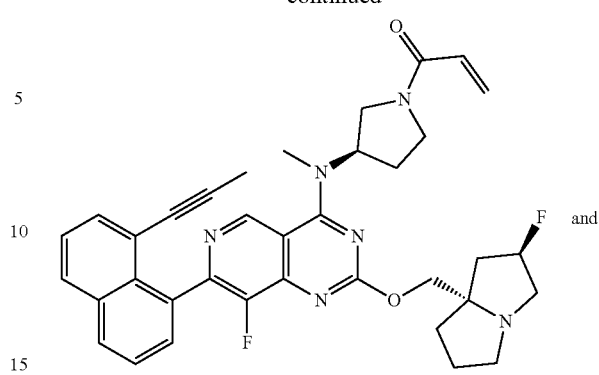
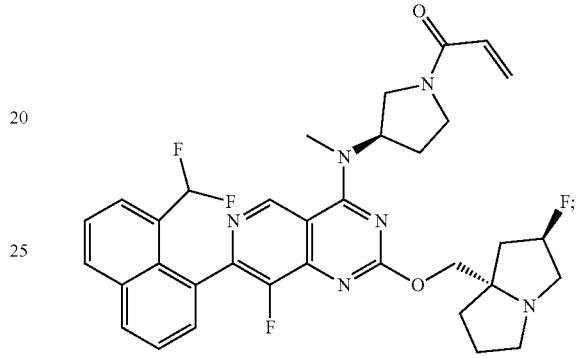
and all salts and isotopologues thereof.
Embodiment 434. The compound of any one of embodiments 1, 11 and 18, selected from the group consisting of:
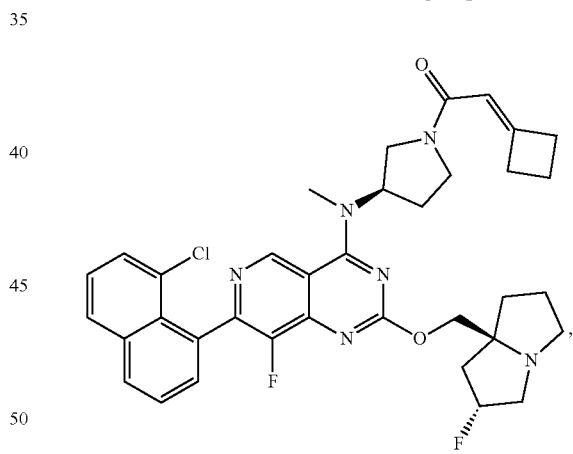
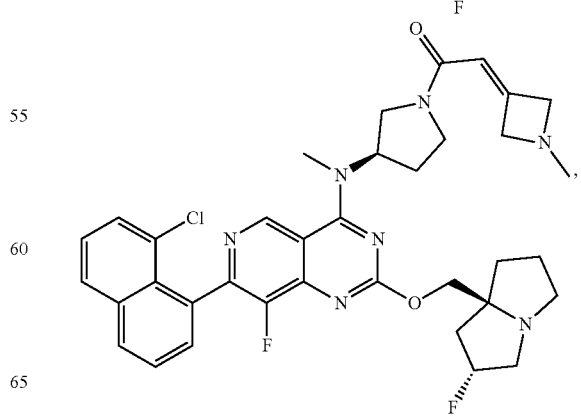

-continued
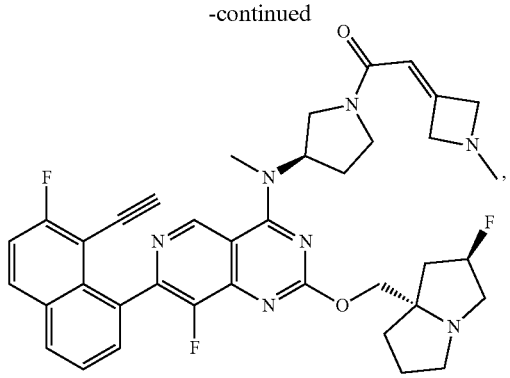
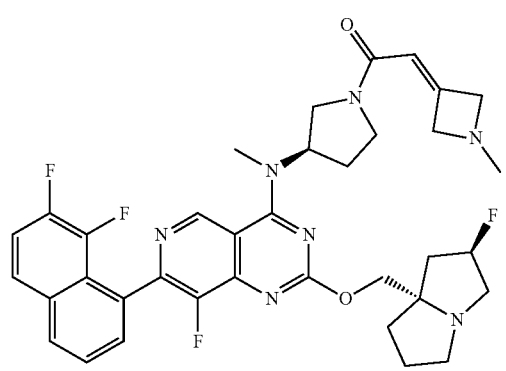
and
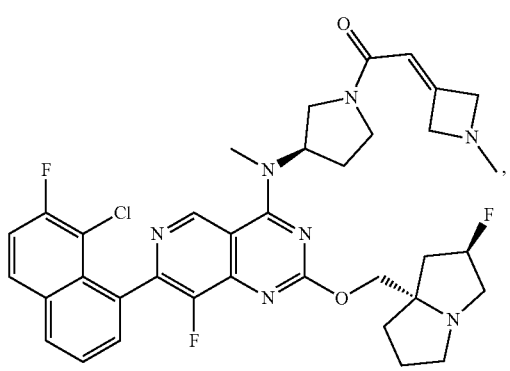
and all salts and isotopologues thereof.
Embodiment 435. The compound of any one of embodiments 1, 11 and 18, selected from the group consisting of:
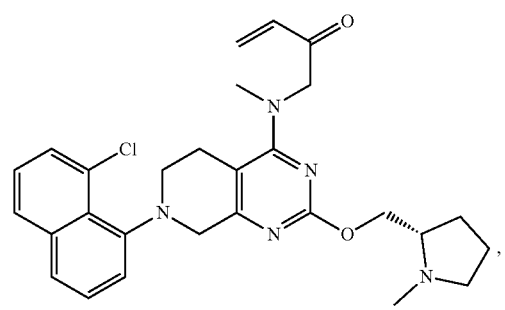
-continued
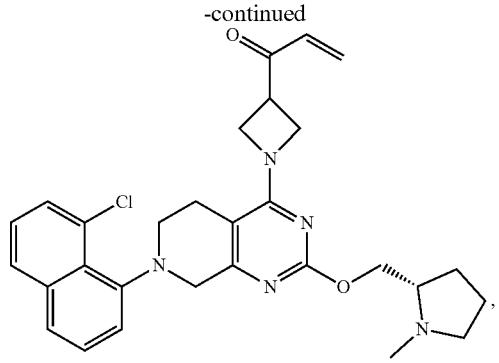
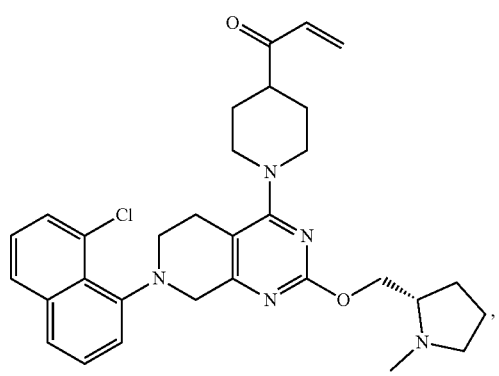
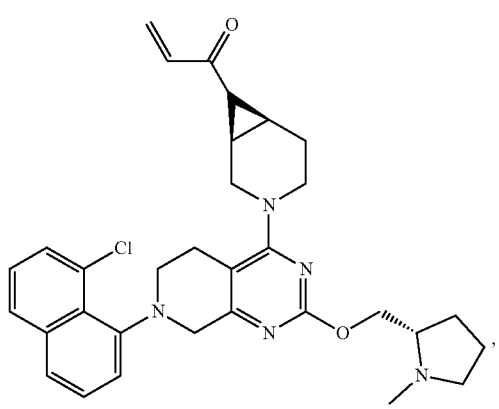
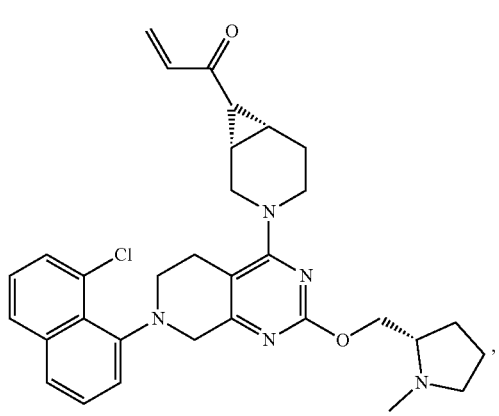

357
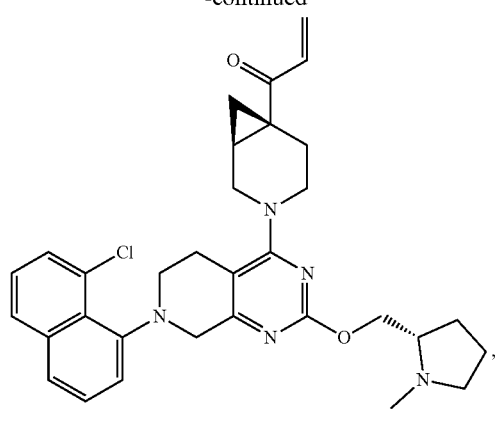
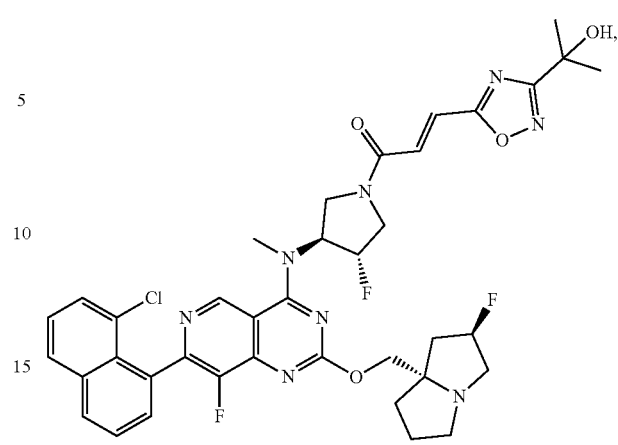
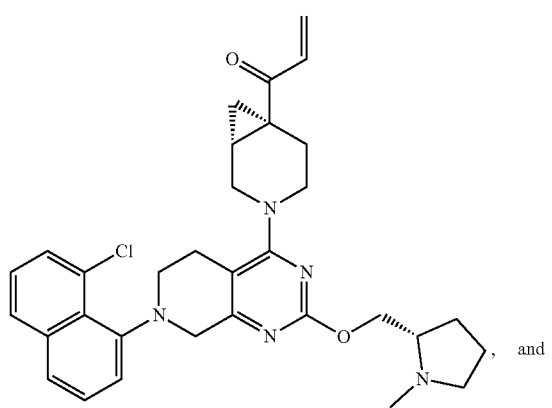
, and
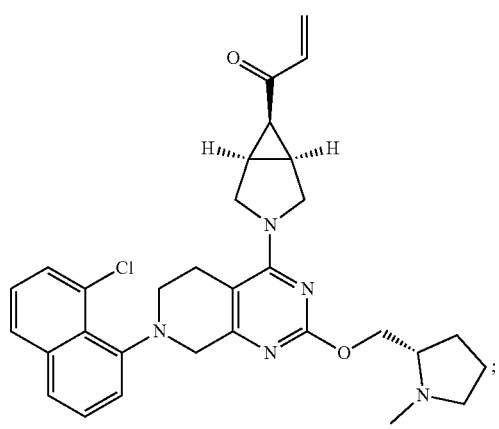
and all salts and isotopologues thereof.
Embodiment 436. The compound of any one of embodiments 1, 11 and 18, selected from the group consisting of:
358
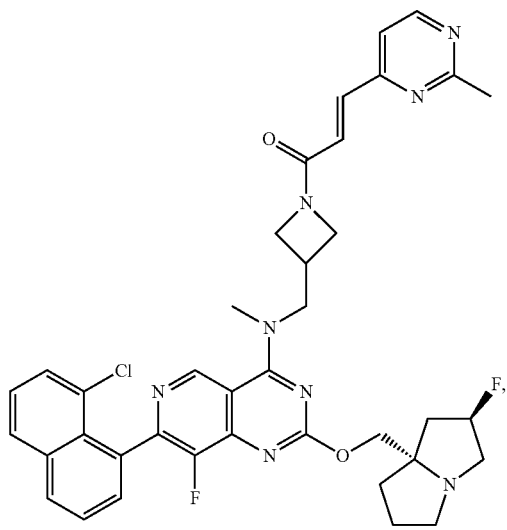

359
-continued
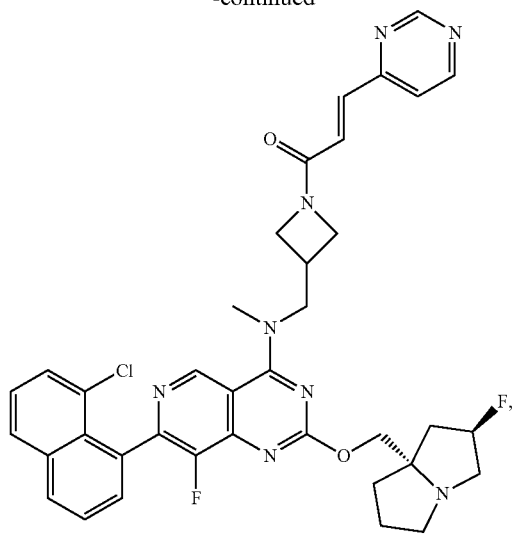
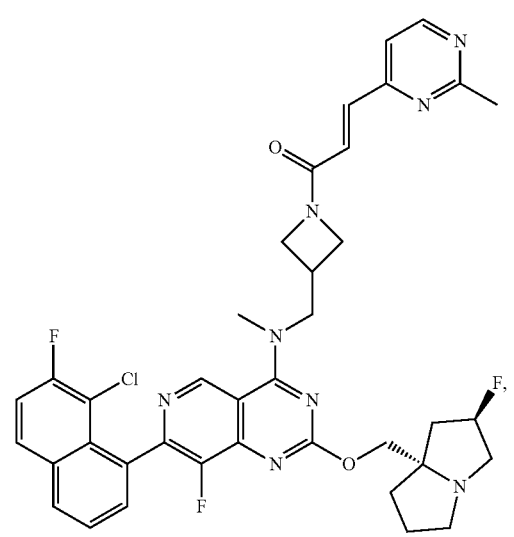
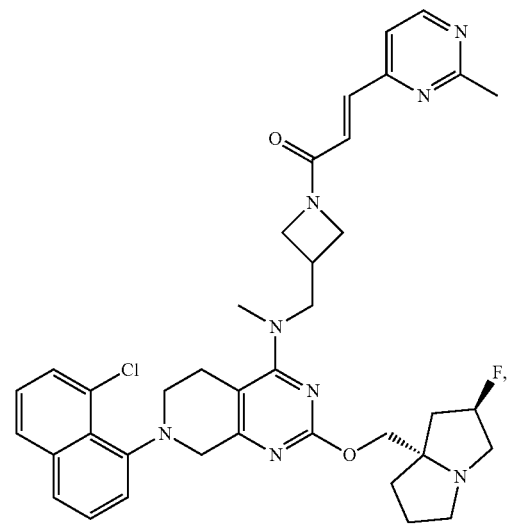
360
-continued
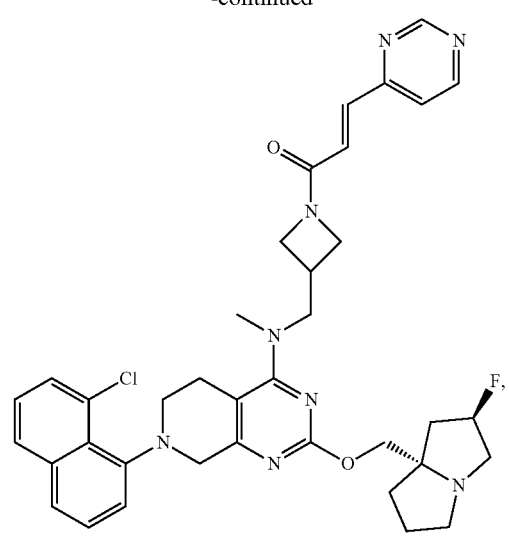
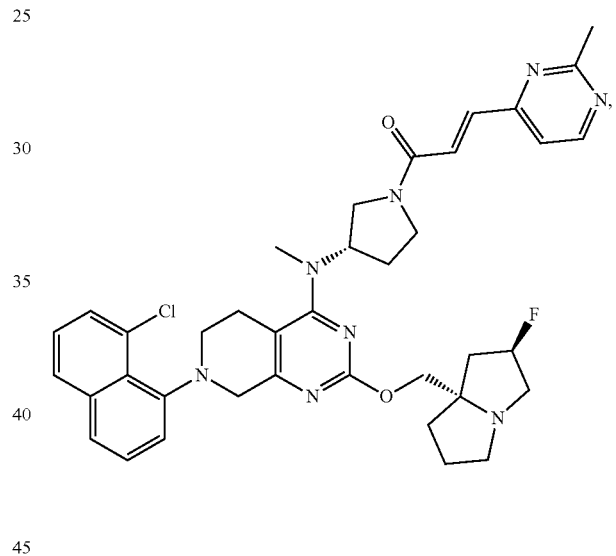
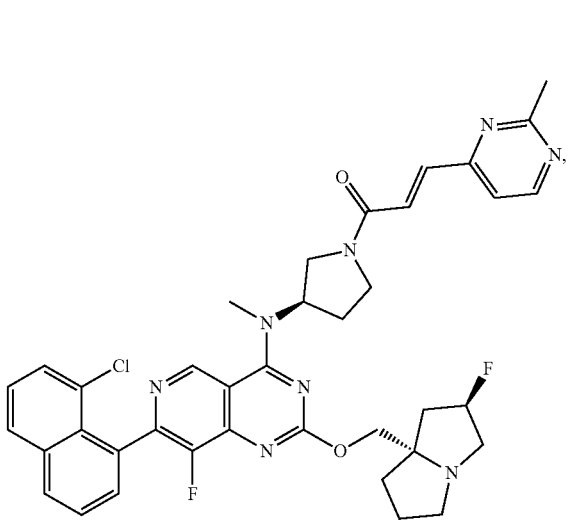

361
-continued
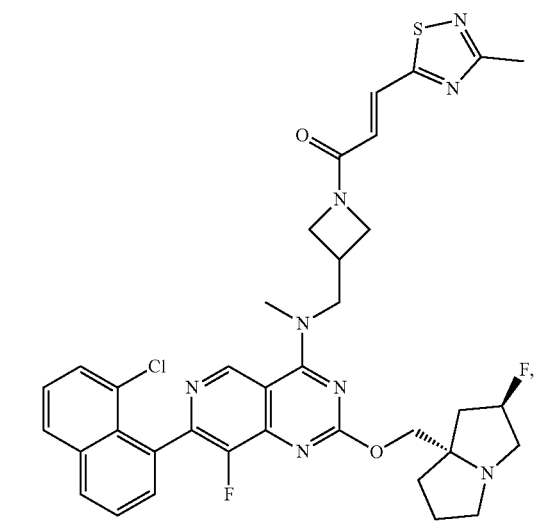
362
-continued
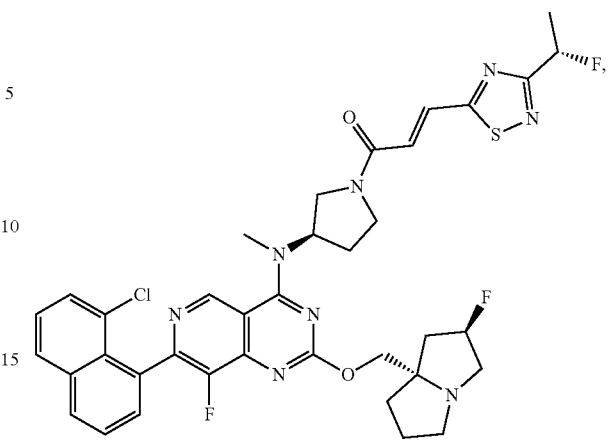
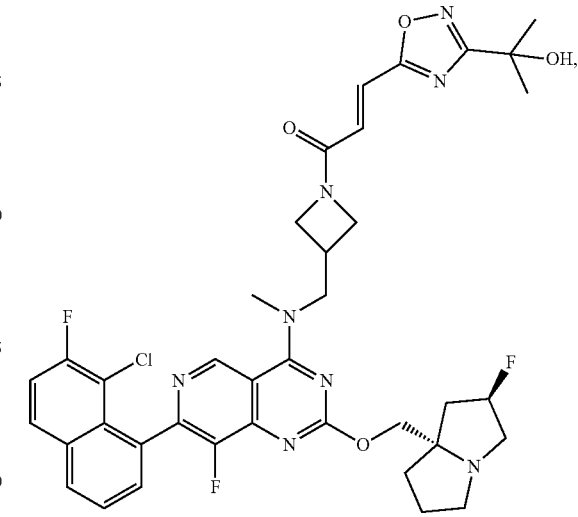
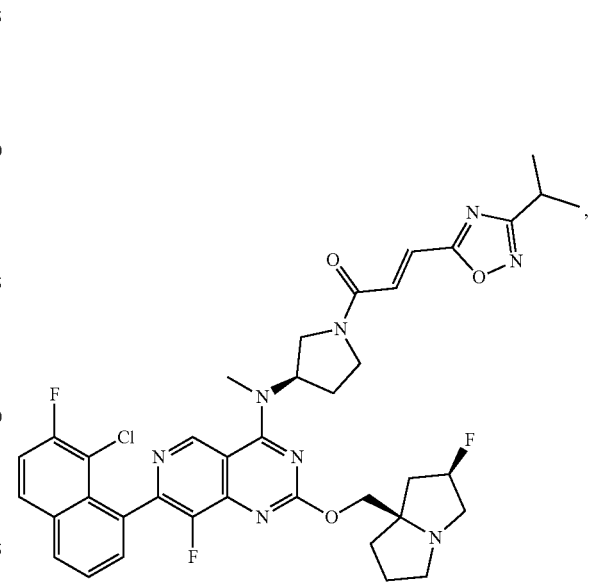

363
-continued
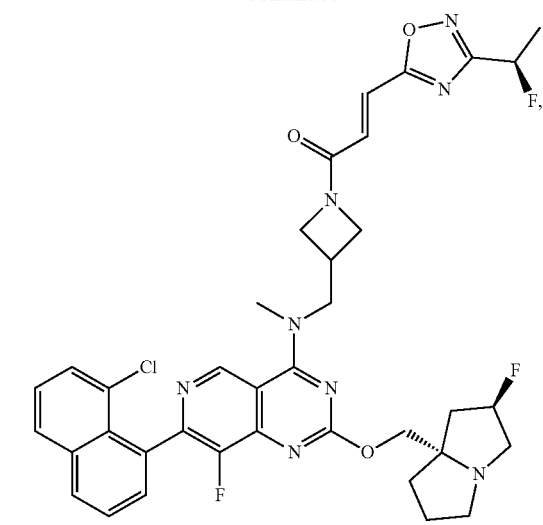
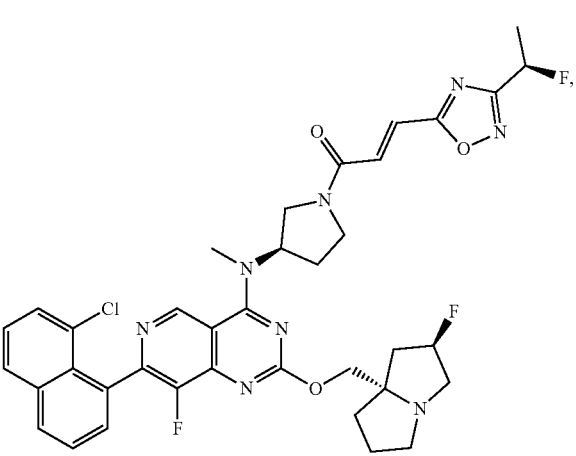
364
-continued
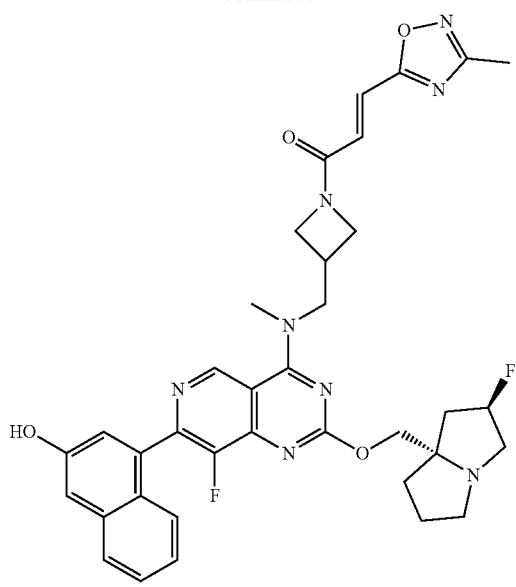
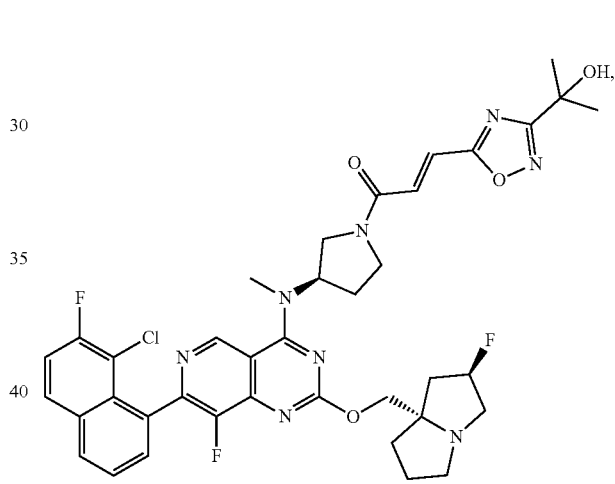
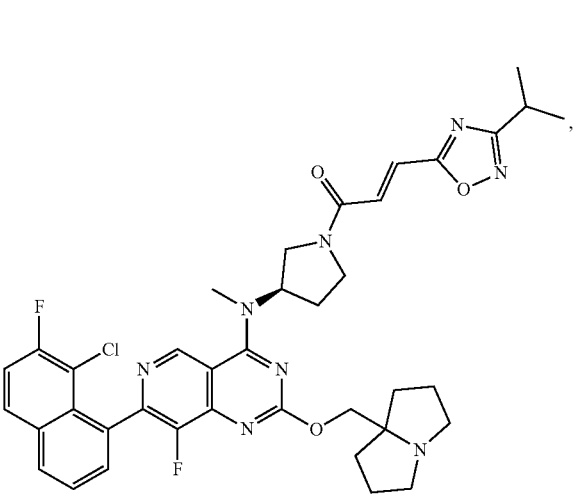
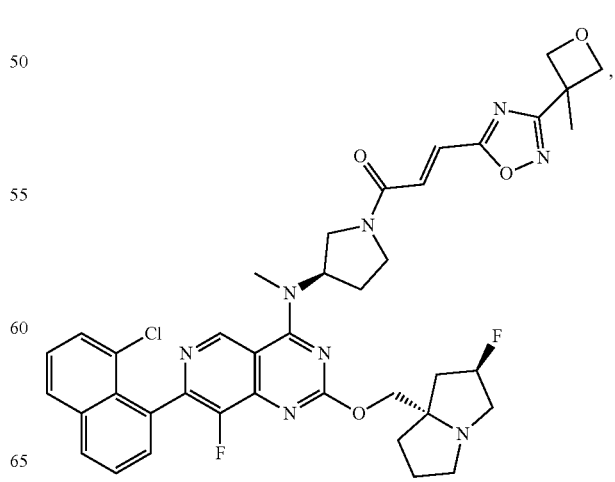

365
-continued
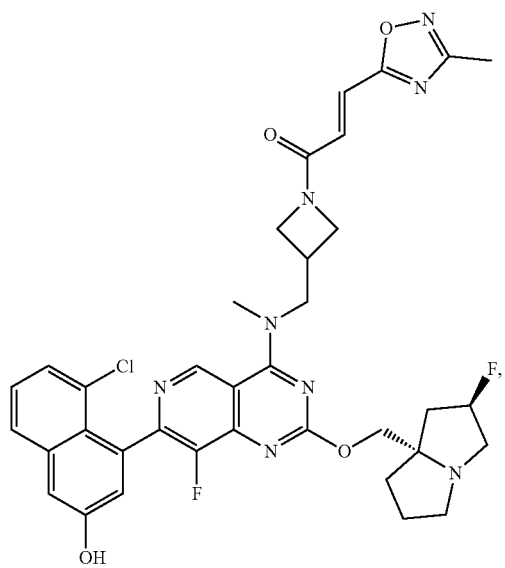
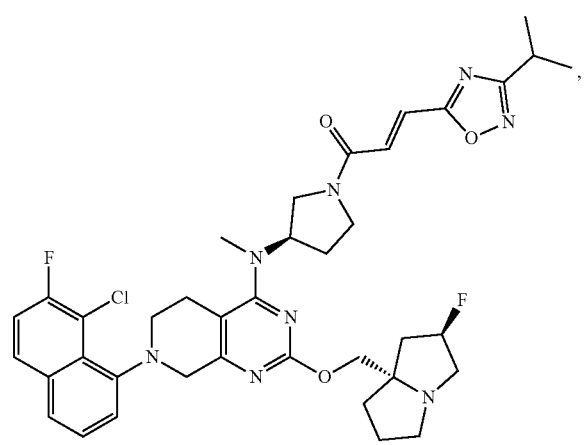
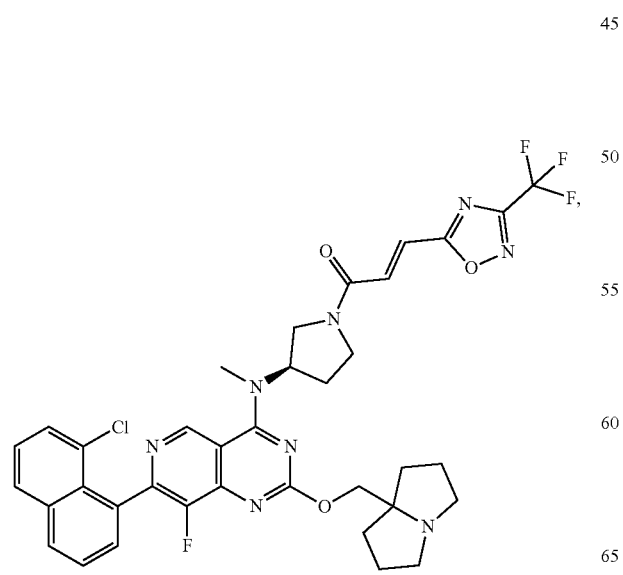
366
-continued
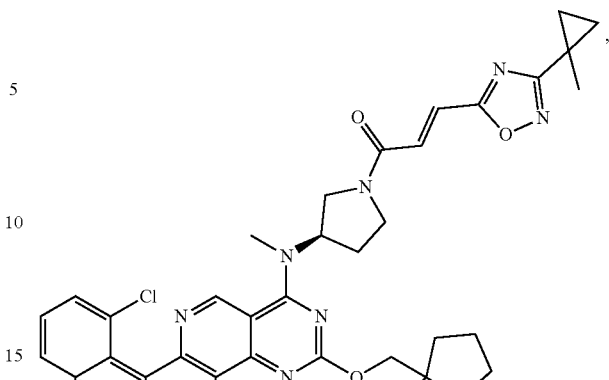
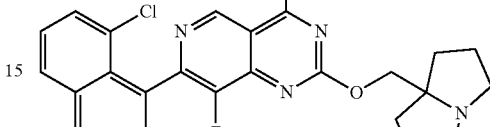
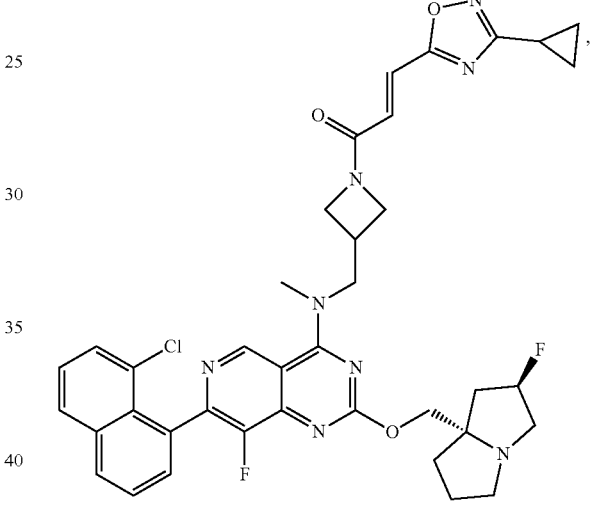
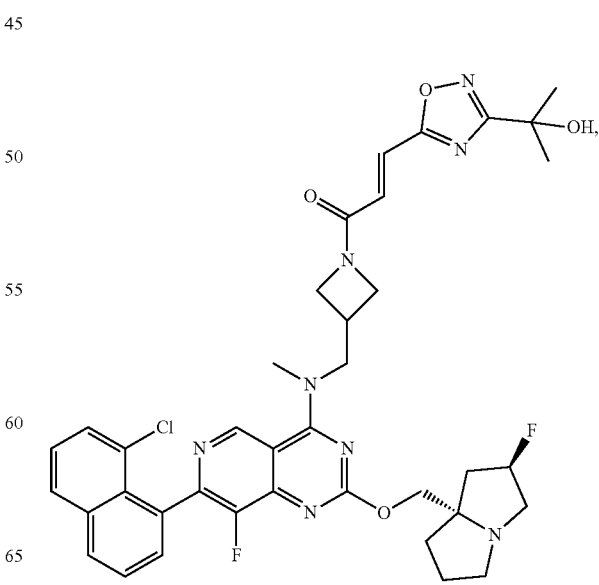

367
-continued
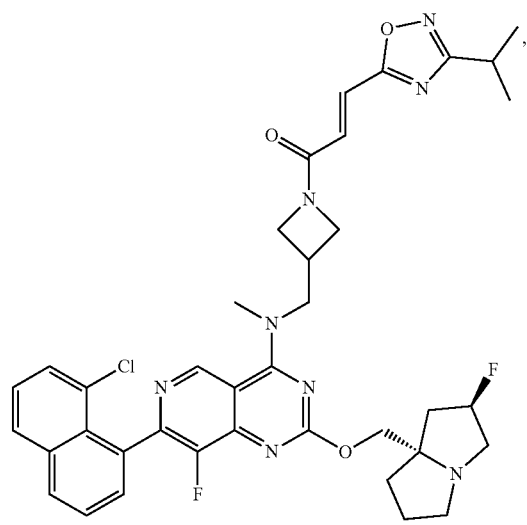
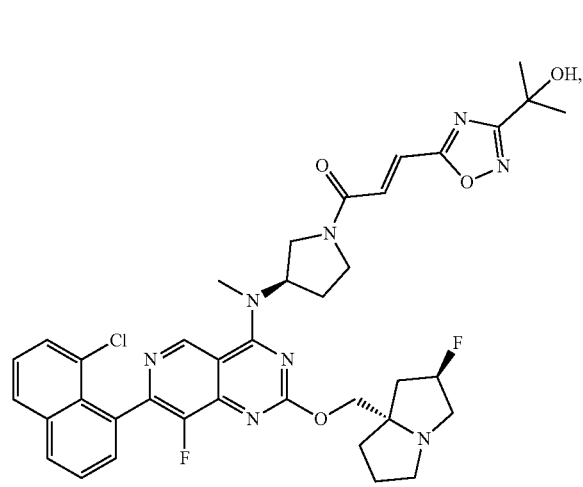
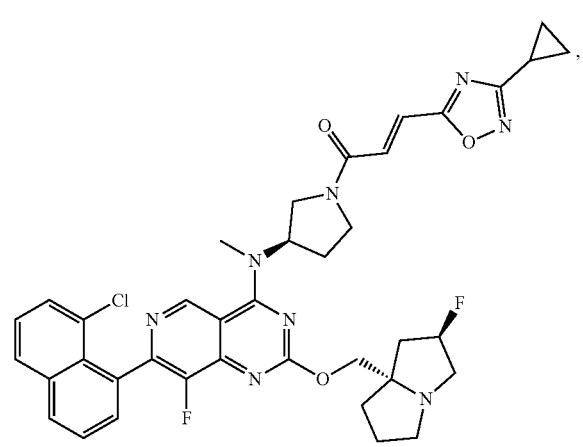
368
-continued
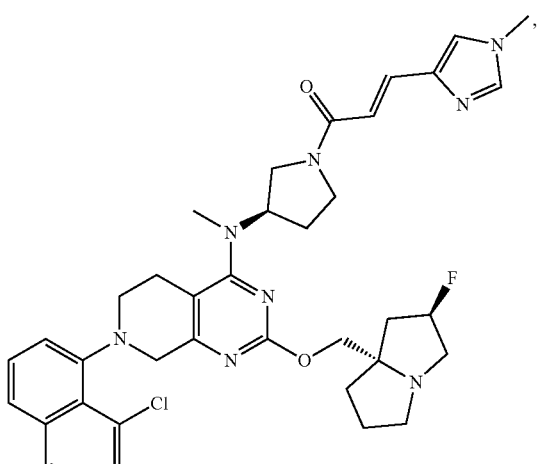
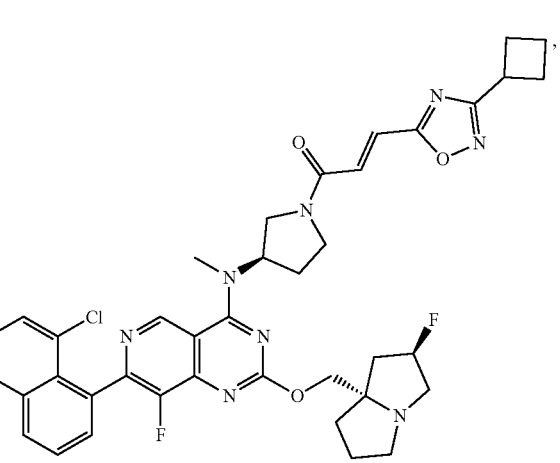
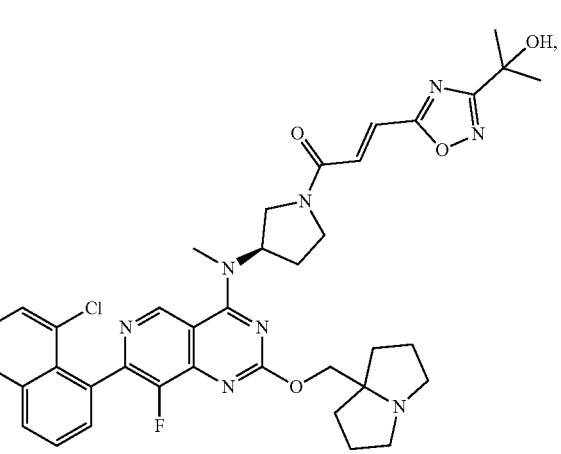

369
-continued
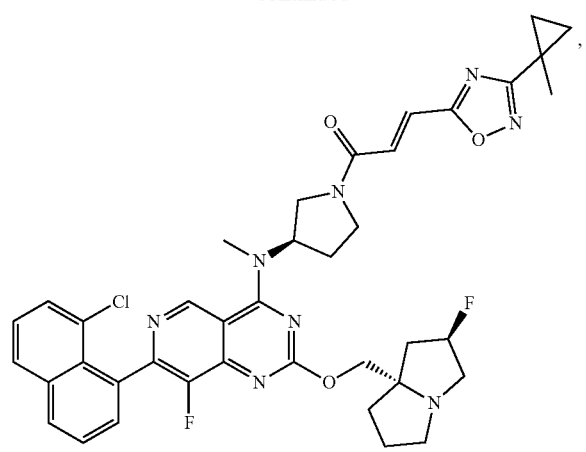
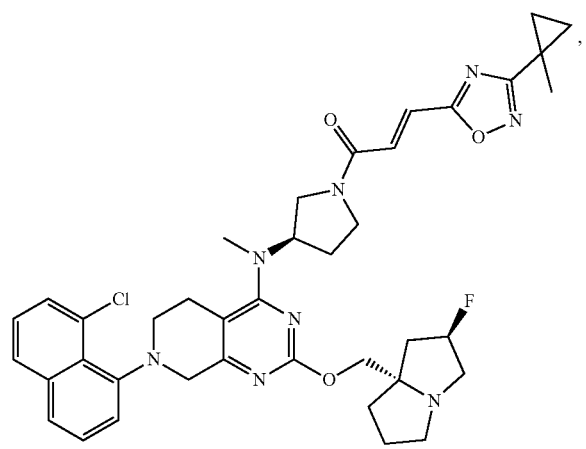
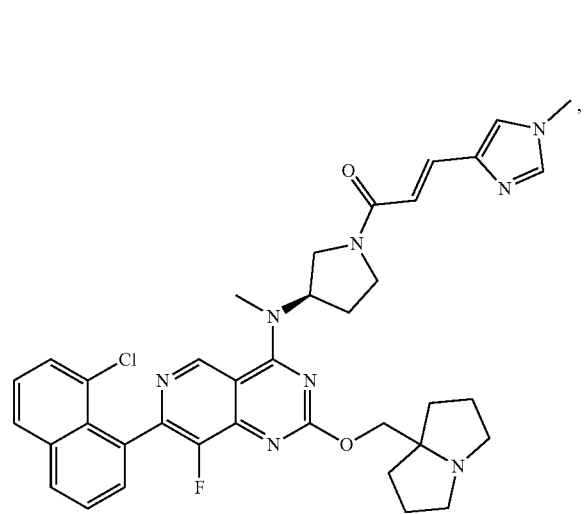
370
-continued
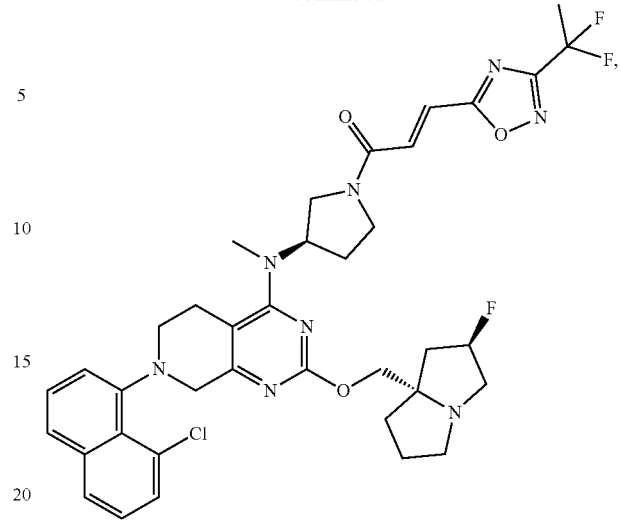
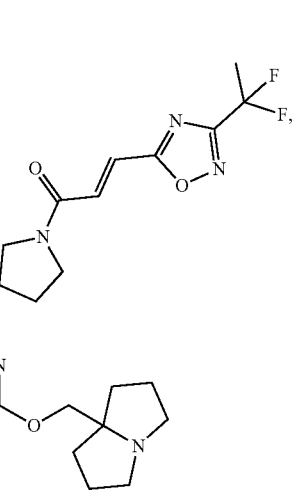
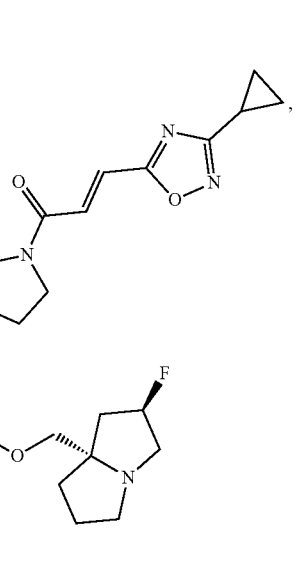

371
-continued
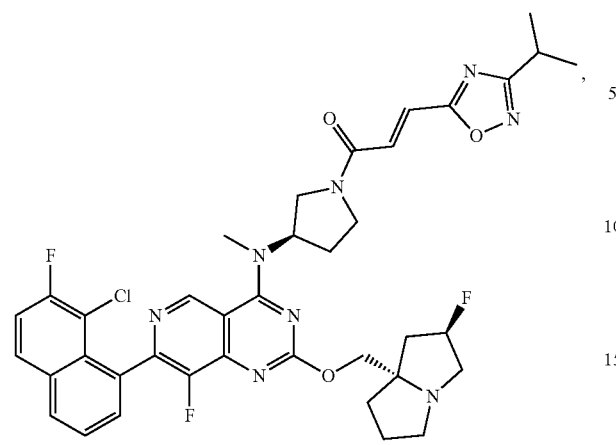
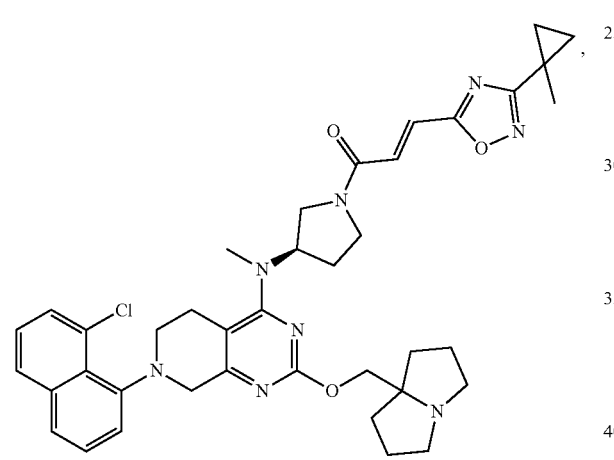
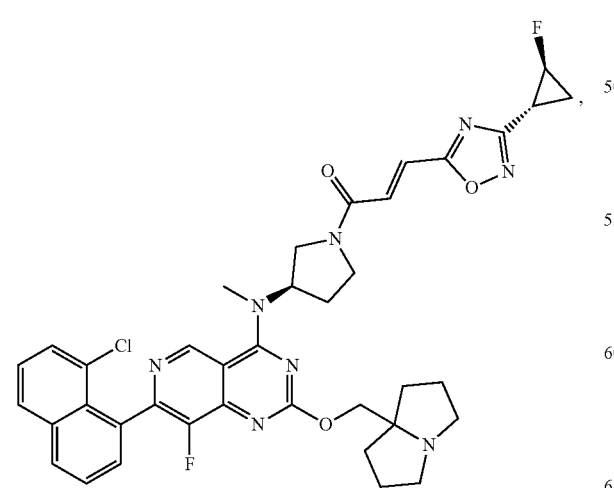
372
-continued
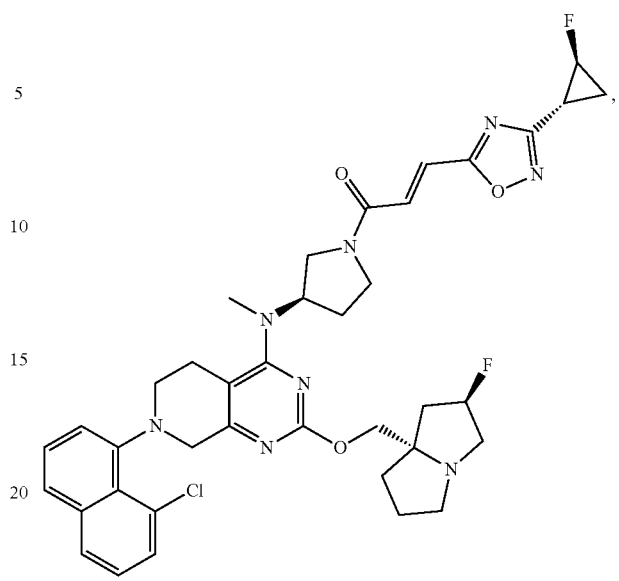
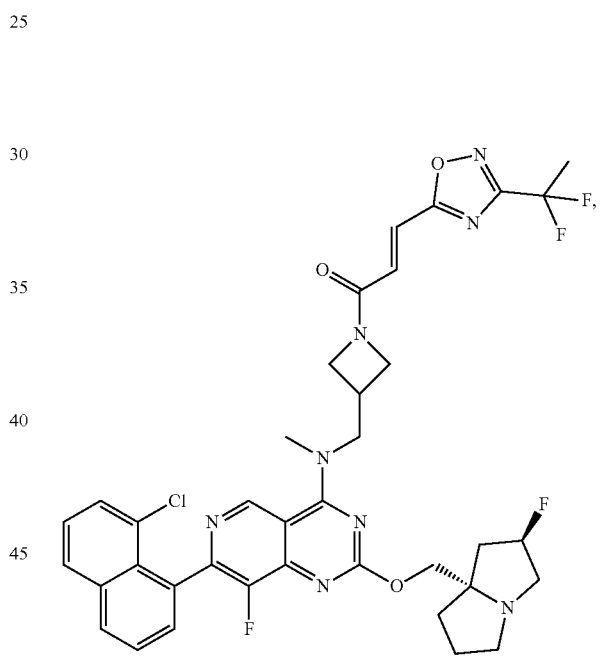
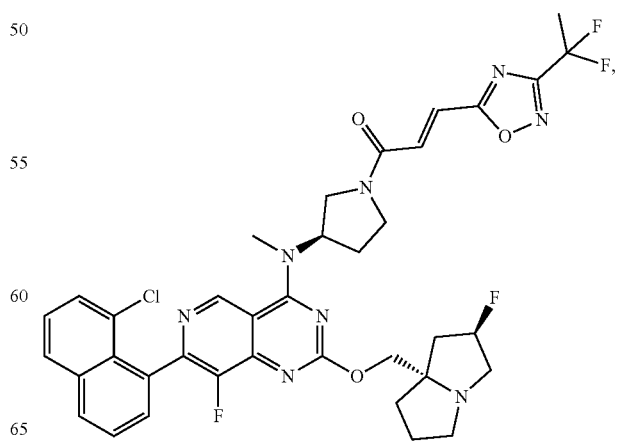

373
-continued
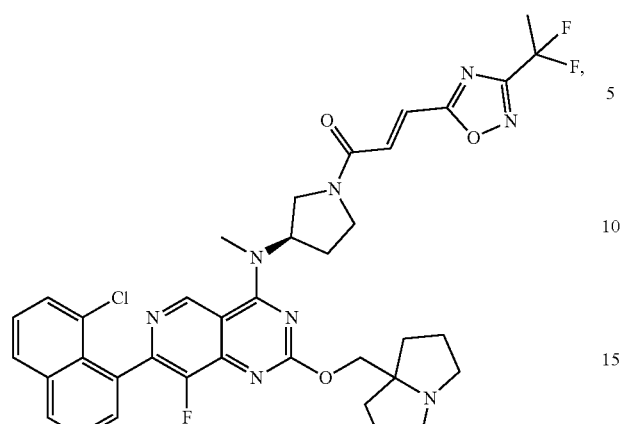
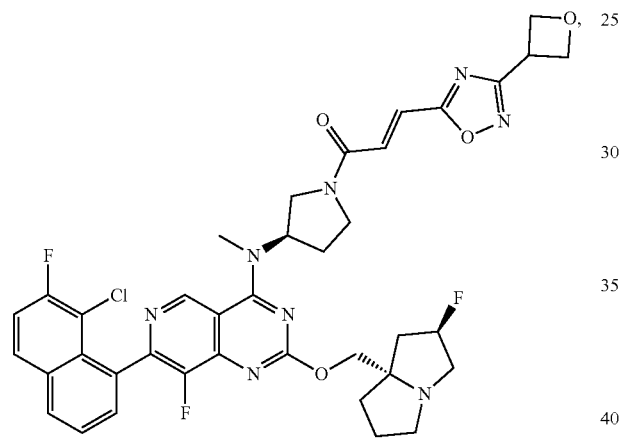
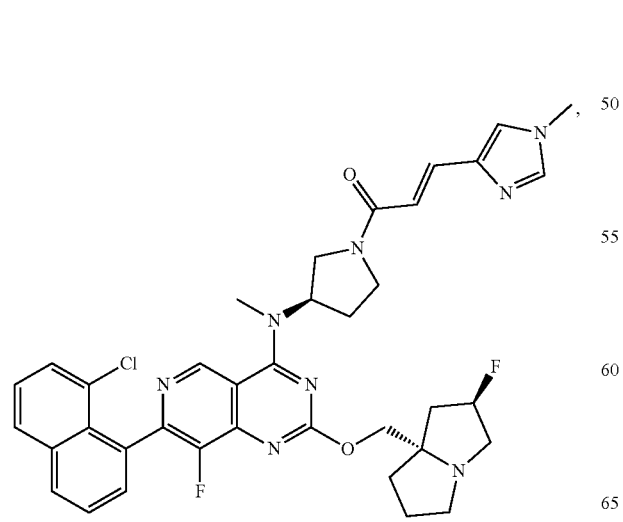
374
-continued
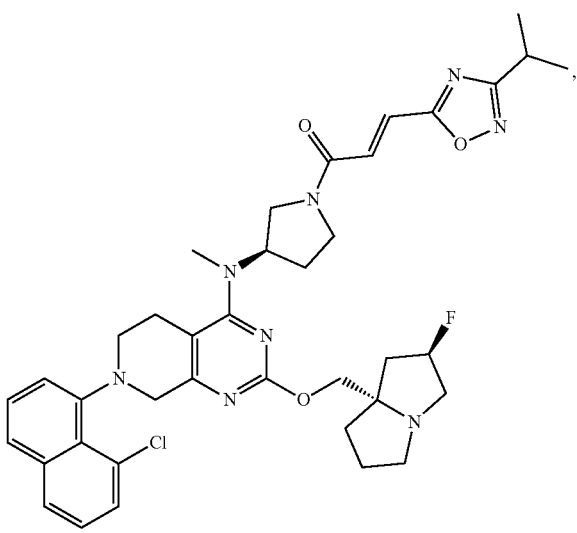
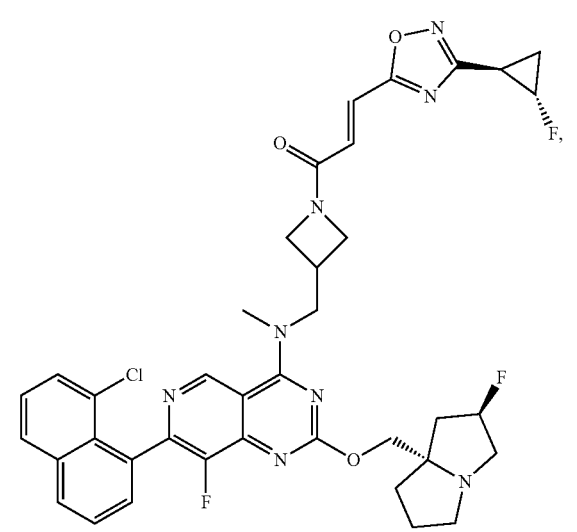

375
-continued
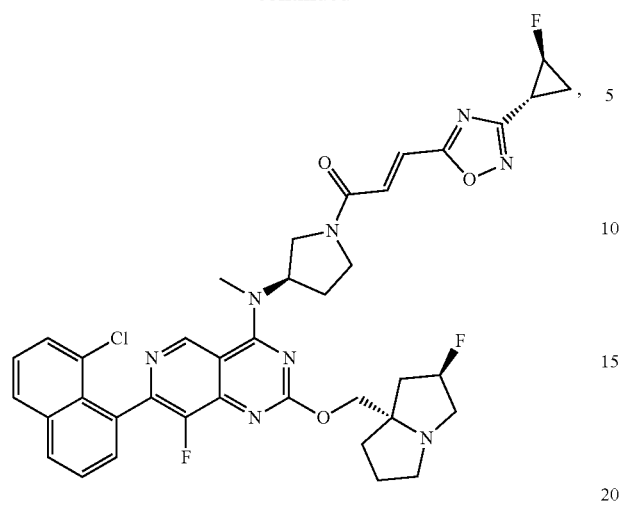
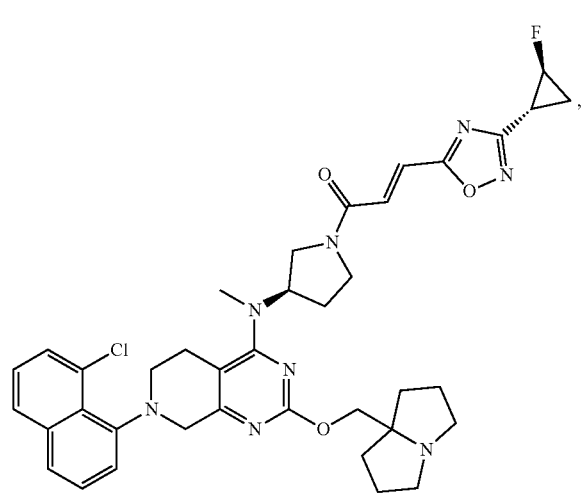
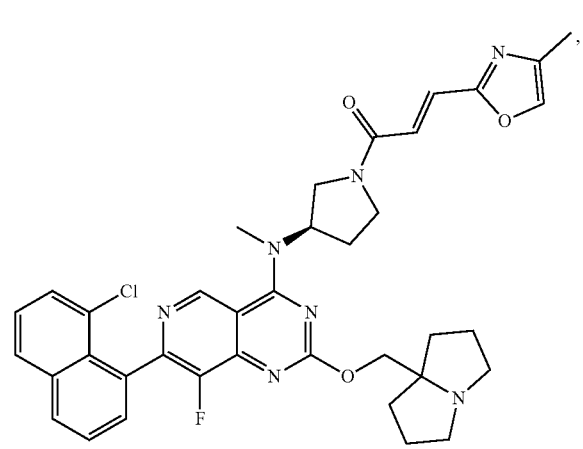
376
-continued
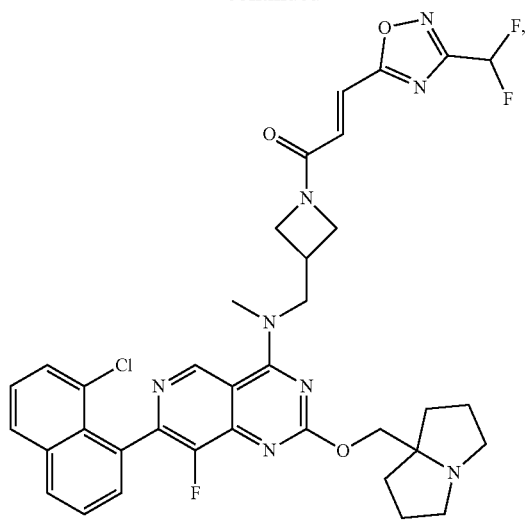
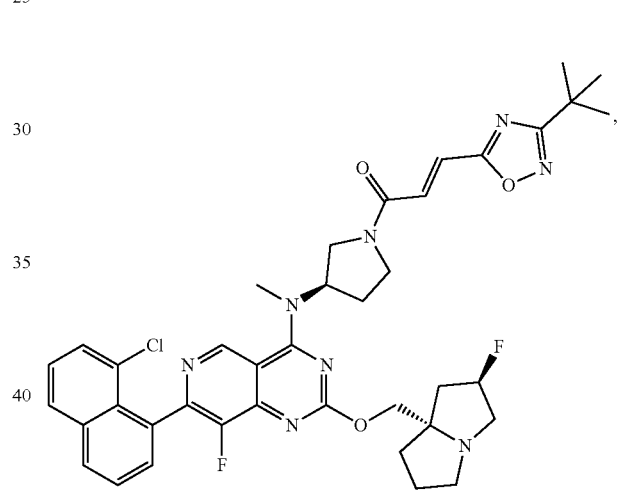
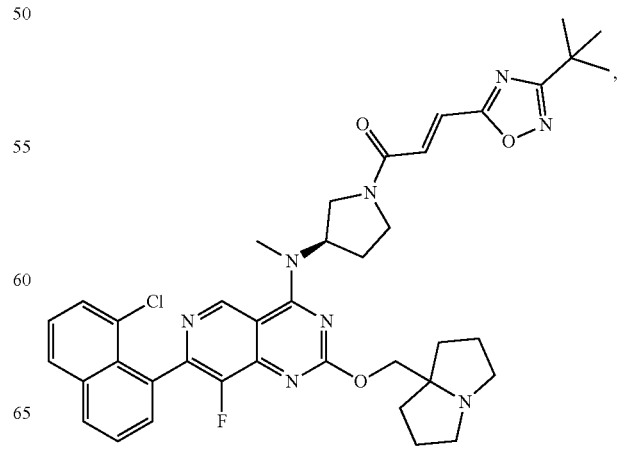

377
-continued
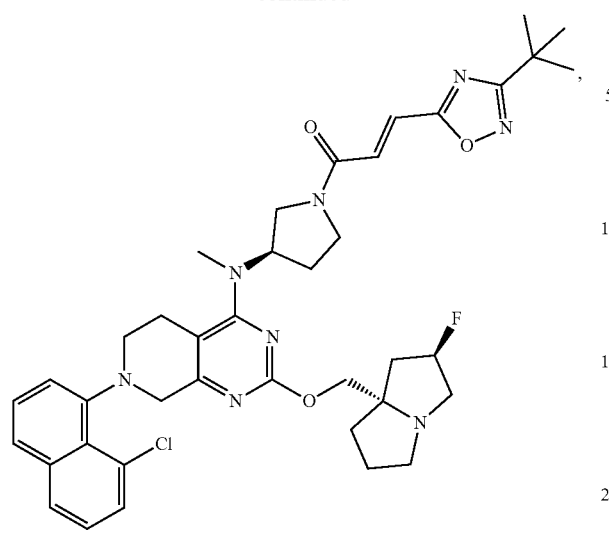
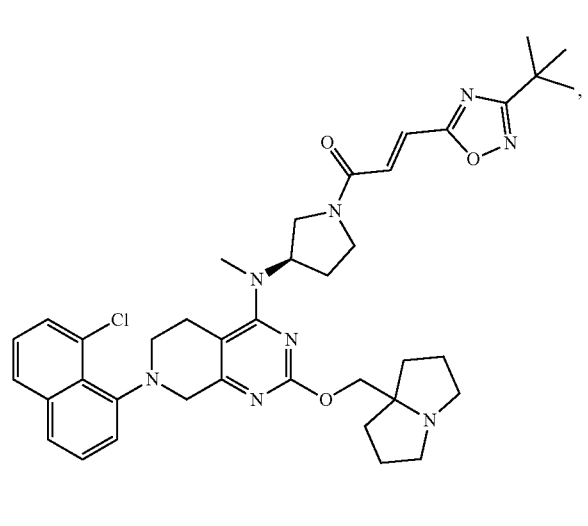
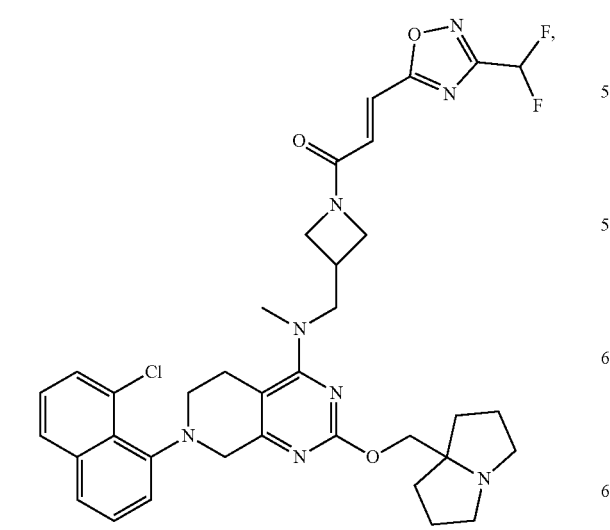
378
-continued
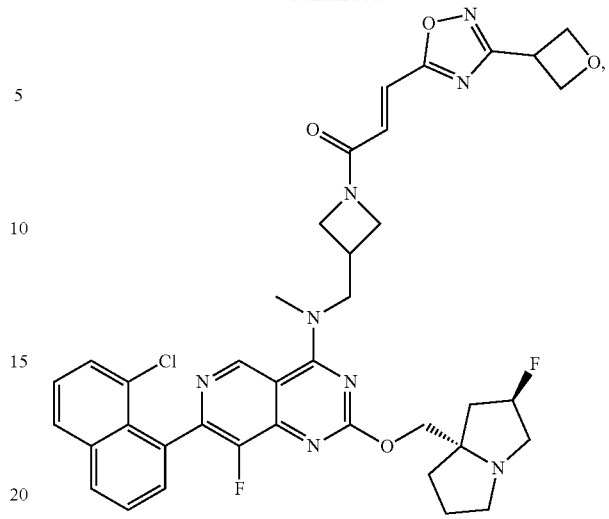

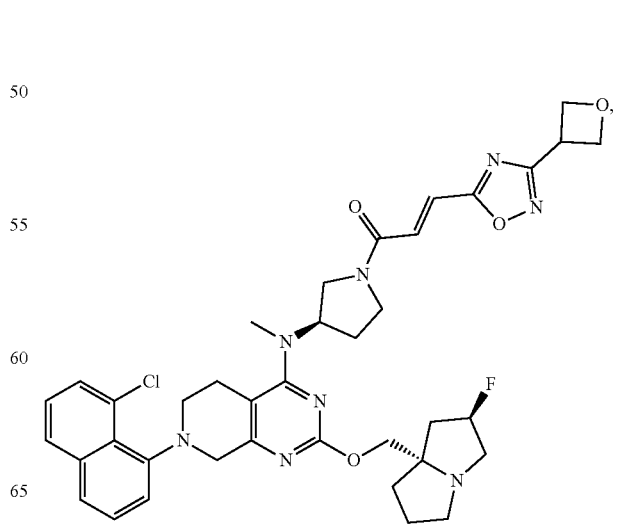

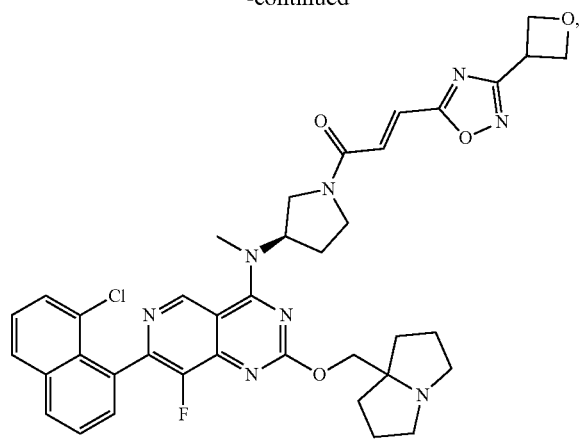
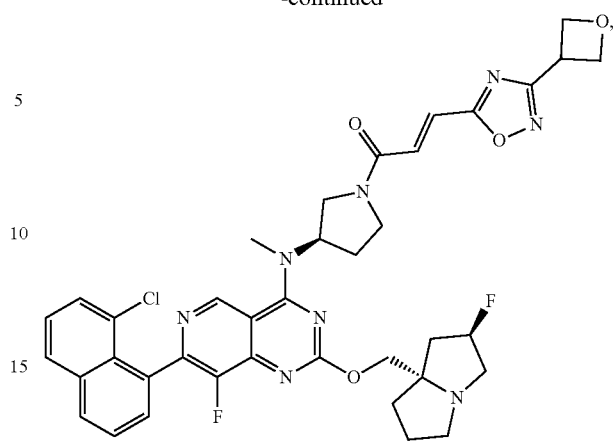
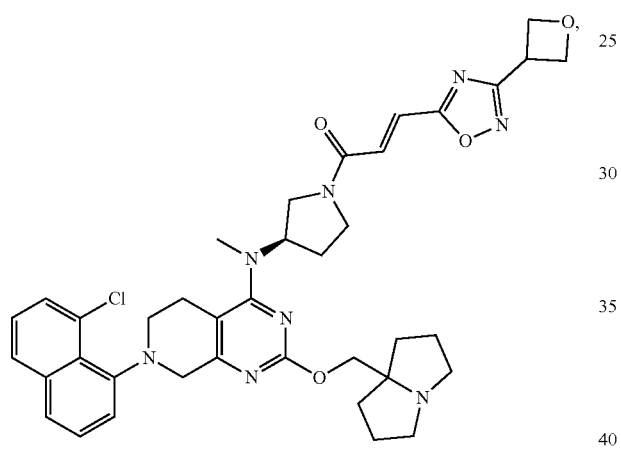
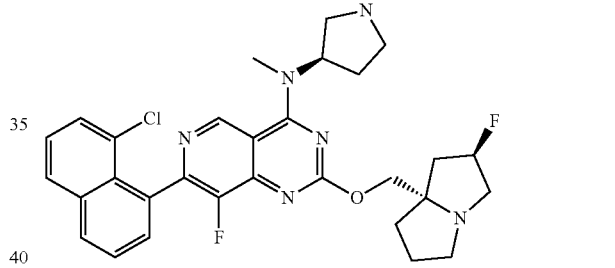
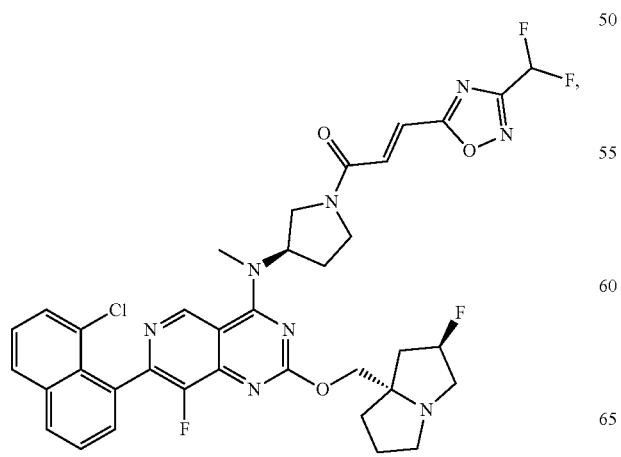
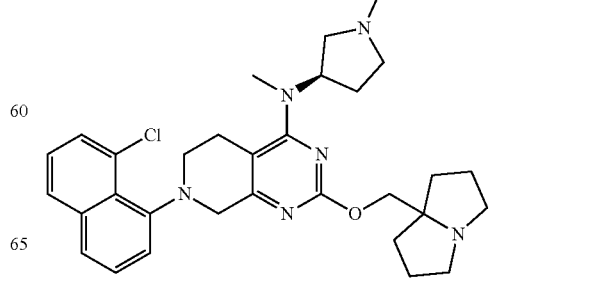

381
-continued
382
-continued
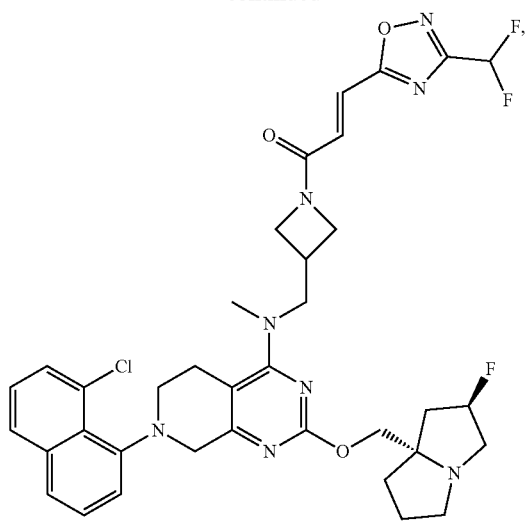
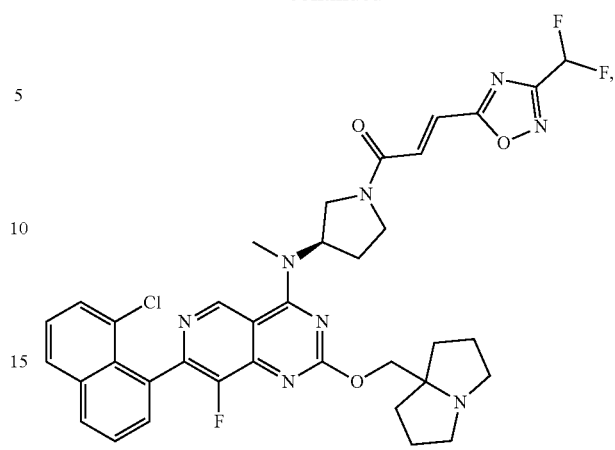

383
-continued
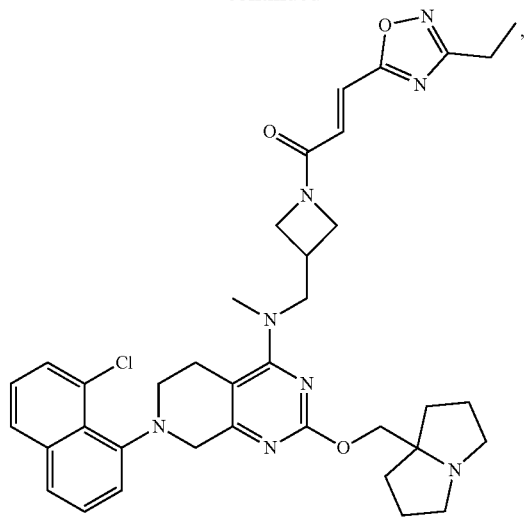
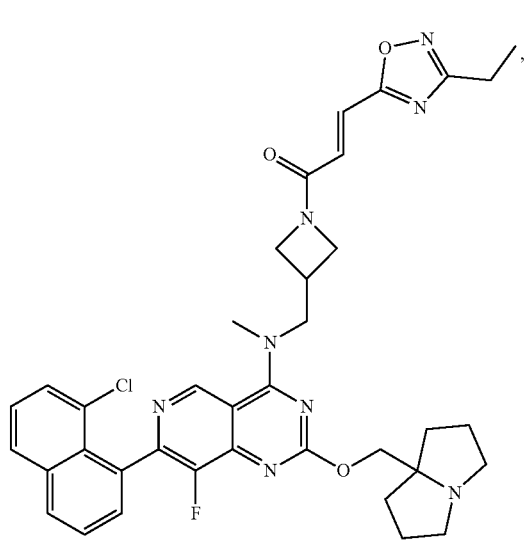
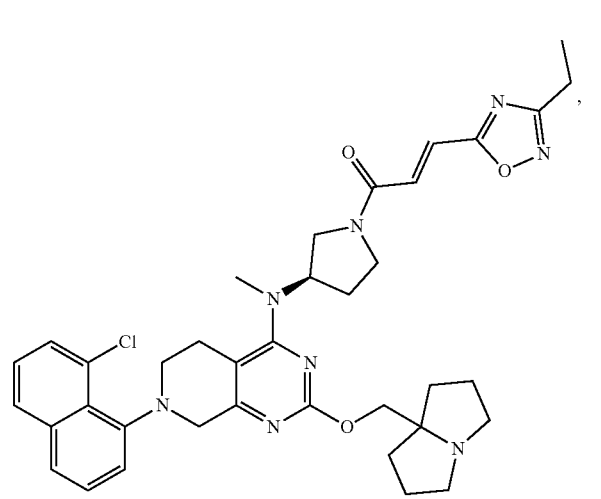
384
-continued
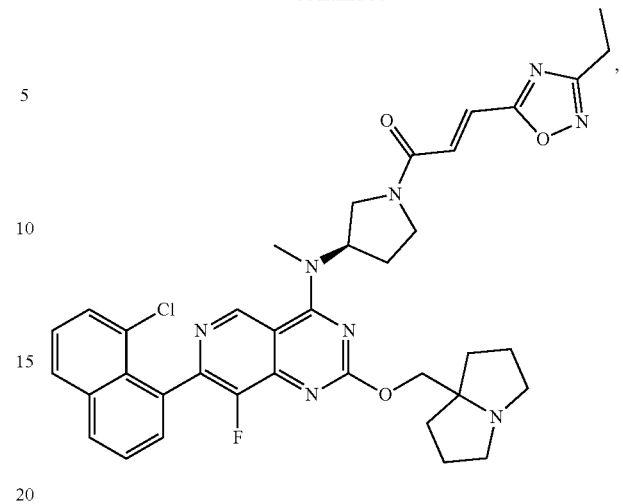
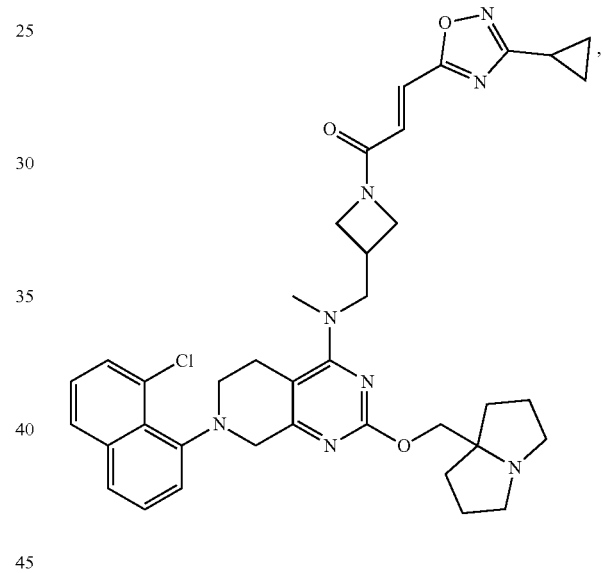
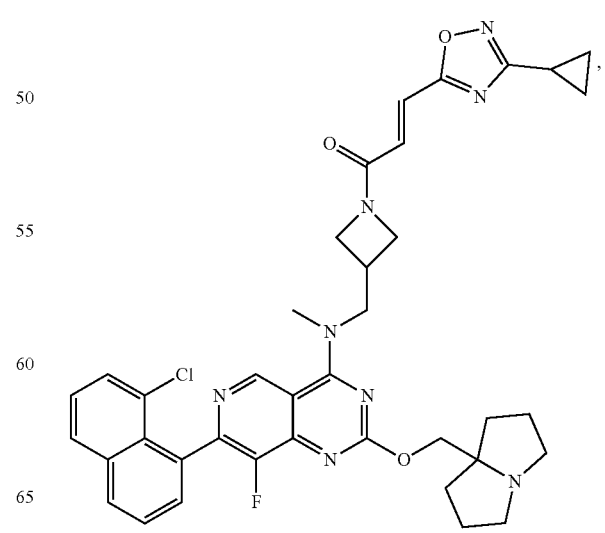

385
-continued
386
-continued
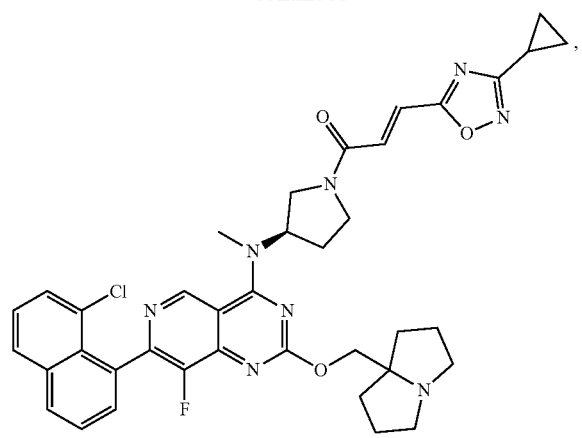
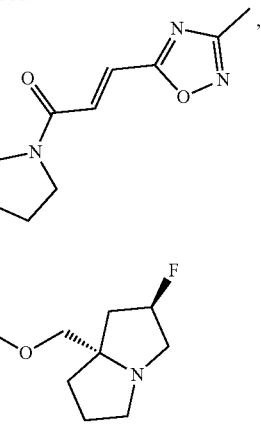
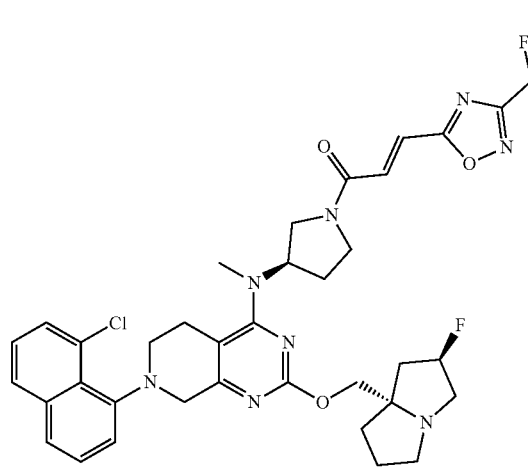
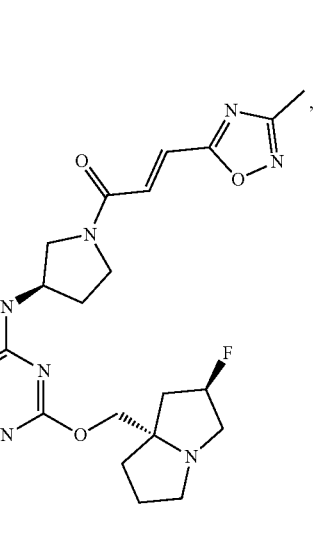
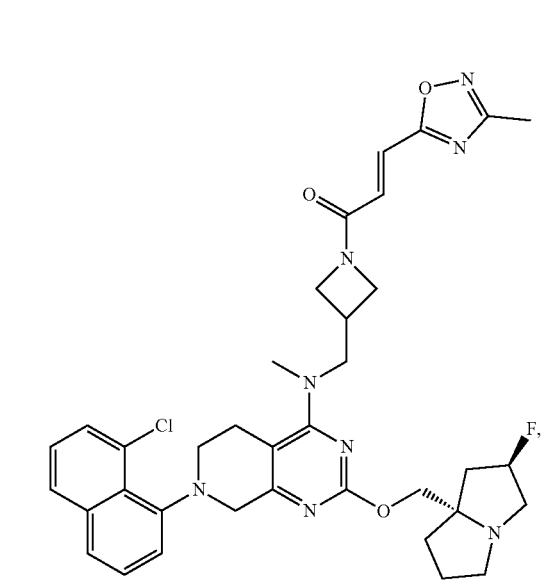
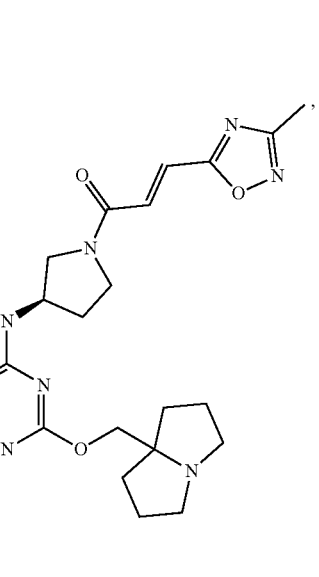

387
-continued
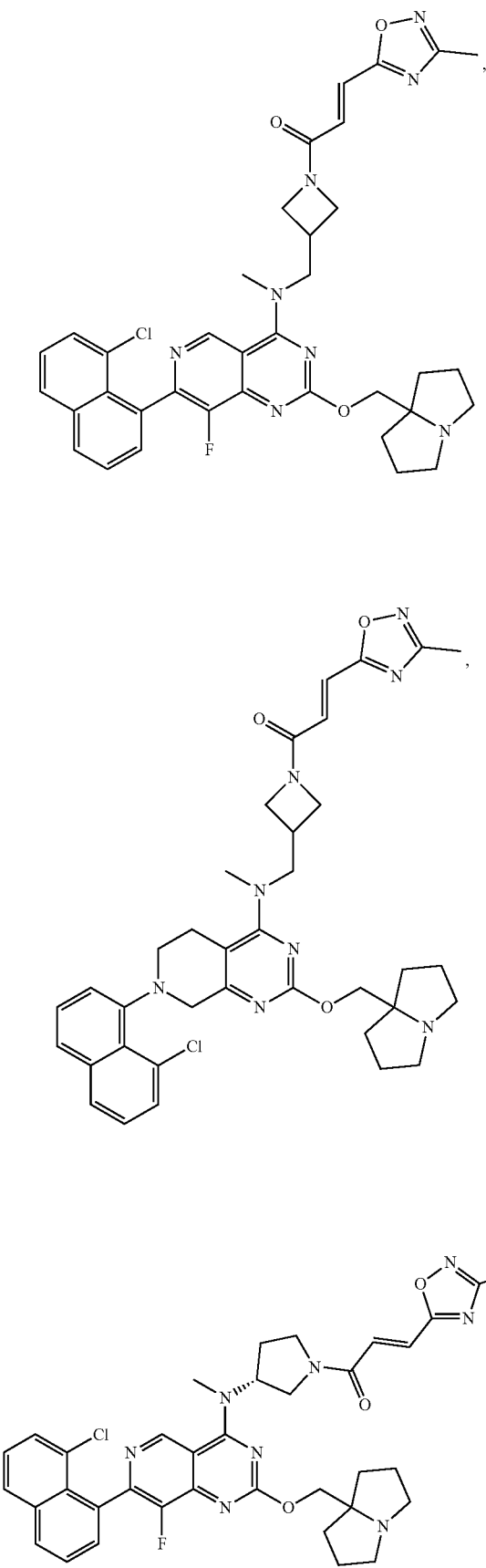
388
-continued
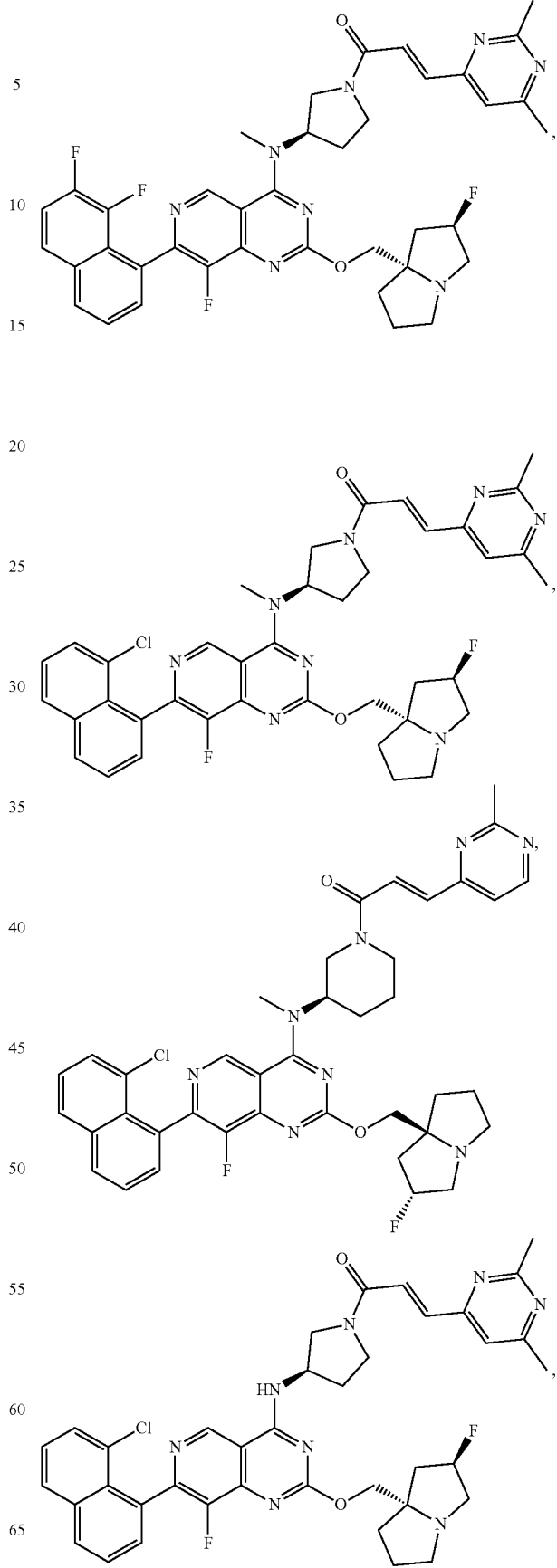

389
-continued
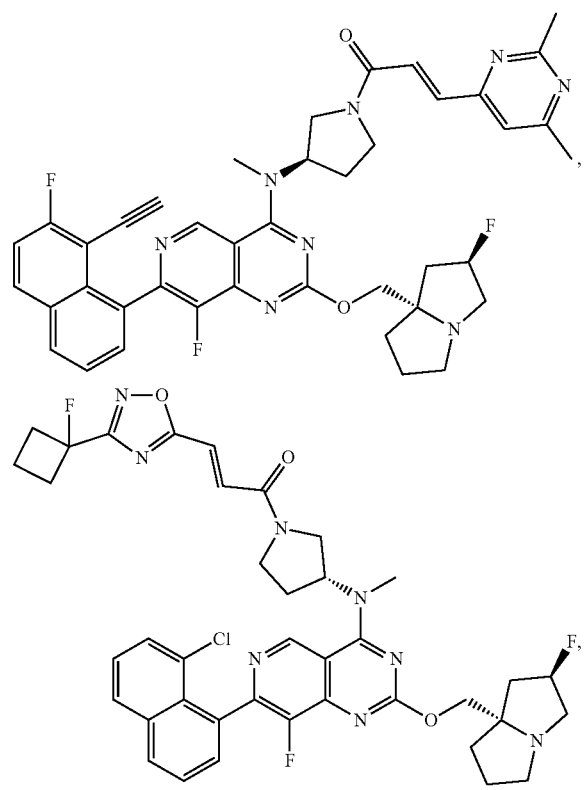
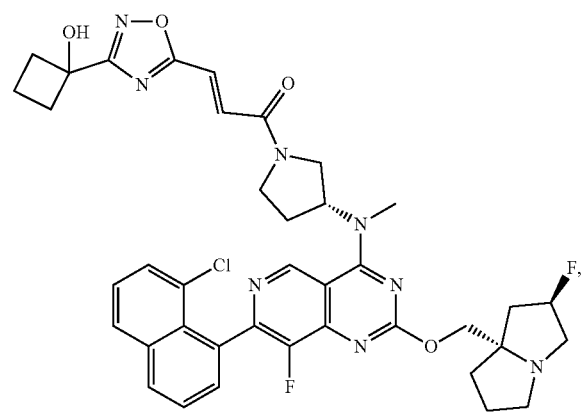
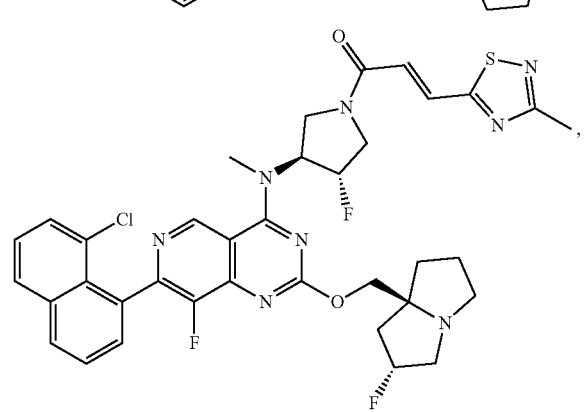
390
-continued
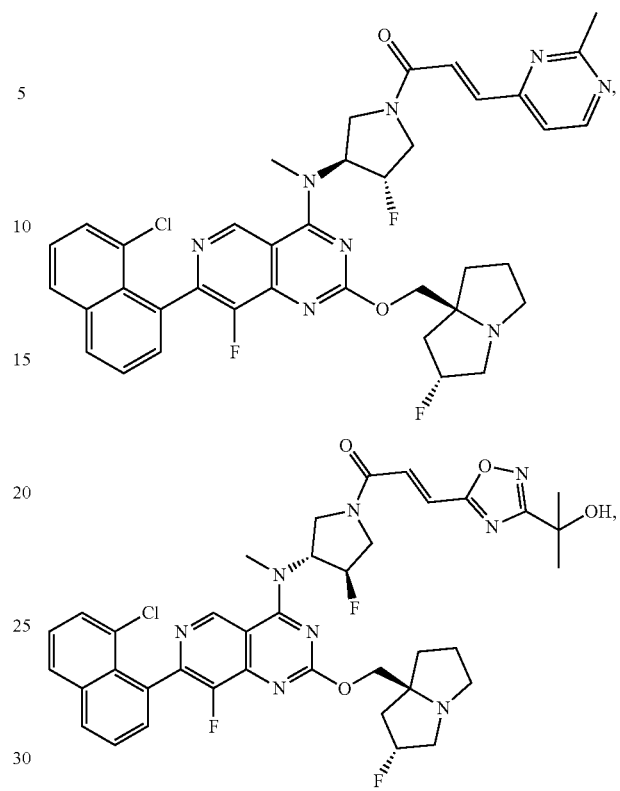
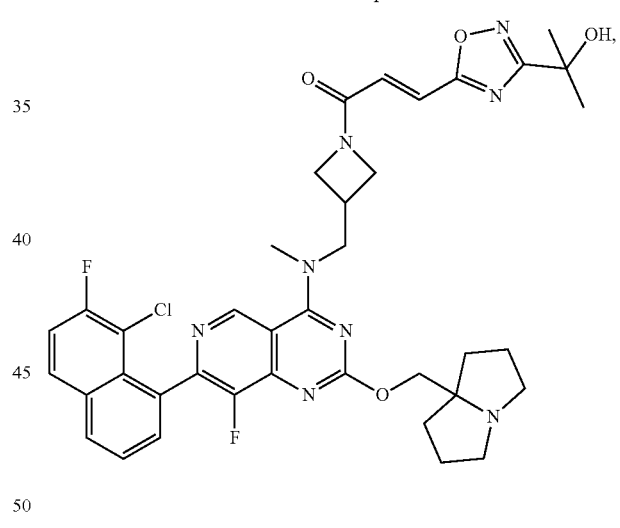
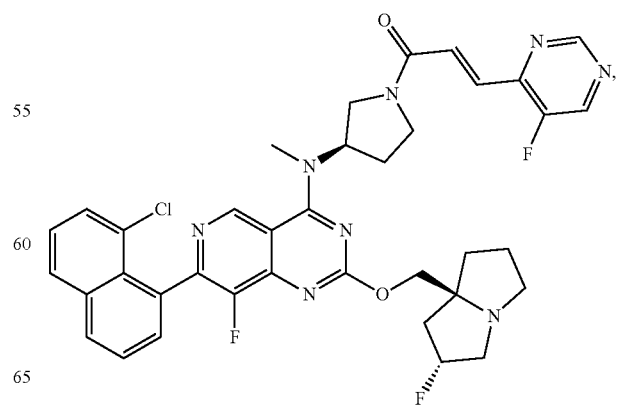

391
-continued
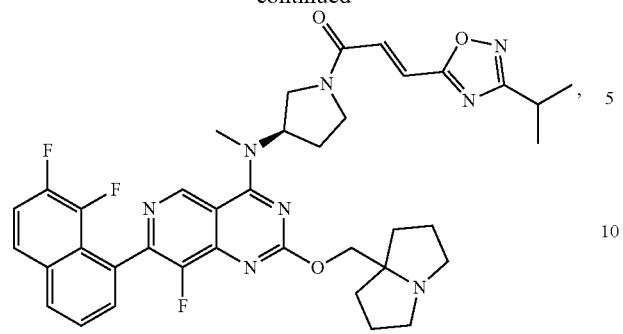

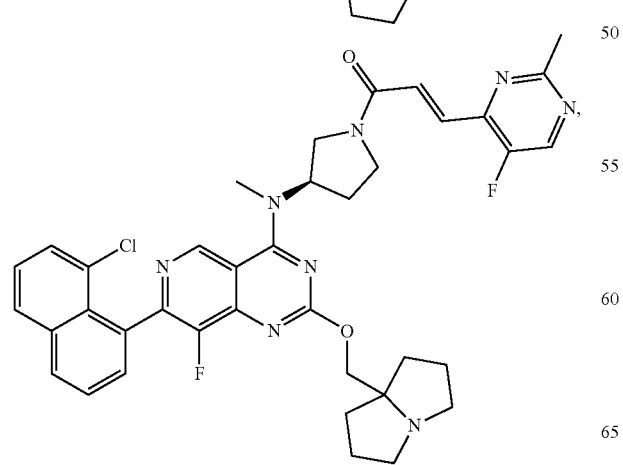
392
-continued
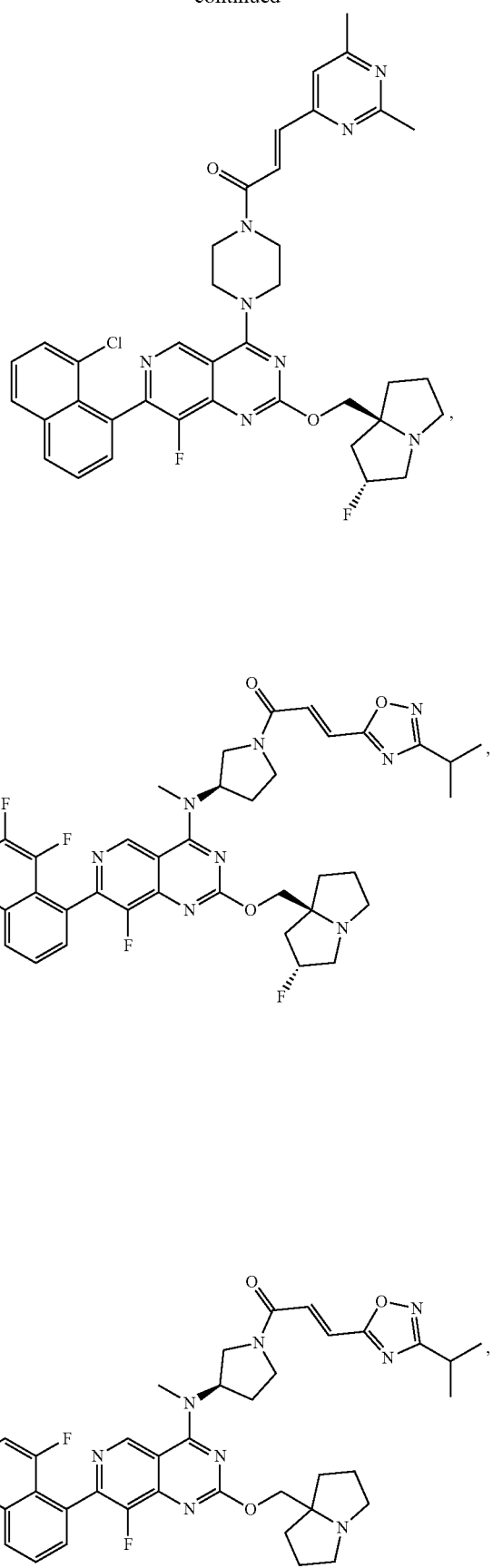

393
-continued
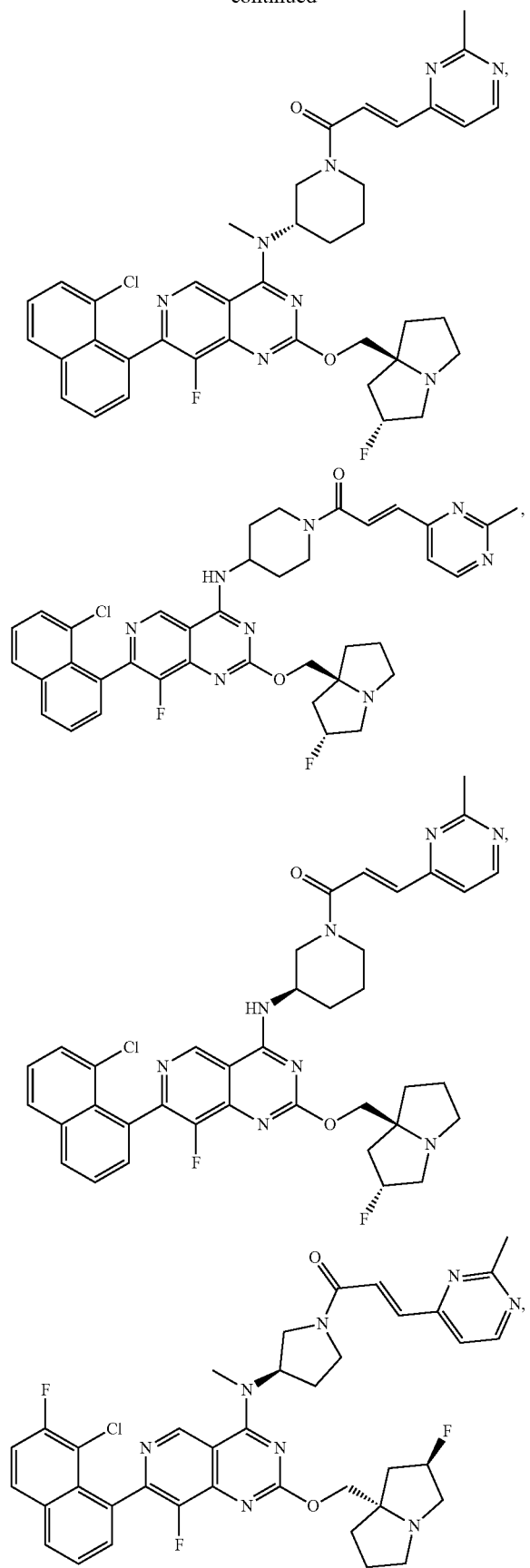
394
-continued
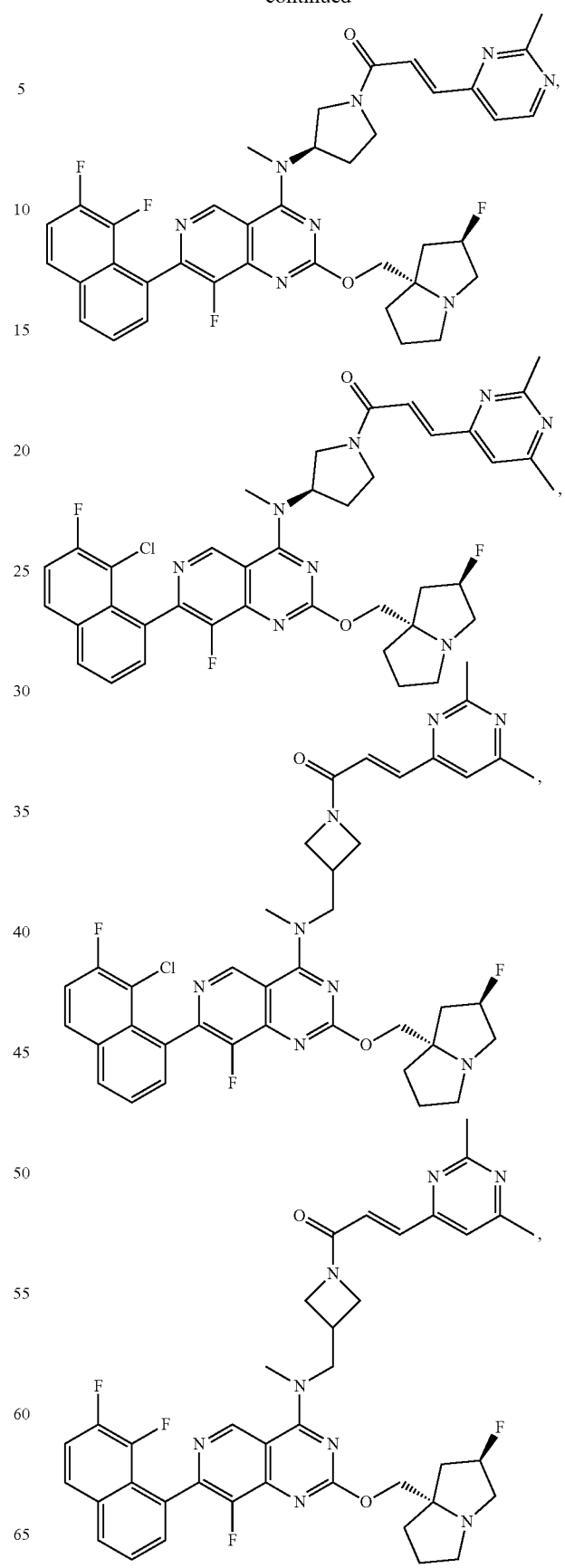

395
-continued
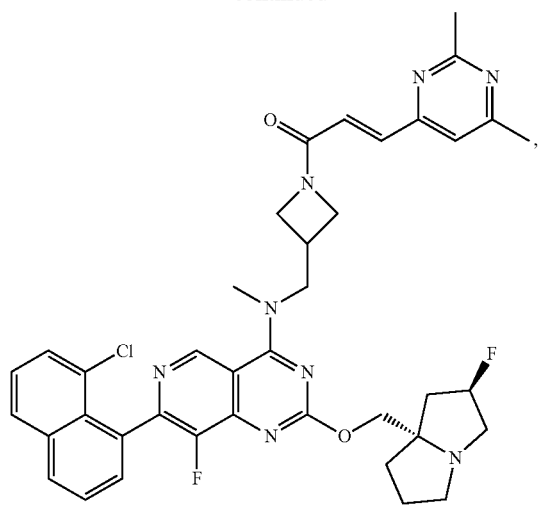
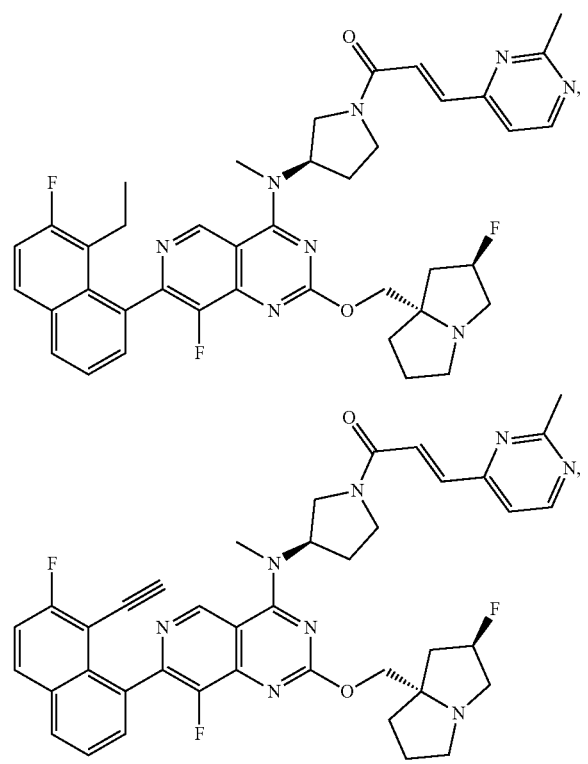
396
-continued
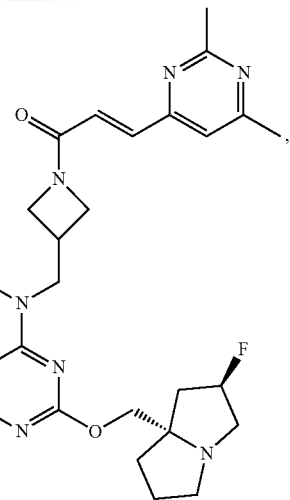
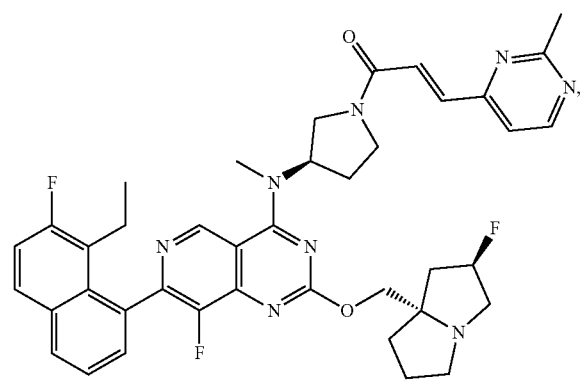
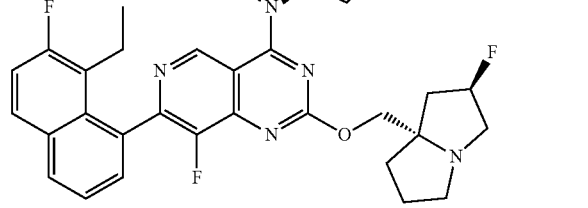

-continued
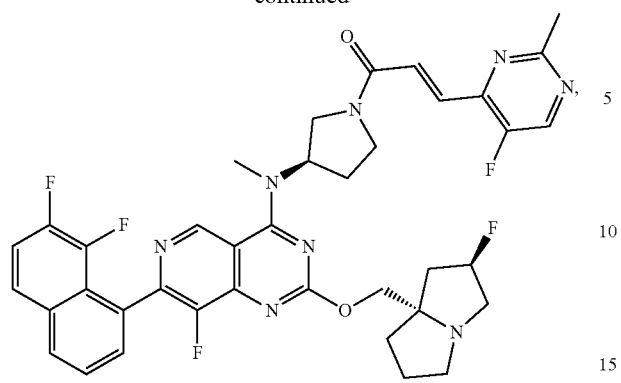
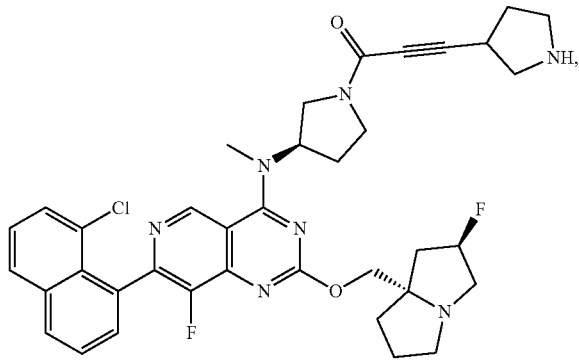
and
all salts and isotopologues thereof.
Embodiment 437. The compound of embodiment 1 or 11, selected from:
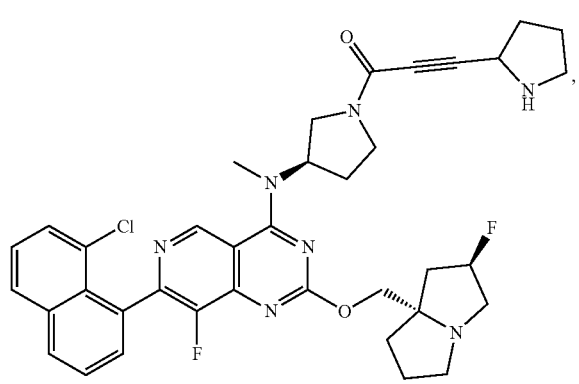
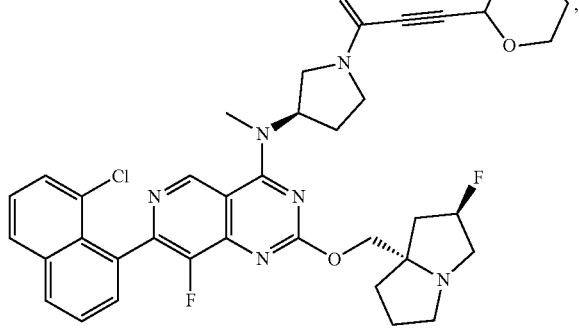
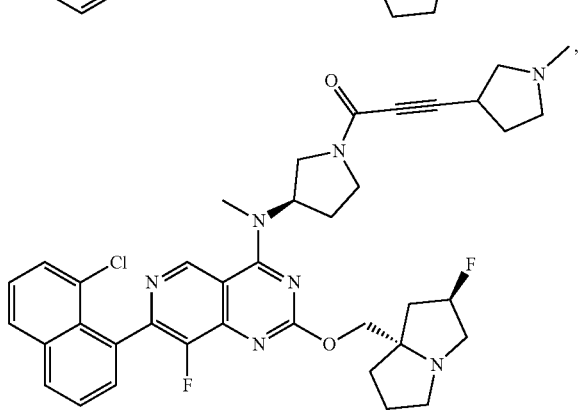

399
-continued
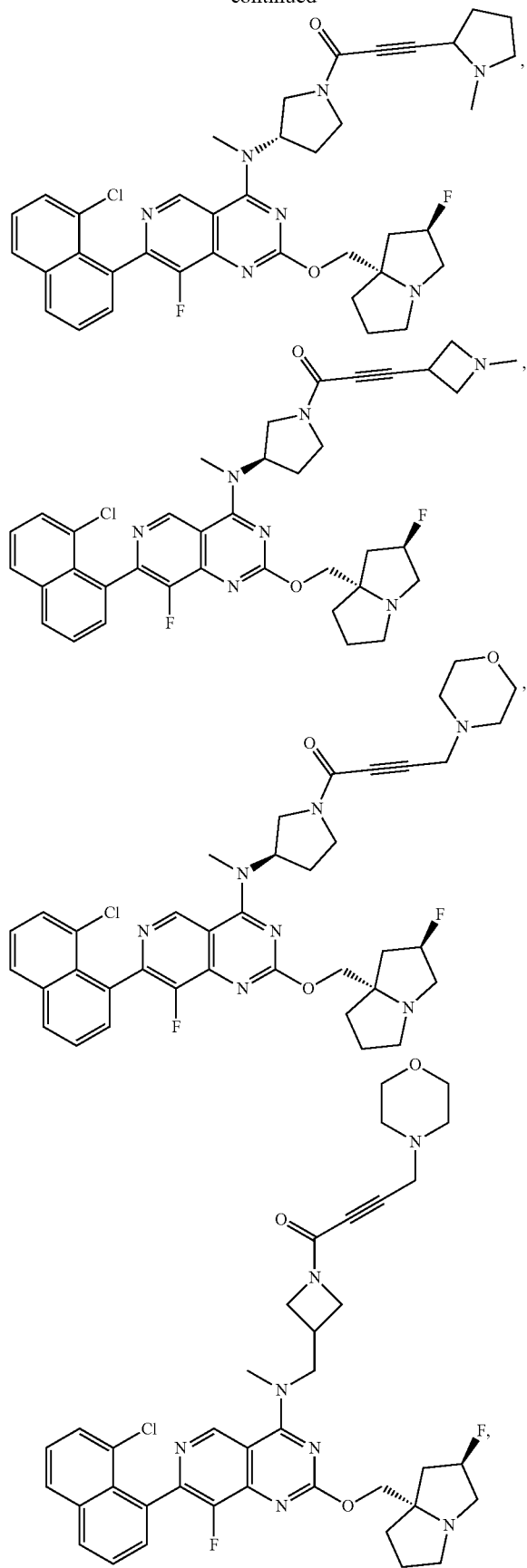
400
-continued
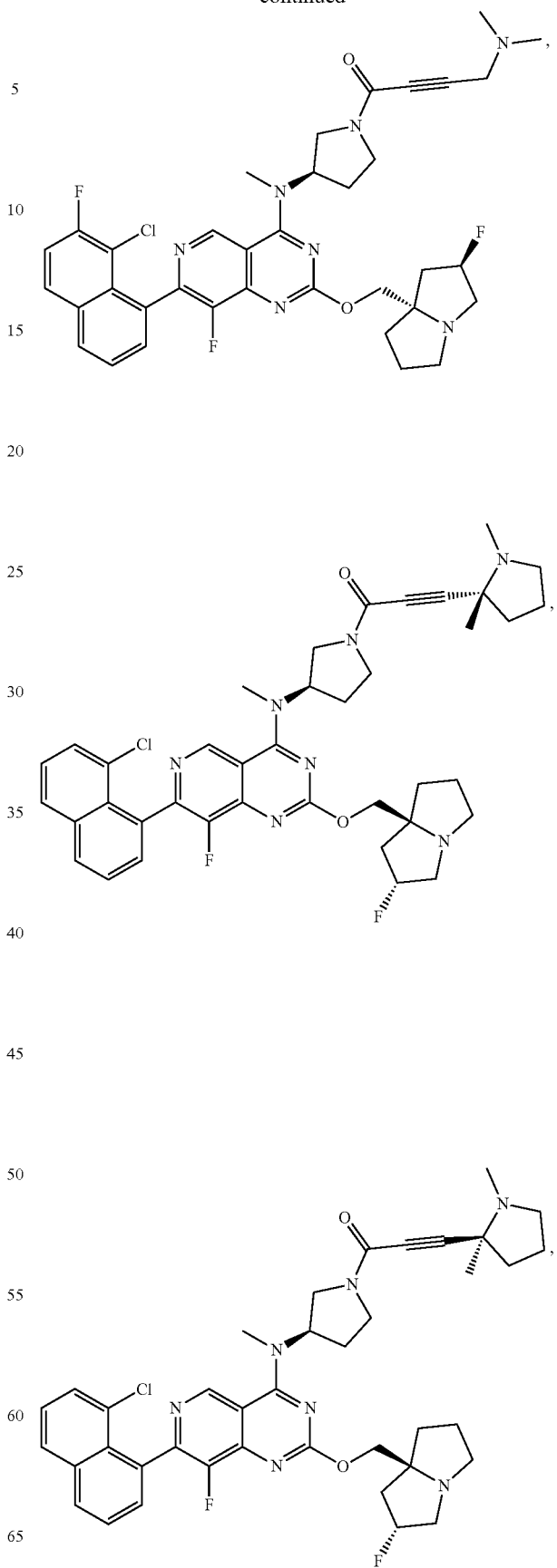

401
-continued
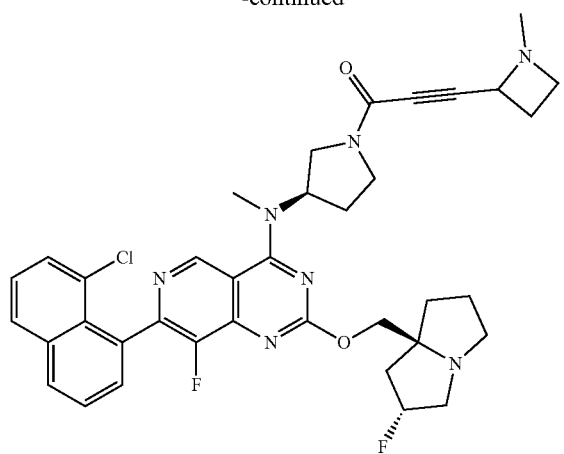
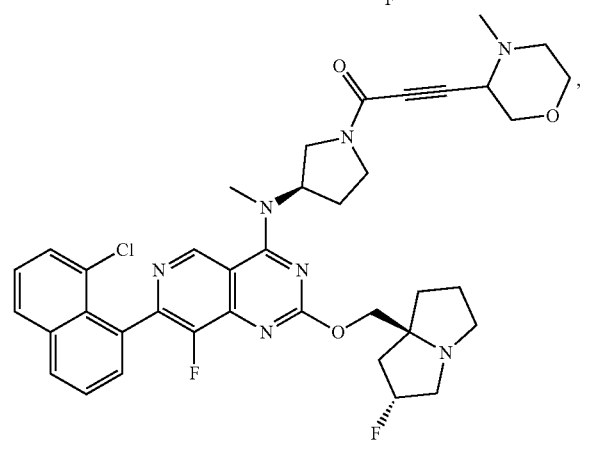
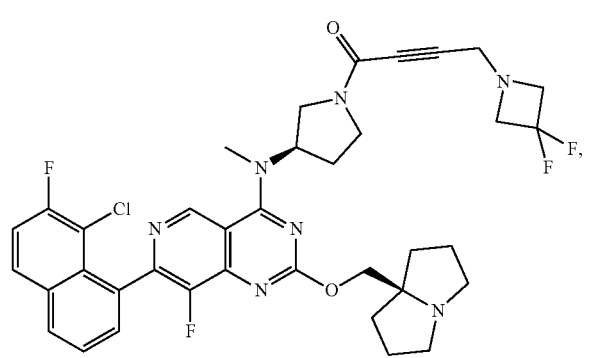
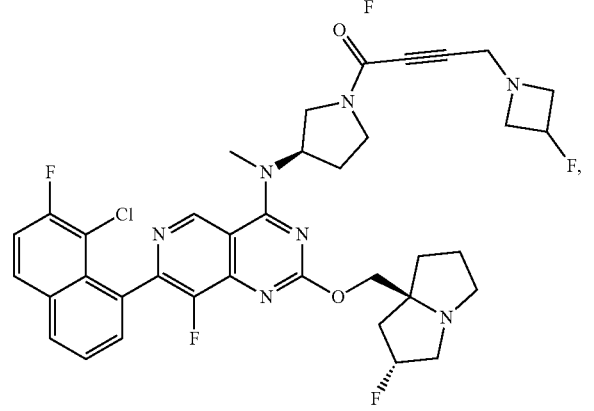
402
-continued
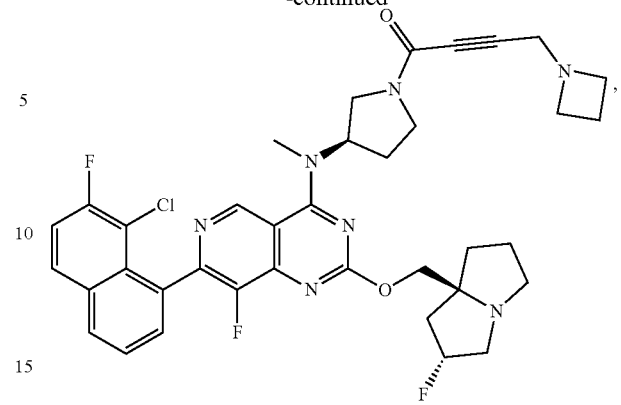
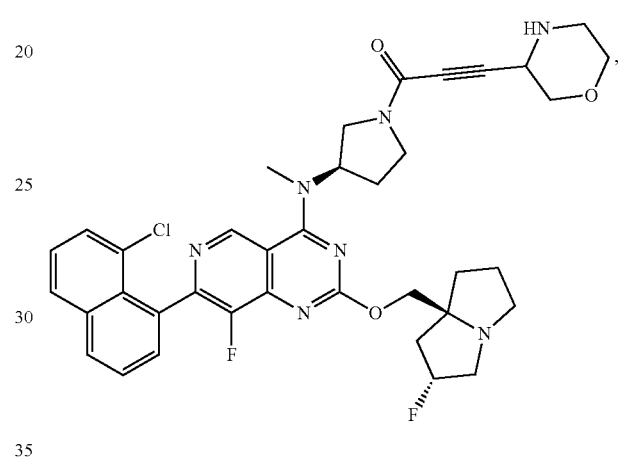
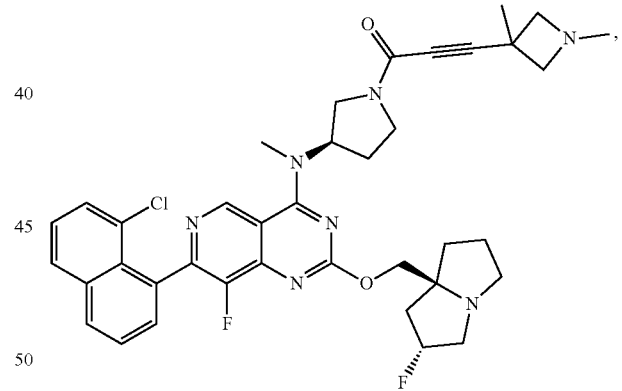
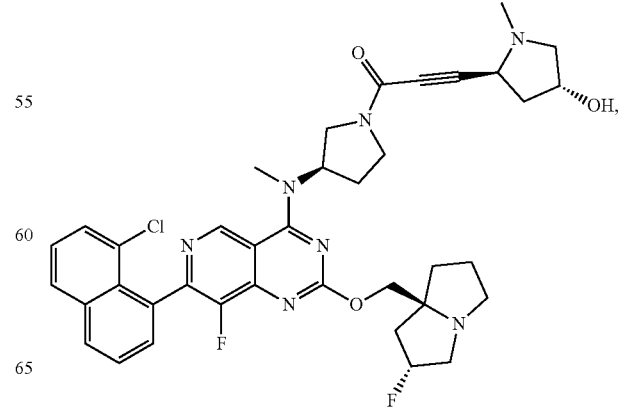

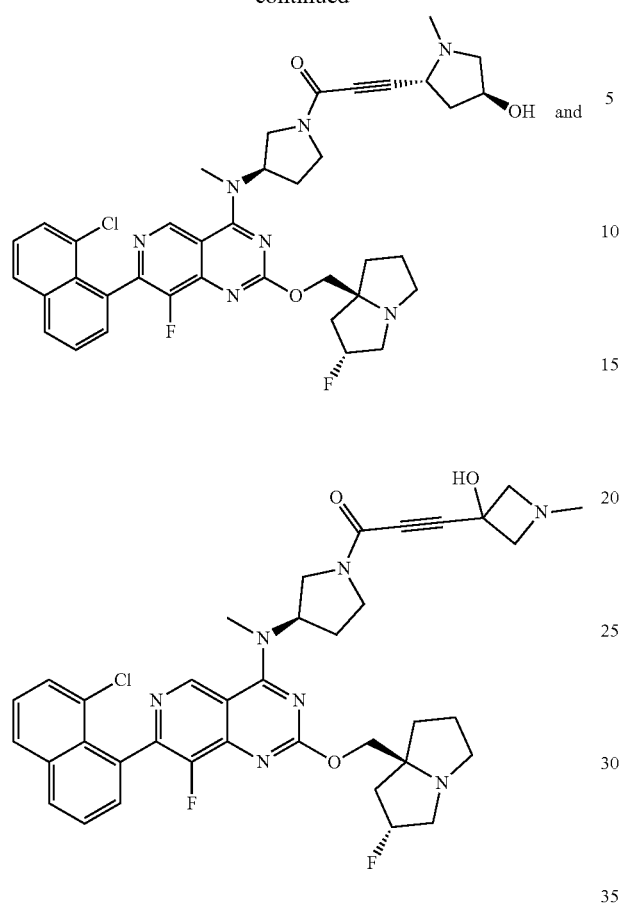
and all salts and isotopologues thereof.
Embodiment 438. The compound of any one of embodiments 1, 11 and 18, selected from:
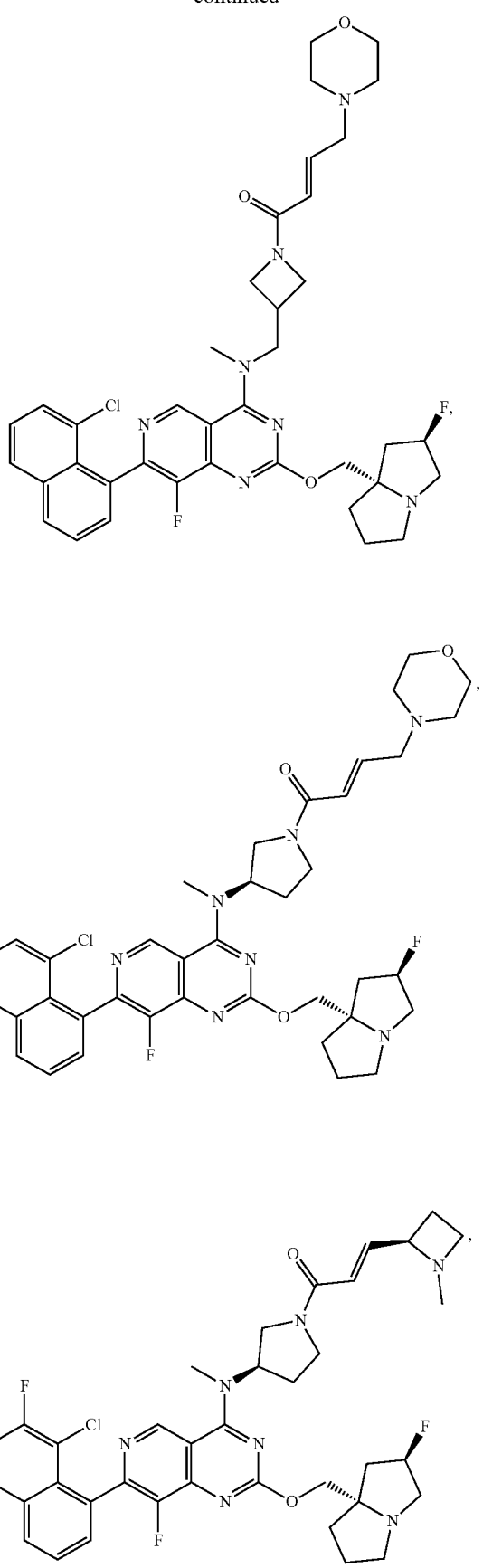

405
-continued
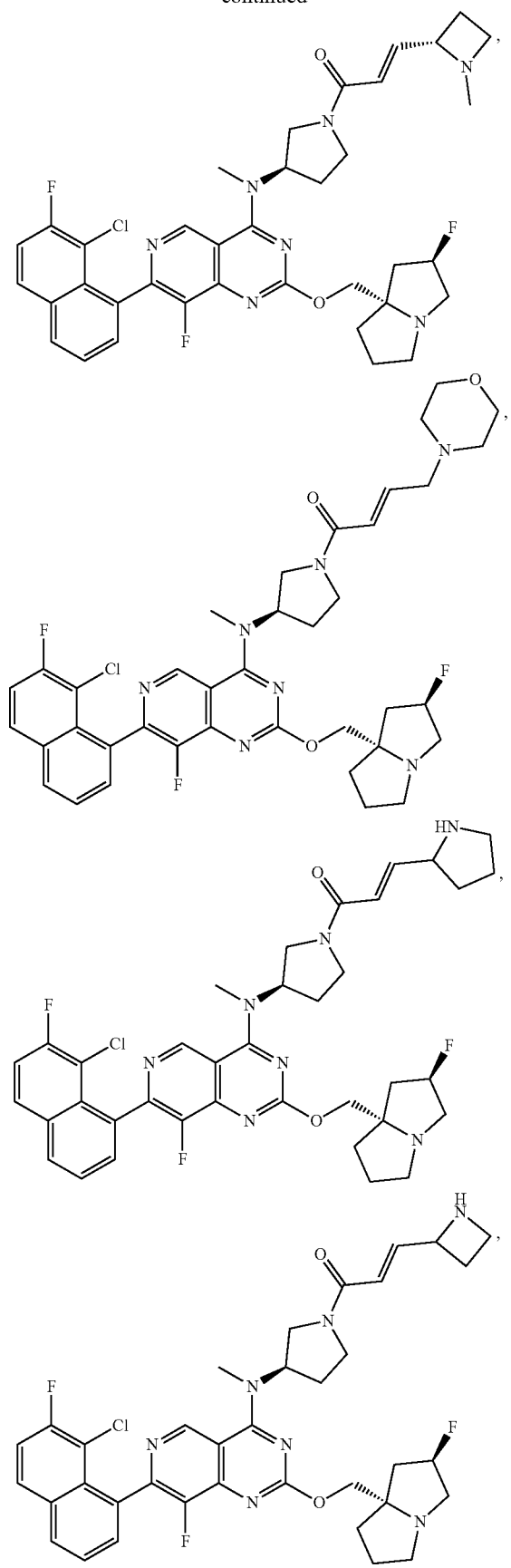
406
-continued
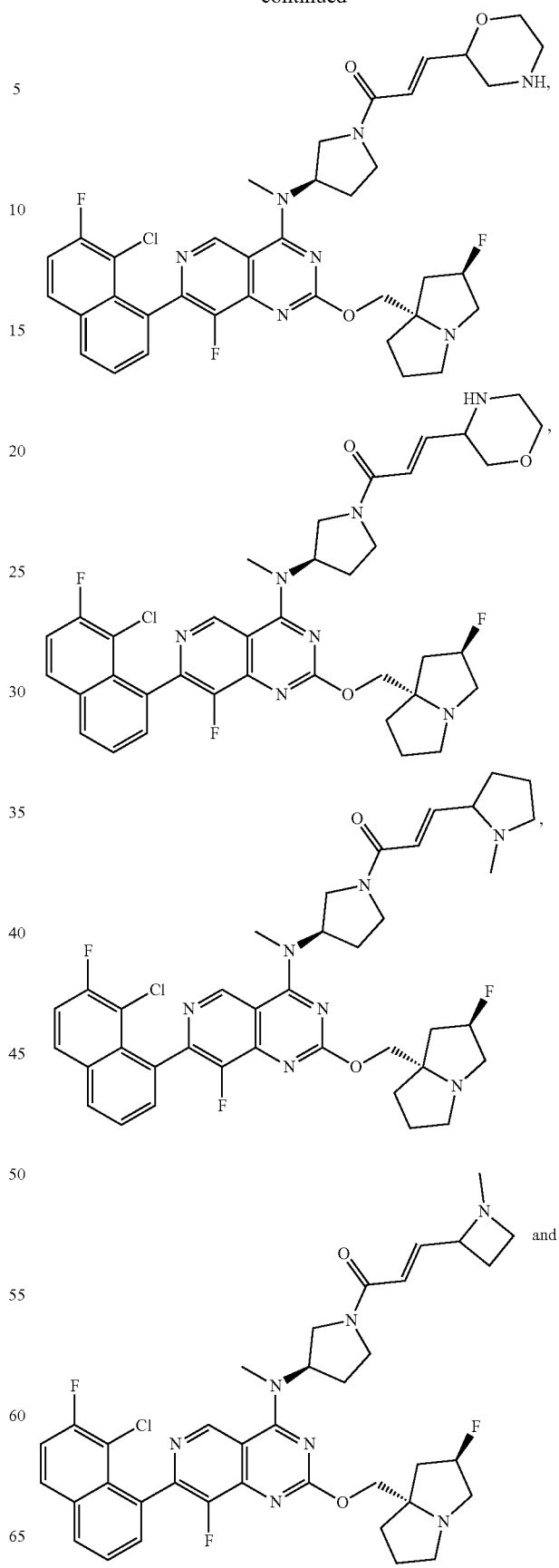

407
-continued
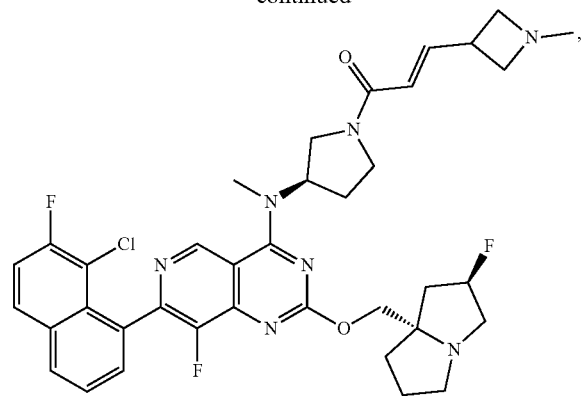
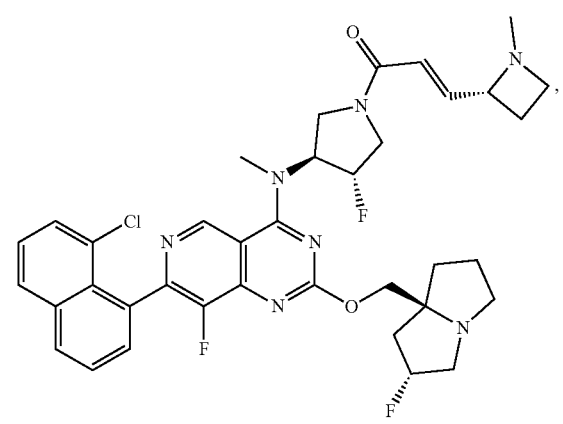
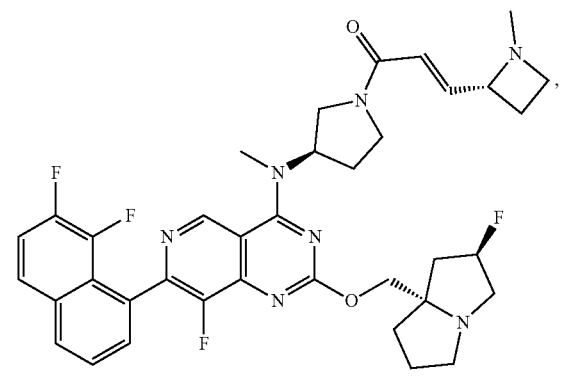
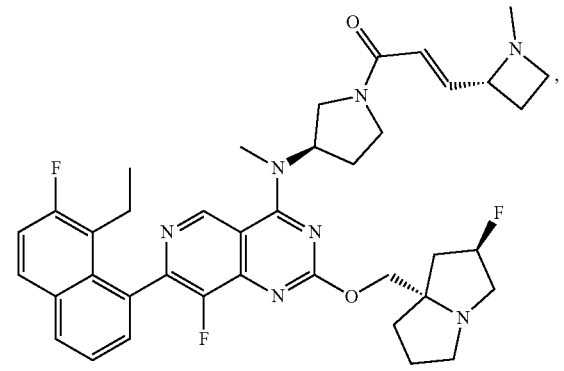
408
-continued
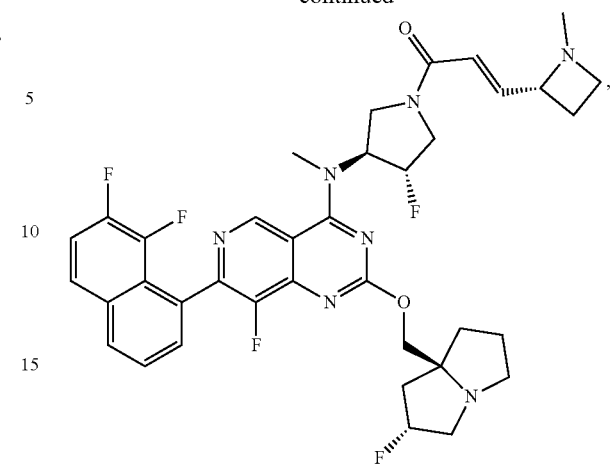
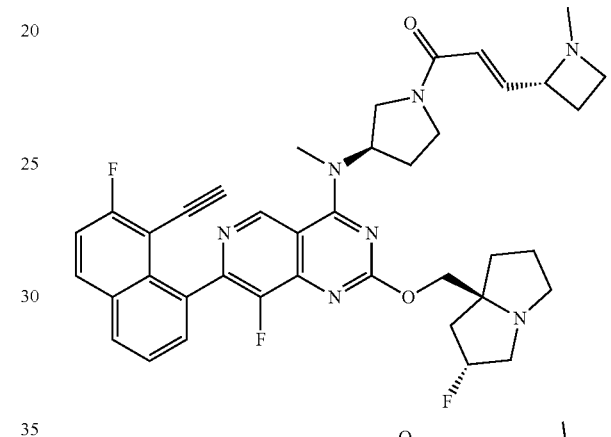
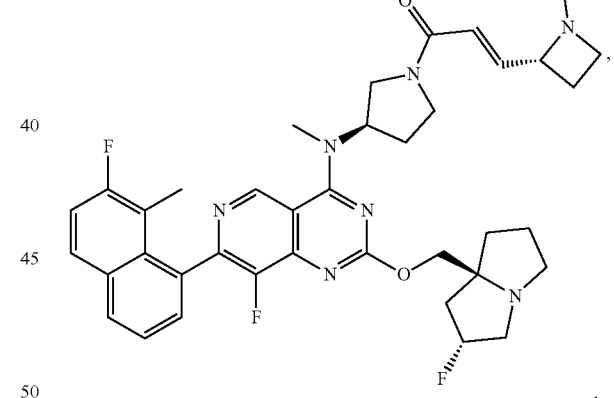
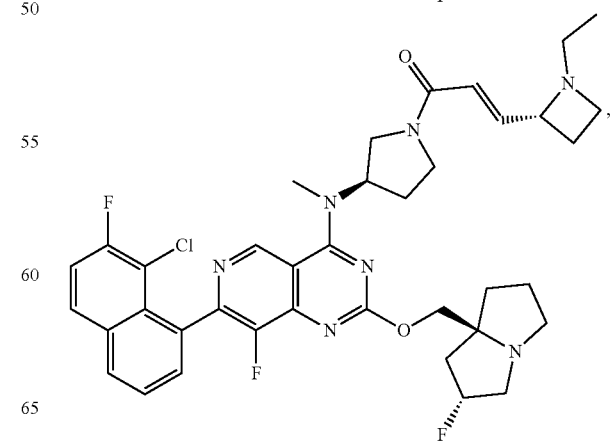

409
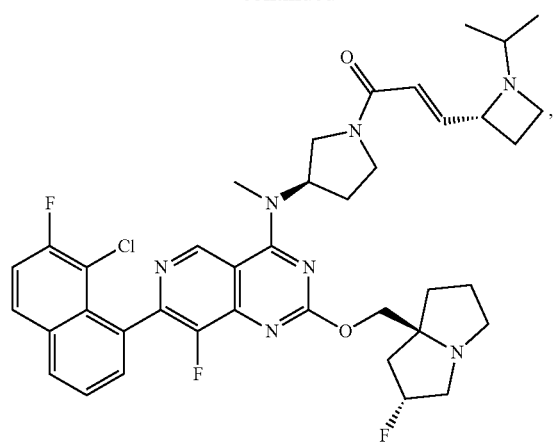
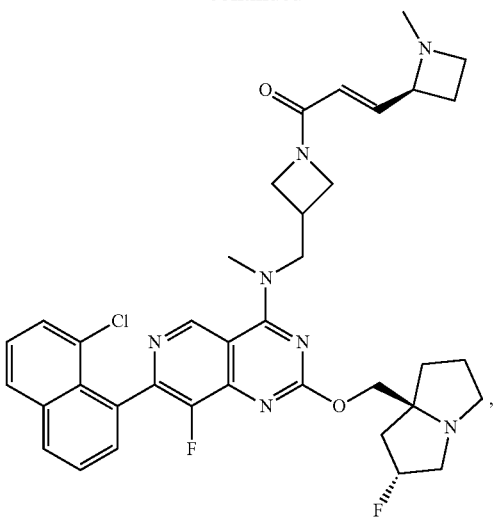
410
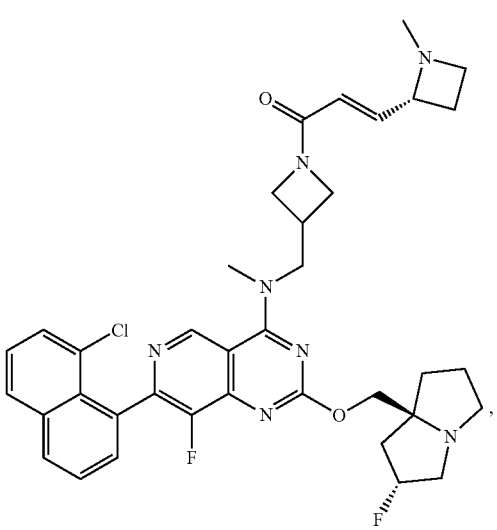
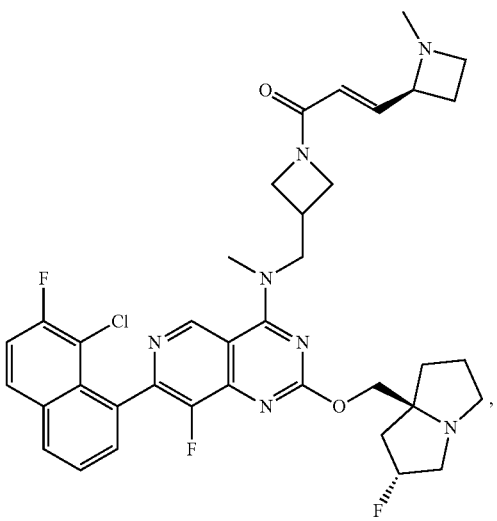

411
-continued
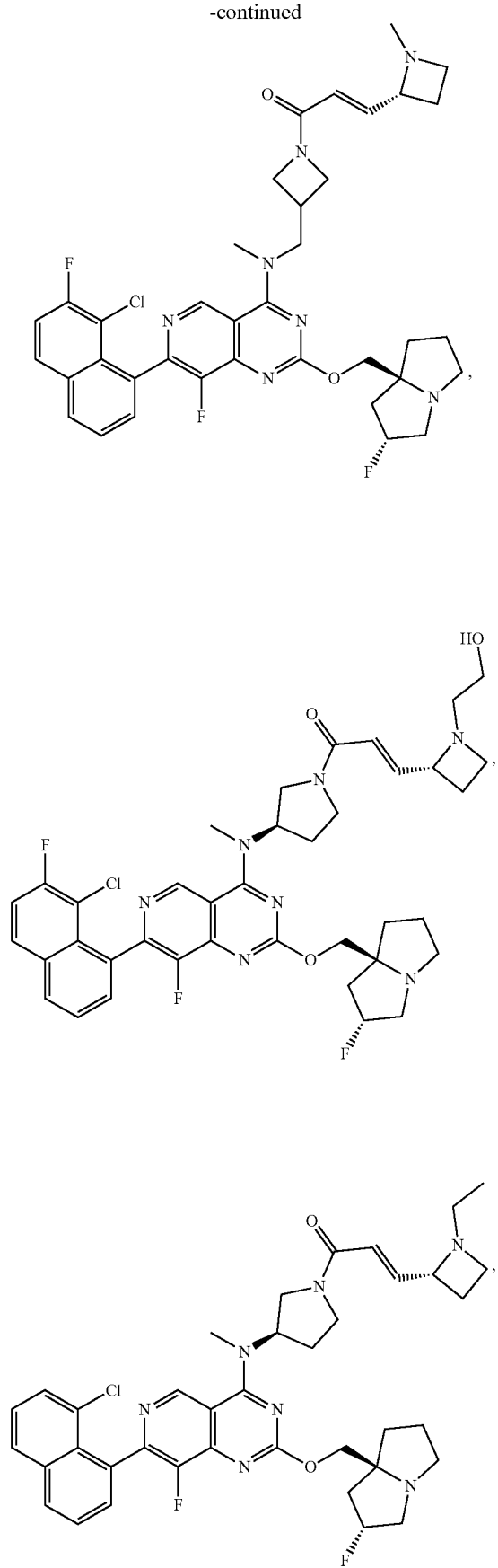
412
-continued
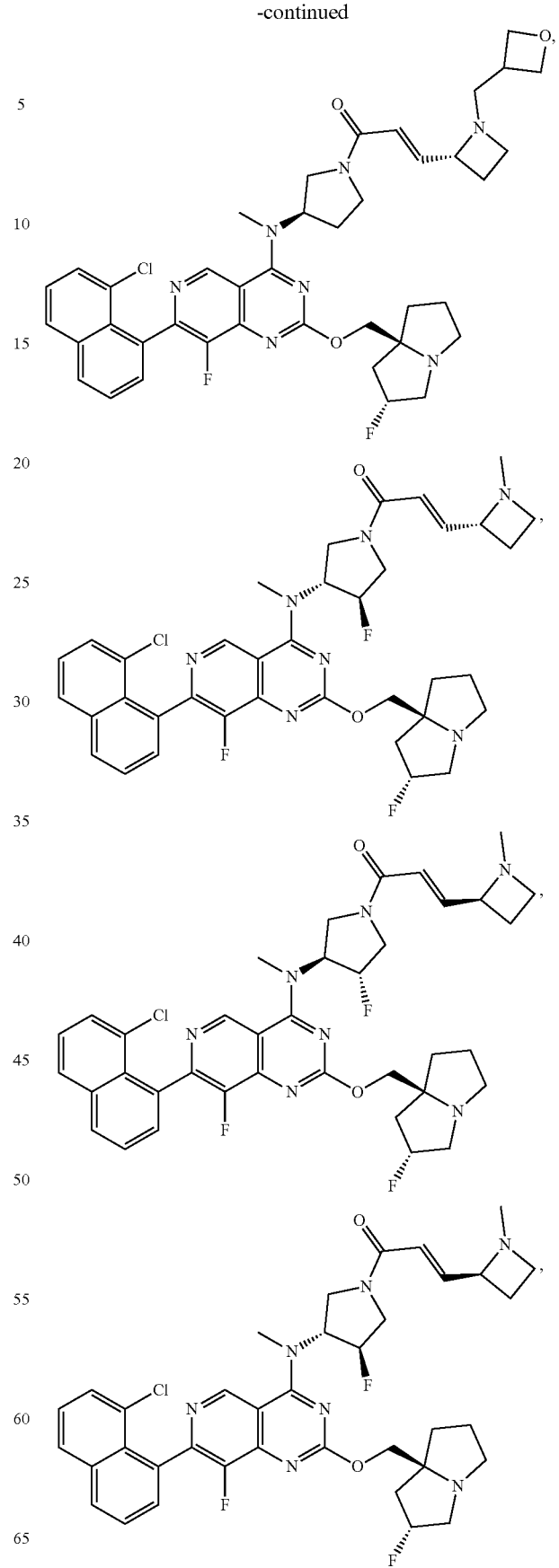

413
-continued
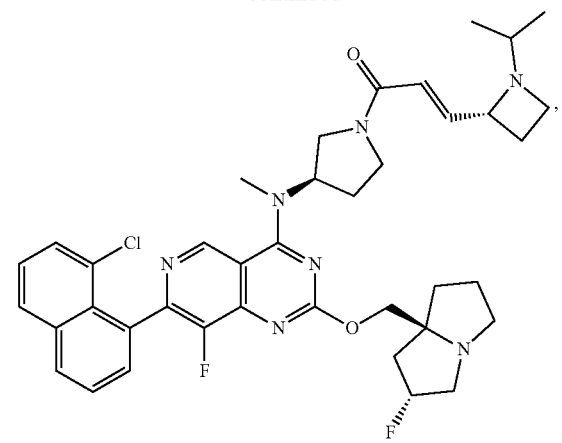
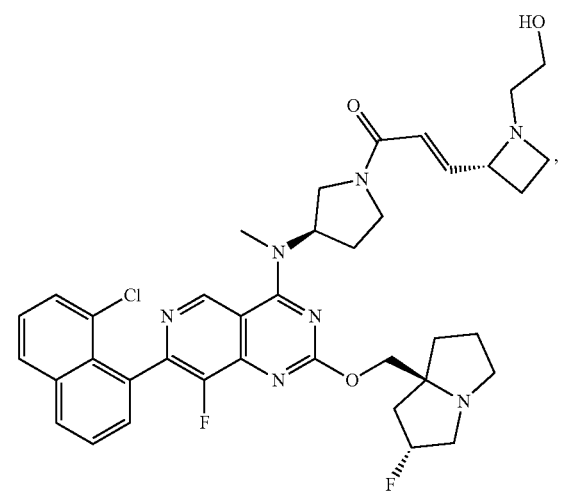
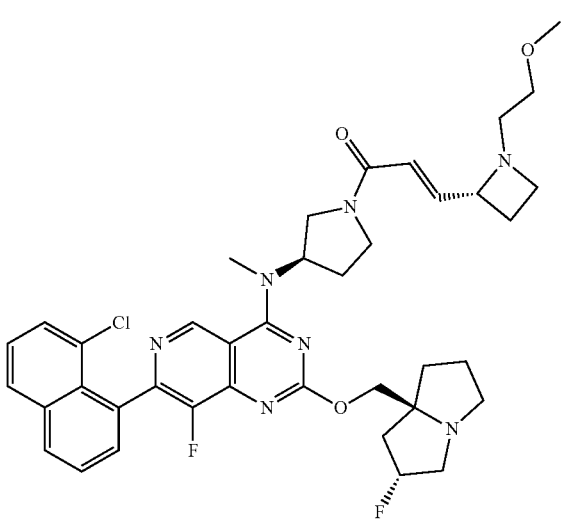
414
-continued
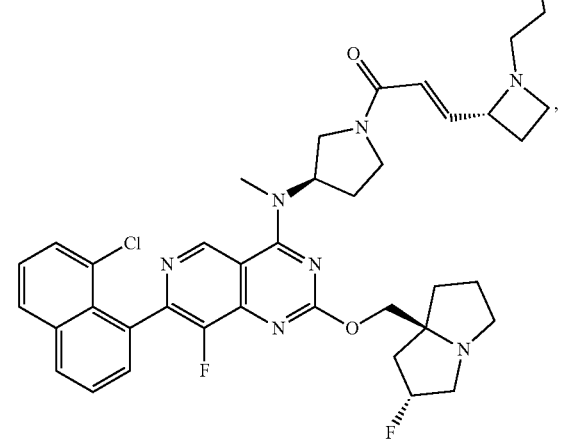

415
-continued
416
-continued
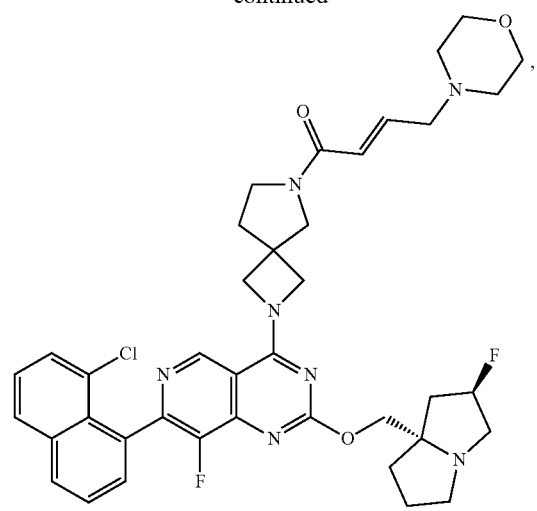
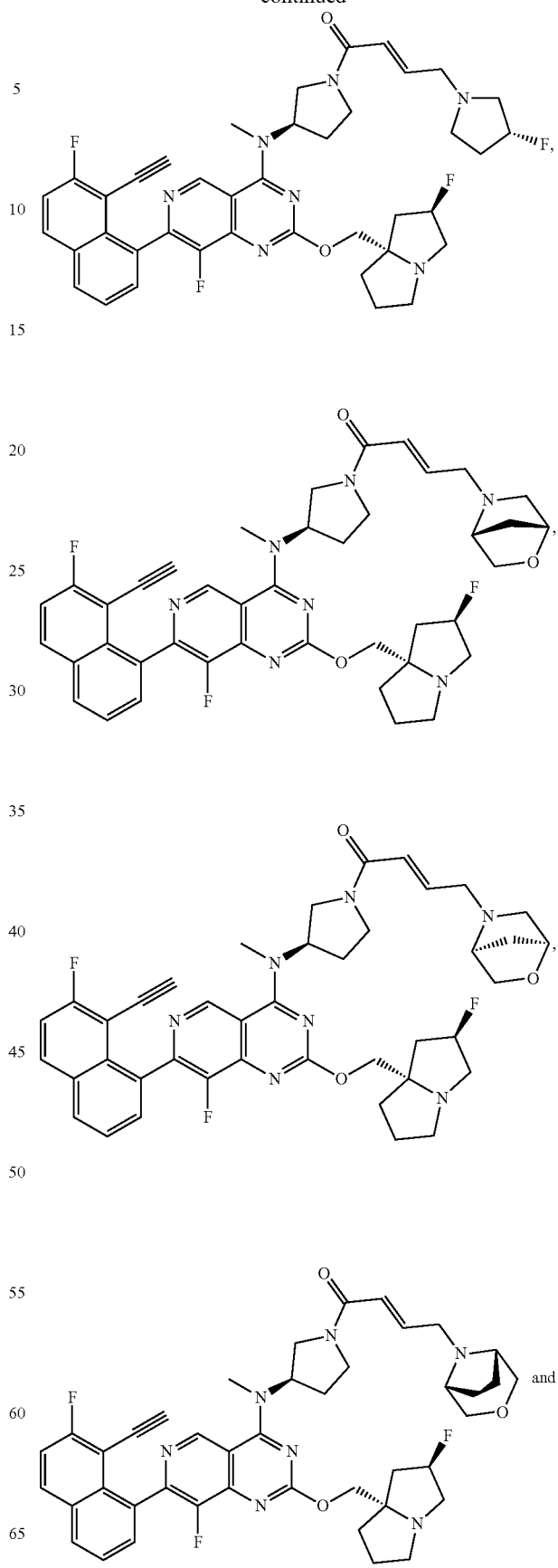

-continued

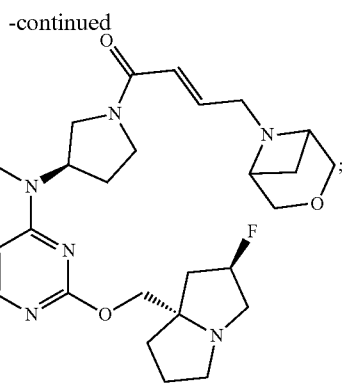

and all salts and isotopologues thereof.

Embodiment 439. The compound of any one of embodiments 1-438, wherein the compound is not a salt.

Embodiment 440. The compound of any one of embodiments 1-438, wherein the compound is a salt.

Embodiment 441. The compound of embodiment 440, wherein the salt is a formate salt.

Embodiment 442. The compound of embodiments 440, wherein the salt is a trifluoroacetate salt.

Embodiment 443. The compound of embodiment 440, wherein the salt is a pharmaceutically acceptable salt.

Embodiment 444. A pharmaceutical formulation comprising the compound of any one of embodiments 1-440, wherein when the compound is a salt, the salt is a pharmaceutically acceptable salt, and a pharmaceutically acceptable carrier.

Embodiment 445. A method of treating or suppressing cancer comprising: administering a therapeutically effective amount of a compound of any one of embodiments 1-440, wherein when the compound is a salt, the salt is a pharmaceutically acceptable salt, or a pharmaceutical formulation according to embodiment 444, to a subject in need thereof.

Embodiment 446. The method of embodiment 445, wherein the cancer is selected from the group consisting of: lung, colorectal, pancreatic, bile duct, thyroid, gall bladder, uterine, mesothelioma, cervical, and bladder cancers.

Embodiment 447. The method of embodiment 445, wherein the cancer is selected from the group consisting of: glioblastoma multiforme, lower grade glioma, head and neck squamous cell carcinoma, papillary thyroid carcinoma, anaplastic thyroid carcinoma, follicular thyroid carcinoma, lung adenocarcinoma, lung squamous cell carcinoma, breast invasive carcinoma, esophageal carcinoma, stomach adenocarcinoma, small intestine adenocarcinoma, colon adenocarcinoma, rectal adenocarcinoma, liver hepatocellular carcinoma, cholangiocarcinoma, gallbladder carcinoma, pancreatic adenocarcinoma, kidney renal clear cell carcinoma, bladder urothelial carcinoma, prostate adenocarcinoma, ovarian serous cystadenocarcinoma, uterine corpus endometrial carcinoma, cervical squamous carcinoma and endocervical adenocarcinoma, skin cutaneous melanoma, acute lymphoblastic leukemia, acute myeloid leukemia, chronic myeloid leukemia, plasma cell myeloma, uterine carcinosarcoma, mesothelioma, adrenocortical carcinoma, brain lower grade glioma, diffuse large B-cell lymphoma, esophageal adenocarcinoma, kidney chromphobe, kidney renal papillary cell carcinoma, pheochromocytoma and paraganglioma, sarcoma, testicular germ cell tumors, thymoma, uveal melanoma, metastatic colorectal cancer, bladder cancer, adenoid cystic carcinoma, myelodysplastic, breast cancer, thyroid carcinoma, glioma, esophageal/stomach cancer, pediatric Wilms' tumor, pediatric acute lymphoid leukemia, chronic lymphocytic leukemia, mature B-cell malignancies, pediatric neuroblastoma, and melanoma.

Embodiment 448. The method of any one of embodiments 445-447, wherein the cancer is a KRAS G12C mediated cancer.

Embodiment 449. The method of any one of embodiments 445-447, wherein the subject has been diagnosed as having a KRAS G12C mediated cancer.

Embodiment 450. The method of any one of embodiments 445-449, wherein the method further comprises administering to the subject a therapeutically effective amount of an additional chemotherapeutic agent.

Embodiment 451. A compound of any one of embodiments 1-440 or a pharmaceutical formulation according to embodiment 444 for use as a medicament.

Embodiment 452. A compound of any one of embodiments 1-440 or a pharmaceutical formulation according to embodiment 444, for use in treating or suppressing cancer wherein when the compound is a salt, the salt is a pharmaceutically acceptable salt.

Embodiment 453. The compound or pharmaceutical composition for use of embodiment 452, wherein the cancer is selected from the group consisting of: lung, colorectal, pancreatic, bile duct, thyroid, gall bladder, uterine, mesothelioma, cervical, and bladder cancers.

Embodiment 454. The compound or pharmaceutical composition for use of embodiment 452, wherein the cancer is selected from the group consisting of: glioblastoma multiforme, lower grade glioma, head and neck squamous cell carcinoma, papillary thyroid carcinoma, anaplastic thyroid carcinoma, follicular thyroid carcinoma, lung adenocarcinoma, lung squamous cell carcinoma, breast invasive carcinoma, esophageal carcinoma, stomach adenocarcinoma, small intestine adenocarcinoma, colon adenocarcinoma, rectal adenocarcinoma, liver hepatocellular carcinoma, cholangiocarcinoma, gallbladder carcinoma, pancreatic adenocarcinoma, kidney renal clear cell carcinoma, bladder urothelial carcinoma, prostate adenocarcinoma, ovarian serous cystadenocarcinoma, uterine corpus endometrial carcinoma, cervical squamous carcinoma and endocervical adenocarcinoma, skin cutaneous melanoma, acute lymphoblastic leukemia, acute myeloid leukemia, chronic myeloid leukemia, plasma cell myeloma, uterine carcinosarcoma, mesothelioma, adrenocortical carcinoma, brain lower grade glioma, diffuse large B-cell lymphoma, esophageal adenocarcinoma, kidney chromophobe, kidney renal papillary cell carcinoma, pheochromocytoma and paraganglioma, sarcoma, testicular germ cell tumors, thymoma, uveal melanoma, metastatic colorectal cancer, bladder cancer, adenoid cystic carcinoma, myelodysplastic, breast cancer, thyroid carcinoma, glioma, esophageal/stomach cancer, pediatric Wilms' tumor, pediatric acute lymphoid leukemia, chronic lymphocytic leukemia, mature B-cell malignancies, pediatric neuroblastoma, and melanoma.

Embodiment 455. The compound or pharmaceutical composition for use of any one of embodiments 452-454, wherein the cancer is a KRAS G12C mediated cancer.

Embodiment 456. The compound or pharmaceutical composition for use of any one of embodiments 452-454, wherein the subject has been diagnosed as having a KRAS G12C mediated cancer.

Embodiment 457. The compound or pharmaceutical composition for use of any one of embodiments 452-456, wherein the compound or pharmaceutical composition is configured for administration with a therapeutically effective amount of an additional chemotherapeutic agent.

Embodiment 458. The compound or pharmaceutical composition for use of any one of embodiments 452-457, wherein the compound or pharmaceutical composition is configured for administration in a therapeutically effective amount.

Embodiment 459. A compound of any one of embodiments 1-440 or a pharmaceutical formulation according to embodiment 444 for use in the manufacturing of a medicament for treating or suppressing cancer comprising, wherein when the compound is a salt, the salt is a pharmaceutically acceptable salt.

Embodiment 460. The compound or pharmaceutical composition for use of embodiment 459, wherein the cancer is selected from the group consisting of lung, colorectal, pancreatic, bile duct, thyroid, gall bladder, uterine, mesothelioma, cervical, and bladder cancers.

Embodiment 461. The compound or pharmaceutical composition for use of embodiment 459, wherein the cancer is selected from the group consisting of: glioblastoma multiforme, lower grade glioma, head and neck squamous cell carcinoma, papillary thyroid carcinoma, anaplastic thyroid carcinoma, follicular thyroid carcinoma, lung adenocarcinoma, lung squamous cell carcinoma, breast invasive carcinoma, esophageal carcinoma, stomach adenocarcinoma, small intestine adenocarcinoma, colon adenocarcinoma, rectal adenocarcinoma, liver hepatocellular carcinoma, cholangiocarcinoma, gallbladder carcinoma, pancreatic adenocarcinoma, kidney renal clear cell carcinoma, bladder urothelial carcinoma, prostate adenocarcinoma, ovarian serous cystadenocarcinoma, uterine corpus endometrial carcinoma, cervical squamous carcinoma and endocervical adenocarcinoma, skin cutaneous melanoma, acute lymphoblastic leukemia, acute myeloid leukemia, chronic myeloid leukemia, plasma cell myeloma, uterine carcinosarcoma, mesothelioma, adrenocortical carcinoma, brain lower grade glioma, diffuse large B-cell lymphoma, esophageal adenocarcinoma, kidney chromophobe, kidney renal papillary cell carcinoma, pheochromocytoma and paraganglioma, sarcoma, testicular germ cell tumors, thymoma, uveal melanoma, metastatic colorectal cancer, bladder cancer, adenoid cystic carcinoma, myelodysplastic, breast cancer, thyroid carcinoma, glioma, esophageal/stomach cancer, pediatric Wilms' tumor, pediatric acute lymphoid leukemia, chronic lymphocytic leukemia, mature B-cell malignancies, pediatric neuroblastoma, and melanoma.

Embodiment 462. The compound or pharmaceutical composition for use of any one of embodiments 459-461, wherein the cancer is a KRAS G12C mediated cancer.

Embodiment 463. The compound or pharmaceutical composition for use of any one of embodiments 459-461, wherein the subject has been diagnosed as having a KRAS GT2C mediated cancer.

Embodiment 464. The compound or pharmaceutical composition for use of any one of embodiments 459-463, wherein the compound or pharmaceutical composition is configured for administration with a therapeutically effective amount of an additional chemotherapeutic agent.

Embodiment 465. The compound or pharmaceutical composition for use of any one of embodiments 459-464, wherein the medicament comprises a therapeutically effective amount of the compound or composition.

Embodiment 466. Use of a compound of any one of embodiments 1-440 or a pharmaceutical formulation according to embodiment 444 in the manufacturing of a medicament for treating or suppressing cancer comprising, wherein when the compound is a salt, the salt is a pharmaceutically acceptable salt.

Embodiment 467. The use of embodiment 466, wherein the cancer is selected from the group consisting of: lung, colorectal, pancreatic, bile duct, thyroid, gall bladder, uterine, mesothelioma, cervical, and bladder cancers.

Embodiment 468. The use of embodiment 466, wherein the cancer is selected from the group consisting of: glioblastoma multiforme, lower grade glioma, head and neck squamous cell carcinoma, papillary thyroid carcinoma, anaplastic thyroid carcinoma, follicular thyroid carcinoma, lung adenocarcinoma, lung squamous cell carcinoma, breast invasive carcinoma, esophageal carcinoma, stomach adenocarcinoma, small intestine adenocarcinoma, colon adenocarcinoma, rectal adenocarcinoma, liver hepatocellular carcinoma, cholangiocarcinoma, gallbladder carcinoma, pancreatic adenocarcinoma, kidney renal clear cell carcinoma, bladder urothelial carcinoma, prostate adenocarcinoma, ovarian serous cystadenocarcinoma, uterine corpus endometrial carcinoma, cervical squamous carcinoma and endocervical adenocarcinoma, skin cutaneous melanoma, acute lymphoblastic leukemia, acute myeloid leukemia, chronic myeloid leukemia, plasma cell myeloma, uterine carcinosarcoma, mesothelioma, adrenocortical carcinoma, brain lower grade glioma, diffuse large B-cell lymphoma, esophageal adenocarcinoma, kidney chromophobe, kidney renal papillary cell carcinoma, pheochromocytoma and paraganglioma, sarcoma, testicular germ cell tumors, thymoma, uveal melanoma, metastatic colorectal cancer, bladder cancer, adenoid cystic carcinoma, myelodysplastic, breast cancer, thyroid carcinoma, glioma, esophageal/stomach cancer, pediatric Wilms' tumor, pediatric acute lymphoid leukemia, chronic lymphocytic leukemia, mature B-cell malignancies, pediatric neuroblastoma, and melanoma.

Embodiment 469. The use of any one of embodiments 466-468, wherein the cancer is a KRAS G12C mediated cancer.

Embodiment 470. The use of any one of embodiments 466-468, wherein the subject has been diagnosed as having a KRAS G12C mediated cancer.

Embodiment 471. The use of any one of embodiments 466-470, wherein the compound or pharmaceutical composition is configured for administration with a therapeutically effective amount of an additional chemotherapeutic agent.

Embodiment 472. The use of any one of embodiments 466-471, wherein the medicament comprises a therapeutically effective amount of the compound or pharmaceutical composition.

Embodiment 473. Use of a compound of any one of embodiments 1-440 or a pharmaceutical formulation according to embodiment 444 for treating or suppressing cancer comprising, wherein when the compound is a salt, the salt is a pharmaceutically acceptable salt.

Embodiment 474. The use of embodiment 473, wherein the cancer is selected from the group consisting of: lung, colorectal, pancreatic, bile duct, thyroid, gall bladder, uterine, mesothelioma, cervical, and bladder cancers.

Embodiment 475. The use of embodiment 473, wherein the cancer is selected from the group consisting of: glioblastoma multiforme, lower grade glioma, head and neck squamous cell carcinoma, papillary thyroid carcinoma, anaplastic thyroid carcinoma, follicular thyroid carcinoma, lung adenocarcinoma, lung squamous cell carcinoma, breast invasive carcinoma, esophageal carcinoma, stomach adenocarcinoma, small intestine adenocarcinoma, colon adenocarcinoma, rectal adenocarcinoma, liver hepatocellular carcinoma, cholangiocarcinoma, gallbladder carcinoma, pancreatic adenocarcinoma, kidney renal clear cell carcinoma, bladder urothelial carcinoma, prostate adenocarcinoma, ovarian serous cystadenocarcinoma, uterine corpus endometrial carcinoma, cervical squamous carcinoma and endocervical adenocarcinoma, skin cutaneous melanoma, acute lymphoblastic leukemia, acute myeloid leukemia, chronic myeloid leukemia, plasma cell myeloma, uterine carcinosarcoma, mesothelioma, adrenocortical carcinoma, brain lower grade glioma, diffuse large B-cell lymphoma, esophageal adenocarcinoma, kidney chromophobe, kidney renal papillary cell carcinoma, pheochromocytoma and paraganglioma, sarcoma, testicular germ cell tumors, thymoma, uveal melanoma, metastatic colorectal cancer, bladder cancer, adenoid cystic carcinoma, myelodysplastic, breast cancer, thyroid carcinoma, glioma, esophageal/stomach cancer, pediatric Wilms' tumor, pediatric acute lymphoid leukemia, chronic lymphocytic leukemia, mature B-cell malignancies, pediatric neuroblastoma, and melanoma.

Embodiment 476. The use of any one of embodiments 473-475, wherein the cancer is a KRAS G12C mediated cancer.

Embodiment 477. The use of any one of embodiments 473-475, wherein the subject has been diagnosed as having a KRAS G12C mediated cancer.

Embodiment 478. The use of any one of embodiments 473-477, wherein the compound or pharmaceutical composition is configured for administration with a therapeutically effective amount of an additional chemotherapeutic agent.

Embodiment 479. The use of any one of embodiments 473-478, wherein use involves a therapeutically effective amount of the compound or composition.

General Synthetic Methods

Compounds of this disclosure can be made in view of the disclosure in the Examples shown below.

The starting materials and reagents used in preparing these compounds are either available from commercial suppliers such as MilliporeSigma., Bachem., etc. or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this disclosure can be synthesized, and various modifications to these schemes can be made and will be suggested to one skilled in the art reading this disclosure. The starting materials and the intermediates, and the final products of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., such as from about 0° C. to about 125° C. and further such as at about room (or ambient) temperature, e.g., about 20° C.

EXAMPLES

The following preparations of compounds of Formula (I), Formula (I-1), Formula (I-2), Formula (II), Formula (II-1) and Formula (II-2) and pharmaceutically acceptable salts thereof are given to enable those skilled in the art to more clearly understand and to practice the present disclosure. They should not be considered as limiting the scope of the disclosure, but merely as being illustrative and representative thereof.

The following abbreviations are used in this section:

| | |
|---|---|
| ACN | Acetonitrile |
| br | broad |
| Boc | tert-butyloxycarbonyl |
| d | doublet |
| dd | doublet of doublets |
| ddd | doublet of doublets of doublets |
| dt | doublet of triplets |
| DCM | dichloromethane |
| ESI+ | Electrospray ionization |
| FA | Formic acid |
| g | grams |
| h | Hour(s) |
| HPLC | High performance liquid chromatography |
| Hz | hertz |
| J | coupling constant |
| LCMS | Liquid chromatography-mass spectrometry |
| m | multiplet |
| M | molar |
| mg | milligrams |
| MHz | megahertz |
| mL | milliliters |
| mmol | millimoles |
| m/z | Mass to charge ratio |
| min | Minute(s) |
| NMR | nuclear magnetic resonance |
| OTf | trifluoromethanesulfonate |
| ppm | parts per million |
| quin | quintet |
| Rt | Retention time |
| s | singlet |
| SFC | Supercritical fluid chromatography |
| t | triplet |
| td | triplet of doublets |
| TFA | Trifluoroacetic acid |
| THF | tetrahydrofuran |
| uL | microliters |
| umol | micromoles |

All reagents were obtained from commercial suppliers and used without further purification unless otherwise stated.

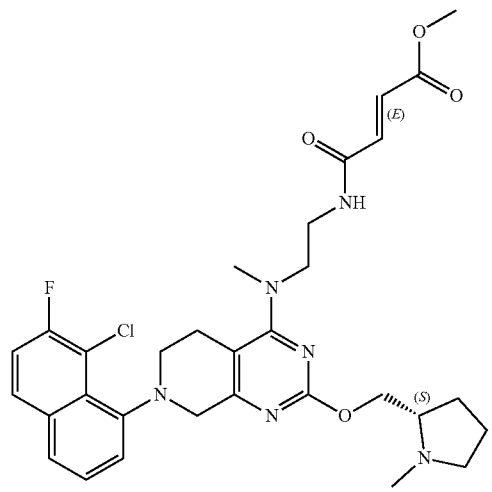

Example 1 (Method 1-A): methyl (S,E)-4-((2-((7-(8-chloro-7-fluoronaphthalen-1-yl)-2-((1-methylpyrrolidin-2-yl)methoxy)-5,6,7,8-tetrahydropyrido[3,4-d]pyrimidin-4-yl)(methyl)amino)ethyl)amino)-4-oxobut-2-enoate

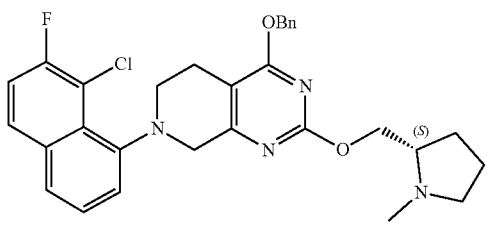

Step 1: (S)-4-(benzyloxy)-7-(8-chloro-7-fluoronaphthalen-1-yl)-2-((1-methylpyrrolidin-2-yl)methoxy)-5,6,7,8-tetrahydropyrido[3,4-d]pyrimidine To a solution of 4-benzyloxy-2-[[(2S)-1-methylpyrrolidin-2-yl]methoxy]-5,6,7,8-tetrahydropyrido[3,4-d]pyrimidine (400 mg, 1.13 mmol) in toluene (5 mL) was added (8-chloro-7-fluoro-1-naphthyl) trifluoromethanesulfonate (445.09 mg, 1.35 mmol), 2-dicyclohexylphosphino-2',6'-diisopropoxybiphenyl (105.32 mg, 225.70 µmol), Tris(dibenzylideneacetone)dipalladium(0) (103.34 mg, 112.85 µmol) and cesium carbonate (1.47 g, 4.51 mmol). The mixture was stirred at 100° C. for 12 h under nitrogen atmosphere. The reaction mixture was filtered, and the filtrate was concentrated in vacuo. The residue was purified by reverse phase HPLC (column: Phenomenex luna C18 250*50 mm*10 µm; mobile phase: (water (0.1% TFA)-ACN; B %: 45%-75%, 10 min) affording (S)-4-(benzyloxy)-7-(8-chloro-7-fluoronaphthalen-1-yl)-2-((1-methylpyrrolidin-2-yl)methoxy)-5,6,7,8-tetrahydropyrido[3,4-d]pyrimidine (260 mg, 36%, trifluoroacetate salt) as a yellow solid. LCMS Rt=0.765 min, m/z=532.2 [M+H]+.

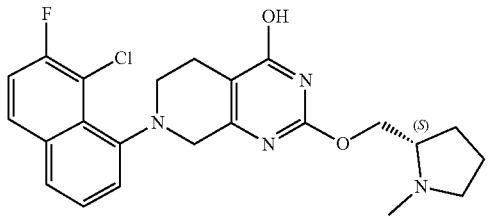

Step 2: (S)-7-(8-chloro-7-fluoronaphthalen-1-yl)-2-((1-methylpyrrolidin-2-yl)methoxy)-5,6,7,8-tetrahydropyrido[3,4-d]pyrimidin-4-ol A mixture of (S)-4-(benzyloxy)-7-(8-chloro-7-fluoronaphthalen-1-yl)-2-((1-methylpyrrolidin-2-yl)methoxy)-5,6,7,8-tetrahydropyrido[3,4-d]pyrimidine (250 mg, 386.36 µmol, trifluoroacetate salt) in trifluoroacetic acid (1 mL) was stirred at 60° C. for 1 h. The reaction mixture was concentrated in vacuo. The residue was quenched with a saturated solution of sodium carbonate (3 mL) at 0° C. and extracted with dichloromethane (3×15 mL). The combined organic layers were dried over sodium sulphate and concentrated in vacuo affording (S)-7-(8-chloro-7-fluoronaphthalen-1-yl)-2-((1-methylpyrrolidin-2-yl)methoxy)-5,6,7,8-tetrahydropyrido[3,4-d]pyrimidin-4-ol (200 mg, crude) as a yellow oil used in next step without further purification. LCMS Rt=0.644 min, m/z=422.2 [M+H]+.

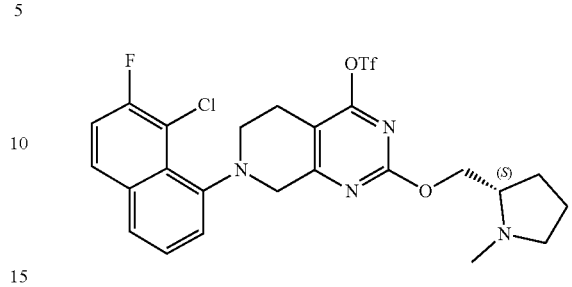

Step 3: (S)-7-(8-chloro-7-fluoronaphthalen-1-yl)-2-((1-methylpyrrolidin-2-yl)methoxy)-5,6,7,8-tetrahydropyrido[3,4-d]pyrimidin-4-yl trifluoromethanesulfonate To a solution of (S)-7-(8-chloro-7-fluoronaphthalen-1-yl)-2-((1-methylpyrrolidin-2-yl)methoxy)-5,6,7,8-tetrahydropyrido[3,4-d]pyrimidin-4-ol (190 mg, 341.15 µmol) in dichloromethane (10 mL) was added triethylamine (138.08 mg, 1.36 mmol) and trifluoromethylsulfonyl trifluoromethanesulfonate (240.63 mg, 852.88 µmol) at 0° C. The mixture was stirred at 25° C. for 1 h under nitrogen atmosphere. The reaction mixture was quenched with water (5 mL) and extracted with dichloromethane (3×10 mL). The combined organic layers were dried over sodium sulphate and concentrated in vacuo affording (S)-7-(8-chloro-7-fluoronaphthalen-1-yl)-2-((1-methylpyrrolidin-2-yl)methoxy)-5,6,7,8-tetrahydropyrido[3,4-d]pyrimidin-4-yl trifluoromethanesulfonate (200 mg, crude) as a yellow oil used in next step without further purification. LCMS Rt=0.762 min, m/z=574.1 [M+H]+.

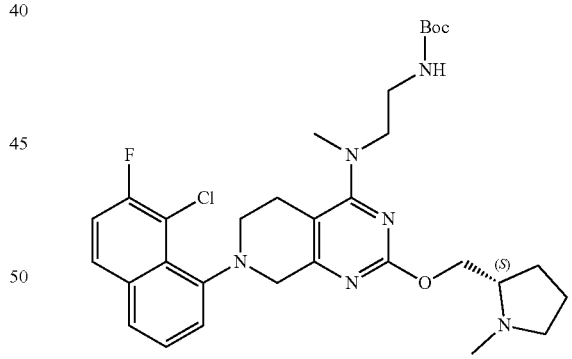

Step 4: (S)-tert-butyl (2-((7-(8-chloro-7-fluoronaphthalen-1-yl)-2-((1-methylpyrrolidin-2-yl)methoxy)-5,6,7,8-tetrahydropyrido[3,4-d]pyrimidin-4-yl)(methyl)amino)ethyl)carbamate To a solution of (S)-7-(8-chloro-7-fluoronaphthalen-1-yl)-2-((1-methylpyrrolidin-2-yl)methoxy)-5,6,7,8-tetrahydropyrido[3,4-d]pyrimidin-4-yl trifluoromethanesulfonate (100 mg, 173.92 µmol) in N,N-dimethylformaldehyde (1 mL) was added N-ethyl-N-isopropylpropan-2-amine (89.91 mg, 695.68 µmol) and tert-butyl N-[2-(methylamino)ethyl]carbamate (45.46 mg, 260.88 µmol) at 0° C. The mixture was stirred at 25° C. for 1 h. The reaction mixture was filtered, and the filtrate was concentrated in vacuo. The residue was purified by reverse phase HPLC (column: Phenomenex Luna 80*30 mm*3 µm; mobile phase: (water (TFA)-ACN; B %:15%-45%, 8 min) affording (S)-tert-butyl (2-((7-(8-chloro-7-fluoronaphthalen-1-yl)-2-((1-methylpyrrolidin-2-yl)methoxy)-5,6,7,8-tetrahydropyrido[3,4-d]pyrimidin-4-yl)(methyl)amino)ethyl)carbamate (100 mg, 81%, trifluoroacetate salt) as a yellow solid. LCMS Rt=1.585 min, m/z=598.3 [M+H]+.

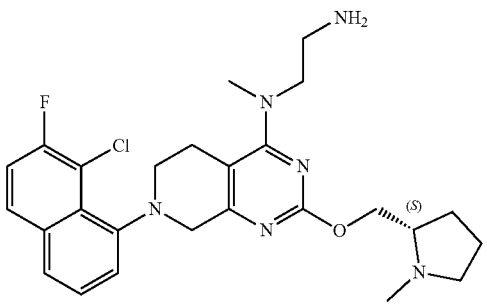

Step 5: (S)—$N^1$-(7-(8-chloro-7-fluoronaphthalen-1-yl)-2-((1-methylpyrrolidin-2-yl)methoxy)-5,6,7,8-tetrahydropyrido[3,4-d]pyrimidin-4-yl)-$N_1$-methylethane-1,2-diamine A mixture of (S)-tert-butyl (2-((7-(8-chloro-7-fluoronaphthalen-1-yl)-2-((1-methylpyrrolidin-2-yl)methoxy)-5,6,7,8-tetrahydropyrido[3,4-d]pyrimidin-4-yl)(methyl)amino)ethyl)carbamate (90 mg, 126.20 µmol, trifluoroacetate salt) in 4.0 M hydrochloric acid in ethyl acetate acetate (1 mL) was stirred at 25° C. for 1 h. The reaction mixture was concentrated in vacuo affording (S)—$N^1$-(7-(8-chloro-7-fluoronaphthalen-1-yl)-2-((1-methylpyrrolidin-2-yl)methoxy)-5,6,7,8-tetrahydropyrido[3,4-d]pyrimidin-4-yl)-N-methylethane-1,2-diamine (50 mg, crude, hydrochloride salt) as a yellow solid used in next step without further purification. LCMS Rt=0.585 min, m/z=498.3 [M+H]+.

Step 6: methyl (S,E)-4-((2-((7-(8-chloro-7-fluoronaphthalen-1-yl)-2-((1-methylpyrrolidin-2-yl)methoxy)-5,6,7,8-tetrahydropyrido[3,4-d]pyrimidin-4-yl)(methyl)amino)ethyl)amino)-4-oxobut-2-enoate To a solution of (S)—$N^1$-(7-(8-chloro-7-fluoronaphthalen-1-yl)-2-((1-methylpyrrolidin-2-yl)methoxy)-5,6,7,8-tetrahydropyrido[3,4-d]pyrimidin-4-yl)-$N^1$-methylethane-1,2-diamine (40 mg, 80.16 µmol) in dichloromethane (1 mL) was added (E)-4-methoxy-4-oxobut-2-enoic acid (5.21 mg, 40.08 µmol), N-ethyl-N-isopropylpropan-2-amine (20.72 mg, 160.31 µmol) and 2,4,6-tripropyl-1,3,5,2,4,6-trioxatriphosphorinane-2,4,6-trioxide (38.26 mg, 60.12 µmol, 50% in ethyl acetate) at 0° C. The mixture was stirred at 25° C. for 0.5 h under nitrogen atmosphere. The reaction mixture was concentrated in vacuo and purified by reverse phase HPLC (column: Waters Xbridge BEH C18 100*30 mm*10 µm; mobile phase: (water ($NH_4HCO_3$)-ACN; B %: 40%-70%, 8 min) affording methyl (S,E)-4-((2-((7-(8-chloro-7-fluoronaphthalen-1-yl)-2-((1-methylpyrrolidin-2-yl)methoxy)-5,6,7,8-tetrahydropyrido[3,4-d]pyrimidin-4-yl)(methyl)amino)ethyl)amino)-4-oxobut-2-enoate (4.13 mg, 17%) as a yellow oil:$^1$H NMR (400 MHz, Acetonitrile-d3) δ 7.92 (dd, J=5.8, 9.0 Hz, 1H), 7.73 (d, J=8.1 Hz, 1H), 7.56-7.39 (m, 3H), 7.38-7.25 (m, 1H), 6.87 (d, J=15.4 Hz, 1H), 6.65 (d, J=15.5 Hz, 1H), 4.38-4.30 (m, 1H), 4.24-4.10 (m, 2H), 3.89-3.80 (m, 1H), 3.79-3.69 (m, 4H), 3.66-3.49 (m, 4H), 3.31-3.21 (m, 1H), 3.18 (s, 3H), 3.15-3.01 (m, 2H), 2.69 (br d, J=14.8 Hz, 1H), 2.63 (br s, 1H), 2.42 (s, 3H), 2.32-2.28 (m, 1H), 2.02 (br d, J=8.1 Hz, 1H), 1.83-1.66 (m, 3H). LCMS Rt=3.162 min, m/z=610.3 [M+H]+.

LCMS (5 to 95% acetonitrile in water+0.03% ammonium bicarbonate over 6 mins) retention time 3.162 min, ESI+ found [M+H]=610.3.

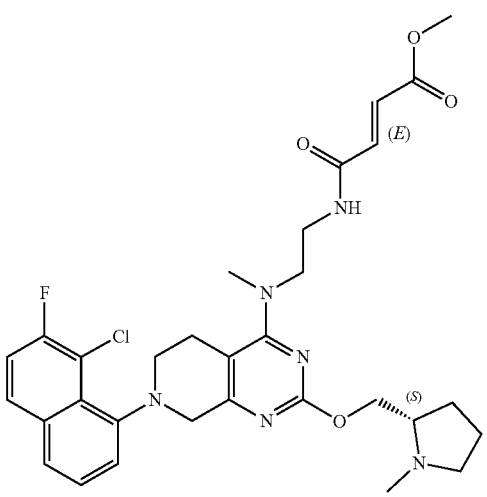

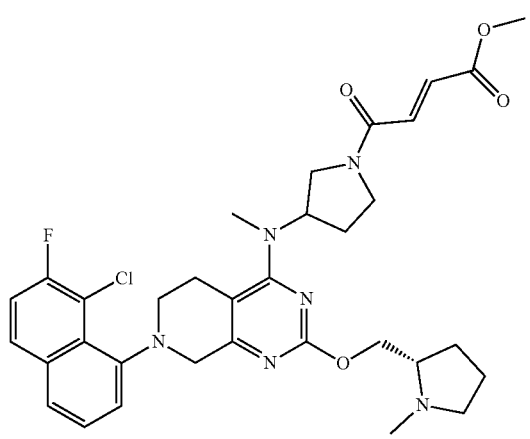 [SMILES: COC(=O)/C=C/C(=O)N1CCC(N(C)c2nc(OC[C@@H]3CCCN3C)nc3c2CCN(c2cccc4ccc(F)c(Cl)c24)C3)C1]

Example 2 (Method 1-A13): methyl (E)-4-(3-((7-(8-chloro-7-fluoronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-4-oxobut-2-enoate

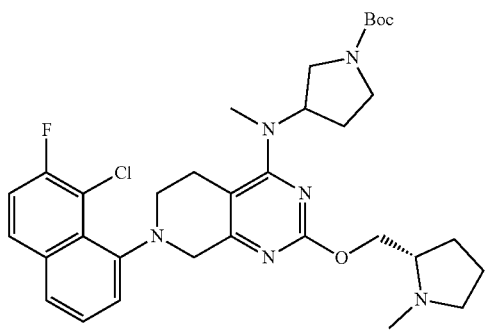 [SMILES: CN(c1nc(OC[C@@H]2CCCN2C)nc2c1CCN(c1cccc3ccc(F)c(Cl)c13)C2)C1CCN(C(=O)OC(C)(C)C)C1]

Step 1: tert-butyl 3-((7-(8-chloro-7-fluoronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidine-1-carboxylate The substitution reaction was prepared in a similar fashion to Example 1 (Method 1-A), Step 4, substituting tert-butyl 3-(methylamino)pyrrolidine-1-carboxylate for tert-butyl N-[2-(methylamino)ethyl]carbamate. The crude was purified by reverse phase HPLC (column: Phenomenex Luna 80*30 mm*3 μm; mobile phase: (water (TFA)-ACN; B %:15%-45%, 8 min) affording tert-butyl 3-((7-(8-chloro-7-fluoronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidine-1-carboxylate (14 mg, 11trifluoroacetate salt) as a white solid. LCMS Rt=0.721 min, m/z=624.3 [M+H]+.

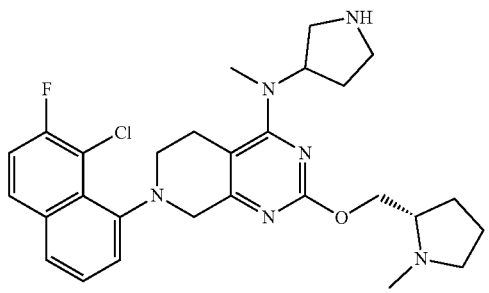 [SMILES: CN(c1nc(OC[C@@H]2CCCN2C)nc2c1CCN(c1cccc3ccc(F)c(Cl)c13)C2)C1CCNC1]

Step 2: 7-(8-chloro-7-fluoronaphthalen-1-yl)-N-methyl-2-(((S)-1-methylpyrrolidin-2-yl)methoxy)-N-(pyrrolidin-3-yl)-5,6,7,8-tetrahydropyrido[3,4-d]pyrimidin-4-amine The deprotection of Boc was prepared in a similar fashion to Example 1 (Method 1-A), Step 5. The mixture was concentrated to dryness in vacuo affording 7-(8-chloro-7-fluoronaphthalen-1-yl)-N-methyl-2-(((S)-1-methylpyrrolidin-2-yl)methoxy)-N-(pyrrolidin-3-yl)-5,6,7,8-tetrahydropyrido[3,4-d]pyrimidin-4-amine (12 mg, crude, hydrochloride salt) as a white solid, which was used in next step without further purification. LCMS Rt=0.603 min, m/z=524.3 [M+H]+.

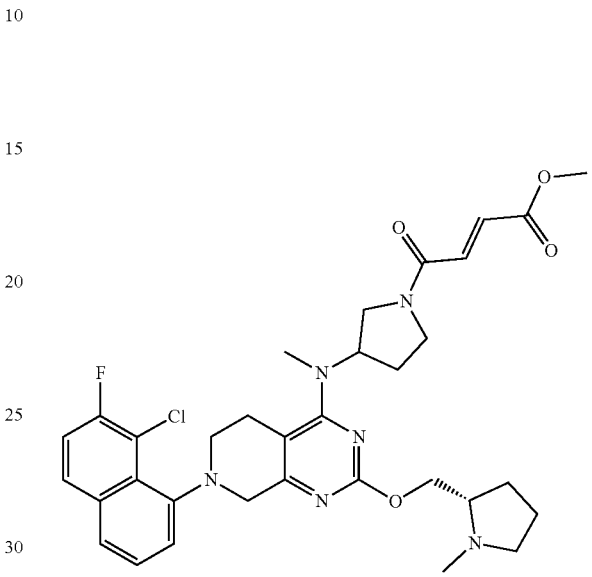

Step 3: methyl (E)-4-(3-((7-(8-chloro-7-fluoronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-4-oxobut-2-enoate The amide coupling reaction was prepared in a similar fashion to Example 1 (Method 1-A), Step 6. The crude product was purified by reverse phase HPLC (column: Phenomenex Luna 80*30 mm*3 μm; mobile phase: (water (FA)-ACN; B %: 1%-35%, 8 min) affording methyl (E)-4-(3-((7-(8-chloro-7-fluoronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-4-oxobut-2-enoate (1.9 mg, 12%, formate salt) as a yellow oil: $^1$H NMR (400 MHz, Acetonitrile-d3) δ 7.89 (dd, J=8.94, 5.84 Hz, 1H) 7.69 (br d, J=8.11 Hz, 1H), 7.49 (td, J=7.60, 3.04 Hz, 1H), 7.44-7.36 (m, 2H), 7.31-7.20 (m, 1H), 6.73-6.65 (m, 1H), 4.90-4.75 (m, 1H), 4.49-4.40 (m, 1H), 4.38-4.28 (m, 1H), 4.22 (br d, J=17.29 Hz, 1H), 3.96-3.84 (m, 1H), 3.78-3.70 (m, 5H), 3.66-3.58 (m, 1H), 3.56-3.43 (m, 2H), 3.41-3.34 (m, 1H), 3.18-3.04 (m, 3H), 3.00-2.96 (m, 3H), 2.64-2.57 (m, 5H), 2.13-2.06 (m, 2H), 1.87-1.81 (m, 1H), 1.79-1.69 (m, 1H), 1.64-1.40 (m, 2H). LCMS Rt=2.196 min, m/z=636.3 [M+H]+.

LCMS (5 to 95% acetonitrile in water+0.1% trifluoroacetic acid over 6 mins) retention time 2.196 min, ESI+ found [M+H]=636.3.

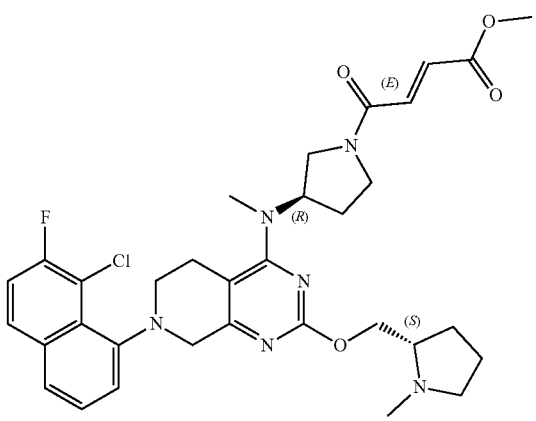

Example 3 (Method 1-A14): methyl (E)-4-((R)-3-((7-(8-chloro-7-fluoronaphthalen-1-yl)-2-(((S)-1-methylpyrrolidin-2-yl)methoxy)-5,6,7,8-tetrahydro-pyrido[3,4-d]pyrimidin-4-yl)(methyl)amino)pyrrolidin-1-yl)-4-oxobut-2-enoate

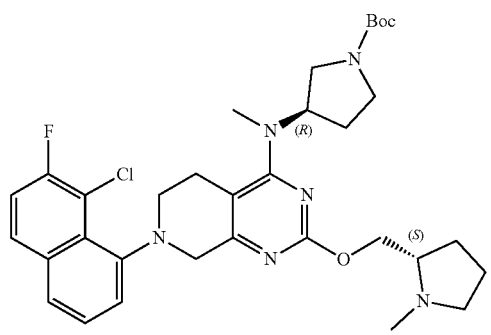

Step 1: (R)-tert-butyl 3-((7-(8-chloro-7-fluoronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidine-1-carboxylate The substitution reaction was prepared in a similar fashion to Example 1 (Method 1-A), Step 4, substituting tert-butyl (R)-3-(methylamino)pyrrolidine-1-carboxylate for tert-butyl N-[2-(methylamino)ethyl]carbamate. The crude product was purified by reverse phase HPLC (column: Phenomenex Luna 80*30 mm*3 μm; mobile phase: (water (TFA)-ACN; B %: 15%-50%, 8 min) affording (R)-tert-butyl 3-((7-(8-chloro-7-fluoronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidine-1-carboxylate (20 mg, 16%, trifluoroacetate salt) as a white solid. LCMS Rt=0.727 min, m/z=624.3 [M+H]+.

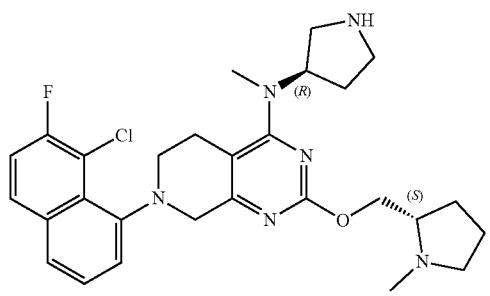

Step 2: 7-(8-chloro-7-fluoronaphthalen-1-yl)-N-methyl-2-(((S)-1-methylpyrrolidin-2-yl)methoxy)-N—((R)-pyrrolidin-3-yl)-5,6,7,8-tetrahydropyrido[3,4-d]pyrimidin-4-amine The deprotection of Boc reaction was prepared in a similar fashion to Example 1 (Method 1-A), Step 5. The mixture was concentrated to dryness in vacuo affording 7-(8-chloro-7-fluoronaphthalen-1-yl)-N-methyl-2-(((S)-1-methylpyrrolidin-2-yl)methoxy)-N—((R)-pyrrolidin-3-yl)-5,6,7,8-tetrahydropyrido[3,4-d]pyrimidin-4-amine (17 mg, crude, hydrochloride salt) as a white solid used in next step without further purification. LCMS Rt=0.700 min, m/z=524.3 [M+H]+.

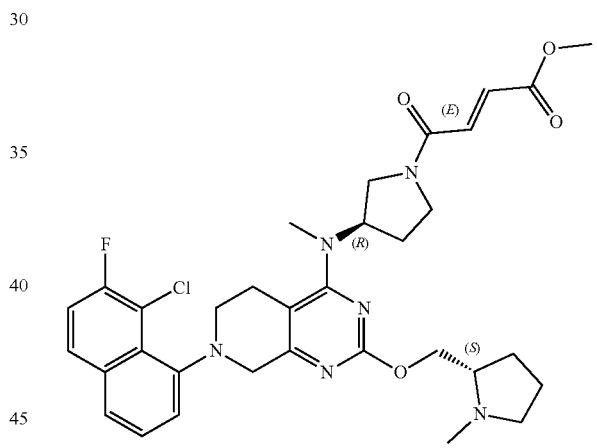

Step 3: methyl (E)-4-((R)-3-((7-(8-chloro-7-fluoronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-4-oxobut-2-enoate The amide coupling reaction was prepared in a similar fashion to Example 1 (Method 1-A, Step 6). The residue was purified by reverse phase HPLC (column: Phenomenex Luna 80*30 mm*3 μm; mobile phase: (water (FA)-ACN; B %: 5%-40%, 8 min) affording methyl (E)-4-((R)-3-((7-(8-chloro-7-fluoronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-4-oxobut-2-enoate (5 mg, 23.38%) as a yellow oil: $^1$H NMR (400 MHz, DMSO-d6) δ 8.04 (dd, J=5.9, 9.0 Hz, 1H), 7.81 (br d, J=7.9 Hz, 1H), 7.62 (t, J=8.9 Hz, 1H), 7.55 (br d, J=3.4 Hz, 1H), 7.50-7.38 (m, 1H), 7.37-7.22 (m, 1H), 6.88-6.56 (m, 1H), 5.00-4.65 (m, 1H), 4.40-4.03 (m, 3H), 3.98-3.87 (m, 1H), 3.86-3.60 (m, 9H), 3.19-3.04 (m, 3H), 3.03-2.94 (m, 3H), 2.65-2.54 (m, 5H), 2.28-1.94 (m, 2H), 1.88-1.34 (m, 4H). LCMS Rt=2.179 min, m/z=636.3 [M+H]+.

LCMS (5 to 95% acetonitrile in water+0.1% trifluoroacetic acid over 6 mins) retention time 2.179 min, ESI+ found [M+H]=636.3.

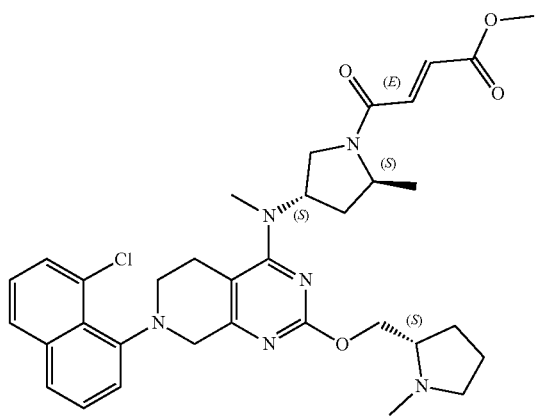

Example 4 (Method 1-A19): methyl (E)-4-((2S,4S)-4-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)-2-methylpyrrolidin-1-yl)-4-oxobut-2-enoate petroleum ether) affording (2S,4S)-tert-butyl 4-(((benzyloxy)carbonyl)amino)-2-methylpyrrolidine-1-carboxylate (600 mg, 71.8%) as a yellow oil: ¹H NMR (400 MHz, DMSO-d6) δ 7.56-7.55 (m, 1H), 7.40-7.32 (m, 5H), 5.09 (s, 2H), 4.09-4.05 (m, 1H), 3.92-3.82 (m, 1H), 3.44-3.39 (m, 1H), 3.17-3.12 (m, 1H), 2.01-1.92 (m, 1H), 1.79-1.74 (m, 1H), 1.41 (s, 9H), 1.20-1.16 (m, 3H).

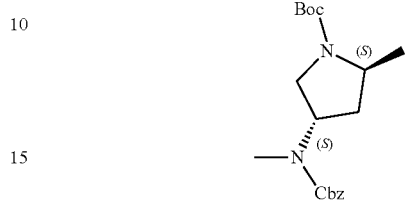

Step 2: (2S,4S)-tert-butyl 4-(((benzyloxy)carbonyl)(methyl)amino)-2-methylpyrrolidine-1-carboxylate To a solution of (2S,4S)-tert-butyl 4-(((benzyloxy)carbonyl)amino)-2-methylpyrrolidine-1-carboxylate (600 mg, 1.79 mmol) in N,N-dimethylformaldehyde (7 mL) was added sodium hydride (143.52 mg, 3.59 mmol, 60%) at 0° C. and stirred at 0° C. for 0.5 h. Iodomethane (382.00 mg, 2.69 mmol) was added into the above solution and stirred at 25° C. for 2 h. The mixture was diluted with water (20 mL) and extracted with ethyl acetate (3×20 mL). The combined organic layers were dried over sodium sulphate and concentrated in vacuo. The resulting residue was purified by column chromatography (silica gel, 100-200 mesh, 0-15% ethyl acetate in petroleum ether) affording (2S,4S)-tert-butyl 4-(((benzyloxy)carbonyl)(methyl)amino)-2-methylpyrrolidine-1-carboxylate (500 mg, 80%) as a yellow gum: ¹H NMR (400 MHz, DMSO-d6) δ 7.40-7.35 (m, 5H), 5.11 (s, 2H), 4.76-4.72 (m, 1H), 3.93-3.88 (m, 1H) 3.43-3.39 (m, 1H), 3.25-3.20 (m, 1H), 2.79 (s, 3H), 2.25-2.18 (m, 1H), 1.70-1.67 (m, 1H), 1.41 (s, 9H), 1.20-1.16 (m, 3H).

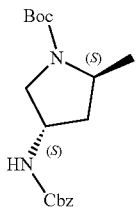

Step 1: (2S,4S)-tert-butyl 4-(((benzyloxy)carbonyl)amino)-2-methylpyrrolidine-1-carboxylate To a solution of tert-butyl (2S,4S)-4-amino-2-methylpyrrolidine-1-carboxylate (500 mg, 2.50 mmol) in tetrahydrofuran (5 mL) was added sodium hydroxide (2 M, 3.75 mL) and benzyl carbonochloridate (426.48 mg, 2.50 mmol) at 0° C., then the mixture was stirred at 20° C. for 2 h. The mixture was diluted with water (10 mL) and extracted with ethyl acetate (3×5 mL). The combined organic layers were dried over sodium sulphate and concentrated in vacuo. The resulting residue was purified by column chromatography (silica gel, 100-200 mesh, 0-15% ethyl acetate in

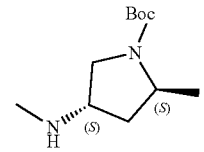

Step 3: (2S,4S)-tert-butyl 2-methyl-4-(methylamino)pyrrolidine-1-carboxylate

To a solution of (2S,4S)-tert-butyl 4-(((benzyloxy)carbonyl)(methyl)amino)-2-methylpyrrolidine-1-carboxylate (500 mg, 1.43 mmol) in ethyl acetate (6 mL) was added 10% Palladium on carbon (10 mg, 10% purity). Then the mixture was degassed and purged with hydrogen for 3 times and stirred at 25° C. for 12 h under hydrogen. The mixture was filtered and the filtrate concentrated in vacuo affording (2S,4S)-tert-butyl 2-methyl-4-(methylamino)pyrrolidine-1-carboxylate (280 mg, crude) as a colorless oil, which was used in the next step without further purification. LCMS Rt=0.250 min, m/z=241.2 [M+H]+.

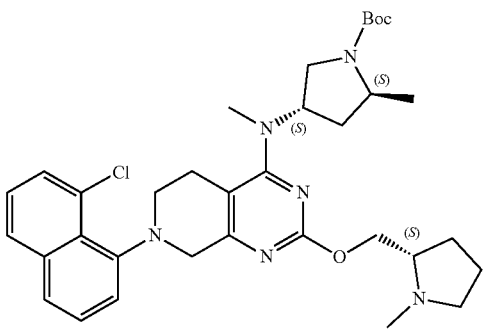

Step 4: (2S,4S)-tert-butyl 4-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)-2-methylpyrrolidine-1-carboxylate The substitution reaction was prepared in a similar fashion to Example 1 (Method 1-A), Step 4, substituting (S)-7-(8-chloronaphthalen-1-yl)-2-((1-methylpyrrolidin-2-yl)methoxy)-5,6,7,8-tetrahydropyrido[3,4-d]pyrimidin-4-yl trifluoromethanesulfonate for (S)-7-(8-chloro-7-fluoronaphthalen-1-yl)-2-((1-methylpyrrolidin-2-yl)methoxy)-5,6,7,8-tetrahydropyrido[3,4-d]pyrimidin-4-yl trifluoromethanesulfonate. The crude product was purified by reverse phase HPLC (Phenomenex Luna 80*30 mm*3 μm column; 10%-50% acetonitrile in 1% TFA in water, 8 min gradient) affording (2S,4S)-tert-butyl 4-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)-2-methylpyrrolidine-1-carboxylate (160 mg, 31%) as a yellow gum. LCMS Rt=0.726 min, m/z=620.3 [M+H]+.

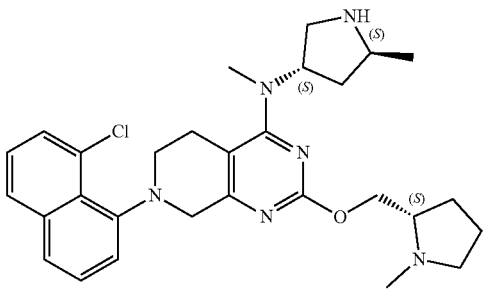

Step 5: 7-(8-chloronaphthalen-1-yl)-N-methyl-2-(((S)-1-methylpyrrolidin-2-yl)methoxy)-N-((3S,5S)-5-methylpyrrolidin-3-yl)-5,6,7,8-tetrahydropyrido[3,4-d]pyrimidin-4-amine The deprotection of Boc was prepared in a similar fashion to Example 1 (Method 1-A), Step 5. The mixture was concentrated to dryness in vacuo affording 7-(8-chloronaphthalen-1-yl)-N-methyl-2-(((S)-1-methylpyrrolidin-2-yl)methoxy)-N-((3S,5S)-5-methylpyrrolidin-3-yl)-5,6,7,8-tetrahydropyrido[3,4-d]pyrimidin-4-amine (140 mg, crude, hydrochloride salt) as a yellow gum, which was used in the next step without further purification. LCMS Rt=0.477 min, m/z=520.3 [M+H]+.


Step 6: methyl (E)-4-((2S,4S)-4-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)-2-methylpyrrolidin-1-yl)-4-oxobut-2-enoate The amide coupling reaction was prepared in a similar fashion to Example 1 (Method 1-A), Step 6. The crude product was purified by reverse phase HPLC (column: Waters Xbridge BEH C18 100*25 mm*5 μm; mobile phase: (water (ammonium bicarbonate)-ACN; B %: 50%-80%, 10 min) affording methyl (E)-4-((2S,4S)-4-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)-2-methylpyrrolidin-1-yl)-4-oxobut-2-enoate (14.35 mg, 23%) as a yellow oil: $^1$H NMR (400 MHz, Acetonitrile-d3) δ 7.88 (d, J=8.1 Hz, 1H), 7.71 (d, J=8.0 Hz, 1H), 7.61-7.49 (m, 2H), 7.42 (t, J=7.8 Hz, 1H), 7.38-7.33 (m, 1H), 7.31-7.21 (m, 1H), 6.80-6.66 (m, 1H), 5.09-4.97 (m, 1H), 4.47-4.31 (m, 2H), 4.26 (br d, J=17.3 Hz, 1H), 4.21-4.08 (m, 1H), 4.01-3.89 (m, 1H), 3.82-3.71 (m, 4H), 3.68-3.50 (m, 2H), 3.32-3.16 (m, 1H), 3.15-3.00 (m, 2H), 2.98-2.93 (m, 3H), 2.69-2.58 (m, 2H), 2.42 (d, J=2.4 Hz, 3H) 2.37-2.29 (m, 2H), 2.01 (br d, J=7.1 Hz, 1H), 1.88-1.67 (m, 4H), 1.36-1.22 (m, 3H). LCMS Rt=3.707 min, m/z=632.3 [M+H]+.

LCMS (5 to 95% acetonitrile in water+10 mM ammonium bicarbonate over 6 mins) retention time 3.707 min, ESI+ found [M+H]=632.3.


Example 5 (Method 1-A12): (E)-1-(3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-4-methoxybut-2-en-1-one

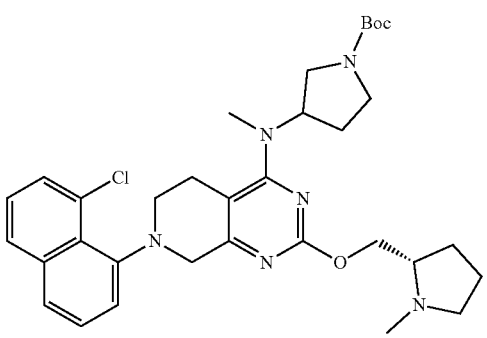 [SMILES: CN(c1nc(OC[C@@H]2CCCN2C)nc2c1CCN(c1cccc3cccc(Cl)c13)C2)C1CCN(C(=O)OC(C)(C)C)C1]

Step 1: tert-butyl 3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidine-1-carboxylate The substitution reaction was prepared in a similar fashion to Example 1 (Method 1-A), Step 4, substituting (S)-7-(8-chloronaphthalen-1-yl)-2-((1-methylpyrrolidin-2-yl)methoxy)-5,6,7,8-tetrahydropyrido[3,4-d]pyrimidin-4-yl trifluoromethanesulfonate for (S)-7-(8-chloro-7-fluoronaphthalen-1-yl)-2-((1-methylpyrrolidin-2-yl)methoxy)-5,6,7,8-tetrahydropyrido[3,4-d]pyrimidin-4-yl trifluoromethanesulfonate, and substituting tert-butyl 3-(methylamino)pyrrolidine-1-carboxylate for tert-butyl (2-(methylamino)ethyl)carbamate. The resulting residue was purified by column chromatography (silica gel, 100-200 mesh, 0-100% ethyl acetate in petroleum ether) affording tert-butyl 3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidine-1-carboxylate (500 mg, 37%) a yellow solid. LCMS Rt=0.720 min, m/z=606.31 [M+H]+.

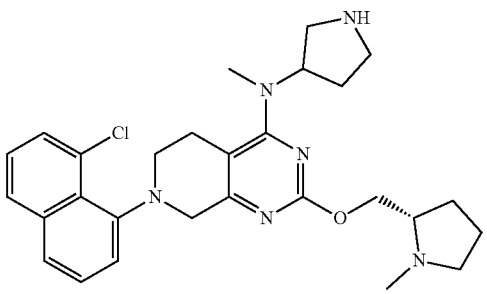 [SMILES: CN(c1nc(OC[C@@H]2CCCN2C)nc2c1CCN(c1cccc3cccc(Cl)c13)C2)C1CCNC1]

Step 2: 7-(8-chloro-1-naphthyl)-N-methyl-2-[[(2S)-1-methylpyrrolidin-2-yl]methoxy]-N-pyrrolidin-3-yl-6,8-dihydro-5H-pyrido[3,4-d]pyrimidin-4-amine The deprotection of Boc was prepared in a similar fashion to Example 1 (Method 1-A), Step 5. The reaction mixture was concentrated to dryness in vacuo affording 7-(8-chloro-1-naphthyl)-N-methyl-2-[[(2S)-1-methylpyrrolidin-2-yl]methoxy]-N-pyrrolidin-3-yl-6,8-dihydro-5H-pyrido[3,4-d]pyrimidin-4-amine (160 mg, crude, hydrochloride salt) as a red solid, which was used in next step without further purification. LCMS Rt=0.520 min, m/z=506.26 [M+H]+.

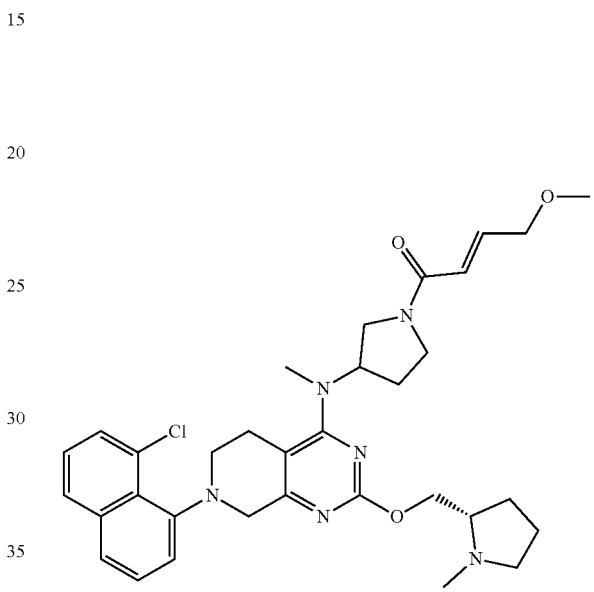

Step 3: (E)-1-(3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-4-methoxybut-2-en-1-one The amide coupling reaction was prepared in a similar fashion to Example 1 (Method 1-A), Step 6, substituting (E)-4-methoxybut-2-enoic acid for (E)-4-methoxy-4-oxobut-2-enoic acid. The resulting residue was purified by reverse phase HPLC (column: Waters Xbridge Prep OBD C18 150*40 mm*10 μm; mobile phase: (water (NH4HCO3)-ACN; B %: 40%-70%, 8 min) affording (E)-1-(3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-4-methoxybut-2-en-1-one (2.23 mg, 4%) as a yellow oil: $^1$H NMR (400 MHz, Acetonitrile-d3) δ ppm 7.80-7.75 (m, 1H), 7.63-7.57 (m, 1H), 7.50-7.38 (m, 2H), 7.35-7.29 (m, 1H), 7.27-7.22 (m, 1H), 6.75-6.63 (m, 1H), 6.37-6.24 (m, 1H), 4.81-4.61 (m, 1H), 4.28-4.11 (m, 2H), 4.08-3.94 (m, 3H), 3.86-3.57 (m, 3H), 3.52-3.40 (m, 2H), 3.35-3.24 (m, 4H), 3.08-2.93 (m, 1H), 2.96-2.86 (m, 4H), 2.57-2.46 (m, 2H), 2.32-2.27 (m, 3H), 2.20-2.15 (m, 2H), 2.08-1.97 (m, 2H), 1.94-1.88 (m, 1H), 1.71-1.53 (m, 3H). LCMS Rt=3.206 min, m/z=604.3 [M+H]+.

LCMS (5 to 95% acetonitrile in water+0.03% ammonium bicarbonate over 6 mins) retention time 3.206 min, ESI+ found [M+H]=604.3.

LCMS (5 to 95% acetonitrile in water+0.1% trifluoroacetic acid over 6 mins) retention time 2.162 min, ESI+ found [M+H]=618.3.

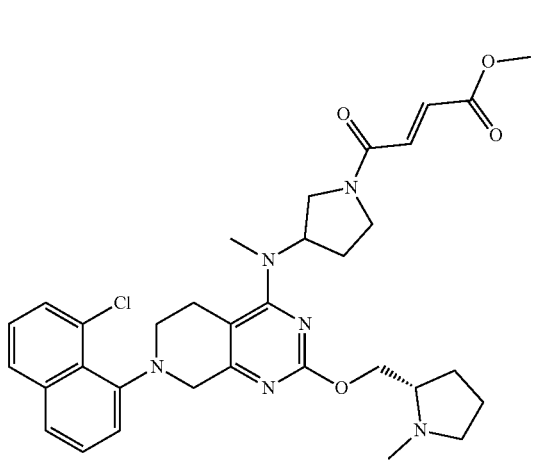 [SMILES: COC(=O)/C=C/C(=O)N1CCC(N(C)c2nc(OC[C@@H]3CCCN3C)nc3c2CCN(c2cccc4cccc(Cl)c24)C3)C1]

Example 6 (Method 1-A2): methyl (E)-4-(3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-4-oxobut-2-enoate The amide coupling reaction was prepared in a similar fashion to Example 1 (Method 1-A), Step 6, substituting 7-(8-chloro-1-naphthyl)-N-methyl-2-[[(2S)-1-methylpyrrolidin-2-yl]methoxy]-N-pyrrolidin-3-yl-6,8-dihydro-5H-pyrido[3,4-d]pyrimidin-4-amine (as prepared in Example 5 Step 2) for (S)—N$^1$-(7-(8-chloro-7-fluoronaphthalen-1-yl)-2-((1-methylpyrrolidin-2-yl)methoxy)-5,6,7,8-tetrahydropyrido[3,4-d]pyrimidin-4-yl)-N$^1$-methylethane-1,2-diamine. The mixture was purified by reverse phase HPLC (column: Phenomenex Luna 80*30 mm*3 μm; mobile phase: (water(0.1% TFA)-ACN; B %: 25%-55%, 8 min) affording methyl (E)-4-(3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-4-oxobut-2-enoate (9.68 mg, 12%, trifluoroacetate salt) as a yellow oil: $^1$H NMR (400 MHz, Acetonitrile-d3) δ 7.87 (d, J=8.2 Hz, 1H), 7.73 (br d, J=8.0 Hz, 1H), 7.60-7.49 (m, 2H), 7.44-7.39 (m, 1H), 7.37-7.22 (m, 2H), 6.74-6.68 (m, 1H), 5.15-5.01 (m, 1H), 4.75-4.59 (m, 2H), 4.34 (br d, J=17.8 Hz, 2H), 3.98-3.84 (m, 2H), 3.76 (d, J=4.3 Hz, 3H), 3.73-3.52 (m, 4H), 3.48-3.26 (m, 2H), 3.19-3.04 (m, 5H), 2.92 (br s, 3H), 2.71 (br d, J=15.4 Hz, 1H), 2.39-2.17 (m, 3H), 2.16-1.98 (m, 3H) LCMS Rt=2.162 min, m/z=618.3 [M+H]+.

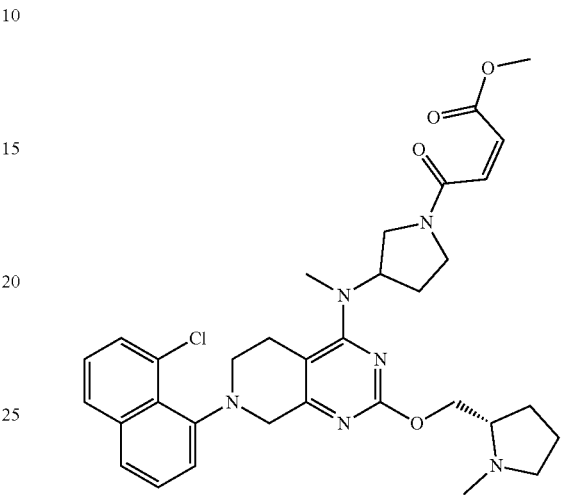

Example 7 (Method 1-A10): methyl (Z)-4-(3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-4-oxobut-2-enoate The amide coupling reaction was prepared from 7-(8-chloro-1-naphthyl)-N-methyl-2-[[(2S)-1-methylpyrrolidin-2-yl]methoxy]-N-pyrrolidin-3-yl-6,8-dihydro-5H-pyrido[3,4-d]pyrimidin-4-amine (as prepared in Example 5 Step 2), in a similar fashion to Example 1 (Method 1-A), Step 6, substituting (Z)-4-methoxy-4-oxobut-2-enoic acid for (E)-4-methoxy-4-oxobut-2-enoic acid. The residue was purified by reverse phase HPLC (column: Phenomenex Luna 80*30 mm*3 μm; mobile phase: (water (FA)-ACN; B %: 1%-40%, 8 min) affording methyl (Z)-4-(3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-4-oxobut-2-enoate (4.87 mg, 7%, formate salt) as a yellow solid: $^1$H NMR (400 MHz, Acetonitrile-d3) δ ppm 8.29 (s, 1H), 7.87 (d, J=8.00 Hz, 1H), 7.70 (br d, J=8.25 Hz, 1H), 7.63-7.48 (m, 2H), 7.46-7.38 (m, 1H), 7.37-7.27 (m, 1H), 6.73-6.47 (m, 1H), 6.20-5.97 (m, 1H), 4.90-4.73 (m, 1H), 4.52-4.40 (m, 1H), 4.26 (br d, J=17.39 Hz, 2H), 3.98-3.82 (m, 1H), 3.80-3.67 (m, 5H), 3.66-3.49 (m, 2H), 3.47-3.17 (m, 5H), 3.16-3.03 (m, 3H), 3.02-2.94 (m, 3H), 2.87 (br d, J=3.63 Hz, 2H), 2.05-2.24 (m, 3H), 1.88 (br s, 2H), 1.42-1.64 (m, 1H). LCMS Rt=2.054 min, m/z=618.3 [M+H]+.

LCMS (5 to 95% acetonitrile in water+0.1% trifluoroacetic acid over 6 mins) retention time 2.054 min, ESI+ found [M+H]=618.3.

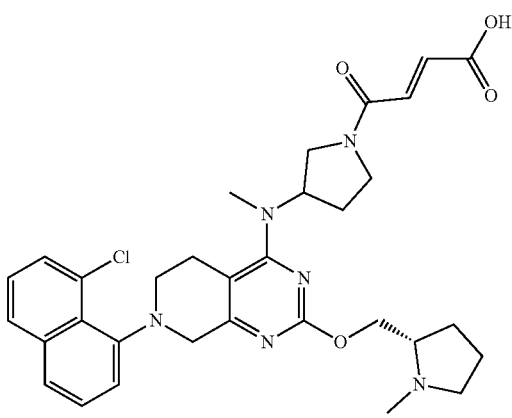 [SMILES: CN(c1nc(OC[C@@H]2CCCN2C)nc2c1CCN(c1cccc3cccc(Cl)c13)C2)C1CCN(C(=O)/C=C/C(=O)O)C1]

Example 8 (Method 1-A16): (E)-4-(3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-4-oxobut-2-enoic acid The amide coupling reaction was prepared from 7-(8-chloro-1-naphthyl)-N-methyl-2-[[(2S)-1-methylpyrrolidin-2-yl]methoxy]-N-pyrrolidin-3-yl-6,8-dihydro-5H-pyrido[3,4-d]pyrimidin-4-amine (as prepared in Example 5 Step 2), in a similar fashion to Example 1 (Method 1-A), Step 6, substituting fumaric acid for (E)-4-methoxy-4-oxobut-2-enoic acid. The resulting residue was purified by reverse phase HPLC (column: Phenomenex Luna 80*30 mm*3 μm; mobile phase: (water (FA)-ACN; B %: 5%-45%, 8 min) affording (E)-4-(3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-4-oxobut-2-enoic acid (45 mg, 34%, formate salt) as a white solid: $^1$H NMR (400 MHz, DMSO-d6) δ ppm 7.93 (d, J=8.19 Hz, 1H), 7.71-7.83 (m, 1H), 7.51-7.63 (m, 2H), 7.46-7.42 (m, 1H), 7.30-7.43 (m, 1H), 7.22-7.18 (m, 1H), 6.64-6.60 (m, 1H), 4.68-4.95 (m, 1H), 4.25-4.39 (m, 2H), 4.11-4.24 (m, 3H), 4.07-4.04 (m, 1H), 3.83-3.98 (m, 3H), 3.72-3.80 (m, 3H), 3.04-3.13 (m, 2H), 2.93-3.03 (m, 4H), 2.82-2.93 (m, 1H), 2.59 (br s, 2H), 2.12-2.23 (m, 1H), 1.95-2.05 (m, 1H), 1.58-1.84 (m, 3H), 1.42-1.56 (m, 1H). LCMS Rt=2.591 min, m/z=604.2 [M+H]+.

LCMS (5 to 95% acetonitrile in water+0.03% ammonium bicarbonate over 6 mins) retention time 2.591 min, ESI+ found [M+H]=604.2.

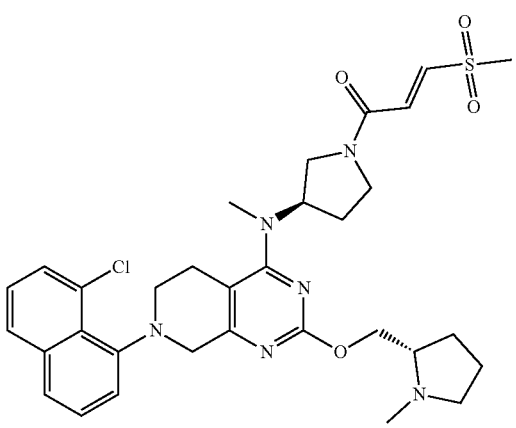 [SMILES: CN1CCC[C@H]1COc1nc2c(c(N(C)[C@@H]3CCN(C(=O)/C=C/S(C)(=O)=O)C3)n1)CCN(c1cccc3cccc(Cl)c13)C2]

Example 9 (Method 1-A21): (E)-1-((R)-3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-3-(methylsulfonyl)prop-2-en-1-one

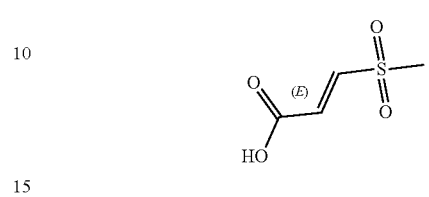

Step 1: (E)-3-methylsulfonylprop-2-enoic acid

A mixture of 2,3-dibromopropanoic acid (19.54 g, 84.28 mmol) and sodium ethanesulfinate (11.72 g, 126.43 mmol) in N,N-dimethylformaldehyde (30 mL) was stirred at 80° C. for 12 h. The reaction mixture was concentrated to dryness in vacuo. The resulting residue was purified by reverse phase HPLC (column: Phenomenex luna C18 250*50 mm*10 μm; mobile phase: (water (TFA)-ACN; B %: 1%-20%, 10 min) affording (E)-3-methylsulfonylprop-2-enoic acid (8 g, 63%) as a yellow oil: $^1$H NMR (400 MHz, DMSO-d6) δ ppm 7.65-7.61 (d, J=15.6 Hz, 1H), 6.64-6.60 (d, J=15.6 Hz, 1H), 3.17 (s, 3H).

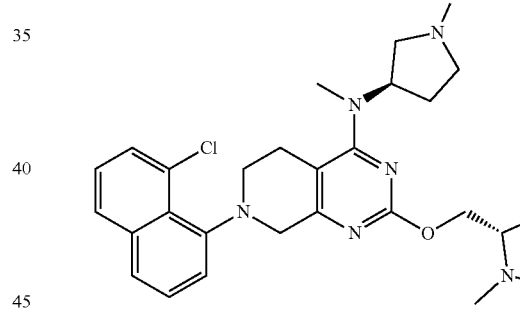

Step 2: tert-butyl (R)-3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidine-1-carboxylate The substitution reaction of (S)-7-(8-chloronaphthalen-1-yl)-2-((1-methylpyrrolidin-2-yl)methoxy)-5,6,7,8-tetrahydropyrido[3,4-d]pyrimidin-4-yl trifluoromethanesulfonate was prepared in a similar fashion to Example 1 (Method 1-A), Step 4, substituting tert-butyl (R)-3-(methylamino)pyrrolidine-1-carboxylate for tert-butyl N-[2-(methylamino)ethyl]carbamate. The resulting residue was purified by column chromatography (silica gel, 100-200 mesh, 0-50% ethyl acetate in petroleum ether) affording tert-butyl (R)-3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidine-1-carboxylate (270 mg, 32%) as a brown gum. LCMS Rt=0.942 min, m/z=606.3 [M+H]+.

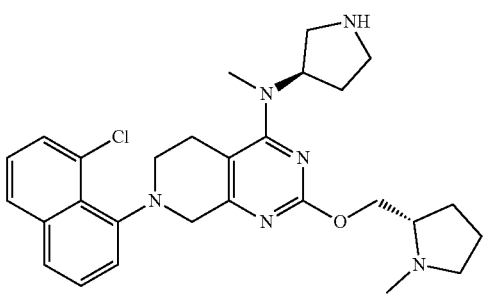 [SMILES: CN1CCC[C@H]1COc1nc2c(c(N(C)[C@@H]3CCNC3)n1)CCN(c1cccc3cccc(Cl)c13)C2]

Step 3: 7-(8-chloro-1-naphthyl)-N-methyl-2-[[(2S)-1-methylpyrrolidin-2-yl]methoxy]-N-[(3R)-pyrrolidin-3-yl]-6,8-dihydro-5H-pyrido[3,4-d]pyrimidin-4-amine The deprotection of Boc was prepared in a similar fashion to Example 1 (Method 1-A), Step 5. The reaction mixture was concentrated in vacuo affording 7-(8-chloro-1-naphthyl)-N-methyl-2-[[(2S)-1-methylpyrrolidin-2-yl]methoxy]-N-[(3R)-pyrrolidin-3-yl]-6,8-dihydro-5H-pyrido[3,4-d]pyrimidin-4-amine (240 mg, crude, hydrochloride salt) as a brown gum, which was used in the next step without further purification. LCMS Rt=0.453 min, m/z=506.3 [M+H]+.

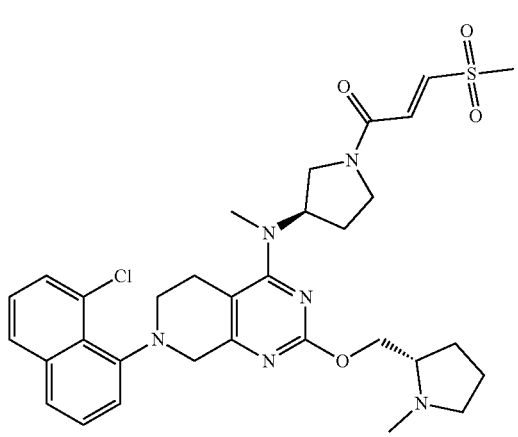 [SMILES: CN1CCC[C@H]1COc1nc2c(c(N(C)[C@@H]3CCN(C(=O)/C=C/S(C)(=O)=O)C3)n1)CCN(c1cccc3cccc(Cl)c13)C2]

Step 4: (E)-1-((R)-3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-3-(methylsulfonyl)prop-2-en-1-one The amide coupling reaction was prepared in a similar fashion to Example 1 (Method 1-A), Step 6, substituting (E)-3-methylsulfonylprop-2-enoic acid for (E)-4-methoxy-4-oxobut-2-enoic acid. The mixture was purified by reverse phase HPLC (column: Waters Xbridge BEH C18 100*30 mm*10 μm; mobile phase: (water(NH₄HCO₃)-ACN; B %: 35%-55%, 8 min) affording (E)-1-((R)-3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-3-(methylsulfonyl)prop-2-en-1-one (6.29 mg, 10%) as a yellow solid: ¹H NMR (400 MHz, Acetonitrile-d3) δ 7.87-7.82 (m, 1H), 7.71-7.65 (m, 1H), 7.55 (d, J=7.4 Hz, 1H), 7.53-7.47 (m, 1H), 7.39 (t, J=7.8 Hz, 1H), 7.36-7.30 (m, 2H), 7.22-7.11 (m, 1H), 4.92-4.71 (m, 1H), 4.41-4.29 (m, 1H), 4.27-4.20 (m, 1H), 4.19-4.06 (m, 1H), 3.98-3.85 (m, 1H), 3.68 (s, 2H), 3.66-3.58 (m, 1H), 3.57-3.49 (m, 1H), 3.48-3.36 (m, 1H), 3.28-3.04 (m, 3H), 3.03-3.00 (m, 3H), 2.99-2.94 (m, 3H), 2.72-2.56 (m, 2H), 2.47-2.36 (m, 4H), 2.11-1.98 (m, 2H), 1.86-1.55 (m, 4H). LCMS Rt=3.449 min, m/z=638.2 [M+H]+.

LCMS (5 to 95% acetonitrile in water+0.03% ammonium bicarbonate over 6 mins) retention time 3.449 min, ESI+ found [M+H]=638.2.

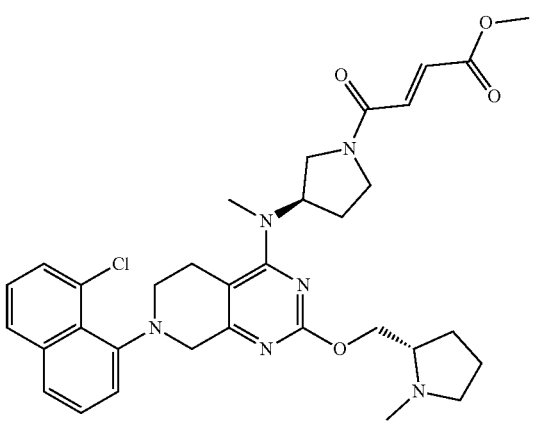 [SMILES: COC(=O)/C=C/C(=O)N1CC[C@@H](N(C)c2nc(OC[C@@H]3CCCN3C)nc3c2CCN(c2cccc4cccc(Cl)c24)C3)C1]

Example 10 (Method 1-A7): methyl (E)-4-((R)-3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-4-oxobut-2-enoate The amide coupling reaction was prepared in a similar fashion to Example 1 (Method 1-A), Step 6, substituting 7-(8-chloronaphthalen-1-yl)-N-methyl-2-(((S)-1-methylpyrrolidin-2-yl)methoxy)-N—((R)-pyrrolidin-3-yl)-5,6,7,8-tetrahydropyrido[3,4-d]pyrimidin-4-amine (prepared according to Example 9 Step 3) for (S)—N¹-(7-(8-chloro-7-fluoronaphthalen-1-yl)-2-((1-methylpyrrolidin-2-yl)methoxy)-5,6,7,8-tetrahydropyrido[3,4-d]pyrimidin-4-yl)-N¹-methylethane-1,2-diamine. The residue was purified by reverse phase HPLC (column: Phenomenex Luna 80*30 mm*3 μm; mobile phase: (water (FA)-ACN; B %: 5%-40%, 8 min) affording methyl (E)-4-((R)-3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-4-oxobut-2-enoate (16.03 mg, 30%, formate salt) as a yellow solid: ¹H NMR (400 MHz, Acetonitrile-d3) δ ppm 7.84 (d, J=8.13 Hz, 1H), 7.67 (d, J=8.13 Hz, 1H), 7.57-7.45 (m, 2H,) 7.42-7.36 (m, 1H), 7.34-7.27 (m, 1H), 7.26-7.18 (m, 1H), 6.74-6.62 (m, 1H), 4.92-4.67 (m, 1H), 4.41-4.29 (m, 1H), 4.25-4.13 (m, 2H), 3.96-3.79 (m, 1H), 3.77-3.66 (m, 5H), 3.63-3.32 (m, 3H), 3.31-3.19 (m, 1H), 3.18-3.01 (m, 3H), 2.98-2.94 (m, 3H), 2.79-2.74 (m, 1H), 2.61-2.57 (m, 1H), 2.39-2.29 (m, 3H), 2.09-2.22 (m, 2H), 1.50-1.86 (m, 4H). LCMS Rt=2.114 min, m/z=618.3 [M+H]+.

LCMS (5 to 95% acetonitrile in water+0.1% trifluoroacetic acid over 6 mins) retention time 2.114 min, ESI+ found [M+H]=618.3.

LCMS (5 to 95% acetonitrile in water+0.03% ammonium bicarbonate over 6 mins) retention time 3.519 min, ESI+ found [M+H]=646.3.

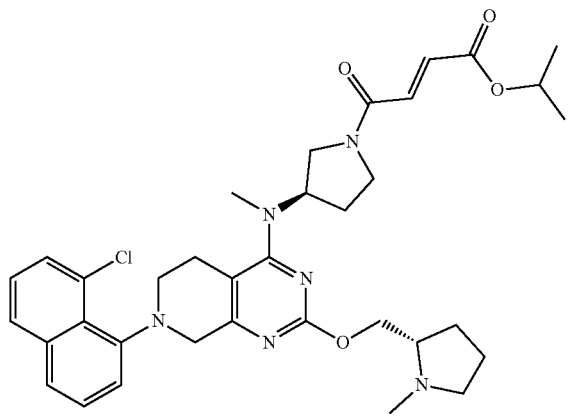 [SMILES: CC(C)OC(=O)/C=C/C(=O)N1CC[C@@H](N(C)c2nc(OC[C@@H]3CCCN3C)nc3c2CCN(c2cccc4cccc(Cl)c24)C3)C1]

Example 11 (Method 1-A24): isopropyl (E)-4-((R)-3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-4-oxobut-2-enoate The amide coupling reaction was prepared in a similar fashion to Example 1 (Method 1-A), Step 6, substituting 7-(8-chloronaphthalen-1-yl)-N-methyl-2-(((S)-1-methylpyrrolidin-2-yl)methoxy)-N—((R)-pyrrolidin-3-yl)-5,6,7,8-tetrahydropyrido[3,4-d]pyrimidin-4-amine (prepared according to Example 9 Step 3) for (S)—N$^1$-(7-(8-chloro-7-fluoronaphthalen-1-yl)-2-((1-methylpyrrolidin-2-yl)methoxy)-5,6,7,8-tetrahydropyrido[3,4-d]pyrimidin-4-yl)-N$^1$-methylethane-1,2-diamine, and substituting (E)-4-isopropoxy-4-oxobut-2-enoic acid for (E)-4-methoxy-4-oxobut-2-enoic acid. The reaction mixture was purified by reverse phase HPLC (Phenomenex C18 75*30 mm*3 μm column; 60%-90% acetonitrile in a ammonium bicarbonate solution in water, 8 min gradient) affording isopropyl (E)-4-((R)-3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-4-oxobut-2-enoate (12.14 mg, 13%) as yellow solid: $^1$H NMR (400 MHz, Acetonitrile-d3) δ 7.85 (d, J=7.9 Hz, 1H), 7.68 (br d, J=8.5 Hz, 1H), 7.58-7.54 (m, 1H), 7.50 (dt, J=2.8, 7.7 Hz, 1H), 7.43-7.37 (m, 1H), 7.32 (br t, J=6.3 Hz, 1H), 7.28-7.15 (m, 1H), 6.69-6.59 (m, 1H), 5.13-4.99 (m, 1H), 4.89-4.71 (m, 1H), 4.34-4.19 (m, 2H), 4.08 (td, J=5.7, 10.8 Hz, 1H), 3.97-3.81 (m, 1H), 3.80-3.49 (m, 4H), 3.48-3.33 (m, 1H), 3.31-3.04 (m, 2H), 3.01-2.92 (m, 4H), 2.66-2.47 (m, 2H), 2.34 (br d, J=4.1 Hz, 3H), 2.26-2.17 (m, 4H) 1.74-1.59 (m, 3H), 1.27 (dt, J=2.0, 4.1 Hz, 6H). LCMS Rt=3.519 min, m/z=646.3 [M+H]+.

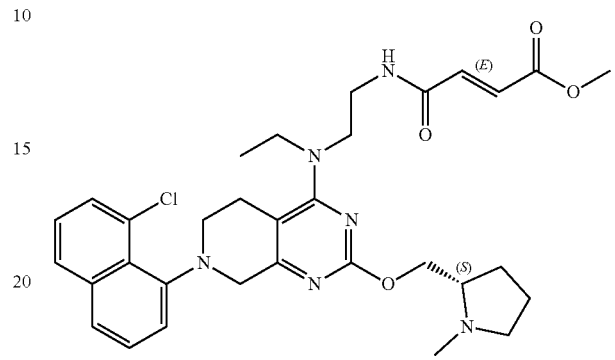

Example 12 (Method 1-A3): methyl (S,E)-4-((2-((7-(8-chloronaphthalen-1-yl)-2-((1-methylpyrrolidin-2-yl)methoxy)-5,6,7,8-tetrahydropyrido[3,4-d]pyrimidin-4-yl)(ethyl)amino)ethyl)amino)-4-oxobut-2-enoate

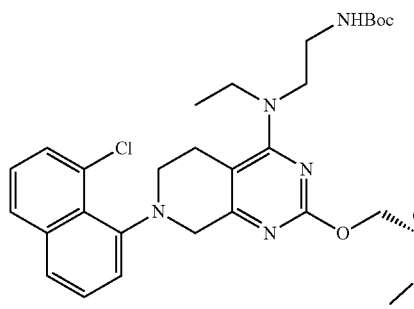

Step 1: tert-butyl (S)-(2-((7-(8-chloronaphthalen-1-yl)-2-((1-methylpyrrolidin-2-yl)methoxy)-5,6,7,8-tetrahydropyrido[3,4-d]pyrimidin-4-yl)(ethyl)amino)ethyl)carbamate The substitution reaction of (S)-7-(8-chloronaphthalen-1-yl)-2-((1-methylpyrrolidin-2-yl)methoxy)-5,6,7,8-tetrahydropyrido[3,4-d]pyrimidin-4-yl trifluoromethanesulfonate was prepared in a similar fashion to Example 1 (Method 1-A), Step 4, substituting tert-butyl (2-(ethylamino)ethyl)carbamate for tert-butyl N-[2-(methylamino)ethyl]carbamate. The crude product was purified by column chromatography (silica gel, 100-200 mesh, 0-80% ethyl acetate in petroleum ether) affording tert-butyl (S)-(2-((7-(8-chloronaphthalen-1-yl)-2-((1-methylpyrrolidin-2-yl)methoxy)-5,6,7,8-tetrahydropyrido[3,4-d]pyrimidin-4-yl)(ethyl) amino)ethyl)carbamate (300 mg, 47%) as a white solid. LCMS Rt=0.701 min, m/z=594.3 [M+H]+.

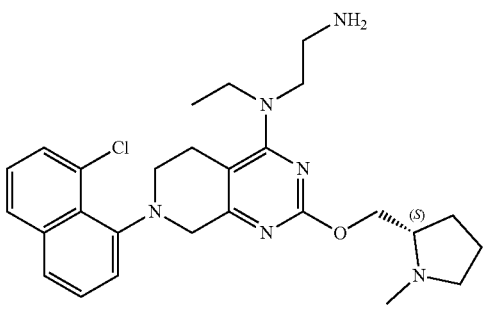

Step 2: N'-[7-(8-chloro-1-naphthyl)-2-[[(2S)-1-methylpyrrolidin-2-yl]methoxy]-6,8-dihydro-5H-pyrido[3,4-d]pyrimidin-4-yl]-N'-ethyl-ethane-1,2-diamine The deprotection of Boc was prepared in a similar fashion to Example 1 (Method 1-A), Step 5. The resultant mixture was concentrated to dryness in vacuo affording N'-[7-(8-chloro-1-naphthyl)-2-[[(2S)-1-methylpyrrolidin-2-yl]methoxy]-6,8-dihydro-5H-pyrido[3,4-d]pyrimidin-4-yl]-N'-ethyl-ethane-1,2-diamine (200 mg, 80%) as a brown solid, which was used in the next step without further purification. LCMS Rt=1.125 min, m/z=494.3 [M+H]+.

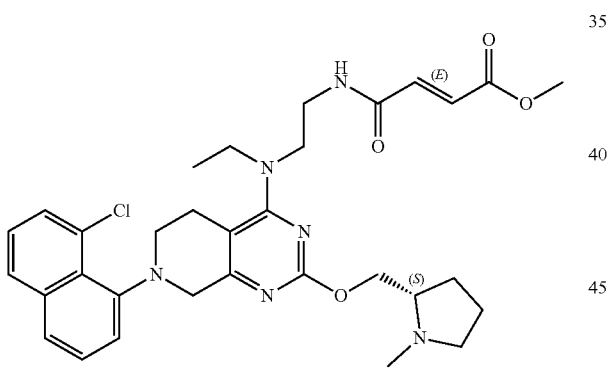

Step 3: methyl (S,E)-4-((2-((7-(8-chloronaphthalen-1-yl)-2-((1-methylpyrrolidin-2-yl)methoxy)-5,6,7,8-tetrahydropyrido[3,4-d]pyrimidin-4-yl)(ethyl)amino)ethyl)amino)-4-oxobut-2-enoate The amide-coupling reaction was prepared in a similar fashion to Example 1 (Method 1-A), Step 6. The crude product was purified by reverse phase HPLC (column: Waters Xbridge BEH C18 100*30 mm*10 μm; mobile phase: [water(NH₄HCO₃)-ACN]; B %: 45%-75%, 8 min) affording methyl (S,E)-4-((2-((7-(8-chloronaphthalen-1-yl)-2-((1-methylpyrrolidin-2-yl)methoxy)-5,6,7,8-tetrahydropyrido[3,4-d]pyrimidin-4-yl)(ethyl)amino)ethyl)amino)-4-oxobut-2-enoate (31.13 mg, 24%) as a yellow solid: ¹H NMR (400 MHz, Acetonitrile-d3) δ 7.95-7.65 (m, 1H), 7.63-7.21 (m, 5H), 7.01-6.81 (m, 1H), 6.75-6.52 (m, 1H), 4.47-4.05 (m, 2H), 3.92-3.75 (m, 3H), 3.65-3.45 (m, 3H), 3.30-2.95 (m, 4H), 2.75-2.55 (m, 1H), 2.50-2.40 (m, 4H), 2.30-2.10 (m, 6H), 1.75-1.55 (m, 4H), 1.15-1.05 (m, 3H). LCMS Rt=3.292 min, m/z=606.3 [M+H]+.

LCMS (5 to 95% acetonitrile in water+0.03% ammonium bicarbonate over 6 mins) retention time 3.292 min, ESI+ found [M+H]=606.3.

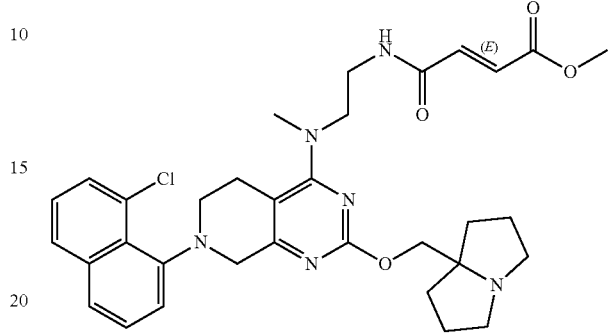

Example 13 (Method 1-A6): Methyl (E)-4-((2-((7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl)(methyl)amino)ethyl)amino)-4-oxobut-2-enoate

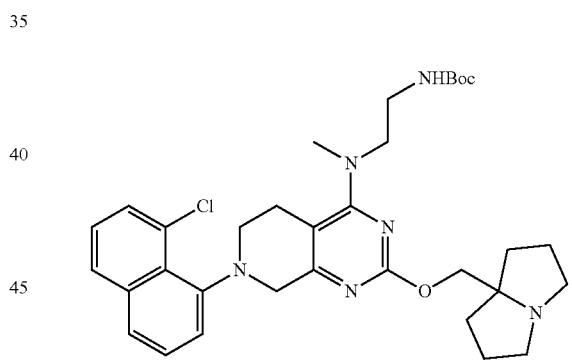

Step 1: tert-butyl (2-((7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl)(methyl)amino)ethyl)carbamate The substitution reaction was prepared in a similar fashion to Example 1 (Method 1-A), Step 4, substituting 7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl trifluoromethanesulfonate for (S)-7-(8-chloro-7-fluoronaphthalen-1-yl)-2-((1-methylpyrrolidin-2-yl)methoxy)-5,6,7,8-tetrahydropyrido[3,4-d]pyrimidin-4-yl trifluoromethanesulfonate. The crude product was purified by column chromatography (silica gel, 100-200 mesh, 0-100% methanol in dichloromethane) affording tert-butyl (2-((7-(8-chloronaphthalen-1-yl)-2-((tetrahydro-1H-pyrrolizin-7a(5H)-yl)methoxy)-5,6,7,8-tetrahydropyrido[3,4-d]

pyrimidin-4-yl)(methyl)amino)ethyl)carbamate (580 mg, 90%) as a brown oil. LCMS Rt=1.740 min, m/z=606.3 [M+H]+.

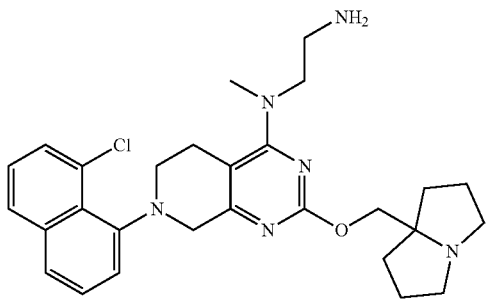 [SMILES: CN(CCN)c1nc(OCC23CCCN2CCC3)nc2c1CCN(c1cccc3cccc(Cl)c13)C2]

Step 2: N'-(7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl)-N$^1$-methylethane-1,2-diamine The deprotection of Boc was prepared in a similar fashion to Example 1 (Method 1-A), Step 5. The resultant mixture was concentrated to dryness in vacuo and the crude product was purified by reverse phase HPLC (column: Phenomenex luna C18 250*50 mm*10 μm; mobile phase: (water(TFA)-ACN; B %: 15%-45%, 10 min) affording N'-(7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl)-N'-methylethane-1,2-diamine (160 mg, 27%, trifluoroacetate salt) as a yellow solid, which was used in the next step without further purification. LCMS Rt=0.599 min, m/z=506.2 [M+H]+.

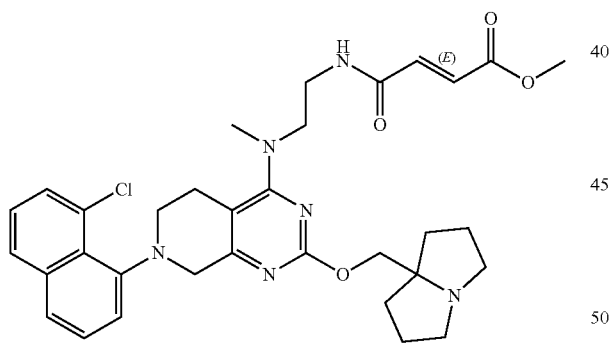

Step 3: Methyl (E)-4-((2-((7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl)(methyl)amino)ethyl)amino)-4-oxobut-2-enoate The amide coupling reaction was prepared in a similar fashion to Example 1 (Method 1-A), Step 6. The crude product was purified by reverse phase HPLC (column: Waters Xbridge Prep OBD C18 150*40 mm*10 μm; mobile phase: [water(NH$_4$HCO$_3$)-ACN]; B %: 35%-65%, 8 min) affording methyl (E)-4-((2-((7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl)(methyl)amino)ethyl)amino)-4-oxobut-2-enoate (38 mg, 23%) as a pale yellow solid: $^1$H NMR (400 MHz, Acetonitrile-d3) δ 7.87 (dd, J=8.2, 0.89 Hz, 1H), 7.70 (d, J=7.6 Hz, 1H), 7.49-7.60 (m, 2H), 7.40-7.45 (m, 1H), 7.38 (br s, 1H), 7.33 (dd, J=7.6, 0.95 Hz, 1H), 6.86 (d, J=15.5 Hz, 1H), 6.63 (d, J=15.5 Hz, 1H), 4.21 (d, 1H), 3.96-4.01 (m, 2H), 3.78-3.86 (m, 1H), 3.76 (s, 3H), 3.75-3.71 (d, 1H), 3.49-3.64 (m, 4H), 3.20-3.30 (m, 1H), 3.16 (s, 3H), 3.03-3.12 (m, 1H), 2.95-3.02 (m, 2H), 2.58-2.72 (m, 3H), 1.72-1.95 (m, 6H), 1.56-1.68 (m, 2H). LCMS Rt=2.774 min, m/z=618.3 [M+H]+.

LCMS (5 to 95% acetonitrile in water+0.03% ammonium bicarbonate over 6 mins) retention time 2.774 min, ESI+ found [M+H]=618.3.

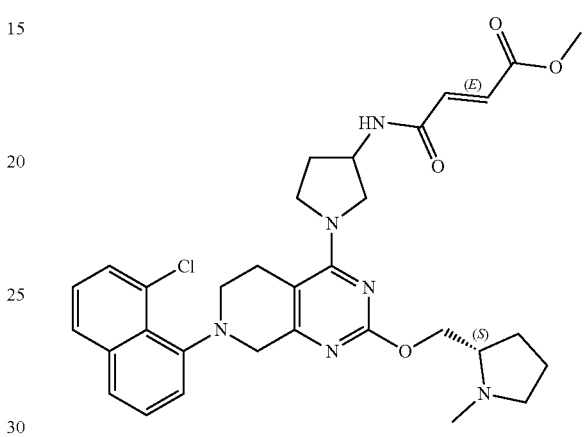

Example 14 (Method 1-A5): methyl (E)-4-((1-(7-(8-chloronaphthalen-1-yl)-2-(((S)-1-methylpyrrolidin-2-yl)methoxy)-5,6,7,8-tetrahydropyrido[3,4-d]pyrimidin-4-yl)pyrrolidin-3-yl)amino)-4-oxobut-2-enoate

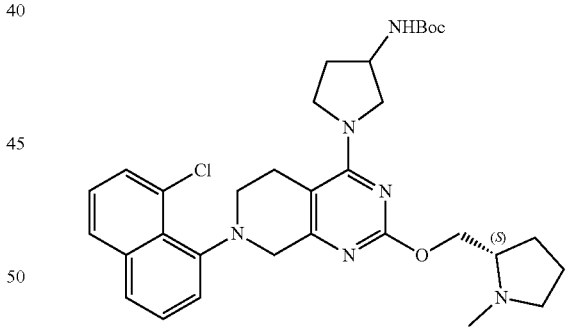

Step 1: tert-butyl N-[1-[7-(8-chloro-1-naphthyl)-2-[[(2S)-1-methylpyrrolidin-2-yl]methoxy]-6,8-dihydro-5H-pyrido[3,4-d]pyrimidin-4-yl]pyrrolidin-3-yl]carbamate The substitution reaction was prepared in a similar fashion to Example 1 (Method 1-A), Step 4, substituting (S)-7-(8-chloronaphthalen-1-yl)-2-((1-methylpyrrolidin-2-yl)methoxy)-5,6,7,8-tetrahydropyrido[3,4-d]pyrimidin-4-yl trifluoromethanesulfonate for (S)-7-(8-chloro-7-fluoronaphthalen-1-yl)-2-((1-methylpyrrolidin-2-yl)methoxy)-5,6,7,8-tetrahydropyrido[3,4-d]pyrimidin-4-yl trifluoromethanesulfonate, and substituting tert-butyl pyrrolidin-3- ylcarbamate for tert-butyl N-[2-(methylamino)ethyl]carbamate. The crude product was purified by column chromatography (silica gel, 100-200 mesh, 0-10% methanol in dichloromethane) affording tert-butyl N-[1-[7-(8-chloro-1-naphthyl)-2-[[(2S)-1-methylpyrrolidin-2-yl]methoxy]-6,8-dihydro-5H-pyrido[3,4-d]pyrimidin-4-yl]pyrrolidin-3-yl]carbamate (210 mg, 37%) as a brown solid, which was used in the next step without further purification. LCMS Rt=0.667 min, m/z=592.2 [M+H]+.

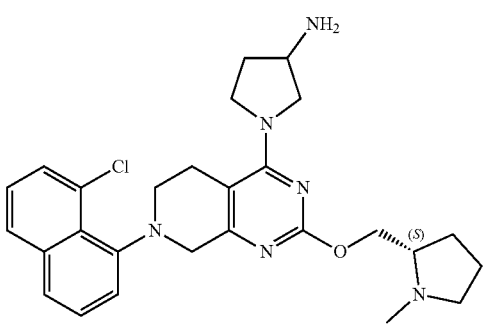

Step 2: 1-[7-(8-chloro-1-naphthyl)-2-[[(2S)-1-methylpyrrolidin-2-yl]methoxy]-6,8-dihydro-5H-pyrido[3,4-d]pyrimidin-4-yl]pyrrolidin-3-amine The deprotection of Boc was prepared in a similar fashion to Example 1 (Method 1-A), Step 6. The resultant mixture was concentrated in vacuo affording 1-[7-(8-chloro-1-naphthyl)-2-[[(2S)-1-methylpyrrolidin-2-yl]methoxy]-6,8-dihydro-5H-pyrido[3,4-d]pyrimidin-4-yl]pyrrolidin-3-amine (80 mg, crude, hydrochloride salt) as a brown solid, which was used in the next step without further purification. LCMS Rt=0.556 min, m/z=492.2 [M+H]+.

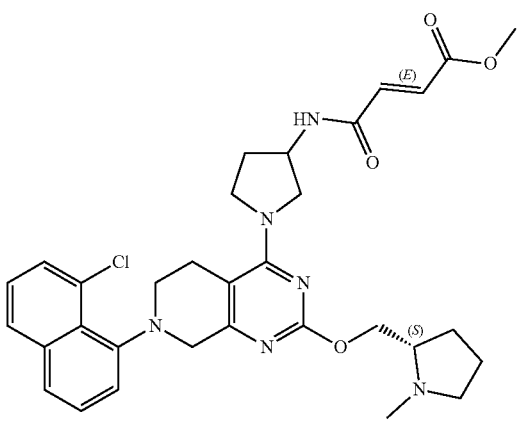

Step 3: methyl (E)-4-((1-(7-(8-chloronaphthalen-1-yl)-2-(((S)-1-methylpyrrolidin-2-yl)methoxy)-5,6,7,8-tetrahydropyrido[3,4-d]pyrimidin-4-yl)pyrrolidin-3-yl)amino)-4-oxobut-2-enoate The amide coupling reaction was prepared in a similar fashion to Example 1 (Method 1-A), Step 6. The reaction mixture was concentrated in vacuo and purified by reverse phase HPLC (column: Waters Xbridge BEH C18 100*30 mm*10 μm; mobile phase: (water(10 mM NH4HCO3)-ACN; B %: 30%-60%, 8 min) affording methyl (E)-4-((1-(7-(8-chloronaphthalen-1-yl)-2-(((S)-1-methylpyrrolidin-2-yl)methoxy)-5,6,7,8-tetrahydropyrido[3,4-d]pyrimidin-4-yl)pyrrolidin-3-yl)amino)-4-oxobut-2-enoate (9.37 mg, 10%) as a white solid: $^1$H NMR (400 MHz, Acetonitrile-d3) δ 7.84 (d, J=8.3 Hz, 1H), 7.66 (dd, J=3.8, 7.8 Hz, 1H), 7.58-7.45 (m, 2H), 7.42-7.27 (m, 2H), 7.25-7.15 (m, 1H), 6.94-6.85 (m, 1H), 6.73-6.62 (m, 1H), 4.54-4.41 (m, 1H), 4.29 (dd, J=5.0, 10.9 Hz, 1H), 4.16-4.05 (m, 2H), 4.00-3.76 (m, 3H), 3.74 (d, J=2.4 Hz, 3H), 3.71-3.64 (m, 2H), 3.58-3.46 (m, 1H), 3.39-3.20 (m, 1H), 3.13-2.96 (m, 2H), 2.88-2.76 (m, 1H), 2.60-2.52 (m, 1H), 2.38 (s, 3H), 2.28-2.17 (m, 4H), 1.78-1.57 (m, 3H). LCMS Rt=3.143 min, m/z =604.3 [M+H]+.

LCMS (5 to 95% acetonitrile in water+0.03% ammonium bicarbonate over 6 mins) retention time 3.143 min, ESI+ found [M+H]=604.3.

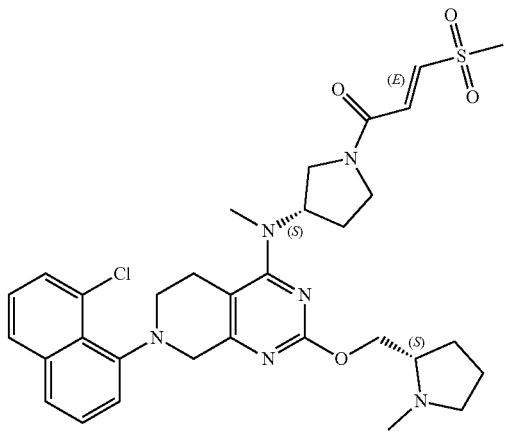

Example 15 (Method 1-A22): (E)-1-((S)-3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-3-(methylsulfonyl)prop-2-en-1-one

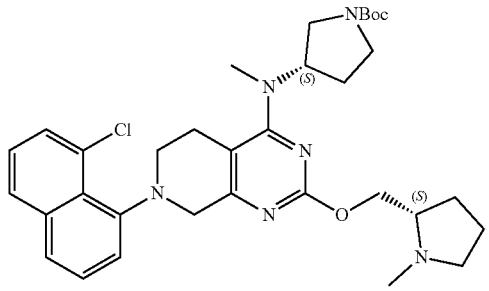

Step 1: (S)-tert-butyl 3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidine-1-carboxylate The substitution reaction was prepared in a similar fashion to Example 1 (Method 1-A), Step 4, substituting tert-butyl (S)-3-(methylamino)pyrrolidine-1-carboxylate for tert-butyl N-[2-(methylamino)ethyl]carbamate. The resulting residue was purified by column chromatography (silica gel, 100-200 mesh, 0-30% methanol in dichloromethane) affording (S)-tert-butyl 3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidine-1-carboxylate (200 mg, 37%) as a brown oil. LCMS Rt=0.953 min, m/z=606.3 [M+H]+.

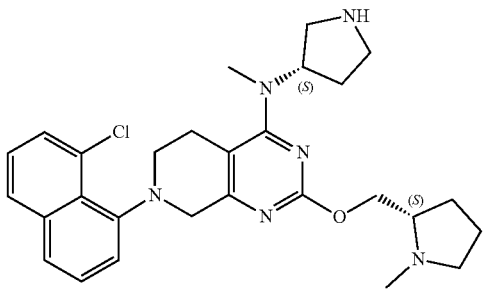

Step 2: 7-(8-chloro-1-naphthyl)-N-methyl-2-[[(2S)-1-methylpyrrolidin-2-yl]methoxy]-N-[(3S)-pyrrolidin-3-yl]-6,8-dihydro-5H-pyrido[3,4-d]pyrimidin-4-amine The deprotection of Boc was prepared in a similar fashion to Example 1 (Method 1-A), Step 5. The resulting mixture was concentrated to dryness in vacuo affording 7-(8-chloro-1-naphthyl)-N-methyl-2-[[(2S)-1-methylpyrrolidin-2-yl]methoxy]-N-[(3S)-pyrrolidin-3-yl]-6,8-dihydro-5H-pyrido[3,4-d]pyrimidin-4-amine (100 mg, 56%, hydrochloride salt) as a brown oil, which was used in the next step without further purification. LCMS Rt=0.896 min, m/z=506.4 [M+H]+.

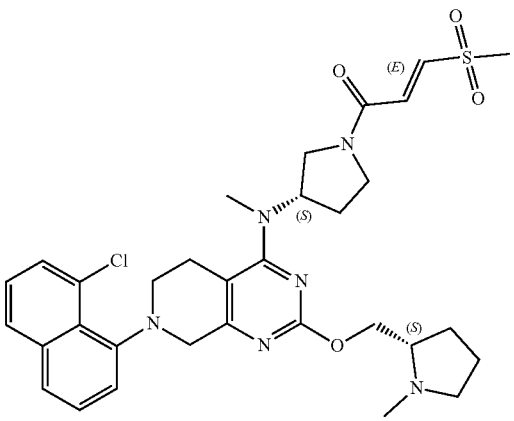

Step 3: (E)-1-((S)-3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-3-(methylsulfonyl)prop-2-en-1-one The amide coupling reaction was prepared in a similar fashion to Example 1 (Method 1-A), Step 6, substituting (E)-3-(methylsulfonyl)acrylic acid for (E)-4-methoxy-4-oxobut-2-enoic acid. The crude product was purified by reverse phase HPLC (neutral condition, column: Waters Xbridge BEH C18 100*30 mm*10 μm; mobilephase: (water (NH$_4$HCO$_3$)-ACN; B %: 50%-80%, 10 min) affording (E)-1-((S)-3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidin-1-yl)-3-(methylsulfonyl)prop-2-en-1-one (2.43 mg, 1.89%) as a brown solid: $^1$H NMR (400 MHz, Acetonitrile-d3) δ 7.90 (d, J=8.11 Hz, 1H), 7.76-7.71 (m, 1H), 7.61 (dd, J=7.39, 0.83 Hz, 1H), 7.55 (td, J=7.81, 4.29 Hz, 1H), 7.46 (d, J=7.75 Hz, 1H), 7.43-7.35 (m, 2H), 7.24-7.17 (m, 1H), 4.98-4.78 (m, 1H), 4.44 (br s, 1H), 4.36-4.23 (m, 2H), 4.16-3.59 (m, 5H), 3.58-3.41 (m, 2H), 1.91-1.74 (m, 3H), 3.40-3.10 (m, 4H), 3.09-3.05 (m, 3H), 3.04-3.00 (m, 3 H), 2.64 (br s, 1H), 2.57 (br s, 3H), 2.25-2.05 (m, 3H) LCMS Rt=2.056 min, m/z=638.2 [M +H]+.

LCMS (5 to 95% acetonitrile in water+0.03% ammonium bicarbonate over 6 mins) retention time 2.056 min, ESI+ found [M+H]=638.2.

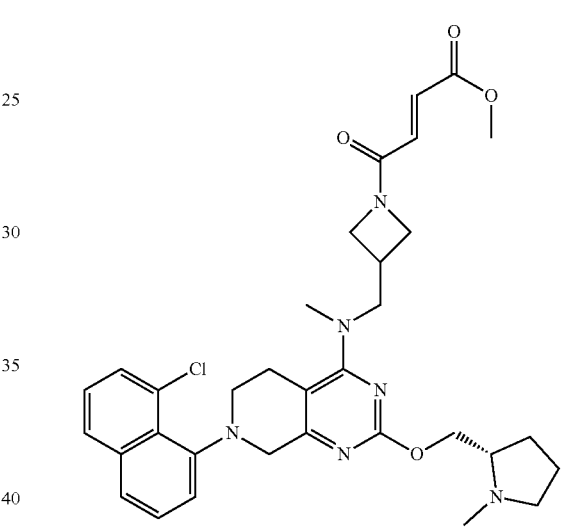

Example 16 (Method 1-A4): methyl (S,E)-4-(3-(((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)methyl)azetidin-1-yl)-4-oxobut-2-enoate The amide coupling reaction was prepared in a similar fashion to Example 1 (Method 1-A), Step 6, substituting (S)—N-(azetidin-3-ylmethyl)-7-(8-chloronaphthalen-1-yl)-N-methyl-2-((1-methylpyrrolidin-2-yl)methoxy)-5,6,7,8-tetrahydropyrido[3,4-d]pyrimidin-4-amine for (S)—N$^1$-(7-(8-chloro-7-fluoronaphthalen-1-yl)-2-((1-methylpyrrolidin-2-yl)methoxy)-5,6,7,8-tetrahydropyrido[3,4-d]pyrimidin-4-yl)-N$^1$-methylethane-1,2-diamine. The crude product was purified by reverse phase HPLC (column: Phenomenex Luna 80*30 mm*3 μm; mobile phase: (water(FA)-ACN; B %: 5%-35%, 8 min) affording methyl (S,E)-4-(3-(((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)methyl)azetidin-1-yl)-4-oxobut-2-enoate (7.43 mg, 4%, formate salt) as a pale yellow solid: $^1$H NMR (400 MHz, Acetonitrile-d3) δ 7.90-7.79 (m, 1H), 7.67 (br d, J=7.6 Hz, 1H), 7.60-7.46 (m, 2H), 7.44-7.35 (m, 1H), 7.34-7.27 (m, 1H), 7.02-6.90 (m, 1H), 6.69-6.59 (m, 1H), 4.39-4.24 (m, 2H), 4.23-4.16 (m, 1H), 4.14-3.95 (m, 4H), 3.82-3.75 (m, 1H), 3.75-3.65 (m, 4H), 3.64-3.48 (m, 2H), 3.29-3.14 (m, 2H), 3.10 (d, J=2.0 Hz, 3H), 3.09-3.01 (m, 2H), 3.00-2.93 (m, 1H), 2.63 (br d, J=14.6 Hz, 1H), 2.56-2.48 (m, 1H), 2.36 (s, 3H), 2.13-2.08 (m, 1H), 1.79-1.60 (m, 3H). LCMS Rt=2.101 min, m/z=618.3 [M+H]+.

LCMS (5 to 95% acetonitrile in water+0.03% ammonium bicarbonate over 6 mins) retention time 2.101 min, ESI+ found [M+H]=618.3.

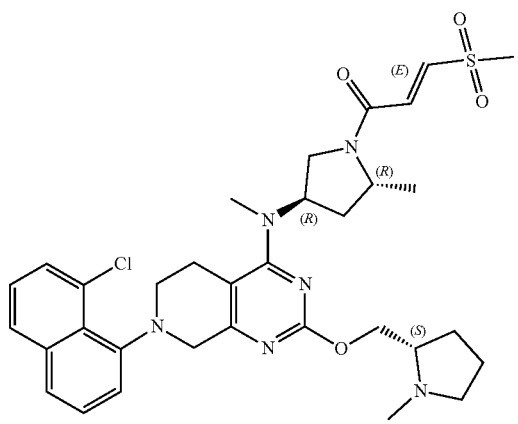

Example 17 (Method 1-A18): methyl (E)-4-((2R,4R)-4-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)-2-methylpyrrolidin-1-yl)-4-oxobut-2-enoate 7-(8-chloronaphthalen-1-yl)-N-methyl-2-(((S)-1-methylpyrrolidin-2-yl)methoxy)-N-((3R,5R)-5-methylpyrrolidin-3-yl)-5,6,7,8-tetrahydropyrido[3,4-d]pyrimidin-4-amine was prepared in a similar manner to that described in Example 4, substituting tert-butyl (2R,4R)-4-amino-2-methyl-pyrrolidine-1-carboxylate for tert-butyl (2S,4S)-4-amino-2-methyl-pyrrolidine-1-carboxylate. The amide coupling reaction was prepared in a similar fashion to Example 1 (Method 1-A), Step 6, substituting 7-(8-chloronaphthalen-1-yl)-N-methyl-2-(((S)-1-methylpyrrolidin-2-yl)methoxy)-N-((3R,5R)-5-methylpyrrolidin-3-yl)-5,6,7,8-tetrahydropyrido[3,4-d]pyrimidin-4-amine for (S)—$N^1$-(7-(8-chloro-7-fluoronaphthalen-1-yl)-2-((1-methylpyrrolidin-2-yl)methoxy)-5,6,7,8-tetrahydropyrido[3,4-d]pyrimidin-4-yl)-$N^1$-methylethane-1,2-diamine. The crude product was purified by reverse phase HPLC (column: Waters Xbridge BEH C18 100*30 mm*10 μm; mobile phase: (water (NH$_4$HCO$_3$)-ACN; B %: 50%-80%, 10 min)) affording methyl (E)-4-((2R,4R)-4-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)-2-methylpyrrolidin-1-yl)-4-oxobut-2-enoate (10.49 mg, 18.47%) as a white solid: $^1$H NMR (400 MHz, Acetonitrile-d3) δ 7.85 (d, J=7.9 Hz, 1H), 7.68 (d, J=7.9 Hz, 1H), 7.56 (d, J=7.5 Hz, 1H), 7.53-7.48 (m, 1H), 7.43-7.37 (m, 1H), 7.36-7.31 (m, 1H), 7.30-7.19 (m, 1H), 6.77-6.64 (m, 1H), 5.10-4.91 (m, 1H), 4.45-4.27 (m, 2H), 4.26-4.08 (m, 2H), 4.07-4.00 (m, 1H), 3.80-3.69 (m, 4H), 3.64-3.49 (m, 2H), 3.26-3.02 (m, 3H), 2.97-2.93 (m, 3H), 2.73-2.56 (m, 2H), 2.45-2.39 (m, 3H), 2.33-2.25 (m, 2H), 2.02-1.99 (m, 1H), 1.87-1.64 (m, 4H), 1.32-1.18 (m, 3H). LCMS Rt=2.172 min, m/z=632.3 [M+H]+.

LCMS (5 to 95% acetonitrile in water+0.03% ammonium bicarbonate over 6 mins) retention time 2.172 min, ESI+ found [M+H]=632.3.

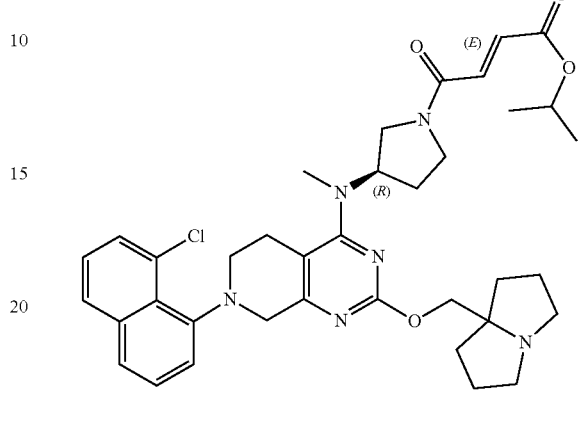

Example 18 (Method 1-A23): isopropyl (R,E)-4-(3-((7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl)(methyl)amino)pyrrolidin-1-yl)-4-oxobut-2-enoate

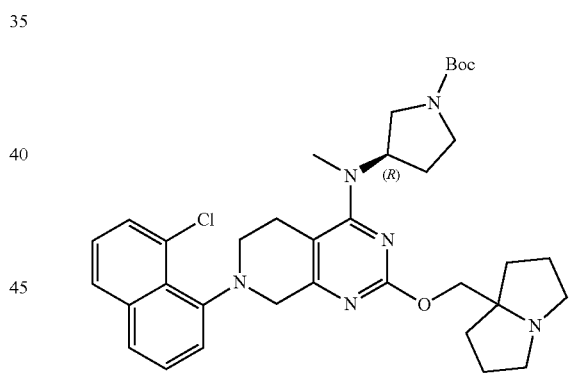

Step 1: tert-butyl (R)-3-((7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl)(methyl)amino)pyrrolidine-1-carboxylate The substitution reaction was prepared in a similar fashion to Example 1 (Method 1-A), Step 4, substituting tert-butyl (R)-3-(methylamino)pyrrolidine-1-carboxylate for tert-butyl N-[2-(methylamino)ethyl]carbamate. The resulting residue was purified by column chromatography (silica gel, 100-200 mesh, 10-100% ethyl acetate in petroleum ether) affording tert-butyl (R)-3-((7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl)(methyl)amino)pyrrolidine-1-carboxylate (900 mg, 44.31%) as a yellow oil. LCMS Rt=0.707 min, m/z=632.3 [M+H]+.

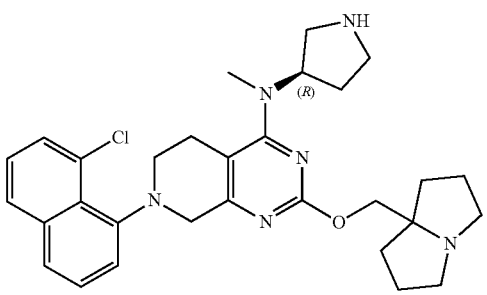

Step 2: (R)-7-(8-chloronaphthalen-1-yl)-2-((hexa-hydro-1H-pyrrolizin-7a-yl)methoxy)-N-methyl-N-(pyrrolidin-3-yl)-5,6,7,8-tetrahydropyrido[3,4-d]pyrimidin-4-amine The deprotection of Boc was prepared in a similar fashion to Example 1 (Method 1-A), Step 5. The reaction mixture was concentrated in vacuo and the crude product was purified by reverse phase HPLC (Phenomenex luna C18 250*50 mm*10 μm; mobile phase: (water (TFA)-ACN; B %: 20%-50%, 10 min) affording (R)-7-(8-chloronaphthalen-1-yl)-2-((hexahydro-1H-pyrrolizin-7a-yl)methoxy)-N-methyl-N-(pyrrolidin-3-yl)-5,6,7,8-tetrahydropyrido[3,4-d]pyrimidin-4-amine (200 mg, 21.74%, trifluoroacetate salt) as a yellow oil, which was used in the next step without further purification. LCMS Rt=0.721 min, m/z=532.3 [M+H]+.

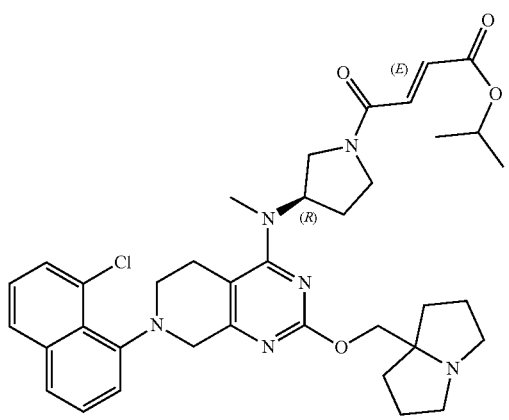

Step 3: isopropyl (R,E)-4-(3-((7-(8-chloronaphtha-len-1-yl)-2-((tetrahydro-1H-pyrrolizin-7a(5H)-yl)methoxy)-5,6,7,8-tetrahydropyrido[3,4-d]pyrimidin-4-yl)(methyl)amino)pyrrolidin-1-yl)-4-oxobut-2-enoate The amide coupling reaction was prepared in a similar fashion to Example 1 (Method 1-A), Step 6, substituting (E)-4-isopropoxy-4-oxobut-2-enoic acid for (E)-4-methoxy-4-oxobut-2-enoic acid. The crude product was purified by reverse phase HPLC (Phenomenex Luna 80*30 mm*3 μm; mobile phase: (water (FA)-ACN]; B %: 15%-50%, 8 min) affording isopropyl (R,E)-4-(3-((7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl)(methyl)amino)pyrrolidin-1-yl)-4-oxobut-2-enoate (12.89 mg, 37%, formate salt) as a yellow solid: $^1$H NMR (400 MHz, Acetonitrile-d3) δ 7.90-7.86 (m, 1H), 7.71 (dd, J=8.07, 1.22 Hz, 1H), 7.60-7.50 (m, 2H), 7.46-7.40 (m, 1H), 7.35 (t, J=7.15 Hz, 1H), 7.32-7.25 (m, 1H), 6.73-6.63 (m, 1H), 5.15-4.96 (m, 1H), 4.92-4.75 (m, 1H), 4.31-4.23 (m, 1H), 4.15-4.07 (m, 2H), 4.00-3.84 (m, 1H), 3.81-3.73 (m, 1H), 3.71-3.59 (m, 1H), 3.58-3.51 (m, 1H), 3.50-3.39 (m, 1H), 3.33-3.18 (m, 1H), 3.17-3.08 (m, 3H), 3.02-2.97 (m, 3H), 2.71-2.61 (m, 4H), 2.32-2.10 (m, 2H), 2.04-1.99 (m, 2H), 1.94-1.83 (m, 4H), 1.74-1.64 (m, 2H), 1.33-1.28 (m, 6H). LCMS Rt=2.274 min, m/z=672.3 [M+H]+.

LCMS (5 to 95% acetonitrile in water+0.03% ammonium bicarbonate over 6 mins) retention time 2.274 min, ESI+ found [M+H]=672.3.

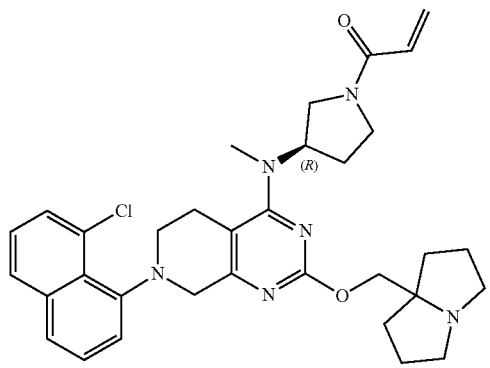

Example 19 (Method 1-A25): (R)-1-(3-((7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl)(methyl)amino)pyrrolidin-1-yl)prop-2-en-1-one The amide coupling reaction was prepared in a similar fashion to Example 1 (Method 1-A), Step 6, substituting (R)-7-(8-chloronaphthalen-1-yl)-2-((hexahydro-1H-pyrrolizin-7a-yl)methoxy)-N-methyl-N-(pyrrolidin-3-yl)-5,6,7,8-tetrahydropyrido[3,4-d]pyrimidin-4-amine (Example 18 Step 2) for (S)—N[1]-(7-(8-chloro-7-fluoronaphthalen-1-yl)-2-((1-methylpyrrolidin-2-yl)methoxy)-5,6,7,8-tetrahydropyrido[3,4-d]pyrimidin-4-yl)-N'-methylethane-1,2-diamine, and substituting acrylic acid for (E)-4-methoxy-4-oxobut-2-enoic acid. The residue was purified by reverse phase HPLC (column: Waters Xbridge Prep OBD C18 150*40 mm*10 μm; mobile phase: (water (NH4HCO3)-ACN; B %: 35%-65%, 8 min) affording (R)-1-(3-((7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl)(methyl)amino)pyrrolidin-1-yl)prop-2-en-1-one (66.75 mg, 34%) as a yellow oil: $^1$H NMR (400 MHz, Acetonitrile-d3) δ 7.90-7.86 (m, 1H), 7.74-7.68 (m, 1H), 7.60-7.50 (m, 2H), 7.45-7.39 (m, 1H), 7.38-7.32 (m, 1H), 6.65-6.50 (m, 1H), 6.28-6.18 (m, 1H), 5.71-5.62 (m, 1H), 4.91-4.73 (m, 1H), 4.31-4.21 (m, 1H), 4.09-4.03 (m, 2H), 3.96-3.67 (m, 3H), 3.66-3.50 (m, 2H), 3.47-3.36 (m, 1H), 3.34-3.22 (m, 1H), 3.21-3.14 (m, 1H), 3.13-3.04 (m, 2H), 3.01-2.98 (m, 3H), 2.70-2.59 (m, 3H), 2.14-2.06 (m, 2H), 1.94-1.73 (m, 6H), 1.70-1.59 (m, 2H). LCMS Rt =3.112 min, m/z=586.3 [M+H]+.

LCMS (5 to 95% acetonitrile in water+0.03% ammonium bicarbonate over 6 mins) retention time 3.112 min, ESI+ found [M+H]=586.3.

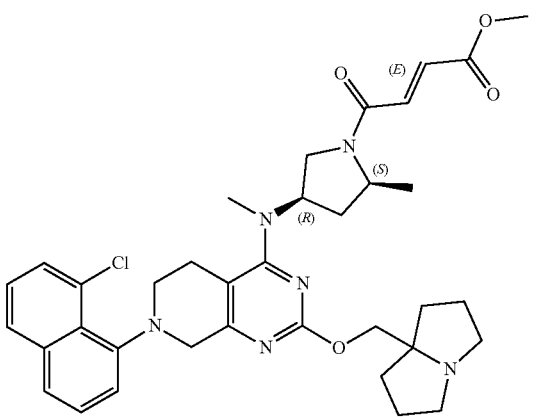

Example 20 (Method 1-A26): methyl (E)-4-((2S, 4R)-4-((7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl)(methyl)amino)-2-methylpyrrolidin-1-yl)-4-oxobut-2-enoate 7-(8-chloronaphthalen-1-yl)-N-methyl-N-((3R,5S)-5-methylpyrrolidin-3-yl)-2-((tetrahydro-1H-pyrrolizin-7a(5H)-yl)methoxy)-5,6,7,8-tetrahydropyrido[3,4-d]pyrimidin-4-amine was prepared in a similar manner to that described in Example 4, substituting tert-butyl (2S,4R)-4-amino-2-methyl-pyrrolidine-1-carboxylate for tert-butyl (2S,4S)-4-amino-2-methyl-pyrrolidine-1-carboxylate, and substituting 7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl trifluoromethanesulfonate for (S)-7-(8-chloronaphthalen-1-yl)-2-((1-methylpyrrolidin-2-yl)methoxy)-5,6,7,8-tetrahydropyrido[3,4-d]pyrimidin-4-yl trifluoromethanesulfonate.

The amide coupling reaction was prepared in a similar fashion to Example 1 (Method 1-A), Step 6, substituting 7-(8-chloronaphthalen-1-yl)-N-methyl-N-((3R,5S)-5-methylpyrrolidin-3-yl)-2-((tetrahydro-1H-pyrrolizin-7a(5H)-yl)methoxy)-5,6,7,8-tetrahydropyrido[3,4-d]pyrimidin-4-amine for (S)—N$^1$-(7-(8-chloro-7-fluoronaphthalen-1-yl)-2-((1-methylpyrrolidin-2-yl)methoxy)-5,6,7,8-tetrahydropyrido[3,4-d]pyrimidin-4-yl)-N$^1$-methylethane-1,2-diamine. The crude product was purified by reverse phase HPLC (Phenomenex Luna 80*30 mm*3 μm; mobile phase: (water (FA)-ACN; B %: 10%-40%, 8 min) affording methyl (E)-4-((2S,4R)-4-((7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl)(methyl)amino)-2-methylpyrrolidin-1-yl)-4-oxobut-2-enoate (14.85 mg, 4%) as a yellow solid: $^1$H NMR (400 MHz, Acetonitrile-d3) δ 7.85 (d, J=8.1 Hz, 1H), 7.68 (d, J=8.1 Hz, 1H), 7.57-7.49 (m, 2H), 7.40 (t, J=7.9 Hz, 1H), 7.33 (br d, J=7.2 Hz, 1H), 7.27-7.17 (m, 1H), 6.73-6.62 (m, 1H), 4.67-4.50 (m, 1H), 4.25-4.21 (m, 1H), 4.10-4.01 (m, 3H), 3.76-3.74 (m, 3H), 3.61-3.49 (m, 2H), 3.31-3.05 (m, 5H), 2.99-2.96 (m, 3H), 2.69 (br d, J=7.2 Hz, 2H), 2.59 (br d, J=15.3 Hz, 2H), 1.88-1.74 (m, 7H), 1.71-1.61 (m, 3H), 1.36 (br d, J=5.7 Hz, 3H). LCMS Rt=2.292 min, m/z=658.3 [M+H]+.

LCMS (5 to 95% acetonitrile in water+0.03% ammonium bicarbonate over 6 mins) retention time 2.292 min, ESI+ found [M+H]=658.3.

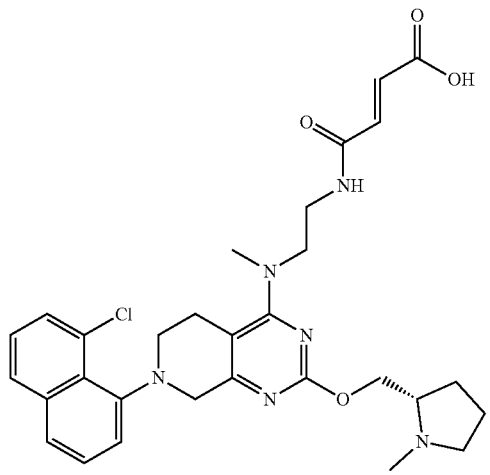 [SMILES: CN(CCNC(=O)/C=C/C(=O)O)c1nc(OC[C@@H]2CCCN2C)nc2c1CCN(c1cccc3cccc(Cl)c13)C2]

Example 21 (Method 1-A9): (S,E)-4-((2-((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)ethyl)amino)-4-oxobut-2-enoic acid

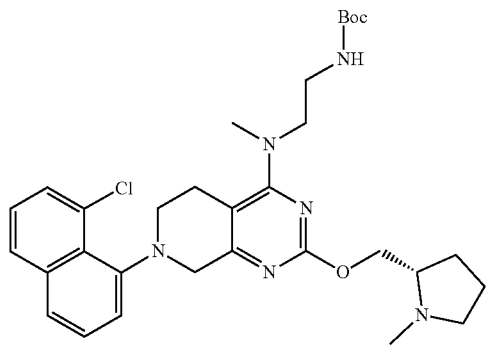 [SMILES: CN(CCNC(=O)OC(C)(C)C)c1nc(OC[C@@H]2CCCN2C)nc2c1CCN(c1cccc3cccc(Cl)c13)C2]

Step 1: tert-butyl (S)-(2-((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)ethyl)carbamate The substitution reaction was prepared in a similar fashion to Example 1 (Method 1-A), Step 4. The crude product was purified by column chromatography (silica gel, 100-200 mesh, 0-100% ethyl acetate in petroleum ether) affording tert-butyl (S)-(2-((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)ethyl)carbamate (4 g, 87.19%) as a brown solid. LCMS Rt=0.841 min, m/z=580.3 [M+H]+.

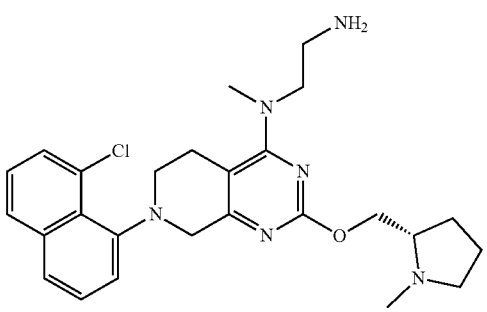 [SMILES: CN(CCN)c1nc(OC[C@@H]2CCCN2C)nc2c1CCN(c1cccc3cccc(Cl)c13)C2]

Step 2: N'-[7-(8-chloro-1-naphthyl)-2-[[(2S)-1-methylpyrrolidin-2-yl]methoxy]-6,8-dihydro-5H-pyrido[3,4-d]pyrimidin-4-yl]-N'-methyl-ethane-1,2-diamine The deprotection of Boc was prepared in a similar fashion to Example 1 (Method 1-A), Step 5. The reaction mixture was concentrated to dryness in vacuo affording N-[7-(8-chloro-1-naphthyl)-2-[[(2S)-1-methylpyrrolidin-2-yl]methoxy]-6,8-dihydro-5H-pyrido[3,4-d]pyrimidin-4-yl]-N-methyl-ethane-1,2-diamine (4 g, crude, hydrochloride salt) as a brown solid, which was used in next step without further purification. LCMS Rt=0.671 min, m/z=481.4 [M+H]+.

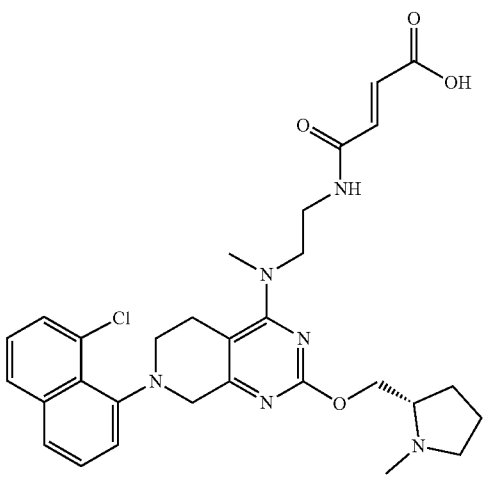 [SMILES: CN(CCNC(=O)/C=C/C(=O)O)c1nc(OC[C@@H]2CCCN2C)nc2c1CCN(c1cccc3cccc(Cl)c13)C2]

Step 3: (S,E)-4-((2-((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)ethyl)amino)-4-oxobut-2-enoic acid The amide coupling reaction was prepared in a similar fashion to Example 1 (Method 1-A), Step 6, substituting fumaric acid for (E)-4-methoxy-4-oxobut-2-enoic acid. The crude product was purified by reverse phase HPLC (column: Waters Xbridge BEH C18 100*30 mm*10 μm; mobile phase: (water(NH$_4$HCO$_3$)-ACN; B %: 30%-60%, 8 min) affording (S,E)-4-((2-((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)ethyl)amino)-4-oxobut-2-enoic acid (9.43 mg, 7.53%) as a yellow solid: $^1$H NMR (400 MHz, Acetonitrile-d3) δ 11.17 (br s, 1H), 7.84 (d, J=7.6 Hz, 1H), 7.66 (d, J=8.1 Hz, 1H), 7.55 (dd, J=1.1, 7.4 Hz, 1H), 7.49 (t, J=7.9 Hz, 1H), 7.41-7.36 (m, 1H), 7.31-7.26 (m, 1H), 5.99 (dd, J=10.3, 13.4 Hz, 1H), 5.66 (dd, J=8.4, 13.5 Hz, 1H), 4.79-4.58 (m, 1H), 4.56-4.39 (m, 1H), 4.20-4.12 (m, 2H), 3.69-3.59 (m, 3H), 3.54-3.44 (m, 2H), 3.19 (d, J=1.5 Hz, 3H), 2.92-2.91 (m, 1H), 3.09-2.90 (m, 3H), 2.87 (d, J=1.3 Hz, 3H), 2.70-2.66 (m, 1H), 2.34-2.23 (m, 2H), 2.11-2.01 (m, 3H). LCMS Rt=1.929 min, m/z=578.2 [M+H]+.

LCMS (5 to 95% acetonitrile in water+0.1% trifluoroacetic acid over 6 mins) retention time 1.929 min, ESI+ found [M+H]=578.2

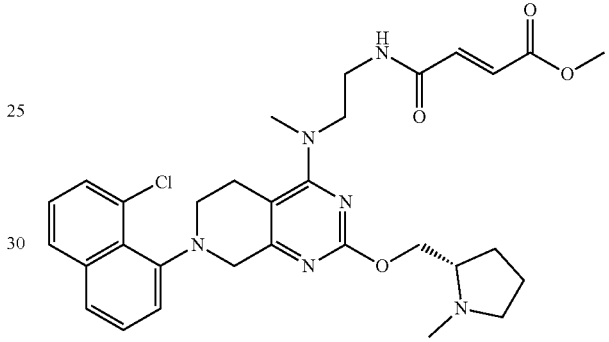

Example 22 (Method 1-A1): methyl (S,E)-4-((2-((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)ethyl)amino)-4-oxobut-2-enoate The amide coupling reaction was prepared in a similar fashion to Example 1 (Method 1-A), Step 6, starting from N-[7-(8-chloro-1-naphthyl)-2-[[(2S)-1-methylpyrrolidin-2-yl]methoxy]-6,8-dihydro-5H-pyrido[3,4-d]pyrimidin-4-yl]-N-methyl-ethane-1,2-diamine (Example 21 Step 2). The crude product was purified by reverse phase HPLC (column: Phenomenex Luna 80*30 mm*3 μm; mobile phase: (water (0.1% TFA)-ACN; B %: 15%-40%, 8 min) affording methyl (S,E)-4-((2-((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)ethyl)amino)-4-oxobut-2-enoate (17.63 mg, 13.89%, trifluoroacetate salt) as a yellow solid: $^1$H NMR (400 MHz, Acetonitrile-d3) δ ppm 10.78-10.49 (m, 1H), 7.90 (d, J=7.38 Hz, 1H), 7.76 (d, J=8.13 Hz, 1H), 7.64-7.48 (m, 2H), 7.48-7.34 (m, 2H), 6.92 (d, J=15.51 Hz, 1H), 6.67 (d, J=15.51 Hz, 1H), 4.90-4.62 (m, 2H), 4.30 (br d, J=18.01 Hz, 1H), 4.01-3.68 (m, 8H), 3.67-3.47 (m, 3H), 3.44-3.24 (m, 4H), 3.18-3.04 (m, 2H), 2.95 (s, 3H), 2.88-2.76 (m, 1H), 2.39-2.28 (m, 1H), 2.20-2.08 (m, 3H). LCMS Rt=2.048 min, m/z=592.3 [M+H]+.

LCMS (5 to 95% acetonitrile in water+0.1% trifluoroacetic acid over 6 mins) retention time 2.048 min, ESI+ found [M+H]=592.3

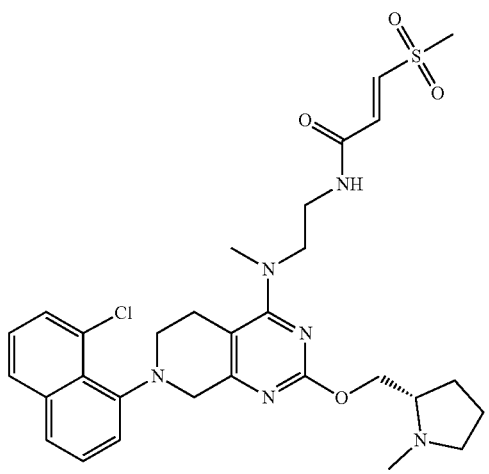 [SMILES: CN(CCNC(=O)/C=C/S(C)(=O)=O)c1nc(OC[C@@H]2CCCN2C)nc2c1CCN(c1cccc3cccc(Cl)c13)C2]

Example 23 (Method 1-A17): (S,E)-N-(2-((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)ethyl)-3-(methylsulfonyl)acrylamide The amide coupling reaction was prepared in a similar fashion to Example 1 (Method 1-A), Step 6, starting from N-[7-(8-chloro-1-naphthyl)-2-[[(2S)-1-methylpyrrolidin-2-yl]methoxy]-6,8-dihydro-5H-pyrido[3,4-d]pyrimidin-4-yl]-N-methyl-ethane-1,2-diamine (Example 21 Step 2), and substituting (E)-3-(methylsulfonyl)acrylic acid for (E)-4-methoxy-4-oxobut-2-enoic acid. The crude product was purified by reverse phase HPLC (Xbridge BEH C18 100*30 mm*10 µm; mobile phase: (water (NH$_4$HCO$_3$)-ACN]; B %: 40%-70%, 10 min) affording (S,E)-N-(2-((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)ethyl)-3-(methylsulfonyl)acrylamide (57.05 mg, 6.02%) as a yellow solid: $^1$H NMR (400 MHz, Acetonitrile-d3) δ 7.87-7.81 (m, 1H), 7.67 (d, J=8.5 Hz, 1H), 7.55 (dd, J=1.0, 7.5 Hz, 1H), 7.50 (t, J=7.8 Hz, 1H), 7.39 (t, J=7.8 Hz, 2H), 7.32 (d, J=7.0 Hz, 1H), 7.23 (d, J=15.0 Hz, 1H), 6.78 (dd, J=1.5, 15.0 Hz, 1H), 4.28-4.26 (m, 1H), 4.19 (br d, J=16.5 Hz, 1H), 4.09 (dd, J=6.3, 10.8 Hz, 1H), 3.86-3.77 (m, 1H), 3.73-3.67 (m, 1H), 3.57-3.48 (m, 4H), 3.23-3.12 (m, 5H), 3.09-3.03 (m, 1H), 3.01-2.98 (m, 4H), 2.65 (br d, J=16.0 Hz, 1H), 2.58-2.54 (m, 1H), 2.37 (s, 3H), 2.24 (br s, 1H), 1.77-1.63 (m, 3H). LCMS Rt=2.795 min, m/z=612.2 [M+H]+.

LCMS (5 to 95% acetonitrile in water+0.1% trifluoroacetic acid over 6 mins) retention time 2.795 min, ESI+ found [M+H]=612.2

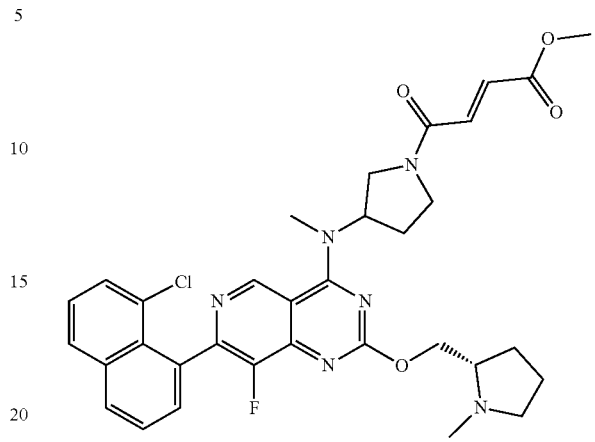

Example 24 (Method 1-All): methyl (E)-4-(3-((7-(8-chloronaphthalen-1-yl)-8-fluoro-2-(((S)-1-methylpyrrolidin-2-yl)methoxy)pyrido[4,3-d]pyrimidin-4-yl)(methyl)amino)pyrrolidin-1-yl)-4-oxobut-2-enoate The amide coupling reaction was prepared in a similar fashion to Example 1 (Method 1-A), Step 6, substituting 7-(8-chloronaphthalen-1-yl)-8-fluoro-N-methyl-2-(((S)-1-methylpyrrolidin-2-yl)methoxy)-N-(pyrrolidin-3-yl)pyrido[4,3-d]pyrimidin-4-amine for (S)—N$^1$-(7-(8-chloro-7-fluoronaphthalen-1-yl)-2-((1-methylpyrrolidin-2-yl)methoxy)-5,6,7,8-tetrahydropyrido[3,4-d]pyrimidin-4-yl)-N$^1$-methylethane-1,2-diamine. The residue was purified by reverse phase HPLC (column: Phenomenex C18 80*40 mm*3 µm; mobile phase: (water(NH$_4$HCO$_3$)-ACN; B %:30%-65%, 8 min) affording methyl (E)-4-(3-((7-(8-chloronaphthalen-1-yl)-8-fluoro-2-(((S)-1-methylpyrrolidin-2-yl)methoxy)pyrido[4,3-d]pyrimidin-4-yl)(methyl)amino)pyrrolidin-1-yl)-4-oxobut-2-enoate (8.24 mg, 12%) as a yellow oil: $^1$H NMR (400 MHz, Acetonitrile-d3) δ 9.26-9.20 (m, 1H), 8.17 (d, J=7.7 Hz, 1H), 8.06 (d, J=8.2 Hz, 1H), 7.73 (s, 1H), 7.69-7.64 (m, 2H), 7.57 (d, J=7.7 Hz, 1H), 7.32 (s, 1H), 6.80-6.72 (m, 1H), 5.53-5.35 (m, 1H), 4.54-4.45 (m, 1H), 4.38-4.30 (m, 1H), 4.20-3.88 (m, 2H), 3.80 (d, J=7.1 Hz, 3H), 3.47 (s, 3H), 3.08-3.00 (m, 1H), 2.72-2.62 (m, 1H), 2.44 (s, 3H), 2.38-2.24 (m, 3H), 2.15 (br s, 1H), 2.06-2.01 (m, 1H), 1.89-1.66 (m, 4H). LCMS Rt=2.109 min, m/z=632.2 [M +H]+.

LCMS (5 to 95% acetonitrile in water+10 mM ammonium bicarbonate over 6 mins) retention time 2.109 min, ESI+ found [M+H]=632.2.

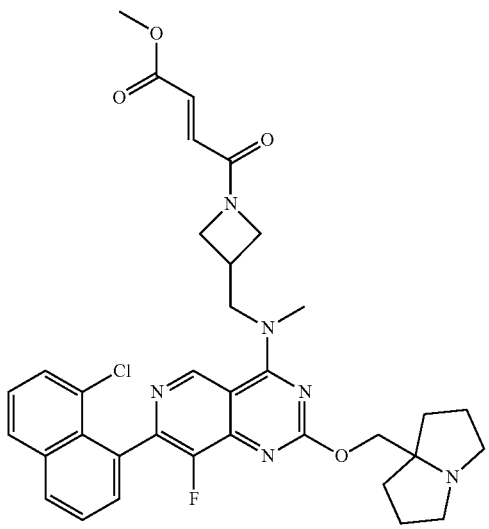 [SMILES: COC(=O)/C=C/C(=O)N1CC(CN(C)c2nc(OCC34CCCN3CCC4)nc3c(F)c(-c4cccc5cccc(Cl)c45)ncc23)C1]

Example 25 (Method 1-A20): methyl (E)-4-(3-(((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)methyl)azetidin-1-yl)-4-oxobut-2-enoate The amide coupling reaction was prepared in a similar fashion to Example 1 (Method 1-A), Step 6, substituting N-(azetidin-3-ylmethyl)-7-(8-chloronaphthalen-1-yl)-8-fluoro-N-methyl-2-((tetrahydro-1H-pyrrolizin-7a(5H)-yl)methoxy)pyrido[4,3-d]pyrimidin-4-amine for (S)—N¹-(7-(8-chloro-7-fluoronaphthalen-1-yl)-2-((1-methylpyrrolidin-2-yl)methoxy)-5,6,7,8-tetrahydropyrido[3,4-d]pyrimidin-4-yl)-N¹-methylethane-1,2-diamine. The crude product was purified by reverse phase HPLC (column: Waters Xbridge BEH C18 100*30 mm*10 μm; mobile phase: (water (NH₄HCO3)-ACN; B %: 30%-60%, 10 min) affording methyl (E)-4-(3-(((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)methyl)azetidin-1-yl)-4-oxobut-2-enoate (10.81 mg, 22.29%) as a yellow solid: ¹H NMR (400 MHz, Acetonitrile-d3) 9.22 (s, 1H), 8.12 (dd, J=1.1, 8.1 Hz, 1H), 8.01 (d, J=8.1 Hz, 1H), 7.72-7.66 (m, 1H), 7.64-7.59 (m, 2H), 7.54-7.49 (m, 1H), 6.99 (dd, J=1.2, 15.4 Hz, 1H), 6.66 (d, J=15.5 Hz, 1H), 4.42 (t, J=8.7 Hz, 1H), 4.28-4.19 (m, 2H), 4.17-4.08 (m, 4H), 3.93-3.85 (m, 1H), 3.74 (s, 3H), 3.60-3.56 (m, 3H), 3.27-3.19 (m, 1H), 3.02-2.94 (m, 2H), 2.63-2.57 (m, 2H), 1.92-1.91 (m, 1H), 1.89-1.73 (m, 6H), 1.65-1.58 (m, 2H). LCMS Rt=2.058 min, m/z=658.3 [M+H]+.

LCMS (5 to 95% acetonitrile in water+0.1% trifluoroacetic acid over 6 mins) retention time 2.058 min, ESI+ found [M+H]=658.3

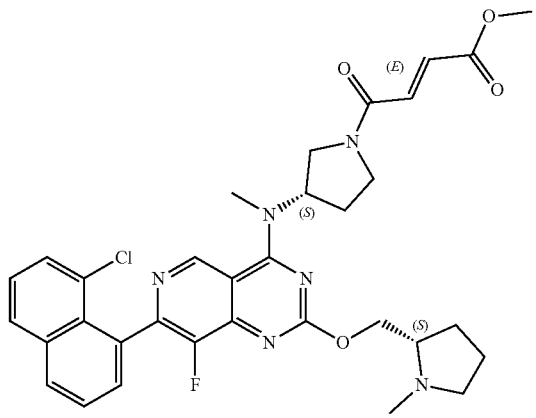

Example 26 (Method 1-A15): methyl (E)-4-((S)-3-((7-(8-chloronaphthalen-1-yl)-8-fluoro-2-(((S)-1-methylpyrrolidin-2-yl)methoxy)pyrido[4,3-d]pyrimidin-4-yl)(methyl)amino)pyrrolidin-1-yl)-4-oxobut-2-enoate

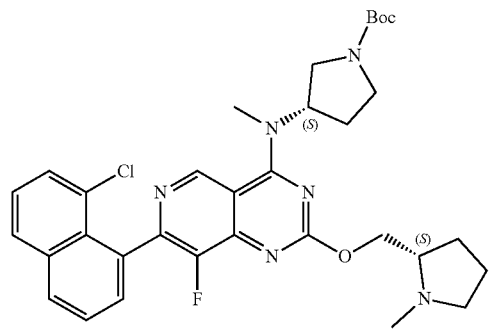

Step 1: (S)-tert-butyl 3-((7-(8-chloronaphthalen-1-yl)-8-fluoro-2-(((S)-1-methylpyrrolidin-2-yl)methoxy)pyrido[4,3-d]pyrimidin-4-yl)(methyl)amino)pyrrolidine-1-carboxylate The substitution reaction was prepared in a similar fashion to Example 28 (Method 2-C), Step 4, substituting (S)-4-chloro-7-(8-chloronaphthalen-1-yl)-8-fluoro-2-((1-methylpyrrolidin-2-yl)methoxy)pyrido[4,3-d]pyrimidine for 4-chloro-7-(8-chloronaphthalen-1-yl)-8-fluoro-2-((hexahydro-1H-pyrrolizin-7a-yl)methoxy)pyrido[4,3-d]pyrimidine, and substituting tert-butyl (S)-3-(methylamino)pyrrolidine-1-carboxylate for tert-butyl 3-(methylaminomethyl)azetidine-1-carboxylate. The crude product was purified by flash column (ISCO 20 g silica, 0-40% dichloromethane in methanol, gradient over 20 min) affording (S)-tert-butyl 3-((7-(8-chloronaphthalen-1-yl)-8-fluoro-2-(((S)-1-methylpyrrolidin-2-yl)methoxy)pyrido[4,3-d]pyrimidin-4-yl)(methyl)amino)pyrrolidine-1-carboxylate (150 mg, 60%) as an orange oil. LCMS Rt=0.808 min, m/z=620.2 [M+H]+.

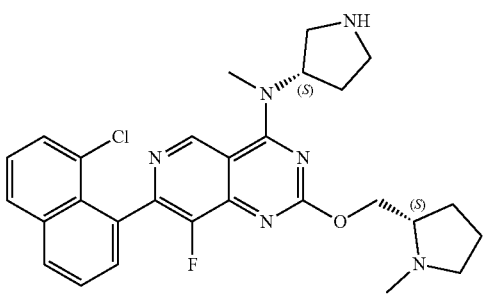

Step 2: 7-(8-chloro-1-naphthyl)-8-fluoro-N-methyl-2-[[(2S)-1-methylpyrrolidin-2-yl]methoxy]-N-[(3S)-pyrrolidin-3-yl]pyrido[4,3-d]pyrimidin-4-amine The deprotection of Boc was prepared in a similar fashion to Example 28 (Method 2-C), step 5. The reaction mixture was concentrated to dryness in vacuo and the crude product was purified by reverse phase HPLC (Phenomenex Luna 80*30 mm*3 μm; mobile phase: [water(TFA)-ACN]; B %: 15%-45%, 8 min) affording 7-(8-chloro-1-naphthyl)-8-fluoro-N-methyl-2-[[(2S)-1-methylpyrrolidin-2-yl]methoxy]-N-[(3S)-pyrrolidin-3-yl]pyrido[4,3-d]pyrimidin-4-amine (60 mg, 70%) as a pale yellow oil. LCMS Rt=0.551 min, m/z=520.2 [M+H]+.

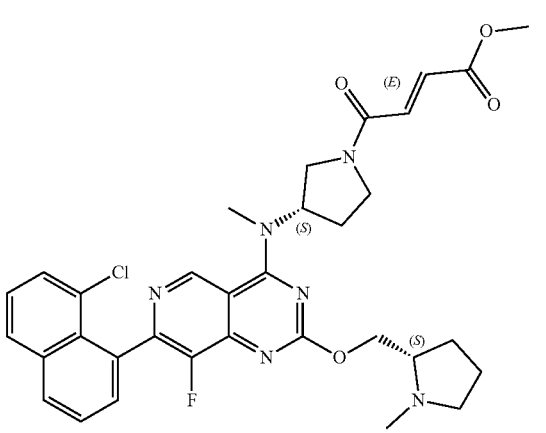

Step 3: methyl (E)-4-((S)-3-((7-(8-chloronaphthalen-1-yl)-8-fluoro-2-(((S)-1-methylpyrrolidin-2-yl)methoxy)pyrido[4,3-d]pyrimidin-4-yl)(methyl)amino)pyrrolidin-1-yl)-4-oxobut-2-enoate The amide coupling reaction was prepared in a similar fashion to Example 1 (Method 1-A), Step 6. The crude product was purified by reverse phase HPLC (column: Waters Xbridge BEH C18 100*30 mm*10 μm; mobile phase: [water(NH₄HCO₃)-ACN]; B %: 30%-60%, 10 min) affording methyl (E)-4-((S)-3-((7-(8-chloronaphthalen-1-yl)-8-fluoro-2-(((S)-1-methylpyrrolidin-2-yl)methoxy)pyrido[4,3-d]pyrimidin-4-yl)(methyl)amino)pyrrolidin-1-yl)-4-oxobut-2-enoate (11.29 mg, 30%) as a yellow oil: $^1$H NMR (400 MHz, Acetonitrile-d3) δ 8.82 (s, 1H), 7.82-7.80 (d, J=8 Hz, 1H), 7.71-7.69 (d, J=8 Hz, 1H), 7.38-7.34 (m, 1H), 7.30-7.21 (m, 2H), 7.20-7.16 (m, 1H), 7.02-6.91 (m, 1H), 6.44-6.39 (m, 1H), 5.09-5.01 (m, 1H), 4.17-4.14 (m, 1H), 4.13-3.95 (m, 1H), 3.82-3.50 (m, 2H), 3.47 (s, 3H), 3.45-3.32 (m, 1H), 3.28-3.15 (m, 1H), 3.10 (s, 3H), 2.71-2.68 (m, 1H), 2.43-2.32 (m, 1H), 2.08 (s, 3H), 2.01-1.95 (m, 3H), 1.59-1.52 (m, 1H), 1.45-1.37 (m, 3H). LCMS Rt=2.889 min, m/z=632.2 [M+H]+.

LCMS (5 to 95% acetonitrile in water+0.03% ammonium bicarbonate over 6 mins) retention time 2.889 min, ESI+ found [M+H]=632.2.

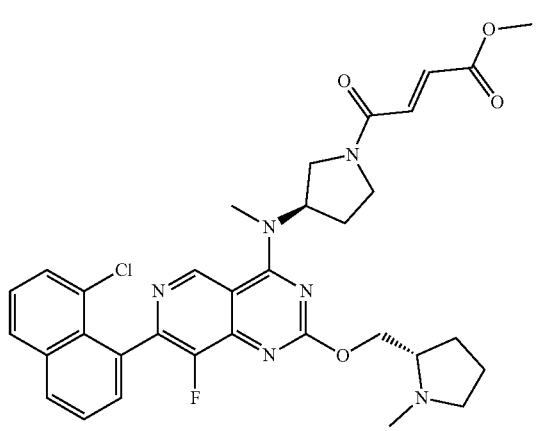 [SMILES: COC(=O)/C=C/C(=O)N1CC[C@@H](N(C)c2nc(OC[C@@H]3CCCN3C)nc3c(F)c(-c4cccc5cccc(Cl)c45)ncc23)C1]

Example 27 (Method 1-A8): methyl (E)-4-((R)-3-((7-(8-chloronaphthalen-1-yl)-8-fluoro-2-(((S)-1-methylpyrrolidin-2-yl)methoxy)pyrido[4,3-d]pyrimidin-4-yl)(methyl)amino)pyrrolidin-1-yl)-4-oxobut-2-enoate The amide coupling reaction was prepared in a similar fashion to Example 1 (Method 1-A), Step 6, substituting 7-(8-chloronaphthalen-1-yl)-8-fluoro-N-methyl-2-(((S)-1-methylpyrrolidin-2-yl)methoxy)-N—((R)-pyrrolidin-3-yl)pyrido[4,3-d]pyrimidin-4-amine for (S)—N$^1$-(7-(8-chloro-7-fluoronaphthalen-1-yl)-2-((1-methylpyrrolidin-2-yl)methoxy)-5,6,7,8-tetrahydropyrido[3,4-d]pyrimidin-4-yl)-N$^1$-methylethane-1,2-diamine. The mixture was purified by reverse phase HPLC (column: Waters Xbridge BEH C18 100*30 mm*10 μm; mobile phase: [water(NH₄HCO₃)-ACN]; B %: 30%-60%, 8 min) affording methyl (E)-4-((R)-3-((7-(8-chloronaphthalen-1-yl)-8-fluoro-2-(((S)-1-methylpyrrolidin-2-yl)methoxy)pyrido[4,3-d]pyrimidin-4-yl)(methyl)amino)pyrrolidin-1-yl)-4-oxobut-2-enoate (9.02 mg, 11%) as a yellow solid: $^1$H NMR (400 MHz, Acetonitrile-d3) δ 9.23-9.14 (m, 1H), 8.15-8.08 (m, 1H), 8.04-7.97 (m, 1H), 7.72-7.66 (m, 1H), 7.65-7.58 (m, 2H), 7.54-7.48 (m, 1H), 7.33-7.23 (m, 1H), 6.76-6.66 (m, 1H), 5.56-5.24 (m, 1H), 4.55-4.41 (m, 1H), 4.38-4.25 (m, 1H), 4.16-3.80 (m, 2H), 3.76 (d, J=7.6 Hz, 3H), 3.73-3.65 (m, 1H), 3.63-3.46 (m, 1H), 3.47-3.43 (m, 3H), 3.06-2.96 (m, 1H), 2.71-2.59 (m, 1H), 2.40 (s, 3H), 2.34-2.23 (m, 3H), 2.05-1.97 (m, 1H), 1.82-1.64 (m, 3H). LCMS Rt=2.897 min, m/z=632.2 [M+H]+.

LCMS (5 to 95% acetonitrile in water+0.03% ammonium bicarbonate over 6 mins) retention time 2.897 min, ESI+ found [M+H]=632.2.

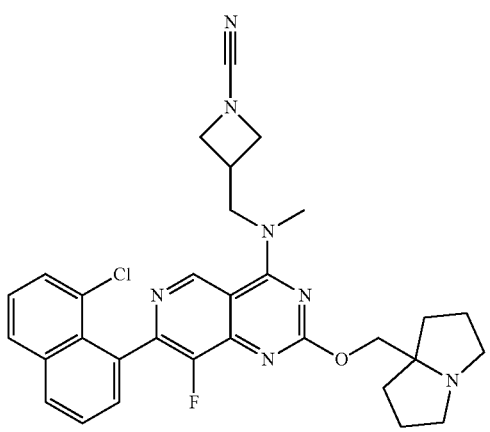 [SMILES: CN(CC1CN(C#N)C1)c1nc(OCC23CCCN2CCC3)nc2c(F)c(-c3cccc4cccc(Cl)c34)ncc12]

Example 28 (Method 2-C): 3-(((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)methyl)azetidine-1-carbonitrile

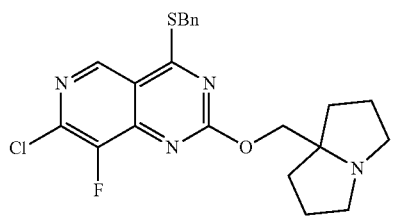

Step 1: 4-(benzylthio)-7-chloro-8-fluoro-2-((hexahydro-1H-pyrrolizin-7a-yl)methoxy)pyrido[4,3-d]pyrimidine To a solution of 4-benzylsulfanyl-2,7-dichloro-8-fluoropyrido[4,3-d]pyrimidine (10 g, 29.39 mmol) in dioxane (300 mL) was added N,N-diisopropylethylamine (11.40 g, 88.18 mmol) and 1,2,3,5,6,7-hexahydropyrrolizin-8-ylmethanol (8.30 g, 58.79 mmol). The mixture was stirred at 80° C. for 1 h. The reaction mixture was diluted with water (100 mL) and extracted with ethyl acetate (2×300 mL). The combined organic layers were dried over sodium sulphate and concentrated under vacuo. The crude residue was diluted with a (10:1) mixture of petroleum ether: ethyl acetate (300 mL) and the resulting precipitate was filtered, affording 4-(benzylthio)-7-chloro-8-fluoro-2-((hexahydro-1H-pyrrolizin-7a-yl)methoxy)pyrido[4,3-d]pyrimidine (7.7 g, 58.87%) as a white solid. LCMS Rt=0.740 min, m/z=444.1 [M+H]+.

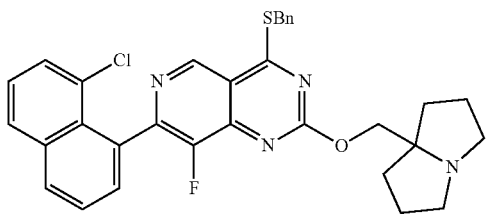

Step 2: 4-(benzylthio)-7-(8-chloronaphthalen-1-yl)-8-fluoro-2-((hexahydro-1H-pyrrolizin-7a-yl)methoxy)pyrido[4,3-d]pyrimidine A mixture of 4-(benzylthio)-7-chloro-8-fluoro-2-((hexahydro-1H-pyrrolizin-7a-yl)methoxy)pyrido[4,3-d]pyrimidine (3.9 g, 8.76 mmol), (8-chloro-1-naphthyl)boronic acid (3.62 g, 17.53 mmol), potassium phosphate (5.58 g, 26.29 mmol), [2-(2-aminophenyl)phenyl]-chloro-palladium:dicyclohexyl-[3-(2,4,6-triisopropylphenyl)phenyl]phosphane (689.63 mg, 876.50 μmol) in water (20 mL) and dioxane (40 mL) was stirred at 60° C. for 1 h under nitrogen atmosphere. The reaction mixture was diluted with water (40 mL) and extracted with ethyl acetate (2×90 mL). The combined organic layers were dried over sodium sulphate and concentrated in vacuo. The resulting residue was purified by column chromatography (silica gel, 100-200 mesh, 80% ethyl acetate in petroleum ether) affording 4-(benzylthio)-7-(8-chloronaphthalen-1-yl)-8-fluoro-2-((hexahydro-1H-pyrrolizin-7a-yl)methoxy)pyrido[4,3-d]pyrimidine (4.5 g, 44.95%) as a yellow solid. LCMS Rt=2.825 min, m/z=570.2 [M+H]+.

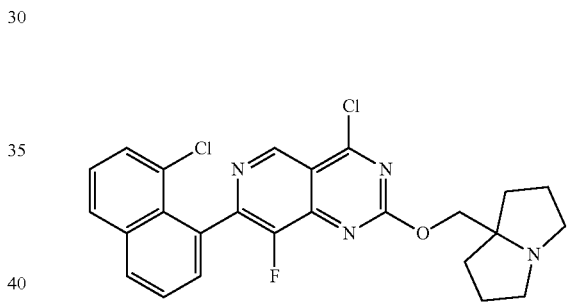

Step 3: 4-chloro-7-(8-chloronaphthalen-1-yl)-8-fluoro-2-((hexahydro-1H-pyrrolizin-7a-yl)methoxy)pyrido[4,3-d]pyrimidine To a solution of 4-(benzylthio)-7-(8-chloronaphthalen-1-yl)-8-fluoro-2-((hexahydro-1H-pyrrolizin-7a-yl)methoxy)pyrido[4,3-d]pyrimidine (100 mg, 175.10 μmol) in acetonitrile (10 mL) was added water (3.15 mg, 175.10 μmol), acetic acid (10.52 mg, 175.10 μmol) and 1,3-dichloro-5,5-dimethyl-imidazolidine-2,4-dione (93.14 mg, 472.77 μmol), then the mixture was stirred at 0° C. for 1 h. The reaction mixture was quenched with saturated sodium sulfite (30 mL) and the aqueous layer extracted with ethyl acetate (2×30 mL). The combined organic layers were dried over sodium sulphate and concentrated in vacuo affording 4-chloro-7-(8-chloronaphthalen-1-yl)-8-fluoro-2-((hexahydro-1H-pyrrolizin-7a-yl)methoxy)pyrido[4,3-d]pyrimidine (80 mg, crude) as a yellow oil, which was used in the next step without further purification. LCMS Rt=0.738 min, m/z=482.1 [M+H]+.

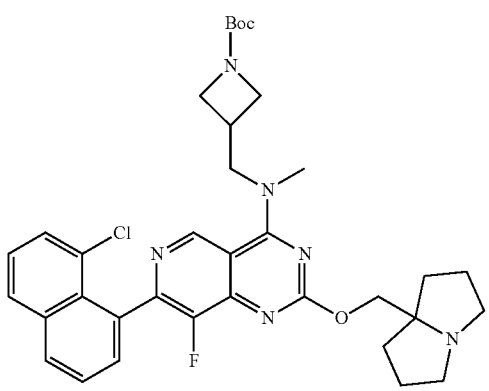 [SMILES: CN(CC1CN(C(=O)OC(C)(C)C)C1)c1nc(OCC23CCCN2CCC3)nc2c(F)c(-c3cccc4cccc(Cl)c34)ncc12]

Step 4: tert-butyl 3-(((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)methyl)azetidine-1-carboxylate To a solution of tert-butyl 3-(methylaminomethyl)azetidine-1-carboxylate (155.38 mg, 775.81 μmol) in N,N-dimethylformaldehyde (1 mL) were added N,N-diisopropylethylamine (200.54 mg, 1.55 mmol) and 4-chloro-7-(8-chloronaphthalen-1-yl)-8-fluoro-2-((hexahydro-1H-pyrrolizin-7a-yl)methoxy)pyrido[4,3-d]pyrimidine (250 mg, 517.21 μmol) at 0° C., then the mixture was stirred at 25° C. for 1 h. The reaction mixture was diluted with water (10 mL) and extracted with ethyl acetate (2×100 mL). The combined organic layers were dried over sodium sulphate and concentrated under vacuo. The resulting residue was purified by reverse phase HPLC (column: Phenomenex luna C18 250*50 mm*10 μm; mobile phase: [water (TFA)-ACN]; B %: 25%-55%, 10 min) affording tert-butyl 3-(((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)methyl)azetidine-1-carboxylate (180 mg, 38.86%, trifluoroacetate salt) as an orange solid. LCMS Rt=0.610 min, m/z=646.3 [M+H]+.

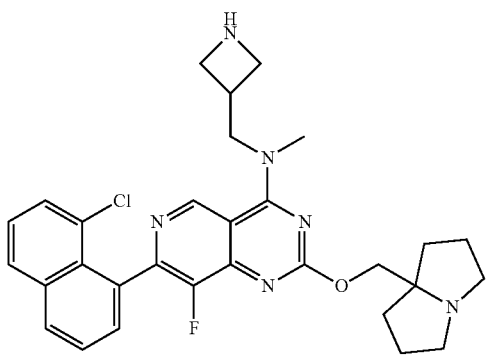 [SMILES: CN(CC1CNC1)c1nc(OCC23CCCN2CCC3)nc2c(F)c(-c3cccc4cccc(Cl)c34)ncc12]

Step 5: N-(azetidin-3-ylmethyl)-7-(8-chloronaphthalen-1-yl)-8-fluoro-2-((hexahydro-1H-pyrrolizin-7a-yl)methoxy)-N-methylpyrido[4,3-d]pyrimidin-4-amine To a solution of tert-butyl 3-(((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)methyl)azetidine-1-carboxylate (100 mg, 154.52 μmol) in dichloromethane (2 mL) was added trifluoroacetic acid (770.00 mg, 6.75 mmol), then the mixture was stirred at 20° C. for 1 h. The reaction mixture was diluted with saturated solution of sodium carbonate (5 mL) and extracted with dichloromethane (2×20 mL). The combined organic layers were dried over sodium sulphate and concentrated in vacuo affording N-(azetidin-3-ylmethyl)-7-(8-chloronaphthalen-1-yl)-8-fluoro-2-((hexahydro-1H-pyrrolizin-7a-yl)methoxy)-N-methylpyrido[4,3-d]pyrimidin-4-amine (100 mg, 97.90%) as a brown gum. LCMS Rt=0.582 min, m/z=546.2 [M+H]+.

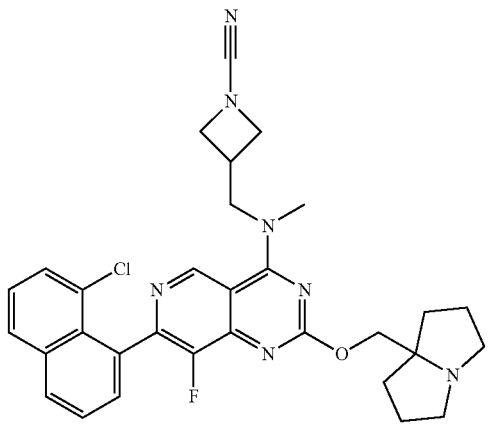 [SMILES: CN(CC1CN(C#N)C1)c1nc(OCC23CCCN2CCC3)nc2c(F)c(-c3cccc4cccc(Cl)c34)ncc12]

Step 6: 3-(((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)methyl)azetidine-1-carbonitrile To a solution of N-(azetidin-3-ylmethyl)-7-(8-chloronaphthalen-1-yl)-8-fluoro-2-((hexahydro-1H-pyrrolizin-7a-yl)methoxy)-N-methylpyrido[4,3-d]pyrimidin-4-amine (50 mg, 75.63 μmol) in dichloromethane (1 mL) was added N,N-diisopropylethylamine (29.32 mg, 226.90 μmol) and bromine cyanide (5.61 mg, 52.94 μmol), then the mixture was stirred at 0° C. for 30 min. The reaction mixture was quenched with saturated sodium carbonate (5 mL) and extracted with dichloromethane (2×10 mL). The combined organic layers were dried over sodium sulphate and concentrated in vacuo. The resulting residue was purified by reverse phase HPLC (column: Phenomenex Luna 80*30 mm*3 μm; mobile phase: [water(FA)-ACN]; B %: 1%-30%, 8 min) affording 3-(((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)methyl)azetidine-1-carbonitrile (10.13 mg, 23.05%, formate salt) as a white solid: $^1$H NMR (400 MHz, Acetonitrile-d3) δ 9.23 (s, 1H), 8.34 (s, 1H), 8.14-8.10 (m, 1H), 8.01 (d, J=8.1 Hz, 1H), 7.71-7.65 (m, 1H), 7.61 (ddd, J=1.1, 2.8, 7.3 Hz, 2H), 7.54-7.48 (m, 1H), 4.42-4.37 (m, 2H), 4.29-4.21 (m, 2H), 4.14-4.09 (m, 3H), 3.57-3.54 (m, 3H), 3.35-3.30 (m, 2H), 3.23 (br d, J=6.6 Hz, 2H), 2.83 (td, J=6.5, 10.9 Hz, 2H), 2.13-2.05 (m, 2H), 2.00-1.95 (m, 4H), 1.86-1.78 (m, 2H). LCMS Rt=2.112 min, m/z=571.2 [M+H]+.

LCMS (5 to 95% acetonitrile in water+0.1% trifluoroacetic acid over 6 min) retention time 2.112 min, ESI+ found [M+H]=571.2.

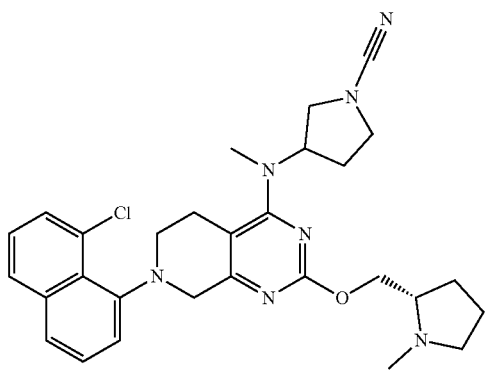 [SMILES: CN(c1nc(OC[C@@H]2CCCN2C)nc2c1CCN(c1cccc3cccc(Cl)c13)C2)C1CCN(C#N)C1]

Example 29 (Method 2-C$_1$): 3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidine-1-carbonitrile The substitution reaction was prepared in a similar fashion to Example 28 (Method 2-C), Step 6, substituting 7-(8-chloronaphthalen-1-yl)-N-methyl-2-(((S)-1-methylpyrrolidin-2-yl)methoxy)-N-(pyrrolidin-3-yl)-5,6,7,8-tetrahydropyrido[3,4-d]pyrimidin-4-amine (see Example 5 Step 2) for N-(azetidin-3-ylmethyl)-7-(8-chloronaphthalen-1-yl)-8-fluoro-N-methyl-2-((tetrahydro-1H-pyrrolizin-7a(5H)-yl)methoxy)pyrido[4,3-d]pyrimidin-4-amine. The crude product was purified by reverse phase HPLC (column: Phenomenex Luna C18 75*30 mm*3 µm; mobile phase: [water(0.2% FA)-ACN]; B %: 1%-40%, 8 min) affording 3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidine-1-carbonitrile (2.87 mg, 3.68%, formate salt) as a yellow oil: $^1$H NMR (400 MHz, Acetonitrile-d3) δ 7.87 (d, J=8.2 Hz, 1H), 7.70 (br d, J=8.2 Hz, 1H), 7.57 (d, J=7.3 Hz, 1H), 7.52 (dt, J=3.6, 7.8 Hz, 1H), 7.41 (t, J=7.8 Hz, 1H), 7.33 (br t, J=6.3 Hz, 1H), 4.84 (br d, J=7.7 Hz, 1H), 4.32 (s, 1H), 4.22 (br s, 1H), 4.18 (br d, J=4.9 Hz, 1H), 3.82-3.63 (m, 2H), 3.61-3.51 (m, 2H), 3.47-3.36 (m, 2H), 3.26-3.13 (m, 1H), 3.12-3.03 (m, 2H), 2.97 (d, J=4.6 Hz, 3H), 2.73-2.69 (m, 1H), 2.62-2.55 (m, 1H), 2.45 (s, 3H), 2.33 (br d, J=8.6 Hz, 1H), 2.25-1.98 (m, 3H), 1.84-1.64 (m, 3H). LCMS Rt=2.153 min, m/z=531.3 [M+H]+.

LCMS (5 to 95% acetonitrile in water+0.1% trifluoroacetic acid over 6 mins) retention time 2.153 min, ESI+ found [M+H]=531.3.

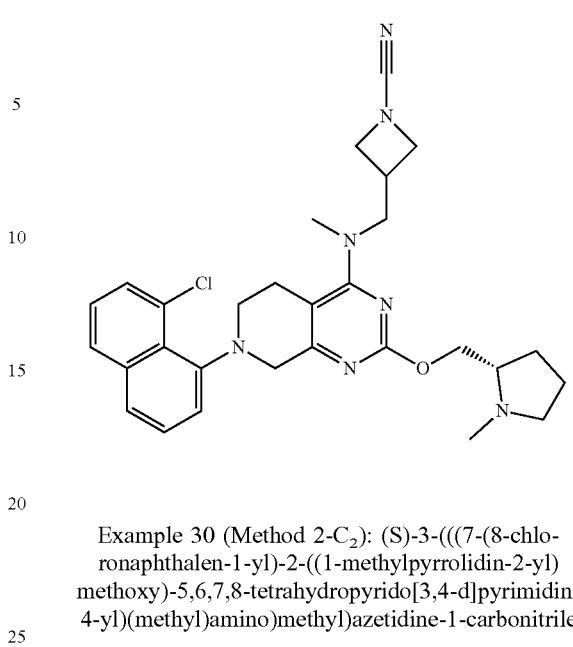

Example 30 (Method 2-C$_2$): (S)-3-(((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)methyl)azetidine-1-carbonitrile

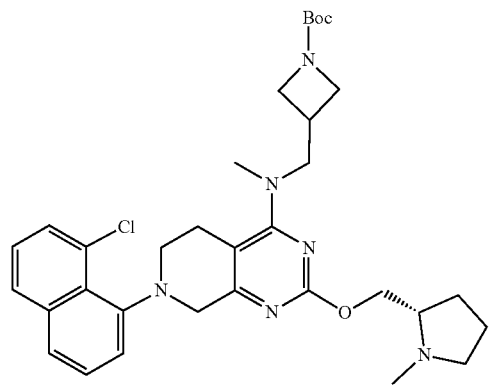 [SMILES: CN(CC1CN(C(=O)OC(C)(C)C)C1)c1nc(OC[C@@H]2CCCN2C)nc2c1CCN(c1cccc3cccc(Cl)c13)C2]

Step 1: tert-butyl (S)-3-(((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)methyl)azetidine-1-carboxylate The substitution reaction was prepared in a similar fashion to Example 1 (Method 1-A), Step 4, starting from (S)-7-(8-chloronaphthalen-1-yl)-2-((1-methylpyrrolidin-2-yl)methoxy)-5,6,7,8-tetrahydropyrido[3,4-d]pyrimidin-4-yl trifluoromethanesulfonate, and substituting tert-butyl 3-((methylamino)methyl)azetidine-1-carboxylate for tert-butyl N-(2-(methylamino)ethyl)carbamate. The crude product was purified by column chromatography (silica gel, 100-200 mesh, 10% methanol in dichloromethane) affording tert-butyl (S)-3-(((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)methyl)azetidine-1-carboxylate (90 mg, 55.04%) as a yellow oil.

LCMS Rt=0.691 min, m/z=606.3 [M+H]+.

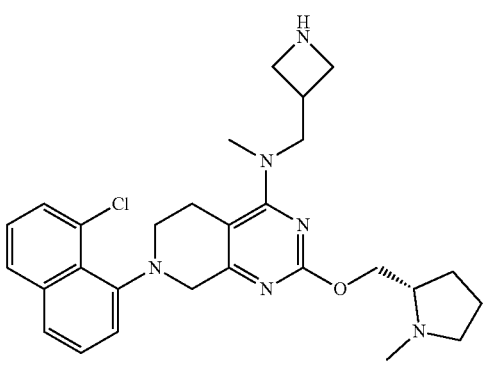 [SMILES: CN(CC1CNC1)c1nc(OC[C@@H]2CCCN2C)nc2c1CCN(c1cccc3cccc(Cl)c13)C2]

Step 2: N-(azetidin-3-ylmethyl)-7-(8-chloro-1-naphthyl)-N-methyl-2-[[(2S)-1-methylpyrrolidin-2-yl]methoxy]-6,8-dihydro-5H-pyrido[3,4-d]pyrimidin-4-amine The deprotection of Boc was prepared in a similar fashion to Example 1 (Method 1-A), Step 5. The crude product was concentrated in vacuo affording N-(azetidin-3-ylmethyl)-7-(8-chloro-1-naphthyl)-N-methyl-2-[[(2S)-1-methylpyrrolidin-2-yl]methoxy]-6,8-dihydro-5H-pyrido[3,4-d]pyrimidin-4-amine (80 mg, crude, trifluoroacetate salt) as yellow oil, which was used in the next step without further purification. LCMS Rt=0.667 min, m/z=506.3 [M+H]+.

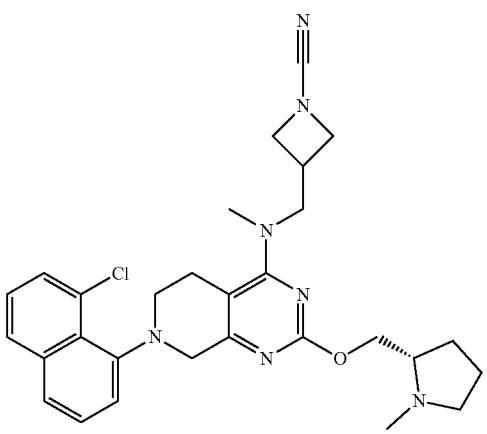 [SMILES: CN(CC1CN(C#N)C1)c1nc(OC[C@@H]2CCCN2C)nc2c1CCN(c1cccc3cccc(Cl)c13)C2]

Step 3: (S)-3-(((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)methyl)azetidine-1-carbonitrile The substitution reaction was prepared in a similar fashion to Example 28 (Method 2-C), Step 6. The crude product was purified by reverse phase HPLC (column: Phenomenex Luna C18 75*30 mm*3 μm; mobile phase: (water (0.2% FA)-ACN; B %: 1%-40%, 8 min) affording (S)-3-(((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)methyl)azetidine-1-carbonitrile (15.06 mg, 18.01%, formate salt) as a yellow oil: $^1$H NMR (400 MHz, Acetonitrile-d3) δ 7.86 (d, J=8.2 Hz, 1H), 7.69 (d, J=7.9 Hz, 1H), 7.59-7.48 (m, 2H), 7.44-7.37 (m, 1H), 7.32 (d, J=7.5 Hz, 1H), 4.44-4.33 (m, 1H), 4.29-4.12 (m, 4H), 4.03-3.93 (m, 2H), 3.91-3.85 (m, 1H), 3.71 (br d, J=17.2 Hz, 1H), 3.60 (td, J=6.8, 13.9 Hz, 1H), 3.55-3.48 (m, 1H), 3.28-3.19 (m, 2H), 3.18-3.10 (m, 1H), 3.08 (s, 3H), 2.97-2.87 (m, 1H), 2.63 (br d, J=15.0 Hz, 1H), 2.59-2.52 (m, 3H), 2.47 (q, J=8.8 Hz, 1H), 2.12-2.01 (m, 1H), 1.96 (td, J=2.5, 4.9 Hz, 1H), 1.90-1.68 (m, 3H). LCMS Rt=2.063 min, m/z=531.3 [M+H]$^+$.

LCMS (5 to 95% acetonitrile in water+0.1% trifluoroacetic acid over 6 mins) retention time 2.063 min, ESI+ found [M+H]=531.3.

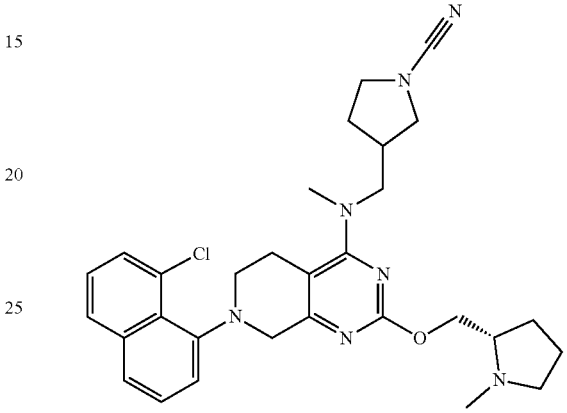

Example 31 (Method 2-C$_3$): 3-(((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)methyl)pyrrolidine-1-carbonitrile

Step 1: tert-butyl 3-(methylaminomethyl)pyrrolidine-1-carboxylate

To a solution of tert-butyl 3-formylpyrrolidine-1-carboxylate (500 mg, 2.51 mmol) and methanamine (779.36 mg, 7.53 mmol, 30% in ethanol) in ethanol (10 mL) was added acetic acid (150.70 mg, 2.51 mmol) and sodium cyanoborohydride (394.25 mg, 6.27 mmol) at 0° C., then the mixture was stirred at 30° C. for 1 h. The reaction mixture was quenched with water (10 mL) and extracted with dichloromethane (3×30 mL). The combined organic layers were dried over sodium sulphate and concentrated in vacuo affording tert-butyl 3-(methylaminomethyl)pyrrolidine-1-carboxylate (180 mg, crude) as yellow oil, which was used in the next step without further purification. LCMS Rt=0.737 min, m/z=214.2 [M+H]+.

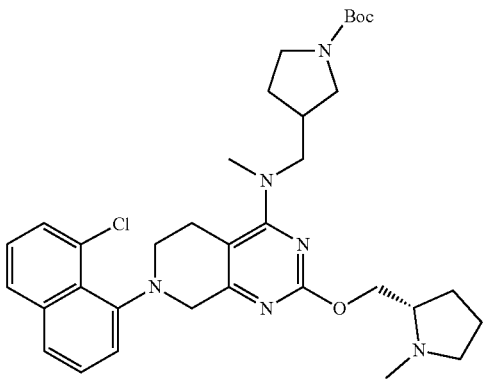 [SMILES: CN(CC1CCN(C(=O)OC(C)(C)C)C1)c1nc(OC[C@@H]2CCCN2C)nc2c1CCN(c1cccc3cccc(Cl)c13)C2]

Step 2: tert-butyl 3-(((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)methyl)pyrrolidine-1-carboxylate The substitution reaction was prepared in a similar fashion to Example 1 (Method 1-A), Step 4, starting from (S)-7-(8-chloronaphthalen-1-yl)-2-((1-methylpyrrolidin-2-yl)methoxy)-5,6,7,8-tetrahydropyrido[3,4-d]pyrimidin-4-yl trifluoromethanesulfonate, and substituting tert-butyl 3-(methylaminomethyl)pyrrolidine-1-carboxylate for tert-butyl N-(2-(methylamino)ethyl)carbamate. The crude product was purified by column chromatography (silica gel, 100-200 mesh, 90% ethyl acetate in petroleum ether) affording tert-butyl 3-(((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)methyl)pyrrolidine-1-carboxylate (75 mg, 44.83%) as a yellow oil. LCMS Rt=0.703 min, m/z=620.3 [M+H]+.

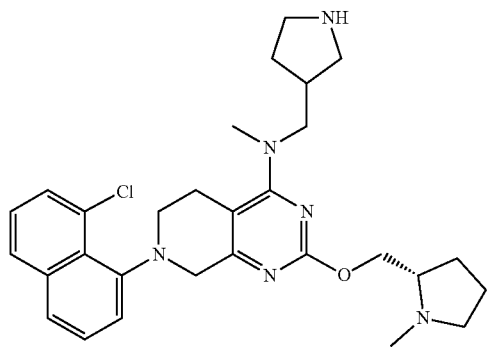 [SMILES: CN(CC1CCNC1)c1nc(OC[C@@H]2CCCN2C)nc2c1CCN(c1cccc3cccc(Cl)c13)C2]

Step 3: 7-(8-chloronaphthalen-1-yl)-N-methyl-2-(((S)-1-methylpyrrolidin-2-yl)methoxy)-N-(pyrrolidin-3-ylmethyl)-5,6,7,8-tetrahydropyrido[3,4-d]pyrimidin-4-amine The deprotection of Boc was prepared in a similar fashion to Example 1 (Method 1-A), Step 5. The mixture was concentrated in vacuo affording 7-(8-chloronaphthalen-1-yl)-N-methyl-2-(((S)-1-methylpyrrolidin-2-yl)methoxy)-N-(pyrrolidin-3-ylmethyl)-5,6,7,8-tetrahydropyrido[3,4-d]pyrimidin-4-amine (50 mg, crude, trifluoroacetate salt) as a yellow oil, which was used in the next step without further purification. LCMS Rt=0.664 min, m/z=520.3 [M+H]+.

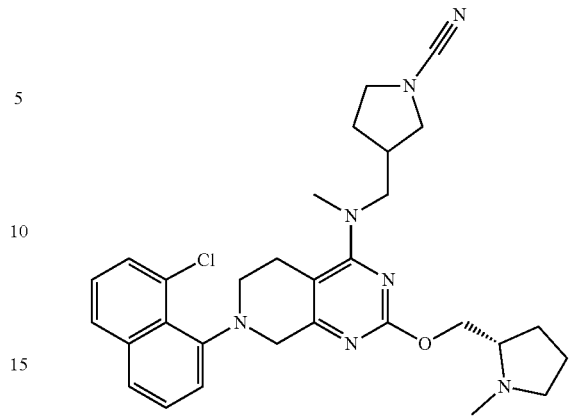

Step 4: 3-(((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)methyl)pyrrolidine-1-carbonitrile The substitution reaction was prepared in a similar fashion to Example 28 (Method 2-C), Step 6. The crude product was purified by reverse phase HPLC (column: Phenomenex Luna C18 75*30 mm*3 μm; mobile phase: (water (0.2% FA)-ACN; B %: 5%-40%, 8 min) affording 3-(((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)methyl)pyrrolidine-1-carbonitrile (2.3 mg, 4.82%, formate salt) as a yellow oil: $^1$H NMR (400 MHz, Acetonitrile-d3) δ 7.89 (d, J=7.9 Hz, 1H), 7.72 (d, J=8.3 Hz, 1H), 7.59 (d, J=7.3 Hz, 1H), 7.54 (dt, J=2.4, 7.9 Hz, 1H), 7.46-7.41 (m, 1H), 7.36 (dd, J=2.6, 7.2 Hz, 1H), 4.36-4.29 (m, 1H), 4.24 (br d, J=17.5 Hz, 1H), 4.14 (dd, J=5.9, 11.1 Hz, 1H), 3.92-3.82 (m, 1H), 3.75 (dd, J=4.0, 17.4 Hz, 1H), 3.56 (br d, J=10.8 Hz, 1H), 3.52-3.44 (m, 2H), 3.43-3.34 (m, 2H), 3.30-3.23 (m, 1H), 3.21 (br d, J=6.7 Hz, 1H), 3.16 (s, 3H), 3.14-3.08 (m, 1H), 3.08-3.01 (m, 1H), 2.76-2.59 (m, 3H), 2.43 (s, 3H), 2.25 (br s, 1H), 2.07-2.02 (m, 1H), 1.83-1.60 (m, 5H). LCMS Rt=2.085 min, m/z=545.3 [M+H]$^+$.

LCMS (5 to 95% acetonitrile in water+0.1% trifluoroacetic acid over 6 mins) retention time 2.085 min, ESI+ found [M+H]=545.3.

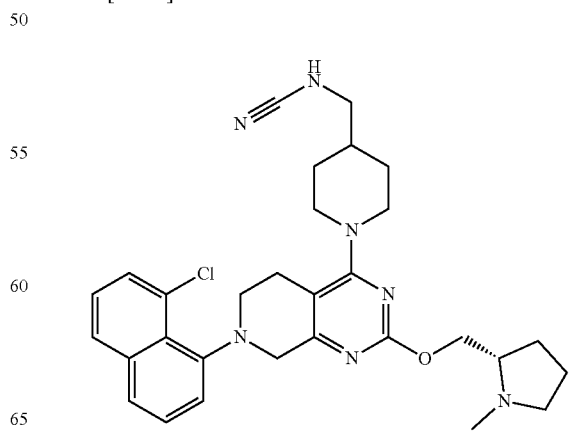

Example 32 (Method 2-C₄): (S)—N-((1-(7-(8-chloronaphthalen-1-yl)-2-((1-methylpyrrolidin-2-yl)methoxy)-5,6,7,8-tetrahydropyrido[3,4-d]pyrimidin-4-yl)piperidin-4-yl)methyl)cyanamide

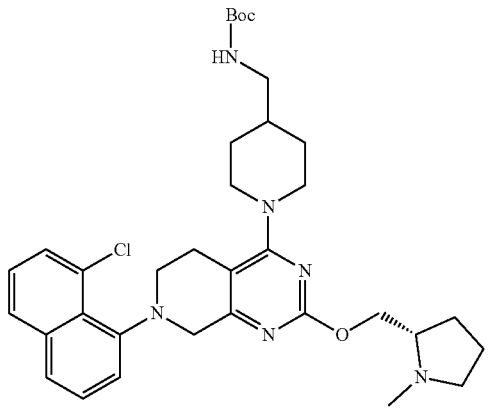 [SMILES: CN1CCC[C@H]1COc1nc2c(c(N3CCC(CNC(=O)OC(C)(C)C)CC3)n1)CCN(c1cccc3cccc(Cl)c13)C2]

Step 1: (S)-tert-butyl ((1-(7-(8-chloronaphthalen-1-yl)-2-((1-methylpyrrolidin-2-yl)methoxy)-5,6,7,8-tetrahydropyrido[3,4-d]pyrimidin-4-yl)piperidin-4-yl)methyl)carbamate The substitution reaction was prepared in a similar fashion to Example 1 (Method 1-A), Step 4, starting from (S)-7-(8-chloronaphthalen-1-yl)-2-((1-methylpyrrolidin-2-yl)methoxy)-5,6,7,8-tetrahydropyrido[3,4-d]pyrimidin-4-yl trifluoromethanesulfonate, and substituting tert-butyl (piperidin-4-ylmethyl)carbamate for tert-butyl (2-(methylamino)ethyl)carbamate. The crude product was purified by column chromatography (silica gel, 100-200 mesh, 90% ethyl acetate in petroleum ether) affording (S)-tert-butyl ((1-(7-(8-chloronaphthalen-1-yl)-2-((1-methylpyrrolidin-2-yl)methoxy)-5,6,7,8-tetrahydropyrido[3,4-d]pyrimidin-4-yl)piperidin-4-yl)methyl)carbamate (150 mg, 27.53%) as a brown oil. LCMS Rt=0.895 min, m/z=620.3 [M+H]+.

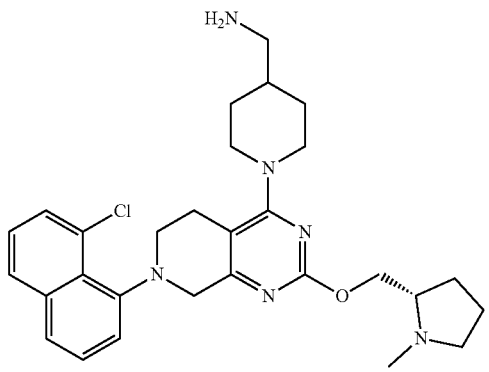 [SMILES: CN1CCC[C@H]1COc1nc2c(c(N3CCC(CN)CC3)n1)CCN(c1cccc3cccc(Cl)c13)C2]

Step 2: (S)-(1-(7-(8-chloronaphthalen-1-yl)-2-((1-methylpyrrolidin-2-yl)methoxy)-5,6,7,8-tetrahydropyrido[3,4-d]pyrimidin-4-yl)piperidin-4-yl)methanamine The deprotection of Boc was prepared in a similar fashion to Example 1 (Method 1-A), Step 5. The mixture was concentrated in vacuo affording (S)-(1-(7-(8-chloronaphthalen-1-yl)-2-((1-methylpyrrolidin-2-yl)methoxy)-5,6,7,8-tetrahydropyrido[3,4-d]pyrimidin-4-yl)piperidin-4-yl)methanamine (288 mg, crude, trifluoroacetate salt) as yellow oil, which was used in the next step without further purification. LCMS Rt=0.695 min, m/z=520.3 [M+H]+.

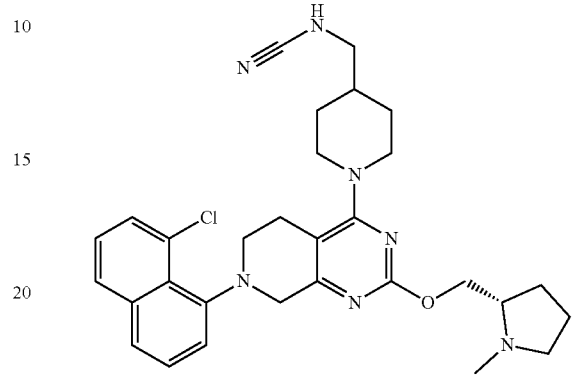

Step 3: (S)—N-((1-(7-(8-chloronaphthalen-1-yl)-2-((1-methylpyrrolidin-2-yl)methoxy)-5,6,7,8-tetrahydropyrido[3,4-d]pyrimidin-4-yl)piperidin-4-yl)methyl)cyanamide The substitution reaction was prepared in a similar fashion to Example 28 (Method 2-C), Step 6. The crude product was purified by reverse phase HPLC (column: Phenomenex Luna C18 75*30 mm*3 µm; mobile phase: (water (0.2% FA)-ACN; B %: 1%-40%, 8 min) affording (S)—N-((1-(7-(8-chloronaphthalen-1-yl)-2-((1-methylpyrrolidin-2-yl)methoxy)-5,6,7,8-tetrahydropyrido[3,4-d]pyrimidin-4-yl)piperidin-4-yl)methyl)cyanamide (5.5 mg, 5.99%, formate salt) as a yellow oil: ¹H NMR (400 MHz, Chloroform-d) δ 7.75 (d, J=7.9 Hz, 1H), 7.60 (d, J=7.9 Hz, 1H), 7.52 (d, J=7.3 Hz, 1H), 7.44 (t, J=7.8 Hz, 1H), 7.33 (t, J=7.8 Hz, 1H), 7.22 (d, J=6.8 Hz, 1H), 4.94-4.52 (m, 2H), 4.45-4.25 (m, 2H), 4.18-4.03 (m, 3H), 3.83 (dd, J=10.8, 17.5 Hz, 2H), 3.56-3.38 (m, 3H), 3.20-2.96 (m, 6H), 2.86 (t, J=12.4 Hz, 2H), 2.73 (d, J=7.9 Hz, 3H), 2.64 (s, 1H), 2.49 (d, J=13.4 Hz, 1H), 2.19 (d, J=4.0 Hz, 1H), 2.04 (s, 1H), 1.80 (s, 1H), 1.67-1.23 (m, 2H). LCMS Rt=3.265 min, m/z=545.3 [M+H]⁺.

LCMS (5 to 95% acetonitrile in water+0.1% ammonium bicarbonate over 6 mins) retention time 3.265 min, ESI+ found [M+H]=545.3.

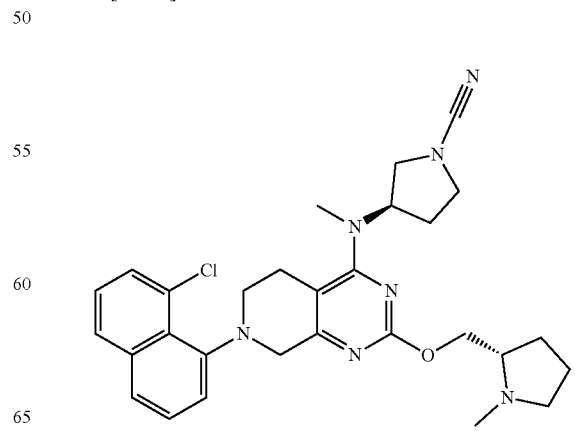

Example 33 (Method 2-C$_5$): (R)-3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidine-1-carbonitrile The substitution reaction was prepared in a similar fashion to Example 28 (Method 2-C), Step 6, starting with 7-(8-chloro-1-naphthyl)-N-methyl-2-[[(2S)-1-methylpyrrolidin-2-yl]methoxy]-N-[(3R)-pyrrolidin-3-yl]-6,8-dihydro-5H-pyrido[3,4-d]pyrimidin-4-amine (see Example 9 Step 3). The crude product was purified by reverse phase HPLC (column: Waters Xbridge BEH C18 100*30 mm*10 μm; mobile phase: (water (NH$_4$HCO$_3$)-ACN; B %: 40%-70%, 10 min) affording (R)-3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)pyrrolidine-1-carbonitrile (20 mg, 30.96%) as a white solid: $^1$H NMR (400 MHz, Acetonitrile-d3) δ 7.86 (d, J=7.7 Hz, 1H), 7.69 (d, J=8.2 Hz, 1H), 7.57 (dd, J=1.2, 7.5 Hz, 1H), 7.51 (dt, J=3.3, 7.8 Hz, 1H), 7.43-7.38 (m, 1H), 7.36-7.30 (m, 1H), 4.89-4.78 (m, 1H), 4.33-4.19 (m, 2H), 4.11 (dd, J=6.2, 10.8 Hz, 1H), 3.81-3.65 (m, 2H), 3.63-3.52 (m, 2H), 3.48-3.36 (m, 2H), 3.30-3.17 (m, 1H), 3.16-3.05 (m, 1H), 2.99-2.96 (m, 2H), 2.96 (s, 1H), 2.64-2.48 (m, 2H), 2.42-2.30 (m, 3H), 2.27-2.19 (m, 1H), 2.27-2.19 (m, 1H), 2.14-2.07 (m, 2H), 1.85-1.55 (m, 4H). LCMS Rt=3.310 min, m/z=531.3 [M+H]$^+$.

LCMS (5 to 95% acetonitrile in water+0.1% ammonium bicarbonate over 6 mins) retention time 3.310 min, ESI+ found [M+H]=531.3

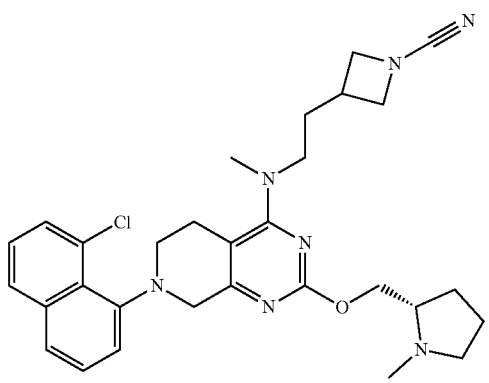 [SMILES: CN(CCC1CN(C#N)C1)c1nc(OC[C@@H]2CCCN2C)nc2c1CCN(c1cccc3cccc(Cl)c13)C2]

Example 34 (Method 2-C$_6$): (S)-3-(2-((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)ethyl)azetidine-1-carbonitrile

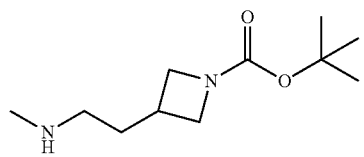

Step 1: tert-butyl 3-[2-(methylamino)ethyl]azetidine-1-carboxylate

To a solution of tert-butyl 3-(2-oxoethyl)azetidine-1-carboxylate (100 mg, 501.89 μmol) in methanol (1 mL) was added methanamine (779.36 mg, 7.53 mmol, 30% in ethanol) and sodium cyanoborohydride (94.62 mg, 1.51 mmol) at 0° C., then the mixture was stirred at 20° C. for 1 h. The reaction mixture was diluted with water (5 mL) and extracted with dichloromethane (2×10 mL). The combined organic layers were dried over sodium sulphate and concentrated in vacuo affording tert-butyl 3-[2-(methylamino)ethyl]azetidine-1-carboxylate (100 mg, crude) as a colorless oil, which was used in the next step without further purification.

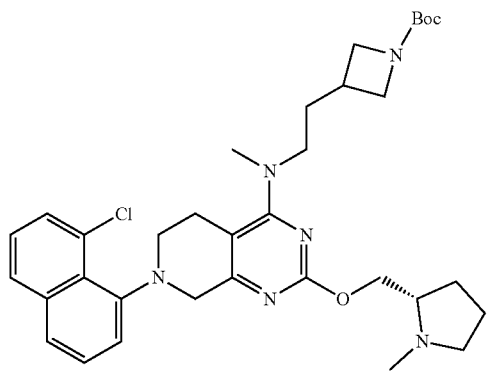 [SMILES: CN(CCC1CN(C(=O)OC(C)(C)C)C1)c1nc(OC[C@@H]2CCCN2C)nc2c1CCN(c1cccc3cccc(Cl)c13)C2]

Step 2: (S)-tert-butyl 3-(2-((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)ethyl)azetidine-1-carboxylate The substitution reaction was prepared in a similar fashion to Example 1 (Method 1-A), Step 4, substituting tert-butyl 3-(2-(methylamino)ethyl)azetidine-1-carboxylate for tert-butyl (2-(methylamino)ethyl)carbamate. The crude product was purified by reverse phase HPLC (column: Phenomenex luna C18 250*50 mm*10 μm; mobile phase: (water (0.1% TFA)-ACN; B %: 25%-55%, 10 min) affording (S)-tert-butyl 3-(2-((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)ethyl)azetidine-1-carboxylate (30 mg, 15.92%, trifluoroacetate salt) as a yellow solid. LCMS Rt=0.908 min, m/z=620.3 [M+H]+.

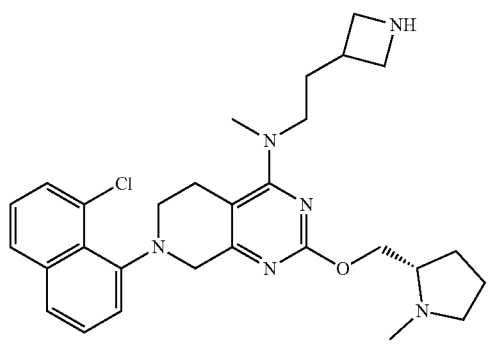 [SMILES: CN(CCC1CNC1)c1nc(OC[C@@H]2CCCN2C)nc2c1CCN(c1cccc3cccc(Cl)c13)C2]

Step 3: (S)—N-(2-(azetidin-3-yl)ethyl)-7-(8-chloronaphthalen-1-yl)-N-methyl-2-((1-methylpyrrolidin-2-yl)methoxy)-5,6,7,8-tetrahydropyrido[3,4-d]pyrimidin-4-amine The deprotection of Boc was prepared in a similar fashion to Example 1 (Method 1-A), Step 5. The crude product was concentrated affording (S)—N-(2-(azetidin-3-yl)ethyl)-7-(8-chloronaphthalen-1-yl)-N-methyl-2-((1-methylpyrrolidin-2-yl)methoxy)-5,6,7,8-tetrahydropyrido[3,4-d]pyrimidin-4-amine (25 mg, 96.47%, trifluoroacetate salt) as a yellow oil, which was used in next step without further purification. LCMS Rt=0.569 min, m/z=520.3 [M +H]+.

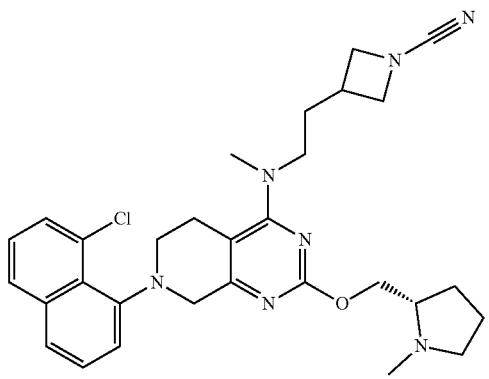 [SMILES: CN(CCC1CN(C#N)C1)c1nc(OC[C@@H]2CCCN2C)nc2c1CCN(c1cccc3cccc(Cl)c13)C2]

Step 4: (S)-3-(2-((7-(8-chloronaphthalen-1-yl)-2-((1-methylpyrrolidin-2-yl)methoxy)-5,6,7,8-tetrahydro-pyrido[3,4-d]pyrimidin-4-yl)(methyl)amino)ethyl) azetidine-1-carbonitrile The substitution reaction was prepared in a similar fashion to Example 28 (Method 2-C), Step 6. The crude product was purified by reverse phase HPLC (column: Phenomenex Luna 80*30 mm*3 μm; mobile phase: (water (0.2% FA)-ACN; B %: 10%-40%, 8 min) affording (S)-3-(2-((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)ethyl)azetidine-1-carbonitrile (4.71 mg, 22.73%, formate salt) as a yellow oil; $^1$H NMR (400 MHz, Acetonitrile-d3) δ 7.83 (d, J=8.11 Hz, 1H), 7.66 (d, J=8.11 Hz, 1H), 7.52-7.56 (m, 1H), 7.48 (t, J=7.78 Hz, 1H), 7.34-7.42 (m, 1H), 7.30 (d, J=7.45 Hz, 1H), 4.37 (dd, J=11.51, 6.03 Hz, 1H), 4.26 (dt, J=11.35, 4.52 Hz, 1H), 4.08-4.22 (m, 3H), 3.78-3.84 (m, 2H), 3.69 (d, J=17.32 Hz, 1H), 3.43-3.56 (m, 2H), 3.31-3.41 (m, 1H) 3.12-3.27 (m, 3H), 3.08 (s, 4H), 2.94-3.02 (m, 1H), 2.62-2.73 (m, 3H), 2.55-2.60 (m, 3H), 2.46-2.54 (m, 1H), 2.02-2.13 (m, 1H), 1.80-1.87 (m, 2H), 1.68-1.78 (m, 1H). LCMS Rt=2.067 min, m/z =545.3 [M+H]+.

LCMS (5 to 95% acetonitrile in water+0.03% trifluoroacetic acid over 6 mins) retention time 2.067 min, ESI+ found [M+H]=545.3

Example 35 (Method 2-C$_7$): 3-((7-(8-chloronaphthalen-1-yl)-8-fluoro-2-(((S)-1-methylpyrrolidin-2-yl)methoxy)pyrido[4,3-d]pyrimidin-4-yl)(methyl)amino)pyrrolidine-1-carbonitrile

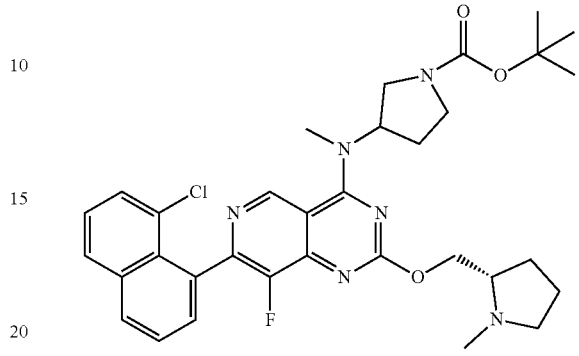

Step 1: tert-butyl 3-((7-(8-chloronaphthalen-1-yl)-8-fluoro-2-(((S)-1-methylpyrrolidin-2-yl)methoxy) pyrido[4,3-d]pyrimidin-4-yl)(methyl)amino)pyrrolidine-1-carboxylate The substitution reaction was prepared in a similar fashion to Example 28 (Method 2-C), Step 4, substituting (S)-4-chloro-7-(8-chloronaphthalen-1-yl)-8-fluoro-2-((1-methylpyrrolidin-2-yl)methoxy)pyrido[4,3-d]pyrimidine for 4-chloro-7-(8-chloronaphthalen-1-yl)-8-fluoro-2-((tetrahydro-1H-pyrrolizin-7a(5H)-yl)methoxy)pyrido[4,3-d]pyrimidine. The crude product was purified by reverse phase HPLC (column: Waters Xbridge BEH C18 250*50 mm*10 μm; mobile phase: (water (NH$_4$HCO$_3$)-ACN; B %: 45%-65%, 10 min) affording tert-butyl 3-((7-(8-chloronaphthalen-1-yl)-8-fluoro-2-(((S)-1-methylpyrrolidin-2-yl)methoxy)pyrido[4,3-d]pyrimidin-4-yl)(methyl)amino)pyrrolidine-1-carboxylate (150 mg, 47.81%) as a yellow oil. LCMS Rt=2.603 min, m/z=620.3 [M+H]$^+$.

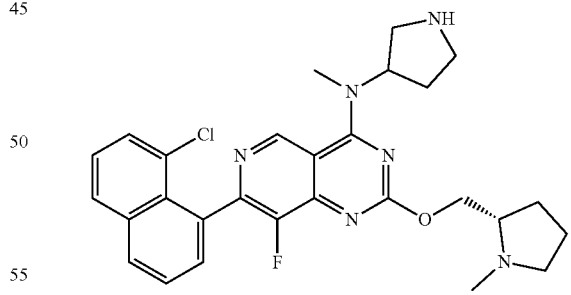

Step 2: 7-(8-chloro-1-naphthyl)-8-fluoro-N-methyl-2-[[(2S)-1-methylpyrrolidin-2-yl]methoxy]-N-pyrrolidin-3-yl-pyrido[4,3-d]pyrimidin-4-amine The deprotection of Boc was prepared in a similar fashion to Example 28 (Method 2-C), Step 5. The mixture was concentrated in vacuo affording 7-(8-chloro-1-naphthyl)-8-fluoro-N-methyl-2-[[(2S)-1-methylpyrrolidin-2-yl] methoxy]-N-pyrrolidin-3-yl-pyrido[4,3-d]pyrimidin-4-

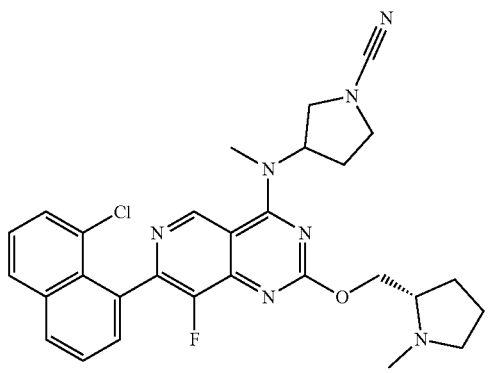 [SMILES: CN(c1nc(OC[C@@H]2CCCN2C)nc2c(F)c(-c3cccc4cccc(Cl)c34)ncc12)C1CCN(C#N)C1]

amine (120 mg, crude) as a yellow oil, which was used in the next step without further purification. LCMS Rt=0.561 min, m/z=520.2 [M+H]⁺.

Example 36 (Method 2-C₈): (R)-3-((7-(8-chloronaphthalen-1-yl)-8-fluoro-2-(((S)-1-methylpyrrolidin-2-yl)methoxy)pyrido[4,3-d]pyrimidin-4-yl)(methyl)amino)pyrrolidine-1-carbonitrile

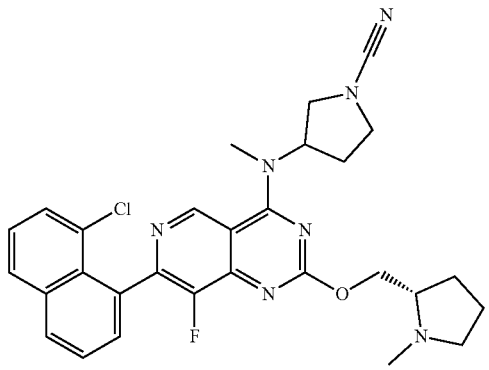 [SMILES: CN(c1nc(OC[C@@H]2CCCN2C)nc2c(F)c(-c3cccc4cccc(Cl)c34)ncc12)C1CCN(C#N)C1]

Step 3: 3-((7-(8-chloronaphthalen-1-yl)-8-fluoro-2-(((S)-1-methylpyrrolidin-2-yl)methoxy)pyrido[4,3-d]pyrimidin-4-yl)(methyl)amino)pyrrolidine-1-carbonitrile

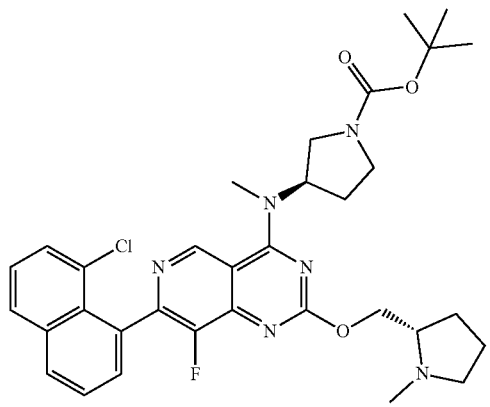 [SMILES: CN1CCC[C@H]1COc1nc(N(C)[C@@H]2CCN(C(=O)OC(C)(C)C)C2)c2cnc(-c3cccc4cccc(Cl)c34)c(F)c2n1]

Step 1: tert-butyl (R)-3-((7-(8-chloronaphthalen-1-yl)-8-fluoro-2-(((S)-1-methylpyrrolidin-2-yl)methoxy)pyrido[4,3-d]pyrimidin-4-yl)(methyl)amino)pyrrolidine-1-carboxylate The substitution reaction was prepared in a similar fashion to Example 28 (Method 2-C), Step 6. The crude product was purified by reverse phase HPLC (column: Waters Xbridge Prep OBD C18 150*40 mm*10 μm; mobile phase: (water (NH₄HCO₃)-ACN; B %: 30%-60%, 8 min) affording 3-((7-(8-chloronaphthalen-1-yl)-8-fluoro-2-(((S)-1-methylpyrrolidin-2-yl)methoxy)pyrido[4,3-d]pyrimidin-4-yl)(methyl)amino)pyrrolidine-1-carbonitrile (1.35 mg, 4.31%) as a white solid: ¹H NMR (400 MHz, Acetonitrile-d3) δ 9.24-9.19 (m, 1H), 8.16 (d, J=7.2 Hz, 1H), 8.06 (d, J=7.8 Hz, 1H), 7.76-7.69 (m, 1H), 7.65 (br d, J=7.6 Hz, 2H), 7.58-7.54 (m, 1H), 5.49-5.38 (m, 1H), 4.53-4.46 (m, 1H), 4.35 (br dd, J=6.3, 10.9 Hz, 1H), 3.88-3.78 (m, 1H), 3.74-3.66 (m, 1H), 3.62-3.51 (m, 2H), 3.46 (s, 3H), 3.09-3.01 (m, 1H), 2.74-2.66 (m, 1H), 2.46 (s, 4H), 2.07-2.01 (m, 2H), 1.82-1.73 (m, 4H). LCMS Rt=2.057 min, m/z=545.2 [M+H]+. LCMS (5 to 95% acetonitrile in water+0.03% ammonium bicarbonate over 6 mins) retention time 2.057 min, ESI+ found [M+H]=545.2.

The substitution reaction was prepared in a similar fashion to Example 28 (Method 2-C), Step 4, substituting (S)-4-chloro-7-(8-chloronaphthalen-1-yl)-8-fluoro-2-((1-methylpyrrolidin-2-yl)methoxy)pyrido[4,3-d]pyrimidine for 4-chloro-7-(8-chloronaphthalen-1-yl)-8-fluoro-2-((tetrahydro-1H-pyrrolizin-7a(5H)-yl)methoxy)pyrido[4,3-d]pyrimidine, and substituting tert-butyl (R)-3-(methylamino)pyrrolidine-1-carboxylate for tert-butyl 3-((methylamino)methyl)azetidine-1-carboxylate. The crude product was purified by column chromatography (silica gel, 100-200 mesh, 0-9% methanol in dichloromethane) affording tert-butyl (R)-3-((7-(8-chloronaphthalen-1-yl)-8-fluoro-2-(((S)-1-methylpyrrolidin-2-yl)methoxy)pyrido[4,3-d]pyrimidin-4-yl)(methyl)amino)pyrrolidine-1-carboxylate (930 mg, 32.94%) as an orange gum. LCMS Rt=0.702 min, m/z=620.2 [M+H]⁺.

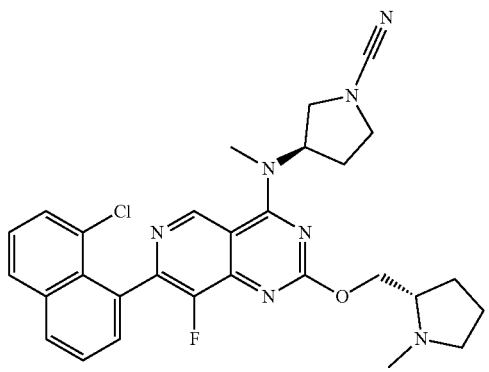 [SMILES: CN1CCC[C@H]1COc1nc(N(C)[C@@H]2CCN(C#N)C2)c2cnc(-c3cccc4cccc(Cl)c34)c(F)c2n1]

Step 2: 7-(8-chloro-1-naphthyl)-8-fluoro-N-methyl-2-[[(2S)-1-methylpyrrolidin-2-yl]methoxy]-N-[(3R)-pyrrolidin-3-yl]pyrido[4,3-d]pyrimidin-4-amine The deprotection of Boc was prepared in a similar fashion to Example 28 (Method 2-C), Step 5. The crude product was purified by reverse phase HPLC (column: Phenomenex luna C18 250*50 mm*10 μm; mobile phase: (water (TFA)-ACN; B %: 20%-50%, 10 min) affording 7-(8-chloro-1-naphthyl)-8-fluoro-N-methyl-2-[[(2S)-1-methylpyrrolidin-2-yl]methoxy]-N-[(3R)-pyrrolidin-3-yl]pyrido[4,3-d]pyrimidin-4-amine (160 mg, 40.72%, trifluoroacetate salt) as a yellow solid. LCMS Rt=0.574 min, m/z=520.2 [M+H]$^+$.

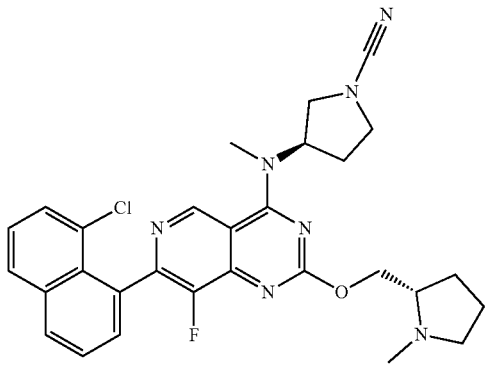

Step 3: (R)-3-((7-(8-chloronaphthalen-1-yl)-8-fluoro-2-(((S)-1-methylpyrrolidin-2-yl)methoxy)pyrido[4,3-d]pyrimidin-4-yl)(methyl)amino)pyrrolidine-1-carbonitrile The substitution reaction was prepared in a similar fashion to Example 28 (Method 2-C), Step 6. The crude product was purified by reverse phase HPLC (column: Phenomenex Luna 80*30 mm*3 μm; mobile phase: (water (FA)-ACN; B %: 5%-45%, 8 min) affording (R)-3-((7-(8-chloronaphthalen-1-yl)-8-fluoro-2-(((S)-1-methylpyrrolidin-2-yl)methoxy)pyrido[4,3-d]pyrimidin-4-yl)(methyl)amino)pyrrolidine-1-carbonitrile (83.22 mg, 58.80%, formate salt) as a pale yellow solid: $^1$H NMR (400 MHz, Acetonitrile-d3) δ 9.24-9.19 (m, 1H), 8.16 (d, J=7.2 Hz, 1H), 8.06 (d, J=7.8 Hz, 1H), 7.76-7.69 (m, 1H), 7.65 (br d, J=7.6 Hz, 2H), 7.58-7.54 (m, 1H), 5.49-5.38 (m, 1H), 4.53-4.46 (m, 1H), 4.35 (br dd, J=6.3, 10.9 Hz, 1H), 3.88-3.78 (m, 1H), 3.74-3.66 (m, 1H), 3.62-3.51 (m, 2H), 3.46 (s, 3H), 3.09-3.01 (m, 1H), 2.74-2.66 (m, 1H), 2.46 (s, 4H), 2.07-2.01 (m, 2H), 1.82-1.73 (m, 4H). LCMS Rt=2.071 min, m/z=545.2 [M+H]+.

LCMS (5 to 95% acetonitrile in water+0.1% trifluoroacetic acid over 6 mins) retention time 2.071 min, ESI+ found [M+H]=545.2.

Example 37 (Method 2-C$_9$): (3aR,6aR)-1-(7-(8-chloronaphthalen-1-yl)-2-(((S)-1-methylpyrrolidin-2-yl)methoxy)-5,6,7,8-tetrahydropyrido[3,4-d]pyrimidin-4-yl)hexahydropyrrolo[3,4-b]pyrrole-5(1H)-carbonitrile

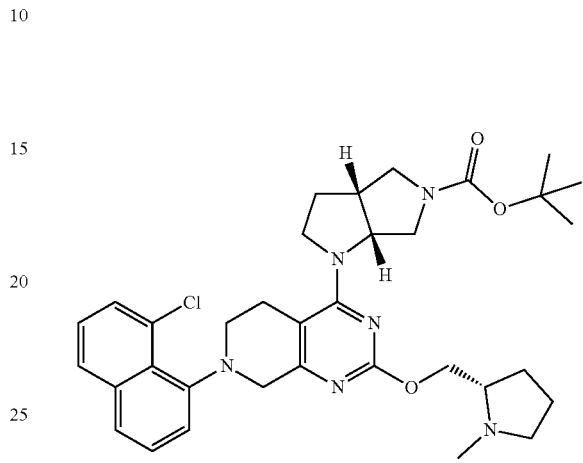

Step 1: tert-butyl (3aR,6aR)-1-[7-(8-chloro-1-naphthyl)-2-[[(2S)-1-methylpyrrolidin-2-yl]methoxy]-6,8-dihydro-5H-pyrido[3,4-d]pyrimidin-4-yl]-2,3,3a,4,6,6a-hexahydropyrrolo[3,4-b]pyrrole-5-carboxylate The substitution reaction was prepared in a similar fashion to Example 1 (Method 1-A), Step 4, starting with (S)-7-(8-chloronaphthalen-1-yl)-2-((1-methylpyrrolidin-2-yl)methoxy)-5,6,7,8-tetrahydropyrido[3,4-d]pyrimidin-4-yl trifluoromethanesulfonate, and substituting tert-butyl (3aR,6aR)-hexahydropyrrolo[3,4-b]pyrrole-5(1H)-carboxylate for tert-butyl (2-(methylamino)ethyl)carbamate. The reaction mixture was quenched with water (2 mL) and then filtrated affording tert-butyl (3aR,6aR)-1-[7-(8-chloro-1-naphthyl)-2-[[(2S)-1-methylpyrrolidin-2-yl]methoxy]-6,8-dihydro-5H-pyrido[3,4-d]pyrimidin-4-yl]-2,3,3a,4,6,6a-hexahydropyrrolo[3,4-b]pyrrole-5-carboxylate (140 mg, crude) as a brown solid, which was used in the next step without further purification. LCMS Rt=0.591 min, m/z=618.3 [M+H]$^+$.

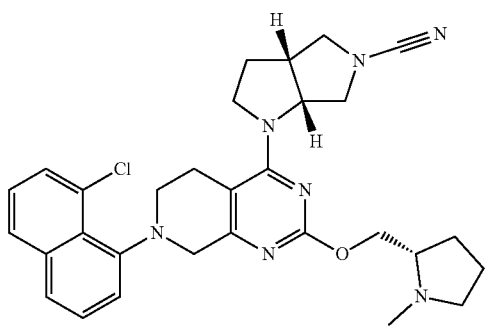 [SMILES: CN1CCC[C@H]1COc1nc2c(c(N3CC[C@@H]4CN(C#N)C[C@@H]43)n1)CCN(c1cccc3cccc(Cl)c13)C2]

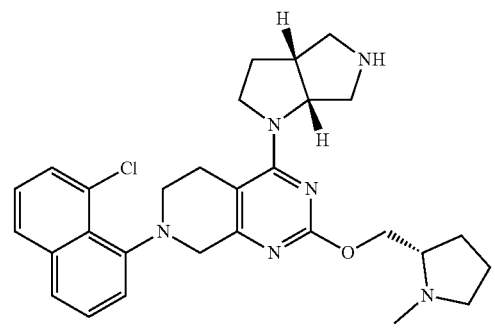 [SMILES: CN1CCC[C@H]1COc1nc2c(c(N3CC[C@@H]4CNC[C@@H]43)n1)CCN(c1cccc3cccc(Cl)c13)C2]

Step 2: 4-[(3aR,6aR)-3,3a, 4,5,6,6a-hexahydro-2H-pyrrolo[3,4-b]pyrrol-1-yl]-7-(8-chloro-1-naphthyl)-2-[[(2S)-1-methylpyrrolidin-2-yl]methoxy]-6,8-dihydro-5H-pyrido[3,4-d]pyrimidine The deprotection of Boc was prepared in a similar fashion to Example 1 (Method 1-A), Step 5. The mixture was concentrated in vacuo affording 4-[(3aR,6aR)-3,3a, 4,5,6,6a-hexahydro-2H-pyrrolo[3,4-b]pyrrol-1-yl]-7-(8-chloro-1-naphthyl)-2-[[(2S)-1-methylpyrrolidin-2-yl]methoxy]-6,8-dihydro-5H-pyrido[3,4-d]pyrimidine (150 mg, crude) as a brown oil, which was used in the next step without further purification. LCMS Rt=0.582 min, m/z=518.2 [M+H]+.

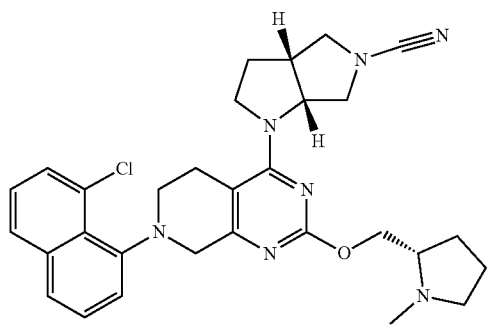 [SMILES: CN1CCC[C@H]1COc1nc2c(c(N3CC[C@@H]4CN(C#N)C[C@@H]43)n1)CCN(c1cccc3cccc(Cl)c13)C2]

Step 3: (3aR,6aR)-1-(7-(8-chloronaphthalen-1-yl)-2-(((S)-1-methylpyrrolidin-2-yl)methoxy)-5,6,7,8-tetrahydropyrido[3,4-d]pyrimidin-4-yl)hexahydropyrrolo[3,4-b]pyrrole-5(1H)-carbonitrile The substitution reaction was prepared in a similar fashion to Example 28 (Method 2-C), Step 6, substituting 4-[(3aR,6aR)-3,3a, 4,5,6,6a-hexahydro-2H-pyrrolo[3,4-b]pyrrol-1-yl]-7-(8-chloro-1-naphthyl)-2-[[(2S)-1-methylpyrrolidin-2-yl]methoxy]-6,8-dihydro-5H-pyrido[3,4-d]pyrimidine for N-(azetidin-3-ylmethyl)-7-(8-chloronaphthalen-1-yl)-8-fluoro-N-methyl-2-((tetrahydro-1H-pyrrolizin-7a(5H)-yl)methoxy)pyrido[4,3-d]pyrimidin-4-amine. The crude product was purified by reverse phase HPLC (column: Phenomenex Luna 80*30 mm*3 μm; mobile phase: (water (FA)-ACN; B %: 5%-35%, 8 min) affording (3aR,6aR)-1-(7-(8-chloronaphthalen-1-yl)-2-(((S)-1-methylpyrrolidin-2-yl)methoxy)-5,6,7,8-tetrahydropyrido[3,4-d]pyrimidin-4-yl)hexahydropyrrolo[3,4-b]pyrrole-5(1H)-carbonitrile (4.32 mg, 6.01%, formate salt) as a white solid: $^1$H NMR (400 MHz, Acetonitrile-d3) δ 7.89-7.80 (m, 1H), 7.72-7.63 (m, 1H), 7.57-7.43 (m, 2H), 7.42-7.23 (m, 2H), 4.85-4.64 (m, 1H), 4.37-4.27 (m, 1H), 4.25-4.11 (m, 2H), 4.05-3.93 (m, 1H), 3.91-3.78 (m, 2H), 3.71-3.54 (m, 3H), 3.44 (dd, J=1.5, 10.8 Hz, 1H), 3.39-3.27 (m, 2H), 3.19-3.08 (m, 2H), 3.03 (dt, J=7.7, 11.2 Hz, 1H), 2.84-2.76 (m, 2H), 2.49-2.45 (m, 3H), 2.39 (dq, J=5.1, 8.7 Hz, 1H), 2.11-2.00 (m, 2H), 1.90-1.65 (m, 4H). LCMS Rt=3.264 min, m/z=543.3 [M+H]+.

LCMS (5 to 95% acetonitrile in water+0.03% ammonium bicarbonate over 6 mins) retention time 3.264 min, ESI+ found [M+H]=543.3.

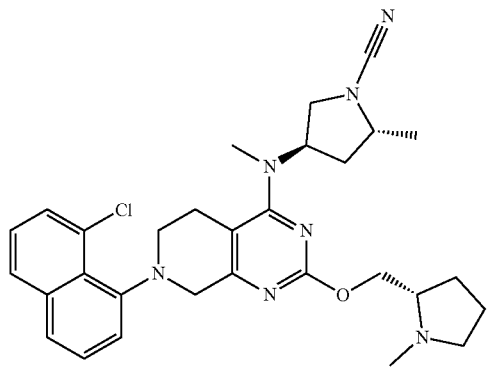 [SMILES: C[C@@H]1C[C@@H](N(C)c2nc(OC[C@@H]3CCCN3C)nc3c2CCN(c2cccc4cccc(Cl)c24)C3)CN1C#N]

Example 38 (Method 2-C$_{10}$): (2R,4R)-4-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)-2-methylpyrrolidine-1-carbonitrile

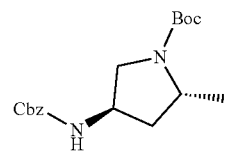 [SMILES: C[C@@H]1C[C@@H](NC(=O)OCc2ccccc2)CN1C(=O)OC(C)(C)C]

Step 1: tert-butyl (2R,4R)-4-(benzyloxycarbonylamino)-2-methyl-pyrrolidine-1-carboxylate To a solution of tert-butyl (2R,4R)-4-amino-2-methyl-pyrrolidine-1-carboxylate (500 mg, 2.50 mmol) in tetrahydrofuran (10 mL) was added benzyl carbonochloridate (425.89 mg, 2.50 mmol) and sodium hydroxide (2 M, 3.74 mL) at 0° C., then the mixture was stirred at 20° C. for 2 h. The reaction mixture was diluted with water (10 mL) and extracted with dichloromethane (2×20 mL). The combined organic layers were dried over sodium sulphate and concentrated in vacuo. The resulting residue was purified by column chromatography (silica gel, 100-200 mesh, 30% ethyl acetate in petroleum ether) affording tert-butyl (2R,4R)-4-(benzyloxycarbonylamino)-2-methyl-pyrrolidine-1-carboxylate (640 mg, 76.66%) as a white solid: $^1$H NMR (400 MHz, Chloroform-d) δ 7.40-7.32 (m, 5H), 5.11 (s, 2H), 4.83-4.72 (m, 1H), 4.34-4.27 (m, 1H), 3.94 (br d, J=3.4 Hz, 1H), 3.64 (br dd, J=6.4, 11.2 Hz, 1H), 3.30-3.21 (m, 1H), 2.03-1.82 (m, 1H), 1.46 (s, 9H), 1.23 (d, J=6.4 Hz, 3H).

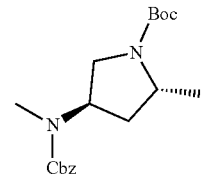

Step 2: tert-butyl (2R,4R)-4-[benzyloxycarbonyl(methyl)amino]-2-methyl-pyrrolidine-1-carboxylate To a solution of tert-butyl (2R,4R)-4-(benzyloxycarbonylamino)-2-methyl-pyrrolidine-1-carboxylate (590 mg, 1.76 mmol) in N,N-dimethylformaldehyde (10 mL) was added sodium hydride (141.13 mg, 3.53 mmol) and the mixture was stirred at 0° C. for 0.5 h, followed by the addition of methyl iodide (375.63 mg, 2.65 mmol). The mixture was stirred at 20° C. for 2 hr. The reaction mixture was diluted with water (10 mL) and extracted with dichloromethane (2×20 mL). The combined organic layers were dried over sodium sulphate and concentrated under vacuo. The resulting residue was purified by column chromatography (silica gel, 100-200 mesh, 30% ethyl acetate in petroleum ether) affording tert-butyl (2R,4R)-4-[benzyloxycarbonyl(methyl)amino]-2-methyl-pyrrolidine-1-carboxylate (360 mg, 54.46%) as a yellow oil.

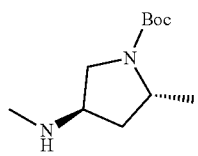

Step 3: tert-butyl (2R,4R)-2-methyl-4-(methylamino)pyrrolidine-1-carboxylate

To a solution of tert-butyl (2R,4R)-4-[benzyloxycarbonyl(methyl)amino]-2-methyl-pyrrolidine-1-carboxylate (320 mg, 918.39 μmol) in ethyl acetate (10 mL) was added palladium on carbon (300 mg, 918.39 μmol, 10% purity). The reaction mixture was degassed with hydrogen for three times and stirred at 20° C. for 2 h under hydrogen atmosphere. The reaction mixture was filtered and the organic layer was concentrated in vacuo affording tert-butyl (2R,4R)-2-methyl-4-(methylamino)pyrrolidine-1-carboxylate (190 mg, crude) as a yellow gum: $^1$H NMR (400 MHz, Chloroform-d) δ 4.04-3.90 (m, 1H), 3.58 (dd, J=6.1, 10.8 Hz, 1H), 3.34-3.08 (m, 2H), 2.44 (s, 3H), 1.88-1.77 (m, 2H), 1.47 (s, 9H), 1.20 (br d, J=6.0 Hz, 3H).

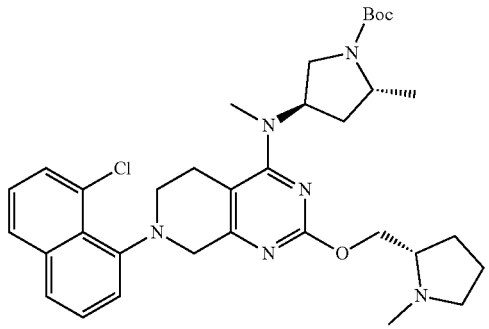 [SMILES: C[C@@H]1C[C@@H](N(C)c2nc(OC[C@@H]3CCCN3C)nc3c2CCN(c2cccc4cccc(Cl)c24)C3)CN1C(=O)OC(C)(C)C]

Step 4: tert-butyl (2R,4R)-4-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)-2-methylpyrrolidine-1-carboxylate The substitution reaction was prepared in a similar fashion to Example 1 (Method 1-A), Step 4, substituting tert-butyl (2R,4R)-2-methyl-4-(methylamino)pyrrolidine-1-carboxylate for tert-butyl (2-(methylamino)ethyl)carbamate. The crude product was purified by reverse phase HPLC (column: Phenomenex Luna 80*30 mm*3 μm; mobile phase: (water (TFA)- ACN; B %: 15%-55%, 8 min) affording tert-butyl (2R,4R)-4-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)-2-methylpyrrolidine-1-carboxylate (180 mg, 38.20%) as a yellow solid. LCMS Rt=1.826 min, m/z =620.3 [M+H]$^+$.

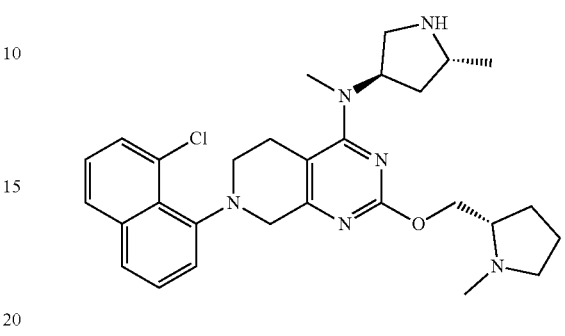

Step 5: 7-(8-chloro-1-naphthyl)-N-methyl-N-[(3R,5R)-5-methylpyrrolidin-3-yl]-2-[[(2S)-1-methylpyrrolidin-2-yl]methoxy]-6,8-dihydro-5H-pyrido[3,4-d]pyrimidin-4-amine The deprotection of Boc group was prepared in a similar fashion to Example 1 (Method 1-A), Step 5. The mixture was concentrated affording 7-(8-chloro-1-naphthyl)-N-methyl-N-[(3R,5R)-5-methylpyrrolidin-3-yl]-2-[[(2S)-1-methylpyrrolidin-2-yl]methoxy]-6,8-dihydro-5H-pyrido[3,4-d]pyrimidin-4-amine (165 mg, crude, trifluoroacetate salt) as a yellow gum, which was used in the next step without further purification. LCMS Rt=0.490 min, m/z=520.3 [M+H]$^+$.

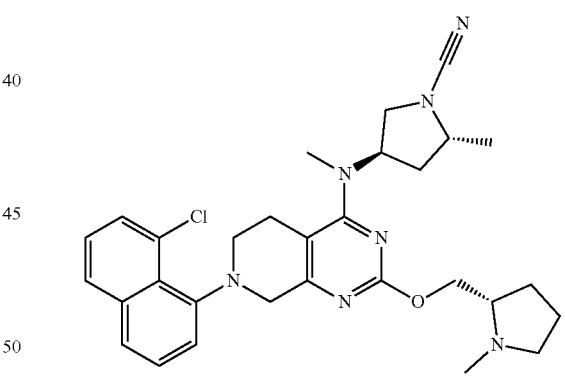

Step 6: (2R,4R)-4-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)-2-methylpyrrolidine-1-carbonitrile The substitution reaction was prepared in a similar fashion to Example 28 (Method 2-C), Step 6, substituting 7-(8-chloronaphthalen-1-yl)-N-methyl-2-(((S)-1-methylpyrrolidin-2-yl)methoxy)-N-((3R,5R)-5-methylpyrrolidin-3-yl)-5,6,7,8-tetrahydropyrido[3,4-d]pyrimidin-4-amine for N-(azetidin-3-ylmethyl)-7-(8-chloronaphthalen-1-yl)-8-fluoro-N-methyl-2-((tetrahydro-1H-pyrrolizin-7a(5H)-yl)methoxy)pyrido[4,3-d]pyrimidin-4-amine. The crude product was purified by reverse phase HPLC (column:

Phenomenex Luna 80*30 mm*3 μm; mobile phase: (water (FA)-ACN; B %: 10%-40%, 8 min) affording (2R,4R)-4-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)-2-methylpyrrolidine-1-carbonitrile (11.38 mg, 22.09%, formate salt) as a yellow oil: $^1$H NMR (400 MHz, Acetonitrile-d3) δ 7.85 (d, J=8.2 Hz, 1H), 7.68 (d, J=8.2 Hz, 1H), 7.55 (dd, J=1.2, 7.5 Hz, 1H), 7.50 (dt, J=2.4, 7.8 Hz, 1H), 7.43-7.37 (m, 1H), 7.34-7.30 (m, 1H), 4.86 (br d, J=2.8 Hz, 1H), 4.36-4.10 (m, 3H), 3.95-3.86 (m, 2H), 3.78-3.65 (m, 2H), 3.57-3.49 (m, 1H), 3.43 (td, J=7.2, 9.9 Hz, 1H), 3.28-3.15 (m, 1H), 3.14-3.06 (m, 1H), 3.05-2.99 (m, 1H), 2.95 (d, J=6.5 Hz, 3H), 2.63-2.54 (m, 2H), 2.44-2.37 (m, 3H), 2.30 (br dd, J=5.9, 7.8 Hz, 1H), 2.03-1.97 (m, 1H), 1.87-1.58 (m, 4H), 1.29 (dd, J=4.6, 6.3 Hz, 3H). LCMS Rt=2.161 min, m/z=545.3 [M+H]+.

LCMS (5 to 95% acetonitrile in water+0.1% trifluoroacetic acid over 6 mins) retention time 2.161 min, ESI+ found [M+H]=545.3.

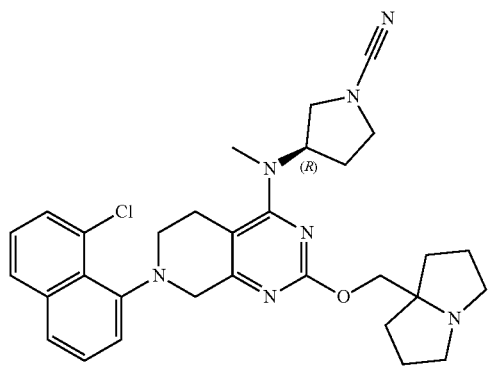

Example 39 (Method 2-C$_{11}$): (R)-3-((7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl)(methyl)amino)pyrrolidine-1-carbonitrile The substitution reaction was prepared in a similar fashion to Example 28 (Method 2-C), Step 6, substituting (R)-7-(8-chloronaphthalen-1-yl)-N-methyl-N-(pyrrolidin-3-yl)-2-((tetrahydro-1H-pyrrolizin-7a(5H)-yl)methoxy)-5,6,7,8-tetrahydropyrido[3,4-d]pyrimidin-4-amine (see Example 18 Step 2) for N-(azetidin-3-ylmethyl)-7-(8-chloronaphthalen-1-yl)-8-fluoro-N-methyl-2-((tetrahydro-1H-pyrrolizin-7a(5H)-yl)methoxy)pyrido[4,3-d]pyrimidin-4-amine. The crude product was purified by reverse phase HPLC (column: Phenomenex Luna 80*30 mm*3 μm; mobile phase: (water (FA)-ACN; B %: 5%-45%, 8 min) affording (R)-3-((7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl)(methyl)amino)pyrrolidine-1-carbonitrile (9 mg, 7.35%, formate salt) as a yellow oil: $^1$H NMR (400 MHz, Acetonitrile-d3) δ 7.87 (d, J=8.1 Hz, 1H), 7.70 (d, J=8.2 Hz, 1H), 7.58 (dd, J=1.2, 7.5 Hz, 1H), 7.52 (dt, J=3.5, 7.9 Hz, 1H), 7.45-7.38 (m, 1H), 7.37-7.29 (m, 1H), 4.95-4.77 (m, 1H), 4.25 (dd, J=3.7, 17.4 Hz, 1H), 4.06 (s, 2H), 3.84-3.76 (m, 1H), 3.75-3.65 (m, 1H), 3.64-3.52 (m, 2H), 3.49-3.34 (m, 2H), 3.32-3.16 (m, 1H), 3.16-3.03 (m, 3H), 2.98 (d, J=4.6 Hz, 3H), 2.68 (td, J=6.7, 10.2 Hz, 2H), 2.64-2.55 (m, 1H), 2.22-2.06 (m, 3H), 1.93-1.75 (m, 5H), 1.73-1.61 (m, 2H). LCMS Rt=2.172 min, m/z=557.3 [M+H]⁺.

LCMS (5 to 95% acetonitrile in water+0.1% trifluoroacetic acid over 6 mins) retention time 2.172 min, ESI+ found [M+H]=557.3.

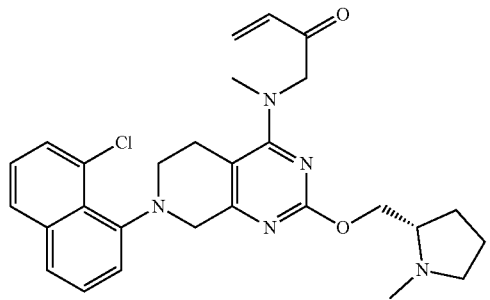 [SMILES: C=CC(=O)CN(C)c1nc(OC[C@@H]2CCCN2C)nc2c1CCN(c1cccc3cccc(Cl)c13)C2]

Example 40 (Method 1-E): (S)-1-((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)but-3-en-2-one

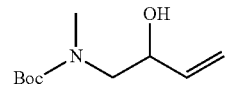

Step 1: tert-butyl (2-hydroxybut-3-en-1-yl)(methyl)carbamate

To a solution of tert-butyl N-methyl-N-(2-oxoethyl)carbamate (10 g, 57.73 mmol) in tetrahydrofuran (400 mL) was added bromo(vinyl)magnesium (1 M, 230.93 mL) at 5° C. The mixture was stirred at 25° C. for 2 h under nitrogen atmosphere. The reaction mixture was quenched with a saturated solution of ammonium chloride (400 mL) at 0° C. and extracted with ethyl acetate (3×200 mL). The combined organic layers were dried over sodium sulphate and concentrated under vacuo affording tert-butyl (2-hydroxybut-3-en-1-yl)(methyl)carbamate (12.4 g, crude) as a yellow oil, which was used in next step without further purification: $^1$H NMR (400 MHz, Chloroform-d) δ 5.78 (ddd, J=5.8, 10.7, 16.9 Hz, 1H), 5.35-5.02 (m, 2H), 4.27 (br d, J=5.3 Hz, 1H), 3.35 (br d, J=14.8 Hz, 3H), 2.95-2.77 (m, 3H), 1.40 (s, 9H).

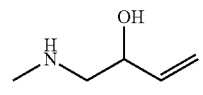

Step 2: 1-(methylamino)but-3-en-2-ol

A mixture of tert-butyl (2-hydroxybut-3-en-1-yl)(methyl) carbamate (1 g, 4.97 mmol) in hydrochloric acid/ethyl acetate (4M, 20 mL) was stirred at 25° C. for 1 h. The reaction mixture was concentrated in vacuo affording 1-(methylamino)but-3-en-2-ol (700 mg, crude, hydrochloric acid salt) as a yellow oil, which was used in next step without further purification. LCMS Rt=0.155 min, m/z=101.08 [M+H]+.

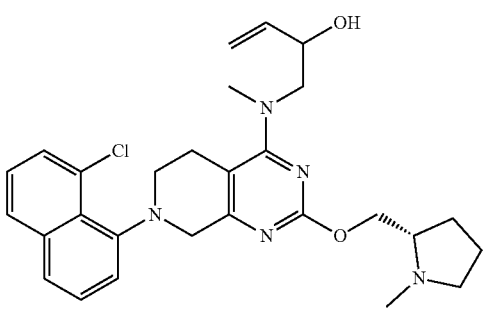 [SMILES: C=CC(O)CN(C)c1nc(OC[C@@H]2CCCN2C)nc2c1CCN(c1cccc3cccc(Cl)c13)C2]

Step 3: 1-((7-(8-chloronaphthalen-1-yl)-2-(((S)-1-methylpyrrolidin-2-yl)methoxy)-5,6,7,8-tetrahydro-pyrido[3,4-d]pyrimidin-4-yl)(methyl)amino)but-3-en-2-ol To a solution of 1-(methylamino)but-3-en-2-ol (617.65 mg, 4.49 mmol, hydrochloric acid salt) in N,N-dimethylformaldehyde (3 mL) was added triethylamine (272.51 mg, 2.69 mmol) and [7-(8-chloro-1-naphthyl)-2-[[(2S)-1-methylpyrrolidin-2-yl]methoxy]-6,8-dihydro-5H-pyrido[3,4-d]pyrimidin-4-yl]trifluoromethanesulfonate (500 mg, 897.69 μmol) at 0° C. The reaction was stirred at 0° C. for 1 h. The mixture was diluted with water (20 mL) and extracted with ethyl acetate (3×50 mL). The combined organic layers were dried over sodium sulphate and concentrated in vacuo. The resulting residue was purified by column chromatography (silica gel, 100-200 mesh, 0-100% methanol in dichloromethane) affording 1-((7-(8-chloronaphthalen-1-yl)-2-(((S)-1-methylpyrrolidin-2-yl)methoxy)-5,6,7,8-tetrahydro-pyrido[3,4-d]pyrimidin-4-yl)(methyl)amino)but-3-en-2-ol (200 mg, 43.85%) as a brown solid. LCMS Rt=2.387 min, m/z =507.24 [M+H]+.

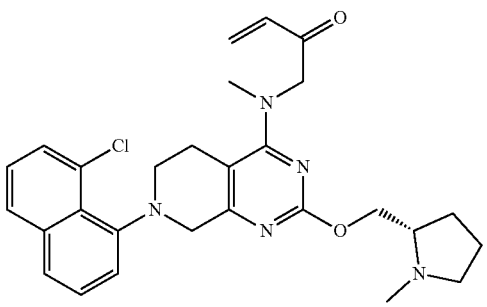 [SMILES: C=CC(=O)CN(C)c1nc(OC[C@@H]2CCCN2C)nc2c1CCN(c1cccc3cccc(Cl)c13)C2]

Step 4: (S)-1-((7-(8-chloronaphthalen-1-yl)-2-((1-methylpyrrolidin-2-yl)methoxy)-5,6,7,8-tetrahydro-pyrido[3,4-d]pyrimidin-4-yl)(methyl)amino)but-3-en-2-one To a solution of 1-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)but-3-en-2-ol (200 mg, 393.66 μmol) in dimethyl sulfoxide (2 mL) and dichloromethane (2 mL) was added 1-hydroxy-1,2-benziodoxol-3 (1H)-one-1-oxide (275.58 mg, 984.15 μmol). The mixture was stirred at 20° C. for 1 h. The reaction mixture was concentrated in vacuo and purified by reverse phase HPLC (column: Phenomenex Gemini-NX 80*40 mm*3 μm; mobile phase: water (10 mM NH$_4$HCO$_3$)-ACN; B %: 40%-70%, 8 min) affording (S)-1-((7-(8-chloronaphthalen-1-yl)-2-((1-methylpyrrolidin-2-yl)methoxy)-5,6,7,8-tetrahydro-pyrido[3,4-d]pyrimidin-4-yl)(methyl)amino)but-3-en-2-one (32.73 mg, 15.79%) as a yellow solid: $^1$H NMR (400 MHz, Acetonitrile-d3) δ 7.87 (d, J=8.2 Hz, 1H), 7.70 (d, J=7.9 Hz, 1H), 7.58 (d, J=7.5 Hz, 1H), 7.52 (t, J=7.8 Hz, 1H), 7.42 (t, J=7.7 Hz, 1H), 7.34 (d, J=7.3 Hz, 1H), 6.56-6.48 (m, 1H), 6.38-6.31 (m, 1H), 5.91 (d, J=10.8 Hz, 1H), 4.67-4.61 (m, 1H), 4.47-4.39 (m, 1H), 4.24-4.12 (m, 2H), 4.01 (dd, J=6.1, 10.7 Hz, 1H), 3.72 (d, J=17.2 Hz, 1H), 3.53 (br s, 1H), 3.33-3.22 (m, 4H), 3.14-3.07 (m, 1H), 3.03-2.98 (m, 1H), 2.72 (br d, J=15.7 Hz, 1H), 2.58-2.51 (m, 1H), 2.37 (s, 3H), 2.28-2.22 (m, 1H), 1.79 (br s, 1H), 1.74-1.69 (m, 2H), 1.63-1.56 (m, 1H). LCMS Rt=3.260 min, m/z=505.22 [M+H]+.

LCMS (5 to 95% acetonitrile in water+0.03% ammonium bicarbonate over 6 mins) retention time 3.260 min, ESI+ found [M+H]=505.22.

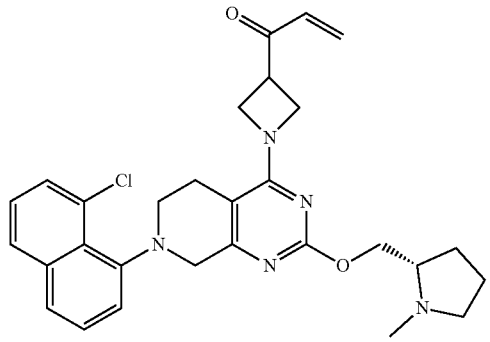 [SMILES: C=CC(=O)C1CN(c2nc(OC[C@@H]3CCCN3C)nc3c2CCN(c2cccc4cccc(Cl)c24)C3)C1]

Example 41 (Method 3-E): (S)-1-(1-(7-(8-chloronaphthalen-1-yl)-2-((1-methylpyrrolidin-2-yl)methoxy)-5,6,7,8-tetrahydropyrido[3,4-d]pyrimidin-4-yl)azetidin-3-yl)prop-2-en-1-one

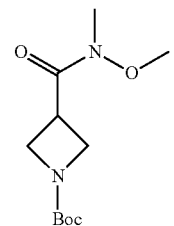 [SMILES: CON(C)C(=O)C1CN(C(=O)OC(C)(C)C)C1]

Step 1: tert-butyl 3-(methoxy(methyl)carbamoyl)azetidine-1-carboxylate

To a solution of N-methoxymethanamine hydrochloride (581.75 mg, 5.96 mmol) in dichloromethane (25 mL) was added 4-methylmorpholine (1.01 g, 9.94 mmol), 1-(tert-butoxycarbonyl)azetidine-3-carboxylic acid (1 g, 4.97 mmol), 1-(3-dimethylaminopropyl)-3-ethylcarbodiimide (1.43 g, 7.46 mmol) and 1-Hydroxybenzotriazole (1.01 g, 7.46 mmol). The mixture was stirred at 25° C. for 12 h. The mixture was diluted with water (20 mL) and extracted with ethyl acetate (3×50 mL). The combined organic layers were dried over sodium sulphate and concentrated in vacuo. The resulting residue was purified by column chromatography (silica gel, 100-200 mesh, 0-100% ethyl acetate in petroleum ether) affording tert-butyl 3-(methoxy(methyl)carbamoyl)azetidine-1-carboxylate (1.16 g, 95.54%) as a colorless oil: $^1$H NMR (400 MHz, Chloroform-d) δ 4.10-4.03 (m, 2H), 4.01-3.94 (m, 2H), 3.63-3.50 (m, 4H), 3.14 (s, 3H), 1.36 (s, 9H). LCMS Rt=1.322 min, m/z=244.14 [M+H]+.

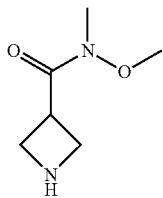

Step 2:
N-methoxy-N-methylazetidine-3-carboxamide

A mixture of tert-butyl 3-(methoxy(methyl)carbamoyl)azetidine-1-carboxylate (300 mg, 1.23 mmol) in dichloromethane (1.5 mL) and trifluoroacetic acid (0.5 mL) was stirred at 25° C. for 1 h. The reaction mixture was concentrated in vacuo affording N-methoxy-N-methylazetidine-3-carboxamide (700 mg, crude, trifluoroacetate salt) as a yellow oil, which was used in next step without further purification. LCMS Rt=0.123 min, m/z=144.09 [M+H]+.

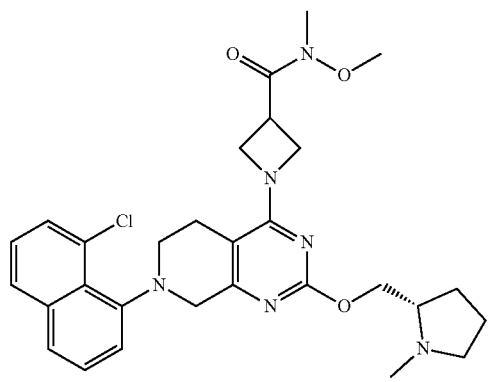 [SMILES: CON(C)C(=O)C1CN(c2nc(OC[C@@H]3CCCN3C)nc3c2CCN(c2cccc4cccc(Cl)c24)C3)C1]

Step 3: (S)-1-(7-(8-chloronaphthalen-1-yl)-2-((1-methylpyrrolidin-2-yl)methoxy)-5,6,7,8-tetrahydropyrido[3,4-d]pyrimidin-4-yl)-N-methoxy-N-methylazetidine-3-carboxamide To a solution of N-methoxy-N-methylazetidine-3-carboxamide (278.13 mg, 1.08 mmol) in N,N-dimethylformaldehyde (5 mL) was added N,N-diisopropylethylamine (278.45 mg, 2.15 mmol) and (S)-7-(8-chloronaphthalen-1-yl)-2-((1-methylpyrrolidin-2-yl)methoxy)-5,6,7,8-tetrahydropyrido[3,4-d]pyrimidin-4-yl trifluoromethanesulfonate (300 mg, 538.62 µmol) at 0° C. The mixture was stirred at 25° C. for 1 h. The mixture was diluted with water (20 mL) and extracted with ethyl acetate (3×50 mL). The combined organic layers were dried over sodium sulphate and concentrated in vacuo. The resulting residue was purified by column chromatography (silica gel, 100-200 mesh, 0-100% methanol in dichloromethane) affording (S)-1-(7-(8-chloronaphthalen-1-yl)-2-((1-methylpyrrolidin-2-yl)methoxy)-5,6,7,8-tetrahydropyrido[3,4-d]pyrimidin-4-yl)-N-methoxy-N-methylazetidine-3-carboxamide (150 mg, 50.54%) as a brown solid. LCMS Rt=0.510 min, m/z=550.25 [M+H]+.

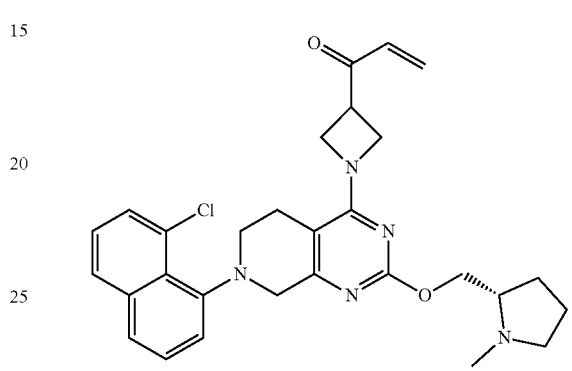

Step 4: (S)-1-(1-(7-(8-chloronaphthalen-1-yl)-2-((1-methylpyrrolidin-2-yl)methoxy)-5,6,7,8-tetrahydropyrido[3,4-d]pyrimidin-4-yl)azetidin-3-yl)prop-2-en-1-one To a solution of (S)-1-(7-(8-chloronaphthalen-1-yl)-2-((1-methylpyrrolidin-2-yl)methoxy)-5,6,7,8-tetrahydropyrido[3,4-d]pyrimidin-4-yl)-N-methoxy-N-methylazetidine-3-carboxamide (50 mg, 90.73 µmol) in tetrahydrofuran (3 mL) was added bromo(vinyl)magnesium (1 M, 362.92 uL) at −78° C. under nitrogen atmosphere. The mixture was stirred at 0° C. for 1 h under nitrogen atmosphere. The reaction mixture was quenched with a saturated solution of ammonium chloride (2 mL) at 0° C. and extracted with ethyl acetate (3×3 mL). The combined organic layers were dried over sodium sulphate and concentrated under vacuo. The resulting residue was purified by reverse phase HPLC (column: Phenomenex Luna 80*30 mm*3 µm; mobile phase: water(0.1% TFA)-ACN; B %: 15%-45%, 8 min) affording (S)-1-(1-(7-(8-chloronaphthalen-1-yl)-2-((1-methylpyrrolidin-2-yl)methoxy)-5,6,7,8-tetrahydropyrido[3,4-d]pyrimidin-4-yl)azetidin-3-yl)prop-2-en-1-one (17.95 mg, 30.98%, trifluoroacetate salt as a white solid: $^1$H NMR (400 MHz, Acetonitrile-d3) δ 7.90 (d, J=7.9 Hz, 1H), 7.76 (d, J=8.1 Hz, 1H), 7.65-7.51 (m, 2H), 7.49-7.32 (m, 2H), 6.51-6.35 (m, 1H), 6.33-6.19 (m, 1H), 6.09 (d, J=10.6 Hz, 1H), 4.77-4.63 (m, 3H), 4.62-4.53 (m, 2H), 4.30-4.05 (m, 2H), 3.92-3.67 (m, 3H), 3.60-3.53 (m, 1H), 3.10-3.01 (m, 3H), 2.95 (br d, J=3.4 Hz, 3H), 2.76 (br d, J=14.3 Hz, 2H), 2.40-2.00 (m, 4H). LCMS Rt =2.069 min, m/z=517.22 [M+H]+.

LCMS (5 to 95% acetonitrile in water+0.1% trifluoroacetic acid over 6 mins) retention time 2.069 min, ESI+ found [M+H]=517.22.

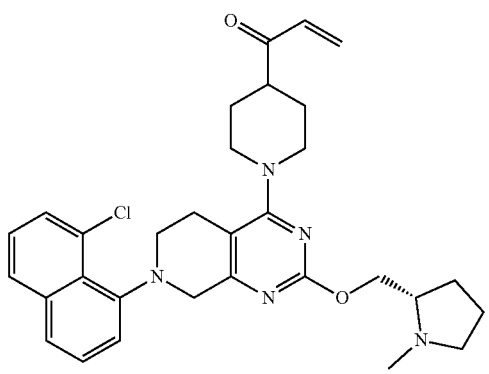 [SMILES: C=CC(=O)C1CCN(c2nc(OC[C@@H]3CCCN3C)nc3c2CCN(c2cccc4cccc(Cl)c24)C3)CC1]

Example 42 (Method 3-E1): (S)-1-(1-(7-(8-chloronaphthalen-1-yl)-2-((1-methylpyrrolidin-2-yl)methoxy)-5,6,7,8-tetrahydropyrido[3,4-d]pyrimidin-4-yl)piperidin-4-yl)prop-2-en-1-one

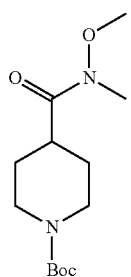 [SMILES: CON(C)C(=O)C1CCN(C(=O)OC(C)(C)C)CC1]

Step 1: tert-butyl 4-(methoxy(methyl)carbamoyl)piperidine-1-carboxylate

The amide formation was prepared in a similar fashion to Example 41 (Example 41 (Method 3-E)), Step 1, substituting 1-tert-butoxycarbonylpiperidine-4-carboxylic acid for 1-(tert-butoxycarbonyl)azetidine-3-carboxylic acid. The crude product was concentrated in vacuo affording tert-butyl 4-(methoxy(methyl)carbamoyl)piperidine-1-carboxylate (2.4 g, crude) as a brown oil, which was used in next step without further purification: ¹H NMR (400 MHz, Dimethylsulfoxide-d6) δ 3.9-4.0 (m, 2H), 3.68 (s, 3H), 3.09 (s, 3H), 2.7-2.9 (m, 3H), 1.63 (br d, 2H, J=11.3 Hz), 1.4-1.4 (m, 9H), 1.35 (br d, 2H, J=3.9 Hz). LCMS Rt=0.659 min, m/z=272.2 [M+H]+.

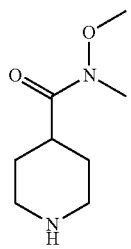

Step 2: N-methoxy-N-methylpiperidine-4-carboxamide

The deprotection of Boc group was prepared in a similar fashion to Example 41 (Method 3-E), Step 2, the reaction mixture was concentrated to dryness in vacuo affording N-methoxy-N-methylpiperidine-4-carboxamide (650 mg, crude, hydrochloric acid salt) as a white solid, which was used in the next step without further purification: ¹H NMR (400 MHz, dimethylsulfoxide-d6) δ 3.68 (s, 3H), 3.23 (br d, J=12.7 Hz, 2H), 3.09 (s, 3H), 3.01-2.86 (m, 3H), 1.87-1.68 (m, 4H).

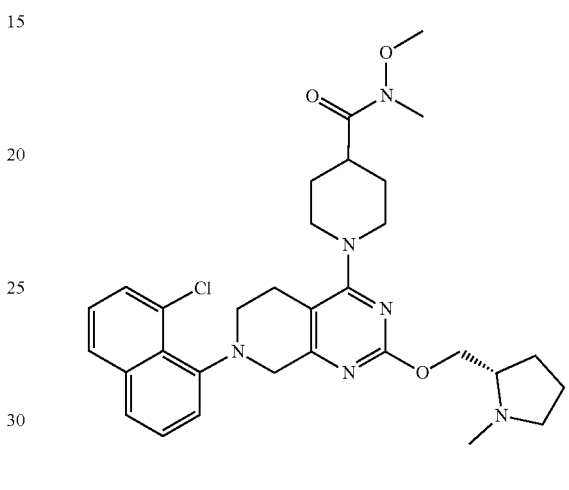

Step 3: (S)-1-(7-(8-chloronaphthalen-1-yl)-2-((1-methylpyrrolidin-2-yl)methoxy)-5,6,7,8-tetrahydropyrido[3,4-d]pyrimidin-4-yl)-N-methoxy-N-methylpiperidine-4-carboxamide The substitution reaction was prepared in a similar fashion to Example 41 (Method 3-E), Step 3, the crude product was purified by reverse phase HPLC (column: Phenomenex Luna 80*30 mm*3 μm; mobile phase: [water(0.1% TFA)-ACN]; B %: 15%-55%, 8 min) affording (S)-1-(7-(8-chloronaphthalen-1-yl)-2-((1-methylpyrrolidin-2-yl)methoxy)-5,6,7,8-tetrahydropyrido[3,4-d]pyrimidin-4-yl)-N-methoxy-N-methylpiperidine-4-carboxamide (38 mg, 10.49%, trifluoroacetate salt) as a yellow solid. LCMS Rt=0.544 min, m/z=578.3 [M+H]+.

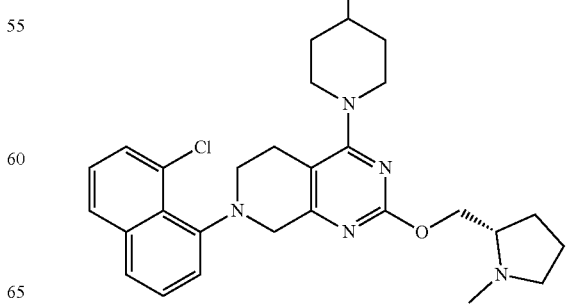

Step 4: (S)-1-(1-(7-(8-chloronaphthalen-1-yl)-2-((1-methylpyrrolidin-2-yl)methoxy)-5,6,7,8-tetrahydropyrido[3,4-d]pyrimidin-4-yl)piperidin-4-yl)prop-2-en-1-one The Grignard reaction was prepared in a similar fashion to Example 41 (Method 3-E), Step 4. The crude product was purified by reverse phase HPLC (column: Phenomenex Luna 80*30 mm*3 μm; mobile phase: (water(0.1% TFA)-ACN; B %: 25%-55%, 8 min) affording (S)-1-(1-(7-(8-chloronaphthalen-1-yl)-2-((1-methylpyrrolidin-2-yl)methoxy)-5,6,7,8-tetrahydropyrido[3,4-d]pyrimidin-4-yl)piperidin-4-yl)prop-2-en-1-one (8.87 mg, 5.43%, trifluoroacetate salt) as a yellow solid: $^1$H NMR (400 MHz, Acetonitrile-d3) δ 7.86 (d, J=8.0 Hz, 1H), 7.72 (d, J=8.1 Hz, 1H), 7.57 (br d, J=7.4 Hz, 1H), 7.51 (t, J=7.8 Hz, 1H), 7.41 (t, J=7.8 Hz, 1H), 7.34 (dd, J=3.1, 7.3 Hz, 1H), 6.55-6.45 (m, 1H), 6.34-6.26 (m, 1H), 5.86 (d, J=10.6 Hz, 1H), 4.71-4.60 (m, 2H), 4.45-4.29 (m, 3H), 3.81 (br d, J=17.8 Hz, 1H), 3.69 (br d, J=5.1 Hz, 2H), 3.52 (br d, J=11.1 Hz, 1H), 3.34-3.19 (m, 7H), 2.91 (s, 3H), 2.59 (br d, J=14.3 Hz, 1H), 2.34-2.22 (m, 1H), 2.14-1.96 (m, 4H), 1.81-1.68 (m, 1H), 1.60 (q, J=11.8 Hz, 1H). LCMS Rt=2.213 min, m/z=545.3 [M+H]+.

LCMS (5 to 95% acetonitrile in water+0.1% trifluoroacetic acid over 6 mins) retention time 2.213 min, ESI+ found [M+H]=545.3

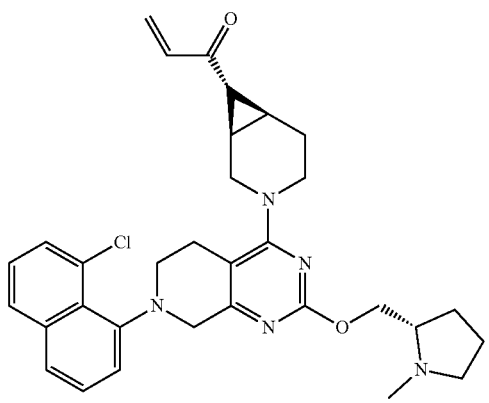

Example 43 (Method 3-E2): 1-((1R,6S,7R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3-azabicyclo[4.1.0]heptan-7-yl)prop-2-en-1-one and 1-((1S,6R,7S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3-azabicyclo[4.1.0]heptan-7-yl)prop-2-en-1-one

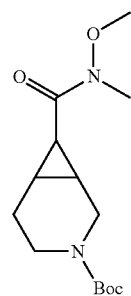 [SMILES: CON(C)C(=O)C1C2CCN(C(=O)OC(C)(C)C)CC21]

Step 1: tert-butyl 7-(methoxy(methyl)carbamoyl)-3-azabicyclo[4.1.0]heptane-3-carboxylate The amide formation was prepared in a similar fashion to Example 41 (Method 3-E), Step 1, substituting 3-tert-butoxycarbonyl-3-azabicyclo[4.1.0]heptane-7-carboxylic acid for 1-(tert-butoxycarbonyl)azetidine-3-carboxylic acid. The crude product was purified by column chromatography (silica gel, 100-200 mesh, 0-100% ethyl acetate in petroleum ether) affording tert-butyl 7-(methoxy(methyl)carbamoyl)-3-azabicyclo[4.1.0]heptane-3-carboxylate (700 mg, 99.00%). LCMS Rt=1.701 min, m/z=284.1 [M+H]+.

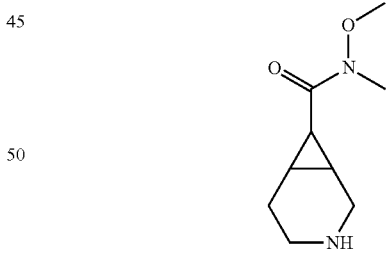

Step 2: N-methoxy-N-methyl-3-azabicyclo[4.1.0]heptane-7-carboxamide

The deprotection of Boc group was prepared in a similar fashion to Example 41 (Method 3-E), Step 2, the reaction mixture was concentrated to dryness in vacuo affording N-methoxy-N-methyl-3-azabicyclo[4.1.0]heptane-7-carboxamide (700 mg, crude, hydrochloric acid salt) as a colorless oil, which was used in next step without further purification. LCMS Rt=0.185 min, m/z =184.1 [M+H]+.

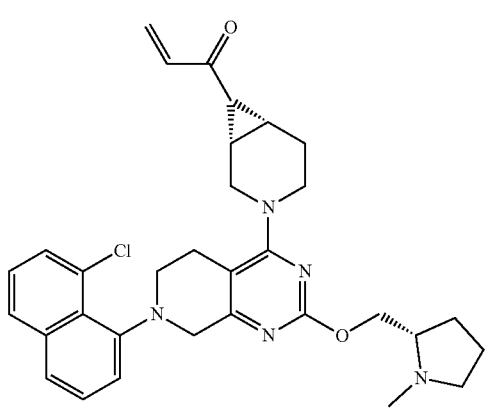

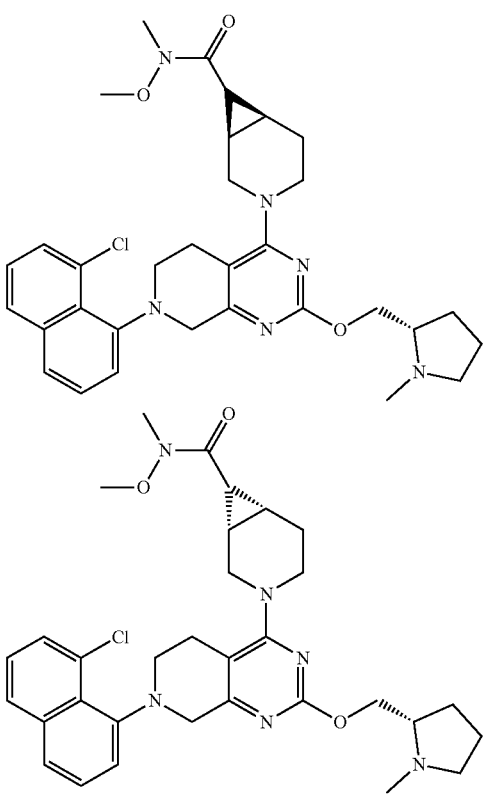

Step 3: (1R,6S,7R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-N-methoxy-N-methyl-3-azabicyclo[4.1.0]heptane-7-carboxamide and (1S,6R,7S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-N-methoxy-N-methyl-3-azabicyclo[4.1.0]heptane-7-carboxamide The substitution reaction was prepared in a similar fashion to Example 41 (Method 3-E), Step 3. The crude product was purified by reverse phase HPLC (column: Phenomenex luna C18 250*50 mm*10 μm; mobile phase: (water(0.1% TFA)-ACN; B %: 20%-50%, 10 min) affording 3-[7-(8-chloro-1-naphthyl)-2-[[(2S)-1-methylpyrrolidin-2-yl]methoxy]-6,8-dihydro-5H-pyrido[3,4-d]pyrimidin-4-yl]-N-methoxy-N-methyl-3-azabicyclo[4.1.0]heptane-7-carboxamide (250 mg, 50%, trifluoroacetate salt) as a yellow solid. The racemic material was further purified by Super Critical Fluid Chromatography (SFC) to give arbitrarily assigned:

(1R,6S,7R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-N-methoxy-N-methyl-3-azabicyclo[4.1.0]heptane-7-carboxamide (Peak 1, retention time=2.900 min) (75 mg, 14.06%) as a yellow solid. LCMS Rt =0.644 min, m/z=590.3 [M+H]+.

(1S,6R,7S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-N-methoxy-N-methyl-3-azabicyclo[4.1.0]heptane-7-carboxamide (Peak 2, retention time=4.561 min) (100 mg, 18.75%) as a yellow solid. LCMS Rt=0.644 min, m/z=590.3 [M+H]+.

SFC (column: Phenomenex-Cellulose-2 (250 mm*30 mm, 10 μm); mobile phase: [0.1% NH$_3$H$_2$O in MeOH]; B %: 50%-50%, 8 min).

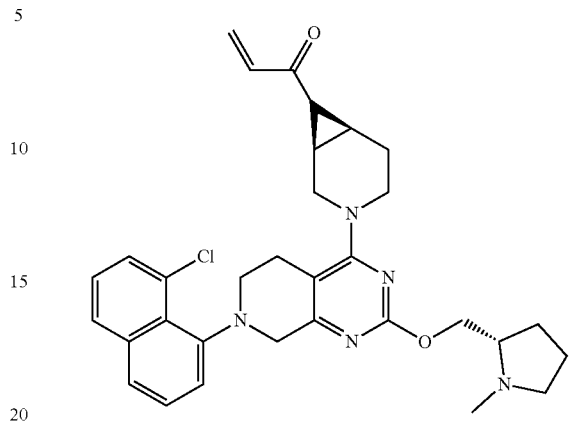

Step 4: 1-((1R,6S,7R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3-azabicyclo[4.1.0]heptan-7-yl)prop-2-en-1-one The Grignard reaction was prepared in a similar fashion to Example 41 (Method 3-E), Step 4. The crude product was purified by reverse phase HPLC (column: Phenomenex Luna 80*30 mm*3 μm; mobile phase: (water(0.2% FA)-ACN; B %: 5%-45%, 8 min) affording 1-((1R,6S,7R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3-azabicyclo[4.1.0]heptan-7-yl)prop-2-en-1-one (5.24 mg, 16.27%, formate salt) as a white solid: $^1$H NMR (400 MHz, Acetonitrile-d3) δ 7.93-7.82 (m, 1H), 7.71 (t, J=7.4 Hz, 1H), 7.61-7.48 (m, 2H), 7.45-7.30 (m, 2H), 6.55-6.44 (m, 1H), 6.34-6.18 (m, 1H), 5.91-5.80 (m, 1H), 4.35-4.21 (m, 2H), 4.19-4.06 (m, 2H), 3.85-3.66 (m, 2H), 3.62-3.49 (m, 2H), 3.28-3.17 (m, 1H), 3.11 (dt, J=2.8, 10.9 Hz, 1H), 3.06-3.01 (m, 1H), 2.91 (ddd, J=6.4, 9.8, 13.6 Hz, 1H), 2.65-2.54 (m, 2H), 2.48 (br t, J=4.2 Hz, 1H), 2.41 (s, 3H), 2.25-2.22 (m, 2H), 2.16-2.07 (m, 2H), 2.02-1.99 (m, 1H), 1.93-1.84 (m, 2H), 1.77-1.68 (m, 2H). LCMS Rt=2.204 min, m/z=557.3 [M+H]+.

LCMS (5 to 95% acetonitrile in water+0.1% trifluoroacetic acid over 6 mins) retention time 2.204 min, ESI+ found [M+H]=557.3.

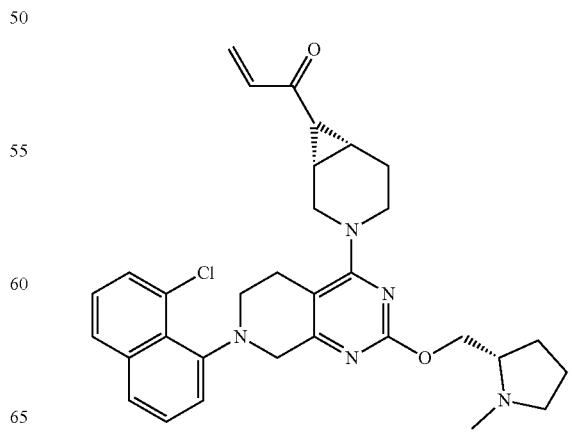

Step 4: 1-((1S,6R,7S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3-azabicyclo[4.1.0]heptan-7-yl)prop-2-en-1-one The Grignard reaction was prepared in a similar fashion to Example 41 (Method 3-E), Step 4. The crude product was purified by reverse phase HPLC (column: Phenomenex Luna 80*30 mm*3 μm; mobile phase: (water(0.2% FA)-ACN; B %: 5%-45%, 8 min) affording 1-((1S,6R,7S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3-azabicyclo[4.1.0]heptan-7-yl)prop-2-en-1-one (3.64 mg, 11.34%, formate salt) as a white solid: $^1$H NMR (400 MHz, Acetonitrile-d3) δ 7.89 (br d, J=8.19 Hz, 1H), 7.68-7.75 (m, 1H), 7.48-7.62 (m, 2H), 7.30-7.47 (m, 2H), 6.43-6.56 (m, 1H), 6.19-6.37 (m, 1H), 5.81-5.93 (m, 1H), 4.22-4.40 (m, 2H), 4.08-4.20 (m, 2H), 3.67-3.88 (m, 2H), 3.49-3.64 (m, 2H), 3.18-3.31 (m, 1H), 3.08-3.17 (m, 1H), 3.06 (br d, J=5.99 Hz, 1H), 2.92 (ddd, J=13.78, 9.99, 5.93 Hz, 1H), 2.60-2.71 (m, 2H), 2.52-2.59 (m, 1H), 2.44-2.51 (m, 3H), 2.25-2.34 (m, 2H), 2.02-2.16 (m, 2H), 1.83-1.96 (m, 2H), 1.65-1.83 (m, 3H).

LCMS Rt=2.202 min, m/z=557.3 [M+H]+. LCMS (5 to 95% acetonitrile in water+0.1% trifluoroacetic acid over 6 mins) retention time 2.202 min, ESI+ found [M+H]=557.3.

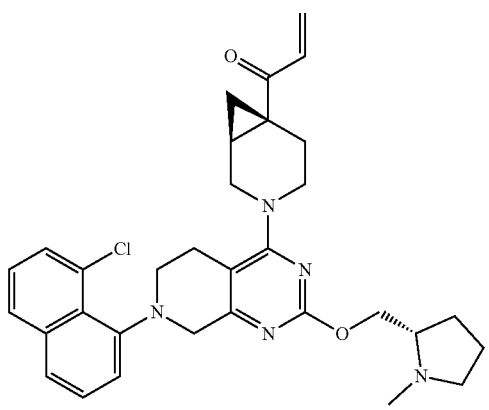

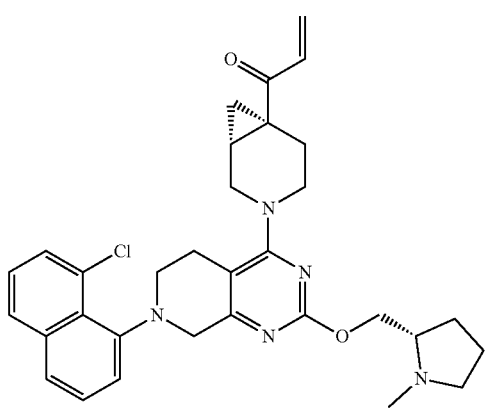

Example 44 (Method 3-E3): 1-((1S,6R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3-azabicyclo[4.1.0]heptan-6-yl)prop-2-en-1-one and 1-((1R,6S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3-azabicyclo[4.1.0]heptan-6-yl)prop-2-en-1-one

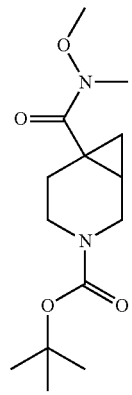 [SMILES: CON(C)C(=O)C12CCN(C(=O)OC(C)(C)C)CC1C2]

Step 1: tert-butyl 6-[methoxy(methyl)carbamoyl]-3-azabicyclo[4.1.0]heptane-3-carboxylate The amide formation was prepared in a similar fashion to Example 41 (Method 3-E), Step 1, substituting 3-(tert-butoxycarbonyl)-3-azabicyclo[4.1.0]heptane-6-carboxylic acid for 1-(tert-butoxycarbonyl)azetidine-3-carboxylic acid. The crude product was purified by column chromatography (silica gel, 100-200 mesh, 0-100% ethyl acetate in petroleum ether) affording tert-butyl 6-[methoxy(methyl)carbamoyl]-3-azabicyclo[4.1.0]heptane-3-carboxylate (1.1 g, 94.28%) as a colorless oil: $^1$H NMR (400 MHz, Chloroform-d) δ 3.72 (s, 3H), 3.42-3.34 (m, 1H), 3.22-3.17 (m, 3H), 3.00-2.85 (m, 3H), 2.09-1.84 (m, 2H), 1.51-1.42 (m, 10H), 1.31-1.11 (m, 1H), 0.53 (dd, J=5.3, 6.1 Hz, 1H). LCMS Rt=0.194 min, m/z=284.2 [M+H]+.

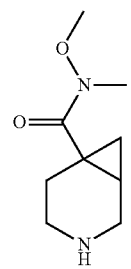

Step 2: N-methoxy-N-methyl-3-azabicyclo[4.1.0]heptane-6-carboxamide

The deprotection of Boc group was prepared in a similar fashion to Example 41 (Method 3-E), Step 2. The reaction mixture was concentrated to dryness in vacuo affording N-methoxy-N-methyl-3-azabicyclo[4.1.0]heptane-6-carboxamide (700 mg, crude, hydrochloric acid salt) as a white solid, which was used in next step without further purification. LCMS Rt=0.175 min, m/z =184.1 [M+H]+.

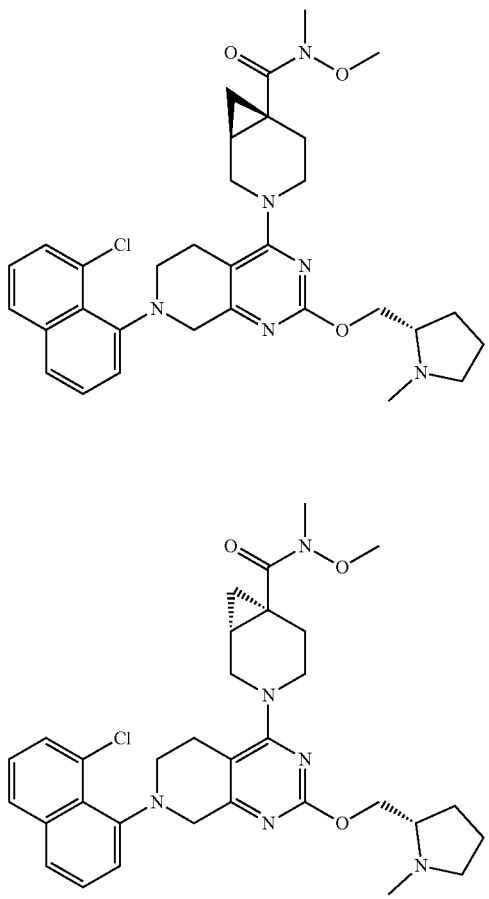

Step 3: (1S,6R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-N-methoxy-N-methyl-3-azabicyclo[4.1.0]heptane-6-carboxamide and (1R,6S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-N-methoxy-N-methyl-3-azabicyclo[4.1.0]heptane-6-carboxamide The substitution reaction was prepared in a similar fashion to Example 41 (Method 3-E), Step 3. The crude product was purified by reverse phase HPLC (column: Kromasil C18 (250*50 mm*10 μm); mobile phase: (water (10 mM NH₄HCO₃)-ACN; B %: 50%-80%, 10 min) affording 3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-N-methoxy-N-methyl-3-azabicyclo[4.1.0]heptane-6-carboxamide (400 mg, 85.33%) as a white solid. The racemic material was further purified by SFC to give arbitrarily assigned:

(1S,6R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-N-methoxy-N-methyl-3-azabicyclo[4.1.0]heptane-6-carboxamide (Peak 1, retention time=3.054 min) (50 mg, 10.67%) as a yellow solid. LCMS Rt=0.965 min, m/z=590.28 [M+H]+.

(1R,6S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-N-methoxy-N-methyl-3-azabicyclo[4.1.0]heptane-6-carboxamide (Peak 2, retention time=4.201 min) (50 mg, 10.67%) as a yellow solid. LCMS Rt=0.965 min, m/z=590.28 [M+H]+.

SFC (column: Phenomenex-Cellulose-2 (250 mm*30 mm, 10 μm); mobile phase: ([0.1% NH₃H₂O in MeOH]; B %: 60%-60%, 11 min).

Step 4: 1-((1S,6R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3-azabicyclo[4.1.0]heptan-6-yl)prop-2-en-1-one The Grignard reaction was prepared in a similar fashion to Example 41 (Method 3-E), Step 4. The crude product was purified by reverse phase HPLC (column: Phenomenex Luna 80*30 mm*3 μm; mobile phase: (water(0.2% FA)-ACN; B %: 15%-55%, 8 min) affording 1-((1S,6R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3-azabicyclo[4.1.0]heptan-6-yl)prop-2-en-1-one (2 mg, 9.69%, formate salt) as a yellow solid: ¹H NMR (400 MHz, Acetonitrile-d3) δ 7.89 (br d, J=8.19 Hz, 1H), 7.68-7.74 (m, 1H), 7.56-7.61 (m, 1H), 7.48-7.55 (m, 1H), 7.40-7.46 (m, 1H), 7.28-7.39 (m, 1H), 6.51-6.62 (m, 1H), 6.24-6.32 (m, 1H), 5.67-5.74 (m, 1H), 4.28-4.36 (m, 1H), 4.21-4.28 (m, 1H), 4.08-4.16 (m, 1H), 3.71-3.85 (m, 2H), 3.60-3.69 (m, 1H), 3.46-3.59 (m, 2H), 3.39 (s, 1H), 3.32-3.45 (m, 1H), 3.18-3.29 (m, 1H), 3.01-3.17 (m, 2H), 2.86-2.96 (m, 1H), 2.75-2.84 (m, 1H), 2.49-2.65 (m, 2H), 2.42 (d, J=3.79 Hz, 2H), 2.00-2.07 (m, 2H), 1.63-1.91 (m, 5H), 1.50 (td, J=8.80, 4.89 Hz, 1H), 0.99-1.20 (m, 1H). LCMS Rt=2.198 min, m/z=557.3 [M+H]⁺.

LCMS (5 to 95% acetonitrile in water+0.1% trifluoroacetic acid over 6 mins) retention time 2.198 min, ESI+ found [M+H]=557.3.

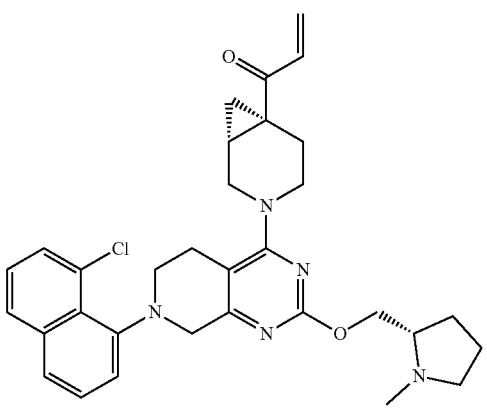 [SMILES: C=CC(=O)[C@@]12CCN(c3nc(OC[C@@H]4CCCN4C)nc4c3CCN(c3cccc5cccc(Cl)c35)C4)C[C@@H]1C2]

Step 4: 1-((1R,6S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3-azabicyclo[4.1.0]heptan-6-yl)prop-2-en-1-one The Grignard reaction was prepared in a similar fashion to Example 41 (Method 3-E), Step 4. The crude product was purified by reverse phase HPLC (column: Phenomenex Luna 80*30 mm*3 μm; mobile phase: (water(0.2% FA)-ACN; B %: 15%-45%, 8 min) affording 1-((1R,6S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3-azabicyclo[4.1.0]heptan-6-yl)prop-2-en-1-one (5 mg, 19.08%, formate salt) as a white solid: $^1$H NMR (400 MHz, Acetonitrile-d3) δ 7.87 (d, J=8.13 Hz, 1H), 7.70 (t, J=6.69 Hz, 1H), 7.47-7.60 (m, 2H), 7.39-7.45 (m, 1H), 7.28-7.38 (m, 1H), 6.51-6.61 (m, 1H), 6.22-6.32 (m, 1H), 5.66-5.73 (m, 1H), 4.32-4.39 (m, 1H), 4.20-4.30 (m, 1H), 4.17 (dd, J=10.94, 5.94 Hz, 1H), 3.91-4.12 (m, 1H), 3.69-3.83 (m, 2H), 3.60-3.67 (m, 1H), 3.48-3.57 (m, 1H), 3.03-3.28 (m, 4H), 2.91 (ddd, J=13.41, 10.98, 4.88 Hz, 1H), 2.67-2.83 (m, 2H), 2.56 (br d, J=14.63 Hz, 1H), 2.46 (d, J=1.75 Hz, 3H), 2.32-2.38 (m, 2H), 1.99-2.06 (m, 2H), 1.68-1.87 (m, 3H), 1.49 (td, J=8.91, 4.82 Hz, 1H), 1.00-1.18 (m, 1H). LCMS Rt=2.207 min, m/z=557.26 [M+H]+.

LCMS (5 to 95% acetonitrile in water+0.1% trifluoroacetic acid over 6 mins) retention time 2.207 min, ESI+ found [M+H]=557.26.

Example 45 (Method 3-E4): 1-((1R,5S,6R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3-azabicyclo[3.1.0]hexan-6-yl)prop-2-en-1-one

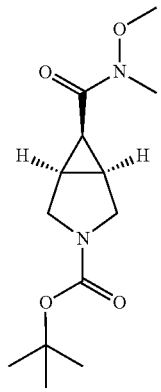 [SMILES: CON(C)C(=O)[C@@H]1[C@@H]2CN(C(=O)OC(C)(C)C)C[C@@H]21]

Step 1: (1R,5S,6S)-tert-butyl 6-(methoxy(methyl)carbamoyl)-3-azabicyclo[3.1.0]hexane-3-carboxylate The amide formation was prepared in a similar fashion to Example 41 (Method 3-E), Step 1, substituting (1S,5R)-3-tert-butoxycarbonyl-3-azabicyclo[3.1.0]hexane-6-carboxylic acid for 1-(tert-butoxycarbonyl)azetidine-3-carboxylic acid. The crude product was purified by column chromatography (silica gel, 100-200 mesh, 0-100% ethyl acetate in petroleum ether) affording (1R,5S,6S)-tert-butyl 6-(methoxy(methyl)carbamoyl)-3-azabicyclo[3.1.0]hexane-3-carboxylate (4.7 g, 98.78%) as a yellow oil: $^1$H NMR (400 MHz, Chloroform-d) δ 3.64 (br s, 3H), 3.33 (br s, 2H), 3.14-3.01 (m, 2H), 2.79 (s, 3H), 1.89-1.74 (m, 3H), 1.35 (s, 9H). LCMS Rt=0.481 min, m/z=270.16 [M+H]+.

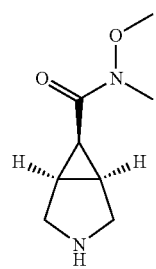

Step 2: (1R,5S,6S)—N-methoxy-N-methyl-3-azabicyclo[3.1.0]hexane-6-carboxamide

The deprotection of Boc group was prepared in a similar fashion to Example 41 (Method 3-E), Step 2. The reaction mixture was concentrated in vacuo affording (1R,5S,6S)—N-methoxy-N-methyl-3-azabicyclo[3.1.0]hexane-6-carboxamide (400 mg, crude, hydrochloric acid salt) as a brown solid, which was used in the next step without further purification. LCMS Rt=0.107 min, m/z=170.11 [M+H]+.

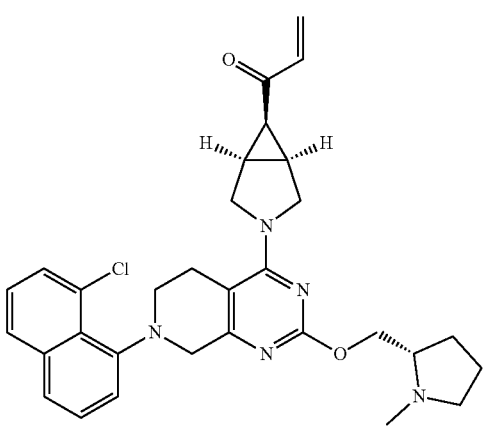

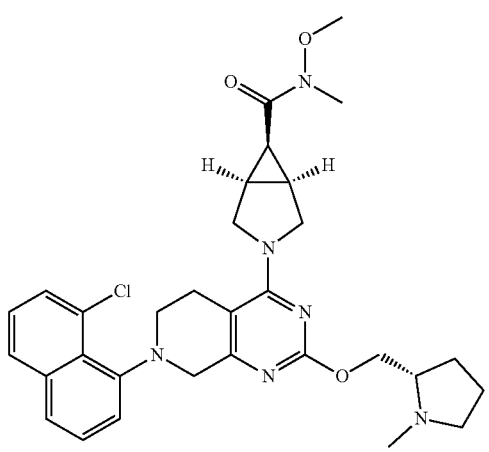 [SMILES: CON(C)C(=O)[C@@H]1[C@@H]2CN(c3nc(OC[C@@H]4CCCN4C)nc4c3CCN(c3cccc5cccc(Cl)c35)C4)C[C@@H]21]

Step 3: (1R,5S,6S)-3-(7-(8-chloronaphthalen-1-yl)-
2-(((S)-1-methylpyrrolidin-2-yl)methoxy)-5,6,7,8-
tetrahydropyrido[3,4-d]pyrimidin-4-yl)-N-methoxy-
N-methyl-3-azabicyclo[3.1.0]hexane-6-carboxamide The substitution reaction was prepared in a similar fashion to Example 41 (Method 3-E), Step 3. The crude product was purified by reverse phase HPLC (column: Waters Xbridge BEH C18 250*50 mm*10 μm; mobile phase: (water(NH$_4$HCO$_3$)-ACN; B %: 30%-70%, 10 min) affording (1R,5S,6S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-N-methoxy-N-methyl-3-azabicyclo[3.1.0]hexane-6-carboxamide (300 mg, 75.00%) as a yellow solid. LCMS Rt=0.900 min, m/z=576.26 [M+H]+.

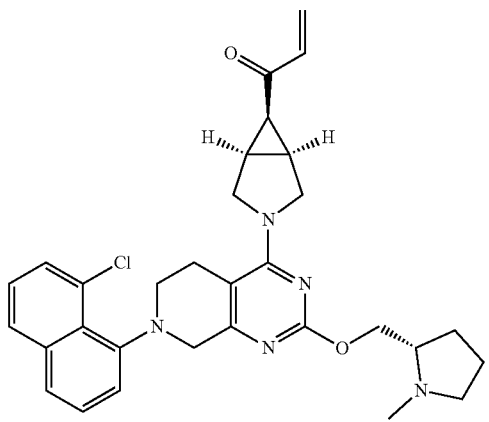 [SMILES: C=CC(=O)[C@@H]1[C@@H]2CN(c3nc(OC[C@@H]4CCCN4C)nc4c3CCN(c3cccc5cccc(Cl)c35)C4)C[C@@H]21]

Step 4: 1-((1R,5S,6R)-3-(7-(8-chloronaphthalen-1-
yl)-2-(((S)-1-methylpyrrolidin-2-yl)methoxy)-5,6,7,
8-tetrahydropyrido[3,4-d]pyrimidin-4-yl)-3-azabicy-
clo[3.1.0]hexan-6-yl)prop-2-en-1-one The Grignard reaction was prepared in a similar fashion to Example 41 (Method 3-E), Step 4. The resulting residue was purified by reverse phase HPLC (column: Phenomenex Luna 80*30 mm*3 μm; mobile phase: [water (FA)-ACN]; B %: 1%-35%, 8 min) affording 1-((1R,5S,6R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-

3-azabicyclo[3.1.0]hexan-6-yl)prop-2-en-1-one (2.52 mg, 99.55%, formate salt) as a yellow oil: $^1$H NMR (400 MHz, Acetonitrile-d3) δ 8.34 (s, 1H), 7.87 (dd, J=0.7, 8.1 Hz, 1H), 7.69 (d, J=8.0 Hz, 1H), 7.57 (dd, J=1.0, 7.4 Hz, 1H), 7.52 (t, J=7.8 Hz, 1H), 7.45-7.39 (m, 1H), 7.32 (d, J=7.4 Hz, 1H), 6.37-6.32 (m, 2H), 5.94 (dd, J=4.3, 7.6 Hz, 1H), 4.33-4.26 (m, 2H), 4.15-4.09 (m, 2H), 4.02 (d, J=11.4 Hz, 1H), 3.82 (dd, J=4.0, 11.4 Hz, 1H), 3.71 (d, J=16.9 Hz, 1H), 3.60 (dd, J=4.0, 11.3 Hz, 1H), 3.56-3.49 (m, 1H), 3.23 (ddd, J=5.6, 9.9, 15.3 Hz, 1H), 3.10-3.02 (m, 2H), 2.77-2.65 (m, 2H), 2.44 (s, 3H), 2.18-2.13 (m, 2H), 2.09-2.05 (m, 1H), 2.04-1.99 (m, 1H), 1.84 (br s, 4H). LCMS Rt=2.066 min, m/z=543.24 [M+H]+.

LCMS (5 to 95% acetonitrile in water+0.1% trifluoroacetic acid over 6 mins) retention time 2.066 min, ESI+ found [M+H]=543.24.

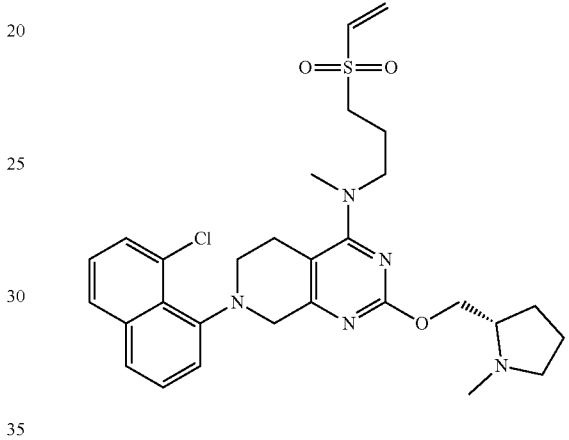

Example 46 (Method 4-V): (S)-7-(8-chloronaphtha-
len-1-yl)-N-methyl-2-((1-methylpyrrolidin-2-yl)
methoxy)-N-(3-(vinylsulfonyl)propyl)-5,6,7,8-tetra-
hydropyrido[3,4-d]pyrimidin-4-amine

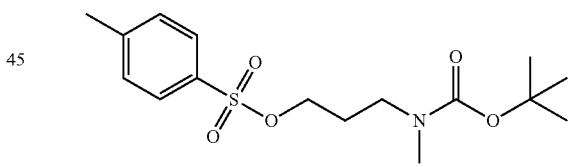

Step 1:
3-((tert-butoxycarbonyl)(methyl)amino)propyl
4-methylbenzenesulfonate

To a solution of tert-butyl N-(3-hydroxypropyl)-N-methyl-carbamate (2 g, 10.57 mmol) in dichloromethane (20 mL) was added triethylamine (2.14 g, 21.14 mmol), N,N-dimethylpyridin-4-amine (64.55 mg, 528.40 μmol) and a solution of 4-methylbenzene-1-sulfonyl chloride (2.01 g, 10.57 mmol) in dichloromethane (10 mL) at 0° C. The reaction mixture was stirred at 30° C. for 2 h. The reaction mixture was quenched with 0.5 M hydrochloric acid (300 mL) and extracted with ethyl acetate (3×300 mL). The combined organic layers were dried over sodium sulphate and concentrated to dryness in vacuo affording 3-((tert-butoxycarbonyl)(methyl)amino)propyl 4-methylbenzenesulfonate (3.1 g, crude) as a yellow oil, which was used in the next step without further purification. LCMS Rt=0.652 min, m/z=343.2 [M+H]+.

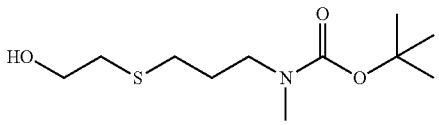 [SMILES: CN(CCCSCCO)C(=O)OC(C)(C)C]

Step 2: tert-butyl (3-((2-hydroxyethyl)thio)propyl)(methyl)carbamate

To a solution of 3-((tert-butoxycarbonyl)(methyl)amino) propyl 4-methylbenzenesulfonate (2.63 g, 7.65 mmol) in toluene (26 mL) was added 1,8-diazabicyclo[5.4.0]undec-7-ene (1.75 g, 11.47 mmol) and 2-sulfanylethanol (896.00 mg, 11.47 mmol). The mixture was stirred at 30° C. for 12 h. The reaction mixture was diluted with water (30 ml) and extracted with ethyl acetate (3×20 mL). The combined organic layers were washed with brine (20 mL), dried over sodium sulphate, filtered and concentrated to dryness in vacuo. The resulting residue was purified by column chromatography (silica gel, 100-200 mesh, 0-100% ethyl acetate in petroleum ether) affording tert-butyl (3-((2-hydroxyethyl)thio)propyl)(methyl)carbamate (1.5 g, 78.68%) as a colorless oil. LCMS Rt=0.581 min m/z=249.1 [M+H]+.

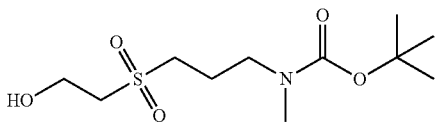 [SMILES: CN(CCCS(=O)(=O)CCO)C(=O)OC(C)(C)C]

Step 3: tert-butyl (3-((2-hydroxyethyl)sulfonyl)propyl)(methyl)carbamate

To a solution of tert-butyl (3-((2-hydroxyethyl)thio)propyl)(methyl)carbamate (1.5 g, 6.02 mmol) in methanol (30 mL) and tetrahydrofuran (30 mL) was added a solution of potassium peroxomonosulfate (14.79 g, 24.06 mmol) in water (30 mL). The mixture was stirred at 30° C. for 2 h. The reaction mixture was quenched with a saturated solution of sodium sulfite (200 mL) at 0° C. and concentrated in vacuo to remove methanol and tetrahydrofuran, then extracted with ethyl acetate (2×100 mL). The combined organic layers were washed with brine (2×50 mL), dried over sodium sulphate, and concentrated in vacuo affording tert-butyl (3-((2-hydroxyethyl)sulfonyl)propyl)(methyl)carbamate (1.6 g, crude) as a colorless oil, which was used in the next step without further purification: ¹H NMR (400 MHz, Chloroform-d) δ 4.12-4.04 (m, 2H), 3.39-3.33 (m, 2H), 3.23-3.17 (m, 2H), 3.15-3.07 (m, 2H), 2.85 (s, 3H), 2.11-2.04 (m, 2H), 1.44 (s, 9H).

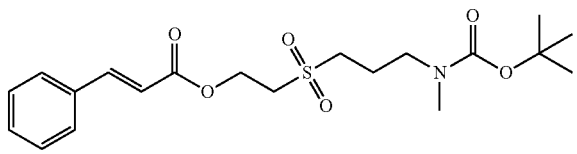 [SMILES: CN(CCCS(=O)(=O)CCOC(=O)/C=C/c1ccccc1)C(=O)OC(C)(C)C]

Step 4: 2-((3-((tert-butoxycarbonyl)(methyl)amino) propyl)sulfonyl)ethyl cinnamate To a solution of tert-butyl (3-((2-hydroxyethyl)sulfonyl) propyl)(methyl)carbamate (1.6 g, 5.69 mmol), (E)-3-phenylprop-2-enoic acid (842.51 mg, 5.69 mmol), and N,N-dimethylpyridin-4-amine (69.47 mg, 568.65 µmol) in dichloromethane (20 mL) was added N-(3-dimethylaminopropyl)-N-ethylcarbodiimide (1.31 g, 6.82 mmol). The mixture was stirred at 30° C. for 12 h. The reaction mixture was concentrated in vacuo and the crude product was purified by column chromatography (silica gel, 100-200 mesh, 0-100% ethyl acetate in petroleum ether) affording 2-((3-((tert-butoxycarbonyl)(methyl)amino)propyl)sulfonyl)ethyl cinnamate (2.2 g, 94.01%) as a yellow solid. LCMS Rt=0.800 min, m/z=411.2 [M+H]+.

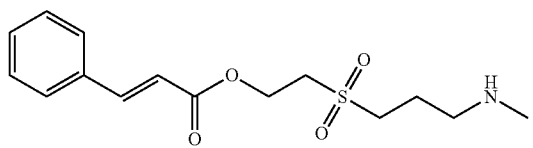 [SMILES: CNCCCS(=O)(=O)CCOC(=O)/C=C/c1ccccc1]

Step 5: 2-((3-(methylamino)propyl)sulfonyl)ethyl cinnamate

A solution of 2-((3-((tert-butoxycarbonyl)(methyl)amino) propyl)sulfonyl)ethyl cinnamate (2.2 g, 5.35 mmol) in 4.0 M hydrogen chloride in ethyl acetate (20 mL) was stirred at 25° C. for 10 min. The reaction mixture was concentrated in vacuo affording 2-((3-(methylamino)propyl)sulfonyl)ethyl cinnamate (1.66 g, crude, hydrochloride salt) as a white solid, which was used in the next step without further purification. LCMS Rt=0.731 min, m/z=311.1 [M+H]+.

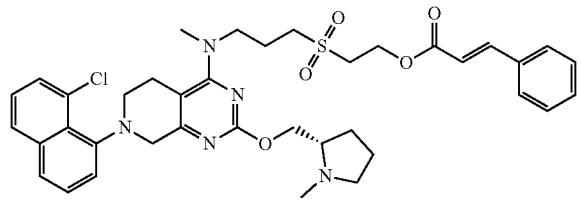 [SMILES: CN(CCCS(=O)(=O)CCOC(=O)/C=C/c1ccccc1)c1nc(OC[C@@H]2CCCN2C)nc2c1CCN(c1cccc3cccc(Cl)c13)C2]

Step 6: (S)-2-((3-((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)propyl)sulfonyl)ethyl cinnamate The substitution reaction was prepared in a similar fashion to Example 1 (Method 1-A), Step 4, substituting 2-((3-(methylamino)propyl)sulfonyl)ethyl cinnamate for tert-butyl (2-(methylamino)ethyl)carbamate. The crude product was purified by reverse phase HPLC (column: Phenomenex Luna C18 150*30 mm*5 µm; mobile phase: (water (0.1% TFA)-ACN; B %: 20%-50%, 8 min) affording (S)-2-((3-((7-(8-chloronaphthalen-1-yl)-2-((1-methylpyrrolidin-2-yl) methoxy)-5,6,7,8-tetrahydropyrido[3,4-d]pyrimidin-4-yl) (methyl)amino)propyl)sulfonyl)ethyl cinnamate (240 mg, 71.1%, trifluoroacetate salt) as a yellow solid. LCMS Rt=1.679 min, m/z=717.3 [M+H]+.

513

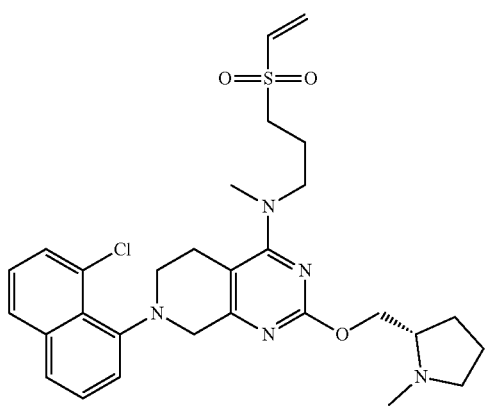 [SMILES: C=CS(=O)(=O)CCCN(C)c1nc(OC[C@@H]2CCCN2C)nc2c1CCN(c1cccc3cccc(Cl)c13)C2]

Step 7: (S)-7-(8-chloronaphthalen-1-yl)-N-methyl-2-((1-methylpyrrolidin-2-yl)methoxy)-N-(3-(vinylsulfonyl)propyl)-5,6,7,8-tetrahydropyrido[3,4-d]pyrimidin-4-amine To a solution of (S)-2-((3-((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)propyl)sulfonyl)ethyl cinnamate (150 mg, 180.22 μmol, trifluoroacetate salt) in acetone (1 mL) and water (1 mL) was added sodium bicarbonate (22.71 mg, 270.33 μmol). The mixture was stirred at 50° C. for 12 h. The reaction mixture was filtered and the filtrate was concentrated to dryness in vacuo. The residue was purified by reverse phase HPLC (column: Phenomenex Luna 80*30 mm*3 μm; mobile phase: ([water (0.1% TFA)-ACN]; B %: 10%-35%, 8 min) affording (S)-7-(8-chloronaphthalen-1-yl)-N-methyl-2-((1-methylpyrrolidin-2-yl)methoxy)-N-(3-(vinylsulfonyl)propyl)-5,6,7,8-tetrahydropyrido[3,4-d]pyrimidin-4-amine (31.2 mg, 24.35%, trifluoroacetate salt) as a yellow oil: $^1$H NMR (400 MHz, Acetonitrile-d3) δ 7.90 (d, J=8.0 Hz, 1H), 7.75 (d, J=8.1 Hz, 1H), 7.64-7.50 (m, 2H), 7.47-7.35 (m, 2H), 6.82 (ddd, J=1.7, 10.0, 16.6 Hz, 1H), 6.36 (d, J=16.5 Hz, 1H), 6.24 (d, J=10.0 Hz, 1H), 4.77-4.59 (m, 2H), 4.31 (br d, J=17.6 Hz, 1H), 3.90-3.70 (m, 5H), 3.56 (br dd, J=2.4, 9.2 Hz, 1H), 3.32 (d, J=3.3 Hz, 4H), 3.16-3.05 (m, 4H), 2.94 (d, J=2.1 Hz, 3H), 2.81 (br d, J=14.9 Hz, 1H), 2.40-2.19 (m, 2H), 2.17-2.00 (m, 4H). LCMS Rt=2.066 min, m/z=569.2 [M+H]+.

LCMS (5 to 95% acetonitrile in water+0.1% trifluoroacetic acid over 6 mins) retention time 2.066 min, ESI+ found [M+H]=569.2.

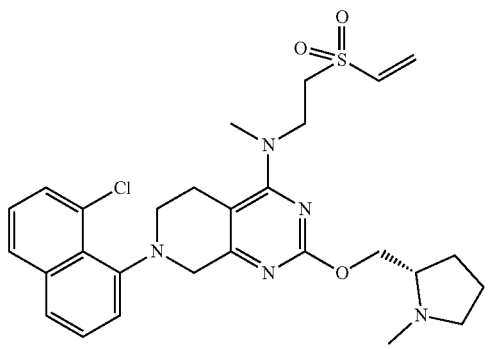 [SMILES: C=CS(=O)(=O)CCN(C)c1nc(OC[C@@H]2CCCN2C)nc2c1CCN(c1cccc3cccc(Cl)c13)C2]

514

Example 47 (Method 4-V1): (S)-7-(8-chloronaphthalen-1-yl)-N-methyl-2-((1-methylpyrrolidin-2-yl)methoxy)-N-(2-(vinylsulfonyl)ethyl)-5,6,7,8-tetrahydropyrido[3,4-d]pyrimidin-4-amine

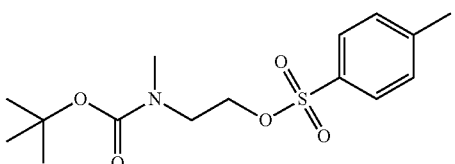

Step 1: 2-((tert-butoxycarbonyl)(methyl)amino)ethyl 4-methylbenzenesulfonate

The acylation was prepared in a similar fashion to Example 46 (Method 4-V), Step 1, substituting tert-butyl (2-hydroxyethyl)(methyl)carbamate for tert-butyl (3-hydroxypropyl)(methyl)carbamate. The crude product was concentrated in vacuo affording 2-((tert-butoxycarbonyl)(methyl)amino)ethyl 4-methylbenzenesulfonate (6 g, crude) as yellow oil, which was used in the next step without further purification: $^1$H NMR (400 MHz, Chloroform-d) δ 7.71 (d, J=8.3 Hz, 2H), 7.28 (br d, J=8.0 Hz, 2H), 4.12-3.99 (m, 3H), 3.39 (br d, J=4.8 Hz, 2H), 3.18-3.10 (m, 2H), 2.38 (s, 3H), 1.37-1.26 (m, 9H). LCMS Rt=0.646 min, m/z=329.1 [M+H]+.

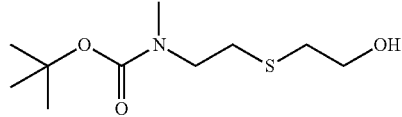

Step 2: tert-butyl (2-((2-hydroxyethyl)thio)ethyl)(methyl)carbamate

The substitution reaction was prepared in a similar fashion to Example 46 (Method 4-V), Step 2. The crude product was purified by column chromatography (silica gel, 100-200 mesh, 10-50% ethyl acetate in petroleum ether) affording tert-butyl (2-((2-hydroxyethyl)thio)ethyl)(methyl)carbamate (1.7 g, 39.66%) as yellow oil: $^1$H NMR (400 MHz, Chloroform-d) δ 3.68 (t, J=5.8 Hz, 2H), 3.33 (br d, J=5.0 Hz, 2H), 2.81 (br s, 3H), 2.69 (br t, J=5.6 Hz, 2H), 2.61 (br d, J=6.5 Hz, 2H), 1.39 (s, 9H). LCMS Rt=0.598 min, m/z=235.1 [M+H]+.

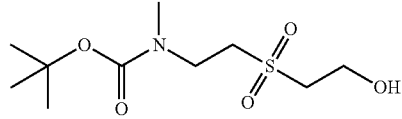 [SMILES: CN(CCS(=O)(=O)CCO)C(=O)OC(C)(C)C]

Step 3: tert-butyl (2-((2-hydroxyethyl)sulfonyl)ethyl)(methyl)carbamate

The epoxidation was prepared in a similar fashion to Example 46 (Method 4-V), Step 3. The crude product was concentrated in vacuo affording tert-butyl (2-((2-hydroxyethyl)sulfonyl)ethyl)(methyl)carbamate (1.7 g, crude) as a colorless oil, which was used in the next step without further purification: ¹H NMR (400 MHz, Chloroform-d) δ 4.19-4.10 (m, 2H), 3.71 (t, J=7.0 Hz, 2H), 3.39 (br s, 2H), 3.28 (br s, 2H), 2.94 (s, 3H), 1.49 (s, 9H). LCMS Rt =1.860 min, m/z=267.1 [M+H]+.

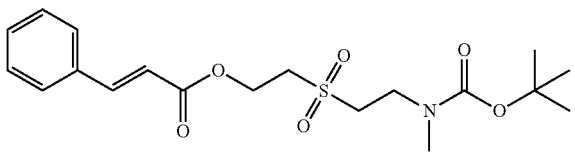 [SMILES: CN(CCS(=O)(=O)CCOC(=O)/C=C/c1ccccc1)C(=O)OC(C)(C)C]

Step 4: 2-((2-((tert-butoxycarbonyl)(methyl)amino)ethyl)sulfonyl)ethyl cinnamate The ester coupling reaction was prepared in a similar fashion to Example 46 (Method 4-V), Step 4. The crude product was purified by column chromatography (silica gel, 100-200 mesh, 10-50% ethyl acetate in petroleum ether) affording 2-((2-((tert-butoxycarbonyl)(methyl)amino)ethyl)sulfonyl)ethyl cinnamate (2.1 g, 83.08%) as a colorless oil. LCMS Rt=0.657 min, m/z=397.2 [M+H]+.

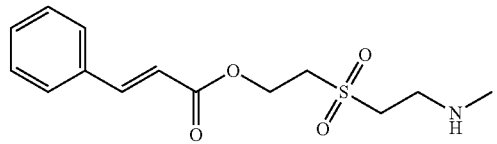 [SMILES: CNCCS(=O)(=O)CCOC(=O)/C=C/c1ccccc1]

Step 5: 2-((2-(methylamino)ethyl)sulfonyl)ethyl cinnamate

The deprotection of Boc was prepared in a similar fashion to Example 46 (Method 4-V), Step 5. The mixture was concentrated in vacuo affording 2-((2-(methylamino)ethyl)sulfonyl)ethyl cinnamate (1.6 g, crude, hydrochloride salt) as a white solid, which was used in the next step without further purification. LCMS Rt=0.423 min, m/z=297.1 [M+H]+.

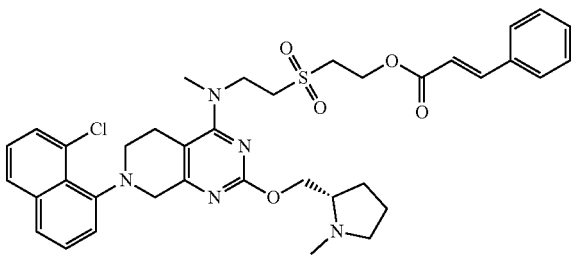 [SMILES: CN(CCS(=O)(=O)CCOC(=O)/C=C/c1ccccc1)c1nc(OC[C@@H]2CCCN2C)nc2c1CCN(c1cccc3cccc(Cl)c13)C2]

Step 6: (S)-2-((2-((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)ethyl)sulfonyl)ethyl cinnamate The substitution reaction was prepared in a similar fashion to Example 46 (Method 4-V), Step 6. The crude product was purified by reverse phase HPLC (column: Phenomenex luna C18 250*50 mm*10 μm; mobile phase: (water (0.1% TFA)-ACN; B %: 20%-50%, 10 min) affording (S)-2-((2-((7-(8-chloronaphthalen-1-yl)-2-((1-methylpyrrolidin-2-yl)methoxy)-5,6,7,8-tetrahydropyrido[3,4-d]pyrimidin-4-yl)(methyl)amino)ethyl)sulfonyl)ethyl cinnamate (700 mg, 47.65%, trifluoroacetate salt) as a white solid. LCMS Rt=0.927 min, m/z=703.3 [M+H]+.

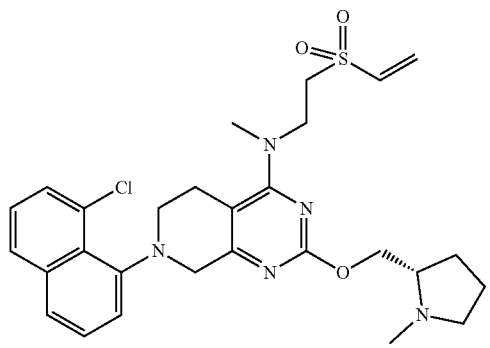 [SMILES: C=CS(=O)(=O)CCN(C)c1nc(OC[C@@H]2CCCN2C)nc2c1CCN(c1cccc3cccc(Cl)c13)C2]

Step 7: (S)-7-(8-chloronaphthalen-1-yl)-N-methyl-2-((1-methylpyrrolidin-2-yl)methoxy)-N-(2-(vinylsulfonyl)ethyl)-5,6,7,8-tetrahydropyrido[3,4-d]pyrimidin-4-amine The elimination reaction was prepared in a similar fashion to Example 46 (Method 4-V), Step 7. The crude product was purified by reverse phase HPLC (column: Phenomenex Luna 80*30 mm*3 μm; mobile phase: (water (0.2% FA)-ACN; B %: 10%-45%, 8 min) affording (S)-7-(8-chloronaphthalen-1-yl)-N-methyl-2-((1-methylpyrrolidin-2-yl)methoxy)-N-(2-(vinylsulfonyl)ethyl)-5,6,7,8-tetrahydropyrido[3,4-d]pyrimidin-4-amine (112 mg, 39.37%, formate salt) as a yellow solid: ¹H NMR (400 MHz, Acetonitrile-d3) δ 8.36 (s, 1H), 7.87 (br d, J=8.0 Hz, 1H), 7.70 (br d, J=8.1 Hz, 1H), 7.61-7.48 (m, 2H), 7.41 (br t, J=7.8 Hz, 1H), 7.33 (br d, J=7.4 Hz, 1H), 6.85 (ddd, J=3.9, 10.0, 16.4 Hz, 1H), 6.34 (br d, J=16.5 Hz, 1H), 6.20 (br d, J=9.9 Hz, 1H), 4.45 (td, J=5.8, 11.5 Hz, 1H), 4.31 (br dd, J=2.7, 10.9 Hz, 1H), 4.22 (br d, J=17.1 Hz, 1H), 3.98-3.82 (m, 2H), 3.73 (br d, J=17.5 Hz, 1H), 3.57-3.49 (m, 2H), 3.45-3.38 (m, 1H), 3.29 (br d, J=3.4 Hz, 1H), 3.22-3.15 (m, 3H), 3.13-2.99 (m, 3H), 2.72-2.51 (m, 5H), 2.19-2.08 (m, 1H), 1.92-1.71 (m, 3H). LCMS Rt=2.117 min, m/z=555.2 [M+H]+.

LCMS (5 to 95% acetonitrile in water+0.1% trifluoroacetic acid over 6 mins) retention time 2.117 min, ESI+ found [M+H]=555.2.

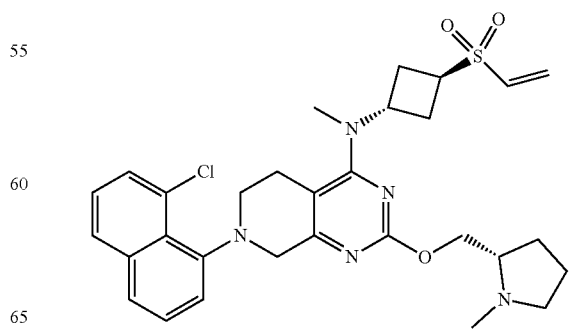

Example 48 (Method 5-V): 7-(8-chloronaphthalen-1-yl)-N-methyl-2-(((S)-1-methylpyrrolidin-2-yl)methoxy)-N-((1r,3S)-3-(vinylsulfonyl)cyclobutyl)-5,6,7,8-tetrahydropyrido[3,4-d]pyrimidin-4-amine

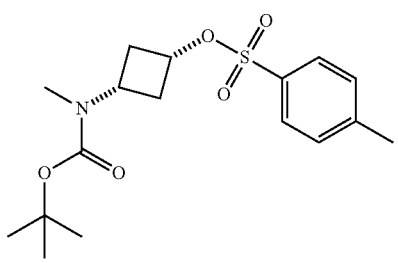 [SMILES: Cc1ccc(S(=O)(=O)O[C@H]2C[C@@H](N(C)C(=O)OC(C)(C)C)C2)cc1]

Step 1: cis-3-((tert-butoxycarbonyl)(methyl)amino)cyclobutyl 4-methylbenzenesulfonate The acylation was prepared in a similar fashion to Example 46 (Method 4-V), Step 1, substituting tert-butyl (cis-3-hydroxycyclobutyl)(methyl)carbamate for tert-butyl (3-hydroxypropyl)(methyl)carbamate. The crude product was concentrated in vacuo affording cis-3-((tert-butoxycarbonyl)(methyl)amino)cyclobutyl 4-methylbenzenesulfonate (1.7 g, 89%) as a yellow oil, which was used in the next step without further purification: $^1$H NMR (400 MHz, Chloroform-d) δ 7.86-7.76 (m, 2H), 7.38 (d, J=8.1 Hz, 2H), 4.52 (m, 1H), 4.06 (m, 1H), 2.79 (s, 3H), 2.59-2.51 (m, 2H), 2.49 (s, 3H), 2.34-2.23 (m, 2H), 1.45 (s, 9H). LCMS Rt=0.820 min, m/z=355.2 [M+H]+.

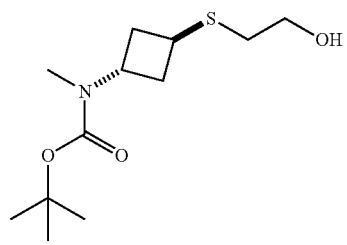 [SMILES: CN(C(=O)OC(C)(C)C)[C@H]1C[C@H](SCCO)C1]

Step 2: trans-tert-butylN-[3-(2-hydroxyethylsulfanyl)cyclobutyl]-N-methyl-carbamate The substitution reaction was prepared in a similar fashion to Example 46 (Method 4-V), Step 2. The crude product was purified by column chromatography (silica gel, 100-200 mesh, 0-10% ethyl acetate in petroleum ether) affording trans-tert-butyl N-[3-(2-hydroxyethylsulfanyl)cyclobutyl]-N-methyl-carbamate (1.1 g, 93%) as a colorless oil: $^1$H NMR (400 MHz, Chloroform-d) δ 4.76 (br s, 1H), 3.76-3.66 (m, 3H), 3.40-3.31 (m, 1H), 2.80 (s, 2H), 2.71-2.67 (m, 2H), 2.58-2.54 (m, 2H), 2.18-2.11 (m, 2H), 1.44 (s, 9H). LCMS Rt=1.486 min, m/z=261.1 [M+H]+.

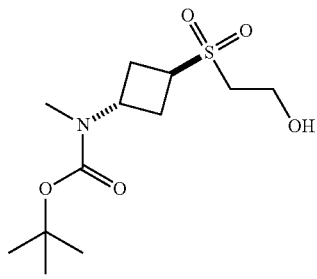 [SMILES: CN(C(=O)OC(C)(C)C)[C@H]1C[C@H](S(=O)(=O)CCO)C1]

Step 3: trans-tert-butyl N-[3-(2-hydroxyethylsulfonyl)cyclobutyl]-N-methyl-carbamate The epoxidation was prepared in a similar fashion to Example 46 (Method 4-V), Step 3. The crude product was purified by column chromatography (silica gel, 100-200 mesh, 0-100% ethyl acetate in petroleum ether) affording trans-tert-butyl N-[3-(2-hydroxyethylsulfonyl)cyclobutyl]-N-methyl-carbamate (400 mg, 59.40%) as a colorless oil: $^1$H NMR (400 MHz, Chloroform-d) δ 4.52 (quin, J=8.6 Hz, 1H), 4.12-3.99 (m, 3H), 3.73-3.63 (m, 1H), 3.13-3.09 (m, 2H), 2.77 (s, 3H), 2.72-2.68 (m, 3H), 2.32 (br s, 1H), 1.39 (s, 9H). LCMS Rt=0.580 min, m/z=293.1 [M+H]+.

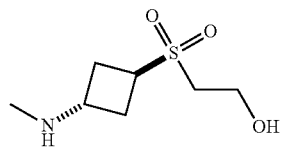

Step 4: trans-2-[3-(methylamino)cyclobutyl]sulfonylethanol

The deprotection of Boc was prepared in a similar fashion to Example 46 (Method 4-V), Step 5. The mixture was concentrated in vacuo affording trans-2-[3-(methylamino)cyclobutyl]sulfonylethanol (50 mg, 98%, hydrochloride salt) as a white solid, which was used in the next step without further purification. LCMS Rt=0.180 min, m/z=193.1 [M+H]+.

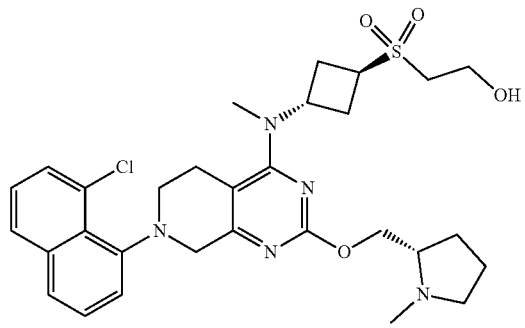 [SMILES: CN1CCC[C@H]1COc1nc2c(c(N(C)[C@H]3C[C@H](S(=O)(=O)CCO)C3)n1)CCN(c1cccc3cccc(Cl)c13)C2]

Step 5: 2-((trans-3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)cyclobutyl)sulfonyl)ethanol The substitution reaction was prepared in a similar fashion to Example 46 (Method 4-V), Step 6. The crude product was purified by reverse phase HPLC (column: Phenomenex luna C18 250*50 mm*10 μm; mobile phase: (water (0.1% TFA)-ACN; B %: 20%-50%, 10 min) affording 2-((trans-3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)cyclobutyl)sulfonyl)ethanol (250 mg, 43.33%, trifluoroacetate salt) as a yellow oil. LCMS Rt=0.615 min, m/z=599.2 [M+H]+.

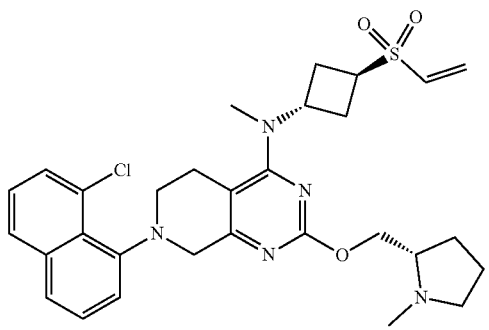 [SMILES: C=CS(=O)(=O)[C@H]1C[C@H](N(C)c2nc(OC[C@@H]3CCCN3C)nc3c2CCN(c2cccc4cccc(Cl)c24)C3)C1]

Step 6: 7-(8-chloronaphthalen-1-yl)-N-methyl-2-(((S)-1-methylpyrrolidin-2-yl)methoxy)-N-((1r,3S)-3-(vinylsulfonyl)cyclobutyl)-5,6,7,8-tetrahydropyrido[3,4-d]pyrimidin-4-amine To a solution of 2-((trans-3-((7-(8-chloronaphthalen-1-yl)-2-(((S)-1-methylpyrrolidin-2-yl)methoxy)-5,6,7,8-tetrahydropyrido[3,4-d]pyrimidin-4-yl)(methyl)amino)cyclobutyl)sulfonyl)ethanol (100 mg, 140.02 μmol, trifluoroacetate salt) in dichloromethane (2 mL) and triethylamine (70.84 mg, 700.1 μmol) was added methanesulfonyl chloride (80.20 mg, 700.1 μmol) at 0° C. The mixture was stirred at 0° C. for 2 h. The reaction mixture was quenched with saturated water (0.5 ml) at 0° C. and extracted with DCM (3×4 mL). The combined organic layers were dried over sodium sulphate and concentrated in vacuo. The residue was purified by reverse phase HPLC (column: Phenomenex Luna 80*30 mm*3 μm; mobile phase: (water (0.2% FA)-ACN; B %: 22%-52%, 8 min) affording 7-(8-chloronaphthalen-1-yl)-N-methyl-2-(((S)-1-methylpyrrolidin-2-yl)methoxy)-N-((1r,3S)-3-(vinylsulfonyl)cyclobutyl)-5,6,7,8-tetrahydropyrido[3,4-d]pyrimidin-4-amine (27.45 mg, 29.01%, formate salt) as a yellow solid: $^1$H NMR (400 MHz, Acetonitrile-d3) δ 7.88 (dd, J=1.0, 8.1 Hz, 1H), 7.75-7.68 (m, 1H), 7.62-7.50 (m, 2H), 7.46-7.33 (m, 2H), 6.78 (dd, J=10.0, 16.6 Hz, 1H), 6.39 (d, J=16.6 Hz, 1H), 6.25 (d, J=10.0 Hz, 1H), 4.69 (quin, J=8.3 Hz, 1H), 4.37 (td, J=5.8, 11.4 Hz, 1H), 4.30-4.20 (m, 2H), 3.75 (d, J=17.4 Hz, 1H), 3.65 (tt, J=4.3, 8.8 Hz, 1H), 3.56 (br d, J=11.3 Hz, 1H), 3.26-3.16 (m, 2H), 3.16-3.02 (m, 2H), 2.98 (s, 3H), 2.93-2.87 (m, 1H), 2.72-2.69 (m, 2H), 2.65-2.59 (m, 2H), 2.54 (s, 3H), 2.49-2.43 (m, 2H), 2.11-2.02 (m, 1H), 1.88-1.79 (m, 2H), 1.79-1.69 (m, 1H). LCMS Rt=2.149 min, m/z=581.2 [M+H]+.

LCMS (5 to 95% acetonitrile in water+0.1% trifluoroacetic acid over 6 mins) retention time 2.149 min, ESI+ found [M+H]=581.2

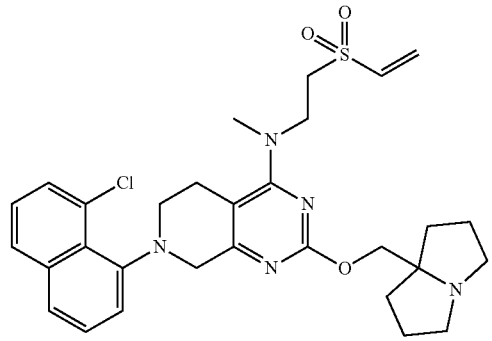 [SMILES: C=CS(=O)(=O)CCN(C)c1nc(OCC23CCCN2CCC3)nc2c1CCN(c1cccc3cccc(Cl)c13)C2]

Example 49 (Method 4-V2): 7-(8-chloronaphthalen-1-yl)-2-((hexahydro-1H-pyrrolizin-7a-yl)methoxy)-N-methyl-N-(2-(vinylsulfonyl)ethyl)-5,6,7,8-tetrahydropyrido[3,4-d]pyrimidin-4-amine

Step 1: 2-((2-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)ethyl)sulfonyl)ethyl cinnamate The substitution reaction was prepared in a similar fashion to Example 46 (Method 4-V), Step 6, substituting 7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl trifluoromethanesulfonate for (S)-7-(8-chloronaphthalen-1-yl)-2-((1-methylpyrrolidin-2-yl)methoxy)-5,6,7,8-tetrahydropyrido[3,4-d]pyrimidin-4-yl trifluoromethanesulfonate, and substituting 2-((2-(methylamino)ethyl)sulfonyl)ethyl cinnamate (see Example 47 Step 5) for 2-((3-(methylamino)propyl)sulfonyl)ethyl cinnamate. The crude product was purified by reverse phase HPLC (column: Phenomenex Luna C18 150*30 mm*5 μm; mobile phase: (water (TFA)-ACN; B %: 15%-55%, 8 min) affording 2-((2-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)ethyl)sulfonyl)ethyl cinnamate (65 mg, 20.76%, trifluoroacetate salt) as a white solid. LCMS Rt=1.792 min, m/z=729.3 [M+H]+.

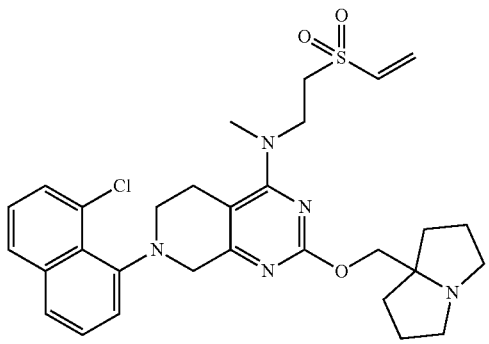 [SMILES: C=CS(=O)(=O)CCN(C)c1nc(OCC23CCCN2CCC3)nc2c1CCN(c1cccc3cccc(Cl)c13)C2]

Step 2: 7-(8-chloronaphthalen-1-yl)-2-((hexahydro-1H-pyrrolizin-7a-yl)methoxy)-N-methyl-N-(2-(vinylsulfonyl)ethyl)-5,6,7,8-tetrahydropyrido[3,4-d]pyrimidin-4-amine The elimination reaction was prepared in a similar fashion to Example 46 (Method 4-V), Step 7. The crude product was purified by reverse phase HPLC (column: Phenomenex Luna 80*30 mm*3 μm; mobile phase: [water (FA)-ACN]; B %: 15%-45%, 8 min) affording 7-(8-chloronaphthalen-1-yl)-2-((hexahydro-1H-pyrrolizin-7a-yl)methoxy)-N-methyl-N-(2-(vinylsulfonyl)ethyl)-5,6,7,8-tetrahydropyrido[3,4-d]pyrimidin-4-amine (5 mg, 17.20%, formate salt) as a white solid: $^1$H NMR (400 MHz, Acetonitrile-d3) δ 7.89 (d, J=7.5 Hz, 1H), 7.72 (d, J=7.8 Hz, 1H), 7.59 (dd, J=1.1, 7.5 Hz, 1H), 7.54 (t, J=7.8 Hz, 1H), 7.47-7.40 (m, 1H), 7.35 (d, J=7.0 Hz, 1H), 6.95-6.84 (m, 1H), 6.37 (d, J=16.6 Hz, 1H), 6.22 (d, J=9.9 Hz, 1H), 4.37-4.27 (m, 2H), 4.24 (br d, J=17.1 Hz, 1H), 4.05-3.82 (m, 2H), 3.75 (br d, J=17.4 Hz, 1H), 3.64-3.51 (m, 2H), 3.50-3.35 (m, 3H), 3.33-3.17 (m, 4H), 3.15-3.05 (m, 1H), 3.02-2.84 (m, 3H), 2.17-2.08 (m, 2H), 2.06-1.99 (m, 4H), 1.87 (br dd, J=6.5, 12.7 Hz, 2H). LCMS Rt=2.135 min, m/z=581.2 [M+H]+.

LCMS (5 to 95% acetonitrile in water+0.1% trifluoroacetic acid over 6 mins) retention time 2.135 min, ESI+ found [M+H]=581.2.

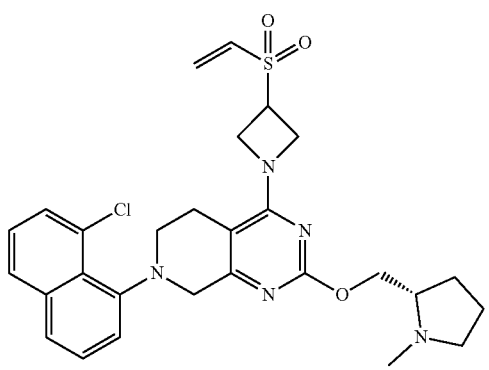 [SMILES: C=CS(=O)(=O)C1CN(c2nc(OC[C@@H]3CCCN3C)nc3c2CCN(c2cccc4cccc(Cl)c24)C3)C1]

Example 50 (Method 5-V1): (S)-7-(8-chloronaphthalen-1-yl)-2-((1-methylpyrrolidin-2-yl)methoxy)-4-(3-(vinylsulfonyl)azetidin-1-yl)-5,6,7,8-tetrahydropyrido[3,4-d]pyrimidine

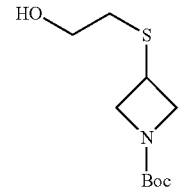 [SMILES: CC(C)(C)OC(=O)N1CC(SCCO)C1]

Step 1: tert-butyl 3-((2-hydroxyethyl)thio)azetidine-1-carboxylate

The substitution reaction was prepared in a similar fashion to Example 48 (Method 5-V), Step 2, substituting tert-butyl 3-iodoazetidine-1-carboxylate for 3-((tert-butoxycarbonyl)(methyl)amino)propyl 4-methylbenzenesulfonate. The crude product was concentrated in vacuo affording tert-butyl 3-((2-hydroxyethyl)thio)azetidine-1-carboxylate (2.8 g, crude) as a colorless oil, which was used in the next step without further purification: $^1$H NMR (400 MHz, Chloroform-d) δ 4.27-4.23 (m, 2H), 3.80-3.75 (m, 2H), 3.68-3.62 (m, 2H), 3.65-3.55 (m, 1H), 2.75-2.68 (m, 2H), 1.43 (s, 9H).

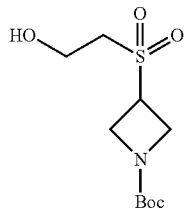 [SMILES: CC(C)(C)OC(=O)N1CC(S(=O)(=O)CCO)C1]

Step 2: tert-butyl 3-((2-hydroxyethyl)sulfonyl)azetidine-1-carboxylate

The epoxidation was prepared in a similar fashion to Example 48 (Method 5-V), Step 3.
The crude product was purified by column chromatography (silica gel, 100-200 mesh, 0-10% ethyl acetate in petroleum ether) affording tert-butyl 3-((2-hydroxyethyl)sulfonyl)azetidine-1-carboxylate (250 mg, 19.79%) as a colorless oil: $^1$H NMR (400 MHz, Chloroform-d) δ 4.31-4.29 (m, 2H), 4.17-4.09 (m, 4H), 3.20-3.18 (m, 2H), 2.51-2.48 (m, 1H), 1.44 (s, 9H).

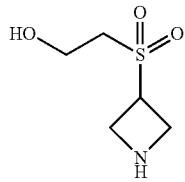

Step 3: 2-(azetidin-3-ylsulfonyl)ethanol

The deprotection of Boc was prepared in a similar fashion to Example 48 (Method 5-V), Step 4. The reaction mixture was concentrated in vacuo affording 2-(azetidin-3-ylsulfonyl)ethanol (120 mg, crude, trifluoroacetate salt) as a colorless oil, which was used in the next step without further purification. LCMS Rt=0.450 min, m/z=165.1 [M+H]+.

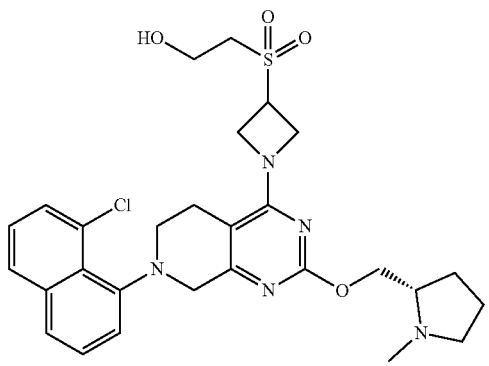 [SMILES: CN1CCC[C@H]1COc1nc2c(c(N3CC(S(=O)(=O)CCO)C3)n1)CCN(c1cccc3cccc(Cl)c13)C2]

Step 4: (S)-2-((1-(7-(8-chloronaphthalen-1-yl)-2-((1-methylpyrrolidin-2-yl)methoxy)-5,6,7,8-tetrahydropyrido[3,4-d]pyrimidin-4-yl)azetidin-3-yl)sulfonyl)ethanol The substitution reaction was prepared in a similar fashion to Example 48 (Method 5-V), Step 5. The crude product was concentrated in vacuo affording (S)-2-((1-(7-(8-chloronaphthalen-1-yl)-2-((1-methylpyrrolidin-2-yl)methoxy)-5,6,7,8-tetrahydropyrido[3,4-d]pyrimidin-4-yl)azetidin-3-yl)sulfonyl)ethanol (120 mg, crude) as a pale yellow oil, which was used in the next step without further purification. LCMS Rt=0.680 min, m/z=571.2 [M+H]+.

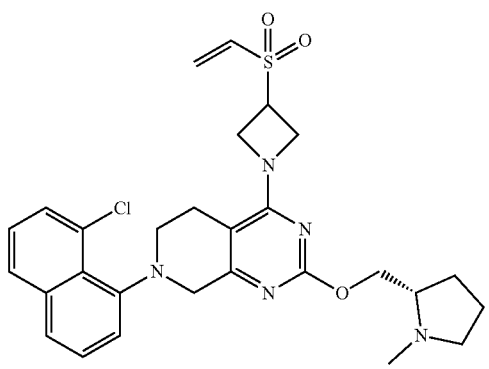 [SMILES: C=CS(=O)(=O)C1CN(c2nc(OC[C@@H]3CCCN3C)nc3c2CCN(c2cccc4cccc(Cl)c24)C3)C1]

Step 5: (S)-7-(8-chloronaphthalen-1-yl)-2-((1-methylpyrrolidin-2-yl)methoxy)-4-(3-(vinylsulfonyl)azetidin-1-yl)-5,6,7,8-tetrahydropyrido[3,4-d]pyrimidine The elimination reaction was prepared in a similar fashion to Example 48 (Method 5-V), Step 6. The crude product was purified by reverse phase HPLC (column: Waters Xbridge BEH C18 100*30 mm*10 μm; mobile phase: (water (NH₄HCO₃)-ACN; B %: 45%-75%, 10 min) affording (S)-7-(8-chloronaphthalen-1-yl)-2-((1-methylpyrrolidin-2-yl)methoxy)-4-(3-(vinylsulfonyl)azetidin-1-yl)-5,6,7,8-tetrahydropyrido[3,4-d]pyrimidine (11.7 mg, 11.52%) as a yellow solid: ¹H NMR (400 MHz, Acetonitrile-d3) δ 7.85-7.83 (d, J=8.4, 1H), 7.68-7.66 (m, 1H), 7.55 (d, J=7.4 Hz, 1H), 7.53-7.47 (m, 1H), 7.39 (t, J=7.8 Hz, 1H), 7.34-7.30 (m, 1H), 6.81-6.77 (m, 1H), 6.47-6.43 (d, J=16.4, 1H), 6.32-6.29 (d, J=10, 1H), 4.55-4.51 (m, 2H), 4.49-4.45 (m, 1H), 4.37-4.34 (m, 1H), 4.25-4.21 (m, 1H), 4.12-4.07 (m, 3H), 3.73-3.69 (m, 1H), 3.51-3.47 (m, 1H), 3.11-3.08 (m, 2H), 2.95-2.91 (m, 1H), 2.55-2.45 (m, 2H), 2.23 (s, 3H), 2.27-2.25 (m, 1H), 1.71-1.67 (m, 4H). LCMS Rt=3.115 min, m/z=553.2 [M+H]+.

LCMS (5 to 95% acetonitrile in water+0.03% ammonium bicarbonate over 6 mins) retention time 3.115 min, ESI+ found [M+H]=553.2.

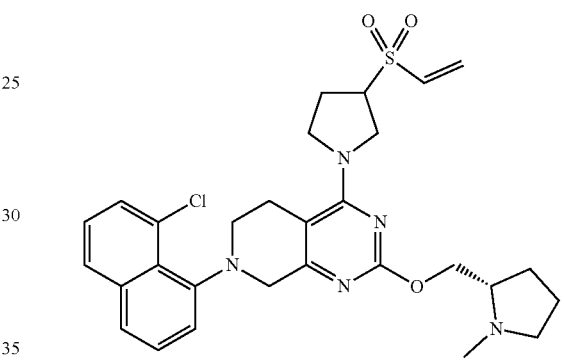

Example 51 (Method 5-V2): 7-(8-chloronaphthalen-1-yl)-2-(((S)-1-methylpyrrolidin-2-yl)methoxy)-4-(3-(vinylsulfonyl)pyrrolidin-1-yl)-5,6,7,8-tetrahydropyrido[3,4-d]pyrimidine

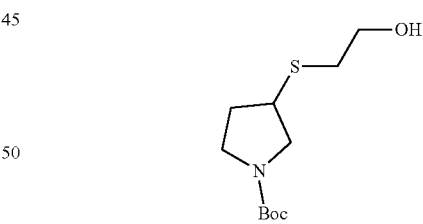

Step 1: tert-butyl 3-((2-hydroxyethyl)thio)pyrrolidine-1-carboxylate

The substitution reaction was prepared in a similar fashion to Example 48 (Method 5-V), Step 2, substituting tert-butyl 3-iodopyrrolidine-1-carboxylate for 3-((tert-butoxycarbonyl)(methyl)amino)propyl 4-methylbenzenesulfonate. The crude product was purified by column chromatography (silica gel, 100-200 mesh, 0-100% ethyl acetate in petroleum ether) affording tert-butyl 3-((2-hydroxyethyl)thio)pyrrolidine-1-carboxylate (500 mg, 60.06%) as a colorless oil. LCMS Rt=0.720 min, m/z=247.1 [M+H]+.

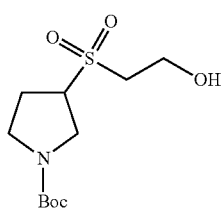 [SMILES: CC(C)(C)OC(=O)N1CCC(S(=O)(=O)CCO)C1]

Step 2: tert-butyl 3-((2-hydroxyethyl)sulfonyl)pyrrolidine-1-carboxylate

The epoxidation was prepared in a similar fashion to Example 48 (Method 5-V), Step 3. The crude product was purified by column chromatography (silica gel, 100-200 mesh, 0-100% ethyl acetate in petroleum ether) affording tert-butyl 3-((2-hydroxyethyl)sulfonyl)pyrrolidine-1-carboxylate (500 mg, 49.19%) as a colorless oil. LCMS Rt=0.620 min, m/z=279.1 [M+H]+.

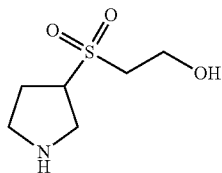 [SMILES: O=S(=O)(CCO)C1CCNC1]

Step 3: 2-(pyrrolidin-3-ylsulfonyl)ethanol

The deprotection of Boc was prepared in a similar fashion to Example 48 (Method 5-V), Step 4. The reaction mixture was concentrated in vacuo affording 2-(pyrrolidin-3-ylsulfonyl)ethanol (400 mg, crude, hydrochloride salt) as a white solid, which was used in the next step without further purification: $^1$H NMR (400 MHz, Deuterium oxide) δ 4.52 (br t, J=5.4 Hz, 1H), 4.29-4.22 (m, 1H), 4.06-4.00 (m, 2H), 3.85-3.68 (m, 4H), 3.45-3.40 (m, 1H), 2.54-2.49 (m, 2H).

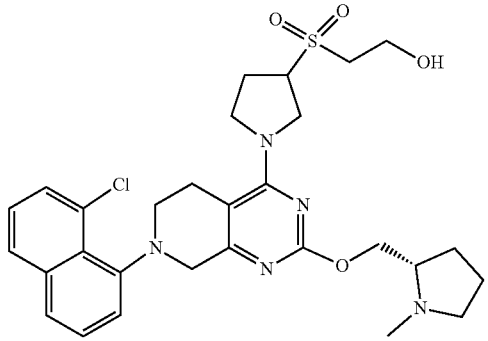 [SMILES: CN1CCC[C@H]1COc1nc2c(c(N3CCC(S(=O)(=O)CCO)C3)n1)CCN(c1cccc3cccc(Cl)c13)C2]

Step 4: 2-((1-(7-(8-chloronaphthalen-1-yl)-2-(((S)-1-methylpyrrolidin-2-yl)methoxy)-5,6,7,8-tetrahydropyrido[3,4-d]pyrimidin-4-yl)pyrrolidin-3-yl)sulfonyl)ethanol The substitution was prepared in a similar fashion to Example 48 (Method 5-V), Step 5. The crude product was concentrated in vacuo affording 2-((1-(7-(8-chloronaphthalen-1-yl)-2-(((S)-1-methylpyrrolidin-2-yl)methoxy)-5,6,7,8-tetrahydropyrido[3,4-d]pyrimidin-4-yl)pyrrolidin-3-yl)sulfonyl)ethanol (180 mg, crude) as a yellow gum, which was used in next step without further purification. LCMS Rt=1.310 min, m/z=585.2 [M+H]+.

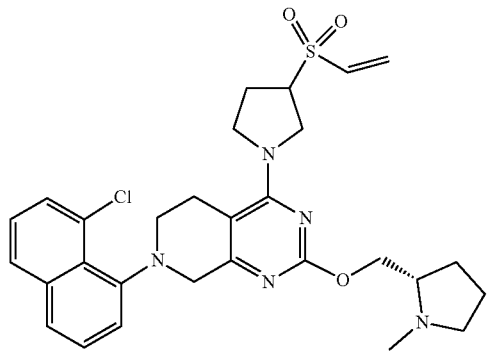 [SMILES: C=CS(=O)(=O)C1CCN(c2nc(OC[C@@H]3CCCN3C)nc3c2CCN(c2cccc4cccc(Cl)c24)C3)C1]

Step 5: 7-(8-chloronaphthalen-1-yl)-2-(((S)-1-methylpyrrolidin-2-yl)methoxy)-4-(3-(vinylsulfonyl)pyrrolidin-1-yl)-5,6,7,8-tetrahydropyrido[3,4-d]pyrimidine The elimination reaction was prepared in a similar fashion to Example 48 (Method 5-V), Step 6. The crude product was purified by reverse phase HPLC (column: Phenomenex Luna C18 150*30 mm*5 μm; mobile phase: (water (FA)-ACN; B %: 13%-43%, 8 min) affording 7-(8-chloronaphthalen-1-yl)-2-(((S)-1-methylpyrrolidin-2-yl)methoxy)-4-(3-(vinylsulfonyl)pyrrolidin-1-yl)-5,6,7,8-tetrahydropyrido[3,4-d]pyrimidine (60 mg, 30.61%, formate salt) as a brown gum: $^1$H NMR (400 MHz, Acetonitrile-d3) δ 8.23 (s, 1H), 7.85 (dd, J=1.1, 8.2 Hz, 1H), 7.67 (d, J=8.1 Hz, 1H), 7.55 (dd, J=1.2, 7.3 Hz, 1H), 7.50 (t, J=7.8 Hz, 1H), 7.42-7.37 (m, 1H), 7.31 (d, J=7.3 Hz, 1H), 6.80 (ddd, J=6.2, 10.0, 16.5 Hz, 1H), 6.40 (dd, J=3.9, 16.6 Hz, 1H), 6.27 (dd, J=2.7, 10.0 Hz, 1H), 4.38-4.31 (m, 1H), 4.23-4.16 (m, 1H), 4.14-4.06 (m, 2H), 4.02-3.68 (m, 6H), 3.57-3.49 (m, 1H), 3.33-3.25 (m, 1H), 3.17-3.05 (m, 2H), 2.78 (br s, 2H), 2.47 (s, 3H), 2.40-2.28 (m, 3H), 2.07-1.98 (m, 1H), 1.80-1.74 (m, 2H). LCMS Rt=2.082 min, m/z=567.2 [M+H]+.

LCMS (5 to 95% acetonitrile in water+0.03% ammonium bicarbonate over 6 mins) retention time 2.082 min, ESI+ found [M+H]=567.2.

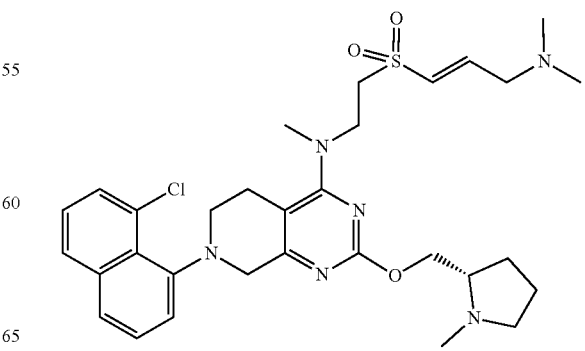

Example 52 (Method 6-V): (S,E)-7-(8-chloronaphthalen-1-yl)-N-(2-((3-(dimethylamino)prop-1-en-1-yl)sulfonyl)ethyl)-N-methyl-2-((1-methylpyrrolidin-2-yl)methoxy)-5,6,7,8-tetrahydropyrido[3,4-d]pyrimidin-4-amine

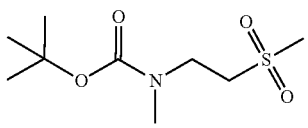

Step 1: tert-butyl N-methyl-N-(2-methylsulfonylethyl)carbamate

To a solution of tert-butyl N-(2-hydroxyethyl)-N-methyl-carbamate (20 g, 114.14 mmol) in dichloromethane (100 mL) was added triethylamine (23.10 g, 228.28 mmol) and methylsulfonyl methanesulfonate (39.77 g, 228.28 mmol) at 0° C. The mixture was stirred at 0° C. for 1 h. The reaction mixture was quenched with a saturated solution of sodium bicarbonate (100 mL) and extracted with dichloromethane (3×50 ml). The combined organic layers were dried over sodium sulphate and concentrated in vacuo affording tert-butyl N-methyl-N-(2-methylsulfonylethyl)carbamate (22.2 g, crude) as a brown oil, which was used in the next step without further purification.

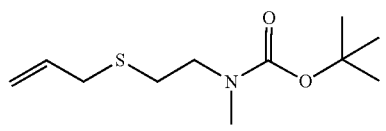

Step 2: tert-butyl (2-(allylthio)ethyl)(methyl)carbamate

To a solution of tert-butyl N-methyl-N-(2-methylsulfonylethyl)carbamate (22.2 g, 93.42 mmol) in toluene (100 mL) was added 1,8-Diazabicyclo[5.4.0]undec-7-ene (42.67 g, 280.26 mmol) and prop-2-ene-1-thiol (7.62 g, 102.76 mmol). The mixture was stirred at 25° C. for 1 h. The reaction mixture was quenched with water (100 mL) and extracted with dichloromethane (3×50 ml). The combined organic layers were dried over sodium sulphate and concentrated in vacuo. The resulting residue was purified by column chromatography (silica gel, 100-200 mesh, 0-100% ethyl acetate in petroleum ether) affording tert-butyl (2-(allylthio)ethyl)(methyl)carbamate (16 g, 74.03%) as a black oil. LCMS Rt=0.715 min, m/z=231.1 [M+H]+.

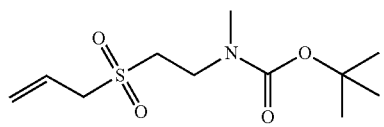 [SMILES: C=CCS(=O)(=O)CCN(C)C(=O)OC(C)(C)C]

Step 3: tert-butyl N-(2-allylsulfonylethyl)-N-methyl-carbamate

To a solution of tert-butyl (2-(allylthio)ethyl)(methyl)carbamate (11 g, 47.55 mmol) in water (10 mL) and acetonitrile (10 mL) was added Oxone@ (64.71 g, 105.25 mmol) at −10° C. The mixture was stirred at 25° C. for 2 h. The reaction mixture was concentrated in vacuo affording tert-butyl N-(2-allylsulfonylethyl)-N-methyl-carbamate (10 g, crude) as a black oil, which was used in the next step without further purification. LCMS Rt=0.671 min, m/z=263.1 [M+H]+.

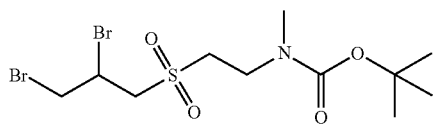 [SMILES: CN(CCS(=O)(=O)CC(Br)CBr)C(=O)OC(C)(C)C]

Step 4: tert-butyl N-[2-(2,3-dibromopropylsulfonyl)ethyl]-N-methyl-carbamate

To a solution of tert-butyl N-(2-allylsulfonylethyl)-N-methyl-carbamate (2 g, 7.59 mmol) in trichloromethane (20 mL) was added bromine (1.82 g, 11.39 mmol) at 0° C. The mixture was stirred at 0° C. for 0.5 h. The mixture was concentrated in vacuo affording tert-butyl N-[2-(2,3-dibromopropylsulfonyl)ethyl]-N-methyl-carbamate (3 g, crude) as a yellow oil, which was used in the next step without further purification. LCMS Rt=0.729 min, m/z=321.0/323.0 [M+H]+.

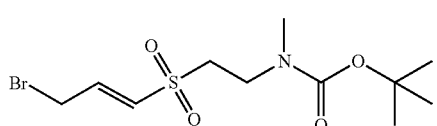

Step 5: tert-butylN-[2-[(E)-3-bromoprop-1-enyl]sulfonylethyl]-N-methyl-carbamate To a solution of tert-butyl N-[2-(2,3-dibromopropylsulfonyl)ethyl]-N-methyl-carbamate (3 g, 7.09 mmol) in tetrahydrofuran (30 mL) was added triethylamine (1.43 g, 14.18 mmol). The mixture was stirred at 0° C. for 1 h. The reaction mixture was diluted with water (50 mL) and extracted with dichloromethane (2×20 mL). The combined organics were washed with brine (15 mL), dried over sodium sulphate and concentrated in vacuo affording tert-butyl N-[2-[(E)-3-bromoprop-1-enyl]sulfonylethyl]-N-methyl-carbamate (1.8 g, crude) as a yellow oil, which was used in the next step without further purification. LCMS Rt=0.699 min, m/z=341.0/343.0 [M+H]+.

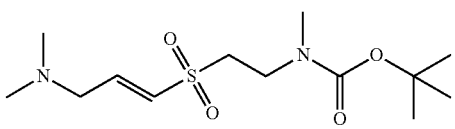 [SMILES: CN(C)C/C=C/S(=O)(=O)CCN(C)C(=O)OC(C)(C)C]

Step 6: tert-butylN-[2-[(E)-3-(dimethylamino)prop-1-enyl]sulfonylethyl]-N-methyl-carbamate To a solution of tert-butyl N-[2-[(E)-3-bromoprop-1-enyl]sulfonylethyl]-N-methyl-carbamate (2.5 g, 7.30 mmol) and N-ethyl-N-isopropylpropan-2-amine (1.89 g, 14.61 mmol)

in dichloromethane (50 mL) was added N-methylmethanamine (1.65 g, 14.61 mmol, 40% purity). The mixture was stirred at 0° C. for 2 h. The reaction mixture was diluted with water (50 mL) and extracted with dichloromethane (3×50 mL). The combined organic layers were dried over sodium sulphate and concentrated in vacuo affording tert-butyl N-[2-[(E)-3-(dimethylamino)prop-1-enyl]sulfonylethyl]-N-methyl-carbamate (2 g, crude) as a yellow oil, which was used in the next step without further purification: $^1$H NMR (400 MHz, Chloroform-d) δ 7.01-6.82 (m, 1H), 6.53 (br d, J=15.1 Hz, 1H), 3.66-3.59 (m, 2H), 3.37-3.32 (m, 2H), 3.18-3.13 (m, 2H), 2.92-2.89 (m, 3H), 2.28 (s, 6H), 1.46 (s, 9H). LCMS Rt=0.483 min, m/z=306.2 [M+H]+.

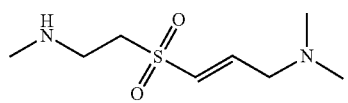

Step 7: (E)-N,N-dimethyl-3-[2-(methylamino)ethyl-sulfonyl]prop-2-en-1-amine

To a solution of tert-butyl N-[2-[(E)-3-(dimethylamino)prop-1-enyl]sulfonylethyl]-N-methyl-carbamate (500 mg, 1.63 mmol) in dichloromethane (3 mL) was added trifluoroacetic acid (1 mL, 13.51 mmol). The mixture was stirred at 25° C. for 0.5 h. The reaction mixture was concentrated in vacuo affording (E)-N,N-dimethyl-3-[2-(methylamino)ethylsulfonyl]prop-2-en-1-amine (400 mg, crude, trifluoroacetate salt) as a yellow oil, which was used in the next step without further purification. LCMS Rt=0.184 min, m/z=206.1 [M+H]+.

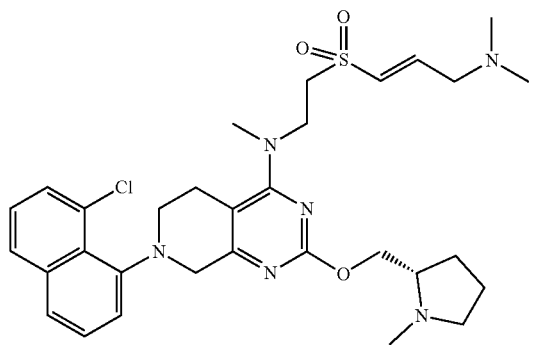 [SMILES: CN(C)C/C=C/S(=O)(=O)CCN(C)c1nc(OC[C@@H]2CCCN2C)nc2c1CCN(c1cccc3cccc(Cl)c13)C2]

Step 8: (S,E)-7-(8-chloronaphthalen-1-yl)-N-(2-((3-(dimethylamino)prop-1-en-1-yl)sulfonyl)ethyl)-N-methyl-2-((1-methylpyrrolidin-2-yl)methoxy)-5,6,7,8-tetrahydropyrido[3,4-d]pyrimidin-4-amine The substitution reaction was prepared in a similar fashion to Example 1 (Method 1-A), Step 4, substituting (E)-N,N-dimethyl-3-((2-(methylamino)ethyl)sulfonyl)prop-2-en-1-amine for tert-butyl (2-(methylamino)ethyl)carbamate, and substituting (S)-7-(8-chloronaphthalen-1-yl)-2-((1-methylpyrrolidin-2-yl)methoxy)-5,6,7,8-tetrahydropyrido[3,4-d]pyrimidin-4-yl trifluoromethanesulfonate for (S)-7-(8-chloro-7-fluoronaphthalen-1-yl)-2-((1-methylpyrrolidin-2-yl)methoxy)-5,6,7,8-tetrahydropyrido[3,4-d]pyrimidin-4-yl trifluoromethanesulfonate. The crude product was purified by reverse phase HPLC (column: Phenomenex Luna C18 200*40 mm*10 μm; mobile phase: (water (FA)-acetonitrile; B %: 1%-30%, 8 min) affording (S,E)-7-(8-chloronaphthalen-1-yl)-N-(2-((3-(dimethylamino)prop-1-en-1-yl)sulfonyl)ethyl)-N-methyl-2-((1-methylpyrrolidin-2-yl)methoxy)-5,6,7,8-tetrahydropyrido[3,4-d]pyrimidin-4-amine (54.59 mg, 10.56%, formate salt) as a yellow oil: $^1$H NMR (400 MHz, Acetonitrile-d3) δ 8.26 (br s, 1H), 7.85 (d, J=7.4 Hz, 1H), 7.68 (d, J=7.9 Hz, 1H), 7.58-7.47 (m, 2H), 7.42-7.35 (m, 1H), 7.32 (d, J=7.5 Hz, 1H), 6.79 (td, J=5.5, 15.2 Hz, 1H), 6.62 (dd, J=1.4, 15.3 Hz, 1H), 4.42 (br dd, J=5.5, 11.3 Hz, 1H), 4.37-4.29 (m, 1H), 4.20 (br d, J=17.3 Hz, 1H), 3.94-3.79 (m, 2H), 3.72 (br d, J=17.1 Hz, 1H), 3.60-3.36 (m, 4H), 3.34-3.19 (m, 3H), 3.16 (s, 3H), 3.14-3.03 (m, 3H), 2.57 (br s, 5H), 2.22 (s, 5H), 2.16-2.08 (m, 1H), 1.91-1.73 (m, 3H). LCMS Rt=1.926 min, m/z=612.3 [M+H]+.

LCMS (5 to 95% acetonitrile in water+0.1% trifluoroacetic acid over 6 mins) retention time 1.926 min, ESI+ found [M+H]=612.3.

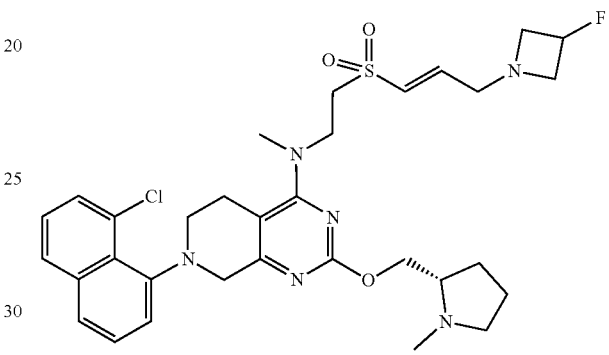

Example 53 (Method 6-V1): 7-(8-chloro-1-naphthyl)-N-[2-[(E)-3-(3-fluoroazetidin-1-yl)prop-1-enyl]sulfonylethyl]-N-methyl-2-[[(2S)-1-methylpyrrolidin-2-yl]methoxy]-6,8-dihydro-5H-pyrido[3,4-d]pyrimidin-4-amine

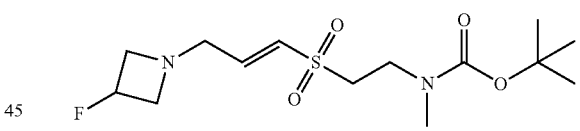

Step 1: tert-butylN-[2-[(E)-3-(3-fluoroazetidin-1-yl)prop-1-enyl]sulfonylethyl]-N-methyl-carbamate The substitution reaction was prepared in a similar fashion to Example 52 (Method 6-V), Step 6, substituting 3-fluoroazetidine hydrochloride for N-methylmethanamine. The crude product was concentrated in vacuo affording tert-butyl N-[2-[(E)-3-(3-fluoroazetidin-1-yl)prop-1-enyl]sulfonylethyl]-N-methyl-carbamate (200 mg, crude) as a colorless gum, which was used in the next step without further purification. LCMS Rt=0.788 min, m/z=336.2 [M+H]+.

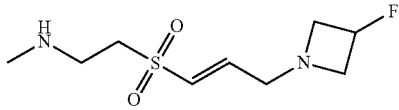

Step 2: 2-[(E)-3-(3-fluoroazetidin-1-yl)prop-1-enyl]sulfonyl-N-methyl-ethanamine The deprotection of Boc was prepared in a similar fashion to Example 52 (Method 6-V), Step 7. The reaction mixture was concentrated in vacuo affording 2-[(E)-3-(3-fluoroazetidin-1-yl)prop-1-enyl]sulfonyl-N-methyl-ethanamine (200 mg, crude, trifluoroacetate salt) as a pale yellow gum, which was used in the next step without further purification. LCMS Rt=0.529 min, m/z=236.1 [M+H]+.

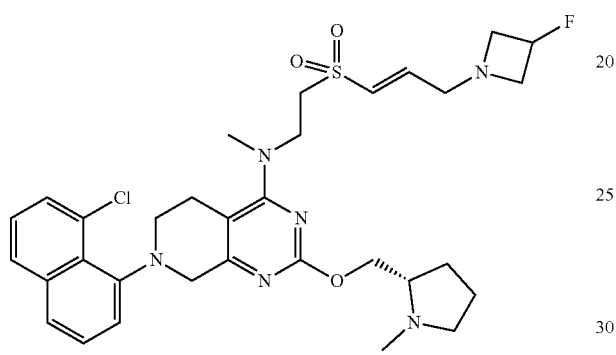

Step 3: 7-(8-chloro-1-naphthyl)-N-[2-[(E)-3-(3-fluoroazetidin-1-yl)prop-1-enyl]sulfonylethyl]-N-methyl-2-[[(2S)-1-methylpyrrolidin-2-yl]methoxy]-6,8-dihydro-5H-pyrido[3,4-d]pyrimidin-4-amine The substitution reaction was prepared in a similar fashion to Example 52 (Method 6-V), Step 8. The crude product was purified by reverse phase HPLC (column: Waters Xbridge BEH C18 100*30 mm*10 μm; mobile phase: [water(sodium bicarbonate)- acetonitrile]; B %: 55%-75%, 8 min) affording 7-(8-chloro-1-naphthyl)-N-[2-[(E)-3-(3-fluoroazetidin-1-yl)prop-1-enyl]sulfonylethyl]-N-methyl-2-[[(2S)-1-methylpyrrolidin-2-yl]methoxy]-6,8-dihydro-5H-pyrido[3,4-d]pyrimidin-4-amine (7.26 mg, 13.31%) as a yellow oil: $^1$H NMR (400 MHz, Acetonitrile-d3) δ 7.89-7.80 (m, 1H), 7.68 (d, J=8.00 Hz, 1H), 7.58-7.45 (m, 2H), 7.43-7.36 (m, 1H), 7.35-7.29 (m, 1H), 6.79-6.66 (m, 1H), 6.59-6.46 (m, 1H), 5.25-4.95 (m, 1H), 4.43-4.31 (m, 1H), 4.26-4.11 (m, 2H), 3.92 (ddt, J=14.15, 8.74, 5.44, 5.44 Hz, 1H), 3.84-3.75 (m, 1H), 3.74-3.67 (m, 1H), 3.66-3.56 (m, 2H), 3.55-3.43 (m, 2H), 3.37 (dt, J=8.57, 5.35 Hz, 1H), 3.31 (br dd, J=4.32, 1.81 Hz, 1H), 3.24-3.16 (m, 3H), 3.15-3.12 (m, 2H), 3.11-3.01 (m, 2H), 2.79-2.60 (m, 3H), 2.48-2.41 (m, 3H), 2.40-2.25 (m, 2H), 2.06-1.99 (m, 1H), 1.84-1.63 (m, 3H). LCMS Rt=3.527 min, m/z=642.3 [M+H]+.

LCMS (5 to 95% acetonitrile in water+0.03% ammonium bicarbonate over 6 mins) retention time 3.527 min, ESI+ found [M+H]=642.3.

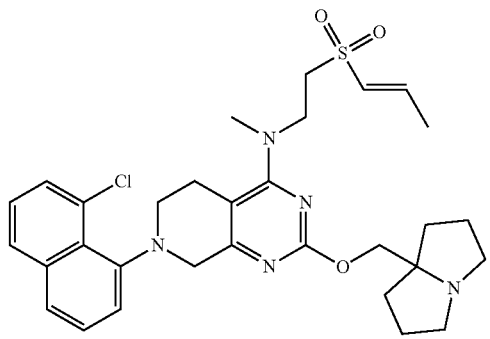 [SMILES: C/C=C/S(=O)(=O)CCN(C)c1nc(OCC23CCCN2CCC3)nc2c1CCN(c1cccc3cccc(Cl)c13)C2]

Example 54 (Method 5-V3): (E)-7-(8-chloronaphthalen-1-yl)-2-((hexahydro-1H-pyrrolizin-7a-yl)methoxy)-N-methyl-N-(2-(prop-1-en-1-ylsulfonyl)ethyl)-5,6,7,8-tetrahydropyrido[3,4-d]pyrimidin-4-amine

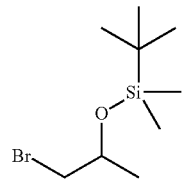

Step 1: ((1-bromopropan-2-yl)oxy)(tert-butyl)dimethylsilane

To a solution of 1-bromopropan-2-ol (7 g, 50.36 mmol) in dichloromethane (60 mL) was added tert-butylchlorodimethylsilane (9.11 g, 60.44 mmol) and imidazole (4.11 g, 60.44 mmol). The mixture was stirred at 20° C. for 12 h. The reaction mixture was concentrated in vacuo affording ((1-bromopropan-2-yl)oxy)(tert-butyl)dimethylsilane (12.75 g, crude) as a colorless oil, which was used in the next step without further purification.

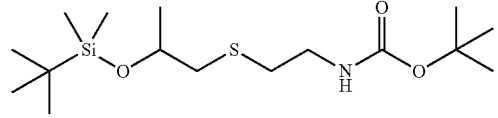 [SMILES: CC(CSCCNC(=O)OC(C)(C)C)O[Si](C)(C)C(C)(C)C]

Step 2: tert-butyl (2-((2-((tert-butyldimethylsilyl)oxy)propyl)thio)ethyl)carbamate The substitution reaction was prepared in a similar fashion to Example 46 (Method 4-V), Step 2, substituting ((1-bromopropan-2-yl)oxy)(tert-butyl)dimethylsilane for 3-((tert-butoxycarbonyl)(methyl)amino)propyl 4-methylbenzenesulfonate. The crude product was purified by column chromatography (silica gel, 100-200 mesh, 0-100% ethyl acetate in petroleum ether) affording tert-butyl (2-((2-((tert-butyldimethylsilyl)oxy)propyl)thio)ethyl)carbamate (12 g, 68.2%) as a white solid: $^1$H NMR (400 MHz, Chloroform-d) δ 4.92 (br s, 1H), 3.91 (q, J=5.9 Hz, 1H), 3.29 (br s, 2H), 2.65 (t, J=6.5 Hz, 2H), 2.61-2.46 (m, 1H), 1.72-1.53 (m, 1H), 1.43 (s, 9H), 1.20 (d, J=6.1 Hz, 3H), 0.87 (s, 9H), 0.06 (d, J=5.0 Hz, 6H).

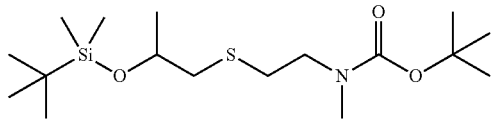 [SMILES: CC(CSCCN(C)C(=O)OC(C)(C)C)O[Si](C)(C)C(C)(C)C]

Step 3: tert-butyl (2-((2-((tert-butyldimethylsilyl)oxy)propyl)thio)ethyl)(methyl)carbamate To a solution of tert-butyl (2-((2-((tert-butyldimethylsilyl)oxy)propyl)thio)ethyl)carbamate (3 g, 8.58 mmol) in N,N-dimethylformaldehyde (20 mL) was added iodomethane (3.65 g, 25.74 mmol) and sodium hydride (1.03 g, 25.74 mmol, 60% purity) at 0° C. The mixture was stirred at 25° C. for 2 h. The reaction mixture was quenched with saturated ammonium chloride (20 mL) at 0° C. and extracted with ethyl acetate (3×20 mL). The combined organic layers were dried over sodium sulphate and concentrated in vacuo. The resulting residue was purified by column chromatography (silica gel, 100-200 mesh, 5-80% ethyl acetate in petroleum ether) affording tert-butyl (2-((2-((tert-butyldimethylsilyl)oxy)propyl)thio)ethyl)(methyl)carbamate (2 g, 64.1%) as a yellow oil: ¹H NMR (400 MHz, Chloroform-d) δ 2.80 (s, 3H), 2.73 (br s, 1H), 2.57 (br d, J=6.1 Hz, 2H), 2.54-2.41 (m, 2H), 1.69-1.50 (m, 2H), 1.38 (s, 9H), 1.13 (br d, J=6.0 Hz, 3H), 0.81 (s, 9H), -0.01 (br d, J=5.3 Hz, 6H).

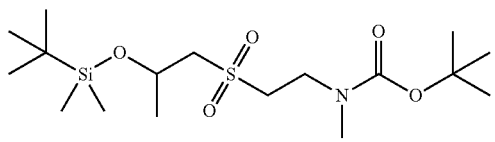 [SMILES: CC(CS(=O)(=O)CCN(C)C(=O)OC(C)(C)C)O[Si](C)(C)C(C)(C)C]

Step 4: tert-butyl (2-((2-((tert-butyldimethylsilyl)oxy)propyl)sulfonyl)ethyl)(methyl)carbamate The epoxidation was prepared in a similar fashion to Example 48 (Method 5-V), Step 3.

The crude product was purified by column chromatography (silica gel, 100-200 mesh, 0-100% ethyl acetate in petroleum ether) affording tert-butyl (2-((2-((tert-butyldimethylsilyl)oxy)propyl)sulfonyl)ethyl)(methyl)carbamate (1.2 g, 55.15%) as a yellow solid: ¹H NMR (400 MHz, Chloroform-d) δ 4.39-4.30 (m, 1H), 3.56 (br t, J=6.5 Hz, 2H), 3.15 (br s, 2H), 2.87-2.81 (m, 2H), 2.80-2.74 (m, 3H), 1.34 (s, 9H), 1.18 (d, J=6.3 Hz, 3H), 0.77 (s, 9H), 0.04-0.05 (m, 6H).

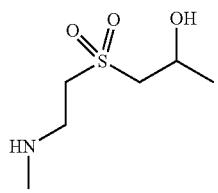

Step 5: 1-((2-(methylamino)ethyl)sulfonyl)propan-2-ol

The deprotection of Boc was prepared in a similar fashion to Example 48 (Method 5-V), Step 4. The reaction mixture was concentrated to dryness in vacuo affording 1-((2-(methylamino)ethyl)sulfonyl)propan-2-ol (180 mg, crude, trifluoroacetate salt) as a yellow oil, which was used in next step without further purification. LCMS Rt=0.175 min, m/z=181.1 [M+H]+.

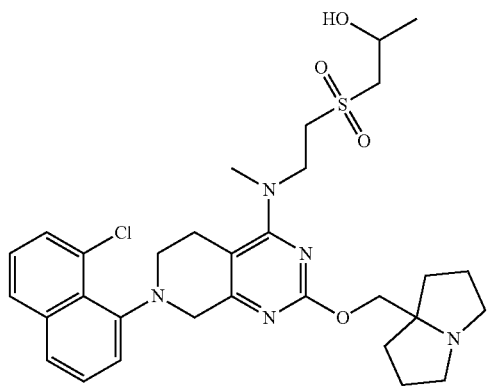 [SMILES: CC(O)CS(=O)(=O)CCN(C)c1nc(OCC23CCCN2CCC3)nc2c1CCN(c1cccc3cccc(Cl)c13)C2]

Step 6: 1-((2-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)ethyl)sulfonyl)propan-2-ol The substitution reaction was prepared in a similar fashion to Example 48 (Method 5-V), Step 5. The crude product was purified by reverse phase HPLC (column: Phenomenex Luna C18 150*30 mm*5 µm; mobile phase: (water(trifluoroacetic acid)- acetonitrile; B %: 25%-65%, 8 min) affording 1-((2-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)ethyl)sulfonyl)propan-2-ol (50 mg, 20.02%, trifluoroacetate salt) as a yellow oil. LCMS Rt=2.136 min, m/z=613.3 [M+H]+.

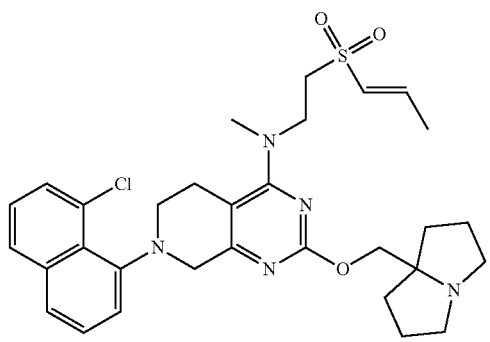 [SMILES: C/C=C/S(=O)(=O)CCN(C)c1nc(OCC23CCCN2CCC3)nc2c1CCN(c1cccc3cccc(Cl)c13)C2]

Step 7: (E)-7-(8-chloronaphthalen-1-yl)-2-((hexahydro-1H-pyrrolizin-7a-yl)methoxy)-N-methyl-N-(2-(prop-1-en-1-ylsulfonyl)ethyl)-5,6,7,8-tetrahydropyrido[3,4-d]pyrimidin-4-amine The elimination was prepared in a similar fashion to Example 48 (Method 5-V), Step 6. The crude product was firstly purified by reverse phase HPLC (column: Phenomenex Luna 80*30 mm*3 μm; mobile phase: (water (formic acid)-acetonitrile; B %: 10%-40%, 8 min) affording (E)-7-(8-chloronaphthalen-1-yl)-2-((hexahydro-1H-pyrrolizin-7a-yl)methoxy)-N-methyl-N-(2-(prop-1-en-1-ylsulfonyl) ethyl)-5,6,7,8-tetrahydropyrido[3,4-d]pyrimidin-4-amine (8.93 mg, 18.72%, formate salt) as a yellow oil: $^1$H NMR (400 MHz, Acetonitrile-d3) δ 8.35 (s, 1H), 7.88 (d, J=8.1 Hz, 1H), 7.71 (d, J=7.9 Hz, 1H), 7.60-7.50 (m, 2H), 7.46-7.39 (m, 1H), 7.35 (d, J=7.5 Hz, 1H), 6.92-6.80 (m, 1H), 6.48 (dd, J=1.6, 15.0 Hz, 1H), 4.23 (d, J=17.4 Hz, 1H), 4.17-4.13 (m, 2H), 3.98-3.90 (m, 1H), 3.88-3.79 (m, 1H), 3.75 (d, J=17.4 Hz, 1H), 3.57-3.45 (m, 2H), 3.39-3.32 (m, 1H), 3.26-3.22 (m, 1H), 3.18-3.17 (m, 3H), 3.13-3.08 (m, 1H), 2.80-2.74 (m, 2H), 2.68 (br d, J=15.3 Hz, 2H), 2.42 (br s, 1H), 2.06-2.01 (m, 2H), 1.96-1.93 (m, 3H), 1.93 (d, J=1.6 Hz, 2H), 1.91-1.85 (m, 2H), 1.78-1.71 (m, 2H). LCMS Rt=2.144 min, m/z=595.2 [M+H]+.

LCMS (5 to 95% acetonitrile in water+0.1% trifluoroacetic acid over 6 mins) retention time 2.144 min, ESI+ found [M+H]=595.2.

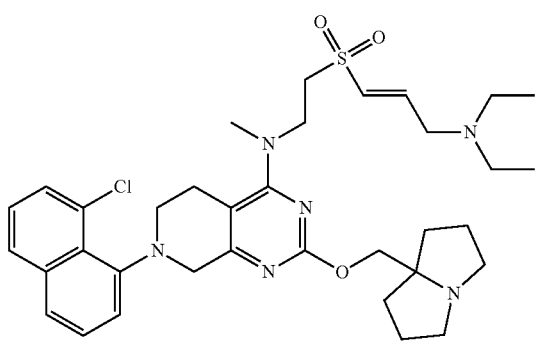 [SMILES: CCN(CC)C/C=C/S(=O)(=O)CCN(C)c1nc(OCC23CCCN2CCC3)nc2c1CCN(c1cccc3cccc(Cl)c13)C2]

Example 55 (Method 6-V2): (E)-7-(8-chloronaphthalen-1-yl)-N-(2-((3-(diethylamino)prop-1-en-1-yl)sulfonyl)ethyl)-2-((hexahydro-1H-pyrrolizin-7a-yl)methoxy)-N-methyl-5,6,7,8-tetrahydropyrido[3,4-d]pyrimidin-4-amine

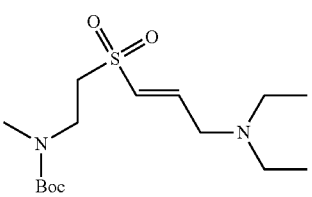 [SMILES: CCN(CC)C/C=C/S(=O)(=O)CCN(C)C(=O)OC(C)(C)C]

Step 1: (E)-tert-butyl (2-((3-(diethylamino)prop-1-en-1-yl)sulfonyl)ethyl)(methyl)carbamate The substitution was prepared in a similar fashion to Example 52 (Method 6-V), Step 6, substituting N-ethylethanamine for N-methylmethanamine. The crude product was concentrated in vacuo affording (E)-tert-butyl (2-((3-(diethylamino)prop-1-en-1-yl)sulfonyl)ethyl)(methyl)carbamate (100 mg, crude) as a yellow gum. LCMS Rt=0.833 min, m/z=334.2 [M+H]+.

Step 2: (E)-N,N-diethyl-3-((2-(methylamino)ethyl)sulfonyl)prop-2-en-1-amine

The deprotection of Boc was prepared in a similar fashion to Example 52 (Method 6-V), Step 7. The mixture was concentrated to dryness in vacuo affording (E)-N,N-diethyl-3-[2-(methylamino)ethylsulfonyl]prop-2-en-1-amine (100 mg, crude, trifluoroacetate salt) as a brown gum, which was used in the next step without further purification. LCMS Rt=0.581 min, m/z=

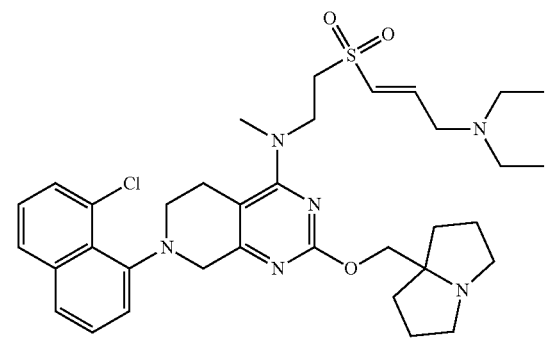 [SMILES: CCN(CC)C/C=C/S(=O)(=O)CCN(C)c1nc(OCC23CCCN2CCC3)nc2c1CCN(c1cccc3cccc(Cl)c13)C2]

Step 3: (E)-7-(8-chloronaphthalen-1-yl)-N-(2-((3-(diethylamino)prop-1-en-1-yl)sulfonyl)ethyl)-2-((hexahydro-1H-pyrrolizin-7a-yl)methoxy)-N-methyl-5,6,7,8-tetrahydropyrido[3,4-d]pyrimidin-4-amine The substitution reaction was prepared in a similar fashion to Example 52 (Method 6-V), Step 8. The crude product was purified by reverse phase HPLC (column: Waters Xbridge BEH C18 100*30 mm*10 μm; mobile phase: (water (ammonium bicarbonate)-acetonitrile]; B %: 40%-70%, 10 min) affording (E)-7-(8-chloronaphthalen-1-yl)-N-(2-((3-(diethylamino)prop-1-en-1-yl)sulfonyl)ethyl)-2-((hexahydro-1H-pyrrolizin-7a-yl)methoxy)-N-methyl-5,6,7,8-tetrahydropyrido[3,4-d]pyrimidin-4-amine (8.64 mg, 13.8%) as a yellow oil: $^1$H NMR (400 MHz, Acetonitrile-d3) δ 7.85 (d, J=7.2 Hz, 1H), 7.68 (d, J=7.6 Hz, 1H), 7.57-7.47 (m, 2H), 7.42-7.37 (m, 1H), 7.32 (d, J=7.5 Hz, 1H), 6.82 (td, J=5.3, 15.1 Hz, 1H), 6.66-6.56 (m, 1H), 4.20 (d, J=17.0 Hz, 1H), 3.96 (s, 2H), 3.93-3.85 (m, 1H), 3.79 (ddd, J=5.7, 8.7, 14.2 Hz, 1H), 3.71 (br d, J=17.5 Hz, 1H), 3.54-3.43 (m, 2H), 3.40-3.31 (m, 1H), 3.27-3.15 (m, 4H), 3.13 (s, 3H), 3.08-3.04 (m, 1H), 3.00-2.93 (m, 2H), 2.65-2.58 (m, 2H), 2.51-2.43 (m, 4H), 1.87-1.72 (m, 6H), 1.59 (td, J=7.2, 12.1 Hz, 2H), 0.96 (t, J=7.2 Hz, 6H). LCMS Rt=2.964 min, m/z=666.3 [M+H]+.

LCMS (5 to 95% acetonitrile in water+0.03% ammonium bicarbonate over 6 mins) retention time 2.964 min, ESI+ found [M+H]=666.3.

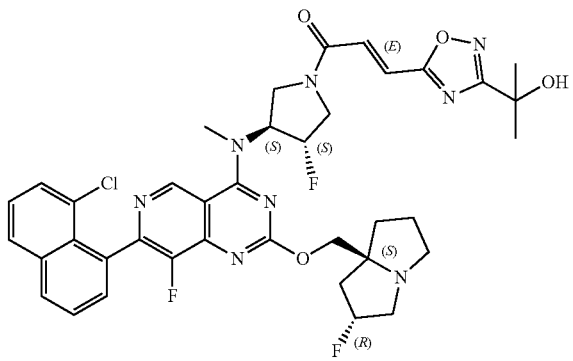

Example 56 (Method 1): (E)-1-((3S,4S)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidin-1-yl)-3-(3-(2-hydroxypropan-2-yl)-1,2,4-oxadiazol-5-yl)prop-2-en-1-one

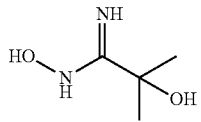

Step 1: N, 2-dihydroxy-2-methylpropanimidamide

The hydroxylimidamide formation was prepared in a similar fashion to Method #1, Step 1. The resulting residue was purified by column chromatography (silica gel, 100-200 mesh, 0-100% ethyl acetate in petroleum ether) affording N, 2-dihydroxy-2-methylpropanimidamide (2.2 g, crude) as a white solid, used in next step without any further purification. LCMS Rt=0.351 min, m/z=118.1 [M+H]⁺.

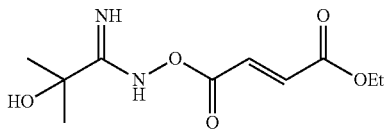 [SMILES: CCOC(=O)/C=C/C(=O)ONC(=N)C(C)(C)O]

Step 3: (E)-ethyl 4-((2-hydroxy-2-methylpropanimidamido)oxy)-4-oxobut-2-enoate

The amide coupling reaction was prepared in a similar fashion to Method #1, Step 2. The resulting residue was purified by column chromatography (silica gel, 100-200 mesh, 0-100% ethyl acetate in petroleum ether) affording (E)-ethyl 4-((2-hydroxy-2-methylpropanimidamido)oxy)-4-oxobut-2-enoate (2.2 g, 49.89%) as a white solid. LCMS Rt=0.552 min, m/z=244.1 [M+H]⁺.

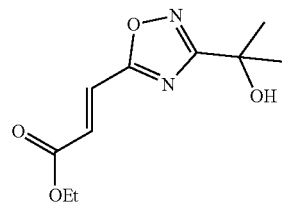 [SMILES: CCOC(=O)/C=C/c1nc(C(C)(C)O)no1]

Step 4: (E)-ethyl 3-(3-(2-hydroxypropan-2-yl)-1,2,4-oxadiazol-5-yl)acrylate

The cyclization reaction was prepared in a similar fashion to Method #1, Step 3. The resulting residue was purified by column chromatography (silica gel, 100-200 mesh, 0-100% ethyl acetate in petroleum ether) affording (E)-ethyl 3-(3-(2-hydroxypropan-2-yl)-1,2,4-oxadiazol-5-yl)acrylate (350 mg, 40%) as a white solid: ¹H NMR (400 MHz, Chloroform-d) δ 7.41 (d, J=16.0 Hz, 1H), 6.97 (d, J=16.0 Hz, 1H), 4.31-4.17 (m, 2H), 1.64-1.55 (m, 6H), 1.34-1.23 (m, 3H). LCMS Rt =0.590 min, m/z=226.1 [M+H]⁺.

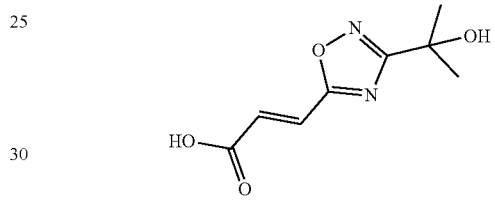

Step 5: (E)-3-(3-(2-hydroxypropan-2-yl)-1,2,4-oxadiazol-5-yl)acrylic acid

The hydrolysis reaction was prepared in a similar fashion to Method #1, Step 4. The crude product was concentrated in vacuo affording (E)-3-(3-(2-hydroxypropan-2-yl)-1,2,4-oxadiazol-5-yl)acrylic acid (180 mg, 55.94%) as a white solid. LCMS Rt=0.467 min, m/z=198.1 [M+H]⁺.

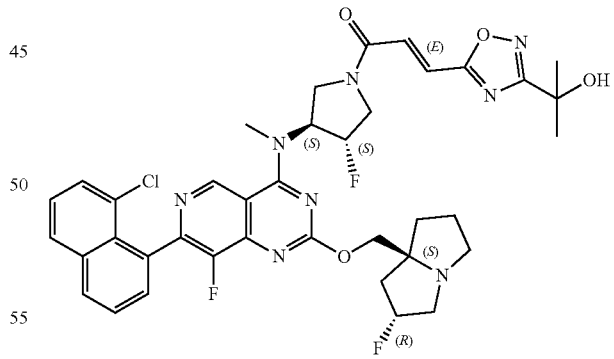

Step 6: (E)-1-((3S,4S)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidin-1-yl)-3-(3-(2-hydroxypropan-2-yl)-1,2,4-oxadiazol-5-yl)prop-2-en-1-one The amide coupling reaction was prepared in a similar fashion to Method #1, Step 10. The crude was purified by reverse phase HPLC (column: Waters Xbridge Prep OBD C18 150*40 mm*10 μm; mobile phase: [water (NH₄HCO₃)-acetonitrile]; B %: 35%-65%, 8 min) affording (E)-1-((3S,4S)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidin-1-yl)-3-(3-(2-hydroxypropan-2-yl)-1,2,4-oxadiazol-5-yl)prop-2-en-1-one (25.3 mg, 22.65%) as a yellow solid: ¹H NMR (400 MHz, Acetonitrile-d3) δ 9.27 (s, 1H), 8.15 (dd, J=1.1, 8.1 Hz, 1H), 8.05 (d, J=7.5 Hz, 1H), 7.80-7.75 (m, 1H), 7.67-7.59 (m, 2H), 7.55-7.45 (m, 1H), 7.39-7.29 (m, 2H), 5.80-5.54 (m, 1H), 5.41-5.13 (m, 2H), 4.52-4.33 (m, 1H), 4.25-4.13 (m, 3H), 4.11-3.99 (m, 1H), 3.96-3.80 (m, 1H), 3.63-3.54 (m, 3H), 3.23-3.05 (m, 3H), 2.97-2.85 (m, 1H), 2.14-2.03 (m, 3H), 1.93-1.80 (m, 3H), 1.61 (d, J=6.9 Hz, 6H). LCMS Rt=2.418 min, m/z=762.3 [M+H]+.

LCMS (5 to 95% acetonitrile in water+0.03% ammonium bicarbonate over 6 mins) retention time 2.418 min, ESI+ found [M+H]=762.3.

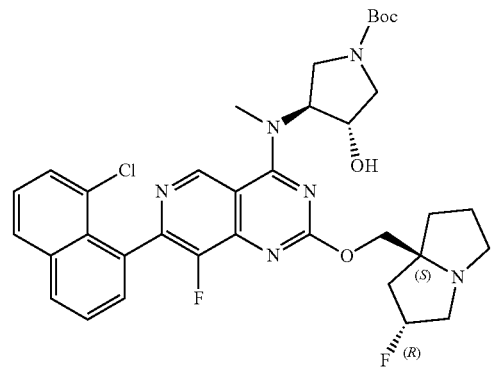

Example 57 (Method 6): 1-((3S,4S)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-hydroxypyrrolidin-1-yl)prop-2-en-1-one

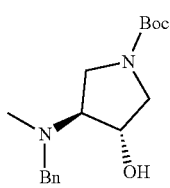 [SMILES: CN(Cc1ccccc1)[C@H]1CN(C(=O)OC(C)(C)C)C[C@@H]1O]

Step 1: (3S,4S)-tert-butyl 3-(benzyl(methyl)amino)-4-hydroxypyrrolidine-1-carboxylate The reductive amination was prepared in a similar fashion to Method #6, Step 1. The residue was purified by column chromatography (silica gel, 100-200 mesh, 0-100% ethyl acetate in petroleum ether) affording (3S,4S)-tert-butyl 3-(benzyl(methyl)amino)-4-hydroxypyrrolidine-1-carboxylate (2.2 g, 76.43%) as a colorless oil: ¹H NMR (400 MHz, Chloroform-d) 7.42-7.21 (m, 5H), 4.43-4.32 (m, 1H), 3.84-3.60 (m, 4H), 3.46-3.06 (m, 3H), 2.29 (s, 3H), 1.50 (s, 9H).

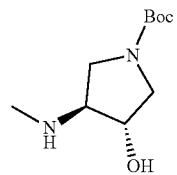

Step 2: (3S,4S)-tert-butyl 3-hydroxy-4-(methylamino)pyrrolidine-1-carboxylate

The deprotection of Bn group was prepared in a similar fashion to Method #6, Step 6. The mixture was concentrated to dryness in vacuo affording (3S,4S)-tert-butyl 3-hydroxy-4-(methylamino)pyrrolidine-1-carboxylate (1.4 g, crude) as a colorless oil, used in next step without any further purification.

Step 3: (3S,4S)-tert-butyl 3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-hydroxypyrrolidine-1-carboxylate The substitution reaction was prepared in a similar fashion to Method #1, Step 8. The residue was purified by reverse phase HPLC (column: Phenomenex luna C18 250*50 mm*10 μm; mobile phase: [water (trifluoroacetic acid)-acetonitrile]; B %: 20%-50%, 10 min) affording (3S,4S)-tert-butyl 3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-hydroxypyrrolidine-1-carboxylate (170 mg, 26.80%, trifluoroacetate salt) as a yellow oil. LCMS Rt=1.479 min, m/z=680.3 [M+H]+.

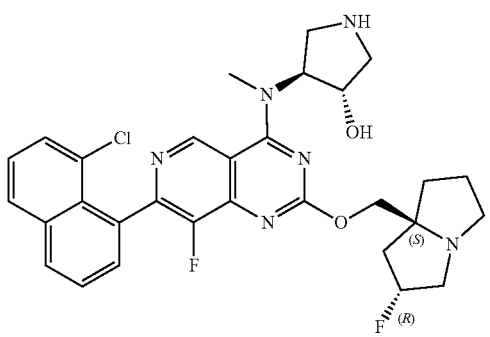

Step 4: (3S,4S)-4-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-3-ol The de-Boc protecting reaction was prepared in a similar fashion to Method #1, Step 9. The reaction mixture was concentrated in vacuo (3S,4S)-4-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-3-ol (10 mg, crude, trifluoroacetate salt) as a yellow oil, used in next step without further purification. LCMS Rt=0.573 min, m/z=580.2 [M+H]$^+$.

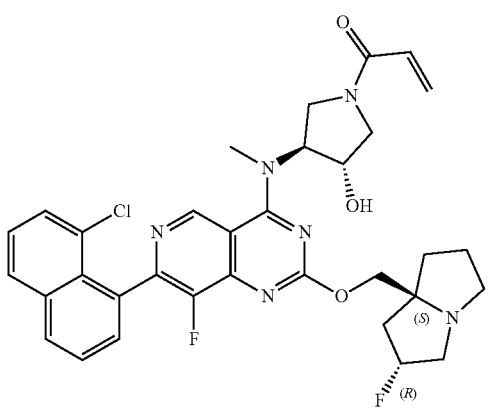

Step 5: 1-((3S,4S)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-hydroxypyrrolidin-1-yl)prop-2-en-1-one The amide coupling reaction was prepared in a similar fashion to Method #6, Step 13. The residue was purified by reverse phase HPLC (column: Waters Xbridge Prep OBD C18 150*40 mm*10 um; mobile phase: [water (NH$_4$HCO$_3$)-acetonitrile]; B %: 30%-60%, 8 min) affording 1-((3S,4S)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-hydroxypyrrolidin-1-yl)prop-2-en-1-one (15.02 mg, 19.66%) as a yellow oil: $^1$H NMR (400 MHz, Acetonitrile-d3) δ 9.28 (dd, J=2.5, 11.8 Hz, 1H), 8.14 (d, J=7.8 Hz, 1H), 8.03 (d, J=8.3 Hz, 1H), 7.74-7.58 (m, 3H), 7.55-7.51 (m, 1H), 6.61-6.52 (m, 1H), 6.26 (br d, J=16.8 Hz, 1H), 5.73-5.68 (m, 1H), 5.35 (br s, 1H), 4.73-4.64 (m, 1H), 4.26-4.22 (m, 1H), 4.19 (d, J=1.9 Hz, 1H), 4.17-4.10 (m, 1H), 4.02-4.01 (m, 1H), 4.08-3.94 (m, 1H), 3.76-3.51 (m, 1H), 3.46-3.42 (m, 3H), 3.29-3.12 (m, 3H), 3.10 (s, 1H), 2.96-2.89 (m, 1H), 2.24-2.18 (m, 1H), 2.15-2.12 (m, 1H), 2.07 (br d, J=7.5 Hz, 1H), 1.96-1.81 (m, 3H). LCMS Rt=2.783 min, m/z=634.2 [M+H]+.

LCMS (5 to 95% acetonitrile in water+0.03% ammonium bicarbonate over 6 mins) retention time 2.783 min, ESI+ found [M+H]=634.2.

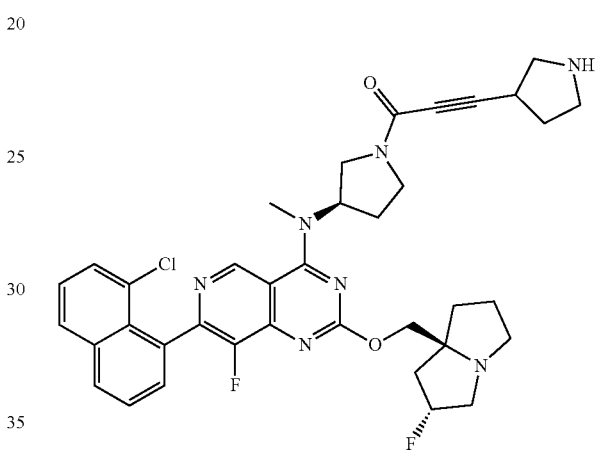

Example 58 (Method 7): 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(pyrrolidin-3-yl)prop-2-yn-1-one

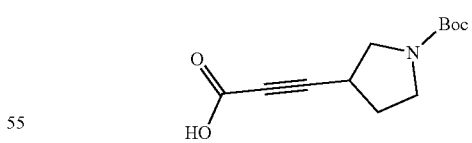

Step 1: 3-(1-(tert-butoxycarbonyl)pyrrolidin-3-yl)propiolic acid

The carbonylation reaction was prepared in a similar fashion to Method #7, Step 1. The mixture was concentrated in vacuo affording 3-(1-(tert-butoxycarbonyl)pyrrolidin-3-yl)propiolic acid (430 mg, crude) as a yellow oil, used in next step without any further purification.

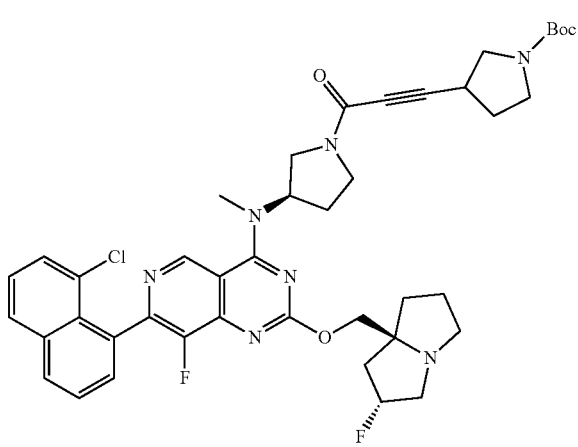 [SMILES: CN(c1nc(OC[C@@]23CCCN2C[C@H](F)C3)nc2c(F)c(-c3cccc4cccc(Cl)c34)ncc12)[C@@H]1CCN(C(=O)C#CC2CCN(C(=O)OC(C)(C)C)C2)C1]

Step 2: tert-butyl 3-(3-((R)-3-((7-(8-chloronaphtha-len-1-yl)-8-fluoro-2-(((2R,7aS)-2-fluorohexahydro-1H-pyrrolizin-7a-yl)methoxy)pyrido[4,3-d]pyrimi-din-4-yl)(methyl)amino)pyrrolidin-1-yl)-3-oxoprop-1-yn-1-yl)pyrrolidine-1-carboxylate The amide coupling reaction was prepared in a similar fashion to Method #7, Step 2. The crude was purified by reverse phase HPLC (column: Phenomenex Luna 80*30 mm*3 μm; mobile phase: [water (trifluoroacetic acid)-acetonitrile]; B %: 30%-60%, 8 min) affording tert-butyl 3-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)pyrrolidine-1-carboxylate (130 mg, 29.73%, trifluoroacetate salt) as a white solid. LCMS Rt=0.768 min, m/z=785.3 [M+H]+.

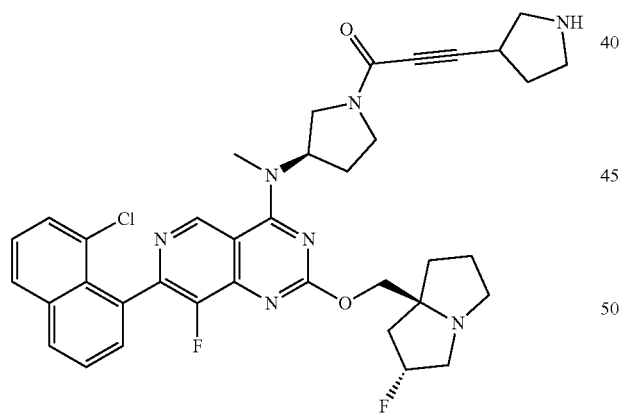

Step 3: 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(pyrrolidin-3-yl)prop-2-yn-1-one The de-Boc protecting reaction was prepared in a similar fashion to Method #7, Step 3. The residue was purified by reverse phase HPLC (column: Phenomenex Luna C18 75*30 mm*3 μm; mobile phase: [water (formic acid)-acetonitrile]; B %: 1%-35%, 8 min) affording 1-((R)-3-((7-(8-chloronaphthalen-1-yl)-8-fluoro-2-(((2R,7aS)-2-fluoro-hexahydro-1H-pyrrolizin-7a-yl)methoxy)pyrido[4,3-d]pyrimidin-4-yl)(methyl)amino)pyrrolidin-1-yl)-3-(pyrrolidin-3-yl)prop-2-yn-1-one (8.51 mg, 8.72%, formate salt) as a white solid: $^1$H NMR (400 MHz, Acetonitrile-d3) δ 9.24 (br d, J=7.0 Hz, 1H), 8.38-8.02 (m, 3H), 7.78-7.53 (m, 4H), 5.39-5.19 (m, 2H), 4.21-4.04 (m, 4H), 3.95-3.77 (m, 2H), 3.73-3.60 (m, 2H), 3.48-3.38 (m, 4H), 3.32-3.23 (m, 1H), 3.10 (br d, J=8.3 Hz, 2H), 3.02 (br s, 1H), 2.84 (br d, J=4.0 Hz, 2H), 2.32 (br s, 2H), 2.17-1.99 (m, 4H), 1.89-1.72 (m, 4H). LCMS Rt=1.945 min, m/z=685.3 [M+H]+.

LCMS (5 to 95% acetonitrile in water+0.03% ammonium bicarbonate over 6 mins) retention time 1.945 min, ESI+ found [M+H]=685.3.

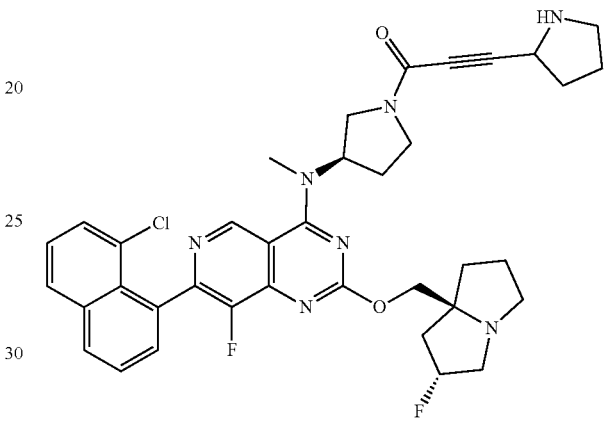

Example 59 (Method 7): 1-((R)-3-((7-(8-chloronaphthalen-1-yl)-8-fluoro-2-(((2R,7aS)-2-fluoro-tetrahydro-1H-pyrrolizin-7a(5H)-yl)methoxy)pyrido[4,3-d]pyrimidin-4-yl)(methyl)amino)pyrrolidin-1-yl)-3-(pyrrolidin-2-yl)prop-2-yn-1-one

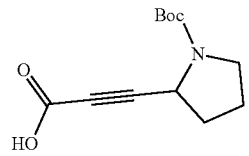 [SMILES: CC(C)(C)OC(=O)N1CCCC1C#CC(=O)O]

Step 1: 3-(1-(tert-butoxycarbonyl)pyrrolidin-2-yl) propiolic acid

Prepared according to Method #7, Step 1. To a solution of tert-butyl 2-ethynylpyrrolidine-1-carboxylate (100 mg, 512.14 μmol) in tetrahydrofuran (10 mL) was added n-butyl-lithium (2.5 M, 102.43 uL) at −78° C. under nitrogen. The mixture was stirred at −78° C. for 0.5 h, then added carbon dioxide. The mixture was stirred at −78° C. for 1 h. The reaction mixture was quenched with saturated ammonium chloride (5 mL) at 0° C. then added potassium hydrogen sulfate (5 mL), and extracted with ethyl acetate (3×10 mL). The combined organic layers were dried over sodium sulphate and concentrated in vacuo affording 3-(1-(tert-butoxy-carbonyl)pyrrolidin-2-yl)propiolic acid (110 mg, crude) as a yellow oil, used in next step without any further purification

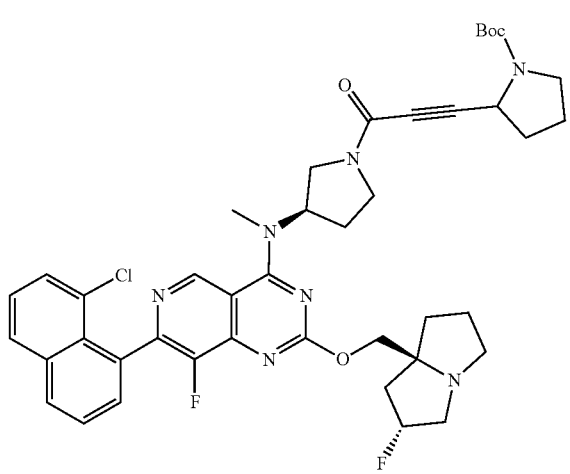 [SMILES: CN(c1nc(OC[C@@]23CCCN2C[C@H](F)C3)nc2c(F)c(-c3cccc4cccc(Cl)c34)ncc12)[C@@H]1CCN(C(=O)C#CC2CCCN2C(=O)OC(C)(C)C)C1]

Step 2: tert-butyl 2-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)pyrrolidine-1-carboxylate Prepared according to Method #7, Step 2. The amide coupling reaction was prepared in a similar fashion to Method #1, Step 10. The mixture was diluted with water (10 mL) and extracted with ethyl acetate (3×10 mL). The combined organic layers were dried over sodium sulphate and concentrated in vacuo affording tert-butyl 2-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)pyrrolidine-1-carboxylate (200 mg, crude) as a yellow oil, used in next step without any further purification. LCMS Rt=0.708 min, m/z=785.3 [M+H]$^+$.

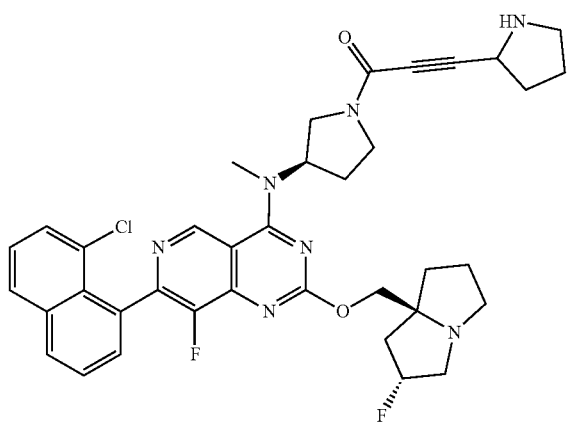 [SMILES: CN(c1nc(OC[C@@]23CCCN2C[C@H](F)C3)nc2c(F)c(-c3cccc4cccc(Cl)c34)ncc12)[C@@H]1CCN(C(=O)C#CC2CCCN2)C1]

Step 3: 1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(pyrrolidin-2-yl)prop-2-yn-1-one Prepared according to Method #7, Step 3. The deprotection of Boc group was prepared in a similar fashion to Method #1, Step 9. The residue was purified by reverse phase HPLC (column: Phenomenex Luna C18 75*30 mm*3 μm; mobile phase: [water (formic acid)-acetonitrile]; B %:1%-35%, 8 min) affording 1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(pyrrolidin-2-yl)prop-2-yn-1-one (14.08 mg, 14.77%, formate salt) as a yellow oil: $^1$H NMR (400 MHz, Acetonitrile-d3) δ 9.22 (dd, J=2.1, 7.6 Hz, 1H), 8.25 (s, 1H), 8.15 (d, J=8.1 Hz, 1H), 8.04 (d, J=8.1 Hz, 1H), 7.75-7.61 (m, 3H), 7.57-7.50 (m, 1H), 5.49-5.25 (m, 2H), 4.38-4.24 (m, 2H), 4.18-4.05 (m, 1H), 4.02-3.86 (m, 1H), 3.82-3.62 (m, 2H), 3.54-3.38 (m, 5H), 3.36-3.16 (m, 3H), 3.09-3.03 (m, 1H), 3.00-2.92 (m, 1H), 2.43-2.26 (m, 4H), 2.24-2.07 (m, 3H), 2.06-2.01 (m, 1H), 1.95-1.84 (m, 3H), 1.84-1.76 (m, 1H). LCMS Rt=1.942 min, m/z=685.3 [M+H]+.

LCMS (5 to 95% acetonitrile in water+0.1% formic acid over 6 mins) retention time 1.942 min, ESI+ found [M+H] =685.3.

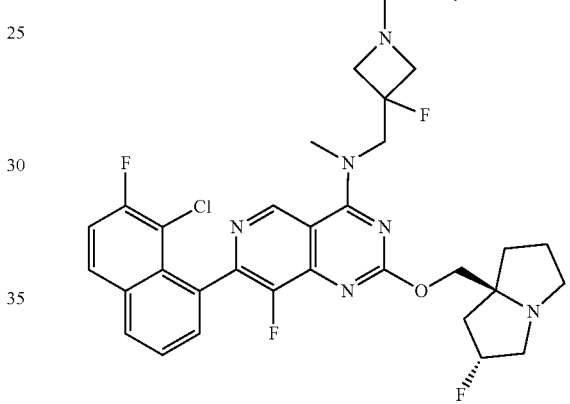

Example 60 (Method 1)$_1$-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)-3-fluoroazetidine-1-yl)prop-2-en-1-one

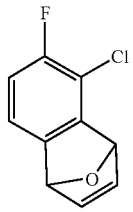 [SMILES: Fc1ccc2c(c1Cl)C1C=CC2O1]

Step 1:
5-chloro-6-fluoro-1,4-dihydro-1,4-epoxynaphthalene

To a solution of 1-bromo-3-chloro-2,4-difluoro-benzene (30 g, 131.91 mmol) and furan (17.96 g, 263.81 mmol) in toluene (500 mL) was added n-butyllithium (2.5 M, 63.32 mL) at −40° C. under nitrogen atmosphere. The mixture was stirred at 25° C. for 12 h. The mixture was quenched with a saturated solution of ammonium chloride (600 mL) dropwise at 0° C., exacted with ethyl acetate (3×200 ml). The organic layers were concentrated in vacuo affording 5-chloro-6-fluoro-1,4-dihydro-1,4-epoxynaphthalene (28 g, crude) as a brown oil used in the next step without further purification.

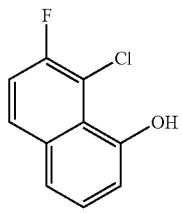

Step 2: 8-chloro-7-fluoronaphthalen-1-ol

To a solution of 5-chloro-6-fluoro-1,4-dihydro-1,4-epoxynaphthalene (28.00 g, 142.42 mmol) in ethanol (100 mL) was added hydrogenchloride (142.42 mL). The mixture was stirred at 80° C. for 6 h. The mixture was quenched with a saturated solution of sodium bicarbonate (500 mL) dropwise at 0° C., exacted with ethyl acetate (3×500 mL). The organic layers were concentrated in vacuo and the residue was purified by column chromatography (silica gel, 100-200 mesh, 0-5% ethyl acetate in petroleum ether) affording 8-chloro-7-fluoronaphthalen-1-ol (10 g, 35.71%) as a yellow solid. LCMS Rt=0.565 min, m/z=196.0 [M+H]+.

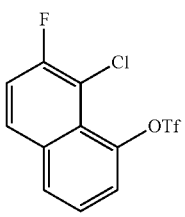 [SMILES: O=S(=O)(Oc1cccc2ccc(F)c(Cl)c12)C(F)(F)F]

Step 3: 8-chloro-7-fluoronaphthalen-1-yl trifluoromethanesulfonate

A mixture of 8-chloro-7-fluoronaphthalen-1-ol (9 g, 45.78 mmol), N-ethyl-N,N-diisopropylamine (35.50 g, 274.66 mmol) in dichloromethane (100 mL) was stirred for 10 minutes at 20° C. Then trifluoromethylsulfonic anhydride (16.79 g, 59.51 mmol) was added dropwise into the mixture at −10° C. The resulting mixture was stirred at −10° C. for 20 min under nitrogen atmosphere and then diluted with water (100 mL) and extracted with dichloromethane (3×100 mL). The organic layers were concentrated in vacuo and the residue was purified by column chromatography (silica gel, 100-200 mesh, 0-5% ethyl acetate in petroleum ether) affording 8-chloro-7-fluoronaphthalen-1-yl trifluoromethanesulfonate (14 g, 93.05%) as a yellow solid. LCMS Rt=0.734 min, m/z=328.0 [M+H]+.

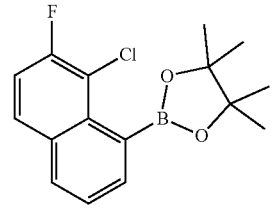 [SMILES: CC1(C)OB(c2cccc3ccc(F)c(Cl)c23)OC1(C)C]

Step 4: 2-(8-chloro-7-fluoronaphthalen-1-yl)-4,4,5,5-tetramethyl-1,3,2-dioxaborolane A mixture of 8-chloro-7-fluoronaphthalen-1-yl trifluoromethanesulfonate (20 g, 60.85 mmol), bis(pinacol)diborane (30.91 g, 121.70 mmol), (1,1'-bis(diphenylphosphino)ferrocene)palladium(II) dichloride (4.45 g, 6.09 mmol), potassium acetate (29.86 g, 304.26 mmol) in N,N-dimethylformamide (400 mL) was stirred at 80° C. for 12 h under nitrogen atmosphere. The reaction mixture was diluted with water (400 mL) and extracted with ethyl acetate (3×400 mL). The organic layers were concentrated in vacuo and the residue was purified by column chromatography (silica gel, 100-200 mesh, 0-5% ethyl acetate in petroleum ether) affording 2-(8-chloro-7-fluoronaphthalen-1-yl)-4,4,5,5-tetramethyl-1,3,2-dioxaborolane (18 g, 96.49%) as a yellow solid. LCMS Rt=0.847 min, m/z=306.1 [M+H]$^+$.

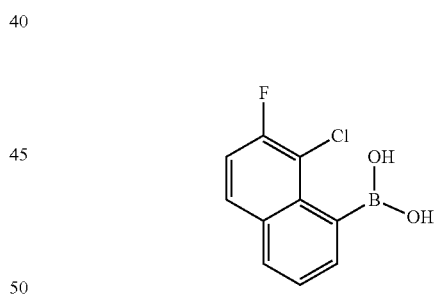

Step 5: (8-chloro-7-fluoronaphthalen-1-yl)boronic acid

To a solution of 2-(8-chloro-7-fluoronaphthalen-1-yl)-4,4,5,5-tetramethyl-1,3,2-dioxaborolane (18 g, 58.71 mmol) in acetonitrile (200 mL) and water (60 mL) was added ammonium acetate (18.10 g, 234.86 mmol) and sodium periodate (50.23 g, 234.86 mmol). The mixture was stirred at 70° C. for 12 h. The reaction mixture was diluted with water (100 mL) and extracted with ethyl acetate (2×200 mL). The organic layers were concentrated in vacuo. The crude product was purified by reverse phase HPLC (column: column: Phenomenex luna C18 (250*70 mm, 10 μm); mobile phase: [water (trifluoroacetic acid)-acetonitrile]; B %: 15%-45%, 25 min) affording (8-chloro-7-fluoronaphthalen-1-yl)boronic acid (4.9 g, 37.18%) as a yellow solid. LCMS Rt=0.694 min, m/z=224.0 [M+H]+.

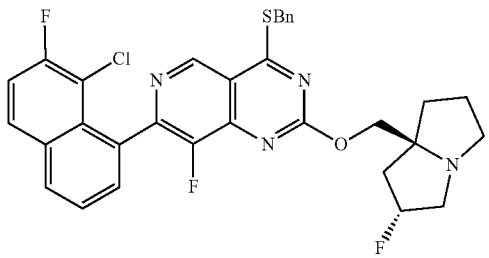 [SMILES: Fc1ccc2cccc(-c3ncc4c(Cl)nc(OC[C@@]56CCCN5C[C@H](F)C6)nc4c3F)c2c1Cl]

Step 6: 4-(benzylthio)-7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidine The Suzuki reaction was prepared in a similar fashion to Method #1, Step 6. The crude product was purified by column chromatography (silica gel, 100-200 mesh, 2%-100% ethyl acetate in petroleum ether) affording 4-(benzylthio)-7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidine (2.7 g, 62.39%) as a yellow oil. LCMS Rt=0.655 min, m/z=606.2 [M+H]+.

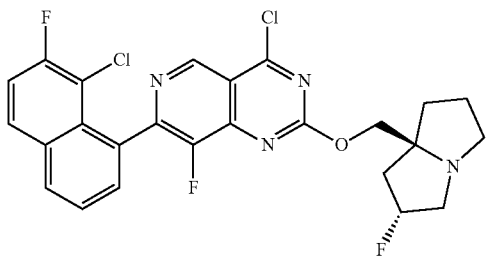

Step 7: 4-chloro-7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidine The chlorination reaction was prepared in a similar fashion to Method #1, Step 7. The crude product 4-chloro-7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidine (200 mg, crude) as a yellow liquid used in the next step without further purification. LCMS Rt=0.716 min, m/z=518.1 [M+H]+.

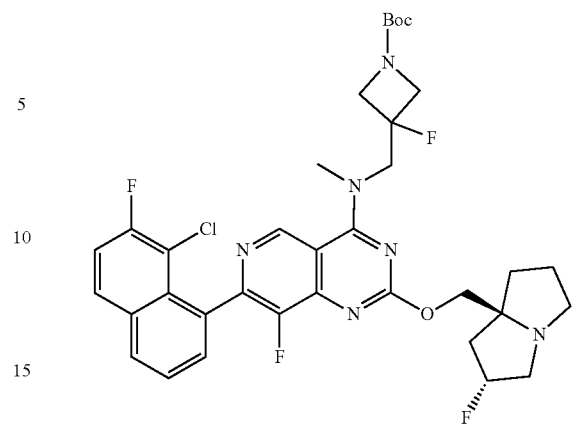

Step 8: tert-butyl 3-(((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)methyl)-3-fluoroazetidine-1-carboxylate The substitution reaction was prepared in a similar fashion to Method #1, Step 8. The residue was purified by reverse phase HPLC (column: Phenomenex Luna 80*30 mm*3 μm; mobile phase: [water (trifluoroacetic acid)-acetonitrile]; B %: 30%-60%, 8 min) affording tert-butyl 3-(((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)methyl)-3-fluoroazetidine-1-carboxylate (110 mg, 35.04%, trifluoroacetate salt) as a yellow oil. LCMS Rt=0.941 min, m/z=700.3 [M+H]+.

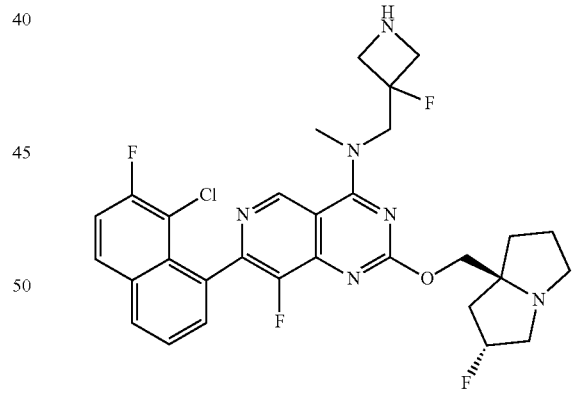

Step 9: 7-(8-chloro-7-fluoronaphthalen-1-yl)-8-fluoro-N-((3-fluoroazetidin-3-yl)methyl)-2-(((2R,7aS)-2-fluorohexahydro-1H-pyrrolizin-7a-yl)methoxy)-N-methylpyrido[4,3-d]pyrimidin-4-amine The de-Boc protecting reaction was prepared in a similar fashion to Method #1, Step 9. The mixture was concentrated in vacuo affording 7-(8-chloro-7-fluoronaphthalen-1-yl)-8-fluoro-N-((3-fluoroazetidin-3-yl)methyl)-2-(((2R,7aS)-2-fluorohexahydro-1H-pyrrolizin-7a-yl)methoxy)-N-methylpyrido[4,3-d]pyrimidin-4-amine (110 mg, crude, trifluoroacetate salt) as a yellow oil, used in the next step without further purification. LCMS Rt=0.600 min, m/z=600.2 [M+H]+.

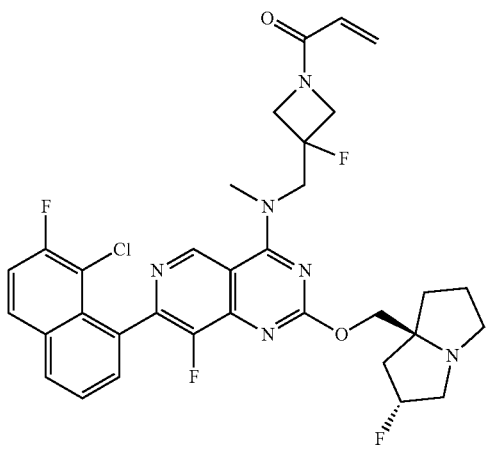 [SMILES: C=CC(=O)N1CC(F)(CN(C)c2nc(OC[C@@]34CCCN3C[C@H](F)C4)nc3c(F)c(-c4cccc5ccc(F)c(Cl)c45)ncc23)C1]

Step 10: 1-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)-3-fluoroazetidin-1-yl)prop-2-en-1-one The amide coupling reaction was prepared in a similar fashion to Method #1, Step 10. The residue was purified by reverse phase HPLC (column: Waters Xbridge Prep OBD C18 150*40 mm*10 μm; mobile phase: [water (NH$_4$HCO$_3$)-acetonitrile]; B %: 30%-60%, 8 min) affording 1-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)-3-fluoroazetidin-1-yl)prop-2-en-1-one (29.89 mg, 31.08%) as a white solid: $^1$H NMR (400 MHz, Acetonitrile-d3) δ 9.32 (s, 1H), 8.17-8.12 (m, 1H), 8.08 (dd, J=5.6, 9.1 Hz, 1H), 7.71-7.65 (m, 2H), 7.53 (t, J=8.9 Hz, 1H), 6.34-6.17 (m, 2H), 5.68 (dd, J=2.4, 9.9 Hz, 1H), 5.35-5.15 (m, 1H), 4.63-4.49 (m, 3H), 4.40-4.26 (m, 2H), 4.20-4.03 (m, 3H), 3.69 (d, J=1.0 Hz, 3H), 3.16-3.10 (m, 2H), 3.05 (s, 1H), 2.93-2.85 (m, 1H), 2.22-2.13 (m, 2H), 2.08 (br s, 1H), 2.05-1.99 (m, 1H), 1.85 (dt, J=3.8, 9.8 Hz, 2H). LCMS Rt=2.999 min, m/z=654.2 [M+H]+.

LCMS (5 to 95% acetonitrile in water+0.03% ammonium bicarbonate over 6 mins) retention time 2.999 min, ESI+ found [M+H]=654.2.

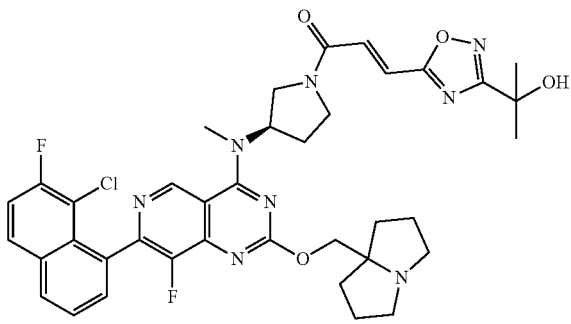 [SMILES: CN(c1nc(OCC23CCCN2CCC3)nc2c(F)c(-c3cccc4ccc(F)c(Cl)c34)ncc12)[C@@H]1CCN(C(=O)/C=C/c2nc(C(C)(C)O)no2)C1]

Example 61 (Method 1): (R,E)-1-(3-((7-(8-chloro-7-fluoronaphthalen-1-yl)-8-fluoro-2-((hexahydro-1H-pyrrolizin-7a-yl)methoxy)pyrido[4,3-d]pyrimidin-4-yl)(methyl)amino)pyrrolidin-1-yl)-3-(3-(2-hydroxypropan-2-yl)-1,2,4-oxadiazol-5-yl)prop-2-en-1-one

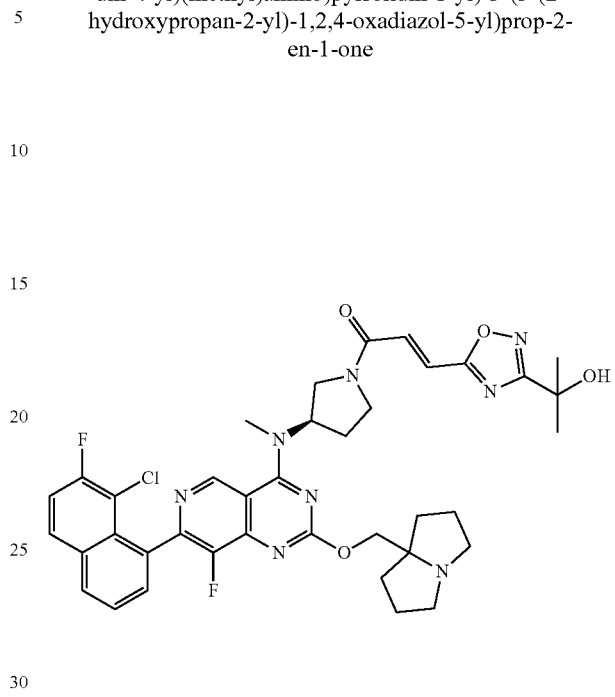

Step 1: (R,E)-1-(3-((7-(8-chloro-7-fluoronaphthalen-1-yl)-8-fluoro-2-((hexahydro-1H-pyrrolizin-7a-yl)methoxy)pyrido[4,3-d]pyrimidin-4-yl)(methyl)amino)pyrrolidin-1-yl)-3-(3-(2-hydroxypropan-2-yl)-1,2,4-oxadiazol-5-yl)prop-2-en-1-one The amide coupling reaction was prepared in a similar fashion to Method #1, Step 10. The crude was purified by reverse phase HPLC (column: Waters Xbridge Prep OBD C18 150*40 mm*10 um; mobile phase: [water (NH$_4$HCO$_3$)-Acetonitrile]; B %: 30%-60%, 8 min.) affording (R,E)-1-(3-((7-(8-chloro-7-fluoronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-(2-hydroxypropan-2-yl)-1,2,4-oxadiazol-5-yl)prop-2-en-1-one (6.83 mg, 5.66%) as a yellow oil: $^1$H NMR (400 MHz, Acetonitrile-d3) δ 9.24 (s, 1H), 8.20-8.15 (m, 1H), 8.11 (dd, J=5.7, 9.1 Hz, 1H), 7.74-7.69 (m, 2H), 7.58-7.49 (m, 2H), 7.46-7.39 (m, 1H), 5.50-5.36 (m, 1H), 4.29-4.24 (m, 2H), 4.06 (br dd, J=4.3, 12.1 Hz, 1H), 3.96-3.88 (m, 1H), 3.86-3.78 (m, 1H), 3.67-3.57 (m, 1H), 3.48 (s, 3H), 3.09 (br dd, J=5.6, 10.0 Hz, 2H), 2.73-2.65 (m, 2H), 2.40 (br d, J=2.9 Hz, 1H), 2.06-2.00 (m, 4H), 1.88 (td, J=5.7, 11.5 Hz, 4H), 1.75-1.67 (m, 2H), 1.61 (d, J=8.8 Hz, 6H). LCMS Rt=2.589 min, m/z=744.3 [M+H]$^+$.

LCMS (5 to 95% acetonitrile in water+0.03% ammonium bicarbonate over 6 mins) retention time 2.589 min, ESI+ found [M+H]=744.3.

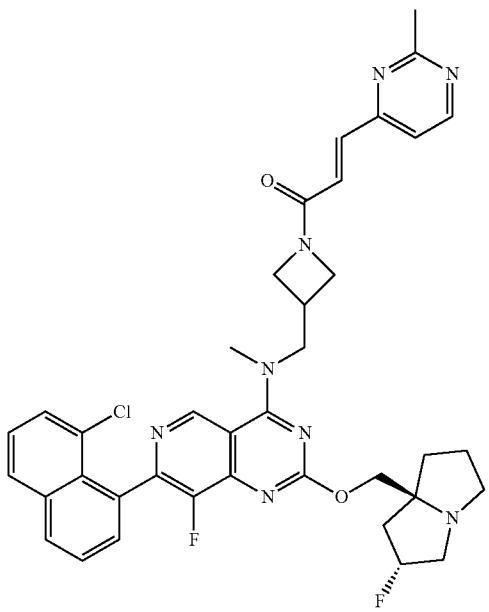 [SMILES: Cc1nccc(/C=C/C(=O)N2CC(CN(C)c3nc(OC[C@@]45CCCN4C[C@H](F)C5)nc4c(F)c(-c5cccc6cccc(Cl)c56)ncc34)C2)n1]

Example 62 (Method 8): (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(2-methylpyrimidin-4-yl)prop-2-en-1-one

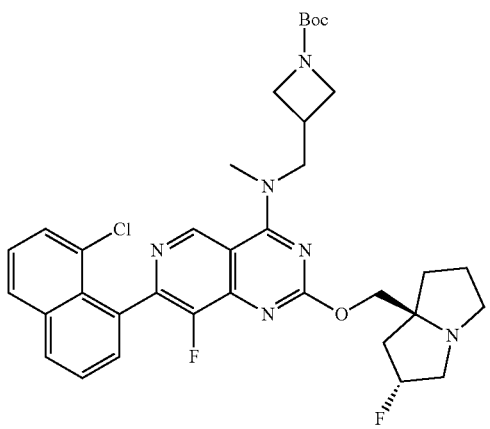 [SMILES: CN(CC1CN(C(=O)OC(C)(C)C)C1)c1nc(OC[C@@]23CCCN2C[C@H](F)C3)nc2c(F)c(-c3cccc4cccc(Cl)c34)ncc12]

Step 1: tert-butyl 3-(((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)methyl)azetidine-1-carboxylate The substitution reaction was prepared in a similar fashion to Method #1, Step 8. The crude product was purified by column chromatography (silica gel, 100-200 mesh, 10%-30% ethyl acetate in petroleum ether) affording tert-butyl 3-(((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)methyl)azetidine-1-carboxylate (1 g, 60.18%) as a brown oil. LCMS Rt=0.796 min, m/z=664.3 [M+H]+.

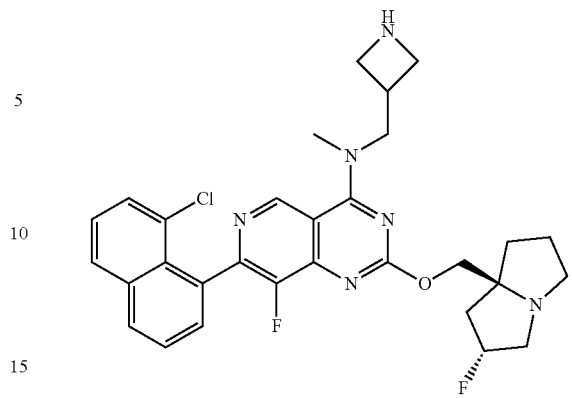

Step 2: N-(azetidin-3-ylmethyl)-7-(8-chloronaphthalen-1-yl)-8-fluoro-2-(((2R,7aS)-2-fluorohexahydro-1H-pyrrolizin-7a-yl)methoxy)-N-methylpyrido[4,3-d]pyrimidin-4-amine The de-Boc protecting reaction was prepared in a similar fashion to Method #1, Step 9. The reaction mixture was concentrated in vacuo affording N-(azetidin-3-ylmethyl)-7-(8-chloronaphthalen-1-yl)-8-fluoro-2-(((2R,7aS)-2-fluorohexahydro-1H-pyrrolizin-7a-yl)methoxy)-N-methylpyrido[4,3-d]pyrimidin-4-amine (151 mg, crude, trifluoroacetate salt), used in next step without further purification. LCMS Rt=0.497 min, m/z=564.2 [M+H]+.

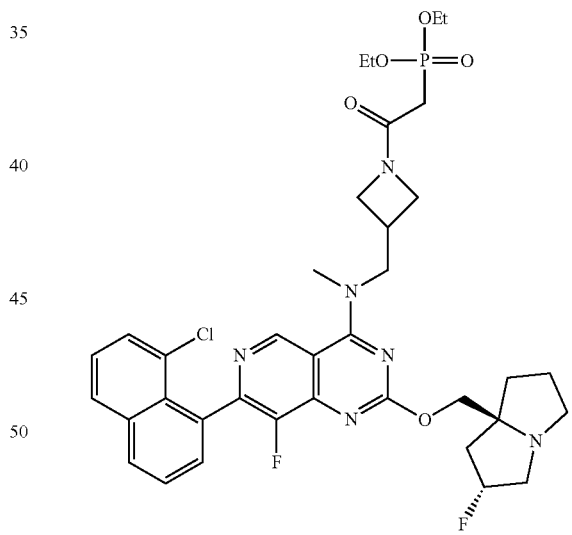

Step 3: diethyl (2-(3-(((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)methyl)azetidin-1-yl)-2-oxoethyl)phosphonate The amide coupling reaction was prepared in a similar fashion to Method #8, Step 3. The crude was purified by reverse phase HPLC (column: Waters Xbridge Prep OBD C18 150*40 mm*10 μm; mobile phase: [water (NH4HCO3)-acetonitrile]; B %: 35%-65%, 8 min) affording diethyl (2-(3-(((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)methyl)azetidin-1-yl)-2-oxoethyl)phosphonate (37 mg, 22.39%) as a white solid. LCMS Rt=0.762 min, m/z=742.3 [M+H]+.

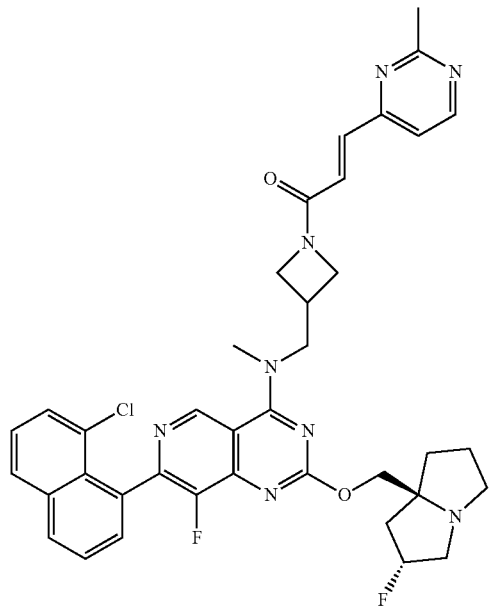 [SMILES: Cc1nccc(/C=C/C(=O)N2CC(CN(C)c3nc(OC[C@@]45CCCN4C[C@H](F)C5)nc4c(F)c(-c5cccc6cccc(Cl)c56)ncc34)C2)n1]

Step 4: (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(2-methylpyrimidin-4-yl)prop-2-en-1-one The Horner-Wadsworth-Emmons reaction was prepared in a similar fashion to Method #8, Step 4. The crude was purified by reverse phase HPLC(column: Waters Xbridge BEH C18 100*30 mm*10 μm; mobile phase: [water (NH4HCO3)-acetonitrile]; B %: 25%-65%, 8 min) affording (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(2-methylpyrimidin-4-yl)prop-2-en-1-one (17.47 mg, 48.88%) as a white amorphous solid: $^1$H NMR (400 MHz, Acetonitrile-d3) δ 9.24 (s, 1H), 8.67 (d, J=5.1 Hz, 1H), 8.12 (d, J=8.1 Hz, 1H), 8.02 (d, J=8.1 Hz, 1H), 7.71-7.66 (m, 1H), 7.64-7.58 (m, 2H), 7.54-7.48 (m, 1H), 7.43-7.36 (m, 1H), 7.31 (d, J=5.1 Hz, 1H), 7.25-7.19 (m, 1H), 5.31-5.11 (m, 1H), 4.46 (t, J=8.4 Hz, 1H), 4.32-4.22 (m, 2H), 4.20-4.06 (m, 4H), 3.96-3.87 (m, 1H), 3.62-3.55 (m, 3H), 3.29-3.18 (m, 1H), 3.14-3.00 (m, 3H), 2.90-2.80 (m, 1H), 2.67-2.62 (m, 3H), 2.10-1.98 (m, 3H), 1.87-1.77 (m, 3H). LCMS Rt=0.963 min, m/z=710.3 [M+H]+.

LCMS (5 to 95% acetonitrile in water+0.1% ammonium bicarbonate over 6 mins) retention time 0.963 min, ESI+ found [M+H]=710.3.

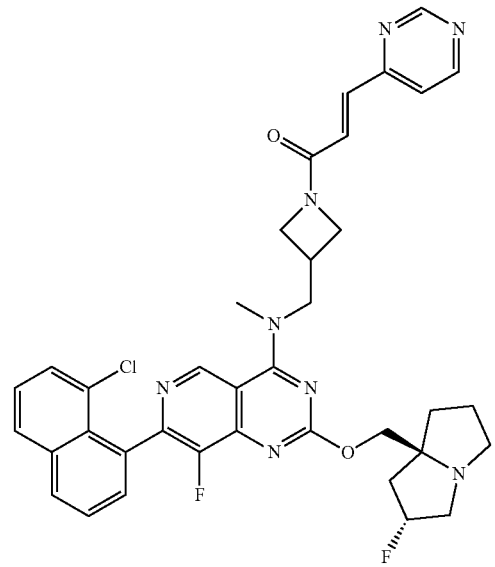 [SMILES: CN(CC1CN(C(=O)/C=C/c2ccncn2)C1)c1nc(OC[C@@]23CCCN2C[C@H](F)C3)nc2c(F)c(-c3cccc4cccc(Cl)c34)ncc12]

Example 63 (Method 8): (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(pyrimidin-4-yl)prop-2-en-1-one

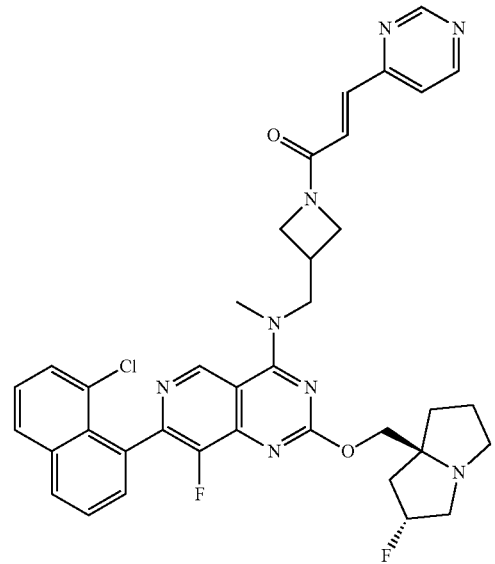 [SMILES: CN(CC1CN(C(=O)/C=C/c2ccncn2)C1)c1nc(OC[C@@]23CCCN2C[C@H](F)C3)nc2c(F)c(-c3cccc4cccc(Cl)c34)ncc12]

Step 1: (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(pyrimidin-4-yl)prop-2-en-1-one The Homer-Wadsworth-Emmons reaction was prepared in a similar fashion to Method #8, Step 4. The crude was purified by reverse phase HPLC (column: Waters Xbridge Prep OBD C18 150*40 mm*10 um; mobile phase: [water (NH4HCO3)-acetonitrile]; B %: 30%-60%, 8 min) affording (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(pyrimidin-4-yl)prop-2-en-1-one (26.4 mg, 17.02%) as a pale yellow amorphous solid: $^1$H NMR (400 MHz, Acetonitrile-d3) δ 9.24 (s, 1H), 9.14 (s, 1H), 8.80-8.75 (m, 1H), 8.12 (d, J=7.4 Hz, 1H), 8.02 (d, J=8.1 Hz, 1H), 7.72-7.65 (m, 1H), 7.64-7.58 (m, 2H), 7.56-7.49 (m, 2H), 7.46-7.40 (m, 1H), 7.32-7.21 (m, 1H), 5.32-5.12 (m, 1H), 4.47 (t, J=8.5 Hz, 1H), 4.33-4.24 (m, 2H), 4.23-4.03 (m, 4H), 3.97-3.86 (m, 1H), 3.64-3.55 (m, 3H), 3.28-3.18 (m, 1H), 3.13-3.02 (m, 3H), 2.91-2.80 (m, 1H), 2.11-1.98 (m, 3H), 1.90-1.73 (m, 3H). LCMS Rt=2.833 min, m/z=696.3 [M+H]$^+$.

LCMS (5 to 95% acetonitrile in water+0.1% ammonium bicarbonate over 6 mins) retention time 2.833 min, ESI+ found [M+H]=696.3.

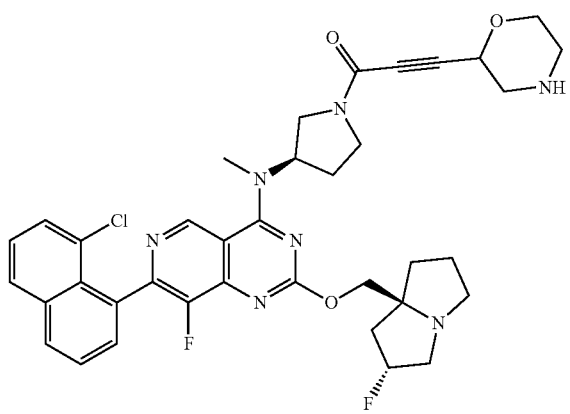 [SMILES: CN(c1nc(OC[C@@]23CCCN2C[C@H](F)C3)nc2c(F)c(-c3cccc4cccc(Cl)c34)ncc12)[C@@H]1CCN(C(=O)C#CC2CNCCO2)C1]

Example 64 (Method 7): 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(morpholin-2-yl)prop-2-yn-1-one

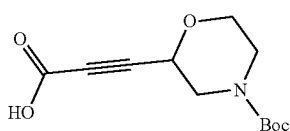 [SMILES: CC(C)(C)OC(=O)N1CCOC(C#CC(=O)O)C1]

Step 1:
3-(4-(tert-butoxycarbonyl)morpholin-2-yl)propiolic acid

The carbonylation reaction was prepared in a similar fashion to Method #7, Step 1. The mixture was concentrated in vacuo affording 3-(4-(tert-butoxycarbonyl)morpholin-2-yl)propiolic acid (80 mg, crude) as a yellow oil, used in next step without any further purification.

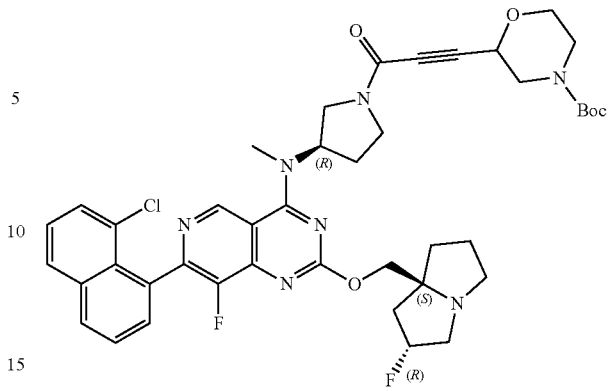

Step 2: tert-butyl 2-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)morpholine-4-carboxylate The amide coupling reaction was prepared in a similar fashion to Method #7, Step 2. The residue was purified by reverse phase HPLC (column: Phenomenex Luna 80*30 mm*3 μm; mobile phase: [water (trifluoroacetic acid)-acetonitrile]; B %: 20%-50%, 8 min) affording tert-butyl 2-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)morpholine-4-carboxylate (30 mg, 14.53%, trifluoroacetic salt) as a white solid. LCMS Rt=1.717 min, m/z=801.3 [M+H]$^+$.

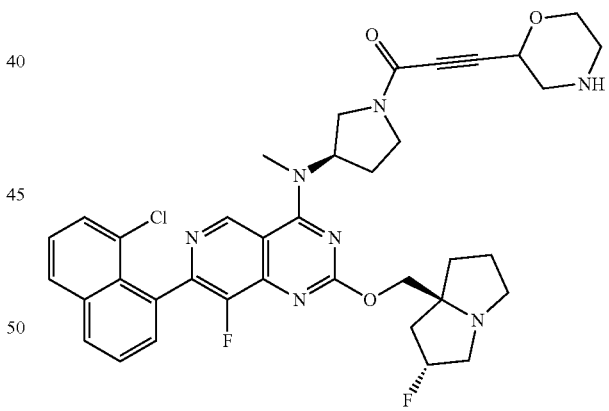

Step 3: 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(morpholin-2-yl)prop-2-yn-1-one The de-Boc protecting reaction was prepared in a similar fashion to Method #7, Step 3. The residue was purified by reverse phase HPLC (column: Waters Xbridge BEH C18 100*30 mm*10 um; mobile phase:[water (NH$_4$HCO$_3$)-acetonitrile]; B %: 30%-60%, 8 min) affording 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(morpholin-2-yl)prop-2-yn-1-one (3.47 mg, 11.70%) as a yellow solid: ¹H NMR (400 MHz, Acetonitrile-d3) δ 9.22 (dd, J=1.5, 4.5 Hz, 1H), 8.16 (d, J=8.3 Hz, 1H), 8.05 (d, J=8.3 Hz, 1H), 7.77-7.69 (m, 1H), 7.69-7.63 (m, 2H), 7.59-7.51 (m, 1H), 5.53-5.14 (m, 2H), 4.57-4.40 (m, 1H), 4.26-4.14 (m, 2H), 4.05-3.67 (m, 4H), 3.60-3.49 (m, 2H), 3.48-3.43 (m, 3H), 3.25-3.16 (m, 2H), 3.13-3.01 (m, 2H), 2.99-2.90 (m, 1H), 2.90-2.82 (m, 1H), 2.82-2.75 (m, 2H), 2.44-2.30 (m, 3H), 2.17-2.04 (m, 3H), 1.93-1.85 (m, 2H). LCMS Rt=0.961 min, m/z=701.3 [M+H]⁺.

LCMS (5 to 95% acetonitrile in water+0.03% ammonium bicarbonate over 6 mins) retention time 0.961 min, ESI+ found [M+H]=701.3

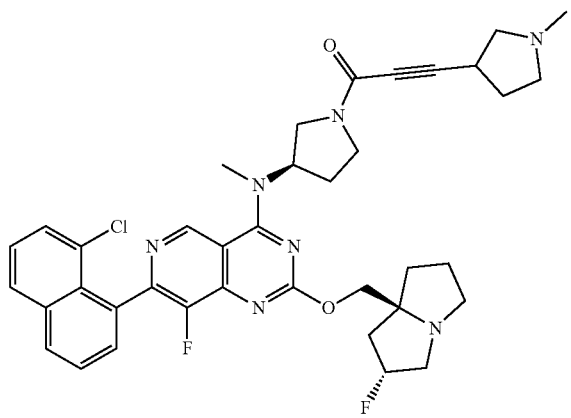 [SMILES: CN1CCC(C#CC(=O)N2CC[C@@H](N(C)c3nc(OC[C@@]45CCCN4C[C@H](F)C5)nc4c(F)c(-c5cccc6cccc(Cl)c56)ncc34)C2)C1]

Example 65 (Method 7): 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(1-methylpyrrolidin-3-yl)prop-2-yn-1-one

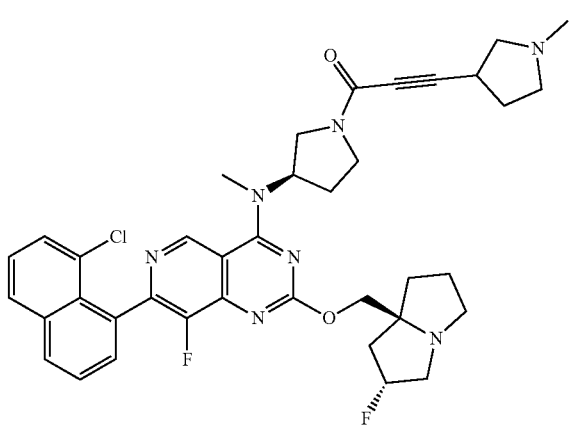 [SMILES: CN1CCC(C#CC(=O)N2CC[C@@H](N(C)c3nc(OC[C@@]45CCCN4C[C@H](F)C5)nc4c(F)c(-c5cccc6cccc(Cl)c56)ncc34)C2)C1]

Step 1: 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(1-methylpyrrolidin-3-yl)prop-2-yn-1-one The starting material was prepared as in Example 58.
The reductive amination reaction was prepared in a similar fashion to Method #7, Step 4. The residue was purified by reverse phase HPLC (column: Waters Xbridge BEH C18 100*30 mm*10 μm; mobile phase: [water (NH₄HCO₃)-acetonitrile]; B %: 35%-65%, 8 min) affording 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(1-methylpyrrolidin-3-yl)prop-2-yn-1-one (16.99 mg, 24.27%) as a white solid: ¹H NMR (400 MHz, Acetonitrile-d3) δ 9.25-9.18 (m, 1H), 8.15 (d, J=8.3 Hz, 1H), 8.05 (d, J=8.3 Hz, 1H), 7.74-7.69 (m, 1H), 7.67-7.61 (m, 2H), 7.57-7.50 (m, 1H), 5.45-5.16 (m, 2H), 4.26-4.20 (m, 1H), 4.19-4.12 (m, 1H), 4.00-3.85 (m, 1H), 3.79-3.63 (m, 2H), 3.48 (br s, 1H), 3.47-3.39 (m, 4H), 3.19-3.13 (m, 2H), 3.10 (s, 1H), 2.97-2.89 (m, 1H), 2.87-2.79 (m, 1H), 2.60-2.45 (m, 3H), 2.40-2.34 (m, 2H), 2.33 (s, 1H), 2.29 (s, 1H), 2.27-2.17 (m, 4H), 2.13 (br s, 1H), 2.11-2.05 (m, 1H), 1.93-1.85 (m, 3H). LCMS Rt=0.865 min, m/z=699.3 [M+H]⁺.

LCMS (5 to 95% acetonitrile in water+0.03% ammonium bicarbonate over 6 mins) retention time 3.014 min, ESI+ found [M+H]=699.3.

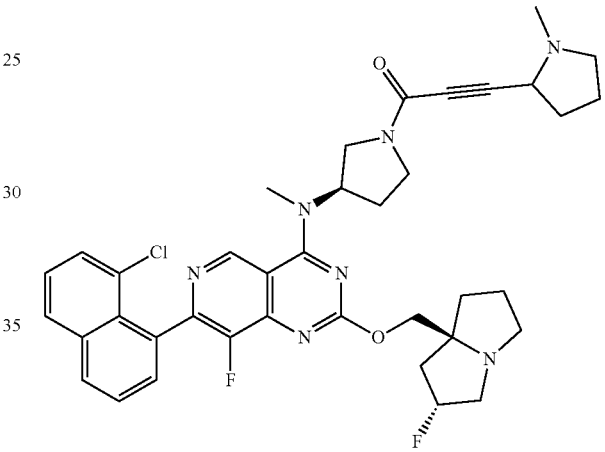

Example 66 (Method 7-Master):1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(1-methylpyrrolidin-2-yl)prop-2-yn-1-one

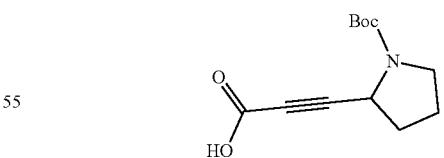

Step 1: 3-(1-(tert-butoxycarbonyl)pyrrolidin-2-yl)propiolic acid

To a solution of tert-butyl 2-ethynylpyrrolidine-1-carboxylate (100 mg, 512.14 μmol) in tetrahydrofuran (10 mL) was added n-butyllithium (2.5 M, 102.43 uL) at −78° C. under nitrogen. The mixture was stirred at −78° C. for 0.5 h, then added carbon dioxide. The mixture was stirred at -78° C. for 1 h. The reaction mixture was quenched with saturated ammonium chloride (5 mL) at 0° C. then added potassium hydrogen sulfate (5 mL), and extracted with ethyl acetate (3×10 mL). The combined organic layers were dried over sodium sulphate and concentrated in vacuo affording 3-(1-(tert-butoxycarbonyl)pyrrolidin-2-yl)propiolic acid (110 mg, crude) as a yellow oil, used in next step without any further purification

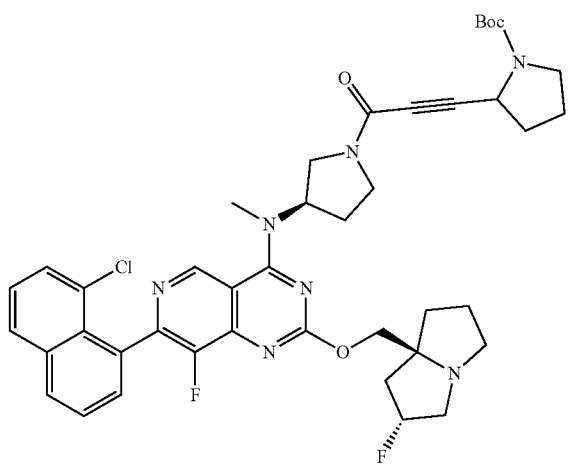 [SMILES: CN(c1nc(OC[C@@]23CCCN2C[C@H](F)C3)nc2c(F)c(-c3cccc4cccc(Cl)c34)ncc12)[C@@H]1CCN(C(=O)C#CC2CCCN2C(=O)OC(C)(C)C)C1]

Step 2: tert-butyl 2-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)pyrrolidine-1-carboxylate The amide coupling reaction was prepared in a similar fashion to Method #1, Step 10. The mixture was diluted with water (10 mL) and extracted with ethyl acetate (3×10 mL). The combined organic layers were dried over sodium sulphate and concentrated in vacuo affording tert-butyl 2-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)pyrrolidine-1-carboxylate (200 mg, crude) as a yellow oil, used in next step without any further purification. LCMS Rt=0.708 min, m/z=785.3 [M+H]+.

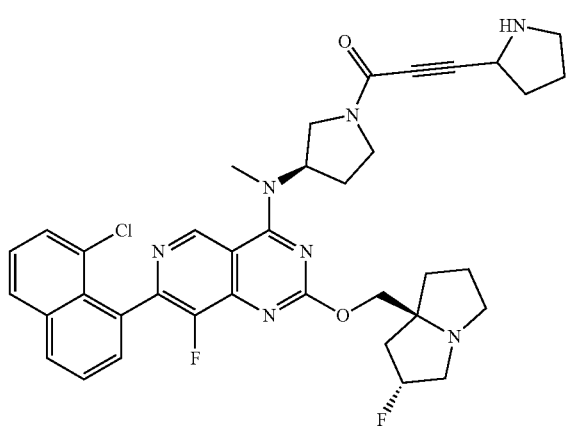 [SMILES: CN(c1nc(OC[C@@]23CCCN2C[C@H](F)C3)nc2c(F)c(-c3cccc4cccc(Cl)c34)ncc12)[C@@H]1CCN(C(=O)C#CC2CCCN2)C1]

Step 3: 1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(pyrrolidin-2-yl)prop-2-yn-1-one The deprotection of Boc group was prepared in a similar fashion to Method #1, Step 9. The residue was purified by reverse phase HPLC (column: Phenomenex Luna C18 75*30 mm*3 μm; mobile phase: [water (formic acid)-acetonitrile]; B %:1%-35%, 8 min) affording 1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(pyrrolidin-2-yl)prop-2-yn-1-one (14.08 mg, 14.77%, formate salt) as a yellow oil: $^1$H NMR (400 MHz, Acetonitrile-d3) δ 9.22 (dd, J=2.1, 7.6 Hz, 1H), 8.25 (s, 1H), 8.15 (d, J=8.1 Hz, 1H), 8.04 (d, J=8.1 Hz, 1H), 7.75-7.61 (m, 3H), 7.57-7.50 (m, 1H), 5.49-5.25 (m, 2H), 4.38-4.24 (m, 2H), 4.18-4.05 (m, 1H), 4.02-3.86 (m, 1H), 3.82-3.62 (m, 2H), 3.54-3.38 (m, 5H), 3.36-3.16 (m, 3H), 3.09-3.03 (m, 1H), 3.00-2.92 (m, 1H), 2.43-2.26 (m, 4H), 2.24-2.07 (m, 3H), 2.06-2.01 (m, 1H), 1.95-1.84 (m, 3H), 1.84-1.76 (m, 1H). LCMS Rt=1.942 min, m/z=685.3 [M+H]+.

LCMS (5 to 95% acetonitrile in water+0.1% formic acid over 6 mins) retention time 1.942 min, ESI+ found [M+H]=685.3.

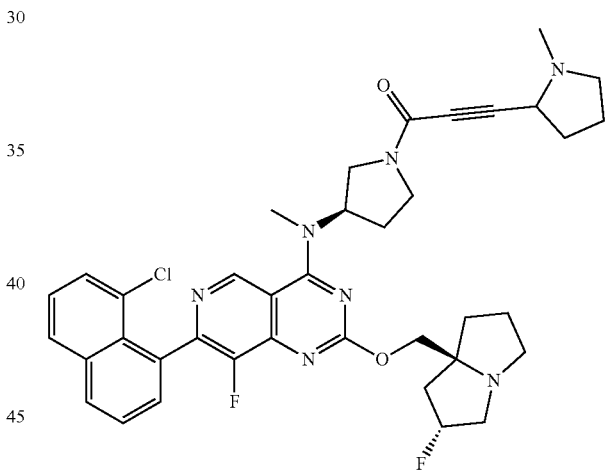

Step 4: 1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(1-methylpyrrolidin-2-yl)prop-2-yn-1-one The reductive amination was prepared in a similar fashion to Method #6, Step 1. The residue was purified by reverse phase HPLC (column: Waters Xbridge BEH C18 100*30 mm*10 μm; mobile phase: [water (NH$_4$HCO$_3$)-acetonitrile]; B %: 10%-70%, 8 min) affording 1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(1-methylpyrrolidin-2-yl)prop-2-yn-1-one (10.78 mg, 20.21%) as a yellow oil: $^1$H NMR (400 MHz, Acetonitrile-d3) δ 9.28-9.13 (m, 1H), 8.15 (d, J=8.3 Hz, 1H), 8.05 (d, J=8.1 Hz, 1H), 7.78-7.61 (m, 3H), 7.58-7.49 (m, 1H), 5.46-5.17 (m, 2H), 4.30-4.06 (m, 3H), 4.04-3.87 (m, 1H), 3.84-3.65 (m, 2H), 3.56-3.48 (m, 1H), 3.47-3.43 (m, 3H), 3.43-3.35 (m, 1H), 3.29-3.12 (m, 2H), 3.09 (s, 1H), 2.97-2.85 (m, 1H), 2.85-2.71 (m, 1H), 2.50-2.43 (m, 1H), 2.43-2.35 (m, 4H), 2.26-2.18 (m, 2H), 2.13 (br s, 2H), 2.09-2.05 (m, 1H), 1.94-1.76 (m, 5H). LCMS Rt=3.054 min, m/z=699.3 [M+H]+.

LCMS (5 to 95% acetonitrile in water+0.03% ammonium bicarbonate over 6 mins) retention time 3.054 min, ESI+ found [M+H]=699.3.

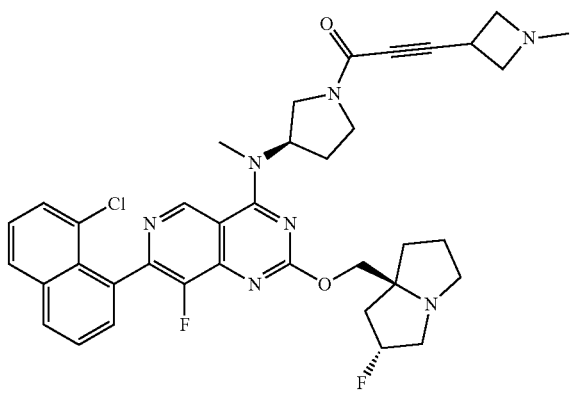 [SMILES: CN1CC(C#CC(=O)N2CC[C@@H](N(C)c3nc(OC[C@@]45CCCN4C[C@H](F)C5)nc4c(F)c(-c5cccc6cccc(Cl)c56)ncc34)C2)C1]

Example 67 (Method 7): 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(1-methylazetidin-3-yl)prop-2-yn-1-one

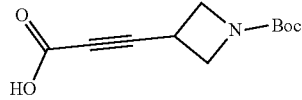

Step 1: 3-(1-(tert-butoxycarbonyl)azetidin-3-yl)propiolic acid

The carbonylation reaction was prepared in a similar fashion to Method #7, Step 1. The reaction mixture was quenched with saturated aqueous ammonium chloride (5 mL) at 0° C., then added potassium hydrogen sulfate (10 mL) adjust PH<3 and extracted with ethyl acetate (3×10 mL). The combined organic layers were concentrated in vacuo affording 3-(1-(tert-butoxycarbonyl)azetidin-3-yl) propiolic acid (280 mg, 45.06%) as a yellow oil, used in next step without any further purification. LCMS Rt=0.842 min, m/z=225.1 [M+H]+.

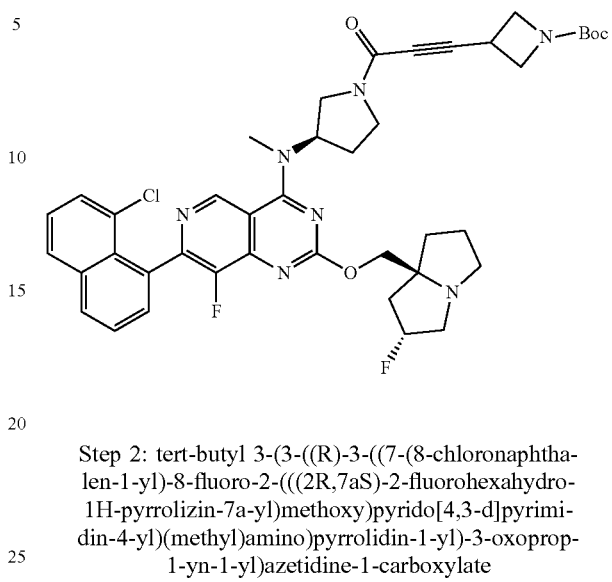

Step 2: tert-butyl 3-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)azetidine-1-carboxylate The amide coupling reaction was prepared in a similar fashion to Method #7, Step 2. The mixture was diluted with water (20 mL) and extracted with ethyl acetate (3×50 mL). The combined organic phase was dried over anhydrous sodium sulphate, filtered and concentrated in vacuo affording tert-butyl 3-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino) pyrrolidin-1-yl)-3-oxoprop-1-yn-1-yl)azetidine-1-carboxylate (300 mg, crude) as a yellow oil, used in next step without any further purification. LCMS Rt=0.495 min, m/z=771.3 [M+H]+.

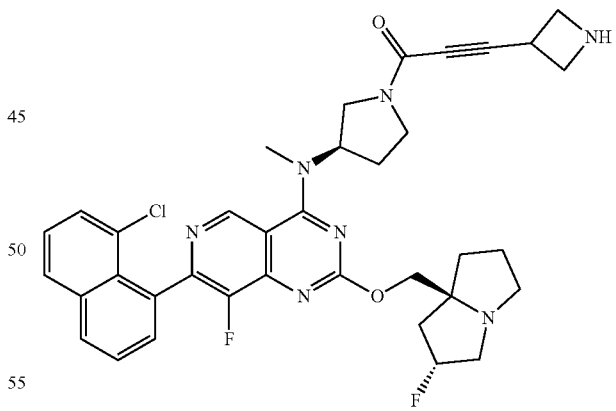

Step 3: 3-(azetidin-3-yl)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)prop-2-yn-1-one The de-Boc protecting reaction was prepared in a similar fashion to Method #7, Step 3. The mixture was concentrated in vacuo. The residue was purified by reverse phase HPLC (column: Phenomenex luna C18 250*50 mm*10 μm; mobile phase: [water (trifluoroacetic acid)-acetonitrile]; B %: 20%-50%, 10 min) affording 3-(azetidin-3-yl)-1-((R)-3-((7-(8-chloronaphthalen-1-yl)-8-fluoro-2-(((2R,7aS)-2-fluoro-hexahydro-1H-pyrrolizin-7a-yl)methoxy)pyrido[4,3-d]pyrimidin-4-yl)(methyl)amino)pyrrolidin-1-yl)prop-2-yn-1-one (90 mg, 34.47%, trifluoroacetic salt) as a yellow oil. LCMS Rt=0.589 min, m/z=671.3 [M+H]⁺.

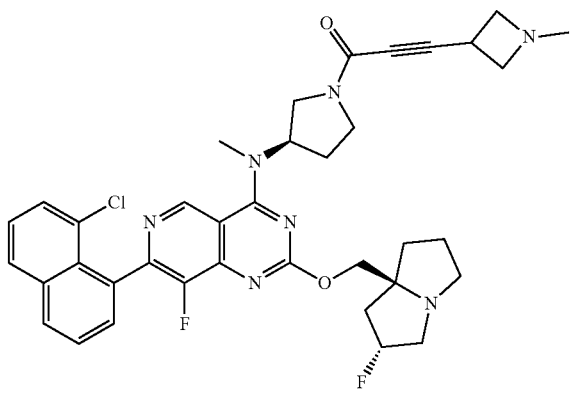 [SMILES: CN1CC(C#CC(=O)N2CC[C@@H](N(C)c3nc(OC[C@@]45CCCN4C[C@H](F)C5)nc4c(F)c(-c5cccc6cccc(Cl)c56)ncc34)C2)C1]

Step 4: 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(1-methylazetidin-3-yl)prop-2-yn-1-one The reductive amination reaction was prepared in a similar fashion to Method #7, Step 4. The residue was purified by reverse phase HPLC(colunn: Waters Xbridge Prep OBD C18 150*40 mm*10 um; mobile phase: [water (NH₄HCO₃)-acetonitrile]; B %: 20%-60%, 8 min) affording 1-((R)-3-((7-(8-chloronaphthalen-1-yl)-8-fluoro-2-(((2R,7aS)-2-fluoro-hexahydro-1H-pyrrolizin-7a-yl)methoxy)pyrido[4,3-d]pyrimidin-4-yl)(methyl)amino)pyrrolidin-1-yl)-3-(1-methylazetidin-3-yl)prop-2-yn-1-one (15.05 mg, 21.11%) as a white amorphous solid: ¹H NMR (400 MHz, Acetonitrile-d3) δ 9.28-9.13 (m, 1H), 8.15 (d, J=8.3 Hz, 1H), 8.05 (d, J=8.1 Hz, 1H), 7.78-7.61 (m, 3H), 7.58-7.49 (m, 1H), 5.46-5.17 (m, 2H), 4.30-4.06 (m, 3H), 4.04-3.87 (m, 1H), 3.84-3.65 (m, 2H), 3.56-3.48 (m, 1H), 3.47-3.43 (m, 3H), 3.43-3.35 (m, 1H), 3.29-3.12 (m, 2H), 3.09 (s, 1H), 2.97-2.85 (m, 1H), 2.85-2.71 (m, 1H), 2.50-2.43 (m, 1H), 2.43-2.35 (m, 4H), 2.26-2.18 (m, 2H), 2.13 (br s, 2H), 2.09-2.05 (m, 1H), 1.94-1.76 (m, 3H). LCMS Rt=2.916 min, m/z=685.3 [M+H]⁺.

LCMS (5 to 95% acetonitrile in water+0.03% ammonium bicarbonate over 6 mins) retention time 2.916 min, ESI+ found [M+H]=685.3.

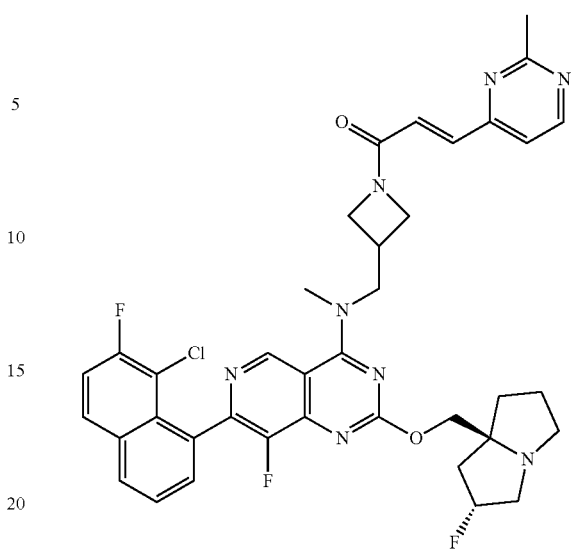

Example 68 (Method 8): (E)-1-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(2-methylpyrimidin-4-yl)prop-2-en-1-one

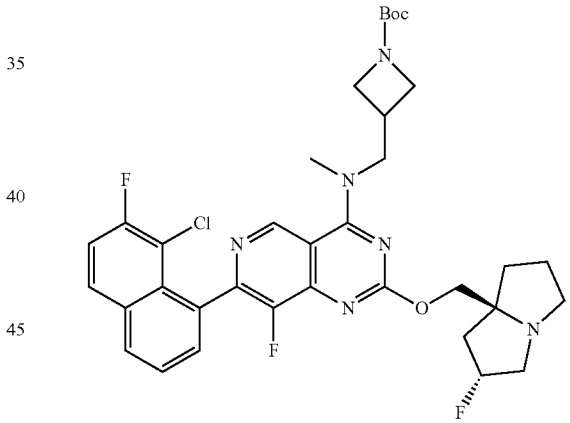

Step 1: tert-butyl 3-(((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)methyl)azetidine-1-carboxylate The substitution reaction was prepared in a similar fashion to Method #1, Step 8. The residue was purified by reverse phase HPLC (column: Phenomenex luna C18 250*50 mm*10 μm; mobile phase: [water (trifluoroacetic acid)-acetonitrile]; B %: 30%-60%, 10 min) affording tert-butyl 3-(((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)methyl)azetidine-1-carboxylate (340 mg, 25.85%, trifluoroacetate salt) as a white solid. LCMS Rt=0.719 min, m/z=682.3 [M+H]⁺.

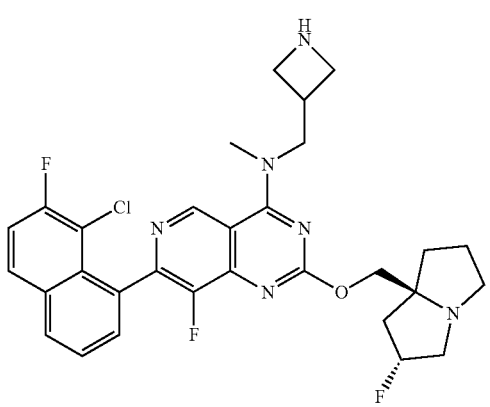 [SMILES: CN(CC1CNC1)c1nc(OC[C@@]23CCCN2C[C@H](F)C3)nc2c(F)c(-c3cccc4ccc(F)c(Cl)c34)ncc12]

Step 2: N-(azetidin-3-ylmethyl)-7-(8-chloro-7-fluoronaphthalen-1-yl)-8-fluoro-2-(((2R,7aS)-2-fluorohexahydro-1H-pyrrolizin-7a-yl)methoxy)-N-methylpyrido[4,3-d]pyrimidin-4-amine

The deprotection of Boc group was prepared in a similar fashion to Method #1, Step 9. The reaction mixture was concentrated in vacuo affording N-(azetidin-3-ylmethyl)-7-(8-chloro-7-fluoronaphthalen-1-yl)-8-fluoro-2-(((2R,7aS)-2-fluorohexahydro-1H-pyrrolizin-7a-yl)methoxy)-N-methylpyrido[4,3-d]pyrimidin-4-amine (190 mg, crude, trifluoroacetate salt) as a yellow oil, used in next step without any further purification. LCMS Rt=0.533 min, m/z=582.2 [M+H]$^+$.

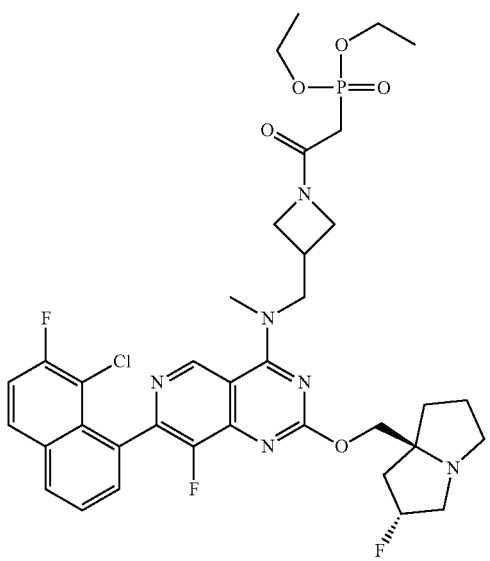 [SMILES: CCOP(=O)(CC(=O)N1CC(CN(C)c2nc(OC[C@@]34CCCN3C[C@H](F)C4)nc3c(F)c(-c4cccc5ccc(F)c(Cl)c45)ncc23)C1)OCC]

Step 3: diethyl (2-(3-(((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)methyl)azetidin-1-yl)-2-oxoethyl)phosphonate

The amide coupling reaction was prepared in a similar fashion to Method #8, Step 3. The reaction mixture was concentrated in vacuo affording diethyl (2-(3-(((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)methyl)azetidin-1-yl)-2-oxoethyl)phosphonate (190 mg, crude) as a yellow oil, used in next step without any further purification. LCMS Rt=0.548 min, m/z=760.3 [M+H]$^+$.

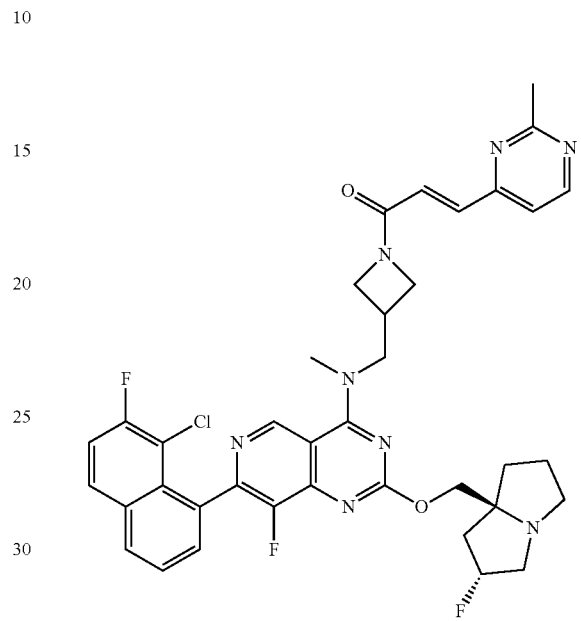

Step 4: (E)-1-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(2-methylpyrimidin-4-yl)prop-2-en-1-one

The Horner-Wadsworth-Emmons reaction was prepared in a similar fashion to Method #8, Step 4. The residue was purified by reverse phase HPLC(column: Phenomenex Luna C18 75*30 mm*3 μm; mobile phase: [water (formic acid)-acetonitrile]; B %: 10%-40%, 8 min) affording (E)-1-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(2-methylpyrimidin-4-yl)prop-2-en-1-one (6.64 mg, 3.43%, formate salt) as a yellow oil: $^1$H NMR (400 MHz, Acetonitrile-d3) δ 9.29 (s, 1H), 8.71 (d, J=5.0 Hz, 1H), 8.20-8.16 (m, 1H), 8.11 (dd, J=5.7, 9.0 Hz, 1H), 7.74-7.68 (m, 2H), 7.56 (t, J=9.0 Hz, 1H), 7.48-7.41 (m, 1H), 7.36 (d, J=5.0 Hz, 1H), 7.30-7.24 (m, 1H), 5.40-5.16 (m, 1H), 4.51 (t, J=8.4 Hz, 1H), 4.34-4.26 (m, 2H), 4.23-4.17 (m, 3H), 4.01-3.91 (m, 1H), 3.64 (s, 3H), 3.29-3.23 (m, 1H), 3.21-3.17 (m, 1H), 3.12 (br s, 1H), 2.97-2.88 (m, 2H), 2.69 (s, 3H), 2.29-2.18 (m, 1H), 2.17-2.12 (m, 1H), 2.11-2.04 (m, 1H), 1.94-1.79 (m, 4H). LCMS Rt=2.159 min, m/z=728.3 [M+H]$^+$.

LCMS (5 to 95% acetonitrile in water+0.1% trifluoroacetic acid over 6 mins) retention time 2.159 min, ESI+ found [M+H]=728.3.

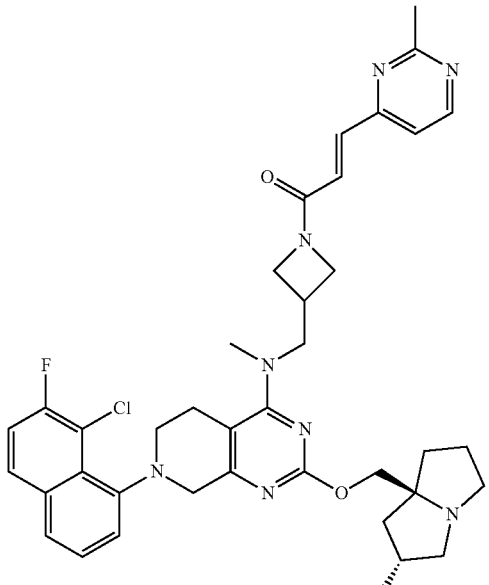

Example 69 (Method 9-Master): (E)-1-(3-(((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)methyl)azetidin-1-yl)-3-(2-methylpyrimidin-4-yl)prop-2-en-1-one

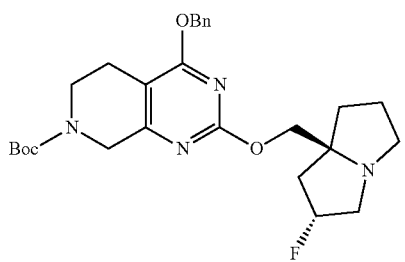 [SMILES: CC(C)(C)OC(=O)N1CCc2c(nc(OC[C@@]34CCCN3C[C@H](F)C4)nc2OCc2ccccc2)C1]

Step 1: tert-butyl 4-(benzyloxy)-2-(((2R,7aS)-2-fluorohexahydro-1H-pyrrolizin-7a-yl)methoxy)-5,6-dihydropyrido[3,4-d]pyrimidine-7(8H)-carboxylate The substitution reaction was prepared in a similar fashion to Method #4, Step 4. The reaction mixture was concentrated in vacuo affording tert-butyl 4-(benzyloxy)-2-(((2R,7aS)-2-fluorohexahydro-1H-pyrrolizin-7a-yl)methoxy)-5,6-dihydropyrido[3,4-d]pyrimidine-7(8H)-carboxylate (143 g, crude) as a yellow oil used in the next step without further purification. LCMS Rt=0.592 min, m/z=498.3 [M+H]+.

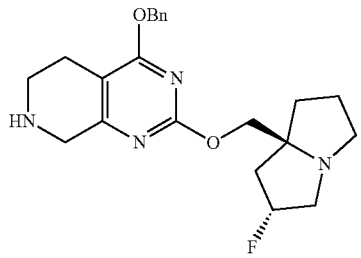 [SMILES: F[C@H]1CN2CCC[C@@]2(COc2nc3c(c(OCc4ccccc4)n2)CCNC3)C1]

Step 2: 4-(benzyloxy)-2-(((2R,7aS)-2-fluorohexahydro-1H-pyrrolizin-7a-yl)methoxy)-5,6,7,8-tetrahydropyrido[3,4-d]pyrimidine The deprotection of Boc was prepared in a similar fashion to Method #4, Step 5. The reaction mixture was concentrated in vacuo affording 4-(benzyloxy)-2-(((2R,7aS)-2-fluorohexahydro-1H-pyrrolizin-7a-yl)methoxy)-5,6,7,8-tetrahydropyrido[3,4-d]pyrimidine (75 g, crude) as a yellow oil used in the next step without further purification. LCMS Rt=0.414 min, m/z=398.2 [M+H]+.

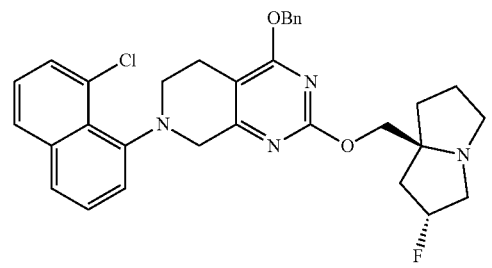

Step 3: 4-(benzyloxy)-7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidine The Buchwald reaction was prepared in a similar fashion to Method #4, Step 6. The crude product was purified by column chromatography (silica gel, 100-200 mesh, 0-100% ethyl acetate in petroleum ether) affording 4-(benzyloxy)-7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidine (36 g, 73.31%) as a brown oil. LCMS Rt=0.669 min, m/z=558.2 [M+H]+.

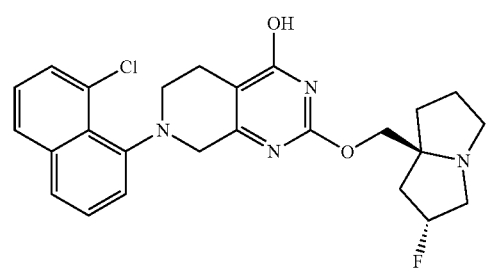 [SMILES: F[C@H]1CN2CCC[C@@]2(COc2nc3c(c(OCc4ccccc4)n2)CCN(c2cccc4cccc(Cl)c24)C3)C1]

Step 4: 7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-ol The deprotection of Bn was prepared in a similar fashion to Method #4, Step 7. The reaction mixture was concentrated in vacuo affording 7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-ol (44 g, crude) as a brown oil used in the next step without further purification. LCMS Rt=0.561 min, m/z=468.2 [M+H]$^+$.

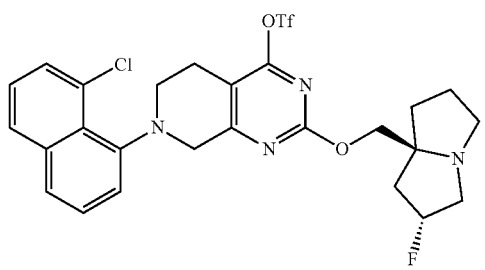 [SMILES: O=S(=O)(Oc1nc(OC[C@@]23CCCN2C[C@H](F)C3)nc2c1CCN(c1cccc3cccc(Cl)c13)C2)C(F)(F)F]

Step 5: 7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl trifluoromethanesulfonate The sulfonylation reaction was prepared in a similar fashion to Method #4, Step 8. The reaction mixture was concentrated in vacuo affording 7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl trifluoromethanesulfonate (7 g, crude) as a black oil used in the next step without further purification. LCMS Rt=1.748 min, m/z=600.1 [M+H]$^+$.

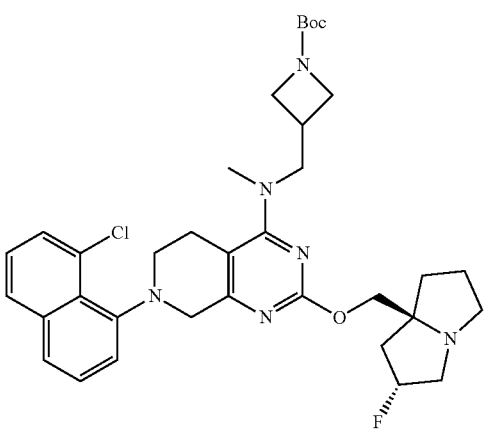 [SMILES: CN(CC1CN(C(=O)OC(C)(C)C)C1)c1nc(OC[C@@]23CCCN2C[C@H](F)C3)nc2c1CCN(c1cccc3cccc(Cl)c13)C2]

Step 6: tert-butyl 3-(((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)methyl)azetidine-1-carboxylate The substitution reaction was prepared in a similar fashion to Method #4, Step 9. The crude product was purified by column chromatography (silica gel, 100-200 mesh, 0-100% ethyl acetate in petroleum ether) affording (R)-tert-butyl 3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidine-1-carboxylate (2.5 g, 65.92%) as a yellow oil. LCMS Rt=1.595 min, m/z=650.3 [M+H]$^+$.

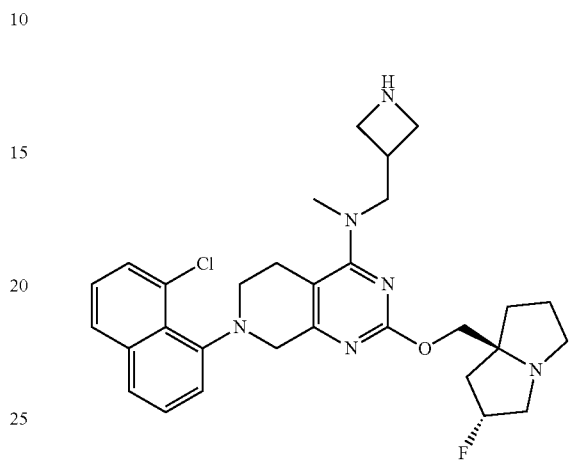

Step 7: N-(azetidin-3-ylmethyl)-7-(8-chloronaphthalen-1-yl)-2-(((2R,7aS)-2-fluorohexahydro-1H-pyrrolizin-7a-yl)methoxy)-N-methyl-5,6,7,8-tetrahydropyrido[3,4-d]pyrimidin-4-amine The deprotection of Boc was prepared in a similar fashion to Method #1, Step 9. The reaction mixture was concentrated in vacuo affording N-(azetidin-3-ylmethyl)-7-(8-chloronaphthalen-1-yl)-2-(((2R,7aS)-2-fluorohexahydro-1H-pyrrolizin-7a-yl)methoxy)-N-methyl-5,6,7,8-tetrahydropyrido[3,4-d]pyrimidin-4-amine (0.5 g, crude, trifluoroacetate salt) as a yellow oil used in the next step without further purification. LCMS Rt=0.600 min, m/z=550.3 [M+H]$^+$.

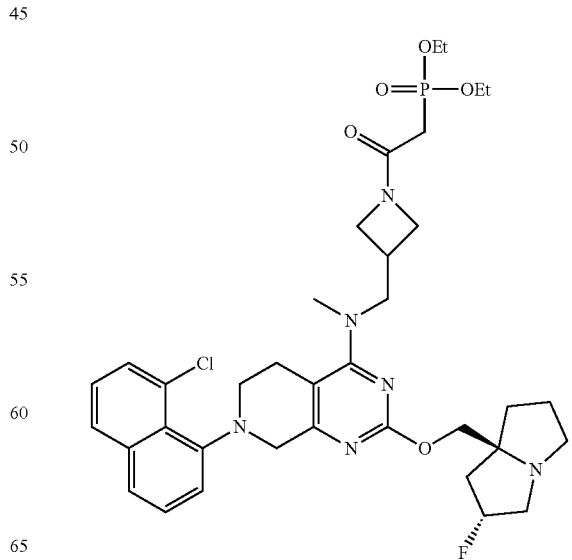

Step 8: diethyl (2-(3-(((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)methyl)azetidin-1-yl)-2-oxoethyl)phosphonate The amide coupling reaction was prepared in a similar fashion to Method #8, Step 3. The crude product was purified by reverse phase HPLC (column: Phenomenex luna C18 250*50 mm*10 μm; mobile phase: [water (trifluoroacetic acid)- acetonitrile]; B %: 20%-50%, 10 min) affording diethyl (2-(3-(((7-(8-chloronaphthalen-1-yl)-2-(((2R,7aS)-2-fluorohexahydro-TH-pyrrolizin-7a-yl)methoxy)-5,6,7,8-tetrahydropyrido[3,4-d]pyrimidin-4-yl)(methyl)amino)methyl)azetidin-1-yl)-2-oxoethyl)phosphonate (300 mg, 45.60%) as a yellow solid. LCMS Rt=1.476 min, m/z=728.3 [M+H]+.

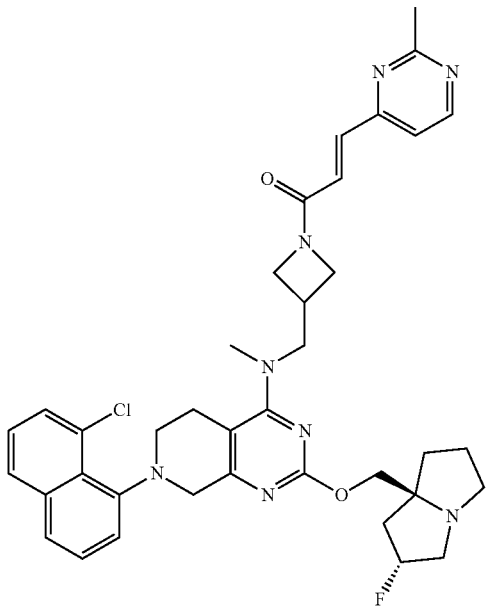 [SMILES: Cc1nccc(/C=C/C(=O)N2CC(CN(C)c3nc(OC[C@@]45CCCN4C[C@H](F)C5)nc4c3CCN(c3cccc5cccc(Cl)c35)C4)C2)n1]

Step 9: (E)-1-(3-(((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)methyl)azetidin-1-yl)-3-(2-methylpyrimidin-4-yl)prop-2-en-1-one The Homer-Wadsworth-Emmons reaction was prepared in a similar fashion to Method #8, Step 4. The crude product was purified by reverse phase HPLC (column: Waters Xbridge Prep OBD C18 150*40 mm*10 um; mobile phase: [water (ammonium bicarbonate)- acetonitrile]; B %: 45%-75%, 8 min) affording (E)-1-(3-(((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)methyl)azetidin-1-yl)-3-(2-methylpyrimidin-4-yl)prop-2-en-1-one (52.22 mg, 53.83%) as a yellow oil: $^1$H NMR (400 MHz, Acetonitrile-d3) δ 8.69 (dd, J=1.4, 5.1 Hz, 1H), 7.86 (d, J=8.1 Hz, 1H), 7.69 (dd, J=2.3, 8.0 Hz, 1H), 7.62-7.47 (m, 2H), 7.44-7.36 (m, 2H), 7.36-7.30 (m, 2H), 7.22 (dd, J=10.8, 15.4 Hz, 1H), 5.36-5.11 (m, 1H), 4.47-4.34 (m, 1H), 4.31-4.15 (m, 2H), 4.15-3.81 (m, 5H), 3.77-3.66 (m, 2H), 3.65-3.48 (m, 2H), 3.33-3.18 (m, 1H), 3.15 (d, J=2.5 Hz, 3H), 3.13-3.10 (m, 2H), 3.07 (br d, J=5.4 Hz, 1H), 3.05 (br s, 1H), 2.92-2.83 (m, 1H), 2.69-2.66 (m, 3H), 2.18-2.11 (m, 2H), 2.06 (br s, 1H), 2.00 (br d, J=7.9 Hz, 1H), 1.92-1.74 (m, 3H). LCMS Rt=2.996 min, m/z=696.3 [M+H]+.

LCMS (5 to 95% acetonitrile in water+0.03% ammonium bicarbonate over 6 mins) retention time 2.996 min, ESI+ found [M+H]=696.3.

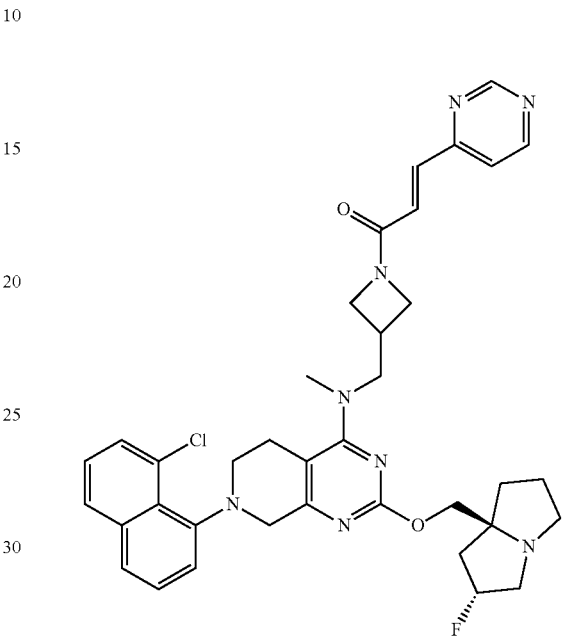

Example 70 (Method 9): (E)-1-(3-(((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)methyl)azetidin-1-yl)-3-(pyrimidin-4-yl)prop-2-en-1-one

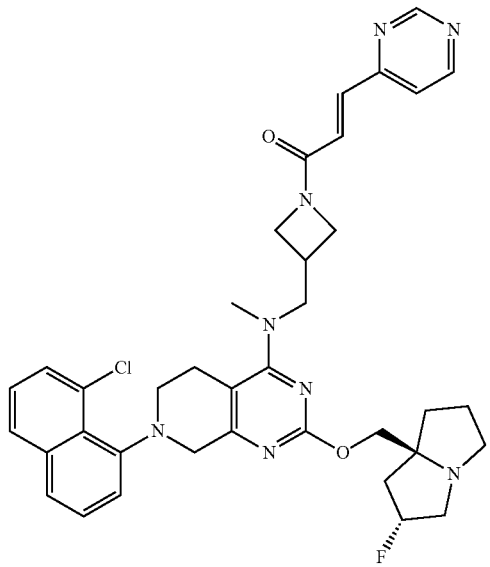 [SMILES: CN(CC1CN(C(=O)/C=C/c2ccncn2)C1)c1nc(OC[C@@]23CCCN2C[C@H](F)C3)nc2c1CCN(c1cccc3cccc(Cl)c13)C2]

Step 1: (E)-1-(3-(((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)methyl)azetidin-1-yl)-3-(pyrimidin-4-yl)prop-2-en-1-one The Homer-Wadsworth-Emmons reaction was prepared in a similar fashion to Method #9, Step 9.

The crude product was purified by reverse phase HPLC (column: Waters Xbridge Prep OBD C18 150*40 mm*10 μm; mobile phase: [water (ammonium bicarbonate)-acetonitrile]; B %: 35%-65%, 8 min) affording (E)-1-(3-(((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)methyl)azetidin-1-yl)-3-(pyrimidin-4-yl)prop-2-en-1-one (32.03 mg, 34.06%) as a white solid: $^1$H NMR (400 MHz, Acetonitrile-d3) δ 9.22-9.12 (m, 1H), 8.80 (d, J=5.1 Hz, 1H), 7.87 (d, J=8.1 Hz, 1H), 7.70 (d, J=8.3 Hz, 1H), 7.60-7.48 (m, 3H), 7.47-7.37 (m, 2H), 7.36-7.31 (m, 1H), 7.26 (dd, J=10.6, 15.4 Hz, 1H), 5.37-5.10 (m, 1H), 4.49-4.36 (m, 1H), 4.31-4.16 (m, 2H), 4.14-3.81 (m, 5H), 3.79-3.66 (m, 2H), 3.66-3.50 (m, 2H), 3.31-3.20 (m, 1H), 3.15 (d, J=3.0 Hz, 3H), 3.13 (br d, J=3.5 Hz, 2H), 3.07-3.02 (m, 1H), 2.94-2.84 (m, 1H), 2.67 (br d, J=15.0 Hz, 1H), 2.15-2.09 (m, 2H), 2.07 (br s, 1H), 2.02 (br d, J=3.3 Hz, 1H), 1.91-1.78 (m, 3H). LCMS Rt=3.138 min, m/z=682.3 [M+H]+.

LCMS (5 to 95% acetonitrile in water+0.03% ammonium bicarbonate over 6 mins) retention time 3.138 min, ESI+ found [M+H]=682.3.

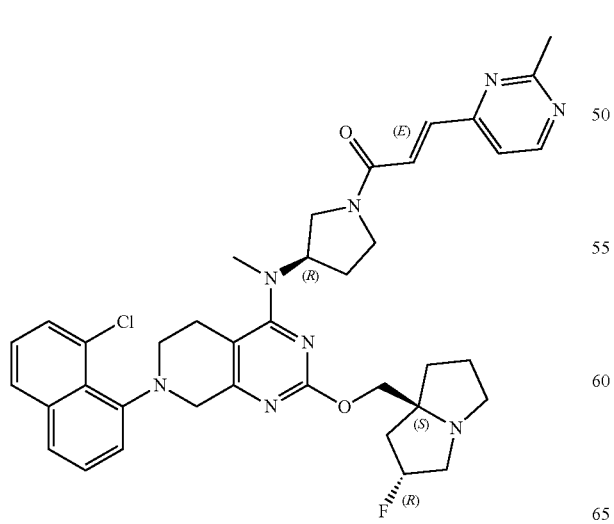

Example 71 (Method 9): (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(2-methylpyrimidin-4-yl)prop-2-en-1-one

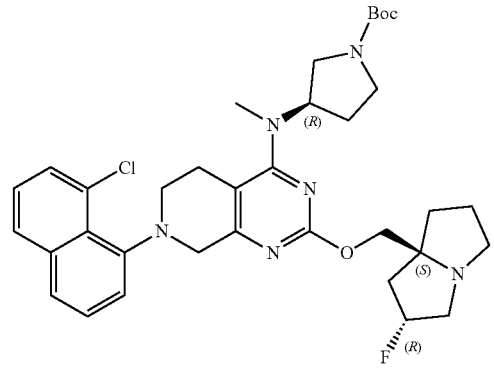

Step 1: (R)-tert-butyl 3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidine-1-carboxylate The substitution reaction was prepared in a similar fashion to Method #4, Step 9. The crude product was purified by column chromatography (silica gel, 100-200 mesh, 0-100% ethyl acetate in petroleum ether) affording (R)-tert-butyl 3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidine-1-carboxylate (1.81 g, 60.04%) as a yellow oil. LCMS Rt=1.652 min, m/z=650.3 [M+H]$^+$.

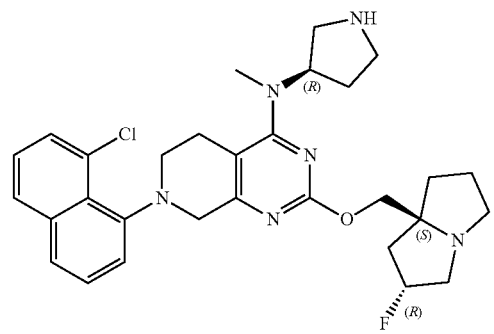

Step 2: 7-(8-chloronaphthalen-1-yl)-2-(((2R,7aS)-2-fluorohexahydro-1H-pyrrolizin-7a-yl)methoxy)-N-methyl-N—((R)-pyrrolidin-3-yl)-5,6,7,8-tetrahydropyrido[3,4-d]pyrimidin-4-amine The deprotection of Boc was prepared in a similar fashion to Method #1, Step 9. The reaction mixture was concentrated in vacuo affording 7-(8-chloronaphthalen-1-yl)-2-(((2R,7aS)-2-fluorohexahydro-1H-pyrrolizin-7a-yl)methoxy)-N-methyl-N—((R)-pyrrolidin-3-yl)-5,6,7,8-tetrahydropyrido

[3,4-d]pyrimidin-4-amine (1.9 g, crude, trifluoroacetate salt) as a yellow oil used in the next step without further purification. LCMS Rt=0.509 min, m/z=550.3 [M+H]⁺.

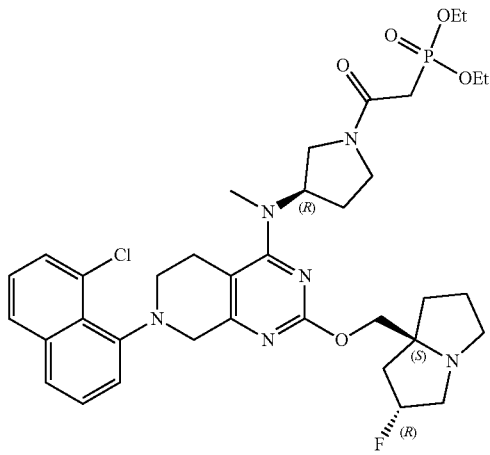

Step 3: diethyl (2-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-2-oxoethyl)phosphonate The amide coupling reaction was prepared in a similar fashion to Method #9, Step 8. The crude product was purified by column chromatography (silica gel, 100-200 mesh, 0-100% ethyl acetate in petroleum ether) affording diethyl (2-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-2-oxoethyl)phosphonate (1.9 g, 96.28%) as a yellow oil.

LCMS Rt=0.628 min, m/z=728.3 [M+H]⁺.

Step 4: (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(2-methylpyrimidin-4-yl)prop-2-en-1-one The Homer-Wadsworth-Emmons reaction was prepared in a similar fashion to Method #9, Step 9. The crude product was purified by reverse phase prep-HPLC (column: Waters Xbridge Prep OBD C18 150*40 mm*10 μm; mobile phase: [water (NH₄HCO₃)-acetonitrile]; B %: 45%-75%, 8 min) affording (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(2-methylpyrimidin-4-yl)prop-2-en-1-one (8.22 mg, 5.59%) as a white solid: ¹H NMR (400 MHz, Acetonitrile-d3) δ 8.73-8.66 (m, 1H), 7.87 (d, J=8.1 Hz, 1H), 7.70 (br d, J=8.0 Hz, 1H), 7.61-7.38 (m, 5H), 7.38-7.30 (m, 2H), 5.38-5.11 (m, 1H), 4.93-4.73 (m, 1H), 4.31-4.15 (m, 1H), 4.11-3.91 (m, 3H), 3.87-3.62 (m, 3H), 3.60-3.40 (m, 2H), 3.24-2.97 (m, 8H), 2.94-2.79 (m, 1H), 2.71-2.59 (m, 4H), 2.18-2.11 (m, 2H), 2.10-2.01 (m, 2H), 1.93-1.67 (m, 4H). LCMS Rt=3.238 min, m/z=696.3 [M+H]⁺.

LCMS (5 to 95% acetonitrile in water+0.1% trifluoroacetic acid over 6 mins) retention time 3.238 min, ESI+ found [M+H]=696.3.

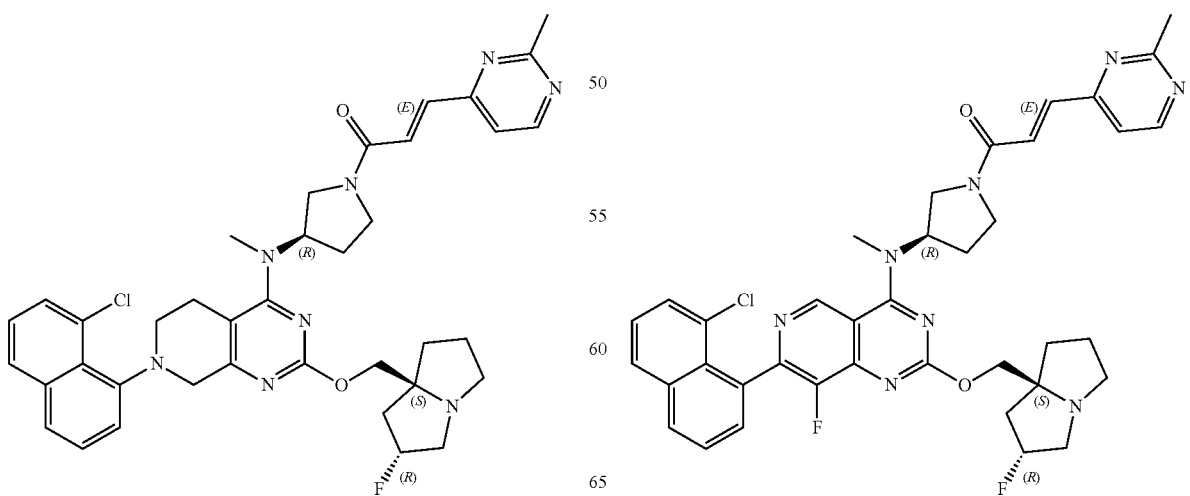

Example 72 (Method 8): (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(2-methylpyrimidin-4-yl)prop-2-en-1-one

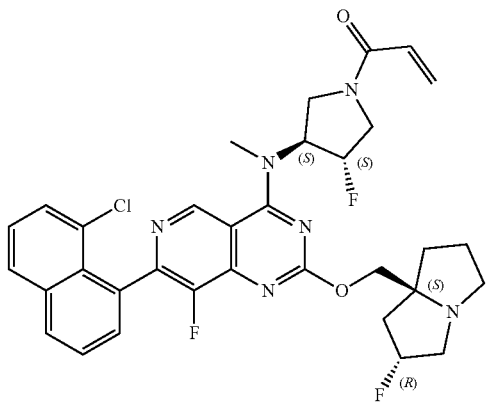

Example 73 (Method 6): 1-((3S,4S)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidin-1-yl)prop-2-en-1-one

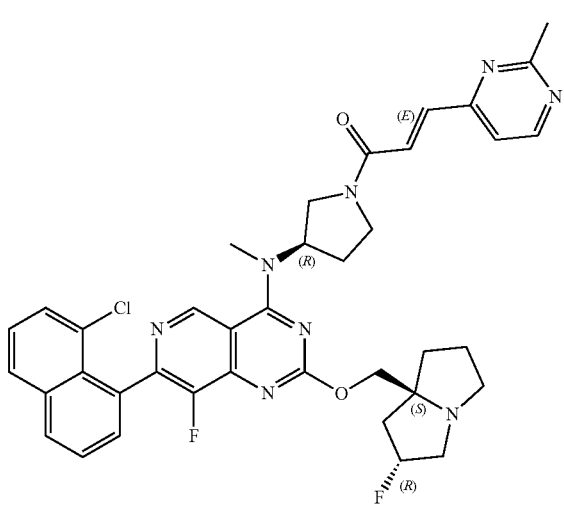

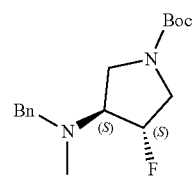

Step 1: (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(2-methylpyrimidin-4-yl)prop-2-en-1-one Step 1: (3S,4S)-tert-butyl 3-(benzyl(methyl)amino)-4-fluoropyrrolidine-1-carboxylate The reductive amination was prepared in a similar fashion to Method #6, Step 1. The residue was purified by column chromatography (silica gel, 100-200 mesh, 0-10% ethyl acetate in petroleum ether) affording (3S,4S)-tert-butyl 3-(benzyl(methyl)amino)-4-fluoropyrrolidine-1-carboxylate (1.5 g, 66.3%) as a yellow oil. LCMS Rt=0.613 min, m/z=308.2 [M+H]$^+$.

The Homer-Wadsworth-Emmons reaction was prepared in a similar fashion to Method #8, Step 4. The crude was purified by reverse phase HPLC (column: column: Waters Xbridge BEH C18 100*30 mm*10 μm; mobile phase: [water (NH$_4$HCO$_3$)-acetonitrile]; B %: 35%-65%, 8 min) affording (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(2-methylpyrimidin-4-yl)prop-2-en-1-one (20.43 mg, 42.47%) as a brown solid: $^1$H NMR (400 MHz, Acetonitrile-d3) δ 9.32-9.14 (m, 1H), 8.79-8.63 (m, 1H), 8.25-7.95 (m, 2H), 7.81-7.69 (m, 1H), 7.68-7.59 (m, 2H), 7.58-7.44 (m, 3H), 7.36 (br dd, J=4.8, 9.1 Hz, 1H), 5.52-5.09 (m, 2H), 4.26-4.20 (m, 1H), 4.19-4.11 (m, 1H), 4.09-3.98 (m, 1H), 3.96-3.73 (m, 2H), 3.70-3.54 (m, 1H), 3.52-3.40 (m, 3H), 3.24-3.00 (m, 3H), 2.96-2.80 (m, 1H), 2.75-2.62 (m, 3H), 2.50-2.31 (m, 2H), 2.14-2.06 (m, 2H), 1.86 (br s, 4H). LCMS Rt=2.922 min, m/z=710.3 [M+H]$^+$.

LCMS (5 to 95% acetonitrile in water +0.03% ammonium bicarbonate over 6 mins) retention time 2.922 min, ESI+ found [M+H]=710.3.

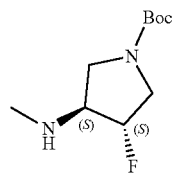

Step 2: (3S,4S)-tert-butyl 3-fluoro-4-(methylamino)pyrrolidine-1-carboxylate

The deprotection of Bn group was prepared in a similar fashion to Method #6, Step 6. The mixture was concentrated in vacuo affording (3S,4S)-tert-butyl 3-fluoro-4-(methylamino)pyrrolidine-1-carboxylate (550 mg, crude) as a white oil, used in next step without any further purification.

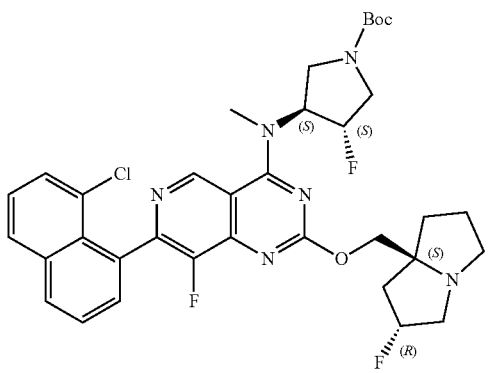

Step 3: (3S,4S)-tert-butyl 3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidine-1-carboxylate The substitution reaction was prepared in a similar fashion to Method #1, Step 8. The residue was purified by reverse phase HPLC (column: Phenomenex Luna 80*30 mm*3 μm; mobile phase: [water (trifluoroacetic acid)-acetonitrile]; B %: 10%-40%, 8 min) affording (3S,4S)-tert-butyl 3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidine-1-carboxylate (25 mg, crude, trifluoroacetic salt) as a white solid. LCMS Rt=1.770 min, m/z=682.3 [M+H]$^+$.

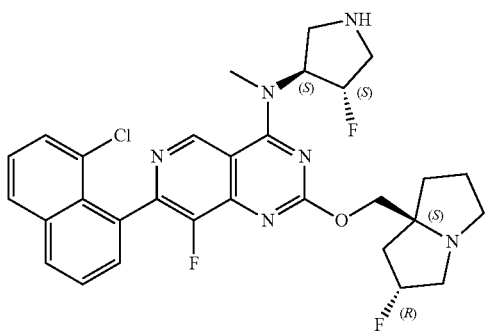

Step 4: 7-(8-chloronaphthalen-1-yl)-8-fluoro-2-(((2R,7aS)-2-fluorohexahydro-1H-pyrrolizin-7a-yl)methoxy)-N-((3S,4S)-4-fluoropyrrolidin-3-yl)-N-methylpyrido[4,3-d]pyrimidin-4-amine The de-Boc protecting reaction was prepared in a similar fashion to Method #1, Step 9. The reaction mixture was concentrated in vacuo affording 7-(8-chloronaphthalen-1-yl)-8-fluoro-2-(((2R,7aS)-2-fluorohexahydro-1H-pyrrolizin-7a-yl)methoxy)-N-((3S,4S)-4-fluoropyrrolidin-3-yl)-N-methylpyrido[4,3-d]pyrimidin-4-amine (22.45 mg, trifluoroacetate salt) as a yellow solid.

LCMS Rt=0.876 min, m/z=582.2 [M+H]$^+$.

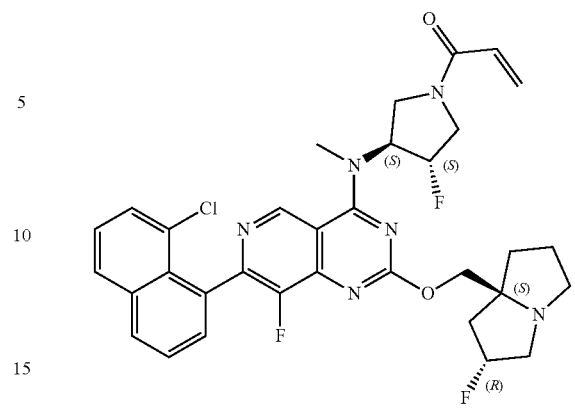

Step 5: 1-((3S,4S)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidin-1-yl)prop-2-en-1-one The amide coupling reaction was prepared in a similar fashion to Method #6, Step 13. The residue was purified by reverse phase HPLC (column: Waters Xbridge BEH C18 100*30 mm*10 um; mobile phase: [water (NH$_4$HCO$_3$)-acetonitrile]; B %: 40%-70%, 8 min) affording 1-((3S,4S)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidin-1-yl)prop-2-en-1-one (5.3 mg, 20.00%) as a yellow solid: $^1$H NMR (400 MHz, Acetonitrile-d3) δ 9.36-9.20 (m, 1H), 8.15 (d, J=8.0 Hz, 1H), 8.04 (d, J=8.1 Hz, 1H), 7.76-7.68 (m, 1H), 7.67-7.61 (m, 2H), 7.58-7.50 (m, 1H), 6.60 (dd, J=10.4, 16.8 Hz, 1H), 6.30 (br d, J=16.8 Hz, 1H), 5.75 (ddd, J=1.9, 5.2, 10.3 Hz, 1H), 5.70-5.49 (m, 1H), 5.42-5.18 (m, 2H), 4.41-4.07 (m, 4H), 3.99-3.72 (m, 2H), 3.52 (dd, J=3.9, 5.3 Hz, 3H), 3.29-3.06 (m, 3H), 3.06-2.87 (m, 1H), 2.22-2.05 (m, 4H), 1.93-1.82 (m, 2H). LCMS Rt=1.012 min, m/z=636.2 [M+H]$^+$.

LCMS (5 to 95% acetonitrile in water+0.03% ammonium bicarbonate over 6 mins) retention time 1.012 min, ESI+ found [M+H]=636.2.

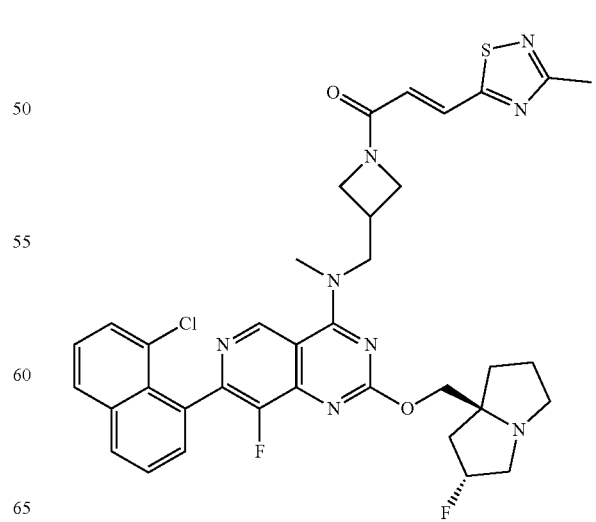

Example 74 (Method 8): (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-methyl-1,2,4-thiadiazol-5-yl)prop-2-en-1-one

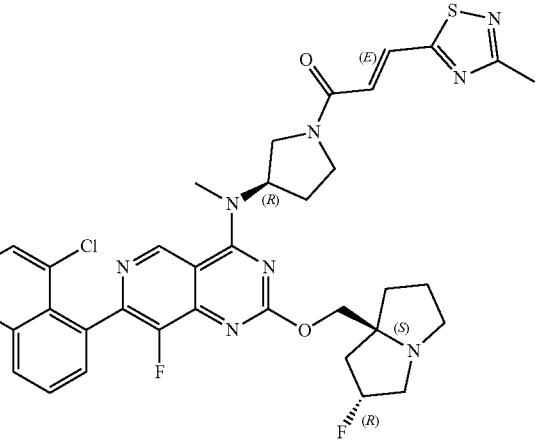

Example 75 (Method 8): (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-methyl-1,2,4-thiadiazol-5-yl)prop-2-en-1-one

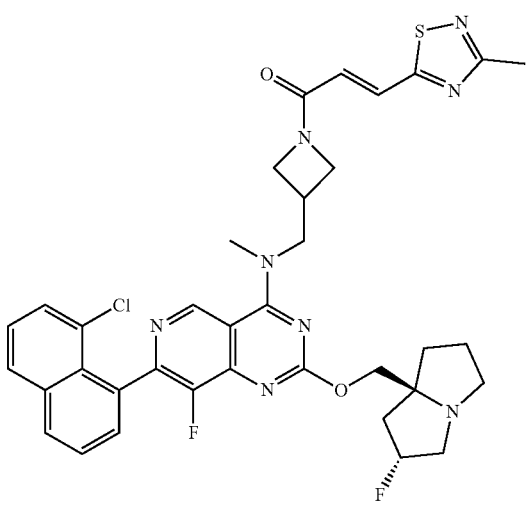 [SMILES: Cc1nsc(/C=C/C(=O)N2CC(CN(C)c3nc(OC[C@@]45CCCN4C[C@H](F)C5)nc4c(F)c(-c5cccc6cccc(Cl)c56)ncc34)C2)n1]

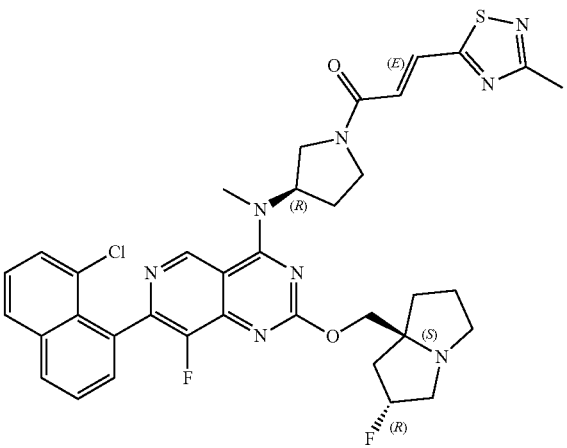

Step 1: (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-methyl-1,2,4-thiadiazol-5-yl)prop-2-en-1-one The Horner-Wadsworth-Emmons reaction was prepared in a similar fashion to Method #8, Step 4. The residue was purified by reverse phase HPLC (column: Waters Xbridge BEH C18 100*30 mm*10 μm; mobile phase: [water (NH₄HCO₃)-acetonitrile]; B %: 35%-65%, 8 min) affording (E)-1-[3-[[[7-(8-chloro-1-naphthyl)-8-fluoro-2-[[(2R,8S)-2-fluoro-1,2,3,5,6,7-hexahydropyrrolizin-8-yl]methoxy]pyrido[4,3-d]pyrimidin-4-yl]-methyl-amino]methyl]azetidin-1-yl]-3-(3-methyl-1,2,4-thiadiazol-5-yl)prop-2-en-1-one (26.37 mg, 34.16%) as a white solid. $^1$H NMR (400 MHz, Acetonitrile-d3) δ 9.17 (s, 1H), 8.18 (s, 1H), 6.63-6.50 (m, 1H), 6.49 (s, 1H), 6.27-6.17 (m, 1H), 5.71-5.61 (m, 1H), 5.42-5.22 (m, 2H), 4.36-4.25 (m, 2H), 3.92 (dd, J=8.1, 12.8 Hz, 1H), 3.88-3.75 (m, 1H), 3.62 (br s, 1H), 3.57-3.42 (m, 1H), 3.38 (s, 3H), 3.36 (br s, 1H), 3.34-3.16 (m, 2H), 2.99 (br d, J=5.6 Hz, 1H), 2.40-2.25 (m, 3H), 2.24 (s, 3H), 2.21 (br s, 1H), 2.19-2.10 (m, 1H), 2.03-1.94 (m, 3H), 1.93-1.85 (m, 3H). LCMS Rt=2.203 min, m/z =716.2 [M+H]⁺.

LCMS (5 to 95% acetonitrile in water+0.03% ammonium bicarbonate over 6 min) retention time 2.203 min, ESI+ found [M+H]=716.2.

Step 1: (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-methyl-1,2,4-thiadiazol-5-yl)prop-2-en-1-one The Horner-Wadsworth-Emmons reaction was prepared in a similar fashion to Method #8, Step 4. The crude was purified by reverse phase HPLC (column: Waters Xbridge Prep OBD C18 150*40 mm*10 μm; mobile phase: [water (NH₄HCO₃)-acetonitrile]; B %: 35%-65%, 8 min) affording (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-methyl-1,2,4-thiadiazol-5-yl)prop-2-en-1-one (30.39 mg, 39.36%) as a white solid: $^1$H NMR (400 MHz, Acetonitrile-d3) δ 9.34-9.08 (m, 1H), 8.23-7.97 (m, 2H), 7.84-7.68 (m, 2H), 7.68-7.59 (m, 2H), 7.57-7.48 (m, 1H), 7.41-7.20 (m, 1H), 5.54-5.06 (m, 2H), 4.29-4.14 (m, 2H), 4.14-3.85 (m, 2H), 3.83-3.72 (m, 1H), 3.70-3.49 (m, 1H), 3.45 (s, 3H), 3.23-3.03 (m, 3H), 2.95-2.84 (m, 1H), 2.65 (d, J=12.1 Hz, 3H), 2.43 (br d, J=6.1 Hz, 1H), 2.34 (br d, J=6.4 Hz, 1H), 2.23-2.17 (m, 1H), 2.13-2.03 (m, 2H), 1.95-1.78 (m, 3H). LCMS Rt=2.222 min, m/z=716.2 [M+H]+.

LCMS (5 to 95% acetonitrile in water+0.03% ammonium bicarbonate over 6 mins) retention time 2.222 min, ESI+ found [M+H]=716.2.

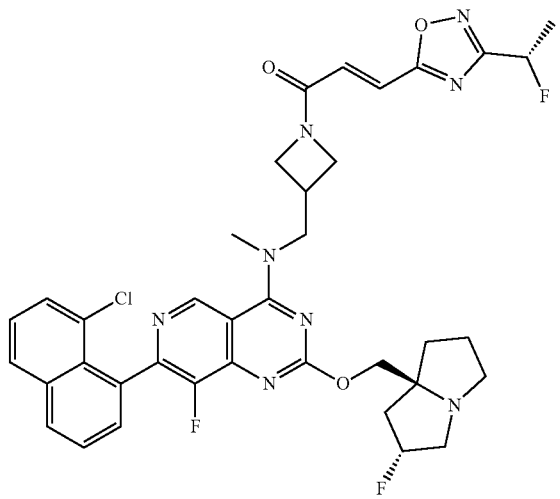 [SMILES: C[C@H](F)c1noc(/C=C/C(=O)N2CC(CN(C)c3nc(OC[C@@]45CCCN4C[C@H](F)C5)nc4c(F)c(-c5cccc6cccc(Cl)c56)ncc34)C2)n1]

Example 76 (Method 1): (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-((S)-1-fluoroethyl)-1,2,4-oxadiazol-5-yl)prop-2-en-1-one

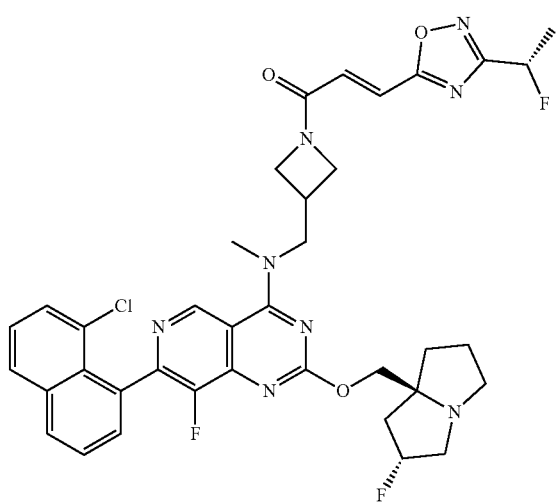 [SMILES: C[C@H](F)c1noc(/C=C/C(=O)N2CC(CN(C)c3nc(OC[C@@]45CCCN4C[C@H](F)C5)nc4c(F)c(-c5cccc6cccc(Cl)c56)ncc34)C2)n1]

Step 1: (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-((S)-1-fluoroethyl)-1,2,4-oxadiazol-5-yl)prop-2-en-1-one The amide coupling reaction was prepared in a similar fashion to Method #1, Step 10. The residue was purified by reverse phase HPLC (column: Waters Xbridge BEH C18 100*30 mm*10 μm; mobile phase: [water (NH₄HCO₃)-acetonitrile]; B %: 35%-65%, 8 min) affording (E)-1-[3-[[[7-(8-chloro-1-naphthyl)-8-fluoro-2-[[(2R,8S)-2-fluoro-1,2,3,5,6,7-hexahydropyrrolizin-8-yl]methoxy]pyrido[4,3-d]pyrimidin-4-yl]-methyl-amino]methyl]azetidin-1-yl]-3-[3-[(1S)-1-fluoroethyl]-1,2,4-oxadiazol-5-yl]prop-2-en-1-one (22.7 mg, 20.45%) as a yellow solid. ¹H NMR (400 MHz, Acetonitrile-d3) δ 9.28 (s, 1H), 8.15 (d, J=8.3 Hz, 1H), 8.05 (d, J=7.5 Hz, 1H), 7.74-7.69 (m, 1H), 7.64 (br d, J=7.4 Hz, 2H), 7.57-7.51 (m, 1H), 7.42-7.36 (m, 1H), 7.28-7.22 (m, 1H), 5.94-5.76 (m, 1H), 5.40-5.19 (m, 1H), 4.55-4.47 (m, 1H), 4.31 (br s, 1H), 4.26-4.20 (m, 3H), 4.17 (br d, J=1.4 Hz, 1H), 4.04-3.94 (m, 1H), 3.62 (s, 3H), 3.32-3.27 (m, 1H), 3.26-3.19 (m, 2H), 3.18-3.13 (m, 1H), 3.00-2.91 (m, 1H), 2.27-2.22 (m, 2H), 2.09 (br d, J=9.1 Hz, 2H), 1.94-1.87 (m, 3H), 1.79-1.71 (m, 3H). LCMS Rt=3.116 min, m/z=732.3 [M+H]⁺.

LCMS (5 to 95% acetonitrile in water+0.03% ammonium bicarbonate over 6 min) retention time 3.116 min, ESI+ found [M+H]=732.3.

Example 77 (Method 5-Master): (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-((S)-1-fluoroethyl)-1,2,4-oxadiazol-5-yl)prop-2-en-1-one

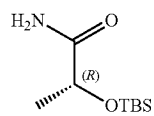

Step 1: (R)-2-((tert-butyldimethylsilyl)oxy)propanamide

To a solution of (2R)-2-hydroxypropanamide (10 g, 112.24 mmol) in N,N-dimethylformamide (250 mL) was added pyridine (35.51 g, 448.97 mmol) and tert-butyl-chloro-dimethyl-silane (33.83 g, 224.48 mmol). The mixture was stirred at 25° C. for 12 h. The reaction mixture was quenched with water (200 mL), and then extracted with ethyl acetate (3×200 mL), dried over sodium sulphate, filtered and concentrated to dryness in vacuo. The residue was purified by column chromatography (silica gel, 100-200 mesh, 5-50% ethyl acetate in petroleum ether) affording (2R)-2-[tert-butyl(dimethyl)silyl]oxypropanamide (16 g, 70.1%) as a colorless oil.

LCMS Rt=0.624 min, m/z=203.1 [M+H]+.

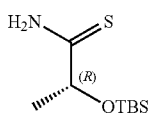

Step 2: (R)-2-((tert-butyldimethylsilyl)oxy)propanethioamide

To a solution of (2R)-2-[tert-butyl(dimethyl)silyl]oxypropanamide (14.00 g, 68.85 mmol) in 2-methyloxolane (200 mL) was added lawesson's reagent (13.92 g, 34.42 mmol) and sodium carbonate (8.03 g, 75.73 mmol). The mixture was stirred at 80° C. for 1 h. The reaction mixture was quenched with water (200 mL), and extracted with ethyl acetate (3×200 mL), dried over sodium sulphate, filtered and concentrated to dryness in vacuo affording (R)-2-((tert-butyldimethylsilyl)oxy)propanethioamide (16 g, crude) as a colorless oil, used in next step without any further purification. LCMS Rt=0.700 min, m/z=219.1 [M+H]+.

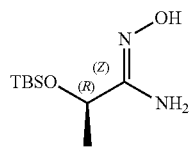

Step 3: (R,Z)-2-((tert-butyldimethylsilyl)oxy)-N'-hydroxypropanimidamide

To a solution of (R)-2-((tert-butyldimethylsilyl)oxy)propanethioamide (16 g, 72.92 mmol) in ethanol (100 mL) and water (50 mL) was added triethylamine (22.14 g, 218.76 mmol), hydroxylamine hydrochloride (10.13 g, 145.84 mmol). The mixture was stirred at 25° C. for 12 h. The reaction mixture was quenched with water (200 mL) and extracted with ethyl acetate (3×200 mL), dried over sodium sulphate, filtered and concentrated to dryness in vacuo affording (R,Z)-2-((tert-butyldimethylsilyl)oxy)-N'-hydroxypropanimidamide (16 g, crude) as a white solid, used in next step without any further purification. LCMS Rt=0.473 min, m/z=218.2 [M+H]+.

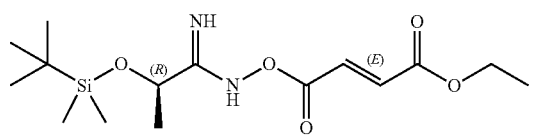

Step 4: (R,E)-ethyl 6-imino-2,2,3,3,5-pentamethyl-9-oxo-4,8-dioxa-7-aza-3-siladodec-10-en-12-oate The coupling reaction was prepared in a similar fashion to Method #1, Step 2, the mixture was concentrated to dryness in vacuo affording (R,E)-ethyl 6-imino-2,2,3,3,5-pentamethyl-9-oxo-4,8-dioxa-7-aza-3-siladodec-10-en-12-oate (19 g, crude) as a yellow oil, used in next step without any further purification. LCMS Rt=0.728 min, m/z=344.2 [M+H]+.

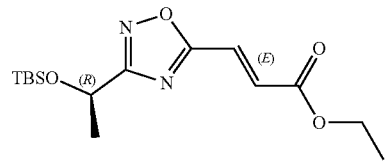

Step 5: (R,E)-ethyl 3-(3-(1-((tert-butyldimethylsilyl)oxy)ethyl)-1,2,4-oxadiazol-5-yl)acrylate The cyclization reaction was prepared in a similar fashion to Method #1, Step 3, the mixture was purified by column chromatography (silica gel, 100-200 mesh, 0-10% ethyl acetate in petroleum ether) affording (R,E)-ethyl 3-(3-(1-((tert-butyldimethylsilyl)oxy)ethyl)-1,2,4-oxadiazol-5-yl)acrylate (9 g, 52.76%) as a yellow oil. LCMS Rt=1.208 min, m/z=326.2 [M+H]+.

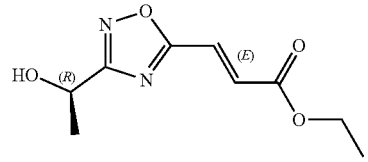

Step 6: (R,E)-ethyl 3-(3-(1-hydroxyethyl)-1,2,4-oxadiazol-5-yl)acrylate

The deprotection of TBS group was prepared in a similar fashion to Method #2, Step 10, the mixture was concentrated in vacuo affording (R,E)-ethyl 3-(3-(1-hydroxyethyl)-1,2,4-oxadiazol-5-yl)acrylate (3.8 g, crude) as a yellow oil, used in next step without any further purification. LCMS Rt=0.470 min, m/z=212.1 [M+H]+.

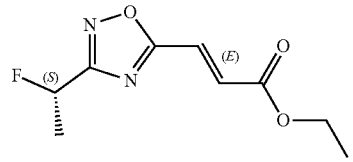

Step 7: (S,E)-ethyl 3-(3-(1-fluoroethyl)-1,2,4-oxadiazol-5-yl)acrylate

To a solution of ethyl (E)-3-[3-[(1R)-1-hydroxyethyl]-1,2,4-oxadiazol-5-yl]prop-2-enoate (1 g, 4.71 mmol) in dichloromethane (20 mL) was added diethylamino sulfur trifluoride (1.14 g, 7.07 mmol) at −78° C. under nitrogen atmosphere. The mixture was stirred at 25° C. for 12 h. The reaction mixture was quenched with water (50 mL), extracted with ethyl acetate (3×50 mL), dried over sodium sulphate, filtered and concentrated to dryness in vacuo affording ethyl (S,E)-ethyl 3-(3-(1-fluoroethyl)-1,2,4-oxadi-azol-5-yl)acrylate (950 mg, crude) as a yellow oil, used in next step without any further purification. LCMS Rt=0.584 min, m/z=214.1 [M+H]⁺.

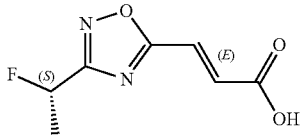

Step 8: (S,E)-3-(3-(1-fluoroethyl)-1,2,4-oxadiazol-5-yl)acrylic acid

The hydrolysis reaction was prepared in a similar fashion to Method #1, Step 4, the mixture was concentrated to dryness in vacuo affording (S,E)-3-(3-(1-fluoroethyl)-1,2,4-oxadiazol-5-yl)acrylic acid (600 mg, crude) as a white solid, used in next step without any further purification. LCMS Rt =0.163 min, m/z=186.0 [M+H]⁺.

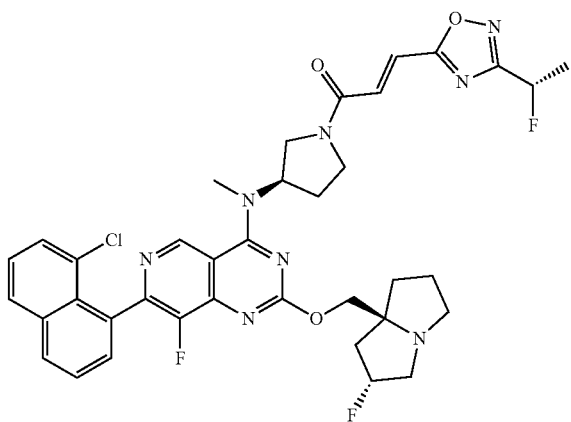 [SMILES: C[C@H](F)c1noc(/C=C/C(=O)N2CC[C@@H](N(C)c3nc(OC[C@@]45CCCN4C[C@H](F)C5)nc4c(F)c(-c5cccc6cccc(Cl)c56)ncc34)C2)n1]

Step 9: (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-((S)-1-fluoroethyl)-1,2,4-oxadiazol-5-yl)prop-2-en-1-one The amide coupling reaction was prepared in a similar fashion to Method #1, Step 10. The residue was purified by reverse phase HPLC (column: Waters Xbridge Prep OBD C18 150*40 mm*10 μm; mobile phase: [water (NH₄HCO₃)-acetonitrile]; B %: 35%-65%, 8 min) affording (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-((S)-1-fluoroethyl)-1,2,4-oxadiazol-5-yl)prop-2-en-1-one (14.91 mg, 13.53%) as a yellow oil: ¹H NMR (400 MHz, Acetonitrile-d3) δ 9.24 (s, 1H), 8.16 (d, J=7.9 Hz, 1H), 8.05 (d, J=8.1 Hz, 1H), 7.75-7.69 (m, 1H), 7.68-7.62 (m, 2H), 7.60-7.52 (m, 2H), 7.48-7.41 (m, 1H), 5.99-5.74 (m, 1H), 5.57-5.21 (m, 2H), 4.41-4.07 (m, 3H), 4.06-3.89 (m, 1H), 3.85-3.53 (m, 2H), 3.51-3.47 (m, 3H), 3.46-3.07 (m, 3H), 3.07-2.92 (m, 1H), 2.49-2.37 (m, 2H), 2.36-2.27 (m, 2H), 2.26-2.22 (m, 2H), 2.13 (br s, 1H), 1.81-1.71 (m, 4H). LCMS Rt=3.156 min, m/z=732.3 [M +H]⁺.

LCMS (5 to 95% acetonitrile in water+0.03% ammonium bicarbonate over 6 mins) retention time 3.156 min, ESI+ found [M+H]=732.3.

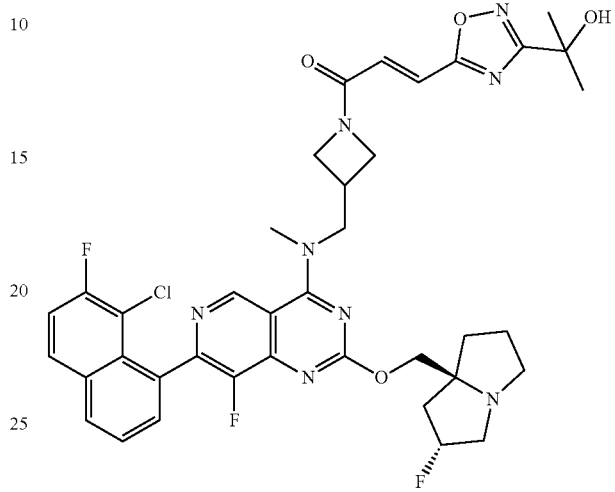

Example 78 (Method 1): (E)-1-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-(2-hydroxypropan-2-yl)-1,2,4-oxadiazol-5-yl)prop-2-en-1-one

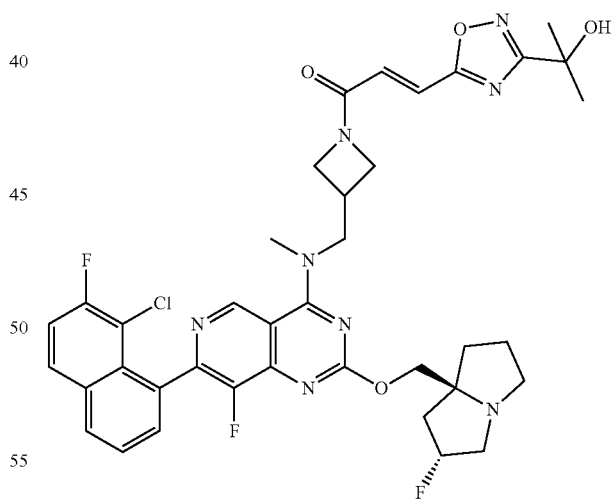

Step 1: (E)-1-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-(2-hydroxypropan-2-yl)-1,2,4-oxadiazol-5-yl)prop-2-en-1-one The amide coupling reaction was prepared in a similar fashion to Method #1, Step 10. The crude was purified by reverse phase HPLC (column: Waters Xbridge BEH C18 100*30 mm*10 μm; mobile phase: [water (NH₄HCO₃)-acetonitrile]; B %: 25%-65%, 8 min) affording (E)-1-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-(2-hydroxypropan-2-yl)-1,2,4-oxadiazol-5-yl)prop-2-en-1-one (11.22 mg, 18.88%) as a yellow solid: ¹H NMR (400 MHz, Acetonitrile-d3) δ 9.27 (s, 1H), 8.19-8.13 (m, 1H), 8.11-8.06 (m, 1H), 7.71-7.66 (m, 2H), 7.57-7.52 (m, 1H), 7.40-7.29 (m, 1H), 7.24-7.13 (m, 1H), 5.35-5.18 (m, 1H), 4.50 (t, J=8.6 Hz, 1H), 4.27-4.12 (m, 5H), 3.97 (dt, J=6.0, 9.7 Hz, 1H), 3.61 (s, 3H), 3.30-3.24 (m, 1H), 3.16-3.06 (m, 3H), 2.94-2.87 (m, 1H), 2.20-2.01 (m, 5H), 1.90-1.85 (m, 2H), 1.59 (s, 6H). LCMS Rt=0.992 min, m/z=762.3 [M+H]⁺.

LCMS (5 to 95% acetonitrile in water+0.1% ammonium bicarbonate over 6 mins) retention time 0.992 min, ESI+ found [M+H]=762.3.

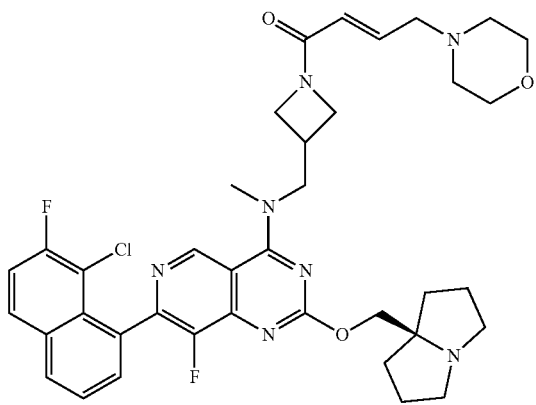

Example 79 (Method 8): (E)-1-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-4-morpholinobut-2-en-1-one

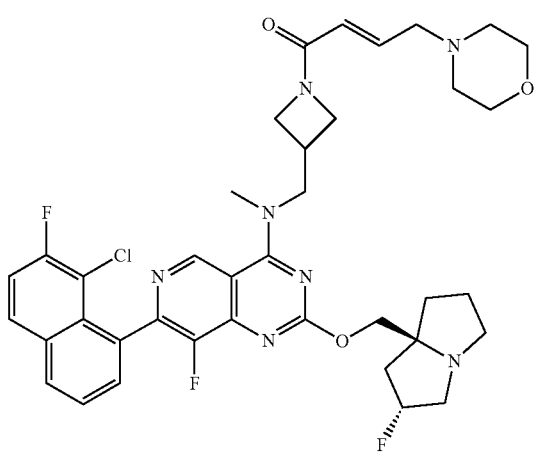

Step 1: (E)-1-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-4-morpholinobut-2-en-1-one The Horner-Wadsworth-Emmons reaction was prepared in a similar fashion to Method #8, Step 4. The crude was purified by reverse phase HPLC (column: Waters Xbridge BEH C18 100*30 mm*10 μm; mobile phase: [water (NH₄HCO₃)-acetonitrile]; B %: 25%-65%, 8 min) affording (E)-1-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-4-morpholinobut-2-en-1-one (4.92 mg, 24.06%) as a white solid: ¹H NMR (400 MHz, Acetonitrile-d3) δ 9.23 (s, 1H), 8.13 (dd, J=2.8, 6.8 Hz, 1H), 8.09-8.03 (m, 1H), 7.70-7.64 (m, 2H), 7.51 (t, J=8.9 Hz, 1H), 6.64 (td, J=6.2, 15.4 Hz, 1H), 6.10 (br d, J=15.5 Hz, 1H), 5.35-5.18 (m, 1H), 4.37-4.27 (m, 1H), 4.21-4.05 (m, 6H), 3.83 (br dd, J=8.8, 14.8 Hz, 1H), 3.62-3.59 (m, 3H), 3.57 (s, 3H), 3.21-3.14 (m, 3H), 3.11-3.05 (m, 3H), 2.95-2.86 (m, 1H), 2.38 (br d, J=4.0 Hz, 4H), 2.10 (br s, 2H), 2.04 (br d, J=7.8 Hz, 1H), 1.87 (br dd, J=6.4, 11.3 Hz, 3H), 1.79-1.74 (m, 1H). LCMS Rt=2.828 min, m/z=735.3 [M+H]+.

LCMS (5 to 95% acetonitrile in water+0.1% ammonium bicarbonate over 6 mins) retention time 2.828 min, ESI+ found [M+H]=735.3.

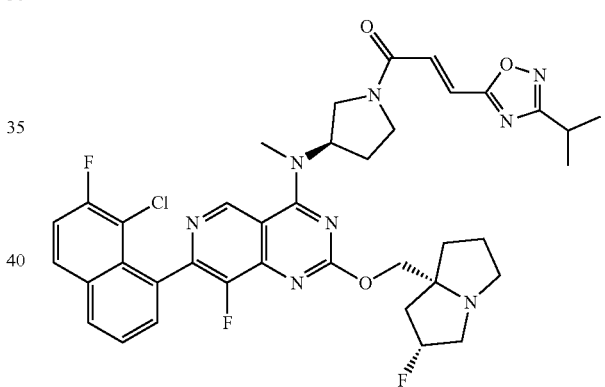

Example 80 (Method 1): (E)-1-((R)-3-((7-(8-chloro-7-fluoronaphthalen-1-yl)-8-fluoro-2-(((2R,7aR)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-isopropyl-1,2,4-oxadiazol-5-yl)prop-2-en-1-one

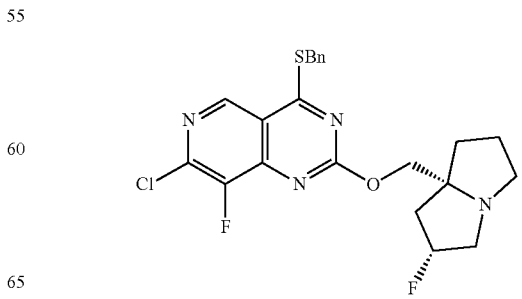

Step 1: 4-(benzylthio)-7-chloro-8-fluoro-2-(((2R, 7aR)-2-fluorohexahydro-1H-pyrrolizin-7a-yl) methoxy)pyrido[4,3-d]pyrimidine The substitution reaction was prepared in a similar fashion to Method #1, Step 5. The mixture was diluted with water (20 mL) and extracted with ethyl acetate (3×50 mL). The combined organic layers were dried over sodium sulphate and concentrated in vacuo affording 4-(benzylthio)-7-chloro-8-fluoro-2-(((2R,7aR)-2-fluorohexahydro-1H-pyrrolizin-7a-yl)methoxy)pyrido[4,3-d]pyrimidine (3.4 g, crude) as a brown oil, used into the next step without further purification. LCMS Rt=0.572 min, m/z=462.1 [M+H]⁺.

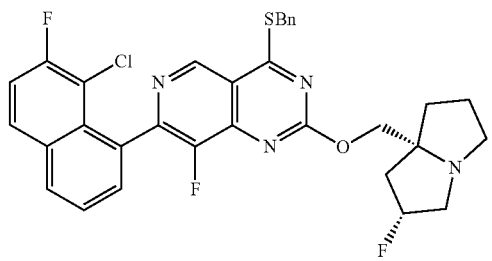

Step 2: 4-(benzylthio)-7-(8-chloro-7-fluoronaphthalen-1-yl)-8-fluoro-2-(((2R,7aR)-2-fluorohexahydro-1H-pyrrolizin-7a-yl)methoxy)pyrido[4,3-d]pyrimidine The Suzuki reaction was prepared in a similar fashion to Method #1, Step 6. The residue was purified by column chromatography (silica gel, 100-200 mesh, 0-100% ethyl acetate in petroleum ether) affording 4-(benzylthio)-7-(8-chloro-7-fluoronaphthalen-1-yl)-8-fluoro-2-(((2R,7aR)-2-fluorohexahydro-1H-pyrrolizin-7a-yl)methoxy)pyrido[4,3-d]pyrimidine (1.2 g, 26.91%) as a brown oil. LCMS Rt=0.640 min, m/z=606.2 [M+H]⁺.

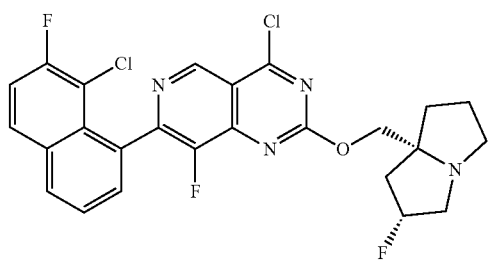 [SMILES: Fc1ccc2cccc(-c3ncc4c(Cl)nc(OC[C@]56CCCN5C[C@H](F)C6)nc4c3F)c2c1Cl]

Step 3: 4-chloro-7-(8-chloro-7-fluoronaphthalen-1-yl)-8-fluoro-2-(((2R,7aR)-2-fluorohexahydro-1H-pyrrolizin-7a-yl)methoxy)pyrido[4,3-d]pyrimidine The chlorination reaction was prepared in a similar fashion to Method #1, Step 7. The reaction mixture was concentrated to dryness in vacuo affording 4-chloro-7-(8-chloro-7-fluoronaphthalen-1-yl)-8-fluoro-2-(((2R,7aR)-2-fluorohexahydro-1H-pyrrolizin-7a-yl)methoxy)pyrido[4,3-d]pyrimidine (684 mg, crude) as a yellow oil, used in next step without any further purification. LCMS Rt=0.574 min, m/z=518.1 [M+H]⁺.

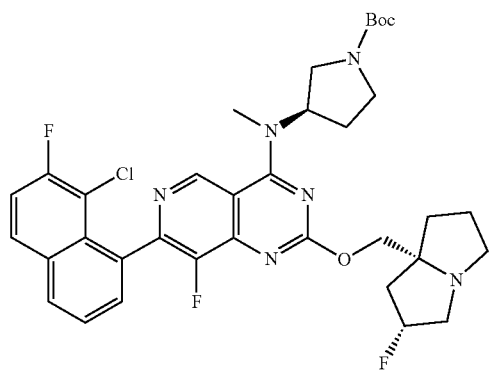 [SMILES: CN(c1nc(OC[C@]23CCCN2C[C@H](F)C3)nc2c(F)c(-c3cccc4ccc(F)c(Cl)c34)ncc12)[C@@H]1CCN(C(=O)OC(C)(C)C)C1]

Step 4: (R)-tert-butyl 3-((7-(8-chloro-7-fluoronaphthalen-1-yl)-8-fluoro-2-(((2R,7aR)-2-fluorohexahydro-1H-pyrrolizin-7a-yl)methoxy)pyrido[4,3-d]pyrimidin-4-yl)(methyl)amino)pyrrolidine-1-carboxylate The substitution reaction was prepared in a similar fashion to Method #1, Step 8. The residue was purified by reverse phase HPLC (column: Phenomenex luna C18 250*50 mm*10 μm; mobile phase: [water (trifluoroacetic acid)-acetonitrile]; B %: 30%-60%, 10 min) affording (R)-tert-butyl 3-((7-(8-chloro-7-fluoronaphthalen-1-yl)-8-fluoro-2-(((2R,7aR)-2-fluorohexahydro-1H-pyrrolizin-7a-yl)methoxy)pyrido[4,3-d]pyrimidin-4-yl)(methyl)amino) pyrrolidine-1-carboxylate (270 mg, 21.49%, trifluoroacetate salt) as a white solid. LCMS Rt=0.618 min, m/z=682.3 [M+H]⁺.

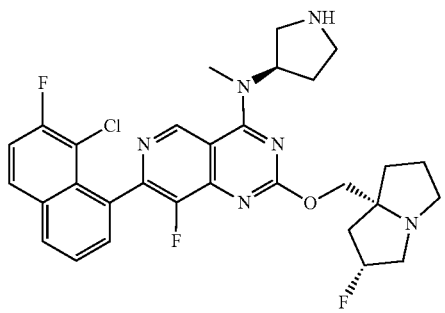 [SMILES: CN(c1nc(OC[C@]23CCCN2C[C@H](F)C3)nc2c(F)c(-c3cccc4ccc(F)c(Cl)c34)ncc12)[C@@H]1CCNC1]

Step 5: 7-(8-chloro-7-fluoronaphthalen-1-yl)-8-fluoro-2-(((2R,7aR)-2-fluorohexahydro-1H-pyrrolizin-7a-yl)methoxy)-N-methyl-N—((R)-pyrrolidin-3-yl)pyrido[4,3-d]pyrimidin-4-amine The deprotection of Boc group was prepared in a similar fashion to Method #1, Step 9. The reaction mixture was concentrated in vacuo affording 7-(8-chloro-7-fluoronaphthalen-1-yl)-8-fluoro-2-(((2R,7aR)-2-fluorohexahydro-1H-pyrrolizin-7a-yl)methoxy)-N-methyl-N—((R)-pyrrolidin-3-yl)pyrido[4,3-d]pyrimidin-4-amine (200 mg, crude, trifluoroacetate salt) as a brown oil, used in next step without any further purification. LCMS Rt=0.469 min, m/z=582.2 [M+H]⁺.

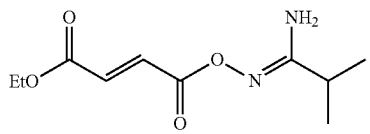 [SMILES: CCOC(=O)/C=C/C(=O)O/N=C(\N)C(C)C]

Step 6: (E)-ethyl 4-(((Z)-(1-amino-2-methylpropy-lidene)amino)oxy)-4-oxobut-2-enoate The amide coupling reaction was prepared in a similar fashion to Method #1, Step 2. The mixture was concentrated in vacuo affording (E)-ethyl 4-(((Z)-(1-amino-2-methylpropylidene)amino)oxy)-4-oxobut-2-enoate (15 g, crude) used in next step without further purification. LCMS Rt=0.545 min, m/z=228.1 [M+H]$^+$.

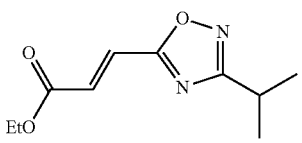

Step 7: (E)-ethyl 3-(3-isopropyl-1,2,4-oxadiazol-5-yl)acrylate

The cyclization reaction was prepared in a similar fashion to Method #1, Step 3. The mixture was concentrated in vacuo affording (E)-ethyl 3-(3-isopropyl-1,2,4-oxadiazol-5-yl)acrylate (15 g, crude), used in next step without further purification. LCMS Rt=0.740 min, m/z=210.1 [M+H]$^+$.

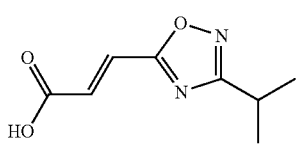

Step 8: (E)-3-(3-isopropyl-1,2,4-oxadiazol-5-yl) acrylic acid

The hydrolysis reaction was prepared in a similar fashion to Method #1, Step 4. The mixture was concentrated in vacuo affording (E)-3-(3-isopropyl-1,2,4-oxadiazol-5-yl) acrylic acid (8 g, 92.32%) as a white solid: $^1$H NMR (400 MHz, Chloroform-d) δ 11.85-11.36 (m, 1H), 7.53 (d, J=16.0 Hz, 1H), 6.97 (d, J=16.0 Hz, 1H), 3.10 (s, 1H), 1.30 (d, J=7.0 Hz, 6H).

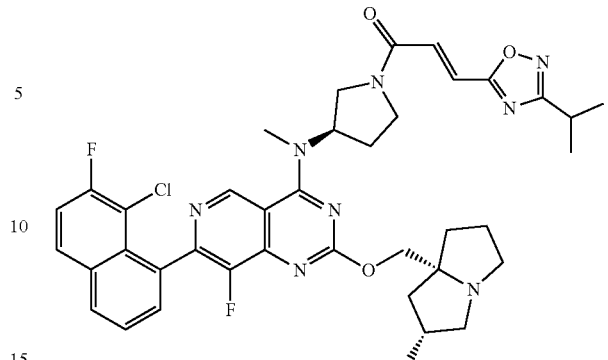

Step 9: (E)-1-((R)-3-((7-(8-chloro-7-fluoronaphtha-len-1-yl)-8-fluoro-2-(((2R,7aR)-2-fluorotetrahydro-1H-pyrrolizin-7a(5H)-yl)methoxy)pyrido[4,3-d]py-rimidin-4-yl)(methyl)amino)pyrrolidin-1-yl)-3-(3-isopropyl-1,2,4-oxadiazol-5-yl)prop-2-en-1-one The amide coupling reaction was prepared in a similar fashion to Method #1, Step 10. The residue was purified by reverse phase HPLC(column: Waters Xbridge BEH C18 100*30 mm*10 um; mobile phase: [water (NH$_4$HCO$_3$)-acetonitrile]; B %: 40%-70%, 8 min) affording (E)-1-((R)-3-((7-(8-chloro-7-fluoronaphthalen-1-yl)-8-fluoro-2-(((2R,7aR)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-isopropyl-1,2,4-oxadiazol-5-yl)prop-2-en-1-one (37.32 mg, 34.00%) as a white solid: $^1$H NMR (400 MHz, Acetonitrile-d3) δ 9.25-9.19 (m, 1H), 8.18-8.06 (m, 2H), 7.73-7.66 (m, 2H), 7.57-7.49 (m, 1H), 7.48-7.34 (m, 2H), 5.52-5.22 (m, 2H), 4.32-4.19 (m, 2H), 4.10-3.97 (m, 1H), 3.96-3.74 (m, 2H), 3.70-3.52 (m, 1H), 3.46 (s, 3H), 3.40-3.25 (m, 1H), 3.19-3.08 (m, 1H), 3.06-2.99 (m, 1H), 2.95-2.78 (m, 1H), 2.63 (br dd, J=5.9, 10.4 Hz, 1H), 2.48-2.33 (m, 3H), 2.07-1.99 (m, 1H), 1.93-1.82 (m, 3H), 1.78-1.69 (m, 1H), 1.35 (dd, J=7.0, 8.8 Hz, 6H). LCMS Rt=2.353 min, m/z=746.3 [M+H]$^+$.

LCMS (5 to 95% acetonitrile in water+0.1% trifluoroacetic acid over 6 mins) retention time 2.353 min, ESI+ found [M+H]=746.3.

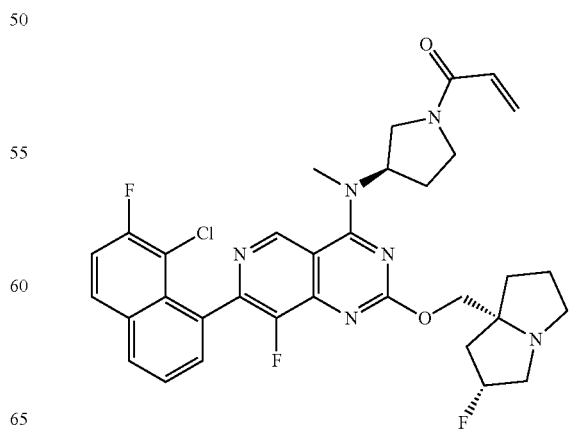

Example 81 (Method 1): 1-((R)-3-((7-(8-chloro-7-fluoronaphthalen-1-yl)-8-fluoro-2-(((2R,7aR)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one

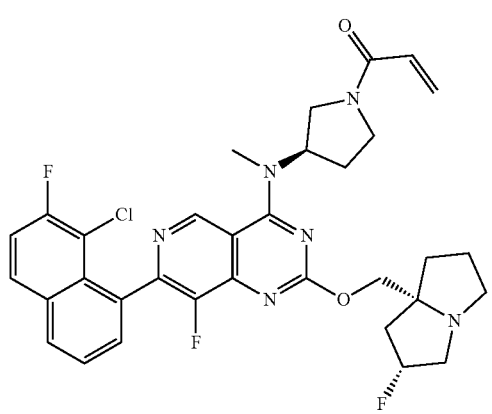 [SMILES: C=CC(=O)N1CC[C@@H](N(C)c2nc(OC[C@]34CCCN3C[C@H](F)C4)nc3c(F)c(-c4cccc5ccc(F)c(Cl)c45)ncc23)C1]

Step 1: 1-((R)-3-((7-(8-chloro-7-fluoronaphthalen-1-yl)-8-fluoro-2-(((2R,7aR)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one The amide coupling reaction was prepared in a similar fashion to Method #1, Step 10. The crude was purified by reverse phase HPLC (column: Waters Xbridge BEH C18 100*30 mm*10 um; mobile phase: [water (NH$_4$HCO$_3$)-acetonitrile]; B %: 30%-60%, 8 min) affording 1-((R)-3-((7-(8-chloro-7-fluoronaphthalen-1-yl)-8-fluoro-2-(((2R,7aR)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (27.41 mg, 28.51%) as a white solid: $^1$H NMR (400 MHz, Acetonitrile-d3) δ 9.22-9.04 (m, 1H), 8.13-7.96 (m, 2H), 7.67-7.57 (m, 2H), 7.46 (t, J=8.9 Hz, 1H), 6.60-6.42 (m, 1H), 6.23-6.11 (m, 1H), 5.68-5.56 (m, 1H), 5.39-5.16 (m, 2H), 4.24-4.12 (m, 2H), 4.06-3.72 (m, 2H), 3.65-3.40 (m, 2H), 3.36 (s, 3H), 3.32-3.20 (m, 1H), 2.94 (td, J=6.1, 10.5 Hz, 1H), 2.87-2.72 (m, 1H), 2.59-2.52 (m, 1H), 2.37-2.19 (m, 3H), 1.97-1.90 (m, 1H), 1.86-1.75 (m, 3H), 1.69-1.61 (m, 1H). LCMS Rt=2.128 min, m/z=636.2 [M+H]+.

LCMS (5 to 95% acetonitrile in water+0.1% trifluoroacetic acid over 6 mins) retention time 2.128 min, ESI+ found [M+H]=636.2.

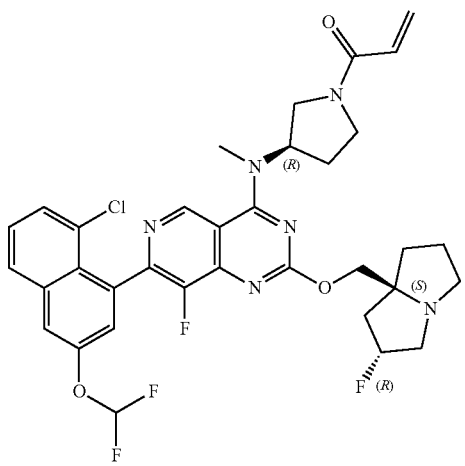

Example 82 (Method 3-Master): 1-((R)-3-((7-(8-chloro-3-(difluoromethoxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one

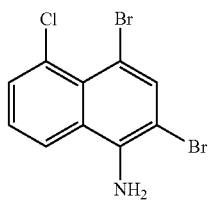 [SMILES: Nc1c(Br)cc(Br)c2c(Cl)cccc12]

Step 1: 2,4-dibromo-5-chloronaphthalen-1-amine

To a solution of 5-chloronaphthalen-1-amine (20 g, 112.59 mmol) in chloroform (250 mL) was added bromine (53.98 g, 337.78 mmol, 17.41 mL) at 0° C. The mixture was stirred at 50° C. for 12 h. The reaction mixture was quenched with saturated sodium bicarbonate (500 mL) and extracted with dichloromethane (3×300 mL). The combined organic layers were dried over sodium sulphate and concentrated in vacuo. The crude residue was diluted with tert-butyl methyl ether (50 mL) and the resulting precipitate was filtered affording 2,4-dibromo-5-chloronaphthalen-1-amine (40 g, crude) as a brown solid, used in next step without further purification. LCMS Rt=0.829 min, m/z=334.9 [M+H]$^+$.

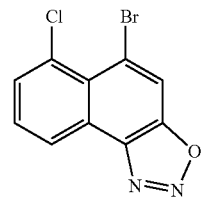 [SMILES: Clc1cccc2c1c(Br)cc1onnc12]

Step 2: 5-bromo-6-chloronaphtho[1,2-d][1,2,3]oxadiazole

To a solution of 2,4-dibromo-5-chloro-naphthalen-1-amine (26 g, 77.51 mmol) in acetic acid (300 mL) was added sodium propionate (30 mL) and sodium nitrite (8.02 g, 116.27 mmol) at 0° C. The mixture was stirred at 25° C. for 1 h. The reaction mixture was quenched with water (200 mL) and extracted with dichloromethane (3×100 mL). The combined organic layers were dried over sodium sulphate and concentrated in vacuo. The crude residue was diluted with tert-butyl methyl ether (50 mL) and the resulting precipitate was filtered affording 5-bromo-6-chloronaphtho[1,2-d][1,2,3]oxadiazole (14 g, crude) as a brown solid, used in next step without any further purification: $^1$H NMR (400 MHz, Acetonitrile-d3) δ 7.86-7.48 (m, 3H), 7.31-7.25 (m, 1H).

LCMS Rt=0.707 min, m/z=283.9 [M+H]$^+$.

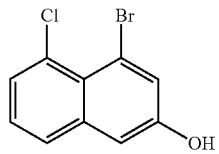 [SMILES: Oc1cc(Br)c2c(Cl)cccc2c1]

Step 3: 4-bromo-5-chloronaphthalen-2-ol

To a solution of 5-bromo-6-chloronaphtho[1,2-d][1,2,3]oxadiazole (12 g, 42.33 mmol) in ethanol (80 mL) and tetrahydrofuran (80 mL) was added sodium borohydride (2.67 g, 70.58 mmol) at 0° C. The mixture was stirred at 25° C. for 1 h. The mixture was quenched with hydrochloric acid (1M, 50 mL) and extracted with ethyl acetate (3×100 mL). The combined organic layers were dried over sodium sulphate and concentrated in vacuo. The resulting residue was purified by column chromatography (silica gel, 100-200 mesh, 0-100% ethyl acetate in petroleum ether) affording 4-bromo-5-chloronaphthalen-2-ol (2.7 g, 24.77%) as a black oil: $^1$H NMR (400 MHz, Chloroform-d) δ 7.64-7.57 (m, 2H), 7.50 (dd, J=1.2, 7.5 Hz, 1H), 7.34-7.27 (m, 1H), 7.17 (d, J=2.6 Hz, 1H), 5.24 (br s, 1H). LCMS Rt=0.792 min, m/z=257.9 [M+H]+.

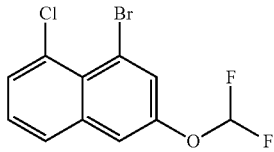 [SMILES: FC(F)Oc1cc(Br)c2c(Cl)cccc2c1]

Step 4: 1-bromo-8-chloro-3-(difluoromethoxy)naphthalene

To a solution of 4-bromo-5-chloro-naphthalen-2-ol (500 mg, 1.94 mmol) in N,N-dimethylformaldehyde (10 mL) was added potassium carbonate (322.03 mg, 2.33 mmol) and ethyl 2-chloro-2,2-difluoro-acetate (369.38 mg, 2.33 mmol). The mixture was diluted with water (2 mL) and extracted with ethyl acetate (3×5 mL). The combined organic layers were dried over sodium sulphate and concentrated in vacuo affording 1-bromo-8-chloro-3-(difluoromethoxy)naphthalene (600 mg, crude) as a yellow oil, used in next step without any further purification.

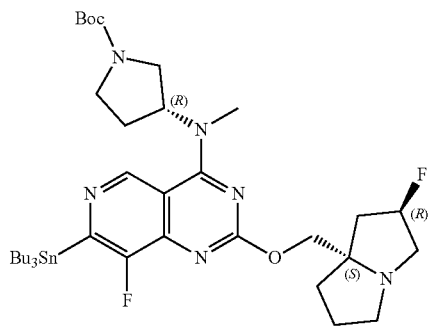

Step 5: (R)-tert-butyl 3-((8-fluoro-2-(((2R,7aS)-2-fluorohexahydro-1H-pyrrolizin-7a-yl)methoxy)-7-(tributylstannyl)pyrido[4,3-d]pyrimidin-4-yl)(methyl)amino)pyrrolidine-1-carboxylate A mixture of tributyl(tributylstannyl)stannane (4.73 g, 8.16 mmol), (R)-tert-butyl 3-((7-chloro-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (57.22 mg, 204.05 µmol), lithium chloride (432.48 mg, 10.20 mmol) and (1E,4E)-1,5-diphenylpenta-1,4-dien-3-one; palladium (373.70 mg, 408.10 µmol) in dioxane (200 mL) was degassed and purged with nitrogen for 3 times, and then the mixture was stirred at 110° C. for 12 h under nitrogen atmosphere. The reaction mixture was concentrated in vacuo. The crude product was purified by column chromatography (silica gel, 100-200 mesh, 2%-100% ethyl acetate in petroleum ether) affording (R)-tert-butyl 3-((8-fluoro-2-(((2R,7aS)-2-fluorohexahydro-1H-pyrrolizin-7a-yl)methoxy)-7-(tributylstannyl)pyrido[4,3-d]pyrimidin-4-yl)(methyl)amino)pyrrolidine-1-carboxylate (3.3 g, 74%) as a yellow oil. LCMS Rt=0.757 min, m/z=794.4 [M+H]$^+$.

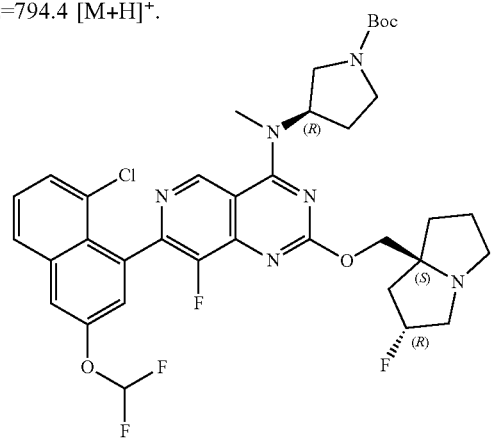

Step 6: (R)-tert-butyl 3-((7-(8-chloro-3-(difluoromethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate A mixture of (R)-tert-butyl 3-((8-fluoro-2-(((2R,7aS)-2-fluorohexahydro-1H-pyrrolizin-7a-yl)methoxy)-7-(tributylstannyl)pyrido[4,3-d]pyrimidin-4-yl)(methyl)amino)pyrrolidine-1-carboxylate (400 mg, 504.02 µmol), 1-bromo-8-chloro-3-(difluoromethoxy)naphthalene (309.99 mg, 1.01 mmol) and palladium; tritert-butylphosphane (128.79 mg, 252.01 µmol) in dioxane (2 mL) was degassed and purged with nitrogen for 3 times, then the mixture was stirred at 100° C. for 12 h under nitrogen atmosphere. The reaction mixture was concentrated to dryness in vacuo. The resulting residue was purified by reverse phase HPLC (column: Phenomenex luna C18 250*50 mm*10 µm; mobile phase: [water (trifluoroacetic acid)-acetonitrile]; B %: 30%-60%, 10 min) affording (R)-tert-butyl 3-((7-(8-chloro-3-(difluoromethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (100 mg, 23.47%, trifluoroacetate salt) as a yellow solid. LCMS Rt=0.947 min, m/z=730.3 [M+H]$^+$.

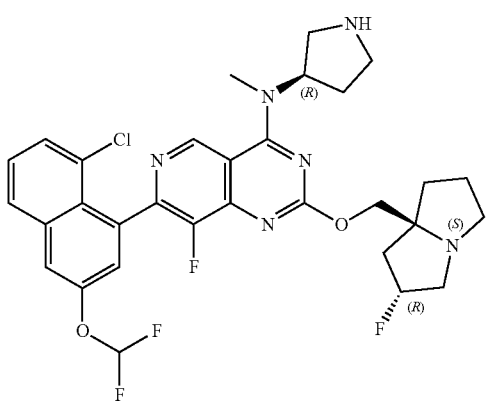

Step 7: 7-(8-chloro-3-(difluoromethoxy)naphthalen-1-yl)-8-fluoro-2-(((2R,7aS)-2-fluorohexahydro-1H-pyrrolizin-7a-yl)methoxy)-N-methyl-N—((R)-pyrrolidin-3-yl)pyrido[4,3-d]pyrimidin-4-amine The de-Boc protecting reaction was prepared in a similar fashion to Method #1, Step 9. The reaction mixture concentrated to dryness in vacuo affording 7-(8-chloro-3-(difluoromethoxy)naphthalen-1-yl)-8-fluoro-2-(((2R,7aS)-2-fluorohexahydro-1H-pyrrolizin-7a-yl)methoxy)-N-methyl-N—((R)-pyrrolidin-3-yl)pyrido[4,3-d]pyrimidin-4-amine (50 mg, crude, trifluoroacetate salt) as a yellow oil, used in next step without any further purification. LCMS Rt =0.582 min, m/z=630.2 [M+H]$^+$.

Step 8: 1-((R)-3-((7-(8-chloro-3-(difluoromethoxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one The amide coupling reaction was prepared in a similar fashion to Method #1, Step 10. The residue was purified by reverse phase HPLC (column: Waters Xbridge Prep OBD C18 150*40 mm*10 um; mobile phase: [water (NH$_4$HCO$_3$)-acetonitrile]; B %: 40%-70%, 8 min) affording 1-((R)-3-((7-(8-chloro-3-(difluoromethoxy)naphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (7.93 mg, 16.73%) as a yellow amorphous solid: $^1$H NMR (400 MHz, Acetonitrile-d3) δ 9.21 (s, 1H), 8.01 (br d, J=8.0 Hz, 1H), 7.85 (s, 1H), 7.66-7.52 (m, 2H), 7.52-7.43 (m, 1H), 7.00 (t, J=73.7 Hz, 1H), 6.69-6.52 (m, 1H), 6.26 (br d, J=16.8 Hz, 1H), 5.69 (br t, J=8.3 Hz, 1H), 5.45-5.18 (m, 2H), 4.27-4.20 (m, 1H), 4.18-4.13 (m, 1H), 4.03 (br dd, J=8.4, 48.0 Hz, 1H), 3.93-3.79 (m, 1H), 3.71-3.62 (m, 2H), 3.44 (s, 3H), 3.22-3.12 (m, 2H), 3.08 (s, 1H), 2.96-2.86 (m, 1H), 2.44-2.36 (m, 1H), 2.31 (br dd, J=8.3, 14.5 Hz, 1H), 2.12 (br s, 1H), 2.07 (br d, J=6.8 Hz, 1H), 1.93-1.80 (m, 4H). LCMS Rt=3.069 min, m/z=684.2 [M+H]$^+$.

LCMS (5 to 95% acetonitrile in water+0.03% ammonium bicarbonate over 6 mins) retention time 3.069 min, ESI+ found [M+H]=684.2.

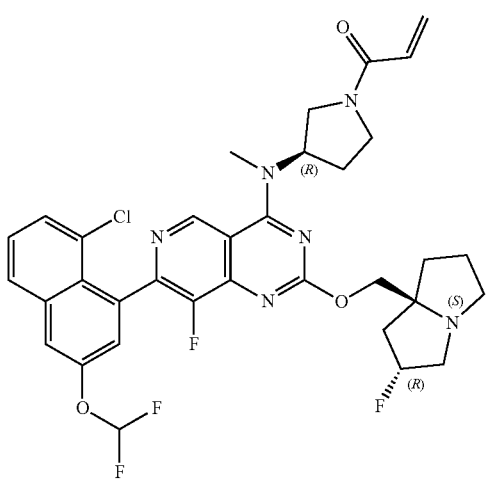

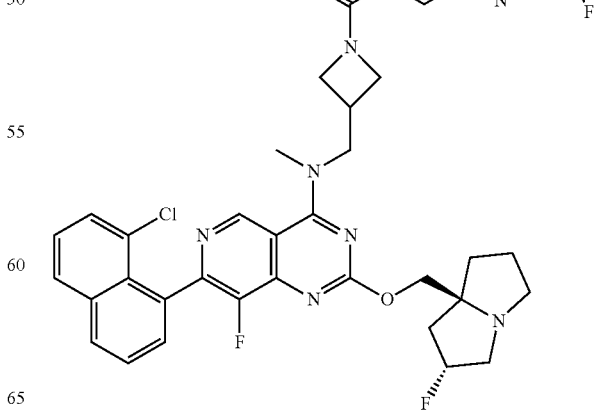

Example 83 (Method 1): (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-((R)-1-fluoroethyl)-1,2,4-oxadiazol-5-yl)prop-2-en-1-one

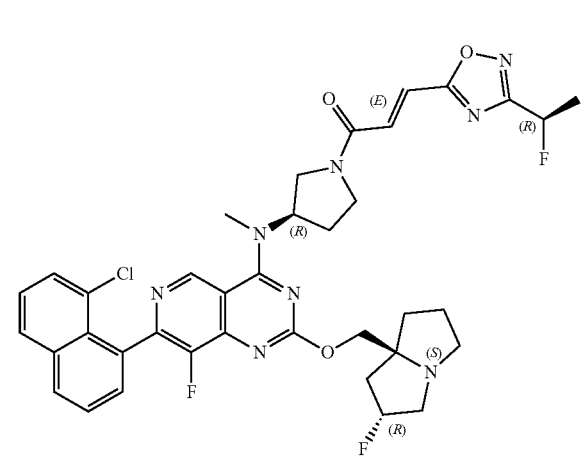

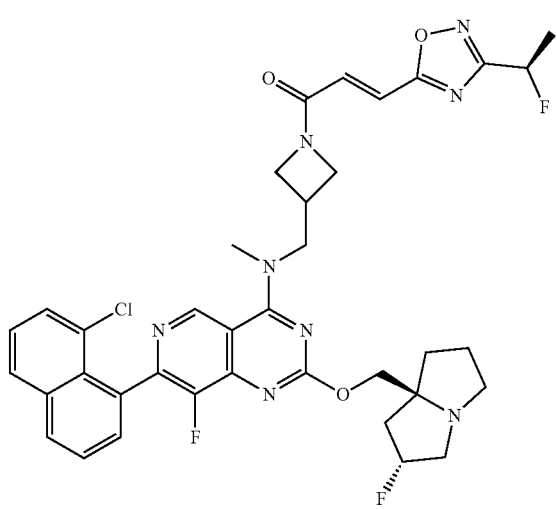 [SMILES: C[C@@H](F)c1noc(/C=C/C(=O)N2CC(CN(C)c3nc(OC[C@@]45CCCN4C[C@H](F)C5)nc4c(F)c(-c5cccc6cccc(Cl)c56)ncc34)C2)n1]

Step 1: (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-((R)-1-fluoroethyl)-1,2,4-oxadiazol-5-yl)prop-2-en-1-one The amide coupling reaction was prepared in a similar fashion to Method #1, Step 10. The residue was purified by reverse phase HPLC (column: Waters Xbridge BEH C18 100*30 mm*10 μm; mobile phase: [water (NH₄HCO₃)-acetonitrile]; B %: 35%-65%, 8 min) affording (E)-1-[3-[[[7-(8-chloro-1-naphthyl)-8-fluoro-2-[[(2R,8S)-2-fluoro-1,2,3,5,6,7-hexahydropyrrolizin-8-yl]methoxy]pyrido[4,3-d]pyrimidin-4-yl]-methyl-amino]methyl]azetidin-1-yl]-3-[3-[(1R)-1-fluoroethyl]-1,2,4-oxadiazol-5-yl]prop-2-en-1-one (29.28 mg, 26.30%) as a white solid. LCMS Rt=3.119 min, m/z=732.3 [M+H]⁺.

LCMS (5 to 95% acetonitrile in water+0.03% ammonium bicarbonate over 6 min) retention time 3.119 min, ESI+ found [M+H]=732.3.

Example 84 (Method 5): (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-((R)-1-fluoroethyl)-1,2,4-oxadiazol-5-yl)prop-2-en-1-one

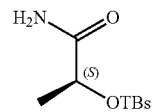

Step 1:
(S)-2-((tert-butyldimethylsilyl)oxy)propanamide

The TBS protection reaction was prepared in a similar fashion to Method #5, Step 1. The mixture was purified by column chromatography (silica gel, 100-200 mesh, 7-20% ethyl acetate in petroleum ether) affording (S)-2-((tert-butyldimethylsilyl)oxy)propanamide (7.6 g, 73.99%) as a brown oil. LCMS Rt=0.626 min, m/z=203.1 [M+H]⁺.

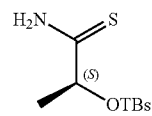

Step 2: (S)-2-((tert-butyldimethylsilyl)oxy)propanethioamide

The sulfamide formation was prepared in a similar fashion to Method #5, Step 2. The mixture was concentrated to dryness in vacuo affording (S)-2-((tert-butyldimethylsilyl)oxy)propanethioamide (7.9 g, crude) as a yellow oil, used in next step without any further purification. LCMS Rt=0.691 min, m/z=219.1 [M+H]⁺.

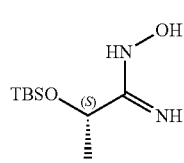

Step 3: (S)-2-((tert-butyldimethylsilyl)oxy)-N-hydroxypropanimidamide

The hydroxylimidamide formation was prepared in a similar fashion to Method #5, Step 3. The mixture was concentrated to dryness in vacuo affording (S)-2-((tert-butyldimethylsilyl)oxy)-N-hydroxypropanimidamide (6.4 g, crude) as a gray oil, used in next step without any further purification. LCMS Rt=0.604 min, m/z=218.2 [M+H]$^+$.

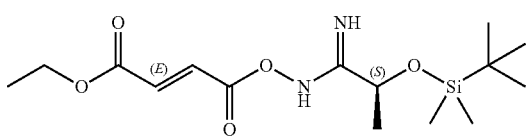

Step 4: (S,E)-ethyl 6-imino-2,2,3,3,5-pentamethyl-9-oxo-4,8-dioxa-7-aza-3-siladodec-10-en-12-oate The coupling reaction was prepared in a similar fashion to Method #5, Step 4. The mixture was concentrated to dryness in vacuo affording (S,E)-ethyl 6-imino-2,2,3,3,5-pentamethyl-9-oxo-4,8-dioxa-7-aza-3-siladodec-10-en-12-oate (10.6 g, crude) as a brown oil, used in the next step without further purification. LCMS Rt=0.732 min, m/z=344.2 [M+H]$^+$.

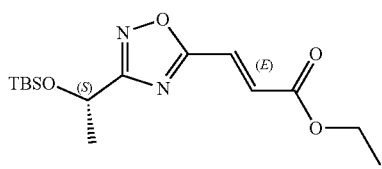

Step 5: (S,E)-ethyl 3-(3-(1-(((tert-butyldimethylsilyl)oxy)ethyl)-1,2,4-oxadiazol-5-yl)acrylate The cyclization reaction was prepared in a similar fashion to Method #5, Step 5. The residue was purified by column chromatography (silica gel, 100-200 mesh, 2-5% ethyl acetate in petroleum ether) affording (S,E)-ethyl 3-(3-(1-(((tert-butyldimethylsilyl)oxy)ethyl)-1,2,4-oxadiazol-5-yl) acrylate (3.4 g, 34.17%) as a yellow oil. LCMS Rt=0.817 min, m/z=326.2 [M+H]$^+$.

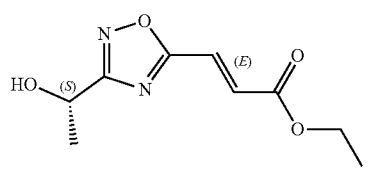

Step 6: (S,E)-ethyl 3-(3-(1-hydroxyethyl)-1,2,4-oxadiazol-5-yl)acrylate

The deprotection of TBS group was prepared in a similar fashion to Method #5, Step 6. The mixture was concentrated to dryness in vacuo affording (S,E)-ethyl 3-(3-(1-hydroxyethyl)-1,2,4-oxadiazol-5-yl)acrylate (1.8 g, crude) as a brown oil, used in next step without further purification. LCMS Rt=0.467 min, m/z=212.1 [M+H]$^+$.

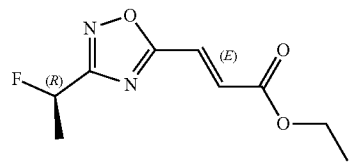

Step 7: (R,E)-ethyl 3-(3-(1-fluoroethyl)-1,2,4-oxadiazol-5-yl)acrylate

The substitution to introduce F was prepared in a similar fashion to Method #5, Step 7. The mixture was concentrated in vacuo affording (R,E)-ethyl 3-(3-(1-fluoroethyl)-1,2,4-oxadiazol-5-yl)acrylate (1.08 g, crude) as a brown oil, used in next step without further purification. LCMS Rt =0.588 min, m/z=214.1 [M+H]$^+$.

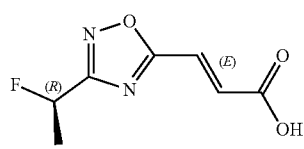

Step 8: (R,E)-3-(3-(1-fluoroethyl)-1,2,4-oxadiazol-5-yl)acrylic acid

The hydrolysis reaction was prepared in a similar fashion to Method #5, Step 8. The mixture was concentrated in vacuo affording (R,E)-3-(3-(1-fluoroethyl)-1,2,4-oxadiazol-5-yl)acrylic acid (700 mg, crude) as a white solid, used in next step without further purification: $^1$H NMR (400 MHz, Chloroform-d) δ 11.62-11.01 (m, 1H), 7.55 (d, J=16.1 Hz, 1H), 7.04 (d, J=16.1 Hz, 1H), 5.87-5.53 (m, 1H), 1.85-1.60 (m, 3H).

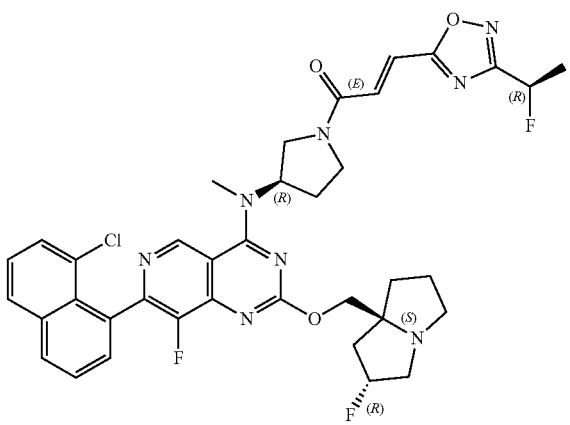

Step 9: (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-((R)-1-fluoroethyl)-1,2,4-oxadiazol-5-yl)prop-2-en-1-one The amide coupling reaction was prepared in a similar fashion to Method #5, Step 9. The residue was purified by reverse phase HPLC (column: Waters Xbridge Prep OBD C18 150*40 mm*10 μm; mobile phase: [water (NH$_4$HCO$_3$)-acetonitrile]; B %: 35%-65%, 8 min) affording (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-((R)-1-fluoroethyl)-1,2,4-oxadiazol-5-yl)prop-2-en-1-one (12.57 mg, 11.43%) as a white solid: $^1$H NMR (400 MHz, Acetonitrile-d3) δ 9.22 (s, 1H), 8.15 (d, J=7.6 Hz, 1H), 8.05 (d, J=8.0 Hz, 1H), 7.79-7.68 (m, 1H), 7.64 (br d, J=7.4 Hz, 2H), 7.59-7.51 (m, 2H), 7.47 (d, J=5.1 Hz, 1H), 5.97-5.73 (m, 1H), 5.50-5.17 (m, 2H), 4.31-4.11 (m, 3H), 4.10-3.98 (m, 1H), 3.97-3.74 (m, 2H), 3.47 (s, 3H), 3.25-3.03 (m, 3H), 3.01-2.88 (m, 1H), 2.48-2.32 (m, 2H), 2.23 (br d, J=4.5 Hz, 2H), 2.14 (br d, J=2.4 Hz, 2H), 2.10 (br s, 1H), 1.85-1.63 (m, 4H). LCMS Rt=3.165 min, m/z=732.3 [M+H]$^+$.

LCMS (5 to 95% acetonitrile in water+0.03% ammonium bicarbonate over 6 mins) retention time 3.165 min, ESI+ found [M+H]=732.3.

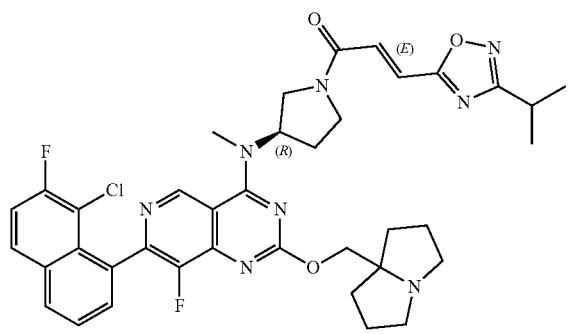

Example 85 (Method 1): (R,E)-1-(3-((7-(8-chloro-7-fluoronaphthalen-1-yl)-8-fluoro-2-((hexahydro-1H-pyrrolizin-7a-yl)methoxy)pyrido[4,3-d]pyrimidin-4-yl)(methyl)amino)pyrrolidin-1-yl)-3-(3-isopropyl-1,2,4-oxadiazol-5-yl)prop-2-en-1-one

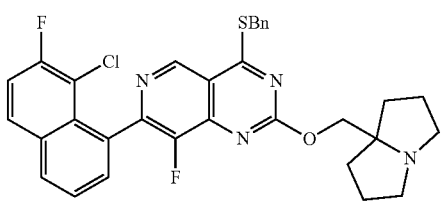

Step 1: 4-(benzylthio)-7-(8-chloro-7-fluoronaphthalen-1-yl)-8-fluoro-2-((hexahydro-1H-pyrrolizin-7a-yl)methoxy)pyrido[4,3-d]pyrimidine The Suzuki reaction was prepared in a similar fashion to Method #1, Step 6. The mixture was diluted with water (20 mL) and extracted with ethyl acetate (3×50 mL). The combined organic layers were dried over sodium sulphate, concentrated in vacuo and purified by column chromatography (silica gel, 100-200 mesh, 0-100% ethyl acetate in petroleum ether) affording 4-(benzylthio)-7-(8-chloro-7-fluoronaphthalen-1-yl)-8-fluoro-2-((hexahydro-1H-pyrrolizin-7a-yl)methoxy)pyrido[4,3-d]pyrimidine (1 g, crude) as a yellow oil, used in next step without any further purification. LCMS Rt=0.759 min, m/z=588.2 [M+H]$^+$.

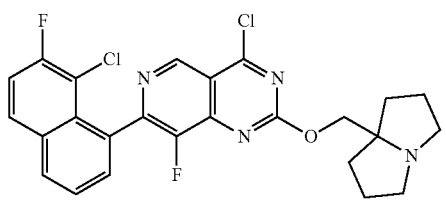 [SMILES: Fc1ccc2cccc(-c3ncc4c(Cl)nc(OCC56CCCN5CCC6)nc4c3F)c2c1Cl]

Step 2: 4-chloro-7-(8-chloro-7-fluoronaphthalen-1-yl)-8-fluoro-2-((hexahydro-1H-pyrrolizin-7a-yl)methoxy)pyrido[4,3-d]pyrimidine The chlorination reaction was prepared in a similar fashion to Method #1, Step 7. The mixture was concentrated to dryness in vacuo affording 4-chloro-7-(8-chloro-7-fluoronaphthalen-1-yl)-8-fluoro-2-((hexahydro-1H-pyrrolizin-7a-yl)methoxy)pyrido[4,3-d]pyrimidine (510 mg, crude) as a yellow oil, used in next step without any further purification. LCMS Rt=0.678 min, m/z=500.1 [M+H]$^+$.

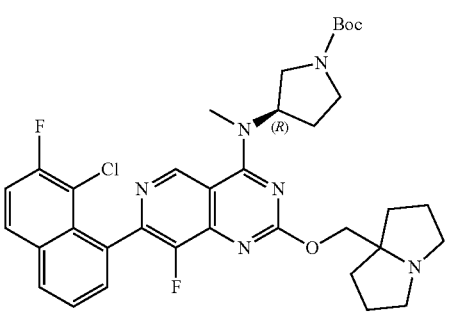

Step 3: (R)-tert-butyl 3-((7-(8-chloro-7-fluoronaphthalen-1-yl)-8-fluoro-2-((hexahydro-1H-pyrrolizin-7a-yl)methoxy)pyrido[4,3-d]pyrimidin-4-yl)(methyl)amino)pyrrolidine-1-carboxylate The substitution reaction was prepared in a similar fashion to Method #1, Step 8. The residue was purified by reverse phase HPLC (column: C18-1 150*30 mm*5 μm; mobile phase: [water (formic acid)-acetonitrile]; B %: 15%-60%, 8 min) affording (R)-tert-butyl 3-((7-(8-chloro-7-fluoronaphthalen-1-yl)-8-fluoro-2-((hexahydro-1H-pyrrolizin-7a-yl)methoxy)pyrido[4,3-d]pyrimidin-4-yl)(methyl)amino)pyrrolidine-1-carboxylate (30 mg, 8.87%, formate salt) as a pale yellow solid. LCMS Rt=1.734 min, m/z=664.3 [M+H]$^+$.

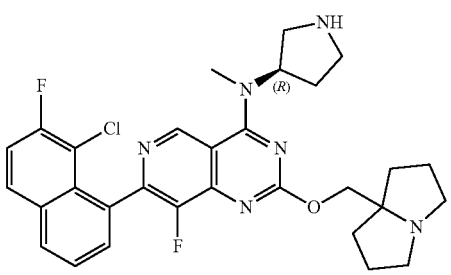

Step 4: (R)-7-(8-chloro-7-fluoronaphthalen-1-yl)-8-fluoro-2-((hexahydro-1H-pyrrolizin-7a-yl)methoxy)-N-methyl-N-(pyrrolidin-3-yl)pyrido[4,3-d]pyrimidin-4-amine The de-Boc protecting reaction was prepared in a similar fashion to Method #1, Step 9. The mixture was concentrated to dryness in vacuo affording (R)-7-(8-chloro-7-fluoronaphthalen-1-yl)-8-fluoro-2-((hexahydro-1H-pyrrolizin-7a-yl)methoxy)-N-methyl-N-(pyrrolidin-3-yl)pyrido[4,3-d]pyrimidin-4-amine (25 mg, crude, trifluoroacetate salt) as a yellow solid, used in next step without any further purification. LCMS Rt=0.633 min, m/z=564.2 [M+H]$^+$.

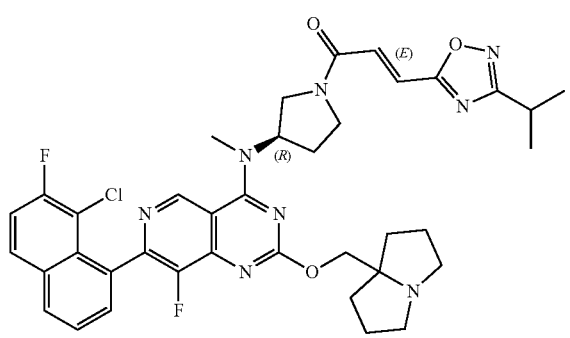

Step 5: (R,E)-1-(3-((7-(8-chloro-7-fluoronaphthalen-1-yl)-8-fluoro-2-((hexahydro-1H-pyrrolizin-7a-yl)methoxy)pyrido[4,3-d]pyrimidin-4-yl)(methyl)amino)pyrrolidin-1-yl)-3-(3-isopropyl-1,2,4-oxadiazol-5-yl)prop-2-en-1-one The amide coupling reaction was prepared in a similar fashion to Method #1, Step 10. The residue was purified by reverse phase HPLC (column: Phenomenex Luna C18 75*30 mm*3 μm; mobile phase: [water (formic acid)-Acetonitrile]; B %: 10%-40%, 8 min) affording (R,E)-1-(3-((7-(8-chloro-7-fluoronaphthalen-1-yl)-8-fluoro-2-((hexahydro-1H-pyrrolizin-7a-yl)methoxy)pyrido[4,3-d]pyrimidin-4-yl)(methyl)amino)pyrrolidin-1-yl)-3-(3-isopropyl-1,2,4-oxadiazol-5-yl)prop-2-en-1-one (4.93 mg, 15.28%, formate salt) as a yellow amorphous solid: $^1$H NMR (400 MHz, Acetonitrile-d3) δ 9.25-9.19 (m, 1H), 8.20-8.15 (m, 1H), 8.10 (dd, J=5.7, 9.0 Hz, 1H), 7.74-7.68 (m, 2H), 7.59-7.51 (m, 1H), 7.50-7.36 (m, 2H), 5.50-5.36 (m, 1H), 4.33-4.14 (m, 3H), 4.11-4.00 (m, 1H), 3.98-3.74 (m, 2H), 3.70-3.52 (m, 1H), 3.47 (s, 3H), 3.21-3.09 (m, 1H), 3.05-2.94 (m, 2H), 2.67-2.58 (m, 2H), 2.52-2.41 (m, 1H), 2.41-2.32 (m, 1H), 2.27-2.17 (m, 1H), 1.91-1.79 (m, 4H), 1.71-1.61 (m, 2H), 1.36 (dd, J=7.0, 9.2 Hz, 6H). LCMS Rt=2.993 min, m/z=728.3 [M+H]$^+$.

LCMS (5 to 95% acetonitrile in water+0.1% formic acid over 6 mins) retention time 2.993 min, ESI+ found [M+H]=728.3.

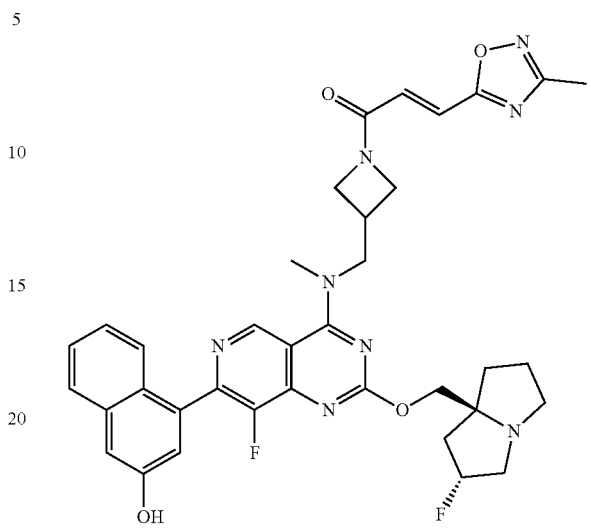

Example 86 (Method 2): (E)-1-(3-(((8-fluoro-2-(((2R,7aS)-2-fluorotetrahydro-1H-pyrrolizin-7a(5H)-yl)methoxy)-7-(3-hydroxynaphthalen-1-yl)pyrido[4,3-d]pyrimidin-4-yl)(methyl)amino)methyl)azetidin-1-yl)-3-(3-methyl-1,2,4-oxadiazol-5-yl)prop-2-en-1-one

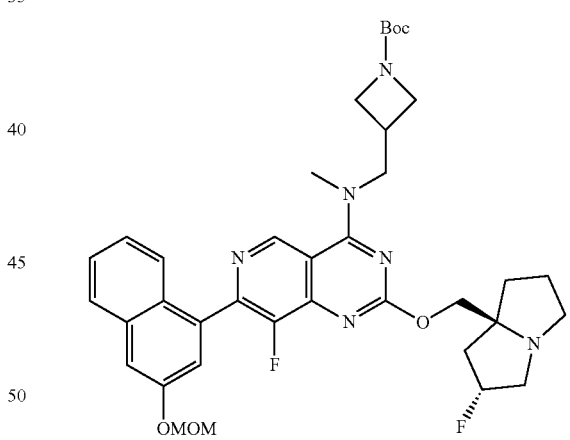

Step 3: tert-butyl 3-(((8-fluoro-2-(((2R,7aS)-2-fluorohexahydro-1H-pyrrolizin-7a-yl)methoxy)-7-(3-(methoxymethoxy)naphthalen-1-yl)pyrido[4,3-d]pyrimidin-4-yl)(methyl)amino)methyl)azetidine-1-carboxylate The Suzuki reaction was prepared in a similar fashion to Method #2, Step 5. The residue was purified by reverse phase HPLC (column: C18-1 150*30 mm*5 μm; mobile phase: [water (trifluoroacetic acid)-acetonitrile]; B %: 30%-75%, 8 min) affording tert-butyl 3-(((8-fluoro-2-(((2R,7aS)-2-fluorohexahydro-1H-pyrrolizin-7a-yl)methoxy)-7-(3-(methoxymethoxy)naphthalen-1-yl)pyrido[4,3-d]pyrimidin- 4-yl)(methyl)amino)methyl)azetidine-1-carboxylate (110 mg, 25.65%, trifluoroacetate salt) as a yellow oil. LCMS Rt=0.916 min, m/z=690.3 [M+H]⁺.

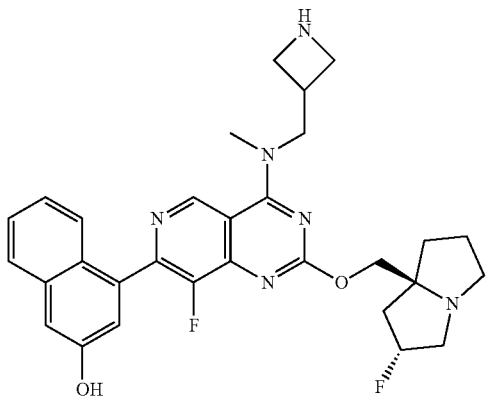 [SMILES: CN(CC1CNC1)c1nc(OC[C@@]23CCCN2C[C@H](F)C3)nc2c(F)c(-c3cc(O)cc4ccccc34)ncc12]

Step 4: 4-(4-((azetidin-3-ylmethyl)(methyl)amino)-8-fluoro-2-(((2R,7aS)-2-fluorohexahydro-1H-pyrrolizin-7a-yl)methoxy)pyrido[4,3-d]pyrimidin-7-yl)naphthalen-2-ol The de-Boc and MOM protecting reaction was prepared in a similar fashion to Method #2, Step 6. The residue was purified by reverse phase HPLC(column: Phenomenex Luna 80*30 mm*3 µm; mobile phase: [water (trifluoroacetic acid)-acetonitrile]; B %: 5%-35%, 8 min) affording 4-(4-((azetidin-3-ylmethyl)(methyl)amino)-8-fluoro-2-(((2R,7aS)-2-fluorohexahydro-1H-pyrrolizin-7a-yl)methoxy)pyrido[4,3-d]pyrimidin-7-yl)naphthalen-2-ol (70 mg, 73.19% yield, trifluoroacetate salt) as a yellow solid. LCMS Rt=0.728 min, m/z=546.3 [M+H]⁺.

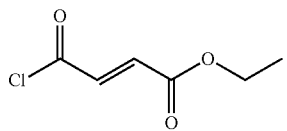

Step 5: (E)-ethyl 4-chloro-4-oxobut-2-enoate

A mixture of (E)-4-ethoxy-4-oxo-but-2-enoic acid (13 g, 90.20 mmol), oxalyl dichloride (12.59 g, 99.22 mmol) and N,N-dimethylformaldehyde (659.27 mg, 9.02 mmol) in dichloromethane (80 mL) was stirred at 20° C. for 0.5 h. The reaction mixture was concentrated in vacuo affording (E)-ethyl 4-chloro-4-oxobut-2-enoate (14 g, crude) as a yellow oil used in the next step without further purification.

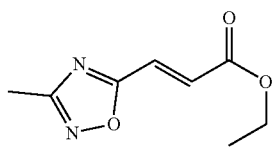

Step 6: (E)-ethyl 3-(3-methyl-1,2,4-oxadiazol-5-yl)acrylate

The cyclization reaction was prepared in a similar fashion to Method #1, Step 3. The crude product was concentrated in vacuo and purified by column chromatography (silica gel, 100-200 mesh, 0-10% ethyl acetate in petroleum ether) affording (E)-ethyl 3-(3-methyl-1,2,4-oxadiazol-5-yl)acrylate (4.9 g, 85%) as a brown oil: ¹H NMR (400 MHz, Chloroform-d) δ 7.46-7.34, (m, 1H), 6.98-6.88 (m, 1H), 4.24 (q, J=7.13 Hz, 2H), 2.38 (s, 3H), 1.32-1.26 (m, 3H). LCMS Rt=0.383 min, m/z=182.1 [M+H]⁺.

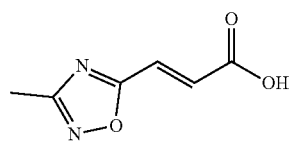

Step 7: (E)-3-(3-methyl-1,2,4-oxadiazol-5-yl)acrylic acid

The hydrolysis reaction was prepared in a similar fashion to Method #1, Step 4. The crude product was concentrated in vacuo affording (E)-3-(3-methyl-1,2,4-oxadiazol-5-yl)acrylic acid (860 mg, crude) as a colorless oil used in the next step without further purification: ¹H NMR (400 MHz, Methanol-d4) δ 7.34 (d, J=16.1 Hz, 1H), 6.87 (d, J=16.1 Hz, 1H), 2.31 (s, 3H). LCMS Rt =0.200 min, m/z=154.0 [M+H]⁺.

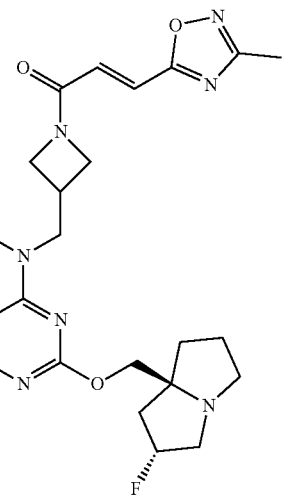

Step 8: (E)-1-(3-(((8-fluoro-2-(((2R,7aS)-2-fluorotetrahydro-1H-pyrrolizin-7a(5H)-yl)methoxy)-7-(3-hydroxynaphthalen-1-yl)pyrido[4,3-d]pyrimidin-4-yl)(methyl)amino)methyl)azetidin-1-yl)-3-(3-methyl-1,2,4-oxadiazol-5-yl)prop-2-en-1-one The amide coupling reaction was prepared in a similar fashion to Method #1, Step 10. The residue was purified by reverse phase HPLC(column: Waters Xbridge Prep OBD C18 150*40 mm*10 um; mobile phase: [water (NH₄HCO₃)-acetonitrile]; B %: 30%-60%, 8 min) affording (E)-1-(3-

(((8-fluoro-2-(((2R,7aS)-2-fluorotetrahydro-1H-pyrrolizin-7a(5H)-yl)methoxy)-7-(3-hydroxynaphthalen-1-yl)pyrido[4,3-d]pyrimidin-4-yl)(methyl)amino)methyl)azetidin-1-yl)-3-(3-methyl-1,2,4-oxadiazol-5-yl)prop-2-en-1-one (4.14 mg, 15.18%) as a yellow oil: $^1$H NMR (400 MHz, Acetonitrile-d3) δ 9.35 (s, 1H), 7.86-7.82 (m, 1H), 7.63 (br d, J=9.4 Hz, 1H), 7.51-7.47 (m, 1H), 7.36-7.29 (m, 4H), 7.23-7.17 (m, 1H), 5.40-5.19 (m, 1H), 4.54-4.45 (m, 1H), 4.34-4.30 (m, 1H), 4.27 (br d, J=11.4 Hz, 1H), 4.24-4.19 (m, 3H), 4.18-4.14 (m, 1H), 3.97 (dd, J=5.8, 10.6 Hz, 1H), 3.62 (s, 3H), 3.27-3.19 (m, 3H), 3.17-3.12 (m, 1H), 3.00-2.90 (m, 1H), 2.42-2.39 (m, 3H), 2.30-2.25 (m, 2H), 2.09 (br dd, J=2.3, 6.8 Hz, 2H), 1.80 (dt, J=1.9, 4.7 Hz, 2H). LCMS Rt=2.776 min, m/z=682.3 [M+H]+.

LCMS (5 to 95% acetonitrile in water+0.03% ammonium bicarbonate over 6 mins) retention time 2.776 min, ESI+ found [M+H]=682.3.

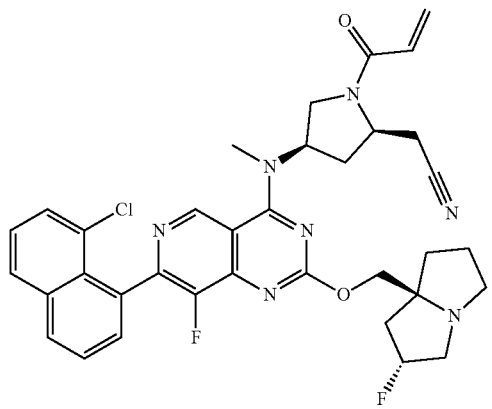 [SMILES: C=CC(=O)N1C[C@H](N(C)c2nc(OC[C@@]34CCCN3C[C@H](F)C4)nc3c(F)c(-c4cccc5cccc(Cl)c45)ncc23)C[C@@H]1CC#N]

Example 87 (Method 6): 2-((2R,4R)-1-acryloyl-4-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-2-yl)acetonitrile

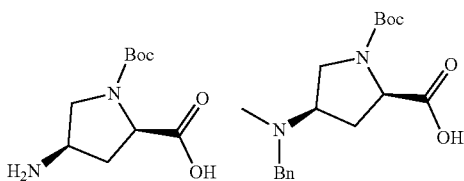

Step 1: (2R,4R)-4-(benzyl(methyl)amino)-1-(tert-butoxycarbonyl)pyrrolidine-2-carboxylic acid The reductive amination was prepared in a similar fashion to Method #6, Step 1. The residue was purified by column chromatography (silica gel, 100-200 mesh, 0-100% ethyl acetate in petroleum ether) affording (2R,4R)-4-(benzyl(methyl)amino)-1-(tert-butoxycarbonyl)pyrrolidine-2-carboxylic acid as a white solid. LCMS Rt=0.533 min, m/z=230.1 [M+H]+.

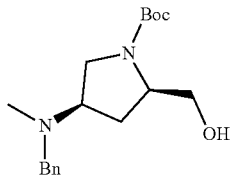 [SMILES: CN(Cc1ccccc1)[C@@H]1C[C@H](CO)N(C(=O)OC(C)(C)C)C1]

Step 2: (2R,4R)-tert-butyl 4-(benzyl(methyl)amino)-2-(hydroxymethyl)pyrrolidine-1-carboxylate The reduction reaction was prepared in a similar fashion to Method #6, Step 2. The mixture was quenched with sodium sulfate decahydrate (1 g) at 0° C., and dried over sodium sulphate and concentrated in vacuo affording (2R,4R)-tert-butyl 4-(benzyl(methyl)amino)-2-(hydroxymethyl)pyrrolidine-1-carboxylate (3 g, 84.62%) as a colorless oil. LCMS Rt=0.443 min, m/z=320.2 [M+H]+.

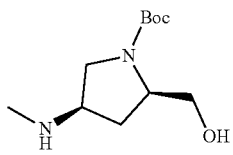 [SMILES: CN[C@@H]1C[C@H](CO)N(C(=O)OC(C)(C)C)C1]

Step 3: (2R,4R)-tert-butyl 2-(hydroxymethyl)-4-(methylamino)pyrrolidine-1-carboxylate The deprotection of Bn group was prepared in a similar fashion to Method #6, Step 6, the mixture was concentrated to dryness in vacuo affording (2R,4R)-tert-butyl 2-(hydroxymethyl)-4-(methylamino)pyrrolidine-1-carboxylate (2.9 g, crude) as a yellow oil, used in next step without further purification.

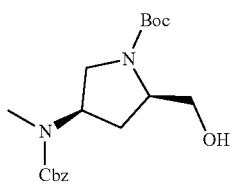 [SMILES: CN(C(=O)OCc1ccccc1)[C@@H]1C[C@H](CO)N(C(=O)OC(C)(C)C)C1]

Step 4: (2R,4R)-tert-butyl 4-(((benzyloxy)carbonyl)(methyl)amino)-2-(hydroxymethyl)pyrrolidine-1-carboxylate To a solution of (2R,4R)-tert-butyl 2-(hydroxymethyl)-4-(methylamino)pyrrolidine-1-carboxylate (2.4 g, 10.42 mmol) in tetrahydrofuran (20 mL) and water (20 mL) was added sodium carbonate (3.31 g, 31.26 mmol) and benzyl carbonochloridate (3.56 g, 20.84 mmol). The mixture was stirred at 20° C. for 12 h. The reaction mixture was extracted with ethyl acetate (3×30 mL). The combined organic layers were washed with brine (30 mL), dried over sodium sulphate, filtered and concentrated to dryness in vacuo. The residue was purified by column chromatography (silica gel, 100-200 mesh, 10-50% ethyl acetate in petroleum ether) affording (2R,4R)-tert-butyl 4-(((benzyloxy)carbonyl)(methyl)amino)-2-(hydroxymethyl)pyrrolidine-1-carboxylate (1.4 g, 36.86%) as a white solid: $^1$H NMR (400 MHz, Chloroform-d) δ 7.33-7.23 (m, 5H), 5.16-5.02 (m, 2H), 3.92-3.84 (m, 1H), 3.73-3.60 (m, 2H), 3.59-3.49 (m, 1H), 3.40-3.29 (m, 2H), 3.12-3.01 (m, 1H), 2.83-2.69 (m, 3H), 2.10-2.01 (m, 1H), 1.62-1.58 (m, 1H), 1.42-1.33 (m, 9H). LCMS Rt=0.636 min, m/z=364.2 [M+H]$^+$.

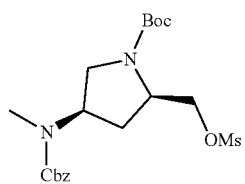 [SMILES: CN(C(=O)OCc1ccccc1)[C@@H]1C[C@H](COS(C)(=O)=O)N(C(=O)OC(C)(C)C)C1]

Step 5: (2R,4R)-tert-butyl 4-(((benzyloxy)carbonyl)(methyl)amino)-2-(((methylsulfonyl)oxy)methyl)pyrrolidine-1-carboxylate The mesylation reaction was prepared in a similar fashion to Method #6, Step 3, the mixture was concentrated in vacuo affording (2R,4R)-tert-butyl 4-(((benzyloxy)carbonyl)(methyl)amino)-2-(((methylsulfonyl)oxy)methyl)pyrrolidine-1-carboxylate (2 g, crude) as a yellow oil, used in next step without any further purification. LCMS Rt=0.781 min, m/z=442.2 [M+H]+.

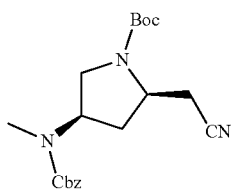 [SMILES: CN(C(=O)OCc1ccccc1)[C@@H]1C[C@H](CC#N)N(C(=O)OC(C)(C)C)C1]

Step 6: (2R,4R)-tert-butyl 4-(((benzyloxy)carbonyl)(methyl)amino)-2-(cyanomethyl)pyrrolidine-1-carboxylate The substitution to introduce nitrile group was prepared in a similar fashion to Method #6, Step 4, the mixture was concentrated in vacuo affording (2R,4R)-tert-butyl 4-(((benzyloxy)carbonyl)(methyl)amino)-2-(cyanomethyl)pyrrolidine-1-carboxylate (1.4 g, crude) as a yellow oil, used in next step without further purification.

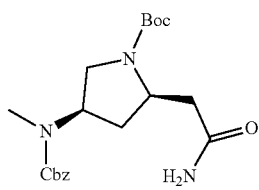 [SMILES: CN(C(=O)OCc1ccccc1)[C@@H]1C[C@H](CC(N)=O)N(C(=O)OC(C)(C)C)C1]

Step 7: (2R,4R)-tert-butyl 2-(2-amino-2-oxoethyl)-4-(((benzyloxy)carbonyl)(methyl)amino)pyrrolidine-1-carboxylate The hydrolysis of nitrile group was prepared in a similar fashion to Method #6, Step 5, the residue was purified by reverse phase HPLC (column: Phenomenex luna C18 (250*70 mm, 10 μm); mobile phase: [water (trifluoroacetic acid)-acetonitrile]; B %: 26%-56%, 20 min) affording (2R,4R)-tert-butyl 2-(2-amino-2-oxoethyl)-4-(((benzyloxy)carbonyl)(methyl)amino)pyrrolidine-1-carboxylate (950 mg, 64.73%) as a white solid: $^1$H NMR (400 MHz, Chloroform-d) δ 7.37-7.22 (m, 5H), 6.31-5.94 (m, 2H), 5.13-4.95 (m, 2H), 4.65-4.47 (m, 1H), 4.02-3.89 (m, 1H), 3.73-3.56 (m, 1H), 3.11-3.00 (m, 1H), 2.80 (s, 3H), 2.61 (br s, 2H), 2.30-2.06 (m, 2H), 1.46-1.32 (m, 9H). LCMS Rt=0.610 min, m/z=391.2 [M+H]$^+$.

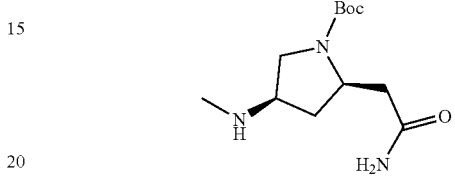

Step 8: (2R,4R)-tert-butyl 2-(2-amino-2-oxoethyl)-4-(methylamino)pyrrolidine-1-carboxylate The deprotection of Cbz group was prepared in a similar fashion to Method #6, Step 6, the mixture was concentrated to dryness in vacuo affording (2R,4R)-tert-butyl 2-(2-amino-2-oxoethyl)-4-(methylamino)pyrrolidine-1-carboxylate (310 mg, crude) as a colorless oil, used in next step without any further purification.

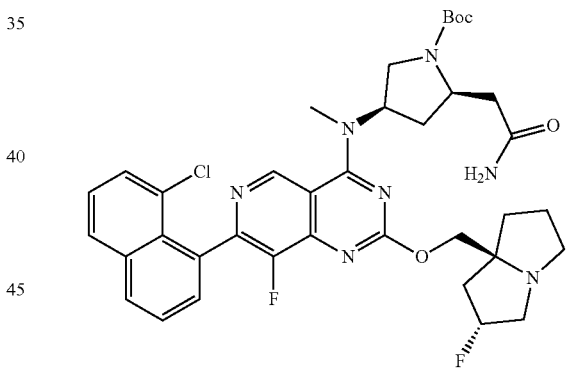

Step 9: (2R,4R)-tert-butyl 2-(2-amino-2-oxoethyl)-4-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate The substitution reaction was prepared in a similar fashion to Method #1, Step 8. The residue was purified by reverse phase HPLC (column: C18-1 150*30 mm*5 μm; mobile phase: [water (trifluoroacetic acid)-acetonitrile]; B %: 5%-50%, 8 min) affording (2R,4R)-tert-butyl 2-(2-amino-2-oxoethyl)-4-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (70 mg, crude) as a white solid, used in next step without any further purification. LCMS Rt=0.579 min, m/z=721.3 [M+H]$^+$.

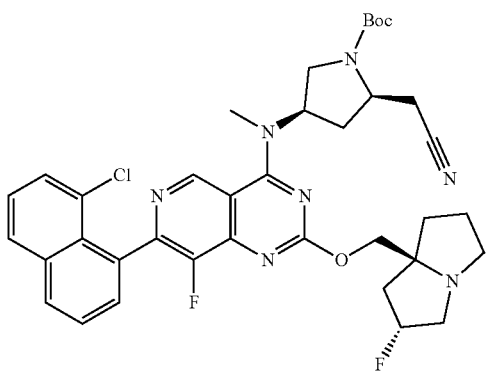 [SMILES: CN(c1nc(OC[C@@]23CCCN2C[C@H](F)C3)nc2c(F)c(-c3cccc4cccc(Cl)c34)ncc12)[C@@H]1C[C@H](CC#N)N(C(=O)OC(C)(C)C)C1]

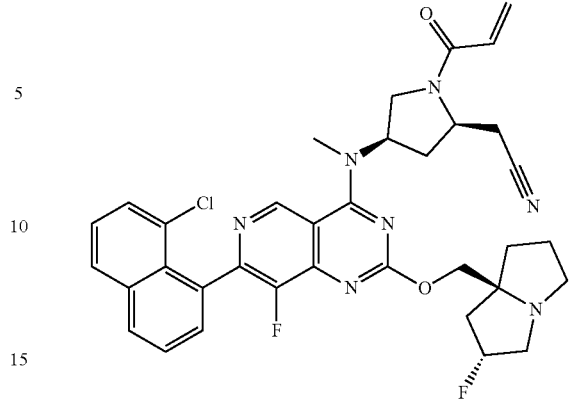

Step 10: (2R,4R)-tert-butyl 4-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-2-(cyanomethyl)pyrrolidine-1-carboxylate The dehydration reaction was prepared in a similar fashion to Method #6, Step 11. The mixture was concentrated in vacuo affording (2R,4R)-tert-butyl 4-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-2-(cyanomethyl)pyrrolidine-1-carboxylate (68 mg, crude) as a yellow oil, used in next step without further purification. LCMS Rt=0.618 min, m/z=703.3 [M+H]$^+$.

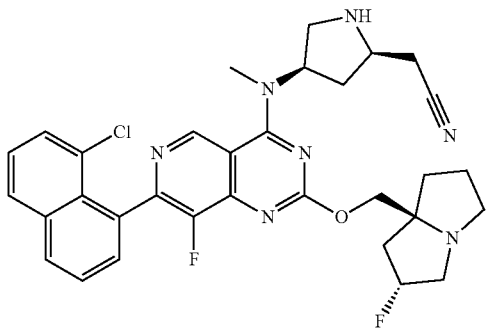 [SMILES: CN(c1nc(OC[C@@]23CCCN2C[C@H](F)C3)nc2c(F)c(-c3cccc4cccc(Cl)c34)ncc12)[C@H]1CN[C@@H](CC#N)C1]

Step 11: 2-((2R,4R)-4-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-2-yl)acetonitrile The de-Boc protecting reaction was prepared in a similar fashion to Method #1, Step 9. The reaction mixture was concentrated in vacuo affording 2-((2R,4R)-4-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-2-yl)acetonitrile (58 mg, crude, trifluoroacetic salt) as a yellow oil, used in next step without any further purification. LCMS Rt=0.475 min, m/z=603.2 [M+H]$^+$.

Step 12: 2-((2R,4R)-1-acryloyl-4-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-2-yl)acetonitrile The amide coupling reaction was prepared in a similar fashion to Method #6, Step 13. The residue was purified by reverse phase HPLC (column: Waters Xbridge Prep OBD C18 150*40 mm*10 um; mobile phase: [water (NH$_4$HCO$_3$)-acetonitrile]; B %: 30%-60%, 8 min) affording 2-((2R,4R)-1-acryloyl-4-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-2-yl)acetonitrile (9.07 mg, 13.83%) as a yellow amorphous solid: $^1$H NMR (400 MHz, Acetonitrile-d3) δ 9.27-9.17 (m, 1H), 8.23-8.12 (m, 1H), 8.10-8.03 (m, 1H), 7.76-7.70 (m, 1H), 7.69-7.62 (m, 2H), 7.59-7.52 (m, 1H), 6.67-6.55 (m, 1H), 6.36-6.27 (m, 1H), 5.80-5.73 (m, 1H), 5.39-5.19 (m, 2H), 4.41-4.31 (m, 1H), 4.25-4.21 (m, 1H), 4.18-4.13 (m, 1H), 3.81-3.66 (m, 1H), 3.55-3.44 (m, 3H), 3.32-3.21 (m, 1H), 3.19-3.14 (m, 2H), 3.10-3.07 (m, 1H), 3.05-2.97 (m, 1H), 2.97-2.89 (m, 1H), 2.75-2.66 (m, 1H), 2.31-2.20 (m, 4H), 2.15-2.12 (m, 1H), 2.10-2.03 (m, 1H), 1.93-1.86 (m, 2H). LCMS Rt=2.786 min, m/z=657.2 [M+H]$^+$.

LCMS (5 to 95% acetonitrile in water+0.03% ammonium bicarbonate over 6 mins) retention time 2.786 min, ESI+ found [M+H]=657.2.

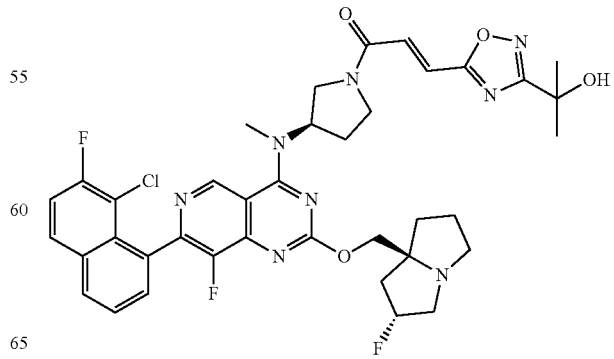

619

Example 88 (Method 1): (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-(2-hydroxypropan-2-yl)-1,2,4-oxadiazol-5-yl)prop-2-en-1-one

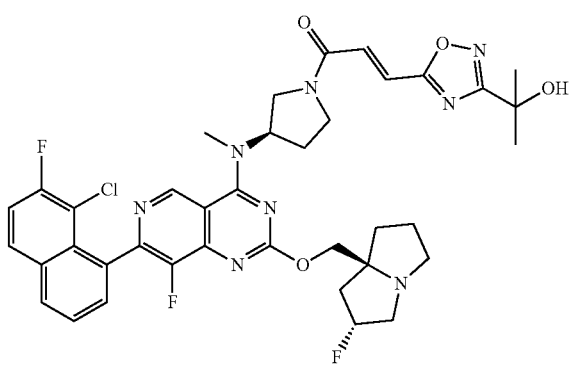 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)/C=C/c2nc(C(C)(C)O)no2)C1]

Step 1: (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-(2-hydroxypropan-2-yl)-1,2,4-oxadiazol-5-yl)prop-2-en-1-one The amide coupling reaction was prepared in a similar fashion to Method #1, Step 10. The residue was purified by prep-HPLC (column: Waters Xbridge Prep OBD C18 150*40 mm*10 um; mobile phase: [water (NH$_4$HCO$_3$)-acetonitrile]; B %: 30%-60%, 8 min) affording (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-(2-hydroxypropan-2-yl)-1,2,4-oxadiazol-5-yl)prop-2-en-1-one (6.69 mg, 6.09%) as a yellow oil: $^1$H NMR (400 MHz, Acetonitrile-d3) δ 9.23 (t, J=1.9 Hz, 1H), 8.19-8.14 (m, 1H), 8.10 (dd, J=5.7, 9.1 Hz, 1H), 7.73-7.67 (m, 2H), 7.58-7.38 (m, 3H), 5.45-5.19 (m, 2H), 4.28-4.23 (m, 1H), 4.21-4.16 (m, 1H), 4.11-3.99 (m, 1H), 3.87-3.75 (m, 1H), 3.70-3.52 (m, 2H), 3.48 (s, 3H), 3.21-3.14 (m, 2H), 3.10 (br d, J=2.5 Hz, 1H), 2.96-2.88 (m, 1H), 2.50-2.35 (m, 2H), 2.11-2.03 (m, 2H), 1.93-1.83 (m, 4H), 1.60 (d, J=7.6 Hz, 6H).

LCMS Rt=2.974 min, m/z=762.3 [M+H]$^+$.

LCMS (5 to 95% acetonitrile in water+0.03% ammonium bicarbonate over 6 mins) retention time 2.974 min, ESI+ found [M+H]=762.3.

620

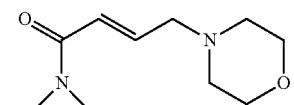

Example 89 (Method 8): (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-4-morpholinobut-2-en-1-one

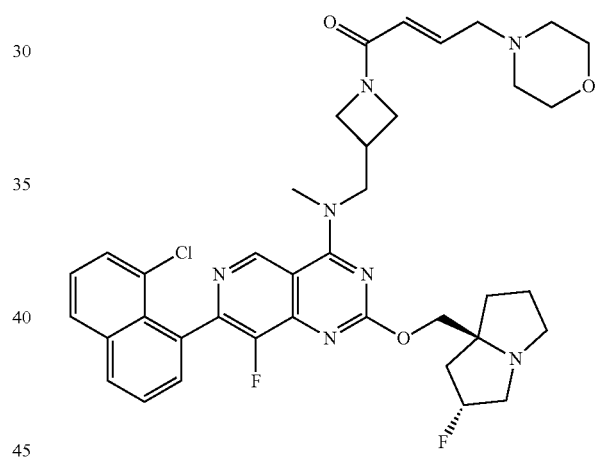

Step 1: (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-4-morpholinobut-2-en-1-one The Homer-Wadsworth-Emmons reaction was prepared in a similar fashion to Method #8, Step 4. The crude was purified by reverse phase HPLC (column: Phenomenex Luna C18 75*30 mm*3 μm; mobile phase: [water (formic acid)-acetonitrile]; B %: 10%-40%, 8 min) affording (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-4-morpholinobut-2-en-1-one (24.21 mg, 25.80%, formic acid salt) as a brown solid: $^1$H NMR (400 MHz, Acetonitrile-d3) δ 9.27 (s, 1H), 8.23 (s, 1H), 8.15 (dd, J=1.0, 8.1 Hz, 1H), 8.04 (d, J=7.5 Hz, 1H), 7.74-7.68 (m, 1H), 7.65-7.62 (m, 1H), 7.57-7.50 (m, 1H), 6.67 (td, J=6.2, 15.4 Hz, 1H), 6.14 (br d, J=15.3 Hz, 1H), 5.45-5.27 (m, 1H), 4.39-4.26 (m, 3H), 4.19 (br d, J=7.1 Hz, 2H), 4.15-4.05 (m, 2H), 3.95-3.81 (m, 1H), 3.69-3.62 (m, 4H), 3.60 (s, 3H), 3.41 (br s, 1H), 3.33-3.25 (m, 1H), 3.20 (br dd, J=6.3, 13.5 Hz, 1H), 3.12 (d, J=6.1 Hz, 2H), 3.08-2.96 (m, 1H), 2.44-2.34 (m, 4H), 2.30-2.20 (m, 2H), 2.16 (br d, J=8.8 Hz, 1H), 2.05-1.87 (m, 4H). LCMS Rt=1.903 min, m/z=717.3 [M+H]+.

LCMS (5 to 95% acetonitrile in water+0.1% trifluoroacetic acid over 6 mins) retention time 1.903 min, ESI+ found [M+H]=717.3.

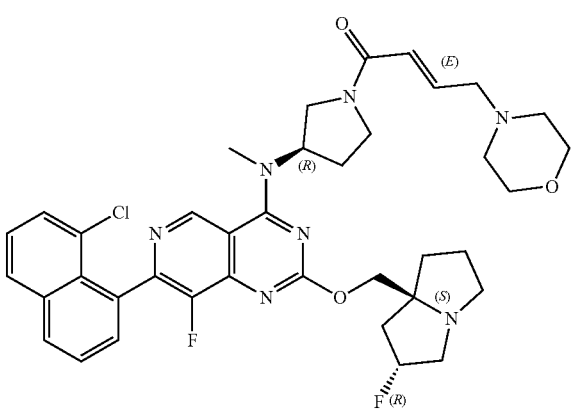

Example 90 (Method 8): (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-4-morpholinobut-2-en-1-one

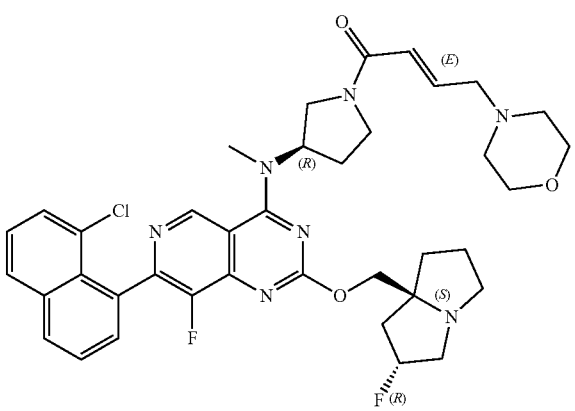

Step 1: (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-4-morpholinobut-2-en-1-one The Homer-Wadsworth-Emmons reaction was prepared in a similar fashion to Method #8, Step 4. The residue was purified by reverse phase HPLC (column: Phenomenex Luna C18 75*30 mm*3 µm; mobile phase: [water (formic acid)-acetonitrile]; B %: 10%-40%, 8 min) affording (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-4-morpholinobut-2-en-1-one (24.21 mg, 25.80%, formate salt) as a brown solid: 1H NMR (400 MHz, Acetonitrile-d3) δ 9.18 (d, J=1.5 Hz, 1H), 8.12 (d, J=8.2 Hz, 1H), 8.01 (d, J=8.2 Hz, 1H), 7.71-7.65 (m, 1H), 7.64-7.57 (m, 2H), 7.54-7.47 (m, 1H), 6.76-6.66 (m, 1H), 6.33 (s, 1H), 5.45-5.16 (m, 2H), 4.23-4.16 (m, 1H), 4.14-3.99 (m, 2H), 3.97-3.87 (m, 1H), 3.86-3.70 (m, 1H), 3.65-3.58 (m, 4H), 3.58-3.48 (m, 1H), 3.41 (s, 3H), 3.30-3.06 (m, 4H), 3.05 (s, 1H), 2.94-2.84 (m, 1H), 2.40 (br s, 4H), 2.36-2.23 (m, 2H), 2.17 (br s, 2H), 2.11-2.01 (m, 2H), 1.86 (br dd, J=9.6, 19.3 Hz, 2H). LCMS Rt=2.679 min, m/z=717.3 [M+H]+.

LCMS (5 to 95% acetonitrile in water+0.1% formic acid over 6 mins) retention time 2.679 min, ESI+ found [M+H]=717.3.

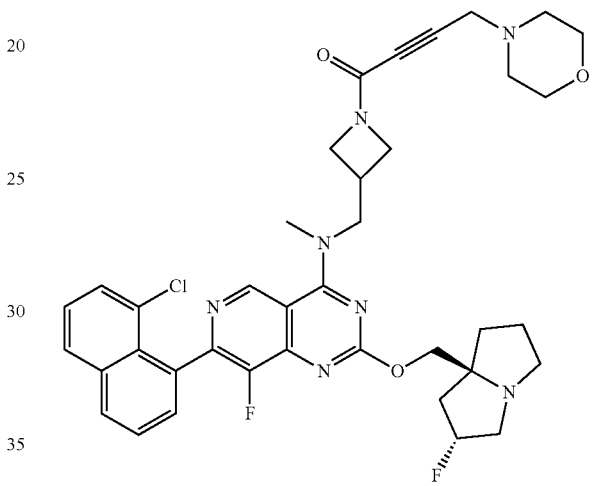

Example 91 (Method 1): 1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-4-morpholinobut-2-yn-1-one

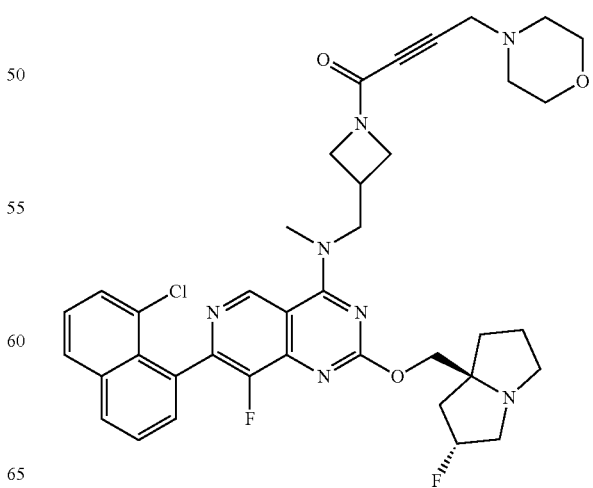

Step 1: 1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-4-morpholinobut-2-yn-1-one The amide coupling reaction was prepared in a similar fashion to Method #1, Step 10. The residue was purified by reverse phase HPLC(column: Waters Xbridge Prep OBD C18 150*40 mm*10 μm; mobile phase: [water (NH₄HCO₃)-acetonitrile]; B %: 35%-65%, 8 min) affording 1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-4-morpholinobut-2-yn-1-one (33.47 mg, 9.99%) as a yellow solid: $^1$H NMR (400 MHz, Acetonitrile-d3) δ 9.26 (s, 1H), 8.15 (d, J=9.0 Hz, 1H), 8.05 (d, J=7.8 Hz, 1H), 7.74-7.69 (m, 1H), 7.64 (d, J=7.3 Hz, 2H), 7.56-7.52 (m, 1H), 5.38-5.19 (m, 1H), 4.36-4.24 (m, 2H), 4.21-4.15 (m, 2H), 4.13-4.02 (m, 3H), 3.91-3.85 (m, 1H), 3.68 (br d, J=4.5 Hz, 1H), 3.64 (br d, J=4.8 Hz, 2H), 3.61-3.59 (m, 3H), 3.47 (s, 1H), 3.31-3.21 (m, 2H), 3.19-3.14 (m, 2H), 3.09 (s, 1H), 2.95-2.88 (m, 1H), 2.54-2.47 (m, 4H), 2.14-2.12 (m, 2H), 2.06 (br s, 2H), 1.92-1.87 (m, 2H), 1.83-1.78 (m, 1H). LCMS Rt=2.847 min, m/z=715.3 [M+H]⁺.

LCMS (5 to 95% acetonitrile in water+0.03% ammonium bicarbonate over 6 mins) retention time 2.847 min, ESI+ found [M+H]=715.3.

Step 1: 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-4-morpholinobut-2-yn-1-one The amide coupling reaction was prepared in a similar fashion to Method #1, Step 10. The residue was purified by reverse phase HPLC (column: Waters Xbridge Prep OBD C18 150*40 mm*10 μm; mobile phase: [water (NH₄HCO₃)-acetonitrile]; B %: 35%-65%, 8 min) affording 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-4-morpholinobut-2-yn-1-one (3.74 mg, 3.55%) as a yellow solid: $^1$H NMR (400 MHz, Acetonitrile-d3) δ 9.22 (d, J=4.3 Hz, 1H), 8.15 (d, J=7.9 Hz, 1H), 8.05 (d, J=7.5 Hz, 1H), 7.75-7.69 (m, 1H), 7.64 (br d, J=6.8 Hz, 2H), 7.58-7.52 (m, 1H), 5.45-5.21 (m, 2H), 4.29-4.09 (m, 3H), 4.08-3.79 (m, 2H), 3.78-3.72 (m, 1H), 3.70-3.66 (m, 2H), 3.65-3.59 (m, 2H), 3.53 (s, 1H), 3.49 (s, 1H), 3.48-3.44 (m, 3H), 3.23-3.14 (m, 2H), 3.11 (br s, 1H), 2.98-2.90 (m, 1H), 2.55 (td, J=4.7, 15.5 Hz, 4H), 2.43-2.34 (m, 2H), 2.11-2.06 (m, 2H), 2.03 (s, 1H), 1.93-1.82 (m, 3H). LCMS Rt=2.897 min, m/z=715.3 [M+H]⁺.

LCMS (5 to 95% acetonitrile in water+0.03% ammonium bicarbonate over 6 mins) retention time 2.897 min, ESI+ found [M+H]=715.3

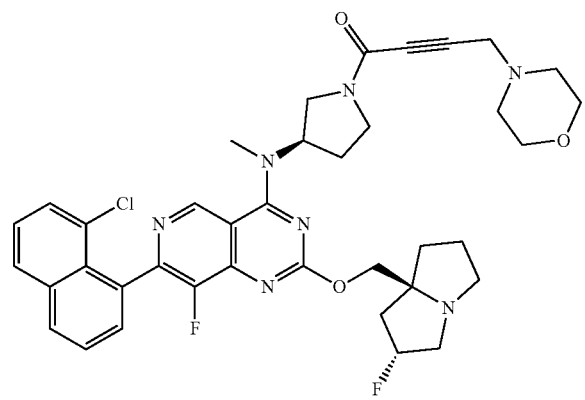 [SMILES: CN(c1nc(OC[C@@]23CCCN2C[C@H](F)C3)nc2c(F)c(-c3cccc4cccc(Cl)c34)ncc12)[C@@H]1CCN(C(=O)C#CCN2CCOCC2)C1]

Example 92 (Method 1): 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-4-morpholinobut-2-yn-1-one

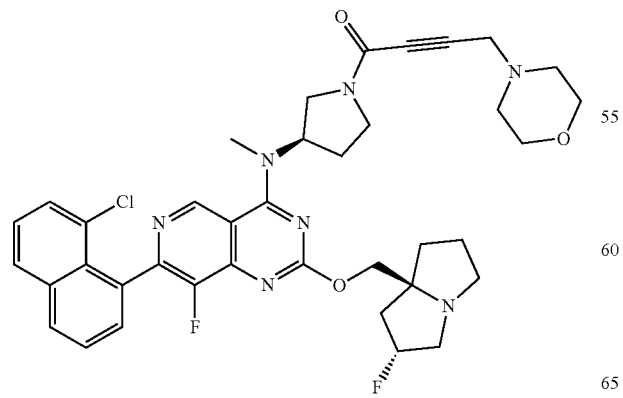

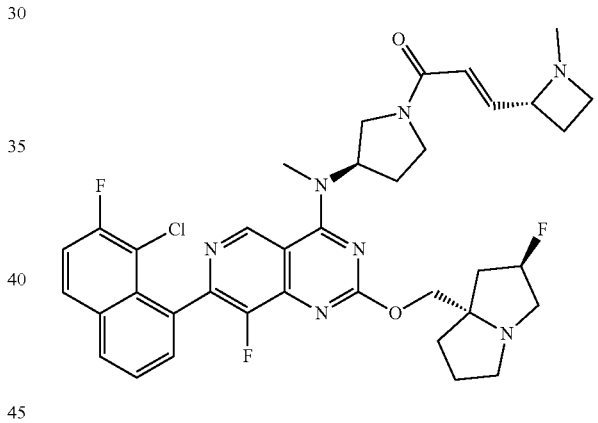

Example 93 (Method 8): (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-methylazetidin-2-yl)prop-2-en-1-one

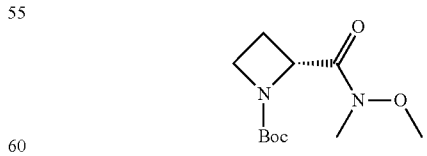

Step 1: tert-butyl (2R)-2-[methoxy(methyl)carbamoyl]azetidine-1-carboxylate

The amide coupling reaction was prepared in a similar fashion to Method #8, Step 1. The resulting residue was purified by column chromatography (silica gel, 100-200 mesh, 0-20% ethyl acetate in petroleum ether) affording tert-butyl (2R)-2-[methoxy(methyl)carbamoyl]azetidine-1-carboxylate (10 g, 86.71%) as a colorless oil. LCMS Rt=0.501 min, m/z=244.1 [M+H]+.

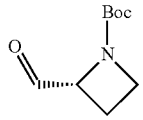

Step 2: tert-butyl (2R)-2-formylazetidine-1-carboxylate

The reductive reaction was prepared in a similar fashion to Method #8, Step 2. The mixture was concentrated in vacuo affording tert-butyl (2R)-2-formylazetidine-1-carboxylate (100 mg, crude) as a colorless oil used in the next step without further purification.

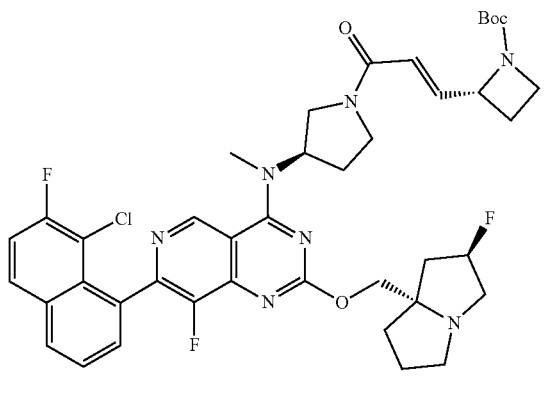 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)/C=C/[C@H]2CCN2C(=O)OC(C)(C)C)C1]

Step 3: (R)-tert-butyl 2-((E)-3-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-en-1-yl)azetidine-1-carboxylate The Homer-Wadsworth-Emmons reaction was prepared in a similar fashion to Method #8, Step 3, the reaction mixture was concentrated in vacuo affording (R)-tert-butyl 2-((E)-3-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-en-1-yl)azetidine-1-carboxylate (200 mg, crude) as a yellow oil. LCMS Rt=0.611 min, m/z=791.3 [M+H]+.

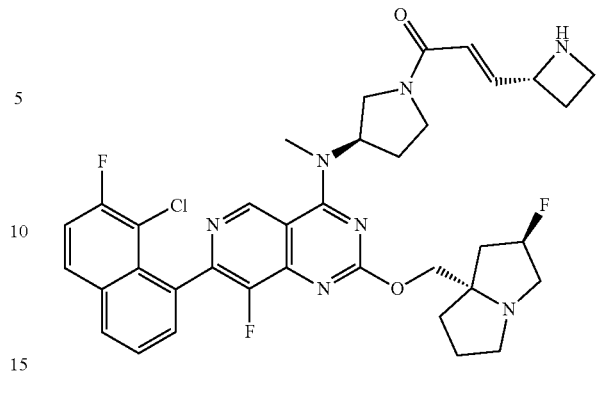

Step 4: (E)-3-((R)-azetidin-2-yl)-1-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)prop-2-en-1-one The deprotection of Boc group was prepared in a similar fashion to Method #1, Step 9. The reaction mixture was concentrated in vacuo affording (E)-3-((R)-azetidin-2-yl)-1-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)prop-2-en-1-one (130 mg, crude, trifluoroacetate salt) as a yellow oil, used in the next step without further purification.

LCMS Rt=0.758 min, m/z=691.3 [M+H]+.

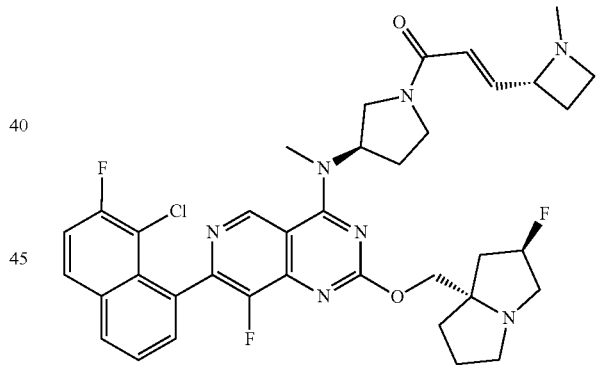

Step 5: (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-methylazetidin-2-yl)prop-2-en-1-one The reductive amination reaction was prepared in a similar fashion to Method #8, Step 6. The residue was purified by prep-HPLC (column: Waters Xbridge Prep OBD C18 150*40 mm*10 μm; mobile phase: [water (NH4HCO3)-acetonitrile]; B %: 25%-55%, 8 min) affording (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-methylazetidin-2-yl)prop-2-en-1-one (5.45 mg, 4.62%) as a yellow solid: 1H NMR (400 MHz, Acetonitrile-d3) δ 9.21 (d, J=2.1 Hz, 1H), 8.16 (dd, J=3.4, 6.2 Hz, 1H), 8.09 (dd, J=5.8, 9.1 Hz, 1H), 7.73-7.66 (m, 2H), 7.54 (t, J=8.9 Hz, 1H), 6.79 (dd, J=5.7, 15.1 Hz, 1H), 6.40 (dd, J=11.3, 14.6 Hz, 1H), 5.46-5.19 (m, 2H), 4.27-4.19 (m, 1H), 4.19-4.04 (m, 2H), 4.02-3.77 (m, 2H), 3.72-3.63 (m, 1H), 3.60-3.52 (m, 1H), 3.47-3.43 (m, 3H), 3.34-3.27 (m, 1H), 3.22-3.11 (m, 2H), 3.08 (s, 1H), 2.96-2.87 (m, 1H), 2.86-2.77 (m, 1H), 2.46-2.37 (m, 1H), 2.36-2.28 (m, 1H), 2.26 (d, J=8.3 Hz, 3H), 2.20 (br d, J=4.4 Hz, 2H), 2.13 (br s, 1H), 2.11-2.04 (m, 1H), 1.95-1.81 (m, 4H). LCMS Rt=2.938 min, m/z=705.3 [M+H]$^+$.

LCMS (5 to 95% acetonitrile in water+0.03% ammonium bicarbonate over 6 mins) retention time 2.938 min, ESI+ found [M+H]=705.3.

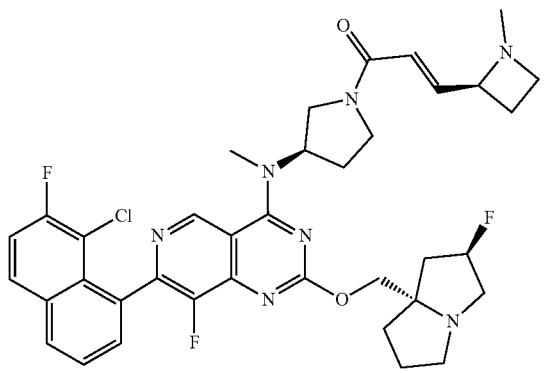 [SMILES: CN1CC[C@H]1/C=C/C(=O)N1CC[C@@H](N(C)c2nc(OC[C@@]34CCCN3C[C@H](F)C4)nc3c(F)c(-c4cccc5ccc(F)c(Cl)c45)ncc23)C1]

Example 94 (Method 8-Master): (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl) methoxy)pyrido[4,3-d]pyrimidin-4-yl)(methyl) amino)pyrrolidin-1-yl)-3-((S)-1-methylazetidin-2-yl) prop-2-en-1-one

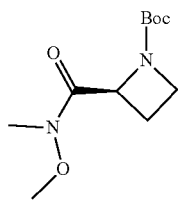 [SMILES: CON(C)C(=O)[C@@H]1CCN1C(=O)OC(C)(C)C]

Step 1: tert-butyl (2S)-2-[methoxy(methyl)carbamoyl]azetidine-1-carboxylate

To a solution of (2S)-1-tert-butoxycarbonylazetidine-2-carboxylic acid (2 g, 9.94 mmol) and N-methoxymethanamine; hydrochloride (1.16 g, 11.93 mmol) in N,N-dimethylformaldehyde (20 mL) were added 4-methylmorpholine (1.21 g, 11.93 mmol), 1-hydroxybenzotriazole (1.61 g, 11.93 mmol) and 3-(ethyliminomethyleneamino)-N,N-dimethyl-propan-1-amine; hydrochloride (2.29 g, 11.93 mmol) at 0° C. The mixture was stirred at 20° C. for 12 h. The reaction mixture was diluted with water (10 mL) and extracted with ethyl acetate (2×100 mL). The combined organic layers were dried over sodium sulphate and concentrated under vacuo, the resulting residue was purified by column chromatography (silica gel, 100-200 mesh, 0-35% ethyl acetate in petroleum ether) affording tert-butyl (2S)-2-[methoxy(methyl)carbamoyl]azetidine-1-carboxylate (2.1 g, 85.62%) as a colorless oil.

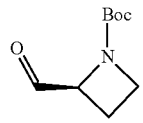 [SMILES: CC(C)(C)OC(=O)N1CC[C@H]1C=O]

Step 2: tert-butyl (2S)-2-formylazetidine-1-carboxylate

To a solution of tert-butyl (2S)-2-[methoxy(methyl)carbamoyl]azetidine-1-carboxylate (100 mg, 409.36 μmol) in tetrahydrofuran (2 mL) was added diisobutylalumane (1 M, 818.71 uL) at 0° C.

The mixture was stirred at 20° C. for 0.5 h under nitrogen. The reaction mixture was quenched with water (10 mL) and extracted with ethyl acetate (2×100 mL). The combined organic layers were dried over sodium sulphate and concentrated in vacuo affording tert-butyl (2S)-2-formylazetidine-1-carboxylate (75 mg, crude) as a yellow oil, used in the next step without further purification.

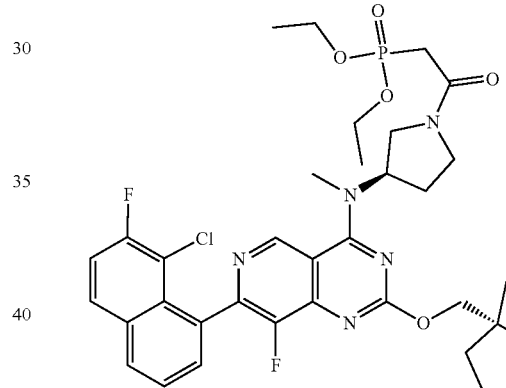

Step 3: diethyl (2-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-2-oxoethyl)phosphonate To a solution of 7-(8-chloro-7-fluoro-1-naphthyl)-8-fluoro-2-[[(2R,8S)-2-fluoro-1,2,3,5,6,7-hexahydropyrrolizin-8-yl]methoxy]-N-methyl-N-[(3R)-pyrrolidin-3-yl] pyrido[4,3-d]pyrimidin-4-amine (1.8 g, 2.58 mmol) in dichloromethane (15 mL) was added N,N-Diisopropylethylamine (1.33 g, 10.33 mmol), 2-diethoxyphosphorylacetic acid (1.01 g, 5.16 mmol) and 2,4,6-tripropyl-1,3,5,2λ5,4λ5,6λ5-trioxatriphosphinane 2,4,6-trioxide (3.29 g, 5.16 mmol). The mixture was stirred at 0° C. for 1 h. The reaction mixture was concentrated in vacuo. The resulting residue was purified by reverse phase HPLC affording (column: Phenomenex luna C18 (250*70 mm, 10 um); mobile phase: [water (trifluoroacetic acid)-acetonitrile]; B %: 22%-52%, 20 min) affording diethyl (2-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-2-oxoethyl) phosphonate (1.2 g, 53.10%, trifluoroacetate salt) as a yellow solid. LCMS Rt=0.794 min, m/z=760.3 [M+H]⁺.

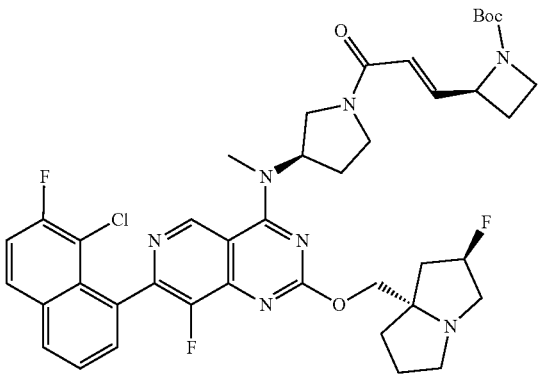 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)/C=C/[C@@H]2CCN2C(=O)OC(C)(C)C)C1]

Step 4: (S)-tert-butyl 2-((E)-3-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-en-1-yl)azetidine-1-carboxylate To a solution of 1-[(3R)-3-[[7-(8-chloro-7-fluoro-1-naphthyl)-8-fluoro-2-[[(2R,8S)-2-fluoro-1,2,3,5,6,7-hexahydropyrrolizin-8-yl]methoxy]pyrido[4,3-d]pyrimidin-4-yl]-methyl-amino]pyrrolidin-1-yl]-2-diethoxyphosphoryl-ethanone (120 mg, 157.65 µmol) in acetonitrile (2 mL) was added lithium; chloride (13.37 mg, 315.30 µmol) and N,N-diisopropylethylamine (61.13 mg, 472.96 µmol), tert-butyl (2S)-2-formylazetidine-1-carboxylate (87.60 mg, 472.96 µmol). The mixture was stirred at 25° C. for 1 h, the reaction mixture was diluted with water (10 mL) and extracted with ethyl acetate (2×100 mL). The combined organic layers were dried over sodium sulphate and concentrated under vacuo affording (S)-tert-butyl 2-((E)-3-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-en-1-yl)azetidine-1-carboxylate (134 mg, crude) as a yellow oil, used in next step without any further purification. LCMS Rt=0.613 min, m/z=791.3 [M+H]⁺.

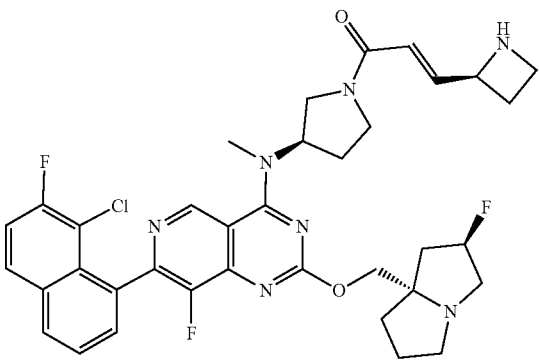 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)/C=C/[C@@H]2CCN2)C1]

Step 5: (E)-3-((S)-azetidin-2-yl)-1-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)prop-2-en-1-one The deprotection of Boc group was prepared in a similar fashion to Method #1, Step 9. The reaction mixture was concentrated in vacuo affording (E)-3-((S)-azetidin-2-yl)-1-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)prop-2-en-1-one (110 mg, crude, trifluoroacetic acid salt) as a yellow oil, used in next step without any further purification. LCMS Rt=0.590 min, m/z=691.3 [M+H]⁺.

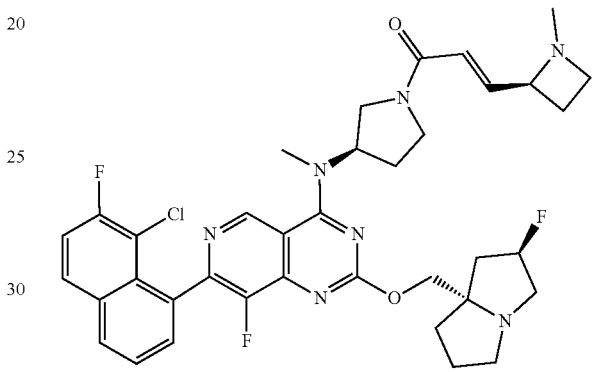

Step 6: (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((S)-1-methylazetidin-2-yl)prop-2-en-1-one The reductive amination was prepared in a similar fashion to Method #7, Step 4. The residue was purified by prep-HPLC (column: Waters Xbridge Prep OBD C18 150*40 mm*10 um; mobile phase: [water (NH₄HCO3)-acetonitrile]; B %: 25%-55%, 8 min) affording (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((S)-1-methylazetidin-2-yl)prop-2-en-1-one (12.63 mg, 12.57%) as a yellow solid: ¹H NMR (400 MHz, Acetonitrile-d3) δ 9.18 (t, J=2.5 Hz, 1H), 8.15-8.09 (m, 1H), 8.05 (dd, J=5.8, 9.0 Hz, 1H), 7.69-7.63 (m, 2H), 7.51 (t, J=8.9 Hz, 1H), 6.76 (ddd, J=2.4, 5.6, 15.1 Hz, 1H), 6.41-6.32 (m, 1H), 5.42-5.15 (m, 2H), 4.22-4.16 (m, 1H), 4.14-4.08 (m, 1H), 4.05 (br d, J=8.1 Hz, 1H), 3.98-3.75 (m, 2H), 3.69-3.59 (m, 1H), 3.55-3.48 (m, 1H), 3.44-3.40 (m, 3H), 3.32-3.22 (m, 1H), 3.16-3.09 (m, 2H), 3.05 (s, 1H), 2.92-2.84 (m, 1H), 2.84-2.73 (m, 1H), 2.40-2.33 (m, 1H), 2.32-2.26 (m, 1H), 2.23 (d, J=9.6 Hz, 3H), 2.19-2.10 (m, 2H), 2.09 (br d, J=2.4 Hz, 1H), 2.04 (br s, 1H), 1.92-1.78 (m, 4H). LCMS Rt=2.951 min, m/z=705.3 [M+H]⁺.

LCMS (5 to 95% acetonitrile in water+0.03% ammonium bicarbonate over 6 mins) retention time 2.951 min, ESI+ found [M+H]=705.3.

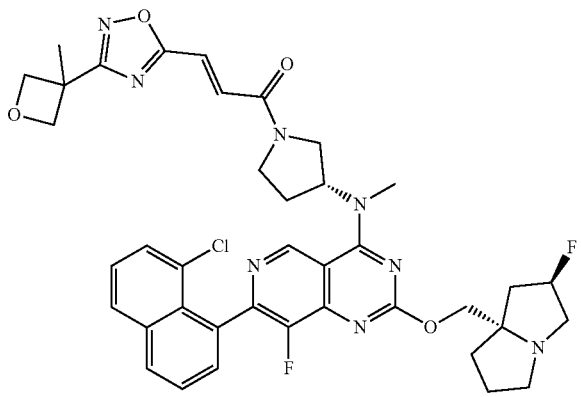 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2nc(C3(C)COC3)no2)C1]

Example 95 (Method 1-Master): (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-(3-methyloxetan-3-yl)-1,2,4-oxadiazol-5-yl)prop-2-en-1-one

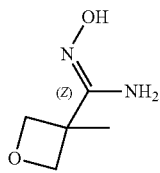

Step 1: (Z)—N'-hydroxy-3-methyloxetane-3-carboximidamide

To a solution of 3-methyloxetane-3-carbonitrile (1 g, 10.30 mmol) in ethanol (10 mL) were added hydroxylamine hydrochloride (1.07 g, 15.45 mmol) and potassium carbonate (2.85 g, 20.59 mmol), the mixture was stirred at 80° C. for 2 h. The mixture was concentrated to dryness in vacuo. The mixture was diluted with water (5 mL) and extracted with ethyl acetate (2×10 mL).

The combined organic layers were dried over sodium sulphate and concentrated in vacuo affording (Z)—N'-hydroxy-3-methyloxetane-3-carboximidamide (510 mg, crude) as a white solid, used in next step without any further purification: $^1$H NMR (400 MHz, Dimethyl sulfoxide-d6) δ 9.64-9.45 (m, 1H), 8.30-8.09 (m, 2H), 4.80 (d, J=5.9 Hz, 2H), 4.15 (d, J=6.0 Hz, 2H), 1.63-1.57 (m, 3H).

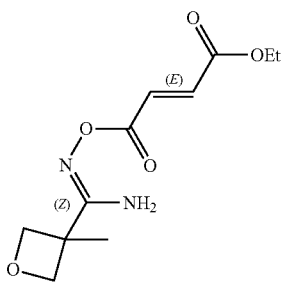 [SMILES: CCOC(=O)/C=C/C(=O)O/N=C(\N)C1(C)COC1]

Step 2: (E)-ethyl 4-(((Z)-(amino(3-methyloxetan-3-yl)methylene)amino)oxy)-4-oxobut-2-enoate To a solution of 2,5-dioxopyrrolidin-1-yl ethyl fumarate (891.44 mg, 3.70 mmol) in dioxane (10 mL) were added potassium carbonate (1.18 g, 8.53 mmol) and (Z)—N'-hydroxy-3-methyloxetane-3-carboximidamide (370 mg, 2.84 mmol) at 0° C., the mixture was stirred at 25° C. for 3 h. The mixture was diluted with water (10 mL) and extracted with ethyl acetate (2×20 mL). The combined organic layers were dried over sodium sulphate and concentrated in vacuo affording (E)-ethyl 4-(((Z)-(amino(3-methyloxetan-3-yl)methylene)amino)oxy)-4-oxobut-2-enoate (330 mg, crude) as a pale yellow oil, used in next step without any further purification. LCMS Rt=0.629 min, m/z=256.1 [M+H]$^+$.

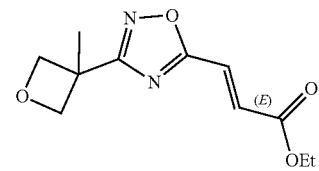 [SMILES: CCOC(=O)/C=C/c1nc(C2(C)COC2)no1]

Step 3: (E)-ethyl 3-(3-(3-methyloxetan-3-yl)-1,2,4-oxadiazol-5-yl)acrylate

To a solution of (E)-ethyl 4-(((Z)-(amino(3-methyloxetan-3-yl)methylene)amino)oxy)-4-oxobut-2-enoate (330 mg, 1.29 mmol) in toluene (3 mL) was added pyridine (152.80 mg, 1.93 mmol), the mixture was stirred at 110° C. for 12 h. The mixture was diluted with water (5 mL) and extracted with ethyl acetate (2×10 mL). The combined organic layers were dried over sodium sulphate and concentrated in vacuo affording (E)-ethyl 3-(3-(3-methyloxetan-3-yl)-1,2,4-oxadiazol-5-yl)acrylate (250 mg, crude) as a brown oil, used in next step without any further purification. LCMS Rt=0.758 min, m/z=238.1 [M+H]$^+$.

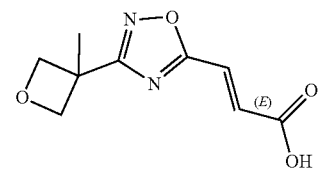

Step 4: (E)-3-(3-(3-methyloxetan-3-yl)-1,2,4-oxadiazol-5-yl)acrylic acid

To a solution of (E)-ethyl 3-(3-(3-methyloxetan-3-yl)-1,2,4-oxadiazol-5-yl)acrylate (100 mg, 419.75 µmol) in tetrahydrofuran (1 mL) was added lithium hydroxide monohydrate (2 M, 419.75 uL) at 0° C., the mixture was stirred at 0° C. for 0.5 h. The mixture was quenched with saturated citric acid at 0° C. to adjust pH=4. The mixture was diluted with water (3 mL) and extracted with ethyl acetate (3×5 mL). The combined organic layers were dried over sodium sulphate and concentrated in vacuo affording (E)-3-[3-(3-methyloxetan-3-yl)-1,2,4-oxadiazol-5-yl]prop-2-enoic acid (160 mg, crude) as a yellow oil, used in next step without any further purification.

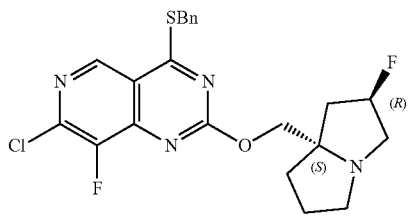

Step 5: 4-(benzylthio)-7-chloro-8-fluoro-2-(((2R, 7aS)-2-fluorohexahydro-1H-pyrrolizin-7a-yl) methoxy)pyrido[4,3-d]pyrimidine To a solution of 4-benzylsulfanyl-2,7-dichloro-8-fluoro-pyrido[4,3-d]pyrimidine (30 g, 88.18 mmol) in dioxane (500 mL) was added N,N-diisopropylethylamine (34.19 g, 264.55 mmol, 46.08 mL) and ((2R,7aS)-2-fluorohexahydro-1H-pyrrolizin-7a-yl)methanol (21.06 g, 132.27 mmol). The mixture was stirred at 80° C. for 1 h. The mixture was diluted with water (200 mL) and extracted with ethyl acetate (3×200 mL). The combined organic layers were dried over sodium sulphate and concentrated in vacuo. The crude residue was diluted with a (10:1) mixture of petroleum ether: ethyl acetate (110 mL) and the resulting precipitate was filtered affording 4-(benzylthio)-7-chloro-8-fluoro-2-(((2R, 7aS)-2-fluorohexahydro-1H-pyrrolizin-7a-yl)methoxy) pyrido[4,3-d]pyrimidine (25 g, 61%) as a brown solid. LCMS Rt=0.577 min, m/z=462.1 [M+H]$^+$.

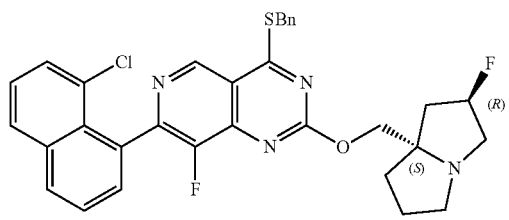

Step 6: 4-(benzylthio)-7-(8-chloronaphthalen-1-yl)-8-fluoro-2-(((2R,7aS)-2-fluorohexahydro-1H-pyrrolizin-7a-yl)methoxy)pyrido[4,3-d]pyrimidine A mixture of 4-(benzylthio)-7-chloro-8-fluoro-2-(((2R, 7aS)-2-fluorohexahydro-1H-pyrrolizin-7a-yl)methoxy) pyrido[4,3-d]pyrimidine (21 g, 45.36 mmol), (8-chloro-1-naphthyl)boronic acid (18.73 g, 90.72 mmol), [2-(2-aminophenyl)phenyl]-chloro-palladium; dicyclohexyl-[3-(2,4,6-triisopropylphenyl)phenyl]phosphane (3.57 g, 4.54 mmol) and potassium phosphate (28.89 g, 136.09 mmol) in dioxane (300 mL) and water (100 mL) was degassed and purged with nitrogen for 3 times. Then the mixture was stirred at 60° C. for 1 h under nitrogen atmosphere. The mixture was diluted with water (100 mL) and extracted with ethyl acetate (3×100 mL). The combined organic layers were dried over sodium sulphate and concentrated in vacuo. The residue was purified by column chromatography (silica gel, 100-200 mesh, 20%-100% ethyl acetate in petroleum ether) affording 4-(benzylthio)-7-(8-chloronaphthalen-1-yl)-8-fluoro-2-(((2R,7aS)-2-fluorohexahydro-1H-pyrrolizin-7a-yl)methoxy)pyrido[4,3-d]pyrimidine (14 g, 52.39%) as a yellow oil. LCMS Rt=0.616 min, m/z=588.2 [M+H]$^+$.

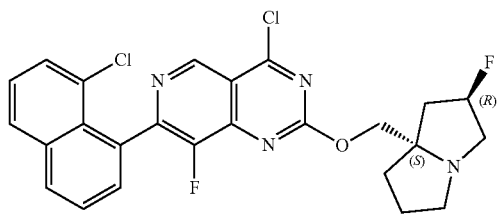

Step 7: 4-chloro-7-(8-chloronaphthalen-1-yl)-8-fluoro-2-(((2R,7aS)-2-fluorohexahydro-1H-pyrrolizin-7a-yl)methoxy)pyrido[4,3-d]pyrimidine To a solution of 4-(benzylthio)-7-(8-chloronaphthalen-1-yl)-8-fluoro-2-(((2R,7aS)-2-fluorohexahydro-1H-pyrrolizin-7a-yl)methoxy)pyrido[4,3-d]pyrimidine (0.3 g, 509.25 μmol) in acetonitrile (2 mL) was added water (917.68 ug, 50.93 μmol) and acetic acid (3.06 mg, 50.93 μmol). A solution of 1,3-dichloro-5,5-dimethyl-imidazolidine-2,4-dione (301.00 mg, 1.53 mmol) in acetonitrile (1 mL) was added into the above solution at 0° C., then stirred at 0° C. for 1 h. The reaction mixture was quenched with saturated sodium sulfite (5 mL) and extracted with ethyl acetate (2×10 mL). The combined organic layers were dried over sodium sulphate and concentrated in vacuo affording 4-chloro-7-(8-chloronaphthalen-1-yl)-8-fluoro-2-(((2R, 7aS)-2-fluorohexahydro-1H-pyrrolizin-7a-yl)methoxy) pyrido[4,3-d]pyrimidine (255 mg, crude) as a yellow oil, used in next step without any further purification. LCMS Rt=0.568 min, m/z=500.1 [M+H]$^+$.

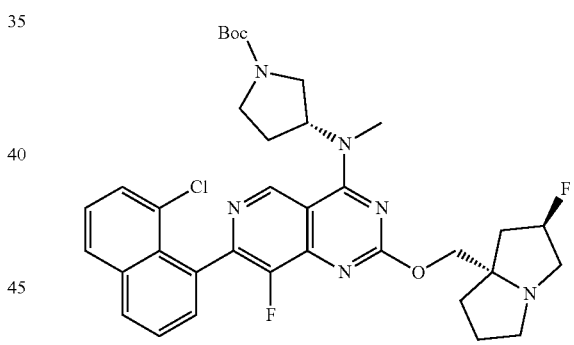

Step 8: (R)-tert-butyl 3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate To a solution of 4-chloro-7-(8-chloronaphthalen-1-yl)-8-fluoro-2-(((2R,7aS)-2-fluorohexahydro-1H-pyrrolizin-7a-yl)methoxy)pyrido[4,3-d]pyrimidine (1.5 g, 2.99 mmol) in tetrahydrofuran (30 mL) was added N,N-diisopropylethylamine (1.16 g, 8.98 mmol) and tert-butyl (3R)-3-(methylamino)pyrrolidine-1-carboxylate (1.50 g, 7.48 mmol). The mixture was stirred at −20° C. for 1 h. The mixture was diluted with water (20 mL) and extracted with ethyl acetate (3×50 mL). The combined organic layers were dried over sodium sulphate and concentrated in vacuo. The residue was purified by column chromatography (silica gel, 100-200 mesh, 20-50% ethyl acetate in petroleum ether) affording (R)-tert-butyl 3-((7-(8-chloronaphthalen-1-yl)-8-fluoro-2-

(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (920 mg, 46.23%) as a yellow oil. LCMS Rt=0.651 min, m/z=664.3 [M+H]+

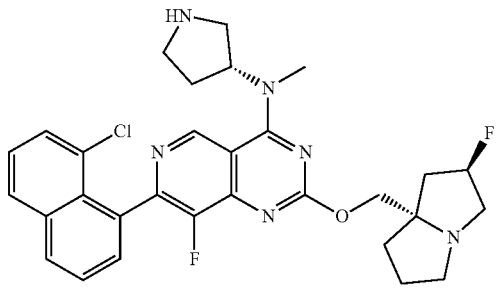 [SMILES: CN(c1nc(OC[C@@]23CCCN2C[C@H](F)C3)nc2c(F)c(-c3cccc4cccc(Cl)c34)ncc12)[C@@H]1CCNC1]

Step 9: 7-(8-chloronaphthalen-1-yl)-8-fluoro-2-(((2R,7aS)-2-fluorohexahydro-1H-pyrrolizin-7a-yl)methoxy)-N-methyl-N—((R)-pyrrolidin-3-yl)pyrido[4,3-d]pyrimidin-4-amine A mixture of (R)-tert-butyl 3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (70 mg, 105.24 μmol) in hydrochloric acid in ethyl acetate (4 M, 1 mL) was stirred at 25° C. for 1 h. The mixture was concentrated to dryness in vacuo affording 7-(8-chloronaphthalen-1-yl)-8-fluoro-2-(((2R,7aS)-2-fluorohexahydro-1H-pyrrolizin-7a-yl)methoxy)-N-methyl-N—((R)-pyrrolidin-3-yl)pyrido[4,3-d]pyrimidin-4-amine (63 mg, crude, hydrochloride salt) as a yellow oil, used in next step without any further purification. LCMS Rt=0.647 min, m/z=564.2 [M+H]+.

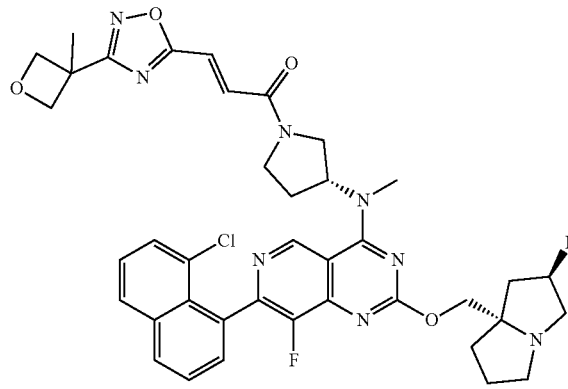 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2nc(C3(C)COC3)no2)C1]

Step 10: (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-methyloxetan-3-yl)-1,2,4-oxadiazol-5-yl)prop-2-en-1-one To a solution of 7-(8-chloronaphthalen-1-yl)-8-fluoro-2-(((2R,7aS)-2-fluorohexahydro-1H-pyrrolizin-7a-yl)methoxy)-N-methyl-N—((R)-pyrrolidin-3-yl)pyrido[4,3-d]pyrimidin-4-amine (63 mg, 104.74 μmol, hydrochloride salt) in N,N-dimethylformaldehyde (1 mL) were added N,N-diisopropylethylamine (67.68 mg, 523.68 μmol), (E)-3-[3-(3-methyloxetan-3-yl)-1,2,4-oxadiazol-5-yl]prop-2-enoic acid (33.02 mg, 157.10 μmol) and 2,4,6-tripropyl-1,3,5,2,4,6-trioxatriphosphinane 2,4,6-trioxide (99.97 mg, 157.10 μmol) at 0° C., the mixture was stirred at 25° C. for 1 h. The reaction mixture was concentrated in vacuo and the residue was purified by reverse phase HPLC (column: Waters Xbridge Prep OBD C18 150*40 mm*10 μm; mobile phase: [water (NH4HCO3)-acetonitrile]; B %: 35%-65%, 8 min) affording (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-methyloxetan-3-yl)-1,2,4-oxadiazol-5-yl)prop-2-en-1-one (6.99 mg, 8.81%) as a yellow amorphous solid: $^1$H NMR (400 MHz, Acetonitrile-d3) δ 9.20 (s, 1H), 8.12 (d, J=8.1 Hz, 1H), 8.02 (d, J=8.0 Hz, 1H), 7.73-7.66 (m, 1H), 7.65-7.58 (m, 2H), 7.55-7.37 (m, 3H), 5.47-5.16 (m, 2H), 4.98-4.88 (m, 2H), 4.57 (t, J=6.6 Hz, 2H), 4.26-4.16 (m, 2H), 4.10-3.71 (m, 3H), 3.68-3.50 (m, 1H), 3.45 (s, 3H), 3.27-3.06 (m, 3H), 2.96-2.85 (m, 1H), 2.49-2.20 (m, 4H), 1.88 (br s, 3H), 1.76 (d, J=7.5 Hz, 4H). LCMS Rt=2.873 min, m/z=756.3 [M+H]$^+$.

LCMS (5 to 95% acetonitrile in water+0.03% ammonium bicarbonate over 6 mins) retention time 2.873 min, ESI+ found [M+H]=756.3.

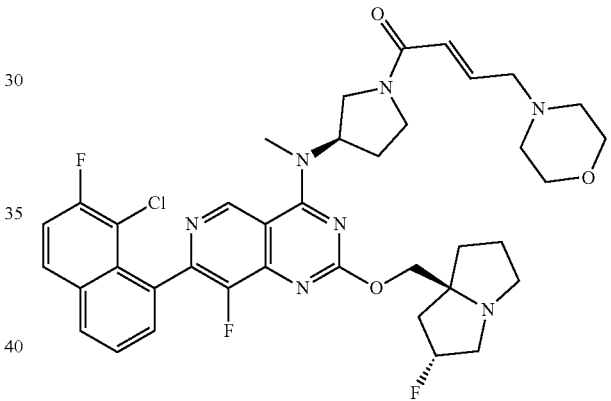

Example 96 (Method 8): (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-4-morpholinobut-2-en-1-one

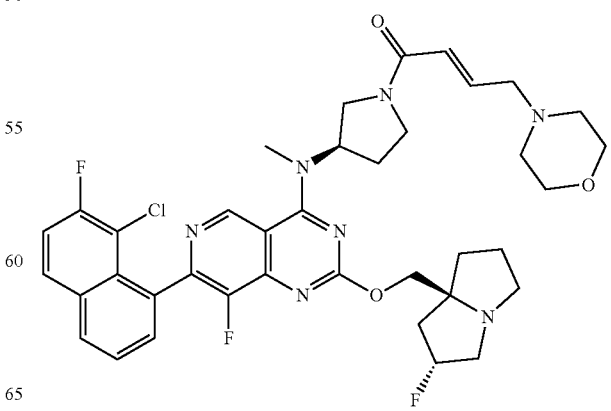

Step 1: (E)-1-((R)-3-((7-(8-chloro-7-fluoronaphtha-len-1-yl)-8-fluoro-2-(((2R,7aS)-2-fluorotetrahydro-1H-pyrrolizin-7a(5H)-yl)methoxy)pyrido[4,3-d]py-rimidin-4-yl)(methyl)amino)pyrrolidin-1-yl)-4-morpholinobut-2-en-1-one The Homer-Wadsworth-Emmons reaction was prepared in a similar fashion to Method #8, Step 4. The residue was purified by reverse phase HPLC (column: Waters Xbridge BEH C18 100*30 mm*10 μm; mobile phase: [water (NH₄HCO₃)-acetonitrile]; B %: 30%-60%, 8 min) affording (E)-1-((R)-3-((7-(8-chloro-7-fluoronaphthalen-1-yl)-8-fluoro-2-(((2R,7aS)-2-fluorotetrahydro-1H-pyrrolizin-7a (5H)-yl)methoxy)pyrido[4,3-d]pyrimidin-4-yl)(methyl) amino)pyrrolidin-1-yl)-4-morpholinobut-2-en-1-one (32.88 mg, 38.64%) as a yellow solid. $^1$H NMR (400 MHz, Acetonitrile-d3) δ 9.24-9.20 (m, 1H), 8.19-8.14 (m, 1H), 8.09 (dd, J=5.7, 9.1 Hz, 1H), 7.73-7.67 (m, 2H), 7.55 (t, J=8.9 Hz, 1H), 6.80-6.71 (m, 1H), 6.48-6.38 (m, 1H), 5.44-5.18 (m, 2H), 4.26-4.20 (m, 1H), 4.17-4.12 (m, 1H), 4.10-3.93 (m, 1H), 3.91-3.79 (m, 1H), 3.70-3.63 (m, 5H), 3.62-3.48 (m, 1H), 3.46-3.44 (m, 3H), 3.19-3.11 (m, 4H), 3.08 (s, 1H), 2.95-2.88 (m, 1H), 2.43 (br d, J=1.9 Hz, 4H), 2.35-2.28 (m, 1H), 2.22-2.18 (m, 1H), 2.13 (br d, J=2.5 Hz, 2H), 2.10-2.03 (m, 1H), 1.95-1.84 (m, 3H). LCMS Rt=1.879 min, m/z=735.3 [M+H]⁺.

LCMS (5 to 95% acetonitrile in water+0.03% ammonium bicarbonate over 6 min) retention time 1.879 min, ESI+ found [M+H]=735.3.

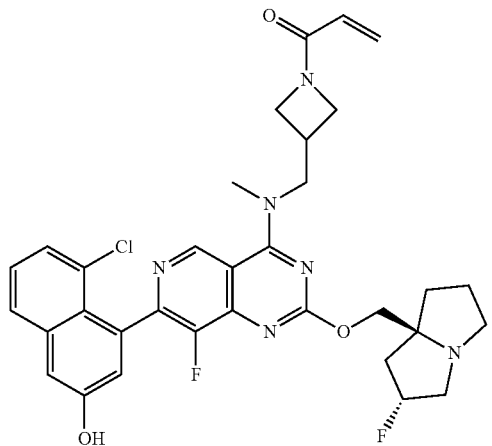 [SMILES: C=CC(=O)N1CC(CN(C)c2nc(OC[C@@]34CCCN3C[C@H](F)C4)nc3c(F)c(-c4cc(O)cc5cccc(Cl)c45)ncc23)C1]

Example 97 (Method 3):1-(3-(((7-(8-chloro-3-hy-droxynaphthalen-1-yl)-8-fluoro-2-(((2R,7aS)-2-fluo-rotetrahydro-1H-pyrrolizin-7a(5H)-yl)methoxy) pyrido[4,3-d]pyrimidin-4-yl)(methyl)amino)methyl) azetidin-1-yl)prop-2-en-1-one

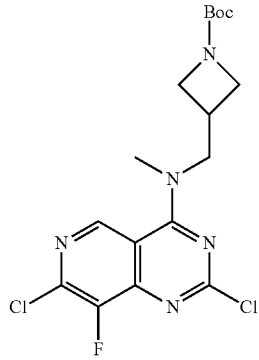 [SMILES: CN(CC1CN(C(=O)OC(C)(C)C)C1)c1nc(Cl)nc2c(F)c(Cl)ncc12]

Step 1: tert-butyl 3-[[(2,7-dichloro-8-fluoro-pyrido [4,3-d]pyrimidin-4-yl)-methyl-amino]methyl]azeti-dine-1-carboxylate The substitution reaction was prepared in a similar fashion to Method #2, Step 3. The mixture was concentrated in vacuo affording tert-butyl 3-[[(2,7-dichloro-8-fluoro-pyrido [4,3-d]pyrimidin-4-yl)-methyl-amino]methyl]azetidine-1-carboxylate (7 g, crude) as a brown solid, used in the next step without further purification. LCMS Rt=0.826 min, m/z=415.1 [M+H]⁺.

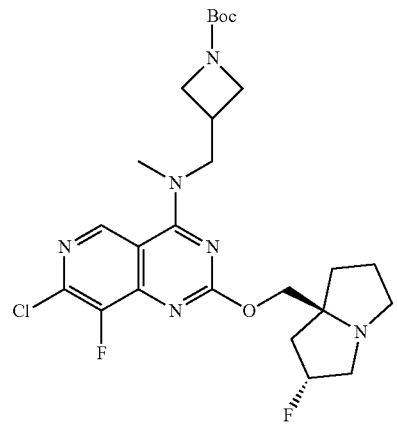 [SMILES: CN(CC1CN(C(=O)OC(C)(C)C)C1)c1nc(OC[C@@]23CCCN2C[C@H](F)C3)nc2c(F)c(Cl)ncc12]

Step 2: tert-butyl 3-(((7-chloro-8-fluoro-2-(((2R, 7aS)-2-fluorohexahydro-1H-pyrrolizin-7a-yl) methoxy)pyrido[4,3-d]pyrimidin-4-yl)(methyl) amino)methyl)azetidine-1-carboxylate The substitution reaction was prepared in a similar fashion to Method #2, Step 4. The crude product was purified by column chromatography (silica gel, 100-200 mesh, 80-100% ethyl acetate in petroleum ether) affording tert-butyl 3-(((7-chloro-8-fluoro-2-(((2R,7aS)-2-fluorohexa-hydro-1H-pyrrolizin-7a-yl)methoxy)pyrido[4,3-d]pyrimi-din-4-yl)(methyl)amino)methyl)azetidine-1-carboxylate (2 g, 44.12%) as a yellow solid: $^1$H NMR (400 MHz, Chloro-form-d) δ 8.87 (s, 1H), 5.41-5.18 (m, 1H), 4.30-4.19 (m, 2H), 4.08 (q, J=8.3 Hz, 4H), 3.81-3.74 (m, 2H), 3.53-3.48 (m, 3H), 3.35-3.17 (m, 3H), 3.09-2.95 (m, 2H), 2.29-2.08 (m, 3H), 2.00-1.84 (m, 3H), 1.45 (s, 9H). LCMS Rt=0.645 min, m/z=538.2 [M+H]⁺.

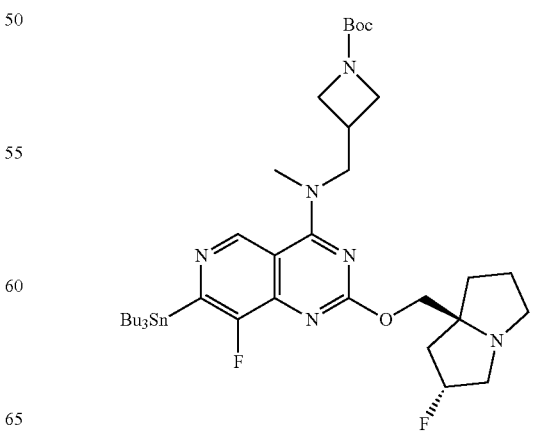

Step 3: tert-butyl 3-(((8-fluoro-2-(((2R,7aS)-2-fluorohexahydro-1H-pyrrolizin-7a-yl)methoxy)-7-(tributylstannyl)pyrido[4,3-d]pyrimidin-4-yl)(methyl)amino)methyl)azetidine-1-carboxylate The tin reagent formation was prepared in a similar fashion to Method #3, Step 5. The residue was purified by column chromatography (silica gel, 100-200 mesh, 80-100% ethyl acetate in petroleum ether) affording tert-butyl 3-(((8-fluoro-2-(((2R,7aS)-2-fluorohexahydro-1H-pyrrolizin-7a-yl)methoxy)-7-(tributylstannyl)pyrido[4,3-d]pyrimidin-4-yl)(methyl)amino)methyl)azetidine-1-carboxylate (2.5 g, 84.90%) as a yellow oil. LCMS Rt=2.437 min, m/z=794.4 [M+H]+.

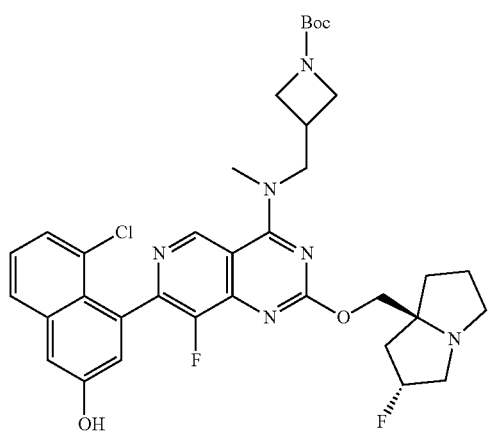 [SMILES: CN(CC1CN(C(=O)OC(C)(C)C)C1)c1nc(OC[C@@]23CCCN2C[C@H](F)C3)nc2c(F)c(-c3cc(O)cc4cccc(Cl)c34)ncc12]

Step 4: tert-butyl 3-(((7-(8-chloro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)methyl)azetidine-1-carboxylate The Stille reaction was prepared in a similar fashion to Method #3, Step 6. The mixture was stirred at 100° C. for 3 h under nitrogen atmosphere. The mixture was quenched by water (50 mL), exacted with ethyl acetate (3×100 mL). The organic layers were concentrated in vacuo and purified by reverse phase HPLC (column: Phenomenex luna C18 250*50 mm*10 μm; mobile phase: [water (trifluoroacetic acid)-acetonitrile]; B %: 20%-50%, 10 min) affording tert-butyl 3-(((7-(8-chloro-3-hydroxynaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)methyl)azetidine-1-carboxylate (400 mg, 72%) as a yellow solid. LCMS Rt=0.686 min, m/z=680.3 [M+H]+.

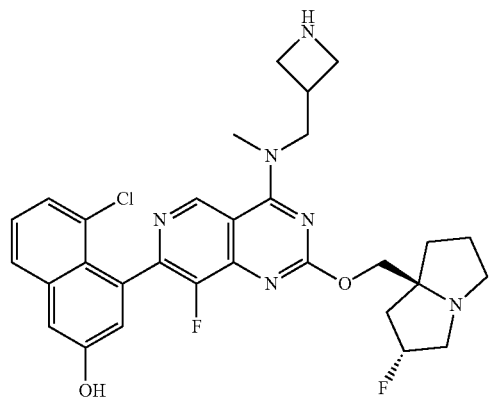 [SMILES: CN(CC1CNC1)c1nc(OC[C@@]23CCCN2C[C@H](F)C3)nc2c(F)c(-c3cc(O)cc4cccc(Cl)c34)ncc12]

Step 5: 4-(4-((azetidin-3-ylmethyl)(methyl)amino)-8-fluoro-2-(((2R,7aS)-2-fluorohexahydro-1H-pyrrolizin-7a-yl)methoxy)pyrido[4,3-d]pyrimidin-7-yl)-5-chloronaphthalen-2-ol The de-Boc protecting reaction was prepared in a similar fashion to Method #3, Step 7. The reaction mixture was concentrated in vacuo affording 4-(4-((azetidin-3-ylmethyl)(methyl)amino)-8-fluoro-2-(((2R,7aS)-2-fluorohexahydro-1H-pyrrolizin-7a-yl)methoxy)pyrido[4,3-d]pyrimidin-7-yl)-5-chloronaphthalen-2-ol (200 mg, crude, trifluoroacetate salt), used in next step without further purification. LCMS Rt=0.549 min, m/z=580.2 [M+H]+.

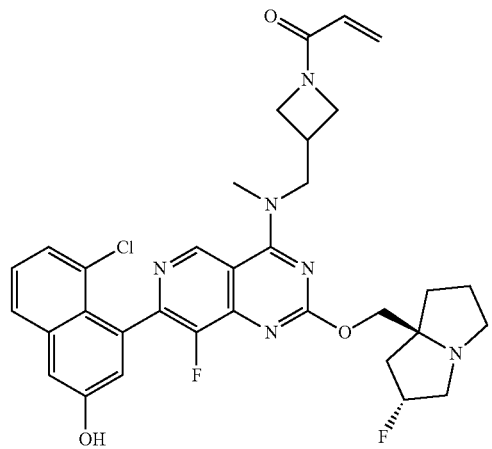 [SMILES: C=CC(=O)N1CC(CN(C)c2nc(OC[C@@]34CCCN3C[C@H](F)C4)nc3c(F)c(-c4cc(O)cc5cccc(Cl)c45)ncc23)C1]

Step 6: 1-(3-(((7-(8-chloro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)prop-2-en-1-one The amide coupling reaction was prepared in a similar fashion to Method #3, Step 8. The crude was purified by reverse phase HPLC (column: Waters Xbridge Prep OBD C18 150*40 mm*10 um; mobile phase: [water (NH4HCO3)-acetonitrile]; B %: 20%-50%, 8 min) affording 1-(3-(((7-(8-chloro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)

prop-2-en-1-one (9.71 mg, 8.22%) as white amorphous solid. ¹H NMR (400 MHz, Acetonitrile-d3) δ 9.21 (s, 1H), 7.83-7.77 (m, 1H), 7.43-7.36 (m, 3H), 7.18 (d, J=2.0 Hz, 1H), 6.34-6.24 (m, 1H), 6.19-6.12 (m, 1H), 5.62 (dd, J=1.5, 9.9 Hz, 1H), 5.35-5.16 (m, 1H), 4.34 (br t, J=8.4 Hz, 1H), 4.21-4.07 (m, 6H), 3.85 (br d, J=5.3 Hz, 1H), 3.56 (s, 3H), 3.23-3.03 (m, 5H), 2.93-2.85 (m, 1H), 2.08-2.02 (m, 3H), 1.86 (br d, J=3.0 Hz, 3H). LCMS Rt=0.948 min, m/z=634.2 [M+H]⁺.

LCMS (5 to 95% acetonitrile in water+0.1% ammonium bicarbonate over 6 mins) retention time 0.948 min, ESI+ found [M+H]=634.2.

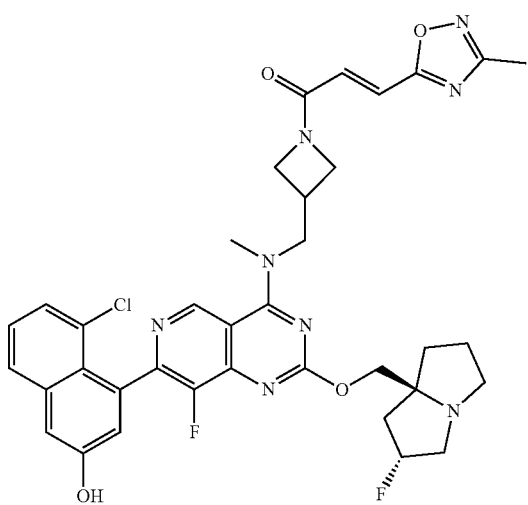 [SMILES: Cc1noc(/C=C/C(=O)N2CC(CN(C)c3nc(OC[C@@]45CCCN4C[C@H](F)C5)nc4c(F)c(-c5cc(O)cc6cccc(Cl)c56)ncc34)C2)n1]

Example 98 (Method 3): (E)-1-(3-(((7-(8-chloro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-methyl-1,2,4-oxadiazol-5-yl)prop-2-en-1-one Step 1: (E)-1-(3-(((7-(8-chloro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-methyl-1,2,4-oxadiazol-5-yl)prop-2-en-1-one The amide coupling reaction was prepared in a similar fashion to Method #3, Step 8. The crude was purified by reverse phase HPLC (column: Phenomenex Luna C18 75*30 mm*3 μm; mobile phase: [water (formic acid)-acetonitrile]; B %: 20%-60%, 8 min) affording (E)-1-(3-(((7-(8-chloro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-methyl-1,2,4-oxadiazol-5-yl)prop-2-en-1-one (4.27 mg, 5.91%, formate salt) as a white amorphous solid: ¹H NMR (400 MHz, Acetonitrile-d3) δ 9.22 (s, 1H), 7.82-7.77 (m, 1H), 7.59-7.31 (m, 4H), 7.29-7.12 (m, 2H), 5.35-5.11 (m, 1H), 4.46 (br t, J=8.5 Hz, 1H), 4.33-3.95 (m, 6H), 3.95-3.89 (m, 1H), 3.58 (s, 3H), 3.12 (br s, 3H), 3.04 (br d, J=7.9 Hz, 1H), 2.92-2.82 (m, 1H), 2.41-2.35 (m, 3H), 2.02 (br d, J=8.3 Hz, 2H), 1.92-1.72 (m, 4H). LCMS Rt=2.823 min, m/z=716.2 [M+H]⁺.

LCMS (5 to 95% acetonitrile in water+0.1% trifluoroacetic acid over 6 mins) retention time 2.823 min, ESI+ found [M+H]=716.2

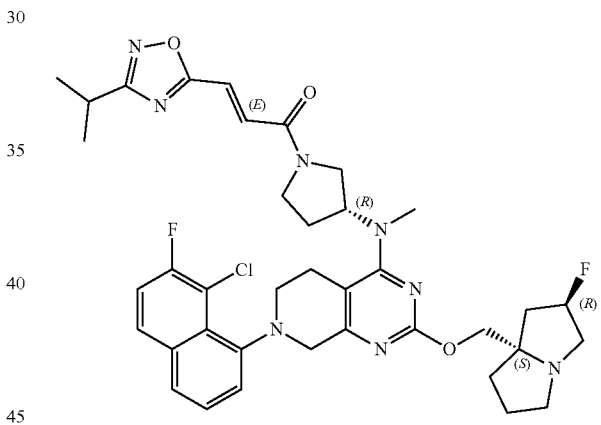

Example 99 (Method 4): (E)-1-((R)-3-((7-(8-chloro-7-fluoronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-isopropyl-1,2,4-oxadiazol-5-yl)prop-2-en-1-one

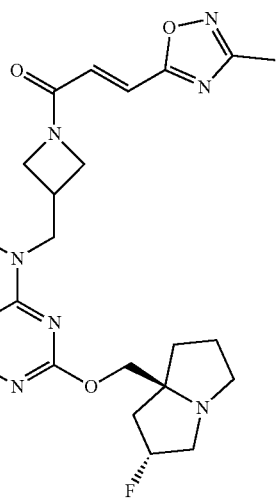

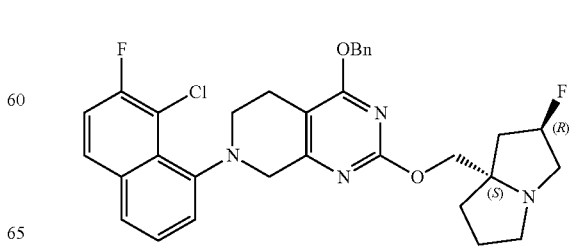

Step 1: 4-(benzyloxy)-7-(8-chloro-7-fluoronaphthalen-1-yl)-2-(((2R,7aS)-2-fluorohexahydro-1H-pyrrolizin-7a-yl)methoxy)-5,6,7,8-tetrahydropyrido[3,4-d]pyrimidine The Buchwald reaction was prepared in a similar fashion to Method #4, Step 6. The mixture was purified by column chromatography (silica gel, 100-200 mesh, 80-100% ethyl acetate in petroleum ether) affording 4-(benzyloxy)-7-(8-chloro-7-fluoronaphthalen-1-yl)-2-(((2R,7aS)-2-fluorohexahydro-1H-pyrrolizin-7a-yl)methoxy)-5,6,7,8-tetrahydropyrido[3,4-d]pyrimidine (530 mg, 21.96%) as a yellow oil. LCMS Rt=1.007 min, m/z=576.2 [M+H]⁺.

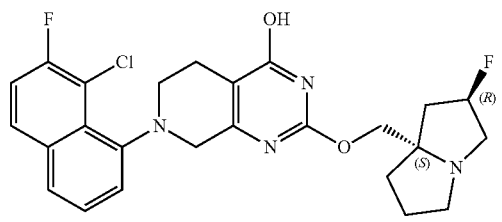

Step 2: 7-(8-chloro-7-fluoronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-ol The hydrogenation reaction was prepared in a similar fashion to Method #4, Step 7.

The reaction mixture was filtered and the filtrate was concentrated in vacuo affording 7-(8-chloro-7-fluoronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-ol (340 mg, crude) as a yellow oil, used in next step without further purification. LCMS Rt=0.776 min, m/z=486.2 [M+H]⁺.

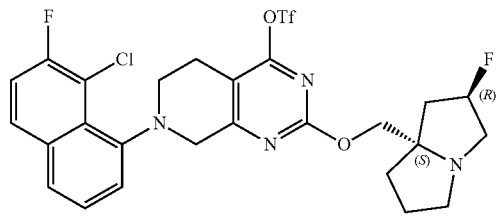

Step 3: 7-(8-chloro-7-fluoronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl trifluoromethanesulfonate The sulfonylation reaction was prepared in a similar fashion to Method #4, Step 8. The mixture was diluted with water (20 mL) and extracted with dichloromethane (3×50 mL). The combined organic layers were dried over sodium sulphate and concentrated in vacuo affording 7-(8-chloro-7-fluoronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl trifluoromethanesulfonate (400 mg, crude) as a yellow oil, used in next step without further purification. LCMS Rt=0.925 min, m/z=618.1 [M+H]⁺.

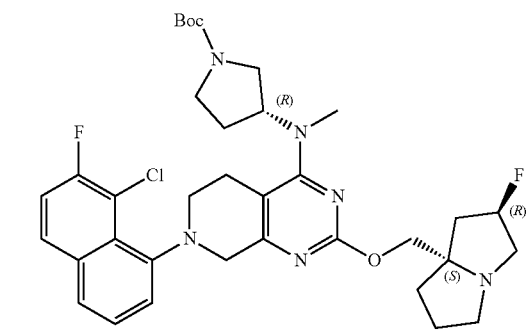

Step 4: (R)-tert-butyl 3-((7-(8-chloro-7-fluoronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidine-1-carboxylate The substitution reaction was prepared in a similar fashion to Method #4, Step 9. The resulting residue was purified by reverse phase HPLC (column: Phenomenex Luna 80*30 mm*3 μm; mobile phase: [water (trifluoroacetic acid)-acetonitrile]; B %: 30%-65%, 8 min) affording (R)-tert-butyl 3-((7-(8-chloro-7-fluoronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidine-1-carboxylate (160 mg, 36.15%, trifluoroacetate salt) as a red oil. LCMS Rt=0.784 min, m/z=668.3 [M+H]⁺.

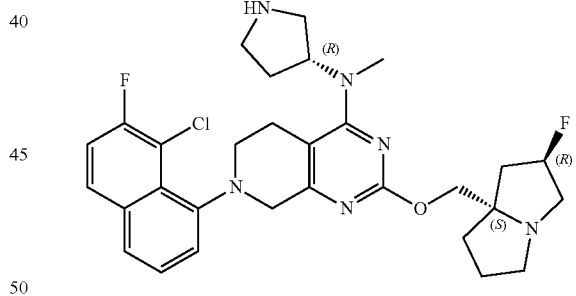

Step 5: 7-(8-chloro-7-fluoronaphthalen-1-yl)-2-(((2R,7aS)-2-fluorohexahydro-1H-pyrrolizin-7a-yl)methoxy)-N-methyl-N—((R)-pyrrolidin-3-yl)-5,6,7,8-tetrahydropyrido[3,4-d]pyrimidin-4-amine The deprotection of Boc reaction was prepared in a similar fashion to Method #1, Step 9. The reaction mixture was concentrated in vacuo affording 7-(8-chloro-7-fluoronaphthalen-1-yl)-2-(((2R,7aS)-2-fluorohexahydro-1H-pyrrolizin-7a-yl)methoxy)-N-methyl-N—((R)-pyrrolidin-3-yl)-5,6,7,8-tetrahydropyrido[3,4-d]pyrimidin-4-amine (80 mg, crude, trifluoroacetic salt) as a yellow oil, used in next step without further purification. LCMS Rt=0.585 min, m/z=568.3 [M+H]⁺.

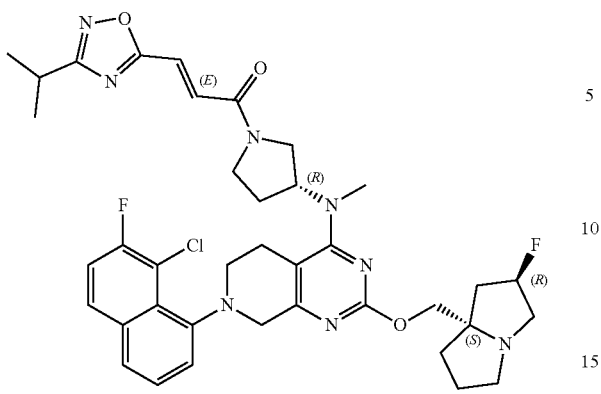

Step 6: (E)-1-((R)-3-((7-(8-chloro-7-fluoronaphtha-len-1-yl)-2-(((2R,7aS)-2-fluorohexahydro-1H-pyr-rolizin-7a-yl)methoxy)-5,6,7,8-tetrahydropyrido[3,4-d]pyrimidin-4-yl)(methyl)amino)pyrrolidin-1-yl)-3-(3-isopropyl-1,2,4-oxadiazol-5-yl)prop-2-en-1-one The amide coupling reaction was prepared in a similar fashion to Method #4, Step 11. The crude product was purified by reverse phase prep-HPLC (column: Waters Xbridge Prep OBD C18 150*40 mm*10 μm; mobile phase: [water (NH₄HCO₃)-acetonitrile]; B %: 35%-65%, 8 min) affording (E)-1-((R)-3-((7-(8-chloro-7-fluoronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-isopropyl-1,2,4-oxadiazol-5-yl)prop-2-en-1-one (23.48 mg, 22.71%) as a yellow solid: $^1$H NMR (400 MHz, Acetonitrile-d3) δ 7.94-7.89 (m, 1H), 7.72 (br d, J=8.0 Hz, 1H), 7.55-7.32 (m, 5H), 5.35-5.13 (m, 1H), 4.91-4.75 (m, 1H), 4.30-4.21 (m, 1H), 4.20-4.05 (m, 1H), 4.05-3.98 (m, 1H), 3.98-3.92 (m, 1H), 3.90-3.78 (m, 1H), 3.77-3.63 (m, 2H), 3.58-3.41 (m, 2H), 3.34-3.22 (m, 1H), 3.20-3.08 (m, 4H), 3.07-3.03 (m, 1H), 3.02 (s, 1H), 3.00 (s, 2H), 2.94-2.83 (m, 1H), 2.69-2.58 (m, 1H), 2.43-2.22 (m, 2H), 2.10-2.05 (m, 1H), 2.05-1.98 (m, 2H), 1.94-1.75 (m, 3H), 1.42-1.28 (m, 6H). LCMS Rt=3.572 min, m/z=732.3 [M+H]⁺.

LCMS (5 to 95% acetonitrile in water+0.1% trifluoroacetic acid over 6 mins) retention time 3.572 min, ESI+ found [M+H]=732.3.

Example 100 (Method 2): (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-(trifluoromethyl)-1,2,4-oxadiazol-5-yl)prop-2-en-1-one

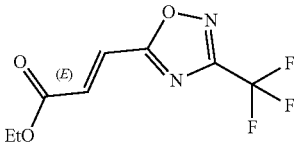 [SMILES: CCOC(=O)/C=C/c1nc(C(F)(F)F)no1]

Step 1: (E)-ethyl 3-(3-(trifluoromethyl)-1,2,4-oxadiazol-5-yl)acrylate

The cyclization reaction was prepared in a similar fashion to Method #1, Step 3. The resulting residue was purified by column chromatography (silica gel, 100-200 mesh, 50-100% ethyl acetate in petroleum ether) affording (E)-ethyl 3-(3-(trifluoromethyl)-1,2,4-oxadiazol-5-yl)acrylate (700 mg, 37.96%) as a yellow oil: $^1$H NMR (400 MHz, Chloroform-d) δ 7.46 (d, J=16.1 Hz, 1H), 7.09 (d, J=16.1 Hz, 1H), 4.27 (q, J=7.1 Hz, 2H), 1.29 (t, J=7.1 Hz, 3H).

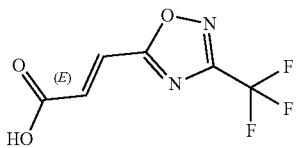 [SMILES: O=C(O)/C=C/c1nc(C(F)(F)F)no1]

Step 2: (E)-3-(3-(trifluoromethyl)-1,2,4-oxadiazol-5-yl)acrylic acid

The hydrolysis reaction was prepared in a similar fashion to Method #1, Step 4. The reaction mixture was quenched with hydrochloric acid (1M, 1 mL) and adjusted pH to 2, then extracted with dichloromethane (3×10 mL). The combined organic layers were dried over sodium sulphate and concentrated in vacuo affording (E)-3-(3-(trifluoromethyl)-1,2,4-oxadiazol-5-yl)acrylic acid (500 mg, crude) as a yellow oil, used in next step without any further purification. LCMS Rt=0.449 min, m/z=208.0 [M+H]⁺.

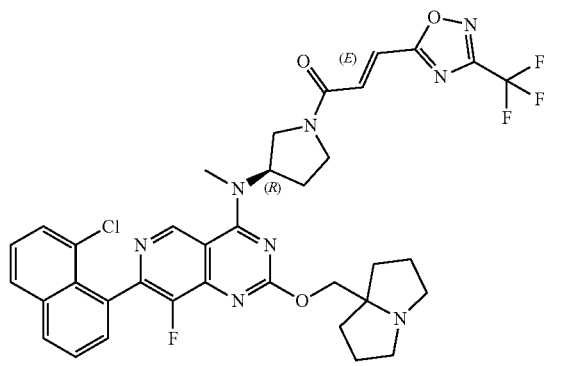

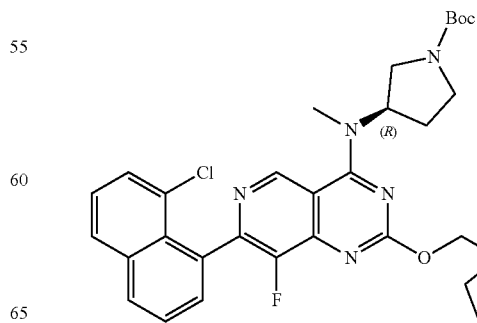

Step 3: (R)-tert-butyl 3-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidine-1-carboxylate The Suzuki reaction was prepared in a similar fashion to Method #2, Step 5. The crude was purified by column chromatography (silica gel, 100-200 mesh, 80-100% methanol in dichloromethane) affording (R)-tert-butyl 3-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidine-1-carboxylate (840 mg, 46.21%) as a yellow oil. LCMS Rt=0.725 min, m/z=646.3 [M+H]$^+$.

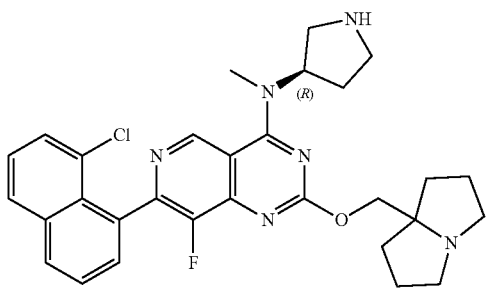

Step 4: (R)-7-(8-chloronaphthalen-1-yl)-8-fluoro-2-((hexahydro-1H-pyrrolizin-7a-yl)methoxy)-N-methyl-N-(pyrrolidin-3-yl)pyrido[4,3-d]pyrimidin-4-amine The deprotection of Boc reaction was prepared in a similar fashion to Method #1, Step 9. The reaction mixture was concentrated in vacuo affording (R)-7-(8-chloronaphthalen-1-yl)-8-fluoro-2-((hexahydro-1H-pyrrolizin-7a-yl)methoxy)-N-methyl-N-(pyrrolidin-3-yl)pyrido[4,3-d]pyrimidin-4-amine (90 mg, crude, trifluoroacetic salt) as a brown solid, used in next step without further purification. LCMS Rt=0.568 min, m/z=546.2 [M+H]$^+$.

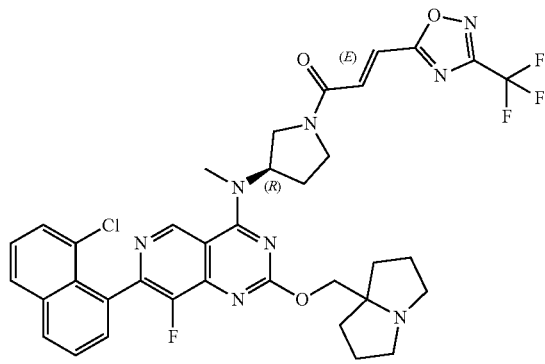

Step 5: (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-(trifluoromethyl)-1,2,4-oxadiazol-5-yl)prop-2-en-1-one The amide coupling reaction was prepared in a similar fashion to Method #2, Step 7. The crude product was purified by reverse phase prep-HPLC (column: Waters Xbridge Prep OBD C18 150*40 mm*10 um; mobile phase: [water (NH$_4$HCO$_3$)-acetonitrile]; B %: 45%-75%, 8 min) affording (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-(trifluoromethyl)-1,2,4-oxadiazol-5-yl)prop-2-en-1-one (46.25 mg, 40.47%) as a yellow amorphous solid: 1H NMR (400 MHz, Acetonitrile-d3) δ 9.24-9.17 (m, 1H), 8.12 (d, J=8.0 Hz, 1H), 8.04-7.99 (m, 1H), 7.73-7.57 (m, 4H), 7.57-7.43 (m, 2H), 5.51-5.30 (m, 1H), 4.36-4.18 (m, 2H), 4.09-3.97 (m, 1H), 3.93-3.85 (m, 1H), 3.84-3.75 (m, 1H), 3.66-3.51 (m, 1H), 3.48-3.40 (m, 3H), 3.24-3.10 (m, 2H), 2.83-2.68 (m, 2H), 2.48-2.38 (m, 1H), 2.34 (br dd, J=8.4, 15.6 Hz, 1H), 2.09-1.96 (m, 3H), 1.92-1.84 (m, 3H), 1.80-1.67 (m, 2H). LCMS Rt=3.103 min, m/z=736.2 [M+H]$^+$.

LCMS (5 to 95% acetonitrile in water+0.03% ammonium bicarbonate over 6 mins) retention time 3.103 min, ESI+ found [M+H]=736.2.

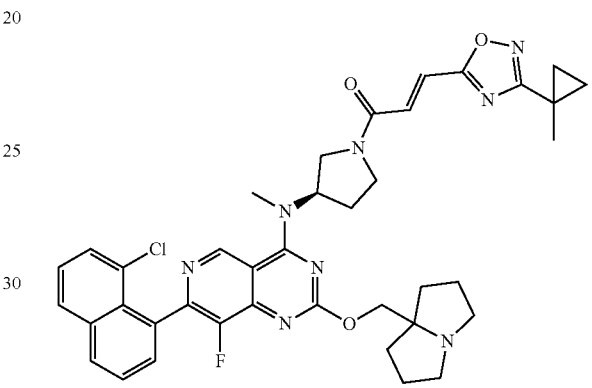

Example 101 (Method 2): (R,E)-1-(3-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidin-1-yl)-3-(3-(1-methylcyclopropyl)-1,2,4-oxadiazol-5-yl)prop-2-en-1-one

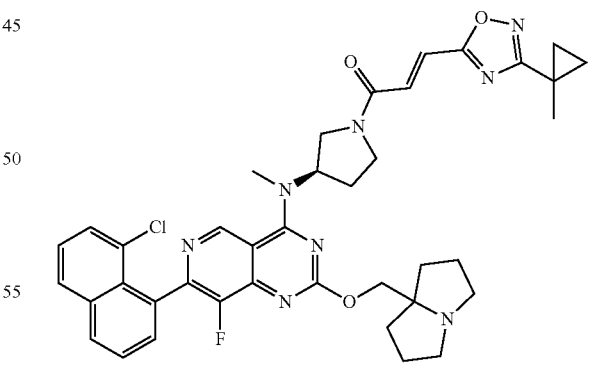

Step 1: (R,E)-1-(3-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidin-1-yl)-3-(3-(1-methylcyclopropyl)-1,2,4-oxadiazol-5-yl)prop-2-en-1-one The amide coupling reaction was prepared in a similar fashion to Method #2, Step 7. The crude product was purified by reverse phase prep-HPLC (column: Phenomenex Luna C18 75*30 mm*3 μm; mobile phase: [water (formic acid)-acetonitrile]; B %: 10%-40%, 8 min) affording (R,E)-1-(3-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidin-1-yl)-3-(3-(1-methylcyclopropyl)-1,2,4-oxadiazol-5-yl)prop-2-en-1-one (11.87 mg, 10.40%, formate salt) as a white solid: $^1$H NMR (400 MHz, Acetonitrile-d3) δ 9.23 (s, 1H), 8.35 (s, 1H), 8.15 (d, J=8.1 Hz, 1H), 8.04 (d, J=8.1 Hz, 1H), 7.74-7.69 (m, 1H), 7.68-7.61 (m, 2H), 7.57-7.51 (m, 1H), 7.48-7.40 (m, 1H), 7.37-7.29 (m, 1H), 5.43 (td, J=7.7, 15.0 Hz, 1H), 4.36 (s, 1H), 4.28-4.15 (m, 1H), 4.06-3.98 (m, 1H), 3.95-3.84 (m, 1H), 3.82-3.73 (m, 1H), 3.69-3.54 (m, 1H), 3.47 (s, 3H), 3.28-3.20 (m, 2H), 2.81-2.72 (m, 2H), 2.48-2.31 (m, 2H), 2.13-2.03 (m, 2H), 1.96-1.86 (m, 4H), 1.84-1.73 (m, 2H), 1.51 (d, J=8.0 Hz, 3H), 1.25-1.16 (m, 2H), 0.98-0.89 (m, 2H). LCMS Rt=2.330 min, m/z=722.3 [M+H]$^+$.

LCMS (5 to 95% acetonitrile in water+0.1% formate acid over 6 mins) retention time 2.330 min, ESI+ found [M+H]=722.3

Step 1: tert-butyl 2-((E)-3-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-en-1-yl)pyrrolidine-1-carboxylate The Horner-Wadsworth-Emmons reaction was prepared in a similar fashion to Method #8, Step 4. The reaction mixture was concentrated in vacuo affording tert-butyl 2-((E)-3-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-en-1-yl)pyrrolidine-1-carboxylate (130 mg, crude) as a white solid, used in next step without any further purification. LCMS Rt=0.617 min, m/z=805.3 [M+H]$^+$.

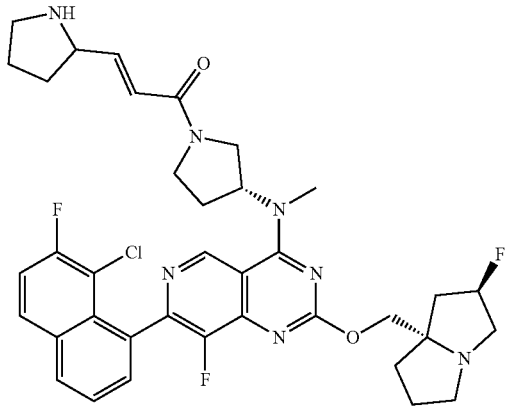 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)/C=C/C2CCCN2)C1]

Example 102 (Method 8): (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(pyrrolidin-2-yl)prop-2-en-1-one

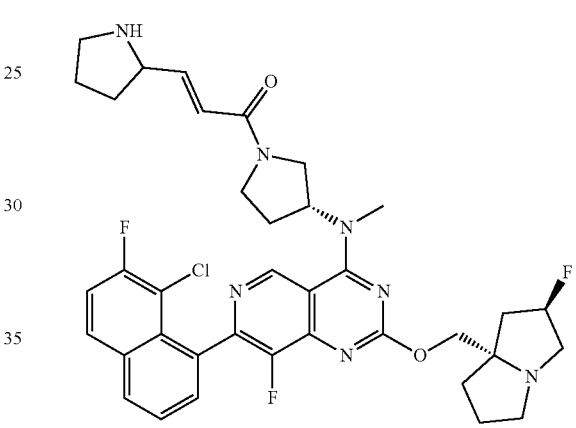

Step 2: (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(pyrrolidin-2-yl)prop-2-en-1-one The deprotection of Boc group was prepared in a similar fashion to Method #8, Step 5. The residue was purified by reverse phase HPLC(column: Phenomenex Luna C18 75*30 mm*3 μm; mobile phase: [water (formic acid)-acetonitrile]; B %: 10%-40%, 8 min) affording (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(pyrrolidin-2-yl)prop-2-en-1-one (19.06 mg, 32.23%, formate salt) as a yellow oil: $^1$H NMR (400 MHz, Acetonitrile-d3) δ 9.26-9.15 (m, 1H), 8.50-8.27 (m, 1H), 8.14 (br d, J=3.6 Hz, 1H), 8.07 (br dd, J=5.7, 8.9 Hz, 1H), 7.73-7.62 (m, 2H), 7.53 (br t, J=8.9 Hz, 1H), 6.90-6.77 (m, 1H), 6.64-6.53 (m, 1H), 5.46-5.21 (m, 2H), 4.38-4.21 (m, 2H), 4.19-4.06 (m, 1H), 4.04-3.76 (m, 2H), 3.67-3.51 (m, 2H), 3.48-3.40 (m, 4H), 3.35-3.17 (m, 4H), 3.10-2.92 (m, 1H), 2.43-2.25 (m, 4H), 2.23-2.00 (m, 5H), 1.95-1.71 (m, 3H). LCMS Rt=1.974 min, m/z=705.3 [M+H]$^+$.

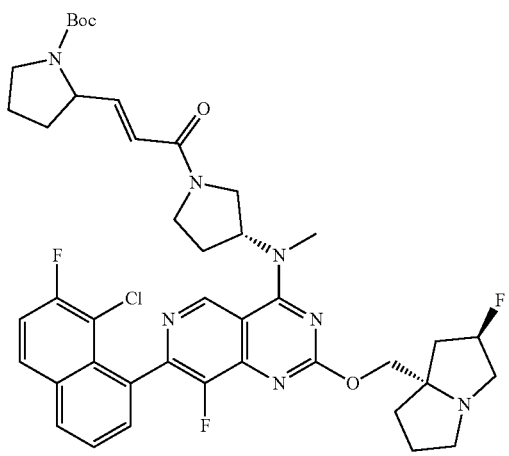 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)/C=C/C2CCCN2C(=O)OC(C)(C)C)C1]

LCMS (5 to 95% acetonitrile in water+0.1% trifluoroacetic acid over 6 mins) retention time 1.974 min, ESI+ found [M+H]=705.3.

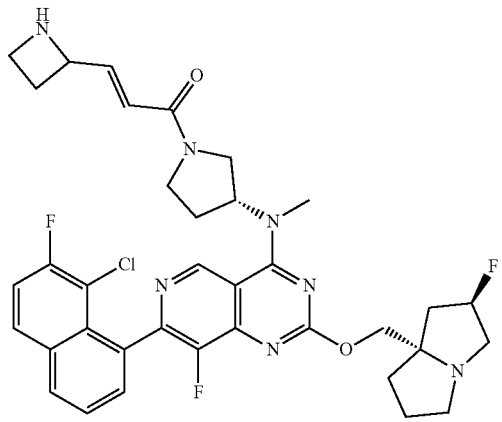

Example 103 (Method 8): (E)-3-(azetidin-2-yl)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one

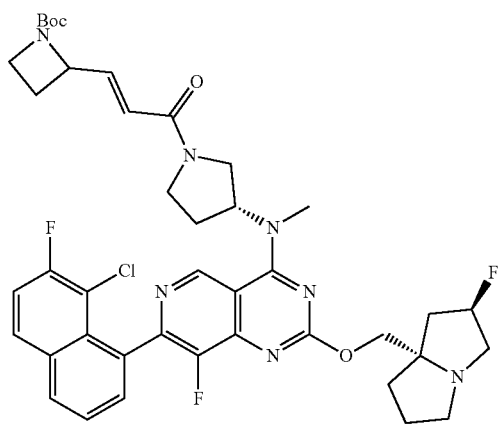 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)/C=C/C2CCN2C(=O)OC(C)(C)C)C1]

Step 1: tert-butyl 2-((E)-3-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-en-1-yl)azetidine-1-carboxylate The Horner-Wadsworth-Emmons reaction was prepared in a similar fashion to Method #8, Step 4. The combined organic layers were concentrated under vacuo affording tert-butyl 2-((E)-3-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-en-1-yl)azetidine-1-carboxylate (100 mg, crude) as a yellow oil. LCMS Rt=0.858 min, m/z=791.3 [M+H]$^+$.

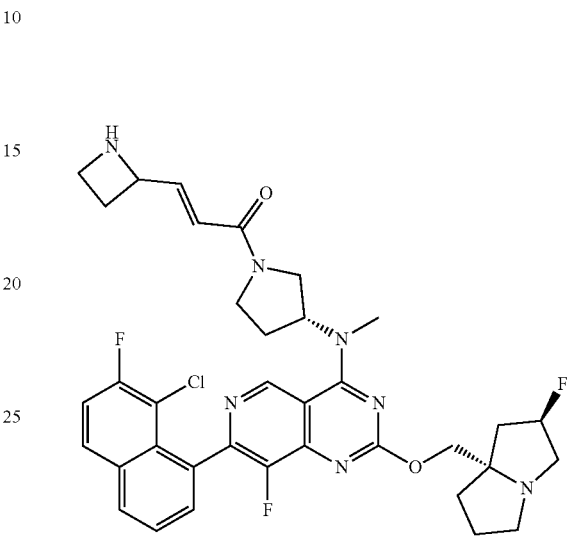

Step 2: (E)-3-(azetidin-2-yl)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one The deprotection of Boc group was prepared in a similar fashion to Method #8, Step 5. The residue was purified by reverse phase HPLC (column: Waters Xbridge Prep OBD C18 150*40 mm*10 um; mobile phase: [water (NH$_4$HCO$_3$)-acetonitrile]; B %: 30%-60%, 8 min) affording (E)-3-(azetidin-2-yl)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (10.72 mg, 24.54%) as a yellow amorphous solid: $^1$H NMR (400 MHz, Acetonitrile-d3) δ 9.20 (s, 1H), 8.18-8.03 (m, 2H), 7.76-7.62 (m, 2H), 7.53 (t, J=8.9 Hz, 1H), 6.90 (ddd, J=2.9, 5.4, 15.0 Hz, 1H), 6.40 (dd, J=10.3, 14.9 Hz, 1H), 5.47-5.18 (m, 2H), 4.49 (quin, J=6.9 Hz, 1H), 4.26-4.10 (m, 2H), 4.08-3.77 (m, 2H), 3.74-3.47 (m, 3H), 3.46-3.42 (m, 3H), 3.30-3.20 (m, 1H), 3.19-3.11 (m, 2H), 3.07 (s, 1H), 2.95-2.85 (m, 1H), 2.48-2.34 (m, 2H), 2.33-2.26 (m, 1H), 2.19 (br d, J=4.4 Hz, 3H), 2.11 (br d, J=3.0 Hz, 2H), 1.91-1.84 (m, 2H). LCMS Rt=2.767 min, m/z=691.3 [M+H]$^+$.

LCMS (5 to 95% acetonitrile in water+0.03% ammonium bicarbonate over 6 mins) retention time 2.767 min, ESI+ found [M+H]=691.3.

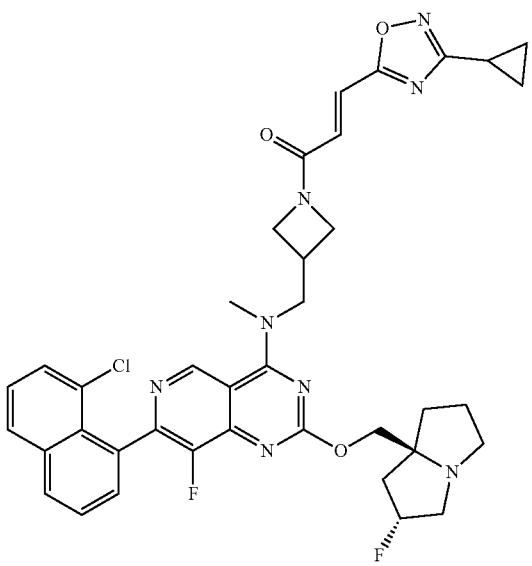 [SMILES: CN(CC1CN(C(=O)/C=C/c2nc(C3CC3)no2)C1)c1nc(OC[C@@]23CCCN2C[C@H](F)C3)nc2c(F)c(-c3cccc4cccc(Cl)c34)ncc12]

Example 104 (Method 1): (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-cyclopropyl-1,2,4-oxadiazol-5-yl)prop-2-en-1-one

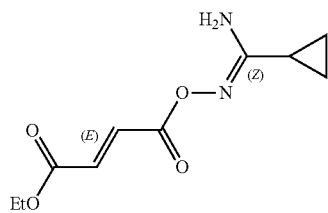 [SMILES: CCOC(=O)/C=C/C(=O)O/N=C(\N)C1CC1]

Step 1: (E)-ethyl 4-(((Z)-(amino(cyclopropyl)methylene)amino)oxy)-4-oxobut-2-enoate The amide coupling reaction was prepared in a similar fashion to Method #1, Step 2. The reaction mixture was concentrated in vacuo affording (E)-ethyl 4-(((Z)-(amino(cyclopropyl)methylene)amino)oxy)-4-oxobut-2-enoate (9 g, crude) as a brown oil, used in next step without further purification. LCMS Rt=0.539 min, m/z=226.1 [M+H]⁺.

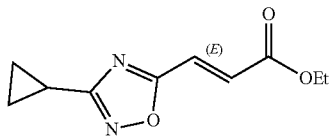 [SMILES: CCOC(=O)/C=C/c1nc(C2CC2)no1]

Step 2: (E)-ethyl 3-(3-cyclopropyl-1,2,4-oxadiazol-5-yl)acrylate

The cyclization reaction was prepared in a similar fashion to Method #1, Step 3.

The resulting residue was purified by column chromatography (silica gel, 100-200 mesh, 20% ethyl acetate in petroleum ether) affording (E)-ethyl 3-(3-cyclopropyl-1,2,4-oxadiazol-5-yl)acrylate (5.6 g, 67.61%) as a yellow oil. LCMS Rt=0.709 min, m/z=208.1 [M+H]⁺.

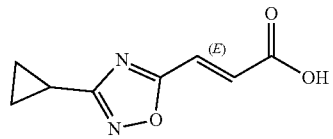 [SMILES: O=C(O)/C=C/c1nc(C2CC2)no1]

Step 3: (E)-3-(3-cyclopropyl-1,2,4-oxadiazol-5-yl)acrylic acid

The hydrolysis reaction was prepared in a similar fashion to Method #1, Step 4.

The reaction mixture was concentrated in vacuo affording (E)-3-(3-cyclopropyl-1,2,4-oxadiazol-5-yl)prop-2-enoic acid (1.5 g, crude) as a white solid, used in next step without further purification: $^1$H NMR (400 MHz, Chloroform-d) δ 7.51 (d, J=16.1 Hz, 1H), 6.98 (d, J=16.1 Hz, 1H), 2.19-2.14 (m, 1H), 1.14-1.04 (m, 4H).

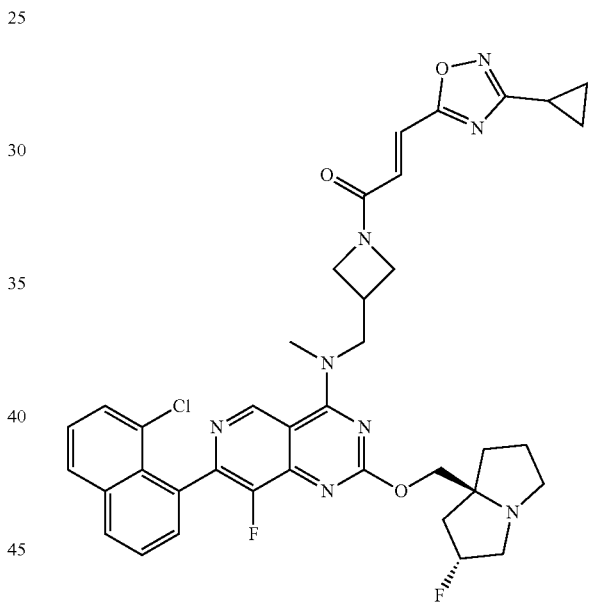

Step 4: (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-cyclopropyl-1,2,4-oxadiazol-5-yl)prop-2-en-1-one The amide coupling reaction was prepared in a similar fashion to Method #1, Step 10. The crude was purified by reverse phase HPLC (column: Waters Xbridge Prep OBD C18 150*40 mm*10 μm; mobile phase: [water (NH₄HCO₃)-acetonitrile]; B %: 35%-65%, 8 min) affording (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-cyclopropyl-1,2,4-oxadiazol-5-yl)prop-2-en-1-one (32.23 mg, 14.80%) as a yellow solid: $^1$H NMR (400 MHz, Acetonitrile-d3) δ 9.27 (s, 1H), 8.15 (d, J=8.4 Hz, 1H), 8.05 (d, J=8.1 Hz, 1H), 7.74-7.69 (m, 1H), 7.64 (br d, J=7.0 Hz, 2H), 7.57-7.51 (m, 1H), 7.31-7.26 (m, 1H), 7.17-7.11 (m, 1H), 5.36-5.18 (m, 1H), 4.48 (t, J=8.8 Hz, 1H), 4.31-4.11 (m, 6H), 4.00-3.91 (m, 1H), 3.61 (s, 3H), 3.30-3.22 (m, 1H), 3.15 (br s, 1H), 3.11-3.07 (m, 1H), 2.95-2.87 (m, 1H), 2.14-2.11 (m, 3H), 2.08-2.04 (m, 1H), 1.92-1.84 (m, 3H), 1.33-1.19 (m, 1H), 1.11 (dd, J=2.8, 8.3 Hz, 2H), 1.01-0.97 (m, 2H). LCMS Rt=3.139 min, m/z=726.3 [M+H]⁺.

LCMS (5 to 95% acetonitrile in water+0.1% ammonium bicarbonate over 6 mins) retention time 3.139 min, ESI+ found [M+H]=726.3

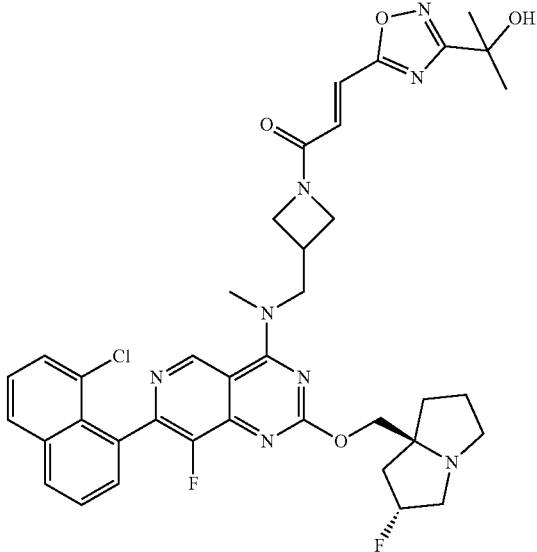 [SMILES: CN(CC1CN(C(=O)/C=C/c2nc(C(C)(C)O)no2)C1)c1nc(OC[C@@]23CCCN2C[C@H](F)C3)nc2c(F)c(-c3cccc4cccc(Cl)c34)ncc12]

Example 105 (Method 1): (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-(2-hydroxypropan-2-yl)-1,2,4-oxadiazol-5-yl)prop-2-en-1-one Step 1: (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-(2-hydroxypropan-2-yl)-1,2,4-oxadiazol-5-yl)prop-2-en-1-one The amide coupling reaction was prepared in a similar fashion to Method #1, Step 10. The residue was purified by reverse phase HPLC(column: Waters Xbridge Prep OBD C18 150*40 mm*10 um; mobile phase: [water (NH₄HCO₃)-acetonitrile]; B %: 30%-55%, 8 min) affording (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-(2-hydroxypropan-2-yl)-1,2,4-oxadiazol-5-yl)prop-2-en-1-one (33.47 mg, 9.99%) as a yellow amorphous solid: ¹H NMR (400 MHz, Acetonitrile-d3) δ 9.24 (s, 1H), 8.12 (d, J=8.2 Hz, 1H), 8.04-7.99 (m, 1H), 7.73-7.66 (m, 1H), 7.61 (br d, J=7.5 Hz, 2H), 7.54-7.47 (m, 1H), 7.34-7.28 (m, 1H), 7.20-7.14 (m, 1H), 5.34-5.14 (m, 1H), 4.51-4.43 (m, 1H), 4.32-4.21 (m, 2H), 4.20-4.16 (m, 2H), 4.15-4.05 (m, 2H), 3.98-3.89 (m, 1H), 3.58 (s, 3H), 3.29-3.18 (m, 1H), 3.17-3.04 (m, 3H), 2.91-2.83 (m, 1H), 2.13-2.10 (m, 2H), 2.08 (br s, 1H), 2.05-1.97 (m, 2H), 1.84 (br d, J=3.3 Hz, 2H), 1.57 (s, 6H). LCMS Rt=2.905 min, m/z=744.3 [M+H]⁺.

LCMS (5 to 95% acetonitrile in water+0.03% ammonium bicarbonate over 6 mins) retention time 2.905 min, ESI+ found [M+H]=744.3.

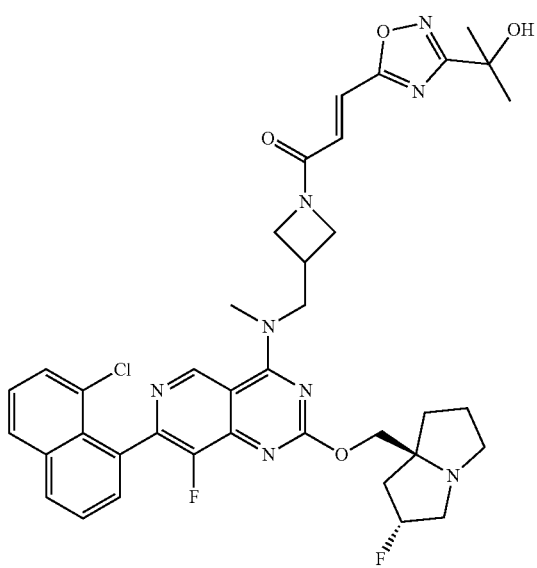 [SMILES: CN(CC1CN(C(=O)/C=C/c2nc(C(C)(C)O)no2)C1)c1nc(OC[C@@]23CCCN2C[C@H](F)C3)nc2c(F)c(-c3cccc4cccc(Cl)c34)ncc12]

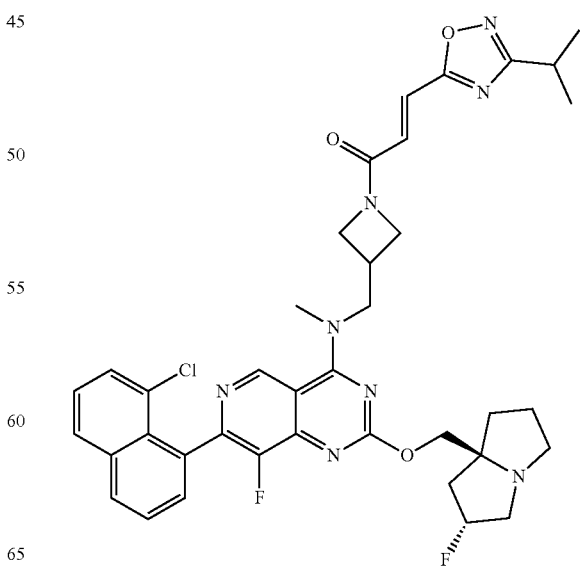

Example 106 (Method 1): (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-isopropyl-1,2,4-oxadiazol-5-yl)prop-2-en-1-one

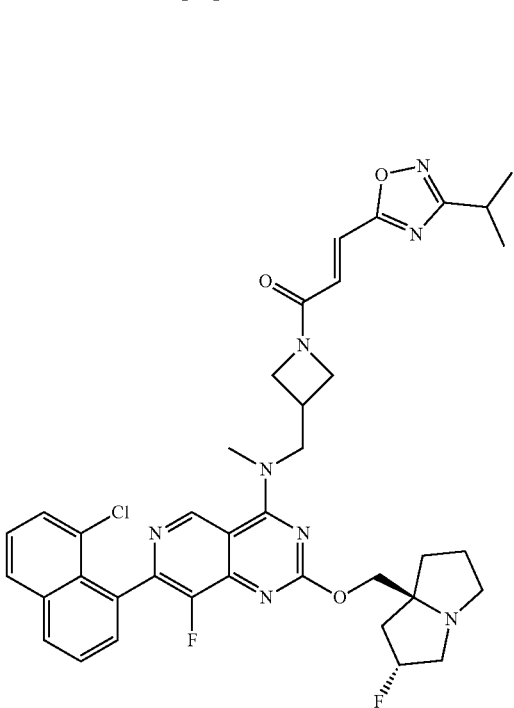

Step 1: (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-isopropyl-1,2,4-oxadiazol-5-yl)prop-2-en-1-one The amide coupling reaction was prepared in a similar fashion to Method #1, Step 10. The residue was purified by reverse phase HPLC(column: Waters Xbridge Prep OBD C18 150*40 mm*10 μm; mobile phase: [water (NH₄HCO₃)-acetonitrile]; B %: 35%-65%, 8 min) affording (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-isopropyl-1,2,4-oxadiazol-5-yl)prop-2-en-1-one (43.24 mg, 19.89%) as a yellow solid: ¹H NMR (400 MHz, Acetonitrile-d3) δ 9.28 (s, 1H), 8.16 (d, J=8.3 Hz, 1H), 8.06 (d, J=7.6 Hz, 1H), 7.76-7.70 (m, 1H), 7.65 (br d, J=7.5 Hz, 2H), 7.58-7.52 (m, 1H), 7.35 (d, J=15.8 Hz, 1H), 7.22-7.16 (m, 1H), 5.37-5.19 (m, 1H), 4.51 (t, J=8.6 Hz, 1H), 4.34-4.15 (m, 6H), 4.01-3.94 (m, 1H), 3.63 (s, 3H), 3.30-3.24 (m, 1H), 3.16 (br d, J=7.1 Hz, 2H), 3.09 (br s, 1H), 2.95-2.89 (m, 1H), 2.15 (br d, J=2.3 Hz, 1H), 2.11 (br s, 1H), 2.07 (br d, J=1.6 Hz, 1H), 2.05 (br dd, J=1.9, 4.8 Hz, 1H), 1.92-1.84 (m, 3H), 1.35 (d, J=6.8 Hz, 6H). LCMS Rt=3.208 min, m/z =728.3 [M+H]⁺.

LCMS (5 to 95% acetonitrile in water+0.03% ammonium bicarbonate over 6 mins) retention time 3.208 min, ESI+ found [M+H]=728.3.

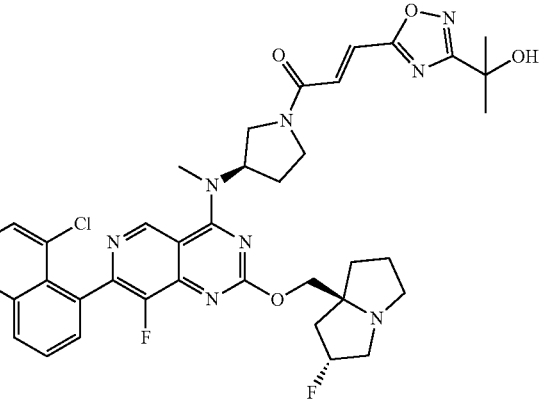

Example 107 (Method 1): (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-(2-hydroxypropan-2-yl)-1,2,4-oxadiazol-5-yl)prop-2-en-1-one

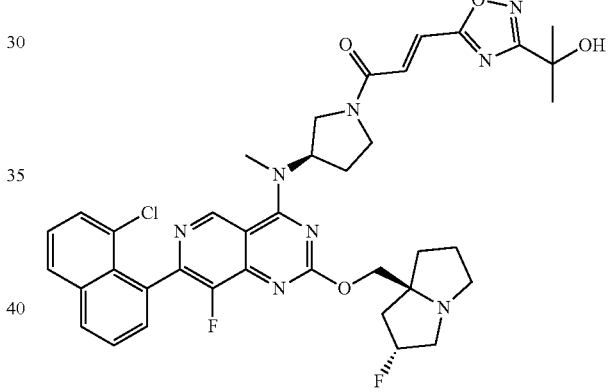

Step 1: (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-(2-hydroxypropan-2-yl)-1,2,4-oxadiazol-5-yl)prop-2-en-1-one The amide coupling reaction was prepared in a similar fashion to Method #1, Step 10. The crude was purified by reverse phase HPLC (column: Waters Xbridge Prep OBD C18 150*40 mm*10 um; mobile phase: [water (NH₄HCO₃)-acetonitrile]; B %: 30%-60%, 8 min) affording (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-(2-hydroxypropan-2-yl)-1,2,4-oxadiazol-5-yl)prop-2-en-1-one (15.78 mg, 14.98%) as a yellow amorphous solid: ¹H NMR (400 MHz, Acetonitrile-d3) δ 9.19 (t, J=1.8 Hz, 1H), 8.12 (dd, J=1.0, 8.1 Hz, 1H), 8.02 (d, J=7.4 Hz, 1H), 7.71-7.66 (m, 1H), 7.65-7.59 (m, 2H), 7.54-7.35 (m, 3H), 5.46-5.15 (m, 2H), 4.23-4.11 (m, 2H), 4.07-3.97 (m, 1H), 3.88-3.76 (m, 1H), 3.67-3.48 (m, 2H), 3.44 (s, 3H), 3.14-

3.05 (m, 2H), 2.92-2.83 (m, 1H), 2.47-2.38 (m, 1H), 2.36-2.28 (m, 1H), 2.11-1.99 (m, 4H), 1.92-1.74 (m, 4H), 1.58 (d, J=7.6 Hz, 6H). LCMS Rt=2.799 min, m/z =744.3 [M+H]⁺.

LCMS (5 to 95% acetonitrile in water+0.03% ammonium bicarbonate over 6 mins) retention time 2.799 min. ESI+ found [M+H]=744.3.

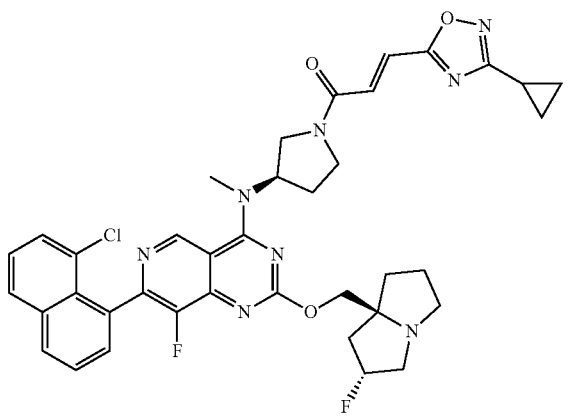 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2nc(C3CC3)no2)C1]

Example 108 (Method 1): (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-cyclopropyl-1,2,4-oxadiazol-5-yl)prop-2-en-1-one

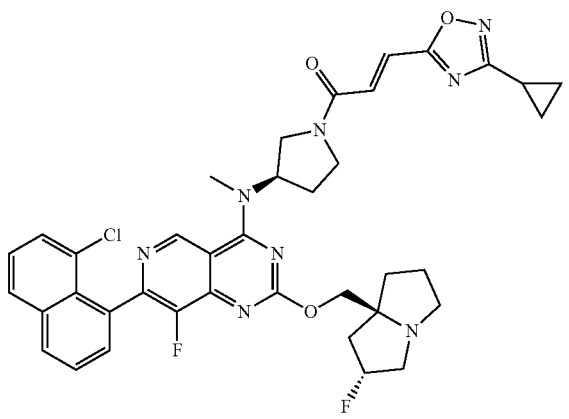 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2nc(C3CC3)no2)C1]

Step 1: (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-cyclopropyl-1,2,4-oxadiazol-5-yl)prop-2-en-1-one The amide coupling reaction was prepared in a similar fashion to Method #1, Step 10. The crude was purified by reverse phase HPLC (column: Waters Xbridge Prep OBD C18 150*40 mm*10 um; mobile phase: [water (NH₄HCO₃)-acetonitrile]; B %: 40%-70%, 8 min) affording (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-cyclopropyl-1,2,4-oxadiazol-5-yl)prop-2-en-1-one (47.77 mg, 45.73%) as a yellow solid: ¹H NMR (400 MHz, Acetonitrile-d3) δ 9.22 (s, 1H), 8.15 (d, J=8.0 Hz, 1H), 8.04 (d, J=8.1 Hz, 1H), 7.75-7.69 (m, 1H), 7.67-7.61 (m, 2H), 7.57-7.51 (m, 1H), 7.49-7.39 (m, 1H), 7.38-7.30 (m, 1H), 5.48-5.36 (m, 1H), 5.35-5.16 (m, 1H), 4.26-4.16 (m, 2H), 4.09-3.98 (m, 1H), 3.97-3.82 (m, 1H), 3.81-3.74 (m, 1H), 3.70-3.50 (m, 1H), 3.46 (s, 3H), 3.22-3.06 (m, 3H), 2.97-2.86 (m, 1H), 2.47-2.32 (m, 2H), 2.15-2.00 (m, 4H), 1.93-1.79 (m, 3H), 1.15-1.07 (m, 2H), 1.04-0.93 (m, 2H). LCMS Rt=2.241 min, m/z=726.3 [M+H]⁺.

LCMS (5 to 95% acetonitrile in water+0.03% ammonium bicarbonate over 6 mins) retention time 2.241 min. ESI+ found [M+H]=726.3.

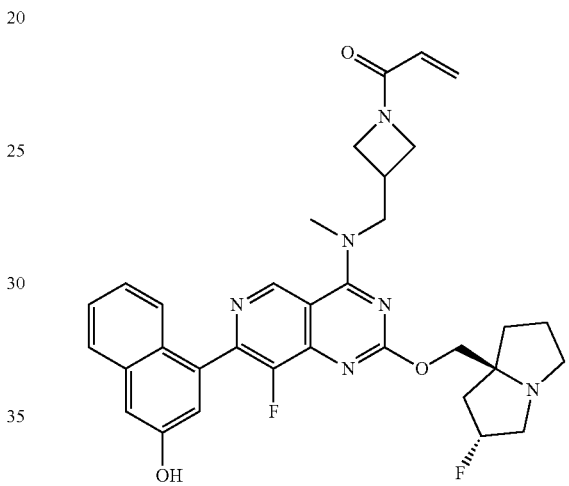

Example 109 (Method 2): 1-(3-(((8-fluoro-2-(((2R,7aS)-2-fluorotetrahydro-1H-pyrrolizin-7a(5H)-yl)methoxy)-7-(3-hydroxynaphthalen-1-yl)pyrido[4,3-d]pyrimidin-4-yl)(methyl)amino)methyl)azetidin-1-yl)prop-2-en-1-one

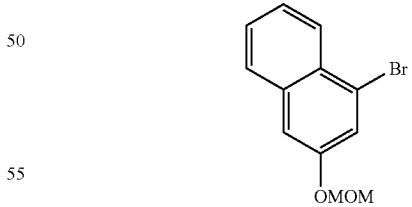

Step 1: 1-bromo-3-(methoxymethoxy)naphthalene

The MOM protection was prepared in a similar fashion to Method #2, Step 1, the residue was purified by column chromatography (silica gel, 100-200 mesh, 0-5% ethyl acetate in petroleum ether) affording 1-bromo-3-(methoxymethoxy)naphthalene (9 g, 93.95%) as a red oil. LCMS Rt=0.913 min, m/z=266.0 [M+H]⁺.

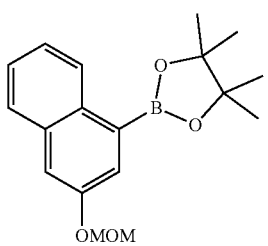

Step 2: 2-(3-(methoxymethoxy)naphthalen-1-yl)-4,4,5,5-tetramethyl-1,3,2-dioxaborolane The borate formation was prepared in a similar fashion to Method #2, Step 2, the residue was purified by reverse phase HPLC (column: Phenomenex C18 250*100 mm 10u; mobile phase: [water (NH4HCO3)-acetonitrile]; B %: 65%-95%, 20 min) affording 2-(3-(methoxymethoxy)naphthalen-1-yl)-4,4,5,5-tetramethyl-1,3,2-dioxaborolane (5 g, 85.02%) as a white solid. LCMS Rt=0.929 min, m/z=314.2 [M+H]+.

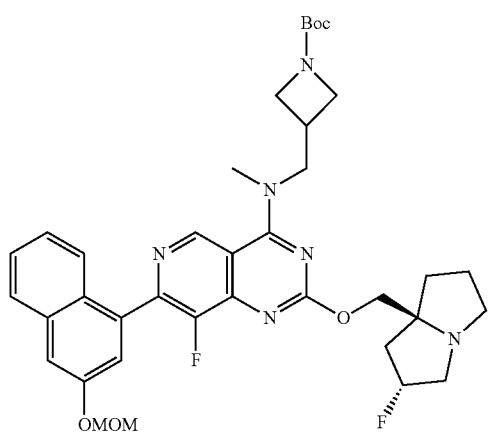

Step 3: tert-butyl 3-(((8-fluoro-2-(((2R,7aS)-2-fluorohexahydro-1H-pyrrolizin-7a-yl)methoxy)-7-(3-(methoxymethoxy)naphthalen-1-yl)pyrido[4,3-d]pyrimidin-4-yl)(methyl)amino)methyl)azetidine-1-carboxylate The Suzuki reaction was prepared in a similar fashion to Method #2, Step 5. The residue was purified by reverse phase HPLC (column: C18-1 150*30 mm*5 μm; mobile phase: [water (trifluoroacetic acid)-acetonitrile]; B %: 20%-65%, 8 min) affording tert-butyl 3-(((8-fluoro-2-(((2R,7aS)-2-fluorohexahydro-1H-pyrrolizin-7a-yl)methoxy)-7-(3-(methoxymethoxy)naphthalen-1-yl)pyrido[4,3-d]pyrimidin-4-yl)(methyl)amino)methyl)azetidine-1-carboxylate (320 mg, 42.86%, trifluoroacetate salt) as a yellow oil. LCMS Rt=0.717 min, m/z=690.3 [M+H]+.

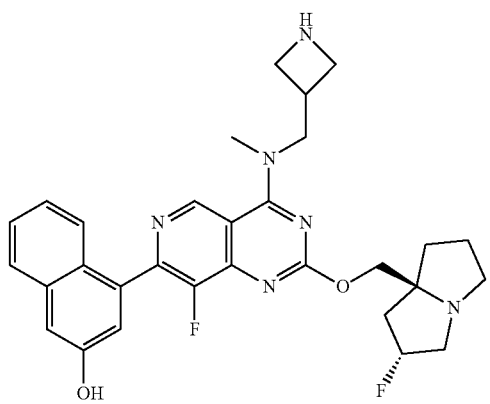 [SMILES: CN(CC1CNC1)c1nc(OC[C@@]23CCCN2C[C@H](F)C3)nc2c(F)c(-c3cc(O)cc4ccccc34)ncc12]

Step 4: 4-(4-((azetidin-3-ylmethyl)(methyl)amino)-8-fluoro-2-(((2R,7aS)-2-fluorohexahydro-1H-pyrrolizin-7a-yl)methoxy)pyrido[4,3-d]pyrimidin-7-yl)naphthalen-2-ol The de-Boc and MOM protecting reaction was prepared in a similar fashion to Method #2, Step 6. The mixture was concentrated in vacuo affording 4-(4-((azetidin-3-ylmethyl)(methyl)amino)-8-fluoro-2-(((2R,7aS)-2-fluorohexahydro-1H-pyrrolizin-7a-yl)methoxy)pyrido[4,3-d]pyrimidin-7-yl)naphthalen-2-ol (80 mg, crude, trifluoroacetate salt) as a yellow oil, used in the next step without further purification. LCMS Rt=0.529 min, m/z=546.3 [M+H]+.

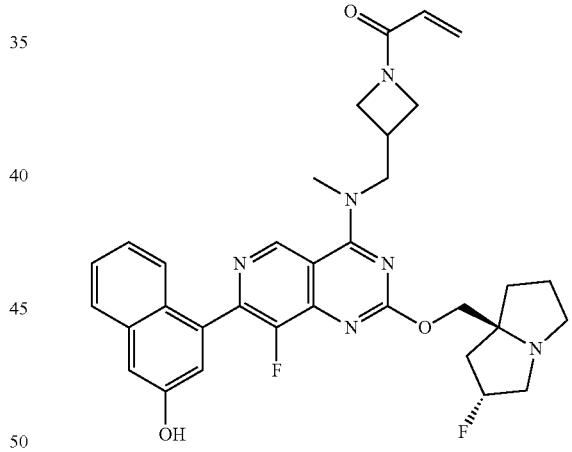

Step 5: 1-(3-(((8-fluoro-2-(((2R,7aS)-2-fluorotetrahydro-1H-pyrrolizin-7a(5H)-yl)methoxy)-7-(3-hydroxynaphthalen-1-yl)pyrido[4,3-d]pyrimidin-4-yl)(methyl)amino)methyl)azetidin-1-yl)prop-2-en-1-one The amide coupling reaction was prepared in a similar fashion to Method #2, Step 7. The residue was purified by reverse phase HPLC (column: Waters Xbridge Prep OBD C18 150*40 mm*10 um; mobile phase: [water (NH4HCO3)-acetonitrile]; B %: 20%-50%, 8 min) affording 1-(3-(((8-fluoro-2-(((2R,7aS)-2-fluorotetrahydro-1H-pyrrolizin-7a(5H)-yl)methoxy)-7-(3-hydroxynaphthalen-1-yl)pyrido[4,3-d]pyrimidin-4-yl)(methyl)amino)methyl)azetidin-1-yl)prop-2-en-1-one (10.32 mg, 12.59%) as a yellow solid: 1H NMR (400 MHz, Acetonitrile-d3) δ 9.34 (s, 1H), 7.84 (d, J=8.3 Hz, 1H), 7.63 (br d, J=7.6 Hz, 1H), 7.52-7.47 (m, 1H), 7.36 (d, J=2.3 Hz, 1H), 7.33-7.28 (m, 2H), 6.39-6.24 (m, 1H), 6.23-6.11 (m, 1H), 5.66 (dd, J=2.4, 10.0 Hz, 1H), 5.43-5.16 (m, 1H), 4.37 (t, J=8.3 Hz, 1H), 4.26-4.08 (m, 6H), 3.89 (br dd, J=5.8, 9.4 Hz, 1H), 3.61 (s, 3H), 3.27-3.14 (m, 4H), 2.28-2.20 (m, 3H), 1.89-1.76 (m, 4H). LCMS Rt=2.669 min, m/z=600.3 [M+H]+.

LCMS (5 to 95% acetonitrile in water+0.03% ammonium bicarbonate over 6 mins) retention time 2.669 min, ESI+ found [M+H]=600.3.

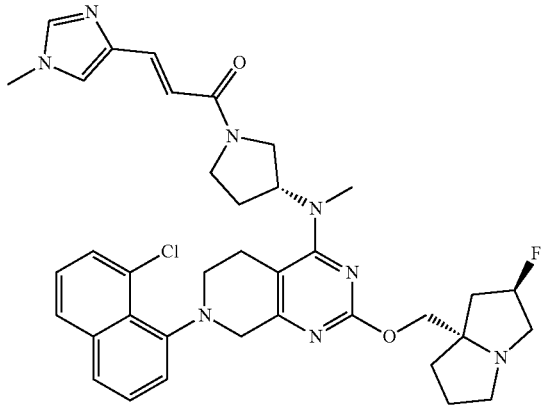 [SMILES: CN(c1nc(OC[C@@]23CCCN2C[C@H](F)C3)nc2c1CCN(c1cccc3cccc(Cl)c13)C2)[C@@H]1CCN(C(=O)/C=C/c2cn(C)cn2)C1]

Example 110 (Method 9): (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(1-methyl-1H-imidazol-4-yl)prop-2-en-1-one

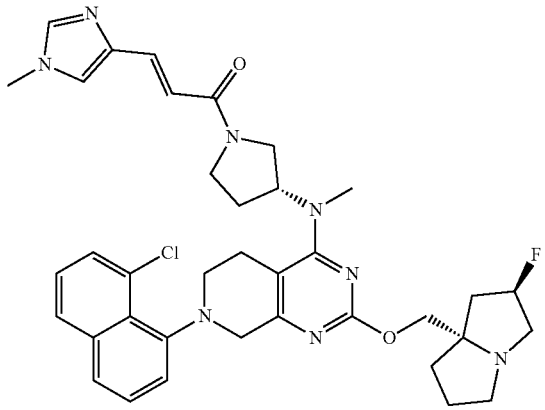 [SMILES: CN(c1nc(OC[C@@]23CCCN2C[C@H](F)C3)nc2c1CCN(c1cccc3cccc(Cl)c13)C2)[C@@H]1CCN(C(=O)/C=C/c2cn(C)cn2)C1]

Step 1: (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(1-methyl-1H-imidazol-4-yl)prop-2-en-1-one The Homer-Wadsworth-Emmons reaction was prepared in a similar fashion to Method #9, Step 9. The crude product was purified by reverse phase prep-HPLC (column: Waters Xbridge Prep OBD C18 150*40 mm*10 μm; mobile phase: [water (NH4HCO3)-acetonitrile]; B %: 40%-70%, 8 min) affording (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(1-methyl-1H-imidazol-4-yl)prop-2-en-1-one (23.62 mg, 22.52%) as a yellow solid: 1H NMR (400 MHz, Acetonitrile-d3) δ 7.87 (d, J=8.1 Hz, 1H), 7.70 (d, J=8.3 Hz, 1H), 7.57 (d, J=7.1 Hz, 1H), 7.52 (dt, J=3.8, 7.8 Hz, 1H), 7.48-7.38 (m, 3H), 7.34 (t, J=6.8 Hz, 1H), 7.23 (br s, 1H), 6.92-6.80 (m, 1H), 5.37-5.11 (m, 1H), 4.90-4.68 (m, 1H), 4.25 (br d, J=17.1 Hz, 1H), 4.13-4.04 (m, 1H), 4.04-3.90 (m, 2H), 3.89-3.70 (m, 2H), 3.67 (d, J=2.0 Hz, 3H), 3.65-3.57 (m, 1H), 3.56-3.48 (m, 1H), 3.47-3.35 (m, 1H), 3.32-3.17 (m, 1H), 3.16-3.03 (m, 4H), 3.02-2.94 (m, 3H), 2.93-2.81 (m, 1H), 2.62 (br d, J=12.8 Hz, 1H), 2.22-2.14 (m, 2H), 2.13-1.99 (m, 3H), 1.92-1.76 (m, 3H). LCMS Rt=2.033 min, m/z=684.3 [M+H]+.

LCMS (5 to 95% acetonitrile in water+0.1% trifluoroacetic acid over 6 mins) retention time 2.033 min, ESI+ found [M+H]=684.3.

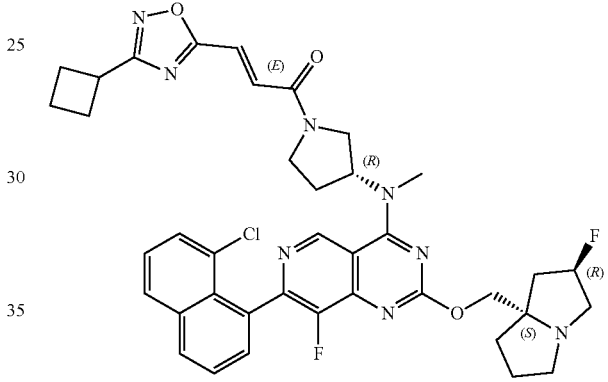

Example 111 (Method 1): (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-cyclobutyl-1,2,4-oxadiazol-5-yl)prop-2-en-1-one

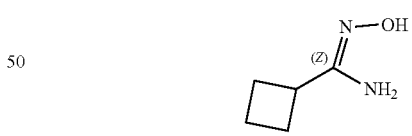

Step 1: (Z)—N'-hydroxycyclobutanecarboximidamide

The hydroxylimidamide formation was prepared in a similar fashion to Method #1, Step 1. The reaction mixture was concentrated to dryness in vacuo affording (Z)—N-hydroxycyclobutanecarboximidamide (5.8 g, crude) as a white oil, used in the next step without any further purification: 1H NMR (400 MHz, Dimethylsulfoxide-d6) δ 8.93-8.69 (m, 1H), 5.36-5.06 (m, 2H), 2.96-2.80 (m, 1H), 2.18-2.05 (m, 2H), 2.03-1.91 (m, 2H), 1.90-1.76 (m, 1H) 1.76-1.65 (m, 1H).

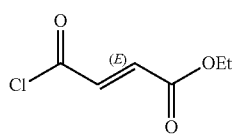

Step 2: (E)-ethyl 4-chloro-4-oxobut-2-enoate

To a mixture of (E)-4-ethoxy-4-oxo-but-2-enoic acid (9.5 g, 65.92 mmol) and imethylformaldehyde (481.80 mg, 6.59 mmol) in dichloromethane (90 mL) was added oxalyl dichloride (10.04 g, 79.10 mmol) at 0° C. under nitrogen atmosphere. The mixture was stirred at 0° C. for 30 min under nitrogen atmosphere. The reaction mixture was concentrated to dryness in vacuo affording (E)-ethyl 4-chloro-4-oxobut-2-enoate (10 g, crude) as a yellow oil, used in next step without any further purification.

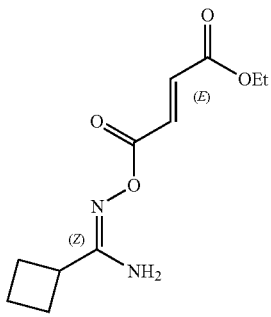 [SMILES: CCOC(=O)/C=C/C(=O)O/N=C(\N)C1CCC1]

Step 3: (E)-ethyl 4-(((Z)-(amino(cyclobutyl)methylene)amino)oxy)-4-oxobut-2-enoate To a mixture of (Z)—N-hydroxycyclobutanecarboximidamide (5.8 g, 50.81 mmol) and potassium carbonate (10.53 g, 76.22 mmol) in dioxane (50 mL) was added ethyl (E)-ethyl 4-chloro-4-oxobut-2-enoate (9.91 g, 60.97 mmol). The mixture was degassed and purged with nitrogen for 3 times. The mixture was stirred at 20° C. for 30 min under nitrogen atmosphere. The reaction mixture was concentrated to dryness in vacuo affording (E)-ethyl 4-(((Z)-(amino(cyclobutyl)methylene)amino)oxy)-4-oxobut-2-enoate (11.9 g, crude) as a white solid, used in next step without any further purification. LCMS Rt=0.425 min, m/z=240.1 [M+H]+.

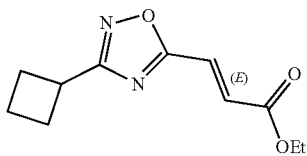 [SMILES: CCOC(=O)/C=C/c1nc(C2CCC2)no1]

Step 4: (E)-ethyl 3-(3-cyclobutyl-1,2,4-oxadiazol-5-yl)acrylate

The cyclization reaction was prepared in a similar fashion to Method #1, Step 3. The mixture was diluted with water (20 mL) and extracted with ethyl acetate (3×50 mL). The combined organic layers were dried over sodium sulphate and concentrated in vacuo affording (E)-ethyl 3-(3-cyclobutyl-1,2,4-oxadiazol-5-yl)acrylate (5.3 g, crude) as a a brown solid, used in next step without any further purification. LCMS Rt=0.583 min, m/z=222.1 [M+H]+.

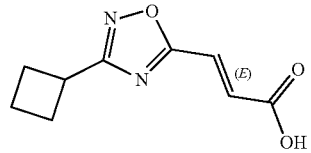 [SMILES: O=C(O)/C=C/c1nc(C2CCC2)no1]

Step 5: (E)-3-(3-cyclobutyl-1,2,4-oxadiazol-5-yl) acrylic acid

The hydrolysis reaction was prepared in a similar fashion to Method #1, Step 4. The crude was purified by reverse phase HPLC (column: Phenomenex Luna C18 200*40 mm*10 um; mobile phase: [water (formic acid)- Acetonitrile]; B %: 24%-54%, 10 min) affording (E)-3-(3-cyclobutyl-1,2,4-oxadiazol-5-yl)acrylic acid (240 mg, 5.18%) as a white solid. LCMS Rt=0.237 min, m/z=194.1 [M+H]+.

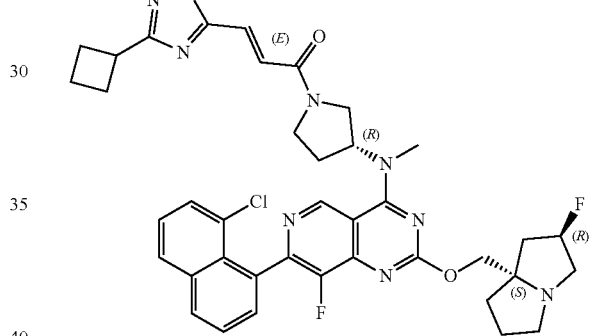

Step 6: (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-cyclobutyl-1,2,4-oxadiazol-5-yl)prop-2-en-1-one The amide coupling was prepared in a similar fashion to Method #1, Step 10. The residue was purified by reverse phase HPLC: (column: Waters Xbridge Prep OBD C18 150*40 mm*10 μm; mobile phase: [water (NH4HCO3)—Acetonitrile]; B %: 50%-80%, 8 min) affording (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-cyclobutyl-1,2,4-oxadiazol-5-yl)prop-2-en-1-one (23.48 mg, 16.71%) as a yellow amorphous solid: $^1$H NMR (400 MHz, Acetonitrile-d3) δ 9.22 (t, J=1.9 Hz, 1H), 8.15 (dd, J=1.2, 8.2 Hz, 1H), 8.05 (dd, J=0.9, 8.2 Hz, 1H), 7.75-7.68 (m, 1H), 7.67-7.62 (m, 2H), 7.57-7.52 (m, 1H), 7.50-7.34 (m, 2H), 5.49-5.17 (m, 2H), 4.30-4.10 (m, 3H), 4.09-3.99 (m, 1H), 3.95-3.78 (m, 1H), 3.77-3.68 (m, 1H), 3.67-3.50 (m, 1H), 3.49-3.43 (m, 3H), 3.20-3.04 (m, 3H), 2.95-2.85 (m, 1H), 2.49-2.32 (m, 6H), 2.26-2.19 (m, 1H), 2.13-2.00 (m, 4H), 1.93-1.81 (m, 3H). LCMS Rt=3.298 min, m/z=740.3 [M+H]+.

LCMS (5 to 95% acetonitrile in water+0.03% ammonium bicarbonate over 6 mins) retention time 3.298 min, ESI+ found [M+H]=740.3.

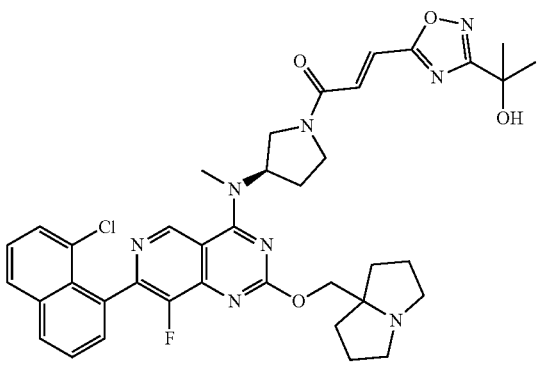 [SMILES: CN(c1nc(OCC23CCCN2CCC3)nc2c(F)c(-c3cccc4cccc(Cl)c34)ncc12)[C@@H]1CCN(C(=O)/C=C/c2nc(C(C)(C)O)no2)C1]

Example 112 (Method 2): (R,E)-1-(3-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidin-1-yl)-3-(3-(2-hydroxypropan-2-yl)-1,2,4-oxadiazol-5-yl)prop-2-en-1-one

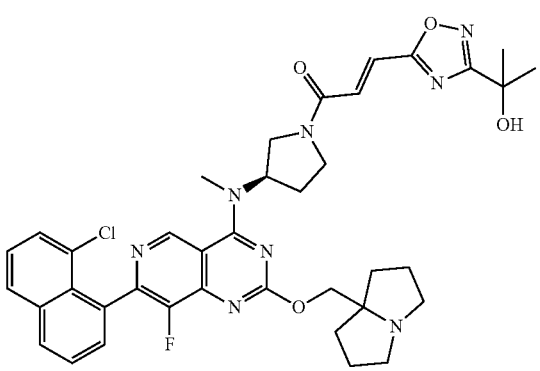 [SMILES: CN(c1nc(OCC23CCCN2CCC3)nc2c(F)c(-c3cccc4cccc(Cl)c34)ncc12)[C@@H]1CCN(C(=O)/C=C/c2nc(C(C)(C)O)no2)C1]

Step 1: (R,E)-1-(3-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidin-1-yl)-3-(3-(2-hydroxypropan-2-yl)-1,2,4-oxadiazol-5-yl)prop-2-en-1-one The amide coupling reaction was prepared in a similar fashion to Method #2, Step 7. The crude product was purified by reverse phase prep-HPLC (column: Waters Xbridge Prep OBD C18 150*40 mm*10 um; mobile phase: [water (NH$_4$HCO$_3$)-acetonitrile]; B %: 30%-60%, 8 min) affording (R,E)-1-(3-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidin-1-yl)-3-(3-(2-hydroxypropan-2-yl)-1,2,4-oxadiazol-5-yl)prop-2-en-1-one (20.59 mg, 18.00%) as a yellow amorphous solid: $^1$H NMR (400 MHz, Acetonitrile-d3) δ 9.22-9.15 (m, 1H), 8.16-8.08 (m, 1H), 8.04-7.98 (m, 1H), 7.72-7.66 (m, 1H), 7.65-7.59 (m, 2H), 7.54-7.42 (m, 2H), 7.41-7.34 (m, 1H), 5.52-5.27 (m, 1H), 4.26-4.11 (m, 3H), 4.07-3.95 (m, 1H), 3.92-3.83 (m, 1H), 3.82-3.72 (m, 1H), 3.68-3.55 (m, 1H), 3.49-3.40 (m, 3H), 3.02-2.91 (m, 2H), 2.64-2.54 (m, 2H), 2.48-2.29 (m, 2H), 2.19-2.02 (m, 2H), 1.89-1.71 (m, 4H), 1.68-1.52 (m, 8H). LCMS Rt=2.699 min, m/z=726.3 [M+H]$^+$.

LCMS (5 to 95% acetonitrile in water+0.03% ammonium bicarbonate over 6 mins) retention time 2.699 min, ESI+ found [M+H]=726.3.

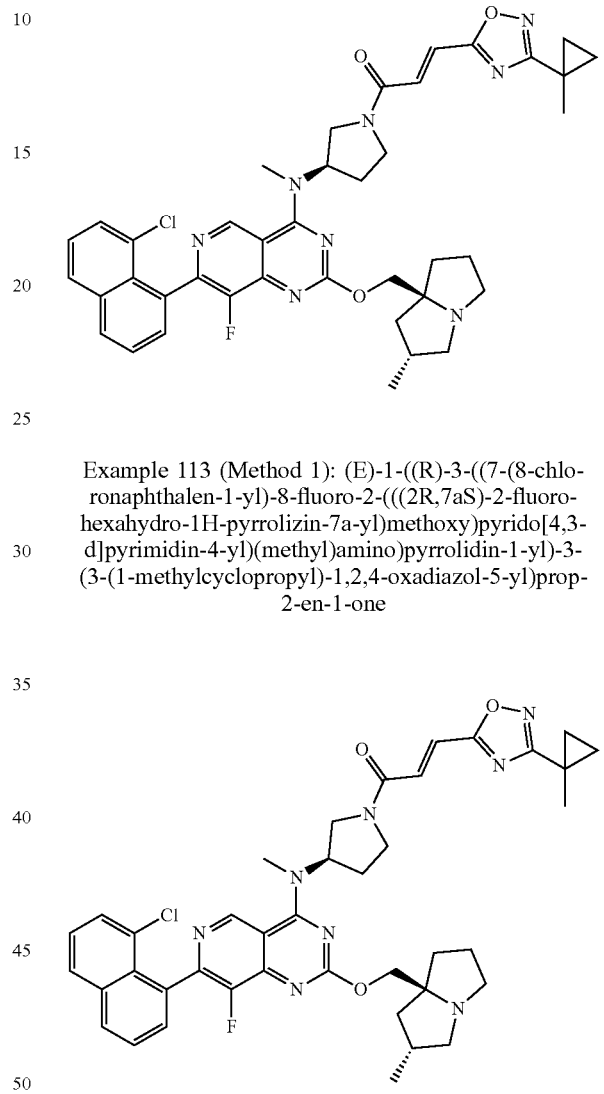

Example 113 (Method 1): (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-(1-methylcyclopropyl)-1,2,4-oxadiazol-5-yl)prop-2-en-1-one Step 1: (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-(1-methylcyclopropyl)-1,2,4-oxadiazol-5-yl)prop-2-en-1-one The amide coupling reaction was prepared in a similar fashion to Method #1, Step 10. The residue was purified by reverse phase HPLC (column: Waters Xbridge Prep OBD C18 150*40 mm*10 μm; mobile phase: [water (NH$_4$HCO$_3$)-acetonitrile]; B %: 45%-75%, 8 min) affording (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-(1- methylcyclopropyl)-1,2,4-oxadiazol-5-yl)prop-2-en-1-one (54.34 mg, 39.53%) as a white solid: ¹H NMR (400 MHz, Acetonitrile-d3) δ 9.21 (s, 1H), 8.14 (d, J=8.0 Hz, 1H), 8.04 (d, J=8.0 Hz, 1H), 7.79-7.67 (m, 1H), 7.67-7.60 (m, 2H), 7.57-7.49 (m, 1H), 7.47-7.27 (m, 2H), 5.50-5.16 (m, 2H), 4.24-4.12 (m, 2H), 4.01 (br d, J=3.6 Hz, 1H), 3.94-3.67 (m, 2H), 3.66-3.49 (m, 1H), 3.45 (s, 3H), 3.23-3.04 (m, 3H), 2.99-2.82 (m, 1H), 2.43 (br d, J=6.1 Hz, 1H), 2.41-2.27 (m, 2H), 2.27-2.15 (m, 2H), 2.14-2.02 (m, 2H), 1.85 (br s, 1H), 1.51 (d, J=8.1 Hz, 3H), 1.27-1.14 (m, 2H), 1.02-0.88 (m, 2H). LCMS Rt=3.306 min, m/z=740.3 [M+H]⁺.

LCMS (5 to 95% acetonitrile in water+0.03% ammonium bicarbonate over 6 mins) retention time 3.306 min. ESI+ found [M+H]=740.3.

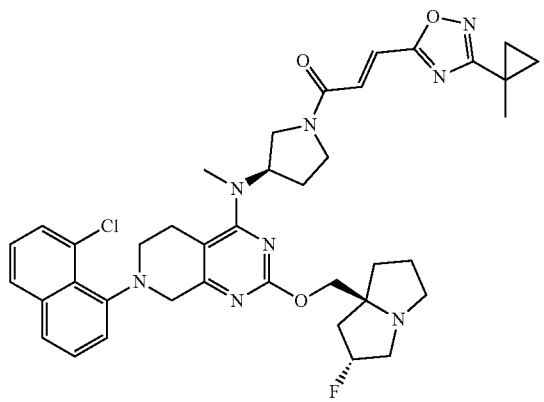 [SMILES: CN(c1nc(OC[C@@]23CCCN2C[C@H](F)C3)nc2c1CCN(c1cccc3cccc(Cl)c13)C2)[C@@H]1CCN(C(=O)/C=C/c2nc(C3(C)CC3)no2)C1]

Example 114 (Method 4): (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino) pyrrolidin-1-yl)-3-(3-(1-methylcyclopropyl)-1,2,4-oxadiazol-5-yl)prop-2-en-1-one

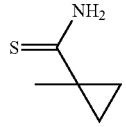

Step 1: 1-methylcyclopropanecarbothioamide

The sulfamide formation was prepared in a similar fashion to Method #5, Step 2. The resulting residue was purified by column chromatography (silica gel, 100-200 mesh, 50% ethyl acetate in petroleum ether) affording 1-methylcyclopropanecarbothioamide (1.8 g, 77.45%) as a white solid: ¹H NMR (400 MHz, Dimethyl sulfoxide-d6) δ 9.43 (br s, 1H), 8.69 (br s, 1H), 1.36-1.29 (m, 5H), 0.74 (q, J=3.6 Hz, 2H).

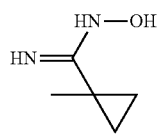

Step 2: N-hydroxy-1-methylcyclopropanecarboximidamide

The hydroxylimidamide formation was prepared in a similar fashion to Method #5, Step 3. The resulting residue was purified by column chromatography (silica gel, 100-200 mesh, 40% ethyl acetate in petroleum ether) affording N-hydroxy-1-methyl-cyclopropanecarboxamidine (1.53 g, 85.78%) as a yellow gum: ¹H NMR (400 MHz, Dimethyl sulfoxide-d6) δ 8.98-8.81 (m, 1H), 5.29-5.09 (m, 2H), 1.23-1.12 (m, 3H), 0.81 (br d, J=8.2 Hz, 2H), 0.50-0.34 (m, 2H).

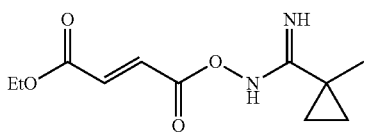 [SMILES: CCOC(=O)/C=C/C(=O)ONC(=N)C1(C)CC1]

Step 3: (E)-ethyl 4-((1-methylcyclopropanecarboximidamido)oxy)-4-oxobut-2-enoate The amide coupling reaction was prepared in a similar fashion to Method #1, Step 2. The crude product was purified by column chromatography (silica gel, 100-200 mesh, 30% ethyl acetate in petroleum ether) affording (E)-ethyl 4-((1-methylcyclopropanecarboximidamido)oxy)-4-oxobut-2-enoate (1.85 g, 57.45%) as a white solid. LCMS Rt=0.630 min, m/z=240.1 [M+H]⁺.

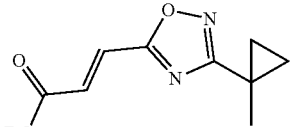

Step 4: (E)-ethyl 3-(3-(1-methylcyclopropyl)-1,2,4-oxadiazol-5-yl)acrylate

The cyclization reaction was prepared in a similar fashion to Method #1, Step 3. The resulting residue was purified by column chromatography (silica gel, 100-200 mesh, 20% ethyl acetate in petroleum ether) affording (E)-ethyl 3-(3-(1-methylcyclopropyl)-1,2,4-oxadiazol-5-yl)acrylate (1.2 g, 70.12%) as a yellow gum. LCMS Rt=0.820 min, m/z=222.1 [M+H]⁺.

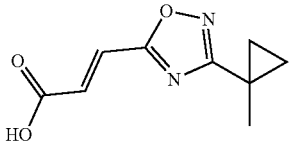

Step 5: (E)-3-(3-(1-methylcyclopropyl)-1,2,4-oxadiazol-5-yl)acrylic acid

The hydrolysis reaction was prepared in a similar fashion to Method #1, Step 4.

The reaction mixture was concentrated in vacuo affording (E)-3-(3-(1-methylcyclopropyl)-1,2,4-oxadiazol-5-yl) acrylic acid (800 mg, crude) as a white solid, used in next step without further purification. LCMS Rt=0.638 min, m/z=194.1 [M+H]$^+$.

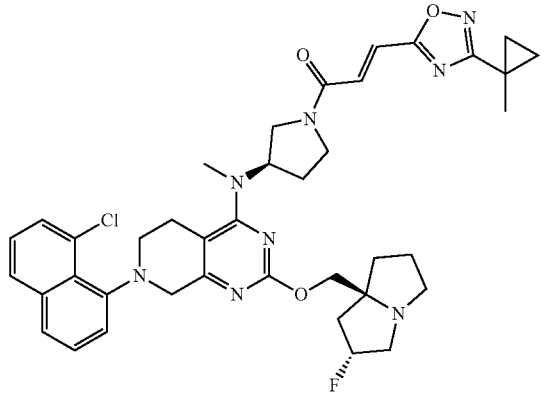 [SMILES: CN(c1nc(OC[C@@]23CCCN2C[C@H](F)C3)nc2c1CCN(c1cccc3cccc(Cl)c13)C2)[C@@H]1CCN(C(=O)/C=C/c2nc(C3(C)CC3)no2)C1]

Step 6: (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-(1-methylcyclopropyl)-1,2,4-oxadiazol-5-yl)prop-2-en-1-one The amide coupling reaction was prepared in a similar fashion to Method #4, Step 11. The crude product was purified by reverse phase prep-HPLC (column: Waters Xbridge BEH C18 100*30 mm*10 μm; mobile phase: [water (NH$_4$HCO$_3$)-acetonitrile]; B %: 60%-90%, 10 min) affording (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-(1-methylcyclopropyl)-1,2,4-oxadiazol-5-yl)prop-2-en-1-one (29.72 mg, 25.02%) as a yellow solid: $^1$H NMR (400 MHz, Acetonitrile-d3) δ 7.87 (d, J=8.0 Hz, 1H), 7.70 (br d, J=7.9 Hz, 1H), 7.58 (d, J=7.1 Hz, 1H), 7.53 (br d, J=4.1 Hz, 1H), 7.43 (d, J=7.6 Hz, 1H), 7.41-7.26 (m, 3H), 5.35-5.13 (m, 1H), 4.92-4.73 (m, 1H), 4.32-4.21 (m, 1H), 4.19-4.05 (m, 1H), 4.05-3.97 (m, 1H), 3.95 (br d, J=1.1 Hz, 1H), 3.89-3.77 (m, 1H), 3.62 (br d, J=2.5 Hz, 2H), 3.58-3.51 (m, 1H), 3.50-3.40 (m, 1H), 3.34-3.17 (m, 1H), 3.06 (br dd, J=3.9, 11.6 Hz, 4H), 3.03-2.97 (m, 3H), 2.94-2.82 (m, 1H), 2.63 (br d, J=14.4 Hz, 1H), 2.42-2.19 (m, 3H), 2.11-2.00 (m, 2H), 1.93-1.76 (m, 3H), 1.51 (d, J=3.4 Hz, 3H), 1.23-1.17 (m, 2H), 0.97-0.91 (m, 2H). LCMS Rt=3.500 min, m/z=726.3 [M+H]$^+$.

LCMS (5 to 95% acetonitrile in water+0.1% trifluoroacetic acid over 6 mins) retention time 3.500 min, ESI+ found [M+H]=726.3.

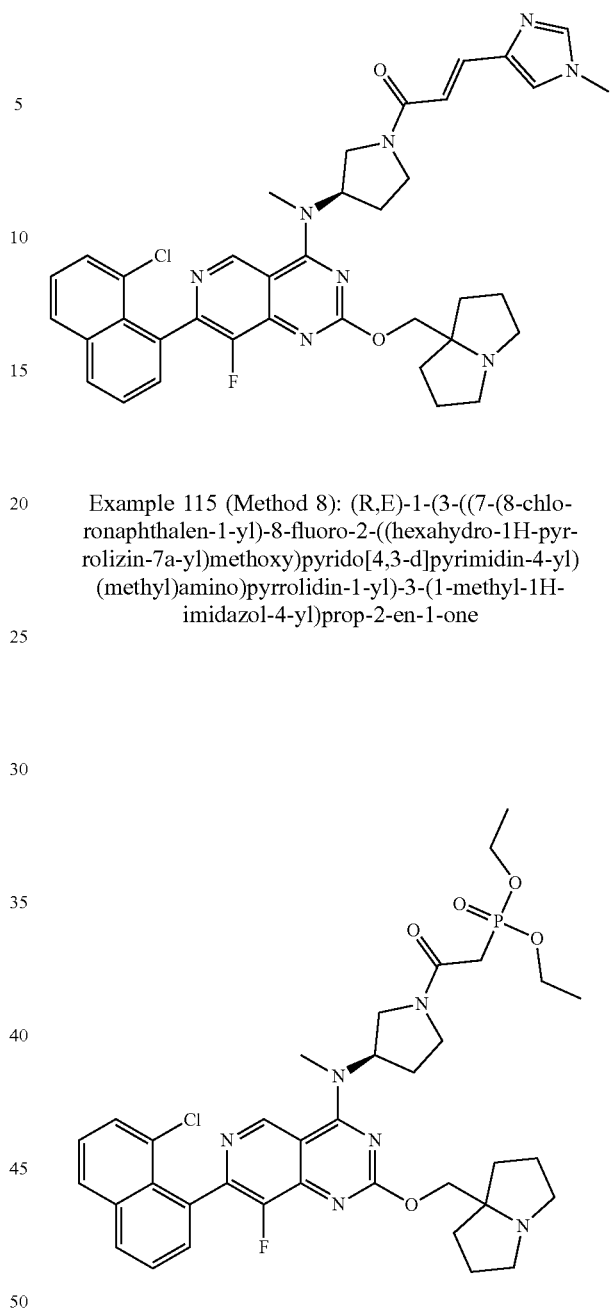

Example 115 (Method 8): (R,E)-1-(3-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidin-1-yl)-3-(1-methyl-1H-imidazol-4-yl)prop-2-en-1-one

Step 1: (R)-diethyl (2-(3-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidin-1-yl)-2-oxoethyl)phosphonate The amide coupling reaction was prepared in a similar fashion to Method #8, Step 3. The crude product was purified by reverse phase HPLC (column: Phenomenex Luna 80*30 mm*3 μm; mobile phase: [water (trifluoroacetic acid)-acetonitrile]; B %: 20%-55%, 8 min) affording (R)-diethyl (2-(3-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidin-1-yl)-2-oxoethyl) phosphonate (90 mg, 96.99%, trifluoroacetate salt) as a yellow oil. LCMS Rt=1.755 min, m/z=724.3 [M+H]$^+$.

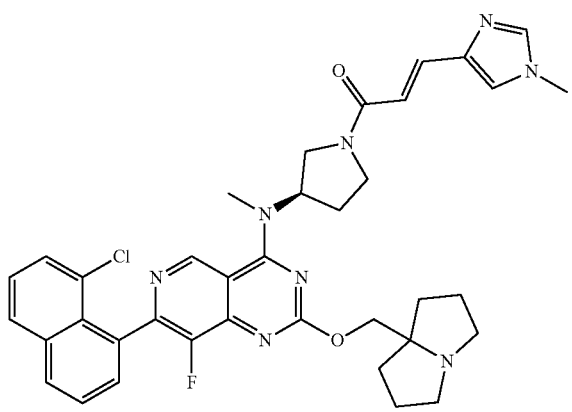 [SMILES: CN(c1nc(OCC23CCCN2CCC3)nc2c(F)c(-c3cccc4cccc(Cl)c34)ncc12)[C@@H]1CCN(C(=O)/C=C/c2cn(C)cn2)C1]

Step 2: (R,E)-1-(3-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidin-1-yl)-3-(1-methyl-1H-imidazol-4-yl)prop-2-en-1-one The Homer-Wadsworth-Emmons reaction was prepared in a similar fashion to Method #8, Step 4. The crude product was purified by reverse phase HPLC (column: Waters Xbridge BEH C18 100*30 mm*10 μm; mobile phase: [water (NH$_4$HCO$_3$)-acetonitrile]; B %: 25%-55%, 10 min) affording (R,E)-1-(3-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidin-1-yl)-3-(1-methyl-1H-imidazol-4-yl)prop-2-en-1-one (42.71 mg, 65.23%) as a yellow oil: $^1$H NMR (400 MHz, Acetonitrile-d3) δ 9.18 (s, 1H), 8.12 (dd, J=1.1, 8.1 Hz, 1H), 8.01 (d, J=7.5 Hz, 1H), 7.71-7.66 (m, 1H), 7.64-7.59 (m, 2H), 7.54-7.48 (m, 1H), 7.47-7.39 (m, 2H), 7.21 (d, J=5.1 Hz, 1H), 6.87 (dd, J=9.6, 15.1 Hz, 1H), 5.48-5.28 (m, 1H), 4.20-4.08 (m, 2H), 4.02-3.90 (m, 1H), 3.88-3.79 (m, 1H), 3.78-3.69 (m, 1H), 3.65 (d, J=5.4 Hz, 3H), 3.61-3.45 (m, 1H), 3.42 (s, 3H), 3.00-2.90 (m, 2H), 2.62-2.53 (m, 2H), 2.45-2.35 (m, 1H), 2.34-2.24 (m, 1H), 2.01-1.95 (m, 1H), 1.92-1.71 (m, 5H), 1.66-1.56 (m, 2H). LCMS Rt=2.438 min, m/z=680.3 [M+H]$^+$.

LCMS (5 to 95% acetonitrile in water+0.03% ammonium bicarbonate over 6 mins) retention time 2.438 min, ESI+ found [M+H]=680.3.

Example 116 (Method 4): (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-(1,1-difluoroethyl)-1,2,4-oxadiazol-5-yl)prop-2-en-1-one

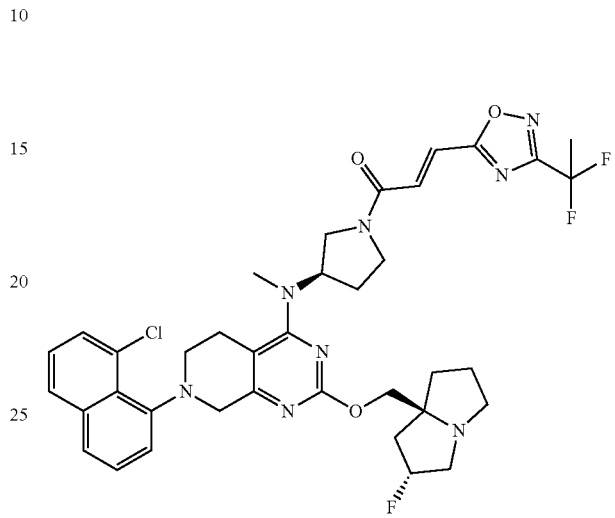

Step 1: (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-(1,1-difluoroethyl)-1,2,4-oxadiazol-5-yl)prop-2-en-1-one The amide coupling reaction was prepared in a similar fashion to Method #4, Step 11. The crude product was purified by reverse phase prep-HPLC (column: Waters Xbridge Prep OBD C18 150*40 mm*10 um; mobile phase: [water (NH$_4$HCO$_3$)-acetonitrile]; B %: 55%-90%, 8 min) affording (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-(1,1-difluoroethyl)-1,2,4-oxadiazol-5-yl)prop-2-en-1-one (39.75 mg, 38.45%) as a yellow solid: $^1$H NMR (400 MHz, Acetonitrile-d3) δ 7.85 (d, J=8.1 Hz, 1H), 7.69 (br d, J=8.0 Hz, 1H), 7.60-7.53 (m, 2H), 7.52-7.47 (m, 1H), 7.47-7.41 (m, 1H), 7.41-7.37 (m, 1H), 7.32 (t, J=7.1 Hz, 1H), 5.35-5.13 (m, 1H), 4.92-4.72 (m, 1H), 4.28-4.14 (m, 1H), 4.11-3.91 (m, 3H), 3.89-3.75 (m, 1H), 3.74-3.62 (m, 2H), 3.57-3.39 (m, 2H), 3.30-3.12 (m, 3H), 3.11-3.03 (m, 2H), 3.01-2.96 (m, 3H), 2.93-2.82 (m, 1H), 2.60 (br d, J=14.8 Hz, 1H), 2.30-2.19 (m, 1H), 2.19-2.14 (m, 2H), 2.13-2.10 (m, 2H), 2.09-2.04 (m, 2H), 2.04-1.99 (m, 1H), 1.92-1.77 (m, 3H). LCMS Rt=3.399 min, m/z=736.3 [M+H]$^+$.

LCMS (5 to 95% acetonitrile in water+0.1% trifluoroacetic acid over 6 mins) retention time 3.399 min, ESI+ found [M+H]=736.3.

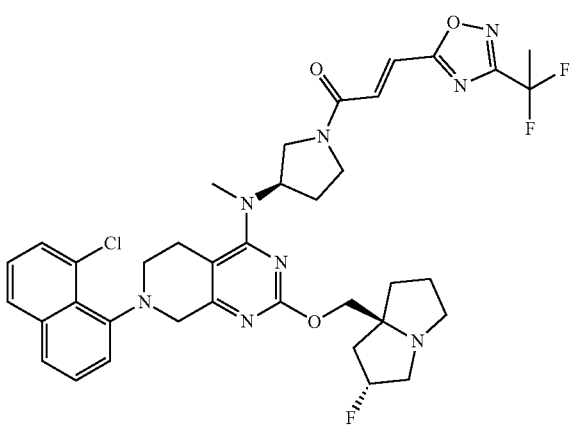 [SMILES: CN(c1nc(OC[C@@]23CCCN2C[C@H](F)C3)nc2c1CCN(c1cccc3cccc(Cl)c13)C2)[C@@H]1CCN(C(=O)/C=C/c2nc(C(C)(F)F)no2)C1]

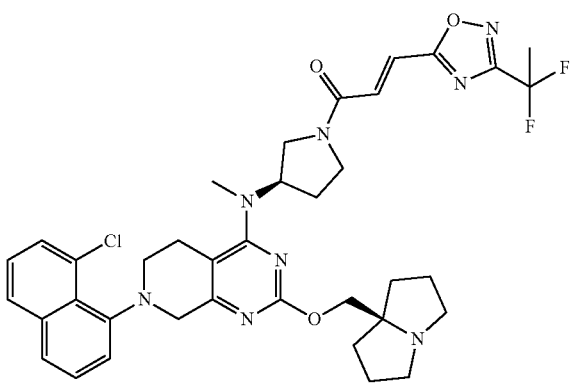

Example 117 (Method 4-Master): (R,E)-1-(3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)-(3-(1,1-difluoroethyl)-1,2,4-oxadiazol-5-yl)prop-2-en-1-one

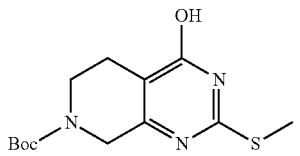 [SMILES: CSc1nc(O)c2c(n1)CN(C(=O)OC(C)(C)C)CC2]

Step 1: tert-butyl 4-hydroxy-2-(methylthio)-5,6-dihydropyrido[3,4-d]pyrimidine-7(8H)-carboxylate To a solution of 1-tert-butyl 4-ethyl 3-oxopiperidine-1,4-dicarboxylate (100 g, 368.58 mmol) in methanol (1.5 L) was added sodium methoxide (99.55 g, 1.84 mol) and 2-methylisothiourea (124.88 g, 667.02 mmol, sulfate salt). The reaction mixture was stirred at 25° C. for 16 h, then quenched with 2.0 M hydrochloric acid and concentrated to dryness in vacuo to remove methanol. The aqueous layer was diluted with water (1 L) and the resulting precipitate was filtered and washed with ethanol (200 mL) affording tert-butyl 4-hydroxy-2-(methylthio)-5,6-dihydropyrido[3,4-d]pyrimidine-7(8H)-carboxylate (184 g, crude) as a white solid used in the next step without any further purification: $^1$H NMR (400 MHz, Chloroform-d) δ 4.56 (br s, 2H), 4.36-4.27 (m, 2H), 3.63-3.57 (m, 2H), 2.59-2.55 (m, 3H), 1.49 (s, 9H). LCMS Rt=0.553 min, m/z =297.1 [M+H]$^+$.

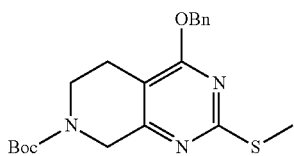 [SMILES: CSc1nc2c(c(OCc3ccccc3)n1)CCN(C(=O)OC(C)(C)C)C2]

Step 2: tert-butyl 4-(benzyloxy)-2-(methylthio)-5,6-dihydropyrido[3,4-d]pyrimidine-7(8H)-carboxylate To a solution of tert-butyl 4-hydroxy-2-(methylthio)-5,6-dihydropyrido[3,4-d]pyrimidine-7(8H)-carboxylate (92 g, 309.38 mmol) in toluene (1.2 L) was added argentiooxycarbonyloxysilver (93.84 g, 340.31 mmol) and (bromomethyl)benzene (63.50 g, 371.25 mmol) at 0° C. The reaction mixture was stirred at 110° C. for 8 h. The resulting viscous mass was diluted with water (1 L) and extracted with ethyl acetate (3×1 L). The combined organic layers were dried over sodium sulphate and concentrated in vacuo. The crude residue was diluted with a (10:1) mixture of petroleum ether: ethyl acetate (1 L) and the resulting precipitate was filtered affording tert-butyl 4-(benzyloxy)-2-(methylthio)-5,6-dihydropyrido[3,4-d]pyrimidine-7(8H)-carboxylate (93 g, crude) as a white solid used in the next step without any further purification: $^1$H NMR (400 MHz, Chloroform-d) δ 7.44-7.40 (m, 2H), 7.40-7.31 (m, 3H), 5.46 (s, 2H), 4.48 (br s, 2H), 3.64 (br t, J=5.6 Hz, 2H), 2.65 (br s, 2H), 2.54 (s, 3H), 1.48 (s, 9H). LCMS Rt=0.769 min, m/z=387.2 [M +H]$^+$.

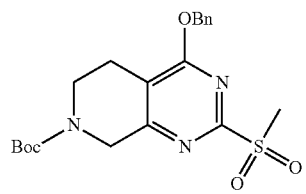 [SMILES: CC(C)(C)OC(=O)N1CCc2c(nc(S(C)(=O)=O)nc2OCc2ccccc2)C1]

Step 3: tert-butyl 4-(benzyloxy)-2-(methylsulfonyl)-5,6-dihydropyrido[3,4-d]pyrimidine-7(8H)-carboxylate To a solution of tert-butyl 4-(benzyloxy)-2-(methylthio)-5,6-dihydropyrido[3,4-d]pyrimidine-7(8H)-carboxylate (75 g, 193.55 mmol) in dichloromethane (1 L) was added methyl 3-chlorobenzoperoxoate (110.02 g, 541.94 mmol, 85% purity). The mixture was stirred at 0° C. for 3 h. The reaction mixture was quenched with a saturated solution of sodium sulfite (1 L), and extracted with ethyl acetate (3×1 L). The combined organic layers were dried over sodium sulphate and concentrated in vacuo. The crude was diluted with a (10:1) mixture of petroleum ether: ethyl acetate (1 L), the resulting precipitate was filtered and washed with a (10:1) mixture of petroleum ether: ethyl acetate (500 mL) affording tert-butyl 4-(benzyloxy)-2-(methylsulfonyl)-5,6-dihydropyrido[3,4-d]pyrimidine-7(8H)-carboxylate (75 g, crude) as a white solid used in the next step without any further purification: $^1$H NMR (400 MHz, Chloroform-d) δ 7.48-7.43 (m, 2H), 7.42-7.35 (m, 3H), 5.54 (s, 2H), 4.65 (s, 2H), 3.70 (br t, J=5.7 Hz, 2H), 3.29 (s, 3H), 2.78 (br s, 2H), 1.49 (s, 9H). LCMS Rt=0.675 min, m/z=419.2 [M+H]$^+$.

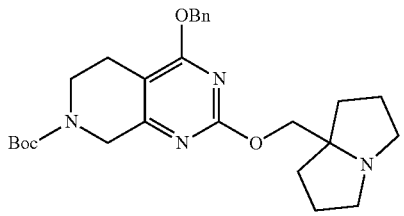 [SMILES: CC(C)(C)OC(=O)N1CCc2c(nc(OCC34CCCN3CCC4)nc2OCc2ccccc2)C1]

Step 4: tert-butyl 4-(benzyloxy)-2-((hexahydro-1H-pyrrolizin-7a-yl)methoxy)-5,6-dihydropyrido[3,4-d]pyrimidine-7(8H)-carboxylate To a solution of (hexahydro-1H-pyrrolizin-7a-yl)methanol (30 g, 212.45 mmol) cooled to −10° C. in toluene (300 mL) was added sodium tert-butoxide (15.31 g, 159.34 mmol) and a solution of tert-butyl 4-(benzyloxy)-2-(methylsulfonyl)-5,6-dihydropyrido[3,4-d]pyrimidine-7(8H)-carboxylate (44.56 g, 106.23 mmol) in toluene (500 mL) was added at −10° C., and the reaction mixture was stirred at −10° C. for another 10 min. The reaction mixture was quenched with a saturated solution of ammonium chloride (1 L) at 0° C., and extracted with ethyl acetate (3×1 L). The combined organic layers were dried over sodium sulphate and concentrated under vacuo affording tert-butyl 4-(benzyloxy)-2-((hexahydro-1H-pyrrolizin-7a-yl)methoxy)-5,6-dihydropyrido[3,4-d]pyrimidine-7(8H)-carboxylate (54.33 g, crude) as a yellow oil used in next step without any further purification: ¹H NMR (400 MHz, Chloroform-d) δ 7.33-7.28 (m, 2H), 7.25-7.22 (m, 1H), 7.16-7.12 (m, 1H), 7.09-7.05 (m, 1H), 5.32 (s, 2H), 4.35 (s, 2H), 4.05-3.95 (m, 2H), 3.53 (br s, 2H), 2.99 (td, J=5.4, 10.4 Hz, 2H), 2.52 (br dd, J=3.1, 6.2 Hz, 3H), 2.25 (s, 1H), 1.99-1.91 (m, 2H), 1.79-1.69 (m, 4H), 1.54 (td, J=7.6, 12.7 Hz, 2H), 1.36 (s, 9H).

LCMS Rt=0.586 min, m/z=480.3 [M+H]⁺.

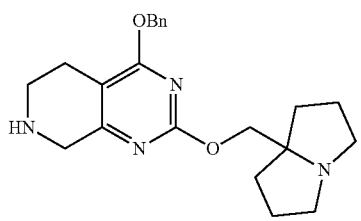 [SMILES: c1ccc(COc2nc(OCC34CCCN3CCC4)nc3c2CCNC3)cc1]

Step 5: 4-(benzyloxy)-2-((hexahydro-1H-pyrrolizin-7a-yl)methoxy)-5,6,7,8-tetrahydropyrido[3,4-d]pyrimidine A mixture of tert-butyl 4-benzyloxy-2-(1,2,3,5,6,7-hexahydropyrrolizin-8-ylmethoxy)-6,8-dihydro-5H-pyrido[3,4-d]pyrimidine-7-carboxylate (54 g, 112.36 mmol) in hydrochloric acid/ethyl acetate (4M, 600 mL) was stirred at 25° C. for 0.5 h. The reaction mixture was concentrated in vacuo. The crude residue was diluted with a saturated solution of sodium carbonate (300 mL) at 0° C., and extracted with a 10:1 mixture of dichloromethane: isopropanol (3×300 mL). The combined organic layers were dried over sodium sulphate and concentrated under vacuo affording 4-(benzyloxy)-2-((hexahydro-1H-pyrrolizin-7a-yl)methoxy)-5,6,7,8-tetrahydropyrido[3,4-d]pyrimidine (40 g, crude) as a brown oil used in next step without any further purification: ¹H NMR (400 MHz, Chloroform-d) δ 7.44-7.40 (m, 2H), 7.39-7.31 (m, 3H), 5.43 (s, 2H), 4.07 (s, 2H), 3.87 (s, 2H), 3.14-3.05 (m, 4H), 2.66-2.53 (m, 4H), 2.00-1.55 (m, 8H). LCMS Rt=0.413 min, m/z=380.2 [M+H]⁺.

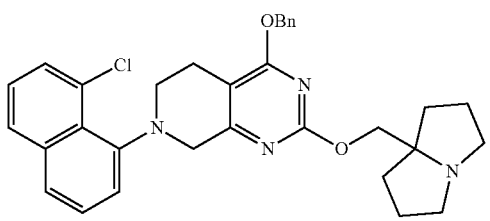 [SMILES: Clc1cccc2cccc(N3CCc4c(nc(OCC56CCCN5CCC6)nc4OCc4ccccc4)C3)c12]

Step 6: 4-(benzyloxy)-7-(8-chloronaphthalen-1-yl)-2-((hexahydro-1H-pyrrolizin-7a-yl)methoxy)-5,6,7,8-tetrahydropyrido[3,4-d]pyrimidine A mixture of 4-(benzyloxy)-2-((hexahydro-1H-pyrrolizin-7a-yl)methoxy)-5,6,7,8-tetrahydropyrido[3,4-d]pyrimidine (38.78 g, 101.92 mmol), 1-bromo-8-chloronaphthalene (44.31 g, 183.46 mmol), (1E,4E)-1,5-diphenylpenta-1,4-dien-3-one; palladium (9.33 g, 10.19 mmol), dicyclohexyl-[2-(2,6-diisopropoxyphenyl)phenyl]phosphane (9.51 g, 20.38 mmol) and cesium carbonate (132.83 g, 407.69 mmol) in toluene (500 mL) was degassed and purged with nitrogen 3 times, then the reaction mixture was stirred at 100° C. for 12 h under nitrogen atmosphere. The reaction mixture was concentrated in vacuo. The crude was diluted with water (1 L) and extracted with ethyl acetate (3×1 L). The combined organic layers were dried over sodium sulphate and concentrated in vacuo. The resulting residue was purified by column chromatography (silica gel, 100-200 mesh, 0-100% ethyl acetate in petroleum ether) affording 4-(benzyloxy)-7-(8-chloronaphthalen-1-yl)-2-((hexahydro-1H-pyrrolizin-7a-yl)methoxy)-5,6,7,8-tetrahydropyrido[3,4-d]pyrimidine (42.55 g, 77.15%) as a brown oil. LCMS Rt=0.670 min, m/z =540.2 [M+H]⁺.

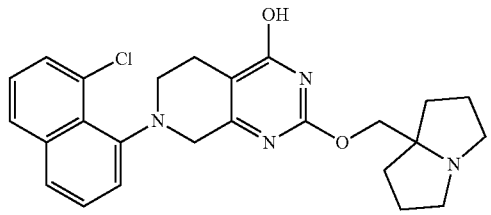 [SMILES: Oc1nc(OCC23CCCN2CCC3)nc2c1CCN(c1cccc3cccc(Cl)c13)C2]

Step 7: 7-(8-chloronaphthalen-1-yl)-2-((hexahydro-1H-pyrrolizin-7a-yl)methoxy)-5,6,7,8-tetrahydropyrido[3,4-d]pyrimidin-4-ol A mixture of 4-(benzyloxy)-7-(8-chloronaphthalen-1-yl)-2-((hexahydro-1H-pyrrolizin-7a-yl)methoxy)-5,6,7,8-tetrahydropyrido[3,4-d]pyrimidine (41 g, 75.77 mmol) in trifluoroacetic acid (500 mL) was stirred at 60° C. for 0.5 h. The reaction mixture was concentrated in vacuo. The crude was quenched with a saturated solution of sodium carbonate (300 mL) at 0° C., and extracted with dichloromethane (3×150 mL). The combined organic layers were dried over sodium sulphate and concentrated in vacuo affording 7-(8-chloronaphthalen-1-yl)-2-((hexahydro-1H-pyrrolizin-7a-yl)methoxy)-5,6,7,8-tetrahydropyrido[3,4-d]pyrimidin-4-ol (45 g, crude) as a brown solid used in next step without any further purification: ¹H NMR (400 MHz, Chloroform-d) δ 7.62 (d, J=8.0 Hz, 1H), 7.47 (d, J=7.9 Hz, 1H), 7.40 (dd, J=0.9, 7.4 Hz, 1H), 7.21-7.15 (m, 2H), 7.10 (br d, J=7.1 Hz, 1H), 4.60 (s, 1H), 4.36-4.24 (m, 2H), 3.68-3.52 (m, 3H), 3.48-3.36 (m, 1H), 3.06-2.94 (m, 1H), 2.90-2.69 (m, 3H), 2.14-1.67 (m, 10H). LCMS Rt=0.557 min, m/z=450.2 [M+H]⁺.

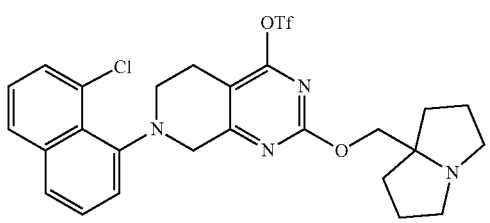 [SMILES: O=S(=O)(Oc1nc(OCC23CCCN2CCC3)nc2c1CCN(c1cccc3cccc(Cl)c13)C2)C(F)(F)F]

Step 8: 7-(8-chloronaphthalen-1-yl)-2-((hexahydro-1H-pyrrolizin-7a-yl)methoxy)-5,6,7,8-tetrahydropyrido[3,4-d]pyrimidin-4-yl trifluoromethanesulfonate To a solution of 7-(8-chloronaphthalen-1-yl)-2-((hexahydro-1H-pyrrolizin-7a-yl)methoxy)-5,6,7,8-tetrahydropyrido[3,4-d]pyrimidin-4-ol (1 g, 2.22 mmol) and triethylamine (1.35 g, 13.30 mmol) in dichloromethane (450 mL) was added trifluoromethylsulfonyl trifluoromethanesulfonate (1.56 g, 5.54 mmol) in dichloromethane (50 mL) at 0° C. under nitrogen atmosphere. The mixture was stirred at 25° C. for 1 h under nitrogen atmosphere. The reaction mixture was quenched with water (40 mL) and extracted with dichloromethane (3×100 mL). The combined organic layers were dried over sodium sulphate and concentrated in vacuo affording 7-(8-chloronaphthalen-1-yl)-2-((hexahydro-1H-pyrrolizin-7a-yl)methoxy)-5,6,7,8-tetrahydropyrido[3,4-d]pyrimidin-4-yl trifluoromethanesulfonate (1.2 g, crude) used in next step without any further purification. LCMS Rt=0.788 min, m/z=582.1 [M+H]⁺.

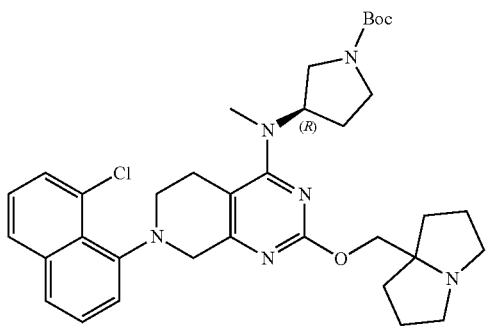

Step 9: (R)-tert-butyl 3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidine-1-carboxylate To a solution of 7-(8-chloronaphthalen-1-yl)-2-((hexahydro-1H-pyrrolizin-7a-yl)methoxy)-5,6,7,8-tetrahydropyrido[3,4-d]pyrimidin-4-yl trifluoromethanesulfonate (2.59 g, 4.44 mmol), N-ethyl-N-isopropylpropan-2-amine (2.87 g, 22.21 mmol) in N,N-dimethylformaldehyde (5 mL) was added tert-butyl (3R)-3-(methylamino)pyrrolidine-1-carboxylate (1.78 g, 8.88 mmol) at 0° C. The mixture was stirred at 25° C. for 12 h. The reaction mixture was quenched by addition water (20 mL) and extracted with ethyl acetate (3×20 mL). The combined organic layers were dried over sodium sulphate and concentrated in vacuo. The resulting residue was purified by column chromatography (silica gel, 100-200 mesh, 10-100% ethyl acetate in petroleum ether) affording (R)-tert-butyl 3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidine-1-carboxylate (2 g, 71.10%) as a yellow oil. LCMS Rt=1.659 min, m/z=632.3 [M+H]⁺.

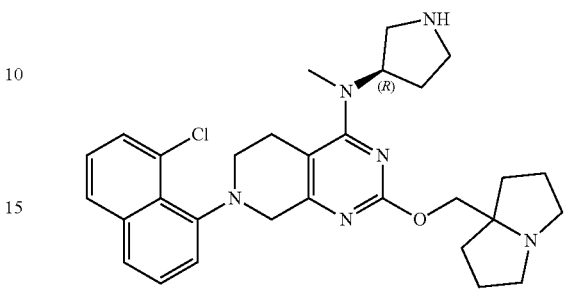

Step 10: (R)-7-(8-chloronaphthalen-1-yl)-2-((hexahydro-1H-pyrrolizin-7a-yl)methoxy)-N-methyl-N-(pyrrolidin-3-yl)-5,6,7,8-tetrahydropyrido[3,4-d]pyrimidin-4-amine The deprotection of Boc was prepared in a similar fashion to Method #1, Step 9.

The reaction mixture was concentrated in vacuo and the crude product was purified by reverse phase HPLC (Phenomenex Luna 80*30 mm*3 μm; mobile phase: [water (trifluoroacetic acid)-acetonitrile]; B %: 5%-45%, 8 min) affording (R)-7-(8-chloronaphthalen-1-yl)-2-((hexahydro-1H-pyrrolizin-7a-yl)methoxy)-N-methyl-N-(pyrrolidin-3-yl)-5,6,7,8-tetrahydropyrido[3,4-d]pyrimidin-4-amine (220 mg, 35.88%, trifluoroacetate salt) as a white solid. LCMS Rt=0.722 min, m/z=532.3 [M+H]⁺.

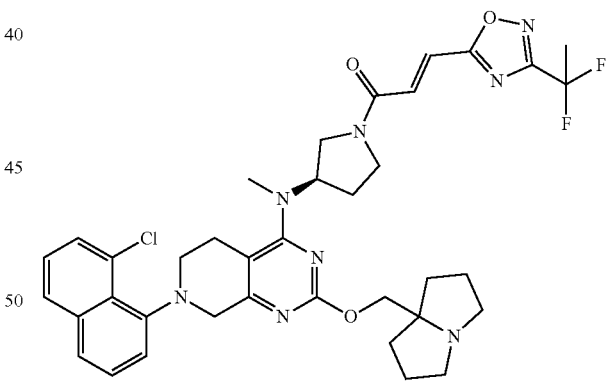

Step 11: (R,E)-1-(3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)-(3-(1,1-difluoroethyl)-1,2,4-oxadiazol-5-yl)prop-2-en-1-one The amide coupling reaction was prepared in a similar fashion to Method #1, Step 10. The crude product was purified by reverse phase HPLC (column: Waters Xbridge Prep OBD C18 150*40 mm*10 um; mobile phase: [water (ammonium bicarbonate)- acetonitrile]; B %: 40%-70%, 8 min) affording (R,E)-1-(3-((7-(8-chloronaphthalen-1-yl)-2-

((hexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-(1,1-difluoroethyl)-1,2,4-oxadiazol-5-yl)prop-2-en-1-one(31.95 mg, 26.92%) as a yellow solid: ¹H NMR (400 MHz, Acetonitrile-d3) δ 7.88 (d, J=8.1 Hz, 1H), 7.71 (br d, J=8.2 Hz, 1H), 7.63-7.50 (m, 3H), 7.49-7.40 (m, 2H), 7.38-7.32 (m, 1H), 4.94-4.76 (m, 1H), 4.34-4.14 (m, 1H), 4.09-3.93 (m, 3H), 3.92-3.65 (m, 3H), 3.60-3.41 (m, 2H), 3.36-3.06 (m, 2H), 3.05-2.91 (m, 5H), 2.68-2.55 (m, 3H), 2.22-2.15 (m, 2H), 2.14-2.06 (m, 3H), 1.96-1.89 (m, 2H), 1.88-1.73 (m, 4H), 1.68-1.56 (m, 2H). LCMS Rt=2.361 min, m/z=718.3 [M+H]⁺.

LCMS (5 to 95% acetonitrile in water+0.1% trifluoroacetic acid over 6 mins) retention time 2.361 min, ESI+ found [M+H]=718.3.

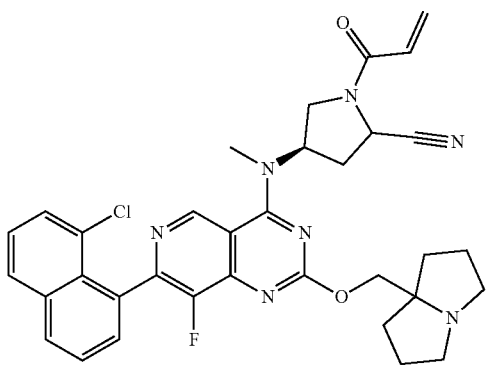 [SMILES: C=CC(=O)N1C[C@H](N(C)c2nc(OCC34CCCN3CCC4)nc3c(F)c(-c4cccc5cccc(Cl)c45)ncc23)CC1C#N]

Example 118 (Method 6): (4R)-1-acryloyl-4-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidine-2-carbonitrile

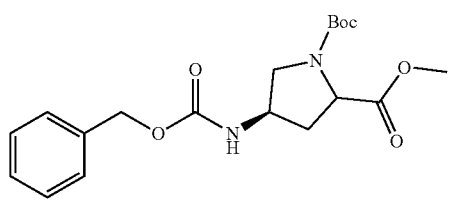 [SMILES: COC(=O)C1C[C@@H](NC(=O)OCc2ccccc2)CN1C(=O)OC(C)(C)C]

Step 1: (4R)-1-tert-butyl 2-methyl 4-(((benzyloxy)carbonyl)amino)pyrrolidine-1,2-dicarboxylate To a solution of (4R)-1-tert-butyl 2-methyl 4-aminopyrrolidine-1,2-dicarboxylate (9.6 g, 39.30 mmol) in tetrahydrofuran (90 mL) and water (30 mL) was added sodium carbonate (83.30 g, 785.97 mmol) and benzyl carbonochloridate (8.04 g, 47.16 mmol) at 0° C. The mixture was stirred at 20° C. for 1 h. The reaction mixture was quenched with saturated ammonium chloride (70 mL) at 0° C. and extracted with dichloromethane (3×50 mL). The combined organic layers were dried over sodium sulphate and concentrated in vacuo. The residue was purified by column chromatography (silica gel, 100-200 mesh, 0-100% ethyl acetate in petroleum ether) affording (4R)-1-tert-butyl 2-methyl 4-(((benzyloxy)carbonyl)amino)pyrrolidine-1,2-dicarboxylate (13 g, 87.42%) as a yellow oil: ¹H NMR (400 MHz, Chloroform-d) δ 7.34-7.21 (m, 5H), 5.09-4.96 (m, 2H), 4.37-4.15 (m, 2H), 3.80-3.62 (m, 4H), 3.52-3.15 (m, 1H), 2.34 (br s, 1H), 2.28-2.04 (m, 1H), 1.96-1.78 (m, 1H), 1.36 (br d, J=17.8 Hz, 9H). LCMS Rt=0.589 min, m/z=378.2 [M+H]⁺.

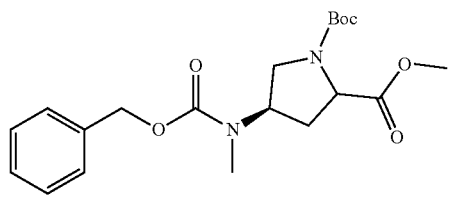 [SMILES: COC(=O)C1C[C@@H](N(C)C(=O)OCc2ccccc2)CN1C(=O)OC(C)(C)C]

Step 2: (4R)-1-tert-butyl 2-methyl 4-(((benzyloxy)carbonyl)(methyl)amino)pyrrolidine-1,2-dicarboxylate To a solution of (4R)-1-tert-butyl 2-methyl 4-(((benzyloxy)carbonyl)amino)pyrrolidine-1,2-dicarboxylate (13 g, 34.35 mmol) in N,N-dimethylformaldehyde (100 mL) was added methyl iodide (24.38 g, 171.77 mmol) and sodium hydride (2.75 g, 68.71 mmol, 60% purity) at 0° C., then stirred at 25° C. for 1 h. The reaction mixture was quenched with saturated ammonium chloride (100 mL) at 0° C. and extracted with dichloromethane (3×100 mL). The combined organic layers were dried over sodium sulphate and concentrated in vacuo. The residue was purified by column chromatography (silica gel, 100-200 mesh, 0-100% ethyl acetate in petroleum ether) affording (4R)-1-tert-butyl 2-methyl 4-(((benzyloxy)carbonyl)(methyl)amino)pyrrolidine-1,2-dicarboxylate (10 g, 74.17%) as a yellow oil: ¹H NMR (400 MHz, Chloroform-d) δ 7.34-7.22 (m, 5H), 5.15-5.00 (m, 2H), 4.95-4.58 (m, 1H), 4.40-4.07 (m, 1H), 3.71-3.64 (m, 3H), 3.37-3.19 (m, 1H), 2.78 (s, 3H), 2.42-2.15 (m, 1H), 2.13-2.00 (m, 1H), 1.97-1.84 (m, 1H), 1.40-1.32 (m, 9H).

LCMS Rt=0.607 min, m/z=392.2 [M+H]⁺.

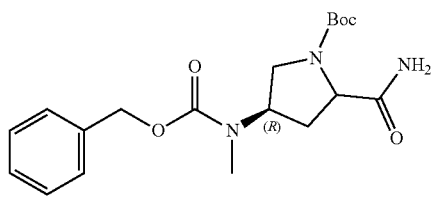

Step 3: (4R)-tert-butyl 4-(((benzyloxy)carbonyl)(methyl)amino)-2-carbamoylpyrrolidine-1-carboxylate A mixture of (4R)-1-tert-butyl 2-methyl 4-(((benzyloxy)carbonyl)(methyl)amino)pyrrolidine-1,2-dicarboxylate (8 g, 20.39 mmol) in ammonium hydroxide (80 mL) was stirred at 50° C. for 12 h. The reaction mixture was filtered and the filtrate was concentrated in vacuo. The residue was purified by column chromatography (silica gel, 100-200 mesh, 0-100% ethyl acetate in petroleum ether) affording (4R)-tert-butyl 4-(((benzyloxy)carbonyl)(methyl)amino)-2-carbamoylpyrrolidine-1-carboxylate (2.0 g, 25.99%) as a yellow oil. LCMS Rt=0.510 min, m/z=377.2 [M+H]⁺.

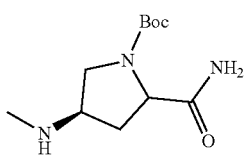 [SMILES: CN[C@@H]1CC(C(N)=O)N(C(=O)OC(C)(C)C)C1]

Step 4: (4R)-tert-butyl 2-carbamoyl-4-(methyl-amino)pyrrolidine-1-carboxylate

The deprotection of Cbz group was prepared in a similar fashion to Method #6, Step 6. The mixture was concentrated in vacuo affording (4R)-tert-butyl 2-carbamoyl-4-(methyl-amino)pyrrolidine-1-carboxylate (2.0 g, crude) as a brown oil, used in next step without any further purification. LCMS Rt=0.117 min, m/z=243.2 [M+H]$^+$.

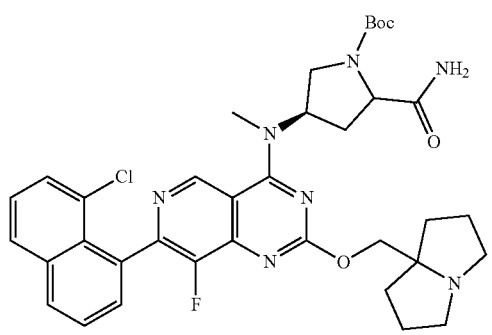 [SMILES: CN(c1nc(OCC23CCCN2CCC3)nc2c(F)c(-c3cccc4cccc(Cl)c34)ncc12)[C@@H]1CC(C(N)=O)N(C(=O)OC(C)(C)C)C1]

Step 5: (4R)-tert-butyl 2-carbamoyl-4-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidine-1-carboxylate The substitution reaction was prepared in a similar fashion to Method #1, Step 8, the residue was purified by reverse phase HPLC (column: Phenomenex luna C18 250*50 mm*10 μm; mobile phase: [water (trifluoroacetic acid)-acetonitrile]; B %: 20%-50%, 10 min) affording (4R)-tert-butyl 2-carbamoyl-4-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidine-1-carboxylate (310 mg, 46.58%, trifluoroacetate salt) as a white solid. LCMS Rt=0.806 min, m/z=689.3 [M+H]$^+$.

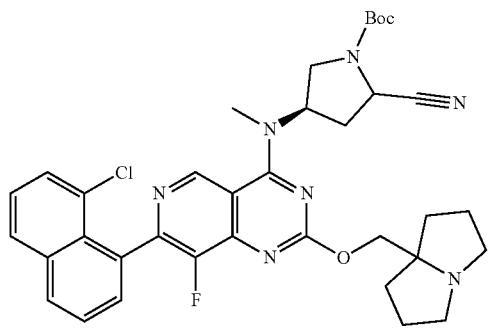 [SMILES: CN(c1nc(OCC23CCCN2CCC3)nc2c(F)c(-c3cccc4cccc(Cl)c34)ncc12)[C@@H]1CC(C#N)N(C(=O)OC(C)(C)C)C1]

Step 6: (4R)-tert-butyl 4-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)-2-cyanopyrrolidine-1-carboxylate The dehydration reaction was prepared in a similar fashion to Method #6, Step 11, the mixture was concentrated in vacuo affording (4R)-tert-butyl 4-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)-2-cyanopyrrolidine-1-carboxylate (80 mg, crude) as a yellow oil, used in next step without any further purification. LCMS Rt=2.254 min, m/z=671.3 [M+H]$^+$.

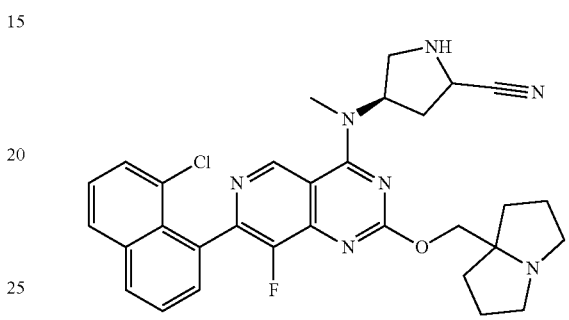

Step 7: (4R)-4-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidine-2-carbonitrile The deprotection of Boc group was prepared in a similar fashion to Method #1, Step 9. The reaction mixture was concentrated in vacuo affording (4R)-4-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidine-2-carbonitrile (70 mg, crude, trifluoroacetate salt) as a brown oil, used in next step without any further purification. LCMS Rt=0.748 min, m/z=571.2 [M+H]$^+$.

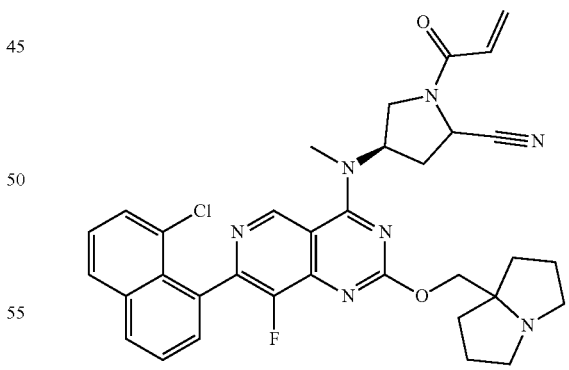

Step 8: (4R)-1-acryloyl-4-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidine-2-carbonitrile The amide coupling reaction was prepared in a similar fashion to Method #6, Step 13. The crude product was purified by reverse phase HPLC (column: Waters Xbridge Prep OBD C18 150*40 mm*10 µm; mobile phase: [water (NH₄HCO₃)-acetonitrile]; B %: 25%-65%, 8 min) affording (5.15 mg, 6.33%) as a yellow amorphous solid: ¹H NMR (400 MHz, Acetonitrile-d3) δ 9.20 (d, J=8.1 Hz, 1H), 8.14 (d, J=7.9 Hz, 1H), 8.03 (d, J=8.3 Hz, 1H), 7.74-7.68 (m, 1H), 7.67-7.59 (m, 3H), 7.56-7.49 (m, 1H), 6.64-6.48 (m, 1H), 6.44-6.29 (m, 1H), 5.85-5.56 (m, 1H), 5.38-4.71 (m, 1H), 4.22-4.12 (m, 3H), 3.92-3.69 (m, 1H), 3.50 (d, J=1.0 Hz, 1H), 3.43 (s, 1H), 3.02-2.91 (m, 2H), 2.67-2.56 (m, 3H), 1.94 (s, 3H), 1.88-1.71 (m, 5H), 1.68-1.59 (m, 2H). LCMS Rt=2.743 min, m/z=625.2 [M+H]⁺.

LCMS (5 to 95% acetonitrile in water+0.03% ammonium bicarbonate over 6 mins) retention time 2.743 min, ESI+ found [M+H]=625.2.

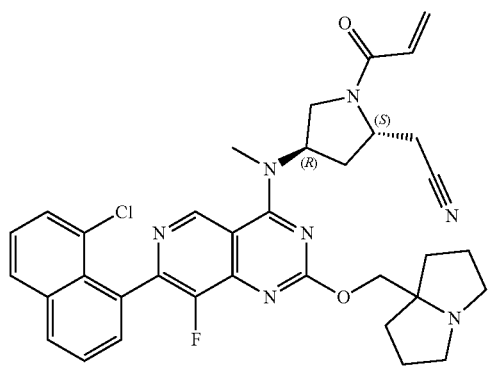

Example 119 (Method 6-Master): 2-((2S,4R)-1-acryloyl-4-((7-(8-chloronaphthalen-1-yl)-8-fluoro-2-((tetrahydro-1H-pyrrolizin-7a(5H)-yl)methoxy) pyrido[4,3-d]pyrimidin-4-yl)(methyl)amino) pyrrolidin-2-yl)acetonitrile

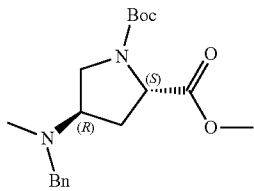

Step 1: (2S,4R)-1-tert-butyl 2-methyl 4-(benzyl (methyl)amino)pyrrolidine-1,2-dicarboxylate To a solution of (2S,4R)-1-tert-butyl 2-methyl 4-aminopyrrolidine-1,2-dicarboxylate (10 g, 40.94 mmol) in methanol (500 mL) was added acetic acid (245.83 mg, 4.09 mmol), sodium cyanoborohydride (7.72 g, 40.94 mmol) and benzaldehyde (4.34 g, 40.94 mmol), the reaction was stirred at 0° C. for 2 h, then formaldehyde (6.64 g, 81.87 mmol, 37% purity) was added to the mixture, then the mixture was stirred at 0° C. for 1 h. The reaction mixture was quenched with saturated sodium bicarbonate (30 mL) at 0° C. and extracted with dichloromethane (3×30 mL). The combined organic layers were dried over sodium sulphate and concentrated in vacuo and purified by column chromatography (silica gel, 100-200 mesh, 0-5% ethyl acetate in petroleum ether) affording (2S,4R)-1-tert-butyl 2-methyl 4-(benzyl (methyl)amino)pyrrolidine-1,2-dicarboxylate (10 g, 70.11%) as a yellow oil. LCMS Rt=0.452 min, m/z=348.2 [M+H]⁺.

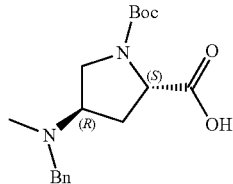

Step 2: (2S,4R)-tert-butyl 4-(benzyl(methyl)amino)-2-(hydroxymethyl)pyrrolidine-1-carboxylate To a solution of (2S,4R)-1-tert-butyl 2-methyl 4-(benzyl (methyl)amino)pyrrolidine-1,2-dicarboxylate (10 g, 28.70 mmol) in tetrahydrofuran (500 mL) was added lithium aluminium hydride (2.18 g, 57.40 mmol), the reaction was stirred at 0° C. for 1 h. The mixture was quenched with sodium sulfate decahydrate (1 g) at 0° C., and dried over sodium sulphate and concentrated in vacuo affording (2S, 4R)-tert-butyl 4-(benzyl(methyl)amino)-2-(hydroxymethyl) pyrrolidine-1-carboxylate (9.5 g, crude) as a yellow oil, used in the next step without further purification.

LCMS Rt=0.959 min, m/z=320.2 [M+H]⁺.

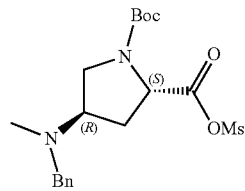

Step 3: (2S,4R)-tert-butyl 4-(benzyl(methyl)amino)-2-(((methylsulfonyl)oxy)methyl)pyrrolidine-1-carboxylate To a solution of (2S,4R)-tert-butyl 4-(benzyl(methyl) amino)-2-(hydroxymethyl)pyrrolidine-1-carboxylate (9.2 g, 28.71 mmol) in dichloromethane (200 mL) was added triethylamine (5.81 g, 57.42 mmol) and methylsulfonyl methanesulfonate (15.00 g, 86.14 mmol), the reaction was stirred at 0° C. for 1 h. The mixture was diluted with water (2 mL) at 0° C. and extracted with dichloromethane (3×10 mL). The combined organic layers were dried over sodium sulphate and concentrated in vacuo affording (2S,4R)-tert-butyl 4-(benzyl(methyl)amino)-2-(((methylsulfonyl)oxy) methyl)pyrrolidine-1-carboxylate (8 g, crude) as a yellow oil, used in the next step without further purification. LCMS Rt=1.099 min, m/z=398.2 [M+H]⁺.

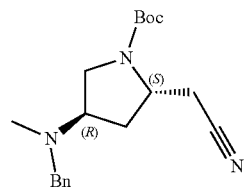

Step 4: (2S,4R)-tert-butyl 4-(benzyl(methyl)amino)-2-(cyanomethyl)pyrrolidine-1-carboxylate To a solution of (2S,4R)-tert-butyl 4-(benzyl(methyl)amino)-2-(((methylsulfonyl)oxy)methyl)pyrrolidine-1-carboxylate (16 g, 40.15 mmol) in dimethyl sulfoxide (100 mL) was added potassium cyanide (18.26 g, 280.42 mmol). The reaction was stirred at 60° C. for 12 h. The mixture was diluted with water (50 mL) at 0° C. and extracted with ethyl acetate (3×100 mL). The combined organic layers were dried over sodium sulphate and concentrated in vacuo affording (2S,4R)-tert-butyl 4-(benzyl(methyl)amino)-2-(cyanomethyl)pyrrolidine-1-carboxylate (8 g, crude) as a yellow oil, used in the next step without further purification. LCMS Rt=0.553 min, m/z=329.2 [M+H]$^+$.

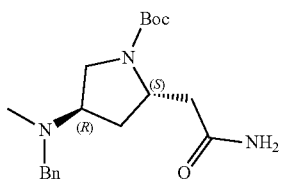

Step 5: (2S,4R)-tert-butyl 2-(2-amino-2-oxoethyl)-4-(benzyl(methyl)amino)pyrrolidine-1-carboxylate To a solution of (2S,4R)-tert-butyl 4-(benzyl(methyl)amino)-2-(cyanomethyl)pyrrolidine-1-carboxylate (8 g, 24.28 mmol) in dimethyl sulfoxide (100 mL) was added potassium carbonate (10.07 g, 72.85 mmol) and hydrogen peroxide (34.86 g, 307.46 mmol), the reaction was stirred at 60° C. for 12 h. The reaction mixture was quenched with saturated sodium sulfite (100 mL) at 0° C. and extracted with dichloromethane (3×100 mL). The combined organic layers were dried over sodium sulphate and concentrated in vacuo and purified by reverse phase HPLC (column: Phenomenex luna c18 250 mm*100 mm*10 μm; mobile phase: [water (trifluoroacetic acid)-acetonitrile]; B %: 5%-35%, 20 min) affording (2S,4R)-tert-butyl 2-(2-amino-2-oxoethyl)-4-(benzyl(methyl)amino)pyrrolidine-1-carboxylate (5 g, 44.62%, trifluoroacetate salt) as a yellow solid. LCMS Rt=0.577 min, m/z=347.2 [M+H]$^+$.

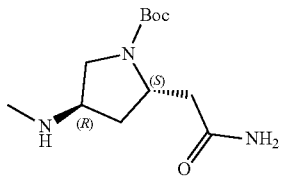

Step 6: (2S,4R)-tert-butyl 2-(2-amino-2-oxoethyl)-4-(methylamino)pyrrolidine-1-carboxylate To a solution of (2S,4R)-tert-butyl 2-(2-amino-2-oxoethyl)-4-(benzyl(methyl)amino)pyrrolidine-1-carboxylate (2.3 g, 4.98 mmol, trifluoroacetate salt) in methanol (50 mL) was added palladium on carbon (50 mg, 10% purity) and the mixture was stirred 25° C. for 1 h under hydrogen atmosphere. The reaction mixture was filtered and the filtrate was concentrated in vacuo affording (2S,4R)-tert-butyl 2-(2-amino-2-oxoethyl)-4-(methylamino)pyrrolidine-1-carboxylate (2.06 g, crude) as a yellow oil, used in next step without further purification. LCMS Rt=0.880 min, m/z=257.2 [M+H]$^+$.

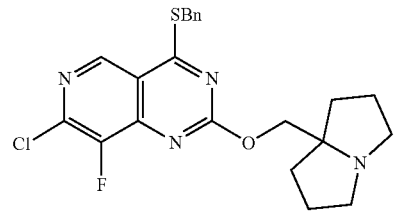

Step 7: 4-(benzylthio)-7-chloro-8-fluoro-2-((tetrahydro-1H-pyrrolizin-7a(5H)-yl)methoxy)pyrido[4,3-d]pyrimidine The substitution reaction was prepared in a similar fashion to Method #1, Step 5. The residue was purified by column chromatography (silica gel, 100-200 mesh, 0-100% ethyl acetate in petroleum ether) affording 4-(benzylthio)-7-chloro-8-fluoro-2-((hexahydro-1H-pyrrolizin-7a-yl)methoxy)pyrido[4,3-d]pyrimidine (10 g, 47.79%) as a yellow oil. LCMS Rt=0.694 min, m/z =444.1 [M+H]$^+$.

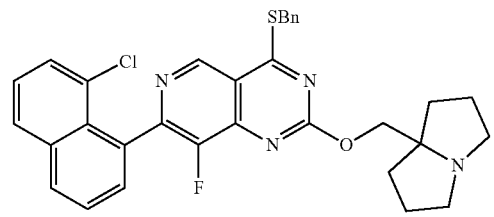

Step 8: 4-(benzylthio)-7-(8-chloronaphthalen-1-yl)-8-fluoro-2-((tetrahydro-1H-pyrrolizin-7a(5H)-yl)methoxy)pyrido[4,3-d]pyrimidine The suzuki reaction was prepared in a similar fashion to Method #1, Step 6. The mixture was purified by column chromatography (silica gel, 100-200 mesh, 10-50% ethyl acetate in petroleum ether) affording 4-(benzylthio)-7-(8-chloronaphthalen-1-yl)-8-fluoro-2-((tetrahydro-1H-pyrrolizin-7a(5H)-yl)methoxy)pyrido[4,3-d]pyrimidine (4.5 g, 80.45%) as a yellow solid. LCMS Rt=0.818 min, m/z=570.2 [M+H]$^+$.

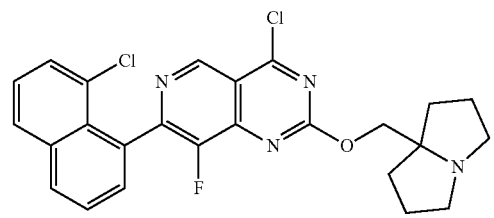 [SMILES: Fc1c(-c2cccc3cccc(Cl)c23)ncc2c(Cl)nc(OCC34CCCN3CCC4)nc12]

Step 9: 4-chloro-7-(8-chloronaphthalen-1-yl)-8-fluoro-2-((hexahydro-1H-pyrrolizin-7a-yl)methoxy)pyrido[4,3-d]pyrimidine The chlorination reaction was prepared in a similar fashion to Method #1, Step 7, the mixture was dried over sodium sulphate affording 4-chloro-7-(8-chloronaphthalen-1-yl)-8-fluoro-2-((hexahydro-1H-pyrrolizin-7a-yl)methoxy)pyrido[4,3-d]pyrimidine (400 mg, crude) as a yellow liquid, used in next step without any further purification. LCMS Rt=0.837 min, m/z=482.1 [M +H]+.

chloronaphthalen-1-yl)-8-fluoro-2-((hexahydro-1H-pyrrolizin-7a-yl)methoxy)pyrido[4,3-d]pyrimidin-4-yl)(methyl)amino)-2-(cyanomethyl)pyrrolidine-1-carboxylate (70 mg, crude) as a brown solid, used in the next step without further purification. LCMS Rt=0.776 min, m/z=685.3 [M+H]+.

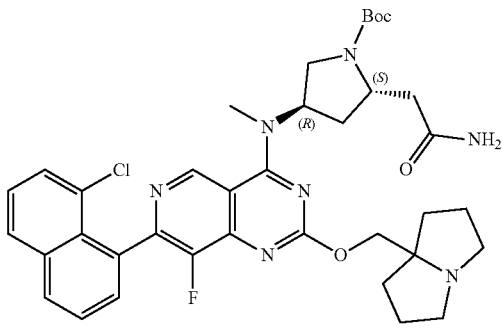

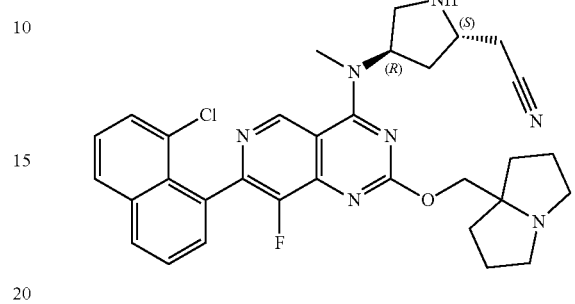

Step 10: (2S,4R)-tert-butyl 2-(2-amino-2-oxoethyl)-4-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidine-1-carboxylate The substitution reaction was prepared in a similar fashion to Method #1, Step 8. The mixture was purified by reverse phase HPLC (column: C18-1 150*30 mm*5 μm; mobile phase: [water (trifluoroacetic acid)-acetonitrile]; B %: 5%-50%, 8 min) affording (2S,4R)-tert-butyl 2-(2-amino-2-oxoethyl)-4-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidine-1-carboxylate (80 mg, 9.45%, trifluoroacetate salt) as a yellow solid. LCMS Rt=0.579 min, m/z=703.3 [M+H]+.

Step 12: 2-((2S,4R)-4-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidin-2-yl)acetonitrile The deprotection of Boc was prepared in a similar fashion to Method #1, Step 9. The reaction mixture was quenched with saturated sodium carbonate (3 mL) at 0° C. and extracted with dichloromethane (3×5 mL). The combined organic layers were dried over sodium sulphate and concentrated in vacuo affording 2-((2S,4R)-4-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidin-2-yl)acetonitrile (60 mg, crude) as a yellow oil, used in next step without further purification.
LCMS Rt=0.665 min, m/z=585.2 [M+H]+.

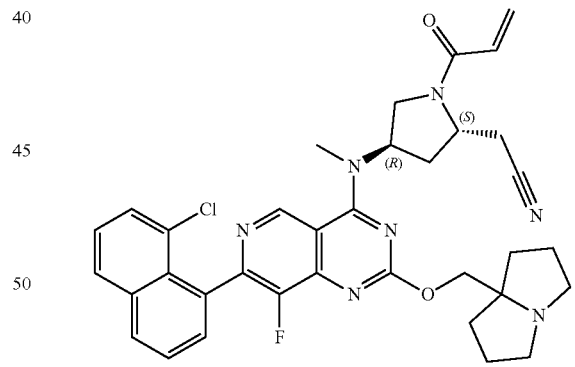

Step 11: (2S,4R)-tert-butyl 4-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)-2-(cyanomethyl)pyrrolidine-1-carboxylate To a solution of (2S,4R)-tert-butyl 2-(2-amino-2-oxoethyl)-4-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidine-1-carboxylate (70 mg, 99.40 μmol) in DCM (2 mL) was added Py (7.86 mg, 99.40 μmol), trifluoroacetic acid A (104.38 mg, 497.00 μmol). The mixture was stirred at 0° C. for 1 h. The mixture was concentrated in vacuo affording (2S,4R)-tert-butyl 4-((7-(8-

Step 13: 2-((2S,4R)-1-acryloyl-4-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-2-yl)acetonitrile The amide coupling reaction was prepared in a similar fashion to Method #1, Step 10. The residue was purified by reverse phase HPLC (column: Waters Xbridge Prep OBD C18 150*40 mm*10 μm; mobile phase: [water (NH4HCO3)-acetonitrile]; B %: 25%-55%, 8 min) affording 2-((2S,4R)-1-acryloyl-4-((7-(8-chloronaphthalen-1-yl)-8-fluoro-2-((tetrahydro-1H-pyrrolizin-7a(5H)-yl)methoxy)pyrido[4,3-d]

pyrimidin-4-yl)(methyl)amino)pyrrolidin-2-yl)acetonitrile (8.16 mg, 12.45%) as a yellow amorphous solid: $^1$H NMR (400 MHz, Acetonitrile-d3) δ 9.20 (s, 1H), 8.15 (dd, J=1.1, 8.1 Hz, 1H), 8.04 (dd, J=0.9, 8.2 Hz, 1H), 7.76-7.67 (m, 1H), 7.67-7.62 (m, 2H), 7.56-7.51 (m, 1H), 6.61 (dd, J=10.4, 16.5 Hz, 1H), 6.32 (dd, J=2.0, 16.8 Hz, 1H), 5.81-5.64 (m, 2H), 4.56 (br t, J=7.8 Hz, 1H), 4.26-4.16 (m, 3H), 3.79 (ddd, J=7.8, 10.6, 15.3 Hz, 1H), 3.42 (d, J=0.9 Hz, 3H), 3.07-2.99 (m, 2H), 2.91 (br d, J=3.4 Hz, 1H), 2.69-2.59 (m, 3H), 2.41-2.31 (m, 2H), 2.02-1.98 (m, 2H), 1.85 (br dd, J=5.9, 11.6 Hz, 4H), 1.71-1.61 (m, 2H). LCMS Rt=2.710 min, m/z=639.3 [M+H]$^+$.

LCMS (5 to 95% acetonitrile in water+0.03% ammonium bicarbonate over 6 mins) retention time 2.710 min, ESI+ found [M+H]=639.3.

Step 1: (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-cyclopropyl-1,2,4-oxadiazol-5-yl)prop-2-en-1-one The amide coupling reaction was prepared in a similar fashion to Method #4, Step 11. The crude was purified by reverse phase HPLC (column: Waters Xbridge Prep OBD C18 150*40 mm*10 µm; mobile phase: [water (NH$_4$HCO$_3$)-acetonitrile]; B %: 45%-75%, 8 min) affording (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-cyclopropyl-1,2,4-oxadiazol-5-yl)prop-2-en-1-one (14.87 mg, 17.50%) as a yellow oil: $^1$H NMR (400 MHz, Acetonitrile-d3) δ=7.74 (d, J=8.0 Hz, 1H), 7.58 (br d, J=8.1 Hz, 1H), 7.47-7.43 (m, 1H), 7.40 (dt, J=4.3, 7.8 Hz, 1H), 7.34-7.26 (m, 2H), 7.25-7.16 (m, 2H), 5.24-5.00 (m, 1H), 4.80-4.60 (m, 1H), 4.19-4.10 (m, 1H), 3.95-3.75 (m, 3H), 3.74-3.29 (m, 5H), 3.23-2.91 (m, 5H), 2.88-2.84 (m, 3H), 2.80-2.71 (m, 1H), 2.54-2.45 (m, 1H), 2.19-2.06 (m, 1H), 2.00-1.86 (m, 4H), 1.79-1.65 (m, 3H), 1.03-0.95 (m, 2H), 0.91-0.82 (m, 2H). LCMS Rt=2.432 min, m/z=712.3 [M+H]$^+$.

LCMS (5 to 95% acetonitrile in water+0.03% ammonium bicarbonate over 6 mins) retention time 2.432 min, ESI+ found [M+H]=712.3.

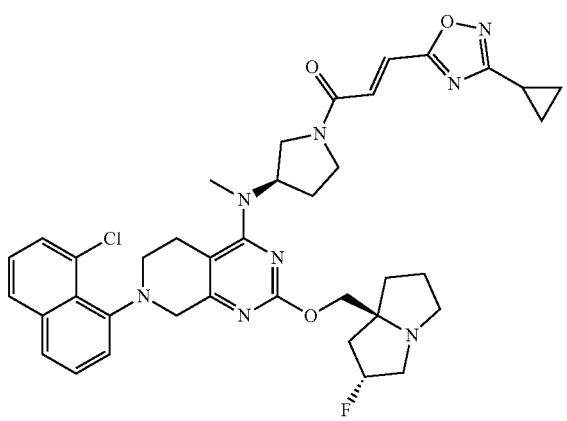 [SMILES: CN(c1nc(OC[C@@]23CCCN2C[C@H](F)C3)nc2c1CCN(c1cccc3cccc(Cl)c13)C2)[C@@H]1CCN(C(=O)/C=C/c2nc(C3CC3)no2)C1]

Example 120 (Method 4): (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-cyclopropyl-1,2,4-oxadiazol-5-yl)prop-2-en-1-one

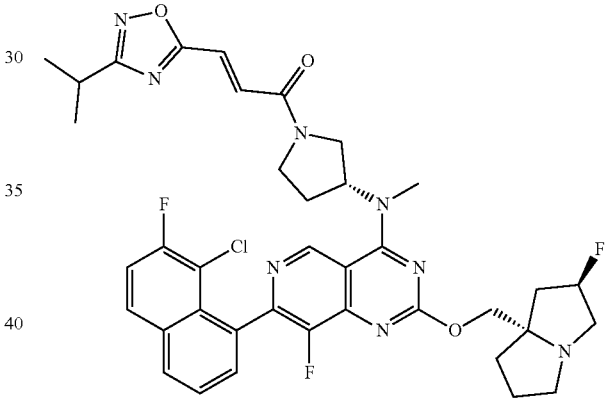

Example 121 (Method 1): (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-isopropyl-1,2,4-oxadiazol-5-yl)prop-2-en-1-one

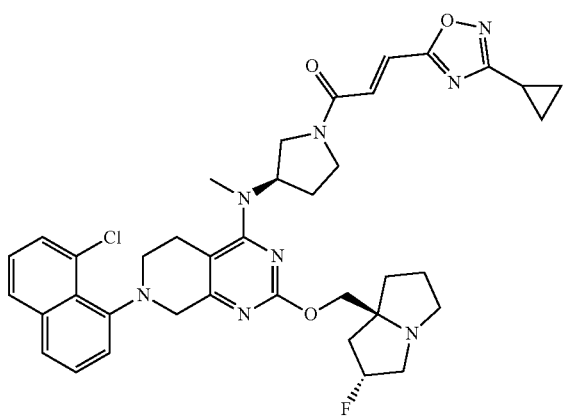 [SMILES: CN(c1nc(OC[C@@]23CCCN2C[C@H](F)C3)nc2c1CCN(c1cccc3cccc(Cl)c13)C2)[C@@H]1CCN(C(=O)/C=C/c2nc(C3CC3)no2)C1]

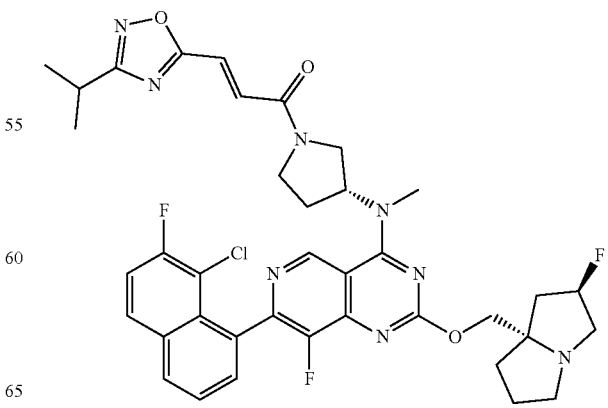

Step 1: (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-isopropyl-1,2,4-oxadiazol-5-yl)prop-2-en-1-one The amide coupling reaction was prepared in a similar fashion to Method #1, Step 10. The residue was purified by reverse phase HPLC (column: Waters Xbridge BEH C18 100*30 mm*10 um; mobile phase: [water ($NH_4HCO_3$)-acetonitrile]; B %: 40%-70%, 8 min) affording (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-isopropyl-1,2,4-oxadiazol-5-yl)prop-2-en-1-one (22.78 mg, 19.75%) as a yellow solid. $^1$H NMR (400 MHz, Acetonitrile-d3) δ 9.28-9.13 (m, 1H), 8.17-8.01 (m, 2H), 7.71-7.63 (m, 2H), 7.55-7.47 (m, 1H), 7.46-7.32 (m, 2H), 5.48-5.14 (m, 2H), 4.24-4.18 (m, 1H), 4.16-4.10 (m, 1H), 4.06-3.95 (m, 1H), 3.92-3.83 (m, 1H), 3.82-3.69 (m, 1H), 3.67-3.49 (m, 1H), 3.43 (s, 3H), 3.19-2.98 (m, 4H), 2.95-2.82 (m, 1H), 2.50-2.26 (m, 2H), 2.18-2.03 (m, 3H), 1.91-1.75 (m, 3H), 1.32 (dd, J=7.0, 8.6 Hz, 6H). LCMS Rt=3.281 min, m/z=746.3 [M+H]$^+$.

LCMS (5 to 95% acetonitrile in water+0.03% ammonium bicarbonate over 6 min) retention time 3.281 min, ESI+ found [M+H]=746.3.

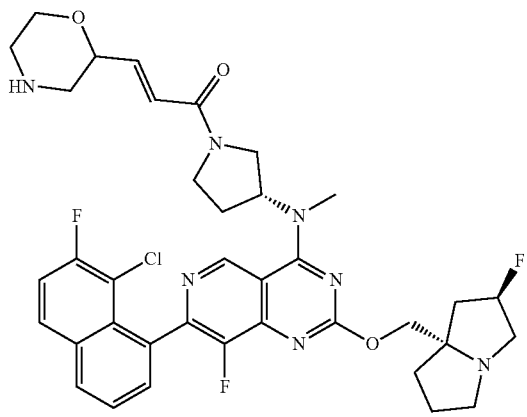

Example 122 (Method 8): (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-(oxetan-3-yl)-1,2,4-oxadiazol-5-yl)prop-2-en-1-one

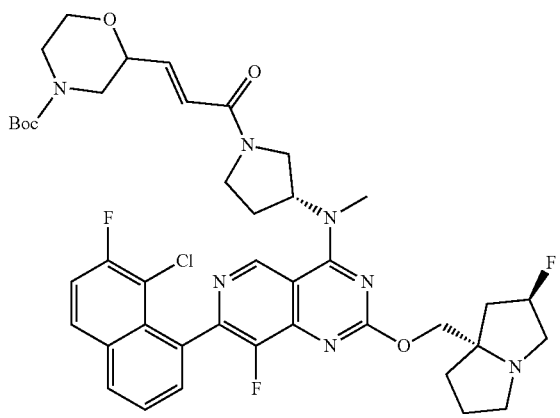 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)/C=C/C2CN(C(=O)OC(C)(C)C)CCO2)C1]

Step 1: tert-butyl 2-((E)-3-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-en-1-yl)morpholine-4-carboxylate The Homer-Wadsworth-Emmons reaction was prepared in a similar fashion to Method #8, Step 4. The reaction mixture was concentrated in vacuo affording tert-butyl 2-((E)-3-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-en-1-yl)morpholine-4-carboxylate (40 mg, crude) as a white solid, used in next step without any further purification. LCMS Rt=0.724 min, m/z=821.3 [M+H]$^+$.

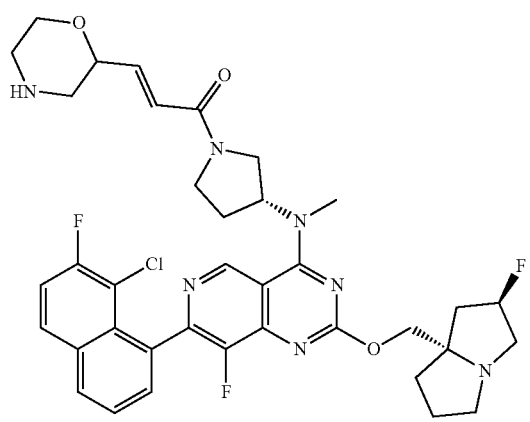 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)/C=C/C2CNCCO2)C1]

Step 2: (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-(oxetan-3-yl)-1,2,4-oxadiazol-5-yl)prop-2-en-1-one The deprotection of Boc group was prepared in a similar fashion to Method #8, Step 5. The residue was purified by reverse phase HPLC(column: Phenomenex Luna C18 75*30 mm*3 μm; mobile phase: [water (formic acid)-acetonitrile]; B %: 10%-40%, 8 min) affording (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-(oxetan-3-yl)-1,2,4-oxadiazol-5-yl)prop-2-en-1-one (7.5 mg, 19.96%, formic acid salt) as a white solid: $^1$H NMR (400 MHz, Acetonitrile-d3) δ 9.22 (s, 1H), 8.26 (s, 1H), 8.19-8.13 (m, 1H), 8.09 (dd, J=5.8, 9.0 Hz, 1H), 7.74-7.67 (m, 2H), 7.54 (t, J=8.9 Hz, 1H), 6.74-6.67 (m, 1H), 6.49-6.40 (m, 1H), 5.40 (br s, 1H), 5.37-5.24 (m, 1H), 4.37-4.25 (m, 2H), 4.24-4.01 (m, 2H), 4.00-3.79 (m, 3H), 3.72-3.51 (m, 3H), 3.45 (br s, 3H), 3.33 (br d, J=2.1 Hz, 2H), 3.00 (br s, 2H), 2.93-2.73 (m, 3H), 2.71-2.42 (m, 2H), 2.42-2.05 (m, 6H). LCMS Rt=1.881 min, m/z=721.3 [M +H]$^+$.

LCMS (5 to 95% acetonitrile in water+0.1% trifluoroacetic acid over 6 mins) retention time 1.881 min, ESI+ found [M+H]=721.3.

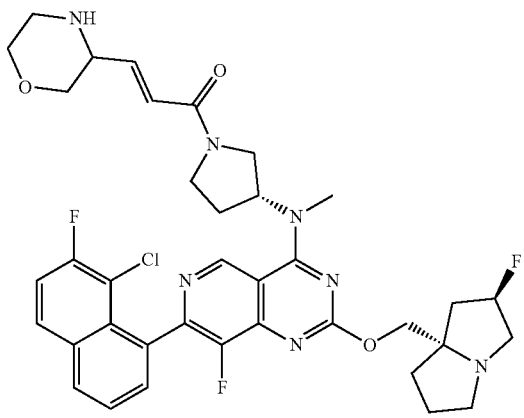 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)/C=C/C2COCCN2)C1]

Example 123 (Method 8): (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(morpholin-3-yl)prop-2-en-1-one

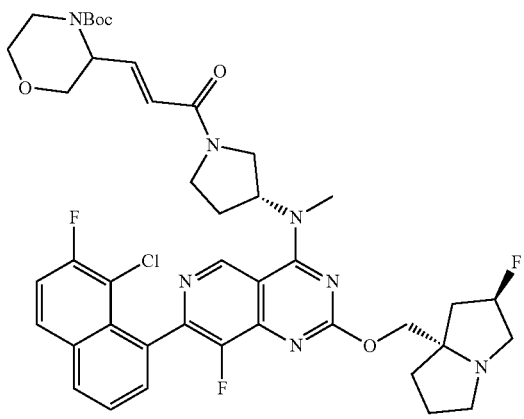 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)/C=C/C2COCCN2C(=O)OC(C)(C)C)C1]

Step 1: tert-butyl 3-((E)-3-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-en-1-yl)morpholine-4-carboxylate The Homer-Wadsworth-Emmons reaction was prepared in a similar fashion to Method #8, Step 4. The combined organic layers were concentrated under vacuo affording tert-butyl 3-((E)-3-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-en-1-yl)morpholine-4-carboxylate (100 mg, crude) as a yellow oil, used in the next step without further purification. LCMS Rt=0.602 min, m/z=821.3 [M+H]$^+$.

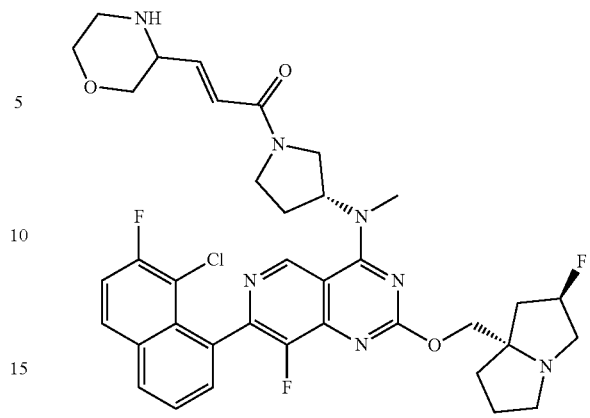

Step 2: (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(morpholin-3-yl)prop-2-en-1-one The deprotection of Boc group was prepared in a similar fashion to Method #5, Step 5. The residue was purified by reverse phase HPLC (column: Phenomenex Luna C18 75*30 mm*3 μm; mobile phase: [water (formic acid)-acetonitrile]; B %: 10%-40%, 8 min) affording (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(morpholin-3-yl)prop-2-en-1-one (16.01 mg, 13.01%, formate salt) as a yellow oil: $^1$H NMR (400 MHz, Acetonitrile-d3) δ 9.25-9.18 (m, 1H), 8.28 (br s, 1H), 8.18-8.05 (m, 2H), 7.73-7.66 (m, 2H), 7.54 (t, J=8.9 Hz, 1H), 6.72-6.62 (m, 1H), 6.58-6.32 (m, 1H), 5.49-5.27 (m, 2H), 4.48-4.29 (m, 2H), 4.20-4.08 (m, 1H), 4.06-3.73 (m, 4H), 3.52 (br d, J=8.8 Hz, 7H), 3.37-3.14 (m, 3H), 3.13-2.85 (m, 3H), 2.49-2.13 (m, 6H), 2.11-2.00 (m, 2H). LCMS Rt=1.966 min, m/z=721.3 [M+H]$^+$.

LCMS (5 to 95% acetonitrile in water+0.1% trifluoroacetic acid over 6 mins) retention time 1.966 min, ESI+ found [M+H]=721.3.

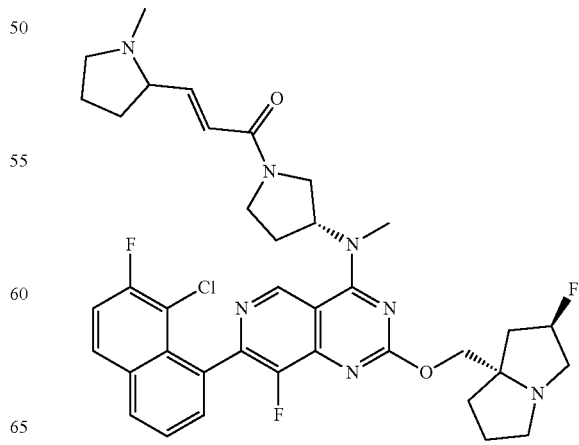

Example 124 (Method 7): (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(1-methylpyrrolidin-2-yl)prop-2-en-1-one

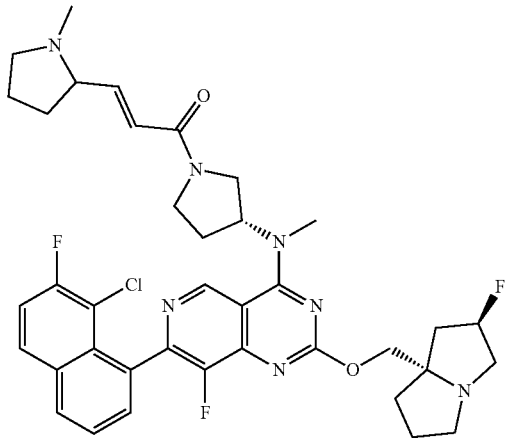 [SMILES: CN1CCCC1/C=C/C(=O)N1CC[C@@H](N(C)c2nc(OC[C@@]34CCCN3C[C@H](F)C4)nc3c(F)c(-c4cccc5ccc(F)c(Cl)c45)ncc23)C1]

Step 1: (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(1-methylpyrrolidin-2-yl)prop-2-en-1-one The reductive amination reaction was prepared in a similar fashion to Method #7, Step 4. The residue was purified by prep-HPLC (column: Phenomenex Luna C18 75*30 mm*3 μm; mobile phase: [water (formic acid)-acetonitrile]; B %: 10%-40%, 8 min) affording (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(1-methylpyrrolidin-2-yl)prop-2-en-1-one (19.24 mg, 31.44%, formic acid salt) as a yellow oil: $^1$H NMR (400 MHz, Acetonitrile-d3) δ 9.23 (s, 1H), 8.33 (br s, 1H), 8.17 (dd, J=3.6, 5.8 Hz, 1H), 8.11 (dd, J=5.7, 9.0 Hz, 1H), 7.76-7.68 (m, 2H), 7.56 (t, J=8.9 Hz, 1H), 6.70 (dd, J=8.3, 15.2 Hz, 1H), 6.52-6.35 (m, 1H), 5.47-5.23 (m, 2H), 4.38-4.21 (m, 2H), 4.18-3.80 (m, 2H), 3.73-3.57 (m, 1H), 3.52-3.41 (m, 4H), 3.37-3.16 (m, 4H), 3.10-2.93 (m, 2H), 2.56 (s, 1H), 2.47-2.36 (m, 4H), 2.35-2.27 (m, 2H), 2.24-2.06 (m, 3H), 1.96-1.70 (m, 5H). LCMS Rt=1.976 min, m/z=719.3 [M+H]$^+$.

LCMS (5 to 95% acetonitrile in water+0.1% trifluoroacetic acid over 6 mins) retention time 1.976 min, ESI+ found [M+H]=719.3.

Example 125 (Method 8): (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(1-methylazetidin-2-yl)prop-2-en-1-one

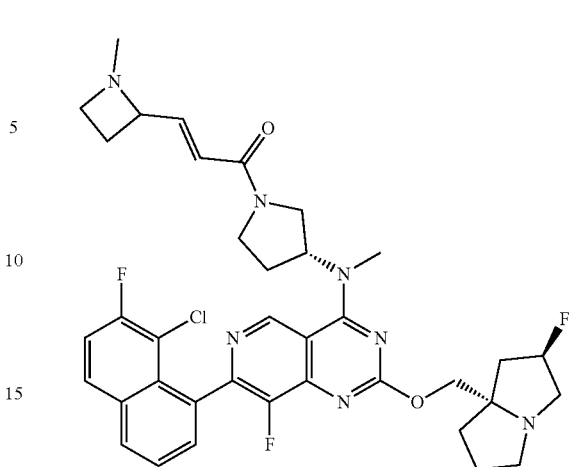

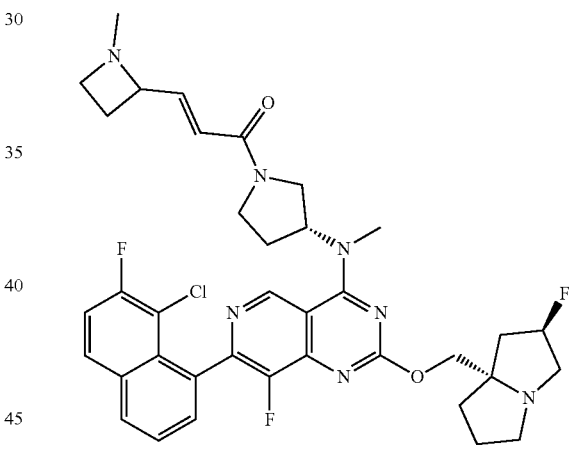

Step 1: (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(1-methylazetidin-2-yl)prop-2-en-1-one The reductive amination reaction was prepared in a similar fashion to Method #8, Step 6. The residue was purified by reverse phase HPLC (column: Waters Xbridge Prep OBD C18 150*40 mm*10 um; mobile phase: [water (NH$_4$HCO$_3$)-acetonitrile]; B %: 30%-60%, 8 min) affording (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(1-methylazetidin-2-yl)prop-2-en-1-one (30.75 mg, 17.18%) as a yellow solid: $^1$H NMR (400 MHz, Acetonitrile-d3) δ 9.21 (br d, J=1.8 Hz, 1H), 8.19-8.14 (m, 1H), 8.10 (dd, J=5.6, 9.1 Hz, 1H), 7.72-7.68 (m, 2H), 7.55 (t, J=8.9 Hz, 1H), 6.79 (dd, J=5.6, 15.1 Hz, 1H), 6.40 (dd, J=12.3, 14.4

Hz, 1H), 5.47-5.19 (m, 2H), 4.27-4.21 (m, 1H), 4.18-4.13 (m, 1H), 4.02-3.80 (m, 2H), 3.72-3.62 (m, 1H), 3.61-3.49 (m, 2H), 3.46 (br d, J=3.1 Hz, 3H), 3.36-3.28 (m, 1H), 3.19-3.13 (m, 2H), 3.08 (s, 1H), 2.97-2.87 (m, 1H), 2.86-2.77 (m, 1H), 2.48-2.33 (m, 2H), 2.26 (d, J=8.3 Hz, 3H), 2.13 (br s, 3H), 2.09-2.06 (m, 1H), 1.90 (br dd, J=7.9, 17.4 Hz, 4H). LCMS Rt=2.971 min, m/z=705.3 [M+H]$^+$.

LCMS (5 to 95% acetonitrile in water+0.03% ammonium bicarbonate over 6 mins) retention time 2.971 min, ESI+ found [M+H]=705.3.

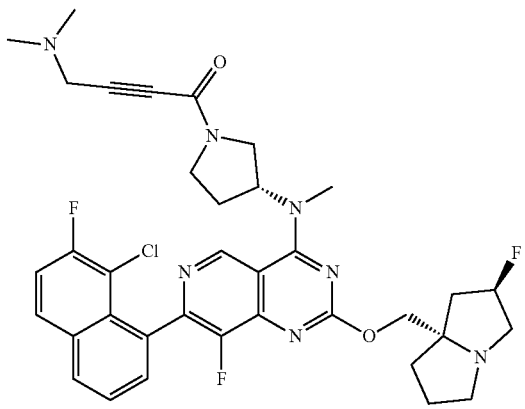 [SMILES: CN(C)CC#CC(=O)N1CC[C@@H](N(C)c2nc(OC[C@@]34CCCN3C[C@H](F)C4)nc3c(F)c(-c4cccc5ccc(F)c(Cl)c45)ncc23)C1]

Example 126 (Method 1): 1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-4-(dimethylamino)but-2-yn-1-one

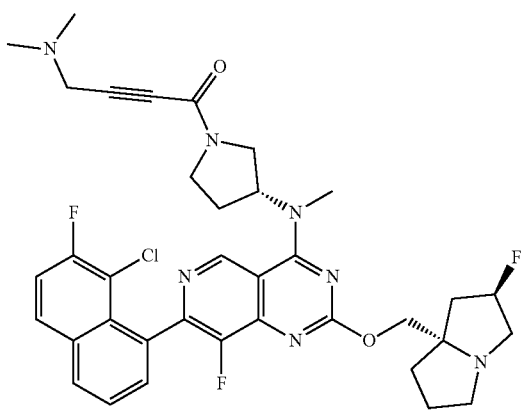 [SMILES: CN(C)CC#CC(=O)N1CC[C@@H](N(C)c2nc(OC[C@@]34CCCN3C[C@H](F)C4)nc3c(F)c(-c4cccc5ccc(F)c(Cl)c45)ncc23)C1]

Step 1: 1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-4-(dimethylamino)but-2-yn-1-one The amide coupling reaction was prepared in a similar fashion to Method #1, Step 10. The residue was purified by reverse phase HPLC (column: Waters Xbridge Prep OBD C18 150*40 mm*10 μm; mobile phase: [water (NH$_4$HCO$_3$)-acetonitrile]; B %: 30%-60%, 8 min) affording 1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-4-(dimethylamino)but-2-yn-1-one (18.72 mg, 10.37%) as a yellow solid: $^1$H NMR (400 MHz, Acetonitrile-d3) δ 9.20 (dd, J=1.6, 4.5 Hz, 1H), 8.18-8.11 (m, 1H), 8.08 (dd, J=5.7, 9.1 Hz, 1H), 7.72-7.64 (m, 2H), 7.53 (t, J=8.9 Hz, 1H), 5.46-5.17 (m, 2H), 4.24-4.18 (m, 1H), 4.17-4.11 (m, 1H), 4.05-3.86 (m, 1H), 3.80-3.66 (m, 2H), 3.56-3.47 (m, 1H), 3.46 (d, J=3.5 Hz, 2H), 3.43 (s, 3H), 3.20-3.09 (m, 2H), 3.07 (s, 1H), 2.95-2.86 (m, 1H), 2.43-2.31 (m, 2H), 2.29 (s, 3H), 2.28-2.22 (m, 3H), 2.18 (br s, 2H), 2.11 (br d, J=2.9 Hz, 1H), 2.08-2.03 (m, 1H), 1.90-1.83 (m, 2H). LCMS Rt=2.948 min, m/z=691.3 [M+H]$^+$.

LCMS (5 to 95% acetonitrile in water+0.03% ammonium bicarbonate over 6 mins) retention time 2.948 min, ESI+ found [M+H]=691.3.

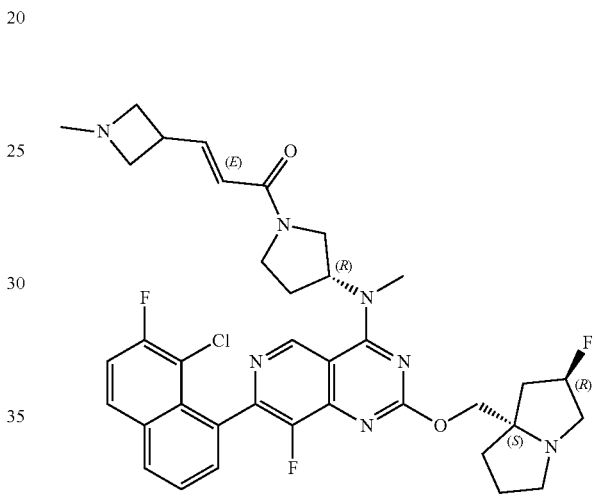

Example 127 (Method 8): (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(1-methylazetidin-3-yl)prop-2-en-1-one

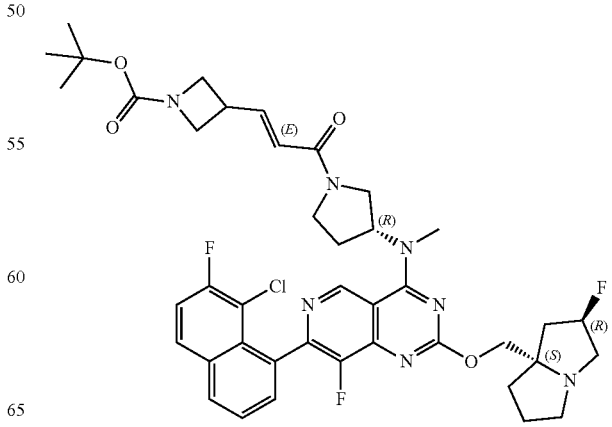

Step 1: tert-butyl 3-((E)-3-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-en-1-yl)azetidine-1-carboxylate The Homer-Wadsworth-Emmons reaction was prepared in a similar fashion to Method #8, Step 4. The combined organic layers were concentrated under vacuo affording tert-butyl 3-((E)-3-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-en-1-yl)azetidine-1-carboxylate (200 mg, crude) as a yellow oil, used in the next step without further purification. LCMS Rt=0.600 min, m/z=791.3 [M+H]⁺.

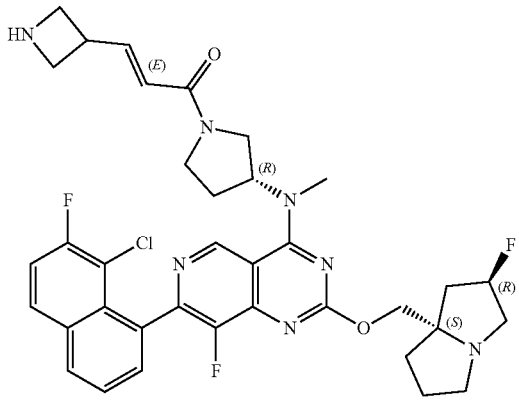

Step 2: (E)-3-(azetidin-2-yl)-1-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)prop-2-en-1-one The deprotection of Boc group was prepared in a similar fashion to Method #8, Step 5. The reaction mixture was concentrated under vacuo affording (E)-3-(azetidin-2-yl)-1-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)prop-2-en-1-one (150 mg, crude, trifluoroacetic acid salt) as a yellow oil. LCMS Rt=0.662 min, m/z=691.3 [M+H]⁺.

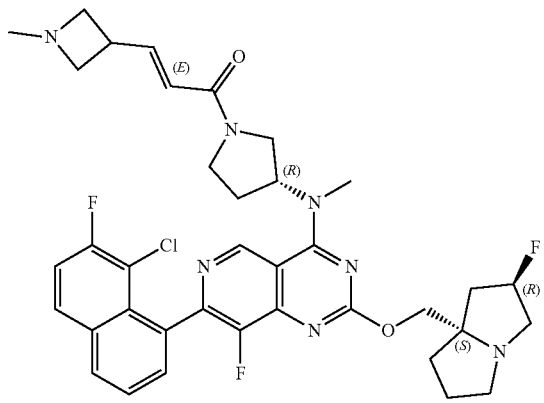

Step 3: (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(1-methylazetidin-3-yl)prop-2-en-1-one The reductive amination reaction was prepared in a similar fashion to Method #8, Step 6. The residue was purified by reverse phase HPLC (column: Waters Xbridge BEH C18 100*30 mm*10 um; mobile phase: [water (NH₄HCO₃)-acetonitrile]; B %: 30%-60%, 8 min) affording (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(1-methylazetidin-3-yl)prop-2-en-1-one (30.75 mg, 17.18%) as a yellow solid. ¹HNMR (400 MHz, Acetonitrile-d3) δ 9.21 (s, 1H), 8.21-8.04 (m, 2H), 7.78-7.64 (m, 2H), 7.54 (t, J=8.9 Hz, 1H), 7.01-6.88 (m, 1H), 6.39-6.16 (m, 1H), 5.48-5.16 (m, 2H), 4.26-4.19 (m, 1H), 4.17-4.11 (m, 1H), 4.11-4.02 (m, 1H), 4.01-3.92 (m, 1H), 3.91-3.77 (m, 1H), 3.69-3.52 (m, 2H), 3.49-3.39 (m, 6H), 3.26-3.19 (m, 1H), 3.18-3.12 (m, 2H), 3.08 (s, 1H), 2.99-2.88 (m, 3H), 2.43-2.37 (m, 1H), 2.31 (br d, J=5.6 Hz, 1H), 2.24 (d, J=5.4 Hz, 3H), 2.12 (br d, J=2.6 Hz, 1H), 2.09-2.05 (m, 1H), 1.88 (br dd, J=7.3, 10.8 Hz, 2H). LCMS Rt =1.874 min, m/z=705.3 [M+H]⁺.

LCMS (5 to 95% acetonitrile in water+0.03% ammonium bicarbonate over 6 min) retention time 1.874 min, ESI+ found [M+H]=705.3.

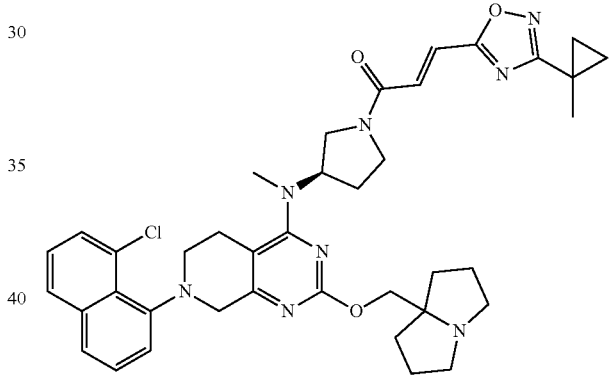

Example 128 (Method 4): (R,E)-1-(3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-(1-methylcyclopropyl)-1,2,4-oxadiazol-5-yl)prop-2-en-1-one

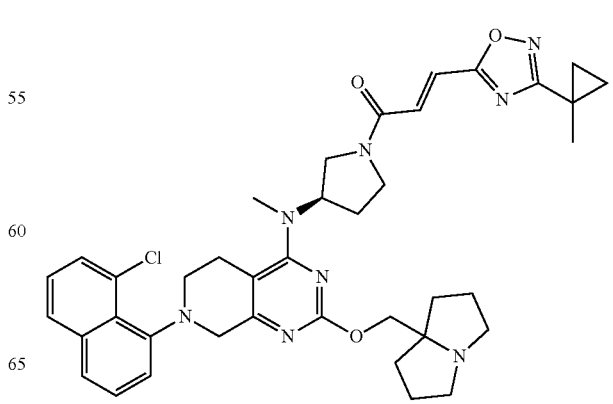

Step 1: (R,E)-1-(3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-(1-methylcyclopropyl)-1,2,4-oxadiazol-5-yl)prop-2-en-1-one The amide coupling reaction was prepared in a similar fashion to Method #4, Step 11. The crude product was purified by reverse phase HPLC (column: Waters Xbridge Prep OBD C18 150*40 mm*10 μm; mobile phase: [water (ammonium bicarbonate- acetonitrile]; B %: 60%-95%, 8 min) affording (R,E)-1-(3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-(1-methylcyclopropyl)-1,2,4-oxadiazol-5-yl)prop-2-en-1-one (5.17 mg, 4.28%) as a yellow oil: $^1$H NMR (400 MHz, Acetonitrile-d3) δ 7.85 (d, J=8.0 Hz, 1H), 7.68 (br d, J=8.4 Hz, 1H), 7.55 (d, J=7.5 Hz, 1H), 7.50 (dt, J=3.9, 7.8 Hz, 1H), 7.42-7.35 (m, 2H), 7.35-7.26 (m, 2H), 4.88-4.74 (m, 1H), 4.29-4.21 (m, 1H), 4.16-3.89 (m, 3H), 3.87-3.59 (m, 3H), 3.57-3.40 (m, 2H), 3.15-3.02 (m, 3H), 3.01-2.95 (m, 3H), 2.73-2.56 (m, 4H), 1.96 (br s, 2H), 1.92-1.75 (m, 6H), 1.71-1.60 (m, 2H), 1.49 (d, J=3.3 Hz, 3H), 1.20-1.14 (m, 2H), 0.94-0.89 (m, 2H). LCMS Rt=3.436 min, m/z=708.3 [M+H]$^+$.

LCMS (5 to 95% acetonitrile in water+0.03% ammonium bicarbonate over 6 mins) retention time 3.436 min, ESI+ found [M+H]=708.3.

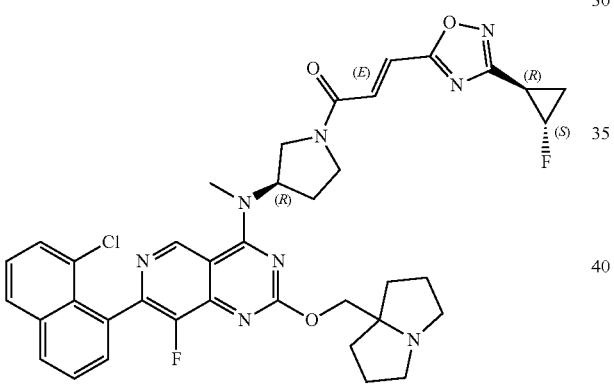

Example 129 (Method 2): (E)-1-((R)-3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-((1R,2S)-2-fluorocyclopropyl)-1,2,4-oxadiazol-5-yl)prop-2-en-1-one

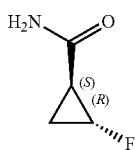

Step 1: (1S,2R)-2-fluorocyclopropanecarboxamide

The amide coupling reaction was prepared in a similar fashion to Method #5, Step 1. The resulting residue was purified by column chromatography (silica gel, 100-200 mesh, 90-100% ethyl acetate in petroleum ether) affording (1S,2R)-2-fluorocyclopropanecarboxamide (6.5 g, 65.62%) as a white solid: $^1$H NMR (400 MHz, Methanol-d4) δ 4.85-4.60 (m, 1H), 2.15-2.00 (m, 1H), 1.47-1.31 (m, 1H), 1.23 (qd, J=6.5, 12.8 Hz, 1H).

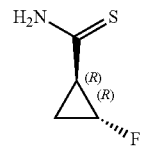

Step 2: (1R,2R)-2-fluorocyclopropanecarbothioamide

The sulfamide formation was prepared in a similar fashion to Method #5, Step 2.

The crude residue was purified by column chromatography (silica gel, 100-200 mesh, 0-20% ethyl acetate in petroleum ether) affording (1R,2R)-2-fluorocyclopropanecarbothioamide (3 g, 86.52%) as a white solid: $^1$H NMR (400 MHz, Methanol-d4) δ 4.88 (ddd, J=1.5, 3.4, 6.1 Hz, 0.5H), 4.72 (ddd, J=1.4, 3.5, 6.0 Hz, 0.5H), 2.53-2.39 (m, 1H), 1.64-1.56 (m, 1H), 1.56-1.43 (m, 1H).

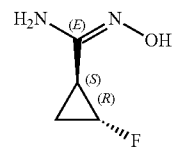

Step 3: (1S,2R,E)-2-fluoro-N'-hydroxycyclopropanecarboximidamide

The hydroxylimidamide formation was prepared in a similar fashion to Method #5, Step 3, the crude product was purified by flash column (silica gel, 100-200 mesh, 0-20% ethyl acetate in petroleum ether) affording (1S,2R,E)-2-fluoro-N'-hydroxycyclopropanecarboximidamide (2.6 g, 87.44%) as a yellow gum: $^1$H NMR (400 MHz, Methanol-d4) δ 4.84-4.63 (m, 1H), 1.91 (dddd, J=1.9, 7.3, 11.3, 18.5 Hz, 1H), 1.36-1.23 (m, 1H), 1.14 (qd, J=6.9, 11.2 Hz, 1H).

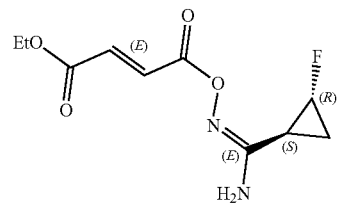

Step 4: (E)-ethyl 4-(((E)-(amino((1S,2R)-2-fluorocyclopropyl)methylene)amino)oxy)-4-oxobut-2-enoate The amide coupling reaction was prepared in a similar fashion to Method #5, Step 4.

The crude product was purified by flash column (silica gel, 100-200 mesh, 0-20% ethyl acetate in petroleum ether)

affording (E)-ethyl 4-(((E)-(amino((1S,2R)-2-fluorocyclopropyl)methylene)amino)oxy)-4-oxobut-2-enoate (3.6 g, 69.64%) as a yellow oil: ¹H NMR (400 MHz, Methanol-d4) δ 7.00-6.85 (m, 2H), 4.93 (ddd, J=2.0, 3.2, 6.2 Hz, 0.5H), 4.77 (ddd, J=2.1, 3.3, 6.1 Hz, 0.5H), 4.26 (q, J=7.1 Hz, 2H), 2.01-1.92 (m, 1H), 1.45-1.35 (m, 1H), 1.34-1.30 (m, 3H), 1.30-1.22 (m, 1H).

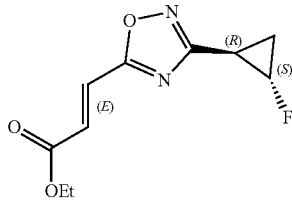

Step 5: (E)-ethyl 3-(3-((1R,2S)-2-fluorocyclopropyl)-1,2,4-oxadiazol-5-yl)acrylate The cyclization reaction was prepared in a similar fashion to Method #5, Step 5.

The resulting residue was purified by column chromatography (silica gel, 100-200 mesh, 30-50% ethyl acetate in petroleum ether) affording (E)-ethyl 3-(3-((1R,2S)-2-fluorocyclopropyl)-1,2,4-oxadiazol-5-yl)acrylate (1.5 g, 80.97%) as a yellow oil: ¹H NMR (400 MHz, Methanol-d4) δ 7.44 (d, J=16.0 Hz, 1H), 7.00 (d, J=16.1 Hz, 1H), 5.08-4.88 (m, 1H), 4.30 (q, J=7.1 Hz, 2H), 2.71-2.55 (m, 1H), 1.79-1.62 (m, 1H), 1.44-1.36 (m, 1H), 1.36-1.32 (m, 3H). LCMS Rt=0.768 min, m/z=226.1 [M+H]⁺.

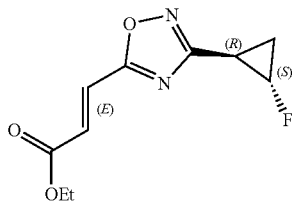

Step 6: (E)-3-(3-((1R,2S)-2-fluorocyclopropyl)-1,2,4-oxadiazol-5-yl)acrylic acid The hydrolysis reaction was prepared in a similar fashion to Method #5, Step 8.

The reaction mixture was quenched with hydrochloric acid (1M, 20 mL) and adjusted pH to 2, then extracted with dichloromethane (3×20 mL). The combined organic layers were dried over sodium sulphate and concentrated in vacuo affording (E)-3-(3-((1R,2S)-2-fluorocyclopropyl)-1,2,4-oxadiazol-5-yl)acrylic acid (1.2 g, 91.33%) as a white solid, used in next step without any further purification: ¹H NMR (400 MHz, Chloroform-d) δ 7.52 (d, J=16.0 Hz, 1H), 7.00 (d, J=16.0 Hz, 1H), 5.08-4.81 (m, 1H), 2.63 (dddd, J=1.9, 7.0, 11.1, 17.0 Hz, 1H), 1.77-1.62 (m, 1H), 1.41 (qd, J=6.8, 12.1 Hz, 1H). LCMS Rt=0.572 min, m/z=198.0 [M+H]⁺.

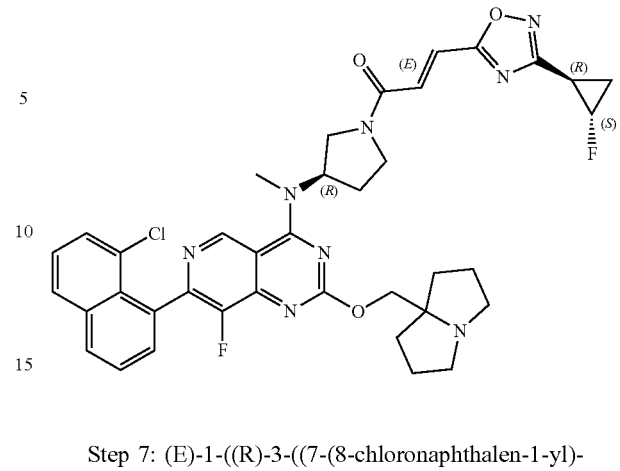

Step 7: (E)-1-((R)-3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-((1R,2S)-2-fluorocyclopropyl)-1,2,4-oxadiazol-5-yl)prop-2-en-1-one The amide coupling reaction was prepared in a similar fashion to Method #2, Step 7. The residue was purified by reverse phase HPLC (column: Waters Xbridge BEH C18 100*30 mm*10 μm; mobile phase: [water (NH₄HCO₃)-acetonitrile]; B %: 35%-65%, 10 min) affording (E)-1-((R)-3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-((1R,2S)-2-fluorocyclopropyl)-1,2,4-oxadiazol-5-yl)prop-2-en-1-one (8.97 mg, 7.72%) as a yellow solid: ¹H NMR (400 MHz, Acetonitrile-d3) δ 9.21 (t, J=1.8 Hz, 1H), 8.15 (d, J=8.0 Hz, 1H), 8.04 (d, J=7.6 Hz, 1H), 7.74-7.68 (m, 1H), 7.67-7.61 (m, 2H), 7.57-7.51 (m, 1H), 7.51-7.40 (m, 1H), 7.37 (d, J=5.3 Hz, 1H), 5.49-5.32 (m, 1H), 5.10-4.85 (m, 1H), 4.22-4.15 (m, 2H), 4.08-3.98 (m, 1H), 3.96-3.72 (m, 2H), 3.69-3.51 (m, 1H), 3.48-3.41 (m, 3H), 3.32-3.04 (m, 1H), 2.98 (dt, J=3.5, 9.4 Hz, 2H), 2.69-2.55 (m, 3H), 2.49-2.39 (m, 1H), 2.39-2.29 (m, 2H), 1.74 (br dd, J=3.7, 7.3 Hz, 5H), 1.69-1.59 (m, 2H), 1.44-1.31 (m, 1H). LCMS Rt=2.359 min, m/z=726.3 [M+H]⁺.

LCMS (5 to 95% acetonitrile in water+0.1% trifluoroacetic acid over 6 mins) retention time 2.359 min, ESI+ found [M+H]=726.3.

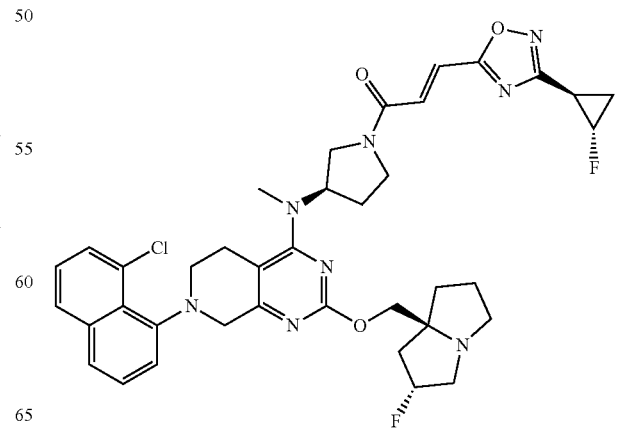

Example 130 (Method 4): (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-((1R,2S)-2-fluorocyclopropyl)-1,2,4-oxadiazol-5-yl)prop-2-en-1-one

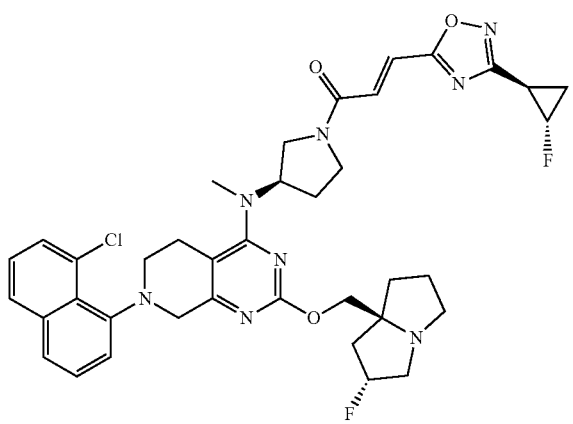 [SMILES: CN(c1nc(OC[C@@]23CCCN2C[C@H](F)C3)nc2c1CCN(c1cccc3cccc(Cl)c13)C2)[C@@H]1CCN(C(=O)/C=C/c2nc([C@H]3C[C@@H]3F)no2)C1]

Step 1: (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-((1R,2S)-2-fluorocyclopropyl)-1,2,4-oxadiazol-5-yl)prop-2-en-1-one The amide coupling reaction was prepared in a similar fashion to Method #4, Step 11. The crude was purified by reverse phase HPLC (column: Waters Xbridge BEH C18 100*30 mm*10 μm; mobile phase: [water (NH$_4$HCO$_3$)-acetonitrile]; B %: 50%-80%, 10 min) affording (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-((1R,2S)-2-fluorocyclopropyl)-1,2,4-oxadiazol-5-yl)prop-2-en-1-one (32.58 mg, 32.72%) as a yellow solid: $^1$H NMR (400 MHz, Acetonitrile-d3) δ 7.88 (d, J=8.3 Hz, 1H), 7.73-7.68 (m, 1H), 7.60-7.56 (m, 1H), 7.55-7.50 (m, 1H), 7.48-7.39 (m, 2H), 7.39-7.30 (m, 2H), 5.38-5.13 (m, 1H), 5.12-4.89 (m, 1H), 4.88-4.72 (m, 1H), 4.34-4.22 (m, 1H), 4.19-4.05 (m, 1H), 4.05-3.97 (m, 1H), 3.96-3.91 (m, 1H), 3.89-3.77 (m, 1H), 3.77-3.61 (m, 2H), 3.59-3.41 (m, 2H), 3.19 (br s, 1H), 3.16-3.07 (m, 3H), 3.07-3.03 (m, 1H), 3.02-2.98 (m, 3H), 2.93-2.83 (m, 1H), 2.70-2.59 (m, 2H), 2.37-2.19 (m, 2H), 2.14-2.10 (m, 1H), 2.09-2.00 (m, 2H), 1.92-1.69 (m, 4H), 1.42-1.32 (m, 1H). LCMS Rt=2.455 min, m/z=730.3 [M+H]$^+$.

LCMS (5 to 95% acetonitrile in water+0.03% ammonium bicarbonate over 6 mins) retention time 2.455 min, ESI+ found [M+H]=730.3.

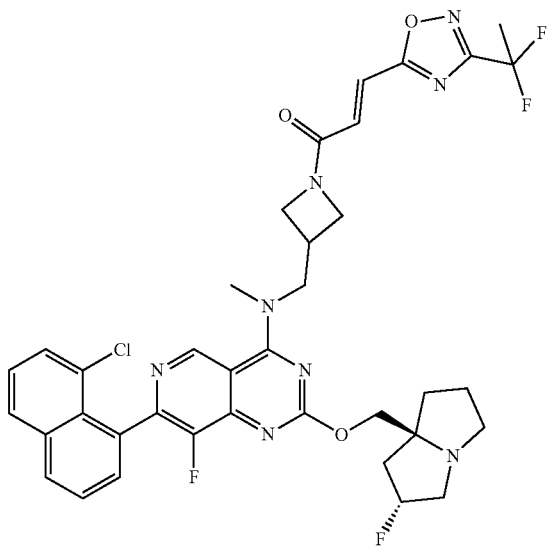 [SMILES: CN(CC1CN(C(=O)/C=C/c2nc(C(C)(F)F)no2)C1)c1nc(OC[C@@]23CCCN2C[C@H](F)C3)nc2c(F)c(-c3cccc4cccc(Cl)c34)ncc12]

Example 131 (Method 1): (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-(1,1-difluoroethyl)-1,2,4-oxadiazol-5-yl)prop-2-en-1-one

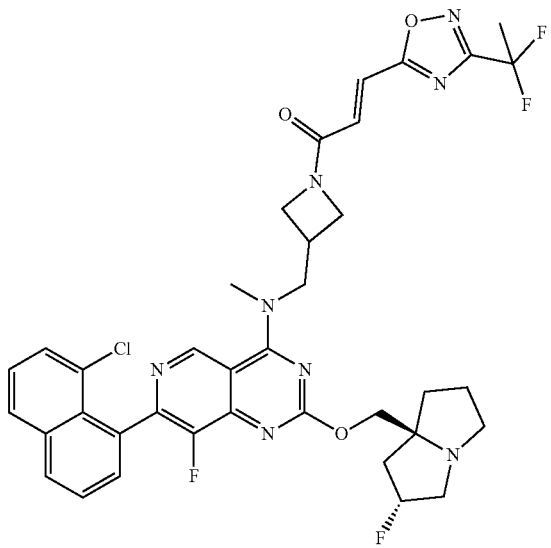 [SMILES: CN(CC1CN(C(=O)/C=C/c2nc(C(C)(F)F)no2)C1)c1nc(OC[C@@]23CCCN2C[C@H](F)C3)nc2c(F)c(-c3cccc4cccc(Cl)c34)ncc12]

Step 1: (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-(1,1-difluoroethyl)-1,2,4-oxadiazol-5-yl)prop-2-en-1-one The amide coupling reaction was prepared in a similar fashion to Method #1, Step 10. The residue was purified by reverse phase HPLC (column: Waters Xbridge Prep OBD C18 150*40 mm*10 um; mobile phase: [water (NH$_4$HCO$_3$)-acetonitrile]; B %: 40%-70%, 8 min) affording (E)-1-(3-

(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-(1,1-difluoroethyl)-1,2,4-oxadiazol-5-yl)prop-2-en-1-one (10.4 mg, 6.28%) as a white solid: ¹H NMR (400 MHz, Acetonitrile-d3) δ 9.28 (s, 1H), 8.16 (d, J=8.4 Hz, 1H), 8.06 (d, J=8.2 Hz, 1H), 7.76-7.70 (m, 1H), 7.65 (br d, J=7.7 Hz, 2H), 7.58-7.53 (m, 1H), 7.46-7.40 (m, 1H), 7.34-7.28 (m, 1H), 5.39-5.19 (m, 1H), 4.53 (t, J=8.9 Hz, 1H), 4.28-4.19 (m, 4H), 4.05-3.95 (m, 1H), 3.63 (s, 3H), 3.32-3.08 (m, 5H), 2.96-2.88 (m, 1H), 2.17 (br s, 3H), 2.13 (s, 3H), 2.08 (s, 2H), 1.92-1.86 (m, 2H). LCMS Rt=2.284 min, m/z=750.3 [M+H]⁺.

LCMS (5 to 95% acetonitrile in water+0.1% trifluoroacetic acid over 6 mins) retention time 2.284 min, ESI+ found [M+H]=750.3.

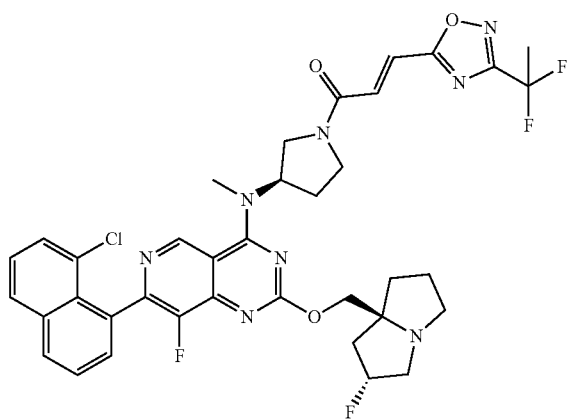 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2nc(C(C)(F)F)no2)C1]

Example 132 (Method 1): (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-(1,1-difluoroethyl)-1,2,4-oxadiazol-5-yl)prop-2-en-1-one

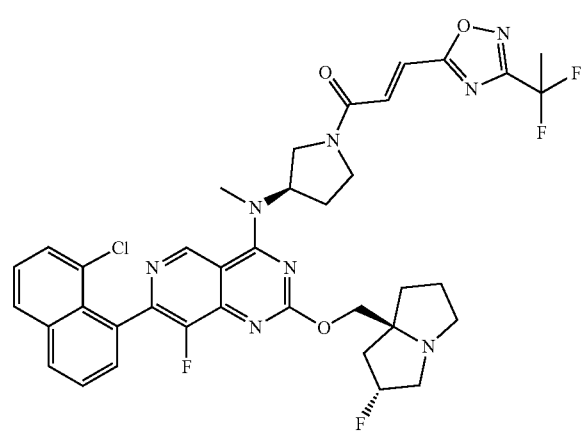 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2nc(C(C)(F)F)no2)C1]

Step 1: (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-(1,1-difluoroethyl)-1,2,4-oxadiazol-5-yl)prop-2-en-1-one The amide coupling reaction was prepared in a similar fashion to Method #1, Step 10. The residue was purified by reverse phase HPLC (column: Waters Xbridge Prep OBD C18 150*40 mm*10 um; mobile phase: [water (NH₄HCO₃)-acetonitrile]; B %: 40%-70%, 8 min) affording (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-(1,1-difluoroethyl)-1,2,4-oxadiazol-5-yl)prop-2-en-1-one (10.07 mg, 15.89%) as a yellow amorphous solid: ¹H NMR (400 MHz, Acetonitrile-d3) δ 9.12 (t, J=1.8 Hz, 1H), 8.04 (dd, J=1.1, 8.1 Hz, 1H), 7.96-7.92 (m, 1H), 7.63-7.59 (m, 1H), 7.56-7.51 (m, 2H), 7.50-7.44 (m, 1H), 7.45-7.41 (m, 1H), 7.40-7.33 (m, 1H), 5.38-5.27 (m, 1H), 5.26-5.09 (m, 1H), 4.17-4.12 (m, 1H), 4.10-4.02 (m, 1H), 3.99-3.90 (m, 1H), 3.89-3.77 (m, 1H), 3.75-3.65 (m, 1H), 3.60-3.42 (m, 1H), 3.36 (s, 3H), 3.13-2.96 (m, 3H), 2.86-2.77 (m, 1H), 2.39-2.22 (m, 2H), 2.16-2.06 (m, 3H), 2.01-1.92 (m, 3H), 1.83-1.66 (m, 3H). LCMS Rt=2.305 min, m/z=750.3 [M+H]⁺.

LCMS (5 to 95% acetonitrile in water+0.03% ammonium bicarbonate over 6 mins) retention time 2.305 min, ESI+ found [M+H]=750.3

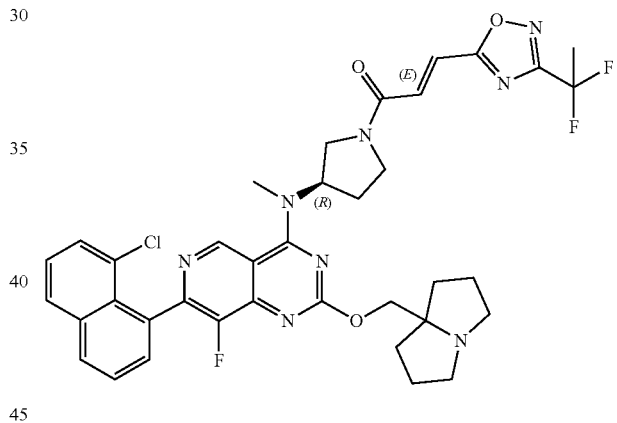

Example 133 (Method 1): (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-(1,1-difluoroethyl)-1,2,4-oxadiazol-5-yl)prop-2-en-1-one

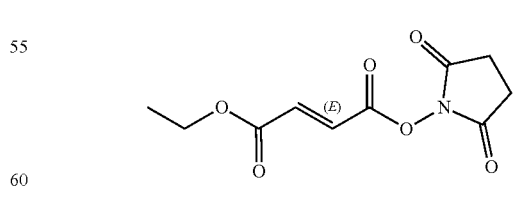

Step 1: (E)-ethyl 4-(((E)-(1-amino-2,2-difluoropropylidene)amino)oxy)-4-oxobut-2-enoate To a solution of (E)-4-ethoxy-4-oxo-but-2-enoic acid (5 g, 34.69 mmol), 1-hydroxypyrrolidine-2,5-dione (12 g, 104.27

711 mmol) in acetonitrile (100 mL) was added 1-(3-Dimethylaminopropyl)-3-ethylcarbodiimide (13.30 g, 69.38 mmol) at 0° C. The mixture was stirred at 25° C. for 12 h. The mixture was diluted with water (50 mL) and extracted with ethyl acetate (3×50 mL). The combined organic layers were dried over sodium sulphate and concentrated in vacuo affording (E)-ethyl 4-(((E)-(1-amino-2,2-difluoropropylidene)amino)oxy)-4-oxobut-2-enoate (16.8 g, crude) as a yellow oil, used into the next step without further purification.

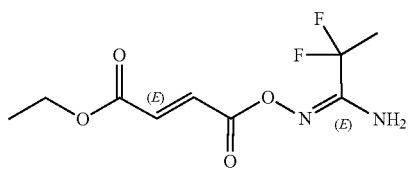 [SMILES: CCOC(=O)/C=C/C(=O)O/N=C(/N)C(C)(F)F]

Step 2: (E)-ethyl 4-(((E)-(1-amino-2,2-difluoropropylidene)amino)oxy)-4-oxobut-2-enoate To a solution of 2,2-difluoro-N'-hydroxy-propanamidine (2.4 g, 19.34 mmol) in dioxane (100 mL) was added potassium carbonate (8.02 g, 58.02 mmol) and O4-(2,5-dioxopyrrolidin-1-yl) O1-ethyl (E)-but-2-enedioate (6.06 g, 25.14 mmol) at 0° C. The mixture was stirred at 25° C. for 12 h. The mixture was diluted with water (20 mL) and extracted with ethyl acetate (3×50 mL). The combined organic layers were dried over sodium sulphate and concentrated in vacuo affording (E)-ethyl 4-(((E)-(1-amino-2,2-difluoropropylidene)amino)oxy)-4-oxobut-2-enoate (3.6 g, crude) as a brown oil, used in next step without further purification. LCMS Rt=0.510 min, m/z=250.1 [M+H]$^+$.

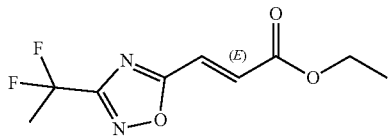 [SMILES: CCOC(=O)/C=C/c1nc(C(C)(F)F)no1]

Step 3: ethyl (E)-3-[3-(1,1-difluoroethyl)-1,2,4-oxadiazol-5-yl]prop-2-enoate

The cyclization reaction was prepared in a similar fashion to Method #1, Step 3. The residue was purified by column chromatography (silica gel, 100-200 mesh, 0-100% ethyl acetate in petroleum ether) affording ethyl (E)-3-[3-(1,1-difluoroethyl)-1,2,4-oxadiazol-5-yl]prop-2-enoate (1.1 g, 32.04%) as a white solid. LCMS Rt=0.633 min, m/z=232.1 [M+H]$^+$.

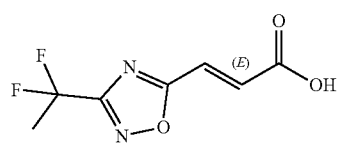

712

Step 4: (E)-3-[3-(1,1-difluoroethyl)-1,2,4-oxadiazol-5-yl]prop-2-enoic acid

The hydrolysis reaction was prepared in a similar fashion to Method #1, Step 4.

The reaction mixture was quenched with hydrochloric acid (1M, 20 mL) and adjusted pH to 2, then extracted with dichloromethane (3×20 mL). The combined organic layers were dried over sodium sulphate and concentrated in vacuo affording (E)-3-[3-(1,1-difluoroethyl)-1,2,4-oxadiazol-5-yl]prop-2-enoic acid (1 g, crude) as a white solid, used in next step without further purification.

LCMS Rt=0.545 min, m/z=204.0 [M+H]$^+$.

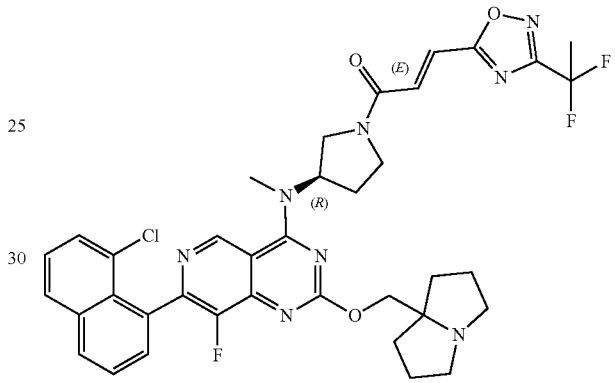

Step 5: (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-(1,1-difluoroethyl)-1,2,4-oxadiazol-5-yl)prop-2-en-1-one The amide coupling reaction was prepared in a similar fashion to Method #1, Step 10. The residue was purified by reverse phase HPLC(column: Phenomenex Luna C18 75*30 mm*3 µm; mobile phase: [water (formic acid)-acetonitrile]; B %: 20%-50%, 8 min) affording (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-(1,1-difluoroethyl)-1,2,4-oxadiazol-5-yl)prop-2-en-1-one (2.24 mg, 1.90%, formate salt) as a white solid: $^1$H NMR (400 MHz, Acetonitrile-d3) δ 9.22 (s, 1H), 8.15 (d, J=8.1 Hz, 1H), 8.05 (d, J=8.1 Hz, 1H), 7.75-7.69 (m, 1H), 7.64 (br d, J=7.4 Hz, 2H), 7.61-7.52 (m, 2H), 7.50-7.44 (m, 1H), 5.52-5.36 (m, 1H), 4.26-4.20 (m, 2H), 4.10-4.00 (m, 1H), 3.95-3.76 (m, 2H), 3.71-3.53 (m, 1H), 3.47 (s, 3H), 3.11-2.98 (m, 2H), 2.74-2.61 (m, 2H), 2.48-2.37 (m, 2H), 2.12 (dt, J=8.1, 19.2 Hz, 4H), 1.93-1.78 (m, 5H), 1.75-1.64 (m, 2H). LCMS Rt=2.354 min, m/z=732.3 [M+H]$^+$.

LCMS (5 to 95% acetonitrile in water+0.1% trifluoroacetic acid over 6 mins) retention time 2.354 min, ESI+ found [M+H]=732.3.

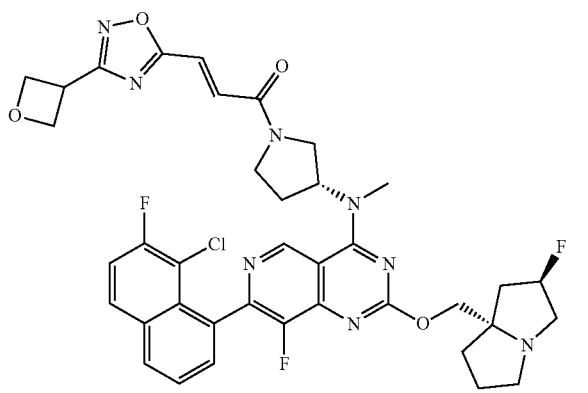 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)/C=C/c2nc(C3COC3)no2)C1]

Example 134 (Method 1): (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-(oxetan-3-yl)-1,2,4-oxadiazol-5-yl)prop-2-en-1-one

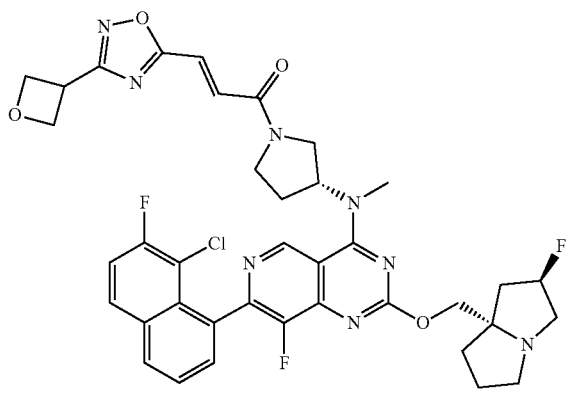 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)/C=C/c2nc(C3COC3)no2)C1]

Step 1: (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-(oxetan-3-yl)-1,2,4-oxadiazol-5-yl)prop-2-en-1-one The amide coupling reaction was prepared in a similar fashion to Method #1, Step 10. The residue was purified by reverse phase HPLC (column: Waters Xbridge Prep OBD C18 150*40 mm*10 μm; mobile phase: [water (NH$_4$HCO$_3$)-acetonitrile]; B %: 35%-65%, 8 min) affording (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-(oxetan-3-yl)-1,2,4-oxadiazol-5-yl)prop-2-en-1-one (32.88 mg, 27.31%) as a white solid: $^1$H NMR (400 MHz, Acetonitrile-d3) δ 9.22 (s, 1H), 8.20-8.05 (m, 2H), 7.74-7.65 (m, 2H), 7.59-7.50 (m, 2H), 7.49-7.40 (m, 1H), 5.48-5.16 (m, 2H), 5.00 (dt, J =6.1, 8.4 Hz, 2H), 4.88-4.80 (m, 2H), 4.52-4.41 (m, 1H), 4.26-4.21 (m, 1H), 4.18-4.12 (m, 1H), 4.07-3.99 (m, 1H), 3.95-3.76 (m, 2H), 3.71-3.52 (m, 1H), 3.47 (s, 2H), 3.41 (br s, 1H), 3.22-3.03 (m, 3H), 2.90 (quin, J=7.1 Hz, 1H), 2.51-2.31 (m, 2H), 2.12 (br s, 2H), 2.09-2.01 (m, 1H), 1.93-1.84 (m, 3H). LCMS Rt=2.183 min, m/z=760.3 [M+H]$^+$.

LCMS (5 to 95% acetonitrile in water+0.1% trifluoroacetic acid over 6 mins) retention time 2.183 min, ESI+ found [M+H]=760.3.

Example 135 (Method 8): (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(1-methyl-1H-imidazol-4-yl)prop-2-en-1-one

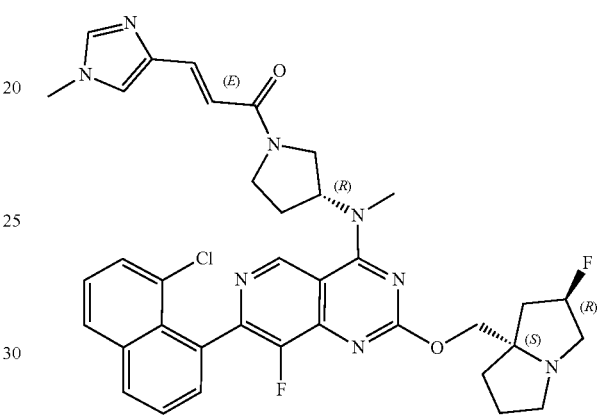

Step 1: (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(1-methyl-1H-imidazol-4-yl)prop-2-en-1-one The Homer-Wadsworth-Emmons reaction was prepared in a similar fashion to Method #8, Step 4. The crude was purified by reverse phase HPLC (column: Waters Xbridge Prep OBD C18 150*40 mm*10 um; mobile phase: [water (NH$_4$HCO$_3$)-acetonitrile]; B %: 40%-70%, 8 min) affording (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(1-methyl-1H-imidazol-4-yl)prop-2-en-1-one (23.62 mg, 22.52%) as a yellow solid: $^1$H NMR (400 MHz, Acetonitrile-d3) δ 9.22 (s, 1H), 8.15 (dd, J=1.1, 8.1 Hz, 1H), 8.07-8.01 (m, 1H), 7.75-7.69 (m, 1H), 7.67-7.62 (m, 2H), 7.57-7.51 (m, 1H), 7.50-7.44 (m, 2H), 7.24 (d, J=4.1 Hz, 1H), 6.90 (dd, J=9.2, 15.1 Hz, 1H), 5.48-5.18 (m, 2H), 4.31-4.23 (m, 1H), 4.21-4.15 (m, 1H), 4.05-3.94 (m, 1H), 3.90-3.70 (m, 2H), 3.68 (d, J=5.0 Hz, 3H), 3.63-3.50 (m, 1H), 3.46 (d, J=2.1 Hz, 3H), 3.19 (br d, J=9.9 Hz, 2H), 3.12 (br s, 1H), 2.99-2.88 (m, 1H), 2.46-2.39 (m, 1H), 2.36-2.28 (m, 2H), 2.15 (br s, 1H), 2.09 (br d, J=10.6 Hz, 1H), 1.94-1.83 (m, 3H). LCMS Rt=2.810 min, m/z=698.3 [M+H]$^+$.

LCMS (5 to 95% acetonitrile in water+0.03% ammonium bicarbonate over 6 mins) retention time 2.810 min, ESI+ found [M+H]=698.3.

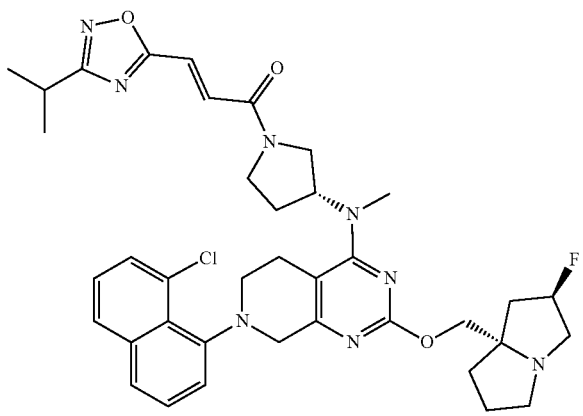 [SMILES: CC(C)c1noc(/C=C/C(=O)N2CC[C@@H](N(C)c3nc(OC[C@@]45CCCN4C[C@H](F)C5)nc4c3CCN(c3cccc5cccc(Cl)c35)C4)C2)n1]

Example 136 (Method 4): (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-isopropyl-1,2,4-oxadiazol-5-yl)prop-2-en-1-one

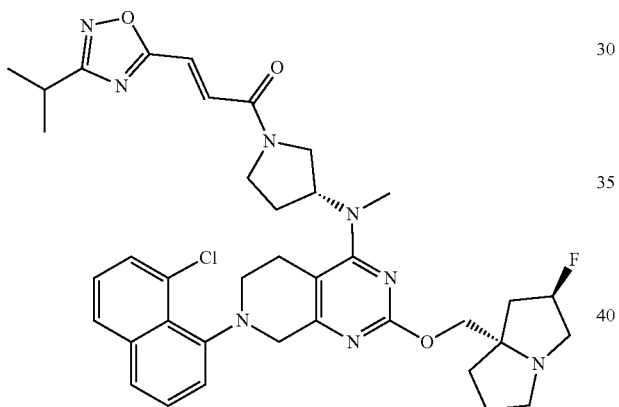

Step 1: (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-isopropyl-1,2,4-oxadiazol-5-yl)prop-2-en-1-one The amide coupling reaction was prepared in a similar fashion to Method #4, Step 11. The reaction mixture was purified by reverse phase HPLC (column: Waters Xbridge Prep OBD C18 150*40 mm*10 μm; mobile phase: [water (NH$_4$HCO$_3$)-acetonitrile]; B %: 55%-85%, 8 min) affording (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-isopropyl-1,2,4-oxadiazol-5-yl)prop-2-en-1-one (28.97 mg, 32.39%) as a yellow oil: $^1$H NMR (400 MHz, Acetonitrile-d3) δ 7.85 (d, J=8.1 Hz, 1H), 7.70-7.65 (m, 1H), 7.55 (dd, J=1.1, 7.4 Hz, 1H), 7.50 (dt, J=4.1, 7.8 Hz, 1H), 7.46-7.29 (m, 4H), 5.35-5.09 (m, 1H), 4.86-4.73 (m, 1H), 4.28-4.15 (m, 1H), 4.07-3.89 (m, 3H), 3.86-3.75 (m, 1H), 3.74-3.59 (m, 2H), 3.57-3.38 (m, 2H), 3.31-3.15 (m, 1H), 3.14-3.01 (m, 5H), 3.00-2.95 (m, 3H), 2.90-2.81 (m, 1H), 2.64-2.56 (m, 1H), 2.29-2.16 (m, 2H), 2.12-2.01 (m, 3H), 1.86-1.74 (m, 3H), 1.34-1.30 (m, 6H). LCMS Rt=3.448 min, m/z=714.3 [M+H]$^+$.

LCMS (5 to 95% acetonitrile in water+0.03% ammonium bicarbonate over 6 mins) retention time 3.448 min, ESI+ found [M+H]=714.3.

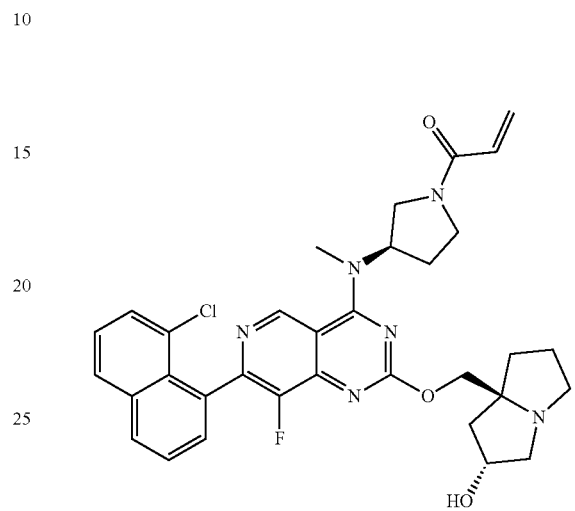

Example 137 (Method 1): 1-((R)-3-((7-(8-chloronaphthalen-1-yl)-8-fluoro-2-(((2R,7aS)-2-hydroxytetrahydro-1H-pyrrolizin-7a(5H)-yl)methoxy)pyrido[4,3-d]pyrimidin-4-yl)(methyl)amino)pyrrolidin-1-yl)prop-2-en-1-one

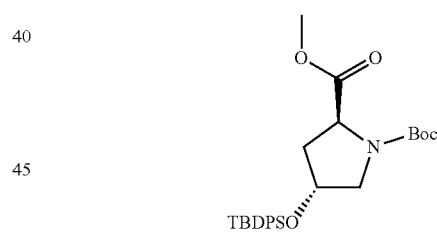

Step 1: (2S,4R)-1-tert-butyl 2-methyl 4-((tert-butyldiphenylsilyl)oxy)pyrrolidine-1,2-dicarboxylate To a solution of O1-tert-butyl O2-methyl (2S,4R)-4-hydroxypyrrolidine-1,2-dicarboxylate (10 g, 40.77 mmol) in N,N-dimethylformaldehyde (100 mL) was added imidazole (8.33 g, 122.31 mmol) and tert-butylchlorodiphenylsilane (33.62 g, 122.31 mmol) at 0° C. The mixture was stirred at 25° C. for 3 h. The reaction mixture was diluted with water (500 mL) and extracted with dichloromethane (2×200 mL). The combined organic layers were dried over sodium sulphate and concentrated under vacuo. The resulting residue was purified by column chromatography (silica gel, 100-200 mesh, 10% ethyl acetate in petroleum ether) affording (2S, 4R)-1-tert-butyl 2-methyl 4-((tert-butyldiphenylsilyl)oxy)pyrrolidine-1,2-dicarboxylate (13.25 g, 67.19%) as a white solid. LCMS Rt=0.961 min, m/z=483.2 [M+H]$^+$.

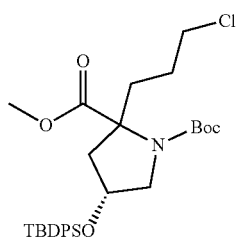

Step 2: (4R)-1-tert-butyl 2-methyl 4-((tert-butyldiphenylsilyl)oxy)-2-(3-chloropropyl)pyrrolidine-1,2-dicarboxylate To a solution of (2S,4R)-1-tert-butyl 2-methyl 4-((tert-butyldiphenylsilyl)oxy)pyrrolidine-1,2-dicarboxylate (12.2 g, 25.22 mmol) in tetrahydrofuran (200 mL) was added lithium diisopropyl amide (2 M, 13.87 mL) at −78° C. for 2 h, followed by the addition of 1-chloro-3-iodo-propane (10.31 g, 50.45 mmol) at −78° C. The mixture was stirred at 25° C. for 12 h. The reaction mixture was quenched with saturated sodium bicarbonate (50 mL) and the aqueous layer extracted with ethyl acetate (2×50 mL). The combined organic layers were dried over sodium sulphate and concentrated in vacuo. The resulting residue was purified by column chromatography (silica gel, 100-200 mesh, 10% dichloromethane in petroleum ether) affording (4R)-1-tert-butyl 2-methyl 4-((tert-butyldiphenylsilyl)oxy)-2-(3-chloropropyl)pyrrolidine-1,2-dicarboxylate (10 g, 70.77%) as a yellow oil. LCMS Rt=0.995 min, m/z=559.3 [M+H]$^+$.

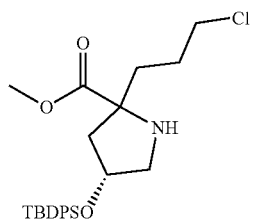

Step 3: (4R)-methyl 4-((tert-butyldiphenylsilyl)oxy)-2-(3-chloropropyl)pyrrolidine-2-carboxylate To a solution of (4R)-1-tert-butyl 2-methyl 4-((tert-butyldiphenylsilyl)oxy)-2-(3-chloropropyl)pyrrolidine-1,2-dicarboxylate (9.5 g, 16.96 mmol) in dichloromethane (150 mL) was added trifluoroacetic acid (77.00 g, 675.32 mmol). The mixture was stirred at 25° C. for 0.5 h. The reaction mixture was concentrated in vacuo affording (4R)-methyl 4-((tert-butyldiphenylsilyl)oxy)-2-(3-chloropropyl)pyrrolidine-2-carboxylate (9.7 g, crude, trifluoroacetate salt) as a brown oil, used in next step without further purification. LCMS Rt=0.647 min, m/z=459.2 [M+H]$^+$.

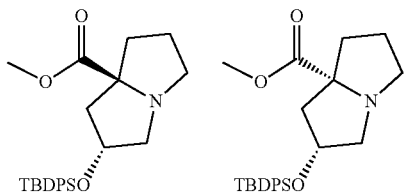

Step 4: (2R,7aS)-methyl 2-((tert-butyldiphenylsilyl)oxy)hexahydro-1H-pyrrolizine-7a-carboxylate and (2R,7aR)-methyl 2-((tert-butyldiphenylsilyl)oxy)hexahydro-1H-pyrrolizine-7a-carboxylate To a solution of methyl (4R)-methyl 4-((tert-butyldiphenylsilyl)oxy)-2-(3-chloropropyl)pyrrolidine-2-carboxylate (9.7 g, 16.90 mmol, trifluoroacetic acid salt) in methanol (150 mL) was added potassium carbonate (7.01 g, 50.69 mmol) and potassium iodide (280.48 mg, 1.69 mmol). The mixture was stirred at 35° C. for 1.5 h. The mixture was diluted with water (30 mL) and extracted with ethyl acetate (3×100 mL). The combined organic layers were dried over sodium sulphate and concentrated in vacuo. Two diastereoisomers were detected and the crude product was purified by reverse phase HPLC (column: Welch Xtimate C18 250*100 mm #10 um; mobile phase: [water (NH$_4$HCO$_3$)-acetonitrile]; B %: 70%-100%, 20 min) affording (2R,7aS)-methyl 2-((tert-butyldiphenylsilyl)oxy)hexahydro-1H-pyrrolizine-7a-carboxylate (2 g, 32.51%) as a white oil and (2R,7aR)-methyl 2-((tert-butyldiphenylsilyl)oxy)hexahydro-1H-pyrrolizine-7a-carboxylate (1.2 g, 19.81%) as a white oil.
LCMS Rt=3.095 min, m/z=423.2 [M+H]$^+$.

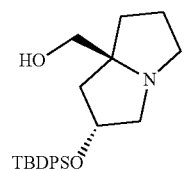

Step 5: ((2R,7aS)-2-((tert-butyldiphenylsilyl)oxy)hexahydro-1H-pyrrolizin-7a-yl)methanol To a solution of methyl (2R,7aS)-methyl 2-((tert-butyldiphenylsilyl)oxy)hexahydro-1H-pyrrolizine-7a-carboxylate (2 g, 4.72 mmol) in tetrahydrofuran (30 mL) was added lithium aluminum hydride (358.34 mg, 9.44 mmol) at 0° C. The mixture was stirred at 0° C. for 1 h. The reaction mixture was quenched with sodium sulfafe decahydrate. The mixture was filtered and the filtrate was concentrated in vacuo affording ((2R,7aS)-2-((tert-butyldiphenylsilyl)oxy)hexahydro-1H-pyrrolizin-7a-yl)methanol (1.8 g, crude) as a yellow oil, used in next step without further purification. LCMS Rt=0.734 min, m/z=395.2 [M+H]$^+$.

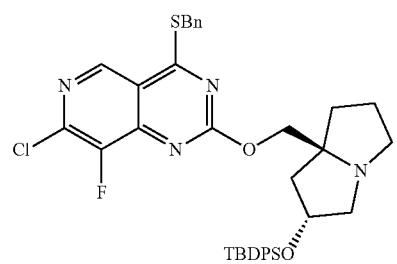

Step 6: 4-(benzylthio)-2-(((2R,7aS)-2-((tert-butyldiphenylsilyl)oxy)hexahydro-1H-pyrrolizin-7a-yl)methoxy)-7-chloro-8-fluoropyrido[4,3-d]pyrimidine The substitution reaction was prepared in a similar fashion to Method #1, Step 5. The combined organic layers were dried over sodium sulphate and concentrated in vacuo affording 4-(benzylthio)-2-(((2R,7aS)-2-((tert-butyldiphenylsilyl)oxy)hexahydro-1H-pyrrolizin-7a-yl)methoxy)-7-chloro-8-fluoropyrido[4,3-d]pyrimidine (2.6 g, crude) as a brown oil, used in next step without further purification. LCMS Rt=0.739 min, m/z=698.2 [M+H]⁺.

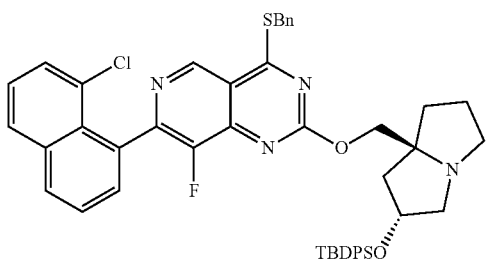

Step 7: 4-(benzylthio)-2-(((2R,7aS)-2-((tert-butyldiphenylsilyl)oxy)hexahydro-1H-pyrrolizin-7a-yl)methoxy)-7-(8-chloronaphthalen-1-yl)-8-fluoropyrido[4,3-d]pyrimidine The Suzuki reaction was prepared in a similar fashion to Method #1, Step 6. The resulting residue was purified by column chromatography (silica gel, 100-200 mesh, 50% ethyl acetate in petroleum ether) affording 4-(benzylthio)-2-(((2R,7aS)-2-((tert-butyldiphenylsilyl)oxy)hexahydro-1H-pyrrolizin-7a-yl)methoxy)-7-(8-chloronaphthalen-1-yl)-8-fluoropyrido[4,3-d]pyrimidine (1 g, 32.58%) as a brown oil. LCMS Rt=0.782 min, m/z=824.3 [M+H]⁺.

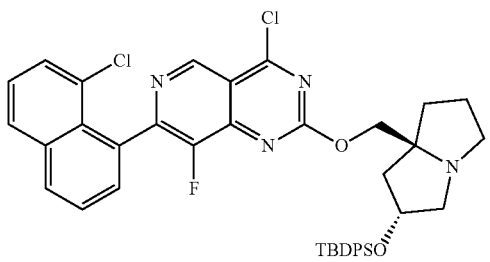

Step 8: 2-(((2R,7aS)-2-((tert-butyldiphenylsilyl)oxy)hexahydro-1H-pyrrolizin-7a-yl)methoxy)-4-chloro-7-(8-chloronaphthalen-1-yl)-8-fluoropyrido[4,3-d]pyrimidine The chlorination reaction was prepared in a similar fashion to Method #1, Step 7. The reaction mixture was concentrated in vacuo affording 2-(((2R,7aS)-2-((tert-butyldiphenylsilyl)oxy)hexahydro-1H-pyrrolizin-7a-yl)methoxy)-4-chloro-7-(8-chloronaphthalen-1-yl)-8-fluoropyrido[4,3-d]pyrimidine (400 mg, crude) as a brown oil, used in next step without any further purification. LCMS Rt=0.982 min, m/z=736.2 [M+H]⁺.

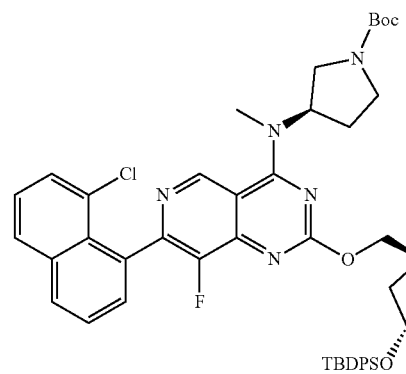

Step 9: (R)-tert-butyl 3-((2-(((2R,7aS)-2-((tert-butyldiphenylsilyl)oxy)hexahydro-1H-pyrrolizin-7a-yl)methoxy)-7-(8-chloronaphthalen-1-yl)-8-fluoropyrido[4,3-d]pyrimidin-4-yl)(methyl)amino)pyrrolidine-1-carboxylate The substitution reaction was prepared in a similar fashion to Method #1, Step 8. The resulting residue was purified by reverse phase HPLC (column: Phenomenex Luna 80*30 mm*3 µm; mobile phase: [water (trifluoroacetic acid)-acetonitrile]; B %: 45%-85%, 8 min) affording (R)-tert-butyl 3-((2-(((2R,7aS)-2-((tert-butyldiphenylsilyl)oxy)hexahydro-1H-pyrrolizin-7a-yl)methoxy)-7-(8-chloronaphthalen-1-yl)-8-fluoropyrido[4,3-d]pyrimidin-4-yl)(methyl)amino)pyrrolidine-1-carboxylate (120 mg, 21.38%, trifluoroacetate salt) as a white solid. LCMS Rt=0.872 min, m/z =900.4 [M+H]⁺.

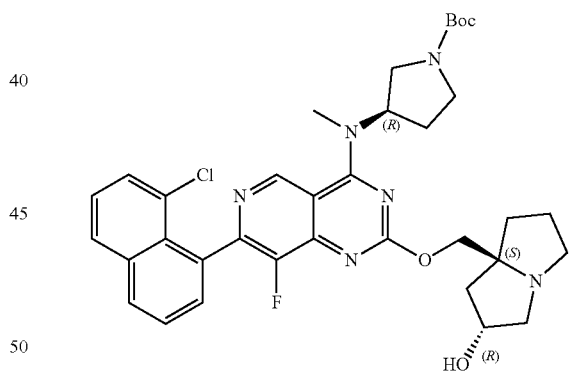

Step 10: (R)-tert-butyl 3-((7-(8-chloronaphthalen-1-yl)-8-fluoro-2-(((2R,7aS)-2-hydroxyhexahydro-1H-pyrrolizin-7a-yl)methoxy)pyrido[4,3-d]pyrimidin-4-yl)(methyl)amino)pyrrolidine-1-carboxylate A mixture of (R)-tert-butyl 3-((2-(((2R,7aS)-2-((tert-butyldiphenylsilyl)oxy)hexahydro-1H-pyrrolizin-7a-yl)methoxy)-7-(8-chloronaphthalen-1-yl)-8-fluoropyrido[4,3-d]pyrimidin-4-yl)(methyl)amino)pyrrolidine-1-carboxylate (100 mg, 98.46 µmol, trifluoroacetate salt), N,N-diethylethanamine; trihydrofluoride (158.73 mg, 984.64 µmol) in tetrahydrofuran (5 mL) was stirred at 25° C. for 12 h. The reaction mixture was concentrated in vacuo affording (R)-tert-butyl 3-((7-(8-chloronaphthalen-1-yl)-8-fluoro-2-(((2R, 7aS)-2-hydroxyhexahydro-1H-pyrrolizin-7a-yl)methoxy) pyrido[4,3-d]pyrimidin-4-yl)(methyl)amino)pyrrolidine-1-carboxylate (65 mg, crude) as a brown oil, used in next step without further purification. LCMS Rt=0.704 min, m/z=662.3 [M+H]$^+$.

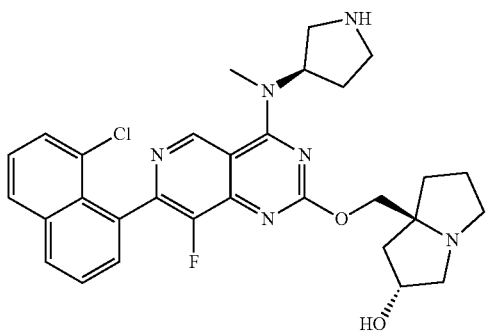 [SMILES: CN(c1nc(OC[C@@]23CCCN2C[C@H](O)C3)nc2c(F)c(-c3cccc4cccc(Cl)c34)ncc12)[C@@H]1CCNC1]

Step 11: (2R,7aS)-7a-(((7-(8-chloronaphthalen-1-yl)-8-fluoro-4-(methyl((R)-pyrrolidin-3-yl)amino)pyrido[4,3-d]pyrimidin-2-yl)oxy)methyl)hexahydro-1H-pyrrolizin-2-ol The deprotection of Boc group was prepared in a similar fashion to Method #1, Step 9. The reaction mixture was concentrated in vacuo affording (2R,7aS)-7a-(((7-(8-chloronaphthalen-1-yl)-8-fluoro-4-(methyl((R)-pyrrolidin-3-yl)amino)pyrido[4,3-d]pyrimidin-2-yl)oxy)methyl)hexahydro-1H-pyrrolizin-2-ol (66 mg, crude, trifluoroacetate salt) as a brown oil, used in next step without further purification. LCMS Rt=0.549 min, m/z=562.2 [M+H]$^+$.

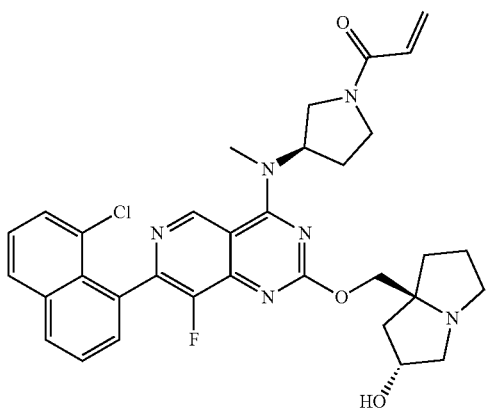 [SMILES: C=CC(=O)N1CC[C@@H](N(C)c2nc(OC[C@@]34CCCN3C[C@H](O)C4)nc3c(F)c(-c4cccc5cccc(Cl)c45)ncc23)C1]

Step 12: 1-((R)-3-((7-(8-chloronaphthalen-1-yl)-8-fluoro-2-(((2R,7aS)-2-hydroxytetrahydro-1H-pyrrolizin-7a(5H)-yl)methoxy)pyrido[4,3-d]pyrimidin-4-yl)(methyl)amino)pyrrolidin-1-yl)prop-2-en-1-one The amide coupling reaction was prepared in a similar fashion to Method #1, Step 10. The resulting residue was purified by reverse phase HPLC (column: Waters Xbridge Prep OBD C18 150*40 mm*10 um; mobile phase: [water (NH$_4$HCO$_3$)-acetonitrile]; B %: 20%-50%, 8 min) affording 1-((R)-3-((7-(8-chloronaphthalen-1-yl)-8-fluoro-2-(((2R,7aS)-2-hydroxytetrahydro-1H-pyrrolizin-7a(5H)-yl)methoxy)pyrido[4,3-d]pyrimidin-4-yl)(methyl)amino)pyrrolidin-1-yl)prop-2-en-1-one (12.33 mg, 22.55%) as a white solid: $^1$H NMR (400 MHz, Acetonitrile-d3) δ 9.21 (s, 1H), 8.15 (d, J=7.6 Hz, 1H), 8.04 (d, J=8.0 Hz, 1H), 7.76-7.68 (m, 1H), 7.67-7.60 (m, 2H), 7.58-7.50 (m, 1H), 6.68-6.53 (m, 1H), 6.26 (td, J=2.9, 16.8 Hz, 1H), 5.76-5.65 (m, 1H), 5.47-5.30 (m, 1H), 4.58-4.37 (m, 1H), 4.19 (br d, J=1.8 Hz, 2H), 4.15-3.97 (m, 1H), 3.87 (br s, 1H), 3.78-3.63 (m, 1H), 3.63-3.50 (m, 1H), 3.45 (s, 3H), 3.22 (br dd, J=4.9, 10.3 Hz, 1H), 3.15-3.04 (m, 1H), 3.00-2.85 (m, 1H), 2.65 (br dd, J=5.8, 10.1 Hz, 2H), 2.42 (br s, 2H), 2.26 (br dd, J=6.0, 13.0 Hz, 3H), 1.94-1.84 (m, 2H), 1.72 (dd, J=6.3, 12.9 Hz, 1H). LCMS Rt=2.554 min, m/z=616.2 [M+H]$^+$.

LCMS (5 to 95% acetonitrile in water+0.03% ammonium bicarbonate over 6 mins) retention time 2.554 min, ESI+ found [M+H]=616.2.

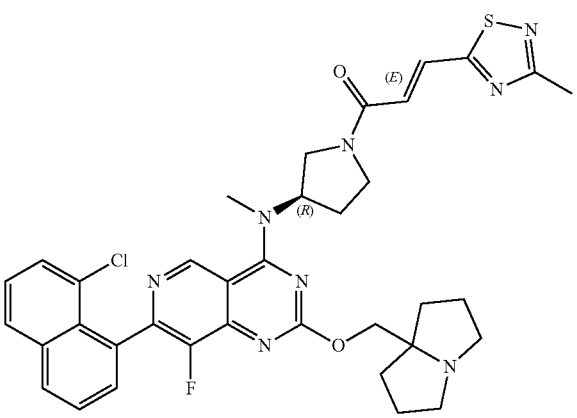

Example 138 (Method 9): (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-methyl-1,2,4-thiadiazol-5-yl)prop-2-en-1-one

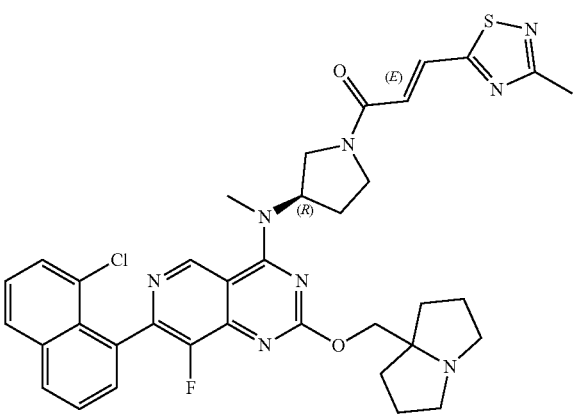

Step 1: (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-methyl-1,2,4-thiadiazol-5-yl)prop-2-en-1-one The Horner-Wadsworth-Emmons reaction was prepared in a similar fashion to Method #9, Step 9. The reaction mixture was purified by reverse phase HPLC (column: Waters Xbridge Prep OBD C18 150*40 mm*10 um; mobile phase: [water (NH$_4$HCO$_3$)-acetonitrile]; B %: 35%-70%, 8 min) affording (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-methyl-1,2,4-thiadiazol-5-yl)prop-2-en-1-one (18.54 mg, 25.61%) as a yellow amorphous solid: $^1$H NMR (400 MHz, Acetonitrile-d3) δ 9.24-9.19 (m, 1H), 8.15 (dd, J=1.0, 8.1 Hz, 1H), 8.05 (dd, J=0.8, 8.2 Hz, 1H), 7.80-7.69 (m, 2H), 7.68-7.62 (m, 2H), 7.58-7.50 (m, 1H), 7.40-7.29 (m, 1H), 5.50-5.29 (m, 1H), 4.28-4.14 (m, 3H), 4.10-3.98 (m, 1H), 3.91-3.77 (m, 1H), 3.70-3.52 (m, 1H), 3.47 (s, 3H), 3.03-2.93 (m, 2H), 2.66 (d, J=10.4 Hz, 3H), 2.61 (br s, 1H), 2.50-2.42 (m, 1H), 2.39-2.32 (m, 1H), 2.00-1.99 (m, 1H), 1.96-1.92 (m, 2H), 1.88-1.78 (m, 4H), 1.69-1.60 (m, 2H). LCMS Rt=2.741 min, m/z=698.2 [M+H]$^+$.

LCMS (5 to 95% acetonitrile in water+0.03% ammonium bicarbonate over 6 mins) retention time 2.741 min, ESI+ found [M+H]=698.2.

Example 139 (Method 1): (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-((1R,2S)-2-fluorocyclopropyl)-1,2,4-oxadiazol-5-yl)prop-2-en-1-one

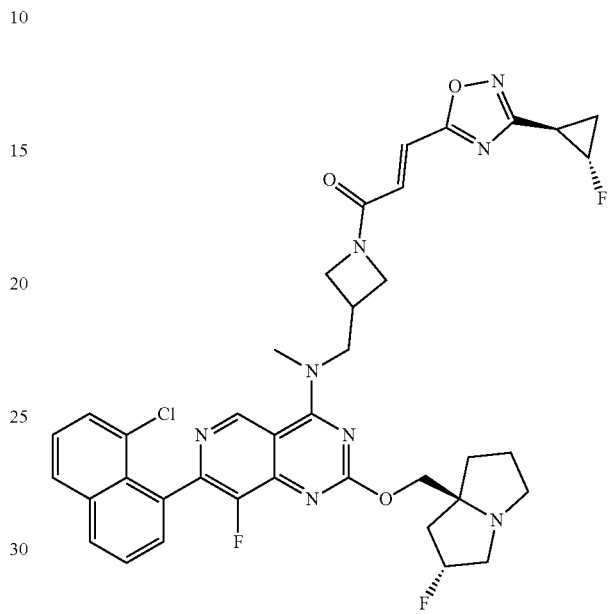

Step 1: (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-((1R,2S)-2-fluorocyclopropyl)-1,2,4-oxadiazol-5-yl)prop-2-en-1-one The amide coupling reaction was prepared in a similar fashion to Method #1, Step 10. The residue was purified by reverse phase HPLC (column: Waters Xbridge Prep OBD C18 150*40 mm*10 μm; mobile phase: [water (NH$_4$HCO$_3$)-acetonitrile]; B %: 45%-75%, 8 min) affording (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-((1R,2S)-2-fluorocyclopropyl)-1,2,4-oxadiazol-5-yl)prop-2-en-1-one (37.78 mg, 24.60%) as a yellow amorphous solid: $^1$H NMR (400 MHz, Acetonitrile-d3) δ 9.24 (s, 1H), 8.16-8.07 (m, 1H), 8.05-7.97 (m, 1H), 7.73-7.65 (m, 1H), 7.64-7.56 (m, 2H), 7.55-7.47 (m, 1H), 7.31-7.23 (m, 1H), 7.17-7.08 (m, 1H), 5.34-5.14 (m, 1H), 5.07-4.83 (m, 1H), 4.51-4.41 (m, 1H), 4.34-4.03 (m, 6H), 3.99-3.86 (m, 1H), 3.58 (s, 3H), 3.22 (br dd, J=6.6, 11.8 Hz, 1H), 3.15-3.06 (m, 2H), 3.06-3.00 (m, 1H), 2.93-2.82 (m, 1H), 2.70-2.55 (m, 1H), 2.12-1.97 (m, 3H), 1.91-1.77 (m, 3H), 1.76-1.61 (m, 1H), 1.39-1.29 (m, 1H). LCMS Rt=3.150 min, m/z=744.3 [M+H]$^+$.

LCMS (5 to 95% acetonitrile in water+0.03% ammonium bicarbonate over 6 mins) retention time 3.150 min, ESI+ found [M+H]=744.3.

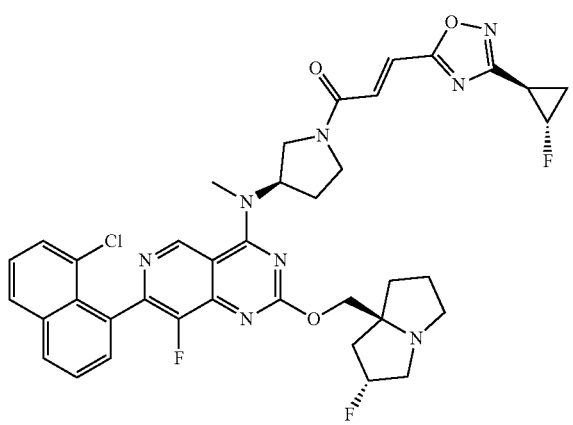 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2nc([C@H]3C[C@@H]3F)no2)C1]

Example 140 (Method 1): (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-((1R,2S)-2-fluorocyclopropyl)-1,2,4-oxadiazol-5-yl)prop-2-en-1-one

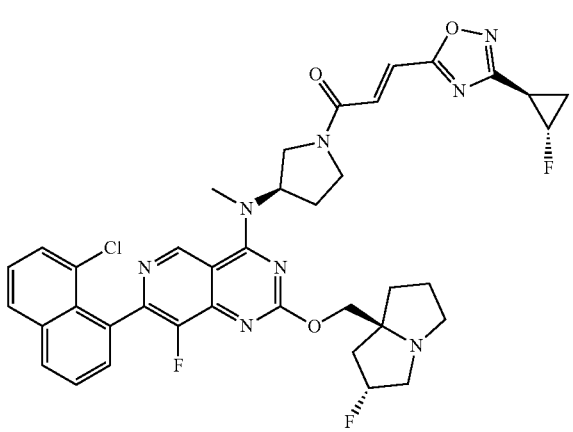 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2nc([C@H]3C[C@@H]3F)no2)C1]

Step 1: (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-((1R,2S)-2-fluorocyclopropyl)-1,2,4-oxadiazol-5-yl)prop-2-en-1-one The amide coupling reaction was prepared in a similar fashion to Method #1, Step 10. The residue was purified by reverse phase HPLC (column: Waters Xbridge Prep OBD C18 150*40 mm*10 μm; mobile phase: [water (NH₄HCO₃)-acetonitrile]; B %: 45%-75%, 8 min) affording (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-((1R,2S)-2-fluorocyclopropyl)-1,2,4-oxadiazol-5-yl)prop-2-en-1-one (32.73 mg, 35.19%) as a yellow oil: ¹H NMR (400 MHz, Acetonitrile-d3) δ 9.19 (t, J=1.9 Hz, 1H), 8.12 (d, J=8.0 Hz, 1H), 8.02 (d, J=8.3 Hz, 1H), 7.73-7.66 (m, 1H), 7.65-7.56 (m, 2H), 7.54-7.47 (m, 1H), 7.46-7.37 (m, 1H), 7.36-7.26 (m, 1H), 5.49-5.17 (m, 2H), 5.08-4.85 (m, 1H), 4.22 (br d, J=1.9 Hz, 2H), 4.05-3.95 (m, 1H), 3.93-3.67 (m, 2H), 3.63-3.51 (m, 1H), 3.43 (s, 3H), 3.04 (br s, 2H), 2.92-2.83 (m, 1H), 2.68-2.59 (m, 1H), 2.46-2.38 (m, 1H), 2.35-2.29 (m, 1H), 2.11-1.98 (m, 3H), 1.93-1.63 (m, 5H), 1.40-1.28 (m, 1H). LCMS Rt=2.271 min, m/z=744.3 [M+H]⁺.

LCMS (5 to 95% acetonitrile in water+0.03% ammonium bicarbonate over 6 mins) retention time 2.271 min, ESI+ found [M+H]=744.3

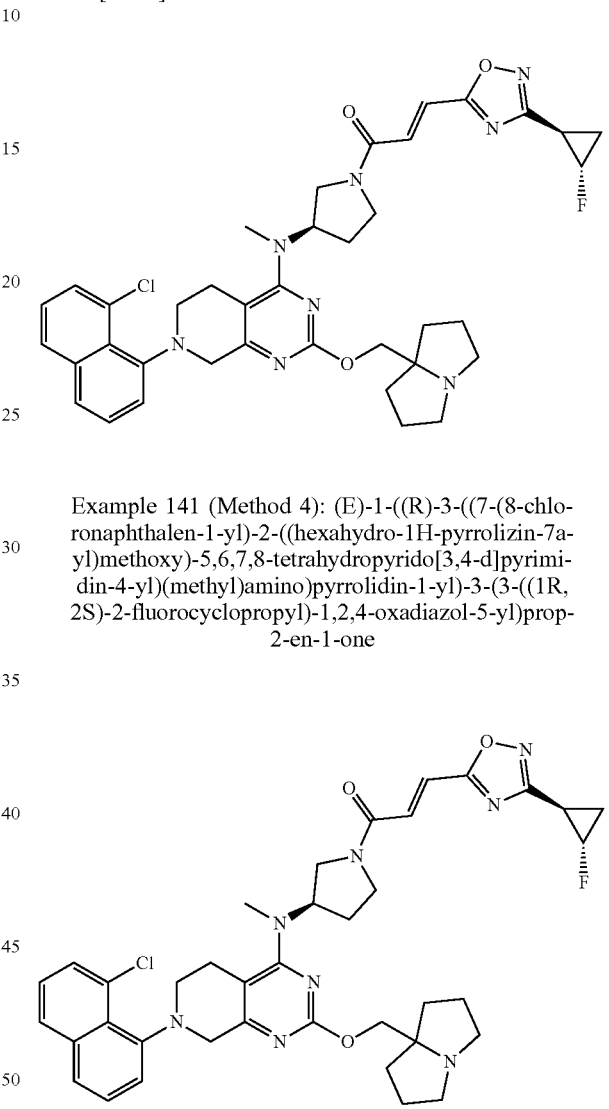

Example 141 (Method 4): (E)-1-((R)-3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-((1R,2S)-2-fluorocyclopropyl)-1,2,4-oxadiazol-5-yl)prop-2-en-1-one Step 1: (E)-1-((R)-3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-((1R,2S)-2-fluorocyclopropyl)-1,2,4-oxadiazol-5-yl)prop-2-en-1-one The amide coupling reaction was prepared in a similar fashion to Method #4, Step 11. The crude product was purified by reverse phase HPLC (column: Waters Xbridge Prep OBD C18 150*40 mm*10 μm; mobile phase: [water (ammonium bicarbonate- acetonitrile]; B %: 45%-75%, 8 min) affording (E)-1-((R)-3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-((1R,2S)-2-fluorocyclopropyl)-1,2,4-oxadiazol-5-yl)prop-2-en-1-one (5.26 mg, 4.67%) as a yellow oil: ¹H NMR (400 MHz, Acetonitrile-d3) δ 7.85 (d, J=8.3 Hz, 1H), 7.68 (br d, J=8.4 Hz, 1H), 7.55 (d, J=7.5 Hz, 1H), 7.53-7.47 (m, 1H), 7.37 (s, 2H), 7.35-7.25 (m, 2H), 5.08-4.85 (m, 1H), 4.85-4.70 (m, 1H), 4.31-4.19 (m, 1H), 4.05-3.93 (m, 2H), 3.92-3.60 (m, 3H), 3.58-3.49 (m, 1H), 3.48-3.38 (m, 1H), 3.32-3.16 (m, 1H), 3.15-3.08 (m, 1H), 3.06-2.85 (m, 5H), 2.73-2.49 (m, 4H), 2.32-2.16 (m, 3H), 1.93-1.86 (m, 2H), 1.85-1.64 (m, 5H), 1.63-1.51 (m, 2H), 1.40-1.28 (m, 1H). LCMS Rt=3.142 min, m/z=712.3 [M+H]⁺.

LCMS (5 to 95% acetonitrile in water+0.03% ammonium bicarbonate over 6 mins) retention time 3.142 min, ESI+ found [M+H]=712.3.

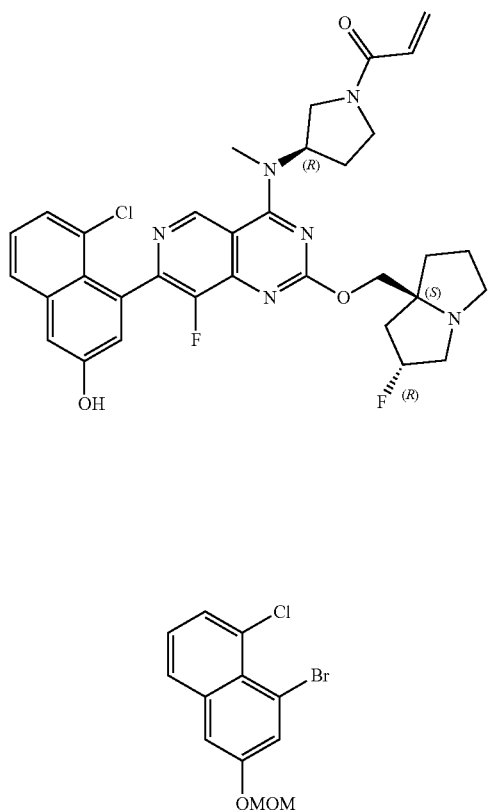

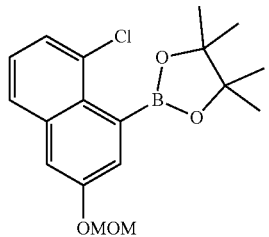

Step 2: 2-(8-chloro-3-(methoxymethoxy)naphthalen-1-yl)-4,4,5,5-tetramethyl-1,3,2-dioxaborolane The Borate formation was prepared in a similar fashion to Method #2, Step 2. The residue was purified by column chromatography (silica gel, 100-200 mesh, 0-10% ethyl acetate in petroleum ether) affording 2-(8-chloro-3-(methoxymethoxy)naphthalen-1-yl)-4,4,5,5-tetramethyl-1,3,2-dioxaborolane (1.5 g, 46.34%) as a green oil: ¹H NMR (400 MHz, Chloroform-d) δ 7.70-7.66 (m, 1H), 7.48-7.42 (m, 2H), 7.39-7.32 (m, 2H), 5.33 (s, 2H), 3.55-3.53 (m, 3H), 1.50-1.46 (m, 12H). LCMS Rt=0.758 min, m/z=348.1 [M+H]⁺.

Step 3: (R)-tert-butyl 3-((7-(8-chloro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate Step 1: 1-bromo-8-chloro-3-(methoxymethoxy)naphthalene The MOM protection reaction was prepared in a similar fashion to Method #2, Step 1. The residue was purified by column chromatography (silica gel, 100-200 mesh, 0-10% ethyl acetate in petroleum ether) affording 1-bromo-8-chloro-3-(methoxymethoxy)naphthalene (2.8 g, 62.92%) as a yellow oil: ¹H NMR (400 MHz, Chloroform-d) δ 7.64-7.55 (m, 2H), 7.47-7.38 (m, 1H), 7.31-7.28 (m, 1H), 7.25-7.20 (m, 1H), 5.19 (s, 2H), 3.44 (s, 3H). LCMS Rt=0.953 min, m/z=302.0 [M+H]⁺.

The Suzuki reaction was prepared in a similar fashion to Method #2, Step 5. The residue was purified by reverse phase HPLC (column: Phenomenex Luna 80*30 mm*3 μm; mobile phase: [water (trifluoroacetic acid)-acetonitrile]; B %: 20%-50%, 8 min) affording (R)-tert-butyl 3-((7-(8-chloro-3-(methoxymethoxy)naphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (24 mg, 7.14%) as a yellow solid. LCMS Rt=1.808 min, m/z=724.3 [M+H]⁺

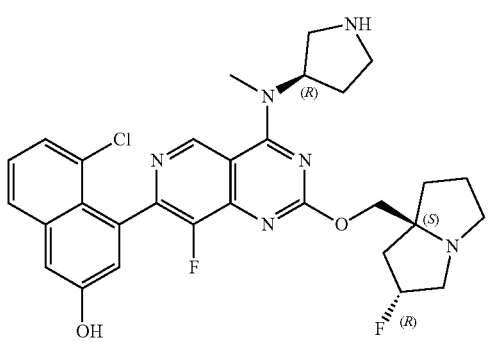

Step 4: 5-chloro-4-(8-fluoro-2-(((2R,7aS)-2-fluoro-hexahydro-1H-pyrrolizin-7a-yl)methoxy)-4-(methyl((R)-pyrrolidin-3-yl)amino)pyrido[4,3-d]pyrimidin-7-yl)naphthalen-2-ol The de-Boc and MOM protecting reaction was prepared in a similar fashion to Method #2, Step 6. The reaction mixture concentrated to dryness in vacuo affording 5-chloro-4-(8-fluoro-2-(((2R,7aS)-2-fluorohexahydro-1H-pyrrolizin-7a-yl)methoxy)-4-(methyl((R)-pyrrolidin-3-yl)amino)pyrido[4,3-d]pyrimidin-7-yl)naphthalen-2-ol (20 mg, crude, trifluoroacetic salt) as a brown oil, used in next step without any further purification.

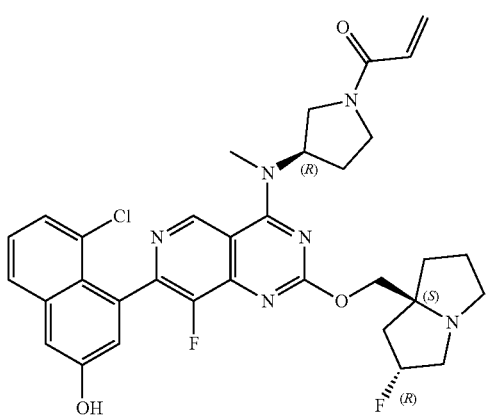

Step 5: 1-((R)-3-((7-(8-chloro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one The amide coupling reaction was prepared in a similar fashion to Method #2, Step 7. The residue was purified by reverse phase HPLC: column: Waters Xbridge BEH C18 100*30 mm*10 μm; mobile phase: [water (NH$_4$HCO$_3$)-acetonitrile]; B %: 30%-60%, 8 min affording 1-((R)-3-((7-(8-chloro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (2.30 mg, 10.43%) as a yellow amorphous solid: $^1$H NMR (400 MHz, Acetonitrile-d3) δ 9.18 (s, 1H), 7.83-7.77 (m, 1H), 7.46-7.34 (m, 3H), 7.27-7.15 (m, 1H), 6.67-6.48 (m, 1H), 6.32-6.16 (m, 1H), 5.67 (ddd, J=2.3, 6.7, 10.3 Hz, 1H), 5.42-5.16 (m, 2H), 4.30-4.17 (m, 2H), 4.14-4.02 (m, 1H), 3.99-3.75 (m, 2H), 3.70-3.62 (m, 1H), 3.59-3.51 (m, 1H), 3.42 (s, 3H), 3.22 (br d, J=12.0 Hz, 2H), 3.17-3.13 (m, 1H), 2.99-2.91 (m, 1H), 2.42-2.36 (m, 2H), 2.29 (br dd, J=5.4, 7.9 Hz, 3H), 1.91-1.70 (m, 3H). LCMS Rt=2.760 min, m/z=634.2 [M+H]$^+$.

LCMS (5 to 95% acetonitrile in water+0.03% ammonium bicarbonate over 6 mins) retention time 2.760 min, ESI+ found [M+H]=634.2.

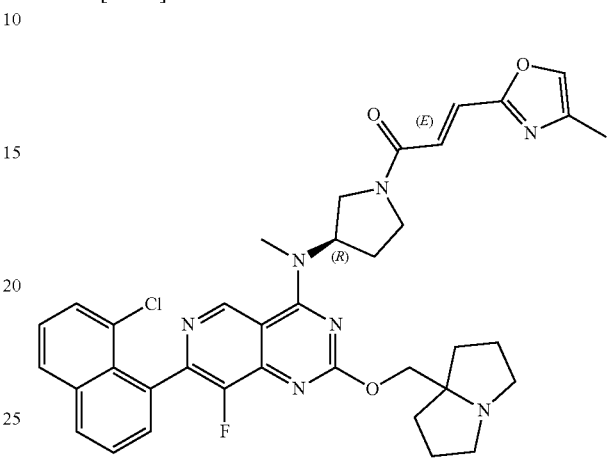

Example 143 (Method 9): (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(4-methyloxazol-2-yl)prop-2-en-1-one

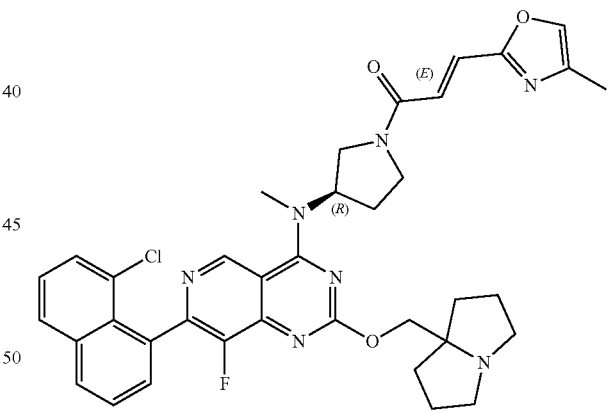

Step 1: (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(4-methyloxazol-2-yl)prop-2-en-1-one The Homer-Wadsworth-Emmons reaction was prepared in a similar fashion to Method #9, Step 9. The reaction mixture was purified by reverse phase HPLC (column: Waters Xbridge Prep OBD C18 150*40 mm*10 um; mobile phase: [water (NH$_4$HCO$_3$)-acetonitrile]; B %: 25%-55%, 8 min) affording (R,E)-1-(3-((7-(8-chloronaphthalen-1-yl)-8-fluoro-2-((tetrahydro-1H-pyrrolizin-7a(5H)-yl)methoxy)

pyrido[4,3-d]pyrimidin-4-yl)(methyl)amino)pyrrolidin-1-yl)-3-(4-methyloxazol-2-yl)prop-2-en-1-one (27.68 mg, 37.08%) as a white solid: $^1$H NMR (400 MHz, Acetonitrile-d3) δ 9.28-9.15 (m, 1H), 8.14 (d, J=8.0 Hz, 1H), 8.04 (d, J=8.0 Hz, 1H), 7.74-7.68 (m, 1H), 7.67-7.57 (m, 3H), 7.56-7.51 (m, 1H), 7.33-7.25 (m, 1H), 7.21-7.09 (m, 1H), 5.48-5.31 (m, 1H), 4.21-4.16 (m, 2H), 4.09-3.96 (m, 1H), 3.92-3.81 (m, 1H), 3.80-3.71 (m, 1H), 3.68-3.50 (m, 1H), 3.45 (s, 3H), 3.04-2.92 (m, 2H), 2.68-2.55 (m, 2H), 2.48-2.39 (m, 1H), 2.37-2.31 (m, 1H), 2.29-2.22 (m, 1H), 2.18 (d, J=9.0 Hz, 3H), 2.14 (br s, 1H), 1.90-1.75 (m, 4H), 1.68-1.60 (m, 2H). LCMS Rt=2.198 min, m/z=681.3 [M+H]$^+$.

LCMS (5 to 95% acetonitrile in water+0.1% trifluoroacetic acid over 6 mins) retention time 2.198 min, ESI+ found [M+H]=681.3.

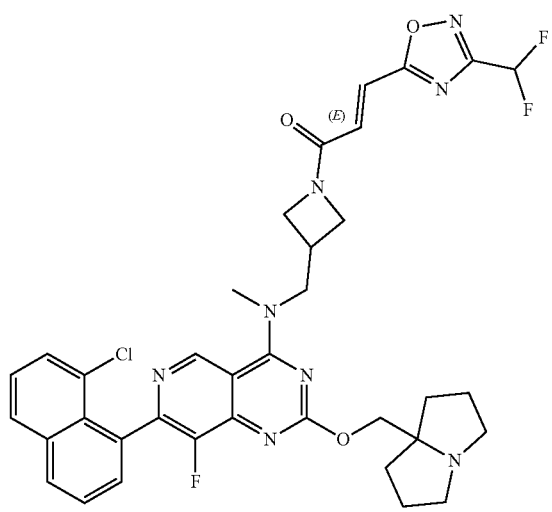 [SMILES: CN(CC1CN(C(=O)/C=C/c2nc(C(F)F)no2)C1)c1nc(OCC23CCCN2CCC3)nc2c(F)c(-c3cccc4cccc(Cl)c34)ncc12]

Example 144 (Method 1): (E)-1-(3-(((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)methyl)azetidin-1-yl)-3-(3-(difluoromethyl)-1,2,4-oxadiazol-5-yl)prop-2-en-1-one

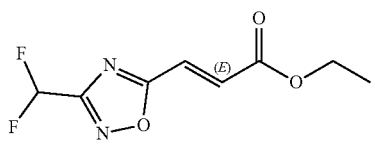

Step 1: (E)-ethyl 3-(3-(difluoromethyl)-1,2,4-oxadiazol-5-yl)acrylate

The cyclization reaction was prepared in a similar fashion to Method #1, Step 3. The crude product was concentrated in vacuo and purified by column chromatography (silica gel, 100-200 mesh, 0-10% ethyl acetate in petroleum ether) affording (E)-ethyl 3-(3-(difluoromethyl)-1,2,4-oxadiazol-5-yl)acrylate (2.2 g, 55.50%) as a yellow oil. LCMS Rt=0.730 min, m/z=218.1 [M+H]$^+$.

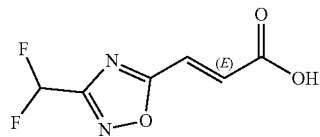 [SMILES: O=C(O)/C=C/c1nc(C(F)F)no1]

Step 2: (E)-3-(3-(difluoromethyl)-1,2,4-oxadiazol-5-yl)acrylic acid

The hydrolysis reaction was prepared in a similar fashion to Method #1, Step 4. The reaction mixture was quenched with hydrochloric acid (1M, 20 mL) and adjusted pH to 2, then extracted with dichloromethane (3×20 mL). The combined organic layers were dried over sodium sulphate and concentrated in vacuo affording (E)-3-(3-(difluoromethyl)-1,2,4-oxadiazol-5-yl)acrylic acid (870 mg, crude) as a yellow solid, used in next step without further purification. LCMS Rt=0.344 min, m/z=190.0 [M+H]$^+$.

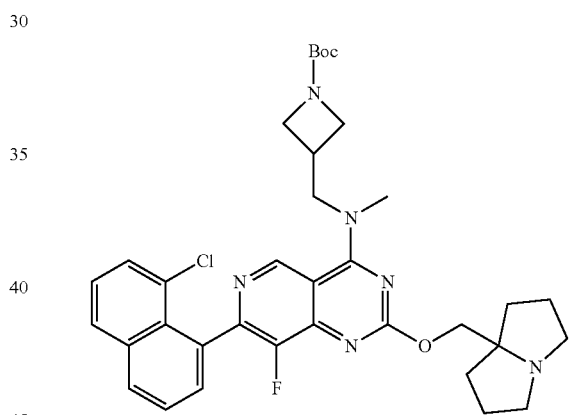

Step 3: tert-butyl 3-(((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)methyl)azetidine-1-carboxylate The substitution reaction was prepared in a similar fashion to Method #1, Step 8. The reaction mixture was diluted with water (10 mL) and extracted with ethyl acetate (2×10 mL).

The combined organic layers were dried over sodium sulphate and concentrated under vacuo. The resulting residue was purified by reverse phase HPLC (column: Waters Xbridge Prep OBD C18 150*40 mm*10 μm; mobile phase: [water (NH$_4$HCO$_3$)-acetonitrile]; B %: 40%-70%, 8 min) affording tert-butyl 3-(((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)methyl)azetidine-1-carboxylate (140 mg, 20.08%) as an orange solid. LCMS Rt=0.736 min, m/z=646.3 [M+H]+.

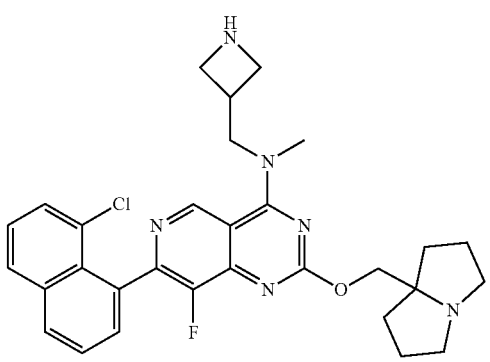 [SMILES: CN(CC1CNC1)c1nc(OCC23CCCN2CCC3)nc2c(F)c(-c3cccc4cccc(Cl)c34)ncc12]

Step 5: N-(azetidin-3-ylmethyl)-7-(8-chloronaphthalen-1-yl)-8-fluoro-2-((hexahydro-1H-pyrrolizin-7a-yl)methoxy)-N-methylpyrido[4,3-d]pyrimidin-4-amine The deprotection of Boc reaction was prepared in a similar fashion to Method #1, Step 9. The reaction mixture was diluted with saturated solution of sodium carbonate (5 mL) and extracted with dichloromethane (2×20 mL). The combined organic layers were dried over sodium sulphate and concentrated in vacuo affording N-(azetidin-3-ylmethyl)-7-(8-chloronaphthalen-1-yl)-8-fluoro-2-((hexahydro-1H-pyrrolizin-7a-yl)methoxy)-N-methylpyrido[4,3-d]pyrimidin-4-amine (59 mg, crude) as a brown gum. LCMS Rt=0.629 min, m/z=546.2 [M+H]$^+$.

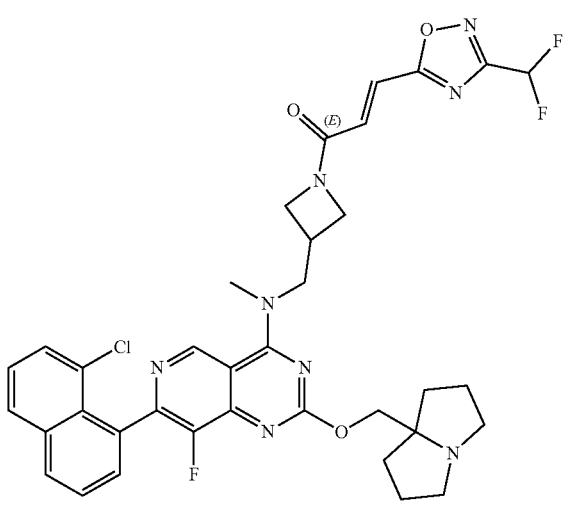 [SMILES: CN(CC1CN(C(=O)/C=C/c2nc(C(F)F)no2)C1)c1nc(OCC23CCCN2CCC3)nc2c(F)c(-c3cccc4cccc(Cl)c34)ncc12]

Step 6: (E)-1-(3-(((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)methyl)azetidin-1-yl)-3-(3-(difluoromethyl)-1,2,4-oxadiazol-5-yl)prop-2-en-1-one The amide coupling reaction was prepared in a similar fashion to Method #1, Step 10. The crude product was purified by reverse phase HPLC (column: Phenomenex Luna C18 75*30 mm*3 μm; mobile phase: [water (formic acid)-acetonitrile]; B %: 15%-45%, 8 min) affording (E)-1-(3-(((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)methyl)azetidin-1-yl)-3-(3-(difluoromethyl)-1,2,4-oxadiazol-5-yl)prop-2-en-1-one (6.94 mg, 10.15%, formate salt) as a yellow oil: $^1$H NMR (400 MHz, Acetonitrile-d3) δ 9.25-9.20 (m, 1H), 8.12 (d, J=7.8 Hz, 1H), 8.02 (d, J=7.4 Hz, 1H), 7.71-7.66 (m, 1H), 7.63-7.58 (m, 2H), 7.54-7.48 (m, 1H), 7.42-7.27 (m, 2H), 7.14-6.84 (m, 1H), 4.54-4.47 (m, 1H), 4.33 (br d, J=5.1 Hz, 2H), 4.24-4.12 (m, 3H), 4.01-3.92 (m, 1H), 3.62-3.54 (m, 3H), 3.31-3.18 (m, 3H), 2.83-2.72 (m, 3H), 2.15-2.00 (m, 4H), 1.91 (br s, 2H), 1.82-1.72 (m, 2H). LCMS Rt=2.337 min, m/z=718.2 [M+H]$^+$.

LCMS (5 to 95% acetonitrile in water+0.1% trifluoroacetic acid over 6 mins) retention time 2.337 min, ESI+ found [M+H]=718.2.

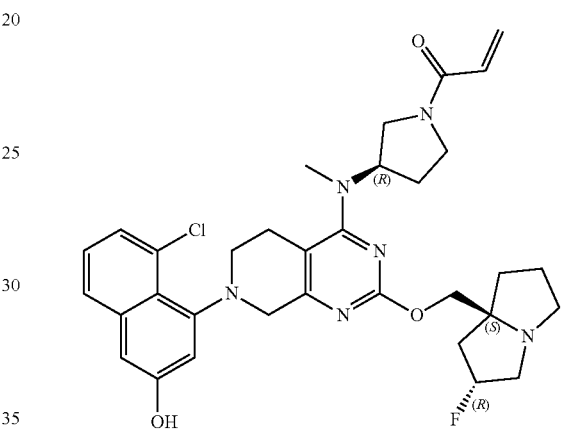

Example 145 (Method 4): 1-((R)-3-((7-(8-chloro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)prop-2-en-1-one

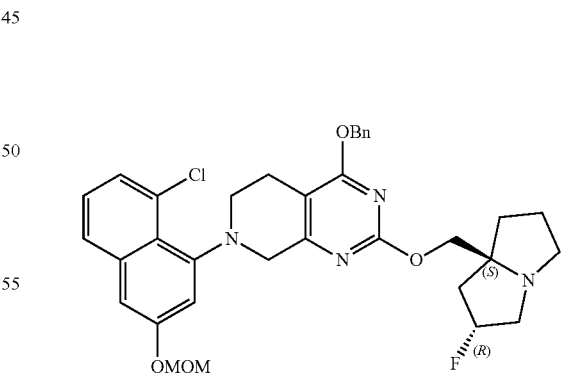

Step 1: 4-(benzyloxy)-7-(8-chloro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidine The Buchwald reaction was prepared in a similar fashion to Method #4, Step 6. The residue was purified by column chromatography (silica gel, 100-200 mesh, 0-100% ethyl acetate in petroleum ether) affording 4-(benzyloxy)-7-(8-chloro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidine (1.26 g, 60.07%) as a brown oil. LCMS Rt=0.876 min, m/z=618.2 [M+H]⁺.

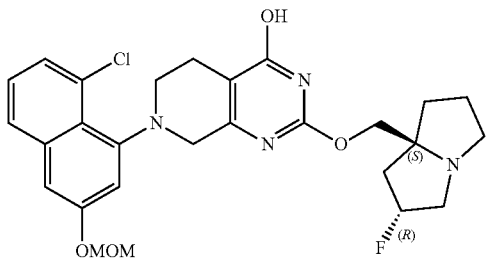

Step 2: 7-(8-chloro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-ol The hydrogenation reaction was prepared in a similar fashion to Method #4, Step 7. The reaction mixture was filtered and the filtrate was concentrated in vacuo affording 7-(8-chloro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-ol (700 mg, crude) as a brown solid, used in next step without any further purification. LCMS Rt=0.735 min, m/z=528.2 [M+H]⁺.

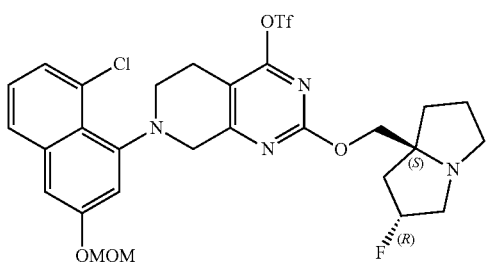

Step 3: 7-(8-chloro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl trifluoromethanesulfonate The sulfonylation reaction was prepared in a similar fashion to Method #4, Step 8. The reaction mixture was quenched with saturated sodium bicarbonate (300 mL) and extracted with dichloromethane (3×100 mL). The combined organic layers were dried over sodium sulphate and concentrated in vacuo affording 7-(8-chloro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl trifluoromethanesulfonate (660 mg, crude) as a brown oil, used in the next step without further purification. LCMS Rt=0.857 min, m/z=660.1 [M+H]⁺.

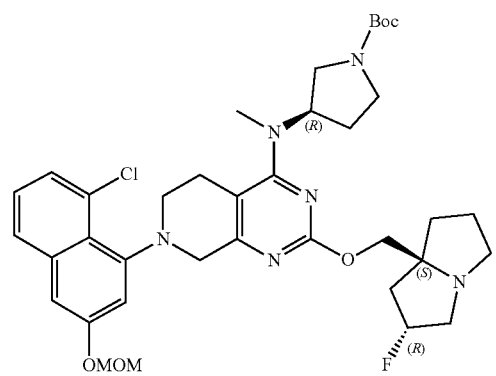

Step 4: (R)-tert-butyl 3-((7-(8-chloro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidine-1-carboxylate The substitution reaction was prepared in a similar fashion to Method #4, Step 9, the crude product was purified by column chromatography (silica gel, 100-200 mesh, 0-100% methanol in dichloromethane) affording (R)-tert-butyl 3-((7-(8-chloro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidine-1-carboxylate (420 mg, 59.14%) as a brown oil. LCMS Rt=0.816 min, m/z=710.3 [M+H]⁺.

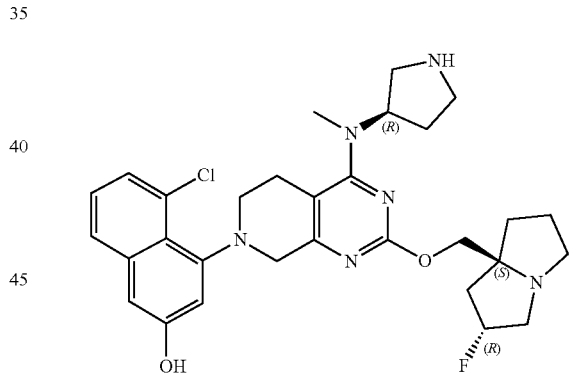

Step 5: 5-chloro-4-(2-(((2R,7aS)-2-fluorohexahydro-1H-pyrrolizin-7a-yl)methoxy)-4-(methyl((R)-pyrrolidin-3-yl)amino)-5,6-dihydropyrido[3,4-d]pyrimidin-7(8H)-yl)naphthalen-2-ol The deprotection of Boc and MOM groups was prepared in a similar fashion to Method #2, Step 6. The crude product was purified by reverse phase HPLC (column: Waters Xbridge Prep OBD C18 150*40 mm*10 um; mobile phase: [water (NH₄HCO₃)-acetonitrile]; B %: 30%-60%, 8 min) affording 5-chloro-4-(2-(((2R,7aS)-2-fluorohexahydro-1H-pyrrolizin-7a-yl)methoxy)-4-(methyl((R)-pyrrolidin-3-yl)amino)-5,6-dihydropyrido[3,4-d]pyrimidin-7(8H)-yl)naphthalen-2-ol (20 mg, 16.72%) as a white solid. LCMS Rt=0.652, m/z=566.3 [M+H]⁺.

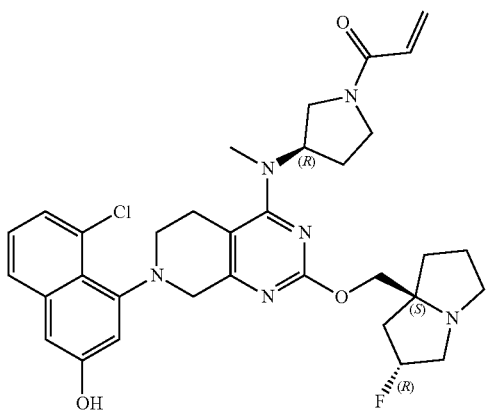

Step 6: 1-((R)-3-((7-(8-chloro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)prop-2-en-1-one The amide coupling reaction was prepared in a similar fashion to Method #4, Step 11. The crude product was purified by reverse phase HPLC (column: Waters Xbridge BEH C18 100*30 mm*10 μm; mobile phase: [water (NH$_4$HCO$_3$)-acetonitrile]; B %: 25%-55%, 10 min) affording 1-((R)-3-((7-(8-chloro-3-hydroxynaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)prop-2-en-1-one (1.78 mg, 7.76%) as a yellow solid: $^1$H NMR (400 MHz, Acetonitrile-d3) δ 7.69-7.60 (m, 1H), 7.38-7.26 (m, 2H), 7.03-6.88 (m, 2H), 6.66-6.49 (m, 1H), 6.31-6.16 (m, 1H), 5.73-5.60 (m, 1H), 5.38-5.16 (m, 1H), 4.90-4.69 (m, 1H), 4.24 (br d, J=17.3 Hz, 1H), 4.13-3.98 (m, 2H), 3.96-3.64 (m, 3H), 3.63-3.48 (m, 2H), 3.47-3.34 (m, 1H), 3.32-3.16 (m, 3H), 3.16-3.01 (m, 3H), 3.00-2.89 (m, 4H), 2.65-2.55 (m, 1H), 2.13 (br d, J=7.0 Hz, 3H), 2.09-2.03 (m, 2H), 1.82 (br s, 3H). LCMS Rt=2.113 min, m/z=620.3 [M+H]$^+$.

LCMS (5 to 95% acetonitrile in water+0.1% trifluoroacetic acid over 6 mins) retention time 2.113 min, ESI+ found [M+H]=620.3.

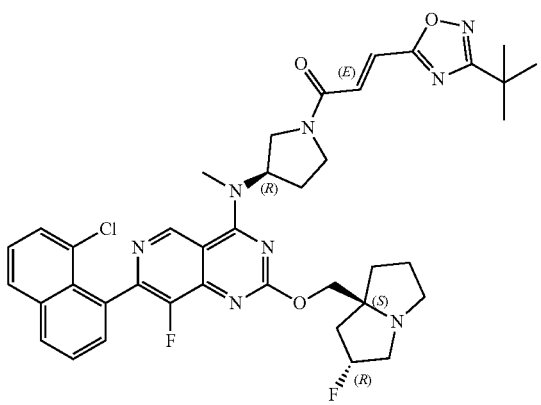

Example 146 (Method 1): (E)-3-(3-(tert-butyl)-1,2,4-oxadiazol-5-yl)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one

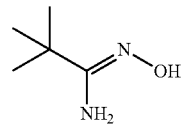

Step 1: (Z)—N'-hydroxypivalimidamide

The hydroxylimidamide formation was prepared in a similar fashion to Method #1, Step 1. The resulting residue was purified by column chromatography (silica gel, 100-200 mesh, 0-100% ethyl acetate in petroleum ether) affording (Z)—N'-hydroxypivalimidamide (3.54 g, 25%) as a blue solid: $^1$H NMR (400 MHz, Dimethylsulfoxide-d6) δ 8.91-8.76 (m, 1H), 5.27-5.13 (m, 2H), 1.08 (s, 9H).

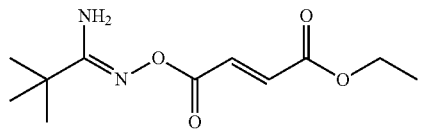 [SMILES: CCOC(=O)/C=C/C(=O)O/N=C(\N)C(C)(C)C]

Step 3: (E)-ethyl 4-(((Z)-(1-amino-2,2-dimethylpropylidene)amino)oxy)-4-oxobut-2-enoate The amide coupling reaction was prepared in a similar fashion to Method #1, Step 2. The reaction mixture was purified by column chromatography (silica gel, 100-200 mesh, 0-100% ethyl acetate in petroleum ether) affording (E)-ethyl 4-(((Z)-(1-amino-2,2-dimethylpropylidene)amino)oxy)-4-oxobut-2-enoate (1.14 g, 56%) as a white solid: $^1$H NMR (400 MHz, Chloroform-d) δ 7.06-6.87 (m, 2H), 4.88-4.71 (m, 2H), 4.35-4.18 (m, 2H), 1.33 (t, J=7.1 Hz, 3H), 1.30-1.26 (m, 9H).

LCMS Rt=0.636 min, m/z=242.1 [M+H]$^+$.

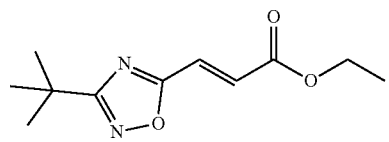 [SMILES: CCOC(=O)/C=C/c1nc(C(C)(C)C)no1]

Step 4: (E)-ethyl 3-(3-(tert-butyl)-1,2,4-oxadiazol-5-yl)acrylate

The cyclization reaction was prepared in a similar fashion to Method #1, Step 3. The crude was purified by column chromatography (silica gel, 100-200 mesh, 0-100% ethyl acetate in petroleum ether) affording (E)-ethyl 3-(3-(tert-butyl)-1,2,4-oxadiazol-5-yl)acrylate (730 mg, 68%) as a colorless oil: $^1$H NMR (400 MHz, Chloroform-d) δ 7.53-

7.44 (m, 1H), 7.05-6.93 (m, 1H), 4.37-4.22 (m, 2H), 1.40 (s, 9H), 1.37-1.32 (m, 3H). LCMS Rt=0.907 min, m/z=224.1 [M+H]⁺.

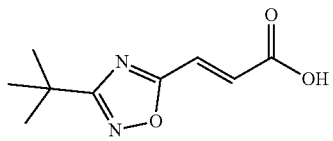

Step 5: (E)-3-(3-(tert-butyl)-1,2,4-oxadiazol-5-yl) acrylic acid

The hydrolysis reaction was prepared in a similar fashion to Method #1, Step 4.

The reaction mixture was quenched with hydrochloric acid (6 M, 10 mL) at 0° C. adjust pH=2 and extracted with ethyl acetate (2×30 mL). The combined organic layers were dried over sodium sulphate and concentrated in vacuo affording (E)-3-(3-(tert-butyl)-1,2,4-oxadiazol-5-yl)acrylic acid (330 mg, crude) as a white solid, used in next step without any further purification: $^1$H NMR (400 MHz, Chloroform-d) δ 7.64-7.55 (m, 1H), 7.08-6.98 (m, 1H), 1.44-1.39 (m, 9H). LCMS Rt=0.455 min, m/z=196.1 [M+H]⁺

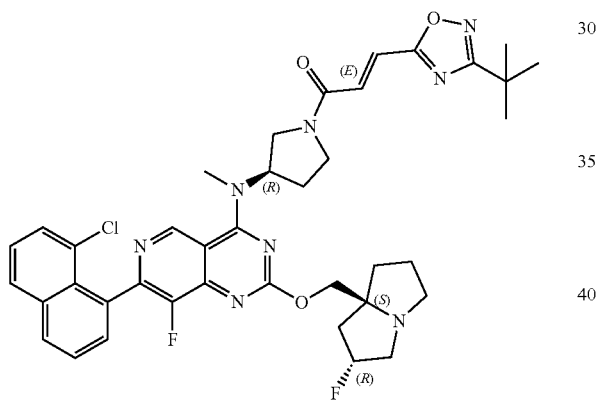

Step 6: (E)-3-(3-(tert-butyl)-1,2,4-oxadiazol-5-yl)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl) amino)pyrrolidin-1-yl)prop-2-en-1-one The amide coupling reaction was prepared in a similar fashion to Method #1, Step 10. The residue was purified by reverse phase HPLC (column: Waters Xbridge Prep OBD C18 150*40 mm*10 um; mobile phase: [water (NH₄HCO₃)-acetonitrile]; B %: 40%-75%, 8 min) affording (E)-3-(3-(tert-butyl)-1,2,4-oxadiazol-5-yl)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido [4,3-d]pyrimidin-4-yl)(methyl)amino)pyrrolidin-1-yl)prop-2-en-1-one (19.4 mg, 22.04%) as a white solid: $^1$H NMR (400 MHz, Acetonitrile-d3) δ 9.28-9.10 (m, 1H), 8.18-8.12 (m, 1H), 8.04 (d, J=8.0 Hz, 1H), 7.76-7.69 (m, 1H), 7.68-7.59 (m, 2H), 7.57-7.49 (m, 1H), 7.48-7.36 (m, 2H), 5.50-5.17 (m, 2H), 4.30-4.10 (m, 3H), 4.03 (br s, 1H), 3.94-3.61 (m, 2H), 3.47 (s, 3H), 3.24-3.05 (m, 3H), 2.91 (br s, 1H), 2.36 (br d, J=6.1 Hz, 3H), 2.13 (br s, 3H), 1.92-1.84 (m, 2H), 1.39 (d, J=7.9 Hz, 9H). LCMS Rt=2.401 min, m/z=742.3 [M+H]⁺.

LCMS (5 to 95% acetonitrile in water+0.03% ammonium bicarbonate over 6 mins) retention time 2.401 min. ESI+ found [M+H]=742.3.

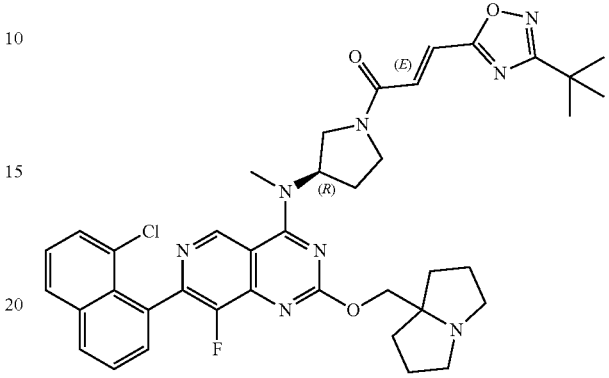

Example 147 (Method 2): (R,E)-3-(3-(tert-butyl)-1,2,4-oxadiazol-5-yl)-1-(3-((7-(8-chloronaphthalen-1-yl)-8-fluoro-2-((hexahydro-1H-pyrrolizin-7a-yl) methoxy)pyrido[4,3-d]pyrimidin-4-yl)(methyl) amino)pyrrolidin-1-yl)prop-2-en-1-one

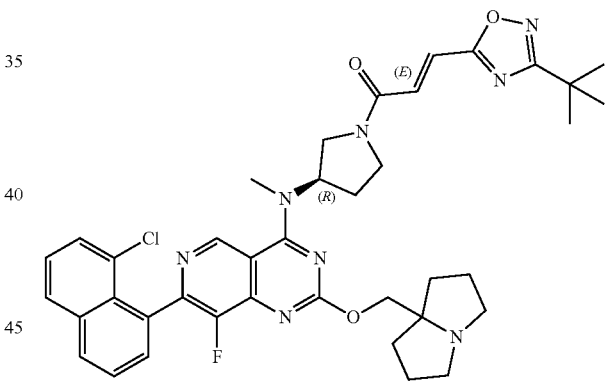

Step 1: (R,E)-3-(3-(tert-butyl)-1,2,4-oxadiazol-5-yl)-1-(3-((7-(8-chloronaphthalen-1-yl)-8-fluoro-2-((hexahydro-1H-pyrrolizin-7a-yl)methoxy)pyrido[4,3-d]pyrimidin-4-yl)(methyl)amino)pyrrolidin-1-yl) prop-2-en-1-one The amide coupling reaction was prepared in a similar fashion to Method #2, Step 7. The crude was purified by reverse phase HPLC (column: Waters Xbridge Prep OBD C18 150*40 mm*10 um; mobile phase: [water (NH₄HCO₃)-acetonitrile]; B %: 40%-70%, 8 min) affording (R,E)-3-(3-(tert-butyl)-1,2,4-oxadiazol-5-yl)-1-(3-((7-(8-chloronaphthalen-1-yl)-8-fluoro-2-((hexahydro-1H-pyrrolizin-7a-yl) methoxy)pyrido[4,3-d]pyrimidin-4-yl)(methyl)amino) pyrrolidin-1-yl)prop-2-en-1-one (11.98 mg, 12.76%) as a yellow amorphous solid: $^1$H NMR (400 MHz, Acetonitrile-d3) δ 9.22 (t, J=1.9 Hz, 1H), 8.15 (d, J=7.1 Hz, 1H), 8.05 (d, J=8.0 Hz, 1H), 7.76-7.69 (m, 1H), 7.68-7.62 (m, 2H), 7.56-7.50 (m, 1H), 7.48-7.29 (m, 2H), 5.51-5.31 (m, 1H), 4.23-4.16 (m, 2H), 4.10-3.99 (m, 1H), 3.97-3.84 (m, 1H), 3.83-3.75 (m, 1H), 3.69-3.52 (m, 1H), 3.47 (s, 3H), 3.03-2.93 (m, 2H), 2.67-2.56 (m, 2H), 2.46 (dt, J=6.0, 7.8 Hz, 1H), 2.40-2.32 (m, 1H), 1.93 (br s, 1H), 1.90-1.76 (m, 5H), 1.69-1.59 (m, 2H), 1.40 (d, J=8.0 Hz, 9H). LCMS Rt=2.358 min, m/z=724.3 [M+H]⁺.

LCMS (5 to 95% acetonitrile in water+0.03% ammonium bicarbonate over 6 mins) retention time 2.358 min, ESI+ found [M+H]=724.3.

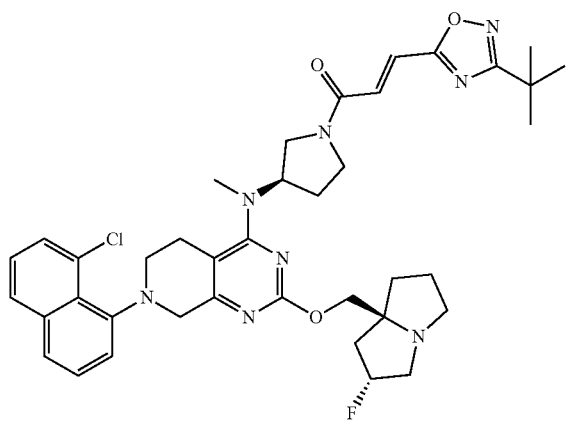 [SMILES: CN(c1nc(OC[C@@]23CCCN2C[C@H](F)C3)nc2c1CCN(c1cccc3cccc(Cl)c13)C2)[C@@H]1CCN(C(=O)/C=C/c2nc(C(C)(C)C)no2)C1]

Example 148 (Method 4): (E)-3-(3-(tert-butyl)-1,2,4-oxadiazol-5-yl)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)prop-2-en-1-one

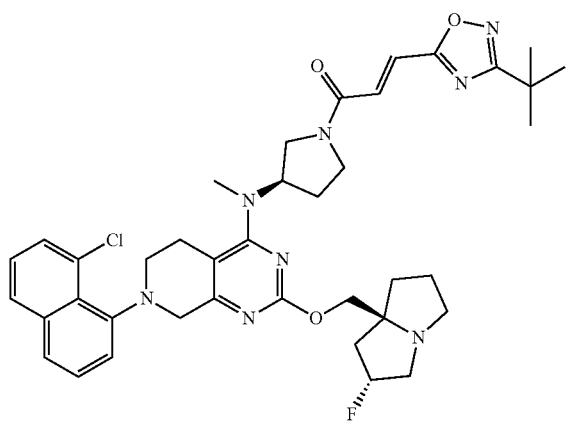 [SMILES: CN(c1nc(OC[C@@]23CCCN2C[C@H](F)C3)nc2c1CCN(c1cccc3cccc(Cl)c13)C2)[C@@H]1CCN(C(=O)/C=C/c2nc(C(C)(C)C)no2)C1]

Step 1: (E)-3-(3-(tert-butyl)-1,2,4-oxadiazol-5-yl)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)prop-2-en-1-one The amide coupling reaction was prepared in a similar fashion to Method #4, Step 11. The crude product was purified by reverse phase HPLC (column: Waters Xbridge BEH C18 100*30 mm*10 μm; mobile phase: [water (ammonium bicarbonate)- acetonitrile]; B %: 50%-85%, 10 min) affording (E)-3-(3-(tert-butyl)-1,2,4-oxadiazol-5-yl)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)prop-2-en-1-one (48.81 mg, 49.16%) as a yellow oil: ¹H NMR (400 MHz, Acetonitrile-d3) δ 7.84 (d, J=7.9 Hz, 1H), 7.67 (br d, J=7.7 Hz, 1H), 7.56-7.45 (m, 2H), 7.41-7.28 (m, 4H), 5.32-5.09 (m, 1H), 4.90-4.71 (m, 1H), 4.25-4.09 (m, 1H), 4.06-3.85 (m, 3H), 3.84-3.60 (m, 3H), 3.56-3.37 (m, 2H), 3.31-3.17 (m, 1H), 3.15-2.99 (m, 4H), 2.98-2.93 (m, 3H), 2.92-2.78 (m, 1H), 2.66-2.56 (m, 1H), 2.12-1.96 (m, 5H), 1.90-1.71 (m, 3H), 1.39-1.31 (m, 9H). LCMS Rt=3.572 min, m/z=728.3 [M+H]⁺.

LCMS (5 to 95% acetonitrile in water+0.03% ammonium bicarbonate over 6 mins) retention time 3.572 min, ESI+ found [M+H]=728.3.

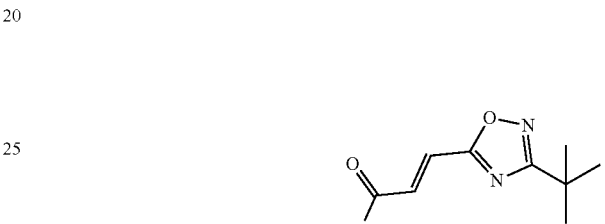

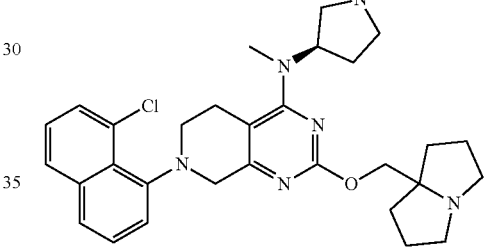

Example 149 (Method 4): (R,E)-3-(3-(tert-butyl)-1,2,4-oxadiazol-5-yl)-1-(3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)prop-2-en-1-one

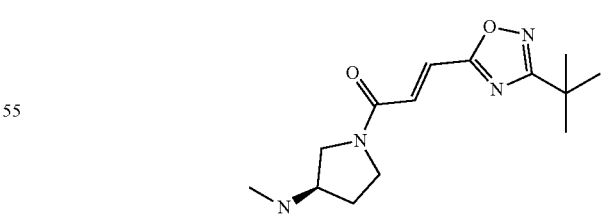

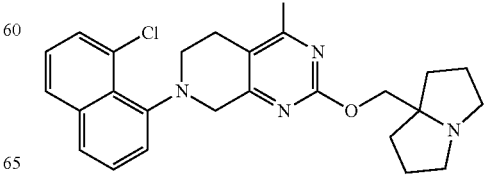

743

Step 1: (R,E)-3-(3-(tert-butyl)-1,2,4-oxadiazol-5-yl)-1-(3-((7-(8-chloronaphthalen-1-yl)-2-((hexahydro-1H-pyrrolizin-7a-yl)methoxy)-5,6,7,8-tetrahydro-pyrido[3,4-d]pyrimidin-4-yl)(methyl)amino) pyrrolidin-1-yl)prop-2-en-1-one The amide coupling reaction was prepared in a similar fashion to Method #4, Step 11. The crude product was purified by reverse phase HPLC (column: Waters Xbridge Prep OBD C18 150*40 mm*10 um; mobile phase: [water (ammonium bicarbonate- acetonitrile]; B %: 50%-80%, 8 min) affording (R,E)-3-(3-(tert-butyl)-1,2,4-oxadiazol-5-yl)-1-(3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)prop-2-en-1-one (21.33 mg, 23.55%) as a yellow solid: $^1$HNMR (400 MHz, Acetonitrile-d3) δ 7.88-7.81 (m, 1H), 7.68 (br d, J=8.1 Hz, 1H), 7.57-7.46 (m, 2H), 7.46-7.36 (m, 2H), 7.36-7.29 (m, 2H), 4.95-4.66 (m, 1H), 4.30-4.19 (m, 1H), 4.18-3.77 (m, 4H), 3.76-3.60 (m, 2H), 3.57-3.38 (m, 2H), 3.16 (br s, 1H), 3.15-3.06 (m, 1H), 3.05-2.85 (m, 5H), 2.66-2.51 (m, 3H), 2.43-2.26 (m, 2H), 1.92-1.85 (m, 2H), 1.85-1.71 (m, 4H), 1.59 (br dd, J=6.9, 12.3 Hz, 2H), 1.41-1.30 (m, 9H). LCMS Rt=3.512 min, m/z=710.4 [M+H]$^+$.

LCMS (5 to 95% acetonitrile in water+0.03% ammonium bicarbonate over 6 mins) retention time 3.512 min, ESI+ found [M+H]=710.4.

744

Example 150 (Method 4): (E)-1-(3-(((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)methyl)azetidin-1-yl)-3-(3-(difluoromethyl)-1,2,4-oxadiazol-5-yl)prop-2-en-1-one

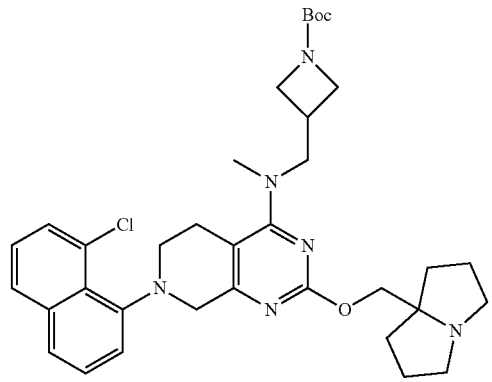 [SMILES: CN(CC1CN(C(=O)OC(C)(C)C)C1)c1nc(OCC23CCCN2CCC3)nc2c1CCN(c1cccc3cccc(Cl)c13)C2]

Step 1: tert-butyl 3-(((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl) amino)methyl)azetidine-1-carboxylate The substitution reaction was prepared in a similar fashion to Method #4, Step 9.

The reaction mixture was concentrated in vacuo and purified by reverse phase HPLC (column: Waters Xbridge Prep OBD C18 150*40 mm*10 um; mobile phase: [(water (ammonium bicarbonate)- acetonitrile]; B %: 55%-85%, 8 min) affording tert-butyl 3-(((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)methyl) azetidine-1-carboxylate (150 mg 33.55%) as a brown oil. LCMS Rt=0.884 min, m/z=632.3 [M+H]$^+$.

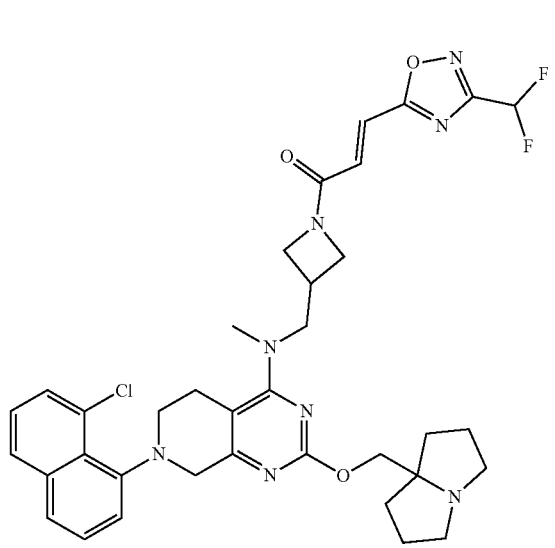 [SMILES: CN(CC1CN(C(=O)/C=C/c2nc(C(F)F)no2)C1)c1nc(OCC23CCCN2CCC3)nc2c1CCN(c1cccc3cccc(Cl)c13)C2]

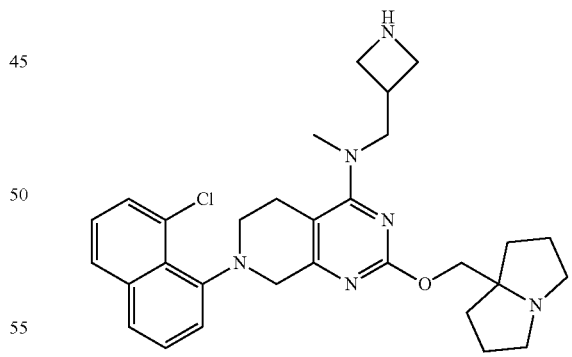

Step 2: N-(azetidin-3-ylmethyl)-7-(8-chloronaphthalen-1-yl)-2-((hexahydro-1H-pyrrolizin-7a-yl) methoxy)-N-methyl-5,6,7,8-tetrahydropyrido[3,4-d] pyrimidin-4-amine The deprotection of Boc was prepared in a similar fashion to Method #1, Step 9.

The mixture was concentrated in vacuo affording N-(azetidin-3-ylmethyl)-7-(8-chloronaphthalen-1-yl)-2-((hexahydro-1H-pyrrolizin-7a-yl)methoxy)-N-methyl-5,6,7,8-tetrahydropyrido[3,4-d]pyrimidin-4-amine (143 mg crude, trifluoroacetate salt) as orange oil used in next step without any further purification. LCMS Rt=0.628 min, m/z=532.3 [M+H]+.

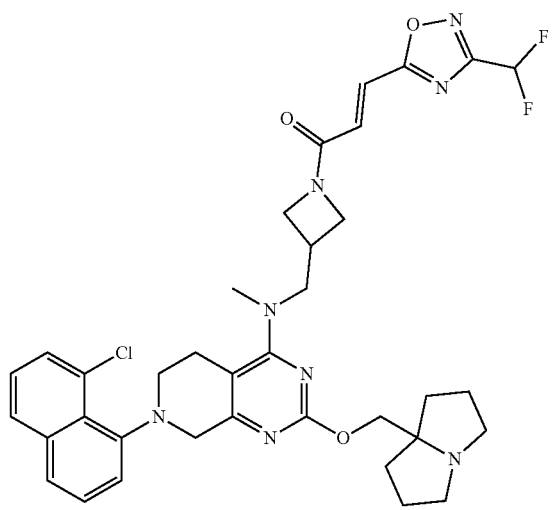

Step 3: (E)-1-(3-(((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl) amino)methyl)azetidin-1-yl)-3-(3-(difluoromethyl)-1,2,4-oxadiazol-5-yl)prop-2-en-1-one The amide coupling reaction was prepared in a similar fashion to Method #4, Step 11. The reaction mixture was concentrated in vacuo and purified by reverse phase HPLC (column: Phenomenex Luna C18 75*30 mm*3 μm; mobile phase: [water (formate)- acetonitrile]; B %: 30%-70%, 8 min) affording (E)-1-(3-(((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)methyl)azetidin-1-yl)-3-(3-(difluoromethyl)-1,2,4-oxadiazol-5-yl) prop-2-en-1-one (7.7 mg 4.85%, formate salt) as a yellow oil: $^1$H NMR (400 MHz, Acetonitrile-d3) δ 7.84 (d, J=8.1 Hz, 1H), 7.67 (d, J=8.1 Hz, 1H), 7.57-7.47 (m, 2H), 7.45-7.34 (m, 2H), 7.34-7.20 (m, 2H), 7.13-6.80 (m, 1H), 4.49-4.35 (m, 1H), 4.24-4.13 (m, 3H), 4.11-3.95 (m, 2H), 3.91-3.78 (m, 1H), 3.75-3.61 (m, 2H), 3.55-3.48 (m, 1H), 3.29-3.18 (m, 3H), 3.13-3.00 (m, 5H), 2.79-2.72 (m, 2H), 2.64 (br d, J=15.1 Hz, 2H), 2.00 (br dd, J=6.5, 12.1 Hz, 2H), 1.92-1.81 (m, 4H), 1.77-1.68 (m, 2H). LCMS Rt=2.367 min, m/z=704.3 [M+H]+.

LCMS (5 to 95% acetonitrile in water+0.1% trifluoroacetic acid over 6 mins) retention time 2.367 min, ESI+ found [M+H]=704.3.

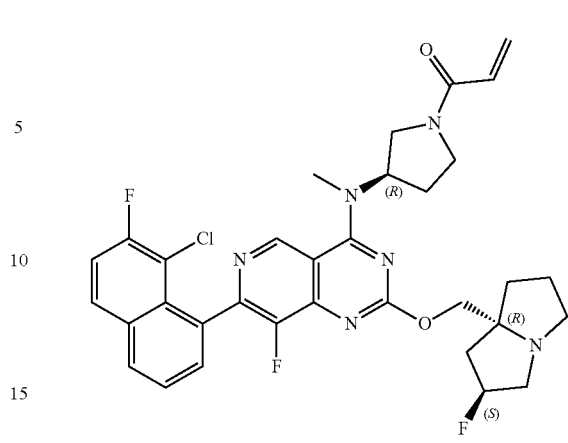

Example 151 (Method 1): 1-((R)-3-((7-(8-chloro-7-fluoronaphthalen-1-yl)-8-fluoro-2-(((2S,7aR)-2-fluorohexahydro-1H-pyrrolizin-7a-yl)methoxy)pyrido[4,3-d]pyrimidin-4-yl)(methyl)amino)pyrrolidin-1-yl) prop-2-en-1-one

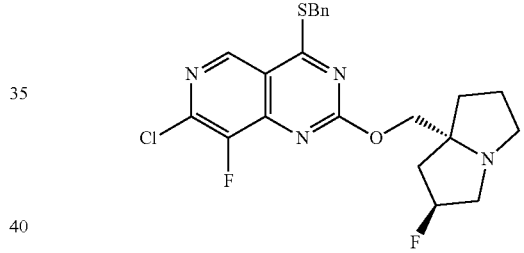

Step 1: 4-(benzylthio)-7-chloro-8-fluoro-2-(((2S,7aR)-2-fluorohexahydro-1H-pyrrolizin-7a-yl) methoxy)pyrido[4,3-d]pyrimidine To a solution of 4-(benzylthio)-2,7-dichloro-8-fluoropyrido[4,3-d]pyrimidine (2 g, 5.88 mmol) and ((2S,7aR)-2-fluorohexahydro-1H-pyrrolizin-7a-yl)methanol (1.40 g, 8.82 mmol) in dioxane (3 mL) was added N,N-diisopropylethylamine (2.28 g, 17.64 mmol). The mixture was stirred at 80° C. for 1 h. The mixture was diluted with water (20 mL) and extracted with ethyl acetate (3×50 mL). The combined organic layers were dried over sodium sulphate and concentrated in vacuo affording 4-(benzylthio)-7-chloro-8-fluoro-2-(((2S,7aR)-2-fluorohexahydro-1H-pyrrolizin-7a-yl)methoxy)pyrido[4,3-d]pyrimidine (2.3 g, crude) as a yellow solid, used in the next step without further purification: $^1$H NMR (400 MHz, Chloroform-d) δ 8.98-8.89 (m, 1H), 7.48 (d, J=6.8 Hz, 2H), 7.40-7.31 (m, 3H), 5.45-5.33 (m, 1H), 5.29-5.20 (m, 1H), 4.66 (s, 2H), 3.38-3.20 (m, 4H), 3.06-3.00 (m, 1H), 2.30-2.12 (m, 3H), 2.05-1.96 (m, 3H). LCMS Rt=0.577 min, m/z=462.1 [M+H]+.

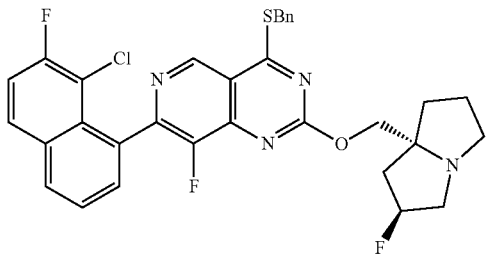

Step 2: 4-(benzylthio)-7-(8-chloro-7-fluoronaphtha-len-1-yl)-8-fluoro-2-(((2S,7aR)-2-fluorohexahydro-1H-pyrrolizin-7a-yl)methoxy)pyrido[4,3-d]pyrimidine To a solution of 4-(benzylthio)-7-chloro-8-fluoro-2-(((2S,7aR)-2-fluorohexahydro-1H-pyrrolizin-7a-yl)methoxy)pyrido[4,3-d]pyrimidine (700.00 mg, 1.51 mmol) in dioxane (13 mL) and water (4 mL) were added (8-chloro-7-fluoro-1-naphthyl)boronic acid (441.15 mg, 1.97 mmol), potassium phosphate (962.90 mg, 4.54 mmol) and methanesulfonic acid(2-dicyclohexylphosphino-2',4',6'-triisopropyl-1,1'-biphenyl)[2-(2'-amino-1,1'-biphenyl)]palladium(II) (118.97 mg, 151.21 μmol), then the mixture was heated to 60° C. and stirred for 2 h under nitrogen atmosphere. The mixture was diluted with water (20 mL), extracted with dichloromethane (2×20 mL). The combined organic layers were concentrated to dryness in vacuo and purified by column chromatography (silica gel, 100-200 mesh, 0-12% methanol in dichloromethane) affording 4-(benzylthio)-7-(8-chloro-7-fluoronaphtha-len-1-yl)-8-fluoro-2-(((2S,7aR)-2-fluorohexahydro-1H-pyrrolizin-7a-yl)methoxy)pyrido[4,3-d]pyrimidine (700 mg, 76.26%) as a yellow oil. LCMS Rt=0.859 min, m/z=606.2 [M+H]+.

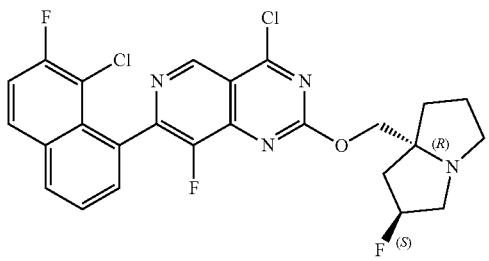

Step 3: 4-chloro-7-(8-chloro-7-fluoronaphthalen-1-yl)-8-fluoro-2-(((2S,7aR)-2-fluorohexahydro-1H-pyrrolizin-7a-yl)methoxy)pyrido[4,3-d]pyrimidine The chlorination reaction was prepared in a similar fashion to Method #1, Step 7. The reaction mixture was concentrated in vacuo affording 4-chloro-7-(8-chloro-7-fluoronaphthalen-1-yl)-8-fluoro-2-(((2S,7aR)-2-fluorohexahydro-1H-pyrrolizin-7a-yl)methoxy)pyrido[4,3-d]pyrimidine (320 mg, crude) as a yellow oil, used in next step without any further purification. LCMS Rt=0.573 min, m/z=518.1 [M+H]+.

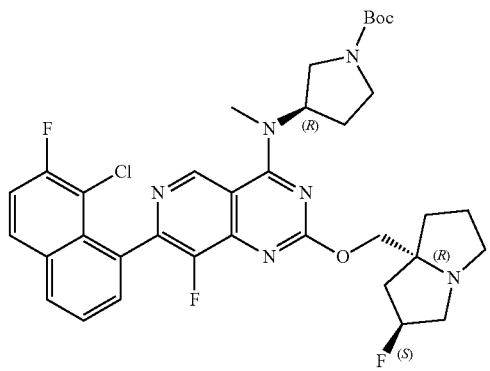

Step 4: (R)-tert-butyl 3-((7-(8-chloro-7-fluoronaph-thalen-1-yl)-8-fluoro-2-(((2S,7aR)-2-fluorohexa-hydro-1H-pyrrolizin-7a-yl)methoxy)pyrido[4,3-d]pyrimidin-4-yl)(methyl)amino)pyrrolidine-1-carboxylate The substitution reaction was prepared in a similar fashion to Method #1, Step 8. The reaction mixture was quenched with water (30 mL) at 0° C. and extracted with ethyl acetate (3×100 mL). The combined organic layers were dried over sodium sulphate and concentrated in vacuo affording (R)-tert-butyl 3-((7-(8-chloro-7-fluoronaphthalen-1-yl)-8-fluoro-2-(((2S,7aR)-2-fluorohexahydro-1H-pyrrolizin-7a-yl)methoxy)pyrido[4,3-d]pyrimidin-4-yl)(methyl)amino)pyrrolidine-1-carboxylate (510 mg, crude) as a yellow oil, used in the next step without further purification. LCMS Rt=0.625 min, m/z=683.2 [M+H]+.

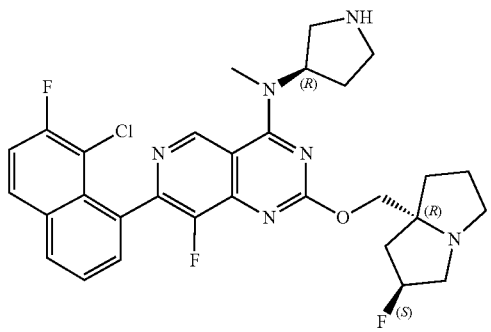

Step 5: 7-(8-chloro-7-fluoronaphthalen-1-yl)-8-fluoro-2-(((2S,7aR)-2-fluorohexahydro-1H-pyr-rolizin-7a-yl)methoxy)-N-methyl-N—((R)-pyrroli-din-3-yl)pyrido[4,3-d]pyrimidin-4-amine The deprotection of Boc was prepared in a similar fashion to Method #1, Step 9. The reaction mixture was concentrated in vacuo affording 7-(8-chloro-7-fluoronaphthalen-1-yl)-8-fluoro-2-(((2S,7aR)-2-fluorohexahydro-1H-pyrrolizin-7a-yl)methoxy)-N-methyl-N—((R)-pyrrolidin-3-yl)pyrido[4,3-d]pyrimidin-4-amine (500 mg, crude, trifluoroacetate salt) as a yellow oil. LCMS Rt=0.564 min, m/z=582.2 [M+H]+.

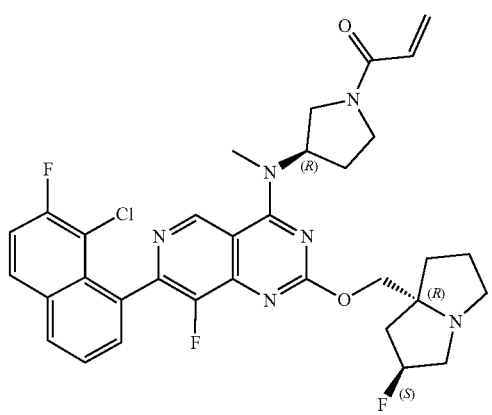

10 Step 6: 1-((R)-3-((7-(8-chloro-7-fluoronaphthalen-1-yl)-8-fluoro-2-(((2S,7aR)-2-fluorohexahydro-1H-pyrrolizin-7a-yl)methoxy)pyrido[4,3-d]pyrimidin-4-yl)(methyl)amino)pyrrolidin-1-yl)prop-2-en-1-one The amide coupling reaction was prepared in a similar fashion to Method #1, Step 10. The reaction mixture was diluted with water (2 mL) and extracted with dichloromethane (2×2 mL). The combined organic layers were dried over sodium sulphate and concentrated in vacuo. The resulting residue was purified by reverse phase HPLC (column: Waters Xbridge Prep OBD C18 150*40 mm*10 μm; mobile phase: [water (NH$_4$HCO$_3$)-acetonitrile]; B %: 35%-65%, 8 min) affording 1-((R)-3-((7-(8-chloro-7-fluoronaphthalen-1-yl)-8-fluoro-2-(((2S,7aR)-2-fluorohexahydro-1H-pyrrolizin-7a-yl)methoxy)pyrido[4,3-d]pyrimidin-4-yl)(methyl)amino)pyrrolidin-1-yl)prop-2-en-1-one (24.46 mg, 5.00%) as a white solid: $^1$H NMR (400 MHz, Acetonitrile-d3) δ 9.32-9.11 (m, 1H), 8.22-7.99 (m, 2H), 7.76-7.66 (m, 2H), 7.55 (t, J=8.9 Hz, 1H), 6.71-6.52 (m, 1H), 6.34-6.19 (m, 1H), 5.70 (ddd, J=2.2, 6.1, 10.3 Hz, 1H), 5.44-5.34 (m, 1H), 4.29-4.13 (m, 2H), 4.12-3.93 (m, 1H), 3.92-3.78 (m, 1H), 3.77-3.53 (m, 2H), 3.52-3.42 (m, 4H), 3.23-3.07 (m, 3H), 2.98-2.87 (m, 1H), 2.47-2.22 (m, 4H), 2.11-2.06 (m, 1H), 1.94-1.79 (m, 3H). LCMS Rt=2.108 min, m/z=636.2 [M+H]$^+$.

LCMS (5 to 95% acetonitrile in water+0.03% ammonium bicarbonate over 6 mins) retention time 2.108 min, ESI+ found [M+H]=636.2.

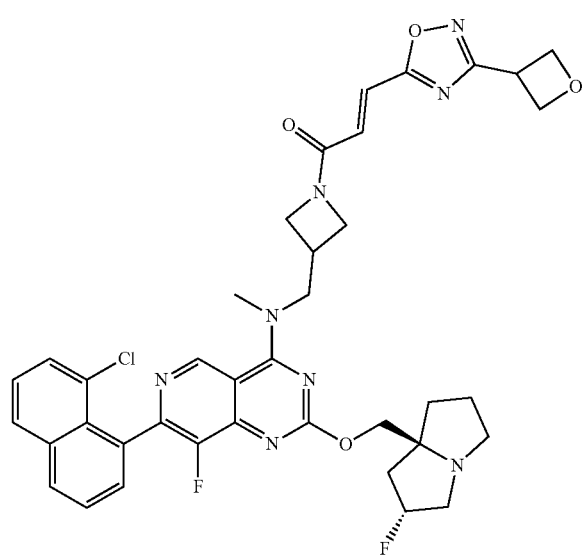 [SMILES: CN(CC1CN(C(=O)/C=C/c2nc(C3COC3)no2)C1)c1nc(OC[C@@]23CCCN2C[C@H](F)C3)nc2c(F)c(-c3cccc4cccc(Cl)c34)ncc12]

Example 152 (Method 1): (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-(oxetan-3-yl)-1,2,4-oxadiazol-5-yl)prop-2-en-1-one

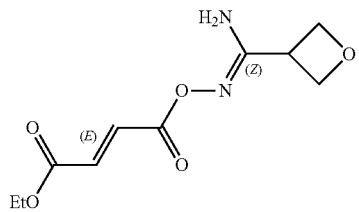 [SMILES: CCOC(=O)/C=C/C(=O)O/N=C(\N)C1COC1]

Step 1: (E)-ethyl 4-(((Z)-(amino(oxetan-3-yl)methylene)amino)oxy)-4-oxobut-2-enoate The amide coupling reaction was prepared in a similar fashion to Method #1, Step 2.

The reaction mixture was concentrated in vacuo affording (E)-ethyl 4-(((Z)-(amino(oxetan-3-yl)methylene)amino)oxy)-4-oxobut-2-enoate (1.1 g, crude) as a brown oil, used in next step without further purification. LCMS Rt=0.430 min, m/z=242.1 [M+H]$^+$.

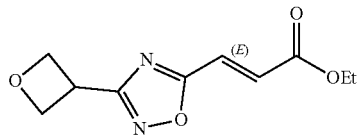 [SMILES: CCOC(=O)/C=C/c1nc(C2COC2)no1]

Step 2: (E)-ethyl 3-(3-(oxetan-3-yl)-1,2,4-oxadiazol-5-yl)acrylate

The cyclization reaction was prepared in a similar fashion to Method #1, Step 3.

The resulting residue was purified by column chromatography (silica gel, 100-200 mesh, 20% ethyl acetate in petroleum ether) (E)-ethyl 3-(3-(oxetan-3-yl)-1,2,4-oxadiazol-5-yl)acrylate (1.1 g, crude) as a yellow oil, used in next step without further purification. LCMS Rt=0.671 min, m/z =224.1 [M+H]$^+$.

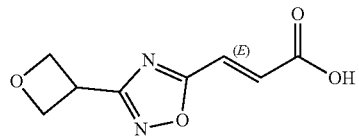 [SMILES: O=C(O)/C=C/c1nc(C2COC2)no1]

Step 3: (E)-3-(3-(oxetan-3-yl)-1,2,4-oxadiazol-5-yl)acrylic acid

The hydrolysis reaction was prepared in a similar fashion to Method #1, Step 4.

The reaction mixture was concentrated in vacuo affording (E)-3-(3-(oxetan-3-yl)-1,2,4-oxadiazol-5-yl)acrylic acid (570 mg, crude) as a white solid, used in next step without further purification.

LCMS Rt=0.221 min, m/z=196.1 [M+H]⁺.

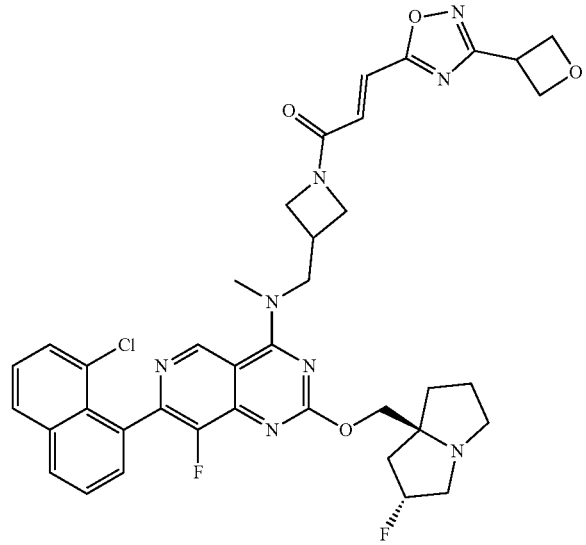 [SMILES: CN(CC1CN(C(=O)/C=C/c2nc(C3COC3)no2)C1)c1nc(OC[C@@]23CCCN2C[C@H](F)C3)nc2c(F)c(-c3cccc4cccc(Cl)c34)ncc12]

Step 4: (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-(oxetan-3-yl)-1,2,4-oxadiazol-5-yl)prop-2-en-1-one The amide coupling reaction was prepared in a similar fashion to Method #1, Step 10. The residue was purified by reverse phase HPLC(column: Phenomenex Luna C18 75*30 mm*3 μm; mobile phase: [column: Phenomenex Luna C18 75*30 mm*3 μm; mobile phase: [water (formic acid)-acetonitrile]; B %: 10%-50%, 8 min) affording (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-(oxetan-3-yl)-1,2,4-oxadiazol-5-yl)prop-2-en-1-one (7.09 mg, 5.00%, formic acid salt) as a white solid: ¹H NMR (400 MHz, Acetonitrile-d3) δ 9.31-9.22 (m, 1H), 8.23-8.13 (m, 1H), 8.04 (d, J=8.1 Hz, 1H), 7.75-7.68 (m, 1H), 7.67-7.58 (m, 2H), 7.57-7.49 (m, 1H), 7.42-7.21 (m, 2H), 5.42-5.19 (m, 1H), 4.99 (dd, J=6.0, 8.4 Hz, 2H), 4.82 (t, J=6.3 Hz, 2H), 4.55-4.40 (m, 2H), 4.28 (br d, J=11.5 Hz, 2H), 4.25-4.22 (m, 1H), 4.21-4.17 (m, 2H), 3.98 (dt, J=5.8, 9.8 Hz, 1H), 3.61 (s, 3H), 3.29-3.16 (m, 4H), 2.97-2.93 (m, 1H), 2.32-2.21 (m, 1H), 2.19-2.14 (m, 1H), 2.13-2.07 (m, 1H), 1.96-1.78 (m, 4H). LCMS Rt=2.131 min, m/z=742.3 [M+H]⁺.

LCMS (5 to 95% acetonitrile in water+0.1% trifluoroacetic acid over 6 mins) retention time 2.131 min, ESI+ found [M+H]=742.3.

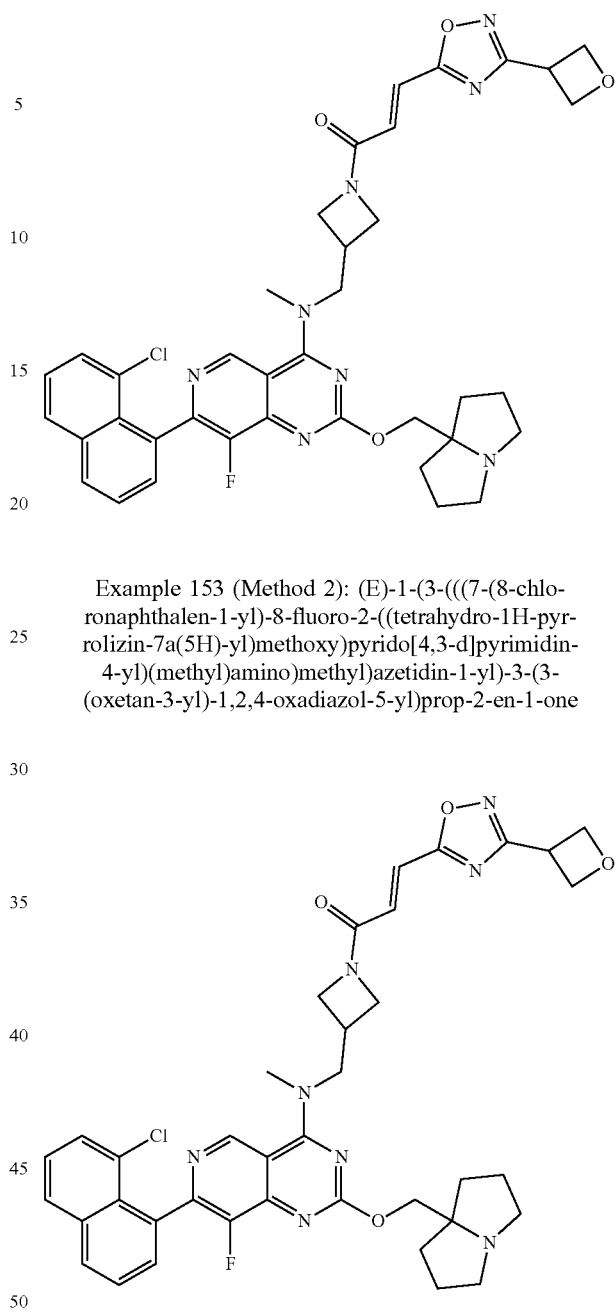

Example 153 (Method 2): (E)-1-(3-(((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)methyl)azetidin-1-yl)-3-(3-(oxetan-3-yl)-1,2,4-oxadiazol-5-yl)prop-2-en-1-one Step 1: (E)-1-(3-(((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)methyl)azetidin-1-yl)-3-(3-(oxetan-3-yl)-1,2,4-oxadiazol-5-yl)prop-2-en-1-one The amide coupling reaction was prepared in a similar fashion to Method #2, Step 7. The reaction mixture was purified by reverse phase HPLC (column: Waters Xbridge BEH C18 100*30 mm*10 um; mobile phase: [water (NH₄HCO₃)-acetonitrile]; B %: 30%-60%, 8 min) affording (E)-1-(3-(((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)methyl)azetidin-1-yl)-3-(3-(oxetan-3-yl)-1,2,4-oxadiazol-5-yl)prop-2-en-1-one (1.77 mg, 1.08%) as a white solid. ¹H NMR (400 MHz, Acetonitrile-d3) δ 9.26 (s, 1H), 8.14 (d, J=8.1 Hz, 1H), 8.04 (d, J=8.1 Hz, 1H), 7.74-7.68 (m, 1H), 7.67-7.59 (m, 1H), 7.59 (br d, J=4.3 Hz, 1H), 7.57-7.50 (m, 1H), 7.57-7.49 (m, 1H), 7.43-7.32 (m, 1H), 7.27-7.19 (m, 1H), 4.99 (dd, J=6.1, 8.4 Hz, 2H), 4.82 (t, J=6.3 Hz, 2H), 4.54-4.42 (m, 1H), 4.42 (br s, 1H), 4.37-4.25 (m, 1H), 4.22-4.09 (m, 4H), 3.96 (dt, J=6.1, 9.4 Hz, 1H), 3.61 (s, 3H), 3.32-3.19 (m, 1H), 3.02-2.92 (m, 2H), 2.65-2.54 (m, 2H), 1.95-1.90 (m, 1H), 1.95-1.73 (m, 5H), 1.70-1.58 (m, 1H), 1.71-1.58 (m, 1H). LCMS Rt=2.682 min, m/z=724.3 [M+H]⁺.

LCMS (5 to 95% acetonitrile in water+0.03% ammonium bicarbonate over 6 mins) retention time 2.682 min, ESI+ found [M+H]=724.3.

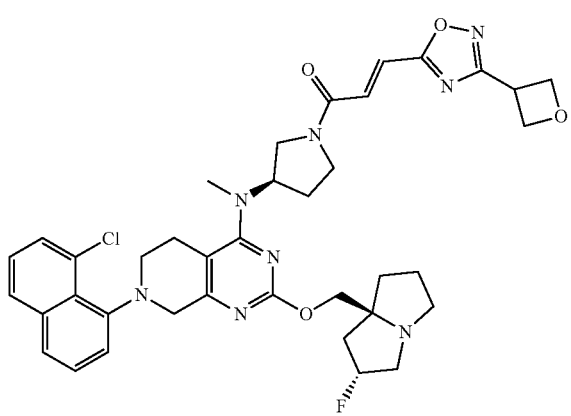 [SMILES: CN(c1nc(OC[C@@]23CCCN2C[C@H](F)C3)nc2c1CCN(c1cccc3cccc(Cl)c13)C2)[C@@H]1CCN(C(=O)/C=C/c2nc(C3COC3)no2)C1]

Example 154 (Method 4): (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-(oxetan-3-yl)-1,2,4-oxadiazol-5-yl)prop-2-en-1-one

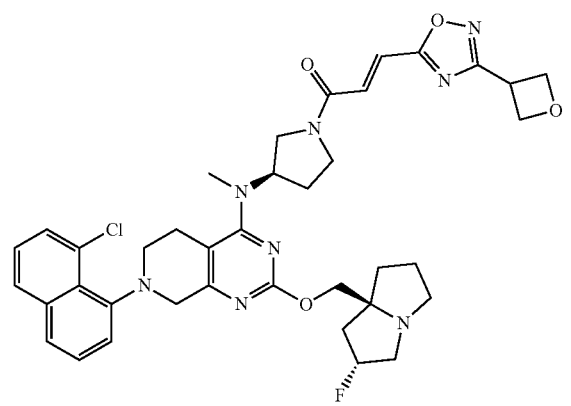 [SMILES: CN(c1nc(OC[C@@]23CCCN2C[C@H](F)C3)nc2c1CCN(c1cccc3cccc(Cl)c13)C2)[C@@H]1CCN(C(=O)/C=C/c2nc(C3COC3)no2)C1]

Step 1: (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-(oxetan-3-yl)-1,2,4-oxadiazol-5-yl)prop-2-en-1-one The amide coupling reaction was prepared in a similar fashion to Method #4, Step 11. The crude product was purified by reverse phase HPLC (column: Waters Xbridge Prep OBD C18 150*40 mm*10 μm; mobile phase: [water (ammonium bicarbonate)- acetonitrile]; B %: 45%-75%, 8 min) affording (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-(oxetan-3-yl)-1,2,4-oxadiazol-5-yl)prop-2-en-1-one (13.28 mg, 9.99%) as a yellow solid: ¹H NMR (400 MHz, Acetonitrile-d3) δ 7.87 (d, J=8.1 Hz, 1H), 7.70 (br d, J=8.1 Hz, 1H), 7.59-7.48 (m, 3H), 7.47-7.38 (m, 2H), 7.37-7.31 (m, 1H), 5.36-5.14 (m, 1H), 5.04-4.95 (m, 2H), 4.91-4.74 (m, 3H), 4.53-4.41 (m, 1H), 4.31-4.15 (m, 1H), 4.11-3.91 (m, 3H), 3.90-3.64 (m, 3H), 3.59-3.40 (m, 2H), 3.33-3.21 (m, 1H), 3.16-3.04 (m, 4H), 3.02-2.97 (m, 3H), 2.95-2.81 (m, 1H), 2.62 (br d, J=14.8 Hz, 1H), 2.40-2.29 (m, 1H), 2.23-2.19 (m, 1H), 2.18-2.14 (m, 1H), 2.08 (br s, 2H), 1.94-1.72 (m, 3H). LCMS Rt=3.298 min, m/z=728.3 [M+H]⁺.

LCMS (5 to 95% acetonitrile in water+0.03% ammonium bicarbonate over 6 mins) retention time 3.298 min, ESI+ found [M+H]=728.3.

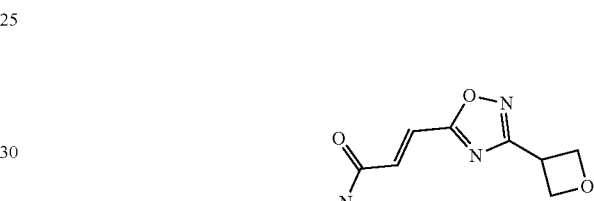


Example 155 (Method 1): (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-(oxetan-3-yl)-1,2,4-oxadiazol-5-yl)prop-2-en-1-one

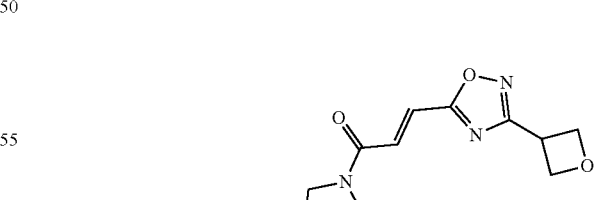

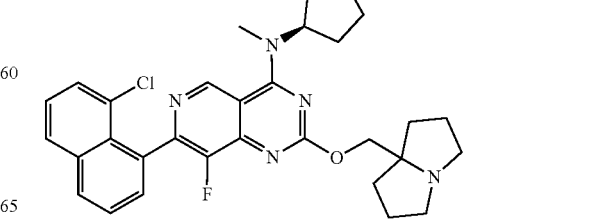

Step 1: (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-(oxetan-3-yl)-1,2,4-oxadiazol-5-yl)prop-2-en-1-one The amide coupling reaction was prepared in a similar fashion to Method #1, Step 10. The reaction mixture was purified by reverse phase HPLC (column: Waters Xbridge Prep OBD C18 150*40 mm*10 μm; mobile phase: [water (NH$_4$HCO$_3$)-acetonitrile]; B %: 25%-55%, 8 min) affording (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-(oxetan-3-yl)-1,2,4-oxadiazol-5-yl)prop-2-en-1-one (19.46 mg, 13.44%) as a yellow solid: $^1$H NMR (400 MHz, Acetonitrile-d3) δ 9.22 (t, J=1.7 Hz, 1H), 8.15 (dd, J=1.1, 8.1 Hz, 1H), 8.07-8.02 (m, 1H), 7.76-7.69 (m, 1H), 7.67-7.62 (m, 2H), 7.58-7.50 (m, 2H), 7.49-7.41 (m, 1H), 5.50-5.34 (m, 1H), 5.00 (dt, J=6.0, 8.3 Hz, 2H), 4.83 (td, J=6.3, 10.4 Hz, 2H), 4.52-4.41 (m, 1H), 4.26-4.15 (m, 2H), 4.10-4.00 (m, 1H), 3.97-3.74 (m, 2H), 3.70-3.52 (m, 1H), 3.46 (s, 3H), 2.99 (qd, J=5.1, 10.3 Hz, 2H), 2.66-2.56 (m, 2H), 2.50-2.29 (m, 3H), 1.92-1.74 (m, 5H), 1.65 (br dd, J=4.8, 7.4 Hz, 2H). LCMS Rt=2.122 min, m/z=724.3 [M+H]$^+$.

LCMS (5 to 95% acetonitrile in water+0.1% trifluoroacetic acid over 6 mins) retention time 2.122 min, ESI+ found [M+H]=724.3.

Step 1: (R,E)-1-(3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-(oxetan-3-yl)-1,2,4-oxadiazol-5-yl)prop-2-en-1-one The amide coupling reaction was prepared in a similar fashion to Method #4, Step 11. The crude product was purified by reverse phase HPLC (column: Waters Xbridge Prep OBD C18 150*40 mm*10 μm; mobile phase: [water (ammonium bicarbonate- acetonitrile]; B %: 45%-75%, 8 min) affording (R,E)-1-(3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-(oxetan-3-yl)-1,2,4-oxadiazol-5-yl)prop-2-en-1-one (14.23 mg, 7.11%) as a yellow solid: $^1$H NMR (400 MHz, Acetonitrile-d3) δ 7.89-7.84 (m, 1H), 7.73-7.68 (m, 1H), 7.58 (d, J=7.4 Hz, 1H), 7.55-7.49 (m, 2H), 7.46-7.43 (m, 1H), 7.43-7.39 (m, 1H), 7.38-7.32 (m, 1H), 5.02-4.96 (m, 2H), 4.89-4.78 (m, 3H), 4.51-4.42 (m, 1H), 4.27 (br dd, J=4.3, 17.3 Hz, 1H), 4.09-3.94 (m, 3H), 3.90-3.78 (m, 1H), 3.76-3.66 (m, 2H), 3.59-3.42 (m, 2H), 3.34-3.18 (m, 1H), 3.16-3.05 (m, 2H), 3.03 (br s, 4H), 2.69-2.58 (m, 3H), 2.32-2.11 (m, 3H), 1.95-1.92 (m, 1H), 1.90-1.76 (m, 4H), 1.65 (dtd, J=3.4, 7.8, 11.6 Hz, 2H). LCMS Rt=3.036 min, m/z=710.3 [M+H]$^+$.

LCMS (5 to 95% acetonitrile in water+0.03% ammonium bicarbonate over 6 mins) retention time 3.036 min, ESI+ found [M+H]=710.3.

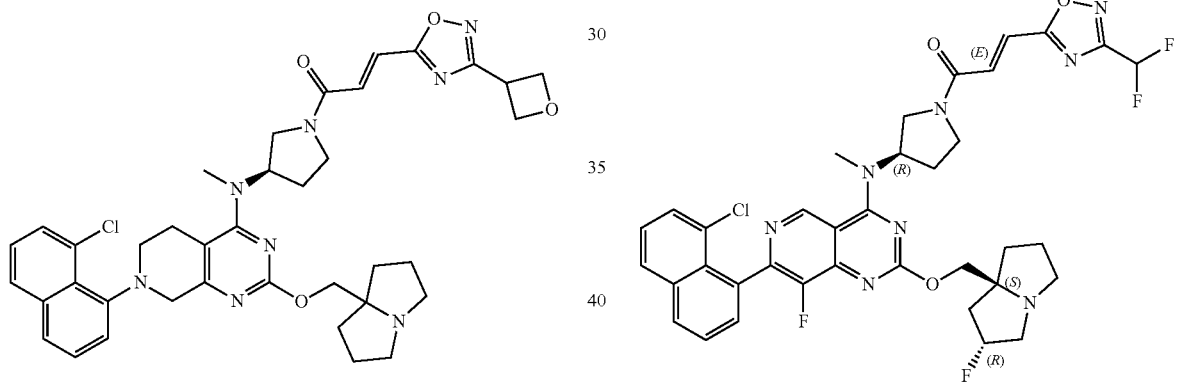

Example 156 (Method 4): (R,E)-1-(3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-(oxetan-3-yl)-1,2,4-oxadiazol-5-yl)prop-2-en-1-one Example 157 (Method 1): (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-(difluoromethyl)-1,2,4-oxadiazol-5-yl)prop-2-en-1-one

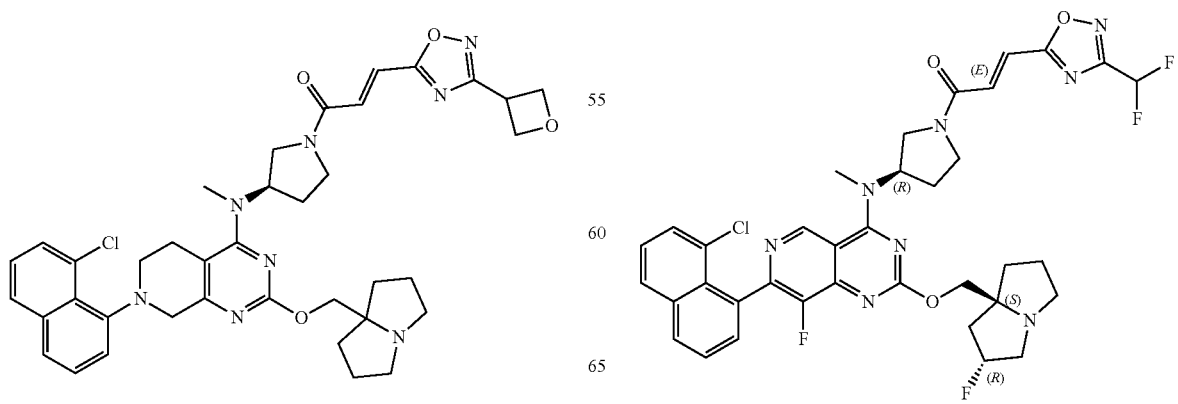

Step 1: (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-(difluoromethyl)-1,2,4-oxadiazol-5-yl)prop-2-en-1-one The amide coupling reaction was prepared in a similar fashion to Method #1, Step 10. The residue was purified by reverse phase HPLC (column: Waters Xbridge BEH C18 100*30 mm*10 µm; mobile phase: [water (NH$_4$HCO$_3$)-acetonitrile]; B %: 50%-80%, 10 min) affording (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-(difluoromethyl)-1,2,4-oxadiazol-5-yl)prop-2-en-1-one (12.93 mg, 18.02%) as a yellow solid: $^1$H NMR (400 MHz, Acetonitrile-d3) δ 9.20 (t, J=1.7 Hz, 1H), 8.12 (dd, J=1.1, 8.1 Hz, 1H), 8.05-7.98 (m, 1H), 7.72-7.66 (m, 1H), 7.65-7.59 (m, 2H), 7.58 (s, 1H), 7.52-7.48 (m, 1H), 7.47 (s, 1H), 7.00 (d, J=7.6 Hz, 1H), 5.35 (br d, J=8.3 Hz, 1H), 5.34-5.15 (m, 1H), 4.26-4.13 (m, 2H), 4.08-3.96 (m, 1H), 3.94-3.72 (m, 2H), 3.68-3.50 (m, 1H), 3.47-3.42 (m, 3H), 3.25-3.04 (m, 3H), 2.95-2.84 (m, 1H), 2.49-2.39 (m, 1H), 2.38-2.29 (m, 1H), 2.20 (br d, J=4.4 Hz, 1H), 2.07 (br s, 2H), 1.92-1.79 (m, 3H). LCMS Rt=3.015 min, m/z=736.2 [M+H]$^+$.

LCMS (5 to 95% acetonitrile in water+0.03% ammonium bicarbonate over 6 mins) retention time 3.015 min. ESI+ found [M+H]=736.2.

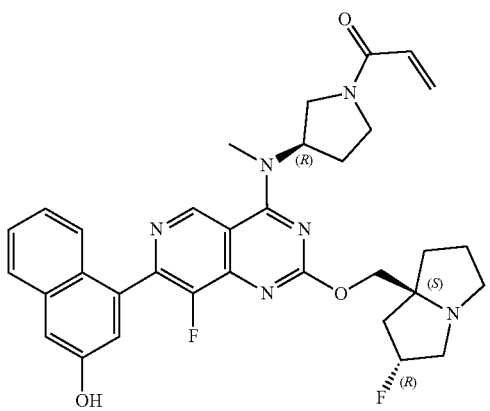

Example 158 (Method 2-Master): 1-((R)-3-((8-fluoro-2-(((2R,7aS)-2-fluorohexahydro-1H-pyrrolizin-7a-yl)methoxy)-7-(3-hydroxynaphthalen-1-yl)pyrido[4,3-d]pyrimidin-4-yl)(methyl)amino)pyrrolidin-1-yl)prop-2-en-1-one

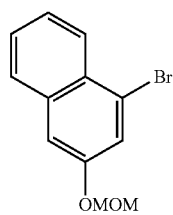

Step 1: 1-bromo-3-(methoxymethoxy)naphthalene

To a solution of 4-bromonaphthalen-2-ol (8 g, 35.86 mmol) and N-ethyl-N-isopropylpropan-2-amine (23.18 g, 179.32 mmol) in dichloromethane (20 mL) was added chloro(methoxy)methane (7.51 g, 93.28 mmol) at 0° C. The mixture was stirred at 25° C. for 12 h. The reaction mixture was quenched with saturated sodium bicarbonate (20 mL) at 0° C. and extracted with dichloromethane (3×20 mL). The combined organic layers were dried over sodium sulphate and concentrated in vacuo. The resulting residue was purified by column chromatography (silica gel, 100-200 mesh, 0-100% ethyl acetate in petroleum ether) affording 1-bromo-3-(methoxymethoxy)naphthalene (9 g, 93.95%) as a red oil: $^1$H NMR (400 MHz, Chloroform-d) δ 8.08-8.01 (m, TH), 7.66-7.58 (m, TH), 7.48 (d, J=2.3 Hz, 1H), 7.40-7.31 (m, 2H), 7.28 (d, J=2.1 Hz, 1H), 5.17 (s, 2H), 3.41 (s, 3H). LCMS Rt=0.895 min, m/z=266.0 [M+H]$^+$.

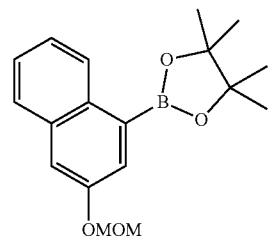

Step 2: 2-(3-(methoxymethoxy)naphthalen-1-yl)-4,4,5,5-tetramethyl-1,3,2-dioxaborolane A mixture of 1-bromo-3-(methoxymethoxy)naphthalene (5 g, 18.72 mmol), 4,4,5,5-tetramethyl-2-(4,4,5,5-tetramethyl-1,3,2-dioxaborolan-2-yl)-1,3,2-dioxaborolane (4.75 g, 18.72 mmol), [1,1-Bis(diphenylphosphino)ferrocene]palladium(II)Dichloride (1.37 g, 1.87 mmol) and potassium; acetate (3.67 g, 37.44 mmol) in dioxane (300 mL) was degassed and purged with nitrogen for 3 times, and the mixture was stirred at 100° C. for 12 h under nitrogen atmosphere.

The reaction mixture was concentrated in vacuo and the residue was purified by reverse phase HPLC (column: Phenomenex C18 250*100 mm 10 u; mobile phase: [water (NH$_4$HCO$_3$)-acetonitrile]; B %: 65%-95%, 20 min) affording 2-[3-(methoxymethoxy)-1-naphthyl]-4,4,5,5-tetramethyl-1,3,2-dioxaborolane (5 g, 85.02%) as a white solid: $^1$H NMR (400 MHz, Chloroform-d) δ 8.62-8.55 (m, 1H), 7.74-7.62 (m, 2H), 7.40 (d, J=2.4 Hz, 1H), 7.33 (tt, J=5.3, 7.2 Hz, 2H), 5.22 (s, 2H), 3.43 (s, 3H), 1.33 (s, 12H). LCMS Rt=0.929 min, m/z=314.2 [M+H]$^+$.

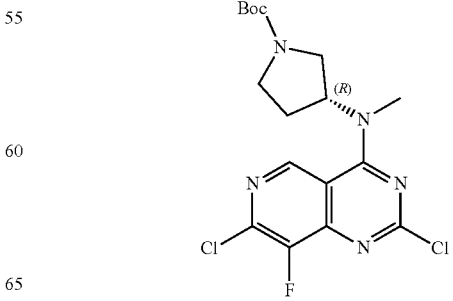

Step 3: tert-butyl (3R)-3-[(2,7-dichloro-8-fluoro-pyrido[4,3-d]pyrimidin-4-yl)-methyl-amino]pyrrolidine-1-carboxylate To a solution of 2,4,7-trichloro-8-fluoro-pyrido[4,3-d]pyrimidine (7 g, 27.73 mmol) in N,N-dimethylformaldehyde (15 mL) was added tert-butyl (3R)-3-(methylamino)pyrrolidine-1-carboxylate (4.44 g, 22.18 mmol) and N-ethyl-N-isopropylpropan-2-amine (10.75 g, 83.18 mmol) at 0° C. and the mixture was stirred 25° C. for 12 h under nitrogen atmosphere. The mixture was diluted with water (50 mL) and extracted with ethyl acetate (3×50 mL). The combined organic layers were dried over sodium sulphate and concentrated in vacuo affording tert-butyl (3R)-3-[(2,7-dichloro-8-fluoro-pyrido[4,3-d]pyrimidin-4-yl)-methyl-amino]pyrrolidine-1-carboxylate (13 g, crude) as a brown solid, used in the next step without further purification. LCMS Rt=0.869 min, m/z=416.1 [M+H]$^+$.

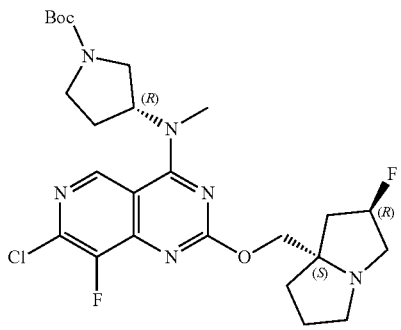

Step 4: (R)-tert-butyl 3-((7-chloro-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate To a solution of tert-butyl (3R)-3-[(2,7-dichloro-8-fluoro-pyrido[4,3-d]pyrimidin-4-yl)-methyl-amino]pyrrolidine-1-carboxylate (5.9 g, 14.17 mmol) in dioxane (70 mL) was added [(2R,8S)-2-fluoro-1,2,3,5,6,7-hexahydropyrrolizin-8-yl]methanol (6.77 g, 42.52 mmol) and N-ethyl-N-isopropylpropan-2-amine (7.33 g, 56.69 mmol). Then the mixture was stirred at 100° C. for 12 h under nitrogen atmosphere. The reaction mixture was concentrated in vacuo. The residue was purified by column chromatography (silica gel, 100-200 mesh, 30-50% ethyl acetate in petroleum ether) affording (R)-tert-butyl 3-((7-chloro-8-fluoro-2-(((2R,7aS)-2-fluorohexahydro-TH-pyrrolizin-7a-yl)methoxy)pyrido[4,3-d]pyrimidin-4-yl)(methyl)amino)pyrrolidine-1-carboxylate (5.7 g, 74%) as a yellow solid. LCMS Rt=0.655 min, m/z=539.1 [M+H]$^+$.

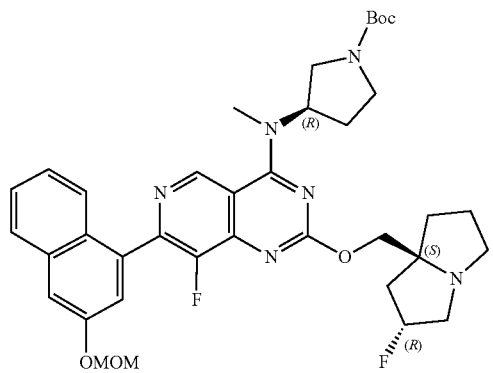

Step 5: (R)-tert-butyl 3-((8-fluoro-2-(((2R,7aS)-2-fluorohexahydro-1H-pyrrolizin-7a-yl)methoxy)-7-(3-(methoxymethoxy)naphthalen-1-yl)pyrido[4,3-d]pyrimidin-4-yl)(methyl)amino)pyrrolidine-1-carboxylate A mixture of (R)-tert-butyl 3-((7-chloro-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (590 mg, 1.09 mmol), 2-[3-(methoxymethoxy)-1-naphthyl]-4,4,5,5-tetramethyl-1,3,2-dioxaborolane (684.92 mg, 2.18 mmol), potassium phosphate (694.12 mg, 3.27 mmol) and [2-(2-aminophenyl)phenyl]-chloro-palladium; dicyclohexyl-[3-(2,4,6-triisopropylphenyl)phenyl]phosphane (85.76 mg, 109.00 μmol) in dioxane (10 mL) and water (3 mL) was degassed and purged with nitrogen for 3 times, then the mixture was stirred at 60° C. for 1 h under nitrogen atmosphere. The mixture was diluted with water (20 mL) and extracted with ethyl acetate (3×50 mL). The combined organic layers were dried over sodium sulphate and concentrated in vacuo. The resulting residue was purified by reverse phase HPLC (column: Phenomenex luna C18 250*50 mm*10 μm; mobile phase: [water (trifluoroacetic acid)-acetonitrile]; B %: 30%-60%, 10 min) affording (R)-tert-butyl 3-((8-fluoro-2-(((2R,7aS)-2-fluorohexahydro-1H-pyrrolizin-7a-yl)methoxy)-7-(3-(methoxymethoxy)naphthalen-1-yl)pyrido[4,3-d]pyrimidin-4-yl)(methyl)amino)pyrrolidine-1-carboxylate (230 mg, 31%, trifluoroacetate salt) as a yellow solid. LCMS Rt=2.241 min, m/z=690.3 [M+H]$^+$.

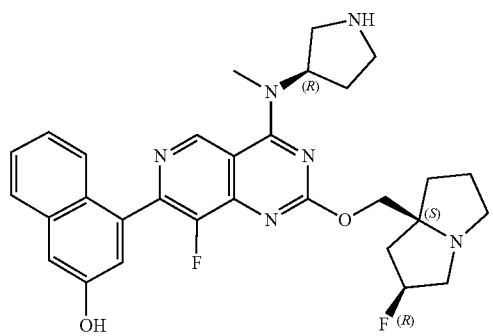

Step 6: 4-(8-fluoro-2-(((2R,7aS)-2-fluorohexahydro-1H-pyrrolizin-7a-yl)methoxy)-4-(methyl((R)-pyrrolidin-3-yl)amino)pyrido[4,3-d]pyrimidin-7-yl)naphthalen-2-ol A mixture of (R)-tert-butyl 3-((8-fluoro-2-(((2R,7aS)-2-fluorohexahydro-1H-pyrrolizin-7a-yl)methoxy)-7-(3-(methoxymethoxy)naphthalen-1-yl)pyrido[4,3-d]pyrimidin-4-yl)(methyl)amino)pyrrolidine-1-carboxylate (49 mg, 70.93 μmol) in dichloromethane (0.5 mL) and trifluoroacetic acid (0.5 mL) was stirred at 25° C. for 0.5 h. The reaction mixture was concentrated in vacuo affording 4-(8-fluoro-2-(((2R,7aS)-2-fluorohexahydro-1H-pyrrolizin-7a-yl)methoxy)-4-(methyl((R)-pyrrolidin-3-yl)amino)pyrido[4,3-d]pyrimidin-7-yl)naphthalen-2-ol (50 mg, crude, trifluoroacetate salt) as a yellow oil, used in the next step without further purification. LCMS Rt=0.435 min, m/z=546.3 [M+H]$^+$.

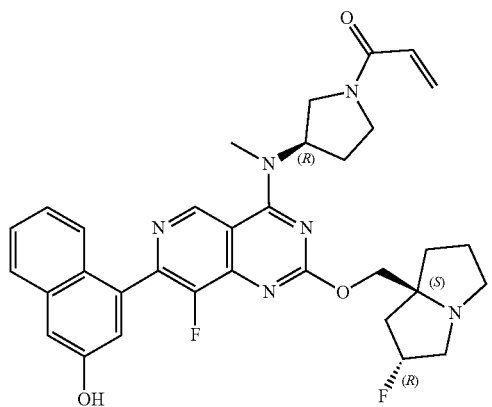

Step 7: 1-((R)-3-((8-fluoro-2-(((2R,7aS)-2-fluorohexahydro-1H-pyrrolizin-7a-yl)methoxy)-7-(3-hydroxynaphthalen-1-yl)pyrido[4,3-d]pyrimidin-4-yl)(methyl)amino)pyrrolidin-1-yl)prop-2-en-1-one The amide coupling reaction was prepared in a similar fashion to Method #1, Step 10. The reaction mixture was concentrated in vacuo and purified by reverse phase HPLC (column: Phenomenex Luna C18 75*30 mm*3 μm; mobile phase: [water (formic acid)-acetonitrile]; B %: 10%-40%, 8 min) affording 1-((R)-3-((8-fluoro-2-(((2R,7aS)-2-fluorohexahydro-1H-pyrrolizin-7a-yl)methoxy)-7-(3-hydroxynaphthalen-1-yl)pyrido[4,3-d]pyrimidin-4-yl)(methyl)amino)pyrrolidin-1-yl)prop-2-en-1-one (3.34 mg, 6%, formate salt) as a yellow oil: $^1$H NMR (400 MHz, Acetonitrile-d3) δ 9.50 (s, 1H), 8.06 (d, J=8.3 Hz, 1H), 7.88 (br d, J=8.6 Hz, 1H), 7.75-7.70 (m, 1H), 7.58 (d, J=2.3 Hz, 1H), 7.57-7.51 (m, 2H), 6.85 (dt, J=10.4, 16.4 Hz, 1H), 6.55-6.45 (m, 1H), 5.95 (ddd, J=2.3, 7.3, 10.1 Hz, 1H), 5.67-5.57 (m, 1H), 5.48 (br s, 1H), 4.56-4.40 (m, 2H), 4.36-4.18 (m, 1H), 4.17-4.02 (m, 1H), 3.95-3.87 (m, 1H), 3.82-3.81 (m, 1H), 3.81 (dd, J=7.6, 12.8 Hz, 1H), 3.74 (br s, 3H), 3.53-3.41 (m, 2H), 3.41-3.33 (m, 1H), 3.23-3.14 (m, 1H), 2.67-2.59 (m, 2H), 2.57-2.46 (m, 2H), 2.42-2.31 (m, 1H), 2.42-2.30 (m, 1H), 2.19-2.11 (m, 2H). LCMS Rt=2.711 min, m/z=600.3 [M+H]$^+$.

LCMS (5 to 95% acetonitrile in water+0.03% ammonium bicarbonate over 6 mins) retention time 2.711 min, ESI+ found [M+H]=600.3.

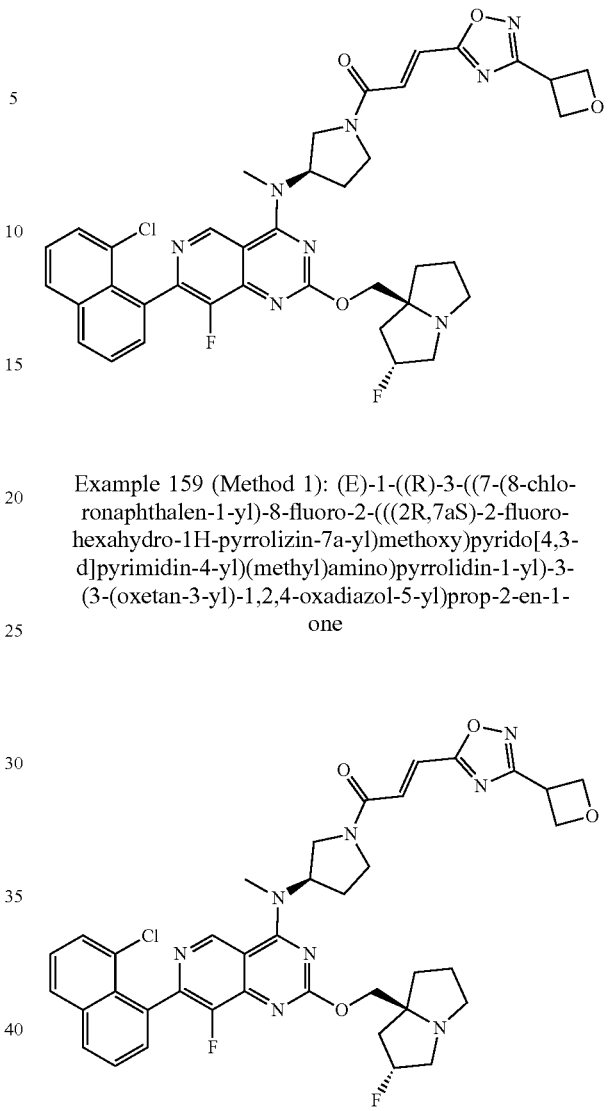

Example 159 (Method 1): (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-(oxetan-3-yl)-1,2,4-oxadiazol-5-yl)prop-2-en-1-one

Step 1: (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-(oxetan-3-yl)-1,2,4-oxadiazol-5-yl)prop-2-en-1-one The amide coupling reaction was prepared in a similar fashion to Method #1, Step 10. The residue was purified by reverse phase HPLC (column: Waters Xbridge BEH C18 100*30 mm*10 μm; mobile phase: [water (NH$_4$HCO$_3$)-acetonitrile]; B %: 25%-75%, 10 min) affording (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-(oxetan-3-yl)-1,2,4-oxadiazol-5-yl)prop-2-en-1-one (25.43 mg, 19.36%) as a white solid: $^1$H NMR (400 MHz, Acetonitrile-d3) δ 9.25-9.19 (m, 1H), 8.15 (dd, J=1.0, 8.1 Hz, 1H), 8.07-8.01 (m, 1H), 7.74-7.68 (m, 1H), 7.67-7.61 (m, 2H), 7.59-7.40 (m, 3H), 5.39-5.18 (m, 1H), 5.00 (dt, J=6.1, 8.2 Hz, 2H), 4.89-4.77 (m, 2H), 4.53-4.43 (m, 1H), 4.26-4.21 (m, 1H), 4.19-4.13 (m, 1H), 4.09-3.99 (m, 1H), 3.97-3.74 (m, 2H), 3.71-3.52 (m, 1H), 3.47 (s, 3H), 3.20-3.06 (m, 3H), 2.96-2.86 (m, 1H), 2.49-2.41 (m, 1H), 2.40-2.32 (m, 1H), 2.26-2.22 (m, 2H), 2.13 (br s, 1H), 2.10-2.05 (m, 1H), 1.94-1.82 (m, 3H). LCMS Rt=2.159 min, m/z=742.3 [M+H]⁺.

LCMS (5 to 95% acetonitrile in water+0.03% ammonium bicarbonate over 6 mins) retention time 2.159 min, ESI+ found [M+H]=742.3

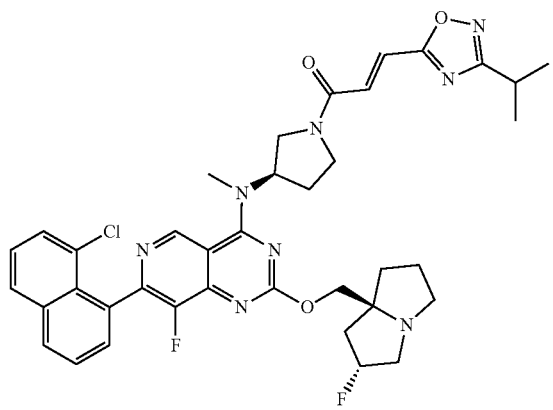 [SMILES: CC(C)c1noc(/C=C/C(=O)N2CC[C@@H](N(C)c3nc(OC[C@@]45CCCN4C[C@H](F)C5)nc4c(F)c(-c5cccc6cccc(Cl)c56)ncc34)C2)n1]

Example 160 (Method 1): (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-isopropyl-1,2,4-oxadiazol-5-yl)prop-2-en-1-one

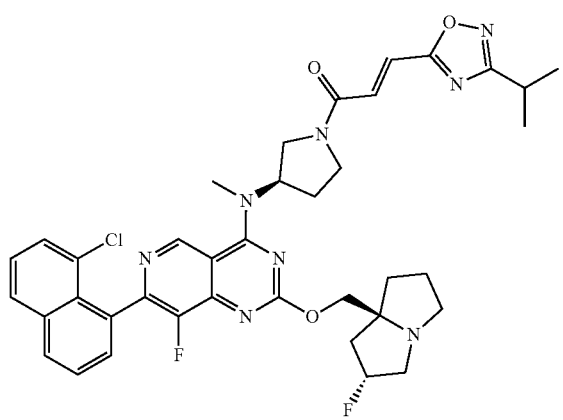 [SMILES: CC(C)c1noc(/C=C/C(=O)N2CC[C@@H](N(C)c3nc(OC[C@@]45CCCN4C[C@H](F)C5)nc4c(F)c(-c5cccc6cccc(Cl)c56)ncc34)C2)n1]

Step 1: (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-isopropyl-1,2,4-oxadiazol-5-yl)prop-2-en-1-one The amide coupling reaction was prepared in a similar fashion to Method #1, Step 10. The crude was purified by reverse phase HPLC (column: Waters Xbridge Prep OBD C18 150*40 mm*10 µm; mobile phase: [water (NH₄HCO₃)-acetonitrile]; B %: 45%-75%, 8 min) affording (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-isopropyl-1,2,4-oxadiazol-5-yl)prop-2-en-1-one (40.11 mg, 11.07%) as a yellow solid: ¹HNMR (400 MHz, Acetonitrile-d3) δ 9.25-9.19 (m, 1H), 8.15 (d, J=8.1 Hz, 1H), 8.04 (d, J=8.1 Hz, 1H), 7.75-7.69 (m, 1H), 7.67-7.61 (m, 2H), 7.57-7.50 (m, 1H), 7.49-7.43 (m, 1H), 7.43-7.36 (m, 1H), 5.49-5.37 (m, 1H), 5.35 (br d, J=6.1 Hz, 1H), 4.25-4.20 (m, 1H), 4.17-4.12 (m, 1H), 4.09-3.99 (m, 1H), 3.94-3.86 (m, 1H), 3.84-3.74 (m, 1H), 3.69-3.51 (m, 1H), 3.46 (s, 3H), 3.21-3.10 (m, 3H), 3.08 (br d, J=2.9 Hz, 1H), 2.96-2.84 (m, 1H), 2.51-2.40 (m, 1H), 2.40-2.30 (m, 1H), 2.24 (br d, J=5.5 Hz, 1H), 2.12 (br s, 1H), 2.07 (br d, J=5.4 Hz, 1H), 1.92-1.77 (m, 3H), 1.38-1.27 (m, 6H). LCMS Rt=2.285 min, m/z=728.3 [M+H]⁺.

LCMS (5 to 95% acetonitrile in water+0.03% ammonium bicarbonate over 6 mins) retention time 2.285 min. ESI+ found [M+H]=728.3.

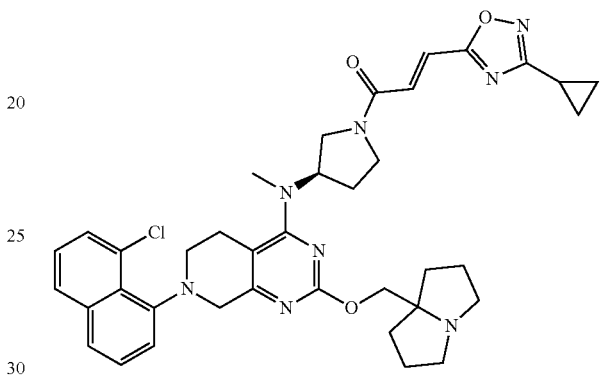

Example 161 (Method 4): (R,E)-1-(3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-cyclopropyl-1,2,4-oxadiazol-5-yl)prop-2-en-1-one

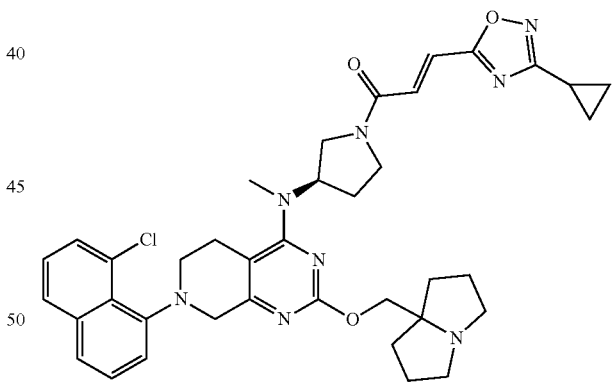

Step 1: (R,E)-1-(3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-cyclopropyl-1,2,4-oxadiazol-5-yl)prop-2-en-1-one The amide coupling reaction was prepared in a similar fashion to Method #4, Step 11. The crude product was purified by reverse phase HPLC (column: Waters Xbridge Prep OBD C18 150*40 mm*10 um; mobile phase: [water (ammonium bicarbonate- acetonitrile]; B %: 40%-70%, 8 min) affording (R,E)-1-(3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-(oxetan-3-yl)-1,2,4-oxadiazol-5-yl)prop-2-en-1-one (51.9 mg, 15.73%) as a yellow solid: ¹HNMR (400 MHz, Acetonitrile-d3) δ 7.91-7.82 (m, 1H), 7.75-7.69 (m, 1H), 7.61-7.49 (m, 2H), 7.47-7.39 (m, 2H), 7.38-7.27 (m, 2H), 4.92-4.73 (m, 1H), 4.30-4.14 (m, 1H), 4.08-3.88 (m, 3H), 3.87-3.64 (m, 3H), 3.61-3.40 (m, 2H), 3.34-3.06 (m, 3H), 3.04-2.92 (m, 5H), 2.68-2.56 (m, 3H), 2.33-2.23 (m, 2H), 2.13 (br d, J=4.8 Hz, 1H), 1.93 (br d, J=5.9 Hz, 1H), 1.87-1.73 (m, 4H), 1.69-1.57 (m, 2H), 1.14-1.07 (m, 2H), 1.04-0.95 (m, 2H). LCMS Rt=3.268 min, m/z=694.3 [M+H]⁺.

LCMS (5 to 95% acetonitrile in water+0.03% ammonium bicarbonate over 6 mins) retention time 3.268 min, ESI+ found [M+H]=694.3.

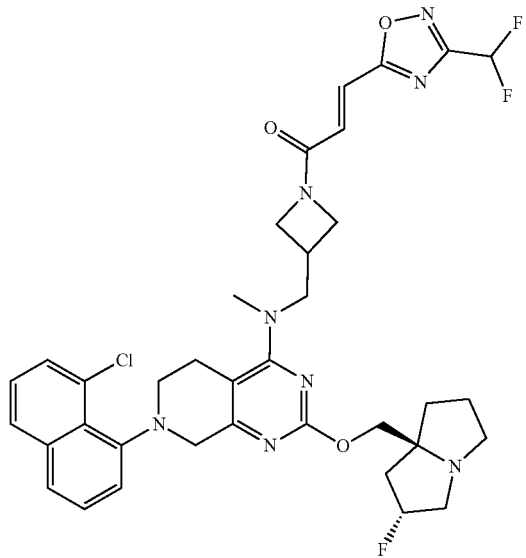 [SMILES: CN(CC1CN(C(=O)/C=C/c2nc(C(F)F)no2)C1)c1nc(OC[C@@]23CCCN2C[C@H](F)C3)nc2c1CCN(c1cccc3cccc(Cl)c13)C2]

Example 162 (Method 4): (E)-1-(3-(((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)methyl)azetidin-1-yl)-3-(3-(difluoromethyl)-1,2,4-oxadiazol-5-yl)prop-2-en-1-one Step 1: (E)-1-(3-(((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)methyl)azetidin-1-yl)-3-(3-(difluoromethyl)-1,2,4-oxadiazol-5-yl)prop-2-en-1-one The amide coupling reaction was prepared in a similar fashion to Method #4, Step 11. The crude product was purified by reverse phase HPLC (column: Waters Xbridge Prep OBD C18 150*40 mm*10 μm; mobile phase: [water (ammonium bicarbonate)- acetonitrile]; B %: 55%-90%, 8 min) affording (E)-1-(3-(((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)methyl)azetidin-1-yl)-3-(3-(difluoromethyl)-1,2,4-oxadiazol-5-yl)prop-2-en-1-one (10.21 mg, 5.84%) as a yellow solid: ¹H NMR (400 MHz, Acetonitrile-d3) δ 7.86 (d, J=8.1 Hz, 1H), 7.69 (d, J=8.1 Hz, 1H), 7.52 (s, 2H), 7.45-7.36 (m, 2H), 7.36-7.24 (m, 2H), 7.16-6.88 (m, 1H), 5.35-5.14 (m, 1H), 4.42 (q, J=8.3 Hz, 1H), 4.22 (br d, J=17.0 Hz, 1H), 4.16-4.09 (m, 1H), 4.09-4.04 (m, 1H), 4.03-3.98 (m, 1H), 3.97-3.90 (m, 1H), 3.89-3.84 (m, 1H), 3.74 (s, 1H), 3.71-3.62 (m, 1H), 3.61-3.46 (m, 2H), 3.23 (br d, J=11.5 Hz, 1H), 3.16-3.01 (m, 8H), 2.92-2.82 (m, 1H), 2.66 (br d, J=15.1 Hz, 1H), 2.16-2.02 (m, 3H), 1.92-1.76 (m, 3H). LCMS Rt=3.440 min, m/z=722.3 [M+H]⁺.

LCMS (5 to 95% acetonitrile in water+0.03% ammonium bicarbonate over 6 mins) retention time 3.440 min, ESI+ found [M+H]=722.3.

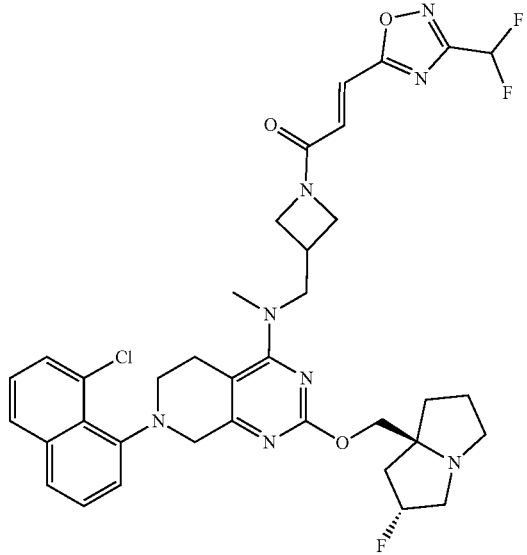 [SMILES: CN(CC1CN(C(=O)/C=C/c2nc(C(F)F)no2)C1)c1nc(OC[C@@]23CCCN2C[C@H](F)C3)nc2c1CCN(c1cccc3cccc(Cl)c13)C2]

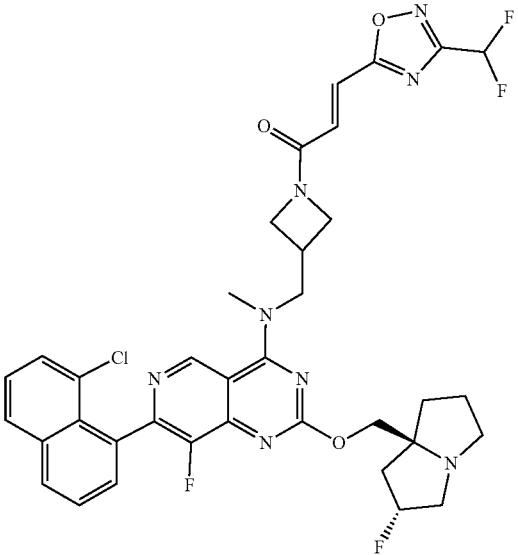 [SMILES: CN(CC1CN(C(=O)/C=C/c2nc(C(F)F)no2)C1)c1nc(OC[C@@]23CCCN2C[C@H](F)C3)nc2c(F)c(-c3cccc4cccc(Cl)c34)ncc12]

Example 163 (Method 1): (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-(difluoromethyl)-1,2,4-oxadiazol-5-yl)prop-2-en-1-one

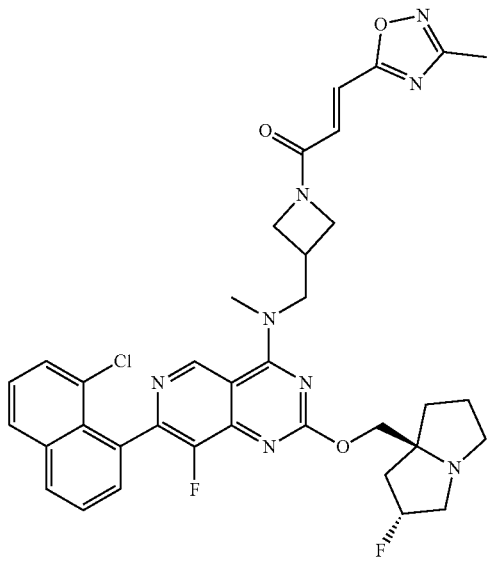

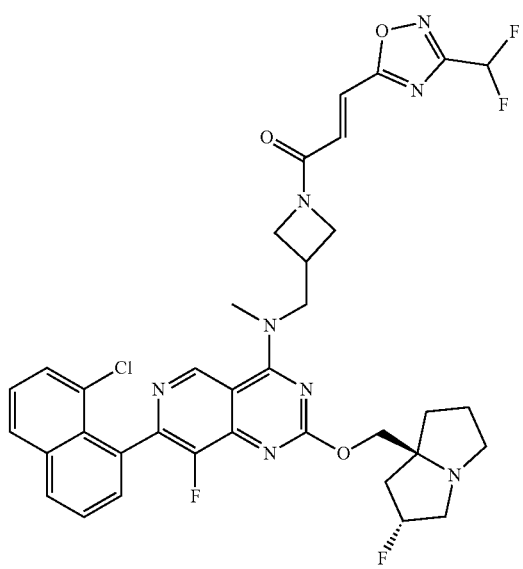 [SMILES: CN(CC1CN(C(=O)/C=C/c2nc(C(F)F)no2)C1)c1nc(OC[C@@]23CCCN2C[C@H](F)C3)nc2c(F)c(-c3cccc4cccc(Cl)c34)ncc12]

Step 1: (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-(difluoromethyl)-1,2,4-oxadiazol-5-yl)prop-2-en-1-one The amide coupling reaction was prepared in a similar fashion to Method #1, Step 10. The residue was purified by reverse phase HPLC(column: Phenomenex Luna C18 75*30 mm*3 μm; mobile phase: [water (formic acid)-acetonitrile]; B %: 10%-40%, 8 min) affording (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-(difluoromethyl)-1,2,4-oxadiazol-5-yl)prop-2-en-1-one (5.06 mg, 7.33%, formate salt) as a yellow solid: $^1$H NMR (400 MHz, Acetonitrile-d3) δ 9.28 (s, 1H), 8.19-8.13 (m, 1H), 8.07-8.02 (m, 1H), 7.75-7.69 (m, 1H), 7.67-7.61 (m, 2H), 7.58-7.51 (m, 1H), 7.46-7.40 (m, 1H), 7.36-7.29 (m, 1H), 5.44-5.18 (m, 1H), 4.58-4.48 (m, 1H), 4.36-4.31 (m, 1H), 4.29-4.20 (m, 4H), 4.20-4.15 (m, 1H), 4.05-3.93 (m, 1H), 3.64-3.60 (m, 3H), 3.31-3.19 (m, 3H), 3.19-3.15 (m, 1H), 3.01-2.90 (m, 1H), 2.08 (br d, J=9.5 Hz, 3H), 1.95-1.82 (m, 3H), 1.31-1.31 (m, 1H). LCMS Rt=2.344 min, m/z=736.2 [M+H]$^+$.

LCMS (5 to 95% acetonitrile in water+0.1% trifluoroacetic acid over 6 mins) retention time 2.344 min, ESI+ found [M+H]=736.2.

Example 164 (Method 1): (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-methyl-1,2,4-oxadiazol-5-yl)prop-2-en-1-one

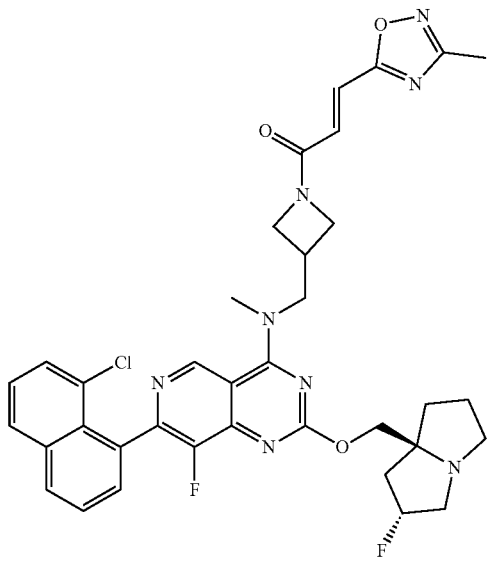 [SMILES: Cc1noc(/C=C/C(=O)N2CC(CN(C)c3nc(OC[C@@]45CCCN4C[C@H](F)C5)nc4c(F)c(-c5cccc6cccc(Cl)c56)ncc34)C2)n1]

Step 1: (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-methyl-1,2,4-oxadiazol-5-yl)prop-2-en-1-one The amide coupling reaction was prepared in a similar fashion to Method #1, Step 10. The residue was purified by reverse phase HPLC (column: Waters Xbridge BEH C18 100*30 mm*10 um; mobile phase: [water (formic acid)- acetonitrile]; B %: 10%-40%, 8 min) affording (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(3-methyl-1,2,4-oxadiazol-5-yl)prop-2-en-1-one (5.06 mg, 7.33%, formic acid salt) as a yellow solid. ¹H NMR (400 MHz, Acetonitrile-d3) δ 9.28-9.21 (m, 1H), 8.20-8.07 (m, 1H), 8.05-7.95 (m, 1H), 7.72-7.66 (m, 1H), 7.65-7.57 (m, 2H), 7.54-7.49 (m, 1H), 7.34-7.28 (m, 1H), 7.19-7.13 (m, 1H), 5.35-5.14 (m, 1H), 4.52-4.42 (m, 1H), 4.34-4.25 (m, 1H), 4.25-4.12 (m, 4H), 4.11-4.03 (m, 1H), 3.97-3.88 (m, 1H), 3.58 (s, 3H), 3.26-3.20 (m, 1H), 3.17 (br d, 2H), 3.04 (br s, 1H), 2.91-2.83 (m, 1H), 2.40-2.36 (m, 3H), 2.10-1.99 (m, 3H), 1.86-1.75 (m, 3H). LCMS Rt=2.212 min, m/z=700.3 [M+H]⁺.

LCMS (5 to 95% acetonitrile in water+0.03% ammonium bicarbonate over 6 min) retention time 2.212 min, ESI+ found [M+H]=700.3.

Step 1: (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-(difluoromethyl)-1,2,4-oxadiazol-5-yl)prop-2-en-1-one The amide coupling reaction was prepared in a similar fashion to Method #2, Step 7. The reaction mixture was purified by reverse phase HPLC (column: Waters Xbridge Prep OBD C18 150*40 mm*10 um; mobile phase: [water (NH₄HCO₃)-acetonitrile]; B %: 30%-65%, 8 min) affording (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-(difluoromethyl)-1,2,4-oxadiazol-5-yl)prop-2-en-1-one (20.76 mg, 17.20%) as a yellow amorphous solid: ¹H NMR (400 MHz, Acetonitrile-d3) δ 9.13 (d, J=1.4 Hz, 1H), 8.06 (d, J=8.1 Hz, 1H), 7.96 (d, J=8.1 Hz, 1H), 7.66-7.60 (m, 1H), 7.58-7.54 (m, 2H), 7.53-7.48 (m, 1H), 7.46 (d, J=8.0 Hz, 1H), 7.44-7.37 (m, 1H), 7.09-6.78 (m, 1H), 5.42-5.26 (m, 1H), 4.14 (s, 2H), 4.01-3.91 (m, 1H), 3.87-3.67 (m, 2H), 3.58-3.46 (m, 1H), 3.38 (s, 3H), 3.01-2.92 (m, 2H), 2.62-2.55 (m, 2H), 2.39-2.30 (m, 2H), 1.81-1.71 (m, 5H), 1.65-1.53 (m, 3H). LCMS Rt=2.364 min, m/z=718.2 [M+H]⁺.

LCMS (5 to 95% acetonitrile in water+0.1% trifluoroacetic acid over 6 mins) retention time 2.364 min, ESI+ found [M+H]=718.2.

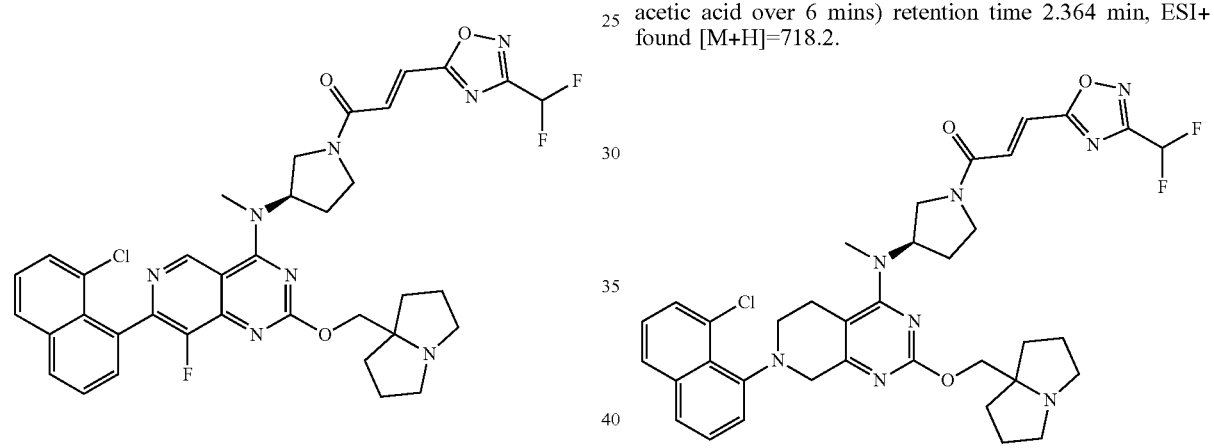

Example 165 (Method 2): (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-(difluoromethyl)-1,2,4-oxadiazol-5-yl)prop-2-en-1-one Example 166 (Method 4): (R,E)-1-(3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-(difluoromethyl)-1,2,4-oxadiazol-5-yl)prop-2-en-1-one

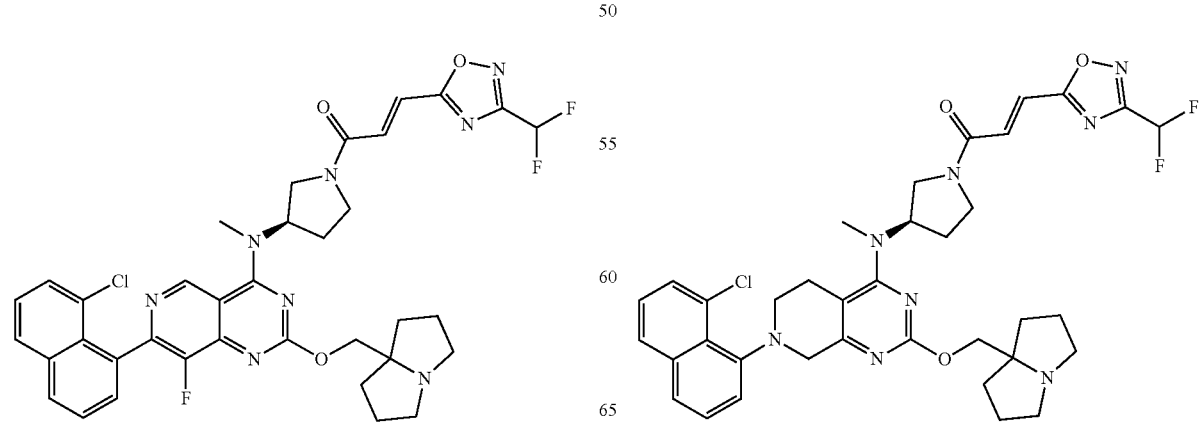

Step 1: (R,E)-1-(3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-(difluoromethyl)-1,2,4-oxadiazol-5-yl)prop-2-en-1-one The amide coupling reaction was prepared in a similar fashion to Method #4, Step 11. The crude product was purified by reverse phase HPLC (column: Waters Xbridge Prep OBD C18 150*40 mm*10 μm; mobile phase: [water (ammonium bicarbonate- acetonitrile]; B %: 55%-90%, 8 min) affording (R,E)-1-(3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-(difluoromethyl)-1,2,4-oxadiazol-5-yl)prop-2-en-1-one (51.9 mg, 15.73%) as a yellow solid: $^1$H NMR (400 MHz, Acetonitrile-d3) δ 7.87 (d, J=8.3 Hz, 1H), 7.74-7.73 (m, 1H), 7.63-7.55 (m, 2H), 7.55-7.44 (m, 2H), 7.44-7.39 (m, 1H), 7.34 (t, J=7.1 Hz, 1H), 7.17-6.88 (m, 1H), 4.94-4.71 (m, 1H), 4.28-4.16 (m, 1H), 4.06-3.88 (m, 3H), 3.86-3.61 (m, 3H), 3.58-3.43 (m, 2H), 3.32-3.17 (m, 1H), 3.15-3.06 (m, 1H), 3.04-2.90 (m, 5H), 2.66-2.54 (m, 3H), 2.33-2.09 (m, 3H), 1.92 (br d, J=6.9 Hz, 1H), 1.88-1.73 (m, 4H), 1.67-1.55 (m, 2H). LCMS Rt=3.110 min, m/z=704.3 [M+H]$^+$.

LCMS (5 to 95% acetonitrile in water+0.03% ammonium bicarbonate over 6 mins) retention time 3.110 min, ESI+ found [M+H]=704.3.

Step 1: (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-isopropyl-1,2,4-oxadiazol-5-yl)prop-2-en-1-one The amide coupling reaction was prepared in a similar fashion to Method #2, Step 7. The reaction mixture was purified by reverse phase HPLC (column: column: Waters Xbridge Prep OBD C18 150*40 mm*10 um; mobile phase: [water (NH$_4$HCO$_3$)-acetonitrile]; B %: 35%-65%, 8 min.) affording (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-isopropyl-1,2,4-oxadiazol-5-yl)prop-2-en-1-one (372.29 mg, 48.40%) as a yellow amorphous solid: $^1$H NMR (400 MHz, Acetonitrile-d3) δ 9.22-9.16 (m, 1H), 8.15-8.09 (m, 1H), 8.01 (d, J=8.1 Hz, 1H), 7.72-7.65 (m, 1H), 7.65-7.58 (m, 2H), 7.54-7.46 (m, 1H), 7.46-7.31 (m, 2H), 5.50-5.29 (m, 1H), 4.31-4.15 (m, 2H), 4.07-3.95 (m, 1H), 3.92-3.83 (m, 1H), 3.82-3.72 (m, 1H), 3.68-3.47 (m, 1H), 3.46-3.41 (m, 3H), 3.20-3.01 (m, 3H), 2.74-2.62 (m, 2H), 2.45-2.37 (m, 1H), 2.36-2.28 (m, 1H), 2.05-1.96 (m, 2H), 1.86 (tt, J=6.6, 12.9 Hz, 4H), 1.75-1.64 (m, 2H), 1.32 (dd, J=7.0, 8.9 Hz, 6H). LCMS Rt =3.000 min, m/z=710.3 [M+H]$^+$.

LCMS (5 to 95% acetonitrile in water+0.03% ammonium bicarbonate over 6 mins s) retention time 3.000 min, ESI+ found [M+H]=710.3.

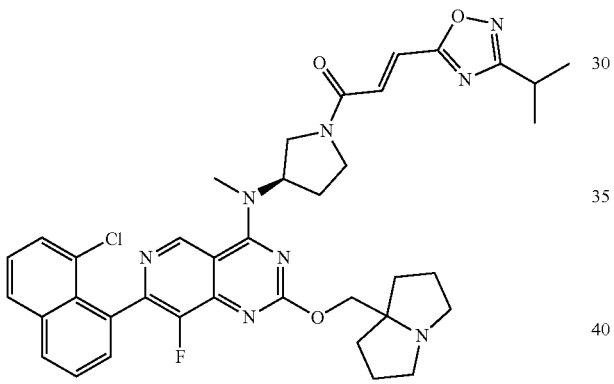

Example 167 (Method 2): (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-isopropyl-1,2,4-oxadiazol-5-yl)prop-2-en-1-one

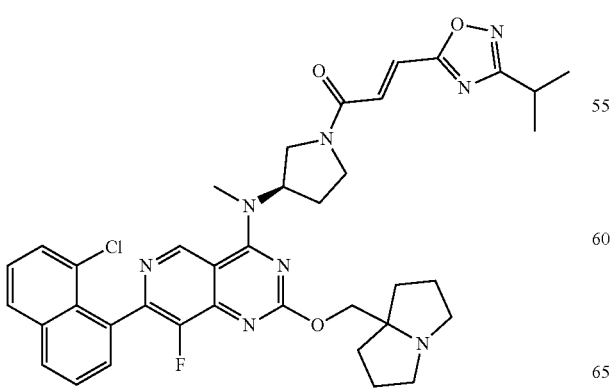

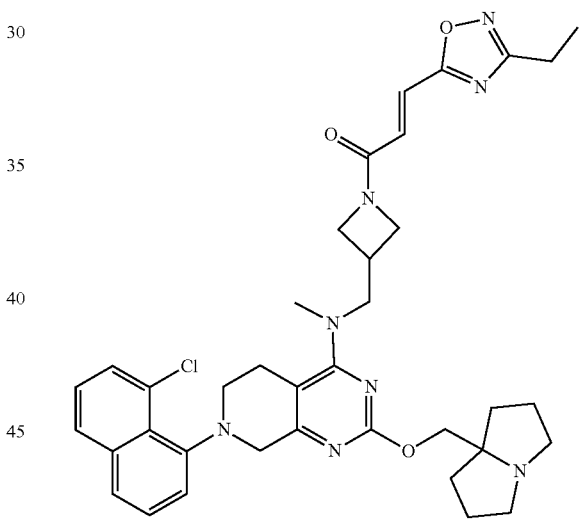

Example 168 (Method 4): (E)-1-(3-(((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)methyl)azetidin-1-yl)-3-(3-ethyl-1,2,4-oxadiazol-5-yl)prop-2-en-1-one

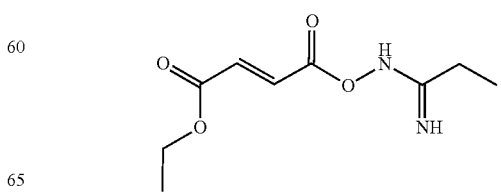

Step 1: (E)-ethyl 4-oxo-4-(propionimidamidooxy)but-2-enoate

The amide coupling reaction was prepared in a similar fashion to Method #1, Step 2.

The reaction mixture was concentrated in vacuo affording (E)-ethyl 4-oxo-4-(propionimidamidooxy)but-2-enoate (7.3 g, crude) as a yellow oil used in next step without further purification. LCMS Rt=0.508 min, m/z=214.1 [M+H]$^+$.

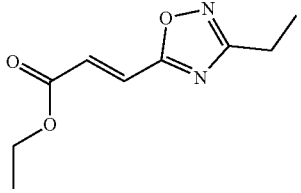

Step 2: (E)-ethyl 3-(3-ethyl-1,2,4-oxadiazol-5-yl)acrylate

The cyclization reaction was prepared in a similar fashion to Method #1, Step 3.

The reaction mixture was concentrated in vacuo affording (E)-ethyl 3-(3-ethyl-1,2,4-oxadiazol-5-yl)acrylate (5 g, crude) as a yellow oil used in next step without any further purification. LCMS Rt =0.595 min, m/z=196.1 [M+H]$^+$.

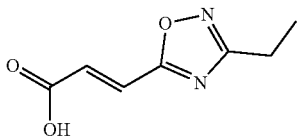

Step 4: (E)-3-(3-ethyl-1,2,4-oxadiazol-5-yl)acrylic acid

The hydrolysis reaction was prepared in a similar fashion to Method #1, Step 4.

The reaction mixture was concentrated in vacuo affording (E)-3-(3-ethyl-1,2,4-oxadiazol-5-yl)acrylic acid (4 g, crude) as a yellow oil used in next step without further purification. LCMS Rt 10=0.435 min, m/z=168.1 [M+H]$^+$.

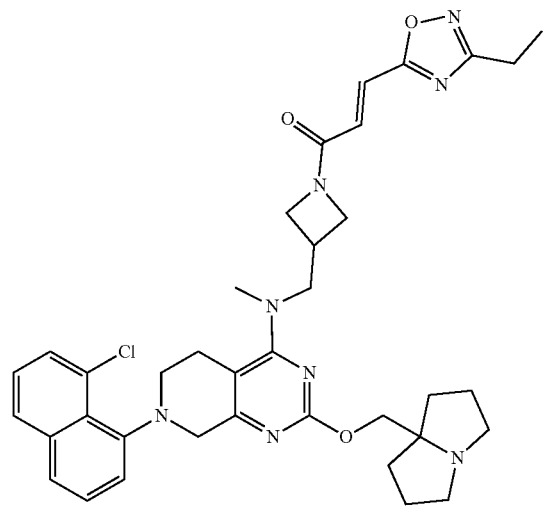 [SMILES: CCc1noc(/C=C/C(=O)N2CC(CN(C)c3nc(OCC45CCCN4CCC5)nc4c3CCN(c3cccc5cccc(Cl)c35)C4)C2)n1]

Step 5: (E)-1-(3-(((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)methyl)azetidin-1-yl)-3-(3-ethyl-1,2,4-oxadiazol-5-yl)prop-2-en-1-one The amide coupling reaction was prepared in a similar fashion to Method #4, Step 11.

The reaction mixture was concentrated in vacuo and purified by reverse phase HPLC (column: Waters Xbridge Prep OBD C18 150*40 mm*10 um; mobile phase: [water (ammonium bicarbonate)- acetonitrile]; B %: 40%-70%, 8 min) affording (E)-1-(3-(((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)methyl)azetidin-1-yl)-3-(3-ethyl-1,2,4-oxadiazol-5-yl)prop-2-en-1-one (7.5 mg 6.45%) as a yellow solid: $^1$H NMR (400 MHz, Acetonitrile-d3) δ 7.89-7.80 (m, 1H), 7.70-7.63 (m, 1H), 7.56-7.45 (m, 2H), 7.39 (dt, J=3.8, 7.8 Hz, 1H), 7.33-7.19 (m, 2H), 7.17-7.07 (m, 1H), 4.45-4.32 (m, 1H), 4.24-4.00 (m, 4H), 3.98-3.90 (m, 2H), 3.87-3.77 (m, 1H), 3.75-3.62 (m, 2H), 3.61-3.46 (m, 2H), 3.29-3.13 (m, 2H), 3.12-3.08 (m, 3H), 2.97 (br s, 2H), 2.80-2.72 (m, 2H), 2.66-2.54 (m, 3H), 1.89-1.71 (m, 6H), 1.62-1.53 (m, 2H), 1.32-1.25 (m, 3H). LCMS Rt=1.059 min, m/z=682.3 [M+H]$^+$.

LCMS (5 to 95% acetonitrile in water+0.03% ammonium bicarbonate over 6 mins) retention time 1.059 min, ESI+ found [M+H]=682.3.

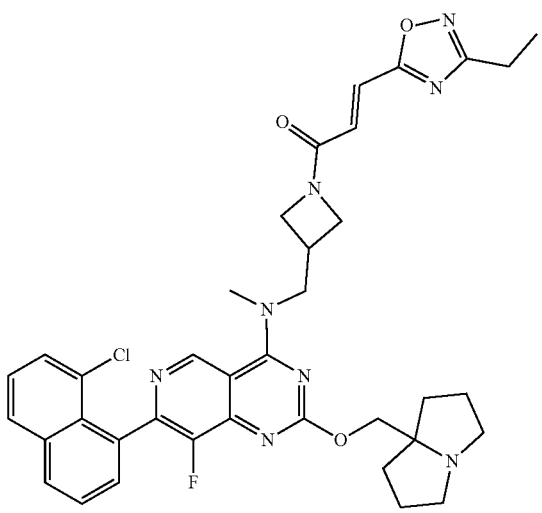 [SMILES: CCc1noc(/C=C/C(=O)N2CC(CN(C)c3nc(OCC45CCCN4CCC5)nc4c(F)c(-c5cccc6cccc(Cl)c56)ncc34)C2)n1]

Example 169 (Method 2): (E)-1-(3-(((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)methyl)azetidin-1-yl)-3-(3-ethyl-1,2,4-oxadiazol-5-yl)prop-2-en-1-one

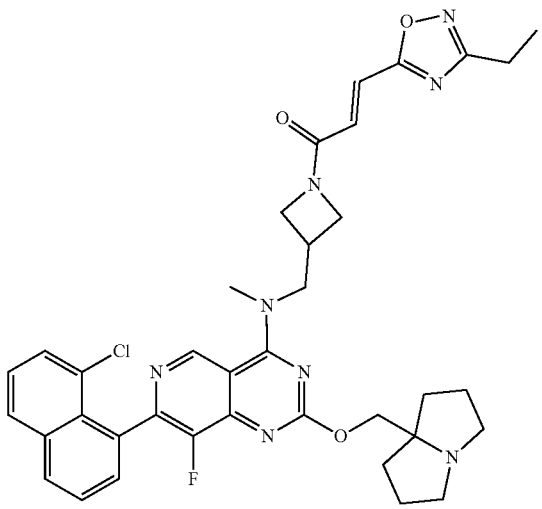 [SMILES: CCc1noc(/C=C/C(=O)N2CC(CN(C)c3nc(OCC45CCCN4CCC5)nc4c(F)c(-c5cccc6cccc(Cl)c56)ncc34)C2)n1]

Step 1: (E)-1-(3-(((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)methyl)azetidin-1-yl)-3-(3-ethyl-1,2,4-oxadiazol-5-yl)prop-2-en-1-one The amide coupling reaction was prepared in a similar fashion to Method #2, Step 7. The reaction mixture was purified by reverse phase HPLC (column: Waters Xbridge Prep OBD C18 150*40 mm*10 μm; mobile phase: [water (NH$_4$HCO$_3$)-acetonitrile]; B %: 35%-65%, 8 min) affording (E)-1-(3-(((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)methyl)azetidin-1-yl)-3-(3-ethyl-1,2,4-oxadiazol-5-yl)prop-2-en-1-one (7.45 mg, 6.17%) as a white amorphous solid: $^1$H NMR (400 MHz, Acetonitrile-d3) δ 9.26-9.21 (m, 1H), 8.15-8.07 (m, 1H), 8.04-7.98 (m, 1H), 7.72-7.66 (m, 1H), 7.63-7.59 (m, 2H), 7.54-7.49 (m, 1H), 7.34-7.27 (m, 1H), 7.18-7.11 (m, 1H), 4.51-4.43 (m, 1H), 4.34-4.20 (m, 2H), 4.18-4.08 (m, 4H), 3.96-3.88 (m, 1H), 3.58 (s, 3H), 3.28-3.19 (m, 1H), 2.98-2.91 (m, 2H), 2.76 (q, J=7.5 Hz, 2H), 2.61-2.55 (m, 2H), 1.90 (br d, J=6.3 Hz, 1H), 1.86-1.73 (m, 5H), 1.64-1.57 (m, 2H), 1.29 (t, J=7.6 Hz, 3H). LCMS Rt=2.686 min, m/z=696.3 [M+H]$^+$.

LCMS (5 to 95% acetonitrile in water+0.03% ammonium bicarbonate over 6 mins s) retention time 2.686 min, ESI+ found [M+H]=696.3.

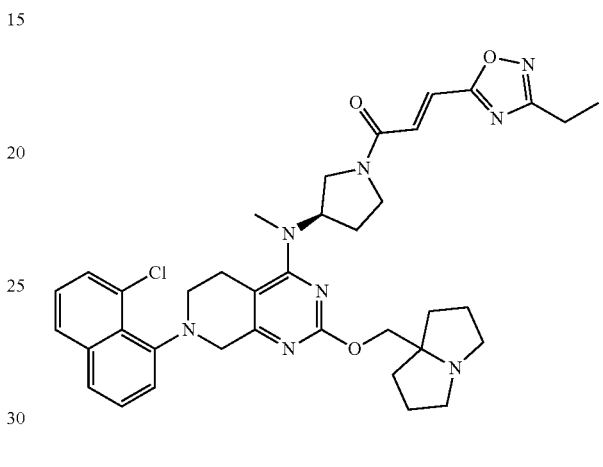

Example 170 (Method 4): (R,E)-1-(3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-ethyl-1,2,4-oxadiazol-5-yl)prop-2-en-1-one

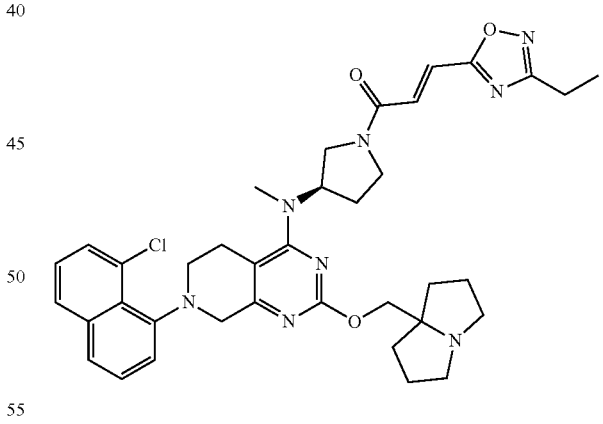

Step 1: (R,E)-1-(3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-ethyl-1,2,4-oxadiazol-5-yl)prop-2-en-1-one The amide coupling reaction was prepared in a similar fashion to Method #4, Step 11. The reaction mixture was concentrated in vacuo and purified by reverse phase HPLC (column: Waters Xbridge Prep OBD C18 150*40 mm*10 μm; mobile phase: [water (ammonium bicarbonate)-acetonitrile]; B %: 35%-65%, 8 min) affording (R,E)-1-(3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-ethyl-1,2,4-oxadiazol-5-yl)prop-2-en-1-one (15.56 mg, 23.79%) as a yellow oil: $^1$H NMR (400 MHz, Acetonitrile-d3) δ 7.91-7.79 (m, 1H), 7.74-7.62 (m, 1H), 7.59-7.55 (m, 1H), 7.54-7.46 (m, 1H), 7.45-7.38 (m, 2H), 7.37-7.35 (m, 1H), 7.35-7.31 (m, 1H), 4.08-4.00 (m, 1H), 3.99-3.77 (m, 3H), 3.76-3.57 (m, 3H), 3.55-3.34 (m, 2H), 3.31-3.16 (m, 2H), 3.16-3.01 (m, 2H), 2.83-2.70 (m, 3H), 2.51 (br s, 3H), 2.30-2.29 (m, 1H), 2.28 (br s, 1H), 2.26-2.08 (m, 4H), 2.01 (br d, J=2.5 Hz, 1H), 1.89-1.50 (m, 6H), 1.32 (t, J=7.6 Hz, 3H). LCMS Rt=3.204 min, m/z=682.3 [M+H]$^+$.

LCMS (5 to 95% acetonitrile in water+0.03% ammonium bicarbonate over 6 mins) retention time 3.204 min, ESI+ found [M+H]=682.3.

Example 171 (Method 2): (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-ethyl-1,2,4-oxadiazol-5-yl)prop-2-en-1-one

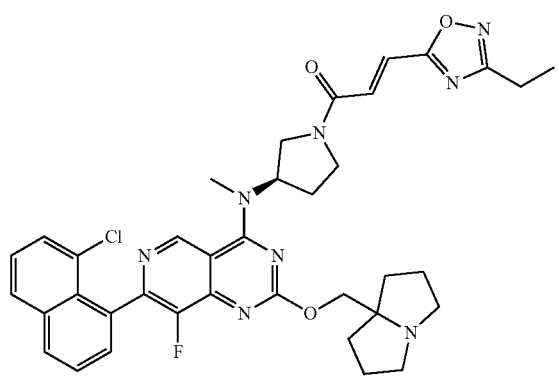 [SMILES: CCc1noc(/C=C/C(=O)N2CC[C@@H](N(C)c3nc(OCC45CCCN4CCC5)nc4c(F)c(-c5cccc6cccc(Cl)c56)ncc34)C2)n1]

Step 1: (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-ethyl-1,2,4-oxadiazol-5-yl)prop-2-en-1-one The amide coupling reaction was prepared in a similar fashion to Method #2, Step 7. The reaction mixture was purified by reverse phase HPLC (column: Waters Xbridge Prep OBD C18 150*40 mm*10 um; mobile phase: [water (NH$_4$HCO$_3$)-acetonitrile]; B %: 30%-60%, 8 min) affording (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-ethyl-1,2,4-oxadiazol-5-yl)prop-2-en-1-one (18.13 mg, 17.19%) as a yellow oil: $^1$H NMR (400 MHz, Acetonitrile-d3) δ 9.20 (d, J=1.8 Hz, 1H), 8.14 (d, J=8.1 Hz, 1H), 8.03 (d, J=7.8 Hz, 1H), 7.75-7.67 (m, 1H), 7.67-7.60 (m, 2H), 7.56-7.49 (m, 1H), 7.49-7.34 (m, 2H), 5.51-5.29 (m, 1H), 4.24-4.15 (m, 2H), 4.02 (br dd, J=8.7, 12.3 Hz, 1H), 3.90-3.76 (m, 1H), 3.54 (br s, 1H), 3.45 (s, 3H), 3.03-2.91 (m, 2H), 2.79 (qd, J=7.6, 10.9 Hz, 2H), 2.60 (qd, J=6.8, 9.8 Hz, 2H), 2.47-2.39 (m, 1H), 2.33 (br s, 1H), 2.00-1.92 (m, 3H), 1.89-1.74 (m, 4H), 1.68-1.57 (m, 2H), 1.32 (td, J=7.5, 10.1 Hz, 3H). LCMS Rt=2.227 min, m/z=696.3 [M+H]$^+$.

LCMS (5 to 95% acetonitrile in water+0.1% trifluoroacetic acid over 6 mins) retention time 2.227 min, ESI+ found [M+H]=696.3.


Example 172 (Method 4): (E)-1-(3-(((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)methyl)azetidin-1-yl)-3-(3-cyclopropyl-1,2,4-oxadiazol-5-yl)prop-2-en-1-one

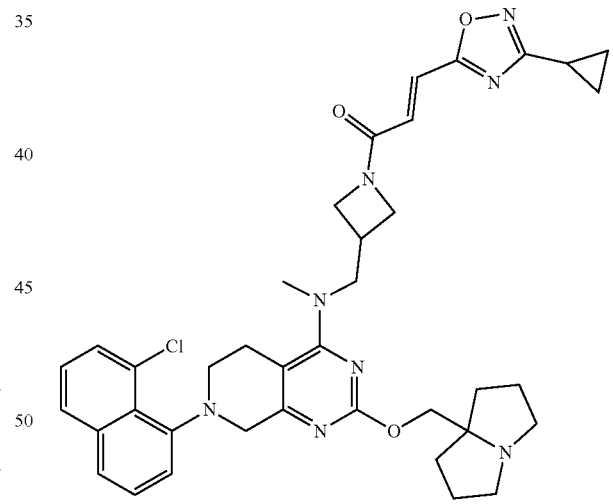

Step 1: (E)-1-(3-(((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)methyl)azetidin-1-yl)-3-(3-cyclopropyl-1,2,4-oxadiazol-5-yl)prop-2-en-1-one The amide coupling reaction was prepared in a similar fashion to Method #4, Step 11. The reaction mixture was concentrated in vacuo and purified by reverse phase HPLC (Waters Xbridge Prep OBD C18 150*40 mm*10 um; mobile phase: [water (ammonium bicarbonate)- acetonitrile]; B %: 35%-65%, 8 min) affording (E)-1-(3-(((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)methyl)azetidin-1-yl)-3-(3-cyclopropyl-1,2,4-oxadiazol-5-yl)prop-2-en-1-one (15.54 mg, 15.26%) as a yellow solid: 1H NMR (400 MHz, Acetonitrile-d3) δ 7.84 (d, J=8.1 Hz, 1H), 7.70-7.64 (m, 1H), 7.57-7.47 (m, 2H), 7.39 (dt, J=3.1, 7.8 Hz, 1H), 7.31 (d, J=7.5 Hz, 1H), 7.27-7.20 (m, 1H), 7.13-7.03 (m, 1H), 4.42-4.32 (m, 1H), 4.13 (br d, J=8.5 Hz, 2H), 4.11-4.00 (m, 2H), 3.99-3.87 (m, 3H), 3.84-3.63 (m, 3H), 3.60-3.48 (m, 2H), 3.23-3.15 (m, 1H), 3.12-3.09 (m, 3H), 3.09-3.04 (m, 1H), 2.96-2.88 (m, 2H), 2.65 (br s, 3H), 1.91-1.85 (m, 2H), 1.82-1.71 (m, 4H), 1.60-1.53 (m, 2H), 1.11-1.05 (m, 2H), 0.97-0.90 (m, 2H) LCMS Rt =2.204 min, m/z=694.3 [M+H]+.

LCMS (5 to 95% acetonitrile in water+0.03% ammonium bicarbonate over 6 mins) retention time 2.204 min, ESI+ found [M+H]=694.3.

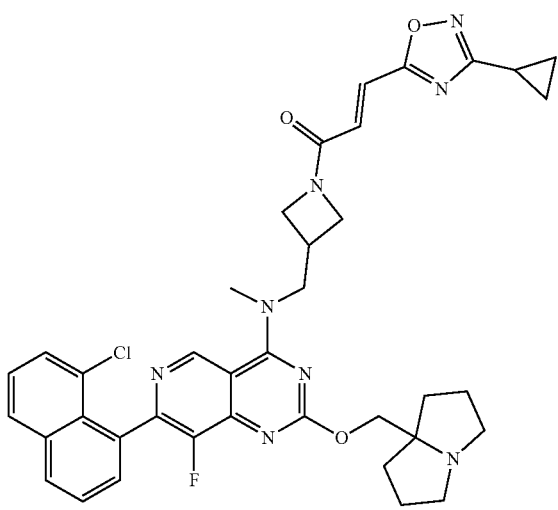 [SMILES: CN(CC1CN(C(=O)/C=C/c2nc(C3CC3)no2)C1)c1nc(OCC23CCCN2CCC3)nc2c(F)c(-c3cccc4cccc(Cl)c34)ncc12]

Example 173 (Method 2): (E)-1-(3-(((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)methyl)azetidin-1-yl)-3-(3-cyclopropyl-1,2,4-oxadiazol-5-yl)prop-2-en-1-one

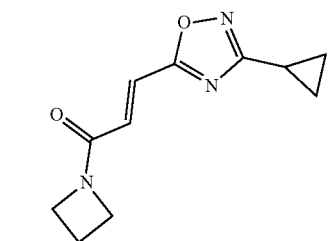

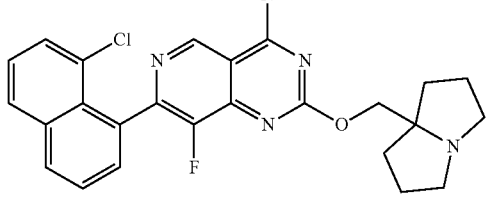

Step 1: (E)-1-(3-(((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)methyl)azetidin-1-yl)-3-(3-cyclopropyl-1,2,4-oxadiazol-5-yl)prop-2-en-1-one The amide coupling reaction was prepared in a similar fashion to Method #2, Step 7. The reaction mixture was purified by reverse phase HPLC (column: Waters Xbridge BEH C18 100*30 mm*10 µm; mobile phase: [water (NH4HCO3)-acetonitrile]; B %: 30%-60%, 10 min) affording (E)-1-(3-(((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)methyl)azetidin-1-yl)-3-(3-cyclopropyl-1,2,4-oxadiazol-5-yl)prop-2-en-1-one (50.12 mg, 25.96%) as a white solid: 1H NMR (400 MHz, Acetonitrile-d3) δ 9.32 (s, 1H), 8.20 (d, J=7.6 Hz, 1H), 8.10 (d, J=8.3 Hz, 1H), 7.81-7.74 (m, 1H), 7.70 (br d, J=7.4 Hz, 2H), 7.62-7.56 (m, 1H), 7.38-7.30 (m, 1H), 7.26-7.10 (m, 1H), 4.59-4.49 (m, 1H), 4.41-4.29 (m, 2H), 4.28-4.14 (m, 4H), 4.05-3.96 (m, 1H), 3.67 (s, 3H), 3.31 (br s, 1H), 3.15-3.04 (m, 2H), 2.77-2.66 (m, 2H), 1.95-1.83 (m, 6H), 1.77-1.67 (m, 3H), 1.19-1.15 (m, 2H), 1.06-1.02 (m, 2H). LCMS Rt=2.747 min, m/z=708.3 [M+H]+.

LCMS (5 to 95% acetonitrile in water+0.03% ammonium bicarbonate over 6 mins s) retention time 2.747 min, ESI+ found [M+H]=708.3.

Example 174 (Method 2): (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-cyclopropyl-1,2,4-oxadiazol-5-yl)prop-2-en-1-one

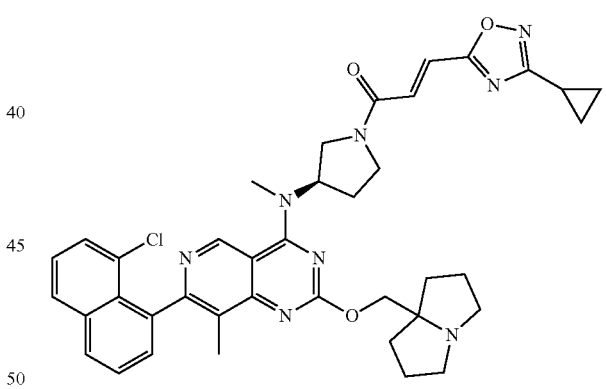

Step 1: (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-cyclopropyl-1,2,4-oxadiazol-5-yl)prop-2-en-1-one The amide coupling reaction was prepared in a similar fashion to Method #2, Step 7. The reaction mixture was purified by reverse phase HPLC (column: Waters Xbridge Prep OBD C18 150*40 mm*10 um; mobile phase: [water (NH4HCO3)-acetonitrile]; B %: 30%-60%, 8 min) affording (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-cyclopropyl-1,2,4-oxadiazol-5-yl)prop-2-en-1-one (28 mg, 20.77%)

as a yellow amorphous solid: $^{1}$H NMR (400 MHz, Acetonitrile-d3) δ 9.26-9.21 (m, 1H), 8.17 (d, J=7.5 Hz, 1H), 8.09-8.04 (m, 1H), 7.77-7.71 (m, 1H), 7.69-7.63 (m, 2H), 7.56 (s, 1H), 7.44 (d, J=12.1 Hz, 1H), 7.40-7.31 (m, 1H), 5.53-5.34 (m, 1H), 4.25-4.18 (m, 2H), 4.13-3.99 (m, 1H), 3.98-3.73 (m, 2H), 3.48 (s, 3H), 3.09-2.96 (m, 2H), 2.71-2.61 (m, 2H), 2.51-2.42 (m, 1H), 2.41-2.33 (m, 1H), 2.15-2.05 (m, 3H), 1.93-1.78 (m, 5H), 1.73-1.63 (m, 2H), 1.16-1.10 (m, 1H), 1.16-1.08 (m, 1H), 1.05-0.97 (m, 2H). LCMS Rt=2.257 min, m/z=708.3 [M+H]$^{+}$.

LCMS (5 to 95% acetonitrile in water+0.1% trifluoroacetic acid over 6 mins) retention time 2.257 min, ESI+ found [M+H]=708.3.

Step 1: (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-(difluoromethyl)-1,2,4-oxadiazol-5-yl)prop-2-en-1-one The amide coupling reaction was prepared in a similar fashion to Method #4, Step 11. The crude product was purified by reverse phase HPLC (column: Waters Xbridge Prep OBD C18 150*40 mm*10 um; mobile phase: [water (ammonium bicarbonate)- acetonitrile]; B %: 50%-80%, 8 min) affording (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-(difluoromethyl)-1,2,4-oxadiazol-5-yl)prop-2-en-1-one (5.63 mg, 10.36%) as a yellow oil: $^{1}$H NMR (400 MHz, Acetonitrile-d3) δ 7.93-7.86 (m, 1H), 7.72 (br d, J=8.1 Hz, 1H), 7.64-7.34 (m, 6H), 7.20-6.89 (m, 1H), 5.42-5.15 (m, 1H), 4.99-4.73 (m, 1H), 4.28 (br dd, J=5.1, 17.3 Hz, 1H), 4.18-4.09 (m, 1H), 4.08-3.95 (m, 2H), 3.90-3.79 (m, 1H), 3.77-3.65 (m, 2H), 3.62-3.44 (m, 2H), 3.29-3.10 (m, 5H), 3.02 (d, J=4.9 Hz, 3H), 2.97-2.89 (m, 1H), 2.64 (br d, J=15.5 Hz, 1H), 2.22-2.16 (m, 3H), 2.07 (br d, J=4.8 Hz, 2H), 1.96-1.79 (m, 3H). LCMS Rt=3.328 min, m/z=722.3 [M+H]+.

LCMS (5 to 95% acetonitrile in water+0.03% ammonium bicarbonate over 6 mins) retention time 3.328 min, ESI+ found [M+H]=722.3.

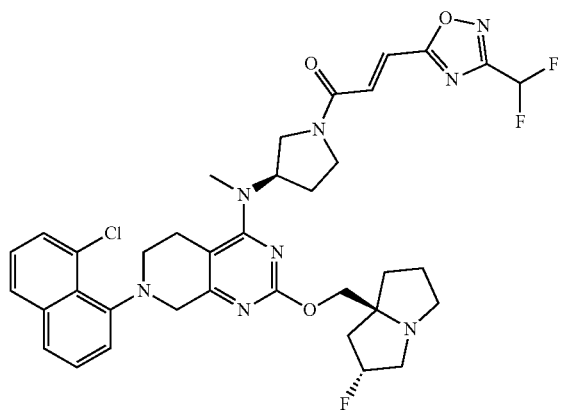 [SMILES: CN(c1nc(OC[C@@]23CCCN2C[C@H](F)C3)nc2c1CCN(c1cccc3cccc(Cl)c13)C2)[C@@H]1CCN(C(=O)/C=C/c2nc(C(F)F)no2)C1]

Example 175 (Method 4): (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-(difluoromethyl)-1,2,4-oxadiazol-5-yl)prop-2-en-1-one

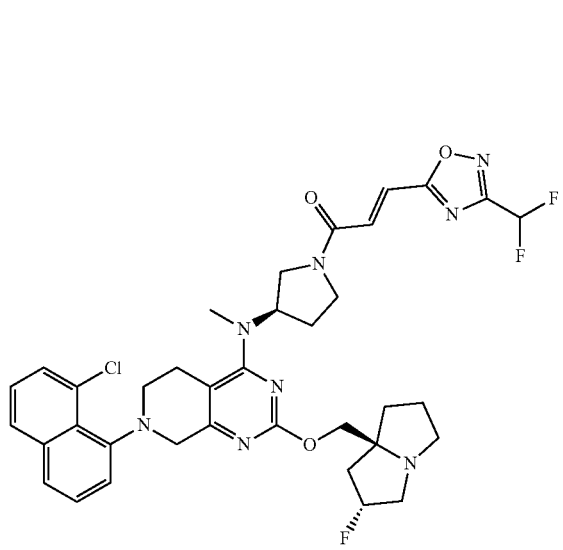 [SMILES: CN(c1nc(OC[C@@]23CCCN2C[C@H](F)C3)nc2c1CCN(c1cccc3cccc(Cl)c13)C2)[C@@H]1CCN(C(=O)/C=C/c2nc(C(F)F)no2)C1]

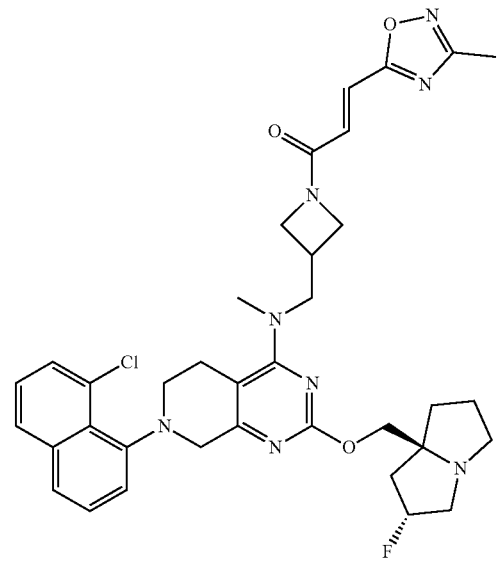 [SMILES: Cc1noc(/C=C/C(=O)N2CC(CN(C)c3nc(OC[C@@]45CCCN4C[C@H](F)C5)nc4c3CCN(c3cccc5cccc(Cl)c35)C4)C2)n1]

Example 176 (Method 4): (E)-1-(3-(((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)methyl)azetidin-1-yl)-3-(3-methyl-1,2,4-oxadiazol-5-yl)prop-2-en-1-one

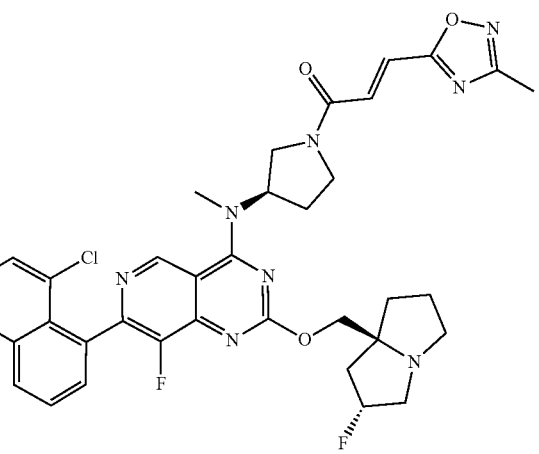

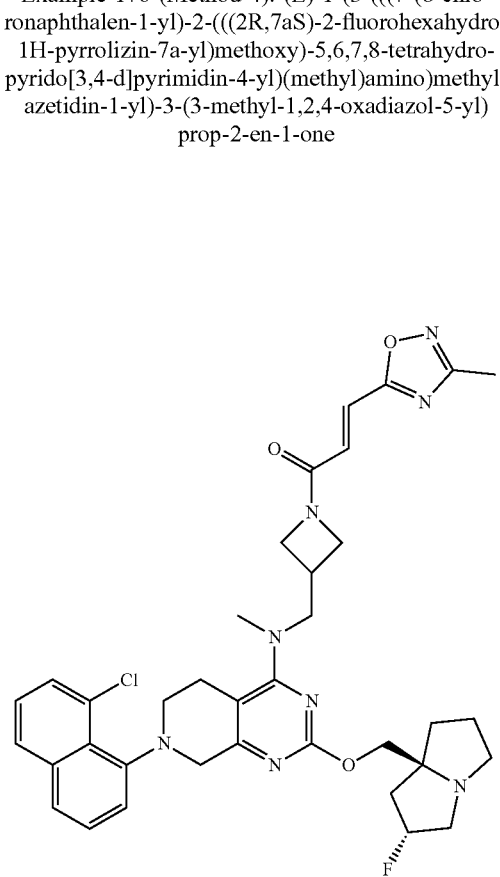

Example 177 (Method 1): (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-methyl-1,2,4-oxadiazol-5-yl)prop-2-en-1-one

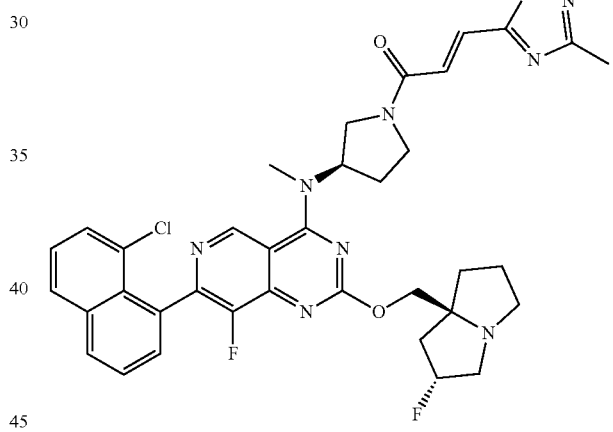

Step 1: (E)-1-(3-(((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)methyl)azetidin-1-yl)-3-(3-methyl-1,2,4-oxadiazol-5-yl)prop-2-en-1-one The amide coupling reaction was prepared in a similar fashion to Method #4, Step 11. The crude product was purified by reverse phase HPLC (column: Waters Xbridge Prep OBD C18 150*40 mm*10 μm; mobile phase: [water (ammonium bicarbonate)- acetonitrile]; B %: 50%-85%, 8 min) affording (E)-1-(3-(((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)methyl)azetidin-1-yl)-3-(3-methyl-1,2,4-oxadiazol-5-yl)prop-2-en-1-one (18.11 mg, 11.56%) as a white solid: $^1$H NMR (400 MHz, Acetonitrile-d3) δ 7.87 (d, J=8.2 Hz, 1H), 7.69 (d, J=8.1 Hz, 1H), 7.59-7.49 (m, 2H), 7.41 (dt, J=2.9, 7.8 Hz, 1H), 7.35-7.28 (m, 2H), 7.19-7.11 (m, 1H), 5.35-5.14 (m, 1H), 4.40 (q, J=8.2 Hz, 1H), 4.26-4.18 (m, 1H), 4.15-3.99 (m, 3H), 3.99-3.90 (m, 1H), 3.86 (dd, J=6.5, 11.1 Hz, 1H), 3.78-3.48 (m, 4H), 3.31-3.19 (m, 1H), 3.16-2.98 (m, 8H), 2.94-2.84 (m, 1H), 2.65 (br d, J=15.2 Hz, 1H), 2.41 (s, 3H), 2.14 (br s, 1H), 2.07 (br s, 2H), 1.93-1.75 (m, 3H). LCMS Rt=3.324 min, m/z=686.3 [M+H]+.

LCMS (5 to 95% acetonitrile in water+0.03% ammonium bicarbonate over 6 mins) retention time 3.324 min, ESI+ found [M+H]=686.3.

Step 1: (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-methyl-1,2,4-oxadiazol-5-yl)prop-2-en-1-one The amide coupling reaction was prepared in a similar fashion to Method #1, Step 10. The residue was purified by reverse phase HPLC (column: Waters Xbridge Prep OBD C18 150*40 mm*10 um; mobile phase: [water (NH$_4$HCO$_3$)-acetonitrile]; B %: 40%-70%, 8 min) affording (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-methyl-1,2,4-oxadiazol-5-yl)prop-2-en-1-one (10.07 mg, 15.89%) as a yellow amorphous solid: $^1$H NMR (400 MHz, Acetonitrile-d3) δ 9.21-9.16 (m, 1H), 8.14-8.09 (m, 1H), 8.04-7.98 (m, 1H), 7.72-7.66 (m, 1H), 7.64-7.58 (m, 2H), 7.54-7.49 (m, 1H), 7.44 (d, J=12.4 Hz, 1H), 7.40-7.33 (m, 1H), 5.45-5.15 (m, 2H), 4.24-4.15 (m, 3H), 4.16-4.09 (m, 1H), 4.06-3.95 (m, 2H), 3.92-3.71 (m, 1H), 3.43 (s, 3H), 3.13-3.02 (m, 3H), 2.93-2.83 (m, 1H), 2.38 (d, J=8.3 Hz, 3H), 2.33-2.29 (m, 1H), 2.11-2.00 (m, 3H), 1.89-1.79 (m, 3H). LCMS Rt=3.047 min, m/z=700.3 [M+H]⁺.

LCMS (5 to 95% acetonitrile in water+0.03% ammonium bicarbonate over 6 mins) retention time 3.047 min, ESI+ found [M+H]=700.3

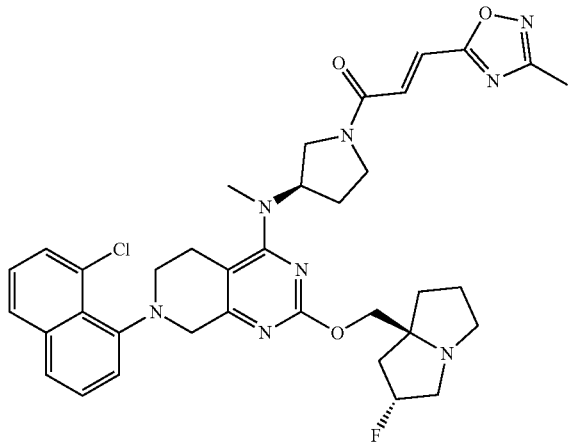 [SMILES: Cc1noc(/C=C/C(=O)N2CC[C@@H](N(C)c3nc(OC[C@@]45CCCN4C[C@H](F)C5)nc4c3CCN(c3cccc5cccc(Cl)c35)C4)C2)n1]

Example 178 (Method 4): (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-methyl-1,2,4-oxadiazol-5-yl)prop-2-en-1-one

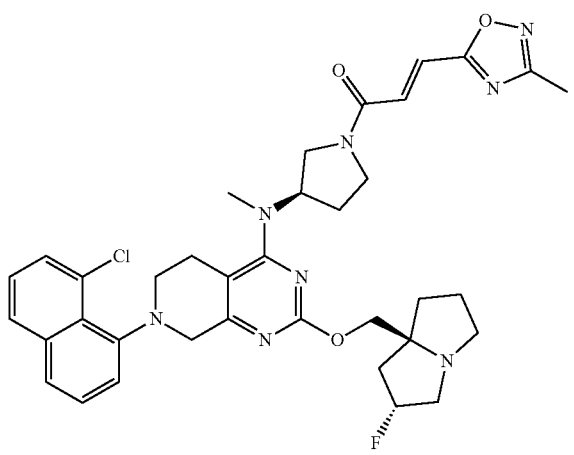 [SMILES: Cc1noc(/C=C/C(=O)N2CC[C@@H](N(C)c3nc(OC[C@@]45CCCN4C[C@H](F)C5)nc4c3CCN(c3cccc5cccc(Cl)c35)C4)C2)n1]

Step 1: (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-methyl-1,2,4-oxadiazol-5-yl)prop-2-en-1-one The amide coupling reaction was prepared in a similar fashion to Method #4, Step 11. The reaction mixture was concentrated in vacuo and purified by reverse phase HPLC (column: Waters Xbridge Prep OBD C18 150*40 mm*10 µm; mobile phase: [water (ammonium bicarbonate)-acetonitrile]; B %: 50%-85%, 8 min) affording (E)-1-((R)-3-((7-(8-chloronaphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-methyl-1,2,4-oxadiazol-5-yl)prop-2-en-1-one (17.87 mg, 12.03%) as a white solid: ¹H NMR (400 MHz, Acetonitrile-d3) δ 7.87 (br d, J=7.9 Hz, 1H), 7.70 (br d, J=7.7 Hz, 1H), 7.60-7.47 (m, 2H), 7.47-7.30 (m, 4H), 5.36-5.14 (m, 1H), 4.92-4.74 (m, 1H), 4.30-4.13 (m, 1H), 4.10-3.90 (m, 3H), 3.87-3.76 (m, 1H), 3.75-3.62 (m, 2H), 3.60-3.39 (m, 2H), 3.35-3.20 (m, 1H), 3.16-3.04 (m, 4H), 2.99 (br d, J=4.8 Hz, 3H), 2.94-2.82 (m, 1H), 2.62 (br d, J=14.5 Hz, 1H), 2.41 (br d, J=4.9 Hz, 3H), 2.15 (br d, J=7.0 Hz, 1H), 2.08 (br s, 1H), 2.05-1.96 (m, 3H), 1.93-1.74 (m, 3H). LCMS Rt=2.318 min, m/z=686.3 [M+H]+.

LCMS (5 to 95% acetonitrile in water+0.03% ammonium bicarbonate over 6 mins) retention time 2.318 min, ESI+ found [M+H]=686.3.

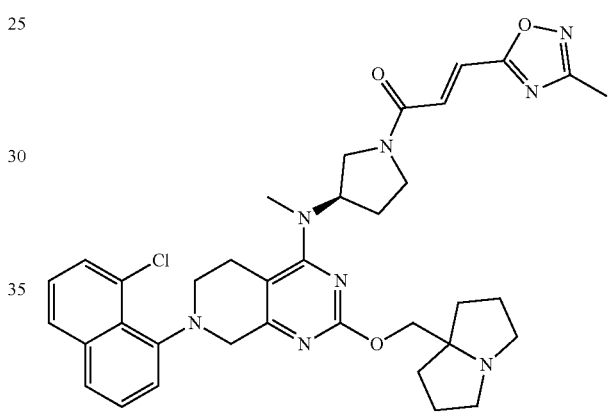

Example 179 (Method 4): (R,E)-1-(3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-methyl-1,2,4-oxadiazol-5-yl)prop-2-en-1-one

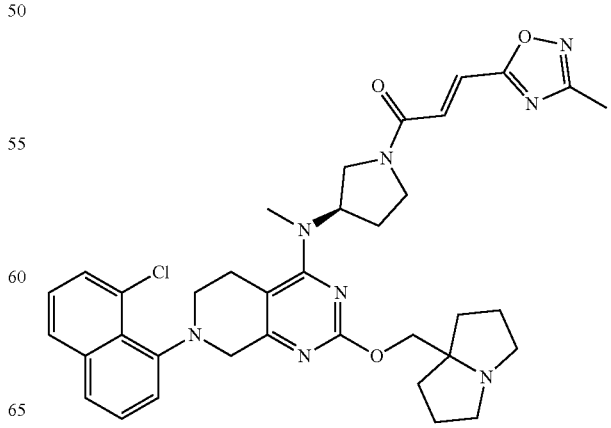

Step 1: (R,E)-1-(3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-methyl-1,2,4-oxadiazol-5-yl)prop-2-en-1-one The amide coupling reaction was prepared in a similar fashion to Method #4, Step 11. The reaction mixture was concentrated in vacuo and purified by reverse phase HPLC column: Waters Xbridge BEH C18 100*30 mm*10 μm; mobile phase: [water (ammonium bicarbonate)-acetonitrile]; B %: 60%-90%, 8 min) affording (R,E)-1-(3-((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)pyrrolidin-1-yl)-3-(3-methyl-1,2,4-oxadiazol-5-yl)prop-2-en-1-one (17.87 mg, 12.03%) as a white solid: $^1$H NMR (400 MHz, Acetonitrile-d3) δ 7.83 (d, J=8.1 Hz, 1H), 7.66 (br d, J=8.3 Hz, 1H), 7.54 (d, J=7.4 Hz, 1H), 7.50-7.46 (m, 1H), 7.41-7.39 (m, 1H), 7.36 (d, J=9.1 Hz, 1H), 7.35-7.27 (m, 2H), 4.89-4.73 (m, 1H), 4.26-4.19 (m, 1H), 4.07-3.85 (m, 4H), 3.81-3.74 (m, 1H), 3.71-3.59 (m, 2H), 3.55-3.42 (m, 2H), 3.23 (br d, J=4.4 Hz, 1H), 3.11-3.05 (m, 1H), 2.98-2.95 (m, 3H), 2.91 (br d, J=5.5 Hz, 1H), 2.62-2.54 (m, 3H), 2.38-2.35 (m, 3H), 1.90-1.84 (m, 2H), 1.84-1.66 (m, 5H), 1.66-1.47 (m, 3H) LCMS Rt=2.336 min, m/z=668.3 [M+H]$^+$.

LCMS (5 to 95% acetonitrile in water+0.03% ammonium bicarbonate over 6 mins) retention time 2.336 min, ESI+ found [M+H]=668.3

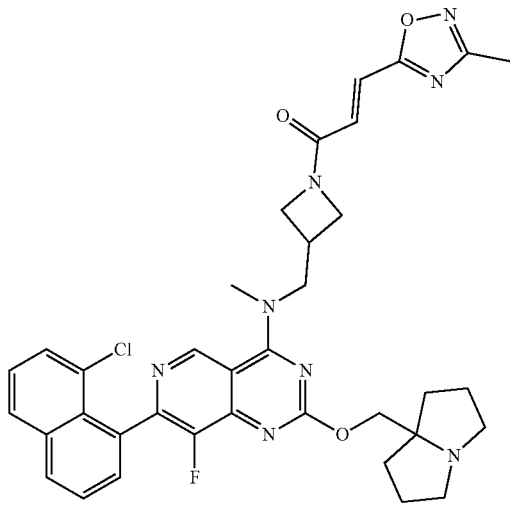 [SMILES: Cc1noc(/C=C/C(=O)N2CC(CN(C)c3nc(OCC45CCCN4CCC5)nc4c(F)c(-c5cccc6cccc(Cl)c56)ncc34)C2)n1]

Example 180 (Method 2): (E)-1-(3-(((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)methyl)azetidin-1-yl)-3-(3-methyl-1,2,4-oxadiazol-5-yl)prop-2-en-1-one

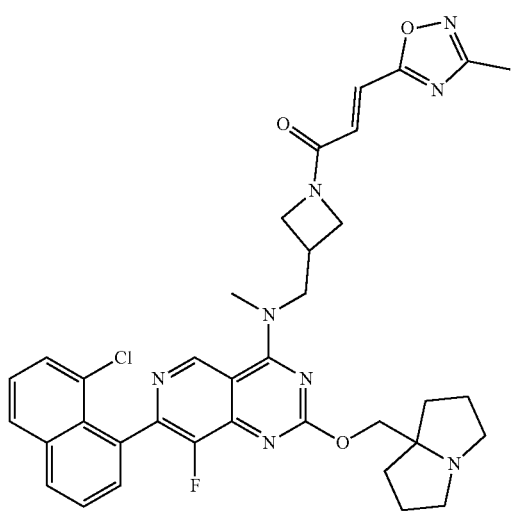 [SMILES: Cc1noc(/C=C/C(=O)N2CC(CN(C)c3nc(OCC45CCCN4CCC5)nc4c(F)c(-c5cccc6cccc(Cl)c56)ncc34)C2)n1]

Step 1: (E)-1-(3-(((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)methyl)azetidin-1-yl)-3-(3-methyl-1,2,4-oxadiazol-5-yl)prop-2-en-1-one The amide coupling reaction was prepared in a similar fashion to Method #2, Step 7. The reaction mixture was purified by reverse phase HPLC (column: C18-1 150*30 mm*5 μm; mobile phase: [water (NH$_4$HCO$_3$)-acetonitrile]; B %: 35%-65%, 10 min) affording (E)-1-(3-(((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)methyl)azetidin-1-yl)-3-(3-methyl-1,2,4-oxadiazol-5-yl)prop-2-en-1-one (12.75 mg, 11.22%) as a pale yellow amorphous solid: $^1$H NMR (400 MHz, Acetonitrile-d3) δ 9.23 (s, 1H), 8.12 (dd, J=0.9, 8.2 Hz, 1H), 8.02 (d, J=8.1 Hz, 1H), 7.71-7.66 (m, 1H), 7.63-7.59 (m, 2H), 7.54-7.49 (m, 1H), 7.33-7.28 (m, 1H), 7.18-7.13 (m, 1H), 4.51-4.43 (m, 1H), 4.35-4.19 (m, 2H), 4.17-4.07 (m, 4H), 3.97-3.88 (m, 1H), 3.60-3.55 (m, 3H), 3.27-3.20 (m, 1H), 3.01-2.94 (m, 2H), 2.63-2.56 (m, 2H), 2.40-2.34 (m, 3H), 1.97-1.96 (m, 1H), 1.90 (s, 1H), 1.86-1.75 (m, 4H), 1.66-1.58 (m, 2H). LCMS Rt=2.541 min, m/z=682.3 [M+H]$^+$.

LCMS (5 to 95% acetonitrile in water+0.03% ammonium bicarbonate over 6 mins s) retention time 2.541 min, ESI+ found [M+H]=682.3.

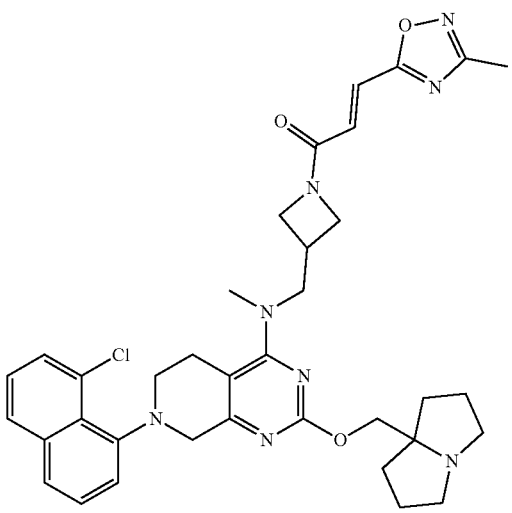 [SMILES: Cc1noc(/C=C/C(=O)N2CC(CN(C)c3nc(OCC45CCCN4CCC5)nc4c3CCN(c3cccc5cccc(Cl)c35)C4)C2)n1]

Example 181 (Method 4): (E)-1-(3-(((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)methyl)azetidin-1-yl)-3-(3-methyl-1,2,4-oxadiazol-5-yl)prop-2-en-1-one

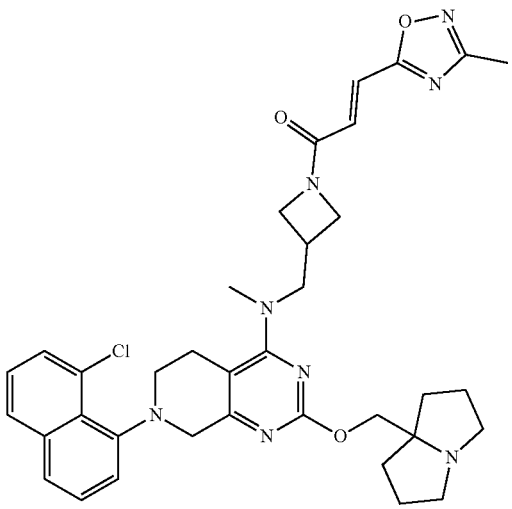 [SMILES: Cc1noc(/C=C/C(=O)N2CC(CN(C)c3nc(OCC45CCCN4CCC5)nc4c3CCN(c3cccc5cccc(Cl)c35)C4)C2)n1]

Step 1: (E)-1-(3-(((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)methyl)azetidin-1-yl)-3-(3-methyl-1,2,4-oxadiazol-5-yl)prop-2-en-1-one The amide coupling reaction was prepared in a similar fashion to Method #4, Step 11. The reaction mixture was concentrated in vacuo and purified by reverse phase HPLC column: Waters Xbridge Prep OBD C18 150*40 mm*10 um; mobile phase: [water (ammonium bicarbonate]; B %: 35%-65%, 8 min. affording (E)-1-(3-(((7-(8-chloronaphthalen-1-yl)-2-((hexahydro-1H-pyrrolizin-7a-yl)methoxy)-5,6,7,8-tetrahydropyrido[3,4-d]pyrimidin-4-yl)(methyl)amino)methyl)azetidin-1-yl)-3-(3-methyl-1,2,4-oxadiazol-5-yl)prop-2-en-1-one (19.84 mg, 21.32%) as a yellow solid: $^1$H NMR (400 MHz, Acetonitrile-d3) δ 7.87-7.81 (m, 1H), 7.70-7.63 (m, 1H), 7.57-7.46 (m, 2H), 7.42-7.35 (m, 1H), 7.26 (d, J=2.6 Hz, 2H), 7.17-7.08 (m, 1H), 4.38 (q, J=8.4 Hz, 1H), 4.25-4.18 (m, 1H), 4.17-3.95 (m, 3H), 3.88 (m, 2H), 3.85-3.55 (m, 3H), 3.54-3.48 (m, 1H), 3.27-3.16 (m, 1H), 3.16-3.01 (m, 5H), 2.96-2.88 (m, 2H), 2.68-2.50 (m, 3H), 2.41-2.32 (m, 3H), 1.91-1.84 (m, 2H), 1.83-1.67 (m, 4H), 1.61-1.51 (m, 2H) LCMS Rt=2.945 min, m/z=668.3 [M+H]$^+$.

LCMS (5 to 95% acetonitrile in water+0.03% ammonium bicarbonate over 6 mins) retention time 2.945 min, ESI+ found [M+H]=668.3

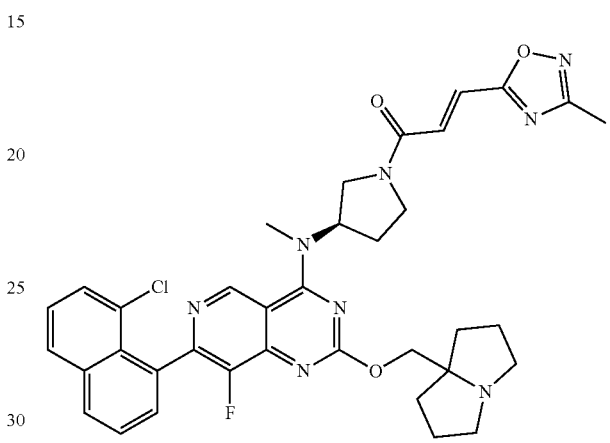

Example 182 (Method 2): (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-methyl-1,2,4-oxadiazol-5-yl)prop-2-en-1-one

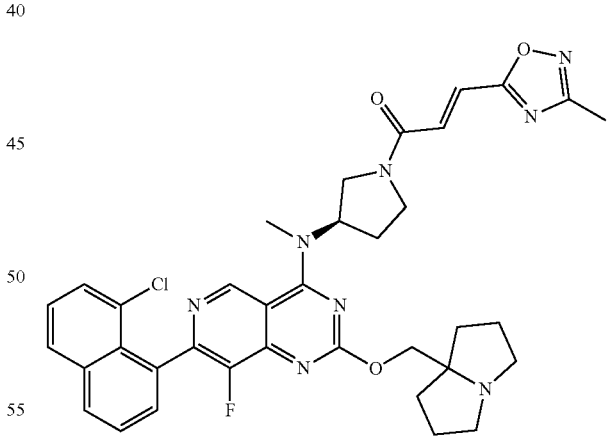

Step 1: (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-methyl-1,2,4-oxadiazol-5-yl)prop-2-en-1-one The amide coupling reaction was prepared in a similar fashion to Method #2, Step 7. The reaction mixture was purified by reverse phase HPLC (column: Waters Xbridge BEH C18 100*30 mm*10 um; mobile phase: [water (NH$_4$HCO$_3$)-acetonitrile]; B %: 30%-60%, 8 min) affording (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-methyl-1,2,4-oxadiazol-5-yl)prop-2-en-1-one (27.19 mg, 20.84%) as a pale yellow amorphous solid: $^1$H NMR (400 MHz, Acetonitrile-d3) δ 9.19-9.15 (m, 1H), 8.14-8.10 (m, 1H), 8.03-7.99 (m, 1H), 7.71-7.66 (m, 1H), 7.64-7.59 (m, 2H), 7.53-7.48 (m, 1H), 7.47-7.41 (m, 1H), 7.40-7.33 (m, 1H), 5.47-5.28 (m, 1H), 4.22-4.14 (m, 2H), 4.06-3.96 (m, 1H), 3.93-3.70 (m, 2H), 3.65-3.48 (m, 1H), 3.44-3.38 (m, 3H), 3.02-2.91 (m, 2H), 2.65-2.54 (m, 2H), 2.43-2.31 (m, 5H), 1.99-1.95 (m, 1H), 1.91-1.73 (m, 5H), 1.67-1.57 (m, 2H). LCMS Rt=2.177 min, m/z=682.3 [M+H]$^+$.

LCMS (5 to 95% acetonitrile in water+0.1% trifluoroacetic acid over 6 mins) retention time 2.177 min, ESI+ found [M+H]=682.3.

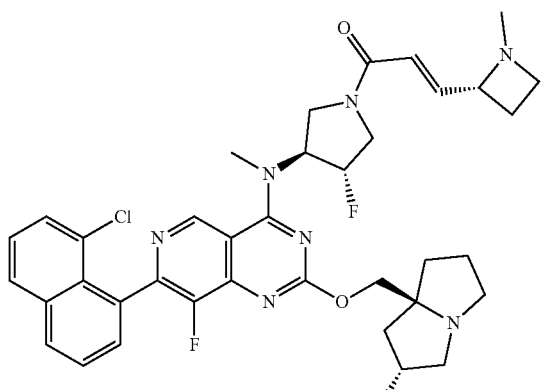

Example 183 (Method 11): (E)-1-((3S,4S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-((R)-1-methylazetidin-2-yl)prop-2-en-1-one

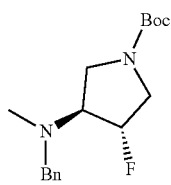

Step 1: (3S,4S)-tert-butyl 3-(benzyl(methyl)amino)-4-fluoropyrrolidine-1-carboxylate The reductive amination was prepared in a similar fashion to Method #6, Step 1, the crude residue was purified by column chromatography (silica gel, 100-200 mesh, 20-50% ethyl acetate in petroleum ether) affording (3S,4S)-tert-butyl 3-(benzyl(methyl)amino)-4-fluoropyrrolidine-1-carboxylate (2.01 g, 66.56%) as a yellow oil. LCMS Rt=0.617 min, m/z=308.2 [M+H]$^+$.

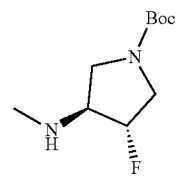

Step 2: (3S,4S)-tert-butyl 3-fluoro-4-(methylamino)pyrrolidine-1-carboxylate

The deprotection of benzyl group was prepared in a similar fashion to Method #6, Step 6. The mixture was filtered and the filtrate was concentrated in vacuo affording (3S,4S)-tert-butyl 3-fluoro-4-(methylamino)pyrrolidine-1-carboxylate (6.3 g, crude) as a yellow oil, used in next step without further purification. LCMS Rt=0.525 min, m/z=218.1 [M+H]$^+$.

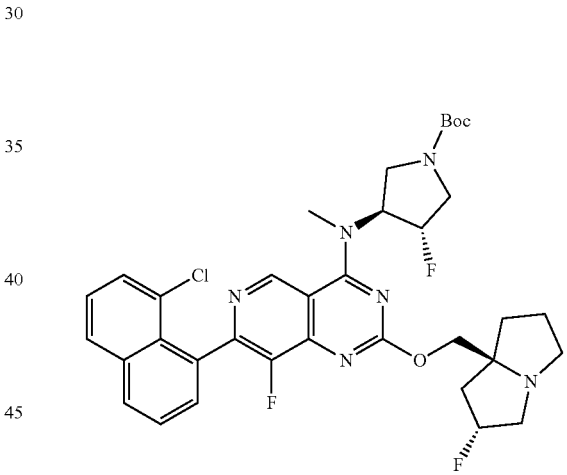

Step 3: (3S,4S)-tert-butyl 3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidine-1-carboxylate The substitution reaction was prepared in a similar fashion to Method #1, Step 8. The residue was purified by prep-HPLC (column: Phenomenex luna C18 (250*70 mm, 15 μm); mobile phase: [water (TFA)-ACN]; B %: 33%-63%, 22 min) affording (3S,4S)-tert-butyl 3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidine-1-carboxylate (270 mg, 77.70%, trifluoroacetate salt) as a white solid. LCMS Rt=0.770 min, m/z=682.3 [M+H]$^+$.

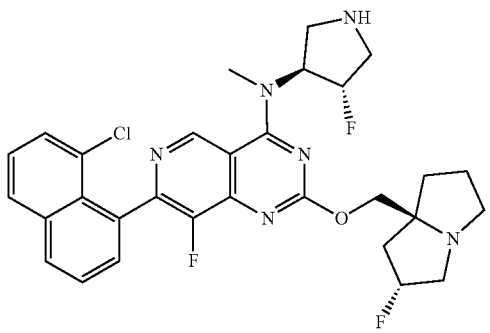 [SMILES: CN(c1nc(OC[C@@]23CCCN2C[C@H](F)C3)nc2c(F)c(-c3cccc4cccc(Cl)c34)ncc12)[C@H]1CNC[C@@H]1F]

Step 4: 7-(8-chloronaphthalen-1-yl)-8-fluoro-2-(((2R,7aS)-2-fluorohexahydro-1H-pyrrolizin-7a-yl)methoxy)-N-((3S,4S)-4-fluoropyrrolidin-3-yl)-N-methylpyrido[4,3-d]pyrimidin-4-amine The deprotection of Boc group was prepared in a similar fashion to Method #1, Step 9. The reaction mixture was concentrated in vacuo affording 7-(8-chloronaphthalen-1-yl)-8-fluoro-2-(((2R,7aS)-2-fluorohexahydro-1H-pyrrolizin-7a-yl)methoxy)-N-((3S,4S)-4-fluoropyrrolidin-3-yl)-N-methylpyrido[4,3-d]pyrimidin-4-amine (255 mg, crude, trifluoroacetic acid salt) as a yellow oil and used in next step without any further purification. LCMS Rt=0.617 min, m/z=582.2 [M+H]$^+$.

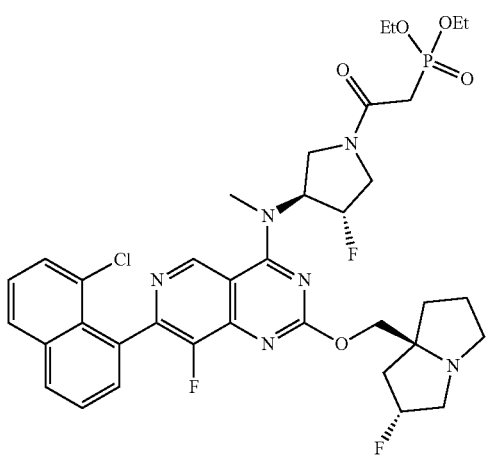 [SMILES: CCOP(=O)(CC(=O)N1C[C@H](F)[C@@H](N(C)c2nc(OC[C@@]34CCCN3C[C@H](F)C4)nc3c(F)c(-c4cccc5cccc(Cl)c45)ncc23)C1)OCC]

Step 5: diethyl (2-((3S,4S)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidin-1-yl)-2-oxoethyl)phosphonate The amide coupling reaction was prepared in a similar fashion to Method #8, Step 3. The residue was purified by prep-HPLC (column: C18-1 150*30 mm*5 μm; mobile phase: [water (TFA)-ACN]; B %: 15%-60%, 8 min) affording diethyl (2-((3S,4S)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidin-1-yl)-2-oxoethyl)phosphonate (180 mg, 54.07%, trifluoroacetate salt) as a yellow solid. LCMS Rt=0.696 min, m/z=760.3 [M+H]$^+$.

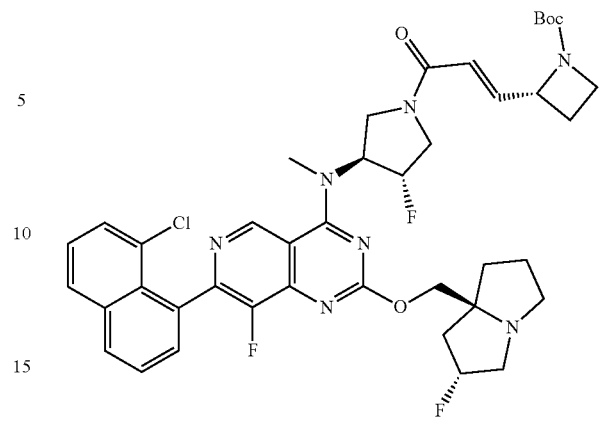

Step 6: (R)-tert-butyl 2-((E)-3-((3S,4S)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidin-1-yl)-3-oxoprop-1-en-1-yl)azetidine-1-carboxylate The Horner-Wadsworth-Emmons reaction was prepared in a similar fashion to Method #8, Step 4. The reaction mixture was concentrated in vacuo affording (R)-tert-butyl 2-((E)-3-((3S,4S)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidin-1-yl)-3-oxoprop-1-en-1-yl)azetidine-1-carboxylate (110 mg, crude) as a yellow oil and used in next step without any further purification. LCMS Rt=0.751 min, m/z=791.3 [M+H]$^+$.

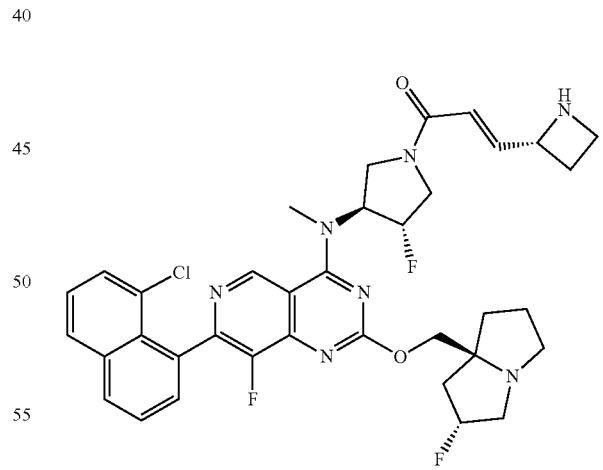

Step 7: (E)-3-((R)-azetidin-2-yl)-1-((3S,4S)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidin-1-yl)prop-2-en-1-one The deprotection of Boc group was prepared in a similar fashion to Method #11, Step 12. The reaction mixture was concentrated in vacuo affording (E)-3-((R)-azetidin-2-yl)-1-((3S,4S)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidin-1-yl)prop-2-en-1-one (100 mg, crude, trifluoroacetic acid salt) as a yellow oil and used in next step without any further purification. LCMS Rt=0.625 min, m/z=691.3 [M+H]⁺.

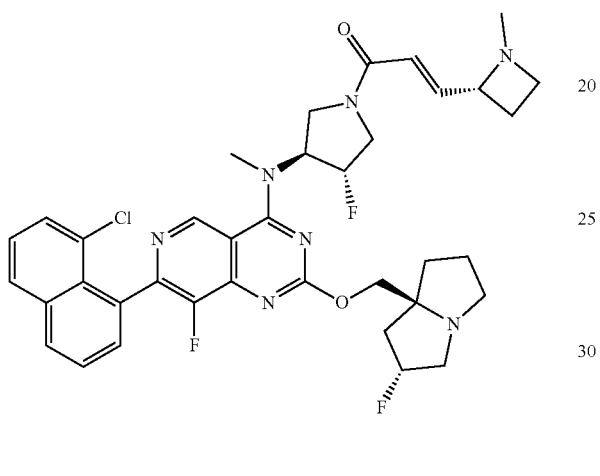

Step 8: (E)-1-((3S,4S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-((R)-1-methylazetidin-2-yl)prop-2-en-1-one The reductive amination was prepared in a similar fashion to Method #11, Step 13.

The residue was purified by prep-HPLC (column: Waters Xbridge BEH C18 100*30 mm*10 μm; mobile phase: [water (NH₄HCO₃)-ACN]; B %: 35%-65%, 8 min) affording (E)-1-((3S,4S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-((R)-1-methylazetidin-2-yl)prop-2-en-1-one (7.82 mg, 6.99%) as a white solid: ¹H NMR (400 MHz, Acetonitrile-d3) δ 9.21 (s, 1H), 8.12 (d, J=8.1 Hz, 1H), 8.02 (d, J=8.3 Hz, 1H), 7.72-7.66 (m, 1H), 7.64-7.58 (m, 2H), 7.54-7.48 (m, 1H), 6.85-6.75 (m, 1H), 6.37 (br dd, J=4.1, 15.0 Hz, 1H), 5.69-5.47 (m, 1H), 5.34-5.16 (m, 2H), 4.20-4.06 (m, 3H), 3.96-3.62 (m, 3H), 3.49 (br d, J=5.4 Hz, 3H), 3.31-3.24 (m, 1H), 3.12 (br s, 2H), 3.05 (br s, 1H), 2.93-2.75 (m, 3H), 2.24 (br d, J=9.3 Hz, 4H), 2.10-2.00 (m, 3H), 1.90-1.82 (m, 4H). LCMS Rt=2.823 min, m/z=705.3 [M+H]⁺.

LCMS (5 to 95% acetonitrile in water+0.03% ammonium bicarbonate over 6 mins) retention time 2.823 min, ESI+ found [M+H]=705.3.

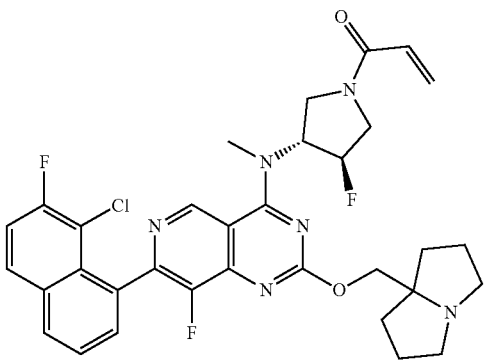 [SMILES: C=CC(=O)N1C[C@@H](F)[C@H](N(C)c2nc(OCC34CCCN3CCC4)nc3c(F)c(-c4cccc5ccc(F)c(Cl)c45)ncc23)C1]

Example 184 (Method 1): 1-((3R,4R)-3-((7-(8-chloro-7-fluoronaphthalen-1-yl)-8-fluoro-2-((hexahydro-1H-pyrrolizin-7a-yl)methoxy)pyrido[4,3-d]pyrimidin-4-yl)(methyl)amino)-4-fluoropyrrolidin-1-yl)prop-2-en-1-one

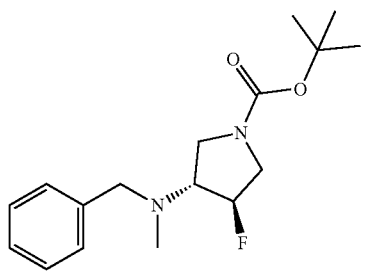 [SMILES: CN(Cc1ccccc1)[C@@H]1CN(C(=O)OC(C)(C)C)C[C@H]1F]

Step 1: (3R,4R)-tert-butyl 3-(benzyl(methyl)amino)-4-fluoropyrrolidine-1-carboxylate The reductive amination was prepared in a similar fashion to Method #6, Step 1. The residue was purified by column chromatography (silica gel, 100-200 mesh, 0-100% ethyl acetate in petroleum ether) affording (3R,4R)-tert-butyl 3-(benzyl(methyl)amino)-4-fluoropyrrolidine-1-carboxylate (15 g, 99.34%) as a colorless oil. LCMS Rt=0.627 min, m/z=308.2 [M+H]⁺.

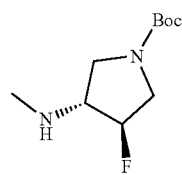

Step 2: (3R,4R)-tert-butyl 3-fluoro-4-(methylamino)pyrrolidine-1-carboxylate

The deprotection of the benzyl group was prepared in a similar fashion to Method #6, Step 6.

The mixture was concentrated in vacuo affording (3R,4R)-tert-butyl 3-fluoro-4-(methylamino)pyrrolidine-1-carboxylate (12 g, crude) as a colorless oil and used in the next step without further purification. LCMS Rt=0.525 min, m/z=218.1 [M+H]⁺.

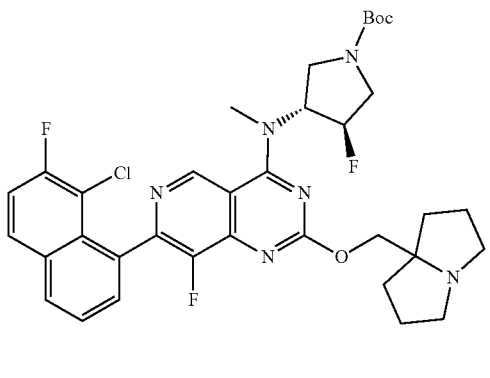 [SMILES: CN(c1nc(OCC23CCCN2CCC3)nc2c(F)c(-c3cccc4ccc(F)c(Cl)c34)ncc12)[C@@H]1CN(C(=O)OC(C)(C)C)C[C@H]1F]

Step 3: (3R,4R)-tert-butyl 3-((7-(8-chloro-7-fluoronaphthalen-1-yl)-8-fluoro-2-((hexahydro-1H-pyrrolizin-7a-yl)methoxy)pyrido[4,3-d]pyrimidin-4-yl)(methyl)amino)-4-fluoropyrrolidine-1-carboxylate The substitution reaction was prepared in a similar fashion to Method #1, Step 8. The residue was purified by reverse phase HPLC (column: Phenomenex luna C18 250*50 mm*10 μm; mobile phase: [water (TFA)-ACN]; B %: 25%-55%, 10 min) affording (3R,4R)-tert-butyl 3-((7-(8-chloro-7-fluoronaphthalen-1-yl)-8-fluoro-2-((hexahydro-1H-pyrrolizin-7a-yl)methoxy)pyrido[4,3-d]pyrimidin-4-yl)(methyl)amino)-4-fluoropyrrolidine-1-carboxylate (90 mg, 10.88%, trifluoroacetate salt) as a white solid. LCMS Rt=0.771 min, m/z=682.3 [M+H]⁺.

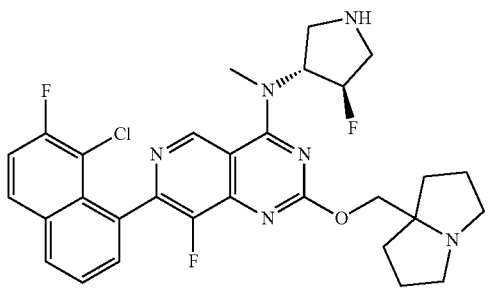 [SMILES: CN(c1nc(OCC23CCCN2CCC3)nc2c(F)c(-c3cccc4ccc(F)c(Cl)c34)ncc12)[C@@H]1CNC[C@H]1F]

Step 4: 7-(8-chloro-7-fluoronaphthalen-1-yl)-8-fluoro-N-((3R,4R)-4-fluoropyrrolidin-3-yl)-2-((hexahydro-1H-pyrrolizin-7a-yl)methoxy)-N-methylpyrido[4,3-d]pyrimidin-4-amine The de-Boc protecting reaction was prepared in a similar fashion to Method #1, Step 9. The mixture was concentrated to dryness in vacuo affording 7-(8-chloro-7-fluoronaphthalen-1-yl)-8-fluoro-N-((3R,4R)-4-fluoropyrrolidin-3-yl)-2-((hexahydro-1H-pyrrolizin-7a-yl)methoxy)-N-methylpyrido[4,3-d]pyrimidin-4-amine (80 mg, crude, trifluoroacetate salt) as a yellow oil and used in next step without any further purification. LCMS Rt=0.764 min, m/z=582.2 [M+H]⁺.

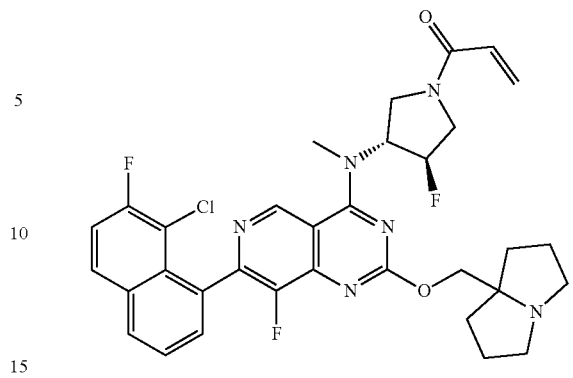

Step 5: 1-((3R,4R)-3-((7-(8-chloro-7-fluoronaphthalen-1-yl)-8-fluoro-2-((hexahydro-1H-pyrrolizin-7a-yl)methoxy)pyrido[4,3-d]pyrimidin-4-yl)(methyl)amino)-4-fluoropyrrolidin-1-yl)prop-2-en-1-one The amide coupling reaction was prepared in a similar fashion to Method #1, Step 10. The residue was purified by reverse phase HPLC (column: Phenomenex Luna C18 75*30 mm*3 μm; mobile phase: [water (FA)- Acetonitrile]; B %: 10%-40%, 8 min) affording 1-((3R,4R)-3-((7-(8-chloro-7-fluoronaphthalen-1-yl)-8-fluoro-2-((hexahydro-1H-pyrrolizin-7a-yl)methoxy)pyrido[4,3-d]pyrimidin-4-yl)(methyl)amino)-4-fluoropyrrolidin-1-yl)prop-2-en-1-one (4.94 mg, 5.75%, formate salt) as a white amorphous solid: ¹H NMR (400 MHz, Acetonitrile-d3) δ 9.32 (s, 1H), 8.36 (s, 1H), 8.18-8.23 (m, 1H), 8.14 (dd, J=9.1, 5.7 Hz, 1H), 7.71-7.78 (m, 2H), 7.59 (t, J=8.9 Hz, 1H), 6.66 (dt, J=16.8 Hz, J=10.0 Hz, 1H), 6.30-6.39 (m, 1H), 5.76-5.81 (m, 1H), 5.62 (dt, J=6.9, 3.4 Hz, 1H), 5.26-5.45 (m, 1H), 4.42 (d, J=6.3 Hz, 2H), 4.31-4.40 (m, 1H), 4.13-4.23 (m, 1H), 3.78-4.04 (m, 2H), 3.58 (t, J=5.3 Hz, 3H), 3.30 (br dd, J=9.6, 6.7 Hz, 2H), 2.79-2.87 (m, 2H), 2.12 (br dd, J=12.6, 6.1 Hz, 2H), 2.01-2.07 (m, 2H), 1.91-1.98 (m, 2H), 1.79-1.89 (m, 2H). LCMS Rt=2.722 min, m/z=636.2 [M+H]⁺.

LCMS (5 to 95% acetonitrile in water+0.03% ammonium bicarbonate over 6 mins) retention time 2.722 min, ESI+ found [M+H]=636.2.

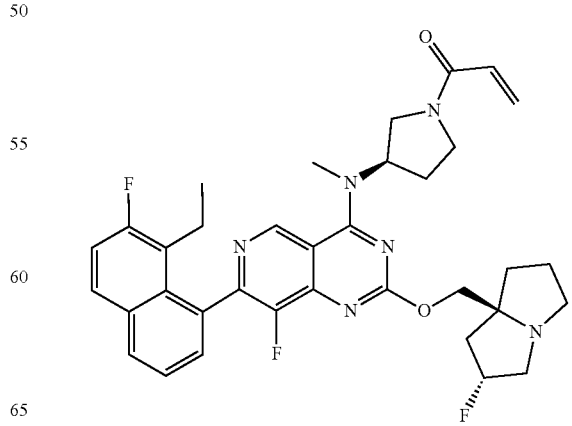

Example 185 (Method 1): 1-((R)-3-((7-(8-ethyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one

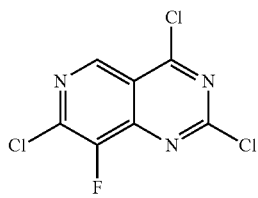 [SMILES: Fc1c(Cl)ncc2c(Cl)nc(Cl)nc12]

Step 1: 2,4,7-trichloro-8-fluoropyrido[4,3-d]pyrimidine

To a solution of 7-chloro-8-fluoropyrido[4,3-d]pyrimidine-2,4-diol (100 g, 464 mmol) and trichlorophosphate (500 mL) in anhydrous toluene (600 mL) was added N,N-diisopropylethylamine (148 g, 1.15 mol) at 0° C. under a nitrogen atmosphere. The mixture was stirred at 110° C. for 12 h. The mixture was diluted with water (5 L) and extracted with ethyl acetate (3×2 L). The reaction mixture was concentrated in vacuo affording 2,4,7-trichloro-8-fluoropyrido[4,3-d]pyrimidine (117 g, crude) as a yellow oil and used in next step without any further purification. LCMS Rt=0.725 min, m/z=251.9 [M+H]$^+$.

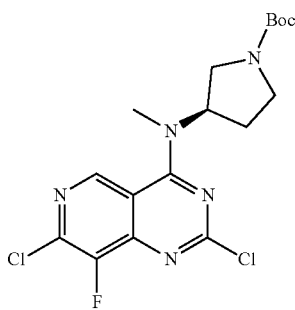 [SMILES: CN(c1nc(Cl)nc2c(F)c(Cl)ncc12)[C@@H]1CCN(C(=O)OC(C)(C)C)C1]

Step 2: (R)-tert-butyl 3-((2,7-dichloro-8-fluoropyrido[4,3-d]pyrimidin-4-yl)(methyl)amino)pyrrolidine-1-carboxylate To a solution of 2,4,7-trichloro-8-fluoropyrido[4,3-d]pyrimidine (177 g, 701 mmol) in tetrahydrofuran (2400 mL) and N,N-diisopropylethylamine (119 g, 927 mmol) was added (R)-tert-butyl 3-(methylamino)pyrrolidine-1-carboxylate (79 g, 394 mmol) at 0° C. under a nitrogen atmosphere. The mixture was stirred at 0° C. for 0.5 h. The mixture was diluted with water (5 L) and extracted with ethyl acetate (3×2 L). The combined organic layers were dried over sodium sulphate and concentrated in vacuo. The crude residue was diluted with tert-butyl methyl ether (400 mL) and the resulting precipitate was filtered affording (R)-tert-butyl 3-((2,7-dichloro-8-fluoropyrido[4,3-d]pyrimidin-4-yl)(methyl)amino)pyrrolidine-1-carboxylate (120 g, 62.18%) as a light yellow solid and used in the next step without further purification. LCMS Rt=0.798 min, m/z=416.1 [M+H]$^+$.

Step 3: (R)-tert-butyl 3-((7-chloro-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate To a solution of ((2R,7aS)-2-fluorohexahydro-1H-pyrrolizin-7a-yl)methanol (38.24 g, 240.22 mmol) and 4A MS (25 g) in dioxane (1000 mL) were added (R)-tert-butyl 3-((2,7-dichloro-8-fluoropyrido[4,3-d]pyrimidin-4-yl)(methyl)amino)pyrrolidine-1-carboxylate (50 g, 120.11 mmol) and N,N-diisopropylethylamine (46.57 g, 360.34 mmol) and the mixture was stirred at 100° C. for 24 h under a nitrogen atmosphere. The mixture was filtered and the filter cake was diluted with a mixture of petroleum ether: ethyl acetate (14 L, 2.5:1) for two times. The resulting precipitate was filtered and concentrated to dryness in vacuo affording (R)-tert-butyl 3-((7-chloro-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (160 g, crude) as a white solid and used in next step without any further purification: $^1$H NMR (400 MHz, Chloroform-d) δ 8.87 (s, 1H), 5.39-5.29 (m, 1H), 5.21 (br s, 1H), 4.32-4.25 (m, 1H), 4.24-4.15 (m, 1H), 3.82 (dd, J=11.2, 8.0 Hz, 1H), 3.66 (br d, J=4.0 Hz, 1H), 3.47-3.39 (m, 2H), 3.37 (s, 3H), 3.32-3.22 (m, 2H), 3.17 (br s, 1H), 3.04-2.93 (m, 1H), 2.34-2.08 (m, 5H), 2.04-1.78 (m, 3H), 1.49 (s, 9H). LCMS Rt=0.545 min, m/z=539.2 [M+H]$^+$.

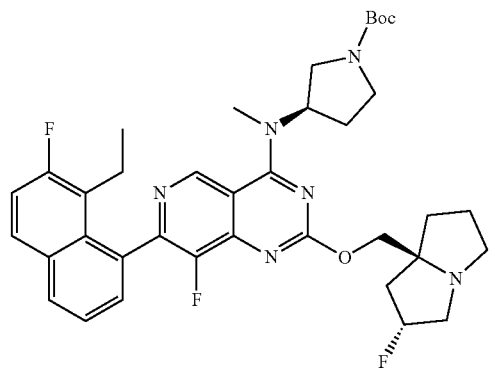 [SMILES: CCc1c(F)ccc2cccc(-c3ncc4c(N(C)[C@@H]5CCN(C(=O)OC(C)(C)C)C5)nc(OC[C@@]56CCCN5C[C@H](F)C6)nc4c3F)c12]

Step 4: tert-butyl (R)-3-((7-(8-ethyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidine-1-carboxylate A mixture of tert-butyl (R)-3-((7-chloro-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidine-1-carboxylate (2 g, 3.71 mmol), 2-(8-ethyl-7-fluoro-1-naphthyl)-4,4,5,5-tetramethyl-1,3,2-dioxaborolane (1.67 g, 5.57 mmol), potassium phosphate (2.36 g, 11.13 mmol) and Chloro(2-dicyclohexylphosphino-2',4',6'-triisopropyl-1,1'-biphenyl)[2-(2'-amino-1,1'-biphenyl)]palladium(II) (583.88 mg, 742.09 μmol) in dioxane (150 mL) and water (50 mL) was degassed and purged with nitrogen for 3 times and the mixture was stirred at 60° C. for 12 h under a nitrogen atmosphere. The reaction mixture was quenched by water (30 mL) and extracted with ethyl acetate (3×90 mL). The combined organic layers were dried over sodium sulphate and concentrated in vacuo. The result residue was purified by reverse phase HPLC (column: Welch Xtimate C18 250*70 mm* 10 um; mobile phase: [water (TFA)-ACN]; B %: 25%-55%, 20 min) affording tert-butyl (R)-3-((7-(8-ethyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidine-1-carboxylate (1 g, 34.08%, trifluoroacetate salt) as a white solid. LCMS Rt=1.596 min, m/z=677.3 [M+H]$^+$.

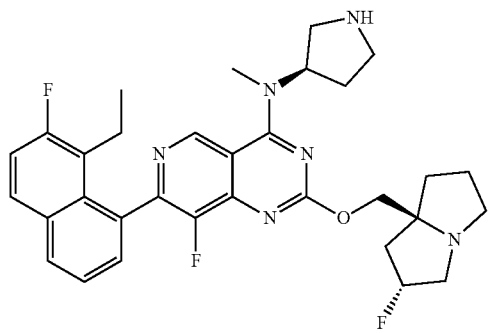 [SMILES: CCc1c(F)ccc2cccc(-c3ncc4c(N(C)[C@@H]5CCNC5)nc(OC[C@@]56CCCN5C[C@H](F)C6)nc4c3F)c12]

Step 5: 7-(8-ethyl-7-fluoronaphthalen-1-yl)-8-fluoro-2-(((2R,7aS)-2-fluorotetrahydro-1H-pyrrolizin-7a(5H)-yl)methoxy)-N-methyl-N—((R)-pyrrolidin-3-yl)pyrido[4,3-d]pyrimidin-4-amine A solution of tert-butyl (R)-3-((7-(8-ethyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidine-1-carboxylate (235 mg, 297.17 μmol, trifluoroacetate salt) in 4M hydrochloric acid in ethyl acetate (10 mL) was stirred at 25° C. for 0.5 h. The reaction mixture was concentrated to dryness in vacuo affording 7-(8-ethyl-7-fluoronaphthalen-1-yl)-8-fluoro-2-(((2R,7aS)-2-fluorotetrahydro-1H-pyrrolizin-7a(5H)-yl)methoxy)-N-methyl-N—((R)-pyrrolidin-3-yl)pyrido[4,3-d]pyrimidin-4-amine (200 mg, crude, hydrochloride salt) as a yellow solid and used in the next step without further purification. LCMS Rt=0.537 min, m/z=577.3 [M+H]$^+$.

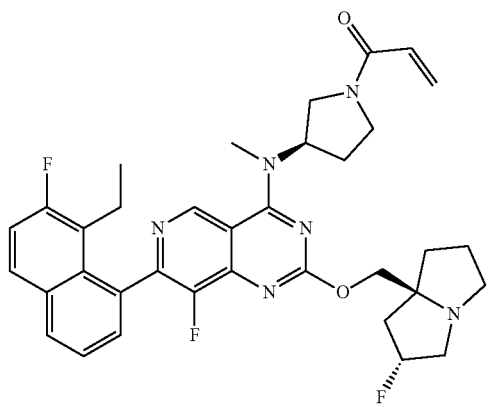 [SMILES: C=CC(=O)N1CC[C@@H](N(C)c2nc(OC[C@@]34CCCN3C[C@H](F)C4)nc3c(F)c(-c4cccc5ccc(F)c(CC)c45)ncc23)C1]

Step 6: 1-((R)-3-((7-(8-ethyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one To a solution of 7-(8-ethyl-7-fluoronaphthalen-1-yl)-8-fluoro-2-(((2R,7aS)-2-fluorotetrahydro-1H-pyrrolizin-7a(5H)-yl)methoxy)-N-methyl-N—((R)-pyrrolidin-3-yl)pyrido[4,3-d]pyrimidin-4-amine (200 mg, 326.20 μmol, hydrochloride salt) and N-ethyl-N-isopropylpropan-2-amine (210.79 mg, 1.63 mmol) in dichloromethane (2 mL) was added acrylic acid (47.01 mg, 652.41 μmol) and 2,4,6-tripropyl-1,3,5,2,4,6-trioxatriphosphinane-2,4,6-trioxide (415.17 mg, 652.41 μmol, 50% purity) (in ethyl acetate) at 0° C. The mixture was stirred at 25° C. for 1 h. The reaction mixture was concentrated in vacuo and purified by reverse phase HPLC (column: Waters Xbridge Prep OBD C18 150*40 mm*10 μm; mobile phase: [water (NH$_4$HCO$_3$)-ACN]; B %: 30%-60%, 8 min) affording 1-((R)-3-((7-(8-ethyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (83.75 mg, 40.46%) as a yellow amorphous solid: $^1$H NMR (400 MHz, Acetonitrile-d3) δ 9.19 (s, 1H), 8.05 (d, J=8.0 Hz, 1H), 7.93 (dd, J=6.1, 9.0 Hz, 1H), 7.58-7.52 (m, 1H), 7.51-7.45 (m, 1H), 7.38 (t, J=9.4 Hz, 1H), 6.66-6.52 (m, 1H), 6.24 (td, J=2.5, 16.8 Hz, 1H), 5.67 (ddd, J=2.2, 5.9, 10.3 Hz, 1H), 5.45-5.13 (m, 2H), 4.24-4.18 (m, 1H), 4.15-4.10 (m, 1H), 4.10-3.77 (m, 2H), 3.66 (br d, J=9.6 Hz, 2H), 3.42 (s, 3H), 3.19-3.08 (m, 2H), 3.06 (s, 1H), 2.94-2.84 (m, 1H), 2.56-2.43 (m, 1H), 2.42-2.34 (m, 1H), 2.33-2.21 (m, 2H), 2.20-2.16 (m, 1H), 2.10 (d, J=3.0 Hz, 1H), 2.07-2.00 (m, 1H), 1.92-1.78 (m, 3H), 0.80 (t, J=7.4 Hz, 3H). LCMS Rt=3.095 min, m/z=631.3 [M+H]$^+$.

LCMS (5 to 95% acetonitrile in water+0.03% ammonium bicarbonate over 6 mins) retention time 3.095 min, ESI+ found [M+H]=631.3.

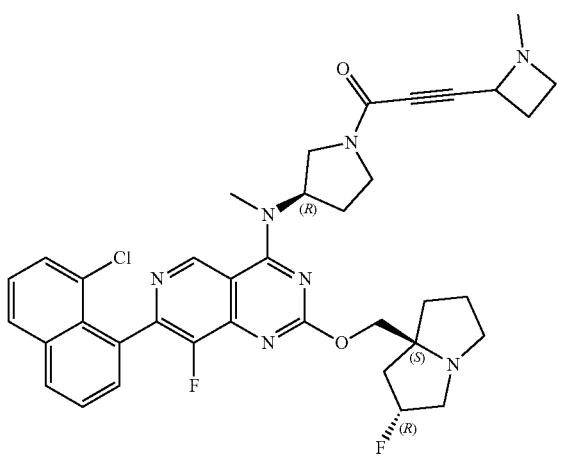

Example 186 (Method 7): 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(1-methylazetidin-2-yl)prop-2-yn-1-one

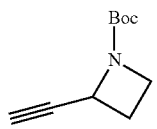

Step 1: tert-butyl 2-ethynylazetidine-1-carboxylate

To a solution of tert-butyl 2-formylazetidine-1-carboxylate (400 mg, 2.16 mmol) in methanol (5 mL) was added 1-diazo-1-dimethoxyphosphoryl-propan-2-one (622.32 mg, 3.24 mmol) and potassium carbonate (596.94 mg, 4.32 mmol) and the reaction was stirred at 20° C. for 12 h. The reaction mixture was concentrated in vacuo and purified by column chromatography (silica gel, 100-200 mesh, 10-15% ethyl acetate in petroleum ether) affording tert-butyl 2-ethynylazetidine-1-carboxylate (280 mg, 71.54%) as a yellow oil: $^1$H NMR (400 MHz, Chloroform-d) δ 4.76-4.67 (m, 1H), 3.98-3.89 (m, 1H), 3.88-3.80 (m, 1H), 2.55-2.45 (m, 2H), 2.31-2.22 (m, 1H), 1.45 (s, 9H).

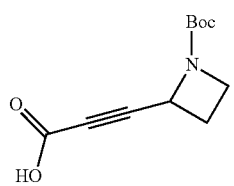 [SMILES: CC(C)(C)OC(=O)N1CCC1C#CC(=O)O]

Step 2: 3-(1-(tert-butoxycarbonyl)azetidin-2-yl)propiolic acid

To a solution of tert-butyl 2-ethynylazetidine-1-carboxylate (50 mg, 275.89 µmol) in tetrahydrofuran (1 mL) was added dropwise butyl lithium (2.5 M, 143.46 uL) at −70° C., stirred for 1 h and subsequently drikold was added (12.14 mg, 275.89 µmol). The mixture was stirred for 1 h at 20° C. The mixture was quenched with saturated ammonium chloride (1 mL) and concentrated to dryness in vacuo. The crude was triturated with methanol and filtered to give filtrate. The filtrate was concentrated to dryness in vacuo affording 3-(1-(tert-butoxycarbonyl)azetidin-2-yl)propiolic acid (75 mg, crude) as a brown oil and used in next step without any further purification.

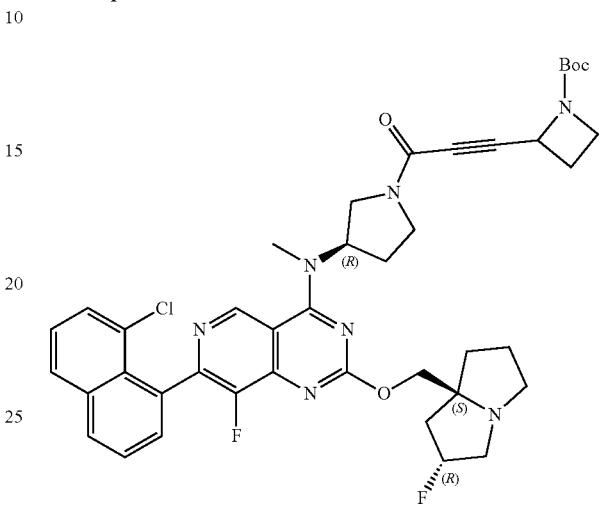

Step 3: tert-butyl 2-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)azetidine-1-carboxylate The amide coupling reaction was prepared in a similar fashion to Method #7, Step 2. The reaction mixture was concentrated in vacuo and purified by column chromatography (silica gel, 100-200 mesh, 0-10% methanol in dichloromethane) affording tert-butyl 2-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)azetidine-1-carboxylate (140 mg, 95.96%) as a yellow oil. LCMS Rt=0.677 min, m/z=771.3 [M+H]$^+$.

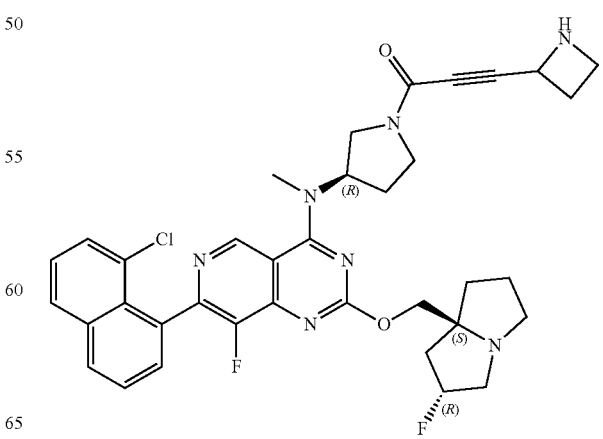

Step 4: 3-(azetidin-2-yl)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)prop-2-yn-1-one The deprotection of Boc group was prepared in a similar fashion to Method #7, Step 3. The mixture was concentrated to dryness in vacuo affording 3-(azetidin-2-yl)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)prop-2-yn-1-one (100 mg, crude, trifluoroacetate salt) as a yellow solid used in next step without any further purification.

LCMS Rt=0.531 min, m/z=671.3 [M+H]$^+$.

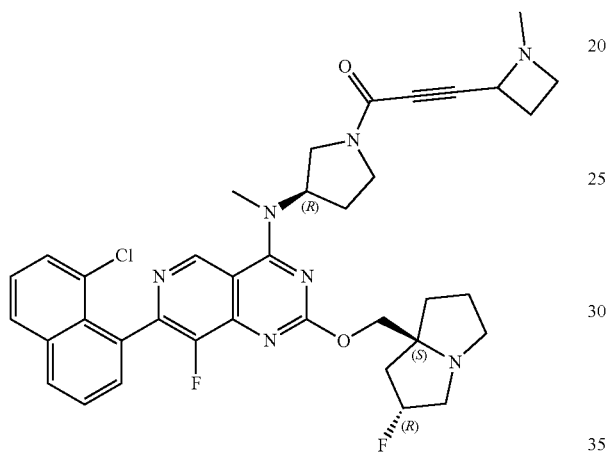

Step 6: 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(1-methylazetidin-2-yl)prop-2-yn-1-one The reductive amination was prepared in a similar fashion to Method #7, Step 4. The mixture was concentrated to dryness in vacuo and purified by reverse phase HPLC (column: Waters Xbridge Prep OBD C18 150*40 mm*10 μm; mobile phase: [water (NH$_4$HCO$_3$)-ACN]; B %: 25%-65%, 8 min) affording 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(1-methylazetidin-2-yl)prop-2-yn-1-one (12.47 mg, 12.22%) as a yellow amorphous solid: $^1$H NMR (400 MHz, Acetonitrile-d3) δ 9.21-9.14 (m, 1H), 8.12 (d, J=7.9 Hz, 1H), 8.02 (d, J=8.0 Hz, 1H), 7.72-7.66 (m, 1H), 7.65-7.59 (m, 2H), 7.54-7.49 (m, 1H), 5.43-5.15 (m, 2H), 4.21-4.12 (m, 2H), 4.02-3.62 (m, 4H), 3.51-3.40 (m, 4H), 3.27 (tdd, J=3.9, 7.7, 11.2 Hz, 1H), 3.15-3.04 (m, 3H), 2.95-2.83 (m, 2H), 2.39-2.31 (m, 2H), 2.27 (d, J=13.5 Hz, 3H), 2.22-2.17 (m, 2H), 2.10 (br d, J=2.1 Hz, 3H), 1.90-1.79 (m, 3H). LCMS Rt=2.966 min, m/z=685.3 [M+H]$^+$.

LCMS (5 to 95% acetonitrile in water+0.03% ammonium bicarbonate over 6 mins) retention time 2.966 min, ESI+ found [M+H]=685.3.

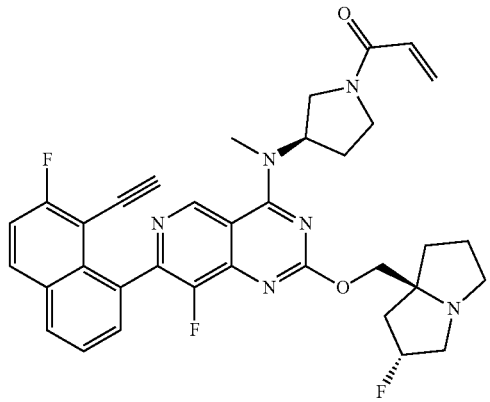 [SMILES: C#Cc1c(F)ccc2cccc(-c3ncc4c(N(C)[C@@H]5CCN(C(=O)C=C)C5)nc(OC[C@@]56CCCN5C[C@H](F)C6)nc4c3F)c12]

Example 187 (Method 1): 1-((R)-3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)prop-2-en-1-one

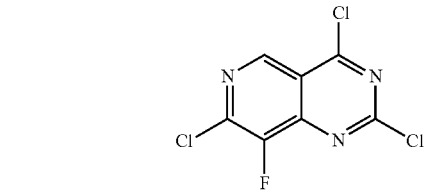 [SMILES: Fc1c(Cl)ncc2c(Cl)nc(Cl)nc12]

Step 1: 2,4,7-trichloro-8-fluoropyrido[4,3-d]pyrimidine

To a solution of 7-chloro-8-fluoropyrido[4,3-d]pyrimidine-2,4-diol (100 g, 464 mmol) and trichlorophosphate (500 mL) in anhydrous toluene (600 mL) was added N,N-diisopropylethylamine (148 g, 1.15 mol) at 0° C. under a nitrogen atmosphere. The mixture was stirred at 110° C. for 12 h. The mixture was diluted with water (5 L) and extracted with ethyl acetate (3×2 L). The reaction mixture was concentrated in vacuo affording 2,4,7-trichloro-8-fluoropyrido[4,3-d]pyrimidine (117 g, crude) as a yellow oil and used in next step without any further purification. LCMS Rt=0.725 min, m/z=251.9 [M+H]$^+$.

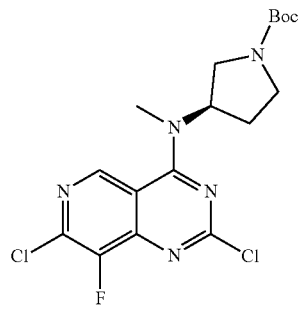 [SMILES: CN(c1nc(Cl)nc2c(F)c(Cl)ncc12)[C@@H]1CCN(C(=O)OC(C)(C)C)C1]

Step 2: (R)-tert-butyl 3-((2,7-dichloro-8-fluoro-pyrido[4,3-d]pyrimidin-4-yl)(methyl)amino)pyrrolidine-1-carboxylate To a solution of 2,4,7-trichloro-8-fluoropyrido[4,3-d]pyrimidine (177 g, 701 mmol) in tetrahydrofuran (2400 mL) and N,N-diisopropylethylamine (119 g, 927 mmol) was added (R)-tert-butyl 3-(methylamino)pyrrolidine-1-carboxylate (79 g, 394 mmol) at 0° C. under a nitrogen atmosphere. The mixture was stirred at 0° C. for 0.5 h. The mixture was diluted with water (5 L) and extracted with ethyl acetate (3×2 L). The combined organic layers were dried over sodium sulphate and concentrated in vacuo. The crude residue was diluted with tert-butyl methyl ether (400 mL) and the resulting precipitate was filtered affording (R)-tert-butyl 3-((2,7-dichloro-8-fluoropyrido[4,3-d]pyrimidin-4-yl)(methyl)amino)pyrrolidine-1-carboxylate (120 g, 62.18%) as a light yellow solid. LCMS Rt=0.798 min, m/z=416.1 [M+H]$^+$.

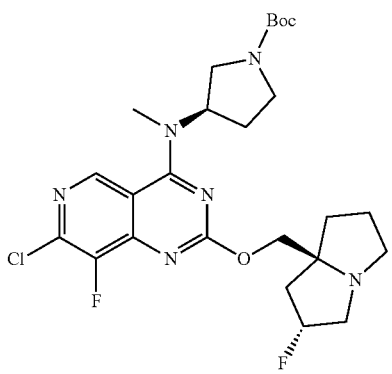 [SMILES: CN(c1nc(OC[C@@]23CCCN2C[C@H](F)C3)nc2c(F)c(Cl)ncc12)[C@@H]1CCN(C(=O)OC(C)(C)C)C1]

Step 3: (R)-tert-butyl 3-((7-chloro-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate To a solution of ((2R,7aS)-2-fluorohexahydro-1H-pyrrolizin-7a-yl)methanol (38.24 g, 240.22 mmol) and 4A MS (25 g) in dioxane (1000 mL) were added (R)-tert-butyl 3-((2,7-dichloro-8-fluoropyrido[4,3-d]pyrimidin-4-yl)(methyl)amino)pyrrolidine-1-carboxylate (50 g, 120.11 mmol) and N,N-diisopropylethylamine (46.57 g, 360.34 mmol) and the mixture was stirred at 100° C. for 24 h under a nitrogen atmosphere. The mixture was filtered and the filter cake was diluted with a mixture of petroleum ether:ethyl acetate (14 L, 2.5:1) twice. The resulting precipitate was filtered and concentrated to dryness in vacuo affording (R)-tert-butyl 3-((7-chloro-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (160 g, crude) as a white solid and used in next step without any further purification: $^1$H NMR (400 MHz, Chloroform-d) δ 8.87 (s, 1H), 5.39-5.29 (m, 1H), 5.21 (br s, 1H), 4.32-4.25 (m, 1H), 4.24-4.15 (m, 1H), 3.82 (dd, J=11.2, 8.0 Hz, 1H), 3.66 (br d, J=4.0 Hz, 1H), 3.47-3.39 (m, 2H), 3.37 (s, 3H), 3.32-3.22 (m, 2H), 3.17 (br s, 1H), 3.04-2.93 (m, 1H), 2.34-2.08 (m, 5H), 2.04-1.78 (m, 3H), 1.49 (s, 9H). LCMS Rt=0.545 min, m/z=539.2 [M+H]$^+$.

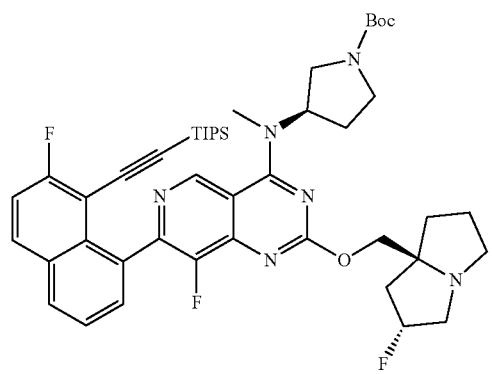

Step 4: (R)-tert-butyl 3-((8-fluoro-7-(7-fluoro-8-((triisopropylsilyl)ethynyl)naphthalen-1-yl)-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate To a solution of (R)-tert-butyl 3-((7-chloro-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (21.34 g, 39.59 mmol) in dioxane (500 mL) and water (100 mL) was added [2-fluoro-8-(4,4,5,5-tetramethyl-1,3,2-dioxaborolan-2-yl)-1-naphthyl]ethynyl-triisopropyl-silane (18.81 g, 41.57 mmol), potassium phosphate (25.21 g, 118.77 mmol) and [2-(2-aminophenyl)phenyl]-chloro-palladium; Bis(1-adamantyl)-butyl-phosphane (2.65 g, 3.96 mmol), the resulting mixture was heated to 90° C. and stirred for 12 h under a nitrogen atmosphere. The mixture was poured into water (200 mL) and concentrated under reduced pressure to remove dioxane, diluted with water (500 mL) and extracted with ethyl acetate (3×300 mL). The combined organic layers were dried over sodium sulphate and concentrated in vacuo. The residue was purified by column chromatography (silica gel, 100-200 mesh, 0-100% tetrahydrofuran in petroleum ether). The product was dissolved into ethyl acetate (220 mL) followed by the addition of 2-silylethanethiol (10 g, 108.42 mmol), then the mixture was stirred at 75° C. for 12 h to remove residue Pd. The reaction mixture was filtered and the filter cake was concentrated to dryness in vacuo affording (R)-tert-butyl 3-((8-fluoro-7-(7-fluoro-8-((triisopropylsilyl)ethynyl)naphthalen-1-yl)-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (25 g, 76.16%) as a yellow solid. LCMS Rt=0.872 min, m/z=829.4 [M+H]$^+$.

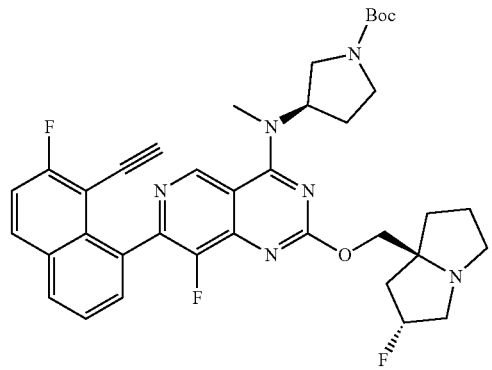 [SMILES: C#Cc1c(F)ccc2cccc(-c3ncc4c(N(C)[C@@H]5CCN(C(=O)OC(C)(C)C)C5)nc(OC[C@@]56CCCN5C[C@H](F)C6)nc4c3F)c12]

Step 5: (R)-tert-butyl 3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate To a solution of (R)-tert-butyl 3-((8-fluoro-7-(7-fluoro-8-((triisopropylsilyl)ethynyl)naphthalen-1-yl)-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (7 g, 8.44 mmol) in acetonitrile (120 mL) was added cesium fluoride (7.70 g, 50.66 mmol), the mixture was stirred at 25° C. for 12 h. To the reaction mixture was added water (200 ml) and concentrated under reduced pressure to remove acetonitrile, diluted further with water (100 mL) and extracted with ethyl acetate (3×100 mL). The combined organic layers were dried over sodium sulphate and concentrated in vacuo. The residue was diluted with a mixture of petroleum ether: ethyl acetate (180 mL, 5:1) twice. The resulting precipitate was filtered and concentrated to dryness in vacuo affording (R)-tert-butyl 3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (4.5 g, 79.23%) as a yellow solid: $^1$H NMR (400 MHz, Chloroform-d) δ 9.12 (s, 1H), 8.00-7.93 (m, 2H), 7.59 (br d, J=7.8 Hz, 2H), 7.34 (t, J=8.8 Hz, 1H), 5.41-5.33 (m, 1H), 5.22 (br s, 1H), 4.34-4.27 (m, 1H), 4.25-4.20 (m, 1H), 3.91-3.83 (m, 1H), 3.74-3.63 (m, 1H), 3.47-3.39 (m, 5H), 3.31-3.23 (m, 2H), 3.21-3.16 (m, 1H), 3.03-2.95 (m, 1H), 2.90-2.84 (m, 1H), 2.29 (br s, 1H), 2.26-2.19 (m, 2H), 2.14 (br d, J=10.8 Hz, 1H), 1.95 (dt, J=5.0, 11.3 Hz, 4H), 1.50 (s, 9H). LCMS Rt=0.673 min, m/z=673.3 [M+H]$^+$.

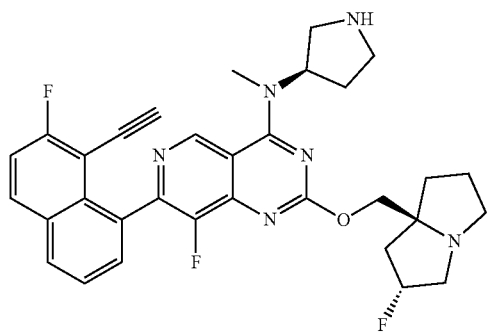 [SMILES: C#Cc1c(F)ccc2cccc(-c3ncc4c(N(C)[C@@H]5CCNC5)nc(OC[C@@]56CCCN5C[C@H](F)C6)nc4c3F)c12]

Step 6: 7-(8-ethynyl-7-fluoronaphthalen-1-yl)-8-fluoro-2-(((2R,7aS)-2-fluorohexahydro-1H-pyrrolizin-7a-yl)methoxy)-N-methyl-N—((R)-pyrrolidin-3-yl)pyrido[4,3-d]pyrimidin-4-amine A mixture of (R)-tert-butyl 3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (5 g, 7.43 mmol) in hydrochloric acid/dioxane (4M, 80 mL) was stirred at 25° C. for 1 h. The reaction mixture was concentrated in vacuo affording 7-(8-ethynyl-7-fluoronaphthalen-1-yl)-8-fluoro-2-(((2R,7aS)-2-fluorohexahydro-1H-pyrrolizin-7a-yl)methoxy)-N-methyl-N—((R)-pyrrolidin-3-yl)pyrido[4,3-d]pyrimidin-4-amine (4.8 g, crude, 2 hydrochloride salt) as a yellow solid and used in next step without any further purification. LCMS Rt=0.558 min, m/z=573.3 [M+H]$^+$.

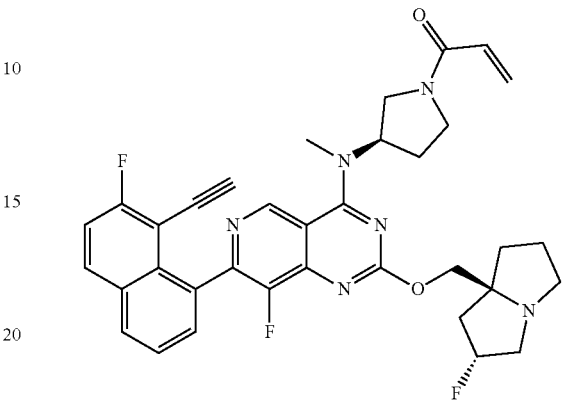

Step 7: 1-((R)-3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)prop-2-en-1-one To a solution of 7-(8-ethynyl-7-fluoronaphthalen-1-yl)-8-fluoro-2-(((2R,7aS)-2-fluorohexahydro-1H-pyrrolizin-7a-yl)methoxy)-N-methyl-N—((R)-pyrrolidin-3-yl)pyrido[4,3-d]pyrimidin-4-amine (50 g, 77.45 mmol, double hydrochloride salt) in tetrahydrofuran (1.5 L) and water (0.3 L) was added sodium bicarbonate (50.26 g, 619.63 mmol) and prop-2-enoyl chloride (14.02 g, 154.91 mmol) at 0° C. under a nitrogen atmosphere. The mixture was stirred at 0° C. for 0.5 h under a nitrogen atmosphere. The mixture was diluted with water (1.5 L) and extracted with ethyl acetate (3×1 L). The combined organic layers were dried over sodium sulphate and concentrated in vacuo. The residue was triturated in a mixture of ethyl acetate: petroleum ether (1:1, 1 L) overnight and filtered. The filter cake was dried and triturated in a mixture of ethyl acetate: ethanol (8:1, 600 mL) and then filtered. The filter cake was dried and then dissolved into ethyl acetate: ethanol (5:1, 500 mL) at 60° C., followed by addition of petroleum ether (500 mL) to form a supersaturated solution and filtered. The filtrate was cooled down and petroleum ether (500 mL) was added slowly. The resulting precipitate was filtered affording 1-((R)-3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)prop-2-en-1-one (26 g, 53.57%) as a light yellow solid: $^1$H NMR (400 MHz, Acetonitrile-d3) δ 9.17-9.14 (m, 1H), 8.14-8.09 (m, 2H), 7.69-7.64 (m, 2H), 7.45 (t, J=9.0 Hz, 1H), 6.59 (dt, J=10.4, 16.0 Hz, 1H), 6.24 (td, J=2.5, 16.8 Hz, 1H), 5.67 (ddd, J=2.4, 5.2, 10.2 Hz, 1H), 5.42-5.30 (m, 1H), 5.19 (br s, 1H), 4.22-4.17 (m, 1H), 4.14-4.09 (m, 1H), 4.09-3.79 (m, 2H), 3.74-3.45 (m, 2H), 3.43 (s, 3H), 3.28-3.22 (m, 1H), 3.19-3.08 (m, 2H), 3.06 (s, 3H), 2.93-2.85 (m, 1H), 2.43-2.25 (m, 2H), 2.11-2.00 (m, 3H), 1.91-1.78 (m, 3H). LCMS Rt=3.787 min, m/z=627.3 [M+H]$^+$.

LCMS (5 to 95% acetonitrile in water+0.03% ammonium bicarbonate over 6 mins) retention time 3.787 min, ESI+ found [M+H]=627.3.

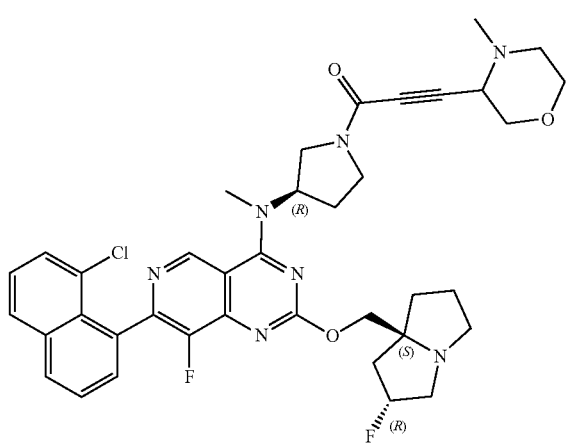

Example 188 (Method 7): 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(4-methylmorpholin-3-yl)prop-2-yn-1-one

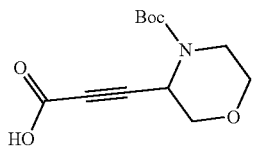 [SMILES: CC(C)(C)OC(=O)N1CCOCC1C#CC(=O)O]

Step 1:
3-(4-(tert-butoxycarbonyl)morpholin-3-yl)propiolic acid

The carbonylation reaction was prepared in a similar fashion to Method #7, Step 1. The aqueous layer was concentrated to dryness in vacuo affording 3-(4-(tert-butoxycarbonyl)morpholin-3-yl)propiolic acid (90 mg, crude) as colourless oil and used in the next step without further purification: $^1$H NMR (400 MHz, Chloroform-d) δ 4.99-4.64 (m, 1H), 4.00-3.79 (m, 2H), 3.74-3.51 (m, 2H), 3.30-3.15 (m, 2H), 1.50-1.31 (m, 9H).

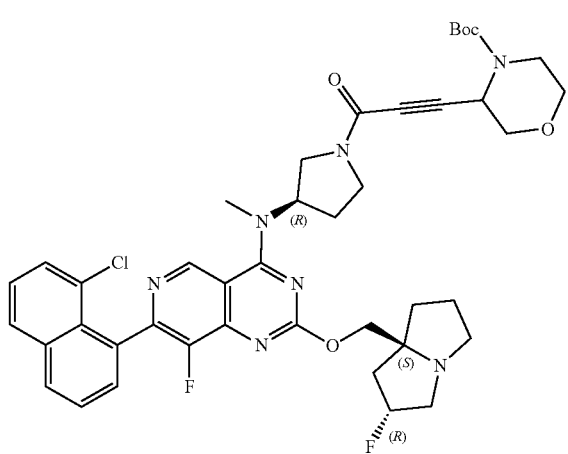

Step 2: tert-butyl 3-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)morpholine-4-carboxylate The amide coupling reaction was prepared in a similar fashion to Method #7, Step 2. The reaction mixture was concentrated to dryness in vacuo affording tert-butyl 3-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)morpholine-4-carboxylate (140 mg, crude) as a yellow oil used in next step without any further purification. LCMS Rt=0.661 min, m/z=801.3 [M+H]$^+$.

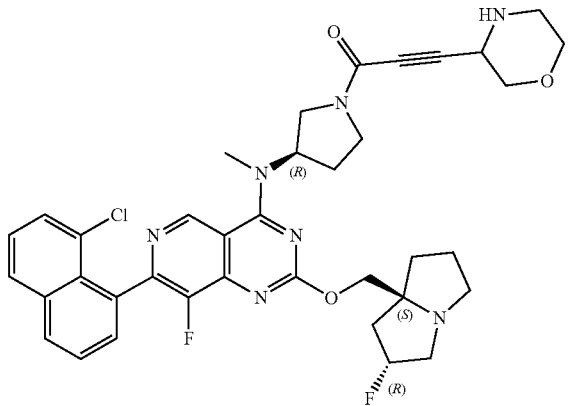

Step 4: 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(morpholin-3-yl)prop-2-yn-1-one The deprotection of Boc group was prepared in a similar fashion to Method #7, Step 3. The mixture was concentrated to dryness in vacuo affording 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(morpholin-3-yl)prop-2-yn-1-one (100 mg, crude, trifluoroacetate salt) as a yellow oil and used in next step without any further purification. LCMS Rt=0.547 min, m/z=701.3 [M+H]$^+$.

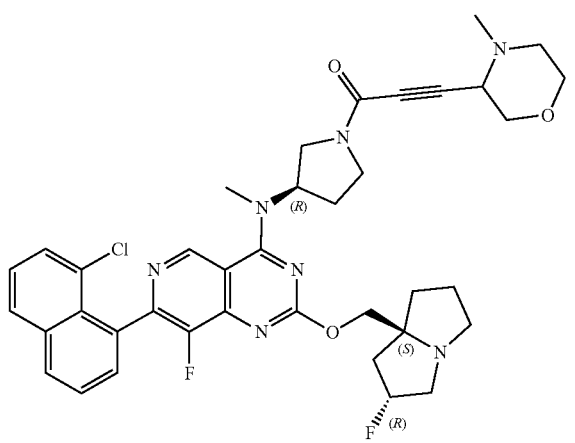

Step 5: 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(4-methylmorpholin-3-yl)prop-2-yn-1-one The reductive amination was prepared in a similar fashion to Method #7, Step 4. The mixture was concentrated to dryness in vacuo and purified by reverse phase HPLC (column: Waters Xbridge Prep OBD C18 150*40 mm*10 μm; mobile phase: [water (NH$_4$HCO$_3$)-ACN]; B %: 25%-65%, 8 min) affording 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(4-methylmorpholin-3-yl)prop-2-yn-1-one (19.50 mg, 22.94%) as a pale yellow amorphous solid: $^1$H NMR (400 MHz, Acetonitrile-d3) δ 9.22-9.14 (m, 1H), 8.12 (d, J=8.0 Hz, 1H), 8.02 (d, J=7.9 Hz, 1H), 7.72-7.65 (m, 1H), 7.65-7.57 (m, 2H), 7.54-7.48 (m, 1H), 5.42-5.17 (m, 2H), 4.21-4.13 (m, 2H), 4.02-3.86 (m, 1H), 3.77-3.60 (m, 5H), 3.50-3.39 (m, 5H), 3.17-3.03 (m, 3H), 2.93-2.85 (m, 1H), 2.68-2.56 (m, 1H), 2.37-2.30 (m, 5H), 2.13-1.96 (m, 4H), 1.92-1.75 (m, 4H). LCMS Rt=2.916 min, m/z=715.3 [M+H]$^+$.

LCMS (5 to 95% acetonitrile in water+0.03% ammonium bicarbonate over 6 mins) retention time 2.916 min, ESI+ found [M+H]=715.3.

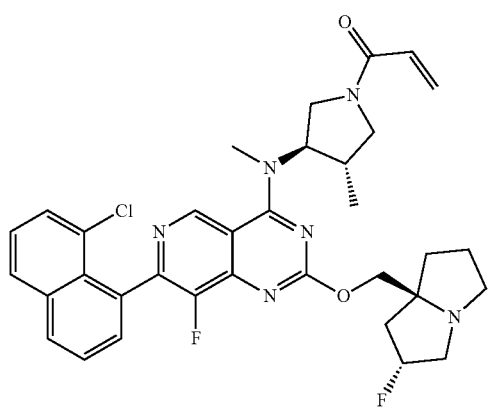 [SMILES: C=CC(=O)N1C[C@H](C)[C@@H](N(C)c2nc(OC[C@@]34CCCN3C[C@H](F)C4)nc3c(F)c(-c4cccc5cccc(Cl)c45)ncc23)C1]

Example 189 (Method 1): 1-((3R,4S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-methylpyrrolidin-1-yl)prop-2-en-1-one

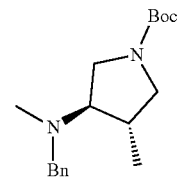 [SMILES: C[C@H]1CN(C(=O)OC(C)(C)C)C[C@@H]1N(C)Cc1ccccc1]

Step 1: tert-butyl (3R,4S)-3-(benzyl(methyl)amino)-4-methylpyrrolidine-1-carboxylate The reductive amination was prepared in a similar fashion to Method #6, Step 1. The residue was purified by column chromatography (silica gel, 100-200 mesh, 0-10% ethyl acetate in petroleum ether) affording tert-butyl (3R,4S)-3-(benzyl(methyl)amino)-4-methylpyrrolidine-1-carboxylate (1.9 g, 86.21%) as a colorless oil. LCMS Rt=0.613 min, m/z=304.2 [M+H]$^+$.

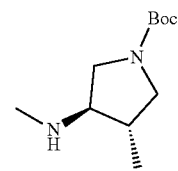

Step 2: tert-butyl (3S,4R)-3-methyl-4-(methylamino)pyrrolidine-1-carboxylate

The deprotection of the benzyl group was prepared in a similar fashion to Method #6, Step 6.

The mixture was filtered and concentrated in vacuo affording tert-butyl (3S,4R)-3-methyl-4-(methylamino)pyrrolidine-1-carboxylate (1.1 g, crude) as a colorless oil and used in next step without any further purification.

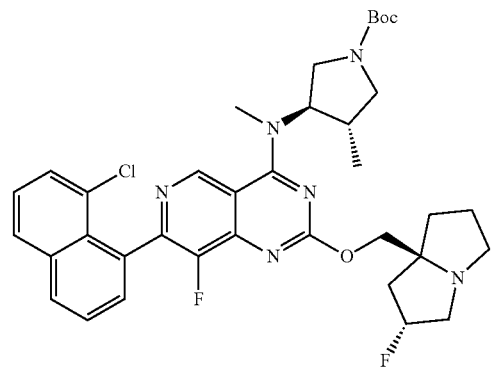 [SMILES: C[C@H]1CN(C(=O)OC(C)(C)C)C[C@@H]1N(C)c1nc(OC[C@@]23CCCN2C[C@H](F)C3)nc2c(F)c(-c3cccc4cccc(Cl)c34)ncc12]

Step 3: tert-butyl (3R,4S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-methylpyrrolidine-1-carboxylate The substitution reaction was prepared in a similar fashion to Method #1, Step 8. The residue was purified by reverse phase HPLC (column: Phenomenex luna C18 250*50 mm*10 μm; mobile phase: [water (TFA)-ACN]; B %: 30%-70%, 10 min) affording tert-butyl (3R,4S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-methylpyrrolidine-1-carboxylate (140 mg, 22.12%, trifluoroacetate salt) as a white solid. LCMS Rt=0.782 min, m/z=678.3 [M+H]⁺.

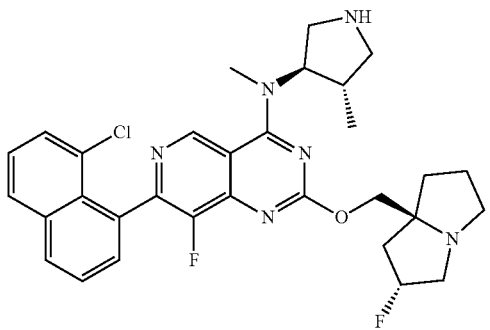 [SMILES: C[C@H]1CNC[C@@H]1N(C)c1nc(OC[C@@]23CCCN2C[C@H](F)C3)nc2c(F)c(-c3cccc4cccc(Cl)c34)ncc12]

Step 4: 7-(8-chloronaphthalen-1-yl)-8-fluoro-2-(((2R,7aS)-2-fluorotetrahydro-1H-pyrrolizin-7a(5H)-yl)methoxy)-N-methyl-N-((3R,4S)-4-methylpyrrolidin-3-yl)pyrido[4,3-d]pyrimidin-4-amine The de-Boc protecting reaction was prepared in a similar fashion to Method #1, Step 9. The reaction mixture was concentrated in vacuo affording 7-(8-chloronaphthalen-1-yl)-8-fluoro-2-(((2R,7aS)-2-fluorotetrahydro-1H-pyrrolizin-7a(5H)-yl)methoxy)-N-methyl-N-((3R,4S)-4-methylpyrrolidin-3-yl)pyrido[4,3-d]pyrimidin-4-amine (90 mg, crude, trifluoroacetate salt) as a yellow oil and used in the next step without further purification. LCMS Rt=0.632 min, m/z=578.2 [M+H]⁺.

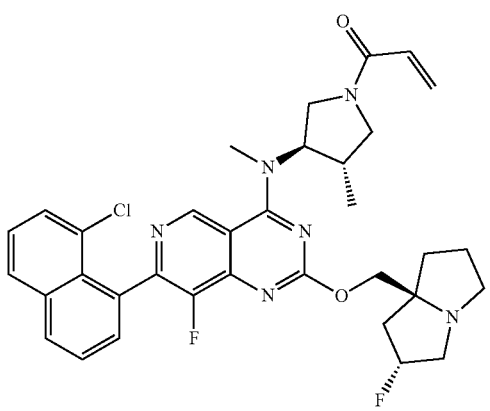 [SMILES: C=CC(=O)N1C[C@H](C)[C@@H](N(C)c2nc(OC[C@@]34CCCN3C[C@H](F)C4)nc3c(F)c(-c4cccc5cccc(Cl)c45)ncc23)C1]

Step 5: 1-((3R,4S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-methylpyrrolidin-1-yl)prop-2-en-1-one The amide coupling reaction was prepared in a similar fashion to Method #1, Step 10. The residue was purified by reverse phase HPLC (column: Waters Xbridge Prep OBD C18 150*40 mm*10 μm; mobile phase: [water (NH₄HCO₃)-ACN]; B %: 40%-60%, 8 min) affording 1-((3R,4S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-methylpyrrolidin-1-yl)prop-2-en-1-one (35.99 mg, 43.78%) as a white solid: ¹H NMR (400 MHz, Acetonitrile-d3) δ 9.28-9.25 (m, 1H), 8.15 (d, J=8.0 Hz, 1H), 8.04 (d, J=7.6 Hz, 1H), 7.74-7.64 (m, 2H), 7.64-7.60 (m, 1H), 7.57-7.50 (m, 1H), 6.60 (td, J=10.7, 16.8 Hz, 1H), 6.32-6.20 (m, 1H), 5.75-5.65 (m, 1H), 5.36-5.18 (m, 1H), 5.06-4.92 (m, 1H), 4.27-4.21 (m, 1H), 4.19-4.14 (m, 1H), 4.03-3.95 (m, 1H), 3.70-3.51 (m, 1H), 3.48-3.43 (m, 3H), 3.28 (dt, J=1.7, 10.0 Hz, 1H), 3.17 (br d, J=9.1 Hz, 2H), 3.11-3.04 (m, 1H), 2.97-2.88 (m, 1H), 2.81-2.63 (m, 1H), 2.20-2.15 (m, 1H), 2.16 (br s, 1H), 2.17-2.03 (m, 2H), 1.93-1.80 (m, 3H), 1.18-1.09 (m, 3H). LCMS Rt=2.206 min, m/z=632.3 [M+H]⁺.

LCMS (5 to 95% acetonitrile in water+0.03% ammonium bicarbonate over 6 mins) retention time 2.206 min, ESI+ found [M+H]=632.3.

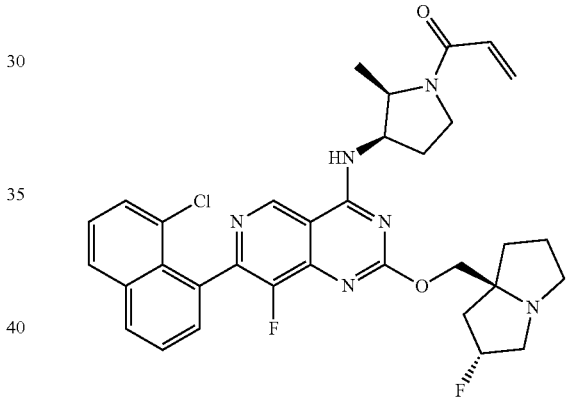

Example 190 (Method 1): 1-((2R,3R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)-2-methylpyrrolidin-1-yl)prop-2-en-1-one

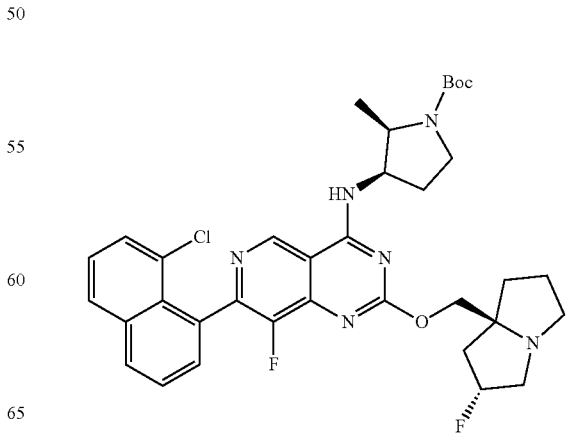

Step 1: tert-butyl (2R,3R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)-2-methylpyrrolidine-1-carboxylate The substitution reaction was prepared in a similar fashion to Method #1, Step 8. The residue was purified by reverse phase HPLC (column: Phenomenex C18 80*30 mm*3 μm; mobile phase: [water (TFA)-ACN]; B %: 25%-55%, 8 min) affording tert-butyl (2R,3R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)-2-methylpyrrolidine-1-carboxylate (80 mg, 30.15%, trifluoroacetate salt) as a white solid. LCMS Rt=0.763 min, m/z=664.3 [M+H]$^+$.

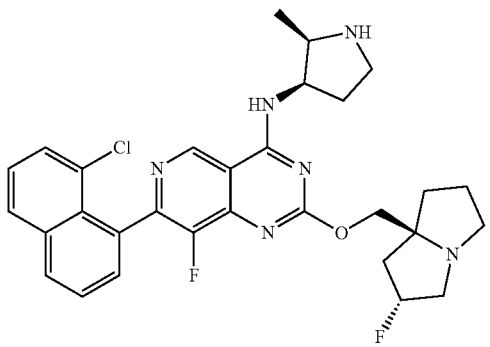 [SMILES: C[C@H]1NCC[C@H]1Nc1nc(OC[C@@]23CCCN2C[C@H](F)C3)nc2c(F)c(-c3cccc4cccc(Cl)c34)ncc12]

Step 2: 7-(8-chloronaphthalen-1-yl)-8-fluoro-2-(((2R,7aS)-2-fluorotetrahydro-1H-pyrrolizin-7a(5H)-yl)methoxy)-N-((2R,3R)-2-methylpyrrolidin-3-yl)pyrido[4,3-d]pyrimidin-4-amine The de-Boc protecting reaction was prepared in a similar fashion to Method #1, Step 9. The reaction mixture was concentrated in vacuo affording 7-(8-chloronaphthalen-1-yl)-8-fluoro-2-(((2R,7aS)-2-fluorotetrahydro-1H-pyrrolizin-7a(5H)-yl)methoxy)-N-((2R,3R)-2-methylpyrrolidin-3-yl)pyrido[4,3-d]pyrimidin-4-amine (50 mg, crude, trifluoroacetate salt) as a yellow solid, used in the next step without further purification. LCMS Rt=0.618 min, m/z=564.2 [M+H]$^+$.

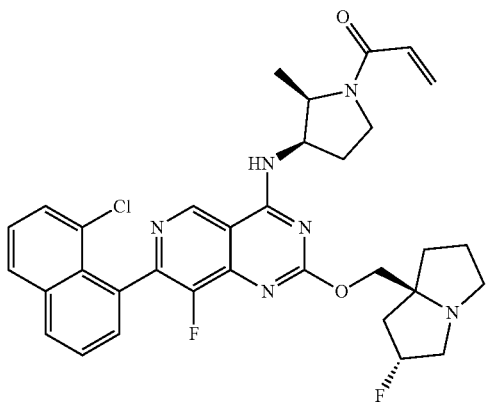 [SMILES: C=CC(=O)N1CC[C@@H](Nc2nc(OC[C@@]34CCCN3C[C@H](F)C4)nc3c(F)c(-c4cccc5cccc(Cl)c45)ncc23)[C@H]1C]

Step 3: 1-((2R,3R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)-2-methylpyrrolidin-1-yl)prop-2-en-1-one The amide coupling reaction was prepared in a similar fashion to Method #1, Step 10. The residue was purified by reverse phase HPLC (column: Waters Xbridge BEH C18 100*30 mm*10 μm; mobile phase: [water (NH$_4$HCO$_3$)-ACN]; B %: 40%-70%, 8 min) affording 1-((2R,3R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)-2-methylpyrrolidin-1-yl)prop-2-en-1-one (5.02 mg, 9.05%) as a yellow solid: $^1$H NMR (400 MHz, Acetonitrile-d3) δ 9.08 (d, J=4.6 Hz, 1H), 8.06 (d, J=8.0 Hz, 1H), 7.95 (d, J=8.1 Hz, 1H), 7.65-7.59 (m, 1H), 7.54 (br d, J=6.3 Hz, 2H), 7.49-7.42 (m, 1H), 7.35-7.24 (m, 1H), 6.59-6.47 (m, 1H), 6.20 (br dd, J=7.3, 16.6 Hz, 1H), 5.64-5.57 (m, 1H), 5.29-5.09 (m, 1H), 4.66-4.56 (m, 1H), 4.19-4.11 (m, 1H), 4.10-4.01 (m, 1H), 3.79-3.69 (m, 1H), 3.61-3.51 (m, 1H), 3.08 (br d, J=7.3 Hz, 2H), 3.01 (s, 1H), 2.88-2.79 (m, 1H), 2.34-2.23 (m, 2H), 2.07-1.96 (m, 3H), 1.85-1.75 (m, 3H), 1.07-0.98 (m, 3H). LCMS Rt=2.945 min, m/z=618.2 [M+H]$^+$.

LCMS (5 to 95% acetonitrile in water+0.03% ammonium bicarbonate over 6 mins) retention time 2.945 min, ESI+ found [M+H]=618.2.

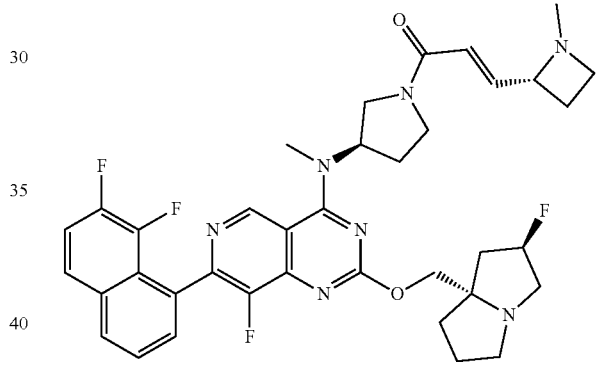

Example 191 (Method 11): (E)-1-((R)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-methylazetidin-2-yl)prop-2-en-1-one

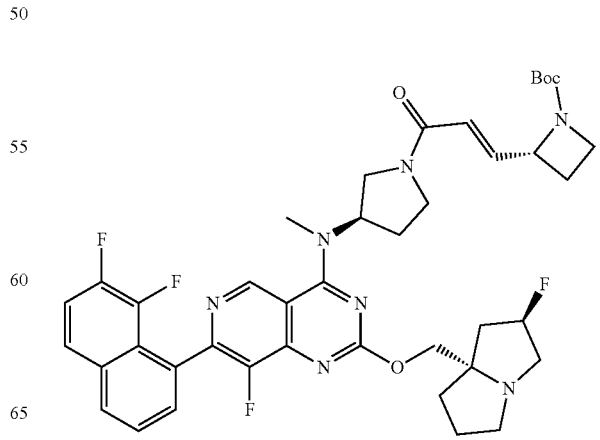

Step 1: tert-butyl (R)-2-((E)-3-((R)-3-((7-(7, 8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-oxoprop-1-en-1-yl)azetidine-1-carboxylate The amide coupling reaction was prepared in a similar fashion to Method #11, Step 11. The resulting residue was purified by column chromatography (silica gel, 100-200 mesh, 0-10% methanol in dichloromethane) affording tert-butyl (R)-2-((E)-3-((R)-3-((7-(7, 8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-oxoprop-1-en-1-yl)azetidine-1-carboxylate (530 mg, 58.12%) as a yellow gum. LCMS Rt=0.691 min, m/z=775.4 [M+H]⁺.

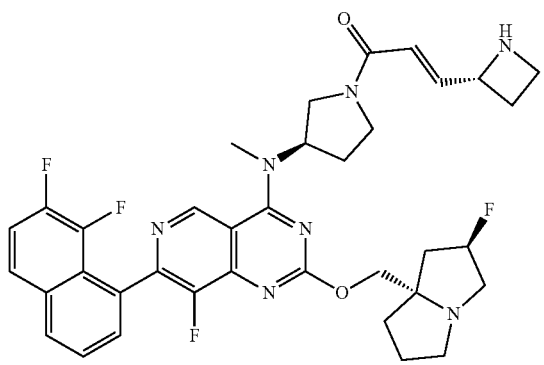 [SMILES: CN(c1nc(OC[C@@]23CCCN2C[C@H](F)C3)nc2c(F)c(-c3cccc4ccc(F)c(F)c34)ncc12)[C@@H]1CCN(C(=O)/C=C/[C@H]2CCN2)C1]

Step 2: (E)-3-((R)-azetidin-2-yl)-1-((R)-3-((7-(7, 8-difluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)prop-2-en-1-one The deprotection of Boc group was prepared in a similar fashion to Method #11, Step 12. The reaction mixture was concentrated in vacuo affording (E)-3-((R)-azetidin-2-yl)-1-((R)-3-((7-(7, 8-difluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)prop-2-en-1-one (530 mg, crude, trifluoroacetic acid salt) as a yellow oil and used in next step without any further purification. LCMS Rt=0.515 min, m/z=675.3 [M+H]⁺.

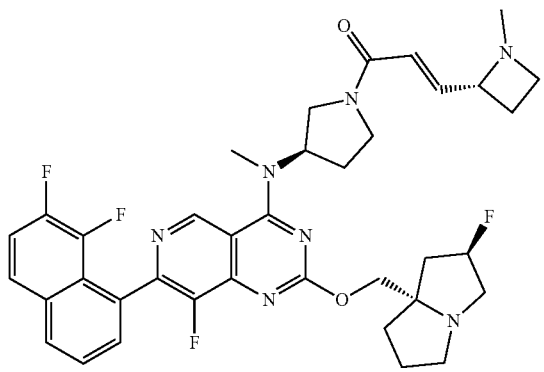 [SMILES: CN1CC[C@@H]1/C=C/C(=O)N1CC[C@@H](N(C)c2nc(OC[C@@]34CCCN3C[C@H](F)C4)nc3c(F)c(-c4cccc5ccc(F)c(F)c45)ncc23)C1]

Step 3: (E)-1-((R)-3-((7-(7, 8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-methylazetidin-2-yl)prop-2-en-1-one The reductive amination was prepared in a similar fashion to Method #11, Step 13. The residue was purified by prep-HPLC (column: Waters Xbridge Prep OBD C18 150*40 mm*10 um; mobile phase: [water (NH₄HCO₃)-ACN]; B %: 30%-60%, 8 min) affording (E)-1-((R)-3-((7-(7, 8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-methylazetidin-2-yl)prop-2-en-1-one (101.33 mg, 21.89%) as a yellow solid: ¹H NMR (400 MHz, Chloroform-d) δ 9.17 (s, 1H), 7.97 (br d, J=8.3 Hz, 1H), 7.72 (ddd, J=1.9, 4.5, 6.7 Hz, 1H), 7.68-7.57 (m, 2H), 7.45-7.36 (m, 1H), 7.06-6.93 (m, 1H), 6.37 (br dd, J=12.4, 14.6 Hz, 1H), 5.53-5.40 (m, 1H), 5.38-5.19 (m, 1H), 4.34-3.95 (m, 4H), 3.74-3.56 (m, 3H), 3.49-3.39 (m, 4H), 3.36-3.17 (m, 3H), 3.07-2.83 (m, 2H), 2.54-2.41 (m, 1H), 2.39-2.29 (m, 5H), 2.26-2.14 (m, 3H), 2.05-1.90 (m, 4H). LCMS Rt=2.705 min, m/z=689.3 [M+H]⁺.

LCMS (5 to 95% acetonitrile in water+0.03% ammonium bicarbonate over 6 mins) retention time 2.705 min, ESI+ found [M+H]=689.3.

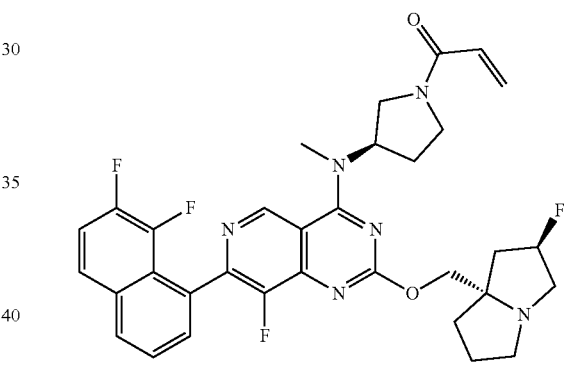

Example 192 (Method 1): 1-((R)-3-((7-(7, 8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one

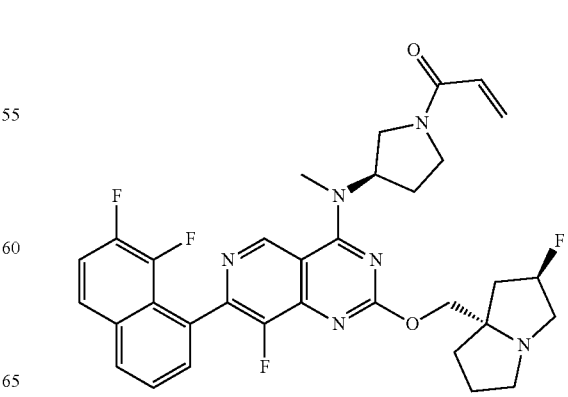

Step 1: 1-((R)-3-((7-(7, 8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one The amide coupling reaction was prepared in a similar fashion to Method #1, Step 10. The residue was purified by reverse phase HPLC(column: Waters Xbridge Prep OBD C18 150*40 mm*10 μm; mobile phase: [water ($NH_4HCO_3$)-ACN]; B %: 30%-60%, 8 min) affording 1-((R)-3-((7-(7, 8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (158.81 mg, 15.36%) as a yellow amorphous solid: $^1$H NMR (400 MHz, Chloroform-d) δ 9.21-9.13 (m, 1H), 7.97 (br dd, J=1.3, 7.8 Hz, 1H), 7.72 (br d, J=2.0 Hz, 1H), 7.68-7.56 (m, 2H), 7.44-7.36 (m, 1H), 6.55-6.41 (m, 2H), 5.81-5.69 (m, 1H), 5.50-5.19 (m, 2H), 4.35-4.27 (m, 1H), 4.24-3.87 (m, 3H), 3.74-3.65 (m, 1H), 3.63-3.52 (m, 1H), 3.46 (dd, J=3.6, 7.8 Hz, 3H), 3.33-3.22 (m, 2H), 3.18 (br s, 1H), 2.99 (br dd, J=5.4, 8.9 Hz, 1H), 2.28 (br d, J=6.4 Hz, 5H), 1.99-1.86 (m, 3H). LCMS Rt=2.926 min, m/z=620.3 [M+H]$^+$.

LCMS (5 to 95% acetonitrile in water+0.03% ammonium bicarbonate over 6 mins) retention time 2.926 min, ESI+ found [M+H]=620.3.

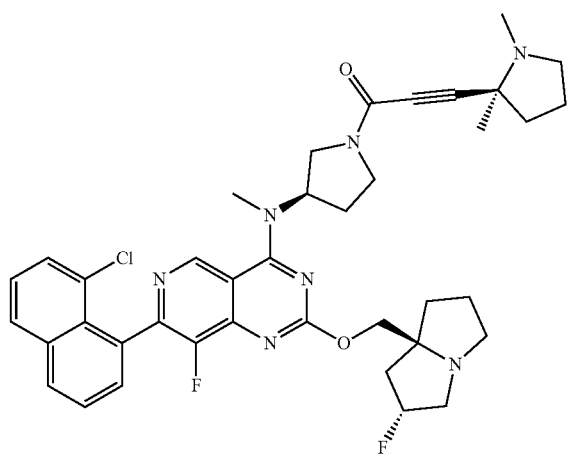 [SMILES: CN(c1nc(OC[C@@]23CCCN2C[C@H](F)C3)nc2c(F)c(-c3cccc4cccc(Cl)c34)ncc12)[C@@H]1CCN(C(=O)C#C[C@]2(C)CCCN2C)C1]

Example 193 (Method 7): 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-((S)-1,2-dimethylpyrrolidin-2-yl)prop-2-yn-1-one

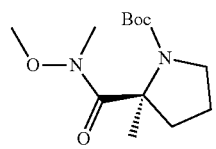 [SMILES: CON(C)C(=O)[C@]1(C)CCCN1C(=O)OC(C)(C)C]

Step 1: (S)-tert-butyl 2-(methoxy(methyl)carbamoyl)-2-methylpyrrolidine-1-carboxylate To a solution of (2S)-1-tert-butoxycarbonyl-2-methylpyrrolidine-2-carboxylic acid (8 g, 34.89 mmol) in N,N-dimethylformaldehyde (100 mL) was added N,N-diisopropylethylamine (13.53 g, 104.68 mmol), 2-(3H-[1,2,3]triazolo[4,5-b]pyridin-3-yl)-1,1,3,3-tetramethylisouronium hexafluorophosphate (19.90 g, 52.34 mmol) and N-methoxymethanamine hydrochloride (6.81 g, 69.79 mmol). The mixture was stirred at 50° C. for 12 h. The residue was diluted with water (100 mL) and extracted with ethyl acetate (3×50 mL). The combined organic layers were dried over sodium sulphate and concentrated in vacuo. The residue was purified by column chromatography (silica gel, 100-200 mesh, 0-30% ethyl acetate in petroleum ether) affording (S)-tert-butyl 2-(methoxy(methyl)carbamoyl)-2-methylpyrrolidine-1-carboxylate (7.6 g, 79.98%) as a yellow oil: $^1$H NMR (400 MHz, Chloroform-d) δ 3.68-3.58 (m, 1H), 3.56-3.52 (m, 3H), 3.34-3.23 (m, 1H), 3.12 (s, 3H), 2.35 (br d, J=10.6 Hz, 1H), 1.94-1.81 (m, 2H), 1.79-1.68 (m, 1H), 1.44 (s, 3H), 1.38-1.33 (m, 9H). LCMS Rt=0.712 min, m/z=272.2 [M+H]$^+$.

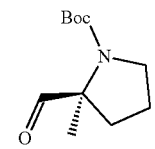

Step 2: (S)-tert-butyl 2-formyl-2-methylpyrrolidine-1-carboxylate

To a solution of (S)-tert-butyl 2-(methoxy(methyl)carbamoyl)-2-methylpyrrolidine-1-carboxylate (3 g, 11.02 mmol) in tetrahydrofuran (2 mL) was added diisobutylalumane in tetrahydrofuran (1 M, 22.03 mL), the mixture was stirred at −78° C. for 1 h. The reaction mixture was quenched with saturated ammonium chloride (30 mL) at 0° C. and extracted with ethyl acetate (3×100 mL). The combined organic layers were dried over sodium sulphate and concentrated in vacuo affording (S)-tert-butyl 2-formyl-2-methylpyrrolidine-1-carboxylate (2 g, crude) as a yellow oil and used in next step without any further purification. LCMS Rt=0.756 min, m/z=213.1 [M+H]$^+$.

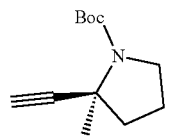

Step 3: (S)-tert-butyl 2-ethynyl-2-methylpyrrolidine-1-carboxylate

To a solution of (S)-tert-butyl 2-formyl-2-methylpyrrolidine-1-carboxylate (2 g, 9.38 mmol) in methanol (2 mL) was added potassium carbonate (2.59 g, 18.76 mmol) and 1-diazo-1-dimethoxyphosphoryl-propan-2-one (2.16 g, 11.25 mmol) at 0° C. The mixture was stirred at 25° C. for 12 h. The reaction mixture diluted with water (2 mL) and extracted with ethyl acetate (3×15 mL). The combined organic layers were dried over sodium sulphate and concentrated in vacuo. The residue was purified by column chromatography (silica gel, 100-200 mesh, 0-10% ethyl acetate in petroleum ether) affording (S)-tert-butyl 2-ethynyl-2-methylpyrrolidine-1-carboxylate (1.1 g, 56.05%) as a white oil: ¹H NMR (400 MHz, Chloroform-d) δ 3.55-3.41 (m, 1H), 3.37-3.25 (m, 1H), 2.21 (br s, 2H), 1.95-1.82 (m, 2H), 1.80-1.68 (m, 1H), 1.54 (br s, 3H), 1.42 (s, 9H). LCMS Rt=0.805 min, m/z=209.1 [M+H]⁺.

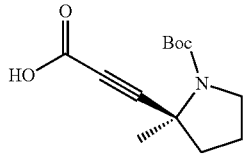 [SMILES: CC(C)(C)OC(=O)N1CCC[C@@]1(C)C#CC(=O)O]

Step 4: (S)-3-(1-(tert-butoxycarbonyl)-2-methylpyrrolidin-2-yl)propiolic acid

The carbonylation reaction was prepared in a similar fashion to Method #7, Step 1. The mixture was concentrated in vacuo affording (S)-3-(1-(tert-butoxycarbonyl)-2-methylpyrrolidin-2-yl)propiolic acid (300 mg, crude) as a yellow oil and used in next step without any further purification.

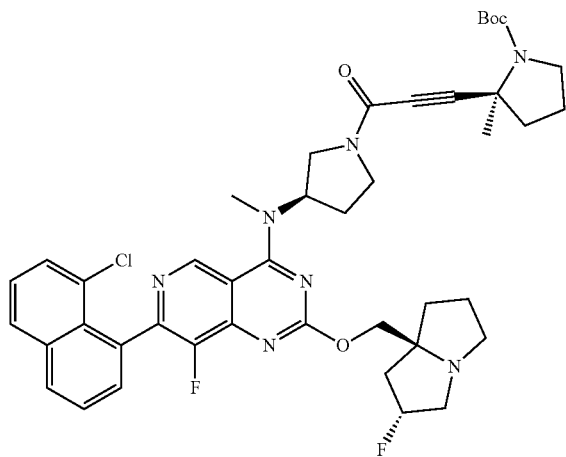 [SMILES: CN(c1nc(OC[C@@]23CCCN2C[C@H](F)C3)nc2c(F)c(-c3cccc4cccc(Cl)c34)ncc12)[C@@H]1CCN(C(=O)C#C[C@]2(C)CCCN2C(=O)OC(C)(C)C)C1]

Step 5: (S)-tert-butyl 2-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)-2-methylpyrrolidine-1-carboxylate The amide coupling reaction was prepared in a similar fashion to Method #7, Step 2. The residue was purified by reverse phase HPLC (column: Phenomenex Luna 80*30 mm*3 μm; mobile phase: [water (TFA)-ACN]; B %: 25%-55%, 8 min) affording (S)-tert-butyl 2-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)-2-methylpyrrolidine-1-carboxylate (20 mg, 6.18%, trifluoroacetic acid salt) as a yellow oil. LCMS Rt=1.690 min, m/z=799.3 [M+H]⁺.

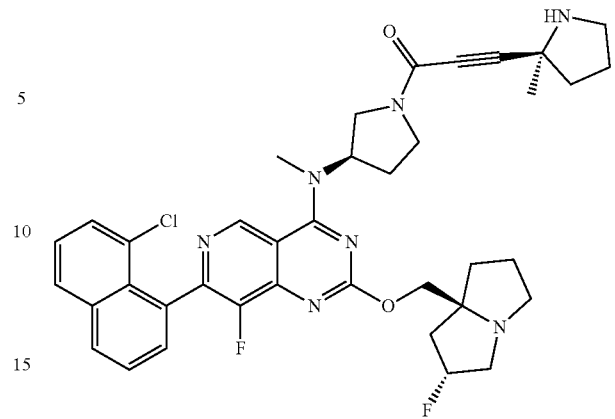

Step 6: 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-((S)-2-methylpyrrolidin-2-yl)prop-2-yn-1-one The deprotection of Boc group was prepared in a similar fashion to Method #7, Step 3. The reaction mixture was concentrated in vacuo affording 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-((S)-2-methylpyrrolidin-2-yl)prop-2-yn-1-one (20 mg, crude, trifluoroacetate salt) as a yellow oil and used in next step without any further purification. LCMS Rt=0.634 min, m/z=699.3 [M+H]⁺.

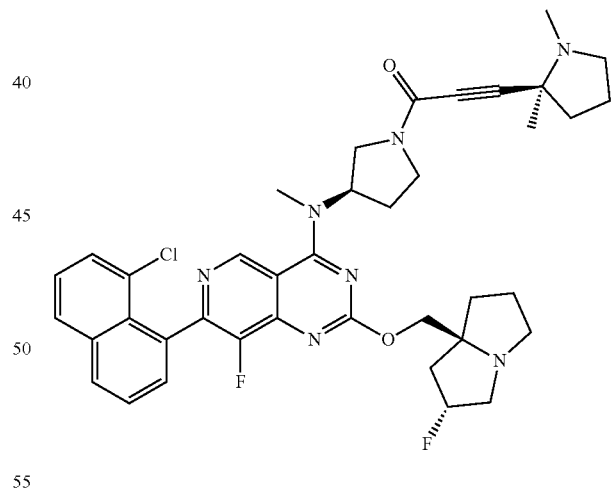

Step 7: 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-((S)-1,2-dimethylpyrrolidin-2-yl)prop-2-yn-1-one The reductive amination was prepared in a similar fashion to Method #7, Step 4. The residue was purified by reverse phase HPLC (column: Waters Xbridge BEH C18 100*30 mm*10 μm; mobile phase: [water (NH₄HCO₃)-ACN]; B %: 35%-65%, 8 min) affording 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-((S)-1,2-dimethylpyrrolidin-2-yl)prop-2-yn-1-one (2.7 mg, 15.36%) as a yellow oil: $^1$H NMR (400 MHz, Acetonitrile-d3) δ 9.27-9.17 (m, 1H), 8.15 (d, J=8.1 Hz, 1H), 8.05 (d, J=8.0 Hz, 1H), 7.76-7.69 (m, 1H), 7.69-7.60 (m, 2H), 7.57-7.48 (m, 1H), 5.46-5.20 (m, 2H), 4.27-4.10 (m, 3H), 4.01-3.87 (m, 1H), 3.83-3.65 (m, 2H), 3.50-3.38 (m, 4H), 3.18 (br d, J=7.6 Hz, 2H), 3.11 (s, 1H), 3.06-2.89 (m, 2H), 2.52-2.43 (m, 1H), 2.43-2.33 (m, 3H), 2.32 (s, 2H), 2.28 (s, 2H), 1.95-1.86 (m, 3H), 1.86-1.69 (m, 4H), 1.40 (d, J=11.1 Hz, 3H). LCMS Rt=3.074 min, m/z=713.3 [M+H]$^+$.

LCMS (5 to 95% acetonitrile in water+0.03% ammonium bicarbonate over 6 mins) retention time 3.074 min, ESI+ found [M+H]=713.3.

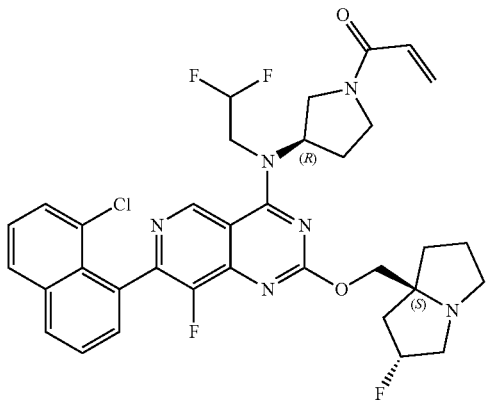

Example 194 (Method 2): 1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(2,2-difluoroethyl)amino)pyrrolidin-1-yl)prop-2-en-1-one

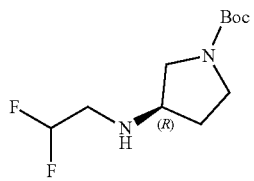

Step 1: tert-butyl (3R)-3-(2,2-difluoroethylamino)pyrrolidine-1-carboxylate

To a solution of tert-butyl (3R)-3-aminopyrrolidine-1-carboxylate (1 g, 5.37 mmol) in dioxane (10 mL) were added N,N-diisopropylethylamine (902.10 mg, 6.98 mmol) and 2,2-difluoroethyl trifluoromethanesulfonate (1.15 g, 5.37 mmol), the mixture was stirred at 20° C. for 12 h. The mixture was diluted with water (10 mL) and extracted with ethyl acetate (3×20 mL). The combined organic layers were dried over sodium sulphate and concentrated in vacuo. The residue was purified by column chromatography (silica gel, 100-200 mesh, 70-100% ethyl acetate in petroleum ether) affording tert-butyl (3R)-3-(2,2-difluoroethylamino)pyrrolidine-1-carboxylate (1.2 g, 80.37%) as a white oil: $^1$H NMR (400 MHz, Chloroform-d) δ 5.77 (tt, J=4.3, 56.4 Hz, 1H), 3.54-3.35 (m, 2H), 3.30 (br d, J=5.8 Hz, 2H), 3.11-2.97 (m, 1H), 2.91 (dt, J=4.1, 15.0 Hz, 2H), 2.04-1.94 (m, 2H), 1.65 (br d, J=3.9 Hz, 1H), 1.40 (s, 9H). LCMS Rt=0.575 min, m/z=250.2 [M+H]$^+$.

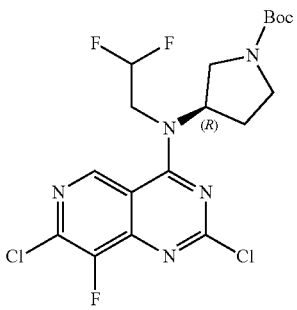

Step 2: tert-butyl (3R)-3-[(2,7-dichloro-8-fluoropyrido[4,3-d]pyrimidin-4-yl)-(2,2-difluoroethyl)amino]pyrrolidine-1-carboxylate The substitution reaction was prepared in a similar fashion to Method #2, Step 3. The residue was purified by column chromatography (silica gel, 100-200 mesh, 0-50% ethyl acetate in petroleum ether) affording tert-butyl (3R)-3-[(2,7-dichloro-8-fluoro-pyrido[4,3-d]pyrimidin-4-yl)-(2,2-difluoroethyl)amino]pyrrolidine-1-carboxylate (1.5 g, 54.76%) as a yellow solid. LCMS Rt=0.819 min, m/z=465.1 [M+H]$^+$.

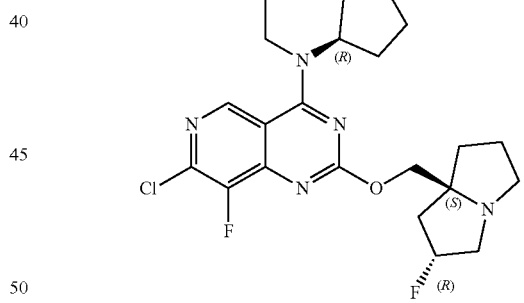

Step 3: (R)-tert-butyl 3-((7-chloro-8-fluoro-2-(((2R,7aS)-2-fluorohexahydro-1H-pyrrolizin-7a-yl)methoxy)pyrido[4,3-d]pyrimidin-4-yl)(2,2-difluoroethyl)amino)pyrrolidine-1-carboxylate The substitution reaction was prepared in a similar fashion to Method #2, Step 4. The residue was purified by column chromatography (silica gel, 100-200 mesh, 0-80% ethyl acetate in petroleum ether) affording (R)-tert-butyl 3-((7-chloro-8-fluoro-2-(((2R,7aS)-2-fluorohexahydro-1H-pyrrolizin-7a-yl)methoxy)pyrido[4,3-d]pyrimidin-4-yl)(2,2-difluoroethyl)amino)pyrrolidine-1-carboxylate (1.5 g, 58.26%) as a yellow solid. LCMS Rt=0.764 min, m/z=588.2 [M+H]$^+$.

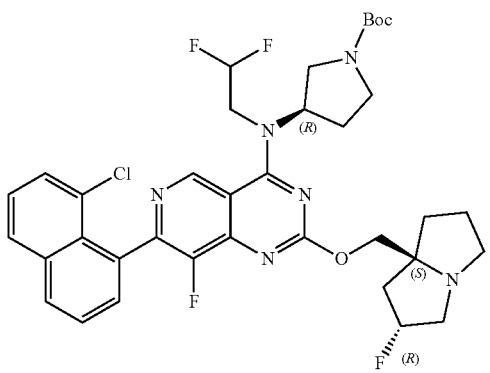

Step 4: (R)-tert-butyl 3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(2,2-difluoroethyl)amino)pyrrolidine-1-carboxylate The Suzuki reaction was prepared in a similar fashion to Method #2, Step 5. The residue was purified by column chromatography (silica gel, 100-200 mesh, 50-100% ethyl acetate in petroleum ether) affording (R)-tert-butyl 3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(2,2-difluoroethyl)amino)pyrrolidine-1-carboxylate (270 mg, 27.42%) as a brown solid. LCMS Rt=0.717 min, m/z=714.3 [M+H]$^+$.

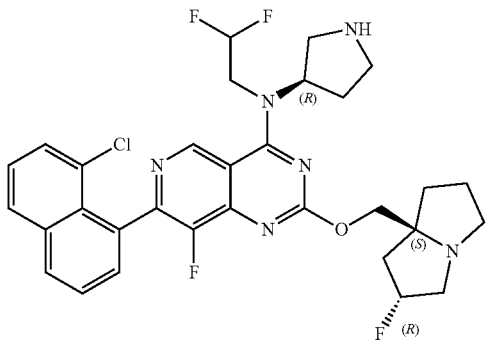

Step 5: 7-(8-chloronaphthalen-1-yl)-N-(2,2-difluoroethyl)-8-fluoro-2-(((2R,7aS)-2-fluorohexahydro-1H-pyrrolizin-7a-yl)methoxy)-N—((R)-pyrrolidin-3-yl)pyrido[4,3-d]pyrimidin-4-amine The deprotection of Boc reaction was prepared in a similar fashion to Method #2, Step 6. The residue was concentrated to dryness in vacuo affording 7-(8-chloronaphthalen-1-yl)-N-(2,2-difluoroethyl)-8-fluoro-2-(((2R,7aS)-2-fluorohexahydro-1H-pyrrolizin-7a-yl)methoxy)-N—((R)-pyrrolidin-3-yl)pyrido[4,3-d]pyrimidin-4-amine (100 mg, crude, trifluoroacetate salt) as a brown oil and used in next step without further purification. LCMS Rt=0.536 min, m/z=614.2 [M+H]$^+$.

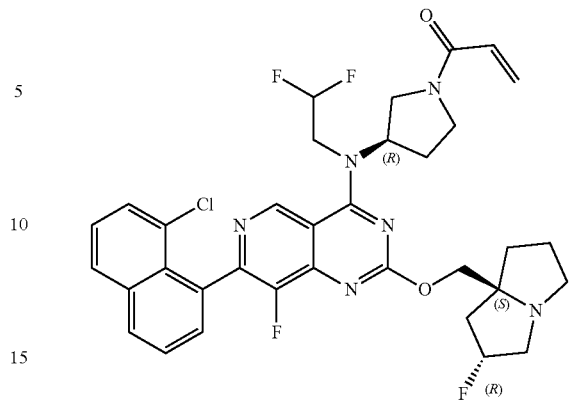

Step 6: 1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(2,2-difluoroethyl)amino)pyrrolidin-1-yl)prop-2-en-1-one The amide coupling reaction was prepared in a similar fashion to Method #2, Step 7. The resulting residue was purified by reverse phase HPLC (column: Waters Xbridge Prep OBD C18 150*40 mm*10 μm; mobile phase: [water (NH$_4$HCO$_3$)— Acetonitrile]; B %: 35%-65%, 8 min.) affording 1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(2,2-difluoroethyl)amino)pyrrolidin-1-yl)prop-2-en-1-one (7.13 mg, 7.62%) as a yellow oil: $^1$H NMR (400 MHz, Acetonitrile-d3) δ 9.16-9.06 (m, 1H), 8.17-8.10 (m, 1H), 8.02 (d, J=8.1 Hz, 1H), 7.74-7.65 (m, 1H), 7.62 (d, J=6.9 Hz, 2H), 7.56-7.47 (m, 1H), 6.62-6.48 (m, 1H), 6.40-6.05 (m, 2H), 5.70-5.61 (m, 1H), 5.36-5.06 (m, 2H), 4.26-4.10 (m, 4H), 4.07-3.67 (m, 3H), 3.64-3.52 (m, 1H), 3.19-3.10 (m, 2H), 3.06 (s, 1H), 2.93-2.85 (m, 1H), 2.18 (br d, J=4.1 Hz, 2H), 2.12-2.00 (m, 3H), 1.91-1.81 (m, 3H). LCMS Rt=3.115 min, m/z=668.2 [M+H]$^+$.

LCMS (5 to 95% acetonitrile in water+0.03% ammonium bicarbonate over 6 mins) retention time 3.115 min, ESI+ found [M+H]=668.2.

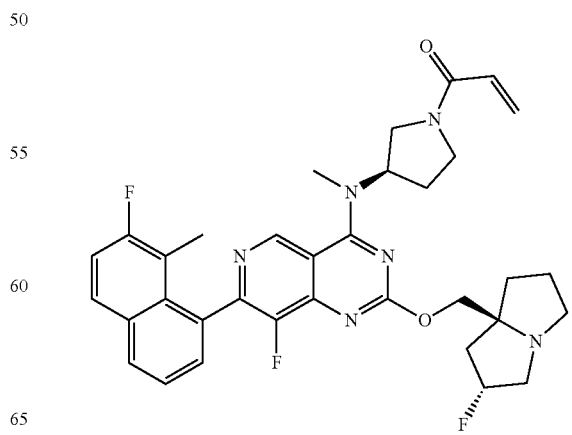

Example 195 (Method 10-Master): 1-((R)-3-((8-fluoro-7-(7-fluoro-8-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one

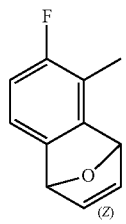

Step 1: 4-fluoro-3-methyl-11-oxatricyclo[6.2.1.02,7]undeca-2,4,6,9-tetraene

A mixture of 1-bromo-2,4-difluoro-3-methyl-benzene (20 g, 96.61 mmol), furan (13.15 g, 193.22 mmol) in toluene (300 mL) was degassed and purged with nitrogen 3 times, subsequently n-butyllithium (2.5 M, 46.37 mL) was added at −20° C., the mixture was stirred at 20° C. for 12 h under a nitrogen atmosphere. The reaction mixture was quenched with saturated ammonium chloride (900 mL) and extracted with dichloromethane (3×500 mL). The combined organic layers were dried over sodium sulphate and concentrated in vacuo. The residue was purified by column chromatography (silica gel, 100-200 mesh, 0-10% ethyl acetate in petroleum ether) affording 4-fluoro-3-methyl-11-oxatricyclo[6.2.1.02,7]undeca-2,4,6,9-tetraene (30 g, 58.75%) was as a yellow oil. LCMS Rt=0.676 min, m/z=176.1 [M+H]⁺.

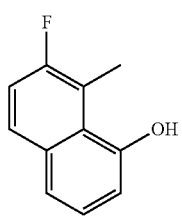

Step 2: 7-fluoro-8-methyl-naphthalen-1-ol

To a solution of 4-fluoro-3-methyl-11-oxatricyclo[6.2.1.02,7]undeca-2,4,6,9-tetraene (30 g, 170.27 mmol) in ethanol (300 mL) was added hydrogenchloride (12 M, 170.27 mL). The mixture was stirred at 80° C. for 2 h. The reaction mixture was concentrated in vacuo. The residue was purified by column chromatography (silica gel, 100-200 mesh, 0-10% ethyl acetate in petroleum ether) affording 7-fluoro-8-methyl-naphthalen-1-ol (16.2 g, 54.00%) as a red solid. LCMS Rt =0.732 min, m/z=176.1 [M+H]⁺.

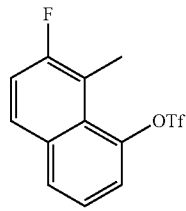 [SMILES: Cc1c(F)ccc2cccc(OS(=O)(=O)C(F)(F)F)c12]

Step 3: (7-fluoro-8-methyl-1-naphthyl) trifluoromethanesulfonate

To a mixture of 7-fluoro-8-methyl-naphthalen-1-ol (5 g, 28.38 mmol) in DCM (50 mL) was added N,N-diisopropylethylamine (22.01 g, 170.27 mmol) and trifluoromethanesulfonic anhydride (10.41 g, 36.89 mmol), the mixture was stirred at 0° C. for 0.5 h under N₂ atmosphere. The reaction mixture was quenched with saturated sodium bicarbonate (50 mL) and extracted with dichloromethane (3×50 mL). The combined organic layers were dried over sodium sulphate and concentrated in vacuo. The residue was purified by column chromatography (silica gel, 100-200 mesh, 0-10% ethyl acetate in petroleum ether) affording (7-fluoro-8-methyl-1-naphthyl) trifluoromethanesulfonate (8 g, 91.45%) as a yellow oil. LCMS Rt=0.951 min, m/z=308.0 [M +H]⁺.

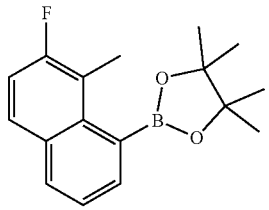 [SMILES: Cc1c(F)ccc2cccc(B3OC(C)(C)C(C)(C)O3)c12]

Step 4: 2-(7-fluoro-8-methyl-1-naphthyl)-4,4,5,5-tetramethyl-1,3,2-dioxaborolane A mixture of (7-fluoro-8-methyl-1-naphthyl) trifluoromethanesulfonate (25 g, 81.10 mmol), 4,4,5,5-tetramethyl-2-(4,4,5,5-tetramethyl-1,3,2-dioxaborolan-2-yl)-1,3,2-dioxaborolane (41.19 g, 162.21 mmol), potassium acetate (39.80 g, 405.52 mmol) and [1,1-bis(diphenylphosphino)ferrocene]dichloropalladium(II) (5.93 g, 8.11 mmol) in dioxane (400 mL) was degassed and purged with nitrogen for 3 times, and the mixture was stirred at 80° C. for 12 h under a nitrogen atmosphere. The mixture was diluted with water (500 mL) and extracted with ethyl acetate (3×500 mL). The combined organic layers were dried over sodium sulphate and concentrated in vacuo. The residue was purified by column chromatography (silica gel, 100-200 mesh, 0-10% ethyl acetate in petroleum ether) affording 2-(7-fluoro-8-methyl-1-naphthyl)-4,4,5,5-tetramethyl-1,3,2-dioxaborolane (23 g, 99.11%) as a yellow solid. LCMS Rt=0.962 min, m/z=286.2 [M+H]⁺.

831

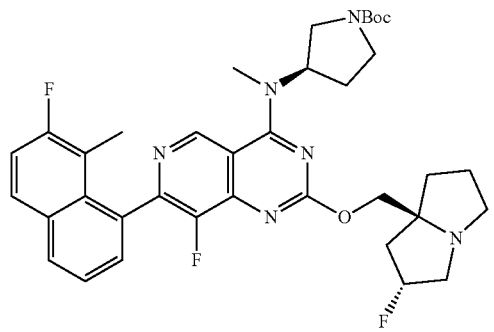

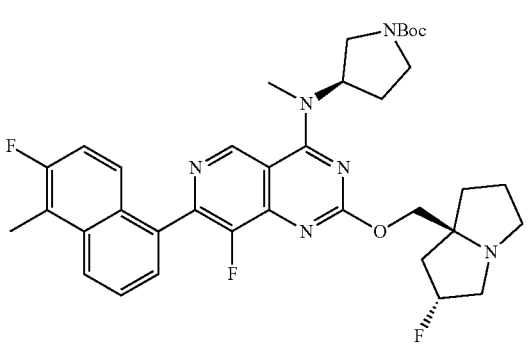

Step 5: (R)-tert-butyl 3-((8-fluoro-7-(7-fluoro-8-methylnaphthalen-1-yl)-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate and tert-butyl (R)-3-((8-fluoro-7-(6-fluoro-5-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino) pyrrolidine-1-carboxylate A mixture of tert-butyl (3R)-3-[[7-chloro-8-fluoro-2-[[(2R,8S)-2-fluoro-1,2,3,5,6,7-hexahydropyrrolizin-8-yl]methoxy]pyrido[4,3-d]pyrimidin-4-yl]-methyl-amino]pyrrolidine-1-carboxylate (1.5 g, 2.78 mmol), 2-(7-fluoro-8-methyl-1-naphthyl)-4,4,5,5-tetramethyl-1,3,2-dioxaborolane (2.39 g, 8.35 mmol), potassium phosphate (1.77 g, 8.35 mmo and [2-(2-aminophenyl)phenyl]-chloropalladium; Bis(1-adamantyl)-butyl-phosphane (372.14 mg, 556.57 μmol) in dioxane (30 mL) and water (10 mL) was degassed and purged with nitrogen 3 times and the mixture was stirred at 100° C. for 12 h under a nitrogen atmosphere. The mixture was diluted with water (10 mL) and extracted with ethyl acetate (3×50 mL). The combined organic layers were dried over sodium sulphate and concentrated in vacuo. The residue was purified by column chromatography (silica gel, 100-200 mesh, 0-100% ethyl acetate in petroleum ether) affording (R)-tert-butyl 3-((8-fluoro-7-(7-fluoro-8-methyl-naphthalen-1-yl)-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate and tert-butyl (R)-3-((8-fluoro-7-(6-fluoro-5-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidine-1-carboxylate (1.8 g, 97.60%) as a brown oil. LCMS Rt=0.790 min, m/z=662.3 [M+H]⁺.

832

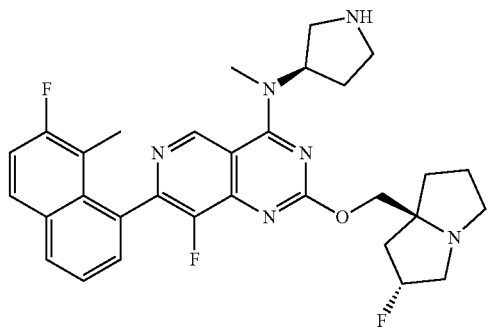 [SMILES: Cc1c(F)ccc2cccc(-c3ncc4c(N(C)[C@@H]5CCNC5)nc(OC[C@@]56CCCN5C[C@H](F)C6)nc4c3F)c12]

Step 6: 8-fluoro-7-(7-fluoro-8-methylnaphthalen-1-yl)-2-(((2R,7aS)-2-fluorohexahydro-1H-pyrrolizin-7a-yl)methoxy)-N-methyl-N—((R)-pyrrolidin-3-yl) pyrido[4,3-d]pyrimidin-4-amine The deprotection of Boc group was prepared in a similar fashion to Method #1, Step 9. The reaction mixture was concentrated in vacuo affording 8-fluoro-7-(7-fluoro-8-methylnaphthalen-1-yl)-2-(((2R,7aS)-2-fluorohexahydro-1H-pyrrolizin-7a-yl)methoxy)-N-methyl-N—((R)-pyrrolidin-3-yl)pyrido[4,3-d]pyrimidin-4-amine (306 mg, crude, trifluoroacetate salt) as a brown oil used as is in the next step. LCMS Rt=0.510 min, m/z=562.3 [M+H]⁺.

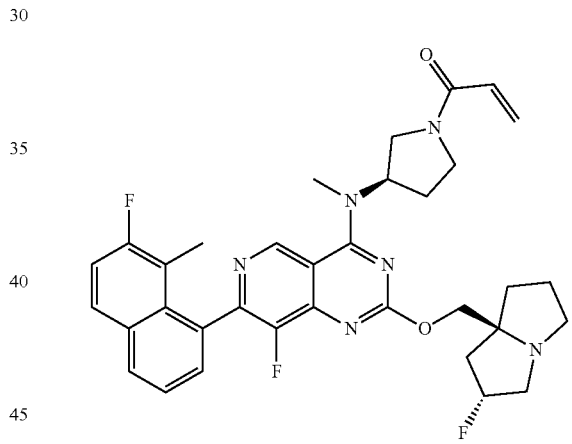

Step 7: 1-((R)-3-((8-fluoro-7-(7-fluoro-8-methyl-naphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one The amide coupling reaction was prepared in a similar fashion to Method #1, Step 10. The reaction mixture was concentrated in vacuo and purified by reverse phase HPLC (neutral condition,column: Waters Xbridge Prep OBD C18 150*40 mm*10 μm; mobile phase: [water ($NH_4HCO_3$)-ACN]; B %: 35%-65%, 8 min) affording 1-((R)-3-((8-fluoro-7-(7-fluoro-8-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (58.14 mg, 20.09%) as a yellow solid: ¹H NMR (400 MHz, Chloroform-d) δ 9.18 (s, 1H), 7.99-7.94 (m, 1H), 7.81 (br t, J=7.1 Hz, 1H), 7.58-7.46 (m, 2H), 7.34-7.28 (m, 1H), 6.58-6.42 (m, 2H), 5.83-5.70 (m, 1H), 5.45 (quin, J=7.8 Hz, 1H), 5.39-5.19 (m, 1H), 4.36-4.28 (m, 1H), 4.27-4.20 (m, 1H), 4.19-3.87 (m, 2H), 3.77-3.66 (m, 1H), 3.64-3.55 (m, 1H), 3.51-3.42 (m, 3H), 3.33-3.15 (m, 3H), 3.06-2.94 (m, 1H), 2.56-2.33 (m, 2H), 2.33-2.24 (m, 2H), 2.22-2.10 (m, 2H), 1.96 (br s, 2H), 1.90-1.64 (m, 3H). LCMS Rt=3.028 min, m/z=616.3 [M+H]⁺.

LCMS (5 to 95% acetonitrile in water+0.03% ammonium bicarbonate over 6 mins) retention time 3.028 min, ESI+ found [M+H]=616.3.

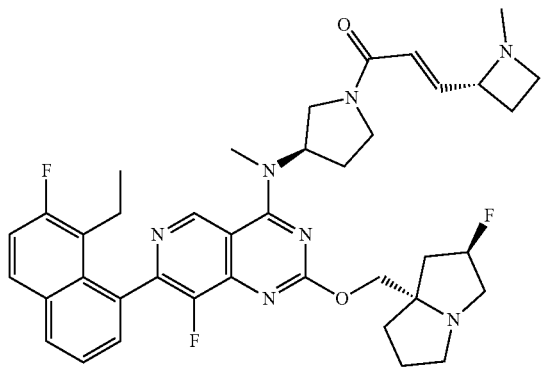 [SMILES: CCc1c(F)ccc2cccc(-c3ncc4c(N(C)[C@@H]5CCN(C(=O)/C=C/[C@H]6CCN6C)C5)nc(OC[C@@]56CCCN5C[C@H](F)C6)nc4c3F)c12]

Example 196 (Method 11): (E)-1-((R)-3-((7-(8-ethyl-7-fluoronaphthalen-1-yl)-8-fluoro-2-(((2R, 7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-methylazetidin-2-yl)prop-2-en-1-one

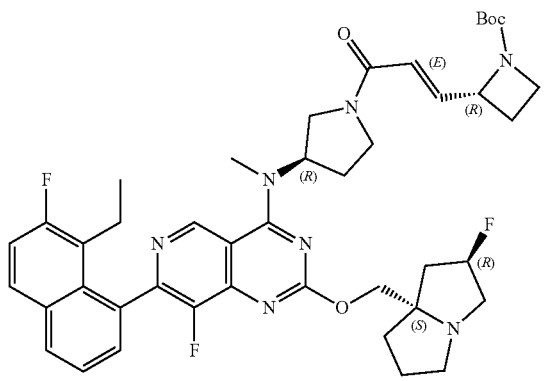

Step 1: tert-butyl (R)-2-((E)-3-((R)-3-((7-(8-ethyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-oxoprop-1-en-1-yl)azetidine-1-carboxylate The amide coupling reaction was prepared in a similar fashion to Method #11, Step 11. The resulting residue was purified by prep-HPLC (column: Phenomenex luna C18 250*50 mm*10 μm; mobile phase: [water (TFA)-ACN]; B %: 20%-50%, 10 min) affording tert-butyl (R)-2-((E)-3-((R)-3-((7-(8-ethyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-oxoprop-1-en-1-yl)azetidine-1-carboxylate (220 mg, 49.96%, trifluoroacetic acid salt) as yellow solid and used in next step without any further purification. LCMS Rt=0.613 min, m/z=785.4 [M+H]⁺.

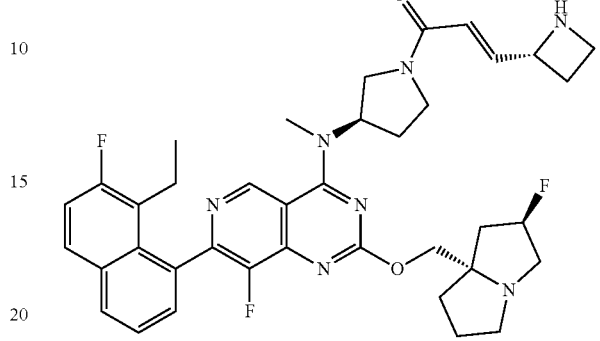

Step 2: (E)-3-((R)-azetidin-2-yl)-1-((R)-3-((7-(8-ethyl-7-fluoronaphthalen-1-yl)-8-fluoro-2-(((2R, 7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one The deprotection of Boc group was prepared in a similar fashion to Method #11, Step 12. The reaction mixture was concentrated in vacuo affording (E)-3-((R)-azetidin-2-yl)-1-((R)-3-((7-(8-ethyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (160 mg, crude, trifluoroacetic acid salt) as a yellow oil and used in next step without any further purification. LCMS Rt=0.548 min, m/z=685.3 [M+H]⁺.

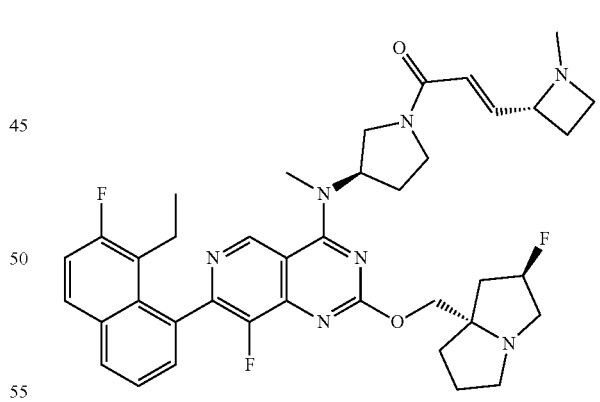

Step 3: (E)-1-((R)-3-((7-(8-ethyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-methylazetidin-2-yl)prop-2-en-1-one The reductive amination was prepared in a similar fashion to Method #11, Step 13. The residue was purified by prep-HPLC (column: Waters Xbridge Prep OBD C18 150*40 mm*10 μm; mobile phase: [water (NH₄HCO₃)-

ACN]; B %: 35%-65%, 8 min) affording (E)-1-((R)-3-((7-(8-ethyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-methylazetidin-2-yl)prop-2-en-1-one (53.91 mg, 36.54%) as a white solid: ¹H NMR (400 MHz, Acetonitrile-d3) δ 9.18 (br s, 1H), 8.04 (br d, J=8.0 Hz, 1H), 7.92 (br t, J=7.2 Hz, 1H), 7.58-7.44 (m, 2H), 7.37 (br t, J=9.3 Hz, 1H), 6.76 (br dd, J=5.3, 15.1 Hz, 1H), 6.37 (br dd, J=11.1, 14.3 Hz, 1H), 5.47-5.14 (m, 2H), 4.25-4.17 (m, 1H), 4.15-4.09 (m, 1H), 4.09-3.90 (m, 1H), 3.89-3.75 (m, 1H), 3.64 (br d, J=8.6 Hz, 1H), 3.56-3.49 (m, 1H), 3.41 (s, 3H), 3.27 (q, J=7.7 Hz, 1H), 3.18-3.07 (m, 2H), 3.05 (br s, 1H), 2.93-2.84 (m, 1H), 2.79 (quin, J=7.6 Hz, 1H), 2.54-2.42 (m, 1H), 2.41-2.33 (m, 1H), 2.27 (br d, J=6.8 Hz, 1H), 2.24 (br s, 3H), 2.20-2.08 (m, 4H), 2.07-1.95 (m, 2H), 1.86 (br dd, J=9.0, 17.5 Hz, 4H), 0.80 (br t, J=7.1 Hz, 3H). LCMS Rt=2.903 min, m/z=699.4 [M+H]⁺.

LCMS (5 to 95% acetonitrile in water+0.03% ammonium bicarbonate over 6 mins) retention time 2.903 min, ESI+ found [M+H]=699.4.

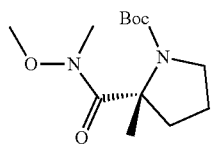 [SMILES: CON(C)C(=O)[C@@]1(C)CCCN1C(=O)OC(C)(C)C]

Example 197 (Method 7): 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-((R)-1,2-dimethylpyrrolidin-2-yl)prop-2-yn-1-one Step 1: (R)-tert-butyl 2-(methoxy(methyl)carbamoyl)-2-methylpyrrolidine-1-carboxylate To a solution of (2R)-1-tert-butoxycarbonyl-2-methylpyrrolidine-2-carboxylic acid (5 g, 21.81 mmol) in N,N-dimethylformamide (30 mL) was added 2-(3H-[1,2,3]triazolo[4,5-b]pyridin-3-yl)-1,1,3,3-tetramethylisouronium hexafluorophosphate (12.44 g, 32.71 mmol) and N,N-diisopropylethylamine (14.09 g, 109.04 mmol) and N-methoxymethanamine hydrochloride (4.25 g, 43.62 mmol), the mixture was stirred at 50° C. for 12 h. The mixture was diluted with water (20 mL) and extracted with ethyl acetate (3×50 mL). The combined organic layers were dried over sodium sulphate and concentrated in vacuo. The residue was purified by column chromatography (silica gel, 100-200 mesh, 0-30% ethyl acetate in petroleum ether) affording (R)-tert-butyl 2-(methoxy(methyl)carbamoyl)-2-methylpyrrolidine-1-carboxylate (5.2 g, 87.55%) as a white solid: ¹H NMR (400 MHz, Chloroform-d) δ 3.77-3.69 (m, 1H), 3.66-3.62 (m, 3H), 3.42-3.31 (m, 1H), 3.22 (s, 3H), 2.50-2.25 (m, 1H), 2.03-1.91 (m, 2H), 1.83-1.74 (m, 1H), 1.57-1.52 (m, 3H), 1.48-1.44 (m, 9H). LCMS Rt=0.712 min, m/z=272.2 [M+H]⁺.

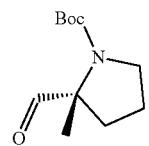

Step 2: (R)-tert-butyl 2-formyl-2-methylpyrrolidine-1-carboxylate

A mixture of tert-butyl (2R)-2-[methoxy(methyl)carbamoyl]-2-methyl-pyrrolidine-1-carboxylate (2 g, 7.34 mmol) in tetrahydrofuran (5 mL) was degassed and purged with nitrogen 3 times, diisobutylalumane in tetrahydrofuran (1 M, 14.69 mL) was added and the mixture was stirred at −78° C. for 0.5 h under a nitrogen atmosphere. The reaction mixture was quenched with saturated ammonium chloride (30 mL) at 0° C., and extracted with ethyl acetate (3×100 mL). The combined organic layers were dried over sodium sulphate and concentrated in vacuo affording (R)-tert-butyl 2-formyl-2-methylpyrrolidine-1-carboxylate (2.6 g, crude) as a white oil and used in next step without any further purification. LCMS Rt=0.756 min, m/z=213.1 [M+H]+

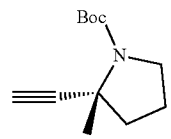

Step 3: (R)-tert-butyl 2-ethynyl-2-methylpyrrolidine-1-carboxylate

To a solution of tert-butyl (2R)-2-formyl-2-methyl-pyrrolidine-1-carboxylate (2.5 g, 11.72 mmol), 1-diazo-1-dimethoxyphosphoryl-propan-2-one (3.38 g, 17.58 mmol) in methanol (40 mL) was added potassium carbonate (4.86 g, 35.17 mmol), the mixture was stirred at 25° C. for 2 h. The reaction mixture was diluted with water (30 mL) and extracted with ethyl acetate (3×50 mL). The combined organic layers were dried over sodium sulphate and concentrated in vacuo. The residue was purified by column chromatography (silica gel, 100-200 mesh, 0-15% ethyl acetate in petroleum ether) affording (R)-tert-butyl 2-ethynyl-2-methylpyrrolidine-1-carboxylate (1.7 g, 69.30%) as a white oil. LCMS Rt=0.805 min, m/z=209.1 [M+H]⁺

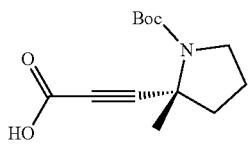 [SMILES: CC(C)(C)OC(=O)N1CCC[C@]1(C)C#CC(=O)O]

Step 4: (R)-3-(1-(tert-butoxycarbonyl)-2-methylpyrrolidin-2-yl)propiolic acid The carbonylation reaction was prepared in a similar fashion to Method #7, Step 1. The mixture was diluted with water (10 mL) and extracted with ethyl acetate (3×20 mL). The combined organic layers were dried over sodium sulphate and concentrated in vacuo affording (R)-3-(1-(tert-butoxycarbonyl)-2-methylpyrrolidin-2-yl)propiolic acid (330 mg, crude) as a white oil and used in next reaction without purification.

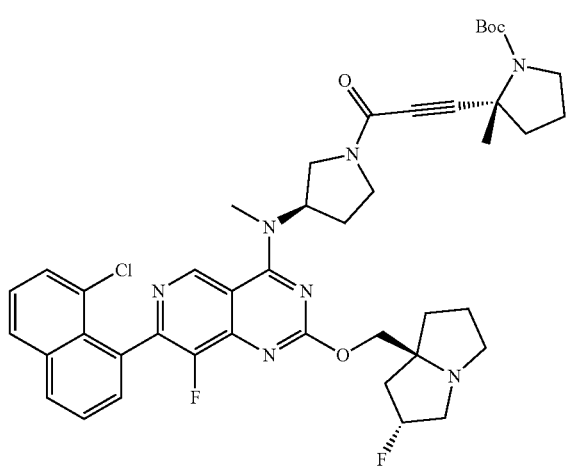 [SMILES: CN(c1nc(OC[C@@]23CCCN2C[C@H](F)C3)nc2c(F)c(-c3cccc4cccc(Cl)c34)ncc12)[C@@H]1CCN(C(=O)C#C[C@@]2(C)CCCN2C(=O)OC(C)(C)C)C1]

Step 5: (R)-tert-butyl 2-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)-2-methylpyrrolidine-1-carboxylate The amide coupling reaction was prepared in a similar fashion to Method #7, Step 2. The residue was purified by reverse phase HPLC (column: Phenomenex luna C18 100*40 mm*3 μm; mobile phase: [water (TFA)-ACN]; B %: 20%-65%, 8 min) affording (R)-tert-butyl 2-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)-2-methylpyrrolidine-1-carboxylate (110 mg, 25.89) as a yellow solid. LCMS Rt=1.690 min, m/z=799.3 [M+H]⁺.

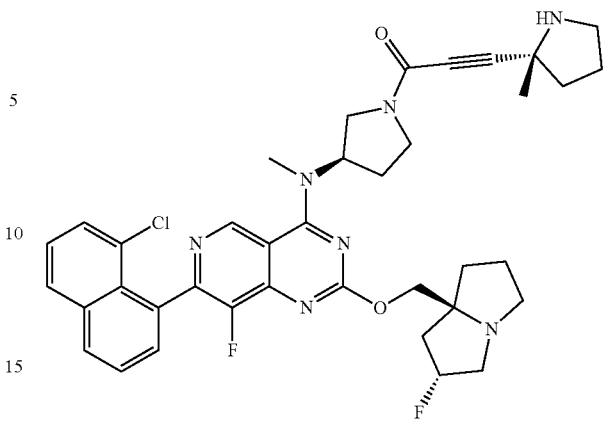

Step 6: 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-((R)-2-methylpyrrolidin-2-yl)prop-2-yn-1-one The deprotection of Boc group was prepared in a similar fashion to Method #7, Step 3. The reaction mixture concentrated in vacuo affording 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-((R)-2-methylpyrrolidin-2-yl)prop-2-yn-1-one (70 mg, crude, trifluoroacetate salt) as a brown oil and used into the next step without further purification. LCMS Rt=0.634 min, m/z=699.3 [M+H]⁺.

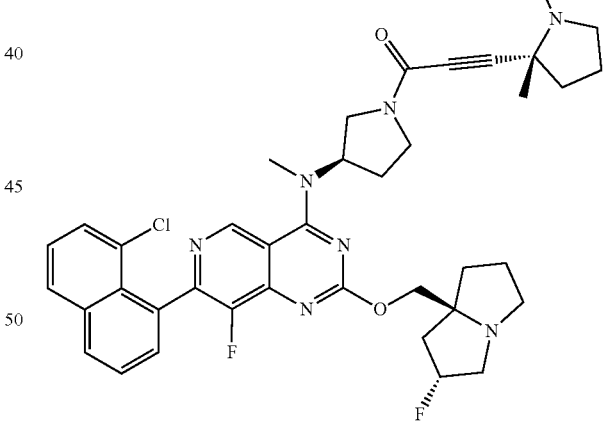

Step 7: 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-((R)-1,2-dimethylpyrrolidin-2-yl)prop-2-yn-1-one The reductive amination was prepared in a similar fashion to Method #7, Step 4. The residue was purified by reverse phase HPLC (column: Waters Xbridge Prep OBD C18 150*40 mm*10 um; mobile phase: [water (NH₄HCO₃)-ACN]; B %: 30%-60%, 8 min) affording 1-((R)-3-((7-(8- chloronaphthalen-1-yl)-8-fluoro-2-(((2R,7aS)-2-fluoro-hexahydro-1H-pyrrolizin-7a-yl)methoxy)pyrido[4,3-d]pyrimidin-4-yl)(methyl)amino)pyrrolidin-1-yl)-3-((R)-1,2-dimethylpyrrolidin-2-yl)prop-2-yn-1-one (23.65 mg, 31.64%) as a yellow amorphous solid: $^1$H NMR (400 MHz, Acetonitrile-d3) δ 9.22-9.15 (m, 1H), 8.12 (d, J=8.1 Hz, 1H), 8.05-7.99 (m, 1H), 7.72-7.66 (m, 1H), 7.64-7.59 (m, 2H), 7.54-7.49 (m, 1H), 5.43-5.34 (m, 1H), 5.33-5.15 (m, 1H), 4.24-4.15 (m, 1H), 4.00-3.85 (m, 1H), 3.79-3.62 (m, 2H), 3.52-3.44 (m, 1H), 3.44-3.38 (m, 3H), 3.19-3.09 (m, 2H), 3.06 (s, 1H), 3.04-2.84 (m, 2H), 2.50-2.31 (m, 3H), 2.29 (s, 2H), 2.25-2.19 (m, 2H), 2.13-2.02 (m, 4H), 1.91-1.82 (m, 3H), 1.81-1.71 (m, 3H), 1.36 (d, J=11.5 Hz, 3H). LCMS Rt=3.073 min, m/z=713.3 [M+H]$^+$.

LCMS (5 to 95% acetonitrile in water+0.03% ammonium bicarbonate over 6 mins) retention time 3.073 min, ESI+ found [M+H]=713.3.

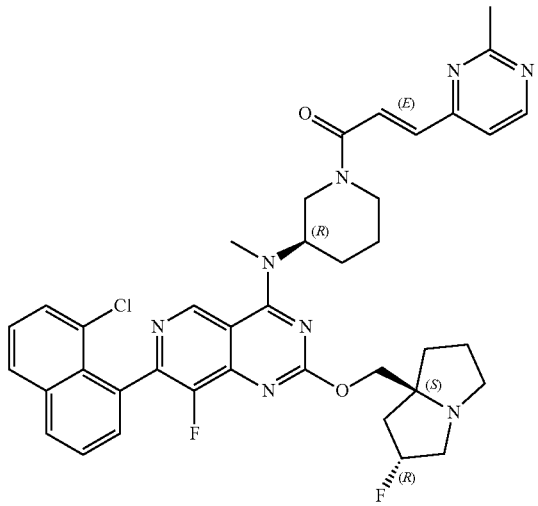

Example 198 (Method 1): (E)-1-((R)-3-((7-(8-chloronaphthalen-1-yl)-8-fluoro-2-(((2R,7aS)-2-fluoro-tetrahydro-1H-pyrrolizin-7a(5H)-yl)methoxy)pyrido[4,3-d]pyrimidin-4-yl)(methyl)amino)piperidin-1-yl)-3-(2-methylpyrimidin-4-yl)prop-2-en-1-one

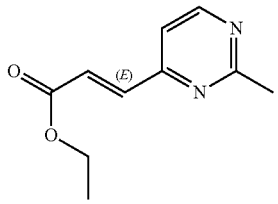

Step 1: (E)-ethyl 3-(2-methylpyrimidin-4-yl)acrylate

To a solution of 4-chloro-2-methyl-pyrimidine (4.9 g, 38.11 mmol) in dioxane (30 mL) and water (10 mL) were added ethyl 3-(4,4,5,5-tetramethyl-1,3,2-dioxaborolan-2-yl)propanoate (13.04 g, 57.17 mmol), potassium phosphate (24.27 g, 114.34 mmol) and [2-(2-aminophenyl)phenyl]-chloro-palladium; dicyclohexyl-[3-(2,4,6-triisopropylphenyl)phenyl]phosphane (3.00 g, 3.81 mmol), the mixture was degassed and purged with nitrogen three times, and subsequently the mixture was stirred at 100° C. for 2 hr under a nitrogen atmosphere. The reaction mixture was diluted with water (20 mL) and extracted with ethyl acetate (2×30 mL). The combined organic layers were dried over sodium sulphate and concentrated in vacuo. The resulting residue was purified by column chromatography (silica gel, 100-200 mesh, 0-20% ethyl acetate in petroleum ether) affording (E)-ethyl 3-(2-methylpyrimidin-4-yl)acrylate (11 g, crude) as an orange gum used in the next step without further purification. LCMS Rt=0.522 min, m/z=192.1 [M+H]$^+$.

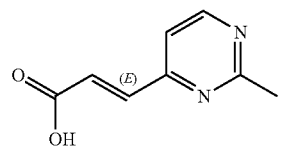

Step 2: (E)-3-(2-methylpyrimidin-4-yl)acrylic acid

To a solution of ethyl (E)-3-(2-methylpyrimidin-4-yl)prop-2-enoate (10 g, 52.03 mmol) in tetrahydrofuran (100 mL) was added lithium hydroxide (2 M, 52.03 mL), the mixture was stirred at 30° C. for 12 h. The mixture was extracted with ethyl acetate (2×80 mL), the aqueous phase was acidified by adding 1M hydrochloric acid dropwise at 0° C. to pH=2, the solid was collected by filtration, rinsed with water (3×10 mL) and concentrated to dryness in vacuo affording (E)-3-(2-methylpyrimidin-4-yl)acrylic acid (3.76 g, 44.03%) as a white solid: $^1$H NMR (400 MHz, DMSO-d6) δ 8.79-8.73 (m, 1H), 7.62-7.56 (m, 1H), 7.50-7.41 (m, 1H), 7.06-6.96 (m, 1H), 2.63 (s, 3H). LCMS Rt=0.243 min, m/z=164.1 [M+H]$^+$.

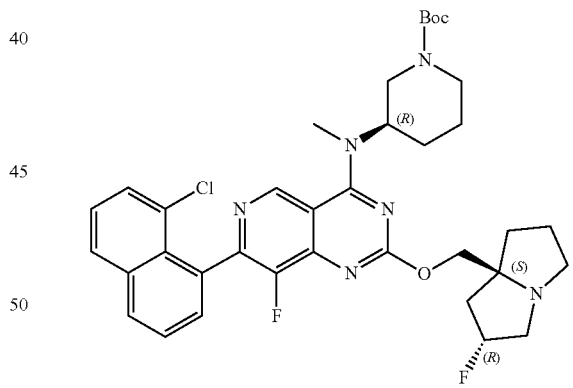

Step 3: (R)-tert-butyl 3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)piperidine-1-carboxylate The substitution reaction was prepared in a similar fashion to Method #1, Step 8. The residue was purified by reverse phase HPLC ((column: Phenomenex C18 80*30 mm*3 μm; mobile phase: [water (TFA)-ACN]; B %: 20%-50%, 8 min) affording (R)-tert-butyl 3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)

(methyl)amino)piperidine-1-carboxylate (70 mg, 14.75%, trifluoroacetate salt) as a white solid. LCMS Rt=1.506 min, m/z=678.3 [M+H]⁺.

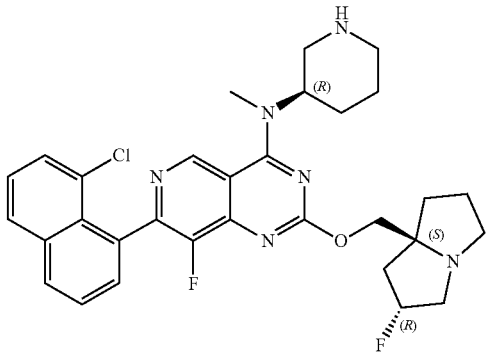

Step 4: 7-(8-chloronaphthalen-1-yl)-8-fluoro-2-(((2R,7aS)-2-fluorohexahydro-1H-pyrrolizin-7a-yl)methoxy)-N-methyl-N—((R)-piperidin-3-yl)pyrido[4,3-d]pyrimidin-4-amine The de-Boc protecting reaction was prepared in a similar fashion to Method #1, Step 9. The mixture was concentrated to dryness in vacuo affording 7-(8-chloronaphthalen-1-yl)-8-fluoro-2-(((2R,7aS)-2-fluorohexahydro-1H-pyrrolizin-7a-yl)methoxy)-N-methyl-N—((R)-piperidin-3-yl)pyrido[4,3-d]pyrimidin-4-amine (30 mg, crude, trifluoroacetate salt) as a yellow oil and used in next step without further purification. LCMS Rt=0.664 min, m/z=578.2 [M+H]⁺.

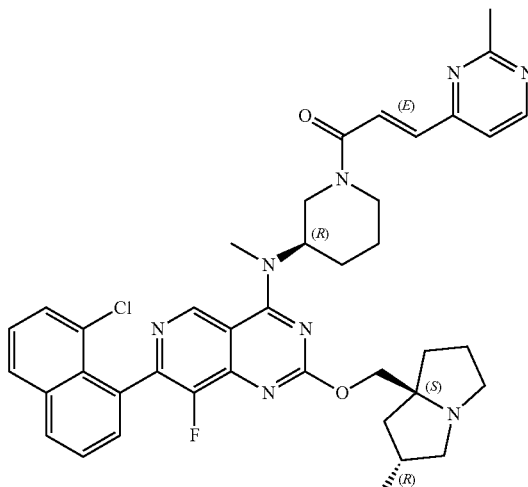

Step 5: (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)piperidin-1-yl)-3-(2-methylpyrimidin-4-yl)prop-2-en-1-one The amide coupling reaction was prepared in a similar fashion to Method #1, Step 10. The residue was purified by reverse phase HPLC (column: Waters Xbridge BEH C18 100*30 mm*10 μm; mobile phase: [water (NH₄HCO₃)—Acetonitrile]; B %: 35%-65%, 8 min) affording (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)piperidin-1-yl)-3-(2-methylpyrimidin-4-yl)prop-2-en-1-one (9 mg, 28.02%) as a yellow solid: ¹H NMR (400 MHz, Acetonitrile-d3) δ 9.29-9.18 (m, 1H), 8.72-8.60 (m, 1H), 8.15 (d, J=7.9 Hz, 1H), 8.04 (d, J=8.0 Hz, 1H), 7.78-7.67 (m, 2H), 7.67-7.59 (m, 2H), 7.57-7.51 (m, 1H), 7.44 (br d, J=15.6 Hz, 1H), 7.35 (br d, J=5.0 Hz, 1H), 5.39-5.01 (m, 1H), 4.99-4.79 (m, 1H), 4.76-4.57 (m, 1H), 4.44-4.26 (m, 1H), 4.24-4.05 (m, 2H), 3.54-3.44 (m, 3H), 3.26-3.11 (m, 2H), 3.10-2.75 (m, 4H), 2.73-2.59 (m, 3H), 2.13 (br dd, J=2.6, 4.9 Hz, 2H), 2.09 (br s, 2H), 1.93-1.83 (m, 3H), 1.80 (td, J=2.4, 4.9 Hz, 1H), 1.77-1.63 (m, 2H). LCMS Rt=2.979 min, m/z=724.3 [M+H]⁺.

LCMS (5 to 95% acetonitrile in water+0.03% ammonium bicarbonate over 6 mins) retention time 2.979 min, ESI+ found [M+H]=724.3.

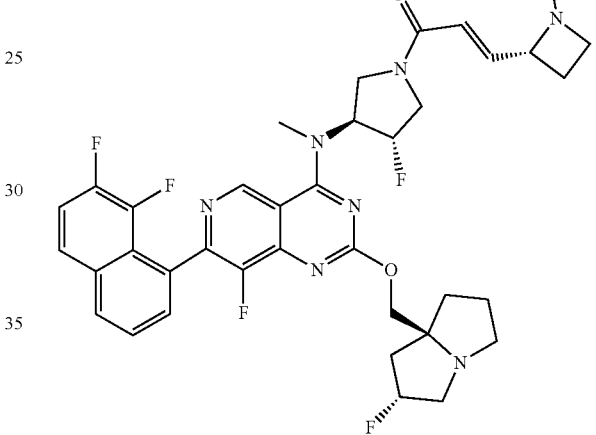

Example 199 (Method 11): (E)-1-((3S,4S)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-((R)-1-methylazetidin-2-yl)prop-2-en-1-one

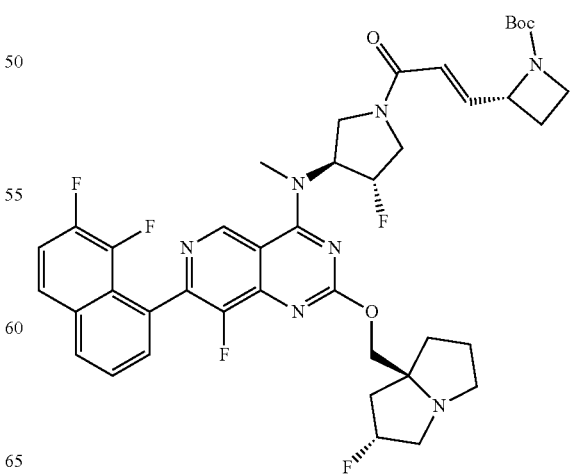

Step 1: tert-butyl (R)-2-((E)-3-((3S,4S)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-oxoprop-1-en-1-yl)azetidine-1-carboxylate The amide coupling reaction was prepared in a similar fashion to Method #11, Step 11. The reaction mixture was diluted with water (5 mL) and extracted with dichloromethane (3×5 mL). The combined organic layers were dried over sodium sulphate and concentrated in vacuo affording tert-butyl (R)-2-((E)-3-((3S,4S)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-oxoprop-1-en-1-yl)azetidine-1-carboxylate (80 mg, crude) as a yellow oil and used in next step without any further purification. LCMS Rt=0.722 min, m/z=693.3 [M+H]$^+$.

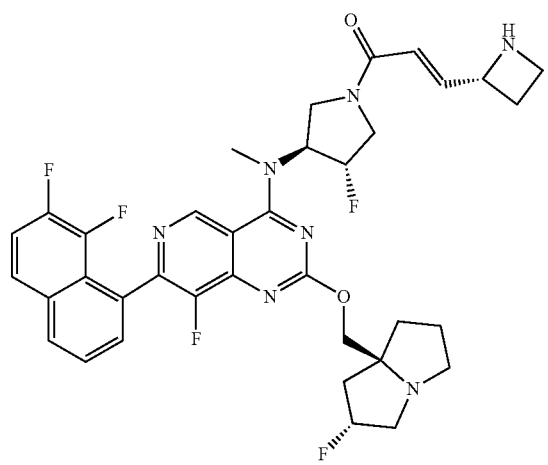 [SMILES: CN(c1nc(OC[C@@]23CCCN2C[C@H](F)C3)nc2c(F)c(-c3cccc4ccc(F)c(F)c34)ncc12)[C@H]1CN(C(=O)/C=C/[C@H]2CCN2)C[C@@H]1F]

Step 2: (E)-3-((R)-azetidin-2-yl)-1-((3S,4S)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)prop-2-en-1-one The deprotection of Boc group was prepared in a similar fashion to Method #11, Step 12. The reaction mixture was concentrated in vacuo affording (E)-3-((R)-azetidin-2-yl)-1-((3S,4S)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)prop-2-en-1-one (80 mg, crude, trifluoroacetic acid salt) as a yellow oil and used in next step without any further purification. LCMS Rt=0.639 min, m/z=693.3 [M+H]$^+$.

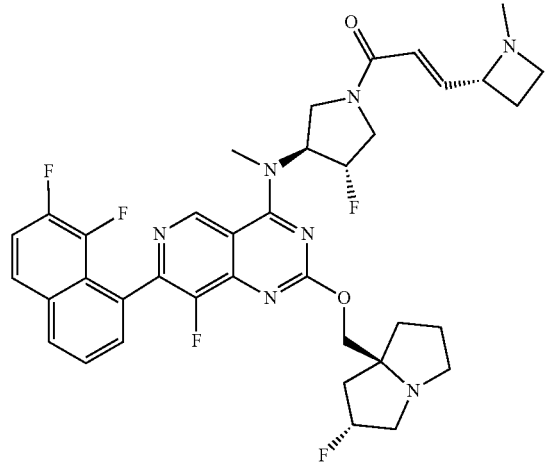 [SMILES: CN1CC[C@@H]1/C=C/C(=O)N1C[C@H](F)[C@@H](N(C)c2nc(OC[C@@]34CCCN3C[C@H](F)C4)nc3c(F)c(-c4cccc5ccc(F)c(F)c45)ncc23)C1]

Step 3: (E)-1-((3S,4S)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-((R)-1-methylazetidin-2-yl)prop-2-en-1-one The reductive amination was prepared in a similar fashion to Method #11, Step 13. The residue was purified by prep-HPLC (column: Phenomenex Luna C18 75*30 mm*3 μm; mobile phase: [water (FA)-ACN]; B %: 1%-35%, 8 min) affording (E)-1-((3S,4S)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-((R)-1-methylazetidin-2-yl)prop-2-en-1-one (2 mg, 2.40%, formic acid salt) as a yellow solid: $^1$H NMR (400 MHz, Acetonitrile-d3) δ 9.28 (s, 1H), 8.11 (br d, J=5.1 Hz, 1H), 7.94-7.86 (m, 1H), 7.71-7.61 (m, 2H), 7.59-7.49 (m, 1H), 6.91-6.74 (m, 1H), 6.41 (br dd, J=7.8, 15.1 Hz, 1H), 5.74-5.51 (m, 1H), 5.40-5.14 (m, 2H), 4.30-4.17 (m, 3H), 4.16-4.04 (m, 1H), 3.97-3.77 (m, 2H), 3.73 (br dd, J=6.4, 12.8 Hz, 1H), 3.52 (br s, 3H), 3.39 (br s, 1H), 3.26-3.08 (m, 3H), 2.99-2.86 (m, 2H), 2.20 (br d, J=7.3 Hz, 3H), 2.15 (br dd, J=6.5, 10.6 Hz, 2H), 2.11-1.98 (m, 3H), 1.88 (br d, J=8.0 Hz, 3H). LCMS Rt=2.012 min, m/z=707.3 [M+H]$^+$.

LCMS (5 to 95% acetonitrile in water+0.1% trifluoroacetic acid over 6 mins) retention time 2.012 min, ESI+ found [M+H]=707.3.

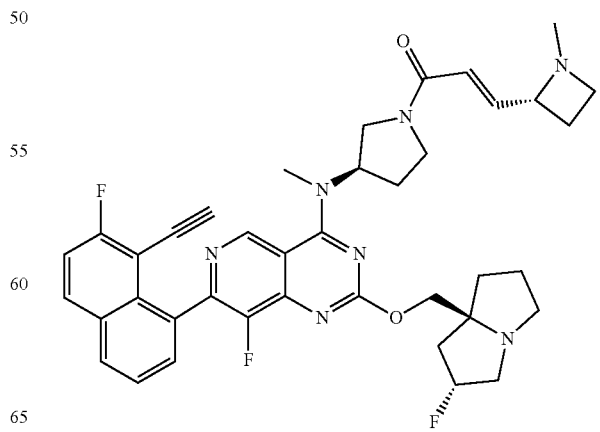

Example 200 (Method 11-Master): (E)-1-((R)-3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-((R)-1-methylazetidin-2-yl)prop-2-en-1-one

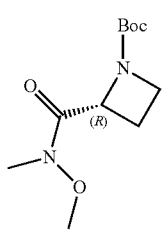

Step 1: tert-butyl (R)-2-(methoxy(methyl)carbamoyl)azetidine-1-carboxylate

To a solution of N-methoxymethanamine (4.85 g, 49.70 mmol, hydrochloric acid salt) in N,N-dimethylformaldehyde (50 mL) was added (2R)-1-tert-butoxycarbonylazetidine-2-carboxylic acid (5 g, 24.85 mmol), 1-(3-Dimethylaminopropyl)-3-ethylcarbodiimide (9.53 g, 49.70 mmol), 1-Hydroxybenzotriazole (6.72 g, 49.70 mmol) and 4-Methylmorpholine (7.54 g, 74.55 mmol), then the mixture was stirred at 20° C. for 2 h. The mixture was diluted with water (20 mL) and extracted with ethyl acetate (3×50 mL). The combined organic layers were dried over sodium sulphate and concentrated in vacuo. The residue was purified by column chromatography (silica gel, 100-200 mesh, 60-80% ethyl acetate in petroleum ether) affording tert-butyl (R)-2-(methoxy(methyl)carbamoyl)azetidine-1-carboxylate (5 g, 82.37%) as a colourless oil. LCMS Rt =0.568 min, m/z=244.1 [M+H]⁺.

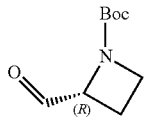

Step 2: tert-butyl (R)-2-formylazetidine-1-carboxylate

To a solution of tert-butyl (R)-2-(methoxy(methyl)carbamoyl)azetidine-1-carboxylate (5 g, 20.47 mmol) in tetrahydrofuran (50 mL) was added diisobutylaluminum hydride in toluene (1 M, 40.94 mL) at −65° C., then the mixture was stirred at −65° C. for 1 h under nitrogen atmosphere. The reaction was quenched with saturated ammonium chloride (20 mL) at 0° C. and extracted with ethyl acetate (2×30 mL). The combined organic layers were dried over sodium sulphate and concentrated in vacuo affording tert-butyl (R)-2-formylazetidine-1-carboxylate (3 g, 79.13%) as a colourless oil and used in the next step without further purification.

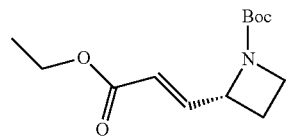 [SMILES: CCOC(=O)/C=C/[C@H]1CCN1C(=O)OC(C)(C)C]

Step 3: tert-butyl (R,E)-2-(3-ethoxy-3-oxoprop-1-en-1-yl)azetidine-1-carboxylate To a solution of ethyl 2-diethoxyphosphorylacetate (3.63 g, 16.20 mmol) in acetonitrile (30 mL) was added tert-butyl (2R)-2-formylazetidine-1-carboxylate (3 g, 16.20 mmol), lithium chloride (2.06 g, 48.59 mmol) and N,N-diisopropylethylamine (6.28 g, 48.59 mmol) and the mixture was stirred at 20° C. for 2 h. The mixture was diluted with water (20 mL) and extracted with ethyl acetate (3×50 mL). The combined organic layers were dried over sodium sulphate and concentrated in vacuo. The residue was purified by column chromatography (silica gel, 100-200 mesh, 40-60% ethyl acetate in petroleum ether) affording tert-butyl (R,E)-2-(3-ethoxy-3-oxoprop-1-en-1-yl)azetidine-1-carboxylate (2.3 g, 55.62%) as a yellow gum. LCMS Rt=0.768 min, m/z=255.2 [M+H]⁺.

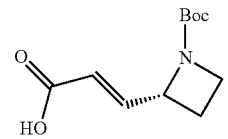 [SMILES: CC(C)(C)OC(=O)N1CC[C@@H]1/C=C/C(=O)O]

Step 4: (R,E)-3-(1-(tert-butoxycarbonyl)azetidin-2-yl)acrylic acid

To a solution of tert-butyl (R,E)-2-(3-ethoxy-3-oxoprop-1-en-1-yl)azetidine-1-carboxylate (500 mg, 1.96 mmol) in dioxane (3 mL) and water (3 mL) was added lithium hydrate (123.27 mg, 2.94 mmol), then the mixture was stirred at 20° C. for 1 h. The reaction mixture was quenched with 1M HCl (6 mL) at 0° C., then extracted with ethyl acetate (3×10 mL). The combined organic layers were dried over sodium sulphate and concentrated in vacuo affording (R,E)-3-(1-(tert-butoxycarbonyl)azetidin-2-yl)acrylic acid (340 mg, 76.39%) as a yellow oil. LCMS Rt=0.567 min, m/z=227.1 [M+H]⁺.

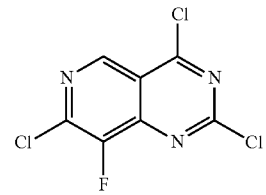 [SMILES: Fc1c(Cl)ncc2c(Cl)nc(Cl)nc12]

Step 5: 2,4,7-trichloro-8-fluoropyrido[4,3-d]pyrimidine

To a solution of 7-chloro-8-fluoropyrido[4,3-d]pyrimidine-2,4-diol (100 g, 464 mmol) and trichlorophosphate (500 mL) in anhydrous toluene (600 mL) was added N,N- diisopropylethylamine (148 g, 1.15 mol) at 0° C. under a nitrogen atmosphere. The mixture was stirred at 110° C. for 12 h. The mixture was diluted with water (5 L) and extracted with ethyl acetate (3×2 L). The reaction mixture was concentrated in vacuo affording 2,4,7-trichloro-8-fluoropyrido[4,3-d]pyrimidine (117 g, crude) as a yellow oil and used in next step without any further purification. LCMS Rt=0.725 min, m/z=251.9 [M+H]$^+$.

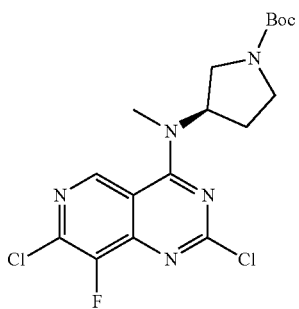 [SMILES: CN(c1nc(Cl)nc2c(F)c(Cl)ncc12)[C@@H]1CCN(C(=O)OC(C)(C)C)C1]

Step 6: (R)-tert-butyl 3-((2,7-dichloro-8-fluoropyrido[4,3-d]pyrimidin-4-yl)(methyl)amino)pyrrolidine-1-carboxylate To a solution of 2,4,7-trichloro-8-fluoropyrido[4,3-d]pyrimidine (177 g, 701 mmol) in tetrahydrofuran (2400 mL) and N,N-diisopropylethylamine (119 g, 927 mmol) was added (R)-tert-butyl 3-(methylamino)pyrrolidine-1-carboxylate (79 g, 394 mmol) at 0° C. under a nitrogen atmosphere. The mixture was stirred at 0° C. for 0.5 h. The mixture was diluted with water (5 L) and extracted with ethyl acetate (3×2 L). The combined organic layers were dried over sodium sulphate and concentrated in vacuo. The crude residue was diluted with tert-butyl methyl ether (400 mL) and the resulting precipitate was filtered affording (R)-tert-butyl 3-((2,7-dichloro-8-fluoropyrido[4,3-d]pyrimidin-4-yl)(methyl)amino)pyrrolidine-1-carboxylate (120 g, 62.18%) as a light yellow solid. LCMS Rt=0.798 min, m/z=416.1 [M+H]$^+$.

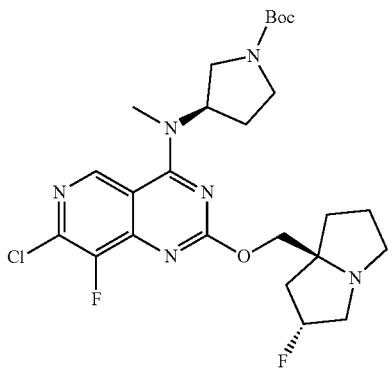 [SMILES: CN(c1nc(OC[C@@]23CCCN2C[C@H](F)C3)nc2c(F)c(Cl)ncc12)[C@@H]1CCN(C(=O)OC(C)(C)C)C1]

Step 7: (R)-tert-butyl 3-((7-chloro-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate To a solution of ((2R,7aS)-2-fluorohexahydro-1H-pyrrolizin-7a-yl)methanol (38.24 g, 240.22 mmol) and 4A MS (25 g) in dioxane (1000 mL) were added (R)-tert-butyl 3-((2,7-dichloro-8-fluoropyrido[4,3-d]pyrimidin-4-yl)(methyl)amino)pyrrolidine-1-carboxylate (50 g, 120.11 mmol) and N,N-diisopropylethylamine (46.57 g, 360.34 mmol), then the mixture was stirred at 100° C. for 24 h under a nitrogen atmosphere. The mixture was filtered and the filter cake was diluted with a mixture of petroleum ether:ethyl acetate (14 L, 2.5:1) for two times. The resulting precipitate was filtered and concentrated to dryness in vacuo affording (R)-tert-butyl 3-((7-chloro-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (160 g, crude) as a white solid and used in next step without any further purification: $^1$H NMR (400 MHz, Chloroform-d) δ 8.87 (s, 1H), 5.39-5.29 (m, 1H), 5.21 (br s, 1H), 4.32-4.25 (m, 1H), 4.24-4.15 (m, 1H), 3.82 (dd, J=11.2, 8.0 Hz, 1H), 3.66 (br d, J=4.0 Hz, 1H), 3.47-3.39 (m, 2H), 3.37 (s, 3H), 3.32-3.22 (m, 2H), 3.17 (br s, 1H), 3.04-2.93 (m, 1H), 2.34-2.08 (m, 5H), 2.04-1.78 (m, 3H), 1.49 (s, 9H). LCMS Rt=0.545 min, m/z=539.2 [M+H]$^+$.

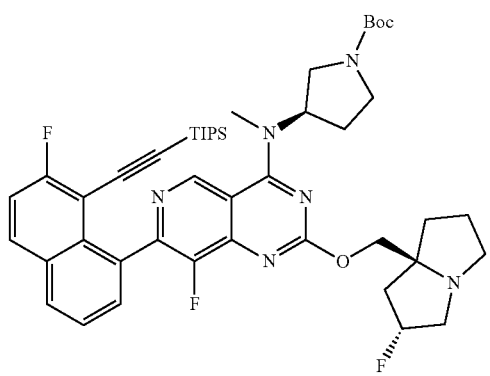

Step 8: (R)-tert-butyl 3-((8-fluoro-7-(7-fluoro-8-((triisopropylsilyl)ethynyl)naphthalen-1-yl)-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate To a solution of (R)-tert-butyl 3-((7-chloro-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (21.34 g, 39.59 mmol) in dioxane (500 mL) and water (100 mL) was added 2-[2-fluoro-8-(4,4,5,5-tetramethyl-1,3,2-dioxaborolan-2-yl)-1-naphthyl]ethynyl-triisopropyl-silane (18.81 g, 41.57 mmol), potassium phosphate (25.21 g, 118.77 mmol) and [2-(2-aminophenyl)phenyl]-chloro-palladium; Bis(1-adamantyl)-butyl-phosphane (2.65 g, 3.96 mmol), then the mixture was heated to 90° C. and stirred for 12 h under a nitrogen atmosphere. The mixture was poured into water (200 mL) and concentrated under reduced pressure to remove dioxane, diluted with water (500 mL) and extracted with ethyl acetate (3×300 mL). The combined organic layers were dried over sodium sulphate and concentrated in vacuo. The residue was purified by column chromatography (silica gel, 100-200 mesh, 0-100% tetrahydrofuran in petroleum ether). The product was dissolved into ethyl acetate (220 mL) followed by the addition of 2-silylethanethiol (10 g, 108.42 mmol) amd the mixture was stirred at 75° C. for 12 h to remove residue Pd. The reaction mixture was filtered and the filter cake was concentrated to dryness in vacuo affording (R)-tert-butyl 3-((8-fluoro-7-(7-fluoro-8-((triisopropylsilyl)ethynyl)naphthalen-1-yl)-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (25 g, 76.16%) as a yellow solid. LCMS Rt=0.872 min, m/z=829.4 [M+H]$^+$.

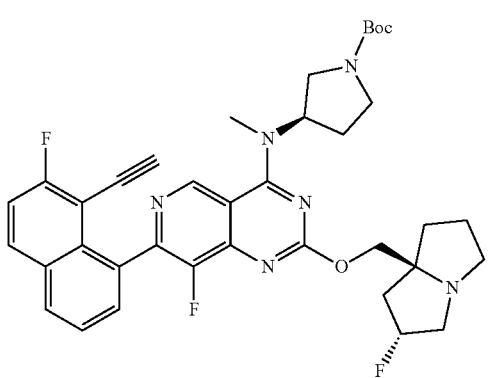 [SMILES: C#Cc1c(F)ccc2cccc(-c3ncc4c(N(C)[C@@H]5CCN(C(=O)OC(C)(C)C)C5)nc(OC[C@@]56CCCN5C[C@H](F)C6)nc4c3F)c12]

Step 9: (R)-tert-butyl 3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate To a solution of (R)-tert-butyl 3-((8-fluoro-7-(7-fluoro-8-((triisopropylsilyl)ethynyl)naphthalen-1-yl)-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (7 g, 8.44 mmol) in acetonitrile (120 mL) was added cesium fluoride (7.70 g, 50.66 mmol) and the mixture was stirred at 25° C. for 12 h. To the reaction mixture was added water (200 ml) and concentrated under reduced pressure to remove acetonitrile, diluted with water (100 mL) and extracted with ethyl acetate (3×100 mL). The combined organic layers were dried over sodium sulphate and concentrated in vacuo. The residue was diluted with a mixture of petroleum ether:ethyl acetate (180 mL, 5:1) for two times. The resulting precipitate was filtered and concentrated to dryness in vacuo affording (R)-tert-butyl 3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (4.5 g, 79.23%) as a yellow solid: $^1$H NMR (400 MHz, Chloroform-d) δ 9.12 (s, 1H), 8.00-7.93 (m, 2H), 7.59 (br d, J=7.8 Hz, 2H), 7.34 (t, J=8.8 Hz, 1H), 5.41-5.33 (m, 1.5H), 5.22 (br s, 0.5H), 4.34-4.27 (m, 1H), 4.25-4.20 (m, 1H), 3.91-3.83 (m, 1H), 3.74-3.63 (m, 1H), 3.47-3.39 (m, 5H), 3.31-3.23 (m, 2H), 3.21-3.16 (m, 1H), 3.03-2.95 (m, 1H), 2.90-2.84 (m, 1H), 2.29 (br s, 1H), 2.26-2.19 (m, 2H), 2.14 (br d, J=10.8 Hz, 1H), 1.95 (dt, J=5.0, 11.3 Hz, 4H), 1.50 (s, 9H).

LCMS Rt=0.673 min, m/z=673.3 [M+H]$^+$.

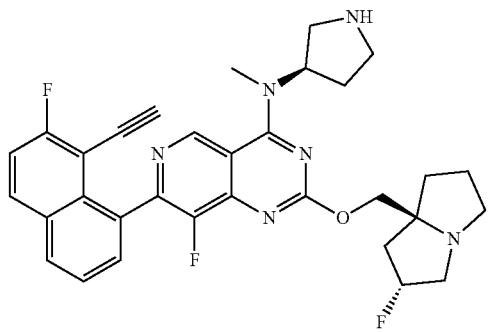 [SMILES: C#Cc1c(F)ccc2cccc(-c3ncc4c(N(C)[C@@H]5CCNC5)nc(OC[C@@]56CCCN5C[C@H](F)C6)nc4c3F)c12]

Step 10: 7-(8-ethynyl-7-fluoronaphthalen-1-yl)-8-fluoro-2-(((2R,7aS)-2-fluorohexahydro-1H-pyrrolizin-7a-yl)methoxy)-N-methyl-N—((R)-pyrrolidin-3-yl)pyrido[4,3-d]pyrimidin-4-amine A mixture of (R)-tert-butyl 3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (5 g, 7.43 mmol) in hydrochloric acid/dioxane (4M, 80 mL) was stirred at 25° C. for 1 h. The reaction mixture was concentrated in vacuo affording 7-(8-ethynyl-7-fluoronaphthalen-1-yl)-8-fluoro-2-(((2R,7aS)-2-fluorohexahydro-1H-pyrrolizin-7a-yl)methoxy)-N-methyl-N—((R)-pyrrolidin-3-yl)pyrido[4,3-d]pyrimidin-4-amine (4.8 g, crude, 2 hydrochloride salt) as a yellow solid and used in next step without any further purification. LCMS Rt=0.558 min, m/z=573.3 [M+H]$^+$.

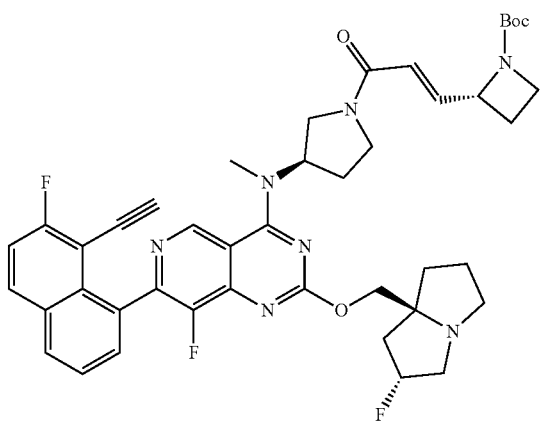 [SMILES: C#Cc1c(F)ccc2cccc(-c3ncc4c(N(C)[C@@H]5CCN(C(=O)/C=C/[C@H]6CCN6C(=O)OC(C)(C)C)C5)nc(OC[C@@]56CCCN5C[C@H](F)C6)nc4c3F)c12]

Step 11: (R)-tert-butyl 2-((E)-3-((R)-3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-en-1-yl)azetidine-1-carboxylate To a solution of (R,E)-3-(1-(tert-butoxycarbonyl)azetidin-2-yl)acrylic acid (388.04 mg, 1.71 mmol) in dichloromethane (8 mL) were added 7-(8-ethynyl-7-fluoronaphthalen-1-yl)-8-fluoro-2-(((2R,7aS)-2-fluorohexahydro-1H-pyrrolizin-7a-yl)methoxy)-N-methyl-N—((R)-pyrrolidin-3-yl)pyrido[4,3-d]pyrimidin-4-amine (800 mg, 1.31 mmol, dihydrochloride salt), N,N-diisopropylethylamine (509.25 mg, 3.94 mmol) and 2-(3H-[1,2,3]triazolo[4,5-b]pyridin-3-yl)-1,1,3,3-tetramethyluronium hexafluorophosphate(V) (749.12 mg, 1.97 mmol) and the mixture was stirred at 20° C. for 1 h. The mixture was diluted with water (15 mL) and extracted with ethyl acetate (3×30 mL). The combined organic layers were dried over sodium sulphate and concentrated in vacuo. The residue was purified by column chromatography (silica gel, 100-200 mesh, 0-20% methanol in dichloromethane) affording (R)-tert-butyl 2-((E)-3-((R)-3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-en-1-yl)azetidine-1-carboxylate (830 mg, 80.82%) as a brown solid. LCMS Rt=0.719 min, m/z=782.4 [M+H]+ a brown oil and used in next step without further purification.

LCMS Rt=0.523 min, m/z=682.3 [M+H]+.

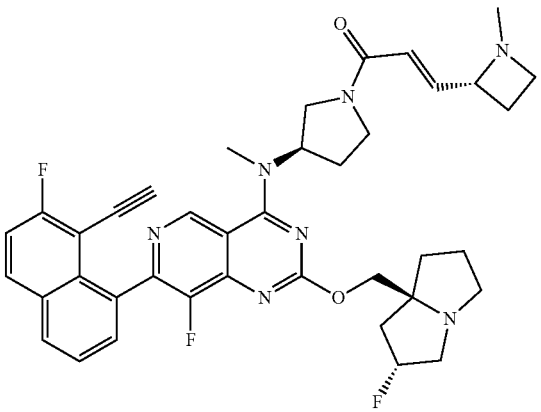

Step 13: (E)-1-((R)-3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-((R)-1-methylazetidin-2-yl)prop-2-en-1-one To a solution of methanal (152.97 mg, 1.88 mmol, 85% purity) in methanol (4 mL) was added acetic acid (3.77 mg, 62.83 μmol) and (E)-3-((R)-azetidin-2-yl)-1-((R)-3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)prop-2-en-1-one (500 mg, 628.32 μmol, trifluoroacetic acid) at 0° C. The mixture was stirred at 20° C. for 0.5 h. Sodium cyanoborohydride (118.45 mg, 1.88 mmol) was added to the reaction mixture and stirred at 20° C. for 2 h. The residue was purified by reverse phase HPLC (column: $C_{18}$-6 100*30 mm*5 μm; mobile phase: [water (FA)-ACN]; B %: 5%-40%, 8 min) affording (E)-1-((R)-3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-((R)-1-methylazetidin-2-yl)prop-2-en-1-one (104.2 mg, 23.41%, formate salt) as a pale yellow solid: $^1$H NMR (400 MHz, Chloroform-d) δ 9.16 (br s, 1H), 8.03-7.93 (m, 2H), 7.81-7.55 (m, 2H), 7.35 (t, J=8.8 Hz, 1H), 7.06-6.94 (m, 1H), 6.73-6.46 (m, 1H), 5.54-5.32 (m, 2H), 5.17-4.80 (m, 4H), 4.72-4.60 (m, 1H), 4.54-4.41 (m, 1H), 4.38-4.22 (m, 1H), 4.17-4.04 (m, 1H), 4.01-3.92 (m, 1H), 3.86-3.69 (m, 3H), 3.63-3.42 (m, 5H), 3.39-3.11 (m, 2H), 3.07-2.90 (m, 1H), 2.62-2.52 (m, 3H), 2.44-2.29 (m, 4H), 2.17 (br dd, J=3.9, 12.4 Hz, 3H). LCMS Rt=1.953 min, m/z=696.3 [M+H]+.

LCMS (5 to 95% acetonitrile in water+0.03% trifluoroacetic acid over 6 mins) retention time 1.953 min, ESI+ found [M+H]=696.3

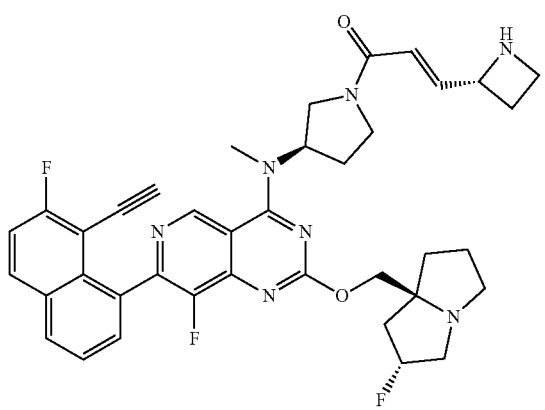 [SMILES: C#Cc1c(F)ccc2cccc(-c3ncc4c(N(C)[C@@H]5CCN(C(=O)/C=C/[C@H]6CCN6)C5)nc(OC[C@@]56CCCN5C[C@H](F)C6)nc4c3F)c12]

Step 12: (E)-3-((R)-azetidin-2-yl)-1-((R)-3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)prop-2-en-1-one A mixture of (R)-tert-butyl 2-((E)-3-((R)-3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-en-1-yl)azetidine-1-carboxylate (500 mg, 639.50 μmol) in dichloromethane (3 mL) and trifluoroacetic acid (1 mL) was stirred at 25° C. for 1 h. The reaction mixture was concentrated in vacuo affording (E)-3-((R)-azetidin-2-yl)-1-((R)-3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)prop-2-en-1-one (500 mg, crude, trifluoroacetate salt) as

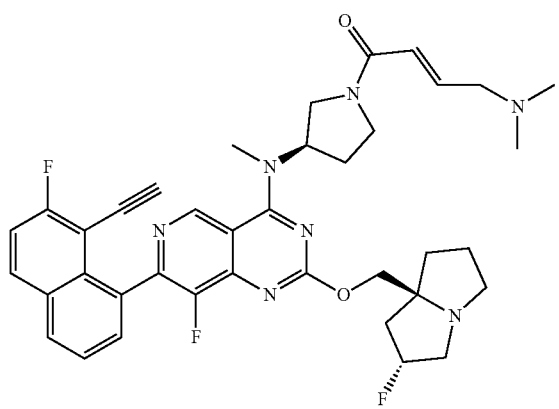 [SMILES: C#Cc1c(F)ccc2cccc(-c3ncc4c(N(C)[C@@H]5CCN(C(=O)/C=C/CN(C)C)C5)nc(OC[C@@]56CCCN5C[C@H](F)C6)nc4c3F)c12]

Example 201 (Method 1): (E)-4-(dimethylamino)-1-((R)-3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)but-2-en-1-one

Step 1: 2,4,7-trichloro-8-fluoropyrido[4,3-d]pyrimidine

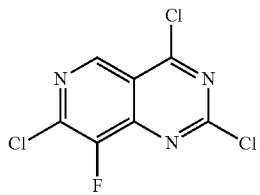 [SMILES: Fc1c(Cl)ncc2c(Cl)nc(Cl)nc12]

To a solution of 7-chloro-8-fluoropyrido[4,3-d]pyrimidine-2,4-diol (100 g, 464 mmol) and trichlorophosphate (500 mL) in anhydrous toluene (600 mL) was added N,N-diisopropylethylamine (148 g, 1.15 mol) at 0° C. under a nitrogen atmosphere. The mixture was stirred at 110° C. for 12 h. The mixture was diluted with water (5 L) and extracted with ethyl acetate (3×2 L). The reaction mixture was concentrated in vacuo affording 2,4,7-trichloro-8-fluoropyrido[4,3-d]pyrimidine (117 g, crude) as a yellow oil and used in next step without any further purification. LCMS Rt=0.725 min, m/z=251.9 [M+H]$^+$.

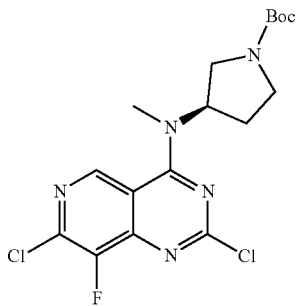 [SMILES: CN(c1nc(Cl)nc2c(F)c(Cl)ncc12)[C@@H]1CCN(C(=O)OC(C)(C)C)C1]

Step 2: (R)-tert-butyl 3-((2,7-dichloro-8-fluoropyrido[4,3-d]pyrimidin-4-yl)(methyl)amino)pyrrolidine-1-carboxylate To a solution of 2,4,7-trichloro-8-fluoropyrido[4,3-d]pyrimidine (177 g, 701 mmol) in tetrahydrofuran (2400 mL) and N,N-diisopropylethylamine (119 g, 927 mmol) was added (R)-tert-butyl 3-(methylamino)pyrrolidine-1-carboxylate (79 g, 394 mmol) at 0° C. under a nitrogen atmosphere. The mixture was stirred at 0° C. for 0.5 h. The mixture was diluted with water (5 L) and extracted with ethyl acetate (3×2 L). The combined organic layers were dried over sodium sulphate and concentrated in vacuo. The crude residue was diluted with tert-butyl methyl ether (400 mL) and the resulting precipitate was filtered affording (R)-tert-butyl 3-((2,7-dichloro-8-fluoropyrido[4,3-d]pyrimidin-4-yl)(methyl)amino)pyrrolidine-1-carboxylate (120 g, 62.18%) as a light yellow solid and used in the next step without further purification. LCMS Rt=0.798 min, m/z=416.1 [M+H]$^+$.

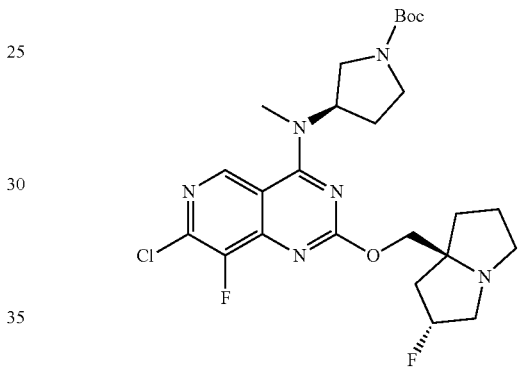

Step 3: (R)-tert-butyl 3-((7-chloro-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate To a solution of ((2R,7aS)-2-fluorohexahydro-1H-pyrrolizin-7a-yl)methanol (38.24 g, 240.22 mmol) and 4A MS (25 g) in dioxane (1000 mL) were added (R)-tert-butyl 3-((2,7-dichloro-8-fluoropyrido[4,3-d]pyrimidin-4-yl)(methyl)amino)pyrrolidine-1-carboxylate (50 g, 120.11 mmol) and N,N-diisopropylethylamine (46.57 g, 360.34 mmol) and the mixture was stirred at 100° C. for 24 h under a nitrogen atmosphere. The mixture was filtered and the filter cake was diluted with a mixture of petroleum ether: ethyl acetate (14 L, 2.5:1) twice. The resulting precipitate was filtered and concentrated to dryness in vacuo affording (R)-tert-butyl 3-((7-chloro-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (160 g, crude) as a white solid and used in next step without any further purification: $^1$H NMR (400 MHz, Chloroform-d) δ 8.87 (s, 1H), 5.39-5.29 (m, 1H), 5.21 (br s, 1H), 4.32-4.25 (m, 1H), 4.24-4.15 (m, 1H), 3.82 (dd, J=11.2, 8.0 Hz, 1H), 3.66 (br d, J=4.0 Hz, 1H), 3.47-3.39 (m, 2H), 3.37 (s, 3H), 3.32-3.22 (m, 2H), 3.17 (br s, 1H), 3.04-2.93 (m, 1H), 2.34-2.08 (m, 5H), 2.04-1.78 (m, 3H), 1.49 (s, 9H). LCMS Rt=0.545 min, m/z=539.2 [M+H]$^+$.

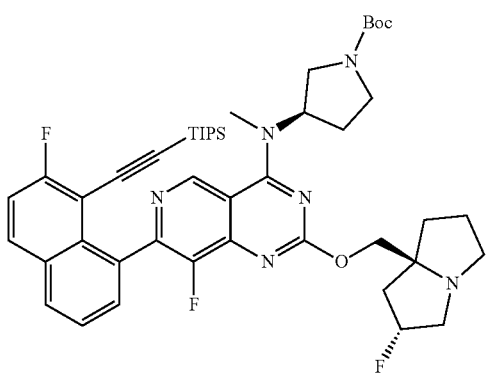

Step 4: (R)-tert-butyl 3-((8-fluoro-7-(7-fluoro-8-((triisopropylsilyl)ethynyl)naphthalen-1-yl)-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate To a solution of (R)-tert-butyl 3-((7-chloro-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (21.34 g, 39.59 mmol) in dioxane (500 mL) and water (100 mL) was added 2-[2-fluoro-8-(4,4,5,5-tetramethyl-1,3,2-dioxaborolan-2-yl)-1-naphthyl]ethynyl-triisopropyl-silane (18.81 g, 41.57 mmol), potassium phosphate (25.21 g, 118.77 mmol) and [2-(2-aminophenyl)phenyl]-chloro-palladium; Bis(1-adamantyl)-butyl-phosphane (2.65 g, 3.96 mmol), then the mixture was heated to 90° C. and stirred for 12 h under a nitrogen atmosphere. The mixture was poured into water (200 mL) and concentrated under reduced pressure to remove dioxane, diluted with water (500 mL) and extracted with ethyl acetate (3×300 mL). The combined organic layers were dried over sodium sulphate and concentrated in vacuo. The residue was purified by column chromatography (silica gel, 100-200 mesh, 0-100% tetrahydrofuran in petroleum ether). The product was dissolved into ethyl acetate (220 mL) followed by the addition of 2-silylethanethiol (10 g, 108.42 mmol) and the mixture was stirred at 75° C. for 12 h to remove residue Pd. The reaction mixture was filtered and the filter cake was concentrated to dryness in vacuo affording (R)-tert-butyl 3-((8-fluoro-7-(7-fluoro-8-((triisopropylsilyl)ethynyl)naphthalen-1-yl)-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (25 g, 76.16%) as a yellow solid. LCMS Rt=0.872 min, m/z=829.4 [M+H]⁺.

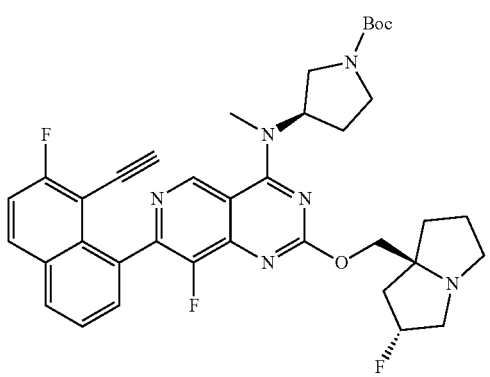 [SMILES: C#Cc1c(F)ccc2cccc(-c3ncc4c(N(C)[C@@H]5CCN(C(=O)OC(C)(C)C)C5)nc(OC[C@@]56CCCN5C[C@H](F)C6)nc4c3F)c12]

Step 5: (R)-tert-butyl 3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate To a solution of (R)-tert-butyl 3-((8-fluoro-7-(7-fluoro-8-((triisopropylsilyl)ethynyl)naphthalen-1-yl)-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (7 g, 8.44 mmol) in acetonitrile (120 mL) was added cesium fluoride (7.70 g, 50.66 mmol) and the mixture was stirred at 25° C. for 12 h. To the reaction mixture was added water (200 ml) and concentrated under reduced pressure to remove acetonitrile, diluted with water (100 mL) and extracted with ethyl acetate (3×100 mL). The combined organic layers were dried over sodium sulphate and concentrated in vacuo. The residue was diluted with a mixture of petroleum ether: ethyl acetate (180 mL, 5:1) twice. The resulting precipitate was filtered and concentrated to dryness in vacuo affording (R)-tert-butyl 3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (4.5 g, 79.23%) as a yellow solid: ¹H NMR (400 MHz, Chloroform-d) δ 9.12 (s, 1H), 8.00-7.93 (m, 2H), 7.59 (br d, J=7.8 Hz, 2H), 7.34 (t, J=8.8 Hz, 1H), 5.41-5.33 (m, 1.5H), 5.22 (br s, 0.5H), 4.34-4.27 (m, 1H), 4.25-4.20 (m, 1H), 3.91-3.83 (m, 1H), 3.74-3.63 (m, 1H), 3.47-3.39 (m, 5H), 3.31-3.23 (m, 2H), 3.21-3.16 (m, 1H), 3.03-2.95 (m, 1H), 2.90-2.84 (m, 1H), 2.29 (br s, 1H), 2.26-2.19 (m, 2H), 2.14 (br d, J=10.8 Hz, 1H), 1.95 (dt, J=5.0, 11.3 Hz, 4H), 1.50 (s, 9H).

LCMS Rt=0.673 min, m/z=673.3 [M+H]⁺.

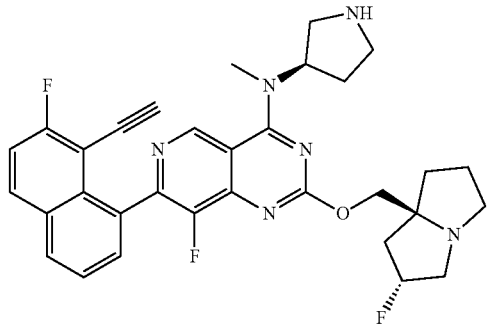 [SMILES: C#Cc1c(F)ccc2cccc(-c3ncc4c(N(C)[C@@H]5CCNC5)nc(OC[C@@]56CCCN5C[C@H](F)C6)nc4c3F)c12]

Step 6: 7-(8-ethynyl-7-fluoronaphthalen-1-yl)-8-fluoro-2-(((2R,7aS)-2-fluorohexahydro-1H-pyrrolizin-7a-yl)methoxy)-N-methyl-N—((R)-pyrrolidin-3-yl)pyrido[4,3-d]pyrimidin-4-amine A mixture of (R)-tert-butyl 3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (5 g, 7.43 mmol) in hydrochloric acid/dioxane (4M, 80 mL) was stirred at 25° C. for 1 h. The reaction mixture was concentrated in vacuo affording 7-(8-ethynyl-7-fluoronaphthalen-1-yl)-8-fluoro-2-(((2R,7aS)-2-fluorohexahydro-1H-pyrrolizin-7a-yl)methoxy)-N-methyl-N—((R)-pyrrolidin-3-yl)pyrido[4,3-d]pyrimidin-4-amine (4.8 g, crude, 2 hydrochloride salt) as a yellow solid and used in next step without any further purification. LCMS Rt=0.558 min, m/z=573.3 [M+H]⁺.

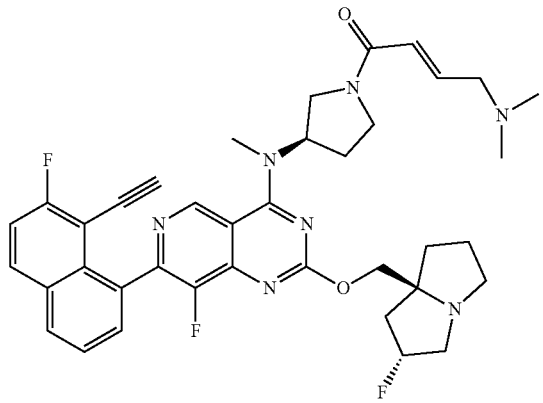 [SMILES: C#Cc1c(F)ccc2cccc(-c3ncc4c(N(C)[C@@H]5CCN(C(=O)/C=C/CN(C)C)C5)nc(OC[C@@]56CCCN5C[C@H](F)C6)nc4c3F)c12]

Step 7: (E)-4-(dimethylamino)-1-((R)-3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)but-2-en-1-one To a solution of (E)-4-(dimethylamino)but-2-enoic acid hydrochloride (21.69 mg, 130.98 μmol) and 7-(8-ethynyl-7-fluoronaphthalen-1-yl)-8-fluoro-2-(((2R,7aS)-2-fluorohexahydro-1H-pyrrolizin-7a-yl)methoxy)-N-methyl-N-((R)-pyrrolidin-3-yl)pyrido[4,3-d]pyrimidin-4-amine (50 mg, 87.32 μmol, hydrochloride salt) in N,N-dimethylformaldehyde (1 mL) was added 2,4,6-tripropyl-1,3,5,2,4,6-trioxatriphosphinane 2,4,6-trioxide (111.13 mg, 174.64 μmol, 50% purity) and N,N-diisopropylethylamine (33.86 mg, 261.95 μmol). The mixture was stirred at 20° C. for 1 h. The mixture was diluted with water (10 mL) and extracted with ethyl acetate (3×20 mL). The combined organic layers were dried over sodium sulphate and concentrated in vacuo. The residue was purified by reverse phase HPLC (column: Phenomenex Luna C18 75*30 mm*3 μm; mobile phase: [water (FA)-ACN]; B %: 1%-35%, 8 min) affording (E)-4-(dimethylamino)-1-((R)-3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)but-2-en-1-one (9.08 mg, 15.21%, formate salt) as a yellow oil: ¹H NMR (400 MHz, Chloroform-d) δ 9.15 (s, 1H), 8.05-7.91 (m, 2H), 7.71-7.51 (m, 2H), 7.41-7.31 (m, 1H), 7.03-6.87 (m, 1H), 6.67-6.40 (m, 1H), 5.50-5.26 (m, 2H), 4.55-4.36 (m, 2H), 4.33-4.16 (m, 1H), 4.11-3.97 (m, 2H), 3.90 (br d, J=7.5 Hz, 2H), 3.69-3.59 (m, 2H), 3.49-3.44 (m, 3H), 3.38-3.25 (m, 2H), 3.11-3.02 (m, 1H), 2.90 (br d, J=8.5 Hz, 1H), 2.56-2.43 (m, 6H), 2.42-2.18 (m, 5H), 2.13-1.99 (m, 3H). LCMS Rt=1.985 min, m/z=684.3 [M+H]⁺.

LCMS (5 to 95% acetonitrile in water+0.03% trifluoroacetic acid over 6 mins) retention time 1.985 min, ESI+ found [M+H]=684.3

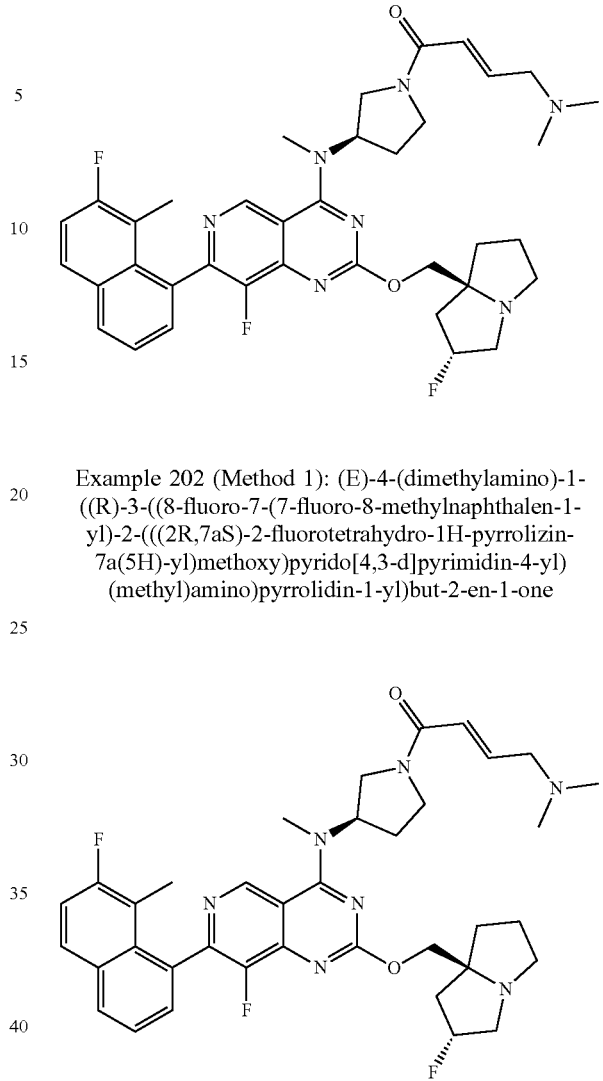

Example 202 (Method 1): (E)-4-(dimethylamino)-1-((R)-3-((8-fluoro-7-(7-fluoro-8-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)but-2-en-1-one Step 1: (E)-4-(dimethylamino)-1-((R)-3-((8-fluoro-7-(7-fluoro-8-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)but-2-en-1-one The amide coupling reaction was prepared in a similar fashion to Method #1, Step 10. The residue was purified by reverse phase HPLC (column: Waters Xbridge BEH C18 100*30 mm*10 μm; mobile phase: [water (NH₄HCO₃)-ACN]; B %: 35%-60%, 8 min) affording (E)-4-(dimethylamino)-1-((R)-3-((8-fluoro-7-(7-fluoro-8-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)but-2-en-1-one (26.07 mg, 31.63%) as a white solid: ¹H NMR (400 MHz, Acetonitrile-d3) δ 9.20 (d, J=2.1 Hz, 1H), 8.04 (dd, J=2.0, 7.4 Hz, 1H), 7.92 (dd, J=6.0, 8.9 Hz, 1H), 7.61-7.48 (m, 2H), 7.38 (t, J=9.3 Hz, 1H), 6.74 (dtd, J=2.4, 6.2, 15.1 Hz, 1H), 6.44-6.31 (m, 1H), 5.43-5.16 (m, 2H), 4.24-4.17 (m, 1H), 4.14 (d, J=2.4 Hz, 1H), 4.11-3.99 (m, 1H), 3.97-3.76 (m, 2H), 3.70-3.47 (m, 2H), 3.45-3.40 (m, 3H), 3.17-3.09 (m, 2H), 3.08-3.01 (m, 3H), 2.92-2.84 (m, 1H), 2.42-2.34 (m, 1H), 2.32-2.25 (m, 1H), 2.19 (d, J=6.4 Hz, 6H), 2.12-2.08 (m, 1H), 2.07-1.99 (m, 1H), 1.92-1.89 (m, 1H), 1.87 (br d, J=2.1 Hz, 4H), 1.85-1.79 (m, 1H). LCMS Rt=2.053 min, m/z=673.3 [M+H]$^+$.

LCMS (5 to 95% acetonitrile in water+0.03% ammonium bicarbonate over 6 mins) retention time 2.053 min, ESI+ found [M+H]=673.3.

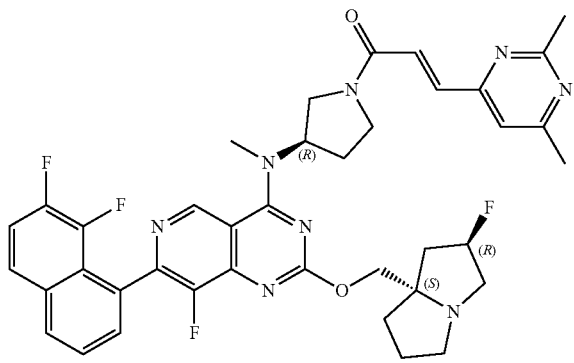

Example 203 (Method 1): (E)-1-((R)-3-((7-(7, 8-difluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(2,6-dimethylpyrimidin-4-yl)prop-2-en-1-one

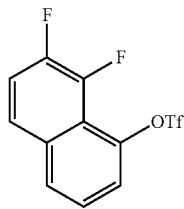 [SMILES: O=S(=O)(Oc1cccc2ccc(F)c(F)c12)C(F)(F)F]

Step 1: (7, 8-difluoro-1-naphthyl) trifluoromethanesulfonate

To a solution of 7, 8-difluoronaphthalen-1-ol (1 g, 5.55 mmol) in dichloromethane (200 mL) was added N,N-diisopropylethylamine (4.30 g, 33.31 mmol). The mixture was stirred at 25° C. for 5 min. Then the trifluoromethanesulfonic anhydride (2.04 g, 7.22 mmol) was added dropwise in the mixture at −40° C. and the mixture was stirred at −40° C. for 55 min under a nitrogen atmosphere. The reaction mixture was concentrated in vacuo and purified by column chromatography (silica gel, 100-200 mesh, 0%-10% ethyl acetate in petroleum ether) affording (7, 8-difluoro-1-naphthyl) trifluoromethanesulfonate (1.1 g, 63.47%) as a yellow oil and used as is in the next step.

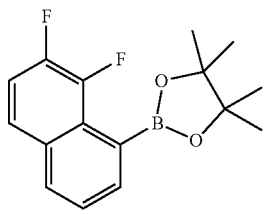 [SMILES: CC1(C)OB(c2cccc3ccc(F)c(F)c23)OC1(C)C]

Step 2: 2-(7, 8-difluoro-1-naphthyl)-4,4,5,5-tetramethyl-1,3,2-dioxaborolane

To a mixture of (7, 8-difluoro-1-naphthyl) trifluoromethanesulfonate (1.1 g, 38.44 mmol), [1,1-Bis(diphenylphosphino)ferrocene]palladium(II)dichloride (281 mg, 3.84 mmol), potassium acetate (1.88 g, 192.18 mmol) and 4,4,5,5-tetramethyl-2-(4,4,5,5-tetramethyl-1,3,2-dioxaborolan-2-yl)-1,3,2-dioxaborolane (1.95 g, 76.87 mmol) in dioxane (15 mL) was degassed and purged with nitrogen for 3 times, and the mixture was stirred at 80° C. for 12 h under a nitrogen atmosphere. The mixture was diluted with water (20 mL) and extracted with ethyl acetate (3×20 mL). The combined organic layers were dried over sodium sulphate and concentrated in vacuo. The residue was purified by column chromatography (silica gel, 100-200 mesh, 0-10% ethyl acetate in petroleum ether) affording 2-(7, 8-difluoro-1-naphthyl)-4,4,5,5-tetramethyl-1,3,2-dioxaborolane (1.35 g, 92.82%) as a yellow solid and used as is in the next step.

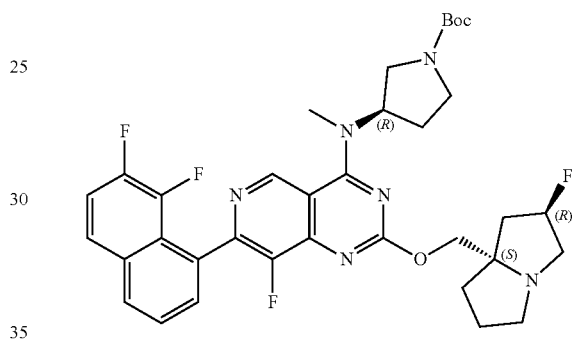

Step 3: (R)-tert-butyl 3-((7-(7, 8-difluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate The Suzuki reaction was prepared in a similar fashion to Method #2, Step 5. The residue was purified by column chromatography (silica gel, 100-200 mesh, 10%-50% methanol in dichloromethane) affording (R)-tert-butyl 3-((7-(7, 8-difluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (550 mg, 88.93%) as a yellow oil. LCMS Rt=0.767 min, m/z=666.3 [M+H]$^+$.

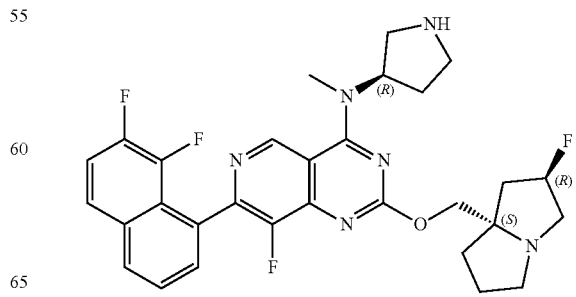

Step 4: 7-(7, 8-difluoronaphthalen-1-yl)-8-fluoro-2-(((2R,7aS)-2-fluorohexahydro-1H-pyrrolizin-7a-yl)methoxy)-N-methyl-N—((R)-pyrrolidin-3-yl)pyrido[4,3-d]pyrimidin-4-amine The de-Boc reaction was prepared in a similar fashion to Method #1, Step 9. The mixture was concentrated to dryness in vacuo affording 7-(7, 8-difluoronaphthalen-1-yl)-8-fluoro-2-(((2R,7aS)-2-fluorohexahydro-1H-pyrrolizin-7a-yl)methoxy)-N-methyl-N—((R)-pyrrolidin-3-yl)pyrido[4,3-d]pyrimidin-4-amine (100 mg, crude, trifluoroacetate salt) as a yellow gum and used in next step without any further purification. LCMS Rt=0.617 min, m/z=566.2 [M+H]⁺.

Step 5: (E)-1-((R)-3-((7-(7, 8-difluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(2,6-dimethylpyrimidin-4-yl)prop-2-en-1-one The amide coupling reaction was prepared in a similar fashion to Method #1, Step 10. The reaction mixture was concentrated in vacuo and the residue was purified by reverse phase HPLC (column: Waters Xbridge Prep OBD C18 150*40 mm*10 μm; mobile phase: [water (NH₄HCO₃)-ACN]; B %: 35%-65%, 8 min) affording (E)-1-((R)-3-((7-(7, 8-difluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(2,6-dimethylpyrimidin-4-yl)prop-2-en-1-one (15.08 mg, 14.09%) as a pale yellow amorphous solid: ¹H NMR (400 MHz, Acetonitrile-d3) δ 9.27 (d, J=2.1 Hz, 1H), 8.20-8.12 (m, 1H), 7.98-7.90 (m, 1H), 7.73 (br d, J=5.7 Hz, 2H), 7.63-7.52 (m, 2H), 7.50-7.42 (m, 1H), 7.28 (d, J=7.7 Hz, 1H), 5.50-5.17 (m, 2H), 4.29-4.23 (m, 1H), 4.20-4.15 (m, 1H), 4.10-3.99 (m, 1H), 3.97-3.76 (m, 2H), 3.71-3.55 (m, 1H), 3.49 (d, J=4.3 Hz, 3H), 3.22-3.16 (m, 1H), 3.15-3.06 (m, 2H), 2.98-2.87 (m, 1H), 2.65 (d, J=11.5 Hz, 3H), 2.49 (d, J=6.1 Hz, 3H), 2.42-2.28 (m, 2H), 2.16-2.06 (m, 3H), 1.95-1.79 (m, 3H). LCMS Rt=2.943 min, m/z=726.3 [M+H]⁺.

LCMS (35 to 65% acetonitrile in water+0.03% ammonium bicarbonate over 8 mins) retention time 2.943 min, ESI+ found [M+H]=726.3.

Example 204 (Method 1): (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(2,6-dimethylpyrimidin-4-yl)prop-2-en-1-one

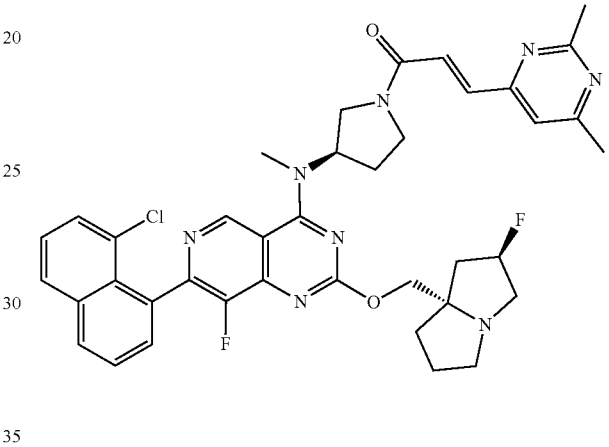

Step 1: (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(2,6-dimethylpyrimidin-4-yl)prop-2-en-1-one The amide coupling reaction was prepared in a similar fashion to Method #1, Step 10. The resulting residue was purified by reverse phase HPLC (column: Waters Xbridge Prep OBD C18 150*40 mm*10 μm; mobile phase: [water (NH₄HCO₃)-ACN]; B %: 35%-65%, 8 min) affording (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(2,6-dimethylpyrimidin-4-yl)prop-2-en-1-one (23.92 mg, 22.34%) as a yellow solid: ¹H NMR (400 MHz, Acetonitrile-d3) δ 9.20 (t, J=2.5 Hz, 1H), 8.12 (dd, J=1.2, 8.2 Hz, 1H), 8.02 (d, J=8.3 Hz, 1H), 7.68 (d, J=8.1 Hz, 1H), 7.65-7.58 (m, 2H), 7.55-7.48 (m, 2H), 7.45-7.36 (m, 1H), 7.23 (d, J=7.0 Hz, 1H), 5.45-5.15 (m, 2H), 4.23-4.19 (m, 1H), 4.18-4.12 (m, 1H), 4.06-3.95 (m, 1H), 3.94-3.70 (m, 2H), 3.66-3.50 (m, 1H), 3.48-3.43 (m, 3H), 3.17-3.04 (m, 3H), 2.93-2.82 (m, 1H), 2.60 (d, J=11.5 Hz, 3H), 2.45 (d, J=6.1 Hz, 3H), 2.36-2.29 (m, 1H), 2.19 (br s, 1H), 2.10-1.99 (m, 3H), 1.90-1.78 (m, 3H). LCMS Rt=2.951 min, m/z=724.3 [M+H]⁺.

LCMS (5 to 95% acetonitrile in water+0.03% ammonium bicarbonate over 6 mins) retention time 2.951 min, ESI+ found [M+H]=724.3.

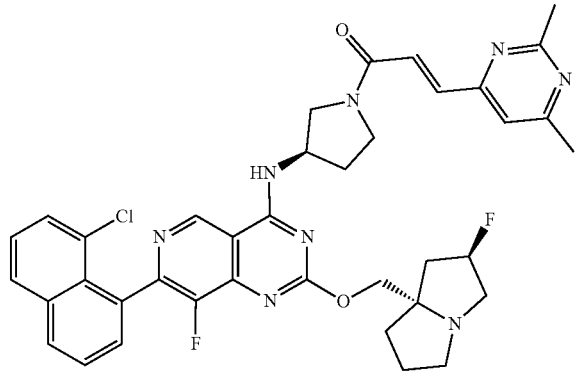 [SMILES: Cc1cc(/C=C/C(=O)N2CC[C@@H](Nc3nc(OC[C@@]45CCCN4C[C@H](F)C5)nc4c(F)c(-c5cccc6cccc(Cl)c56)ncc34)C2)nc(C)n1]

Example 205 (Method 1): (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)pyrrolidin-1-yl)-3-(2,6-dimethylpyrimidin-4-yl)prop-2-en-1-one

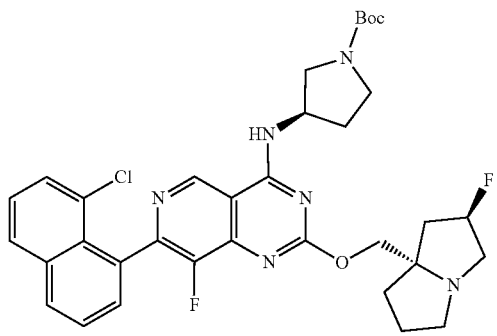 [SMILES: CC(C)(C)OC(=O)N1CC[C@@H](Nc2nc(OC[C@@]34CCCN3C[C@H](F)C4)nc3c(F)c(-c4cccc5cccc(Cl)c45)ncc23)C1]

Step 1: (R)-tert-butyl 3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)pyrrolidine-1-carboxylate The substitution reaction was prepared in a similar fashion to Method #1, Step 8. The reaction mixture was concentrated in vacuo and purified by reverse phase HPLC: (column: Phenomenex Luna 80*30 mm*3 μm; mobile phase: [water (TFA)-ACN]; B %: 15%-55%, 8 min) affording (R)-tert-butyl 3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)pyrrolidine-1-carboxylate (160 mg, 39.55%, trifluoroacetic salt) as a white solid. LCMS Rt=0.601 min, m/z=650.3 [M+H]+.

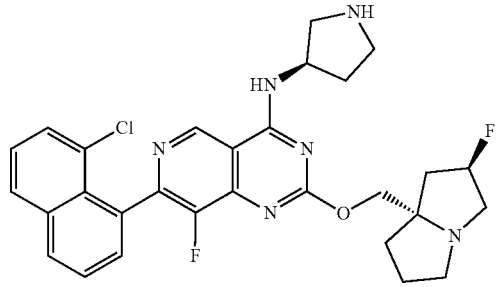 [SMILES: Fc1c(-c2cccc3cccc(Cl)c23)ncc2c(N[C@@H]3CCNC3)nc(OC[C@@]34CCCN3C[C@H](F)C4)nc12]

Step 2: 7-(8-chloronaphthalen-1-yl)-8-fluoro-2-(((2R,7aS)-2-fluorohexahydro-1H-pyrrolizin-7a-yl)methoxy)-N—((R)-pyrrolidin-3-yl)pyrido[4,3-d]pyrimidin-4-amine The deprotection of Boc was prepared in a similar fashion to Method #1, Step 9. The reaction mixture was concentrated in vacuo affording 7-(8-chloronaphthalen-1-yl)-8-fluoro-2-(((2R,7aS)-2-fluorohexahydro-1H-pyrrolizin-7a-yl)methoxy)-N—((R)-pyrrolidin-3-yl)pyrido[4,3-d]pyrimidin-4-amine (70 mg, crude) as a brown oil, used into the next step without further purification. LCMS Rt=0.620 min, m/z=550.2 [M+H]+.

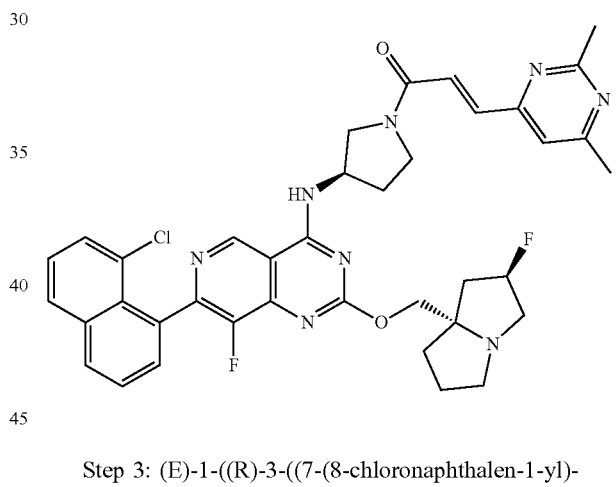

Step 3: (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)pyrrolidin-1-yl)-3-(2,6-dimethylpyrimidin-4-yl)prop-2-en-1-one The amide coupling reaction was prepared in a similar fashion to Method #1, Step 10. The resulting residue was purified by reverse phase HPLC: column: Waters Xbridge Prep OBD C18 150*40 mm*10 μm; mobile phase: [water (NH$_4$HCO$_3$)-ACN]; B %: 30%-60%, 8 min) affording (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)pyrrolidin-1-yl)-3-(2,6-dimethylpyrimidin-4-yl)prop-2-en-1-one (19.32 mg, 25.81%) as a white solid: $^1$H NMR (400 MHz, Acetonitrile-d3) δ 9.12 (br s, 1H), 8.18-7.94 (m, 2H), 7.73-7.55 (m, 3H), 7.52-7.46 (m, 2H), 7.43-7.36 (m, 1H), 7.19 (d, J=8.8 Hz, 1H), 5.42-5.13 (m, 1H), 5.01-4.81 (m, 1H), 4.29-4.06 (m, 3H), 3.99-3.59 (m, 4H), 3.25-3.00 (m, 3H), 2.98-2.78 (m, 1H), 2.58 (d, J=6.6 Hz, 3H), 2.43 (br d, J=4.4 Hz, 3H), 2.36-2.22 (m, 2H), 2.10 (br s, 3H), 1.91-1.73 (m, 3H). LCMS Rt=2.913 min, m/z=710.3 [M+H]⁺.

LCMS (5 to 95% acetonitrile in water+0.03% ammonium bicarbonate over 6 mins) retention time 2.913 min, ESI+ found [M+H]=710.3.

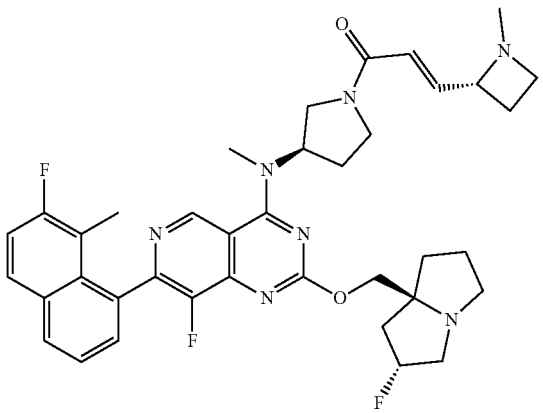 [SMILES: Cc1c(F)ccc2cccc(-c3ncc4c(N(C)[C@@H]5CCN(C(=O)/C=C/[C@H]6CCN6C)C5)nc(OC[C@@]56CCCN5C[C@H](F)C6)nc4c3F)c12]

Example 206 (Method 11): (E)-1-((R)-3-((8-fluoro-7-(7-fluoro-8-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-methylazetidin-2-yl)prop-2-en-1-one

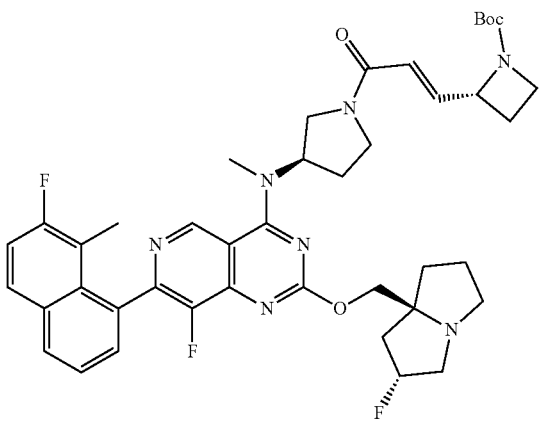 [SMILES: Cc1c(F)ccc2cccc(-c3ncc4c(N(C)[C@@H]5CCN(C(=O)/C=C/[C@H]6CCN6C(=O)OC(C)(C)C)C5)nc(OC[C@@]56CCCN5C[C@H](F)C6)nc4c3F)c12]

Step 1: tert-butyl (R)-2-((E)-3-((R)-3-((8-fluoro-7-(7-fluoro-8-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-oxoprop-1-en-1-yl)azetidine-1-carboxylate The amide coupling reaction was prepared in a similar fashion to Method #11, Step 11. The reaction mixture was diluted with water (10 mL) and extracted with dichloromethane (3×10 mL). The combined organic layers were dried over sodium sulphate and concentrated in vacuo affording tert-butyl (R)-2-((E)-3-((R)-3-((8-fluoro-7-(7-fluoro-8-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-oxoprop-1-en-1-yl)azetidine-1-carboxylate (440 mg, crude) as a yellow oil and used in next step without any further purification. LCMS Rt=0.734 min, m/z =771.4 [M+H]⁺.

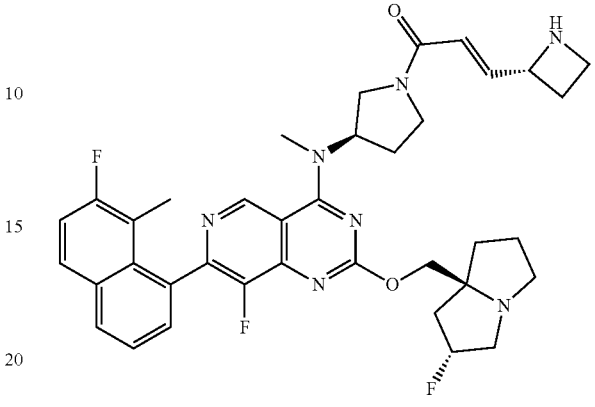

Step 2: (E)-3-((R)-azetidin-2-yl)-1-((R)-3-((8-fluoro-7-(7-fluoro-8-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one The deprotection of Boc group was prepared in a similar fashion to Method #11, Step 12. The reaction mixture was concentrated in vacuo affording (E)-3-((R)-azetidin-2-yl)-1-((R)-3-((8-fluoro-7-(7-fluoro-8-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (100 mg, crude, trifluoroacetic acid salt) as a brown oil and used in next step without any further purification. LCMS Rt=1.176 min, m/z=671.3 [M+H]⁺.

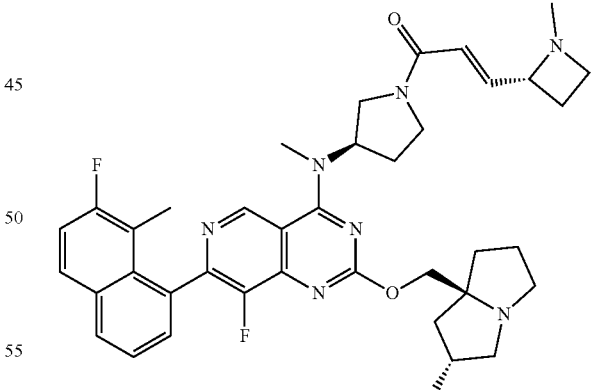

Step 3: (E)-1-((R)-3-((8-fluoro-7-(7-fluoro-8-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-methylazetidin-2-yl)prop-2-en-1-one The reductive amination was prepared in a similar fashion to Method #11, Step 13. The residue was purified by prep-HPLC (column: Waters Xbridge Prep OBD C18 150*40 mm*10 μm; mobile phase: [water (NH₄HCO3)-ACN]; B %: 35%-65%, 8 min) affording (E)-1-((R)-3-((8-fluoro-7-(7-fluoro-8-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-methylazetidin-2-yl)prop-2-en-1-one (5.66 mg, 5.02%) as a white solid: $^1$H NMR (400 MHz, Acetonitrile-d3) δ 9.25-9.16 (m, 1H), 8.05 (dd, J=1.9, 7.4 Hz, 1H), 7.93 (dd, J=6.1, 8.9 Hz, 1H), 7.63-7.49 (m, 2H), 7.38 (t, J=9.4 Hz, 1H), 6.76 (dd, J=5.7, 15.1 Hz, 1H), 6.31 (s, 1H), 5.49-5.15 (m, 2H), 4.25-4.19 (m, 1H), 4.16-4.03 (m, 2H), 3.99-3.75 (m, 2H), 3.70-3.60 (m, 1H), 3.59-3.49 (m, 2H), 3.45-3.39 (m, 4H), 3.33-3.23 (m, 1H), 3.14 (br d, J=7.0 Hz, 2H), 3.06 (s, 1H), 2.93-2.76 (m, 3H), 2.44-2.38 (m, 1H), 2.24 (d, J=7.8 Hz, 4H), 2.10-2.03 (m, 3H), 1.87 (s, 3H), 1.27 (s, 2H). LCMS Rt=2.000 min, m/z=685.3 [M+H]⁺.

LCMS (5 to 95% acetonitrile in water+0.03% ammonium bicarbonate over 6 mins) retention time 2.000 min, ESI+ found [M+H]=685.3.

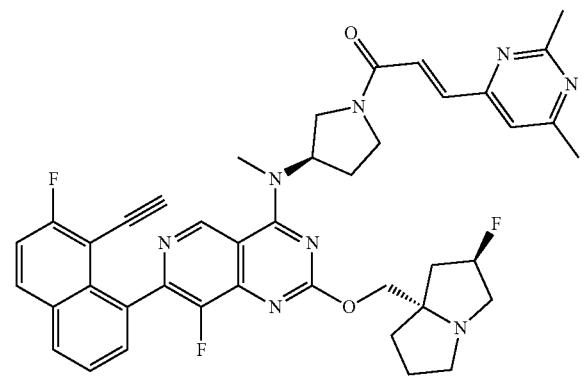

Example 207 (Method 1): (E)-3-(2,6-dimethylpyrimidin-4-yl)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one

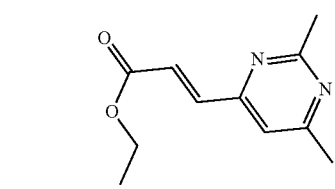

Step 1: ethyl (E)-3-(2,6-dimethylpyrimidin-4-yl)acrylate

A mixture of 4-chloro-2,6-dimethyl-pyrimidine (4 g, 28.05 mmol), ethyl (E)-3-(4,4,5,5-tetramethyl-1,3,2-dioxaborolan-2-yl)prop-2-enoate (7.61 g, 33.66 mmol), potassium phosphate (17.86 g, 84.16 mmol) and chloro(2-dicyclohexylphosphino-2',4',6'-triisopropyl-1,1'-biphenyl)[2-(2'-amino-1,1'-biphenyl)]palladium(II) (2.21 g, 2.81 mmol) in dioxane (60 mL) and water (20 mL) was degassed and purged with nitrogen for 3 times and the mixture was stirred at 100° C. for 2 h under a nitrogen atmosphere. The reaction mixture was diluted with water (30 mL) and extracted with ethyl acetate (3×30 mL). The combined organic layers were dried over sodium sulphate and concentrated in vacuo. The residue was purified by column chromatography (silica gel, 100-200 mesh, 0-100% ethyl acetate in petroleum ether) affording ethyl (E)-3-(2,6-dimethylpyrimidin-4-yl)prop-2-enoate (5 g, 86.42%) as a yellow oil: $^1$H NMR (400 MHz, Chloroform-d) δ 7.52 (d, J=15.6 Hz, 1H), 7.12-7.02 (m, 2H), 4.29 (q, J=7.1 Hz, 2H), 2.72 (s, 3H), 2.53 (s, 3H), 1.27 (d, J=1.4 Hz, 3H). LCMS Rt=0.564 min, m/z=206.1 [M+H]⁺.

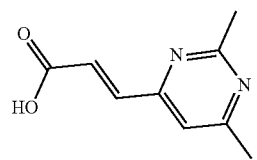

Step 2: (E)-3-(2,6-dimethylpyrimidin-4-yl)acrylic acid

To a solution of ethyl (E)-3-(2,6-dimethylpyrimidin-4-yl)prop-2-enoate (5 g, 24.24 mmol) in tetrahydrofuran (80 mL), methanol (80 mL) and water (80 mL) was added lithium hydroxide monohydrate (1.53 g, 36.37 mmol). The mixture was stirred at 30° C. for 12 h. The reaction mixture was concentrated under reduced pressure to remove tetrahydrofuran and methanol, then extracted with ethyl acetate (3×30 mL). The aqueous phase was adjusted to pH=2 with 1M hydrochloric acid at 0° C., and subsequently extracted with ethyl acetate (3×120 mL). The combined organic layers were dried over sodium sulphate and concentrated in vacuo. The crude residue was diluted with a (5:1) mixture of petroleum ether: ethyl acetate (20 mL) and the resulting precipitate was filtered affording (E)-3-(2,6-dimethylpyrimidin-4-yl)prop-2-enoic acid (3 g, crude) as a yellow solid and used in the next step without further purification. LCMS Rt=0.349 min, m/z=178.1 [M+H]⁺.

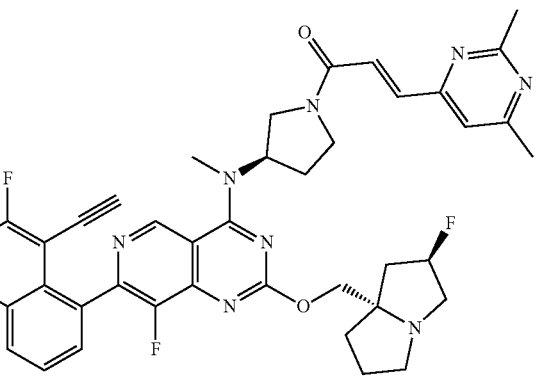

Step 3: (E)-3-(2,6-dimethylpyrimidin-4-yl)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one The amide coupling reaction was prepared in a similar fashion to Method #1, Step 10. The residue was purified by reverse phase HPLC (column: Waters Xbridge Prep OBD C18 150*40 mm*10 μm; mobile phase: [water (NH₄HCO₃)-ACN]; B %: 35%-65%, 8 min) affording (E)-3-(2,6-dimethylpyrimidin-4-yl)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (28.26 mg, 26.48%) as a yellow solid: ¹H NMR (400 MHz, Dimethyl-sulfoxide-d6) δ 9.25-9.18 (m, 1H), 8.28-8.20 (m, 2H), 7.74-7.66 (m, 2H), 7.63 (t, J=9.0 Hz, 1H), 7.59-7.49 (m, 2H), 7.45-7.38 (m, 1H), 5.45-5.16 (m, 2H), 4.26-4.13 (m, 2H), 4.13-4.03 (m, 2H), 4.02-3.77 (m, 2H), 3.67-3.50 (m, 1H), 3.47 (d, J=3.4 Hz, 3H), 3.15-2.99 (m, 3H), 2.87-2.77 (m, 1H), 2.63-2.58 (m, 3H), 2.46 (d, J=7.2 Hz, 3H), 2.44-2.27 (m, 2H), 2.18-2.11 (m, 1H), 2.09-1.97 (m, 2H), 1.88-1.72 (m, 3H). LCMS Rt=2.152 min, m/z=732.3 [M+H]⁺.

LCMS (5 to 95% acetonitrile in water+0.03% ammonium bicarbonate over 6 mins) retention time 2.152 min, ESI+ found [M+H]=732.3.

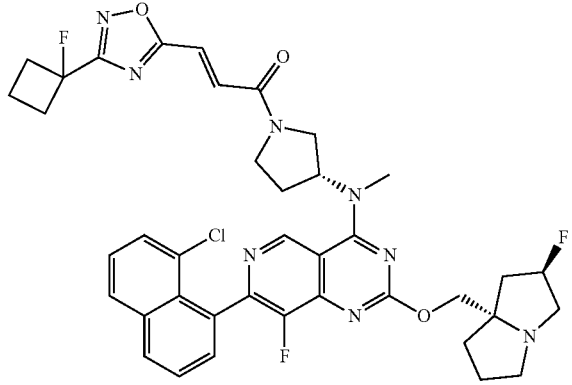 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2nc(C3(F)CCC3)no2)C1]

Example 208 (Method 1): (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-(1-fluorocyclobutyl)-1,2,4-oxadiazol-5-yl)prop-2-en-1-one

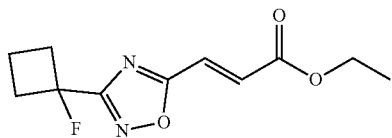 [SMILES: CCOC(=O)/C=C/c1nc(C2(F)CCC2)no1]

Step 1: (E)-ethyl 3-(3-(1-fluorocyclobutyl)-1,2,4-oxadiazol-5-yl)acrylate

The substitution reaction was prepared in a similar fashion to Method #5, Step 7. The mixture was concentrated in vacuo affording (E)-ethyl 3-(3-(1-fluorocyclobutyl)-1,2,4-oxadiazol-5-yl)acrylate (135 mg, crude) as a yellow oil, which was used in the next step without any further purification. LCMS Rt=0.798 min, m/z=240.1 [M+H]⁺.

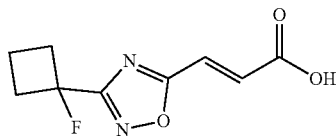 [SMILES: O=C(O)/C=C/c1nc(C2(F)CCC2)no1]

Step 2: (E)-3-(3-(1-fluorocyclobutyl)-1,2,4-oxadiazol-5-yl)acrylic acid

The hydrolysis reaction was prepared in a similar fashion to Method #1, Step 4. The mixture was concentrated in vacuo affording (E)-3-(3-(1-fluorocyclobutyl)-1,2,4-oxadiazol-5-yl)acrylic acid (145 mg, crude) as a yellow solid, which was used in the next step without any further purification. LCMS Rt=0.639 min, m/z=212.1 [M+H]⁺.

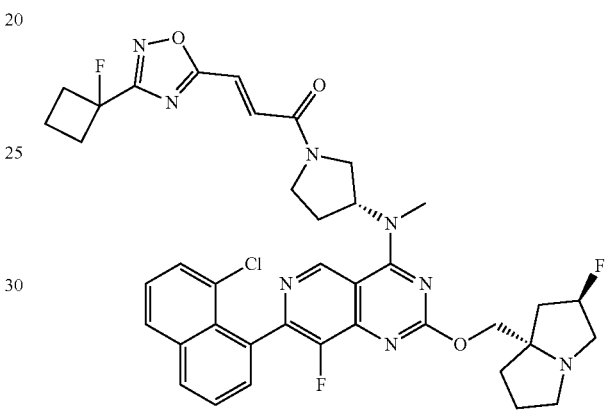

Step 3: (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-(1-fluorocyclobutyl)-1,2,4-oxadiazol-5-yl)prop-2-en-1-one The amide coupling reaction was prepared in a similar fashion to Method #1, Step 10. The residue was purified by reverse phase HPLC (column: Waters Xbridge Prep OBD C18 150*40 mm*10 um; mobile phase: [water(NH₄HCO₃)-ACN]; B %: 40%-70%, 8 min) affording (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-(1-fluorocyclobutyl)-1,2,4-oxadiazol-5-yl)prop-2-en-1-one (12.45 mg, 19.91%) as a yellow oil: ¹H NMR (400 MHz, Acetonitrile-d3) δ 9.23 (s, 1H), 8.16 (d, J=8.1 Hz, 1H), 8.06 (d, J=8.1 Hz, 1H), 7.76-7.70 (m, 1H), 7.69-7.63 (m, 2H), 7.59-7.51 (m, 1H), 7.46 (d, J=12.2 Hz, 1H), 7.42-7.34 (m, 1H), 5.50-5.21 (m, 2H), 4.80 (d, J=7.9 Hz, 1H), 4.67 (d, J=7.9 Hz, 1H), 4.30-4.19 (m, 2H), 4.10-3.99 (m, 1H), 3.92-3.76 (m, 1H), 3.70-3.52 (m, 1H), 3.48 (s, 3H), 3.25-3.14 (m, 2H), 3.01-2.89 (m, 1H), 2.52-2.41 (m, 1H), 2.40-2.31 (m, 2H), 2.25 (br d, J=5.0 Hz, 1H), 2.19-2.08 (m, 3H), 1.95-1.84 (m, 3H), 1.43-1.34 (m, 2H), 1.30-1.22 (m, 2H).

LCMS (5 to 95% acetonitrile in water+0.03% ammonium bicarbonate over 6 mins) retention time 3.063 min, ESI+ found [M+H]=758.3.

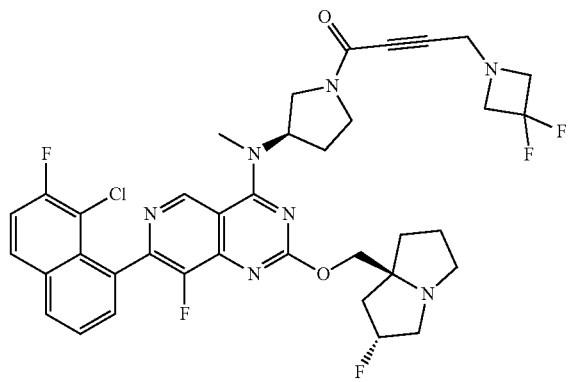 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)C#CCN2CC(F)(F)C2)C1]
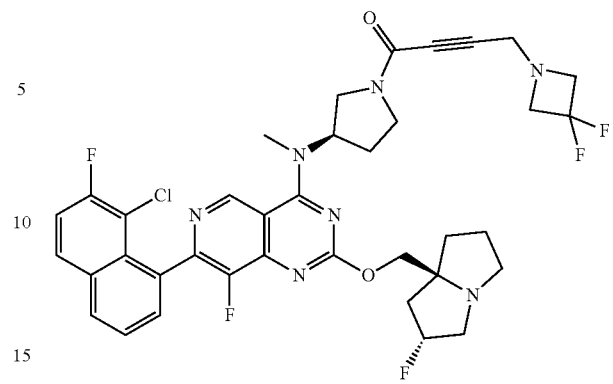

Example 209 (Method 13): 1-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-4-(3,3-difluoroazetidin-1-yl)but-2-yn-1-one Step 2: 1-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-4-(3,3-difluoroazetidin-1-yl)but-2-yn-1-one The substitution reaction was prepared in a similar fashion to Method #13, Step 2. The residue was purified by reverse phase HPLC (neutral conditions; column: Waters Xbridge BEH C18 100*30 mm*10 μm; mobile phase: [water(NH$_4$HCO$_3$)-ACN]; B %: 40%-65%, 8 min) affording 1-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-4-(3,3-difluoroazetidin-1-yl)but-2-yn-1-one (2 mg, 4.47%) as a white solid: $^1$H NMR (400 MHz, Acetonitrile-d3) δ 9.26-9.10 (m, 1H), 8.16 (dd, J=2.9, 6.4 Hz, 1H), 8.10 (dd, J=5.8, 9.0 Hz, 1H), 7.74-7.66 (m, 2H), 7.55 (t, J=8.9 Hz, 1H), 5.44-5.21 (m, 2H), 4.87 (d, J=11.0 Hz, 1H), 4.46-4.29 (m, 1H), 4.26-4.12 (m, 3H), 4.05-3.88 (m, 1H), 3.78-3.62 (m, 5H), 3.54-3.41 (m, 4H), 3.23-3.06 (m, 3H), 2.98-2.83 (m, 1H), 2.48-2.28 (m, 3H), 2.13-2.05 (m, 3H), 1.92-1.86 (m, 2H).

LCMS (5% to 95% acetonitrile in water+0.03% ammonium bicarbonate over 6 mins); retention time 3.063 min, ESI+ found [M+H]=739.3.

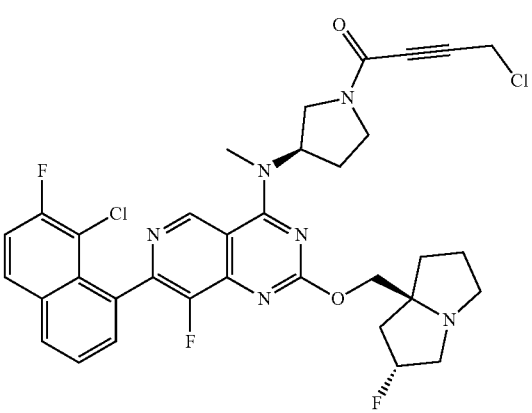 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)C#CCCl)C1]

Step 1: 4-chloro-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)but-2-yn-1-one The amide coupling reaction was prepared in a similar fashion to Method #13, Step 1. The residue was purified by reverse phase HPLC (neutral conditions, column: Waters Xbridge BEH C18 100*30 mm*10 μm; mobile phase: [water(NH$_4$HCO$_3$)-ACN]; B %: 45%-75%, 8 min) affording 4-chloro-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)but-2-yn-1-one (15 mg, 29.98%) as a yellow solid. LCMS Rt=0.681 min, m/z=682.2 [M+H]$^+$.

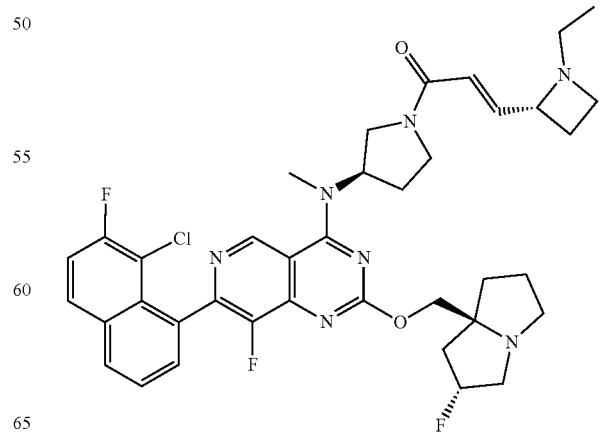

Example 210 (Method 8):(E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-ethylazetidin-2-yl)prop-2-en-1-one

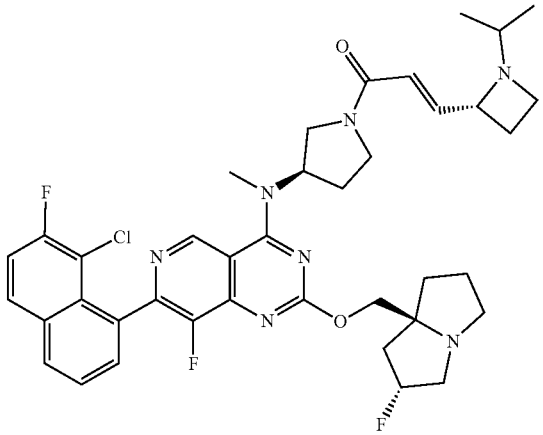

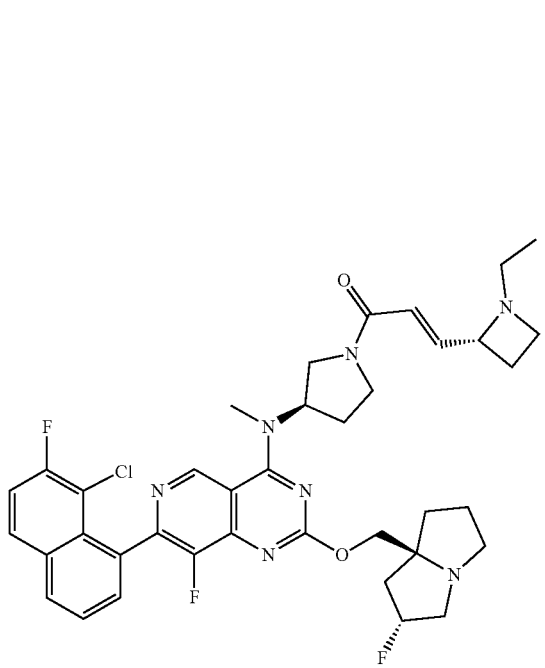 [SMILES: CCN1CC[C@@H]1/C=C/C(=O)N1CC[C@@H](N(C)c2nc(OC[C@@]34CCCN3C[C@H](F)C4)nc3c(F)c(-c4cccc5ccc(F)c(Cl)c45)ncc23)C1]

Step 1: (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-ethylazetidin-2-yl)prop-2-en-1-one The reductive amination was prepared in a similar fashion to Method #8, Step 6. The residue was purified by reverse phase HPLC (column: Waters Xbridge BEH C18 100*30 mm*10 μm; mobile phase: [water(NH$_4$HCO$_3$)-ACN]; B %: 25%-70%, 8 min) affording (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-ethylazetidin-2-yl)prop-2-en-1-one (23.18 mg, 23.44%) as a yellow oil: $^1$H NMR (400 MHz, Acetonitrile-d3) δ 9.31-9.13 (m, 1H), 8.25-8.04 (m, 2H), 7.82-7.64 (m, 2H), 7.56 (t, J=8.9 Hz, 1H), 6.83 (dd, J=5.9, 15.2 Hz, 1H), 6.49-6.34 (m, 1H), 5.53-5.14 (m, 2H), 4.29-4.05 (m, 3H), 4.04-3.77 (m, 1H), 3.74-3.56 (m, 2H), 3.46 (s, 3H), 3.38-3.28 (m, 1H), 3.21-3.07 (m, 3H), 2.98-2.88 (m, 1H), 2.84-2.73 (m, 1H), 2.64-2.51 (m, 1H), 2.46-2.28 (m, 2H), 2.25-2.04 (m, 6H), 1.96-1.80 (m, 4H), 1.04-0.85 (m, 3H).

LCMS (5% to 95% acetonitrile in water+0.03% ammonium bicarbonate over 6 min); retention time 2.994 min, ESI+ found [M+H]=719.3.

Example 211 (Method 8):(E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-isopropylazetidin-2-yl)prop-2-en-1-one

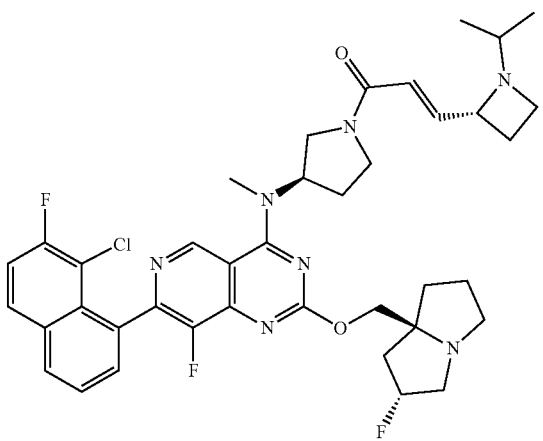 [SMILES: CC(C)N1CC[C@@H]1/C=C/C(=O)N1CC[C@@H](N(C)c2nc(OC[C@@]34CCCN3C[C@H](F)C4)nc3c(F)c(-c4cccc5ccc(F)c(Cl)c45)ncc23)C1]

Step 1: (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-isopropylazetidin-2-yl)prop-2-en-1-one The reductive amination was prepared in a similar fashion to Method #8, Step 6. The residue was purified by reverse phase HPLC (column: Waters Xbridge Prep OBD C18 150*40 mm*10 um; mobile phase: [water(NH$_4$HCO$_3$)-ACN]; B %: 35%-60%, 8 min) affording (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-isopropylazetidin-2-yl)prop-2-en-1-one (24.7 mg, 13.20%) as a yellow solid: $^1$H NMR (400 MHz, Acetonitrile-d3) δ 9.24-9.17 (m, 1H), 8.16 (dd, J=3.3, 6.4 Hz, 1H), 8.10 (dd, J=5.8, 9.0 Hz, 1H), 7.72-7.67 (m, 2H), 7.55 (t, J=8.9 Hz, 1H), 6.86 (dd, J=6.4, 15.1 Hz, 1H), 6.48-6.39 (m, 1H), 5.45-5.19 (m, 2H), 4.27-4.21 (m, 1H), 4.19-4.00 (m, 2H), 3.99-3.88 (m, 1H), 3.87-3.76 (m, 1H), 3.76-3.63 (m, 2H), 3.62-3.49 (m, 1H), 3.45 (s, 3H), 3.33-3.26 (m, 1H), 3.16 (br d, J=6.6 Hz, 2H), 3.08 (s, 1H), 2.95-2.87 (m, 1H), 2.86-2.77 (m, 1H), 2.44-2.36 (m, 2H), 2.35-2.28 (m, 1H), 2.21 (br s, 1H), 2.13 (br s, 2H), 2.10-2.05 (m, 1H), 1.92-1.85 (m, 3H), 0.96-0.84 (m, 6H).

LCMS (5% to 95% acetonitrile in water+0.03% ammonium bicarbonate over 6 min) retention time 3.071 min, ESI+ found [M+H]=733.3.

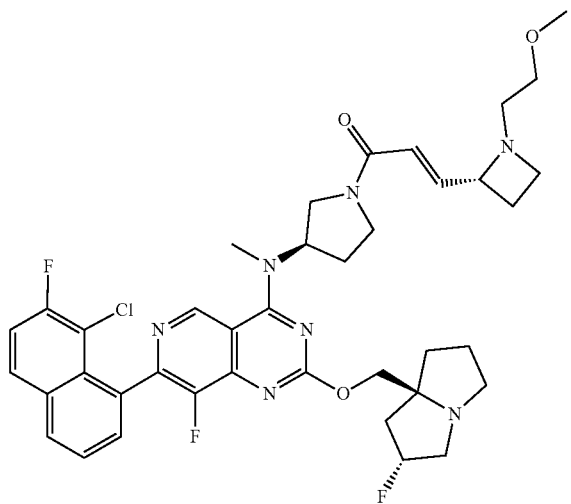

Example 212 (Method 8): (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-(2-methoxyethyl)azetidin-2-yl)prop-2-en-1-one Step 1: (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-(2-methoxyethyl)azetidin-2-yl)prop-2-en-1-one The reductive amination was prepared in a similar fashion to Method #8, Step 6. The residue was purified by reverse phase HPLC (column: Waters Xbridge Prep OBD C18 150*40 mm*10 um; mobile phase: [water($NH_4HCO_3$)-ACN]; B %: 30%-60%, 8 min) affording (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-(2-methoxyethyl)azetidin-2-yl)prop-2-en-1-one (14.63 mg, 10.09%) as a white solid: $^1$H NMR (400 MHz, Acetonitrile-d3) δ 9.21 (br d, J=2.0 Hz, 1H), 8.16 (br dd, J=6.3 Hz, J=3.1 Hz, 1H), 8.09 (dd, J=9.1 Hz, J=5.7 Hz, 1H), 7.67-7.74 (m, 2H), 7.55 (t, J=8.9 Hz, 1H), 6.74-6.86 (m, 1H), 6.38-6.52 (m, 1H), 5.19-5.44 (m, 2H), 4.20-4.27 (m, 1H), 4.10-4.18 (m, 2H), 3.79-4.00 (m, 2H), 3.66-3.73 (m, 1H), 3.50-3.65 (m, 2H), 3.45 (s, 3H), 3.31-3.39 (m, 2H), 3.26 (d, J=19.5 Hz, 2H), 3.12-3.19 (m, 2H), 2.98-3.10 (m, 2H), 2.87-2.95 (m, 2H), 2.50-2.69 (m, 2H), 2.31-2.42 (m, 2H), 2.19-2.25 (m, 2H), 2.13 (br s, 1H), 2.06-2.10 (m, 1H), 1.85-1.94 (m, 4H).

LCMS (5% to 95% acetonitrile in water+0.03% ammonium bicarbonate over 6 min); retention time 2.951 min, ESI+ found [M+H]=749.3.

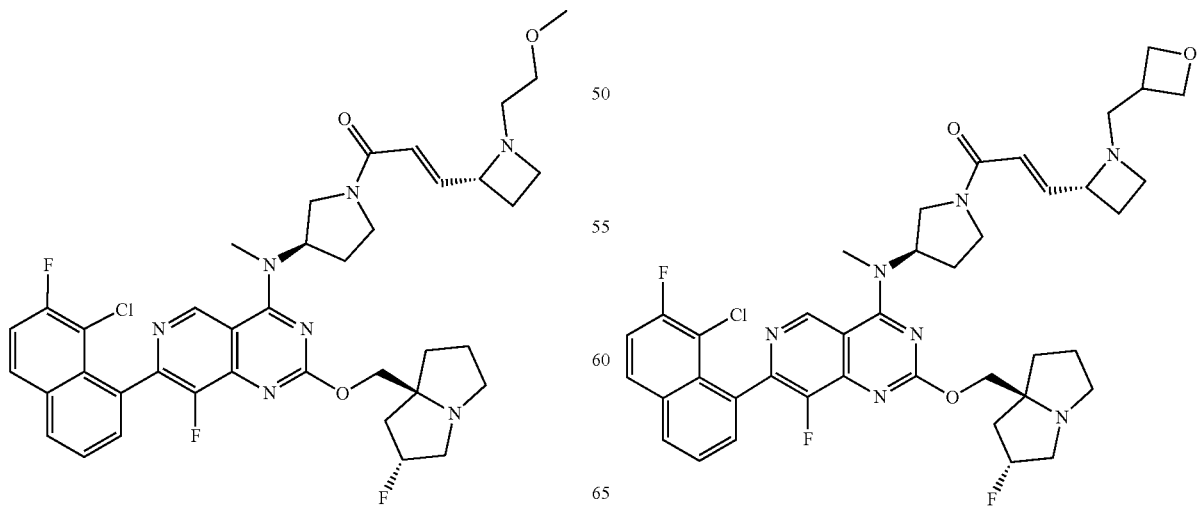

Example 213 (Method 8):(E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-(oxetan-3-ylmethyl)azetidin-2-yl)prop-2-en-1-one

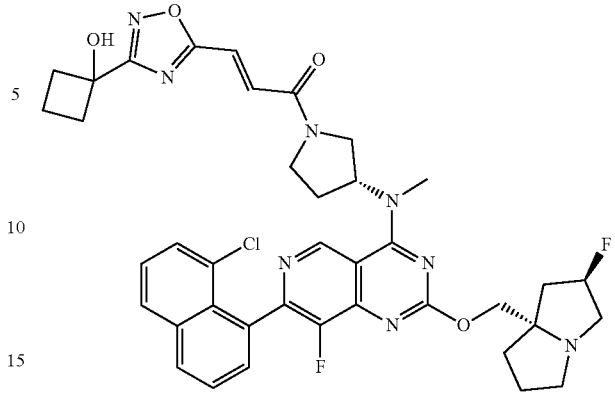

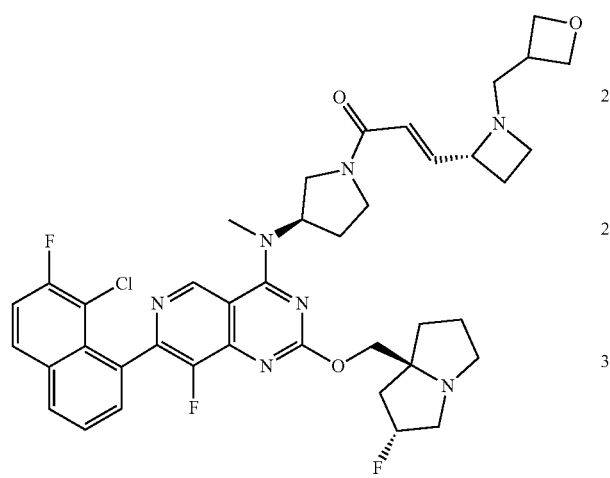

Step 1: (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-(oxetan-3-ylmethyl)azetidin-2-yl)prop-2-en-1-one The reductive amination was prepared in a similar fashion to Method #8, Step 6. The residue was purified by reverse phase HPLC (column: Waters Xbridge Prep OBD C18 150*40 mm*10 um; mobile phase: [water(NH$_4$HCO$_3$)-ACN]; B %: 35%-65%, 8 min) affording (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-(2-methoxyethyl)azetidin-2-yl)prop-2-en-1-one (40.63 mg, 23.51%) as a yellow amorphous solid: $^1$H NMR (400 MHz, Acetonitrile-d3) δ 9.29-9.14 (m, 1H), 8.19-8.13 (m, 1H), 8.09 (dd, J=5.8, 9.1 Hz, 1H), 7.76-7.66 (m, 2H), 7.54 (t, J=8.9 Hz, 1H), 6.79 (dd, J=5.7, 15.1 Hz, 1H), 6.46-6.34 (m, 1H), 5.46-5.18 (m, 2H), 4.70-4.60 (m, 2H), 4.33-4.25 (m, 2H), 4.19-4.04 (m, 2H), 4.02-3.78 (m, 2H), 3.75-3.65 (m, 2H), 3.51 (br s, 1H), 3.48-3.44 (m, 3H), 3.33-3.24 (m, 1H), 3.20-3.13 (m, 2H), 3.09 (s, 1H), 3.06-2.97 (m, 1H), 2.91-2.79 (m, 2H), 2.73-2.64 (m, 1H), 2.46-2.38 (m, 1H), 2.37-2.29 (m, 1H), 2.25-2.16 (m, 3H), 2.13 (br s, 1H), 2.10-2.06 (m, 1H), 1.95-1.83 (m, 4H).

LCMS (5% to 95% acetonitrile in water+0.03% ammonium bicarbonate over 6 min); retention time 2.889 min, ESI+ found [M+H]=761.3.

Example 214 (Method 1):(E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-(1-hydroxycyclobutyl)-1,2,4-oxadiazol-5-yl)prop-2-en-1-one

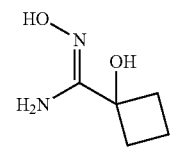

Step 1: N', 1-dihydroxycyclobutanecarboxamidine

The hydroxylimidamide formation was prepared in a similar fashion to Method #1, Step 1. The mixture was concentrated in vacuo affording N', 1-dihydroxycyclobutanecarboxamidine (1.5 g, crude) as a brown oil, which was used in the next step without any further purification. LCMS Rt =0.254 min, m/z=130.1 [M+H]$^+$.

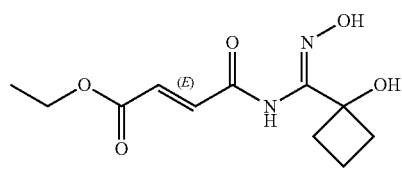 [SMILES: CCOC(=O)/C=C/C(=O)N/C(=N/O)C1(O)CCC1]

Step 2: ethyl (E)-4-[[(E)-N-hydroxy-C-(1-hydroxycyclobutyl)carbonimidoyl]amino]-4-oxo-but-2-enoate The coupling reaction was prepared in a similar fashion to Method #1, Step 2. The mixture was concentrated in vacuo affording ethyl (E)-4-[[(E)-N-hydroxy-C-(1-hydroxycyclobutyl)carbonimidoyl]amino]-4-oxo-but-2-enoate (1.6 g, 58.04%) as a brown oil.

LCMS Rt=0.627 min, m/z=256.1 [M+H]$^+$.

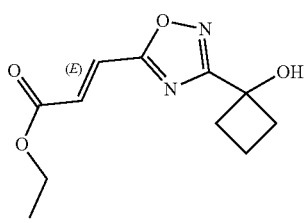 [SMILES: CCOC(=O)/C=C/c1nc(C2(O)CCC2)no1]

Step 3: ethyl (E)-3-(3-(1-hydroxycyclobutyl)-1,2,4-oxadiazol-5-yl)acrylate

The cyclization reaction was prepared in a similar fashion to Method #1, Step 3. The mixture was purified by column chromatography (silica gel, 100-200 mesh, 0-10% ethyl acetate in petroleum ether) affording ethyl (E)-3-(3-(1-hydroxycyclobutyl)-1,2,4-oxadiazol-5-yl)acrylate (600 mg, 64.54%) as a yellow oil. LCMS Rt=0.691 min, m/z=238.1 [M+H]$^+$.

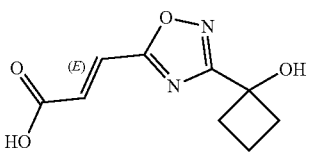 [SMILES: O=C(O)/C=C/c1nc(C2(O)CCC2)no1]

Step 4: (E)-3-[3-(1-hydroxycyclobutyl)-1,2,4-oxadiazol-5-yl]prop-2-enoic acid

The hydrolysis reaction was prepared in a similar fashion to Method #1, Step 4. The mixture was concentrated in vacuo affording (E)-3-[3-(1-hydroxycyclobutyl)-1,2,4-oxadiazol-5-yl]prop-2-enoic acid (150 mg, crude) as a white solid, which was used in the next step without any further purification. LCMS Rt=0.540 min, m/z=210.1 [M+H]$^+$.

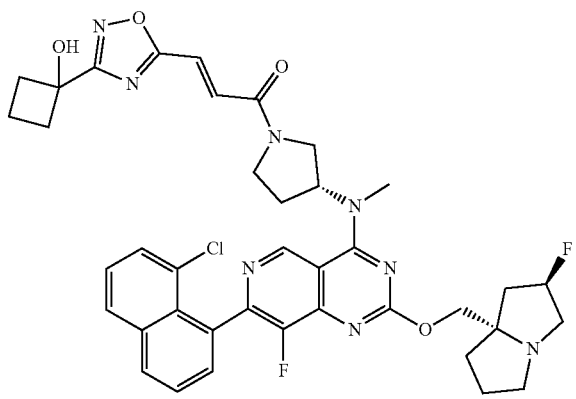 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2nc(C3(O)CCC3)no2)C1]

Step 5: (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-(1-hydroxycyclobutyl)-1,2,4-oxadiazol-5-yl)prop-2-en-1-one The amide coupling reaction was prepared in a similar fashion to Method #1, Step 10. The residue was purified by reverse phase HPLC (column: Waters Xbridge Prep OBD C18 150*40 mm*10 um; mobile phase: [water(NH$_4$HCO$_3$)-ACN]; B %: 35%-65%, 8 min) affording (E)-1-((R)-3-((7-(8-chloronaphthalen-1-yl)-8-fluoro-2-(((2R,7aS)-2-fluoro-tetrahydro-1H-pyrrolizin-7a(5H)-yl)methoxy)pyrido[4,3-d]pyrimidin-4-yl)(methyl)amino)pyrrolidin-1-yl)-3-(3-(1-hydroxycyclobutyl)-1,2,4-oxadiazol-5-yl)prop-2-en-1-one (10.26 mg, 3.66%) as a yellow solid: $^1$H NMR (400 MHz, Acetonitrile-d3) δ 9.19 (s, 1H), 8.15-8.09 (m, 1H), 8.01 (br d, J=8.3 Hz, 1H), 7.71-7.66 (m, 1H), 7.63-7.58 (m, 2H), 7.54-7.36 (m, 3H), 5.47-5.36 (m, 1H), 5.34-5.14 (m, 1H), 4.25-4.10 (m, 3H), 4.05-3.96 (m, 1H), 3.91-3.72 (m, 2H), 3.43 (s, 3H), 3.18-3.11 (m, 1H), 3.09-3.03 (m, 1H), 2.92-2.83 (m, 1H), 2.64-2.52 (m, 2H), 2.47-2.37 (m, 2H), 2.34 (br d, J=7.8 Hz, 4H), 2.12-1.96 (m, 4H), 1.89-1.71 (m, 4H).

LCMS (5% to 95% acetonitrile in water+0.03% ammonium bicarbonate over 6 min); retention time 3.011 min, ESI+ found [M+H]=756.3.

Example 215 (Method 8): (E)-1-((3S,4S)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidin-1-yl)-3-(3-methyl-1,2,4-thiadiazol-5-yl)prop-2-en-1-one

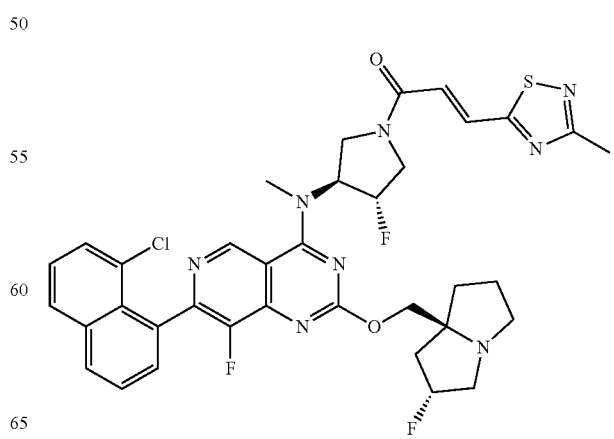

Step 1: (E)-1-((3S,4S)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidin-1-yl)-3-(3-methyl-1,2,4-thiadiazol-5-yl)prop-2-en-1-one The HWE reaction was prepared in a similar fashion to Method #8, Step 4. The residue was purified by reverse phase HPLC (neutral conditions, column: Waters Xbridge Prep OBD C18 150*40 mm*10 μm; mobile phase: [water (NH₄HCO₃)-ACN]; B %: 30%-80%, 8 min) affording (E)-1-((3S,4S)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidin-1-yl)-3-(3-methyl-1,2,4-thiadiazol-5-yl)prop-2-en-1-one (14.76 mg, 18.06%) as a yellow amorphous solid: ¹H NMR (400 MHz, Acetonitrile-d3) δ 9.24 (s, 1H), 8.16-8.07 (m, 1H), 8.01 (d, J=7.6 Hz, 1H), 7.77 (dd, J=5.4, 15.3 Hz, 1H), 7.71-7.65 (m, 1H), 7.64-7.57 (m, 2H), 7.54-7.47 (m, 1H), 7.31 (d, J=15.3 Hz, 1H), 5.75-5.51 (m, 1H), 5.39-5.12 (m, 2H), 4.49-4.32 (m, 1H), 4.24-4.08 (m, 3H), 4.06-3.94 (m, 1H), 3.93-3.79 (m, 1H), 3.60-3.46 (m, 3H), 3.17-3.03 (m, 3H), 2.93-2.80 (m, 1H), 2.66-2.57 (m, 3H), 2.19-2.15 (m, 1H), 2.08 (br dd, J=3.6, 6.9 Hz, 1H), 2.02 (br d, J=7.5 Hz, 1H), 1.91-1.76 (m, 3H).

LCMS (5% to 95% acetonitrile in water+0.03% ammonium bicarbonate over 6 min); retention time 2.958 min, ESI+ found [M+H]=734.2.

Step 1: (E)-1-((3S,4S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-(2-methylpyrimidin-4-yl)prop-2-en-1-one The amide coupling reaction was prepared in a similar fashion to Method #1, Step 10. The crude residue was purified by reverse phase HPLC (column: Waters Xbridge Prep OBD C18 150*40 mm*10 um; mobile phase: [water (NH₄HCO₃)-ACN]; B %: 30%-70%, 8 min) affording (E)-1-((3S,4S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-(2-methylpyrimidin-4-yl)prop-2-en-1-one (10.26 mg, 11.83%) as a yellow amorphous solid: ¹H NMR (400 MHz, Acetonitrile-d3) δ 9.25 (s, 1H), 8.72-8.66 (m, 1H), 8.12 (d, J=7.3 Hz, 1H), 8.02 (d, J=7.6 Hz, 1H), 7.72-7.66 (m, 1H), 7.65-7.59 (m, 2H), 7.57-7.46 (m, 3H), 7.38-7.33 (m, 1H), 5.78-5.53 (m, 1H), 5.37-5.13 (m, 2H), 4.51-4.34 (m, 1H), 4.23-4.09 (m, 3H), 4.06-3.80 (m, 2H), 3.54 (d, J=5.0 Hz, 3H), 3.16-3.01 (m, 3H), 2.92-2.79 (m, 1H), 2.66 (d, J=10.6 Hz, 3H), 2.10-1.99 (m, 3H), 1.90-1.76 (m, 3H).

LCMS (5% to 95% acetonitrile in water+0.03% ammonium bicarbonate over 6 min); retention time 2.803 min. ESI+ found [M+H]=728.3.

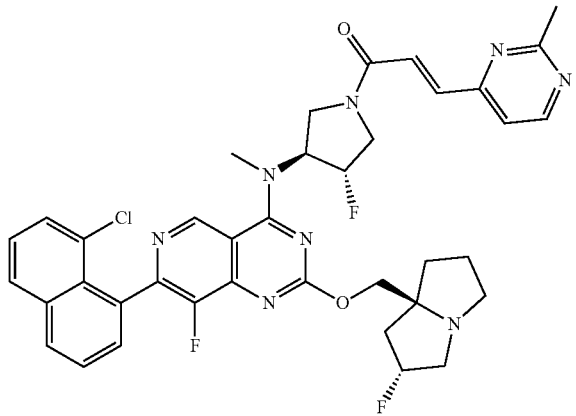 [SMILES: Cc1nccc(/C=C/C(=O)N2C[C@H](F)[C@@H](N(C)c3nc(OC[C@@]45CCCN4C[C@H](F)C5)nc4c(F)c(-c5cccc6cccc(Cl)c56)ncc34)C2)n1]

Example 216 (Method 1): (E)-1-((3S,4S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-(2-methylpyrimidin-4-yl)prop-2-en-1-one

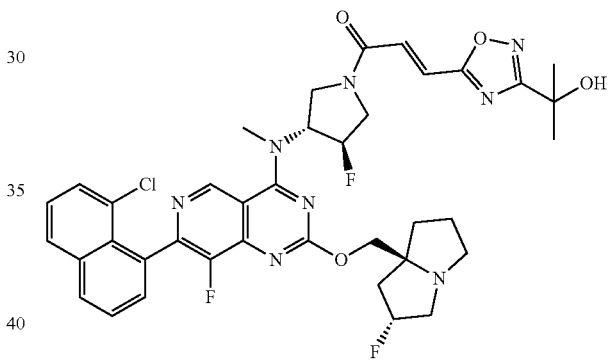

Example 217 (Method 1): (E)-1-((3R,4R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-(3-(2-hydroxypropan-2-yl)-1,2,4-oxadiazol-5-yl)prop-2-en-1-one

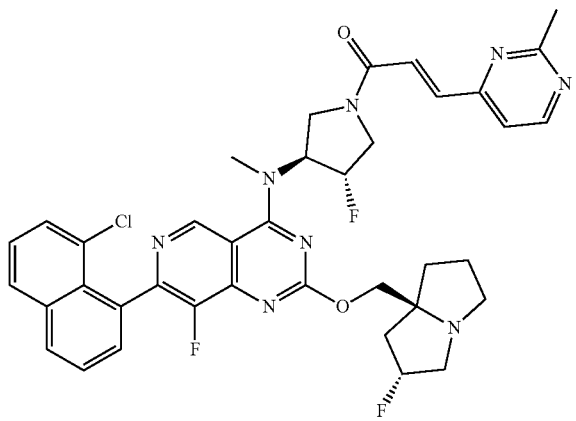 [SMILES: Cc1nccc(/C=C/C(=O)N2C[C@H](F)[C@@H](N(C)c3nc(OC[C@@]45CCCN4C[C@H](F)C5)nc4c(F)c(-c5cccc6cccc(Cl)c56)ncc34)C2)n1]

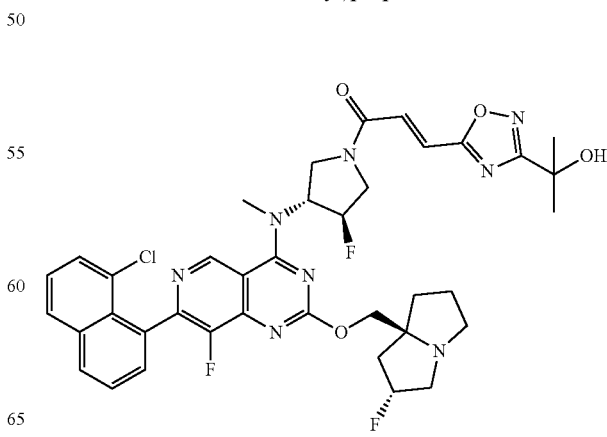

883

Step 1: (E)-1-((3R,4R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-(3-(2-hydroxypropan-2-yl)-1,2,4-oxadiazol-5-yl)prop-2-en-1-one The amide coupling reaction was prepared in a similar fashion to Method #1, Step 10. The crude residue was purified by reverse phase HPLC (column: Waters Xbridge BEH C18 100*30 mm*10 um; mobile phase: [water (NH$_4$HCO$_3$)-ACN]; B %: 45%-75%, 8 min) affording (E)-1-((3R,4R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-(3-(2-hydroxypropan-2-yl)-1,2,4-oxadiazol-5-yl)prop-2-en-1-one (17.69 mg, 39.83%) as a yellow amorphous solid: $^1$H NMR (400 MHz, Acetonitrile-d3) δ 9.28 (s, 1H), 8.16 (d, J=8.1 Hz, 1H), 8.05 (d, J=8.0 Hz, 1H), 7.75-7.69 (m, 1H), 7.67-7.62 (m, 2H), 7.54 (t, J=8.0 Hz, 1H), 7.49-7.40 (m, 2H), 5.82-5.53 (m, 1H), 5.47-5.07 (m, 2H), 4.59-4.33 (m, 1H), 4.31-4.13 (m, 3H), 4.10-3.97 (m, 1H), 3.94 (br d, J=5.0 Hz, 1H), 3.70-3.59 (m, 1H), 3.56 (d, J=5.3 Hz, 3H), 3.29-3.07 (m, 3H), 3.03-2.85 (m, 1H), 2.26-2.18 (m, 2H), 2.12 (br d, J=2.1 Hz, 2H), 1.90 (br d, J=6.5 Hz, 2H), 1.61 (d, J=7.0 Hz, 6H).

LCMS (5% to 95% acetonitrile in water+0.03% ammonium bicarbonate over 6 min); retention time 2.247 min. ESI+ found [M+H]=762.3.

884

Example 218 (Method 8): (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-((S)-1-methylazetidin-2-yl)prop-2-en-1-one

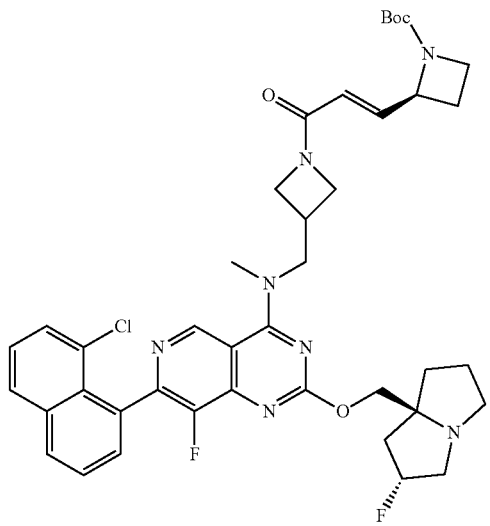

Step 1: tert-butyl (S)-2-((E)-3-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-oxoprop-1-en-1-yl)azetidine-1-carboxylate

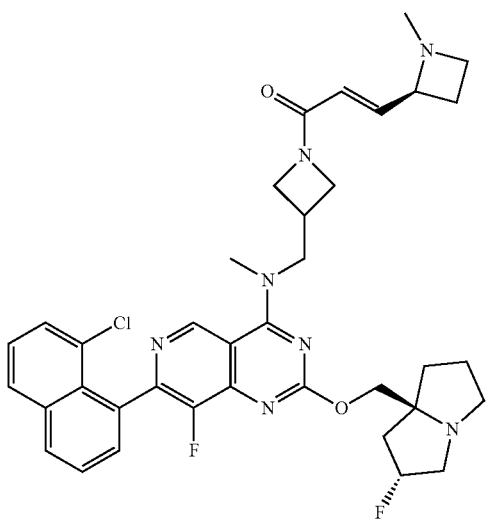 [SMILES: CN(CC1CN(C(=O)/C=C/[C@@H]2CCN2C)C1)c1nc(OC[C@@]23CCCN2C[C@H](F)C3)nc2c(F)c(-c3cccc4cccc(Cl)c34)ncc12]

The HWE reaction was prepared in a similar fashion to Method #8, Step 4. The reaction mixture was diluted with water (5 mL) and extracted with ethyl acetate (3×5 mL). The combined organic layers were dried over sodium sulphate and concentrated in vacuo affording tert-butyl (S)-2-((E)-3-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-oxoprop-1-en-1-yl)azetidine-1-carboxylate (52 mg, crude) as a yellow oil, which was used in the next step without any further purification. LCMS Rt=0.753 min, m/z=773.3 [M+H]$^+$.

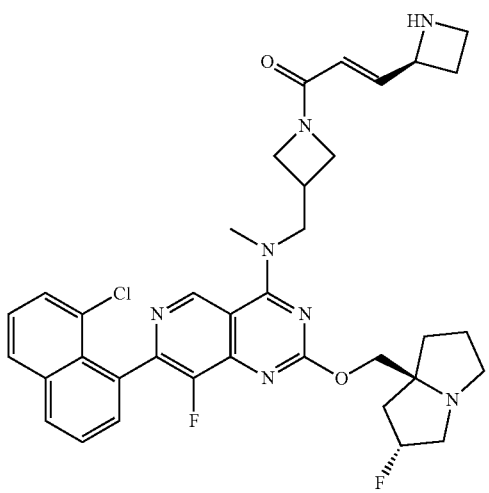 [SMILES: CN(CC1CN(C(=O)/C=C/[C@@H]2CCN2)C1)c1nc(OC[C@@]23CCCN2C[C@H](F)C3)nc2c(F)c(-c3cccc4cccc(Cl)c34)ncc12]

Step 2: (E)-3-((S)-azetidin-2-yl)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)prop-2-en-1-one The deprotection of the Boc group was prepared in a similar fashion to Method #1, Step 9. The reaction mixture was concentrated in vacuo affording (E)-3-((S)-azetidin-2-yl)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)prop-2-en-1-one (60 mg, crude, trifluoroacetic acid salt) as a yellow oil, which was used in the next step without any further purification. LCMS Rt=0.617 min, m/z=673.3 [M+H]$^+$.

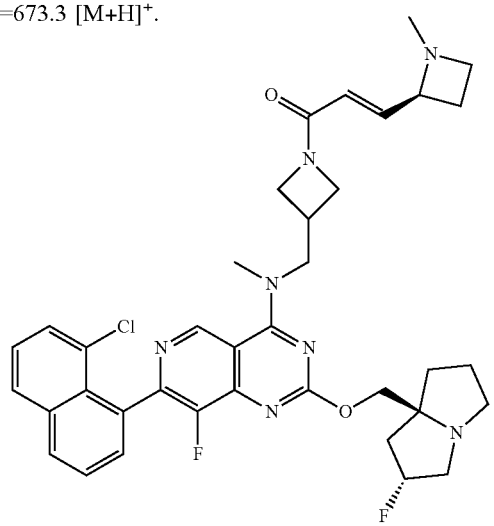

Step 3: (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-((S)-1-methylazetidin-2-yl)prop-2-en-1-one The reductive amination was prepared in a similar fashion to Method #8, Step 6. The residue was purified by prep-HPLC (column: Phenomenex Luna C18 75*30 mm*3 μm; mobile phase: [water(FA)-ACN]; B %: 10%-40%, 8 min) affording (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-((S)-1-methylazetidin-2-yl)prop-2-en-1-one (4.29 mg, 7.00%, formic acid salt) as a white solid: $^1$H NMR (400 MHz, Acetonitrile-d3) δ 9.26 (s, 1H), 8.27 (br s, 1H), 8.15 (d, J=8.1 Hz, 1H), 8.04 (d, J=8.1 Hz, 1H), 7.76-7.68 (m, 1H), 7.64 (d, J=7.5 Hz, 2H), 7.57-7.49 (m, 1H), 6.74 (dd, J=6.0, 15.3 Hz, 1H), 6.13 (d, J=15.3 Hz, 1H), 5.45-5.22 (m, 1H), 4.36 (br t, J=8.6 Hz, 1H), 4.20 (br s, 2H), 4.18-4.08 (m, 3H), 3.92-3.82 (m, 1H), 3.71 (br d, J=7.1 Hz, 1H), 3.60 (s, 3H), 3.40 (br t, J=7.4 Hz, 1H), 3.30-3.19 (m, 3H), 3.16 (br d, J=2.3 Hz, 1H), 3.00-2.91 (m, 2H), 2.31 (s, 3H), 2.27-2.19 (m, 2H), 2.18-2.07 (m, 2H), 2.06-2.00 (m, 1H), 1.96-1.82 (m, 4H).

LCMS (5% to 95% acetonitrile in water+0.1% trifluoroacetic acid over 6 min); retention time 2.873 min, ESI+ found [M+H]=687.3.

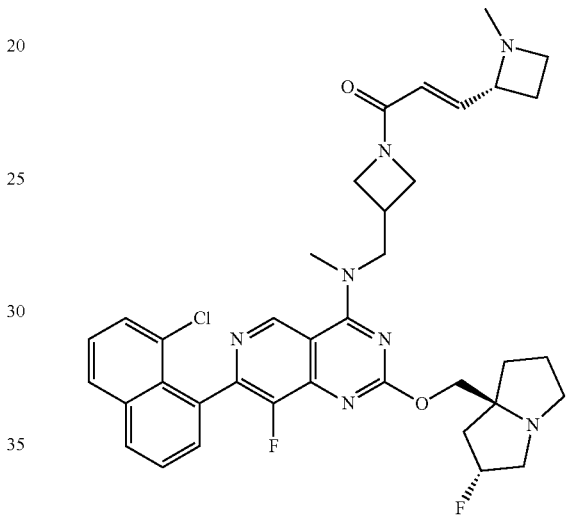

Example 219 (Method 8): (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-((R)-1-methylazetidin-2-yl)prop-2-en-1-one

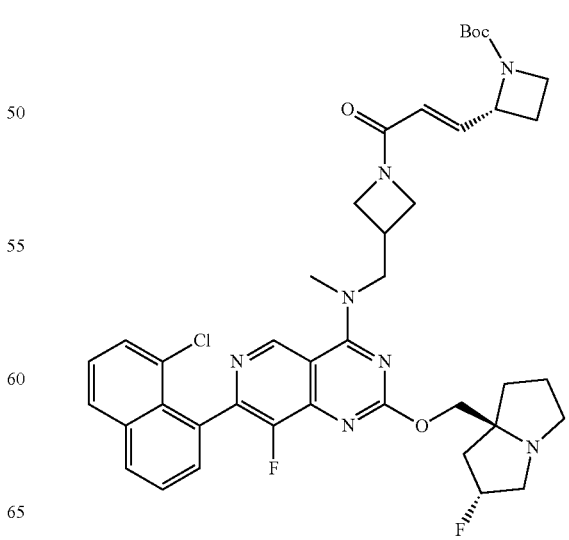

Step 1: tert-butyl (R)-2-((E)-3-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-oxoprop-1-en-1-yl)azetidine-1-carboxylate The HWE reaction was prepared in a similar fashion to Method #8, Step 4. The reaction mixture was diluted with water (5 mL) and extracted with ethyl acetate (3×5 mL). The combined organic layers were dried over sodium sulphate and concentrated in vacuo affording tert-butyl (R)-2-((E)-3-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-oxoprop-1-en-1-yl)azetidine-1-carboxylate (50 mg, crude) as a white solid, which was used in the next step without any further purification. LCMS Rt=0.729 min, m/z=773.3 [M+H]⁺.

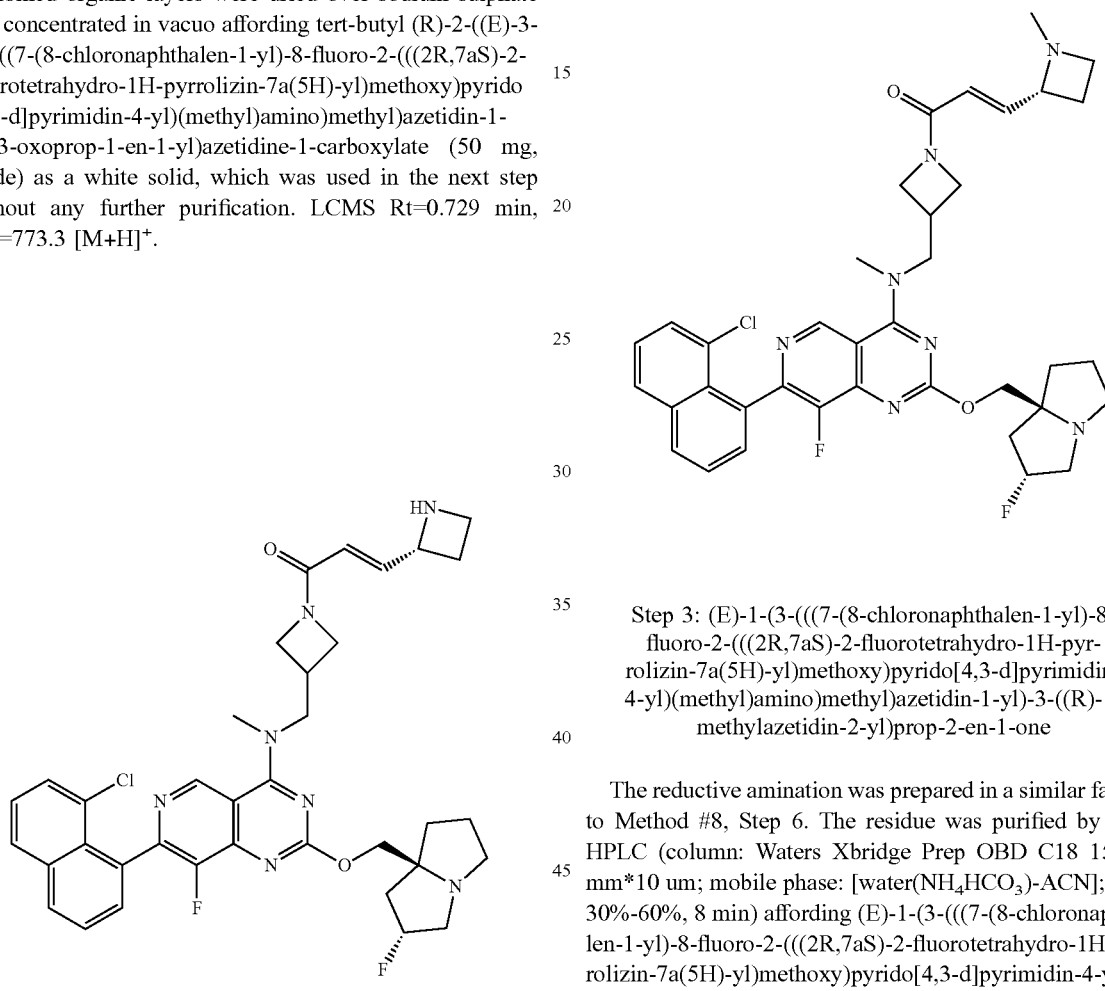

Step 2: (E)-3-((R)-azetidin-2-yl)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)prop-2-en-1-one The deprotection of the Boc group was prepared in a similar fashion to Method #1, Step 9. The reaction mixture was concentrated in vacuo affording (E)-3-((R)-azetidin-2-yl)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)prop-2-en-1-one (50 mg, crude, trifluoroacetic acid salt) as a yellow oil, which was used in the next step without any further purification. LCMS Rt=0.752 min, m/z=673.3 [M+H]⁺.

Step 3: (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-((R)-1-methylazetidin-2-yl)prop-2-en-1-one The reductive amination was prepared in a similar fashion to Method #8, Step 6. The residue was purified by prep-HPLC (column: Waters Xbridge Prep OBD C18 150*40 mm*10 um; mobile phase: [water(NH₄HCO₃)-ACN]; B %: 30%-60%, 8 min) affording (E)-1-(3-(((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-((R)-1-methylazetidin-2-yl)prop-2-en-1-one (6.21 mg, 12.11%) as a yellow amorphous solid: ¹H NMR (400 MHz, Acetonitrile-d3) δ 9.23-9.08 (m, 1H), 8.06 (dd, J=1.2, 8.2 Hz, 1H), 7.95 (dd, J=0.9, 8.1 Hz, 1H), 7.66-7.59 (m, 1H), 7.55 (d, J=7.4 Hz, 2H), 7.49-7.42 (m, 1H), 6.62 (ddd, J=1.7, 5.6, 15.2 Hz, 1H), 6.01 (br d, J=15.4 Hz, 1H), 5.32-5.08 (m, 1H), 4.26 (t, J=8.5 Hz, 1H), 4.15-4.09 (m, 2H), 4.07-3.98 (m, 3H), 3.81-3.72 (m, 1H), 3.53-3.48 (m, 3H), 3.47-3.38 (m, 1H), 3.24-3.17 (m, 1H), 3.15-3.03 (m, 3H), 2.99 (br s, 1H), 2.87-2.78 (m, 1H), 2.76-2.67 (m, 1H), 2.15 (s, 3H), 2.10 (br d, J=3.0 Hz, 2H), 2.03 (br s, 2H), 2.00-1.95 (m, 1H), 1.85-1.75 (m, 4H).

LCMS (5% to 95% acetonitrile in water+0.03% ammonium bicarbonate over 6 min); retention time 2.860 min, ESI+ found [M+H]=687.3.

889

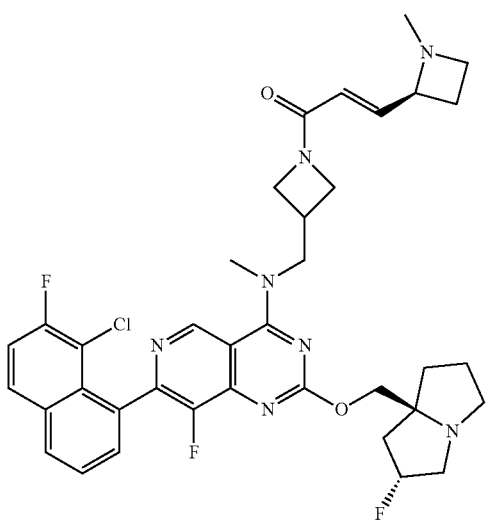 [SMILES: CN(CC1CN(C(=O)/C=C/[C@@H]2CCN2C)C1)c1nc(OC[C@@]23CCCN2C[C@H](F)C3)nc2c(F)c(-c3cccc4ccc(F)c(Cl)c34)ncc12]

Example 220 (Method 8). (E)-1-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-((S)-1-methylazetidin-2-yl)prop-2-en-1-one

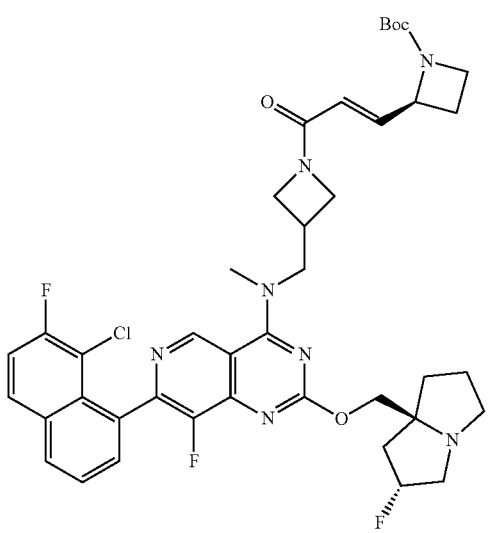 [SMILES: CN(CC1CN(C(=O)/C=C/[C@@H]2CCN2C(=O)OC(C)(C)C)C1)c1nc(OC[C@@]23CCCN2C[C@H](F)C3)nc2c(F)c(-c3cccc4ccc(F)c(Cl)c34)ncc12]

Step 1: tert-butyl (S)-2-((E)-3-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-oxoprop-1-en-1-yl)azetidine-1-carboxylate The HWE reaction was prepared in a similar fashion to Method #8, Step 4. The reaction mixture was diluted with water (5 mL) and extracted with ethyl acetate (3×5 mL). The combined organic layers were dried over sodium sulphate and concentrated in vacuo affording tert-butyl (S)-2-((E)-3-(3-(((7-(8-chloro-7-fluoronaphthalen-1-yl)-8-fluoro-2-

890

(((2R,7aS)-2-fluorotetrahydro-1H-pyrrolizin-7a(5H)-yl)methoxy)pyrido[4,3-d]pyrimidin-4-yl) (methyl) amino) methyl)azetidin-1l-yl)-3-oxoprop-1-en-1-yl)azetidine-1-carboxylate (52 mg, crude) as a yellow oil, used in next step without any further purification. LCMS Rt=0.735 min, m/z=791.3 [M+H]$^+$.

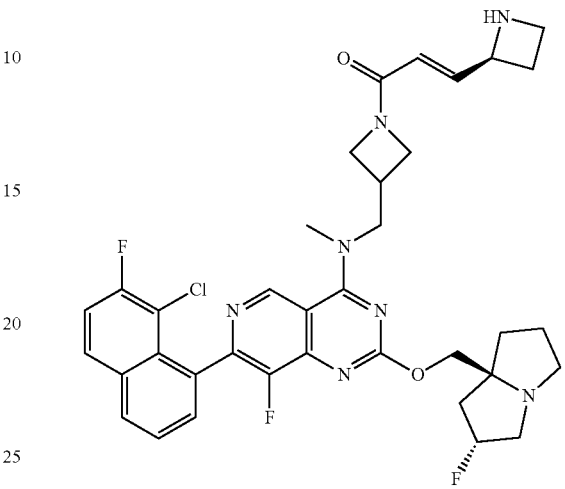

Step 2: (E)-3-((S)-azetidin-2-yl)-1-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)prop-2-en-1-one The deprotection of the Boc group was prepared in a similar fashion to Method #1, Step 9. The reaction mixture was concentrated in vacuo affording (E)-3-((S)-azetidin-2-yl)-1-(3-(((7-(8-chloro-7-fluoronaphthalen-1-yl)-8-fluoro-2-(((2R,7aS)-2-fluorotetrahydro-1H-pyrrolizin-7a(5H)-yl) methoxy)pyrido[4,3-d]pyrimidin-4-yl)(methyl)amino) methyl)azetidin-1-yl)prop-2-en-1-one (50 mg, crude, trifluoroacetic acid salt) as a yellow oil, used in next step without any further purification. LCMS Rt=0.616 min, m/z=691.3 [M+H]$^+$.

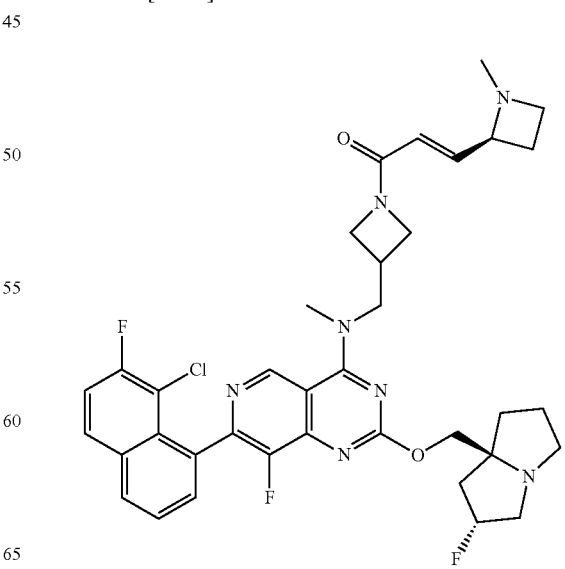

Step 3: (E)-1-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-((S)-1-methylazetidin-2-yl)prop-2-en-1-one The reductive amination was prepared in a similar fashion to Method #8, Step 6. The residue was purified by prep-HPLC (column: Waters Xbridge BEH C18 100*30 mm*10 μm; mobile phase: [water(NH$_4$HCO$_3$)-ACN]; B %: 30%-70%, 8 min) affording (E)-1-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-((S)-1-methylazetidin-2-yl)prop-2-en-1-one (7.65 mg, 14.95%) as a pale yellow solid: $^1$H NMR (400 MHz, Acetonitrile-d3) δ 9.33-9.18 (m, 1H), 8.20-8.13 (m, 1H), 8.09 (dd, J=5.7, 9.1 Hz, 1H), 7.73-7.65 (m, 2H), 7.54 (t, J=8.9 Hz, 1H), 6.71 (dd, J=5.8, 15.3 Hz, 1H), 6.10 (d, J=15.3 Hz, 1H), 5.40-5.16 (m, 1H), 4.42-4.32 (m, 1H), 4.22-4.09 (m, 5H), 3.92-3.79 (m, 1H), 3.63-3.56 (m, 3H), 3.55-3.48 (m, 1H), 3.32-3.26 (m, 1H), 3.24-3.11 (m, 3H), 3.08 (s, 1H), 2.96-2.87 (m, 1H), 2.85-2.70 (m, 1H), 2.26-2.21 (m, 3H), 2.20-2.10 (m, 4H), 2.06 (br s, 1H), 1.94-1.80 (m, 4H).

LCMS (5% to 95% acetonitrile in water+0.03% ammonium bicarbonate over 6 min); retention time 2.891 min, ESI+ found [M+H]=705.3.

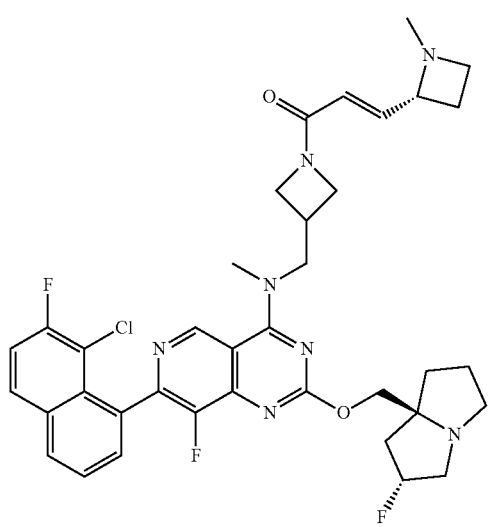 [SMILES: CN(CC1CN(C(=O)/C=C/[C@H]2CCN2C)C1)c1nc(OC[C@@]23CCCN2C[C@H](F)C3)nc2c(F)c(-c3cccc4ccc(F)c(Cl)c34)ncc12]

Example 221 (Method 8): (E)-1-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-((R)-1-methylazetidin-2-yl)prop-2-en-1-one

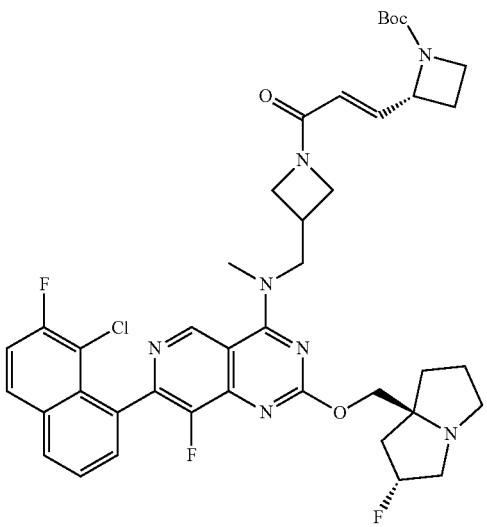 [SMILES: CN(CC1CN(C(=O)/C=C/[C@H]2CCN2C(=O)OC(C)(C)C)C1)c1nc(OC[C@@]23CCCN2C[C@H](F)C3)nc2c(F)c(-c3cccc4ccc(F)c(Cl)c34)ncc12]

Step 1: tert-butyl (R)-2-((E)-3-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-oxoprop-1-en-1-yl)azetidine-1-carboxylate The HWE reaction was prepared in a similar fashion to Method #8, Step 4. The reaction mixture was diluted with water (5 mL) and extracted with ethyl acetate (3×5 mL). The combined organic layers were dried over sodium sulphate and concentrated in vacuo affording tert-butyl (R)-2-((E)-3-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-oxoprop-1-en-1-yl)azetidine-1-carboxylate (50 mg, crude) as a white solid, which was used in the next step without any further purification. LCMS Rt=0.705 min, m/z=791.3 [M+H]$^+$.

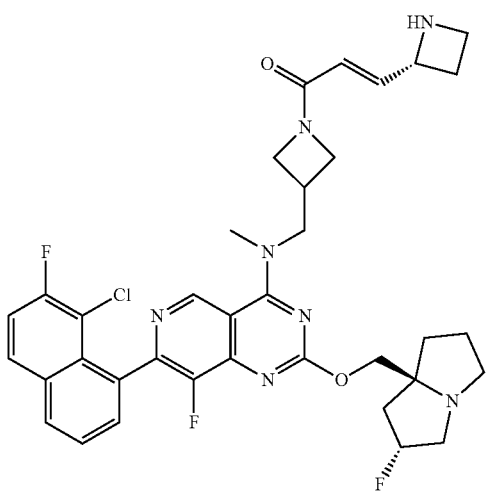 [SMILES: CN(CC1CN(C(=O)/C=C/[C@H]2CCN2)C1)c1nc(OC[C@@]23CCCN2C[C@H](F)C3)nc2c(F)c(-c3cccc4ccc(F)c(Cl)c34)ncc12]

Step 2: (E)-3-((R)-azetidin-2-yl)-1-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)prop-2-en-1-one The deprotection of the Boc group was prepared in a similar fashion to Method #1, Step 9. The reaction mixture was concentrated in vacuo affording (E)-3-((R)-azetidin-2-yl)-1-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)prop-2-en-1-one (50 mg, crude, trifluoroacetic acid salt) as a yellow oil, which was used in the next step without any further purification. LCMS Rt=0.761 min, m/z=691.3 [M+H]⁺.

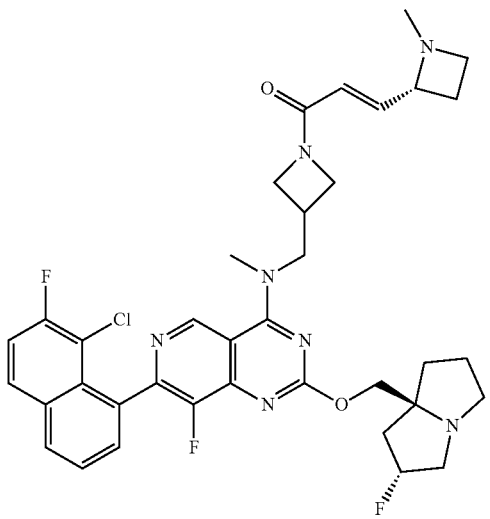

Step 3: (E)-1-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-((R)-1-methylazetidin-2-yl)prop-2-en-1-one The reductive amination was prepared in a similar fashion to Method #8, Step 6. The residue was purified by prep-HPLC (column: Waters Xbridge Prep OBD C18 150*40 mm*10 μm; mobile phase: [water(NH₄HCO₃)-ACN]; B %: 30%-60%, 8 min) affording (E)-1-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-((R)-1-methylazetidin-2-yl)prop-2-en-1-one (10.15 mg, 28.97%) as a yellow oil: ¹H NMR (400 MHz, Acetonitrile-d3) δ 9.31-9.19 (m, 1H), 8.15 (dd, J=3.0, 6.6 Hz, 1H), 8.09 (dd, J=5.8, 9.1 Hz, 1H), 7.72-7.67 (m, 2H), 7.54 (t, J=8.9 Hz, 1H), 6.76-6.66 (m, 1H), 6.10 (br d, J=15.1 Hz, 1H), 5.38-5.19 (m, 1H), 4.41-4.31 (m, 1H), 4.22-4.09 (m, 5H), 3.91-3.79 (m, 1H), 3.62-3.56 (m, 3H), 3.55-3.46 (m, 1H), 3.31-3.26 (m, 1H), 3.23-3.13 (m, 3H), 3.11-3.06 (m, 1H), 2.96-2.87 (m, 1H), 2.84-2.73 (m, 1H), 2.23 (s, 3H), 2.21 (br d, J=2.5 Hz, 1H), 2.17-2.09 (m, 3H), 2.08-2.04 (m, 1H), 1.95-1.83 (m, 4H).

LCMS (5% to 95% acetonitrile in water+0.03% ammonium bicarbonate over 6 min); retention time 2.881 min, ESI+ found [M+H]=705.3.

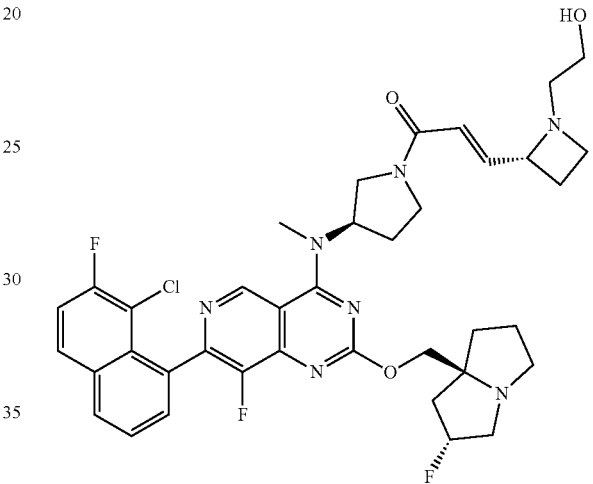

Example 222 (Method 8): (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-(2-hydroxyethyl)azetidin-2-yl)prop-2-en-1-one

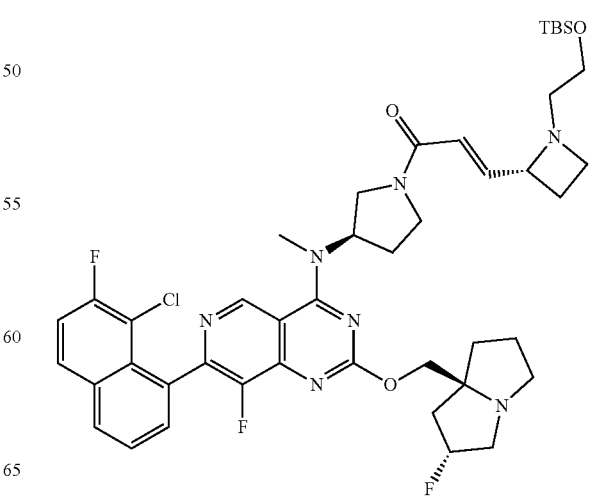

Step 1: (E)-3-((R)-1-(2-((tert-butyldimethylsilyl)oxy)ethyl)azetidin-2-yl)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one The reductive amination reaction was prepared in a similar fashion to Method #8, Step 6. The residue was purified by reverse phase HPLC (column: Phenomenex Luna 80*30 mm*3 μm; mobile phase: [water(TFA)-ACN]; B %: 15%-45%, 8 min) affording (E)-3-((R)-1-(2-((tert-butyldimethylsilyl)oxy)ethyl)azetidin-2-yl)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (26 mg, 27.38%, trifluoroacetate salt) as a yellow solid. LCMS Rt=0.729 min, m/z=849.4 [M+H]+.

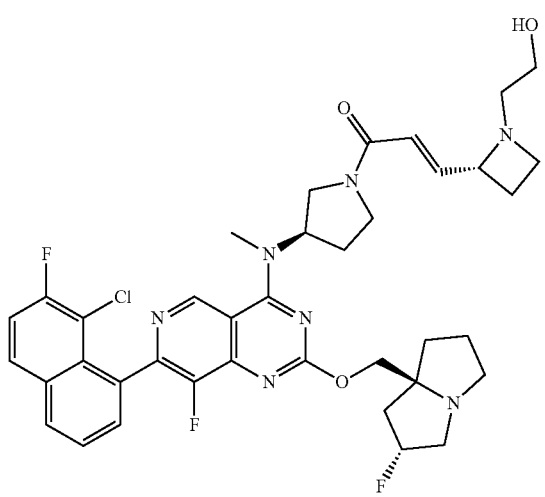 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)/C=C/[C@H]2CCN2CCO)C1]

Step 2: (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-(2-hydroxyethyl)azetidin-2-yl)prop-2-en-1-one To a solution of (E)-3-((R)-1-(2-((tert-butyldimethylsilyl)oxy)ethyl)azetidin-2-yl)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (15 mg, 17.64 μmol, trifluoroacetate salt) in THF (1 mL) was added N,N-diethylethanamine trihydrofluoride (28.43 mg, 176.37 μmol). The mixture was stirred at 25° C. for 12 h. The reaction mixture was concentrated in vacuo, and the residue was purified by reverse phase HPLC (column: Phenomenex Luna C18 75*30 mm*3 μm; mobile phase: [water(FA)-ACN]; B %: 1%-35%, 8 min) affording (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-(2-hydroxyethyl)azetidin-2-yl)prop-2-en-1-one (3.43 mg, 26.42%, formate salt) as a white solid. 1H NMR (400 MHz, Acetonitrile-d3) δ 9.11 (t, J=2.4 Hz, 1H), 8.25 (s, 1H), 8.05 (dd, J=3.5, 6.0 Hz, 1H), 7.89 (dd, J=5.7, 9.1 Hz, 1H), 7.64-7.55 (m, 2H), 7.44 (t, J=8.9 Hz, 1H), 6.83-6.71 (m, 1H), 6.51-6.37 (m, 1H), 5.39-5.04 (m, 2H), 4.30-3.94 (m, 4H), 3.91-3.67 (m, 2H), 3.62-3.48 (m, 3H), 3.43 (br t, J=5.1 Hz, 3H), 3.20-3.07 (m, 4H), 3.01-2.82 (m, 2H), 2.77-2.57 (m, 2H), 2.39-1.98 (m, 8H), 1.89 (br s, 1H), 1.84-1.76 (m, 1H).

LCMS (5% to 95% acetonitrile in water+0.03% ammonium bicarbonate over 6 min); retention time 1.931 min, ESI+ found [M+H]=735.3.

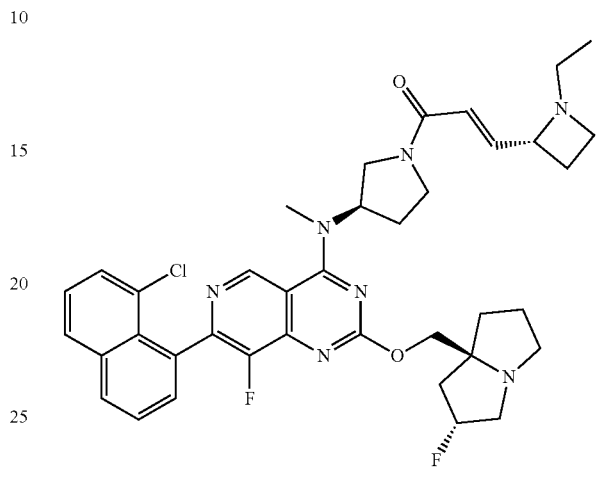

Example 223 (Method 8): (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-ethylazetidin-2-yl)prop-2-en-1-one

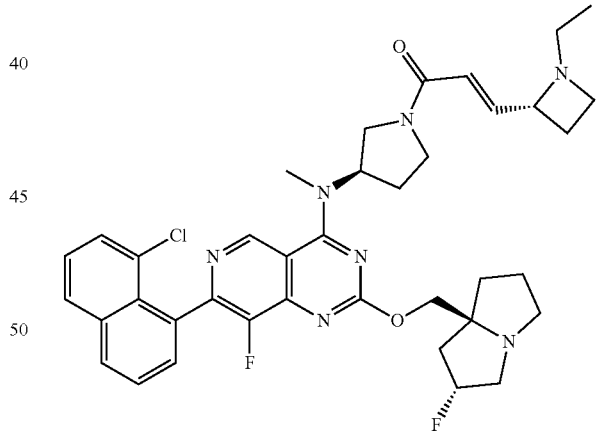

Step 1: (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-ethylazetidin-2-yl)prop-2-en-1-one The reductive amination reaction was prepared in a similar fashion to Method #8, Step 6. The residue was purified by reverse phase HPLC (column: Waters Xbridge BEH C18 100*30 mm*10 um; mobile phase: [water(NH4HCO3)-ACN]; B %: 35%-65%, 8 min) affording (E)-1-((R)-3-((7-

(8-chloronaphthalen-1-yl)-8-fluoro-2-(((2R,7aS)-2-fluoro-tetrahydro-1H-pyrrolizin-7a(5H)-yl)methoxy)pyrido[4,3-d]pyrimidin-4-yl)(methyl)amino)pyrrolidin-1-yl)-3-((R)-1-ethylazetidin-2-yl)prop-2-en-1-one (15.53 mg, 23.63%) as a yellow oil: $^1$H NMR (400 MHz, Acetonitrile-d3) δ 9.22-9.12 (m, 1H), 8.15-8.08 (m, 1H), 8.02 (d, J=8.3 Hz, 1H), 7.72-7.65 (m, 1H), 7.64-7.57 (m, 2H), 7.55-7.47 (m, 1H), 6.79 (dd, J=5.8, 15.1 Hz, 1H), 6.45-6.34 (m, 1H), 5.43-5.15 (m, 2H), 4.24-4.09 (m, 2H), 3.90-3.77 (m, 1H), 3.68-3.54 (m, 2H), 3.42 (s, 3H), 3.32-3.23 (m, 1H), 3.16-3.08 (m, 2H), 3.05 (s, 1H), 2.93-2.84 (m, 1H), 2.82-2.67 (m, 1H), 2.61-2.45 (m, 1H), 2.44-2.23 (m, 3H), 2.39-2.00 (m, 6H), 1.92-1.79 (m, 4H), 1.11-0.88 (m, 3H).

LCMS (5% to 95% acetonitrile in water+0.03% ammonium bicarbonate over 6 min); retention time 2.993 min, ESI+ found [M+H]=701.3.

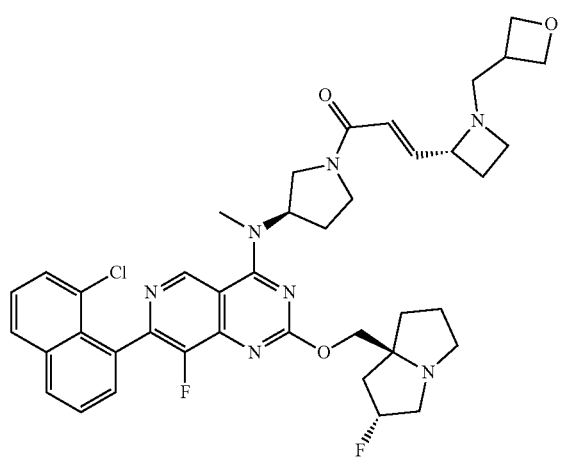 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/[C@H]2CCN2CC2COC2)C1]

Example 224 (Method 8): (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-(oxetan-3-ylmethyl)azetidin-2-yl)prop-2-en-1-one

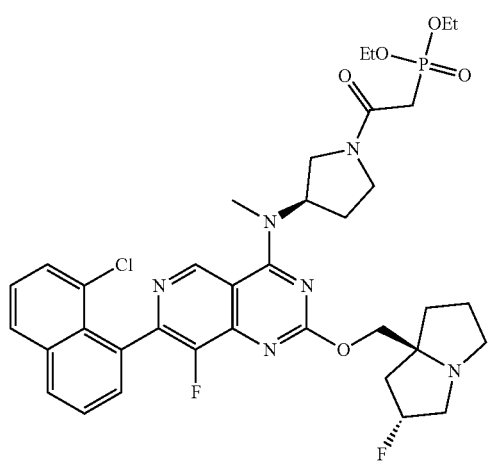 [SMILES: CCOP(=O)(CC(=O)N1CC[C@@H](N(C)c2nc(OC[C@@]34CCCN3C[C@H](F)C4)nc3c(F)c(-c4cccc5cccc(Cl)c45)ncc23)C1)OCC]

Step 1: diethyl (2-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-2-oxoethyl)phosphonate The amide coupling reaction was prepared in a similar fashion to Method #8, Step 3. The crude product was purified by column chromatography (silica gel, 100-200 mesh, 6-7% methanol in dichloromethane) affording diethyl (2-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-2-oxoethyl)phosphonate (700 mg, 72.96%) as an orange gum.

LCMS Rt=0.715 min, m/z=742.3 [M+H]$^+$.

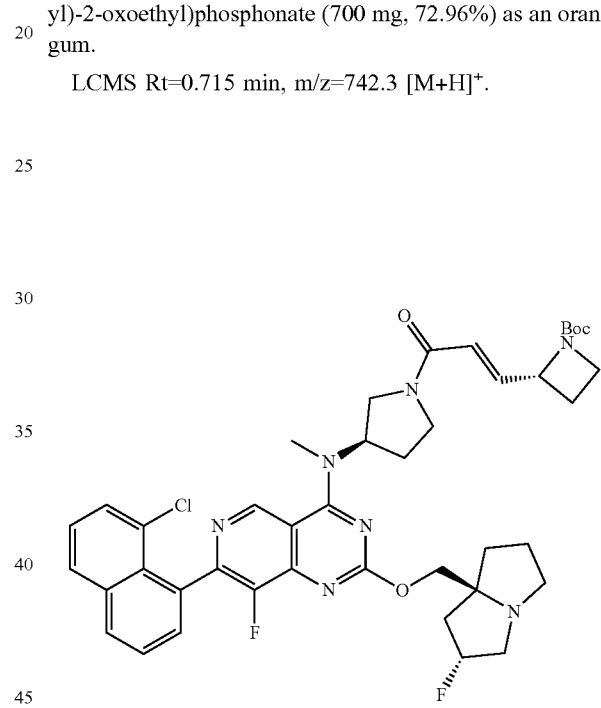

Step 2: tert-butyl (R)-2-((E)-3-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-oxoprop-1-en-1-yl)azetidine-1-carboxylate The HWE reaction was prepared in a similar fashion to Method #8, Step 4. The crude product was purified by column chromatography (silica gel, 100-200 mesh, 50-60% tetrahydrofuran in petroleum ether) affording tert-butyl (R)-2-((E)-3-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-oxoprop-1-en-1-yl)azetidine-1-carboxylate (470 mg, 63.80%) as a yellow solid. LCMS Rt=0.782 min, m/z=773.3 [M+H]$^+$.

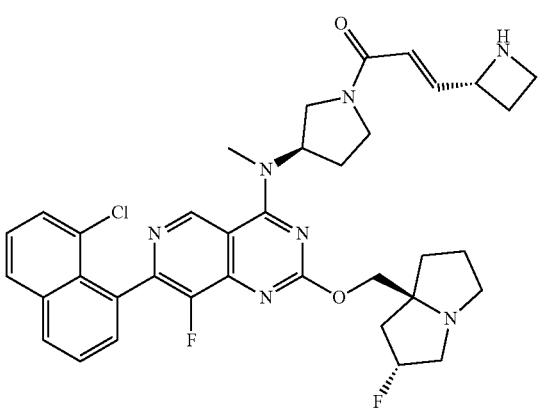 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/[C@H]2CCN2)C1]

Step 3: (E)-3-((R)-azetidin-2-yl)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one The deprotection of the Boc group was prepared in a similar fashion to Method #1, Step 9. The reaction mixture was concentrated in vacuo affording (E)-3-((R)-azetidin-2-yl)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (162 mg, crude, trifluoroacetic acid salt) as a pale yellow solid, which was used in the next step without any further purification. LCMS Rt=0.638 min, m/z=673.3 [M+H]$^+$.

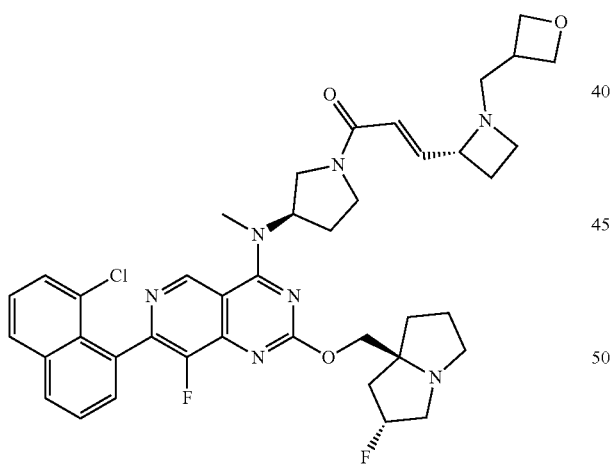

Step 4: (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-(oxetan-3-ylmethyl)azetidin-2-yl)prop-2-en-1-one The reductive amination reaction was prepared in a similar fashion to Method #8, Step 6. The residue was purified by reverse phase HPLC (column: Waters Xbridge Prep OBD C18 150*40 mm*10 um; mobile phase: [water(NH$_4$HCO$_3$)-ACN]; B %: 30%-60%, 8 min) affording (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-(oxetan-3-ylmethyl)azetidin-2-yl)prop-2-en-1-one (10.51 mg, 13.39%) as a yellow amorphous solid: $^1$H NMR (400 MHz, Acetonitrile-d3) δ 9.21-9.15 (m, 1H), 8.12 (d, J=8.1 Hz, 1H), 8.02 (d, J=8.0 Hz, 1H), 7.71-7.66 (m, 1H), 7.65-7.58 (m, 2H), 7.54-7.47 (m, 1H), 6.77 (dd, J=5.7, 15.1 Hz, 1H), 6.42-6.31 (m, 1H), 5.43-5.15 (m, 2H), 4.68-4.56 (m, 2H), 4.32-4.17 (m, 3H), 4.16-4.09 (m, 1H), 4.06-3.76 (m, 2H), 3.72-3.61 (m, 2H), 3.54 (ddd, J=7.4, 12.6, 17.2 Hz, 1H), 3.44-3.41 (m, 3H), 3.30-3.22 (m, 1H), 3.17-3.10 (m, 2H), 3.06 (s, 1H), 2.98 (br dd, J=7.4, 14.6 Hz, 1H), 2.87-2.74 (m, 2H), 2.70-2.61 (m, 1H), 2.43-2.26 (m, 2H), 2.21-2.07 (m, 7H), 1.89-1.84 (m, 2H).

LCMS (5% to 95% acetonitrile in water+0.03% ammonium bicarbonate over 6 min); retention time 2.883 min, ESI+ found [M+H]=743.3.

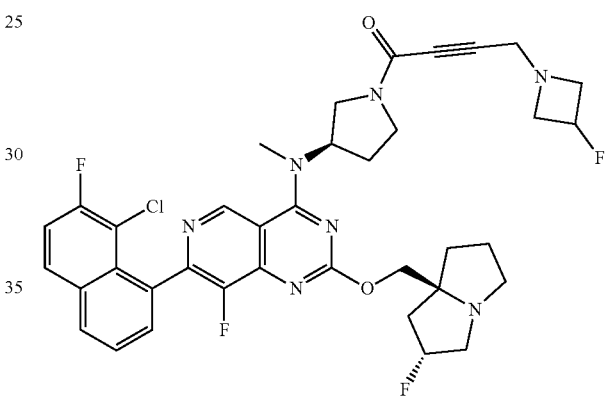

Example 225 (Method 13-master): 1-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-4-(3-fluoroazetidin-1-yl)but-2-yn-1-one

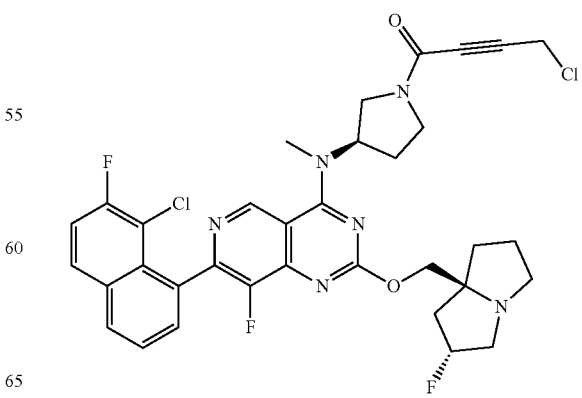

Step 1: 4-chloro-1-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)but-2-yn-1-one The amide coupling reaction was prepared in a similar fashion to Method #1, Step 10. The residue was purified by reverse phase HPLC (TFA condition; column: Phenomenex Luna 80*30 mm*3 µm; mobile phase: [water(TFA)-ACN]; B %: 15%-45%, 8 min) affording 4-chloro-1-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)but-2-yn-1-one (130 mg, 43.32%, trifluoroacetic salt) as a yellow solid. LCMS Rt=1.578 min, m/z=682.2 [M+H]⁺.

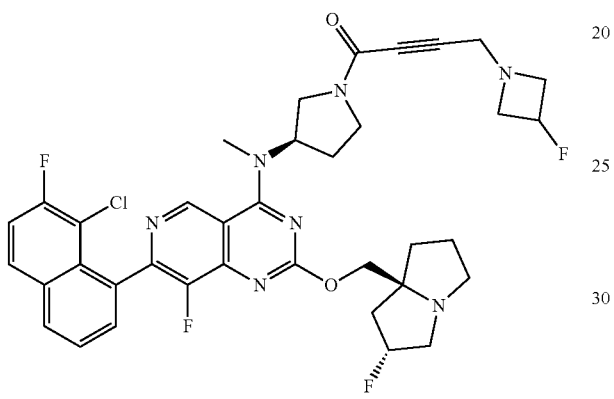

Step 2: 1-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-4-(3-fluoroazetidin-1-yl)but-2-yn-1-one To a solution of 4-chloro-1-((R)-3-((7-(8-chloro-7-fluoronaphthalen-1-yl)-8-fluoro-2-(((2R,7aS)-2-fluorohexahydro-TH-pyrrolizin-7a-yl)methoxy)pyrido[4,3-d]pyrimidin-4-yl)(methyl)amino)pyrrolidin-1-yl)but-2-yn-1-one (50 mg, 73.15 µmol) and 3-fluoroazetidine; hydrochloride (16.32 mg, 146.30 µmol) in N,N-dimethylformaldehyde (1 mL) was added potassium carbonate (30.33 mg, 219.44 µmol). The mixture was stirred at 50° C. for 0.5 h.

The reaction mixture was filtered, and the filtrate was concentrated in vacuo. The residue was purified by reverse phase HPLC (neutral condition; column: Waters Xbridge Prep OBD C18 150*40 mm*10 um; mobile phase: [water (NH₄HCO₃)-ACN]; B %: 25%-45%, 8 min) affording 1-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-4-(3-fluoroazetidin-1-yl)but-2-yn-1-one (4.83 mg, 8.67%) as a yellow solid: ¹H NMR (400 MHz, Acetonitrile-d3) δ 9.22 (s, 1H), 8.17 (br dd, J=3.4, 6.1 Hz, 1H), 8.11 (dd, J=5.8, 9.1 Hz, 1H), 7.76-7.67 (m, 2H), 7.56 (t, J=8.9 Hz, 1H), 5.53-5.00 (m, 3H), 4.28-4.11 (m, 3H), 4.10-3.89 (m, 1H), 3.84-3.74 (m, 1H), 3.70-3.59 (m, 2H), 3.54 (d, J=11.9 Hz, 2H), 3.50-3.44 (m, 4H), 3.44-3.31 (m, 2H), 3.24-3.06 (m, 3H), 2.99-2.87 (m, 1H), 2.47-2.30 (m, 2H), 2.18-2.04 (m, 3H), 1.95-1.81 (m, 3H).

LCMS (5% to 95% acetonitrile in water+0.03% ammonium bicarbonate over 6 min); retention time 2.960 min, ESI+ found [M+H]=721.3.

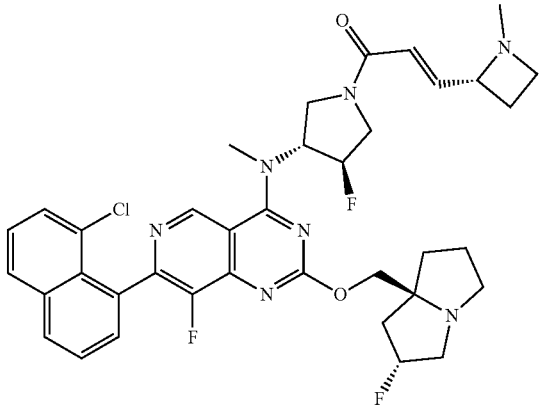 [SMILES: CN1CC[C@@H]1/C=C/C(=O)N1C[C@@H](F)[C@H](N(C)c2nc(OC[C@@]34CCCN3C[C@H](F)C4)nc3c(F)c(-c4cccc5cccc(Cl)c45)ncc23)C1]

Example 226 (Method 8):(E)-1-((3R,4R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-((R)-1-methylazetidin-2-yl)prop-2-en-1-one

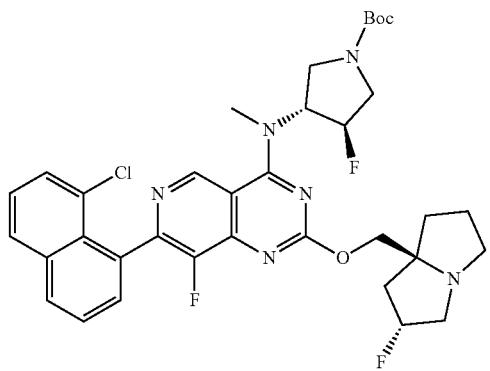 [SMILES: CN(c1nc(OC[C@@]23CCCN2C[C@H](F)C3)nc2c(F)c(-c3cccc4cccc(Cl)c34)ncc12)[C@@H]1CN(C(=O)OC(C)(C)C)C[C@H]1F]

Step 1: (3R,4R)-tert-butyl 3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidine-1-carboxylate The substitution reaction was prepared in a similar fashion to Method #1, Step 8. The residue was purified by prep-HPLC (column: Phenomenex Luna C18 (250*70 mm, 15 µm); mobile phase: [water(TFA)-ACN]; B %: 25%-65%, 24 min) affording (3R,4R)-tert-butyl 3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidine-1-carboxylate (600 mg, 13.98%, trifluoroacetate salt) as a white solid. LCMS Rt=0.764 min, m/z=682.3 [M+H]⁺.

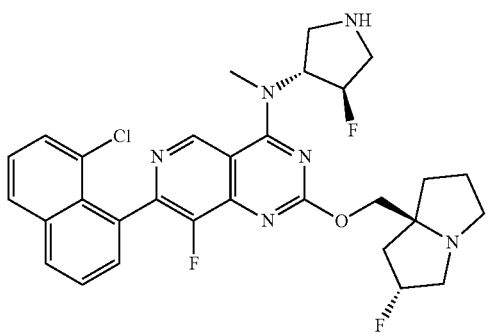 [SMILES: CN(c1nc(OC[C@@]23CCCN2C[C@H](F)C3)nc2c(F)c(-c3cccc4cccc(Cl)c34)ncc12)[C@@H]1CNC[C@H]1F]

Step 2: 7-(8-chloronaphthalen-1-yl)-8-fluoro-2-(((2R,7aS)-2-fluorohexahydro-1H-pyrrolizin-7a-yl)methoxy)-N-((3R,4R)-4-fluoropyrrolidin-3-yl)-N-methylpyrido[4,3-d]pyrimidin-4-amine The deprotection of Boc group was prepared in a similar fashion to Method #1, Step 9. The reaction mixture was concentrated in vacuo affording 7-(8-chloronaphthalen-1-yl)-8-fluoro-2-(((2R,7aS)-2-fluorohexahydro-1H-pyrrolizin-7a-yl)methoxy)-N-((3R,4R)-4-fluoropyrrolidin-3-yl)-N-methylpyrido[4,3-d]pyrimidin-4-amine (550 mg, crude, trifluoroacetic acid salt) as a yellow oil, which was used in the next step without any further purification. LCMS Rt=0.605 min, m/z=582.2 [M+H]$^+$.

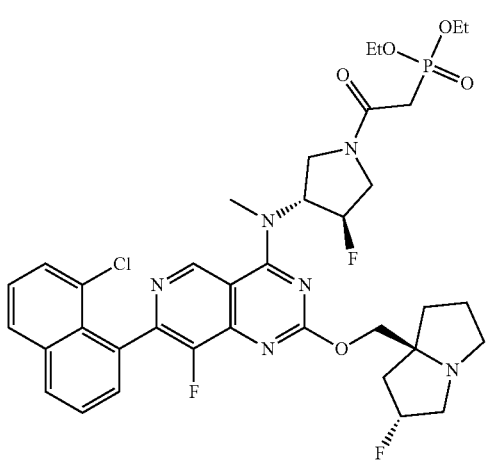 [SMILES: CCOP(=O)(CC(=O)N1C[C@@H](F)[C@H](N(C)c2nc(OC[C@@]34CCCN3C[C@H](F)C4)nc3c(F)c(-c4cccc5cccc(Cl)c45)ncc23)C1)OCC]

Step 3: diethyl (2-((3R,4R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidin-1-yl)-2-oxoethyl)phosphonate The amide coupling reaction was prepared in a similar fashion to Method #8, Step 3. The residue was purified by prep-HPLC (column: Phenomenex Luna 80*30 mm*3 μm; mobile phase: [water(TFA)-ACN]; B %: 10%-45%, 8 min) affording diethyl (2-((3R,4R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidin-1-yl)-2-oxoethyl)phosphonate (120 mg, 47.79%, trifluoroacetate salt) as a yellow solid. LCMS Rt=0.702 min, m/z=760.3 [M+H]$^+$.

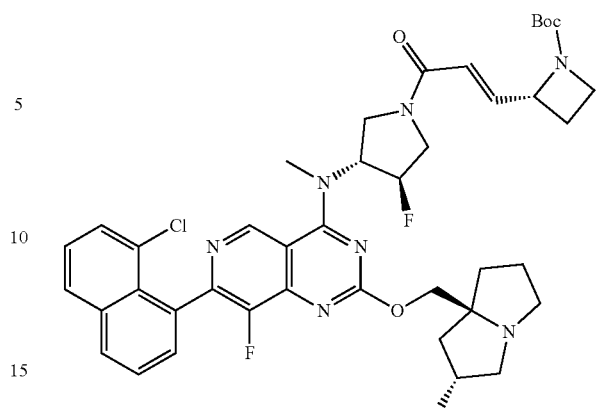

Step 4: (R)-tert-butyl 2-((E)-3-((3R,4R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidin-1-yl)-3-oxoprop-1-en-1-yl)azetidine-1-carboxylate The HWE reaction was prepared in a similar fashion to Method #8, Step 4. The reaction mixture was concentrated in vacuo affording (R)-tert-butyl 2-((E)-3-((3R,4R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidin-1-yl)-3-oxoprop-1-en-1-yl)azetidine-1-carboxylate (60 mg, crude) as a yellow oil, used in next step without any further purification. LCMS Rt=0.755 min, m/z=791.3 [M+H]$^+$.

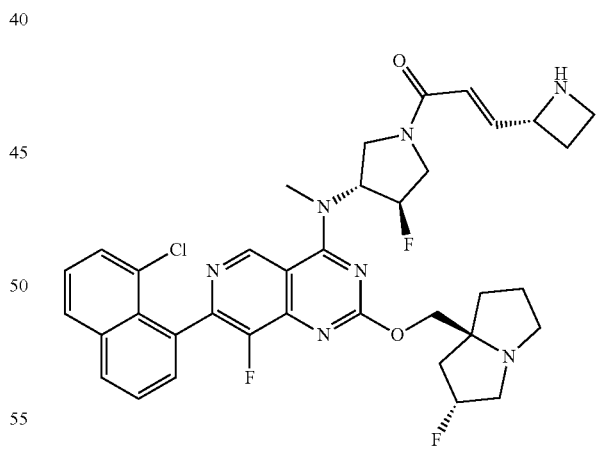

Step 5: (E)-3-((R)-azetidin-2-yl)-1-((3R,4R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidin-1-yl)prop-2-en-1-one The deprotection of the Boc group was prepared in a similar fashion to Method #1, Step 9. The reaction mixture was concentrated in vacuo affording (E)-3-((R)-azetidin-2- yl)-1-((3R,4R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)-4-fluoropyrrolidin-1-yl)prop-2-en-1-one (60 mg, crude, trifluoroacetic acid salt) as a yellow oil, which was used in the next step without any further purification. LCMS Rt=0.623 min, m/z=691.3 [M+H]⁺.

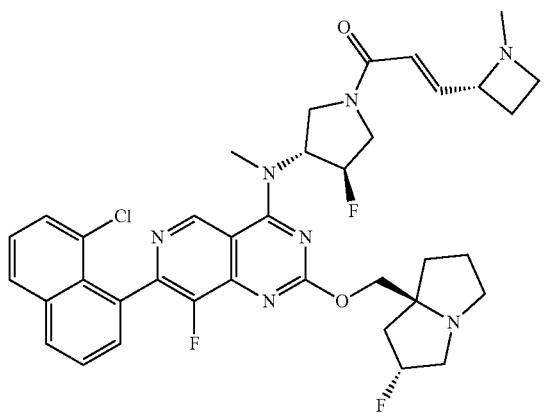 [SMILES: CN1CC[C@@H]1/C=C/C(=O)N1C[C@@H](F)[C@H](N(C)c2nc(OC[C@@]34CCCN3C[C@H](F)C4)nc3c(F)c(-c4cccc5cccc(Cl)c45)ncc23)C1]

Step 6: (E)-1-((3R,4R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-((R)-1-methylazetidin-2-yl)prop-2-en-1-one The reductive amination was prepared in a similar fashion to Method #8, Step 6.

The residue was purified by prep-HPLC (column: Waters Xbridge Prep OBD C18 150*40 mm*10 μm; mobile phase: [water(NH₄HCO₃)-ACN]; B %: 35%-65%, 8 min) affording (E)-1-((3R,4R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-((R)-1-methylazetidin-2-yl)prop-2-en-1-one (7.72 mg, 13.76%) as a white solid: ¹H NMR (400 MHz, Acetonitrile-d3) δ 9.27 (s, 1H), 8.15 (br d, J=8.1 Hz, 1H), 8.05 (br d, J=8.1 Hz, 1H), 7.68-7.75 (m, 1H), 7.61-7.67 (m, 2H), 7.51-7.57 (m, 1H), 6.83 (dd, J=15.1 Hz, J=5.6 Hz, 1H), 6.35-6.46 (m, 1H), 5.55-5.69 (m, 1H), 5.19-5.38 (m, 2H), 4.14-4.25 (m, 3H), 3.76-3.96 (m, 3H), 3.53 (br d, J=4.0 Hz, 3H), 3.31 (br d, J=8.0 Hz, 1H), 3.14 (br d, J=6.4 Hz, 2H), 3.07 (br s, 1H), 2.80-2.96 (m, 3H), 2.28 (s, 2H), 2.26 (s, 1H), 2.19 (br d, J=7.6 Hz, 2H), 2.08-2.16 (m, 3H), 2.06 (br s, 1H), 1.89 (br dd, J=10.6 Hz, J=6.6 Hz, 2H). LCMS Rt=2.961 min, m/z=705.3 [M +H]⁺.

LCMS (5 to 95% acetonitrile in water+0.03% ammonium bicarbonate over 6 mins) retention time 2.961 min, ESI+ found [M+H]=705.3.

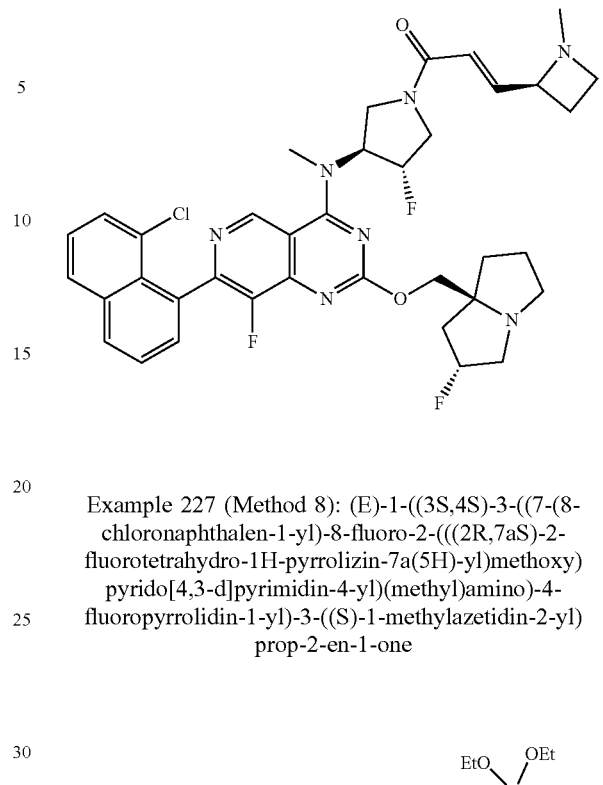

Example 227 (Method 8): (E)-1-((3S,4S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-((S)-1-methylazetidin-2-yl)prop-2-en-1-one

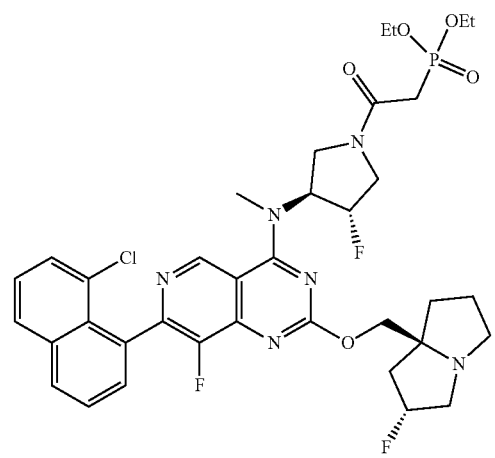 [SMILES: CCOP(=O)(CC(=O)N1C[C@H](F)[C@@H](N(C)c2nc(OC[C@@]34CCCN3C[C@H](F)C4)nc3c(F)c(-c4cccc5cccc(Cl)c45)ncc23)C1)OCC]

Step 1: diethyl (2-((3S,4S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-2-oxoethyl)phosphonate The amide coupling reaction was prepared in a similar fashion to Method #8, Step 3. The residue was purified by prep-HPLC (column: C18 150*30 mm*5 μm; mobile phase: [water(TFA)-ACN]; B %: 15%-60%, 8 min) affording diethyl (2-((3S,4S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-2-oxoethyl)phosphonate (180 mg, 54.07%, trifluoroacetate salt) as a yellow solid. LCMS Rt=0.696 min, m/z=760.3 [M+H]⁺.

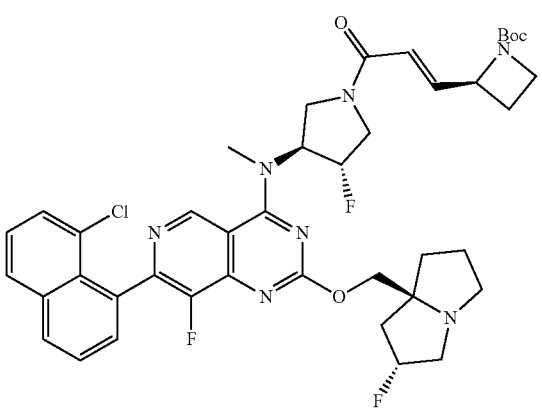 [SMILES: CN(c1nc(OC[C@@]23CCCN2C[C@H](F)C3)nc2c(F)c(-c3cccc4cccc(Cl)c34)ncc12)[C@H]1CN(C(=O)/C=C/[C@@H]2CCN2C(=O)OC(C)(C)C)C[C@@H]1F]

Step 2: tert-butyl (S)-2-((E)-3-((3S,4S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-oxoprop-1-en-1-yl)azetidine-1-carboxylate The HWE reaction was prepared in a similar fashion to Method #8, Step 4. The reaction mixture was concentrated in vacuo affording tert-butyl (S)-2-((E)-3-((3S,4S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-oxoprop-1-en-1-yl)azetidine-1-carboxylate (83 mg, crude) as a yellow oil, which was used in the next step without any further purification. LCMS Rt=0.711 min, m/z=791.3 [M+H]$^+$.

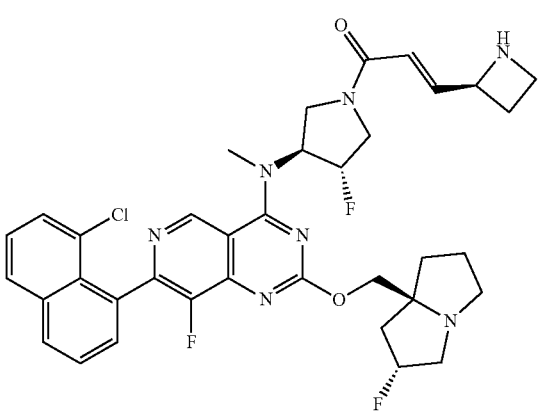 [SMILES: CN(c1nc(OC[C@@]23CCCN2C[C@H](F)C3)nc2c(F)c(-c3cccc4cccc(Cl)c34)ncc12)[C@H]1CN(C(=O)/C=C/[C@@H]2CCN2)C[C@@H]1F]

Step 3: (E)-3-((S)-azetidin-2-yl)-1-((3S,4S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)prop-2-en-1-one The deprotection of the Boc group was prepared in a similar fashion to Method #1, Step 9. The reaction mixture was concentrated in vacuo affording (E)-3-((S)-azetidin-2-yl)-1-((3S,4S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)prop-2-en-1-one (84 mg, crude, trifluoroacetic acid salt) as a yellow solid, which was used in the next step without any further purification. LCMS Rt=0.625 min, m/z=691.3 [M+H]$^+$.

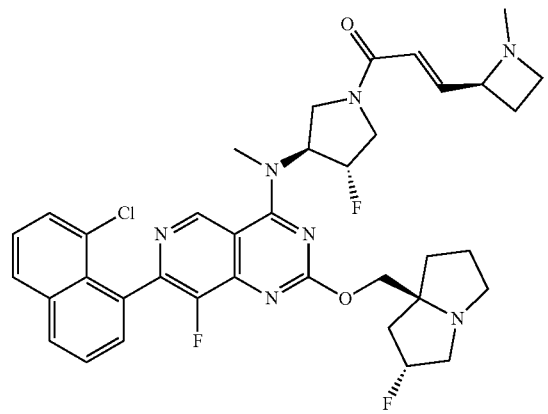 [SMILES: CN1CC[C@H]1/C=C/C(=O)N1C[C@H](F)[C@@H](N(C)c2nc(OC[C@@]34CCCN3C[C@H](F)C4)nc3c(F)c(-c4cccc5cccc(Cl)c45)ncc23)C1]

Step 4: (E)-1-((3S,4S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-((S)-1-methylazetidin-2-yl)prop-2-en-1-one The reductive amination was prepared in a similar fashion to Method #8, Step 6.

The residue was purified by prep-HPLC (column: Waters Xbridge Prep OBD C18 150*40 mm*10 μm; mobile phase: [water(NH$_4$HCO$_3$)-ACN]; B %: 30%-70%, 8 min) affording (E)-1-((3S,4S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-((S)-1-methylazetidin-2-yl)prop-2-en-1-one (3.99 mg, 5.22%) as a yellow oil: $^1$H NMR (400 MHz, Acetonitrile-d3) δ 9.30 (s, 1H), 8.21-8.15 (m, 1H), 8.08 (br d, J=8.1 Hz, 1H), 7.79-7.72 (m, 1H), 7.70-7.63 (m, 2H), 7.60-7.54 (m, 1H), 6.86 (br dd, J=5.4, 15.2 Hz, 1H), 6.43 (br dd, J=5.7, 15.5 Hz, 1H), 5.80-5.53 (m, 1H), 5.47-5.17 (m, 2H), 4.26-4.14 (m, 3H), 4.03-3.75 (m, 3H), 3.61-3.53 (m, 3H), 3.39-3.29 (m, 1H), 3.26-3.15 (m, 2H), 3.13-3.06 (m, 1H), 2.98-2.78 (m, 3H), 2.30 (br s, 3H), 2.21-2.04 (m, 5H), 1.96-1.81 (m, 3H).

LCMS (5% to 95% acetonitrile in water+0.03% ammonium bicarbonate over 6 min); retention time 2.967 min, ESI+ found [M+H]=705.3.

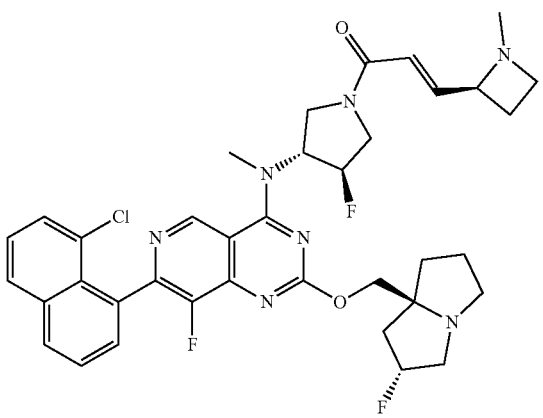 [SMILES: CN1CC[C@H]1/C=C/C(=O)N1C[C@@H](F)[C@H](N(C)c2nc(OC[C@@]34CCCN3C[C@H](F)C4)nc3c(F)c(-c4cccc5cccc(Cl)c45)ncc23)C1]

Example 228 (Method 8): (E)-1-((3R,4R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-((S)-1-methylazetidin-2-yl)prop-2-en-1-one

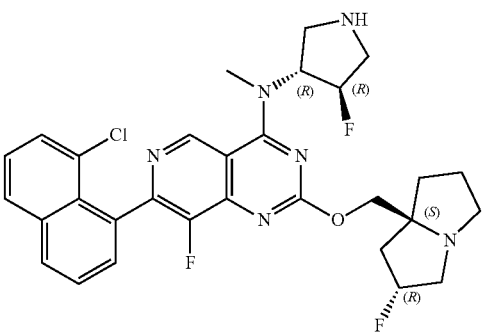

Step 2: 7-(8-chloronaphthalen-1-yl)-8-fluoro-N-((3R,4R)-4-fluoropyrrolidin-3-yl)-2-(((2R,7aS)-2-fluorotetrahydro-1H-pyrrolizin-7a(5H)-yl)methoxy)-N-methylpyrido[4,3-d]pyrimidin-4-amine The deprotection of the Boc was prepared in a similar fashion to Method #1, Step 9. The reaction mixture was concentrated in vacuo affording 7-(8-chloronaphthalen-1-yl)-8-fluoro-N-((3R,4R)-4-fluoropyrrolidin-3-yl)-2-(((2R,7aS)-2-fluorotetrahydro-1H-pyrrolizin-7a(5H)-yl)methoxy)-N-methylpyrido[4,3-d]pyrimidin-4-amine (550 mg, crude) as a yellow solid, which was used in the next step without further purification. LCMS Rt=0.605 min, m/z=582.2 [M+H]$^+$

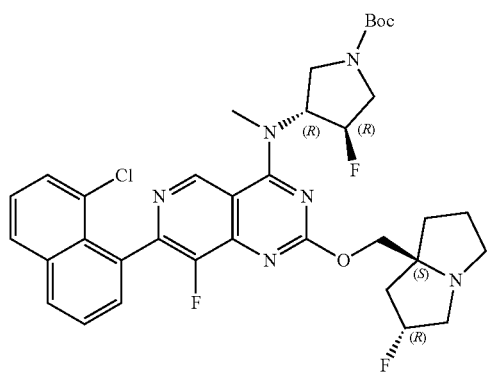

Step 1: tert-butyl (3R,4R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidine-1-carboxylate The substitution reaction was prepared in a similar fashion to Method #1, Step 8. The crude product was purified by reverse phase HPLC (column: Phenomenex Luna C18 (250*70 mm, 15 µm); mobile phase: [water(TFA)-ACN]; B %: 25%-65%, 24 min) affording tert-butyl (3R,4R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidine-1-carboxylate (600 mg, 13.98%, trifluoroacetic salt) as a yellow solid. LCMS Rt=0.769 min, m/z=682.3 [M+H]$^+$.

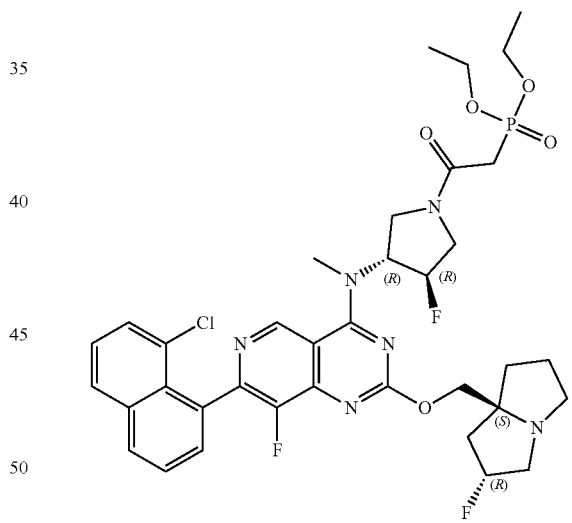

Step 3: diethyl (2-((3R,4R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-2-oxoethyl)phosphonate The amide coupling reaction was prepared in a similar fashion to Method #8, Step 3. The crude product was purified by reverse phase HPLC (column: Phenomenex Luna 80*30 mm*3 µm; mobile phase: [water(TFA)-ACN]; B %: 10%-45%, 8 min) affording diethyl (2-((3R,4R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]

pyrimidin-4-yl)(methyl)amino)-4-fluoropyrrolidin-1-yl)-2-oxoethyl)phosphonate (120 mg, 47.79%, trifluoroacetic salt) as a yellow oil. LCMS Rt=0.706 min, m/z=760.3 [M+H]⁺.

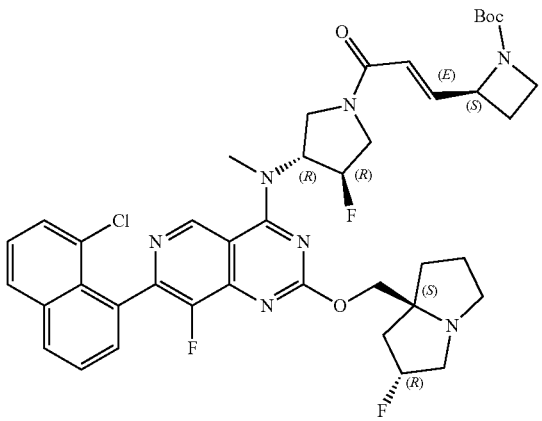

Step 4: tert-butyl (S)-2-((E)-3-((3R,4R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-oxoprop-1-en-1-yl)azetidine-1-carboxylate The HWE reaction was prepared in a similar fashion to Method #8, Step 4. The combined organic layers were concentrated in vacuo affording tert-butyl (S)-2-((E)-3-((3R,4R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-oxoprop-1-en-1-yl)azetidine-1-carboxylate (50 mg, crude) as a brown oil, which was used in the next step without further purification. LCMS Rt=0.753 min, m/z=791.3 [M+H]⁺.

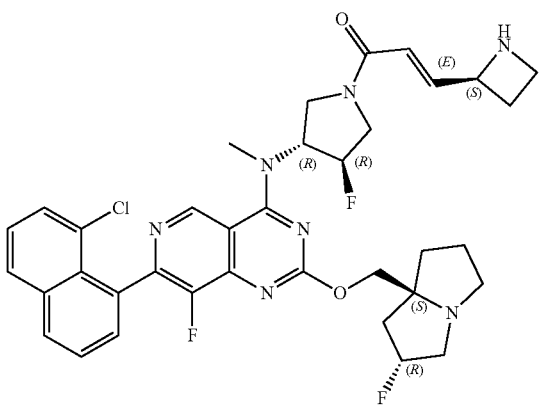

Step 5: (E)-1-((3R,4R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-((S)-azetidin-2-yl)prop-2-en-1-one The deprotection of the Boc group was prepared in a similar fashion to Method #1, Step 9. The crude product was concentrated in vacuo affording (E)-1-((3R,4R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-((S)-azetidin-2-yl)prop-2-en-1-one (43 mg, crude, trifluoroacetic salt) as a brown oil, which was used in the next step without any further purification. LCMS Rt=0.625 min, m/z=691.3 [M+H]⁺.

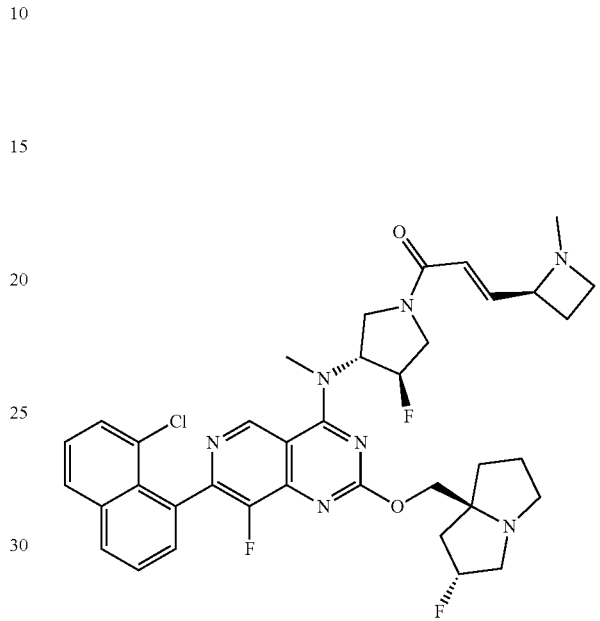

Step 6: (E)-1-((3R,4R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-((S)-1-methylazetidin-2-yl)prop-2-en-1-one The reductive amination was prepared in a similar fashion to Method #8, Step 6. The residue was purified by reverse phase HPLC (column: Waters Xbridge BEH C18 150*40 mm*10 μm; mobile phase: [water(NH₄HCO₃)-ACN]; B %: 35%-65%, 8 min) affording (E)-1-((3R,4R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-((S)-1-methylazetidin-2-yl)prop-2-en-1-one (4.73 mg, 12.52%) as a white solid: ¹H NMR (400 MHz, Acetonitrile-d3) δ 9.27 (s, 1H), 8.23-7.98 (m, 2H), 7.76-7.69 (m, 1H), 7.67-7.61 (m, 2H), 7.57-7.50 (m, 1H), 6.84 (dd, J=5.7, 15.1 Hz, 1H), 6.51-6.28 (m, 1H), 5.79-5.50 (m, 1H), 5.43-5.12 (m, 2H), 4.32-4.08 (m, 4H), 3.94-3.71 (m, 2H), 3.53 (br d, J=5.3 Hz, 3H), 3.40-3.24 (m, 1H), 3.15 (br d, J=5.4 Hz, 2H), 3.07 (br s, 1H), 3.04-2.73 (m, 3H), 2.30-2.23 (m, 4H), 2.12 (br s, 3H), 2.07 (br s, 2H), 1.88 (br d, J=8.1 Hz, 2H). LCMS Rt=2.853 min, m/z=705.3 [M+H]⁺.

LCMS (5% to 95% acetonitrile in water+0.03% ammonium bicarbonate over 6 min); retention time 2.853 min, ESI+ found [M+H]=705.3.

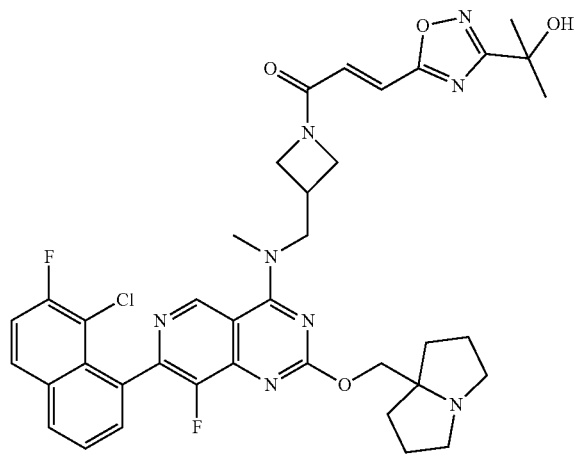 [SMILES: CN(CC1CN(C(=O)/C=C/c2nc(C(C)(C)O)no2)C1)c1nc(OCC23CCCN2CCC3)nc2c(F)c(-c3cccc4ccc(F)c(Cl)c34)ncc12]

Example 229 (Method 2): (E)-1-(3-(((7-(8-chloro-7-fluoronaphthalen-1-yl)-8-fluoro-2-((tetrahydro-1H-pyrrolizin-7a(5H)-yl)methoxy)pyrido[4,3-d]pyrimidin-4-yl)(methyl)amino)methyl)azetidin-1-yl)-3-(3-(2-hydroxypropan-2-yl)-1,2,4-oxadiazol-5-yl)prop-2-en-1-one

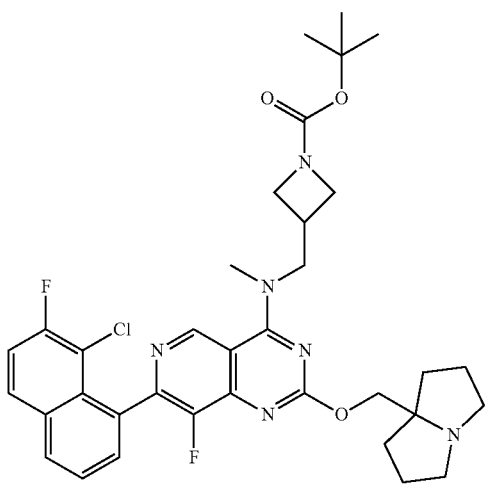 [SMILES: CN(CC1CN(C(=O)OC(C)(C)C)C1)c1nc(OCC23CCCN2CCC3)nc2c(F)c(-c3cccc4ccc(F)c(Cl)c34)ncc12]

Step 1: tert-butyl 3-(((7-(8-chloro-7-fluoronaphthalen-1-yl)-8-fluoro-2-((tetrahydro-1H-pyrrolizin-7a(5H)-yl)methoxy)pyrido[4,3-d]pyrimidin-4-yl)(methyl)amino)methyl)azetidine-1-carboxylate The Suzuki reaction was prepared in a similar fashion to Method #2, Step 5. The crude residue was purified by reverse phase prep-HPLC (column: Waters Xbridge BEH C18 250*50 mm*10 μm; mobile phase: [water(NH$_4$HCO$_3$)-ACN]; B %: 40%-70%, 10 min) affording tert-butyl 3-(((7-(8-chloro-7-fluoronaphthalen-1-yl)-8-fluoro-2-((tetrahydro-1H-pyrrolizin-7a(5H)-yl)methoxy)pyrido[4,3-d]pyrimidin-4-yl)(methyl)amino)methyl)azetidine-1-carboxylate (100 mg, 15.67%) as a white solid. LCMS Rt=2.101 min, m/z=664.3 [M+H]$^+$.

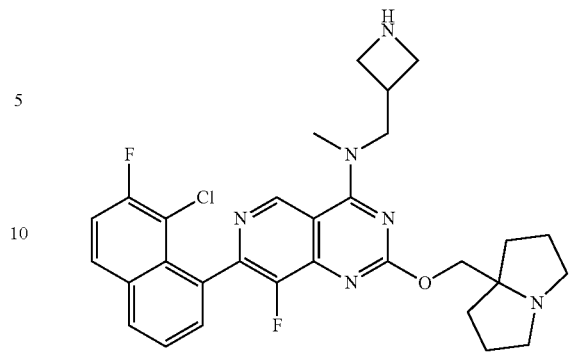

Step 2: N-(azetidin-3-ylmethyl)-7-(8-chloro-7-fluoronaphthalen-1-yl)-8-fluoro-N-methyl-2-((tetrahydro-1H-pyrrolizin-7a(5H)-yl)methoxy)pyrido[4,3-d]pyrimidin-4-amine The deprotection of the Boc group was prepared in a similar fashion to Method #1, Step 9. The reaction mixture was concentrated in vacuo affording N-(azetidin-3-ylmethyl)-7-(8-chloro-7-fluoronaphthalen-1-yl)-8-fluoro-N-methyl-2-((tetrahydro-1H-pyrrolizin-7a(5H)-yl)methoxy)pyrido[4,3-d]pyrimidin-4-amine (80 mg, crude, trifluoroacetic salt) as a white solid, which was used in the next step without further purification. LCMS Rt=0.606 min, m/z=564.2 [M+H]$^+$.

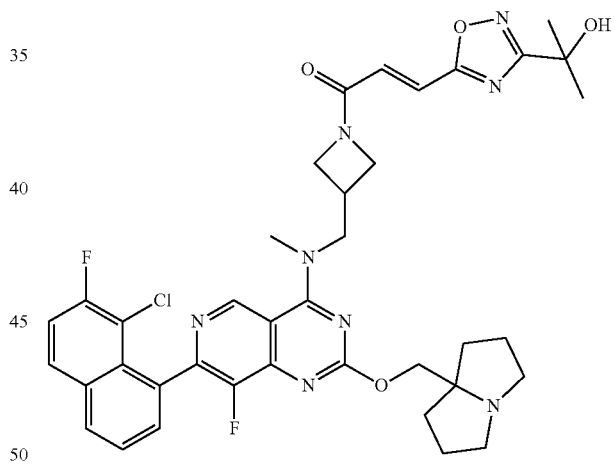

Step 3: (E)-1-(3-(((7-(8-chloro-7-fluoronaphthalen-1-yl)-8-fluoro-2-((tetrahydro-1H-pyrrolizin-7a(5H)-yl)methoxy)pyrido[4,3-d]pyrimidin-4-yl)(methyl)amino)methyl)azetidin-1-yl)-3-(3-(2-hydroxypropan-2-yl)-1,2,4-oxadiazol-5-yl)prop-2-en-1-one The amide coupling reaction was prepared in a similar fashion to Method #2, Step 7. The resulting residue was purified by reverse phase HPLC (column: Waters Xbridge Prep OBD C18 150*40 mm*10 μm; mobile phase: [water(NH$_4$HCO$_3$)-ACN]; B %: 25%-45%, 8 min) affording (E)-1-(3-(((7-(8-chloro-7-fluoronaphthalen-1-yl)-8-fluoro-2-((tetrahydro-1H-pyrrolizin-7a(5H)-yl)methoxy)pyrido[4,3-d]pyrimidin-4-yl)(methyl)amino)methyl)azetidin-1-yl)-3-(3-(2-hydroxypropan-2-yl)-1,2,4-oxadiazol-5-yl)prop-2-en- 1-one (13.82 mg, 13.10%, trifluoroacetate salt) as a white solid: ¹H NMR (400 MHz, Acetonitrile-d3) δ 9.24 (s, 1H), 8.13 (dd, J=3.3, 6.4 Hz, 1H), 8.06 (dd, J=5.8, 9.0 Hz, 1H), 7.68-7.66 (m, 1H), 7.51 (t, J=9.0 Hz, 1H), 7.30-7.23 (m, 1H), 7.20-7.15 (m, 2H), 4.50-4.44 (m, 1H), 4.33-4.23 (m, 2H), 4.23-4.13 (m, 4H), 3.93 (td, J=5.7, 9.4 Hz, 1H), 3.60-3.57 (m, 3H), 3.27-3.21 (m, 1H), 3.08-3.00 (m, 2H), 2.64 (dt, J=6.7, 10.1 Hz, 2H), 2.01-1.96 (m, 2H), 1.83 (dq, J=6.6, 13.5 Hz, 4H), 1.69-1.62 (m, 2H), 1.57 (s, 6H).

LCMS (5% to 95% acetonitrile in water+0.03% ammonium bicarbonate over 6 min); retention time 2.567 min, ESI+ found [M+H]=744.3.

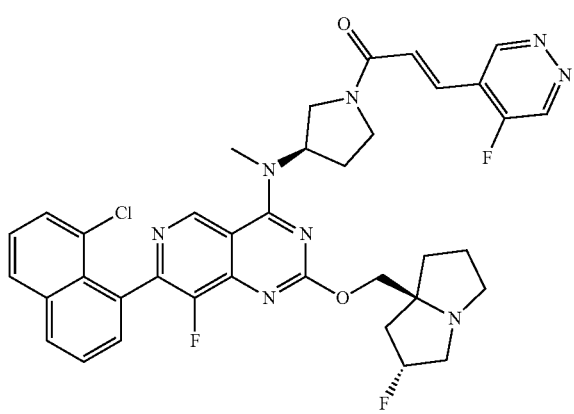 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2cnncc2F)C1]

Example 230 (Method 2): (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(5-fluoropyrimidin-4-yl)prop-2-en-1-one

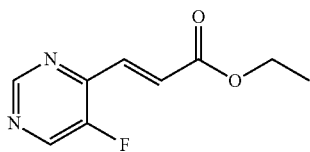

Step 1: ethyl (E)-3-(5-fluoropyrimidin-4-yl)acrylate

A mixture of 4-chloro-5-fluoro-pyrimidine (500 mg, 3.77 mmol), ethyl (E)-3-(4,4,5,5-tetramethyl-1,3,2-dioxaborolan-2-yl)prop-2-enoate (1.28 g, 5.66 mmol), Chloro(2-dicyclohexylphosphino-2',4',6'-triisopropyl-1,1'-biphenyl)[2-(2'-amino-1,1'-biphenyl)]palladium(II) (296.85 mg, 377.29 μmol) and potassium phosphate (2.40 g, 11.32 mmol) in dioxane (8 mL) and water (2 mL) was degassed and purged with nitrogen 3 times. The mixture was stirred at 100° C. for 2 h under a nitrogen atmosphere. The mixture was diluted with water (20 mL) and extracted with ethyl acetate (3×20 mL). The combined organic layers were dried over sodium sulphate and concentrated in vacuo affording ethyl (E)-3-(5-fluoropyrimidin-4-yl)acrylate (1.4 g, crude) as a brown oil, which was used in the next step without any further purification. LCMS Rt=0.707 min, m/z=196.1 [M+H]⁺.

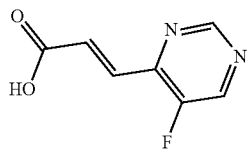 [SMILES: O=C(O)/C=C/c1ncncc1F]

Step 2: (E)-3-(5-fluoropyrimidin-4-yl)acrylic acid

The hydrolysis reaction was prepared in a similar fashion to Method #1, Step 4. The crude product was concentrated in vacuo affording (E)-3-(5-fluoropyrimidin-4-yl)acrylic acid (250 mg, crude) as a brown oil, which was used in the next step without any further purification. LCMS Rt =0.460 min, m/z=168.0 [M+H]⁺.

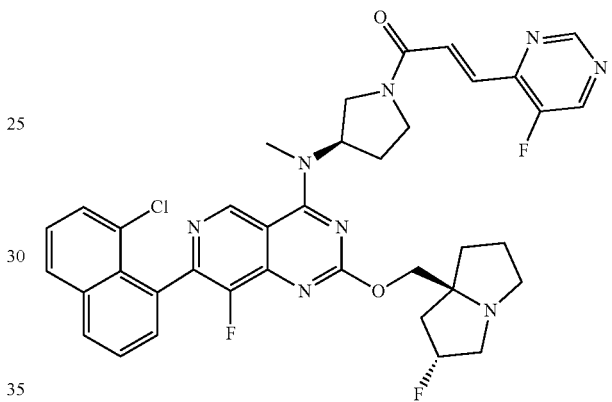

Step 3: (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(5-fluoropyrimidin-4-yl)prop-2-en-1-one The amide coupling reaction was prepared in a similar fashion to Method #2, Step 7. The crude product was purified by reverse phase prep-HPLC (column: Waters Xbridge Prep OBD C18 150*40 mm*10 μm; mobile phase: [water(NH₄HCO₃)-ACN]; B %: 40%-60%, 8 min) affording (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(5-fluoropyrimidin-4-yl)prop-2-en-1-one (18.39 mg, 11.01%) as a brown solid: ¹H NMR (400 MHz, Acetonitrile-d3) δ 9.28-9.20 (m, 1H), 9.01 (dd, J=2.8, 12.6 Hz, 1H), 8.74 (dd, J=2.3, 5.4 Hz, 1H), 8.20-7.99 (m, 2H), 7.73-7.69 (m, 2H), 7.69-7.62 (m, 3H), 7.57-7.51 (m, 1H), 5.50-5.16 (m, 2H), 4.32-4.14 (m, 3H), 4.11-4.00 (m, 1H), 3.97-3.86 (m, 1H), 3.82 (br dd, J=2.9, 8.4 Hz, 1H), 3.50-3.45 (m, 3H), 3.26-3.10 (m, 3H), 3.01-2.89 (m, 1H), 2.51-2.32 (m, 3H), 2.18-2.13 (m, 3H), 1.90 (br s, 2H).

LCMS (5% to 95% acetonitrile in water+0.03% ammonium bicarbonate over 6 min); retention time 2.968 min, ESI+ found [M+H]=714.2.

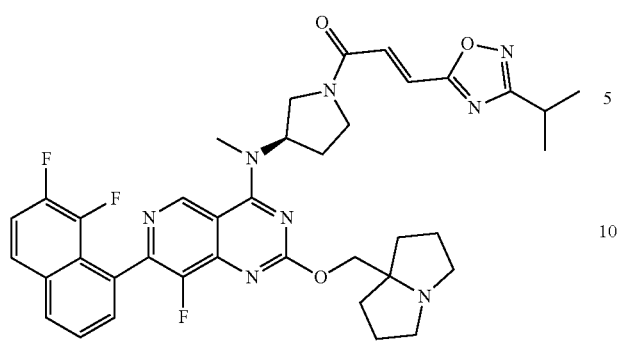

Example 231 (Method 2): (R,E)-1-(3-((7-(7,8-difluoronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-isopropyl-1,2,4-oxadiazol-5-yl)prop-2-en-1-one

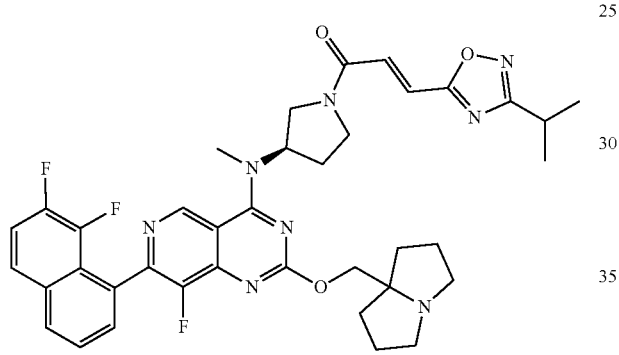

Step 1: (R,E)-1-(3-((7-(7,8-difluoronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-isopropyl-1,2,4-oxadiazol-5-yl)prop-2-en-1-one The amide coupling reaction was prepared in a similar fashion to Method #2, Step 7. The crude product was purified by reverse phase prep-HPLC (column: Waters Xbridge Prep OBD C18 150*40 mm*10 um; mobile phase: [water(NH$_4$HCO$_3$)-ACN]; B %: 40%-70%, 8 min) affording (R,E)-1-(3-((7-(7,8-difluoronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(3-isopropyl-1,2,4-oxadiazol-5-yl)prop-2-en-1-one (31.9 mg, 36.11%) as a white solid: $^1$H NMR (400 MHz, Acetonitrile-d3) δ 9.21 (s, 1H), 8.16-8.06 (m, 1H), 7.94-7.84 (m, 1H), 7.73-7.64 (m, 2H), 7.57-7.31 (m, 3H), 5.51-5.27 (m, 1H), 4.27-4.05 (m, 3H), 4.03-3.95 (m, 1H), 3.82-3.71 (m, 1H), 3.67-3.48 (m, 1H), 3.43 (s, 3H), 3.18-3.06 (m, 1H), 3.01-2.90 (m, 2H), 2.63-2.51 (m, 2H), 2.47-2.09 (m, 4H), 1.86-1.75 (m, 4H), 1.66-1.58 (m, 2H), 1.31 (dd, J=7.0, 8.7 Hz, 6H). LCMS (5% to 95% acetonitrile in water+0.03% ammonium bicarbonate over 6 min); retention time 2.911 min, ESI+ found [M+H]=712.3.

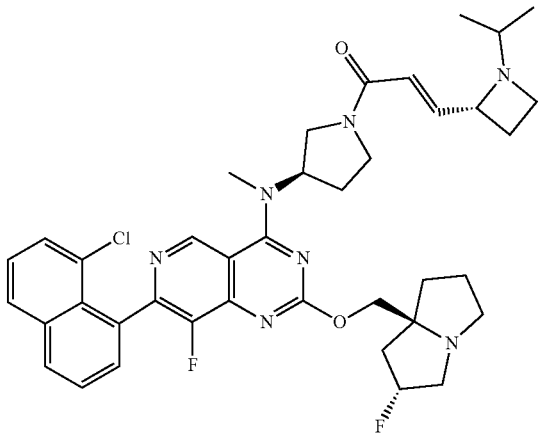 [SMILES: CC(C)N1CC[C@@H]1/C=C/C(=O)N1CC[C@@H](N(C)c2nc(OC[C@@]34CCCN3C[C@H](F)C4)nc3c(F)c(-c4cccc5cccc(Cl)c45)ncc23)C1]

Example 232 (Method 8): (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-isopropylazetidin-2-yl)prop-2-en-1-one

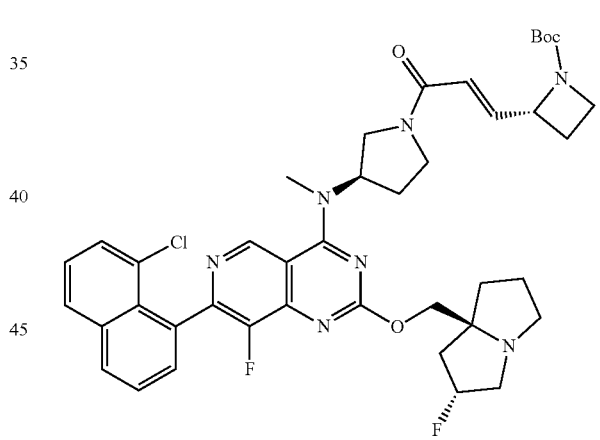

Step 1: tert-butyl (R)-2-((E)-3-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-oxoprop-1-en-1-yl)azetidine-1-carboxylate The HWE reaction was prepared in a similar fashion to Method #8, Step 4. The residue was purified by column chromatography (silica gel, 100-200 mesh, 0-10% ethyl acetate in petroleum ether) affording tert-butyl (R)-2-((E)-3-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-oxoprop-1-en-1-yl)azetidine-1-carboxylate (470 mg, 63.80%) as a yellow solid. LCMS Rt=0.779 min, m/z=773.3 [M+H]$^+$.

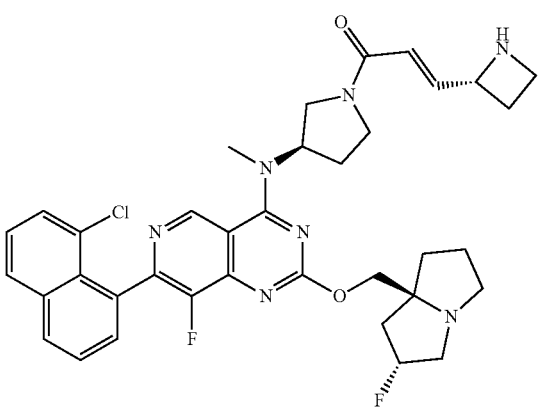 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/[C@H]2CCN2)C1]

Step 2: (E)-3-((R)-azetidin-2-yl)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one The deprotection of the Boc group was prepared in a similar fashion to Method #1, Step 9. The reaction mixture was concentrated in vacuo affording (E)-3-((R)-azetidin-2-yl)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (162 mg, crude, trifluoroacetic acid salt) as a yellow oil, which was used in the next step without any further purification. LCMS Rt=0.618 min, m/z=673.3 [M+H]⁺.

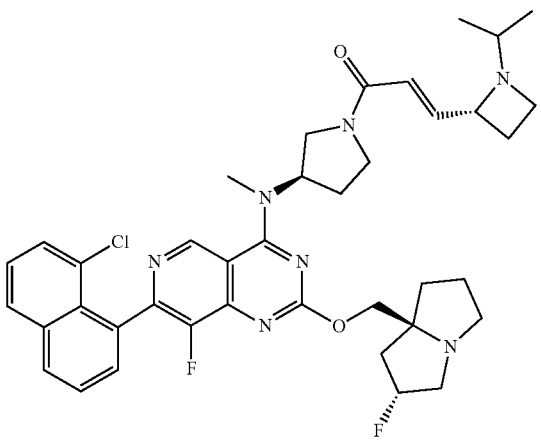 [SMILES: CC(C)N1CC[C@@H]1/C=C/C(=O)N1CC[C@@H](N(C)c2nc(OC[C@@]34CCCN3C[C@H](F)C4)nc3c(F)c(-c4cccc5cccc(Cl)c45)ncc23)C1]

Step 3: (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-isopropylazetidin-2-yl)prop-2-en-1-one The reductive amination was prepared in a similar fashion to Method #8, Step 6. The residue was purified by prep-HPLC (column: Waters Xbridge BEH C18 100*30 mm*10 μm; mobile phase: [water(NH₄HCO₃)-ACN]; B %: 40%-70%, 8 min) affording (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-isopropylazetidin-2-yl)prop-2-en-1-one (8.02 mg, 10.40%) as a yellow amorphous solid: $^1$H NMR (400 MHz, Acetonitrile-d3) δ 9.24-9.14 (m, 1H), 8.12 (d, J=8.0 Hz, 1H), 8.02 (d, J=8.0 Hz, 1H), 7.73-7.65 (m, 1H), 7.65-7.59 (m, 2H), 7.51 (t, J=7.8 Hz, 1H), 6.89-6.78 (m, 1H), 6.47-6.36 (m, 1H), 5.40-5.18 (m, 2H), 4.24-4.08 (m, 2H), 4.08-3.98 (m, 1H), 3.96-3.77 (m, 2H), 3.75-3.61 (m, 2H), 3.59-3.47 (m, 1H), 3.44-3.40 (m, 3H), 3.33-3.24 (m, 1H), 3.17-3.09 (m, 2H), 3.06 (br s, 1H), 2.92-2.76 (m, 2H), 2.45-2.22 (m, 4H), 2.11-2.05 (m, 3H), 1.86 (br s, 3H), 0.92-0.84 (m, 6H).

LCMS (5% to 95% acetonitrile in water+0.03% ammonium bicarbonate over 6 min); retention time 3.050 min, ESI+ found [M+H]=715.3.

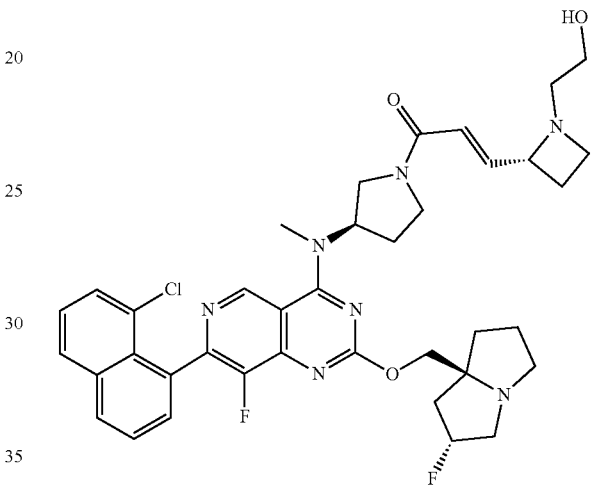

Example 233 (Method 8): (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-(2-hydroxyethyl)azetidin-2-yl)prop-2-en-1-one

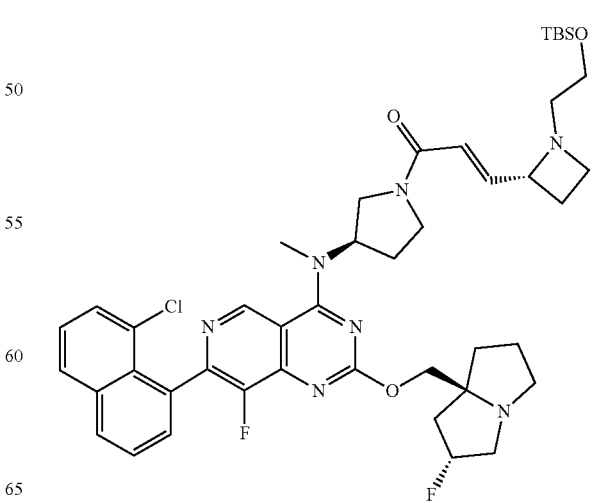

Step 1: (E)-3-((R)-1-(2-((tert-butyldimethylsilyl)oxy)ethyl)azetidin-2-yl)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one The reductive amination was prepared in a similar fashion to Method #8, Step 6. The mixture concentrated in vacuo affording (E)-3-((R)-1-(2-((tert-butyldimethylsilyl)oxy)ethyl)azetidin-2-yl)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (70 mg, crude) as a pale yellow gum, which was used in the next step without any further purification. LCMS Rt=1.141 min, m/z=831.4 [M+H]$^+$.

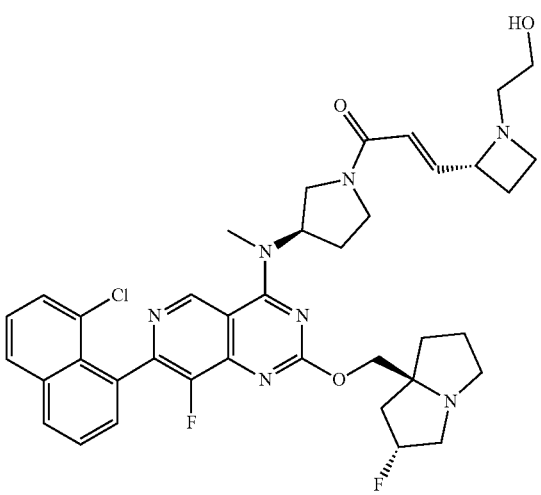 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/[C@H]2CCN2CCO)C1]

Step 2: (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-(2-hydroxyethyl)azetidin-2-yl)prop-2-en-1-one To a solution of (E)-3-((R)-1-(2-((tert-butyldimethylsilyl)oxy)ethyl)azetidin-2-yl)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (70 mg, 84.08 μmol) in tetrahydrofuran (1 mL) was added N,N-diethylethanamine trihydrofluoride (135.55 mg, 137.06 μL). The mixture was stirred at 20° C. for 12 h. The reaction mixture was concentrated in vacuo, and the residue was purified by reverse phase HPLC (column: Waters Xbridge Prep OBD C18 150*40 mm*10 μm; mobile phase: [water (NH$_4$HCO$_3$)-ACN]; B %: 40%-70%, 8 min) affording (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-(2-hydroxyethyl)azetidin-2-yl)prop-2-en-1-one (2.9 mg, 4.66%) as a pale yellow amorphous solid: $^1$H NMR (400 MHz, Acetonitrile-d3) δ 9.23-9.12 (m, 1H), 8.16 (s, 1H), 8.02 (d, J=8.0 Hz, 1H), 7.72-7.66 (m, 1H), 7.65-7.58 (m, 2H), 7.54-7.48 (m, 1H), 6.81 (td, J=6.1, 15.1 Hz, 1H), 6.46 (dd, J=4.9, 15.1 Hz, 1H), 5.41-5.18 (m, 2H), 4.28-4.07 (m, 2H), 3.97-3.76 (m, 2H), 3.73-3.51 (m, 2H), 3.50-3.44 (m, 2H), 3.42 (s, 3H), 3.25-3.09 (m, 3H), 3.03-2.89 (m, 2H), 2.73-2.60 (m, 2H), 2.52 (br d, J=5.5 Hz, 3H), 2.33-2.21 (m, 4H), 2.18-1.96 (m, 4H), 1.91-1.79 (m, 2H).

LCMS (5% to 95% acetonitrile in water+0.03% ammonium bicarbonate over 6 min); retention time 2.639 min, ESI+ found [M+H]=717.3.

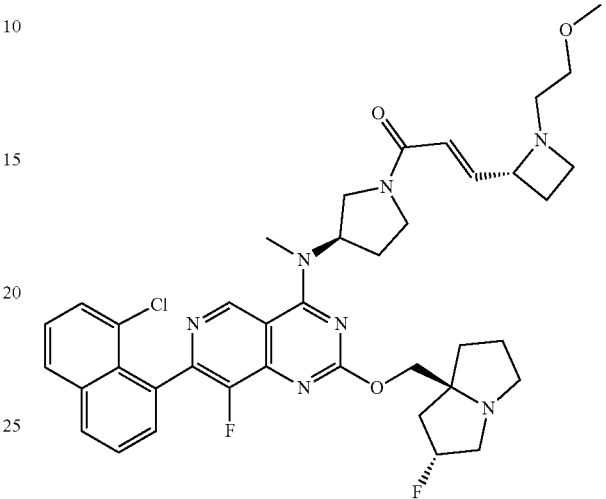

Example 234 (Method 8): (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-(2-methoxyethyl)azetidin-2-yl)prop-2-en-1-one

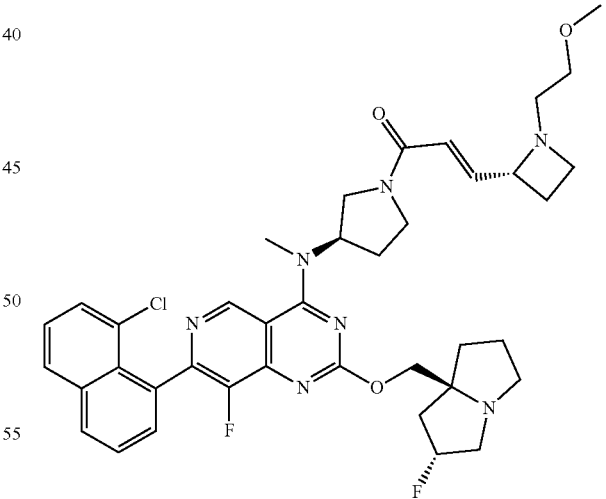

Step 1: (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-(2-methoxyethyl)azetidin-2-yl)prop-2-en-1-one The reductive amination was prepared in a similar fashion to Method #8, Step 6. The residue was purified by prep- HPLC (column: Waters Xbridge BEH C18 100*30 mm*10 μm; mobile phase: [water(NH₄HCO₃)-ACN]; B %: 40%-70%, 8 min.) affording (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-(2-methoxyethyl)azetidin-2-yl)prop-2-en-1-one (8.68 mg, 9.20%) as a yellow amorphous solid: ¹H NMR (400 MHz, Acetonitrile-d3) δ 9.18 (d, J=1.6 Hz, 1H), 8.12 (d, J=7.8 Hz, 1H), 8.02 (d, J=7.8 Hz, 1H), 7.72-7.65 (m, 1H), 7.65-7.58 (m, 2H), 7.55-7.48 (m, 1H), 6.78 (dd, J=5.6, 15.1 Hz, 1H), 6.43 (dd, J=10.7, 14.6 Hz, 1H), 5.42-5.16 (m, 2H), 4.23-4.17 (m, 1H), 4.16-4.03 (m, 2H), 3.99-3.76 (m, 2H), 3.72-3.62 (m, 2H), 3.61-3.46 (m, 1H), 3.43-3.41 (m, 3H), 3.35-3.28 (m, 3H), 3.26 (s, 1H), 3.21 (s, 1H), 3.18-3.09 (m, 2H), 3.05 (s, 1H), 2.92-2.82 (m, 2H), 2.68-2.48 (m, 2H), 2.41-2.27 (m, 2H), 2.18 (br d, J=7.9 Hz, 2H), 2.10 (br d, J=2.5 Hz, 1H), 2.07-2.01 (m, 1H), 1.92-1.83 (m, 4H).

LCMS (5% to 95% acetonitrile in water+0.03% ammonium bicarbonate over 6 min); retention time 2.940 min, ESI+ found [M+H]=731.3.

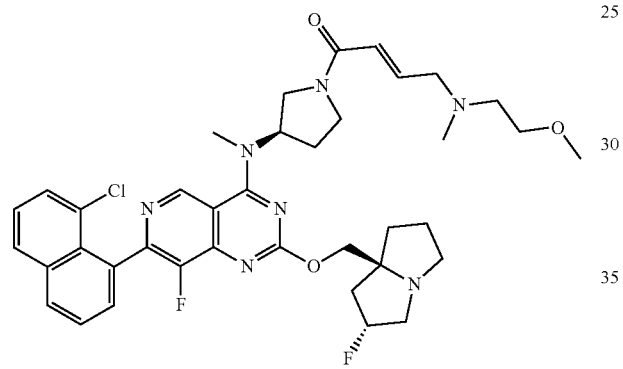

Example 235 (Method 12-master): (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-4-((2-methoxyethyl)(methyl)amino)but-2-en-1-one

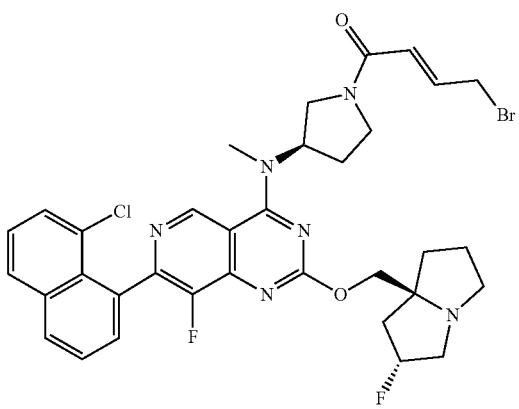 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/CBr)C1]

Step 1: (E)-4-bromo-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)but-2-en-1-one To a solution of 7-(8-chloronaphthalen-1-yl)-8-fluoro-2-(((2R,7aS)-2-fluorohexahydro-1H-pyrrolizin-7a-yl)methoxy)-N-methyl-N—((R)-pyrrolidin-3-yl)pyrido[4,3-d]pyrimidin-4-amine (150 mg, 220.89 μmol, trifluoroacetic acid) in tetrahydrofuran (2 mL) was added N,N-diisopropylethylamine (28.55 mg, 220.89 μmol) and (E)-4-bromobut-2-enoyl chloride (81.04 mg, 441.78 μmol). The mixture was stirred at 25° C. for 1 h. The mixture was filtered, and the filtrate (yellow solution) was used in next step without any purification. LCMS Rt=0.705 min, m/z=710.2 [M+H]⁺.

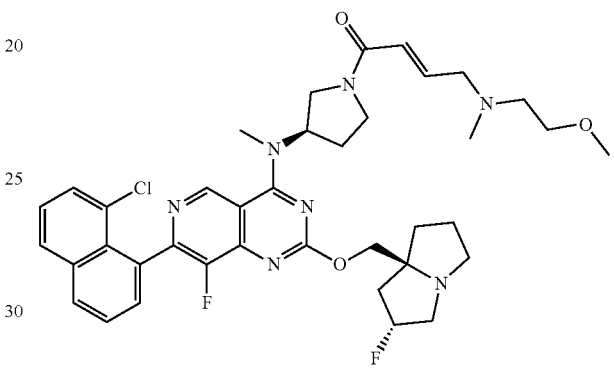

Step 2: (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-4-((2-methoxyethyl)(methyl)amino)but-2-en-1-one To a solution of (E)-4-bromo-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)but-2-en-1-one (assumed 150 mg, 210.67 μmol) in tetrahydrofuran (2 mL) was added N,N-diisopropylethylamine (81.68 mg, 632.00 μmol) and 2-methoxy-N-methyl-ethanamine (56.33 mg, 632.00 μmol). The mixture was stirred at 50° C. for 1 h. The residue was purified by reverse phase HPLC (column: Waters Xbridge Prep OBD C18 150*40 mm*10 μm; mobile phase: [water(NH₄HCO₃)-ACN]; B %: 30%-70%, 8 min) affording (E)-1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-4-((2-methoxyethyl)(methyl)amino)but-2-en-1-one (30.6 mg, 19.83%) as a white solid: ¹H NMR (400 MHz, Acetonitrile-d3) δ 9.26-9.16 (m, 1H), 8.15 (d, J=8.1 Hz, 1H), 8.05 (d, J=8.0 Hz, 1H), 7.76-7.61 (m, 3H), 7.58-7.49 (m, 1H), 6.84-6.69 (m, 1H), 6.45 (dd, J=9.9, 15.1 Hz, 1H), 5.49-5.18 (m, 2H), 4.27-4.20 (m, 1H), 4.18-4.12 (m, 1H), 4.11-3.94 (m, 1H), 3.93-3.78 (m, 1H), 3.72-3.51 (m, 2H), 3.49-3.47 (m, 1H), 3.46-3.45 (m, 3H), 3.30 (d, J=15.5 Hz, 3H), 3.20 (br t, J=6.7 Hz, 2H), 3.17-3.15 (m, 1H), 3.08 (s, 1H), 2.95-2.87 (m, 1H), 2.56 (q, J=6.0 Hz, 2H), 2.46-2.37 (m, 1H), 2.37-2.29 (m, 1H), 2.27 (d, J=6.8 Hz, 3H), 2.23-2.18 (m, 2H), 2.14-2.11 (m, 2H), 2.10-2.05 (m, 1H), 1.93-1.83 (m, 3H).

LCMS (5% to 95% acetonitrile in water+0.03% ammonium bicarbonate over 6 min); retention time 2.920 min, ESI+ found [M+H]=719.3.

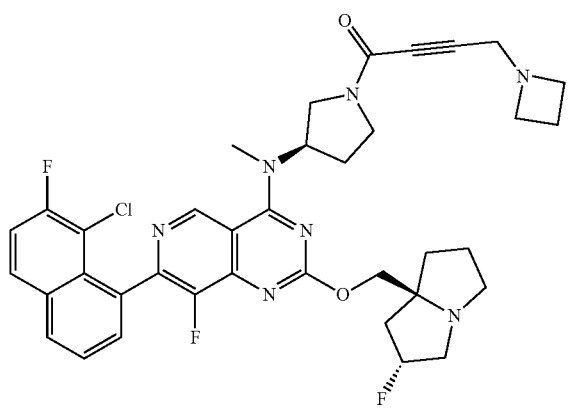 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)C#CCN2CCC2)C1]

Example 236 (Method 13): 4-(azetidin-1-yl)-1-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)but-2-yn-1-one

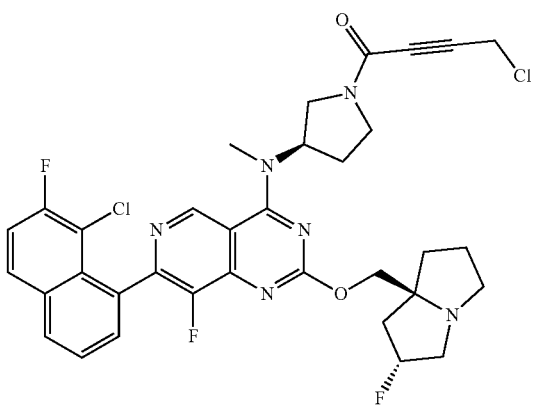 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)C#CCCl)C1]

Step 1: 4-chloro-1-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)but-2-yn-1-one The amide coupling reaction was prepared in a similar fashion to Method #13, Step 1. The residue was purified by reverse phase HPLC (column: Phenomenex Luna 80*30 mm*3 µm; mobile phase: [water(TFA)-ACN]; B %: 15%-45%, 8 min) affording 4-chloro-1-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)but-2-yn-1-one (130 mg, 43.32%) as a yellow solid. LCMS Rt=0.681 min, m/z=682.2 [M+H]+.

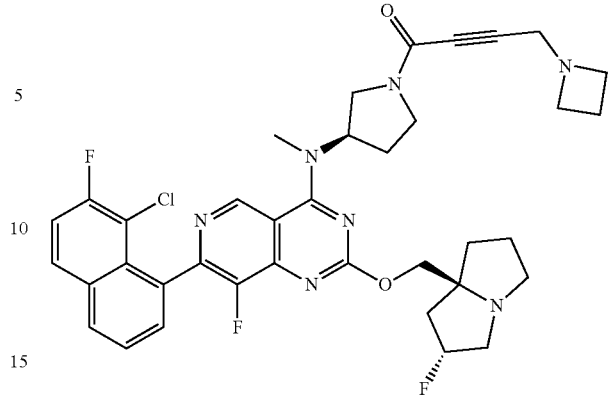

Step 2: 4-(azetidin-1-yl)-1-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)but-2-yn-1-one The substitution reaction was prepared in a similar fashion to Method #13, Step 2. The residue was purified by reverse phase HPLC (column: Waters Xbridge Prep OBD C18 150*40 mm*10 µm; mobile phase: [water(NH$_4$HCO$_3$)-ACN]; B %: 30%-50%, 8 min) affording 4-(azetidin-1-yl)-1-((R)-3-((7-(8-chloro-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)but-2-yn-1-one (3.87 mg, 9.07%) as a yellow oil: $^1$H NMR (400 MHz, Acetonitrile-d3) δ 9.31-9.18 (m, 1H), 8.17 (br dd, J=3.1, 6.1 Hz, 1H), 8.11 (dd, J=5.7, 9.0 Hz, 1H), 7.76-7.68 (m, 2H), 7.56 (t, J=8.9 Hz, 1H), 5.48-5.20 (m, 2H), 4.26-4.20 (m, 1H), 4.20-4.12 (m, 1H), 4.07-3.88 (m, 1H), 3.83-3.72 (m, 1H), 3.58-3.44 (m, 4H), 3.40 (d, J=11.7 Hz, 2H), 3.29 (td, J=7.1, 14.5 Hz, 4H), 3.20-3.01 (m, 4H), 2.99-2.89 (m, 1H), 2.47-2.33 (m, 2H), 2.15-2.00 (m, 5H), 1.93-1.81 (m, 3H).

LCMS (5% to 95% acetonitrile in water+0.03% ammonium bicarbonate over 6 min); retention time 2.948 min, ESI+ found [M+H]=703.3.

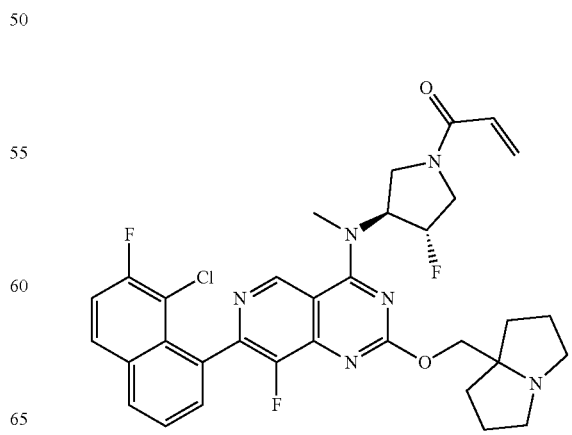

Example 237 (Method 1): 1-((3S,4S)-3-((7-(8-chloro-7-fluoronaphthalen-1-yl)-8-fluoro-2-((tetrahydro-1H-pyrrolizin-7a(5H)-yl)methoxy)pyrido[4,3-d]pyrimidin-4-yl)(methyl)amino)-4-fluoropyrrolidin-1-yl)prop-2-en-1-one

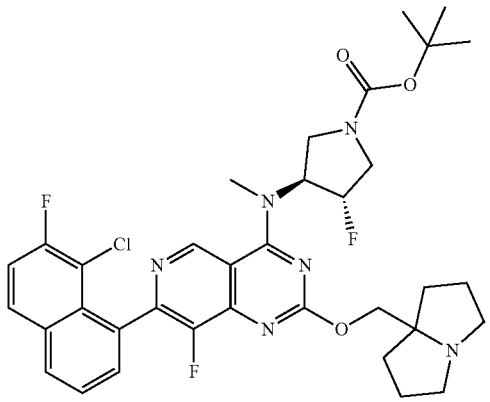 [SMILES: CN(c1nc(OCC23CCCN2CCC3)nc2c(F)c(-c3cccc4ccc(F)c(Cl)c34)ncc12)[C@H]1CN(C(=O)OC(C)(C)C)C[C@@H]1F]

Step 1: tert-butyl (3S,4S)-3-((7-(8-chloro-7-fluoronaphthalen-1-yl)-8-fluoro-2-((tetrahydro-1H-pyrrolizin-7a(5H)-yl)methoxy)pyrido[4,3-d]pyrimidin-4-yl)(methyl)amino)-4-fluoropyrrolidine-1-carboxylate The substitution reaction was prepared in a similar fashion to Method #1, Step 8. The resulting residue was purified by reverse phase HPLC (column: Phenomenex Luna C18 250*50 mm*10 μm; mobile phase: [water(TFA)-ACN]; B %: 25%-55%, 10 min) affording tert-butyl (3S,4S)-3-((7-(8-chloro-7-fluoronaphthalen-1-yl)-8-fluoro-2-((tetrahydro-1H-pyrrolizin-7a(5H)-yl)methoxy)pyrido[4,3-d]pyrimidin-4-yl)(methyl)amino)-4-fluoropyrrolidine-1-carboxylate (110 mg, 35.25%, trifluoroacetate salt) as a white solid. LCMS Rt=0.729 min, m/z=682.3 [M+H]$^+$.

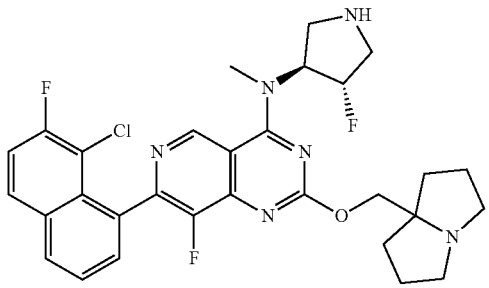 [SMILES: CN(c1nc(OCC23CCCN2CCC3)nc2c(F)c(-c3cccc4ccc(F)c(Cl)c34)ncc12)[C@H]1CNC[C@@H]1F]

Step 2: 7-(8-chloro-7-fluoronaphthalen-1-yl)-8-fluoro-N-((3S,4S)-4-fluoropyrrolidin-3-yl)-N-methyl-2-((tetrahydro-1H-pyrrolizin-7a(5H)-yl)methoxy)pyrido[4,3-d]pyrimidin-4-amine The deprotection of the Boc group was prepared in a similar fashion to Method #1, Step 9. The reaction mixture was concentrated in vacuo affording 7-(8-chloro-7-fluoronaphthalen-1-yl)-8-fluoro-N-((3S,4S)-4-fluoropyrrolidin-3-yl)-N-methyl-2-((tetrahydro-1H-pyrrolizin-7a(5H)-yl) methoxy)pyrido[4,3-d]pyrimidin-4-amine (100 mg, crude, trifluoroacetate salt) as a yellow oil, which was used in the next step without further purification. LCMS Rt=0.622 min, m/z=582.2 [M+H]$^+$.

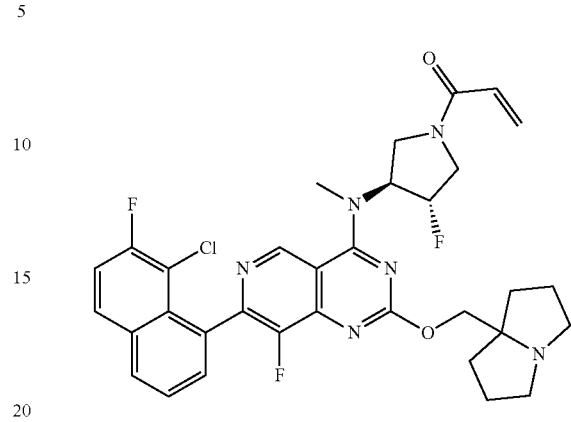

Step 3: 1-((3S,4S)-3-((7-(8-chloro-7-fluoronaphthalen-1-yl)-8-fluoro-2-((tetrahydro-1H-pyrrolizin-7a(5H)-yl)methoxy)pyrido[4,3-d]pyrimidin-4-yl)(methyl)amino)-4-fluoropyrrolidin-1-yl)prop-2-en-1-one The amide coupling reaction was prepared in a similar fashion to Method #1, Step 10. The resulting residue was purified by reverse phase HPLC (column: Waters Xbridge BEH C18 100*30 mm*10 μm; mobile phase: [water (NH$_4$HCO$_3$)-ACN]; B %: 35%-55%, 8 min) affording 1-((3S,4S)-3-((7-(8-chloro-7-fluoronaphthalen-1-yl)-8-fluoro-2-((tetrahydro-1H-pyrrolizin-7a(5H)-yl)methoxy) pyrido[4,3-d]pyrimidin-4-yl)(methyl)amino)-4-fluoropyrrolidin-1-yl)prop-2-en-1-one (28.31 mg, 27.37%) as a white solid: $^1$H NMR (400 MHz, Acetonitrile-d3) δ 9.24 (s, 1H), 8.17-8.10 (m, 1H), 8.06 (dd, J=5.7, 9.0 Hz, 1H), 7.72-7.62 (m, 2H), 7.52 (t, J=8.9 Hz, 1H), 6.63-6.51 (m, 1H), 6.27 (br d, J=16.6 Hz, 1H), 5.72 (td, J=2.4, 10.4 Hz, 1H), 5.67-5.48 (m, 1H), 5.44-5.20 (m, 1H), 4.29-4.19 (m, 1H), 4.19-4.14 (m, 2H), 4.13-3.98 (m, 1H), 3.95-3.82 (m, 1H), 3.81-3.72 (m, 1H), 3.49 (d, J=6.1 Hz, 3H), 3.02-2.92 (m, 2H), 2.64-2.55 (m, 2H), 1.93-1.70 (m, 6H), 1.67-1.52 (m, 2H).

LCMS (5% to 95% acetonitrile in water+0.03% ammonium bicarbonate over 6 min); retention time 2.545 min, ESI+ found [M+H]=636.2.

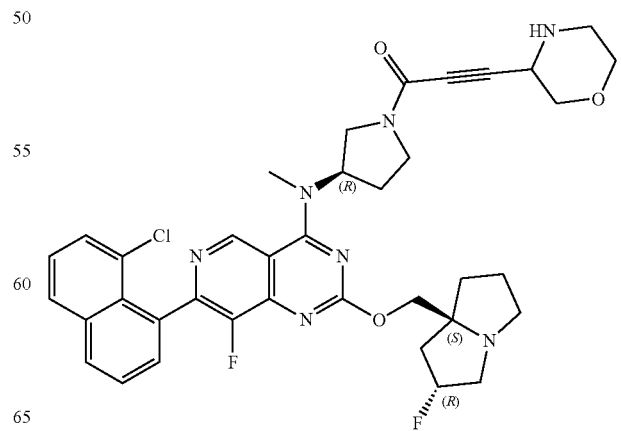

Example 238 (Method 7): 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(morpholin-3-yl)prop-2-yn-1-one

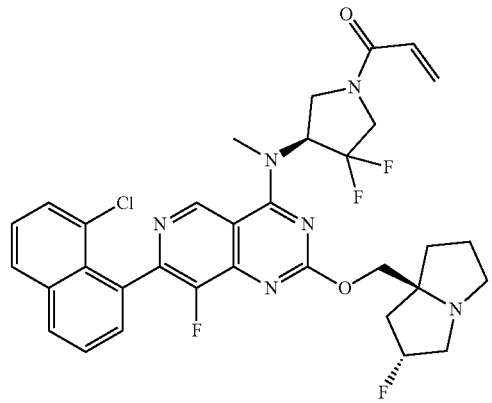

Example 239 (Method 1): 1-((S)-4-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-3,3-difluoropyrrolidin-1-yl)prop-2-en-1-one

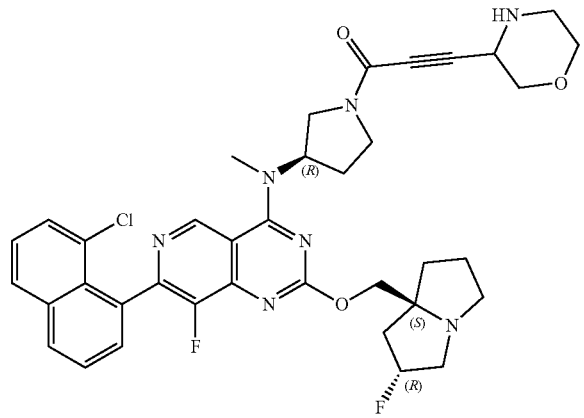

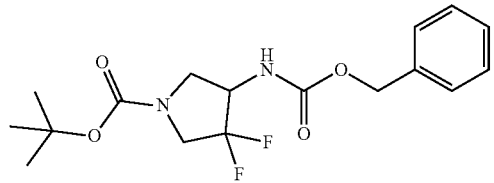 [SMILES: CC(C)(C)OC(=O)N1CC(NC(=O)OCc2ccccc2)C(F)(F)C1]

Step 1: tert-butyl 4-(((benzyloxy)carbonyl)amino)-3,3-difluoropyrrolidine-1-carboxylate Step 1: 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(morpholin-3-yl)prop-2-yn-1-one To a solution of tert-butyl 4-amino-3,3-difluoro-pyrrolidine-1-carboxylate (5 g, 22.50 mmol) in dioxane (30 mL) and water (30 mL) was added sodium carbonate (2.86 g, 27.00 mmol) and benzyl chloroformate (4.61 g, 27.00 mmol) at 0° C. The mixture was stirred at 25° C. for 1 h. The mixture was diluted with water (20 mL) and extracted with ethyl acetate (3×20 mL). The combined organic layers were dried over sodium sulphate and concentrated in vacuo affording tert-butyl 4-(((benzyloxy)carbonyl)amino)-3,3-difluoropyrrolidine-1-carboxylate (9 g, crude) as a yellow oil, which was used in the next step without any further purification. LCMS Rt=0.838 min, m/z=356.2 [M+H]⁺.

The deprotection of the Boc group was prepared in a similar fashion to Method #7, Step 3. The reaction mixture was concentrated in vacuo and purified by reverse phase HPLC (column: Phenomenex Luna C18 75*30 mm*3 μm; mobile phase: [water(FA)-ACN]; B %: 1%-30%, 8 min) affording 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(morpholin-3-yl)prop-2-yn-1-one (2.09 mg, 14.73%, formate salt) as a yellow amorphous solid: ¹H NMR (400 MHz, Acetonitrile-d3) δ 9.22-9.15 (m, 1H), 8.12 (br d, J=8.6 Hz, 1H), 8.02 (d, J=8.1 Hz, 1H), 7.72-7.66 (m, 1H), 7.64-7.59 (m, 2H), 7.55-7.47 (m, 1H), 5.42-5.17 (m, 2H), 4.26-4.09 (m, 3H), 4.01-3.87 (m, 1H), 3.84-3.66 (m, 4H), 3.63-3.54 (m, 3H), 3.54-3.46 (m, 1H), 3.44-3.41 (m, 3H), 3.18 (br d, J=13.0 Hz, 2H), 3.10 (s, 1H), 3.04-2.88 (m, 2H), 2.75-2.65 (m, 1H), 2.27-2.03 (m, 5H), 1.91-1.75 (m, 3H). LCMS Rt=2.646 min, m/z=701.3 [M+H]⁺.

LCMS (5% to 95% acetonitrile in water+0.1% formic acid over 6 min); retention time 2.646 min, ESI+ found [M+H]=701.3.

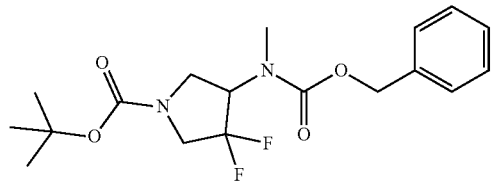 [SMILES: CN(C(=O)OCc1ccccc1)C1CN(C(=O)OC(C)(C)C)CC1(F)F]

Step 2: tert-butyl 4-(((benzyloxy)carbonyl)(methyl)amino)-3,3-difluoropyrrolidine-1-carboxylate To a solution of tert-butyl 4-(((benzyloxy)carbonyl)amino)-3,3-difluoropyrrolidine-1-carboxylate (9 g, 25.26 mmol) in N,N-dimethylformaldehyde (50 mL) was added sodium hydride (3.03 g, 75.77 mmol, 60% purity) and iodomethane (5.38 g, 37.88 mmol). The mixture was stirred at 0° C. for 1 h. The mixture was diluted with water (20 mL) and extracted with ethyl acetate (3×50 mL). The combined organic layers were dried over sodium sulphate and concentrated in vacuo. The residue was purified by column chromatography (silica gel, 100-200 mesh, 0-100% ethyl acetate in petroleum ether) affording tert-butyl 4-(((benzyloxy)carbonyl)(methyl)amino)-3,3-difluoropyrrolidine-1-carboxylate (3.7 g, 39.55%) as a white solid. LCMS Rt=0.885 min, m/z=370.2 [M+H]$^+$.

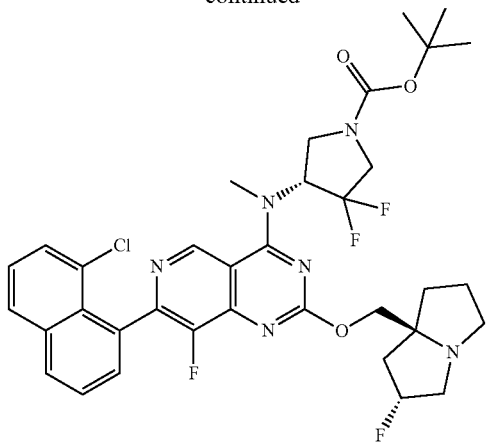

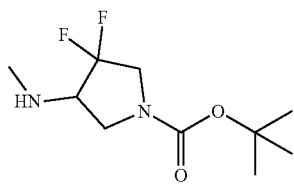 [SMILES: CNC1CN(C(=O)OC(C)(C)C)CC1(F)F]

Step 3: tert-butyl 3,3-difluoro-4-(methylamino)pyrrolidine-1-carboxylate

The deprotection of the Cbz group was prepared in a similar fashion to Method #6, Step 6. The mixture was concentrated to dryness in vacuo affording tert-butyl 3,3-difluoro-4-(methylamino)pyrrolidine-1-carboxylate (1.8 g, crude) as a yellow oil, which was used in the next step without further purification. LCMS Rt=0.502 min, m/z=236.1 [M+H]$^+$.

Step 4: tert-butyl (S)-4-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-3,3-difluoropyrrolidine-1-carboxylate and tert-butyl (R)-4-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-3,3-difluoropyrrolidine-1-carboxylate The substitution reaction was prepared in a similar fashion to Method #1, Step 8. The resulting residue was purified by reverse phase HPLC (column: Waters Xbridge BEH C18 250*50 mm*10 μm; mobile phase: [water(TFA)-ACN]; B %: 35%-55%, 10 min) affording tert-butyl 4-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-3,3-difluoropyrrolidine-1-carboxylate (200 mg, 72.36%, trifluoroacetate salt) as a yellow oil. The racemic material was further purified by SFC (column: DAICEL CHIRALPAK IG (250 mm*30 mm, 10 μm); mobile phase: [50% CO$_2$, 50% 0.1% NH$_3$H$_2$O in EtOH], 11 min) to give:

1. tert-butyl (S)-4-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-3,3-difluoropyrrolidine-1-carboxylate (Peak 1, retention time=1.544 min) (100 mg, 36.18%) as a yellow oil. LCMS Rt=1.660 min, m/z=700.3 [M+H]$^+$; Absolute stereochemistry is assumed based on biological data.

2. tert-butyl (R)-4-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-3,3-difluoropyrrolidine-1-carboxylate (Peak 2, retention time=1.753 min) (50 mg, 18.09%) as a yellow oil. LCMS Rt=1.660 min, m/z=700.3 [M+H]$^+$; Absolute stereochemistry is assumed based on biological data.

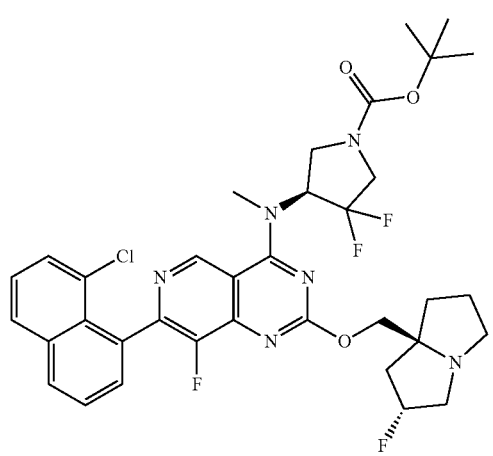

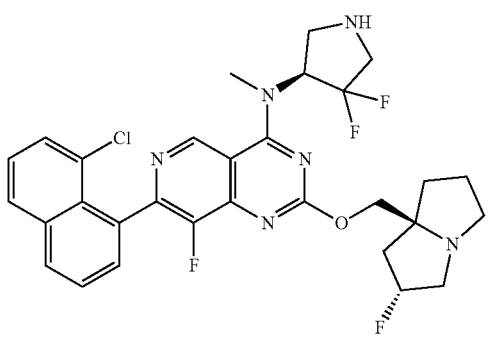 [SMILES: CN(c1nc(OC[C@@]23CCCN2C[C@H](F)C3)nc2c(F)c(-c3cccc4cccc(Cl)c34)ncc12)[C@H]1CNCC1(F)F]

Step 5: 7-(8-chloronaphthalen-1-yl)-N—((S)-4,4-difluoropyrrolidin-3-yl)-8-fluoro-2-(((2R,7aS)-2-fluorotetrahydro-1H-pyrrolizin-7a(5H)-yl)methoxy)-N-methylpyrido[4,3-d]pyrimidin-4-amine The deprotection of the Boc group was prepared in a similar fashion to Method #1, Step 9. The reaction mixture was concentrated in vacuo affording 7-(8-chloronaphthalen-1-yl)-N—((S)-4,4-difluoropyrrolidin-3-yl)-8-fluoro-2-(((2R,7aS)-2-fluorotetrahydro-1H-pyrrolizin-7a(5H)-yl)methoxy)-N-methylpyrido[4,3-d]pyrimidin-4-amine (80 mg, crude, trifluoroacetate salt) as a brown oil, which was used in the next step without further purification. LCMS Rt=0.765 min, m/z=600.2 [M+H]⁺.

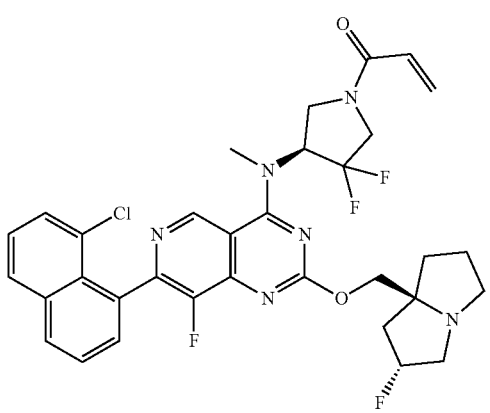 [SMILES: C=CC(=O)N1C[C@H](N(C)c2nc(OC[C@@]34CCCN3C[C@H](F)C4)nc3c(F)c(-c4cccc5cccc(Cl)c45)ncc23)C(F)(F)C1]

Step 6: 1-((S)-4-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-3,3-difluoropyrrolidin-1-yl)prop-2-en-1-one The amide coupling reaction was prepared in a similar fashion to Method #1, Step 10. The resulting residue was purified by reverse phase HPLC (column: Waters Xbridge BEH C18 100*30 mm*10 μm; mobile phase: [water (NH₄HCO₃)-ACN]; B %: 45%-65%, 8 min) affording 1-((S)-4-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-3,3-difluoropyrrolidin-1-yl)prop-2-en-1-one (11.42 mg, 15.56%) as a white solid: ¹H NMR (400 MHz, Acetonitrile-d3) δ 9.32 (d, J=3.8 Hz, 1H), 8.15 (dd, J=0.9, 8.1 Hz, 1H), 8.04 (d, J=8.1 Hz, 1H), 7.74-7.69 (m, 1H), 7.67-7.61 (m, 2H), 7.57-7.51 (m, 1H), 6.68-6.48 (m, 1H), 6.33 (dd, J=2.1, 16.8 Hz, 1H), 5.90-5.69 (m, 2H), 5.40-5.18 (m, 1H), 4.37-4.26 (m, 1H), 4.22 (br d, J=4.6 Hz, 2H), 4.20-3.94 (m, 3H), 3.59 (br d, J=3.8 Hz, 3H), 3.26-3.08 (m, 3H), 2.92 (br d, J=6.9 Hz, 1H), 2.20 (br s, 1H), 2.13 (br s, 1H), 2.09-2.02 (m, 1H), 1.95-1.81 (m, 3H).

LCMS (5% to 95% acetonitrile in water+0.03% ammonium bicarbonate over 6 min); retention time 3.111 min, ESI+ found [M+H]=654.2.

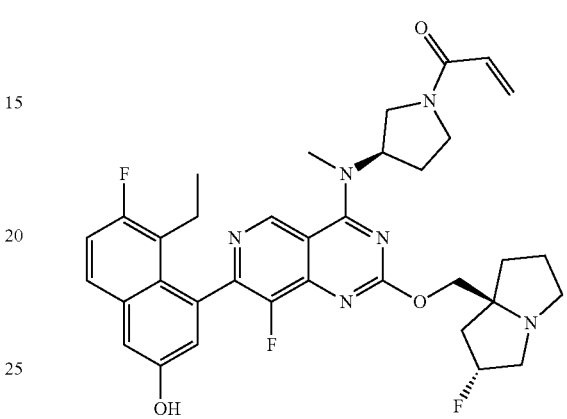

Example 240 (Method 2): 1-((R)-3-((7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one

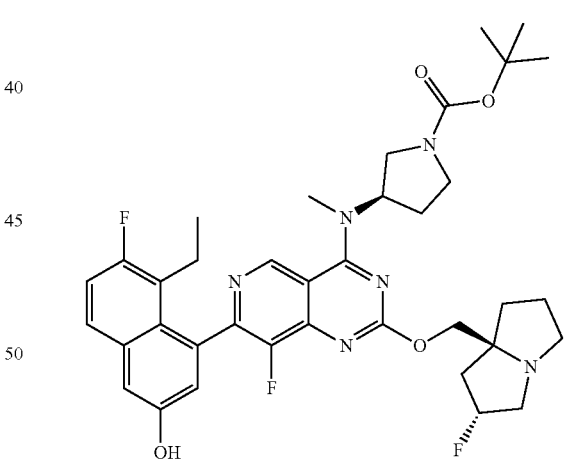

Step 1: tert-butyl (R)-3-((7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidine-1-carboxylate The Suzuki reaction was prepared in a similar fashion to Method #2, Step 5. The crude product was purified by reverse phase prep-HPLC (column: Phenomenex Luna 80*30 mm*3 μm; mobile phase: [water(TFA)-ACN]; B %: 15%-45%, 8 min) affording tert-butyl (R)-3-((7-(8-ethyl-7- fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidine-1-carboxylate (123 mg, 25.97%, trifluoroacetate salt) as a white solid. LCMS Rt=1.583 min, m/z=692.3 [M+H]⁺.

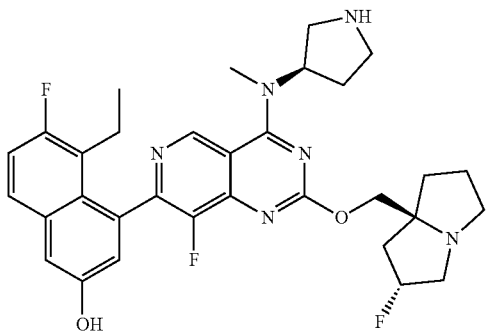 [SMILES: CCc1c(F)ccc2cc(O)cc(-c3ncc4c(N(C)[C@@H]5CCNC5)nc(OC[C@@]56CCCN5C[C@H](F)C6)nc4c3F)c12]

Step 2: 5-ethyl-6-fluoro-4-(8-fluoro-2-(((2R,7aS)-2-fluorotetrahydro-1H-pyrrolizin-7a(5H)-yl)methoxy)-4-(methyl((R)-pyrrolidin-3-yl)amino)pyrido[4,3-d]pyrimidin-7-yl)naphthalen-2-ol The deprotection of the Boc group was prepared in a similar fashion to Method #2, Step 6. The reaction mixture was concentrated in vacuo affording 5-ethyl-6-fluoro-4-(8-fluoro-2-(((2R,7aS)-2-fluorotetrahydro-1H-pyrrolizin-7a(5H)-yl)methoxy)-4-(methyl((R)-pyrrolidin-3-yl)amino)pyrido[4,3-d]pyrimidin-7-yl)naphthalen-2-ol (60 mg, crude, hydrochloric acid salt) as a white solid, which was used in the next step without further purification. LCMS Rt=0.429 min, m/z=592.3 [M+H]⁺.

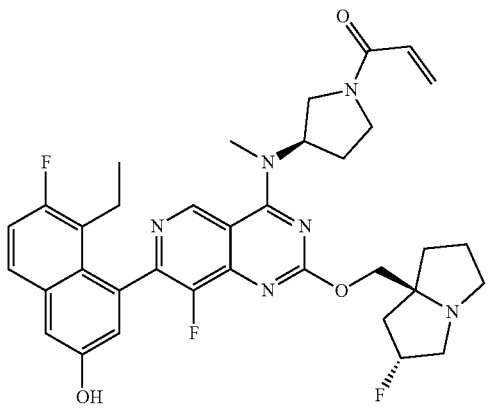 [SMILES: C=CC(=O)N1CC[C@@H](N(C)c2nc(OC[C@@]34CCCN3C[C@H](F)C4)nc3c(F)c(-c4cc(O)cc5ccc(F)c(CC)c45)ncc23)C1]

Step 3: 1-((R)-3-((7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one The amide coupling reaction was prepared in a similar fashion to Method #2, Step 7. The crude product was purified by reverse phase prep-HPLC (column: Phenomenex Luna 80*30 mm*3 μm; mobile phase: [water(TFA)-ACN]; B %: 15%-45%, 8 min) affording 1-((R)-3-((7-(8-ethyl-7-fluoro-3-hydroxynaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (30.28 mg, 44.25%, trifluoroacetic salt) as a white solid: ¹H NMR (400 MHz, Acetonitrile-d3) δ 9.30 (s, 1H), 7.75 (dd, J=5.9, 9.1 Hz, 1H), 7.42-7.27 (m, 2H), 7.14 (dd, J=2.4, 5.4 Hz, 1H), 6.70-6.55 (m, 1H), 6.31-6.23 (m, 1H), 5.77-5.65 (m, 1H), 5.61-5.37 (m, 2H), 4.74-4.45 (m, 4H), 4.16-3.82 (m, 4H), 3.78-3.55 (m, 3H), 3.49 (s, 3H), 3.40-3.27 (m, 1H), 2.59-2.51 (m, 1H), 2.46-2.33 (m, 3H), 2.31-2.21 (m, 3H), 2.16-2.04 (m, 1H), 0.82 (t, J=7.3 Hz, 3H).

LCMS (5% to 95% acetonitrile in water+0.03% ammonium bicarbonate over 6 min); retention time 2.114 min, ESI+ found [M+H]=646.3.

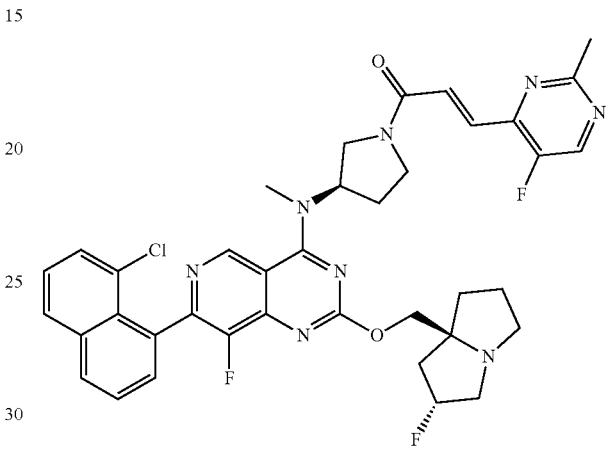

Example 241 (Method 8): (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(5-fluoro-2-methylpyrimidin-4-yl)prop-2-en-1-one

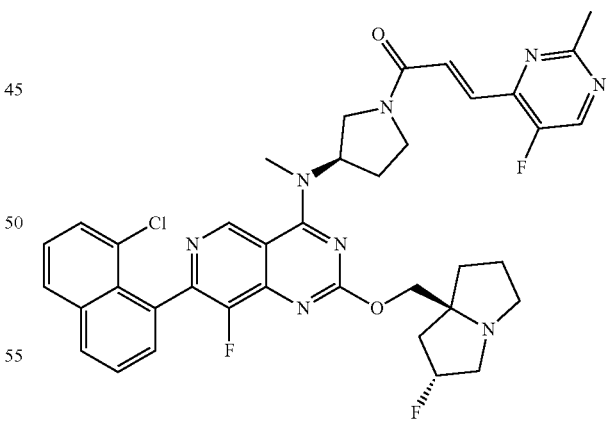

Step 1: (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(5-fluoro-2-methylpyrimidin-4-yl)prop-2-en-1-one The HWE reaction was prepared in a similar fashion to Method #8, Step 4. The crude residue was purified by reverse phase HPLC (column: Waters Xbridge Prep OBD C18 150*40 mm*10 μm; mobile phase: [water(NH₄HCO₃) ACN]; B %: 35%-65%, 8 min) affording (E)-1-((R)-3-((7-(8-chloronaphthalen-1-yl)-8-fluoro-2-(((2R,7aS)-2-fluoro-tetrahydro-1H-pyrrolizin-7a(5H)-yl)methoxy)pyrido[4,3-d]pyrimidin-4-yl)(methyl)amino)pyrrolidin-1-yl)-3-(5-fluoro-2-methylpyrimidin-4-yl)prop-2-en-1-one (19.24 mg, 19.30%) as a yellow solid: $^1$H NMR (400 MHz. Acetonitrile-d3) δ 9.27-9.12 (m, 1H), 8.62-8.50 (m, 1H), 8.11 (d, J=7.9 Hz, 1H), 8.00 (d, J=8.1 Hz, 1H), 7.73-7.64 (m, 2H), 7.64-7.60 (m, 2H), 7.60-7.56 (m, 1H), 7.53-7.47 (m, 1H), 5.44-5.10 (m, 2H), 4.25-4.19 (m, 1H), 4.17-4.10 (m, 1H), 4.07-3.96 (m, 1H), 3.92-3.77 (m, 1H), 3.77-3.63 (m, 1H), 3.62-3.47 (m, 1H), 3.46-3.39 (m, 3H), 3.19-3.13 (m, 1H), 3.12-3.02 (m, 2H), 2.93-2.83 (m, 1H), 2.66 (d, J=19.9 Hz, 3H), 2.45-2.31 (m, 2H), 2.22-2.14 (m, 1H), 2.13-2.03 (m, 2H), 1.93-1.79 (m, 3H).

LCMS (5% to 95% acetonitrile in water+0.03% ammonium bicarbonate over 6 min); retention time 2.197 min, ESI+ found [M+H]=728.3.

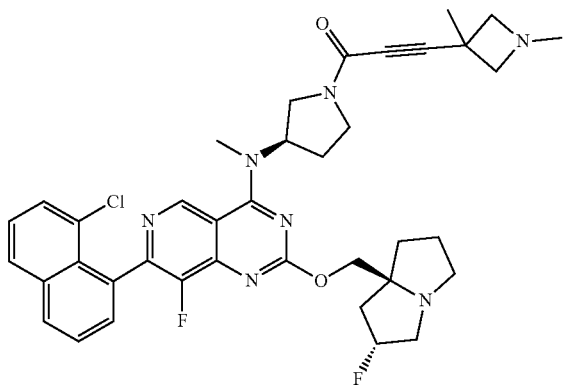 [SMILES: CN1CC(C)(C#CC(=O)N2CC[C@@H](N(C)c3nc(OC[C@@]45CCCN4C[C@H](F)C5)nc4c(F)c(-c5cccc6cccc(Cl)c56)ncc34)C2)C1]

Example 242 (Method 7): 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(1,3-dimethylazetidin-3-yl)prop-2-yn-1-one

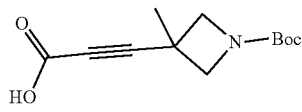 [SMILES: CC1(C#CC(=O)O)CN(C(=O)OC(C)(C)C)C1]

Step 1: 3-(1-tert-butoxycarbonyl-3-methyl-azetidin-3-yl)prop-2-ynoic acid

The carbonylation reaction was prepared in a similar fashion to Method #7, Step 1. The aqueous layer was concentrated in vacuo affording 3-(1-tert-butoxycarbonyl-3-methyl-azetidin-3-yl)prop-2-ynoic acid (320 mg, crude) as a white solid, which was used in the next step without further purification.

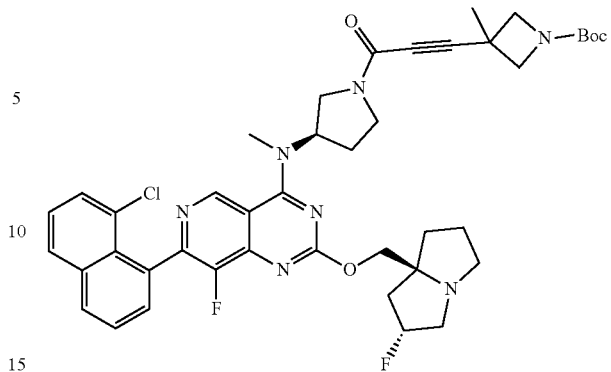

Step 2: tert-butyl 3-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)-3-methylazetidine-1-carboxylate The amide coupling reaction was prepared in a similar fashion to Method #7, Step 2. The residue was purified by column chromatography (silica gel, 100-200 mesh, 0-10% methanol in dichloromethane) affording tert-butyl 3-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)-3-methylazetidine-1-carboxylate (400 mg, 96.69%) as a yellow oil. LCMS Rt=2.564 min, m/z=785.3 [M+H]⁺.

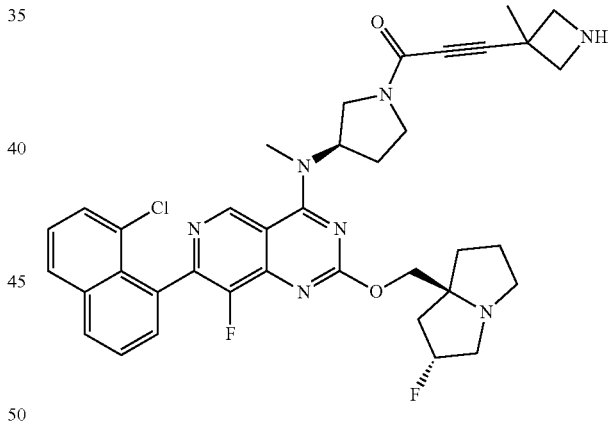

Step 3: 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-methylazetidin-3-yl)prop-2-yn-1-one The deprotection of the Boc group was prepared in a similar fashion to Method #7, Step 3. The mixture was concentrated in vacuo affording 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-methylazetidin-3-yl)prop-2-yn-1-one (150 mg, crude, trifluoroacetate salt) as a yellow solid, which was used in the next step without any further purification. LCMS Rt=2.937 min, m/z=685.3 [M+H]⁺.

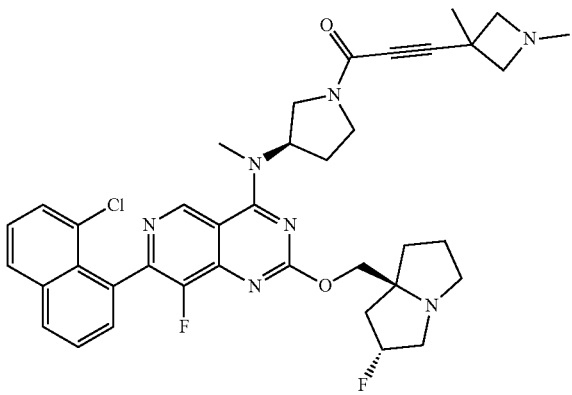 [SMILES: CN1CC(C)(C#CC(=O)N2CC[C@@H](N(C)c3nc(OC[C@@]45CCCN4C[C@H](F)C5)nc4c(F)c(-c5cccc6cccc(Cl)c56)ncc34)C2)C1]

Step 4: 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(1,3-dimethylazetidin-3-yl)prop-2-yn-1-one The reductive amination was prepared in a similar fashion to Method #7, Step 4. The mixture was concentrated in vacuo and purified by reverse phase HPLC (column: Waters Xbridge Prep OBD C18 150*40 mm*10 μm; mobile phase: [water(NH$_4$HCO$_3$)-ACN]; B %: 25%-65%, 8 min) affording 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(1,3-dimethylazetidin-3-yl)prop-2-yn-1-one (20.25 mg, 21.66%) as a yellow amorphous solid: $^1$H NMR (400 MHz, Acetonitrile-d3) δ 9.23-9.12 (m, 1H), 8.12 (d, J=8.0 Hz, 1H), 8.02 (d, J=8.0 Hz, 1H), 7.72-7.66 (m, 1H), 7.64-7.58 (m, 2H), 7.54-7.48 (m, 1H), 5.44-5.15 (m, 2H), 4.21-4.10 (m, 2H), 4.00-3.83 (m, 1H), 3.74-3.66 (m, 1H), 3.50-3.40 (m, 4H), 3.26 (dd, J=6.9, 11.4 Hz, 2H), 3.20-3.10 (m, 4H), 3.06 (s, 1H), 2.94-2.85 (m, 1H), 2.40-2.30 (m, 2H), 2.23 (d, J=12.6 Hz, 2H), 2.10 (br d, J=2.5 Hz, 4H), 1.92-1.75 (m, 4H), 1.52 (d, J=10.3 Hz, 3H).

LCMS (5% to 95% acetonitrile in water+0.03% ammonium bicarbonate over 6 min); retention time 2.987 min, ESI+ found [M+H]=699.3.

Example 243 (Method 1): (E)-1-(4-(7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)piperazin-1-yl)-3-(2,6-dimethylpyrimidin-4-yl)prop-2-en-1-one

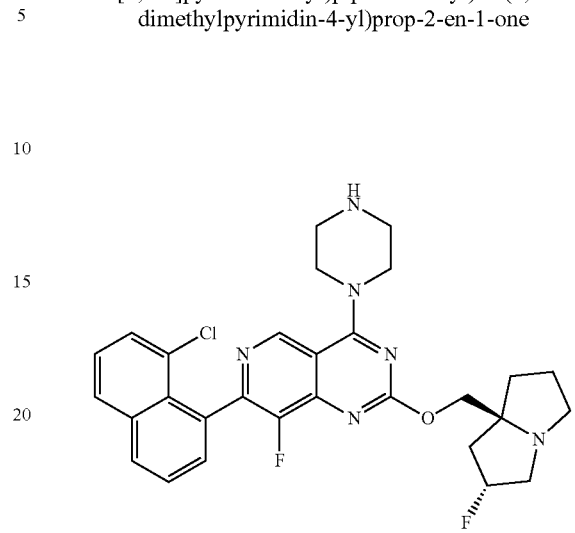

Step 1: 7-(8-chloronaphthalen-1-yl)-8-fluoro-2-(((2R,7aS)-2-fluorotetrahydro-1H-pyrrolizin-7a(5H)-yl)methoxy)-4-(piperazin-1-yl)pyrido[4,3-d]pyrimidine The substitution reaction was prepared in a similar fashion to Method #1, Step 8. The resulting residue was purified by reverse phase HPLC (column: Phenomenex Luna C18 100*40 mm*3 μm; mobile phase: [water(TFA)-ACN]; B %: 1%-45%, 8 min) affording 7-(8-chloronaphthalen-1-yl)-8-fluoro-2-(((2R,7aS)-2-fluorotetrahydro-1H-pyrrolizin-7a(5H)-yl)methoxy)-4-(piperazin-1-yl)pyrido[4,3-d]pyrimidine (300 mg, 37.69%, trifluoroacetate salt) as a white solid. LCMS Rt=0.295 min, m/z=550.2 [M+H]$^+$.

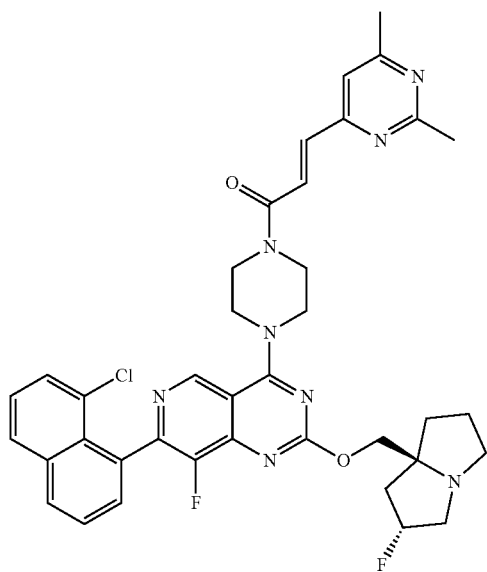 [SMILES: Cc1cc(/C=C/C(=O)N2CCN(c3nc(OC[C@@]45CCCN4C[C@H](F)C5)nc4c(F)c(-c5cccc6cccc(Cl)c56)ncc34)CC2)nc(C)n1]

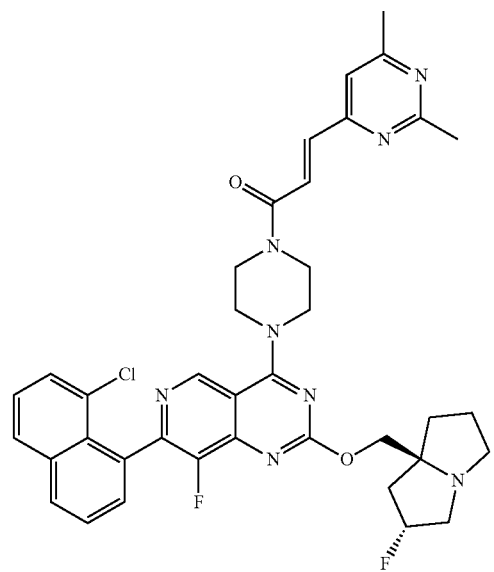 [SMILES: Cc1cc(/C=C/C(=O)N2CCN(c3nc(OC[C@@]45CCCN4C[C@H](F)C5)nc4c(F)c(-c5cccc6cccc(Cl)c56)ncc34)CC2)nc(C)n1]

Step 2: (E)-1-(4-(7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)piperazin-1-yl)-3-(2,6-dimethylpyrimidin-4-yl)prop-2-en-1-one The amide coupling reaction was prepared in a similar fashion to Method #1, Step 10. The resulting residue was purified by reverse phase HPLC (column: Waters Xbridge Prep OBD C18 150*40 mm*10 um; mobile phase: [water (NH$_4$HCO$_3$)-ACN]; B %: 30%-60%, 8 min) affording (E)-1-(4-(7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)piperazin-1-yl)-3-(2,6-dimethylpyrimidin-4-yl)prop-2-en-1-one (30.00 mg, 18.43%) as a yellow amorphous solid: $^1$H NMR (400 MHz, Acetonitrile-d3) δ 9.10 (s, 1H), 8.12 (dd, J=1.3, 8.1 Hz, 1H), 8.01 (dd, J=1.1, 8.2 Hz, 1H), 7.72-7.58 (m, 4H), 7.54-7.48 (m, 1H), 7.41 (d, J=15.1 Hz, 1H), 7.21 (s, 1H), 5.36-5.17 (m, 1H), 4.25-4.19 (m, 1H), 4.15-4.02 (m, 5H), 3.93 (br s, 4H), 3.20-3.10 (m, 2H), 3.08 (s, 1H), 2.95-2.87 (m, 1H), 2.62 (s, 3H), 2.45 (s, 3H), 2.21-2.17 (m, 1H), 2.11 (d, J=3.0 Hz, 1H), 2.09-2.02 (m, 1H), 1.93-1.82 (m, 3H).

LCMS (5% to 95% acetonitrile in water+0.03% ammonium bicarbonate over 6 min); retention time 2.133 min, ESI+ found [M+H]=710.3.

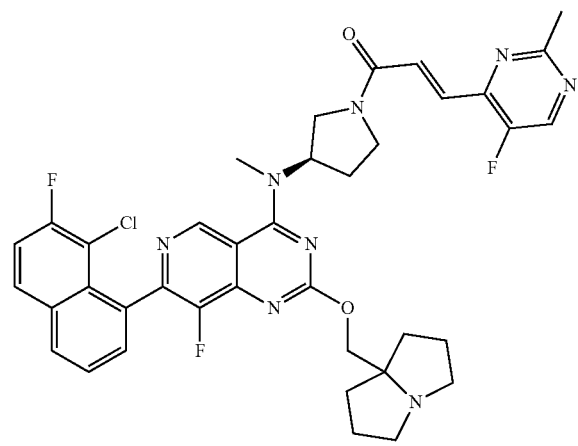 [SMILES: Cc1ncc(F)c(/C=C/C(=O)N2CC[C@@H](N(C)c3nc(OCC45CCCN4CCC5)nc4c(F)c(-c5cccc6ccc(F)c(Cl)c56)ncc34)C2)n1]

Example 244 (Method 1): (R,E)-1-(3-((7-(8-chloro-7-fluoronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(5-fluoro-2-methylpyrimidin-4-yl)prop-2-en-1-one

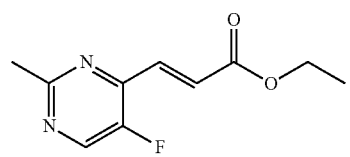

Step 1: ethyl (E)-3-(5-fluoro-2-methylpyrimidin-4-yl)acrylate

A mixture of 4-chloro-5-fluoro-2-methyl-pyrimidine (1 g, 6.82 mmol), ethyl (E)-3-(4,4,5,5-tetramethyl-1,3,2-dioxaborolan-2-yl)prop-2-enoate (2.31 g, 10.24 mmol), [2-(2-aminophenyl)phenyl]-chloro-palladium dicyclohexyl-[3-(2,4,6-triisopropylphenyl)phenyl]phosphane (536.88 mg, 682.36 μmol) and potassium phosphate (4.35 g, 20.47 mmol) in dioxane (30 mL) and water (10 mL) was degassed and purged with nitrogen 3 times. The mixture was stirred at 80° C. for 1.5 h under a nitrogen atmosphere. The mixture was diluted with water (20 mL) and extracted with ethyl acetate (3×50 mL). The combined organic layers were dried over sodium sulphate and concentrated in vacuo. The residue was purified by column chromatography (silica gel, 100-200 mesh, 0-100% ethyl acetate in petroleum ether) affording ethyl (E)-3-(5-fluoro-2-methylpyrimidin-4-yl)acrylate (1.1 g, 31.45%) as a yellow solid.

LCMS Rt=0.753 min, m/z=210.1 [M+H]$^+$.

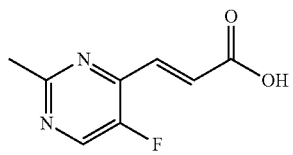

Step 2: (E)-3-(5-fluoro-2-methylpyrimidin-4-yl)acrylic acid

The hydrolysis reaction was prepared in a similar fashion to Method #1, Step 4. The crude product was concentrated in vacuo affording (E)-3-(5-fluoro-2-methylpyrimidin-4-yl)acrylic acid (140 mg, crude) as a brown solid, which was used in the next step without further purification.

LCMS Rt=0.557 min, m/z=182.1 [M+H]$^+$.

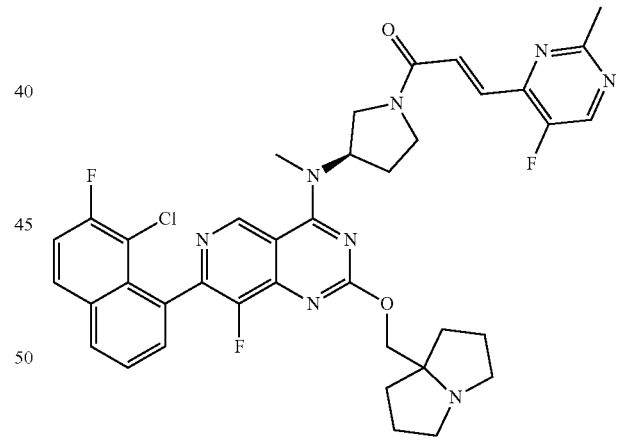

Step 3: (R,E)-1-(3-((7-(8-chloro-7-fluoronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(5-fluoro-2-methylpyrimidin-4-yl)prop-2-en-1-one The amide coupling reaction was prepared in a similar fashion to Method #1, Step 10. The resulting residue was purified by reverse phase HPLC (column: Waters Xbridge Prep OBD C18 150*40 mm*10 μm; mobile phase: [water (NH$_4$HCO$_3$)-ACN]; B %: 25%-55%, 8 min) affording (R,E)-1-(3-((7-(8-chloro-7-fluoronaphthalen-1-yl)-8-fluoro-

943

2-((tetrahydro-1H-pyrrolizin-7a(5H)-yl)methoxy)pyrido[4,3-d]pyrimidin-4-yl)(methyl)amino)pyrrolidin-1-yl)-3-(5-fluoro-2-methylpyrimidin-4-yl)prop-2-en-1-one (25.37 mg, 19.66%) as a brown solid: ¹H NMR (400 MHz, Chloroform-d) δ 9.09 (d, J=2.3 Hz, 1H), 8.45 (dd, J=1.8, 3.8 Hz, 1H), 7.92 (br d, J=7.8 Hz, 1H), 7.86-7.71 (m, 2H), 7.64-7.44 (m, 3H), 7.32 (t, J=8.7 Hz, 1H), 5.66-5.32 (m, 1H), 4.41-4.15 (m, 2H), 4.13-3.91 (m, 2H), 3.88-3.62 (m, 2H), 3.46-3.36 (m, 3H), 2.70-2.61 (m, 4H), 2.17-2.01 (m, 2H), 1.98-1.77 (m, 5H), 1.33-1.07 (m, 3H), 0.86-0.67 (m, 3H).

LCMS (5% to 95% acetonitrile in water+0.03% ammonium bicarbonate over 6 min); retention time 2.262 min, ESI+ found [M+H]=728.3.

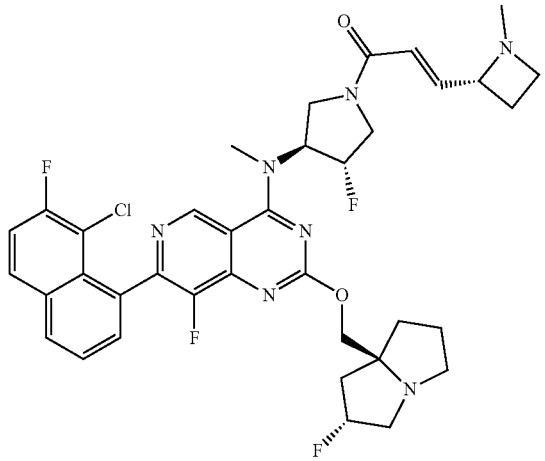 [SMILES: CN1CC[C@@H]1/C=C/C(=O)N1C[C@H](F)[C@@H](N(C)c2nc(OC[C@@]34CCCN3C[C@H](F)C4)nc3c(F)c(-c4cccc5ccc(F)c(Cl)c45)ncc23)C1]

Example 245 (Method 11): (E)-1-((3S,4S)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-((R)-1-methylazetidin-2-yl)prop-2-en-1-one

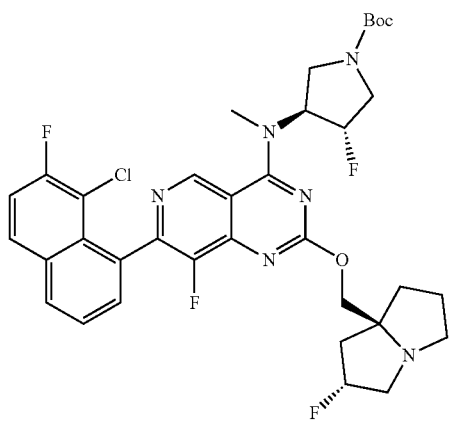 [SMILES: CN(c1nc(OC[C@@]23CCCN2C[C@H](F)C3)nc2c(F)c(-c3cccc4ccc(F)c(Cl)c34)ncc12)[C@H]1CN(C(=O)OC(C)(C)C)C[C@@H]1F]

944

Step 1: tert-butyl (3S,4S)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidine-1-carboxylate The substitution reaction was prepared in a similar fashion to Method #1, Step 8. The residue was purified by prep-HPLC (column: Phenomenex Luna C18 250*50 mm*10 μm; mobile phase: [water(TFA)-ACN]; B %: 15%-55%, 10 min) affording tert-butyl (3S,4S)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidine-1-carboxylate (232 mg, 18.48%, trifluoroacetate salt) as a yellow solid. LCMS Rt=1.473 min, m/z=700.3 [M+H]⁺.

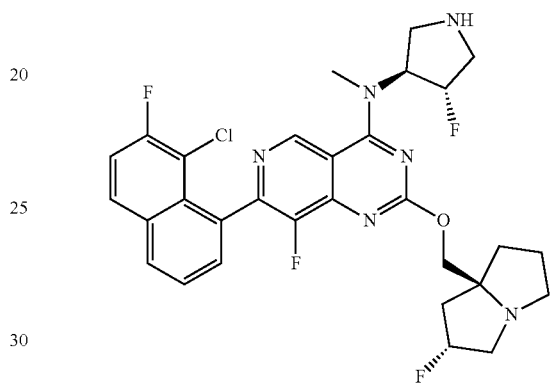

Step 2: 7-(8-chloro-7-fluoronaphthalen-1-yl)-8-fluoro-N-((3S,4S)-4-fluoropyrrolidin-3-yl)-2-(((2R,7aS)-2-fluorotetrahydro-1H-pyrrolizin-7a(5H)-yl)methoxy)-N-methylpyrido[4,3-d]pyrimidin-4-amine The deprotection of the Boc group was prepared in a similar fashion to Method #1, Step 9. The reaction mixture was concentrated in vacuo affording 7-(8-chloro-7-fluoronaphthalen-1-yl)-8-fluoro-N-((3S,4S)-4-fluoropyrrolidin-3-yl)-2-(((2R,7aS)-2-fluorotetrahydro-1H-pyrrolizin-7a(5H)-yl)methoxy)-N-methylpyrido[4,3-d]pyrimidin-4-amine (200 mg, crude, trifluoroacetic acid salt) as a yellow oil, which was used in the next step without any further purification. LCMS Rt=0.482 min, m/z=600.2 [M+H]⁺.

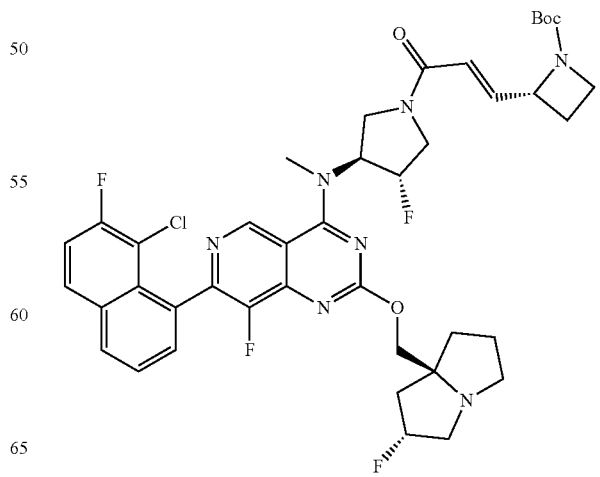

Step 3: tert-butyl (R)-2-((E)-3-((3S,4S)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-oxoprop-1-en-1-yl)azetidine-1-carboxylate The coupling reaction was prepared in a similar fashion to Method #11, Step 11. The reaction mixture was concentrated in vacuo affording tert-butyl (R)-2-((E)-3-((3S,4S)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-oxoprop-1-en-1-yl)azetidine-1-carboxylate (200 mg, crude) as a yellow oil, which was used in the next step without any further purification. LCMS Rt=0.664 min, m/z=810.3 [M+H]⁺.

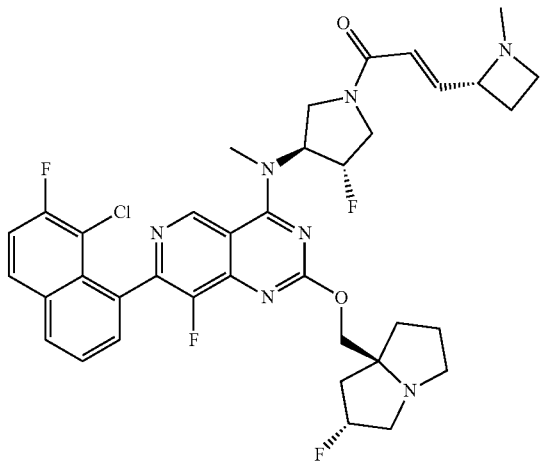

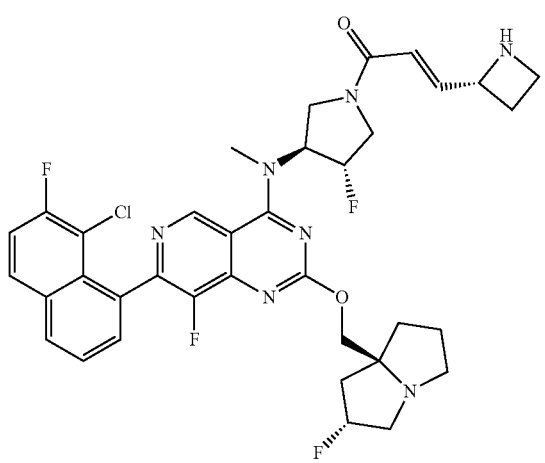 [SMILES: CN(c1nc(OC[C@@]23CCCN2C[C@H](F)C3)nc2c(F)c(-c3cccc4ccc(F)c(Cl)c34)ncc12)[C@H]1CN(C(=O)/C=C/[C@H]2CCN2)C[C@@H]1F]

Step 4: (E)-3-((R)-azetidin-2-yl)-1-((3S,4S)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)prop-2-en-1-one The deprotection of the Boc group was prepared in a similar fashion to Method #11, Step 12. The reaction mixture was concentrated in vacuo affording (E)-3-((R)-azetidin-2-yl)-1-((3S,4S)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)prop-2-en-1-one (200 mg, crude, trifluoroacetic acid salt) as a yellow oil, which was used in the next step without any further purification. LCMS Rt=0.488 min, m/z=710.3 [M+H]⁺.

Step 5: (E)-1-((3S,4S)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-4-fluoropyrrolidin-1-yl)-3-((R)-1-methylazetidin-2-yl)prop-2-en-1-one The reductive amination was prepared in a similar fashion to Method #11, Step 13.

The residue was purified by prep-HPLC (column: Waters Xbridge Prep OBD C18 150*40 mm*10 μm; mobile phase: [water(NH₄HCO₃)-ACN]; B %: 35%-65%, 8 min) affording (E)-1-((3S,4S)-3-((7-(8-chloro-7-fluoronaphthalen-1-yl)-8-fluoro-2-(((2R,7aS)-2-fluorotetrahydro-1H-pyrrolizin-7a (5H)-yl)methoxy)pyrido[4,3-d]pyrimidin-4-yl)(methyl)amino)-4-fluoropyrrolidin-1-yl)-3-((R)-1-methylazetidin-2-yl)prop-2-en-1-one (4.7 mg, 2.63%) as a white solid: ¹H NMR (400 MHz, Chloroform-d) δ 9.23 (s, 1H), 8.06-7.94 (m, 1H), 7.94-7.84 (m, 1H), 7.69-7.53 (m, 2H), 7.40 (br t, J=8.7 Hz, 1H), 7.10-6.92 (m, 1H), 6.63-6.41 (m, 1H), 5.75-5.32 (m, 2H), 5.25-5.02 (m, 1H), 4.69-4.55 (m, 1H), 4.52-4.20 (m, 3H), 4.04-3.34 (m, 10H), 3.28-3.05 (m, 2H), 2.54 (br d, J=19.8 Hz, 3H), 2.48-2.24 (m, 5H), 2.21-2.06 (m, 3H).

LCMS (5% to 95% acetonitrile in water+0.03% ammonium bicarbonate over 6 min); retention time 1.969 min, ESI+ found [M+H]=723.3

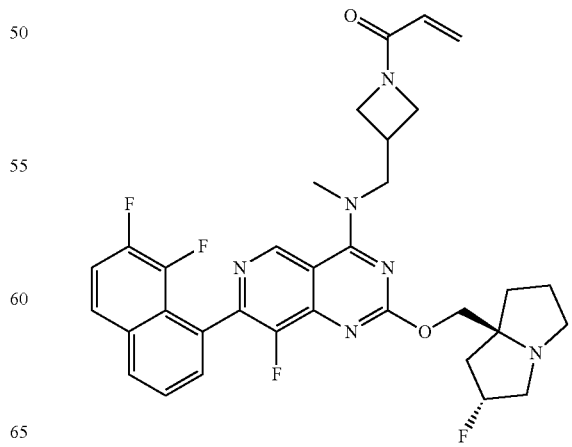

Example 246 (Method 2): 1-(3-(((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)prop-2-en-1-one

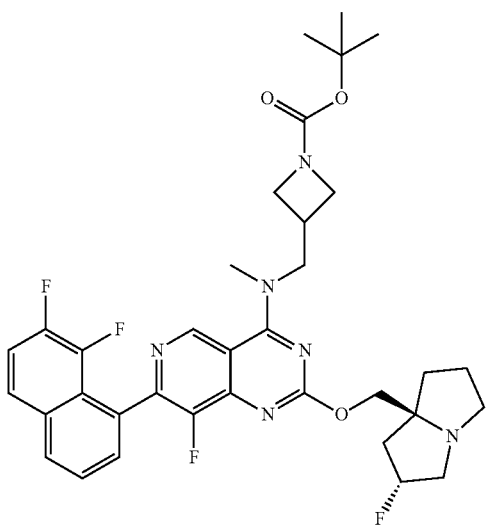 [SMILES: CN(CC1CN(C(=O)OC(C)(C)C)C1)c1nc(OC[C@@]23CCCN2C[C@H](F)C3)nc2c(F)c(-c3cccc4ccc(F)c(F)c34)ncc12]

Step 1: tert-butyl 3-(((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidine-1-carboxylate The Suzuki reaction was prepared in a similar fashion to Method #2, Step 5. The residue was purified by column chromatography (silica gel, 100-200 mesh, 0-100% ethyl acetate in petroleum ether) affording tert-butyl 3-(((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidine-1-carboxylate (300 mg, 58.14%) as a white solid. LCMS Rt=0.691 min, m/z=666.3 [M+H]$^+$.

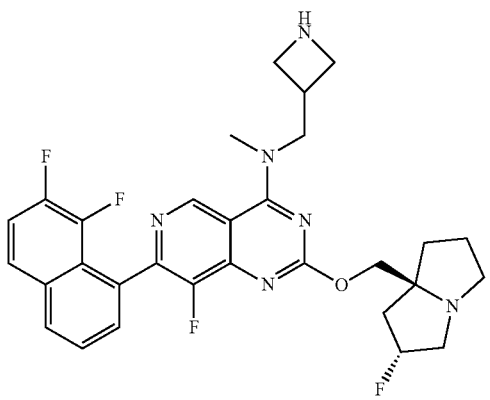 [SMILES: CN(CC1CNC1)c1nc(OC[C@@]23CCCN2C[C@H](F)C3)nc2c(F)c(-c3cccc4ccc(F)c(F)c34)ncc12]

Step 2: N-(azetidin-3-ylmethyl)-7-(7,8-difluoronaphthalen-1-yl)-8-fluoro-2-(((2R,7aS)-2-fluorotetrahydro-1H-pyrrolizin-7a(5H)-yl)methoxy)-N-methylpyrido[4,3-d]pyrimidin-4-amine The deprotection of the Boc group was prepared in a similar fashion to Method #1, Step 9. The reaction mixture was concentrated in vacuo affording N-(azetidin-3-ylmethyl)-7-(7,8-difluoronaphthalen-1-yl)-8-fluoro-2-(((2R,7aS)-2-fluorotetrahydro-1H-pyrrolizin-7a(5H)-yl)methoxy)-N-methylpyrido[4,3-d]pyrimidin-4-amine (100 mg, crude, trifluoroacetic salt) as a yellow oil, which was used in the next step without further purification. LCMS Rt=0.502 min, m/z=566.2 [M+H]$^+$.

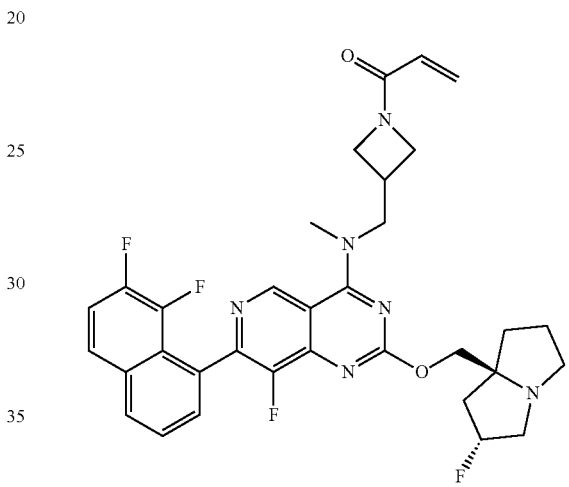

Step 3: 1-(3-(((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)prop-2-en-1-one The amide coupling reaction was prepared in a similar fashion to Method #2, Step 7. The crude product was purified by reverse phase prep-HPLC (column: Waters Xbridge Prep OBD C18 150*40 mm*10 μm; mobile phase: [water(NH$_4$HCO$_3$)-ACN]; B %: 30%-60%, 8 min) affording 1-(3-(((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)prop-2-en-1-one (30.19 mg, 34.45%) as a yellow amorphous solid: $^1$H NMR (400 MHz, Chloroform-d) δ 9.18 (s, 1H), 7.97 (br d, J=7.9 Hz, 1H), 7.72 (br dd, J=4.8, 8.9 Hz, 1H), 7.66-7.57 (m, 2H), 7.44-7.36 (m, 1H), 6.41-6.33 (m, 1H), 6.25-6.16 (m, 1H), 5.70 (br d, J=10.3 Hz, 1H), 5.35 (br s, 1H), 4.40-4.16 (m, 6H), 4.04-3.92 (m, 2H), 3.61 (s, 3H), 3.29-3.14 (m, 4H), 3.03-2.92 (m, 1H), 2.29-2.11 (m, 3H), 2.00-1.85 (m, 3H).

LCMS (5% to 95% acetonitrile in water+0.03% ammonium bicarbonate over 6 min); retention time 2.871 min, ESI+ found [M+H]=620.3.

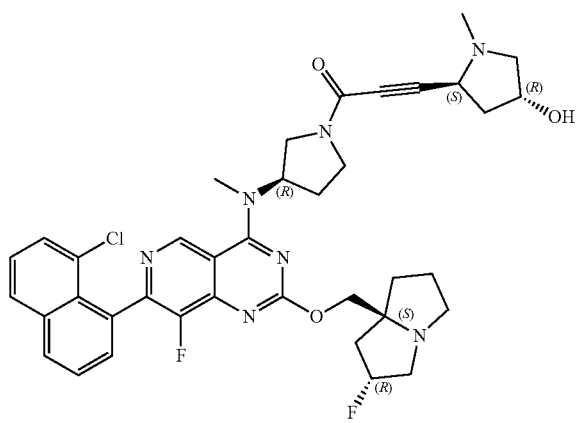

Example 247 (Method 7): 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-((2S,4R)-4-hydroxy-1-methylpyrrolidin-2-yl)prop-2-yn-1-one

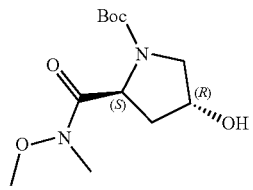

Step 1: tert-butyl (2S,4R)-4-hydroxy-2-(methoxy(methyl)carbamoyl)pyrrolidine-1-carboxylate To a solution of (2S,4R)-1-tert-butoxycarbonyl-4-hydroxy-pyrrolidine-2-carboxylic acid (10 g, 43.24 mmol) in dichloromethane (250 mL) was added N-methoxymethanamine (5.28 g, 86.49 mmol), 4-methylmorpholine (8.75 g, 86.49 mmol), 1-(3-dimethylaminopropyl)-3-ethylcarbodiimide (16.58 g, 86.49 mmol) and 1-hydroxybenzotriazole (11.69 g, 86.49 mmol) at 0° C. The mixture was stirred at 25° C. for 12 h. The reaction mixture was quenched with water (250 mL) and extracted with dichloromethane (3×200 mL). The combined organic layers were dried over sodium sulphate and concentrated in vacuo affording tert-butyl (2S,4R)-4-hydroxy-2-(methoxy(methyl)carbamoyl)pyrrolidine-1-carboxylate (12 g, crude) as a colorless oil, which was used in the next step without any further purification. LCMS Rt=0.461 min, m/z=274.2 [M+H]$^+$.

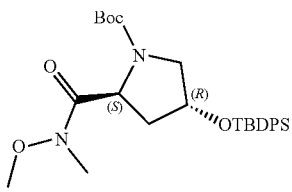

Step 2: (2S,4R)-tert-butyl 4-((tert-butyldiphenylsilyl)oxy)-2-(methoxy(methyl)carbamoyl)pyrrolidine-1-carboxylate To a solution of tert-butyl (2S,4R)-4-hydroxy-2-(methoxy(methyl)carbamoyl)pyrrolidine-1-carboxylate (11 g, 40.10 mmol) in dichloromethane (200 mL) was added tert-butyl-chloro-diphenyl-silane (33.07 g, 120.30 mmol, 30.90 mL) and imidazole (8.19 g, 120.30 mmol). The mixture was stirred at 0° C. for 12 h. The reaction mixture was concentrated in vacuo. The residue was purified by column chromatography (silica gel, 100-200 mesh, 20-50% ethyl acetate in petroleum ether) affording (2S,4R)-tert-butyl 4-((tert-butyldiphenylsilyl)oxy)-2-(methoxy(methyl)carbamoyl)pyrrolidine-1-carboxylate (18 g, 76.2%) as a colorless oil. LCMS Rt =1.037 min, m/z=512.3 [M+H]$^+$.

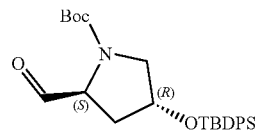

Step 3: tert-butyl (2S,4R)-4-((tert-butyldiphenylsilyl)oxy)-2-formylpyrrolidine-1-carboxylate To a solution of (2S,4R)-tert-butyl 4-((tert-butyldiphenylsilyl)oxy)-2-(methoxy(methyl)carbamoyl)pyrrolidine-1-carboxylate (5 g, 9.75 mmol) in tetrahydrofuran (100 mL) was added diisobutylaluminium hydride (1M, 19.50 mL). The mixture was stirred at −75° C. for 1 h. The reaction mixture was quenched with saturated ammonium chloride (30 mL) at 0° C. and extracted with ethyl acetate (3×100 mL). The combined organic layers were dried over sodium sulphate and concentrated in vacuo affording tert-butyl (2S,4R)-4-((tert-butyldiphenylsilyl)oxy)-2-formylpyrrolidine-1-carboxylate (4 g, crude) as a yellow oil, which was used in next step without any further purification. LCMS Rt=1.038 min, m/z=453.2 [M+H]$^+$.

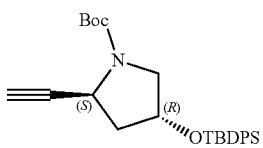

Step 4: tert-butyl (2S,4R)-4-((tert-butyldiphenylsilyl)oxy)-2-ethynylpyrrolidine-1-carboxylate To a solution of tert-butyl (2S,4R)-4-((tert-butyldiphenylsilyl)oxy)-2-formylpyrrolidine-1-carboxylate (4 g, 8.82 mmol) in methanol (100 mL) was added 1-diazo-1-dimethoxyphosphoryl-propan-2-one (5.08 g, 26.45 mmol) and potassium carbonate (3.66 g, 26.45 mmol) at 0° C. The mixture was stirred at 25° C. for 12 h. The reaction mixture was diluted with water (100 mL) and extracted with ethyl acetate (3×100 mL). The combined organic layers were dried over sodium sulphate and concentrated in vacuo. The residue was purified by column chromatography (silica gel, 100-200 mesh, 10-20% ethyl acetate in petroleum ether) affording tert-butyl (2S,4R)-4-((tert-butyldiphenylsilyl)oxy)-2-ethynylpyrrolidine-1-carboxylate (2.1 g, 43.7%) as a colorless oil.

LCMS Rt=1.072 min, m/z=449.2 [M+H]+.

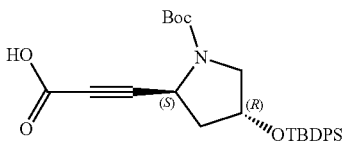

Step 5: 3-((2S,4R)-1-(tert-butoxycarbonyl)-4-((tert-butyldiphenylsilyl)oxy)pyrrolidin-2-yl)propiolic acid To a solution of tert-butyl (2S,4R)-4-((tert-butyldiphenylsilyl)oxy)-2-ethynylpyrrolidine-1-carboxylate (600 mg, 1.33 mmol) in tetrahydrofuran (30 mL) was added n-butyllithium (2.5M, 1.60 mL) and solid carbon dioxide. The mixture was stirred at −78° C. for 1 h. The reaction mixture was quenched with saturated ammonium chloride (30 mL) at 0° C. and then adjust pH=2 with potassium hydrogen sulfate. The mixture was extracted with ethyl acetate (3×30 mL). The combined organic layers were dried over sodium sulphate and concentrated in vacuo affording 3-((2S,4R)-1-(tert-butoxycarbonyl)-4-((tert-butyldiphenylsilyl)oxy)pyrrolidin-2-yl)propiolic acid (350 mg, crude) as a yellow oil, which was used in the next reaction without purification. LCMS Rt=0.967 min, m/z=493.2 [M+H]+.

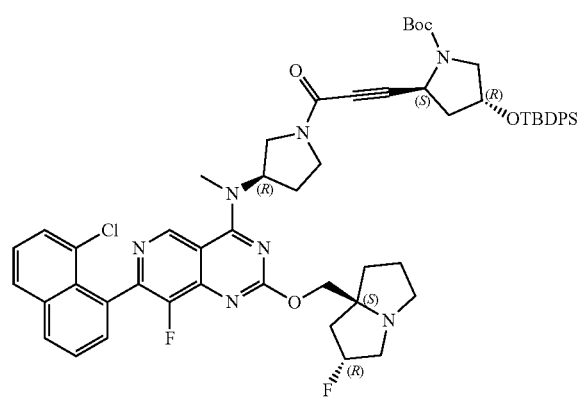

Step 6: (2S,4R)-tert-butyl 4-((tert-butyldiphenylsilyl)oxy)-2-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)pyrrolidine-1-carboxylate The amide coupling reaction was prepared in a similar fashion to Method #7, Step 2. The residue was purified by reversed phase HPLC(column: Phenomenex Luna 80*30 mm*3 μm; mobile phase: [water(TFA)-ACN]; B %: 65%-95%, 8 min) affording (2S,4R)-tert-butyl 4-((tert-butyldiphenylsilyl)oxy)-2-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)pyrrolidine-1-carboxylate (60 mg, 32.56%, trifluoroacetate salt) as a white solid. LCMS Rt=0.970 min, m/z=1039.4 [M+H]+.

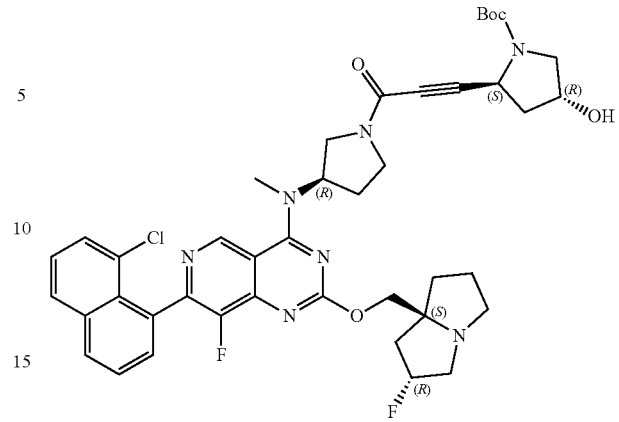

Step 7: (2S,4R)-tert-butyl 2-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)-4-hydroxypyrrolidine-1-carboxylate To a solution of (2S,4R)-tert-butyl 4-((tert-butyldiphenylsilyl)oxy)-2-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)pyrrolidine-1-carboxylate (60 mg, 51.96 μmol, trifluoroacetic acid) in tetrahydrofuran (2 mL) was added N,N-diethylethanamine trihydrofluoride (83.76 mg, 519.60 μmol). The mixture was stirred at 25° C. for 12 h. The reaction mixture was concentrated in vacuo affording (2S,4R)-tert-butyl 2-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)-4-hydroxypyrrolidine-1-carboxylate (40 mg, crude) as a yellow oil, which was used in the next step without any further purification. LCMS Rt=0.754 min, m/z=801.3 [M+H]+.

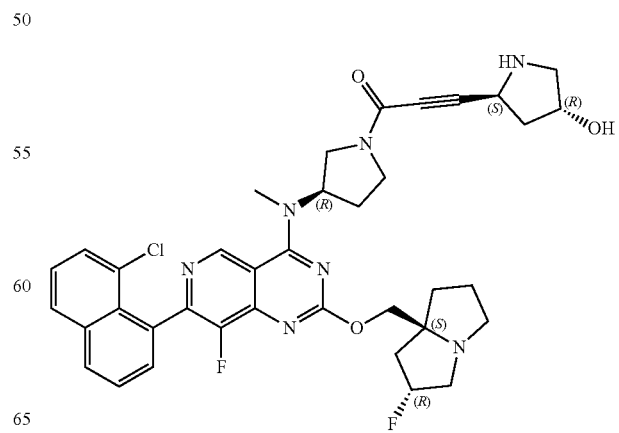

Step 8: 1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((2S,4R)-4-hydroxypyrrolidin-2-yl)prop-2-yn-1-one Deprotection of the Boc group was prepared in a similar fashion to Method #7, Step 3. The crude product was purified by reverse phase HPLC (column: Phenomenex Luna 80*30 mm*3 μm; mobile phase: [water(TFA)-ACN]; B %: 1%-40%, 8 min) affording 1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((2S,4R)-4-hydroxypyrrolidin-2-yl)prop-2-yn-1-one (20 mg, 49.15%, trifluoroacetate salt) as a yellow oil. LCMS Rt=0.601 min, m/z=701.3 [M+H]⁺.

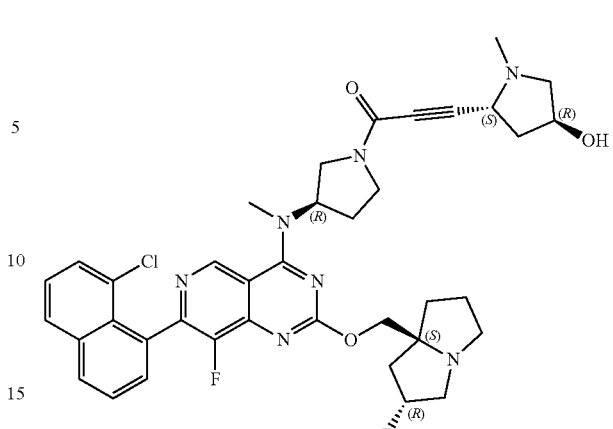

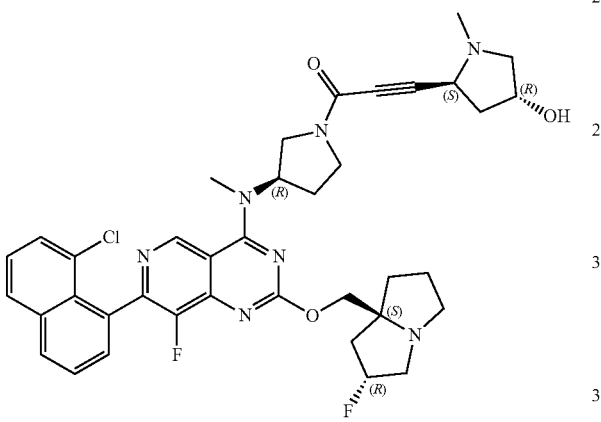

Step 9: 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-((2S,4R)-4-hydroxy-1-methylpyrrolidin-2-yl)prop-2-yn-1-one The reductive amination reaction was prepared in a similar fashion to Method #7, Step 4. The crude product was purified by reverse phase HPLC (column: Waters Xbridge Prep OBD C18 150*40 mm*10 μm; mobile phase: [water (NH₄HCO₃)-ACN]; B %: 30%-50%, 8 min) affording 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-((2S,4R)-4-hydroxy-1-methylpyrrolidin-2-yl)prop-2-yn-1-one (7.85 mg, 88.74%) as a white solid.: ¹H NMR (400 MHz, Chloroform-d) δ 9.12-9.02 (m, 1H), 7.99-7.90 (m, 1H), 7.81 (dd, J=2.8, 8.1 Hz, 1H), 7.57-7.45 (m, 3H), 7.35 (dt, J=3.2, 7.8 Hz, 1H), 5.41-5.14 (m, 2H), 4.44-4.37 (m, 1H), 4.32-4.10 (m, 3H), 3.98-3.78 (m, 2H), 3.70-3.51 (m, 3H), 3.49-3.43 (m, 1H), 3.41-3.34 (m, 3H), 3.25-3.10 (m, 3H), 3.04-2.90 (m, 2H), 2.52-2.43 (m, 2H), 2.41 (s, 2H), 2.36-2.28 (m, 2H), 2.26-2.17 (m, 3H), 2.13-1.94 (m, 4H).

LCMS (5% to 95% acetonitrile in water+0.03% ammonium bicarbonate over 6 min); retention time 1.936 min, ESI+ found [M+H]=715.3.

Example 248 (Method 7): 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-((2R,4S)-4-hydroxy-1-methylpyrrolidin-2-yl)prop-2-yn-1-one

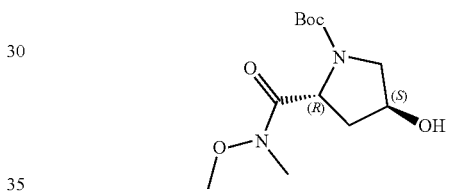

Step 1: (2R,4S)-tert-butyl 4-hydroxy-2-(methoxy(methyl)carbamoyl)pyrrolidine-1-carboxylate To a solution of (2R,4S)-1-(tert-butoxycarbonyl)-4-hydroxypyrrolidine-2-carboxylic acid (9 g, 38.92 mmol) and N-methoxymethanamine hydrochloride (7.59 g, 77.84 mmol) in dichloromethane (90 mL) was added 4-methylmorpholine (15.75 g, 155.68 mmol), 1-(3-dimethylaminopropyl)-3-ethylcarbodiimide (14.92 g, 77.84 mmol) and 1-hydroxybenzotriazole (7.89 g, 58.38 mmol). The mixture was stirred at 25° C. for 12 h. The mixture was diluted with water (200 mL) and extracted with dichloromethane (3×200 mL). The combined organic layers were dried over sodium sulphate and concentrated in vacuo. The residue was purified by column chromatography (silica gel, 100-200 mesh, 50-50% ethyl acetate in petroleum ether) affording (2R,4S)-tert-butyl 4-hydroxy-2-(methoxy(methyl)carbamoyl)pyrrolidine-1-carboxylate (8 g, 74.93%) as a white solid. LCMS Rt=0.487 min, m/z=274.2 [M+H]⁺.

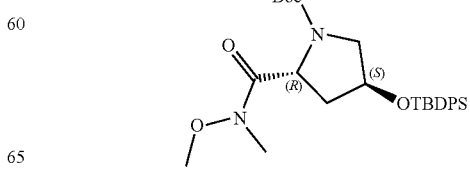

Step 2: (2R,4S)-tert-butyl 4-((tert-butyldiphenylsilyl)oxy)-2-(methoxy(methyl)carbamoyl)pyrrolidine-1-carboxylate To a solution of (2R,4S)-tert-butyl 4-hydroxy-2-(methoxy(methyl)carbamoyl)pyrrolidine-1-carboxylate (8 g, 29.16 mmol) in dichloromethane (80 mL) was added imidazole (9.93 g, 145.82 mmol) and tert-butyl-chloro-diphenyl-silane (16.03 g, 58.33 mmol) at 0° C. The mixture was stirred at 25° C. for 1 h. The mixture was diluted with water (200 mL) and extracted with dichloromethane (3×200 mL). The combined organic layers were dried over sodium sulphate and concentrated in vacuo. The residue was purified by column chromatography (silica gel, 100-200 mesh, 20-50% ethyl acetate in petroleum ether) affording (2R,4S)-tert-butyl 4-((tert-butyldiphenylsilyl)oxy)-2-(methoxy(methyl)carbamoyl)pyrrolidine-1-carboxylate (13 g, 86.94%) as a white oil. LCMS Rt=0.996 min, m/z=512.3 [M+H]$^+$.

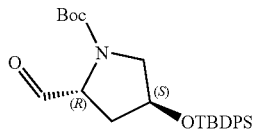

Step 3: (2R,4S)-tert-butyl 4-((tert-butyldiphenylsilyl)oxy)-2-formylpyrrolidine-1-carboxylate To a solution of (2R,4S)-tert-butyl 4-((tert-butyldiphenylsilyl)oxy)-2-(methoxy(methyl)carbamoyl)pyrrolidine-1-carboxylate (1 g, 1.95 mmol) in tetrahydrofuran (10 mL) was added diisobutylaluminium hydride (1 M, 5.85 mL). The mixture was stirred at 0° C. for 1 h. The reaction mixture was quenched with saturated ammonium chloride (20 mL) and extracted with ethyl acetate (3×20 mL). The combined organic layers were dried over sodium sulphate and concentrated in vacuo affording (2R,4S)-tert-butyl 4-((tert-butyldiphenylsilyl)oxy)-2-formylpyrrolidine-1-carboxylate (1 g, crude) as a yellow oil, which was used in the next step without any further purification. LCMS Rt=1.046 min, m/z=453.2 [M+H]$^+$.

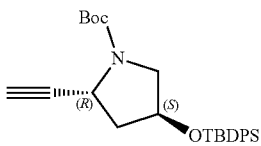

Step 4: tert-butyl (2R,4S)-4-[tert-butyl(diphenyl)silyl]oxy-2-ethynyl-pyrrolidine-1-carboxylate To a solution of (2R,4S)-tert-butyl 4-((tert-butyldiphenylsilyl)oxy)-2-formylpyrrolidine-1-carboxylate (1 g, 2.20 mmol) in methanol (10 mL) was added potassium carbonate (609.31 mg, 4.41 mmol) and 1-diazo-1-dimethoxyphosphoryl-propan-2-one (635.22 mg, 3.31 mmol) at 0° C. The mixture was stirred at 25° C. for 2 h. The mixture was diluted with water (20 mL) and extracted with dichloromethane (3×20 mL). The combined organic layers were dried over sodium sulphate and concentrated in vacuo. The residue was purified by column chromatography (silica gel, 100-200 mesh, 10-20% ethyl acetate in petroleum ether) affording tert-butyl (2R,4S)-4-[tert-butyl(diphenyl)silyl]oxy-2-ethynyl-pyrrolidine-1-carboxylate (500 mg, 50.44%) as a white oil: $^1$H NMR (400 MHz, Chloroform-d) δ 7.61-7.52 (m, 4H), 7.43-7.27 (m, 6H), 4.62-4.41 (m, 1H), 4.39-4.31 (m, 1H), 3.41-3.17 (m, 2H), 2.21-2.06 (m, 2H), 1.92 (br d, J=4.5 Hz, 1H), 1.41 (s, 9H), 0.97 (s, 9H). LCMS Rt=0.937 min, m/z=449.2 [M+H]$^+$.

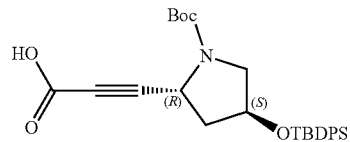

Step 5: 3-((2R,4S)-1-(tert-butoxycarbonyl)-4-((tert-butyldiphenylsilyl)oxy)pyrrolidin-2-yl)propiolic acid To a solution of tert-butyl (2R,4S)-4-[tert-butyl(diphenyl)silyl]oxy-2-ethynyl-pyrrolidine-1-carboxylate (300 mg, 667.18 μmol) in tetrahydrofuran (3 mL) was added solid carbon dioxide and n-butyllithium (2.5M, 533.74 uL). The mixture was stirred at −78° C. for 2 h. The reaction mixture was quenched with saturated ammonium chloride (10 mL) and potassium hydrogen sulfate (10 mL) at 0° C. and extracted with ethyl acetate (3×15 mL). The combined organic layers were dried over sodium sulphate and concentrated in vacuo affording 3-((2R,4S)-1-(tert-butoxycarbonyl)-4-((tert-butyldiphenylsilyl)oxy)pyrrolidin-2-yl)propiolic acid (300 mg, crude) as a yellow oil, which was used in the next step without any further purification. LCMS Rt=0.985 min, m/z=493.2 [M+H]$^+$.

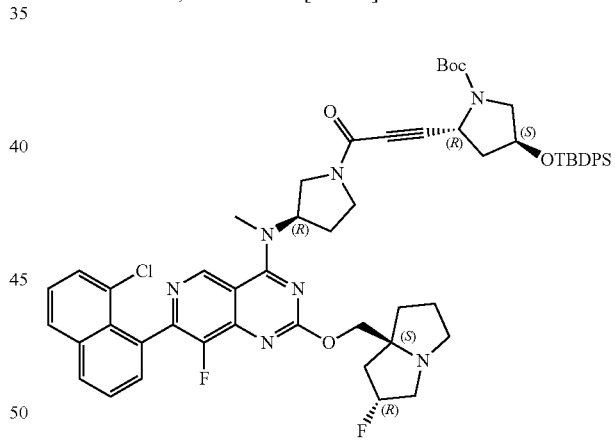

Step 6: (2R,4S)-tert-butyl 4-((tert-butyldiphenylsilyl)oxy)-2-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)pyrrolidine-1-carboxylate The amide coupling reaction was prepared in a similar fashion to Method #7, Step 2. The residue was purified by reverse phase HPLC (column: Phenomenex Luna 80*30 mm*3 μm; mobile phase: [water(TFA)-ACN]; B %: 40%-70%, 8 min) affording (2R,4S)-tert-butyl 4-((tert-butyldiphenylsilyl)oxy)-2-(3-((R)-3-((7-(8-chloronaphthalen-1-yl)-8-fluoro-2-(((2R,7aS)-2-fluorohexahydro-1H-pyrrolizin-7a- yl)methoxy)pyrido[4,3-d]pyrimidin-4-yl)(methyl)amino)pyrrolidin-1-yl)-3-oxoprop-1-yn-1-yl)pyrrolidine-1-carboxylate (35 mg, 17.15%, trifluoroacetate salt) as a yellow solid. LCMS Rt=0.969 min, m/z=1039.4 [M+H]$^+$.

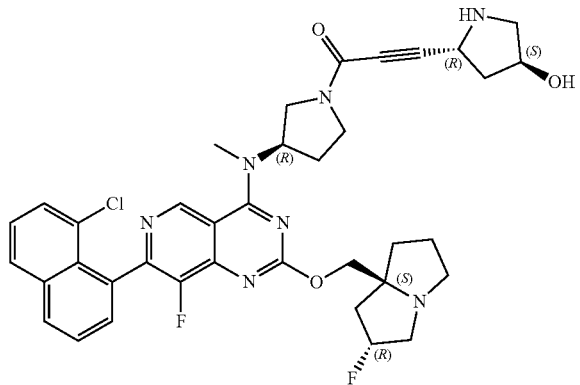

Step 7: 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-((2R,4S)-4-hydroxypyrrolidin-2-yl)prop-2-yn-1-one A mixture of (2R,4S)-tert-butyl 4-((tert-butyldiphenylsilyl)oxy)-2-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)pyrrolidine-1-carboxylate (30 mg, 25.98 μmol, trifluoroacetate salt) in trifluoroacetic acid (1 mL) was stirred at 60° C. for 2 h. The mixture was concentrated in vacuo affording 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-((2R,4S)-4-hydroxypyrrolidin-2-yl)prop-2-yn-1-one (30 mg, crude, trifluoroacetate salt) as a yellow solid, which was used in the next step without any further purification. LCMS Rt=0.544 min, m/z=701.3 [M+H]$^+$.

Step 8: 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-((2R,4S)-4-hydroxy-1-methylpyrrolidin-2-yl)prop-2-yn-1-one The reductive amination reaction was prepared in a similar fashion to Method #7, Step 4. The residue was purified by reverse phase HPLC (column: Waters Xbridge Prep OBD C18 150*40 mm*10 μm; mobile phase: [water(NH$_4$HCO$_3$)-ACN]; B %: 25%-55%, 8 min) affording 1—((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-((2R,4S)-4-hydroxy-1-methylpyrrolidin-2-yl)prop-2-yn-1-one: $^1$H NMR (400 MHz, Acetonitrile-d3) δ 9.20 (dd, J=1.4, 3.6 Hz, 1H), 8.13 (d, J=8.0 Hz, 1H), 8.02 (d, J=8.3 Hz, 1H), 7.72-7.67 (m, 1H), 7.65-7.58 (m, 2H), 7.54-7.50 (m, 1H), 5.45-5.24 (m, 2H), 4.54-4.49 (m, 1H), 4.36-4.32 (m, 2H), 4.22-3.86 (m, 2H), 3.78-3.64 (m, 2H), 3.61-3.57 (m, 1H), 3.47-3.43 (m, 3H), 3.36 (br d, J=14.4 Hz, 2H), 3.29 (br dd, J=2.9, 7.1 Hz, 1H), 3.19 (br s, 2H), 3.07-3.01 (m, 2H), 2.73 (s, 1H), 2.68 (s, 2H), 1.85-1.78 (m, 3H), 1.64-1.53 (m, 2H), 1.48-1.41 (m, 2H), 1.34 (dd, J=6.5, 11.5 Hz, 1H), 1.27 (s, 1H), 0.96 (s, 1H).

LCMS (5% to 95% acetonitrile in water+0.03% ammonium bicarbonate over 6 min); retention time 2.789 min, ESI+ found [M+H]=715.3.

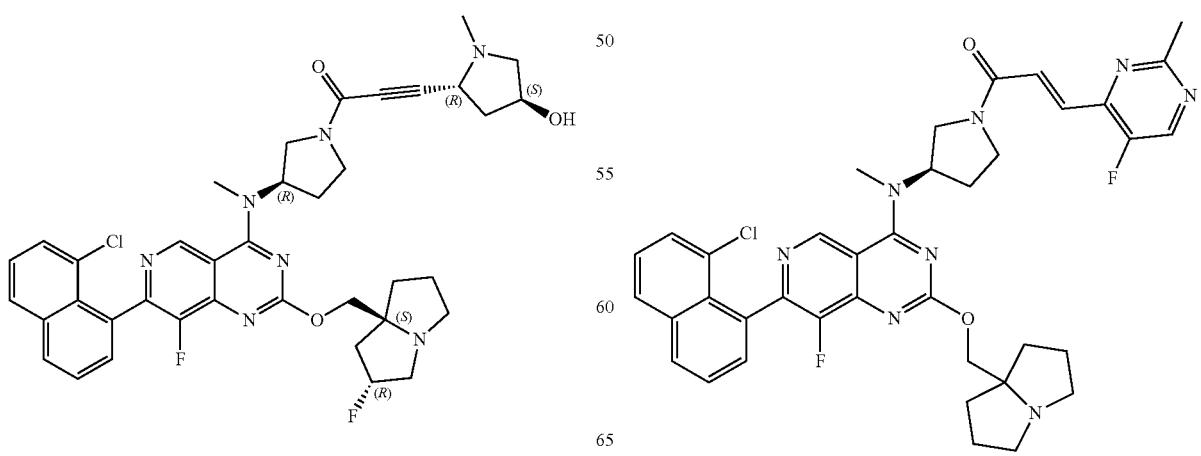

Example 249 (Method 2): (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(5-fluoro-2-methylpyrimidin-4-yl)prop-2-en-1-one

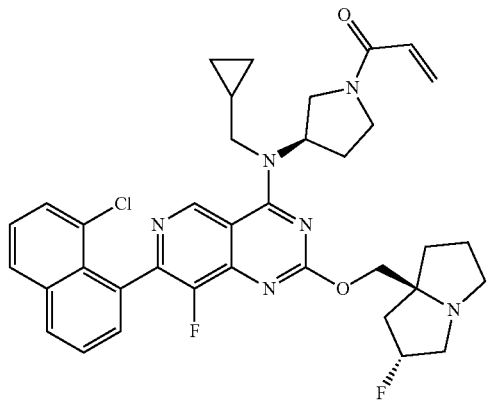 [SMILES: C=CC(=O)N1CC[C@@H](N(CC2CC2)c2nc(OC[C@@]34CCCN3C[C@H](F)C4)nc3c(F)c(-c4cccc5cccc(Cl)c45)ncc23)C1]

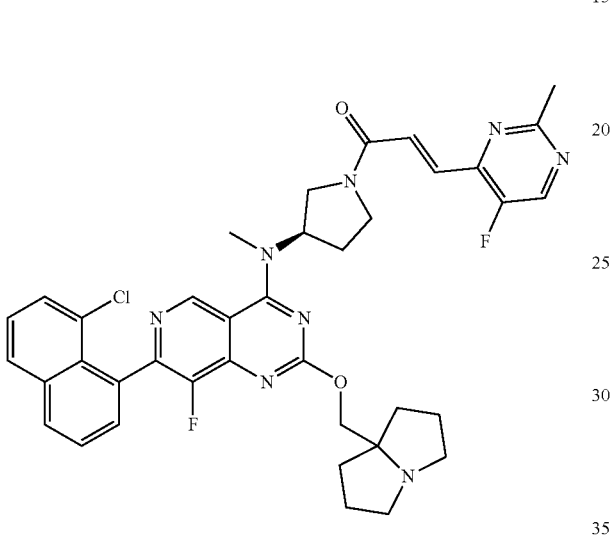

Step 1: (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(5-fluoro-2-methylpyrimidin-4-yl)prop-2-en-1-one The amide coupling reaction was prepared in a similar fashion to Method #2, Step 7. The crude product was purified by reverse phase prep-HPLC (column: Waters Xbridge Prep OBD C18 150*40 mm*10 um; mobile phase: [water(NH₄HCO₃)-ACN]; B %: 35%-65%, 8 min) affording (R,E)-1-(3-((7-(8-chloronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)-3-(5-fluoro-2-methylpyrimidin-4-yl)prop-2-en-1-one (8.56 mg, 7.30%) as a yellow solid: $^1$H NMR (400 MHz, Chloroform-d) δ 9.16 (d, J=2.0 Hz, 1H), 8.52 (dd, J=1.8, 3.8 Hz, 1H), 8.01 (br d, J=7.5 Hz, 1H), 7.93-7.80 (m, 2H), 7.70-7.50 (m, 4H), 7.48-7.36 (m, 1H), 5.65-5.46 (m, 1H), 4.39-4.24 (m, 2H), 4.22-4.02 (m, 2H), 3.77 (dt, J=7.8, 12.9 Hz, 2H), 3.53-3.46 (m, 3H), 3.26-3.01 (m, 2H), 2.74 (d, J=10.5 Hz, 3H), 2.45-2.29 (m, 2H), 1.90 (br s, 1OH).

LCMS (5% to 95% acetonitrile in water+0.03% ammonium bicarbonate over 6 min); retention time 2.793 min, ESI+ found [M+H]=710.3.

Example 250 (Method 2): 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(cyclopropylmethyl)amino)pyrrolidin-1-yl)prop-2-en-1-one

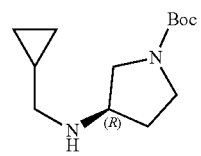

Step 1: tert-butyl (R)-3-((cyclopropylmethyl)amino)pyrrolidine-1-carboxylate To a solution of tert-butyl (3R)-3-aminopyrrolidine-1-carboxylate (1 g, 5.37 mmol) in tetrahydrofuran (10 mL) was added cyclopropanecarbaldehyde (376.32 mg, 5.37 mmol), sodium triacetoxyborohydride (1.71 g, 8.05 mmol), and acetic acid (64.49 mg, 1.07 mmol). The mixture was stirred at 25° C. for 12 h. The mixture was diluted with water (10 mL) and extracted with ethyl acetate (3×50 mL). The combined organic layers were dried over sodium sulphate and concentrated in vacuo. The residue was purified by column chromatography (silica gel, 100-200 mesh, 5-7% methanol in dichloromethane) affording tert-butyl (R)-3-((cyclopropylmethyl)amino)pyrrolidine-1-carboxylate (600 mg, 46.50%) as a white solid.

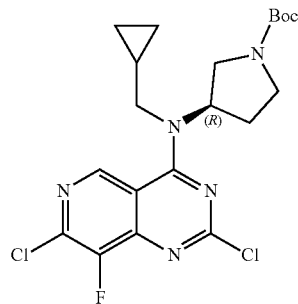

Step 2: (R)-tert-butyl 3-((cyclopropylmethyl)(2,7-dichloro-8-fluoropyrido[4,3-d]pyrimidin-4-yl)amino)pyrrolidine-1-carboxylate The substitution reaction was prepared in a similar fashion to Method #2, Step 3. The residue was purified by column chromatography (silica gel, 100-200 mesh, 10-30% ethyl acetate in petroleum ether) affording (R)-tert-butyl 3-((cyclopropylmethyl)(2,7-dichloro-8-fluoropyrido[4,3-d]pyrimidin-4-yl)amino)pyrrolidine-1-carboxylate (0.5 g, 27.66%) as a yellow oil. LCMS Rt=0.533 min, m/z=455.1 [M+H]+.

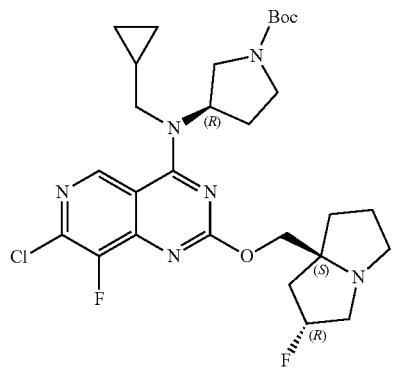

Step 3: (R)-tert-butyl 3-((7-chloro-8-fluoro-2-(((2R,7aS)-2-fluorohexahydro-1H-pyrrolizin-7a-yl)methoxy)pyrido[4,3-d]pyrimidin-4-yl)(cyclopropylmethyl)amino)pyrrolidine-1-carboxylate The substitution reaction was prepared in a similar fashion to Method #2, Step 4. The residue was purified by column chromatography (silica gel, 100-200 mesh, 50-80% ethyl acetate in petroleum ether) affording (R)-tert-butyl 3-((7-chloro-8-fluoro-2-(((2R,7aS)-2-fluorohexahydro-1H-pyrrolizin-7a-yl)methoxy)pyrido[4,3-d]pyrimidin-4-yl)(cyclopropylmethyl)amino)pyrrolidine-1-carboxylate (450 mg, 70.92%) as a yellow solid. LCMS Rt=0.789 min, m/z=578.3 [M+H]+.

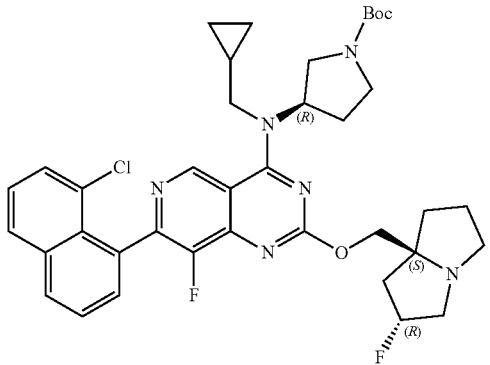

Step 4: (R)-tert-butyl 3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(cyclopropylmethyl)amino)pyrrolidine-1-carboxylate The Suzuki reaction was prepared in a similar fashion to Method #2, Step 5. The residue was purified by column chromatography (silica gel, 100-200 mesh, 90-100% ethyl acetate in petroleum ether) affording (R)-tert-butyl 3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(cyclopropylmethyl)amino)pyrrolidine-1-carboxylate (300 mg, 61.58%) as a yellow solid.

LCMS Rt=0.742 min, m/z=704.3 [M+H]+.

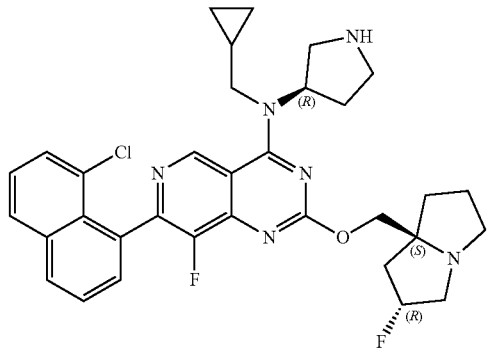

Step 5: 7-(8-chloronaphthalen-1-yl)-N-(cyclopropylmethyl)-8-fluoro-2-(((2R,7aS)-2-fluorohexahydro-1H-pyrrolizin-7a-yl)methoxy)-N—((R)-pyrrolidin-3-yl)pyrido[4,3-d]pyrimidin-4-amine Deprotection of the Boc group was prepared in a similar fashion to Method #2, Step 6. The residue was concentrated in vacuo affording 7-(8-chloronaphthalen-1-yl)-N-(cyclopropylmethyl)-8-fluoro-2-(((2R,7aS)-2-fluorohexahydro-1H-pyrrolizin-7a-yl)methoxy)-N—((R)-pyrrolidin-3-yl)pyrido[4,3-d]pyrimidin-4-amine (100 mg, crude, trifluoroacetate salt) as a brown oil, which was used in the next step without further purification. LCMS Rt=0.591 min, m/z=604.2 [M+H]+.

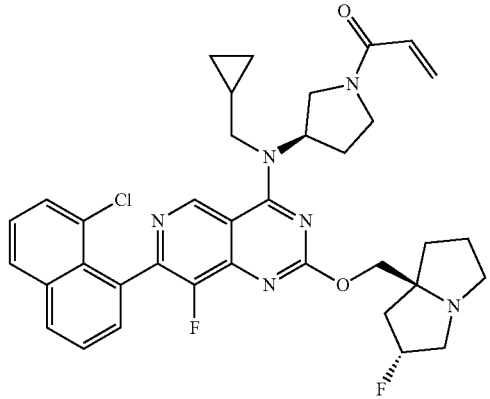 [SMILES: C=CC(=O)N1CC[C@@H](N(CC2CC2)c2nc(OC[C@@]34CCCN3C[C@H](F)C4)nc3c(F)c(-c4cccc5cccc(Cl)c45)ncc23)C1]

Step 6: 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(cyclopropylmethyl)amino)pyrrolidin-1-yl)prop-2-en-1-one The amide coupling reaction was prepared in a similar fashion to Method #2, Step 7.

The crude product was purified by reverse phase HPLC (column: Waters Xbridge Prep OBD C18 150*40 mm*10 μm; mobile phase: [water(NH₄HCO₃)-ACN]; B %: 40%-80%, 8 min) affording 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(cyclopropylmethyl)amino)pyrrolidin-1-yl)prop-2-en-1-one (16.98 mg, 18.13%) as a white solid: ¹H NMR (400 MHz, Chloroform-d) δ 9.29-9.14 (m, 1H), 8.01 (br d, J=7.6 Hz, 1H), 7.89 (br d, J=8.1 Hz, 1H), 7.67-7.50 (m, 3H), 7.47-7.38 (m, 1H), 6.54-6.36 (m, 2H), 5.79-5.66 (m, 1H), 5.43-5.16 (m, 1H), 5.15-4.99 (m, 1H), 4.10 (s, 3H), 4.05-3.86 (m, 1H), 3.55 (br s, 4H), 3.36-3.10 (m, 3H), 3.06-2.90 (m, 1H), 2.54-2.35 (m, 2H), 2.32-2.08 (m, 3H), 2.03-1.81 (m, 3H), 1.24-1.17 (m, 1H), 0.76-0.64 (m, 2H), 0.36-0.21 (m, 2H).

LCMS (5% to 95% acetonitrile in water+0.03% ammonium bicarbonate over 6 min); retention time 3.010 min, ESI+ found [M+H]=658.3

The amide coupling reaction was prepared in a similar fashion to Method #2, Step 7. The crude product was purified by reverse phase prep-HPLC (column: Waters Xbridge Prep OBD C18 150*40 mm*10 um; mobile phase: [water(NH₄HCO₃)-ACN]; B %: 40%-70%, 8 min) affording (E)-1-((R)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-isopropyl-1,2,4-oxadiazol-5-yl)prop-2-en-1-one (77.96 mg, 38.47%) as a white solid: ¹H NMR (400 MHz, Acetonitrile-d3) δ 9.22 (d, J=1.5 Hz, 1H), 8.14-8.07 (m, 1H), 7.89 (ddd, J=1.6, 5.1, 9.2 Hz, 1H), 7.68 (br d, J=5.8 Hz, 2H), 7.57-7.48 (m, 1H), 7.45-7.32 (m, 2H), 5.47-5.13 (m, 2H), 4.25-4.18 (m, 1H), 4.17-4.10 (m, 1H), 4.06-3.96 (m, 1H), 3.94-3.71 (m, 2H), 3.68-3.46 (m, 1H), 3.44 (s, 3H), 3.18-3.04 (m, 4H), 2.95-2.82 (m, 1H), 2.46-2.30 (m, 2H), 2.24-2.12 (m, 3H), 2.07-1.99 (m, 1H), 1.85 (br dd, J=4.6, 7.6 Hz, 2H), 1.32 (dd, J=7.1, 7.7 Hz, 6H).

LCMS (5% to 95% acetonitrile in water+0.03% ammonium bicarbonate over 6 min); retention time 3.092 min, ESI+ found [M+H]=730.3.

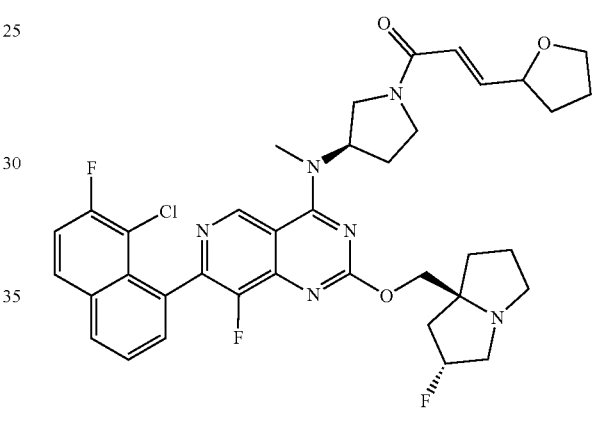

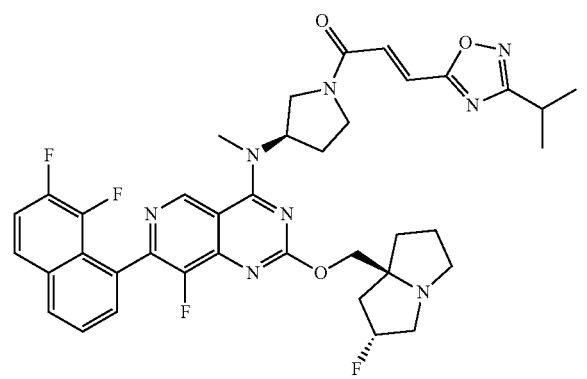 [SMILES: CC(C)c1noc(/C=C/C(=O)N2CC[C@@H](N(C)c3nc(OC[C@@]45CCCN4C[C@H](F)C5)nc4c(F)c(-c5cccc6ccc(F)c(F)c56)ncc34)C2)n1]

Step 1: (E)-1-((R)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(3-isopropyl-1,2,4-oxadiazol-5-yl)prop-2-en-1-one

Example 252 (Method 8): (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(tetrahydrofuran-2-yl)prop-2-en-1-one

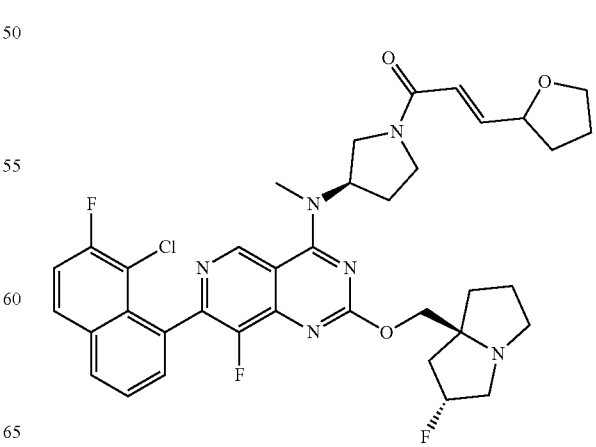

Step 1: (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(tetrahydrofuran-2-yl)prop-2-en-1-one The HWE reaction was prepared in a similar fashion to Method #8, Step 4. The residue was purified by reverse phase HPLC (column: Phenomenex Luna C18 100*40 mm*3 μm; mobile phase: [water(FA)-ACN]; B %: 1%-50%, 8 min) affording (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(tetrahydrofuran-2-yl)prop-2-en-1-one (1 mg, 1.00%, formate salt) as a yellow oil: $^1$H NMR (400 MHz, Acetonitrile-d3) δ 9.21 (d, J=2.0 Hz, 1H), 8.19-8.14 (m, 1H), 8.10 (dd, J=5.7, 9.1 Hz, 1H), 7.75-7.67 (m, 2H), 7.55 (t, J=8.9 Hz, 1H), 6.78 (dd, J=5.3, 15.1 Hz, 1H), 6.48-6.34 (m, 1H), 5.45-5.20 (m, 2H), 4.50 (br t, J=6.5 Hz, 1H), 4.28-4.22 (m, 1H), 4.20-4.15 (m, 1H), 4.13-4.05 (m, 1H), 3.88 (br s, 2H), 3.83-3.77 (m, 2H), 3.68-3.59 (m, 1H), 3.45 (s, 3H), 3.22-3.15 (m, 2H), 3.11 (s, 1H), 2.97-2.90 (m, 1H), 2.12-2.07 (m, 4H), 1.92-1.84 (m, 6H), 1.80 (td, J=2.5, 5.0 Hz, 2H).

LCMS (5% to 95% acetonitrile in water+0.1% trifluoroacetic acid over 6 min); retention time 2.228 min, ESI+ found [M+H]=706.3.

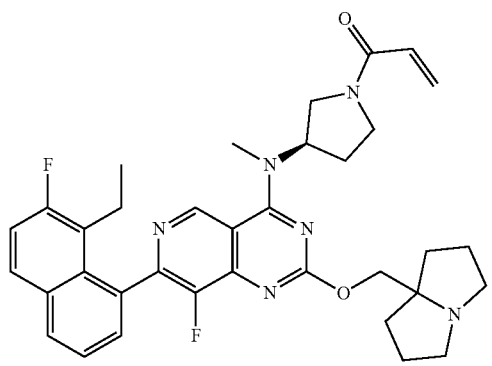 [SMILES: C=CC(=O)N1CC[C@@H](N(C)c2nc(OCC34CCCN3CCC4)nc3c(F)c(-c4cccc5ccc(F)c(CC)c45)ncc23)C1]

Example 253 (Method 2): (R)-1-(3-((7-(8-ethyl-7-fluoronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)prop-2-en-1-one

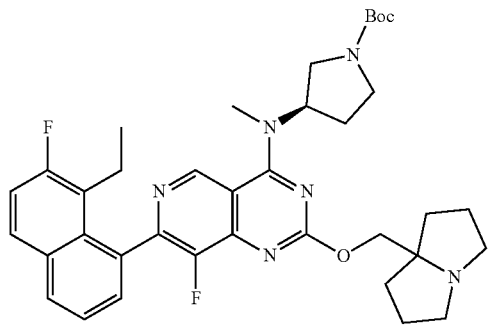 [SMILES: CCc1c(F)ccc2cccc(-c3ncc4c(N(C)[C@@H]5CCN(C(=O)OC(C)(C)C)C5)nc(OCC56CCCN5CCC6)nc4c3F)c12]

Step 1: tert-butyl (R)-3-((7-(8-ethyl-7-fluoronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidine-1-carboxylate The Suzuki reaction was prepared in a similar fashion to Method #2, Step 5. The residue was purified by reverse phase HPLC (column: Phenomenex Luna C18 250*50 mm*10 μm; mobile phase: [water(TFA)-ACN]; B %: 20%-50%, 10 min) affording tert-butyl (R)-3-((7-(8-ethyl-7-fluoronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidine-1-carboxylate (350 mg, 55.36%) as a yellow solid.
LCMS Rt=1.742 min, m/z=658.3 [M+H]$^+$.

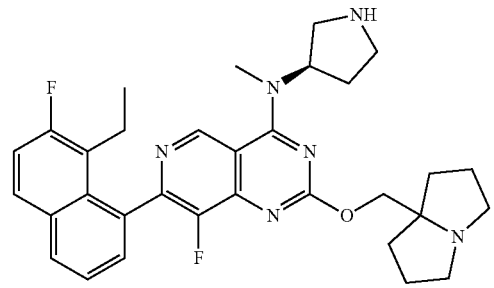 [SMILES: CCc1c(F)ccc2cccc(-c3ncc4c(N(C)[C@@H]5CCNC5)nc(OCC56CCCN5CCC6)nc4c3F)c12]

Step 2: (R)-7-(8-ethyl-7-fluoronaphthalen-1-yl)-8-fluoro-N-methyl-N-(pyrrolidin-3-yl)-2-((tetrahydro-1H-pyrrolizin-7a(5H)-yl)methoxy)pyrido[4,3-d]pyrimidin-4-amine The deprotection of the Boc group was prepared in a similar fashion to Method #2, Step 6. The reaction mixture was concentrated in vacuo affording (R)-7-(8-ethyl-7-fluoronaphthalen-1-yl)-8-fluoro-N-methyl-N-(pyrrolidin-3-yl)-2-((tetrahydro-1H-pyrrolizin-7a(5H)-yl)methoxy)pyrido[4,3-d]pyrimidin-4-amine (200 mg, crude, trifluoroacetate salt) as a white solid, which was used in the next step without further purification. LCMS Rt=0.541 min, m/z=558.3 [M+H]$^+$.

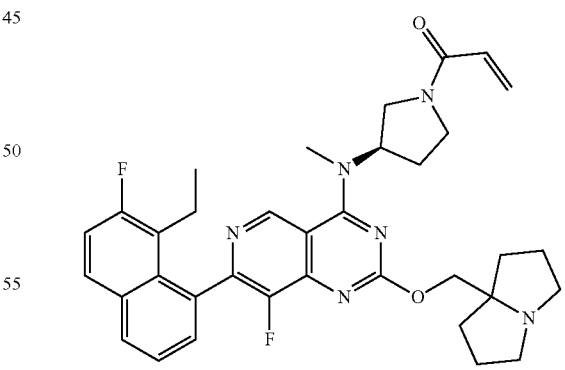

Step 3: (R)-1-(3-((7-(8-ethyl-7-fluoronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)prop-2-en-1-one The amide coupling reaction was prepared in a similar fashion to Method #2, Step 7. The residue was purified by prep-HPLC (column: Waters Xbridge Prep OBD C18 150*40 mm*10 um; mobile phase: [water(NH₄HCO₃)-ACN]; B %: 25%-55%, 8 min) affording (R)-1-(3-(((7-(8-ethyl-7-fluoronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)prop-2-en-1-one (60.44 mg, 89.84%) as a pale yellow amorphous solid: ¹H NMR (400 MHz, Acetonitrile-d3) δ 9.19 (d, J=1.0 Hz, 1H), 8.05 (dd, J=1.1, 8.2 Hz, 1H), 7.93 (dd, J=6.1, 9.0 Hz, 1H), 7.58-7.52 (m, 1H), 7.51-7.46 (m, 1H), 7.38 (t, J=9.4 Hz, 1H), 6.65-6.52 (m, 1H), 6.24 (td, J=2.5, 16.9 Hz, 1H), 5.67 (ddd, J=2.2, 6.2, 10.3 Hz, 1H), 5.46-5.31 (m, 1H), 4.15 (s, 2H), 4.10-3.92 (m, 1H), 3.89-3.79 (m, 1H), 3.68-3.54 (m, 1H), 3.42 (s, 3H), 3.01-2.92 (m, 2H), 2.59 (td, J=6.8, 10.0 Hz, 2H), 2.53-2.45 (m, 1H), 2.43-2.34 (m, 1H), 2.31-2.27 (m, 1H), 2.10 (br d, J=2.5 Hz, 2H), 1.99-1.95 (m, 1H), 1.91 (br s, 1H), 1.87-1.75 (m, 4H), 1.67-1.57 (m, 2H), 0.81 (br t, J=7.4 Hz, 3H).

LCMS (5% to 95% acetonitrile in water+0.03% ammonium bicarbonate over 6 min); retention time 2.873 min, ESI+ found [M+H]=612.3.

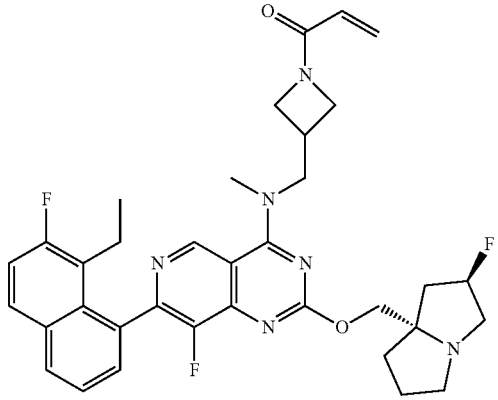 [SMILES: C=CC(=O)N1CC(CN(C)c2nc(OC[C@@]34CCCN3C[C@H](F)C4)nc3c(F)c(-c4cccc5ccc(F)c(CC)c45)ncc23)C1]

Example 254 (Method 2): 1-(3-(((7-(8-ethyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)methyl)azetidin-1-yl)prop-2-en-1-one

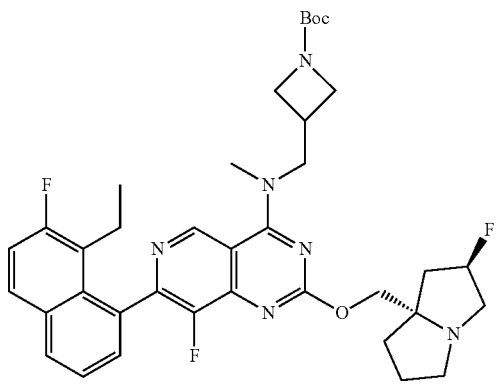 [SMILES: CCc1c(F)ccc2cccc(-c3ncc4c(N(C)CC5CN(C(=O)OC(C)(C)C)C5)nc(OC[C@@]56CCCN5C[C@H](F)C6)nc4c3F)c12]

Step 1: tert-butyl 3-(((7-(8-ethyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)methyl)azetidine-1-carboxylate The Suzuki reaction was prepared in a similar fashion to Method #2, Step 5. The residue was purified by reverse phase HPLC (column: Phenomenex Luna C18 250*50 mm*10 μm; mobile phase: [water(TFA)-ACN]; B %: 25%-55%, 10 min) affording tert-butyl 3-(((7-(8-ethyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)methyl)azetidine-1-carboxylate (300 mg, 40.90%) as yellow solid. LCMS Rt=1.495 min, m/z=676.3 [M+H]⁺.

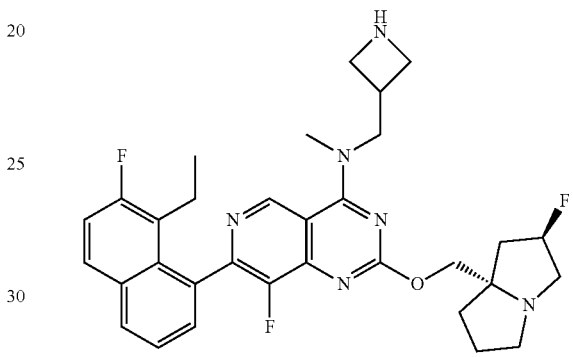

Step 2: N-(azetidin-3-ylmethyl)-7-(8-ethyl-7-fluoronaphthalen-1-yl)-8-fluoro-2-(((2R,7aS)-2-fluorohexahydro-1H-pyrrolizin-7a-yl)methoxy)-N-methylpyrido[4,3-d]pyrimidin-4-amine The deprotection of the Boc group was prepared in a similar fashion to Method #2, Step 6. The mixture was concentrated in vacuo affording N-(azetidin-3-ylmethyl)-7-(8-ethyl-7-fluoronaphthalen-1-yl)-8-fluoro-2-(((2R,7aS)-2-fluorohexahydro-1H-pyrrolizin-7a-yl)methoxy)-N-methylpyrido[4,3-d]pyrimidin-4-amine (150 mg, crude, trifluoroacetate salt), which was used in the next step without further purification. LCMS Rt=0.564 min, m/z=576.3 [M+H]⁺.

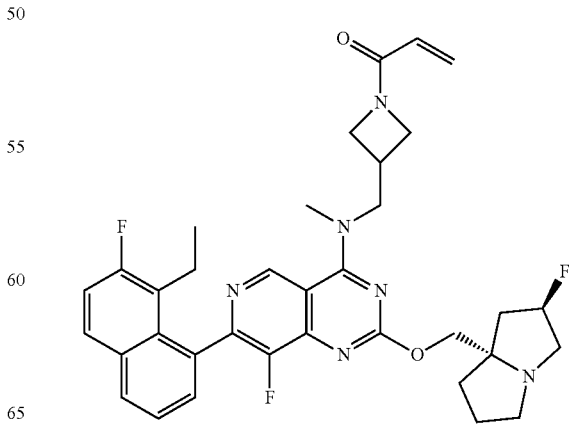

Step 3: 1-(3-(((7-(8-ethyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)methyl)azetidin-1-yl)prop-2-en-1-one The amide coupling reaction was prepared in a similar fashion to Method #2, Step 7. The residue was purified by reverse phase HPLC (column: Waters Xbridge Prep OBD C18 150*40 mm*10 μm; mobile phase: [water(NH$_4$HCO$_3$)-ACN]; B %: 35%-65%, 8 min) affording 1-(3-(((7-(8-ethyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)methyl)azetidin-1-yl)prop-2-en-1-one (34.89 mg, 27.26%) as a yellow amorphous solid: $^1$H NMR (400 MHz, Acetonitrile-d3) δ 9.23 (s, 1H), 8.05 (dd, J=1.3, 8.1 Hz, 1H), 7.93 (dd, J=6.1, 9.0 Hz, 1H), 7.58-7.52 (m, 1H), 7.50-7.44 (m, 1H), 7.38 (t, J=9.4 Hz, 1H), 6.33-6.24 (m, 1H), 6.21-6.12 (m, 1H), 5.64 (dd, J=2.3, 10.1 Hz, 1H), 5.35-5.16 (m, 1H), 4.35 (t, J=8.6 Hz, 1H), 4.26-4.06 (m, 6H), 3.86 (dt, J=5.6, 9.8 Hz, 1H), 3.57 (s, 3H), 3.25-3.17 (m, 1H), 3.17-3.10 (m, 2H), 3.10-3.04 (m, 1H), 2.93-2.84 (m, 1H), 2.55-2.43 (m, 1H), 2.34-2.28 (m, 1H), 2.20-2.15 (m, 1H), 2.14-2.07 (m, 1H), 2.06-1.98 (m, 1H), 1.92-1.76 (m, 3H), 0.81 (t, J=7.4 Hz, 3H).

LCMS (5% to 95% acetonitrile in water+0.03% ammonium bicarbonate over 6 min); retention time 3.058 min, ESI+ found [M+H]=630.3.

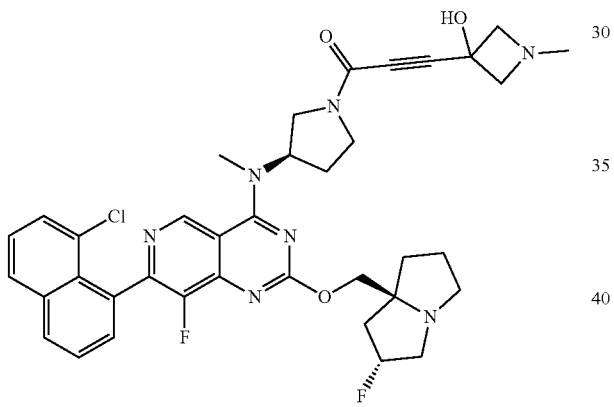

Example 255 (Method 7): 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-hydroxy-1-methylazetidin-3-yl)prop-2-yn-1-one

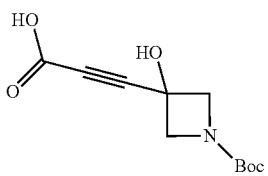 [SMILES: CC(C)(C)OC(=O)N1CC(O)(C#CC(=O)O)C1]

Step 1: 3-(1-tert-butoxycarbonyl-3-hydroxy-azetidin-3-yl)prop-2-ynoic acid

The carbonylation reaction was prepared in a similar fashion to Method #7, Step 1. The aqueous layer was concentrated in vacuo affording 3-(1-tert-butoxycarbonyl-3-hydroxy-azetidin-3-yl)prop-2-ynoic acid (373 mg, crude), which was used in the next step without further purification.

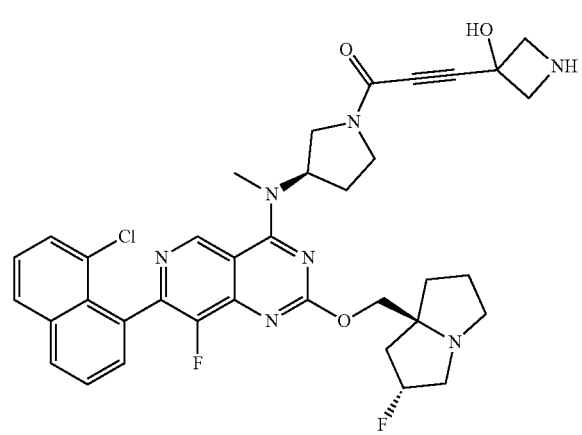 [SMILES: CN(c1nc(OC[C@@]23CCCN2C[C@H](F)C3)nc2c(F)c(-c3cccc4cccc(Cl)c34)ncc12)[C@@H]1CCN(C(=O)C#CC2(O)CNC2)C1]

Step 2: tert-butyl 3-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)-3-hydroxyazetidine-1-carboxylate The amide coupling reaction was prepared in a similar fashion to Method #7, Step 2. The residue was purified by column chromatography (silica gel, 100-200 mesh, 80-100% ethyl acetate in petroleum ether) affording tert-butyl 3-(3-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-oxoprop-1-yn-1-yl)-3-hydroxyazetidine-1-carboxylate (56 mg, 50%) as a yellow solid. LCMS Rt=0.734 min, m/z=787.3 [M+H]$^+$.

Step 3: 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-hydroxyazetidin-3-yl)prop-2-yn-1-one The deprotection of the Boc group was prepared in a similar fashion to Method #7, Step 3. The mixture was concentrated in vacuo affording 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-hydroxyazetidin-3-yl)prop-2-yn-1-one (65 mg, crude, trifluoroacetate salt) as a yellow oil, which was used in the next step without any further purification. LCMS Rt=0.530 min, m/z=687.3 [M+H]+.

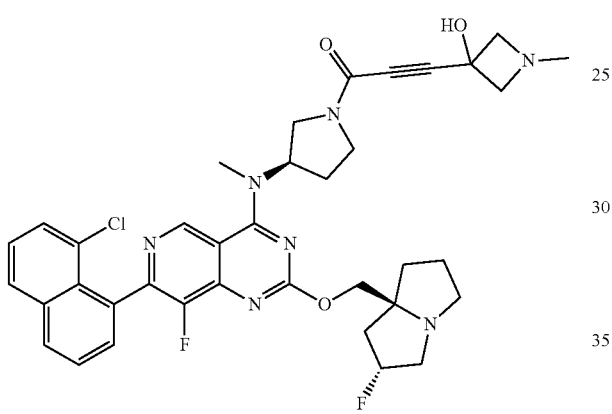

Step 4: 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-hydroxy-1-methylazetidin-3-yl)prop-2-yn-1-one The reductive amination was prepared in a similar fashion to Method #7, Step 4. The residue was purified by reverse phase HPLC (column: Waters Xbridge BEH C18 100*30 mm*10 μm; mobile phase: [water(NH4HCO3)-ACN]; B %: 20%-50%, 8 min) affording 1-((R)-3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(3-hydroxy-1-methylazetidin-3-yl)prop-2-yn-1-one (14.69 mg, 27.72%) as a pale yellow amorphous solid: $^1$H NMR (400 MHz, Chloroform-d) δ 9.19-9.12 (m, 1H), 8.05-7.98 (m, 1H), 7.89 (d, J=8.4 Hz, 1H), 7.70-7.49 (m, 3H), 7.49-7.38 (m, 1H), 5.51-5.33 (m, 1H), 5.31-5.08 (m, 1H), 4.56-4.41 (m, 1H), 4.40-4.14 (m, 2H), 4.13-3.98 (m, 1H), 3.90-3.73 (m, 1H), 3.69 (br t, J=7.1 Hz, 1H), 3.66-3.53 (m, 2H), 3.53-3.48 (m, 3H), 3.45 (s, 1H), 3.38-3.19 (m, 3H), 3.12-2.92 (m, 1H), 2.43-2.38 (m, 3H), 2.36-2.25 (m, 2H), 2.24-2.09 (m, 2H), 2.07-1.75 (m, 6H).

LCMS (5% to 95% acetonitrile in water+0.03% ammonium bicarbonate over 6 min); retention time 2.635 min, ESI+ found [M+H]=701.3.

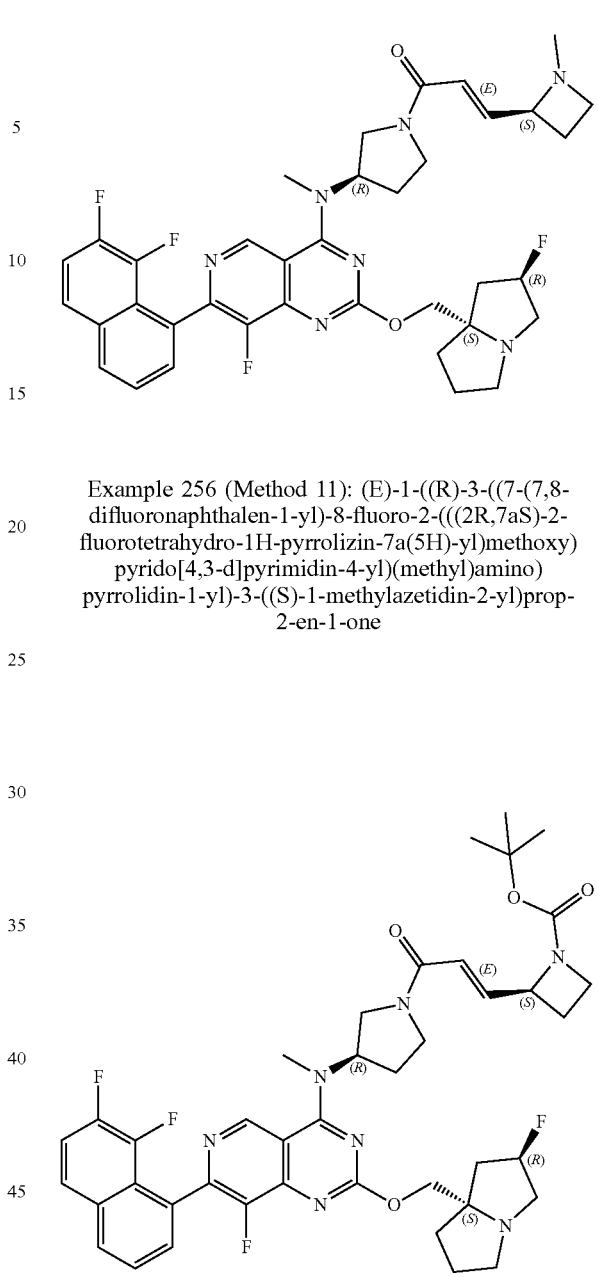

Example 256 (Method 11): (E)-1-((R)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((S)-1-methylazetidin-2-yl)prop-2-en-1-one

Step 1: tert-butyl (S)-2-((E)-3-((R)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-oxoprop-1-en-1-yl)azetidine-1-carboxylate The amide coupling reaction was prepared in a similar fashion to Method #11, Step 11. The crude product was concentrated in vacuo affording tert-butyl (S)-2-((E)-3-((R)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-oxoprop-1-en-1-yl)azetidine-1-carboxylate (400 mg, crude) as a yellow oil. LCMS Rt=0.682 min, m/z=775.4 [M+H]+.

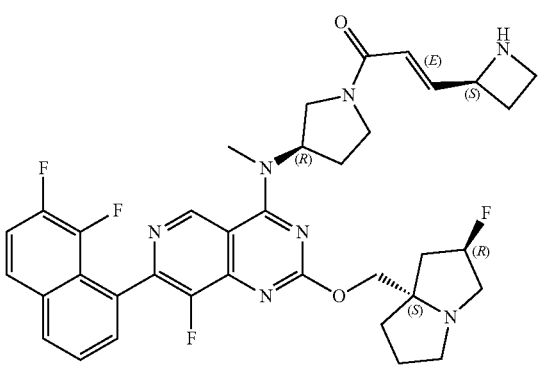

Step 2: (E)-3-((S)-azetidin-2-yl)-1-((R)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one The deprotection of the Boc group was prepared in a similar fashion to Method #11, Step 12. The crude product was concentrated in vacuo affording (E)-3-((S)-azetidin-2-yl)-1-((R)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (400 mg, crude) as a yellow oil, which was used in the next step without any further purification. LCMS Rt =0.541 min, m/z=675.3 [M+H]$^+$.

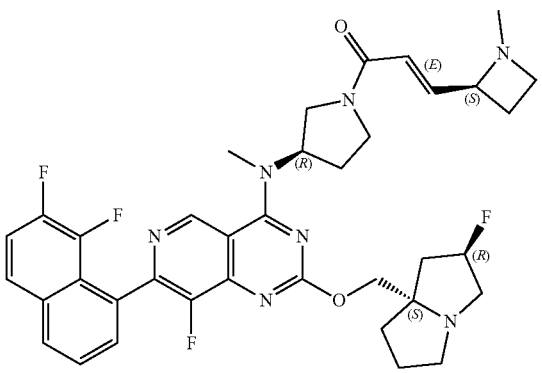

Step 3: (E)-1-((R)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((S)-1-methylazetidin-2-yl)prop-2-en-1-one The reductive amination was prepared in a similar fashion to Method #11, Step 13. The residue was purified by reverse phase HPLC (column: Waters Xbridge BEH C18 250*50 mm*10 µm; mobile phase: [water(NH$_4$HCO$_3$)-ACN]; B %: 30%-50%, 10 min) affording (E)-1-((R)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((S)-1-methylazetidin-2-yl)prop-2-en-1-one (37.05 mg, 10.53%) as a yellow solid: $^1$H NMR (400 MHz, Acetonitrile-d3) δ 9.25 (d, J=3.4 Hz, 1H), 8.18-8.09 (m, 1H), 7.97-7.88 (m, 1H), 7.71 (br d, J=5.6 Hz, 2H), 7.60-7.51 (m, 1H), 6.87-6.72 (m, 1H), 6.49-6.35 (m, 1H), 5.46-5.19 (m, 2H), 4.29-4.15 (m, 2H), 4.12-3.81 (m, 2H), 3.79-3.53 (m, 3H), 3.46 (d, J=5.4 Hz, 4H), 3.38-3.28 (m, 1H), 3.20-3.16 (m, 1H), 3.14-3.08 (m, 1H), 2.98-2.79 (m, 2H), 2.49-2.35 (m, 1H), 2.34-2.26 (m, 4H), 2.12-2.07 (m, 2H), 1.91-1.83 (m, 4H), 1.80 (td, J=2.5, 5.0 Hz, 2H).

LCMS (5% to 95% acetonitrile in water+0.03% ammonium bicarbonate over 6 min); retention time 2.935 min, ESI+ found [M+H]=689.3.

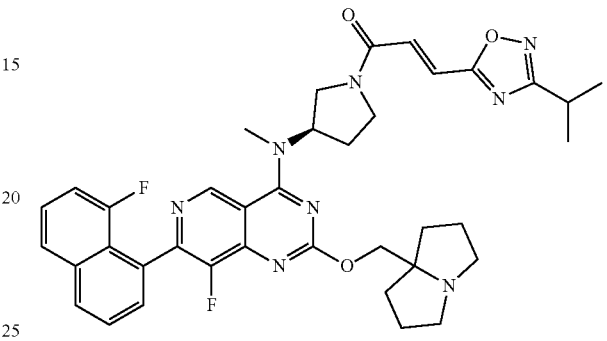

Example 257 (Method 2): (R,E)-1-(3-((8-fluoro-7-(8-fluoronaphthalen-1-yl)-2-((tetrahydro-1H-pyrrolizin-7a(5H)-yl)methoxy)pyrido[4,3-d]pyrimidin-4-yl)(methyl)amino)pyrrolidin-1-yl)-3-(3-isopropyl-1,2,4-oxadiazol-5-yl)prop-2-en-1-one

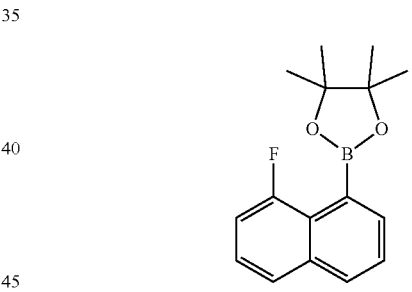

Step 1: 2-(8-fluoronaphthalen-1-yl)-4,4,5,5-tetramethyl-1,3,2-dioxaborolane

To a solution of 1-bromo-8-fluoro-naphthalene (1 g, 4.44 mmol) in tetrahydrofuran (20 mL) was added n-butyllithium (2.5 M, 2.67 mL) under a nitrogen atmosphere. The reaction was stirred at −78° C. for 0.5 h. A mixture of 2-isopropoxy-4,4,5,5-tetramethyl-1,3,2-dioxaborolane (2.48 g, 13.33 mmol) in tetrahydrofuran (10 mL) was added, and the mixture was stirred at −78° C. for 0.5 h. The reaction mixture was quenched with saturated sodium bicarbonate (30 mL) at 0° C. and extracted with dichloromethane (3×100 mL). The combined organic layers were dried over sodium sulphate and concentrated in vacuo affording 2-(8-fluoronaphthalen-1-yl)-4,4,5,5-tetramethyl-1,3,2-dioxaborolane (1.2 g, 99.25%) as a white solid: $^1$H NMR (400 MHz, Chloroform-d) δ 7.82-7.75 (m, 1H), 7.60-7.52 (m, 2H), 7.42 (dd, J=6.9, 8.2 Hz, 1H), 7.31 (dt, J=5.4, 7.9 Hz, 1H), 7.08 (ddd, J=0.8, 7.7, 11.4 Hz, 1H), 1.37 (s, 12H).

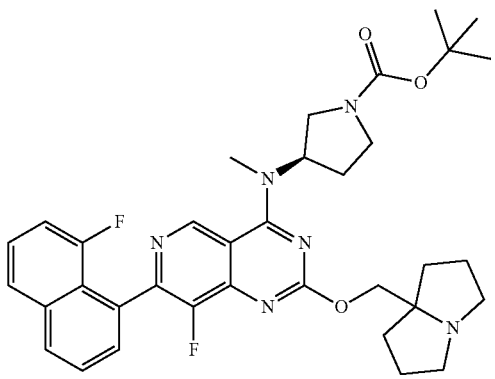 [SMILES: CN(c1nc(OCC23CCCN2CCC3)nc2c(F)c(-c3cccc4cccc(F)c34)ncc12)[C@@H]1CCN(C(=O)OC(C)(C)C)C1]

Step 2: tert-butyl (R)-3-((8-fluoro-7-(8-fluoronaphthalen-1-yl)-2-((tetrahydro-1H-pyrrolizin-7a(5H)-yl)methoxy)pyrido[4,3-d]pyrimidin-4-yl)(methyl)amino)pyrrolidine-1-carboxylate The Suzuki reaction was prepared in a similar fashion to Method #2, Step 5. The crude residue was purified by reverse phase prep-HPLC (column: Phenomenex Luna C18 250*50 mm*10 μm; mobile phase: [water(TFA)-ACN]; B %: 20%-50%, 10 min) affording tert-butyl (R)-3-((8-fluoro-7-(8-fluoronaphthalen-1-yl)-2-((tetrahydro-1H-pyrrolizin-7a(5H)-yl)methoxy)pyrido[4,3-d]pyrimidin-4-yl)(methyl)amino)pyrrolidine-1-carboxylate (560 mg, 78.36%, trifluoroacetate salt) as a yellow solid. LCMS Rt=1.400 min, m/z=630.3 [M+H]+.

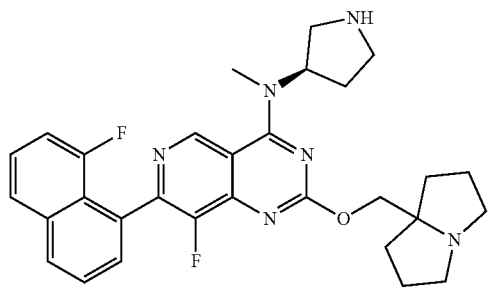 [SMILES: CN(c1nc(OCC23CCCN2CCC3)nc2c(F)c(-c3cccc4cccc(F)c34)ncc12)[C@@H]1CCNC1]

Step 3: (R)-8-fluoro-7-(8-fluoronaphthalen-1-yl)-N-methyl-N-(pyrrolidin-3-yl)-2-((tetrahydro-1H-pyrrolizin-7a(5H)-yl)methoxy)pyrido[4,3-d]pyrimidin-4-amine The deprotection of the Boc group was prepared in a similar fashion to Method #1, Step 9. The reaction mixture was concentrated in vacuo affording (R)-8-fluoro-7-(8-fluoronaphthalen-1-yl)-N-methyl-N-(pyrrolidin-3-yl)-2-((tetrahydro-1H-pyrrolizin-7a(5H)-yl)methoxy)pyrido[4,3-d]pyrimidin-4-amine (160 mg, crude, hydrochloric acid salt) as a yellow oil, which was used in the next step without further purification. LCMS Rt=0.497 min, m/z=530.3 [M+H]+.

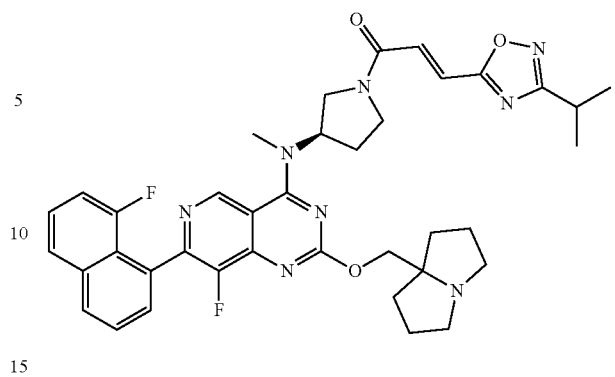

Step 4: (R,E)-1-(3-((8-fluoro-7-(8-fluoronaphthalen-1-yl)-2-((tetrahydro-1H-pyrrolizin-7a(5H)-yl)methoxy)pyrido[4,3-d]pyrimidin-4-yl)(methyl)amino)pyrrolidin-1-yl)-3-(3-isopropyl-1,2,4-oxadiazol-5-yl)prop-2-en-1-one The amide coupling reaction was prepared in a similar fashion to Method #2, Step 7. The crude product was purified by reverse phase prep-HPLC (column: Waters Xbridge Prep OBD C18 150*40 mm*10 μm; mobile phase: [water(NH4HCO3)-ACN]; B %: 30%-60%, 8 min) affording (R,E)-1-(3-((8-fluoro-7-(8-fluoronaphthalen-1-yl)-2-((tetrahydro-1H-pyrrolizin-7a(5H)-yl)methoxy)pyrido[4,3-d]pyrimidin-4-yl)(methyl)amino)pyrrolidin-1-yl)-3-(3-isopropyl-1,2,4-oxadiazol-5-yl)prop-2-en-1-one (92.8 mg, 48.89%) as a yellow amorphous solid: 1H NMR (400 MHz, Acetonitrile-d3) δ 9.23 (s, 1H), 8.13 (br d, J=8.3 Hz, 1H), 7.89 (d, J=8.3 Hz, 1H), 7.76-7.70 (m, 1H), 7.68-7.62 (m, 1H), 7.56 (dt, J=5.0, 7.9 Hz, 1H), 7.51-7.33 (m, 2H), 7.24 (dd, J=7.7, 13.2 Hz, 1H), 5.50-5.32 (m, 1H), 4.27-4.07 (m, 3H), 4.06-3.98 (m, 1H), 3.90 (spt, J=6.1 Hz, 1H), 3.84-3.74 (m, 1H), 3.68-3.48 (m, 1H), 3.45 (s, 3H), 3.21-3.08 (m, 1H), 3.03-2.92 (m, 2H), 2.66-2.54 (m, 2H), 2.49-2.40 (m, 1H), 2.39-2.29 (m, 1H), 2.19-2.09 (m, 1H), 1.88-1.78 (m, 4H), 1.69-1.58 (m, 2H), 1.34 (dd, J=7.0, 8.8 Hz, 6H).

LCMS (5% to 95% acetonitrile in water+0.03% ammonium bicarbonate over 6 min); retention time 2.980 min, ESI+ found [M+H]=694.3.

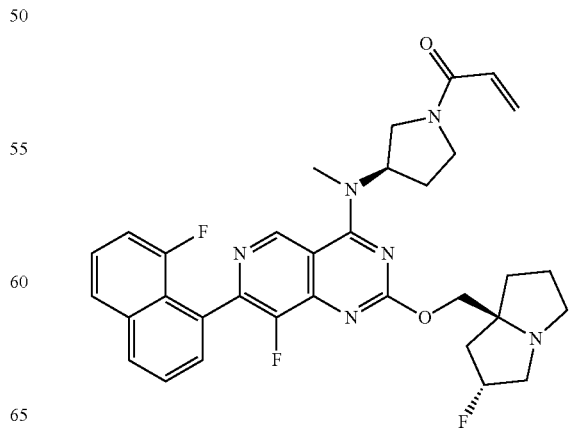

Example 258 (Method 2): 1-((R)-3-((8-fluoro-7-(8-fluoronaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one Step 1: tert-butyl (R)-3-((8-fluoro-7-(8-fluoronaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidine-1-carboxylate

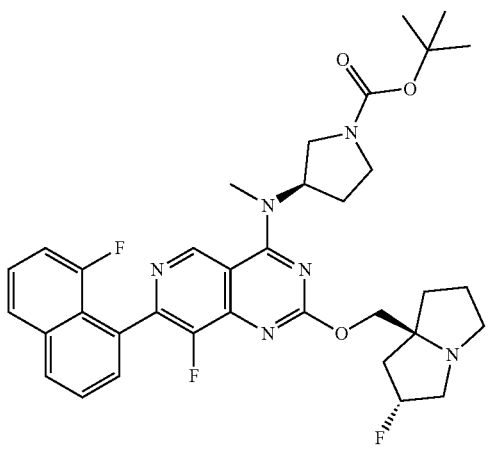 [SMILES: CN(c1nc(OC[C@@]23CCCN2C[C@H](F)C3)nc2c(F)c(-c3cccc4cccc(F)c34)ncc12)[C@@H]1CCN(C(=O)OC(C)(C)C)C1]

The Suzuki reaction was prepared in a similar fashion to Method #2, Step 5. The crude residue was purified by reverse phase prep-HPLC (column: Phenomenex C18 80*30 mm*3 μm; mobile phase: [water(TFA)-ACN]; B %: 15%-45%, 8 min) affording tert-butyl (R)-3-((8-fluoro-7-(8-fluoronaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidine-1-carboxylate (150 mg, 53.00%, trifluoroacetate salt) as a white solid. LCMS Rt=1.431 min, m/z=648.3 [M+H]$^+$.

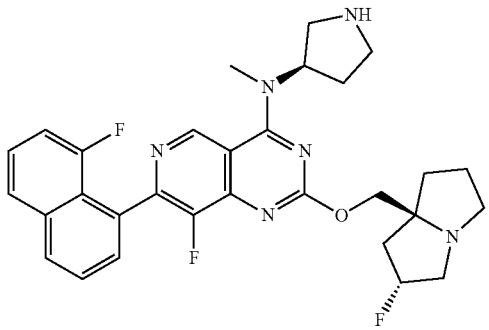 [SMILES: CN(c1nc(OC[C@@]23CCCN2C[C@H](F)C3)nc2c(F)c(-c3cccc4cccc(F)c34)ncc12)[C@@H]1CCNC1]

Step 2: 8-fluoro-7-(8-fluoronaphthalen-1-yl)-2-(((2R,7aS)-2-fluorotetrahydro-1H-pyrrolizin-7a(5H)-yl)methoxy)-N-methyl-N—((R)-pyrrolidin-3-yl)pyrido[4,3-d]pyrimidin-4-amine The deprotection of Boc group was prepared in a similar fashion to Method #1, Step 9. The reaction mixture was concentrated in vacuo affording 8-fluoro-7-(8-fluoronaphthalen-1-yl)-2-(((2R,7aS)-2-fluorotetrahydro-1H-pyrrolizin-7a(5H)-yl)methoxy)-N-methyl-N—((R)-pyrrolidin-3-yl)pyrido[4,3-d]pyrimidin-4-amine (60 mg, crude, trifluoroacetic salt) as a yellow oil, which was used in the next step without further purification. LCMS Rt=0.634 min, m/z=548.3 [M+H]$^+$.

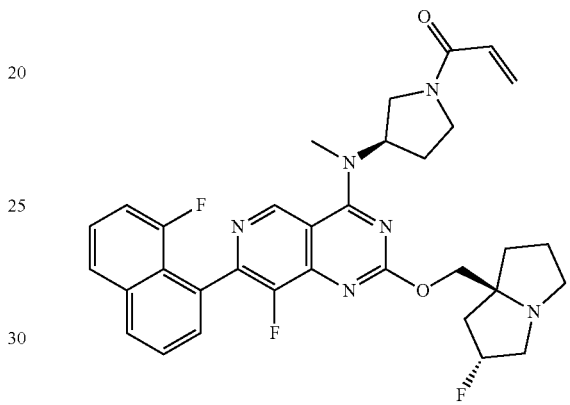

Step 3: 1-((R)-3-((8-fluoro-7-(8-fluoronaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one The amide coupling reaction was prepared in a similar fashion to Method #2, Step 7. The crude product was purified by reverse phase prep-HPLC (column: Waters Xbridge Prep OBD C18 150*40 mm*10 μm; mobile phase: [water(NH$_4$HCO$_3$)-ACN]; B %: 30%-60%, 8 min) affording 1-((R)-3-((8-fluoro-7-(8-fluoronaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (25.2 mg, 46.18%) as a yellow amorphous solid: $^1$H NMR (400 MHz, Acetonitrile-d3) δ 9.22 (s, 1H), 8.12 (br d, J=8.3 Hz, 1H), 7.88 (d, J=8.3 Hz, 1H), 7.76-7.68 (m, 1H), 7.68-7.61 (m, 1H), 7.56 (dt, J=5.1, 8.0 Hz, 1H), 7.23 (dd, J=7.2, 13.2 Hz, 1H), 6.68-6.52 (m, 1H), 6.31-6.21 (m, 1H), 5.74-5.65 (m, 1H), 5.45-5.18 (m, 2H), 4.26-4.19 (m, 1H), 4.17-4.11 (m, 1H), 4.11-3.94 (m, 1H), 3.94-3.79 (m, 1H), 3.72-3.62 (m, 1H), 3.62-3.45 (m, 1H), 3.43 (s, 3H), 3.22-3.12 (m, 2H), 3.12-3.06 (m, 1H), 2.96-2.87 (m, 1H), 2.46-2.35 (m, 1H), 2.35-2.26 (m, 1H), 2.20 (br d, J=6.6 Hz, 1H), 2.12 (d, J=3.1 Hz, 1H), 2.10-2.00 (m, 1H), 1.95-1.90 (m, 1H), 1.89-1.80 (m, 2H).

LCMS (5% to 95% acetonitrile in water+0.03% ammonium bicarbonate over 6 min); retention time 2.891 min, ESI+ found [M+H]=602.3.

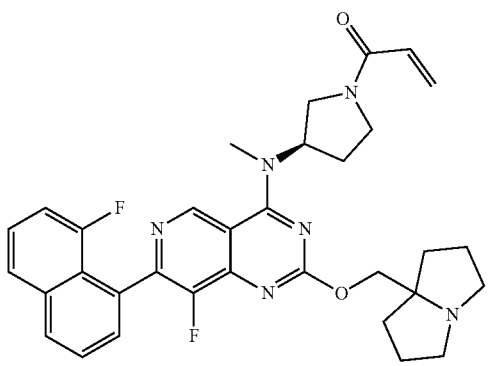 [SMILES: C=CC(=O)N1CC[C@@H](N(C)c2nc(OCC34CCCN3CCC4)nc3c(F)c(-c4cccc5cccc(F)c45)ncc23)C1]

Example 259 (Method 2): (R)-1-(3-((8-fluoro-7-(8-fluoronaphthalen-1-yl)-2-((tetrahydro-1H-pyrrolizin-7a(5H)-yl)methoxy)pyrido[4,3-d]pyrimidin-4-yl)(methyl)amino)pyrrolidin-1-yl)prop-2-en-1-one

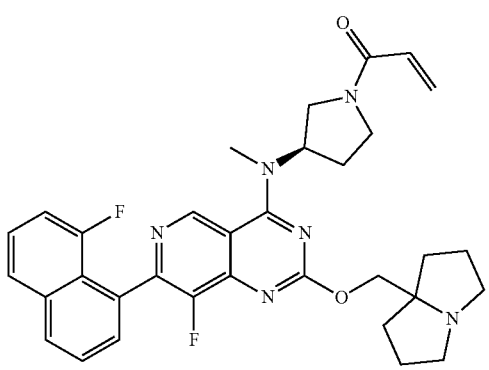 [SMILES: C=CC(=O)N1CC[C@@H](N(C)c2nc(OCC34CCCN3CCC4)nc3c(F)c(-c4cccc5cccc(F)c45)ncc23)C1]

Step 1: (R)-1-(3-((8-fluoro-7-(8-fluoronaphthalen-1-yl)-2-((tetrahydro-1H-pyrrolizin-7a(5H)-yl)methoxy)pyrido[4,3-d]pyrimidin-4-yl)(methyl)amino)pyrrolidin-1-yl)prop-2-en-1-one The amide coupling reaction was prepared in a similar fashion to Method #2, Step 7. The crude product was purified by reverse phase prep-HPLC (column: Waters Xbridge Prep OBD C18 150*40 mm*10 um; mobile phase: [water(NH$_4$HCO$_3$)-ACN]; B %: 25%-55%, 8 min) affording (R)-1-(3-((8-fluoro-7-(8-fluoronaphthalen-1-yl)-2-((tetrahydro-1H-pyrrolizin-7a(5H)-yl)methoxy)pyrido[4,3-d]pyrimidin-4-yl)(methyl)amino)pyrrolidin-1-yl)prop-2-en-1-one (4.3 mg, 7.86%) as a yellow amorphous solid: $^1$H NMR (400 MHz, Acetonitrile-d3) δ 9.26-9.20 (m, 1H), 8.14 (br d, J=8.5 Hz, 1H), 7.89 (d, J=8.3 Hz, 1H), 7.77-7.70 (m, 1H), 7.65 (t, J=6.3 Hz, 1H), 7.57 (dt, J=5.0, 7.9 Hz, 1H), 7.25 (dd, J=7.6, 13.3 Hz, 1H), 6.68-6.53 (m, 1H), 6.33-6.20 (m, 1H), 5.70 (ddd, J=2.2, 6.4, 10.3 Hz, 1H), 5.50-5.28 (m, 1H), 4.19 (s, 2H), 4.14-3.95 (m, 1H), 3.94-3.80 (m, 1H), 3.74-3.64 (m, 1H), 3.63-3.48 (m, 1H), 3.45 (s, 3H), 3.05-2.97 (m, 2H), 2.64 (td, J=6.7, 9.9 Hz, 2H), 2.46-2.37 (m, 1H), 2.35-2.30 (m, 1H), 2.02-1.99 (m, 2H), 1.91-1.87 (m, 1H), 1.87-1.83 (m, 2H), 1.82-1.78 (m, 1H), 1.70-1.62 (m, 2H).

LCMS (5% to 95% acetonitrile in water+0.03% ammonium bicarbonate over 6 min); retention time 2.627 min, ESI+ found [M+H]=584.3.

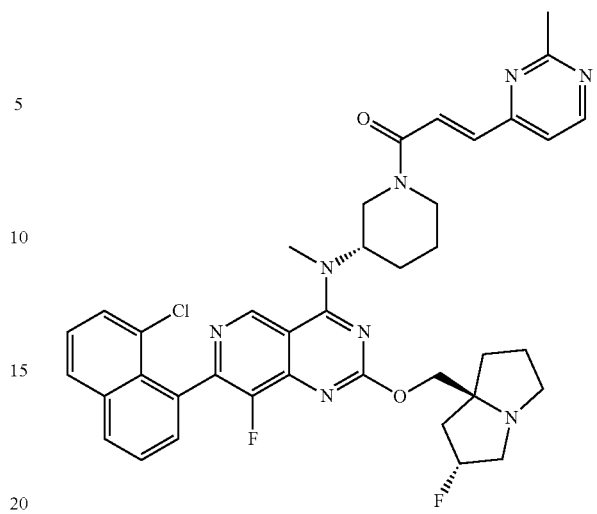

Example 260 (Method 1): (E)-1-((S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)piperidin-1-yl)-3-(2-methylpyrimidin-4-yl)prop-2-en-1-one

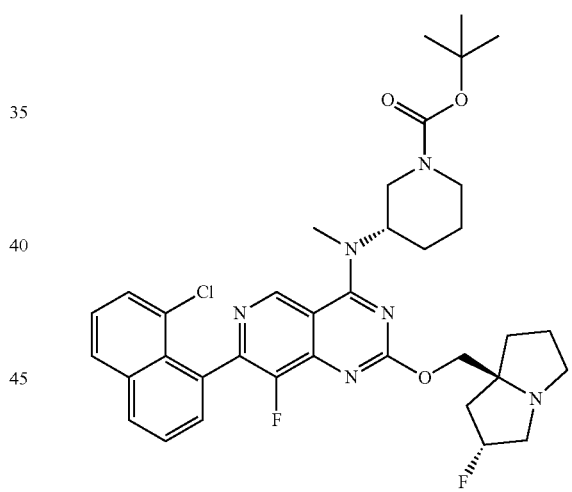

Step 1: tert-butyl (S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)piperidine-1-carboxylate The substitution reaction was prepared in a similar fashion to Method #1, Step 8. The resulting residue was purified by reverse phase HPLC (column: Phenomenex Luna 80*30 mm*3 μm; mobile phase: [water(TFA)-ACN]; B %: 15%-45%, 8 min) affording tert-butyl (S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)piperidine-1-carboxylate (90 mg, 26.05%, trifluoroacetate salt) as a white solid. LCMS Rt=0.729 min, m/z=678.3 [M+H]$^+$.

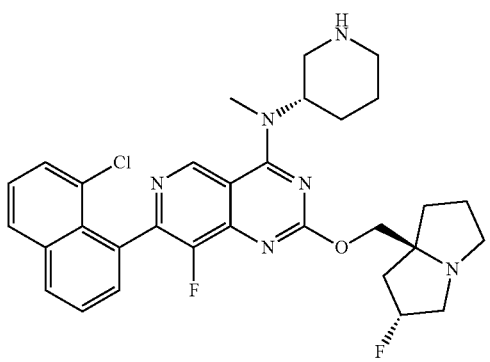 [SMILES: CN(c1nc(OC[C@@]23CCCN2C[C@H](F)C3)nc2c(F)c(-c3cccc4cccc(Cl)c34)ncc12)[C@H]1CCCNC1]

Step 2: 7-(8-chloronaphthalen-1-yl)-8-fluoro-2-(((2R,7aS)-2-fluorotetrahydro-1H-pyrrolizin-7a(5H)-yl)methoxy)-N-methyl-N—((S)-piperidin-3-yl)pyrido[4,3-d]pyrimidin-4-amine The deprotection of the Boc group was prepared in a similar fashion to Method #1, Step 9. The reaction mixture was concentrated in vacuo affording (91 mg, crude, trifluoroacetate salt) as a brown oil, which was used in the next step without further purification. LCMS Rt=0.588 min, m/z=578.2 [M+H]$^+$.

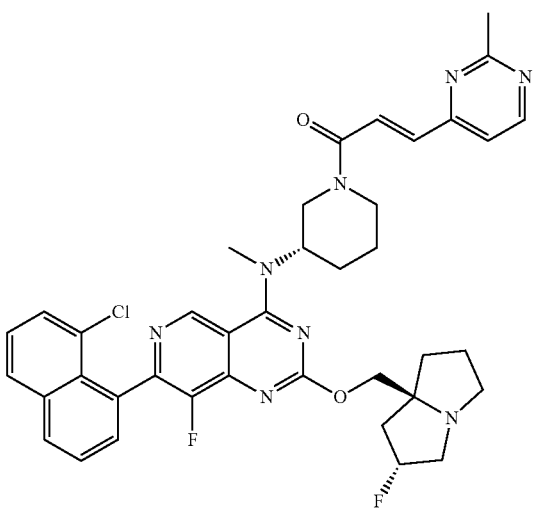 [SMILES: Cc1nccc(/C=C/C(=O)N2CCC[C@H](N(C)c3nc(OC[C@@]45CCCN4C[C@H](F)C5)nc4c(F)c(-c5cccc6cccc(Cl)c56)ncc34)C2)n1]

Step 3: (E)-1-((S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)piperidin-1-yl)-3-(2-methylpyrimidin-4-yl)prop-2-en-1-one The amide coupling reaction was prepared in a similar fashion to Method #1, Step 10. The resulting residue was purified by reverse phase HPLC (column: Waters Xbridge BEH C18 100*30 mm*10 μm; mobile phase: [water (NH$_4$HCO$_3$)-ACN]; B %: 32%-62%, 8 min) affording (E)-1-((S)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)piperidin-1-yl)-3-(2-methylpyrimidin-4-yl)prop-2-en-1-one (11.51 mg, 11.84%) as a white solid: $^1$H NMR (400 MHz, Acetonitrile-d3) δ 9.19-9.10 (m, 1H), 8.63-8.51 (m, 1H), 8.05 (d, J=8.0 Hz, 1H), 7.94 (d, J=8.3 Hz, 1H), 7.73-7.59 (m, 2H), 7.58-7.49 (m, 2H), 7.48-7.39 (m, 1H), 7.38-7.31 (m, 1H), 7.28-7.20 (m, 1H), 5.32-5.01 (m, 1H), 4.99-4.69 (m, 1H), 4.66-4.45 (m, 1H), 4.35-4.18 (m, 1H), 4.17-4.05 (m, 2H), 4.02-3.83 (m, 1H), 3.41-3.34 (m, 3H), 3.13-3.00 (m, 2H), 2.95-2.81 (m, 2H), 2.76-2.63 (m, 1H), 2.62-2.52 (m, 3H), 2.11-1.93 (m, 5H), 1.80 (br s, 3H), 1.70-1.53 (m, 2H).

LCMS (5% to 95% acetonitrile in water+0.03% ammonium bicarbonate over 6 min); retention time 2.976 min, ESI+ found [M+H]=724.3.

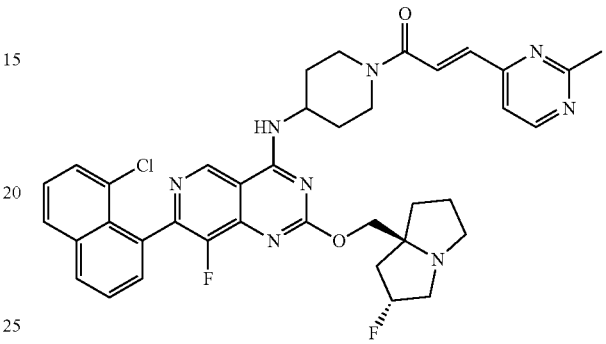

Example 261 (Method 1): (E)-1-(4-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)piperidin-1-yl)-3-(2-methylpyrimidin-4-yl)prop-2-en-1-one

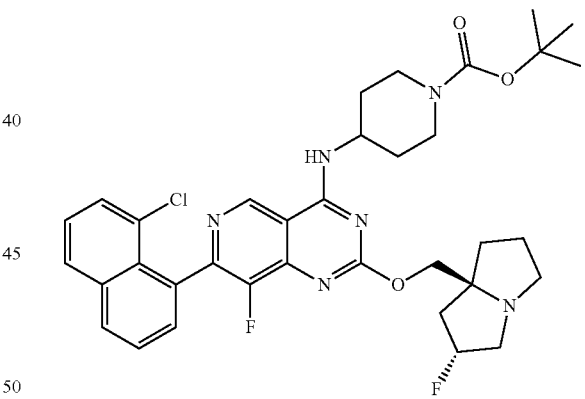

Step 1: tert-butyl 4-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)piperidine-1-carboxylate The substitution reaction was prepared in a similar fashion to Method #1, Step 8. The resulting residue was purified by reverse phase HPLC (column: Phenomenex Luna C18 100*40 mm*3 μm; mobile phase: [water(TFA)-ACN]; B %: 20%-65%, 8 min) affording tert-butyl 4-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)piperidine-1-carboxylate (100 mg, 29.56%, trifluoroacetate salt) as a white solid. LCMS Rt=0.764 min, m/z=664.3 [M+H]$^+$.

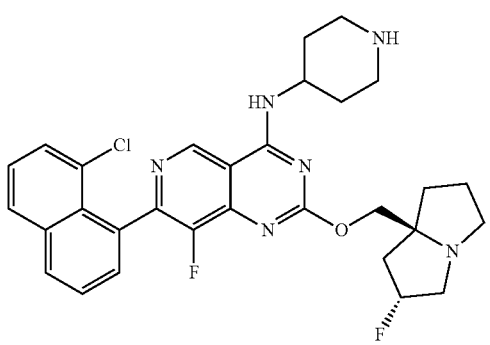 [SMILES: Fc1c(-c2cccc3cccc(Cl)c23)ncc2c(NC3CCNCC3)nc(OC[C@@]34CCCN3C[C@H](F)C4)nc12]

Step 2: 7-(8-chloronaphthalen-1-yl)-8-fluoro-2-(((2R,7aS)-2-fluorotetrahydro-1H-pyrrolizin-7a(5H)-yl)methoxy)-N-(piperidin-4-yl)pyrido[4,3-d]pyrimidin-4-amine The deprotection of the Boc group was prepared in a similar fashion to Method #1, Step 9. The reaction mixture was concentrated in vacuo affording 7-(8-chloronaphthalen-1-yl)-8-fluoro-2-(((2R,7aS)-2-fluorotetrahydro-1H-pyrrolizin-7a(5H)-yl)methoxy)-N-(piperidin-4-yl)pyrido[4,3-d]pyrimidin-4-amine (100 mg, crude, trifluoroacetate salt) as a brown oil, which was used in the next step without further purification. LCMS Rt=0.626 min, m/z=564.2 [M+H]$^+$.

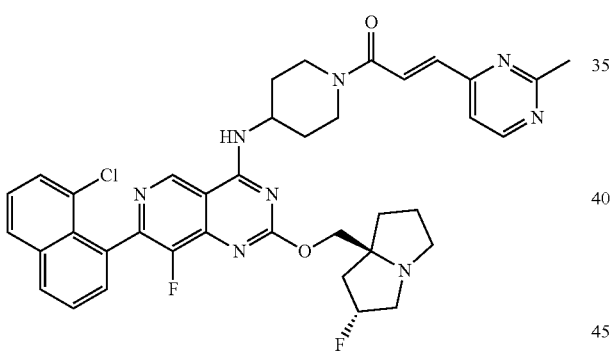

Step 3: (E)-1-(4-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)piperidin-1-yl)-3-(2-methylpyrimidin-4-yl)prop-2-en-1-one The amide coupling reaction was prepared in a similar fashion to Method #1, Step 10. The resulting residue was purified by reverse phase HPLC (column: Waters Xbridge BEH C18 100*30 mm*10 μm; mobile phase: [water (NH$_4$HCO$_3$)-ACN]; B %: 40%-60%, 8 min) affording (E)-1-(4-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)piperidin-1-yl)-3-(2-methylpyrimidin-4-yl)prop-2-en-1-one (16.86 mg, 16.10%) as a white solid: $^1$H NMR (400 MHz, Acetonitrile-d3) δ 9.10 (s, 1H), 8.70 (d, J=5.1 Hz, 1H), 8.14 (d, J=7.9 Hz, 1H), 8.04 (d, J=8.1 Hz, 1H), 7.79-7.68 (m, 2H), 7.63 (d, J=7.6 Hz, 2H), 7.56-7.50 (m, 1H), 7.43 (d, J=15.2 Hz, 1H), 7.36 (d, J=5.0 Hz, 1H), 7.30 (br d, J=6.8 Hz, 1H), 5.40-5.17 (m, 1H), 4.70-4.50 (m, 2H), 4.30-4.11 (m, 3H), 3.38 (br t, J=13.1 Hz, 1H), 3.24-3.08 (m, 3H), 3.04-2.89 (m, 2H), 2.69 (s, 3H), 2.24-2.05 (m, 6H), 1.87 (br s, 2H), 1.78-1.61 (m, 2H). LCMS (5% to 95% acetonitrile in water+0.03% ammonium bicarbonate over 6 min); retention time 2.932 min, ESI+ found [M+H]=710.3.

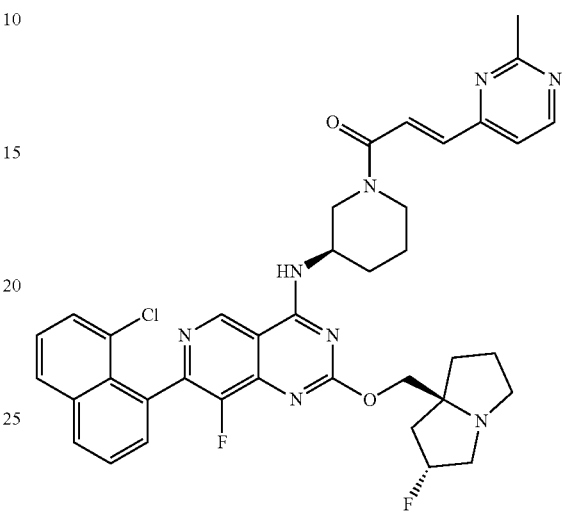

Example 262 (Method 1): (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)piperidin-1-yl)-3-(2-methylpyrimidin-4-yl)prop-2-en-1-one

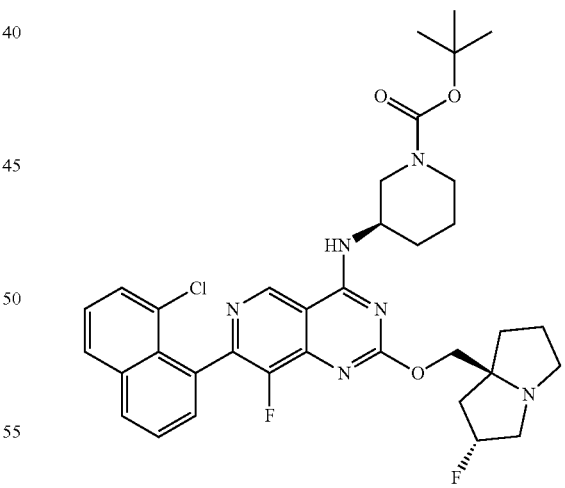

Step 1: tert-butyl (R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)piperidine-1-carboxylate The substitution reaction was prepared in a similar fashion to Method #1, Step 8. The resulting residue was purified by reverse phase HPLC (column: Phenomenex Luna C18

250*50 mm*10 μm; mobile phase: [water(TFA)-ACN]; B %: 30%-70%, 10 min) affording tert-butyl (R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)piperidine-1-carboxylate (80 mg, 17.16%, trifluoroacetate salt) as a white solid. LCMS Rt=0.773 min, m/z=664.3 [M+H]+.

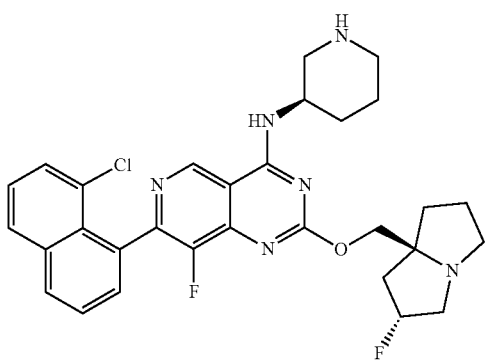 [SMILES: Fc1c(-c2cccc3cccc(Cl)c23)ncc2c(N[C@@H]3CCCNC3)nc(OC[C@@]34CCCN3C[C@H](F)C4)nc12]

Step 2: 7-(8-chloronaphthalen-1-yl)-8-fluoro-2-(((2R,7aS)-2-fluorotetrahydro-1H-pyrrolizin-7a(5H)-yl)methoxy)-N—((R)-piperidin-3-yl)pyrido[4,3-d]pyrimidin-4-amine The deprotection of the Boc group was prepared in a similar fashion to Method #1, Step 9. The reaction mixture was concentrated in vacuo affording 7-(8-chloronaphthalen-1-yl)-8-fluoro-2-(((2R,7aS)-2-fluorotetrahydro-1H-pyrrolizin-7a(5H)-yl)methoxy)-N—((R)-piperidin-3-yl)pyrido[4,3-d]pyrimidin-4-amine (80 mg, crude, trifluoroacetate salt) as a yellow oil, which was used in the next step without further purification. LCMS Rt=0.514 min, m/z=564.2 [M+H]+.

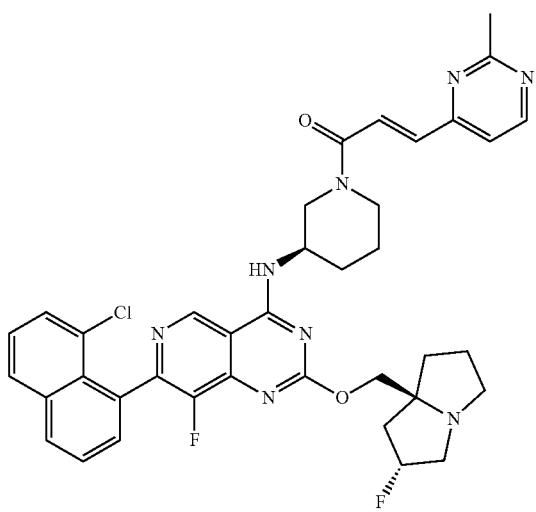 [SMILES: Cc1nccc(/C=C/C(=O)N2CCC[C@@H](Nc3nc(OC[C@@]45CCCN4C[C@H](F)C5)nc4c(F)c(-c5cccc6cccc(Cl)c56)ncc34)C2)n1]

Step 3: (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)piperidin-1-yl)-3-(2-methylpyrimidin-4-yl)prop-2-en-1-one The amide coupling reaction was prepared in a similar fashion to Method #1, Step 10. The resulting residue was purified by reverse phase HPLC (column: Waters Xbridge Prep OBD C18 150*40 mm*10 um; mobile phase: [water (NH4HCO3)-ACN]; B %: 30%-60%, 8 min) affording (E)-1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)amino)piperidin-1-yl)-3-(2-methylpyrimidin-4-yl)prop-2-en-1-one (26.08 mg, 31.13%) as a white solid: $^1$H NMR (400 MHz, Acetonitrile-d3) δ 9.15-8.97 (m, 1H), 8.76-8.52 (m, 1H), 8.20-7.96 (m, 2H), 7.76-7.64 (m, 1H), 7.62-7.56 (m, 2H), 7.55-7.46 (m, 2H), 7.46-7.24 (m, 2H), 7.23-7.05 (m, 1H), 5.37-5.10 (m, 1H), 4.70-4.23 (m, 2H), 4.18-4.06 (m, 2H), 4.00-3.87 (m, 1H), 3.77-3.62 (m, 1H), 3.49-3.27 (m, 1H), 3.18-3.00 (m, 3H), 2.91-2.81 (m, 1H), 2.73-2.63 (m, 3H), 2.24-2.01 (m, 4H), 1.93-1.62 (m, 6H).

LCMS (5% to 95% acetonitrile in water+0.03% ammonium bicarbonate over 6 min); retention time 2.902 min, ESI+ found [M+H]=710.3.

Example 263 (Method 2): 1-((R)-3-((7-(6,8-dichloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one

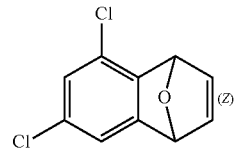 [SMILES: Clc1cc(Cl)c2c(c1)C1C=CC2O1]

Step 1: 5,7-dichloro-1,4-dihydro-1,4-epoxynaphthalene

To a solution of 1-bromo-3,5-dichloro-2-fluoro-benzene (10 g, 41.00 mmol) and furan (5.58 g, 82.00 mmol) in toluene (100 mL) was added n-butyllithium (2.5 M, 19.68 mL) at −15° C. The mixture was stirred at 25° C. for 12 h. The reaction mixture was quenched with saturated ammonium chloride (100 mL) and extracted with petroleum ether (3×50 mL). The combined organic layers were dried over sodium sulphate and concentrated in vacuo affording 5,7-dichloro-1,4-dihydro-1,4-epoxynaphthalene (10 g, crude) as a yellow oil, which was used in the next step without further purification.

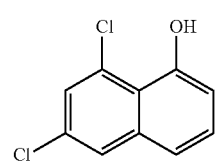 [SMILES: Oc1cccc2cc(Cl)cc(Cl)c12]

Step 2: 6,8-dichloronaphthalen-1-ol

To a solution of 5,7-dichloro-1,4-dihydro-1,4-epoxynaphthalene (10 g, 46.94 mmol) in ethanol (10 mL) was added hydrochloric acid (12 M, 46.94 mL), and the mixture was stirred at 80° C. for 6 h. The reaction mixture was concentrated in vacuo. The residue was suspended in water, and the pH was adjusted to 7 by addition of saturated sodium bicarbonate (500 mL). The mixture was extracted with tert-butyl methyl ether (3×100 mL). The combined organic layers were dried over sodium sulphate and concentrated in vacuo. The residue was purified by column chromatography (silica gel, 100-200 mesh, 0-2% ethyl acetate in petroleum ether) affording 6,8-dichloronaphthalen-1-ol (2.8 g, 28.00%) as a yellow solid: $^1$H NMR (400 MHz, Dimethyl sulfoxide-d6) δ 10.34 (s, 1H), 7.96-7.89 (m, 1H), 7.52-7.48 (m, 1H), 7.43-7.35 (m, 2H), 6.99-6.92 (m, 1H).

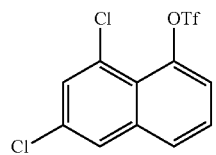 [SMILES: O=S(=O)(Oc1cccc2cc(Cl)cc(Cl)c12)C(F)(F)F]

Step 3: 6,8-dichloronaphthalen-1-yl trifluoromethanesulfonate

To a solution of 6,8-dichloronaphthalen-1-ol (500 mg, 2.35 mmol) in dichloromethane (10 mL) was added N-ethyl-N-isopropylpropan-2-amine (1.21 g, 9.39 mmol) and 4A MS (50 mg) at −40° C. The mixture was stirred at −40° C. for 10 min. Trifluoromethanesulfonic anhydride (993.17 mg, 3.52 mmol) was added, and the mixture was stirred at −40° C. for 30 min. The reaction mixture was diluted with water (5 mL) and extracted with ethyl acetate (3×10 mL). The combined organic layers were dried over sodium sulphate and concentrated in vacuo. The residue was purified by column chromatography (silica gel, 100-200 mesh, 0-5% ethyl acetate in petroleum ether) affording 6,8-dichloronaphthalen-1-yl trifluoromethanesulfonate (350 mg, 43.21%) as a yellow oil.

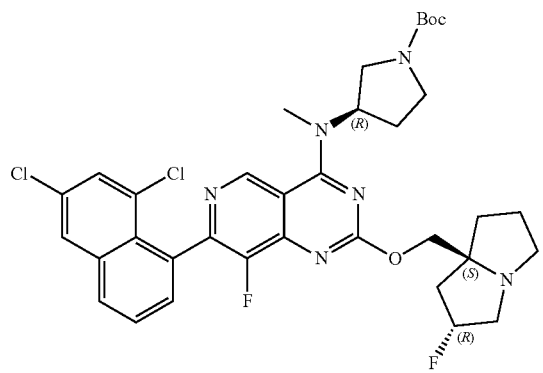

Step 4: (R)-tert-butyl 3-((7-(6,8-dichloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate To a solution of (R)-tert-butyl 3-((8-fluoro-2-(((2R,7aS)-2-fluorohexahydro-1H-pyrrolizin-7a-yl)methoxy)-7-(tributylstannyl)pyrido[4,3-d]pyrimidin-4-yl)(methyl)amino)pyrrolidine-1-carboxylate (140 mg, 176.41 μmol) in dioxane (2 mL) was added 6,8-dichloronaphthalen-1-yl trifluoromethanesulfonate (73.06 mg, 211.69 μmol) and palladium tri-tert-butylphosphane (18.03 mg, 35.28 μmol). The mixture was stirred at 90° C. for 12 h under nitrogen. The reaction mixture was diluted with water (2 mL) and extracted with dichloromethane (3×2 mL). The combined organic layers were dried over sodium sulphate and concentrated in vacuo. The residue was purified by reverse phase HPLC (column: Phenomenex Luna 80*30 mm*3 μm; mobile phase: [water (TFA)-ACN]; B %: 25%-55%, 8 min) affording (R)-tert-butyl 3-((7-(6,8-dichloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (15 mg, 10.45%, trifluoroacetate salt) as a yellow solid. LCMS Rt=0.716 min, m/z=698.2 [M+H]$^+$.

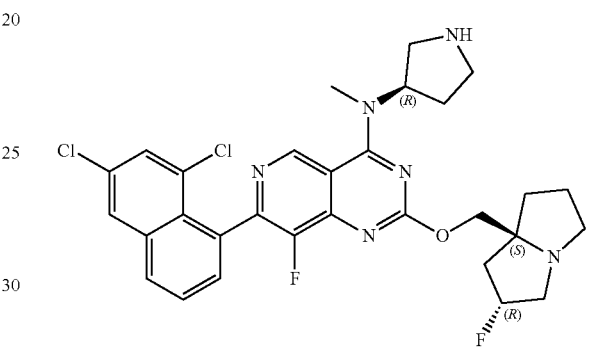

Step 5: 7-(6,8-dichloronaphthalen-1-yl)-8-fluoro-2-(((2R,7aS)-2-fluorohexahydro-1H-pyrrolizin-7a-yl)methoxy)-N-methyl-N—((R)-pyrrolidin-3-yl)pyrido[4,3-d]pyrimidin-4-amine The deprotection of the Boc group was prepared in a similar fashion to Method #2, Step 6. The residue was concentrated in vacuo affording 7-(6,8-dichloronaphthalen-1-yl)-8-fluoro-2-(((2R,7aS)-2-fluorohexahydro-1H-pyrrolizin-7a-yl)methoxy)-N-methyl-N—((R)-pyrrolidin-3-yl)pyrido[4,3-d]pyrimidin-4-amine (10 mg, crude, hydrochloride salt) as a yellow solid. LCMS Rt =0.510 min, m/z=598.2 [M+H]$^+$.

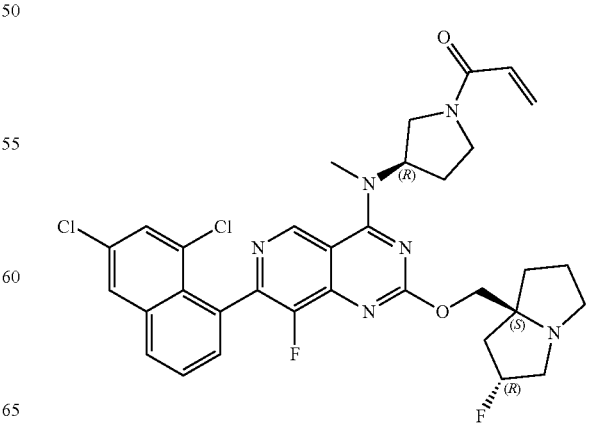

Step 6: 1-((R)-3-((7-(6,8-dichloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one The amide coupling reaction was prepared in a similar fashion to Method #2, Step 7. The resulting residue was purified by reverse phase HPLC (column: Waters Xbridge BEH C18 100*30 mm*10 μm; mobile phase: [water (NH$_4$HCO$_3$)-ACN]; B %: 35%-75%, 8 min) affording 1-((R)-3-((7-(6,8-dichloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (2.82 mg, 13.72%) as a yellow oil: $^1$H NMR (400 MHz, Chloroform-d) δ 9.14 (d, J=2.4 Hz, 1H), 7.92 (br d, J=7.9 Hz, 1H), 7.88 (s, 1H), 7.68-7.61 (m, 1H), 7.61-7.56 (m, 1H), 7.54 (d, J=1.8 Hz, 1H), 6.53-6.40 (m, 2H), 5.80-5.72 (m, 1H), 5.50-5.39 (m, 1H), 5.38-5.19 (m, 1H), 4.37-4.21 (m, 2H), 4.20-4.04 (m, 1H), 3.99 (br dd, J=9.4, 11.8 Hz, 1H), 3.75-3.65 (m, 1H), 3.64-3.53 (m, 1H), 3.51-3.43 (m, 3H), 3.34-3.22 (m, 2H), 3.18 (br s, 1H), 3.05-2.93 (m, 1H), 2.54-2.26 (m, 3H), 2.25-2.09 (m, 2H), 2.03-1.83 (m, 3H).

LCMS (5% to 95% acetonitrile in water+0.03% ammonium bicarbonate over 6 min); retention time 2.996 min, ESI+ found [M+H]=652.2.

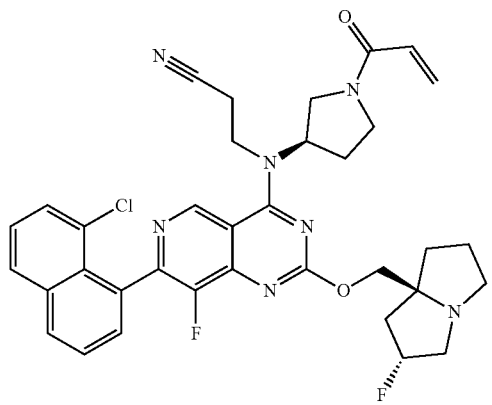 [SMILES: C=CC(=O)N1CC[C@@H](N(CCC#N)c2nc(OC[C@@]34CCCN3C[C@H](F)C4)nc3c(F)c(-c4cccc5cccc(Cl)c45)ncc23)C1]

Example 264 (Method 2): 3-(((R)-1-acryloylpyrrolidin-3-yl)(7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)propanenitrile

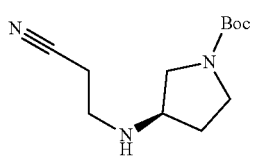

Step 1: (R)-tert-butyl 3-((2-cyanoethyl)amino)pyrrolidine-1-carboxylate

To a solution of prop-2-enenitrile (427.35 mg, 8.05 mmol) in methanol (10 mL) was added dropwise tert-butyl (3R)-3-aminopyrrolidine-1-carboxylate (1 g, 5.37 mmol). The mixture was stirred at 60° C. for 1 h. The reaction mixture was concentrated in vacuo affording (R)-tert-butyl 3-((2-cyanoethyl)amino)pyrrolidine-1-carboxylate (1.1 g, crude) as a yellow oil, which was used in the next step without further purification.

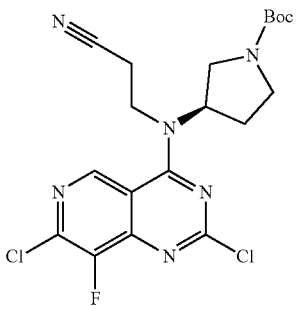 [SMILES: CC(C)(C)OC(=O)N1CC[C@@H](N(CCC#N)c2nc(Cl)nc3c(F)c(Cl)ncc23)C1]

Step 2: tert-butyl (3R)-3-[(2,7-dichloro-8-fluoro-pyrido[4,3-d]pyrimidin-4-yl)-(2-isocyanoethyl)amino]pyrrolidine-1-carboxylate The substitution reaction was prepared in a similar fashion to Method #2, Step 3.

The crude residue was diluted with tert-butyl methyl ether (30 mL), and the resulting precipitate was filtered affording tert-butyl (3R)-3-[(2,7-dichloro-8-fluoro-pyrido[4,3-d]pyrimidin-4-yl)-(2-isocyanoethyl)amino]pyrrolidine-1-carboxylate (1.5 g, 83.17%) as a yellow solid. LCMS Rt=0.774 min, m/z=454.1 [M+H]$^+$.

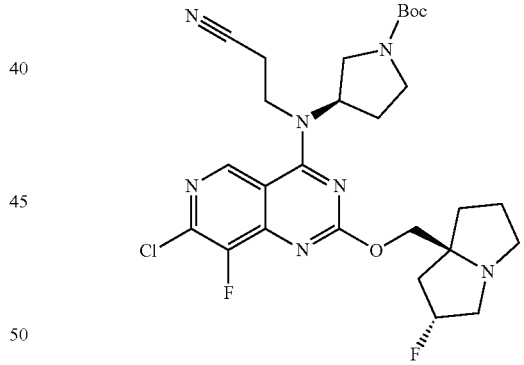

Step 3: (R)-tert-butyl 3-((7-chloro-8-fluoro-2-(((2R,7aS)-2-fluorohexahydro-1H-pyrrolizin-7a-yl)methoxy)pyrido[4,3-d]pyrimidin-4-yl)(2-cyanoethyl)amino)pyrrolidine-1-carboxylate The substitution reaction was prepared in a similar fashion to Method #2, Step 4. The residue was purified by column chromatography (silica gel, 100-200 mesh, 3~10% methanol in dichloromethane) affording (R)-tert-butyl 3-((7-chloro-8-fluoro-2-(((2R,7aS)-2-fluorohexahydro-1H-pyrrolizin-7a-yl)methoxy)pyrido[4,3-d]pyrimidin-4-yl)(2-cyanoethyl)amino)pyrrolidine-1-carboxylate (1.5 g, 81.48%) as a yellow solid. LCMS Rt=0.570 min, m/z=577.2 [M+H]$^+$.

991

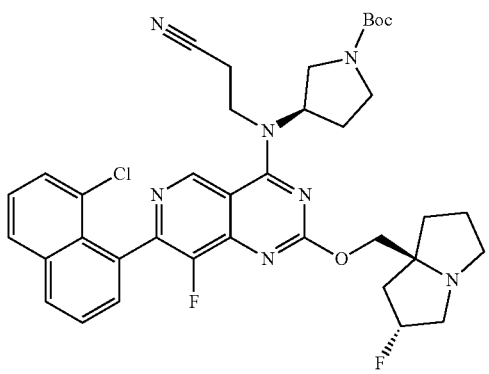 [SMILES: CC(C)(C)OC(=O)N1CC[C@@H](N(CCC#N)c2nc(OC[C@@]34CCCN3C[C@H](F)C4)nc3c(F)c(-c4cccc5cccc(Cl)c45)ncc23)C1]

Step 4: (R)-tert-butyl 3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(2-cyanoethyl)amino)pyrrolidine-1-carboxylate The Suzuki reaction was prepared in a similar fashion to Method #2, Step 5. The residue was purified by column chromatography (silica gel, 100-200 mesh, 50-100% ethyl acetate in petroleum ether) affording (R)-tert-butyl 3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(2-cyanoethyl)amino)pyrrolidine-1-carboxylate (70 mg, 8.21%) as a pale yellow solid. LCMS Rt=2.142 min, m/z=703.3 [M+H]$^+$.

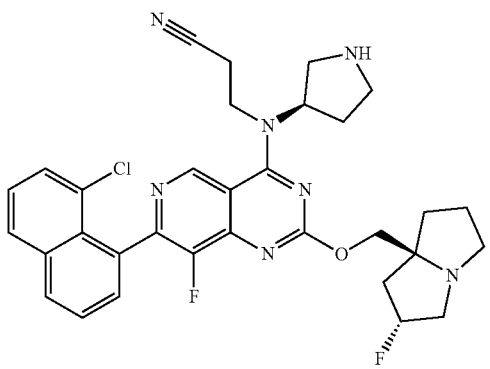 [SMILES: N#CCCN(c1nc(OC[C@@]23CCCN2C[C@H](F)C3)nc2c(F)c(-c3cccc4cccc(Cl)c34)ncc12)[C@@H]1CCNC1]

Step 5: 3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)((R)-pyrrolidin-3-yl)amino)propanenitrile The deprotection of the Boc group was prepared in a similar fashion to Method #2, Step 6. The residue was concentrated in vacuo affording 3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)((R)-pyrrolidin-3-yl)amino)propanenitrile (70 mg, crude, trifluoroacetate salt) as a brown oil, which was used in the next step without further purification. LCMS Rt=0.467 min, m/z=603.2 [M+H]$^+$.

992

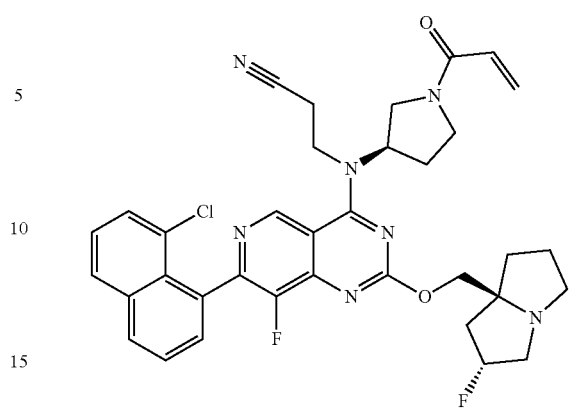

Step 6: 3-(((R)-1-acryloylpyrrolidin-3-yl)(7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)propanenitrile The amide coupling reaction was prepared in a similar fashion to Method #2, Step 7. The crude product was purified by reverse phase-HPLC (column: Waters Xbridge BEH C18 100*30 mm*10 μm; mobile phase: [water (NH$_4$HCO$_3$)-ACN]; B %: 30%-60%, 8 min) affording 3-(((R)-1-acryloylpyrrolidin-3-yl)(7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)propanenitrile (25.23 mg, 39.16%) as a yellow solid: $^1$H NMR (400 MHz, Chloroform-d) δ 9.11-9.04 (m, 1H), 8.07-7.99 (m, 1H), 7.90 (d, J=8.1 Hz, 1H), 7.66-7.52 (m, 3H), 7.50-7.40 (m, 1H), 6.44 (br d, J=4.4 Hz, 2H), 5.81-5.69 (m, 1H), 5.40-5.20 (m, 1H), 5.17 (br s, 1H), 4.37-4.29 (m, 1H), 4.26 (br d, J=9.6 Hz, 1H), 4.20-4.02 (m, 1H), 4.00-3.88 (m, 2H), 3.87-3.71 (m, 1H), 3.71-3.44 (m, 2H), 3.33-3.22 (m, 2H), 3.18 (br s, 1H), 3.13-2.94 (m, 2H), 2.91-2.70 (m, 1H), 2.68-2.52 (m, 1H), 2.37 (br d, J=8.4 Hz, 1H), 2.26 (br s, 1H), 2.22-2.08 (m, 2H), 2.00-1.85 (m, 3H).

LCMS (5% to 95% acetonitrile in water+0.03% ammonium bicarbonate over 6 min); retention time 2.954 min, ESI+ found [M+H]=657.3.

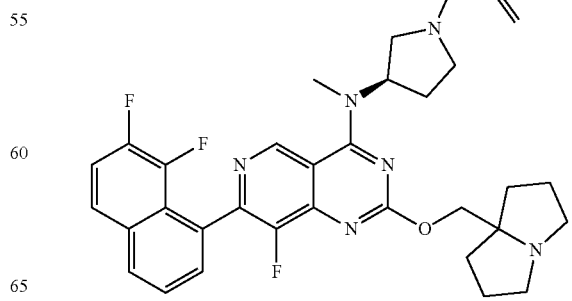

Example 265 (Method 2): (R)-1-(3-((7-(7,8-difluoronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)prop-2-en-1-one

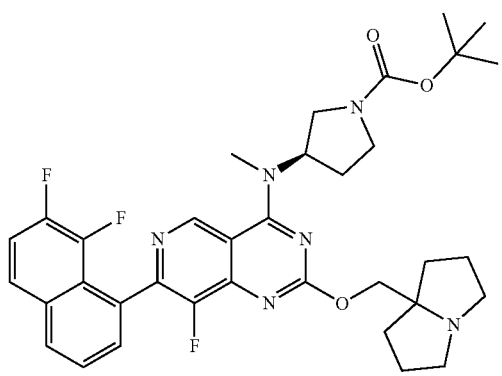 [SMILES: CN(c1nc(OCC23CCCN2CCC3)nc2c(F)c(-c3cccc4ccc(F)c(F)c34)ncc12)[C@@H]1CCN(C(=O)OC(C)(C)C)C1]

Step 1: tert-butyl (R)-3-((7-(7,8-difluoronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidine-1-carboxylate The Suzuki reaction was prepared in a similar fashion to Method #2, Step 5. The crude residue was purified by reverse phase prep-HPLC (column: Phenomenex Luna 80*30 mm*3 μm; mobile phase: [water(TFA)-ACN]; B %: 20%-50%, 8 min) affording tert-butyl (R)-3-((7-(7,8-difluoronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidine-1-carboxylate (150 mg, 60.24%, trifluoroacetate salt) as a black solid. LCMS Rt=1.574 min, m/z=648.3 [M+H]$^+$.

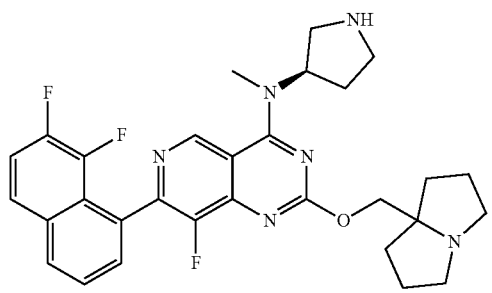 [SMILES: CN(c1nc(OCC23CCCN2CCC3)nc2c(F)c(-c3cccc4ccc(F)c(F)c34)ncc12)[C@@H]1CCNC1]

Step 2: (R)-7-(7,8-difluoronaphthalen-1-yl)-8-fluoro-N-methyl-N-(pyrrolidin-3-yl)-2-((tetrahydro-1H-pyrrolizin-7a(5H)-yl)methoxy)pyrido[4,3-d]pyrimidin-4-amine The deprotection of Boc group was prepared in a similar fashion to Method #1, Step 9. The reaction mixture was concentrated in vacuo affording (R)-7-(7,8-difluoronaphthalen-1-yl)-8-fluoro-N-methyl-N-(pyrrolidin-3-yl)-2-((tetrahydro-1H-pyrrolizin-7a(5H)-yl)methoxy)pyrido[4,3-d]pyrimidin-4-amine (100 mg, crude, hydrochloric acid salt) as a yellow oil, which was used in the next step without further purification. LCMS Rt=0.481 min, m/z=548.3 [M+H]$^+$.

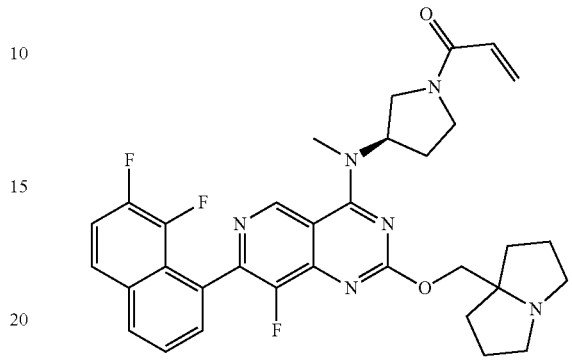

Step 3: (R)-1-(3-((7-(7,8-difluoronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)prop-2-en-1-one The amide coupling reaction was prepared in a similar fashion to Method #2, Step 7. The crude product was purified by reverse phase prep-HPLC (column: Waters Xbridge Prep OBD C18 150*40 mm*10 μm; mobile phase: [water(NH$_4$HCO$_3$)-ACN]; B %: 25%-55%, 8 min) affording (R)-1-(3-((7-(7,8-difluoronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)prop-2-en-1-one (16.07 mg, 15.19%) as a yellow amorphous solid: $^1$H NMR (400 MHz, Chloroform-d) δ 9.16 (s, 1H), 7.97 (br d, J=8.0 Hz, 1H), 7.76-7.68 (m, 1H), 7.67-7.56 (m, 2H), 7.40 (q, J=8.5 Hz, 1H), 6.56-6.39 (m, 2H), 5.80-5.70 (m, 1H), 5.56-5.39 (m, 1H), 4.26 (br s, 2H), 4.19-4.04 (m, 1H), 4.03-3.84 (m, 1H), 3.70 (br d, J=8.1 Hz, 1H), 3.59 (br d, J=9.0 Hz, 1H), 3.46 (br s, 3H), 3.13 (br s, 2H), 2.73-2.60 (m, 2H), 2.53-2.24 (m, 2H), 2.09 (br dd, J=5.9, 11.6 Hz, 2H), 1.89 (br d, J=5.6 Hz, 4H), 1.73-1.68 (m, 2H). LCMS (5% to 95% acetonitrile in water+0.03% ammonium bicarbonate over 6 min); retention time 2.472 min, ESI+ found [M+H] =602.3.

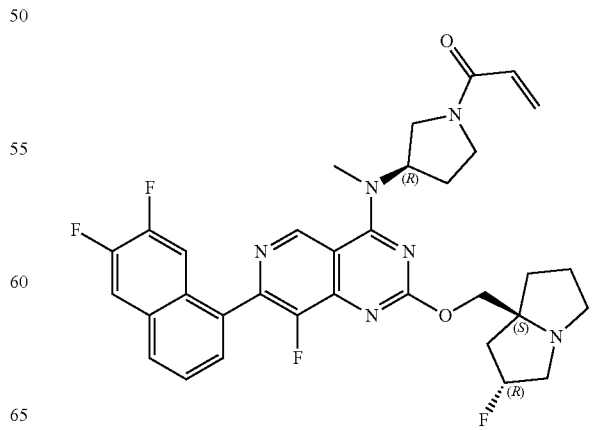

Example 266 (Method 2): 1-((R)-3-((7-(6,7-difluo-ronaphthalen-1-yl)-8-fluoro-2-(((2R,7aS)-2-fluoro-tetrahydro-1H-pyrrolizin-7a(5H)-yl)methoxy)pyrido[4,3-d]pyrimidin-4-yl)(methyl)amino)pyrrolidin-1-yl)prop-2-en-1-one

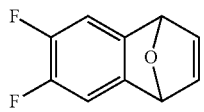

Step 1: 6,7-difluoro-1,4-dihydro-1,4-epoxynaphthalene

To a solution of 1-bromo-2,4,5-trifluoro-benzene (5 g, 23.70 mmol) in toluene (50 mL) was added furan (3.23 g, 47.40 mmol) at −40° C. n-Butyllithium (2.5 M, 12.32 mL) was added, and the mixture was stirred at 25° C. for 12 h under nitrogen. The reaction mixture was quenched with saturated ammonium chloride (50 mL) and extracted with petroleum ether (3×50 mL). The combined organic layers were dried over sodium sulphate and concentrated in vacuo affording 6,7-difluoro-1,4-dihydro-1,4-epoxynaphthalene (5 g, crude) as a yellow oil, which was used in the next step without further purification.

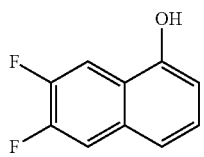 [SMILES: Oc1cccc2cc(F)c(F)cc12]

Step 2: 6,7-difluoronaphthalen-1-ol

To a solution of 6,7-difluoro-1,4-dihydro-1,4-epoxynaph-thalene (5 g, 27.75 mmol) in ethanol (50 mL) was added hydrochloric acid (12 M, 27.75 mL), and the mixture was stirred at 80° C. for 6 h. The reaction mixture was concentrated in vacuo. The residue was suspended in water, and the pH was adjusted to 7 with saturated sodium bicarbonate (500 mL). The mixture was extracted with tert-butyl methyl ether (3×50 mL). The combined organic layers were dried over sodium sulphate and concentrated in vacuo. The residue was purified by column chromatography (silica gel, 100-200 mesh, 0-2% ethyl acetate in petroleum ether) affording 6,7-difluoronaphthalen-1-ol (2.2 g, 44.00%) as a yellow solid: ¹H NMR (400 MHz, DMSO-d6) δ 10.40 (s, 1H), 7.97-7.82 (m, 2H), 7.38-7.29 (m, 2H), 6.89 (dd, J=3.1, 5.4 Hz, 1H).

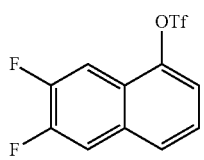 [SMILES: O=S(=O)(Oc1cccc2cc(F)c(F)cc12)C(F)(F)F]

Step 3: 6,7-difluoronaphthalen-1-yl trifluoromethanesulfonate

To a solution of 6,7-difluoronaphthalen-1-ol (800 mg, 4.44 mmol) in dichloromethane (20 mL) was added N-ethyl-N-isopropylpropan-2-amine (2.30 g, 17.76 mmol) and 4A MS (50 mg). The mixture was stirred at −40° C. for 10 min, and trifluoromethanesulfonic anhydride (1.88 g, 6.66 mmol) was added. The mixture was stirred at −40° C. for 30 min. The reaction mixture was diluted with water (5 mL) and extracted with ethyl acetate (3×20 mL). The combined organic layers were dried over sodium sulphate and concentrated in vacuo. The residue was purified by column chromatography (silica gel, 100-200 mesh, 0-5% ethyl acetate in petroleum ether) affording 6,7-difluoronaphthalen-1-yl trifluoromethanesulfonate (800 mg, 57.70%) as a yellow solid.

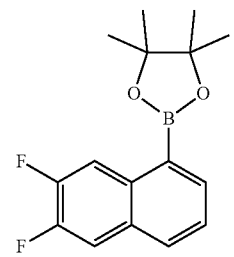 [SMILES: CC1(C)OB(c2cccc3cc(F)c(F)cc23)OC1(C)C]

Step 4: 2-(6,7-difluoronaphthalen-1-yl)-4,4,5,5-tetramethyl-1,3,2-dioxaborolane

To a solution of 6,7-difluoronaphthalen-1-yl trifluoromethanesulfonate (800 mg, 2.56 mmol) in dioxane (10 mL) was added 4,4,5,5-tetramethyl-2-(4,4,5,5-tetramethyl-1,3,2-dioxaborolan-2-yl)-1,3,2-dioxaborolane (976.02 mg, 3.84 mmol), [2-(2-aminophenyl)phenyl]-chloro-palladium dicyclohexyl-[3-(2,4,6-triisopropylphenyl)phenyl]phos-phane (187.49 mg, 256.24 μmol) and potassium acetate (754.41 mg, 7.69 mmol). The mixture was stirred at 100° C. for 12 h. The reaction mixture was diluted with water (10 mL) and extracted with ethyl acetate (3×20 mL). The combined organic layers were dried over sodium sulphate and concentrated in vacuo. The remaining residue was purified by column chromatography (silica gel, 100-200 mesh, 0-2% ethyl acetate in petroleum ether) affording 2-(6,7-difluoronaphthalen-1-yl)-4,4,5,5-tetramethyl-1,3,2-dioxaborolane (600 mg, 80.71%) as a yellow solid: ¹H NMR (400 MHz, Dimethyl sulfoxide-d6) δ 8.52 (dd, J=8.5, 13.3 Hz, 1H), 8.13-7.96 (m, 3H), 7.61-7.53 (m, 1H), 1.37 (s, 12H).

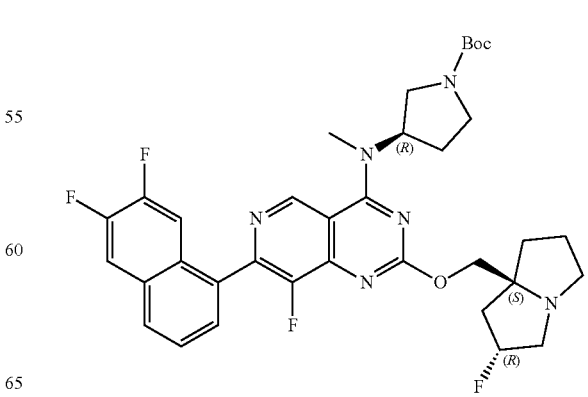

Step 5: tert-butyl (R)-3-((7-(6,7-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidine-1-carboxylate The Suzuki reaction was prepared in a similar fashion to Method #2, Step 5. The residue was purified by column chromatography (silica gel, 100-200 mesh, 50-60% ethyl acetate in petroleum ether) affording tert-butyl (R)-3-((7-(6,7-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidine-1-carboxylate (150 mg, 80.85%) as a yellow oil. LCMS Rt=0.672 min, m/z=666.3 [M+H]$^+$.

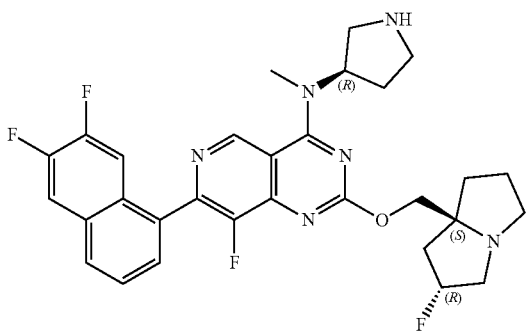

Step 6: 7-(6,7-difluoronaphthalen-1-yl)-8-fluoro-2-(((2R,7aS)-2-fluorotetrahydro-1H-pyrrolizin-7a(5H)-yl)methoxy)-N-methyl-N—((R)-pyrrolidin-3-yl)pyrido[4,3-d]pyrimidin-4-amine The deprotection of the Boc group was prepared in a similar fashion to Method #2, Step 6. The residue was concentrated in vacuo affording 7-(6,7-difluoronaphthalen-1-yl)-8-fluoro-2-(((2R,7aS)-2-fluorotetrahydro-1H-pyrrolizin-7a(5H)-yl)methoxy)-N-methyl-N—((R)-pyrrolidin-3-yl)pyrido[4,3-d]pyrimidin-4-amine (100 mg, crude, hydrochloride salt) as a yellow solid. LCMS Rt=0.566 min, m/z=566.2 [M+H]$^+$.

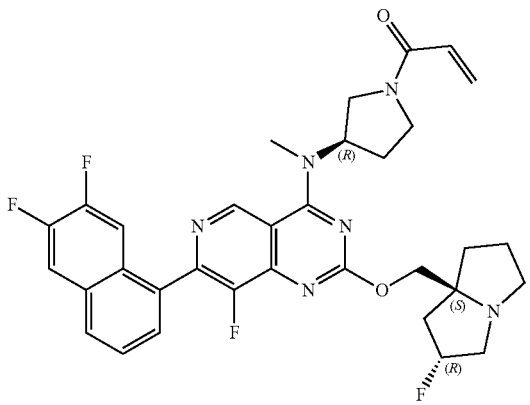

Step 7: 1-((R)-3-((7-(6,7-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one The amide coupling reaction was prepared in a similar fashion to Method #2, Step 7. The resulting residue was purified by reverse phase HPLC (column: Waters Xbridge Prep OBD C18 150*40 mm*10 μm; mobile phase: [water (NH$_4$HCO$_3$)-ACN]; B %: 35%-65%, 8 min) affording 1—((R)-3-((7-(6,7-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (15.78 mg, 15.52%) as a white solid: $^1$H NMR (400 MHz, Chloroform-d) δ 9.24 (s, 1H), 7.95-7.87 (m, 1H), 7.73-7.68 (m, 1H), 7.68-7.56 (m, 3H), 6.54 (s, 2H), 5.80-5.71 (m, 1H), 5.51-5.39 (m, 1H), 5.38-5.19 (m, 1H), 4.36-4.28 (m, 1H), 4.27-4.05 (m, 2H), 4.04-3.87 (m, 1H), 3.76-3.66 (m, 1H), 3.64-3.54 (m, 1H), 3.47 (d, J=8.4 Hz, 3H), 3.31-3.22 (m, 2H), 3.17 (br s, 1H), 3.04-2.93 (m, 1H), 2.52-2.13 (m, 5H), 2.00-1.85 (m, 3H).

LCMS (5% to 95% acetonitrile in water+0.03% ammonium bicarbonate over 6 min); retention time 2.797 min, ESI+ found [M+H]=620.3.

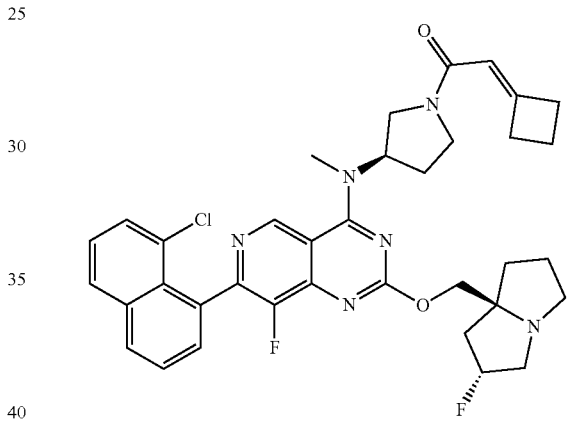

Example 267 (Method 1): 1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-2-cyclobutylideneethan-1-one

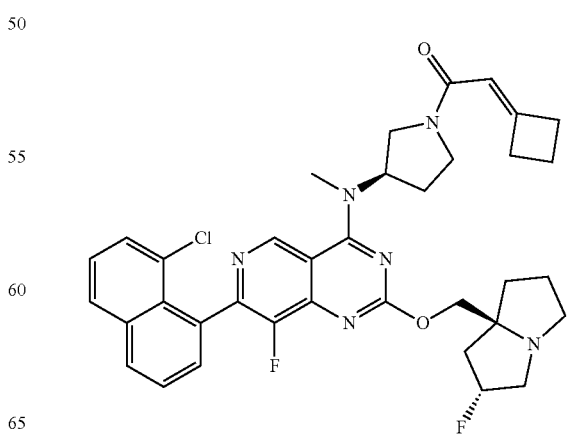

Step 1: 1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-2-cyclobutylideneethan-1-one The amide coupling reaction was prepared in a similar fashion to Method #1, Step 10. The residue was purified by reverse phase HPLC (column: Waters Xbridge Prep OBD C18 150*40 mm*10 um; mobile phase: [water(NH$_4$HCO$_3$)-ACN]; B %: 35%-65%, 8 min) affording 1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-2-cyclobutylideneethan-1-one (24.3 mg, 24.76%) as a yellow solid: $^1$H NMR (400 MHz, Acetonitrile-d3) δ 9.23 (s, 1H), 8.17 (d, J=7.9 Hz, 1H), 8.06 (d, J=8.1 Hz, 1H), 7.77-7.70 (m, 1H), 7.69-7.62 (m, 2H), 7.58-7.53 (m, 1H), 5.95 (br d, J=11.1 Hz, 1H), 5.61-5.22 (m, 2H), 4.36-4.21 (m, 2H), 4.09-3.89 (m, 1H), 3.80 (br dd, J=4.6, 12.0 Hz, 1H), 3.67-3.50 (m, 2H), 3.49-3.43 (m, 3H), 3.38-3.29 (m, 1H), 3.27-3.19 (m, 1H), 3.18-3.11 (m, 2H), 3.10-2.93 (m, 2H), 2.92-2.83 (m, 2H), 2.46-2.36 (m, 2H), 2.31 (br d, J=4.8 Hz, 2H), 2.16-2.03 (m, 6H).

LCMS (5% to 95% acetonitrile in water+0.1% ammonium bicarbonate over 6 min); retention time 3.156 min, ESI+ found [M+H]=658.3.

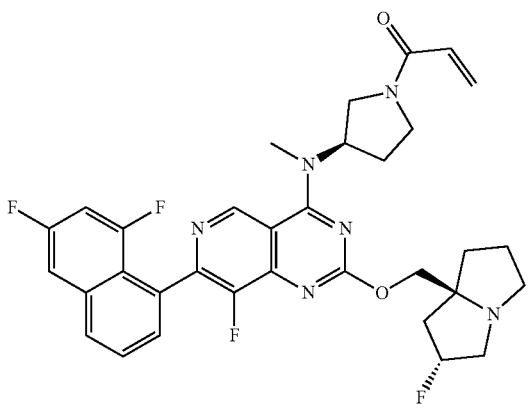 [SMILES: C=CC(=O)N1CC[C@@H](N(C)c2nc(OC[C@@]34CCCN3C[C@H](F)C4)nc3c(F)c(-c4cccc5cc(F)cc(F)c45)ncc23)C1]

Example 268 (Method 2): 1-((R)-3-((7-(6,8-difluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)prop-2-en-1-one

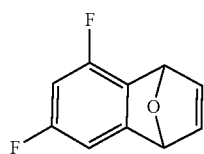 [SMILES: Fc1cc(F)c2c(c1)C1C=CC2O1]

Step 1: 3,5-difluoro-11-oxatricyclo[6.2.1.0$^{2,7}$]undeca-2,4,6,9-tetraene

To a solution of 1-bromo-2,3,5-trifluoro-benzene (5 g, 23.70 mmol) and furan (3.23 g, 47.40 mmol) in toluene (100 mL) was added n-butyllithium (2.5 M, 11.38 mL) at −40° C. under a nitrogen atmosphere. The reaction mixture was quenched with saturated ammonium chloride (100 mL) at 0° C. and extracted with ethyl acetate (3×100 mL). The combined organic layers were dried over sodium sulphate and concentrated in vacuo affording 3,5-difluoro-11-oxatricyclo[6.2.1.0$^{2,7}$]undeca-2,4,6,9-tetraene (8.5 g, crude) as a brown oil, which was used in the next step without any further purification.

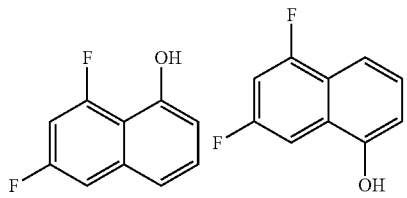

Step 2: 6,8-difluoronaphthalen-1-ol and 5,7-difluoronaphthalen-1-ol

To a solution of 3,5-difluoro-11-oxatricyclo[6.2.1.0$^{2,7}$]undeca-2,4,6,9-tetraene (4.2 g, 23.31 mmol) in ethanol (40 mL) was added hydrochloric acid (12 M, 23.31 mL). The mixture was stirred at 80° C. for 6 h. The mixture was diluted with water (20 mL) and extracted with ethyl acetate (3×50 mL). The combined organic layers were dried over sodium sulphate and concentrated in vacuo. The residue was purified by column chromatography (silica gel, 100-200 mesh, 0-10% ethyl acetate in petroleum ether) affording 6,8-difluoronaphthalen-1-ol (1.8 g, 21.43%) as a yellow solid and 5,7-difluoronaphthalen-1-ol (2.4 g, 28.57%) as a yellow solid.

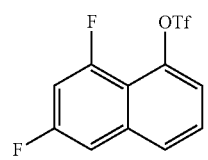 [SMILES: O=S(=O)(Oc1cccc2cc(F)cc(F)c12)C(F)(F)F]

Step 3: (6,8-difluoro-1-naphthyl) trifluoromethanesulfonate

To a mixture of 6,8-difluoronaphthalen-1-ol (1.6 g, 8.88 mmol) in dichloromethane (20 mL) was added N,N-diisopropylethylamine (6.89 g, 53.29 mmol) and trifluoromethanesulfonic anhydride (3.26 g, 11.55 mmol), the mixture was stirred at 0° C. for 0.5 h under a nitrogen atmosphere. The reaction mixture was quenched with saturated sodium bicarbonate (20 mL) and extracted with dichloromethane (3×30 mL). The combined organic layers were dried over sodium sulphate and concentrated in vacuo. The residue was purified by column chromatography (silica gel, 100-200 mesh, 0-10% ethyl acetate in petroleum ether) affording (6,8-difluoro-1-naphthyl) trifluoromethanesulfonate (1.8 g, 64.91%) as a yellow solid. LCMS Rt=0.713 min, m/z=312.0 [M+H]$^+$.

1001

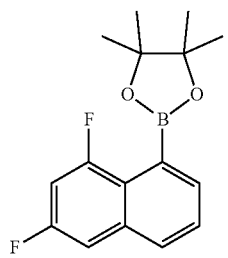 [SMILES: CC1(C)OB(c2cccc3cc(F)cc(F)c23)OC1(C)C]

Step 4: 2-(6,8-difluoro-1-naphthyl)-4,4,5,5-tetramethyl-1,3,2-dioxaborolane

A mixture of (6,8-difluoro-1-naphthyl) trifluoromethanesulfonate (500 mg, 1.60 mmol), 4,4,5,5-tetramethyl-2-(4,4,5,5-tetramethyl-1,3,2-dioxaborolan-2-yl)-1,3,2-dioxaborolane (427.01 mg, 1.68 mmol), potassium acetate (471.52 mg, 4.80 mmol) and [1,1-Bis(diphenylphosphino)ferrocene]dichloropalladium(II) (117.18 mg, 160.15 mmol) in N,N-dimethylformaldehyde (5 mL) was degassed and purged with nitrogen 3 times. The mixture was stirred at 80° C. for 12 h under a nitrogen atmosphere. The mixture was diluted with water (10 mL) and extracted with ethyl acetate (3×30 mL). The combined organic layers were dried over sodium sulphate and concentrated in vacuo. The residue was purified by column chromatography (silica gel, 100-200 mesh, 0-10% ethyl acetate in petroleum ether) affording 2-(6,8-difluoro-1-naphthyl)-4,4,5,5-tetramethyl-1,3,2-dioxaborolane (140 mg, 30.13%) as a yellow oil: $^1$H NMR (400 MHz, Dimethyl sulfoxide-d6) δ 8.06-8.00 (m, TH), 7.75-7.57 (m, 3H), 7.51-7.44 (m, TH), 1.36 (s, 12H). LCMS Rt=0.726 min, m/z=290.1 [M+H]$^+$.

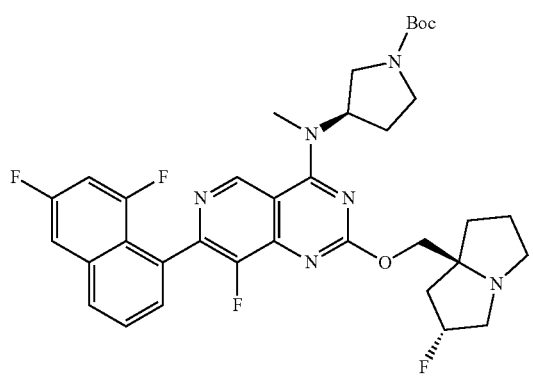 [SMILES: CN(c1nc(OC[C@@]23CCCN2C[C@H](F)C3)nc2c(F)c(-c3cccc4cc(F)cc(F)c34)ncc12)[C@@H]1CCN(C(=O)OC(C)(C)C)C1]

Step 5: (R)-tert-butyl 3-((7-(6,8-difluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate The Suzuki reaction was prepared in a similar fashion to Method #2, Step 5. The residue was purified by reverse phase HPLC (column: Phenomenex Luna 80*30 mm*3 μm; mobile phase: [water(TFA)-ACN]; B %: 15%-50%, 8 min) affording (R)-tert-butyl 3-((7-(6,8-difluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (140 mg, 60.03%) as a white solid. LCMS Rt=0.797 min, m/z=666.3 [M+H]$^+$.

1002

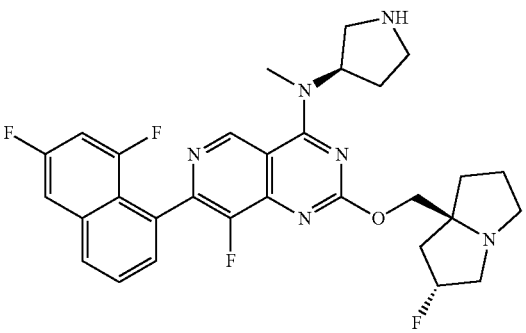 [SMILES: CN(c1nc(OC[C@@]23CCCN2C[C@H](F)C3)nc2c(F)c(-c3cccc4cc(F)cc(F)c34)ncc12)[C@@H]1CCNC1]

Step 6: 7-(6,8-difluoronaphthalen-1-yl)-8-fluoro-2-(((2R,7aS)-2-fluorohexahydro-1H-pyrrolizin-7a-yl)methoxy)-N-methyl-N—((R)-pyrrolidin-3-yl)pyrido[4,3-d]pyrimidin-4-amine The deprotection of the Boc group was prepared in a similar fashion to Method #2, Step 6. The mixture was concentrated in vacuo affording 7-(6,8-difluoronaphthalen-1-yl)-8-fluoro-2-(((2R,7aS)-2-fluorohexahydro-1H-pyrrolizin-7a-yl)methoxy)-N-methyl-N—((R)-pyrrolidin-3-yl)pyrido[4,3-d]pyrimidin-4-amine (130 mg, crude, trifluoroacetate salt) as a brown oil, which was used in the next step without further purification. LCMS Rt=0.617 min, m/z=566.2 [M+H]$^+$.

Step 7: 1-((R)-3-((7-(6,8-difluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)prop-2-en-1-one The amide coupling reaction was prepared in a similar fashion to Method #2, Step 7. The resulting residue was purified by reverse phase HPLC (column: Waters Xbridge Prep OBD C18 100*30 mm*10 um; mobile phase: [water (NH$_4$HCO$_3$)—Acetonitrile]; B %: 40%-70%, 8 min) affording 1-((R)-3-((7-(6,8-difluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)prop-2-en-1-one (38.58 mg, 37.49%) as a pale yellow solid: $^1$H NMR (400 MHz, Acetonitrile-d3) δ 9.15 (d, J=1.4 Hz, 1H), 8.01 (br d, J=8.3 Hz, 1H), 7.68 (t, J=7.7 Hz, 1H), 7.57-7.53 (m, 1H), 7.14-7.06 (m, 1H), 6.60-6.45 (m, 1H), 6.26-6.18 (m, 1H), 5.69-5.61 (m, 1H), 5.15 (br s, 2H), 4.20-4.15 (m, 1H), 4.12-4.07 (m, 1H), 4.06-3.87 (m, 1H), 3.86-3.74 (m, 1H), 3.65-3.57 (m, 1H), 3.57-3.37 (m, 2H), 3.36 (s, 3H), 3.17-3.08 (m, 2H), 3.07-3.03 (m, 1H), 2.90-2.83 (m, 1H), 2.30-2.19 (m, 2H), 2.18-2.10 (m, 1H), 2.08 (d, J=3.3 Hz, 1H), 2.05-1.98 (m, 1H), 1.89-1.78 (m, 3H).

LCMS (5% to 95% acetonitrile in water+0.03% ammonium bicarbonate over 6 min); retention time 3.883 min, ESI+ found [M+H]=620.3

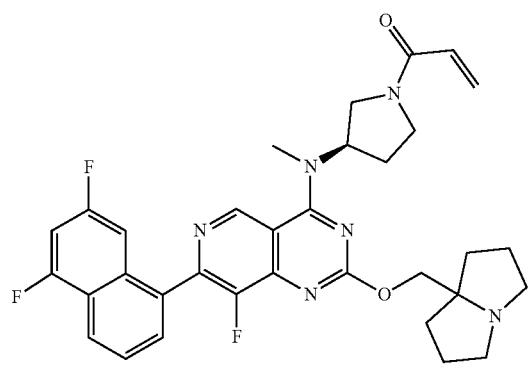 [SMILES: C=CC(=O)N1CC[C@@H](N(C)c2nc(OCC34CCCN3CCC4)nc3c(F)c(-c4cccc5c(F)cc(F)cc45)ncc23)C1]

Example 269 (Method 2): (R)-1-(3-((7-(5,7-difluoronaphthalen-1-yl)-8-fluoro-2-((hexahydro-1H-pyrrolizin-7a-yl)methoxy)pyrido[4,3-d]pyrimidin-4-yl)(methyl)amino)pyrrolidin-1-yl)prop-2-en-1-one

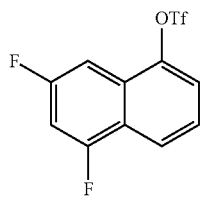 [SMILES: O=S(=O)(Oc1cccc2c(F)cc(F)cc12)C(F)(F)F]

Step 1: (5,7-difluoro-1-naphthyl) trifluoromethanesulfonate

To a mixture of 5,7-difluoronaphthalen-1-ol (2.2 g, 12.21 mmol) in dichloromethane (30 mL) was added N,N-diisopropylethylamine (6.31 g, 48.85 mmol) and trifluoromethanesulfonic anhydride (4.48 g, 15.88 mmol), and the mixture was stirred at 0° C. for 0.5 h under a nitrogen atmosphere. The reaction mixture was quenched with saturated sodium bicarbonate (20 mL) and extracted with dichloromethane (3×30 mL). The combined organic layers were dried over sodium sulphate and concentrated in vacuo. The residue was purified by column chromatography (silica gel, 100-200 mesh, 0-10% ethyl acetate in petroleum ether) affording (5,7-difluoro-1-naphthyl) trifluoromethanesulfonate (2.2 g, 57.70%) as a yellow oil. LCMS Rt=0.720 min, m/z=312.0 [M +H]+.

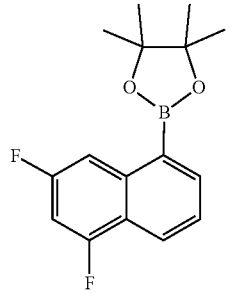 [SMILES: CC1(C)OB(c2cccc3c(F)cc(F)cc23)OC1(C)C]

Step 2: 2-(5,7-difluoro-1-naphthyl)-4,4,5,5-tetramethyl-1,3,2-dioxaborolane

A mixture of (5,7-difluoro-1-naphthyl) trifluoromethanesulfonate (2 g, 6.41 mmol), 4,4,5,5-tetramethyl-2-(4,4,5,5-tetramethyl-1,3,2-dioxaborolan-2-yl)-1,3,2-dioxaborolane (2.44 g, 9.61 mmol), potassium acetate (1.89 g, 19.22 mmol), and [1,1-Bis(diphenylphosphino)ferrocene]dichloropalladium(II) (468.72 mg, 640.59 μmol) in N,N-dimethylformaldehyde (20 mL) was degassed and purged with nitrogen 3 times. The mixture was stirred at 80° C. for 12 h under a nitrogen atmosphere. The mixture was diluted with water (50 mL) and extracted with ethyl acetate (3×50 mL). The combined organic layers were dried over sodium sulphate and concentrated in vacuo. The residue was purified by column chromatography (silica gel, 100-200 mesh, 0-10% ethyl acetate in petroleum ether) affording 2-(5,7-difluoro-1-naphthyl)-4,4,5,5-tetramethyl-1,3,2-dioxaborolane (1.18 g, 63.49%) as a yellow solid: $^1$H NMR (400 MHz, Dimethyl sulfoxide-d6) δ 8.25-8.16 (m, 2H), 8.10 (d, J=6.8 Hz, 1H), 7.61 (dd, J=7.1, 8.3 Hz, 1H), 7.50 (ddd, J=2.4, 9.0, 11.0 Hz, 1H), 1.41-1.35 (m, 12H).

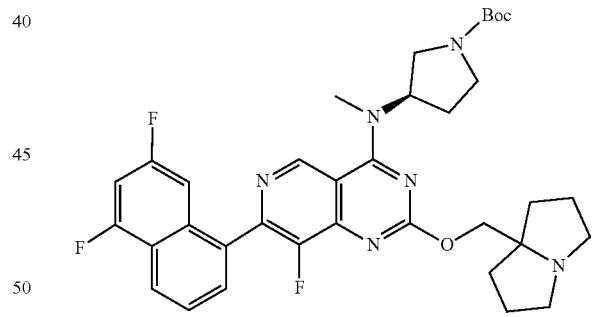

Step 3: (R)-tert-butyl 3-((7-(5,7-difluoronaphthalen-1-yl)-8-fluoro-2-((hexahydro-1H-pyrrolizin-7a-yl)methoxy)pyrido[4,3-d]pyrimidin-4-yl)(methyl)amino)pyrrolidine-1-carboxylate The Suzuki reaction was prepared in a similar fashion to Method #2, Step 5. The residue was purified by phase reverse HPLC (column: Phenomenex Luna 100*40 mm*3 μm; mobile phase: [water(TFA)-ACN]; B %: 35%-80%, 8 min) affording (R)-tert-butyl 3-((7-(5,7-difluoronaphthalen-1-yl)-8-fluoro-2-((hexahydro-1H-pyrrolizin-7a-yl)methoxy)pyrido[4,3-d]pyrimidin-4-yl)(methyl)amino)pyrrolidine-1-carboxylate (200 mg, 27.32%, trifluoroacetate salt) as a white solid. LCMS Rt=0.787 min, m/z=648.3 [M+H]+.

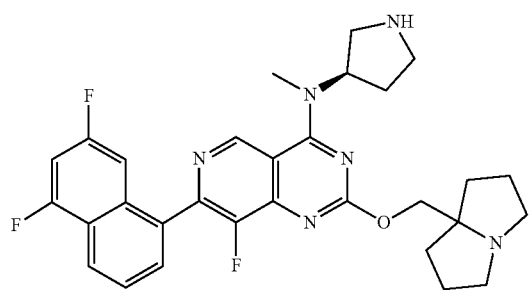 [SMILES: CN(c1nc(OCC23CCCN2CCC3)nc2c(F)c(-c3cccc4c(F)cc(F)cc34)ncc12)[C@@H]1CCNC1]

Step 4: (R)-7-(5,7-difluoronaphthalen-1-yl)-8-fluoro-2-((hexahydro-1H-pyrrolizin-7a-yl)methoxy)-N-methyl-N-(pyrrolidin-3-yl)pyrido[4,3-d]pyrimidin-4-amine The deprotection of the Boc group was prepared in a similar fashion to Method #2, Step 6. The residue was concentrated in vacuo affording (R)-7-(5,7-difluoronaphthalen-1-yl)-8-fluoro-2-((hexahydro-TH-pyrrolizin-7a-yl)methoxy)-N-methyl-N-(pyrrolidin-3-yl)pyrido[4,3-d]pyrimidin-4-amine (100 mg, crude, trifluoroacetate salt) as a brown oil, which was used in the next step without further purification. LCMS Rt=0.643 min, m/z=548.3 [M+H]+.

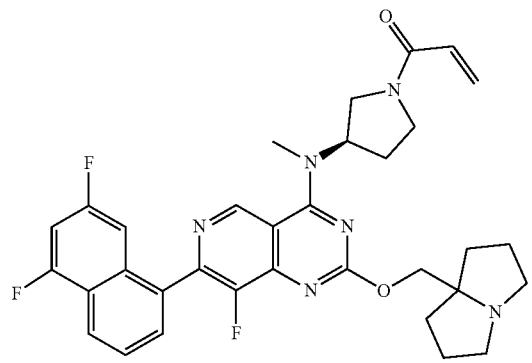 [SMILES: C=CC(=O)N1CC[C@@H](N(C)c2nc(OCC34CCCN3CCC4)nc3c(F)c(-c4cccc5c(F)cc(F)cc45)ncc23)C1]

Step 5: (R)-1-(3-((7-(5,7-difluoronaphthalen-1-yl)-8-fluoro-2-((hexahydro-1H-pyrrolizin-7a-yl)methoxy)pyrido[4,3-d]pyrimidin-4-yl)(methyl)amino)pyrrolidin-1-yl)prop-2-en-1-one The amide coupling reaction was prepared in a similar fashion to Method #2, Step 7. The resulting residue was purified by reverse phase HPLC (column: Waters Xbridge Prep OBD C18 100*30 mm*10 μm; mobile phase: [water (NH$_4$HCO$_3$)—Acetonitrile]; B %: 50%-80%, 8 min) affording (R)-1-(3-((7-(5,7-difluoronaphthalen-1-yl)-8-fluoro-2-((hexahydro-1H-pyrrolizin-7a-yl)methoxy)pyrido[4,3-d]pyrimidin-4-yl)(methyl)amino)pyrrolidin-1-yl)prop-2-en-1-one (16.64 mg, 15.00%) as a white solid: $^1$H NMR (400 MHz, Acetonitrile-d3) δ 9.26 (s, 1H), 8.24 (d, J=8.3 Hz, 1H), 7.82 (d, J=7.0 Hz, 1H), 7.76-7.67 (m, 1H), 7.36 (br d, J=11.0 Hz, 1H), 7.27-7.15 (m, 1H), 6.58 (ddd, J=10.4, 13.7, 16.7 Hz, 1H), 6.24 (td, J=2.7, 16.8 Hz, 1H), 5.73-5.60 (m, 1H), 5.47-5.28 (m, 1H), 4.17 (s, 2H), 4.11-3.92 (m, 1H), 3.91-3.77 (m, 1H), 3.71-3.61 (m, 1H), 3.60-3.40 (m, 4H), 3.02-2.93 (m, 2H), 2.60 (td, J=6.8, 9.9 Hz, 2H), 2.43-2.27 (m, 2H), 1.99-1.96 (m, 1H), 1.93 (br s, 1H), 1.90-1.73 (m, 4H), 1.68-1.59 (m, 2H).

LCMS (5% to 95% acetonitrile in water+0.03% ammonium bicarbonate over 6 min); retention time 2.141 min, ESI+ found [M+H]=602.3.

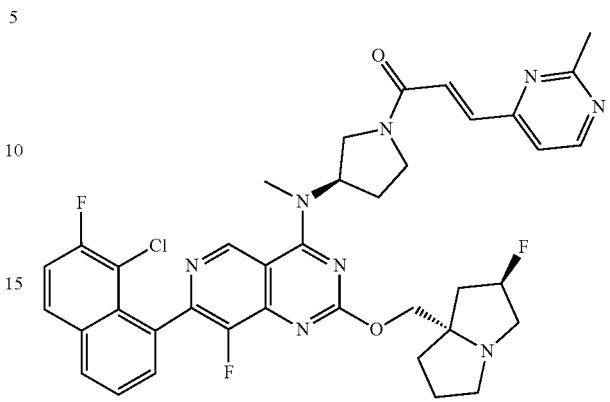

Example 270 (Method 2): (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(2-methylpyrimidin-4-yl)prop-2-en-1-one

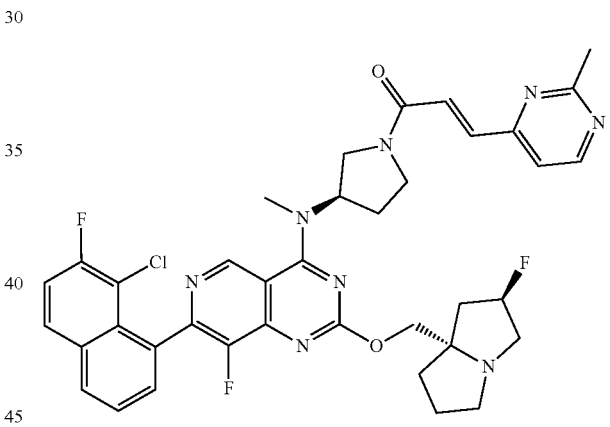

Step 1: (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(2-methylpyrimidin-4-yl)prop-2-en-1-one The amide coupling reaction was prepared in a similar fashion to Method #2, Step 7. The crude product was purified by reverse phase prep-HPLC (column: Phenomenex Luna C18 75*30 mm*3 μm; mobile phase: [water(FA)-ACN]; B %: 1%-30%, 8 min) affording (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(2-methylpyrimidin-4-yl)prop-2-en-1-one (7.97 mg, 7.17%, formate salt) as a white solid: $^1$H NMR (400 MHz, Acetonitrile-d3) δ 9.30-9.18 (m, 1H), 8.68 (dd, J=5.1, 7.9 Hz, 1H), 8.25 (br s, 1H), 8.16-8.04 (m, 2H), 7.78-7.61 (m, 2H), 7.58-7.49 (m, 2H), 7.39 (t, J=5.1 Hz, 1H), 5.49-5.26 (m, 2H), 4.46-4.17 (m, 3H), 4.07-4.00 (m, 1H), 3.78 (br s, 2H), 3.47 (d, J=2.5 Hz, 4H), 3.41-3.23 (m, 2H), 3.11-2.99 (m, 1H), 2.64-2.55 (m, 3H), 2.52-2.33 (m, 3H), 2.32-2.12 (m, 3H), 2.07-1.97 (m, 2H).

LCMS (5% to 95% acetonitrile in water+0.1% formic acid over 6 min); retention time 2.179 min, ESI+ found [M+H]=728.3.

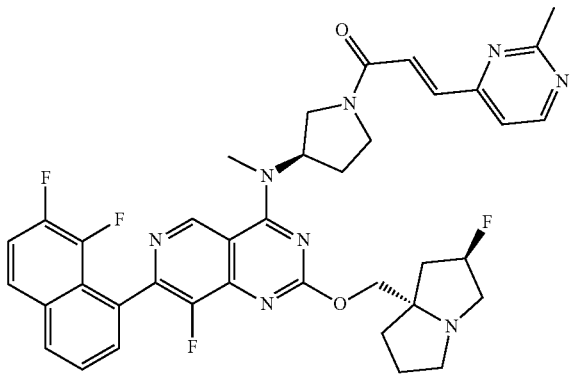 [SMILES: Cc1nccc(/C=C/C(=O)N2CC[C@@H](N(C)c3nc(OC[C@@]45CCCN4C[C@H](F)C5)nc4c(F)c(-c5cccc6ccc(F)c(F)c56)ncc34)C2)n1]

Example 271 (Method 2): (E)-1-((R)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(2-methylpyrimidin-4-yl)prop-2-en-1-one

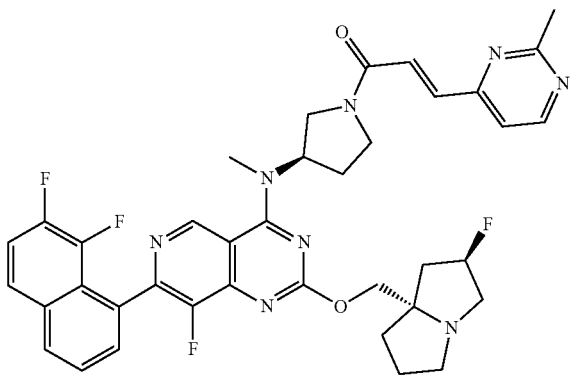 [SMILES: Cc1nccc(/C=C/C(=O)N2CC[C@@H](N(C)c3nc(OC[C@@]45CCCN4C[C@H](F)C5)nc4c(F)c(-c5cccc6ccc(F)c(F)c56)ncc34)C2)n1]

Step 1: (E)-1-((R)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(2-methylpyrimidin-4-yl)prop-2-en-1-one The amide coupling reaction was prepared in a similar fashion to Method #2, Step 7. The crude product was purified by reverse phase prep-HPLC (column: Waters Xbridge Prep OBD C18 150*40 mm*10 um; mobile phase: [water(NH₄HCO₃)-ACN]; B %: 25%-55%, 8 min) affording (E)-1-((R)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(2-methylpyrimidin-4-yl)prop-2-en-1-one (10.05 mg, 10.26%) as a yellow amorphous solid: ¹H NMR (400 MHz, Acetonitrile-d3) δ 9.23 (d, J=3.1 Hz, 1H), 8.68 (t, J=5.4 Hz, 1H), 8.13-8.06 (m, 1H), 7.93-7.84 (m, 1H), 7.71-7.64 (m, 2H), 7.58-7.41 (m, 3H), 7.34 (dd, J=5.2, 6.7 Hz, 1H), 5.48-5.11 (m, 2H), 4.26-4.19 (m, 1H), 4.17-4.10 (m, 1H), 4.08-3.96 (m, 1H), 3.91-3.73 (m, 2H), 3.67-3.50 (m, 1H), 3.45 (d, J=4.6 Hz, 3H), 3.19-3.01 (m, 3H), 2.81 (s, 1H), 2.69-2.61 (m, 3H), 2.48-2.26 (m, 2H), 2.09-1.99 (m, 3H), 1.87-1.78 (m, 3H).

LCMS (5% to 95% acetonitrile in water+0.03% ammonium bicarbonate over 6 min); retention time 2.690 min, ESI+ found [M+H]=712.3.

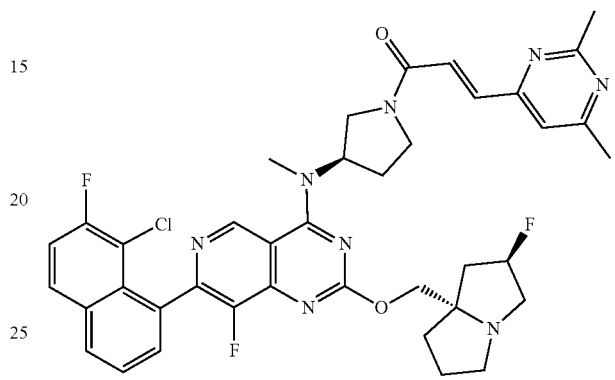

Example 272 (Method 2): (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(2,6-dimethylpyrimidin-4-yl)prop-2-en-1-one

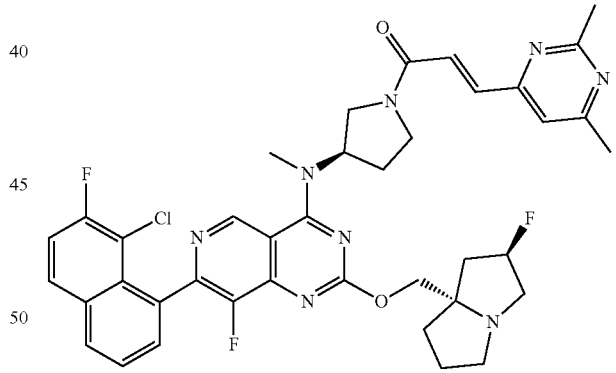

Step 1: (E)-1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(2,6-dimethylpyrimidin-4-yl)prop-2-en-1-one The amide coupling reaction was prepared in a similar fashion to Method #2, Step 7. The crude product was purified by reverse phase prep-HPLC (column: Waters Xbridge Prep OBD C18 150*40 mm*10 um; mobile phase: [water(NH₄HCO₃)-ACN]; B %: 30%-60%, 8 min) affording (E)-1-((R)-3-((7-(8-chloro-7-fluoronaphthalen-1-yl)-8-fluoro-2-(((2R,7aS)-2-fluorotetrahydro-1H-pyrrolizin-7a (5H)-yl)methoxy)pyrido[4,3-d]pyrimidin-4-yl)(methyl)amino)pyrrolidin-1-yl)-3-(2,6-dimethylpyrimidin-4-yl)prop-2-en-1-one (7.97 mg, 7.17%) as a white solid: ¹H NMR (400 MHz, Acetonitrile-d3) δ 9.21-9.16 (m, 1H), 8.14-8.03 (m, 2H), 7.71-7.62 (m, 2H), 7.54-7.46 (m, 2H), 7.44-7.37 (m, 1H), 7.26-7.17 (m, 1H), 5.45-5.09 (m, 2H), 4.27-4.11 (m, 2H), 4.04-3.95 (m, 1H), 3.86 (ddd, J=4.3, 7.6, 12.2 Hz, 1H), 3.80-3.70 (m, 1H), 3.67-3.51 (m, 1H), 3.47-3.40 (m, 3H), 3.19-3.00 (m, 3H), 2.92-2.82 (m, 1H), 2.60 (d, J=14.4 Hz, 3H), 2.47-2.41 (m, 3H), 2.39-2.26 (m, 2H), 2.16-2.00 (m, 3H), 1.91-1.77 (m, 3H).

LCMS (5% to 95% acetonitrile in water+0.03% ammonium bicarbonate over 6 min); retention time 2.964 min, ESI+ found [M+H]=742.3.

Step 1: (E)-1-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(2,6-dimethylpyrimidin-4-yl)prop-2-en-1-one The amide coupling reaction was prepared in a similar fashion to Method #2, Step 7. The crude product was purified by reverse phase prep-HPLC (column: Waters Xbridge Prep OBD C18 150*40 mm*10 μm; mobile phase: [water(NH₄HCO₃)-ACN]; B %: 30%-60%, 8 min) affording (E)-1-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(2,6-dimethylpyrimidin-4-yl)prop-2-en-1-one (29.28 mg, 16.68%) as a white solid: ¹H NMR (400 MHz, Acetonitrile-d3) δ 9.24 (s, 1H), 8.18-8.01 (m, 2H), 7.74-7.63 (m, 2H), 7.51 (t, J=9.0 Hz, 1H), 7.38-7.32 (m, 1H), 7.23-7.15 (m, 2H), 5.32-5.06 (m, 1H), 4.46 (t, J=8.4 Hz, 1H), 4.33-4.22 (m, 2H), 4.20-4.12 (m, 3H), 3.95-3.86 (m, 1H), 3.60-3.53 (m, 3H), 3.29-3.19 (m, 1H), 3.13-3.06 (m, 2H), 3.02 (br s, 1H), 2.90-2.84 (m, 1H), 2.59 (s, 3H), 2.44 (s, 3H), 2.11 (br s, 1H), 2.09-1.96 (m, 3H), 1.88-1.75 (m, 3H).

LCMS (5% to 95% acetonitrile in water+0.03% ammonium bicarbonate over 6 min); retention time 2.909 min, ESI+ found [M+H]=742.3.

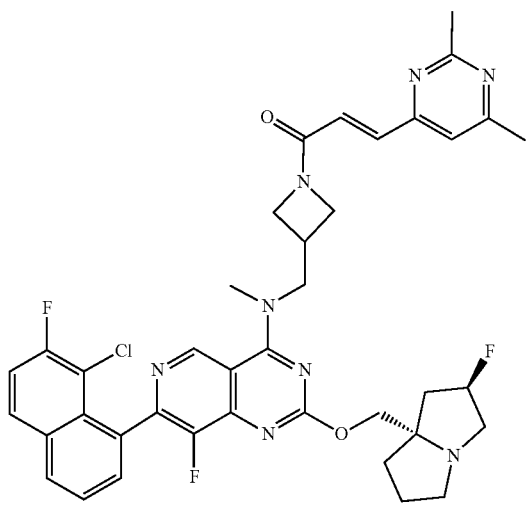 [SMILES: Cc1cc(/C=C/C(=O)N2CC(CN(C)c3nc(OC[C@@]45CCCN4C[C@H](F)C5)nc4c(F)c(-c5cccc6ccc(F)c(Cl)c56)ncc34)C2)nc(C)n1]

Example 273 (Method 2): (E)-1-(3-(((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(2,6-dimethylpyrimidin-4-yl)prop-2-en-1-one

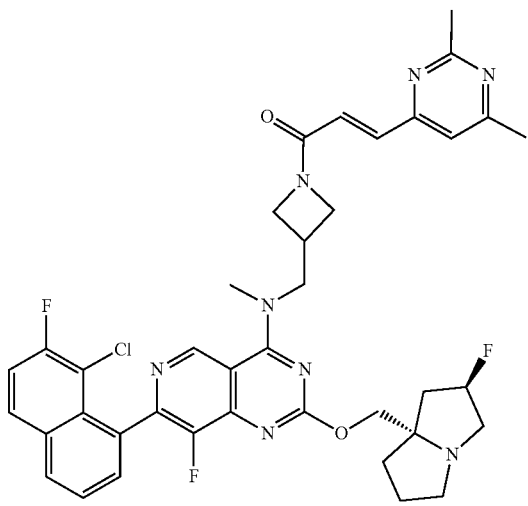

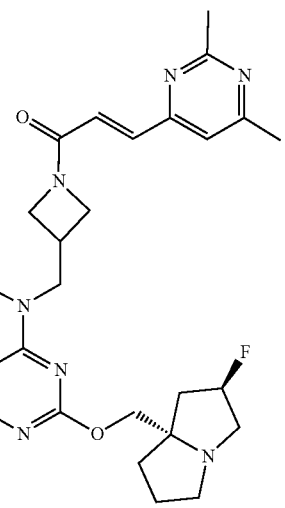

Example 274 (Method 2): (E)-1-(3-(((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(2,6-dimethylpyrimidin-4-yl)prop-2-en-1-one

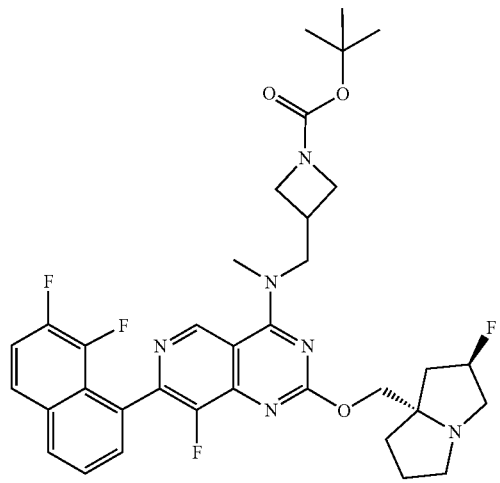 [SMILES: CN(CC1CN(C(=O)OC(C)(C)C)C1)c1nc(OC[C@@]23CCCN2C[C@H](F)C3)nc2c(F)c(-c3cccc4ccc(F)c(F)c34)ncc12]

Step 1: tert-butyl 3-(((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidine-1-carboxylate The Suzuki reaction was prepared in a similar fashion to Method #2, Step 5. The crude product was purified by reverse phase prep-HPLC (column: Phenomenex Luna C18 100*40 mm*3 μm; mobile phase: [water(TFA)-ACN]; B %: 35%-80%, 8 min) affording tert-butyl 3-(((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidine-1-carboxylate (190 mg, 45.18%, trifluoroacetate salt) as a yellow oil. LCMS Rt=1.869 min, m/z=666.3 [M+H]+.

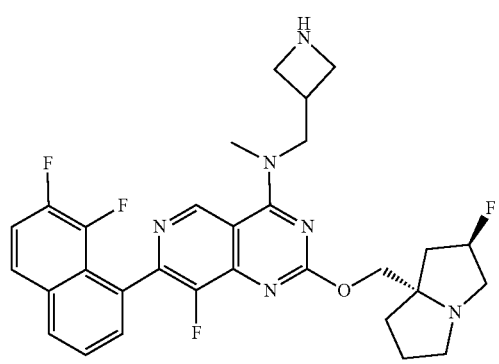 [SMILES: CN(CC1CNC1)c1nc(OC[C@@]23CCCN2C[C@H](F)C3)nc2c(F)c(-c3cccc4ccc(F)c(F)c34)ncc12]

Step 2: N-(azetidin-3-ylmethyl)-7-(7,8-difluoronaphthalen-1-yl)-8-fluoro-2-(((2R,7aS)-2-fluorotetrahydro-1H-pyrrolizin-7a(5H)-yl)methoxy)-N-methylpyrido[4,3-d]pyrimidin-4-amine The deprotection of the Boc group was prepared in a similar fashion to Method #1, Step 9. The reaction mixture was concentrated in vacuo affording N-(azetidin-3-ylmethyl)-7-(7,8-difluoronaphthalen-1-yl)-8-fluoro-2-(((2R,7aS)-2-fluorotetrahydro-1H-pyrrolizin-7a(5H)-yl)methoxy)-N-methylpyrido[4,3-d]pyrimidin-4-amine (90 mg, crude, trifluoroacetic salt) as a yellow oil, which was used in the next step without further purification. LCMS Rt=0.617 min, m/z=566.2 [M+H]+.

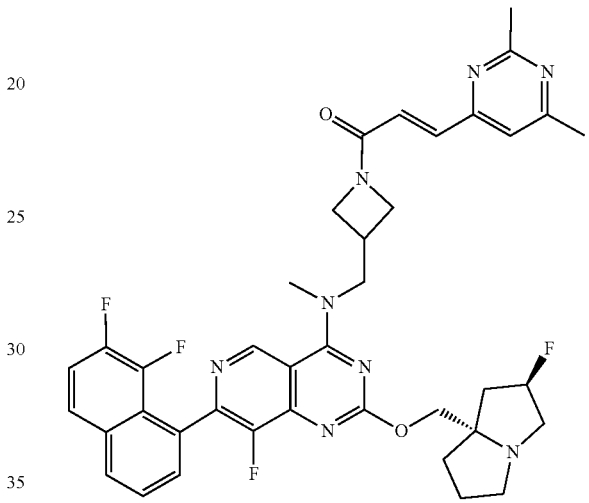

Step 3: (E)-1-(3-(((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(2,6-dimethylpyrimidin-4-yl)prop-2-en-1-one The amide coupling reaction was prepared in a similar fashion to Method #2, Step 7. The crude product was purified by reverse phase prep-HPLC (column: Waters Xbridge Prep OBD C18 150*40 mm*10 μm; mobile phase: [water(NH₄HCO₃)-ACN]; B %: 30%-60%, 8 min) affording (E)-1-(3-(((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)-3-(2,6-dimethylpyrimidin-4-yl)prop-2-en-1-one (13.37 mg, 12.73%) as a yellow amorphous solid: $^1$H NMR (400 MHz, Acetonitrile-d3) δ 9.32-9.21 (m, 1H), 8.17-8.02 (m, 1H), 7.94-7.86 (m, 1H), 7.73-7.62 (m, 2H), 7.57-7.49 (m, 1H), 7.38-7.32 (m, 1H), 7.24-7.15 (m, 2H), 5.30-5.10 (m, 1H), 4.51-4.40 (m, 1H), 4.33-4.23 (m, 1H), 4.21-4.07 (m, 3H), 3.97-3.85 (m, 1H), 3.77-3.64 (m, 1H), 3.63-3.55 (m, 2H), 3.26-3.18 (m, 1H), 3.14-3.05 (m, 2H), 3.04-2.98 (m, 2H), 2.89-2.79 (m, 1H), 2.62-2.54 (m, 3H), 2.47-2.40 (m, 3H), 2.38 (s, 1H), 2.10-1.97 (m, 3H), 1.88-1.66 (m, 3H).
LCMS (5% to 95% acetonitrile in water+0.03% ammonium bicarbonate over 6 min); retention time 2.886 min, ESI+ found [M+H]=726.3.

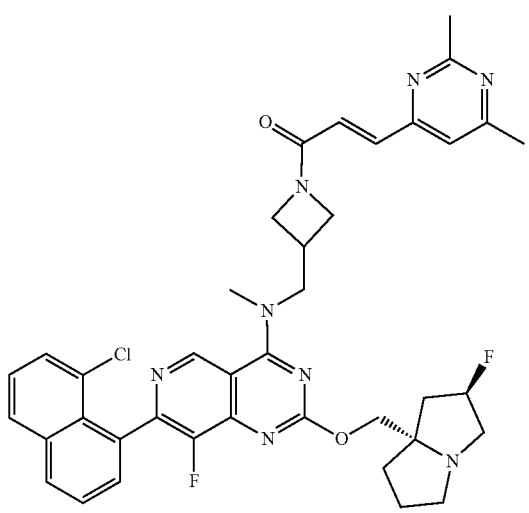 [SMILES: Cc1cc(/C=C/C(=O)N2CC(CN(C)c3nc(OC[C@@]45CCCN4C[C@H](F)C5)nc4c(F)c(-c5cccc6cccc(Cl)c56)ncc34)C2)nc(C)n1]

Example 275 (Method 1): (E)-1-(3-(((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)methyl)azetidin-1-yl)-3-(2,6-dimethylpyrimidin-4-yl)prop-2-en-1-one

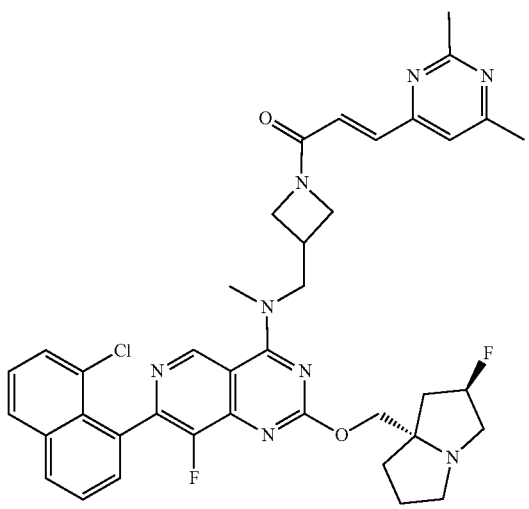 [SMILES: Cc1cc(/C=C/C(=O)N2CC(CN(C)c3nc(OC[C@@]45CCCN4C[C@H](F)C5)nc4c(F)c(-c5cccc6cccc(Cl)c56)ncc34)C2)nc(C)n1]

Step 1: (E)-1-(3-(((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)methyl)azetidin-1-yl)-3-(2,6-dimethylpyrimidin-4-yl)prop-2-en-1-one The amide coupling reaction was prepared in a similar fashion to Method #1, Step 10. The residue was purified by reverse phase HPLC (column: Waters Xbridge Prep OBD C18 150*40 mm*10 μm; mobile phase: [water(NH$_4$HCO$_3$)-ACN]; B %: 30%-60%, 8 min) affording (E)-1-(3-(((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)methyl)azetidin-1-yl)-3-(2,6-dimethylpyrimidin-4-yl)prop-2-en-1-one: $^1$H NMR (400 MHz, Acetonitrile-d3) δ 9.24 (s, 1H), 8.19-8.06 (m, 1H), 8.01 (d, J=7.9 Hz, 1H), 7.71-7.65 (m, 1H), 7.63-7.58 (m, 2H), 7.54-7.48 (m, 1H), 7.38-7.32 (m, 1H), 7.22-7.16 (m, 2H), 5.33-5.06 (m, 1H), 4.45 (br t, J=8.4 Hz, 1H), 4.33-4.21 (m, 2H), 4.20-4.04 (m, 4H), 3.91 (br d, J=5.6 Hz, 1H), 3.58 (s, 3H), 3.28-3.17 (m, 1H), 3.10 (br d, J=12.3 Hz, 2H), 3.06-3.01 (m, 1H), 2.89-2.81 (m, 1H), 2.59 (s, 3H), 2.44 (s, 3H), 2.09-1.97 (m, 3H), 1.87-1.76 (m, 3H).

LCMS (5% to 95% acetonitrile in water+0.03% trifluoroacetic acid over 6 min); retention time 2.872 min, ESI+ found [M+H]=724.3.

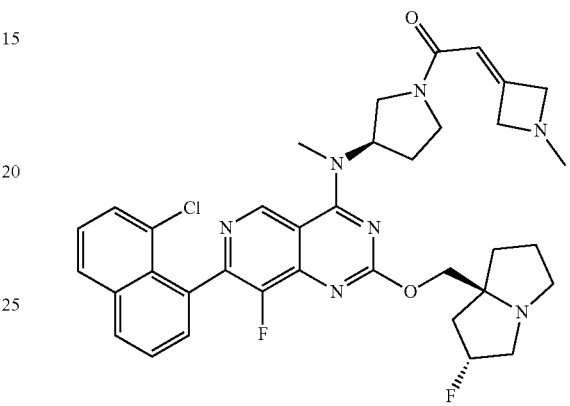

Example 276 (Method 8): 1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-2-(1-methylazetidin-3-ylidene)ethan-1-one

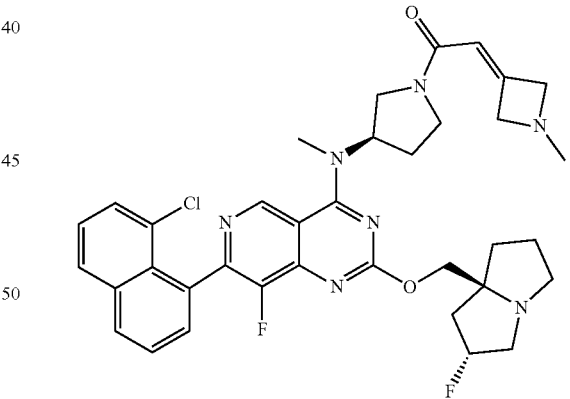

Step 1: 1-((R)-3-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-2-(1-methylazetidin-3-ylidene)ethan-1-one The HWE reaction was prepared in a similar fashion to Method #8, Step 4. The crude product was purified by reverse phase HPLC (column: Waters Xbridge Prep OBD C18 150*40 mm*10 μm; mobile phase: [water(NH$_4$HCO$_3$)-ACN]; B %: 30%-50%, 8 min) affording 1-((R)-3-((7-(8- chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-2-(1-methylazetidin-3-ylidene)ethan-1-one (8.35 mg, 20.32%) as a yellow solid: ¹H NMR (400 MHz, Acetonitrile-d3) δ 9.20 (d, J=2.6 Hz, 1H), 8.15 (d, J=7.8 Hz, 1H), 8.04 (d, J=8.0 Hz, 1H), 7.75-7.69 (m, 1H), 7.67-7.59 (m, 2H), 7.58-7.51 (m, 1H), 6.07-5.97 (m, 1H), 5.43-5.18 (m, 2H), 4.26-4.11 (m, 4H), 4.07-3.89 (m, 3H), 3.88-3.75 (m, 1H), 3.68-3.47 (m, 2H), 3.47-3.37 (m, 3H), 3.16 (br d, J=6.5 Hz, 2H), 3.09 (s, 1H), 2.96-2.88 (m, 1H), 2.41 (d, J=2.0 Hz, 3H), 2.38-2.24 (m, 2H), 2.14-2.02 (m, 3H), 1.94-1.83 (m, 3H).

LCMS (5% to 95% acetonitrile in water+0.1% trifluoroacetic acid over 6 min); retention time 1.918 min, ESI+ found [M+H]=673.3.

reverse phase HPLC (column: Waters Xbridge Prep OBD C18 150*40 mm*10 um; mobile phase: [water(NH₄HCO₃)-ACN]; B %: 40%-70%, 8 min) affording (E)-1-((R)-3-((7-(8-ethyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(2-methylpyrimidin-4-yl)prop-2-en-1-one (39.04 mg, 36.26%) as a gray amorphous solid: ¹H NMR (400 MHz, Dimethylsulfoxide-d6) δ 9.24-9.19 (m, 1H), 8.74-8.66 (m, 1H), 8.07 (d, J=8.0 Hz, 1H), 7.97 (dd, J=6.1, 9.0 Hz, 1H), 7.60-7.52 (m, 2H), 7.52-7.42 (m, 3H), 7.42-7.36 (m, 1H), 5.40-5.07 (m, 2H), 4.19-3.98 (m, 3H), 3.95-3.69 (m, 2H), 3.59-3.43 (m, 1H), 3.42-3.38 (m, 3H), 3.06-2.91 (m, 3H), 2.80-2.69 (m, 1H), 2.58 (d, J=13.0 Hz, 3H), 2.42-2.31 (m, 2H), 2.29-2.21 (m, 1H), 2.20-2.10 (m, 1H), 2.08-1.89 (m, 3H), 1.80-1.65 (m, 3H), 0.75-0.67 (m, 3H).

LCMS (5% to 95% acetonitrile in water+0.03% ammonium bicarbonate over 6 min); retention time 2.275 min, ESI+ found [M+H]=722.3.

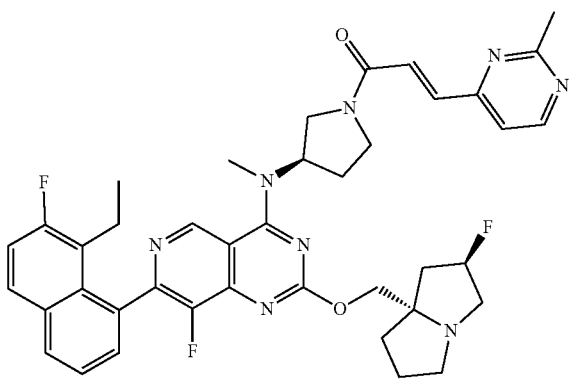

Example 277 (Method 1): (E)-1-((R)-3-((7-(8-ethyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(2-methylpyrimidin-4-yl)prop-2-en-1-one

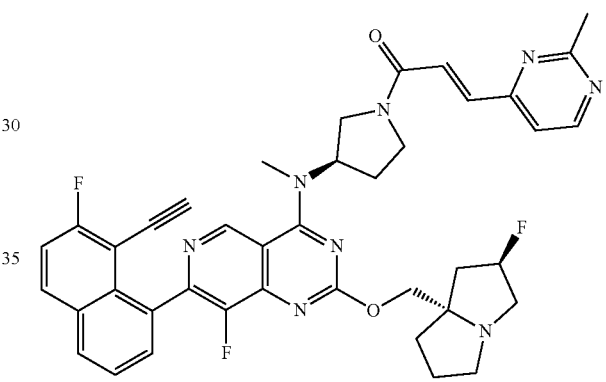

Example 278 (Method 2): (E)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(2-methylpyrimidin-4-yl)prop-2-en-1-one

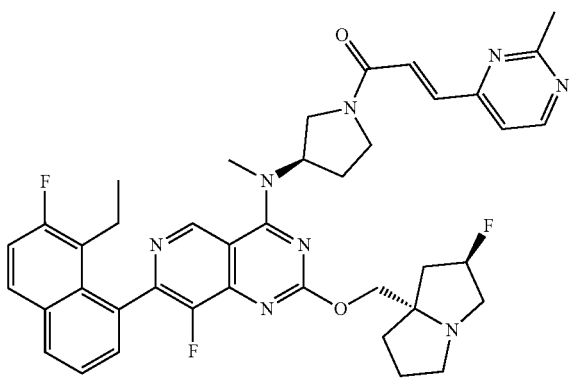 [SMILES: CCc1c(F)ccc2cccc(-c3ncc4c(N(C)[C@@H]5CCN(C(=O)/C=C/c6ccnc(C)n6)C5)nc(OC[C@@]56CCCN5C[C@H](F)C6)nc4c3F)c12]

Step 1: (E)-1-((R)-3-((7-(8-ethyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(2-methylpyrimidin-4-yl)prop-2-en-1-one The amide coupling reaction was prepared in a similar fashion to Method #1, Step 10. The residue was purified by

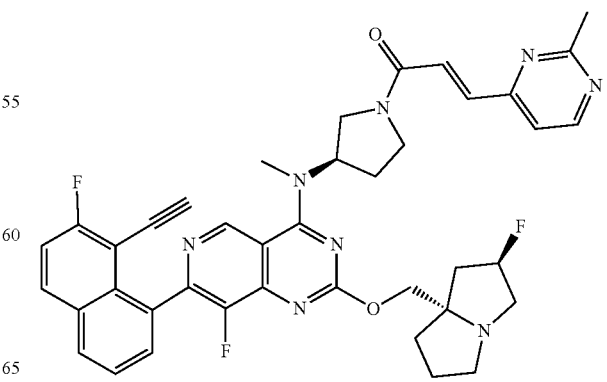

Step 1: (E)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(2-methylpyrimidin-4-yl)prop-2-en-1-one The amide coupling reaction was prepared in a similar fashion to Method #2, Step 7. The crude product was purified by reverse phase prep-HPLC (column: Waters Xbridge Prep OBD C18 150*40 mm*10 um; mobile phase: [water(NH$_4$HCO$_3$)-ACN]; B %: 35%-65%, 8 min) affording (E)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(2-methylpyrimidin-4-yl)prop-2-en-1-one (24.5 mg, 23.41%) as a yellow amorphous solid: $^1$H NMR (400 MHz, Dimethylsulfoxide-d6) δ 9.22 (t, J=4.6 Hz, 1H), 8.82-8.75 (m, 1H), 8.29-8.19 (m, 2H), 7.75-7.67 (m, 2H), 7.67-7.60 (m, 2H), 7.60-7.54 (m, 1H), 7.50-7.43 (m, 1H), 5.45-5.16 (m, 2H), 4.27-4.13 (m, 2H), 4.12-4.01 (m, 2H), 4.00-3.76 (m, 2H), 3.68-3.51 (m, 1H), 3.47 (d, J=2.8 Hz, 3H), 3.15-2.98 (m, 3H), 2.88-2.76 (m, 1H), 2.66 (d, J=12.7 Hz, 3H), 2.48-2.38 (m, 1H), 2.33 (br t, J=8.4 Hz, 1H), 2.18-2.11 (m, 1H), 2.10-1.97 (m, 2H), 1.88-1.72 (m, 3H).

LCMS Rt=2.160 min, m/z=718.3 [M+H]$^+$.

LCMS (5% to 95% acetonitrile in water+0.03% ammonium bicarbonate over 6 min); retention time 2.160 min, ESI+ found [M+H]=718.3.

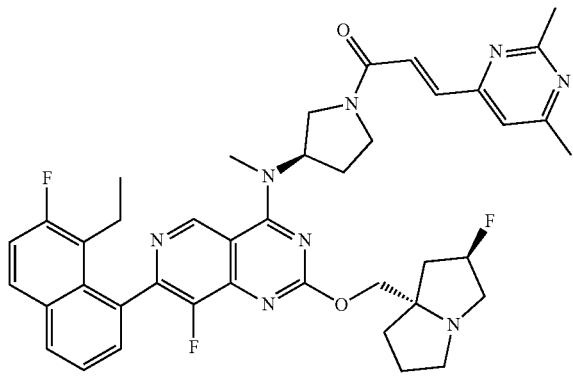 [SMILES: CCc1c(F)ccc2cccc(-c3ncc4c(N(C)[C@@H]5CCN(C(=O)/C=C/c6cc(C)nc(C)n6)C5)nc(OC[C@@]56CCCN5C[C@H](F)C6)nc4c3F)c12]

Example 279 (Method 1): (E)-3-(2,6-dimethylpyrimidin-4-yl)-1-((R)-3-((7-(8-ethyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one

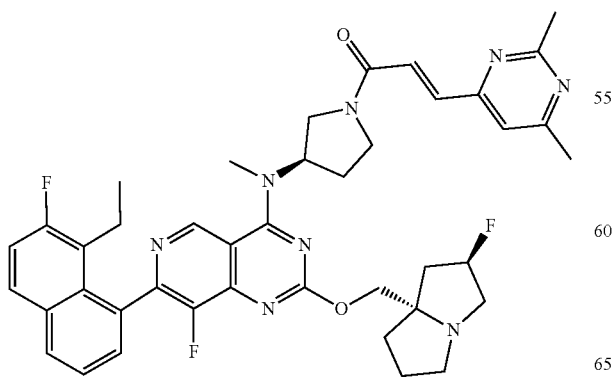

Step 1: (E)-3-(2,6-dimethylpyrimidin-4-yl)-1-((R)-3-((7-(8-ethyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one The amide coupling reaction was prepared in a similar fashion to Method #1, Step 10. The residue was purified by reverse phase HPLC (column: Waters Xbridge Prep OBD C18 150*40 mm*10 μm; mobile phase: [water(NH$_4$HCO$_3$)-ACN]; B %: 40%-70%, 8 min) affording (E)-3-(2,6-dimethylpyrimidin-4-yl)-1-((R)-3-((7-(8-ethyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (25.23 mg, 22.34%) as a yellow amorphous solid: $^1$H NMR (400 MHz, Dimethylsulfoxide-d6) δ 9.31 (t, J=5.4 Hz, 1H), 8.17 (d, J=8.0 Hz, 1H), 8.07 (dd, J=6.1, 9.0 Hz, 1H), 7.67-7.50 (m, 5H), 7.49-7.40 (m, 1H), 5.49-5.14 (m, 2H), 4.30-4.06 (m, 3H), 4.04-3.79 (m, 2H), 3.67-3.53 (m, 1H), 3.51 (br d, J=3.3 Hz, 3H), 3.20-2.97 (m, 4H), 2.90-2.80 (m, 1H), 2.65 (s, 1H), 2.62 (d, J=2.8 Hz, 1H), 2.58-2.53 (m, 2H), 2.49-2.40 (m, 3H), 2.38-2.22 (m, 2H), 2.21-1.97 (m, 3H), 1.92-1.73 (m, 3H), 0.84-0.77 (m, 3H)

LCMS Rt=2.274 min, m/z=736.4 [M+H]$^+$.

LCMS (5% to 95% acetonitrile in water+0.03% ammonium bicarbonate over 6 min); retention time 2.274 min, ESI+ found [M+H]=736.4.

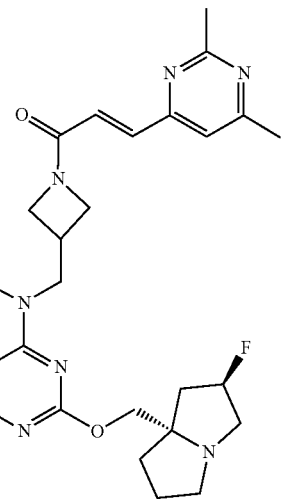

Example 280 (Method 14-master): (E)-3-(2,6-dimethylpyrimidin-4-yl)-1-(3-(((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)prop-2-en-1-one

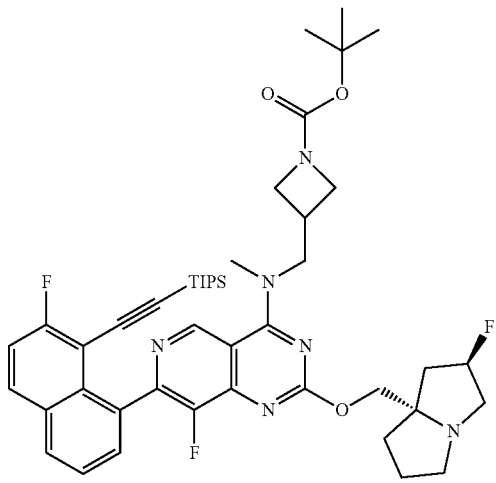

Step 1: tert-butyl 3-(((8-fluoro-7-(7-fluoro-8-((triisopropylsilyl)ethynyl)naphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)methyl)azetidine-1-carboxylate The Suzuki reaction was prepared in a similar fashion to Method #2, Step 5. The residue was purified by column chromatography (silica gel, 100-200 mesh, 0-100% ethyl acetate in petroleum ether) affording tert-butyl 3-(((8-fluoro-7-(7-fluoro-8-((triisopropylsilyl)ethynyl)naphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)methyl)azetidine-1-carboxylate (100 mg, 43.34%) as a brown solid. LCMS Rt =0.977 min, m/z=828.4 [M+H]⁺.

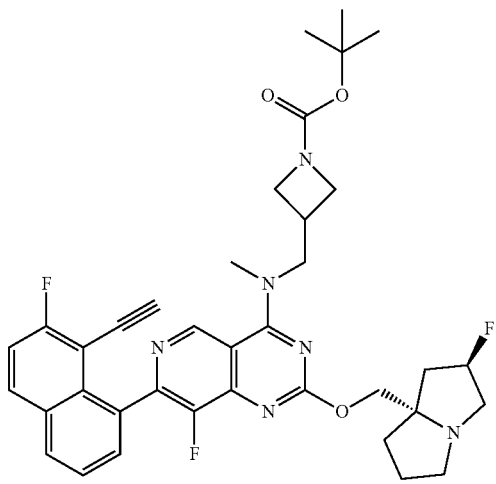 [SMILES: C#Cc1c(F)ccc2cccc(-c3ncc4c(N(C)CC5CN(C(=O)OC(C)(C)C)C5)nc(OC[C@@]56CCCN5C[C@H](F)C6)nc4c3F)c12]

Step 2: tert-butyl 3-(((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidine-1-carboxylate To a solution of tert-butyl 3-(((8-fluoro-7-(7-fluoro-8-((triisopropylsilyl)ethynyl)naphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)methyl)azetidine-1-carboxylate (95 mg, 114.59 μmol) in N,N-dimethylformaldehyde (1 mL) was added cesium fluoride (87.03 mg, 572.93 μmol), and the mixture was stirred at 20° C. for 1 h. The mixture was diluted with water (10 mL) and extracted with ethyl acetate (3×10 mL). The combined organic layers were dried over sodium sulphate and concentrated in vacuo. The residue was purified by column chromatography (silica gel, 100-200 mesh, 0-100% ethyl acetate in petroleum ether) affording tert-butyl 3-(((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidine-1-carboxylate (150 mg, crude) as a yellow oil, which was used in the next step without any further purification. LCMS Rt =0.707 min, m/z=672.3 [M+H]⁺.

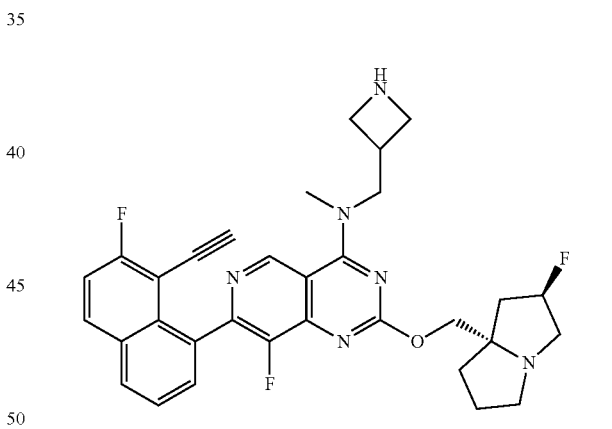

Step 3: N-(azetidin-3-ylmethyl)-7-(8-ethynyl-7-fluoronaphthalen-1-yl)-8-fluoro-2-(((2R,7aS)-2-fluorotetrahydro-1H-pyrrolizin-7a(5H)-yl)methoxy)-N-methylpyrido[4,3-d]pyrimidin-4-amine The deprotection of the Boc group was prepared in a similar fashion to Method #1, Step 9. The reaction mixture was concentrated in vacuo affording N-(azetidin-3-ylmethyl)-7-(8-ethynyl-7-fluoronaphthalen-1-yl)-8-fluoro-2-(((2R,7aS)-2-fluorotetrahydro-1H-pyrrolizin-7a(5H)-yl)methoxy)-N-methylpyrido[4,3-d]pyrimidin-4-amine (80 mg, crude, trifluoroacetic salt) as a brown gum, which was used in the next step without further purification. LCMS Rt=0.536 min, m/z=572.3 [M+H]⁺.

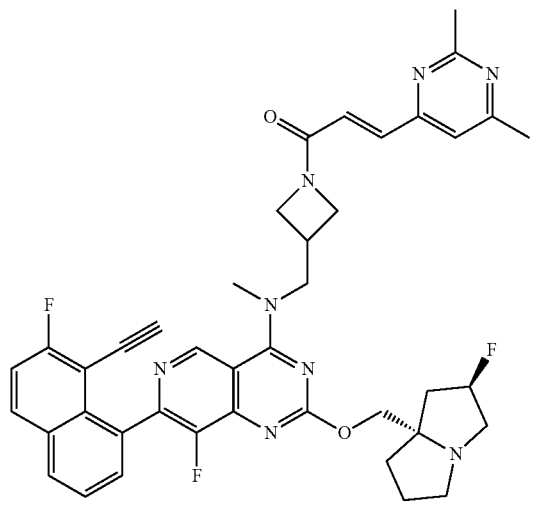 [SMILES: C#Cc1c(F)ccc2cccc(-c3ncc4c(N(C)CC5CN(C(=O)/C=C/c6cc(C)nc(C)n6)C5)nc(OC[C@@]56CCCN5C[C@H](F)C6)nc4c3F)c12]

Step 4: (E)-3-(2,6-dimethylpyrimidin-4-yl)-1-(3-(((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)prop-2-en-1-one The amide coupling reaction was prepared in a similar fashion to Method #2, Step 7. The crude product was purified by reverse phase prep-HPLC (column: Waters Xbridge Prep OBD C18 150*40 mm*10 um; mobile phase: [water(NH₄HCO₃)-ACN]; B %: 40%-60%, 8 min) affording (E)-3-(2,6-dimethylpyrimidin-4-yl)-1-(3-(((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)prop-2-en-1-one (7.23 mg, 8.31%) as a yellow amorphous solid: $^1$H NMR (400 MHz, Dimethylsulfoxide-d6) δ 9.27-9.16 (m, 1H), 8.22-8.14 (m, 2H), 7.72-7.52 (m, 4H), 7.38-7.13 (m, 2H), 5.33-5.16 (m, 1H), 4.56-4.40 (m, 1H), 4.33-4.02 (m, 5H), 3.93-3.86 (m, 1H), 3.76-3.65 (m, 1H), 3.60 (s, 2H), 3.49-3.32 (m, 1H), 3.31-3.14 (m, 3H), 3.01-2.92 (m, 2H), 2.89-2.76 (m, 1H), 2.59 (s, 3H), 2.45 (s, 3H), 2.22-1.96 (m, 3H), 1.89-1.70 (m, 3H).

LCMS (5% to 95% acetonitrile in water+0.03% ammonium bicarbonate over 6 min); retention time 2.640 min, ESI+ found [M+H]=732.3.

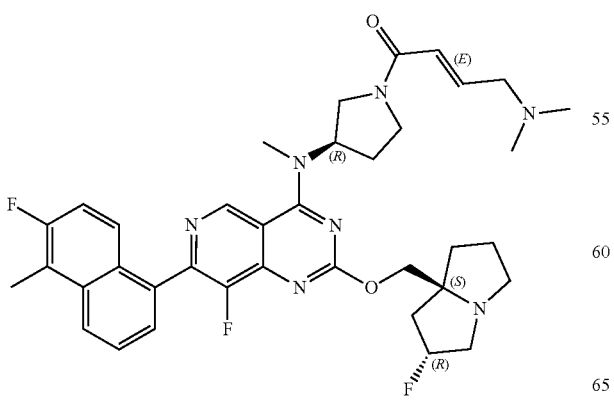

Example 281 (Method 10): (E)-4-(dimethylamino)-1-((R)-3-((8-fluoro-7-(6-fluoro-5-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)but-2-en-1-one

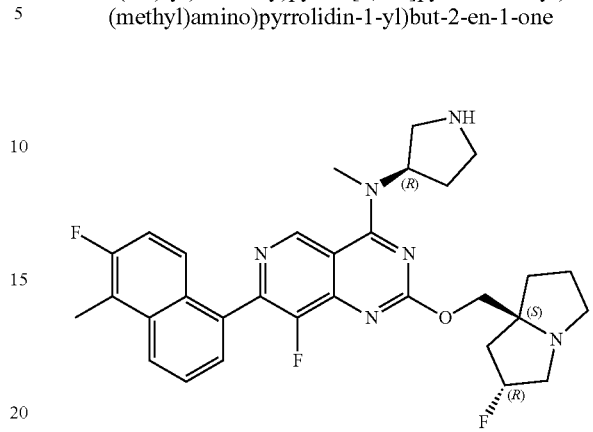

Step 1: 8-fluoro-7-(6-fluoro-5-methylnaphthalen-1-yl)-2-(((2R,7aS)-2-fluorotetrahydro-1H-pyrrolizin-7a(5H)-yl)methoxy)-N-methyl-N—((R)-pyrrolidin-3-yl)pyrido[4,3-d]pyrimidin-4-amine The deprotection of the Boc group was prepared in a similar fashion to Method #10, Step 6. The reaction mixture was concentrated in vacuo affording 8-fluoro-7-(6-fluoro-5-methylnaphthalen-1-yl)-2-(((2R,7aS)-2-fluorotetrahydro-1H-pyrrolizin-7a(5H)-yl)methoxy)-N-methyl-N—((R)-pyrrolidin-3-yl)pyrido[4,3-d]pyrimidin-4-amine (153 mg, crude) as a yellow oil, which was used in the next step without any further purification. LCMS Rt=0.520 min, m/z=562.3 [M+H]⁺.

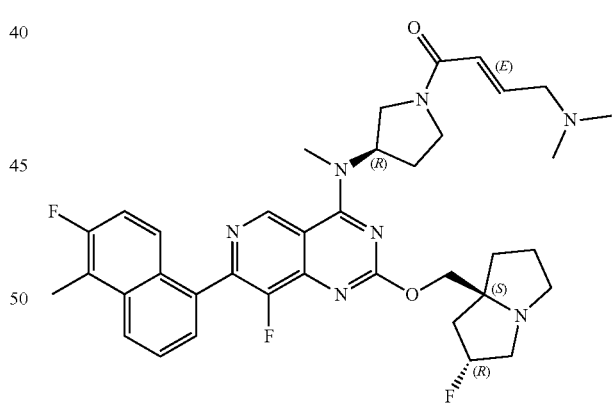

Step 2: (E)-4-(dimethylamino)-1-((R)-3-((8-fluoro-7-(6-fluoro-5-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)but-2-en-1-one The amide coupling reaction was prepared in a similar fashion to Method #10, Step 7. The residue was purified by reverse phase HPLC (neutral condition, column: Waters Xbridge Prep OBD C18 150*40 mm*10 μm; mobile phase: [water(NH₄HCO₃)-ACN]; B %: 35%-65%, 8 min) affording (E)-4-(dimethylamino)-1-((R)-3-((8-fluoro-7-(6-fluoro-5-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)but-2-en-1-one (19.14 mg, 12.17%) as a yellow solid: $^1$H NMR (400 MHz, Acetonitrile-d3) δ 9.29 (d, J=2.0 Hz, 1H), 8.23 (d, J=8.5 Hz, 1H), 7.81-7.72 (m, 1H), 7.70-7.62 (m, 2H), 7.34-7.25 (m, 1H), 6.77 (dtd, J=2.4, 6.2, 15.1 Hz, 1H), 6.47-6.36 (m, 1H), 5.47-5.19 (m, 2H), 4.27-4.21 (m, 1H), 4.20-4.15 (m, 1H), 4.14-3.93 (m, 1H), 3.93-3.79 (m, 1H), 3.72-3.54 (m, 2H), 3.46 (d, J=2.3 Hz, 3H), 3.17 (br dd, J=2.1, 7.3 Hz, 2H), 3.11-3.06 (m, 3H), 2.97-2.88 (m, 1H), 2.66 (d, J=2.0 Hz, 3H), 2.45-2.38 (m, 1H), 2.36-2.31 (m, 1H), 2.23 (d, J=6.0 Hz, 6H), 2.20 (br s, 1H), 2.13 (br d, J=2.8 Hz, 1H), 2.08 (br s, 1H), 1.93-1.83 (m, 3H).

LCMS (5% to 95% acetonitrile in water+0.03% ammonium bicarbonate over 6 min); retention time 2.853 min, ESI+ found [M+H]=673.3.

Example 282 (Method 8): (E)-1-((R)-3-((8-fluoro-7-(6-fluoro-5-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-methylazetidin-2-yl)prop-2-en-1-one Step 1: tert-butyl (R)-2-((E)-3-((R)-3-((8-fluoro-7-(6-fluoro-5-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-oxoprop-1-en-1-yl)azetidine-1-carboxylate The amide coupling reaction was prepared in a similar fashion to Method #1, Step 10. The reaction mixture was concentrated in vacuo affording tert-butyl (R)-2-((E)-3-((R)-3-((8-fluoro-7-(6-fluoro-5-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-oxoprop-1-en-1-yl)azetidine-1-carboxylate (440 mg, crude) as a yellow oil, which was used in the next step without any further purification. LCMS Rt=0.734 min, m/z=771.4 [M+H]$^+$.

Step 2: (E)-3-((R)-azetidin-2-yl)-1-((R)-3-((8-fluoro-7-(6-fluoro-5-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one The deprotection of the Boc group was prepared in a similar fashion to Method #1, Step 9. The reaction mixture was concentrated in vacuo affording (E)-3-((R)-azetidin-2-yl)-1-((R)-3-((8-fluoro-7-(6-fluoro-5-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (100 mg, crude, trifluoroacetic acid salt) as a brown oil, used in next step without any further purification. LCMS Rt=1.229 min, m/z=671.3 [M+H]$^+$.

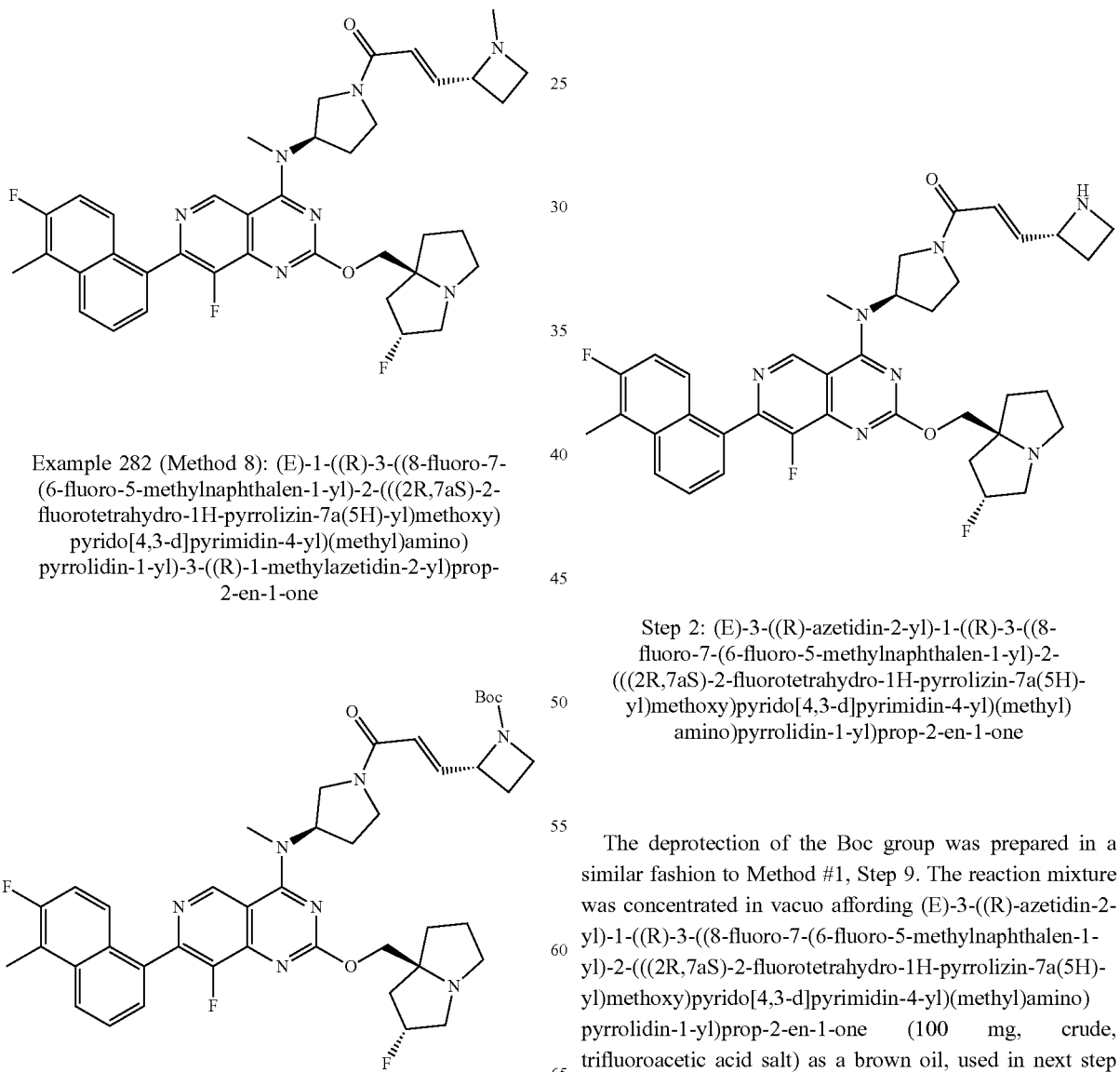

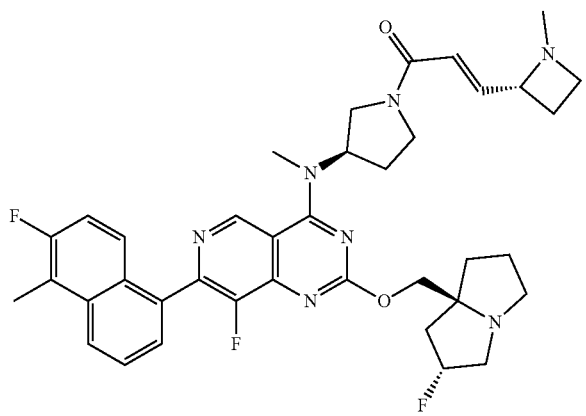 [SMILES: Cc1c(F)ccc2c(-c3ncc4c(N(C)[C@@H]5CCN(C(=O)/C=C/[C@H]6CCN6C)C5)nc(OC[C@@]56CCCN5C[C@H](F)C6)nc4c3F)cccc12]

Step 3: (E)-1-((R)-3-((8-fluoro-7-(6-fluoro-5-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-methylazetidin-2-yl)prop-2-en-1-one The reductive amination was prepared in a similar fashion to Method #8, Step 6. The residue was purified by prep-HPLC (column: Waters Xbridge Prep OBD C18 150*40 mm*10 um; mobile phase: [water(NH₄HCO₃)-ACN]; B %: 35%-65%, 8 min) affording (E)-1-((R)-3-((8-fluoro-7-(6-fluoro-5-methylnaphthalen-1-yl)-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-((R)-1-methylazetidin-2-yl)prop-2-en-1-one (3.75 mg, 3.38%) as a white solid: $^1$H NMR (400 MHz, Acetonitrile-d3) δ 9.29 (d, J=2.6 Hz, 1H), 8.29-8.18 (m, 1H), 7.83-7.69 (m, 1H), 7.69-7.64 (m, 2H), 7.35-7.26 (m, 1H), 6.79 (dd, J=5.8, 15.1 Hz, 1H), 6.46-6.35 (m, 1H), 5.45-5.20 (m, 2H), 4.31-4.07 (m, 3H), 4.02-3.75 (m, 2H), 3.72-3.64 (m, 1H), 3.61-3.51 (m, 2H), 3.46 (d, J=1.9 Hz, 4H), 3.34-3.27 (m, 1H), 3.19-3.14 (m, 2H), 3.09 (s, 1H), 2.97-2.77 (m, 3H), 2.67 (d, J=2.0 Hz, 3H), 2.48-2.37 (m, 1H), 2.35-2.30 (m, 1H), 2.29-2.24 (m, 3H), 1.91-1.85 (m, 3H), 1.36-1.25 (m, 2H).

LCMS (5% to 95% acetonitrile in water+0.1% trifluoroacetic acid over 6 min); retention time 2.063 min, ESI+ found [M+H]=685.3.

Example 283 (Method 1): (E)-3-(2,6-dimethylpyrimidin-4-yl)-1-(3-(((7-(8-ethyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)prop-2-en-1-one

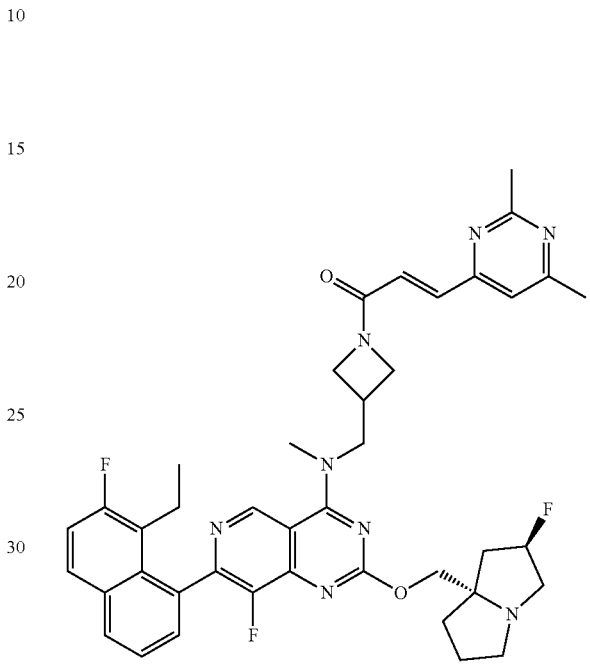

Step 1: (E)-3-(2,6-dimethylpyrimidin-4-yl)-1-(3-(((7-(8-ethyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)prop-2-en-1-one The amide coupling reaction was prepared in a similar fashion to Method #1, Step 10. The reaction mixture was concentrated in vacuo and the residue was purified by reverse phase HPLC (column: Waters Xbridge Prep OBD C18 150*40 mm*10 um; mobile phase: [water(NH₄HCO₃)-ACN]; B %: 25%-55%, 8 min) affording (E)-3-(2,6-dimethylpyrimidin-4-yl)-1-(3-(((7-(8-ethyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)methyl)azetidin-1-yl)prop-2-en-1-one (36.28 mg, 55.09%) as a gray amorphous solid: $^1$H NMR (400 MHz, Dimethylsulfoxide-d6) δ 9.30 (s, 1H), 8.14-8.08 (m, 1H), 8.05-7.98 (m, 1H), 7.58 (br t, J=7.6 Hz, 1H), 7.54-7.47 (m, 2H), 7.46 (d, J=4.8 Hz, 1H), 7.38-7.31 (m, 1H), 7.25-7.16 (m, 1H), 5.31-5.14 (m, 1H), 4.48 (br t, J=8.3 Hz, 1H), 4.32-4.25 (m, 1H), 4.22-4.13 (m, 2H), 4.12-4.02 (m, 2H), 3.96-3.87 (m, 1H), 3.60 (s, 3H), 3.24-3.18 (m, 1H), 3.06 (br d, J=14.5 Hz, 2H), 2.99 (br d, J=9.0 Hz, 1H), 2.82-2.74 (m, 1H), 2.60-2.57 (m, 3H), 2.45-2.42 (m, 3H), 2.34-2.24 (m, 1H), 2.15-1.94 (m, 4H), 1.86-1.66 (m, 4H), 0.80-0.74 (m, 3H).

LCMS (5% to 95% acetonitrile in water+0.03% ammonium bicarbonate over 6 min); retention time 3.051 min, ESI+ found [M+H]=736.4.

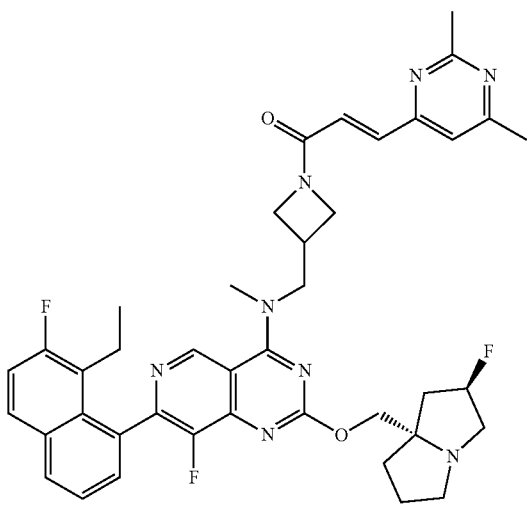 [SMILES: CCc1c(F)ccc2cccc(-c3ncc4c(N(C)CC5CN(C(=O)/C=C/c6cc(C)nc(C)n6)C5)nc(OC[C@@]56CCCN5C[C@H](F)C6)nc4c3F)c12]

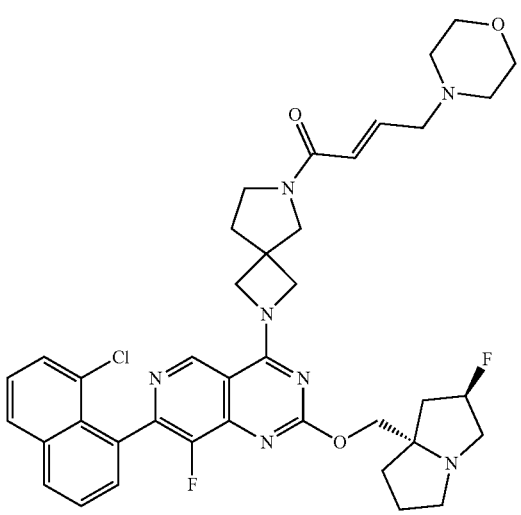 [SMILES: O=C(/C=C/CN1CCOCC1)N1CCC2(C1)CN(c1nc(OC[C@@]34CCCN3C[C@H](F)C4)nc3c(F)c(-c4cccc5cccc(Cl)c45)ncc13)C2]

Example 284 (Method 1): (E)-1-(2-(7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-2,6-diazaspiro[3.4]octan-6-yl)-4-morpholinobut-2-en-1-one

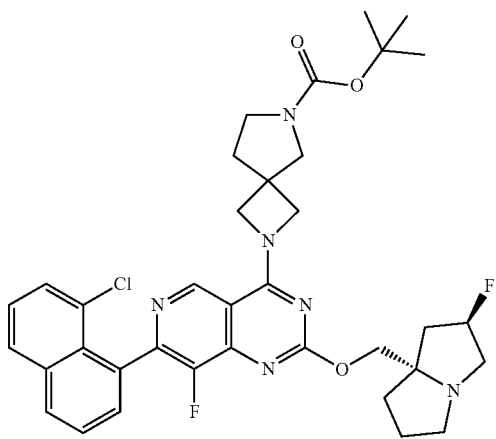 [SMILES: CC(C)(C)OC(=O)N1CCC2(C1)CN(c1nc(OC[C@@]34CCCN3C[C@H](F)C4)nc3c(F)c(-c4cccc5cccc(Cl)c45)ncc13)C2]

Step 1: tert-butyl 2-(7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-2,6-diazaspiro[3.4]octane-6-carboxylate The substitution reaction was prepared in a similar fashion to Method #1, Step 8. The resulting residue was purified by reverse phase HPLC (column: Phenomenex Luna 80*30 mm*3 μm; mobile phase: [water(TFA)-ACN]; B %: 30%-60%, 8 min) affording tert-butyl 2-(7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-2,6-diazaspiro[3.4]octane-6-carboxylate (80 mg, 15.83%, trifluoroacetate salt) as a brown solid. LCMS Rt=0.789 min, m/z=676.3 [M+H]$^+$.

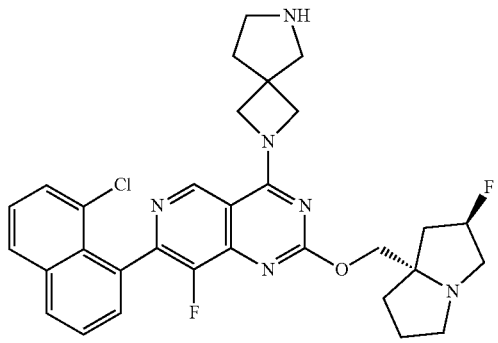 [SMILES: Fc1c(-c2cccc3cccc(Cl)c23)ncc2c(N3CC4(CCNC4)C3)nc(OC[C@@]34CCCN3C[C@H](F)C4)nc12]

Step 2: 7-(8-chloronaphthalen-1-yl)-8-fluoro-2-(((2R,7aS)-2-fluorotetrahydro-1H-pyrrolizin-7a(5H)-yl)methoxy)-4-(2,6-diazaspiro[3.4]octan-2-yl)pyrido[4,3-d]pyrimidine The deprotection of the Boc group was prepared in a similar fashion to Method #1, Step 9. The reaction mixture was concentrated in vacuo affording 7-(8-chloronaphthalen-1-yl)-8-fluoro-2-(((2R,7aS)-2-fluorotetrahydro-1H-pyrrolizin-7a(5H)-yl)methoxy)-4-(2,6-diazaspiro[3.4]octan-2-yl)pyrido[4,3-d]pyrimidine (70 mg, crude, trifluoroacetate salt) as a yellow oil, which was used in the next step without further purification. LCMS Rt=0.525 min, m/z=576.2 [M+H]$^+$.

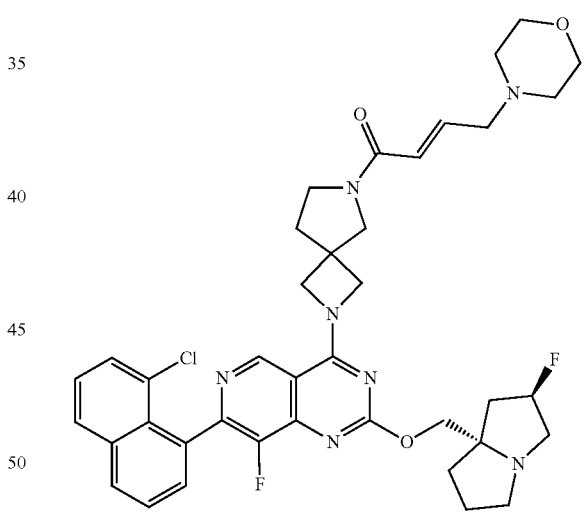

Step 3: (E)-1-(2-(7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)-2,6-diazaspiro[3.4]octan-6-yl)-4-morpholinobut-2-en-1-one The amide coupling reaction was prepared in a similar fashion to Method #1, Step 10. The resulting residue was purified by reverse phase HPLC (column: Waters Xbridge Prep OBD C18 150*40 mm*10 μm; mobile phase: [water (NH$_4$HCO$_3$)-ACN]; B %: 30%-70%, 8 min) affording (E)-1-(2-(7-(8-chloronaphthalen-1-yl)-8-fluoro-2-(((2R,7aS)-2-fluorotetrahydro-1H-pyrrolizin-7a(5H)-yl)methoxy)pyrido

[4,3-d]pyrimidin-4-yl)-2,6-diazaspiro[3.4]octan-6-yl)-4-morpholinobut-2-en-1-one (7.46 mg, 9.83%) as a white solid: ¹H NMR (400 MHz, Acetonitrile-d3) δ 8.91 (s, 1H), 8.11 (br d, J=7.9 Hz, 1H), 8.01 (br d, J=8.3 Hz, 1H), 7.68 (br t, J=7.6 Hz, 1H), 7.62-7.55 (m, 2H), 7.55-7.46 (m, 1H), 6.68 (br s, 1H), 6.42-6.31 (m, 1H), 5.36-5.13 (m, 1H), 4.68 (br d, J=5.6 Hz, 4H), 4.22-4.02 (m, 2H), 3.92-3.70 (m, 2H), 3.67-3.59 (m, 5H), 3.53 (br t, J=6.3 Hz, 1H), 3.19-3.02 (m, 5H), 2.96-2.82 (m, 1H), 2.40 (br s, 4H), 2.35-2.23 (m, 2H), 2.11-2.00 (m, 3H), 1.90-1.73 (m, 3H).

LCMS (5% to 95% acetonitrile in water+0.03% ammonium bicarbonate over 6 min); retention time 1.865 min, ESI+ found [M+H]=729.3.

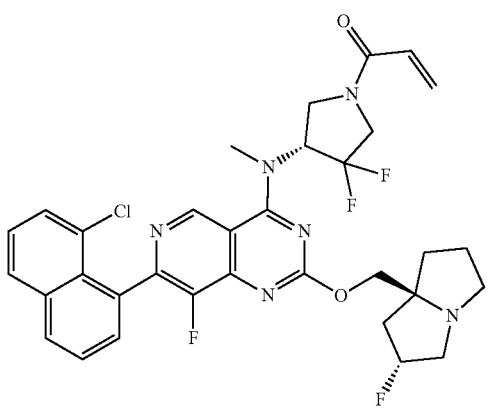 [SMILES: C=CC(=O)N1C[C@@H](N(C)c2nc(OC[C@@]34CCCN3C[C@H](F)C4)nc3c(F)c(-c4cccc5cccc(Cl)c45)ncc23)C(F)(F)C1]

Example 285 (Method 1):1-((R)-4-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-3,3-difluoropyrrolidin-1-yl)prop-2-en-1-one

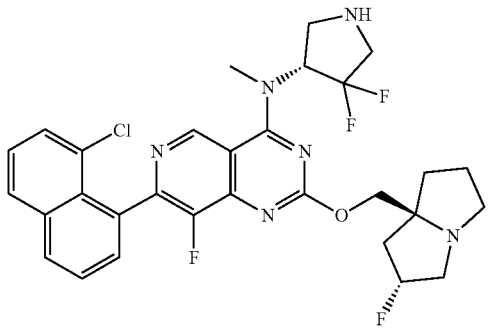 [SMILES: CN(c1nc(OC[C@@]23CCCN2C[C@H](F)C3)nc2c(F)c(-c3cccc4cccc(Cl)c34)ncc12)[C@@H]1CNCC1(F)F]

Step 1: 7-(8-chloronaphthalen-1-yl)-N—((R)-4,4-difluoropyrrolidin-3-yl)-8-fluoro-2-(((2R,7aS)-2-fluorotetrahydro-1H-pyrrolizin-7a(5H)-yl)methoxy)-N-methylpyrido[4,3-d]pyrimidin-4-amine The deprotection of the Boc group was prepared in a similar fashion to Method #1, Step 9. The reaction mixture was concentrated in vacuo affording 7-(8-chloronaphthalen-1-yl)-N—((R)-4,4-difluoropyrrolidin-3-yl)-8-fluoro-2-(((2R,7aS)-2-fluorotetrahydro-1H-pyrrolizin-7a(5H)-yl)methoxy)-N-methylpyrido[4,3-d]pyrimidin-4-amine (80 mg, crude, trifluoroacetate salt) as a brown oil, which was used in the next step without further purification. LCMS Rt=0.765 min, m/z=600.2 [M+H]⁺.

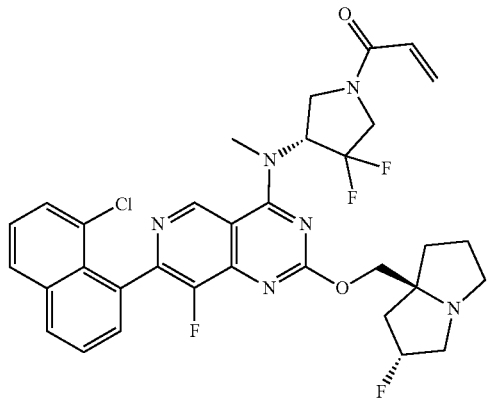 [SMILES: C=CC(=O)N1C[C@@H](N(C)c2nc(OC[C@@]34CCCN3C[C@H](F)C4)nc3c(F)c(-c4cccc5cccc(Cl)c45)ncc23)C(F)(F)C1]

Step 2: 1-((R)-4-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-3,3-difluoropyrrolidin-1-yl)prop-2-en-1-one The amide coupling reaction was prepared in a similar fashion to Method #1, Step 10. The resulting residue was purified by reverse phase HPLC (column: Waters Xbridge Prep OBD C18 150*40 mm*10 μm; mobile phase: [water (NH₄HCO₃)-ACN]; B %: 35%-65%, 8 min) affording 1-((R)-4-((7-(8-chloronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)-3,3-difluoropyrrolidin-1-yl)prop-2-en-1-one (14.54 mg, 31.62%) as a pale yellow amorphous solid: ¹H NMR (400 MHz, Acetonitrile-d3) δ 9.32 (d, J=2.9 Hz, 1H), 8.18-8.14 (m, 1H), 8.05 (d, J=8.1 Hz, 1H), 7.75-7.69 (m, 1H), 7.67-7.62 (m, 2H), 7.57-7.52 (m, 1H), 6.67-6.47 (m, 1H), 6.33 (dd, J=2.1, 16.8 Hz, 1H), 5.91-5.70 (m, 2H), 5.38-5.16 (m, 1H), 4.35-4.26 (m, 1H), 4.25-4.18 (m, 2H), 4.18-3.96 (m, 3H), 3.60 (br s, 3H), 3.19-3.12 (m, 2H), 3.07 (s, 1H), 2.95-2.88 (m, 1H), 2.15-2.10 (m, 2H), 2.08-2.03 (m, 1H), 1.94-1.83 (m, 3H).

LCMS (5% to 95% acetonitrile in water+0.03% ammonium bicarbonate over 6 min); retention time 3.107 min, ESI+ found [M+H]=654.2.

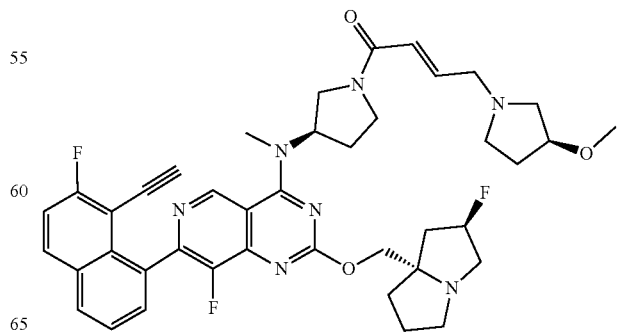

Example 286 (Method 12): (E)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-4-((S)-3-methoxypyrrolidin-1-yl)but-2-en-1-one

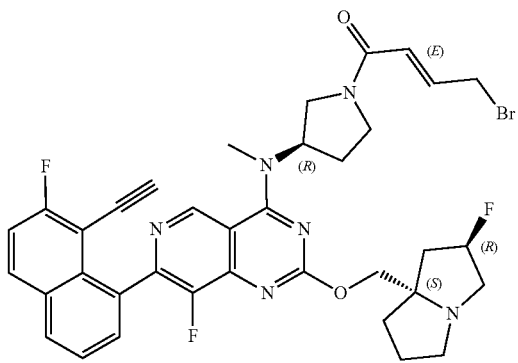

Step 1: (E)-4-bromo-1-((R)-3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)but-2-en-1-one The coupling reaction was prepared in a similar fashion to Method #12, Step 1. The combined organic layers were dried over sodium sulphate and concentrated in vacuo affording (E)-4-bromo-1-((R)-3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)but-2-en-1-one (850 mg, crude) as a brown oil, which was used in the next step without any further purification. LCMS Rt=0.786 min, m/z=718.2 [M+H]⁺.

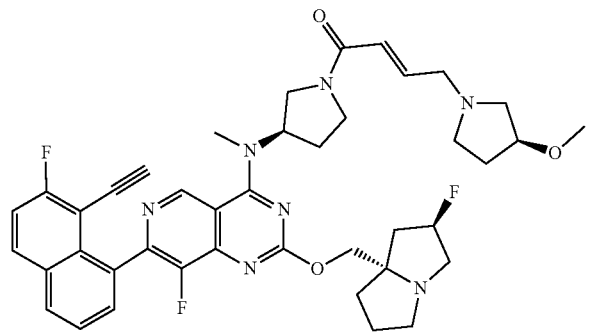 [SMILES: C#Cc1c(F)ccc2cccc(-c3ncc4c(N(C)[C@@H]5CCN(C(=O)/C=C/CN6CC[C@H](OC)C6)C5)nc(OC[C@@]56CCCN5C[C@H](F)C6)nc4c3F)c12]

Step 2: (E)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-4-((S)-3-methoxypyrrolidin-1-yl)but-2-en-1-one The substitution reaction was prepared in a similar fashion to Method #12, Step 2. The reaction mixture was concentrated to dryness in vacuo and purified by reverse phase HPLC (column: Waters Xbridge Prep OBD C18 150*40 mm*10 um; mobile phase: [water (NH₄HCO₃)-ACN]; B %: 35%-65%, 8 min) affording (E)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-4-((S)-3-methoxypyrrolidin-1-yl)but-2-en-1-one (8.63 mg, 8.14%) as a yellow amorphous solid: ¹H NMR (400 MHz, Dimethylsulfoxide-d6) δ 9.19 (t, J=3.8 Hz, 1H), 8.26-8.19 (m, 2H), 7.74-7.65 (m, 2H), 7.61 (t, J=9.0 Hz, 1H), 6.74-6.63 (m, 1H), 6.49-6.36 (m, 1H), 5.37-5.20 (m, 2H), 4.18-4.12 (m, 1H), 4.11-4.03 (m, 2H), 3.92-3.84 (m, 2H), 3.77-3.60 (m, 2H), 3.56-3.45 (m, 1H), 3.43 (d, J=4.0 Hz, 3H), 3.23-3.19 (m, 2H), 3.18-3.15 (m, 3H), 3.12-3.00 (m, 3H), 2.87-2.79 (m, 1H), 2.73-2.64 (m, 1H), 2.60-2.54 (m, 1H), 2.49-2.40 (m, 2H), 2.38-2.24 (m, 2H), 2.16-2.04 (m, 2H), 2.03-1.93 (m, 2H), 1.87-1.64 (m, 4H).

LCMS (5% to 95% acetonitrile in water+0.03% ammonium bicarbonate over 6 min); retention time 2.933 min, ESI+ found [M+H]=739.4.

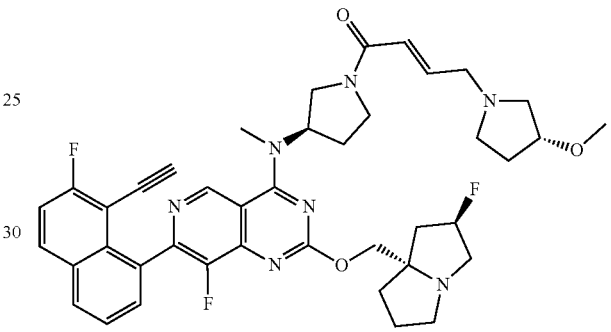

Example 287 (Method 12): (E)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-4-((R)-3-methoxypyrrolidin-1-yl)but-2-en-1-one

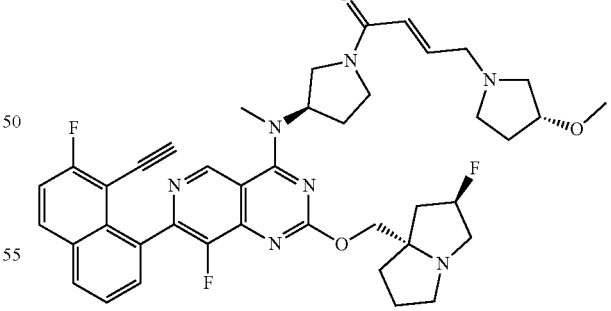

Step 1: (E)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-4-((R)-3-methoxypyrrolidin-1-yl)but-2-en-1-one The substitution reaction was prepared in a similar fashion to Method #12, Step 2. The reaction mixture was concentrated in vacuo and purified by reverse phase HPLC (column: Waters Xbridge Prep OBD C18 150*40 mm*10 µm; mobile phase: [water (NH₄HCO₃)-ACN]; B %: 35%-65%, 8 min) affording (E)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-4-((R)-3-methoxypyrrolidin-1-yl)but-2-en-1-one (7 mg, 6.46%) as a yellow oil: ¹H NMR (400 MHz, Acetonitrile-d3) δ 9.19-9.15 (m, 1H), 8.18-8.10 (m, 2H), 7.72-7.65 (m, 2H), 7.47 (t, J=9.1 Hz, 1H), 6.84-6.74 (m, 1H), 6.46-6.36 (m, 1H), 5.43-5.19 (m, 2H), 4.26-4.19 (m, 1H), 4.16-4.11 (m, 1H), 4.04-3.82 (m, 3H), 3.73-3.52 (m, 2H), 3.45 (s, 3H), 3.30-3.27 (m, 1H), 3.26-3.23 (m, 3H), 3.22 (s, 2H), 3.18-3.13 (m, 2H), 3.08 (s, 1H), 2.97-2.86 (m, 1H), 2.72-2.63 (m, 2H), 2.57 (td, J=3.7, 10.2 Hz, 1H), 2.49-2.37 (m, 3H), 2.19 (br d, J=1.8 Hz, 1H), 2.12 (br d, J=2.6 Hz, 1H), 2.09-2.01 (m, 2H), 1.95-1.84 (m, 3H), 1.78-1.67 (m, 1H).

LCMS (5% to 95% acetonitrile in water+0.03% ammonium bicarbonate over 6 min); retention time 2.929 min, ESI+ found [M+H]=739.4.

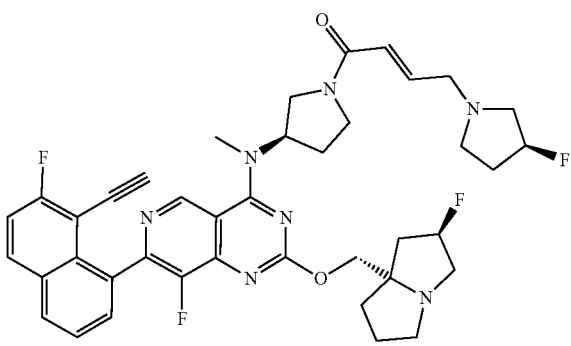

Example 288 (Method 12):(E)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-4-((S)-3-fluoropyrrolidin-1-yl)but-2-en-1-one

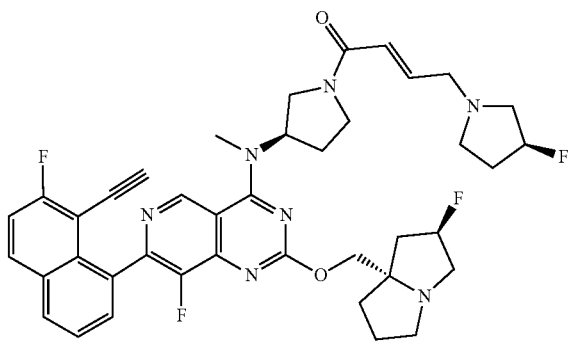 [SMILES: C#Cc1c(F)ccc2cccc(-c3ncc4c(N(C)[C@@H]5CCN(C(=O)/C=C/CN6CC[C@H](F)C6)C5)nc(OC[C@@]56CCCN5C[C@H](F)C6)nc4c3F)c12]

Step 1: (E)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-4-((S)-3-fluoropyrrolidin-1-yl)but-2-en-1-one The substitution reaction was prepared in a similar fashion to Method #12, Step 2. The reaction mixture was concentrated in vacuo and purified by reverse phase HPLC (column: Waters Xbridge Prep OBD C18 150*40 mm*10 µm; mobile phase: [water (NH₄HCO₃)-ACN]; B %: 35%-65%, 8 min) affording (E)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-4-((S)-3-fluoropyrrolidin-1-yl)but-2-en-1-one (8.82 mg, 8.70%) as a yellow amorphous solid. ¹H NMR (400 MHz, Dimethylsulfoxide-d6) δ 9.19 (t, J=3.9 Hz, 1H), 8.27-8.18 (m, 2H), 7.75-7.64 (m, 2H), 7.61 (t, J=9.0 Hz, 1H), 6.79-6.66 (m, 1H), 6.50-6.39 (m, 1H), 5.38-5.24 (m, 2H), 5.23-5.10 (m, 1H), 4.18-4.12 (m, 1H), 4.10-4.03 (m, 2H), 3.95-3.84 (m, 1H), 3.79-3.58 (m, 2H), 3.57-3.45 (m, 1H), 3.43 (d, J=3.8 Hz, 3H), 3.39 (br s, 1H), 3.28-3.23 (m, 2H), 3.15-3.06 (m, 2H), 3.02 (s, 1H), 2.87-2.76 (m, 3H), 2.71-2.55 (m, 1H), 2.35 (td, J=7.5, 14.9 Hz, 2H), 2.28-2.17 (m, 1H), 2.15-2.06 (m, 2H), 2.05-1.88 (m, 2H), 1.87-1.76 (m, 3H).

LCMS (5% to 95% acetonitrile in water+0.03% ammonium bicarbonate over 6 min); retention time 2.966 min, ESI+ found [M+H]=727.3.

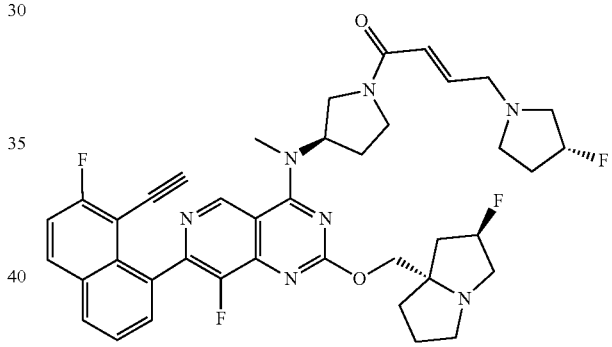

Example 289 (Method 12): (E)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-4-((R)-3-fluoropyrrolidin-1-yl)but-2-en-1-one

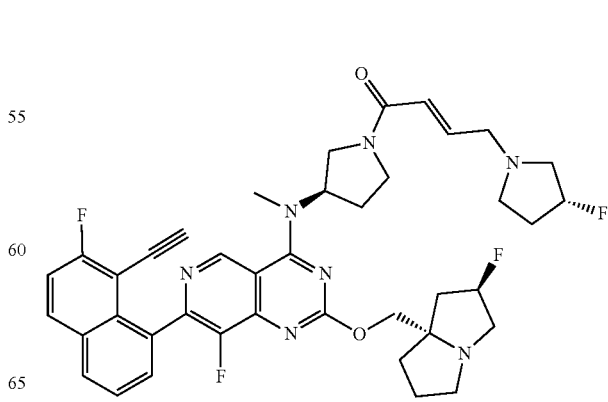

Step 1: (E)-1-((R)-3-((7-(8-ethynyl-7-fluoronaphtha-len-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-4-((R)-3-fluoropyrrolidin-1-yl)but-2-en-1-one The substitution reaction was prepared in a similar fashion to Method #12, Step 2. The reaction mixture was concentrated in vacuo and purified by reverse phase HPLC (column: Waters Xbridge Prep OBD C18 150*40 mm*10 μm; mobile phase: [water (NH$_4$HCO$_3$)-ACN]; B %: 35%-65%, 8 min) affording (E)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-4-((R)-3-fluoropyrrolidin-1-yl)but-2-en-1-one (7 mg, 6.86%) as a yellow solid: $^1$H NMR (400 MHz, Acetonitrile-d3) δ 9.21-9.13 (m, 1H), 8.18-8.08 (m, 2H), 7.74-7.65 (m, 2H), 7.47 (t, J=9.0 Hz, 1H), 6.85-6.75 (m, 1H), 6.50-6.37 (m, 1H), 5.44-5.09 (m, 3H), 4.26-4.21 (m, 1H), 4.18-4.13 (m, 1H), 4.11-3.82 (m, 2H), 3.72-3.62 (m, 1H), 3.57-3.48 (m, 1H), 3.45 (s, 3H), 3.32-3.27 (m, 2H), 3.20-3.14 (m, 2H), 3.13-3.08 (m, 1H), 2.96-2.83 (m, 3H), 2.75-2.59 (m, 1H), 2.40 (br dd, J=7.9, 15.0 Hz, 2H), 2.29 (br s, 1H), 2.20 (br d, J=1.0 Hz, 2H), 2.17-2.11 (m, 2H), 2.04 (br s, 2H), 1.94-1.85 (m, 3H).

LCMS (5% to 95% acetonitrile in water+0.03% ammonium bicarbonate over 6 min); retention time 2.963 min, ESI+ found [M+H]=727.3.

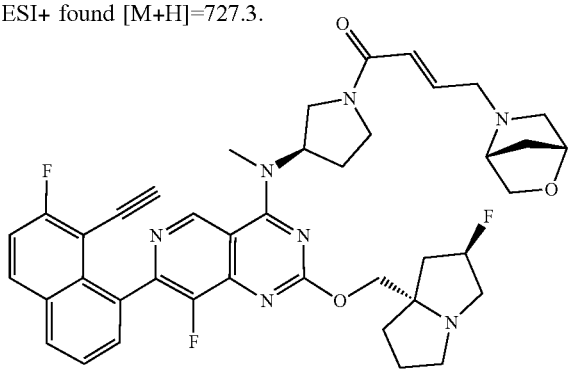

Example 290 (Method 12): (E)-4-((1R,4R)-2-oxa-5-azabicyclo[2.2.1]heptan-5-yl)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)but-2-en-1-one

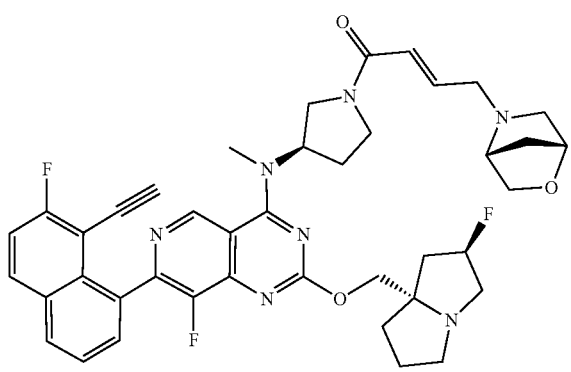 [SMILES: C#Cc1c(F)ccc2cccc(-c3ncc4c(N(C)[C@@H]5CCN(C(=O)/C=C/CN6C[C@H]7C[C@@H]6CO7)C5)nc(OC[C@@]56CCCN5C[C@H](F)C6)nc4c3F)c12]

Step 1: (E)-4-((1R,4R)-2-oxa-5-azabicyclo[2.2.1]heptan-5-yl)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)but-2-en-1-one The substitution reaction was prepared in a similar fashion to Method #12, Step 2. The reaction mixture was concentrated in vacuo and purified by reverse phase HPLC (column: Waters Xbridge Prep OBD C18 150*40 mm*10 μm; mobile phase: [water (NH$_4$HCO$_3$)-ACN]; B %: 30%-60%, 8 min) affording (E)-4-((1R,4R)-2-oxa-5-azabicyclo[2.2.1]heptan-5-yl)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)but-2-en-1-one (9.72 mg, 9.26%) as a yellow amorphous solid: $^1$H NMR (400 MHz, Dimethylsulfoxide-d6) δ 9.19 (t, J=4.0 Hz, 1H), 8.27-8.18 (m, 2H), 7.73-7.64 (m, 2H), 7.61 (t, J=9.0 Hz, 1H), 6.73-6.62 (m, 1H), 6.48-6.37 (m, 1H), 5.37-5.20 (m, 2H), 4.34 (br d, J=8.0 Hz, 1H), 4.17-4.12 (m, 1H), 4.11-4.02 (m, 2H), 3.95-3.81 (m, 2H), 3.77-3.60 (m, 2H), 3.55-3.45 (m, 3H), 3.43 (d, J=4.0 Hz, 3H), 3.39 (br d, J=6.5 Hz, 1H), 3.33-3.25 (m, 2H), 3.15-3.06 (m, 2H), 3.05-3.00 (m, 1H), 2.87-2.79 (m, 1H), 2.78-2.72 (m, 1H), 2.47-2.41 (m, 1H), 2.39-2.24 (m, 2H), 2.18-2.12 (m, 1H), 2.08-1.96 (m, 2H), 1.87-1.80 (m, 1H), 1.78-1.72 (m, 2H), 1.61-1.55 (m, 1H).

LCMS (5% to 95% acetonitrile in water+0.03% ammonium bicarbonate over 6 min); retention time 2.821 min, ESI+ found [M+H]=737.3.

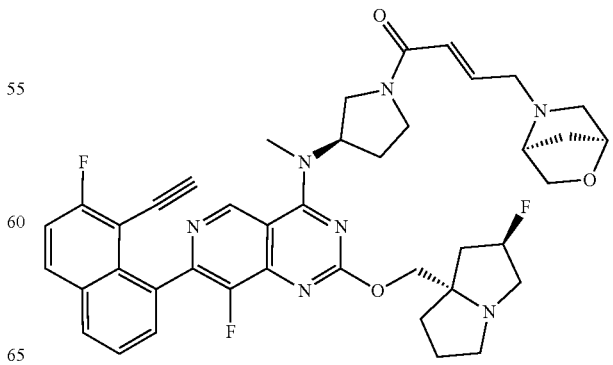

Example 291 (Method 12): (E)-4-((1S,4S)-2-oxa-5-azabicyclo[2.2.1]heptan-5-yl)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)but-2-en-1-one

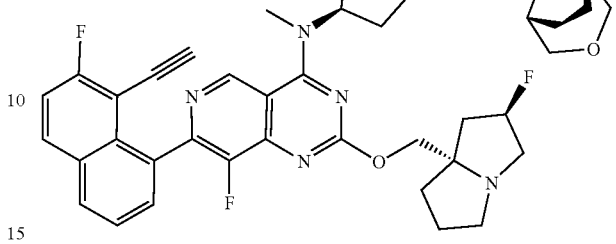

Example 292 (Method 12): (E)-4-((1R,5S)-3-oxa-8-azabicyclo[3.2.1]octan-8-yl)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)but-2-en-1-one

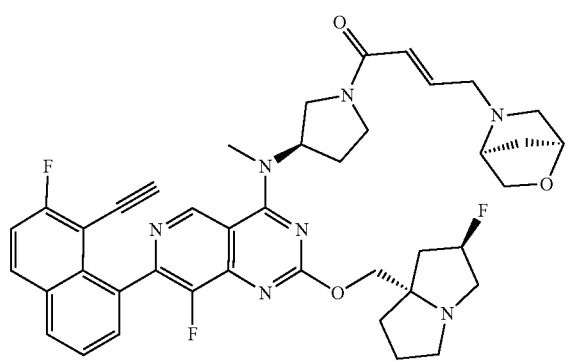

Step 1: (E)-4-((1S,4S)-2-oxa-5-azabicyclo[2.2.1]heptan-5-yl)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)but-2-en-1-one The substitution reaction was prepared in a similar fashion to Method #12, Step 2. The reaction mixture was concentrated in vacuo and purified by reverse phase HPLC (column: Waters Xbridge Prep OBD C18 150*40 mm*10 μm; mobile phase: [water (NH$_4$HCO$_3$)-ACN]; B %: 30%-60%, 8 min) affording (E)-4-((1S,4S)-2-oxa-5-azabicyclo[2.2.1]heptan-5-yl)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)but-2-en-1-one (8 mg, 7.80%) as a yellow solid: $^1$H NMR (400 MHz, Acetonitrile-d3) δ 9.17 (dd, J=2.6, 4.1 Hz, 1H), 8.18-8.09 (m, 2H), 7.72-7.65 (m, 2H), 7.47 (t, J=9.1 Hz, 1H), 6.81-6.71 (m, 1H), 6.48-6.38 (m, 1H), 5.44-5.18 (m, 2H), 4.34 (br d, J=8.4 Hz, 1H), 4.26-4.19 (m, 1H), 4.16-4.12 (m, 1H), 4.09-3.81 (m, 3H), 3.74-3.47 (m, 4H), 3.45 (s, 3H), 3.39 (dt, J=1.6, 6.6 Hz, 1H), 3.32-3.25 (m, 1H), 3.19-3.13 (m, 2H), 3.08 (s, 1H), 2.97-2.88 (m, 1H), 2.85-2.77 (m, 1H), 2.53 (br dd, J=6.6, 9.6 Hz, 1H), 2.46-2.40 (m, 1H), 2.38-2.25 (m, 2H), 2.19-2.15 (m, 1H), 2.12 (br d, J=2.5 Hz, 1H), 2.09-2.04 (m, 1H), 1.94-1.77 (m, 4H), 1.70-1.62 (m, 1H).

LCMS (5% to 95% acetonitrile in water+0.03% ammonium bicarbonate over 6 min); retention time 2.816 min, ESI+ found [M+H]=737.3.

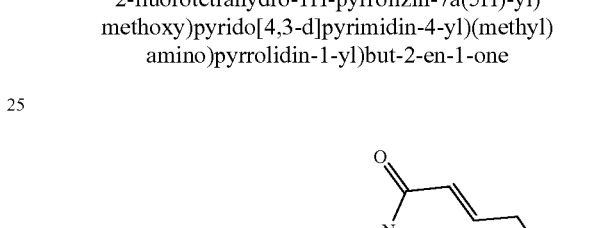

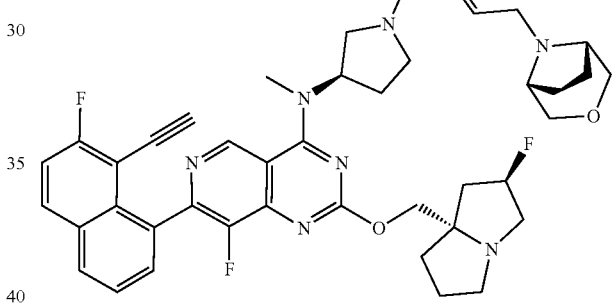

Step 1: (E)-4-((1R,5S)-3-oxa-8-azabicyclo[3.2.1]octan-8-yl)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)but-2-en-1-one The substitution reaction was prepared in a similar fashion to Method #12, Step 2. The reaction mixture was concentrated in vacuo and the residue was purified by reverse phase HPLC (column: Waters Xbridge Prep OBD C18 150*40 mm*10 um; mobile phase: [water (NH$_4$HCO$_3$)-ACN]; B %: 35%-65%, 8 min) affording (E)-4-((1R,5S)-3-oxa-8-azabicyclo[3.2.1]octan-8-yl)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)but-2-en-1-one (7.88 mg, 7.54%) as a yellow amorphous solid: $^1$H NMR (400 MHz, Dimethylsulfoxide-d6) δ 9.19 (t, J=4.6 Hz, 1H), 8.27-8.18 (m, 2H), 7.73-7.64 (m, 2H), 7.61 (t, J=9.0 Hz, 1H), 6.71-6.63 (m, 1H), 6.53-6.42 (m, 1H), 5.37-5.19 (m, 2H), 4.17-4.12 (m, 1H), 4.10-4.03 (m, 2H), 3.95-3.84 (m, 1H), 3.77-3.61 (m, 2H), 3.59-3.49 (m, 3H), 3.43 (br d, J=4.4 Hz, 4H), 3.15-2.98 (m, 8H), 2.87-2.79 (m, 1H), 2.40-2.32 (m, 1H), 2.31-2.24 (m, 1H), 2.18-2.12 (m, 1H), 2.07-1.98 (m, 2H), 1.88-1.82 (m, 3H), 1.81-1.76 (m, 2H), 1.75-1.70 (m, 2H).

LCMS (5% to 95% acetonitrile in water+0.03% ammonium bicarbonate over 6 min); retention time 2.928 min, ESI+ found [M+H]=751.4.

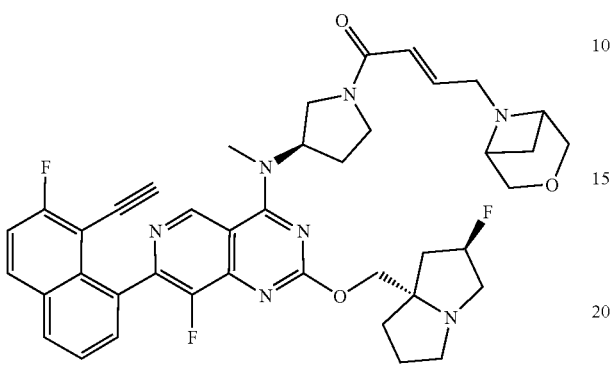

Example 293 (Method 12): (E)-4-(3-oxa-6-azabicyclo[3.1.1]heptan-6-yl)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)but-2-en-1-one

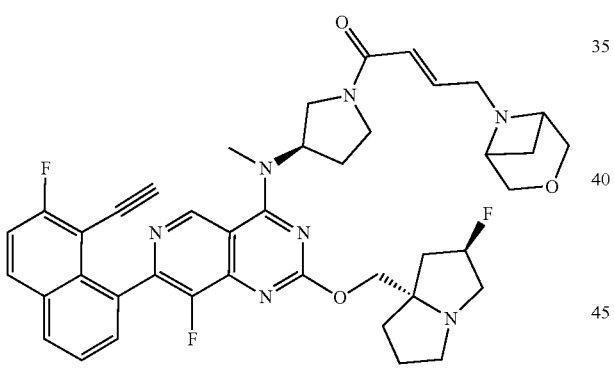

Step 1: (E)-4-(3-oxa-6-azabicyclo[3.1.1]heptan-6-yl)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)but-2-en-1-one The substitution reaction was prepared in a similar fashion to Method #12, Step 2. The resulting residue was purified by reverse phase HPLC (column: Waters Xbridge Prep OBD C18 150*40 mm*10 um; mobile phase: [water (NH$_4$HCO$_3$)-ACN]; B %: 30%-60%, 8 min) affording (E)-4-(3-oxa-6-azabicyclo[3.1.1]heptan-6-yl)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)but-2-en-1-one (7 mg, 6.83%) as a yellow solid: $^1$H NMR (400 MHz, Acetonitrile-d3) δ 9.17 (dd, J=2.4, 4.8 Hz, 1H), 8.18-8.06 (m, 2H), 7.73-7.66 (m, 2H), 7.47 (t, J=9.1 Hz, 1H), 6.78 (td, J=5.3, 15.2 Hz, 1H), 6.51-6.38 (m, 1H), 5.44-5.18 (m, 2H), 4.23-4.11 (m, 4H), 4.09-3.78 (m, 2H), 3.70-3.66 (m, 2H), 3.65-3.59 (m, 1H), 3.56-3.47 (m, 3H), 3.45 (s, 3H), 3.31-3.25 (m, 1H), 3.21-3.12 (m, 2H), 3.08 (s, 1H), 2.95-2.87 (m, 1H), 2.66-2.56 (m, 1H), 2.47-2.37 (m, 1H), 2.34-2.25 (m, 2H), 2.19 (br d, J=1.8 Hz, 1H), 2.17-2.10 (m, 2H), 2.10-1.98 (m, 1H), 1.95-1.84 (m, 3H), 1.84-1.78 (m, 1H).

LCMS (5% to 95% acetonitrile in water+0.03% ammonium bicarbonate over 6 min); retention time 2.833 min, ESI+ found [M+H]=737.3.

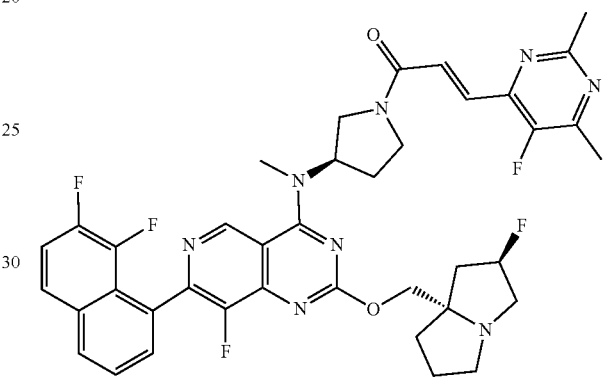

Example 294 (Method 1): (E)-1-((R)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(5-fluoro-2,6-dimethylpyrimidin-4-yl)prop-2-en-1-one

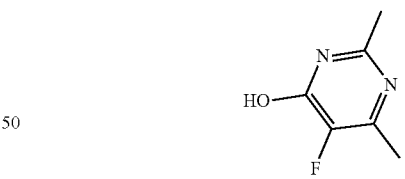

Step 1: 5-fluoro-2,6-dimethylpyrimidin-4-ol

To a solution of acetamidine hydrochloride (702.06 mg, 7.43 mmol) in methanol (15 mL) was added sodium methylate (2.70 mL) and ethyl 2-fluoro-3-oxo-butanoate (1 g, 6.75 mmol). The mixture was stirred at 80° C. for 12 h. The reaction mixture was diluted with water (10 mL) and extracted with dichloromethane (2×10 mL). The combined organic layers were dried over sodium sulphate and concentrated in vacuo affording 5-fluoro-2,6-dimethylpyrimidin-4-ol (850 mg, crude) as a yellow solid, which was used in the next step without further purification. LCMS Rt=0.433 min, m/z=142.1 [M+H]$^+$.

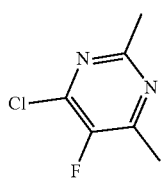

Step 2: 4-chloro-5-fluoro-2,6-dimethylpyrimidine

To a solution of 5-fluoro-2,6-dimethyl-pyrimidin-4-ol (800 mg, 5.63 mmol) in phosphorus oxychloride (10 mL) was added N,N-Diisopropylethylamine (3.64 g, 28.14 mmol). The mixture was stirred at 80° C. for 1 h. The reaction mixture was quenched with saturated sodium bicarbonate (30 mL) and extracted with ethyl acetate (2×100 mL). The combined organic layers were dried over sodium sulphate and concentrated in vacuo affording 4-chloro-5-fluoro-2,6-dimethylpyrimidine (2.5 g, crude) as a brown oil, which was used in the next step without further purification. LCMS Rt=0.543 min, m/z=160.0 [M+H]$^+$.

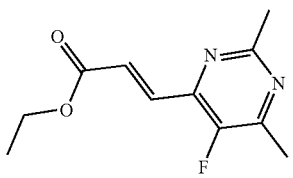 [SMILES: CCOC(=O)/C=C/c1nc(C)nc(C)c1F]

Step 3: (E)-ethyl 3-(5-fluoro-2,6-dimethylpyrimidin-4-yl)acrylate

A mixture of 4-chloro-5-fluoro-2,6-dimethyl-pyrimidine (1 g, 6.23 mmol), ethyl (E)-3-(4,4,5,5-tetramethyl-1,3,2-dioxaborolan-2-yl)prop-2-enoate (1.41 g, 6.23 mmol), [2-(Amino-κN)[1,1-biphenyl]-2-yl-κC]chloro[dicyclohexyl[2,4,6-tris(1-methylethyl)[1,1-biphenyl]-2-yl]phosphine] palladium (489.98 mg, 622.76 µmol), and potassium phosphate (3.97 g, 18.68 mmol) in dioxane (10 mL) and water (5 mL) was degassed and purged with nitrogen 3 times. The mixture was stirred at 100° C. for 2 h under a nitrogen atmosphere. The mixture was diluted with water (30 mL) and extracted with ethyl acetate (3×50 mL). The combined organic layers were dried over sodium sulphate and concentrated in vacuo affording (E)-ethyl 3-(5-fluoro-2,6-dimethylpyrimidin-4-yl)acrylate (2.4 g, crude) as a brown oil, which was used in the next step without further purification. LCMS Rt=0.679 min, m/z=224.1 [M+H]$^+$.

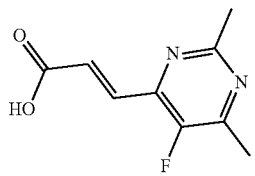

Step 4: (E)-3-(5-fluoro-2,6-dimethylpyrimidin-4-yl)acrylic acid

The hydrolysis reaction was prepared in a similar fashion to Method #1, Step 4. The crude product was concentrated in vacuo affording (E)-3-(5-fluoro-2,6-dimethylpyrimidin-4-yl)acrylic acid (50 mg, crude) as a yellow solid, which was used in the next step without further purification.
LCMS Rt=0.433 min, m/z=196.1 [M+H]$^+$.

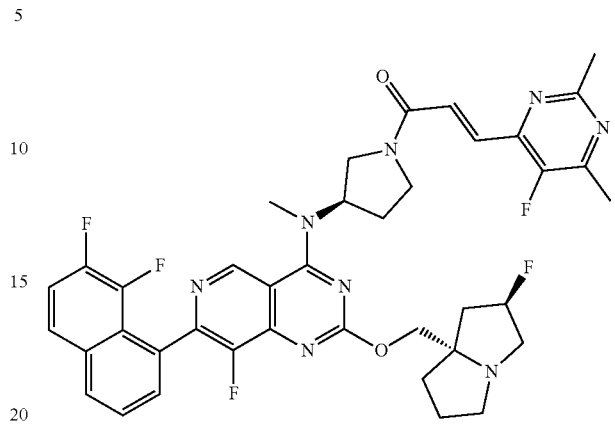

Step 5: (E)-1-((R)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(5-fluoro-2,6-dimethylpyrimidin-4-yl)prop-2-en-1-one The amide coupling reaction was prepared in a similar fashion to Method #1, Step 10. The crude residue was purified by reverse phase HPLC (column: Waters Xbridge BEH C18 100*30 mm*10 µm; mobile phase: [water (NH$_4$HCO$_3$)-ACN]; B %: 40%-70%, 8 min) affording (E)-1-((R)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(5-fluoro-2,6-dimethylpyrimidin-4-yl)prop-2-en-1-one (3.16 mg, 14.14%) as a yellow oil: $^1$H NMR (400 MHz, Acetonitrile-d3) δ 9.42-9.17 (m, 1H), 8.25-8.07 (m, 1H), 7.92 (br dd, J=4.3, 8.6 Hz, 1H), 7.72 (br d, J=5.6 Hz, 2H), 7.66 (br d, J=4.8 Hz, 1H), 7.62 (d, J=13.9 Hz, 1H), 7.59-7.53 (m, 1H), 5.51-5.21 (m, 2H), 4.35-4.18 (m, 2H), 4.11-3.99 (m, 1H), 3.95-3.74 (m, 2H), 3.71-3.60 (m, 1H), 3.48 (d, J=3.1 Hz, 3H), 3.32-3.06 (m, 3H), 3.03-2.90 (m, 1H), 2.62 (d, J=12.3 Hz, 3H), 2.49 (br dd, J=2.8, 4.0 Hz, 3H), 2.14-2.02 (m, 4H), 1.95-1.72 (m, 4H).

LCMS (5% to 95% acetonitrile in water+0.03% ammonium bicarbonate over 6 min); retention time 3.076 min. ESI+ found [M+H]=744.3.

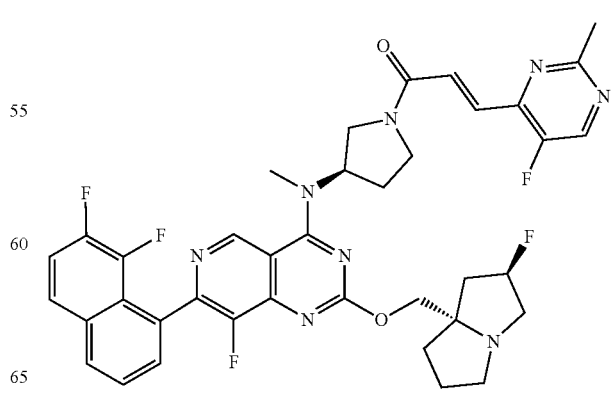

Example 295 (Method 1): (E)-1-((R)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(5-fluoro-2-methylpyrimidin-4-yl)prop-2-en-1-one

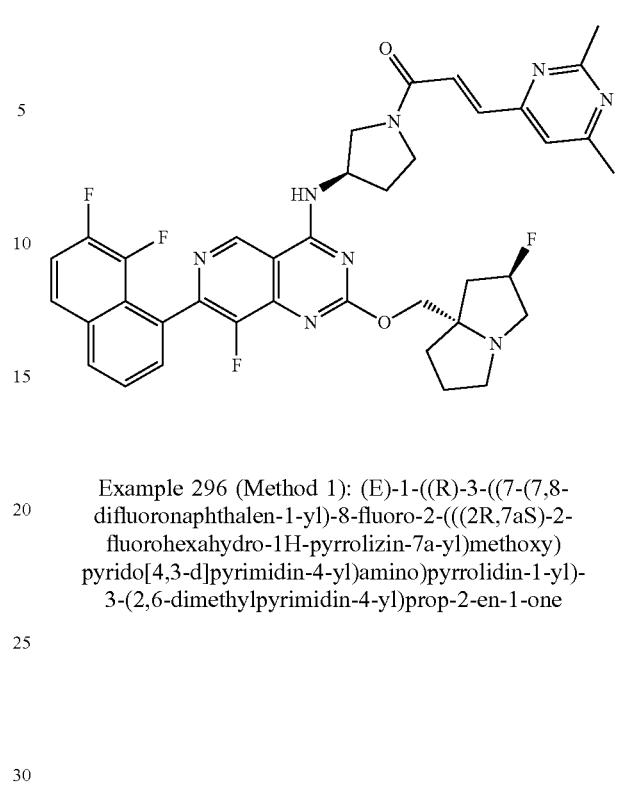

Example 296 (Method 1): (E)-1-((R)-3-((7-(7,8-difluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)pyrrolidin-1-yl)-3-(2,6-dimethylpyrimidin-4-yl)prop-2-en-1-one

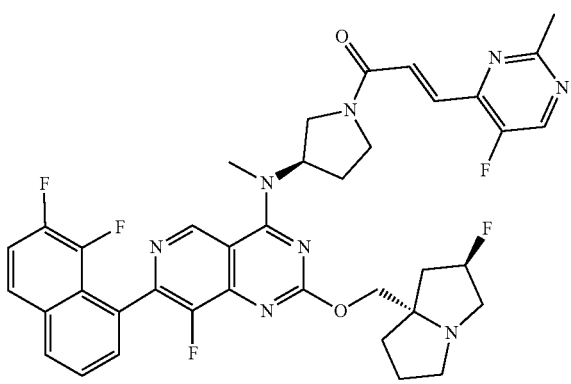 [SMILES: Cc1ncc(F)c(/C=C/C(=O)N2CC[C@@H](N(C)c3nc(OC[C@@]45CCCN4C[C@H](F)C5)nc4c(F)c(-c5cccc6ccc(F)c(F)c56)ncc34)C2)n1]

Step 1: (E)-1-((R)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(5-fluoro-2-methylpyrimidin-4-yl)prop-2-en-1-one The amide coupling reaction was prepared in a similar fashion to Method #1, Step 10. The resulting residue was purified by reverse phase HPLC (column: Waters Xbridge Prep OBD C18 150*40 mm*10 um; mobile phase: [water (NH$_4$HCO$_3$)-ACN]; B %: 30%-60%, 8 min) affording (E)-1-((R)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(5-fluoro-2-methylpyrimidin-4-yl)prop-2-en-1-one (29.25 mg, 27.16%) as a white solid: $^1$H NMR (400 MHz, Acetonitrile-d3) δ 9.24 (s, 1H), 8.60 (dd, J=2.2, 6.6 Hz, 1H), 8.16-8.08 (m, 1H), 7.96-7.85 (m, 1H), 7.73-7.68 (m, 2H), 7.67-7.60 (m, 2H), 7.55 (dt, J=7.8, 9.6 Hz, 1H), 5.48-5.15 (m, 2H), 4.26-4.21 (m, 1H), 4.18-4.12 (m, 1H), 4.08-3.99 (m, 1H), 3.96-3.74 (m, 2H), 3.71-3.51 (m, 1H), 3.46 (s, 3H), 3.21-3.05 (m, 3H), 2.96-2.84 (m, 1H), 2.68 (d, J=14.6 Hz, 3H), 2.51-2.41 (m, 1H), 2.39-2.30 (m, 1H), 2.18-2.04 (m, 3H), 1.88 (br d, J=14.9 Hz, 3H).

LCMS (5% to 95% acetonitrile in water+0.03% ammonium bicarbonate over 6 min); retention time 3.042 min, ESI+ found [M+H]=730.3.

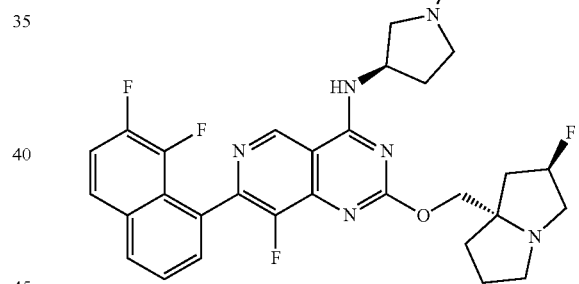

Step 1: (R)-tert-butyl 3-((7-(7,8-difluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)pyrrolidine-1-carboxylate The substitution reaction was prepared in a similar fashion to Method #1, Step 8. The crude product was purified by reverse phase HPLC (column: Waters Xbridge Prep OBD C18 150*40 mm*10 μm; mobile phase: [water (NH$_4$HCO$_3$)-ACN]; B %: 45%-65%, 8 min) affording (R)-tert-butyl 3-((7-(7,8-difluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)pyrrolidine-1-carboxylate (97 mg, 43.89%) as a white solid. LCMS Rt=0.717 min, m/z=652.3 [M+H]$^+$.

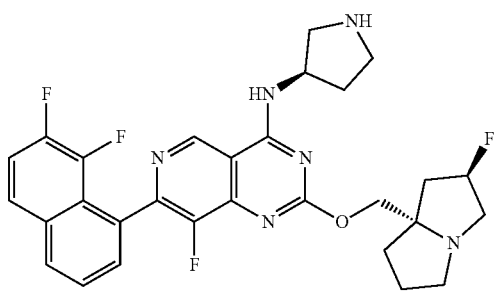 [SMILES: Fc1ccc2cccc(-c3ncc4c(N[C@@H]5CCNC5)nc(OC[C@@]56CCCN5C[C@H](F)C6)nc4c3F)c2c1F]

Step 2: 7-(7,8-difluoronaphthalen-1-yl)-8-fluoro-2-(((2R,7aS)-2-fluorohexahydro-1H-pyrrolizin-7a-yl)methoxy)-N—((R)-pyrrolidin-3-yl)pyrido[4,3-d]pyrimidin-4-amine The deprotection of the Boc group was prepared in a similar fashion to Method #1, Step 9. The reaction mixture was concentrated in vacuo affording 7-(7,8-difluoronaphthalen-1-yl)-8-fluoro-2-(((2R,7aS)-2-fluorohexahydro-1H-pyrrolizin-7a-yl)methoxy)-N—((R)-pyrrolidin-3-yl)pyrido[4,3-d]pyrimidin-4-amine (60 mg, crude, trifluoroacetate salt) as a yellow oil, which was used in the next step without further purification. LCMS Rt=0.518 min, m/z=552.2 [M+H]$^+$.

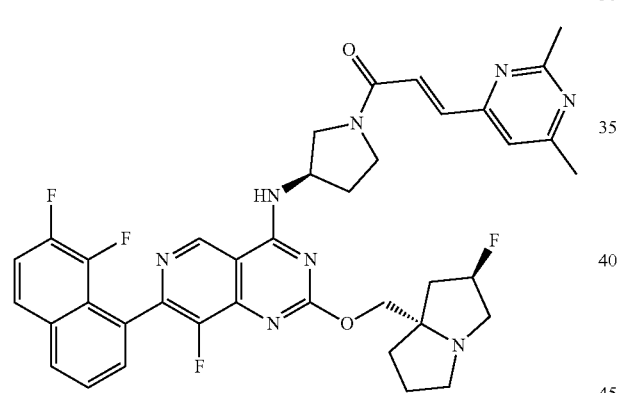

Step 3: (E)-1-((R)-3-((7-(7,8-difluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)pyrrolidin-1-yl)-3-(2,6-dimethylpyrimidin-4-yl)prop-2-en-1-one The amide coupling reaction was prepared in a similar fashion to Method #1, Step 10. The resulting residue was purified by reverse phase HPLC (column: Waters Xbridge Prep OBD C18 150*40 mm*10 μm; mobile phase: [water (NH$_4$HCO$_3$)-ACN]; B %: 45%-65%, 8 min) affording (E)-1-((R)-3-((7-(7,8-difluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)amino)pyrrolidin-1-yl)-3-(2,6-dimethylpyrimidin-4-yl)prop-2-en-1-one (97 mg, 43.89%) as a white solid: $^1$H NMR (400 MHz, Acetonitrile-d3) δ 9.15 (d, J=0.9 Hz, 1H), 8.16-8.09 (m, 1H), 7.91 (ddd, J=1.6, 5.1, 9.2 Hz, 1H), 7.73-7.67 (m, 2H), 7.39 (br s, 4H), 7.24 (d, J=7.5 Hz, 1H), 5.37-5.20 (m, 1H), 5.03-4.90 (m, 1H), 4.29-4.23 (m, 1H), 4.19-4.15 (m, 1H), 4.03-3.62 (m, 4H), 3.22-3.12 (m, 2H), 3.11-3.07 (m, 1H), 2.97-2.86 (m, 1H), 2.62 (d, J=6.8 Hz, 3H), 2.46 (d, J=4.5 Hz, 3H), 2.41-2.30 (m, 1H), 2.28-2.22 (m, 1H), 2.16-2.06 (m, 3H), 1.94-1.81 (m, 3H).

LCMS (5% to 95% acetonitrile in water+0.03% ammonium bicarbonate over 6 min); retention time 2.915 min, ESI+ found [M+H]=712.3.

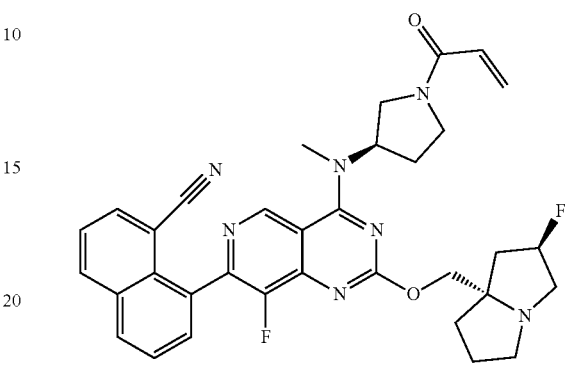

Example 297 (Method 3): 8-(4-(((R)-1-acryloylpyrrolidin-3-yl)(methyl)amino)-8-fluoro-2-(((2R,7aS)-2-fluorotetrahydro-1H-pyrrolizin-7a(5H)-yl)methoxy)pyrido[4,3-d]pyrimidin-7-yl)-1-naphthonitrile

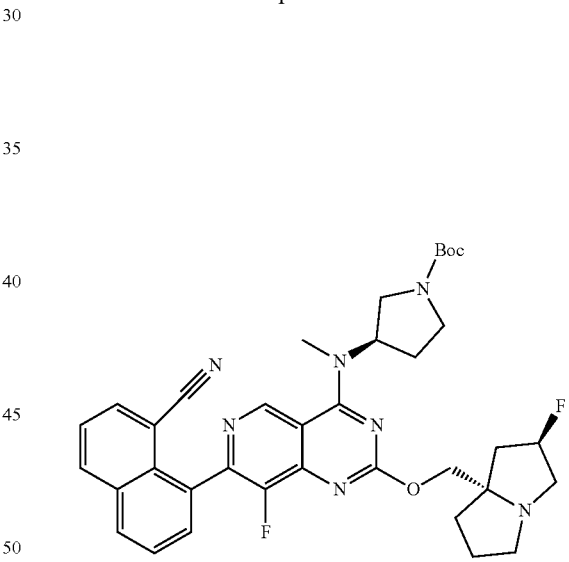

Step 1: tert-butyl (R)-3-((7-(8-cyanonaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidine-1-carboxylate The Stille reaction was prepared in a similar fashion to Method #3, Step 6. The mixture was concentrated in vacuo and purified by reverse phase HPLC (column: Phenomenex luna C18 100*40 mm*3 μm; mobile phase: [water (TFA)-ACN]; B %: 30%-72%, 8 min) affording tert-butyl (R)-3-((7-(8-cyanonaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidine-1-carboxylate (100 mg, 60.51%, trifluoroacetic acid) as a yellow solid. LCMS Rt=1.601 min, m/z=655.3 [M+H]$^+$.

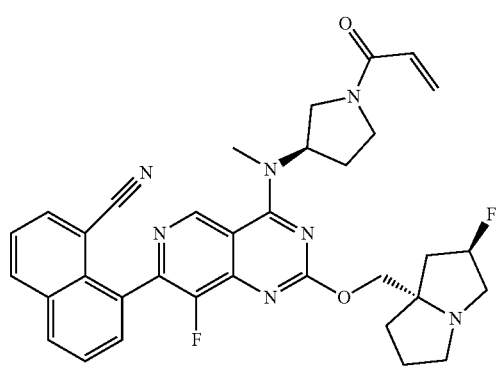 [SMILES: C=CC(=O)N1CC[C@@H](N(C)c2nc(OC[C@@]34CCCN3C[C@H](F)C4)nc3c(F)c(-c4cccc5cccc(C#N)c45)ncc23)C1]

Step 2: 8-(8-fluoro-2-(((2R,7aS)-2-fluorotetrahydro-1H-pyrrolizin-7a(5H)-yl)methoxy)-4-(methyl((R)-pyrrolidin-3-yl)amino)pyrido[4,3-d]pyrimidin-7-yl)-1-naphthonitrile The deprotection of the Boc group was prepared in a similar fashion to Method #1, Step 9. The reaction mixture was concentrated in vacuo affording 8-(8-fluoro-2-(((2R,7aS)-2-fluorotetrahydro-1H-pyrrolizin-7a(5H)-yl)methoxy)-4-(methyl((R)-pyrrolidin-3-yl)amino)pyrido[4,3-d]pyrimidin-7-yl)-1-naphthonitrile (90 mg, crude, trifluoroacetic salt) as a brown oil, which was used in the next step without further purification. LCMS Rt=0.438n, m/z=555.3 [M+H]⁺.

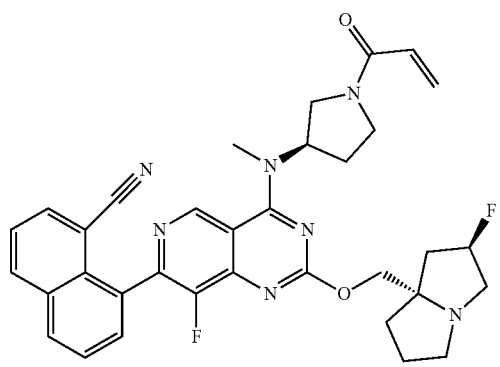 [SMILES: C=CC(=O)N1CC[C@@H](N(C)c2nc(OC[C@@]34CCCN3C[C@H](F)C4)nc3c(F)c(-c4cccc5cccc(C#N)c45)ncc23)C1]

Step 3: 8-(4-(((R)-1-acryloylpyrrolidin-3-yl)(methyl)amino)-8-fluoro-2-(((2R,7aS)-2-fluorotetrahydro-1H-pyrrolizin-7a(5H)-yl)methoxy)pyrido[4,3-d]pyrimidin-7-yl)-1-naphthonitrile The amide coupling reaction was prepared in a similar fashion to Method #3, Step 8. The residue was purified by prep-HPLC (column: Waters Xbridge BEH C18 100*30 mm*10 μm; mobile phase: [water (NH₄HCO₃)-ACN]; B %: 25%-55%, 8 min) affording 8-(4-(((R)-1-acryloylpyrrolidin-3-yl)(methyl)amino)-8-fluoro-2-(((2R,7aS)-2-fluorotetrahydro-1H-pyrrolizin-7a(5H)-yl)methoxy)pyrido[4,3-d]pyrimidin-7-yl)-1-naphthonitrile (16.68 mg, 20.36%) as a yellow amorphous solid: ¹H NMR (400 MHz, Acetonitrile-d3) δ 9.23 (d, J=1.5 Hz, 1H), 8.34 (d, J=7.5 Hz, 1H), 8.23-8.16 (m, 1H), 8.02 (dd, J=1.1, 7.2 Hz, 1H), 7.82-7.75 (m, 2H), 7.67 (dd, J=7.4, 8.1 Hz, 1H), 6.58 (ddd, J=10.3, 15.4, 16.7 Hz, 1H), 6.26-6.20 (m, 1H), 5.67 (ddd, J=2.3, 6.4, 10.3 Hz, 1H), 5.45-5.34 (m, 1H), 5.33-5.17 (m, 1H), 4.24-4.19 (m, 1H), 4.15-4.08 (m, 1H), 3.99-3.77 (m, 2H), 3.69-3.61 (m, 1H), 3.58-3.50 (m, 1H), 3.43 (d, J=1.7 Hz, 3H), 3.17-3.09 (m, 2H), 3.06 (s, 1H), 2.93-2.85 (m, 1H), 2.43-2.35 (m, 1H), 2.33-2.26 (m, 1H), 2.22-2.19 (m, 1H), 2.12-2.05 (m, 2H), 1.91-1.73 (m, 3H).

LCMS (5% to 95% acetonitrile in water+0.03% ammonium bicarbonate over 6 min); retention time 2.770 min. ESI+ found [M+H]=609.3.

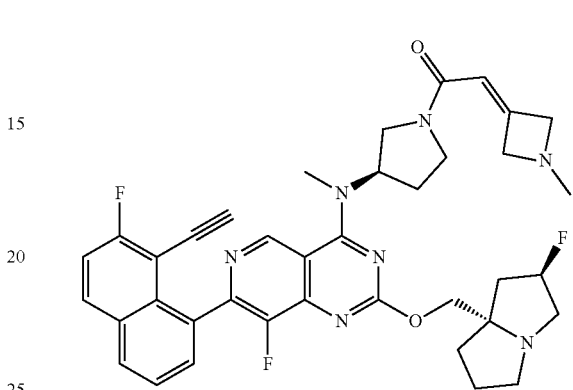

Example 298 (Method 8): 1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-2-(1-methylazetidin-3-ylidene)ethan-1-one

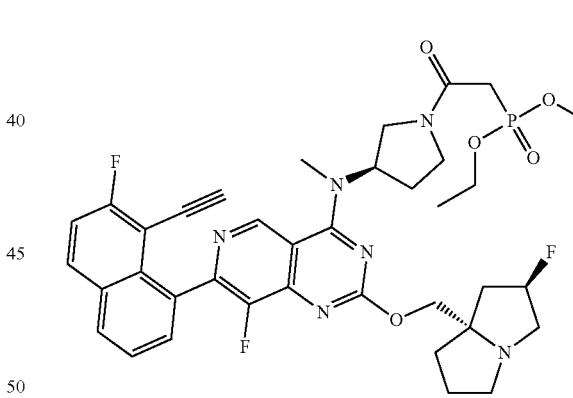

Step 1: diethyl (2-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-2-oxoethyl)phosphonate The amide coupling reaction was prepared in a similar fashion to Method #8, Step 3. The reaction mixture was concentrated in vacuo and purified by column chromatography (silica gel, 100-200 mesh, 0-100% methanol in dichloromethane), affording diethyl (2-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-2-

1049 oxoethyl)phosphonate (150 mg, 68.60%) as a brown oil. LCMS Rt=1.487 min, m/z=750.3 [M+H]⁺.

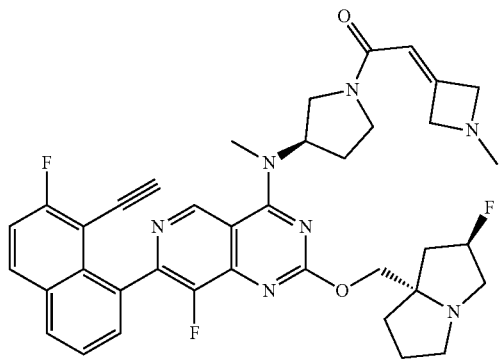 [SMILES: C#Cc1c(F)ccc2cccc(-c3ncc4c(N(C)[C@@H]5CCN(C(=O)C=C6CN(C)C6)C5)nc(OC[C@@]56CCCN5C[C@H](F)C6)nc4c3F)c12]

Step 2: 1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-2-(1-methylazetidin-3-ylidene)ethan-1-one The HWE reaction was prepared in a similar fashion to Method #8, Step 4. The resulting residue was purified by reverse phase HPLC (column: Waters Xbridge Prep OBD C18 150*40 mm*10 μm; mobile phase: [water (NH₄HCO₃)-ACN]; B %: 25%-55%, 8 min) affording 1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-2-(1-methylazetidin-3-ylidene)ethan-1-one (17.92 mg, 18.25%) as a yellow amorphous solid: ¹H NMR (400 MHz, Dimethylsulfoxide-d6) δ 9.20-9.13 (m, 1H), 8.25-8.17 (m, 2H), 7.72-7.63 (m, 2H), 7.60 (t, J=9.0 Hz, 1H), 6.09-6.01 (m, 1H), 5.37-5.19 (m, 2H), 4.17-4.12 (m, 1H), 4.11-4.05 (m, 3H), 4.04-3.97 (m, 1H), 3.92-3.74 (m, 3H), 3.71-3.44 (m, 6H), 3.08 (br d, J=9.0 Hz, 2H), 3.04-2.99 (m, 1H), 2.86-2.78 (m, 1H), 2.37-2.30 (m, 3H), 2.28-2.21 (m, 1H), 2.13 (br s, 1H), 2.06-1.97 (m, 2H), 1.94-1.80 (m, 2H), 1.80-1.67 (m, 2H).

LCMS (5% to 95% acetonitrile in water+0.03% ammonium bicarbonate over 6 min); retention time 2.880 min, ESI+ found [M+H]=681.3.

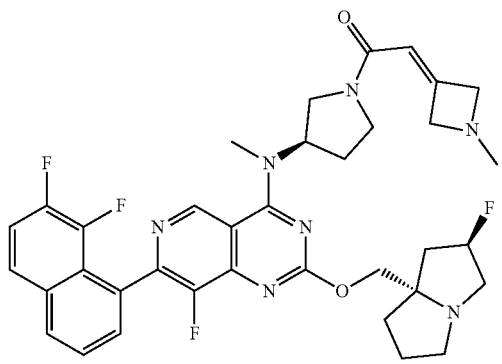 [SMILES: CN1CC(=CC(=O)N2CC[C@@H](N(C)c3nc(OC[C@@]45CCCN4C[C@H](F)C5)nc4c(F)c(-c5cccc6ccc(F)c(F)c56)ncc34)C2)C1]

1050

Example 299 (Method 8): 1-((R)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-2-(1-methylazetidin-3-ylidene)ethan-1-one

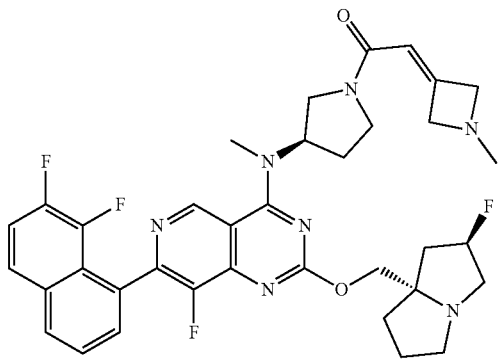 [SMILES: CN1CC(=CC(=O)N2CC[C@@H](N(C)c3nc(OC[C@@]45CCCN4C[C@H](F)C5)nc4c(F)c(-c5cccc6ccc(F)c(F)c56)ncc34)C2)C1]

Step 1: 1-((R)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-2-(1-methylazetidin-3-ylidene)ethan-1-one The HWE reaction was prepared in a similar fashion to Method #8, Step 4. The resulting residue was purified by reverse phase HPLC (column: Waters Xbridge Prep OBD C18 150*40 mm*10 μm; mobile phase: [water (NH₄HCO₃)-ACN]; B %: 25%-55%, 8 min) affording 1-((R)-3-((7-(7,8-difluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-2-(1-methylazetidin-3-ylidene)ethan-1-one (8.15 mg, 7.42%) as a yellow solid: ¹H NMR (400 MHz, Chloroform-d) δ 9.20-9.12 (m, 1H), 8.03-7.92 (m, 1H), 7.77-7.69 (m, 1H), 7.67-7.58 (m, 2H), 7.45-7.35 (m, 1H), 5.88 (br d, J=2.0 Hz, 1H), 5.49-5.38 (m, 1H), 5.37-5.18 (m, 1H), 4.47-4.25 (m, 3H), 4.24-4.17 (m, 1H), 4.13-4.00 (m, 2H), 3.98-3.78 (m, 1H), 3.73-3.60 (m, 1H), 3.59-3.50 (m, 1H), 3.50-3.40 (m, 3H), 3.32-3.15 (m, 3H), 3.05-2.91 (m, 1H), 2.58-2.43 (m, 3H), 2.40-2.10 (m, 5H), 2.05-1.84 (m, 4H).

LCMS (5% to 95% acetonitrile in water+0.03% ammonium bicarbonate over 6 min); retention time 2.902 min, ESI+ found [M+H]=675.3.

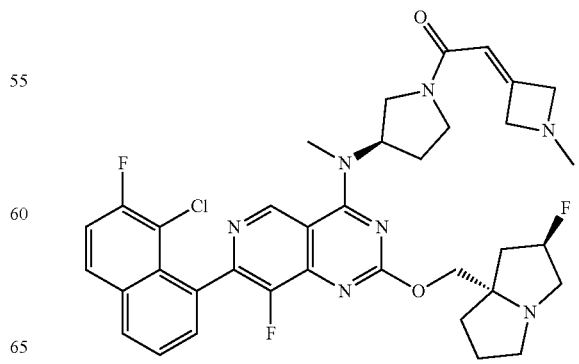

Example 300 (Method 8): 1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-2-(1-methylazetidin-3-ylidene)ethan-1-one

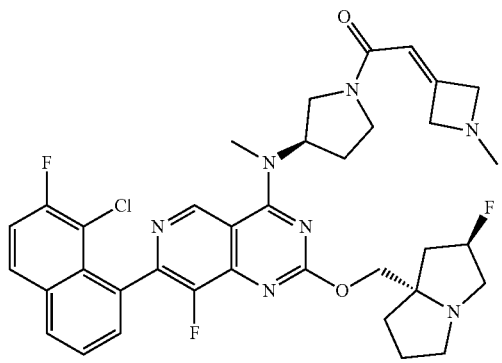 [SMILES: CN1CC(=CC(=O)N2CC[C@@H](N(C)c3nc(OC[C@@]45CCCN4C[C@H](F)C5)nc4c(F)c(-c5cccc6ccc(F)c(Cl)c56)ncc34)C2)C1]

Step 1: 1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-2-(1-methylazetidin-3-ylidene)ethan-1-one The HWE reaction was prepared in a similar fashion to Method #8, Step 4. The resulting residue was purified by reverse phase HPLC (column: Waters Xbridge Prep OBD C18 150*40 mm*10 μm; mobile phase: [water (NH$_4$HCO$_3$)-ACN]; B %: 30%-60%, 8 min) affording 1-((R)-3-((7-(8-chloro-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-2-(1-methylazetidin-3-ylidene)ethan-1-one (16.59 mg, 13.81%) as a white solid: $^1$H NMR (400 MHz, Acetonitrile-d3) δ 9.20 (d, J=2.1 Hz, 1H), 8.21-8.06 (m, 2H), 7.78-7.63 (m, 2H), 7.54 (t, J=8.9 Hz, 1H), 6.08-5.94 (m, 1H), 5.44-5.17 (m, 2H), 4.26-4.11 (m, 4H), 4.09-3.87 (m, 3H), 3.85-3.74 (m, 1H), 3.68-3.48 (m, 2H), 3.44 (br d, J=4.1 Hz, 3H), 3.19-3.04 (m, 3H), 2.98-2.86 (m, 1H), 2.43-2.36 (m, 3H), 2.36-2.24 (m, 2H), 2.17-2.02 (m, 3H), 1.94-1.82 (m, 3H).

LCMS (5% to 95% acetonitrile in water+0.03% ammonium bicarbonate over 6 min); retention time 1.970 min, ESI+ found [M+H]=691.3.

Example 301 (Method 14): (E)-1-((R)-3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(5-fluoro-2-methylpyrimidin-4-yl)prop-2-en-1-one

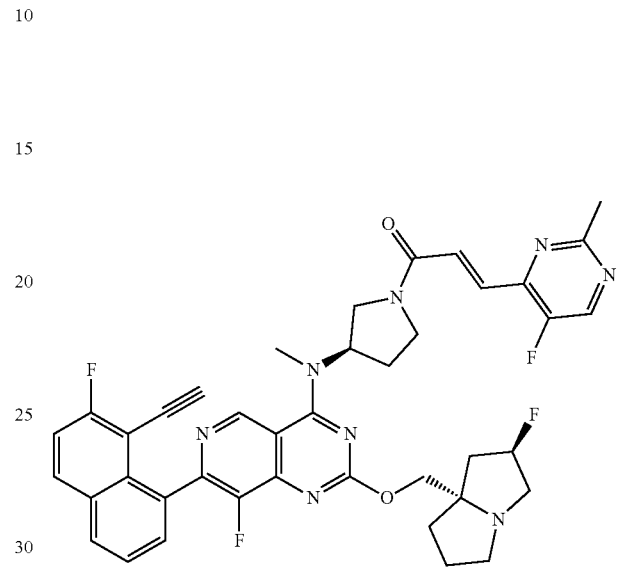

Step 1: (E)-1-((R)-3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(5-fluoro-2-methylpyrimidin-4-yl)prop-2-en-1-one The amide coupling reaction was prepared in a similar fashion to Method #14, Step 4. The crude product was purified by reverse phase HPLC (column: Waters Xbridge Prep OBD C18 150*40 mm*10 μm; mobile phase: [water (NH$_4$HCO$_3$)-ACN]; B %: 40%-65%, 8 min) affording (E)-1-((R)-3-((7-(8-ethynyl-7-fluoronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)-3-(5-fluoro-2-methylpyrimidin-4-yl)prop-2-en-1-one (17.13 mg, 26.49%) as a yellow amorphous solid: $^1$H NMR (400 MHz, Acetonitrile-d3) δ 9.26-9.17 (m, 1H), 8.68-8.57 (m, 1H), 8.22-8.09 (m, 2H), 7.74-7.58 (m, 4H), 7.52-7.42 (m, 1H), 5.51-5.17 (m, 2H), 4.24 (br d, J=10.5 Hz, 1H), 4.18-4.12 (m, 1H), 4.10-4.00 (m, 1H), 3.97-3.69 (m, 2H), 3.67-3.53 (m, 1H), 3.48 (d, J=3.3 Hz, 3H), 3.32-3.25 (m, 1H), 3.19-3.06 (m, 3H), 2.95-2.86 (m, 1H), 2.73-2.65 (m, 3H), 2.53-2.45 (m, 1H), 2.41-2.34 (m, 1H), 2.13 (br d, J=3.3 Hz, 3H), 1.92-1.78 (m, 3H).

LCMS (5% to 95% acetonitrile in water+0.03% ammonium bicarbonate over 6 min); retention time 2.999 min, ESI+ found [M+H]=736.3.

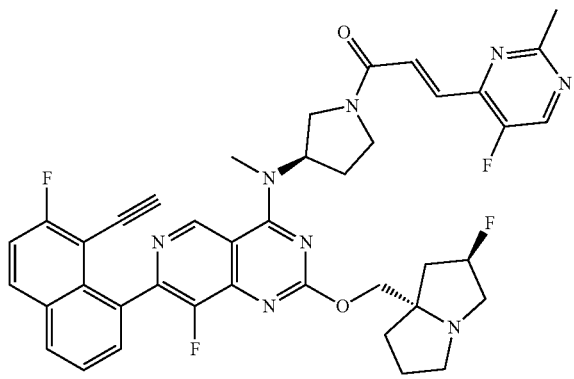

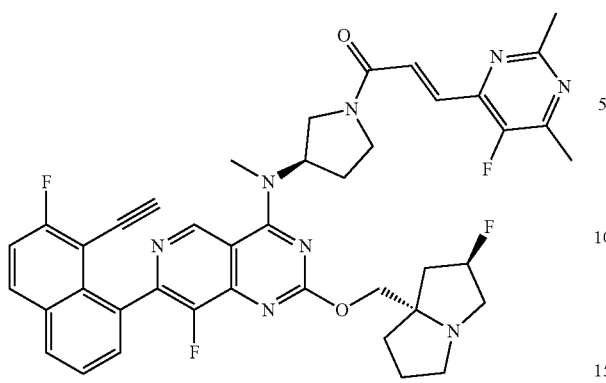

Example 302 (Method 14): (E)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(5-fluoro-2,6-dimethylpyrimidin-4-yl)prop-2-en-1-one

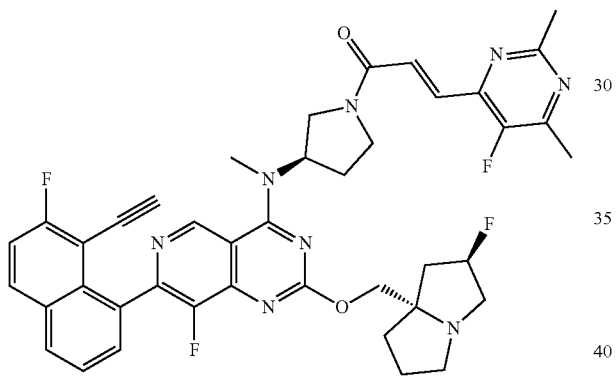

Step 1: (E)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(5-fluoro-2,6-dimethylpyrimidin-4-yl)prop-2-en-1-one The amide coupling reaction was prepared in a similar fashion to Method #14, Step 4. The crude product was purified by reverse phase HPLC (column: Waters Xbridge Prep OBD C18 150*40 mm*10 μm; mobile phase: [water (NH$_4$HCO$_3$)-ACN]; B %: 40%-70%, 8 min) affording (E)-1-((R)-3-((7-(8-ethynyl-7-fluoronaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)-3-(5-fluoro-2,6-dimethylpyrimidin-4-yl)prop-2-en-1-one (16.23 mg, 9.70%) as a white amorphous solid: $^1$H NMR (400 MHz, Acetonitrile-d3) δ 9.22-9.17 (m, 1H), 8.18-8.11 (m, 2H), 7.72-7.65 (m, 3H), 7.64-7.55 (m, 1H), 7.47 (t, J=9.1 Hz, 1H), 5.54-5.17 (m, 2H), 4.32-4.19 (m, 2H), 4.18-4.00 (m, 2H), 3.98-3.67 (m, 2H), 3.65-3.52 (m, 1H), 3.48 (d, J=3.4 Hz, 3H), 3.33-3.25 (m, 1H), 3.17 (br d, J=7.6 Hz, 1H), 3.11-3.06 (m, 1H), 2.97-2.85 (m, 1H), 2.65-2.59 (m, 3H), 2.48 (dd, J=2.6, 4.6 Hz, 3H), 2.16-2.01 (m, 4H), 1.94-1.77 (m, 4H).

LCMS (5% to 95% acetonitrile in water+0.03% ammonium bicarbonate over 6 min); retention time 3.045 min, ESI+ found [M+H]=750.3.

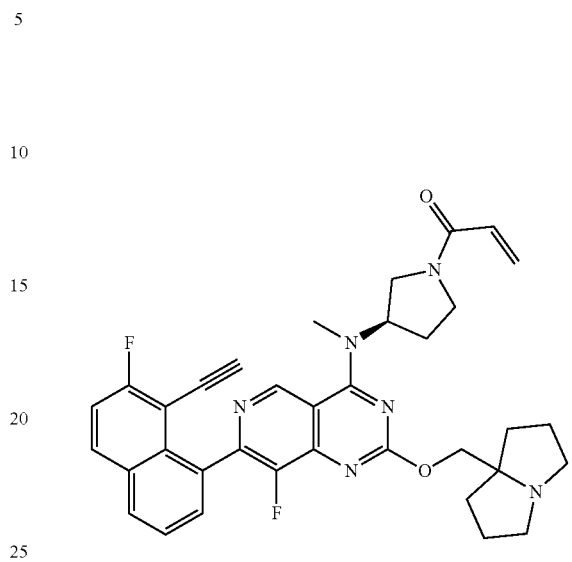

Example 303 (Method 14): (R)-1-(3-((7-(8-ethynyl-7-fluoronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)prop-2-en-1-one

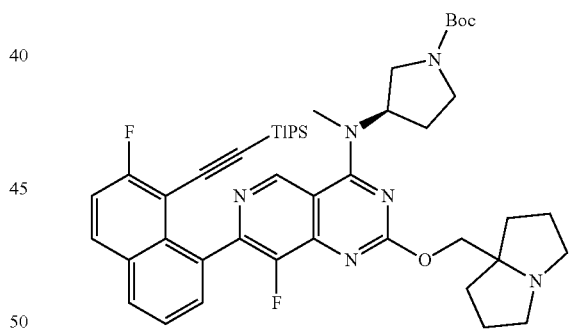

Step 1: tert-butyl (R)-3-((8-fluoro-7-(7-fluoro-8-((triisopropylsilyl)ethynyl)naphthalen-1-yl)-2-((tetrahydro-1H-pyrrolizin-7a(5H)-yl)methoxy)pyrido[4,3-d]pyrimidin-4-yl)(methyl)amino)pyrrolidine-1-carboxylate The Suzuki reaction was prepared in a similar fashion to Method #14, Step 1. The residue was purified by column chromatography (silica gel, 100-200 mesh, 0-100% ethyl acetate in petroleum ether) affording tert-butyl (R)-3-((8-fluoro-7-(7-fluoro-8-((triisopropylsilyl)ethynyl)naphthalen-1-yl)-2-((tetrahydro-1H-pyrrolizin-7a(5H)-yl)methoxy)pyrido[4,3-d]pyrimidin-4-yl)(methyl)amino)pyrrolidine-1-carboxylate (340 mg, 87.36%) as a yellow solid. LCMS Rt=0.873 min, m/z=810.5 [M+H]$^+$.

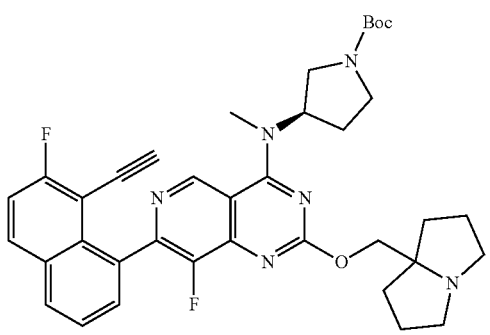 [SMILES: C#Cc1c(F)ccc2cccc(-c3ncc4c(N(C)[C@@H]5CCN(C(=O)OC(C)(C)C)C5)nc(OCC56CCCN5CCC6)nc4c3F)c12]

Step 2: tert-butyl (R)-3-((7-(8-ethynyl-7-fluoronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidine-1-carboxylate The deprotection of the TIPS group was prepared in a similar fashion to Method #14, Step 2. The residue was concentrated in vacuo affording tert-butyl (R)-3-((7-(8-ethynyl-7-fluoronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidine-1-carboxylate (140 mg, crude) as a yellow solid, which was used in the next step without further purification. LCMS Rt=0.648 min, m/z=654.3 [M+H]$^+$.

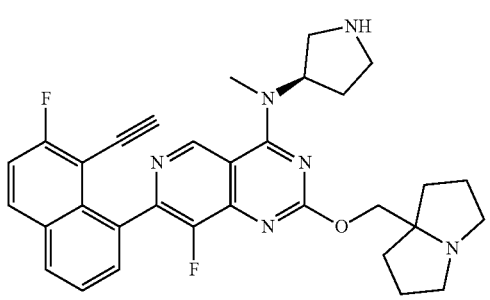 [SMILES: C#Cc1c(F)ccc2cccc(-c3ncc4c(N(C)[C@@H]5CCNC5)nc(OCC56CCCN5CCC6)nc4c3F)c12]

Step 3: (R)-7-(8-ethynyl-7-fluoronaphthalen-1-yl)-8-fluoro-N-methyl-N-(pyrrolidin-3-yl)-2-((tetrahydro-1H-pyrrolizin-7a(5H)-yl)methoxy)pyrido[4,3-d]pyrimidin-4-amine The deprotection of the Boc group was prepared in a similar fashion to Method #14, Step 3. The reaction mixture was concentrated in vacuo affording (R)-7-(8-ethynyl-7-fluoronaphthalen-1-yl)-8-fluoro-N-methyl-N-(pyrrolidin-3-yl)-2-((tetrahydro-1H-pyrrolizin-7a(5H)-yl)methoxy)pyrido[4,3-d]pyrimidin-4-amine (122.55 mg, crude, trifluoroacetic salt) as a yellow oil, which was used in the next step without further purification. LCMS Rt=0.475 min, m/z=554.3 [M+H]$^+$.

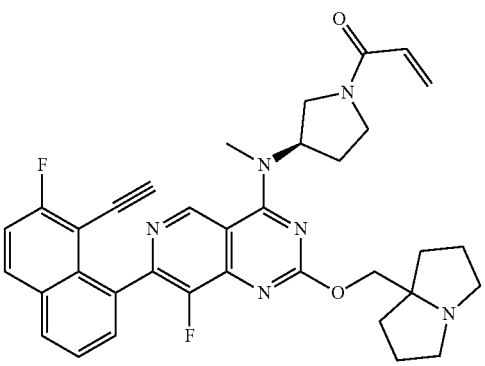 [SMILES: C#Cc1c(F)ccc2cccc(-c3ncc4c(N(C)[C@@H]5CCN(C(=O)C=C)C5)nc(OCC56CCCN5CCC6)nc4c3F)c12]

Step 4: (R)-1-(3-((7-(8-ethynyl-7-fluoronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)prop-2-en-1-one The amide coupling reaction was prepared in a similar fashion to Method #14, Step 4. The crude product was purified by reverse phase prep-HPLC (column: Waters Xbridge Prep OBD C18 150*40 mm*10 um; mobile phase: [water (NH$_4$HCO$_3$)-ACN]; B %: 30%-60%, 8 min) affording (R)-1-(3-((7-(8-ethynyl-7-fluoronaphthalen-1-yl)-8-fluoro-2-((tetrahydro-1H-pyrrolizin-7a(5H)-yl)methoxy)pyrido[4,3-d]pyrimidin-4-yl)(methyl)amino)pyrrolidin-1-yl)prop-2-en-1-one (8.11 mg, 7.27%) as a yellow amorphous solid: $^1$H NMR (400 MHz, Acetonitrile-d3) δ 9.25-9.10 (m, 1H), 8.23-8.07 (m, 2H), 7.76-7.64 (m, 2H), 7.47 (t, J=9.1 Hz, 1H), 6.62 (ddd, J=10.3, 14.1, 16.8 Hz, 1H), 6.26 (td, J=2.4, 16.9 Hz, 1H), 5.70 (ddd, J=2.2, 5.7, 10.3 Hz, 1H), 5.51-5.30 (m, 1H), 4.19 (s, 1H), 4.17-3.82 (m, 2H), 3.79-3.49 (m, 2H), 3.48-3.41 (m, 3H), 3.34-3.25 (m, 1H), 3.08-2.94 (m, 2H), 2.71-2.59 (m, 2H), 2.50-2.37 (m, 1H), 2.14 (br dd, J=2.6, 4.9 Hz, 1H), 2.05-1.99 (m, 2H), 1.92-1.77 (m, 5H), 1.72-1.62 (m, 2H).

LCMS (5% to 95% acetonitrile in water+0.03% ammonium bicarbonate over 6 min); retention time 2.711 min, ESI+ found [M+H]=608.3.

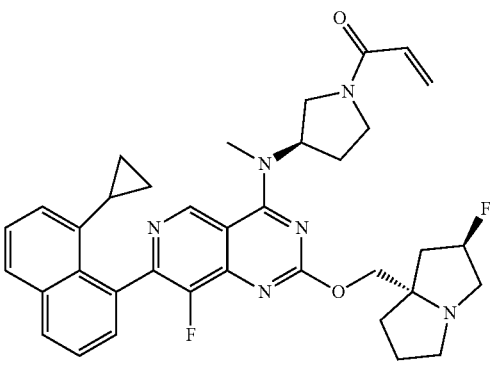 [SMILES: C=CC(=O)N1CC[C@@H](N(C)c2nc(OC[C@@]34CCCN3C[C@H](F)C4)nc3c(F)c(-c4cccc5cccc(C6CC6)c45)ncc23)C1]

Example 304 (Method 1): 1-((R)-3-((7-(8-cyclopropylnaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one

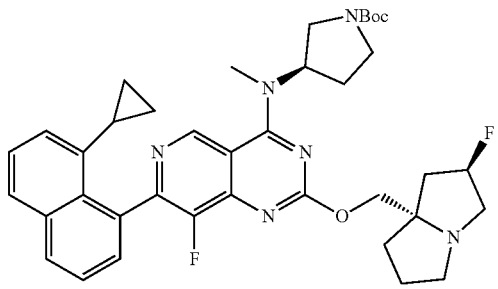 [SMILES: CN(c1nc(OC[C@@]23CCCN2C[C@H](F)C3)nc2c(F)c(-c3cccc4cccc(C5CC5)c34)ncc12)[C@@H]1CCN(C(=O)OC(C)(C)C)C1]

Step 1: tert-butyl (R)-3-((7-(8-cyclopropylnaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidine-1-carboxylate A mixture of (R)-tert-butyl 3-((7-(8-chloronaphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (90 mg, 135.30 μmol), cyclopropylboronic acid (58.11 mg, 676.52 μmol), [1,1'-Bis(diphenylphosphino)ferrocene]dichloropalladium (II) (39.60 mg, 54.12 μmol), Chloro(2-dicyclohexylphosphino-2',4',6'-triisopropyl-1,1'-biphenyl)[2-(2'-amino-1,1'-biphenyl)]palladium(II) (21.29 mg, 27.06 μmol), and caesium carbonate (132.25 mg, 405.91 μmol) in dioxane (1.5 mL) and water (0.5 mL) was degassed and purged with nitrogen 3 times. The mixture was stirred at 100° C. for 1 h under a nitrogen atmosphere. The combined organic layers were dried over sodium sulphate and concentrated in vacuo. The remaining residue was purified by reverse phase HPLC (column: Phenomenex C18 80*30 mm*3 μm; mobile phase: [water (TFA)-ACN]; B %: 35%-65%, 8 min) affording tert-butyl (R)-3-((7-(8-cyclopropylnaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidine-1-carboxylate (32 mg, 35.26%, trifluoroacetic acid salt) as a yellow solid. LCMS Rt=1.850 min, m/z=670.3 [M+H]+.

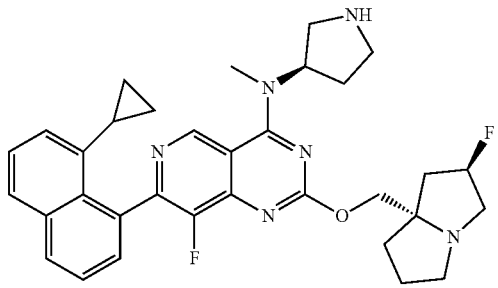 [SMILES: CN(c1nc(OC[C@@]23CCCN2C[C@H](F)C3)nc2c(F)c(-c3cccc4cccc(C5CC5)c34)ncc12)[C@@H]1CCNC1]

Step 2: 7-(8-cyclopropylnaphthalen-1-yl)-8-fluoro-2-(((2R,7aS)-2-fluorotetrahydro-1H-pyrrolizin-7a(5H)-yl)methoxy)-N-methyl-N—((R)-pyrrolidin-3-yl)pyrido[4,3-d]pyrimidin-4-amine The deprotection of the Boc group was prepared in a similar fashion to Method #1, Step 9. The reaction mixture was concentrated in vacuo affording 7-(8-cyclopropylnaphthalen-1-yl)-8-fluoro-2-(((2R,7aS)-2-fluorotetrahydro-1H-pyrrolizin-7a(5H)-yl)methoxy)-N-methyl-N—((R)-pyrrolidin-3-yl)pyrido[4,3-d]pyrimidin-4-amine (25.52 mg, crude, trifluoroacetic acid salt) as a pale yellow oil, which was used in the next step without further purification. LCMS Rt=0.539 min, m/z=570.3 [M+H]+.

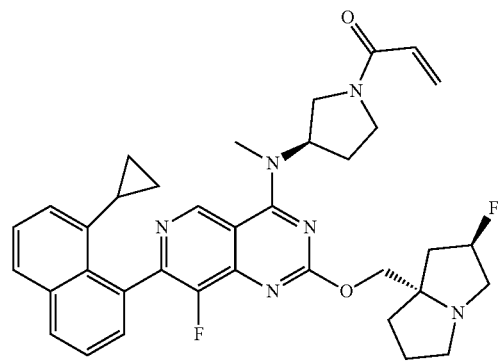 [SMILES: C=CC(=O)N1CC[C@@H](N(C)c2nc(OC[C@@]34CCCN3C[C@H](F)C4)nc3c(F)c(-c4cccc5cccc(C6CC6)c45)ncc23)C1]

Step 3: 1-((R)-3-((7-(8-cyclopropylnaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one The amide coupling reaction was prepared in a similar fashion to Method #1, Step 10. The reaction mixture was concentrated in vacuo and the residue was purified by reverse phase HPLC (column: Waters Xbridge Prep OBD C18 150*40 mm*10 μm; mobile phase: [water (NH$_4$HCO$_3$)-ACN]; B %: 35%-65%, 8 min) affording 1-((R)-3-((7-(8-cyclopropylnaphthalen-1-yl)-8-fluoro-2-(((2R,7aS)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (4.67 mg, 18.95%) as a pale yellow solid: $^1$H NMR (400 MHz, Acetonitrile-d3) δ 9.09 (d, J=2.0 Hz, 1H), 7.96 (d, J=8.1 Hz, 1H), 7.80 (d, J=7.9 Hz, 1H), 7.54-7.48 (m, 1H), 7.47-7.42 (m, 1H), 7.41-7.36 (m, 1H), 7.35-7.31 (m, 1H), 6.66-6.32 (m, 1H), 6.16 (td, J=2.6, 16.9 Hz, 1H), 5.59 (ddd, J=2.3, 6.0, 10.3 Hz, 1H), 5.39-4.99 (m, 2H), 4.18-4.09 (m, 1H), 4.07-4.00 (m, 1H), 3.93-3.69 (m, 2H), 3.65-3.53 (m, 1H), 3.52-3.36 (m, 1H), 3.34-3.26 (m, 3H), 3.09-2.96 (m, 3H), 2.87-2.77 (m, 1H), 2.36-2.27 (m, 1H), 2.24-2.17 (m, 1H), 2.03-1.91 (m, 3H), 1.80-1.75 (m, 2H), 1.58-1.48 (m, 1H), 1.27-1.13 (m, 1H), 0.64-0.35 (m, 1H), 0.34-0.15 (m, 2H), 0.06-0.11 (m, 1H).

LCMS (5% to 95% acetonitrile in water+0.03% ammonium bicarbonate over 6 min); retention time 3.114 min, ESI+ found [M+H]=624.3.

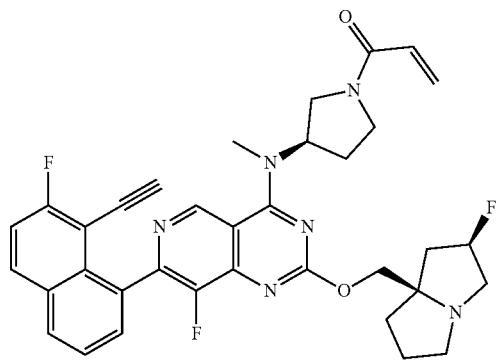 [SMILES: C#Cc1c(F)ccc2cccc(-c3ncc4c(N(C)[C@@H]5CCN(C(=O)C=C)C5)nc(OC[C@]56CCCN5C[C@H](F)C6)nc4c3F)c12]

Example 305 (Method 14): 1-((R)-3-((7-(8-ethynyl-7-fluoronaphthalen-1-yl)-8-fluoro-2-(((2R,7aR)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one

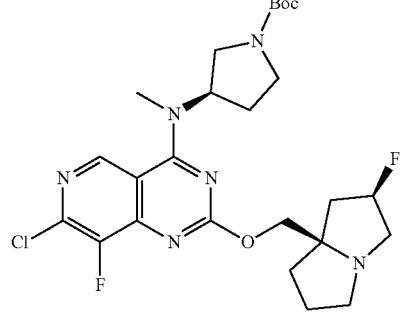 [SMILES: CN(c1nc(OC[C@]23CCCN2C[C@H](F)C3)nc2c(F)c(Cl)ncc12)[C@@H]1CCN(C(=O)OC(C)(C)C)C1]

Step 1: tert-butyl (R)-3-((7-chloro-8-fluoro-2-(((2R,7aR)-2-fluorotetrahydro-1H-pyrrolizin-7a(5H)-yl)methoxy)pyrido[4,3-d]pyrimidin-4-yl)(methyl)amino)pyrrolidine-1-carboxylate The substitution reaction was prepared in a similar fashion to Method #2, Step 4. The residue was purified by column chromatography (silica gel, 100-200 mesh, 70-100% ethyl acetate in petroleum ether) affording tert-butyl (R)-3-((7-chloro-8-fluoro-2-(((2R,7aR)-2-fluorotetrahydro-1H-pyrrolizin-7a(5H)-yl)methoxy)pyrido[4,3-d]pyrimidin-4-yl)(methyl)amino)pyrrolidine-1-carboxylate (500 mg, 77.23%) as a black oil. LCMS Rt=0.615 min, m/z=539.2 [M+H]+.

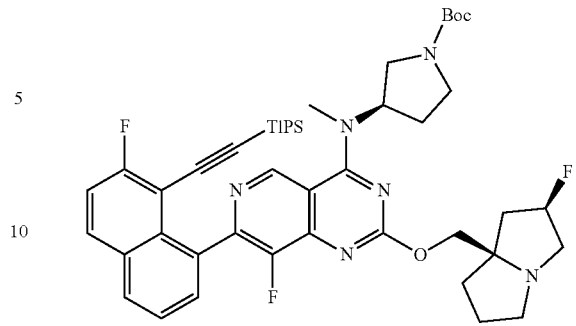

Step 2: tert-butyl (R)-3-((8-fluoro-7-(7-fluoro-8-((triisopropylsilyl)ethynyl)naphthalen-1-yl)-2-(((2R,7aR)-2-fluorotetrahydro-1H-pyrrolizin-7a(5H)-yl)methoxy)pyrido[4,3-d]pyrimidin-4-yl)(methyl)amino)pyrrolidine-1-carboxylate The Suzuki reaction was prepared in a similar fashion to Method #14, Step 1. The residue was purified by column chromatography (silica gel, 100-200 mesh, 0-8% methanol in dichloromethane) affording tert-butyl (R)-3-((8-fluoro-7-(7-fluoro-8-((triisopropylsilyl)ethynyl)naphthalen-1-yl)-2-(((2R,7aR)-2-fluorotetrahydro-1H-pyrrolizin-7a(5H)-yl)methoxy)pyrido[4,3-d]pyrimidin-4-yl)(methyl)amino)pyrrolidine-1-carboxylate (120 mg, 9.10%) as a yellow oil. LCMS Rt=0.930 min, m/z=829.4 [M+H]+.

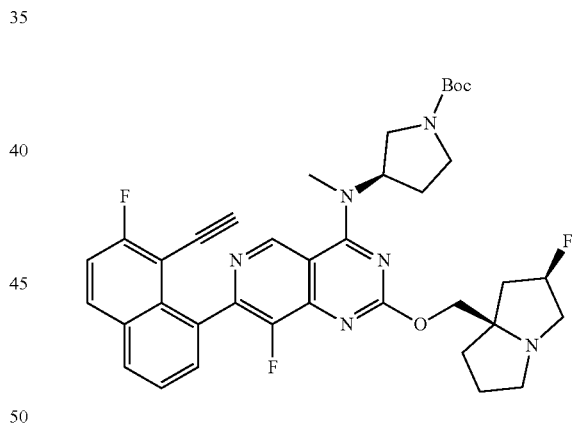

Step 3: tert-butyl (R)-3-((7-(8-ethynyl-7-fluoronaphthalen-1-yl)-8-fluoro-2-(((2R,7aR)-2-fluorotetrahydro-1H-pyrrolizin-7a(5H)-yl)methoxy)pyrido[4,3-d]pyrimidin-4-yl)(methyl)amino)pyrrolidine-1-carboxylate The deprotection of the TIPS group was prepared in a similar fashion to Method #14, Step 2. The residue was purified by column chromatography (silica gel, 100-200 mesh, 0-10% methanol in dichloromethane) affording tert-butyl (R)-3-((7-(8-ethynyl-7-fluoronaphthalen-1-yl)-8-fluoro-2-(((2R,7aR)-2-fluorotetrahydro-1H-pyrrolizin-7a(5H)-yl)methoxy)pyrido[4,3-d]pyrimidin-4-yl)(methyl)amino)pyrrolidine-1-carboxylate (60 mg, 67.22%) as a yellow oil. LCMS Rt=0.673 min, m/z=673.3 [M+H]+.

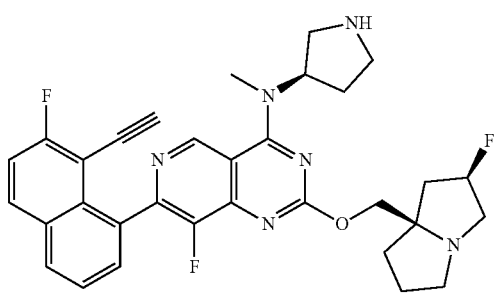 [SMILES: C#Cc1c(F)ccc2cccc(-c3ncc4c(N(C)[C@@H]5CCNC5)nc(OC[C@]56CCCN5C[C@H](F)C6)nc4c3F)c12]

Step 4: 7-(8-ethynyl-7-fluoronaphthalen-1-yl)-8-fluoro-2-(((2R,7aR)-2-fluorotetrahydro-1H-pyrrolizin-7a(5H)-yl)methoxy)-N-methyl-N—((R)-pyrrolidin-3-yl)pyrido[4,3-d]pyrimidin-4-amine The deprotection of the Boc group was prepared in a similar fashion to Method #14, Step 3. The reaction mixture was concentrated in vacuo affording 7-(8-ethynyl-7-fluoronaphthalen-1-yl)-8-fluoro-2-(((2R,7aR)-2-fluorotetrahydro-1H-pyrrolizin-7a(5H)-yl)methoxy)-N-methyl-N—((R)-pyrrolidin-3-yl)pyrido[4,3-d]pyrimidin-4-amine (45 mg, crude, hydrochloric salt) as a yellow oil, which was used in the next step without further purification. LCMS Rt=0.544 min, m/z=573.3 [M+H]$^+$.

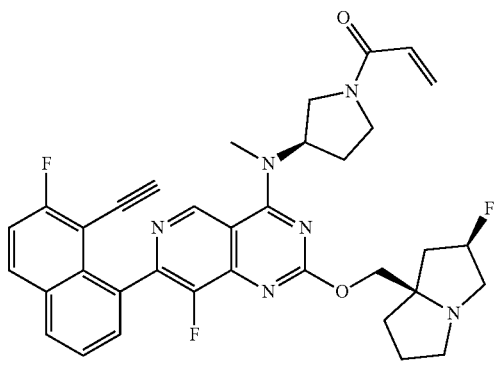 [SMILES: C#Cc1c(F)ccc2cccc(-c3ncc4c(N(C)[C@@H]5CCN(C(=O)C=C)C5)nc(OC[C@]56CCCN5C[C@H](F)C6)nc4c3F)c12]

Step 5: 1-((R)-3-((7-(8-ethynyl-7-fluoronaphthalen-1-yl)-8-fluoro-2-(((2R,7aR)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one The amide coupling reaction was prepared in a similar fashion to Method #14, Step 4. The crude product was purified by reverse phase prep-HPLC (column: Waters Xbridge Prep OBD C18 150*40 mm*10 μm; mobile phase: [water (NH$_4$HCO$_3$)-ACN]; B %: 25%-65%, 8 min) affording 1-((R)-3-((7-(8-ethynyl-7-fluoronaphthalen-1-yl)-8-fluoro-2-(((2R,7aR)-2-fluorotetrahydro-1H-pyrrolizin-7a(5H)-yl)methoxy)pyrido[4,3-d]pyrimidin-4-yl)(methyl)amino)pyrrolidin-1-yl)prop-2-en-1-one (11.35 mg, 22.51%) as a pale yellow solid: $^1$H NMR (400 MHz, Chloroform-d) δ 9.19-9.12 (m, 1H), 8.02-7.92 (m, 2H), 7.67-7.52 (m, 2H), 7.39-7.32 (m, 1H), 6.57-6.39 (m, 2H), 5.79-5.69 (m, 1H), 5.56-5.27 (m, 2H), 4.64-4.42 (m, 2H), 4.30-3.95 (m, 2H), 3.93-3.72 (m, 2H), 3.67-3.56 (m, 1H), 3.48 (br d, J=4.4 Hz, 3H), 3.32-2.84 (m, 3H), 2.83-2.53 (m, 2H), 2.52-2.20 (m, 3H), 2.11-1.75 (m, 4H).

LCMS (5% to 95% acetonitrile in water+0.03% ammonium bicarbonate over 6 min); retention time 2.837 min, ESI+ found [M+H]=627.3.

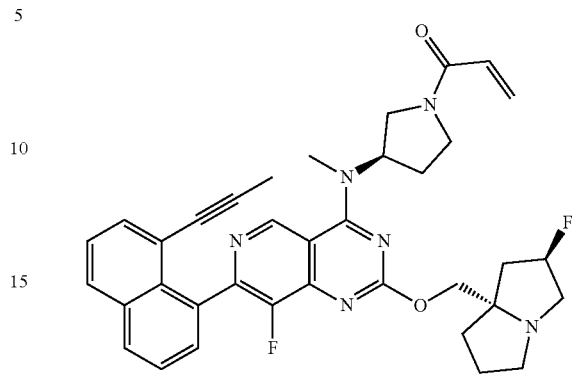

Example 306 (Method 15): 1-((R)-3-((8-fluoro-2-(((2R,7aS)-2-fluorotetrahydro-1H-pyrrolizin-7a(5H)-yl)methoxy)-7-(8-(prop-1-yn-1-yl)naphthalen-1-yl)pyrido[4,3-d]pyrimidin-4-yl)(methyl)amino)pyrrolidin-1-yl)prop-2-en-1-one

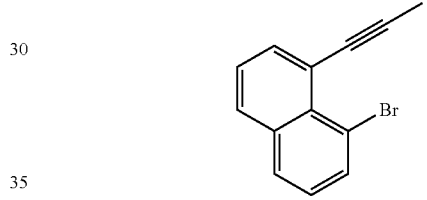

Step 1: 1-bromo-8-(prop-1-yn-1-yl)naphthalene

A mixture of 1,8-dibromonaphthalene (5 g, 17.48 mmol), but-2-ynoic acid (1.76 g, 20.98 mmol), bis(triphenylphosphine)palladium(II) dichloride (613.63 mg, 874.24 μmol), 1,4-bis(diphenylphosphino)butane (745.67 mg, 1.75 mmol) and 1,8-diazabicyclo[5.4.0]undec-7-ene (7.99 g, 52.45 mmol) in DMSO (100 mL) was degassed and purged with nitrogen 3 times. The mixture was stirred at 100° C. for 1 h under a nitrogen atmosphere. The mixture was diluted with water (80 mL) and extracted with methyl tert-butyl ether (3×80 mL). The combined organic layers were dried over sodium sulphate and concentrated in vacuo. The residue was purified by column chromatography (silica gel, 100-200 mesh, 0-100% ethyl acetate in petroleum ether) affording 1-bromo-8-(prop-1-yn-1-yl)naphthalene (4.2 g, 98.00%) as a yellow solid: $^1$H NMR (400 MHz, Chloroform-d) δ 7.94 (d, J=1.1 Hz, 1H), 7.81 (d, J=1.0 Hz, 1H), 7.74 (s, 1H), 7.72 (d, J=2.0 Hz, 1H), 7.25 (s, 1H), 7.23 (s, 1H), 2.13 (s, 3H).

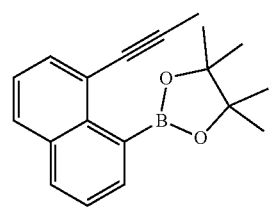 [SMILES: CC#Cc1cccc2cccc(B3OC(C)(C)C(C)(C)O3)c12]

Step 2: 4,4,5,5-tetramethyl-2-(8-(prop-1-yn-1-yl)naphthalen-1-yl)-1,3,2-dioxaborolane To a solution of 1-bromo-8-prop-1-ynyl-naphthalene (500 mg, 2.04 mmol) in tetrahydrofuran (30 mL) was added n-butyllithium (2.5 M, 917.94 uL in n-hexane) and 2-isopropoxy-4,4,5,5-tetramethyl-1,3,2-dioxaborolane (379.53 mg, 2.04 mmol). The mixture was stirred at −78° C. for 1 h. The reaction mixture was quenched with saturated ammonium chloride (30 mL) at 0° C. and extracted with dichloromethane (3×30 mL). The combined organic layers were dried over sodium sulphate and concentrated in vacuo. The crude product was purified by reverse phase HPLC (column: Waters Xbridge Prep OBD C18 150*40 mm*10 um; mobile phase: [water (NH$_4$HCO$_3$)-ACN]; B %: 45%-75%, 8 min) affording 4,4,5,5-tetramethyl-2-(8-(prop-1-yn-1-yl)naphthalen-1-yl)-1,3,2-dioxaborolane (140 mg, 23.49%) as a white solid: $^1$H NMR (400 MHz, Chloroform-d) δ 7.84 (dd, J=1.1, 8.2 Hz, 1H), 7.76 (d, J=8.1 Hz, 1H), 7.74-7.70 (m, 2H), 7.45 (dd, J=6.9, 8.1 Hz, 1H), 7.40-7.36 (m, 1H), 2.20 (s, 3H), 1.45 (s, 12H).

Step 3: tert-butyl (R)-3-((8-fluoro-2-(((2R,7aS)-2-fluorotetrahydro-1H-pyrrolizin-7a(5H)-yl)methoxy)-7-(8-(prop-1-yn-1-yl)naphthalen-1-yl)pyrido[4,3-d]pyrimidin-4-yl)(methyl)amino)pyrrolidine-1-carboxylate

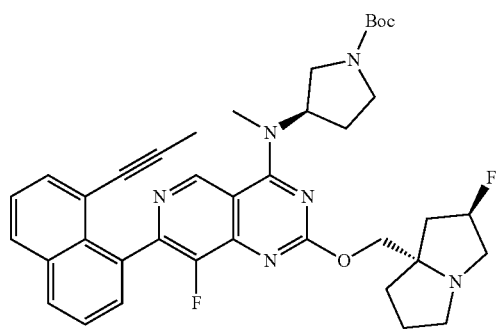

The Suzuki reaction was prepared in a similar fashion to Method #14, Step 1. The resulting residue was purified by reverse phase HPLC (column: Waters Xbridge BEH C18 100*30 mm*10 μm; mobile phase: [water (NH$_4$HCO$_3$)-ACN]; B %: 45%-75%, 8 min) affording tert-butyl (R)-3-((8-fluoro-2-(((2R,7aS)-2-fluorotetrahydro-1H-pyrrolizin-7a(5H)-yl)methoxy)-7-(8-(prop-1-yn-1-yl)naphthalen-1-yl)pyrido[4,3-d]pyrimidin-4-yl)(methyl)amino)pyrrolidine-1-carboxylate (106 mg, 60.78%) as a brown solid. LCMS Rt=0.665 min, m/z=668.3 [M+H]$^+$.

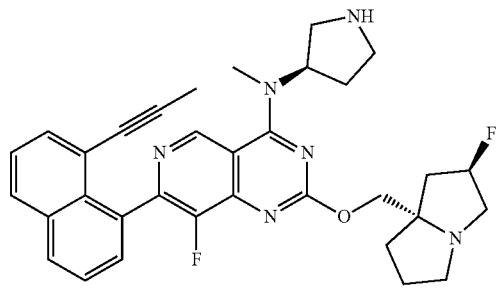

Step 4: 8-fluoro-2-(((2R,7aS)-2-fluorotetrahydro-1H-pyrrolizin-7a(5H)-yl)methoxy)-N-methyl-7-(8-(prop-1-yn-1-yl)naphthalen-1-yl)-N—((R)-pyrrolidin-3-yl)pyrido[4,3-d]pyrimidin-4-amine The deprotection of the Boc group was prepared in a similar fashion to Method #14, Step 3. The reaction mixture was concentrated in vacuo affording 8-fluoro-2-(((2R,7aS)-2-fluorotetrahydro-1H-pyrrolizin-7a(5H)-yl)methoxy)-N-methyl-7-(8-(prop-1-yn-1-yl)naphthalen-1-yl)-N—((R)-pyrrolidin-3-yl)pyrido[4,3-d]pyrimidin-4-amine (87 mg, crude, trifluoroacetic salt) as a yellow oil, which was used in the next step without further purification. LCMS Rt=0.520 min, m/z=568.3 [M+H]$^+$.

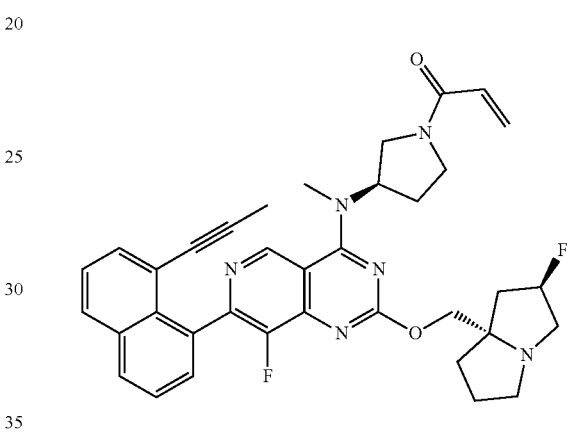

Step 5: 1-((R)-3-((8-fluoro-2-(((2R,7aS)-2-fluorotetrahydro-1H-pyrrolizin-7a(5H)-yl)methoxy)-7-(8-(prop-1-yn-1-yl)naphthalen-1-yl)pyrido[4,3-d]pyrimidin-4-yl)(methyl)amino)pyrrolidin-1-yl)prop-2-en-1-one The amide coupling reaction was prepared in a similar fashion to Method #14, Step 4. The crude product was purified by reverse phase prep-HPLC (column: Waters Xbridge Prep OBD C18 150*40 mm*10 μm; mobile phase: [water (NH$_4$HCO$_3$)-ACN]; B %: 35%-65%, 8 min) affording 1-((R)-3-((8-fluoro-2-(((2R,7aS)-2-fluorotetrahydro-1H-pyrrolizin-7a(5H)-yl)methoxy)-7-(8-(prop-1-yn-1-yl)naphthalen-1-yl)pyrido[4,3-d]pyrimidin-4-yl)(methyl)amino)pyrrolidin-1-yl)prop-2-en-1-one (45.13 mg, 57.53%) as a yellow oil: $^1$H NMR (400 MHz, Acetonitrile-d3) δ 9.24 (d, J=1.5 Hz, 1H), 8.06 (dd, J=0.9, 8.1 Hz, 1H), 7.99 (d, J=7.5 Hz, 1H), 7.67-7.59 (m, 2H), 7.57-7.53 (m, 1H), 7.52-7.47 (m, 1H), 6.65-6.52 (m, 1H), 6.23 (td, J=2.7, 16.8 Hz, 1H), 5.71-5.63 (m, 1H), 5.43-5.16 (m, 2H), 4.24-4.18 (m, 1H), 4.16-4.12 (m, 1H), 4.11-3.93 (m, 1H), 3.92-3.77 (m, 1H), 3.70-3.62 (m, 1H), 3.60-3.45 (m, 1H), 3.42 (s, 3H), 3.18-3.07 (m, 2H), 3.05 (d, J=1.6 Hz, 1H), 2.92-2.84 (m, 1H), 2.42-2.18 (m, 3H), 2.11-2.00 (m, 2H), 1.92-1.78 (m, 3H), 1.27 (dd, J=4.1, 11.7 Hz, 3H).

LCMS (5% to 95% acetonitrile in water+0.03% ammonium bicarbonate over 6 min); retention time 3.899 min, ESI+ found [M+H]=622.3.

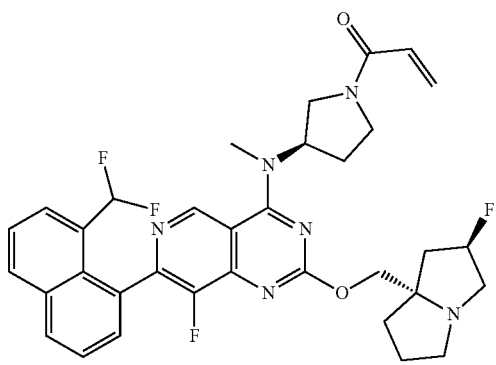

Example 307 (Method 3): 1-((R)-3-((7-(8-(difluoromethyl)naphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)prop-2-en-1-one

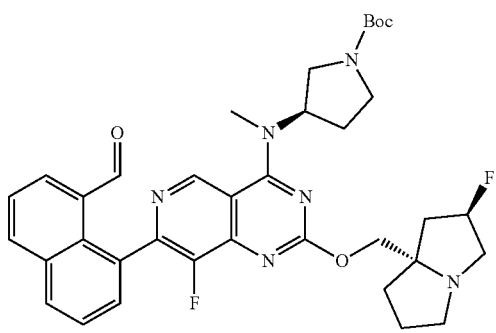

Step 1: (R)-tert-butyl 3-((8-fluoro-2-(((2R,7aS)-2-fluorohexahydro-1H-pyrrolizin-7a-yl)methoxy)-7-(8-formylnaphthalene-1-yl)pyrido[4,3-d]pyrimidin-4-yl)(methyl)amino)pyrrolidine-1-carboxylate The Stille reaction was prepared in a similar fashion to Method #3, Step 6. The organic layers were concentrated in vacuo and purified by reverse phase HPLC (column: Waters Xbridge Prep OBD C18 150*40 mm*10 µm; mobile phase: [water (NH₄HCO₃)-ACN]; B %: 45%-75%, 8 min) affording (R)-tert-butyl 3-((8-fluoro-2-(((2R,7aS)-2-fluorohexahydro-1H-pyrrolizin-7a-yl)methoxy)-7-(8-formylnaphthalen-1-yl)pyrido[4,3-d]pyrimidin-4-yl)(methyl)amino)pyrrolidine-1-carboxylate (50 mg, 28.72%) as a brown solid. LCMS Rt=0.686 min, m/z=658.3 [M+H]⁺.

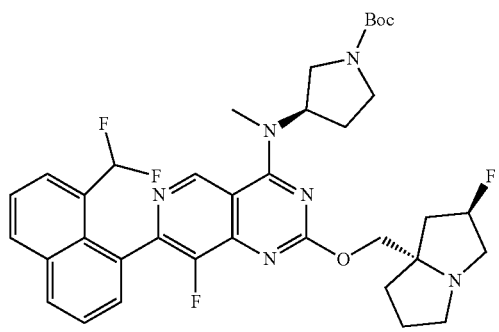

Step 2: (R)-tert-butyl 3-((7-(8-(difluoromethyl)naphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate A mixture of (R)-tert-butyl 3-((8-fluoro-2-(((2R,7aS)-2-fluorohexahydro-1H-pyrrolizin-7a-yl)methoxy)-7-(8-formylnaphthalen-1-yl)pyrido[4,3-d]pyrimidin-4-yl)(methyl)amino)pyrrolidine-1-carboxylate (20 mg, 30.36 µmol) in (diethylamino)sulfur trifluoride hydride (24.47 mg, 151.81 µmol) was stirred at 25° C. for 12 h under a nitrogen atmosphere. The mixture was diluted with water (2 mL) and extracted with ethyl acetate (3×2 mL). The combined organic layers were dried over sodium sulphate and concentrated in vacuo. The residue was purified by reverse phase HPLC (column: Phenomenex Luna 80*30 mm*3 µm; mobile phase: [water(TFA)-ACN]; B %: 30%-60%, 8 min) affording (R)-tert-butyl 3-((7-(8-(difluoromethyl)naphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidine-1-carboxylate (10 mg, 40.00%, trifluoroacetate salt) as a white solid. LCMS Rt=0.749 min, m/z=680.3[M+H]⁺.

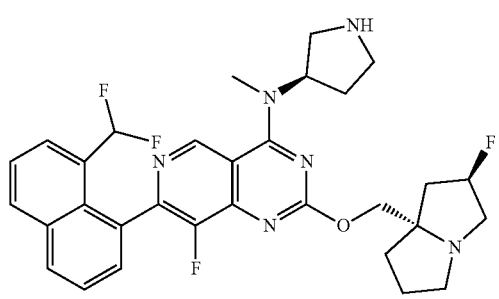 [SMILES: CN(c1nc(OC[C@@]23CCCN2C[C@H](F)C3)nc2c(F)c(-c3cccc4cccc(C(F)F)c34)ncc12)[C@@H]1CCNC1]

Step 3: 7-(8-(difluoromethyl)naphthalen-1-yl)-8-fluoro-2-(((2R,7aS)-2-fluorohexahydro-1H-pyrrolizin-7a-yl)methoxy)-N-methyl-N—((R)-pyrrolidin-3-yl)pyrido[4,3-d]pyrimidin-4-amine The removal of the Boc group was prepared in a similar fashion to Method #1, Step 9. The reaction mixture was concentrated in vacuo affording 7-(8-(difluoromethyl)naphthalen-1-yl)-8-fluoro-2-(((2R,7aS)-2-fluorohexahydro-1H-pyrrolizin-7a-yl)methoxy)-N-methyl-N—((R)-pyrrolidin-3-yl)pyrido[4,3-d]pyrimidin-4-amine (10 mg, crude, trifluoroacetate salt) as a yellow oil, which was used in the next step without further purification. LCMS Rt=0.530 min, m/z=580.2 [M+H]$^+$.

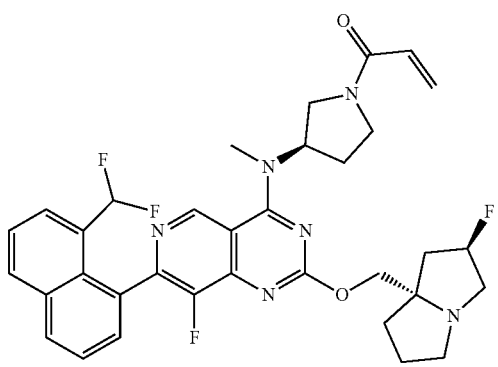

Step 4: 1-((R)-3-((7-(8-(difluoromethyl)naphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)prop-2-en-1-one The amide coupling reaction was prepared in a similar fashion to Method #3, Step 8. The crude residue was purified by reverse phase HPLC (column: Phenomenex C18 75*30 mm*3 µm; mobile phase: [water (NH$_4$HCO$_3$)-ACN]; B %: 25%-80%, 8 min) affording 1-((R)-3-((7-(8-(difluoromethyl)naphthalen-1-yl)-8-fluoro-2-(((2R,7aS)-2-fluorohexahydro-1H-pyrrolizin-7a-yl)methoxy)pyrido[4,3-d]pyrimidin-4-yl)(methyl)amino)pyrrolidin-1-yl)prop-2-en-1-one (1.11 mg, 11.90%) as white amorphous solid: $^1$H NMR (400 MHz, Acetonitrile-d3) δ 8.96 (s, 1H), 8.02-7.86 (m, 3H), 7.58-7.51 (m, 1H), 7.47-7.35 (m, 2H), 7.33-7.22 (m, 1H), 6.47 (ddd, J=10.2, 16.8, 20.4 Hz, 1H), 6.13 (td, J=2.8, 16.8 Hz, 1H), 5.66-5.47 (m, 1H), 5.38-4.91 (m, 2H), 4.21-4.07 (m, 2H), 4.05-3.57 (m, 3H), 3.57-3.48 (m, 1H), 3.44-3.29 (m, 1H), 3.25 (s, 3H), 3.19-3.13 (m, 1H), 3.06 (br s, 1H), 2.92-2.82 (m, 1H), 2.31-2.15 (m, 4H), 1.99 (br d, J=1.0 Hz, 2H), 1.82-1.67 (m, 2H).

LCMS (5% to 95% acetonitrile in water+0.1% ammonium bicarbonate over 6 min); retention time 2.256 min, ESI+ found [M+H]=634.3.

BIOLOGICAL EXAMPLES

Example 308: Inhibition of KRASG1$^2$C and cRAF Binding

The AlphaScreen technology was used to determine IC$_{50}$s for compound inhibition of KRAS G12C (present as the Cys-light (C51S, C80L and C118S), truncated version comprising amino acids 1-169) and cRAF interaction. Compounds were diluted in 100% DMSO and each compound concentration was spotted at 200 nl/well onto low volume, white 384 well plates. The KRAS G12C contained a biotin-AviTag and the cRaf, as Ras-binding domain (amino acids 50-131, RBD), was GST-tagged. KRAS G12C was preloaded with the GTP analogue Guanosine 5'-[β,γ-imido] triphosphate (GMPPNP). The KRAS G12C was diluted in 25 mM Hepes, pH 7.4, 150 mM NaCl, 5 mM MgCl$_2$, 0.01% TritonX-100 and 10 µM GMPPNP and added at 10 ul/well to compound-spotted plates resulting in a DMSO concentration of 2%. Plates were incubated for 19-20 hours. A mixture of RBD and the AlphaScreen streptavidin donor and glutathione acceptor beads diluted in 25 mM Hepes, pH 7.4, 150 mM NaCl, 5 mM MgCl$_2$, 0.01% TritonX-100 and 2% DMSO was then added at 10 ul/well and incubated for 60-90 minutes before the samples were read for emission at 570 nm after excitation of the donor beads at 680 nm. All incubations were performed at room temperature. The final top compound concentration was 50 µM with 1:3 titrations for 10-point dose response curves. Final assay conditions were 0.5 nM KRAS G12C, 0.75 nM RBD and 5 µg/ml each of AlphaScreen donor and acceptor beads. IC$_{50}$s were determined using nonlinear regression fit of [inhibitor] vs. response (4 parameters).

A counter assay was also set up to rule out inhibitors of the AlphaScreen technology itself. Compound plates were incubated for 19-20 hours as above with buffer only. The AlphaScreen beads were added as above except biotin-AviTag-GST was substituted for the RBD. Samples were read and analyzed as above.

Results for compounds are shown in Table 1.
TABLE 1
Inhibition of KRAS G12C and cRAF Binding (IC$_{50}$)
| Synthetic Example | Structure | IC$_{50}$ |
|---|---|---|
| 1 | 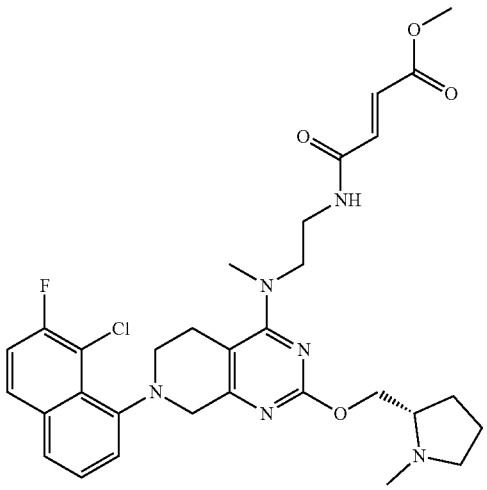 [SMILES: COC(=O)/C=C/C(=O)NCCN(C)c1nc(OC[C@@H]2CCCN2C)nc2c1CCN(c1cccc3ccc(F)c(Cl)c13)C2] | +++ |
| 2 | 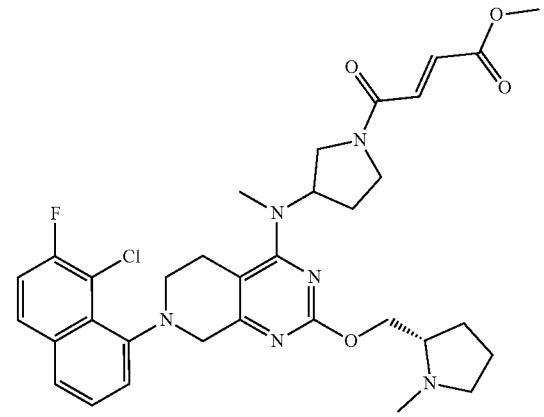 (formate salt) | +++ |
| 3 | 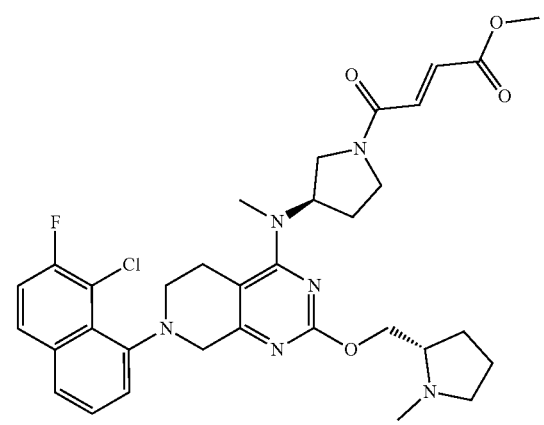 [SMILES: COC(=O)/C=C/C(=O)N1CC[C@@H](N(C)c2nc(OC[C@@H]3CCCN3C)nc3c2CCN(c2cccc4ccc(F)c(Cl)c24)C3)C1] | +++ |

TABLE 1-continued
Inhibition of KRAS G12C and cRAF Binding (IC$_{50}$)
| Synthetic Example | Structure | IC$_{50}$ |
|---|---|---|
| 4 | 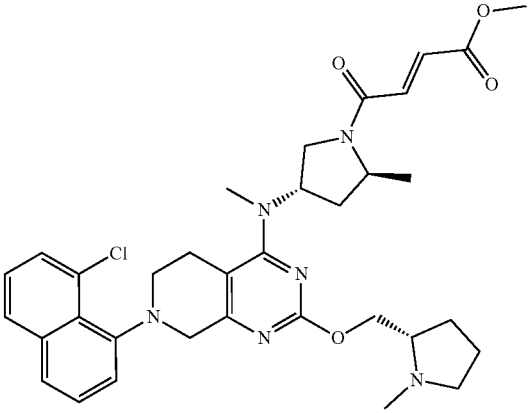 [SMILES: COC(=O)/C=C/C(=O)N1C[C@@H](N(C)c2nc(OC[C@@H]3CCCN3C)nc3c2CCN(c2cccc4cccc(Cl)c24)C3)C[C@@H]1C] | + |
| 5 | 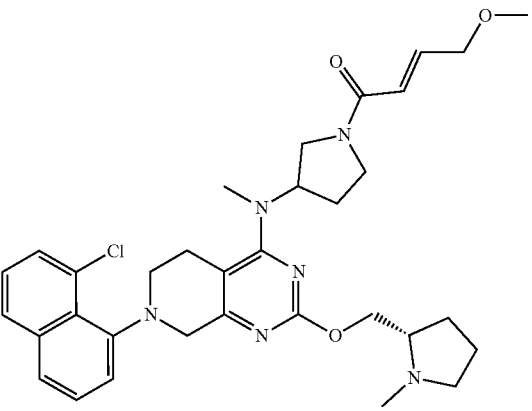 [SMILES: COC/C=C/C(=O)N1CCC(N(C)c2nc(OC[C@@H]3CCCN3C)nc3c2CCN(c2cccc4cccc(Cl)c24)C3)C1] | + |
| 6 | 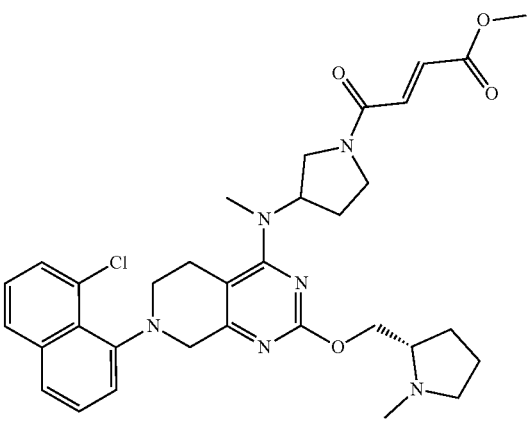 [SMILES: COC(=O)/C=C/C(=O)N1CCC(N(C)c2nc(OC[C@@H]3CCCN3C)nc3c2CCN(c2cccc4cccc(Cl)c24)C3)C1]<br>(trifluoroacetate salt) | +++ |

TABLE 1-continued
Inhibition of KRAS G12C and cRAF Binding (IC$_{50}$)
| Synthetic Example | Structure | IC$_{50}$ |
|---|---|---|
| 7 | 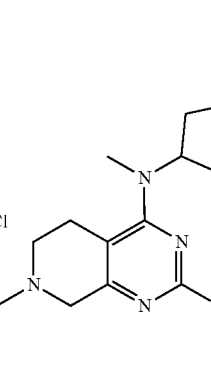 (formate salt) | + |
| 8 | 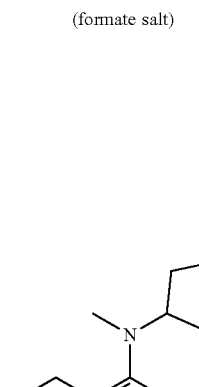 (formate salt) | ++ |
| 9 | 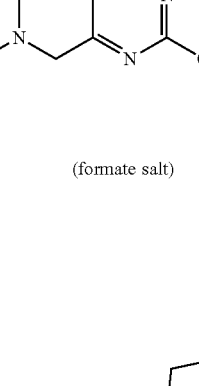 | ++++ |

TABLE 1-continued
Inhibition of KRAS G12C and cRAF Binding (IC$_{50}$)
| Synthetic Example | Structure | IC$_{50}$ |
|---|---|---|
| 10 | 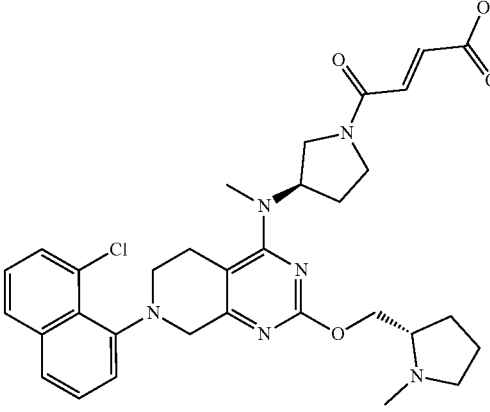 (formate salt) | +++ |
| 11 | 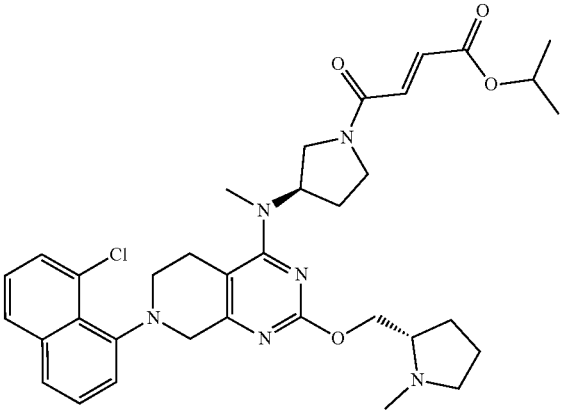 [SMILES: CC(C)OC(=O)/C=C/C(=O)N1CC[C@@H](N(C)c2nc(OC[C@@H]3CCCN3C)nc3c2CCN(c2cccc4cccc(Cl)c24)C3)C1] | +++ |
| 12 | 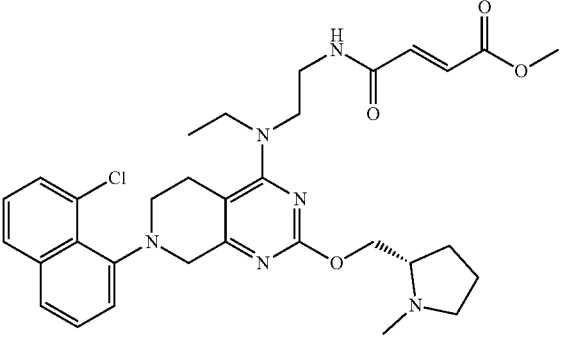 [SMILES: CCN(CCNC(=O)/C=C/C(=O)OC)c1nc(OC[C@@H]2CCCN2C)nc2c1CCN(c1cccc3cccc(Cl)c13)C2] | + |
| 13 | 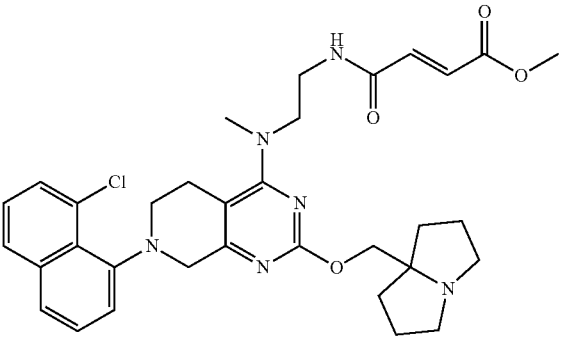 [SMILES: COC(=O)/C=C/C(=O)NCCN(C)c1nc(OCC23CCCN2CCC3)nc2c1CCN(c1cccc3cccc(Cl)c13)C2] | +++ |

TABLE 1-continued
Inhibition of KRAS G12C and cRAF Binding (IC$_{50}$)
| Synthetic Example | Structure | IC$_{50}$ |
|---|---|---|
| 14 | 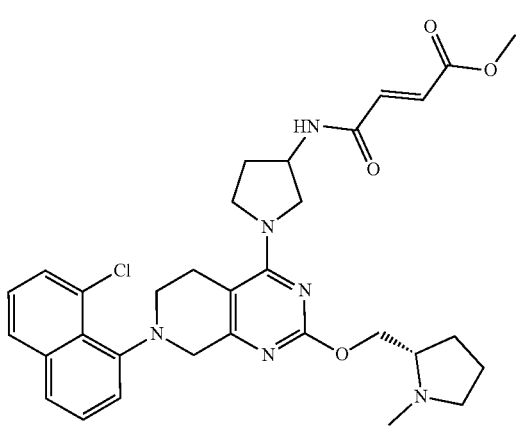 [SMILES: COC(=O)/C=C/C(=O)NC1CCN(c2nc(OC[C@@H]3CCCN3C)nc3c2CCN(c2cccc4cccc(Cl)c24)C3)C1] | + |
| 15 | 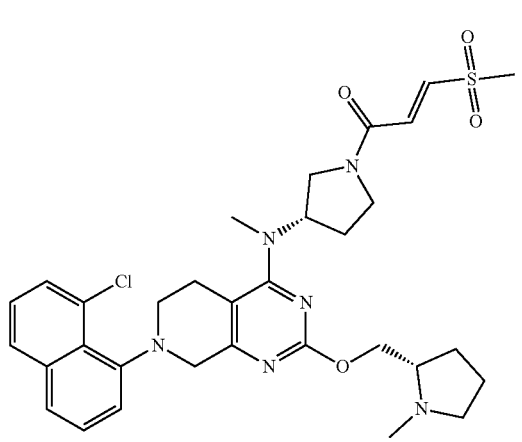 [SMILES: CN1CCC[C@H]1COc1nc2c(c(N(C)[C@H]3CCN(C(=O)/C=C/S(C)(=O)=O)C3)n1)CCN(c1cccc3cccc(Cl)c13)C2] | ++++ |
| 16 | 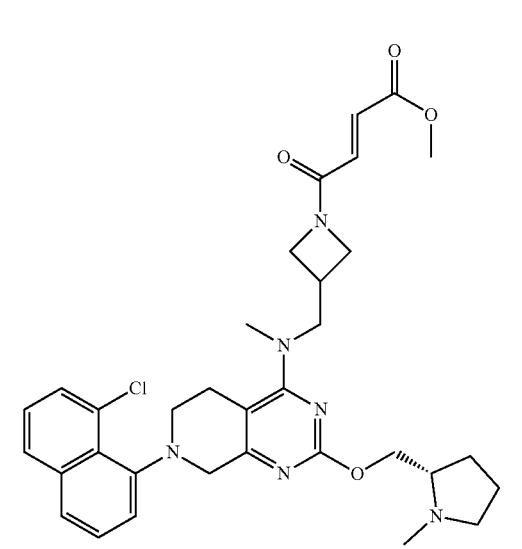 [SMILES: COC(=O)/C=C/C(=O)N1CC(CN(C)c2nc(OC[C@@H]3CCCN3C)nc3c2CCN(c2cccc4cccc(Cl)c24)C3)C1]<br>(formate salt) | +++ |

TABLE 1-continued
Inhibition of KRAS G12C and cRAF Binding (IC$_{50}$)
| Synthetic Example | Structure | IC$_{50}$ |
|---|---|---|
| 17 | 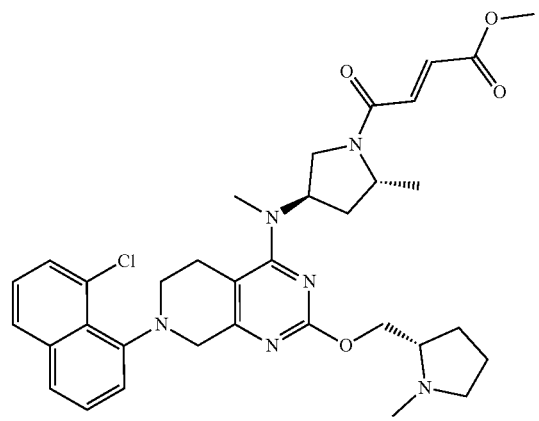 [SMILES: COC(=O)/C=C/C(=O)N1C[C@H](N(C)c2nc(OC[C@@H]3CCCN3C)nc3c2CCN(c2cccc4cccc(Cl)c24)C3)C[C@H]1C] | +++ |
| 18 | 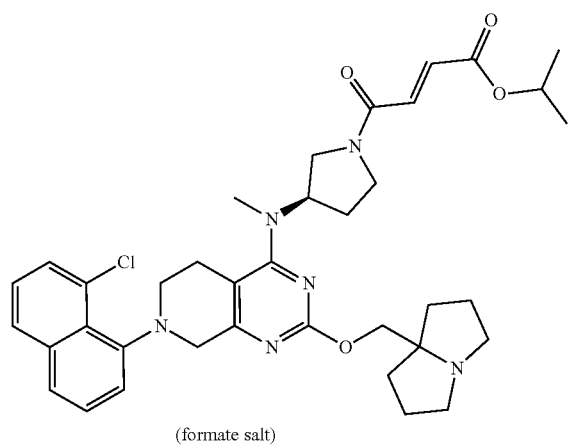 [SMILES: CC(C)OC(=O)/C=C/C(=O)N1CC[C@@H](N(C)c2nc(OCC34CCCN3CCC4)nc3c2CCN(c2cccc4cccc(Cl)c24)C3)C1] (formate salt) | ++++ |
| 19 | 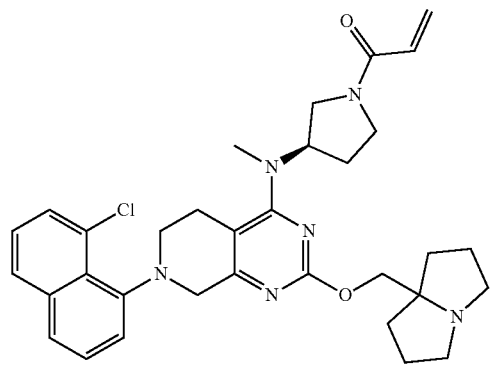 [SMILES: C=CC(=O)N1CC[C@@H](N(C)c2nc(OCC34CCCN3CCC4)nc3c2CCN(c2cccc4cccc(Cl)c24)C3)C1] | +++ |

TABLE 1-continued

Inhibition of KRAS G12C and cRAF Binding (IC$_{50}$)

| Synthetic Example | Structure | IC$_{50}$ |
|---|---|---|
| 20 | 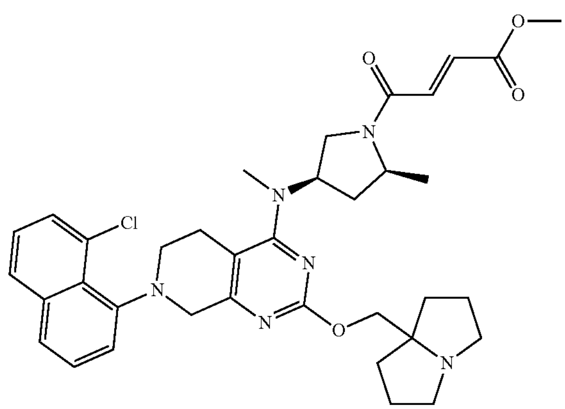 [SMILES: COC(=O)/C=C/C(=O)N1C[C@H](N(C)c2nc(OCC34CCCN3CCC4)nc3c2CCN(c2cccc4cccc(Cl)c24)C3)C[C@@H]1C] | +++ |
| 21 | 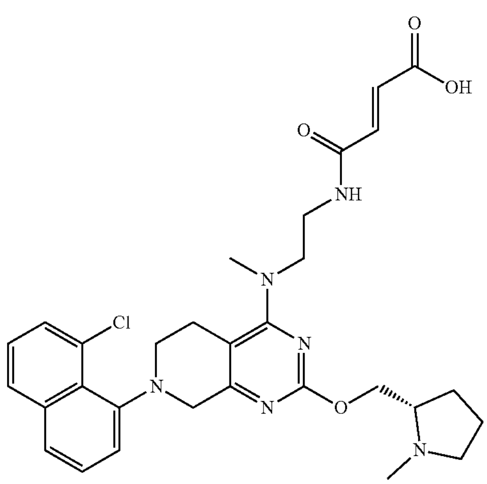 [SMILES: CN(CCNC(=O)/C=C/C(=O)O)c1nc(OC[C@@H]2CCCN2C)nc2c1CCN(c1cccc3cccc(Cl)c13)C2] | + |
| 22 | (trifluroacetate salt) | ++ |

TABLE 1-continued

Inhibition of KRAS G12C and cRAF Binding (IC$_{50}$)

| Synthetic Example | Structure | IC$_{50}$ |
|---|---|---|
| 23 | 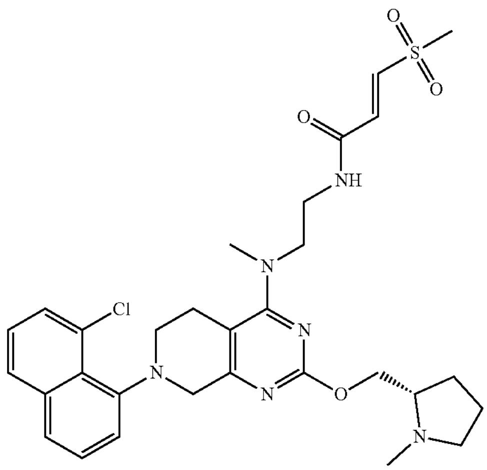 [SMILES: CN(CCNC(=O)/C=C/S(C)(=O)=O)c1nc(OC[C@@H]2CCCN2C)nc2c1CCN(c1cccc3cccc(Cl)c13)C2] | +++ |
| 24 | 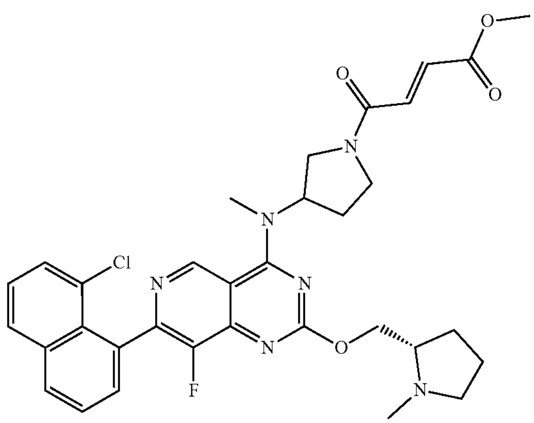 [SMILES: COC(=O)/C=C/C(=O)N1CCC(N(C)c2nc(OC[C@@H]3CCCN3C)nc3c(F)c(-c4cccc5cccc(Cl)c45)ncc23)C1] | ++++ |
| 25 | 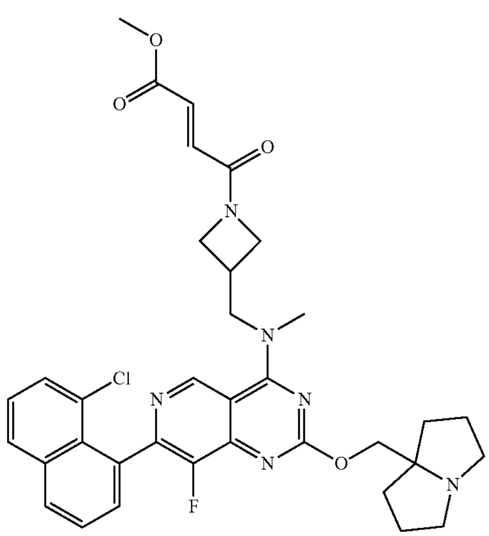 [SMILES: COC(=O)/C=C/C(=O)N1CC(CN(C)c2nc(OCC34CCCN3CCC4)nc3c(F)c(-c4cccc5cccc(Cl)c45)ncc23)C1] | ++++ |

TABLE 1-continued

Inhibition of KRAS G12C and cRAF Binding (IC$_{50}$)

| Synthetic Example | Structure | IC$_{50}$ |
|---|---|---|
| 26 | 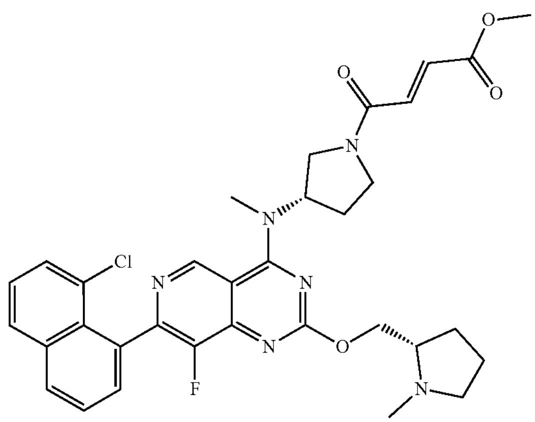 [SMILES: COC(=O)/C=C/C(=O)N1CC[C@H](N(C)c2nc(OC[C@@H]3CCCN3C)nc3c(F)c(-c4cccc5cccc(Cl)c45)ncc23)C1] | + |
| 27 | 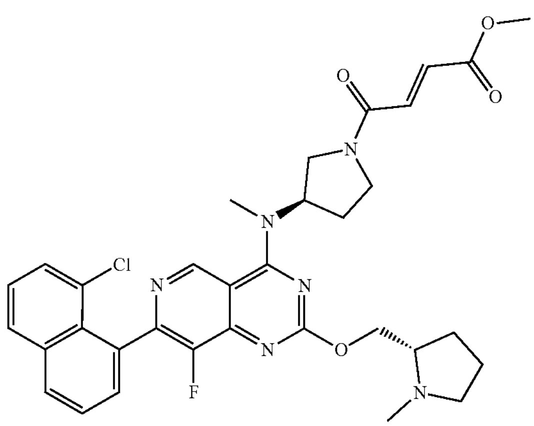 [SMILES: COC(=O)/C=C/C(=O)N1CC[C@@H](N(C)c2nc(OC[C@@H]3CCCN3C)nc3c(F)c(-c4cccc5cccc(Cl)c45)ncc23)C1] | ++++ |
| 28 | (formate salt) | +++ |

TABLE 1-continued
Inhibition of KRAS G12C and cRAF Binding (IC$_{50}$)
| Synthetic Example | Structure | IC$_{50}$ |
|---|---|---|
| 29 | 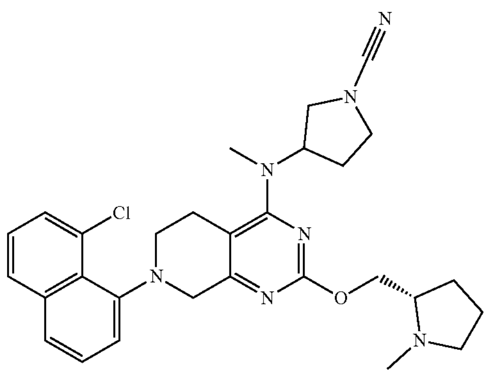 [SMILES: CN(c1nc(OC[C@@H]2CCCN2C)nc2c1CCN(c1cccc3cccc(Cl)c13)C2)C1CCN(C#N)C1] | ++ |
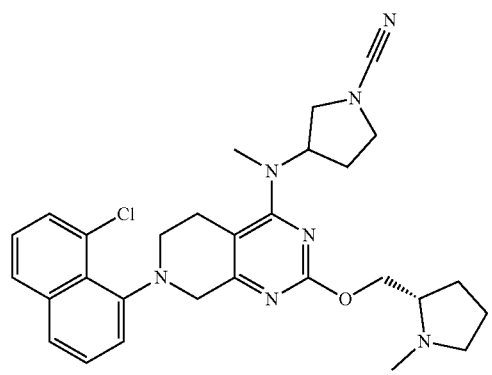
(formate salt)
| 30 | | + |
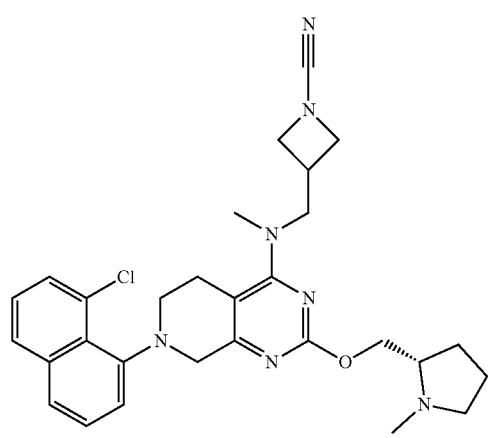 [SMILES: CN(CC1CN(C#N)C1)c1nc(OC[C@@H]2CCCN2C)nc2c1CCN(c1cccc3cccc(Cl)c13)C2]
(formate salt)
| 31 | | + |
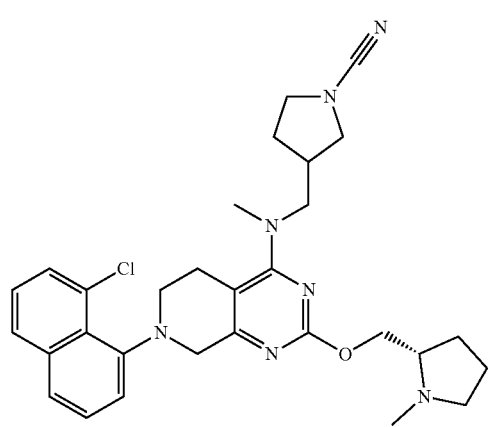 [SMILES: CN(CC1CCN(C#N)C1)c1nc(OC[C@@H]2CCCN2C)nc2c1CCN(c1cccc3cccc(Cl)c13)C2]
(formate salt)

TABLE 1-continued
Inhibition of KRAS G12C and cRAF Binding (IC$_{50}$)
| Synthetic Example | Structure | IC$_{50}$ |
|---|---|---|
| 32 | 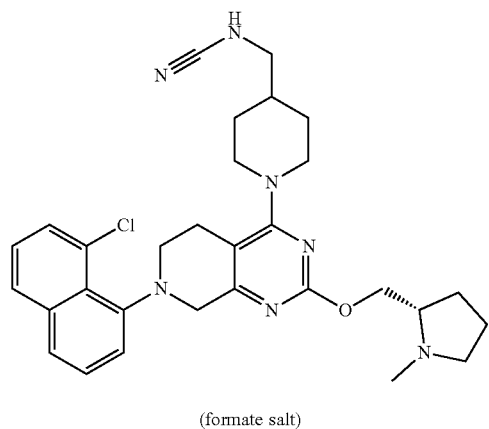<br>(formate salt) | + |
| 33 | 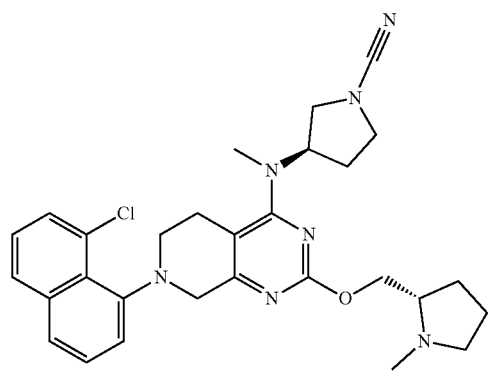 [SMILES: CN1CCC[C@H]1COc1nc2c(c(N(C)[C@@H]3CCN(C#N)C3)n1)CCN(c1cccc3cccc(Cl)c13)C2] | ++ |
| 34 | 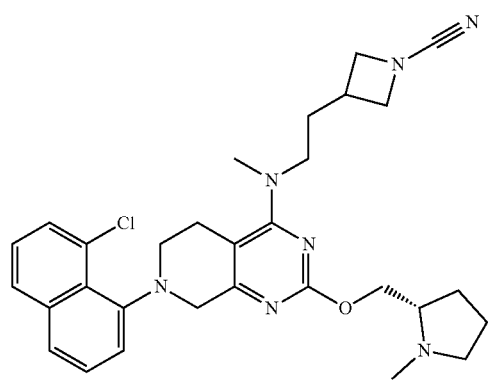 [SMILES: CN(CCC1CN(C#N)C1)c1nc(OC[C@@H]2CCCN2C)nc2c1CCN(c1cccc3cccc(Cl)c13)C2]<br>(formate salt) | ++ |

TABLE 1-continued
Inhibition of KRAS G12C and cRAF Binding (IC$_{50}$)
| Synthetic Example | Structure | IC$_{50}$ |
|---|---|---|
| 35 | 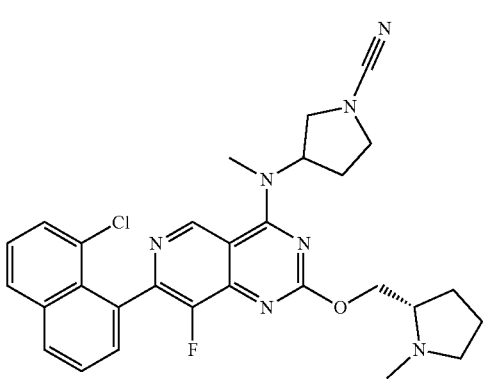 [SMILES: CN(c1nc(OC[C@@H]2CCCN2C)nc2c(F)c(-c3cccc4cccc(Cl)c34)ncc12)C1CCN(C#N)C1] | +++ |
| 36 | 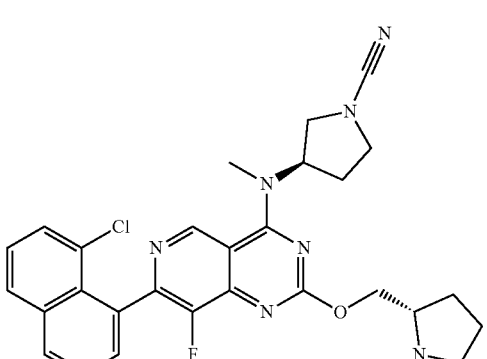<br>(formate salt) | +++ |
| 37 (and) at octahydro-pyrrolopyrrole (abs) at pyrolidine | 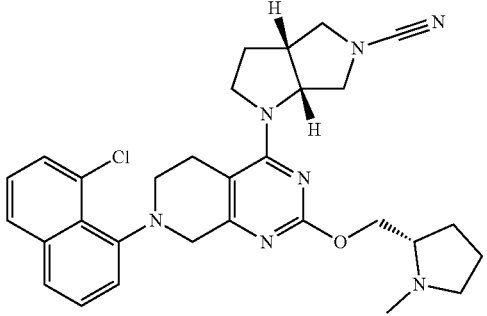 [SMILES: CN1CCC[C@H]1COc1nc2c(c(N3CC[C@@H]4CN(C#N)C[C@@H]43)n1)CCN(c1cccc3cccc(Cl)c13)C2]<br>(formate salt) | ++ |

TABLE 1-continued

Inhibition of KRAS G12C and cRAF Binding (IC$_{50}$)

| Synthetic Example | Structure | IC$_{50}$ |
|---|---|---|
| 38 | (formate salt) | + |
| 39 | (formate salt) | ++ |
| 40 | 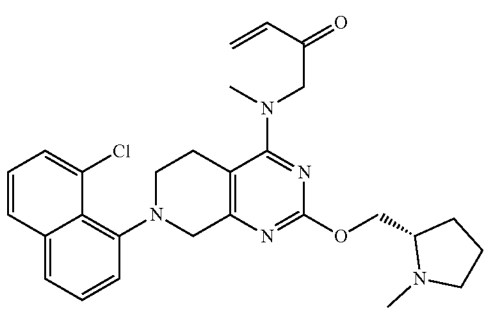 [SMILES: C=CC(=O)CN(C)c1nc(OC[C@@H]2CCCN2C)nc2c1CCN(c1cccc3cccc(Cl)c13)C2] | +++ |
| 41 | (trifluoroacetate salt) | +++ |

TABLE 1-continued
Inhibition of KRAS G12C and cRAF Binding (IC$_{50}$)
| Synthetic Example | Structure | IC$_{50}$ |
|---|---|---|
| 42 | 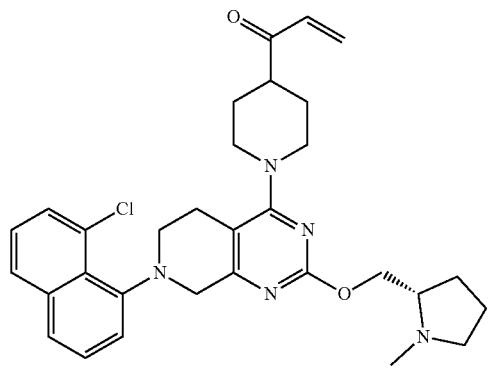 [SMILES: C=CC(=O)C1CCN(c2nc(OC[C@@H]3CCCN3C)nc3c2CCN(c2cccc4cccc(Cl)c24)C3)CC1]<br>(trifluoroacetate salt) | +++ |
| 43 (or) fused piperidine (abs) pyrrolidine | 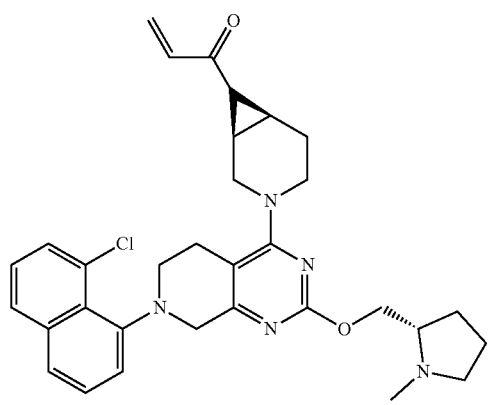<br>(formate salt) | +++ |
| 43 (or) fused piperidine (abs) pyrrolidine | 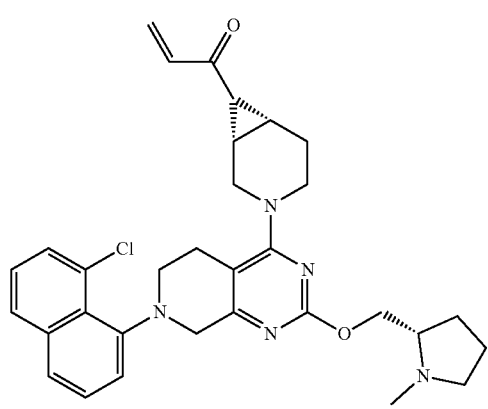<br>(formate salt) | ++ |

TABLE 1-continued
Inhibition of KRAS G12C and cRAF Binding ($IC_{50}$)
| Synthetic Example | Structure | $IC_{50}$ |
|---|---|---|
| 44 (or) fused piperidine (abs) pyrrolidine | 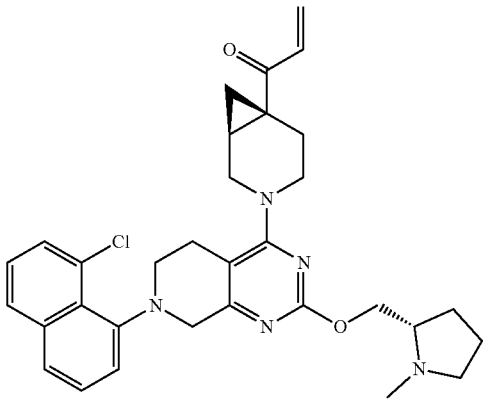 [SMILES: C=CC(=O)[C@]12CCN(c3nc(OC[C@@H]4CCCN4C)nc4c3CCN(c3cccc5cccc(Cl)c35)C4)C[C@H]1C2] (formate salt) | ++++ |
| 44 (or) fused piperidine (abs) pyrrolidine | 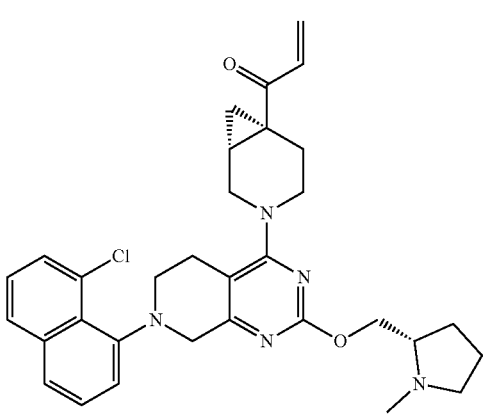 [SMILES: C=CC(=O)[C@@]12CCN(c3nc(OC[C@@H]4CCCN4C)nc4c3CCN(c3cccc5cccc(Cl)c35)C4)C[C@@H]1C2] (formate salt) | +++ |
| 45 | 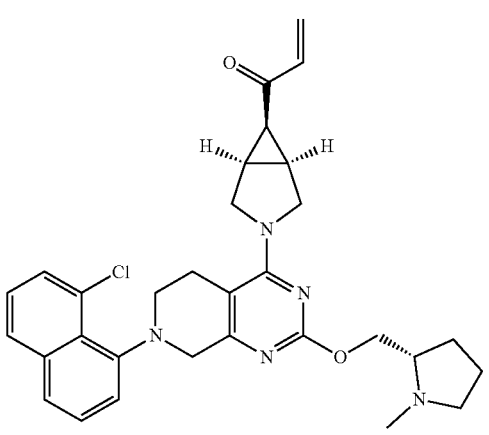 [SMILES: C=CC(=O)[C@@H]1[C@@H]2CN(c3nc(OC[C@@H]4CCCN4C)nc4c3CCN(c3cccc5cccc(Cl)c35)C4)C[C@@H]21] (formate salt) | +++ |

TABLE 1-continued

Inhibition of KRAS G12C and cRAF Binding (IC$_{50}$)

| Synthetic Example | Structure | IC$_{50}$ |
|---|---|---|
| 46 | (trifluoroacetate salt) | + |
| 47 | (formate salt) | +++ |
| 48 | (formate salt) | ++ |

TABLE 1-continued
Inhibition of KRAS G12C and cRAF Binding (IC$_{50}$)
| Synthetic Example | Structure | IC$_{50}$ |
|---|---|---|
| 49 | 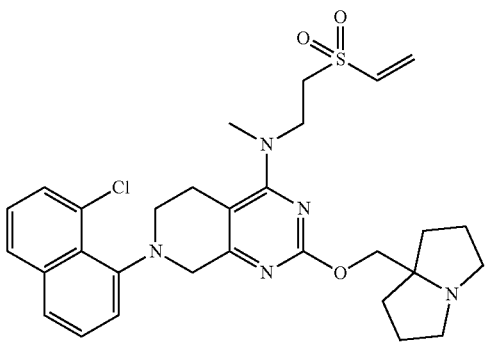 [SMILES: C=CS(=O)(=O)CCN(C)c1nc(OCC23CCCN2CCC3)nc2c1CCN(c1cccc3cccc(Cl)c13)C2]<br>(formate salt) | ++++ |
| 50 | 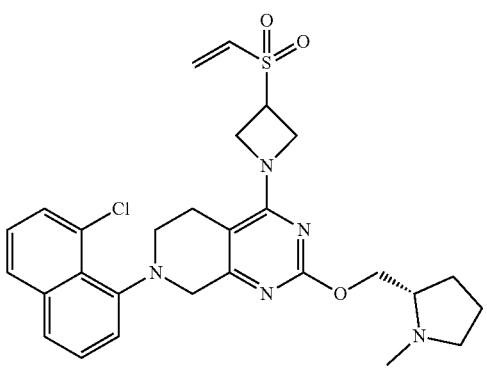 [SMILES: C=CS(=O)(=O)C1CN(c2nc(OC[C@@H]3CCCN3C)nc3c2CCN(c2cccc4cccc(Cl)c24)C3)C1] | + |
| 51 | 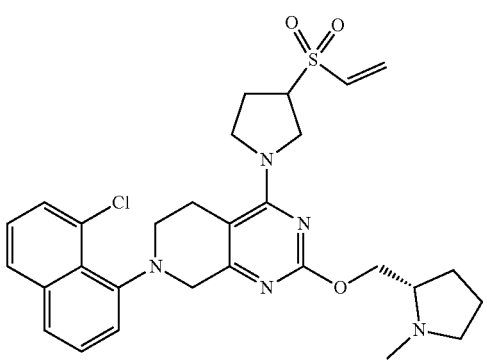 [SMILES: C=CS(=O)(=O)C1CCN(c2nc(OC[C@@H]3CCCN3C)nc3c2CCN(c2cccc4cccc(Cl)c24)C3)C1]<br>(formate salt) | + |
| 52 | 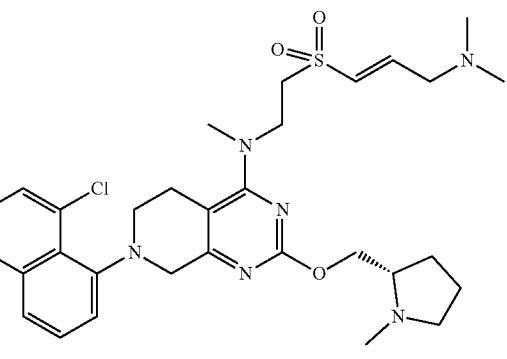<br>(formate salt) | +++ |

TABLE 1-continued
Inhibition of KRAS G12C and cRAF Binding (IC$_{50}$)
| Synthetic Example | Structure | IC$_{50}$ |
|---|---|---|
| 53 | 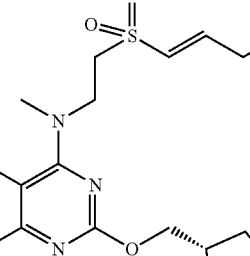 | ++ |
| 54 | 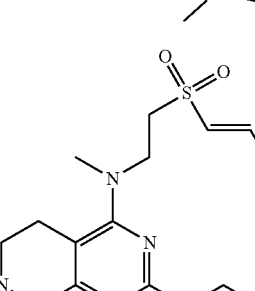 (formate salt) | ++ |
| 55 | 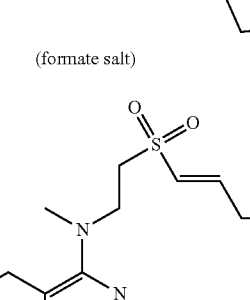 (formate salt) | ++++ |
| 56 | 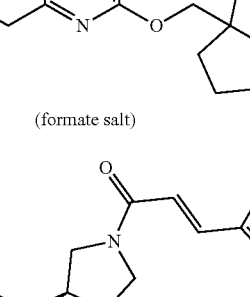 | +++ |

TABLE 1-continued

Inhibition of KRAS G12C and cRAF Binding (IC$_{50}$)

| Synthetic Example | Structure | IC$_{50}$ |
|---|---|---|
| 57 | 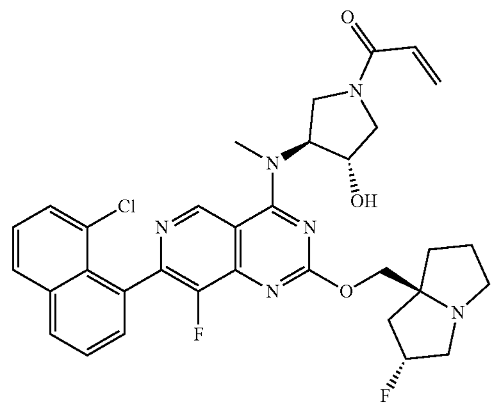 [SMILES: C=CC(=O)N1C[C@H](O)[C@@H](N(C)c2nc(OC[C@@]34CCCN3C[C@H](F)C4)nc3c(F)c(-c4cccc5cccc(Cl)c45)ncc23)C1] | ++ |
| 58 | (formate salt) | +++ |
| 59 | (formate salt) | ++++ |

TABLE 1-continued
Inhibition of KRAS G12C and cRAF Binding (IC$_{50}$)
| Synthetic Example | Structure | IC$_{50}$ |
|---|---|---|
| 60 | 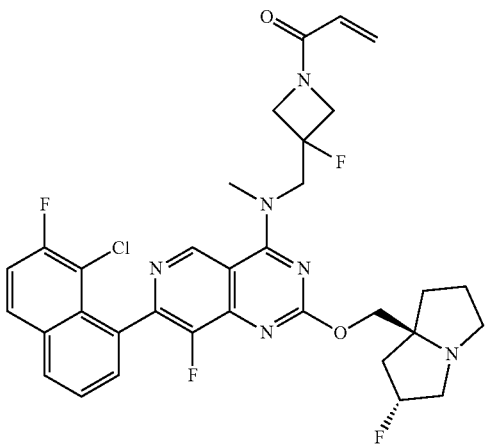 [SMILES: C=CC(=O)N1CC(F)(CN(C)c2nc(OC[C@@]34CCCN3C[C@H](F)C4)nc3c(F)c(-c4cccc5ccc(F)c(Cl)c45)ncc23)C1] | ++ |
| 61 | 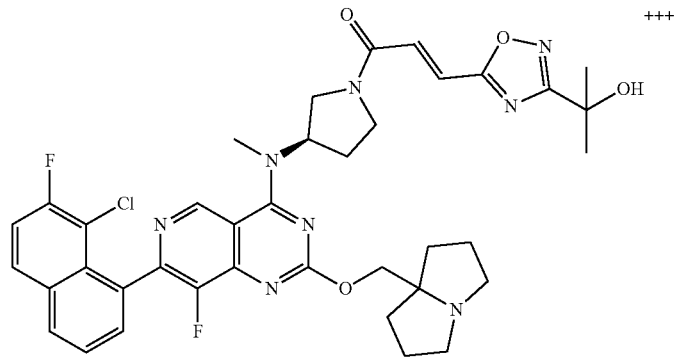 | +++ |
| 62 | 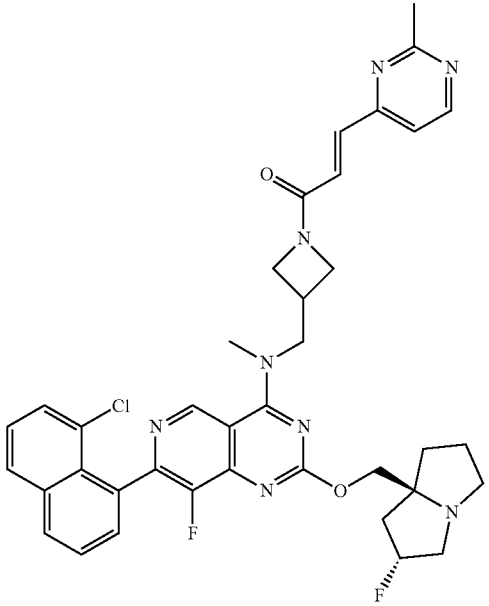 [SMILES: Cc1nccc(/C=C/C(=O)N2CC(CN(C)c3nc(OC[C@@]45CCCN4C[C@H](F)C5)nc4c(F)c(-c5cccc6cccc(Cl)c56)ncc34)C2)n1] | +++ |

TABLE 1-continued

Inhibition of KRAS G12C and cRAF Binding (IC$_{50}$)

| Synthetic Example | Structure | IC$_{50}$ |
|---|---|---|
| 63 | 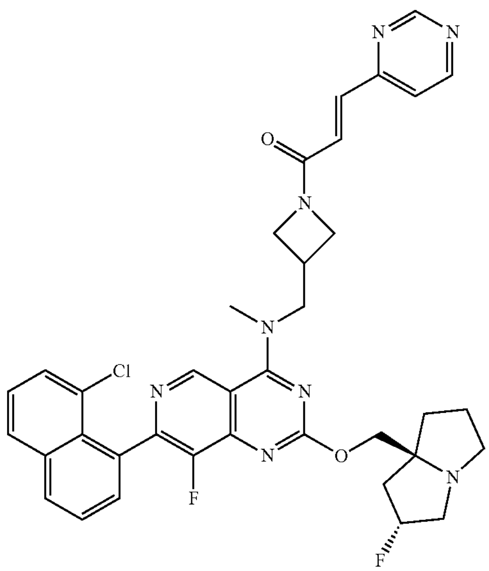 [SMILES: CN(CC1CN(C(=O)/C=C/c2ccncn2)C1)c1nc(OC[C@@]23CCCN2C[C@H](F)C3)nc2c(F)c(-c3cccc4cccc(Cl)c34)ncc12] | +++ |
| 64 | 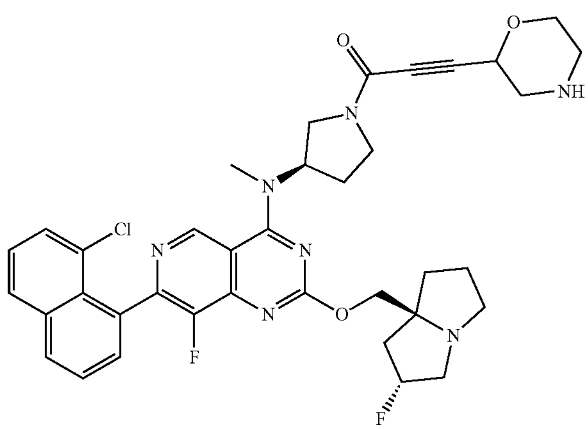 [SMILES: CN(c1nc(OC[C@@]23CCCN2C[C@H](F)C3)nc2c(F)c(-c3cccc4cccc(Cl)c34)ncc12)[C@@H]1CCN(C(=O)C#CC2CNCCO2)C1] | ++++ |
| 65 | 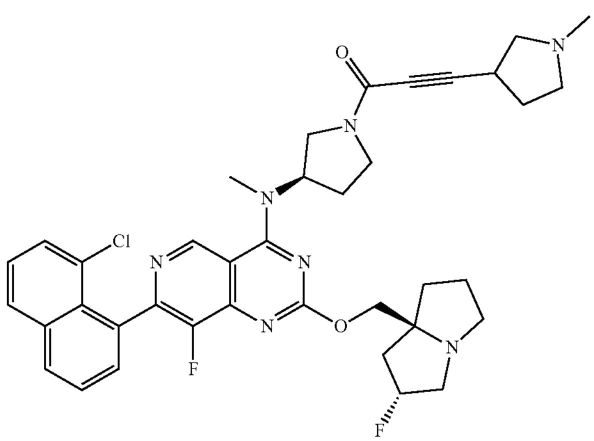 [SMILES: CN1CCC(C#CC(=O)N2CC[C@@H](N(C)c3nc(OC[C@@]45CCCN4C[C@H](F)C5)nc4c(F)c(-c5cccc6cccc(Cl)c56)ncc34)C2)C1] | +++ |

TABLE 1-continued

Inhibition of KRAS G12C and cRAF Binding (IC$_{50}$)

| Synthetic Example | Structure | IC$_{50}$ |
|---|---|---|
| 66 | 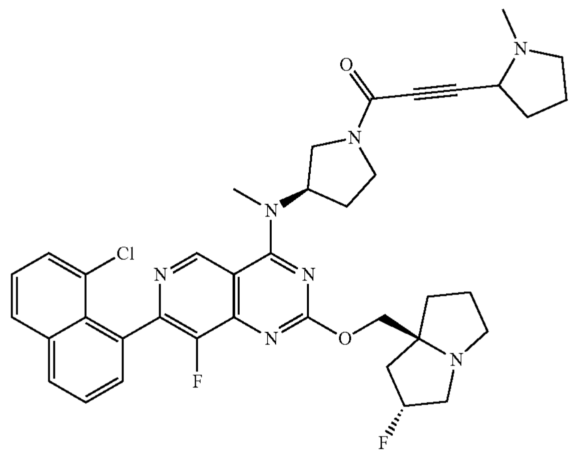 [SMILES: CN1CCCC1C#CC(=O)N1CC[C@@H](N(C)c2nc(OC[C@@]34CCCN3C[C@H](F)C4)nc3c(F)c(-c4cccc5cccc(Cl)c45)ncc23)C1] | +++ |
| 67 | 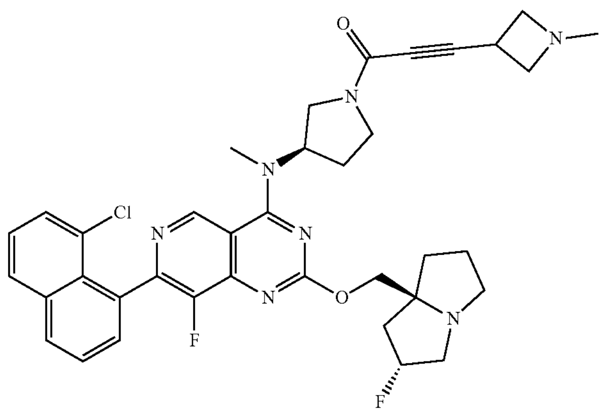 [SMILES: CN1CC(C#CC(=O)N2CC[C@@H](N(C)c3nc(OC[C@@]45CCCN4C[C@H](F)C5)nc4c(F)c(-c5cccc6cccc(Cl)c56)ncc34)C2)C1] | +++ |
| 68 | (formate salt) | +++ |

TABLE 1-continued
Inhibition of KRAS G12C and cRAF Binding (IC$_{50}$)
| Synthetic Example | Structure | IC$_{50}$ |
|---|---|---|
| 69 | 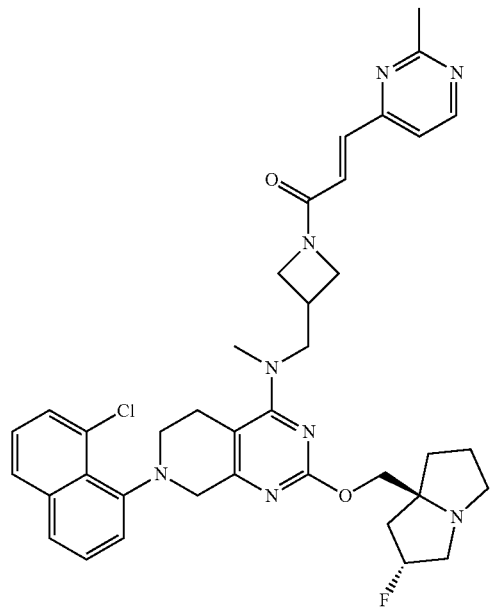 [SMILES: Cc1nccc(/C=C/C(=O)N2CC(CN(C)c3nc(OC[C@@]45CCCN4C[C@H](F)C5)nc4c3CCN(c3cccc5cccc(Cl)c35)C4)C2)n1] | ++ |
| 70 | 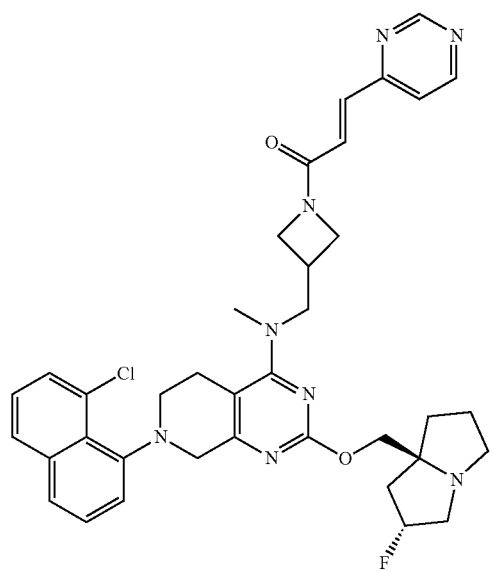 [SMILES: CN(CC1CN(C(=O)/C=C/c2ccncn2)C1)c1nc(OC[C@@]23CCCN2C[C@H](F)C3)nc2c1CCN(c1cccc3cccc(Cl)c13)C2] | +++ |

TABLE 1-continued
Inhibition of KRAS G12C and cRAF Binding (IC$_{50}$)
| Synthetic Example | Structure | IC$_{50}$ |
|---|---|---|
| 71 | 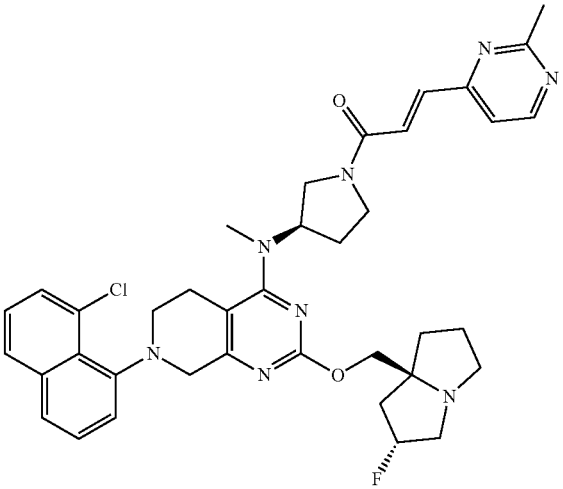 [SMILES: Cc1nccc(/C=C/C(=O)N2CC[C@@H](N(C)c3nc(OC[C@@]45CCCN4C[C@H](F)C5)nc4c3CCN(c3cccc5cccc(Cl)c35)C4)C2)n1] | + |
| 72 | 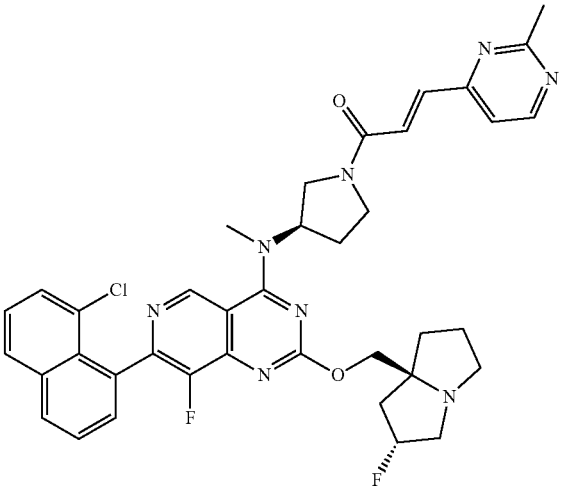 [SMILES: Cc1nccc(/C=C/C(=O)N2CC[C@@H](N(C)c3nc(OC[C@@]45CCCN4C[C@H](F)C5)nc4c(F)c(-c5cccc6cccc(Cl)c56)ncc34)C2)n1] | ++ |
| 73 | 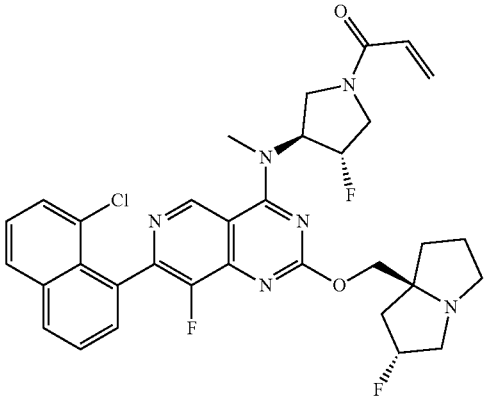 [SMILES: C=CC(=O)N1C[C@H](F)[C@@H](N(C)c2nc(OC[C@@]34CCCN3C[C@H](F)C4)nc3c(F)c(-c4cccc5cccc(Cl)c45)ncc23)C1] | +++ |

TABLE 1-continued

Inhibition of KRAS G12C and cRAF Binding (IC$_{50}$)

| Synthetic Example | Structure | IC$_{50}$ |
|---|---|---|
| 74 | 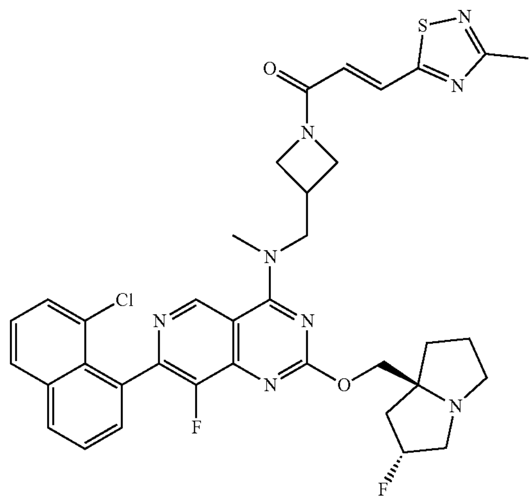 [SMILES: Cc1nsc(/C=C/C(=O)N2CC(CN(C)c3nc(OC[C@@]45CCCN4C[C@H](F)C5)nc4c(F)c(-c5cccc6cccc(Cl)c56)ncc34)C2)n1] | ++ |
| 75 | 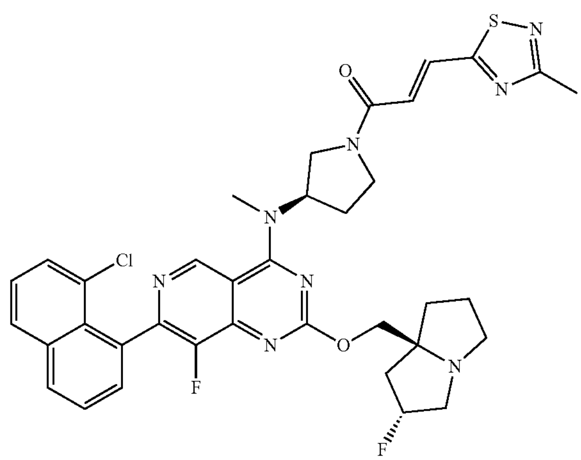 | +++ |
| 76 | 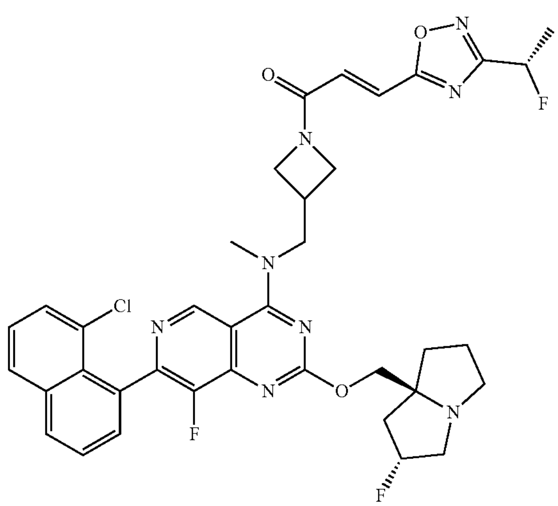 [SMILES: C[C@H](F)c1noc(/C=C/C(=O)N2CC(CN(C)c3nc(OC[C@@]45CCCN4C[C@H](F)C5)nc4c(F)c(-c5cccc6cccc(Cl)c56)ncc34)C2)n1] | ++++ |

TABLE 1-continued

Inhibition of KRAS G12C and cRAF Binding (IC$_{50}$)

| Synthetic Example | Structure | IC$_{50}$ |
|---|---|---|
| 77 | 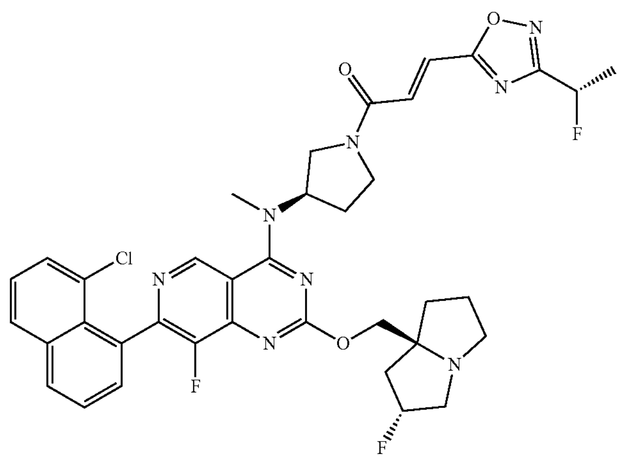 [SMILES: C[C@H](F)c1noc(/C=C/C(=O)N2CC[C@@H](N(C)c3nc(OC[C@@]45CCCN4C[C@H](F)C5)nc4c(F)c(-c5cccc6cccc(Cl)c56)ncc34)C2)n1] | ++++ |
| 78 | 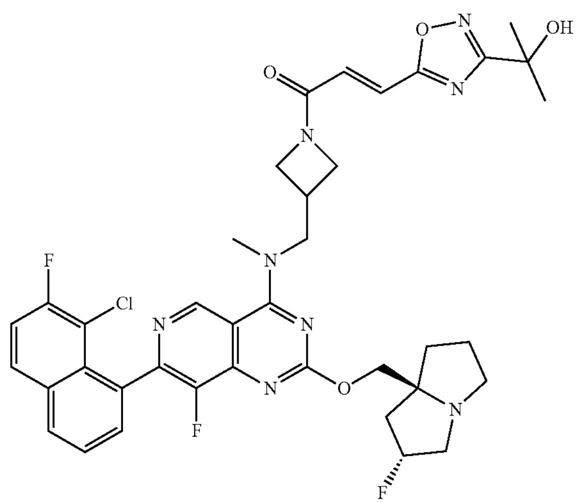 [SMILES: CN(CC1CN(C(=O)/C=C/c2nc(C(C)(C)O)no2)C1)c1nc(OC[C@@]23CCCN2C[C@H](F)C3)nc2c(F)c(-c3cccc4ccc(F)c(Cl)c34)ncc12] | ++++ |
| 79 | 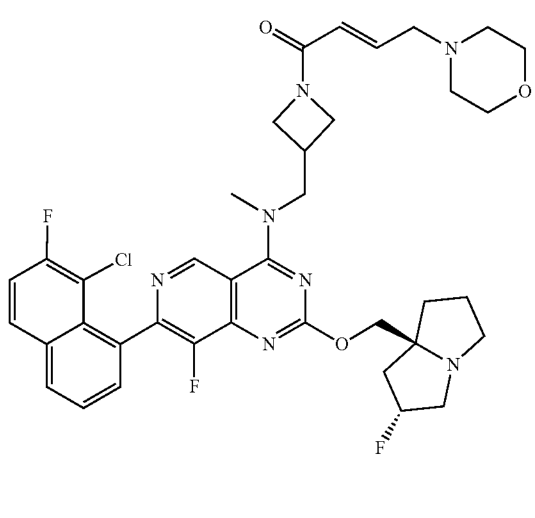 [SMILES: CN(CC1CN(C(=O)/C=C/CN2CCOCC2)C1)c1nc(OC[C@@]23CCCN2C[C@H](F)C3)nc2c(F)c(-c3cccc4ccc(F)c(Cl)c34)ncc12] | +++ |

TABLE 1-continued

Inhibition of KRAS G12C and cRAF Binding (IC$_{50}$)

| Synthetic Example | Structure | IC$_{50}$ |
|---|---|---|
| 80 | 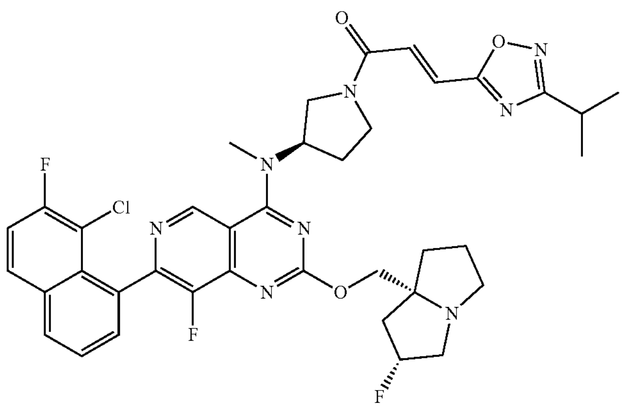 [SMILES: CC(C)c1noc(/C=C/C(=O)N2CC[C@@H](N(C)c3nc(OC[C@]45CCCN4C[C@H](F)C5)nc4c(F)c(-c5cccc6ccc(F)c(Cl)c56)ncc34)C2)n1] | +++ |
| 81 | 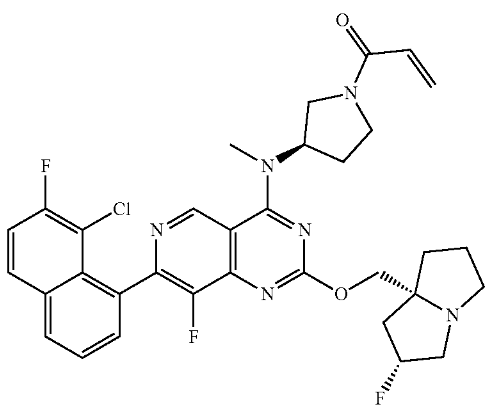 [SMILES: C=CC(=O)N1CC[C@@H](N(C)c2nc(OC[C@]34CCCN3C[C@H](F)C4)nc3c(F)c(-c4cccc5ccc(F)c(Cl)c45)ncc23)C1] | +++ |
| 82 | 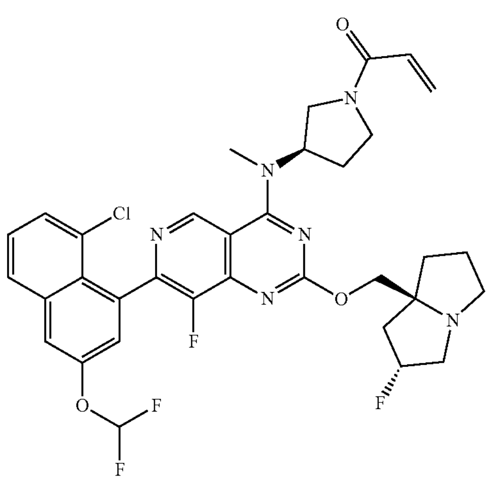 [SMILES: C=CC(=O)N1CC[C@@H](N(C)c2nc(OC[C@@]34CCCN3C[C@H](F)C4)nc3c(F)c(-c4cc(OC(F)F)cc5cccc(Cl)c45)ncc23)C1] | + |

TABLE 1-continued

Inhibition of KRAS G12C and cRAF Binding (IC$_{50}$)

| Synthetic Example | Structure | IC$_{50}$ |
|---|---|---|
| 83 | 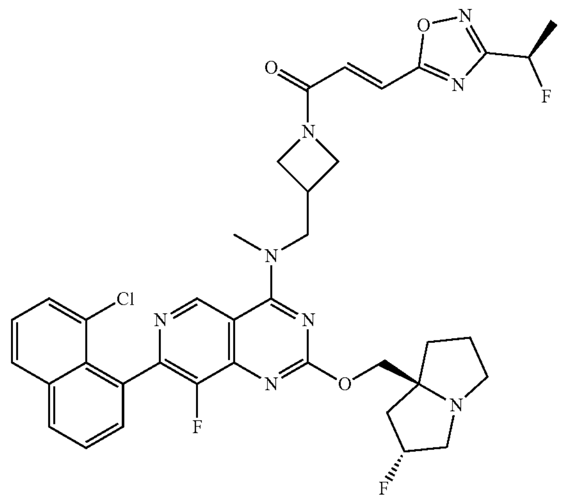 [SMILES: C[C@@H](F)c1noc(/C=C/C(=O)N2CC(CN(C)c3nc(OC[C@@]45CCCN4C[C@H](F)C5)nc4c(F)c(-c5cccc6cccc(Cl)c56)ncc34)C2)n1] | ++++ |
| 84 | 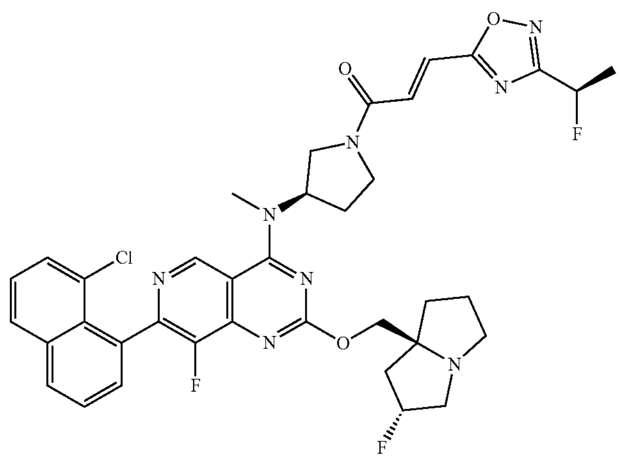 [SMILES: C[C@@H](F)c1noc(/C=C/C(=O)N2CC[C@@H](N(C)c3nc(OC[C@@]45CCCN4C[C@H](F)C5)nc4c(F)c(-c5cccc6cccc(Cl)c56)ncc34)C2)n1] | ++++ |
| 85 | (formate salt) | ++++ |

TABLE 1-continued

Inhibition of KRAS G12C and cRAF Binding (IC$_{50}$)

| Synthetic Example | Structure | IC$_{50}$ |
|---|---|---|
| 86 | 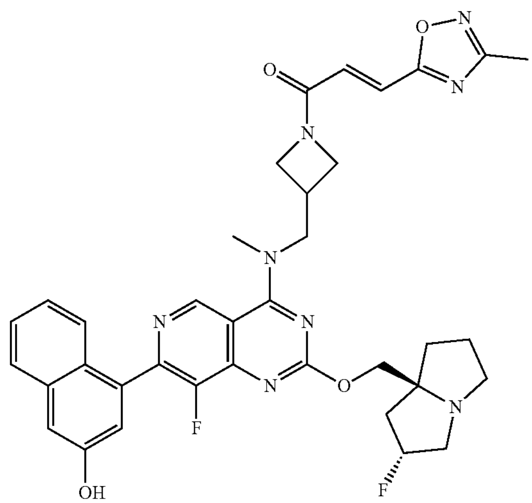 [SMILES: Cc1noc(/C=C/C(=O)N2CC(CN(C)c3nc(OC[C@@]45CCCN4C[C@H](F)C5)nc4c(F)c(-c5cc(O)cc6ccccc56)ncc34)C2)n1] | ++++ |
| 87 | 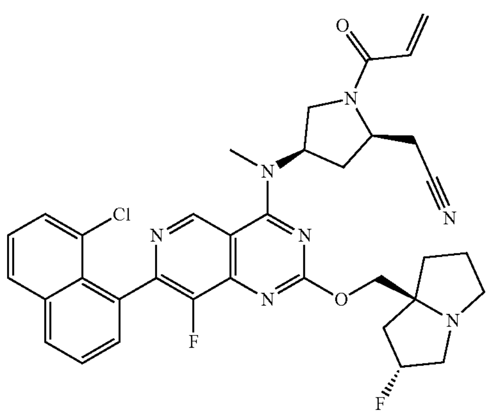 [SMILES: C=CC(=O)N1C[C@H](N(C)c2nc(OC[C@@]34CCCN3C[C@H](F)C4)nc3c(F)c(-c4cccc5cccc(Cl)c45)ncc23)C[C@@H]1CC#N] | ++ |
| 88 | 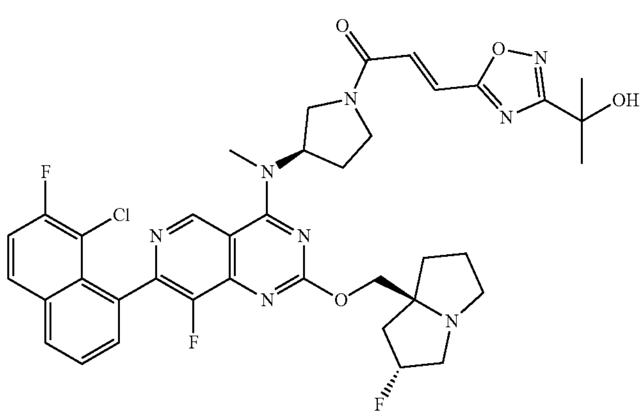 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)/C=C/c2nc(C(C)(C)O)no2)C1] | ++++ |

TABLE 1-continued
Inhibition of KRAS G12C and cRAF Binding (IC$_{50}$)
| Synthetic Example | Structure | IC$_{50}$ |
|---|---|---|
| 89 | 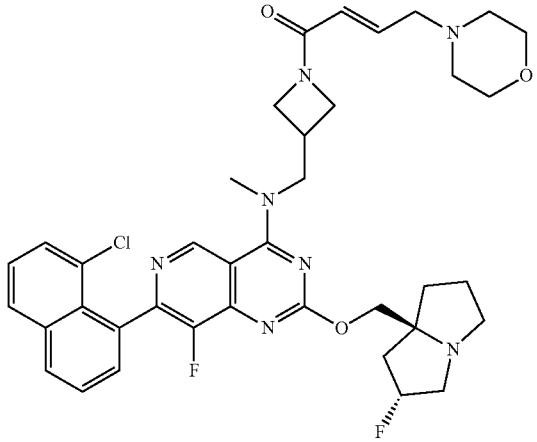 [SMILES: CN(CC1CN(C(=O)/C=C/CN2CCOCC2)C1)c1nc(OC[C@@]23CCCN2C[C@H](F)C3)nc2c(F)c(-c3cccc4cccc(Cl)c34)ncc12] (formate salt) | +++ |
| 90 | 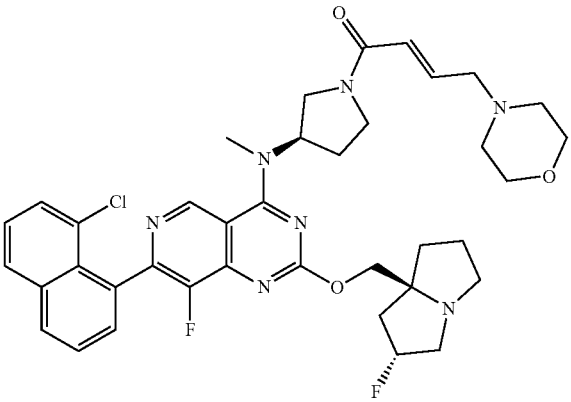 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/CN2CCOCC2)C1] (formate salt) | +++ |
| 91 | 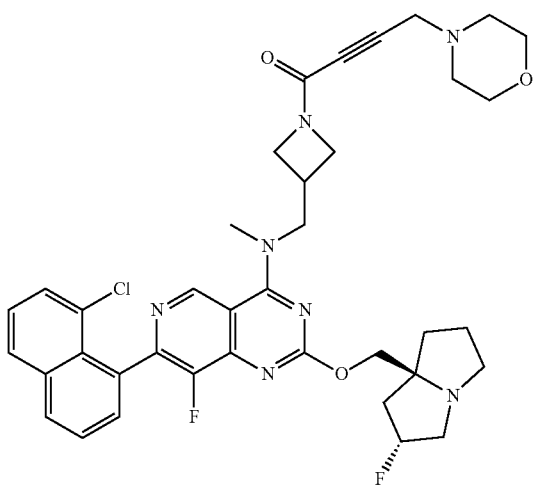 [SMILES: CN(CC1CN(C(=O)C#CCN2CCOCC2)C1)c1nc(OC[C@@]23CCCN2C[C@H](F)C3)nc2c(F)c(-c3cccc4cccc(Cl)c34)ncc12] | ++ |

TABLE 1-continued

Inhibition of KRAS G12C and cRAF Binding (IC$_{50}$)

| Synthetic Example | Structure | IC$_{50}$ |
|---|---|---|
| 92 | 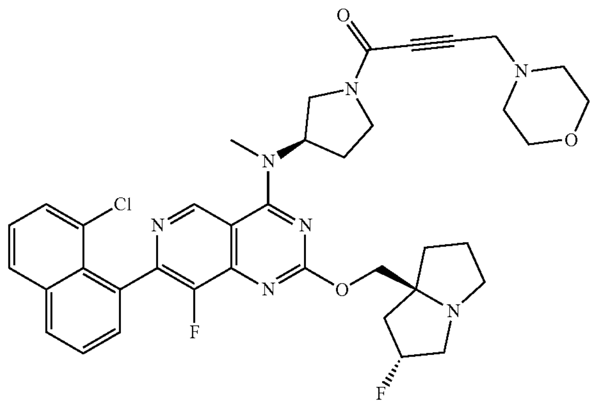 [SMILES: CN(c1nc(OC[C@@]23CCCN2C[C@H](F)C3)nc2c(F)c(-c3cccc4cccc(Cl)c34)ncc12)[C@@H]1CCN(C(=O)C#CCN2CCOCC2)C1] | + |
| 93 | 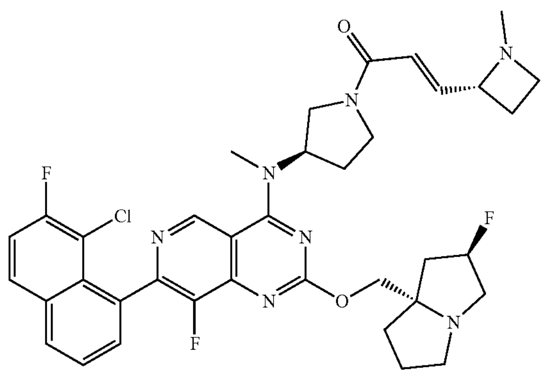 | +++ |
| 94 | 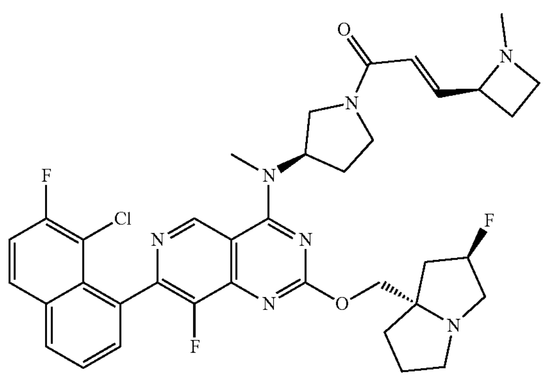 [SMILES: CN1CC[C@H]1/C=C/C(=O)N1CC[C@@H](N(C)c2nc(OC[C@@]34CCCN3C[C@H](F)C4)nc3c(F)c(-c4cccc5ccc(F)c(Cl)c45)ncc23)C1] | +++ |
| 95 | 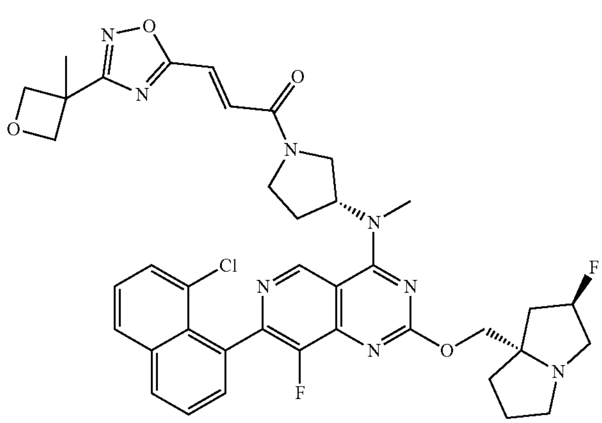 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2nc(C3(C)COC3)no2)C1] | ++++ |

TABLE 1-continued

Inhibition of KRAS G12C and cRAF Binding (IC$_{50}$)

| Synthetic Example | Structure | IC$_{50}$ |
|---|---|---|
| 96 | 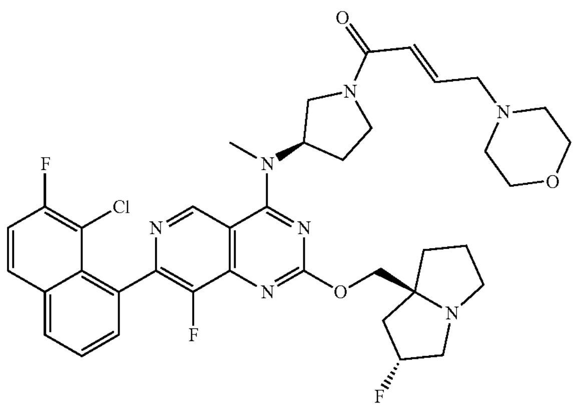 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)/C=C/CN2CCOCC2)C1] | ++ |
| 97 | 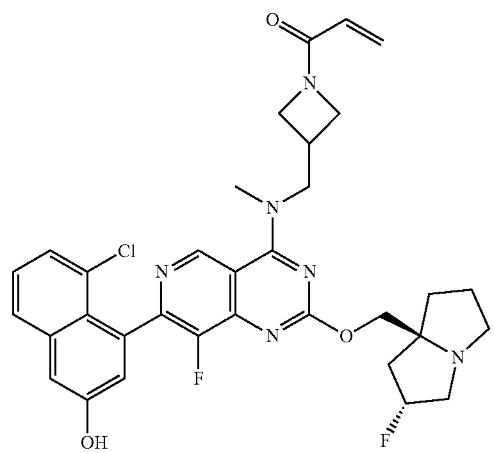 [SMILES: C=CC(=O)N1CC(CN(C)c2nc(OC[C@@]34CCCN3C[C@H](F)C4)nc3c(F)c(-c4cc(O)cc5cccc(Cl)c45)ncc23)C1] | ++++ |
| 98 | (formate salt) | |

TABLE 1-continued

Inhibition of KRAS G12C and cRAF Binding (IC$_{50}$)

| Synthetic Example | Structure | IC$_{50}$ |
|---|---|---|
| 99 | 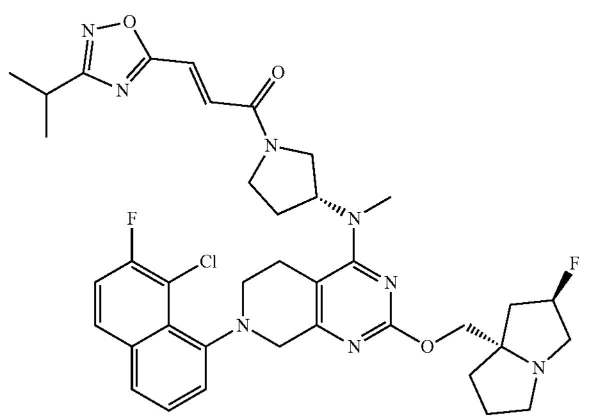 [SMILES: CC(C)c1noc(/C=C/C(=O)N2CC[C@@H](N(C)c3nc(OC[C@@]45CCCN4C[C@H](F)C5)nc4c3CCN(c3cccc5ccc(F)c(Cl)c35)C4)C2)n1] | +++ |
| 100 | 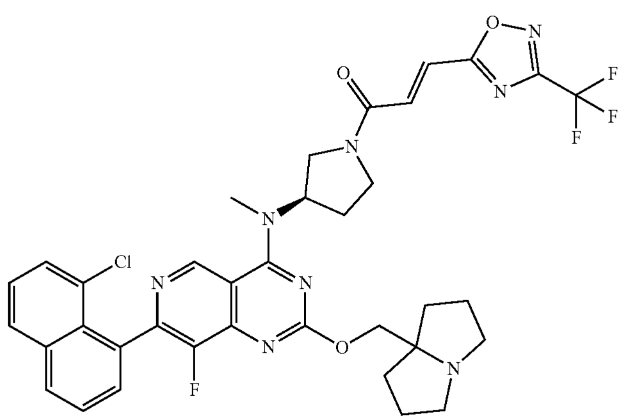 [SMILES: CN(c1nc(OCC23CCCN2CCC3)nc2c(F)c(-c3cccc4cccc(Cl)c34)ncc12)[C@@H]1CCN(C(=O)/C=C/c2nc(C(F)(F)F)no2)C1] | ++++ |
| 101 | (formate salt) | ++++ |

TABLE 1-continued
Inhibition of KRAS G12C and cRAF Binding (IC$_{50}$)
| Synthetic Example | Structure | IC$_{50}$ |
|---|---|---|
| 102 | 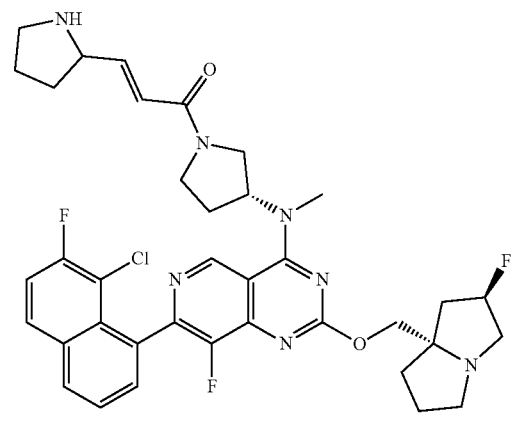 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)/C=C/C2CCCN2)C1] (formate salt) | +++ |
| 103 | 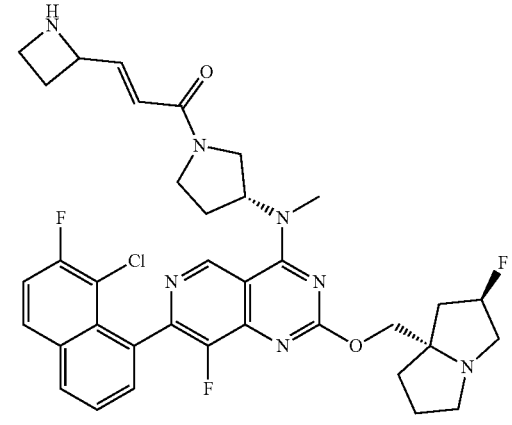 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)/C=C/C2CCN2)C1] | +++ |
| 104 | 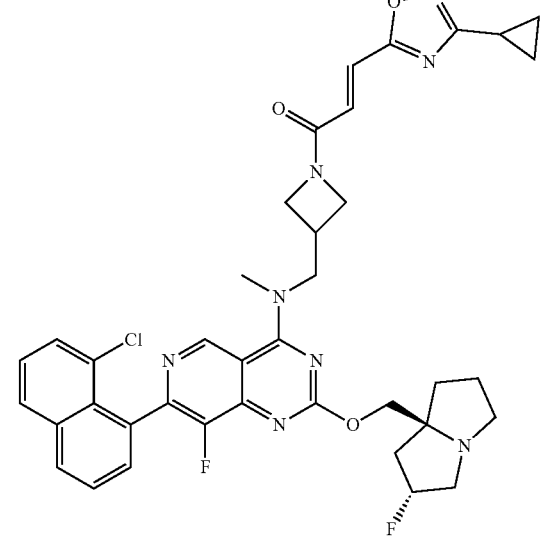 | ++ |

TABLE 1-continued

Inhibition of KRAS G12C and cRAF Binding (IC$_{50}$)

| Synthetic Example | Structure | IC$_{50}$ |
|---|---|---|
| 105 | 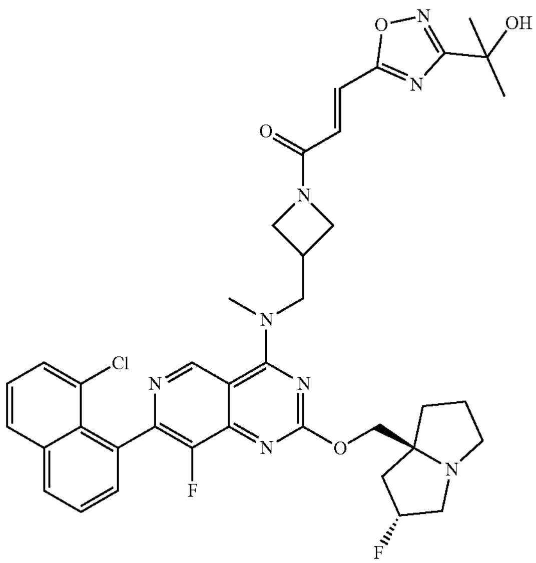 [SMILES: CN(CC1CN(C(=O)/C=C/c2nc(C(C)(C)O)no2)C1)c1nc(OC[C@@]23CCCN2C[C@H](F)C3)nc2c(F)c(-c3cccc4cccc(Cl)c34)ncc12] | ++++ |
| 106 | 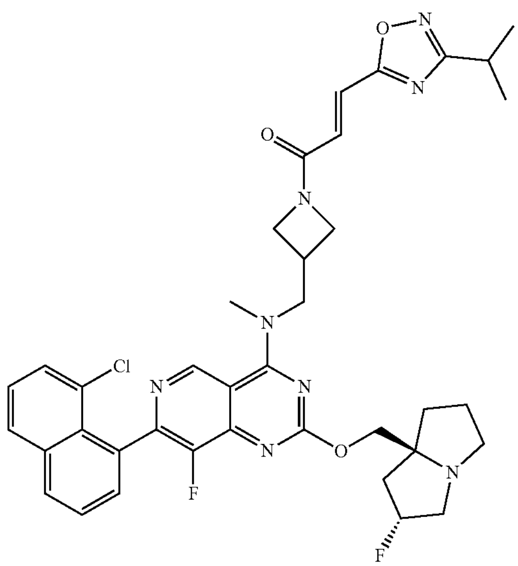 [SMILES: CC(C)c1noc(/C=C/C(=O)N2CC(CN(C)c3nc(OC[C@@]45CCCN4C[C@H](F)C5)nc4c(F)c(-c5cccc6cccc(Cl)c56)ncc34)C2)n1] | +++ |
| 107 | 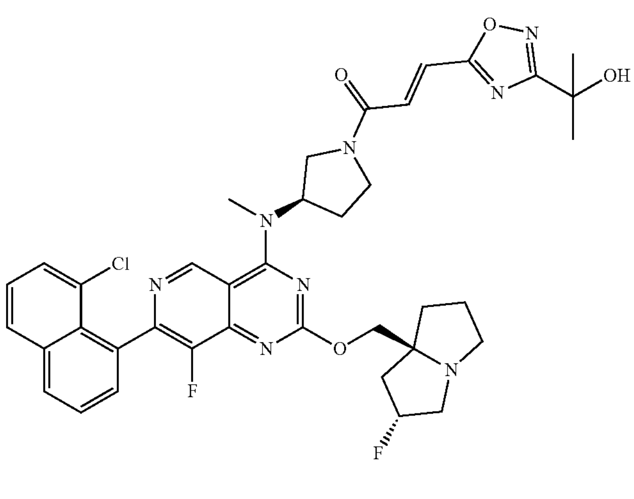 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2nc(C(C)(C)O)no2)C1] | ++++ |

TABLE 1-continued

Inhibition of KRAS G12C and cRAF Binding (IC$_{50}$)

| Synthetic Example | Structure | IC$_{50}$ |
|---|---|---|
| 108 | 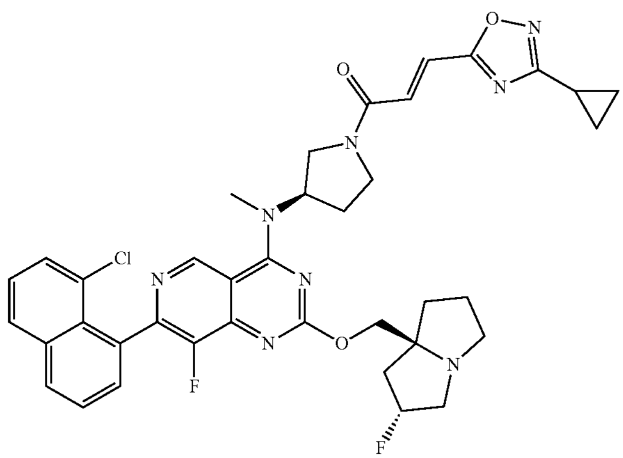 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2nc(C3CC3)no2)C1] | ++++ |
| 109 | 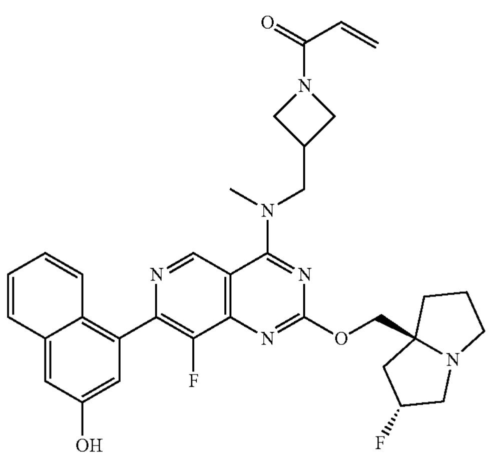 | +++ |
| 110 | 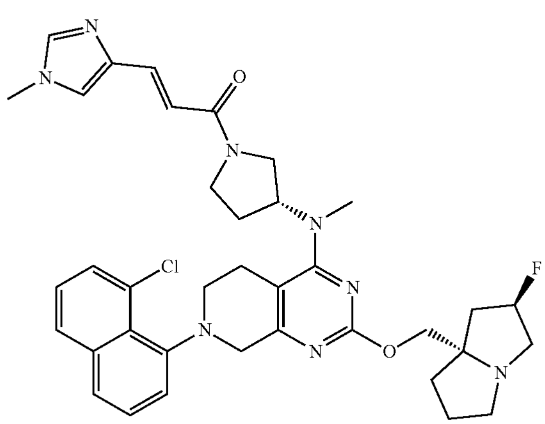 [SMILES: CN(c1nc(OC[C@@]23CCCN2C[C@H](F)C3)nc2c1CCN(c1cccc3cccc(Cl)c13)C2)[C@@H]1CCN(C(=O)/C=C/c2cn(C)cn2)C1] | + |

TABLE 1-continued
Inhibition of KRAS G12C and cRAF Binding (IC$_{50}$)
| Synthetic Example | Structure | IC$_{50}$ |
|---|---|---|
| 111 | 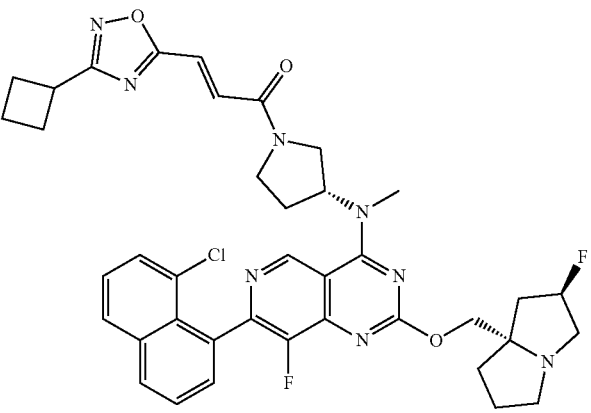 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2nc(C3CCC3)no2)C1] | +++ |
| 112 | 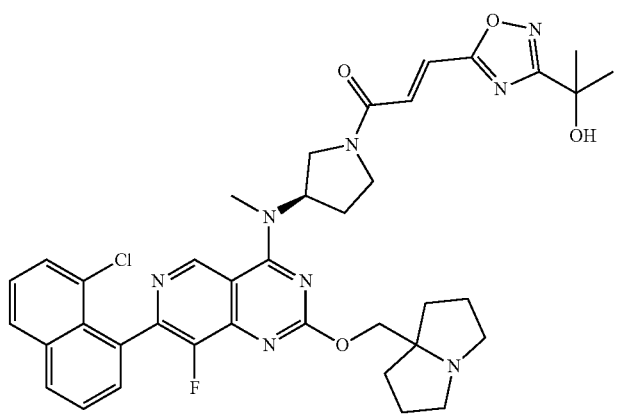 [SMILES: CN(c1nc(OCC23CCCN2CCC3)nc2c(F)c(-c3cccc4cccc(Cl)c34)ncc12)[C@@H]1CCN(C(=O)/C=C/c2nc(C(C)(C)O)no2)C1] | ++++ |
| 113 | 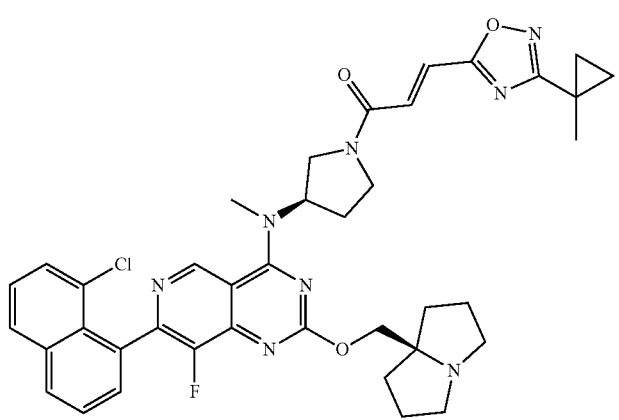 | +++ |

TABLE 1-continued

Inhibition of KRAS G12C and cRAF Binding (IC$_{50}$)

| Synthetic Example | Structure | IC$_{50}$ |
|---|---|---|
| 114 | 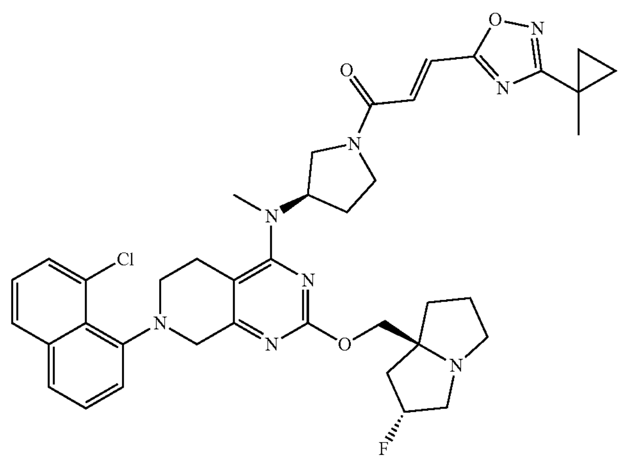 [SMILES: CN(c1nc(OC[C@@]23CCCN2C[C@H](F)C3)nc2c1CCN(c1cccc3cccc(Cl)c13)C2)[C@@H]1CCN(C(=O)/C=C/c2nc(C3(C)CC3)no2)C1] | +++ |
| 115 | 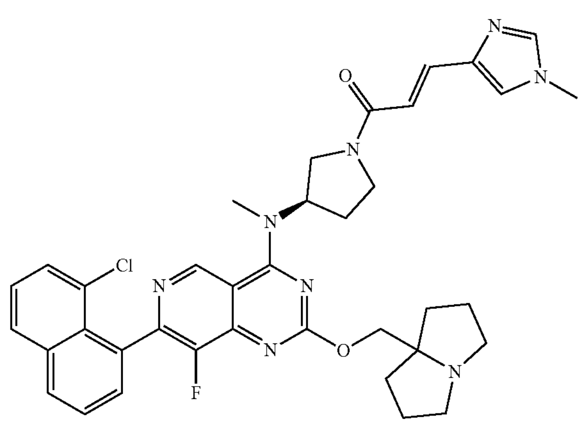 [SMILES: CN(c1nc(OCC23CCCN2CCC3)nc2c(F)c(-c3cccc4cccc(Cl)c34)ncc12)[C@@H]1CCN(C(=O)/C=C/c2cn(C)cn2)C1] | + |
| 116 | 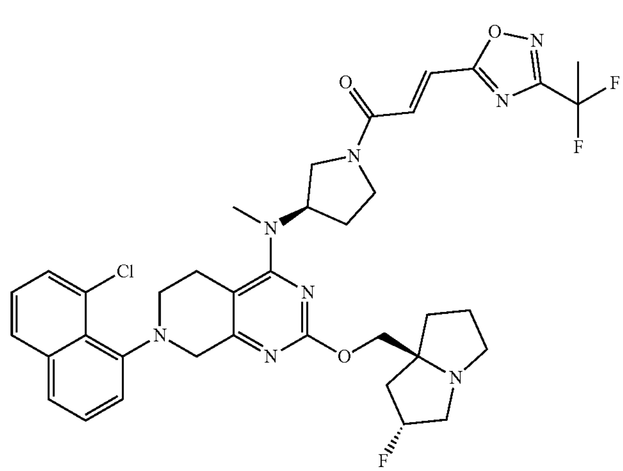 [SMILES: CN(c1nc(OC[C@@]23CCCN2C[C@H](F)C3)nc2c1CCN(c1cccc3cccc(Cl)c13)C2)[C@@H]1CCN(C(=O)/C=C/c2nc(C(C)(F)F)no2)C1] | ++++ |

TABLE 1-continued
Inhibition of KRAS G12C and cRAF Binding (IC$_{50}$)
| Synthetic Example | Structure | IC$_{50}$ |
|---|---|---|
| 117 | 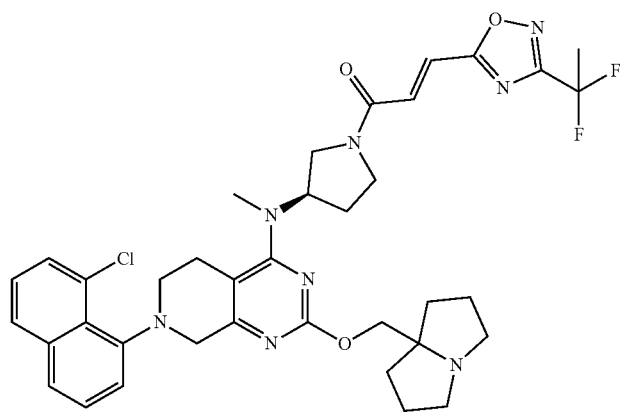 [SMILES: CN(c1nc(OCC23CCCN2CCC3)nc2c1CCN(c1cccc3cccc(Cl)c13)C2)[C@@H]1CCN(C(=O)/C=C/c2nc(C(C)(F)F)no2)C1] | ++++ |
| 118 | 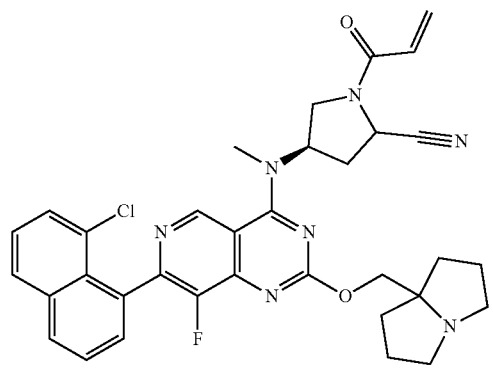 [SMILES: C=CC(=O)N1C[C@H](N(C)c2nc(OCC34CCCN3CCC4)nc3c(F)c(-c4cccc5cccc(Cl)c45)ncc23)CC1C#N] | +++ |
| 119 | 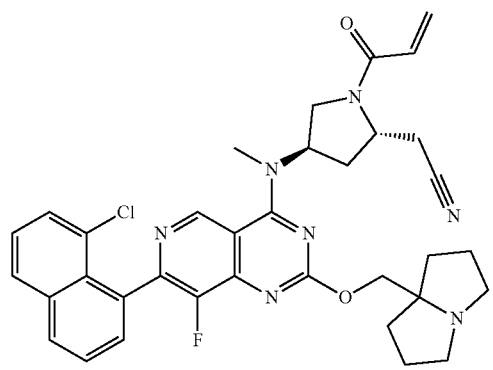 [SMILES: C=CC(=O)N1C[C@H](N(C)c2nc(OCC34CCCN3CCC4)nc3c(F)c(-c4cccc5cccc(Cl)c45)ncc23)C[C@H]1CC#N] | ++ |

TABLE 1-continued
Inhibition of KRAS G12C and cRAF Binding (IC$_{50}$)
| Synthetic Example | Structure | IC$_{50}$ |
|---|---|---|
| 120 | 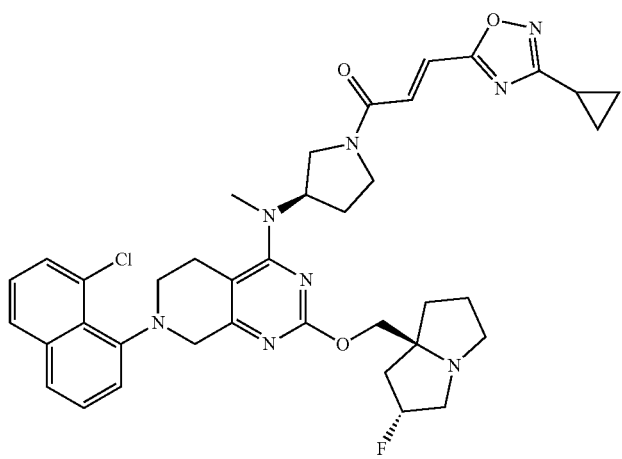 [SMILES: CN(c1nc(OC[C@@]23CCCN2C[C@H](F)C3)nc2c1CCN(c1cccc3cccc(Cl)c13)C2)[C@@H]1CCN(C(=O)/C=C/c2nc(C3CC3)no2)C1] | +++ |
| 121 | 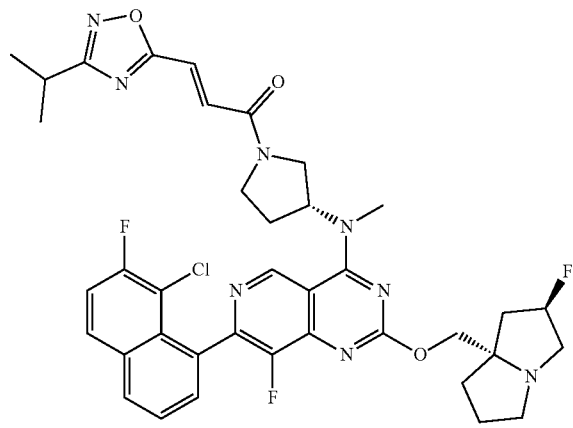 [SMILES: CC(C)c1noc(/C=C/C(=O)N2CC[C@@H](N(C)c3nc(OC[C@@]45CCCN4C[C@H](F)C5)nc4c(F)c(-c5cccc6ccc(F)c(Cl)c56)ncc34)C2)n1] | ++++ |
| 122 | 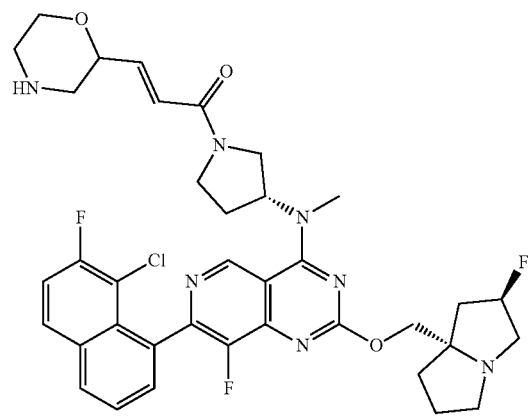 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)/C=C/C2CNCCO2)C1]<br>(formate salt) | ++ |

TABLE 1-continued
Inhibition of KRAS G12C and cRAF Binding (IC$_{50}$)
| Synthetic Example | Structure | IC$_{50}$ |
|---|---|---|
| 123 | 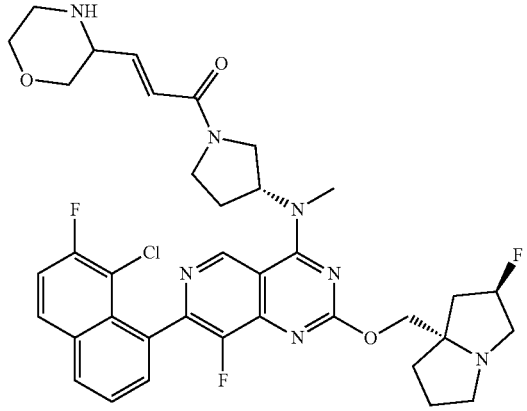 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)/C=C/C2COCCN2)C1]<br>(formate salt) | ++ |
| 124 | 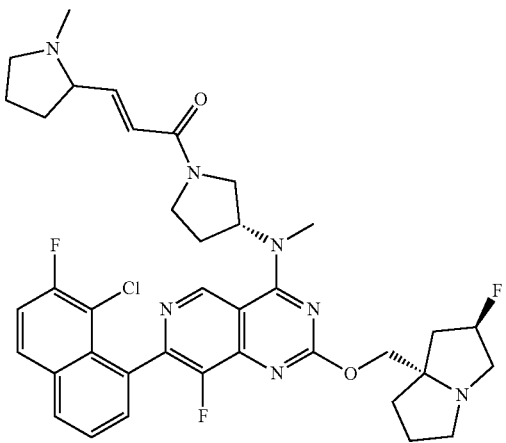 [SMILES: CN1CCCC1/C=C/C(=O)N1CC[C@@H](N(C)c2nc(OC[C@@]34CCCN3C[C@H](F)C4)nc3c(F)c(-c4cccc5ccc(F)c(Cl)c45)ncc23)C1]<br>(formate salt) | +++ |
| 125 | 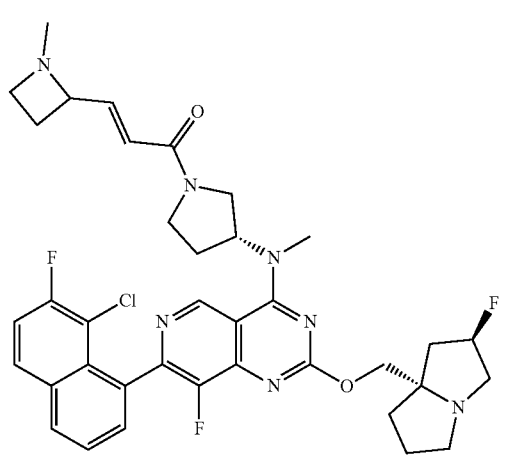 [SMILES: CN1CCC1/C=C/C(=O)N1CC[C@@H](N(C)c2nc(OC[C@@]34CCCN3C[C@H](F)C4)nc3c(F)c(-c4cccc5ccc(F)c(Cl)c45)ncc23)C1] | ++++ |

TABLE 1-continued
Inhibition of KRAS G12C and cRAF Binding (IC$_{50}$)
| Synthetic Example | Structure | IC$_{50}$ |
|---|---|---|
| 126 | 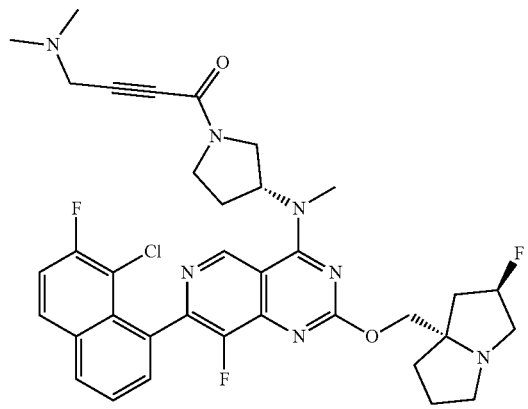 [SMILES: CN(C)CC#CC(=O)N1CC[C@@H](N(C)c2nc(OC[C@@]34CCCN3C[C@H](F)C4)nc3c(F)c(-c4cccc5ccc(F)c(Cl)c45)ncc23)C1] | ++++ |
| 127 | 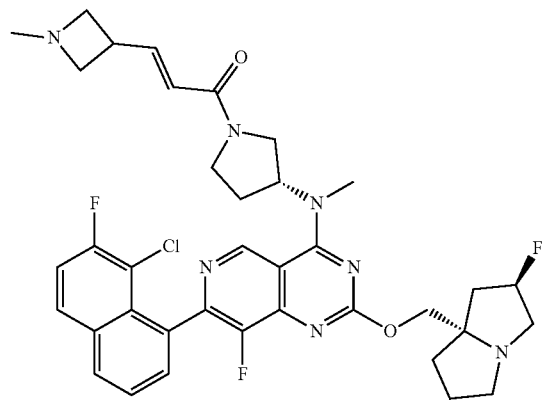 [SMILES: CN1CC(/C=C/C(=O)N2CC[C@@H](N(C)c3nc(OC[C@@]45CCCN4C[C@H](F)C5)nc4c(F)c(-c5cccc6ccc(F)c(Cl)c56)ncc34)C2)C1] | ++ |
| 128 | 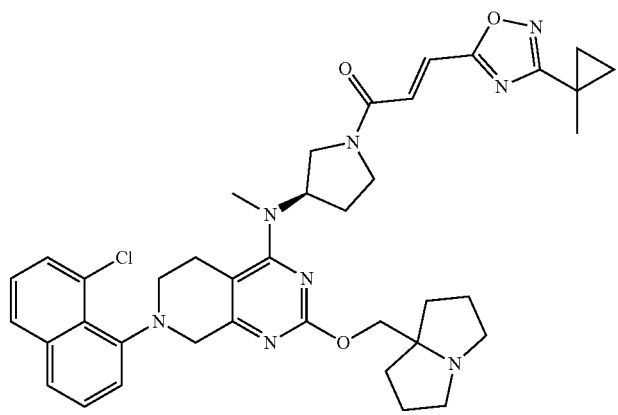 [SMILES: CN(c1nc(OCC23CCCN2CCC3)nc2c1CCN(c1cccc3cccc(Cl)c13)C2)[C@@H]1CCN(C(=O)/C=C/c2nc(C3(C)CC3)no2)C1] | ++ |

TABLE 1-continued

Inhibition of KRAS G12C and cRAF Binding (IC$_{50}$)

| Synthetic Example | Structure | IC$_{50}$ |
|---|---|---|
| 129 | 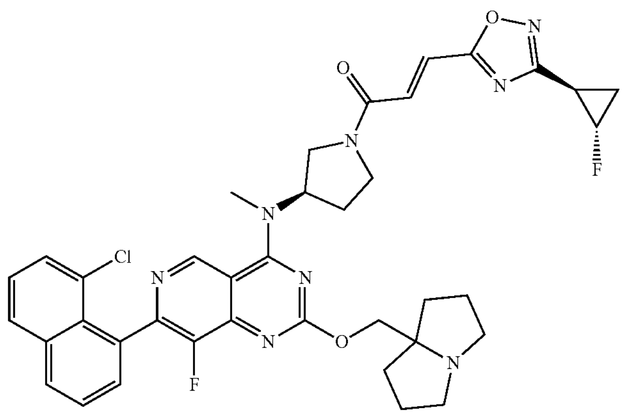 [SMILES: CN(c1nc(OCC23CCCN2CCC3)nc2c(F)c(-c3cccc4cccc(Cl)c34)ncc12)[C@@H]1CCN(C(=O)/C=C/c2nc([C@H]3C[C@@H]3F)no2)C1] | +++ |
| 130 | 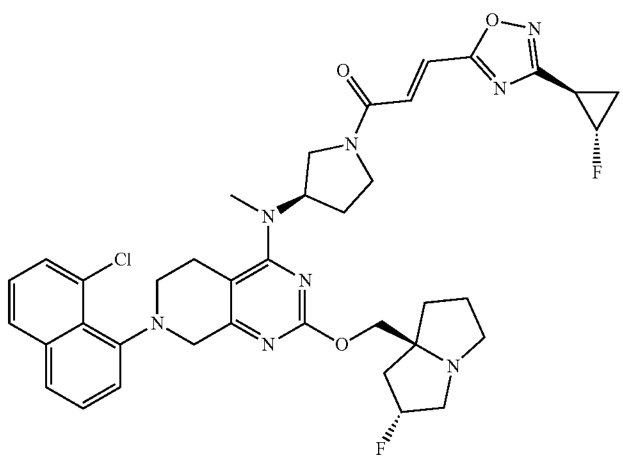 [SMILES: CN(c1nc(OC[C@@]23CCCN2C[C@H](F)C3)nc2c1CCN(c1cccc3cccc(Cl)c13)C2)[C@@H]1CCN(C(=O)/C=C/c2nc([C@H]3C[C@@H]3F)no2)C1] | +++ |
| 131 | 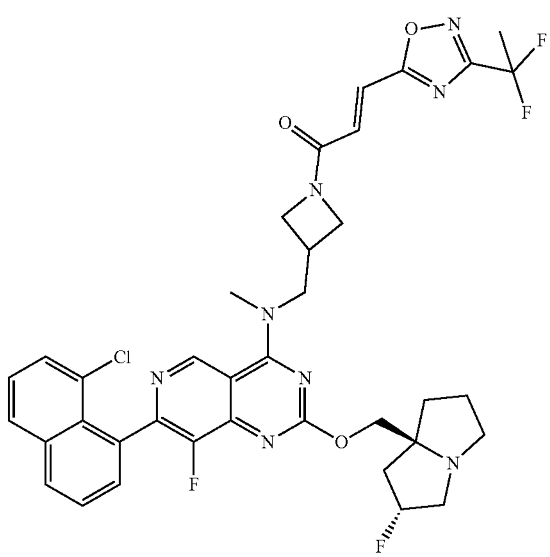 [SMILES: CN(CC1CN(C(=O)/C=C/c2nc(C(C)(F)F)no2)C1)c1nc(OC[C@@]23CCCN2C[C@H](F)C3)nc2c(F)c(-c3cccc4cccc(Cl)c34)ncc12] | ++++ |

TABLE 1-continued

Inhibition of KRAS G12C and cRAF Binding (IC$_{50}$)

| Synthetic Example | Structure | IC$_{50}$ |
|---|---|---|
| 132 | 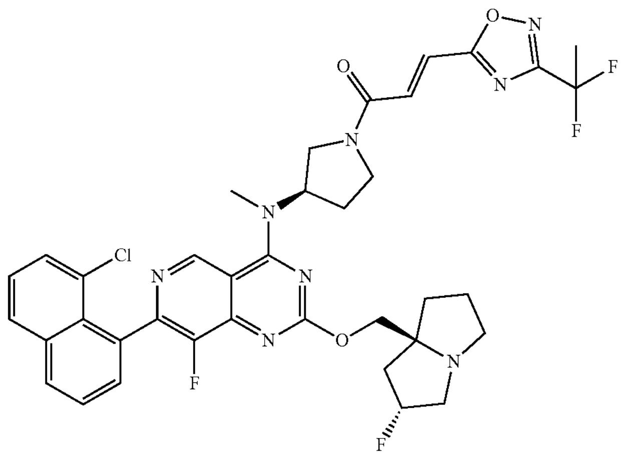 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2nc(C(C)(F)F)no2)C1] | ++++ |
| 133 | (formate salt) | ++++ |
| 134 | 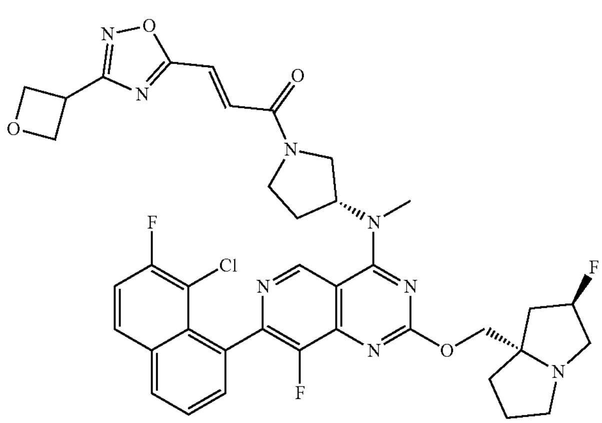 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)/C=C/c2nc(C3COC3)no2)C1] | ++++ |

TABLE 1-continued

Inhibition of KRAS G12C and cRAF Binding (IC$_{50}$)

| Synthetic Example | Structure | IC$_{50}$ |
|---|---|---|
| 135 | 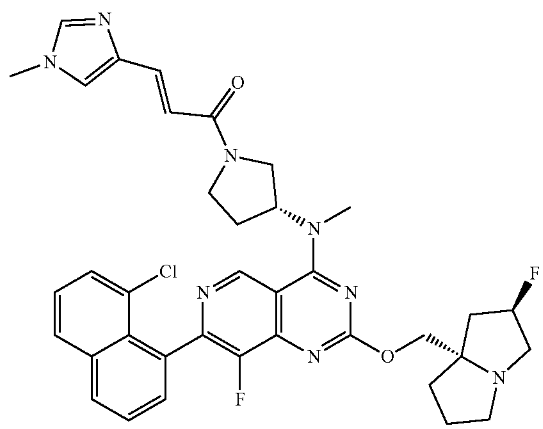 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2cn(C)cn2)C1] | ++ |
| 136 | 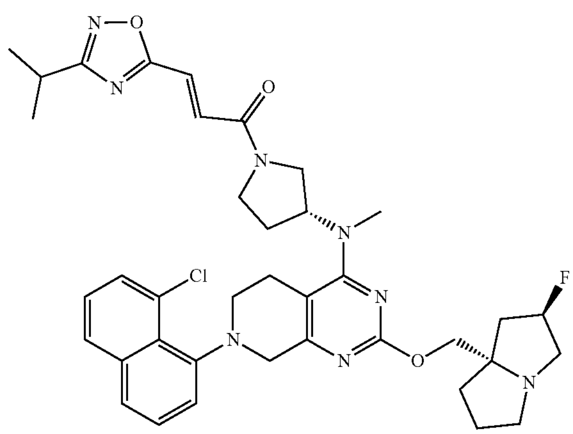 [SMILES: CC(C)c1noc(/C=C/C(=O)N2CC[C@@H](N(C)c3nc(OC[C@@]45CCCN4C[C@H](F)C5)nc4c3CCN(c3cccc5cccc(Cl)c35)C4)C2)n1] | +++ |
| 137 | 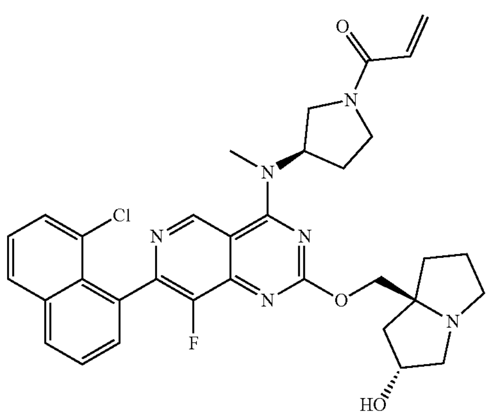 [SMILES: C=CC(=O)N1CC[C@@H](N(C)c2nc(OC[C@@]34CCCN3C[C@H](O)C4)nc3c(F)c(-c4cccc5cccc(Cl)c45)ncc23)C1] | +++ |

TABLE 1-continued

Inhibition of KRAS G12C and cRAF Binding (IC$_{50}$)

| Synthetic Example | Structure | IC$_{50}$ |
|---|---|---|
| 138 | 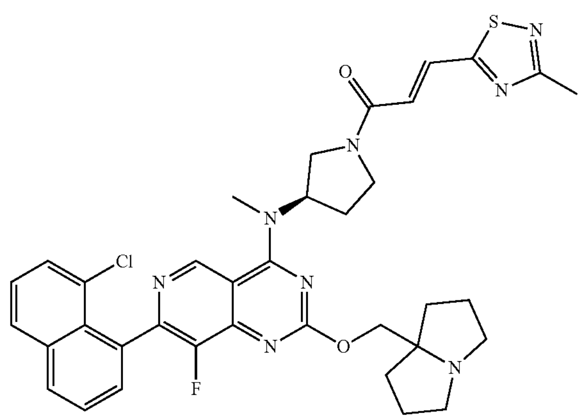 [SMILES: Cc1nsc(/C=C/C(=O)N2CC[C@@H](N(C)c3nc(OCC45CCCN4CCC5)nc4c(F)c(-c5cccc6cccc(Cl)c56)ncc34)C2)n1] | +++ |
| 139 | 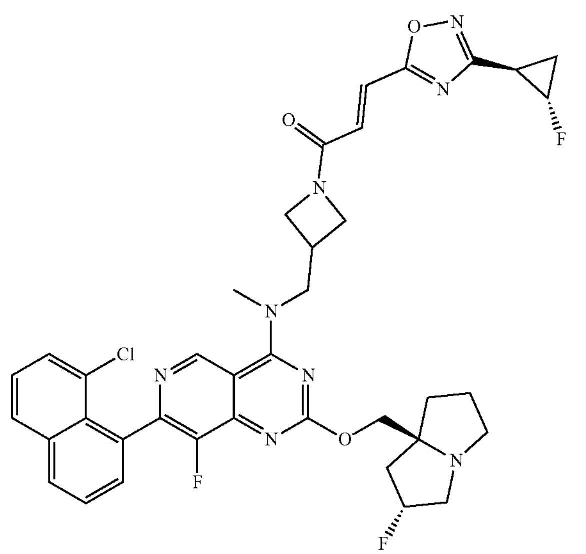 [SMILES: CN(CC1CN(C(=O)/C=C/c2nc([C@H]3C[C@@H]3F)no2)C1)c1nc(OC[C@@]23CCCN2C[C@H](F)C3)nc2c(F)c(-c3cccc4cccc(Cl)c34)ncc12] | +++ |
| 140 | 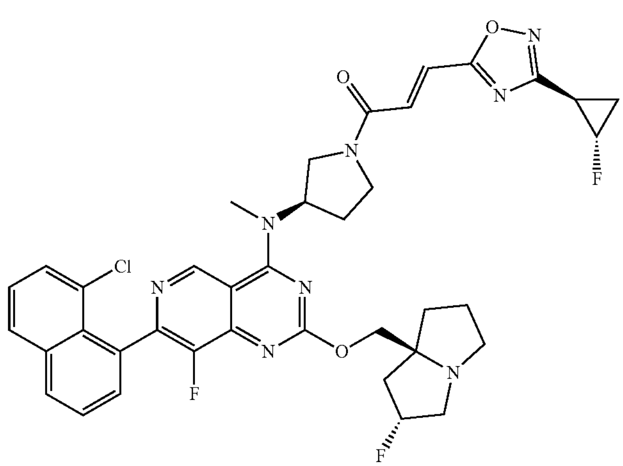 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2nc([C@H]3C[C@@H]3F)no2)C1] | +++ |

TABLE 1-continued
Inhibition of KRAS G12C and cRAF Binding (IC$_{50}$)
| Synthetic Example | Structure | IC$_{50}$ |
|---|---|---|
| 141 | 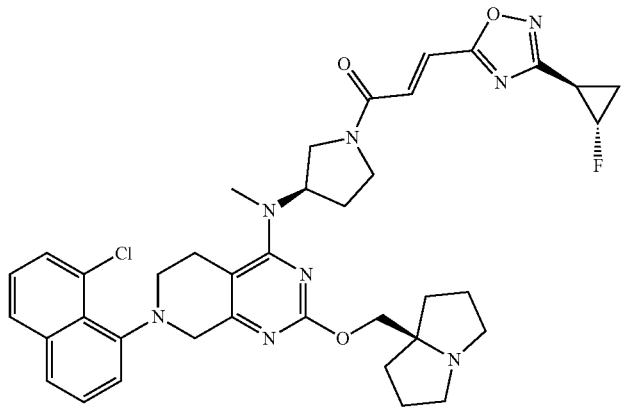 | +++ |
| 142 | 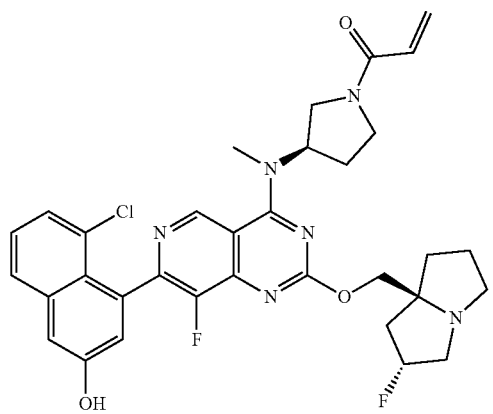 [SMILES: C=CC(=O)N1CC[C@@H](N(C)c2nc(OC[C@@]34CCCN3C[C@H](F)C4)nc3c(F)c(-c4cc(O)cc5cccc(Cl)c45)ncc23)C1] | ++++ |
| 143 | 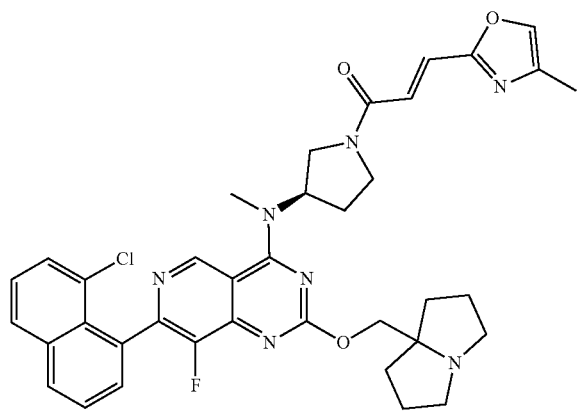 [SMILES: Cc1coc(/C=C/C(=O)N2CC[C@@H](N(C)c3nc(OCC45CCCN4CCC5)nc4c(F)c(-c5cccc6cccc(Cl)c56)ncc34)C2)n1] | ++ |

TABLE 1-continued
Inhibition of KRAS G12C and cRAF Binding (IC$_{50}$)
| Synthetic Example | Structure | IC$_{50}$ |
|---|---|---|
| 144 | 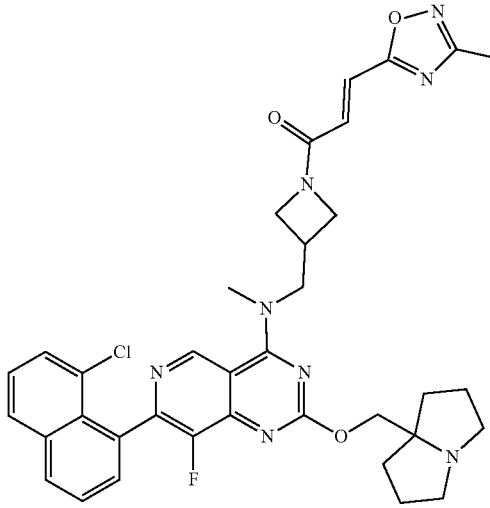 (formate salt) | ++++ |
| 145 | 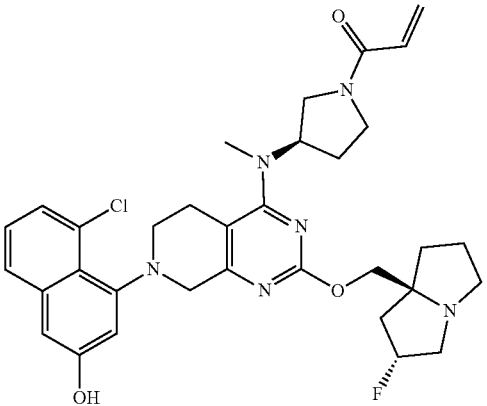 [SMILES: C=CC(=O)N1CC[C@@H](N(C)c2nc(OC[C@@]34CCCN3C[C@H](F)C4)nc3c2CCN(c2cc(O)cc4cccc(Cl)c24)C3)C1] | ++++ |
| 146 | 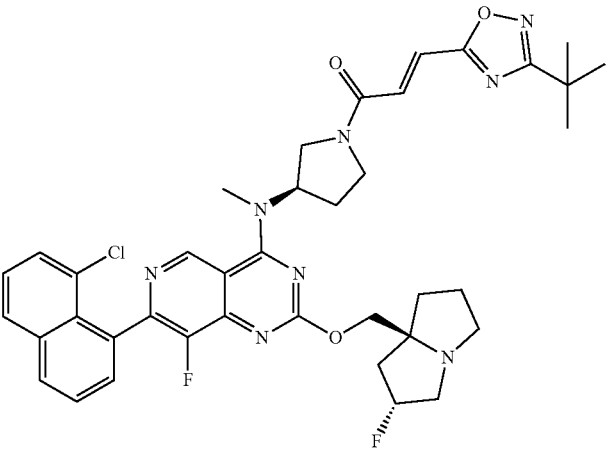 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2nc(C(C)(C)C)no2)C1] | +++ |

TABLE 1-continued

Inhibition of KRAS G12C and cRAF Binding (IC$_{50}$)

| Synthetic Example | Structure | IC$_{50}$ |
|---|---|---|
| 147 | 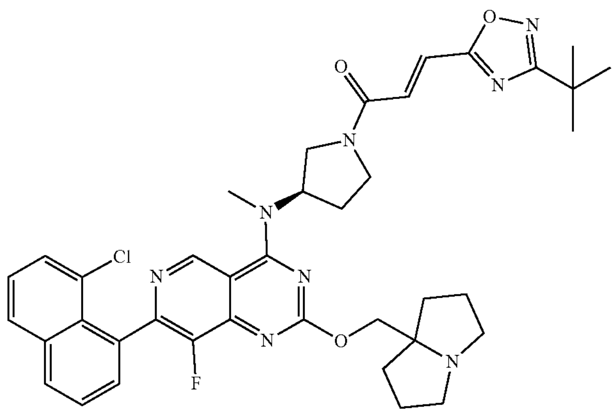 [SMILES: CN(c1nc(OCC23CCCN2CCC3)nc2c(F)c(-c3cccc4cccc(Cl)c34)ncc12)[C@@H]1CCN(C(=O)/C=C/c2nc(C(C)(C)C)no2)C1] | +++ |
| 148 | 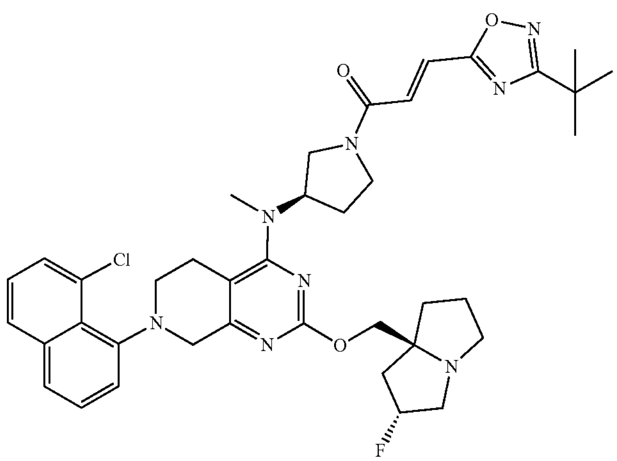 [SMILES: CN(c1nc(OC[C@@]23CCCN2C[C@H](F)C3)nc2c1CCN(c1cccc3cccc(Cl)c13)C2)[C@@H]1CCN(C(=O)/C=C/c2nc(C(C)(C)C)no2)C1] | ++ |
| 149 | 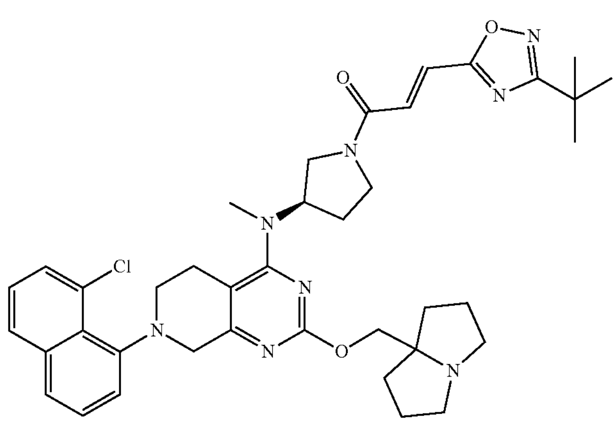 [SMILES: CN(c1nc(OCC23CCCN2CCC3)nc2c1CCN(c1cccc3cccc(Cl)c13)C2)[C@@H]1CCN(C(=O)/C=C/c2nc(C(C)(C)C)no2)C1] | +++ |

TABLE 1-continued
Inhibition of KRAS G12C and cRAF Binding (IC$_{50}$)
| Synthetic Example | Structure | IC$_{50}$ |
|---|---|---|
| 150 | 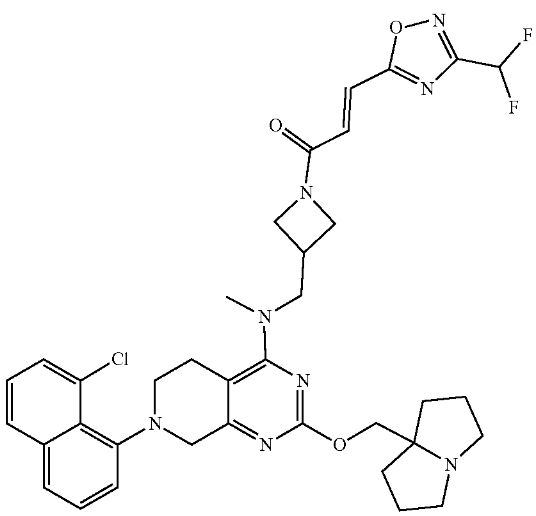 [SMILES: CN(CC1CN(C(=O)/C=C/c2nc(C(F)F)no2)C1)c1nc(OCC23CCCN2CCC3)nc2c1CCN(c1cccc3cccc(Cl)c13)C2] | ++++ |
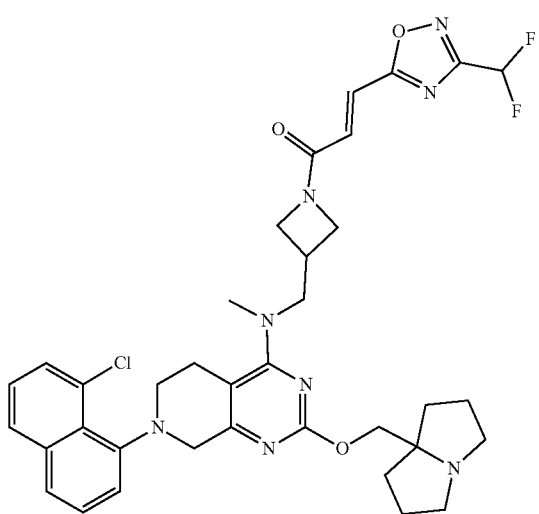
(formate salt)
| 151 | | + |

TABLE 1-continued
Inhibition of KRAS G12C and cRAF Binding (IC$_{50}$)
| Synthetic Example | Structure | IC$_{50}$ |
|---|---|---|
| 152 | 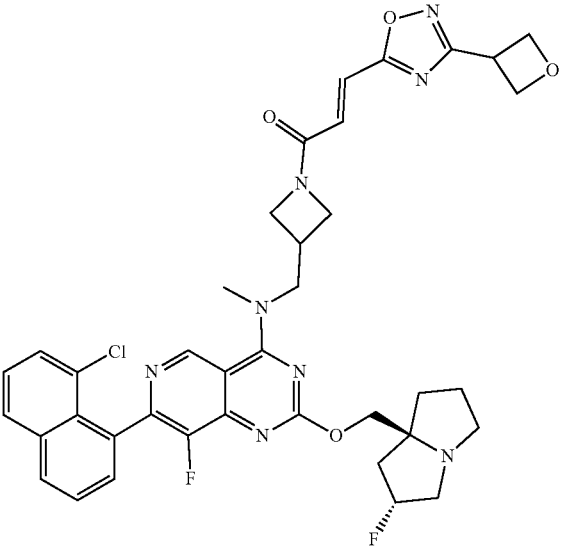 [SMILES: CN(CC1CN(C(=O)/C=C/c2nc(C3COC3)no2)C1)c1nc(OC[C@@]23CCCN2C[C@H](F)C3)nc2c(F)c(-c3cccc4cccc(Cl)c34)ncc12] (formate salt) | ++++ |
| 153 | 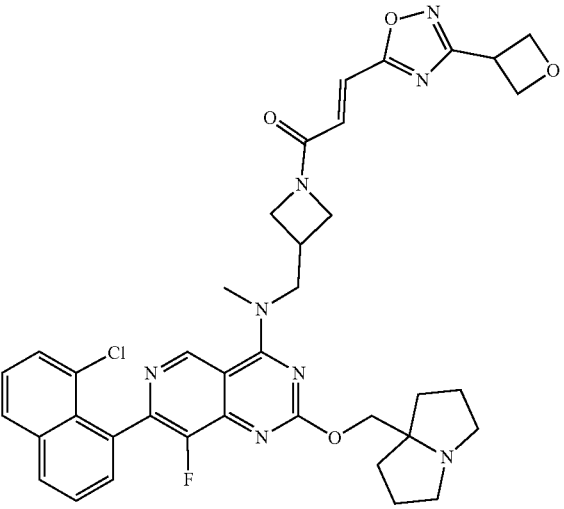 [SMILES: CN(CC1CN(C(=O)/C=C/c2nc(C3COC3)no2)C1)c1nc(OCC23CCCN2CCC3)nc2c(F)c(-c3cccc4cccc(Cl)c34)ncc12] | +++ |
| 154 | 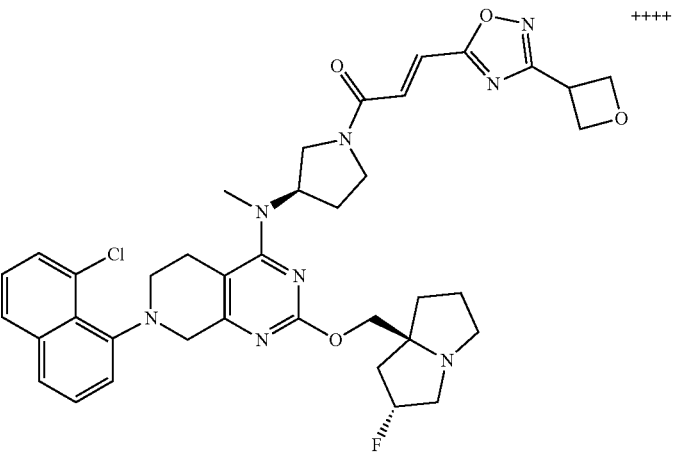 | ++++ |

TABLE 1-continued
Inhibition of KRAS G12C and cRAF Binding (IC$_{50}$)
| Synthetic Example | Structure | IC$_{50}$ |
|---|---|---|
| 155 | 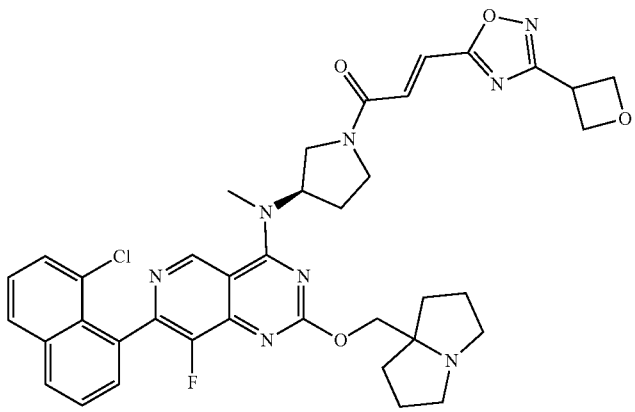 [SMILES: CN(c1nc(OCC23CCCN2CCC3)nc2c(F)c(-c3cccc4cccc(Cl)c34)ncc12)[C@@H]1CCN(C(=O)/C=C/c2nc(C3COC3)no2)C1] | ++++ |
| 156 | 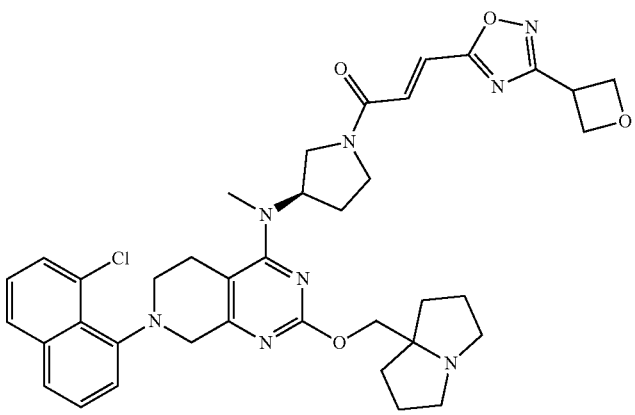 [SMILES: CN(c1nc(OCC23CCCN2CCC3)nc2c1CCN(c1cccc3cccc(Cl)c13)C2)[C@@H]1CCN(C(=O)/C=C/c2nc(C3COC3)no2)C1] | +++ |
| 157 | 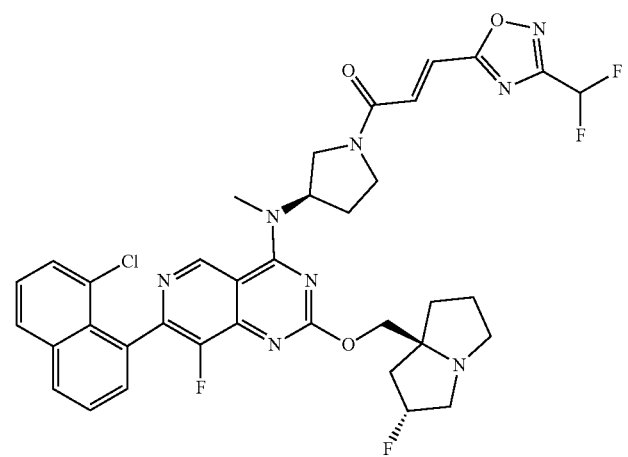 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2nc(C(F)F)no2)C1] | ++++ |

TABLE 1-continued
Inhibition of KRAS G12C and cRAF Binding (IC$_{50}$)
| Synthetic Example | Structure | IC$_{50}$ |
|---|---|---|
| 158 | 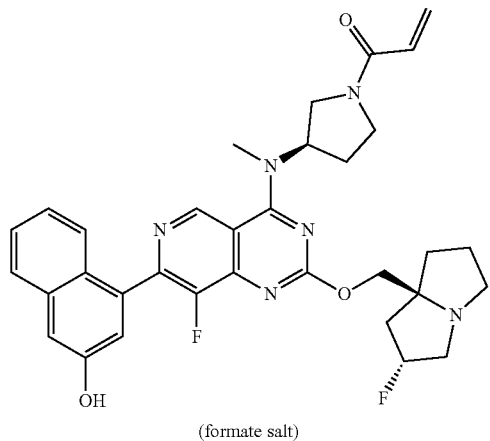 [SMILES: C=CC(=O)N1CC[C@@H](N(C)c2nc(OC[C@@]34CCCN3C[C@H](F)C4)nc3c(F)c(-c4cc(O)cc5ccccc45)ncc23)C1] (formate salt) | ++++ |
| 159 | 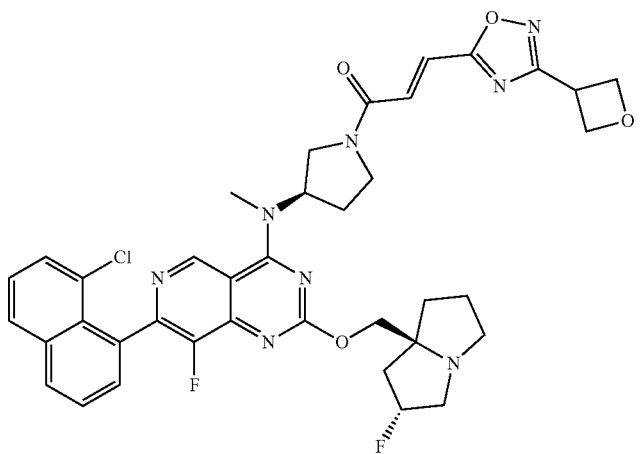 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2nc(C3COC3)no2)C1] | ++++ |
| 160 | 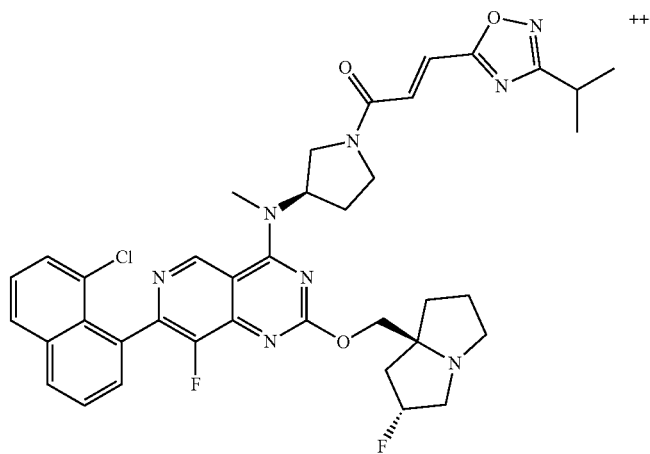 | ++++ |

TABLE 1-continued

Inhibition of KRAS G12C and cRAF Binding (IC$_{50}$)

| Synthetic Example | Structure | IC$_{50}$ |
|---|---|---|
| 161 | 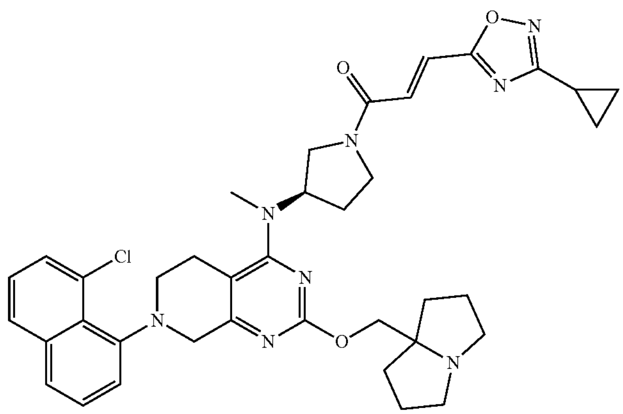 [SMILES: CN(c1nc(OCC23CCCN2CCC3)nc2c1CCN(c1cccc3cccc(Cl)c13)C2)[C@@H]1CCN(C(=O)/C=C/c2nc(C3CC3)no2)C1] | +++ |
| 162 | 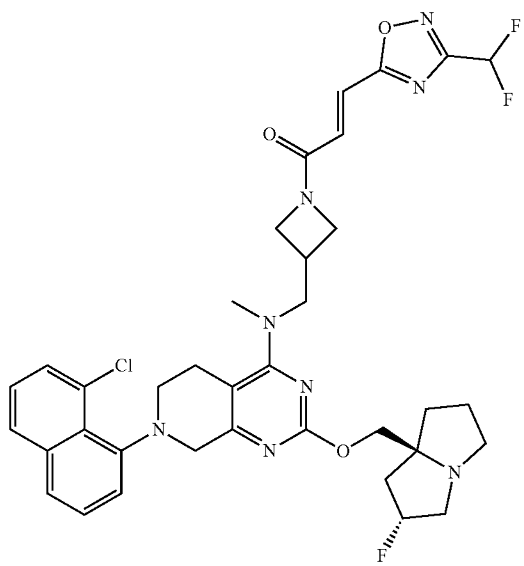 [SMILES: CN(CC1CN(C(=O)/C=C/c2nc(C(F)F)no2)C1)c1nc(OC[C@@]23CCCN2C[C@H](F)C3)nc2c1CCN(c1cccc3cccc(Cl)c13)C2] | ++++ |
| 163 | (formate salt) | ++++ |

TABLE 1-continued
Inhibition of KRAS G12C and cRAF Binding (IC$_{50}$)
| Synthetic Example | Structure | IC$_{50}$ |
|---|---|---|
| 164 | 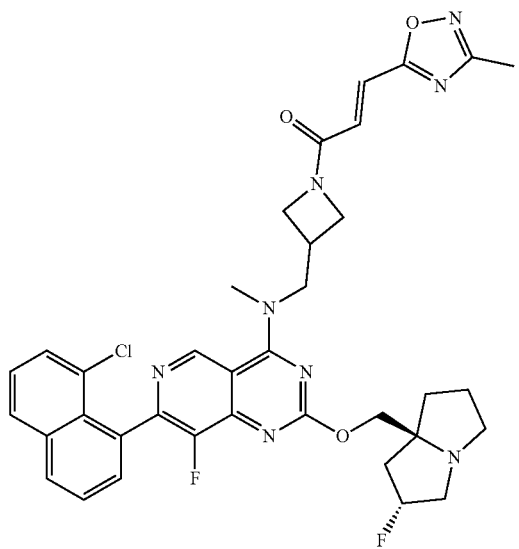<br>(formate salt) | +++ |
| 165 | 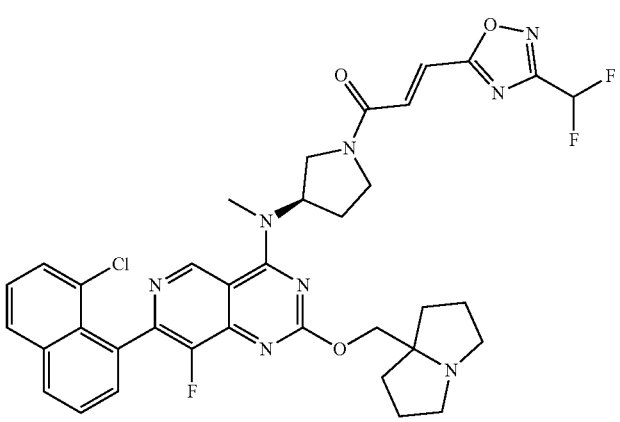 [SMILES: CN(c1nc(OCC23CCCN2CCC3)nc2c(F)c(-c3cccc4cccc(Cl)c34)ncc12)[C@@H]1CCN(C(=O)/C=C/c2nc(C(F)F)no2)C1] | ++++ |
| 166 | 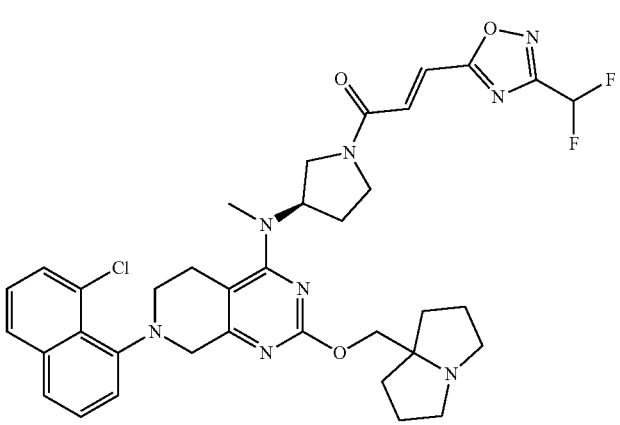 [SMILES: CN(c1nc(OCC23CCCN2CCC3)nc2c1CCN(c1cccc3cccc(Cl)c13)C2)[C@@H]1CCN(C(=O)/C=C/c2nc(C(F)F)no2)C1] | +++ |

TABLE 1-continued

Inhibition of KRAS G12C and cRAF Binding (IC$_{50}$)

| Synthetic Example | Structure | IC$_{50}$ |
|---|---|---|
| 167 | 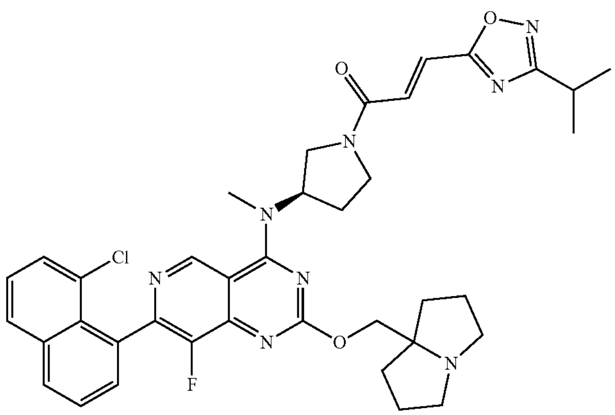 [SMILES: CC(C)c1noc(/C=C/C(=O)N2CC[C@@H](N(C)c3nc(OCC45CCCN4CCC5)nc4c(F)c(-c5cccc6cccc(Cl)c56)ncc34)C2)n1] | ++++ |
| 168 | 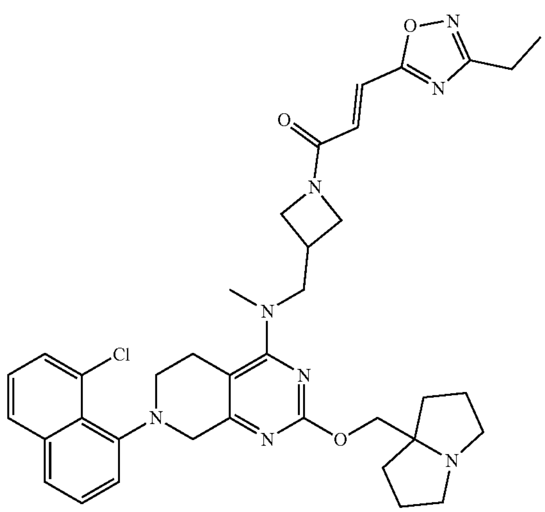 [SMILES: CCc1noc(/C=C/C(=O)N2CC(CN(C)c3nc(OCC45CCCN4CCC5)nc4c3CCN(c3cccc5cccc(Cl)c35)C4)C2)n1] | +++ |
| 169 | 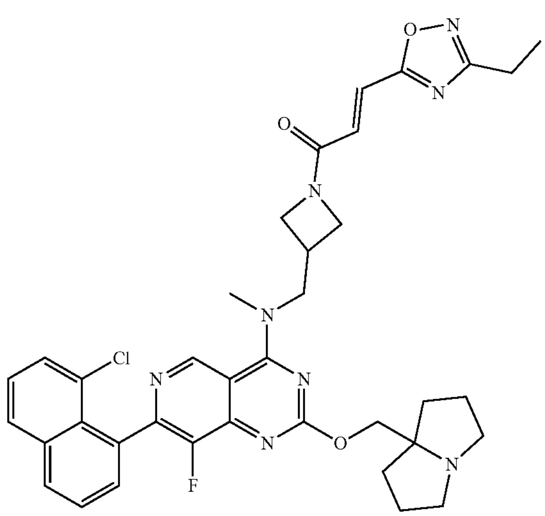 [SMILES: CCc1noc(/C=C/C(=O)N2CC(CN(C)c3nc(OCC45CCCN4CCC5)nc4c(F)c(-c5cccc6cccc(Cl)c56)ncc34)C2)n1] | +++ |

TABLE 1-continued
Inhibition of KRAS G12C and cRAF Binding (IC$_{50}$)
| Synthetic Example | Structure | IC$_{50}$ |
|---|---|---|
| 170 | 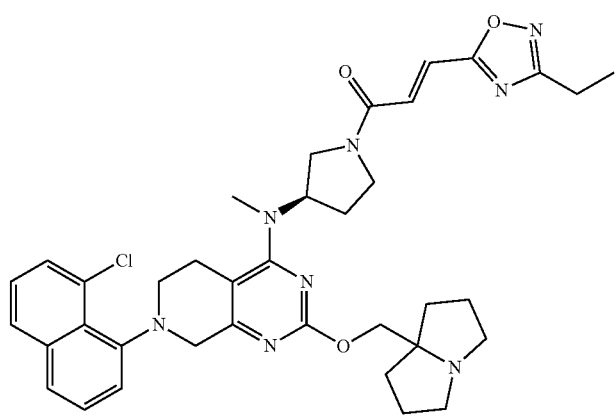 [SMILES: CCc1noc(/C=C/C(=O)N2CC[C@@H](N(C)c3nc(OCC45CCCN4CCC5)nc4c3CCN(c3cccc5cccc(Cl)c35)C4)C2)n1] | +++ |
| 171 | 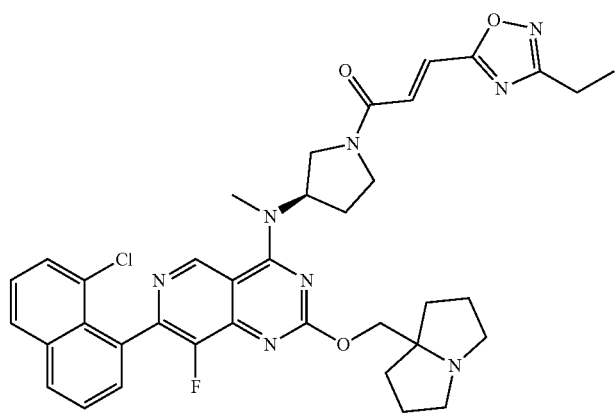 [SMILES: CCc1noc(/C=C/C(=O)N2CC[C@@H](N(C)c3nc(OCC45CCCN4CCC5)nc4c(F)c(-c5cccc6cccc(Cl)c56)ncc34)C2)n1] | +++ |
| 172 | 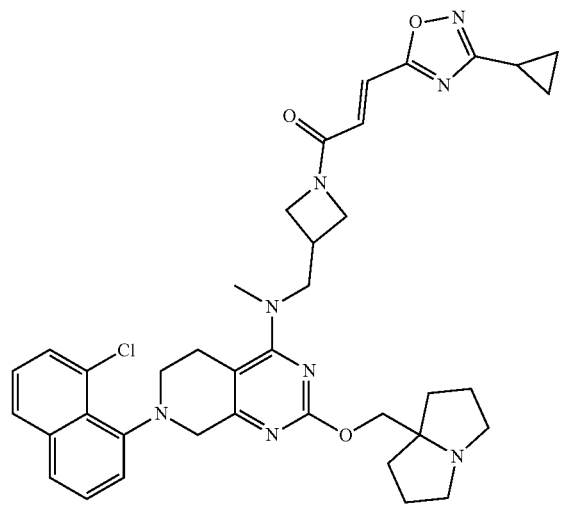 [SMILES: CN(CC1CN(C(=O)/C=C/c2nc(C3CC3)no2)C1)c1nc(OCC23CCCN2CCC3)nc2c1CCN(c1cccc3cccc(Cl)c13)C2] | +++ |

TABLE 1-continued

Inhibition of KRAS G12C and cRAF Binding (IC$_{50}$)

| Synthetic Example | Structure | IC$_{50}$ |
|---|---|---|
| 173 | 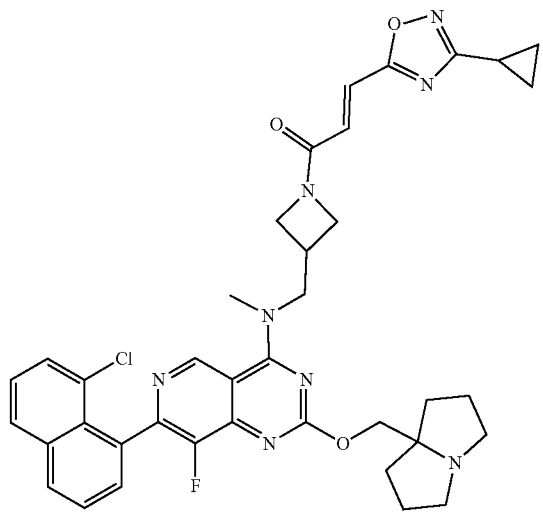 [SMILES: CN(CC1CN(C(=O)/C=C/c2nc(C3CC3)no2)C1)c1nc(OCC23CCCN2CCC3)nc2c(F)c(-c3cccc4cccc(Cl)c34)ncc12] | +++ |
| 174 | 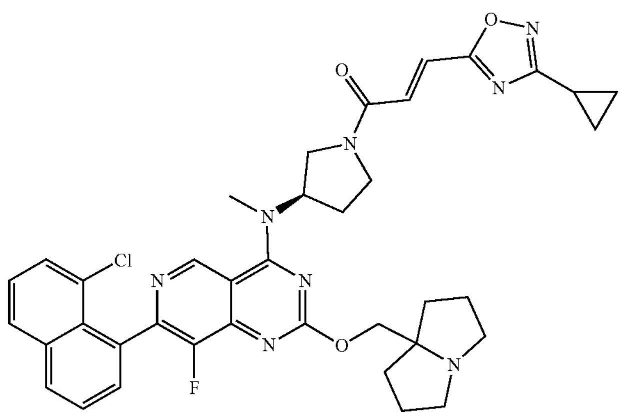 [SMILES: CN(c1nc(OCC23CCCN2CCC3)nc2c(F)c(-c3cccc4cccc(Cl)c34)ncc12)[C@@H]1CCN(C(=O)/C=C/c2nc(C3CC3)no2)C1] | ++++ |
| 175 | 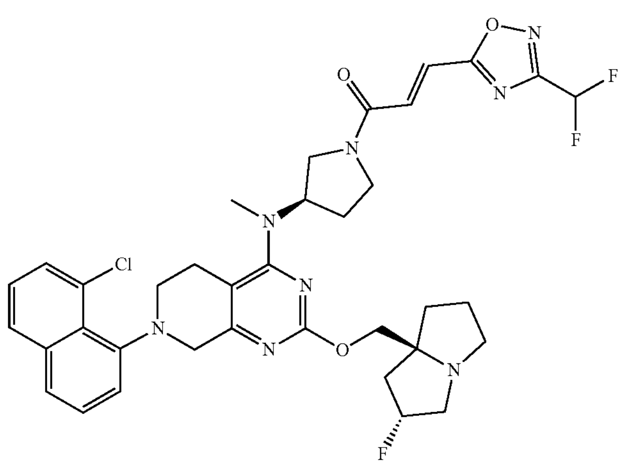 [SMILES: CN(c1nc(OC[C@@]23CCCN2C[C@H](F)C3)nc2c1CCN(c1cccc3cccc(Cl)c13)C2)[C@@H]1CCN(C(=O)/C=C/c2nc(C(F)F)no2)C1] | ++++ |

TABLE 1-continued

Inhibition of KRAS G12C and cRAF Binding (IC$_{50}$)

| Synthetic Example | Structure | IC$_{50}$ |
|---|---|---|
| 176 | 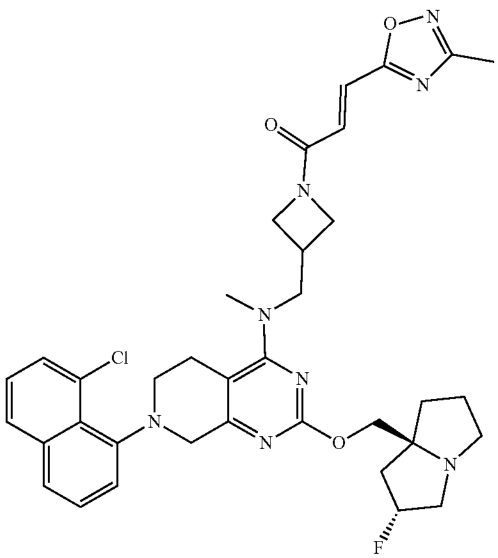 [SMILES: Cc1noc(/C=C/C(=O)N2CC(CN(C)c3nc(OC[C@@]45CCCN4C[C@H](F)C5)nc4c3CCN(c3cccc5cccc(Cl)c35)C4)C2)n1] | ++++ |
| 177 | 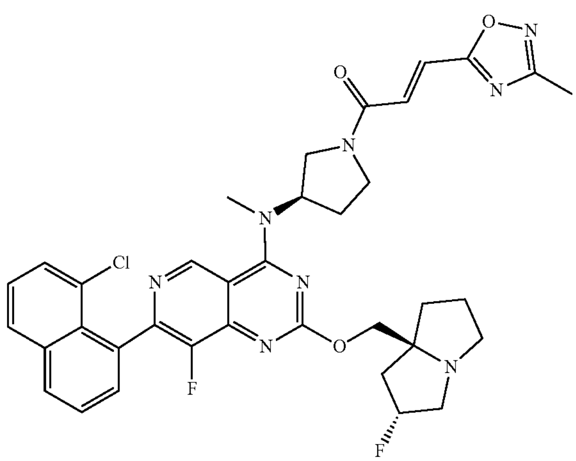 [SMILES: Cc1noc(/C=C/C(=O)N2CC[C@@H](N(C)c3nc(OC[C@@]45CCCN4C[C@H](F)C5)nc4c(F)c(-c5cccc6cccc(Cl)c56)ncc34)C2)n1] | +++ |
| 178 | 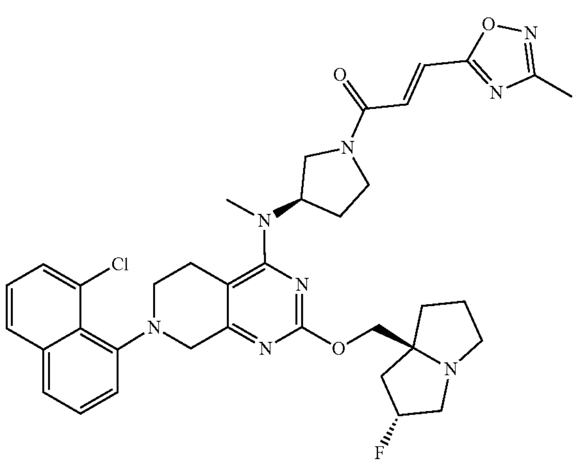 [SMILES: Cc1noc(/C=C/C(=O)N2CC[C@@H](N(C)c3nc(OC[C@@]45CCCN4C[C@H](F)C5)nc4c3CCN(c3cccc5cccc(Cl)c35)C4)C2)n1] | ++++ |

TABLE 1-continued

Inhibition of KRAS G12C and cRAF Binding (IC$_{50}$)

| Synthetic Example | Structure | IC$_{50}$ |
|---|---|---|
| 179 | 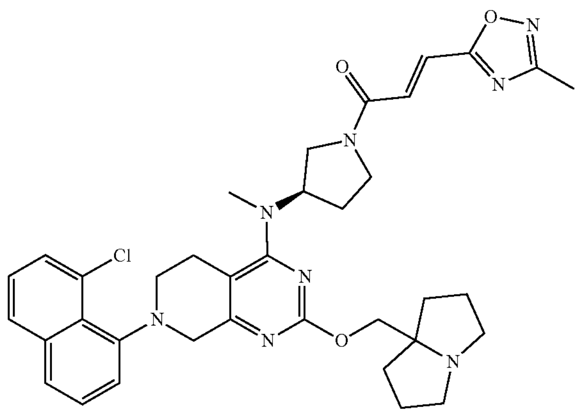 [SMILES: Cc1noc(/C=C/C(=O)N2CC[C@@H](N(C)c3nc(OCC45CCCN4CCC5)nc4c3CCN(c3cccc5cccc(Cl)c35)C4)C2)n1] | +++ |
| 180 | 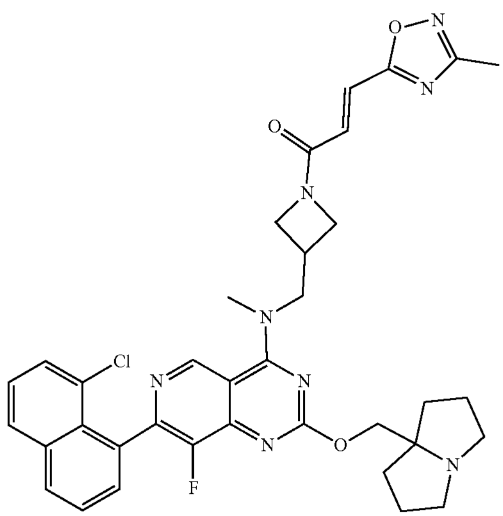 [SMILES: Cc1noc(/C=C/C(=O)N2CC(CN(C)c3nc(OCC45CCCN4CCC5)nc4c(F)c(-c5cccc6cccc(Cl)c56)ncc34)C2)n1] | +++ |
| 181 | 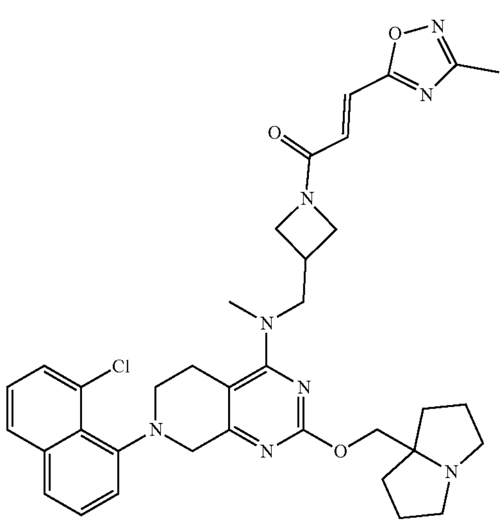 [SMILES: Cc1noc(/C=C/C(=O)N2CC(CN(C)c3nc(OCC45CCCN4CCC5)nc4c3CCN(c3cccc5cccc(Cl)c35)C4)C2)n1] | +++ |

TABLE 1-continued
Inhibition of KRAS G12C and cRAF Binding (IC$_{50}$)
| Synthetic Example | Structure | IC$_{50}$ |
|---|---|---|
| 182 | 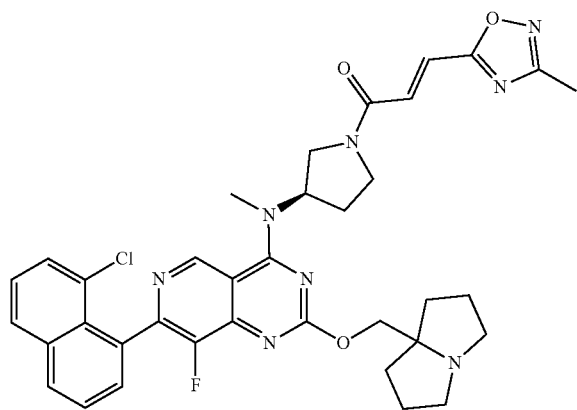 [SMILES: Cc1noc(/C=C/C(=O)N2CC[C@@H](N(C)c3nc(OCC45CCCN4CCC5)nc4c(F)c(-c5cccc6cccc(Cl)c56)ncc34)C2)n1] | ++++ |
| 183 | 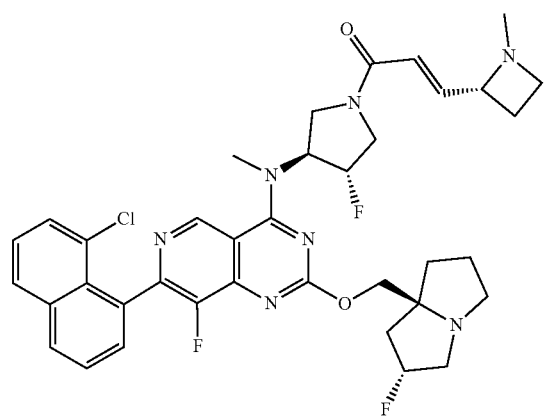 [SMILES: CN1CC[C@@H]1/C=C/C(=O)N1C[C@H](F)[C@@H](N(C)c2nc(OC[C@@]34CCCN3C[C@H](F)C4)nc3c(F)c(-c4cccc5cccc(Cl)c45)ncc23)C1] | ++++ |
| 184 | 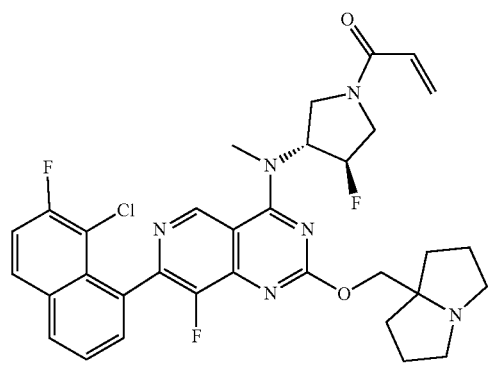 [SMILES: C=CC(=O)N1C[C@@H](F)[C@H](N(C)c2nc(OCC34CCCN3CCC4)nc3c(F)c(-c4cccc5ccc(F)c(Cl)c45)ncc23)C1]<br>Formate salt | +++ |

TABLE 1-continued

Inhibition of KRAS G12C and cRAF Binding (IC$_{50}$)

| Synthetic Example | Structure | IC$_{50}$ |
|---|---|---|
| 185 | 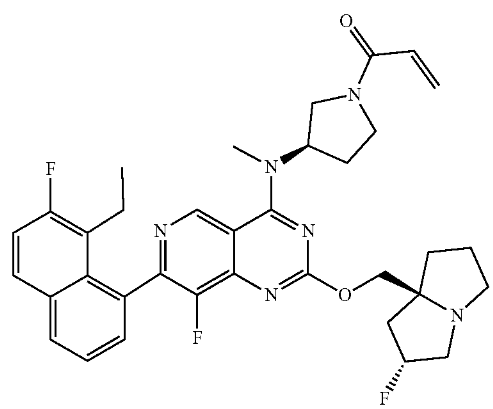 [SMILES: C=CC(=O)N1CC[C@@H](N(C)c2nc(OC[C@@]34CCCN3C[C@H](F)C4)nc3c(F)c(-c4cccc5ccc(F)c(CC)c45)ncc23)C1] | ++ |
| 186 | 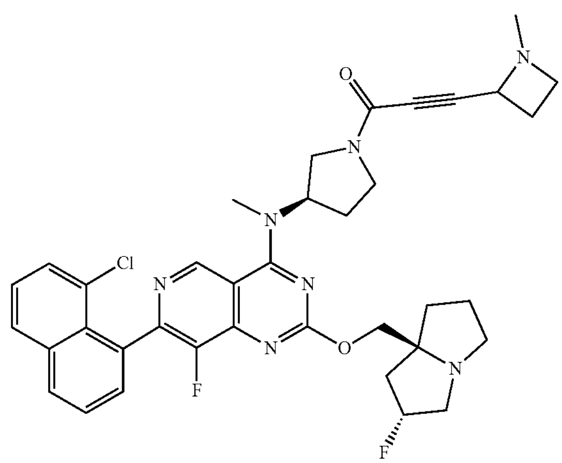 [SMILES: CN1CCC1C#CC(=O)N1CC[C@@H](N(C)c2nc(OC[C@@]34CCCN3C[C@H](F)C4)nc3c(F)c(-c4cccc5cccc(Cl)c45)ncc23)C1] | ++++ |
| 187 | 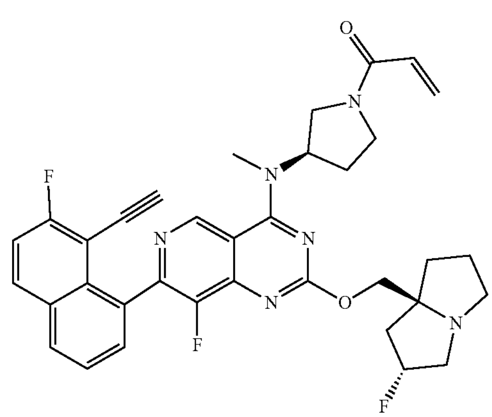 [SMILES: C#Cc1c(F)ccc2cccc(-c3ncc4c(N(C)[C@@H]5CCN(C(=O)C=C)C5)nc(OC[C@@]56CCCN5C[C@H](F)C6)nc4c3F)c12] | ++++ |

TABLE 1-continued

Inhibition of KRAS G12C and cRAF Binding (IC$_{50}$)

| Synthetic Example | Structure | IC$_{50}$ |
|---|---|---|
| 188 | 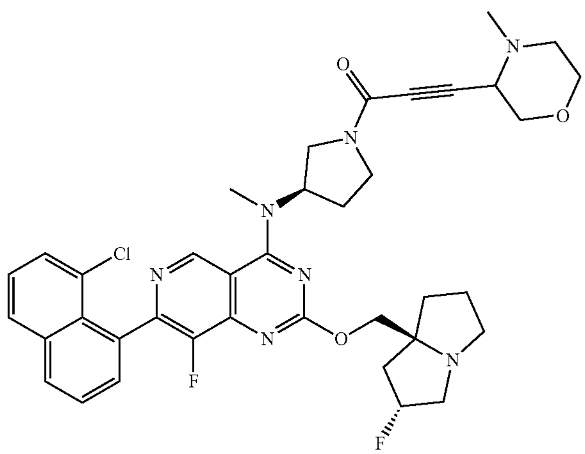 [SMILES: CN1CCOCC1C#CC(=O)N1CC[C@@H](N(C)c2nc(OC[C@@]34CCCN3C[C@H](F)C4)nc3c(F)c(-c4cccc5cccc(Cl)c45)ncc23)C1] | ++ |
| 189 | 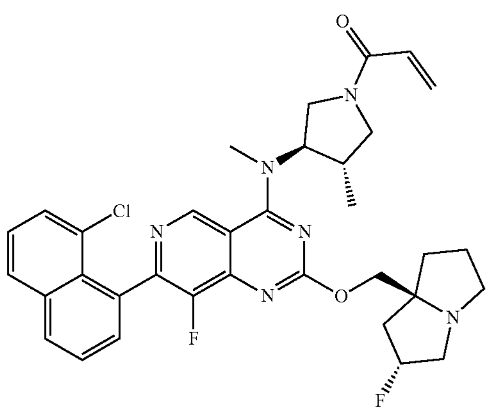 [SMILES: C=CC(=O)N1C[C@H](C)[C@@H](N(C)c2nc(OC[C@@]34CCCN3C[C@H](F)C4)nc3c(F)c(-c4cccc5cccc(Cl)c45)ncc23)C1] | ++ |
| 190 | 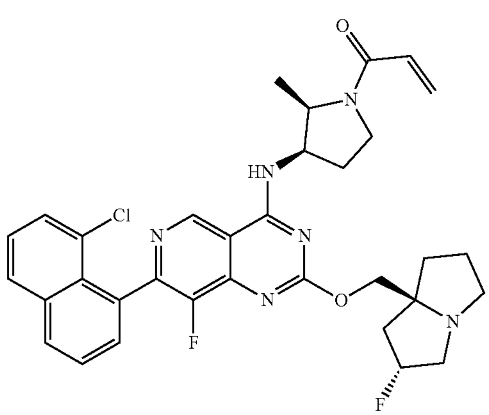 [SMILES: C=CC(=O)N1CC[C@@H](Nc2nc(OC[C@@]34CCCN3C[C@H](F)C4)nc3c(F)c(-c4cccc5cccc(Cl)c45)ncc23)[C@H]1C] | ++ |

TABLE 1-continued

Inhibition of KRAS G12C and cRAF Binding (IC$_{50}$)

| Synthetic Example | Structure | IC$_{50}$ |
|---|---|---|
| 191 | 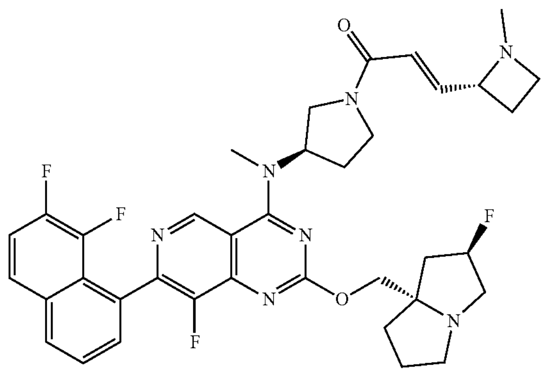 [SMILES: CN1CC[C@@H]1/C=C/C(=O)N1CC[C@@H](N(C)c2nc(OC[C@@]34CCCN3C[C@H](F)C4)nc3c(F)c(-c4cccc5ccc(F)c(F)c45)ncc23)C1] | ++++ |
| 192 | 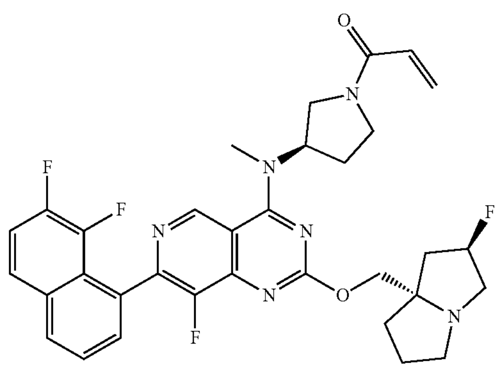 [SMILES: C=CC(=O)N1CC[C@@H](N(C)c2nc(OC[C@@]34CCCN3C[C@H](F)C4)nc3c(F)c(-c4cccc5ccc(F)c(F)c45)ncc23)C1] | +++ |
| 193 | 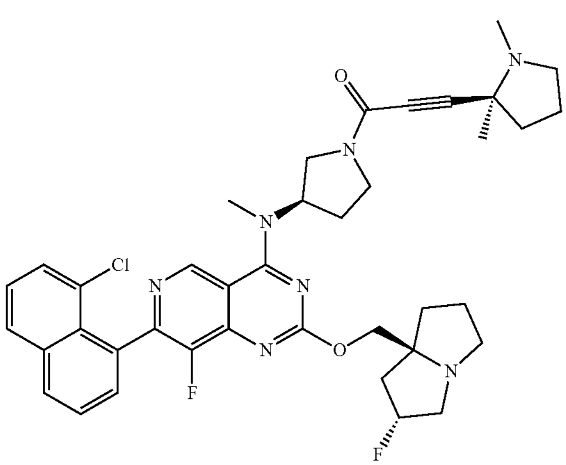 [SMILES: CN(c1nc(OC[C@@]23CCCN2C[C@H](F)C3)nc2c(F)c(-c3cccc4cccc(Cl)c34)ncc12)[C@@H]1CCN(C(=O)C#C[C@]2(C)CCCN2C)C1] | +++ |

TABLE 1-continued

Inhibition of KRAS G12C and cRAF Binding (IC$_{50}$)

| Synthetic Example | Structure | IC$_{50}$ |
|---|---|---|
| 194 | 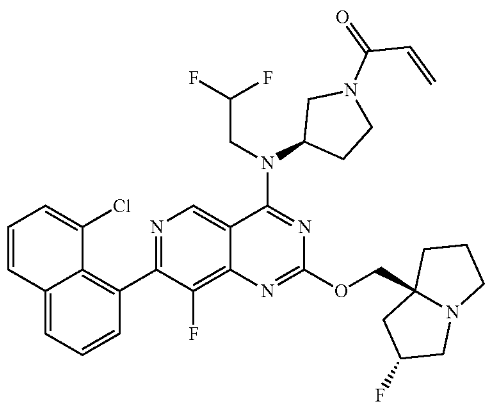 [SMILES: C=CC(=O)N1CC[C@@H](N(CC(F)F)c2nc(OC[C@@]34CCCN3C[C@H](F)C4)nc3c(F)c(-c4cccc5cccc(Cl)c45)ncc23)C1] | +++ |
| 195 | 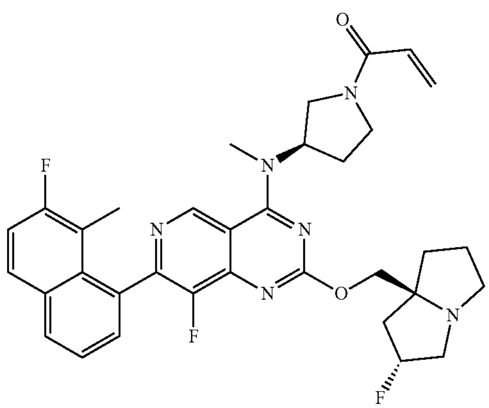 [SMILES: C=CC(=O)N1CC[C@@H](N(C)c2nc(OC[C@@]34CCCN3C[C@H](F)C4)nc3c(F)c(-c4cccc5ccc(F)c(C)c45)ncc23)C1] | +++ |
| 196 | 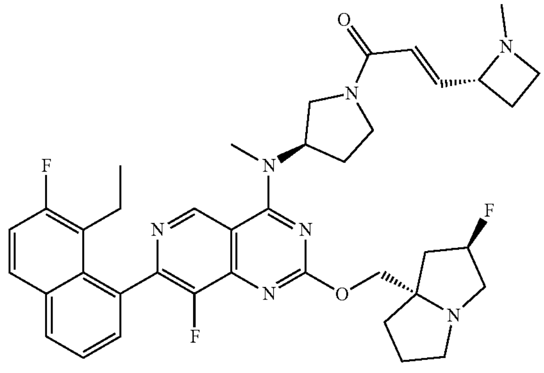 [SMILES: CCc1c(F)ccc2cccc(-c3ncc4c(N(C)[C@@H]5CCN(C(=O)/C=C/[C@H]6CCN6C)C5)nc(OC[C@@]56CCCN5C[C@H](F)C6)nc4c3F)c12] | +++ |

TABLE 1-continued

Inhibition of KRAS G12C and cRAF Binding (IC$_{50}$)

| Synthetic Example | Structure | IC$_{50}$ |
|---|---|---|
| 197 | 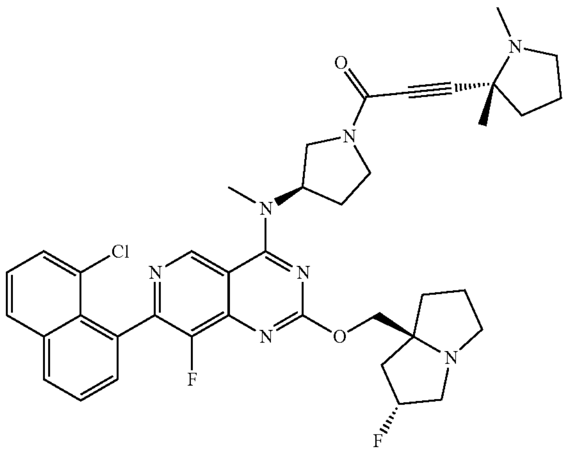 [SMILES: CN(c1nc(OC[C@@]23CCCN2C[C@H](F)C3)nc2c(F)c(-c3cccc4cccc(Cl)c34)ncc12)[C@@H]1CCN(C(=O)C#C[C@@]2(C)CCCN2C)C1] | +++ |
| 198 | 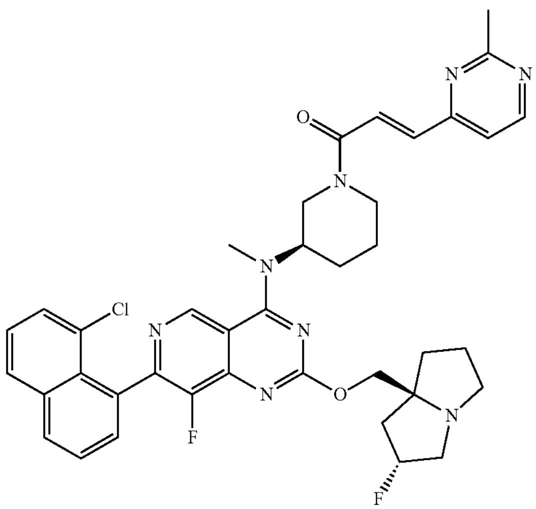 [SMILES: Cc1nccc(/C=C/C(=O)N2CCC[C@@H](N(C)c3nc(OC[C@@]45CCCN4C[C@H](F)C5)nc4c(F)c(-c5cccc6cccc(Cl)c56)ncc34)C2)n1] | + |
| 199 | Formate salt | ++++ |

TABLE 1-continued
Inhibition of KRAS G12C and cRAF Binding (IC$_{50}$)
| Synthetic Example | Structure | IC$_{50}$ |
|---|---|---|
| 200 | 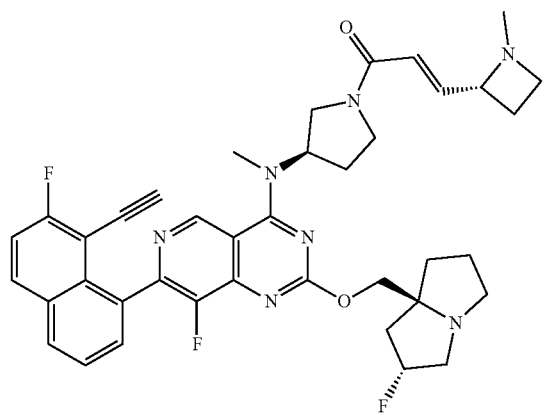 [SMILES: C#Cc1c(F)ccc2cccc(-c3ncc4c(N(C)[C@@H]5CCN(C(=O)/C=C/[C@H]6CCN6C)C5)nc(OC[C@@]56CCCN5C[C@H](F)C6)nc4c3F)c12]\\ Formate salt | ++++ |
| 201 | 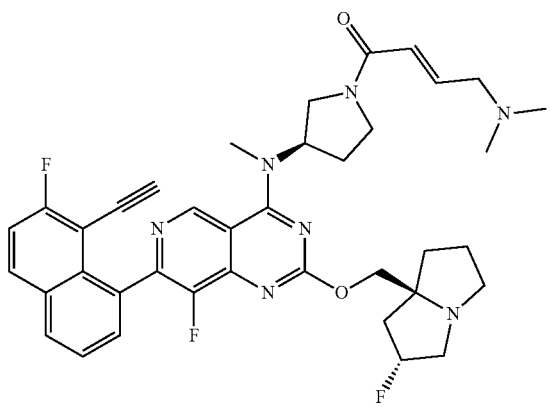 [SMILES: C#Cc1c(F)ccc2cccc(-c3ncc4c(N(C)[C@@H]5CCN(C(=O)/C=C/CN(C)C)C5)nc(OC[C@@]56CCCN5C[C@H](F)C6)nc4c3F)c12]\\ Formate salt | ++++ |
| 202 | 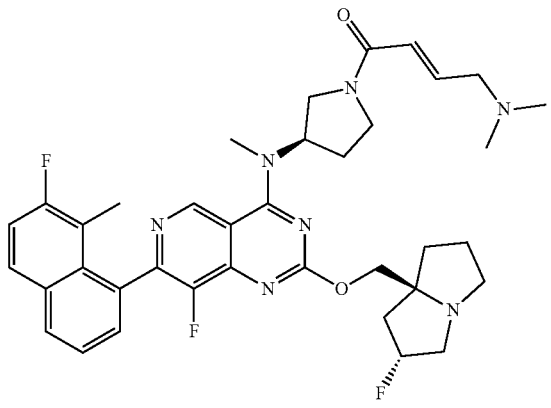 [SMILES: Cc1c(F)ccc2cccc(-c3ncc4c(N(C)[C@@H]5CCN(C(=O)/C=C/CN(C)C)C5)nc(OC[C@@]56CCCN5C[C@H](F)C6)nc4c3F)c12] | +++ |

TABLE 1-continued

Inhibition of KRAS G12C and cRAF Binding (IC$_{50}$)

| Synthetic Example | Structure | IC$_{50}$ |
|---|---|---|
| 203 | 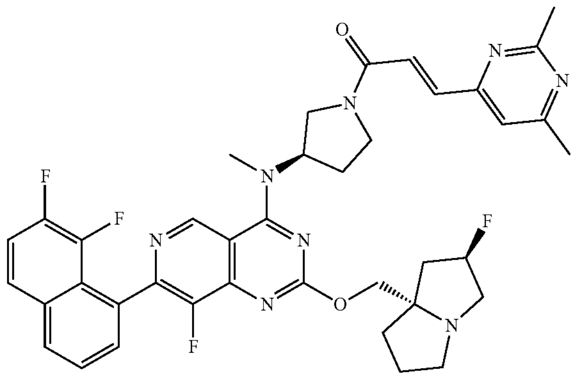 | +++ |
| 204 | 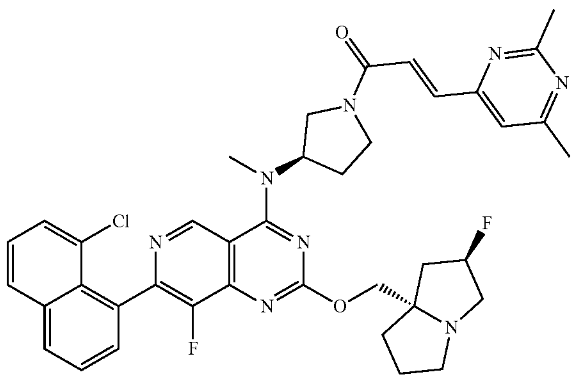 [SMILES: Cc1cc(/C=C/C(=O)N2CC[C@@H](N(C)c3nc(OC[C@@]45CCCN4C[C@H](F)C5)nc4c(F)c(-c5cccc6cccc(Cl)c56)ncc34)C2)nc(C)n1] | ++ |
| 205 | 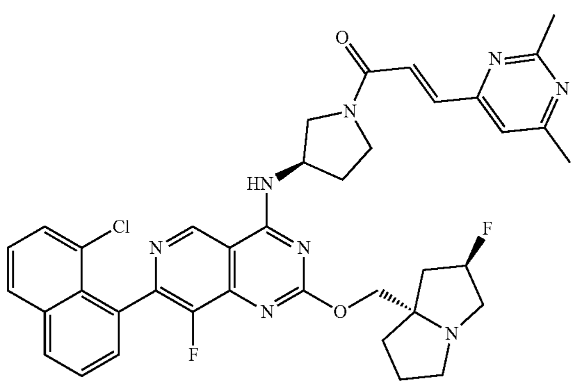 [SMILES: Cc1cc(/C=C/C(=O)N2CC[C@@H](Nc3nc(OC[C@@]45CCCN4C[C@H](F)C5)nc4c(F)c(-c5cccc6cccc(Cl)c56)ncc34)C2)nc(C)n1] | ++ |
| 206 | 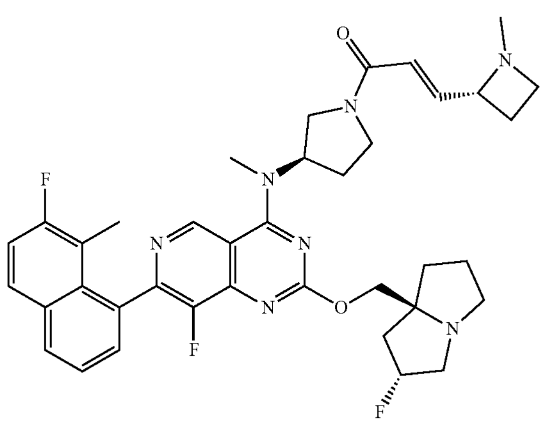 [SMILES: Cc1c(F)ccc2cccc(-c3ncc4c(N(C)[C@@H]5CCN(C(=O)/C=C/[C@H]6CCN6C)C5)nc(OC[C@@]56CCCN5C[C@H](F)C6)nc4c3F)c12] | +++ |

TABLE 1-continued

Inhibition of KRAS G12C and cRAF Binding (IC$_{50}$)

| Synthetic Example | Structure | IC$_{50}$ |
|---|---|---|
| 207 | 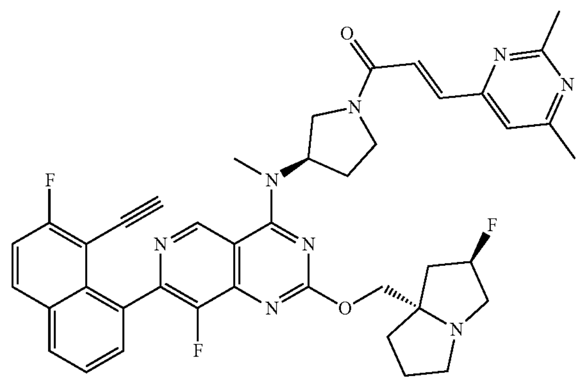 [SMILES: C#Cc1c(F)ccc2cccc(-c3ncc4c(N(C)[C@@H]5CCN(C(=O)/C=C/c6cc(C)nc(C)n6)C5)nc(OC[C@@]56CCCN5C[C@H](F)C6)nc4c3F)c12] | +++ |
| 208 | 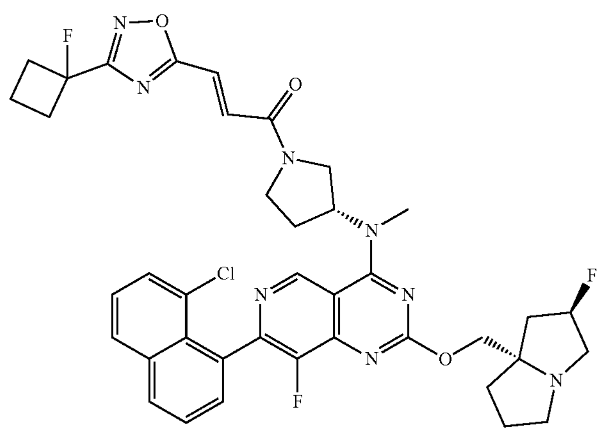 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2nc(C3(F)CCC3)no2)C1] | ++++ |
| 209 | 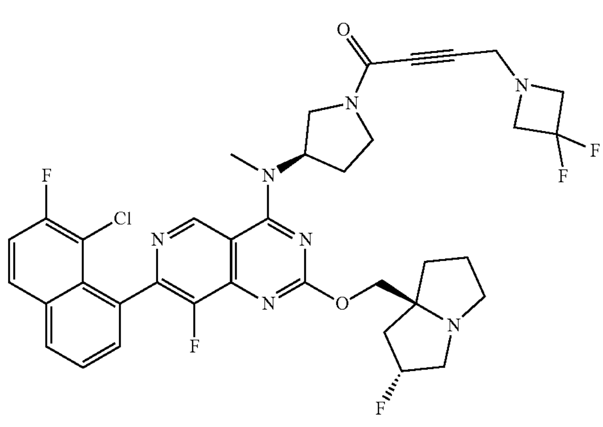 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)C#CCN2CC(F)(F)C2)C1] | +++ |

TABLE 1-continued

Inhibition of KRAS G12C and cRAF Binding (IC$_{50}$)

| Synthetic Example | Structure | IC$_{50}$ |
|---|---|---|
| 210 | 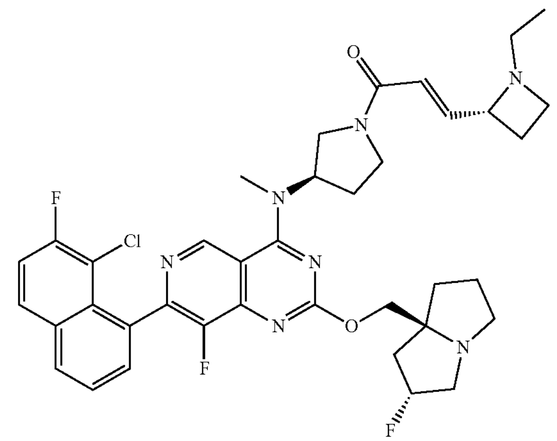 [SMILES: CCN1CC[C@@H]1/C=C/C(=O)N1CC[C@@H](N(C)c2nc(OC[C@@]34CCCN3C[C@H](F)C4)nc3c(F)c(-c4cccc5ccc(F)c(Cl)c45)ncc23)C1] | ++++ |
| 211 | 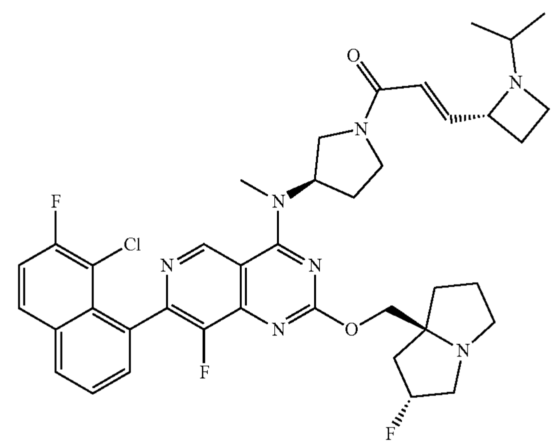 [SMILES: CC(C)N1CC[C@@H]1/C=C/C(=O)N1CC[C@@H](N(C)c2nc(OC[C@@]34CCCN3C[C@H](F)C4)nc3c(F)c(-c4cccc5ccc(F)c(Cl)c45)ncc23)C1] | +++ |
| 212 | 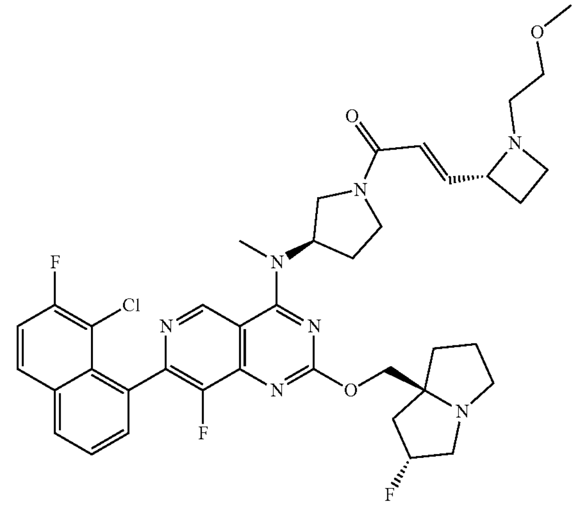 [SMILES: COCCN1CC[C@@H]1/C=C/C(=O)N1CC[C@@H](N(C)c2nc(OC[C@@]34CCCN3C[C@H](F)C4)nc3c(F)c(-c4cccc5ccc(F)c(Cl)c45)ncc23)C1] | +++ |

TABLE 1-continued

Inhibition of KRAS G12C and cRAF Binding (IC$_{50}$)

| Synthetic Example | Structure | IC$_{50}$ |
|---|---|---|
| 213 | 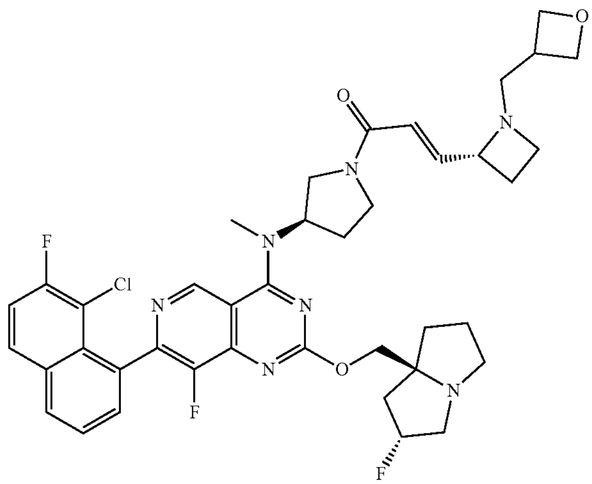 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)/C=C/[C@H]2CCN2CC2COC2)C1] | +++ |
| 214 | 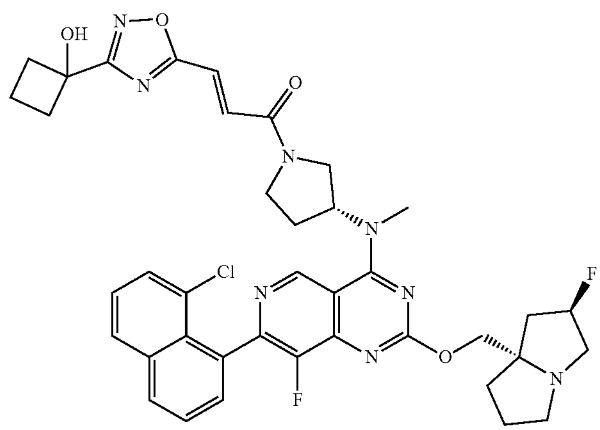 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2nc(C3(O)CCC3)no2)C1] | ++++ |
| 215 | 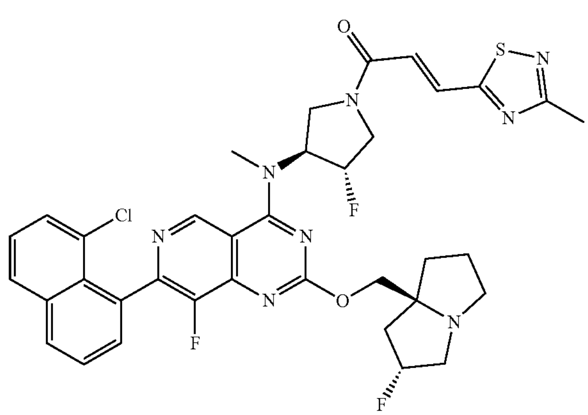 [SMILES: Cc1nsc(/C=C/C(=O)N2C[C@H](F)[C@@H](N(C)c3nc(OC[C@@]45CCCN4C[C@H](F)C5)nc4c(F)c(-c5cccc6cccc(Cl)c56)ncc34)C2)n1] | ++ |

TABLE 1-continued

Inhibition of KRAS G12C and cRAF Binding (IC$_{50}$)

| Synthetic Example | Structure | IC$_{50}$ |
|---|---|---|
| 216 | 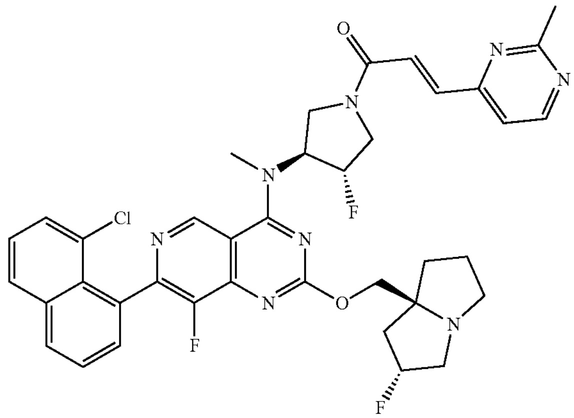 [SMILES: Cc1nccc(/C=C/C(=O)N2C[C@H](F)[C@@H](N(C)c3nc(OC[C@@]45CCCN4C[C@H](F)C5)nc4c(F)c(-c5cccc6cccc(Cl)c56)ncc34)C2)n1] | ++ |
| 217 | 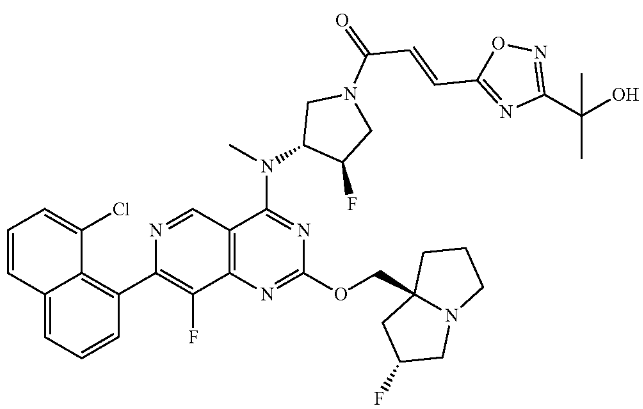 [SMILES: CN(c1nc(OC[C@@]23CCCN2C[C@H](F)C3)nc2c(F)c(-c3cccc4cccc(Cl)c34)ncc12)[C@@H]1CN(C(=O)/C=C/c2nc(C(C)(C)O)no2)C[C@H]1F] | + |
| 218 | formate salt | +++ |

TABLE 1-continued
Inhibition of KRAS G12C and cRAF Binding (IC$_{50}$)
| Synthetic Example | Structure | IC$_{50}$ |
|---|---|---|
| 219 | 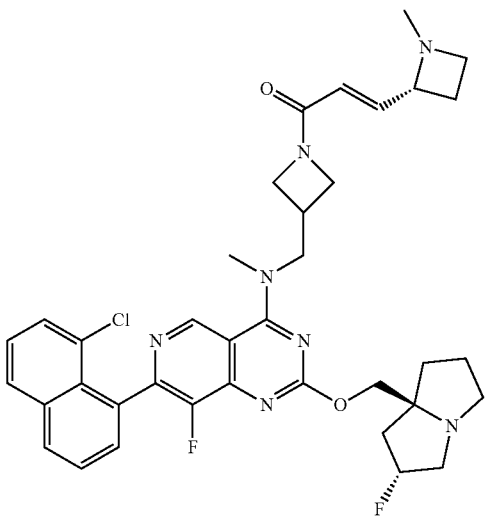 [SMILES: CN(CC1CN(C(=O)/C=C/[C@H]2CCN2C)C1)c1nc(OC[C@@]23CCCN2C[C@H](F)C3)nc2c(F)c(-c3cccc4cccc(Cl)c34)ncc12] | +++ |
| 220 | 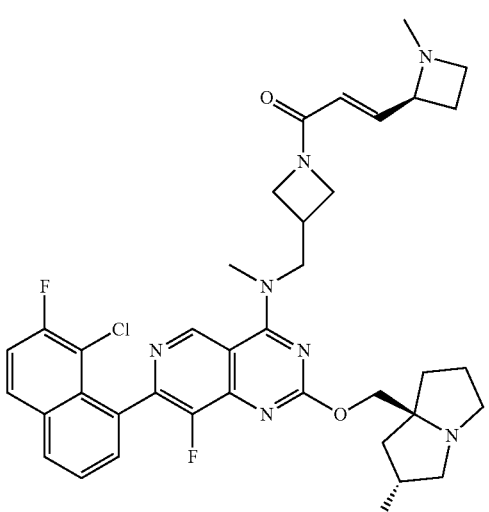 | ++++ |
| 221 | 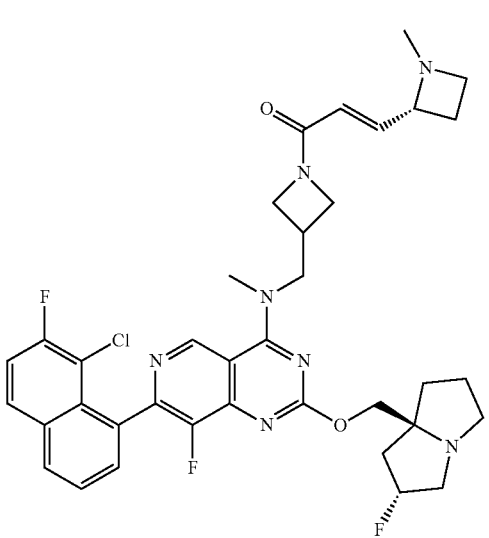 [SMILES: CN(CC1CN(C(=O)/C=C/[C@H]2CCN2C)C1)c1nc(OC[C@@]23CCCN2C[C@H](F)C3)nc2c(F)c(-c3cccc4ccc(F)c(Cl)c34)ncc12] | ++++ |

TABLE 1-continued
Inhibition of KRAS G12C and cRAF Binding (IC$_{50}$)
| Synthetic Example | Structure | IC$_{50}$ |
|---|---|---|
| 222 | 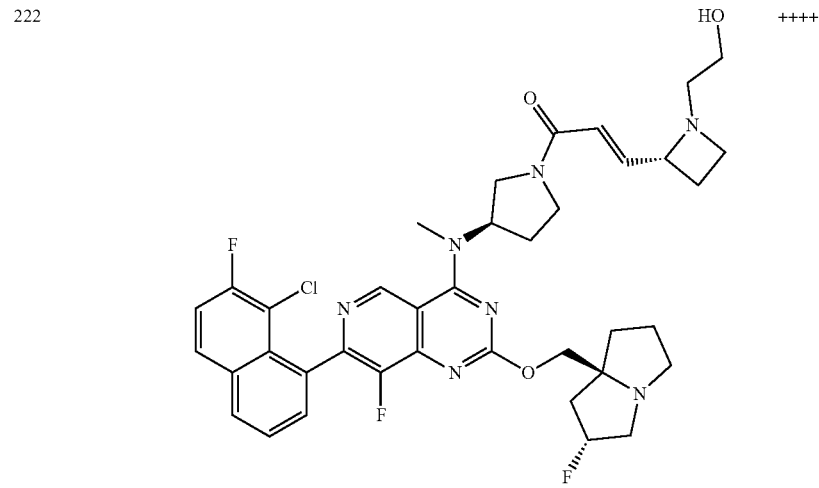<br>Formate salt | ++++ |
| 223 | 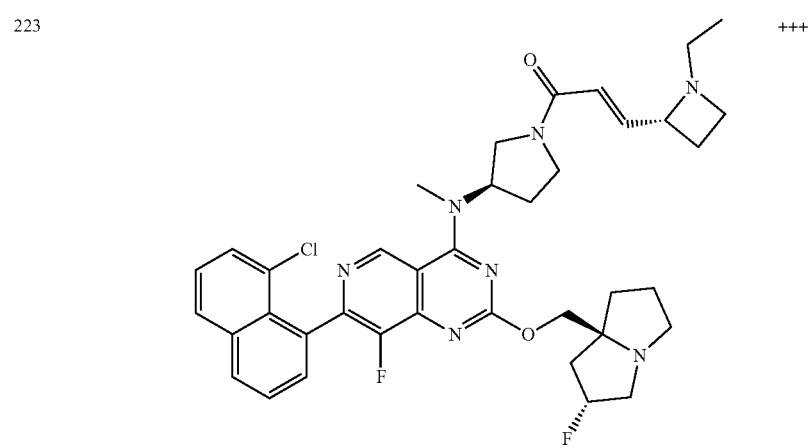 | +++ |
| 224 | 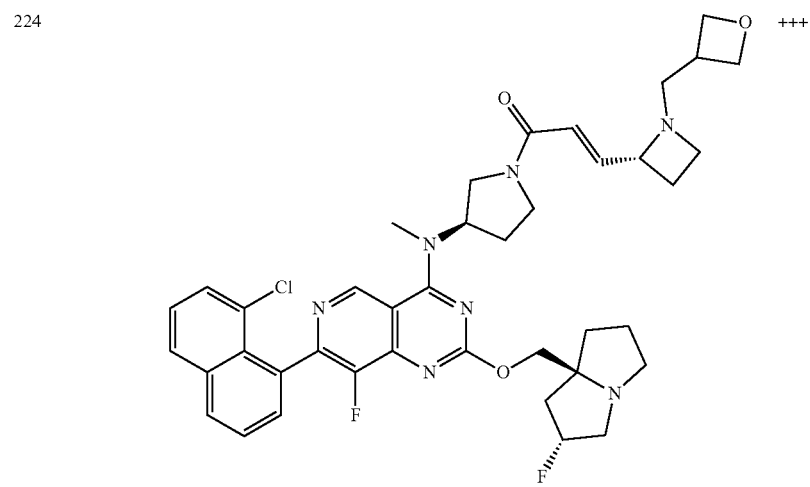 | +++ |

TABLE 1-continued
Inhibition of KRAS G12C and cRAF Binding (IC$_{50}$)
| Synthetic Example | Structure | IC$_{50}$ |
|---|---|---|
| 225 | 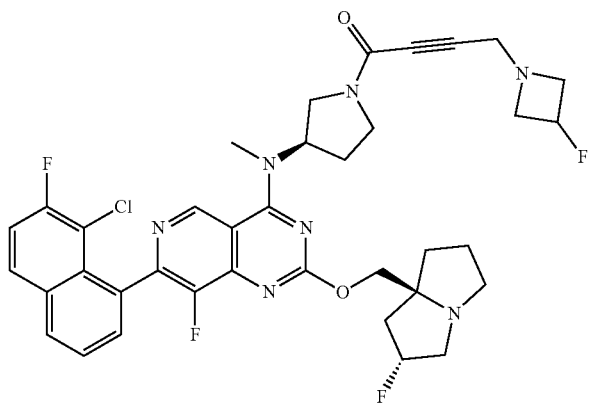 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)C#CCN2CC(F)C2)C1] | +++ |
| 226 | 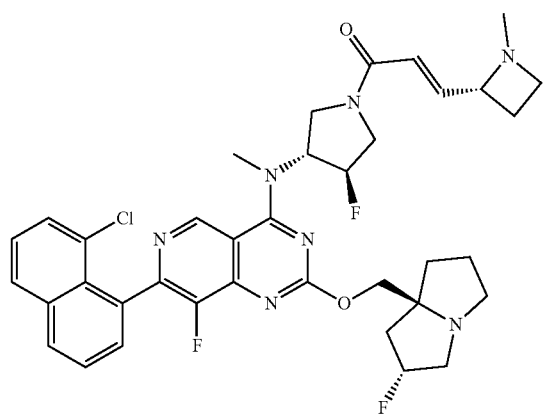 [SMILES: CN1CC[C@@H]1/C=C/C(=O)N1C[C@@H](F)[C@H](N(C)c2nc(OC[C@@]34CCCN3C[C@H](F)C4)nc3c(F)c(-c4cccc5cccc(Cl)c45)ncc23)C1] | ++ |
| 227 | 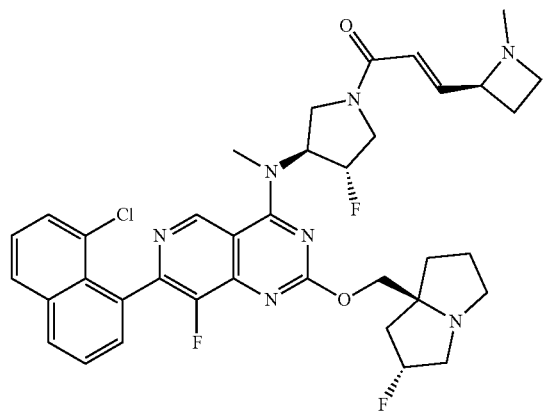 | +++ |

TABLE 1-continued

Inhibition of KRAS G12C and cRAF Binding (IC$_{50}$)

| Synthetic Example | Structure | IC$_{50}$ |
|---|---|---|
| 228 | 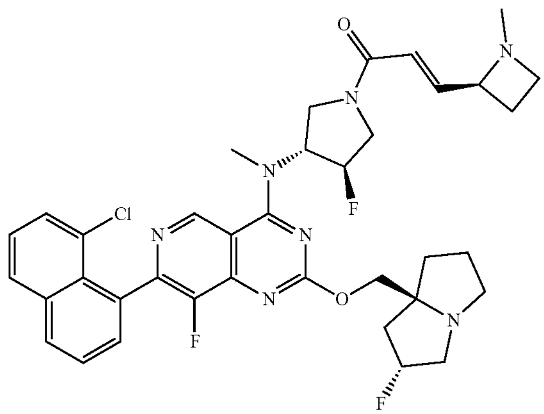 [SMILES: CN1CC[C@H]1/C=C/C(=O)N1C[C@@H](F)[C@H](N(C)c2nc(OC[C@@]34CCCN3C[C@H](F)C4)nc3c(F)c(-c4cccc5cccc(Cl)c45)ncc23)C1] | ++ |
| 229 | 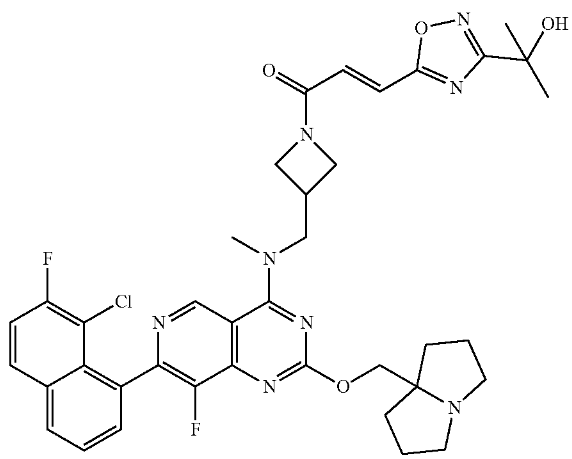 [SMILES: CN(CC1CN(C(=O)/C=C/c2nc(C(C)(C)O)no2)C1)c1nc(OCC23CCCN2CCC3)nc2c(F)c(-c3cccc4ccc(F)c(Cl)c34)ncc12] | ++++ |
|  | trifluoroacetate salt |  |
| 230 | 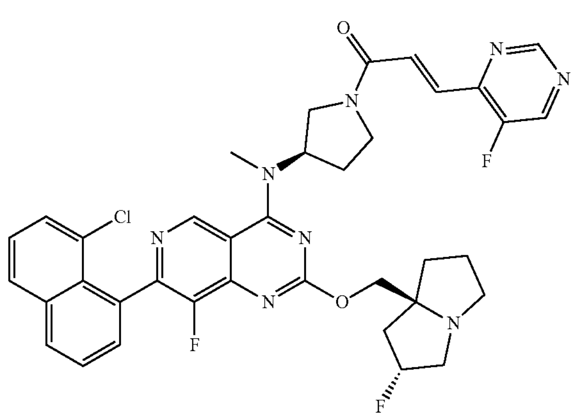 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/c2ncncc2F)C1] | +++ |

TABLE 1-continued
Inhibition of KRAS G12C and cRAF Binding (IC$_{50}$)
| Synthetic Example | Structure | IC$_{50}$ |
|---|---|---|
| 231 | 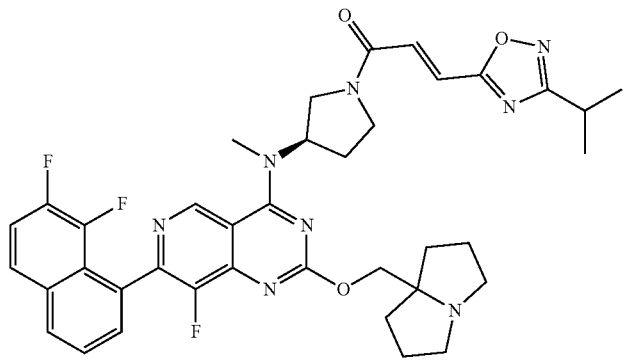 [SMILES: CC(C)c1noc(/C=C/C(=O)N2CC[C@@H](N(C)c3nc(OCC45CCCN4CCC5)nc4c(F)c(-c5cccc6ccc(F)c(F)c56)ncc34)C2)n1] | ++++ |
| 232 | 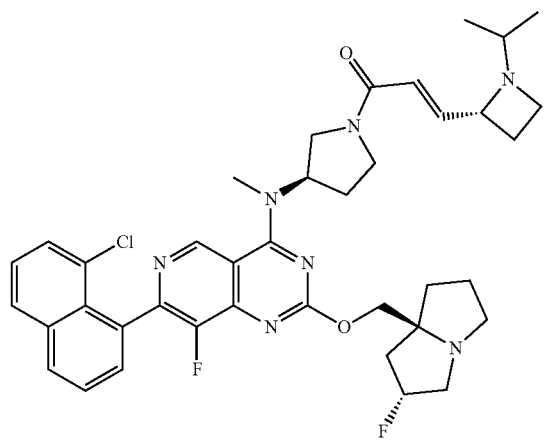 [SMILES: CC(C)N1CC[C@@H]1/C=C/C(=O)N1CC[C@@H](N(C)c2nc(OC[C@@]34CCCN3C[C@H](F)C4)nc3c(F)c(-c4cccc5cccc(Cl)c45)ncc23)C1] | +++ |
| 233 | 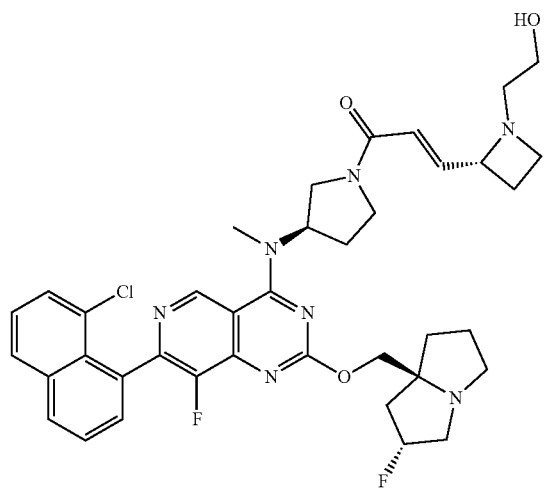 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/[C@H]2CCN2CCO)C1] | +++ |

TABLE 1-continued
Inhibition of KRAS G12C and cRAF Binding (IC$_{50}$)
| Synthetic Example | Structure | IC$_{50}$ |
|---|---|---|
| 234 | 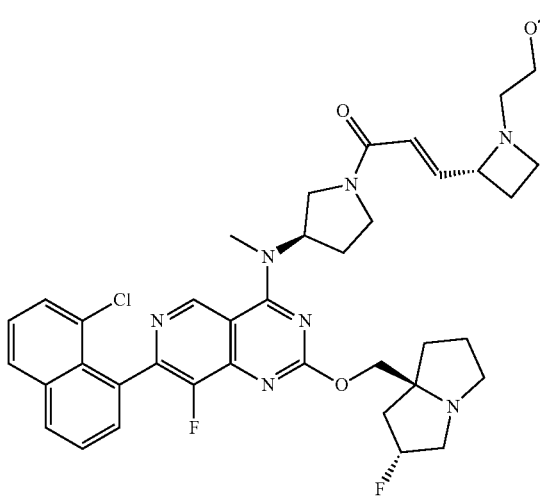 | +++ |
| 235 | 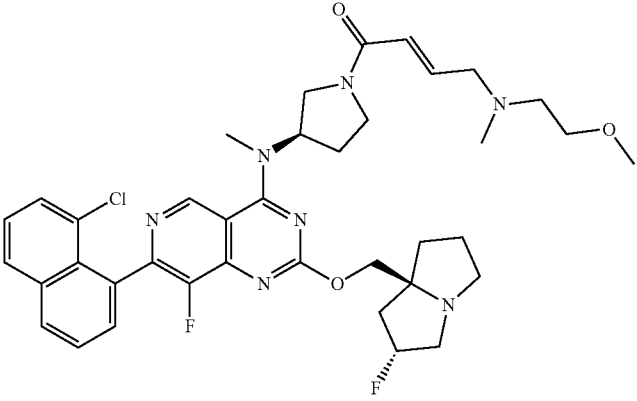 [SMILES: COCCN(C)C/C=C/C(=O)N1CC[C@@H](N(C)c2nc(OC[C@@]34CCCN3C[C@H](F)C4)nc3c(F)c(-c4cccc5cccc(Cl)c45)ncc23)C1] | ++++ |
| 236 | 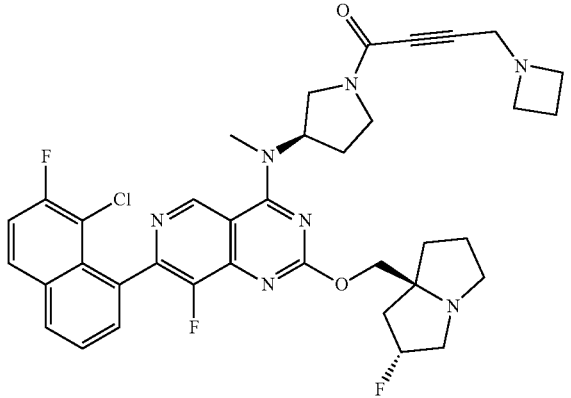 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)C#CCN2CCC2)C1] | ++++ |

TABLE 1-continued
Inhibition of KRAS G12C and cRAF Binding (IC$_{50}$)
| Synthetic Example | Structure | IC$_{50}$ |
|---|---|---|
| 237 | 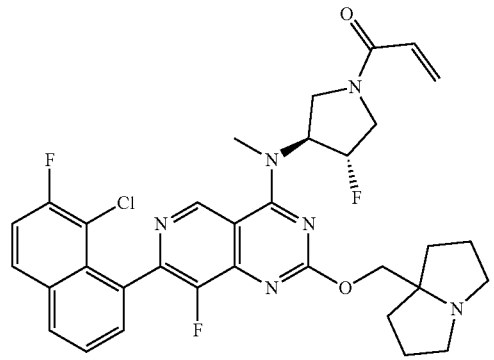 [SMILES: C=CC(=O)N1C[C@H](F)[C@@H](N(C)c2nc(OCC34CCCN3CCC4)nc3c(F)c(-c4cccc5ccc(F)c(Cl)c45)ncc23)C1] | +++ |
| 238 | 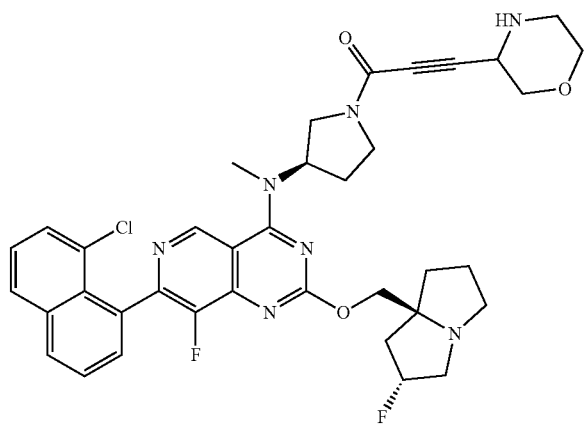  Formate salt | +++ |
| 239 | 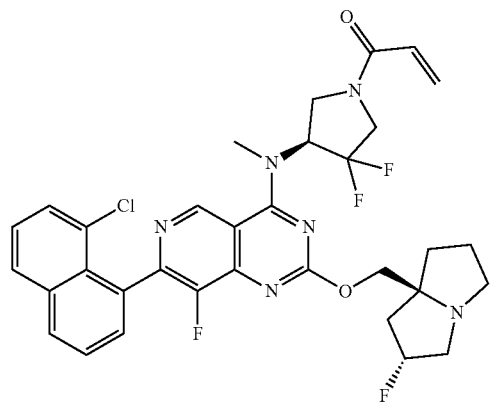 [SMILES: C=CC(=O)N1C[C@H](N(C)c2nc(OC[C@@]34CCCN3C[C@H](F)C4)nc3c(F)c(-c4cccc5cccc(Cl)c45)ncc23)C(F)(F)C1] | +++ |

TABLE 1-continued
Inhibition of KRAS G12C and cRAF Binding (IC$_{50}$)
| Synthetic Example | Structure | IC$_{50}$ |
|---|---|---|
| 240 | 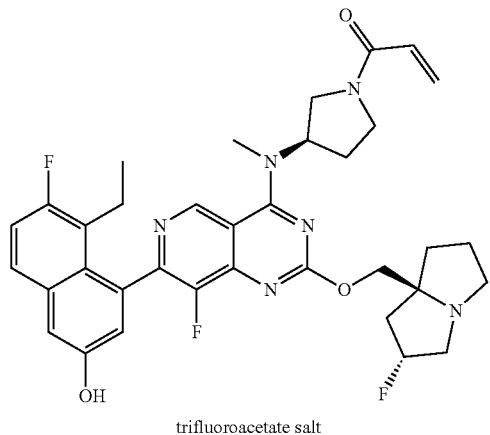 [SMILES: C=CC(=O)N1CC[C@@H](N(C)c2nc(OC[C@@]34CCCN3C[C@H](F)C4)nc3c(F)c(-c4cc(O)cc5ccc(F)c(CC)c45)ncc23)C1] trifluoroacetate salt | ++++ |
| 241 | 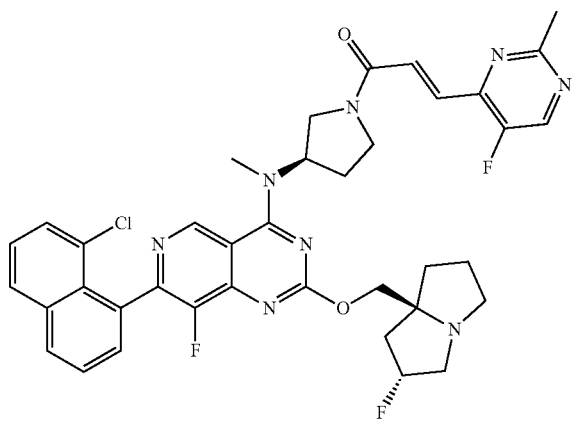 [SMILES: Cc1ncc(F)c(/C=C/C(=O)N2CC[C@@H](N(C)c3nc(OC[C@@]45CCCN4C[C@H](F)C5)nc4c(F)c(-c5cccc6cccc(Cl)c56)ncc34)C2)n1] | ++ |
| 242 | 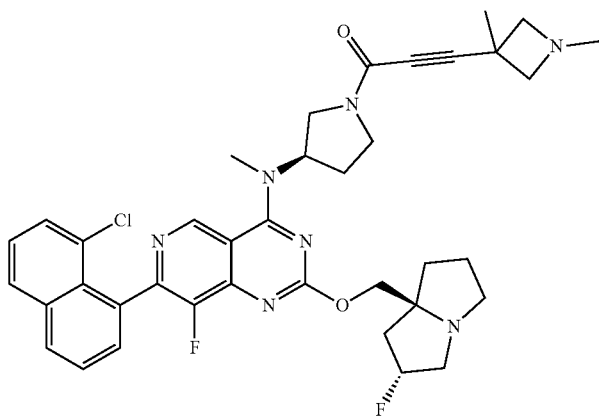 [SMILES: CN1CC(C)(C#CC(=O)N2CC[C@@H](N(C)c3nc(OC[C@@]45CCCN4C[C@H](F)C5)nc4c(F)c(-c5cccc6cccc(Cl)c56)ncc34)C2)C1] | ++++ |

TABLE 1-continued

Inhibition of KRAS G12C and cRAF Binding (IC$_{50}$)

| Synthetic Example | Structure | IC$_{50}$ |
|---|---|---|
| 243 | 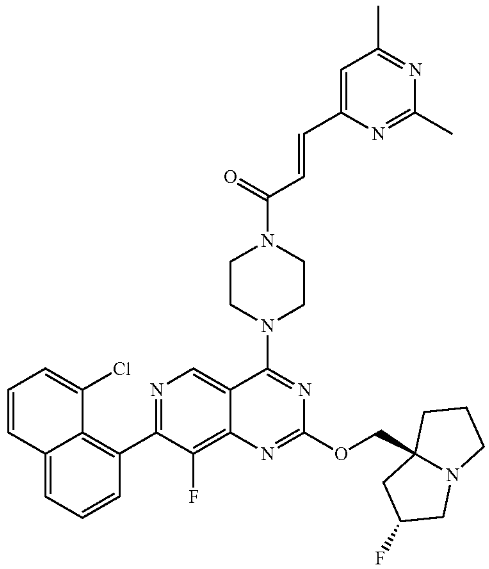 [SMILES: Cc1cc(/C=C/C(=O)N2CCN(c3nc(OC[C@@]45CCCN4C[C@H](F)C5)nc4c(F)c(-c5cccc6cccc(Cl)c56)ncc34)CC2)nc(C)n1] | ++ |
| 244 | 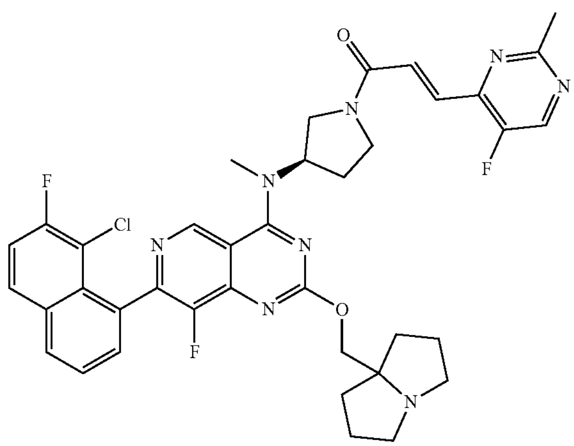 [SMILES: Cc1ncc(F)c(/C=C/C(=O)N2CC[C@@H](N(C)c3nc(OCC45CCCN4CCC5)nc4c(F)c(-c5cccc6ccc(F)c(Cl)c56)ncc34)C2)n1] | ++ |
| 245 | 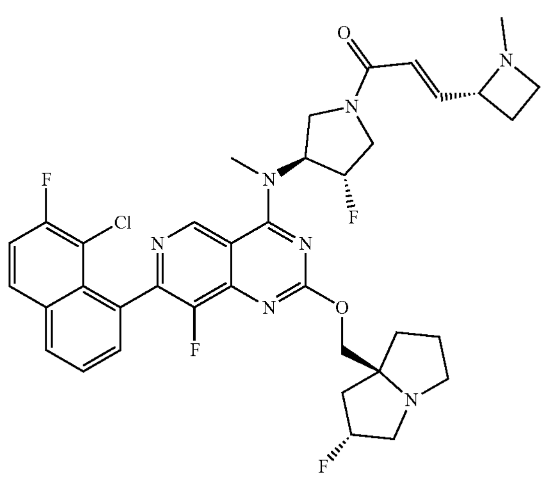 [SMILES: CN1CC[C@@H]1/C=C/C(=O)N1C[C@H](F)[C@@H](N(C)c2nc(OC[C@@]34CCCN3C[C@H](F)C4)nc3c(F)c(-c4cccc5ccc(F)c(Cl)c45)ncc23)C1] | ++++ |

TABLE 1-continued
Inhibition of KRAS G12C and cRAF Binding (IC$_{50}$)
| Synthetic Example | Structure | IC$_{50}$ |
|---|---|---|
| 246 | 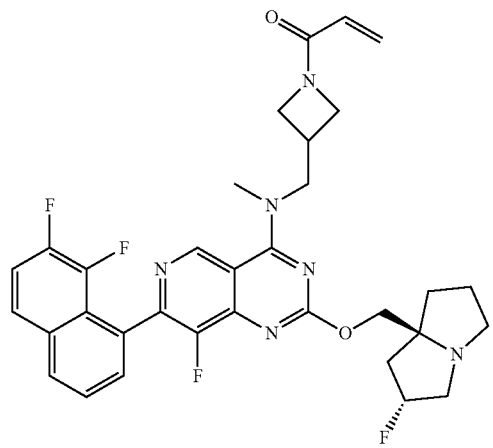 [SMILES: C=CC(=O)N1CC(CN(C)c2nc(OC[C@@]34CCCN3C[C@H](F)C4)nc3c(F)c(-c4cccc5ccc(F)c(F)c45)ncc23)C1] | +++ |
| 247 | 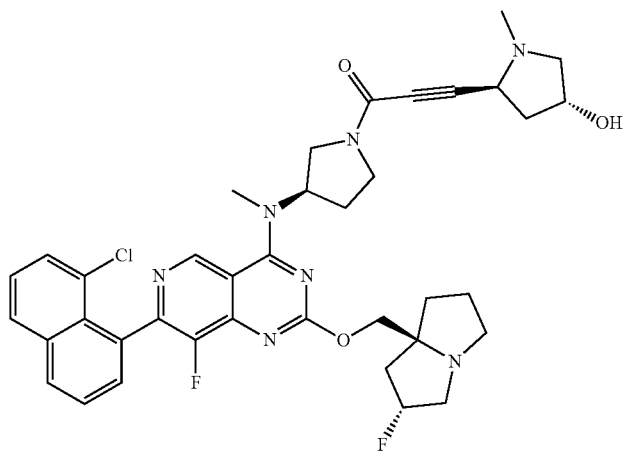 [SMILES: CN1C[C@H](O)C[C@H]1C#CC(=O)N1CC[C@@H](N(C)c2nc(OC[C@@]34CCCN3C[C@H](F)C4)nc3c(F)c(-c4cccc5cccc(Cl)c45)ncc23)C1] | ++++ |
| 248 | 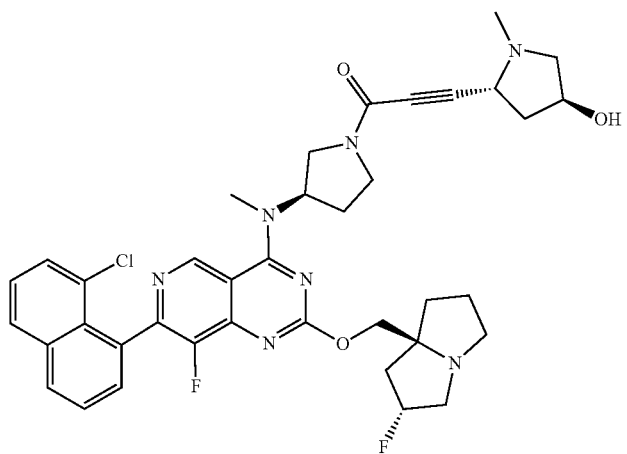 [SMILES: CN1C[C@@H](O)C[C@@H]1C#CC(=O)N1CC[C@@H](N(C)c2nc(OC[C@@]34CCCN3C[C@H](F)C4)nc3c(F)c(-c4cccc5cccc(Cl)c45)ncc23)C1] | +++ |

TABLE 1-continued
Inhibition of KRAS G12C and cRAF Binding (IC$_{50}$)
| Synthetic Example | Structure | IC$_{50}$ |
|---|---|---|
| 249 | 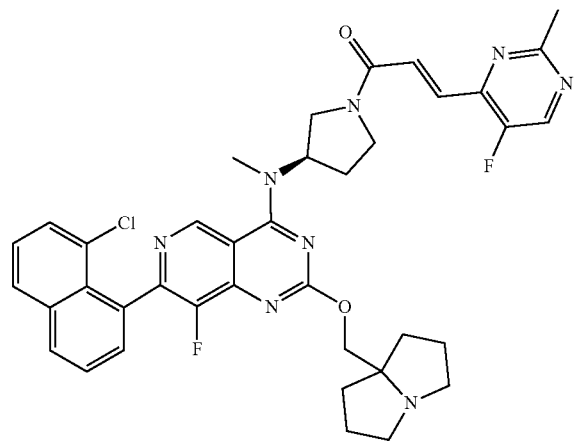 [SMILES: Cc1ncc(F)c(/C=C/C(=O)N2CC[C@@H](N(C)c3nc(OCC45CCCN4CCC5)nc4c(F)c(-c5cccc6cccc(Cl)c56)ncc34)C2)n1] | +++ |
| 250 | 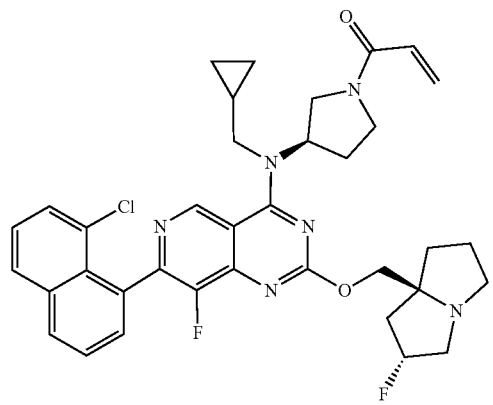 [SMILES: C=CC(=O)N1CC[C@@H](N(CC2CC2)c2nc(OC[C@@]34CCCN3C[C@H](F)C4)nc3c(F)c(-c4cccc5cccc(Cl)c45)ncc23)C1] | ++ |
| 251 | 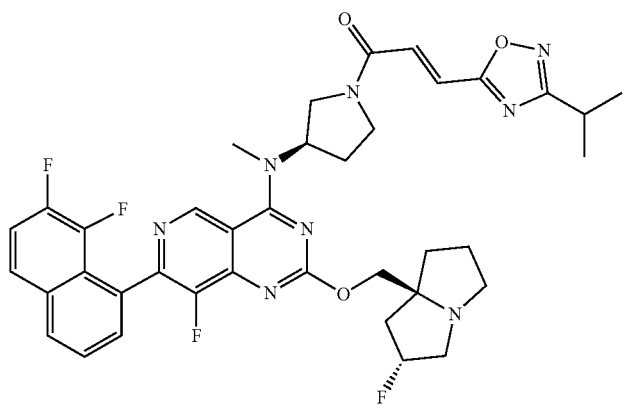 [SMILES: CC(C)c1noc(/C=C/C(=O)N2CC[C@@H](N(C)c3nc(OC[C@@]45CCCN4C[C@H](F)C5)nc4c(F)c(-c5cccc6ccc(F)c(F)c56)ncc34)C2)n1] | ++++ |

TABLE 1-continued
Inhibition of KRAS G12C and cRAF Binding (IC$_{50}$)
| Synthetic Example | Structure | IC$_{50}$ |
|---|---|---|
| 252 | 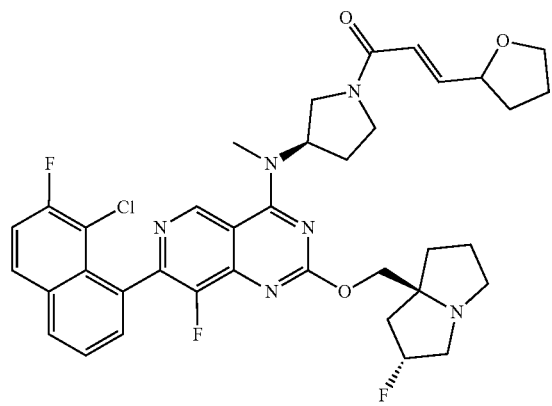 [SMILES: CN(c1nc(OC[C@@]23CCCN2C[C@H](F)C3)nc2c(F)c(-c3cccc4ccc(F)c(Cl)c34)ncc12)[C@@H]1CCN(C(=O)/C=C/C2CCCO2)C1]<br>Formate salt | ++ |
| 253 | 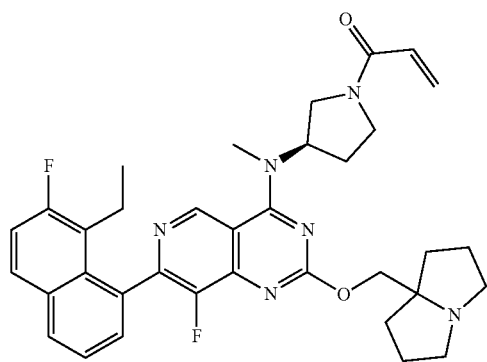 [SMILES: C=CC(=O)N1CC[C@@H](N(C)c2nc(OCC34CCCN3CCC4)nc3c(F)c(-c4cccc5ccc(F)c(CC)c45)ncc23)C1] | ++ |
| 254 | 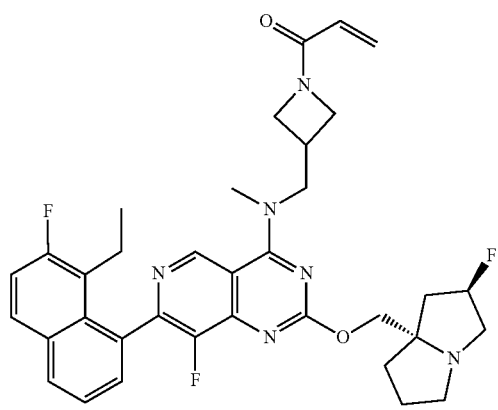 [SMILES: C=CC(=O)N1CC(CN(C)c2nc(OC[C@@]34CCCN3C[C@H](F)C4)nc3c(F)c(-c4cccc5ccc(F)c(CC)c45)ncc23)C1] | +++ |

TABLE 1-continued

Inhibition of KRAS G12C and cRAF Binding (IC$_{50}$)

| Synthetic Example | Structure | IC$_{50}$ |
|---|---|---|
| 255 | 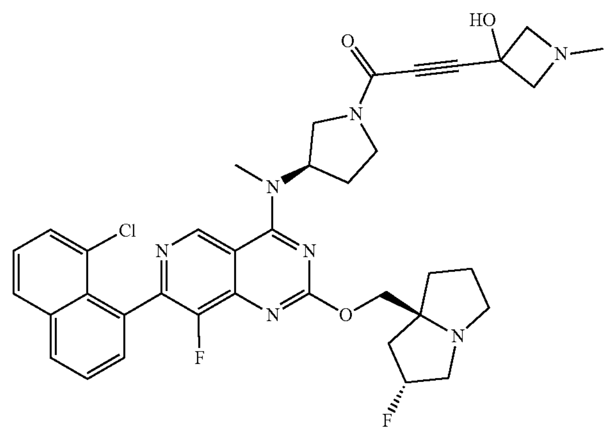 [SMILES: CN1CC(O)(C#CC(=O)N2CC[C@@H](N(C)c3nc(OC[C@@]45CCCN4C[C@H](F)C5)nc4c(F)c(-c5cccc6cccc(Cl)c56)ncc34)C2)C1] | ++++ |
| 256 | 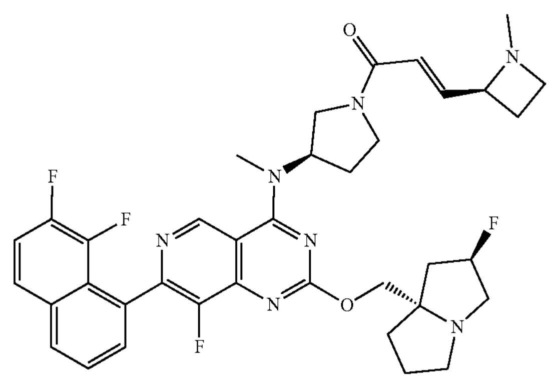 [SMILES: CN1CC[C@H]1/C=C/C(=O)N1CC[C@@H](N(C)c2nc(OC[C@@]34CCCN3C[C@H](F)C4)nc3c(F)c(-c4cccc5ccc(F)c(F)c45)ncc23)C1] | +++ |
| 257 | 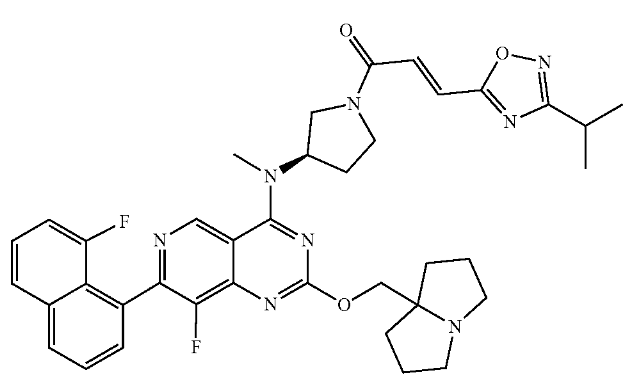 [SMILES: CC(C)c1noc(/C=C/C(=O)N2CC[C@@H](N(C)c3nc(OCC45CCCN4CCC5)nc4c(F)c(-c5cccc6cccc(F)c56)ncc34)C2)n1] | + |

TABLE 1-continued

Inhibition of KRAS G12C and cRAF Binding (IC$_{50}$)

| Synthetic Example | Structure | IC$_{50}$ |
|---|---|---|
| 258 | 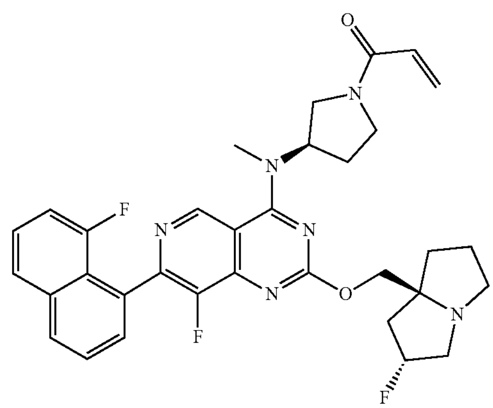 [SMILES: C=CC(=O)N1CC[C@@H](N(C)c2nc(OC[C@@]34CCCN3C[C@H](F)C4)nc3c(F)c(-c4cccc5cccc(F)c45)ncc23)C1] | +++ |
| 259 | 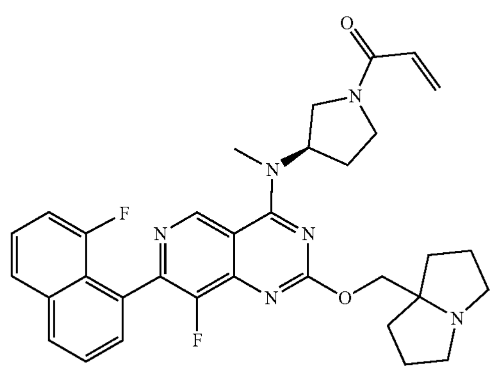 | ++ |
| 260 | 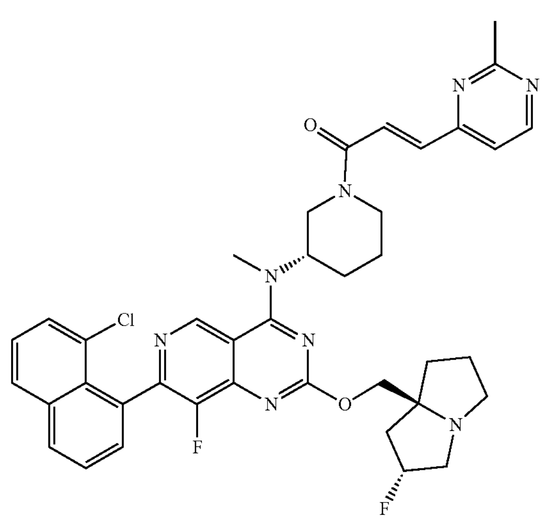 [SMILES: Cc1nccc(/C=C/C(=O)N2CCC[C@H](N(C)c3nc(OC[C@@]45CCCN4C[C@H](F)C5)nc4c(F)c(-c5cccc6cccc(Cl)c56)ncc34)C2)n1] | ++ |

TABLE 1-continued

Inhibition of KRAS G12C and cRAF Binding (IC$_{50}$)

| Synthetic Example | Structure | IC$_{50}$ |
|---|---|---|
| 261 | 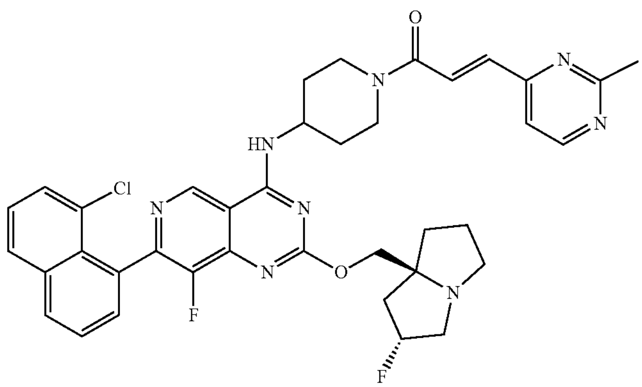 [SMILES: Cc1nccc(/C=C/C(=O)N2CCC(Nc3nc(OC[C@@]45CCCN4C[C@H](F)C5)nc4c(F)c(-c5cccc6cccc(Cl)c56)ncc34)CC2)n1] | + |
| 262 | 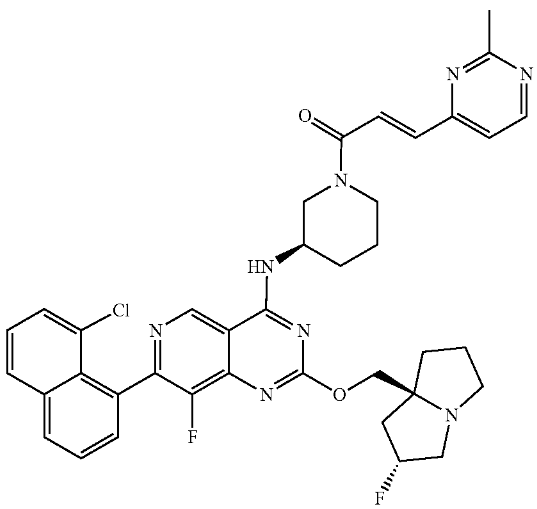 [SMILES: Cc1nccc(/C=C/C(=O)N2CCC[C@@H](Nc3nc(OC[C@@]45CCCN4C[C@H](F)C5)nc4c(F)c(-c5cccc6cccc(Cl)c56)ncc34)C2)n1] | ++ |
| 263 | 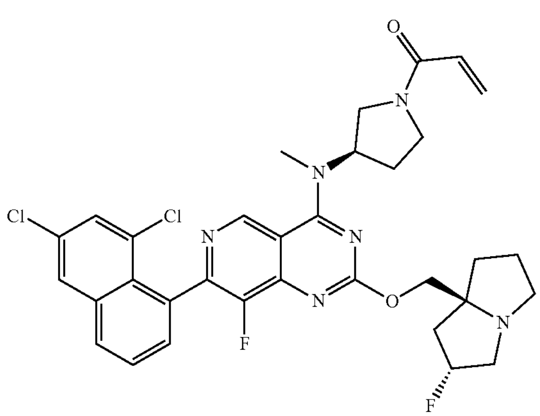 [SMILES: C=CC(=O)N1CC[C@@H](N(C)c2nc(OC[C@@]34CCCN3C[C@H](F)C4)nc3c(F)c(-c4cccc5cc(Cl)cc(Cl)c45)ncc23)C1] | + |

TABLE 1-continued
Inhibition of KRAS G12C and cRAF Binding (IC$_{50}$)
| Synthetic Example | Structure | IC$_{50}$ |
|---|---|---|
| 264 | 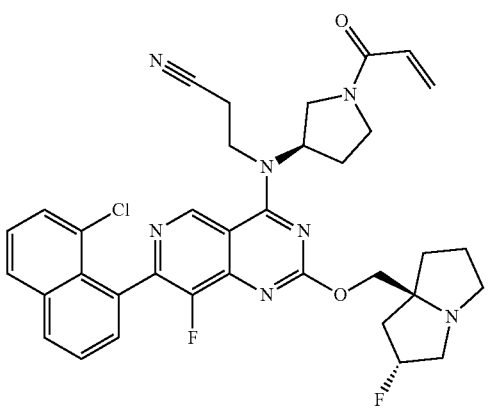 [SMILES: C=CC(=O)N1CC[C@@H](N(CCC#N)c2nc(OC[C@@]34CCCN3C[C@H](F)C4)nc3c(F)c(-c4cccc5cccc(Cl)c45)ncc23)C1] | ++ |
| 265 | 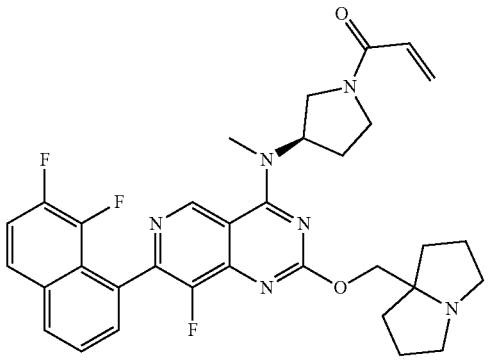 [SMILES: C=CC(=O)N1CC[C@@H](N(C)c2nc(OCC34CCCN3CCC4)nc3c(F)c(-c4cccc5ccc(F)c(F)c45)ncc23)C1] | +++ |
| 266 | 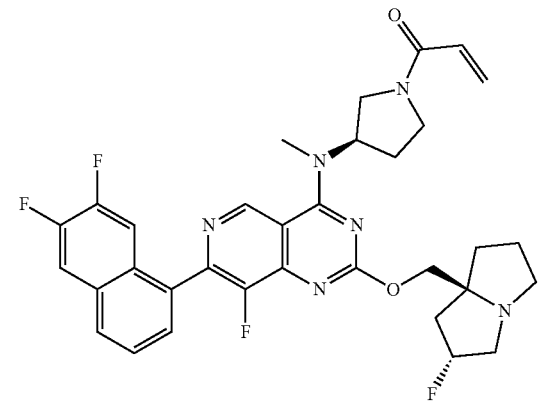 [SMILES: C=CC(=O)N1CC[C@@H](N(C)c2nc(OC[C@@]34CCCN3C[C@H](F)C4)nc3c(F)c(-c4cccc5cc(F)c(F)cc45)ncc23)C1] | ++ |

TABLE 1-continued
Inhibition of KRAS G12C and cRAF Binding (IC$_{50}$)
| Synthetic Example | Structure | IC$_{50}$ |
|---|---|---|
| 267 | 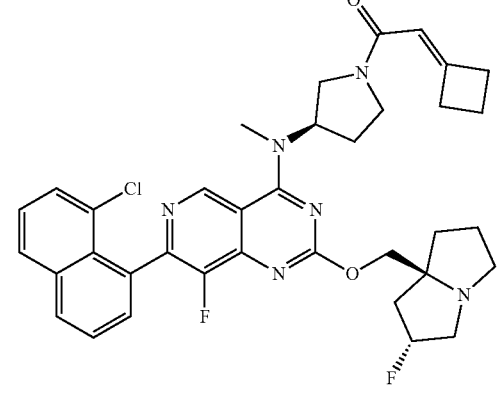 | ++ |
| 268 | 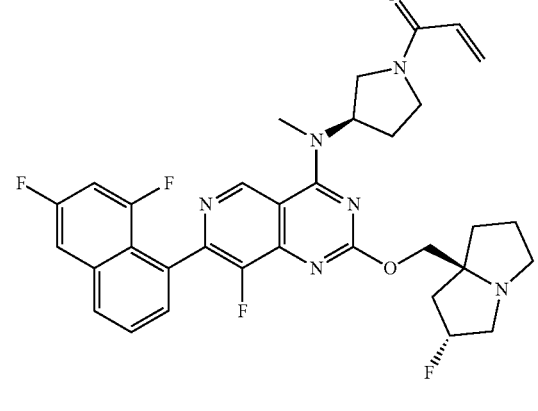 | ++ |
| 269 | 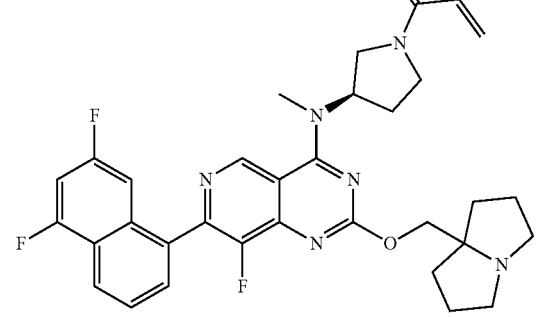 | ++ |

TABLE 1-continued
Inhibition of KRAS G12C and cRAF Binding (IC$_{50}$)
| Synthetic Example | Structure | IC$_{50}$ |
|---|---|---|
| 270 | 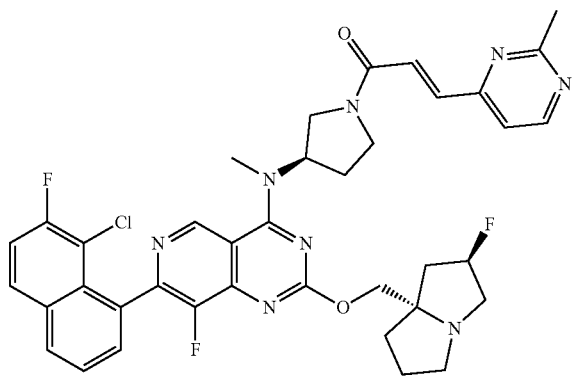 Formate salt | +++ |
| 271 | 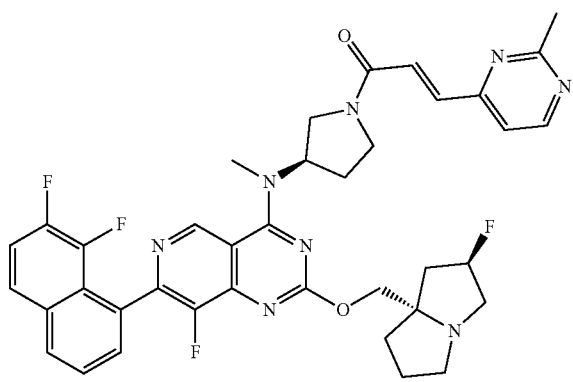 [SMILES: Cc1nccc(/C=C/C(=O)N2CC[C@@H](N(C)c3nc(OC[C@@]45CCCN4C[C@H](F)C5)nc4c(F)c(-c5cccc6ccc(F)c(F)c56)ncc34)C2)n1] | +++ |
| 272 | 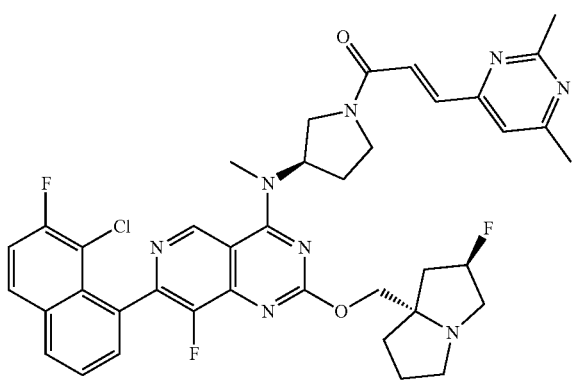 [SMILES: Cc1cc(/C=C/C(=O)N2CC[C@@H](N(C)c3nc(OC[C@@]45CCCN4C[C@H](F)C5)nc4c(F)c(-c5cccc6ccc(F)c(Cl)c56)ncc34)C2)nc(C)n1] | +++ |

TABLE 1-continued

Inhibition of KRAS G12C and cRAF Binding (IC$_{50}$)

| Synthetic Example | Structure | IC$_{50}$ |
|---|---|---|
| 273 | 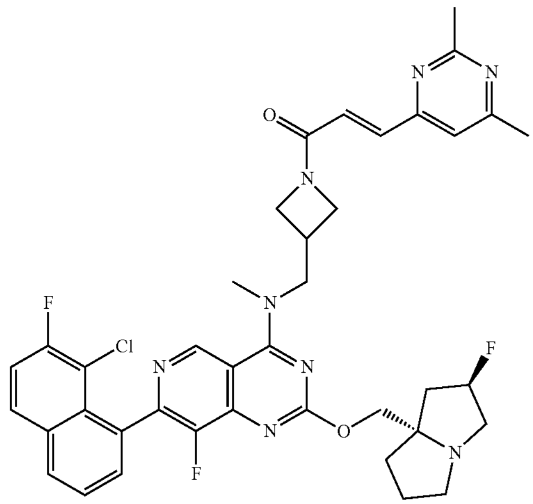 [SMILES: Cc1cc(/C=C/C(=O)N2CC(CN(C)c3nc(OC[C@@]45CCCN4C[C@H](F)C5)nc4c(F)c(-c5cccc6ccc(F)c(Cl)c56)ncc34)C2)nc(C)n1] | ++ |
| 274 | 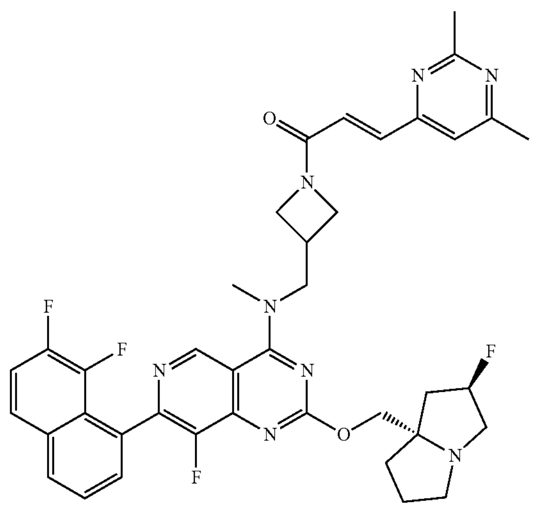 [SMILES: Cc1cc(/C=C/C(=O)N2CC(CN(C)c3nc(OC[C@@]45CCCN4C[C@H](F)C5)nc4c(F)c(-c5cccc6ccc(F)c(F)c56)ncc34)C2)nc(C)n1] | +++ |
| 275 | 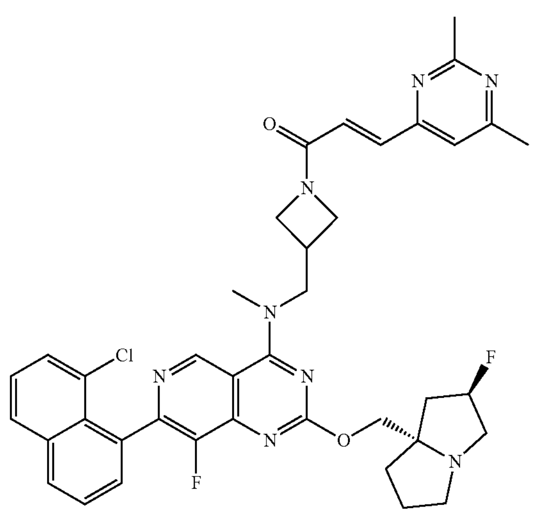 [SMILES: Cc1cc(/C=C/C(=O)N2CC(CN(C)c3nc(OC[C@@]45CCCN4C[C@H](F)C5)nc4c(F)c(-c5cccc6cccc(Cl)c56)ncc34)C2)nc(C)n1] | ++ |

TABLE 1-continued

Inhibition of KRAS G12C and cRAF Binding (IC$_{50}$)

| Synthetic Example | Structure | IC$_{50}$ |
|---|---|---|
| 276 | 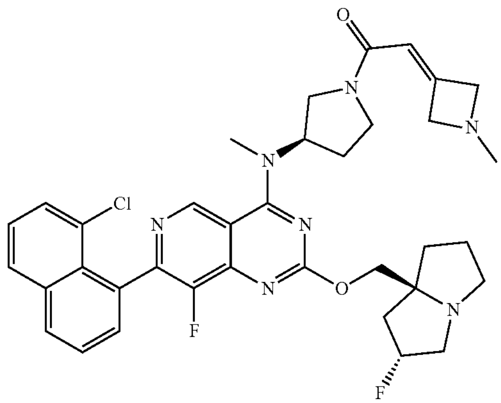 [SMILES: CN1CC(=CC(=O)N2CC[C@@H](N(C)c3nc(OC[C@@]45CCCN4C[C@H](F)C5)nc4c(F)c(-c5cccc6cccc(Cl)c56)ncc34)C2)C1] | +++ |
| 277 | 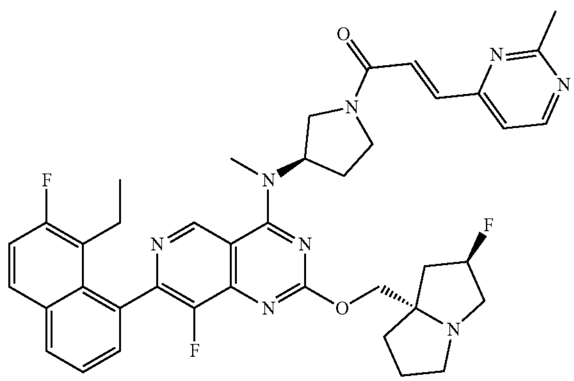 [SMILES: CCc1c(F)ccc2cccc(-c3ncc4c(N(C)[C@@H]5CCN(C(=O)/C=C/c6ccnc(C)n6)C5)nc(OC[C@@]56CCCN5C[C@H](F)C6)nc4c3F)c12] | ++ |
| 278 | 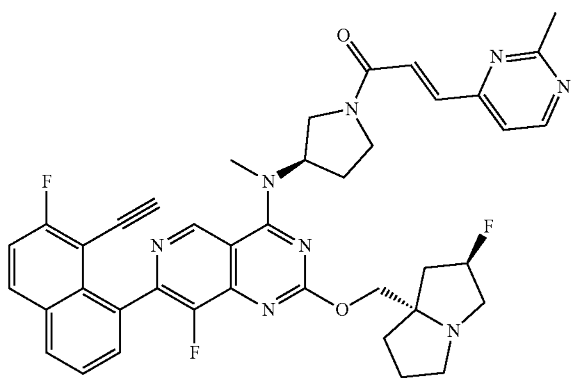 [SMILES: C#Cc1c(F)ccc2cccc(-c3ncc4c(N(C)[C@@H]5CCN(C(=O)/C=C/c6ccnc(C)n6)C5)nc(OC[C@@]56CCCN5C[C@H](F)C6)nc4c3F)c12] | +++ |
| 279 | 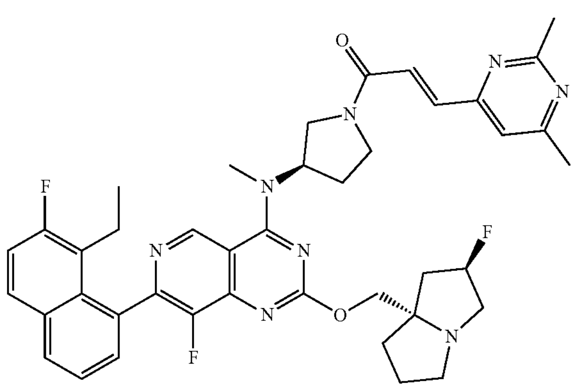 [SMILES: CCc1c(F)ccc2cccc(-c3ncc4c(N(C)[C@@H]5CCN(C(=O)/C=C/c6cc(C)nc(C)n6)C5)nc(OC[C@@]56CCCN5C[C@H](F)C6)nc4c3F)c12] | ++ |

TABLE 1-continued

Inhibition of KRAS G12C and cRAF Binding (IC$_{50}$)

| Synthetic Example | Structure | IC$_{50}$ |
|---|---|---|
| 280 | 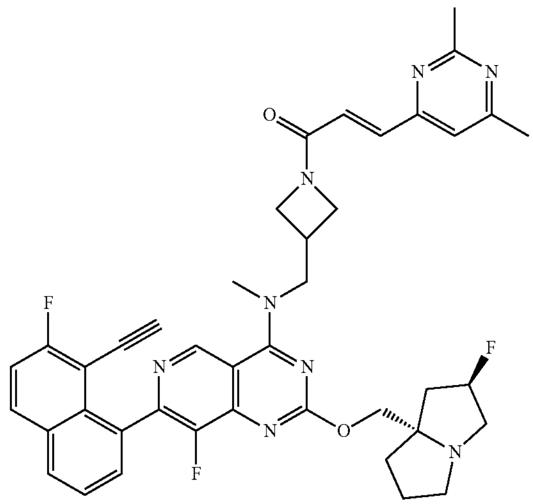 [SMILES: C#Cc1c(F)ccc2cccc(-c3ncc4c(N(C)CC5CN(C(=O)/C=C/c6cc(C)nc(C)n6)C5)nc(OC[C@@]56CCCN5C[C@H](F)C6)nc4c3F)c12] | +++ |
| 281 | 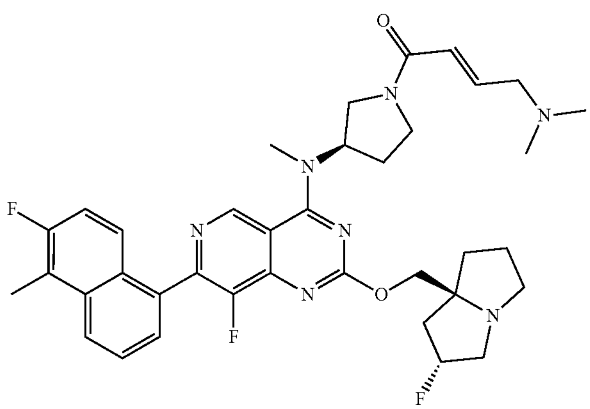 | ++ |
| 282 | 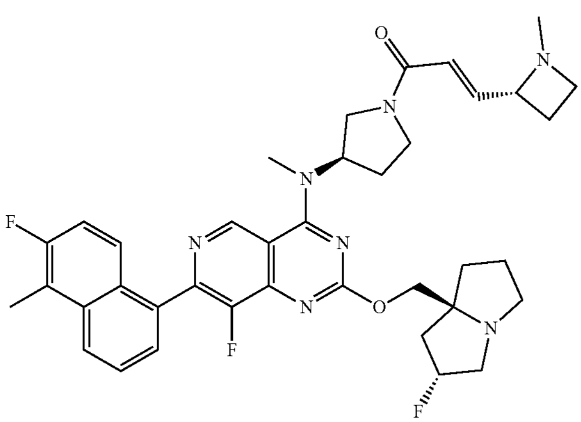 [SMILES: Cc1c(F)ccc2c(-c3ncc4c(N(C)[C@@H]5CCN(C(=O)/C=C/[C@H]6CCN6C)C5)nc(OC[C@@]56CCCN5C[C@H](F)C6)nc4c3F)cccc12] | ++ |

TABLE 1-continued

Inhibition of KRAS G12C and cRAF Binding (IC$_{50}$)

| Synthetic Example | Structure | IC$_{50}$ |
|---|---|---|
| 283 | 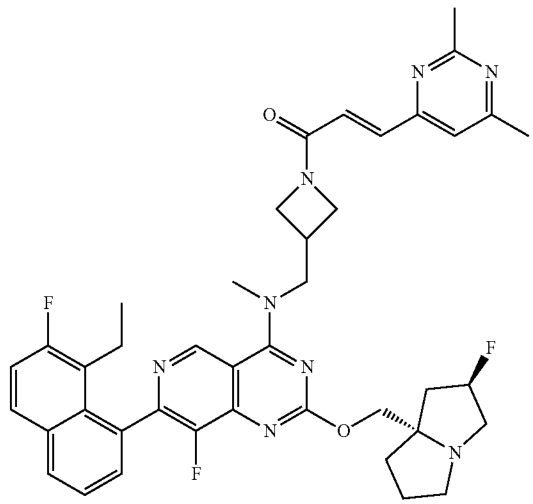 | ++ |
| 284 | 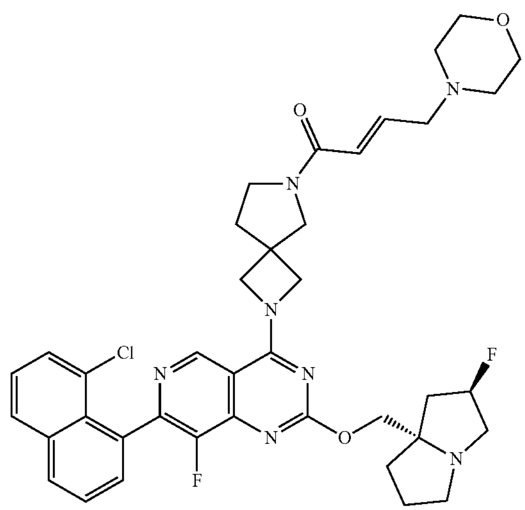 [SMILES: O=C(/C=C/CN1CCOCC1)N1CCC2(C1)CN(c1nc(OC[C@@]34CCCN3C[C@H](F)C4)nc3c(F)c(-c4cccc5cccc(Cl)c45)ncc13)C2] | |
| 285 | 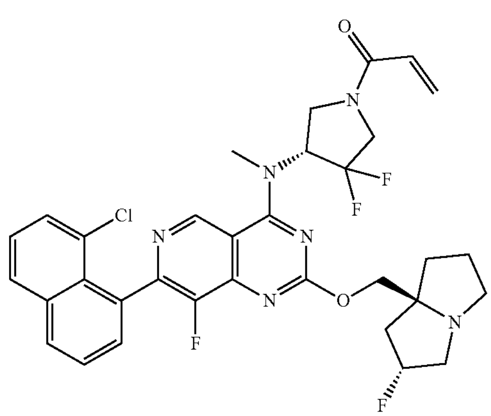 [SMILES: C=CC(=O)N1C[C@@H](N(C)c2nc(OC[C@@]34CCCN3C[C@H](F)C4)nc3c(F)c(-c4cccc5cccc(Cl)c45)ncc23)C(F)(F)C1] | + |

TABLE 1-continued

Inhibition of KRAS G12C and cRAF Binding (IC$_{50}$)

| Synthetic Example | Structure | IC$_{50}$ |
|---|---|---|
| 286 | 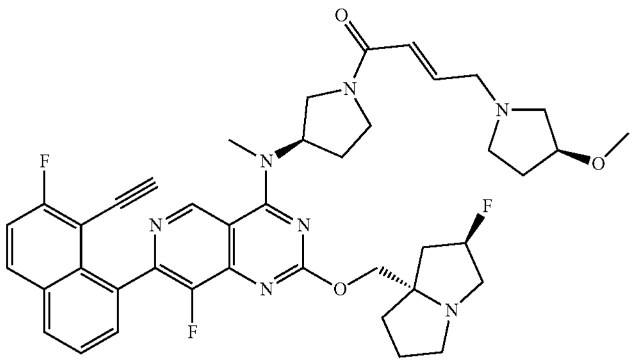 [SMILES: C#Cc1c(F)ccc2cccc(-c3ncc4c(N(C)[C@@H]5CCN(C(=O)/C=C/CN6CC[C@H](OC)C6)C5)nc(OC[C@@]56CCCN5C[C@H](F)C6)nc4c3F)c12] | +++ |
| 287 | 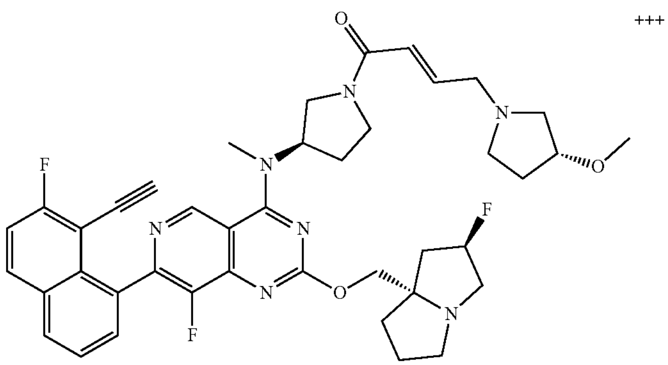 | +++ |
| 288 | 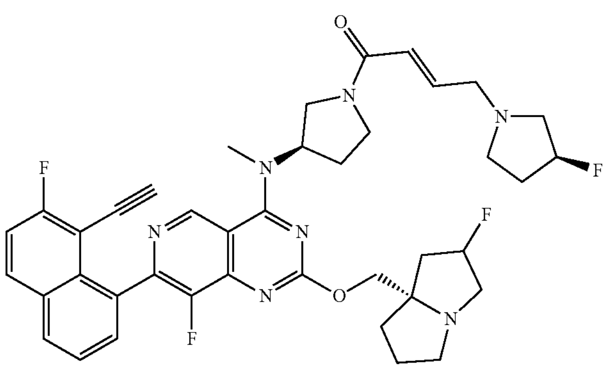 | +++ |
| 289 | 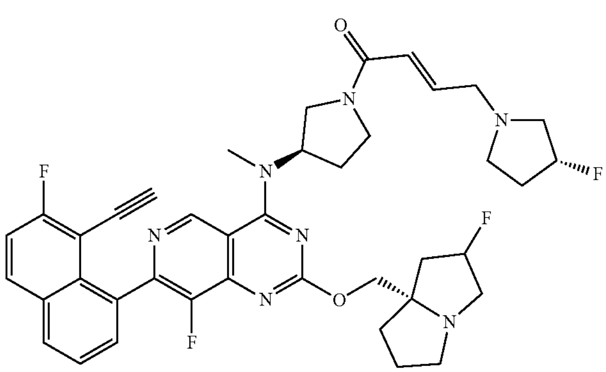 | +++ |

TABLE 1-continued

Inhibition of KRAS G12C and cRAF Binding (IC$_{50}$)

| Synthetic Example | Structure | IC$_{50}$ |
|---|---|---|
| 290 | 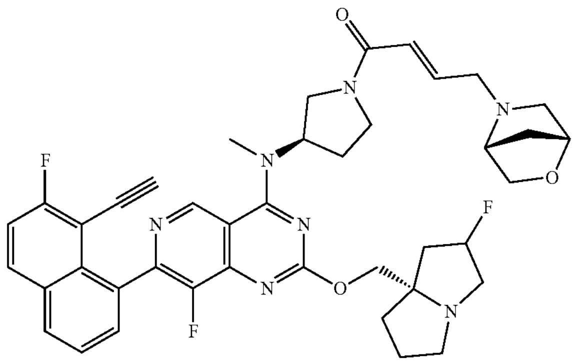 | ++++ |
| 291 | 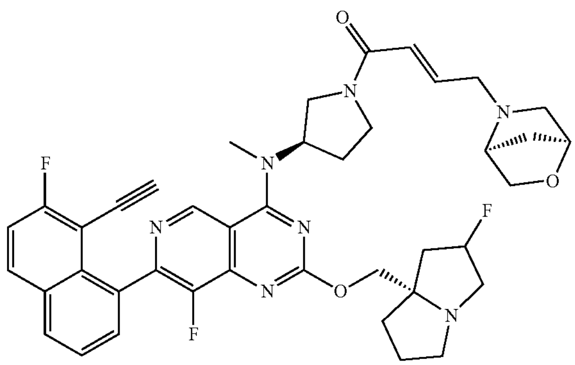 | ++++ |
| 292 | 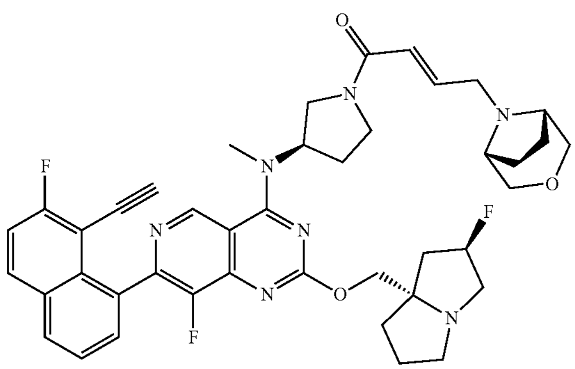 | ++++ |
| 293 | 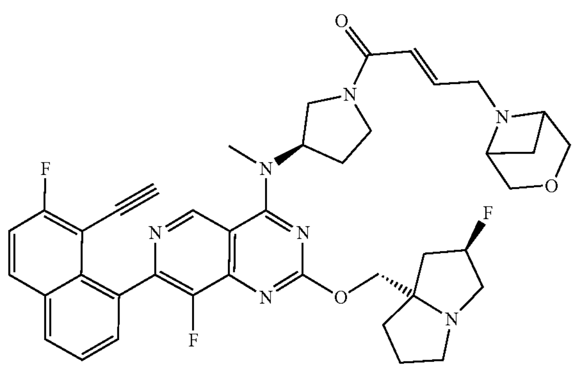 | ++++ |

TABLE 1-continued

Inhibition of KRAS G12C and cRAF Binding (IC$_{50}$)

| Synthetic Example | Structure | IC$_{50}$ |
|---|---|---|
| 294 | 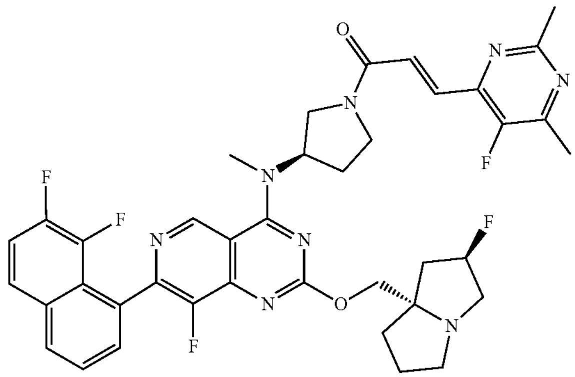 [SMILES: Cc1nc(C)c(F)c(/C=C/C(=O)N2CC[C@@H](N(C)c3nc(OC[C@@]45CCCN4C[C@H](F)C5)nc4c(F)c(-c5cccc6ccc(F)c(F)c56)ncc34)C2)n1] | ++ |
| 295 | 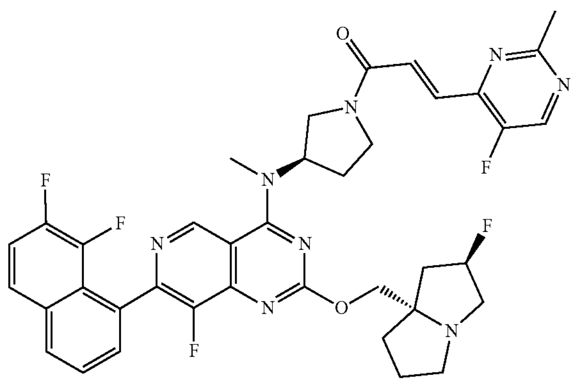 [SMILES: Cc1ncc(F)c(/C=C/C(=O)N2CC[C@@H](N(C)c3nc(OC[C@@]45CCCN4C[C@H](F)C5)nc4c(F)c(-c5cccc6ccc(F)c(F)c56)ncc34)C2)n1] | +++ |
| 296 | 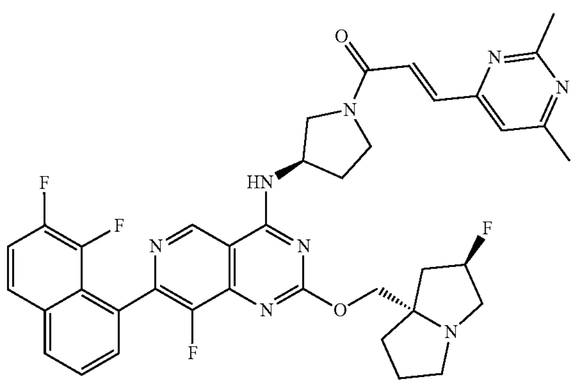 [SMILES: Cc1cc(/C=C/C(=O)N2CC[C@@H](Nc3nc(OC[C@@]45CCCN4C[C@H](F)C5)nc4c(F)c(-c5cccc6ccc(F)c(F)c56)ncc34)C2)nc(C)n1] | +++ |
| 297 | 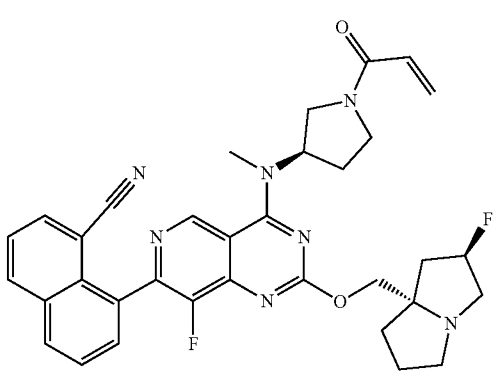 [SMILES: C=CC(=O)N1CC[C@@H](N(C)c2nc(OC[C@@]34CCCN3C[C@H](F)C4)nc3c(F)c(-c4cccc5cccc(C#N)c45)ncc23)C1] | ++ |

TABLE 1-continued

Inhibition of KRAS G12C and cRAF Binding (IC$_{50}$)

| Synthetic Example | Structure | IC$_{50}$ |
|---|---|---|
| 298 | 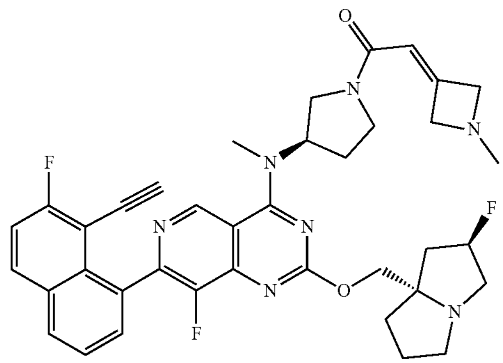 [SMILES: C#Cc1c(F)ccc2cccc(-c3ncc4c(N(C)[C@@H]5CCN(C(=O)C=C6CN(C)C6)C5)nc(OC[C@@]56CCCN5C[C@H](F)C6)nc4c3F)c12] | ++++ |
| 299 | 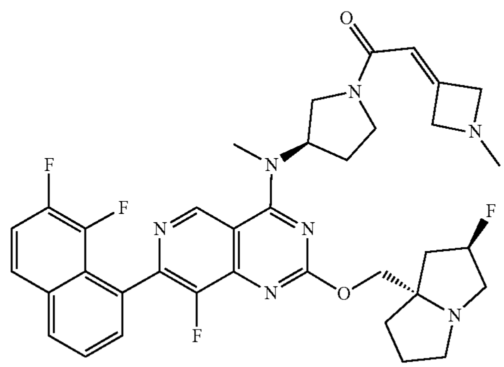 [SMILES: CN1CC(=CC(=O)N2CC[C@@H](N(C)c3nc(OC[C@@]45CCCN4C[C@H](F)C5)nc4c(F)c(-c5cccc6ccc(F)c(F)c56)ncc34)C2)C1] | ++++ |
| 300 | 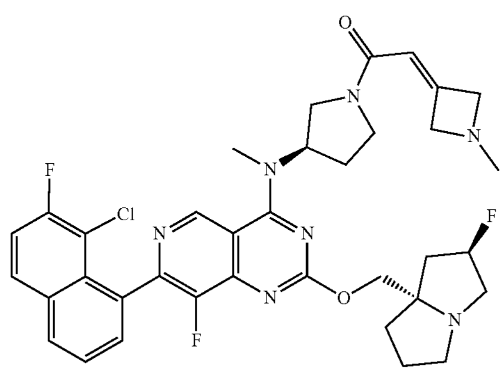 [SMILES: CN1CC(=CC(=O)N2CC[C@@H](N(C)c3nc(OC[C@@]45CCCN4C[C@H](F)C5)nc4c(F)c(-c5cccc6ccc(F)c(Cl)c56)ncc34)C2)C1] | +++ |
| 301 | 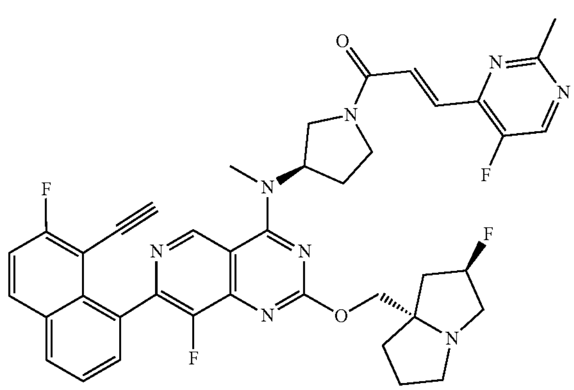 [SMILES: C#Cc1c(F)ccc2cccc(-c3ncc4c(N(C)[C@@H]5CCN(C(=O)/C=C/c6nc(C)ncc6F)C5)nc(OC[C@@]56CCCN5C[C@H](F)C6)nc4c3F)c12] | +++ |

TABLE 1-continued

Inhibition of KRAS G12C and cRAF Binding (IC$_{50}$)

| Synthetic Example | Structure | IC$_{50}$ |
|---|---|---|
| 302 | 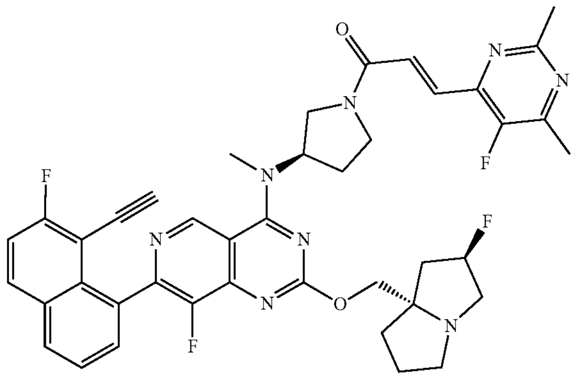 [SMILES: C#Cc1c(F)ccc2cccc(-c3ncc4c(N(C)[C@@H]5CCN(C(=O)/C=C/c6nc(C)nc(C)c6F)C5)nc(OC[C@@]56CCCN5C[C@H](F)C6)nc4c3F)c12] | +++ |
| 303 | 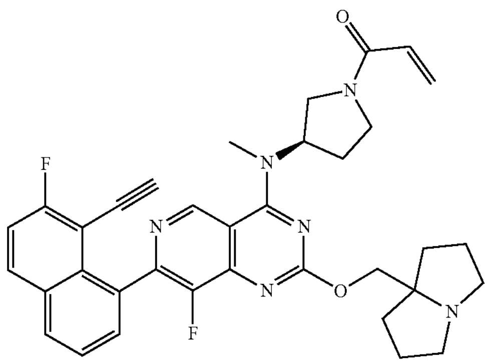 [SMILES: C#Cc1c(F)ccc2cccc(-c3ncc4c(N(C)[C@@H]5CCN(C(=O)C=C)C5)nc(OCC56CCCN5CCC6)nc4c3F)c12] | ++++ |
| 304 | 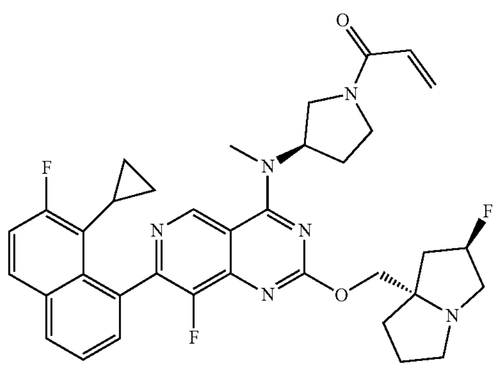 [SMILES: C=CC(=O)N1CC[C@@H](N(C)c2nc(OC[C@@]34CCCN3C[C@H](F)C4)nc3c(F)c(-c4cccc5ccc(F)c(C6CC6)c45)ncc23)C1] | + |
| 305 | 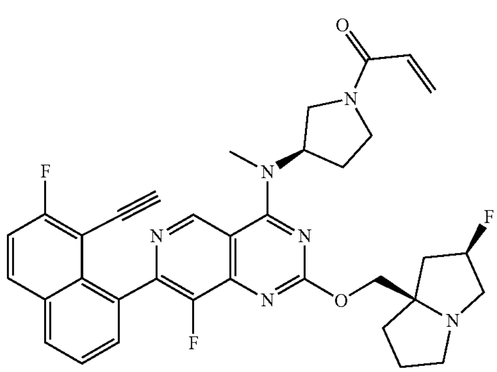 [SMILES: C#Cc1c(F)ccc2cccc(-c3ncc4c(N(C)[C@@H]5CCN(C(=O)C=C)C5)nc(OC[C@]56CCCN5C[C@H](F)C6)nc4c3F)c12] | +++ |

TABLE 1-continued

Inhibition of KRAS G12C and cRAF Binding (IC$_{50}$)

| Synthetic Example | Structure | IC$_{50}$ |
|---|---|---|
| 306 | 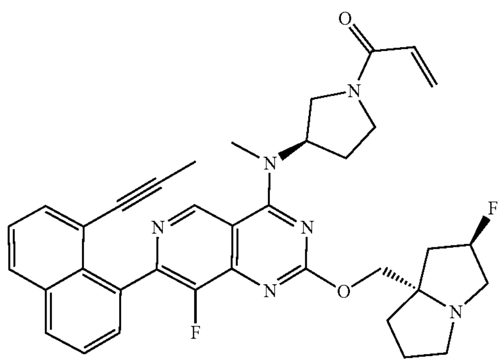 [SMILES: C=CC(=O)N1CC[C@@H](N(C)c2nc(OC[C@@]34CCCN3C[C@H](F)C4)nc3c(F)c(-c4cccc5cccc(C#CC)c45)ncc23)C1] | + |
| 307 | 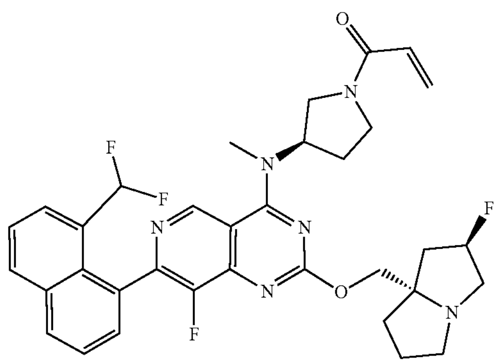 [SMILES: C=CC(=O)N1CC[C@@H](N(C)c2nc(OC[C@@]34CCCN3C[C@H](F)C4)nc3c(F)c(-c4cccc5cccc(C(F)F)c45)ncc23)C1] | + |

* ++++is less than 10 nM, +++is 10 to less than 100 nM, ++is 100 to less than 500 nM, +is greater or equal to 500 nM TABLE 1a Additional exemplary compounds—Inhibition of KRAS$^{G12C}$ and cRAF Binding

| Structure | RAF 1 RBD IC50 |
|---|---|
| | |

TABLE 1a-continued
Additional exemplary compounds—Inhibition of KRAS$^{G12C}$ and cRAF Binding
| Structure | RAF 1 RBD IC50 |
|---|---|
| 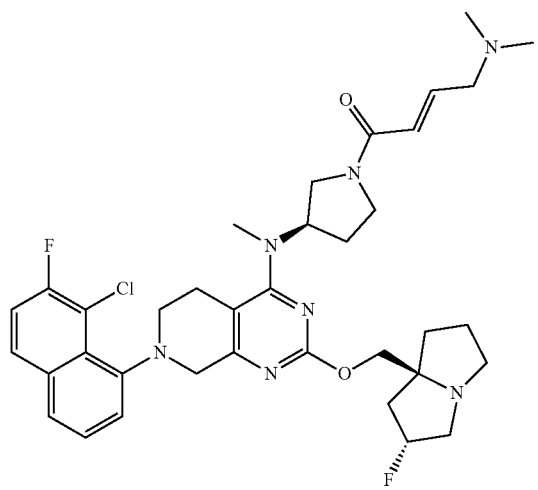 [SMILES: CN(C)C/C=C/C(=O)N1CC[C@@H](N(C)c2nc(OC[C@@]34CCCN3C[C@H](F)C4)nc3c2CCN(c2cccc4ccc(F)c(Cl)c24)C3)C1] | +++ |
| 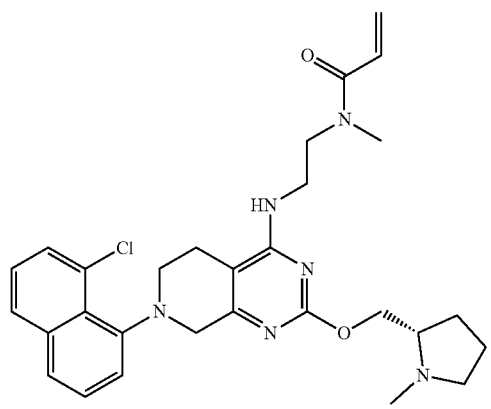 [SMILES: C=CC(=O)N(C)CCNc1nc(OC[C@@H]2CCCN2C)nc2c1CCN(c1cccc3cccc(Cl)c13)C2] | |
| 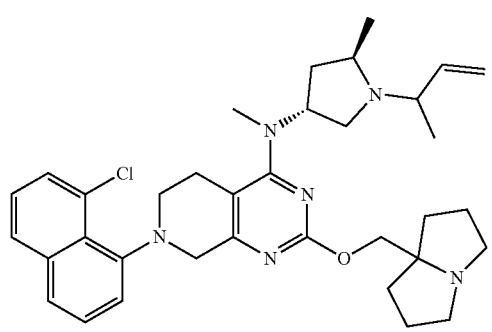 [SMILES: C=CC(C)N1C[C@H](N(C)c2nc(OCC34CCCN3CCC4)nc3c2CCN(c2cccc4cccc(Cl)c24)C3)C[C@H]1C] | + |

TABLE 1a-continued
Additional exemplary compounds—Inhibition of KRAS$^{G12C}$ and cRAF Binding
| Structure | RAF1 RBD IC50 |
|---|---|
| 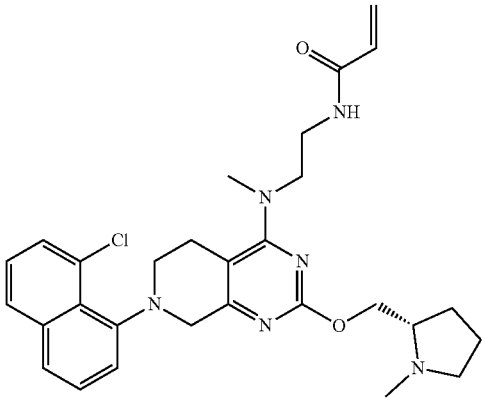 [SMILES: C=CC(=O)NCCN(C)c1nc(OC[C@@H]2CCCN2C)nc2c1CCN(c1cccc3cccc(Cl)c13)C2] | |
| 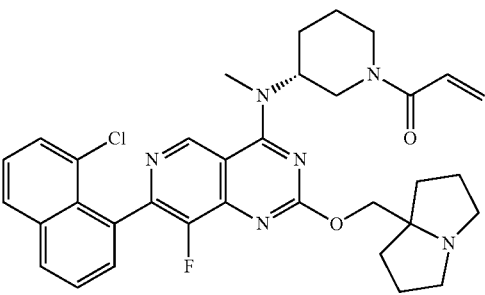 [SMILES: C=CC(=O)N1CCC[C@@H](N(C)c2nc(OCC34CCCN3CCC4)nc3c(F)c(-c4cccc5cccc(Cl)c45)ncc23)C1] | + |
| 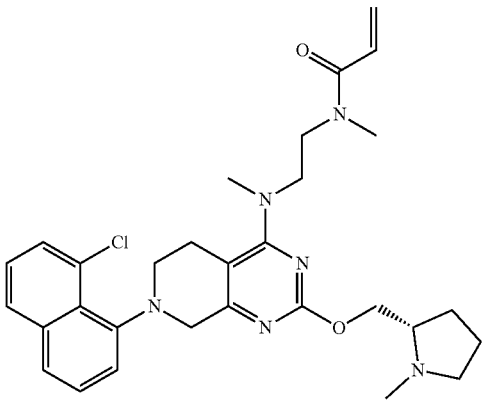 [SMILES: C=CC(=O)N(C)CCN(C)c1nc(OC[C@@H]2CCCN2C)nc2c1CCN(c1cccc3cccc(Cl)c13)C2] | |
| 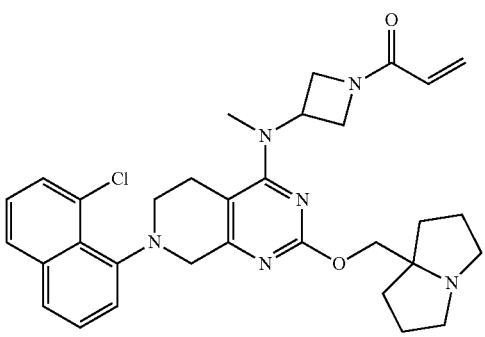 [SMILES: C=CC(=O)N1CC(N(C)c2nc(OCC34CCCN3CCC4)nc3c2CCN(c2cccc4cccc(Cl)c24)C3)C1] | + |

TABLE 1a-continued

Additional exemplary compounds—Inhibition of KRAS$^{G12C}$ and cRAF Binding

| Structure | RAF 1 RBD IC50 |
|---|---|
| | |
| 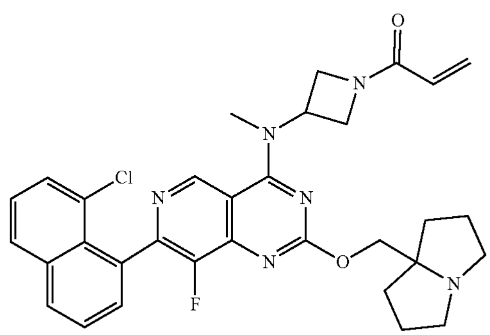 [SMILES: C=CC(=O)N1CC(N(C)c2nc(OCC34CCCN3CCC4)nc3c(F)c(-c4cccc5cccc(Cl)c45)ncc23)C1] | + |
| 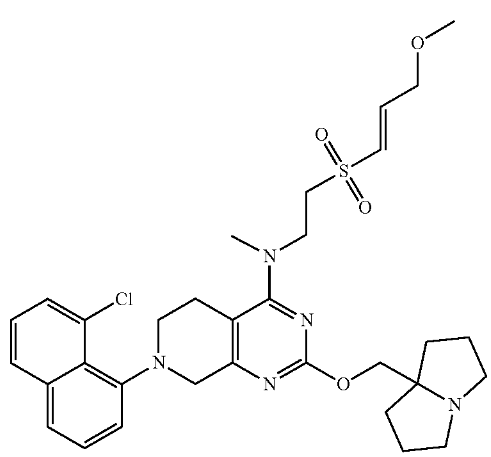 [SMILES: COC/C=C/S(=O)(=O)CCN(C)c1nc(OCC23CCCN2CCC3)nc2c1CCN(c1cccc3cccc(Cl)c13)C2] | ++ |
| | |

TABLE 1a-continued
Additional exemplary compounds—Inhibition of KRAS^{G12C} and cRAF Binding
| Structure | RAF 1 RBD IC50 |
|---|---|
| 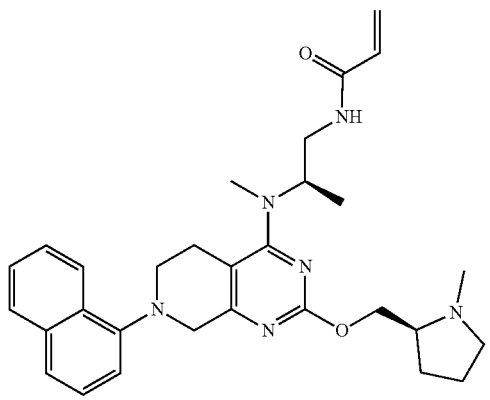 [SMILES: C=CC(=O)NC[C@@H](C)N(C)c1nc(OC[C@@H]2CCCN2C)nc2c1CCN(c1cccc3ccccc13)C2] | |
| 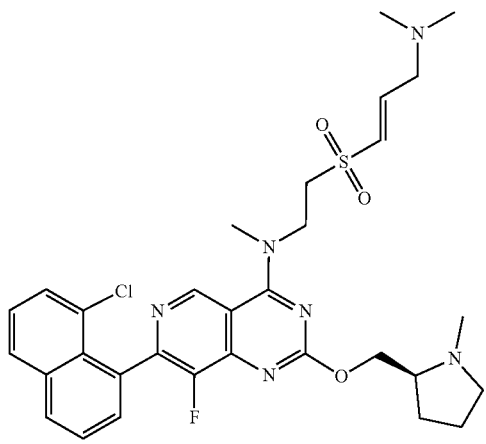 [SMILES: CN(C)C/C=C/S(=O)(=O)CCN(C)c1nc(OC[C@@H]2CCCN2C)nc2c(F)c(-c3cccc4cccc(Cl)c34)ncc12] | +++ |
| 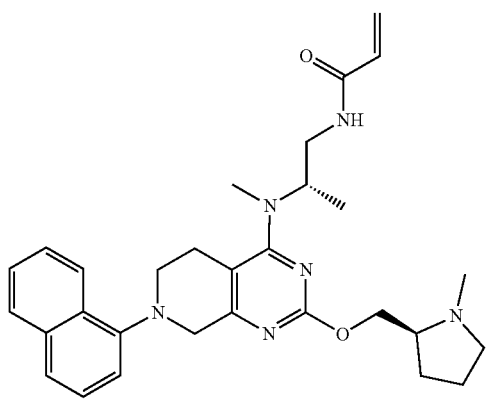 [SMILES: C=CC(=O)NC[C@H](C)N(C)c1nc(OC[C@@H]2CCCN2C)nc2c1CCN(c1cccc3ccccc13)C2] | |

TABLE 1a-continued
Additional exemplary compounds—Inhibition of KRAS$^{G12C}$ and cRAF Binding
| Structure | RAF 1 RBD IC50 |
|---|---|
| 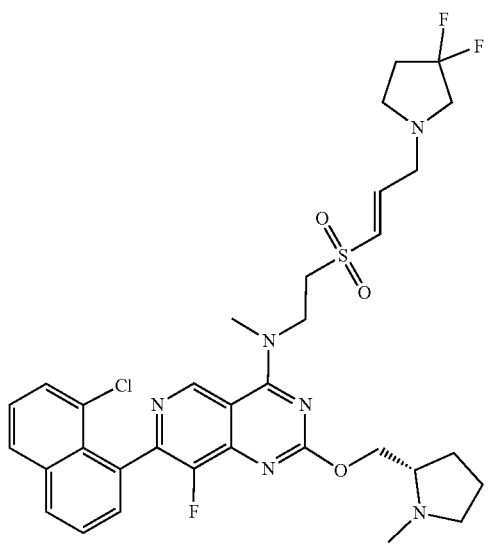 [SMILES: CN(CCS(=O)(=O)/C=C/CN1CCC(F)(F)C1)c1nc(OC[C@@H]2CCCN2C)nc2c(F)c(-c3cccc4cccc(Cl)c34)ncc12] | + |
| 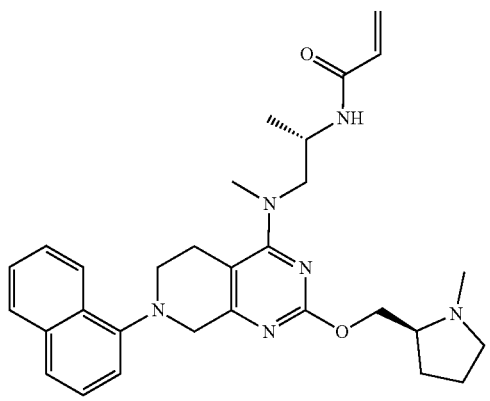 [SMILES: C=CC(=O)N[C@@H](C)CN(C)c1nc(OC[C@@H]2CCCN2C)nc2c1CCN(c1cccc3ccccc13)C2] | |
| 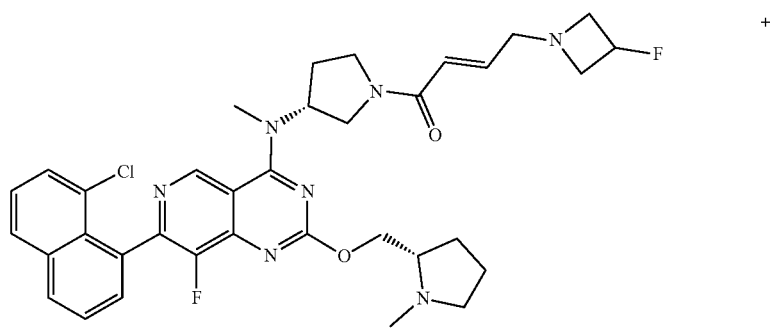 | + |

TABLE 1a-continued
Additional exemplary compounds—Inhibition of KRAS$^{G12C}$ and cRAF Binding
| Structure | RAF 1 RBD IC50 |
|---|---|
| 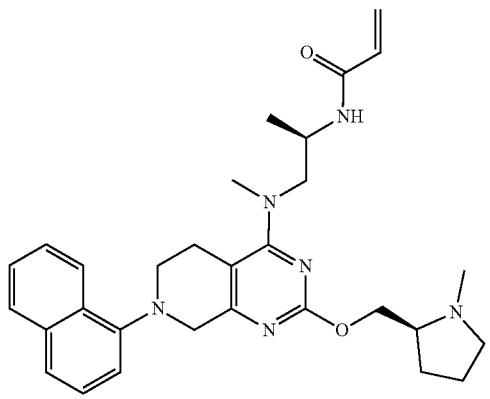 [SMILES: C=CC(=O)N[C@H](C)CN(C)c1nc(OC[C@@H]2CCCN2C)nc2c1CCN(c1cccc3ccccc13)C2] | + |
| 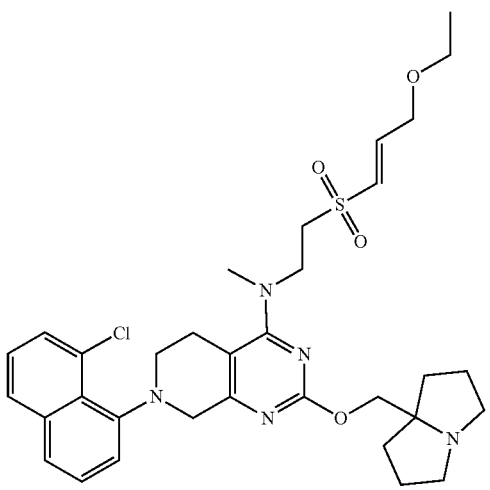 [SMILES: CCOC/C=C/S(=O)(=O)CCN(C)c1nc(OCC23CCCN2CCC3)nc2c1CCN(c1cccc3cccc(Cl)c13)C2] | ++ |
| 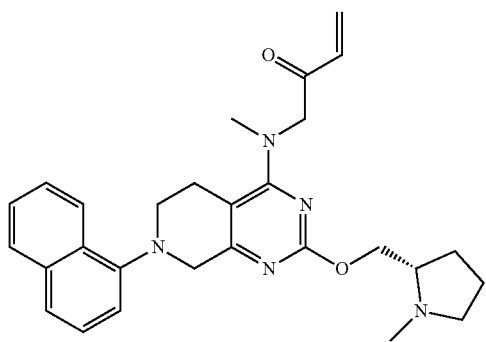 [SMILES: C=CC(=O)CN(C)c1nc(OC[C@@H]2CCCN2C)nc2c1CCN(c1cccc3ccccc13)C2] | |

TABLE 1a-continued
Additional exemplary compounds—Inhibition of KRAS$^{G12C}$ and cRAF Binding
| Structure | RAF 1 RBD IC50 |
|---|---|
| 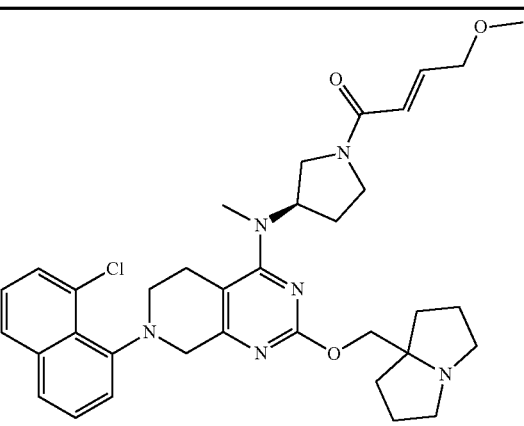 | ++ |
| 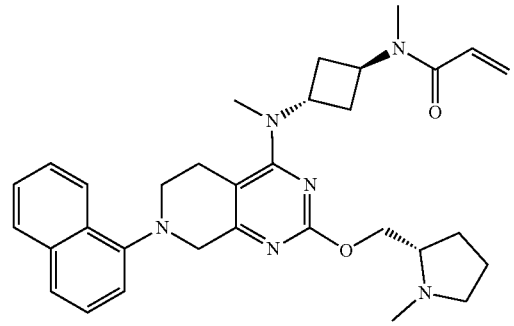 [SMILES: C=CC(=O)N(C)[C@H]1C[C@H](N(C)c2nc(OC[C@@H]3CCCN3C)nc3c2CCN(c2cccc4ccccc24)C3)C1] | |
| 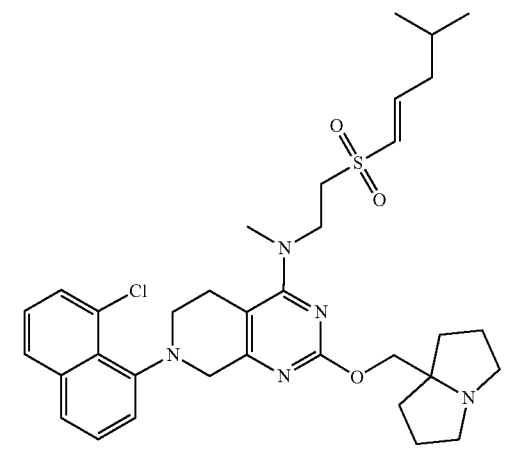 [SMILES: CC(C)C/C=C/S(=O)(=O)CCN(C)c1nc(OCC23CCCN2CCC3)nc2c1CCN(c1cccc3cccc(Cl)c13)C2] | + |
| 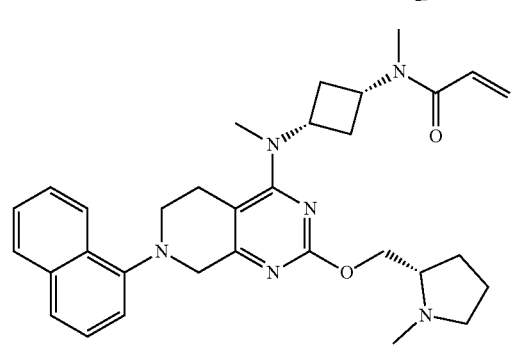 | |

TABLE 1a-continued
Additional exemplary compounds—Inhibition of KRAS$^{G12C}$ and cRAF Binding
| Structure | RAF 1 RBD IC50 |
|---|---|
| 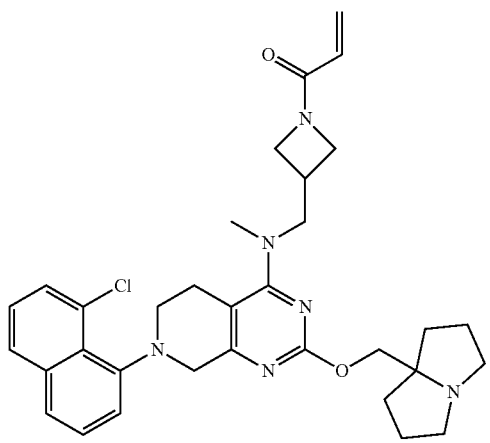 [SMILES: C=CC(=O)N1CC(CN(C)c2nc(OCC34CCCN3CCC4)nc3c2CCN(c2cccc4cccc(Cl)c24)C3)C1] | ++ |
| 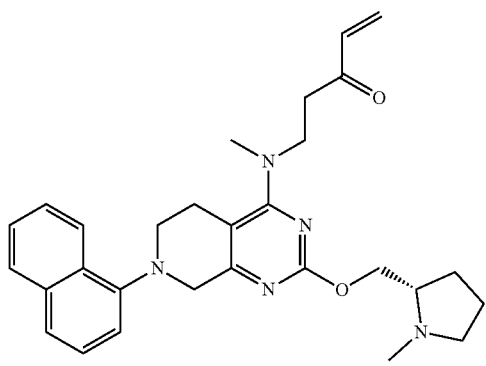 [SMILES: C=CC(=O)CCN(C)c1nc(OC[C@@H]2CCCN2C)nc2c1CCN(c1cccc3ccccc13)C2] | + |
| 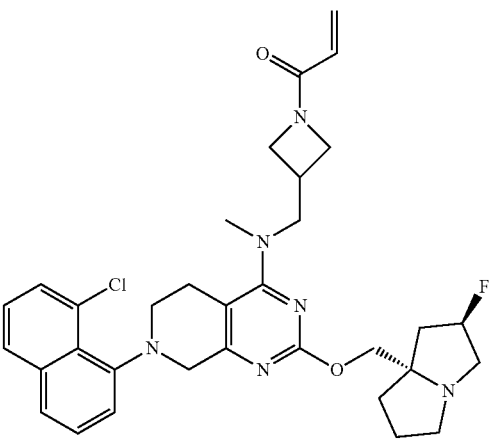 [SMILES: C=CC(=O)N1CC(CN(C)c2nc(OC[C@@]34CCCN3C[C@H](F)C4)nc3c2CCN(c2cccc4cccc(Cl)c24)C3)C1] | ++ |

TABLE 1a-continued
Additional exemplary compounds—Inhibition of KRAS^G12C and cRAF Binding
| Structure | RAF 1 RBD IC50 |
|---|---|
| 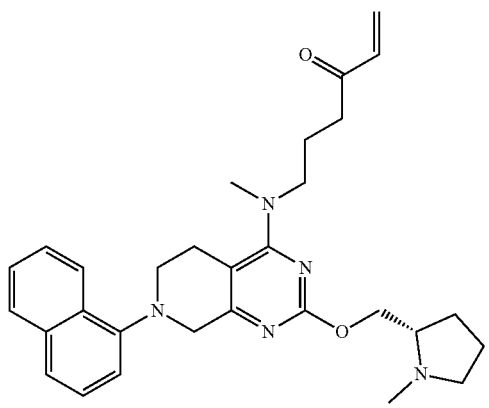 [SMILES: C=CC(=O)CCCN(C)c1nc(OC[C@@H]2CCCN2C)nc2c1CCN(c1cccc3ccccc13)C2] | + |
| 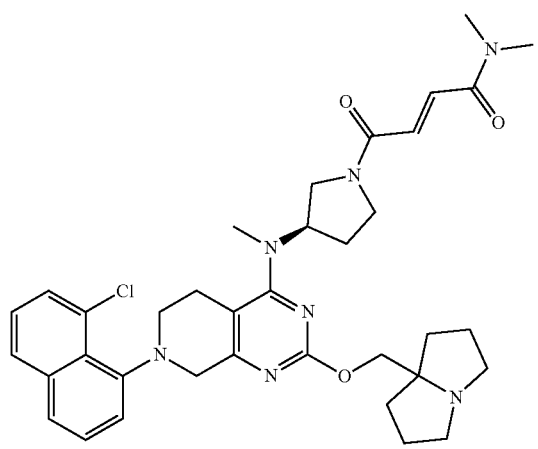 [SMILES: CN(C)C(=O)/C=C/C(=O)N1CC[C@@H](N(C)c2nc(OCC34CCCN3CCC4)nc3c2CCN(c2cccc4cccc(Cl)c24)C3)C1] | + |
| 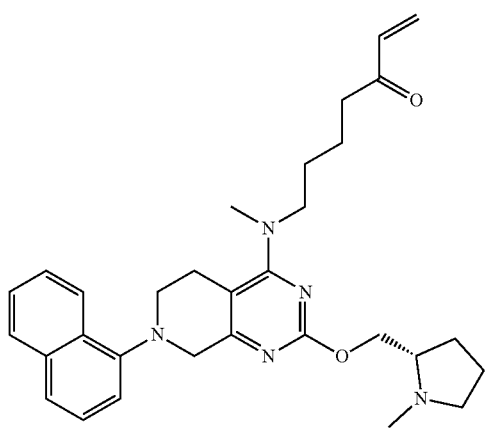 [SMILES: C=CC(=O)CCCCN(C)c1nc(OC[C@@H]2CCCN2C)nc2c1CCN(c1cccc3ccccc13)C2] | ++ |

TABLE 1a-continued

Additional exemplary compounds—Inhibition of KRAS$^{G12C}$ and cRAF Binding

| Structure | RAF1 RBD IC50 |
|---|---|
| | + |
| | + |
| | + |

TABLE 1a-continued
Additional exemplary compounds—Inhibition of KRAS^{G12C} and cRAF Binding
| Structure | RAF1 RBD IC50 |
|---|---|
| 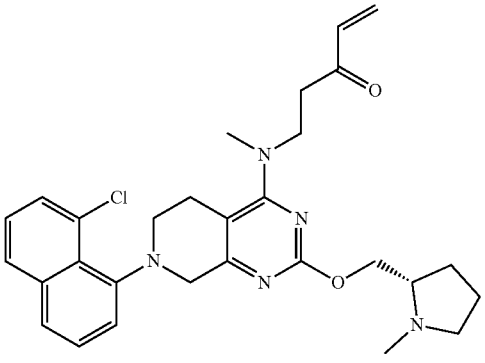 [SMILES: C=CC(=O)CCN(C)c1nc(OC[C@@H]2CCCN2C)nc2c1CCN(c1cccc3cccc(Cl)c13)C2] | +++ |
| 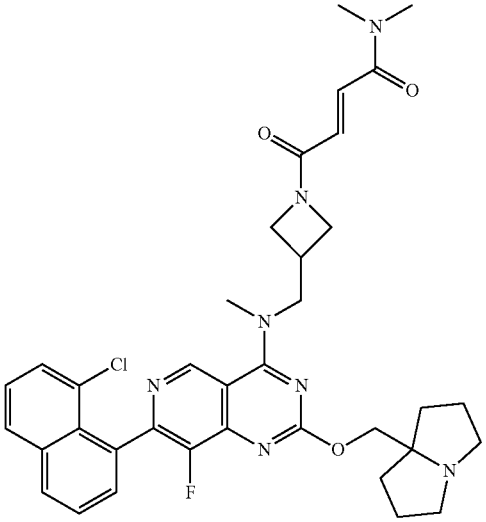 [SMILES: CN(C)C(=O)/C=C/C(=O)N1CC(CN(C)c2nc(OCC34CCCN3CCC4)nc3c(F)c(-c4cccc5cccc(Cl)c45)ncc23)C1] | + |
| 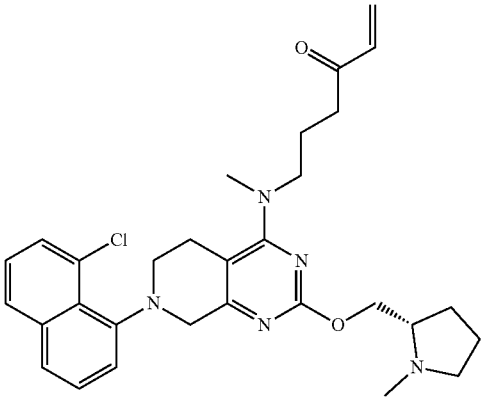 [SMILES: C=CC(=O)CCCN(C)c1nc(OC[C@@H]2CCCN2C)nc2c1CCN(c1cccc3cccc(Cl)c13)C2] | ++++ |

TABLE 1a-continued

Additional exemplary compounds—Inhibition of KRAS$^{G12C}$ and cRAF Binding

| Structure | RAF 1 RBD IC50 |
|---|---|
| 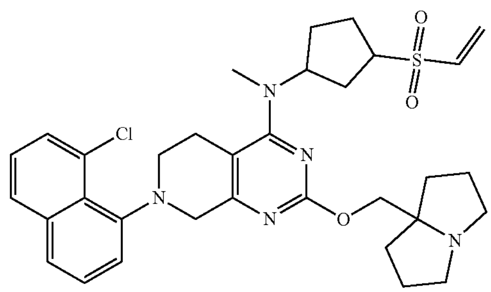 [SMILES: C=CS(=O)(=O)C1CCC(N(C)c2nc(OCC34CCCN3CCC4)nc3c2CCN(c2cccc4cccc(Cl)c24)C3)C1] | +++ |
| | + |
| 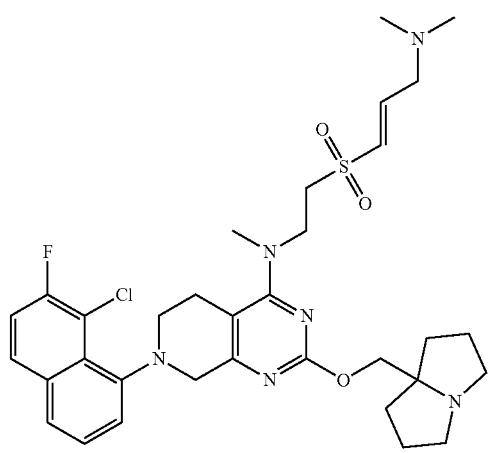 [SMILES: CN(C)C/C=C/S(=O)(=O)CCN(C)c1nc(OCC23CCCN2CCC3)nc2c1CCN(c1cccc3ccc(F)c(Cl)c13)C2] | ++++ |
| | + |

TABLE 1a-continued
Additional exemplary compounds—Inhibition of KRAS^{G12C} and cRAF Binding
| Structure | RAF 1 RBD IC50 |
|---|---|
| 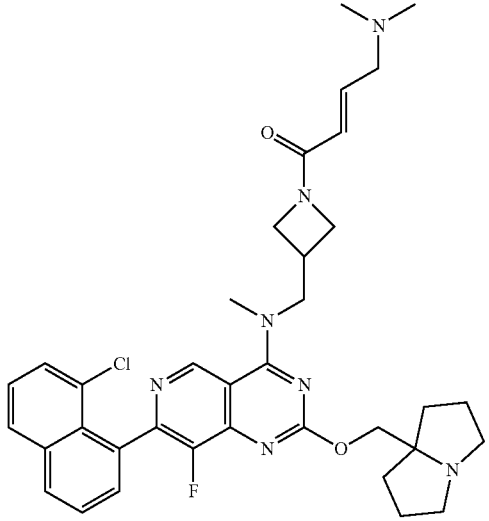 [SMILES: CN(C)C/C=C/C(=O)N1CC(CN(C)c2nc(OCC34CCCN3CCC4)nc3c(F)c(-c4cccc5cccc(Cl)c45)ncc23)C1] | +++ |
| 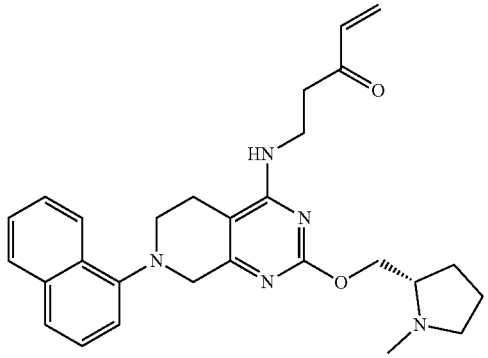 [SMILES: C=CC(=O)CCNc1nc(OC[C@@H]2CCCN2C)nc2c1CCN(c1cccc3ccccc13)C2] | + |
| 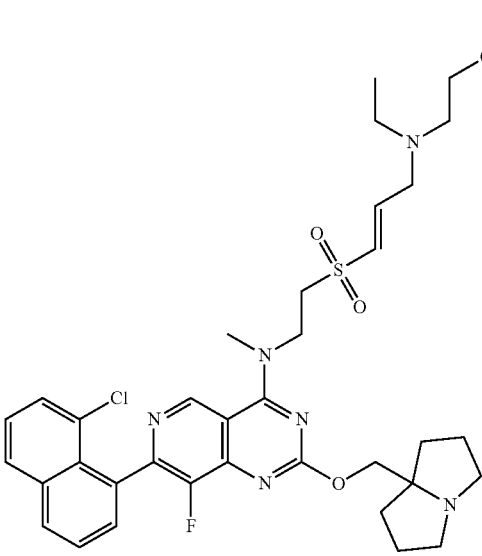 | +++ |

TABLE 1a-continued

Additional exemplary compounds—Inhibition of KRAS$^{G12C}$ and cRAF Binding

| Structure | RAF 1 RBD IC50 |
|---|---|
| | + |
| | + |
| | + |
| | + |

TABLE 1a-continued
Additional exemplary compounds—Inhibition of $KRAS^{G12C}$ and cRAF Binding
| Structure | RAF 1 RBD IC50 |
|---|---|
| 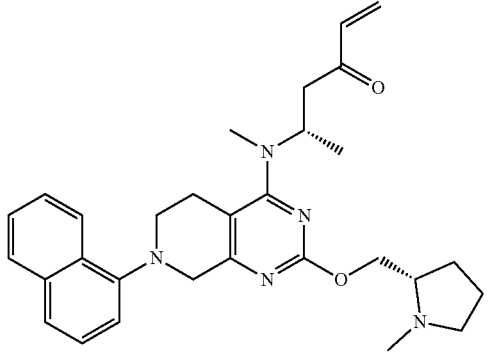 [SMILES: C=CC(=O)C[C@H](C)N(C)c1nc(OC[C@@H]2CCCN2C)nc2c1CCN(c1cccc3ccccc13)C2] | + |
| 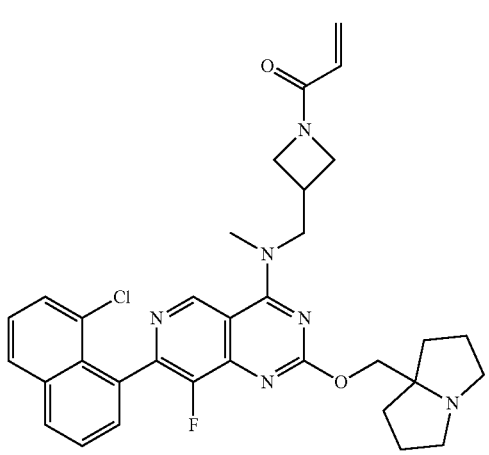 [SMILES: C=CC(=O)N1CC(CN(C)c2nc(OCC34CCCN3CCC4)nc3c(F)c(-c4cccc5cccc(Cl)c45)ncc23)C1] | +++ |
| 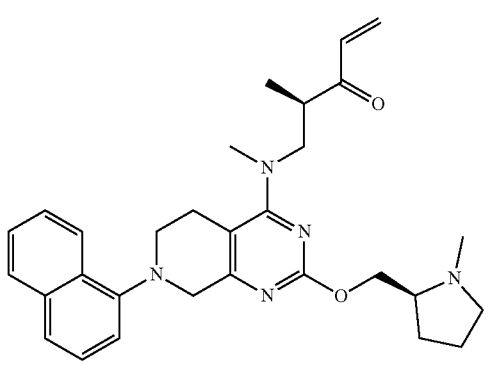 [SMILES: C=CC(=O)[C@H](C)CN(C)c1nc(OC[C@@H]2CCCN2C)nc2c1CCN(c1cccc3ccccc13)C2] | + |
| 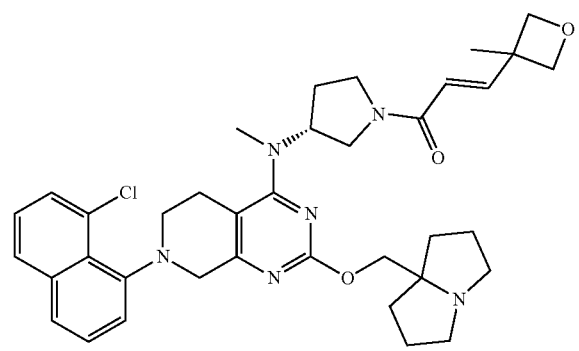 [SMILES: CN(c1nc(OCC23CCCN2CCC3)nc2c1CCN(c1cccc3cccc(Cl)c13)C2)[C@@H]1CCN(C(=O)/C=C/C2(C)COC2)C1] | + |

TABLE 1a-continued
Additional exemplary compounds—Inhibition of $KRAS^{G12C}$ and cRAF Binding
| Structure | RAF 1 RBD IC50 |
|---|---|
| 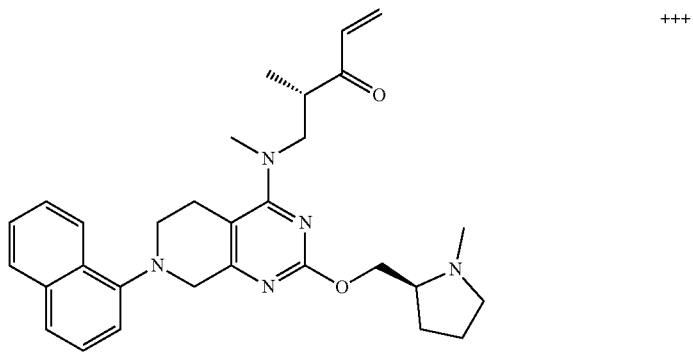 | +++ |
| 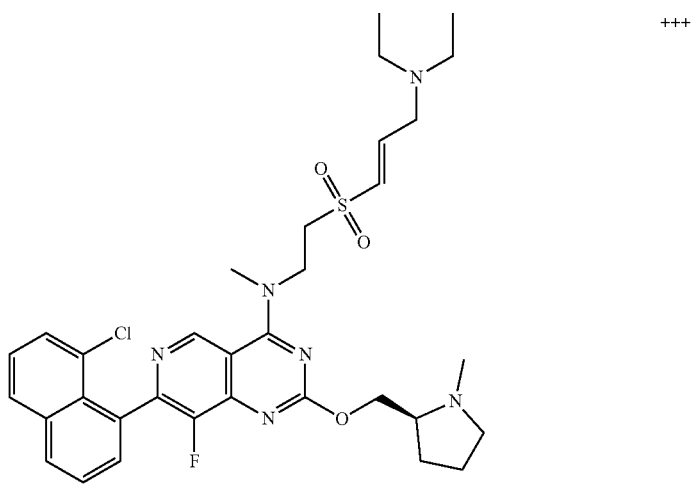 | +++ |
| 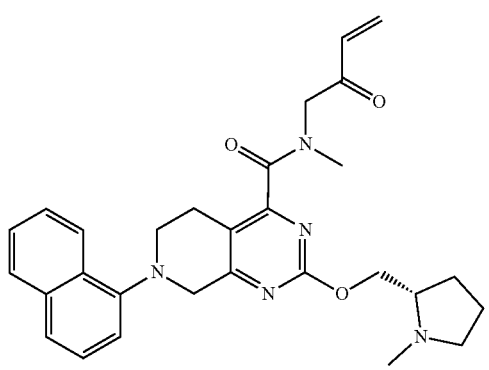 [SMILES: C=CC(=O)CN(C)C(=O)c1nc(OC[C@@H]2CCCN2C)nc2c1CCN(c1cccc3ccccc13)C2] | |

TABLE 1a-continued

Additional exemplary compounds—Inhibition of KRAS$^{G12C}$ and cRAF Binding

| Structure | RAF 1 RBD IC50 |
|---|---|
| 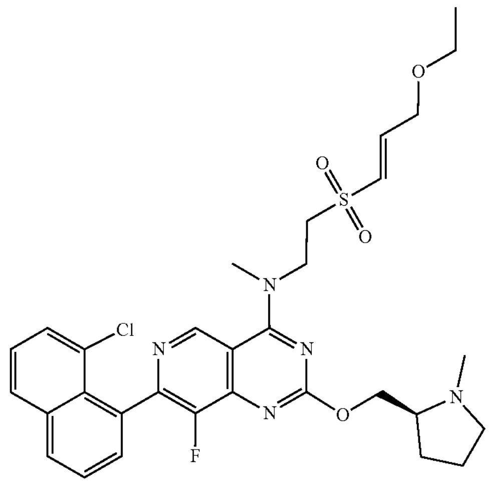 [SMILES: CCOC/C=C/S(=O)(=O)CCN(C)c1nc(OC[C@@H]2CCCN2C)nc2c(F)c(-c3cccc4cccc(Cl)c34)ncc12] | + |
| | |
| 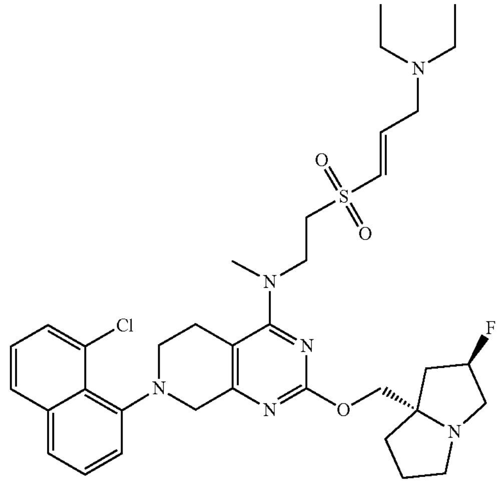 [SMILES: CCN(CC)C/C=C/S(=O)(=O)CCN(C)c1nc(OC[C@@]23CCCN2C[C@H](F)C3)nc2c1CCN(c1cccc3cccc(Cl)c13)C2] | ++++ |

TABLE 1a-continued

Additional exemplary compounds—Inhibition of KRAS$^{G12C}$ and cRAF Binding

| Structure | RAF1 RBD IC50 |
|---|---|
| | |
| | + |
| | |
| | + |

TABLE 1a-continued

Additional exemplary compounds—Inhibition of KRAS$^{G12C}$ and cRAF Binding

| Structure | RAF 1 RBD IC50 |
|---|---|
| | |
| | + |
| | |
| | + |

TABLE 1a-continued
Additional exemplary compounds—Inhibition of KRAS$^{G12C}$ and cRAF Binding
| Structure | RAF 1 RBD IC50 |
|---|---|
| 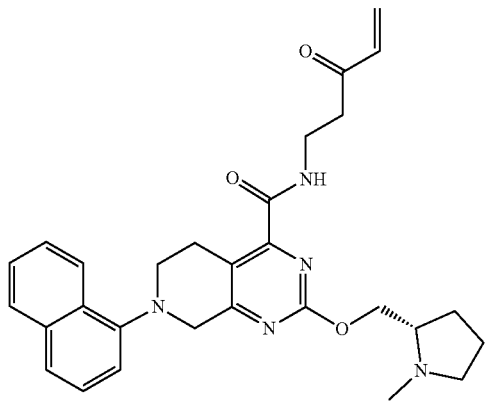 [SMILES: C=CC(=O)CCNC(=O)c1nc(OC[C@@H]2CCCN2C)nc2c1CCN(c1cccc3ccccc13)C2] | |
| 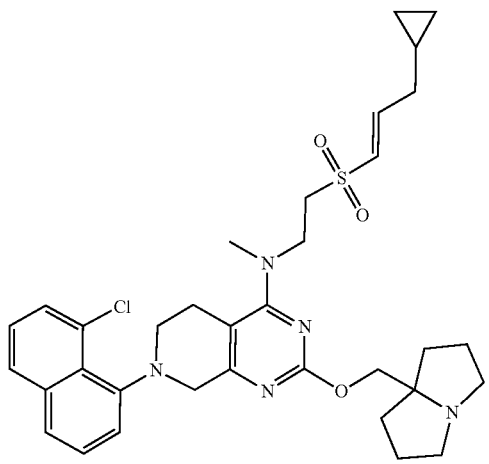 [SMILES: CN(CCS(=O)(=O)/C=C/CC1CC1)c1nc(OCC23CCCN2CCC3)nc2c1CCN(c1cccc3cccc(Cl)c13)C2] | + |
| 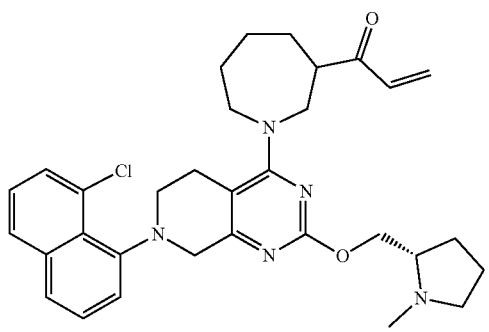 [SMILES: C=CC(=O)C1CCCCN(c2nc(OC[C@@H]3CCCN3C)nc3c2CCN(c2cccc4cccc(Cl)c24)C3)C1] | |

TABLE 1a-continued
Additional exemplary compounds—Inhibition of KRAS$^{G12C}$ and cRAF Binding
| Structure | RAF 1 RBD IC50 |
|---|---|
| 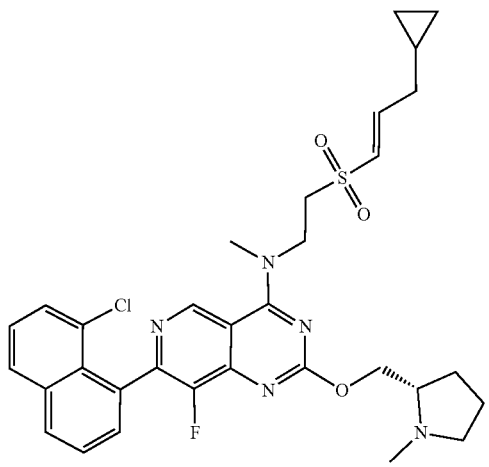 [SMILES: CN(CCS(=O)(=O)/C=C/CC1CC1)c1nc(OC[C@@H]2CCCN2C)nc2c(F)c(-c3cccc4cccc(Cl)c34)ncc12] | + |
| 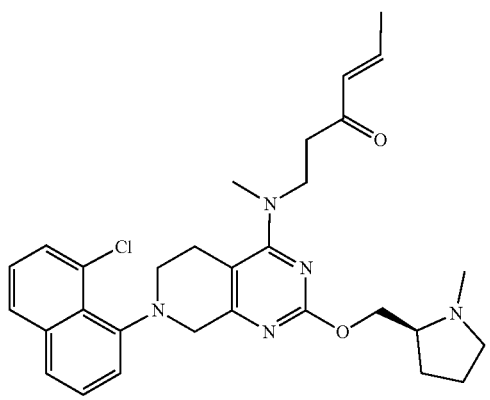 [SMILES: C/C=C/C(=O)CCN(C)c1nc(OC[C@@H]2CCCN2C)nc2c1CCN(c1cccc3cccc(Cl)c13)C2] | + |
| 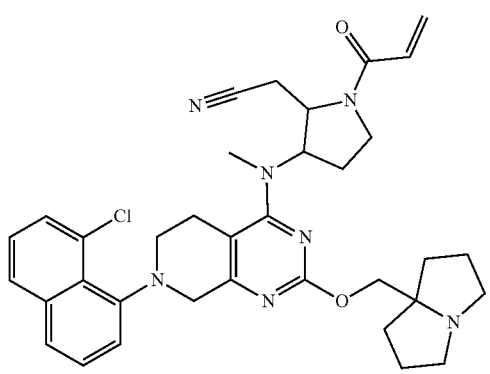 [SMILES: C=CC(=O)N1CCC(N(C)c2nc(OCC34CCCN3CCC4)nc3c2CCN(c2cccc4cccc(Cl)c24)C3)C1CC#N] |  |

TABLE 1a-continued
Additional exemplary compounds—Inhibition of KRAS$^{G12C}$ and cRAF Binding
| Structure | RAF 1 RBD IC50 |
|---|---|
| 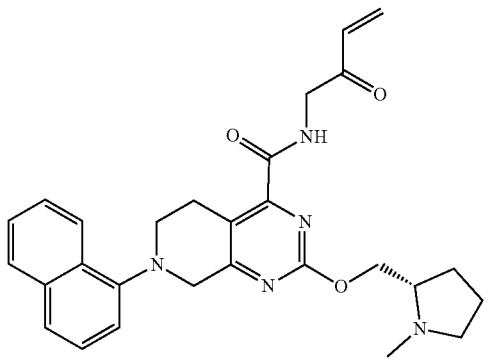 [SMILES: C=CC(=O)CNC(=O)c1nc(OC[C@@H]2CCCN2C)nc2c1CCN(c1cccc3ccccc13)C2] | |
| 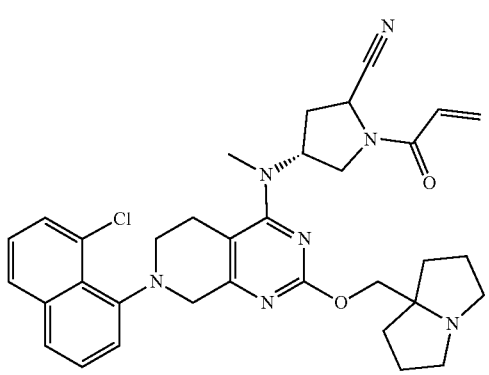 [SMILES: C=CC(=O)N1C[C@H](N(C)c2nc(OCC34CCCN3CCC4)nc3c2CCN(c2cccc4cccc(Cl)c24)C3)CC1C#N] | ++ |
| 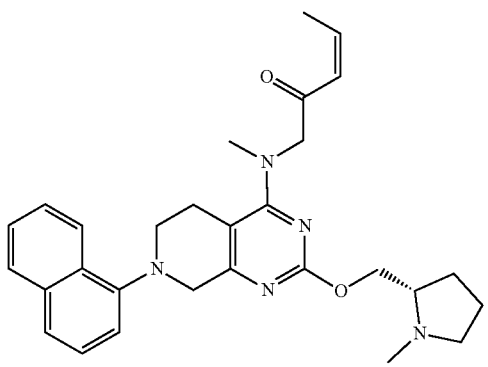 [SMILES: C/C=C\C(=O)CN(C)c1nc(OC[C@@H]2CCCN2C)nc2c1CCN(c1cccc3ccccc13)C2] | |
| 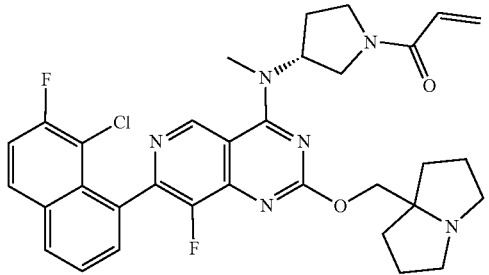 [SMILES: C=CC(=O)N1CC[C@@H](N(C)c2nc(OCC34CCCN3CCC4)nc3c(F)c(-c4cccc5ccc(F)c(Cl)c45)ncc23)C1] | +++ |

TABLE 1a-continued
Additional exemplary compounds—Inhibition of KRAS^{G12C} and cRAF Binding
| Structure | RAF 1 RBD IC50 |
|---|---|
| 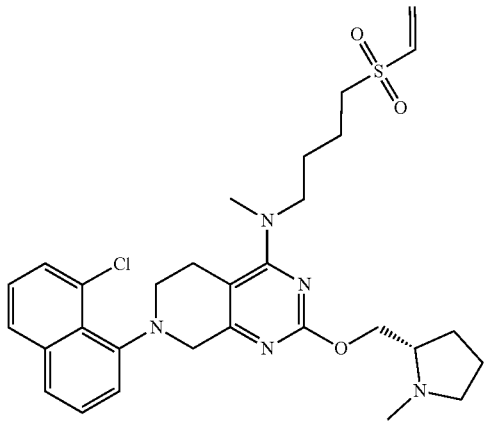 [SMILES: C=CS(=O)(=O)CCCCN(C)c1nc(OC[C@@H]2CCCN2C)nc2c1CCN(c1cccc3cccc(Cl)c13)C2] | |
| 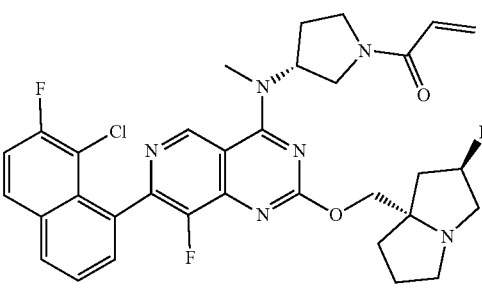 | +++ |
| 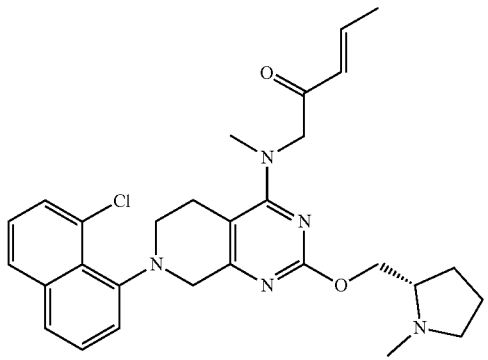 [SMILES: C/C=C/C(=O)CN(C)c1nc(OC[C@@H]2CCCN2C)nc2c1CCN(c1cccc3cccc(Cl)c13)C2] | |
| 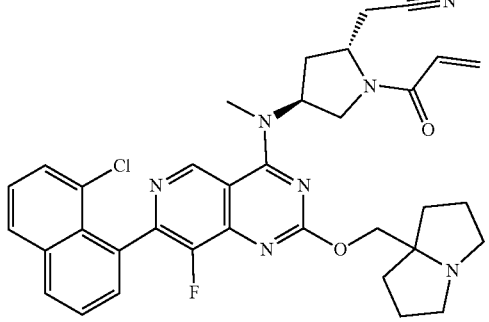 | + |

TABLE 1a-continued
Additional exemplary compounds—Inhibition of KRAS$^{G12C}$ and cRAF Binding
| Structure | RAF1 RBD IC50 |
|---|---|
| 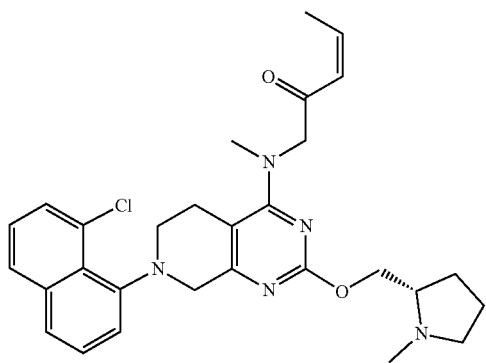 [SMILES: C/C=C\C(=O)CN(C)c1nc(OC[C@@H]2CCCN2C)nc2c1CCN(c1cccc3cccc(Cl)c13)C2] | +++ |
| 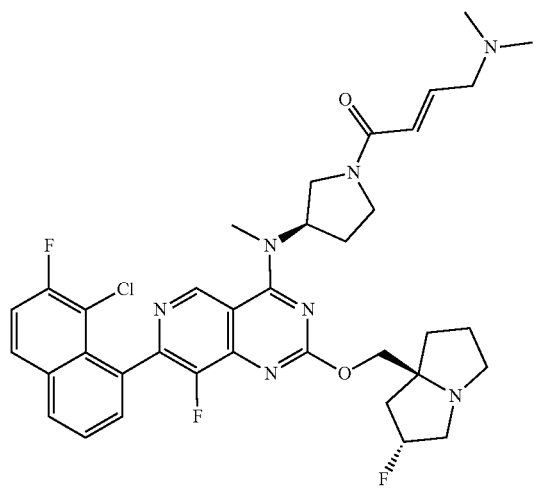 [SMILES: CN(C)C/C=C/C(=O)N1CC[C@@H](N(C)c2nc(OC[C@@]34CCCN3C[C@H](F)C4)nc3c(F)c(-c4cccc5ccc(F)c(Cl)c45)ncc23)C1] | |
| 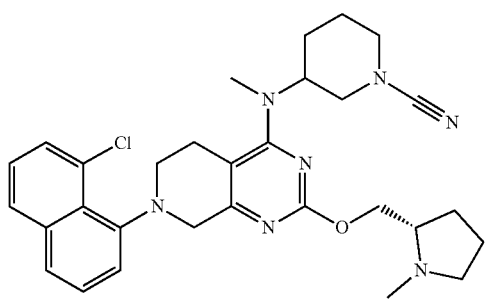 [SMILES: CN(c1nc(OC[C@@H]2CCCN2C)nc2c1CCN(c1cccc3cccc(Cl)c13)C2)C1CCCN(C#N)C1] | |

TABLE 1a-continued
Additional exemplary compounds—Inhibition of $KRAS^{G12C}$ and cRAF Binding
| Structure | RAF 1 RBD IC50 |
|---|---|
| 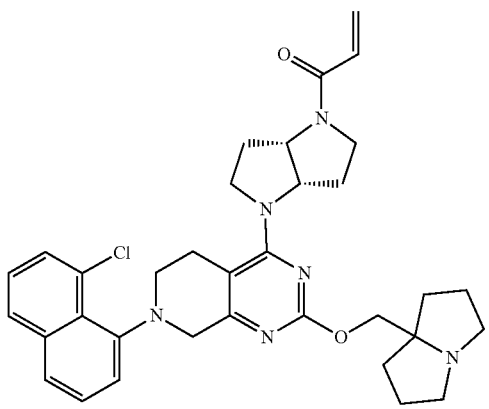 [SMILES: C=CC(=O)N1CC[C@H]2[C@@H]1CCN2c1nc(OCC23CCCN2CCC3)nc2c1CCN(c1cccc3cccc(Cl)c13)C2] | + |
| 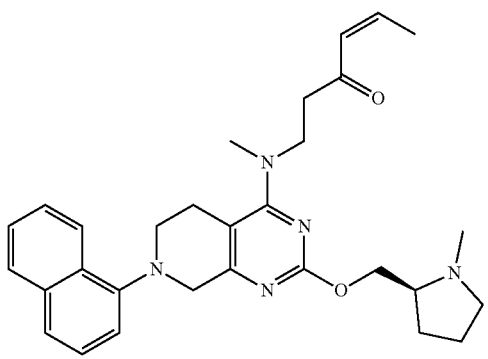 [SMILES: C/C=C\C(=O)CCN(C)c1nc(OC[C@@H]2CCCN2C)nc2c1CCN(c1cccc3ccccc13)C2] | |
| 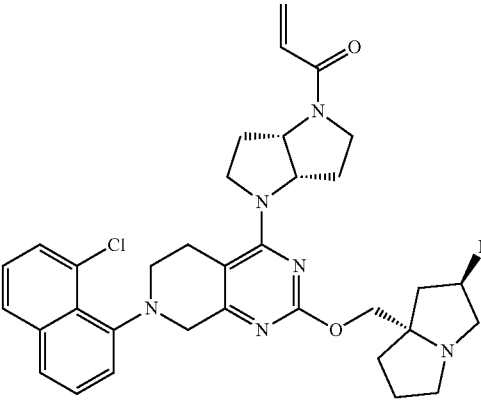 | + |

TABLE 1a-continued
Additional exemplary compounds—Inhibition of KRAS$^{G12C}$ and cRAF Binding
| Structure | RAF 1 RBD IC50 |
|---|---|
| 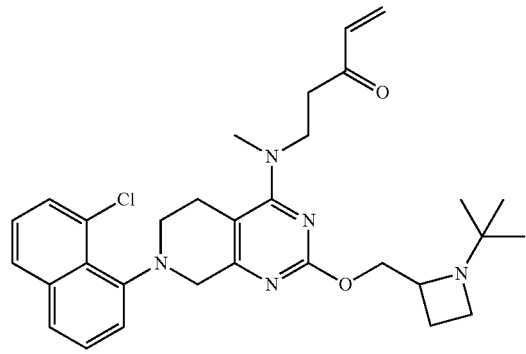 [SMILES: C=CC(=O)CCN(C)c1nc(OCC2CCN2C(C)(C)C)nc2c1CCN(c1cccc3cccc(Cl)c13)C2] | |
| 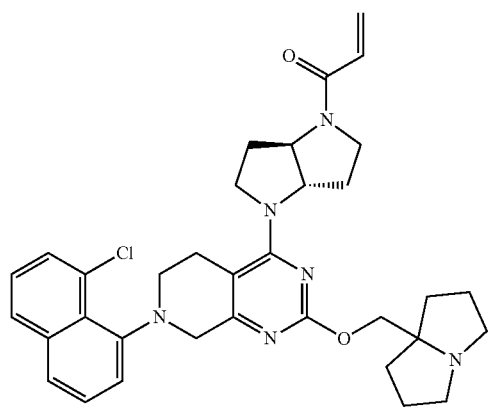 [SMILES: C=CC(=O)N1CC[C@H]2[C@H]1CCN2c1nc(OCC23CCCN2CCC3)nc2c1CCN(c1cccc3cccc(Cl)c13)C2] | + |
| 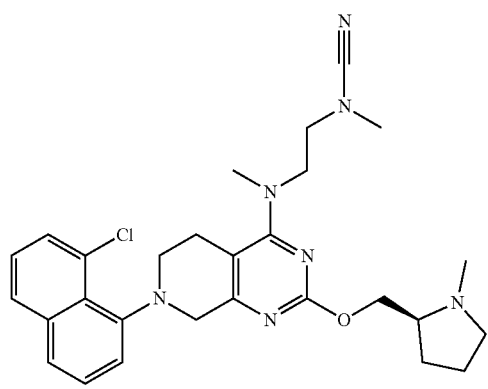 [SMILES: CN(C#N)CCN(C)c1nc(OC[C@@H]2CCCN2C)nc2c1CCN(c1cccc3cccc(Cl)c13)C2] | |

TABLE 1a-continued

Additional exemplary compounds—Inhibition of KRAS^G12C and cRAF Binding

| Structure | RAF1 RBD IC50 |
|---|---|
| 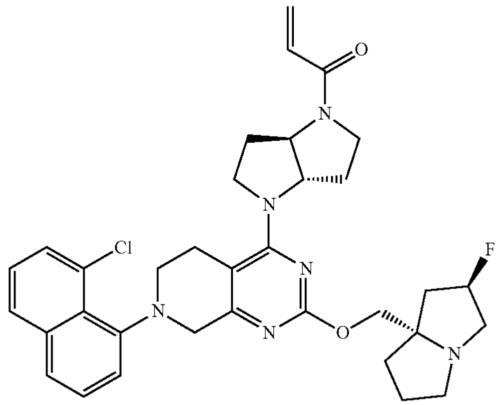 [SMILES: C=CC(=O)N1CC[C@H]2[C@H]1CCN2c1nc(OC[C@@]23CCCN2C[C@H](F)C3)nc2c1CCN(c1cccc3cccc(Cl)c13)C2] | + |
| | +++ |
| | +++ |
| | +++ |

TABLE 1a-continued

Additional exemplary compounds—Inhibition of KRAS$^{G12C}$ and cRAF Binding

| Structure | RAF 1 RBD IC50 |
|---|---|
| 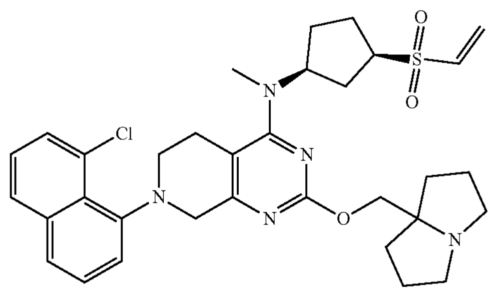 [SMILES: C=CS(=O)(=O)[C@@H]1CC[C@H](N(C)c2nc(OCC34CCCN3CCC4)nc3c2CCN(c2cccc4cccc(Cl)c24)C3)C1] | + |
| | |
| 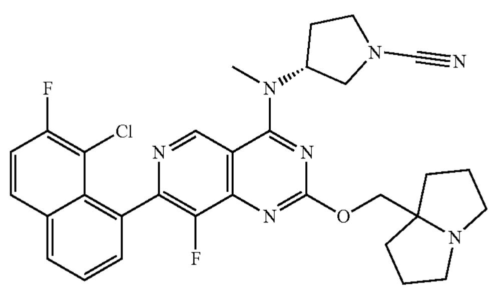 [SMILES: CN(c1nc(OCC23CCCN2CCC3)nc2c(F)c(-c3cccc4ccc(F)c(Cl)c34)ncc12)[C@@H]1CCN(C#N)C1] | +++ |
| | |

TABLE 1a-continued

Additional exemplary compounds—Inhibition of KRAS$^{G12C}$ and cRAF Binding

| Structure | RAF 1 RBD IC50 |
|---|---|
| | +++ |
| | |
| | +++ |

TABLE 1a-continued

Additional exemplary compounds—Inhibition of KRAS$^{G12C}$ and cRAF Binding

| Structure | RAF 1 RBD IC50 |
|---|---|
| | |
| 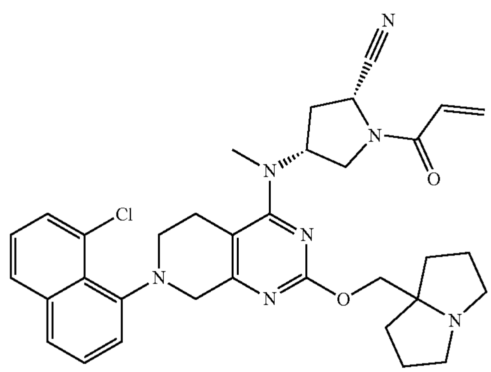 [SMILES: C=CC(=O)N1C[C@H](N(C)c2nc(OCC34CCCN3CCC4)nc3c2CCN(c2cccc4cccc(Cl)c24)C3)C[C@@H]1C#N] | ++ |
| | |
| 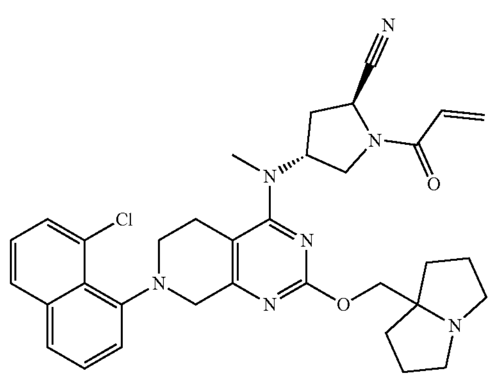 [SMILES: C=CC(=O)N1C[C@H](N(C)c2nc(OCC34CCCN3CCC4)nc3c2CCN(c2cccc4cccc(Cl)c24)C3)C[C@H]1C#N] | +++ |

TABLE 1a-continued
Additional exemplary compounds—Inhibition of KRAS$^{G12C}$ and cRAF Binding
| Structure | RAF 1 RBD IC50 |
|---|---|
| 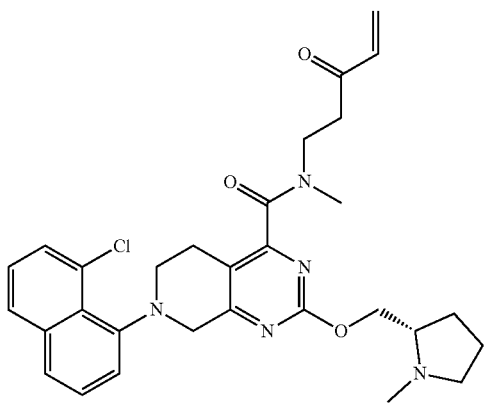 [SMILES: C=CC(=O)CCN(C)C(=O)c1nc(OC[C@@H]2CCCN2C)nc2c1CCN(c1cccc3cccc(Cl)c13)C2] | +++ |
| 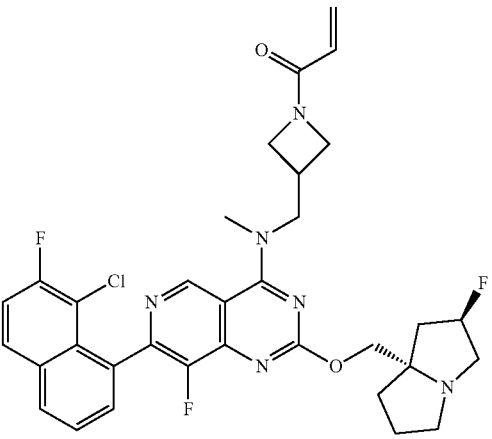 [SMILES: C=CC(=O)N1CC(CN(C)c2nc(OC[C@@]34CCCN3C[C@H](F)C4)nc3c(F)c(-c4cccc5ccc(F)c(Cl)c45)ncc23)C1] | |
| 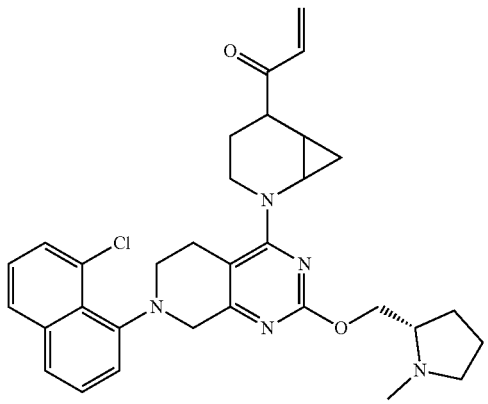 | |

TABLE 1a-continued
Additional exemplary compounds—Inhibition of $KRAS^{G12C}$ and cRAF Binding
| Structure | RAF 1 RBD IC50 |
|---|---|
| 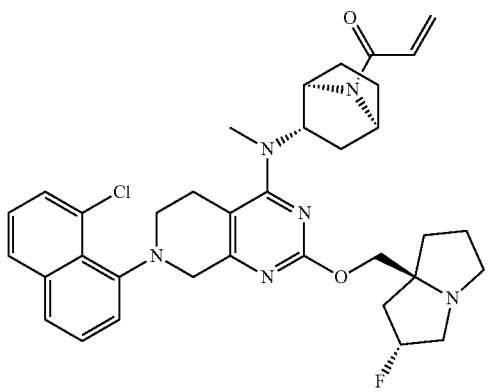 [SMILES: C=CC(=O)N1[C@H]2CC[C@@H]1[C@@H](N(C)c1nc(OC[C@@]34CCCN3C[C@H](F)C4)nc3c1CCN(c1cccc4cccc(Cl)c14)C3)C2] | + |
| 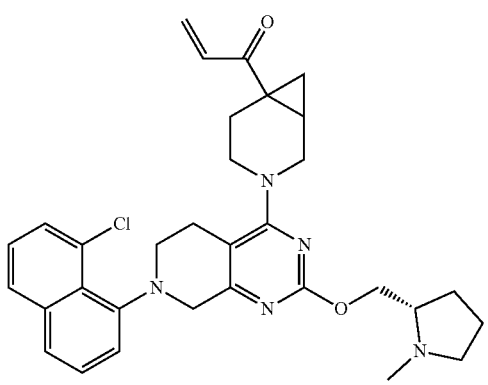 [SMILES: C=CC(=O)C12CCN(c3nc(OC[C@@H]4CCCN4C)nc4c3CCN(c3cccc5cccc(Cl)c35)C4)CC1C2] | ++ |
| 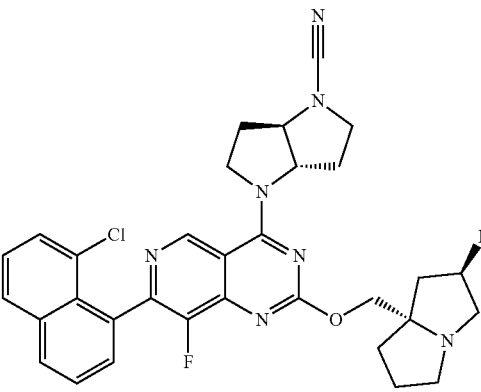 | |

TABLE 1a-continued

Additional exemplary compounds—Inhibition of KRAS$^{G12C}$ and cRAF Binding

| Structure | RAF 1 RBD IC50 |
|---|---|
| | |
| 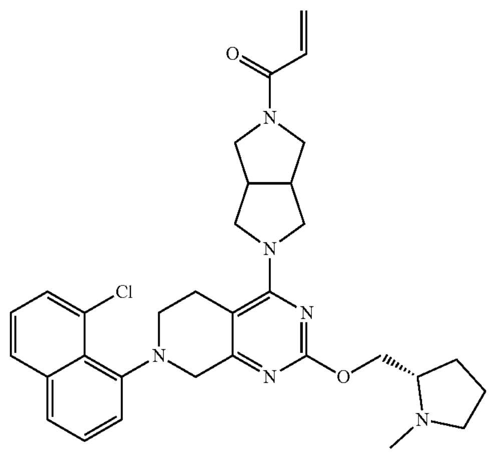 [SMILES: C=CC(=O)N1CC2CN(c3nc(OC[C@@H]4CCCN4C)nc4c3CCN(c3cccc5cccc(Cl)c35)C4)CC2C1] | + |
| | |

TABLE 1a-continued

Additional exemplary compounds—Inhibition of KRAS$^{G12C}$ and cRAF Binding

| Structure | RAF1 RBD IC50 |
|---|---|
| 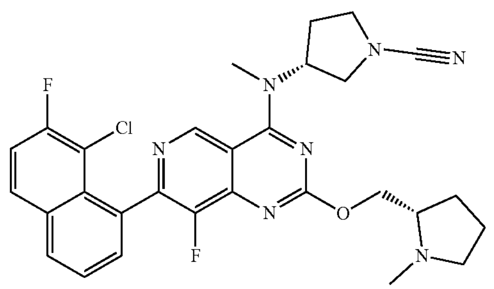 [SMILES: CN1CCC[C@H]1COc1nc(N(C)[C@@H]2CCN(C#N)C2)c2cnc(-c3cccc4ccc(F)c(Cl)c34)c(F)c2n1] | ++ |
| 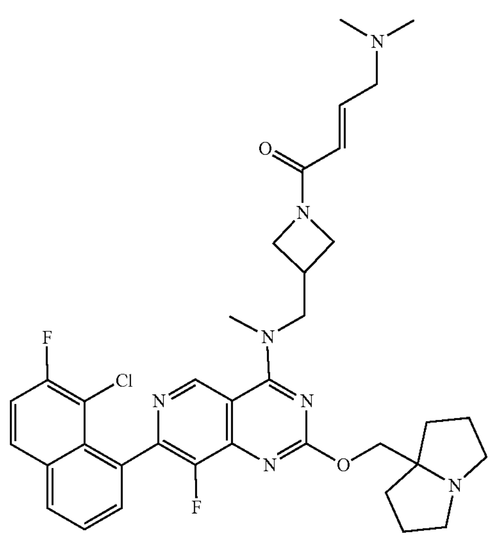 [SMILES: CN(C)C/C=C/C(=O)N1CC(CN(C)c2nc(OCC34CCCN3CCC4)nc3c(F)c(-c4cccc5ccc(F)c(Cl)c45)ncc23)C1] | +++ |

TABLE 1a-continued
*Additional exemplary compounds—Inhibition of KRAS$^{G12C}$ and cRAF Binding*
| Structure | RAF 1 RBD IC50 |
|---|---|
| 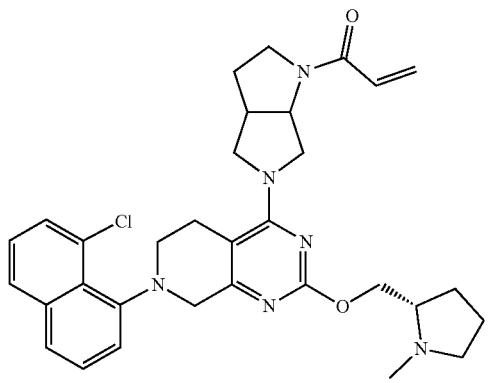 [SMILES: C=CC(=O)N1CCC2CN(c3nc(OC[C@@H]4CCCN4C)nc4c3CCN(c3cccc5cccc(Cl)c35)C4)CC21] | +++ |
| 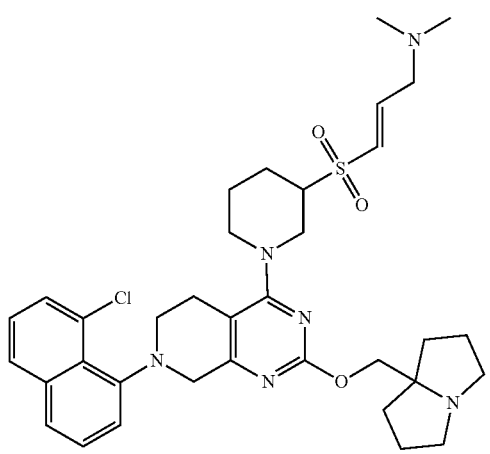 [SMILES: CN(C)C/C=C/S(=O)(=O)C1CCCN(c2nc(OCC34CCCN3CCC4)nc3c2CCN(c2cccc4cccc(Cl)c24)C3)C1] | |
| 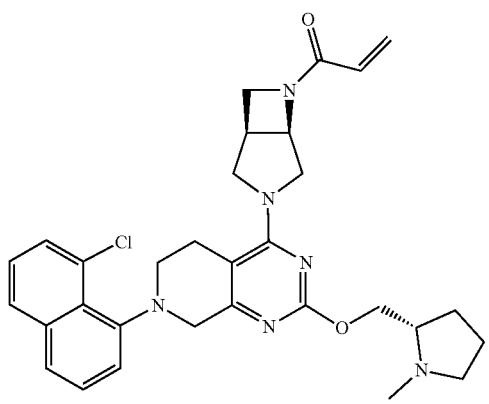 [SMILES: C=CC(=O)N1C[C@@H]2CN(c3nc(OC[C@@H]4CCCN4C)nc4c3CCN(c3cccc5cccc(Cl)c35)C4)C[C@@H]21] | |

TABLE 1a-continued

Additional exemplary compounds—Inhibition of KRAS$^{G12C}$ and cRAF Binding

| Structure | RAF1 RBD IC50 |
|---|---|
| 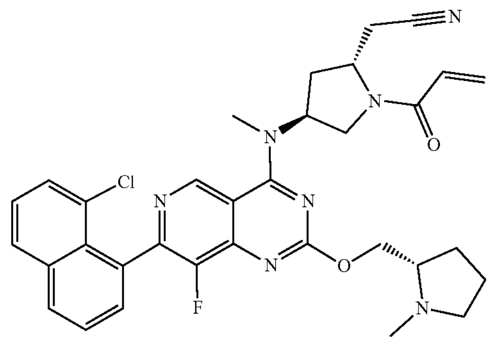 [SMILES: C=CC(=O)N1C[C@@H](N(C)c2nc(OC[C@@H]3CCCN3C)nc3c(F)c(-c4cccc5cccc(Cl)c45)ncc23)C[C@@H]1CC#N] | + |
| | |
| 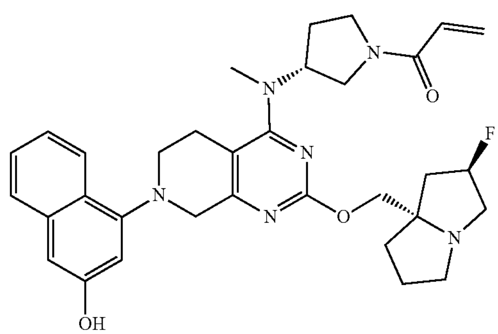 [SMILES: C=CC(=O)N1CC[C@@H](N(C)c2nc(OC[C@@]34CCCN3C[C@H](F)C4)nc3c2CCN(c2cc(O)cc4ccccc24)C3)C1] | ++ |
| | |

TABLE 1a-continued

Additional exemplary compounds—Inhibition of KRAS$^{G12C}$ and cRAF Binding

| Structure | RAF1 RBD IC50 |
|---|---|
| 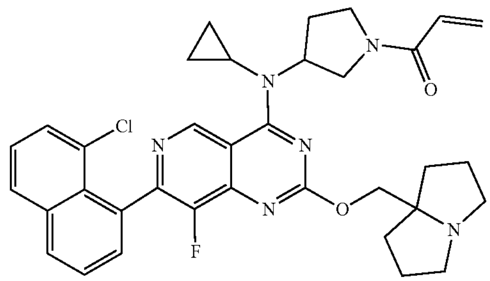 [SMILES: C=CC(=O)N1CCC(N(c2nc(OCC34CCCN3CCC4)nc3c(F)c(-c4cccc5cccc(Cl)c45)ncc23)C2CC2)C1] | + |
| | |
| 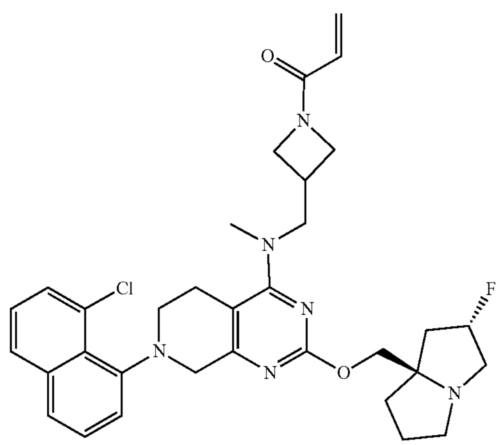 [SMILES: C=CC(=O)N1CC(CN(C)c2nc(OC[C@]34CCCN3C[C@@H](F)C4)nc3c2CCN(c2cccc4cccc(Cl)c24)C3)C1] | ++ |
| | |

TABLE 1a-continued
Additional exemplary compounds—Inhibition of KRAS$^{G12C}$ and cRAF Binding
| Structure | RAF 1 RBD IC50 |
|---|---|
| 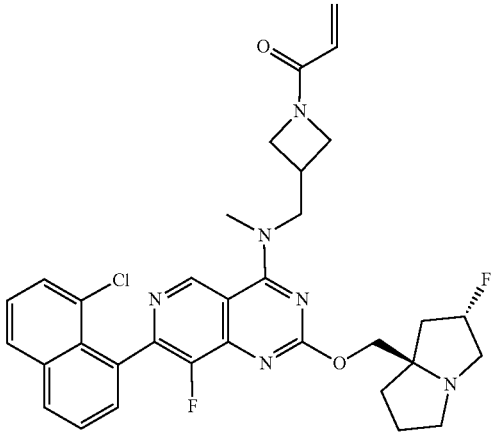 [SMILES: C=CC(=O)N1CC(CN(C)c2nc(OC[C@]34CCCN3C[C@@H](F)C4)nc3c(F)c(-c4cccc5cccc(Cl)c45)ncc23)C1] | ++ |
| 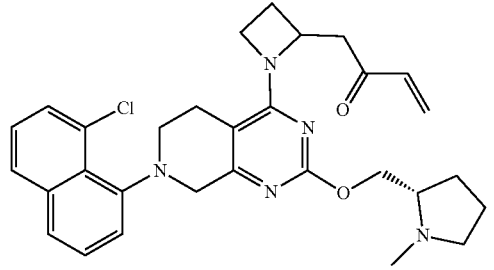 [SMILES: C=CC(=O)CC1CCN1c1nc(OC[C@@H]2CCCN2C)nc2c1CCN(c1cccc3cccc(Cl)c13)C2] | |
| 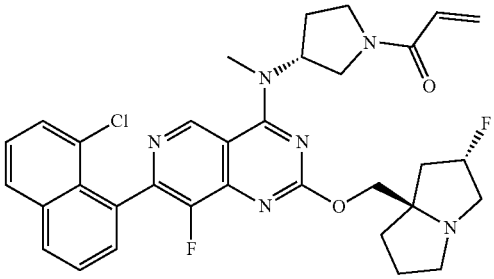 [SMILES: C=CC(=O)N1CC[C@@H](N(C)c2nc(OC[C@]34CCCN3C[C@@H](F)C4)nc3c(F)c(-c4cccc5cccc(Cl)c45)ncc23)C1] | ++ |
| 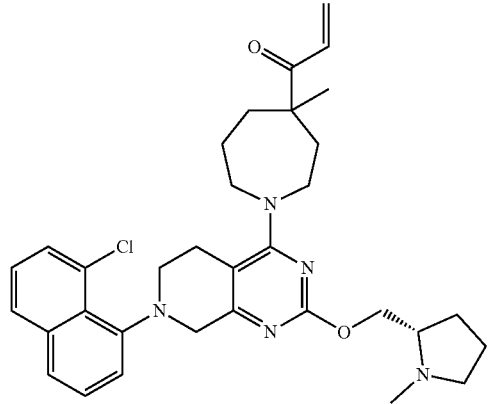 [SMILES: C=CC(=O)C1(C)CCCN(c2nc(OC[C@@H]3CCCN3C)nc3c2CCN(c2cccc4cccc(Cl)c24)C3)CC1] | |

TABLE 1a-continued

Additional exemplary compounds—Inhibition of KRAS$^{G12C}$ and cRAF Binding

| Structure | RAF 1 RBD IC50 |
|---|---|
| | + |
| | |
| | + |

TABLE 1a-continued
Additional exemplary compounds—Inhibition of KRAS$^{G12C}$ and cRAF Binding
| Structure | RAF 1 RBD IC50 |
|---|---|
| 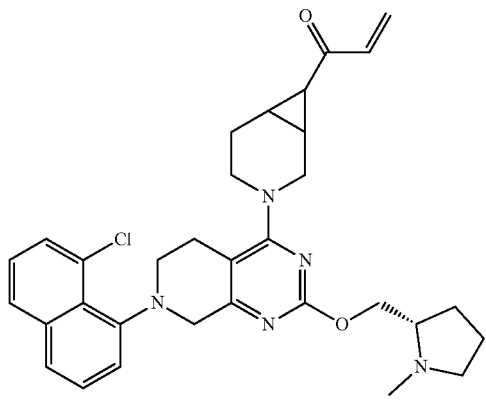 [SMILES: C=CC(=O)C1C2CCN(c3nc(OC[C@@H]4CCCN4C)nc4c3CCN(c3cccc5cccc(Cl)c35)C4)CC21] | |
| 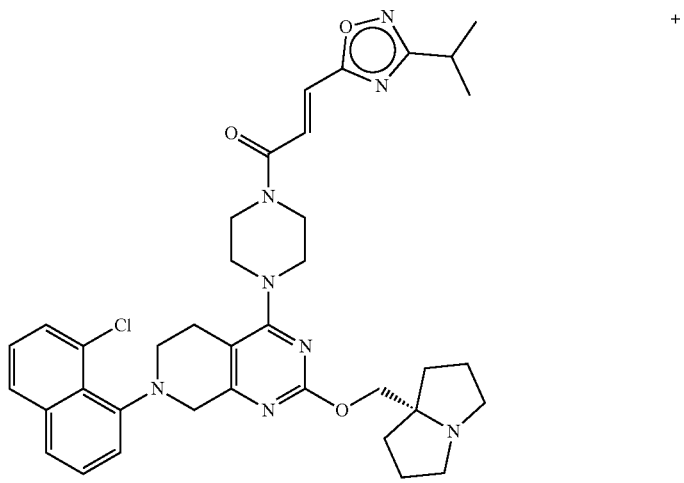 | + |
| 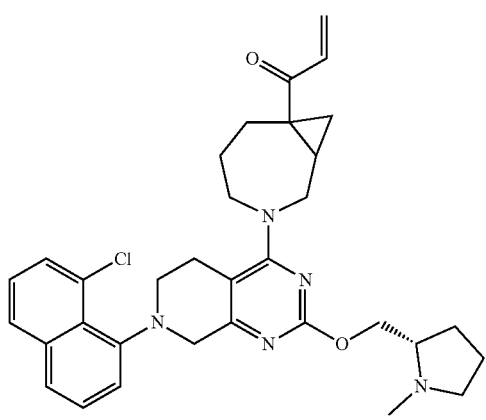 [SMILES: C=CC(=O)C12CCCN(c3nc(OC[C@@H]4CCCN4C)nc4c3CCN(c3cccc5cccc(Cl)c35)C4)CC1C2] | |

TABLE 1a-continued

Additional exemplary compounds—Inhibition of KRAS$^{G12C}$ and cRAF Binding

| Structure | RAF 1 RBD IC50 |
|---|---|
| | + |
| | |
| | + |

TABLE 1a-continued

Additional exemplary compounds—Inhibition of KRAS^G12C and cRAF Binding

| Structure | RAF 1 RBD IC50 |
|---|---|
| | |
| | + |
| | |
| | + |

TABLE 1a-continued
Additional exemplary compounds—Inhibition of KRAS$^{G12C}$ and cRAF Binding
| Structure | RAF 1 RBD IC50 |
|---|---|
| 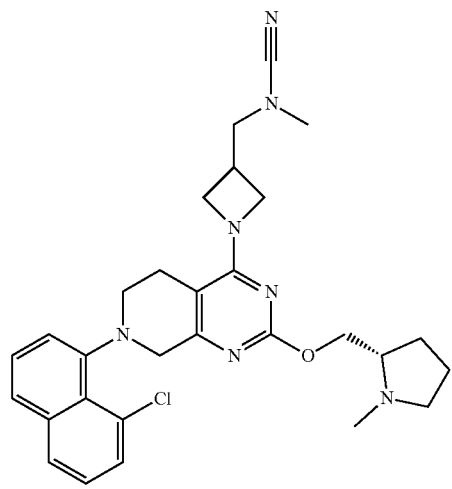 [SMILES: CN(C#N)CC1CN(c2nc(OC[C@@H]3CCCN3C)nc3c2CCN(c2cccc4cccc(Cl)c24)C3)C1] | |
| 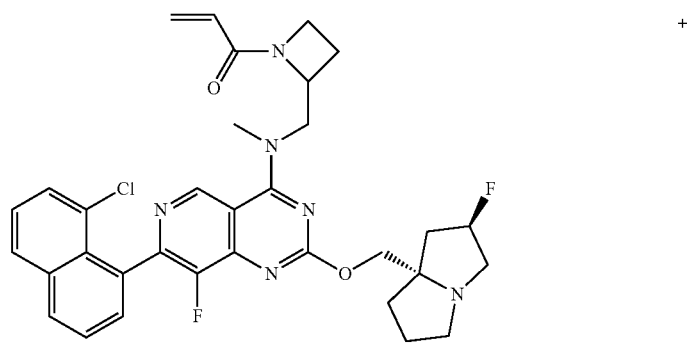 | + |
| 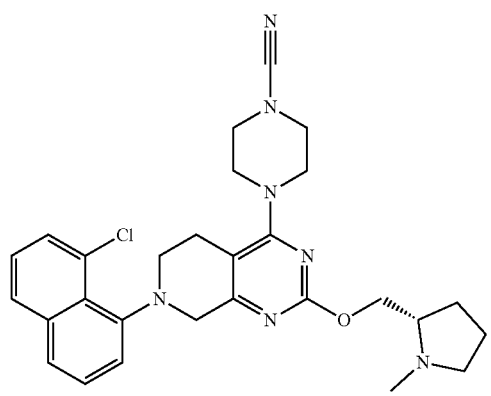 [SMILES: CN1CCC[C@H]1COc1nc2c(c(N3CCN(C#N)CC3)n1)CCN(c1cccc3cccc(Cl)c13)C2] | |

TABLE 1a-continued

Additional exemplary compounds—Inhibition of KRAS$^{G12C}$ and cRAF Binding

| Structure | RAF1 RBD IC50 |
|---|---|
| 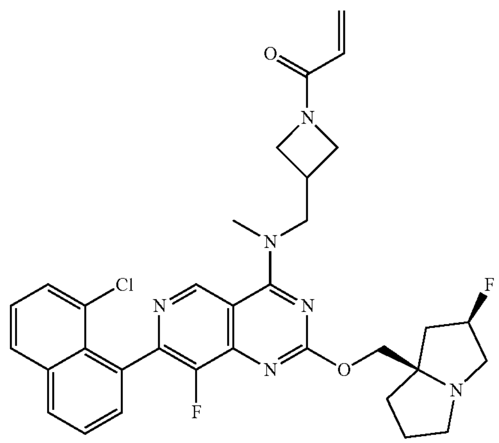 [SMILES: C=CC(=O)N1CC(CN(C)c2nc(OC[C@]34CCCN3C[C@H](F)C4)nc3c(F)c(-c4cccc5cccc(Cl)c45)ncc23)C1] | + |
| 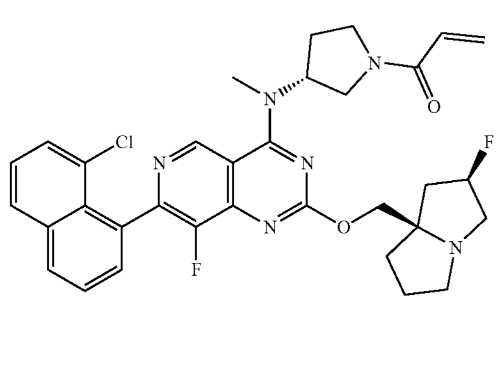 [SMILES: C=CC(=O)N1CC[C@@H](N(C)c2nc(OC[C@]34CCCN3C[C@H](F)C4)nc3c(F)c(-c4cccc5cccc(Cl)c45)ncc23)C1] | ++ |

TABLE 1a-continued

Additional exemplary compounds—Inhibition of KRAS^G12C and cRAF Binding

| Structure | RAF 1 RBD IC50 |
|---|---|
| | |
| 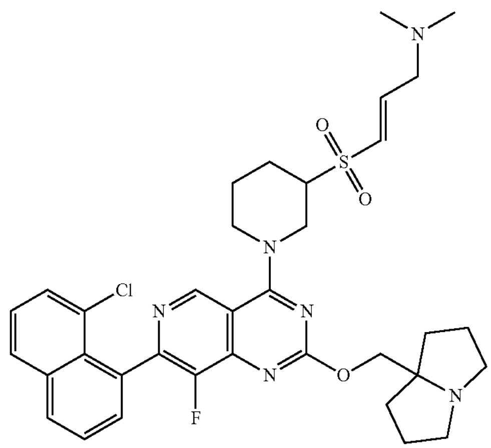 [SMILES: CN(C)C/C=C/S(=O)(=O)C1CCCN(c2nc(OCC34CCCN3CCC4)nc3c(F)c(-c4cccc5cccc(Cl)c45)ncc23)C1] | +++ |
| | |
| 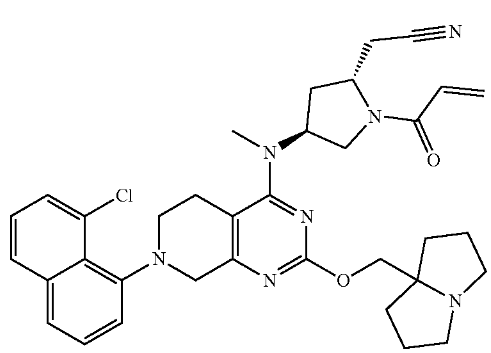 [SMILES: C=CC(=O)N1C[C@@H](N(C)c2nc(OCC34CCCN3CCC4)nc3c2CCN(c2cccc4cccc(Cl)c24)C3)C[C@@H]1CC#N] | + |

TABLE 1a-continued

Additional exemplary compounds—Inhibition of KRAS$^{G12C}$ and cRAF Binding

| Structure | RAF 1 RBD IC50 |
|---|---|
| | |
| | + |
| | |
| | + |

TABLE 1a-continued

Additional exemplary compounds—Inhibition of KRAS$^{G12C}$ and cRAF Binding

| Structure | RAF1 RBD IC50 |
|---|---|
| | |
| | + |
| | |
| | + |

TABLE 1a-continued
Additional exemplary compounds—Inhibition of KRAS$^{G12C}$ and cRAF Binding
| Structure | RAF 1 RBD IC50 |
|---|---|
| 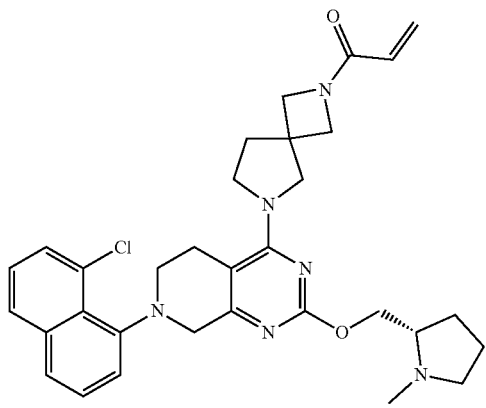 [SMILES: C=CC(=O)N1CC2(CCN(c3nc(OC[C@@H]4CCCN4C)nc4c3CCN(c3cccc5cccc(Cl)c35)C4)C2)C1] | |
| 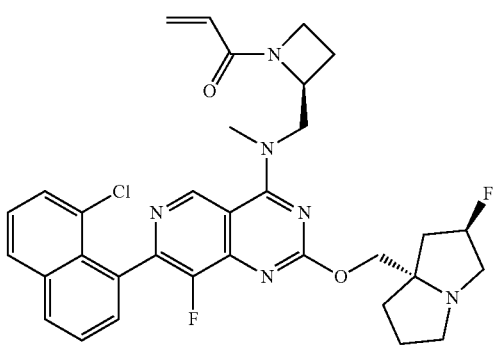 [SMILES: C=CC(=O)N1CC[C@H]1CN(C)c1nc(OC[C@@]23CCCN2C[C@H](F)C3)nc2c(F)c(-c3cccc4cccc(Cl)c34)ncc12] | + |
| 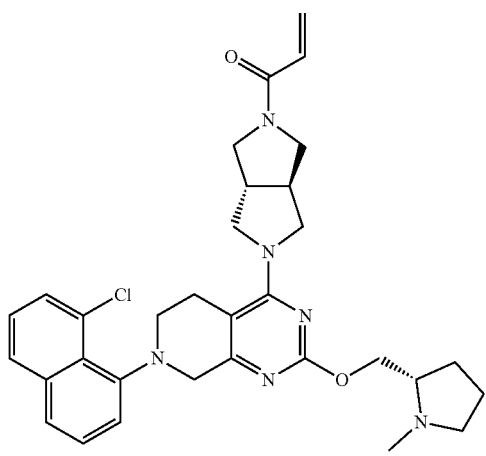 [SMILES: C=CC(=O)N1C[C@H]2CN(c3nc(OC[C@@H]4CCCN4C)nc4c3CCN(c3cccc5cccc(Cl)c35)C4)C[C@@H]2C1] | |

TABLE 1a-continued

Additional exemplary compounds—Inhibition of KRAS^G12C and cRAF Binding

| Structure | RAF 1 RBD IC50 |
|---|---|
| | + |
| | |
| | + |
| | |

TABLE 1a-continued

Additional exemplary compounds—Inhibition of KRAS$^{G12C}$ and cRAF Binding

| Structure | RAF 1 RBD IC50 |
|---|---|
| 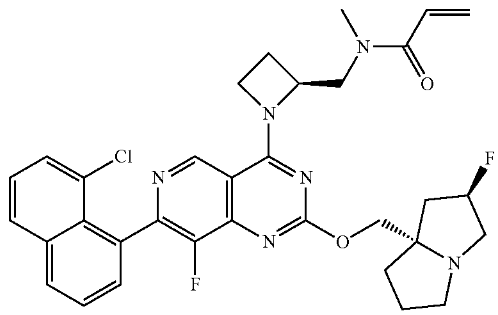 [SMILES: C=CC(=O)N(C)C[C@@H]1CCN1c1nc(OC[C@@]23CCCN2C[C@H](F)C3)nc2c(F)c(-c3cccc4cccc(Cl)c34)ncc12] | + |
| | |
| 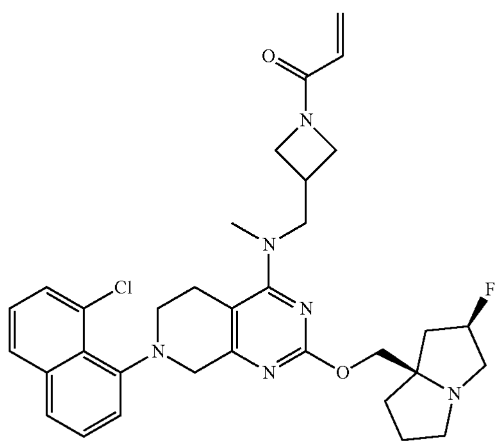 [SMILES: C=CC(=O)N1CC(CN(C)c2nc(OC[C@]34CCCN3C[C@H](F)C4)nc3c2CCN(c2cccc4cccc(Cl)c24)C3)C1] | ++ |
| | |

TABLE 1a-continued

Additional exemplary compounds—Inhibition of KRAS^G12C and cRAF Binding

| Structure | RAF 1 RBD IC50 |
|---|---|
| | +++ |
| | |
| | +++ |
| | |

TABLE 1a-continued

Additional exemplary compounds—Inhibition of KRAS$^{G12C}$ and cRAF Binding

| Structure | RAF 1 RBD IC50 |
|---|---|
| | + |
| | |
| | + |
| | |

TABLE 1a-continued

Additional exemplary compounds—Inhibition of KRAS$^{G12C}$ and cRAF Binding

| Structure | RAF1 RBD IC50 |
|---|---|
| | + |
| | + |
| | |

TABLE 1a-continued
Additional exemplary compounds—Inhibition of $KRAS^{G12C}$ and cRAF Binding
| Structure | RAF 1 RBD IC50 |
|---|---|
| 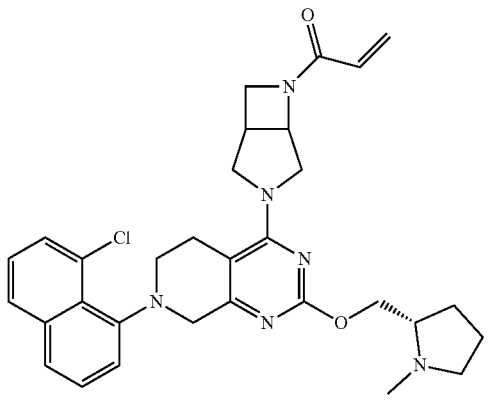 [SMILES: C=CC(=O)N1CC2CN(c3nc(OC[C@@H]4CCCN4C)nc4c3CCN(c3cccc5cccc(Cl)c35)C4)CC21] | |
| 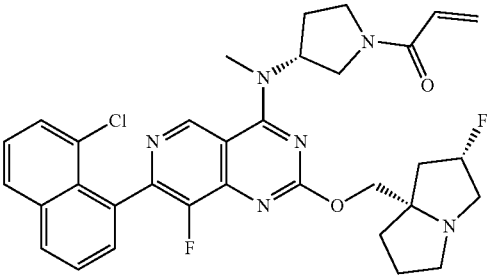 [SMILES: C=CC(=O)N1CC[C@@H](N(C)c2nc(OC[C@@]34CCCN3C[C@@H](F)C4)nc3c(F)c(-c4cccc5cccc(Cl)c45)ncc23)C1] | + |
| 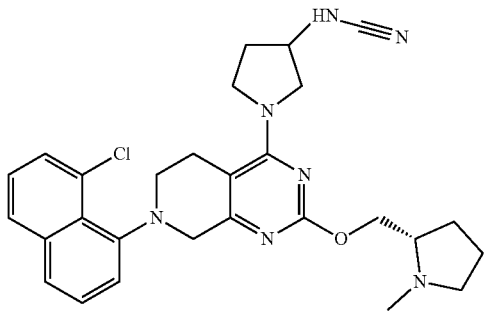 [SMILES: CN1CCC[C@H]1COc1nc2c(c(N3CCC(NC#N)C3)n1)CCN(c1cccc3cccc(Cl)c13)C2] | |
| 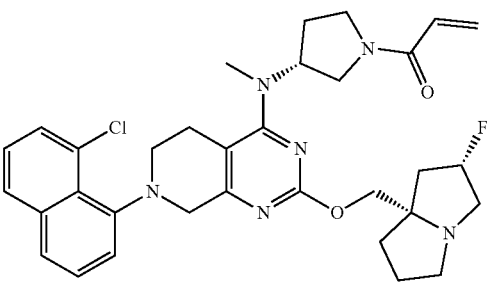 [SMILES: C=CC(=O)N1CC[C@@H](N(C)c2nc(OC[C@@]34CCCN3C[C@@H](F)C4)nc3c2CCN(c2cccc4cccc(Cl)c24)C3)C1] | + |

TABLE 1a-continued

Additional exemplary compounds—Inhibition of KRAS$^{G12C}$ and cRAF Binding

| Structure | RAF 1 RBD IC50 |
|---|---|
| | |
| | + |
| | |
| | + |

TABLE 1a-continued

Additional exemplary compounds—Inhibition of KRAS$^{G12C}$ and cRAF Binding

| Structure | RAF 1 RBD IC50 |
|---|---|
| | |
| 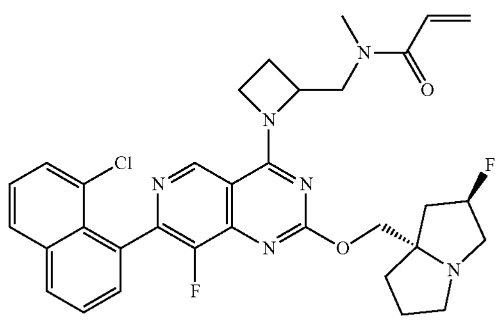 [SMILES: C=CC(=O)N(C)CC1CCN1c1nc(OC[C@@]23CCCN2C[C@H](F)C3)nc2c(F)c(-c3cccc4cccc(Cl)c34)ncc12] | + |
| | |
| 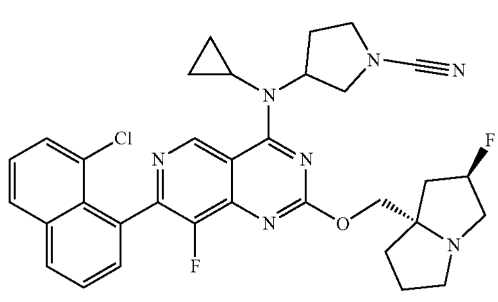 [SMILES: N#CN1CCC(N(c2nc(OC[C@@]34CCCN3C[C@H](F)C4)nc3c(F)c(-c4cccc5cccc(Cl)c45)ncc23)C2CC2)C1] | +++ |

TABLE 1a-continued

Additional exemplary compounds—Inhibition of KRAS$^{G12C}$ and cRAF Binding

| Structure | RAF 1 RBD IC50 |
|---|---|
| | |
| 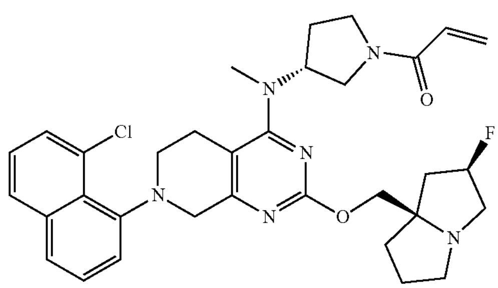 [SMILES: C=CC(=O)N1CC[C@@H](N(C)c2nc(OC[C@]34CCCN3C[C@H](F)C4)nc3c2CCN(c2cccc4cccc(Cl)c24)C3)C1] | + |
| | |
| 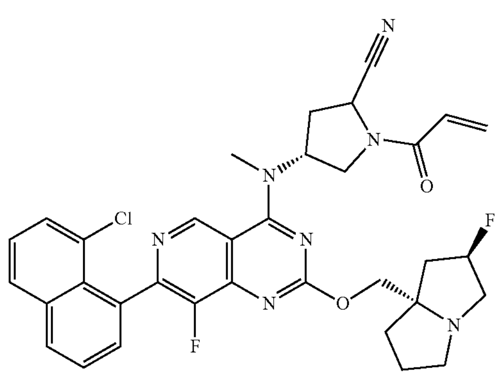 [SMILES: C=CC(=O)N1C[C@H](N(C)c2nc(OC[C@@]34CCCN3C[C@H](F)C4)nc3c(F)c(-c4cccc5cccc(Cl)c45)ncc23)CC1C#N] | +++ |

TABLE 1a-continued
Additional exemplary compounds—Inhibition of $KRAS^{G12C}$ and cRAF Binding
| Structure | RAF 1 RBD IC50 |
|---|---|
| 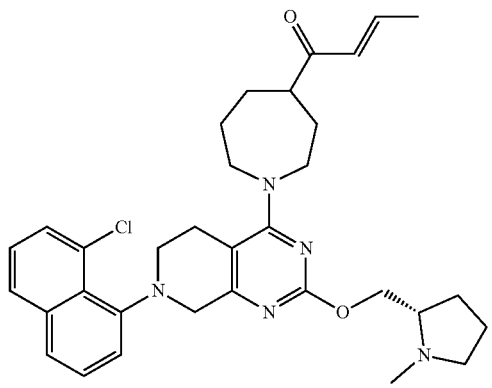 [SMILES: C/C=C/C(=O)C1CCCN(c2nc(OC[C@@H]3CCCN3C)nc3c2CCN(c2cccc4cccc(Cl)c24)C3)CC1] | |
| 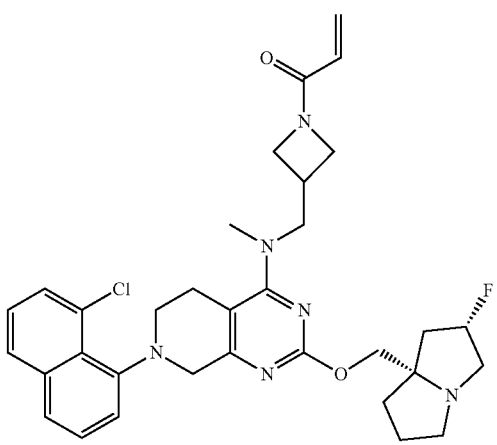 [SMILES: C=CC(=O)N1CC(CN(C)c2nc(OC[C@@]34CCCN3C[C@@H](F)C4)nc3c2CCN(c2cccc4cccc(Cl)c24)C3)C1] | + |
| 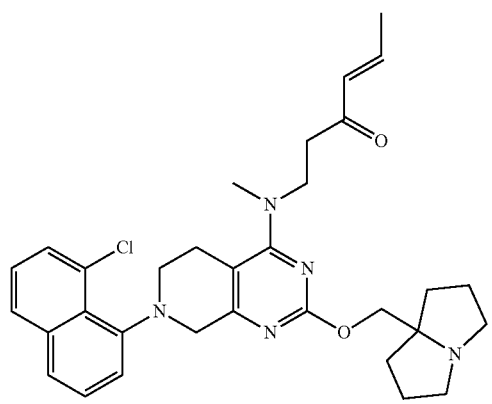 [SMILES: C/C=C/C(=O)CCN(C)c1nc(OCC23CCCN2CCC3)nc2c1CCN(c1cccc3cccc(Cl)c13)C2] | |

TABLE 1a-continued

Additional exemplary compounds—Inhibition of KRAS$^{G12C}$ and cRAF Binding

| Structure | RAF 1 RBD IC50 |
|---|---|
| | + |
| | |
| | + |

TABLE 1a-continued

Additional exemplary compounds—Inhibition of KRAS^G12C and cRAF Binding

| Structure | RAF1 RBD IC50 |
|---|---|
| | |
| | + |
| | |
| | + |

TABLE 1a-continued
Additional exemplary compounds—Inhibition of KRAS$^{G12C}$ and cRAF Binding
| Structure | RAF 1 RBD IC50 |
|---|---|
| 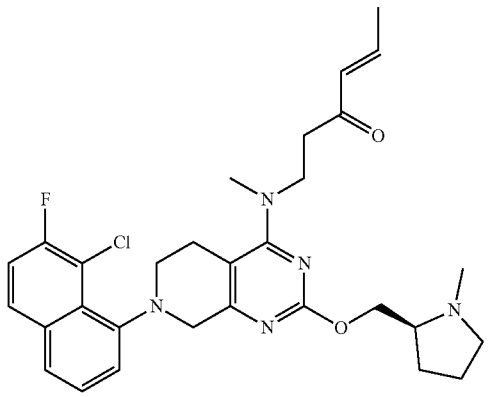 [SMILES: C/C=C/C(=O)CCN(C)c1nc(OC[C@@H]2CCCN2C)nc2c1CCN(c1cccc3ccc(F)c(Cl)c13)C2] | |
| 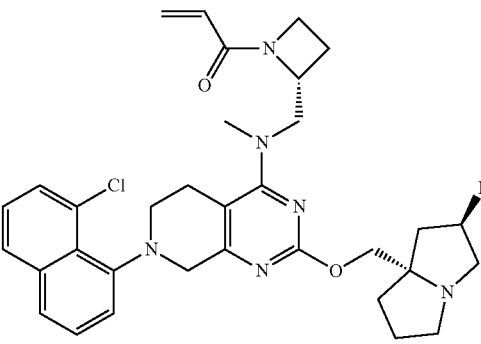 | + |
| 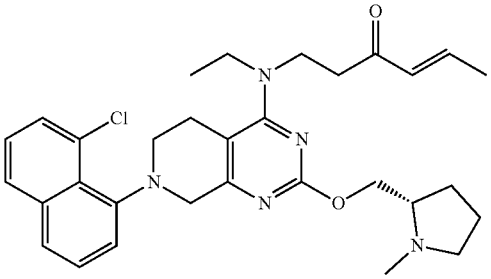 [SMILES: C/C=C/C(=O)CCN(CC)c1nc(OC[C@@H]2CCCN2C)nc2c1CCN(c1cccc3cccc(Cl)c13)C2] | |
| 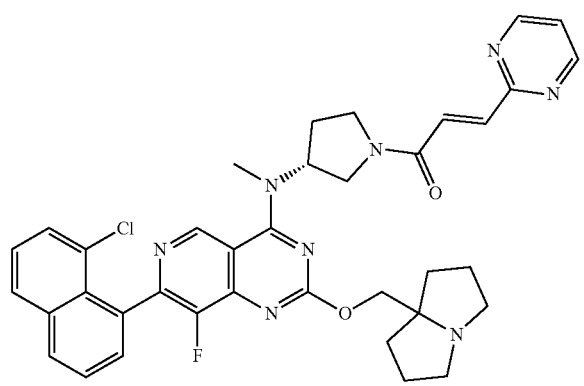 [SMILES: CN(c1nc(OCC23CCCN2CCC3)nc2c(F)c(-c3cccc4cccc(Cl)c34)ncc12)[C@@H]1CCN(C(=O)/C=C/c2ncccn2)C1] | + |

TABLE 1a-continued

Additional exemplary compounds—Inhibition of KRAS$^{G12C}$ and cRAF Binding

| Structure | RAF 1 RBD IC50 |
|---|---|
| | |
| 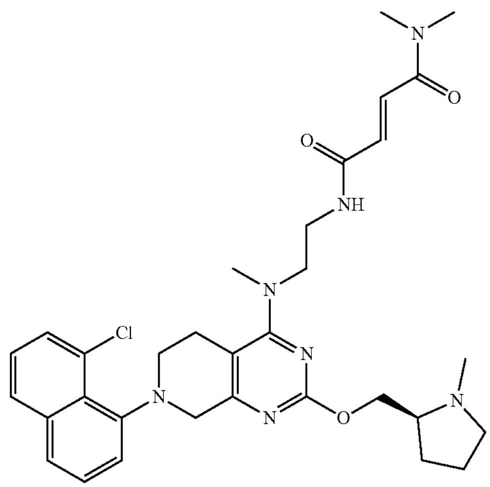 [SMILES: CN(C)C(=O)/C=C/C(=O)NCCN(C)c1nc(OC[C@@H]2CCCN2C)nc2c1CCN(c1cccc3cccc(Cl)c13)C2] | + |
| | |

TABLE 1a-continued
Additional exemplary compounds—Inhibition of KRAS$^{G12C}$ and cRAF Binding
| Structure | RAF 1 RBD IC50 |
|---|---|
| 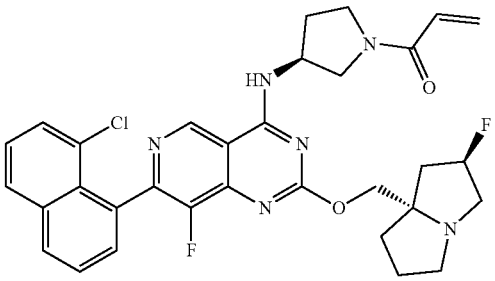 [SMILES: C=CC(=O)N1CC[C@H](Nc2nc(OC[C@@]34CCCN3C[C@H](F)C4)nc3c(F)c(-c4cccc5cccc(Cl)c45)ncc23)C1] | + |
| 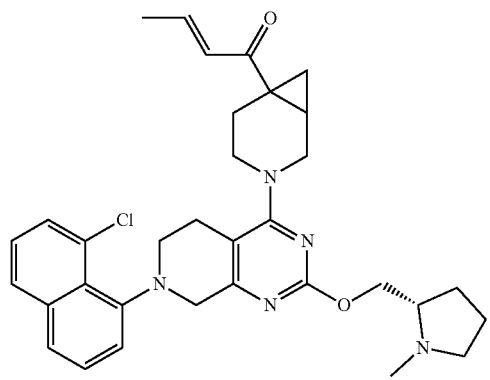 [SMILES: C/C=C/C(=O)C12CCN(c3nc(OC[C@@H]4CCCN4C)nc4c3CCN(c3cccc5cccc(Cl)c35)C4)CC1C2] | |
| 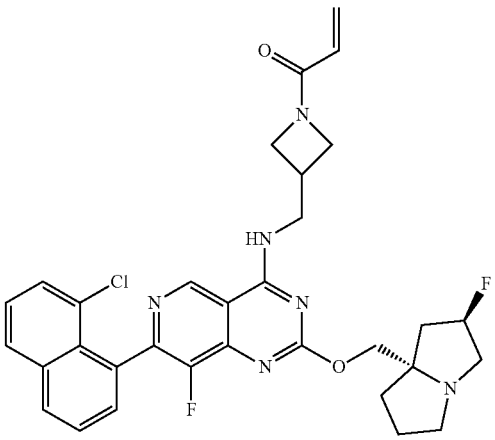 [SMILES: C=CC(=O)N1CC(CNc2nc(OC[C@@]34CCCN3C[C@H](F)C4)nc3c(F)c(-c4cccc5cccc(Cl)c45)ncc23)C1] | ++ |
| 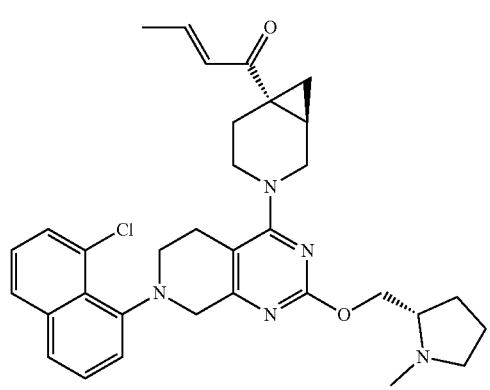 [SMILES: C/C=C/C(=O)[C@@]12CCN(c3nc(OC[C@@H]4CCCN4C)nc4c3CCN(c3cccc5cccc(Cl)c35)C4)C[C@@H]1C2] | |

TABLE 1a-continued

*Additional exemplary compounds—Inhibition of KRAS$^{G12C}$ and cRAF Binding*

| Structure | RAF1 RBD IC50 |
|---|---|
| | + |
| | |
| | + |
| | |

TABLE 1a-continued

Additional exemplary compounds—Inhibition of KRAS^G12C and cRAF Binding

| Structure | RAF 1 RBD IC50 |
|---|---|
| | + |
| | |
| | + |
| | |

TABLE 1a-continued

Additional exemplary compounds—Inhibition of KRAS$^{G12C}$ and cRAF Binding

| Structure | RAF 1 RBD IC50 |
|---|---|
| | + |
| | |
| | + |
| 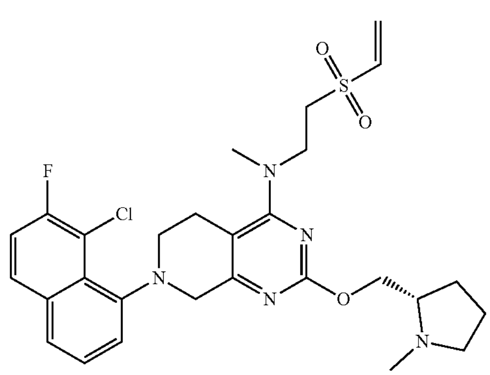 [SMILES: C=CS(=O)(=O)CCN(C)c1nc(OC[C@@H]2CCCN2C)nc2c1CCN(c1cccc3ccc(F)c(Cl)c13)C2] | ++ |

TABLE 1a-continued
Additional exemplary compounds—Inhibition of KRAS$^{G12C}$ and cRAF Binding
| Structure | RAF 1 RBD IC50 |
|---|---|
| 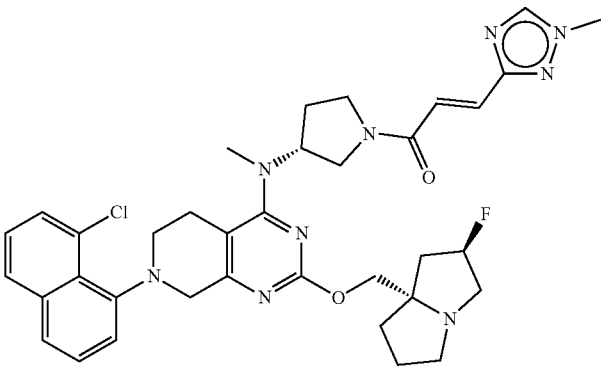 | + |
| 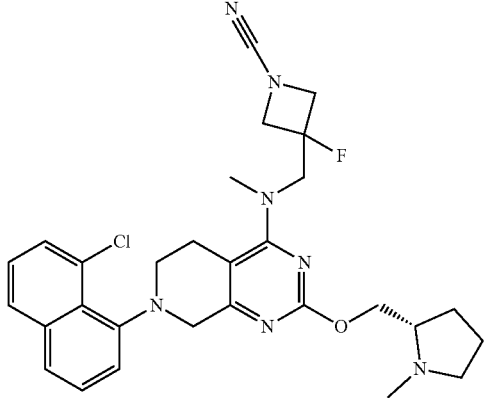 [SMILES: CN(CC1(F)CN(C#N)C1)c1nc(OC[C@@H]2CCCN2C)nc2c1CCN(c1cccc3cccc(Cl)c13)C2] | |
| 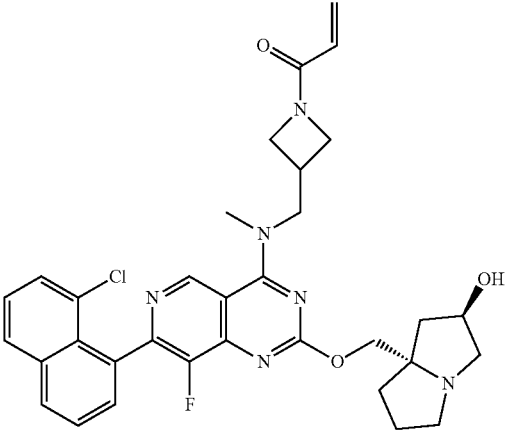 [SMILES: C=CC(=O)N1CC(CN(C)c2nc(OC[C@@]34CCCN3C[C@H](O)C4)nc3c(F)c(-c4cccc5cccc(Cl)c45)ncc23)C1] | + |

TABLE 1a-continued
Additional exemplary compounds—Inhibition of KRAS$^{G12C}$ and cRAF Binding
| Structure | RAF 1 RBD IC50 |
|---|---|
| 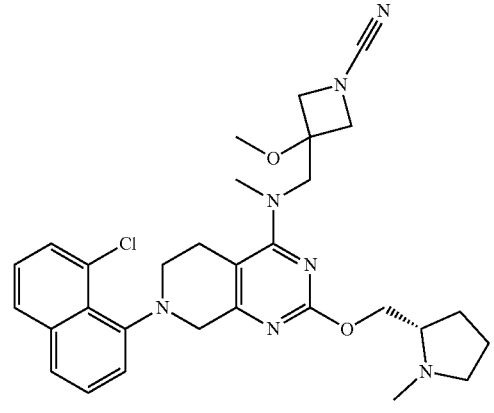 [SMILES: COC1(CN(C)c2nc(OC[C@@H]3CCCN3C)nc3c2CCN(c2cccc4cccc(Cl)c24)C3)CN(C#N)C1] | |
| 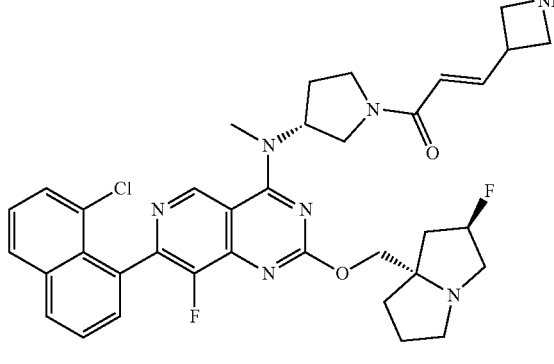 | ++ |
| 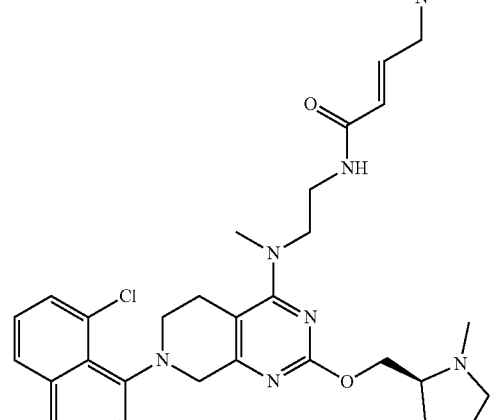 | |

TABLE 1a-continued

Additional exemplary compounds—Inhibition of KRAS$^{G12C}$ and cRAF Binding

| Structure | RAF 1 RBD IC50 |
|---|---|
| 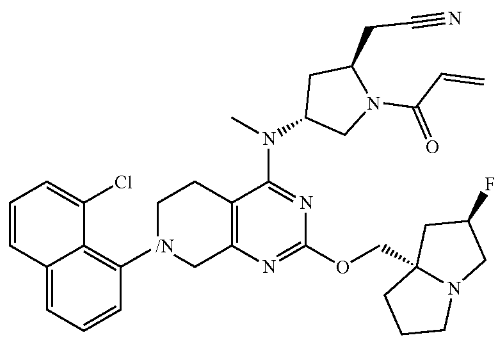 | ++ |
| | |
| 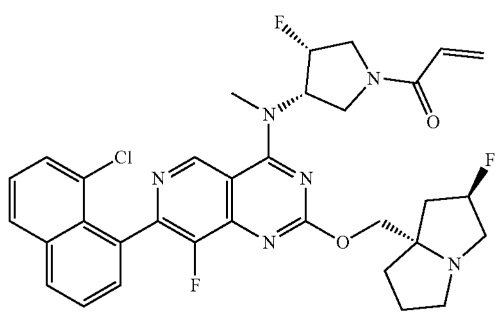 [SMILES: C=CC(=O)N1C[C@@H](F)[C@@H](N(C)c2nc(OC[C@@]34CCCN3C[C@H](F)C4)nc3c(F)c(-c4cccc5cccc(Cl)c45)ncc23)C1] | + |
| | |

TABLE 1a-continued

Additional exemplary compounds—Inhibition of $KRAS^{G12C}$ and cRAF Binding

| Structure | RAF 1 RBD IC50 |
|---|---|
| | + |
| | + |
| | + |

TABLE 1a-continued

Additional exemplary compounds—Inhibition of KRAS$^{G12C}$ and cRAF Binding

| Structure | RAF 1 RBD IC50 |
|---|---|
| | |
| 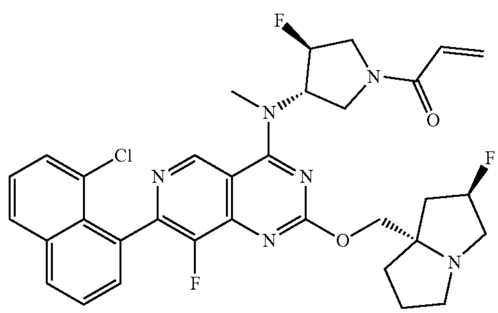 [SMILES: C=CC(=O)N1C[C@H](F)[C@@H](N(C)c2nc(OC[C@@]34CCCN3C[C@H](F)C4)nc3c(F)c(-c4cccc5cccc(Cl)c45)ncc23)C1] | +++ |
| | |
| 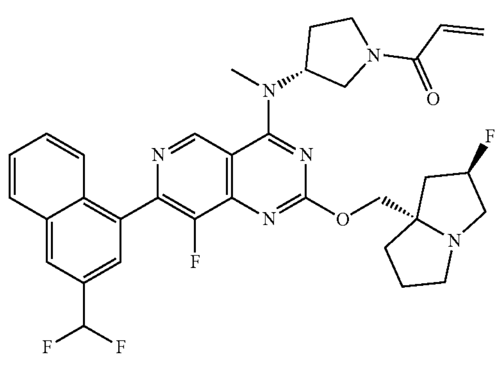 [SMILES: C=CC(=O)N1CC[C@@H](N(C)c2nc(OC[C@@]34CCCN3C[C@H](F)C4)nc3c(F)c(-c4cc(C(F)F)cc5ccccc45)ncc23)C1] | + |

TABLE 1a-continued

Additional exemplary compounds—Inhibition of KRAS$^{G12C}$ and cRAF Binding

| Structure | RAF1 RBD IC50 |
|---|---|
| | |
| | + |
| | |
| | + |

TABLE 1a-continued

Additional exemplary compounds—Inhibition of KRAS$^{G12C}$ and cRAF Binding

| Structure | RAF 1 RBD IC50 |
|---|---|
| | |
| | + |
| | |
| | + |

TABLE 1a-continued
Additional exemplary compounds—Inhibition of KRAS$^{G12C}$ and cRAF Binding
| Structure | RAF 1 RBD IC50 |
|---|---|
| 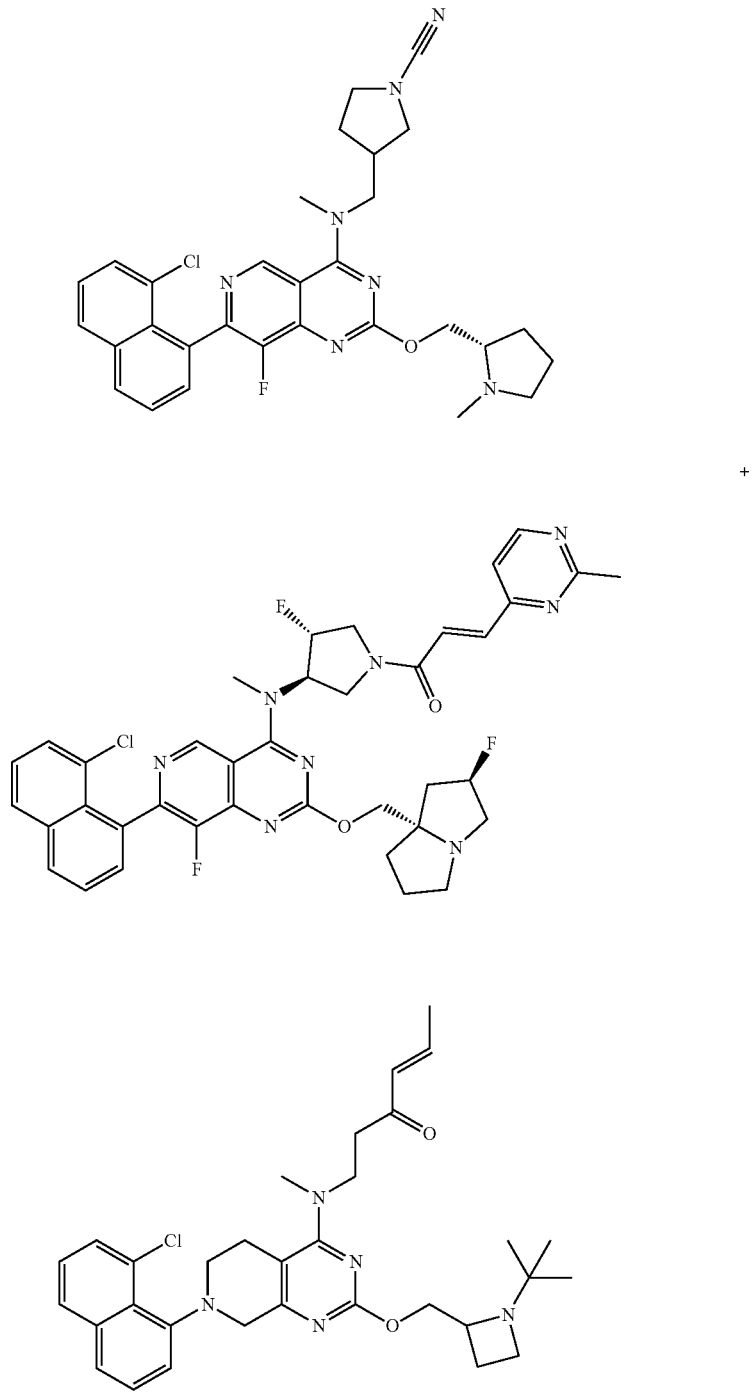 | + |

TABLE 1a-continued

Additional exemplary compounds—Inhibition of KRAS$^{G12C}$ and cRAF Binding

| Structure | RAF 1 RBD IC50 |
|---|---|
| 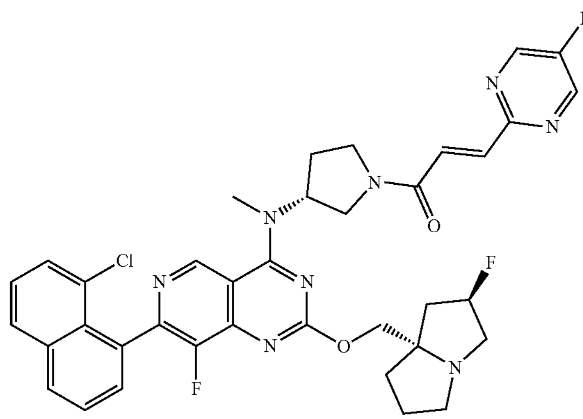 | + |
| 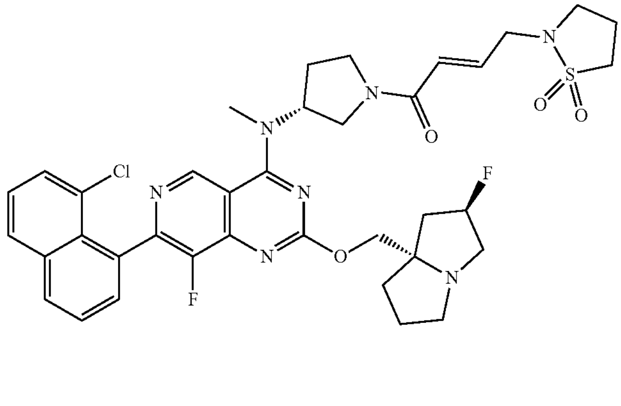 [SMILES: CN(c1nc(OC[C@@]23CCCN2C[C@H](F)C3)nc2c(F)c(-c3cccc4cccc(Cl)c34)ncc12)[C@@H]1CCN(C(=O)/C=C/CN2CCCS2(=O)=O)C1] | ++ |
| | |

TABLE 1a-continued

Additional exemplary compounds—Inhibition of KRAS$^{G12C}$ and cRAF Binding

| Structure | RAF 1 RBD IC50 |
|---|---|
| | |
| | + |
| | |
| | + |

TABLE 1a-continued
Additional exemplary compounds—Inhibition of KRAS$^{G12C}$ and cRAF Binding
| Structure | RAF 1 RBD IC50 |
|---|---|
| 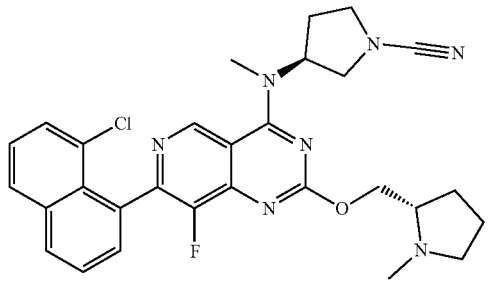 [SMILES: CN1CCC[C@H]1COc1nc(N(C)[C@H]2CCN(C#N)C2)c2cnc(-c3cccc4cccc(Cl)c34)c(F)c2n1] | |
| 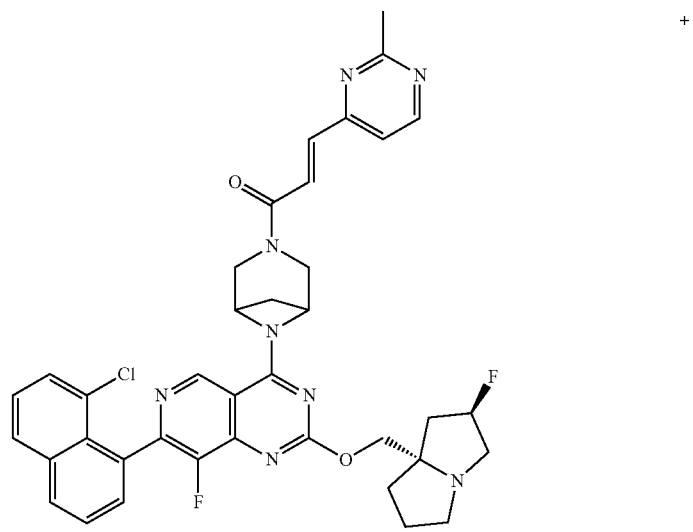 | + |
| 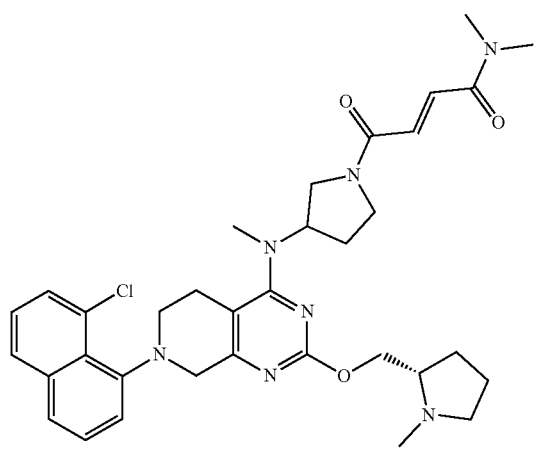 [SMILES: CN(C)C(=O)/C=C/C(=O)N1CCC(N(C)c2nc(OC[C@@H]3CCCN3C)nc3c2CCN(c2cccc4cccc(Cl)c24)C3)C1] | |

TABLE 1a-continued

Additional exemplary compounds—Inhibition of KRAS$^{G12C}$ and cRAF Binding

| Structure | RAF 1 RBD IC50 |
|---|---|
| | + |
| 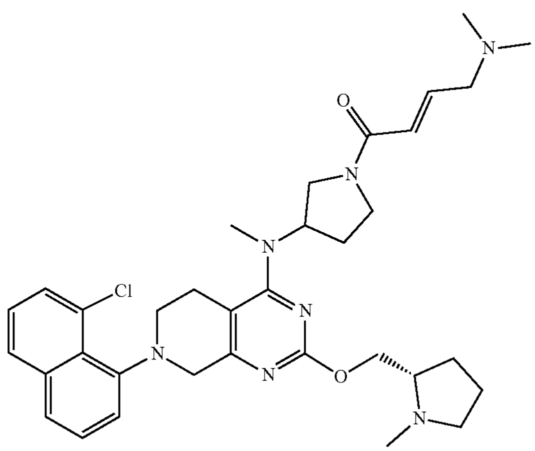 [SMILES: CN(C)C/C=C/C(=O)N1CCC(N(C)c2nc(OC[C@@H]3CCCN3C)nc3c2CCN(c2cccc4cccc(Cl)c24)C3)C1] | ++ |
| | + |

TABLE 1a-continued

Additional exemplary compounds—Inhibition of KRAS$^{G12C}$ and cRAF Binding

| Structure | RAF1 RBD IC50 |
|---|---|
| | |
| 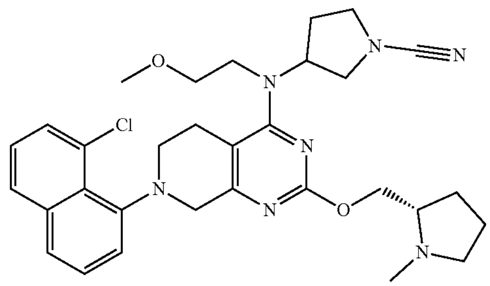 [SMILES: COCCN(c1nc(OC[C@@H]2CCCN2C)nc2c1CCN(c1cccc3cccc(Cl)c13)C2)C1CCN(C#N)C1] | + |
| | |

TABLE 1a-continued

Additional exemplary compounds—Inhibition of KRAS$^{G12C}$ and cRAF Binding

| Structure | RAF 1 RBD IC50 |
|---|---|
| | + |
| | |
| | + |

TABLE 1a-continued
Additional exemplary compounds—Inhibition of KRAS$^{G12C}$ and cRAF Binding
| Structure | RAF1 RBD IC50 |
|---|---|
| 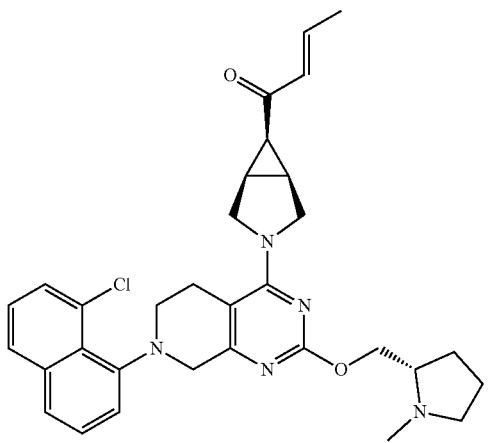 [SMILES: C/C=C/C(=O)[C@@H]1[C@@H]2CN(c3nc(OC[C@@H]4CCCN4C)nc4c3CCN(c3cccc5cccc(Cl)c35)C4)C[C@@H]21] | |
| 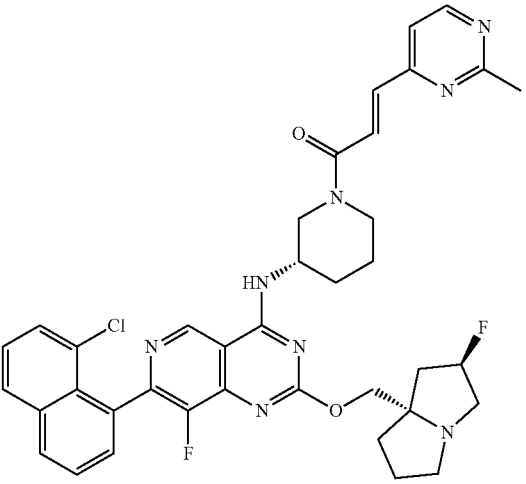 [SMILES: Cc1nccc(/C=C/C(=O)N2CCC[C@H](Nc3nc(OC[C@@]45CCCN4C[C@H](F)C5)nc4c(F)c(-c5cccc6cccc(Cl)c56)ncc34)C2)n1] | + |
| 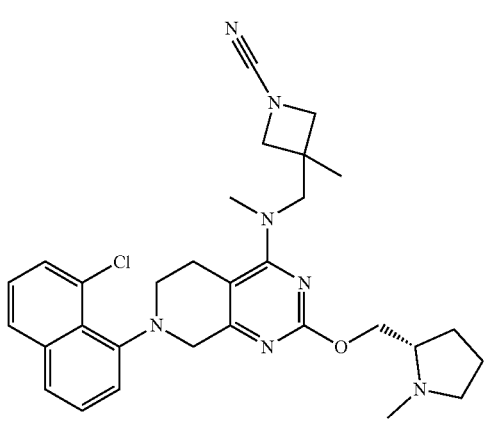 | + |

TABLE 1a-continued

Additional exemplary compounds—Inhibition of $KRAS^{G12C}$ and cRAF Binding

| Structure | RAF1 RBD IC50 |
|---|---|
| | + |
| | |
| | + |

TABLE 1a-continued
Additional exemplary compounds—Inhibition of KRAS$^{G12C}$ and cRAF Binding
| Structure | RAF 1 RBD IC50 |
|---|---|
| 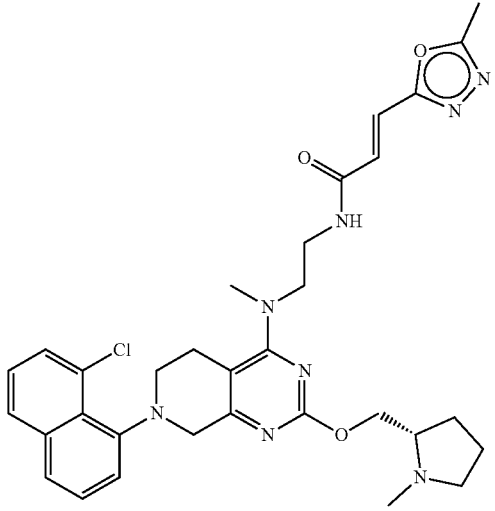 | |
| 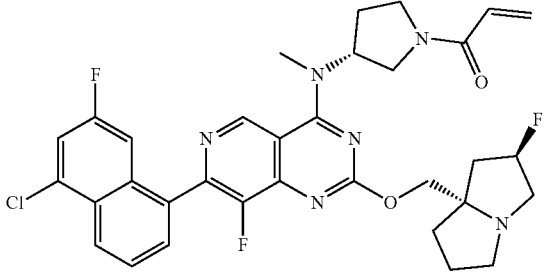 [SMILES: C=CC(=O)N1CC[C@@H](N(C)c2nc(OC[C@@]34CCCN3C[C@H](F)C4)nc3c(F)c(-c4cccc5c(Cl)cc(F)cc45)ncc23)C1] | + |
| 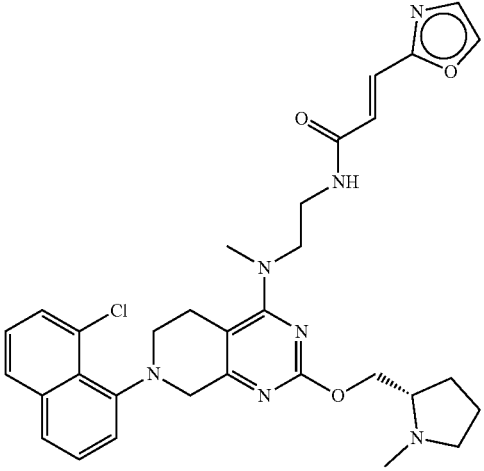 | |

TABLE 1a-continued
Additional exemplary compounds—Inhibition of KRAS$^{G12C}$ and cRAF Binding
| Structure | RAF 1 RBD IC50 |
|---|---|
| 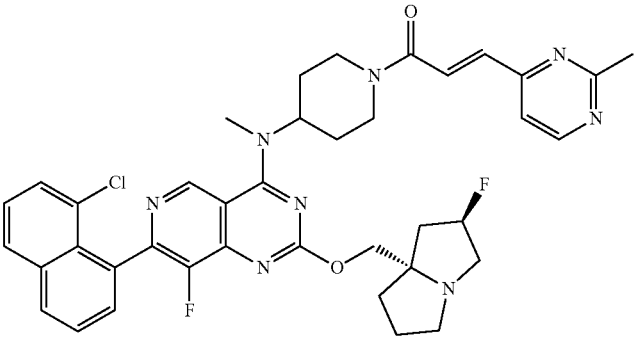 [SMILES: Cc1nccc(/C=C/C(=O)N2CCC(N(C)c3nc(OC[C@@]45CCCN4C[C@H](F)C5)nc4c(F)c(-c5cccc6cccc(Cl)c56)ncc34)CC2)n1] | + |
| 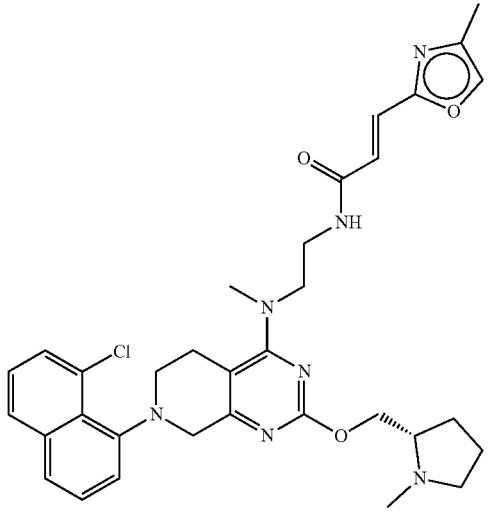 | |
| 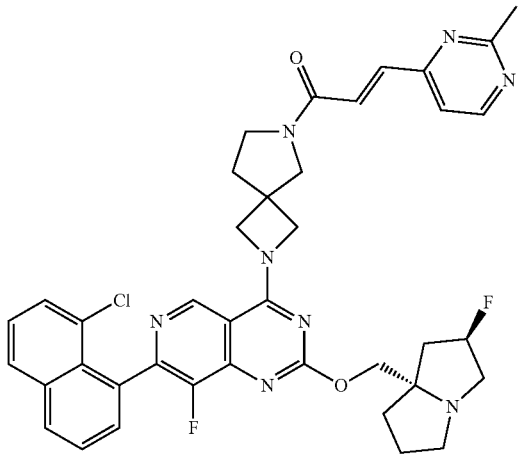 [SMILES: Cc1nccc(/C=C/C(=O)N2CCC3(C2)CN(c2nc(OC[C@@]45CCCN4C[C@H](F)C5)nc4c(F)c(-c5cccc6cccc(Cl)c56)ncc24)C3)n1] | + |

TABLE 1a-continued

Additional exemplary compounds—Inhibition of KRAS^(G12C) and cRAF Binding

| Structure | RAF1 RBD IC50 |
|---|---|
| | |
| | + |
| | |
| | + |

TABLE 1a-continued
Additional exemplary compounds—Inhibition of KRAS$^{G12C}$ and cRAF Binding
| Structure | RAF 1 RBD IC50 |
|---|---|
| 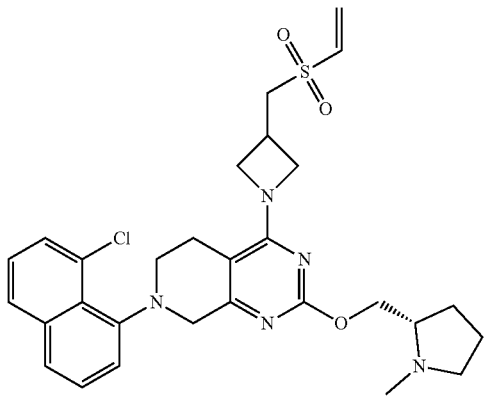 [SMILES: C=CS(=O)(=O)CC1CN(c2nc(OC[C@@H]3CCCN3C)nc3c2CCN(c2cccc4cccc(Cl)c24)C3)C1] | + |
| 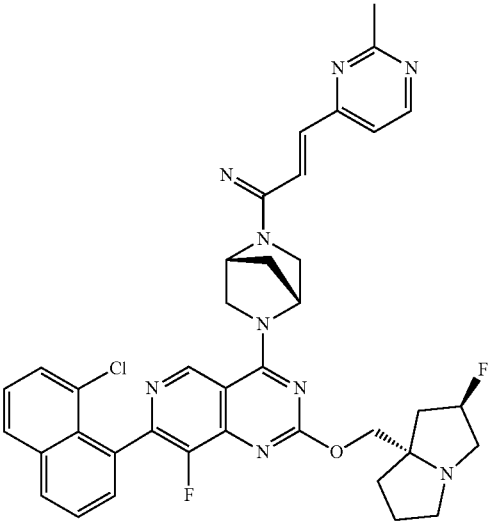 [SMILES: Cc1nccc(/C=C/C(=N)N2C[C@H]3C[C@@H]2CN3c2nc(OC[C@@]34CCCN3C[C@H](F)C4)nc3c(F)c(-c4cccc5cccc(Cl)c45)ncc23)n1] | ++ |
| 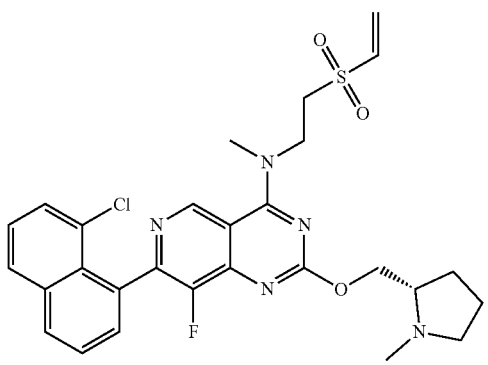 [SMILES: C=CS(=O)(=O)CCN(C)c1nc(OC[C@@H]2CCCN2C)nc2c(F)c(-c3cccc4cccc(Cl)c34)ncc12] | |

TABLE 1a-continued
Additional exemplary compounds—Inhibition of KRAS$^{G12C}$ and cRAF Binding
| Structure | RAF 1 RBD IC50 |
|---|---|
| 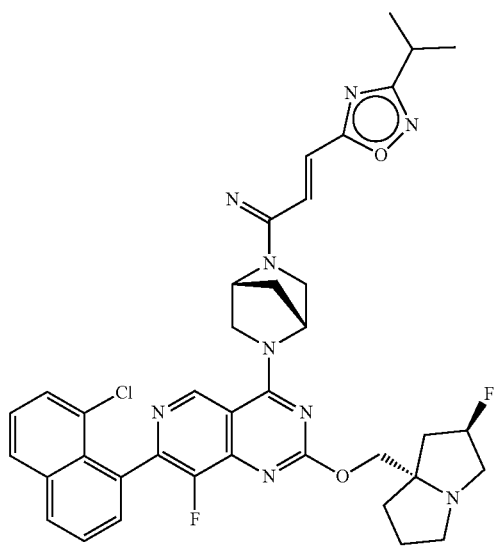 | + |
| 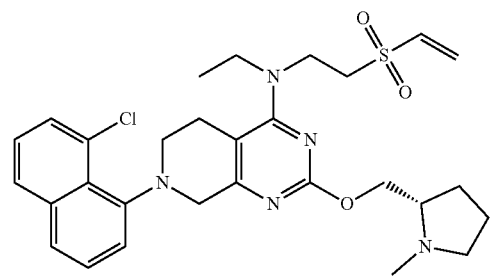 [SMILES: C=CS(=O)(=O)CCN(CC)c1nc(OC[C@@H]2CCCN2C)nc2c1CCN(c1cccc3cccc(Cl)c13)C2] | + |
| 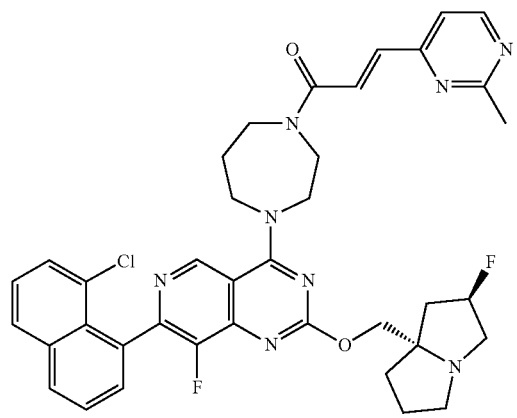 [SMILES: Cc1nccc(/C=C/C(=O)N2CCCN(c3nc(OC[C@@]45CCCN4C[C@H](F)C5)nc4c(F)c(-c5cccc6cccc(Cl)c56)ncc34)CC2)n1] | |

TABLE 1a-continued
Additional exemplary compounds—Inhibition of KRAS$^{G12C}$ and cRAF Binding
| Structure | RAF 1 RBD IC50 |
|---|---|
| 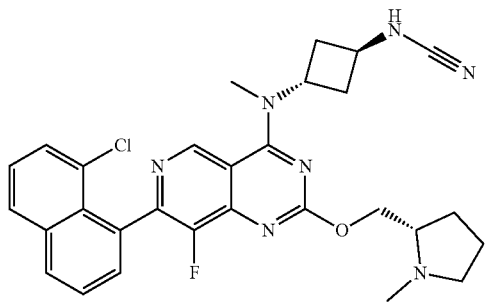 [SMILES: CN1CCC[C@H]1COc1nc(N(C)[C@H]2C[C@H](NC#N)C2)c2cnc(-c3cccc4cccc(Cl)c34)c(F)c2n1] | |
| 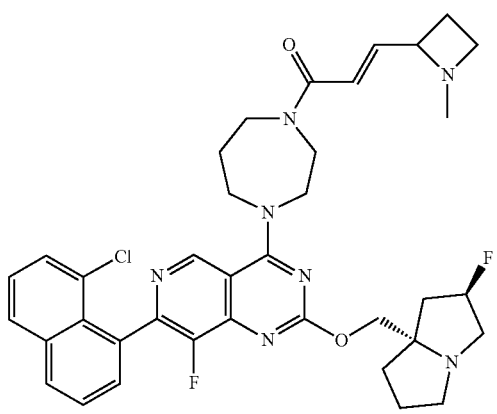 [SMILES: CN1CCC1/C=C/C(=O)N1CCCN(c2nc(OC[C@@]34CCCN3C[C@H](F)C4)nc3c(F)c(-c4cccc5cccc(Cl)c45)ncc23)CC1] | + |
| 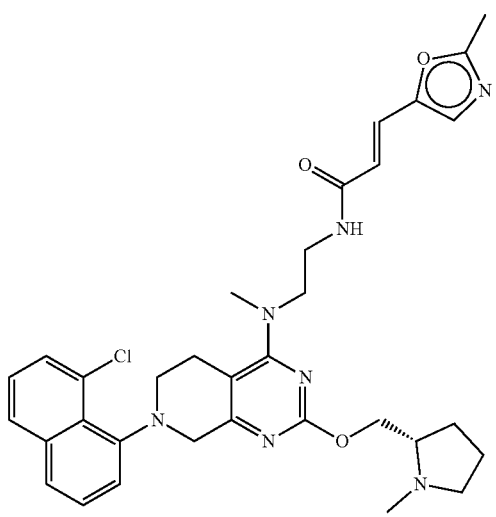 | |

TABLE 1a-continued
Additional exemplary compounds—Inhibition of KRAS$^{G12C}$ and cRAF Binding
| Structure | RAF 1 RBD IC50 |
|---|---|
| 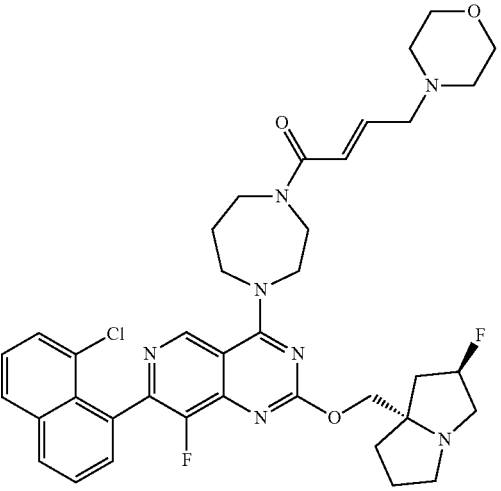 [SMILES: O=C(/C=C/CN1CCOCC1)N1CCCN(c2nc(OC[C@@]34CCCN3C[C@H](F)C4)nc3c(F)c(-c4cccc5cccc(Cl)c45)ncc23)CC1] | + |
| 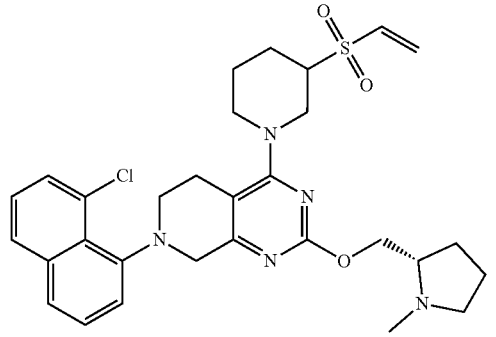 [SMILES: C=CS(=O)(=O)C1CCCN(c2nc(OC[C@@H]3CCCN3C)nc3c2CCN(c2cccc4cccc(Cl)c24)C3)C1] | |
| 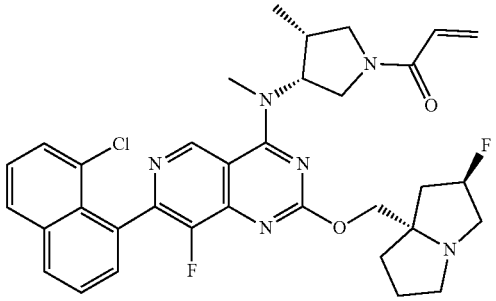 [SMILES: C=CC(=O)N1C[C@@H](C)[C@@H](N(C)c2nc(OC[C@@]34CCCN3C[C@H](F)C4)nc3c(F)c(-c4cccc5cccc(Cl)c45)ncc23)C1] | + |
| 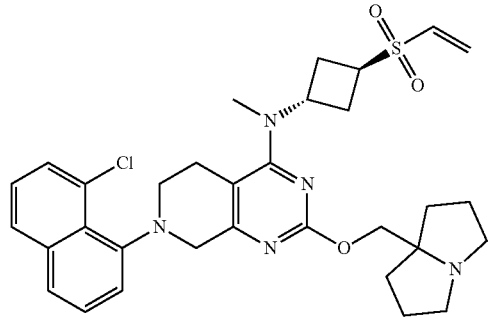 [SMILES: C=CS(=O)(=O)[C@H]1C[C@H](N(C)c2nc(OCC34CCCN3CCC4)nc3c2CCN(c2cccc4cccc(Cl)c24)C3)C1] | ++ |

TABLE 1a-continued

Additional exemplary compounds—Inhibition of KRAS$^{G12C}$ and cRAF Binding

| Structure | RAF1 RBD IC50 |
|---|---|
| | + |
| | |
| | + |

TABLE 1a-continued
Additional exemplary compounds—Inhibition of $KRAS^{G12C}$ and cRAF Binding
| Structure | RAF 1 RBD IC50 |
|---|---|
| 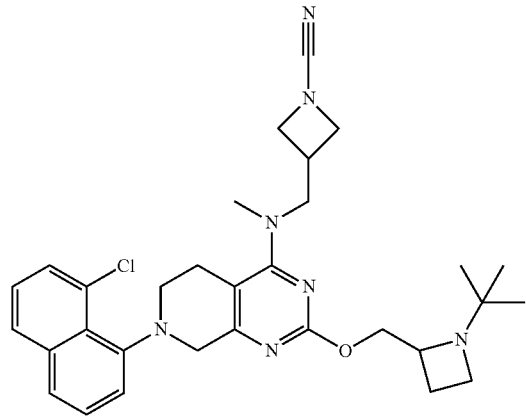 [SMILES: CN(CC1CN(C#N)C1)c1nc(OCC2CCN2C(C)(C)C)nc2c1CCN(c1cccc3cccc(Cl)c13)C2] | |
| 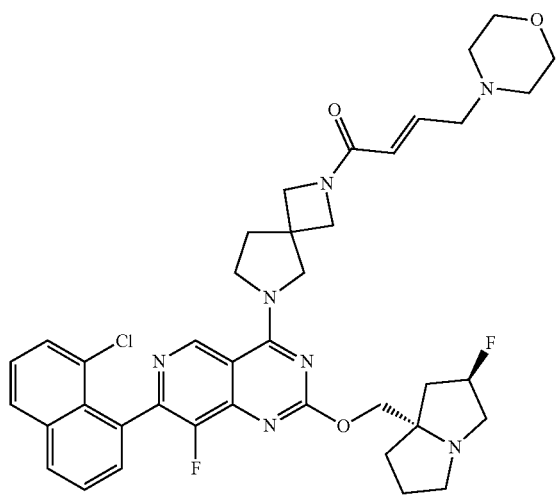 [SMILES: O=C(/C=C/CN1CCOCC1)N1CC2(CCN(c3nc(OC[C@@]45CCCN4C[C@H](F)C5)nc4c(F)c(-c5cccc6cccc(Cl)c56)ncc34)C2)C1] | + |
| 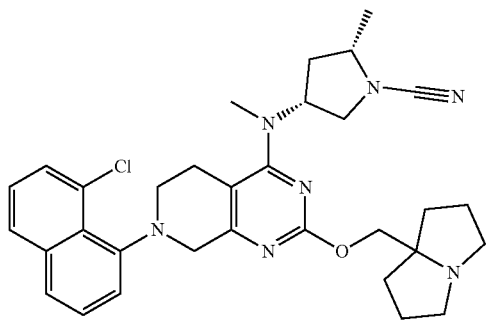 [SMILES: C[C@H]1C[C@@H](N(C)c2nc(OCC34CCCN3CCC4)nc3c2CCN(c2cccc4cccc(Cl)c24)C3)CN1C#N] | |

TABLE 1a-continued

Additional exemplary compounds—Inhibition of KRAS$^{G12C}$ and cRAF Binding

| Structure | RAF 1 RBD IC50 |
|---|---|
| | + |
| 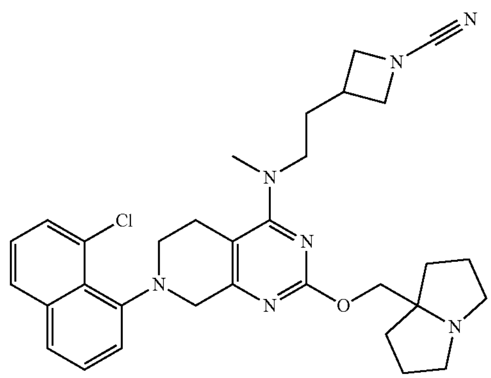 [SMILES: CN(CCC1CN(C#N)C1)c1nc(OCC23CCCN2CCC3)nc2c1CCN(c1cccc3cccc(Cl)c13)C2] | ++ |
| | + |

TABLE 1a-continued

Additional exemplary compounds—Inhibition of KRAS$^{G12C}$ and cRAF Binding

| Structure | RAF1 RBD IC50 |
|---|---|
| | + |
| | + |
| 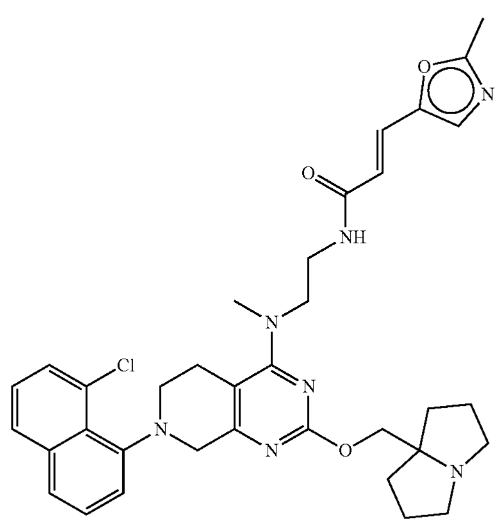 | ++ |

TABLE 1a-continued
Additional exemplary compounds—Inhibition of KRAS$^{G12C}$ and cRAF Binding
| Structure | RAF 1 RBD IC50 |
|---|---|
| 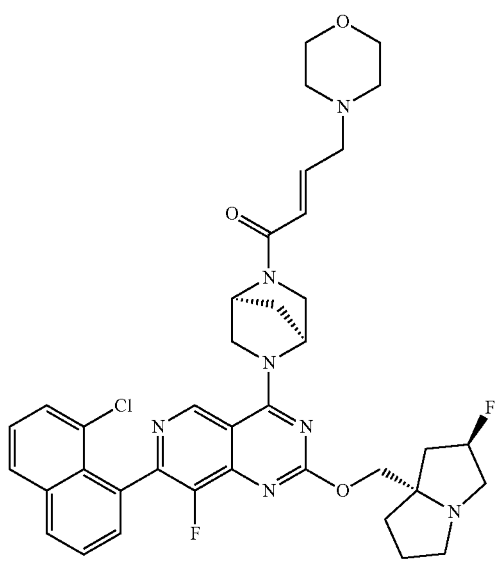 | + |
| 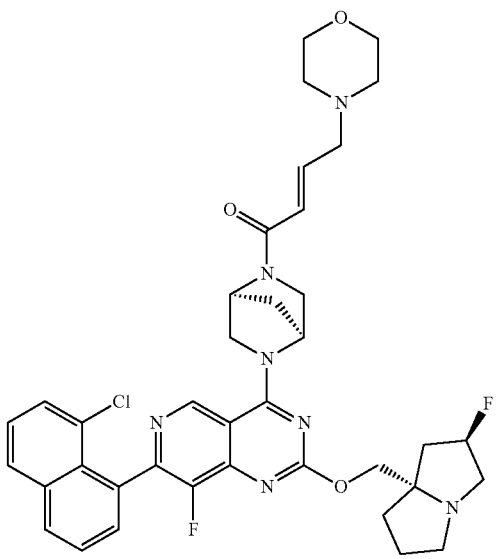 [SMILES: O=C(/C=C/CN1CCOCC1)N1C[C@@H]2C[C@H]1CN2c1nc(OC[C@@]23CCCN2C[C@H](F)C3)nc2c(F)c(-c3cccc4cccc(Cl)c34)ncc12] | ++++ |
| 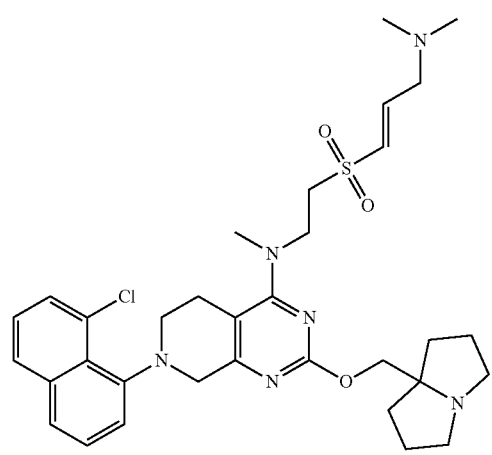 [SMILES: CN(C)C/C=C/S(=O)(=O)CCN(C)c1nc(OCC23CCCN2CCC3)nc2c1CCN(c1cccc3cccc(Cl)c13)C2] | |

TABLE 1a-continued
Additional exemplary compounds—Inhibition of KRAS$^{G12C}$ and cRAF Binding
| Structure | RAF 1 RBD IC50 |
|---|---|
| | + |олн
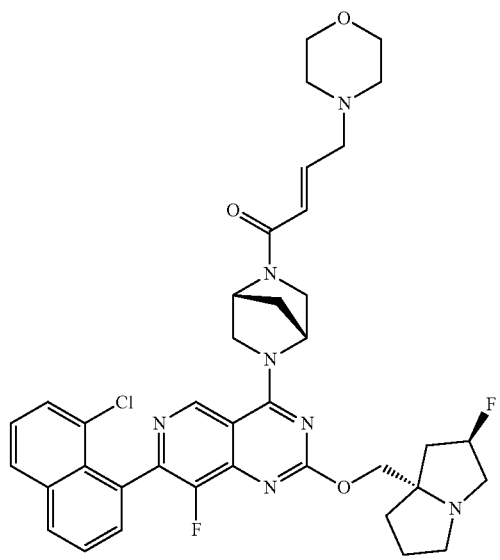 [SMILES: O=C(/C=C/CN1CCOCC1)N1C[C@H]2C[C@@H]1CN2c1nc(OC[C@@]23CCCN2C[C@H](F)C3)nc2c(F)c(-c3cccc4cccc(Cl)c34)ncc12]
++
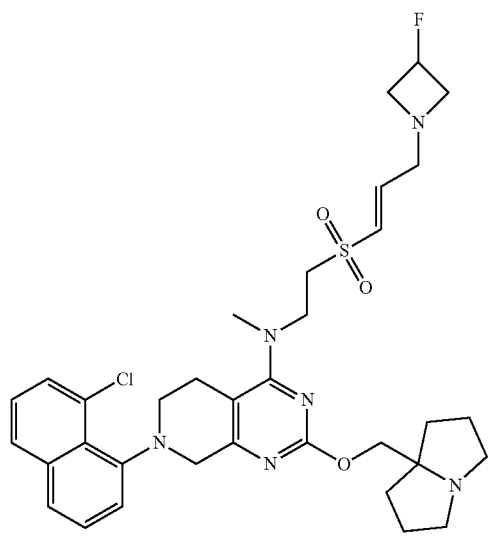 [SMILES: CN(CCS(=O)(=O)/C=C/CN1CC(F)C1)c1nc(OCC23CCCN2CCC3)nc2c1CCN(c1cccc3cccc(Cl)c13)C2]

TABLE 1a-continued

Additional exemplary compounds—Inhibition of KRAS$^{G12C}$ and cRAF Binding

| Structure | RAF 1 RBD IC50 |
|---|---|
| | + |
| | |
| | + |

TABLE 1a-continued

Additional exemplary compounds—Inhibition of KRAS$^{G12C}$ and cRAF Binding

| Structure | RAF1 RBD IC50 |
|---|---|
| | + |
| | + |
| | |

TABLE 1a-continued

Additional exemplary compounds—Inhibition of KRAS$^{G12C}$ and cRAF Binding

| Structure | RAF1 RBD IC50 |
|---|---|
| | + |
| | |
| | + |

TABLE 1a-continued

Additional exemplary compounds—Inhibition of KRAS$^{G12C}$ and cRAF Binding

| Structure | RAF 1 RBD IC50 |
|---|---|
| 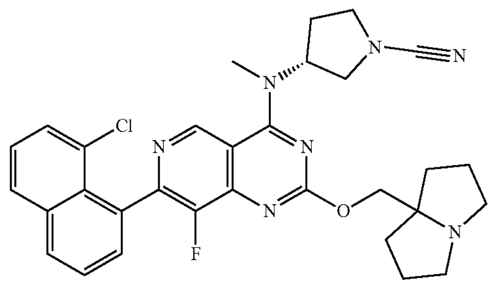 [SMILES: CN(c1nc(OCC23CCCN2CCC3)nc2c(F)c(-c3cccc4cccc(Cl)c34)ncc12)[C@@H]1CCN(C#N)C1] | ++++ |
| 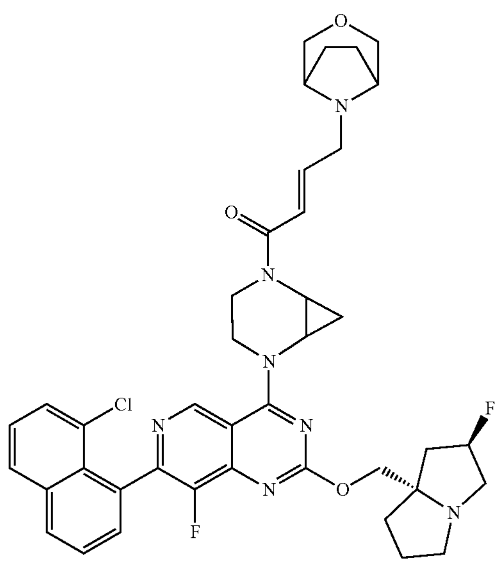 | + |
| 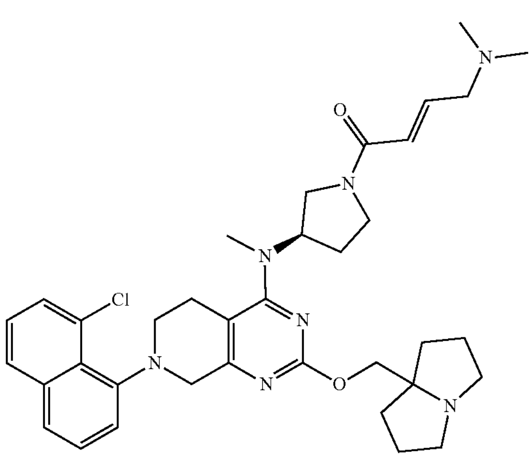 [SMILES: CN(C)C/C=C/C(=O)N1CC[C@@H](N(C)c2nc(OCC34CCCN3CCC4)nc3c2CCN(c2cccc4cccc(Cl)c24)C3)C1] | +++ |

TABLE 1a-continued

Additional exemplary compounds—Inhibition of KRAS$^{G12C}$ and cRAF Binding

| Structure | RAF 1 RBD IC50 |
|---|---|
| | +++ |
| | +++ |
| 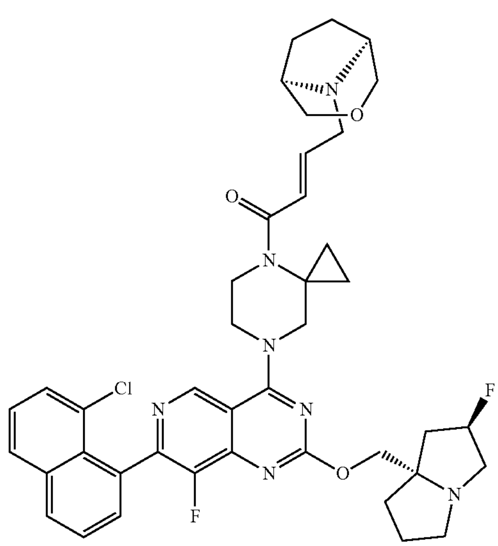 | + |

TABLE 1a-continued
Additional exemplary compounds—Inhibition of $KRAS^{G12C}$ and cRAF Binding
| Structure | RAF 1 RBD IC50 |
|---|---|
| 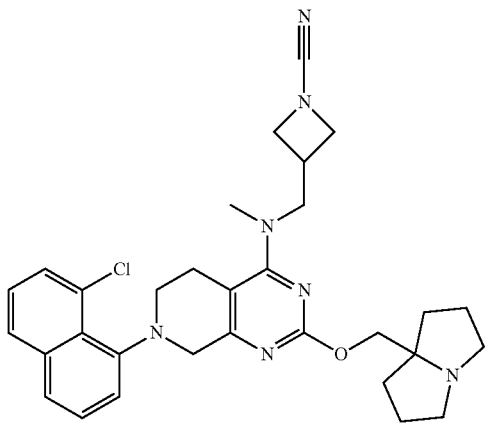 [SMILES: CN(CC1CN(C#N)C1)c1nc(OCC23CCCN2CCC3)nc2c1CCN(c1cccc3cccc(Cl)c13)C2] | ++ |
| 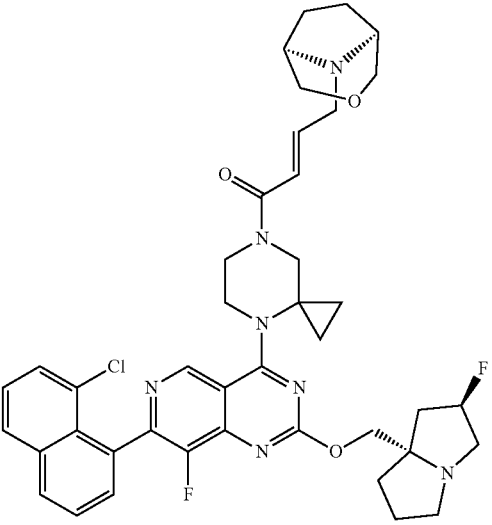 [SMILES: O=C(/C=C/CN1[C@@H]2CC[C@H]1COC2)N1CCN(c2nc(OC[C@@]34CCCN3C[C@H](F)C4)nc3c(F)c(-c4cccc5cccc(Cl)c45)ncc23)C2(CC2)C1] | + |
| 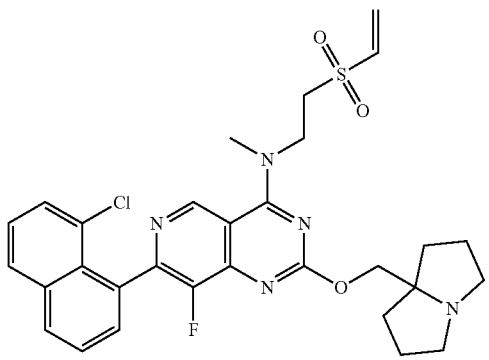 [SMILES: C=CS(=O)(=O)CCN(C)c1nc(OCC23CCCN2CCC3)nc2c(F)c(-c3cccc4cccc(Cl)c34)ncc12] | ++++ |

TABLE 1a-continued

Additional exemplary compounds—Inhibition of KRAS$^{G12C}$ and cRAF Binding

| Structure | RAF 1 RBD IC50 |
|---|---|
| | + |
| | |
| | + |

TABLE 1a-continued
Additional exemplary compounds—Inhibition of KRAS$^{G12C}$ and cRAF Binding
| Structure | RAF 1 RBD IC50 |
|---|---|
| 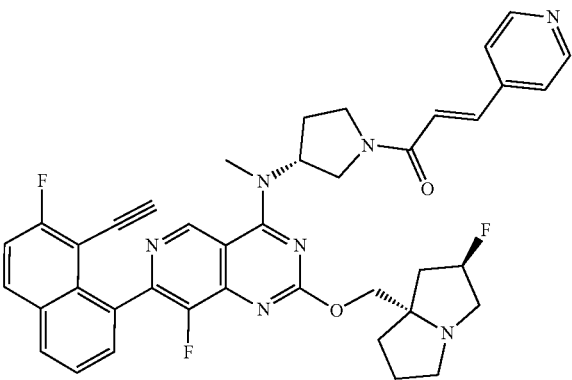 [SMILES: C#Cc1c(F)ccc2cccc(-c3ncc4c(N(C)[C@@H]5CCN(C(=O)/C=C/c6ccncc6)C5)nc(OC[C@@]56CCCN5C[C@H](F)C6)nc4c3F)c12] | ++ |
| 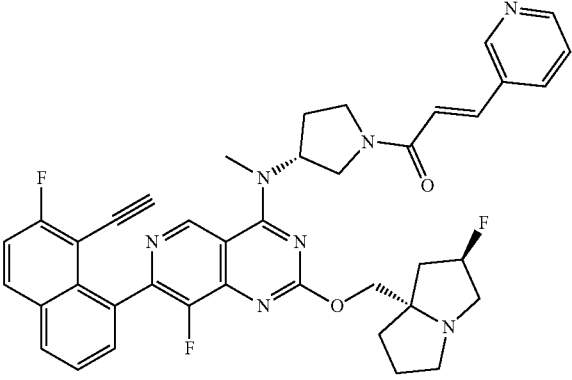 [SMILES: C#Cc1c(F)ccc2cccc(-c3ncc4c(N(C)[C@@H]5CCN(C(=O)/C=C/c6cccnc6)C5)nc(OC[C@@]56CCCN5C[C@H](F)C6)nc4c3F)c12] | + |
| 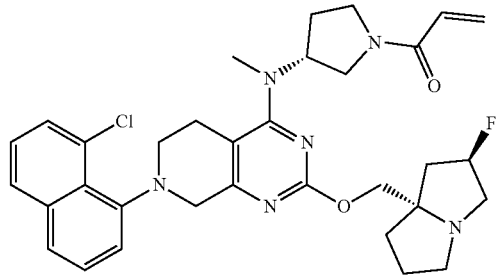 [SMILES: C=CC(=O)N1CC[C@@H](N(C)c2nc(OC[C@@]34CCCN3C[C@H](F)C4)nc3c2CCN(c2cccc4cccc(Cl)c24)C3)C1] | ++ |
| 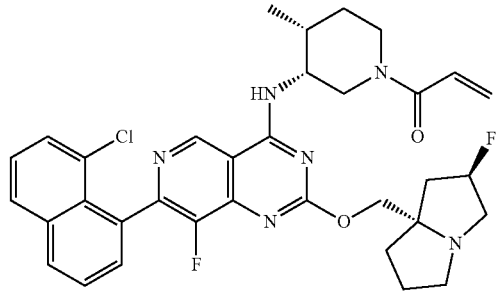 [SMILES: C=CC(=O)N1CC[C@@H](C)[C@@H](Nc2nc(OC[C@@]34CCCN3C[C@H](F)C4)nc3c(F)c(-c4cccc5cccc(Cl)c45)ncc23)C1] | + |

TABLE 1a-continued
Additional exemplary compounds—Inhibition of KRAS$^{G12C}$ and cRAF Binding
| Structure | RAF 1 RBD IC50 |
|---|---|
| 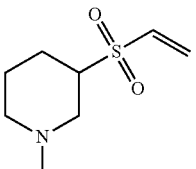 | +++ |
| 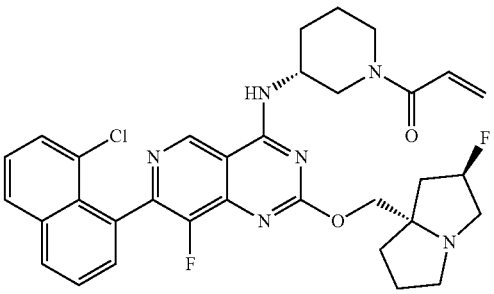 [SMILES: C=CC(=O)N1CCC[C@@H](Nc2nc(OC[C@@]34CCCN3C[C@H](F)C4)nc3c(F)c(-c4cccc5cccc(Cl)c45)ncc23)C1] | + |
| 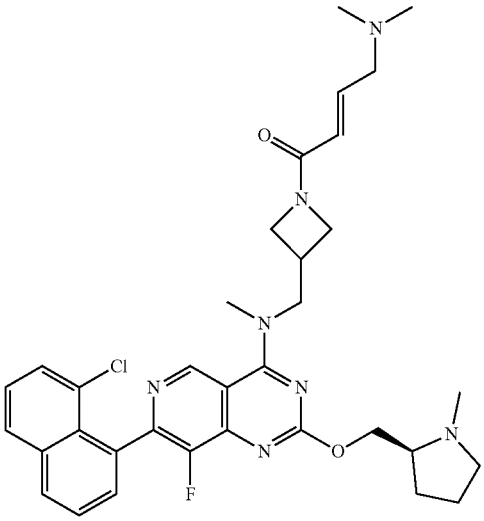 [SMILES: CN(C)C/C=C/C(=O)N1CC(CN(C)c2nc(OC[C@@H]3CCCN3C)nc3c(F)c(-c4cccc5cccc(Cl)c45)ncc23)C1] | |
| 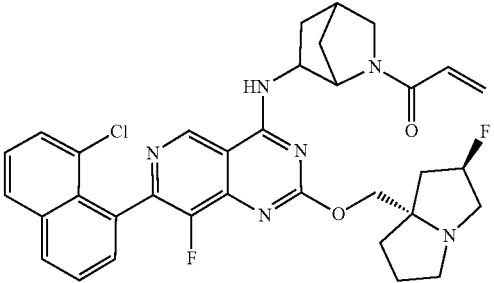 [SMILES: C=CC(=O)N1CC2CC(Nc3nc(OC[C@@]45CCCN4C[C@H](F)C5)nc4c(F)c(-c5cccc6cccc(Cl)c56)ncc34)C1C2] | + |

TABLE 1a-continued
Additional exemplary compounds—Inhibition of KRAS$^{G12C}$ and cRAF Binding
| Structure | RAF 1 RBD IC50 |
|---|---|
| 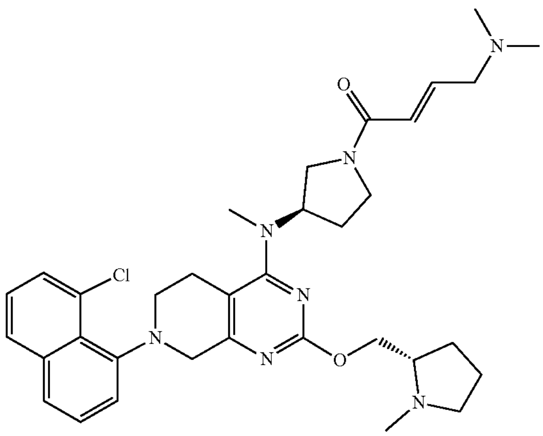 [SMILES: CN(C)C/C=C/C(=O)N1CC[C@@H](N(C)c2nc(OC[C@@H]3CCCN3C)nc3c2CCN(c2cccc4cccc(Cl)c24)C3)C1] | ++ |
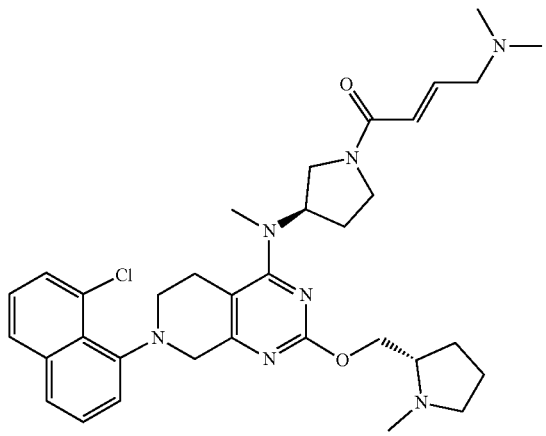
|  | + |
|---|---|
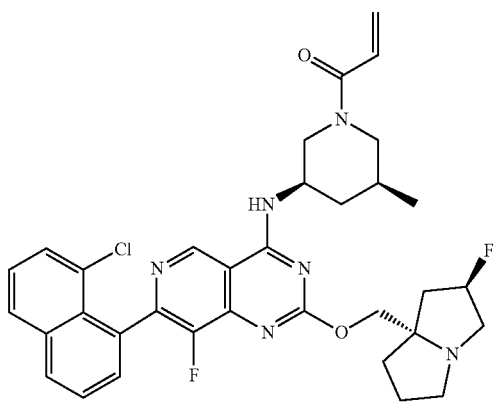 [SMILES: C=CC(=O)N1C[C@@H](C)C[C@@H](Nc2nc(OC[C@@]34CCCN3C[C@H](F)C4)nc3c(F)c(-c4cccc5cccc(Cl)c45)ncc23)C1]
|  | +++ |
|---|---|
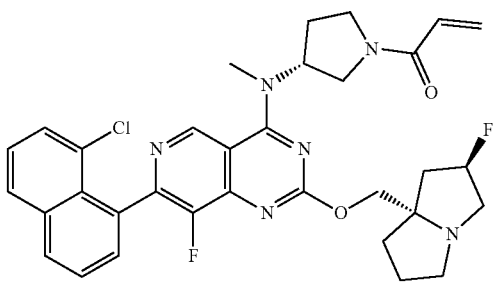 [SMILES: C=CC(=O)N1CC[C@@H](N(C)c2nc(OC[C@@]34CCCN3C[C@H](F)C4)nc3c(F)c(-c4cccc5cccc(Cl)c45)ncc23)C1]

TABLE 1a-continued

Additional exemplary compounds—Inhibition of KRAS$^{G12C}$ and cRAF Binding

| Structure | RAF 1 RBD IC50 |
|---|---|
| | + |
| | |
| | + |
| | |

TABLE 1a-continued
Additional exemplary compounds—Inhibition of KRAS$^{G12C}$ and cRAF Binding
| Structure | RAF1 RBD IC50 |
|---|---|
| 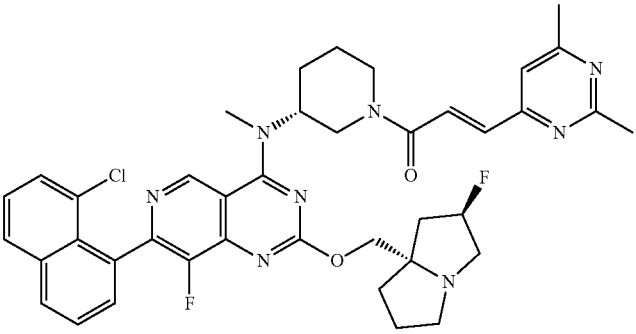 [SMILES: Cc1cc(/C=C/C(=O)N2CCC[C@@H](N(C)c3nc(OC[C@@]45CCCN4C[C@H](F)C5)nc4c(F)c(-c5cccc6cccc(Cl)c56)ncc34)C2)nc(C)n1] | + |
| 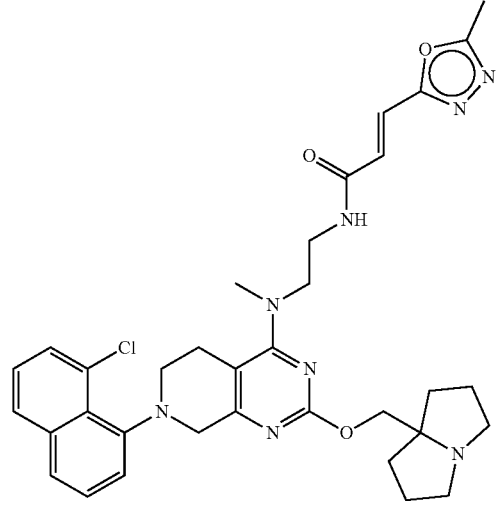 | ++ |
| 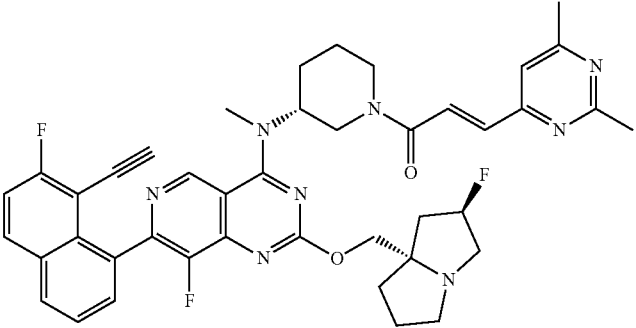 [SMILES: C#Cc1c(F)ccc2cccc(-c3ncc4c(N(C)[C@@H]5CCCN(C(=O)/C=C/c6cc(C)nc(C)n6)C5)nc(OC[C@@]56CCCN5C[C@H](F)C6)nc4c3F)c12] | |

TABLE 1a-continued

*Additional exemplary compounds—Inhibition of KRAS$^{G12C}$ and cRAF Binding*

| Structure | RAF 1 RBD IC50 |
|---|---|
| | |
| 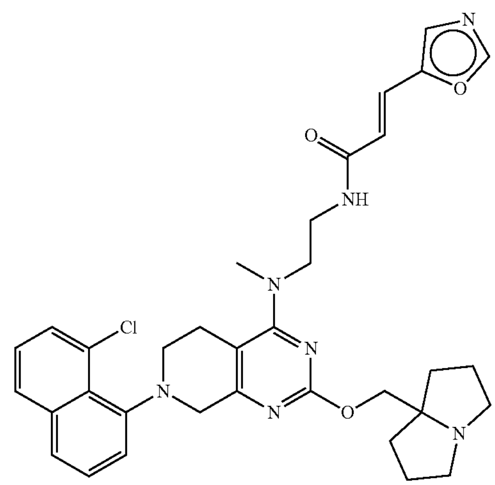 | + |
| | |

TABLE 1a-continued
Additional exemplary compounds—Inhibition of KRAS$^{G12C}$ and cRAF Binding
| Structure | RAF 1 RBD IC50 |
|---|---|
| 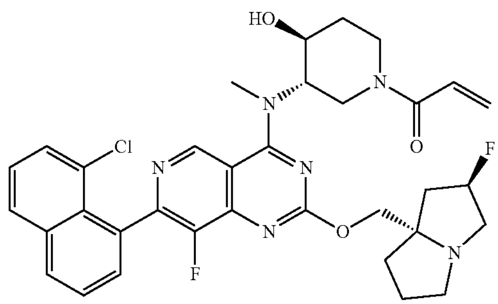 [SMILES: C=CC(=O)N1CC[C@H](O)[C@@H](N(C)c2nc(OC[C@@]34CCCN3C[C@H](F)C4)nc3c(F)c(-c4cccc5cccc(Cl)c45)ncc23)C1] | +++ |
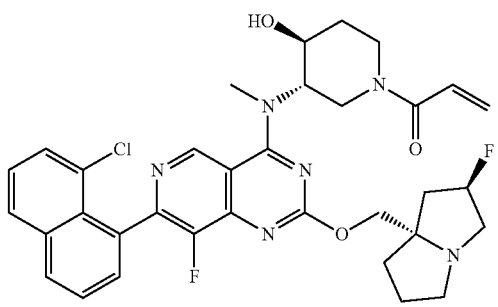
| | + |
|---|---|
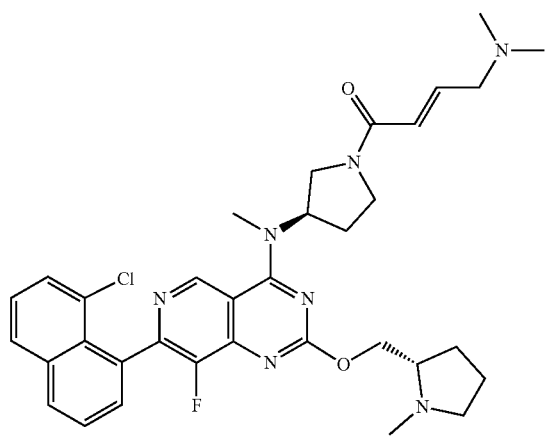 [SMILES: CN(C)C/C=C/C(=O)N1CC[C@@H](N(C)c2nc(OC[C@@H]3CCCN3C)nc3c(F)c(-c4cccc5cccc(Cl)c45)ncc23)C1]
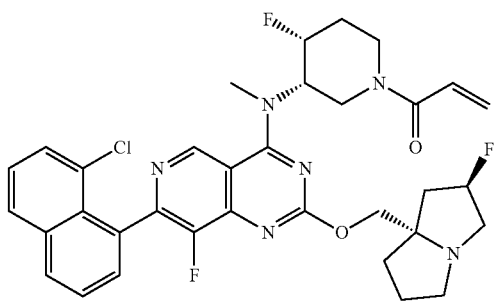 [SMILES: C=CC(=O)N1CC[C@@H](F)[C@@H](N(C)c2nc(OC[C@@]34CCCN3C[C@H](F)C4)nc3c(F)c(-c4cccc5cccc(Cl)c45)ncc23)C1]

TABLE 1a-continued

Additional exemplary compounds—Inhibition of KRAS$^{G12C}$ and cRAF Binding

| Structure | RAF 1 RBD IC50 |
|---|---|
| | |
| 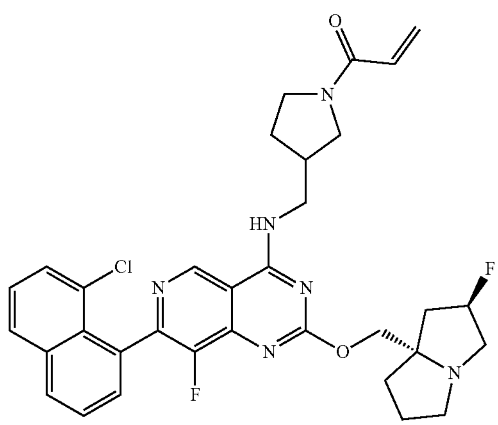 [SMILES: C=CC(=O)N1CCC(CNc2nc(OC[C@@]34CCCN3C[C@H](F)C4)nc3c(F)c(-c4cccc5cccc(Cl)c45)ncc23)C1] | + |
| 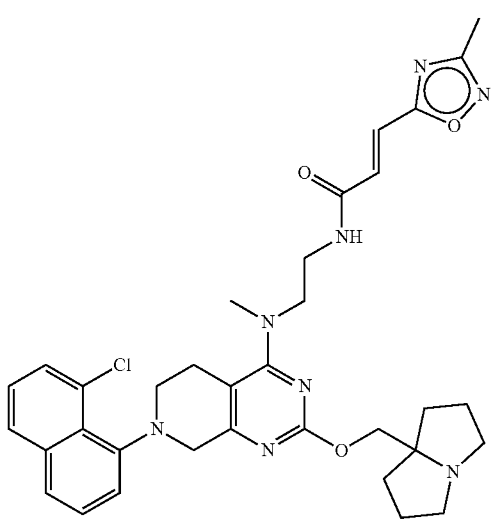 | ++ |

TABLE 1a-continued

Additional exemplary compounds—Inhibition of KRAS$^{G12C}$ and cRAF Binding

| Structure | RAF 1 RBD IC50 |
|---|---|
| | + |
| | + |
| | + |

TABLE 1a-continued

Additional exemplary compounds—Inhibition of KRAS$^{G12C}$ and cRAF Binding

| Structure | RAF 1 RBD IC50 |
|---|---|
| | + |
| | + |
| 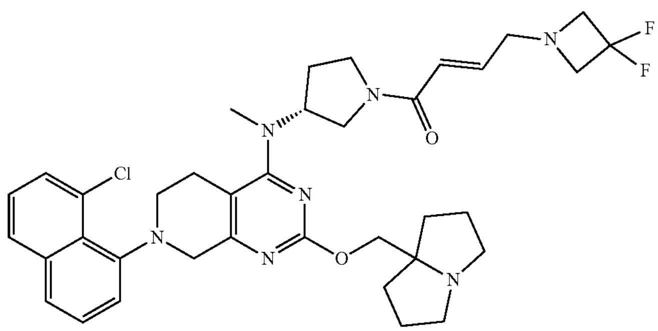 [SMILES: CN(c1nc(OCC23CCCN2CCC3)nc2c1CCN(c1cccc3cccc(Cl)c13)C2)[C@@H]1CCN(C(=O)/C=C/CN2CC(F)(F)C2)C1] | ++ |

TABLE 1a-continued

Additional exemplary compounds—Inhibition of KRAS$^{G12C}$ and cRAF Binding

| Structure | RAF1 RBD IC50 |
|---|---|
| | ++ |
| | ++ |
| 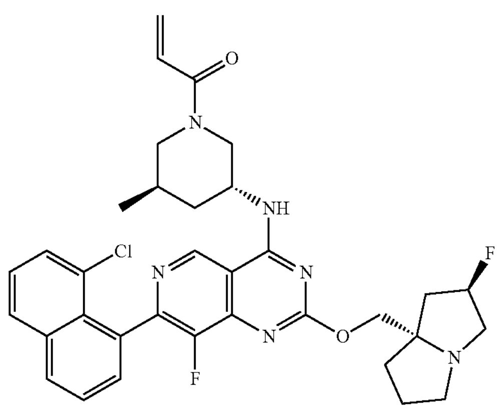 [SMILES: C=CC(=O)N1C[C@H](C)C[C@@H](Nc2nc(OC[C@@]34CCCN3C[C@H](F)C4)nc3c(F)c(-c4cccc5cccc(Cl)c45)ncc23)C1] | + |
| 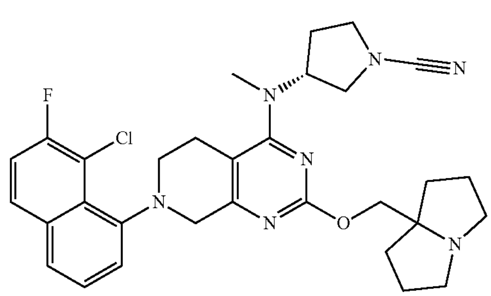 [SMILES: CN(c1nc(OCC23CCCN2CCC3)nc2c1CCN(c1cccc3ccc(F)c(Cl)c13)C2)[C@@H]1CCN(C#N)C1] | +++ |

TABLE 1a-continued
Additional exemplary compounds—Inhibition of KRAS$^{G12C}$ and cRAF Binding
| Structure | RAF 1 RBD IC50 |
|---|---|
| 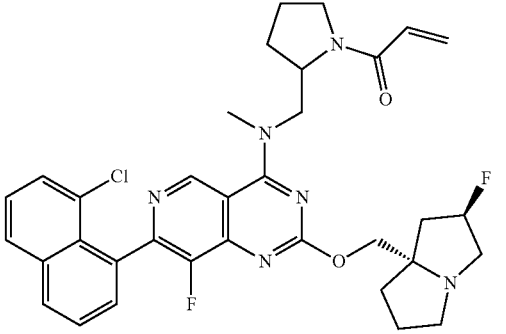 [SMILES: C=CC(=O)N1CCCC1CN(C)c1nc(OC[C@@]23CCCN2C[C@H](F)C3)nc2c(F)c(-c3cccc4cccc(Cl)c34)ncc12] | + |
| 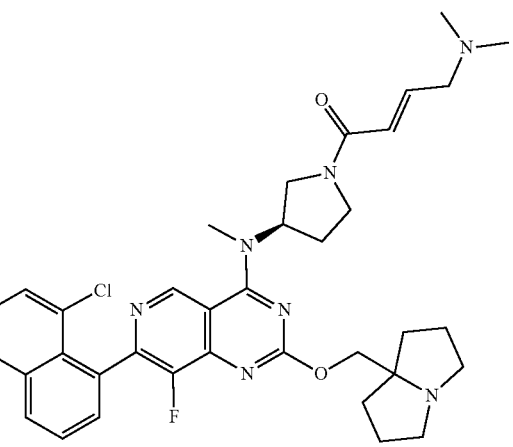 | +++ |
| 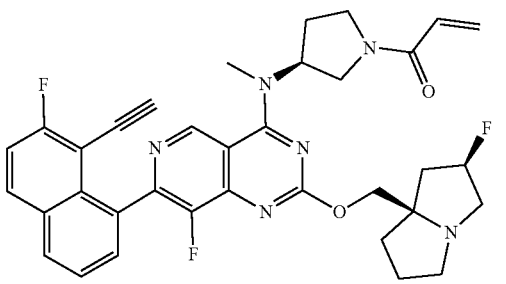 [SMILES: C#Cc1c(F)ccc2cccc(-c3ncc4c(N(C)[C@H]5CCN(C(=O)C=C)C5)nc(OC[C@]56CCCN5C[C@H](F)C6)nc4c3F)c12] | + |
| 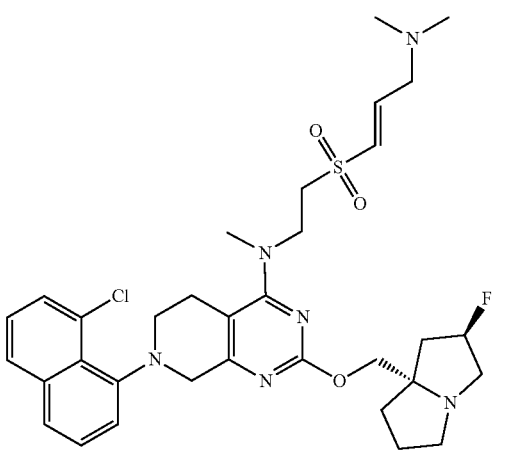 [SMILES: CN(C)C/C=C/S(=O)(=O)CCN(C)c1nc(OC[C@@]23CCCN2C[C@H](F)C3)nc2c1CCN(c1cccc3cccc(Cl)c13)C2] | ++++ |

TABLE 1a-continued
Additional exemplary compounds—Inhibition of KRAS$^{G12C}$ and cRAF Binding
| Structure | RAF 1 RBD IC50 |
|---|---|
| 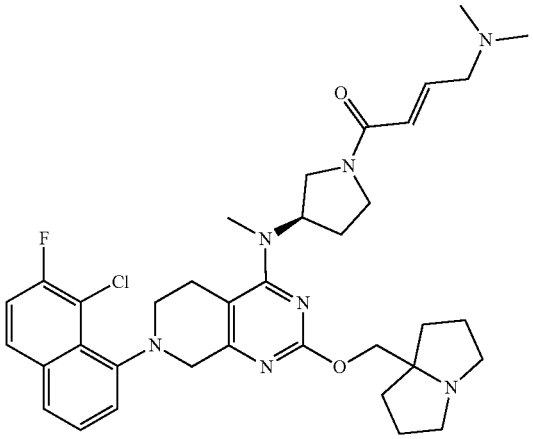 [SMILES: CN(C)C/C=C/C(=O)N1CC[C@@H](N(C)c2nc(OCC34CCCN3CCC4)nc3c2CCN(c2cccc4ccc(F)c(Cl)c24)C3)C1] | ++ |
| 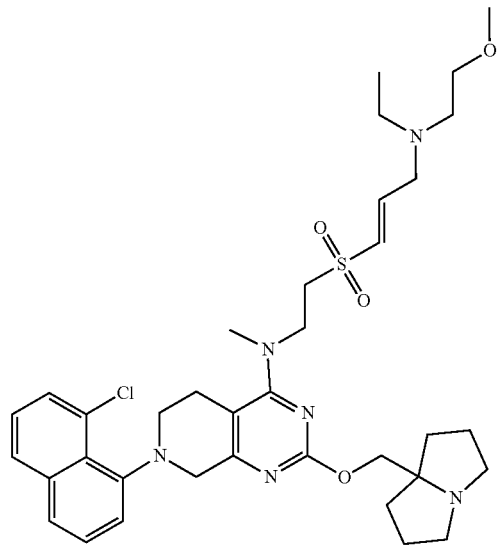 [SMILES: CCN(C/C=C/S(=O)(=O)CCN(C)c1nc(OCC23CCCN2CCC3)nc2c1CCN(c1cccc3cccc(Cl)c13)C2)CCOC] | +++ |
| 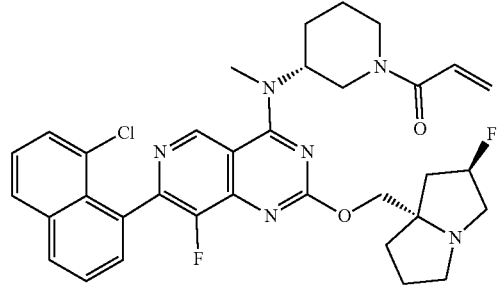 [SMILES: C=CC(=O)N1CCC[C@@H](N(C)c2nc(OC[C@@]34CCCN3C[C@H](F)C4)nc3c(F)c(-c4cccc5cccc(Cl)c45)ncc23)C1] | + |

TABLE 1a-continued
Additional exemplary compounds—Inhibition of KRAS$^{G12C}$ and cRAF Binding
| Structure | RAF 1 RBD IC50 |
|---|---|
| 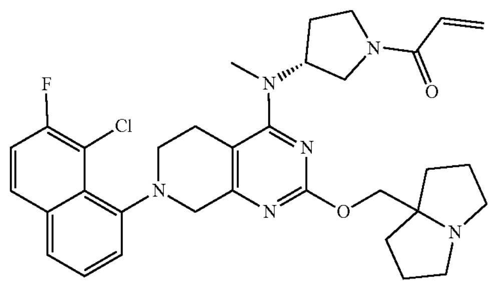 [SMILES: C=CC(=O)N1CC[C@@H](N(C)c2nc(OCC34CCCN3CCC4)nc3c2CCN(c2cccc4ccc(F)c(Cl)c24)C3)C1] | ++ |
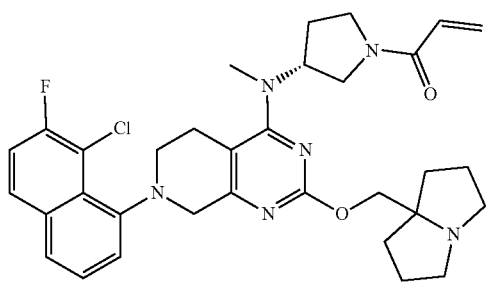
++++
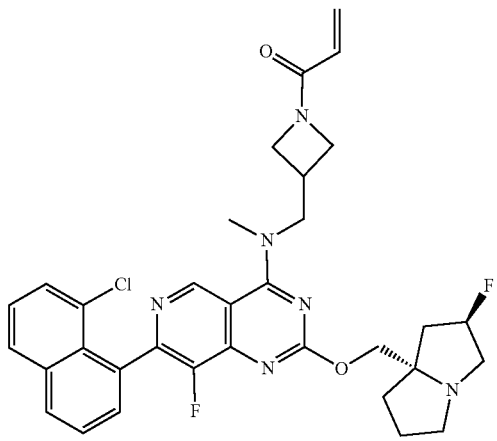 [SMILES: C=CC(=O)N1CC(CN(C)c2nc(OC[C@@]34CCCN3C[C@H](F)C4)nc3c(F)c(-c4cccc5cccc(Cl)c45)ncc23)C1]
++++
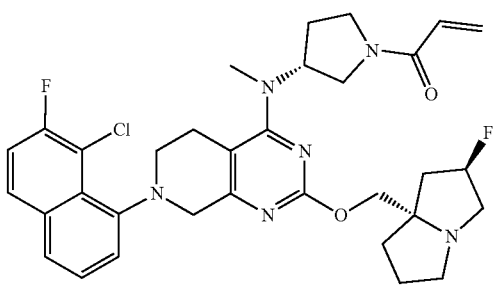 [SMILES: C=CC(=O)N1CC[C@@H](N(C)c2nc(OC[C@@]34CCCN3C[C@H](F)C4)nc3c2CCN(c2cccc4ccc(F)c(Cl)c24)C3)C1]

TABLE 1a-continued

Additional exemplary compounds—Inhibition of KRAS$^{G12C}$ and cRAF Binding

| Structure | RAF 1 RBD IC50 |
|---|---|
| 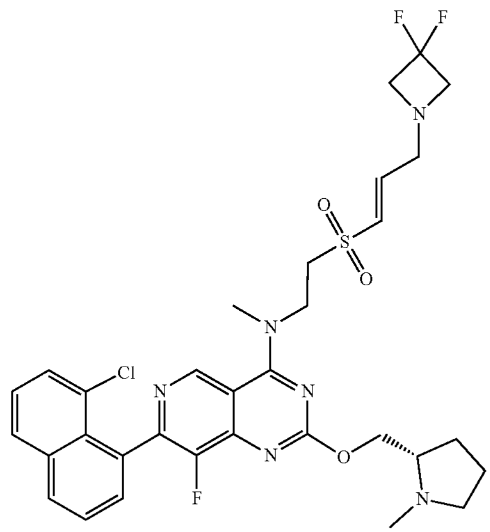 [SMILES: CN(CCS(=O)(=O)/C=C/CN1CC(F)(F)C1)c1nc(OC[C@@H]2CCCN2C)nc2c(F)c(-c3cccc4cccc(Cl)c34)ncc12] | + |
| 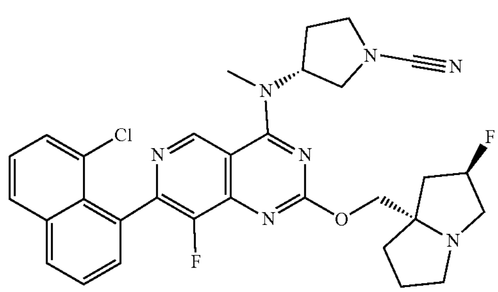 [SMILES: CN(c1nc(OC[C@@]23CCCN2C[C@H](F)C3)nc2c(F)c(-c3cccc4cccc(Cl)c34)ncc12)[C@@H]1CCN(C#N)C1] | +++ |
| 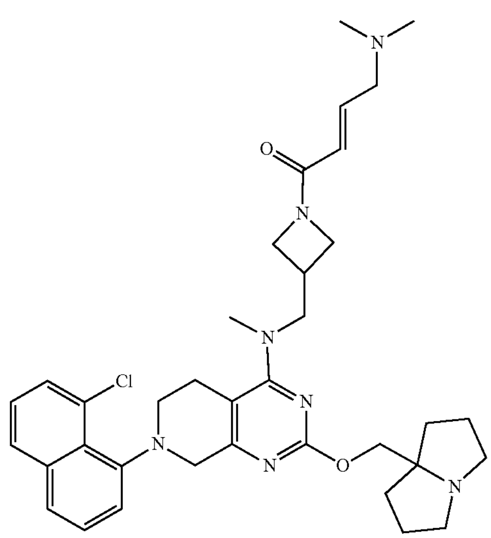 [SMILES: CN(C)C/C=C/C(=O)N1CC(CN(C)c2nc(OCC34CCCN3CCC4)nc3c2CCN(c2cccc4cccc(Cl)c24)C3)C1] | ++ |

TABLE 1a-continued

Additional exemplary compounds—Inhibition of KRAS$^{G12C}$ and cRAF Binding

| Structure | RAF 1 RBD IC50 |
|---|---|
| | +++ |
| 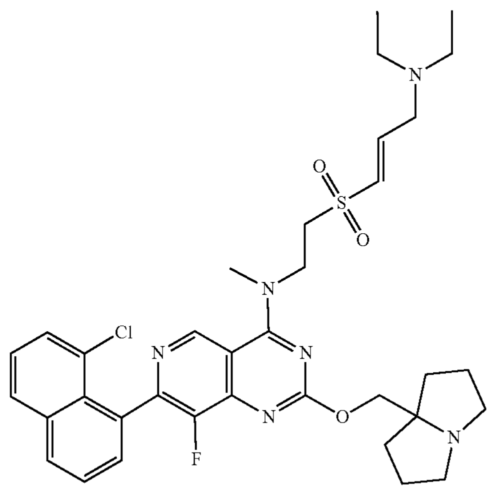 [SMILES: CCN(CC)C/C=C/S(=O)(=O)CCN(C)c1nc(OCC23CCCN2CCC3)nc2c(F)c(-c3cccc4cccc(Cl)c34)ncc12] | ++++ |
| | +++ |

* ++++ is less than 10 nM, +++ is 10 to less than 100 nM, ++ is 100 to less than 500 nM, + is greater or equal to 500 nM Example 309: Inhibition of KRASG$^{12}$C and PI3Ka Binding The AlphaScreen technology was used to determine IC$_{50}$s for compound inhibition of KRAS G12C (present as the Cys-light (C51S, C80L and C118S), truncated version comprising amino acids 1-169) and PI3Ka interaction. Compounds were diluted in 100% DMSO and each compound concentration was spotted at 200 nl/well onto low volume, white 384 well plates. The KRAS G12C contained a biotin-AviTag and the PI3Ka, as Ras-binding domain (amino acids 157-300, RBD), was His-tagged. KRAS G12C was preloaded with the GTP analogue Guanosine 5'-[β,γ-imido] triphosphate (GMPPNP). The KRAS GT2C was diluted in 25 mM Hepes, pH 7.4, 150 mM NaCl, 5 mM MgCl$_2$, 0.0100 TritonX-100 and 10 µM GMPPNP and added at 10 ul/well to compound-spotted plates resulting in a DMR concentration of 2%. Plates were incubated for 2 hours. A mixture of RBD and the AlphaScreen streptavidin donor and nickel chelate acceptor beads diluted in 25 mM Hepes, pH 7.4, 150 mM NaCl, 5 mM MgCl$_2$, 0.0100 TritonX-100 and 2% DMSO was then added at 10 ul/well and incubated for 60-90 minutes before the samples were read for emission at 570 nm after excitation of the donor beads at 680 nm. All incubations were performed at room temperature. The final top compound concentration was 50 µM with 1:3 titrations for 10-point dose response curves. Final assay conditions were 1.5 nM KRAS GT2C, 100 nM RBD, 1.25 ug/ml of AlphaScreen donor beads and 10 µg/ml AlphaLISA acceptor beads. IC$_{50}$s were determined using nonlinear regression fit of [inhibitor] vs. response (4 parameters).

A counter assay was also set up to rule out inhibitors of the AlphaScreen technology itself. Compound plates were incubated for 19-20 hours as above with buffer only. The AlphaScreen beads were added as above except an unrelated biotinylated His-tagged peptide was substituted for the RBD. Samples were read and analyzed as above.

Results for exemplary compounds are shown in Table 2.

TABLE 2

Inhibition of KRAS G12C and PI3Kalpha Binding (IC$_{50}$)

| Compound | PI3Ka RBD IC50 |
| --- | --- |
| 108 | ++++ |
| 109 | ++++ |
| 112 | ++++ |
| 113 | ++++ |
| 116 | ++++ |
| 117 | ++++ |
| 121 | ++++ |
| 125 | ++++ |
| 126 | ++++ |
| 130 | +++ |
| 131 | ++++ |
| 132 | ++++ |
| 133 | ++++ |
| 134 | ++++ |
| 139 | +++ |
| 140 | +++ |
| 142 | ++++ |
| 144 | ++++ |
| 145 | ++++ |
| 146 | ++++ |
| 160 | ++++ |
| 161 | +++ |
| 162 | ++++ |
| 163 | ++++ |
| 164 | ++++ |
| 165 | ++++ |
| 166 | ++++ |
| 167 | ++++ |
| 168 | +++ |
| 169 | ++++ |
| 170 | + |
| 171 | ++++ |
| 172 | +++ |
| 173 | +++ |
| 174 | ++++ |
| 175 | ++++ |
| 176 | ++++ |
| 177 | ++++ |
| 179 | ++++ |
| 180 | ++++ |
| 181 | ++++ |
| 182 | ++++ |
| 183 | ++++ |
| 210 | ++++ |
| 214 | ++++ |
| 231 | ++++ |
| 236 | ++++ |
| 240 | ++++ |
| 245 | ++++ |
| 247 | +++ |
| 248 | +++ |
| 251 | ++++ |
| 255 | ++++ |
| 256 | ++++ |
| 257 | ++++ |
| 258 | +++ |
| 259 | +++ |

Example 310: MCF10A (G12C or G12C-A59G)-KRAS Cell Viability Assay

MCF10A (ATCC, cat. CRL-10317) cells are maintained in MEBM (Lonza, cat. CC-3151) with 1% horse serum (Sigma, cat. H1270), MEGM mammary epithelial cell growth medium SingleQuotsKit (Lonza, cat. CC-4146) and 25 ng/ml Cholera toxin (Sigma, cat. C$_{8052}$). These cells are transduced with either KRAS G12C or G12C/A59G followed by puromycin selection to generate stably expressing cells. For the cell viability assay, 1000 cells of either MCF10A KRAS G12C or MCF10A G12C/A59G are plated in 384-well spheroid microplate (Corning, cat. 3830). The following day, cells are treated with compounds (10 uM top concentration, 3-fold dilution, and 11 doses). 10 uM Tremetinib (MCE, cat. HY-10999/CS-0060) is used as control. The Tecan: HP D300E is used to dispense the compounds. After five days of incubation, celltiter-glo luminescent assay kit (Promega, cat. G7573) is used according to manufacturer's protocol to measure cellular viability using a BioTek plate reader. The data is then imported to and processed in Dotmatics where EC50s were calculated using the Lavenberg-Marquardt 4 parameters fitting procedure, with difference gradients.

Example 311: Treatment of Human Patients

A human patient suffering from a cancer, (e.g., a KRAS mediated cancer, as disclosed herein) can be administered a therapeutically effective dose of a compound disclosed herein (e.g., a compound of Table 1). The treatment can slow down or halt the growth of a tumor, reduce a tumor volume or mass, or eradicate the tumor in the patient.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed:

1. A compound of Formula II:

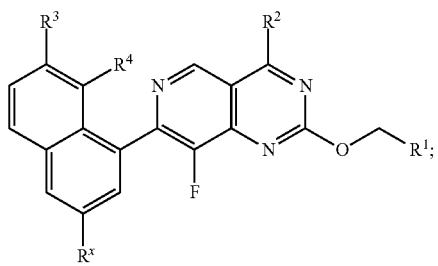

(Formula II)

or a salt thereof, or an isotopologue thereof, or a salt of an isotopologue thereof;
wherein:
  $R^x$ is hydrogen;
  $R^1$ is

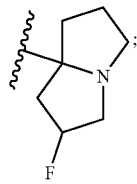 [SMILES: *C12CCCN1CC(F)C2]

$R^2$ is $R^{2c}$;
  $R^3$ is fluoro;
  $R^4$ is fluoro, chloro, methyl, ethyl, or ethynyl;
  $R^{2c}$ is —$NR^{15}R^{16}$;
  $R^{15}$ is methyl;
  $R^{16}$

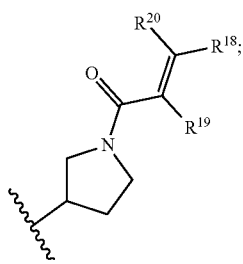

$R^{18}$ is hydrogen, —$(CH_2)_z$—$NR^{22}R^{23}$, —$(CH_2)_u$—$R^{34}$, or $R^{35}$;
  $R^{19}$ is hydrogen;
  $R^{20}$ is hydrogen;
  $R^{22}$ and $R^{23}$ are each methyl;
  z is 1;
  $R^{34}$ is azetidine substituted with 1 instance of methyl, pyrrolidine substituted with 1 instance of methoxy or fluoro, 2-oxa-5-azabicyclo[2.2.1]heptane, 3-oxa-8-azabicyclo[3.2.1]octane, or 3-oxa-6-azabicyclo[3.1.1]heptane;
  u is 0 or 1; and
  $R^{35}$ is

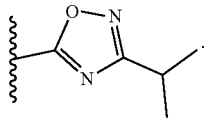 [SMILES: *c1nc(C(C)C)no1]

2. The compound of claim 1, or a salt thereof, or an isotopologue thereof, or a salt of an isotopologue thereof, wherein $R^1$ is

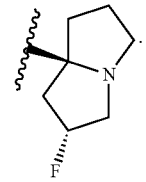

3. The compound of claim 1, or a salt thereof, or an isotopologue thereof, or a salt of an isotopologue thereof, wherein $R^4$ is fluoro or chloro.

4. The compound of claim 1, or a salt thereof, or an isotopologue thereof, or a salt of an isotopologue thereof, wherein $R^4$ is methyl or ethyl.

5. The compound of claim 1, or a salt thereof, or an isotopologue thereof, or a salt of an isotopologue thereof, wherein $R^4$ is ethynyl.

6. The compound of claim 1, or a salt thereof, or an isotopologue thereof, or a salt of an isotopologue thereof, wherein $R^{18}$ is hydrogen.

7. The compound of claim 1, or a salt thereof, or an isotopologue thereof, or a salt of an isotopologue thereof, wherein $R^{18}$ is —$(CH_2)_z$—$NR^{22}R^{23}$.

8. The compound of claim 1, or a salt thereof, or an isotopologue thereof, or a salt of an isotopologue thereof, wherein $R^{18}$ is —$(CH_2)_u$—$R^{34}$.

9. The compound of claim 1, or a salt thereof, or an isotopologue thereof, or a salt of an isotopologue thereof, wherein $R^{18}$ is $R^{35}$.

10. The compound of claim 1, or a salt thereof, or an isotopologue thereof, or a salt of an isotopologue thereof, wherein the compound is 1509
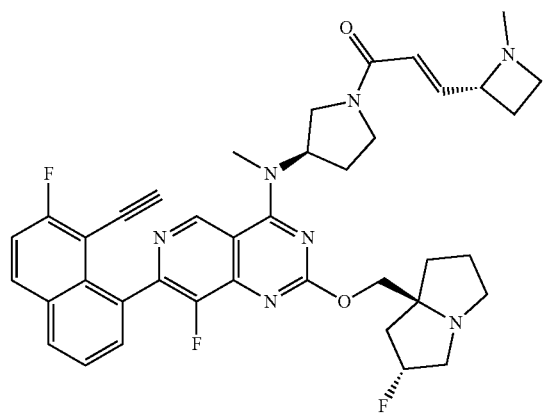
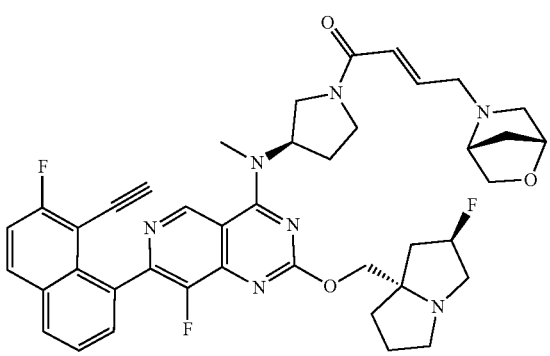
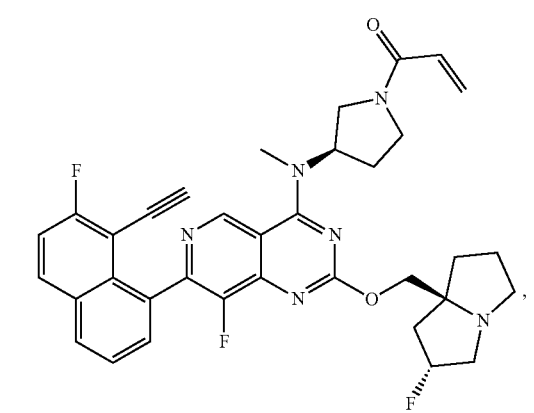
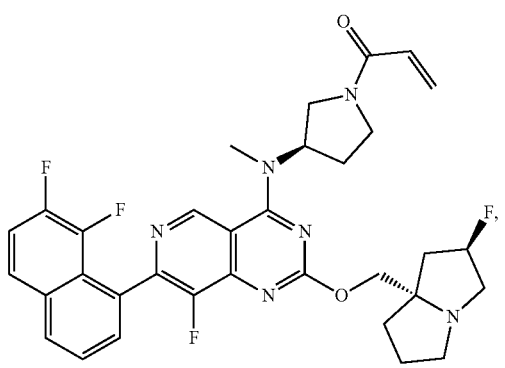
1510
-continued
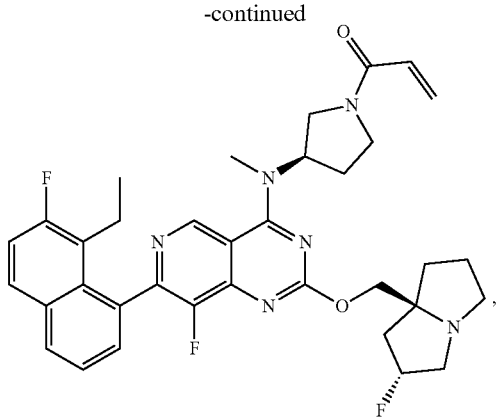
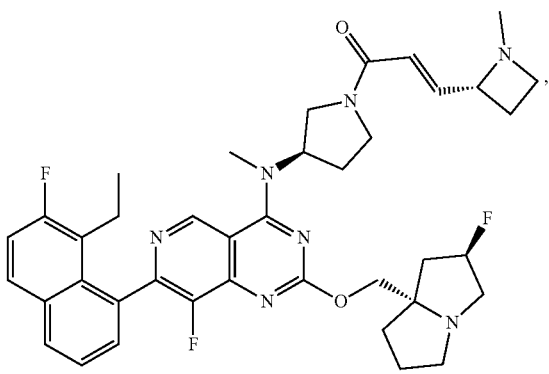
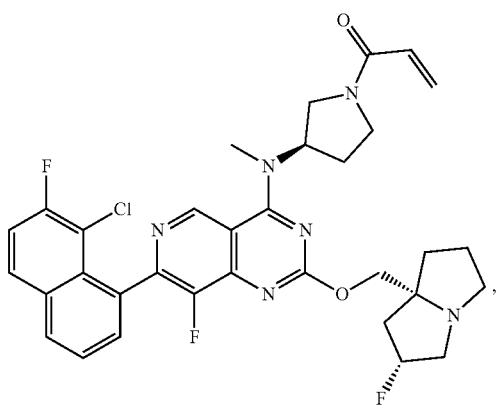
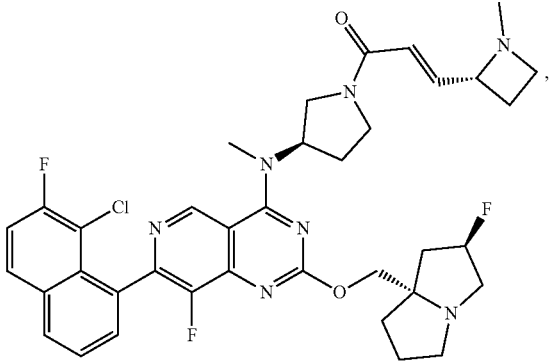

-continued
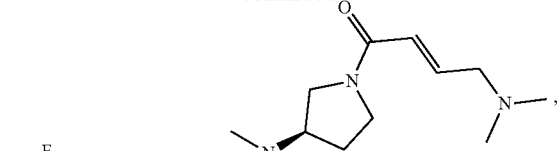
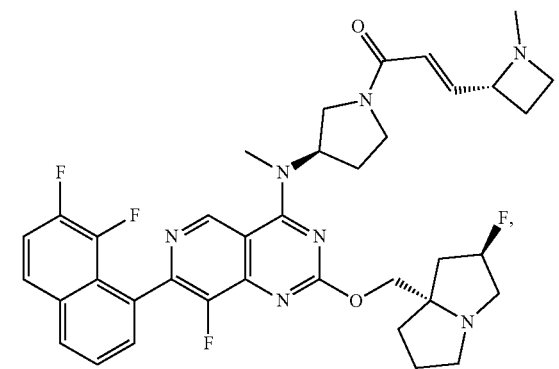
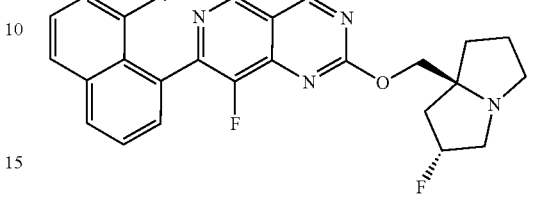
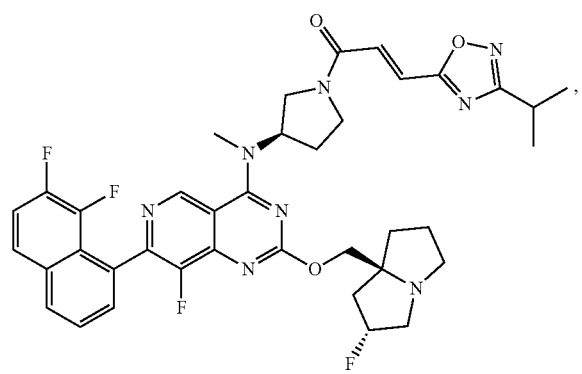
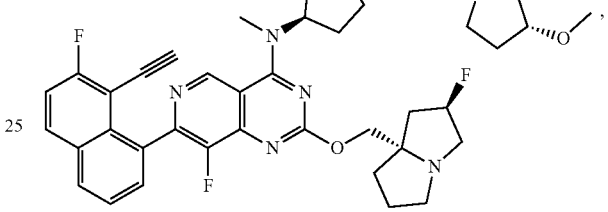
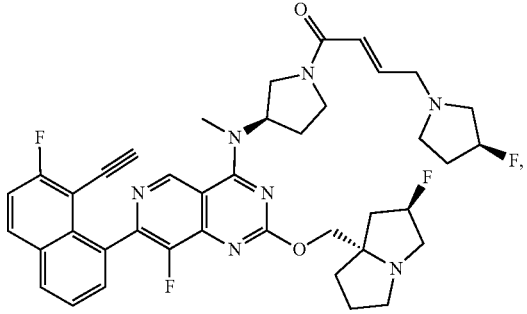
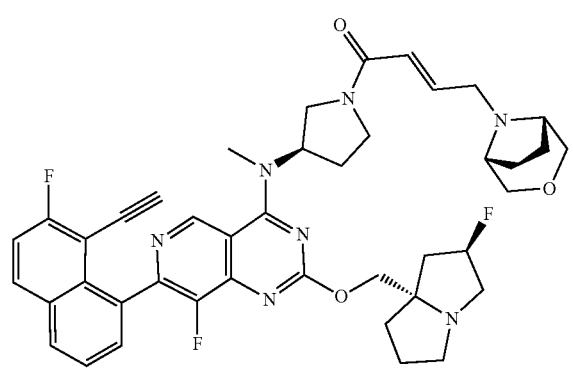
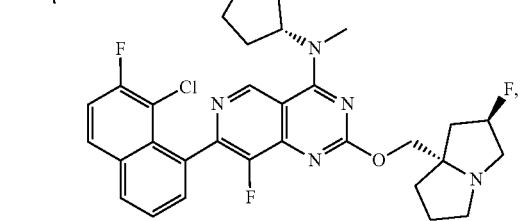
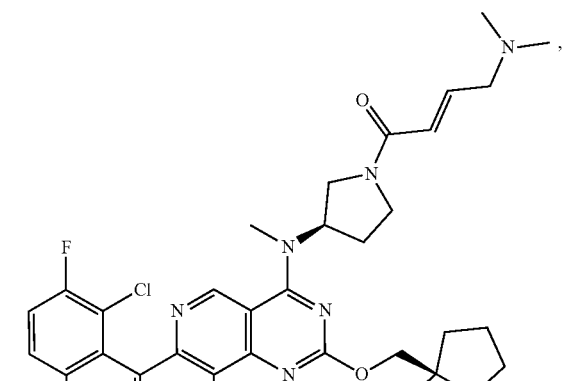
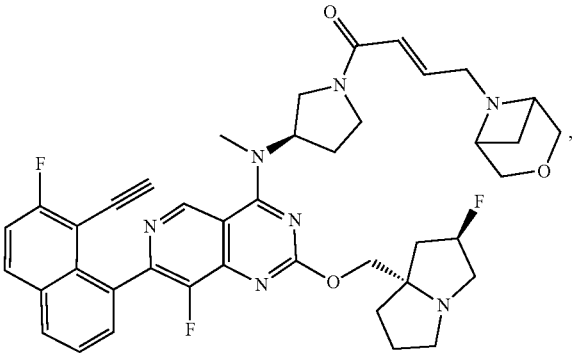

-continued

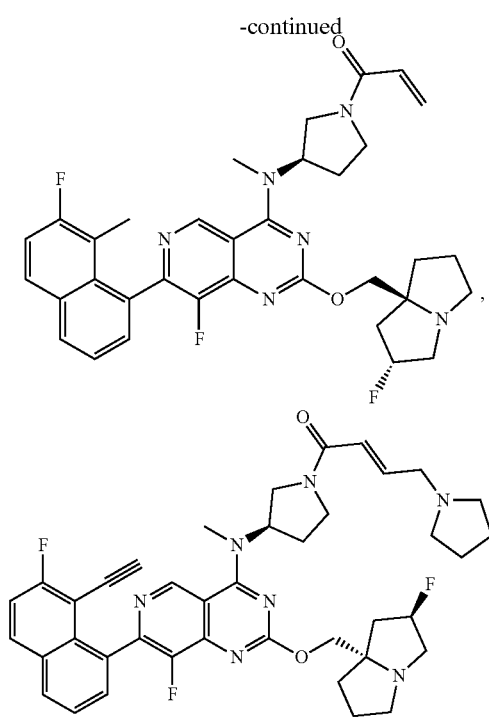

11. The compound of claim 1, wherein the compound is

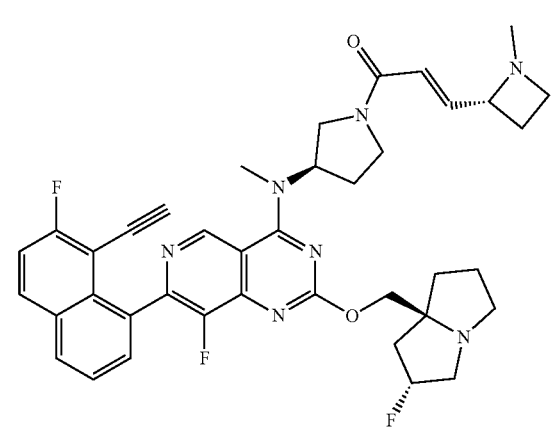

or a pharmaceutically acceptable salt thereof.

12. The compound of claim 1, wherein the compound is

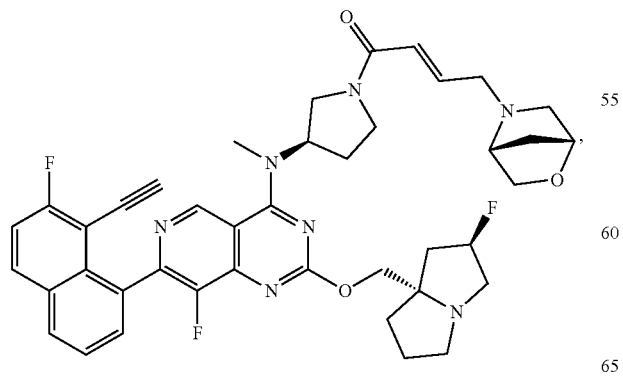

or a pharmaceutically acceptable salt thereof.

13. The compound of claim 1, wherein the compound is

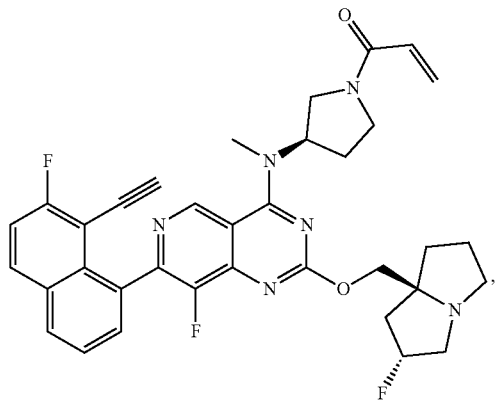 [SMILES: C#Cc1c(F)ccc2cccc(-c3ncc4c(N(C)[C@@H]5CCN(C(=O)C=C)C5)nc(OC[C@@]56CCCN5C[C@H](F)C6)nc4c3F)c12]

or a pharmaceutically acceptable salt thereof.

14. The compound of claim 1, wherein the compound is

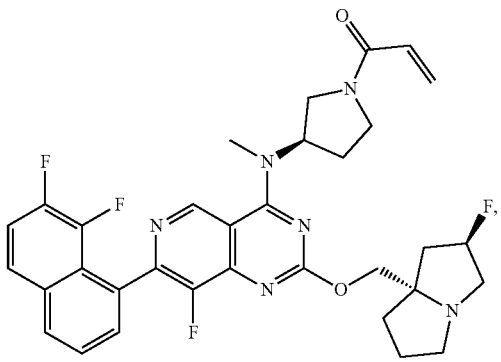 [SMILES: C=CC(=O)N1CC[C@@H](N(C)c2nc(OC[C@@]34CCCN3C[C@H](F)C4)nc3c(F)c(-c4cccc5ccc(F)c(F)c45)ncc23)C1]

or a pharmaceutically acceptable salt thereof.

15. The compound of claim 1, wherein the compound is

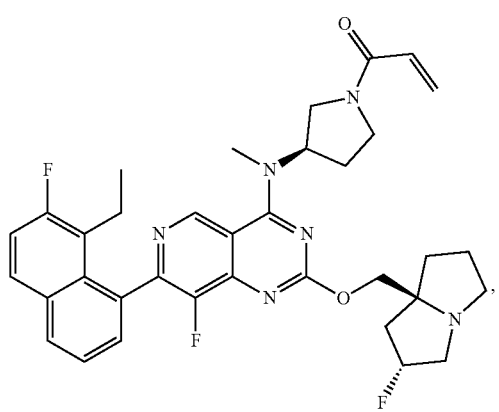 [SMILES: C=CC(=O)N1CC[C@@H](N(C)c2nc(OC[C@@]34CCCN3C[C@H](F)C4)nc3c(F)c(-c4cccc5ccc(F)c(CC)c45)ncc23)C1]

or a pharmaceutically acceptable salt thereof.

16. The compound of claim 1, wherein the compound is

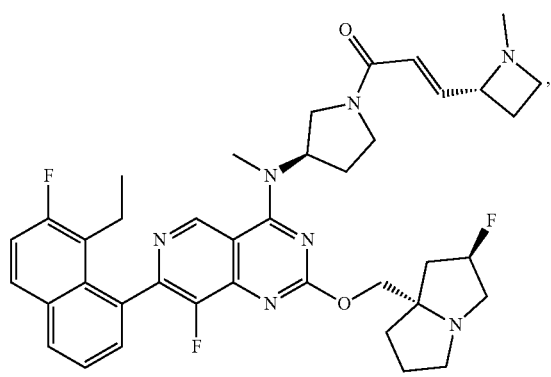 [SMILES: CCc1c(F)ccc2cccc(-c3ncc4c(N(C)[C@@H]5CCN(C(=O)/C=C/[C@H]6CCN6C)C5)nc(OC[C@@]56CCCN5C[C@H](F)C6)nc4c3F)c12]

or a pharmaceutically acceptable salt thereof.

17. The compound of claim 1, wherein the compound is

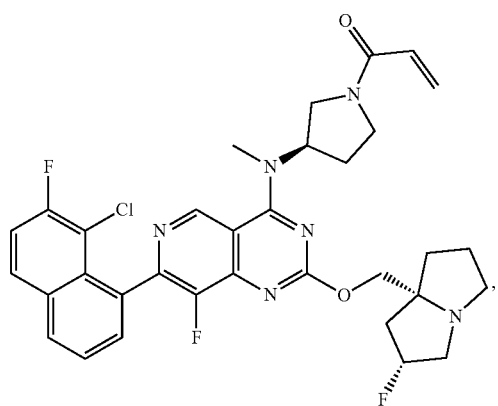 [SMILES: C=CC(=O)N1CC[C@@H](N(C)c2nc(OC[C@]34CCCN3C[C@H](F)C4)nc3c(F)c(-c4cccc5ccc(F)c(Cl)c45)ncc23)C1]

or a pharmaceutically acceptable salt thereof.

18. The compound of claim 1, wherein the compound is

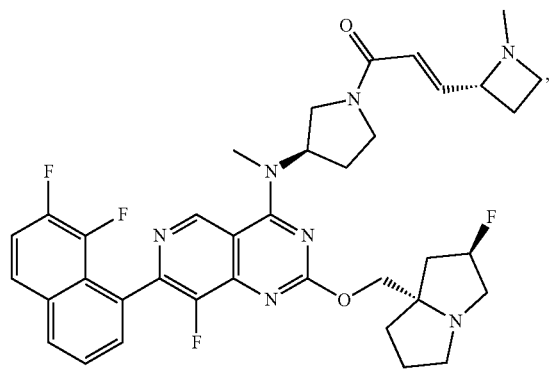 [SMILES: CN1CC[C@@H]1/C=C/C(=O)N1CC[C@@H](N(C)c2nc(OC[C@@]34CCCN3C[C@H](F)C4)nc3c(F)c(-c4cccc5ccc(F)c(F)c45)ncc23)C1]

or a pharmaceutically acceptable salt thereof.

19. The compound of claim 1, wherein the compound is

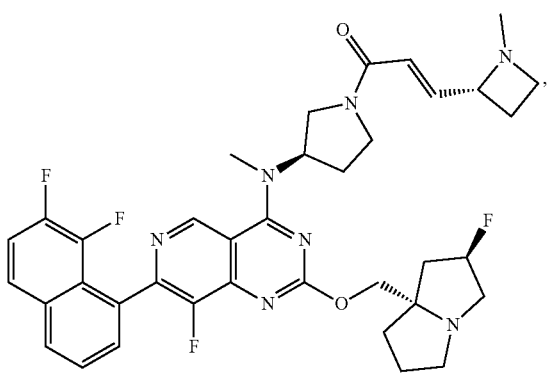 [SMILES: CN1CC[C@@H]1/C=C/C(=O)N1CC[C@@H](N(C)c2nc(OC[C@@]34CCCN3C[C@H](F)C4)nc3c(F)c(-c4cccc5ccc(F)c(F)c45)ncc23)C1]

or a pharmaceutically acceptable salt thereof.

20. The compound of claim 1, where the compound is

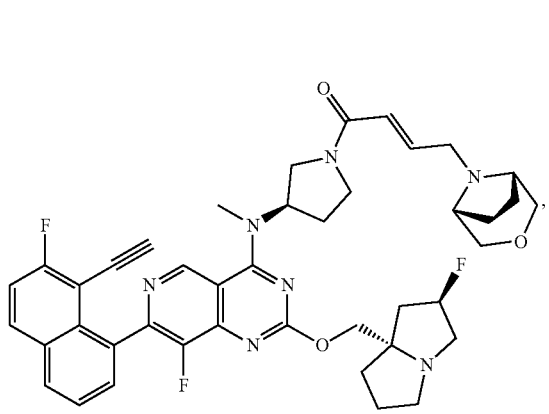

or a pharmaceutically acceptable salt thereof.

21. The compound of claim 1, wherein the compound is

22. The compound of claim 1, wherein the compound is

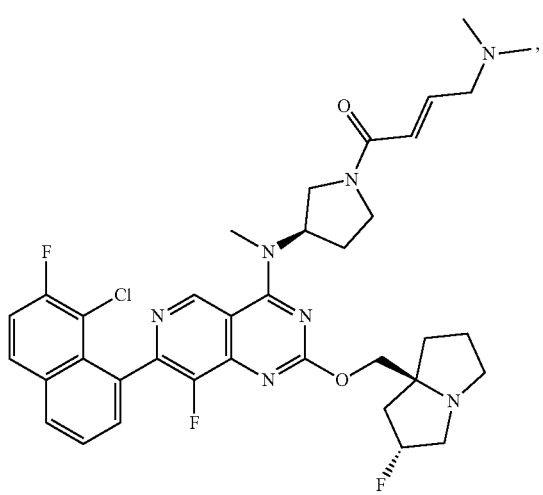 [SMILES: CN(C)C/C=C/C(=O)N1CC[C@@H](N(C)c2nc(OC[C@@]34CCCN3C[C@H](F)C4)nc3c(F)c(-c4cccc5ccc(F)c(Cl)c45)ncc23)C1]

or a pharmaceutically acceptable salt thereof.

23. The compound of claim 1, wherein the compound is

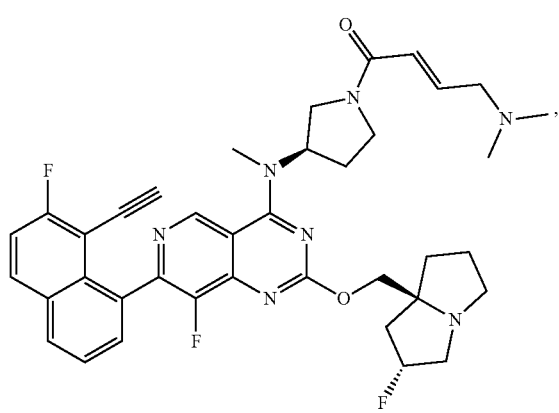 [SMILES: C#Cc1c(F)ccc2cccc(-c3ncc4c(N(C)[C@@H]5CCN(C(=O)/C=C/CN(C)C)C5)nc(OC[C@@]56CCCN5C[C@H](F)C6)nc4c3F)c12]

or a pharmaceutically acceptable salt thereof.

24. The compound of claim 1, wherein the compound is

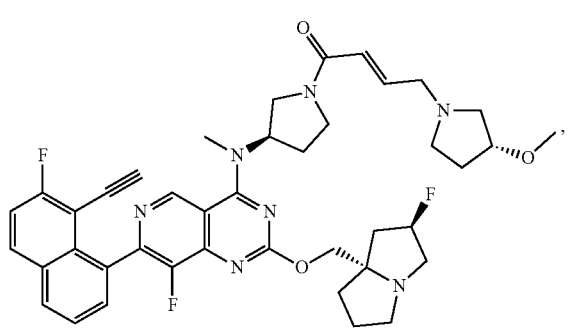 [SMILES: C#Cc1c(F)ccc2cccc(-c3ncc4c(N(C)[C@@H]5CCN(C(=O)/C=C/CN6CC[C@@H](OC)C6)C5)nc(OC[C@@]56CCCN5C[C@H](F)C6)nc4c3F)c12]

or a pharmaceutically acceptable salt thereof.

25. The compound of claim 1, wherein the compound is

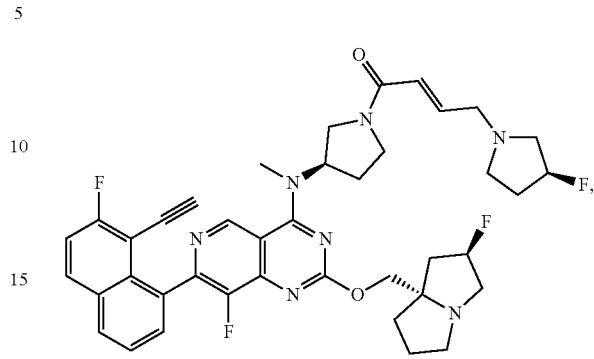

or a pharmaceutically acceptable salt thereof.

26. The compound of claim 1, wherein the compound is

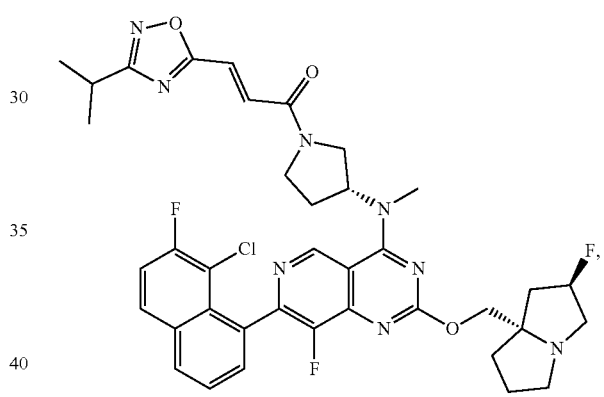

or a pharmaceutically acceptable salt thereof.

27. The compound of claim 1, wherein the compound is

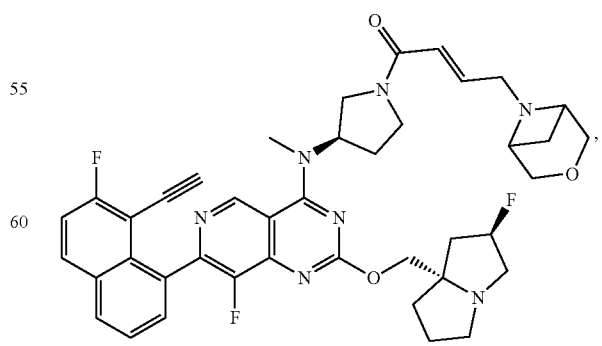

or a pharmaceutically acceptable salt thereof.

28. The compound of claim 1, wherein the compound is
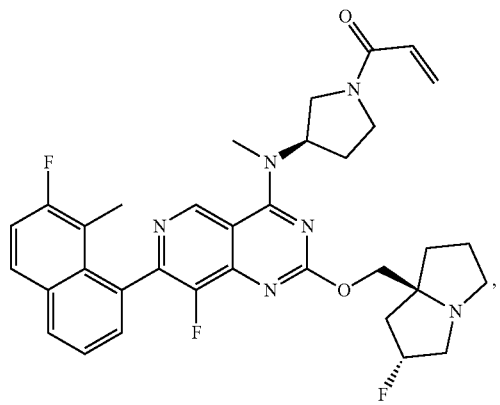 [SMILES: C=CC(=O)N1CC[C@@H](N(C)c2nc(OC[C@@]34CCCN3C[C@H](F)C4)nc3c(F)c(-c4cccc5ccc(F)c(C)c45)ncc23)C1]
or a pharmaceutically acceptable salt thereof.
29. The compound of claim 10, wherein the compound is
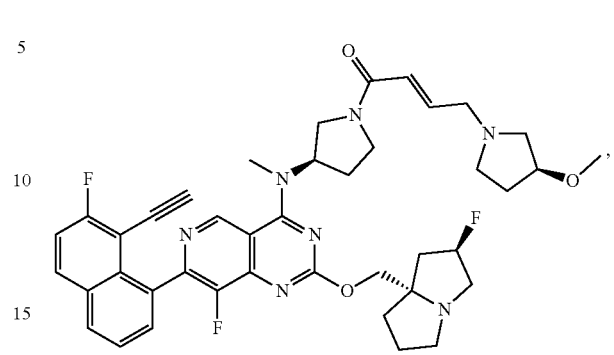
or a pharmaceutically acceptable salt thereof.
* * * * *